US012539292B2

(12) United States Patent
Crew et al.

(10) Patent No.: US 12,539,292 B2
(45) Date of Patent: Feb. 3, 2026

(54) BRM TARGETING COMPOUNDS AND ASSOCIATED METHODS OF USE

(71) Applicants: Arvinas Operations, Inc., New Haven, CT (US); Genentech, Inc., South San Francisco, CA (US)

(72) Inventors: Andrew P. Crew, Guilford, CT (US); Jing Wang, Milford, CT (US); Michael Berlin, Flemington, NJ (US); Peter Dragovich, South San Francisco, CA (US); Huifen Chen, South San Francisco, CA (US); Leanna Staben, South San Francisco, CA (US)

(73) Assignees: Arvinas Operations, Inc., New Haven, CT (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/590,329

(22) Filed: Oct. 1, 2019

(65) Prior Publication Data

US 2020/0038378 A1 Feb. 6, 2020

Related U.S. Application Data

(63) Continuation-in-part of application No. 16/372,345, filed on Apr. 1, 2019, now abandoned.

(60) Provisional application No. 62/797,754, filed on Jan. 28, 2019, provisional application No. 62/651,186, filed on Apr. 1, 2018.

(51) Int. Cl.

| | |
|---|---|
| ***A61K 31/427*** | (2006.01) |
| ***A61K 31/4035*** | (2006.01) |
| ***A61K 31/4245*** | (2006.01) |
| ***A61K 31/437*** | (2006.01) |
| ***A61K 31/4439*** | (2006.01) |
| ***A61K 31/496*** | (2006.01) |
| ***A61K 31/541*** | (2006.01) |
| ***A61K 47/54*** | (2017.01) |

(52) U.S. Cl.

CPC ........ *A61K 31/427* (2013.01); *A61K 31/4035* (2013.01); *A61K 31/4245* (2013.01); *A61K 31/437* (2013.01); *A61K 31/4439* (2013.01); *A61K 31/496* (2013.01); *A61K 31/541* (2013.01); *A61K 47/555* (2017.08)

(58) Field of Classification Search

None

See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Dashaies et al. |
| 9,500,653 | B2 | 11/2016 | Crews et al. |
| 9,632,089 | B2 | 4/2017 | Crews et al. |
| 2008/0214501 | A1 | 9/2008 | Pan et al. |
| 2012/0270800 | A1 | 10/2012 | Verdine et al. |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0291562 | A1 | 10/2015 | Crew et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |

(Continued)

FOREIGN PATENT DOCUMENTS

| | | | |
|---|---|---|---|
| CL | 2014000998 | A1 | 10/2014 |
| CL | 2014000511 | A1 | 12/2014 |

(Continued)

OTHER PUBLICATIONS

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

(Continued)

*Primary Examiner* — Po-Chih Chen

(74) *Attorney, Agent, or Firm* — McCarter & English, LLP; Michael J. DeGrazia; James M. Alburger

(57) ABSTRACT

The present disclosure relates to bifunctional compounds, which find utility as modulators of SMARCA2 or BRM (target protein). In particular, the present disclosure is directed to bifunctional compounds, which contain on one end a ligand that binds to the Von Hippel-Lindau E3 ubiquitin ligase, and on the other end a moiety which binds the target protein, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation or accumulation of the target protein are treated or prevented with compounds and compositions of the present disclosure.

30 Claims, 1 Drawing Sheet

(56) References Cited

U.S. PATENT DOCUMENTS

| | | | | |
|---|---|---|---|---|
| 2017/0281784 | A1 | 10/2017 | Wang et al. | |
| 2017/0307614 | A1 | 10/2017 | Crews et al. | |
| 2017/0327469 | A1 | 11/2017 | Crew et al. | |
| 2018/0015087 | A1 | 1/2018 | Liu et al. | |
| 2018/0072711 | A1 | 3/2018 | Crew et al. | |
| 2018/0099940 | A1 | 4/2018 | Crew et al. | |
| 2018/0125821 | A1 | 5/2018 | Crew et al. | |
| 2018/0147202 | A1 | 5/2018 | Crew et al. | |
| 2018/0155322 | A1 | 6/2018 | Crew et al. | |
| 2018/0177750 | A1 | 6/2018 | Crew et al. | |
| 2018/0179183 | A1 | 6/2018 | Crew et al. | |
| 2018/0193470 | A1 | 7/2018 | Crew et al. | |
| 2018/0215731 | A1 | 8/2018 | Crew et al. | |
| 2018/0228907 | A1 | 8/2018 | Crew et al. | |
| 2018/0237418 | A1 | 8/2018 | Crew et al. | |
| 2018/0256586 | A1 | 9/2018 | Crew et al. | |
| 2018/0353501 | A1 | 12/2018 | Crew et al. | |
| 2019/0151295 | A1 | 5/2019 | Crew et al. | |
| 2020/0306273 | A1* | 10/2020 | Yang .................... | C07D 207/16 |
| 2020/0392131 | A1 | 12/2020 | Crew et al. | |
| 2021/0238193 | A1 | 8/2021 | Mainolfi et al. | |

FOREIGN PATENT DOCUMENTS

| | | | |
|---|---|---|---|
| CL | 2017001687 | A1 | 3/2018 |
| CN | 104736569 | A | 6/2015 |
| CN | 107531668 | A | 1/2018 |
| CN | 108601764 | A | 9/2018 |
| CN | 109152933 | A | 1/2019 |
| EP | 2985285 | | 2/2016 |
| JP | 2018-510851 | A | 4/2018 |
| JP | 2018-512449 | A | 5/2018 |
| WO | WO 2000/066119 | | 11/2000 |
| WO | WO 2002/066512 | | 8/2002 |
| WO | WO 2002/100845 | | 12/2002 |
| WO | WO 2006/113942 | | 10/2006 |
| WO | WO 2007/106670 | | 9/2007 |
| WO | WO 2008/011392 | | 1/2008 |
| WO | WO 2009/015254 | | 1/2009 |
| WO | WO 2010/141805 | | 12/2010 |
| WO | WO 2012/003281 | | 1/2012 |
| WO | WO 2012/040527 | | 3/2012 |
| WO | WO 2012/078559 | | 6/2012 |
| WO | WO 2012/090104 | | 7/2012 |
| WO | WO 2017/176958 | | 10/2012 |
| WO | WO 2013/106643 | | 7/2013 |
| WO | WO 2013/106646 | | 7/2013 |
| WO | WO 2013/170147 | | 11/2013 |
| WO | WO 2014/108452 | | 7/2014 |
| WO | WO 2014/123418 | | 8/2014 |
| WO | WO 2015/000868 | | 1/2015 |
| WO | WO 2015/160845 | | 10/2015 |
| WO | WO 2016/138114 | | 1/2016 |
| WO | WO 2016/105518 | | 6/2016 |
| WO | 2016/149668 | A1 | 9/2016 |
| WO | WO 2016/138114 | A1 | 9/2016 |
| WO | WO 2016/146985 | | 9/2016 |
| WO | WO 2016/169989 | | 10/2016 |
| WO | WO 2016/172134 | | 10/2016 |
| WO | WO 2016/197114 | | 12/2016 |
| WO | 2017/007612 | A1 | 1/2017 |
| WO | WO 2017/011590 | | 1/2017 |
| WO | WO 2017/024317 | | 2/2017 |
| WO | WO 2017/024318 | A1 | 2/2017 |
| WO | WO 2017/024319 | A1 | 2/2017 |
| WO | WO 2017/030814 | | 2/2017 |
| WO | WO 2017/046036 | | 3/2017 |
| WO | WO 2017/079267 | | 5/2017 |
| WO | WO 2017/117473 | | 7/2017 |
| WO | WO 2017/117474 | | 7/2017 |
| WO | WO 2017/176957 | | 10/2017 |
| WO | WO 2017/184995 | A1 | 10/2017 |
| WO | WO 2017/185023 | | 10/2017 |
| WO | WO 2017/185031 | | 10/2017 |
| WO | WO 2017/185034 | | 10/2017 |
| WO | WO 2017/185036 | | 10/2017 |
| WO | WO 2017/197055 | | 11/2017 |
| WO | WO 2017/197056 | A1 | 11/2017 |
| WO | WO 2017/223415 | | 12/2017 |
| WO | WO 2017/223452 | | 12/2017 |
| WO | WO 2018/052945 | | 3/2018 |
| WO | WO 2018/052949 | | 3/2018 |
| WO | WO 2018/064589 | A1 | 4/2018 |
| WO | WO 2018/089736 | A1 | 5/2018 |
| WO | WO 2018/098275 | | 5/2018 |
| WO | WO 2018/098280 | A1 | 5/2018 |
| WO | WO 2018/098288 | | 5/2018 |
| WO | WO 2018/106870 | | 6/2018 |
| WO | WO 2018/148440 | | 8/2018 |
| WO | WO 2019/084030 | A1 | 5/2019 |
| WO | WO 2019/195201 | A1 | 10/2019 |

OTHER PUBLICATIONS

Papillon et al., Discovery of Orally Active Inhibitors of Brahma Homolog (BRM)/SMARCA2 ATPase Activity for the Treatment of Brahma Related Gene 1 (BRG1)/SMARCA4-Mutant Cancers. Journal of Medicinal Chemistry, 2018, 61, 10155-10172.*

Grant & Hackh's Chemical Dictionary (5th Ed. 1987) at p. 148.*

Ahn, et al., "HIF-lalpha peptide derivatives with modifications at the hydroxyproline residue as activators of HIF-lalpha", Bioorg Med Chem Lett. 19(15), 2009, 4403-4405.

Bargagna-Mohan, et al., "Use of PROTACS as molecular probes of angiogenesis", Bioorg Med Chem Left. 15(11) 2005, 2724-2727.

Bondeson DP, et al. (2018) "Lessons in PROTAC Design from Selective Degradation with a Promiscuous Warhead." *Cell Chem Biol* 25(1):78-87 e75.

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule PROTACS", National Chem Biol. 11(8) Aug. 2015, 611-617.

Buckley, et al., "HaloPROTACS: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and HIF1a", Angew Chem Int Ed Engl.51(46), Nov. 12, 2012, 11463-11467.

Buckley, et al., "Targeting the von Hippel-Lindau E3 ubiquitin ligase using small molecules to disrupt the VHL/HIF-1a interaction", Journal of the American Chemical Society, Feb. 27, 2012, 134(10): 4465-4468.

Burslem GM, et al. (2018) "The Advantages of Targeted Protein Degradation Over Inhibition: An RTK Case Study." *Cell Chem Biol* 25(1):67-77 e63.

Burslem, et al., (2017) "Small-Molecule Modulation of Protein Homeostasis." *Chem Rev* 117(17):11269-11301.

Carmony, KC, et al., "PROTAC-Induced Proteolytic Targeting", Methods Mol. Biol., 2012, vol. 832, pp. 627-638.

CAS Registry No. 1004933-70-3, which entered STN on Feb. 21, 2008.

CAS Registry No. 871986-52-6 entered STN Jan. 16, 2006.

Chan, et al., (2018) "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) Bet Inhibitor Scaffolds. " *J Med Chem* 61(2):504-513.

Churcher I (2018) "Protac-Induced Protein Degradation in Drug Discovery: Breaking the Rules or Just Making New Ones?" *J Med Chem* 61(2):444-452.

Corson, et al., "Design and applications of bifunctional small molecules: why two heads are better than one", ACS Chemical Biology vol. 3 No. 11, pp. 677-692; Nov. 21, 2008.

Crew AP, et al. (2018) "Identification and Characterization of Von Hippel-Lindau-Recruiting Proteolysis Targeting Chimeras (PROTACs) of TANK-Binding Kinase 1." *J Med Chem* 61(2):583-598.

Crews, C. M., "Targeting the undruggable proteome: the small molecules of my dreams", *Chem Biol* 17, 551-555, doi:S1074-5521(10)00196-1 [pii] 10.1016/j.chembio1.2010.05.011 (2010).

(56) References Cited

OTHER PUBLICATIONS

Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Han, Xin, et al., Discovery of ARD-69 as a Highly Potent Proteolysis Targeting Chimera (PROTAC) Degrader of Androgen Receptor (AR) for the Treatment of Prostate Cancer, Journal of Medicinal Chemistry 2019 62 (2), 941-964, DOI: 10.1021/acs.jmedchem.8b01631.
Hines, J., et al., "Posttranslational protein knockdown coupled to receptor tyrosine kinase activation with phosphoPROTACs", Proc Natl Acad Sci USA 110, 8942-8947 (2013).
Hon, et al., "Structural basis for the recognition of hydroxyproline in Hlf-1 alpha by pVHL", Nature 417, Jun. 27, 2002, 975-978.
Hu, Jiantao, et al., Discovery of ERD-308 as a Highly Potent Proteolysis Targeting Chimera (PROTAC) Degrader of Estrogen Receptor (ER), DOI: 10.1021/acs.jmedchem.8b01572, Journal of Medicinal Chemistry, vol. 62, pp. 1420-1442, 2019, http:/dx.doi.org/10.1021/acs.imedchem.8b01572.
Huang HT, et al. (2018) "A Chemoproteomic Approach to Query the Degradable Kinome Using a Multi-kinase Degrader." *Cell Chem Biol* 25(1):88-99 e86.
Huang, et al., (2016) "Drugging the undruggables: exploring the ubiquitin system for drug development." *Cell Res* 26(4): 484-498.
Hughes, et al., (2017) "Molecular recognition of ternary complexes: a new dimension in the structure-guided design of chemical degraders." *Essays Biochem* 61(5):505-516.
Itoh, et al., "Development of target protein selective degradation inducer for protein knockdown," Bioorg. Med. Chem., 2011, 19, 3229-3241.
Itoh, et al., "Protein knockdown using methyl bestatin-ligand hybrid molecules: design and synthesis of inducers of ubiquitination-mediated degradation of cellular retinoic acid-binding proteins," J. Am. Chem. Soc., 2010, 132, 5820-5826.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Lu, et al., "Hijacking the E3 ubiquitin ligase cereblon to efficiently target BRD4", Chem Biol 22(6), 2015, 755-763.
Maniaci C, et al. (2017) "Homo-PROTACs: bivalent small-molecule dimerizers of the VHL E3 ubiquitin ligase to induce self-degradation." *Nat Commun* 8(1):830 1-13.
Medline Plus Trusted Health Information for You, www.nim.nih.gov/medlineplus/cancer.html pp.1-10, (2007).
Min, Jung-hyun, et al., "Structure of an HIV-1-alpha-pVHL complex: hydroxyproline recognition in signaling", Jun. 7, 2002, 296: 1886-1889.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Noguchi-Yachide, et al., BET Bromodomain as a Target of Epigenitic Therapy, Chemical and Pharmaceutical Bulletin, Jun. 1, 2016, vol. 64, Iss 6, pp. 540-547.
Ohoka, N. et al. SNIPER(TACC3) induces cytoplasmic vacuolization and sensitizes cancer cells to Bortezomib. Cancer Sci. 108, 1032-1041 (2017).
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Powell, C. E. et al. Chemically Induced Degradation of Anaplastic Lymphoma Kinase (Alk). J. Med. Chem. 61, 4249-4255 (2018).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina et al., "Chemical Inducers of Targeted Protein Degradation," The Journal of Biological Chemistry, 2010, vol. 285, No. 15, pp. 11057-11060.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).

(56) References Cited

OTHER PUBLICATIONS

Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stanton, et al., (2018) "Chemically induced proximity in biology and medicine." *Science* 359(6380).
Sun, B. et al. BET protein proteolysis targeting chimera (PROTAC) exerts potent lethal activity against mantle cell lymphoma cells. Leukemia 32, 343-352 (2018).
Toure, et al., (2016) "Small-Molecule PROTACS: New Approaches to Protein Degradation." *Angew Chem Int Ed Engl* 55(6):1966-1973.
Van Molle, et al., "Dissecting fragment-based lead discovery at the von Hippel-Lindau protein:hypoxia inducible factor la protein-protein interface", Chem Biol. 19(10), Oct. 26, 2012, 1300-1312.
Winter, et al., "Phthalimide Conjugation as a strategy for in vivo target protein degradation", Science, 2015 vol. 348 (6241), pp. 1376-1381 [Pub online: May 21, 2015].
Zengerle, et al., "Selective Small Molecule Induced Degradation of the BET Bromodomain Protein BRD4" ACS Chemical Biology, Jun. 2, 2015, vol. 10, pp. 1770-1777.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).
Farnaby, William, et al., BAF complex vulnerabilities in cancer demonstrated via structure-based PROTAC design, Nature Chemical Biology, Nature Pub Group, New Yourk, vol. 15, No. 7, Jun. 10, 2019.
International Search Report and Written Opinion for PCT/US2020/053815 dated Dec. 7, 2020.
Rydzewski, Real World Drug Discovery 2008, pp. 42-43.

* cited by examiner

BRM TARGETING COMPOUNDS AND ASSOCIATED METHODS OF USE

CROSS-REFERENCE TO RELATED APPLICATIONS

This application is a Continuation-in-part of U.S. Non-provisional application Ser. No. 16/372,345, filed 1 Apr. 2019 and titled BRM TARGETING COMPOUNDS AND ASSOCIATED METHODS OF USE, which claims priority to and the benefit of U.S. Provisional Patent Application Ser. No. 62/651,186, filed: 1 Apr. 2018, titled BRM TARGETING PROTAC COMPOUNDS AND ASSOCIATED METHODS OF USE, and U.S. Provisional Patent Application Ser. No. 62/797,754, filed: 28 Jan. 2019, titled BRM TARGETING PROTAC COMPOUNDS AND ASSOCIATED METHODS OF USE, both of which are incorporated herein by reference in their entirety.

FIELD OF THE INVENTION

The description provides bifunctional compounds comprising a target protein binding moiety and a E3 ubiquitin ligase binding moiety, and associated methods of use. The bifunctional compounds are useful as modulators of targeted ubiquitination, especially with respect to Switch/Sucrose Non Fermentable (SWI/SNF)-Related. Matrix-Associated, Actin-Dependent Regulator of Chromatin, Subfamily A, Member 2 (SMARCA2) (i.e., BRAHMA or BRM), which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Bifunctional compounds such as those that are described in U.S. Patent Application Publications 2015-0291562 and 2014-0356322 (incorporated herein by reference), function to recruit endogenous proteins to an E3 ubiquitin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

The Switch/Sucrose Non Fermentable (SWI/SNF) is a multi-subunit complex that modulates chromatic structure through the activity of two mutually exclusive helicase/ATPase catalytic subunits SWI/SNF-Related, Matrix-Associated, Actin-Dependent Regulator of Chromatin, Subfamily A, Member 2 (SMARCA2, BRAHMA or BRM) and SWI/SNF-Related, Matrix-Associated, Actin-Dependent Regulator of Chromatin, Subfamily A, Member 4 (SMARCA4 or BRG1). The core and the regulatory subunits couple ATP hydrolysis to the perturbation of histone-DNA contacts, thereby providing access points to transcription factors and cognate DNA elements that facilitate gene activation and repression.

Mutations in the genes encoding the twenty canonical SWI/SNF subunits are observed in nearly 20% of all cancers with the highest frequency of mutations observed in rhabdoid tumors, female cancers (including ovarian, uterine, cerical and endometrial), lung adenocarcinoma, gastric adenocarcinoma, melanoma, esophageal, and feanal clear cell carcinoma. Despite having a high degree of homology, and their presumed overlapping functions, SMARCA2 and SMARCA4 have been reported as having different roles in cancer. For example, SMARCA4 is frequently mutated in primary tumors, while SMARCA2 inactivation is infrequent in tumor development. In fact, numerous types of cancer have been shown to be SMARCA4-related (e.g., cancers having a SMARCA4-mutation or a SMARCA4-deficiency, such as lack of expression), including, e.g., lung cancer (such as non-small cell lung cancer).

SMARCA2 has been demonstrated as one of the top essential genes in SMARCA4-related or -mutant cancer cell lines. This is because SMARCA4-deficient patient populations or cells depend exclusively on SMARCA2 activity—i.e., there is a greater incorporation of SMARCA2 into the complex to compensate for the SMARCA4 deficiency. Thus, SMARCA2 may be targeted in SMARCA4-related/deficient cancers. The co-occurrence of the deficiency of the expression of two (or more) genes that leads to cell death is known as, synthetic lethality. Accordingly, synthetic lethality can be leveraged in the treatment of certain SMARCA2/SMARCA4-related cancers.

There is an ongoing need for effective treatment for diseases that are treatable by inhibiting or degrading SMARCA2 (i.e., BRAHMA or BRM). However, non-specific effects, and the inability to target and modulate SMARCA2 remains an obstacle to the development of effective treatments. As such, small-molecule therapeutic agents that target SMARCA2 and that leverage or potentiate VHL's substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., SMARCA4-related/deficient cancer, such as lung cancer or non-small cell lung cancer.

As such, in one aspect the disclosure provides bifunctional or PROTAC compounds, which comprise an E3 ubiquitin ligase binding moiety (i.e., a ligand for an E3 ubiquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM). For example, the structure of the bifunctional compound can be depicted as:

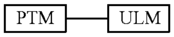

The respective positions of the PTM and ULM moieties as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

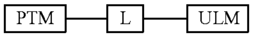

where PTM is a protein/polypeptide targeting moiety, L is a linker, e.g., a bond or a chemical group coupling PTM to ULM, and ULM is a Von Hippel-Lindau E3 ubiquitin ligase (VHL) binding moiety (VLM).

For example, the structure of the bifunctional compound can be depicted as:

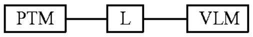

wherein: PTM is a protein/polypeptide targeting moiety; "L" is a linker (e.g. a bond or a chemical linker group) coupling the PTM and a VLM, wherein VLM is Von Hippel-Lindau E3 ubiquitin ligase binding moiety that binds to VHL E3 ligase.

In certain embodiments, the compounds as described herein comprise multiple independently selected ULMs, multiple PTMs, multiple chemical linkers or a combination thereof.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of tram-5-hydroxyproline, where both nitrogen and carboxylic acid in tram-5-hydroxyproline are functionalized as amides.

In an additional aspect, the description provides therapeutic compositions comprising an effective amount of a compound as described herein or salt form thereof, and a pharmaceutic ally acceptable carrier. The therapeutic compositions modulate protein degradation and/or inhibition in a patient or subject, for example, an animal such as a human, and can be used for treating or ameliorating disease states or conditions which are modulated through the degraded/inhibited protein. In certain embodiments, the therapeutic compositions as described herein may be used to effectuate the degradation of proteins of interest for the treatment or amelioration of a disease, e.g., cancer (including at least one of SWI/SNF associated cancer, a cancer with a SMARCA4 mutation, a cancer with a SMARCA4-deficiency, or a combination thereof), such as lung cancer (e.g., non-small cell lung cancer). In yet another aspect, the present disclosure provides a method of ubiquitinating/degrading a target protein in a cell. In certain embodiments, the method comprises administering a bifunctional compound as described herein comprising a VLM, preferably linked through a linker moiety, as otherwise described herein, wherein the VLM is coupled to the PTM through a linker to target a protein for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
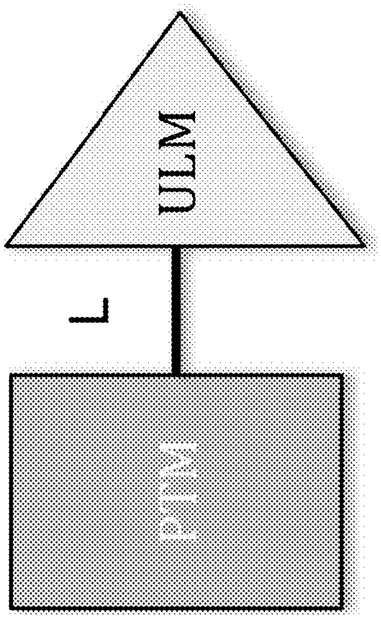
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.
Figure 1B:
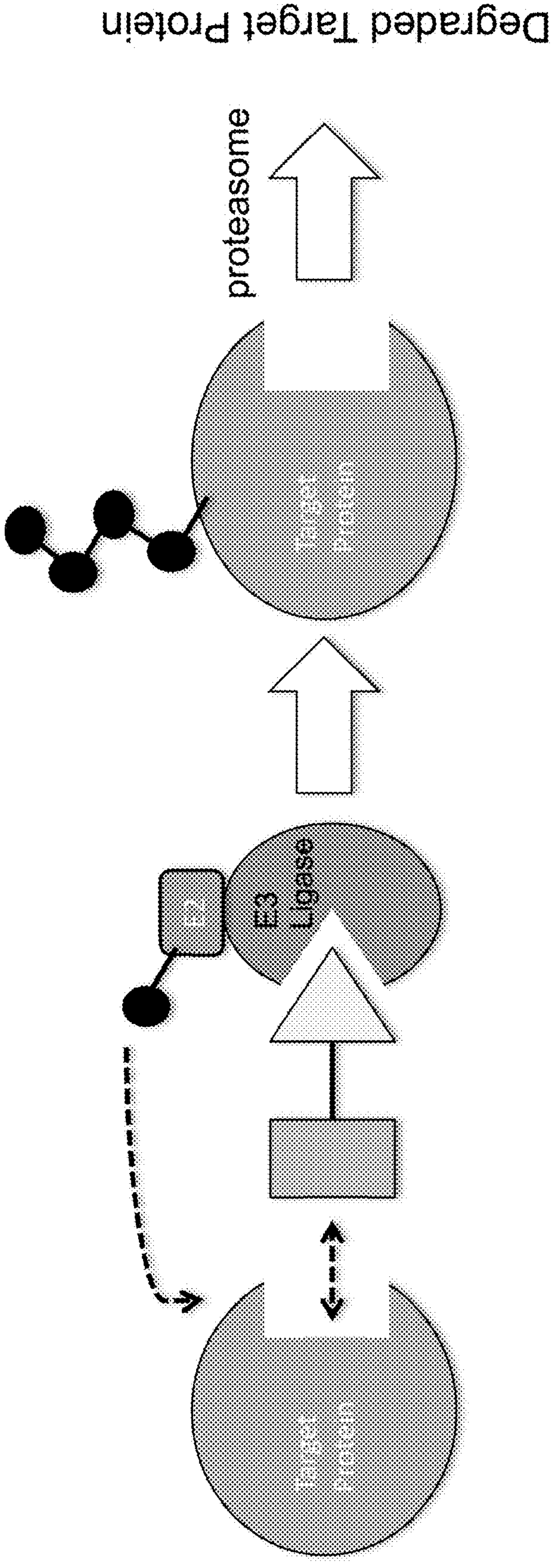

Presently described are compositions and methods that relate to the surprising and unexpected discovery that an E3 ubiquitin ligase protein (e.g., Von Hippel-Lindau E3 ubiquitin ligase (VHL)) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquitin ligase binding moiety ("ULM") coupled to a protein target binding moiety ("PTM"), which result in the ubiquitination of a chosen target protein, which leads to degradation of the target protein by the proteasome (see FIG. 1). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as VHL. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome. As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Absent a specific number of carbon atoms, an alkyl group provided herein is assumed to have one to twelve carbons, one to eight carbons, one to six carbons, or one to four carbons. Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. Alkyl groups may be optionally substituted as provided herein. In some embodiments, the alkyl group is a $C_{1-6}$ alkyl; in some embodiments, it is a $C_{1-4}$ alkyl.

U.S. patent application Ser. No. 15/230,354, filed on Aug. 5, 2016; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639; and International Patent Application No. PCT/US2016/019328, filed Feb. 24, 2016, published as International Patent Application Publication No. WO2016/138114, and International Patent Application No. PCT/US2016/023258, filed Mar. 18, 2016, published as International Patent Application Publication No. WO2016/149668, and U.S. Non-Provisional patent application Ser. No. 15/885,671, filed 31 Jan. 2018, published as U.S. Patent Application Publication No. 2018/0215731, all of which are incorporated herein by reference in their entirety. Furthermore, all references cited herein are incorporated by reference herein in their entirety.

The term "optionally substituted", as used in combination with a substituent defined herein, means that the substituent may, but is not required to be, substituted with one or more suitable functional groups or other substituents as provided herein. For example, a substituent may be optionally substituted with one or more of: halo, cyano, $C_{1-6}$ alkyl, $C_{3-6}$ cycloalkyl, $C_{2-6}$ alkenyl, $C_{2-6}$ alkynyl, halo($C_{1-6}$)alkyl, $C_{1-6}$ alkoxy, halo($C_{1-6}$alkoxy), $C_{1-6}$ alkylthio, $C_{1-6}$ alkylamino, $NH_2$, NH($C_{1-6}$ alkyl), N($C_{1-6}$ alkyl)$_2$, NH($C_{1-6}$ alkoxy), N($C_{1-6}$ alkoxy)$_2$, —C(O)NH$C_{1-6}$ alkyl, —C(O)N($C_{1-6}$ alkyl)$_2$, —C(O)$NH_2$, —C(O)$C_{1-6}$ alkyl, —C(O)$_2$$C_{1-6}$ alkyl, —NHCO($C_{1-6}$ alkyl), —N($C_{1-6}$ alkyl)CO($C_{1-6}$ alkyl), —S(O)$C_{1-6}$ alkyl, —S(O)$_2$$C_{1-6}$ alkyl, oxo, phenyl, benzyl, pyridinyl, pyrrazolyl, thiazolyl, isothiazolyl, or other 5 to 6 membered heteroaryl groups. In some embodiments, each of the above optional substituents are themselves optionally substituted by one or two groups.

The term "cycloalkyl" as used herein refers to a $C_{3-12}$ cyclic alkyl group, and includes bridged and spirocycles (e.g., adamantine). Examples of cycloalkyl groups include cyclopropyl, cyclobutyl, cyclopentyl, cycloheptyl, cyclohexyl, cycloheptyl, cyclooctyl, bicyclo[2.2.1]heptanyl, bicyclo[3.1.1]heptanyl, bicyclo[4.1.0]heptanyl, spiro[3.3]heptanyl, and spiro[3.4]octanyl. In some embodiments, the cycloalkyl group is a $C_{3-6}$ cycloalkyl.

The term "alkenyl" as used herein refers to $C_{2-12}$ alkyl group wherein at least two of the carbon atoms are sp2 hybridized and form a carbon-carbon double bond between them. An alkenyl group provided herein may contain more than one carbon-carbon double bond, but one is preferred. The alkyl portion of an alkenyl group provided herein may be substituted as provided above. In some embodiments, the alkenyl group is a $C_{2-6}$ alkenyl.

The term "alkynyl" as used herein refers to $C_{2-12}$ alkyl group wherein at least two of the carbon atoms are sp hybridized and form a carbon-carbon triple bond between them. An alkynyl group provided herein may contain more than one carbon-carbon triple bond, but one is preferred. The alkyl portion of an alkynyl group provided herein may be substituted as provided above. In some embodiments, the alkynyl group is a $C_{2-6}$ alkynyl.

The terms "alkoxy," "alkylamino" and "alkylthio", are used in their conventional sense, and refer to those alkyl groups attached to the remainder of the molecule via an oxygen atom ("oxy"), an amino group ("amino") or thio group. The term "alkylamino" includes mono-di-alkylamino groups, the alkyl portions can be the same or different.

The terms "halo" by itself or as part of another substituent, mean, unless otherwise stated, a fluorine, chlorine, bromine, or iodine atom, but preferably fluorine or chlorine.

The term "halo($C_{1-x}$ alkyl)" refers to an alkyl that has 1-x carbon atoms and that is substituted with one or more (e.g. 1, 2, 3, 4, 5, or 6) halo groups. For example the term includes an alkyl group having 1-6 carbon atoms that is substituted with one or more halo groups. Non-limiting examples of the term halo($C_1$-$C_6$alkyl) include fluoromethyl, difluoromethyl, trifluoromethyl, chloromethyl, and 2,2,2-trifluoroethyl.

The term "halo($C_{1-x}$ alkoxy)" refers to an alkoxy group that has 1-x carbon atoms and that is substituted with one or more (e.g. 1, 2, 3, 4, 5, or 6) halo groups. For example the term includes an alkoxy group having 1-6 carbon atoms that is substituted with one or more halo groups. Non-limiting examples of the term halo($C_1$-$C_6$alkyl) include fluoromethoxy, difluoromethoxy, trifluoromethoxy, chloromethoxy, and 2,2,2-trifluoroethoxy.

The term "heteroalkyl" refers to a straight- or branched-chain alkyl group, e.g. having from 2 to 14 carbons, such as 2 to 10 carbons in the chain, one or more of which has been replaced by a heteroatom selected from S, O, P and N. Exemplary heteroalkyls include alkyl ethers, secondary and tertiary alkyl amines, alkyl amides, alkyl sulfides, and the like. The group may be a terminal group or a bridging group. As used herein reference to the normal chain when used in the context of a bridging group refers to the direct chain of atoms linking the two terminal positions of the bridging group.

The term "aryl" as used herein refers to a single all carbon aromatic ring or a multiple condensed all carbon ring system wherein at least one of the rings is aromatic. For example, in certain embodiments, an aryl group has 6 to 12 carbon atoms. Aryl includes a phenyl radical. Aryl also includes multiple condensed ring systems (e.g., ring systems comprising 2, 3 or 4 rings) having about 9 to 12 carbon atoms in which at least one ring is aromatic and wherein the other rings may be aromatic or not aromatic. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, naphthyl, 1,2,3,4-tetrahydronaphthyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. A heteroaryl (a single aromatic ring or multiple condensed ring system) can also have about 5 to 12 or about 5 to 10 members within the heteroaryl ring. Multiple condensed ring systems may be optionally substituted with one or more (e.g., 1, 2, 3 or 4) oxo groups on the carbocycle or heterocycle portions of the condensed ring. The rings of a multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole. In one embodiment the term "heteroaryl" refers to a single aromatic ring containing at least one heteroatom. For example, the term includes 5-membered and 6-membered monocyclic aromatic rings that include one or more heteroatoms. Non-limiting examples of heteroaryl include but are not limited to pyridyl, furyl, thiazole, pyrimidine, oxazole, and thiadiazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. Accordingly, a heterocycle (a single saturated or single partially unsaturated ring or multiple condensed ring system) has about 3-20 atoms including about 1-6 heteroatoms within the heterocycle ring system. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). In one embodiment the term heterocycle includes a $C_{2-20}$ heterocycle. In one embodiment the term heterocycle includes a $C_{2-7}$ heterocycle. In one embodiment the term heterocycle includes a $C_{2-5}$ heterocycle. In one embodiment the term heterocycle includes a $C_{2-4}$ heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one. In one embodiment the term "heterocycle" refers to a monocyclic, saturated or partially unsaturated, 3-8 membered ring having at least one heteroatom. For example, the term includes a monocyclic, saturated or partially unsaturated, 4, 5, 6, or 7 membered ring having at least one heteroatom. Non-limiting examples of heterocycle include aziridine, azetidine, pyrrolidine, piperidine, piperidine, piperazine, oxirane, morpholine, and thiomorpholine. The term "9- or 10-membered heterobicycle" as used herein refers to a partially unsaturated or aromatic fused bicyclic ring system having at least one heteroatom. For example, the term 9- or 10-membered heterobicycle includes a bicyclic ring system having a benzo ring fused to a 5-membered or 6-membered saturated, partially unsaturated, or aromatic ring that contains one or more heteroatoms.

As used herein, the term "heteroatom" is meant to include oxygen (O), nitrogen (N), sulfur (S) and silicon (Si). The nitrogen and sulfur can be in an oxidized form when feasible.

As used herein, the term "chiral" refers to molecules which have the property of non-superimposability of the mirror image partner, while the term “achiral” refers to molecules which are superimposable on their mirror image partner.

As used herein, the term “stereoisomers” refers to compounds which have identical chemical constitution, but differ with regard to the arrangement of the atoms or groups in space. As used herein a crossed line “ ” indicates a mixture of E and Z stereoisomers.

As used herein a wavy line “ ” or a dashed line “----” that intersects a bond in a chemical structure indicates the point of attachment of the bond that the wavy bond intersects in the chemical structure to the remainder of a molecule.

“Diastereomer” refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

“Enantiomers” refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., “Stereochemistry of Organic Compounds”, John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereo specificity in a chemical reaction or process. The terms “racemic mixture” and “racemate” refer to an equimolar mixture of two enantiomeric species, devoid of optical activity.

When a bond in a compound formula herein is drawn in a non-stereochemical manner (e.g. flat), the atom to which the bond is attached includes ah stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term “tautomer” or “tautomeric form” refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term “solvate” refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term “hydrate” refers to the complex where the solvent molecule is water.

As used herein, the term “protecting group” refers to a substituent that is commonly employed to block or protect a particular functional group on a compound. For example, an “amino-protecting group” is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a “hydroxy-protecting group” refers to a substituent of a hydroxy group that blocks or protects the hydroxy functionality. Suitable protecting groups include acetyl and silyl. A “carboxy-protecting group” refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis $4^{th}$ edition, Wiley-Interscience, New York, 2006.

As used herein, the term “pharmaceutically acceptable salts” is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, $—P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is a Von Hippel-Lindae E3 ubiquitin ligase (VHL) binding moiety (VLM). In an exemplary embodiment, the ULM is coupled to a target protein binding moiety (PTM) via a chemical linker (L) according to the structure:

PTM-L-ULM (A)

wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

In another aspect, the present disclosure provides bifunctional or multifunctional compounds (e.g., PROTACs) useful for regulating protein activity by inducing the degradation of a target protein. In certain embodiments, the compound comprises a VLM coupled, e.g., linked covalently, directly or indirectly, to a moiety that binds a target protein (i.e., a protein targeting moiety or a "PTM"). In certain embodiments, the VLM and PTM are joined or coupled via a chemical linker (L). The VLM binds VHL, and the PTM recognizes a target protein and the interaction of the respective moieties with their targets facilitates the degradation of the target protein by placing the target protein in proximity to the ubiquitin ligase protein. An exemplary bifunctional compound can be depicted as: PTM-VLM.

In certain embodiments, the bifunctional compound further comprises a chemical linker ("L"). For example, the bifunctional compound can be depicted as: PTM-L-VLM, wherein the PTM is a protein/polypeptide targeting moiety, the L is a chemical linker, and the VLM is a VHL binding moiety.

In certain embodiments, the ULM (e.g., VLM) shows activity or binds to the E3 ubiquitin ligase (e.g., VHL) with an $IC_{50}$ of less than about 200 μM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 μM.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ULMs can further comprise multiple PTMs. In still additional embodiments, the PTMs are the same or, optionally, different. In still further embodiments, wherein the PTMs are different the respective PTMs may bind the same protein target or bind specifically to a different protein target.

In additional embodiments, the description provides the compounds as described herein including their enantiomers, diastereomers, solvates and polymorphs, including pharmaceutically acceptable salt forms thereof, e.g., acid and base salt forms.

Exemplary VLMs

In certain embodiments the compounds as described herein include a means for binding an E3 ubiquitin ligase, e.g., Von Hippel-Lindau E3 ubiquitin ligase. In certain embodiments the ULM is VLM and comprises a chemical structure selected from the group ULM-a:

ULM-a

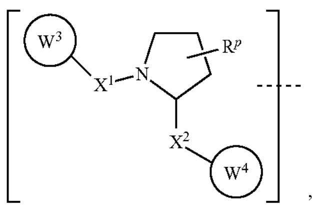

wherein:

- a dashed line indicates the attachment of at least one PTM, another ULM or VLM (i.e., VLM'), or a chemical linker moiety coupling at least one PTM, a ULM' or a VLM' to the other end of the linker;
- $X^1$, $X^2$ of Formula ULM-a are each independently selected from the group of a bond, O, $NR^{Y3}$, $CR^{Y3}R^{Y4}$, C═O, C═S, SO, and $SO_2$;
- $R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3 $R^P$ groups);
- $R^P$ of Formula ULM-a is 0, 1, 2, or 3 groups, each independently selected from the group H, halo, —OH, $C_{1-3}$ alkyl, C═O, alkyl, alkoxy or a combination thereof;
- $W^3$ of Formula ULM-a is selected from the group of an optionally substituted T, an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted T-biheteroaryl, an optionally substituted -T-Heterocyclyl, an optionally substituted -T-biheterocyclyl, an optionally substituted —$NR^1$-T-Aryl, an optionally substituted —$NR^1$-T-Heteroaryl or an optionally substituted —$NR^1$-T-Heterocyclyl;

$X^3$ of Formula ULM-a is C═O, $R^1$, $R^{1a}$, $R^{1b}$;

each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}C$═O, $R^{Y3}C$═S, $R^{Y3}SO$, $R^{Y3}SO_2$, $N(R^{Y3}R^{Y4})C$═O, $N(R^{Y3}R^{Y4})C$═S, $N(R^{Y3}R^{Y4})SO$, and $N(R^{Y3}R^{Y4})SO_2$;

T of Formula ULM-a is selected from the group of an optionally substituted alkyl, —$(CH_2)_n$— group, —$(CH_2)_n$—O—$C_1$-$C_6$ alkyl which is optionally substituted, linear, branched, or —$(CH_2)_n$—O-heterocyclyl which is optionally substituted, wherein each one of the methylene groups is optionally substituted with one or two substituents selected from the group of halogen, methyl, a linear or branched $C_1$-$C_6$ alkyl group optionally substituted by 1 or more halogen or —OH groups, an amino acid side chain optionally substituted or an optionally substituted heterocyclyl;

$W^4$ of Formula ULM-a is an optionally substituted —$NR_1$-T-Aryl wherein the aryl group may be optionally substituted with an optionally substituted 5-6 membered heteroaryl or an optionally substituted aryl, an optionally substituted —$NR_1$-T-Heteroaryl group, wherein the heteroaryl is optionally substituted with an optionally substituted aryl or an optionally substituted heteroaryl, or an optionally substituted —$NR_1$-T-Heterocyclyl, where —$NR_1$ is covalently bonded to $X^2$ and $R^1$ is H or $CH_3$, preferably H.

In certain embodiments, $R^P$ is modified to form a prodrug, including by an ester or ether linkage.

In any aspect or embodiment described herein, T is selected from the group of an optionally substituted alkyl, —$(CH_2)_n$— group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocyclyl, or —OH groups or an amino acid side chain optionally substituted; and n is 0 to 6, often 0, 1, 2, or 3, preferably 0 or 1.

In any aspect or embodiment described herein, $W^4$ of Formula ULM-a is

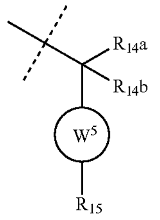
,
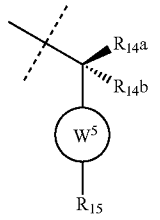
,
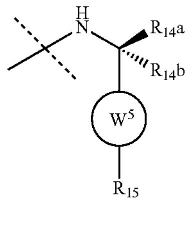
or
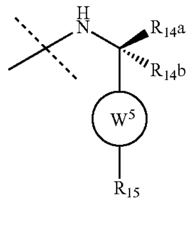
, wherein $R_{14a}$, $R_{14b}$, are each independently selected from the group of H, haloalkyl (e.g., fluoroalkyl), optionally substituted alkyl, optionally substituted alkoxy, optionally substituted hydroxyl alkyl, optionally substituted alkylamine, optionally substituted amide, optionally substituted alkyl-amide, optionally substituted alkyl-cyano, optionally substituted alkyl-phosphate, optionally substituted heteroalkyl, optionally substituted alkyl-heterocycloalkyl, optionally substituted alkoxy-heterocycloalkyl, $COR_{26}$, alkyl-$COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine.

In any of the embodiments, $W^5$ of Formula ULM-a is selected from the group of an optionally substituted phenyl, an optionally substituted napthyl or an optionally substituted 5-10 membered heteroaryl, $R_{15}$ of Formula ULM-a is selected from the group of H, halogen, CN, C≡CH, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, C1-3alkyl, C═O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

ULM-b

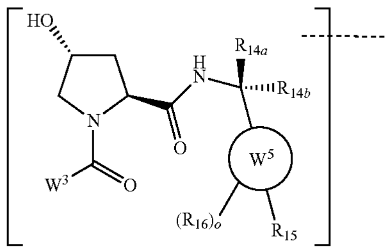
, wherein:

$W^3$ of Formula ULM-b is selected from the group of an optionally substituted aryl, optionally substituted heteroaryl, or

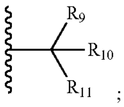

;

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclyl, optionally substituted alkoxy, optionally substituted heteroaryl, optionally substituted aryl,

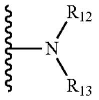

,

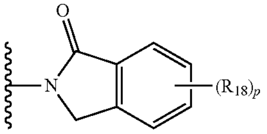

or

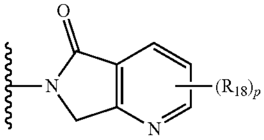

;

$R_{12}$ of Formula ULM-b is selected from the group of H or optionally substituted alkyl;

$R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of Formula ULM-b, are each independently selected from the group of H, haloalkyl (e.g. fluoroalkyl), optionally substituted alkyl, optionally substitute alkoxy, aminomethyl, alkylaminomethyl, alkoxymethyl, optionally substituted hydroxyl alkyl, optionally substituted alkylamine, optionally substituted amide, optionally substituted alkyl-amide, optionally substituted alkyl-cyano, optionally substituted alkyl-phosphate, optionally substituted heteroalkyl, optionally substituted alkyl-heterocycloalkyl, optionally substituted alkoxy-heterocycloalkyl, $COR_{26}$, alkyl-$COR_{26}$, $CONR_{27a}R_{27b}$, $CH_2NHCOR_{26}$, or $(CH_2)N(CH3)COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalkyl, spirocycloalkyl or spiroheterocyclyl, wherein the spiroheterocyclyl is not epoxide or aziridine;

$W^5$ of Formula ULM-b is selected from the group of a phenyl, napthyl, or a 5-10 membered heteroaryl, $R_{15}$ of Formula ULM-b is selected from the group of H, halogen, CN, C≡CH, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}SO_2R_{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl;

each $R_{16}$ of Formula ULM-b is independently selected from the group of halo, CN, optionally substituted alkyl, optionally substituted alkylamine, optionally substituted haloalkyl, hydroxy, or optionally substituted haloalkoxy;

o of Formula ULM-b is 0, 1, 2, 3, or 4;

$R_{18}$ of Formula ULM-b is independently selected from the group of H, halo, optionally substituted alkoxy, cyano, optionally substituted alkyl, haloalkyl, haloalkoxy or a linker;

each $R_{26}$ is independently selected from H, OH, optionally substituted alkyl or $NR_{27a}R_{27b}$;

each $R_{27a}$ and $R_{27b}$ is independently H, optionally substituted alkyl, optionally substituted 3-5 member cycloalkyl, or $R_{27a}$ and $R_{27b}$ together with the nitrogen atom to which they are attached form a 4-6 membered heterocyclyl;

and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, $R_{15}$ of Formula ULM-b is

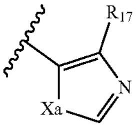

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ of Formula ULM-b is selected from the group methyl, ethyl, isopropyl, and cyclopropyl.

In certain additional embodiments, $R_{15}$ of Formula ULM-b is selected from the group consisting of:

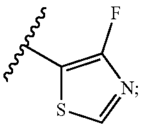

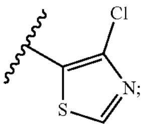

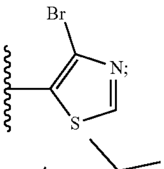

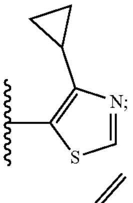

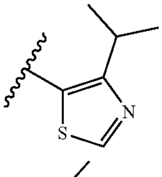

;

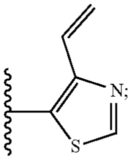

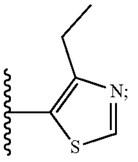

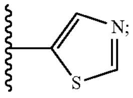

-continued
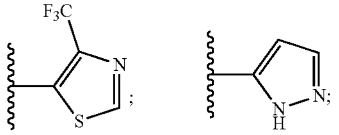
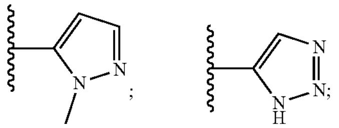
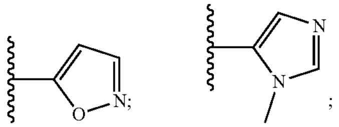
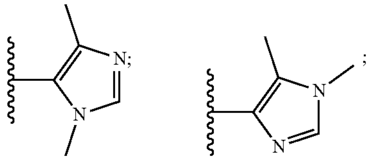
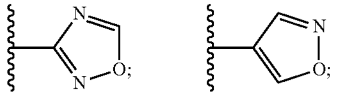
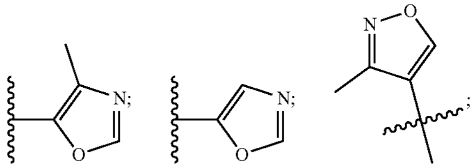
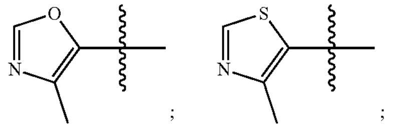
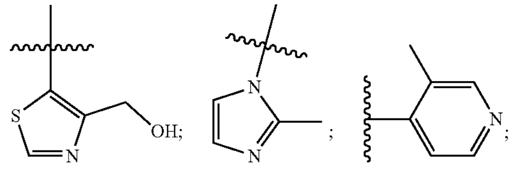
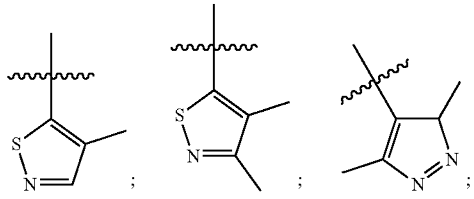
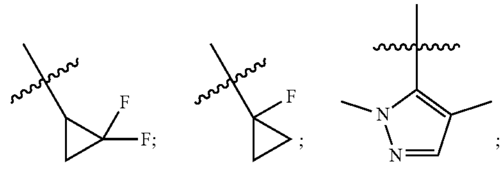
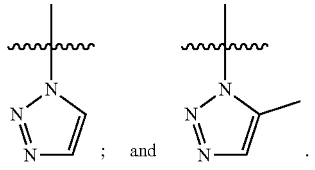
In certain embodiments, $R_{11}$ of Formula ULM-b is selected from the group consisting of:
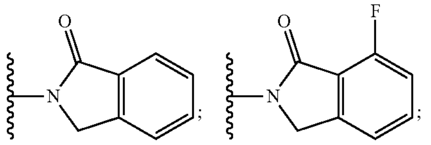
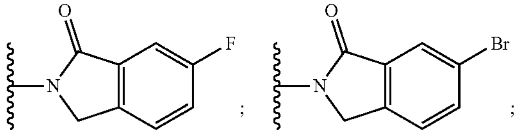
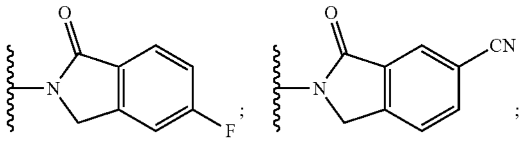
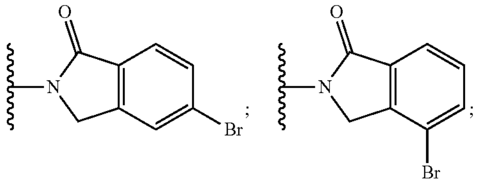
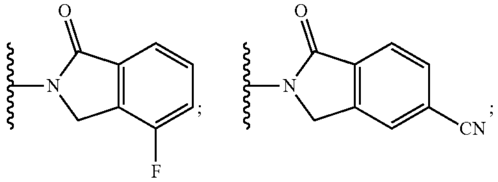
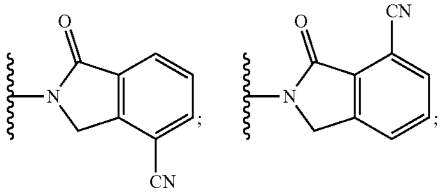
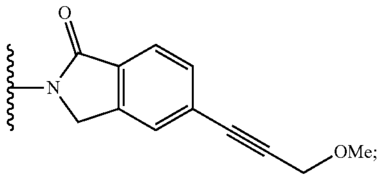
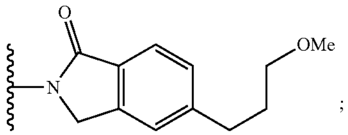
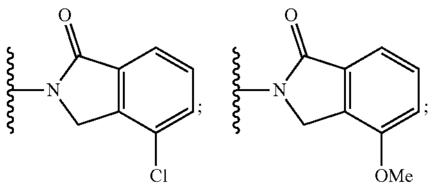
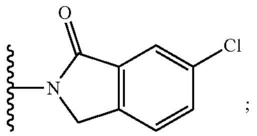
; and -continued

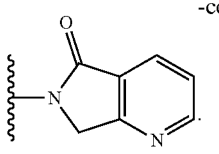

In any aspect or embodiment described herein, $R_{14a}$, $R_{14b}$ of Formula ULM-b, are each independently selected from the group of H, optionally substituted haloalkyl, optionally substituted alkyl, optionally substituted alkoxy, optionally substituted hydroxyl alkyl, optionally substituted alkylamine, optionally substituted amide, optionally substituted alkyl-amide, optionally substituted alkyl-cyano, optionally substituted alkyl-phosphate, optionally substituted heteroalkyl, optionally substituted alkyl-heterocycloalkyl, optionally substituted alkoxy-heterocycloalkyl, $COR_{26}$, alkyl-$COR_{26}$, $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, or $CH_2NCH_3COR_{26}$; and the other of $R_{14a}$ and $R_{14b}$ is H; or $R_{14a}$, $R_{14b}$, together with the carbon atom to which they are attached, form an optionally substituted 3- to 6-membered cycloalkyl, heterocycloalkyl, spirocycloalkyl or spiroheterocyclyl, wherein the spiroheterocyclyl is not epoxide or aziridine, the said spirocycloalkyl or spiroheterocycloalkyl itself being optionally substituted with an alkyl, a haloalkyl, or —$COR_{33}$ where $R_{33}$ is an alkyl or a haloalkyl, wherein $R_{30}$ is selected from H, alkyl, alkynylalkyl, cycloalkyl, heterocycloalkyl, cycloalkylalkyl, heterocycloalkylalkyl, arylalkyl or heteroarylalkyl further optionally substituted; $R_{26}$ and $R_{27}$ are as described above.

In any aspect or embodiment described herein, $R_{15}$ of Formula ULM-b is selected from H, halogen, CN, C≡CH, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{22a}$ $SO_2R_{27b}$, optionally substituted alkyl, optionally substituted haloalkyl (e.g. optionally substituted fluoroalkyl), optionally substituted haloalkoxy, optionally substituted aryl, optionally substituted heteroaryl, optionally substituted cycloalkyl, or optionally substituted heterocyclyl wherein optional substitution of the said aryl, heteroaryl, cycloalkyl and heterocycloalkyl includes $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, $CH_2NCH_3COR_{26}$ or

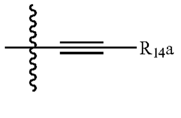

, wherein $R_{26}$, $R_{27}$, $R_{30}$ and $R_{14a}$ are as described above.

In any aspect or embodiment described herein, $R_{14a}$, $R_{14b}$ of Formula ULM-b, are each independently selected from the group of H, optionally substituted haloalkyl, optionally substituted alkyl, $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, or $CH_2NCH_3COR_{26}$; and the other of $R_{14a}$ and $R_{14b}$ is H; or $R_{14a}$, $R_{14b}$, together with the carbon atom to which they are attached, form an optionally substituted 3- to 6-membered spirocycloalkyl or spiroheterocyclyl, wherein the spiroheterocyclyl is not epoxide or aziridine, the said spirocycloalkyl or spiroheterocycloalkyl itself being optionally substituted with an alkyl, a haloalkyl, or —$COR_{33}$ where $R_{33}$ is an alkyl or a haloalkyl, wherein $R_{30}$ is selected from H, alkyl, alkynylalkyl, cycloalkyl, heterocycloalkyl, cycloalkylalkyl, heterocycloalkylalkyl, arylalkyl or heteroarylalkyl further optionally substituted;

$R_{15}$ of Formula ULM-b is selected from H, halogen, CN, C≡CH, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}$ $SO_2R_{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl wherein optional substitution of the said aryl, heteroaryl, cycloalkyl and heterocycloalkyl includes $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, $CH_2NCH_3COR_{26}$ or

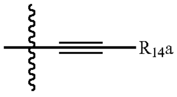

, wherein $R_{26}$, $R_{27}$, $R_{30}$ and $R_{14a}$ are as described above.

In certain embodiments, ULM has a chemical structure selected from the group of:

ULM-c

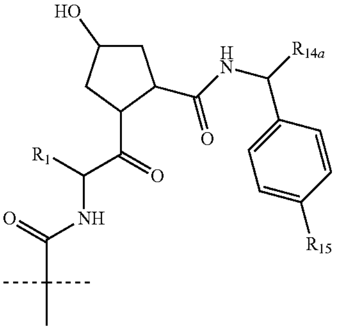

,

ULM-d

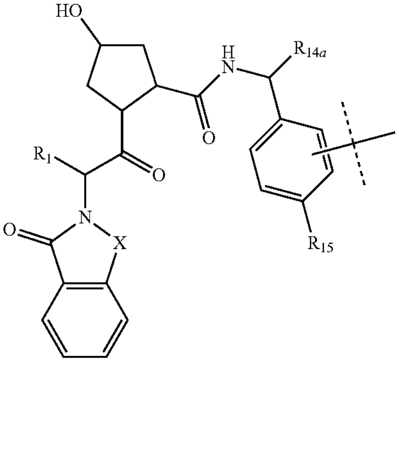

-continued

ULM-e

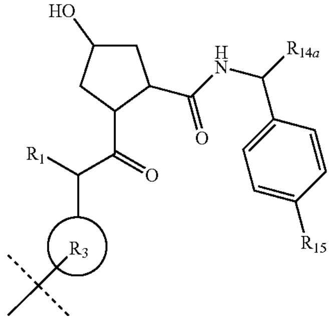

, wherein:

$R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted cycloalkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, C≡CH, OH, $NO_2$, optionally substituted heteroaryl, optionally substituted aryl; optionally substituted alkyl, optionally substituted haloalkyl, optionally substituted haloalkoxy, optionally substituted cycloalkyl, or optionally substituted heterocyclyl;

X of Formulas ULM-c, ULM-d, and ULM-e is C, $CH_2$, or C═O $R_3$ of Formulas ULM-c, ULM-d, and ULM-e is absent or an optionally substituted 5 or 6 membered heteroaryl; and the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

ULM-f

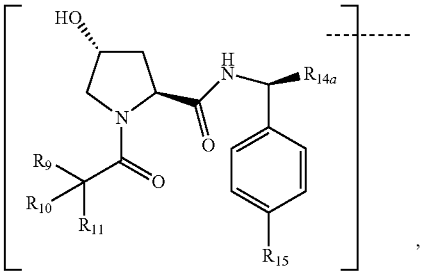

, wherein:

$R_{14a}$ of Formula ULM-f is H, haloalkyl, optionally substituted alkyl, methyl, fluoromethyl, hydroxymethyl, ethyl, isopropyl, or cyclopropyl;

$R_9$ of Formula ULM-f is H;

$R_{10}$ of Formula ULM-f is H, ethyl, isopropyl, tert-butyl, sec-butyl, cyclopropyl, cyclobutyl, cyclopentyl, or cyclohexyl;

$R_{11}$ of Formula ULM-f is

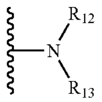 ; 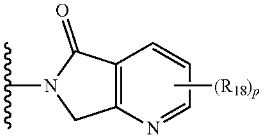 ;

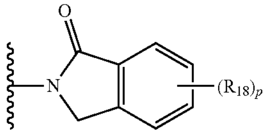 ; 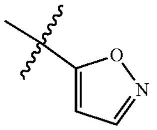 ;

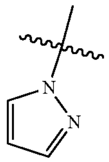 ; 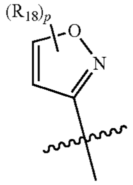 ;

or optionally substituted heteroaryl;

p of Formula ULM-f is 0, 1, 2, 3, or 4;

each $R_{18}$ of Formula ULM-f is independently halo, optionally substituted alkoxy, cyano, optionally substituted alkyl, haloalkyl, haloalkoxy or a linker;

$R_{12}$ of Formula ULM-f is H, C═O;

$R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ of Formula ULM-f is selected from the group consisting of H, halogen, Cl, CN, C≡CH, OH, $NO_2$, optionally substituted haloalkyl, optionally substituted heteroaryl, optionally substituted aryl;

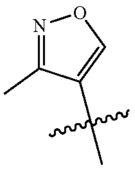 ; 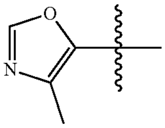 ;

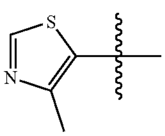 ; 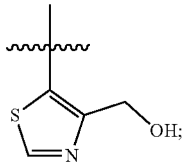

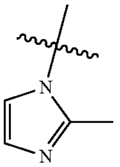 ; 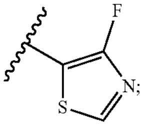 ; 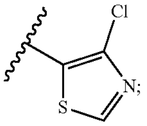 ;

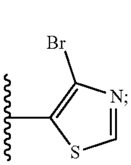 ; 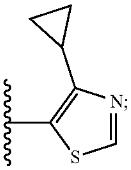 ; 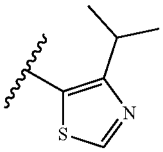 ;

-continued
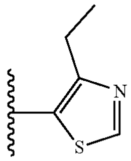
;
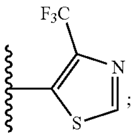
;
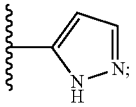
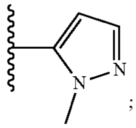
;
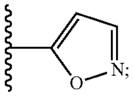
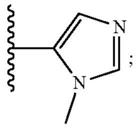
;
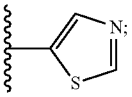
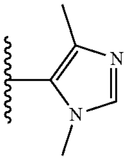
;
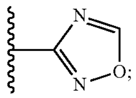
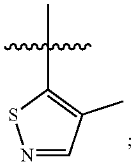
;
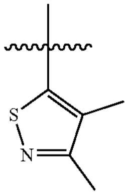
;
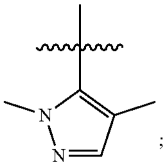
;
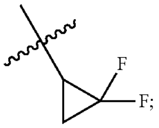
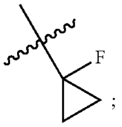
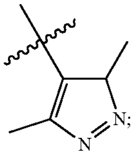
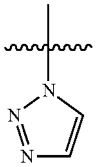
;
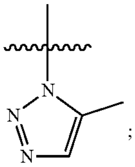
;
and
wherein the dashed line of Formula ULM-f indicates the site of attachment of at least one PTM, another ULM (ULM') or a chemical linker moiety coupling at least one PTM or a ULM' or both to ULM.
In certain embodiments, the ULM is selected from the following structures:
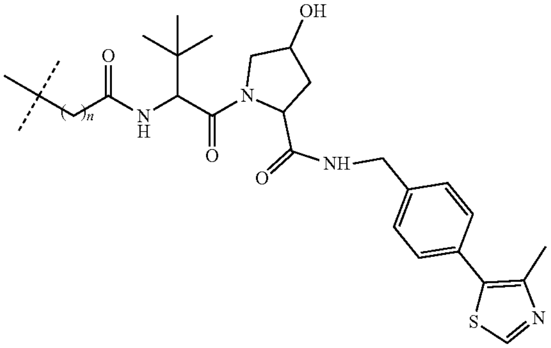
-continued
ULM-a2
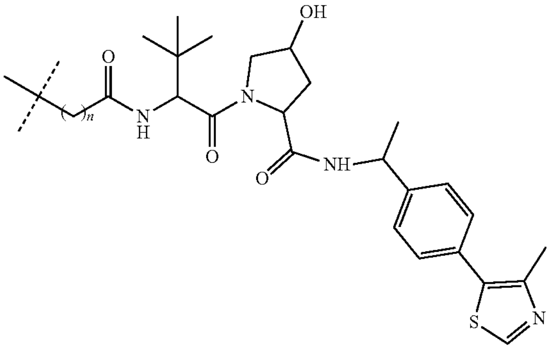
ULM-a3
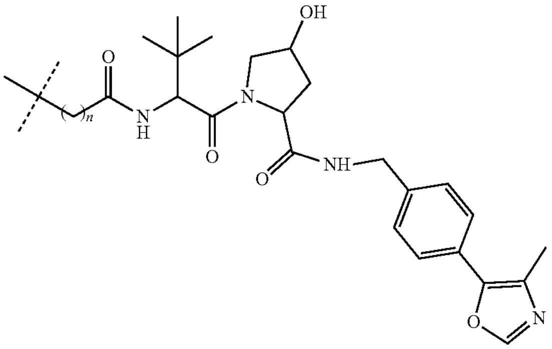
ULM-a4
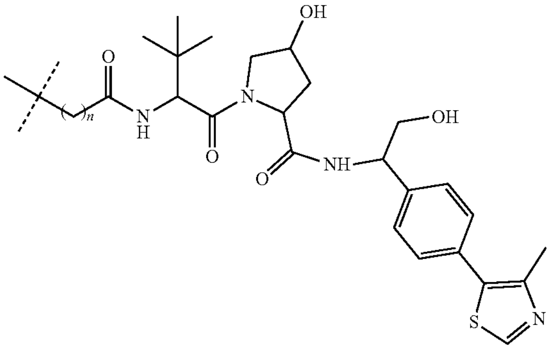
ULM-a5
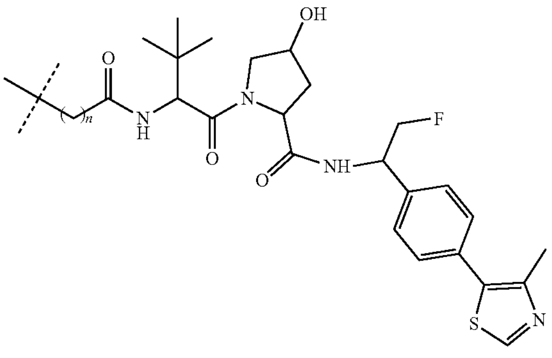

-continued
ULM-a6
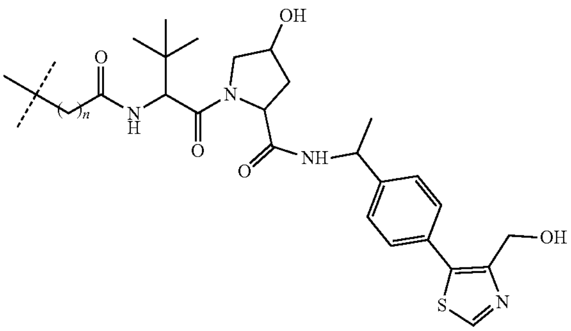
ULM-a7
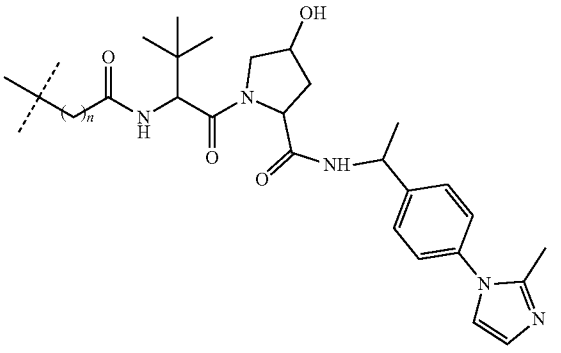
ULM-a8
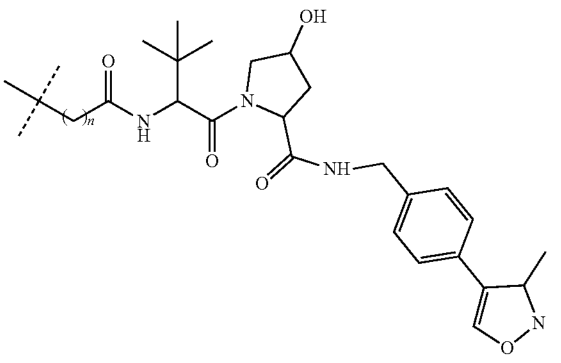
ULM-a9
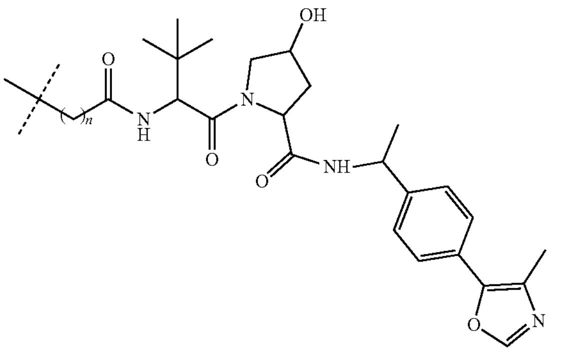
-continued
ULM-a10
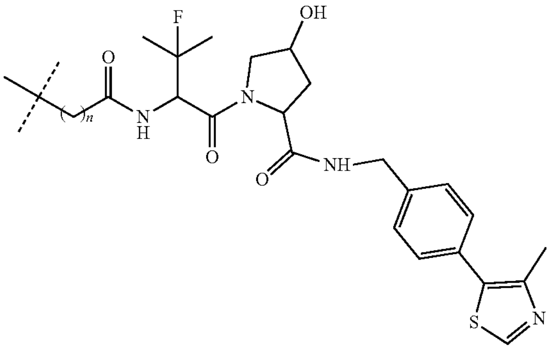
ULM-a11
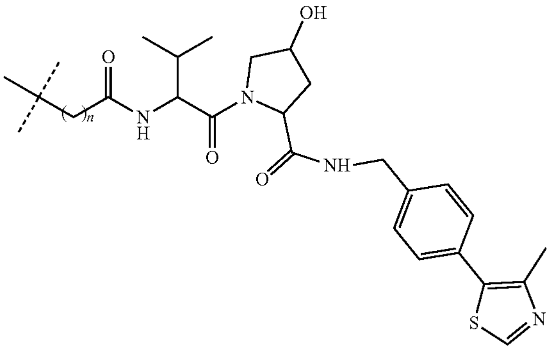
ULM-a12
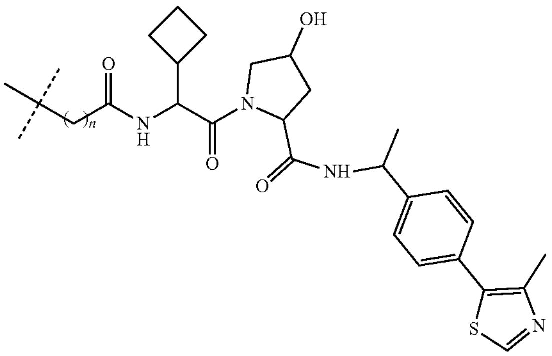
ULM-a13
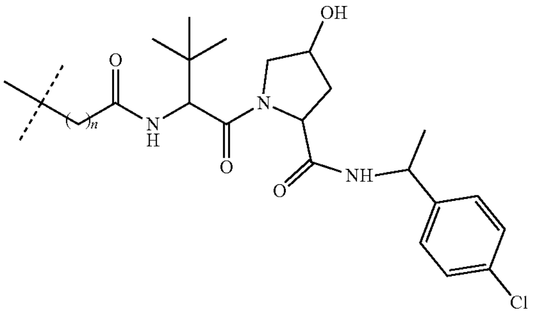

-continued
ULM-a14
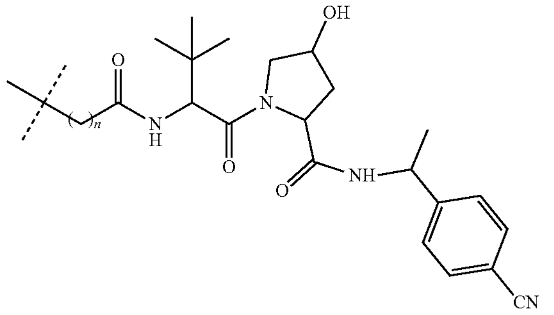
ULM-a15
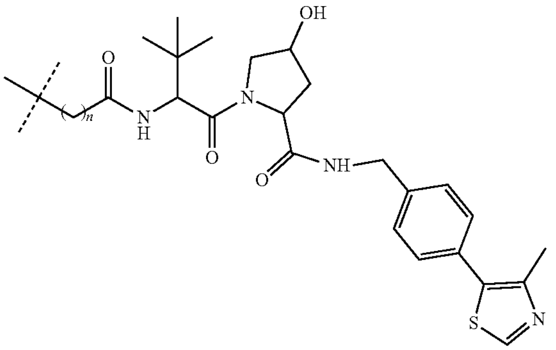
wherein n is 0 or 1.
In certain embodiments, the ULM is selected from the following structures:
ULM-b1
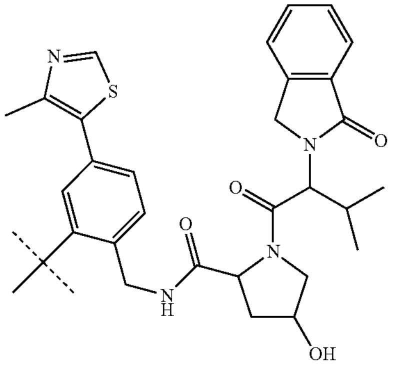
ULM-b2
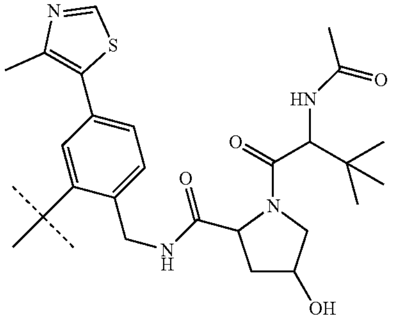
-continued
ULM-b3
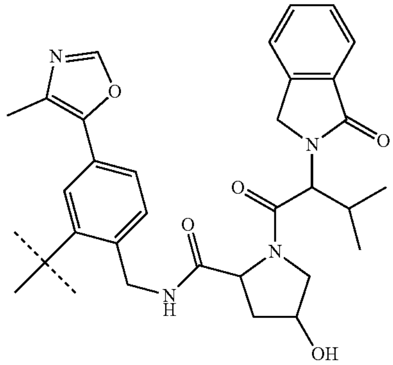
ULM-b4
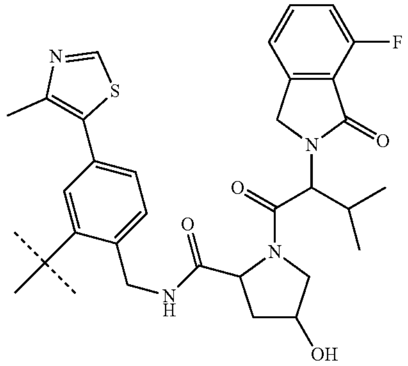
ULM-b5
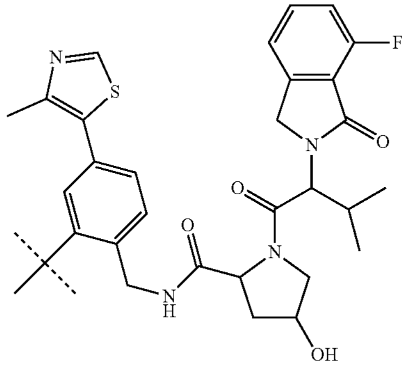
ULM-b6
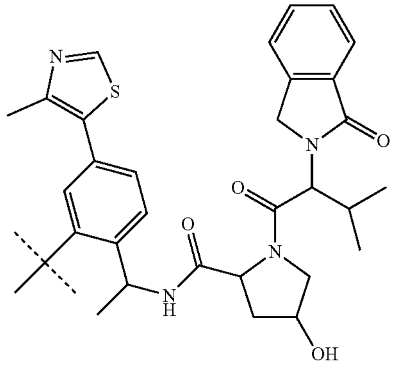

-continued
ULM-b7
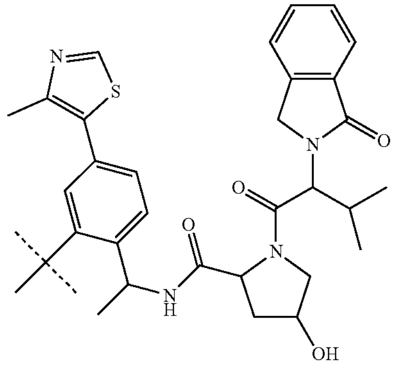
ULM-b8
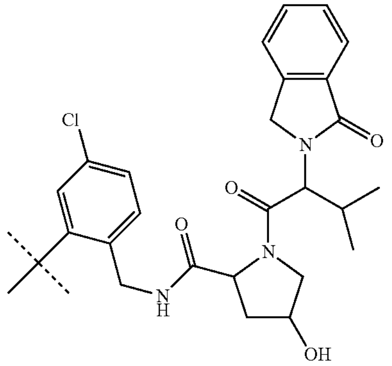
ULM-b9
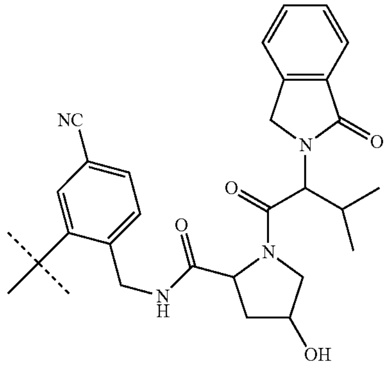
ULM-b10
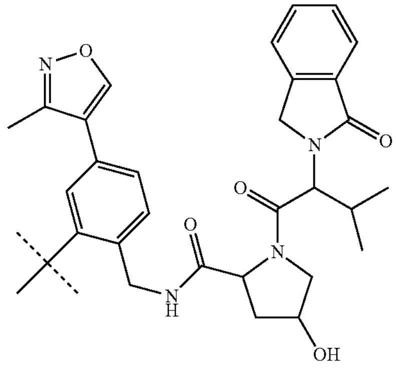
-continued
ULM-b11
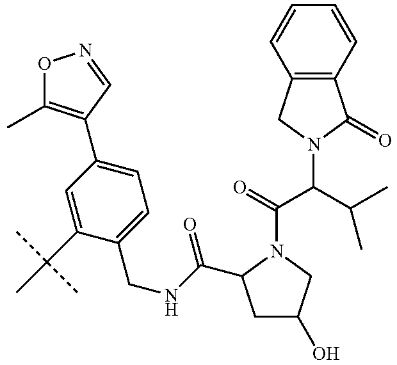
ULM-b12
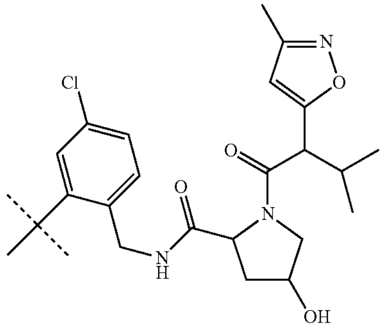
ULM-c1
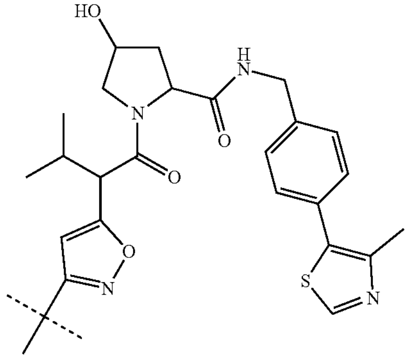
ULM-c2
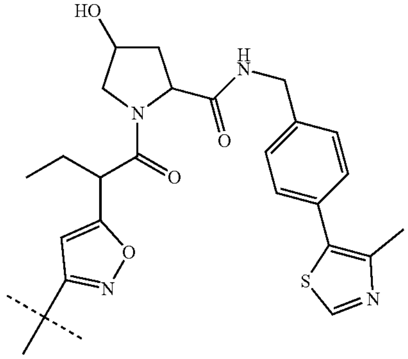

-continued
ULM-c3
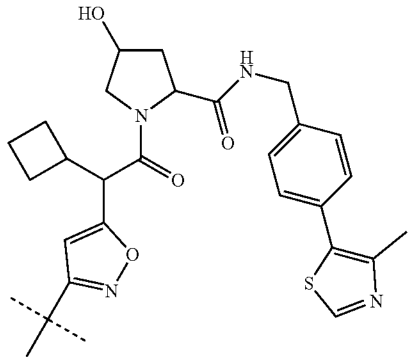
ULM-c4
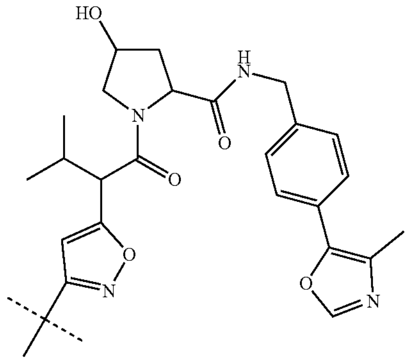
ULM-c5
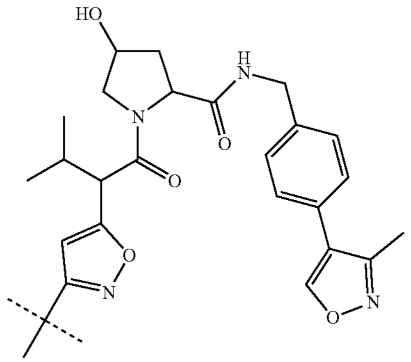
ULM-c6
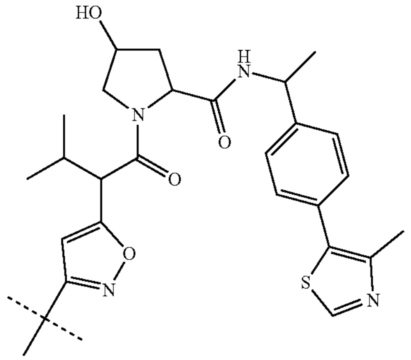
-continued
ULM-c7
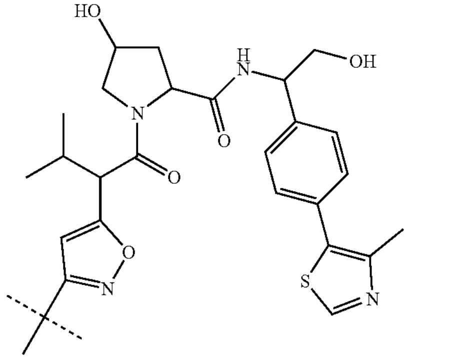
ULM-c8
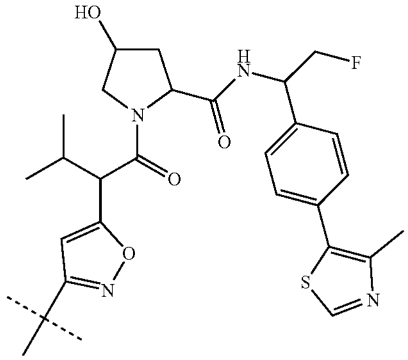
ULM-c9
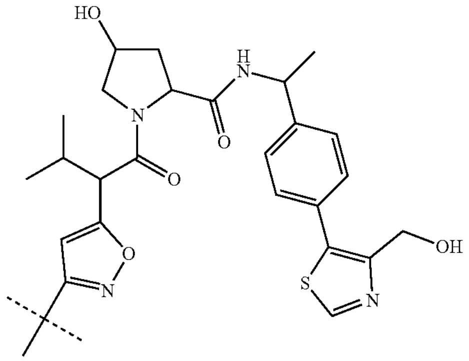
ULM-c10
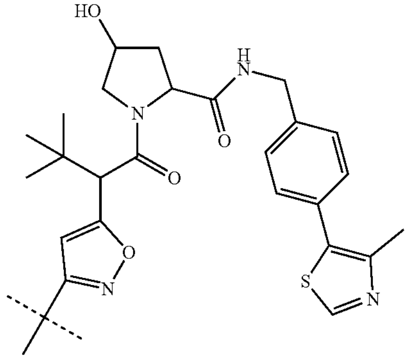

-continued
ULM-c11
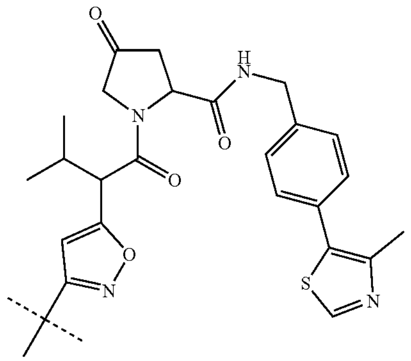
ULM-c12
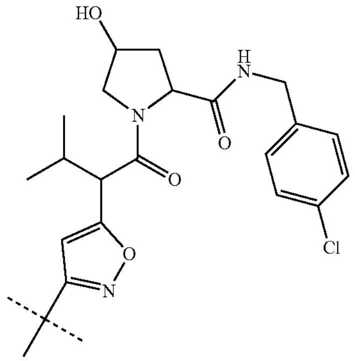
ULM-c13
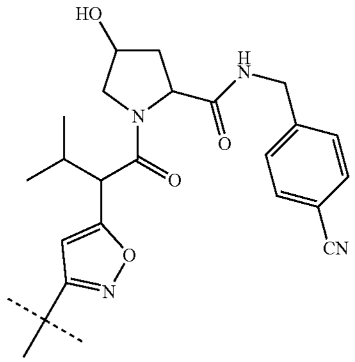
ULM-c14
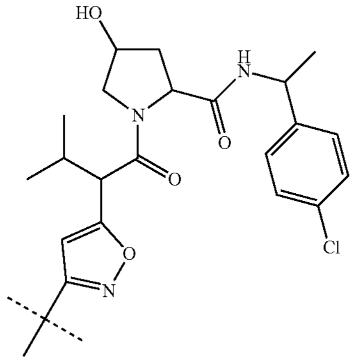
-continued
ULM-c15
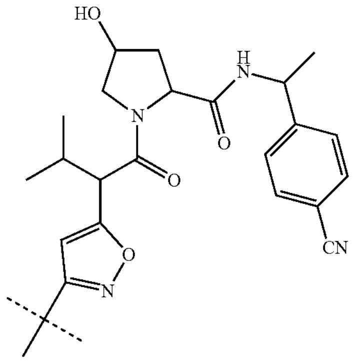
ULM-d1
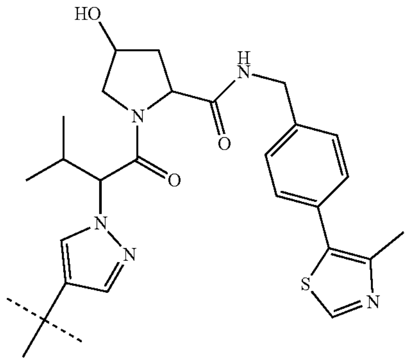
ULM-d2
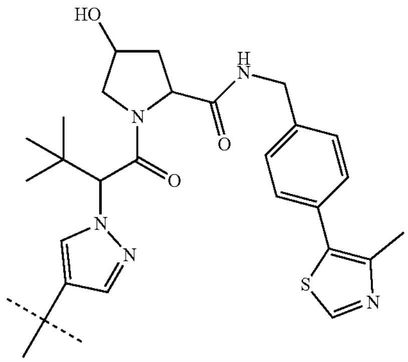
ULM-d3
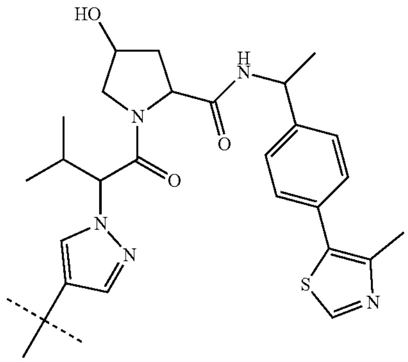

-continued

ULM-d4

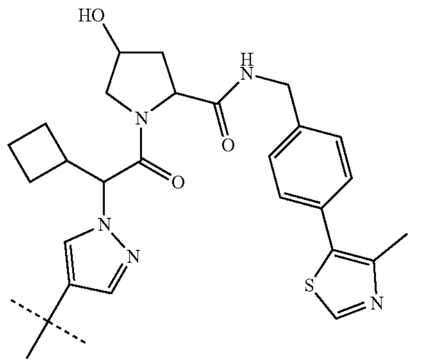

ULM-d5

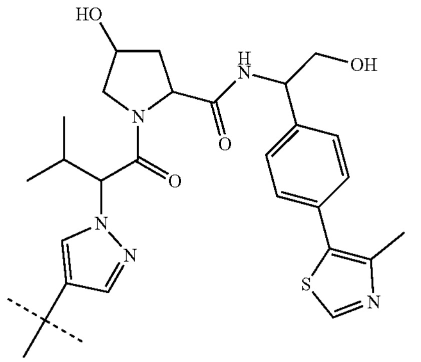

ULM-d6

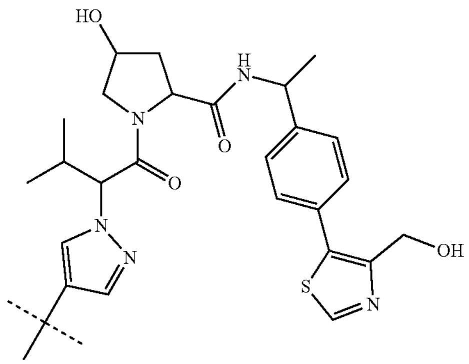

ULM-d7

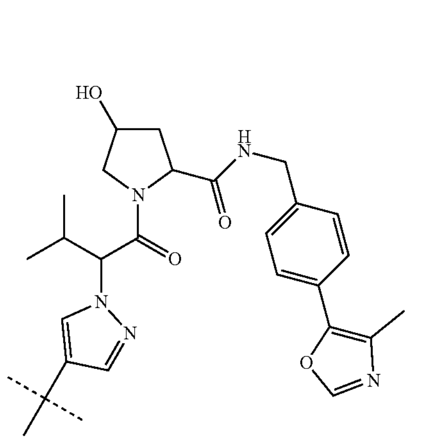

-continued

ULM-d8

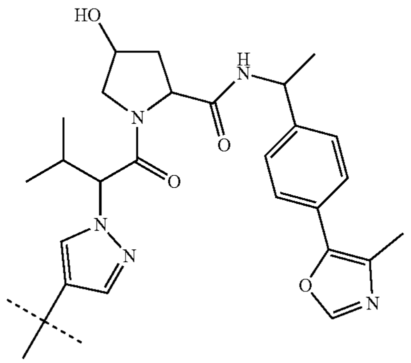

ULM-d9

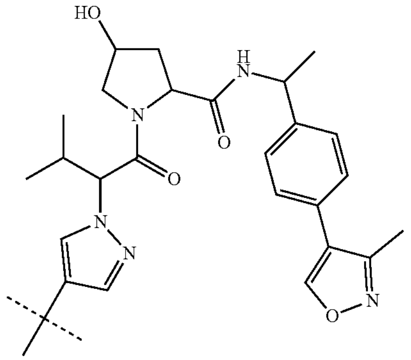

wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b 12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

ULM-g

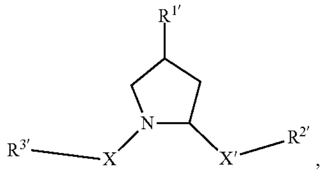

or a pharmaceutic ally acceptable salt thereof, wherein:

$R^1$ of ULM-g is an optionally substituted $C_1$-$C_6$ alkyl group, an optionally substituted —$(CH_2)_n$OH, an optionally substituted —$(CH_2)_n$SH, an optionally substituted $(CH_2)_n$—O—$(C_1$-$C_6)$alkyl group, an optionally substituted $(CH_2)_n$—WCOCW—$(C_0$-$C_6)$alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—($C_1$-$C_6$ alkyl), an optionally substituted —$(CH_2)_n$NHC(O)—R", an optionally substituted —$(CH_2)_n$C(O)—N(R")$_2$, an optionally substituted —$(CH_2)_n$OC(O)—N(R")$_2$, —$(CH_2O)_n$H, an optionally substituted —$(CH_2)_n$OC(O)—($C_1$-$C_6$ alkyl), an optionally substituted —$(CH_2)_n$C(O)—O—($C_1$-$C_6$ alkyl), an optionally substituted —$(CH_2O)_n$COOH, an optionally substituted —$(OCH_2)_n$O—($C_1$-$C_6$ alkyl), an optionally substituted —$(CH_2O)_n$C(O)—($C_1$-$C_6$ alkyl), an optionally substituted —$(OCH_2)_n$NHC(O)—R", an optionally substituted —$(CH_2O)_n$C(O)—N(R")$_2$, —$(CH_2CH_2O)_n$H, an optionally substituted —$(CH_2CH_2O)_n$COOH, an optionally substituted —$(OCH_2CH_2)_n$O—($C_1$-$C_6$ alkyl), an optionally substituted —$(CH_2CH_2O)_n$C(O)—($C_1$-$C_6$ alkyl), an optionally substituted —$(OCH_2CH_2)_n$NHC(O)—R", an optionally substituted —$(CH_2CH_2O)_n$C(O)—N(R")$_2$, an optionally substituted —$SO_2R_S$, an optionally substituted S(O)$R_S$, $NO_2$, CN or halogen (F, Cl, Br, I, preferably F or Cl);

each R" of ULM-g is independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocyclyl group or a —$(CH_2)_m$ N(R")$_2$ group;

X and X' of ULM-g are each independently C═O, C═S, —S(O), S(O)$_2$, (preferably X and X' are both C═O);

$R^{2'}$ of ULM-g is an optionally substituted —$(CH_2)_n$—(C═O)$_u$(NR")$_v$(SO$_2$)$_w$-alkyl group, an optionally substituted —$(CH_2)_n$—(C═O)$_u$(NR")$_v$(SO$_2$)$_w$NR$_{1N}$R$_{2N}$ group, an optionally substituted —$(CH_2)_n$—(C═O)$_u$(NR")$_v$(SO$_2$)$_w$-Aryl, an optionally substituted —$(CH_2)_n$—(C═O)$_u$(NR")$_v$(SO$_2$)$_w$-Heteroaryl, an optionally substituted —$(CH_2)_n$—(C═O)$_v$NR"(SO$_2$)$_w$-Heterocyclyl, an optionally substituted —NR"—$(CH_2)_n$—C(O)$_u$(NR")$_v$(SO$_2$)$_w$-alkyl, an optionally substituted —NR"—$(CH_2)_n$—C(O)$_u$(NR")$_v$(SO$_2$)$_w$—NR$_{1N}$R$_{2N}$, an optionally substituted —NR"—$(CH_2)_n$—C(O)$_u$(NR")$_v$(SO$_2$)$_w$—NR"C(O)R$_{1N}$, an optionally substituted —NR"—$(CH_2)_n$—(C═O)$_u$(NR")$_v$(SO$_2$)$_w$-Aryl, an optionally substituted —NR"—$(CH_2)_n$—(C═O)$_u$(NR")$_v$(SO$_2$)$_w$-Heteroaryl or an optionally substituted —NR"—$(CH_2)_n$—(C═O)$_v$NR"(SO$_2$)$_w$-Heterocyclyl, an optionally substituted —X$^{R2'}$-alkyl group; an optionally substituted —X$^{R2'}$— Aryl group; an optionally substituted —X$^{R2'}$— Heteroaryl group; an optionally substituted —X$^{R2'}$— Heterocyclyl group;

$R^{3'}$ of ULM-g is an optionally substituted alkyl, an optionally substituted —$(CH_2)_n$—(O)$_u$(NR")$_v$(SO$_2$)$_w$-alkyl, an optionally substituted —$(CH_2)_n$—C(O)$_u$(NR")$_v$(SO$_2$)$_w$—NR$_{1N}$R$_{2N}$, an optionally substituted —$(CH_2)_n$—C(O)$_u$(NR")$_v$(SO$_2$)$_w$—NR"C(O)R$_{1N}$, an optionally substituted —$(CH_2)_n$—C(O)$_u$(NR")$_v$(SO$_2$)$_w$—C(O)(R")$_2$, an optionally substituted —$(CH_2)_n$—C(O)$_u$(NR")$_v$(SO$_2$)$_w$-Aryl, an optionally substituted —$(CH_2)_n$—C(O)$_u$(NR")$_v$(SO$_2$)$_w$-Heteroaryl, an optionally substituted —$(CH_2)_n$—C(O)$_u$(NR")$_v$(SO$_2$)$_w$-Heterocyclyl, an optionally substituted —NR"—$(CH_2)_n$—C(O)$_u$(NR")$_v$(SO$_2$)$_w$-alkyl, an optionally substituted —NR"—$(CH_2)_n$—C(O)$_u$(NR")$_v$(SO$_2$)$_w$—NR$_{1N}$R$_{2N}$, an optionally substituted —NR"—$(CH_2)_n$—C(O)$_U$(NR")$_v$(SO$_2$)$_w$—NR"C(O)R$_{1N}$, an optionally substituted —NR"—$(CH_2)_n$—C(O)$_u$(NR")$_v$(SO$_2$)$_w$-Aryl, an optionally substituted —NR"—$(CH_2)_n$—C(O)$_u$(NR")$_v$(SO$_2$)$_w$-Heteroaryl, an optionally substituted —NR$^1$—$(CH_2)_n$—C(O)$_u$(NR")$_v$(SO$_2$)$_w$-Heterocyclyl, an optionally substituted —O—$(CH_2)_n$—(C═O)$_u$(NR")$_v$(SO$_2$)$_w$-alkyl, an optionally substituted —O—$(CH_2)_n$—(C═O)$_u$(NR")$_v$(SO$_2$)$_w$—NR$_{1N}$R$_{2N}$, an optionally substituted —O—$(CH_2)_n$—(C═O)$_u$(NR")$_v$(SO$_2$)$_w$—NR"C(O)R$_{1N}$, an optionally substituted —O—$(CH_2)_n$—(C═O)$_u$(NR")$_v$(SO$_2$)$_w$-Aryl, an optionally substituted —O—$(CH_2)_n$—(C═O)$_u$(NR")$_v$(SO$_2$)$_w$-Heteroaryl or an optionally substituted —O—$(CH_2)_n$—(C═O)$_u$(NR")$_v$(SO$_2$)$_w$-Heterocyclyl; —$(CH_2)_n$—(V)$_{n'}$—$(CH_2)_n$—(V)$_{n'}$-alkyl group, an optionally substituted —$(CH_2)_n$—(V)$_{n'}$—$(CH_2)_n$—(V)$_{n'}$-Aryl group, an optionally substituted —$(CH_2)_n$—(V)$_{n'}$—$(CH_2)_n$—(V)$_{n'}$-Heteroaryl group, an optionally substituted —$(CH_2)_n$—(V)$_{n'}$—$(CH_2)_n$—(V)$_{n'}$-Heterocyclyl group, an optionally substituted —$(CH_2)_n$—N(R$_{1'}$)(C═O)$_{m'}$—(V)$_{n'}$-alkyl group, an optionally substituted —$(CH_2)_n$—N(R$_{1'}$)(C═O)$_{m'}$—(V)$_{n'}$-Aryl group, an optionally substituted —$(CH_2)_n$—N(R$_{1'}$)(C═O)$_{m'}$—(V)$_{n'}$-Heteroaryl group, an optionally substituted —$(CH_2)_n$—N(R$_{1'}$)(C═O)$_{m'}$—(V)$_{n'}$-Heterocyclyl group, an optionally substituted —X$^{R3'}$— alkyl group; an optionally substituted —X$^{R3'}$— Aryl group; an optionally substituted —X$^{R3'}$— Heteroaryl group; an optionally substituted —X$^{R3'}$— Heterocyclyl group;

$R_{1N}$ and $R_{2N}$ of ULM-g are each independently H, $C_1$-$C_6$ alkyl which is optionally substituted with one or two hydroxyl groups and up to three halogen groups or an optionally substituted —$(CH_2)_n$-Aryl, —$(CH_2)_n$-Heteroaryl or —$(CH_2)_n$-Heterocyclyl group;

V of ULM-g is O, S or NR$_1$;

each R$_{1'}$ of ULM-g is independently H or a $C_1$-$C_3$ alkyl group;

X$^{R2'}$ and X$^{R3'}$ of ULM-g are each independently an optionally substituted —CH$_2$)$_n$—, —CH$_2$)$_n$—CH(X$_v$)═CH(X$_v$)— (cis or trans), —CH$_2$)$_n$—CH═CH—, —$(CH_2CH_2O)_n$— or a $C_3$-$C_6$ cycloalkyl group, where X$_v$ is H, a halo or a $C_1$-$C_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group, or a pharmaceutic ally acceptable salt, stereoisomer, solvate or polymorph thereof.

In any of the aspects or embodiments described herein, the ULM and when present, ULM', are each independently a group according to the chemical structure:

ULM-h

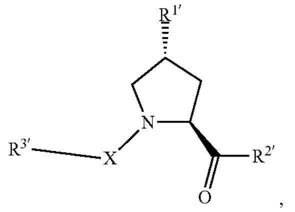

wherein:

each of $R^{1'}$, $R^{2'}$ and $R^{3'}$ of ULM-h are the same as above and X is C═O, C═S, —S(O) group or a $S(O)_2$ group, more preferably a C═O group, and any one or more of $R^{1'}$, $R^{2'}$ and $R^{3'}$ of ULM-h are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

ULM-i

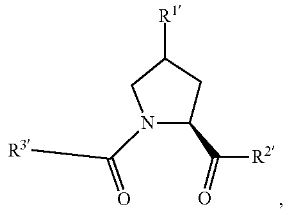

wherein:

any one or more of $R^{1'}$, $R^{2'}$ and $R^{3'}$ of ULM-I are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In further preferred aspects of the disclosure, $R^{1'}$ of ULM-g through ULM-i is preferably a hydroxyl group or a group which may be metabolized to a hydroxyl or carboxylic group, such that the compound represents a prodrug form of an active compound. Exemplary preferred $R^{1'}$ groups include, for example, $-(CH_2)_nOH$, $(CH_2)_n-O-(C_1-C_6)$alkyl group, $-(CH_2)_nCOOH$, $-(CH_2O)_nH$, an optionally substituted $-(CH_2)_nOC(O)-(C_1-C_6$ alkyl), or an optionally substituted $-(CH_2)_nC(O)-O-(C_1-C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C═O, C═S, —S(O) group or a $S(O)_2$ group, more preferably a C═O group;

$R^{2'}$ of ULM-g through ULM-i is preferably an optionally substituted —NH-T-Aryl, an optionally substituted $-N(CH_3)$-T-Aryl, an optionally substituted —NH-T-Heteroaryl group, an optionally substituted $-N(CH_3)$-T-Heteroaryl, an optionally substituted —NH-T-Heterocyclyl, or an optionally substituted $-N(CH_3)$-T-Heterocyclyl preferably H and T is an optionally substituted $-(CH_2)_n-$ group, wherein each one of the methylene groups may be optionally substituted with one or two substituents, preferably selected from halogen, an amino acid sidechain as otherwise described herein or a $C_1$-$C_3$ alkyl group, preferably one or two methyl groups, which may be optionally substituted; and n is 0 to 6, often 0, 1, 2 or 3, preferably 0 or 1. Alternatively, T may also be a $-(CH_2O)_n-$ group, a $-(OCH_2)_n-$ group, a $-(CH_2CH_2O)_n-$ group, a $-(OCH_2CH_2)_n-$ group, all of which groups are optionally substituted.

Preferred Aryl groups for $R^{2'}$ of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methyl substituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

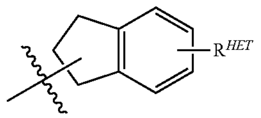

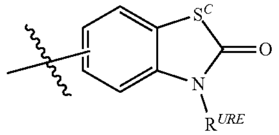

-continued

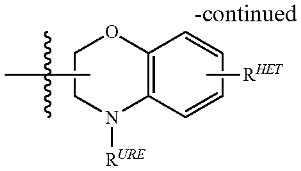

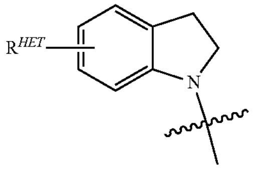

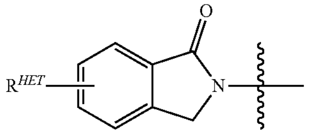

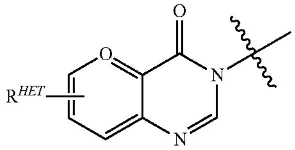

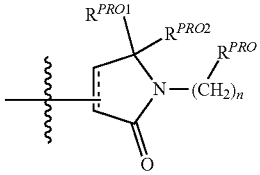

, wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocyclyl, preferably for example piperidine, morpholine, pyrrolidine, tetrahydrofuran);

$R^{PRO}$ of ULM-g through ULM-i is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2\ of\ ULM\text{-}g\ through\ ULM\text{-}i}$ are each independently H, an optionally substituted $C_1$-$C_3$ alkyl group or together form a keto group; and each n of ULM-g through ULM-i is independently 0, 1, 2, 3, 4, 5, or 6 (preferably 0 or 1), or an optionally substituted heterocyclyl, preferably tetrahydrofuran, tetrahydrothiene, piperidine, piperazine or morpholine (each of which groups when substituted, are preferably substituted with a methyl or halo (F, Br, Cl), each of which groups may be optionally attached to a PTM group (including a ULM' group) via a linker group.

In certain preferred aspects

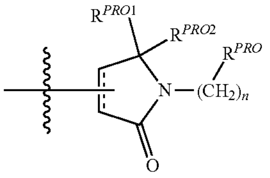

of ULM-g through ULM-i is a

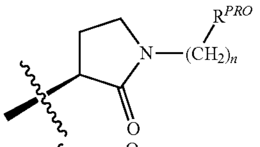

or

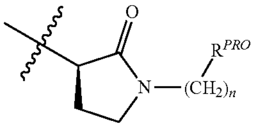

group, where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

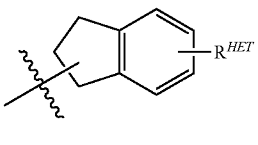

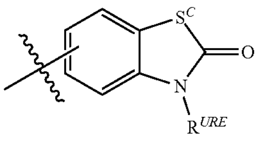

-continued

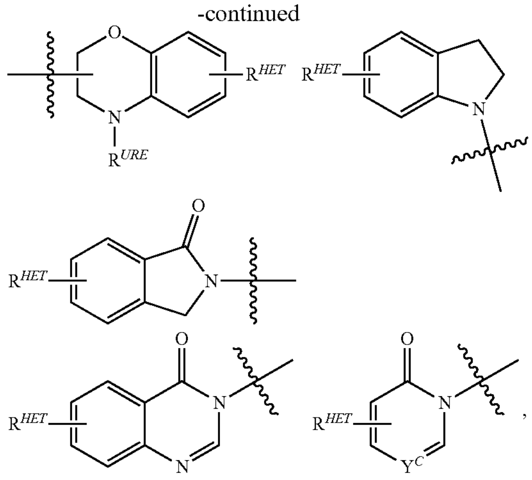

, wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocyclylheterocyclyl groups for $R^{2'}$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

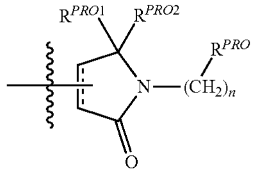

or

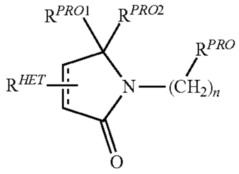

preferably, a

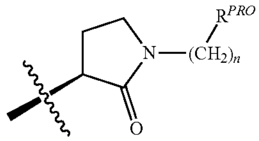

or

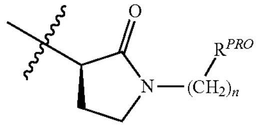

group, wherein:

$R^{PRO}$ of ULM-g through ULM-i is H, optionally substituted $C_1$-$C_6$ alkyl or an optionally substituted aryl, heteroaryl or heterocyclyl group;

$R^{PRO1}$ and $R^{PRO2}$ of ULM-g through ULM-i are each independently H, an optionally substituted $C_1$-$C_3$ alkyl group or together form a keto group and each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted —NH-T-Aryl, an optionally substituted —N($C_1$-$C_3$ alkyl)-T-Aryl, an optionally substituted —NH-T-Heteroaryl group, an optionally substituted —N($C_1$-$C_3$ alkyl)-T-Heteroaryl, an optionally substituted —NH-T-Heterocyclyl, or an optionally substituted —N($C_1$-$C_3$ alkyl)-T-Heterocyclyl, wherein T is an optionally substituted $—(CH_2)_n—$ group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a $—(CH_2O)_n—$ group, a $—(OCH_2)_n—$ group, a $—(CH_2CH_2O)_n—$ group, a $—(OCH_2CH_2)_n—$ group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a $C_1$-$C_6$ alkyl group, an optionally substituted aryl, heteroaryl or heterocyclyl group or a —$(CH_2)_m(R'')_2$ group), each of which may be substituted in ortho-, meta- and/or para-positions of the phenyl ring, preferably para-), or an Aryl (preferably phenyl), Heteroaryl or Heterocyclyl. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methyl substituted pyridine group or an oxapyridine group (where the pyridine group is linked to the phenyl group by an oxygen) or an optionally substituted heterocyclyl (tetrahydrofuran, tetrahydrothiophene, pyrrolidine, piperidine, morpholine, piperazine, tetrahydroquinoline, oxane or thiane. Each of the aryl, heteroaryl or heterocyclyl groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

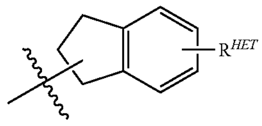

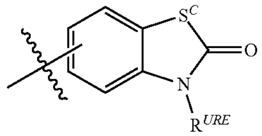

-continued

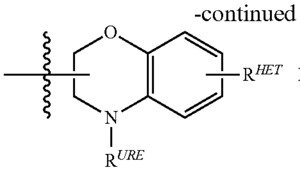

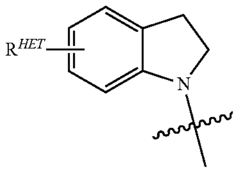

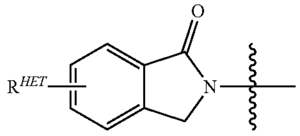

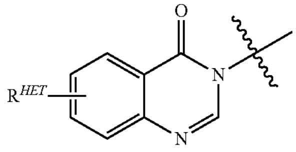

or

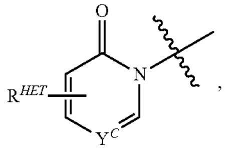

, wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocyclyl groups for $R^{3'}$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

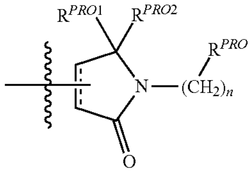

or

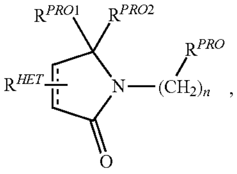

, preferably, a

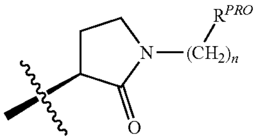

or

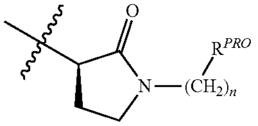

group, wherein:

$R^{PRO}$ of ULM-g through ULM-i is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is 0, 1, 2, 3, 4, 5, or 6 (preferably 0 or 1), wherein each of said heterocyclyl groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted $-NR_1-X^{R2'}$-alkyl group, $-NR_1-X^{R2'}$-Aryl group; an optionally substituted $-NR_1-X^{R2'}$-HET, an optionally substituted $-NR_1-X^{R2'}$-Aryl-HET or an optionally substituted $-NR_1-X^{R2'}$-HET-Aryl, wherein:

$R_1$ of ULM-g through ULM-i is H or a $C_1$-$C_3$ alkyl group (preferably H);

$X^{R2'}$ of ULM-g through ULM-i is an optionally substituted $-CH_2)_n-$, $-CH_2)_n-CH(X_v)=CH(X_v)-$ (cis or trans), $-(CH_2)_n-CH=CH-$, $-(CH_2CH_2O)_n-$ or a $C_3$-$C_6$ cycloalkyl group; and $X_v$ of ULM-g through ULM-i is H, a halo or a $C_1$-$C_3$ alkyl group which is optionally substituted with one or two hydroxyl groups or up to three halogen groups;

Alkyl of ULM-g through ULM-i is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl of ULM-g through ULM-i is an optionally substituted phenyl or naphthyl group (preferably, a phenyl group); and HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

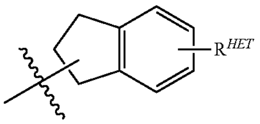

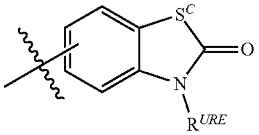

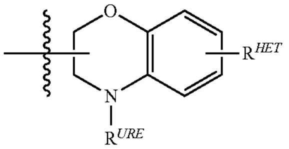

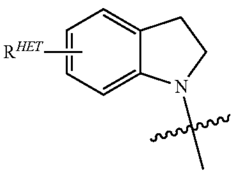

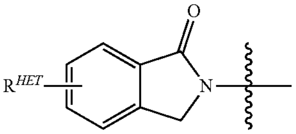

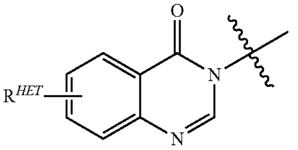

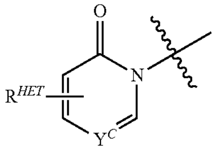

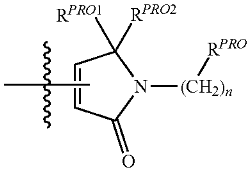

or

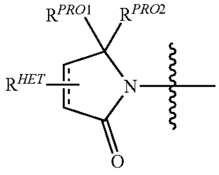

;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative preferred embodiments of the present disclosure, $R^{3'}$ of ULM-g through ULM-i is an optionally substituted —$(CH_2)_n$—$(V)_{n'}$—$(CH_2)_n$—$(V)_{n'}$—$R^{S3'}$ group, an optionally substituted-$(CH_2)_n$—N($R_{1'}$)$(C{=}O)_{m'}$—$(V)_{n'}$—$R^{S3'}$ group, an optionally substituted —$X^{R3'}$-alkyl group, an optionally substituted —$X^{R3'}$-Aryl group; an optionally substituted —$X^{R3'}$-HET group, an optionally substituted —$X^{R3'}$-Aryl-HET group or an optionally substituted —$X^{R3'}$-HET-Aryl group, wherein:

$R^{S3'}$ is an optionally substituted alkyl group ($C_1$-$C_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_{1'}$;

$X^{R3'}$ is —$(CH_2)_n$—, —$(CH_2CH_2O)_n$—, —$CH_2)_n$—CH($X_v$)=CH($X_v$)— (cis or trans), —$CH_2)_n$—CH≡CH—, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

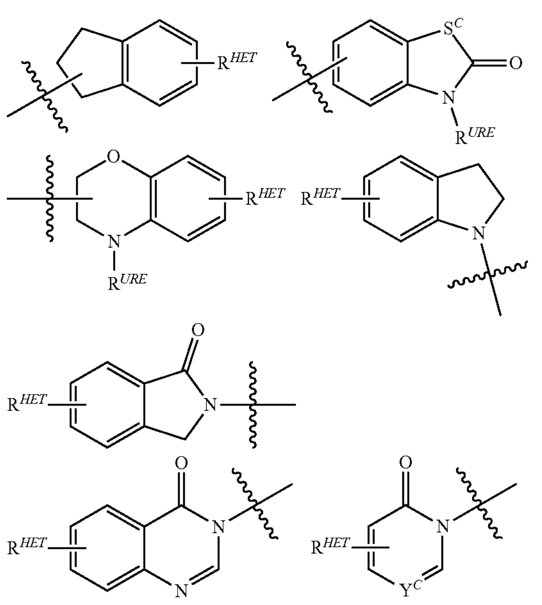

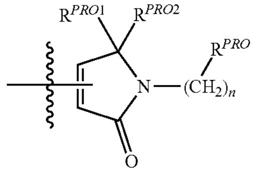
or
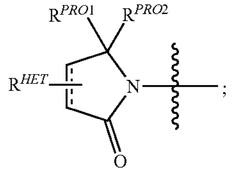
;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$-HET, wherein:

said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_n$O($C_1$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_{m'}$—($C_1$-$C_6$)alkyl group, a —$(V)_{m'}$—$(CH_2CH_2O)_n$—$R^{PEG}$ group where V is O, S or $NR_{1'}$, $R_{1'}$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocyclyl, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

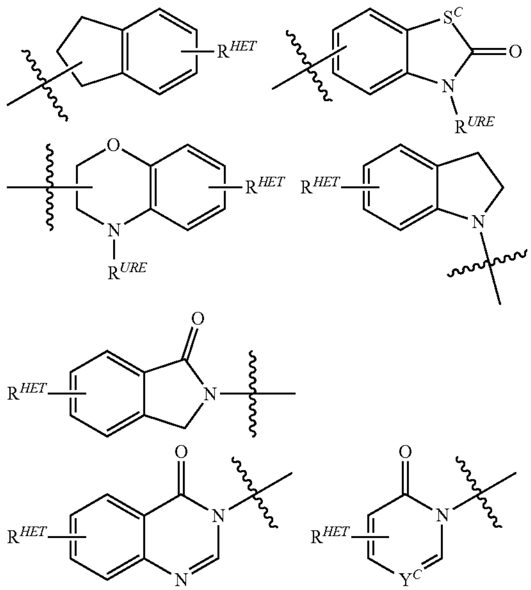

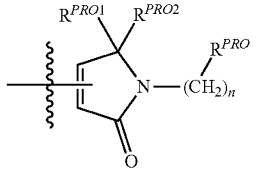

or

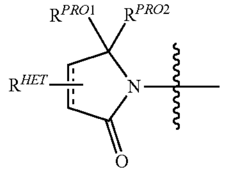

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

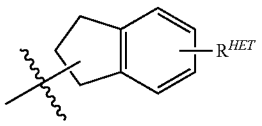

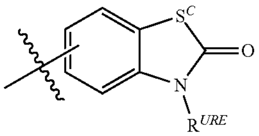

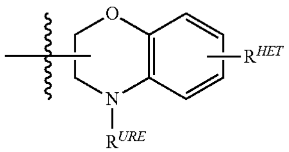

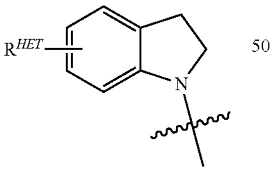

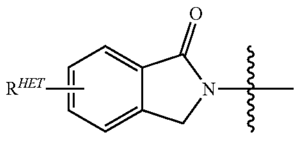

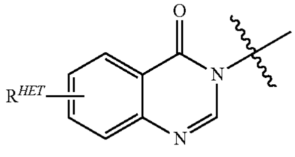

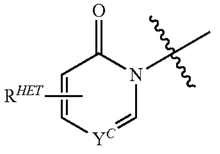

-continued

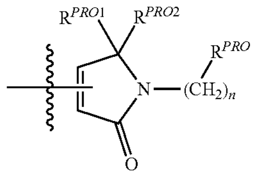

or

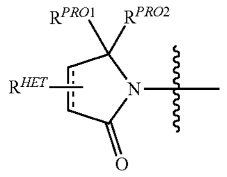

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclyl group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) via a linker group.

In still additional embodiments, preferred compounds include those according to the chemical structure:

ULM-i

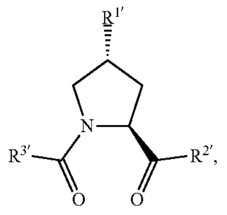

wherein:

$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^{3'}$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —$(CH_2)_nOCH_3$ group where n is 1 or 2 (preferably 2), or a

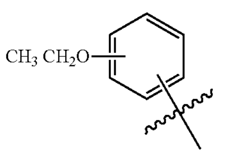

group (the ethyl ether group is preferably meta-substituted on the phenyl moiety), a morpholino group (linked to the carbonyl at the 2- or 3-position;

$R^{3P2}$ of ULM-i is a

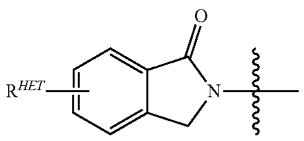

group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

ULM-j

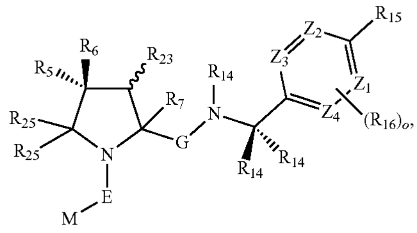

wherein:

each $R_5$ and $R_6$ of ULM-j is independently OH, SH, or optionally substituted alkyl or $R_5$, $R_6$, and the carbon atom to which they are attached form a carbonyl;

$R_7$ of ULM-j is H or optionally substituted alkyl;

E of ULM-j is a bond, C═O, or C═S;

G of ULM-j is a bond, optionally substituted alkyl, —COOH or C=J;

J of ULM-j is O or N—$R_8$;

$R_8$ of ULM-j is H, CN, optionally substituted alkyl or optionally substituted alkoxy;

M of ULM-j is optionally substituted aryl, optionally substituted heteroaryl, optionally substituted heterocyclyl or

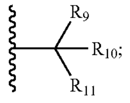

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ of ULM-j is optionally substituted heterocyclyl, optionally substituted alkoxy, optionally substituted heteroaryl, optionally substituted aryl, or

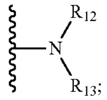

$R_{12}$ of ULM-j is H or optionally substituted alkyl;

$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate, each $R_{14}$ of ULM-j is independently H, haloalkyl, optionally substituted cycloalkyl, optionally substituted alkyl, an azetidine, optionally substituted alkoxy, or optionally substituted heterocyclyl;

$R_{15}$ of ULM-j is H, CN, optionally substituted heteroaryl, haloalkyl, optionally substituted aryl, optionally substituted alkoxy, or optionally substituted heterocyclyl;

each $R_{16}$ of ULM-j is independently halo, optionally substituted alkyl, optionally substituted haloalkyl, optionally substituted CN, or optionally substituted haloalkoxy;

each $R_{25}$ of ULM-j is independently H or optionally substituted alkyl; or both $R_{25}$ groups can be taken together to form an oxo or optionally substituted cycloalkyl group;

$R_{23}$ of ULM-j is H or OH;

$Z_1$, $Z_2$, $Z_3$, and $Z_4$ of ULM-j are independently C or N; and o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C═O and M is

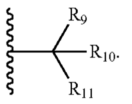

In certain embodiments, wherein E of ULM-j is C═O, $R_{11}$ is optionally substituted heterocyclyl or

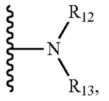

and M is

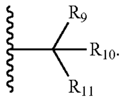

In certain embodiments, wherein E of ULM-j is C═O, M is

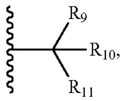

and $R_{11}$ is

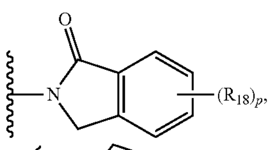

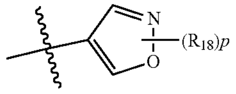 or

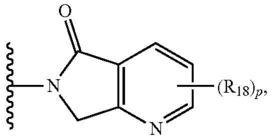

each $R_{18}$ is independently H, halo, optionally substituted alkoxy, cyano, optionally substituted alkyl, haloalkyl, or haloalkoxy; and p is 0, 1, 2, 3, or 4.

In certain embodiments, each $R_{14}$ is independently substituted with at least one of H, hydroxyl, halo, amine, amide, alkoxy, alkyl, haloalkyl, or heterocyclic.

In certain embodiments, $R_{15}$ of ULM-j is a group according to

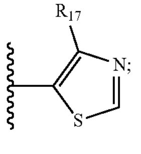

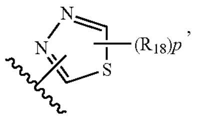

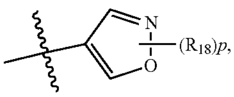

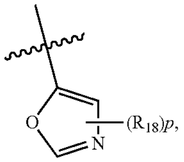

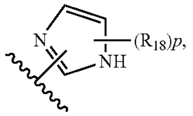

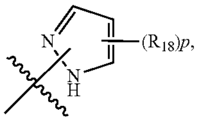

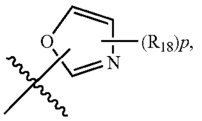

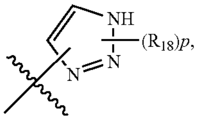

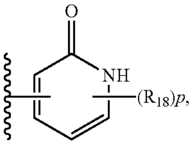

CN, or a haloalkyl, and each $R_{18}$ is independently H, halo, optionally substituted alkoxy, cyano, aminoalkyl, amidoalkyl, optionally substituted alkyl, haloalkyl, or haloalkoxy; and p is 0, 1, 2, 3, or 4.

In certain embodiments, ULM and where present, ULM', are each independently a group according to the chemical structure:

ULM-k

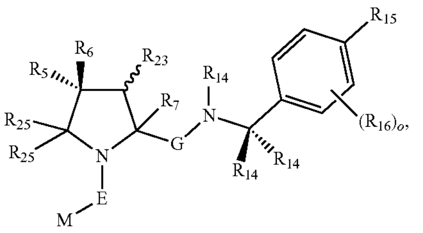

wherein:

G of ULM-k is C=J, J is O;

$R_7$ of ULM-k is H;

each $R_{14}$ of ULM-k is independently H, an amide, an alkyl, e.g., methyl, optionally substituted with one or more $C_1$-$C_6$ alkyl groups or C(O)NR'R";

R' and R" are each independently H, optionally substituted alkyl, or cycloalkyl;

o of ULM-k is 0;

$R_{15}$ of ULM-k is defined as above for ULM-j;

$R_{16}$ of ULM-k is defined is as above for ULM-j; and $R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

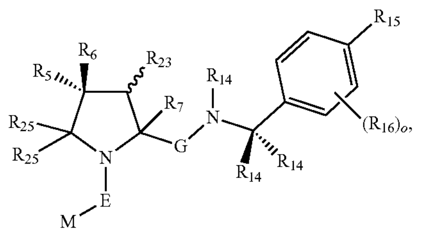

wherein:

G of ULM-k is C=J, J is O;

$R_7$ of ULM-k is H;

each $R_{14}$ of ULM-k is H;

o of ULM-k is 0; and $R_{15}$ of ULM-k is selected from the group consisting of optionally substituted:

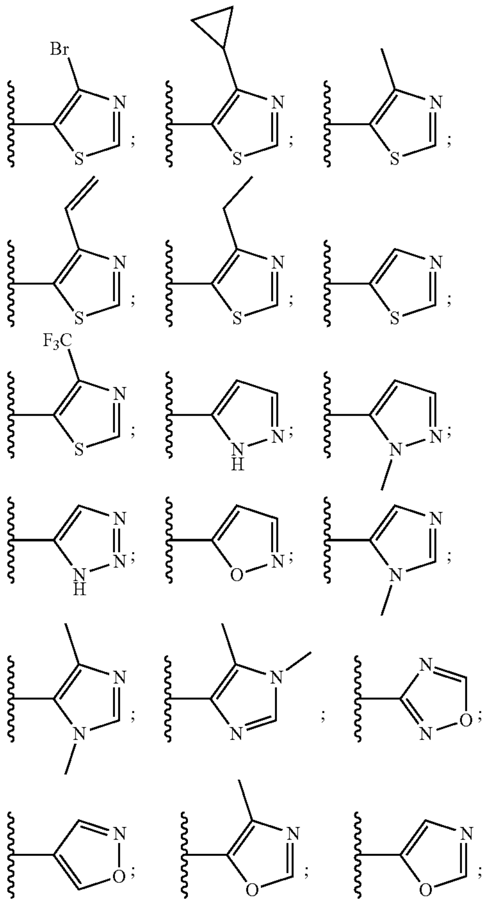

-continued

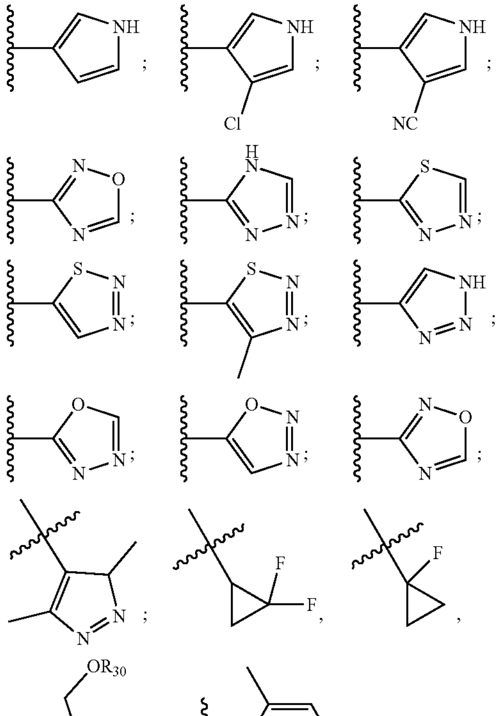

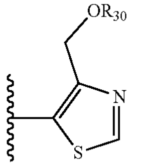

and

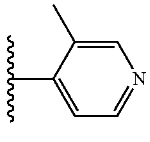

, wherein $R_{30}$ of ULM-k is H or an optionally substituted alkyl.

In other embodiments, ULM and where present, ULM', are each independently a group according to the chemical structure:

ULM-k

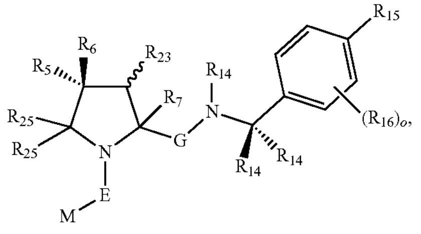

wherein:

E of ULM-k is C=O;

M of ULM-k is

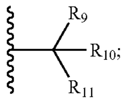

and $R_{11}$ of ULM-k is selected from the group consisting of optionally substituted:

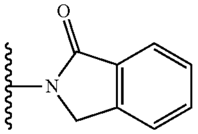
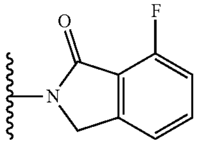
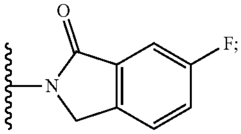
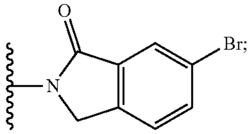
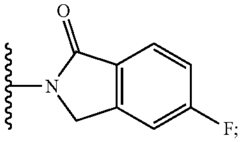
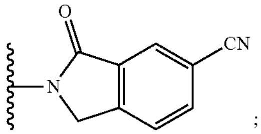
;
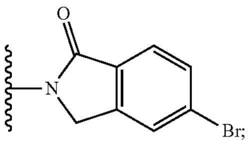
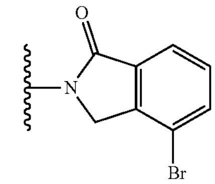
;
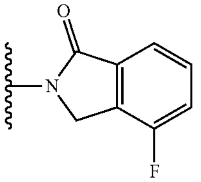
;
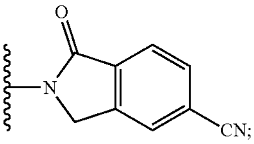
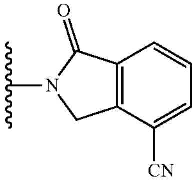
;
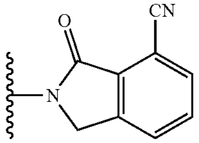
;
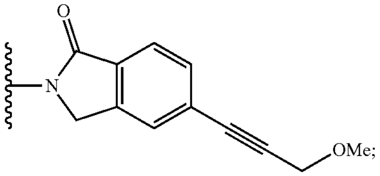
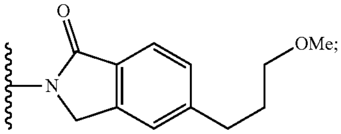
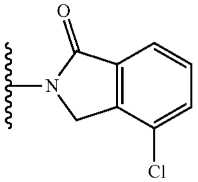
;
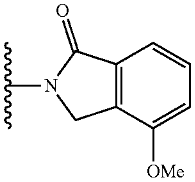
;
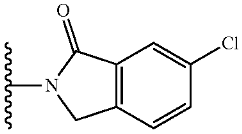
;
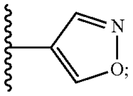
and -continued

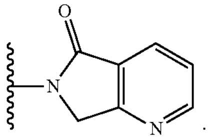
.

In still other embodiments, a compound of the chemical structure,

ULM-k

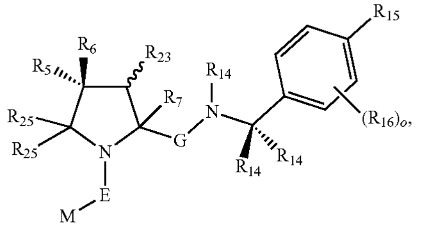

wherein:

E of ULM-k is C═O;

$R_{11}$ of ULM-k is

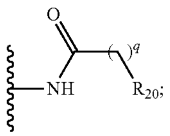

and

M of ULM-k is

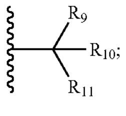

q of ULM-k is 1 or 2;

$R_{20}$ of ULM-k is H, optionally substituted alkyl, optionally substituted cycloalkyl, optionally substituted aryl, or

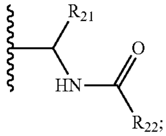

$R_{21}$ of ULM-k is H or optionally substituted alkyl; and $R_{22}$ of ULM-k is H, optionally substituted alkyl, optionally substituted alkoxy, or haloalkyl.

In any embodiment described herein, $R_{11}$ of ULM-j or ULM-k is selected from the group consisting of:

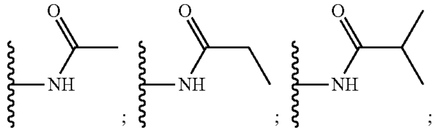
; ; ;
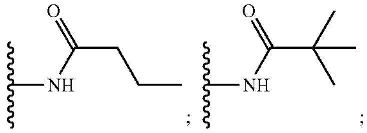
; ;
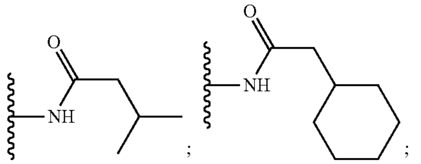
; ;
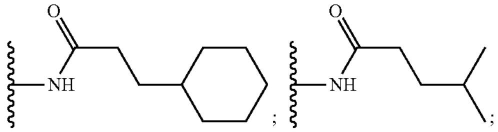
; ;
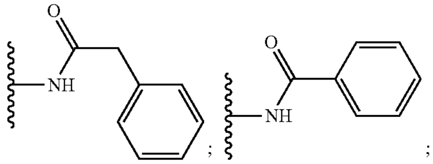
; ;
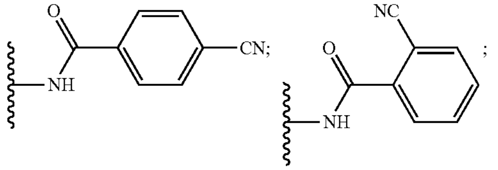
CN; ;
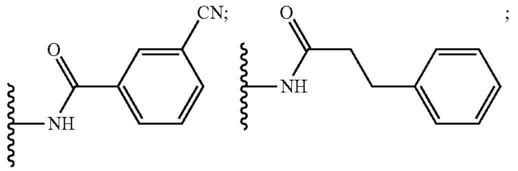
CN; ;
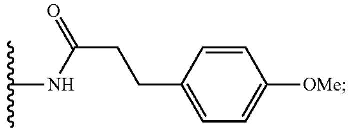
OMe;
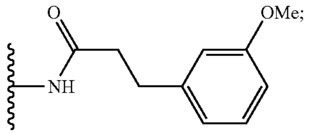
OMe;
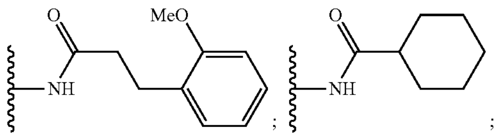
; ;
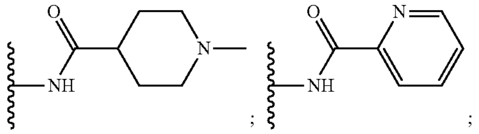
; ;
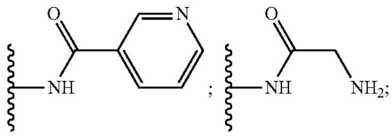
; NH₂;
-continued
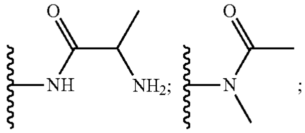
NH₂; ;
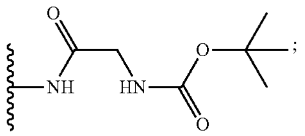
;
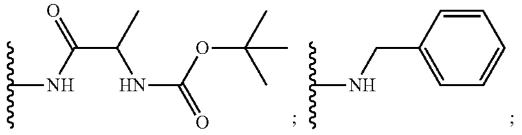
; ;
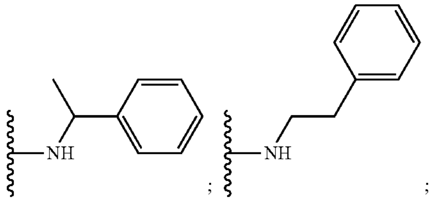
; ;
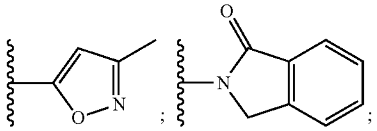
; ;
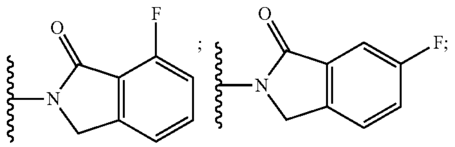
; F;
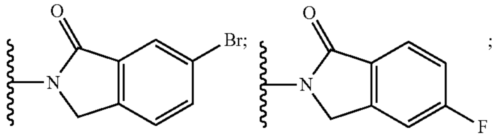
Br; ;
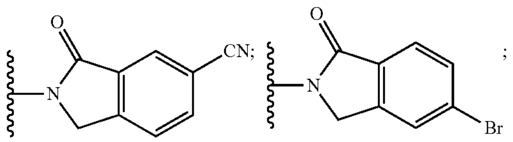
CN; ;
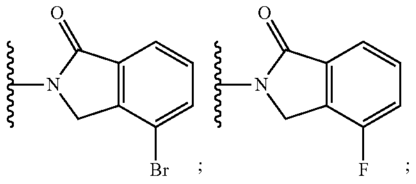
; ;
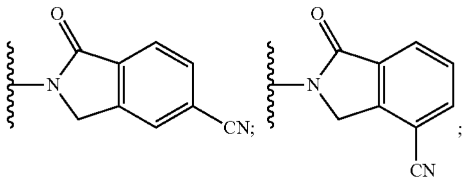
CN; ;
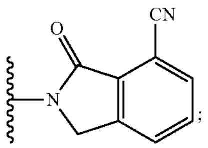
;

-continued
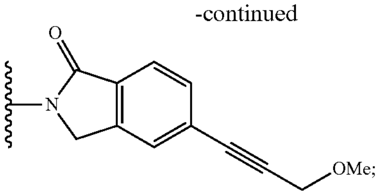
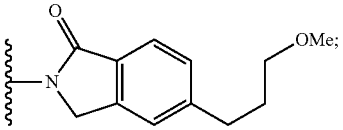
;
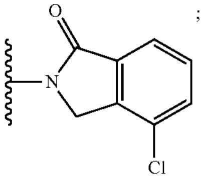
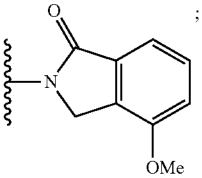
;
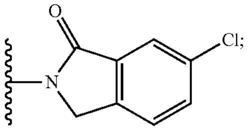
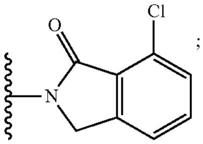
;
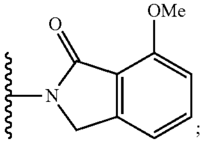
;
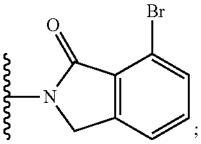
;
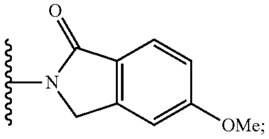
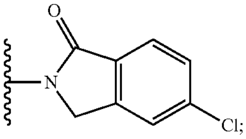
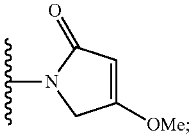
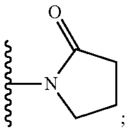
;
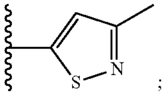
;
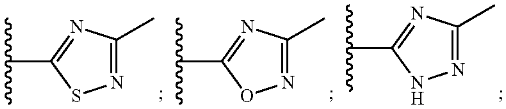
;
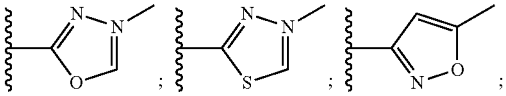
;
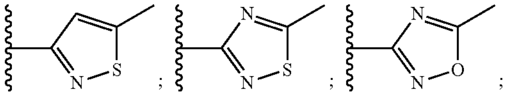
;
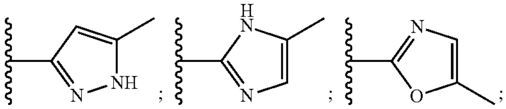
;
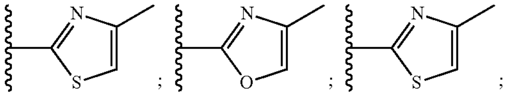
;
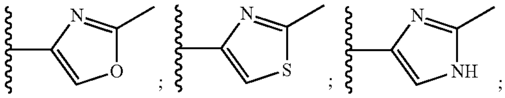
;
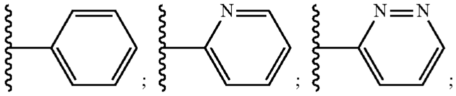
;
-continued
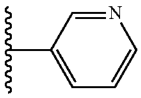
;
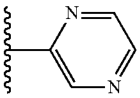
;
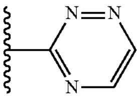
; and
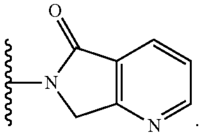
.
In certain embodiments, $R_{11}$ of ULM-j or ULM-k is selected from the group consisting of:
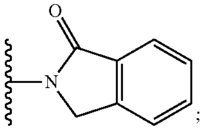
;
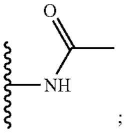
;
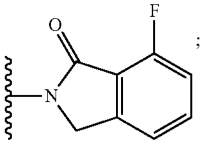
;
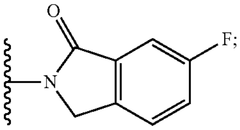
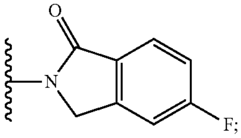
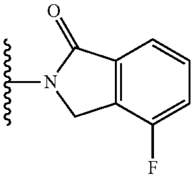
;
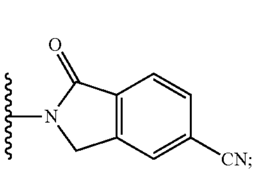
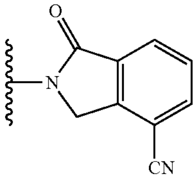
;
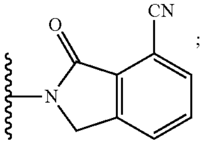
;
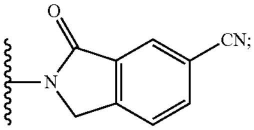
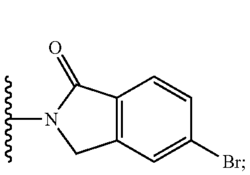
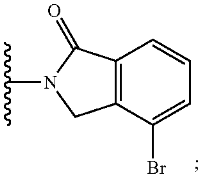
;
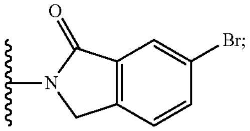
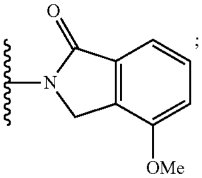
;
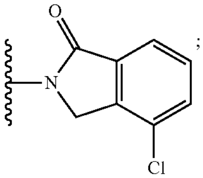
;
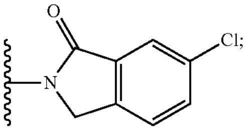

-continued
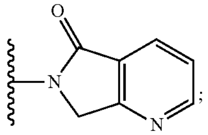
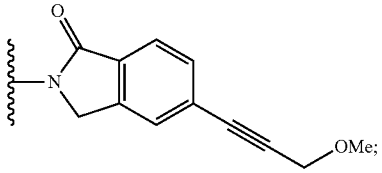
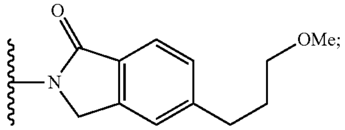
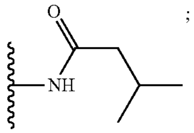
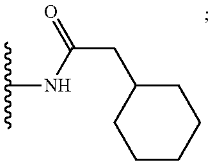
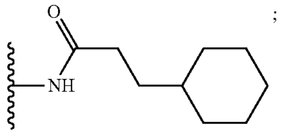
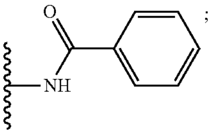
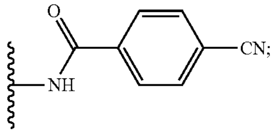
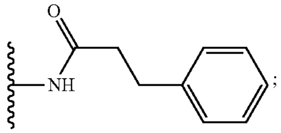
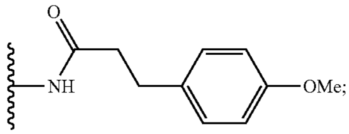
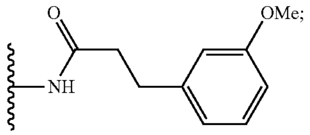
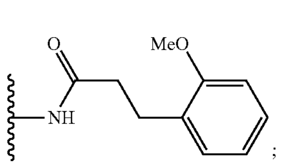
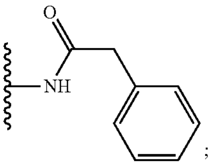
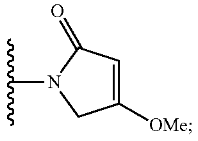
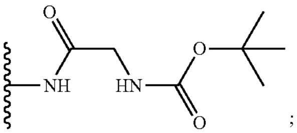
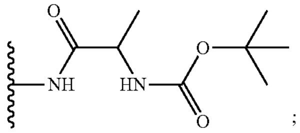
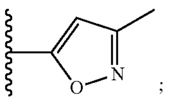
-continued
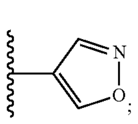
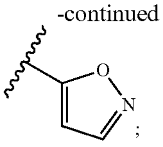
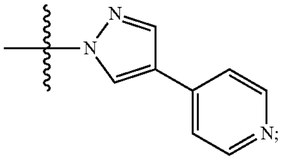
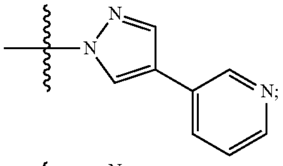
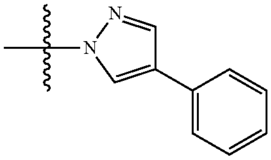
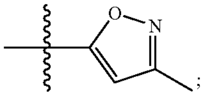
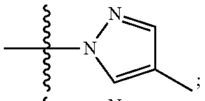
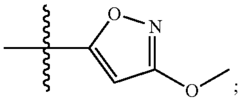
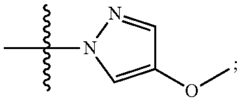
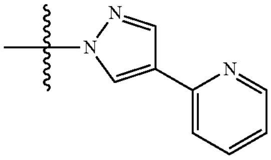
and
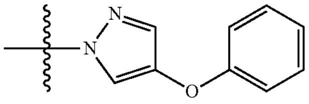
In certain embodiments, ULM (or when present ULM') is a group according to the chemical structure:
ULM-1
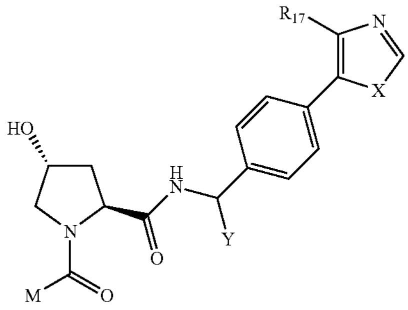
,
wherein:
X of ULM-1 is O or S;
Y of ULM-1 is H, methyl or ethyl;
$R_{17}$ of ULM-1 is H, methyl, ethyl, hydroxymethyl or cyclopropyl;
M of ULM-1 is optionally substituted aryl, optionally substituted heteroaryl, or

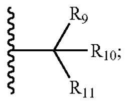

$R_9$ of ULM-1 is H;

$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

R11 of ULM-1 is optionally substituted heteroaromatic, optionally substituted heterocyclyl, optionally substituted aryl or

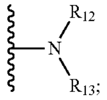

$R_{12}$ of ULM-1 is H or optionally substituted alkyl; and $R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

ULM-m

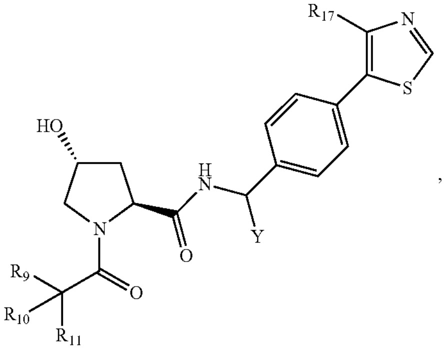

, wherein:

Y of ULM-m is H, methyol or ethyl $R_9$ of ULM-m is H;

$R_{10}$ is isopropyl, tert-butyl, sec-butyl, cyclopentyl, or cyclohexyl;

$R_{11}$ of ULM-m is optionally substituted amide, optionally substituted isoindolinone, optionally substituted isooxazole, optionally substituted heterocyclyls.

In other preferred embodiments of the disclosure, ULM and where present, ULM', are each independently a group according to the chemical structure:

ULM-n

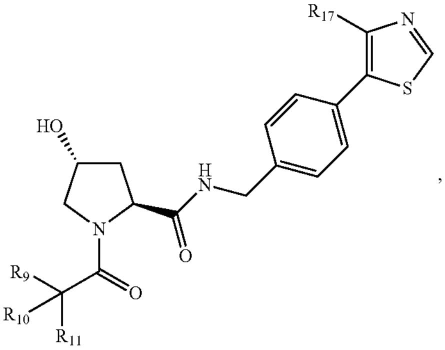

, wherein:

$R_{17}$ of ULM-n is methyl, ethyl, or cyclopropyl; and $R_9$, $R_{10}$, and $R_{11}$ of ULM-n are as defined above. In other instances, $R_9$ is H; and $R_{10}$ of ULM-n is H, alkyl, or cycloalkyl (preferably, isopropyl, tert-butyl, sec-butyl, cyclopentyl, or cyclohexyl).

In other preferred embodiments of the disclosure, ULM and where present, ULM', are each independently a group according to the chemical structure:

ULM-o

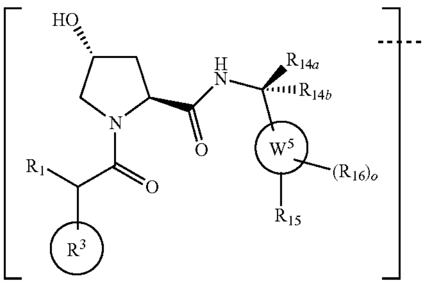

or

ULM-p

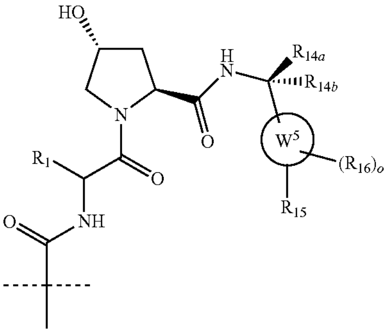

or a pharmaceutically acceptable salt thereof, wherein:

$R_1$ is H, optionally substituted alkyl or optionally substituted cycloalkyl;

$R_3$ is an optionally substituted 5-6 membered heteroaryl;

$W^5$ is optionally substituted phenyl, optionally substituted napthyl or optionally substituted pyridinyl;

one of $R_{14a}$ and $R_{14b}$ is H, optionally substituted alkyl, optionally substituted haloalkyl (e.g., fluoroalkyl), optionally substituted alkoxy, optionally substituted hydroxyl alkyl, optionally substituted alkylamine, optionally substituted heteroalkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalkyl, spirocycloalkyl or spiroheterocyclyl, wherein the spiroheterocyclyl is not epoxide or aziridine;

$R_{15}$ is CN, optionally substituted fluoroalkyl,

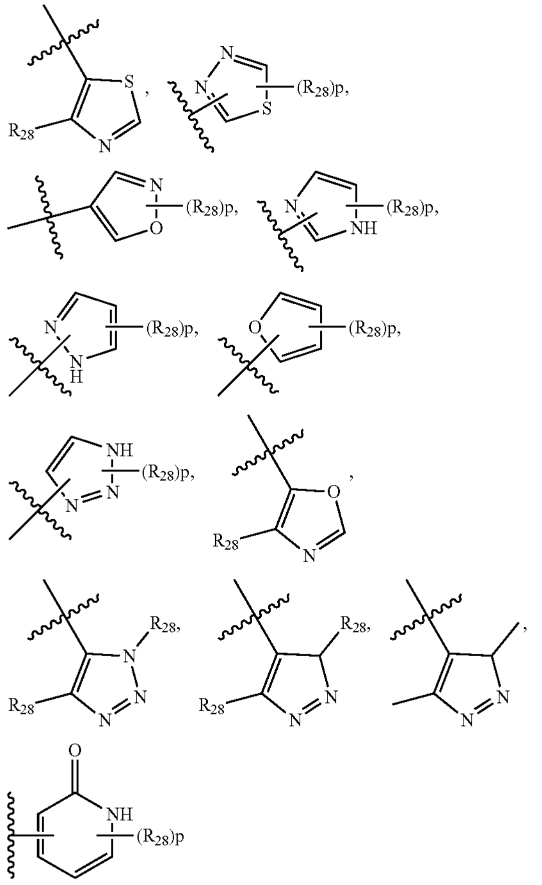

optionally substituted

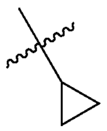 (e.g., 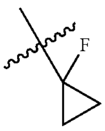, 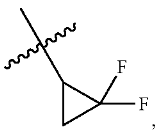,

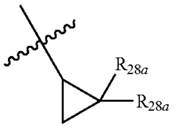 or 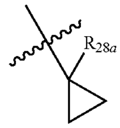, wherein $R_{28a}$ is halo, optionally substituted alkyl or fluoroalkyl, or

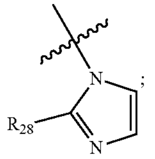;

each $R_{16}$ is independently selected from halo, CN, optionally substituted alkyl, optionally substituted haloalkyl, hydroxy, or haloalkoxy;

each $R_{26}$ is independently H, optionally substituted alkyl or $NR_{27a}R_{27b}$;

each $R_{27a}$ and $R_{27b}$ is independently H, optionally substituted alkyl, optionally substituted cycloalkyl (e.g. optionally substituted 3-5 member cycloalkyl), or $R_{27a}$ and $R_{27b}$ together with the nitrogen atom to which they are attached form a 4-6 membered heterocyclyl;

each $R_{28}$ is independently H, halogen, CN, optionally substituted aminoalkyl, optionally substituted amidoalkyl, optionally substituted haloalkyl, optionally substituted alkyl, optionally substituted alkoxy, optionally substituted heteroalkyl, optionally substituted alkylamine, optionally substituted hydroxyalkyl, amine, optionally substituted alkynyl, or optionally substituted cycloalkyl;

o is 0, 1 or 2; and p is 0, 1, 2, 3, or 4.

In any of the aspects or embodiments described herein, the ULM is of the formula:

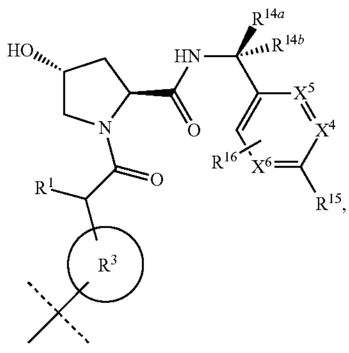

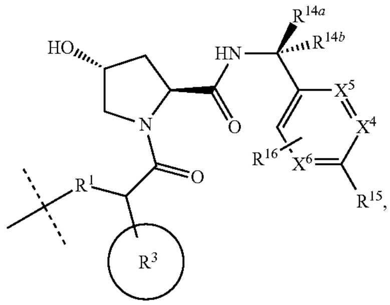

-continued

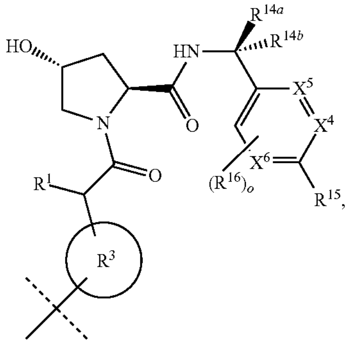

or

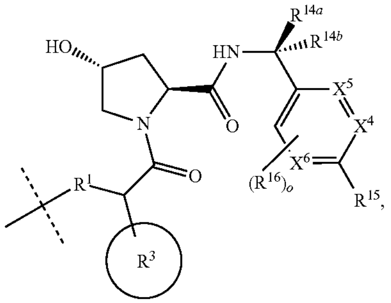

wherein:

each of $X^4$, $X^5$, and $X^6$ is selected from CH and N, wherein no more than 2 are N;

$R^1$ is $C_{1-6}$ alkyl;

$R^3$ is the same as defined for ULM-o and ULM-p one of $R^{14a}$ and $R^{14b}$ is H, optionally substituted alkyl, optionally substituted haloalkyl, optionally substituted alkoxy, optionally substituted hydroxyl alkyl, optionally substituted alkylamine, optionally substituted amide, optionally substituted alkyl-amide, optionally substituted alkyl-cyano, optionally substituted alkyl-phosphate, optionally substituted heteroalkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H; or $R^{14a}$ and $R^{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine;

each $R_{27a}$ and $R_{27b}$ is independently H $C_{1-6}$ alkyl or cycloalkyl (e.g., optionally substituted 3-5 member cycloalkyl);

o is 0, 1, or 2;

q is 1, 2, 3 or 4;

$R^{15}$ is optionally substituted

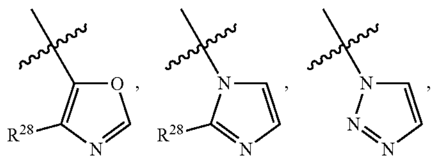

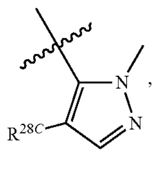

, or CN;

$R^{28}$ is H, methyl, $CH_2N(Me)_2$, $CH_2OH$, $CH_2O(C_{1-4}alkyl)$, $CH_2NHC(O)C_{1-4}alkyl$, $NH_2$,

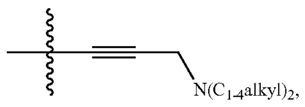

or

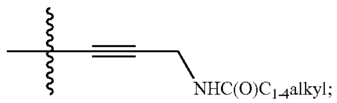

$R^{28C}$ is H, methyl, fluoro, or chloro; and $R^{16}$ is H, $C_{1-4}$alkyl, fluoro, chloro, CN, or $C_{1-4}$alkoxy.

In any aspect or embodiment described herein, $R^{14a}$ and $R^{14b}$ are selected from: H, $C_{1-4}$ alkyl, $C_{1-4}$ cycloalkyl, $C_{1-4}$ haloalkyl, $C_{1-4}$ hydroxyalkyl, $C_{1-4}$ alkyloxyalkyl, $C_{1-4}$ alkyl-$NR_{27a}R_{27b}$ and $CONR_{27a}R_{27b}$.

In any aspect or embodiment described herein, at least one of $R^{14a}$ and $R^{14b}$ is H (e.g., both $R^{14a}$ and $R^{14b}$ are H).

In any aspect or embodiment described herein, at least one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$. Alternatively, in any aspect or embodiment described herein, one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H.

In any aspect or embodiment described herein, $R^{14a}$ and $R^{14b}$ together with the carbon atom to which they are attached form

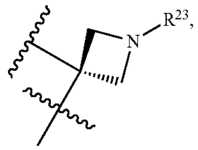

wherein $R^{23}$ is selected from H, $C_{1-4}$alkyl, —C(O)$C_{1-4}$alkyl.

In other preferred embodiments of the disclosure, ULM and where present, ULM', are each independently a group according to the chemical structure:

ULM-q

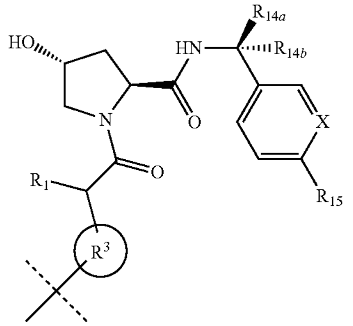

or

-continued

ULM-r

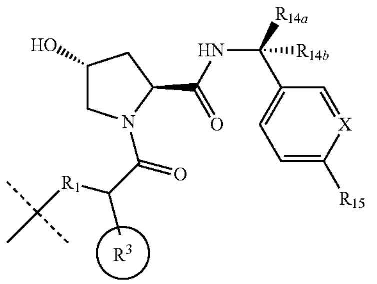

or a pharmaceutically acceptable salt thereof, wherein:

X is CH or N; and $R_1$, $R_3$, $R_{14a}$, $R_{14b}$, and $R_{15}$ of ULM-q and ULM-r are the same as defined for ULM-o and ULM-p.

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

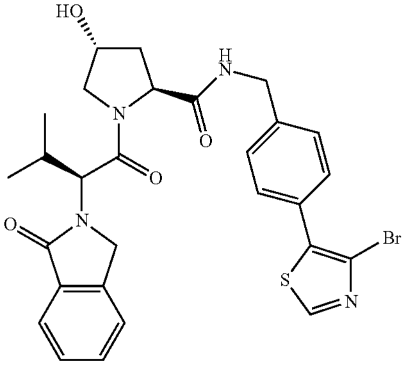

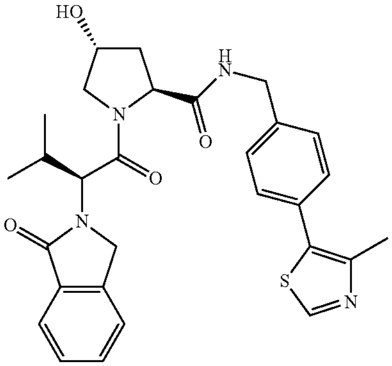

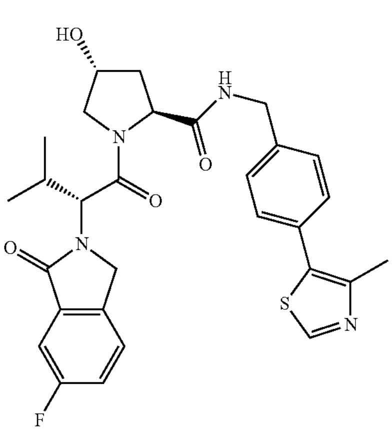

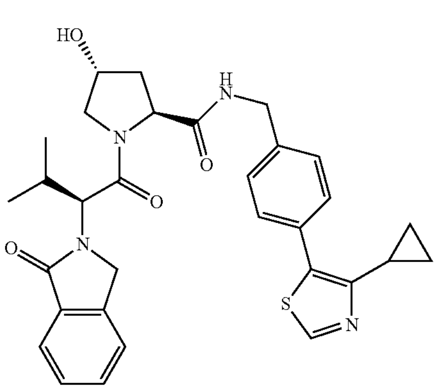

-continued
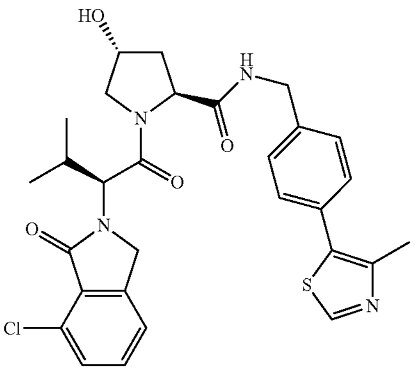
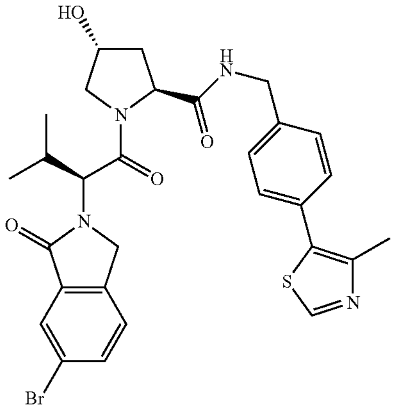
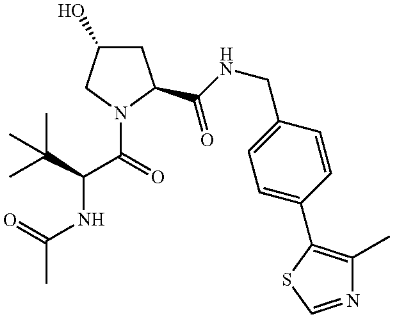
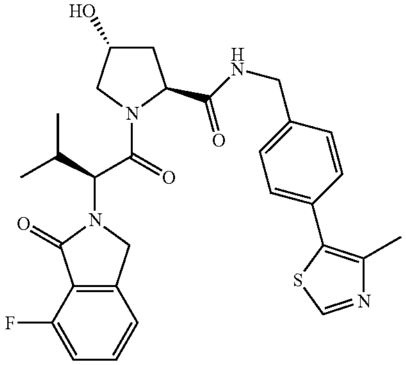
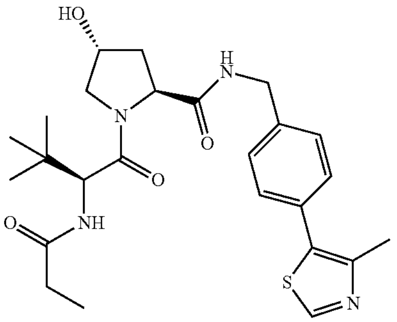
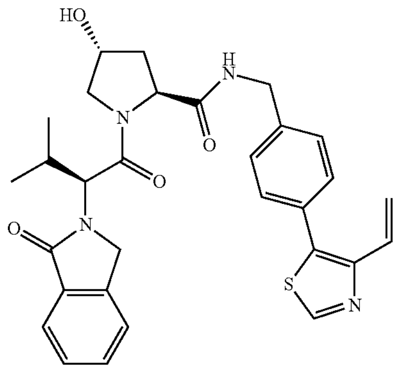
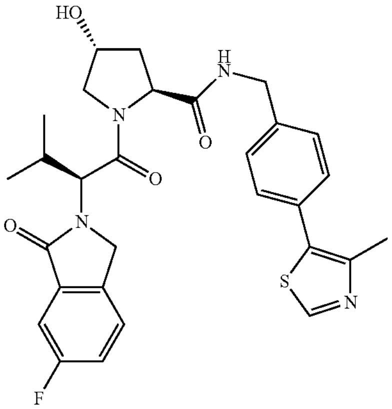
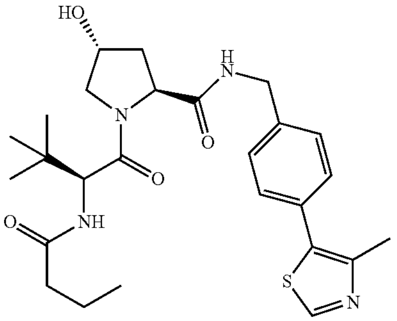

-continued
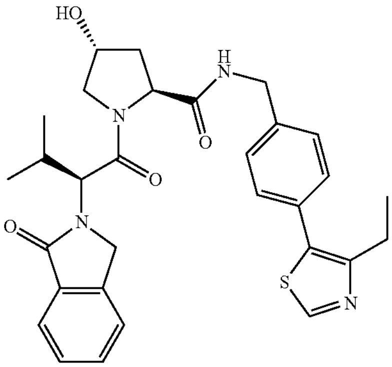
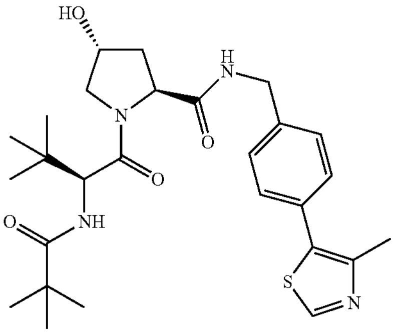
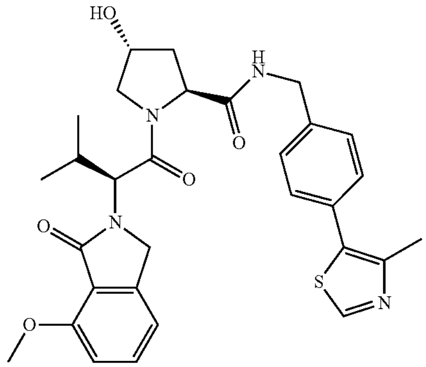
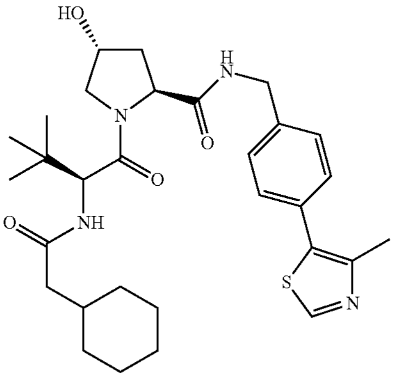
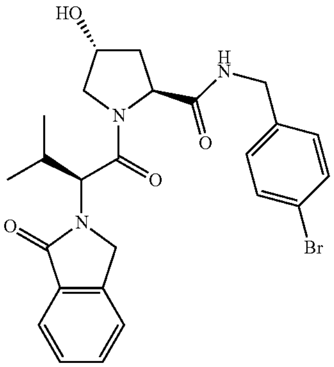
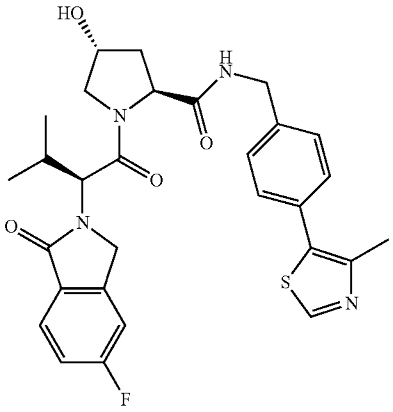
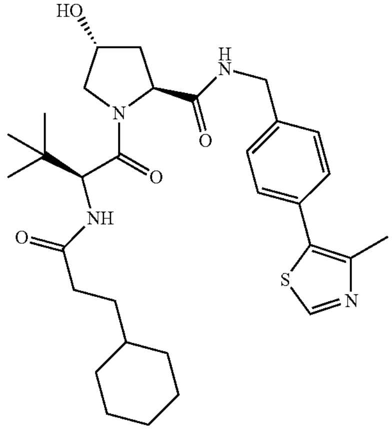
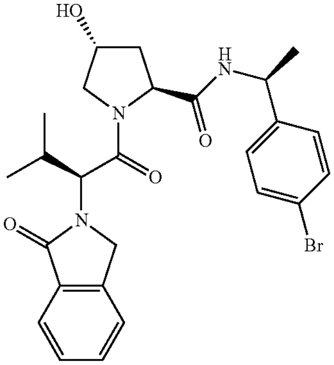

-continued
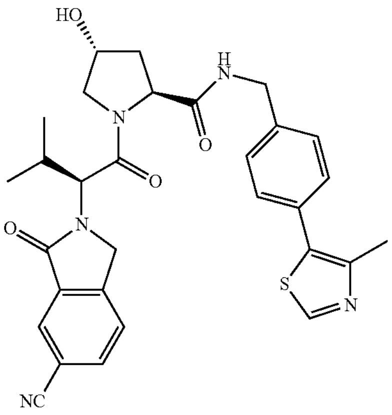
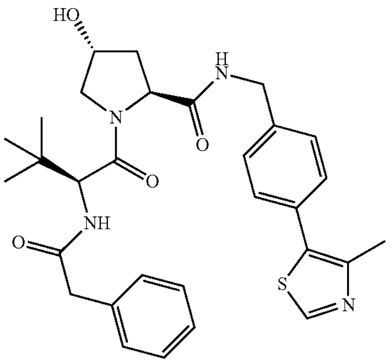
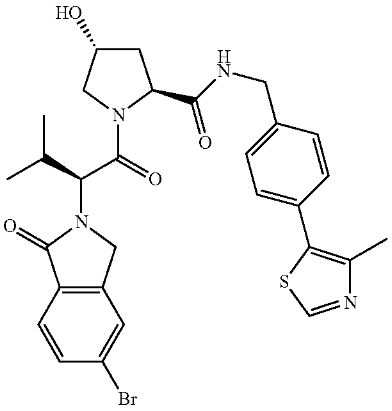
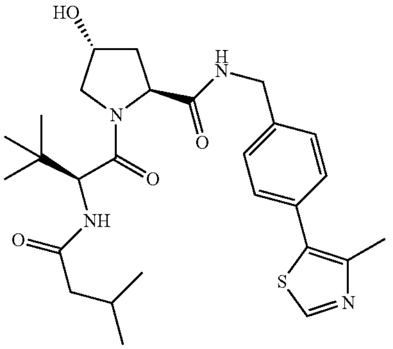
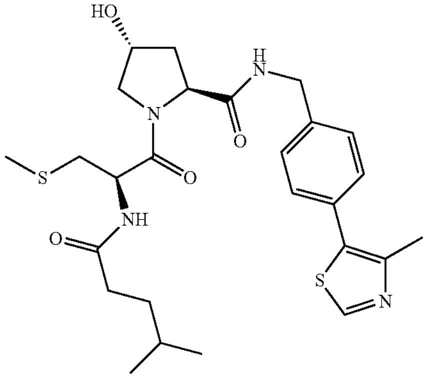
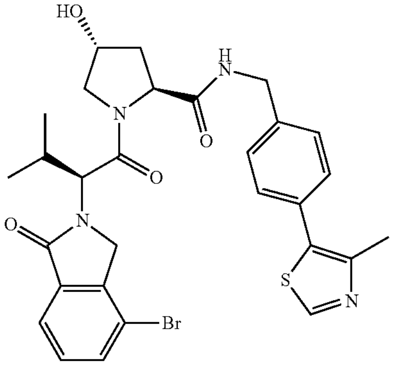
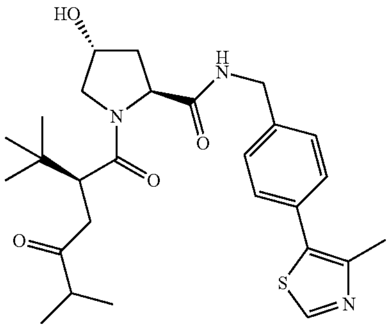
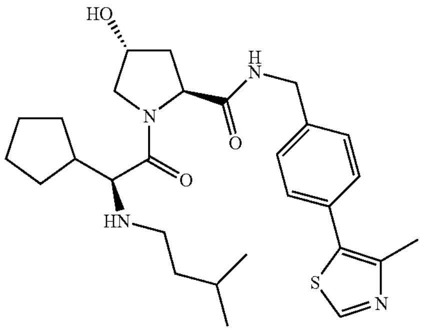

-continued
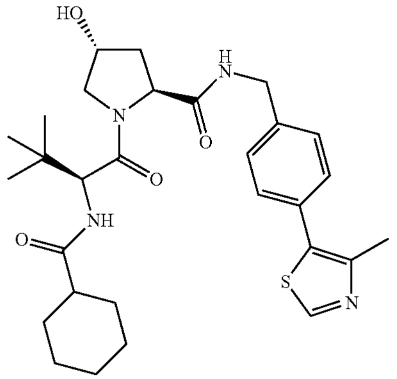
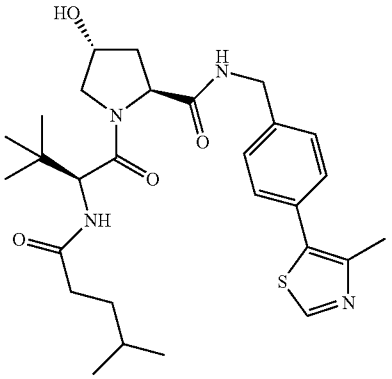
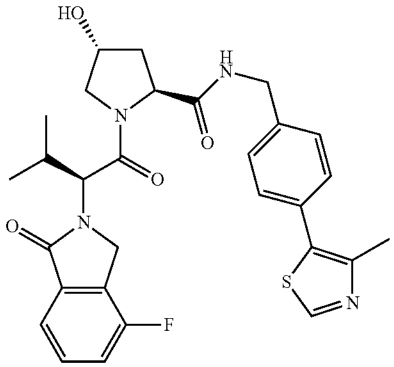
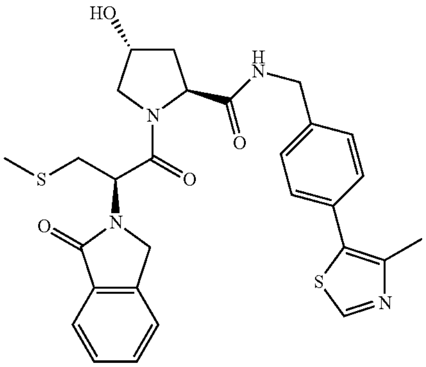
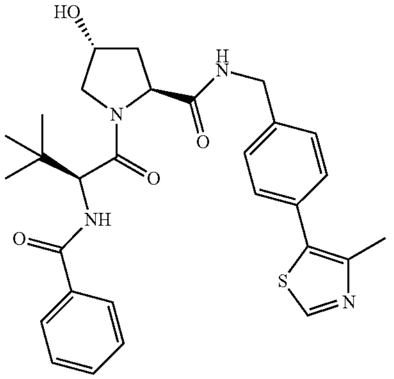
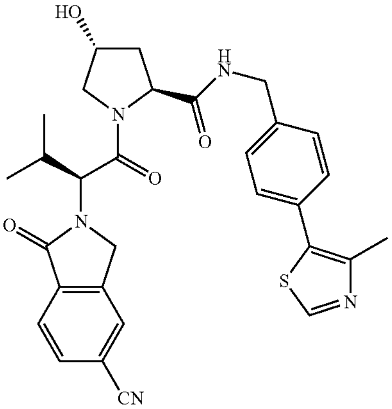
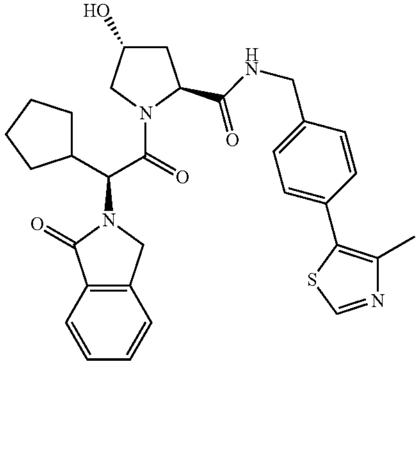
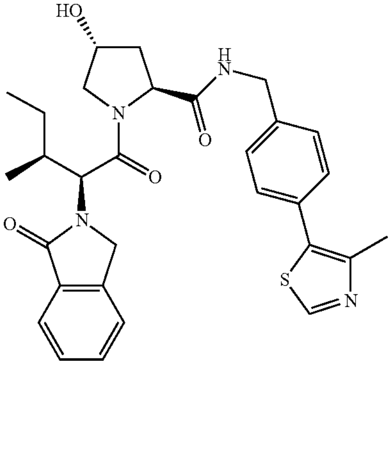

-continued
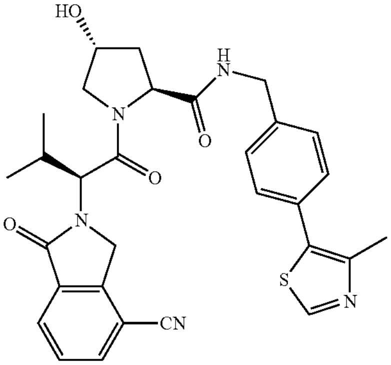
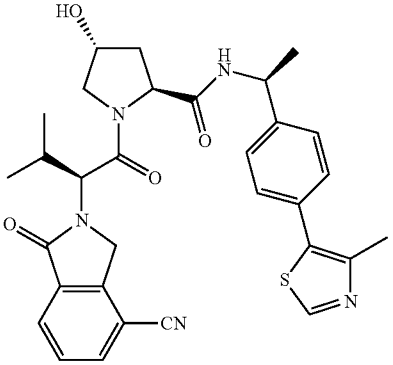
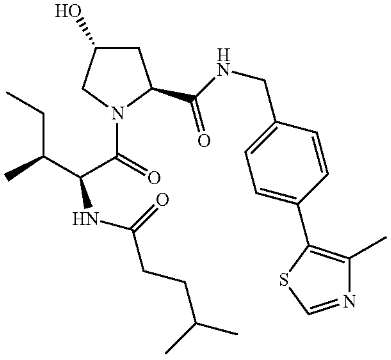
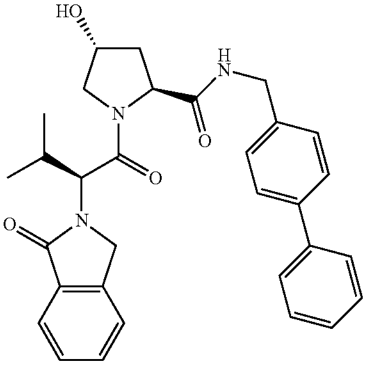
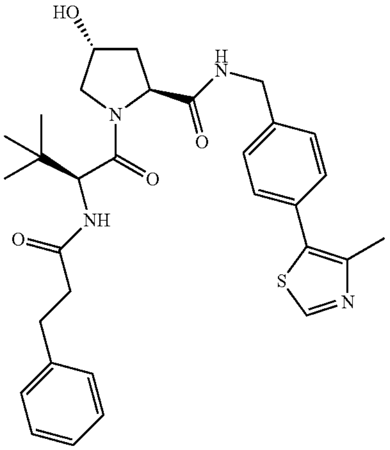
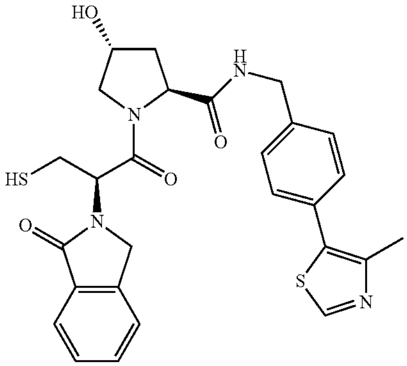
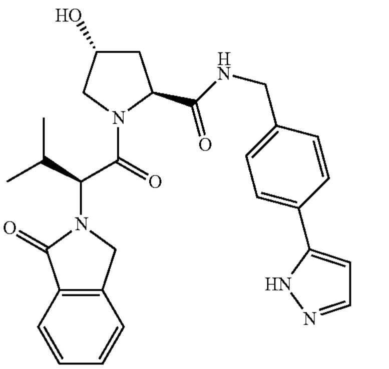
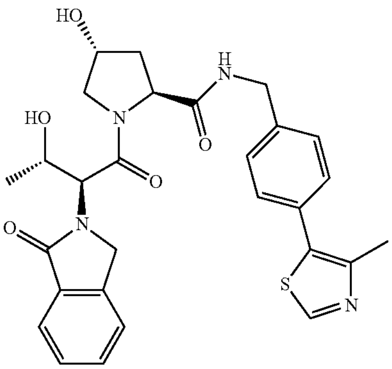

-continued
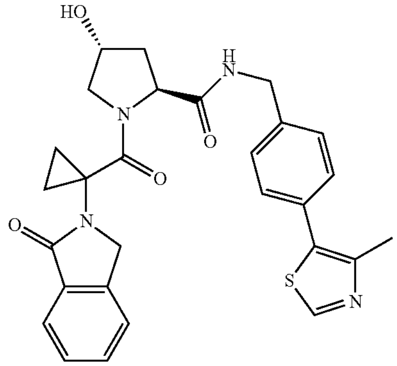
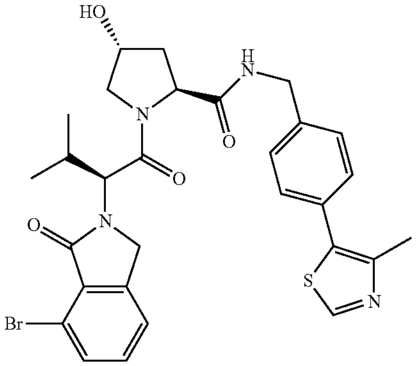
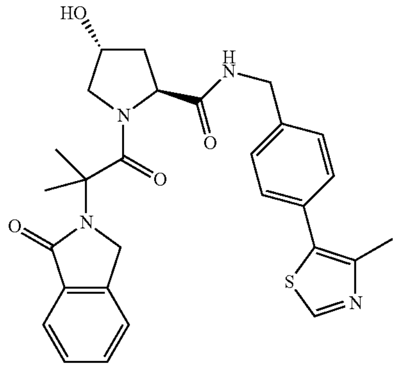
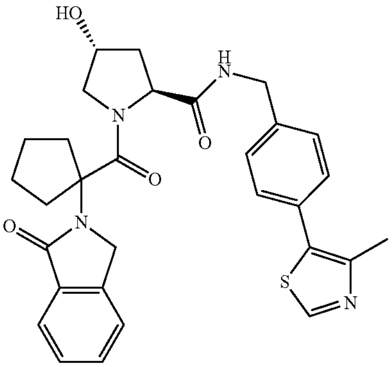
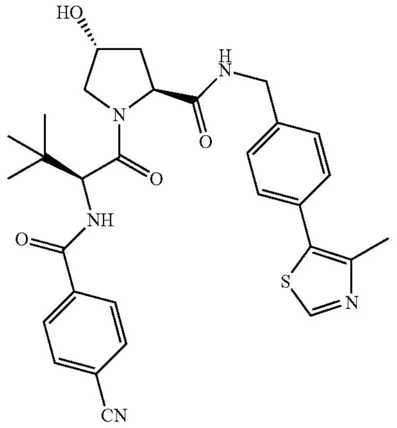
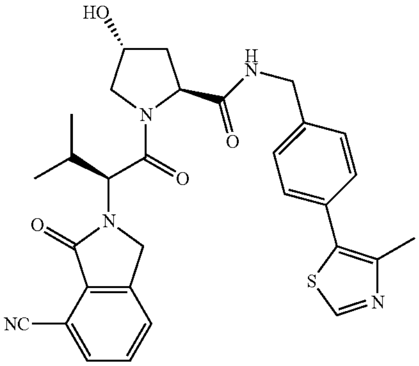
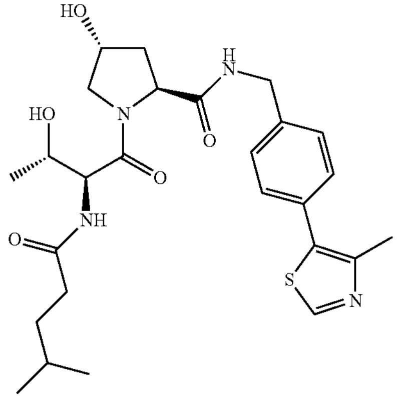
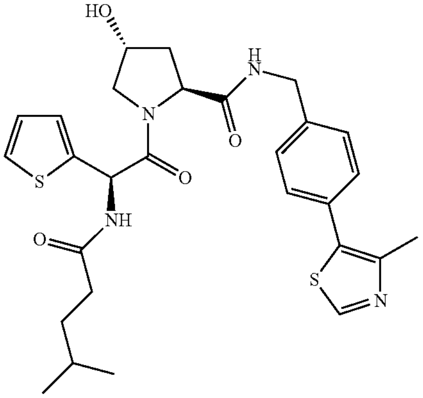

-continued
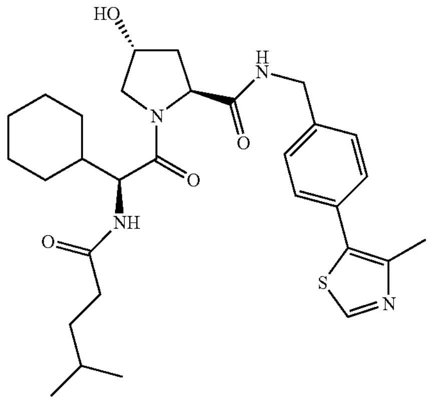
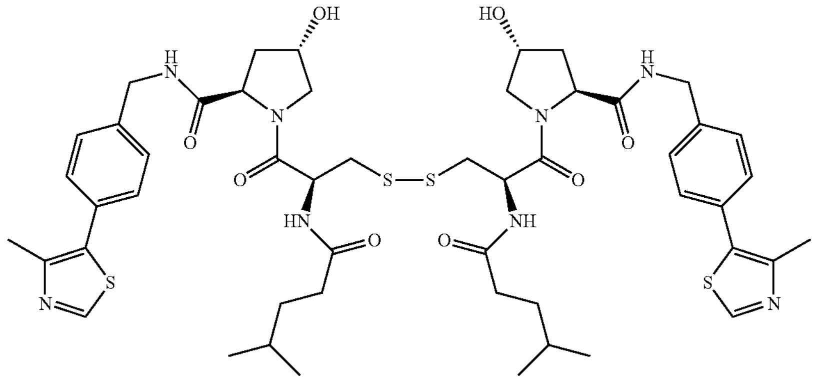
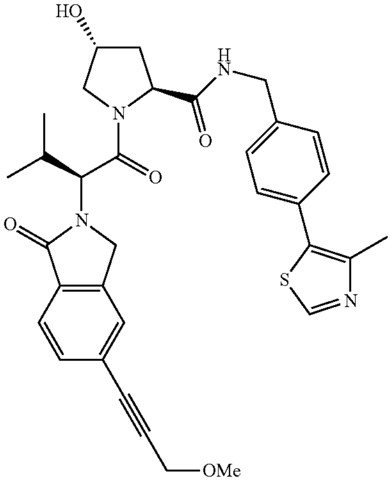
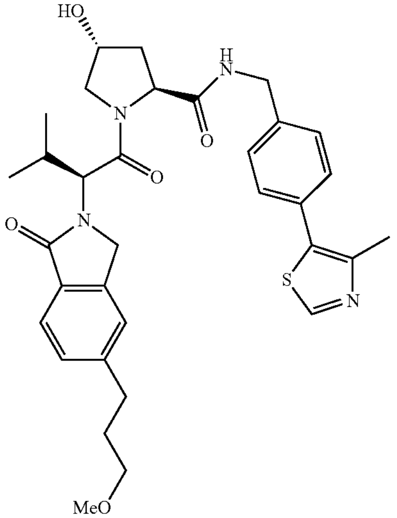
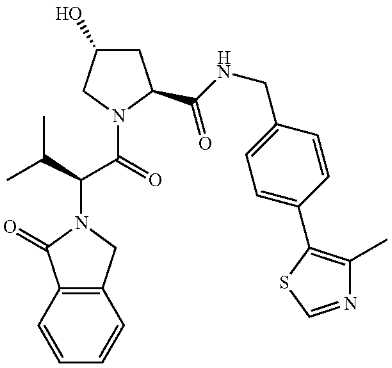
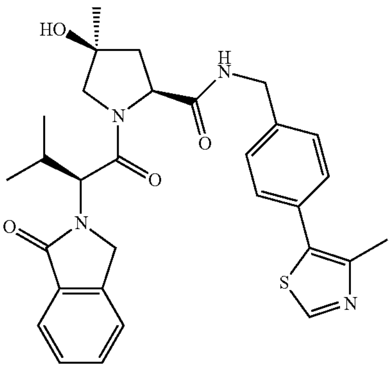

-continued
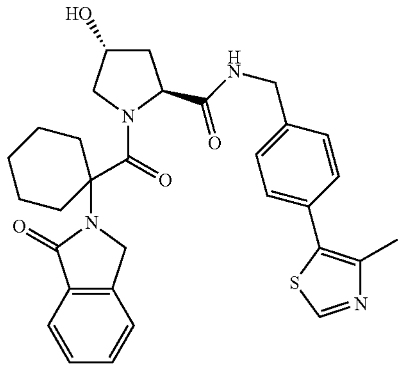
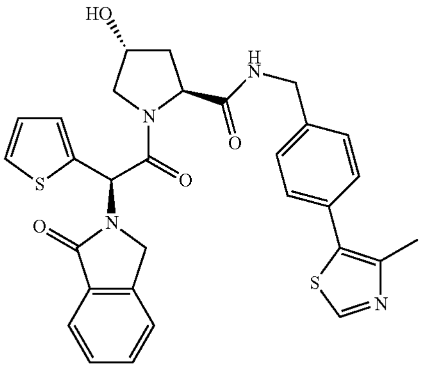
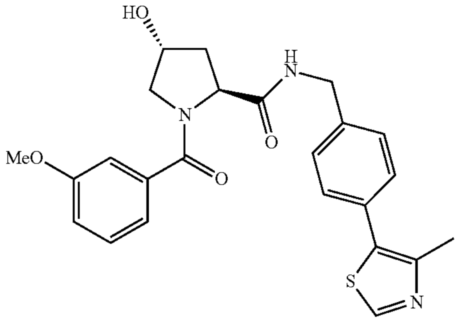
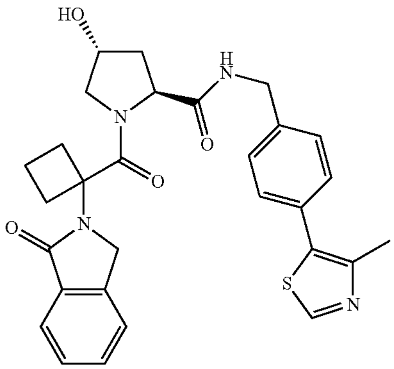
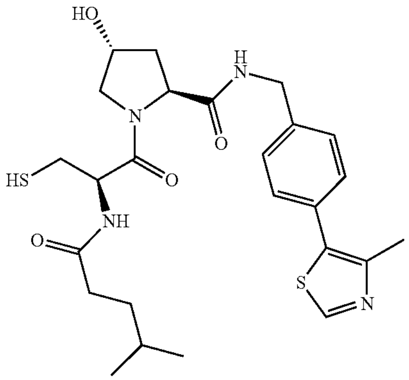
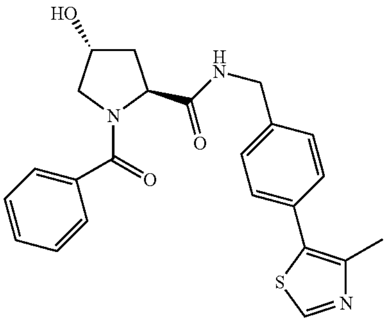
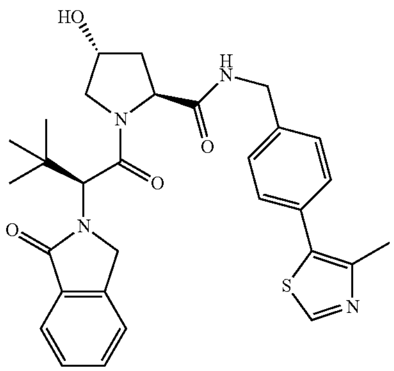
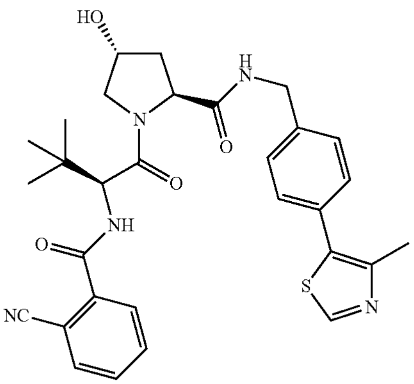

-continued
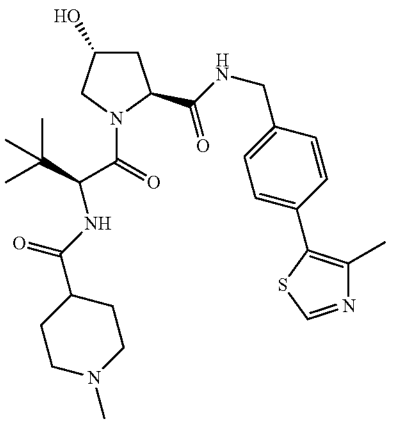
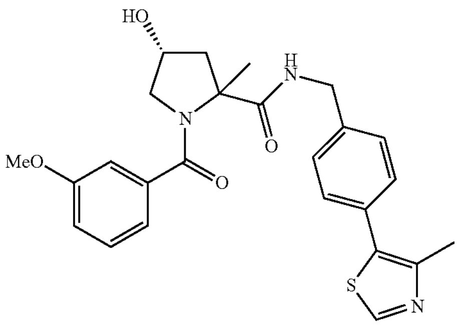
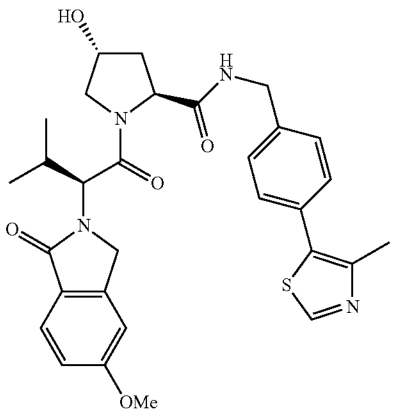
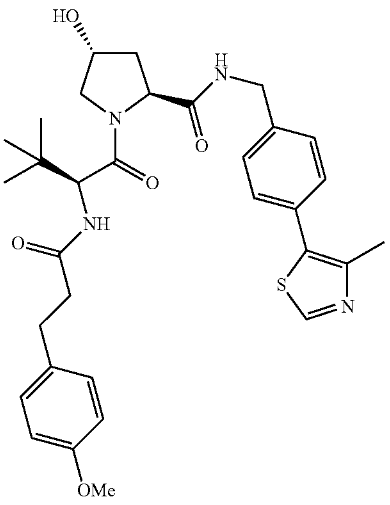
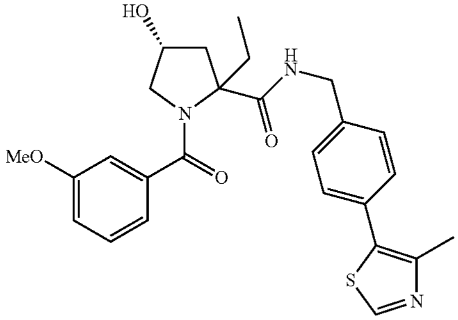
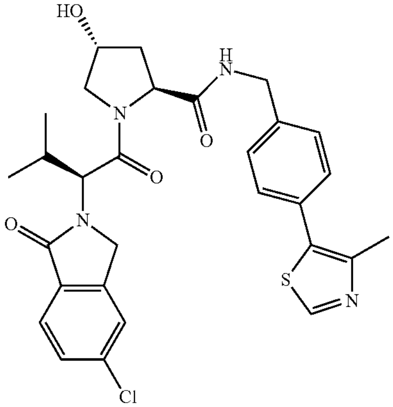

-continued
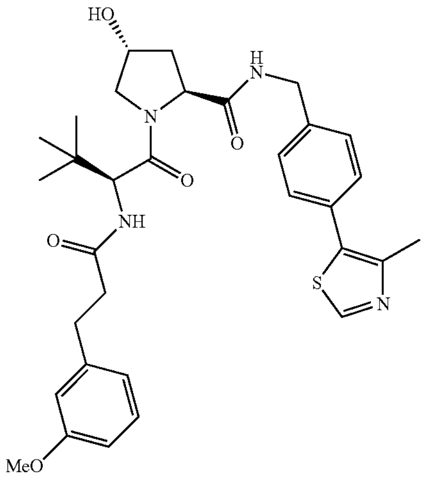
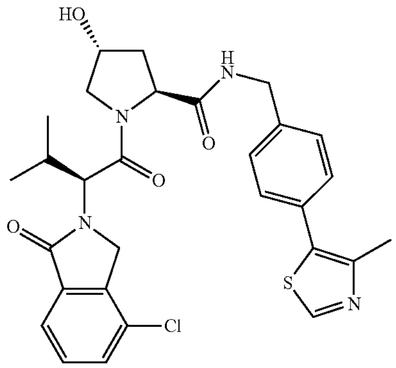
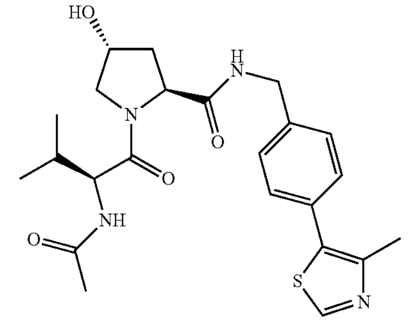
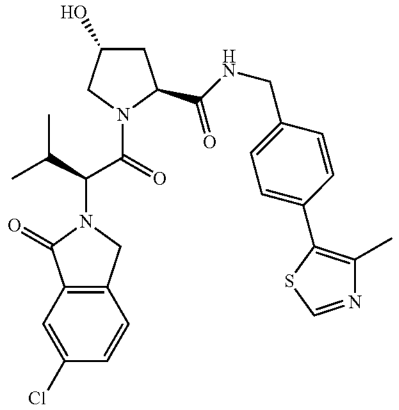
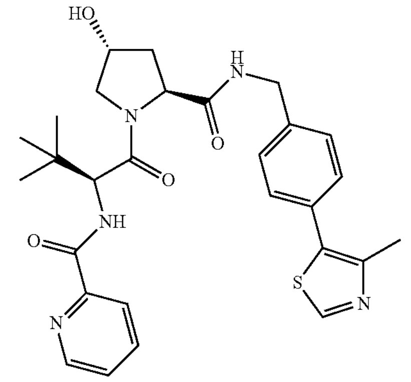
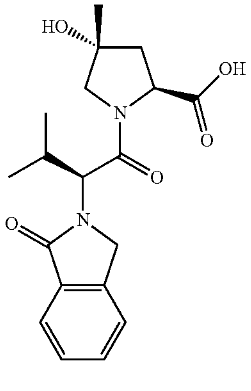
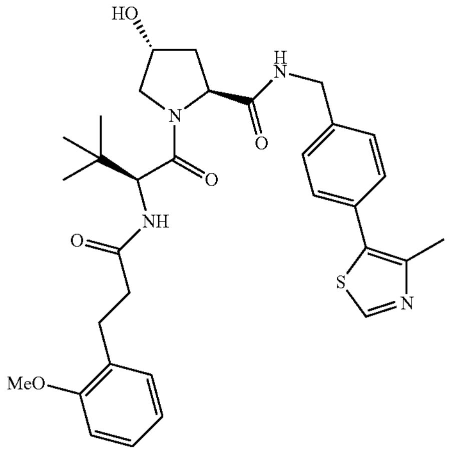
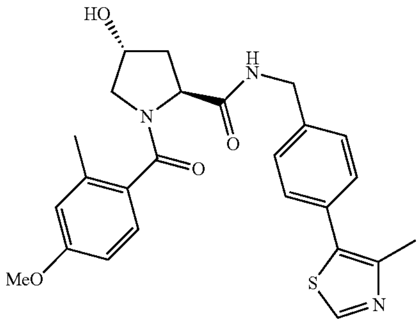
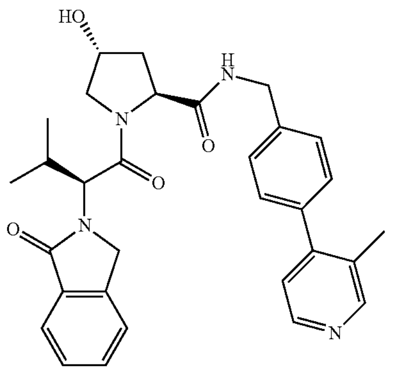

-continued
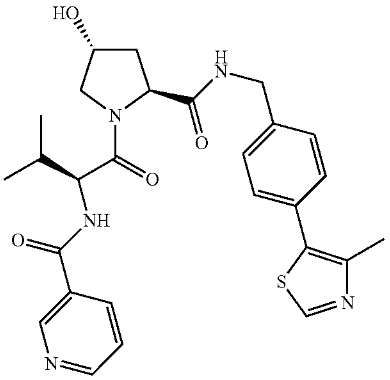
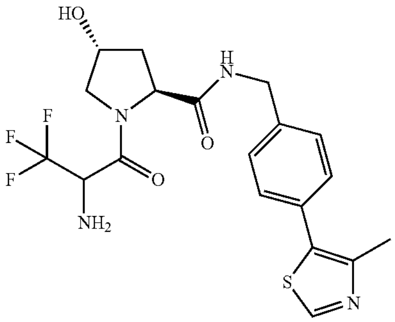
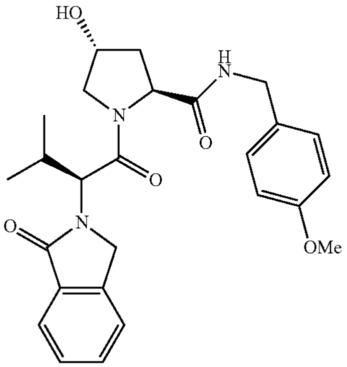
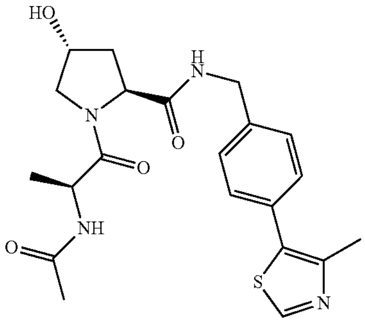
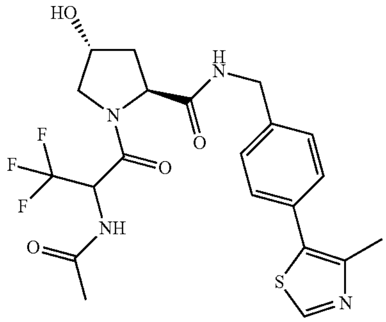
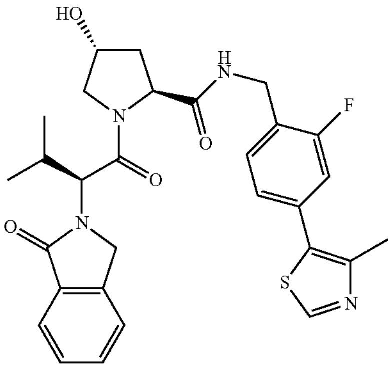
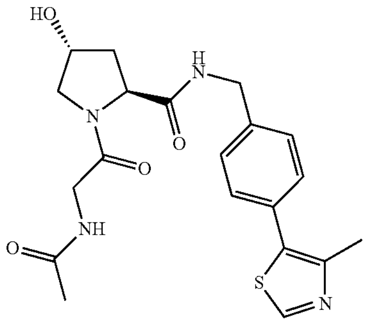
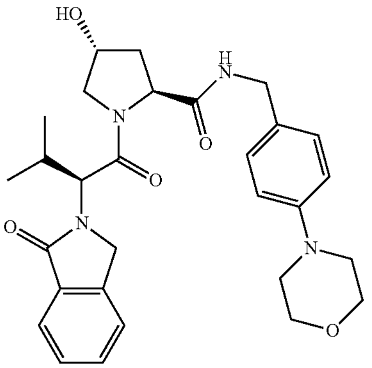
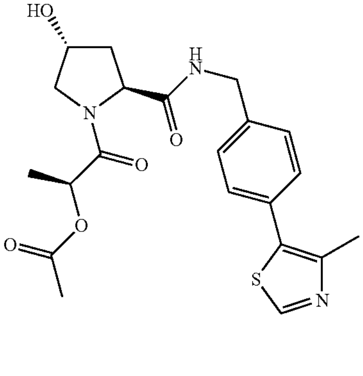
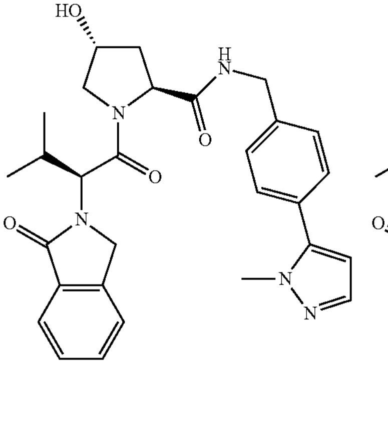
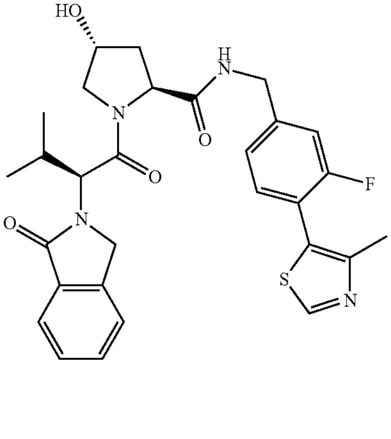

-continued
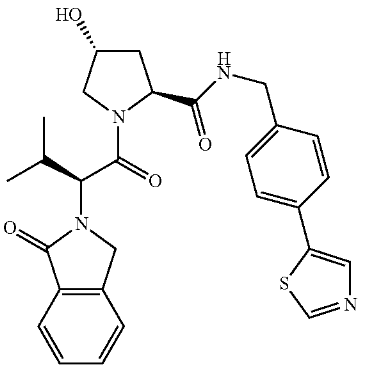
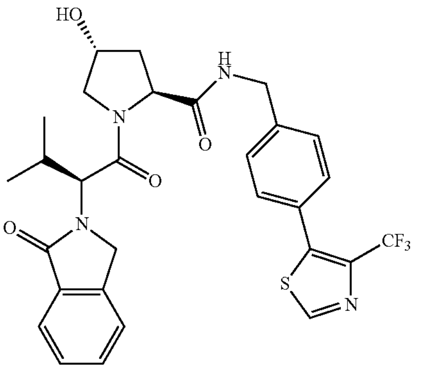
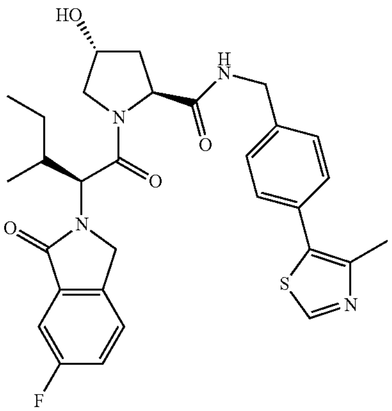
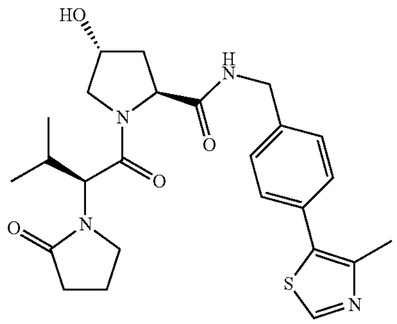
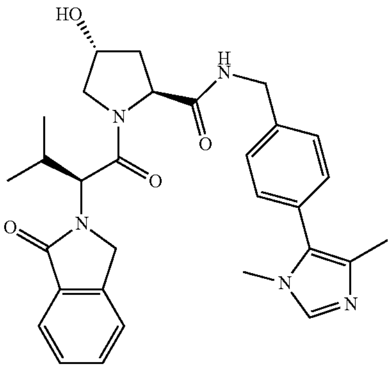
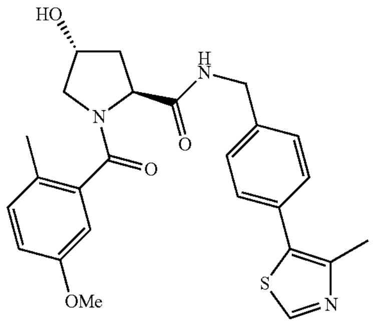
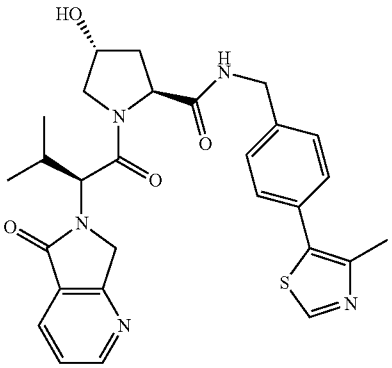
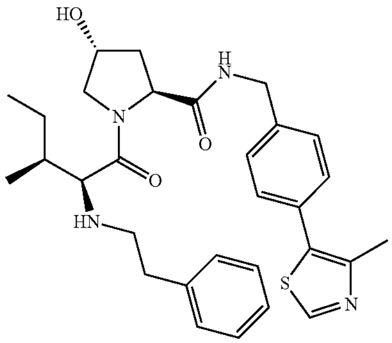

-continued
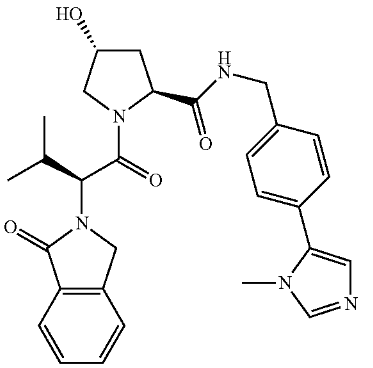
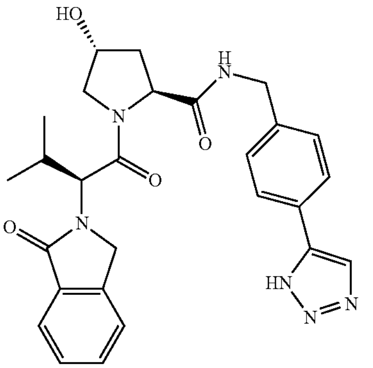
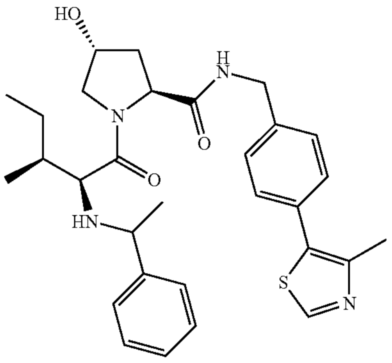
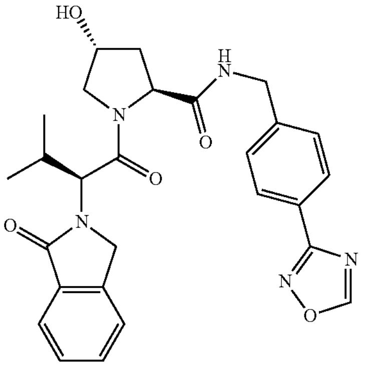
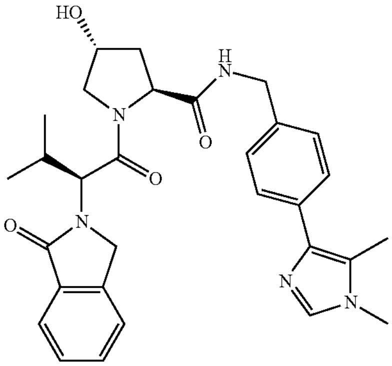
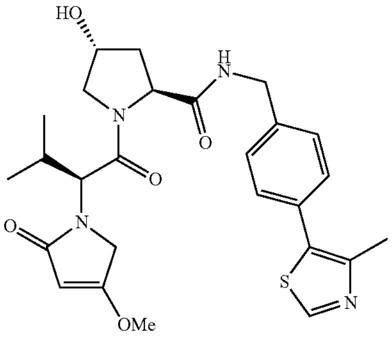
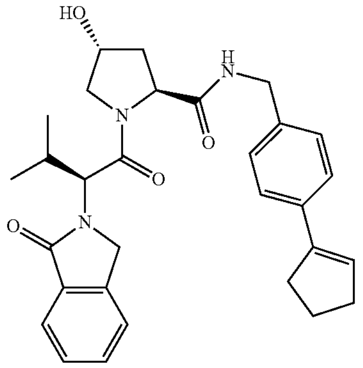
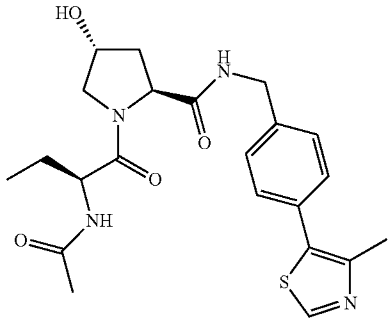
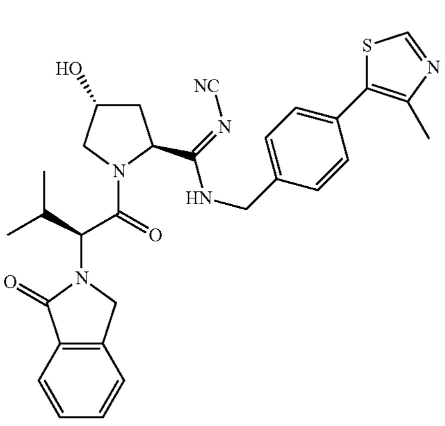
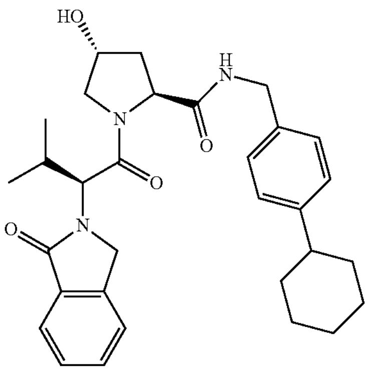

-continued
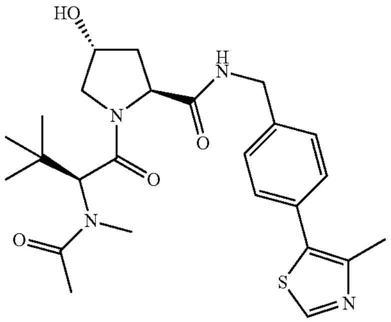
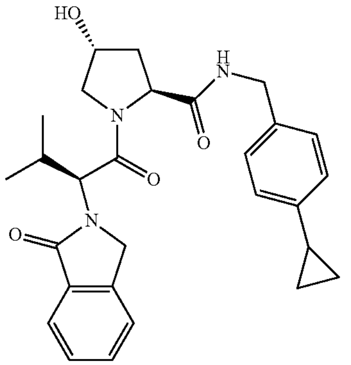
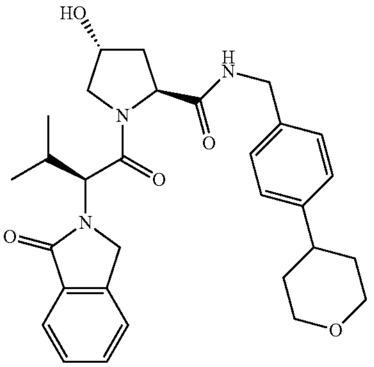
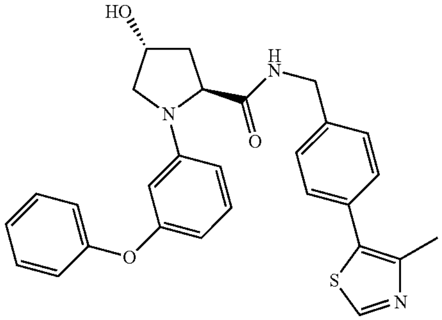
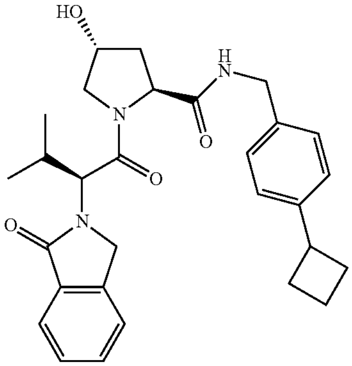
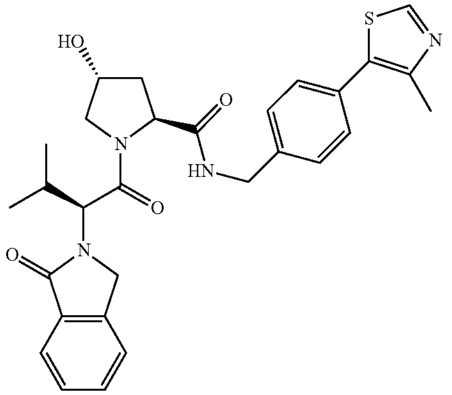
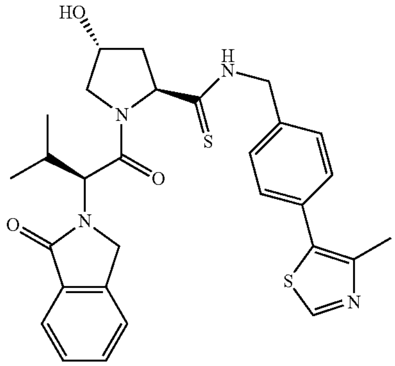
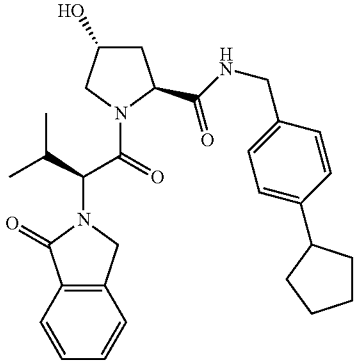
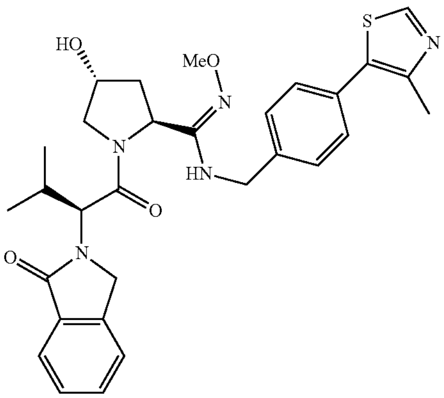

-continued
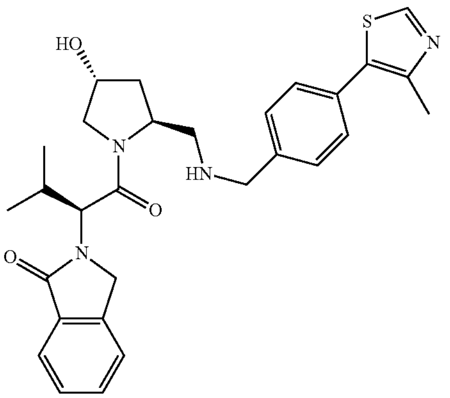
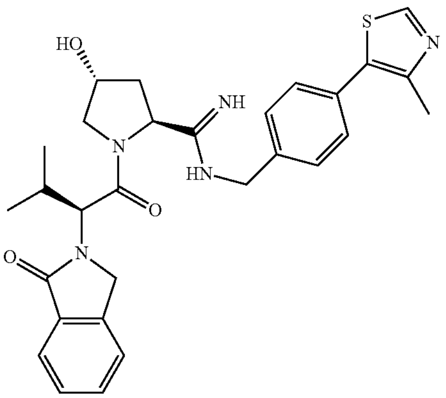
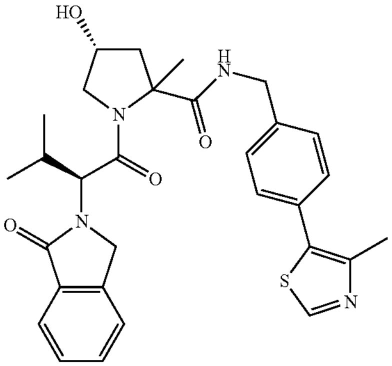
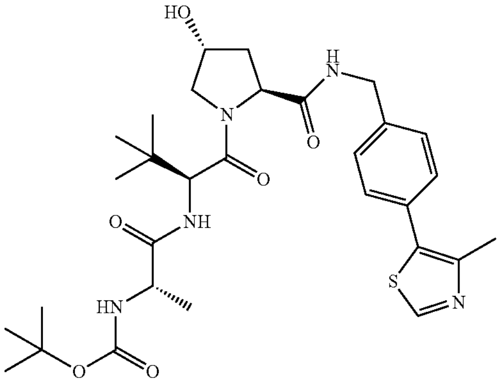
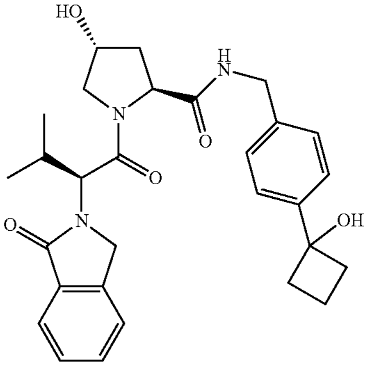
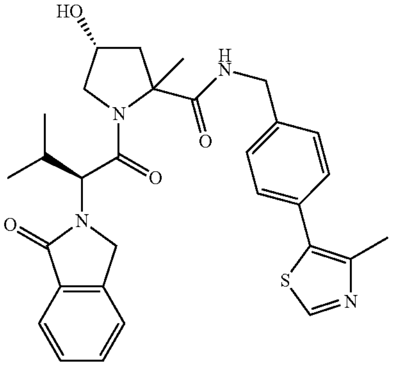
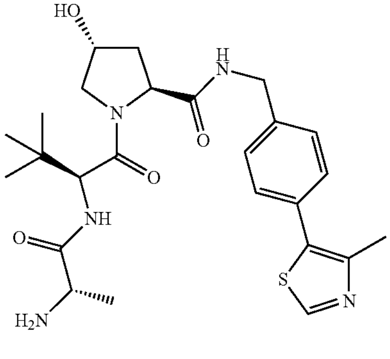
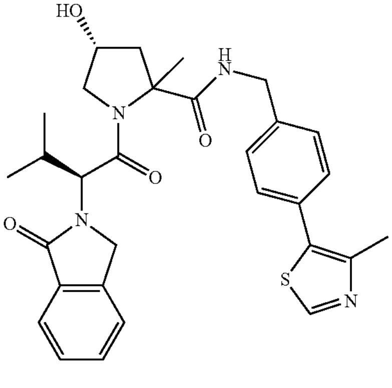

-continued
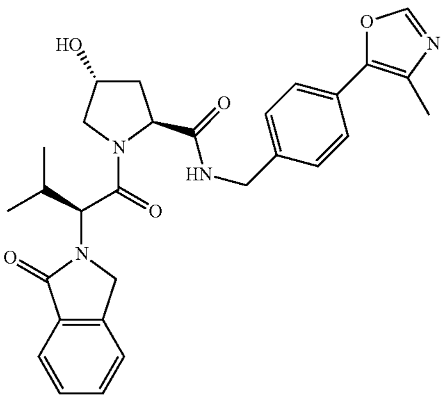
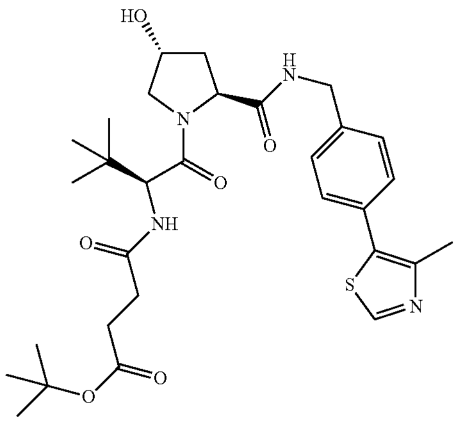
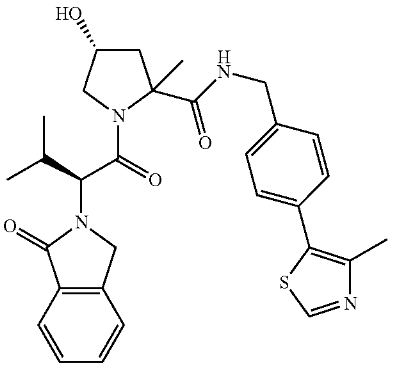
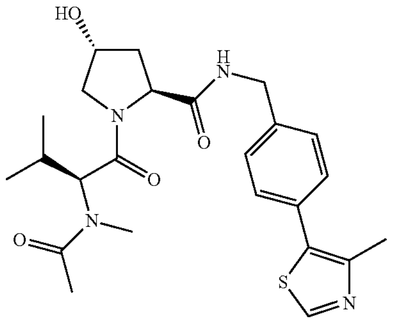
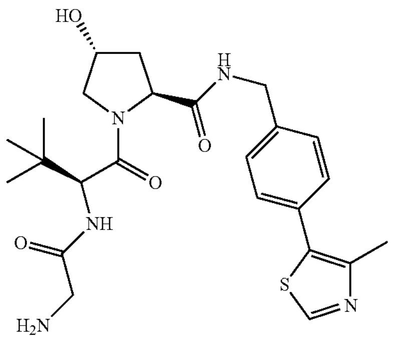
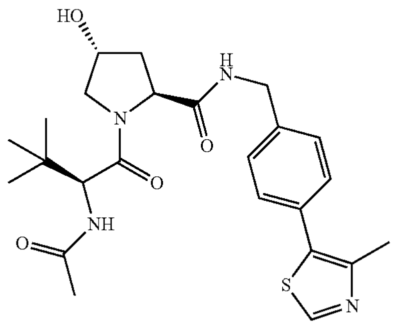
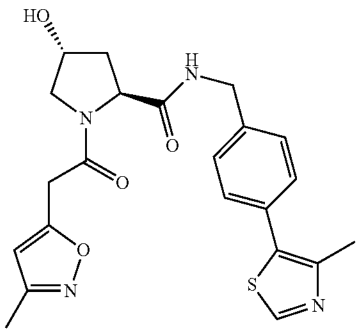
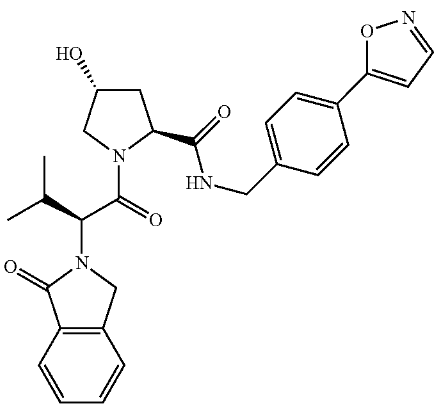
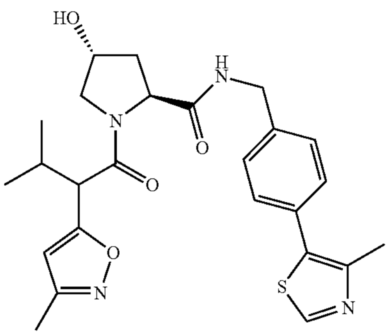

-continued
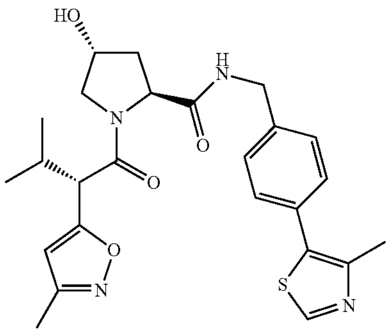
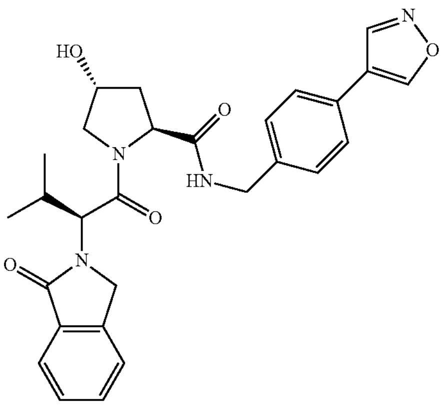
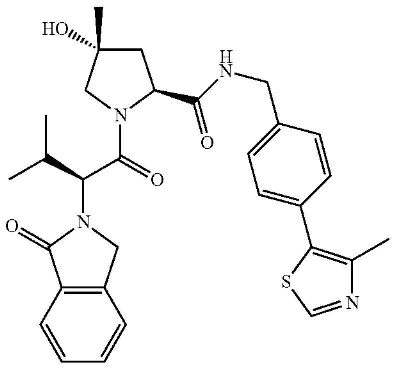
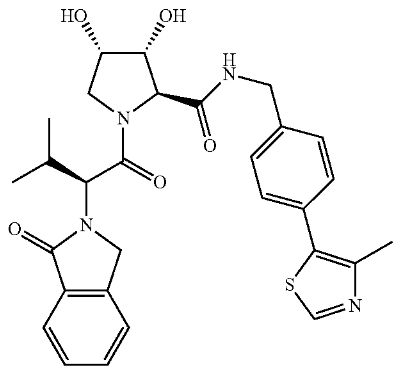
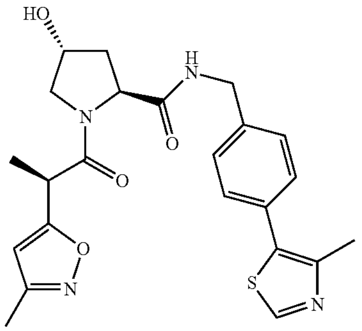
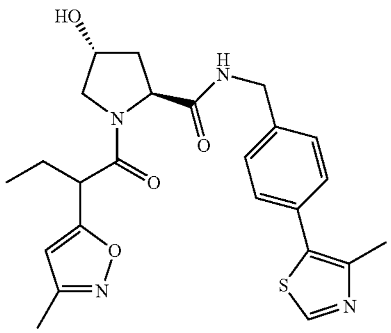
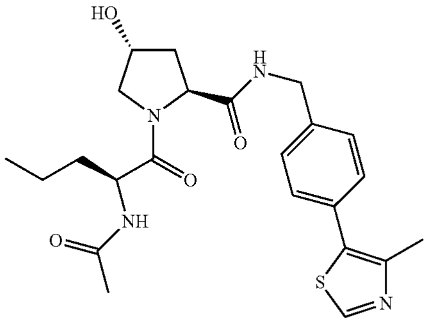
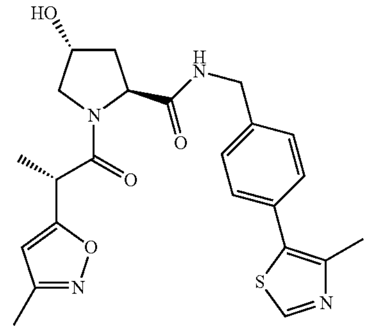

-continued
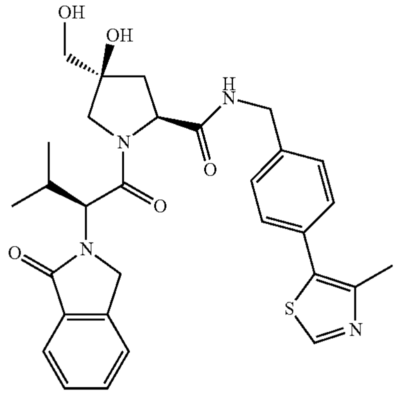
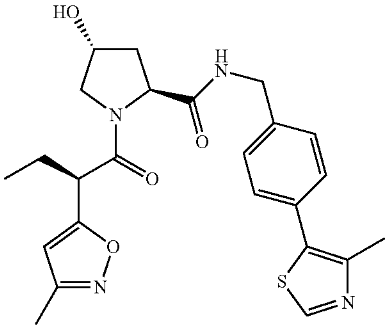
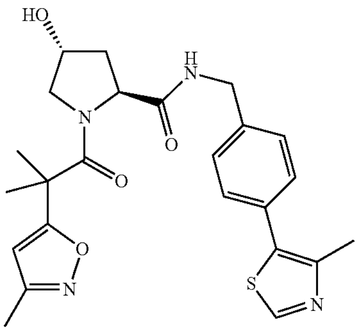
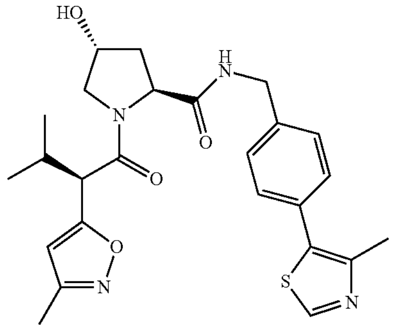
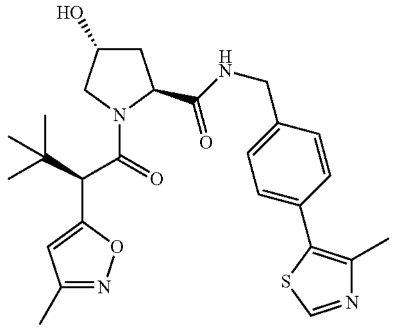
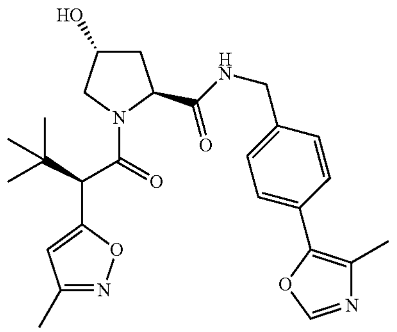
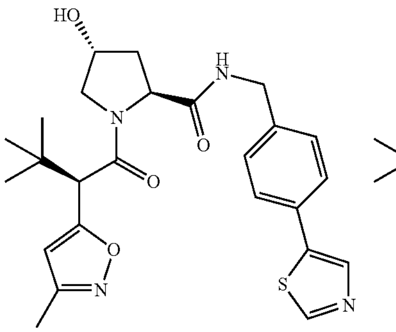
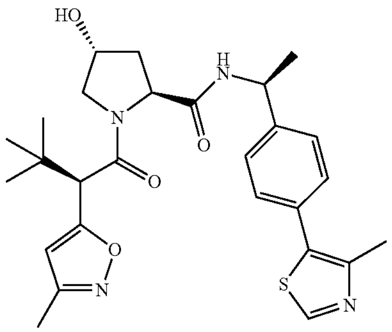
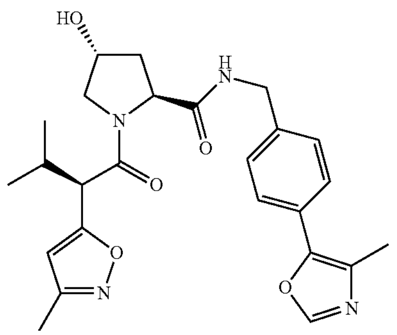
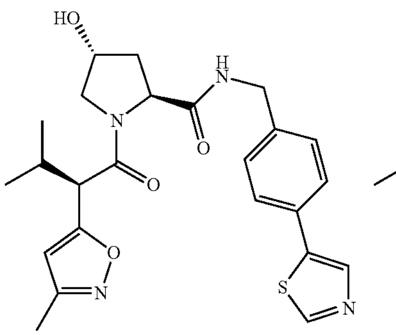
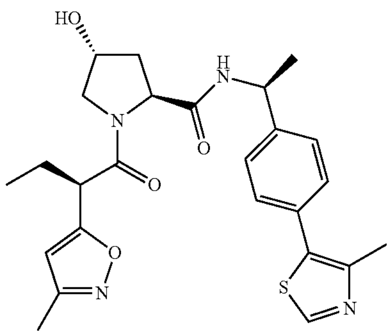
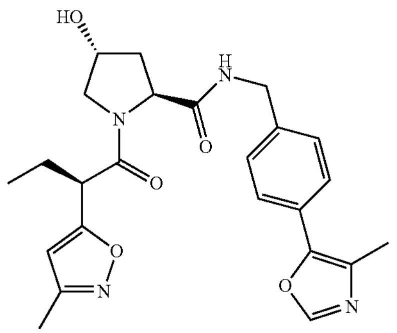
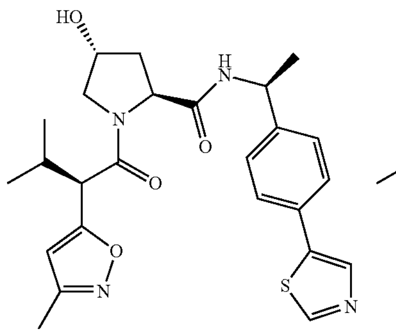
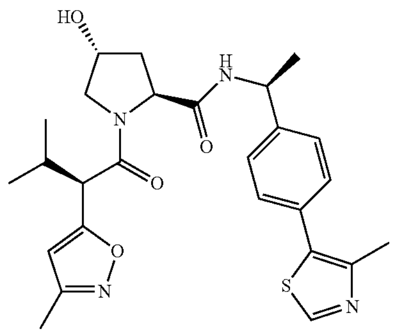

-continued
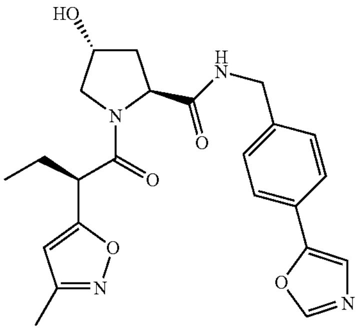
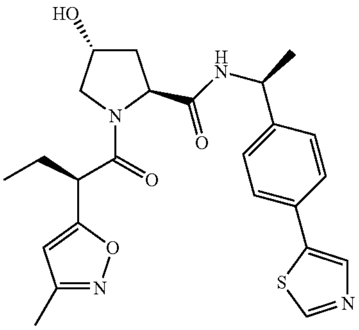
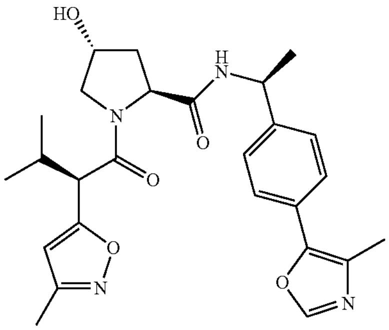
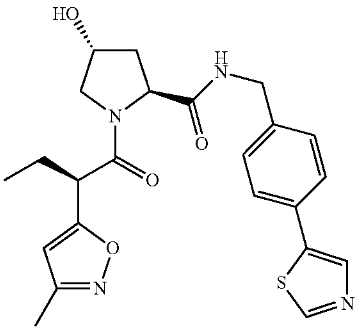
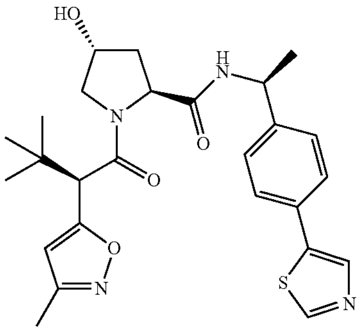
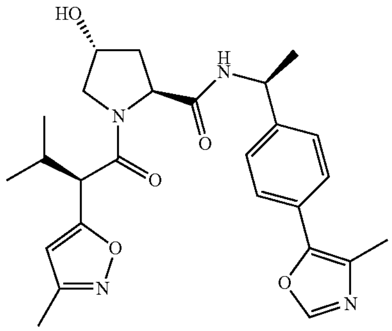
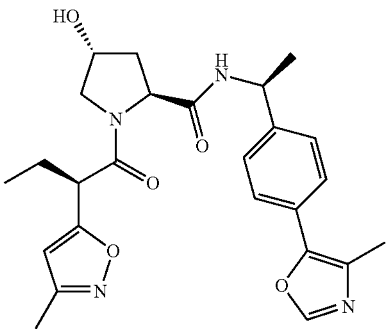
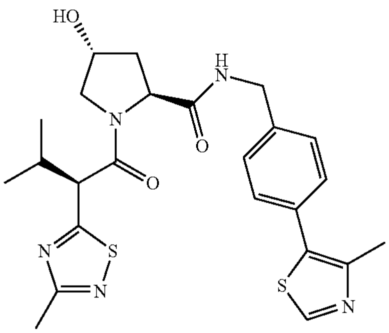
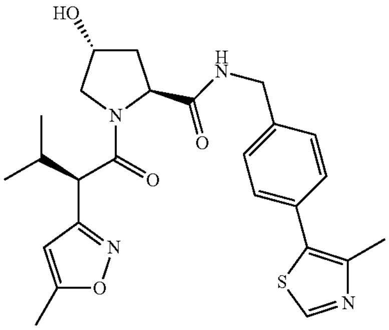
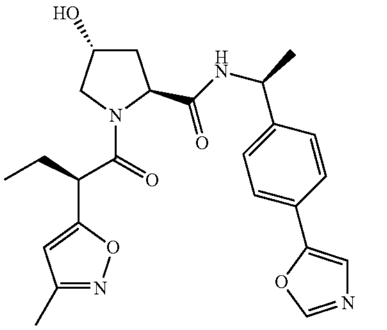
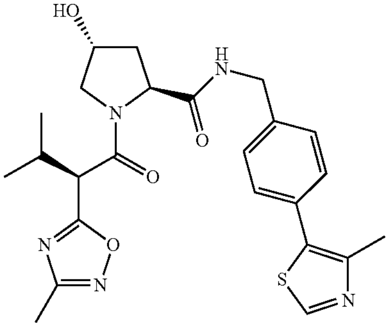
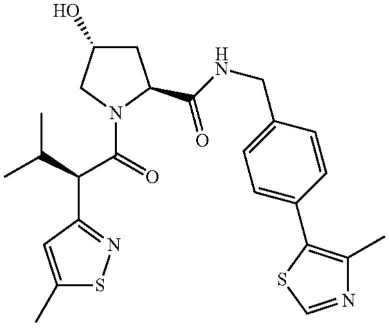

-continued
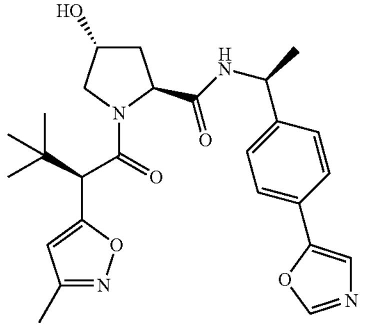
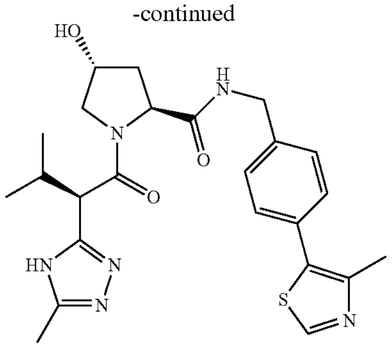
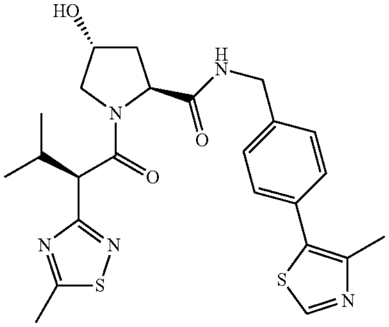
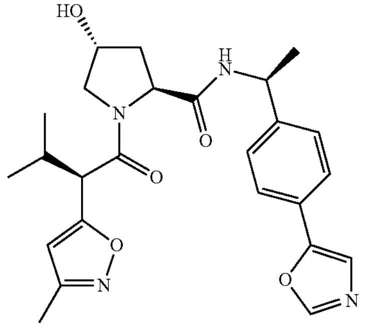
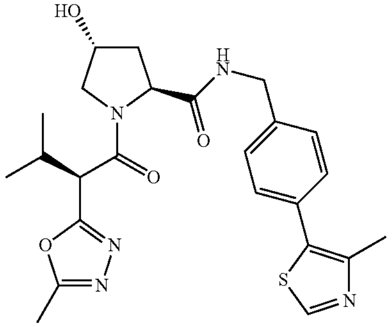
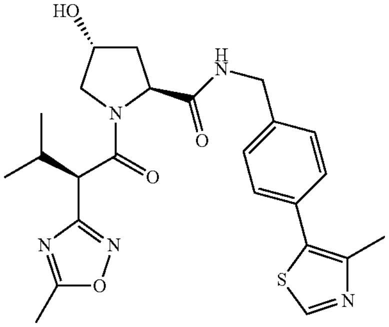
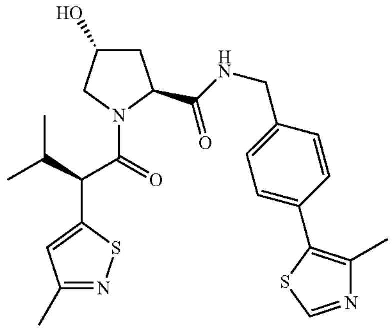
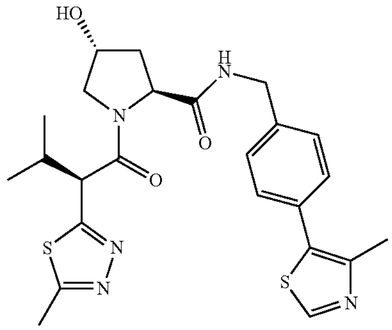
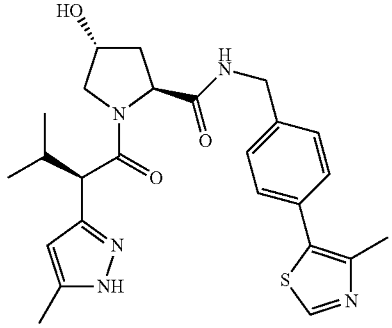
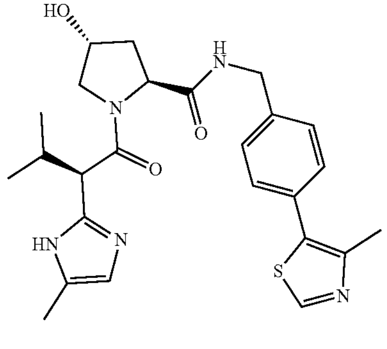
-continued
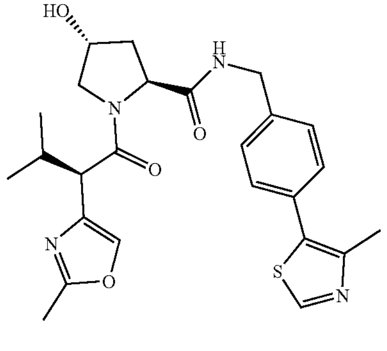

-continued
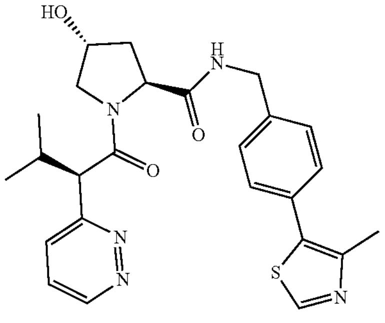
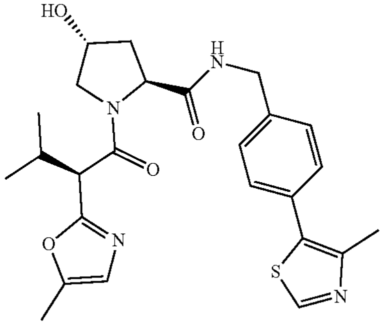
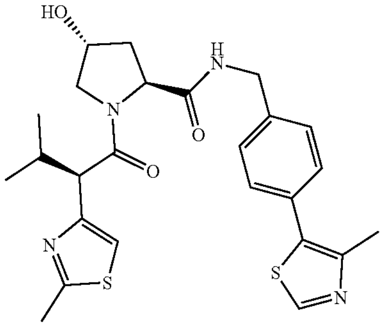
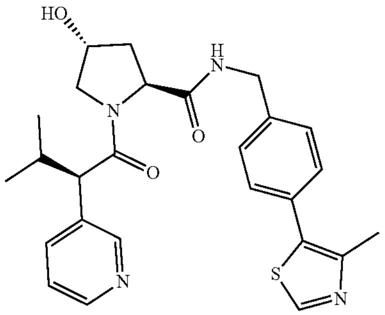
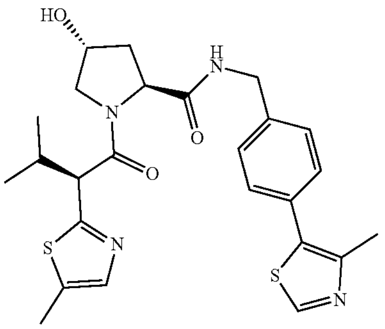
-continued
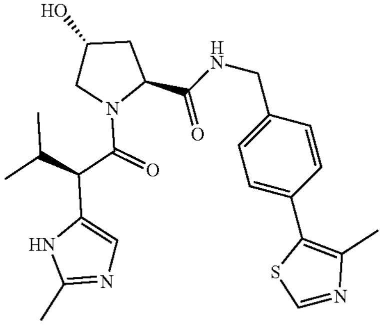
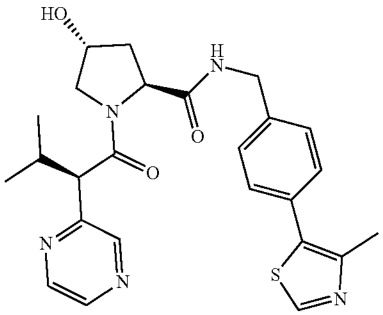
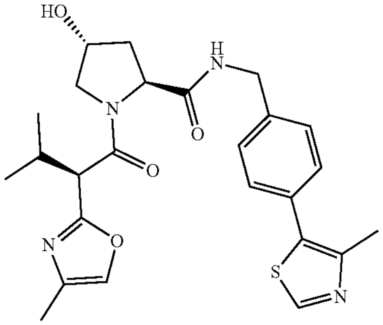
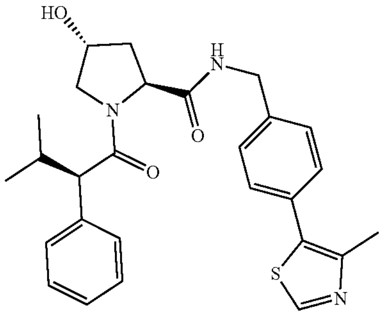
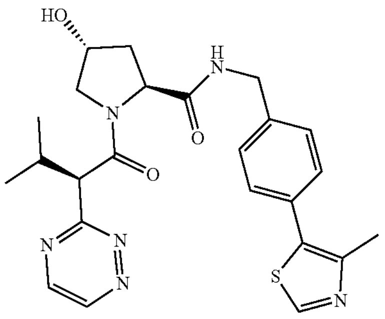

-continued
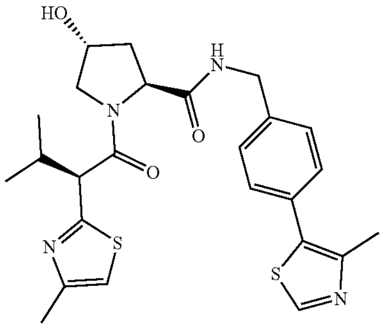
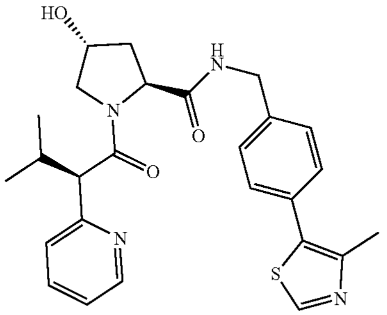
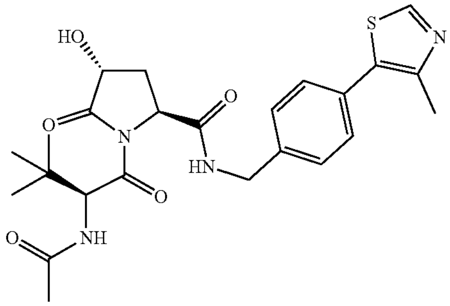
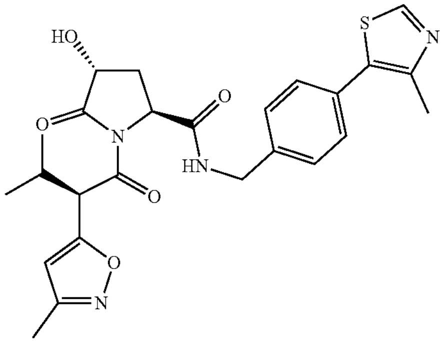
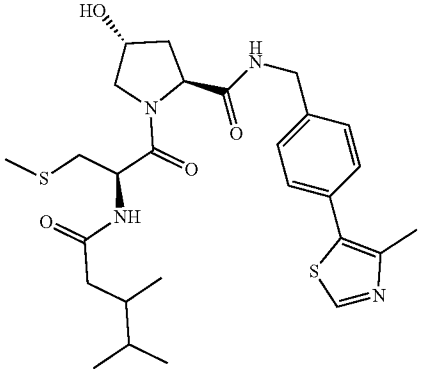
-continued
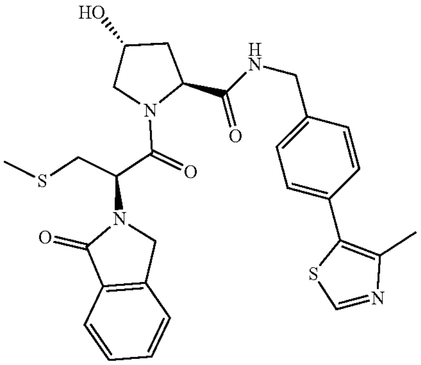
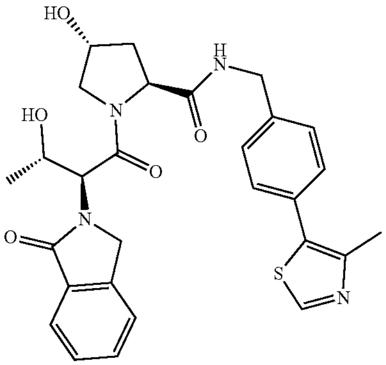
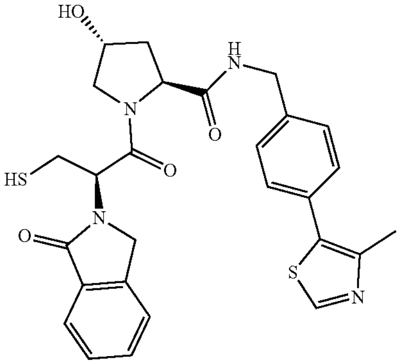
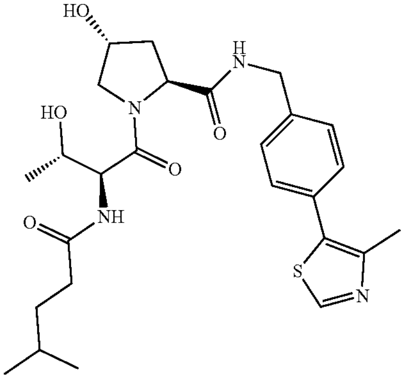

-continued
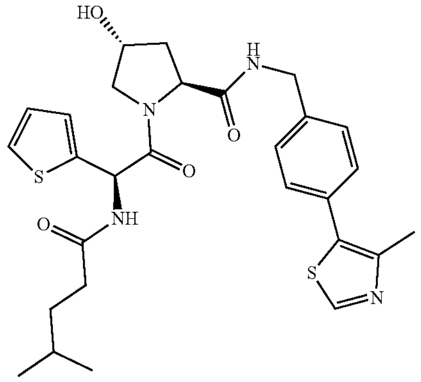
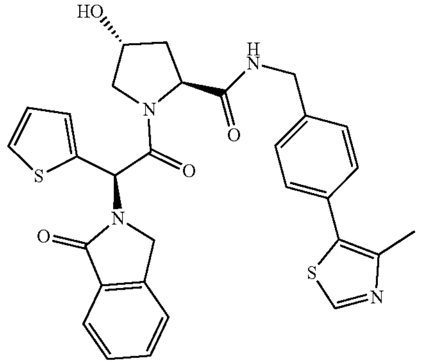
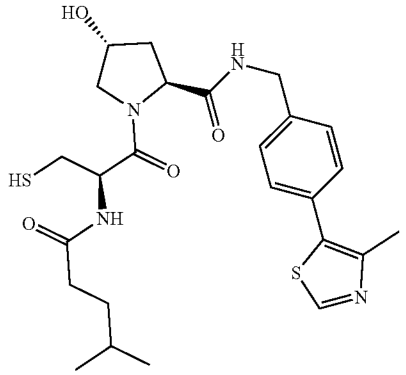
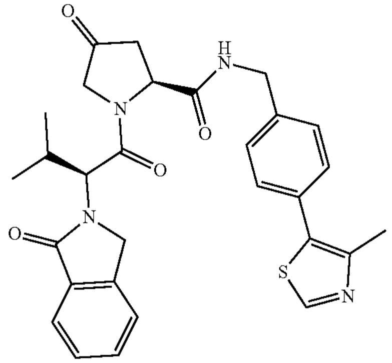
-continued
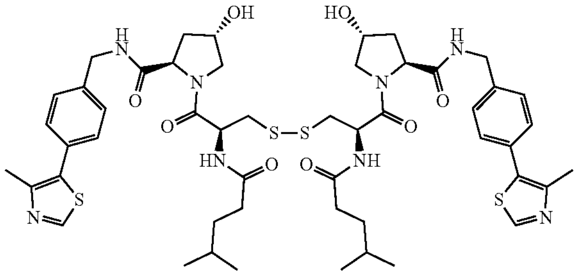
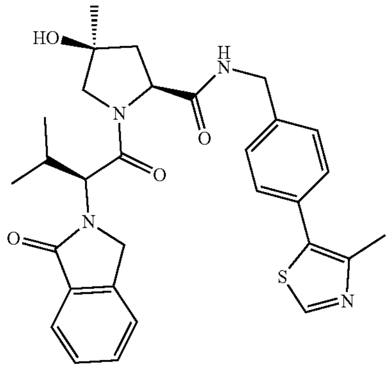
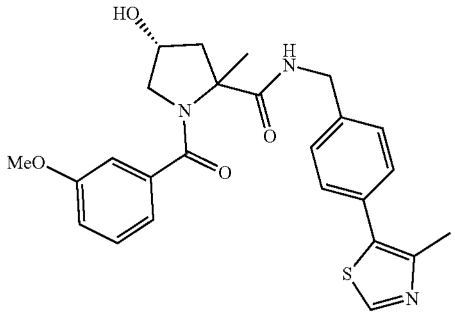
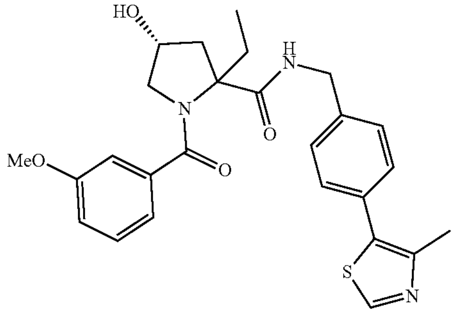
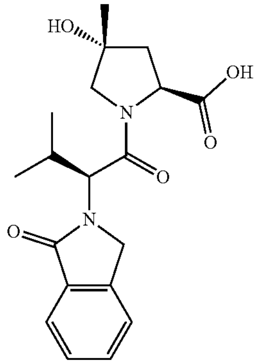

-continued
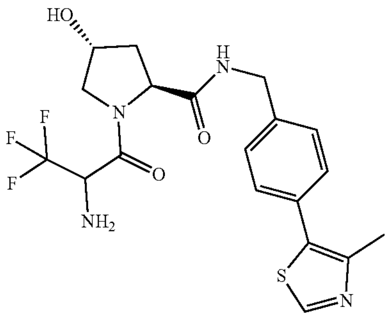
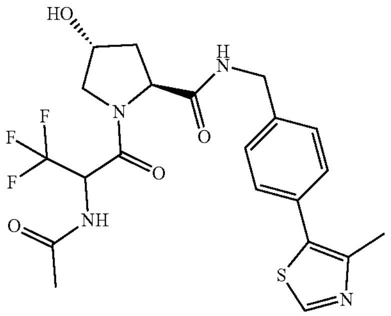
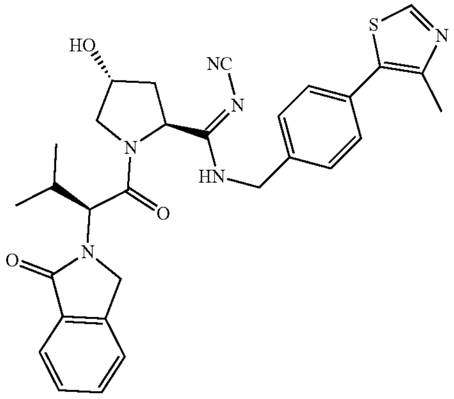
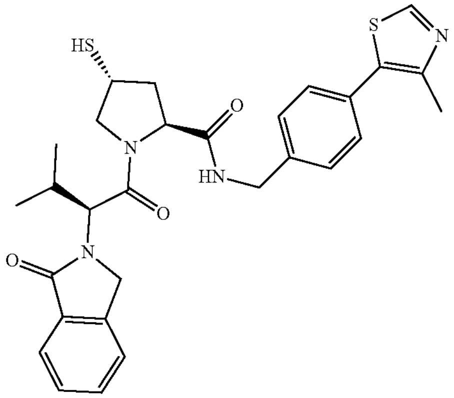
-continued
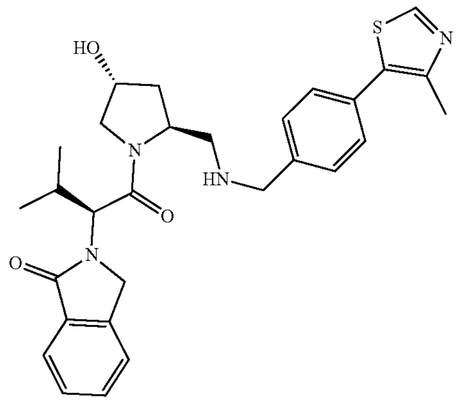
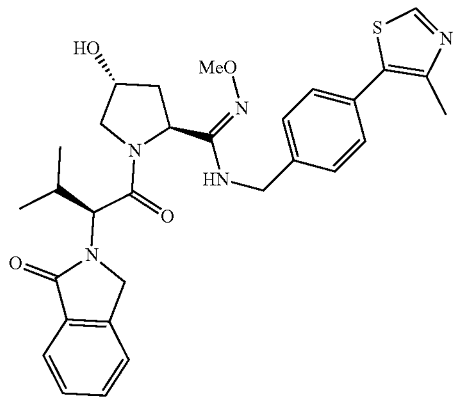
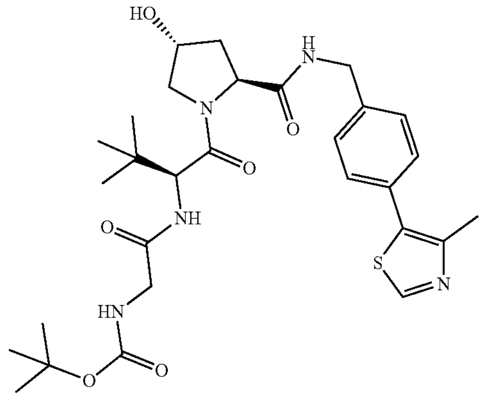
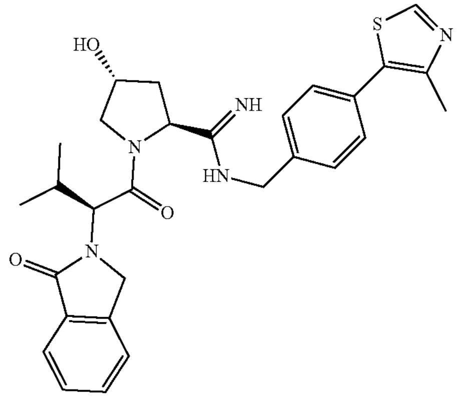

-continued
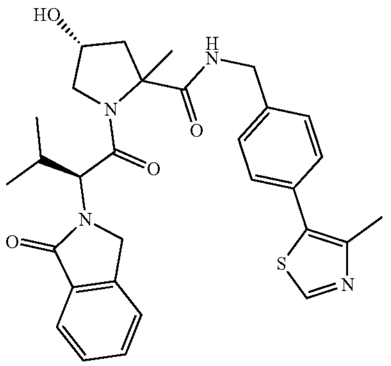
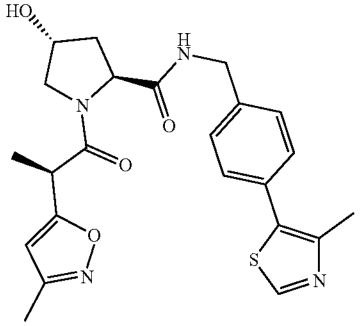
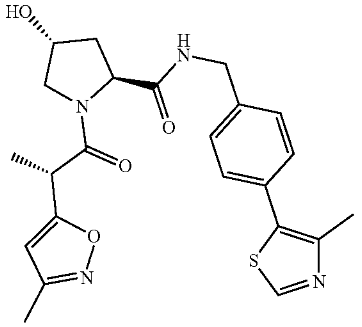
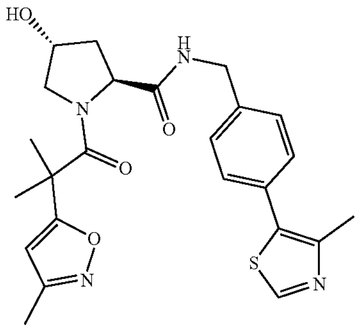
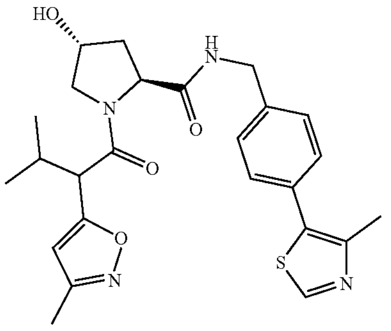
-continued
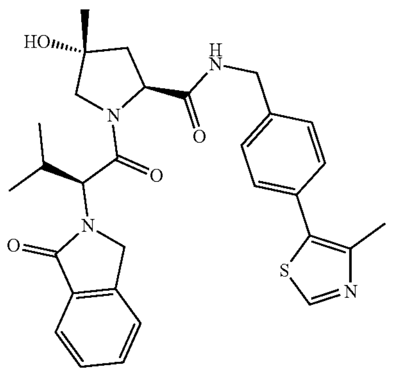
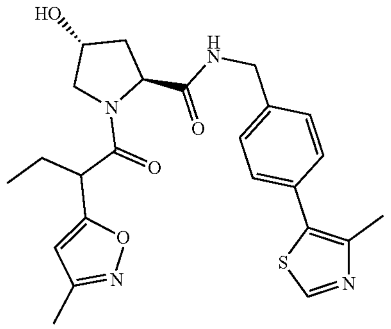
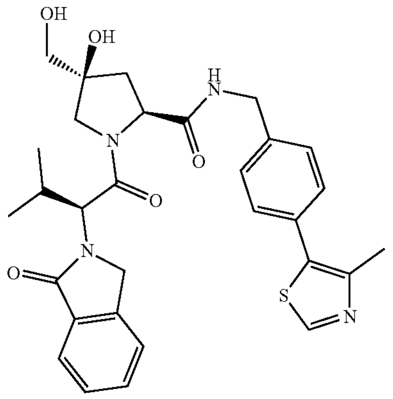
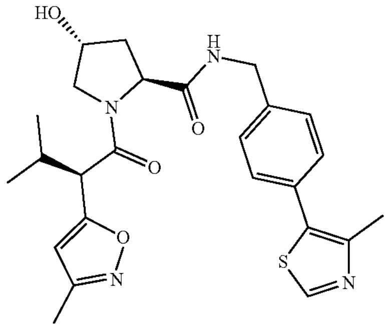

-continued
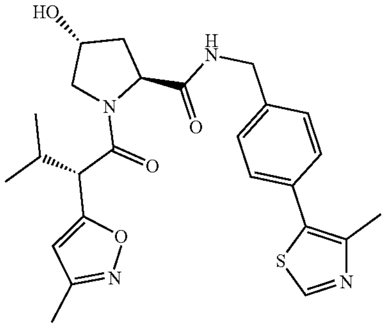
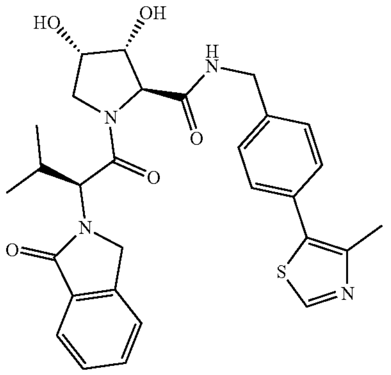
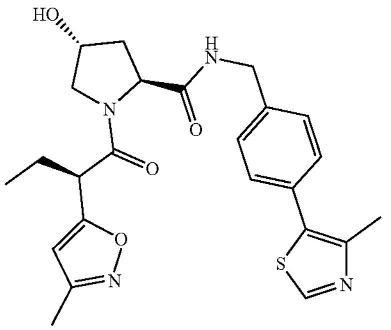
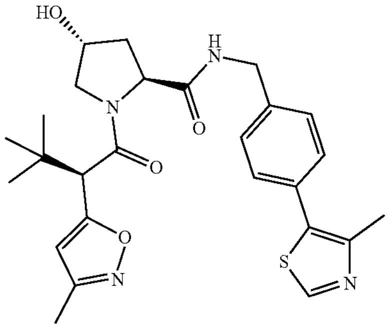
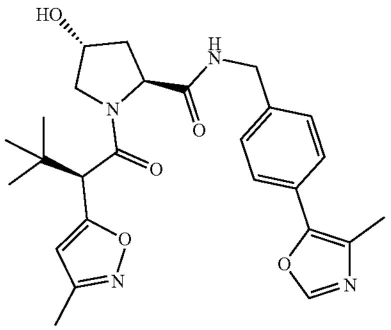
-continued
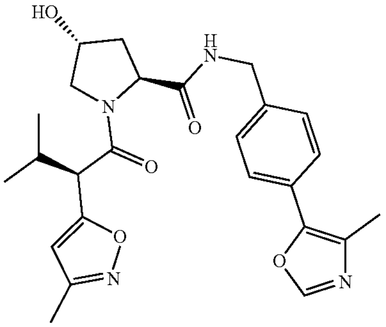
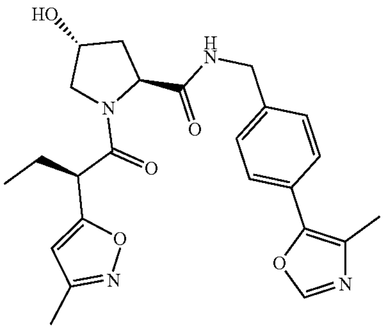
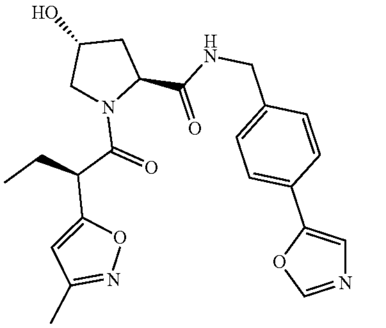
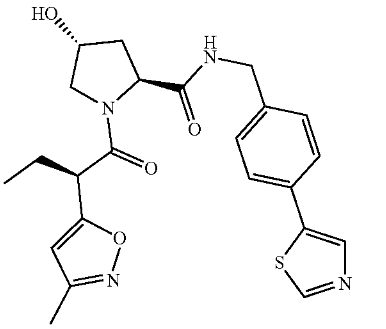
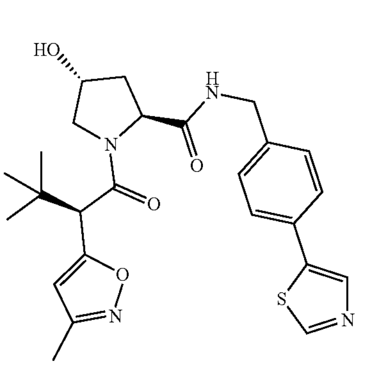

-continued
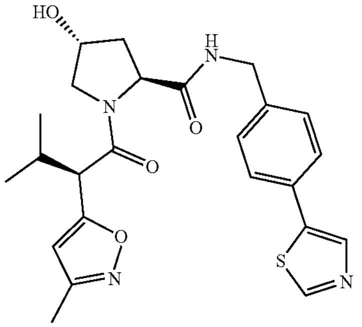
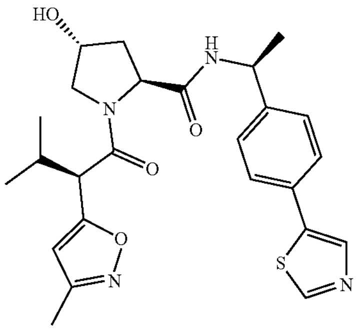
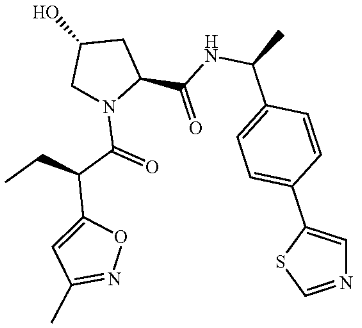
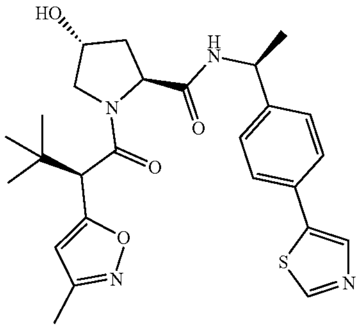
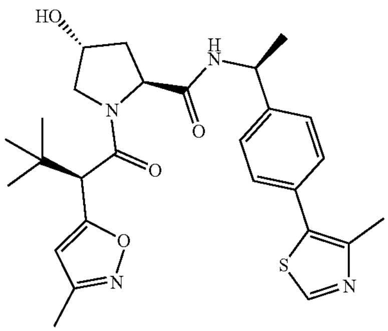
-continued
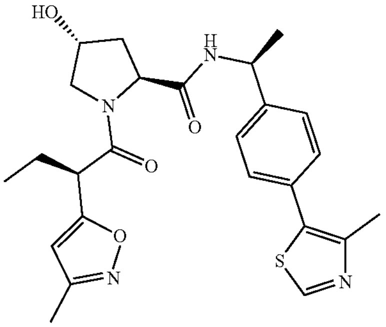
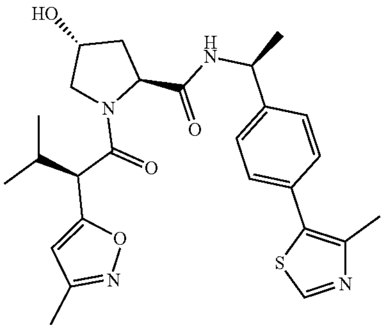
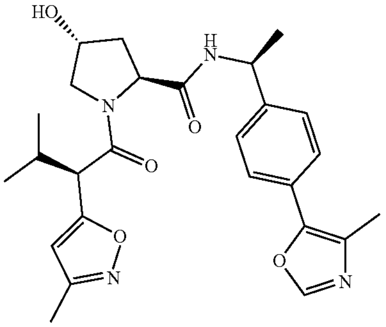
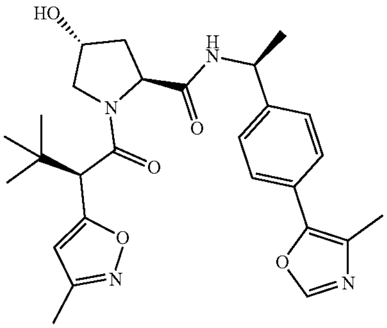
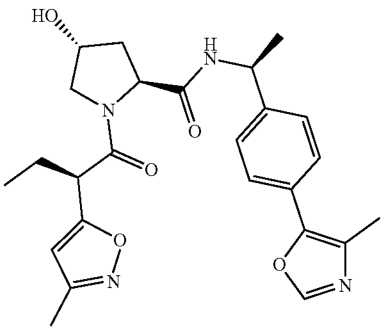

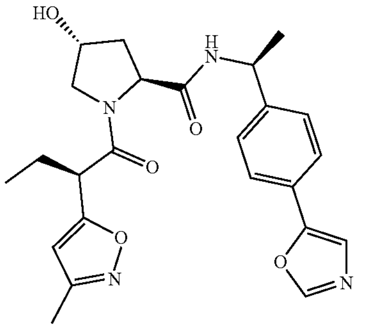
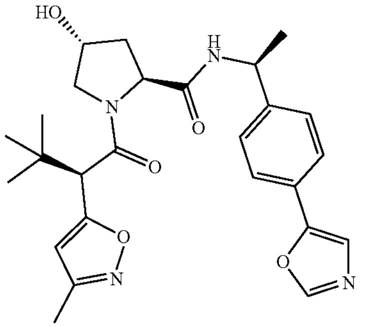
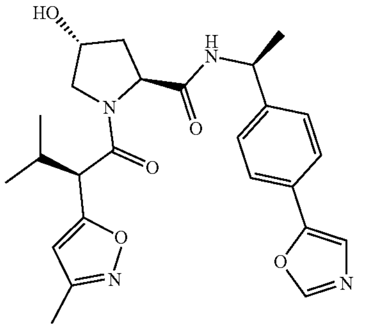
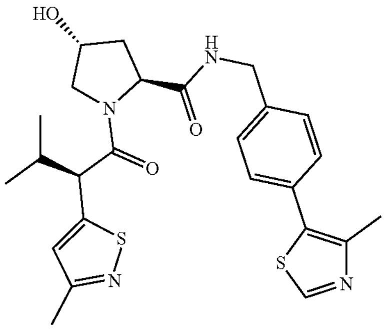
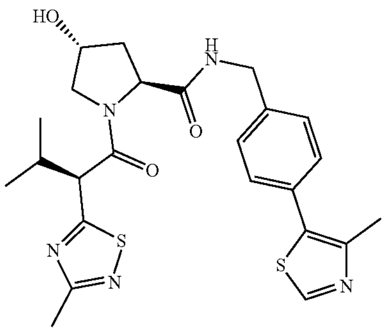
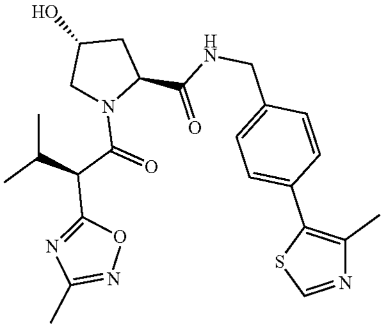
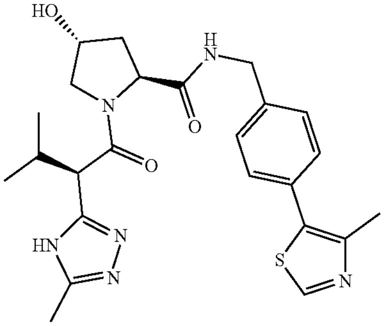
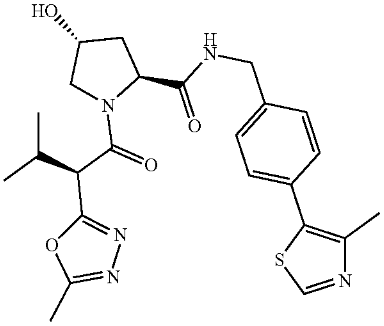
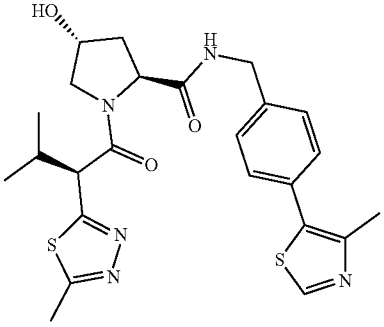
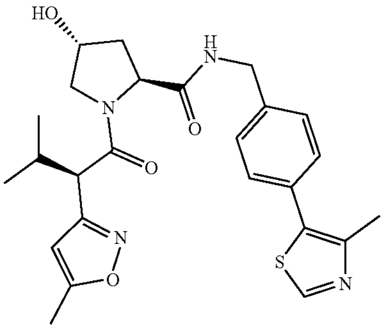

-continued
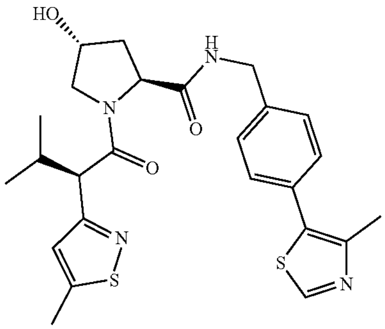
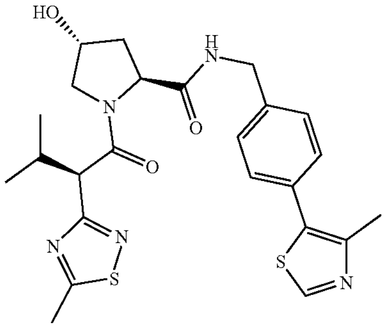
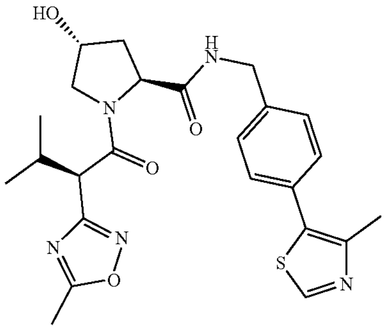
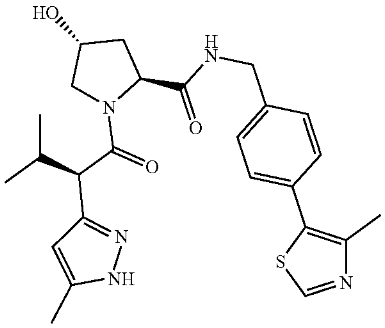
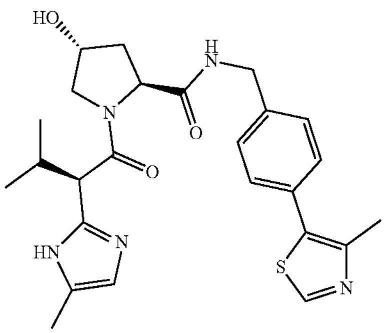
-continued
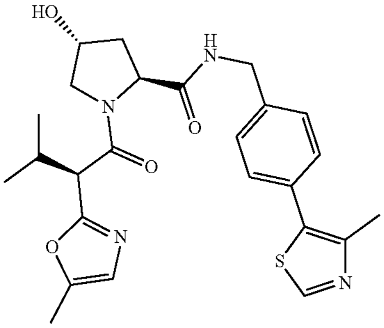
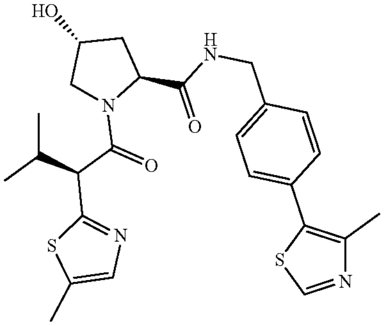
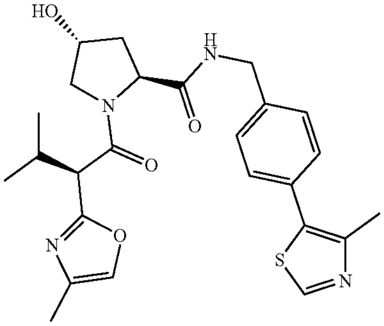
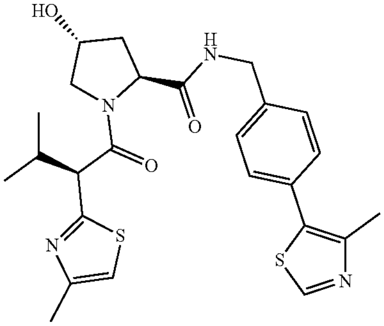
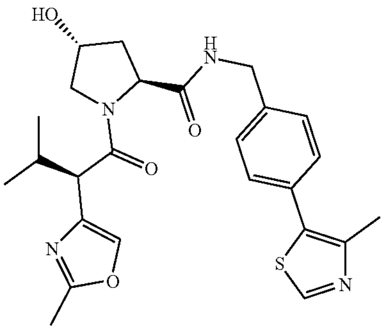

-continued
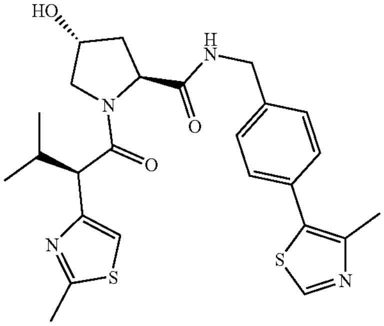
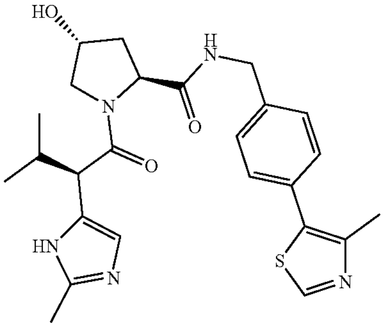
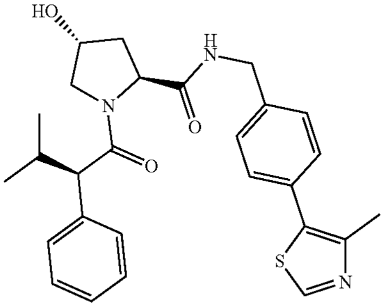
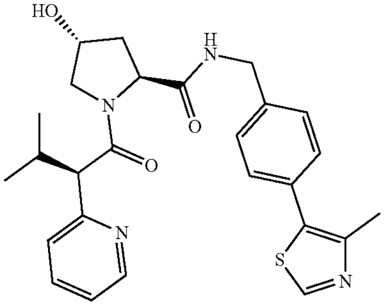
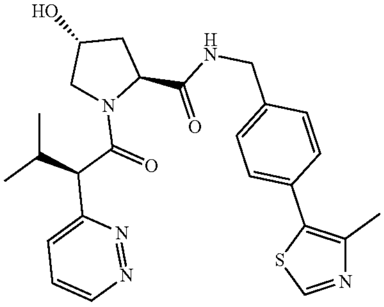
-continued
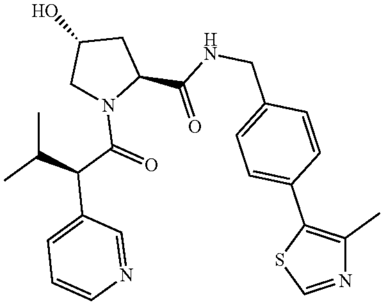
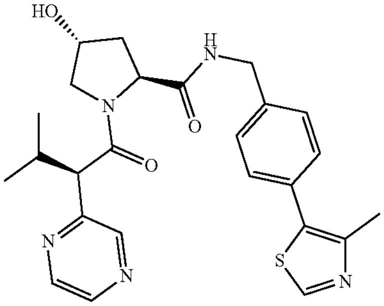
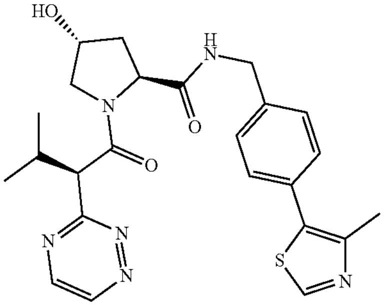
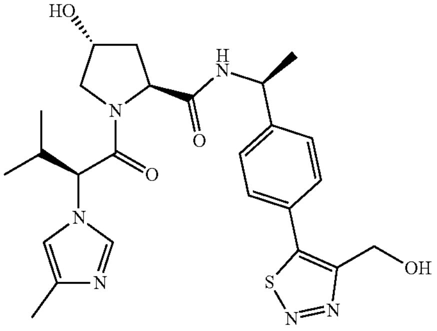
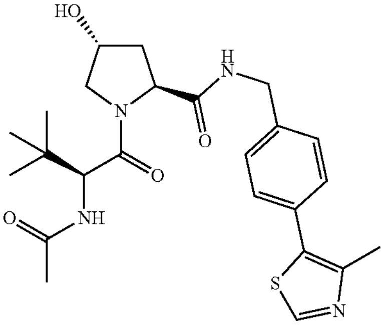

-continued
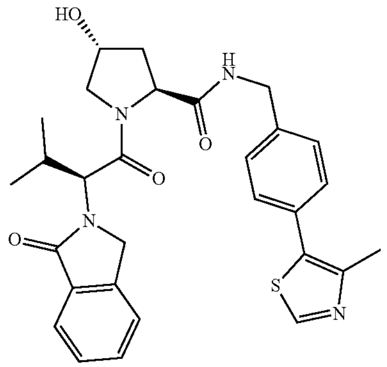
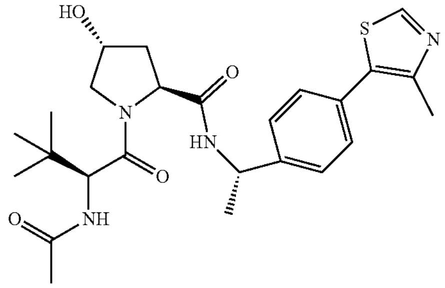
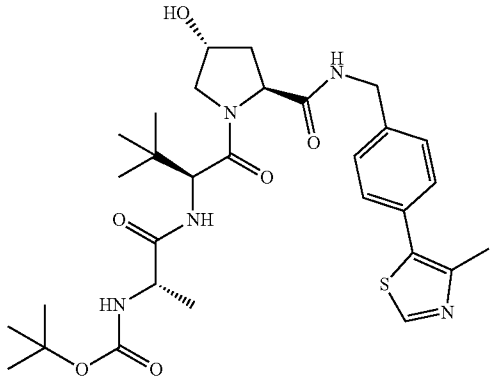
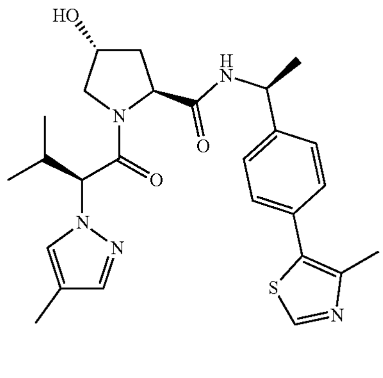
-continued
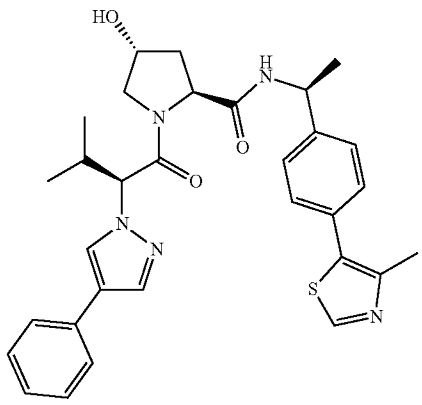
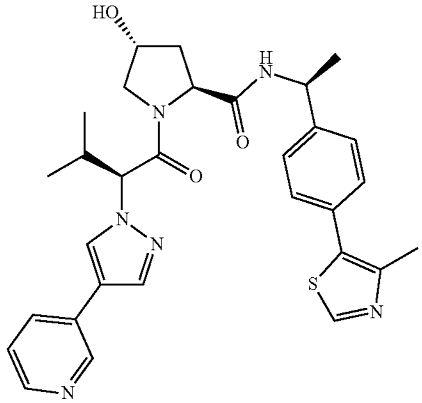
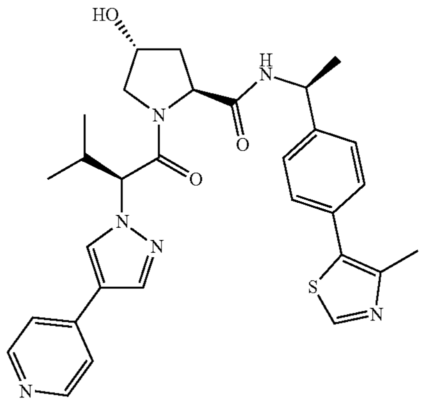
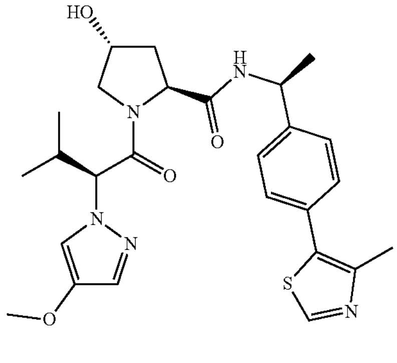

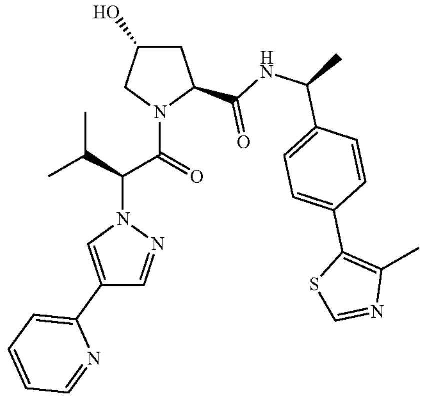
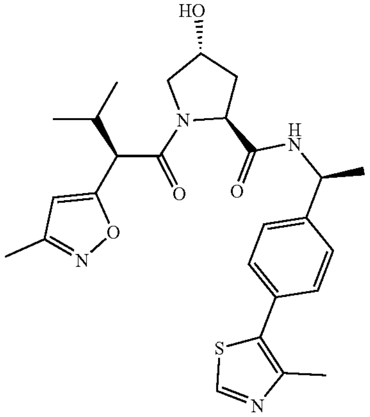
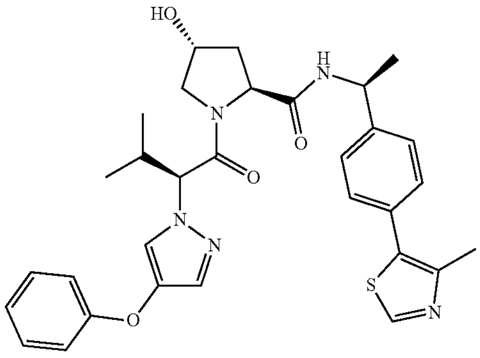
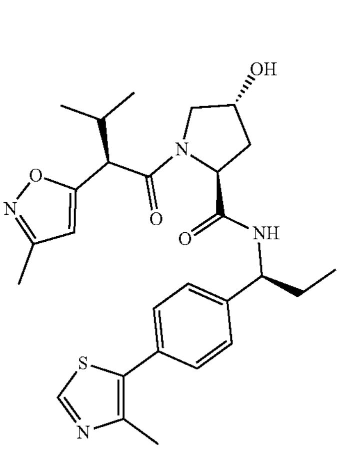
,
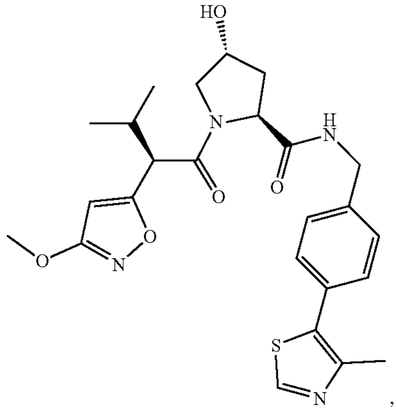
,
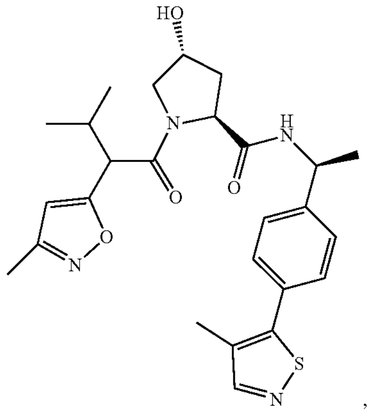
,
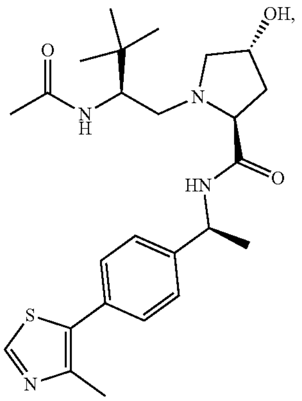
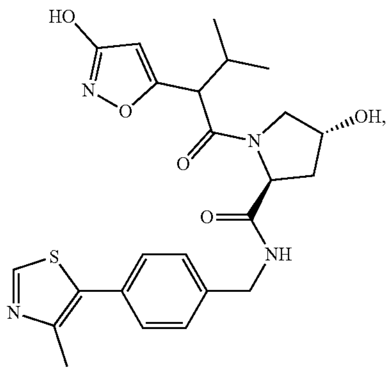

-continued

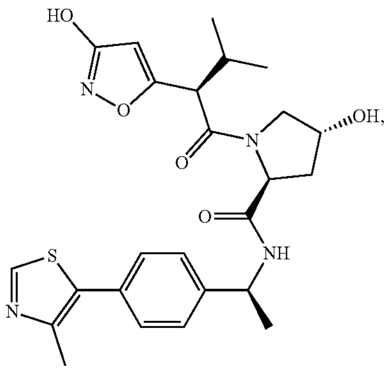

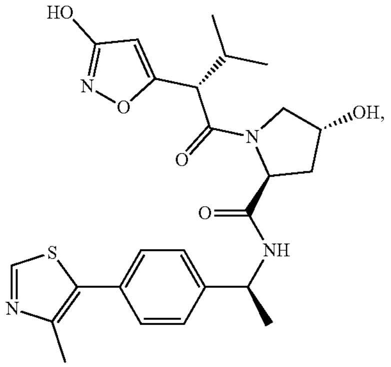

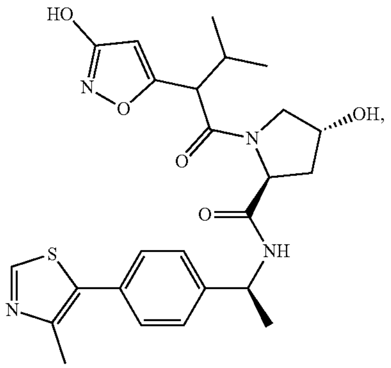

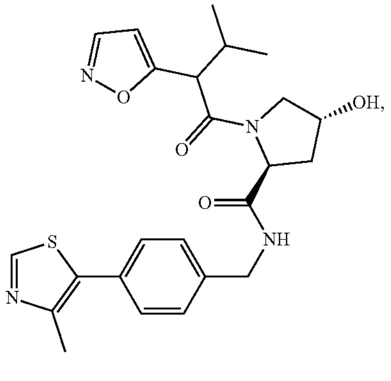

-continued

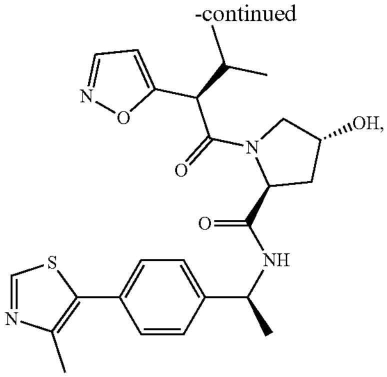

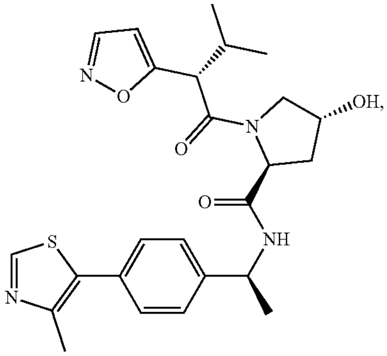

and

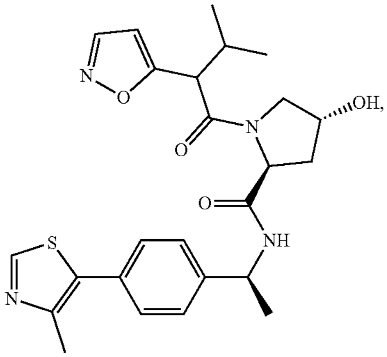

wherein the VLM may be connected to a PTM via a linker, as described herein, at any appropriate location, including, e.g., an aryl, heteroaryl, phenyl, or phenyl of an indole group, optionally via any appropriate functional group, such as an amine, ester, ether, alkyl, or alkoxy.

Exemplary Linkers

In certain embodiments, the compounds as described herein include a means for chemically coupling the PTM to the ULM, e.g., one or more PTMs chemically linked or coupled to one or more ULMs (e.g., at least one of VLM) via a chemical linker (L). In certain embodiments, the linker group L is a group comprising one or more covalently connected structural units (e.g., $-A^L_1 \ldots (A^L)_q-$ or $-(A^L)_q-$), wherein $A^L_1$ is a group coupled to PTM, and $(A^L)_q$ is a group coupled to ULM.

In any aspect or embodiment described herein, the linker (L) to ULM (e.g., VLM, ILM, CLM, or MLM) connection or coupling is a stable L-ULM connection. For example, in any aspect or embodiment described herein, when a linker (L) and a ULM is connected via a heteroatom, any subsequent heteroatom, if present, is separated by at least one single carbon atom (e.g., $-CH_2-$), such as with an acetal or aminal group. By way of further example, in any aspect or embodiment described herein, when a linker (L) and a ULM is connected via a heteroatom, the heteroatom is not part of a ester.

In any aspect or embodiment described herein, the linker group L is a bond or a chemical linker group represented by the formula $-(A^L)_q-$, wherein A is a chemical moiety and q is an integer from 1-100, and wherein L is covalently bound to the PTM and the ULM, and provides for sufficient binding of the PTM to the protein target and the ULM to an E3 ubiquitin ligase to result in target protein ubiquitination.

In any aspect or embodiment described herein, the linker group L is $-(A^L)_q-$, wherein:

$(A^L)_q$ is a group which is connected to at least one of a ULM (such as a VLM), PTM moiety, or a combination thereof;

q of the linker is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR_4$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 0-6 $R^{L1}$ and/or $R^{L2}$ groups, $C_5$-13 spirocycloalkyl optionally substituted with 0-9 $R^{L1}$ and/or $R^{L2}$ groups, $C_{3-11}$ heterocyclyl optionally substituted with 0-6 $R^{L1}$ and/or $R^{L2}$ groups, $C_{5-13}$ spiroheterocyclyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, RN and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$ alkyl)$_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is to $A^L_1$ and $(A^L)_q$ wherein the units $A^L$ couple a PTM to a ULM.

In certain embodiments, e.g., where q of the linker is 2, $(A^L)_q$ is a group which is connected to $A^L_1$ and to a ULM or PTM.

In certain embodiments, e.g., where q of the linker is 1, the structure of the linker group L is $-A^L_1-$, and $A^L_1$ is a group which is connected to a ULM moiety and a PTM moiety.

In certain embodiments, the unit $A^L$ of linker (L) comprises a group represented by a general structure selected from the group consisting of:

$—NR(CH_2)_n$-(lower alkyl)-, $—NR(CH_2)_n$-(lower alkoxyl)-, $—NR(CH_2)_n$-(lower alkoxyl)-$OCH_2$—, $—NR(CH_2)_n$-(lower alkoxyl)-(lower alkyl)-$OCH_2$—, $—NR(CH_2)_n$-(cycloalkyl)-(lower alkyl)-$OCH_2$—, $—NR(CH_2)_n$-(hetero cycloalkyl)-, $—NR(CH_2CH_2O)_n$-(lower alkyl)-O—$CH_2$—, $—NR(CH_2CH_2O)_n$-(hetero cycloalkyl)-O—$CH_2$—, $—NR(CH_2CH_2O)_n$-Aryl-O—$CH_2$—, $NR(CH_2CH_2O)_n$-(hetero aryl)-O—$CH_2$—, $—NR(CH_2CH_2O)_n$-(cyclo alkyl)-O-(hetero aryl)-O—$CH_2$—, $—NR(CH_2CH_2O)_n$-(cyclo alkyl)-O-Aryl-O—$CH_2$—, $—NR(CH_2CH_2O)_n$-(lower alkyl)-NH-Aryl-O—$CH_2$—, $—NR(CH_2CH_2O)_n$-(lower alkyl)-O-Aryl-$CH_2$, $—NR(CH_2CH_2O)_n$-cycloalkyl-O-Aryl-, $—NR(CH_2CH_2O)_n$-cycloalkyl-O-(heteroaryl)l-, $—NR(CH_2CH_2)_n$-(cycloalkyl)-O-(heterocyclyl)-$CH_2$, $—NR(CH_2CH_2)_n$-(heterocyclyl)-(heterocyclyl)-$CH_2$, —N(R1R2)-(heterocyclyl)-$CH_2$; where n of the linker can be 0 to 10;

R of the linker can be H, lower alkyl;

R1 and R2 of the linker can form a ring with the connecting N.

In certain embodiments, the unit $A^L$ of linker (L) comprises a group represented by a general structure selected from the group consisting of:

$—N(R)—(CH_2)_m—O(CH_2)_n—O(CH_2)_o—O(CH_2)_p—O(CH_2)_q—O(CH_2)_r—OCH_2—$, $—O—(CH_2)_m—O(CH_2)_n—O(CH_2)_o—O(CH_2)_p—O(CH_2)_q—O(CH_2)_r—OCH_2—$, $—O—(CH_2)_m—O(CH_2)_n—O(CH_2)_o—O(CH_2)_p—O(CH_2)_q—O(CH_2)_r—O—$; $—N(R)—(CH_2)_m—O(CH_2)_n—O(CH_2)_o—O(CH_2)_p—O(CH_2)_q—O(CH_2)_r—O—$; $(CH2)_m$ $O(CH2)_nO(CH2)_o—O(CH2)_p—O(CH2)_q—O(CH2)_r—O—$; $(CH2)_mO(CH2)_nO(CH2)_o—O(CH2)_p—O(CH2)_q—O(CH2)_r$-OCH2-;

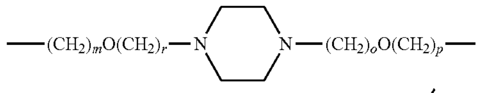
;

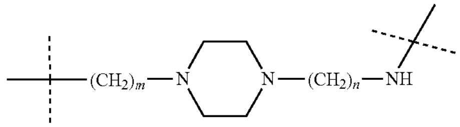
;

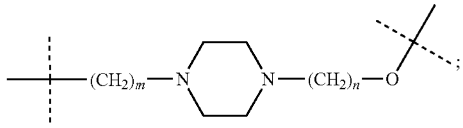
;

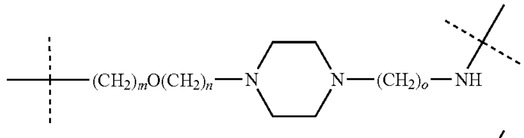
;

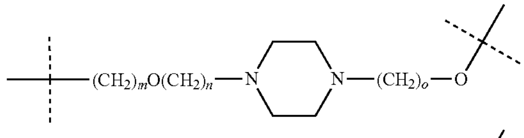
;

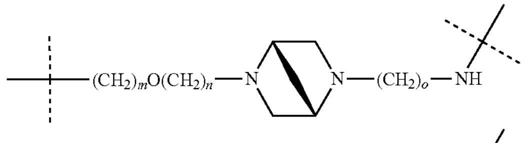
;

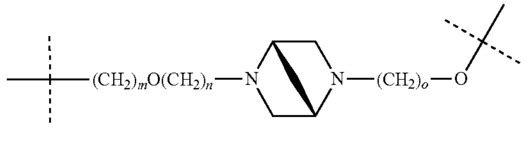

-continued
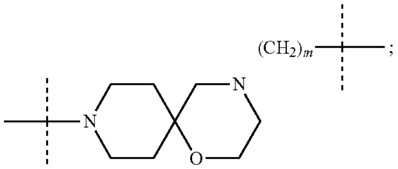
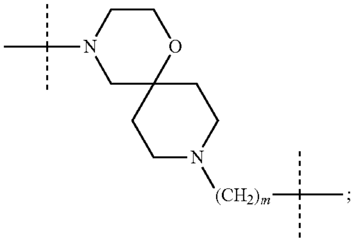
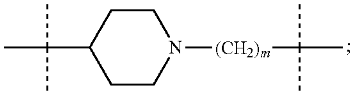
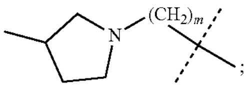
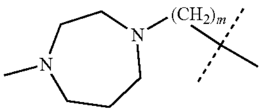
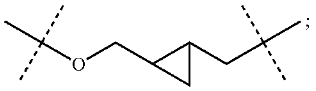
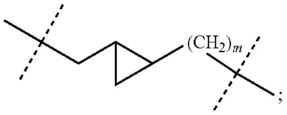
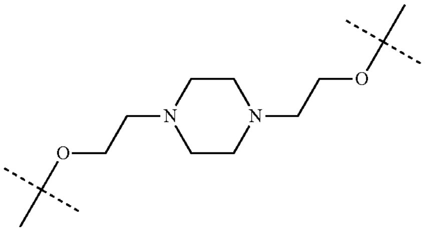
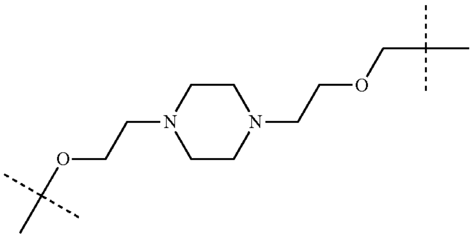
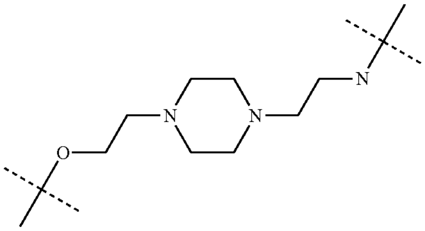
-continued
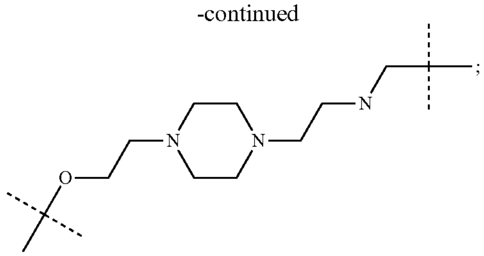
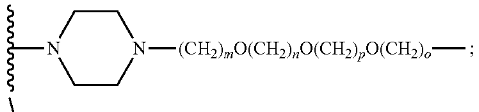
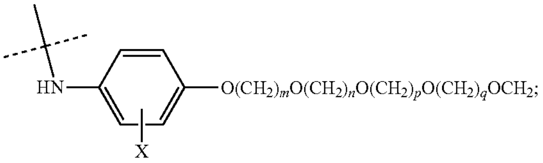
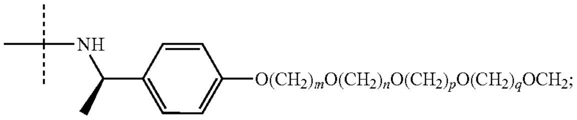
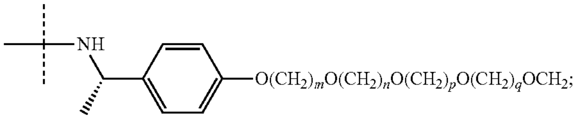
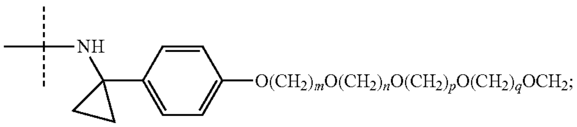
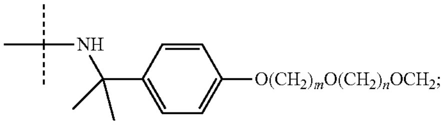
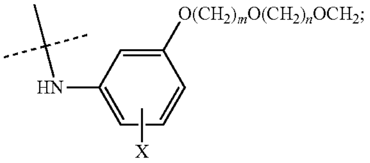
and
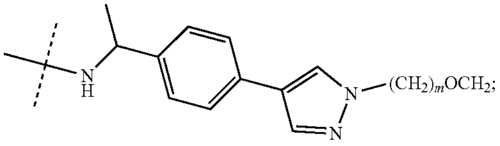
wherein
m, n, o, p, q, and r of the linker are independently 0, 1, 2, 3, 4, 5, 6, 7, 8, 9, 10, 11, 12, 13, 14, 15, 16, 17, 18, 19, 20;
when the number is zero, there is no N—O or O—O bond
R of the linker is H, methyl and ethyl;
X of the linker is H and F
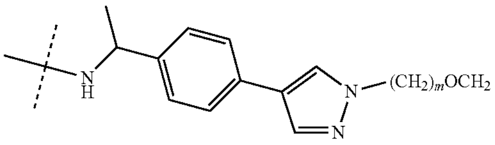
where m of the linker can be 2, 3, 4, 5

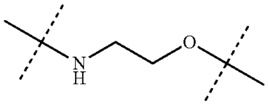
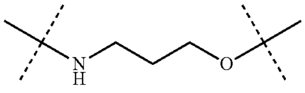
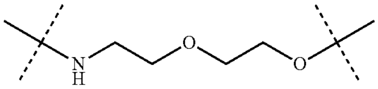
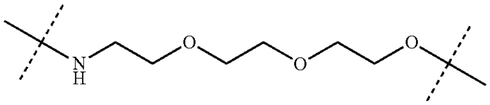
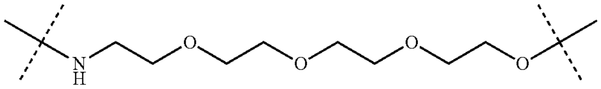
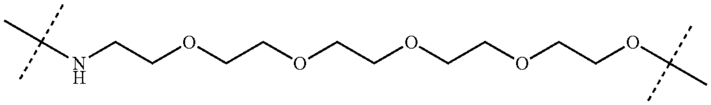
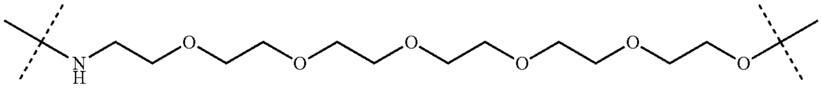
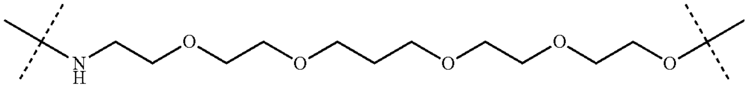
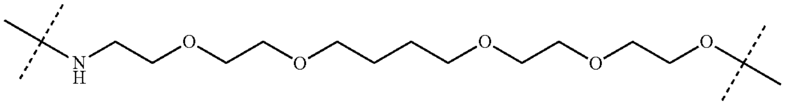
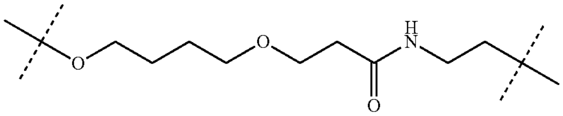
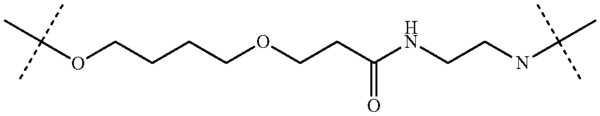
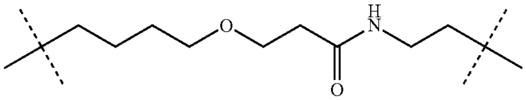
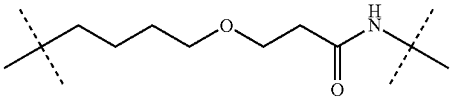
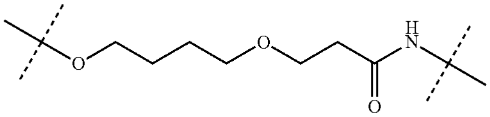
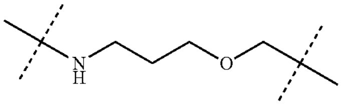
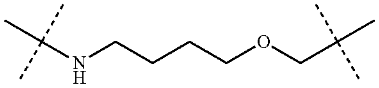
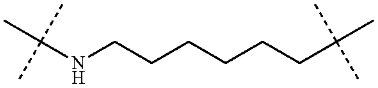
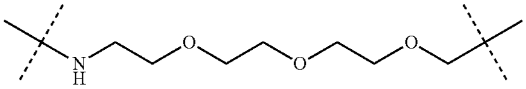
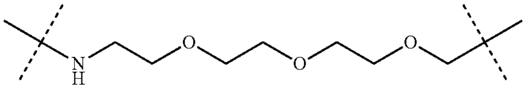
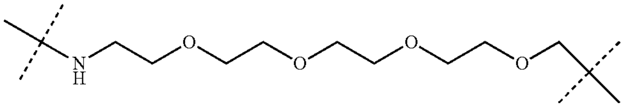
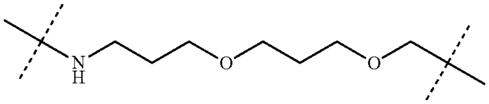
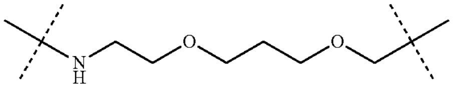
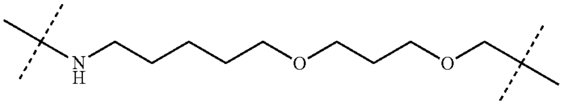
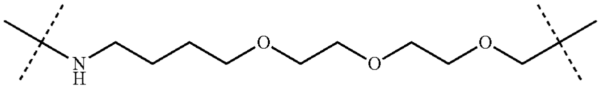
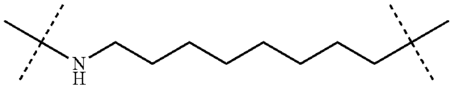
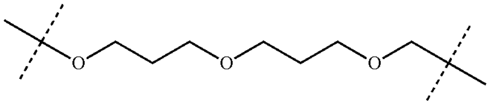
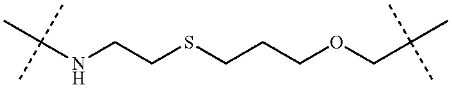
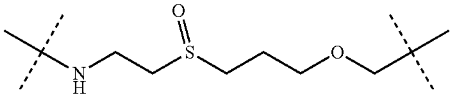
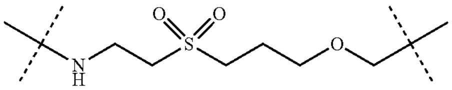
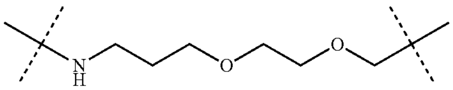
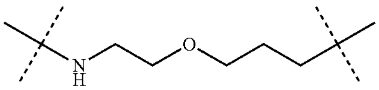

-continued
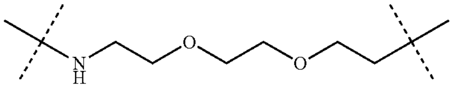
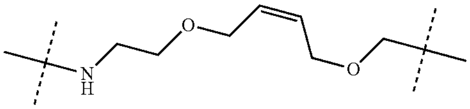
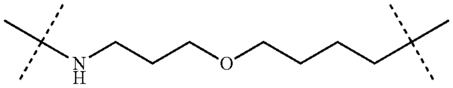
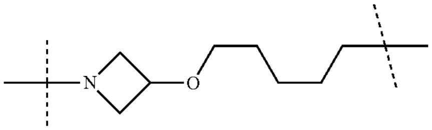
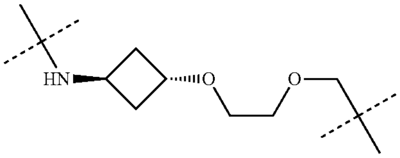
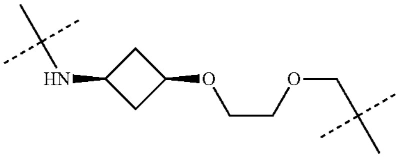
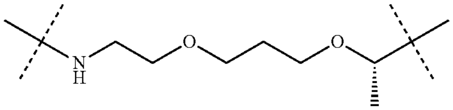
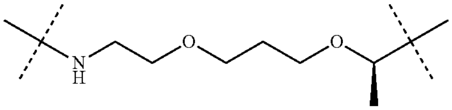
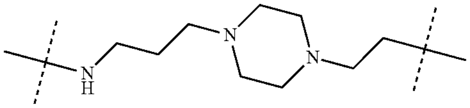
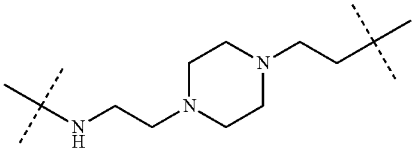
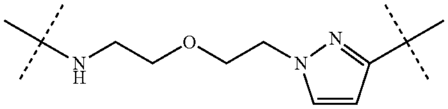
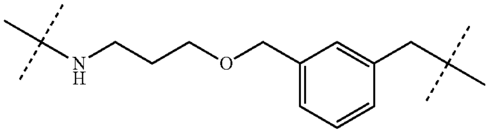
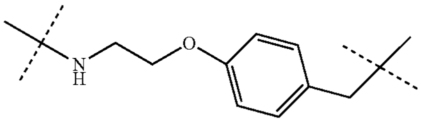
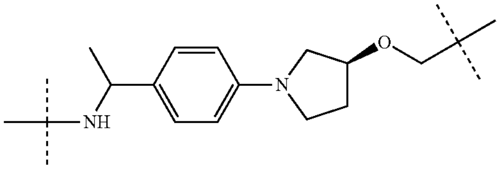
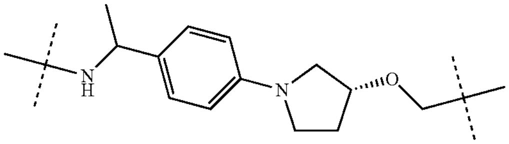
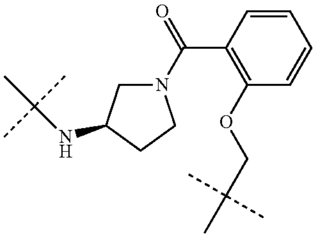
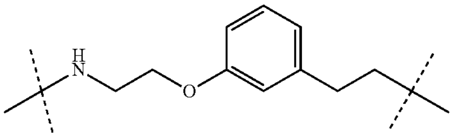
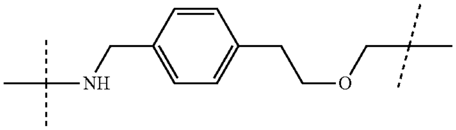
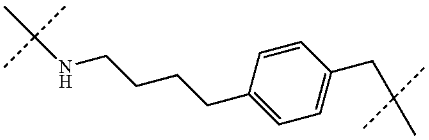
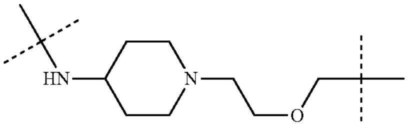
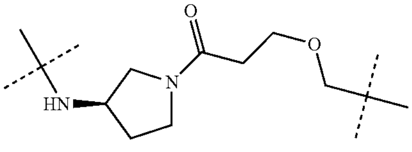
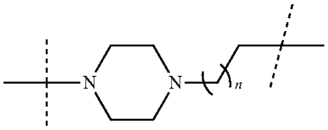

-continued
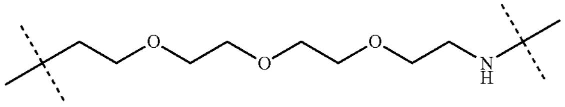
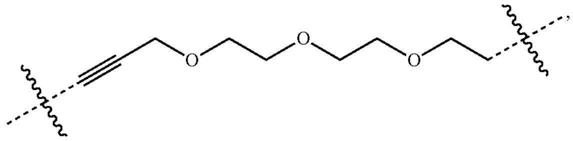
,
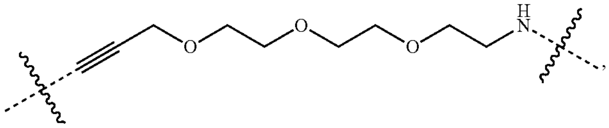
,
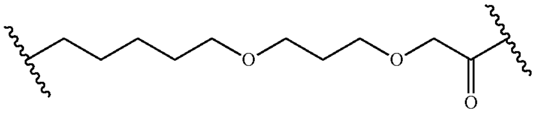
;
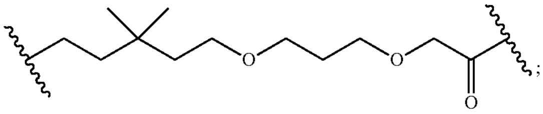
;
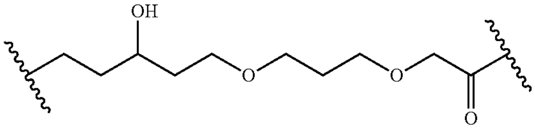
;
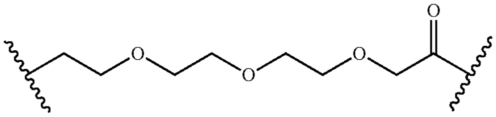
;
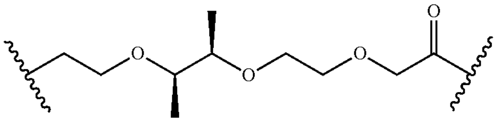
;
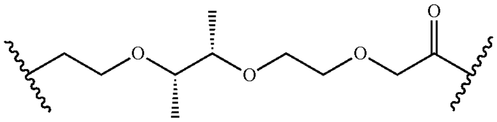
;
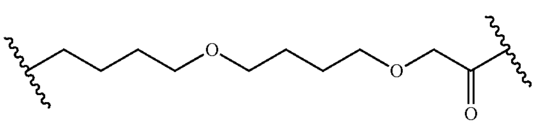
;
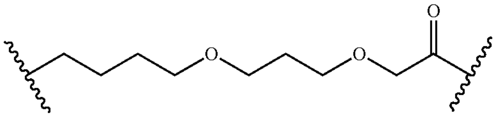
;
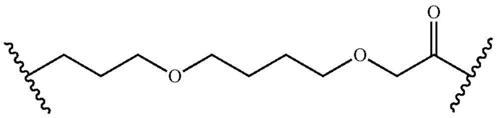
;
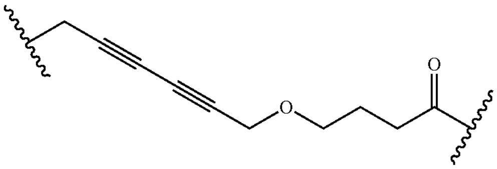
;
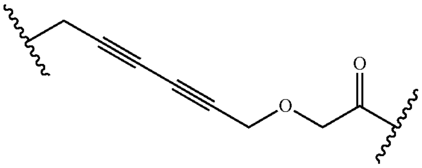
;
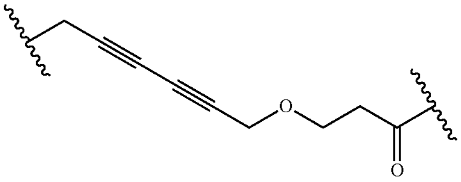
;
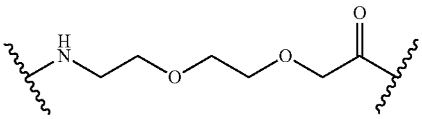
;
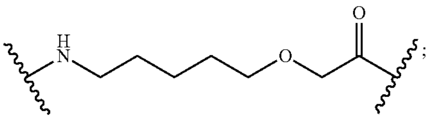
;
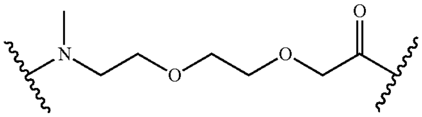
;
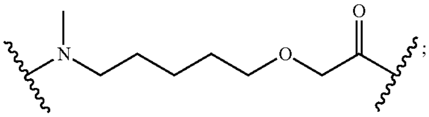
;
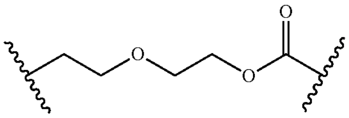
;
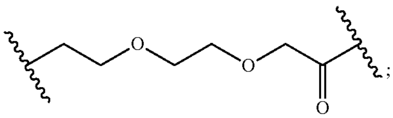
;
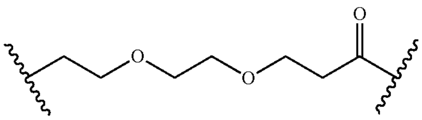
;
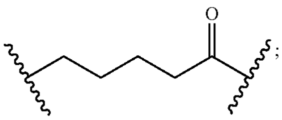
;
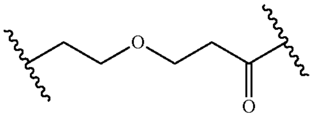
;

-continued
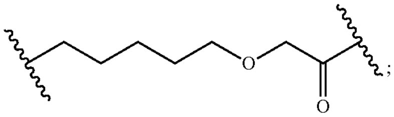;
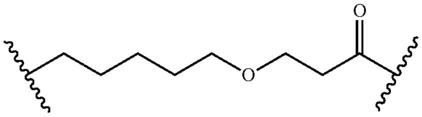;
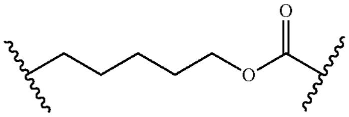;
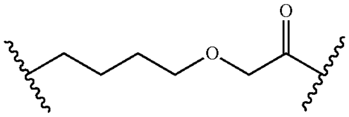;
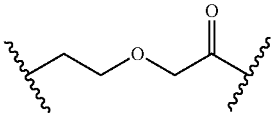;
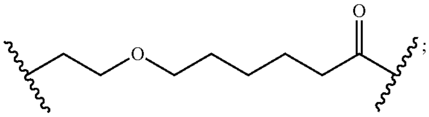;
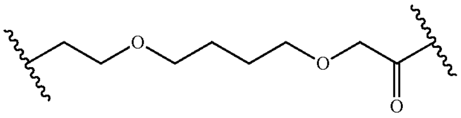;
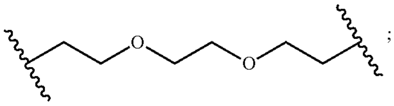;
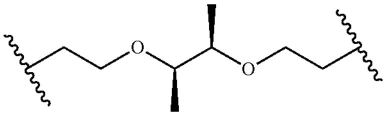;
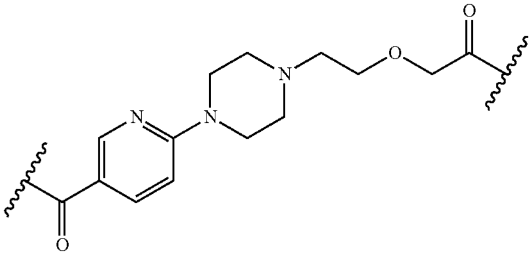;
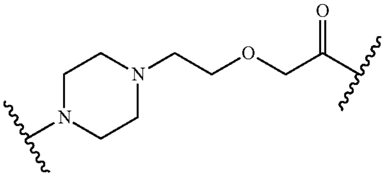;
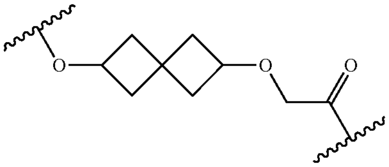;
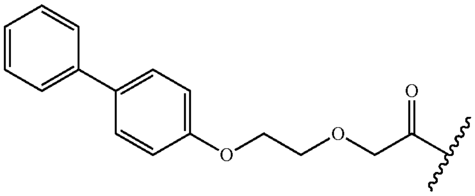;
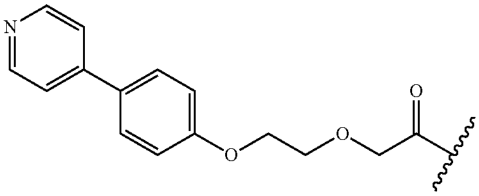;
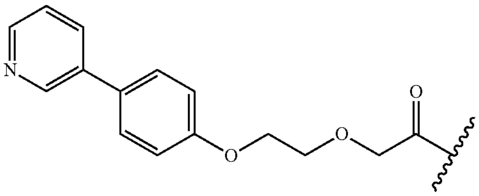;
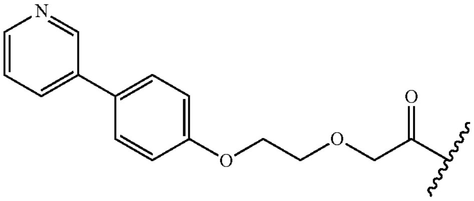;
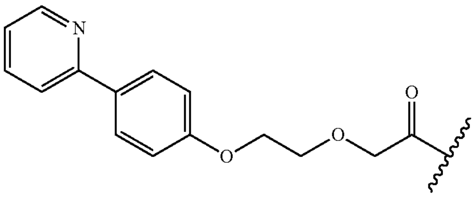;
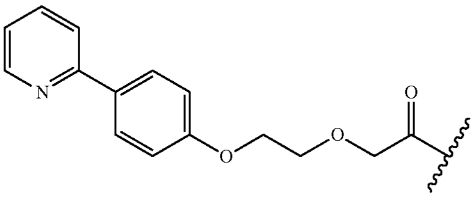;
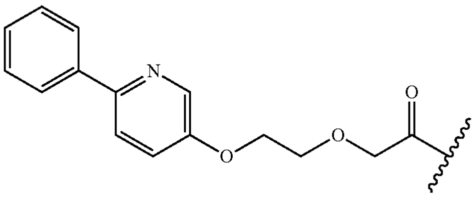;
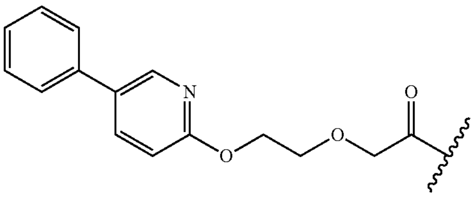;

-continued
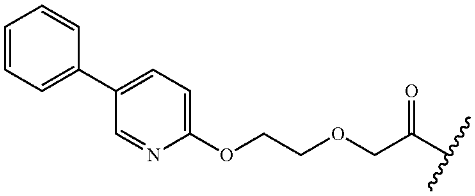
;
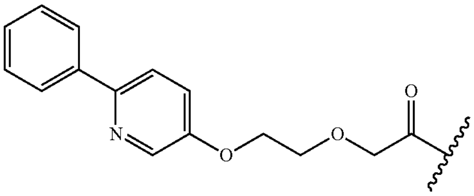
;
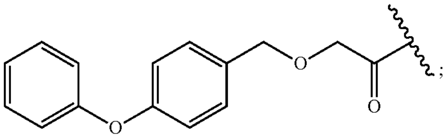
;
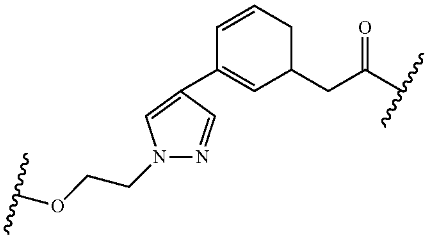
;
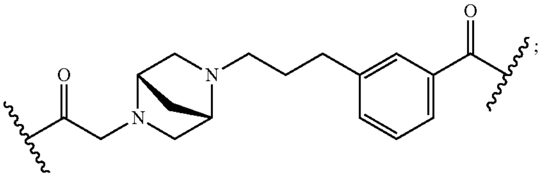
;
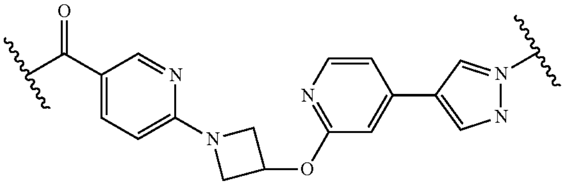
;
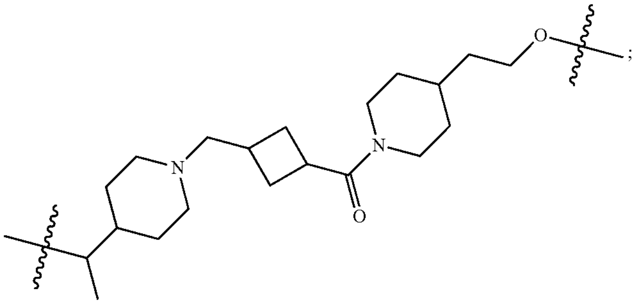
;
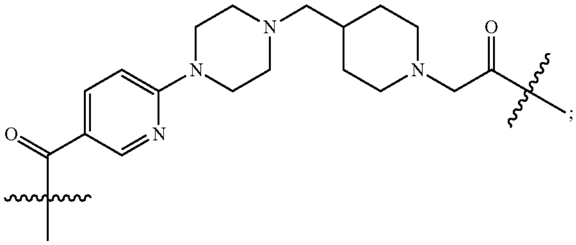
;
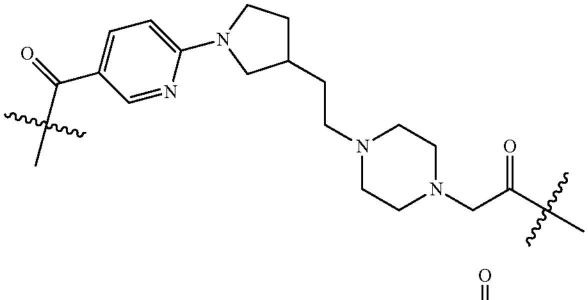
;
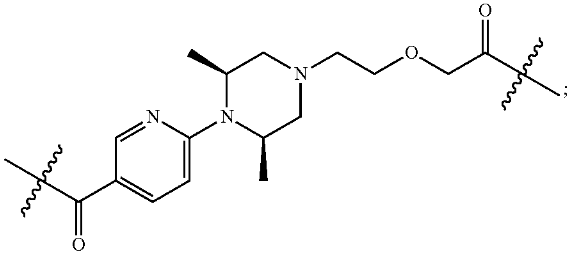
;

-continued
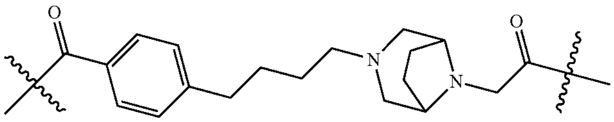
;
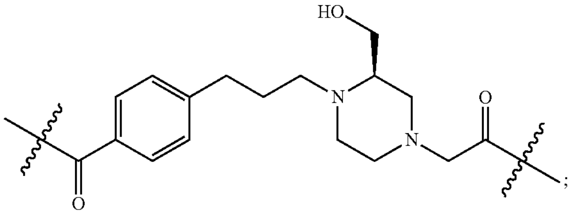
;
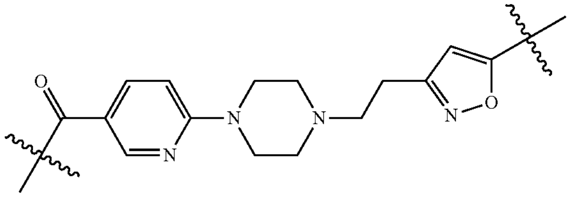
;
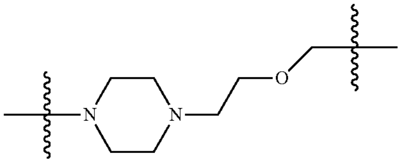
;
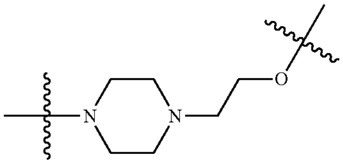
;
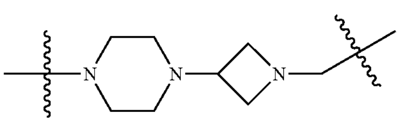
;
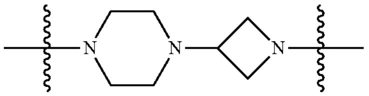
;
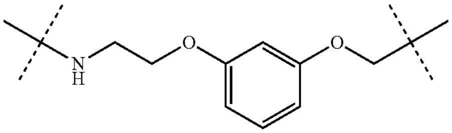
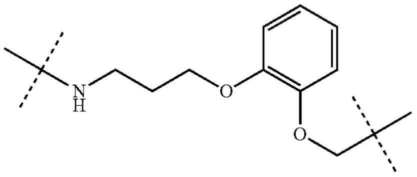
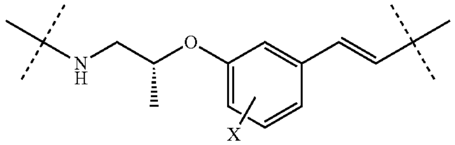
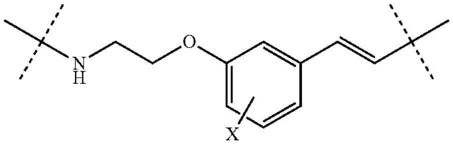
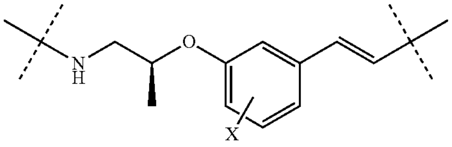
X = H, F
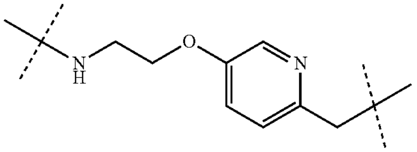
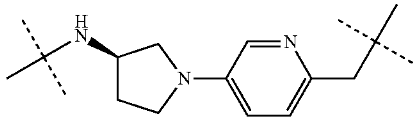
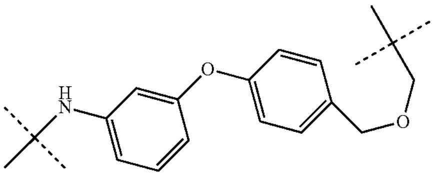
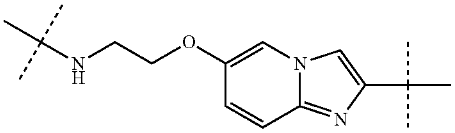
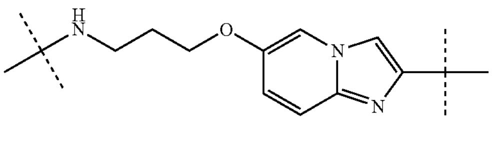
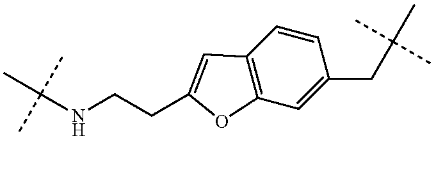

-continued
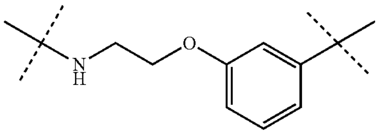
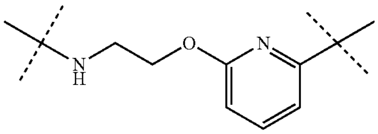
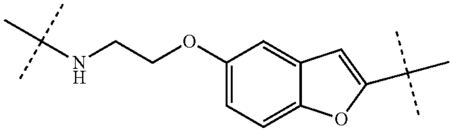
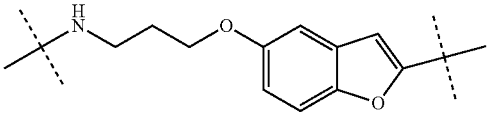
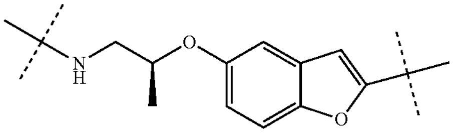
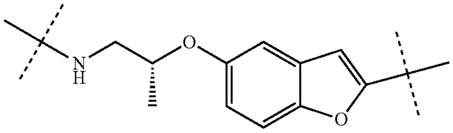
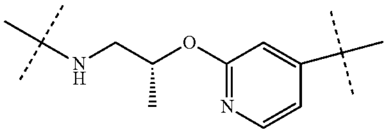
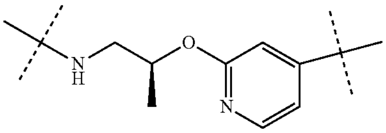
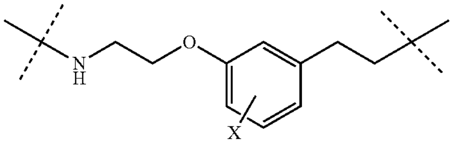
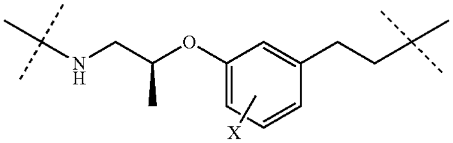
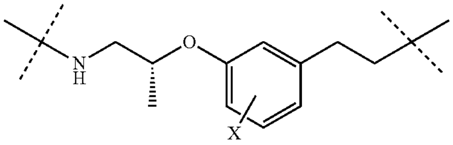
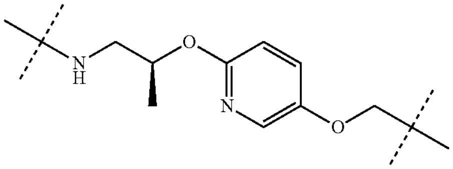
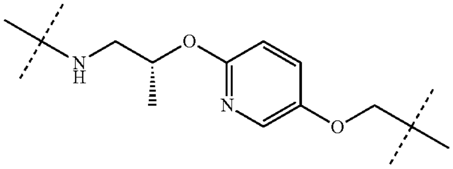
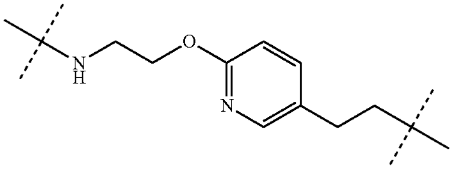
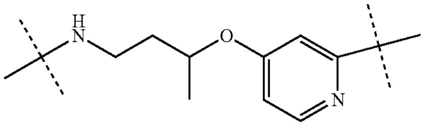
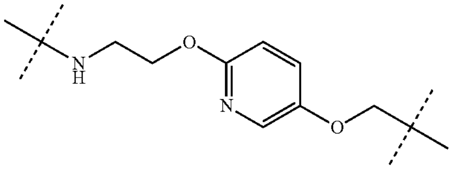
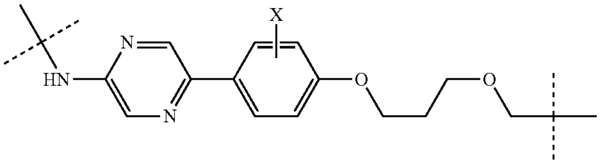
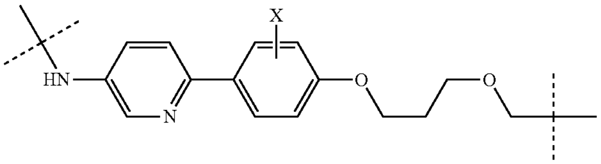
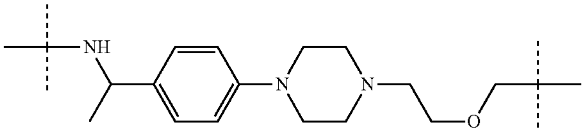

-continued
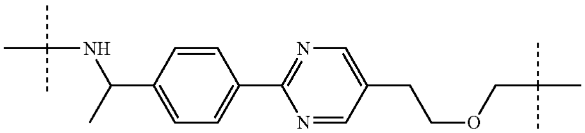
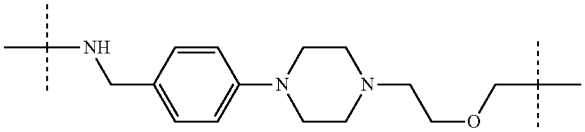
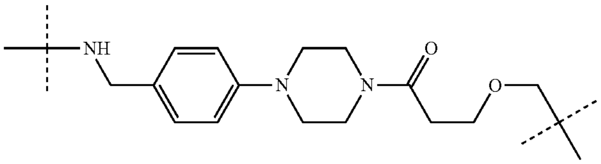
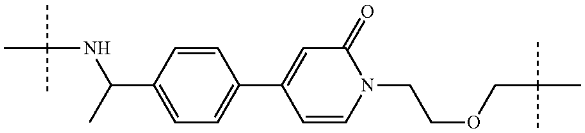
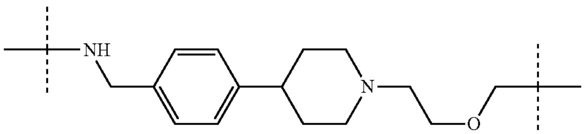
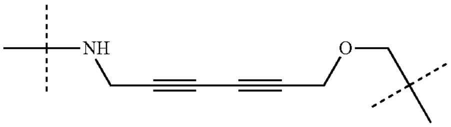
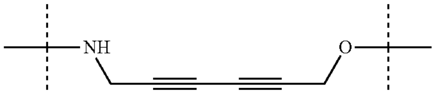
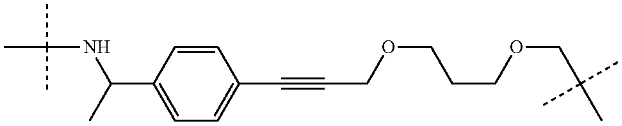
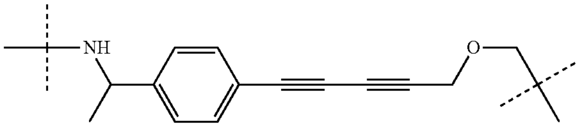
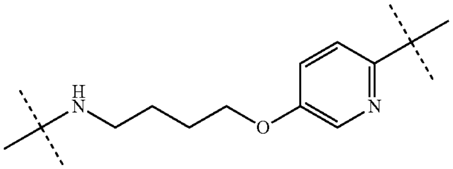
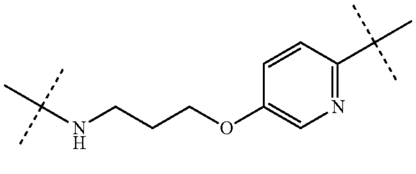
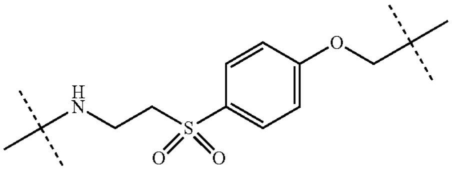
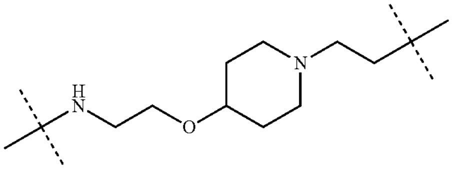
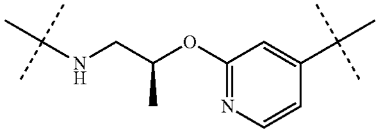
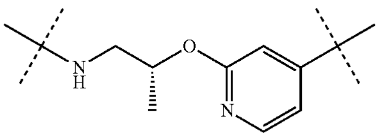

-continued
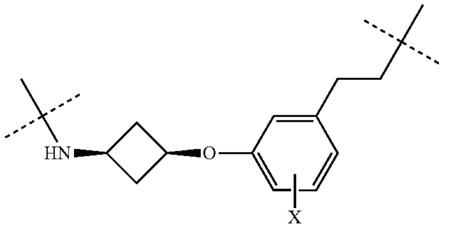
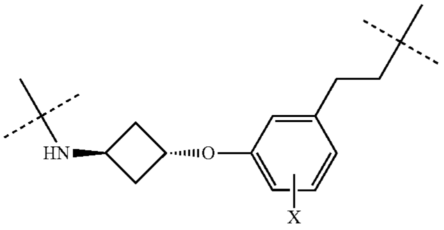
X = H, F
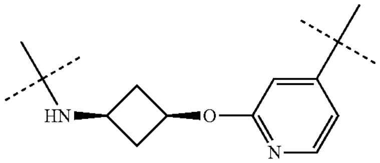
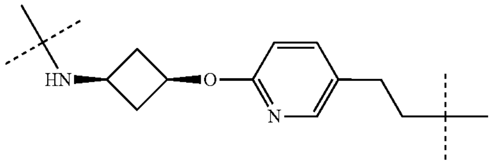
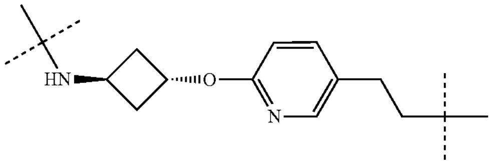
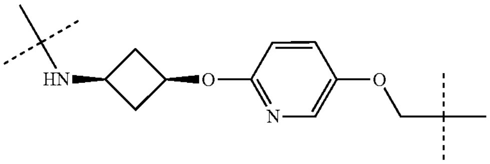
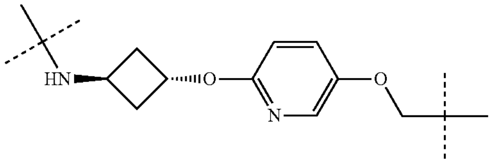
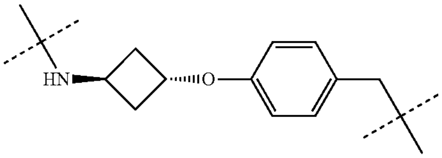
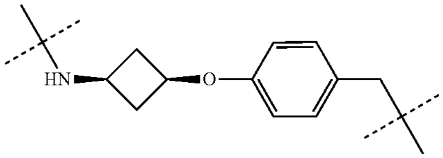
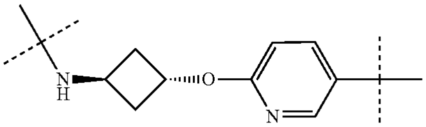
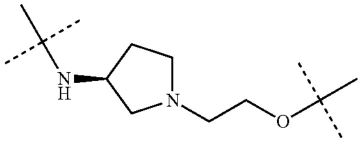
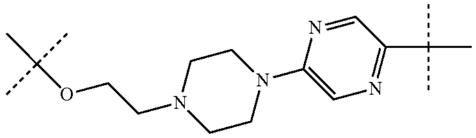
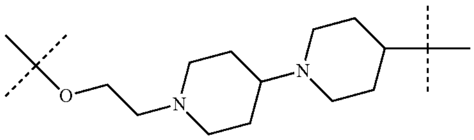
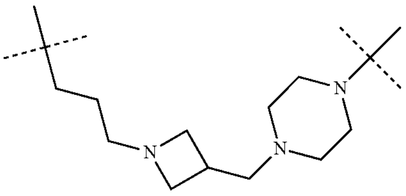
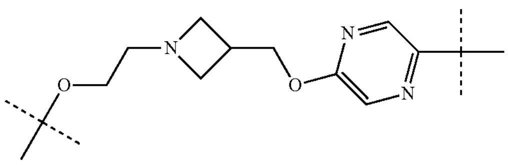
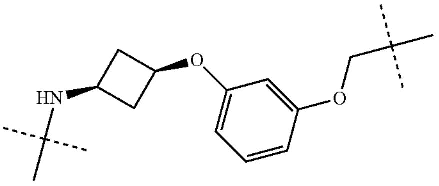
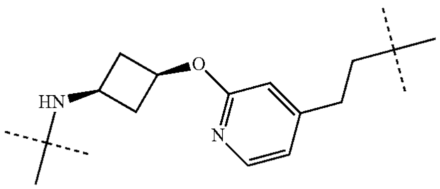
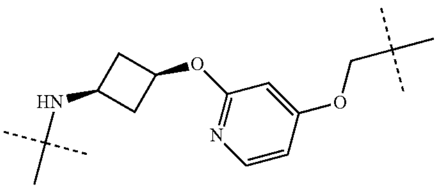

-continued
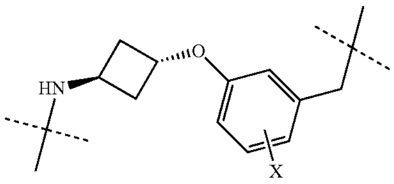
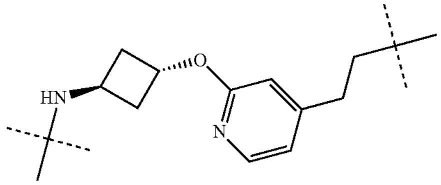
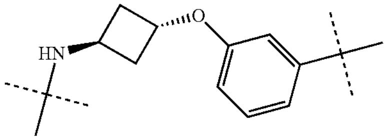
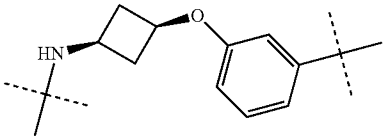
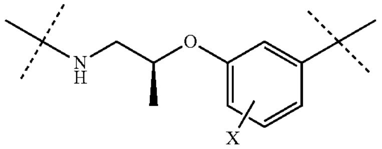
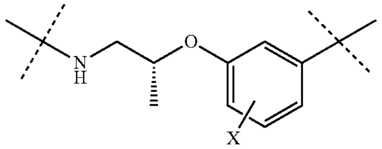
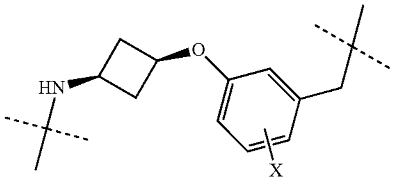
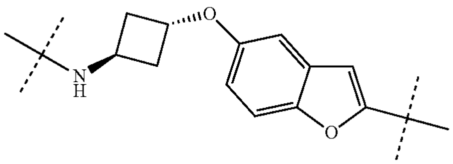
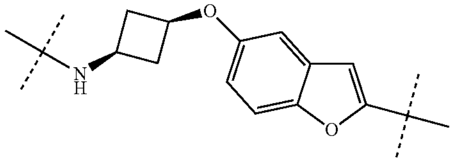
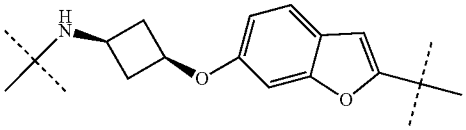
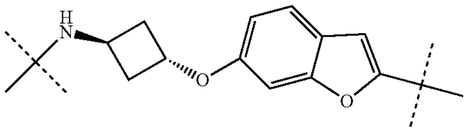
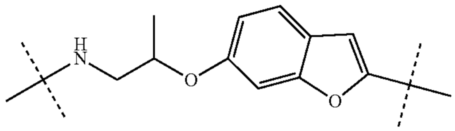
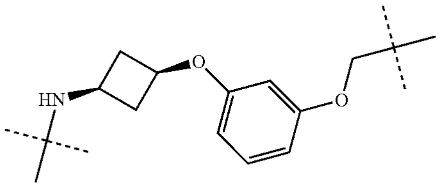
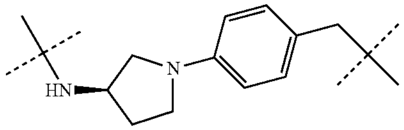
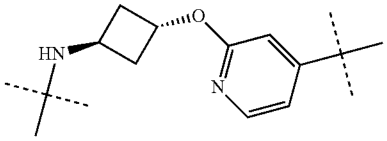
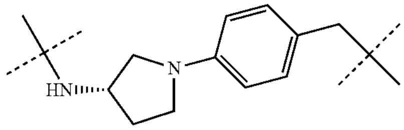
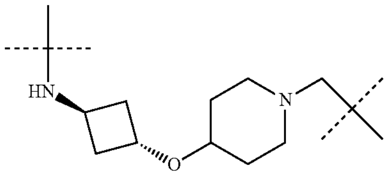
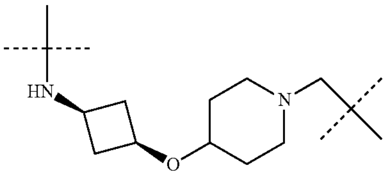
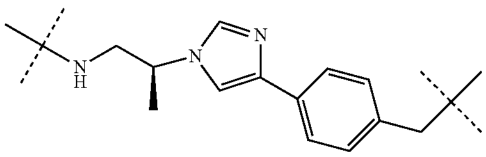
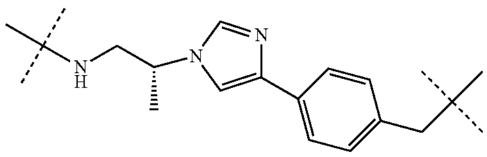

-continued
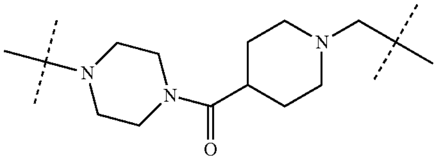
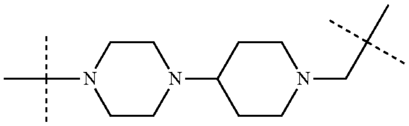
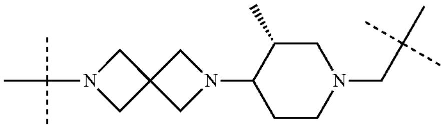
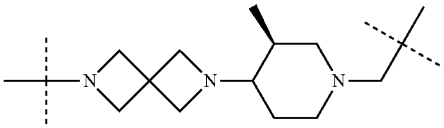
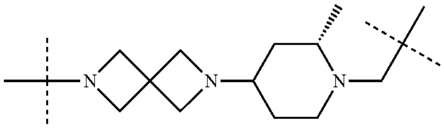
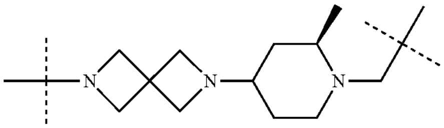
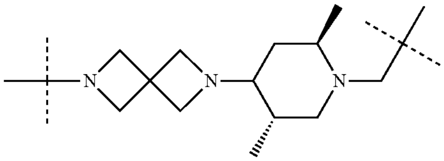
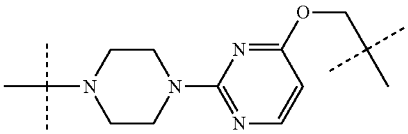
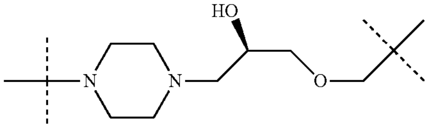
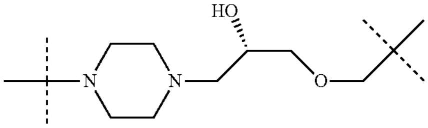
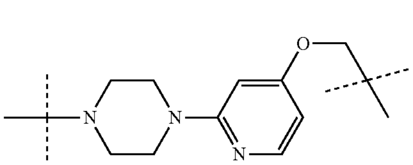
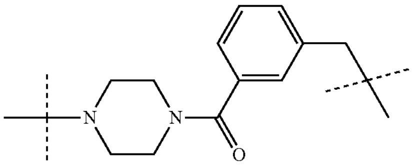
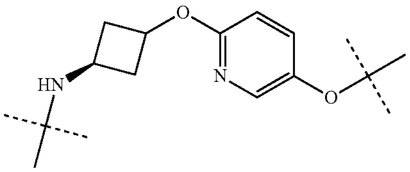
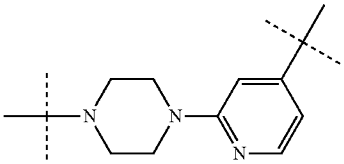
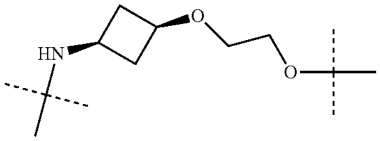
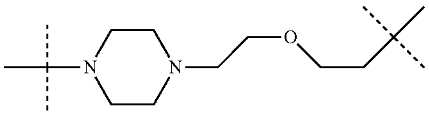
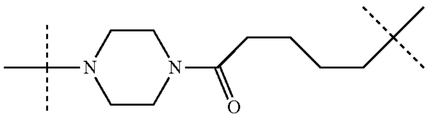
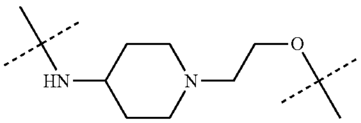
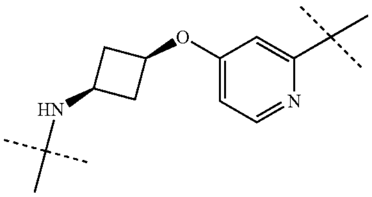
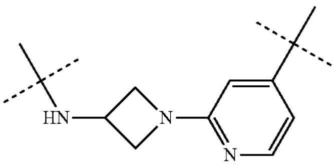
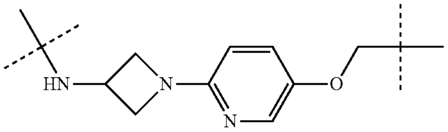
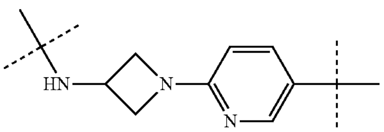
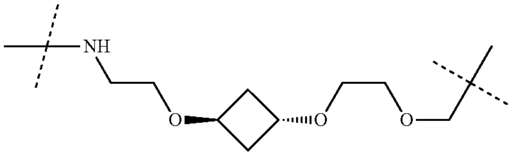

-continued
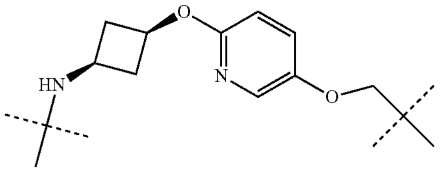
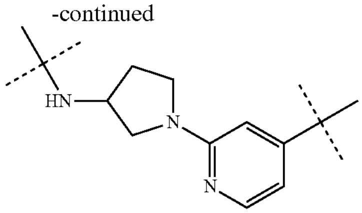
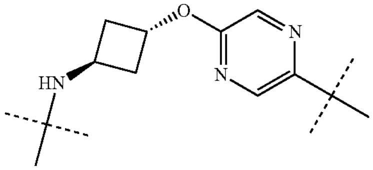
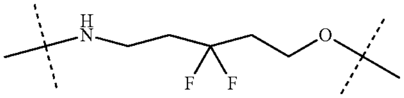
where each n and m of the linker can independently be 0, 1, 2, 3, 4, 5, 6.
In any aspect or embodiment described herein, the unit $A^L$ of linker (L) is selected from the group consisting of:
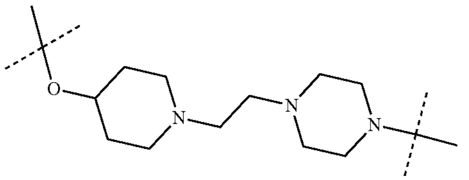
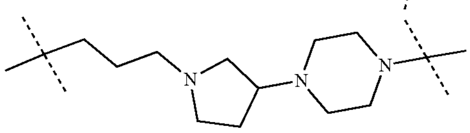
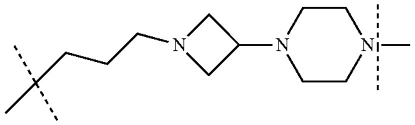
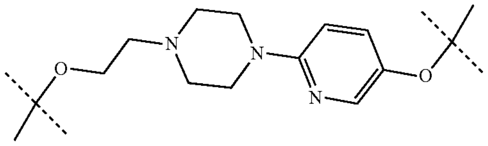
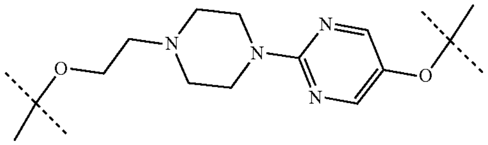
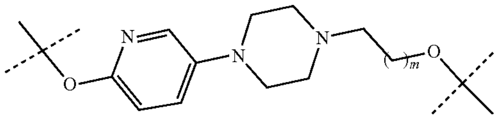
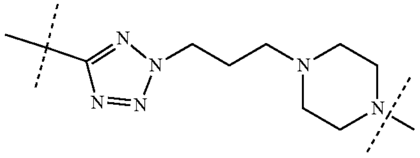
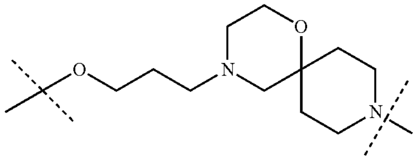
-continued
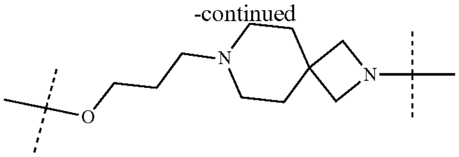
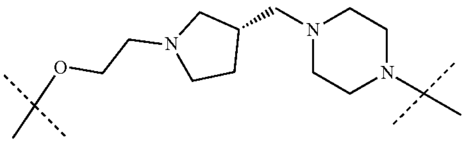
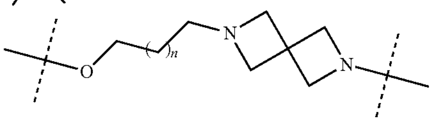
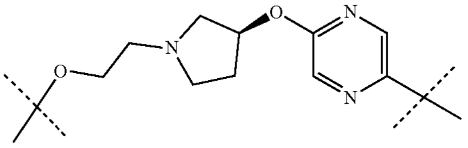
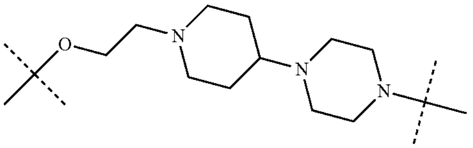
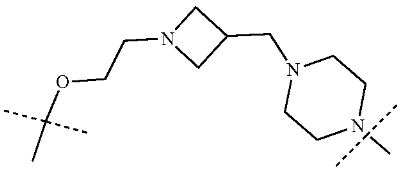
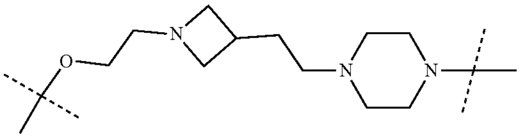
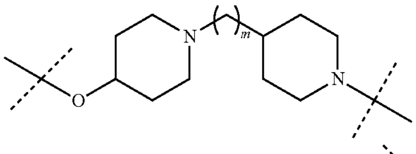
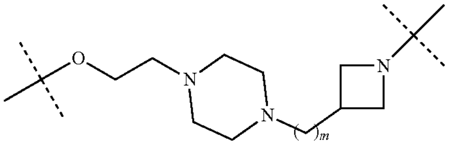

-continued
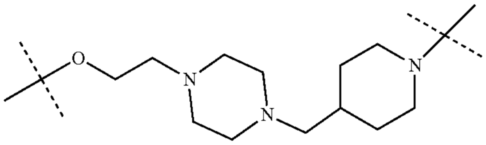
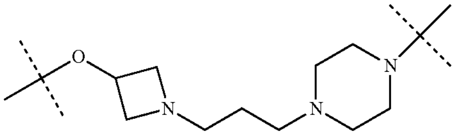
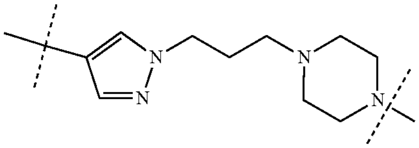
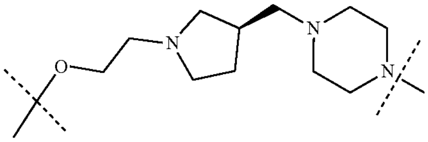
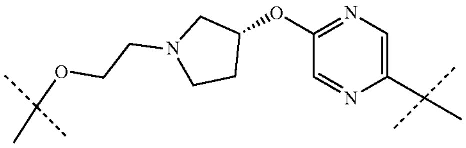
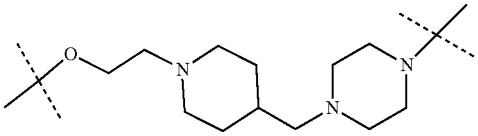
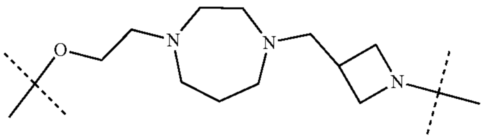
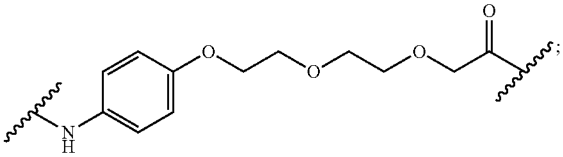 ;
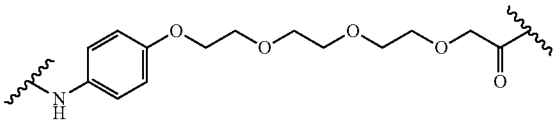 ;
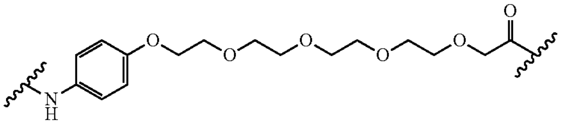 ;
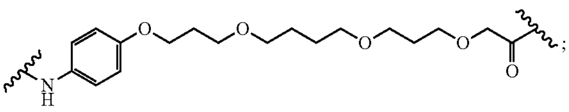 ;
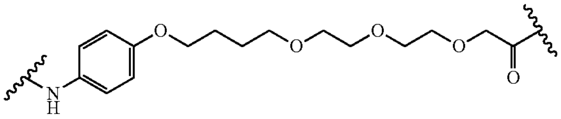 ;
-continued
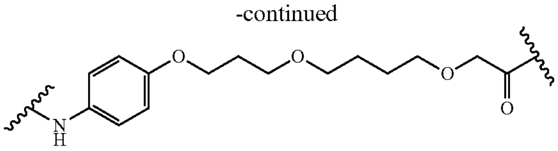 ;
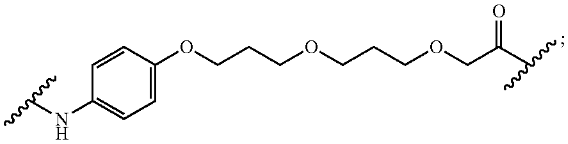 ;
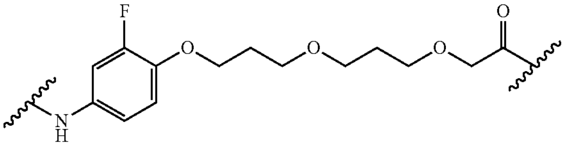 ;
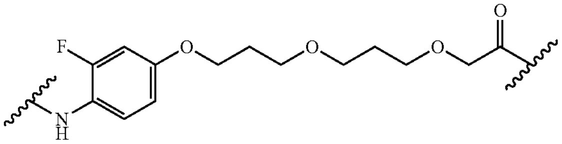 ;
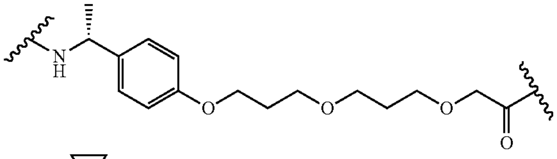 ;
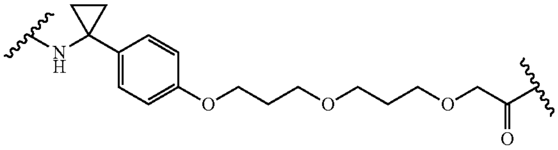 ;
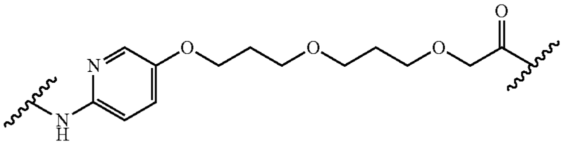 ;
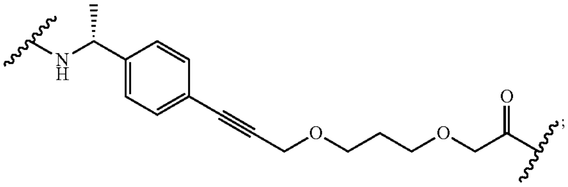 ;
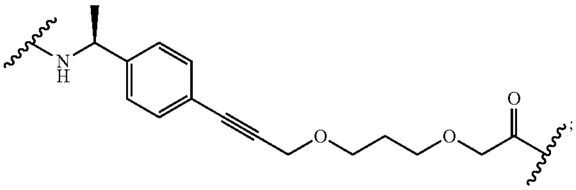 ;
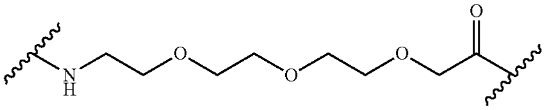 ;
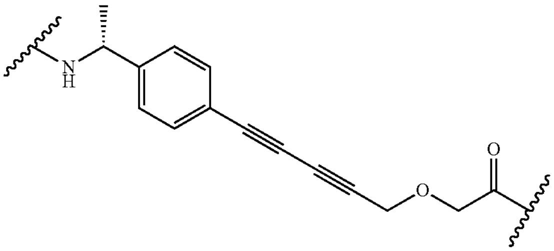 ;

-continued
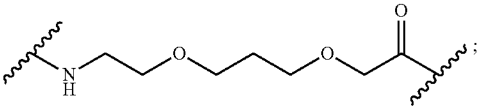
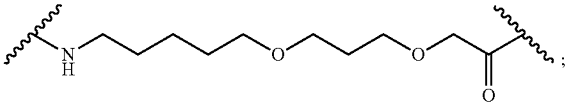
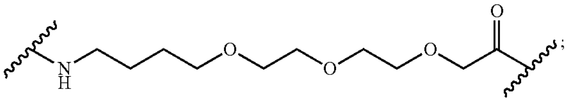
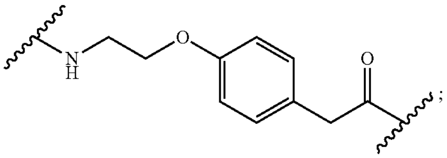
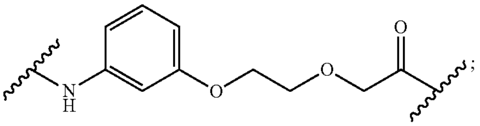
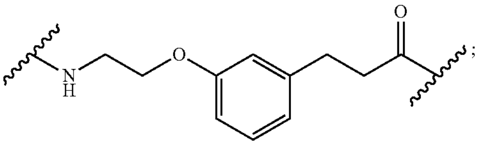
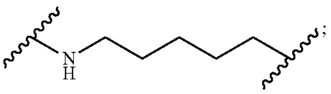
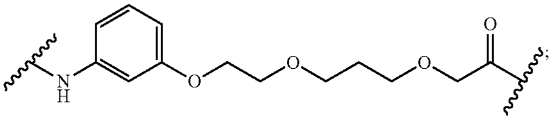
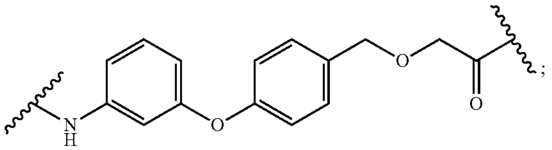
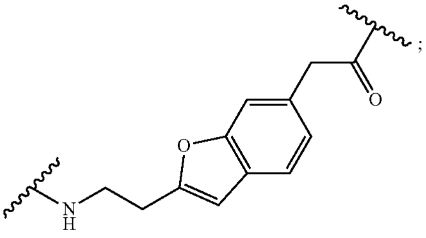
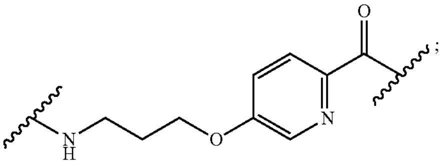
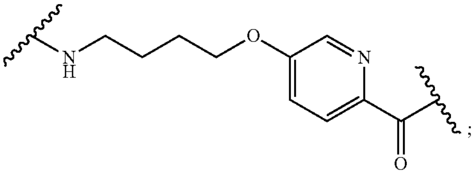
-continued
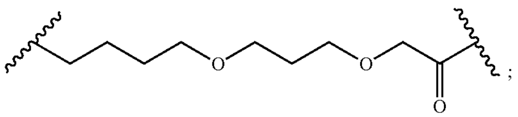
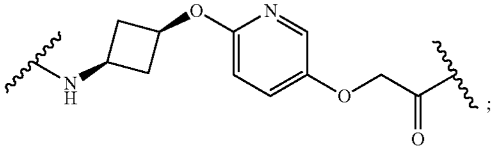
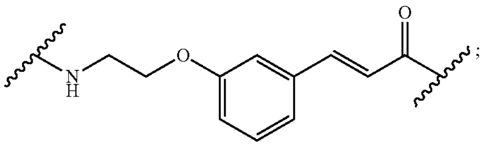
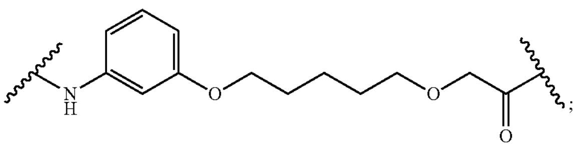
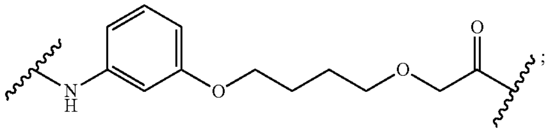
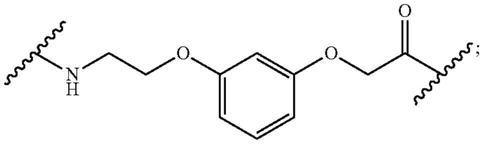
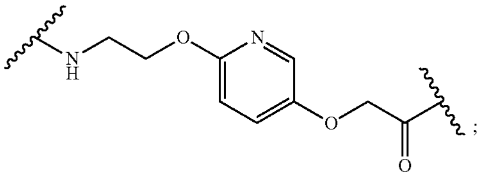
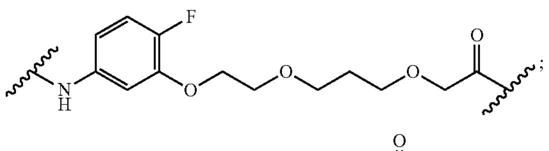
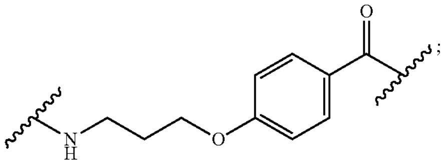
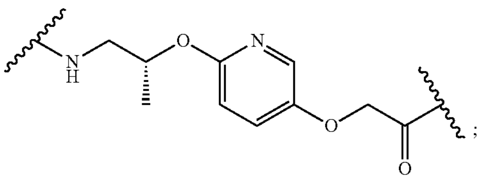
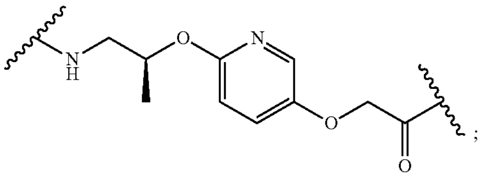

-continued
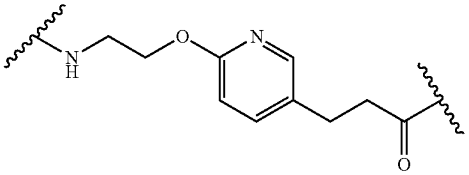
;
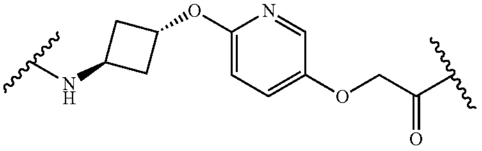
;
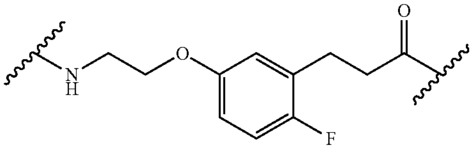
;
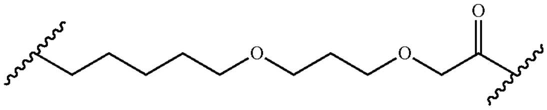
;
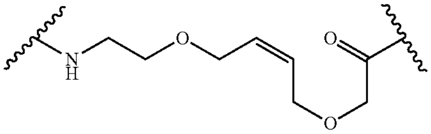
;
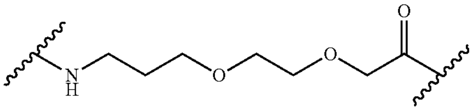
;
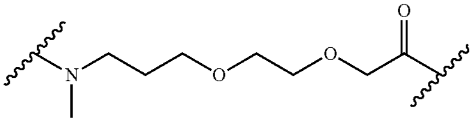
;
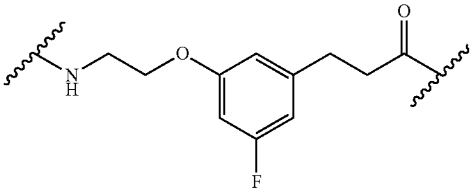
;
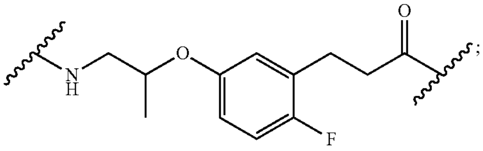
;
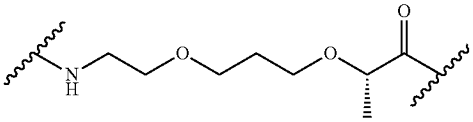
;
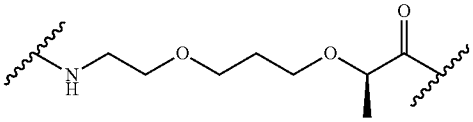
;
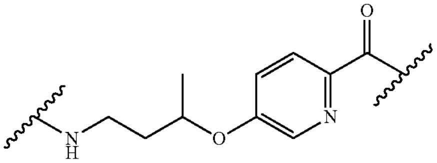
;
-continued
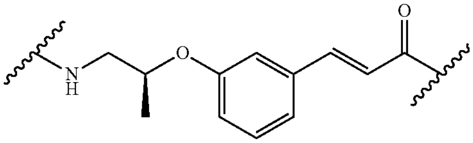
;
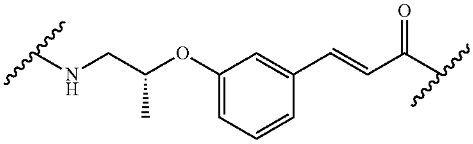
;
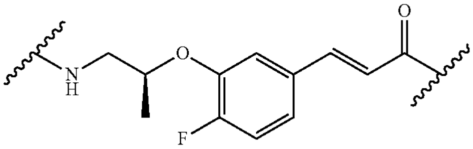
;
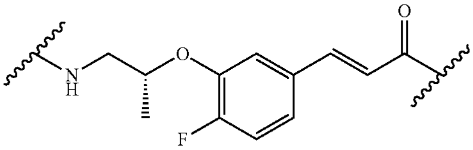
;
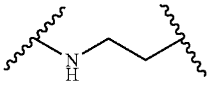
;
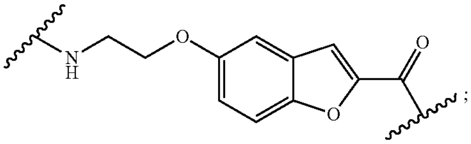
;
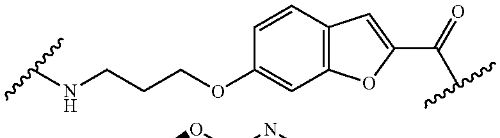
;
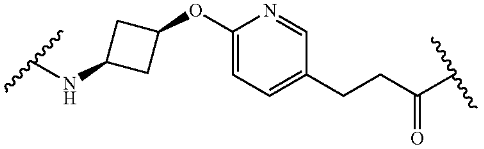
;
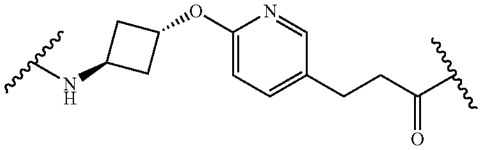
;
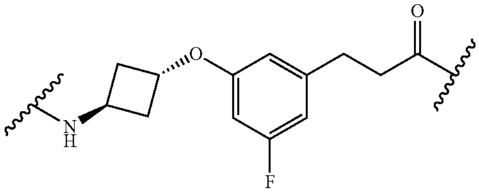
;
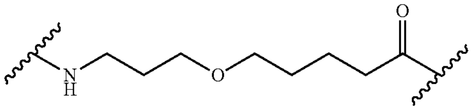
;
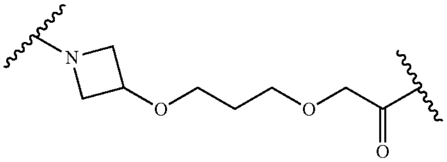
;

-continued
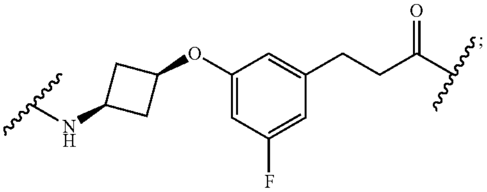
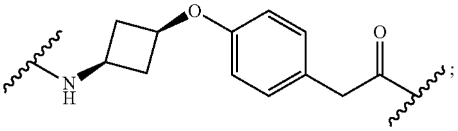
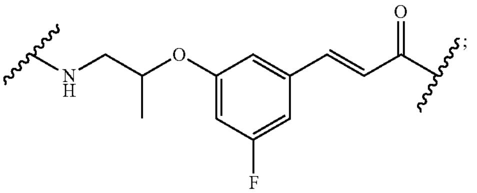
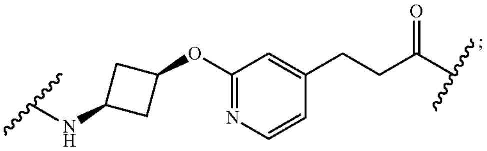
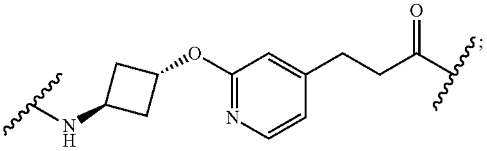
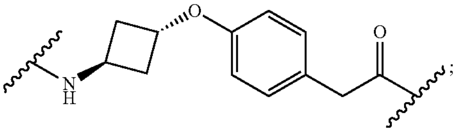
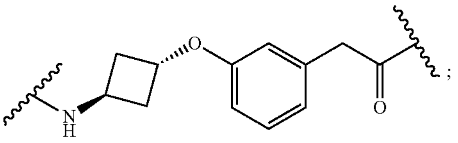
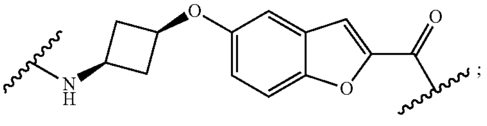
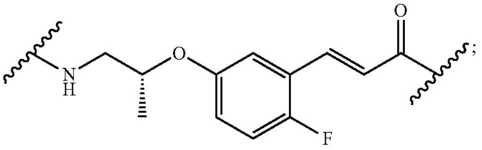
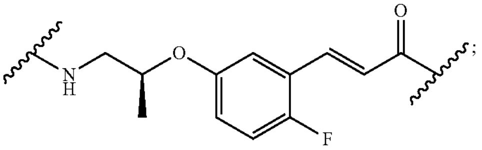
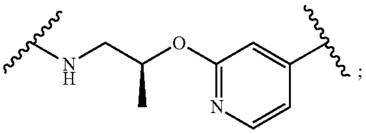
-continued
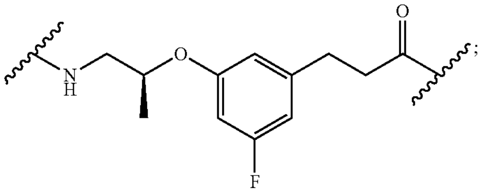
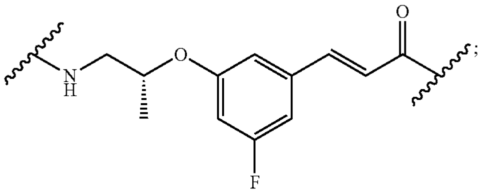
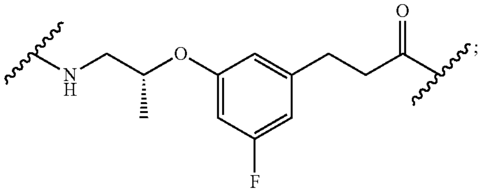
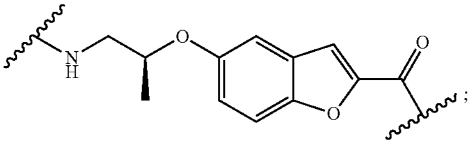
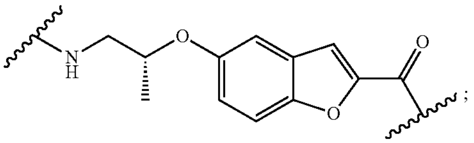
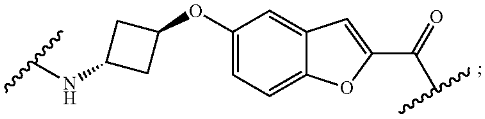
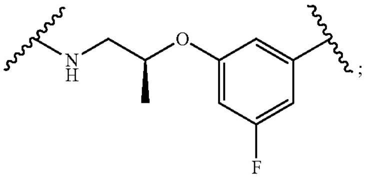
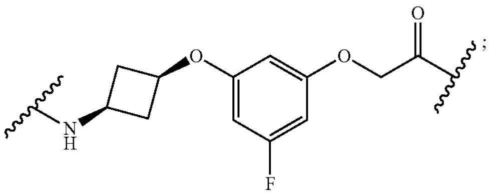
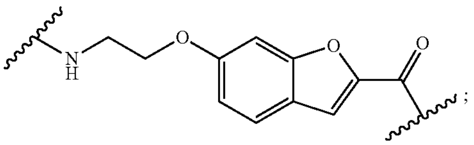
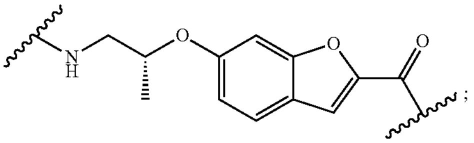

-continued
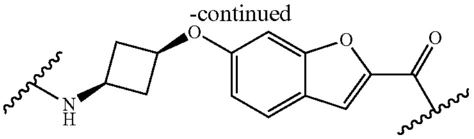
;
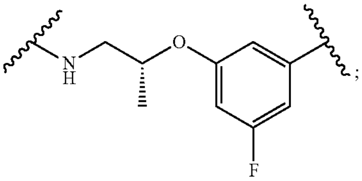
;
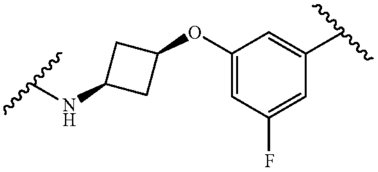
;
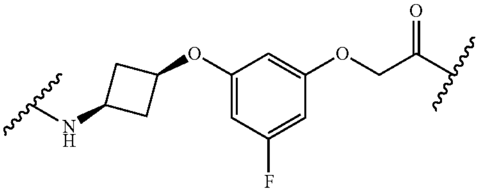
;
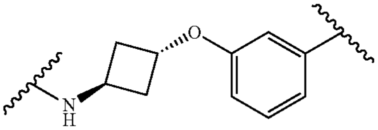
;
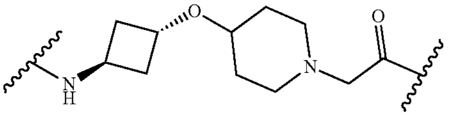
;
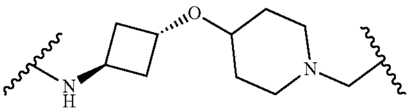
and
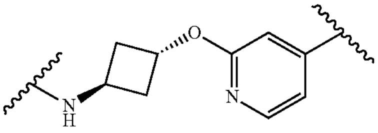
,
wherein each m and n is independently selected from 0, 1, 2, 3, 4, 5, or 6.
In any aspect or embodiment described herein, the unit $A^L$ of linker (L) is selected from the group consisting of:
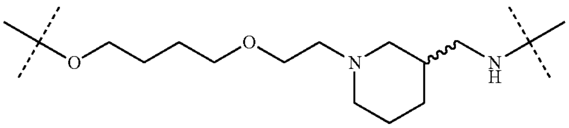
;
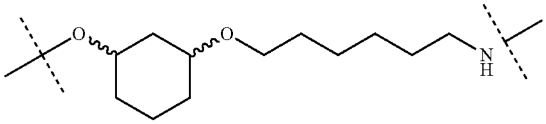
;
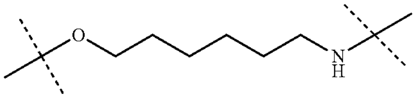
;
-continued
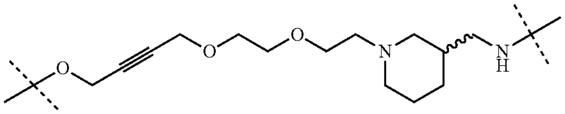
;
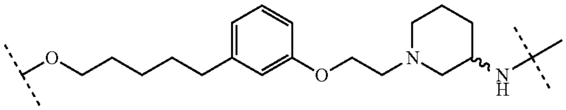
;
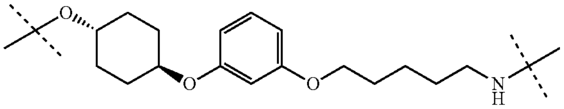
;
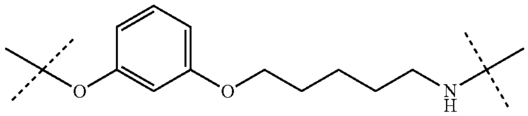
;
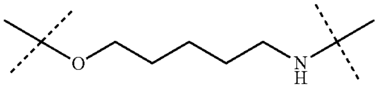
;
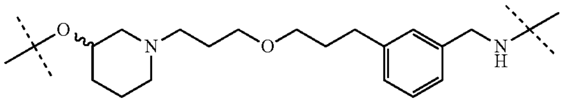
;
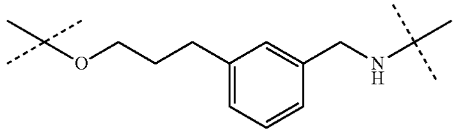
;
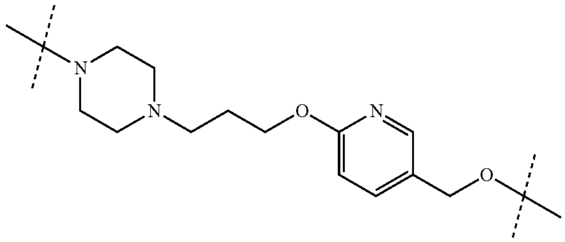
;
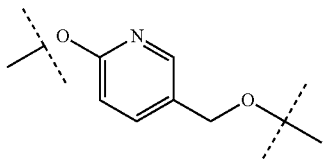
;
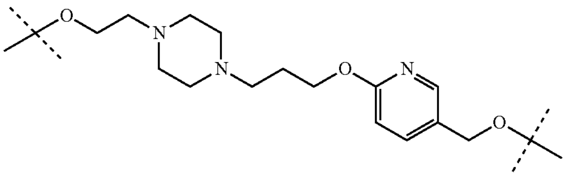
;
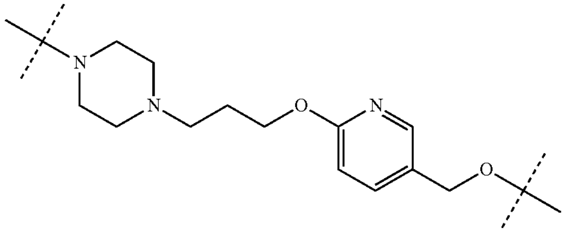
;

-continued
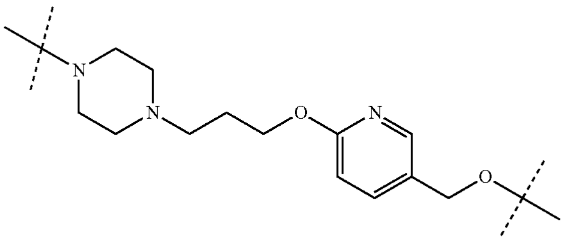
;
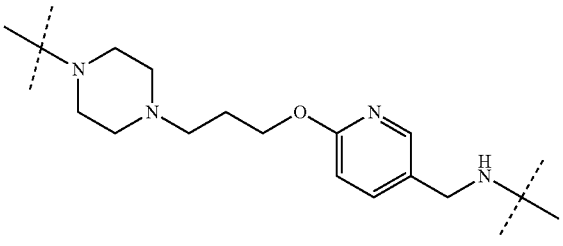
;
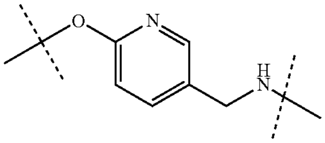
;
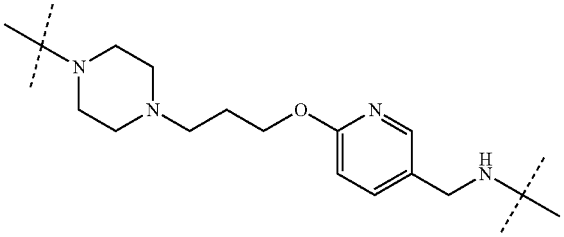
;
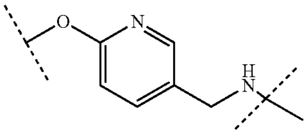
;
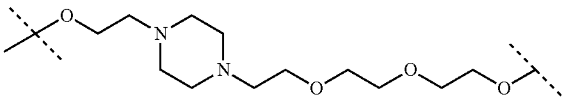
;
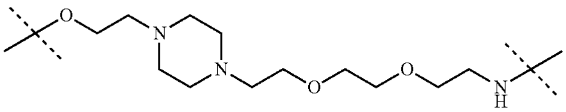
;
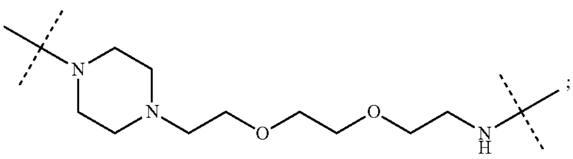
;
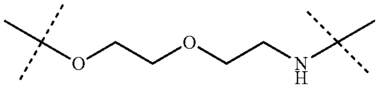
;
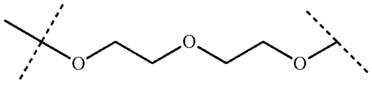
;
-continued
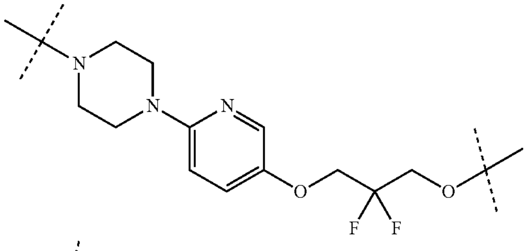
;
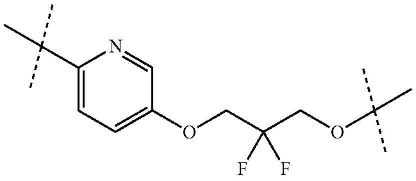
;
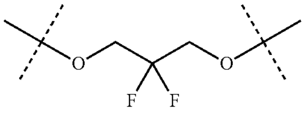
;
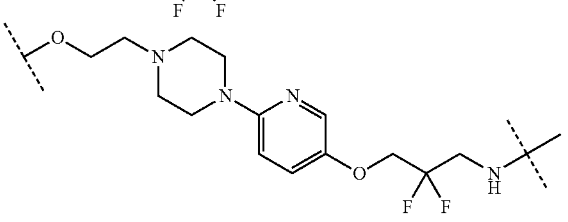
;
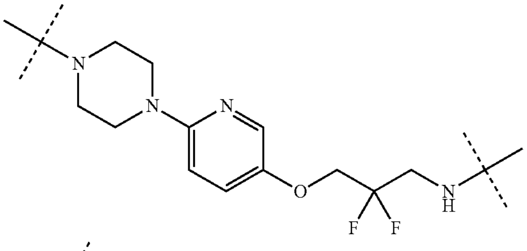
;
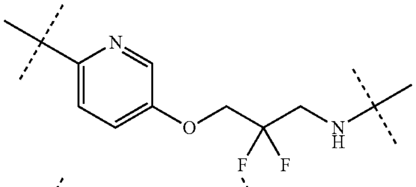
;
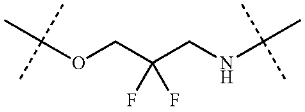
;
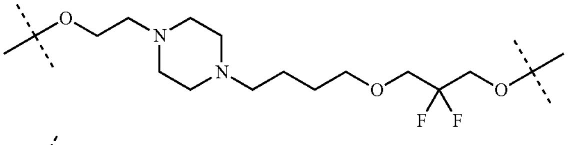
;
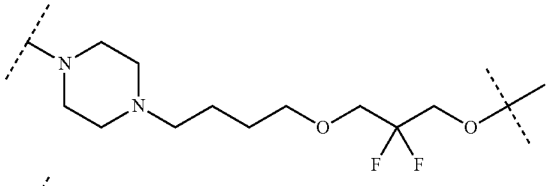
;
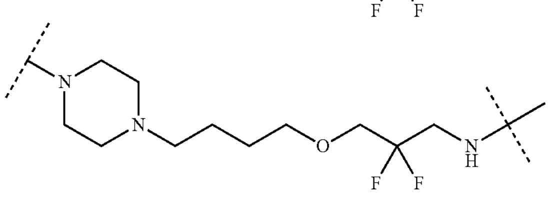
;

-continued
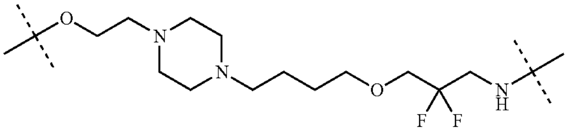
;
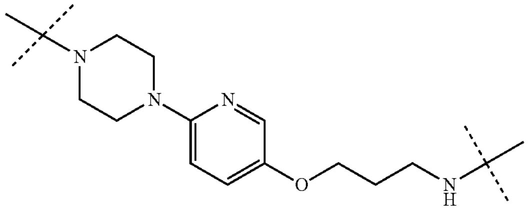
;
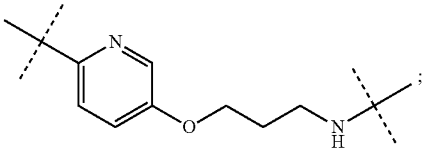
;
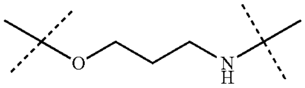
;
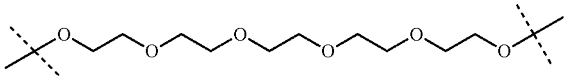
;
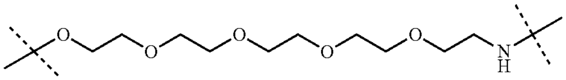
;
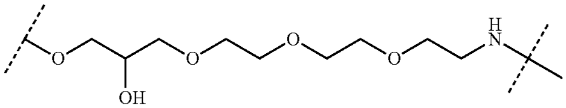
;
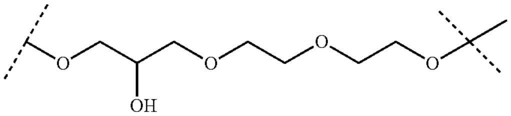
;
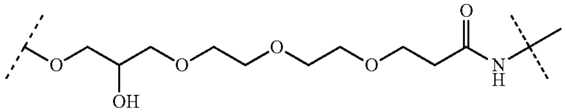
;
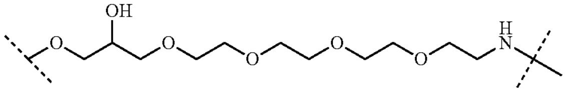
;
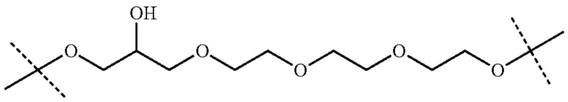
;
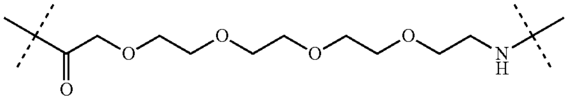
;
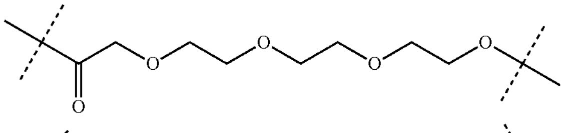
;
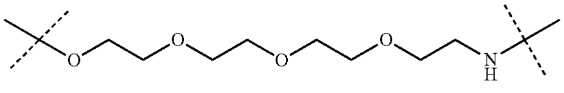
;
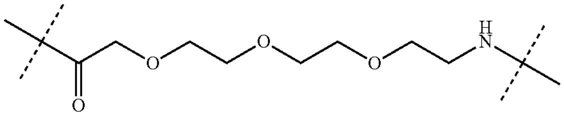
;
-continued
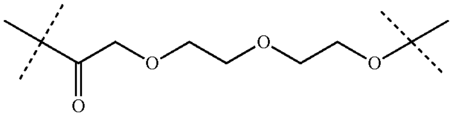
;
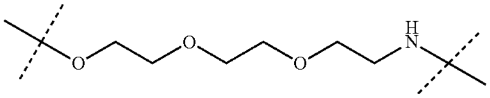
;
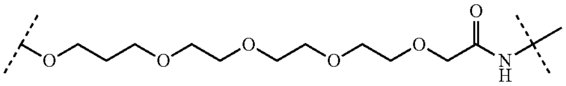
;
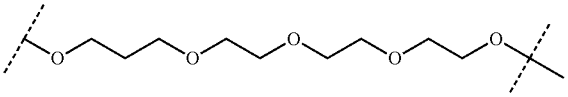
;
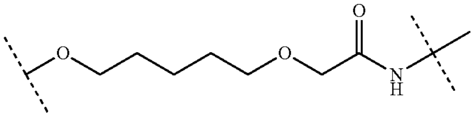
;
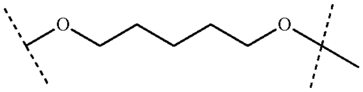
;
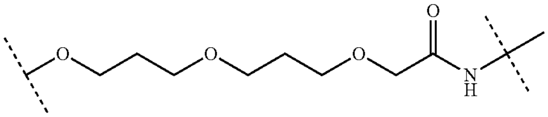
;
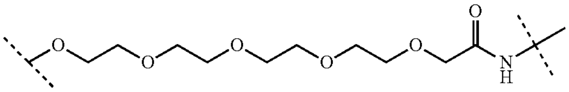
;
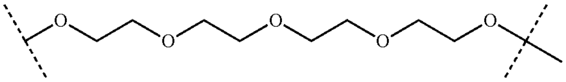
;
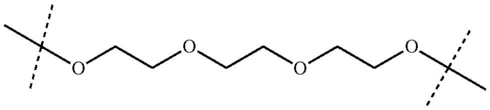
;
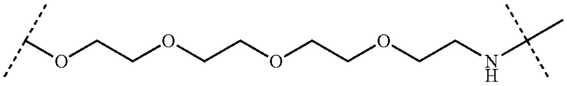
;
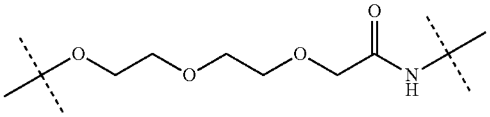
;
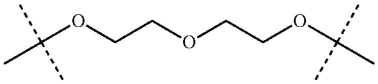
;
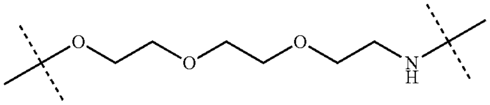
;
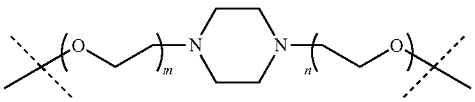
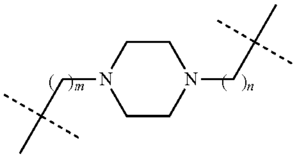

-continued
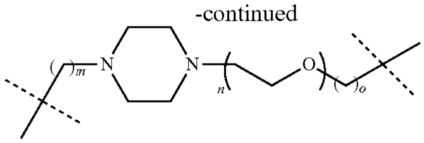
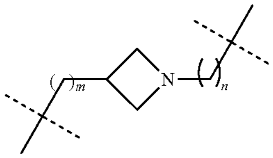
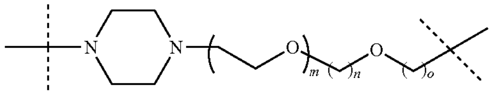
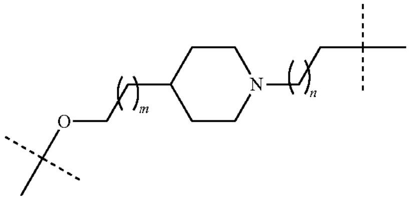
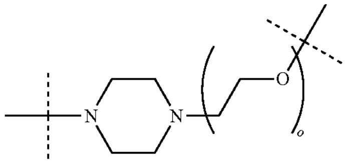
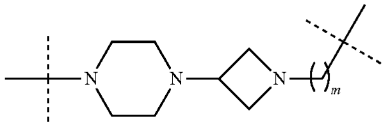
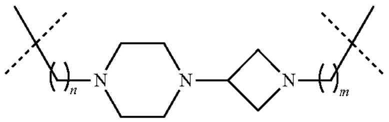
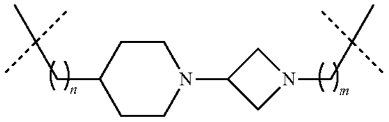
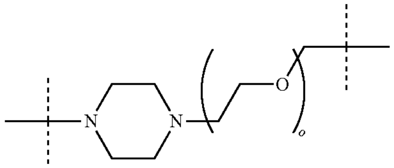
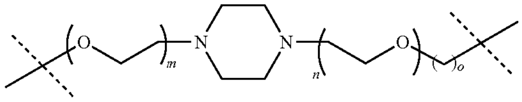
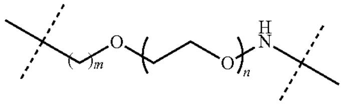
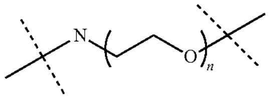
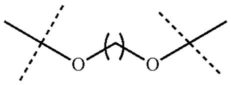
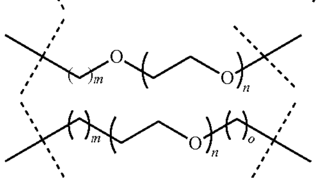
-continued
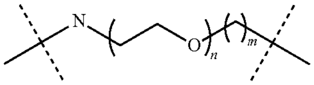
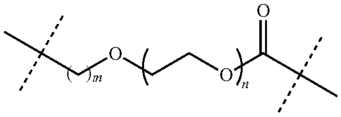
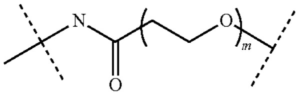
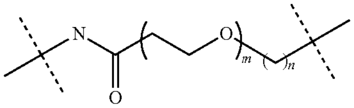
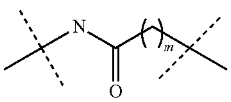
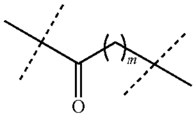
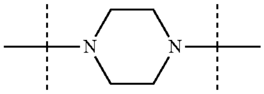
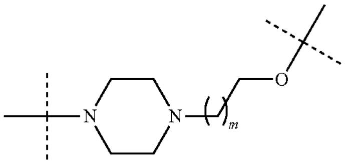
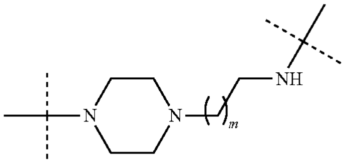
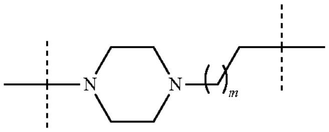
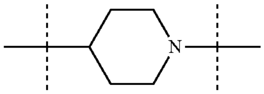
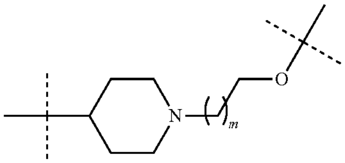
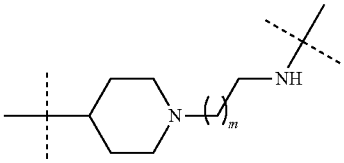
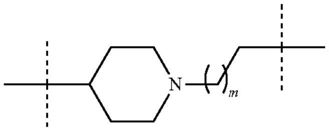

-continued
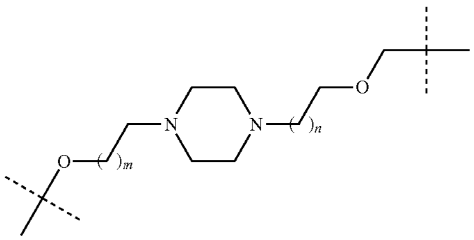
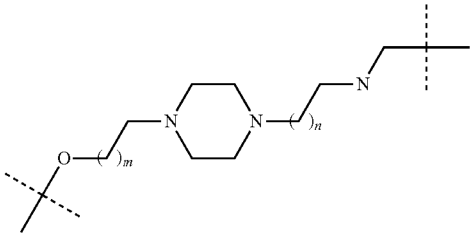
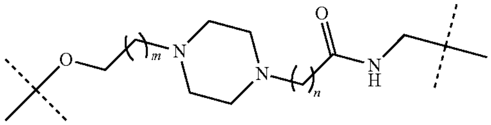
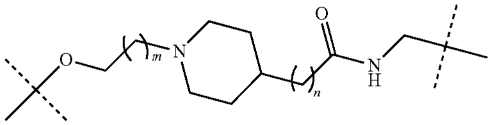
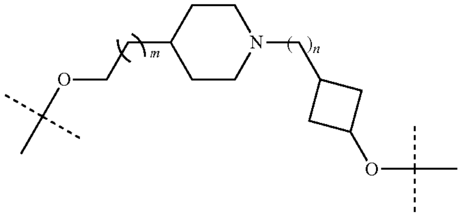
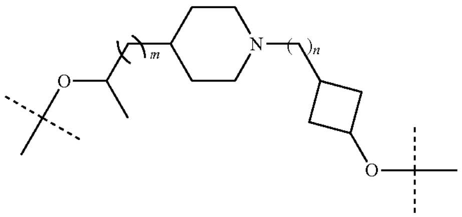
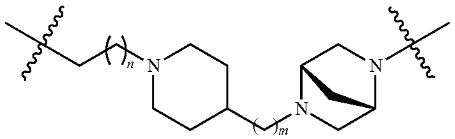
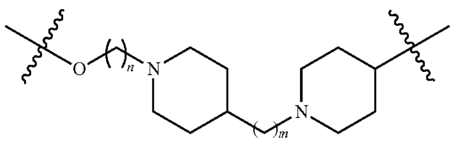
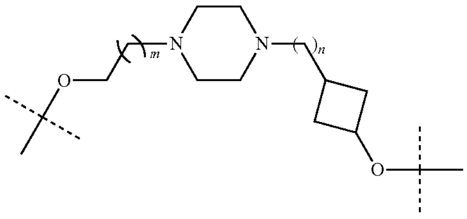
-continued
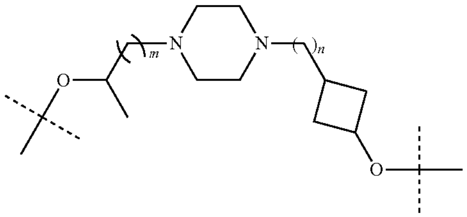
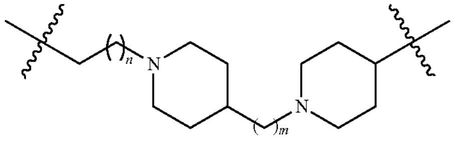
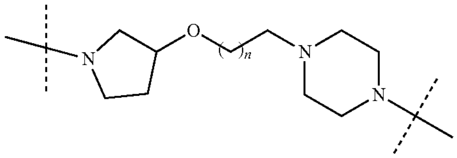
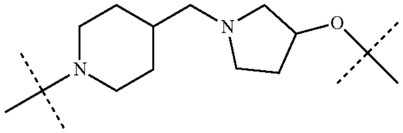
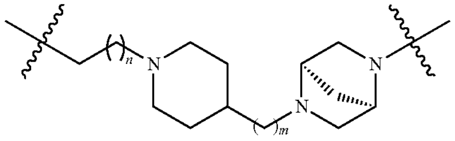
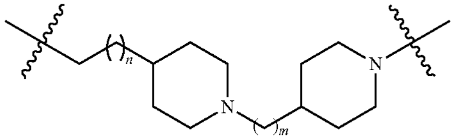
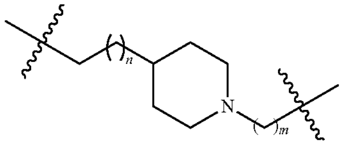
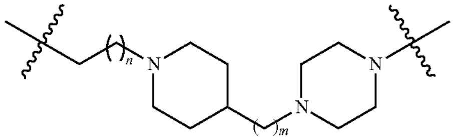
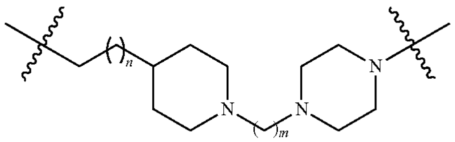
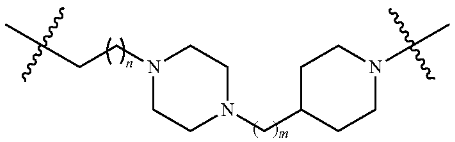
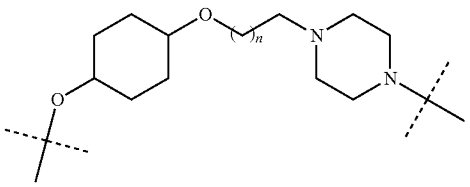

-continued
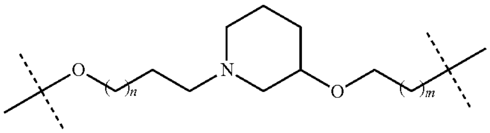
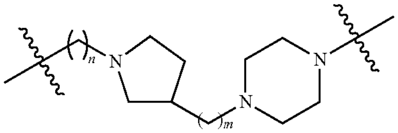
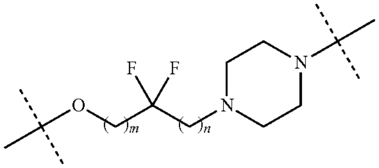
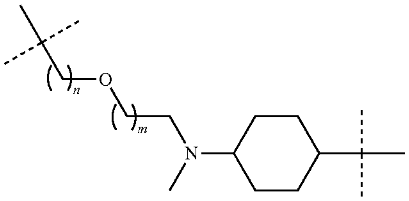
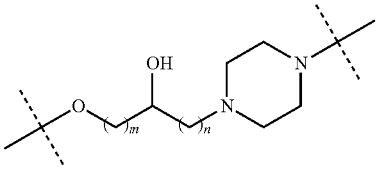
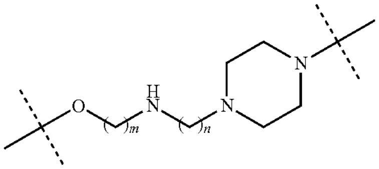
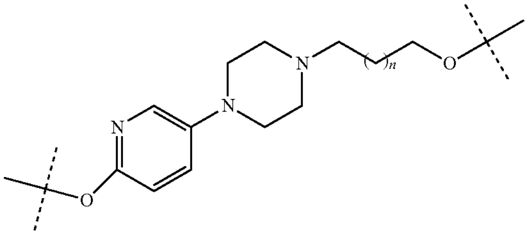
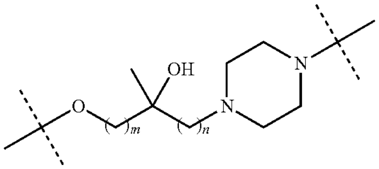
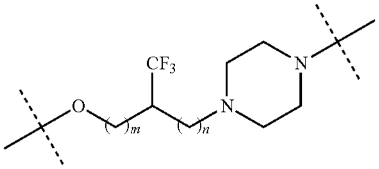
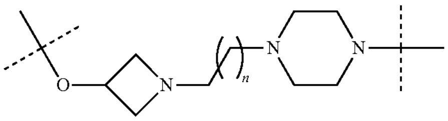
-continued
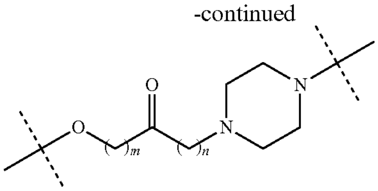
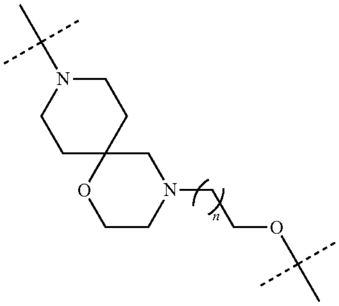
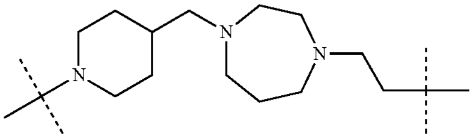
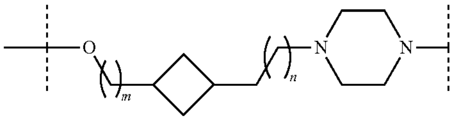
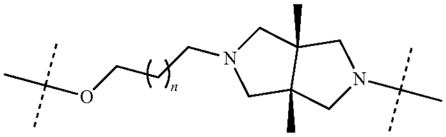
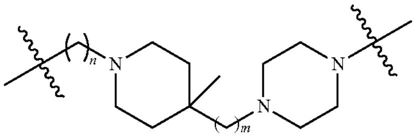
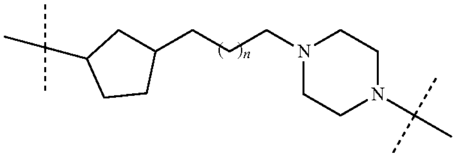
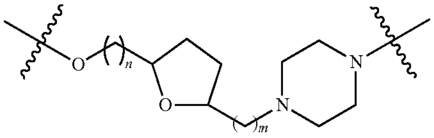
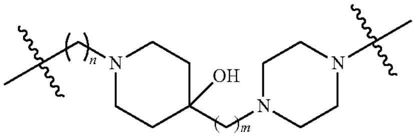
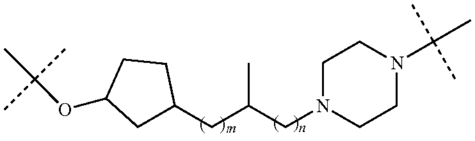
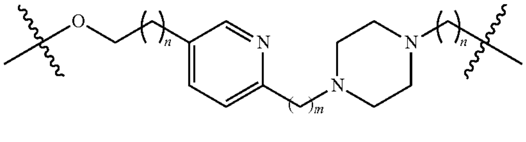

-continued
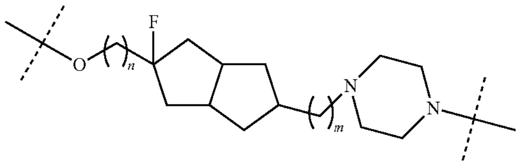
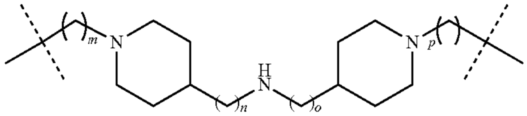
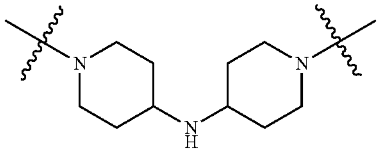
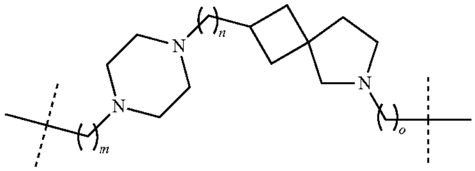
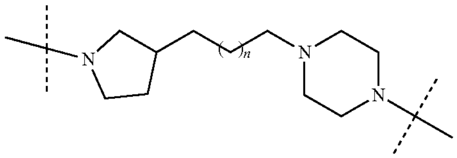
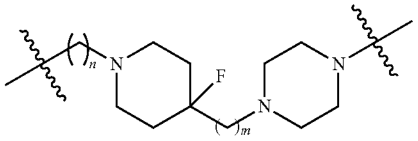
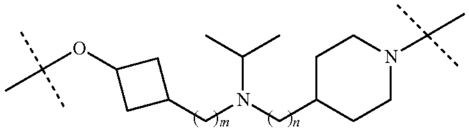
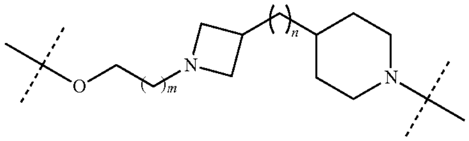
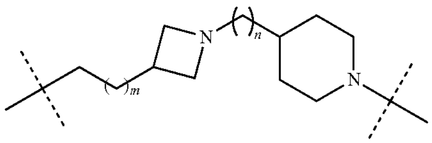
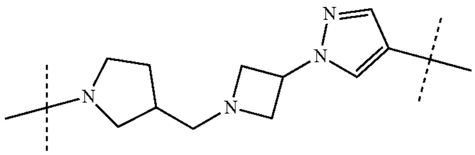
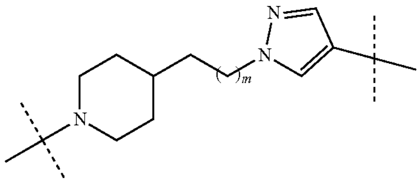
-continued
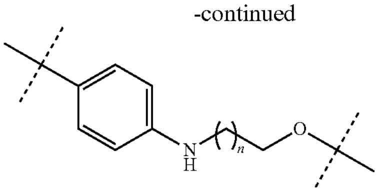
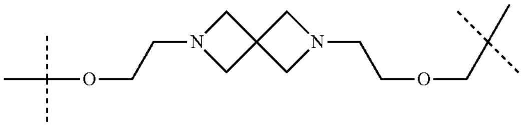
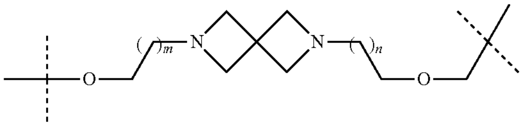
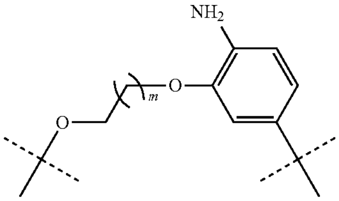
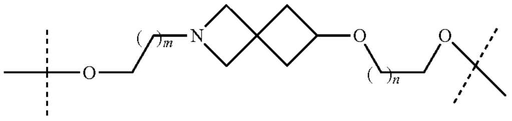
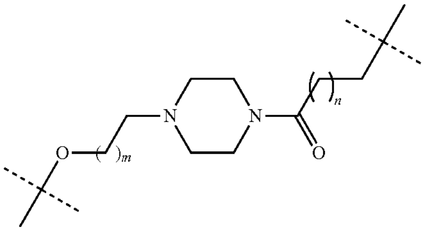
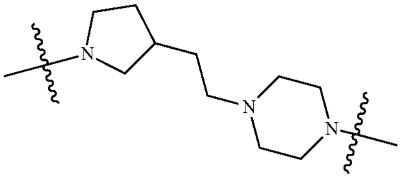
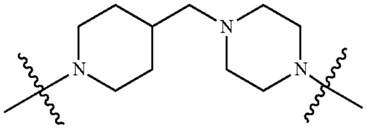
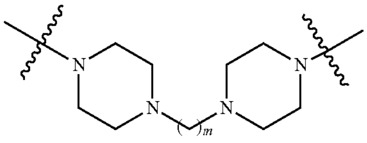
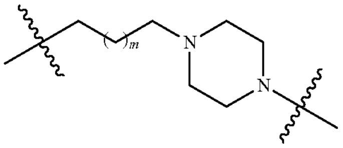
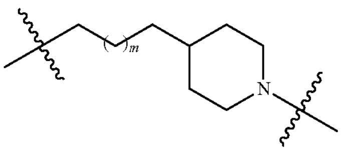

-continued
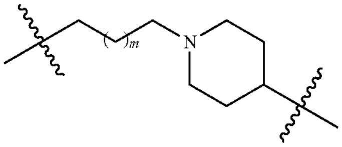
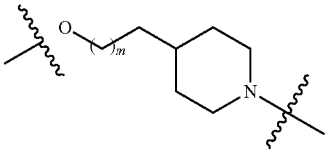
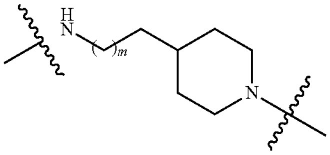
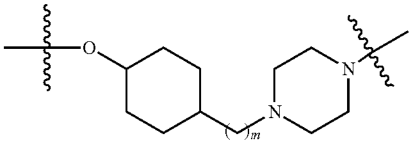
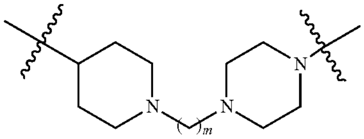
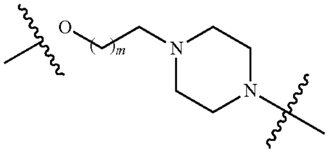
-continued
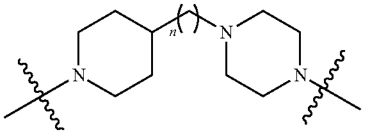
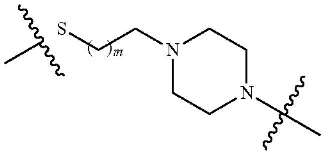
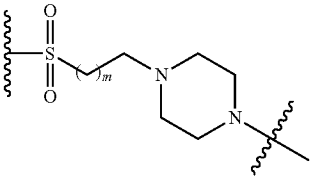
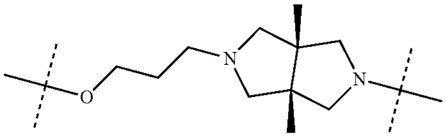
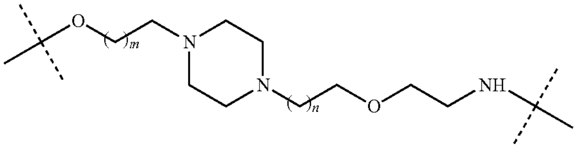
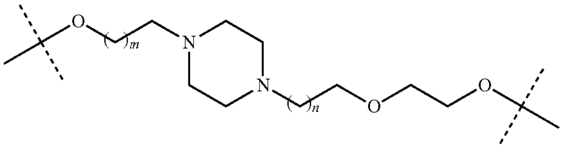
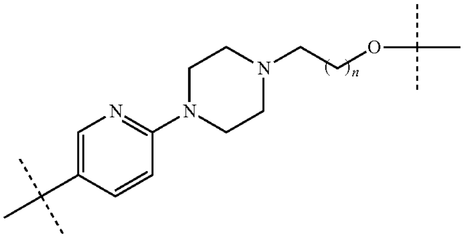
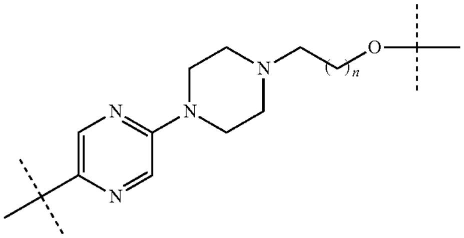
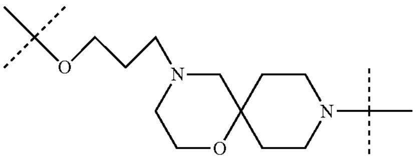
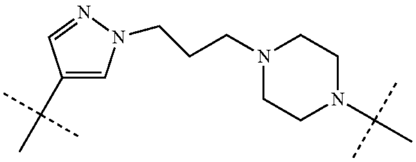
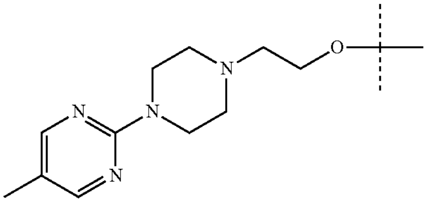
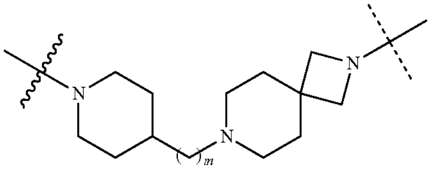

-continued
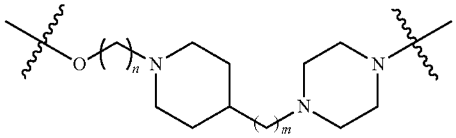
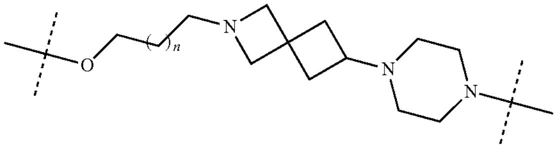
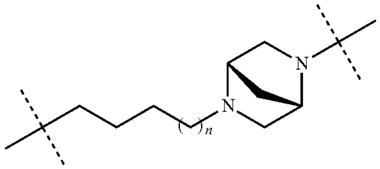
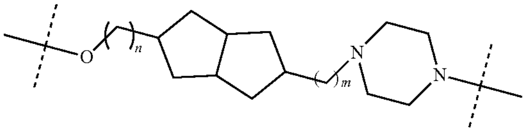
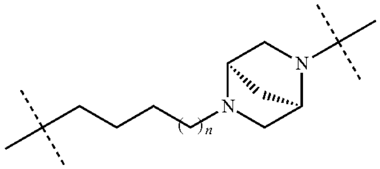
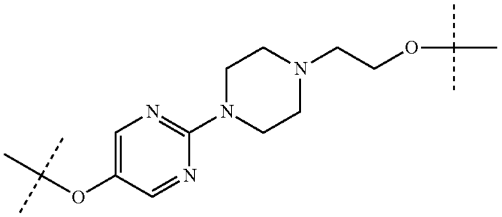
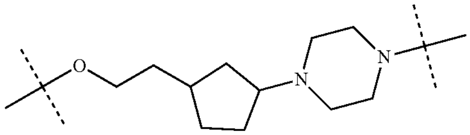
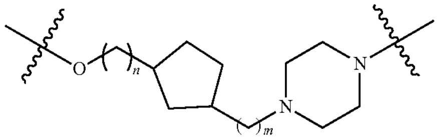
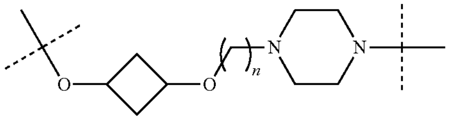
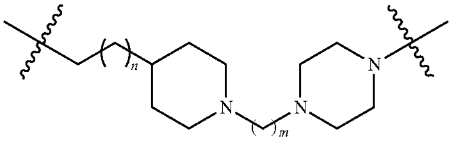
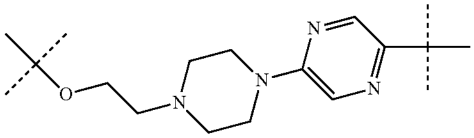
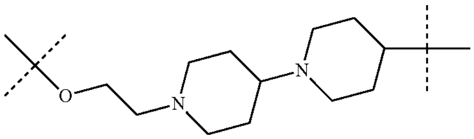
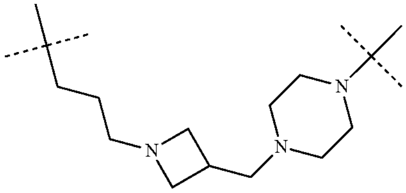
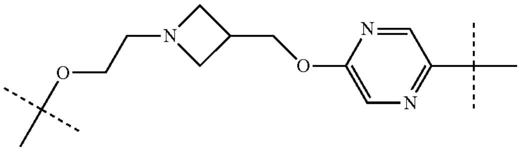
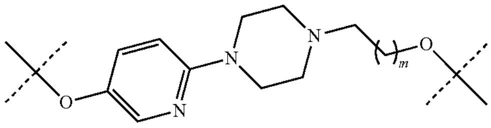
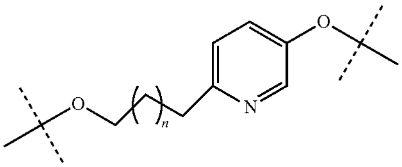
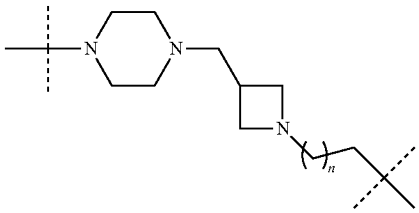
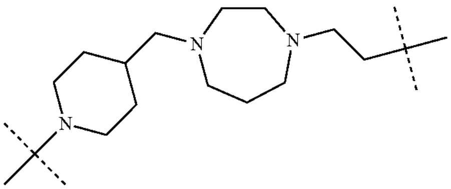
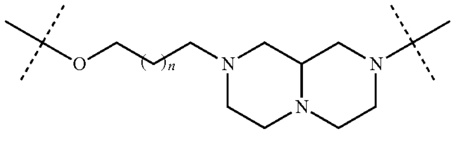
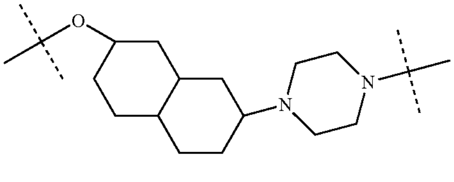

-continued
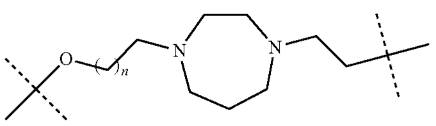
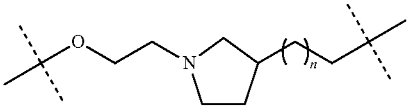
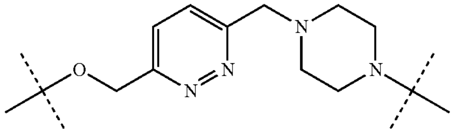
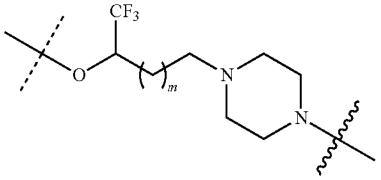
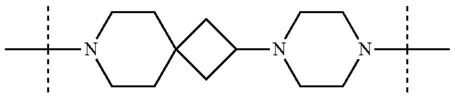
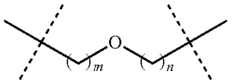
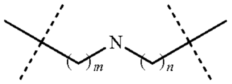
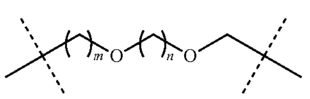
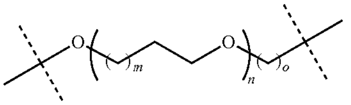
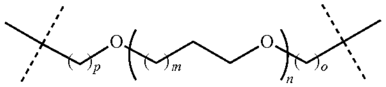
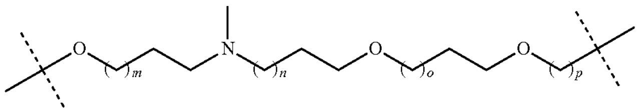
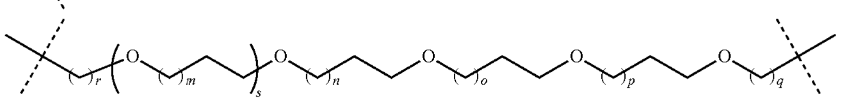
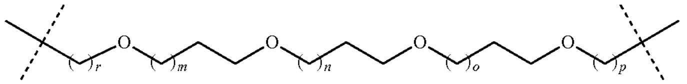
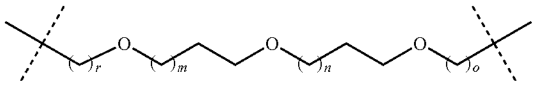
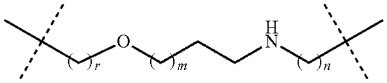
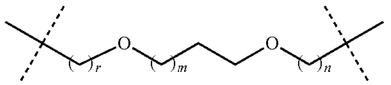
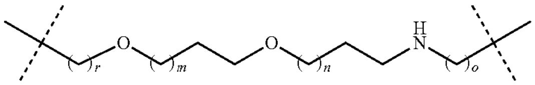
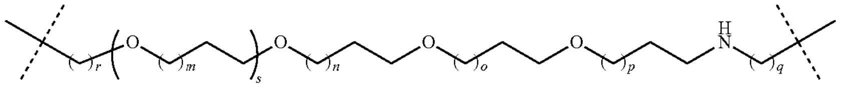
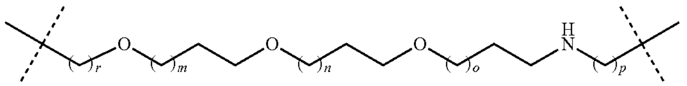
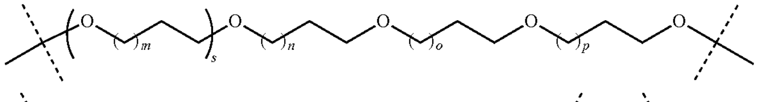
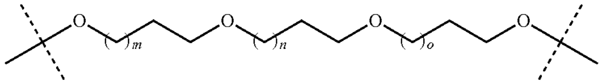
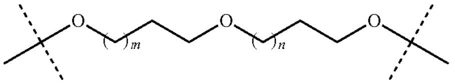
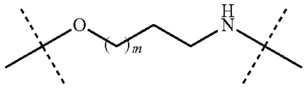
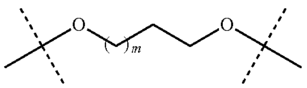
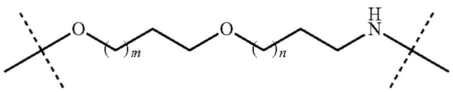
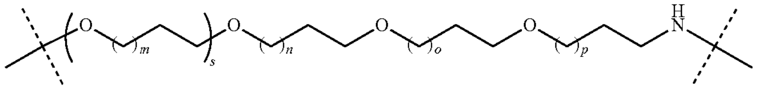
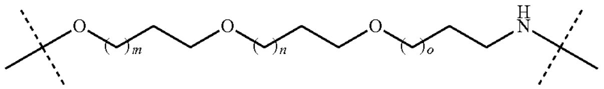
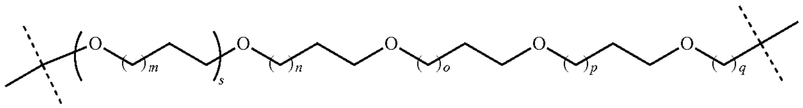

-continued
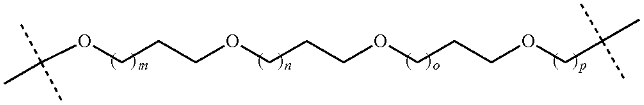
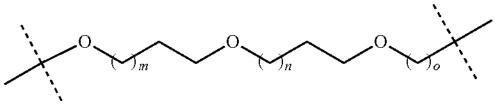
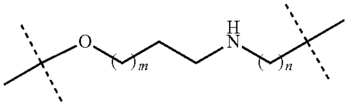
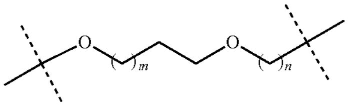
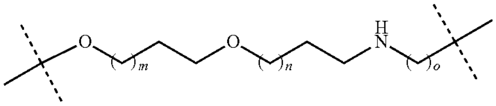
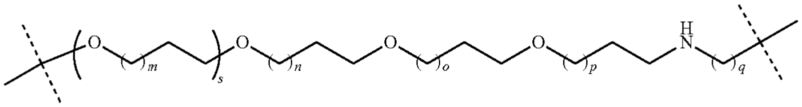
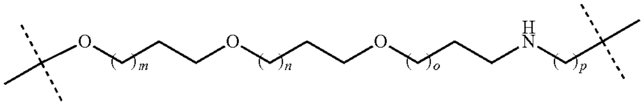
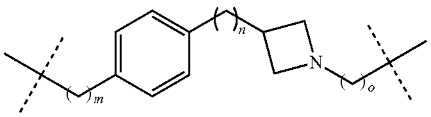
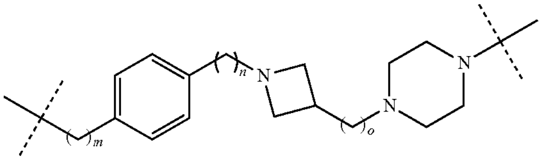
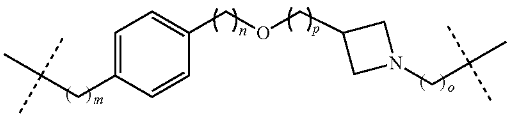
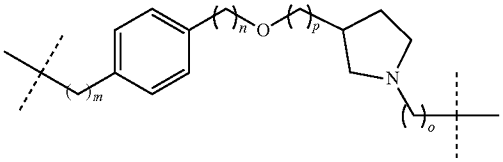
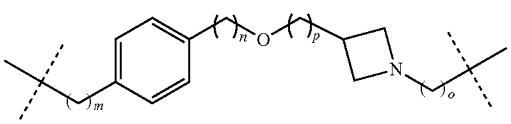
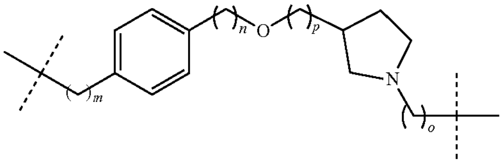
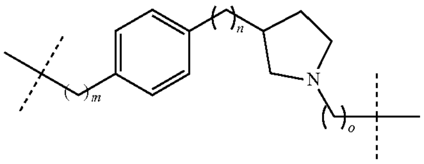
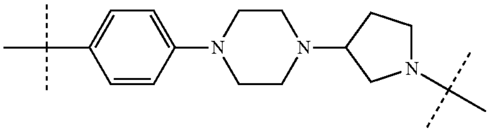
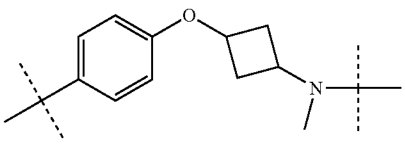
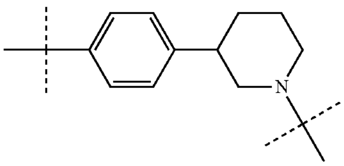
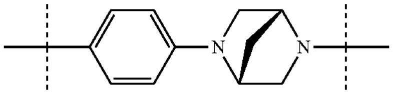
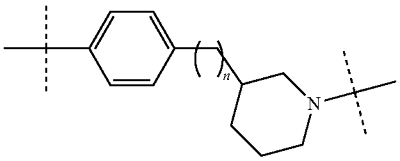

-continued
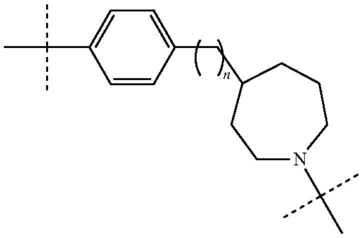
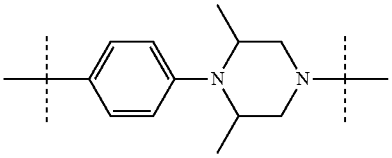
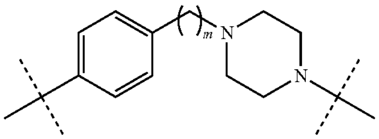
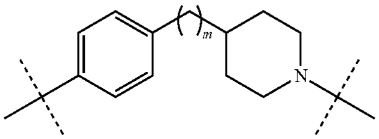
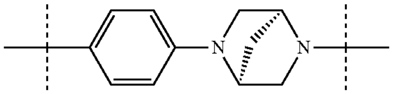
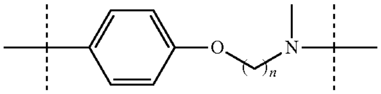
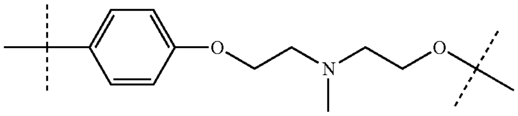
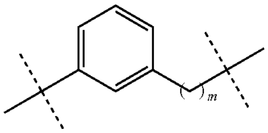
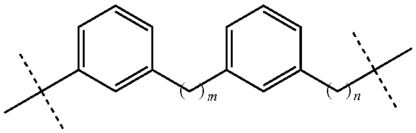
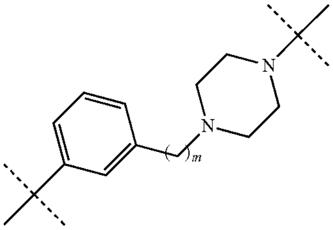
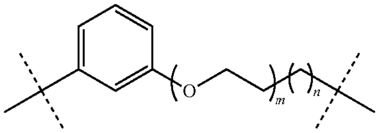
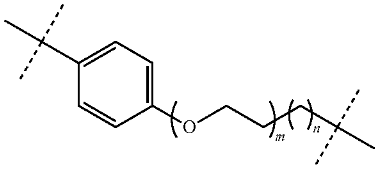
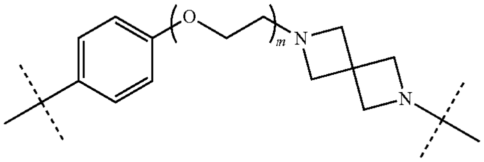
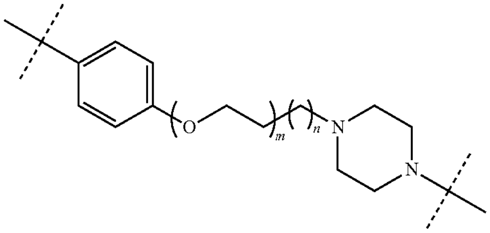
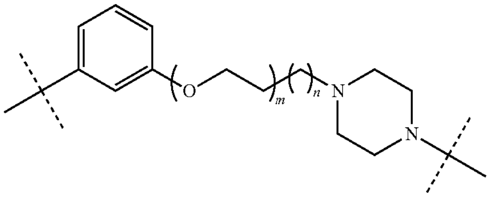
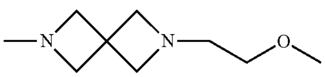
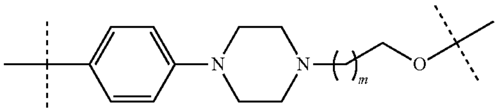
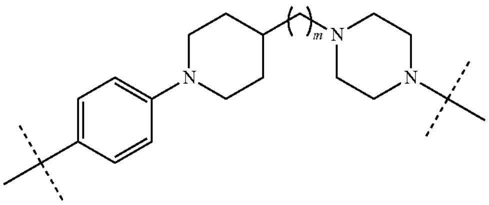

-continued
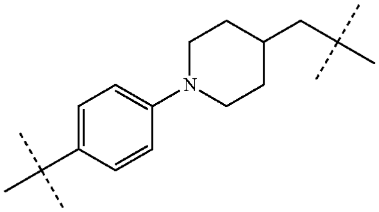
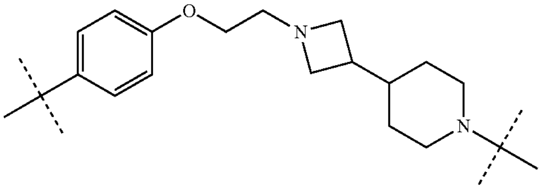
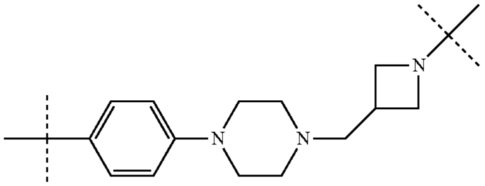
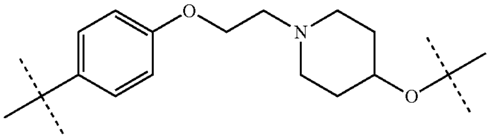
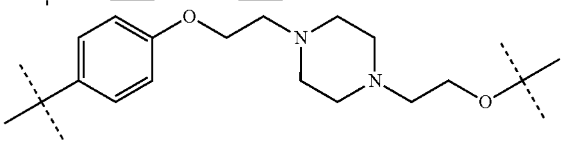
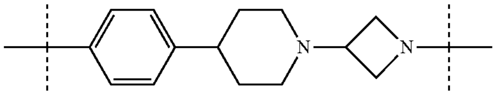
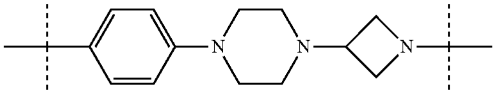
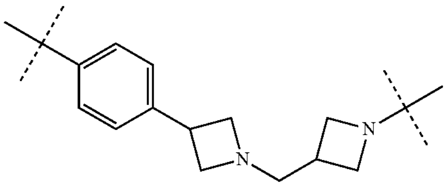
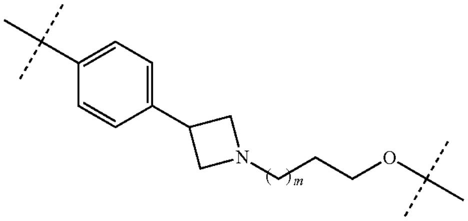
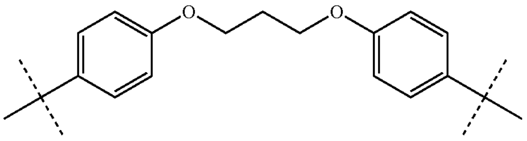
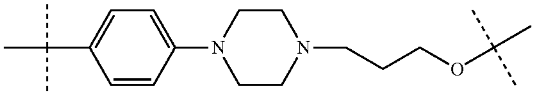
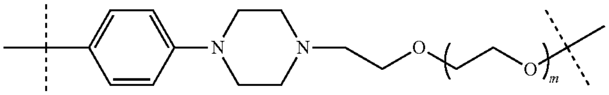
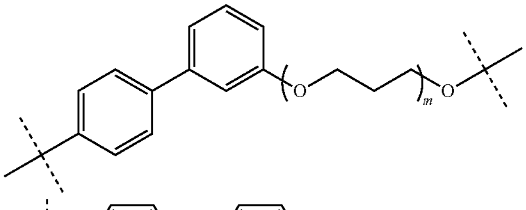
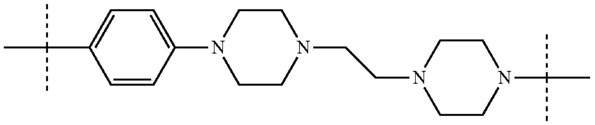
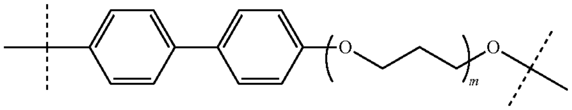
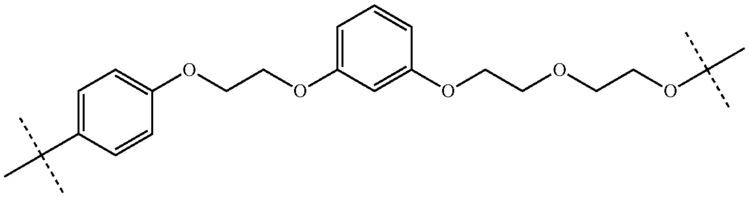
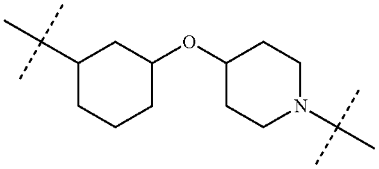
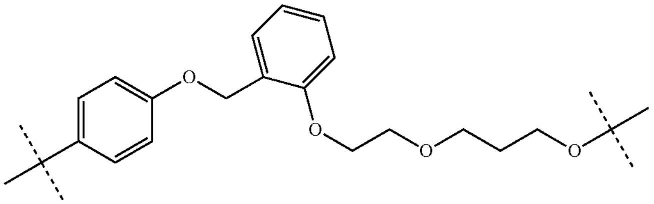
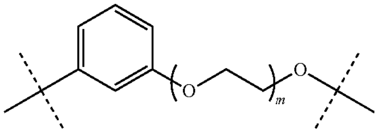

-continued
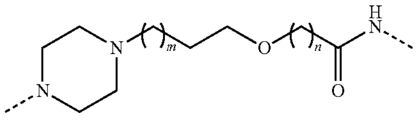
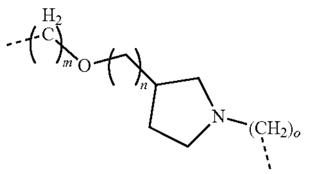
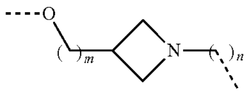
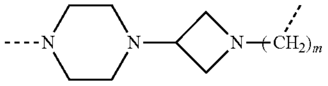
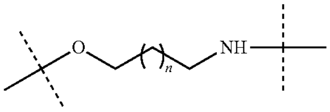
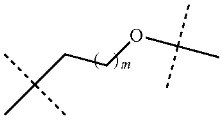
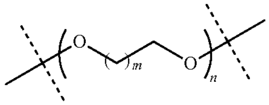
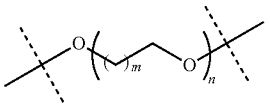
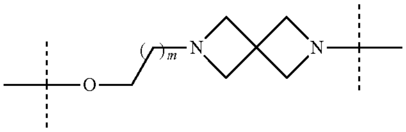
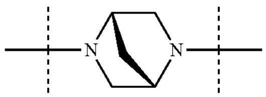
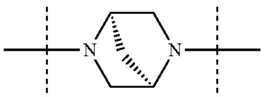
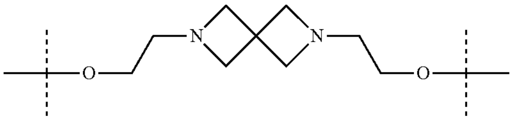
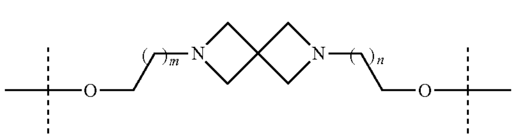
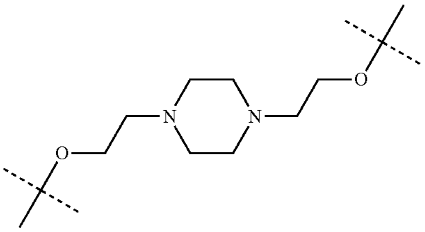
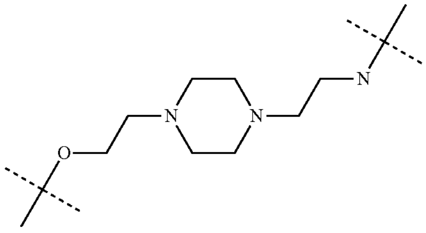
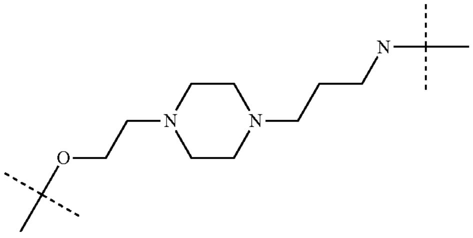
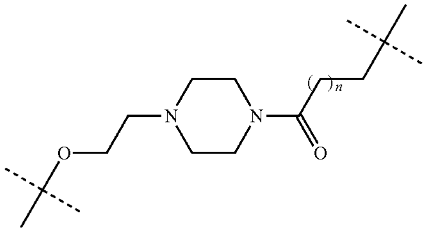
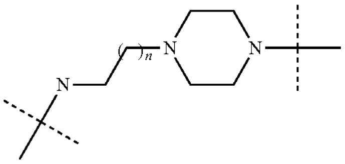
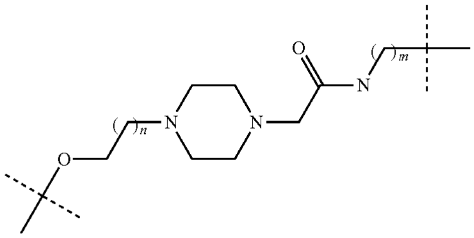
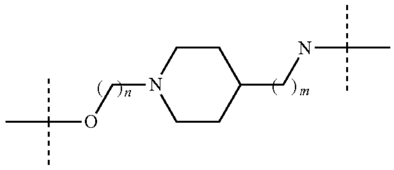
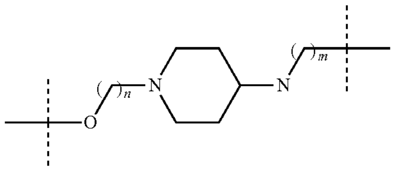
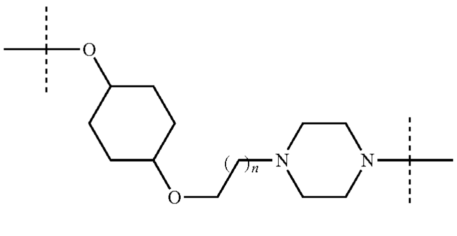

-continued
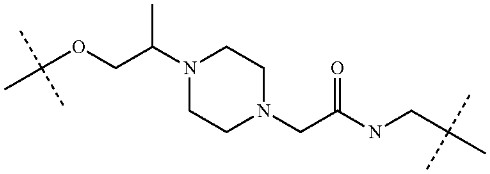
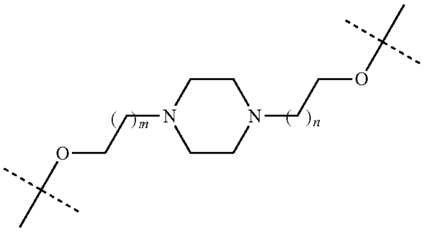
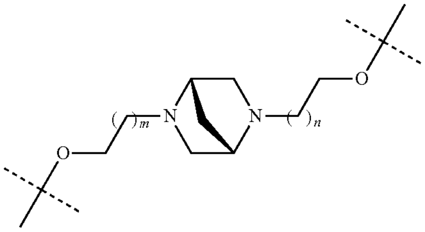
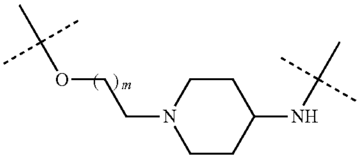
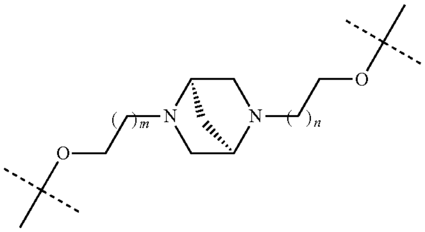
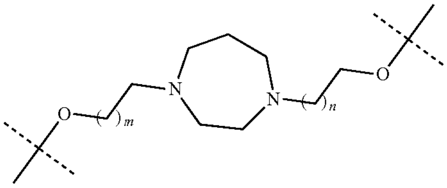
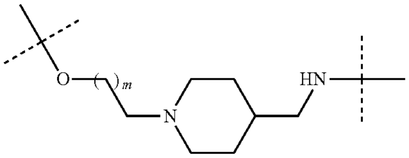
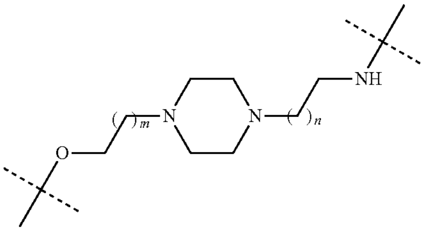
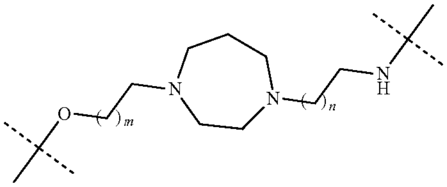
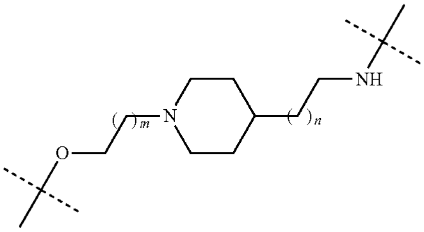
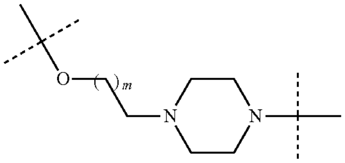
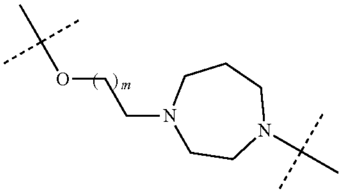
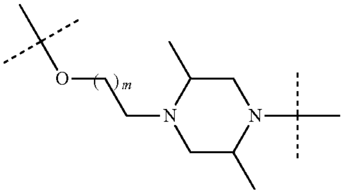
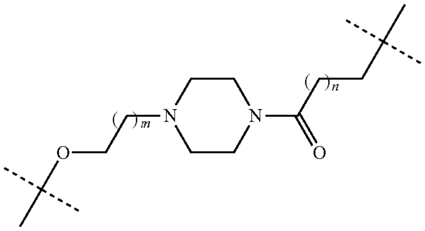
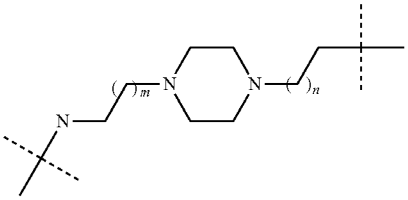

-continued
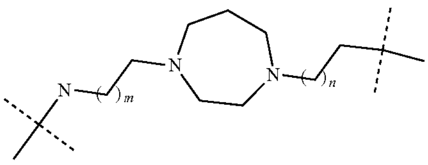
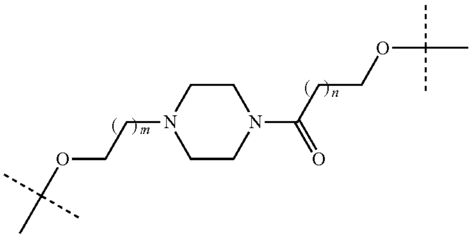
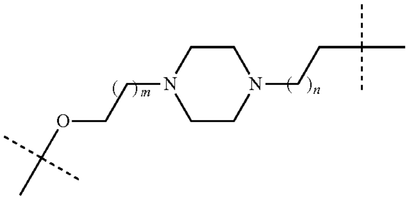
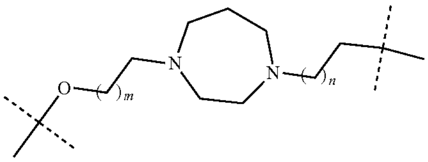
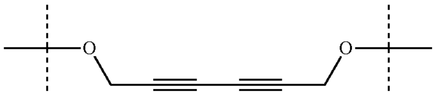
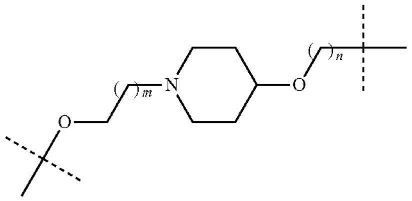
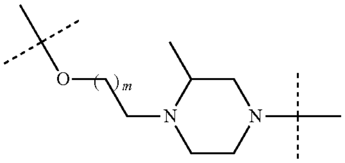
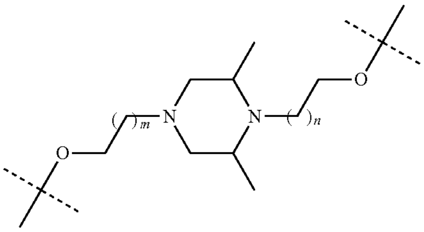
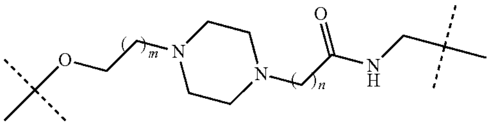
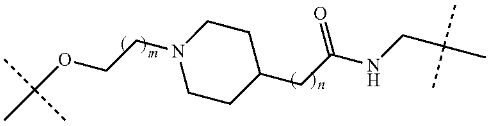
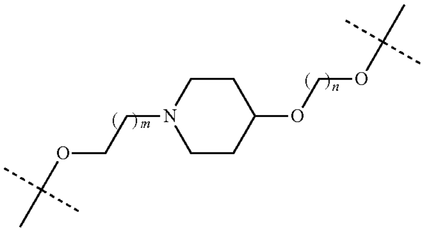
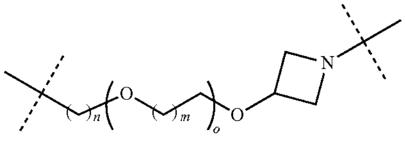
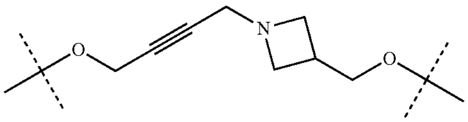
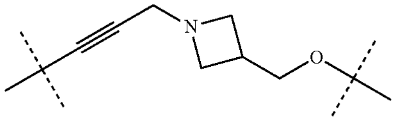
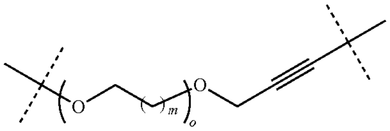
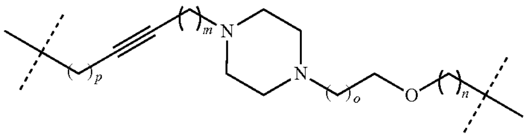
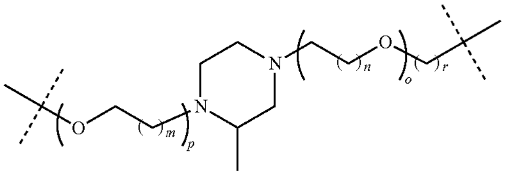

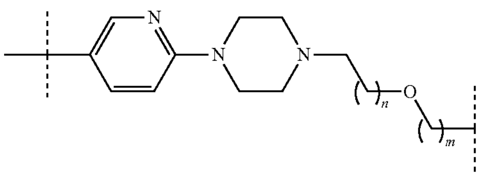
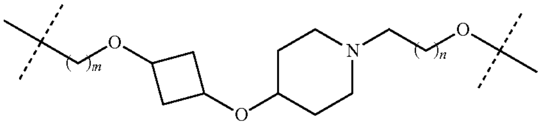
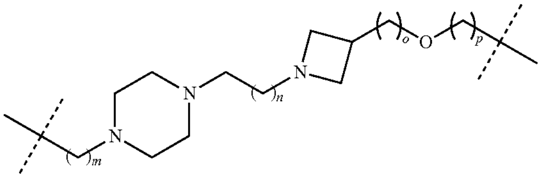
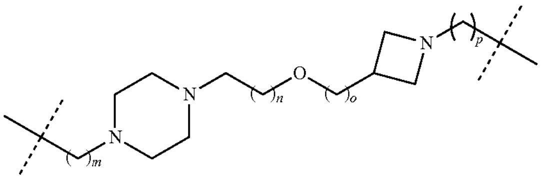
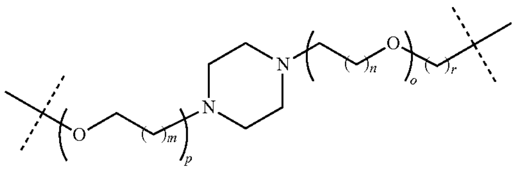
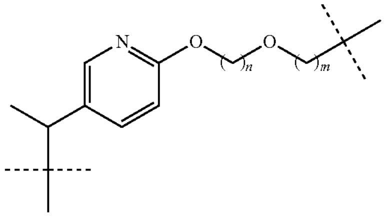
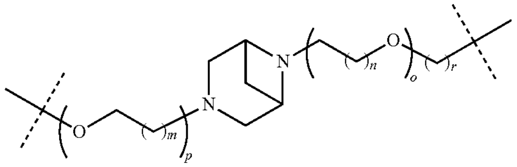
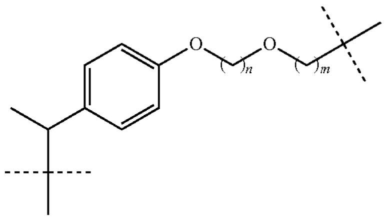
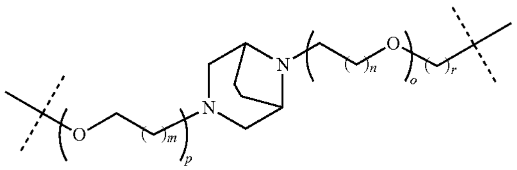
-continued
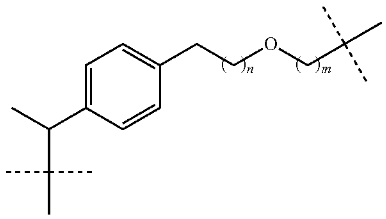
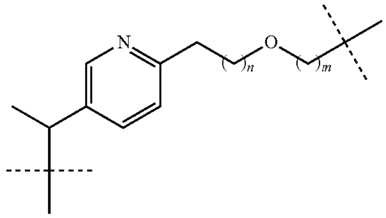
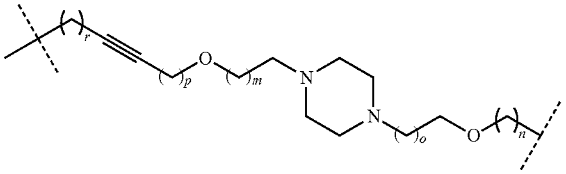
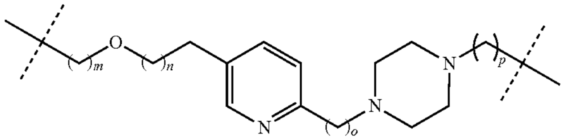
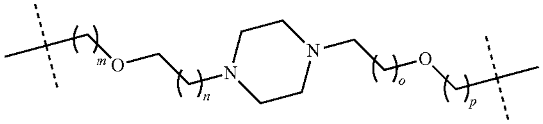
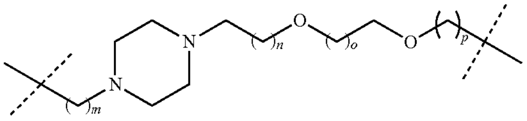
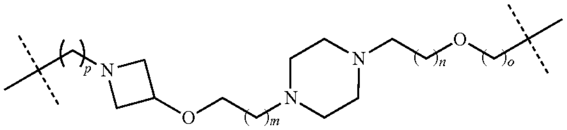
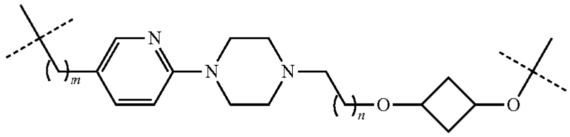
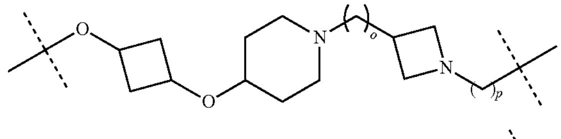
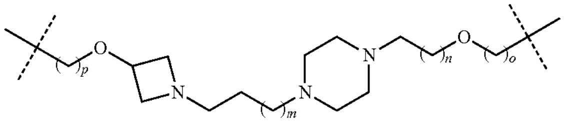
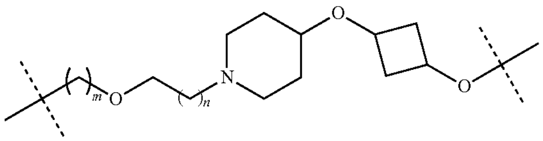

-continued
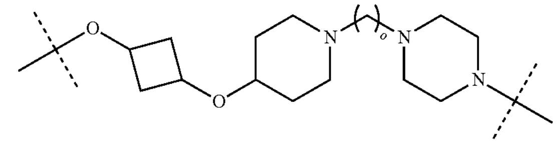
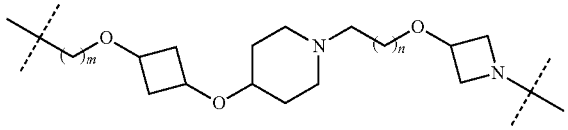
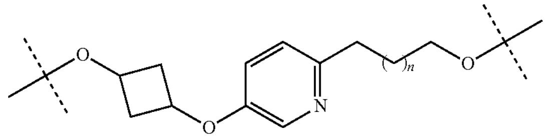
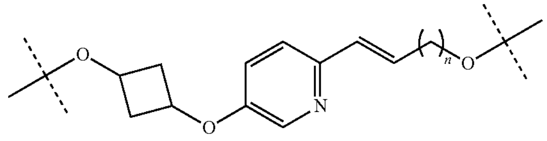
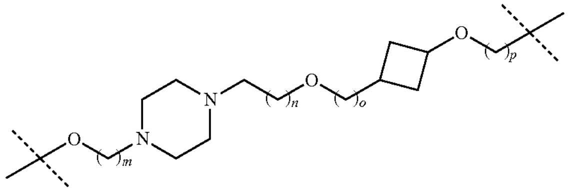
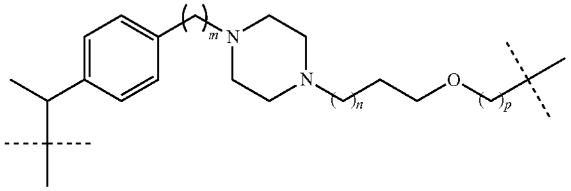
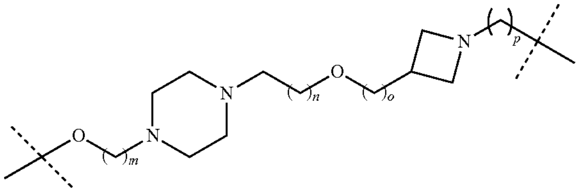
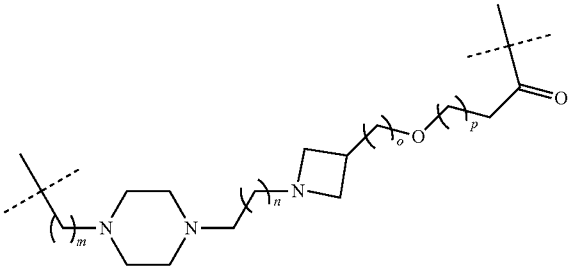
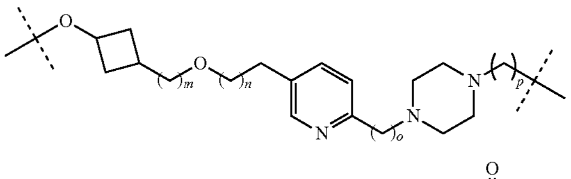
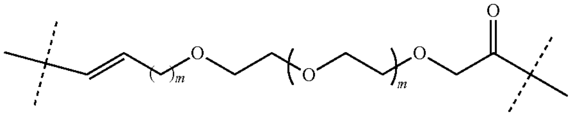
-continued
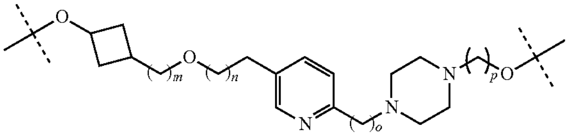
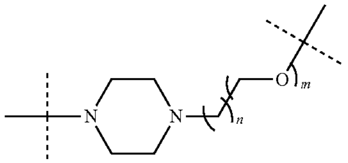
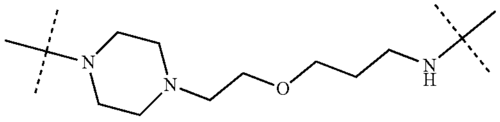
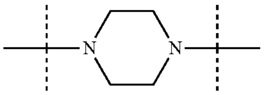
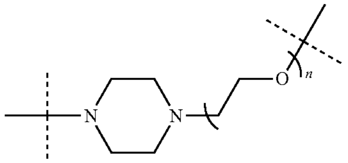
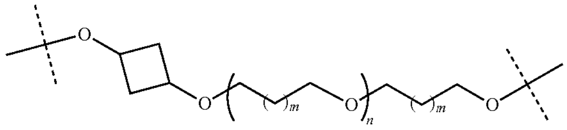
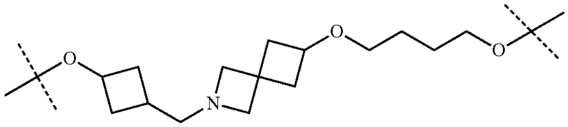
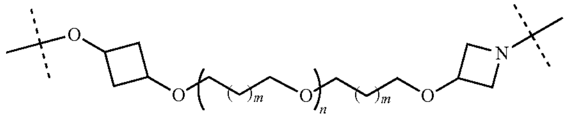
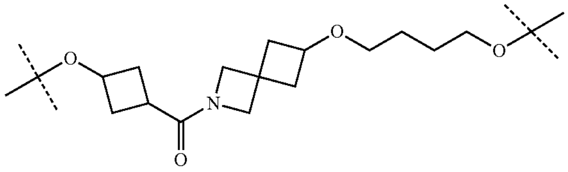
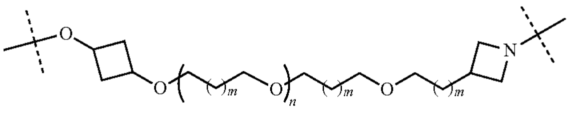
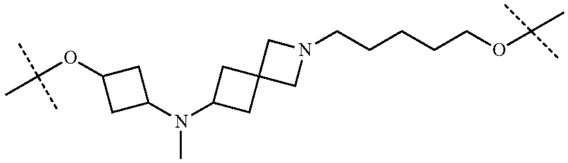
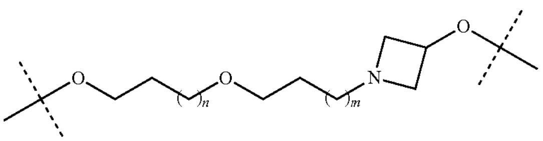

-continued
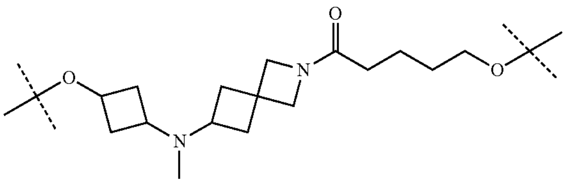
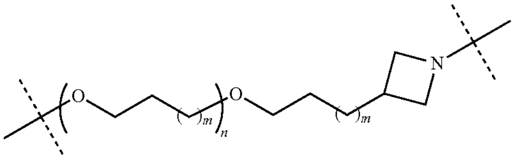
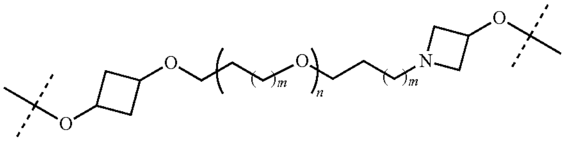
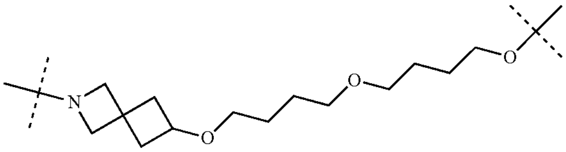
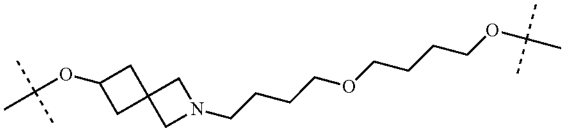
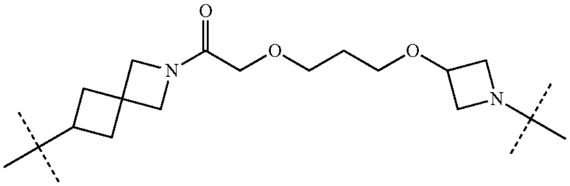
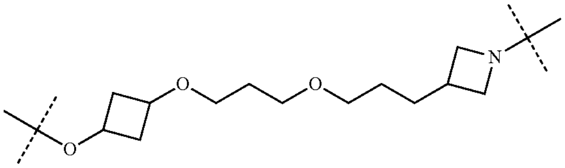
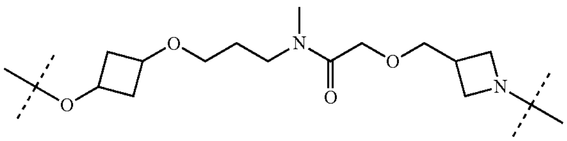
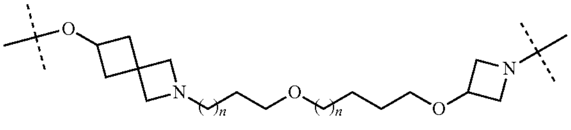
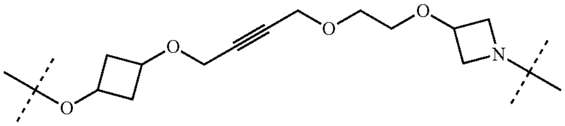
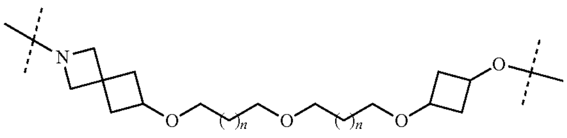
-continued
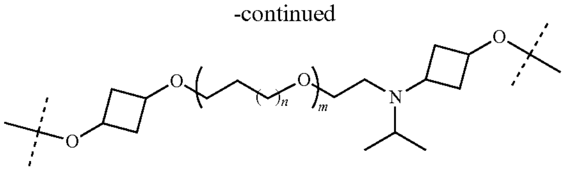
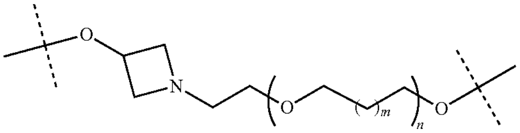
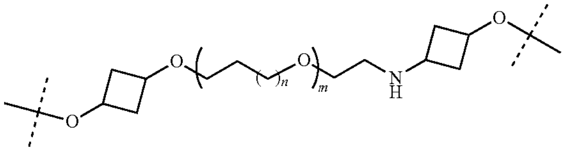
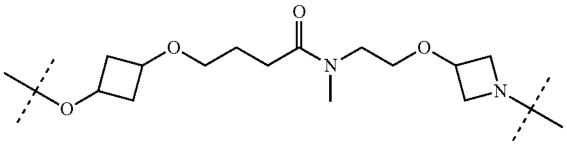
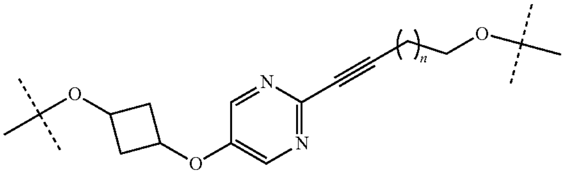
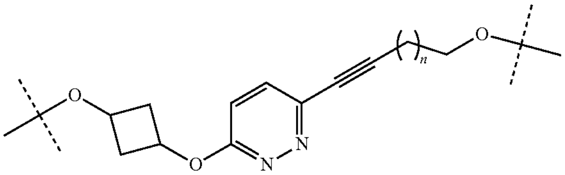
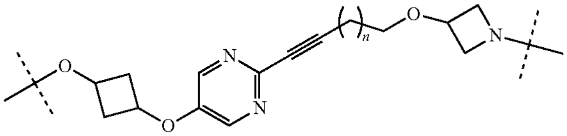
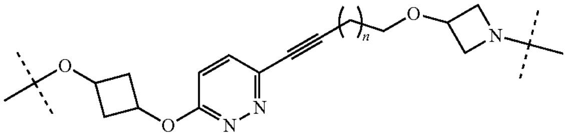
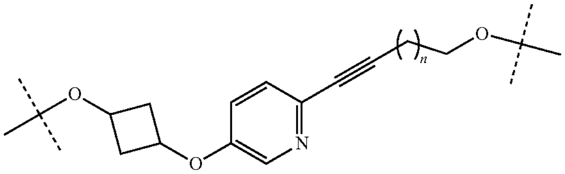
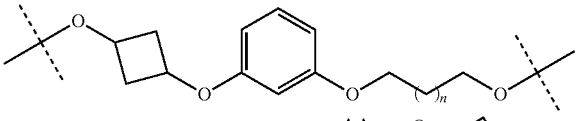
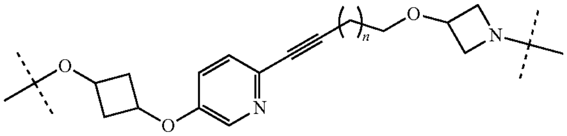
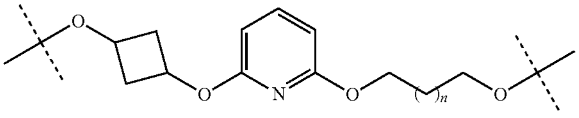

-continued
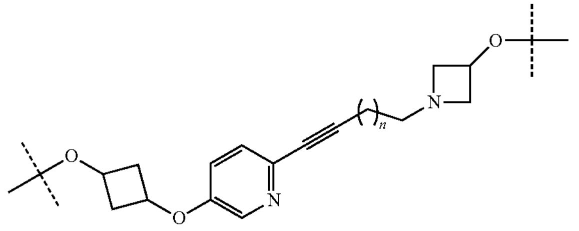
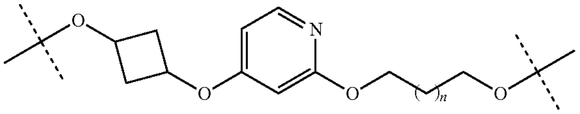
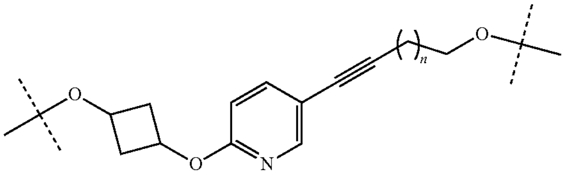
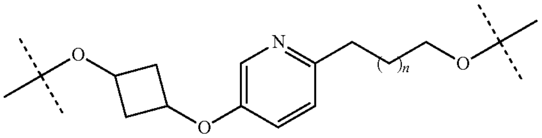
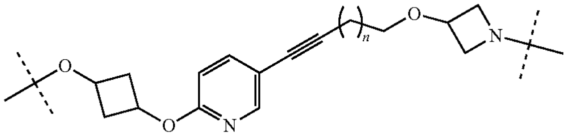
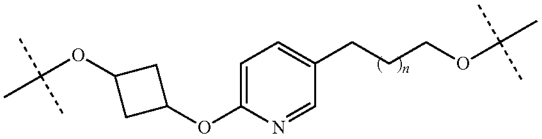
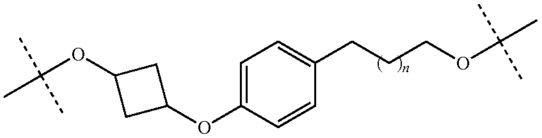
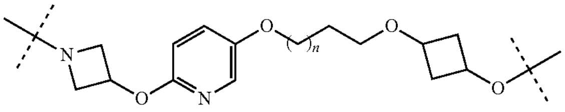
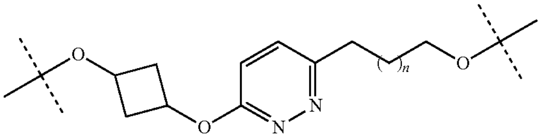
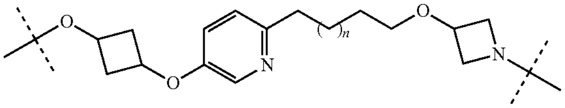
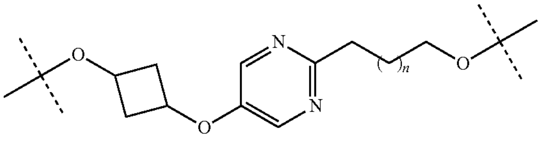
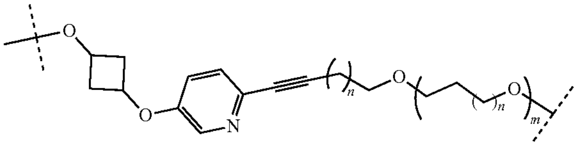
-continued
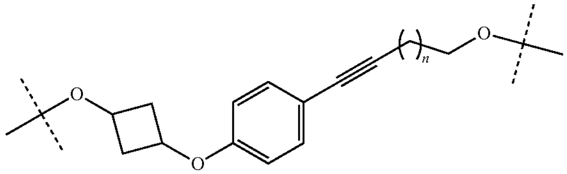
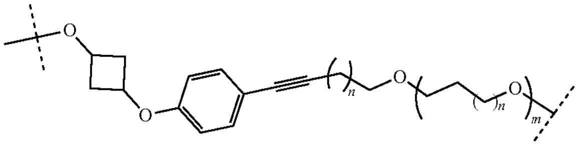
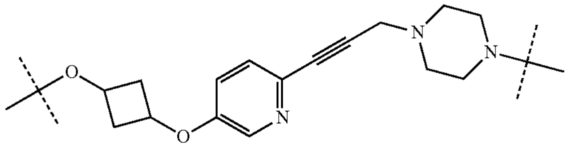
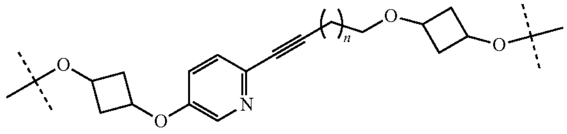
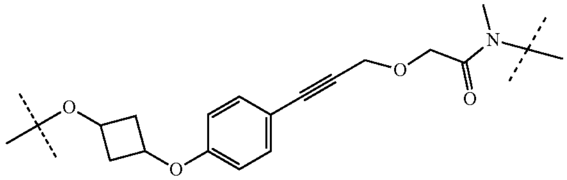
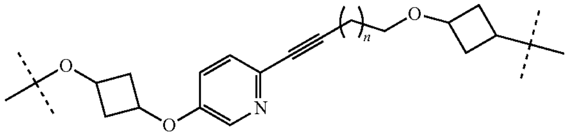
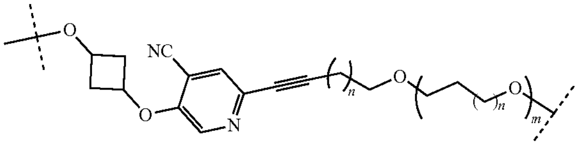
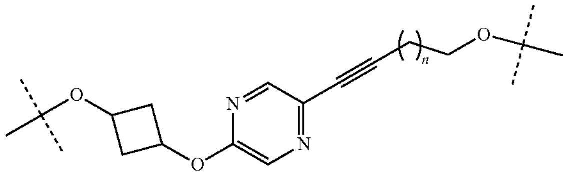
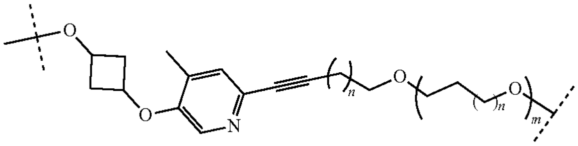
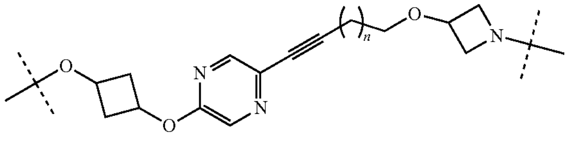
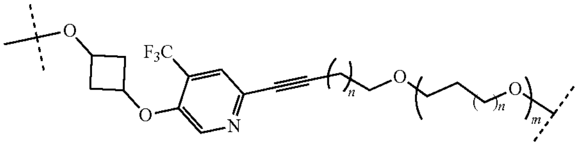

-continued
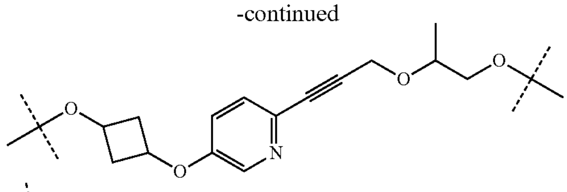
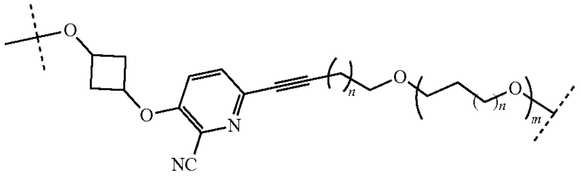
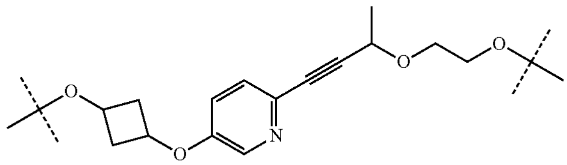
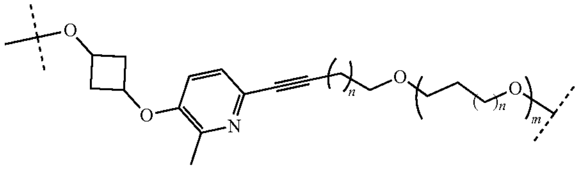
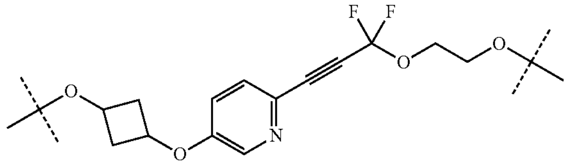
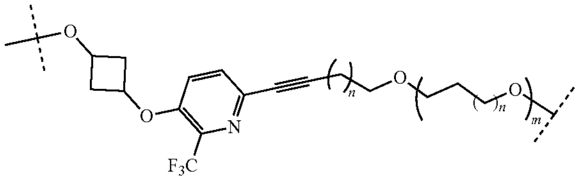
-continued
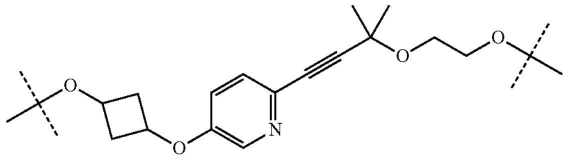
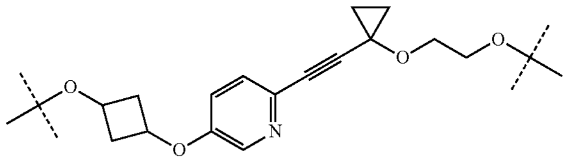
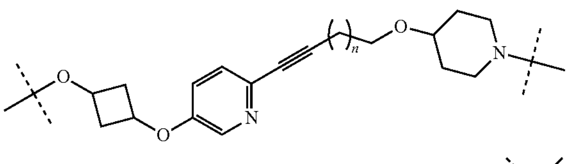
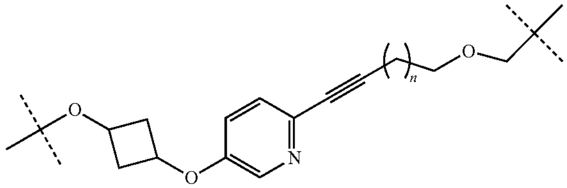
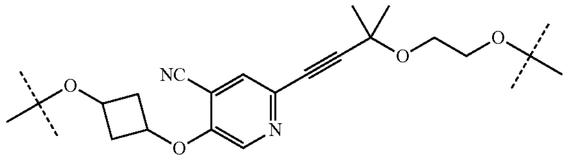
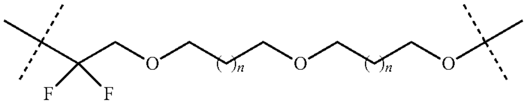
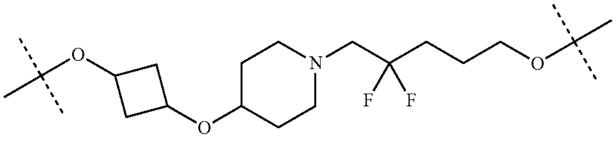
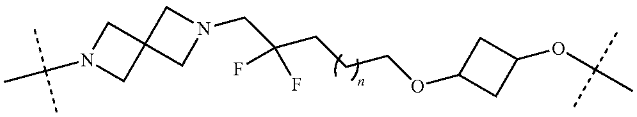
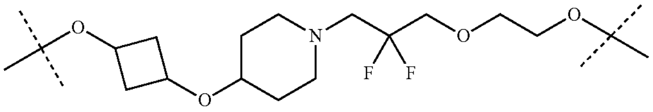
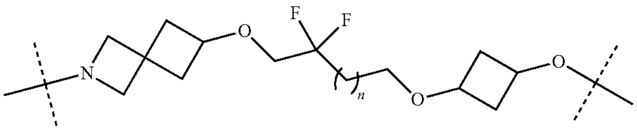
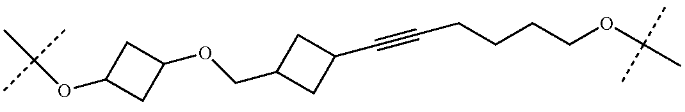

-continued
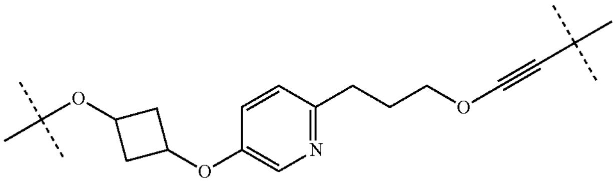
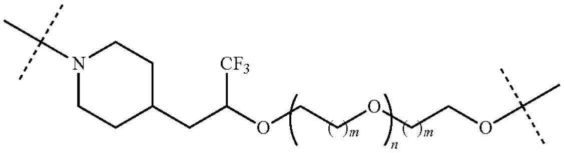
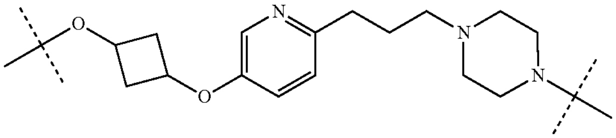
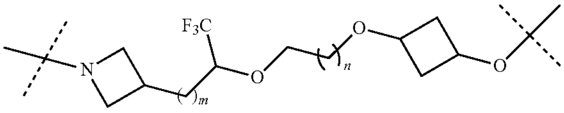
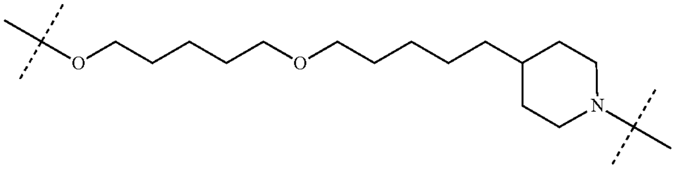
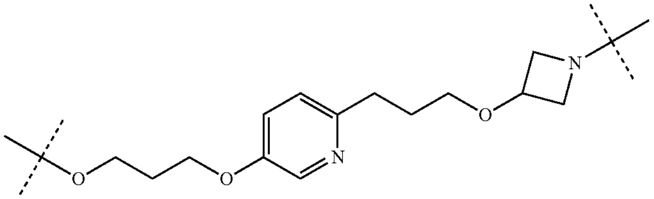
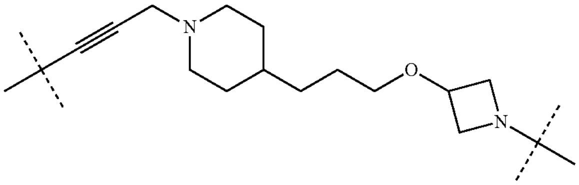
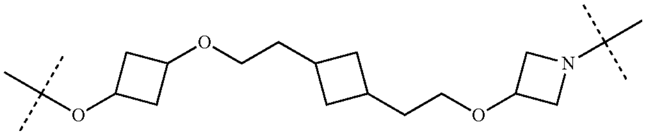
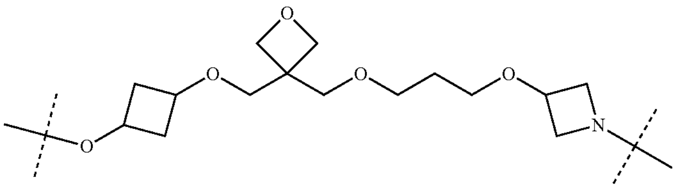
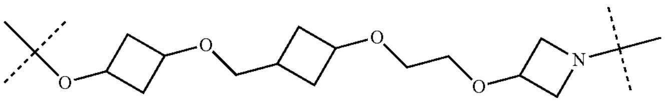
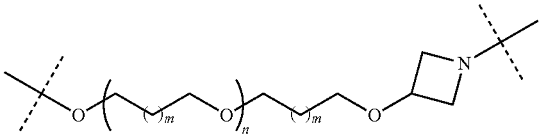
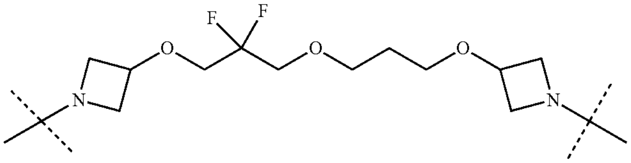
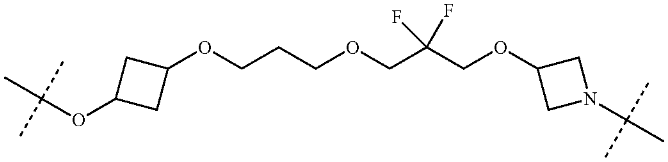
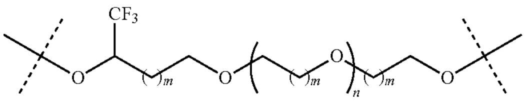

-continued
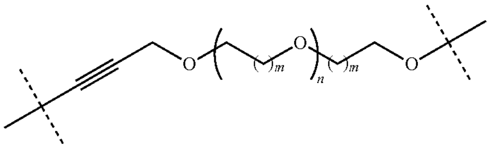
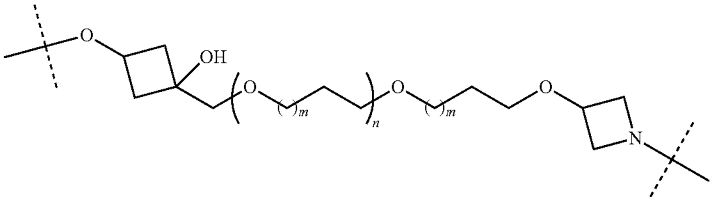
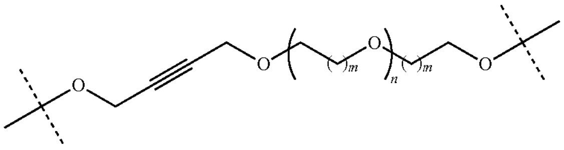
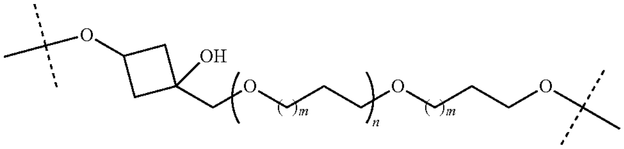
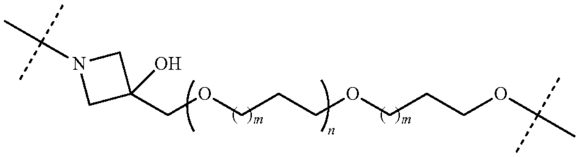
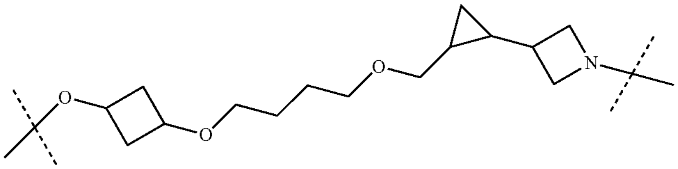
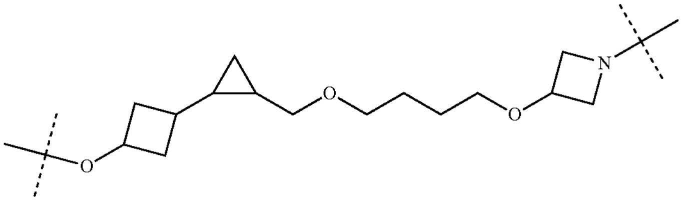
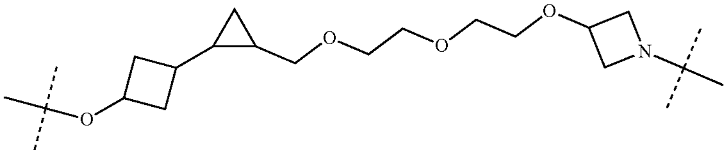
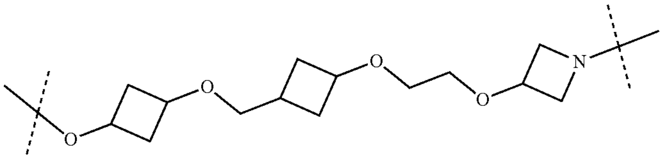
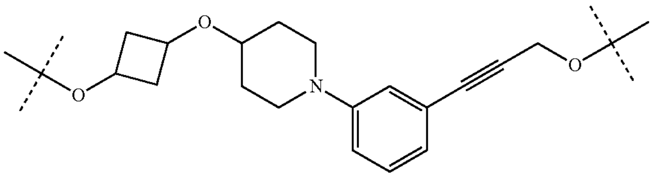
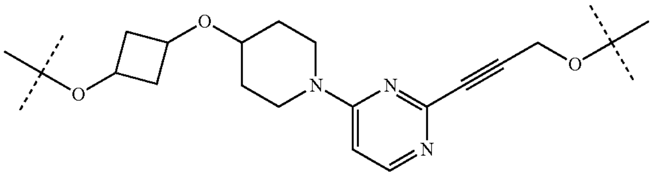

-continued
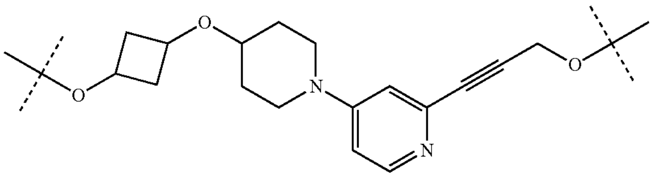
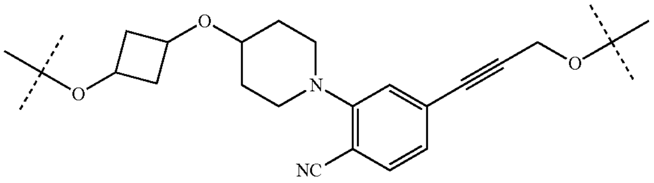
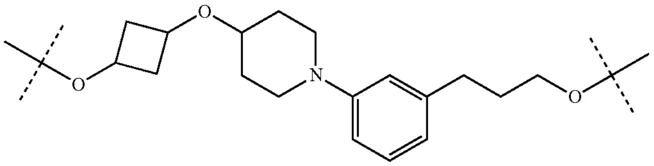
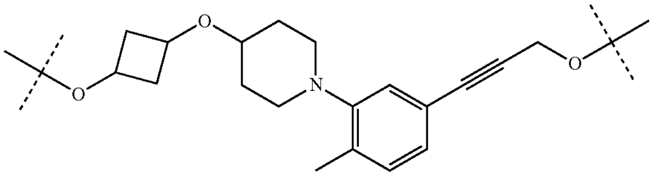
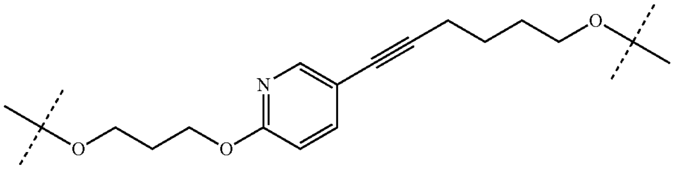
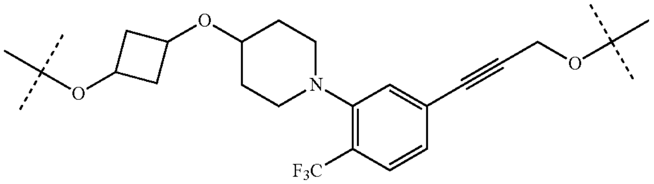
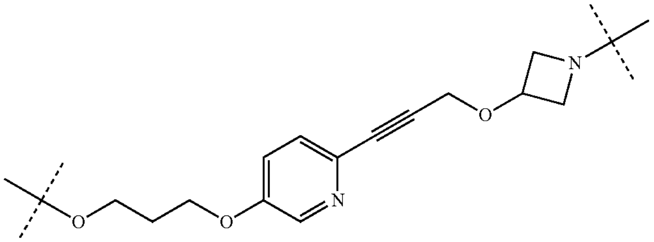
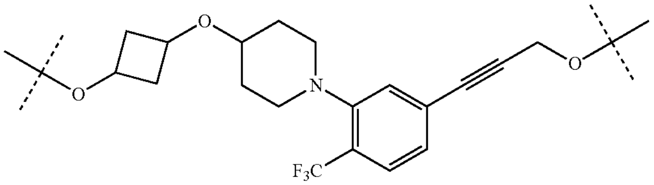
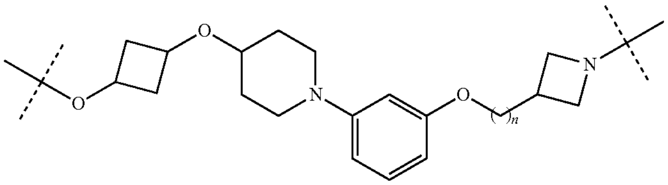

-continued
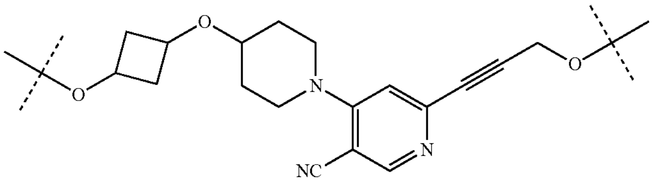
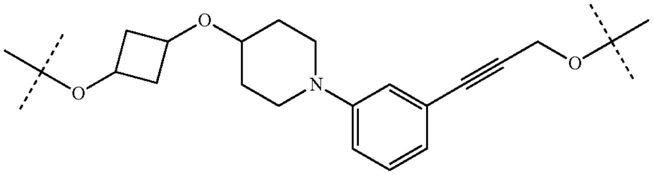
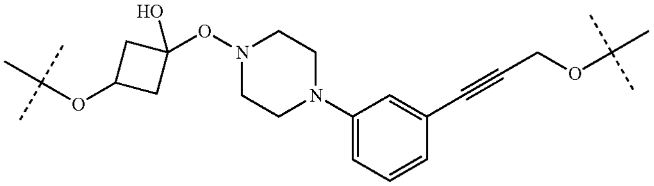
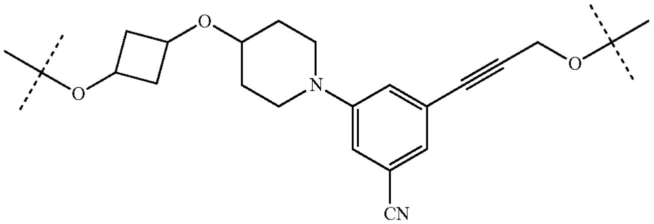
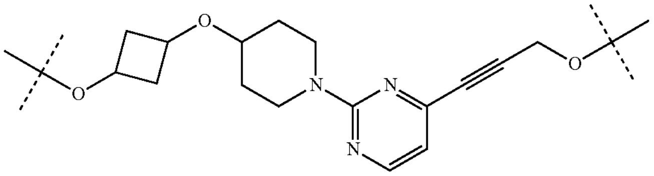
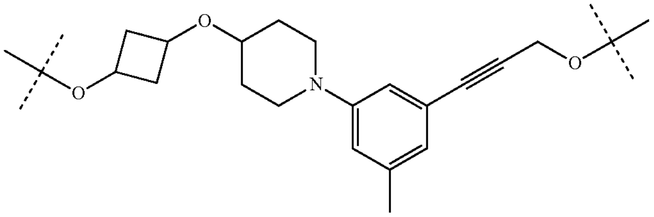
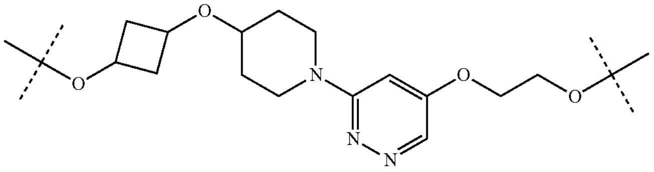
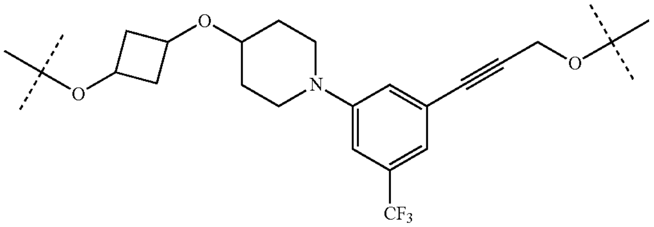
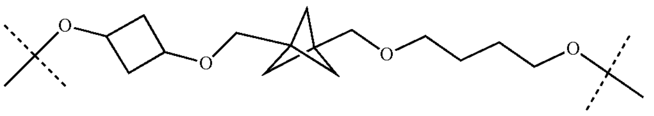

-continued
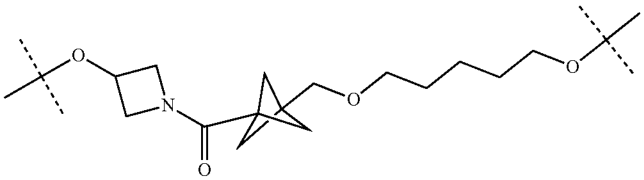
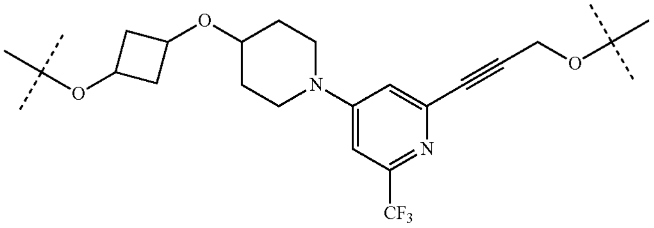
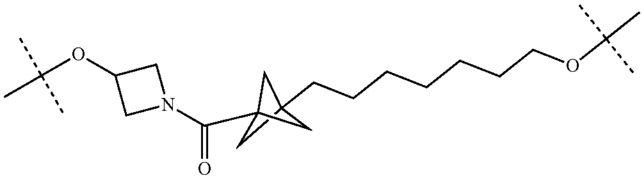
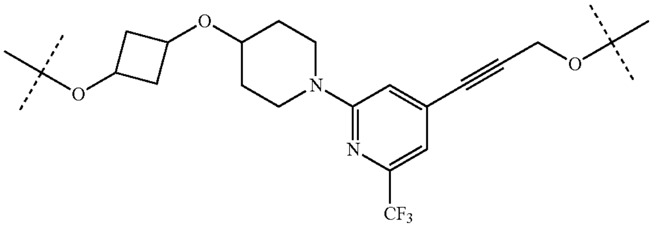
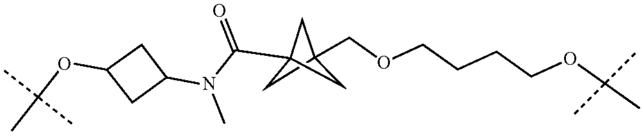
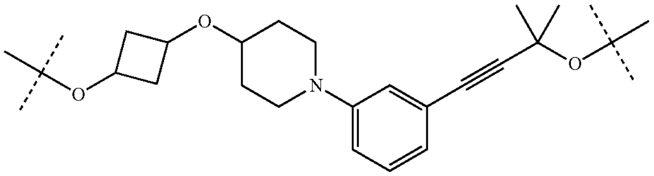
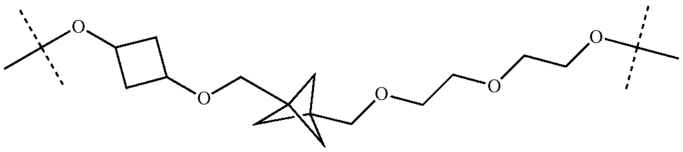
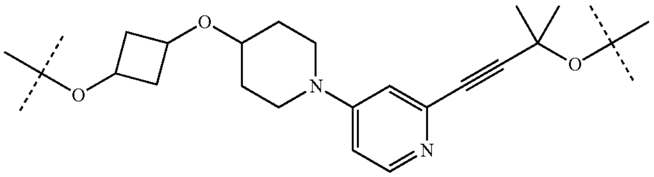
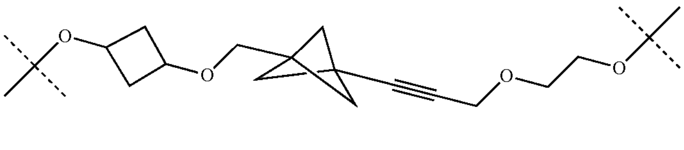

-continued
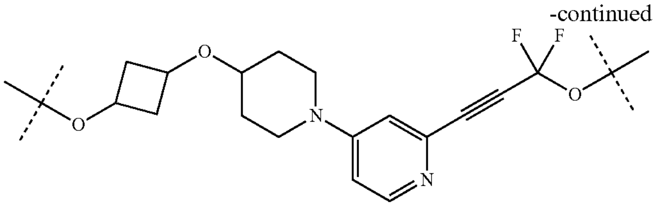
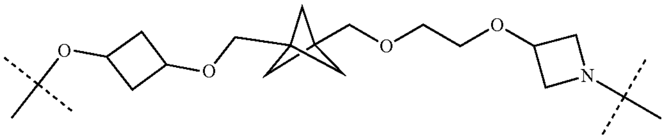
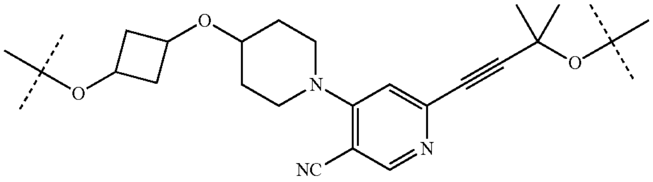
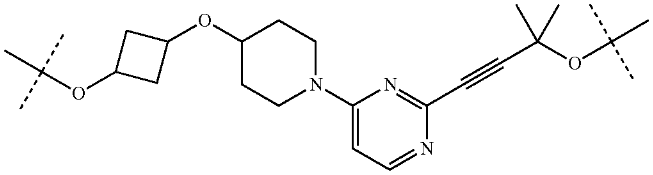
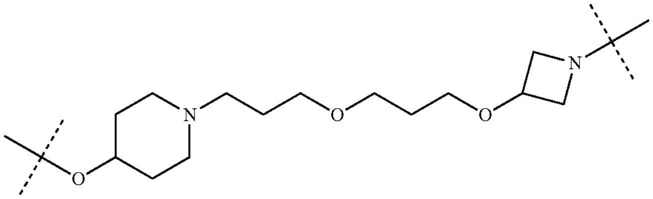
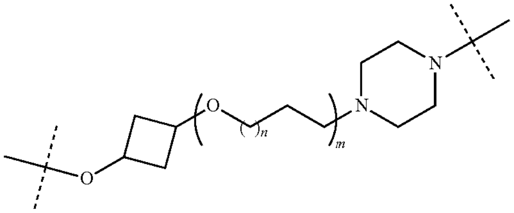
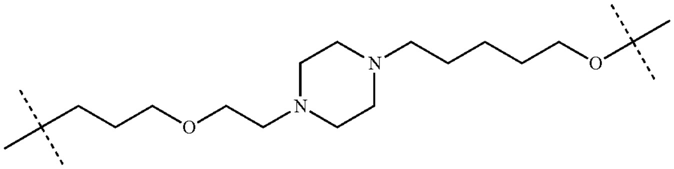
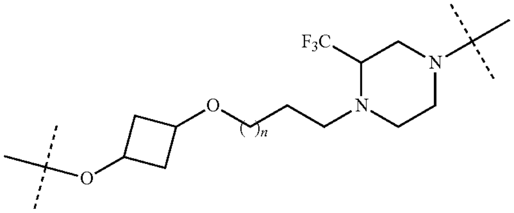
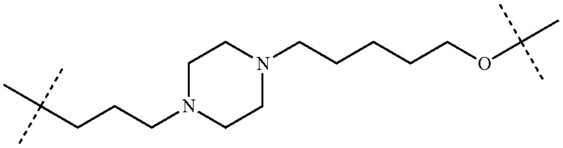
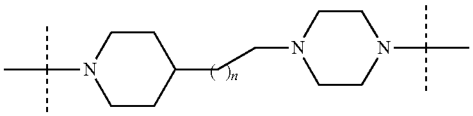
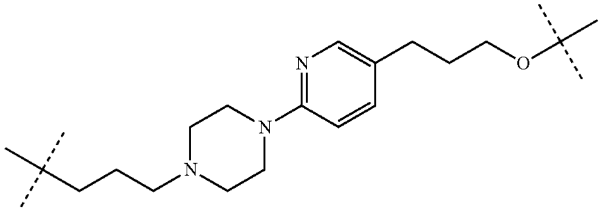

-continued
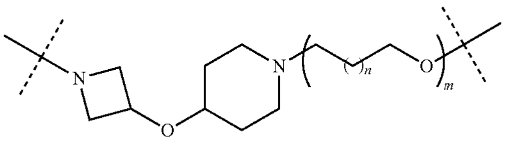
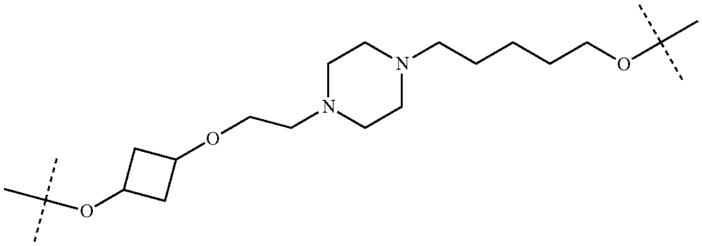
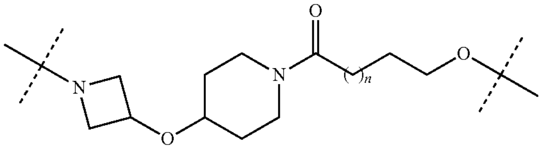
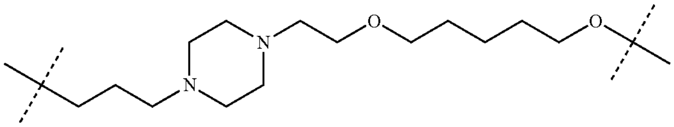
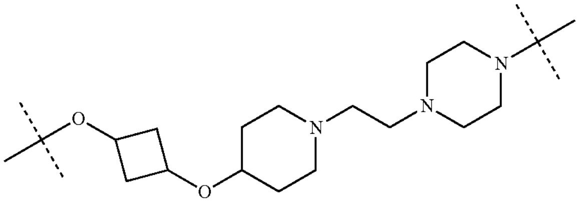
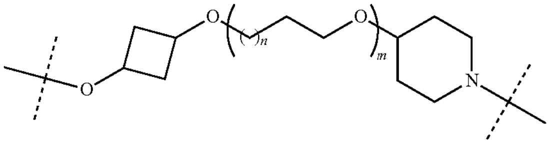
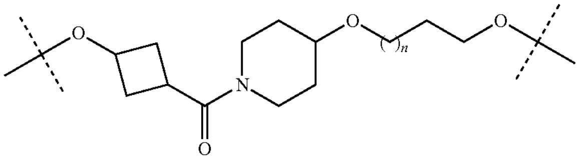
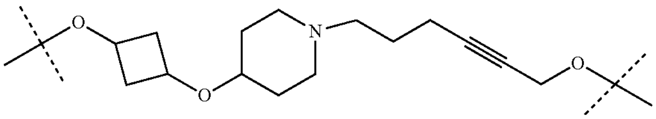
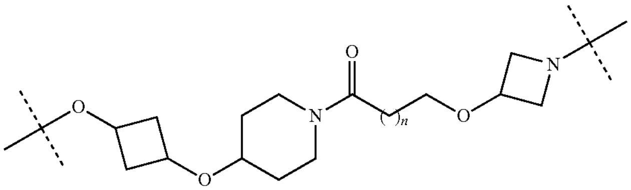
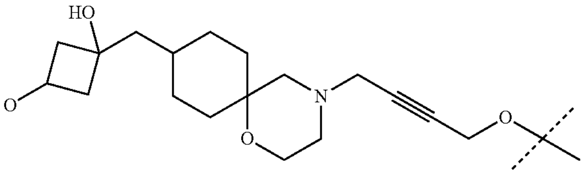
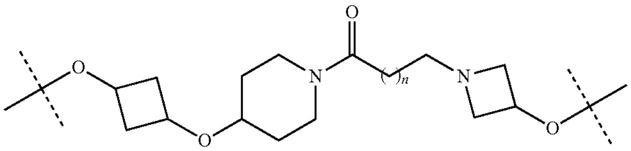

-continued
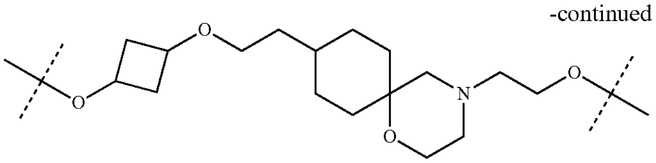
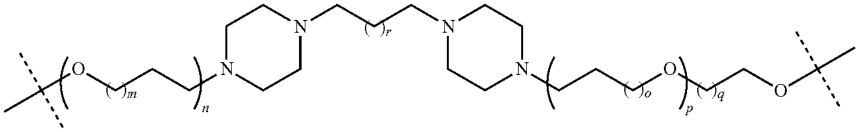
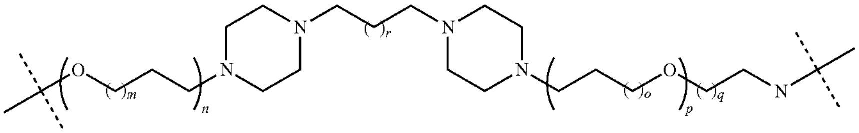
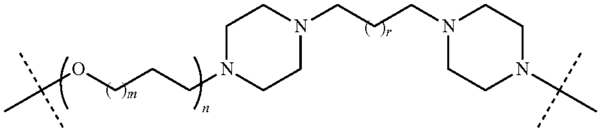
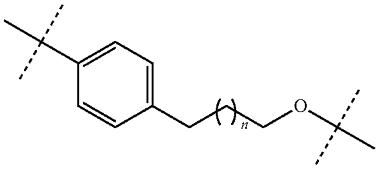
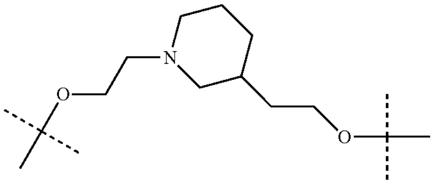
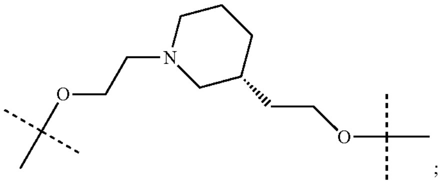
;
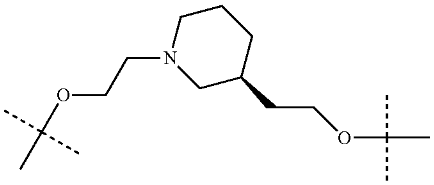
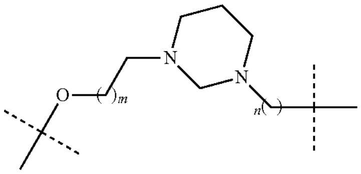
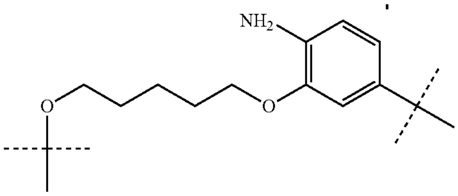
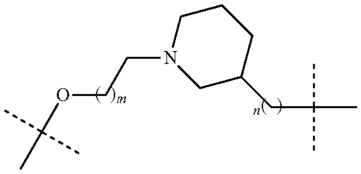
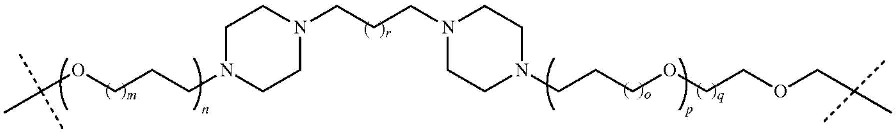
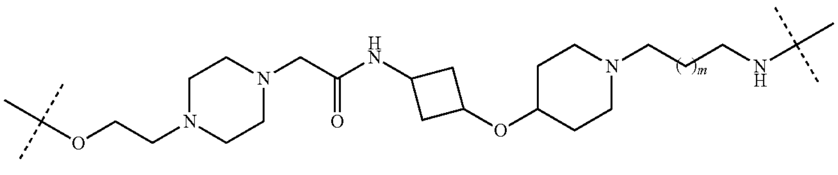
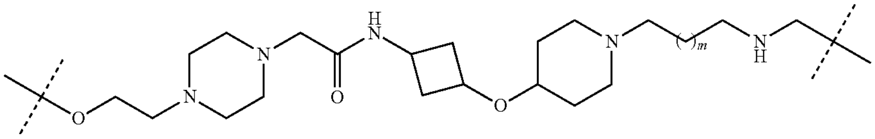

-continued
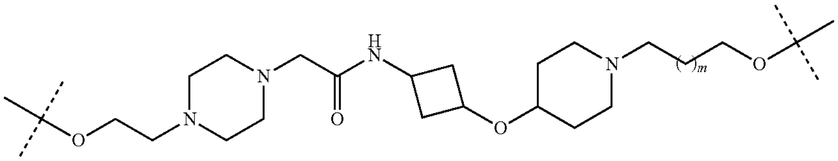
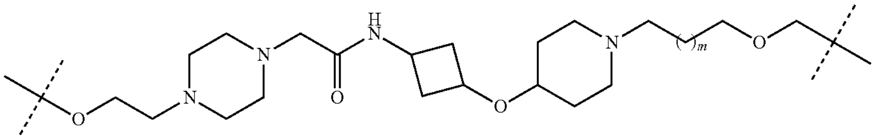
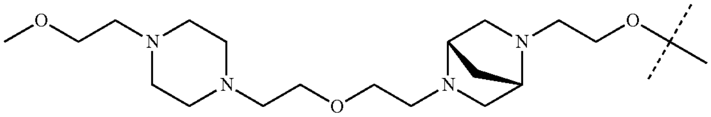
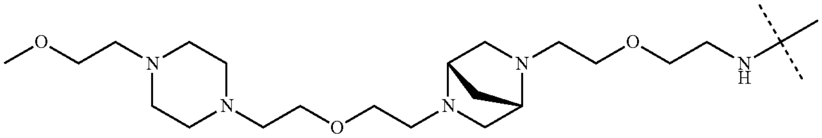
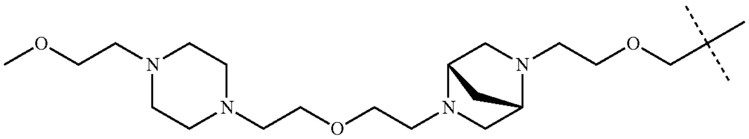
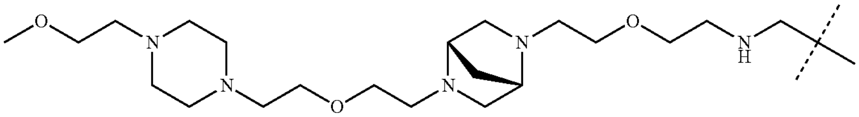
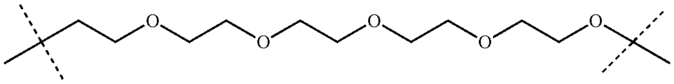
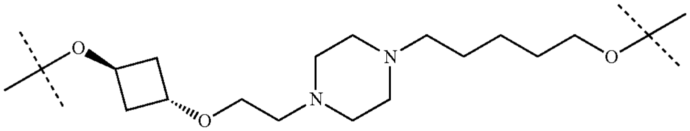
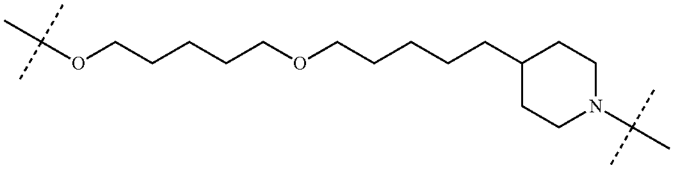
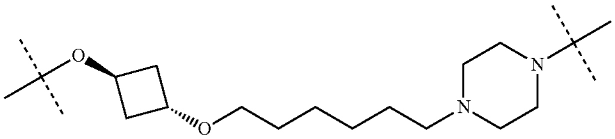
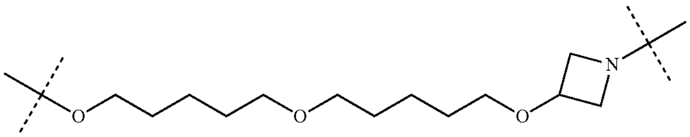
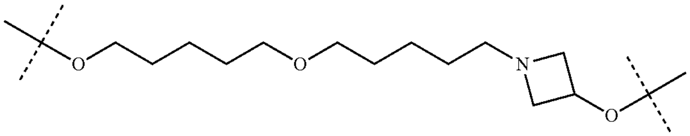

-continued
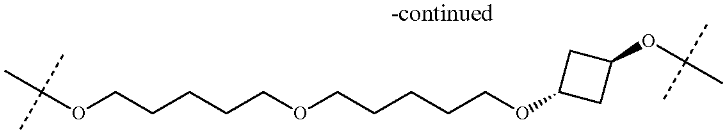
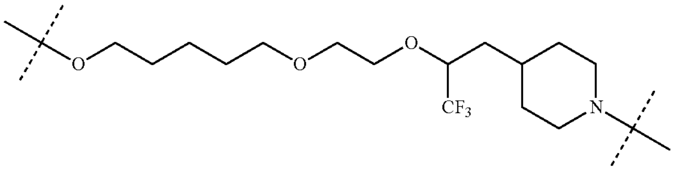
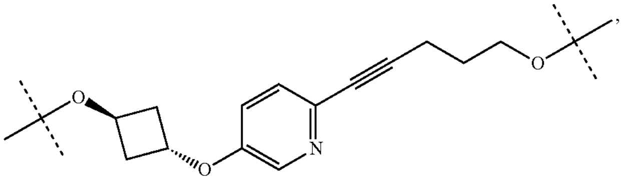
wherein each m, n, o, p, q, r, and s is independently 0, 1, 2, 3, 4, 5, 6, 7, 8, 9, 10, 11, 12, 13, 14, 15, 16, 17, 18, 19, or 20.
In any aspect or embodiment described herein, the unit $A^L$ of linker (L) is selected from the group consisting of:
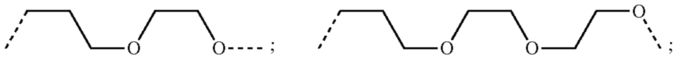
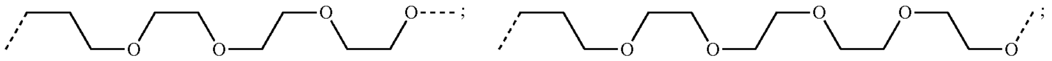
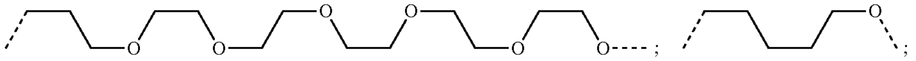
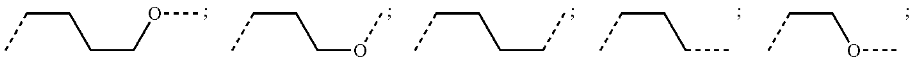
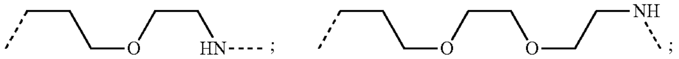
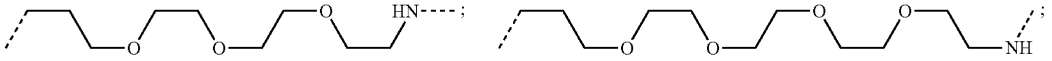
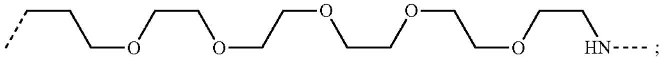
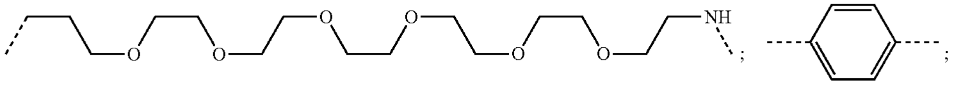
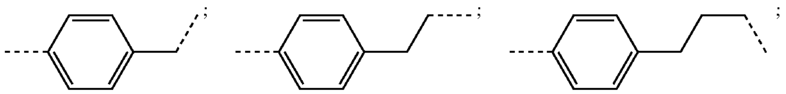
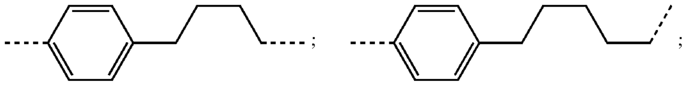
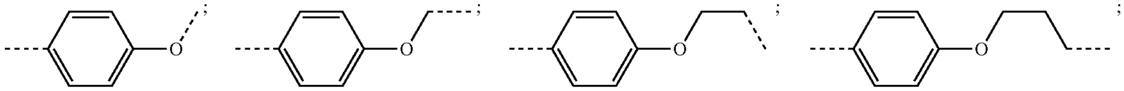
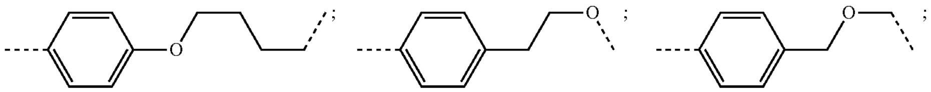
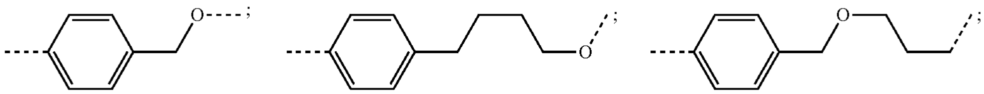

-continued
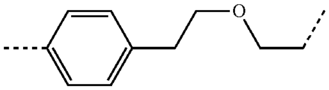 ; 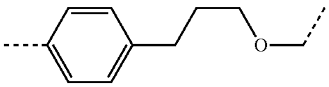 ; 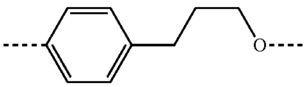 ;
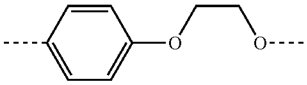 ; 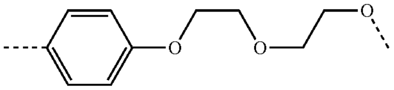 ;
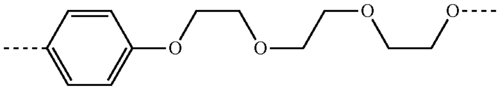 ; 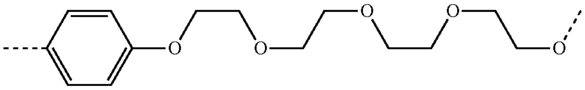 ;
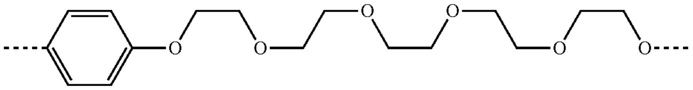 ; 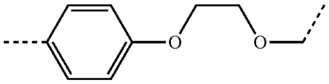 ;
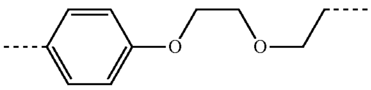 ; 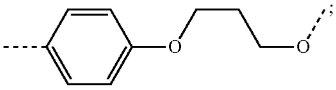 ; 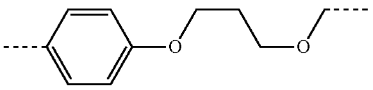 ;
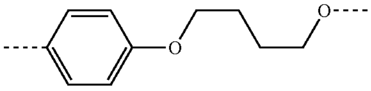 ; 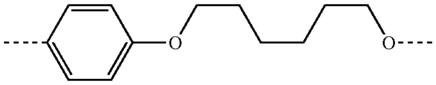 ;
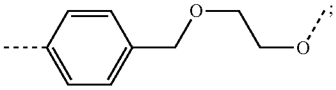 ; 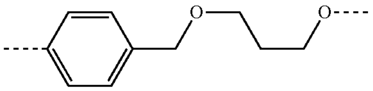 ; 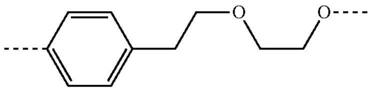 ;
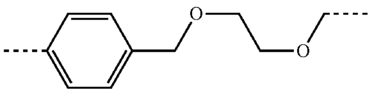 ; 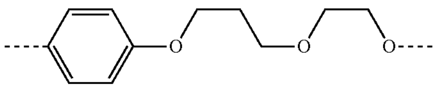 ;
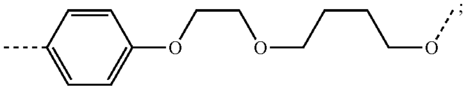 ; 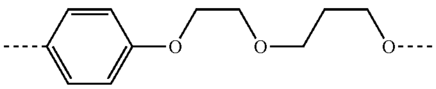 ;
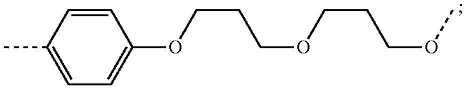 ; 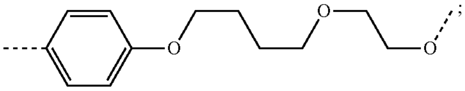 ;
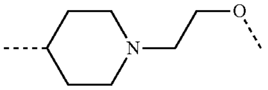 ; 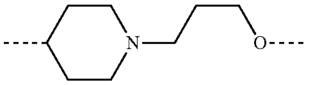 ; 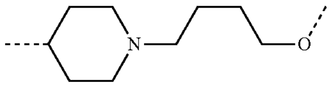 ;
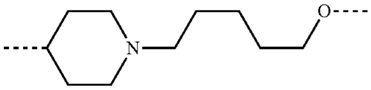 ; 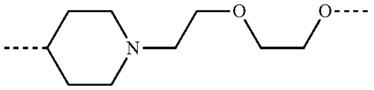 ;
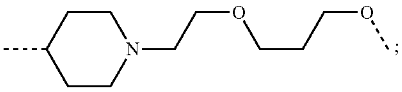 ; 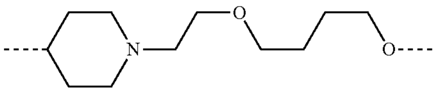 ;
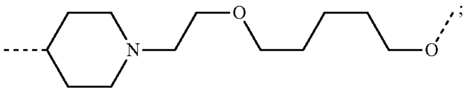 ; 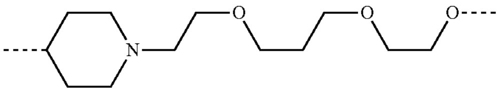 ;
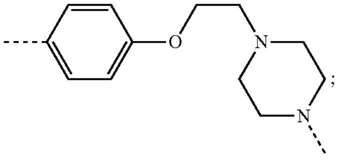 ; 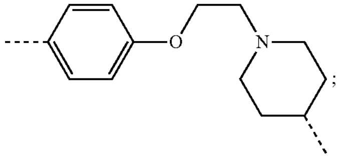 ;
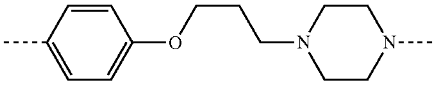 ; 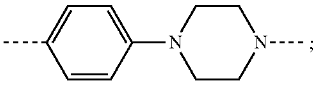 ;
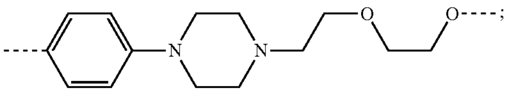 ; 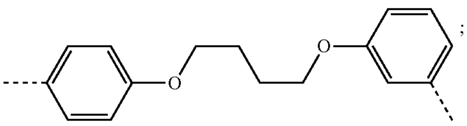 ;

-continued
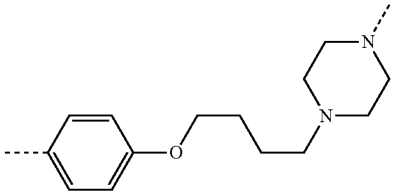 ;
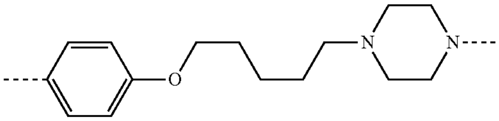 ;
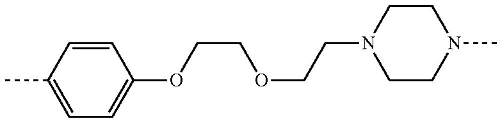 ;
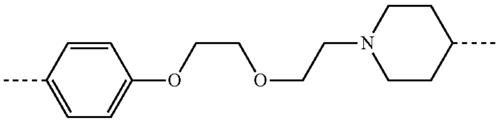 ;
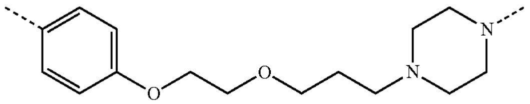 ;
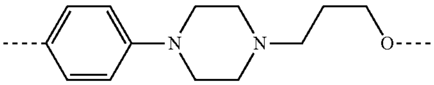 ;
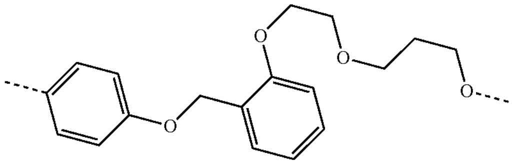 ;
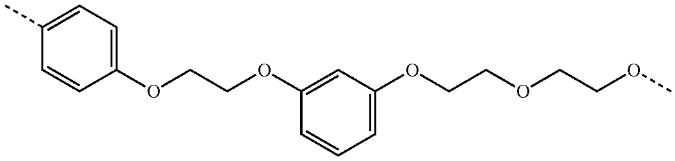 ;
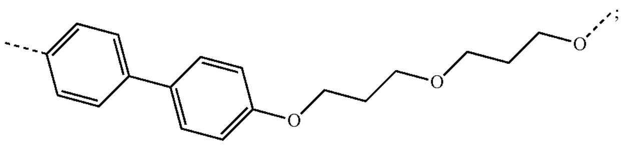 ;
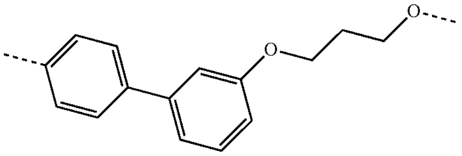 ;
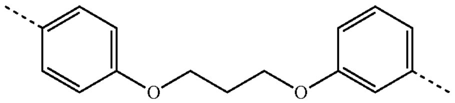 ;
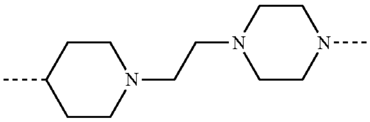 ;
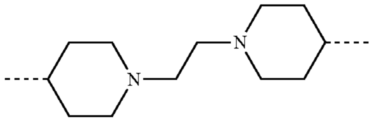 ;
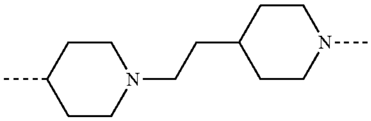 ;
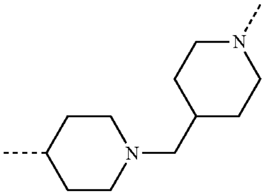 ;
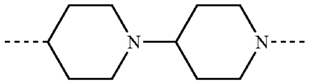 ;
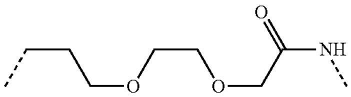 ;
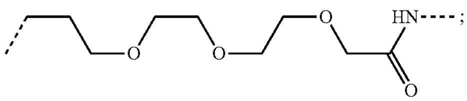 ;
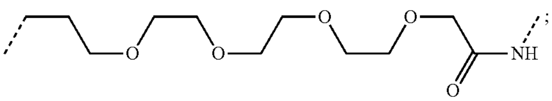 ;
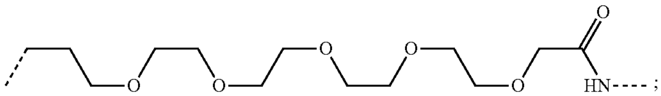 ;
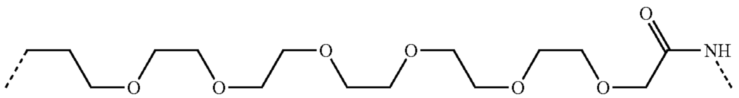 ;
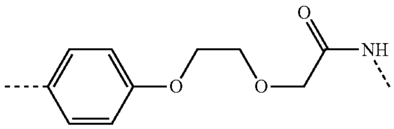 ;
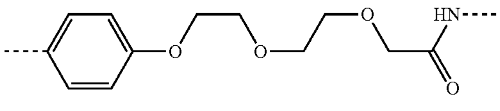 ;

-continued
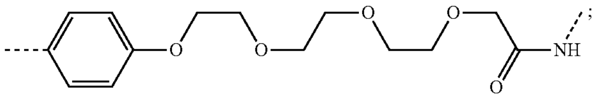 ;
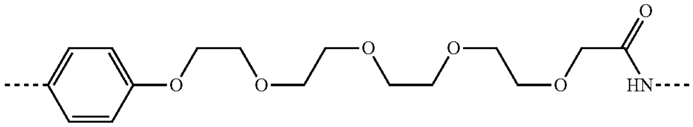 ;
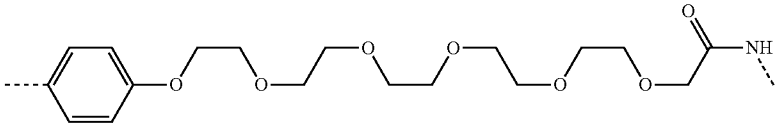 ;
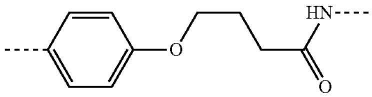 ; 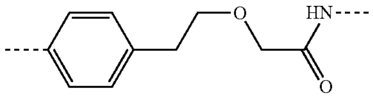 ;
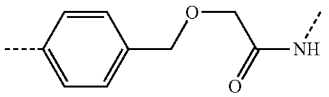 ; 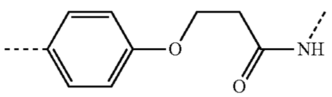 ;
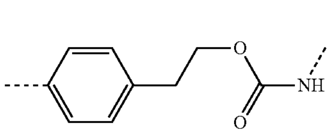 ; 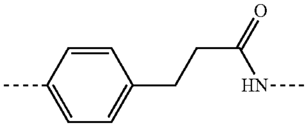 ; 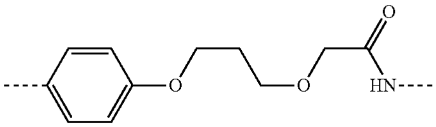 ;
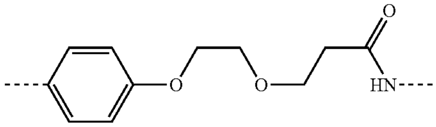 ; 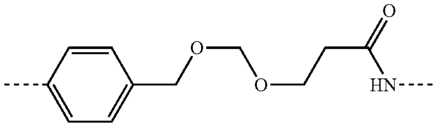 ;
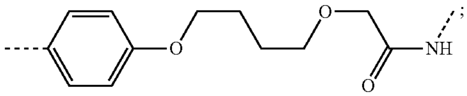 ; 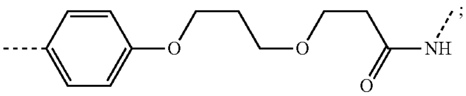 ;
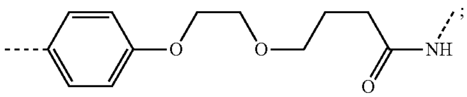 ; 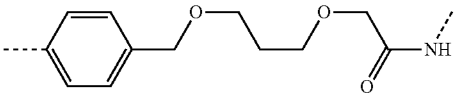 ;
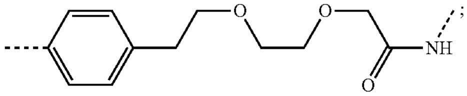 ; 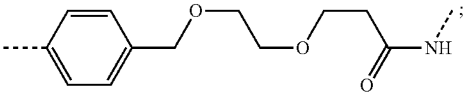 ;
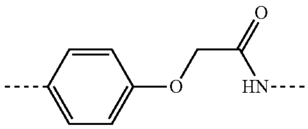 ; 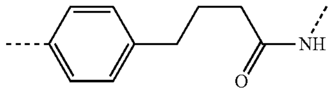 ; 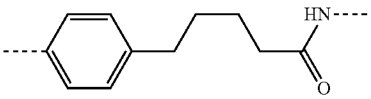 ;
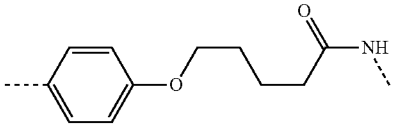 ; 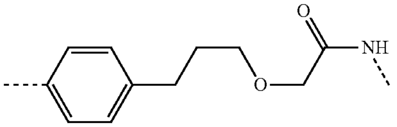 ;
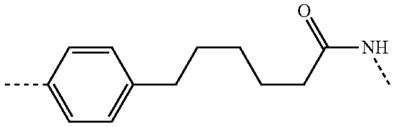 ; 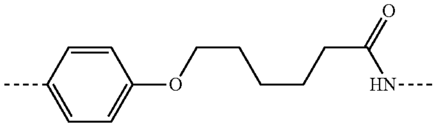 ;
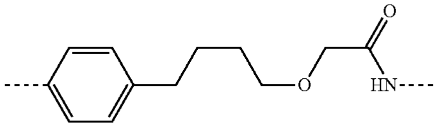 ; 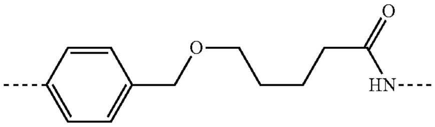 ;

-continued
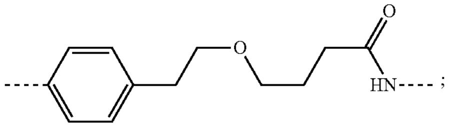
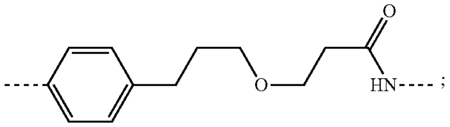
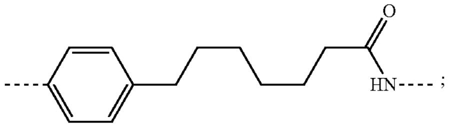
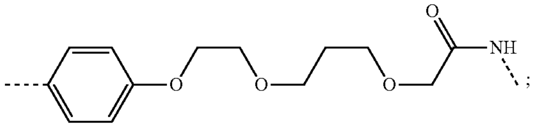
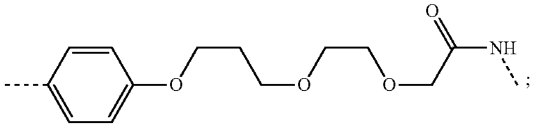
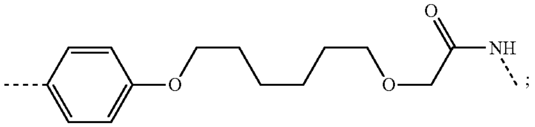
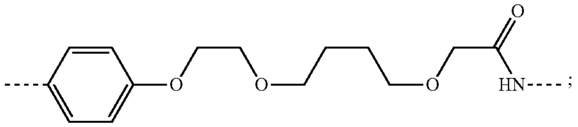
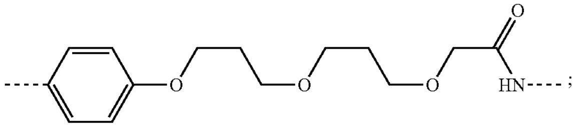
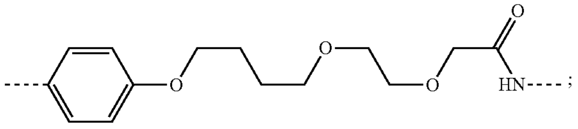
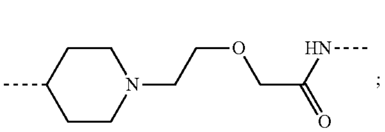
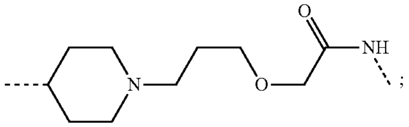
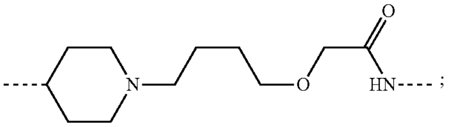
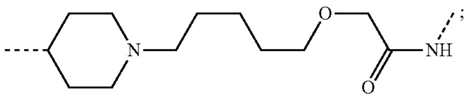
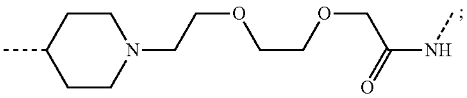
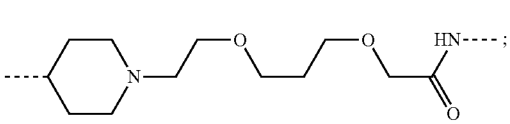
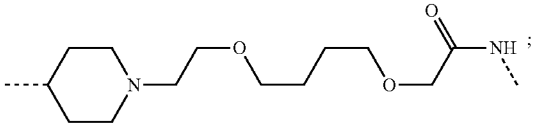
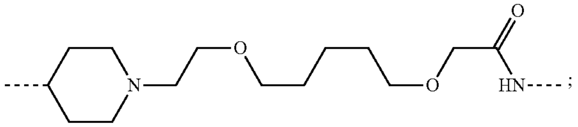
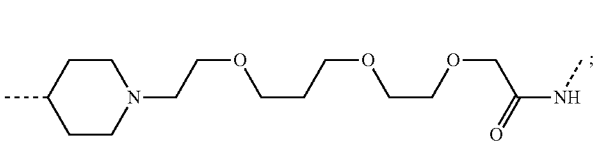
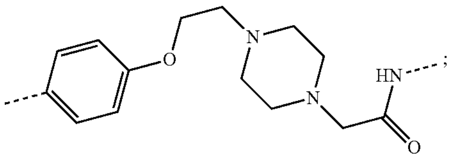
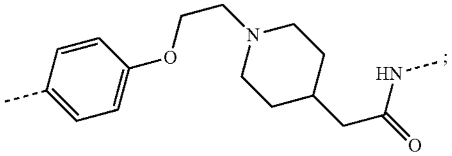
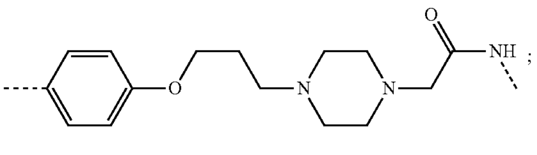
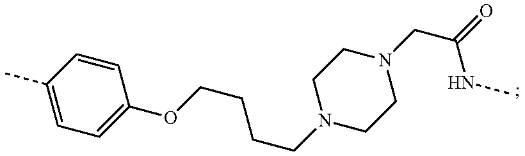
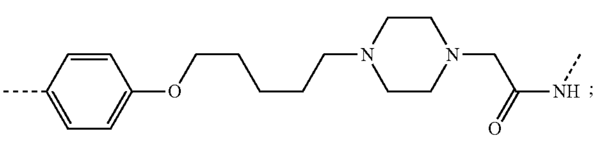

-continued
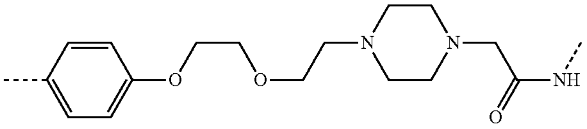 ;
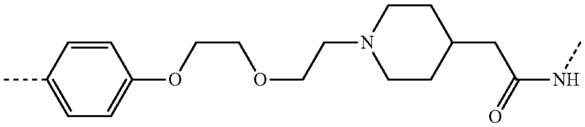 ; 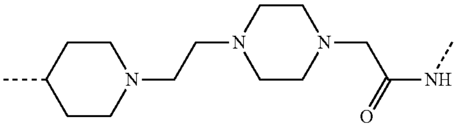 ;
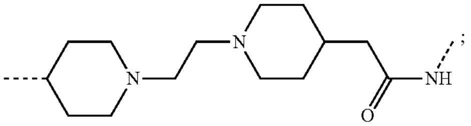 ; 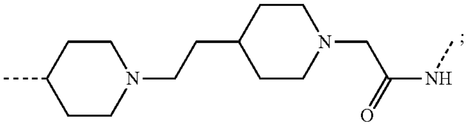 ;
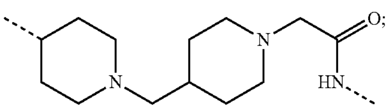 ; 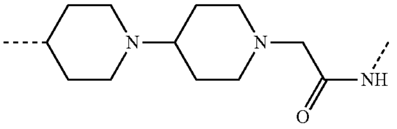 ; 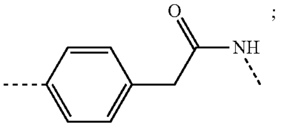 ;
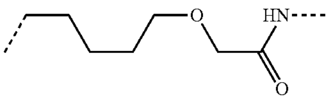 ; 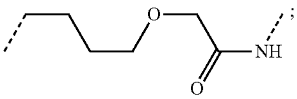 ; 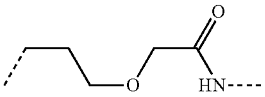 ;
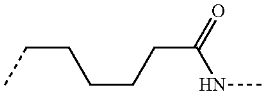 ; 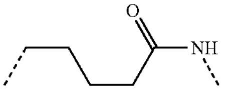 ; 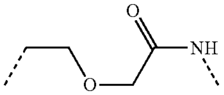 ; 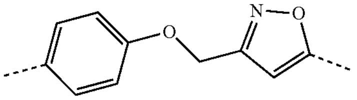 ;
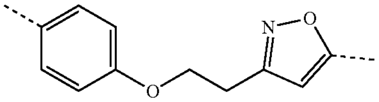 ; 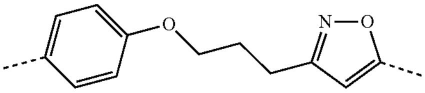 ;
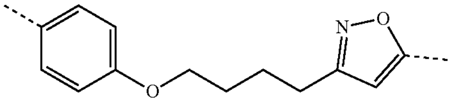 ; 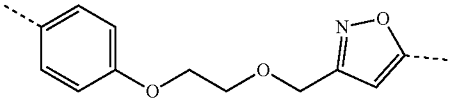 ;
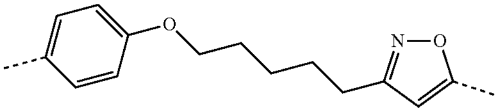 ; 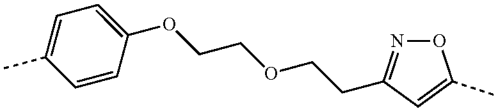 ;
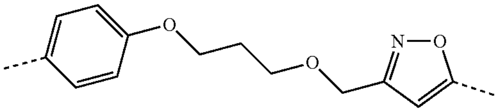 ; 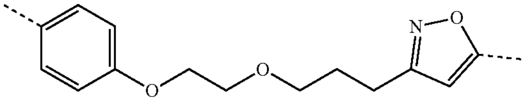 ;
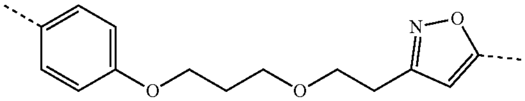 ; 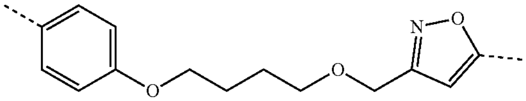 ;
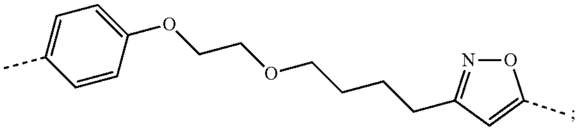 ;
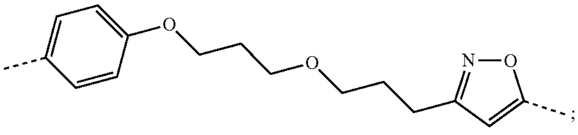 ;
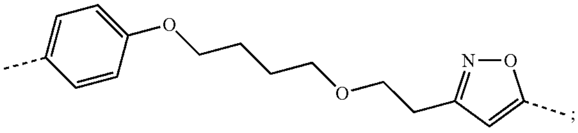 ;

-continued
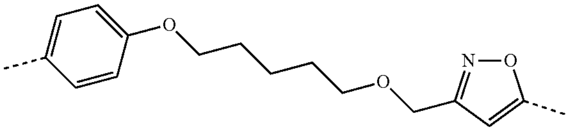
;
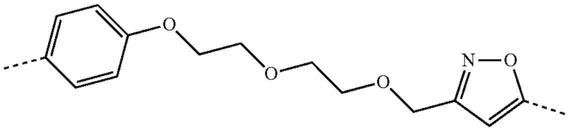
;
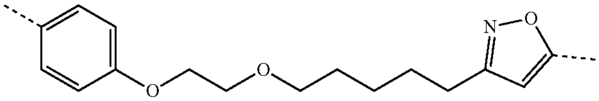
;
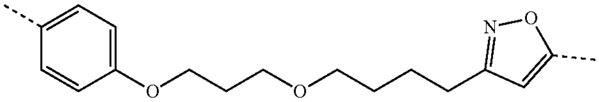
;
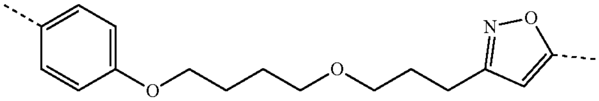
;
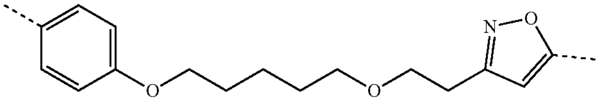
;
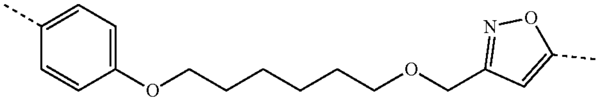
;
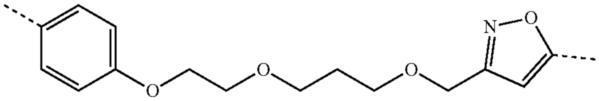
;
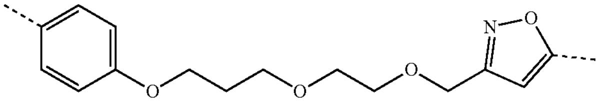
;
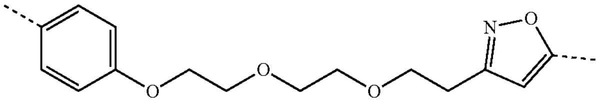
;
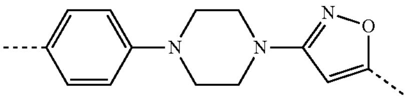
;
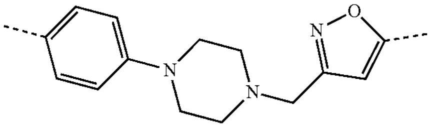
;
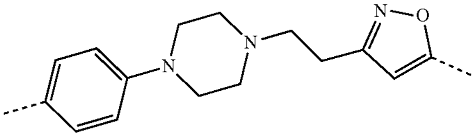
;
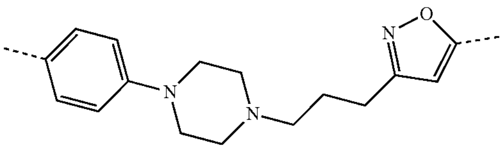
;
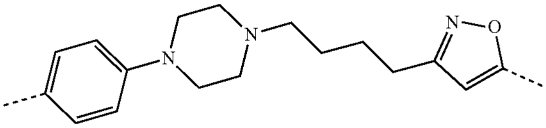
;
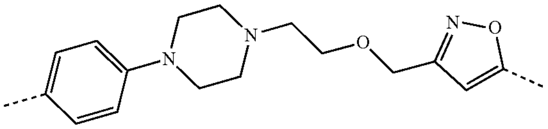
;
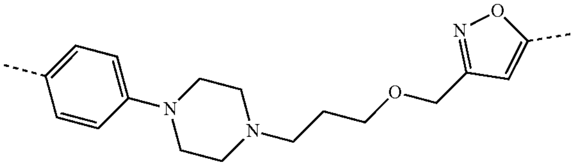
;

-continued
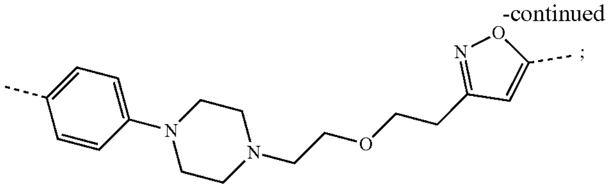 ;
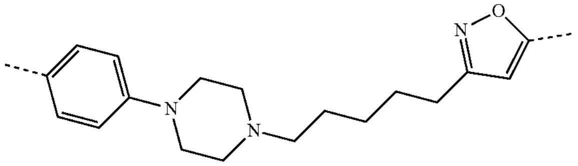 ;
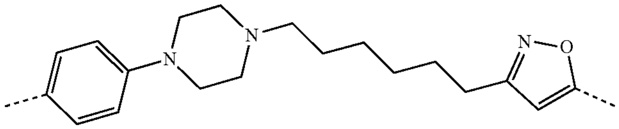 ;
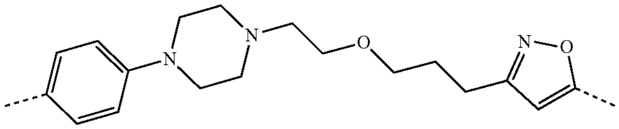 ;
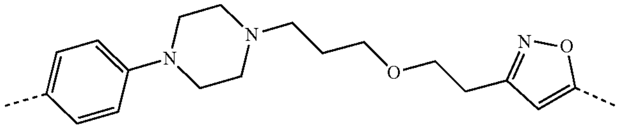 ;
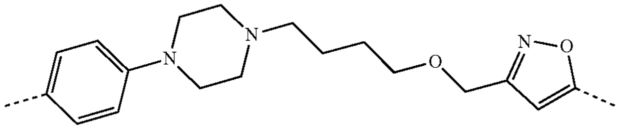 ; 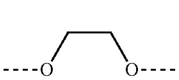 ;
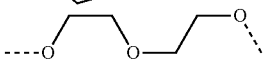 ; 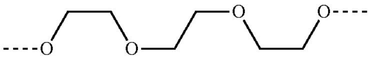 ;
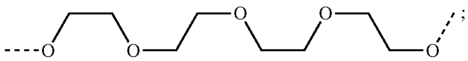 ; 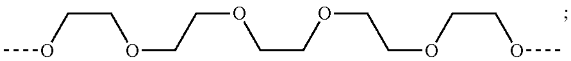 ;
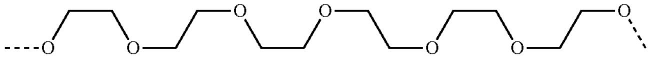 ; 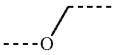 ; 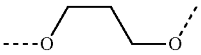 ;
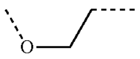 ; 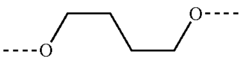 ; 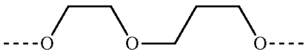 ; 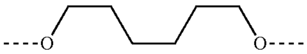 ;
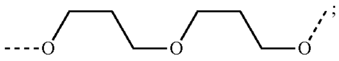 ; 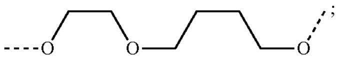 ; 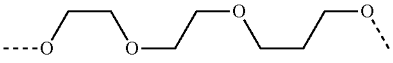 ;
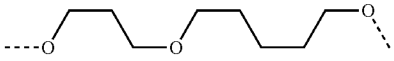 ; 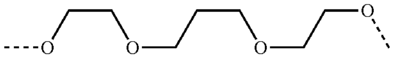 ;
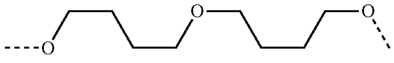 ; 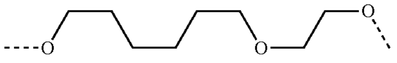 ;
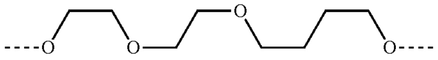 ; 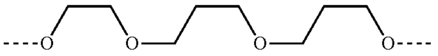 ;
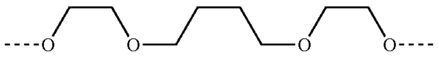 ; 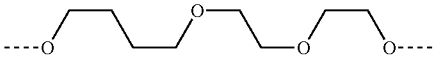 ;
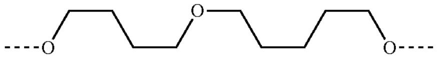 ;
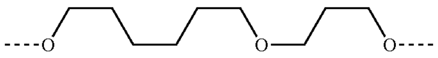 ; 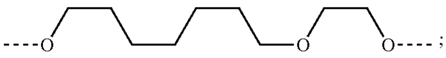 ; 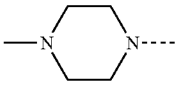 ;

-continued
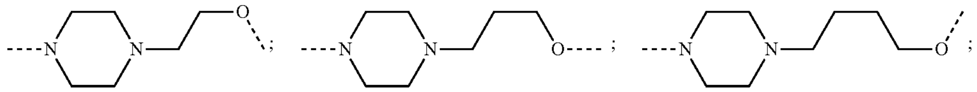
; ; ;
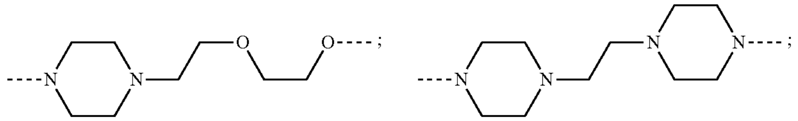
; ;
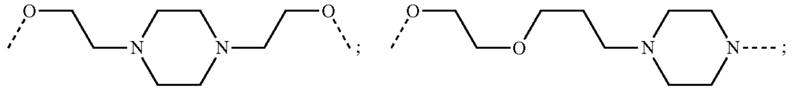
; ;
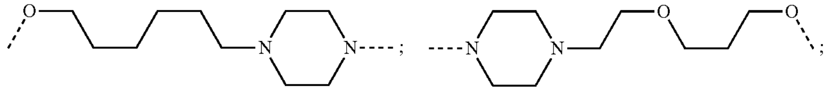
; ;
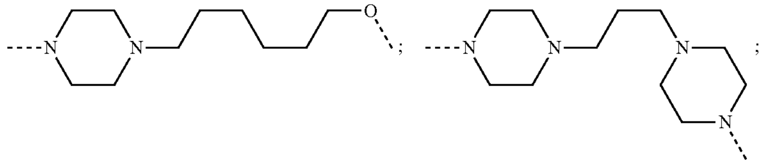
; ;
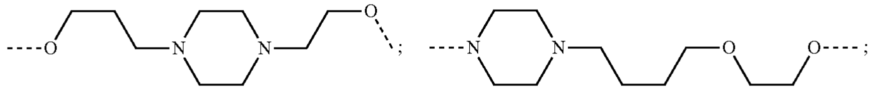
; ;
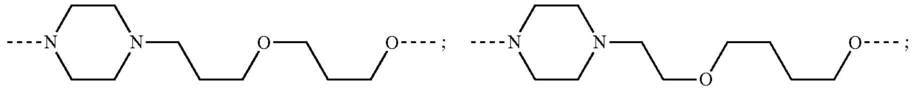
; ;
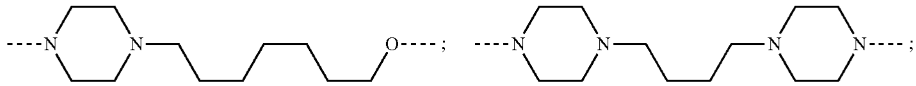
; ;
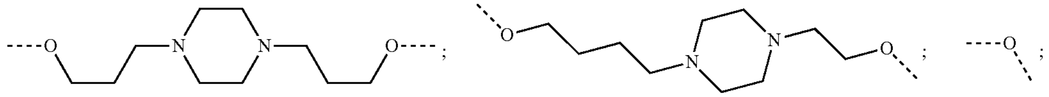
; ; ;
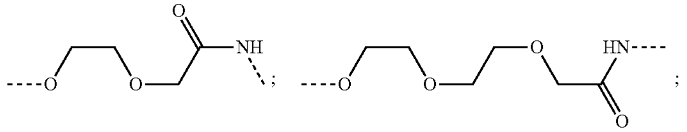
; ;
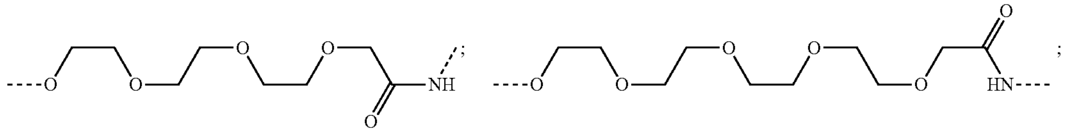
; ;
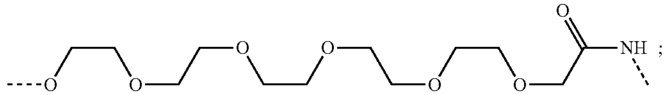
;
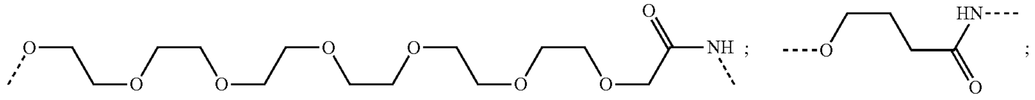
; ;
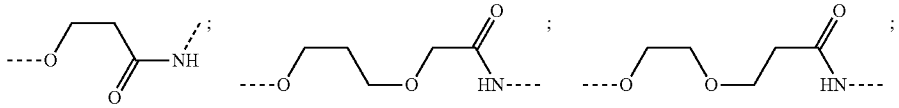
; ; ;
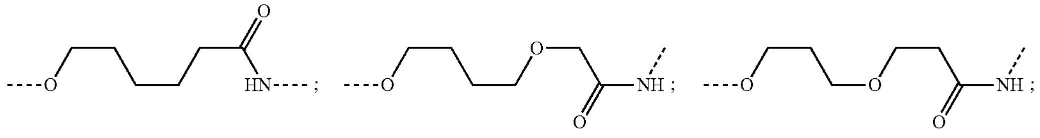
; ; ;
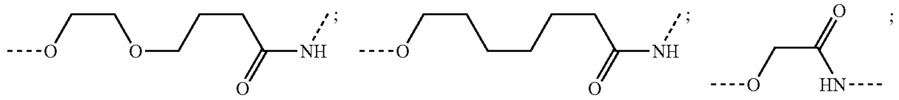
; ; ;

-continued
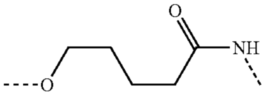 ;
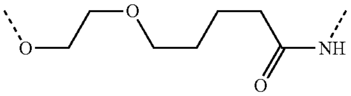 ;
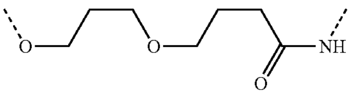 ;
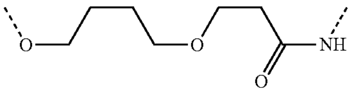 ;
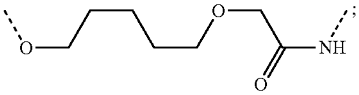 ;
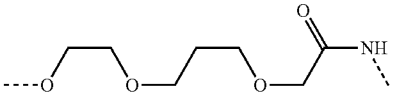 ;
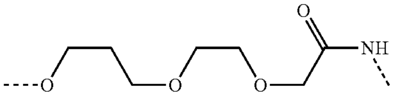 ;
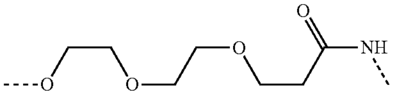 ;
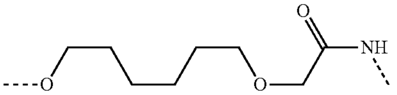 ;
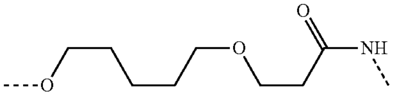 ;
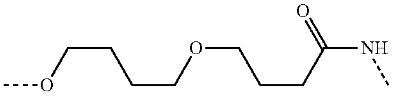 ;
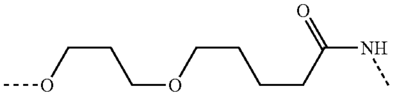 ;
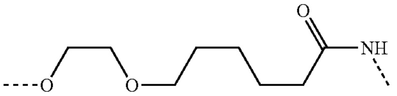 ;
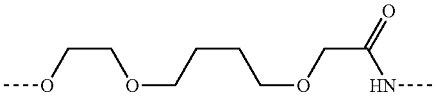 ;
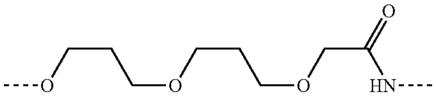 ;
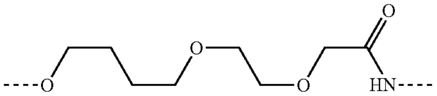 ;
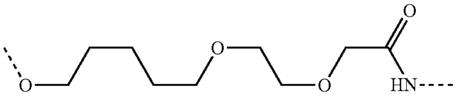 ;
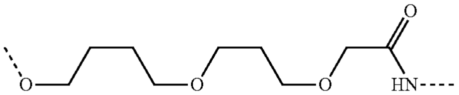 ;
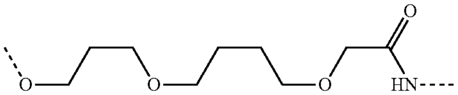 ;
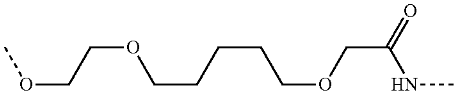 ;
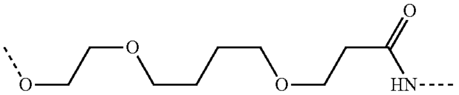 ;
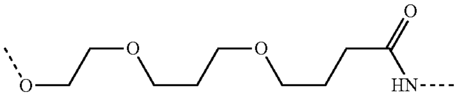 ;
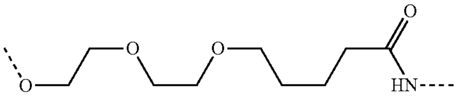 ;
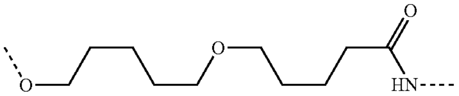 ;
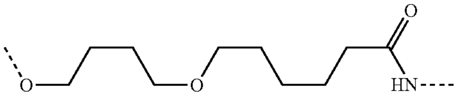 ;
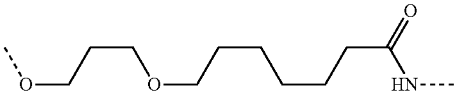 ;
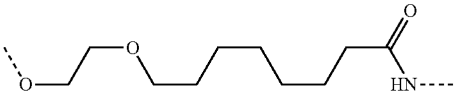 ;
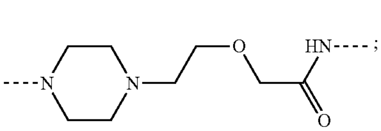 ;
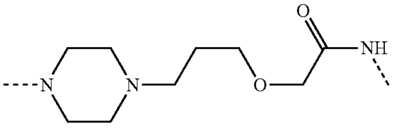 ;
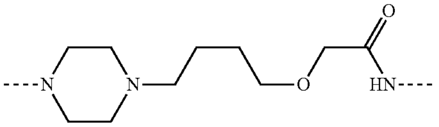 ;
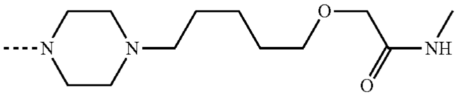 ;
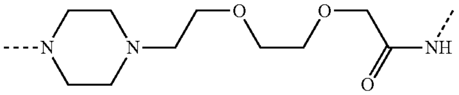 ;
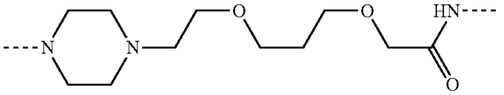 ;

-continued
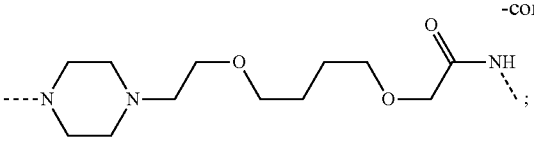
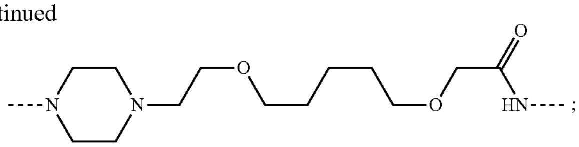
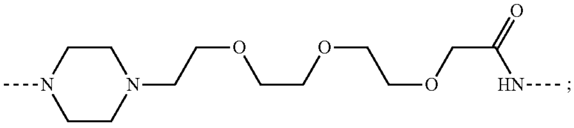
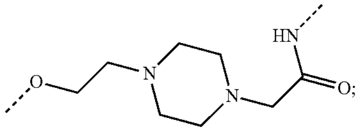
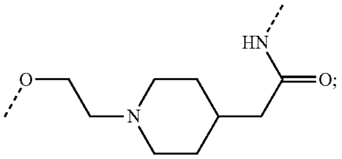
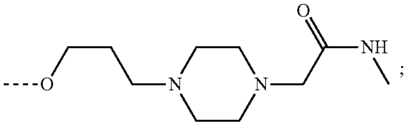
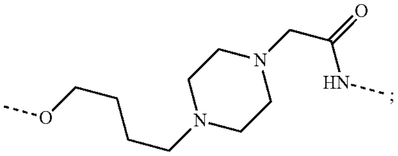
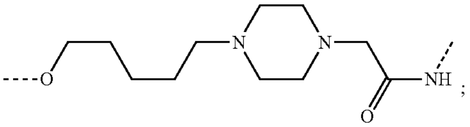
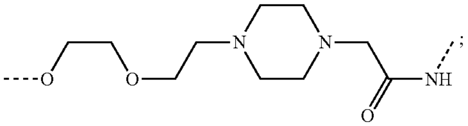
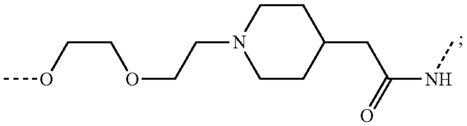
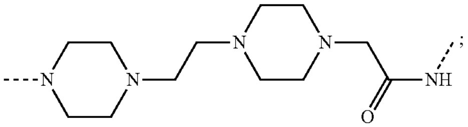
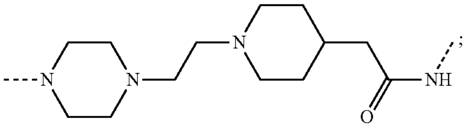
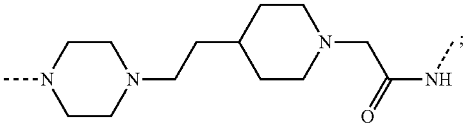
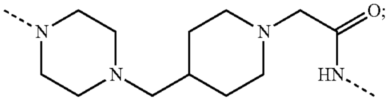
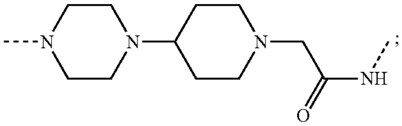
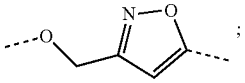
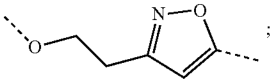
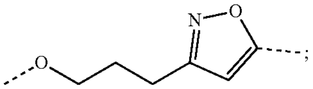
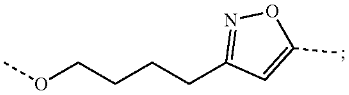
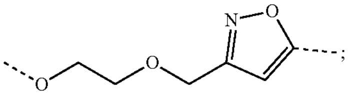
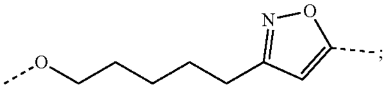
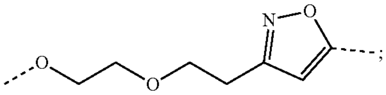
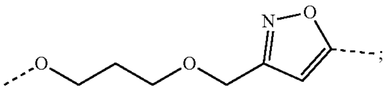
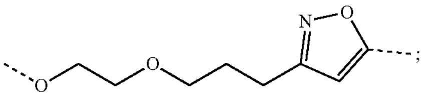
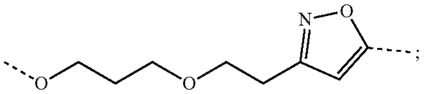
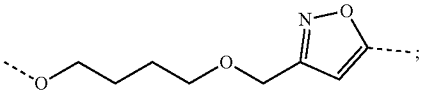
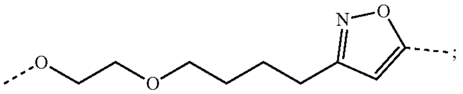
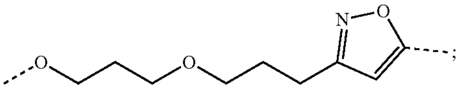
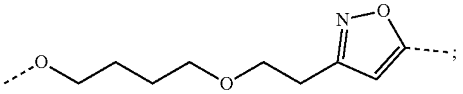
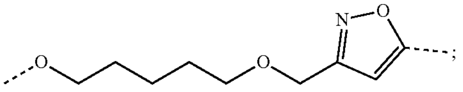
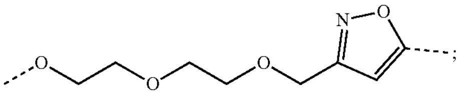
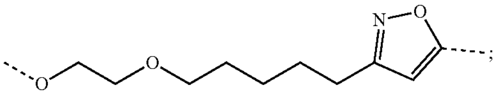

-continued
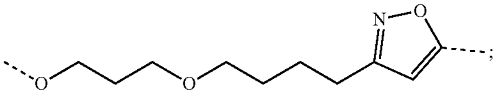;
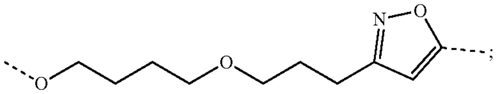;
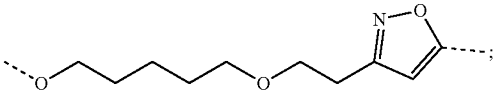;
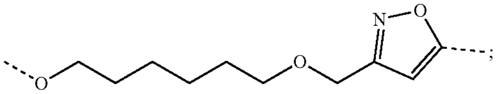;
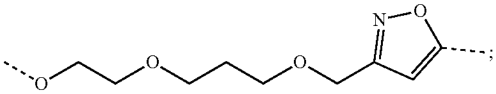;
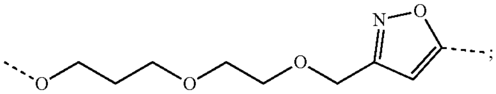;
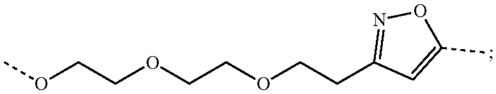;
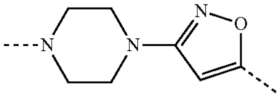;
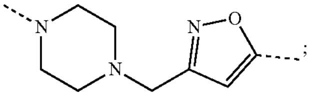;
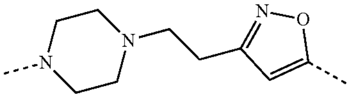;
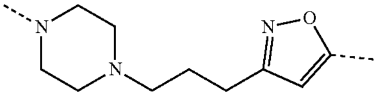;
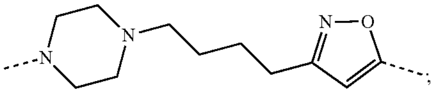;
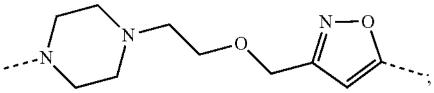;
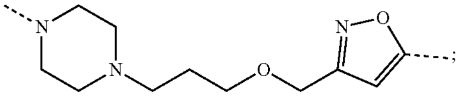;
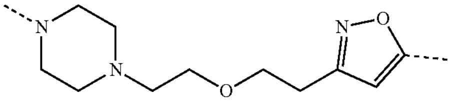;
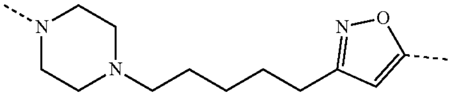;
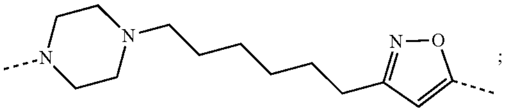;
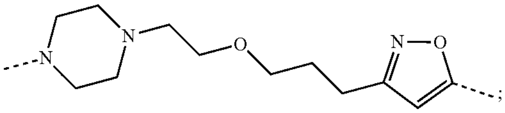;
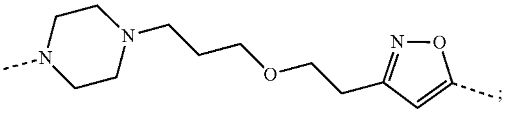;
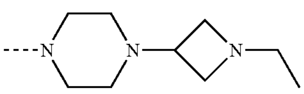;
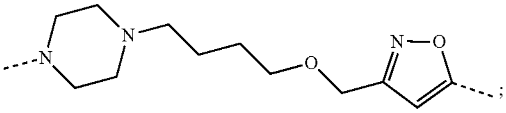;
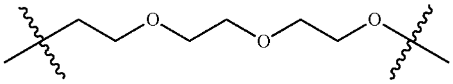;
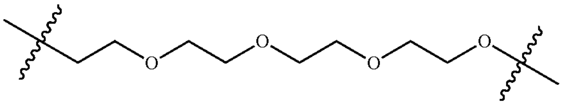;
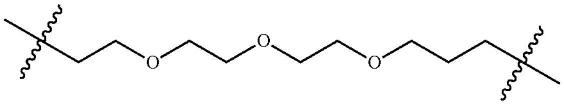;
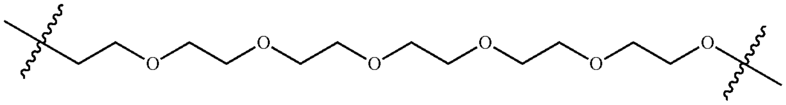;
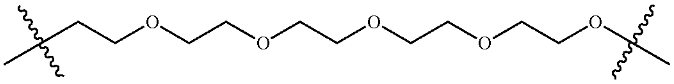;
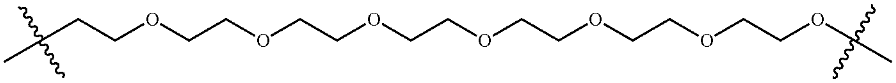;
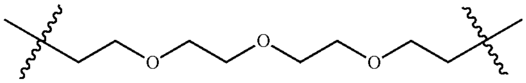;
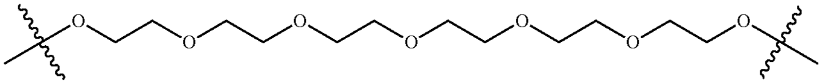;

-continued
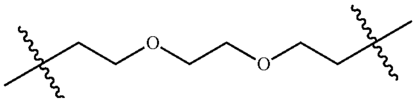
;
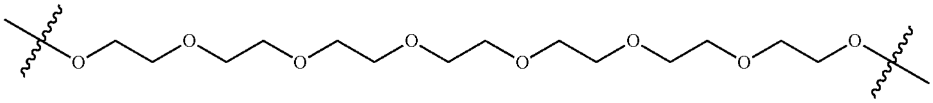
;
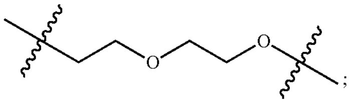
;
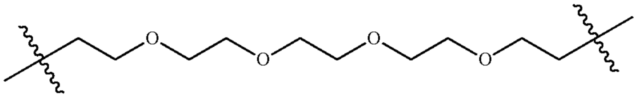
;
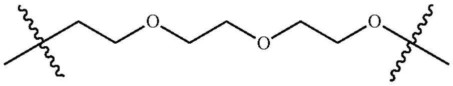
;
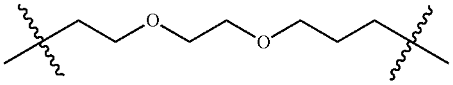
;
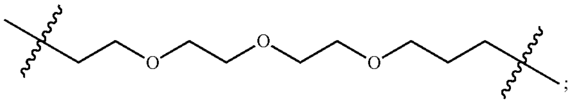
;
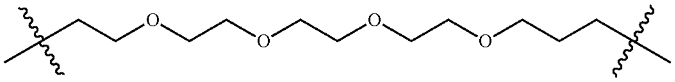
;
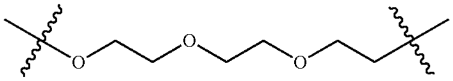
;
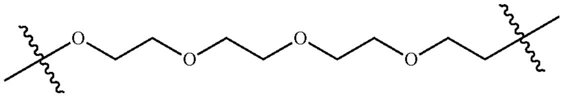
;
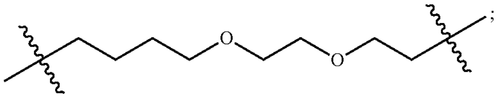
;
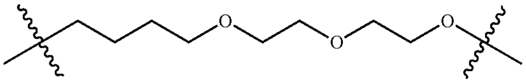
;
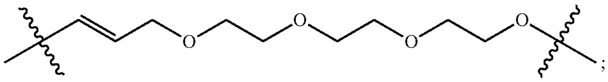
;
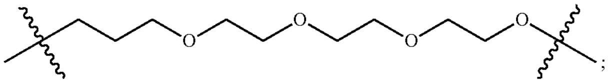
;
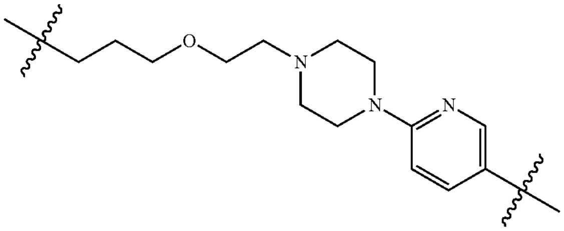
;
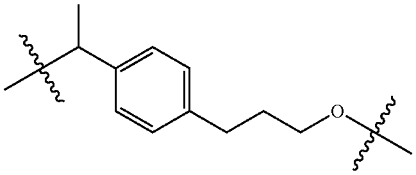
;
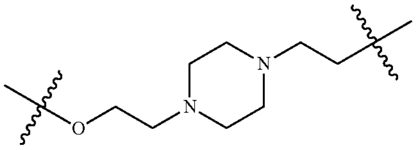
;
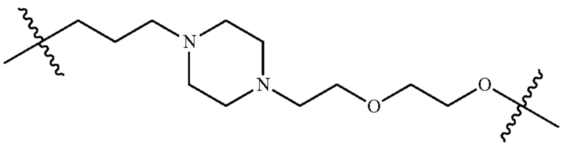
;
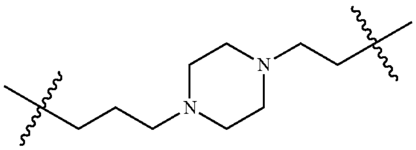
;
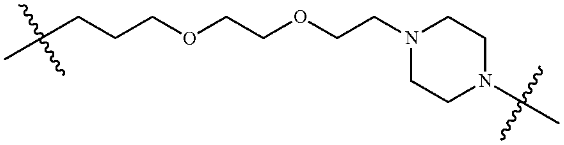
;

-continued
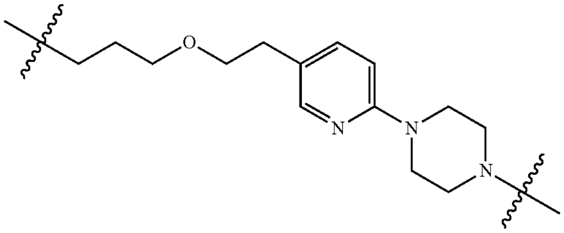
;
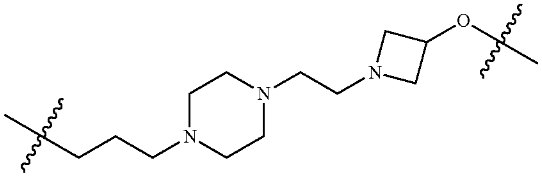
;
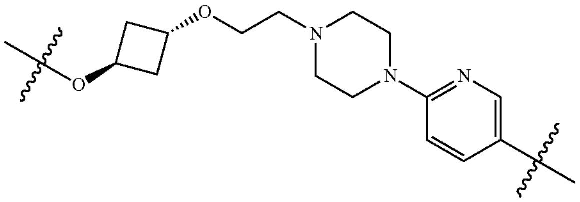
;
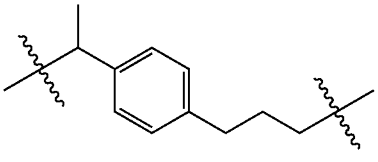
;
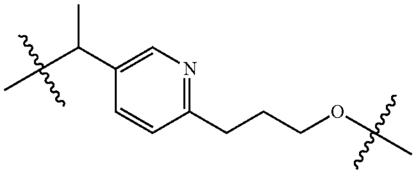
;
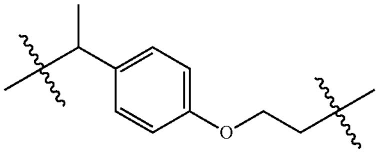
;
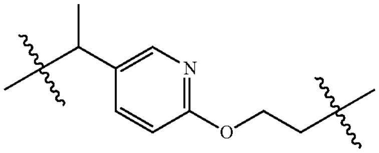
;
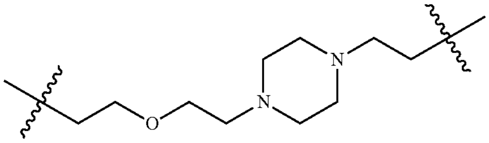
;
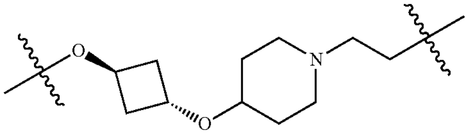
;
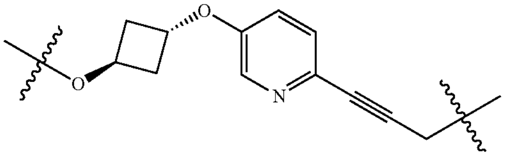
;
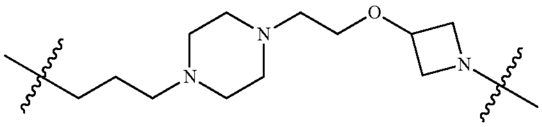
;
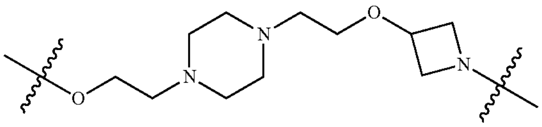
;
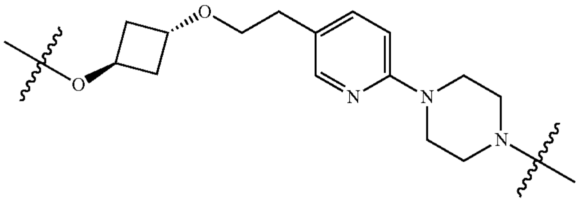
;
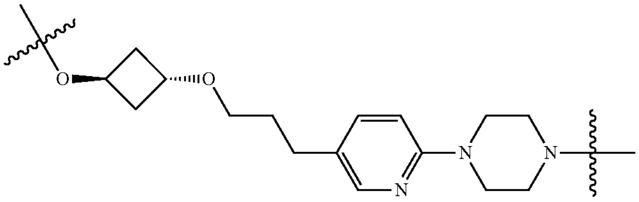
;

-continued
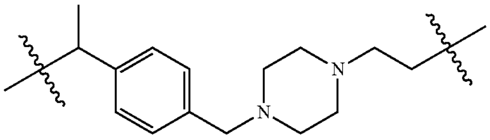
;
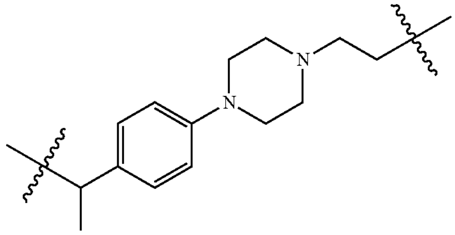
;
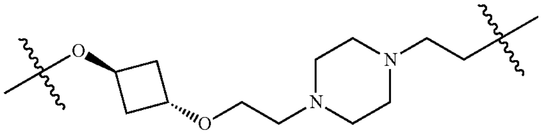
;
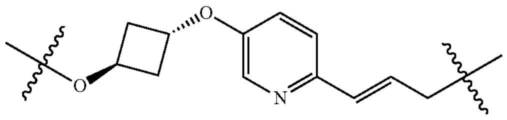
;
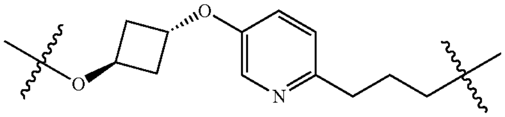
;
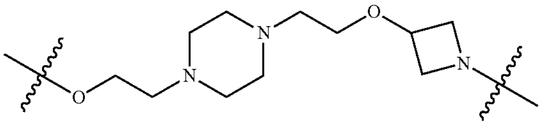
;
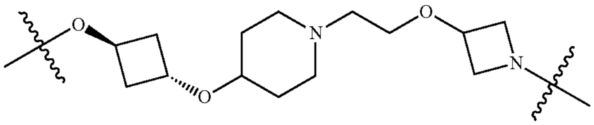
;
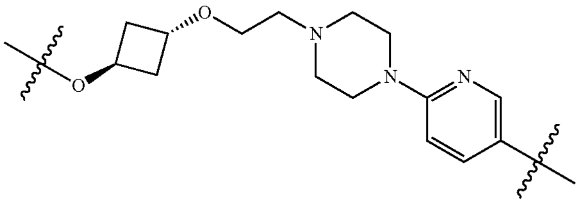
;
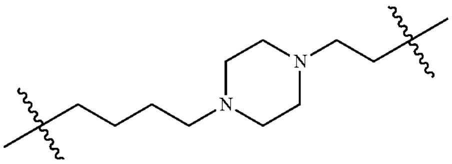
;
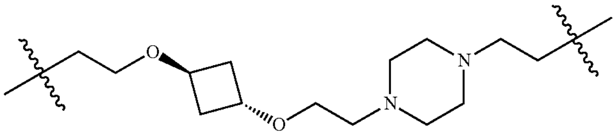
;
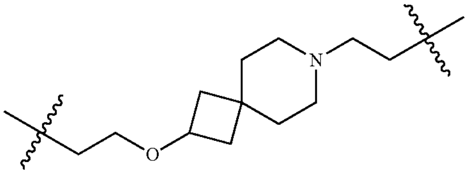
;
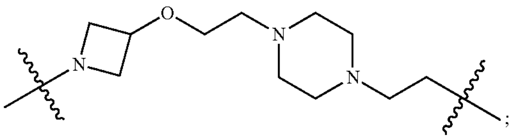
;
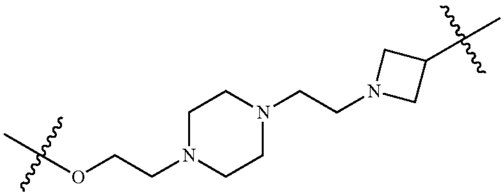
;
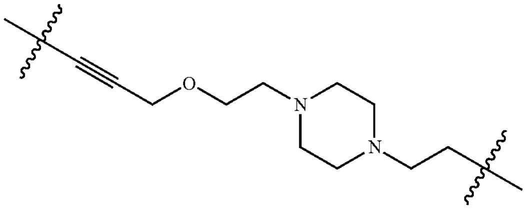
;
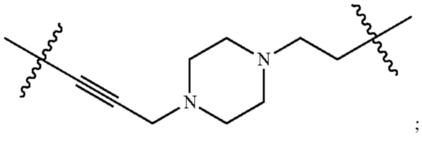
;
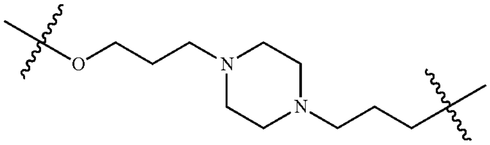
;
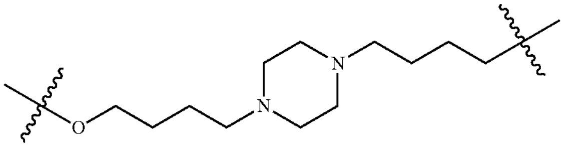
;

-continued
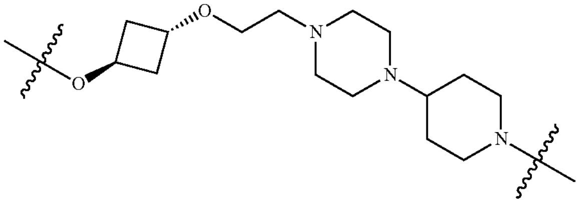
;
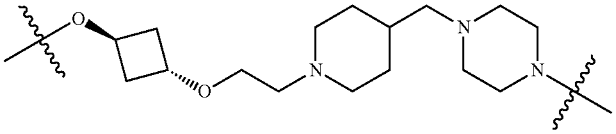
;
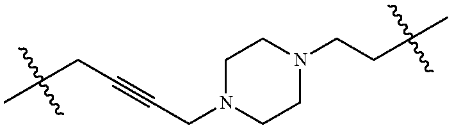
;
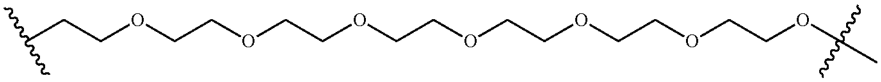
;
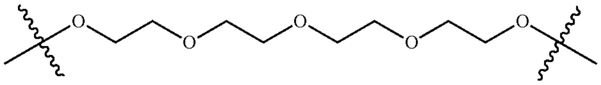
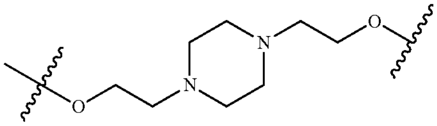
;
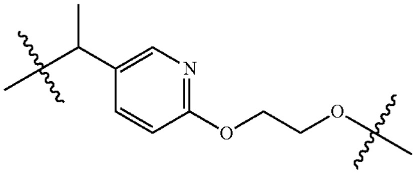
;
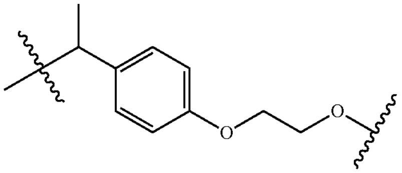
;
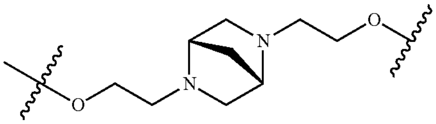
;
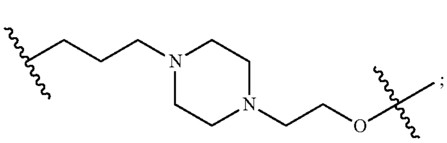
;
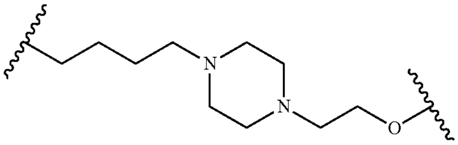
;
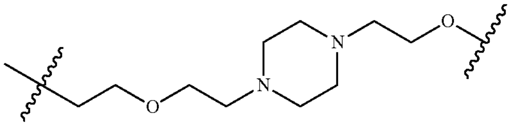
;
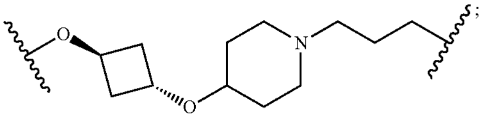
;
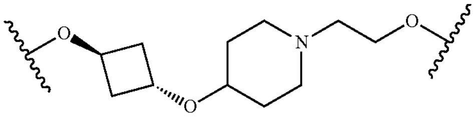
;
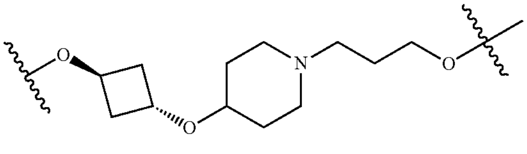
;
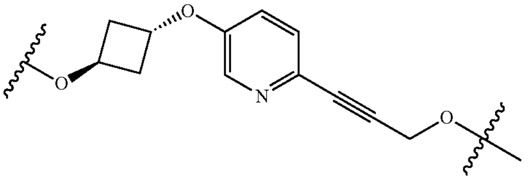
;
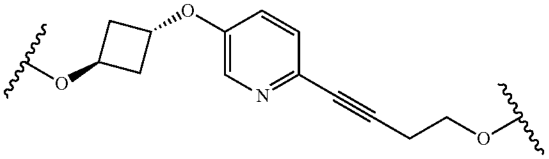
;
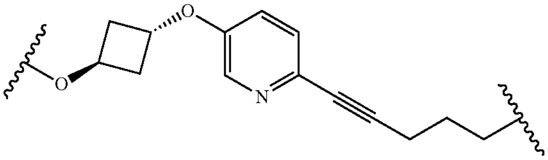
;
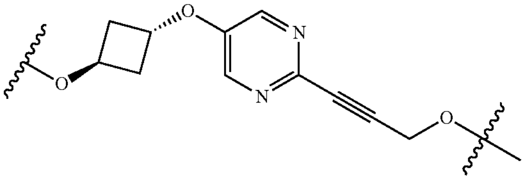
;

-continued
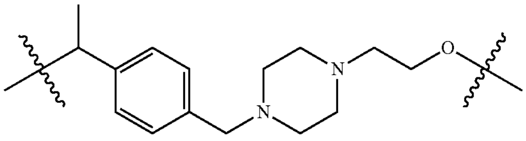
;
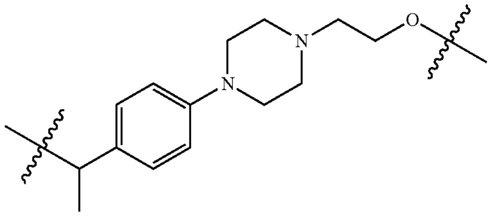
;
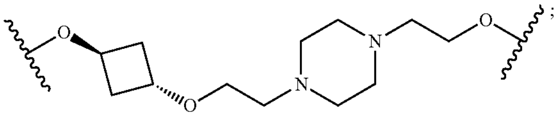
;
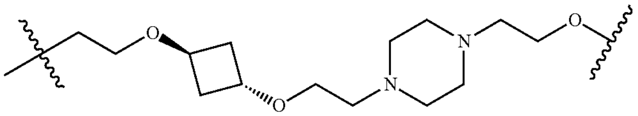
;
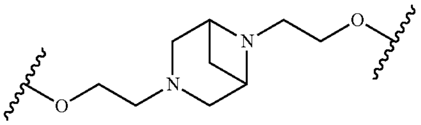
;
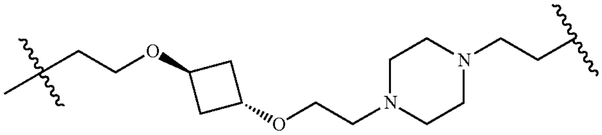
;
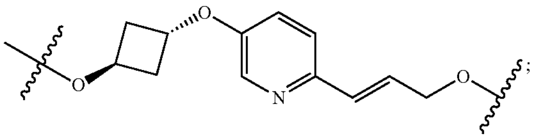
;
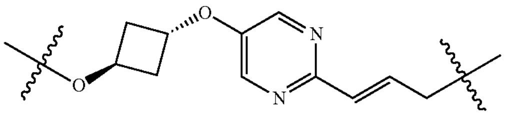
;
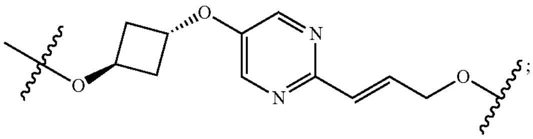
;
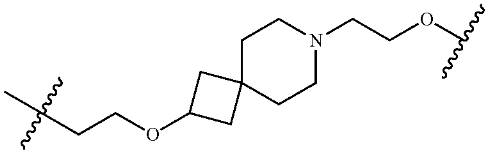
;
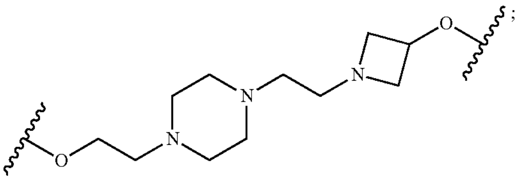
;
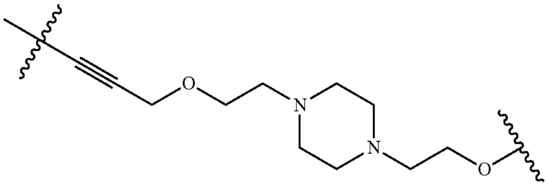
;
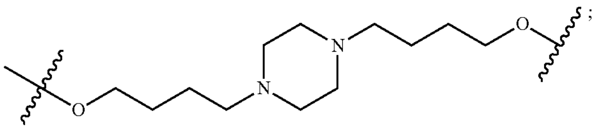
;
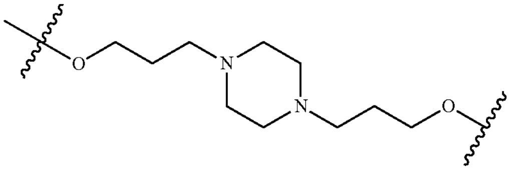
;
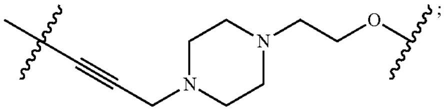
;
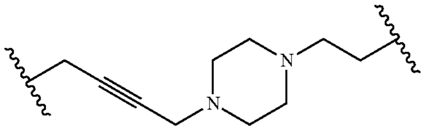
;
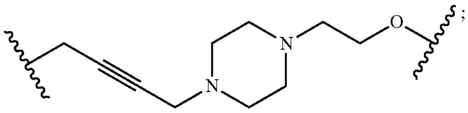
;
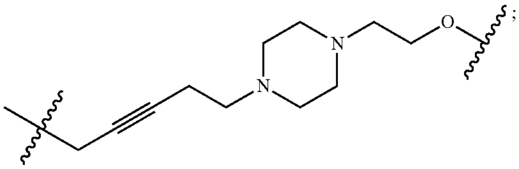
;
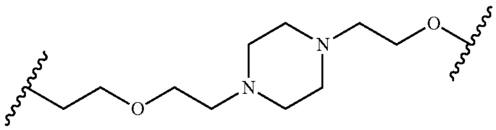
;
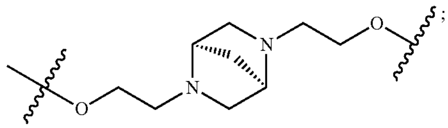
;

-continued
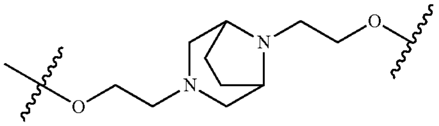
;
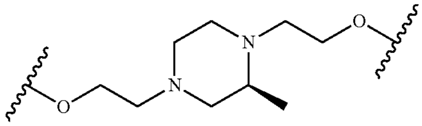
;
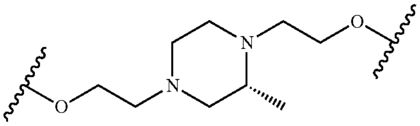
;
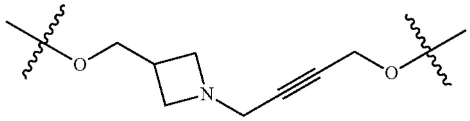
;
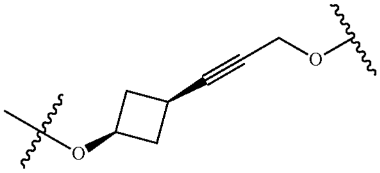
;
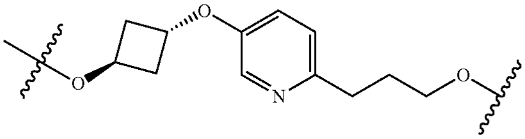
;
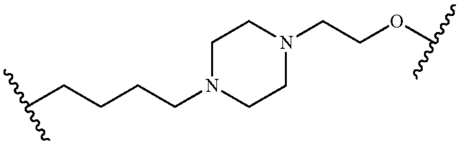
;
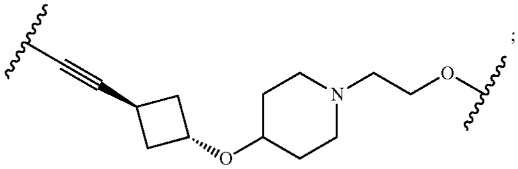
;
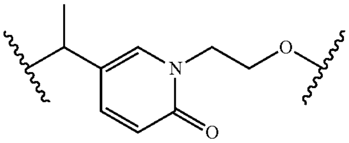
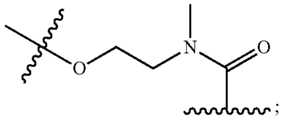
;
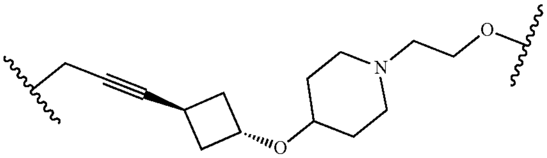
;
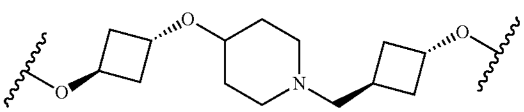
;
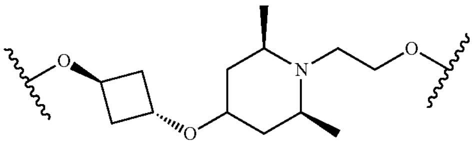
;
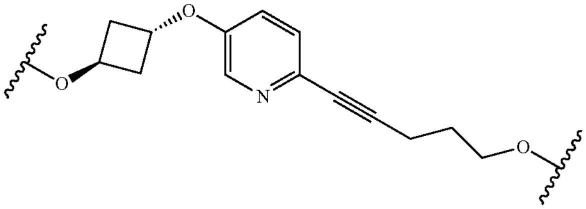
;
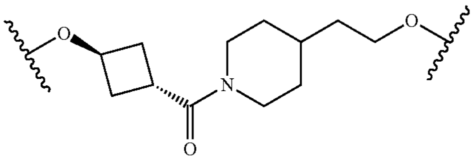
;
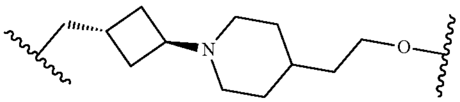
;
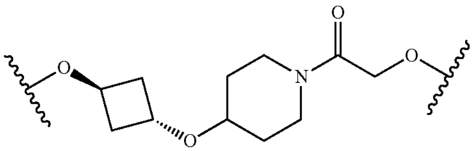
;
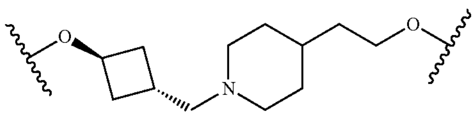
;
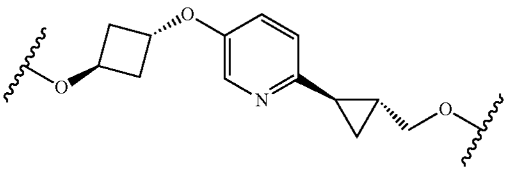
;
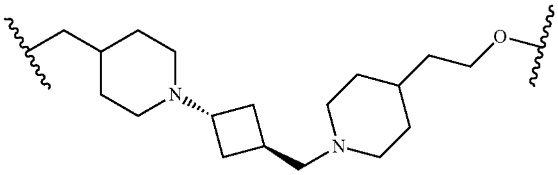
;

-continued
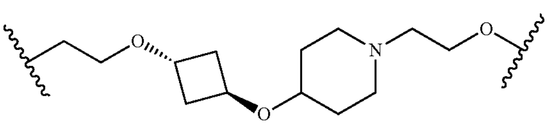
;
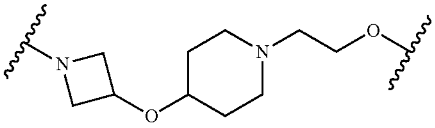
;
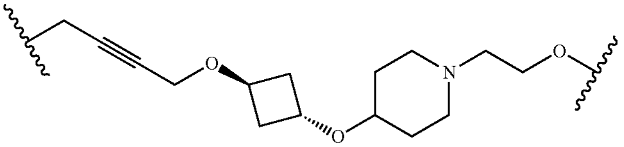
;
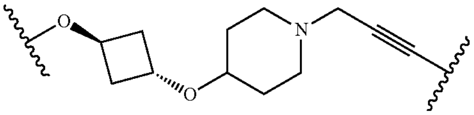
;
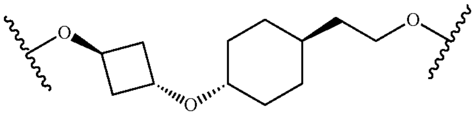
;
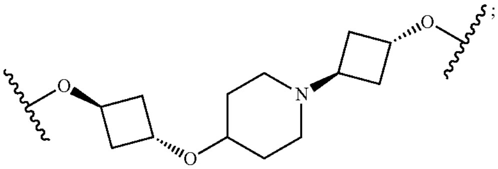
;
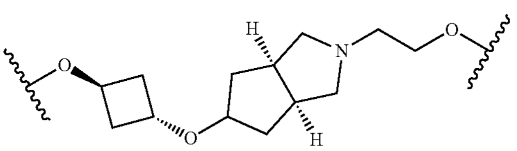
;
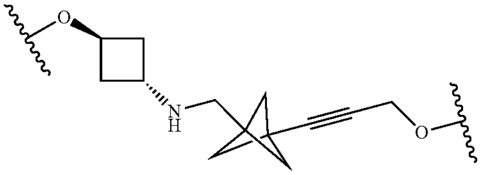
;
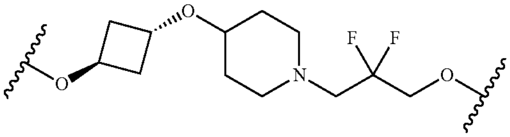
;
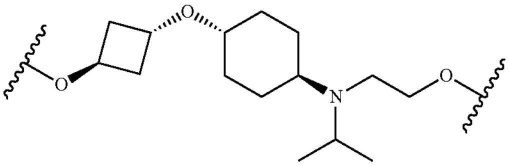
;
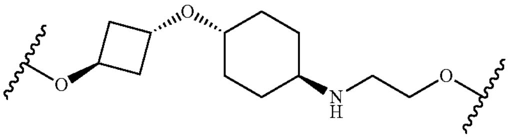
;
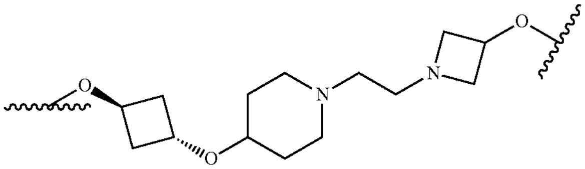
;
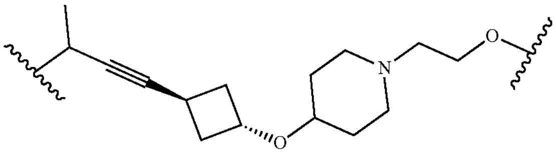
;
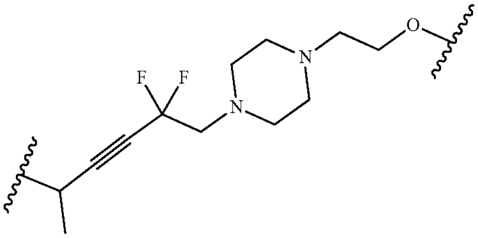
;
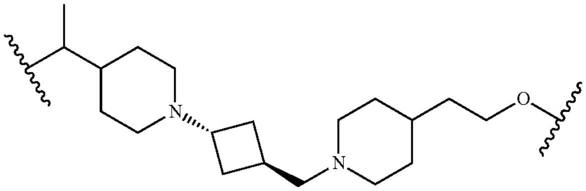
;
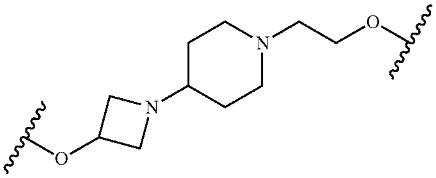
;
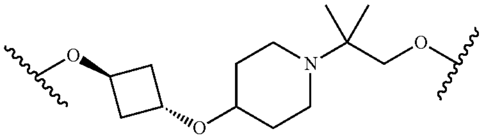
;
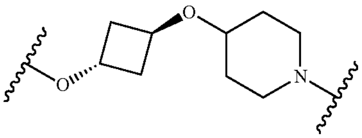
;

-continued
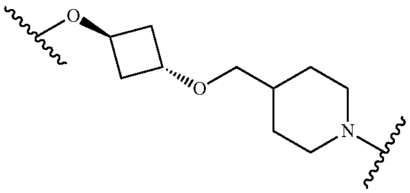
;
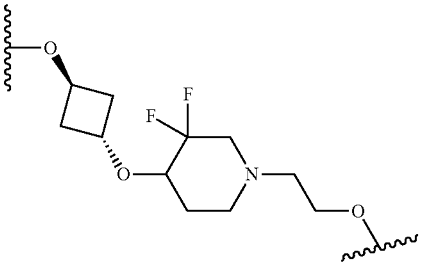
;
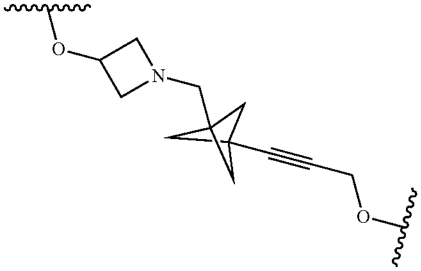
;
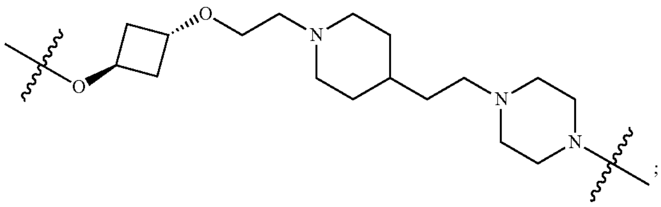
;
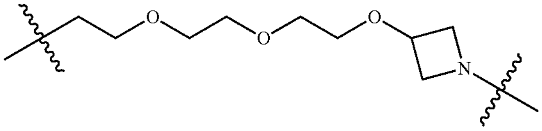
;
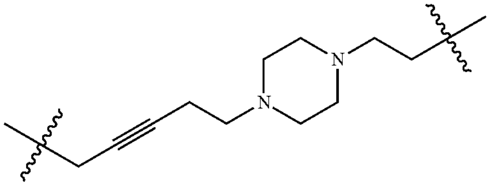
;
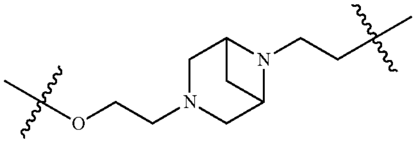
;
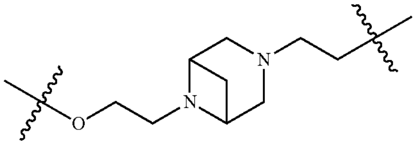
;
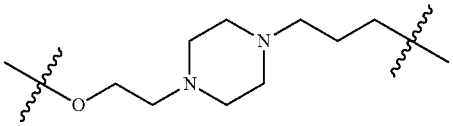
;
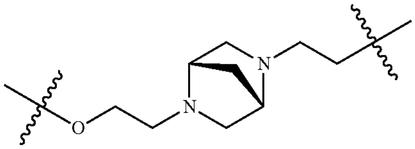
;
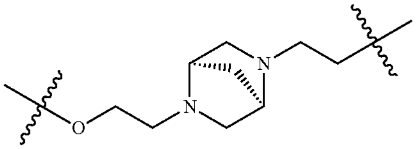
;
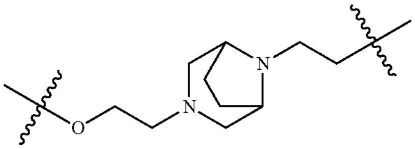
;
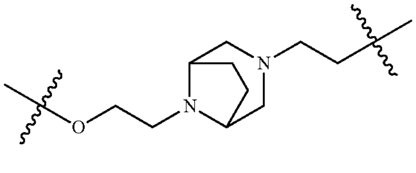
;
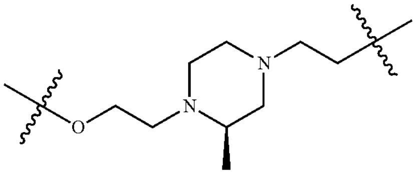
;
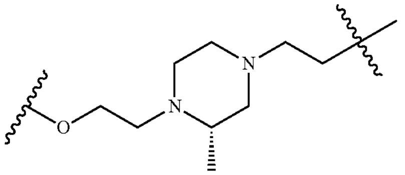
;
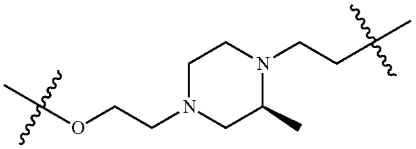
;
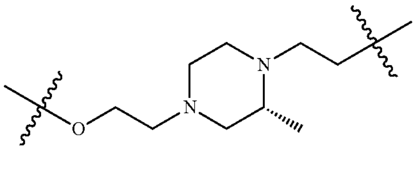
;
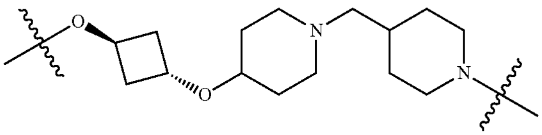
;

-continued
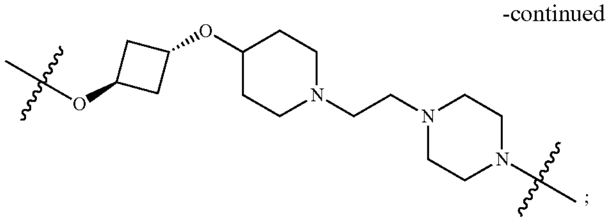 ; 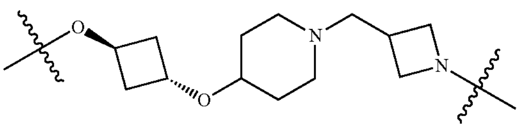 ;
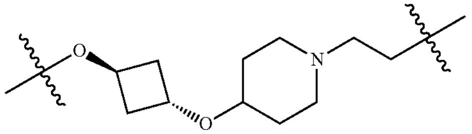 ; 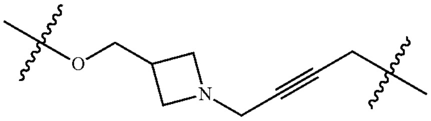 ;
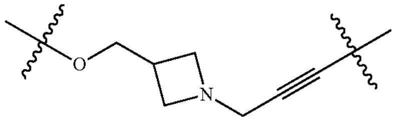 ; 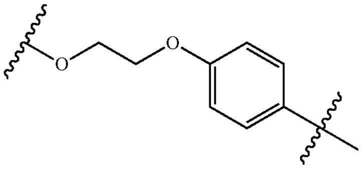 ;
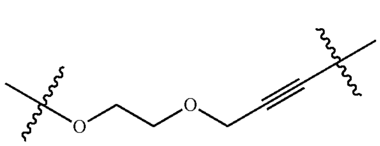 ; 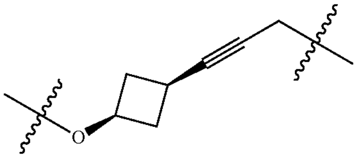 ; and
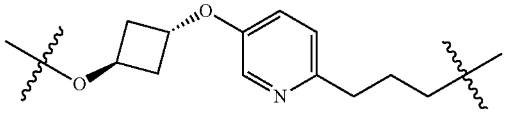 .
In any aspect or embodiment described herein, the linker unit or linker (L) comprises a group represented by a structure selected from the group consisting of: $—O—(CH_2)_m—O(CH_2)_n—O(CH_2)_o—O(CH_2)_p—O(CH_2)_q—O(CH_2)_r—O(CH_2)_s—O(CH_2)_t—$; $O—(CH_2)_m—O(CH_2)_n—O(CH_2)_o—O(CH_2)_p—O(CH_2)_q—O(CH_2)_r—O(CH_2)_s—O—$; $—(CH_2)_m—O(CH_2)_n—O(CH_2)_o—O(CH_2)_p—O(CH_2)_q—O(CH_2)_r—O(CH_2)_s—O(CH_2)_t—$; $—CH{=}CH(CH_2)_m\ O(CH_2)_n—O(CH_2)_o—O(CH_2)_p—O(CH_2)_q—O(CH_2)_r—O(CH_2)_s—O(CH_2)_t—$; $—O(CH_2)_nNCH_3C({=}O)(CH_2)_m—$.
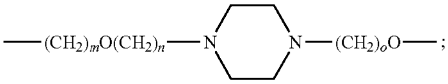 ; 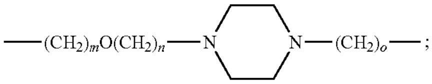 ;
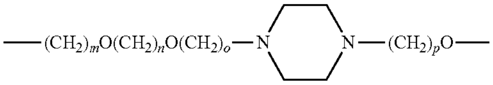 ; 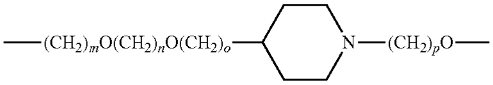 ;
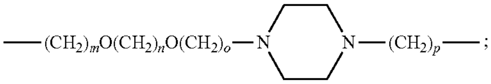 ; 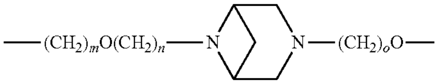 ;
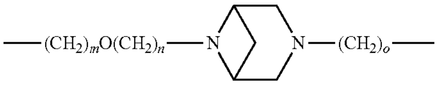 ; 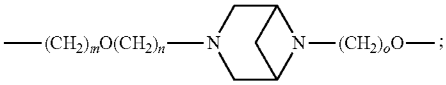 ;
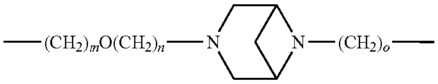 ; 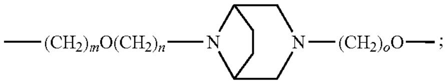 ;
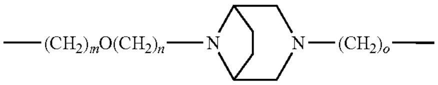 ; 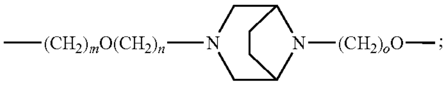 ;
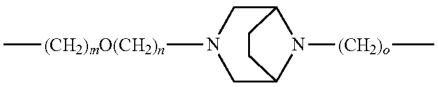 ; 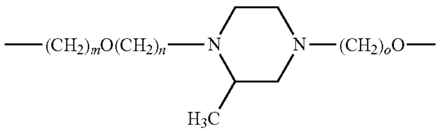 ;

-continued
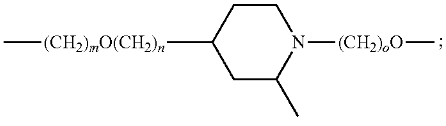 ; 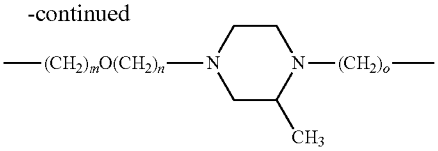 ;
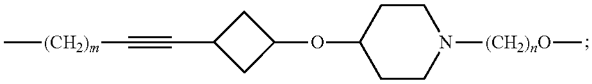 ;
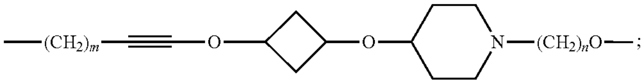 ;
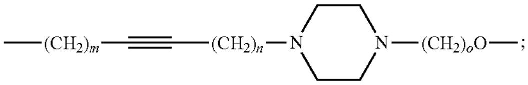 ; 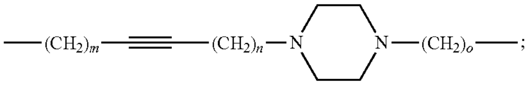 ;
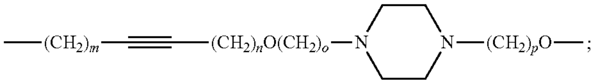 ;
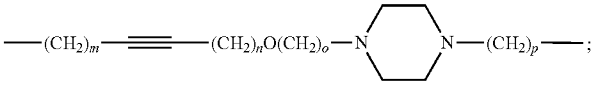 ; 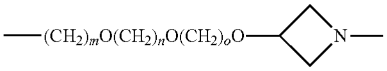 ;
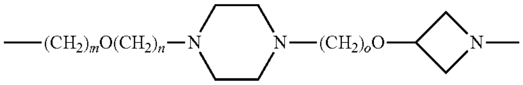 ; 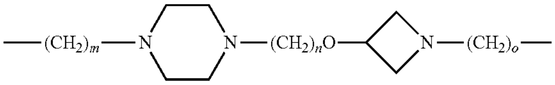 ;
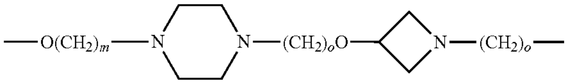 ; 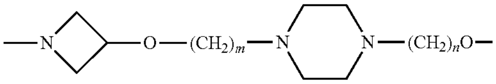 ;
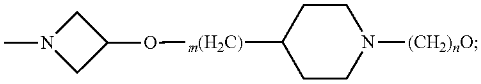 ; 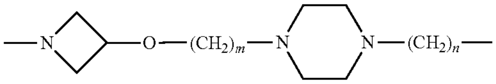 ;
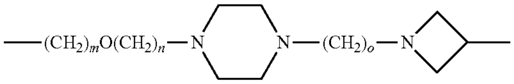 ; 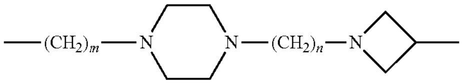 ;
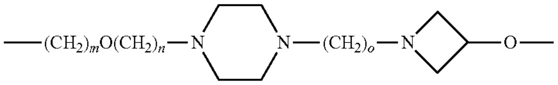 ; 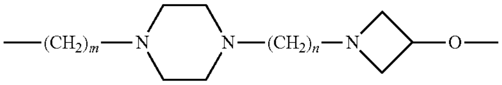 ;
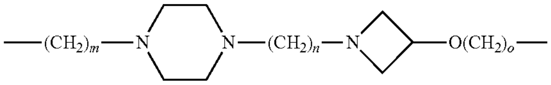 ; 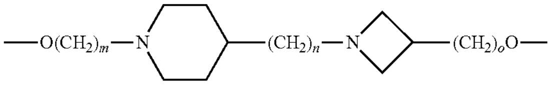 ;
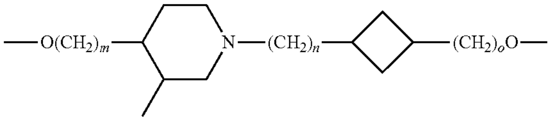 ; 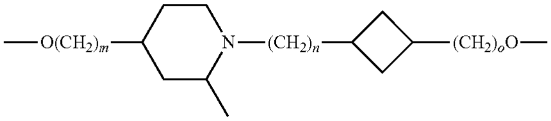 ;
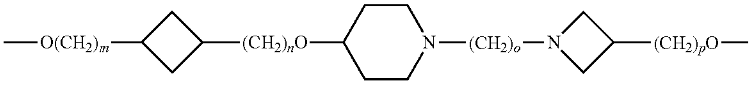 ;
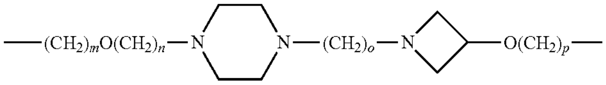 ;
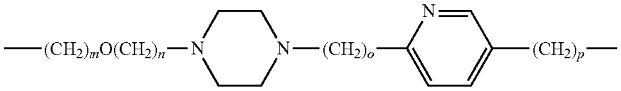 ;
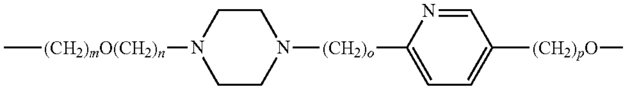 ;
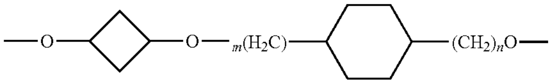 ; 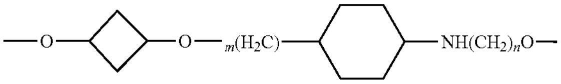 ;
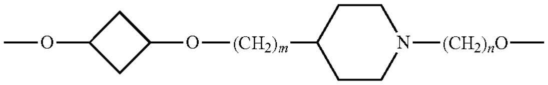 ; 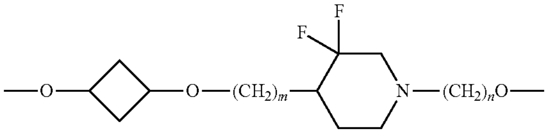 ;

-continued
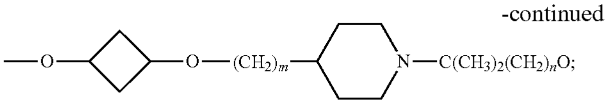
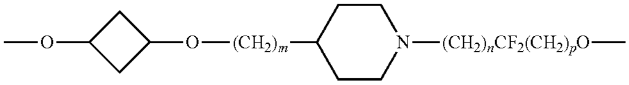 ;
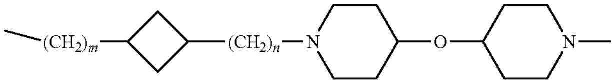 ;
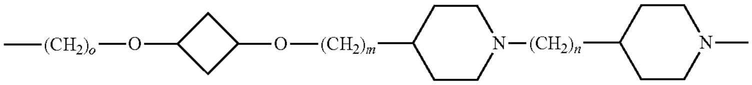 ;
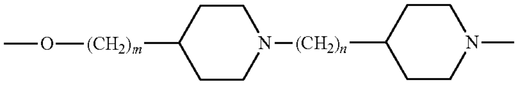 ; 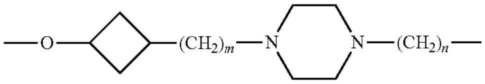 ;
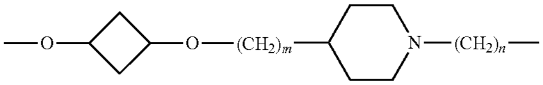 ; 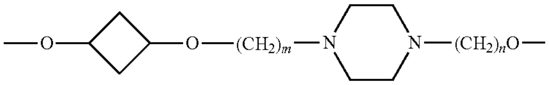 ;
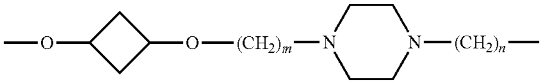 ;
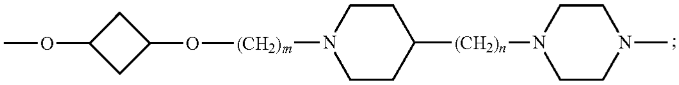 ;
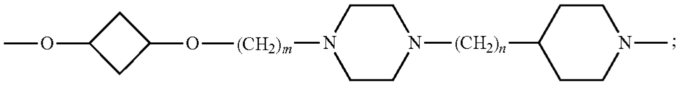 ;
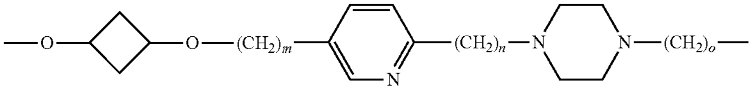 ;
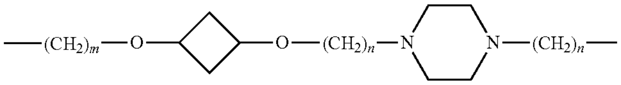 ;
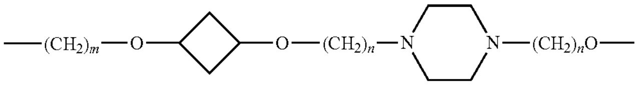 ;
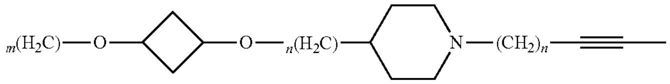 ;
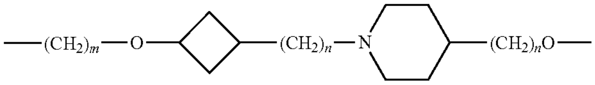 ;
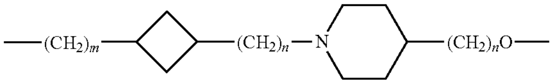 ;
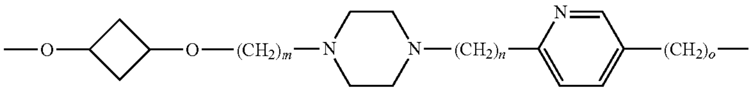 ;
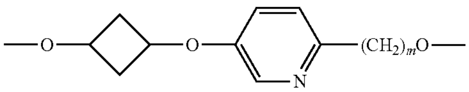 ; 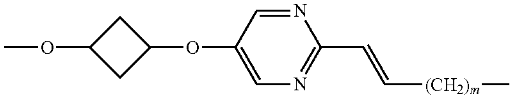 ;
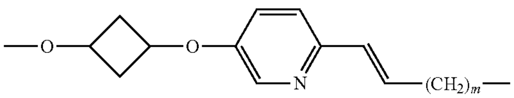 ; 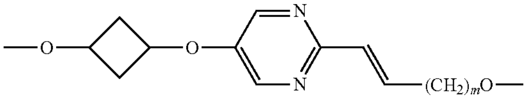 ;
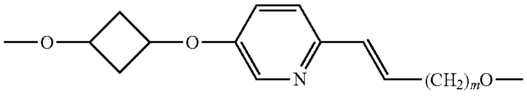 ; 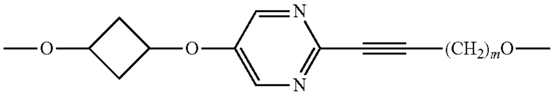 ;
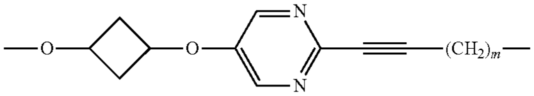 ; 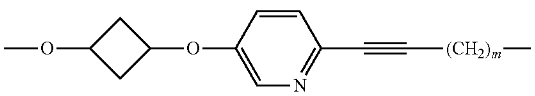 ;

-continued
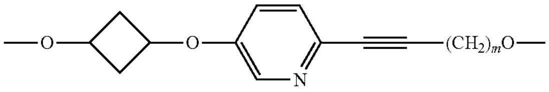 ;
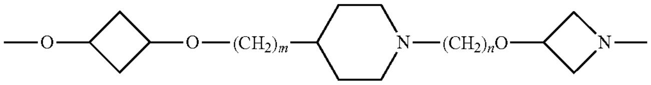 ;
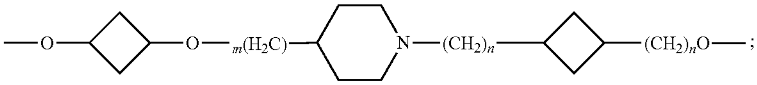 ;
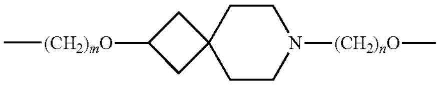 ; 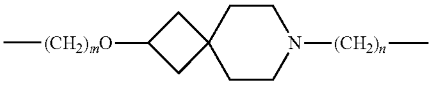 ;
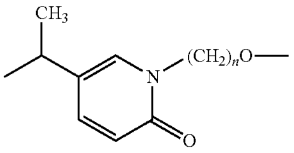 ; 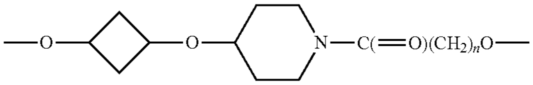 ;
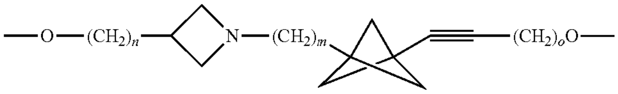 ;
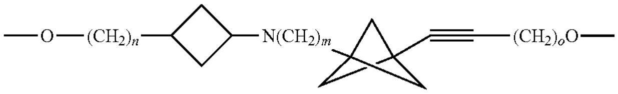 ;
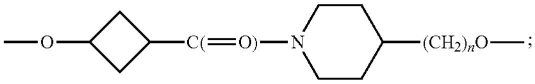 ; 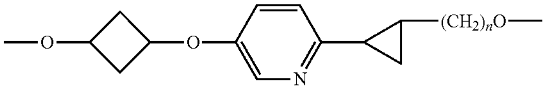 ;
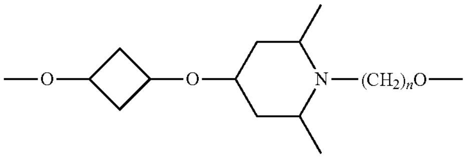 ; 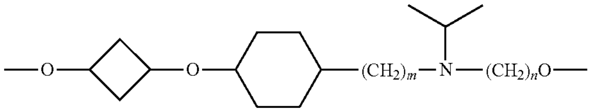
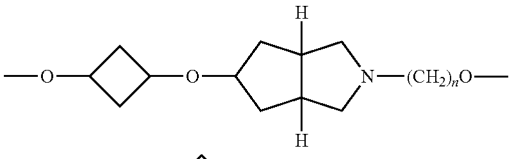 ; 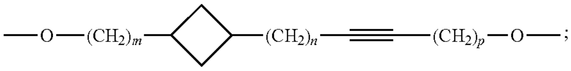 ;
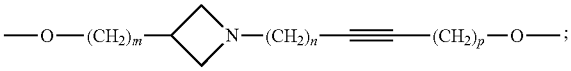 ;
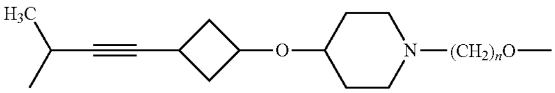 ; 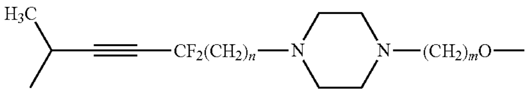 ;
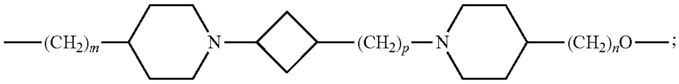 ; 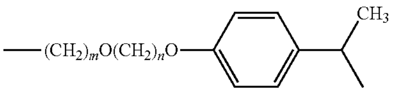 ;
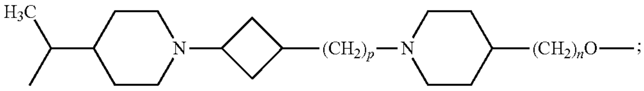 ; 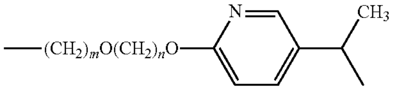 ;
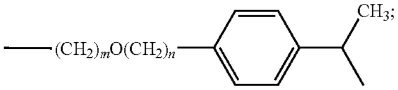 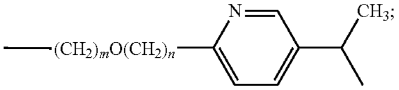
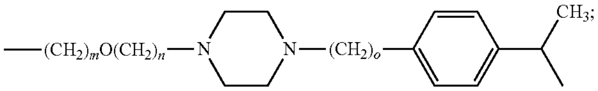
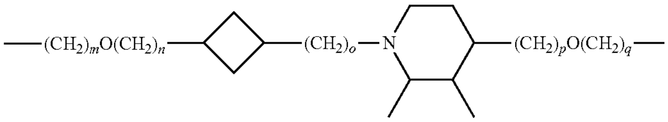 ;

-continued
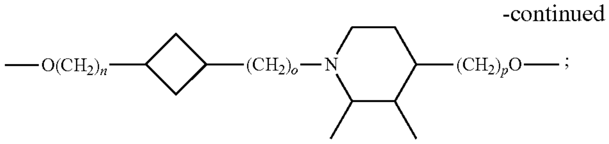
;
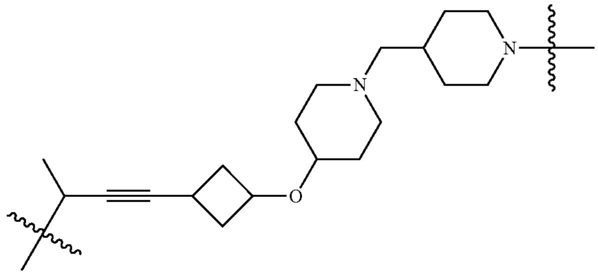
,
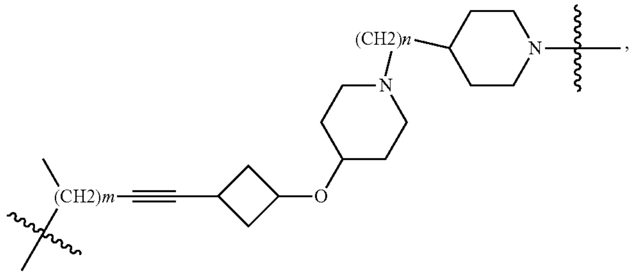
,
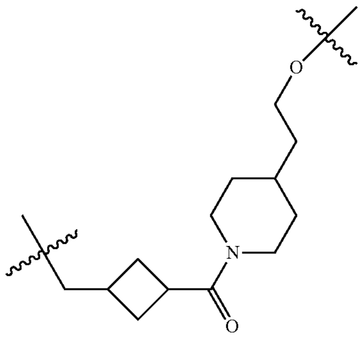
,
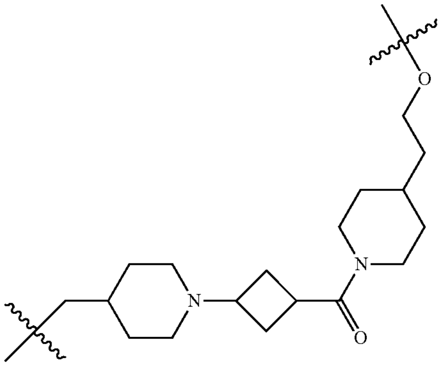
, and
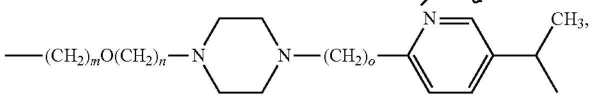
wherein m, n, o, p, q, r, s and t are each independently selected from the integers 0, 1, 2, 3 and 4.
In any aspect or embodiment described herein, the linker (L) is selected from the group consisting of:
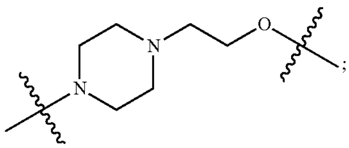
;
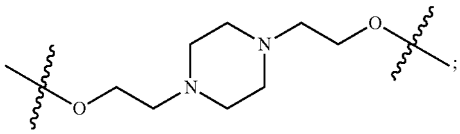
;
-continued
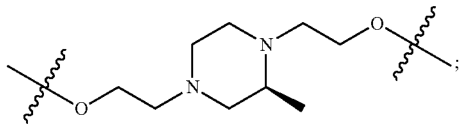
;
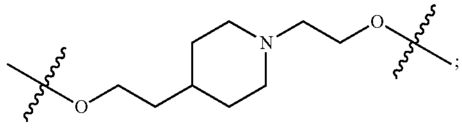
;
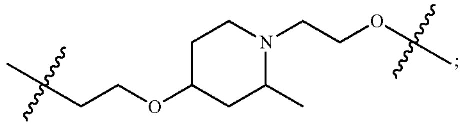
;
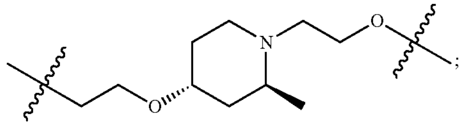
;

-continued
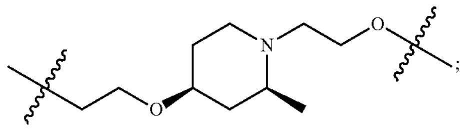
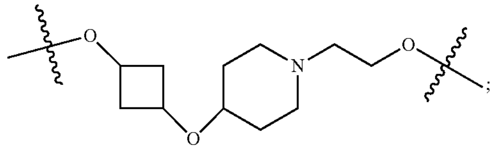
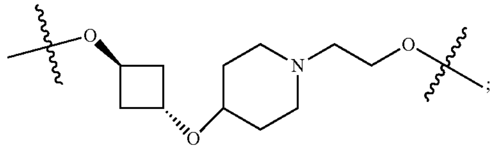
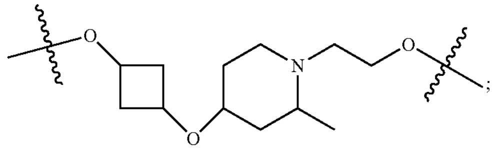
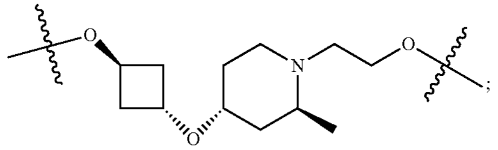
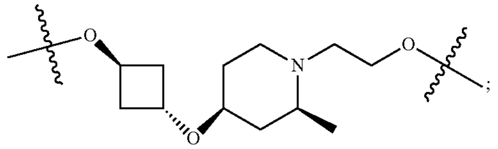
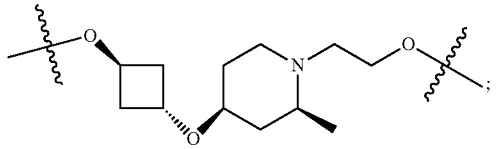
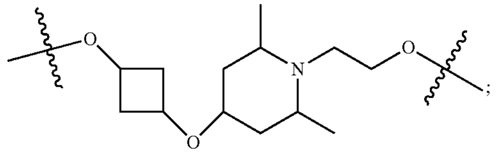
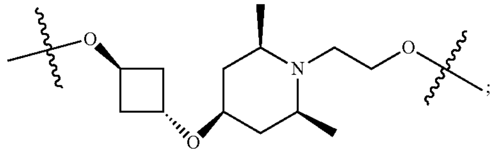
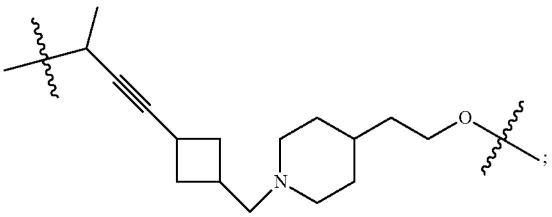
-continued
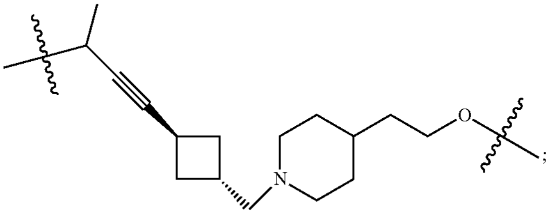
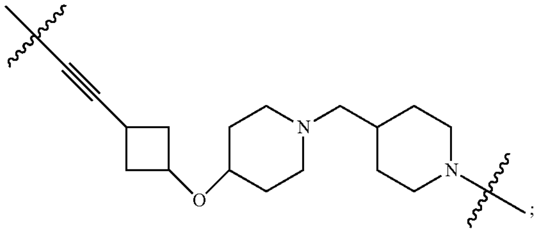
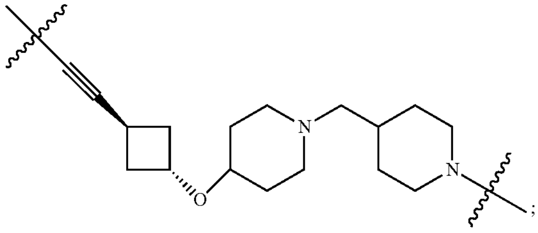
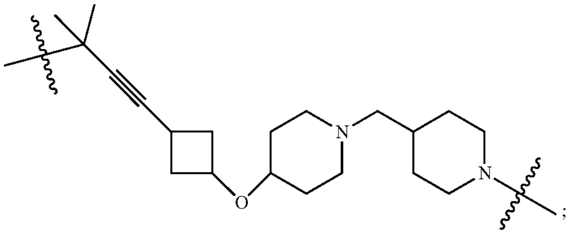
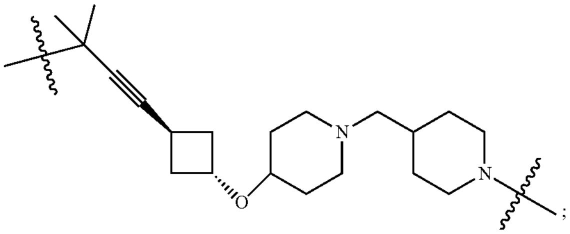
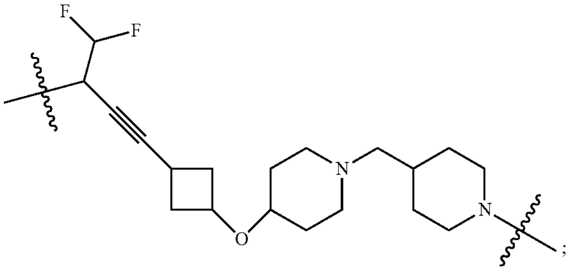
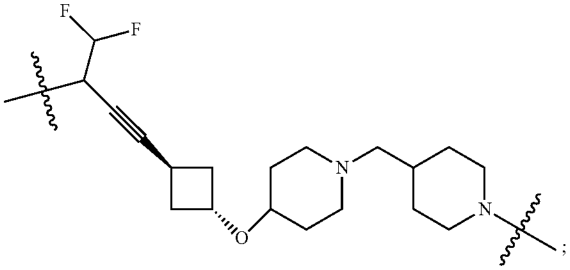

-continued
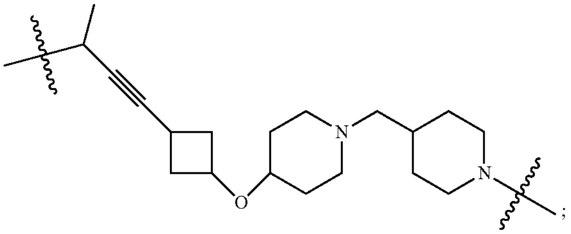
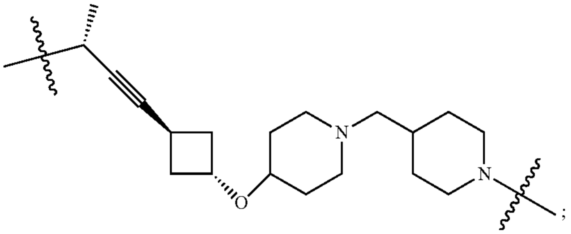
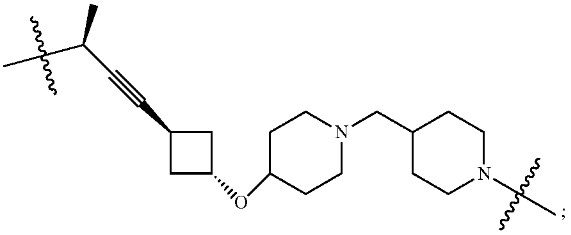
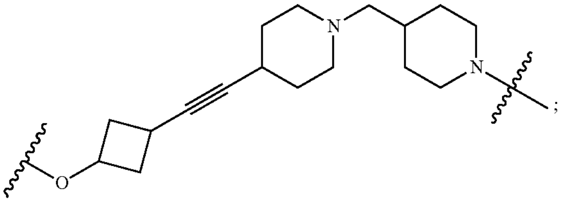
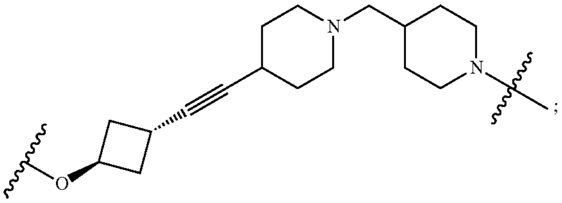
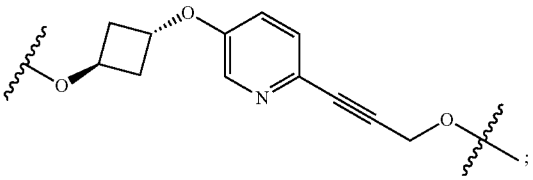
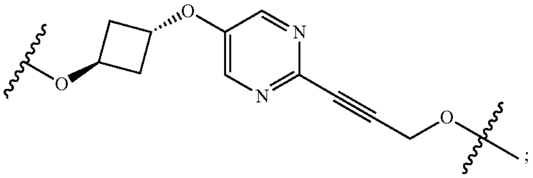
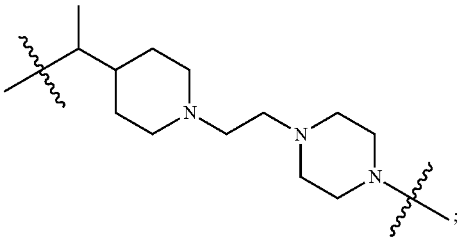
-continued
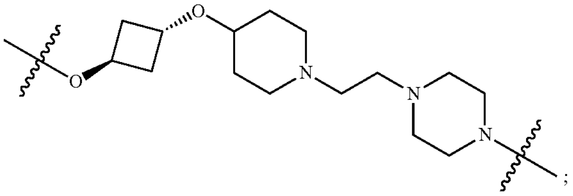
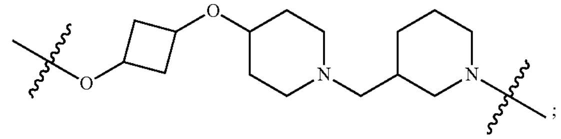
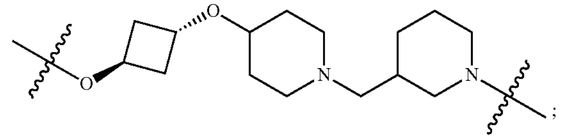
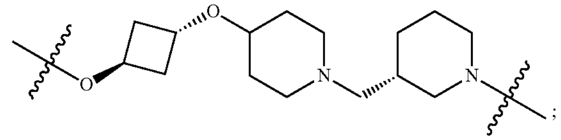
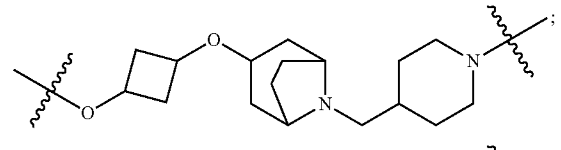
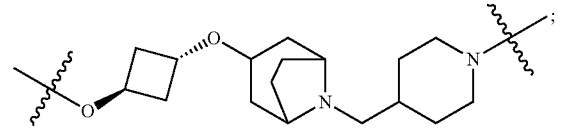
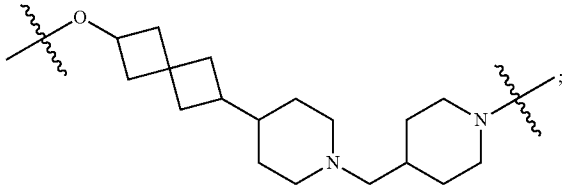
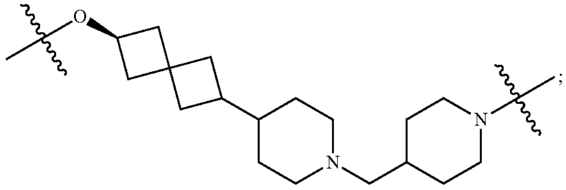
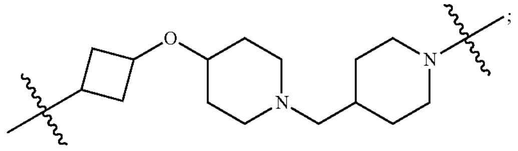
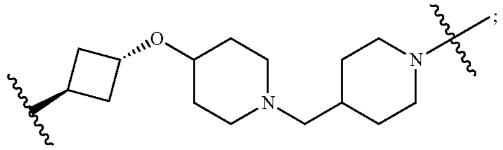
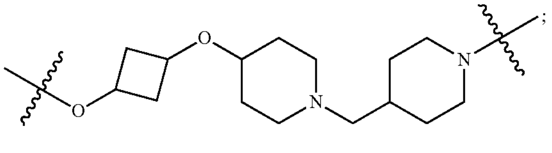

-continued
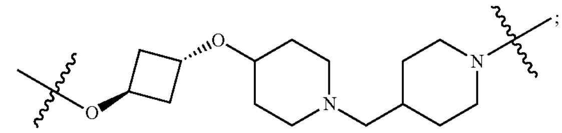
;
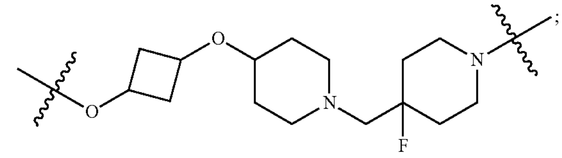
;
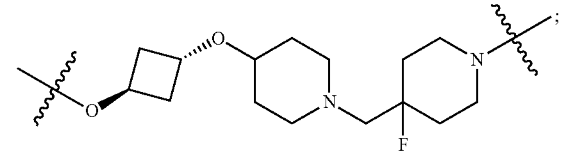
;
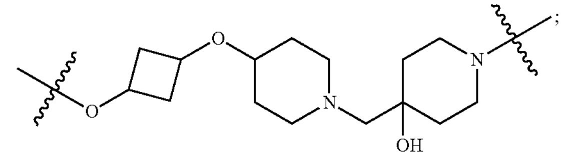
;
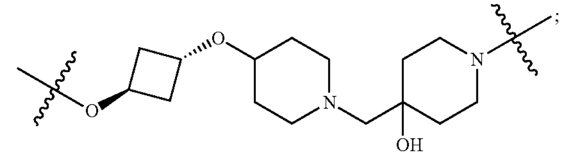
;
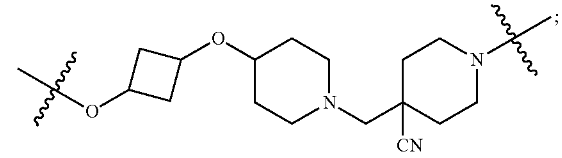
;
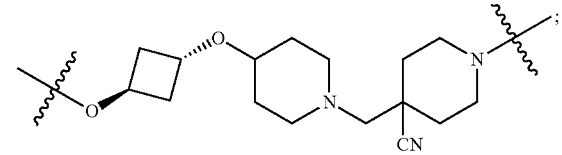
;
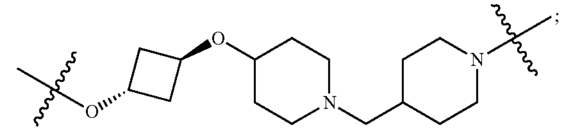
;
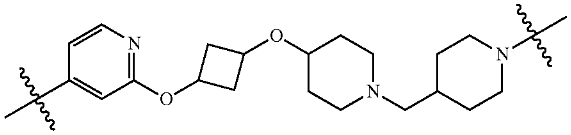
;
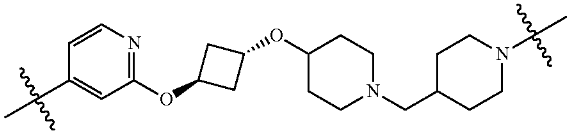
;
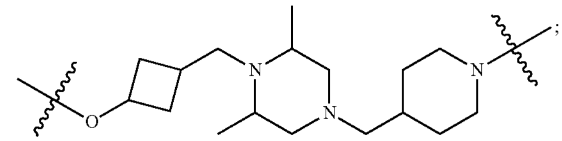
;
-continued
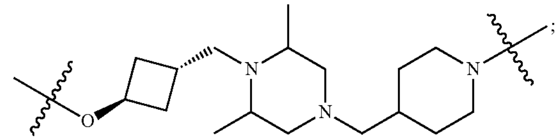
;
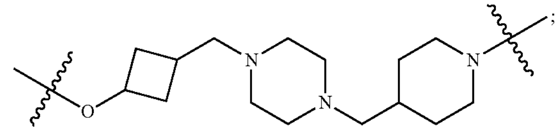
;
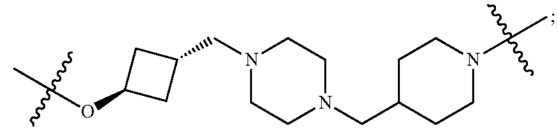
;
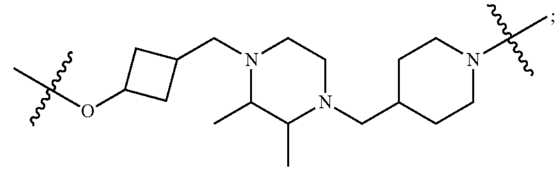
;
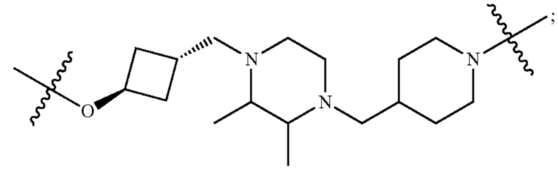
;
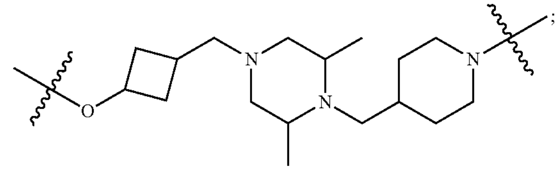
;
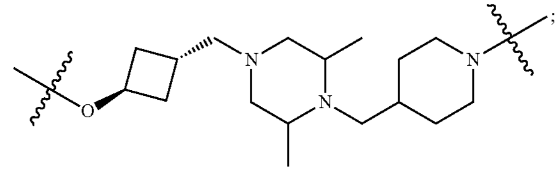
;
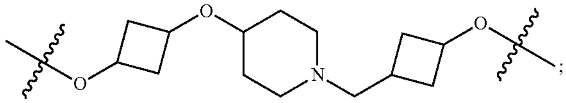
;
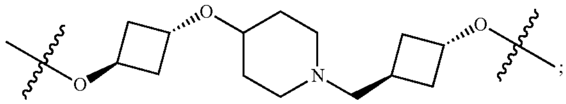
;
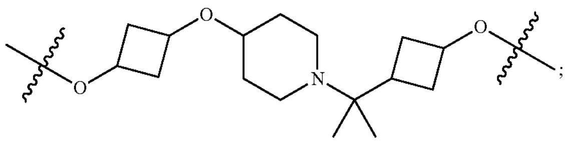
;
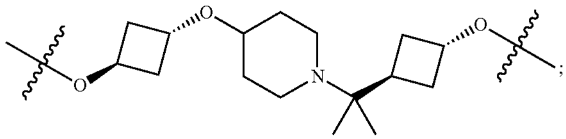
;

-continued
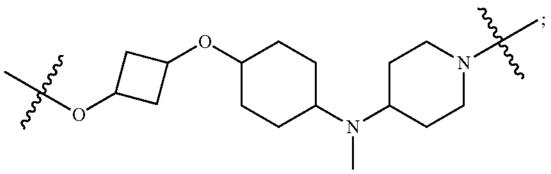
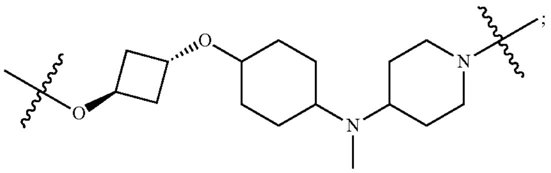
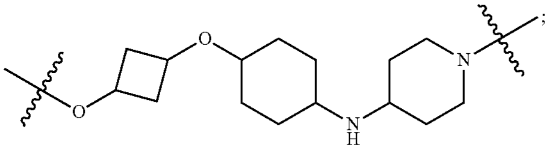
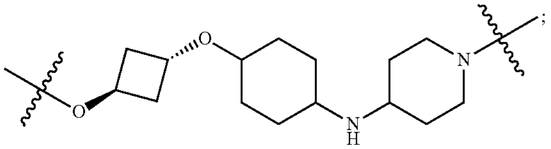
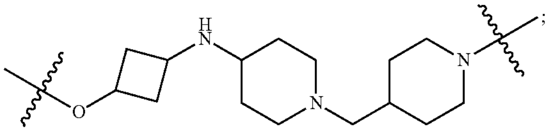
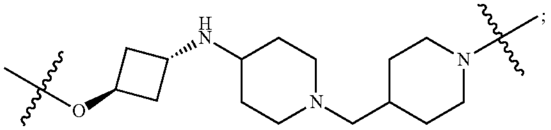
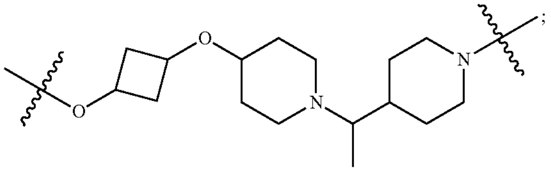
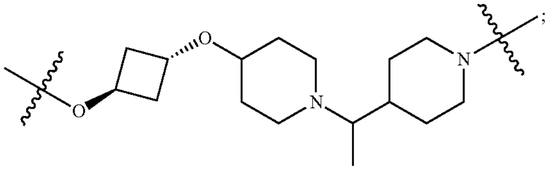
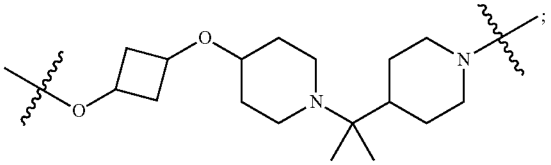
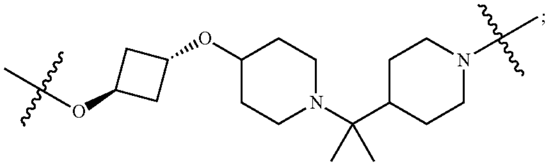
-continued
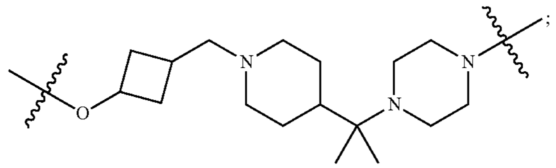
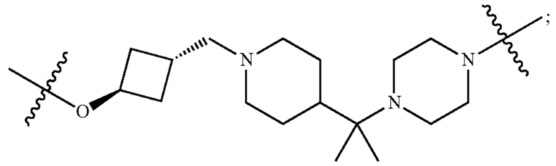
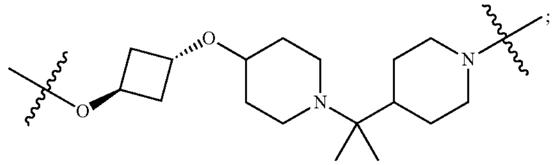
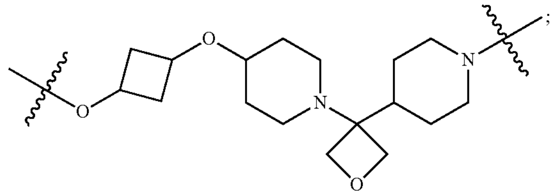
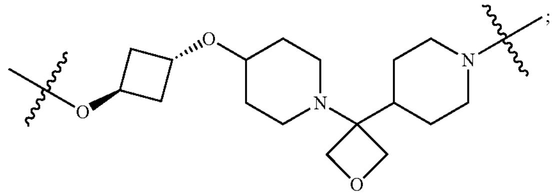
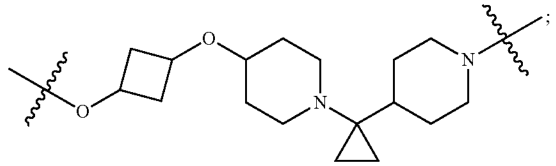
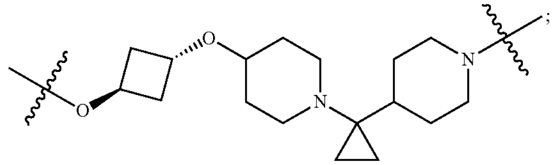
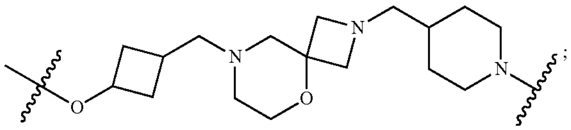
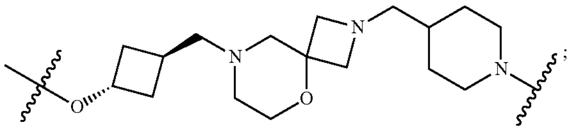
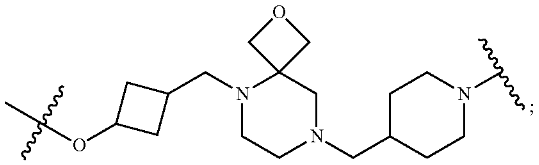

-continued
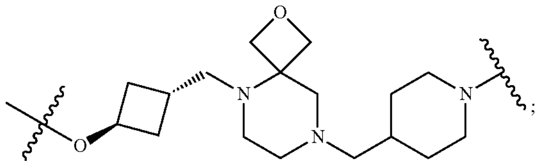
;
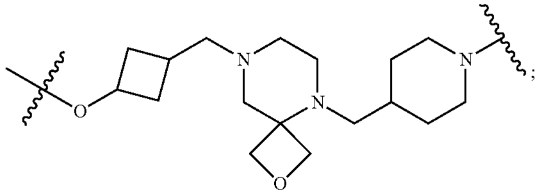
;
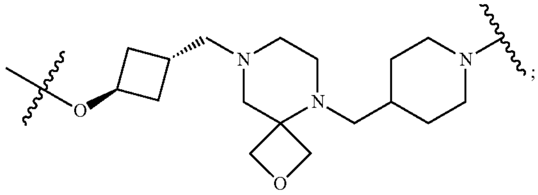
;
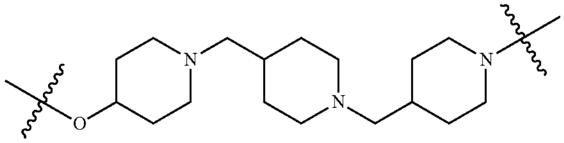
;
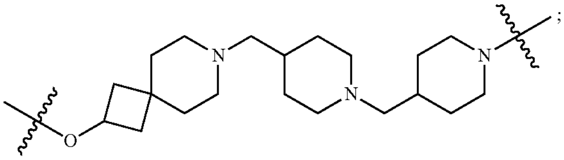
;
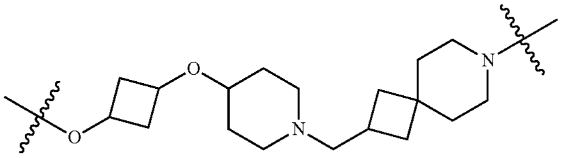
;
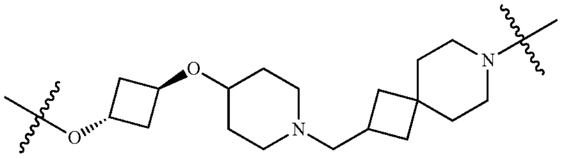
;
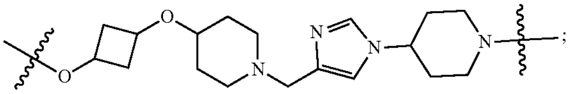
;
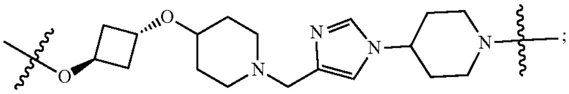
;
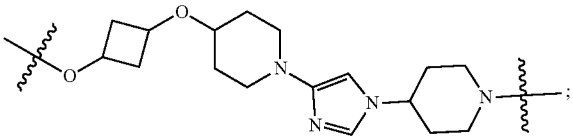
;
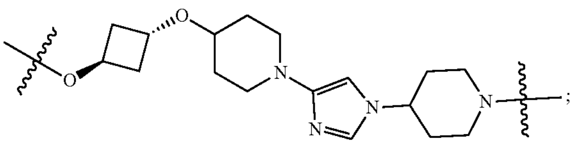
;
-continued
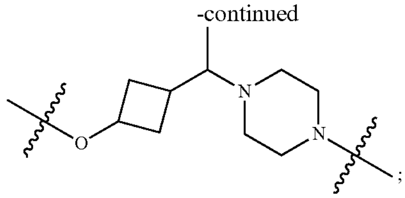
;
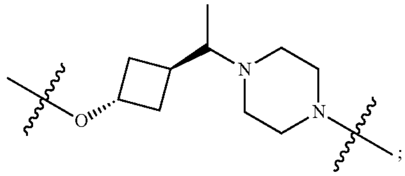
;
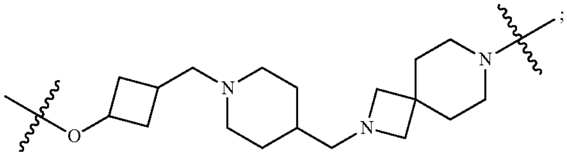
;
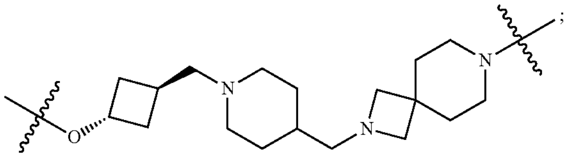
;
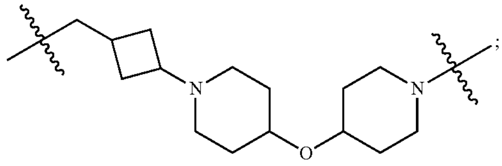
;
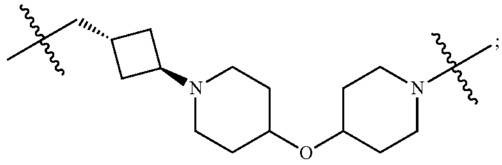
;
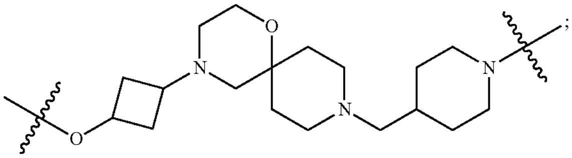
;
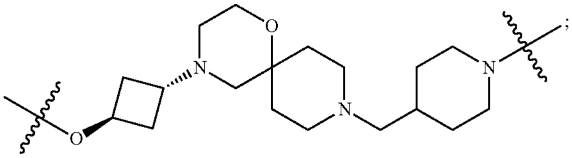
;
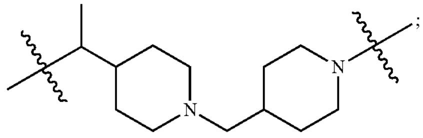
;
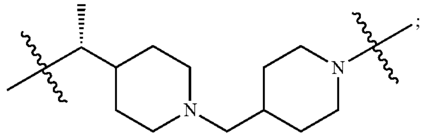
;
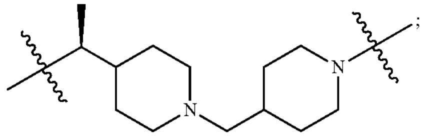
;

-continued
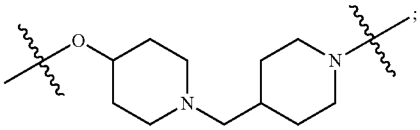
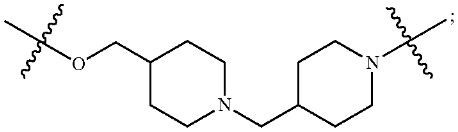
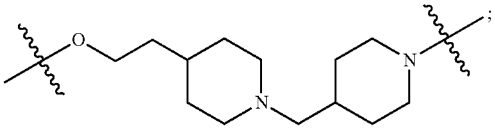
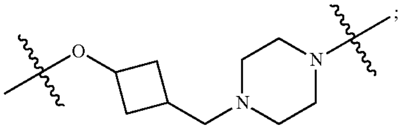
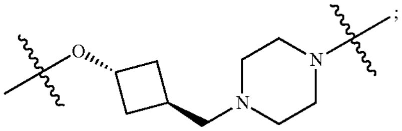
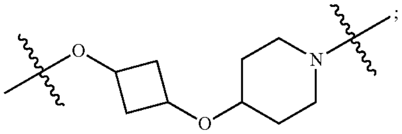
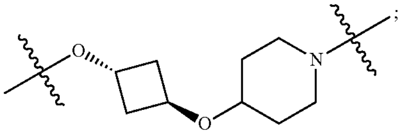
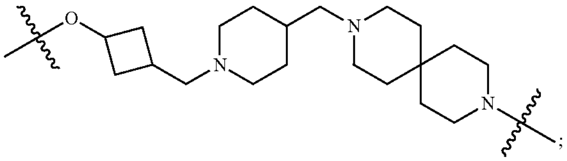
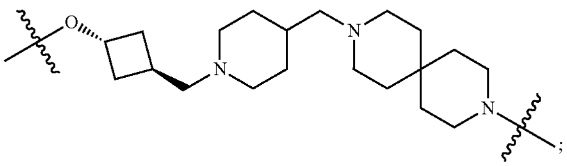
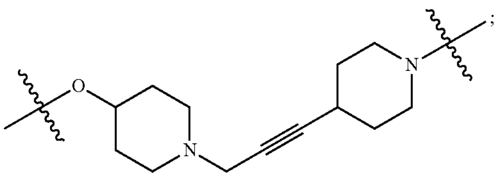
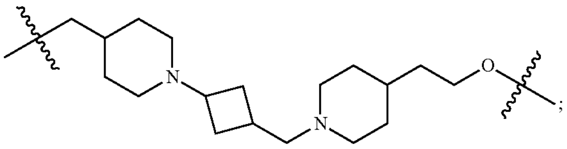
-continued
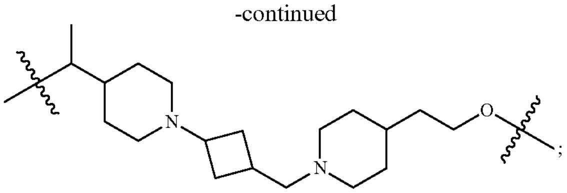
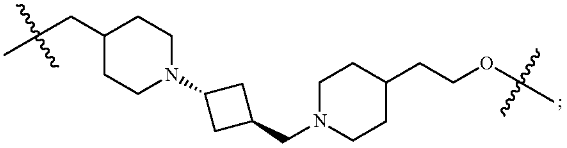
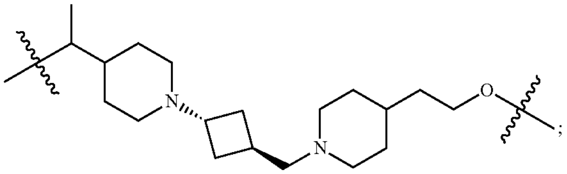
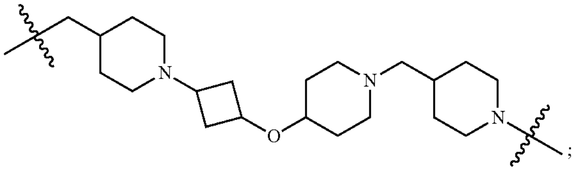
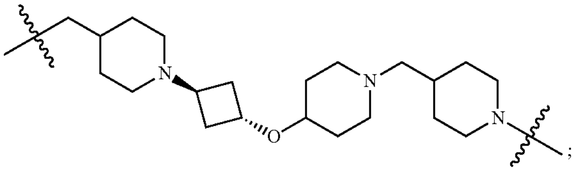
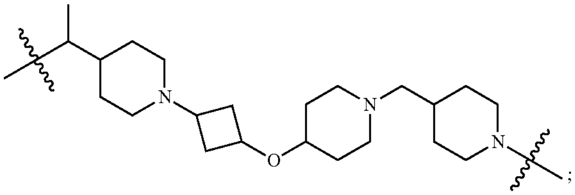
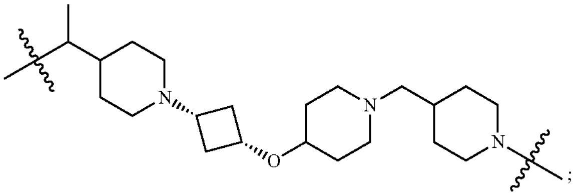
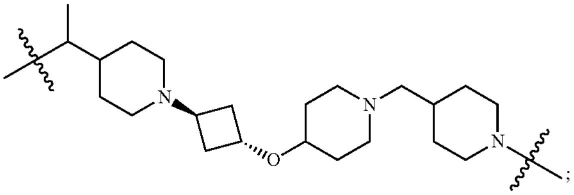
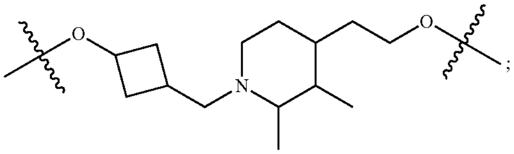
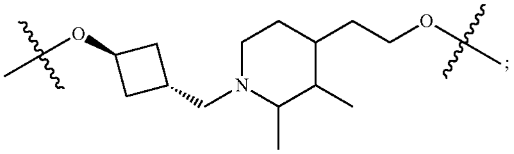

-continued
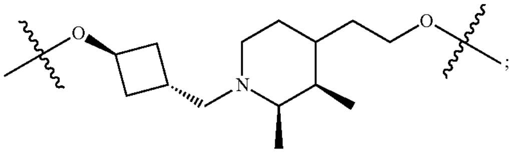;
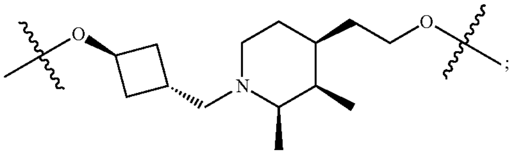;
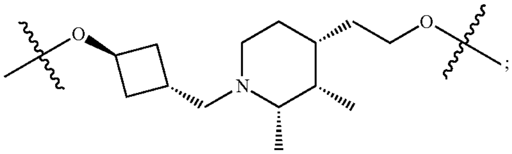;
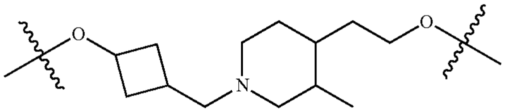;
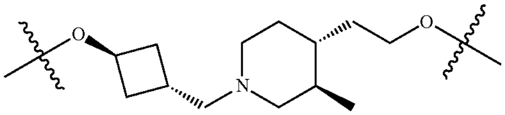;
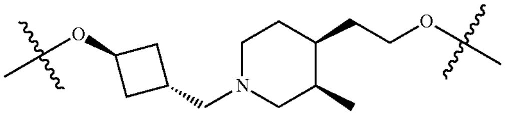;
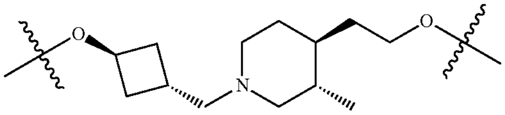;
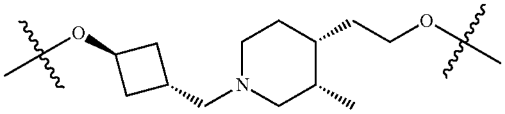;
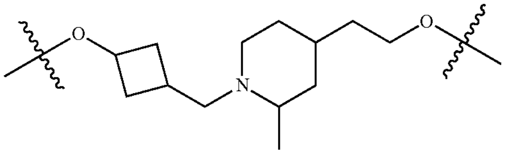;
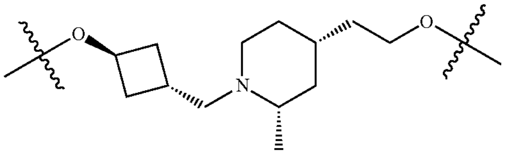;
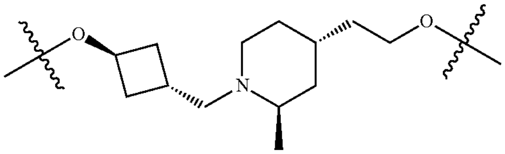;
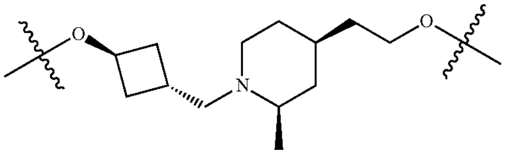;
-continued
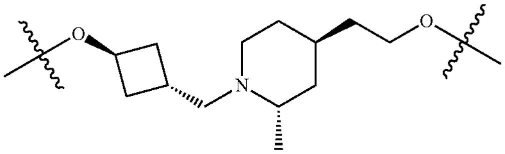;
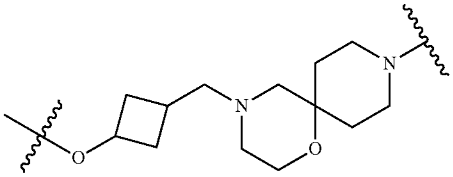;
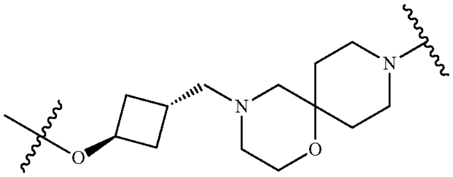;
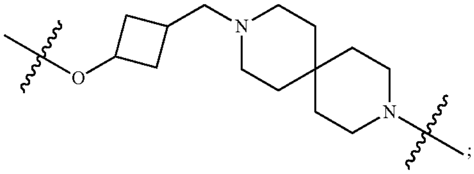;
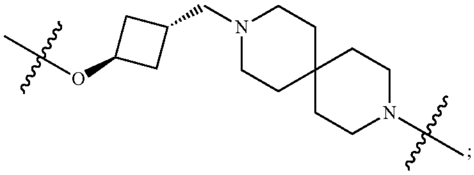;
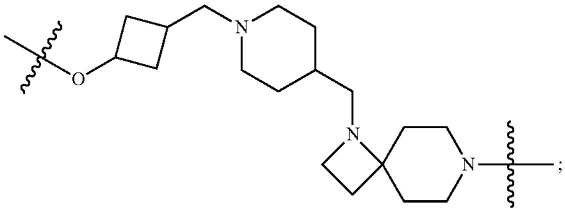;
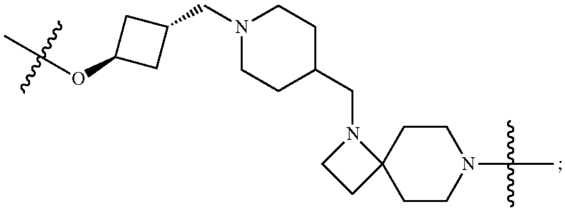;
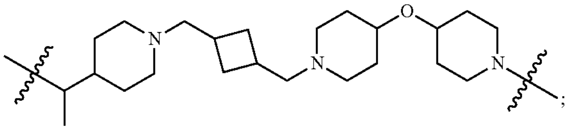;
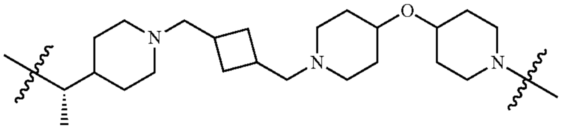;
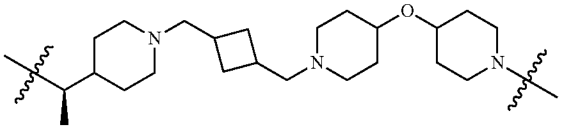;

-continued
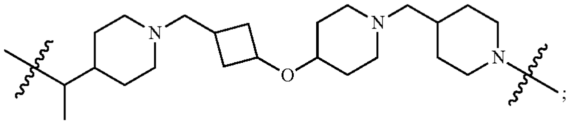
;
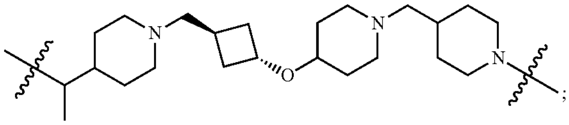
;
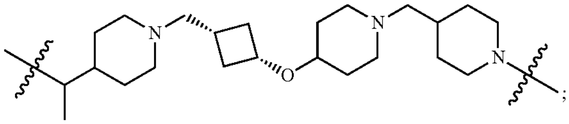
;
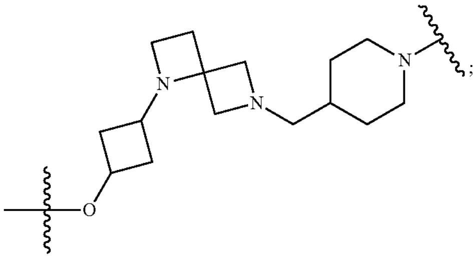
;
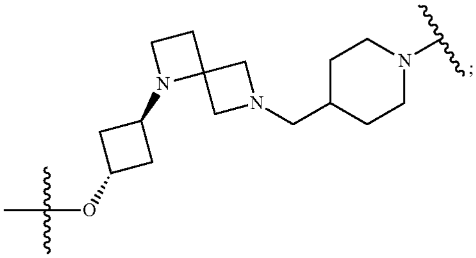
;
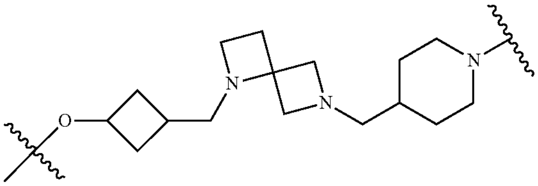
;
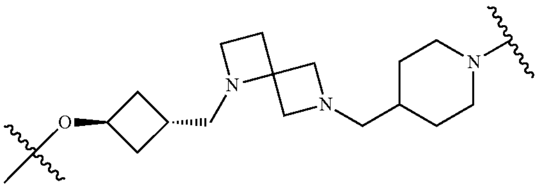
;
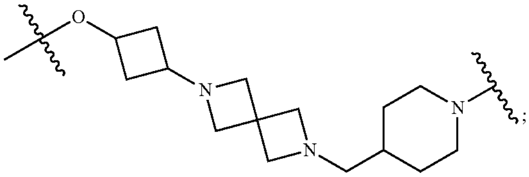
;
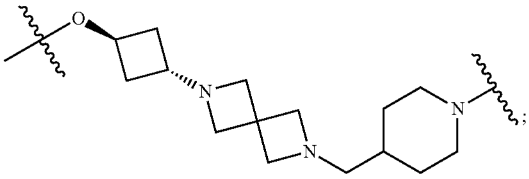
;
-continued
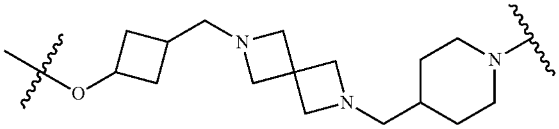
;
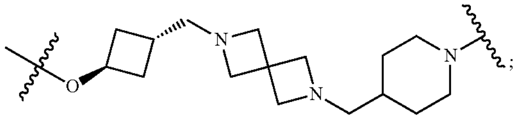
; and
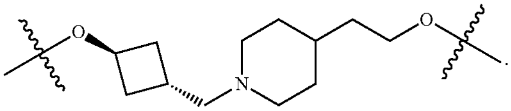
.
In any aspect or embodiment described herein, the linker (L) is selected from the group consisting of:
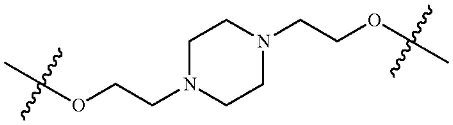
;
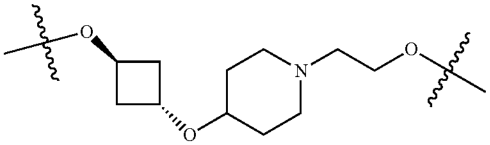
;
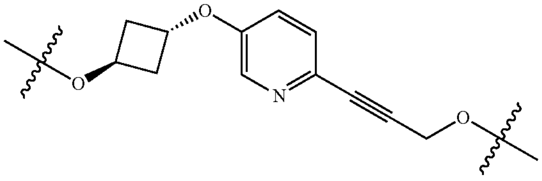
;
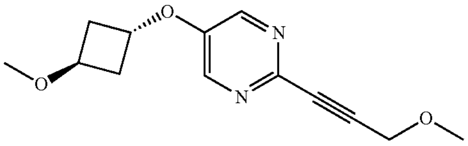
;
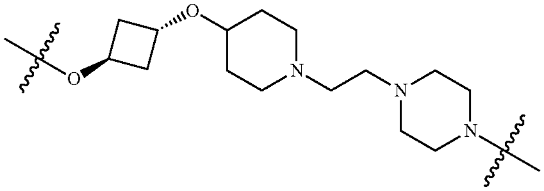
;
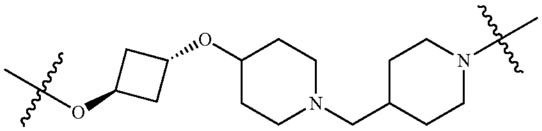
;
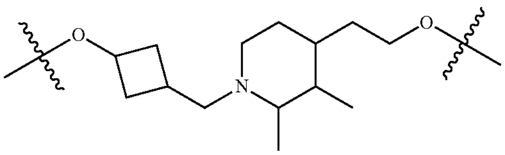
;

-continued

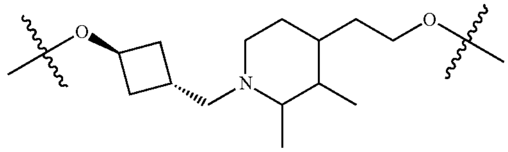

;

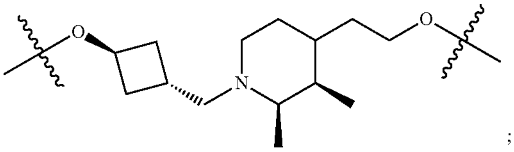

; and

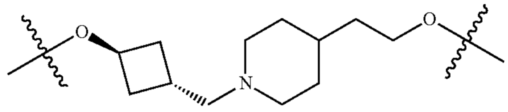

.

In additional embodiments, the linker (L) comprises a structure selected from, but not limited to the structure shown below, where a dashed line indicates the attachment point to the PTM or ULM moieties:

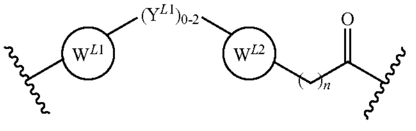

or

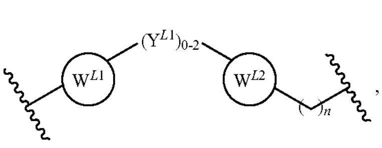

, wherein:

$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, optionally substituted linear or branched $C_1$-$C_6$ alkyl, optionally substituted linear or branched $C_1$-$C_6$ alkoxy, or 2 $R^Q$ groups taken together with the atom they are attached to, form a 4-8 membered ring system containing 0-4 heteroatoms;

$Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);

n is 0-10; and

indicates the attachment point to the PTM or ULM moieties.

In additional embodiments, the linker (L) comprises a structure selected from, but not limited to the structure shown below, where a dashed line indicates the attachment point to the PTM or ULM moieties:

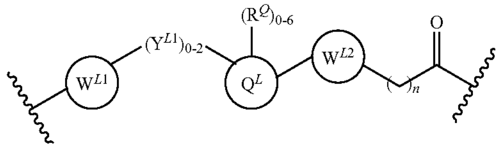

or

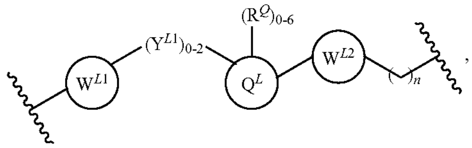

, wherein:

$W^{L1}$ and $W^{L2}$ are each independently absent, aryl, heteroaryl, cyclic, heterocyclyl, $C_{1-6}$ alkyl and optionally one or more C atoms are replaced with O or N, $C_{1-6}$ alkenyl and optionally one or more C atoms are replaced with O, $C_{1-6}$ alkynyl and optionally one or more C atoms are replaced with O, bicyclic, biaryl, biheteroaryl, or biheterocyclyl, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, linear or branched $C_{1-6}$ alkyl optionally substituted by 1 or more halo or $C_{1-6}$ alkoxyl, or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and

indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocyclyl group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described above, which binds to a target protein or polypeptide (e.g., SMARCA2, BRAHMA or BRM), which is ubiquitinated by a ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

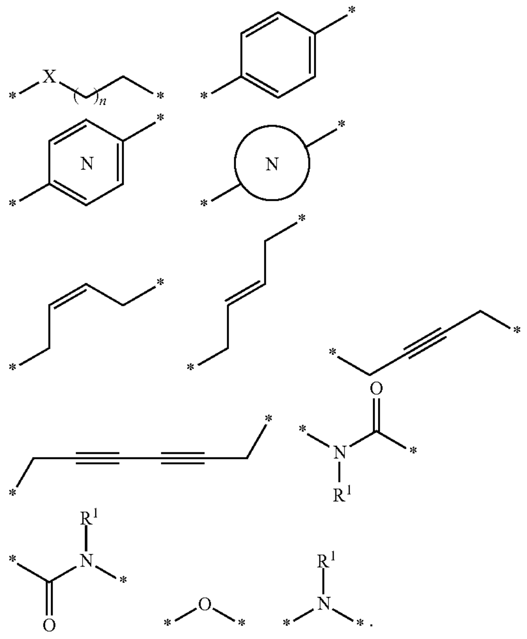

The X is selected from the group consisting of O, N, S, S(O) and $SO_2$; n is integer from 1 to 5; $R^{L1}$ is hydrogen or alkyl,

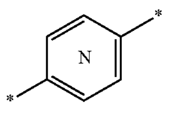

is a mono- or bicyclic aryl or heteroaryl optionally substituted with 1-3 substituents selected from alkyl, halogen, haloalkyl, hydroxy, alkoxy or cyano;

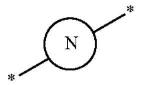

is a mono- or bicyclic cycloalkyl or a heterocyclyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkenyl or alkynyl group, an aryl group or a heterocyclyl group on the ULM and/or PTM groups.

Exemplary PTMs

In any aspect or embodiment of the present disclosure, the PTM group is a moiety, which binds to target proteins, such as Switch/Sucrose Non Fermentable (SWI/SNF)-Related, Matrix-Associated, Actin-Dependent Regulator of Chromatin, Subfamily A, Member 2 (SMARCA2) or BRM. Thus, in any aspect or embodiment described herein, the PTM group is any moiety that binds to SMARCA2 or BRM protein specifically (binds to the target protein SMARCA2, BRAHMA or BRM).

In certain embodiments, the compounds as described herein include a means for binding a target protein, e.g., Brm. As such, in certain aspects, the disclosure provides a bifunctional compound having a means for binding Brm, and a means for binding VHL and a means for chemically coupling the means for binding Brm to the means for binding VHL.

The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target SMARCA2. These binding moieties are linked to the ubiquitin ligase binding moiety preferably through a linker in order to present a target protein (to which the protein target moiety is bound) in proximity to the ubiquitin ligase for ubiquitination and degradation. Any protein (e.g., SMARCA2, BRAHMA or BRM), which can bind to a protein target moiety or PTM group and acted on or degraded by a ubiquitin ligase is a target protein according to the present disclosure.

The present disclosure may be used to treat a number of disease states and/or conditions; including any disease state and/or condition in which proteins are dysregulated (e.g., SMARCA4-deficiency/mutation) and where a patient would benefit from the degradation and/or inhibition of proteins, such as SMARCA2, BRAHMA or BRM.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer such as at least one of a SWI/SNF associated cancer, a SMARCA4-mutation associated cancer, a SMARCA4-deficient cancer, or a cancer with decreased expression of SMARCA4 relative to normal SMARCA4 expression (e.g., decreased expression relative to the expression of non-mutated SMARCA4 or SMARCA4 in a similarly situated non-cancerous cell with wildtype SMARCA4), including lung cancer or non-small cell lung cancer. In any aspect or embodiment described herein, the disease is at least one of SWI/SNF associated cancer, a cancer with a SMARCA4 mutation, a cancer with a SMARCA4-deficiency, or a combination thereof, which may be lung cancer or a non-small cell lung cancer.

In certain additional embodiments, the therapeutic compositions as described herein may be used to effectuate the degradation of proteins of interest for the treatment or amelioration of a disease, e.g., cancer such as at least one of a SWI/SNF associated cancer, a SMARCA2-associated cancer or a cancer with normal or over-expression of SMARCA2.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM) through at least one linker group L.

The protein target may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest, such as SMARCA2 or BRM, and places/presents that protein or polypeptide in proximity to an ubiquitin ligase such that degradation of the protein or polypeptide by ubiquitin ligase may occur. The compositions described below exemplify some of the members of the small molecule target proteins.

In any aspect or embodiment described herein, the PTM of the present disclosure has a chemical structure represented by:

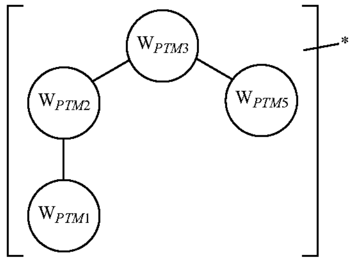

or

Formula I

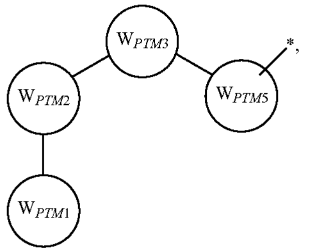

wherein:

- $W_{PTM1}$ is an optionally substituted 5-6-membered aryl or heteroaryl ring (e.g., a 5-6 member aryl or heteroaryl substituted with 0, 1, 2, or 3 substituents selected from hydroxy, halogen, alkoxy, alkyl, haloalkyl, phosphate, amino, alkylamino, cyano or combination thereof);
- $W_{PTM2}$ is an optionally substituted 5-6-membered aryl or heteroaryl ring (e.g., a 5-6 membered aryl or heteroaryl substituted with 0, 1, 2, or 3 substituents selected from hydroxy, halogen, alkoxy, alkyl, haloalkyl, amino, alkylamino and cyano);
- $W_{PTM3}$ is an optionally substituted 3-9-membered aryl or heteroaryl ring (e.g., an optionally substituted 5-6-membered aryl or heteroaryl ring, or a 3-9 or 5-6 membered aryl or heteroaryl substituted with 0, 1, 2, or 3 substituents selected from hydroxy, halogen, alkoxy, alkyl, haloalkyl, amino, alkylamino and cyano), or an optionally substituted 4-9 membered cycloalkyl or heterocyclyl, such as an optionally substituted bridged bicycloalkyl and bridged biheterocyclyl rings (e.g. a 4-9 membered cycloalkyl or heterocyclyl substituted with 0, 1, or 2 substituents selected from hydroxy, halogen, alkoxy, alkyl, haloalkyl, amino, alkylamino and cyano);

$W_{PTM5}$ is absent (such that $W_{PTM3}$ is connected directly to L (linker) or ULM) or an optionally substituted alkyl, an optionally substituted 5-6-membered cycloalkyl, heterocycle, aryl or heteroaryl ring (e.g. a 5-6 membered cycloalkyl, heterocycle, aryl or heteroaryl substituted with 0, 1, or 2 substituents selected from hydroxy, halogen, alkoxy, alkyl, haloalkyl, amino, alkylamino and cyano); and

 is the attachment point to the, linker, ULM group, ULM' group, VLM group, VLM' group.

In any aspect or embodiment described herein, $W_{PTM5}$ is a piperidine.

In certain embodiments, $W_{PTM1}$ comprises a phosphate substitution.

In any aspect or embodiment described herein, the PTM of the PROTAC of the present disclosure is represented by Formula I, wherein at least one of:

$W_{PTM1}$ is an optionally substituted phenyl or a pyridyl (e.g., substituted as described herein, such as a phenyl substituted with a hydroxy or phosphate substituent with or without an additional optional substituent selected as described herein, e.g., substituted with 0, 1, 2, or 3 substituents selected from hydroxy, halogen, alkoxy, alkyl, haloalkyl, amino, alkylamino, cyano or combination thereof);

$W_{PTM2}$ is an optionally substituted 6-membered heteroaryl ring (e.g., substituted as described herein, such as a pyridazine substituted with amino group);

$W_{PTM3}$ is an optionally substituted 5-6-membered heteroaryl (e.g., a pyrazole, pyrrole, imidazole, oxazole, oxadiazole, or triazole);

$W_{PTM5}$ is as described in any aspect or embodiment described herein (e.g., $W_{PTM5}$ may be absent or a pyridine ring); or a combination thereof.

In any aspect or embodiment described herein, for example, an embodiment that includes a PTM of Formula I, $W_{PTM3}$ is a pyrazole or a 6-8-membered heterocyclyl (e.g., a piperazine or a diazabicyclooctane).

In any aspect or embodiment described herein, the PTM of the present disclosure has a chemical structure represented by:

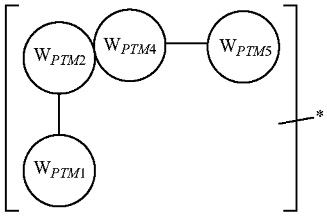

or

Formula II

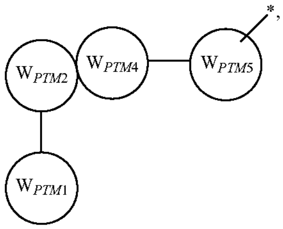

, wherein:

$W_{PTM1}$, $W_{PTM2}$, and $W_{PTM5}$ are as described in any other aspect or embodiment described herein (e.g., $W_{PTM5}$ may or may not be present, such that $W_{PTM4}$ may be connected directly to L (linker) or the ULM);

$W_{PTM4}$ is an optionally substitute 3-7 cycloalkyl or heterocyclyl (e.g., optionally substituted 5-7 cycloalkyl or heterocyclyl or a 5-7 cycloalkyl or heterocyclyl substituted with 0, 1, 2, or 3 substituents selected from hydroxy, halogen, alkoxy, alkyl, haloalkyl, amino, alkylamino and cyano) that is fused with the $W_{PTM2}$ ring; and

 is the attachment point to the, linker, ULM group, ULM' group, VLM group, VLM' group.

In any aspect or embodiment described herein, the PTM of the present disclosure is represented by Formula II, wherein $W_{PTM1}$, $W_{PTM2}$ and $W_{PTM5}$ are as described in any of the aspects or embodiment described herein, and $W_{PTM4}$ is a piperazine ring. For example, in any aspect or embodiment described herein, $W_{PTM2}$ and $W_{PTM4}$ of Formula II taken together constitute a dihydropirazino[2,3-e]pyridazine as shown:

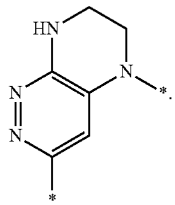

.

In any aspect or embodiment described herein, the PTM of the present disclosure has a chemical structure represented by:

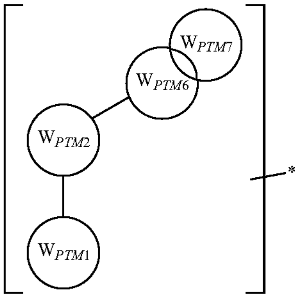

or

Formula III

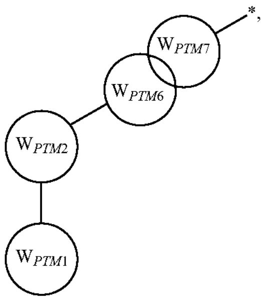

, wherein:

$W_{PTM1}$ and $W_{PTM2}$ are as described in any aspect or embodiment described herein;

$W_{PTM6}$ and $W_{PTM7}$ are independently an optionally 4-7 cycloalkyl or heterocyclyl (e.g., each is independently a 4-7 cycloalkyl or heterocyclyl substituted with 0, 1, or 2 substituents selected from hydroxy, halogen, alkoxy, alkyl, haloalkyl, amino, alkylamino and cyano), and the rings of $W_{PTM6}$ and $W_{PTM7}$ are fused or linked via a spiro connection; and

 is the attachment point to the, linker, ULM group, ULM' group, VLM group, VLM' group.

In any aspect or embodiment described herein, the PTM of the present disclosure has a chemical structure represented by formula III, wherein $W_{PTM1}$ and $W_{PTM2}$ are each independently selected as described in any aspect or embodiment described herein (e.g., $W_{PTM1}$ is a phenyl substituted with a hydroxy substituent with or without an additional optional substituent selected as described herein, $W_{PTM2}$ is a pyridazine substituted with amino group), and $W_{PTM6}$ and $W_{PTM7}$ are a spirocyclic ring system, for example, a spirocyclic ring selected from:

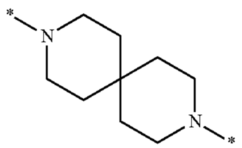

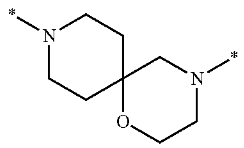

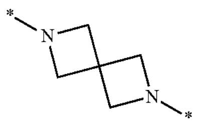

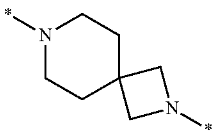

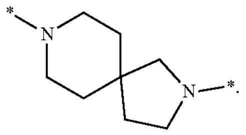

In any aspect or embodiment described herein, the PTM of the the present disclosure is represented by:

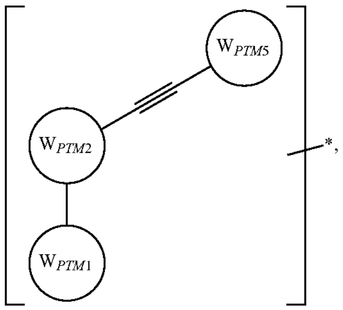

Formula IVa

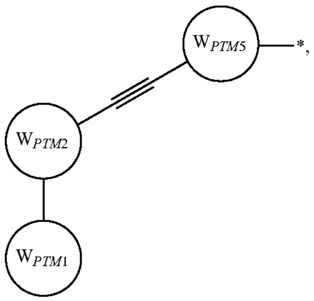

-continued

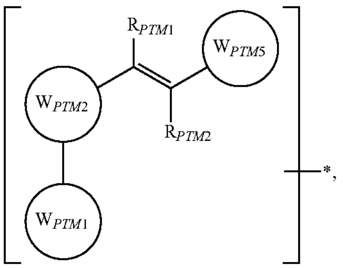

Formula IVb1

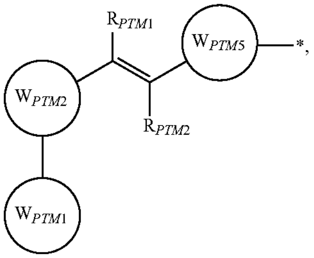

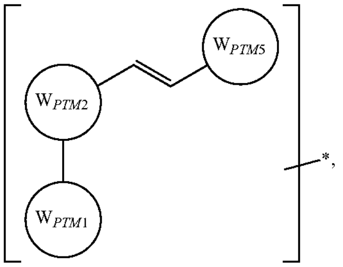

Formula IVb2

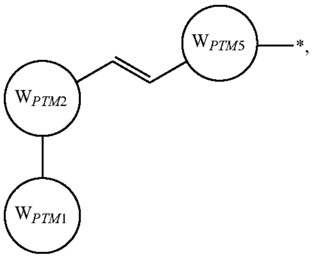

wherein:

$W_{PTM1}$, $W_{PTM2}$, and $W_{PTM5}$ are as described in any other aspect or embodiment described herein;

$R_{PTM1}$ and $R_{PTM2}$ are individually a H, halo, HO, C1-C3 alkyl, C1-C3 haloalkyl, or C1-C3 alkoxy; and

 is the attachment point to the, linker, ULM group, ULM' group, VLM group, VLM' group.

In any aspect or embodiment described herein, the PTM of the present disclosure has the chemical structure represented by Formula IV, wherein at least one of:

$W_{PTM1}$ is a phenyl substituted with a hydroxy or phosphate substituent with or without an additional optional substituent selected as described herein;

$W_{PTM2}$ is a pyridazine substituted with amino group;

$W_{PTM5}$ is absent, a pyrazole ring, or a pyridine ring; or a combination thereof.

In any aspect or embodiment described herein, the PTM of the present disclosure is represented by:

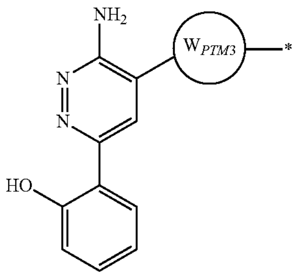

or

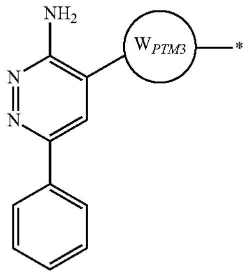

or

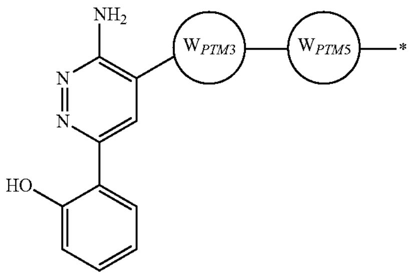

or

Formula V

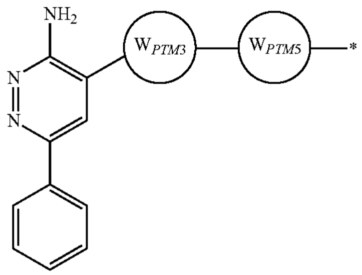

or a pharmaceutically acceptable salt thereof, wherein:

$W_{PTM3}$ is absent or an optionally substituted 5-6-membered heteroaryl, an optionally substituted 4-9 cycloalkyl or heterocyclyl ring, an optionally substituted bridged bicycloalkyl and bridged biheterocyclyl ring; and $W_{PTM5}$ is an optionally substituted 5-6-membered heteroaryl or aryl, e.g., pyridine, or pyridazine.

In any aspect or embodiment described herein, the PTM of the present disclosure is represented by:

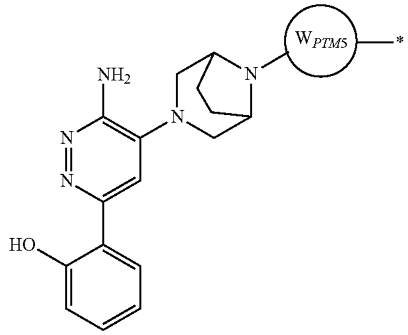

or

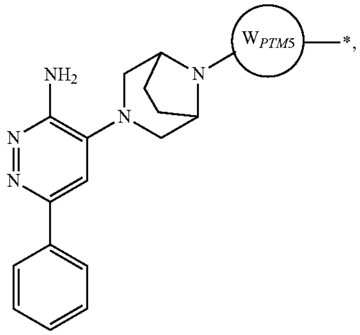

or a pharmaceutically acceptable salt thereof, wherein:

$W_{PTM5}$ is phenyl, pyridine, pyrimidine or pyrazine.

In any aspect or embodiment described herein, the PTM of the present disclosure is represented by:

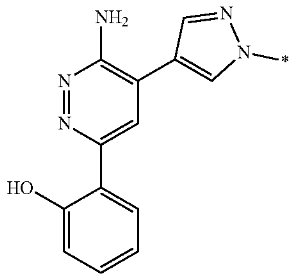

or

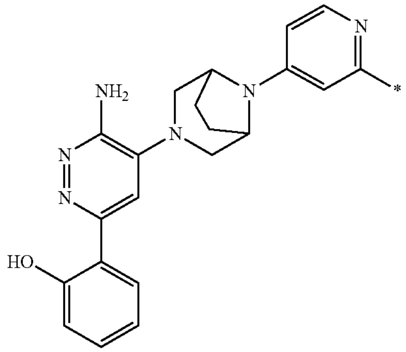

or

-continued

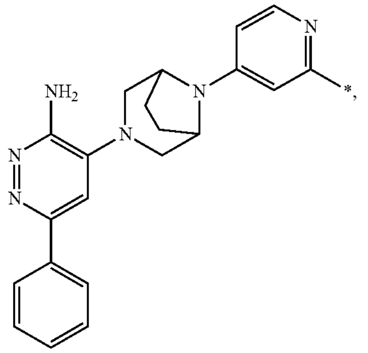

or a pharmaceutically acceptable salt thereof.

In any aspect or embodiment described herein, the PTM of the present disclosure is represented by:

Formula Vb

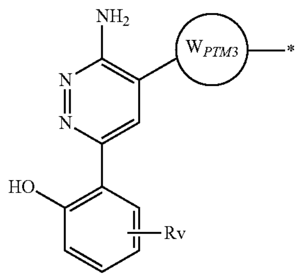

or

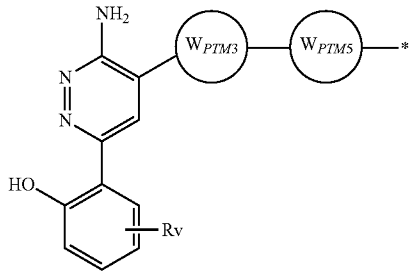

or a pharmaceutically acceptable salt thereof, wherein:

$W_{PTM3}$ is an optionally substituted 5-6-membered heteroaryl, an optionally substituted 4-9 cycloalkyl or heterocyclyl ring, an optionally substituted bridged bicycloalkyl and bridged biheterocyclyl ring;

$W_{PTM5}$ is an optionally substituted 5-6-membered heteroaryl or aryl, e.g., pyridine, or pyridazine;

Rv is 0, 1, 2 or 3 substituents independently selected from hydroxy, halogen, alkoxy, alkyl, haloalkyl, phosphate, amino, alkylamino, cyano or a combination thereof.

In certain embodiments, the hydroxyl group is modified with a phosphate group (i.e., a phosphoester group).

In any aspect or embodiment described herein, the PTM of the present disclosure has a chemical structure represented by:

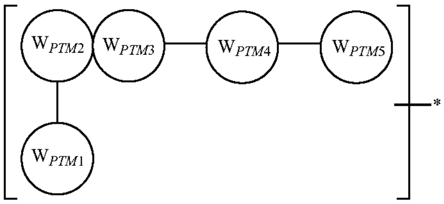

or

Formula VI

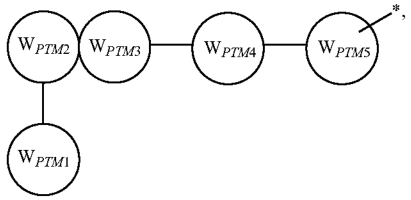

wherein: $W_{PTM1}$ and $W_{PTM2}$ are as described in any other aspect or embodiment described herein (e.g., $W_{PTM5}$ may or may not be present, such that $W_{PTM4}$ may be connected directly to L (linker) or the ULM);

$W_{PTM3}$ is absent or an optionally substituted 5-7 cycloalkyl or heterocyclyl (e.g., 5-7 cycloalkyl or heterocyclyl substituted with 0, 1, 2, or 3 substituents selected from hydroxy, halogen, alkoxy, alkyl, haloalkyl, amino, alkylamino and cyano) that is fused with the $W_{PTM2}$ ring;

$W_{PTM4}$ is an optionally substituted 3-7-membered aryl or heteroaryl ring (e.g., optionally substituted 5-7 cycloalkyl or heterocyclyl, or a 3-7 or a 5-6 membered aryl or heteroaryl substituted with 0, 1, 2, or 3 substituents selected from hydroxy, halogen, alkoxy, alkyl, haloalkyl, amino, alkylamino and cyano), or an optionally substituted 4-9 cycloalkyl or heterocyclyl, such as an optionally substituted bridged bicycloalkyl and bridged biheterocyclyl rings (e.g. a 4-9 cycloalkyl or heterocyclyl substituted with 0, 1, or 2 substituents selected from hydroxy, halogen, alkoxy, alkyl, haloalkyl, amino, alkylamino and cyano);

$W_{PTM5}$ is absent (such that $W_{PTM3}$ is connected directly to L (linker) or ULM) or an optionally substituted alkyl, an optionally substituted 5-6-membered cycloalkyl, heterocycle, aryl or heteroaryl ring (e.g. a 5-6 membered cycloalkyl, heterocycle, aryl or heteroaryl substituted with 0, 1, or 2 substituents selected from hydroxy, halogen, alkoxy, alkyl, haloalkyl, amino, alkylamino and cyano), e.g., an optionally substituted pyrazole ring, or a pyridine ring; and ⁄* is the attachment point to the, linker, ULM group, ULM' group, VLM group, VLM' group.

In any aspect or embodiment described herein, the PTM of the present disclosure has a chemical structure represented by:

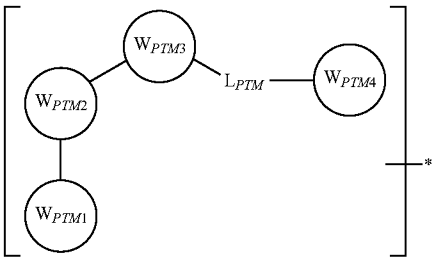

or

-continued

Formula VII

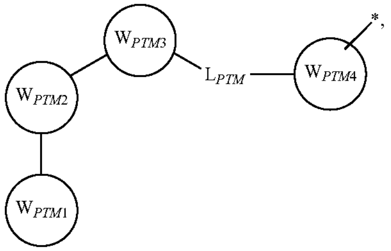

wherein:

$W_{PTM1}$, $W_{PTM2}$, $W_{PTM3}$, and $W_{PTM4}$ are as described in any other aspect or embodiment described herein;

$L_{PTM}$ is C1-C6 alkyl optionally substituted with an C1-C4 alkyl or C1-C3 alkoxy; and

 is the attachment point to the, linker, ULM group, ULM' group, VLM group, VLM' group.

In any aspect or embodiment described herein, the PTM is selected from:

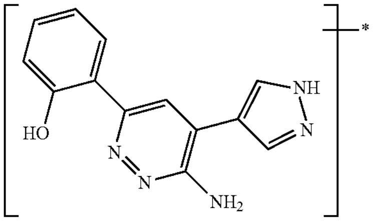

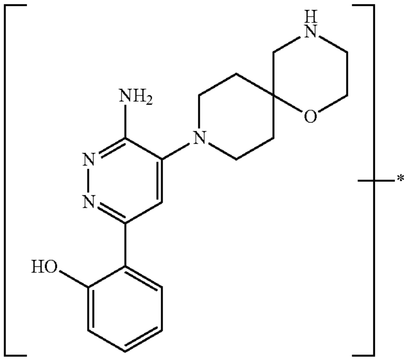

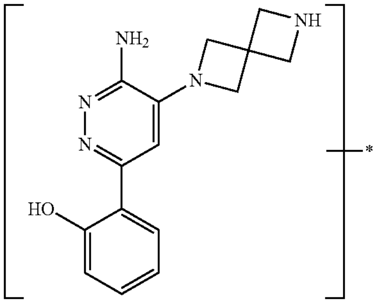

-continued

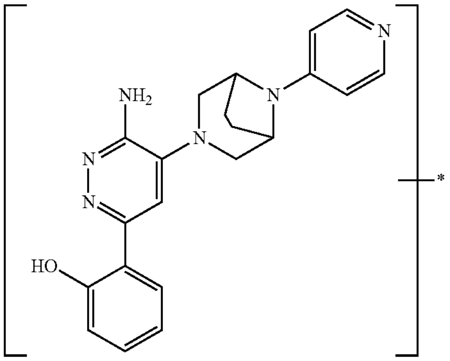

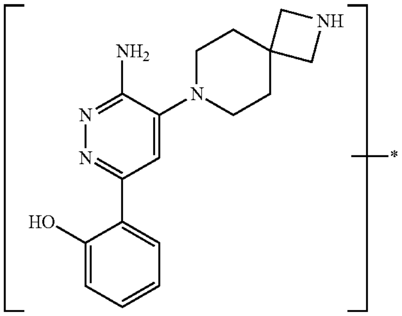

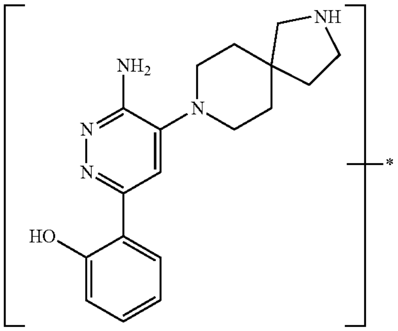

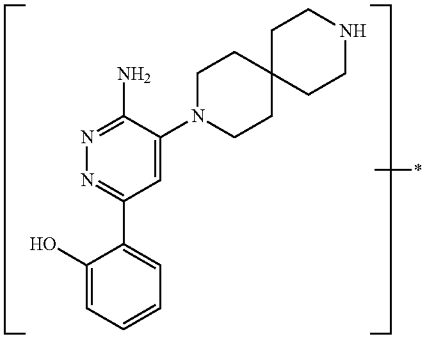

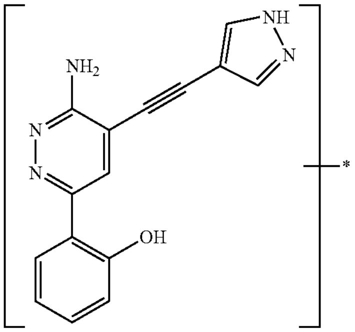

-continued
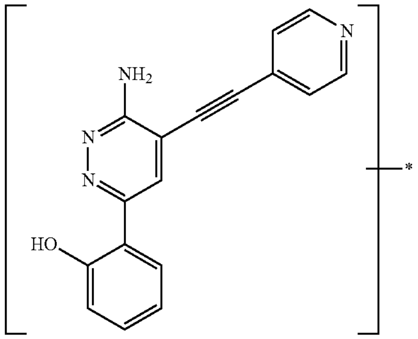
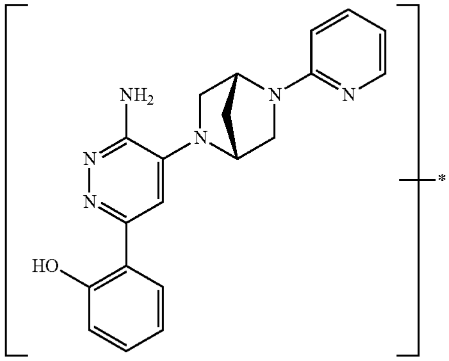
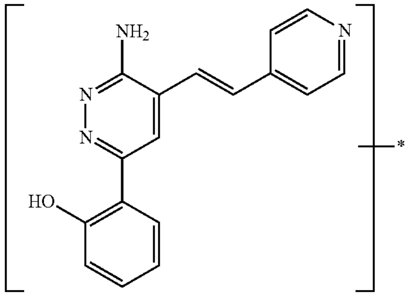
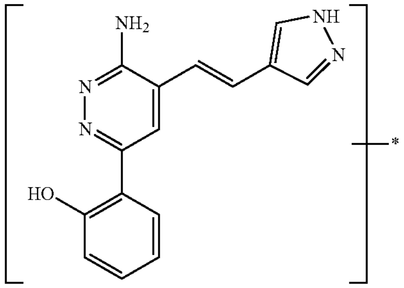
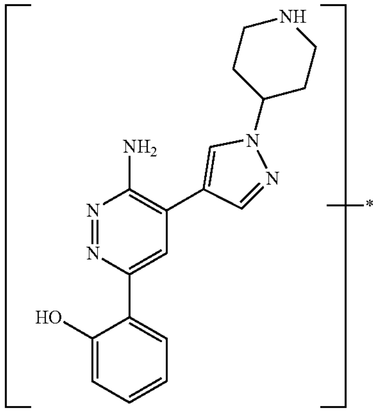
-continued
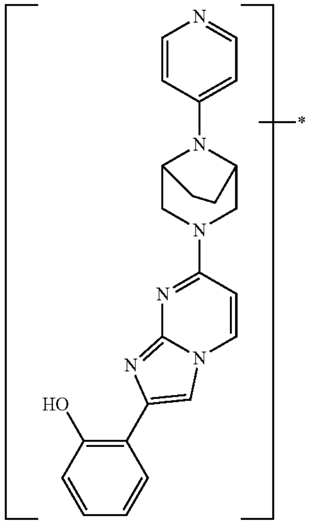
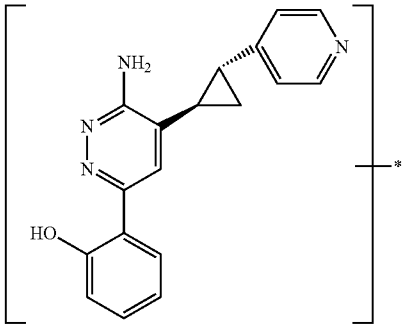
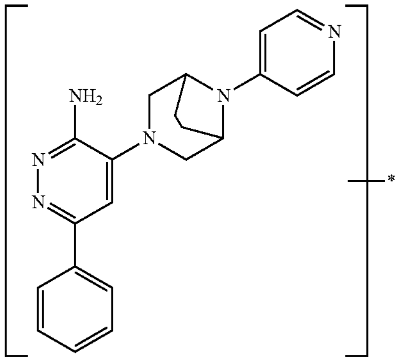
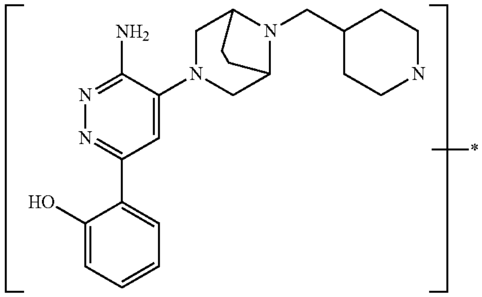

-continued
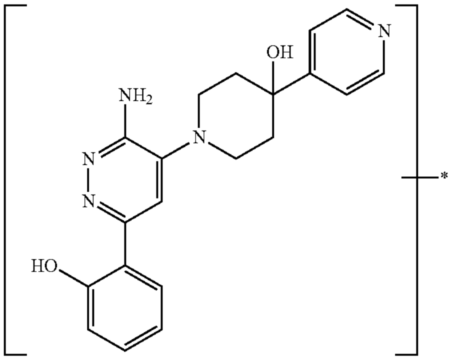
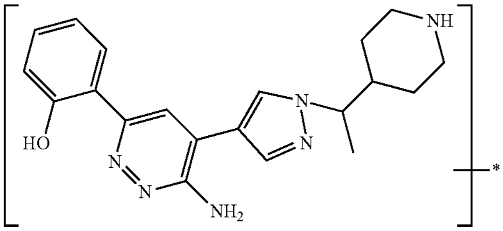
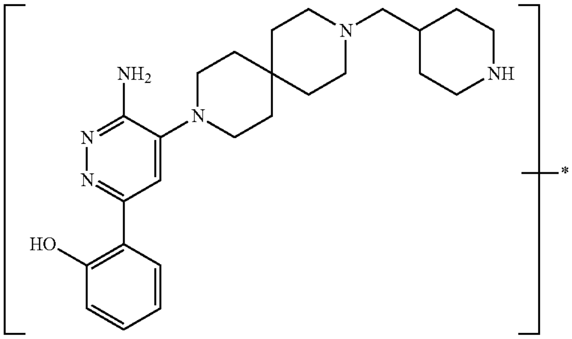
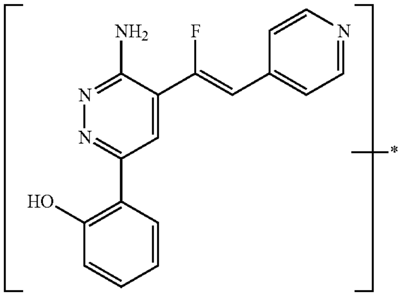
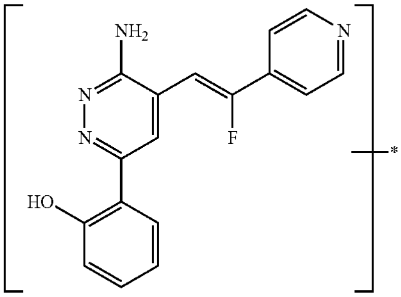
-continued
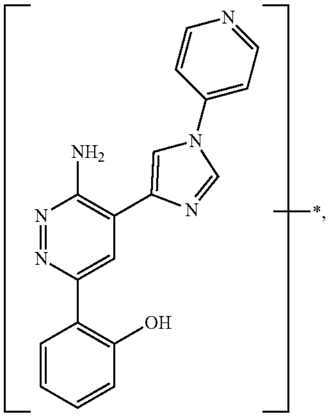
wherein * is the attachment point to the, linker, ULM group, ULM' group, VLM group, VLM' group.
In any aspect or embodiment described herein, the PTM is selected from:
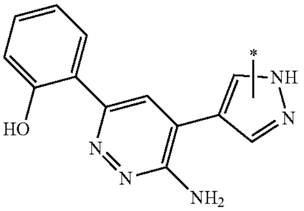
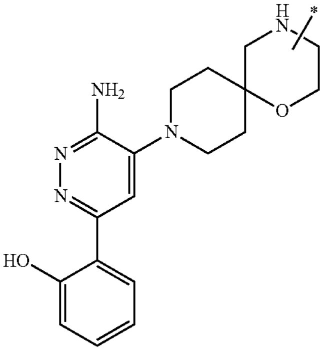
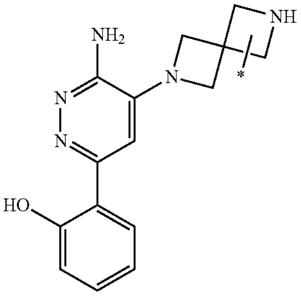

-continued
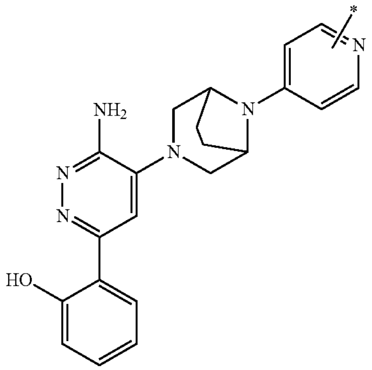
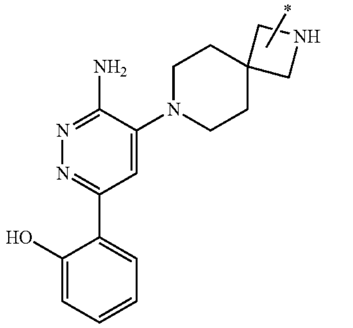
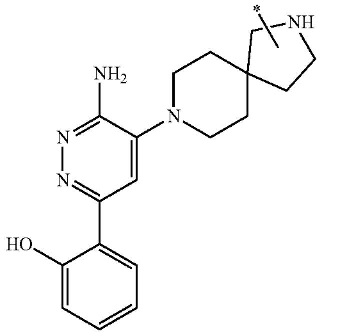
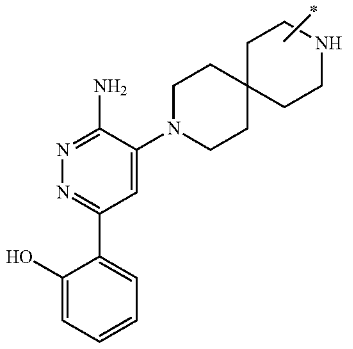
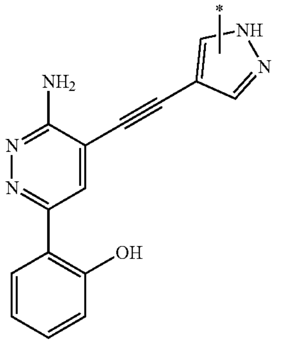
-continued
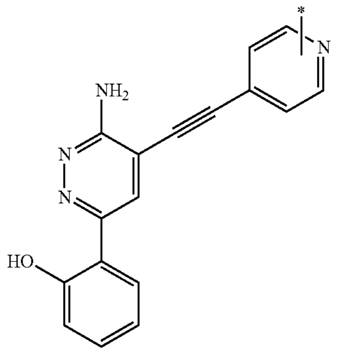
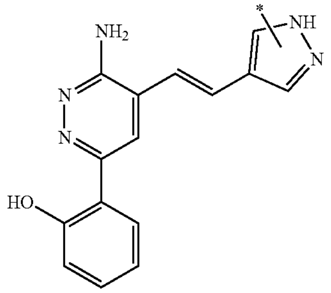
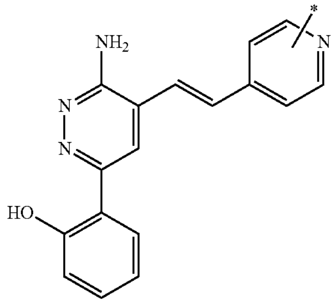
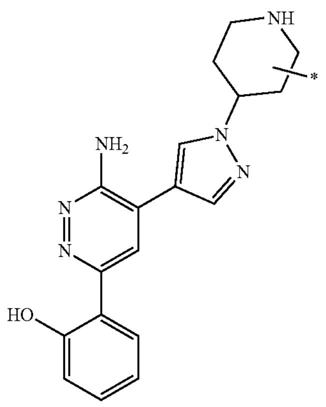

-continued
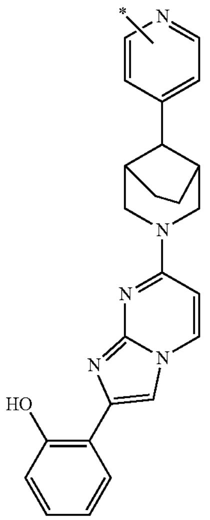
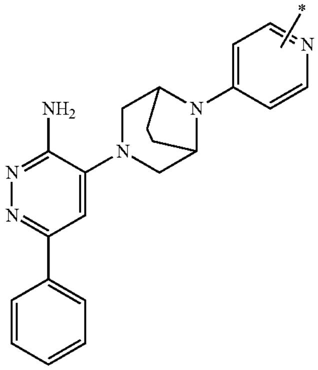
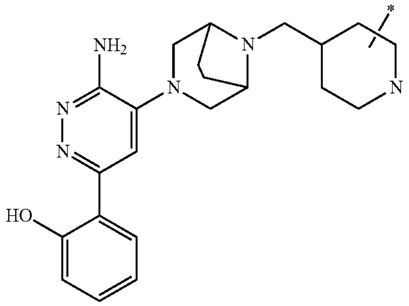
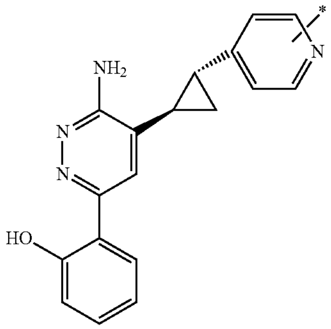
-continued
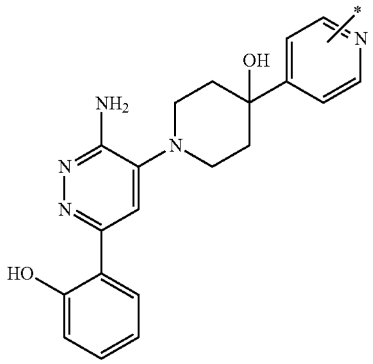
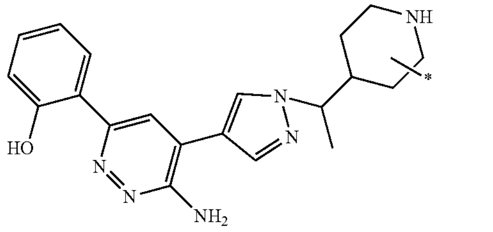
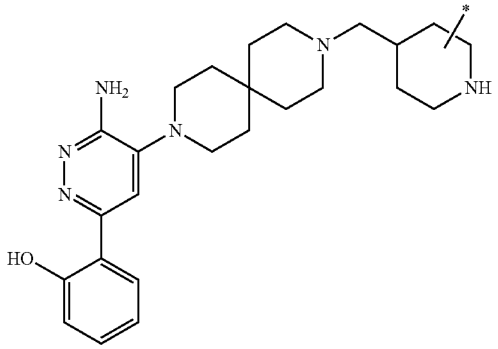
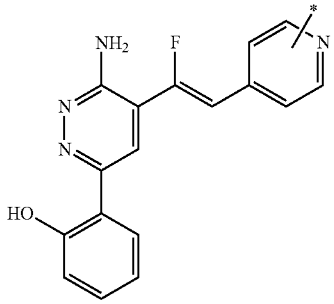
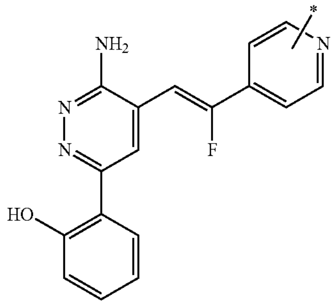

-continued
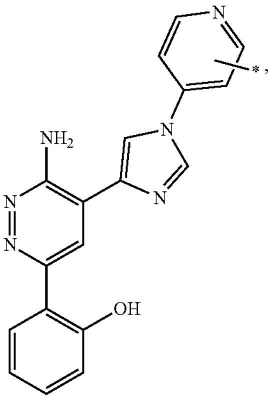
wherein  is the attachment point to the, linker, ULM group, ULM' group, VLM group, VLM' group.
In any aspect or embodiment described herein, the PTM is selected from the group consisting of:
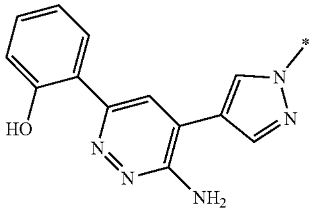
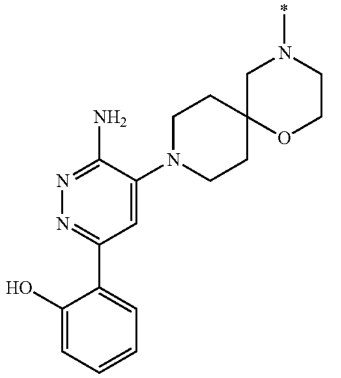
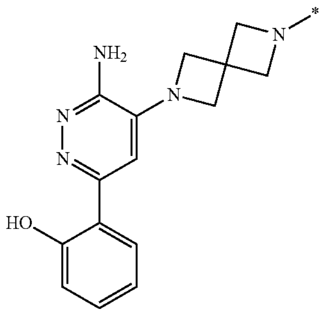
-continued
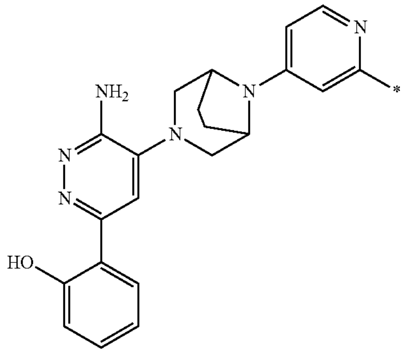
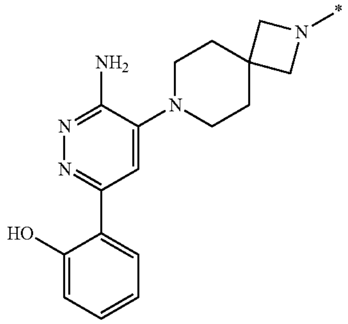
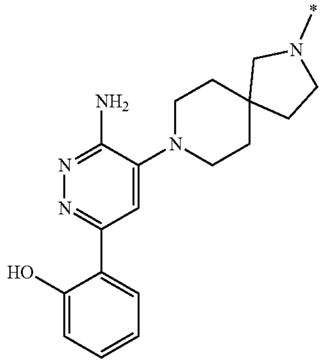
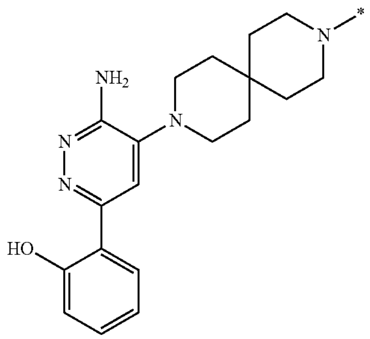

-continued
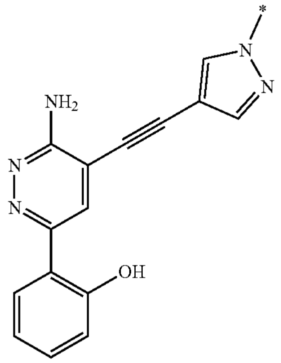
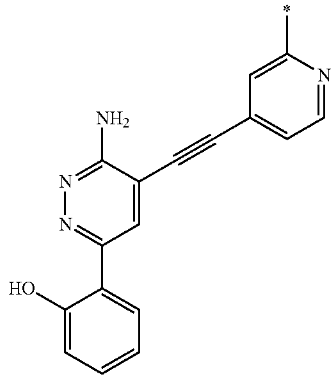
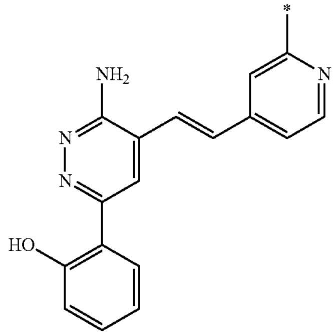
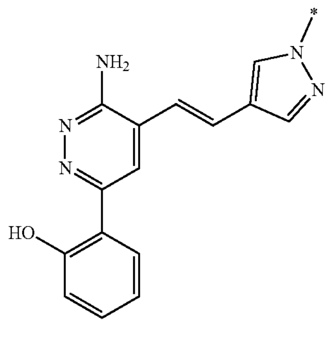
-continued
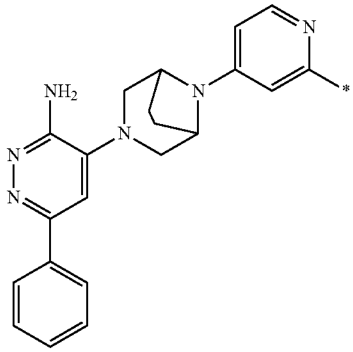
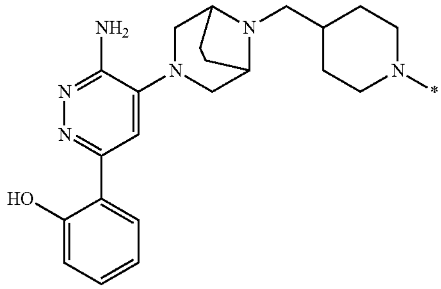
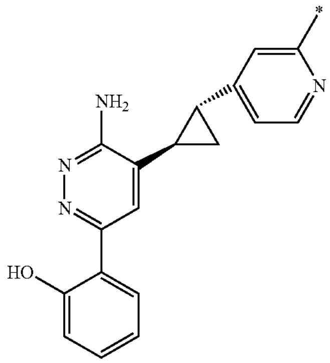
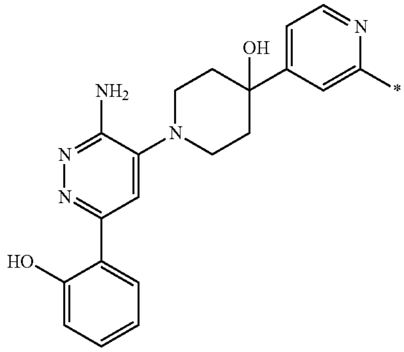
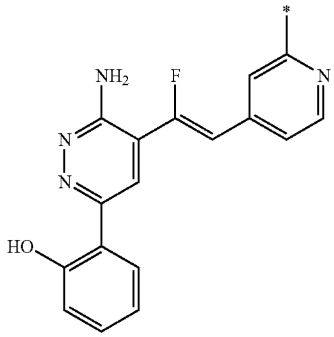

-continued

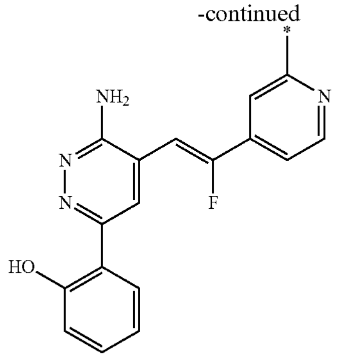

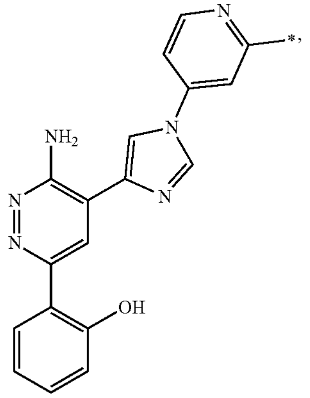

wherein  is the attachment point to the, linker, ULM group, ULM' group, VLM group, VLM' group.

The compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate[i.e., 1,1'-methylene-bis-(2-hydroxy-3 naphthoate)] salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term “parenteral” as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated and the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, including pembrolizumab, among others. In certain preferred aspects of the disclosure, one or more compounds according to the present disclosure are coadministered with another bioactive agent, such as an anti-cancer agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer such as lung cancer, including non-small cell lung cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as a VHL E3 ubiquitin ligase) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl)carbonyl]piperazine, 1-[(6-Formyl-2-indolyl)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approaches

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/VLMs.

With PTMs and ULMs (e.g. VLMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Abbreviations

ACN: acetonitrile
ADDP: 1,1'-(azodicarbonyl)dipiperidine
BAST: N,N-bis(2-methoxyethyl)aminosulfur trifluoride
BPO: benzoyl peroxide
Cbz: Carbonylbezyloxy
DAST: diethylaminosulfur trifluoride
DBE: 1,2-dibromoethane
DCM: dichloromethane
DEAD: diethyl azodicarboxylate
DIAD: diisopropyl azodicarboxylate
DIBAL: disiobutylaluminium hydride
DIEA or DIPEA: diisopropylethylamine
DMA: N,N-dimethylacetamide
DMF: N,N-dimethylformamide
DMP: Dess-Martin periodinane
EA: ethyl acetate
EDCI: 1-ethyl-3-(3-dimethylaminopropyl)carbodiimide
HBTU: N,N,N'N'-tetramethyl-O-(1H-benzotriazol-1-yl) uronium hexafluorophosphate
HMDS: bis9trimethylsilyl)amine
HMPA: hexamethylphosphoramide
LDA: lithium diisopropylamide
MCPBA: meta-chloroperoxybenzoic acid
MsCl: methanesulfonyl chloride
M.W: microwave
NBS: N-bromosuccinimide
NMP: N-methylpyrrolidone
PCC: pyridinium chlorochromate
Pd-118 or Pd(dtpf)$Cl_2$: 1,1'-bis(di-tert-butylphosphino) ferrocene dichloropalladium
Pd(dppf)$Cl_2$: 1,1'-bis(diphenylphosphino)ferrocene dichloropalladium
$Pd(dba)_2$: bis(dibenzylideneacetone)palladium
$Pd_2(dba)_3$: Tris(dibenzylideneacetone)dipalladium
PPTS: pyridium p-tolunesulfonate
PTSA: p-toluenesulfonic acid
RuPhos-Pd-G3: XPhos-Pd-G3: [(2-dicyclohexylphosphino-2',6'-diisopropoxy-1,1'-biphenyl)-2-(2'-amino-1,1'-biphenyl)]palladium(II) methanesulfonate
RuPhos-Pd-G2: Chloro[(2-dicyclohexylphosphino-2',6'-diisopropoxy-1,1'-biphenyl)-2-(2'-amino-1,1'-biphenyl)]palladium(II)
SFC: supercritical fluid chromatography
t-BuXPhos-Pd-G3: [(2-di-tert-butylphosphino-2',4',6'-triisopropyl-1,1'-biphenyl)-2-(2'-amino-1,1'-biphenyl)] palladium(II) methanesulfonate
TEA: trimethylamine
TFA: trifluoroacetic acid
TLC: thin layer chromatography
TMP: 2,2,6,6-tetramethylpiperidine
TEMPO: 2,2,6,6-tetramethylpiperidine-N-oxide
TosCl or TsCl: p-toluenesulfonyl chloride
TsOH: p-toluenesulfonic acid
XantPhos: 4,5-bis(diphenylphosphino)-9,9-dimethylxanthene XPhos: 2-dicyclohexylphosphino-2' 4'6'-triisopropylbiphenyl XPhos-Pd-G3: [(2-dicyclohexylphosphino-2',4',6'-triisopropyl-1,1'-biphenyl)-2-(2'-amino-1,1'-biphenyl)] palladium(II) methanesulfonate 12354-85-7: bis(pentamethylcyclopentadienylrhodium dichloride)

Scheme 1

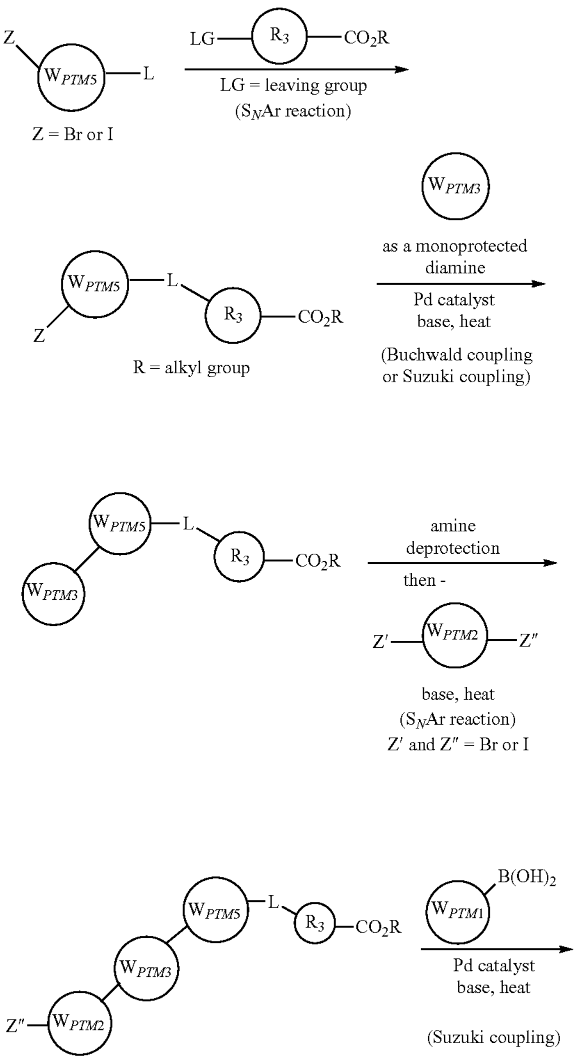

-continued

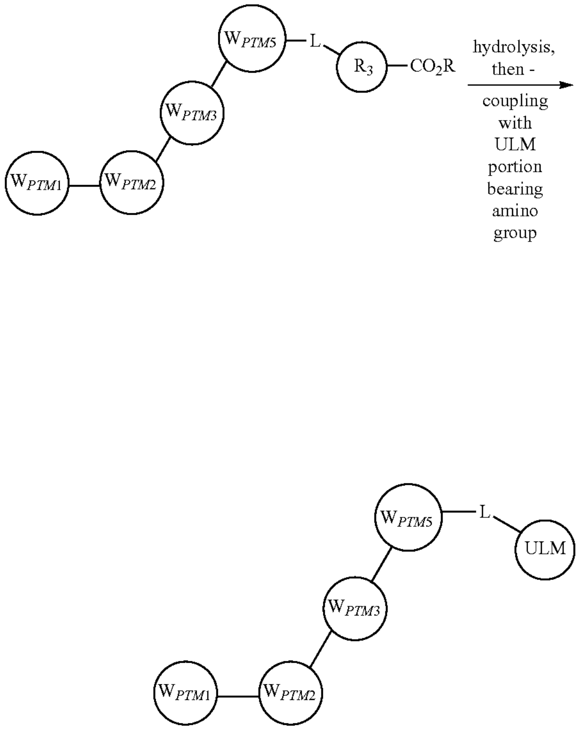

As shown in Scheme 1, a compound having the $W_{PTM5}$ moiety contains a linking group L which includes a nucleophilic group, such as an amino group. Upon reaction with a compound having a good leaving group LG (for instance, a perfluorosulfonyl group $C_4F_9SO_3$—), a coupling product is formed. The coupling product reacts with a monoprotected amine molecule $W_{PTM3}$, under palladium-catalyzed conditions to attach the $W_{PTM3}$ fragment. Following amine deprotection, a more reactive halogen atom selected from Z' and Z" in $W_{PTM5}$-$W_{PTM3}$ undergoes nucleophilic substitution with the free amino group to form $W_{PTM5}$-$W_{PTM3}$-$W_{PTM2}$, which then reacts with a $W_{PTM2}$ boronic acid to furnish the PTM binding group including the $W_{PTM5}$-$W_{PTM3}$-$W_{PTM2}$-$W_{PTM1}$ fragment. Following basic-catalyzed ester hydrolysis, the resulting acid is coupled with the ULM portion bearing an amino group to combine the PTM and ULM binding moieties in one molecule.

Scheme 2

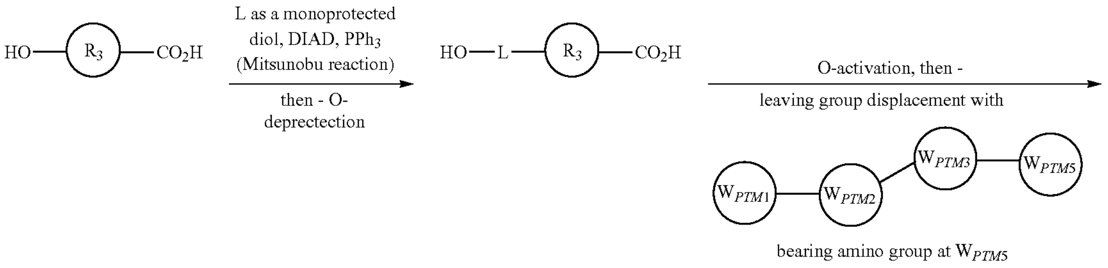

-continued

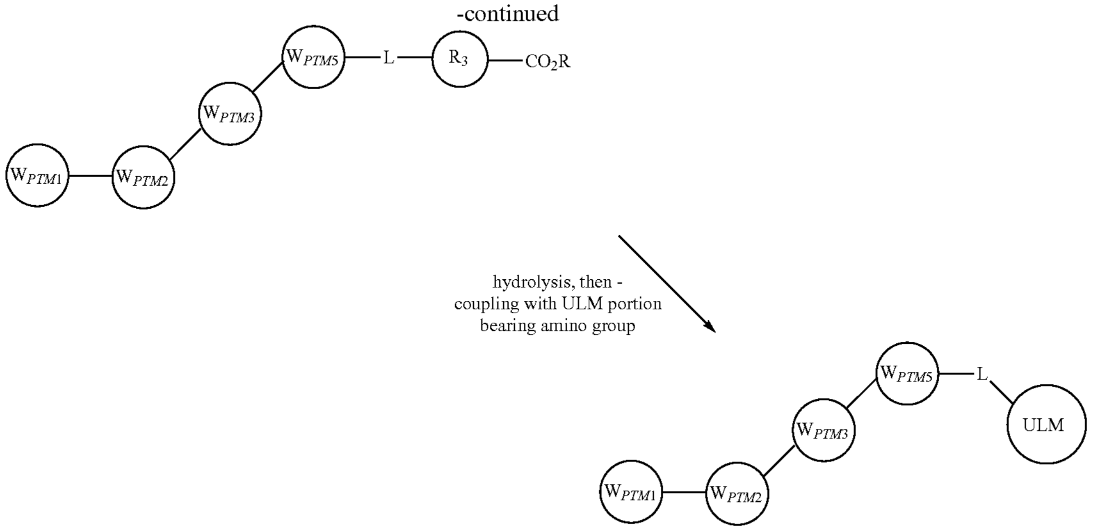

As shown in Scheme 2, a Mitsunobu reaction between a hydroxyl-containing moiety $R_3$ and a monoprotected diol including the linking group L results in a coupling product. Following O-deprotection, the free hydroxyl group is activated, for example as a sulfonate, and is subsequently displaced with the moiety $W_{PTM5}$-$W_{PTM3}$-$W_{PTM2}$-$W_{PTM1}$ bearing an amino group at $W_{PTM5}$. After ester hydrolysis, the resulting acid is coupled with the ULM portion bearing an amino group to combine the PTM and ULM binding moieties in one molecule.

Scheme 3

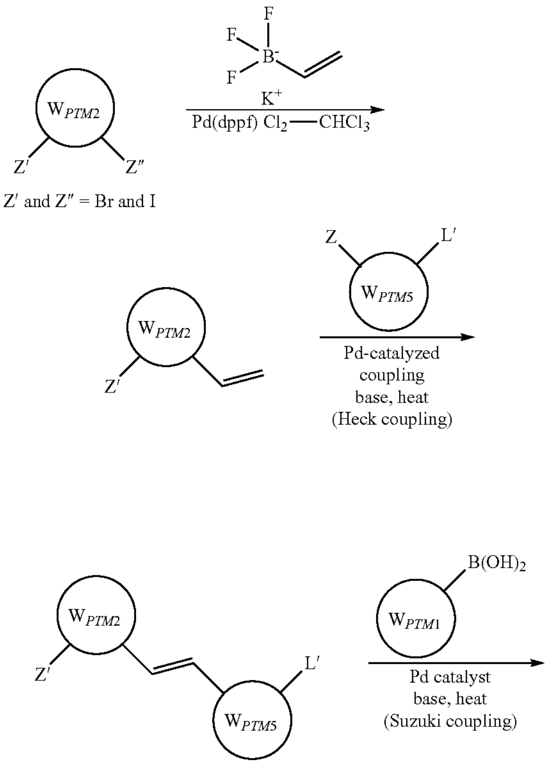

-continued

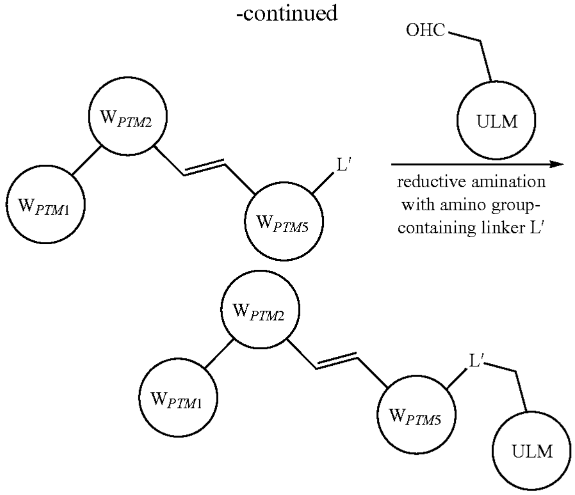

As shown in Scheme 3, a vinyl group is first introduced into a bis-halogenated derivative $W_{PTM2}$. The resulting product then undergoes the palladium-catalyzed Heck coupling reaction with a halogenated moiety $W_{PTM2}$ bearing a linking group L' which includes an optionally protected amino group. To introduce the $W_{PTM1}$ moiety, the halide portion of $W_{PTM2}$-$W_{PTM5}$ is coupled with the appropriate boronic acid under Suzuki conditions, and the resulting amine reacts with the ULM-containing aldehyde to afford the PTM-ULM coupling product.

Scheme 4

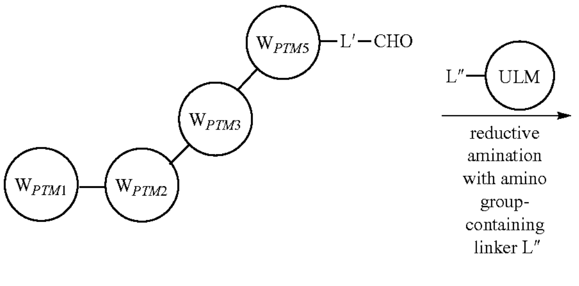

-continued

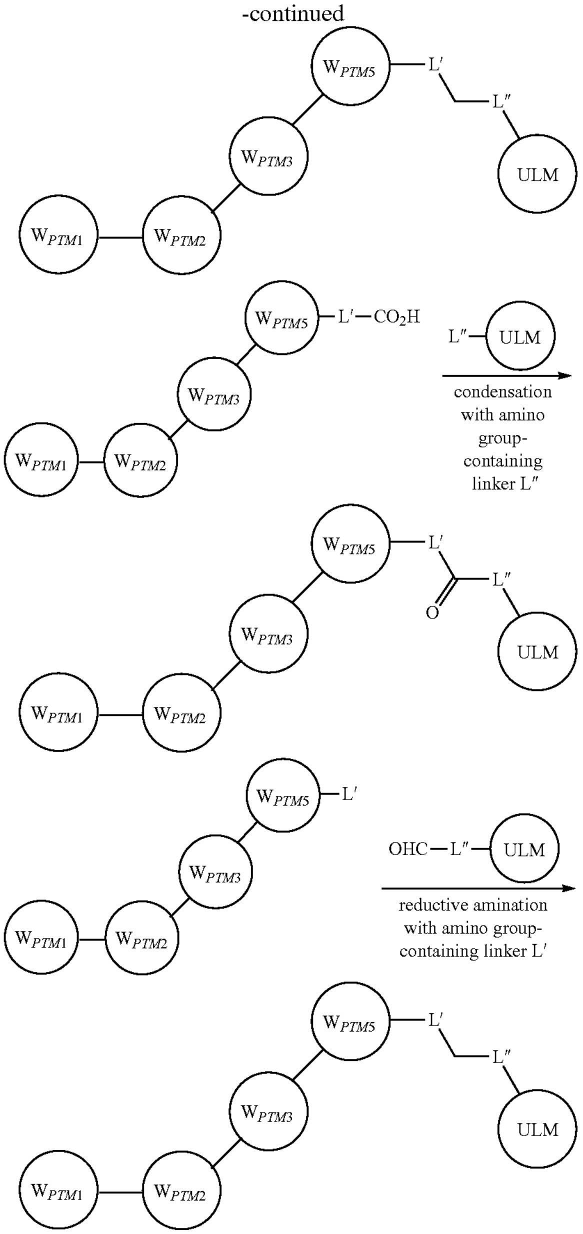

Scheme 4 illustrates exemplary coupling reactions that are utilized for connecting the PTM-binding moiety $W_{PTM5}$-$W_{PTM3}$-$W_{PTM2}$-$W_{PTM1}$ with the ULM-containing portion. Such reactions may include reductive amination using sodium cyanoborohydride as a reducing agent or condensation coupling reactions between a carboxylic acid and a diamine. A person of ordinary skill in the art would be able to select appropriate reagents and conditions to carry out the desired transformations.

Scheme 5

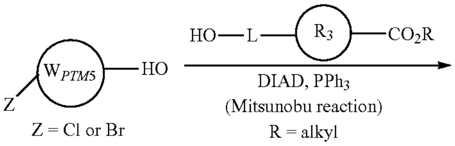

-continued

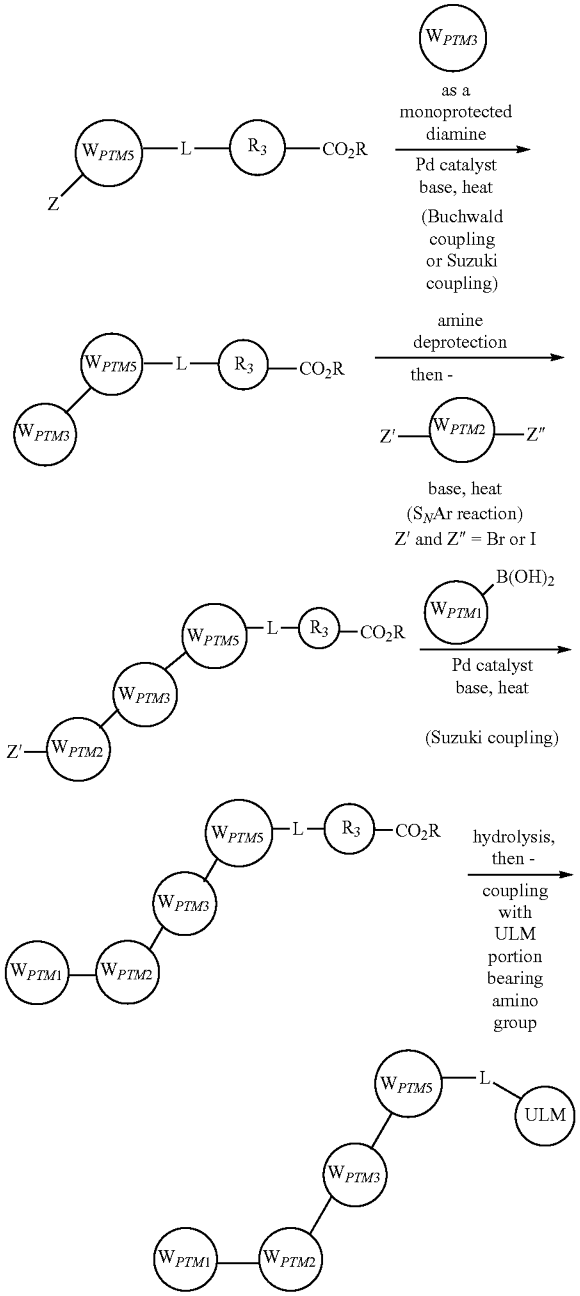

As shown in Scheme 5, a Mitsunobu-type reaction between the hydroxyl-containing moieties $R_3$ and $W_{PTM5}$ results in a coupling product. The halogen atom at $W_{PTM5}$ is then displaced with the monoprotected diamine $W_{PTM3}$ under Suzuki or Buchwald conditions. Following deprotection of the second amino group, a more reactive halogen atom attached to the $W_{PTM2}$ moiety is displaced to form the $W_{PTM5}$-$W_{PTM3}$-$W_{PTM2}$ fragment. The resulting monohalide is then reacted with an appropriate boronic acid under Suzuki conditions to afford the PTM-binding moiety $W_{PTM5}$-$W_{PTM3}$-$W_{PTM2}$-$W_{PTM2}$. Following ester hydrolysis, the resulting acid is then coupled with the ULM portion bearing an amino group to combine the PTM and ULM binding moieties in one molecule.

Scheme 6

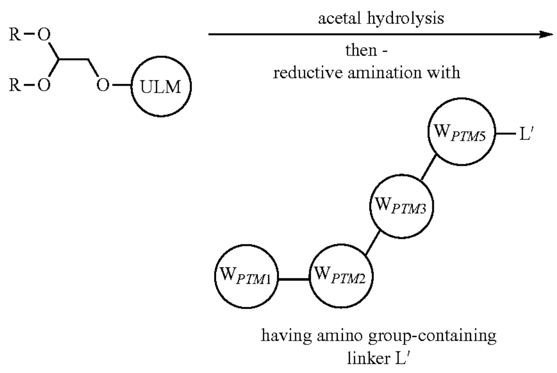

-continued

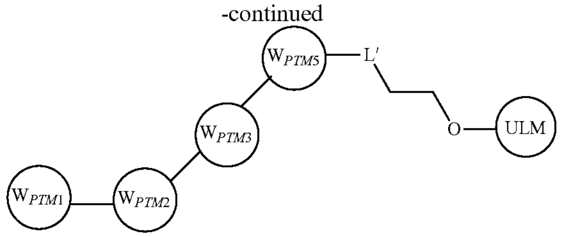

As shown in Scheme 6, the acetal-containing ULM moiety may undergo an acid-catalyzed hydrolysis under sufficiently mild conditions to form an aldehyde, which then reacts with the $W_{PTM5}$-$W_{PTM3}$-$W_{PTM2}$-$W_{PTM2}$ fragment having an amino group-containing linker L' under reductive amination conditions to form the PTM-ULM coupling product. A person of ordinary skill in the art would be able to select appropriate reagents and conditions to carry out the desired transformations.

Scheme 7

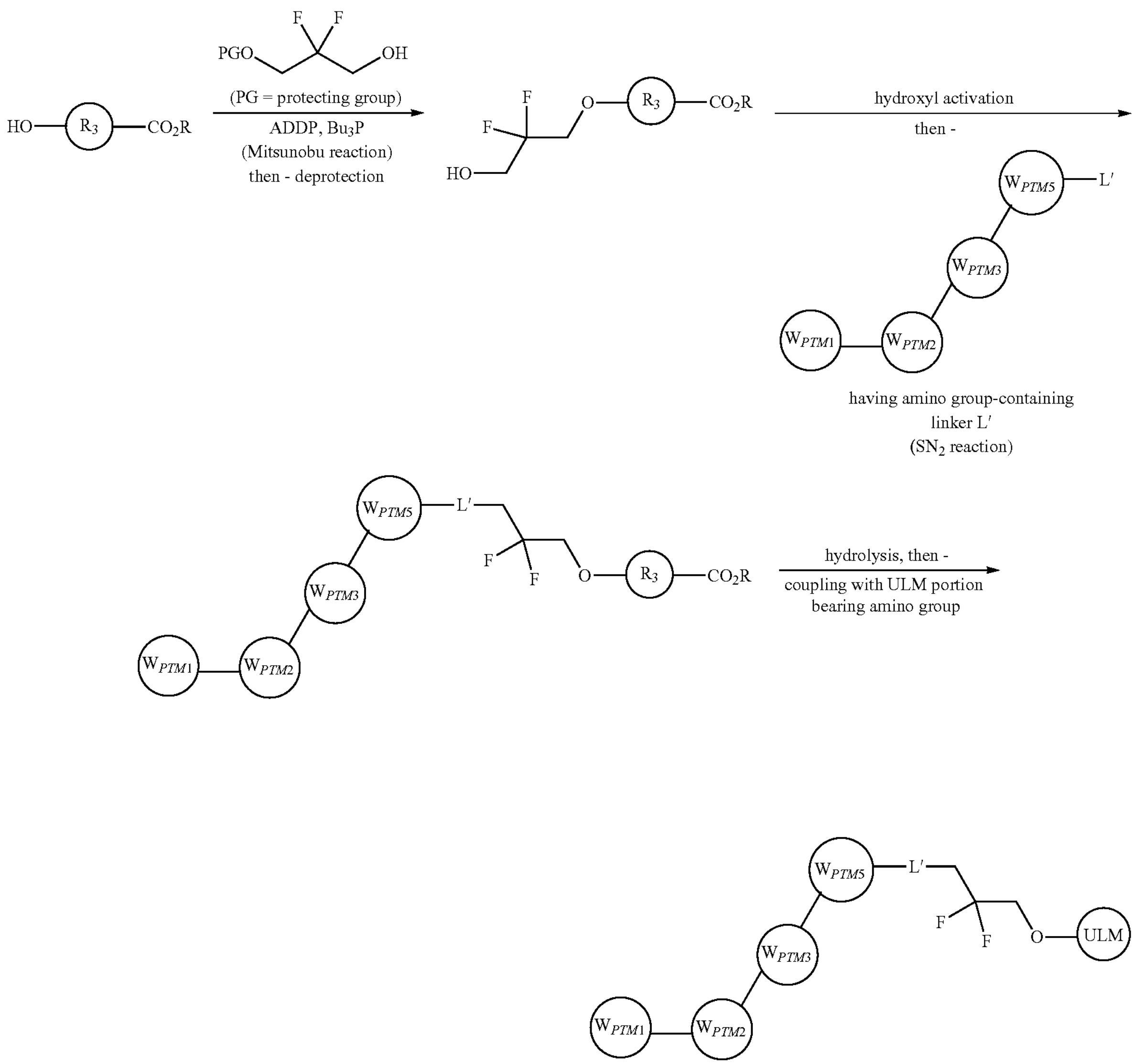

As shown in Scheme 7, a Mitsunobu-type reaction between the hydroxyl-containing moieties $R_3$ and the mono-protected fluorinated diol provides a fluorine-containing intermediate. Following O-deprotection, the free hydroxyl group is activated (for example as a sulfonate) and subsequently displaced with the moiety $W_{PTM5}$-$W_{PTM3}$-$W_{PTM2}$-$W_{PTM1}$ bearing an amino group at $W_{PTM5}$. After ester hydrolysis, the resulting acid is coupled with the ULM portion bearing an amino group to combine the PTM and ULM binding moieties in one molecule.

Scheme 8

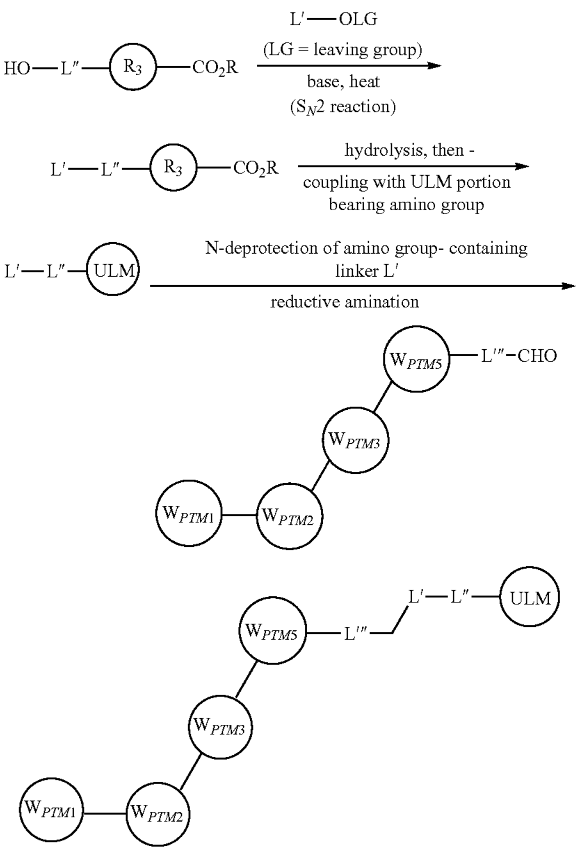

OR

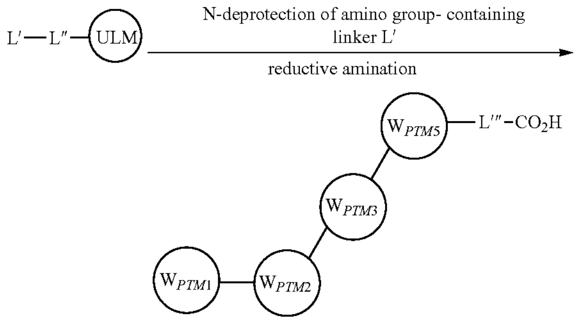

-continued

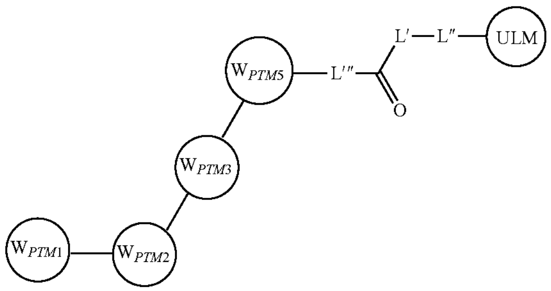

As shown in Scheme 8, nucleophilic displacement of the leaving group in L'-OLG with a hydroxyl group-containing ester including $R_3$ results in a coupling product that combines the linkers L' and L". Subsequent basic hydrolysis and coupling of the resulting acid with the ULM portion bearing an amino group provides a ULM fragment to which two sequential linking groups L' and L" are attached. N-deprotection of the amino group of L' followed by a reductive amination with the $W_{PTM5}$-$W_{PTM3}$-$W_{PTM2}$-$W_{PTM1}$-L'" aldehyde or a condensation with the $W_{PTM5}$-$W_{PTM3}$-$W_{PTM2}$-$W_{PTM1}$-L'" carboxylic acid affords the PTM-ULM coupling product.

Scheme 9

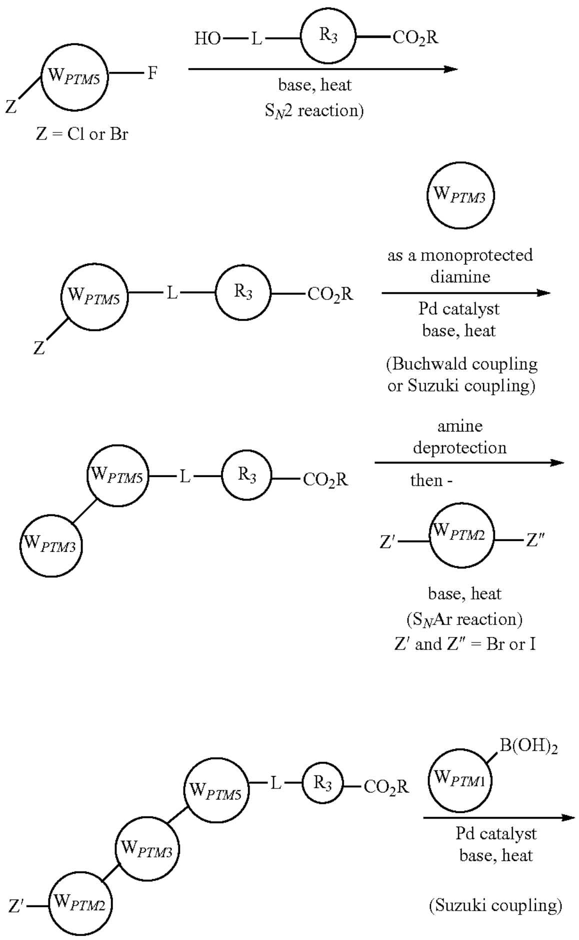

-continued

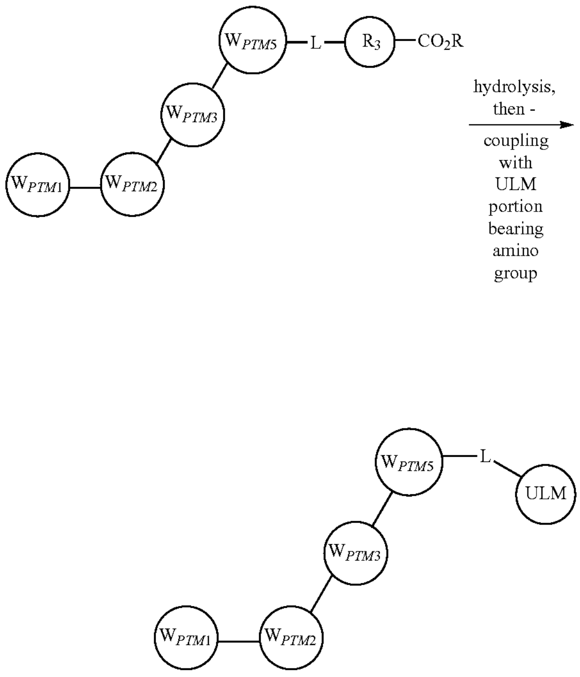

As shown in Scheme 9, nucleophilic displacement of the fluorine atom in the moiety $W_{PTM5}$ with a hydroxyl group-containing compound having $R_3$ provides a $W_{PTM5}$-L-$R_3$ halide, which is coupled under Suzuki or Buchwald conditions to a monoprotected diamine $W_{PTM5}$. Following deprotection of the second amino group, the $W_{PTM3}$-$W_{PTM5}$-L-$R_3$ moiety is then reacted with bis-halogenated $W_{PTM2}$ by a nucleophilic aromatic substitution to provide a monohalide. A subsequent Suzuki reaction with the appropriate boronic acid provides the $W_{PTM1}$-$W_{PTM2}$-$W_{PTM3}$-$W_{PTM5}$-L-$R_3$ ester. The basic hydrolysis and coupling with a ULM portion bearing an amino group provides the PTM-ULM coupling product.

One possible approach to synthesize exemplary compounds of the present disclosure is by following the general synthetic route detailed in the scheme below:

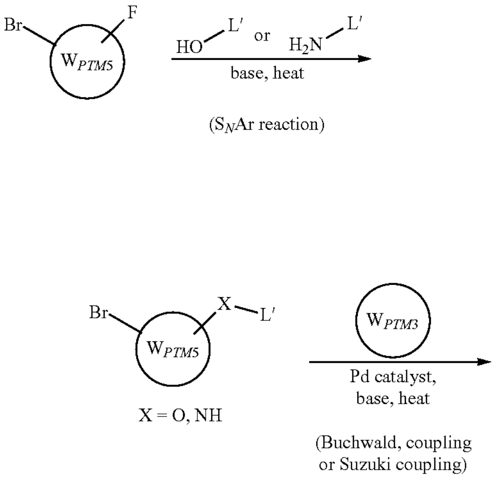

-continued

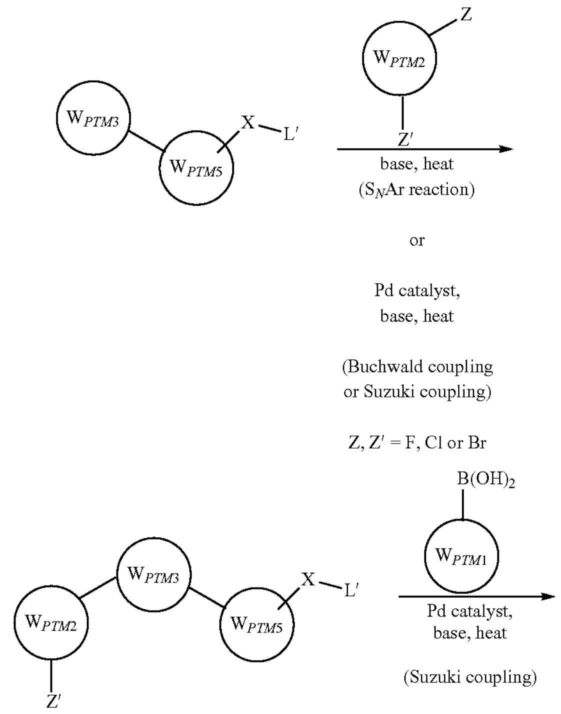

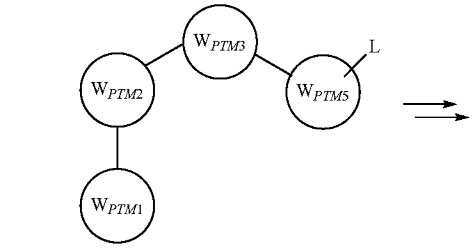

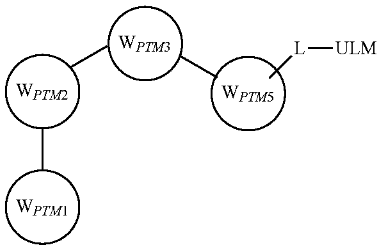

One skilled in the art appreciates that a modified approach can be utilized to attach PTMs via different chemical linkers. For example, in cases where $W_{PTM5}$ is connected to L' via a $CH_2$ group (X=$CH_2$ in the scheme above) one can envision an approach described in the scheme below:

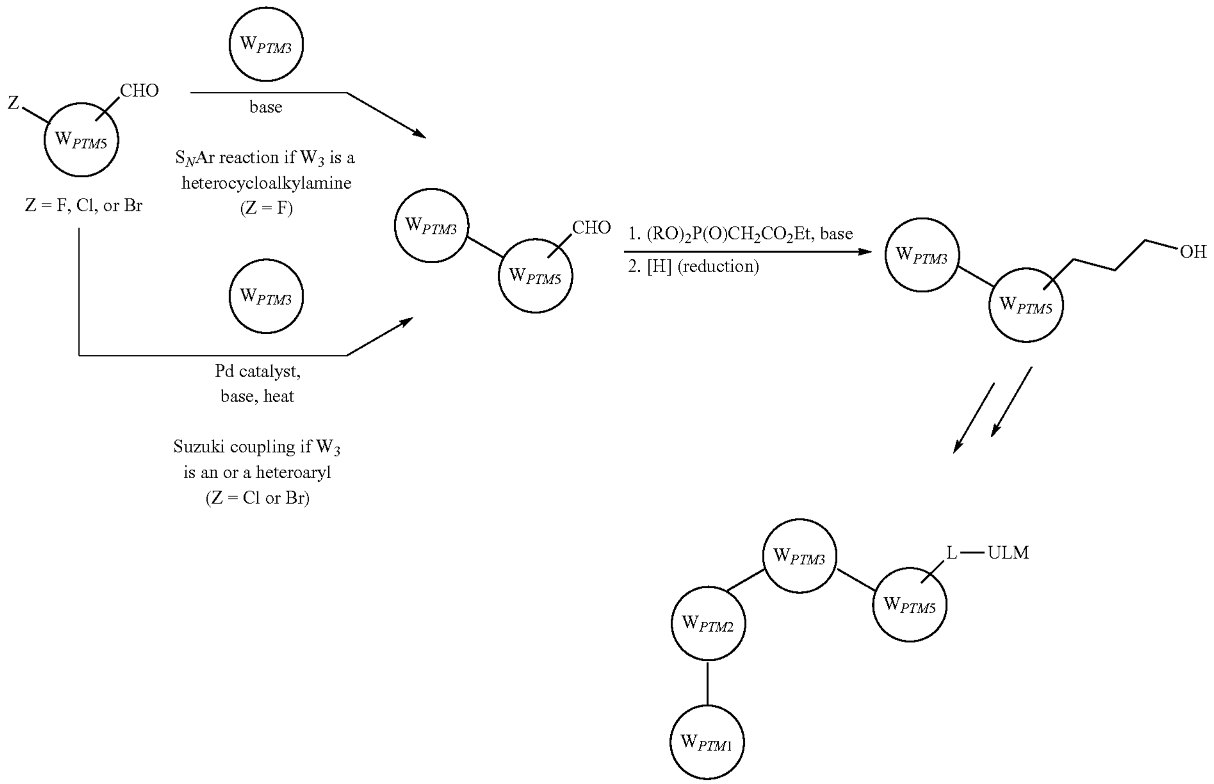
Alternatively, if $W_{PTM5}$ is not present, PTM of an exemplary compound represented by Formula I can be synthesized according to the general scheme below:
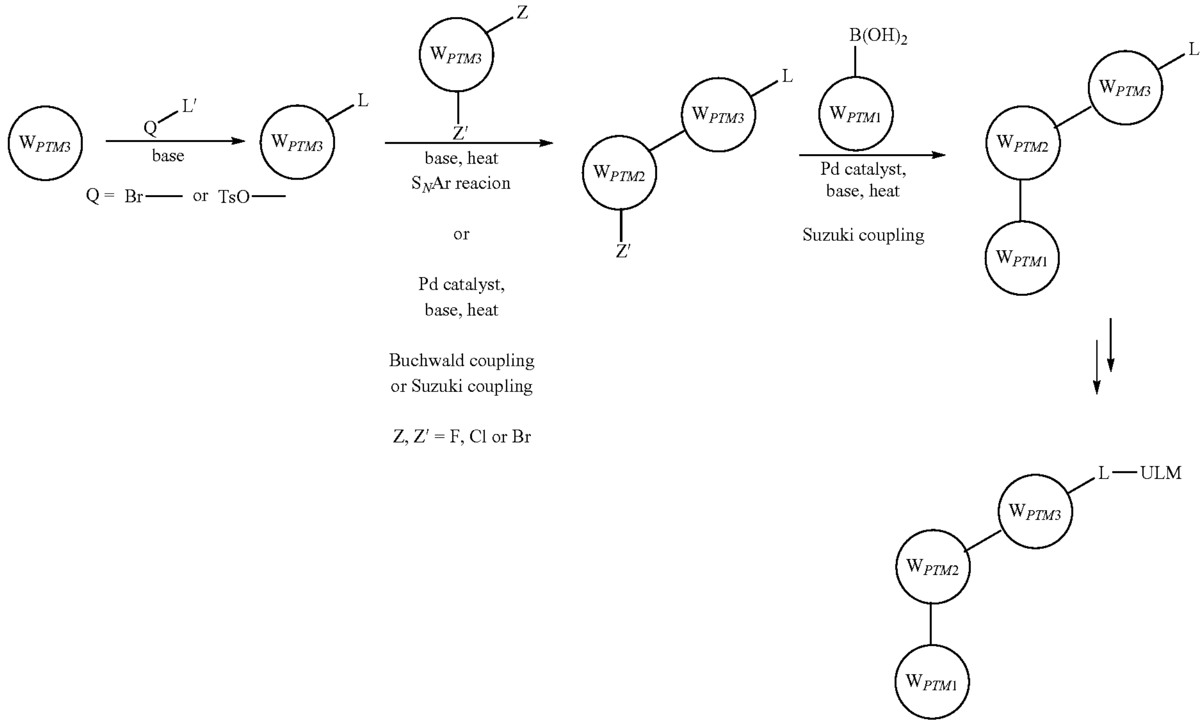

One skilled in the art will appreciate that the general approaches described herein can be modified to adapt to the specific nature of the $W_{PTM1}$, $W_{PTM2}$, $W_{PTM3}$, $W_{PTM4}$, $W_{PTM5}$, $W_{PTM6}$ and $W_{PTM7}$ rings. For example, in some embodiments, exemplary compounds represented by Formula II can be prepared as described in the general synthetic scheme below where one skilled in the art would recognize that additional protection/deprotection steps may be required, depending upon the specific chemical nature of the exemplary compound:

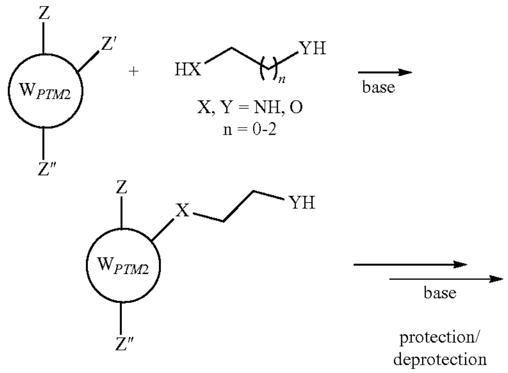

-continued

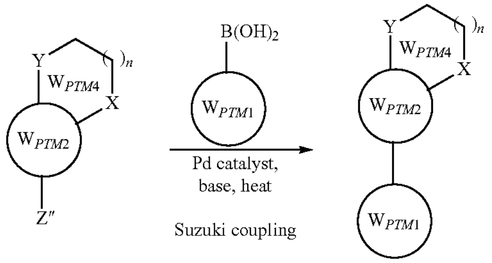

In an embodiment, where X represents NH, the exemplary compound can be prepared according to one of the two schemes shown below, depending on whether $W_{PTM5}$ is present:

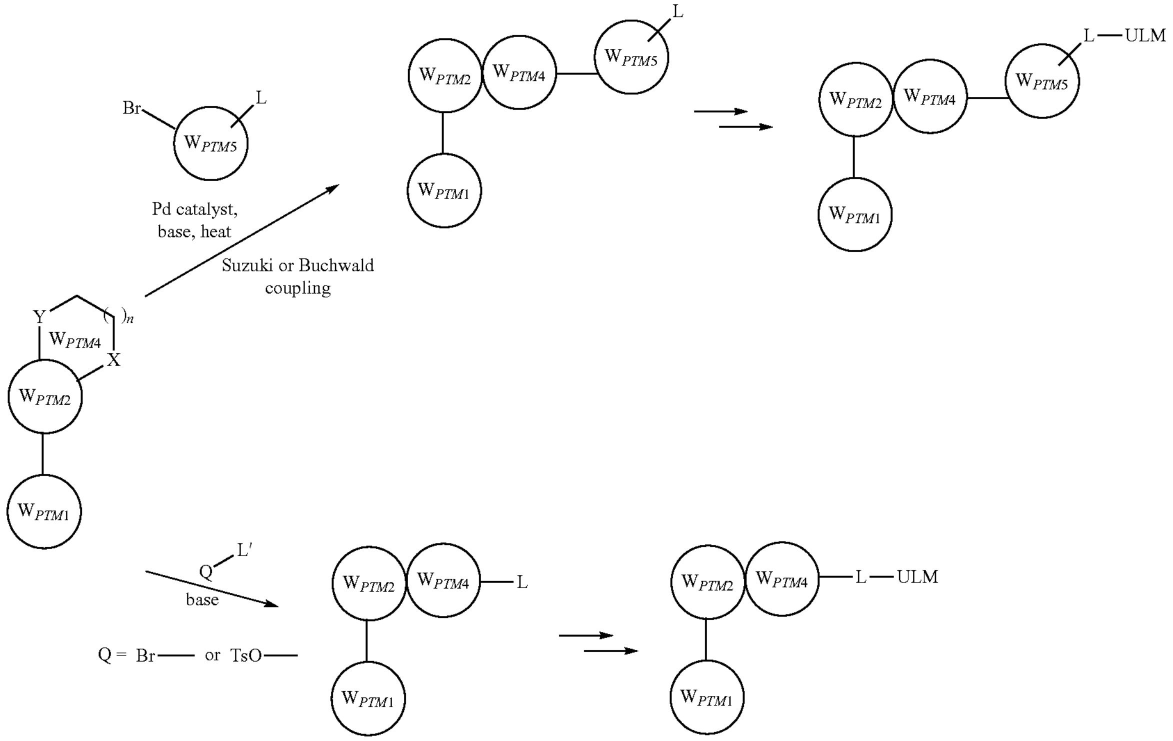

Exemplary PTM represented by general Formula III can be prepared following the general approach described for compounds of Formula I when $W_{PTM5}$ is not present.

Exemplary PTM represented by general Formula IV can be prepared according to the following general scheme:

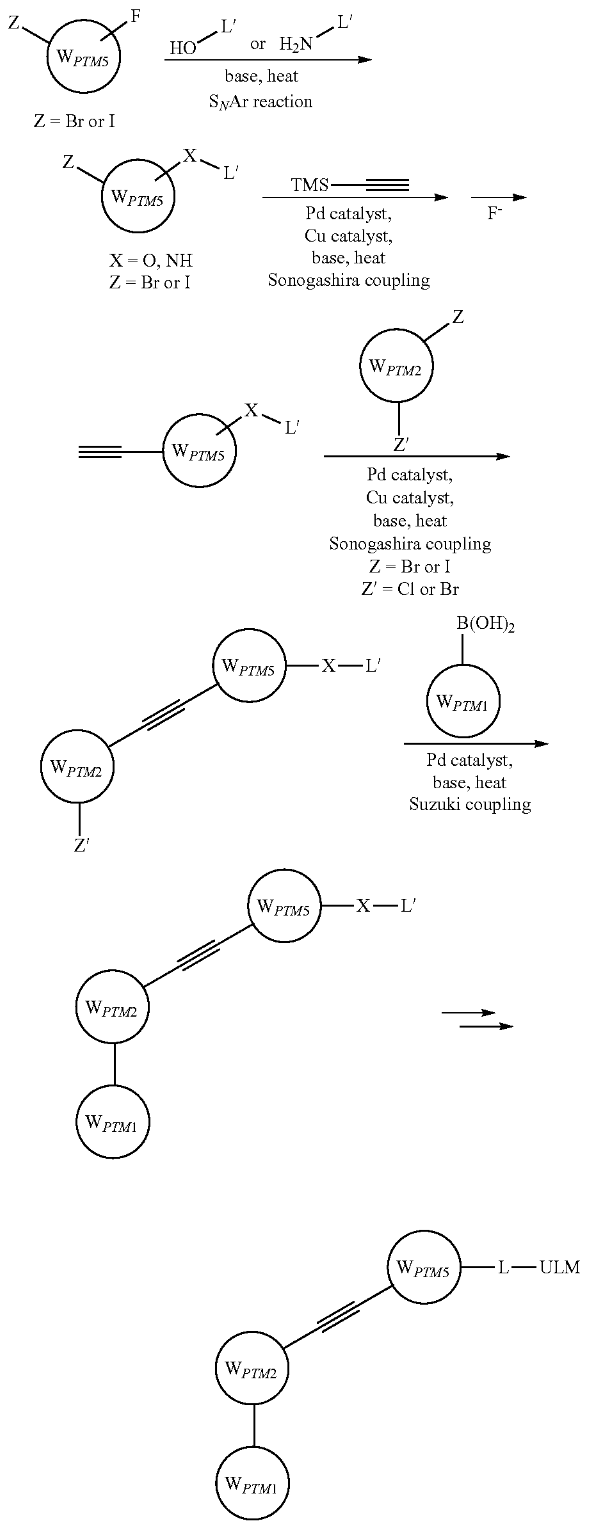

Example Synthesis of Exemplary Compound 11

Step 1

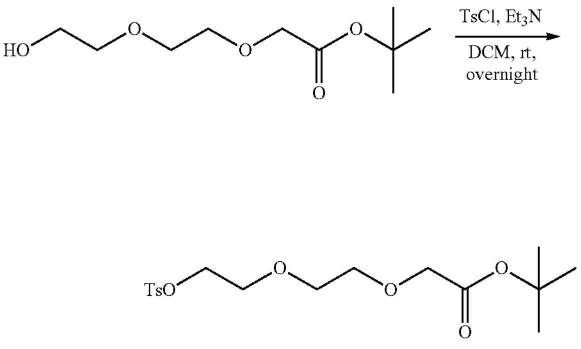

To a mixture of tert-butyl 2-(2-(2-hydroxyethoxy)ethoxy) acetate (1.5 g, 6.8 mmol) and TEA (2.07 g, 20.5 mmol) in DCM (5 mL) was added TsCl (1.95 g, 10.23 mmol) at 0° C. The resulting mixture was warmed to room temperature and stirred for 3 hours. The solution was quenched with water (20 mL), and extracted with DCM. The organic phase was washed with brine (20 mL×2). The organic phase was dried over $Na_2SO_4$, filtered and concentrated. The residue was purified by flash chromatography ($CH_2Cl_2$:MeOH 40:1) to give tert-butyl 2-(2-(2-(tosyloxy)ethoxy)ethoxy)acetate (2.14 g, mmol, 84% yield).

Step 2

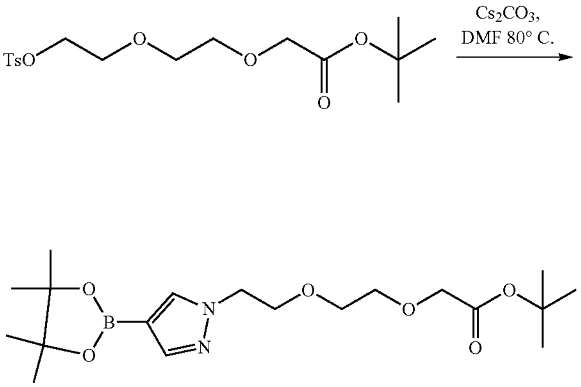

A mixture of 4-(4,4,5,5-tetramethyl-1,3,2-dioxaborolan-2-yl)-1H-pyrazole (1.11 g, 5.722 mmol), tert-butyl 2-(2-(2-(tosyloxy)ethoxy)ethoxy)acetate (2.14 g, 5.722 mmol) and $Cs_2CO_3$ (3.73 g, 11.444 mmol) in dry DMF (10 mL) was heated to 75° C. for 3 hours. The reaction mixture was then cooled to room temperature and diluted with EtOAc (30 mL). The organic layer was washed with water (10 mL) and brine (10 mL×2), dried ($Na_2SO_4$), filtered, and concentrated. The crude residue (2.8 g) was used in the next reaction without further purification.

Step 3

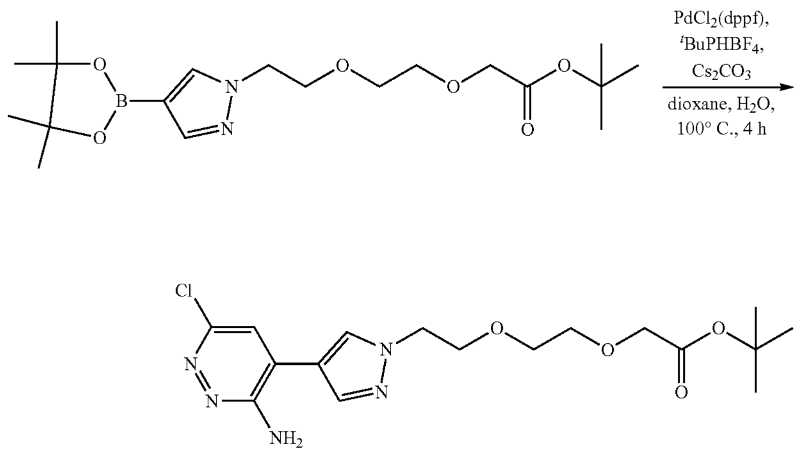

A mixture of tert-butyl 2-(2-(2-(4-(4,4,5,5-tetramethyl-1,3,2-dioxaborolan-2-yl)-1H-pyrazol-1-yl)ethoxy)ethoxy)acetate (1.5 g, 3.79 mmol), 4-bromo-6-chloropyridazin-3-amine (1.1 g, 5.69 mmol), $PdCl_2$(dppf) (555 mg, 0.758 mmol), tBuPHBF$_4$ (441 mg, 1.52 mmol) and $Cs_2CO_3$ (3.09 g, 9.48 mmol) in dioxane (10 ml) and water (1 ml) was heated to 100° C. with stirring for 3 hour under $N_2$. The solid was filtered off, and the filtrate was concentrated. The residue was purified by chromatography ($CH_2C12$:MeOH 30:1) to give tert-butyl 2-(2-(2-(4-(3-amino-6-chloropyridazin-4-yl)-1H-pyrazol-1-yl)ethoxy)ethoxy)acetate (800 mg, 53% yield).

Step 4

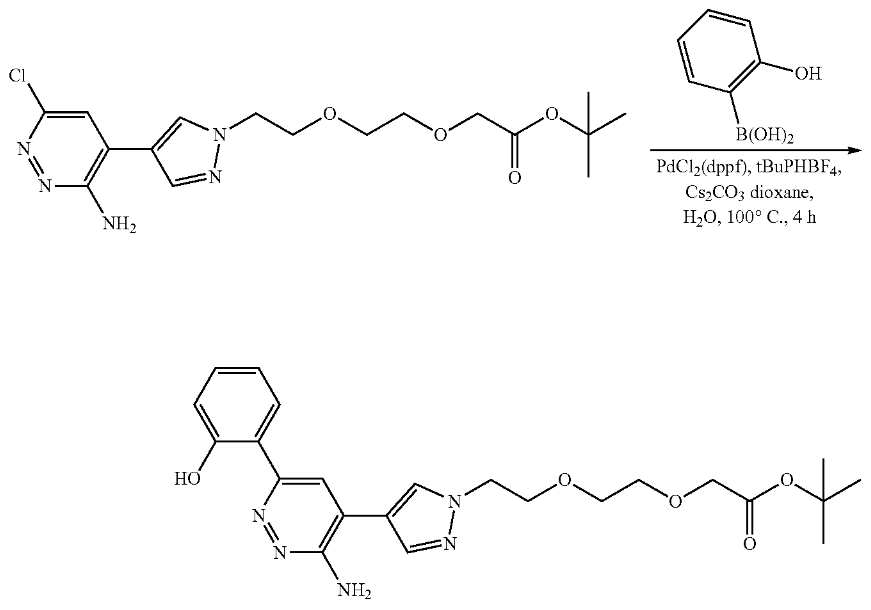 [SMILES: CC(C)(C)OC(=O)COCCOCCn1cc(-c2cc(Cl)nnc2N)cn1 ; OB(O)c1ccccc1O ; CC(C)(C)OC(=O)COCCOCCn1cc(-c2cc(-c3ccccc3O)nnc2N)cn1]

A suspension of tert-butyl 2-(2-(2-(4-(3-amino-6-chloropyridazin-4-yl)-1H-pyrazol-1-yl)ethoxy)ethoxy)acetate (800 mg, 2.02 mmol), (2-hydroxyphenyl)boronic acid (418 mg, 3.03 mmol), cesium carbonate (1.65 g, 5.05 mmol), $PdCl_2$(dppf) (444 mg, 0.606 mmol), and $^t$Bu$_3$PHBF$_4$ (352 mg, 1.212 mmol) in dioxane (10 mL) and water (1 mL) was heated to 100° C. under nitrogen for 3 hours. The mixture was cooled to room temperature and the solid was filtered off. The filtrate was concentrated and purified by chromatography ($CH_2C12$:MeOH 40:1) to afford tert-butyl 2-(2-(2-(4-(3-amino-6-(2-hydroxyphenyl)pyridazin-4-yl)-1H-pyrazol-1-yl)ethoxy)ethoxy)acetate (400 mg, 44% yield).

Step 5

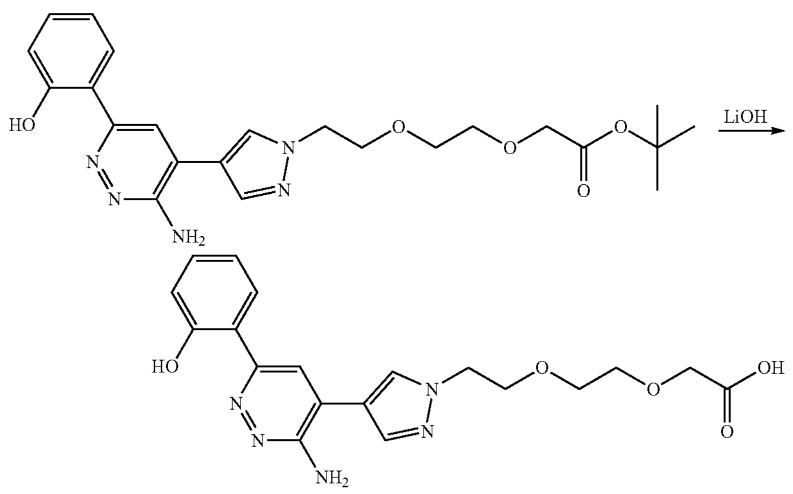

To a solution of tert-butyl 2-(2-(2-(4-(3-amino-6-(2-hydroxyphenyl)pyridazin-4-yl)-1H-pyrazol-1-yl)ethoxy)ethoxy)acetate (400 mg, 0.88 mmol) in THF/$H_2O$ (5 mL, 2:1) was added LiOH (111 mg, 2.64 mmol) at 0° C. The mixture was stirred at 0° C. for 2 hours. The reaction solution was quenched with 1 M HCl. The solution was dried ($Na_2SO_4$), filtered and concentrated under reduced pressure to afford crude 2-(2-(2-(4-(3-amino-6-(2-hydroxyphenyl)pyridazin-4-yl)-1H-pyrazol-1-yl)ethoxy)ethoxy)acetic acid (600 mg), which was used in the next step without further purification.

Step 6

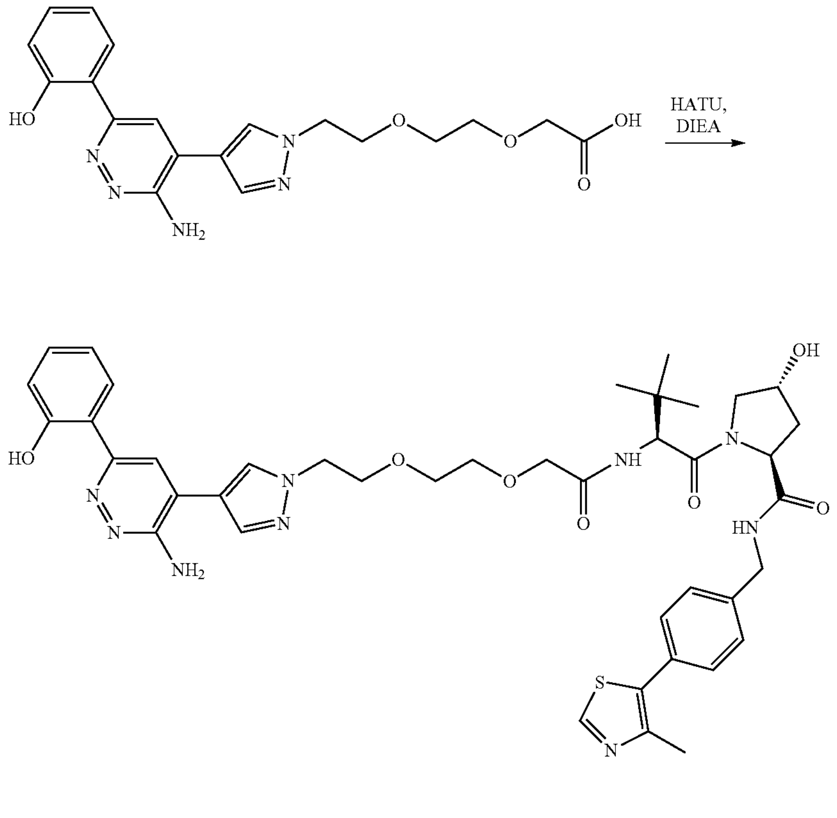 [SMILES: Nc1nnc(-c2ccccc2O)cc1-c1cnn(CCOCCOCC(=O)O)c1 ; Cc1ncsc1-c1ccc(CNC(=O)[C@@H]2C[C@@H](O)CN2C(=O)[C@@H](NC(=O)COCCOCCn2cc(-c3cc(-c4ccccc4O)nnc3N)cn2)C(C)(C)C)cc1]

To a solution of 2-(2-(2-(4-(3-amino-6-(2-hydroxyphenyl)pyridazin-4-yl)-1H-pyrazol-1-yl)ethoxy)ethoxy)acetic acid (200 mg crude), (2S,4R)-1-((S)-2-amino-3,3-dimethylbutanoyl)-4-hydroxy-N-(4-(4-methylthiazol-5-yl)benzyl)pyrrolidine-2-carboxamide (430 mg, 1 mmol), and DIPEA (516 mg, 4 mmol) in DMF (5 mL) was added HATU (570 mg, 1.5 mmol) at 0° C. The reaction mixture was stirred at room temperature for 30 minutes. The mixture was extracted with ethyl acetate (50 mL). The combined organic phases were washed with brine (8 mL×2), dried ($Na_2SO_4$), and filtered. The organic layer was concentrated under reduced pressure. The residue was purified by prep TLC (6% MeOH in DCM) to afford (2S,4R)-1-((S)-2-(2-(2-(2-(4-(3-amino-6-(2-hydroxyphenyl)pyridazin-4-yl)-1H-pyrazol-1-yl)ethoxy)ethoxy)acetamido)-3,3-dimethylbutanoyl)-4-hydroxy-N-(4-(4-methylthiazol-5-yl)benzyl)pyrrolidine-2-carboxamide (22 mg).

$^1$HNMR (400 MHz, MeOD): δ 8.83 (s, 1H), 8.32 (s, 1H), 8.04 (d, J=9.6 Hz, 2H), 7.78 (d, J=7.6 Hz, 1H), 7.65 (d, J=10.0 Hz, 1H), 7.39 (d, J=8.0 Hz, 2H), 7.32-7.34 (m, 2H), 7.28 (m, 1H), 6.95 (d, J=7.6 Hz 2H), 4.69 (d, J=9.6 Hz 1H), 4.44-4.57 (m, 6H), 4.25-4.35 (m, 1H), 3.60-3.99 (m, 11H), 2.46 (s, 3H), 2.23 (m, 1H), 2.08 (m, 1H), 1.01 (s, 9H).

Exemplary Compound 5 was prepared using procedures analogous to those described above for Exemplary Compound 11 as well as procedures known and appreciated to those skilled in the art according to the scheme below:

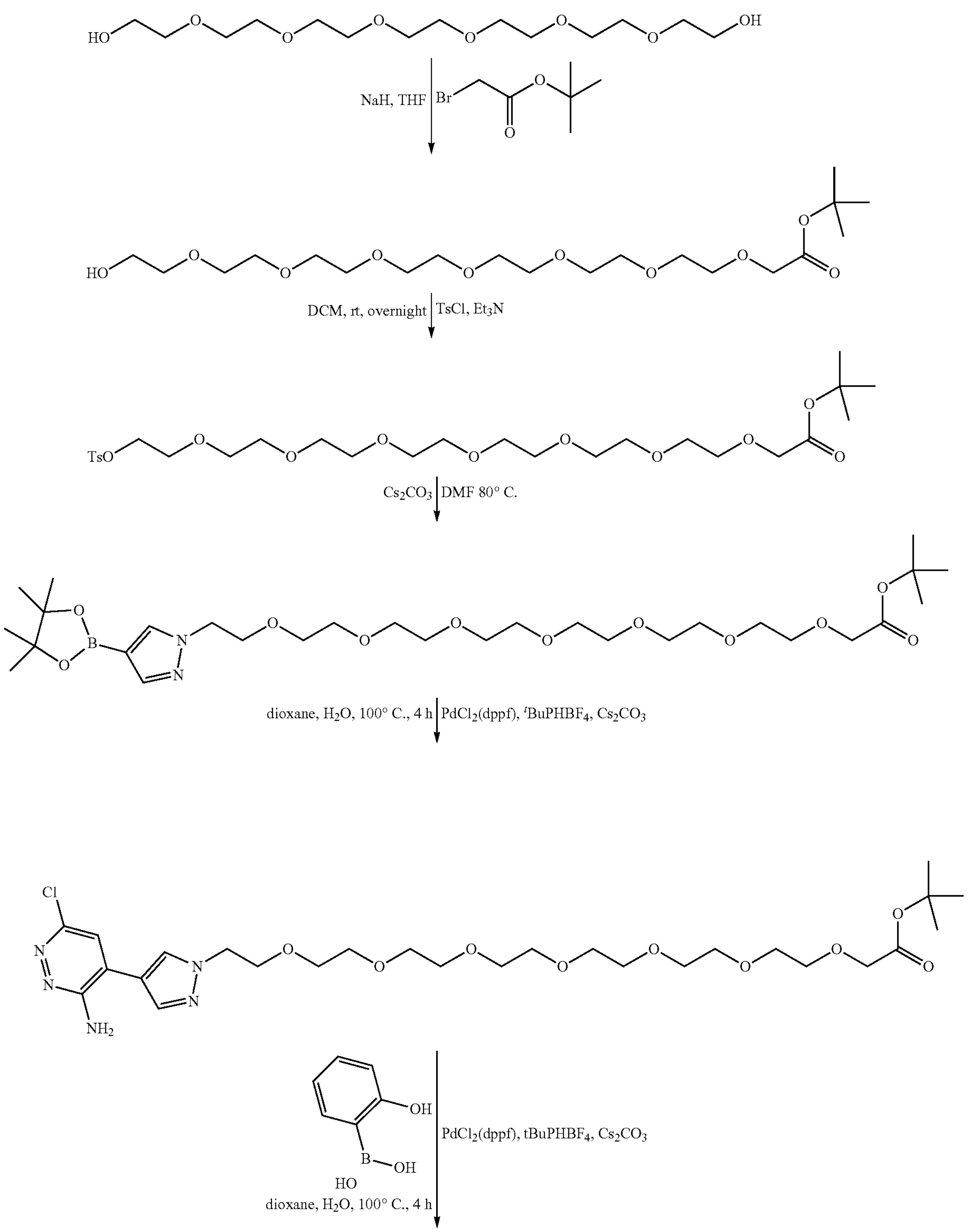

-continued

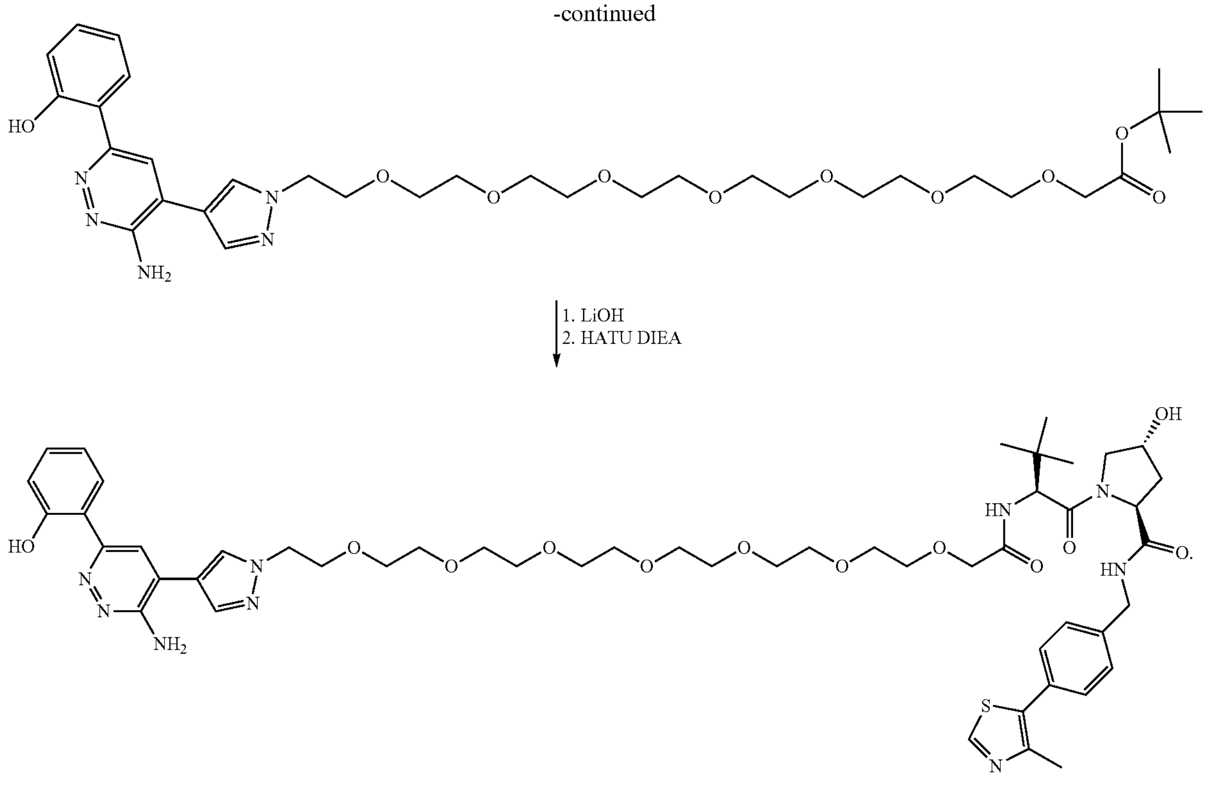

Exemplary Compound 5

Procedures described for Exemplary Compound 11 and Exemplary Compound 5 were used to prepare: Exemplary Compound 1, Exemplary Compound 2, Exemplary Compound 3, Exemplary Compound 4.

Exemplary Synthesis of Exemplary Compound 9

Step 1

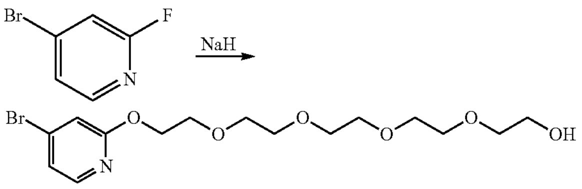

To a solution of 3,6,9,12-tetraoxatetradecane-1,14-diol (13.5 g, 56.8 mmol) in anhydrous DMF (30 mL) was added 60% NaH (1.25 g, 31.2 mmol) at 0° C. The reaction mixture was stirred at room temperature for 0.5 hour. Then 4-bromo-2-fluoropyridine (5 g, 28.4 mmol) was added to the mixture dropwise, and the mixture was heated to 75° C. for 2 hours. The reaction mixture was quenched with water (10 mL) and extracted with EA (200 mL). The organic phase was washed with brine (10 mL), dried ($Na_2SO_4$) and concentrated under reduced pressure. The residue was purified by silica gel column to afford 14-((4-bromopyridin-2-yl)oxy)-3,6,9,12-tetraoxatetradecan-1-ol (9.0 g, 22.9 mmol, 81% yield).

Step 2

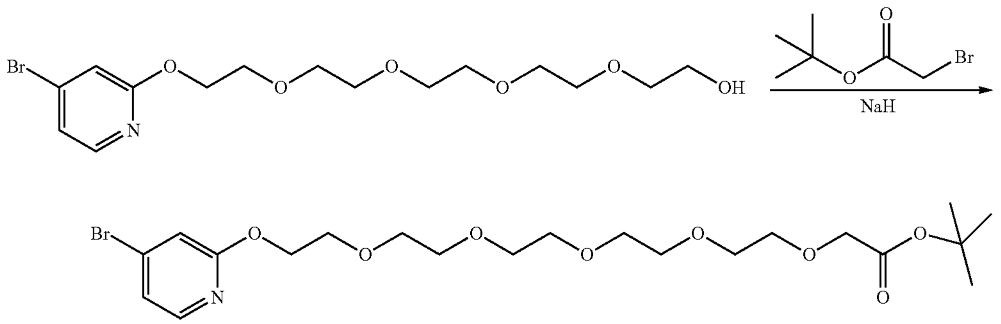

To a solution of 14-((4-bromopyridin-2-yl)oxy)-3,6,9,12-tetraoxatetradecan-1-ol (5.0 g, 12.7 mmol) in anhydrous THF (50 mL) was added 60% NaH (660 mg, 16.5 mmol) at 0° C. The reaction mixture was stirred at room temperature for 40 minutes. Then tert-butyl 2-bromoacetate (4.9 g, 25.4 mmol) was added dropwise to the mixture and stirred at room temperature overnight. The reaction mixture was quenched with 2N $NH_4Cl$ (10 mL) and extracted with EA (200 mL). Then the organic phase was washed with brine (10 mL), dried ($Na_2SO_4$), and concentrated under reduced pressure. The residue was purified by silica gel column to afford tert-butyl 17-((4-bromopyridin-2-yl)oxy)-3,6,9,12,15-pentaoxaheptadecanoate (2.6 g, 5.13 mmol, 40% yield).

Step 3

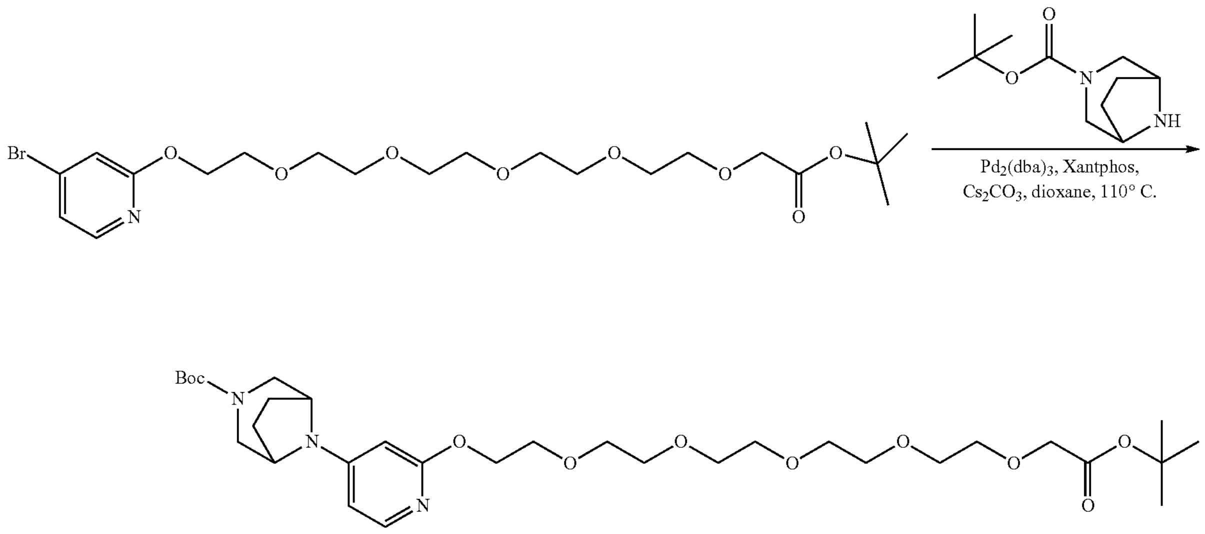

A mixture of tert-butyl 17-((4-bromopyridin-2-yl)oxy)-3,6,9,12,15-pentaoxaheptadecanoate (250 mg, 1.18 mmol), tert-butyl 3,8-diazabicyclo[3.2.1]octane-3-carboxylate (718 mg, 1.4 mmol), cesium carbonate (769 mg, 2.36 mmol), $Pd_2(dba)_3$ (110 mg, 0.12 mmol) and XantPhos (138 mg, 0.24 mmol) in dioxane (5 mL) in a seal tube was heated to 110° C. under nitrogen overnight. The mixture was extracted with EA (100 mL). Then the organic phase was washed with water (10 mL), brine (10 mL), dried ($Na_2SO_4$), and concentrated under reduced pressure. The residue was purified by silica gel column to afford tert-butyl 8-(2-((19,19-dimethyl-17-oxo-3,6,9,12,15,18-hexaoxaicosyl)oxy)pyridin-4-yl)-3,8-diazabicyclo[3.2.1]octane-3-carboxylate (550 mg, 0.86 mmol, 73% yield).

Step 4

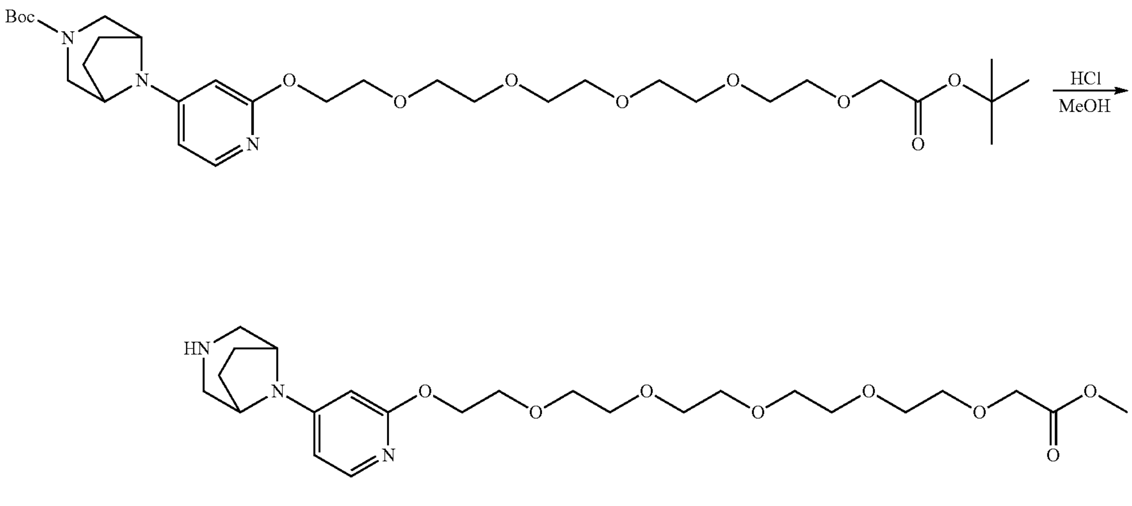

To a solution of tert-butyl 8-(2-((19,19-dimethyl-17-oxo-3,6,9,12,15,18-hexaoxaicosyl)oxy)pyridin-4-yl)-3,8-diazabicyclo[3.2.1]octane-3-carboxylate (550 mg, 0.86 mmol) in MeOH (15 mL) was added HCl in dioxane (6N in dioxane) (5 ml, 30 mmol) at rt. The reaction mixture was stirred at room temperature for 1 hour. The mixture was concentrated under reduced pressure to afford crude methyl 17-((4-(3,8-diazabicyclo[3.2.1]octan-8-yl)pyridin-2-yl)oxy)-3,6,9,12,15-pentaoxaheptadecanoate (0.55 g).

Step

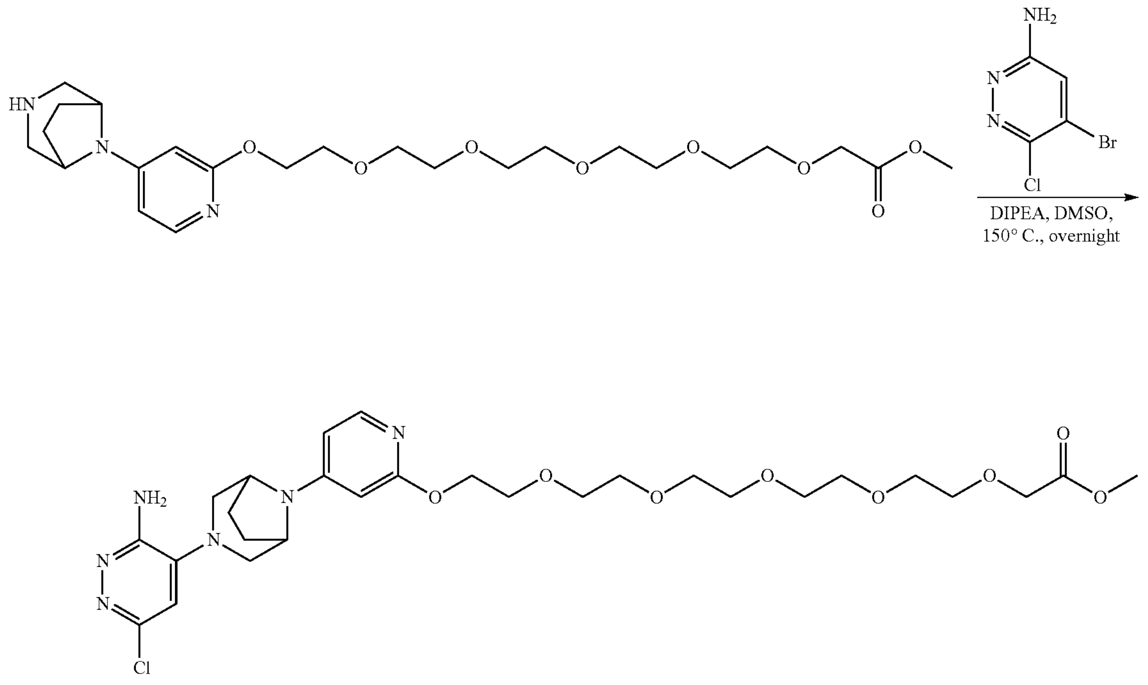

To a solution of crude methyl 17-((4-(3,8-diazabicyclo[3.2.1]octan-8-yl)pyridin-2-yl)oxy)-3,6,9,12,15-pentaoxaheptadecanoate (550 mg crude) in DMSO (5 mL) were added 5-bromo-6-chloropyridazin-3-amine (526 mg, 2.71 mmol) and DIPEA (1.87 g, 14.5 mmol). The solution was stirred at 150° C. overnight. The mixture was extracted with EA (60 mL). The organic phase was washed with water (8 mL) and brine (8 mL). The organic layer was dried ($Na_2SO_4$), filtered and concentrated under reduced pressure. The residue was purified by silica gel column chromatography to afford methyl 17-((4-((1R,5S)-3-(3-amino-6-chloropyridazin-4-yl)-3,8-diazabicyclo[3.2.1]octan-8-yl)pyridin-2-yl)oxy)-3,6,9,12,15-pentaoxaheptadecanoate (400 mg).

Step 6

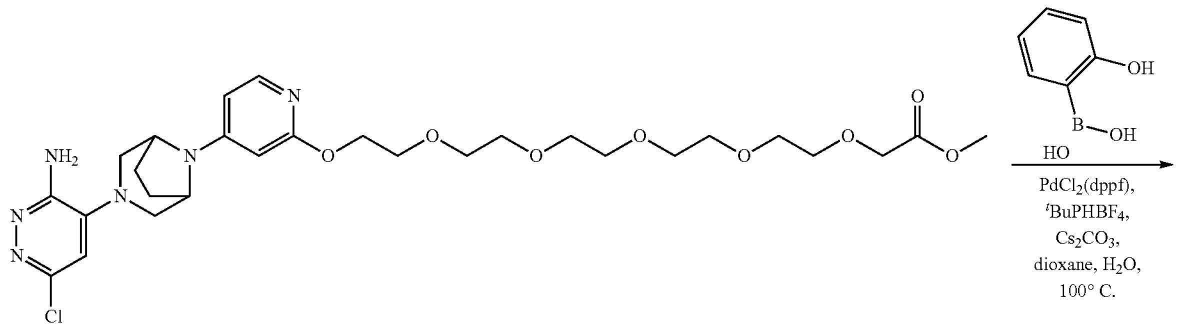

-continued

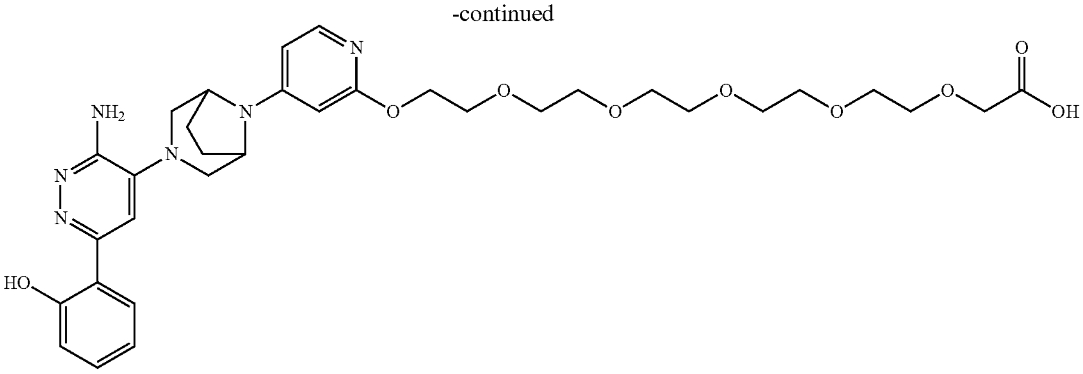

To a solution of methyl 17-((4-((1R,5S)-3-(3-amino-6-chloropyridazin-4-yl)-3,8-diazabicyclo[3.2.1]octan-8-yl)pyridin-2-yl)oxy)-3,6,9,12,15-pentaoxaheptadecanoate (325 mg, 0.52 mmol) and (2-hydroxyphenyl)boronic acid (93 mg, 0.68 mmol) in dioxane (12 mL) and water (1.2 mL) were added cesium carbonate (542 mg, 1.66 mmol), $PdCl_2$(dppf) (73.2 mg, 0.1 mmol) and t-$Bu_3PHBF_4$ (58 mg, 0.2 mmol). The solution was stirred at 100° C. under nitrogen atmosphere for 4 hours. The pH of the solution was adjusted to 5 with 1N HCl. The mixture was filtered and the filtrate was concentrated under reduced pressure to afford the crude 17-((4-((1R,5S)-3-(3-amino-6-(2-hydroxyphenyl)pyridazin-4-yl)-3,8-diazabicyclo[3.2.1]octan-8-yl)pyridin-2-yl)oxy)-3,6,9,12,15-pentaoxaheptadecanoic acid (300 mg), which was used in the next step without further purification.

Step 7

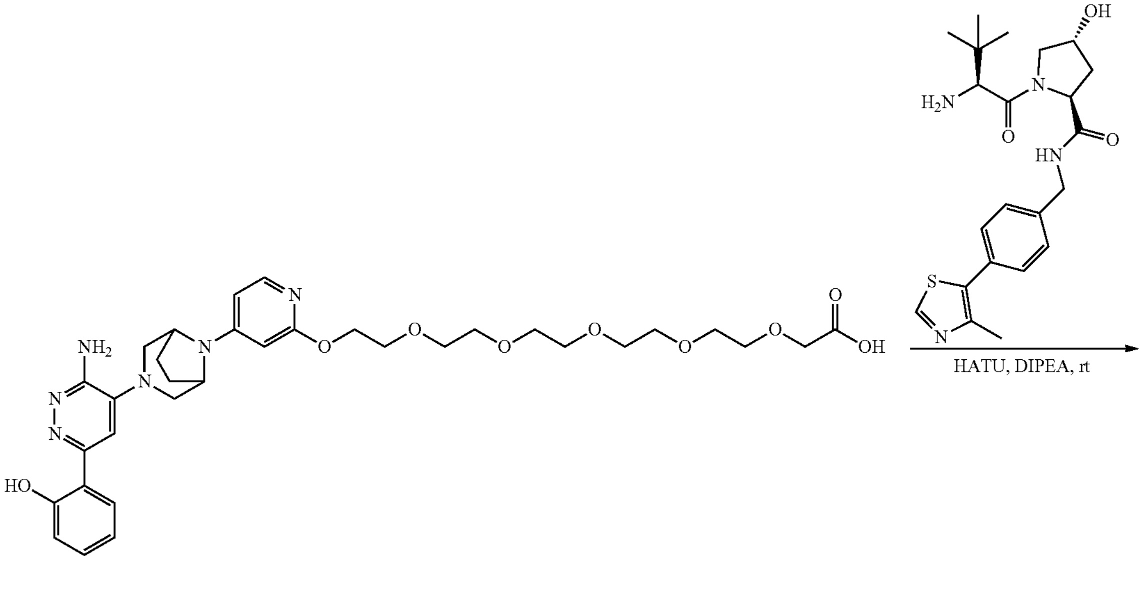

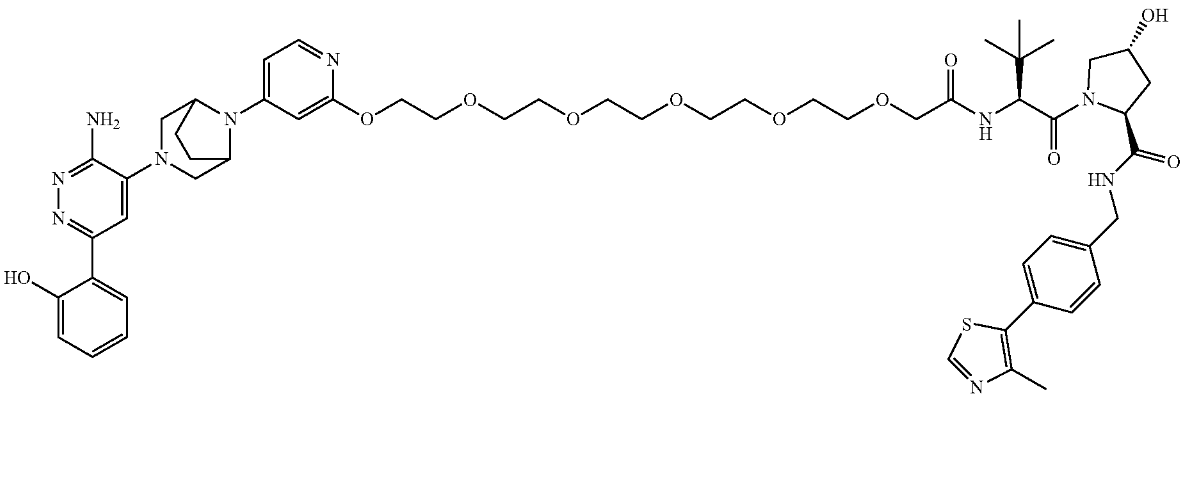

To a solution of crude 17-((4-((1R,5S)-3-(3-amino-6-(2-hydroxyphenyl)pyridazin-4-yl)-3,8-diazabicyclo[3.2.1]octan-8-yl)pyridin-2-yl)oxy)-3,6,9,12,15-pentaoxaheptadecanoic acid (80 mg, 0.12 mmol) and (2S,4R)-1-((S)-2-amino-3,3-dimethylbutanoyl)-4-hydroxy-N-(4-(4-methylthiazol-5-yl)benzyl)pyrrolidine-2-carboxamide (108 mg, 0.24 mmol) in DMF (5 mL) were added DIPEA (124 mg, 0.96 mmol) and HATU (92 mg, 0.24 mmol) at 0° C. The reaction mixture was stirred at rt for 30 minutes. The mixture was extracted with EA (50 mL). The organic phase was washed with water (8 mL) and brine (8 mL). The organic layer was dried ($Na_2SO_4$), filtered and concentrated under reduced pressure. The residue was purified by prep TLC (6% MeOH in DCM) to afford (2S,4R)-1-((S)-20-((4-((1R,5S)-3-(3-amino-6-(2-hydroxyphenyl)pyridazin-4-yl)-3,8-diazabicyclo[3.2.1]octan-8-yl)pyridin-2-yl)oxy)-2-(tert-butyl)-4-oxo-6,9,12,15,18-pentaoxa-3-azaicosanoyl)-4-hydroxy-N-(4-(4-methylthiazol-5-yl)benzyl)pyrrolidine-2-carboxamide (20 mg, 0.018 mmol, 15.0% yield).

$^1H$ NMR (400 MHz, MeOD): δ 8.74 (s, 1H), 7.68-7.66 (m, 2H), 7.34-7.28 (m, 5H), 7.18-7.10 (m, 1H), 6.80-6.78 (m, 2H), 6.43-6.40 (m, 1H), 6.10 (s, 1H), 4.60-4.20 (m, 9H), 3.92-3.89 (m, 2H), 3.80-3.64 (m, 4H), 3.71-3.45 (m, 16H), 3.10-3.00 (m, 1H), 3.00-2.90 (m, 2H), 2.37-2.34 (m, 1H), 2.35 (s, 3H), 2.18-1.99 (m, 6H), 0.92 (s, 9H).

Using analogous procedures, Exemplary Compounds 7, 8, 10 and 35 were prepared.

Exemplary Synthesis of Exemplary Compound 6

Step 1

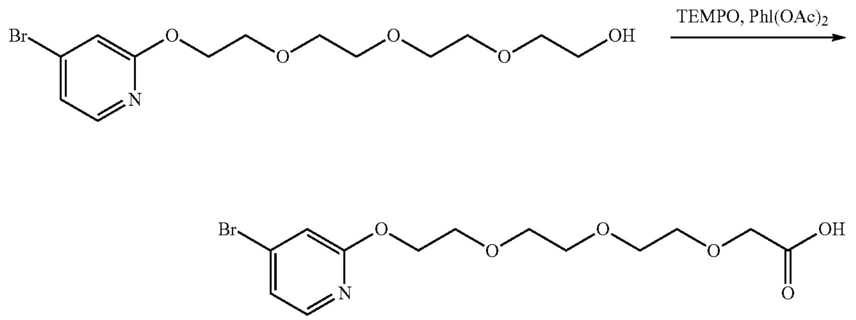

To a solution of 2-(2-(2-(2-((4-bromopyridin-2-yl)oxy)ethoxy)ethoxy)ethoxy)ethan-1-ol (3.49 g, 10 mmol) [prepared using procedure analogous to that described for example A2979] in DCM (50 mL) and $H_2O$ (25 mL) were added $PhI(OAc)_2$ (9.66 g, 30 mmol) and TEMPO (312 mg, 2 mmol). The reaction mixture was stirred at room temperature for 2 hours. The mixture was extracted with EA (100 mL). The organic phase was washed with water (10 ml) and brine (10 ml). The organic layer was dried ($Na_2SO_4$), filtered and concentrated under reduced pressure. The residue was purified by silica gel column chromatography to afford 2-(2-(2-(2-((4-bromopyridin-2-yl)oxy)ethoxy)ethoxy)ethoxy)acetic acid (3.5 g, 9.64 mmol, 96% yield).

Step 2

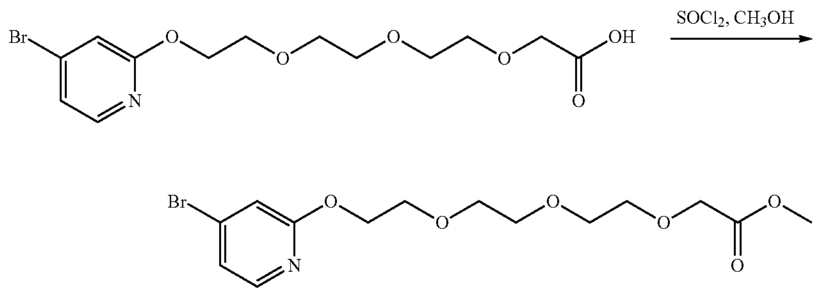

To a solution of 2-(2-(2-(2-((4-bromopyridin-2-yl)oxy)ethoxy)ethoxy)ethoxy)acetic acid (3.0 g, 8.26 mmol) in MeOH (30 mL) was added $SOCl_2$ (4.0 g, 33.9 mmol) dropwise at 0° C. The reaction mixture was stirred at room temperature for 4 hours. The pH of the solution was adjusted to ~8 with saturated $NaHCO_3$. The mixture was extracted with DCM (100 mL). The organic phase was washed with water (10 mL) and brine (10 mL). The organic layer was dried ($Na_2SO_4$), filtered and concentrated under reduced pressure to afford methyl 2-(2-(2-(2-((4-bromopyridin-2-yl)oxy)ethoxy)ethoxy)ethoxy)acetate (2.9 g, 7.69 mmol, 93% yield).

Methyl 2-(2-(2-(2-((4-bromopyridin-2-yl)oxy)ethoxy)ethoxy)ethoxy)acetate was converted to the final compound, (2S,4R)-1-((2S)-14-((4-(3-(3-amino-6-(2-hydroxyphenyl)pyridazin-4-yl)-3,8-diazabicyclo[3.2.1]octan-8-yl)pyridin-2-yl)oxy)-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (Exemplary Compound 6) using procedures analogous to those described for Exemplary Compound 9.

$^1H$NMR (400 MHz, MeOD): δ 8.82 (s, 1H), 7.76-7.74 (m, 2H), 7.42-7.34 (m, 5H), 7.22-7.18 (m, 1H), 6.89-6.86 (m, 2H), 6.53-6.52 (m, 1H), 6.16 (s, 1H), 4.66-4.28 (m, 9H), 4.01-4.00 (m, 2H), 3.82-3.60 (m, 12H), 3.31-3.29 (m, 1H), 3.10-3.08 (m, 2H), 2.51-2.50 (m, 1H), 2.49 (s, 3H), 2.29-2.05 (m, 6H), 2.42-2.29 (m, 2H), 1.01 (s, 9H).

Exemplary Synthesis of Exemplary Compound 20

Step 1

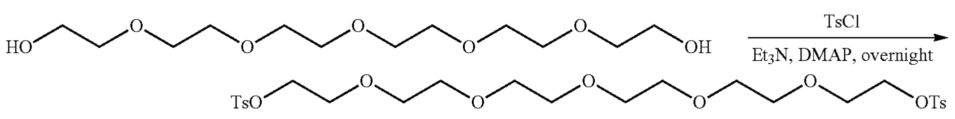

To a solution of 3,6,9,12,15-pentaoxaheptadecane-1,17-diol (4 g, 14.2 mmol) and $Et_3N$ (8.6 g, 85.2 mmol) in DCM (50 mL) was added TsCl (8.1 g, 42.6 mmol). The reaction mixture was stirred at room temperature for 1 hour. The mixture was partitioned between EtOAc (100 mL) and water (10 mL). The organic phase was washed with brine (10 mL). The combined organic layers were dried ($Na_2SO_4$), filtered and concentrated under reduced pressure. The residue was purified by silica gel column chromatography to afford 3,6,9,12,15-pentaoxaheptadecane-1,17-diyl bis(4-methylbenzenesulfonate) (6.0 g, 10.2 mmol, 72% yield).

Step 2

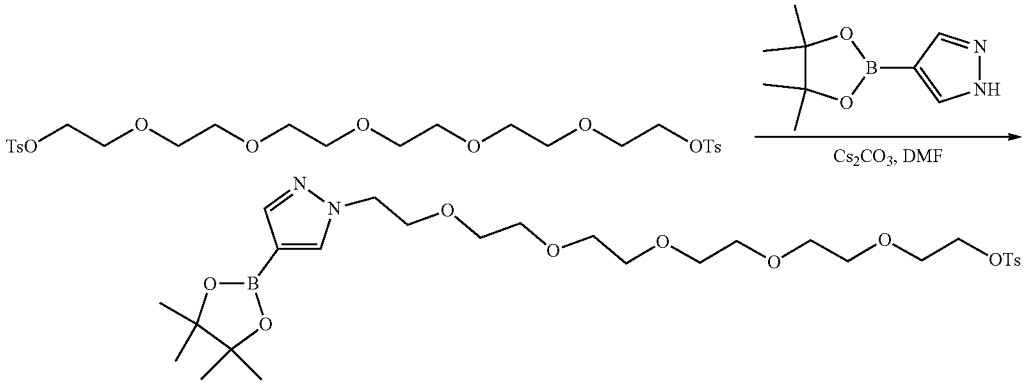

To a solution of 3,6,9,12,15-pentaoxaheptadecane-1,17-diyl bis(4-methylbenzenesulfonate) (3.5 g, 5.93 mmol) in anhydrous DMF (20 mL) were added 4-(4,4,5,5-tetramethyl-1,3,2-dioxaborolan-2-yl)-1H-pyrazole (1.15 g, 5.93 mmol) and $Cs_2CO_3$ (3.87 g, 11.86 mmol). The reaction mixture was stirred at 75° C. for 0.5 hour. The mixture was cooled to rt and partitioned between EtOAc (200 mL) and water (20 mL). The organic phase was washed with brine (20 mL). The combined organic layers were dried ($Na_2SO_4$), filtered and concentrated under reduced pressure. The residue was purified by silica gel column chromatography to afford 17-(4-(4,4,5,5-tetramethyl-1,3,2-dioxaborolan-2-yl)-1H-pyrazol-1-yl)-3,6,9,12,15-pentaoxaheptadecyl 4-methylbenzenesulfonate (0.6 g, 0.98 mmol, 16.5% yield).

Step 3

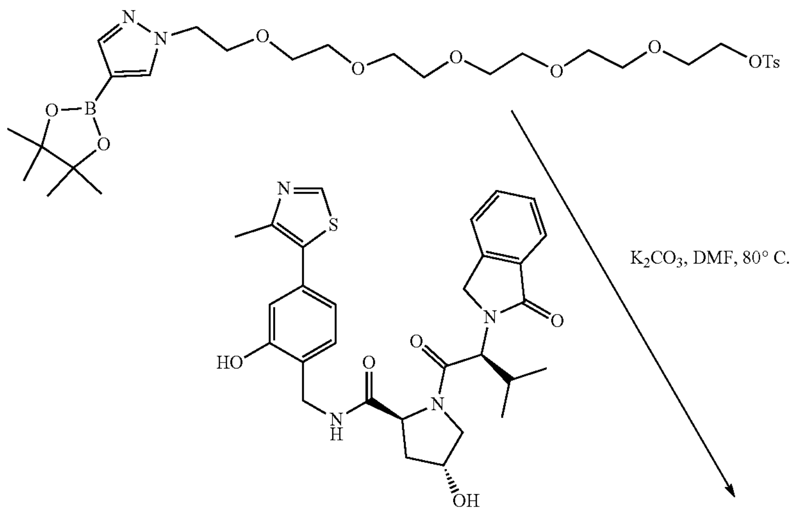

-continued

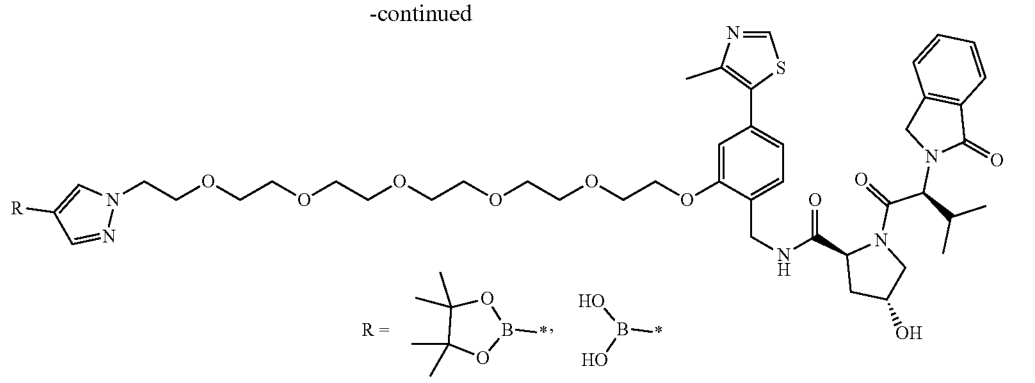

To a solution of 17-(4-(4,4,5,5-tetramethyl-1,3,2-dioxaborolan-2-yl)-1H-pyrazol-1-yl)-3,6,9,12,15-pentaoxaheptadecyl 4-methylbenzenesulfonate (0.3 g, 0.49 mmol) and (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (268 mg, 0.49 mmol) in DMF (5 mL) was added $K_2CO_3$ (135 mg, 0.98 mmol). The mixture was stirred at 80° C. under nitrogen atmosphere for 2 hours. The mixture was extracted with EA (80 mL). The organic phase was washed with water (10 mL) and brine (10 mL). The organic layer was dried ($Na_2SO_4$), filtered and concentrated under reduced pressure. The residue was purified by silica gel column chromatography to afford a mixture of (2S,4R)-4-hydroxy-1-((S)-3-methyl-2-(1-oxoisoindolin-2-yl)butanoyl)-N-(4-(4-methylthiazol-5-yl)-2-((17-(4-(4,4,5,5-tetramethyl-1,3,2-dioxaborolan-2-yl)-1H-pyrazol-1-yl)-3,6,9,12,15-pentaoxaheptadecyl)oxy)benzyl)pyrrolidine-2-carboxamide and (1-(17-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)-3,6,9,12,15-pentaoxaheptadecyl)-1H-pyrazol-4-yl)boronic acid (270 mg, 0.27 mmol, 56% yield).

Step 4

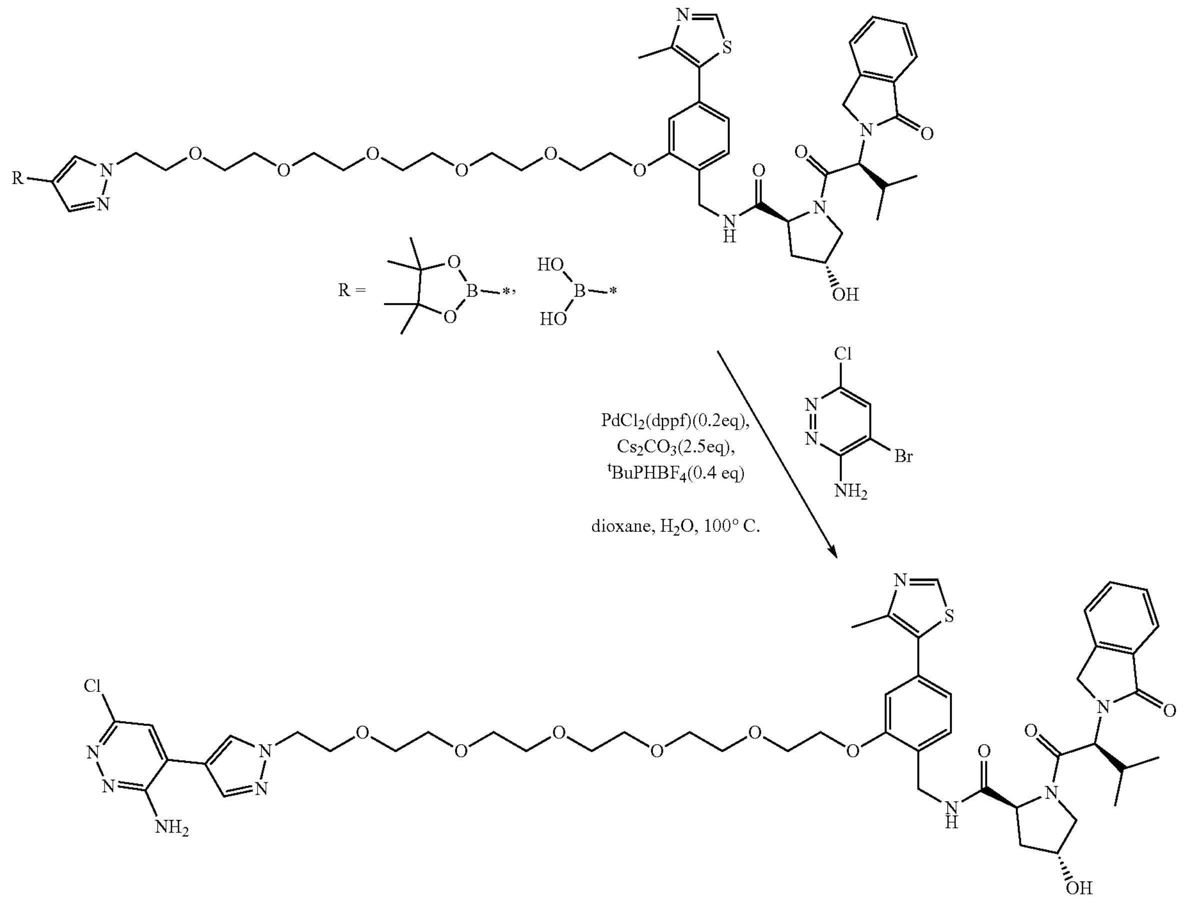

To a solution of the mixture of (2S,4R)-4-hydroxy-1-((S)-3-methyl-2-(1-oxoisoindolin-2-yl)butanoyl)-N-(4-(4-methylthiazol-5-yl)-2-((17-(4-(4,4,5,5-tetramethyl-1,3,2-dioxaborolan-2-yl)-1H-pyrazol-1-yl)-3,6,9,12,15-pentaoxaheptadecyl)oxy)benzyl)pyrrolidine-2-carboxamide and (1-(17-(2-(((2S,4R)-4-hydroxy-1-((S)-3-methyl-2-(1-oxoisoindolin-2-yl)butanoyl)pyrrolidine-2-carboxamido)methyl)-5-(4-methylthiazol-5-yl)phenoxy)-3,6,9,12,15-pentaoxaheptadecyl)-1H-pyrazol-4-yl)boronic acid (270 mg, 0.27 mmol) and 5-bromo-6-chloropyridazin-3-amine (85 mg, 0.41 mmol) in dioxane (20 mL) and water (2 mL) were added cesium carbonate (220 mg, 0.68 mmol), $PdCl_2$(dppf) (40 mg, 0.054 mmol) and t-$Bu_3PHBF_4$ (31 mg, 0.11 mmol). The solution was stirred at 100° C. under nitrogen atmosphere for 4 hours. The mixture was concentrated under reduced pressure. The residue was purified by silica gel column chromatography to afford (2S,4R)—N-(2-((17-(4-(3-amino-6-chloropyridazin-4-yl)-1H-pyrazol-1-yl)-3,6,9,12,15-pentaoxaheptadecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide (175 mg, 0.18 mmol, 67% yield).

Step 5

To a solution of (2S,4R)—N-(2-((17-(4-(3-amino-6-chloropyridazin-4-yl)-1H-pyrazol-1-yl)-3,6,9,12,15-pentaoxaheptadecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide (175 mg, 0.18 mmol) and (2-hydroxyphenyl)boronic acid (32 mg, 0.23 mmol) in dioxane (15 mL) and water (1.5 mL) were added cesium carbonate (176 mg, 0.54 mmol), $PdCl_2$(dppf) (53 mg, 0.072 mmol) and t-$Bu_3PHBF_4$ (42 mg, 0.144 mmol). The solution was stirred at 100° C. under nitrogen atmosphere for 4 hours. The mixture was concentrated under reduced pressure. The residue was purified by silica gel column chromatography to afford (2S,4R)—N-(2-((17-(4-(3-amino-6-(2-hydroxyphenyl)pyridazin-4-yl)-1H-pyrazol-1-yl)-3,6,9,12,15-pentaoxaheptadecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide (24 mg, 0.023 mmol, 13% yield).

$^1$HNMR (400 MHz, MeOD): δ 8.84 (s, 1H), 8.28 (s, 1H), 8.05 (d, J=12.4 Hz, 2H), 7.38-7.81 (m, 6H), 7.36-7.37 (m, 1H), 6.98-7.00 (m, 2H), 6.92 (d, J=7.6 Hz, 2H), 4.37-4.59 (m, 9H), 4.15-4.16 (m, 2H), 3.83-3.96 (m, 6H), 3.46-3.56

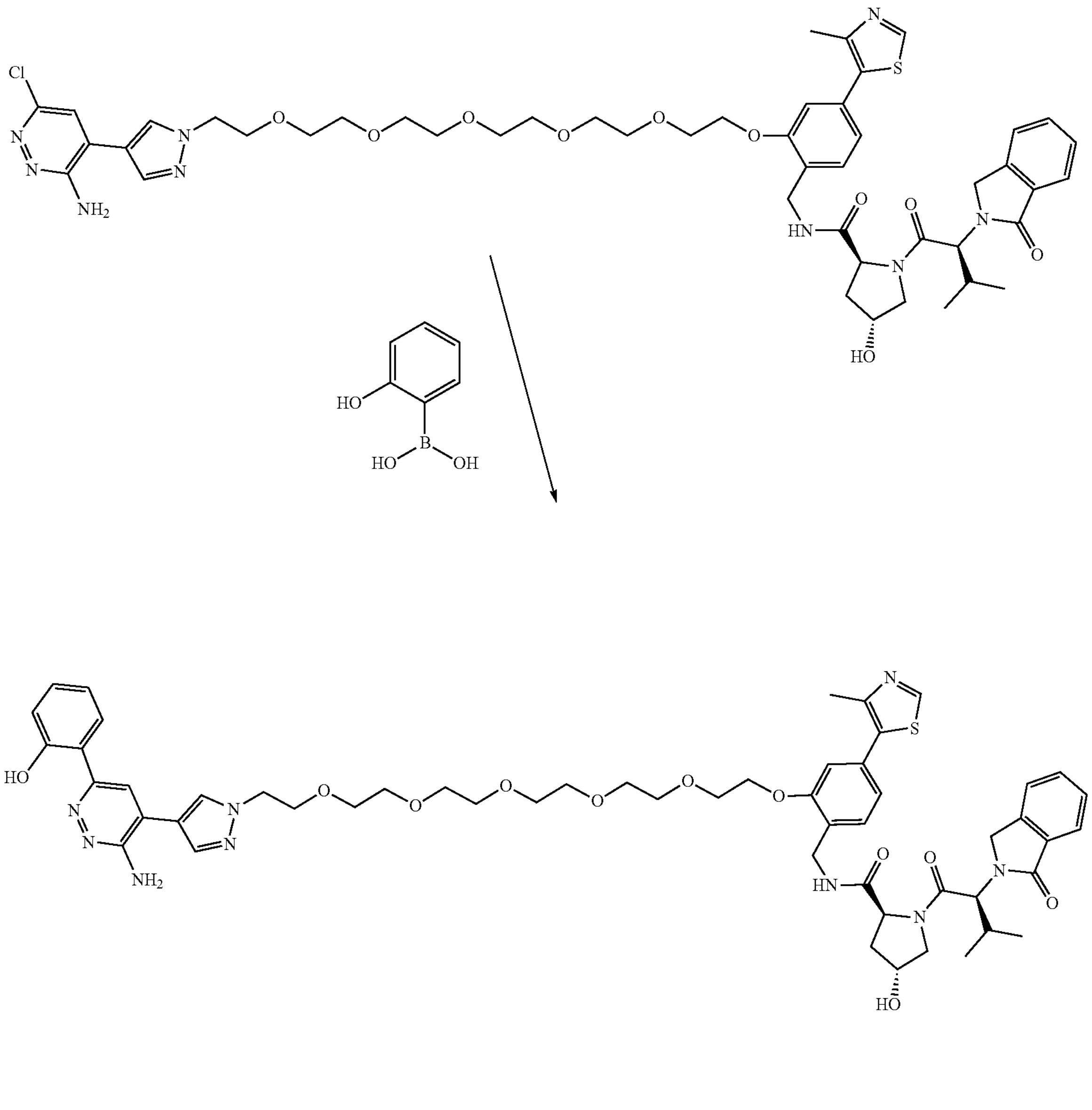 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOCCOCCn2cc(-c3cc(Cl)nnc3N)cn2)c1 ; OB(O)c1ccccc1O ; Cc1ncsc1-c1ccc(CNC(=O)[C@@H]2C[C@@H](O)CN2C(=O)[C@H](C(C)C)N2Cc3ccccc3C2=O)c(OCCOCCOCCOCCOCCOCCn2cc(-c3cc(-c4ccccc4O)nnc3N)cn2)c1]

(m, 16H), 2.46 (s, 3H), 2.44-2.45 (m, 1H), 2.21-2.22 (m, 1H), 2.09-2.10 (m, 1H), 1.03 (d, J=6.4 Hz, 3H), 0.82 (d, J=6.4 Hz, 3H).

Using procedures analogous to those described for Exemplary Compound 20, Exemplary Compounds 12, 13, and 21 were prepared.

Exemplary Synthesis of Exemplary Compound 14

Step 1

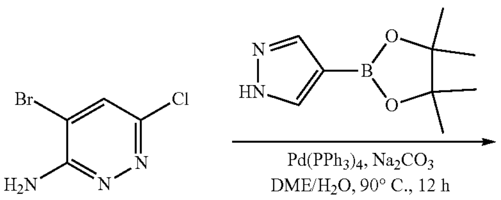

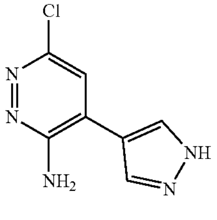

Into a 250-mL round-bottom flask, was placed a solution of 4-(tetramethyl-1,3,2-dioxaborolan-2-yl)-1H-pyrazole (1.5 g, 7.73 mmol, 1.00 equiv) in dioxane/$H_2O$ (1:1) (60 mL), 4-bromo-6-chloropyridazin-3-amine (1.7 g, 8.16 mmol, 1.20 equiv), $Pd(PPh_3)_4$ (800 mg, 0.69 mmol, 0.10 equiv), potassium carbonate (2.9 g, 20.98 mmol, 3.00 equiv). The resulting solution was stirred overnight at 100° C. in an oil bath. The residue was applied onto a silica gel column with dichloromethane/methanol (10:1). This resulted in 1.0 g (66%) of 6-chloro-4-(1H-pyrazol-4-yl)pyridazin-3-amine as a white solid.

Step 2

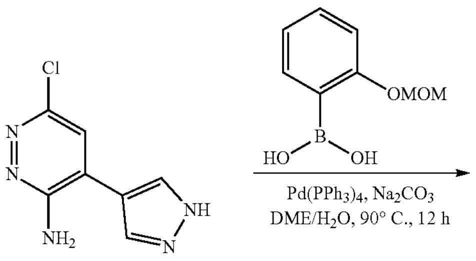

-continued

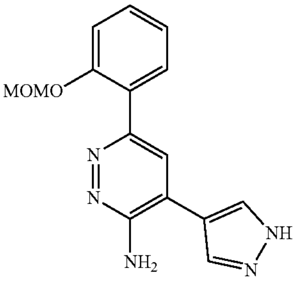

Into a 10-mL sealed tube, was placed a solution of 6-chloro-4-(1H-pyrazol-4-yl)pyridazin-3-amine (390 mg, 1.99 mmol, 1.00 equiv) in dioxane (4 mL), [2-(methoxymethoxy)phenyl]boronic acid (546 mg, 3.00 mmol, 1.50 equiv), $Pd(PPh_3)_4$ (300 mg, 0.26 mmol, 0.20 equiv), a solution of potassium carbonate (552 mg, 3.99 mmol, 2.00 equiv) in water (2 mL). The resulting solution was stirred for 12 hours at 100° C. in an oil bath. The resulting mixture was concentrated under vacuum. The residue was applied onto a silica gel column with dichloromethane/methanol (10:1). This resulted in 120 mg (20%) of 6-[2-(methoxymethoxy)phenyl]-4-(1H-pyrazol-4-yl)pyridazin-3-amine as a yellow solid.

Step 3

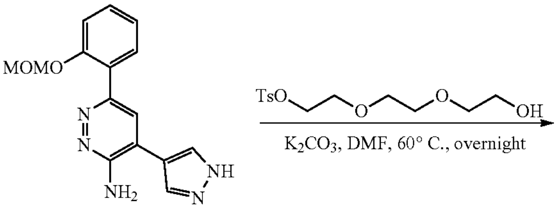

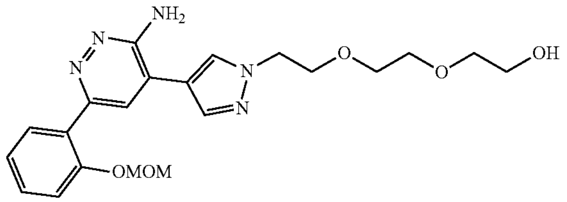

Into a 50-mL round-bottom flask, was placed a solution of 6-[2-(methoxymethoxy)phenyl]-4-(1H-pyrazol-4-yl)pyridazin-3-amine (100 mg, 0.34 mmol, 1.00 equiv) in N,N-dimethylformamide (10 mL), 2-[2-(2-[[(4-methylbenzene)sulfonyl]oxy]ethoxy)ethoxy]ethan-1-ol (100 mg, 0.33 mmol, 1.00 equiv), potassium carbonate (91 mg, 0.66 mmol, 2.00 equiv). The resulting solution was stirred for 12 hours at 70° C. in an oil bath. The resulting solution was extracted with ethyl acetate (20 mL×3) and the organic layers combined and concentrated under vacuum. The residue was applied onto a silica gel column with dichloromethane/methanol (10:1). This resulted in 100 mg (69%) of 2-[2-[2-(4-[3-amino-6-[2-(methoxymethoxy)phenyl]pyridazin-4-yl]-1H-pyrazol-1-yl)ethoxy]ethoxy]ethan-1-ol as yellow oil.

Step 4

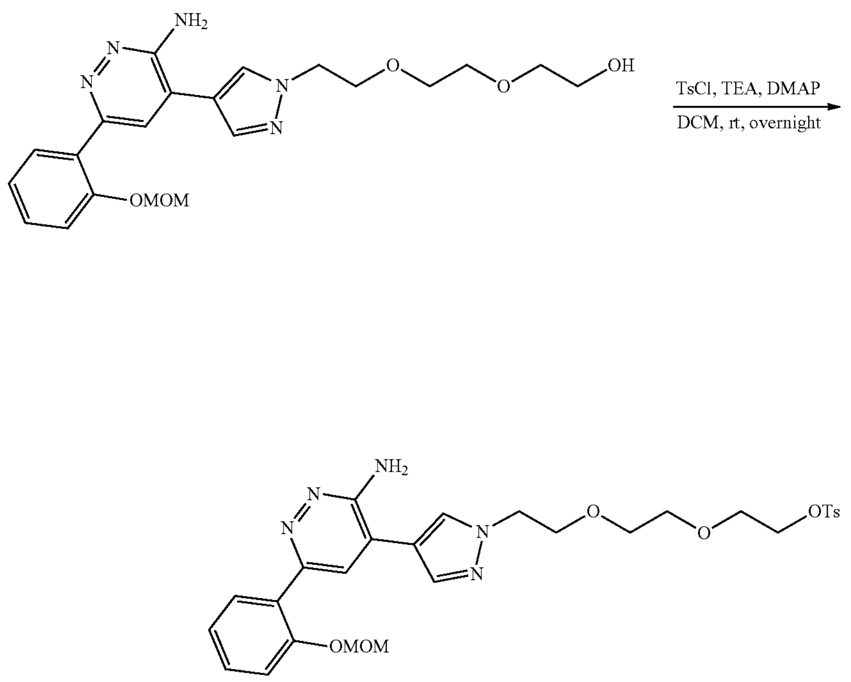

Into a 100-mL round-bottom flask, was placed a solution of 2-[2-[2-(4-[3-amino-6-[2-(methoxymethoxy)phenyl]pyridazin-4-yl]-1H-pyrazol-1-yl)ethoxy]ethoxy]ethan-1-ol (100 mg, 0.23 mmol, 1.00 equiv) in dichloromethane (20 mL), 4-toluene sulfonyl chloride (66.0 mg, 0.35 mmol, 1.50 equiv), triethylamine (47 mg, 0.46 mmol, 2.00 equiv), 4-dimethylaminopyridine (10 mg, 0.08 mmol, 0.30 equiv). The resulting solution was stirred for 16 hours at room temperature. The resulting solution was extracted with ethyl acetate (20 mL×3) and the organic layers combined and concentrated under vacuum. The residue was applied onto a silica gel column eluting with dichloromethane/methanol (10:1). This resulted in 100 mg (74%) of 2-[2-[2-(4-[3-amino-6-[2-(methoxymethoxy)phenyl]pyridazin-4-yl]-1H-pyrazol-1-yl)ethoxy]ethoxy]ethyl 4-methylbenzene-1-sulfonate as a yellow oil.

Step 5

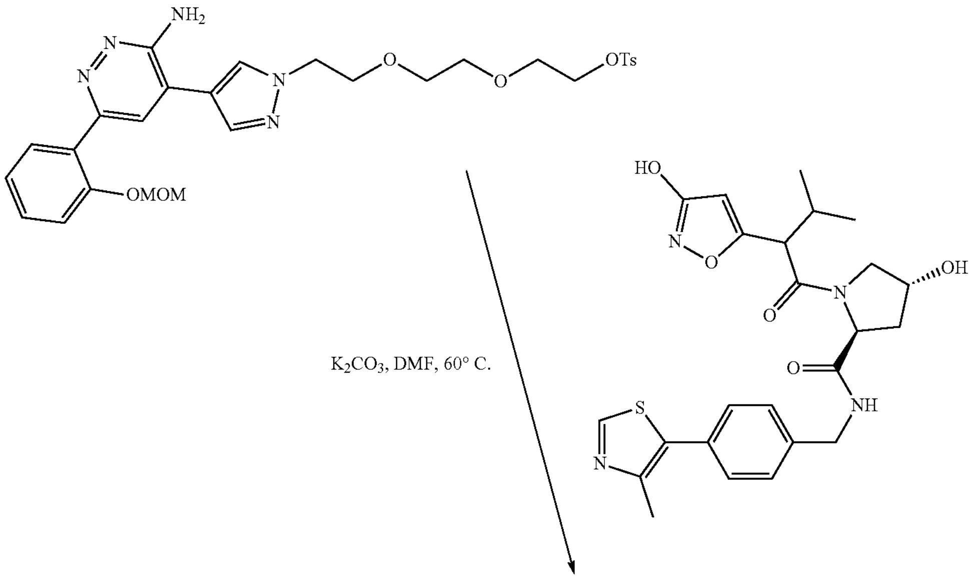

-continued

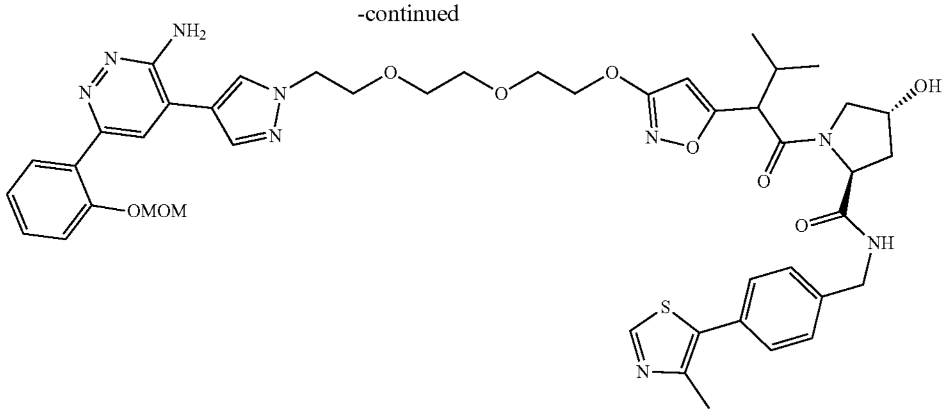

Into a 50-mL round-bottom flask, was placed a solution of 2-[2-[2-(4-[3-amino-6-[2-(methoxymethoxy)phenyl]pyridazin-4-yl]-1H-pyrazol-1-yl)ethoxy]ethoxy]ethyl 4-methylbenzene-1-sulfonate (120 mg, 0.2 mmol, 1.00 equiv) in N,N-dimethylformamide (5 mL), (2S,4R)-4-hydroxy-1-[2-(3-hydroxy-1,2-oxazol-5-yl)-3-methylbutanoyl]-N-[[4-(4-methyl-1,3-thiazol-5-yl)phenyl]methyl]pyrrolidine-2-carboxamide (130 mg, 0.2 mmol, 1.00 equiv) [prepared as described by Qian, Y. et al. in WO 2017/030814], potassium carbonate (100 mg, 0.4 mmol, 2.00 equiv). The resulting solution was stirred for 12 hours at 70° C. The resulting solution was extracted with ethyl acetate (20 mL×3), and the organic layers were combined and concentrated under vacuum. The residue was applied onto a silica gel column eluting with dichloromethane/methanol (10:1). This resulted in 90 mg of (2S,4R)-1-[2-[3-(2-[2-[2-(4-[3-amino-6-[2-(methoxymethoxy)phenyl]pyridazin-4-yl]-1H-pyrazol-1-yl)ethoxy]ethoxy]ethoxy)-1,2-oxazol-5-yl]-3-methylbutanoyl]-4-hydroxy-N-[[4-(4-methyl-1,3-thiazol-5-yl)phenyl]methyl]pyrrolidine-2-carboxamide as a colorless oil.

Step 6

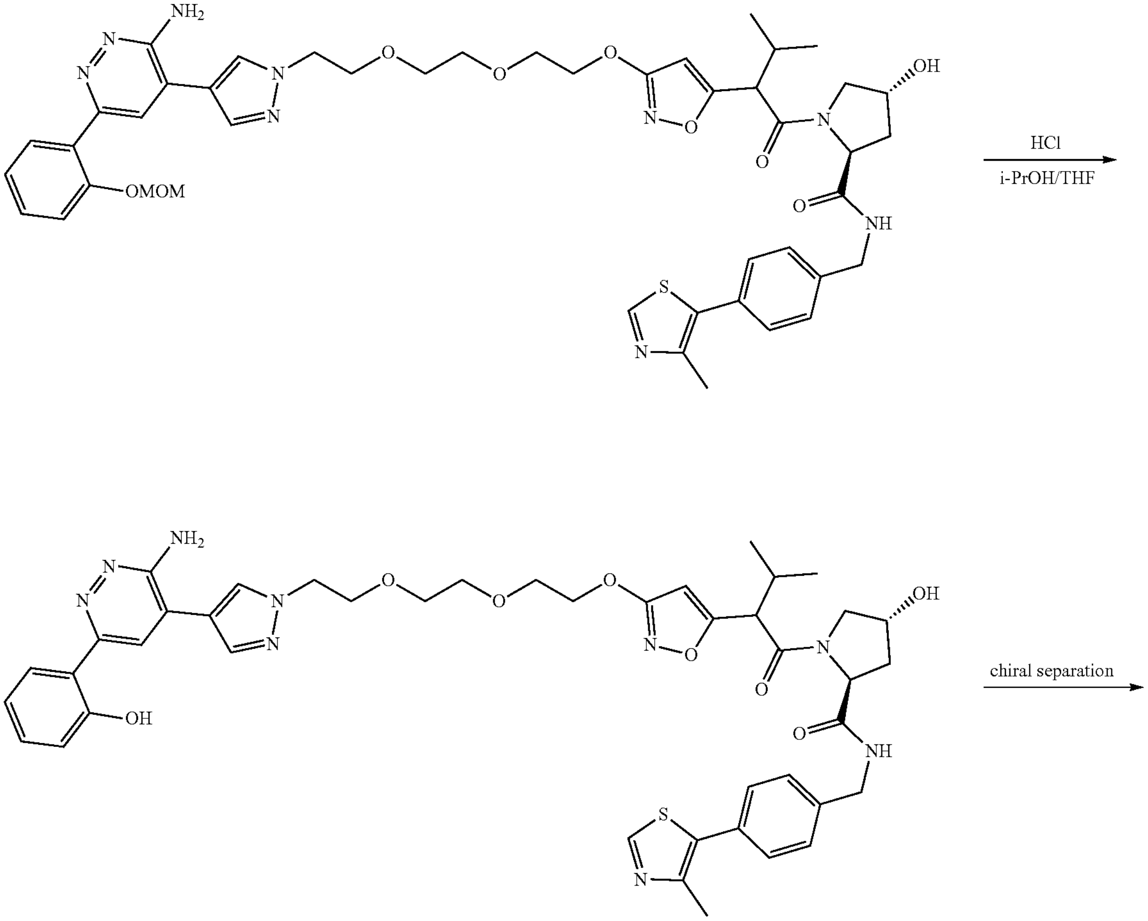

-continued

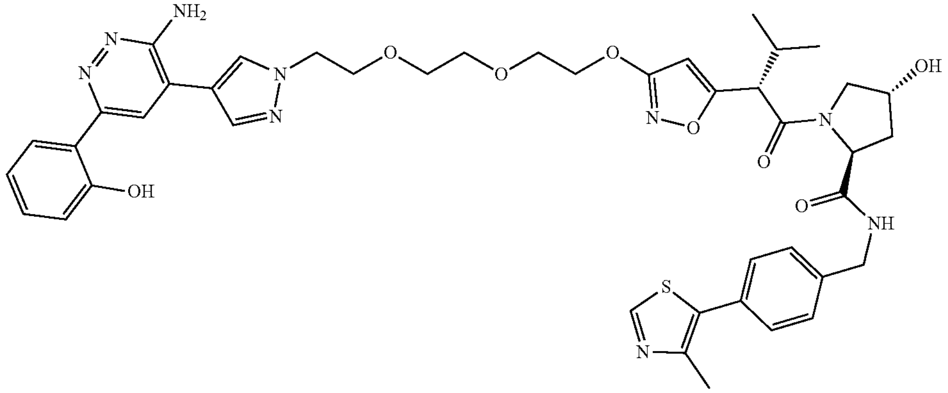

+

Exemplary Compound 14

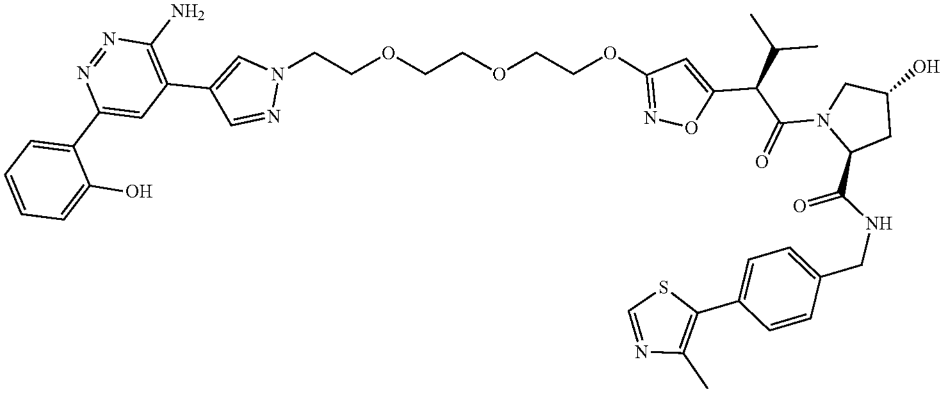

Exemplary Compound 4

Into a 50-mL round-bottom flask, was placed a solution of (2S,4R)-1-[2-[3-(2-[2-[2-(4-[3-amino-6-[2-(methoxymethoxy) phenyl]pyridazin-4-yl]-1H-pyrazol-1-yl)ethoxy]ethoxy]ethoxy)-1,2-oxazol-5-yl]-3-methylbutanoyl]-4-hydroxy-N-[[4-(4-methyl-1,3-thiazol-5-yl) phenyl]methyl]pyrrolidine-2-carboxamide (90.0 mg, 0.10 mmol, 1.00 equiv) in i-propanol (2 mL) and tetrahydrofuran (2 mL), and a solution of concentrated hydrogen chloride solution (12N, 2 mL) was added. The resulting solution was stirred for 1 hour at room temperature. The resulting mixture was concentrated under vacuum. The crude product was purified by Prep-HPLC with the following conditions: Column: XBridge C18 OBD Prep Column, 100 Å, 5 m, 19 mm×250 mm; Mobile Phase A:Water (0.1% FA), Mobile Phase B: ACN; Flow rate: 20 mL/min; Gradient: 32% B to 41% B in 8 min; 254 nm; Rt: 70 min. This resulted in 56 mg (65%) of (2S,4R)-1-[2-(3-[2-[2-(2-[4-[3-amino-6-(2-hydroxyphenyl)pyridazin-4-yl]-1H-pyrazol-1-yl]ethoxy) ethoxy]ethoxy]-1,2-oxazol-5-yl)-3-methylbutanoyl]-4-hydroxy-N-[[4-(4-methyl-1,3-thiazol-5-yl)phenyl]methyl] pyrrolidine-2-carboxamide as a white solid.

The product was purified by Chiral-Prep-HPLC with the following conditions: Column, CHIRAL ART Cellulose-SB, 2*25 cm, 5 um; mobile phase, Hex—HPLC and ethanol—HPLC (hold 50% ethanol—HPLC in 24 min); Detector, UV 220/254 nm. This resulted in 17.8 mg (34%) of (2S,4R)-1-[(2S)-2-(3-[2-[2-(2-[4-[3-amino-6-(2-hydroxyphenyl) pyridazin-4-yl]-1H-pyrazol-1-yl]ethoxy)ethoxy]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide as a white solid[$^1$H NMR (300 MHz, $CD_3OD$): δ 8.82 (d, J=11.1 Hz, 1H), 8.29-8.18 (m, 1H), 8.11-7.89 (m, 2H), 7.80 (d, J=8.2 Hz, 1H), 7.48-7.41 (m, 1H), 7.37-7.30 (m, 3H), 7.30-7.19 (m, 1H), 6.95-6.83 (m, 2H), 5.89 (s, 1H), 4.59-4.41 (m, 2H), 4.40-4.30 (m, 4H), 4.27-4.11 (m, 2H), 3.86 (q, J=5.3 Hz, 2H), 3.75-3.59 (m, 6H), 3.56 (s, 3H), 2.42 (d, J=5.0 Hz, 3H), 2.36-2.10 (m, 2H), 2.04-2.01 (m, J=13.1, 8.1, 4.7 Hz, 1H), 1.26 (s, 1H), 0.99 (d, J=6.6 Hz, 3H), 0.83 (d, J=6.8 Hz, 3H)] and 24.4 mg (47%) of (2S,4R)-1-[(2R)-2-(3-[2-[2-(2-[4-[3-amino-6-(2-hydroxyphenyl)pyridazin-4-yl]-1H-pyrazol-1-yl]ethoxy)ethoxy]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide [1H NMR (300 MHz, $CD_3OD$): δ 8.82 (d, J=6.6 Hz, 1H), 8.26 (dd, J=3.1, 0.8 Hz, 1H), 8.10-7.96 (m, 2H), 7.86-7.75 (m, 1H), 7.45-7.30 (m, 4H), 7.25-7.22 (m, 1H), 6.96-6.84 (m, 2H), 5.88 (s, 1H), 4.70-4.42 (m, 3H), 4.41-4.33 (m, 3H), 4.28-4.17 (m, 2H), 3.87 (t, J=5.0 Hz, 3H), 3.85-3.63 (m, 2H), 3.59-3.57 (m, 6H), 2.41 (d, J=12.2 Hz, 3H), 2.38-2.33 (m, 1H), 2.25-2.12 (m, 1H), 2.06-2.02 (m, 1H), 1.26 (s, 1H), 0.97 (dd, J=6.6, 1.8 Hz, 3H), 0.80 (dd, J=6.6, 1.8 Hz, 3H)] as a white solid.

Exemplary Compounds 16, 17, 18, and 19 were prepared using procedures described above for Exemplary Compound 14 and Exemplary Compound 15.

Exemplary Synthesis of Exemplary Compound 22

Step 1

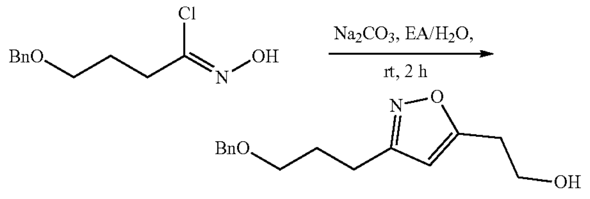

Into a 250-mL round-bottom flask, was placed (Z)-4-(benzyloxy)-N-hydroxybutcarbonimidoyl chloride (8.7 g, 38.21 mmol, 1.00 equiv), but-3-yn-1-ol (3.3 g, 47.08 mmol, 1.23 equiv), ethyl acetate (70 mL), water (70 mL), sodium bicarbonate (4.0 g, 47.61 mmol, 1.25 equiv). The resulting solution was stirred for 2 hours at 25° C. The resulting solution was extracted with ethyl acetate and washed with saturated sodium chloride aqueous solution. The mixture was dried over anhydrous sodium sulfate and concentrated under vacuum. The residue was applied onto a silica gel column eluting with ethyl acetate/petroleum ether (1:1). This resulted in 5.9 g (59%) of 2-[3-[3-(benzyloxy)propyl]-1,2-oxazol-5-yl]ethan-1-ol as a yellow oil.

Step 2

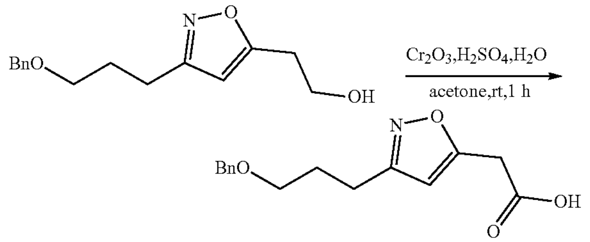

Into a 100-mL round-bottom flask, was placed 2-[3-[3-(benzyloxy)propyl]-1,2-oxazol-5-yl]ethan-1-ol (550.0 mg, 2.10 mmol, 1.00 equiv), acetone (30 mL), $Cr_2O_3$ (100.0 mg), sulfuric acid (0.25 mL), water (1 mL). The resulting solution was stirred for 1 hour at 25° C. The resulting solution was diluted with water. The resulting solution was extracted with ethyl acetate and washed with saturated sodium chloride aqueous solution. The mixture was dried over anhydrous sodium sulfate and concentrated under vacuum. This resulted in 420 mg (72%) of 2-[3-[3-(benzyloxy)propyl]-1,2-oxazol-5-yl]acetic acid as a yellow oil.

Step 3

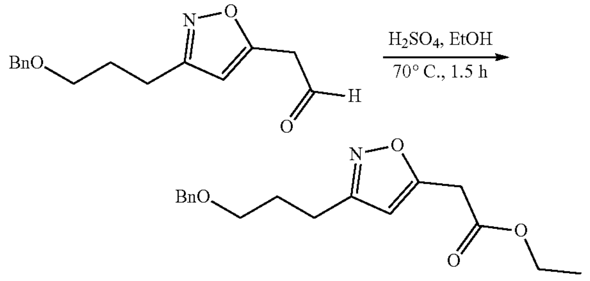

Into a 250-mL round-bottom flask, was placed ethyl 2-[3-[3-(benzyloxy)propyl]-1,2-oxazol-5-yl]acetate (8.0 g, 26.37 mmol, 1.00 equiv), ethanol (50 mL), sulfuric acid (0.1 mL). The resulting solution was stirred for 1.5 hours at 70° C. The resulting mixture was concentrated under vacuum. The crude product was purified by Flash-Prep-HPLC with the following conditions: Column, C18 silica gel; mobile phase, acetonitrile:water=0:100 increasing to acetonitrile: water=60:40 within 49 min; Detector, UV 220 nm. This resulted in 4.5 g (56%) of ethyl 2-[3-[3-(benzyloxy)propyl]-1,2-oxazol-5-yl]acetate as a light yellow oil.

Step 4

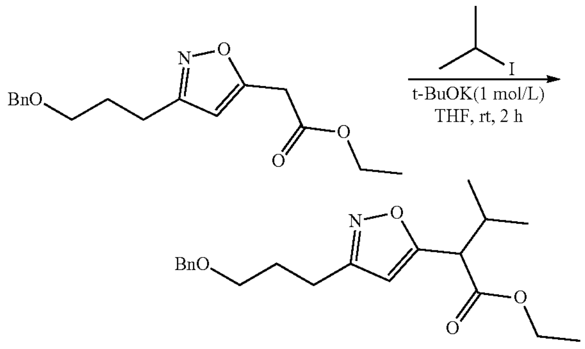

Into a 250-mL 3-necked round-bottom flask purged and maintained with an inert atmosphere of nitrogen, was placed ethyl 2-[3-[3-(benzyloxy)propyl]-1,2-oxazol-5-yl]acetate (4.5 g, 14.83 mmol, 1.00 equiv) and tetrahydrofuran (70 mL). This was followed by the addition of a solution of t-BuOK (2.0 g, 17.82 mmol, 1.20 equiv) in tetrahydrofuran (17.8 mL) dropwise with stirring at 0° C. in 20 minutes. To this was added 2-iodopropane (3.01 g, 17.71 mmol, 1.19 equiv) dropwise with stirring at 0° C. in 2 minutes. The resulting solution was stirred for 2 hours at 25° C. The reaction was then quenched by the water. The resulting solution was extracted with ethyl acetate and washed with saturated sodium chloride aqueous solution. The mixture was dried over anhydrous sodium sulfate and concentrated under vacuum. This resulted in 4.3 g (84%) of ethyl 2-[3-[3-(benzyloxy)propyl]-1,2-oxazol-5-yl]-3-methylbutanoate as an orange oil.

Step 5

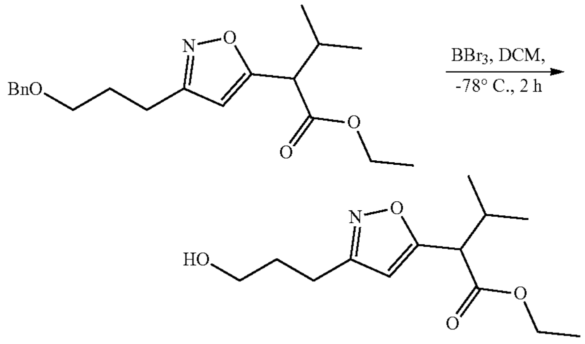

Into a 250-mL 3-necked round-bottom flask purged and maintained with an inert atmosphere of nitrogen, was placed ethyl 2-[3-[3-(benzyloxy)propyl]-1,2-oxazol-5-yl]-3-methylbutanoate (4.2 g, 12.16 mmol, 1.00 equiv) and dichloromethane (100 mL). This was followed by the addition of a solution of $BBr_3$ (5.17 g, 20.64 mmol, 1.70 equiv) in dichloromethane (20.7 mL) dropwise with stirring at −78° C. in 30 minutes. The resulting solution was stirred for 2 hours at −78° C. The reaction was then quenched. The resulting solution was extracted with dichloromethane and washed with saturated sodium chloride aqueous solution. The mixture was dried over anhydrous sodium sulfate and concentrated under vacuum. The crude product was purified by Flash-Prep-HPLC with the following conditions: Column, C18 silica gel; mobile phase, acetonitrile:water=0:100 increasing to acetonitrile:water=23:76 within 25 min; Detector, UV 220 nm. This resulted in 2.6 g (84%) of ethyl 2-[3-(3-hydroxypropyl)-1,2-oxazol-5-yl]-3-methylbutanoate as an orange oil.

Step 6

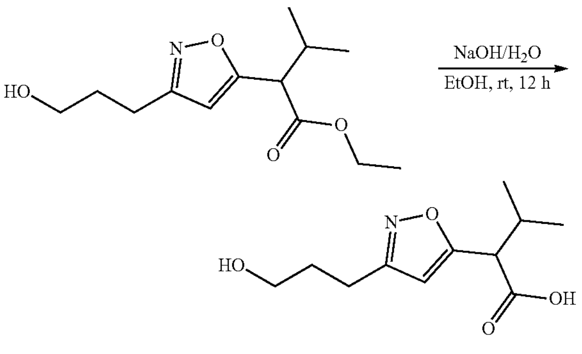

Into a 100-mL round-bottom flask, was placed ethyl 2-[3-(3-hydroxypropyl)-1,2-oxazol-5-yl]-3-methylbutanoate (1.2 g, 4.70 mmol, 1.00 equiv), ethanol (20 mL), water (10 mL), sodium hydroxide (1.9 g, 47.50 mmol, 10.0 equiv). The resulting solution was stirred for 1 overnight at room temperature. The pH value of the solution was adjusted to 6 with hydrogen chloride (2M). The resulting solution was extracted with ethyl acetate and washed with saturated sodium chloride. The mixture was dried over anhydrous sodium sulfate and concentrated under vacuum. This resulted in 800 mg (75%) of 2-[3-(3-hydroxypropyl)-1,2-oxazol-5-yl]-3-methylbutanoic acid as a yellow oil.

Step 7

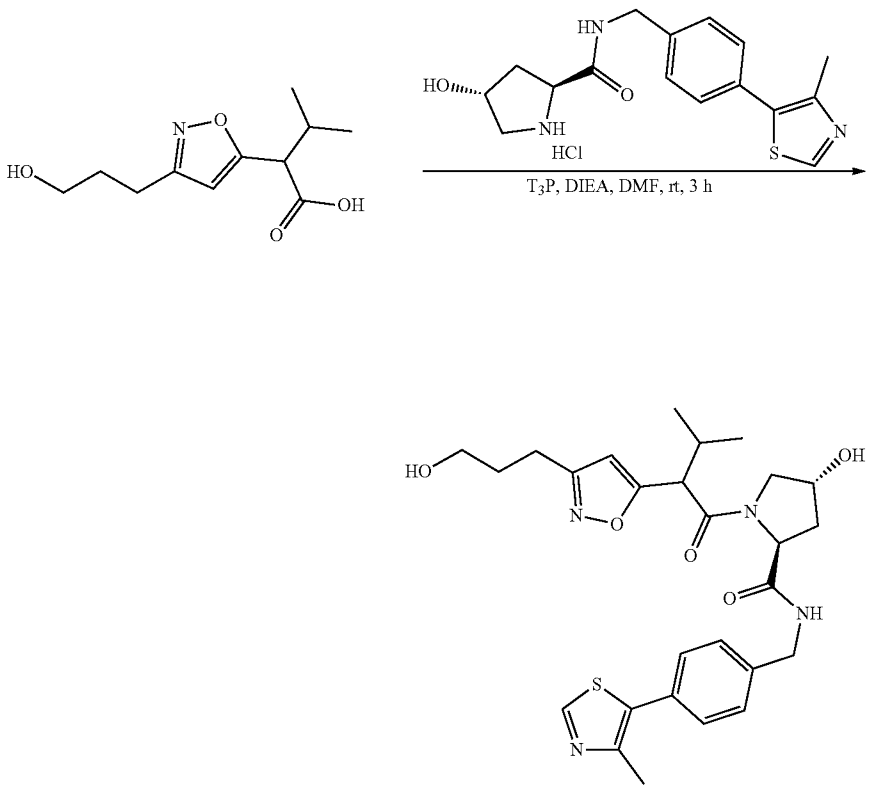

Into a 100-mL round-bottom flask, was placed 2-[3-(3-hydroxypropyl)-1,2-oxazol-5-yl]-3-methylbutanoic acid (800 mg, 3.52 mmol, 1.00 equiv), (2S,4R)-4-hydroxy-N-[[4-(4-methyl-1,3-thiazol-5-yl)phenyl]methyl]pyrrolidine-2-carboxamide hydrochloride (1.24 g, 3.50 mmol, 1.00 equiv), N,N-dimethylformamide (15 mL), N-ethyl-N-isopropylpropan-2-amine (1.82 g, 14.08 mmol, 4.00 equiv), $T_3P$ (1.77 g, 1.20 equiv). The resulting solution was stirred for 2 hours at room temperature. The reaction was then quenched by water. The resulting solution was extracted with ethyl acetate and washed with saturated sodium chloride. The mixture was dried over anhydrous sodium sulfate and concentrated under vacuum. The residue was applied onto a silica gel column eluting with dichloromethane/methanol (5:1). The collected fractions were combined and concentrated under vacuum. This resulted in 870 mg (53%) of (2S,4R)-4-hydroxy-1-[[3-(3-hydroxypropyl)-1,2-oxazol-5-yl]carbonyl]-N-[[4-(4-methyl-1,3-thiazol-5-yl)phenyl]methyl]pyrrolidine-2-carboxamide as a yellow solid.

Step 8

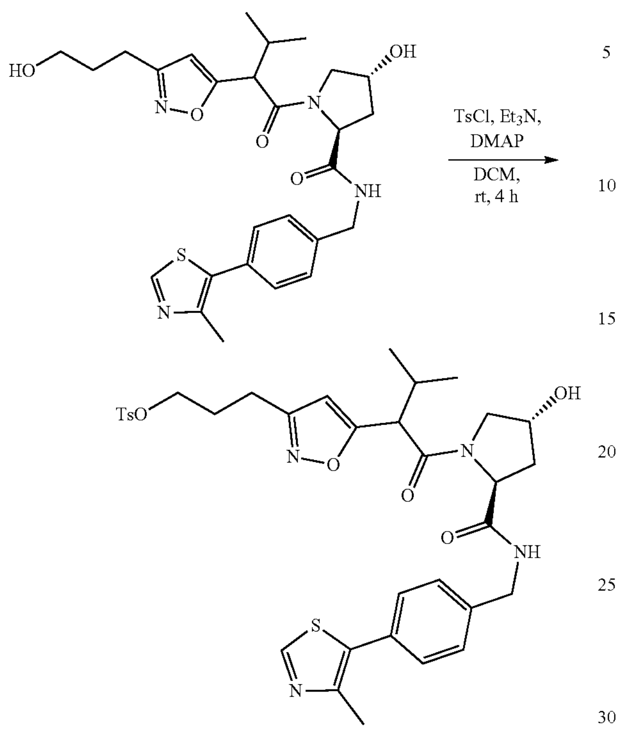

Into a 50-mL round-bottom flask, was placed (2S,4R)-4-hydroxy-1-[2-[3-(3-hydroxypropyl)-1,2-oxazol-5-yl]-3-methylbutanoyl]-N-[[4-(4-methyl-1,3-thiazol-5-yl)phenyl]methyl]pyrrolidine-2-carboxamide (870 mg, 1.65 mmol, 1.00 equiv), dichloromethane (10 mL), 4-methylbenzene-1-sulfonyl chloride (377 mg, 1.98 mmol, 1.20 equiv), triethylamine (334.0 mg, 3.30 mmol, 2.00 equiv), 4-dimethylaminopyridine (40 mg, 0.33 mmol, 0.20 equiv). The resulting solution was stirred for 4 hours at room temperature. The resulting solution was extracted with dichloromethane and washed with water and saturated sodium chloride. The mixture was dried over anhydrous sodium sulfate and concentrated under vacuum. The residue was applied onto a silica gel column eluting with dichloromethane/methanol (10:1). The collected fractions were combined and concentrated under vacuum. This resulted in 600 mg (53%) of 3-(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)propyl 4-methylbenzene-1-sulfonate as a yellow solid.

Step 9

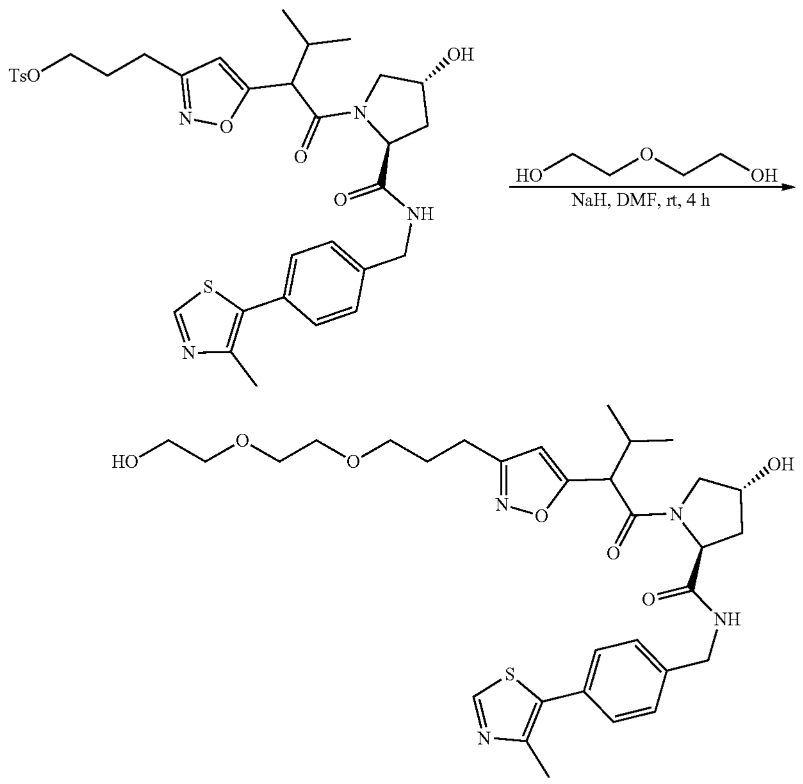

Into a 50-mL round-bottom flask, was placed 2-(2-hydroxyethoxy)ethan-1-ol (273.0 mg, 2.57 mmol, 5.00 equiv) and N,N-dimethylformamide (5 mL). Sodium hydride (41.0 mg, 1.71 mmol, 2.00 equiv) added under 0° C., followed by the addition, after 20 minutes, of 3-(5-[1-[(4S)-4-hydroxy-1-([[4-(4-methyl-1,3-thiazol-5-yl)phenyl]methyl]carbamoyl)pyrrolidin-2-yl]-3-methyl-1-oxobutan-2-yl]-1,2-oxazol-3-yl)propyl 4-methylbenzene-1-sulfonate (350.0 mg, 0.51 mmol, 1.00 equiv). The resulting solution was stirred for 4 hours at room temperature. Reaction mixture was diluted with water and extracted with DCM. Organic phase was dried over sodium sulfate and concentrated, and the residue was subjected to flash chromatography. This resulted in 160 mg (51%) of (4S)-4-hydroxy-2-[2-(3-[3-[2-(2-hydroxyethoxy)ethoxy]propyl]-1,2-oxazol-5-yl)-3-methylbutanoyl]-N-[[4-(4-methyl-1,3-thiazol-5-yl)phenyl]methyl] pyrrolidine-1-carboxamide as a yellow oil.

Step 10

Into a 50-mL round-bottom flask, was placed (2S,4R)-4-hydroxy-1-[2-(3-[3-[2-(2-hydroxyethoxy)ethoxy]propyl]-1,2-oxazol-5-yl)-3-methylbutanoyl]-N-[[4-(4-methyl-1,3-thiazol-5-yl)phenyl]methyl]pyrrolidine-2-carboxamide (160 mg, 0.26 mmol, 1.00 equiv), dichloromethane (5 mL), 4-methylbenzene-1-sulfonyl chloride (59 mg, 0.31 mmol, 1.20 equiv), triethylamine (53 mg, 0.52 mmol, 2.00 equiv), 4-dimethylaminopyridine (6 mg, 0.05 mmol, 0.20 equiv). The resulting solution was stirred for 5 hours at room temperature. The resulting solution was extracted with dichloromethane and washed with water. The mixture was dried over anhydrous sodium sulfate and concentrated under vacuum. The residue was applied onto a silica gel column eluting with dichloromethane/methanol (12:1). The collected fractions were combined and concentrated under

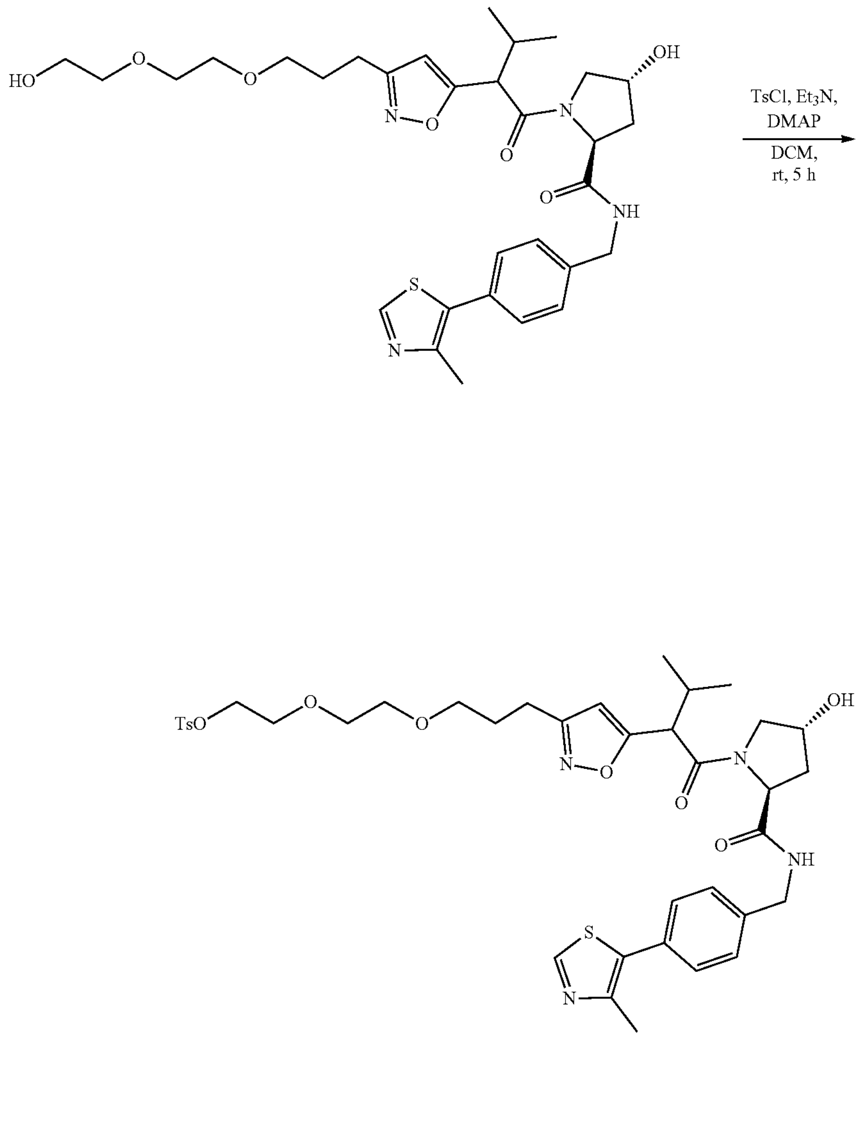

vacuum. This resulted in 72 mg (36%) of 2-[2-[3-(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)propoxy]ethoxy]ethyl 4-methylbenzene-1-sulfonate as a yellow oil.

Step 11

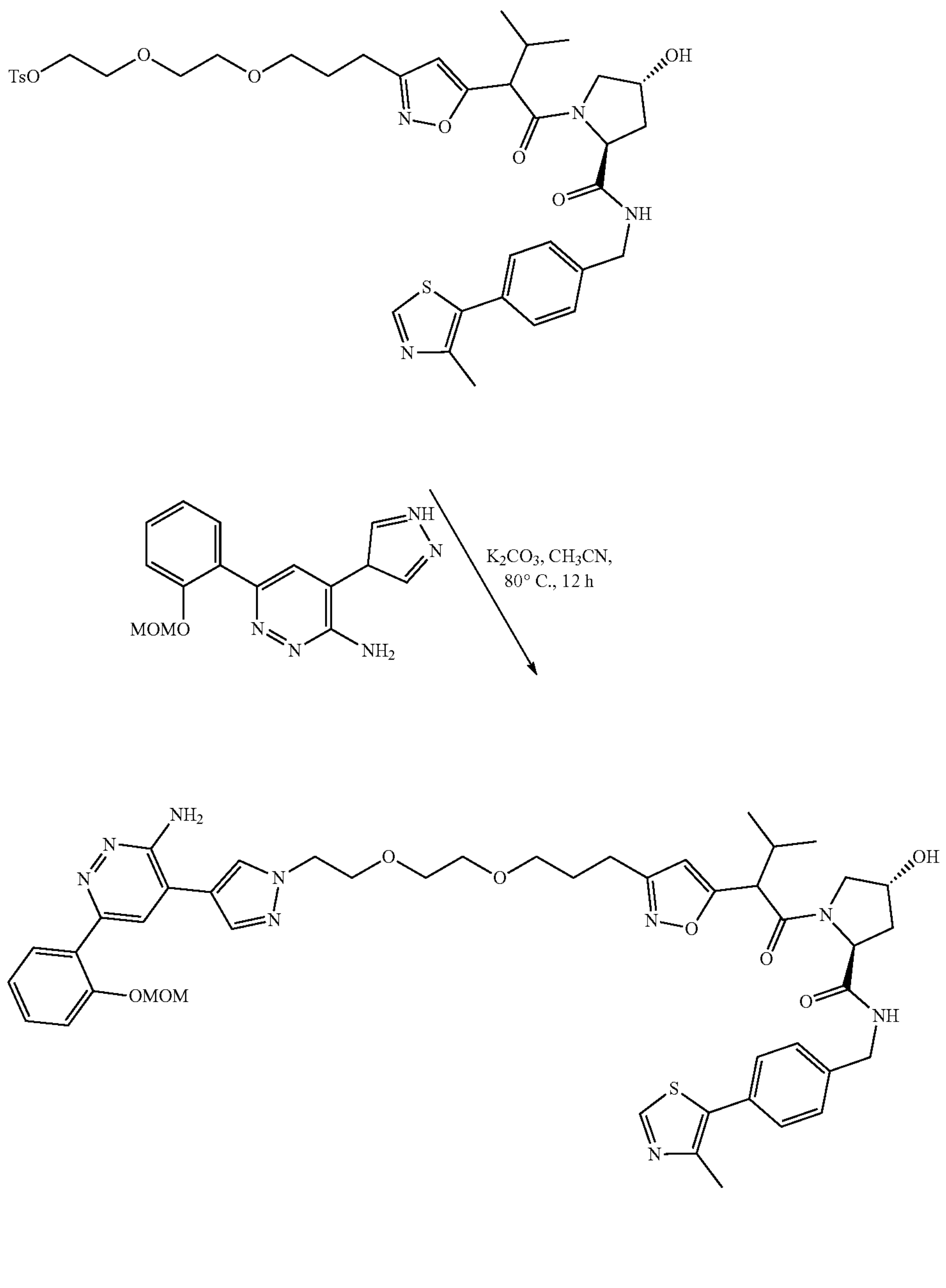

Into a 50-mL round-bottom flask, was placed 2-[2-[3-(5-[1-[(2S,4R)-4-hydroxy-2-([[4-(4-methyl-1,3-thiazol-5-yl)phenyl]methyl]carbamoyl)pyrrolidin-1-yl]-3-methyl-1-oxobutan-2-yl]-1,2-oxazol-3-yl)propoxy]ethoxy]ethyl 4-methylbenzene-1-sulfonate (70 mg, 0.09 mmol, 1.00 equiv), 6-[2-(methoxymethoxy)phenyl]-4-(1H-pyrazol-4-yl)pyridazin-3-amine (27 mg, 0.09 mmol, 1.00 equiv), acetonitrile (2 mL), potassium carbonate (38 mg, 0.27 mmol, 3.00 equiv). The resulting solution was stirred for 1 overnight at 80° C. The resulting solution was extracted with ethyl acetate and washed with water. The mixture was dried over anhydrous sodium sulfate and concentrated under vacuum. The residue was applied onto a silica gel column with dichloromethane/methanol (10:1). The collected fractions were combined and concentrated under vacuum. This resulted in 30 mg (37%) of (2S,4R)-1-[2-[3-(3-[2-[2-(4-[3-amino-6-[2-(methoxymethoxy)phenyl]pyridazin-4-yl]-1H-pyrazol-1-yl)ethoxy]ethoxy]propyl)-1,2-oxazol-5-yl]-3-methylbutanoyl]-4-hydroxy-N-[[4-(4-methyl-1,3-thiazol-5-yl)phenyl]methyl]pyrrolidine-2-carboxamide as a yellow oil.

Step 12

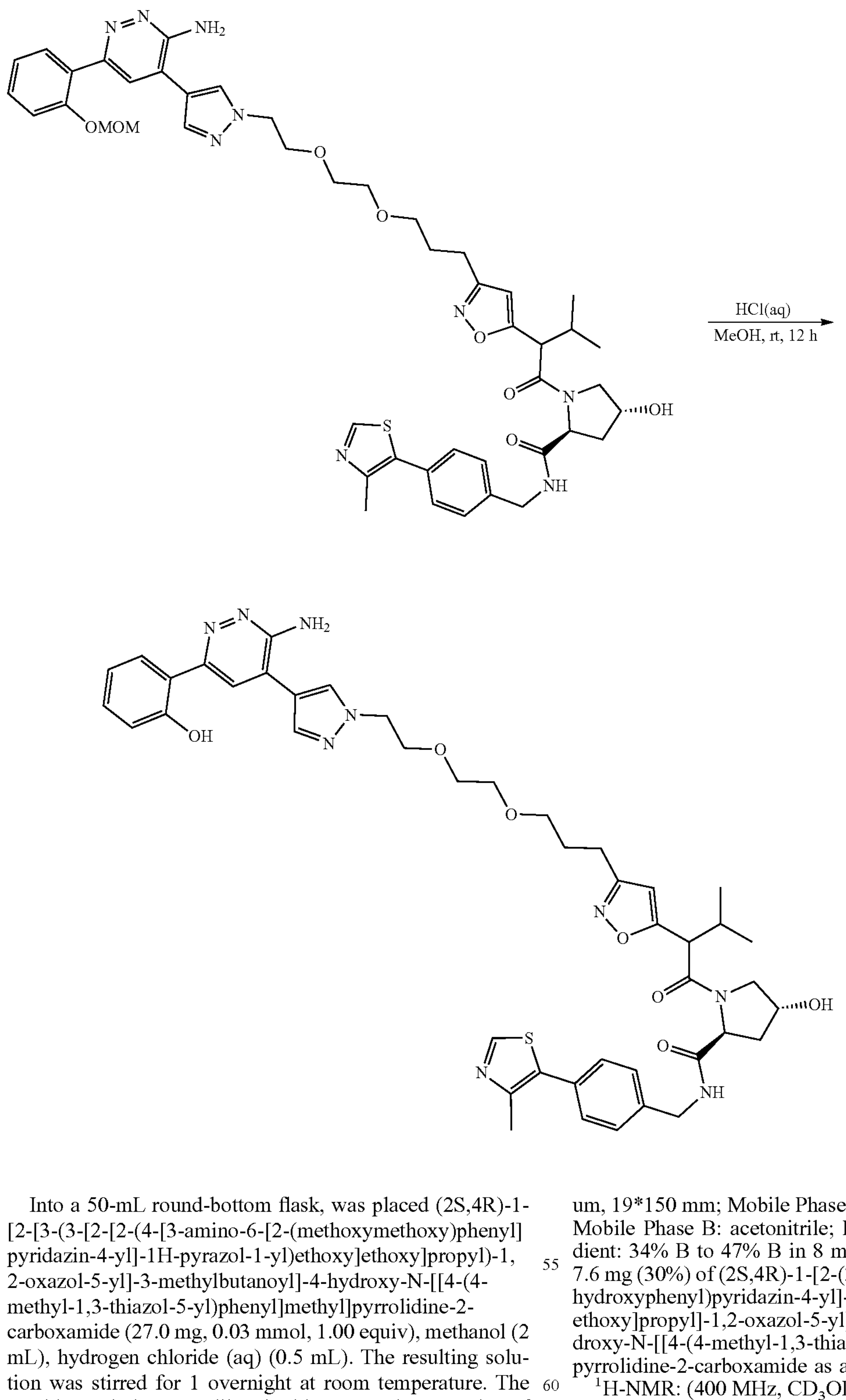

Into a 50-mL round-bottom flask, was placed (2S,4R)-1-[2-[3-(3-[2-[2-(4-[3-amino-6-[2-(methoxymethoxy)phenyl]pyridazin-4-yl]-1H-pyrazol-1-yl)ethoxy]ethoxy]propyl)-1,2-oxazol-5-yl]-3-methylbutanoyl]-4-hydroxy-N-[[4-(4-methyl-1,3-thiazol-5-yl)phenyl]methyl]pyrrolidine-2-carboxamide (27.0 mg, 0.03 mmol, 1.00 equiv), methanol (2 mL), hydrogen chloride (aq) (0.5 mL). The resulting solution was stirred for 1 overnight at room temperature. The resulting solution was diluted with water. The pH value of the solution was adjusted to 8 with sodium carbonate. The resulting solution was extracted with ethyl acetate and washed with water. The mixture was dried over anhydrous sodium sulfate and concentrated under vacuum. The crude product was purified by Prep-HPLC with the following conditions: Column: XBridge Shield RP18 OBD Column, 5 um, 19*150 mm; Mobile Phase A: Water (0.05% $NH_3H_2O$), Mobile Phase B: acetonitrile; Flow rate: 20 mL/min; Gradient: 34% B to 47% B in 8 min; 220 nm. This resulted in 7.6 mg (30%) of (2S,4R)-1-[2-(3-[3-[2-(2-[4-[3-amino-6-(2-hydroxyphenyl)pyridazin-4-yl]-1H-pyrazol-1-yl]ethoxy)ethoxy]propyl]-1,2-oxazol-5-yl)-3-methylbutanoyl]-4-hydroxy-N-[[4-(4-methyl-1,3-thiazol-5-yl)phenyl]methyl]pyrrolidine-2-carboxamide as a white solid.

$^1$H-NMR: (400 MHz, $CD_3OD$) δ8.89-8.83 (m, 1H), 8.31-8.26 (m, 1H), 8.08-8.03 (m, 2H), 7.85-7.81 (m, 1H), 7.46-7.21 (m, 5H), 6.96-6.87 (m, 2H), 6.15 (s, 1H), 4.52-4.44 (m, 5H), 4.41-4.31 (m, 3H), 3.91-3.80 (m, 2H), 3.72-3.65 (m, 1H), 3.61-3.35 (m, 6H), 2.62-2.51 (m, 2H), 2.45-2.33 (m, 3H), 2.22-2.15 (m, 1H), 2.10-2.01 (m, 1H), 1.84-1.72 (m, 2H), 1.30-1.24 (m, 1H), 1.03-0.97 (m, 3H), 0.91-0.75 (m, 3H).

Exemplary Synthesis of Exemplary Compound 23 and Exemplary Compound 24
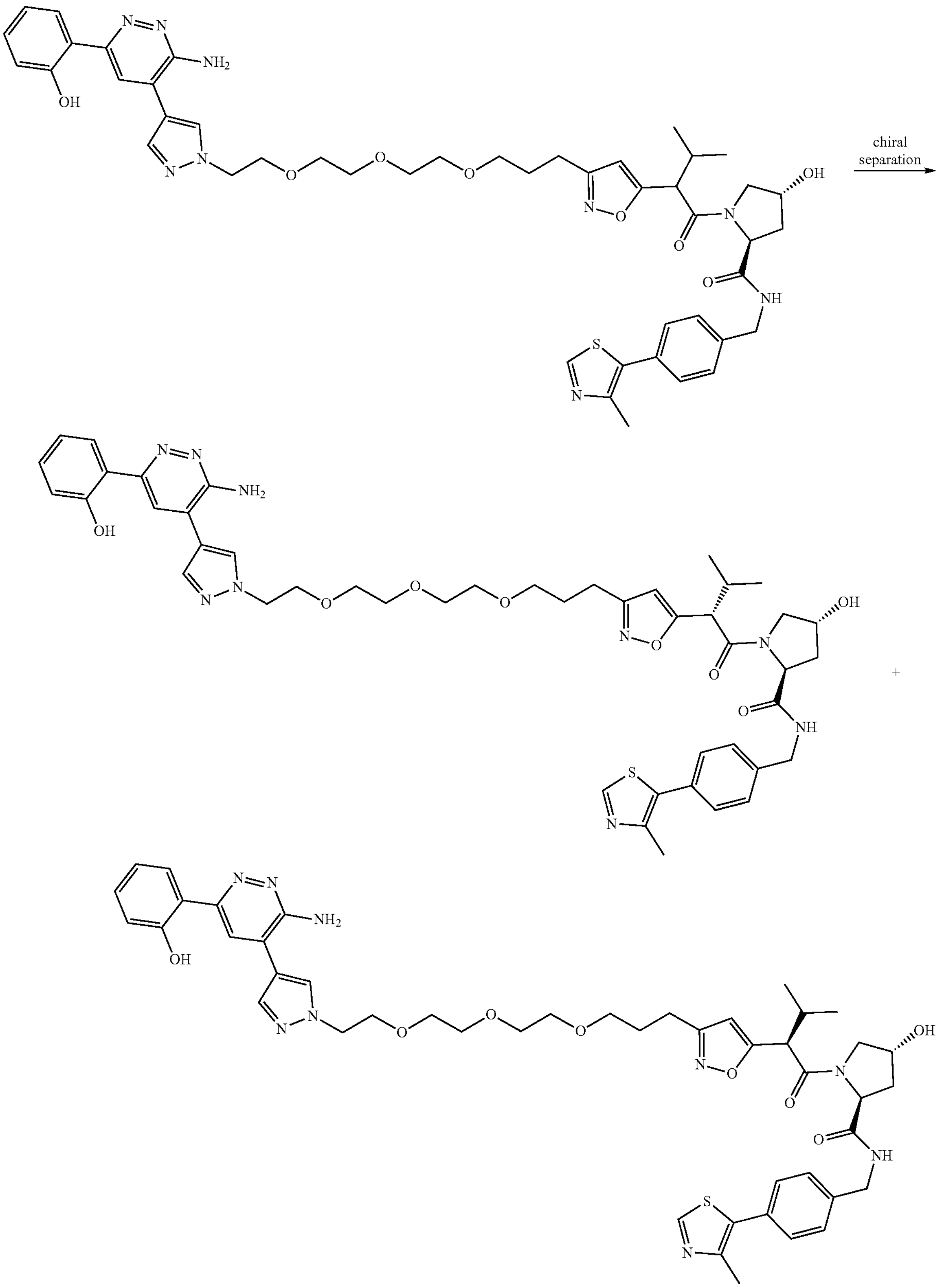

Into a 25-mL round-bottom flask, was placed (2S,4R)-1-[2-[3-(3-[2-[2-(2-[4-[3-amino-6-(2-hydroxyphenyl)pyridazin-4-yl]-1H-pyrazol-1-yl]ethoxy)ethoxy]ethoxy]propyl)-1,2-oxazol-5-yl]-3-methylbutanoyl]-4-hydroxy-N-[[4-(4-methyl-1,3-thiazol-5-yl)phenyl]methyl]pyrrolidine-2-carboxamide (87 mg, 0.10 mmol, 1.00 equiv) [prepared as described for Exemplary Compound 22] and methanol (10 mL). The resulting solution was stirred for 1 hour at 25° C. The crude product was purified by Chiral-Prep-HPLC with the following conditions: Column, CHIRALPAK ID-3; mobile phase, MtBE (0.1% DEA):EtOH=80:20, Size: 0.46*10 cm; 3 um; Detector, UV-254 nm. This resulted in 17 mg (20%) of (2S,4R)-1-[(2S)-2-[3-(3-[2-[2-(2-[4-[3-amino-6-(2-hydroxyphenyl)pyridazin-4- yl]-1H-pyrazol-1-yl]ethoxy)ethoxy]ethoxy]propyl)-1,2-oxazol-5-yl]-3-methylbutanoyl]-4-hydroxy-N-[[4-(4-methyl-1,3-thiazol-5-yl)phenyl]methyl]pyrrolidine-2-carboxamide as an off-white solid[$^1$H NMR (300 MHz, CD3OD, ppm): δ 8.83 (s, 1H), 8.33 (s, 1H), 8.23 (s, 1H), 7.99 (s, 1H), 7.70-7.67 (d, J=9 Hz, 1H), 7.48-7.45 (d, J=9 Hz, 1H), 7.37-7.32 (m, 4H), 7.00-6.97 (m, 2H), 6.19 (s, 1H), 4.61-4.58 (m, 1H), 4.50-4.38 (m, 5H), 3.91-3.86 (m, 3H), 3.60-3.51 (m, 8H), 3.50-3.43 (m, 2H), 3.40-3.34 (m, 2H), 2.57-2.52 (m, 2H), 2.46-2.43 (m, 4H), 2.30-2.23 (m, 1H), 2.10-2.04 (m, 1H), 1.73-1.69 (m, 2H), 1.07-1.05 (d, J=6.6 Hz, 3H), 0.88-0.86 (d, J=6.9 Hz, 3H)] and 21 mg (24%) of (2S,4R)-1-[(2R)-2-[3-(3-[2-[2-(2-[4-[3-amino-6-(2-hydroxyphenyl)pyridazin-4- yl]-1H-pyrazol-1-yl]ethoxy)ethoxy]ethoxy]propyl)-1,2-oxazol-5-yl]-3-methylbutanoyl]-4-hydroxy-N-[[4-(4-methyl-1,3-thiazol-5-yl)phenyl]methyl]pyrrolidine-2-carboxamide as a white solid [$^1$H NMR (300 MHz, CD3OD, ppm): δ 8.88 (s, 1H), 8.37 (s, 1H), 8.31 (s, 1H), 8.04 (s, 1H), 7.69-7.67 (d, J=8.1 Hz, ppm), 7.43-7.39 (m, 5H), 7.03-6.99 (m, 2H), 6.21-6.00 (m, 1H), 4.53-4.48 (m, 3H), 4.44-4.40 (m, 3H), 3.92-3.89 (m, 3H), 3.79-3.76 (m, 1H), 3.62-3.54 (m, 7H), 3.50-3.48 (m, 2H), 3.42-3.40 (m, 2H), 2.64-2.61 (m, 2H), 2.46-2.44 (m, 4H), 2.26-2.18 (m, 1H), 2.13-2.04 (m, 1H), 1.82-1.78 (m, 2H), 1.05-1.02 (d, J=6.6 Hz, 3H), 0.85-0.82 (d, J=6.9 Hz, 3H).

Exemplary Compounds 25 and 26 were prepared using procedures analogous to those described above for Exemplary Compounds 22, 23 and 24.

Exemplary Synthesis of Exemplary Compound 27

Step 1

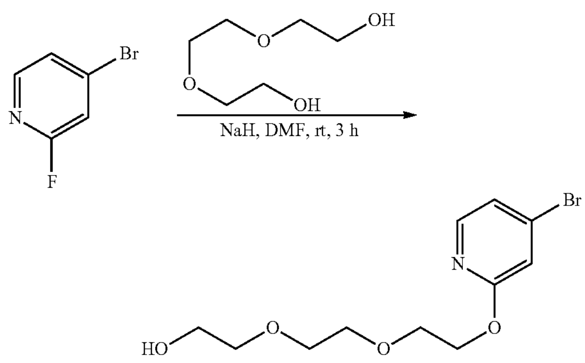

Into a 50 mL round-bottom flask, was placed 2-[2-(2-hydroxyethoxy)ethoxy]ethan-1-ol (257 mg, 1.71 mmol, 3.00 equiv) and N,N-dimethylformamide (5 mL). This was followed by the addition of sodium hydride (34 mg, 1.42 mmol, 1.50 equiv) at 0° C. in 10 minutes. To this was added 4-bromo-2-fluoropyridine (100 mg, 0.57 mmol, 1.00 equiv). The resulting solution was stirred for 3 hours at room temperature. The reaction was then quenched by the addition of 5 mL of water/ice. The resulting solution was extracted with ethyl acetate, and the organic layers were combined. The resulting mixture was washed with saturate sodium chloride. The mixture was dried over anhydrous sodium sulfate. The residue was applied onto a silica gel column with ethyl acetate/petroleum ether (1:1). The collected fractions were combined and concentrated under vacuum. This resulted in 90 mg (52%) of 2-(2-[2-[(4-bromopyridin-2-yl)oxy]ethoxy]ethoxy)ethan-1-ol as a light yellow liquid.

Step 2

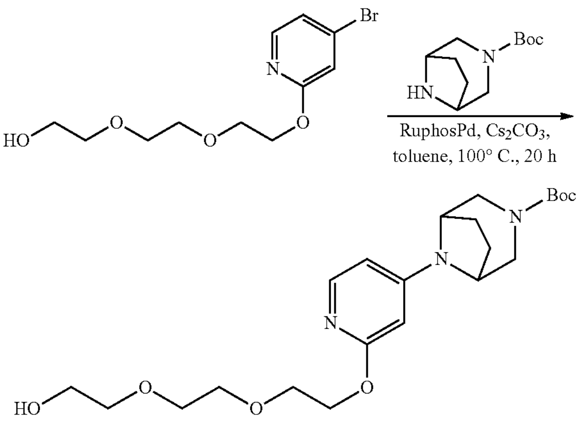

Into a 50 mL round-bottom flask purged and maintained with an inert atmosphere of nitrogen, was placed 2-(2-[2-[(4-bromopyridin-2-yl)oxy]ethoxy]ethoxy)ethan-1-ol (500 mg, 1.63 mmol, 1.00 equiv), tert-butyl 3,8-diazabicyclo[3.2.1]octane-3-carboxylate (347 mg, 1.64 mmol, 1.00 equiv), $Cs_2CO_3$ (1599 mg, 4.91 mmol, 3.00 equiv), toluene (8 mL), Ruphos (69 mg, 0.05 equiv). The resulting solution was stirred for 5 hours at 100° C. in an oil bath. The reaction was then quenched by the addition of 10 mL of water. The resulting solution was extracted with dichloromethane/MeOH and the organic layers combined. The resulting mixture was washed with saturate sodium chloride. The mixture was dried over anhydrous sodium sulfate. The residue was applied onto a silica gel column eluting with dichloromethane/methanol (10:1). The collected fractions were combined and concentrated under vacuum. This resulted in 419 mg (59%) of tert-butyl 8-(2-[2-[2-(2-hydroxyethoxy)ethoxy]ethoxy]pyridin-4-yl)-3,8-diazabicyclo[3.2.1]octane-3-carboxylate as yellow oil.

Step 3

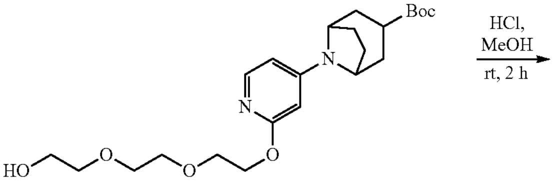

-continued

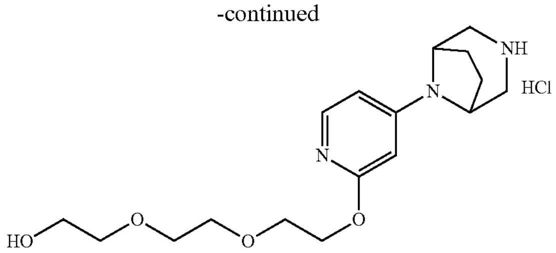

Into a 50 mL round-bottom flask, was placed tert-butyl 8-(2-[2-[2-(2-hydroxyethoxy)ethoxy]ethoxy]pyridin-4-yl)-3,8-diazabicyclo[3.2.1]octane-3-carboxylate (419 mg, 0.96 mmol, 1.00 equiv) and IM HCl in methanol (8 mL). The resulting solution was stirred for 2 hours at room temperature. The resulting mixture was concentrated under vacuum. This resulted in 319 mg (99%) of 2-(2-[2-[(4-[3,8-diazabicyclo[3.2.1]octan-8-yl]pyridin-2-yl)oxy]ethoxy]ethoxy)ethan-1-ol as a yellow oil.

Step 4

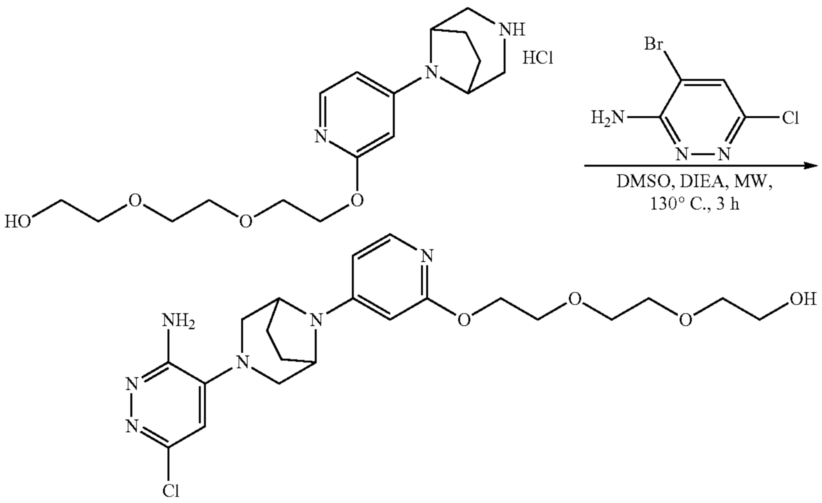

Into a 10 mL microwave tube, was placed 2-(2-[2-[(4-[3,8-diazabicyclo[3.2.1]octan-8-yl]pyridin-2-yl)oxy]ethoxy]ethoxy)ethan-1-ol (319 mg, 0.95 mmol, 1.00 equiv), 4-bromo-6-chloropyridazin-3-amine (780 mg, 3.74 mmol, 4.00 equiv), DMSO (10 mL), DIEA (2 mL). The final reaction mixture was irradiated with microwave radiation for 3 hours at 130° C. The reaction was then quenched by the addition of 10 mL of water. The resulting solution was extracted with ethyl acetate, and organic layers combined. The resulting mixture was washed with saturated sodium chloride. The mixture was dried over anhydrous sodium sulfate. The residue was applied onto a silica gel column eluting with dichloromethane/methanol (10:1). The collected fractions were combined and concentrated under vacuum. This resulted in 260 mg (59%) of 2-[2-[2-([4-[3-(3-amino-6-chloropyridazin-4-yl)-3,8-diazabicyclo[3.2.1]octan-8-yl]pyridin-2-yl]oxy)ethoxy]ethoxy]ethan-1-ol as a yellow solid.

Step 5

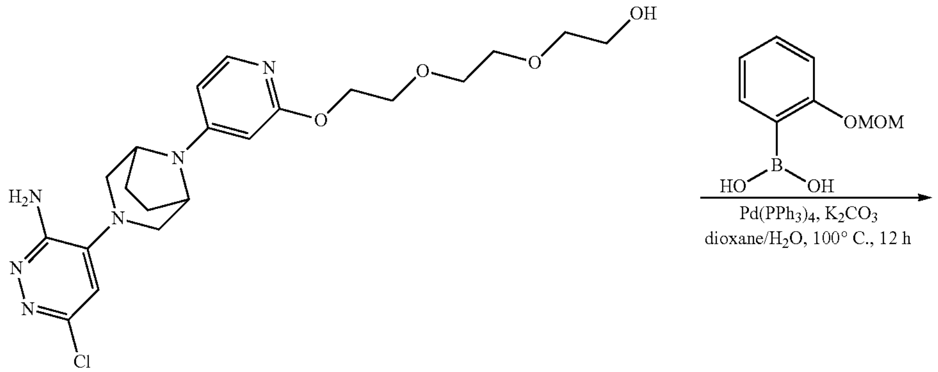

-continued

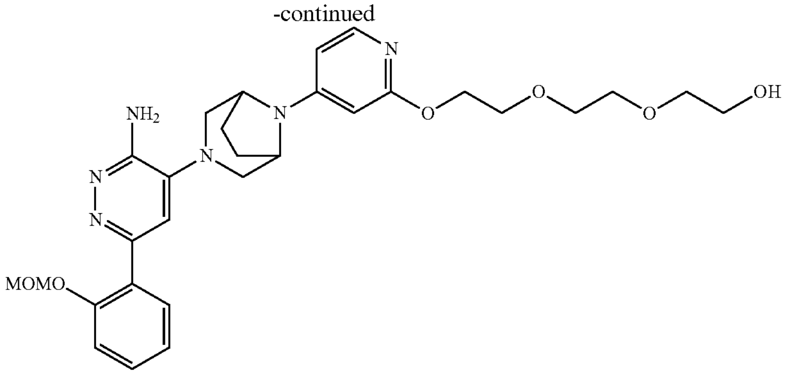

Into a 10 mL microwave tube purged and maintained under nitrogen atmosphere was placed 2-[2-[2-([4-[3-(3-amino-6-chloropyridazin-4-yl)-3,8-diazabicyclo[3.2.1]octan-8-yl]pyridin-2-yl]oxy)ethoxy]ethoxy]ethan-1-ol (295 mg, 0.63 mmol, 1.00 equiv), [2-(methoxymethoxy)phenyl] boronic acid (223 mg, 1.23 mmol, 2.00 equiv), potassium carbonate (254 mg, 1.84 mmol, 3.00 equiv), dioxane (4 mL), water (1 mL), $Pd(PPh_3)_4$ (70 mg, 0.06 mmol, 0.10 equiv). The resulting solution was stirred overnight at 100° C. The reaction was then quenched by the addition of water. The resulting solution was extracted with dichloromethane/MeOH and the organic layers combined. The resulting mixture was washed with saturate sodium chloride. The mixture was dried over anhydrous sodium sulfate. The residue was applied onto a silica gel column eluting with dichloromethane/methanol (10:1). The collected fractions were combined and concentrated under vacuum. This resulted in 221 mg (61%) of 2-[2-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethoxy)ethoxy]ethan-1-ol as a yellow solid.

Step 6

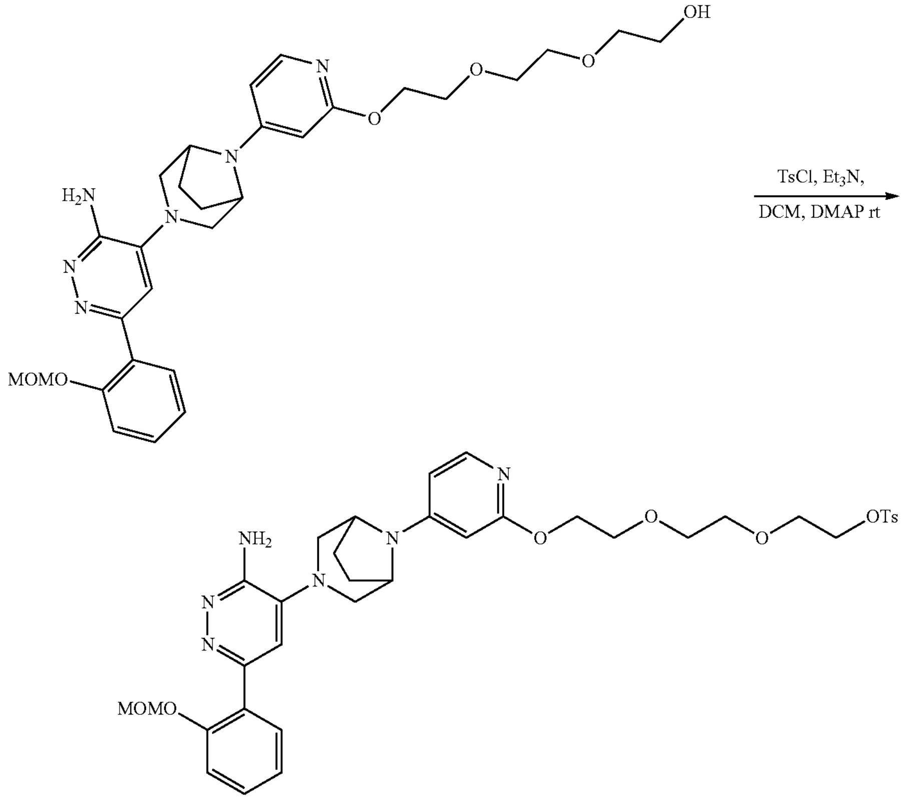

Into a 50 mL round-bottom flask, was placed 2-[2-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethoxy)ethoxy]ethan-1-ol (100 mg, 0.18 mmol, 1.00 equiv), TsCl (50 mg, 0.26 mmol, 1.50 equiv), dichloromethane (5 mL), triethylamine (0.3 mL), 4-dimethylaminopyridine (2 mg, 0.02 mmol, 0.10 equiv). The resulting solution was stirred for 2 hours at room temperature. The reaction was then quenched by the addition of water. The resulting solution was extracted with ethyl acetate and the organic layers combined. The resulting mixture was washed with saturated sodium chloride. The mixture was dried over anhydrous sodium sulfate. The residue was applied onto a silica gel column eluting with dichloromethane/methanol (10:1). The collected fractions were combined and concentrated under vacuum. This resulted in 97 mg (76%) of 2-[2-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethoxy)ethoxy]ethyl 4-methylbenzene-1-sulfonate as a yellow solid.

Step 7

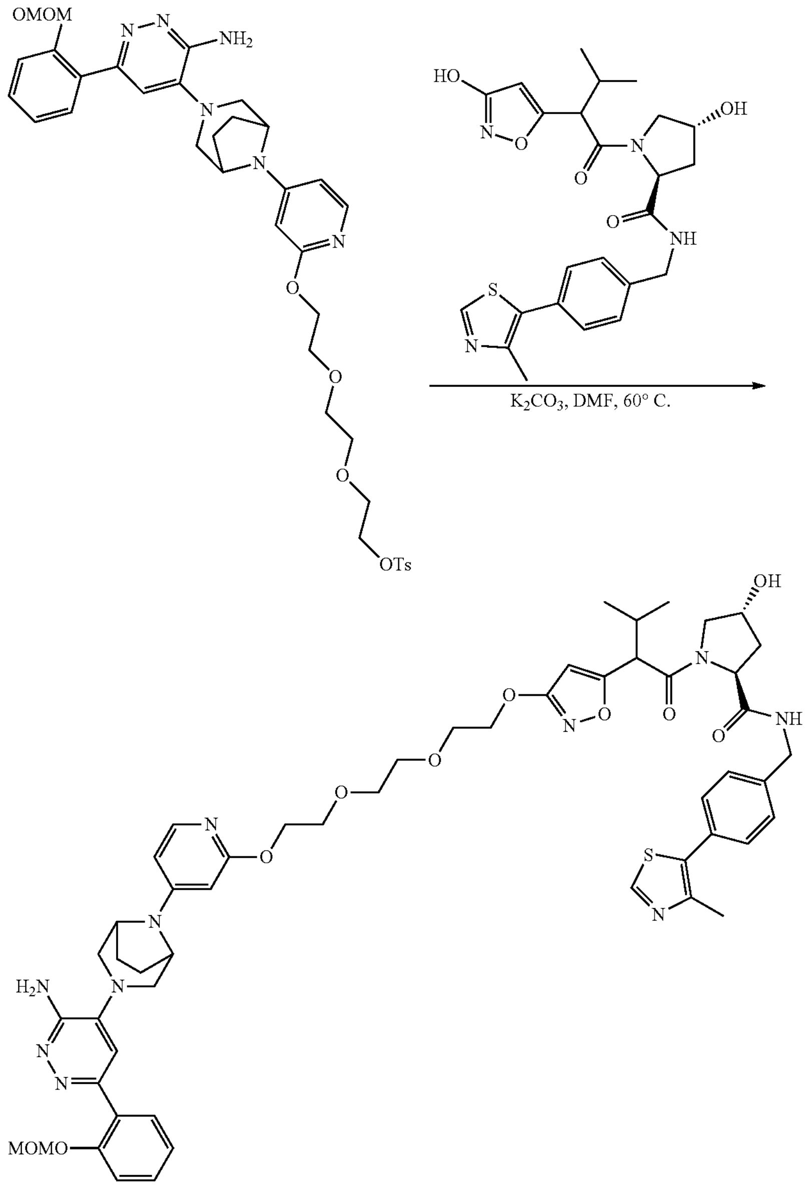

Into a 50 mL round-bottom flask, was placed 2-[2-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethoxy)ethoxy]ethyl 4-methylbenzene-1-sulfonate (87 mg, 0.12 mmol, 1.00 equiv), N,N-dimethylformamide (54 mg, 0.75 mmol, 1.00 equiv), (2S,4R)-4-hydroxy-1-[2-(3-hydroxy-1,2-oxazol-5-yl)-3-methylbutanoyl]-N-[4-(4-methyl-1,3-thiazol-5-yl)phenyl]methylpyrrolidine-2-carboxamide (79 mg, 0.16 mmol, 2.00 equiv), $Cs_2CO_3$ (5 g, 15.35 mmol, 127.15 equiv). The resulting solution was stirred for 4 hours at room temperature. The resulting solution was extracted with dichloromethane/MeOH, and the organic layers combined. The resulting mixture was washed with saturated sodium chloride. The mixture was dried over anhydrous sodium sulfate. The residue was applied onto a silica gel column eluting with dichloromethane/methanol (5:1). The collected fractions were combined and concentrated under vacuum. This resulted in 124 mg (99%) of (2S,4R)-1-[2-(3-[2-[2-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethoxy)ethoxy]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide as a yellow solid.

Step 8
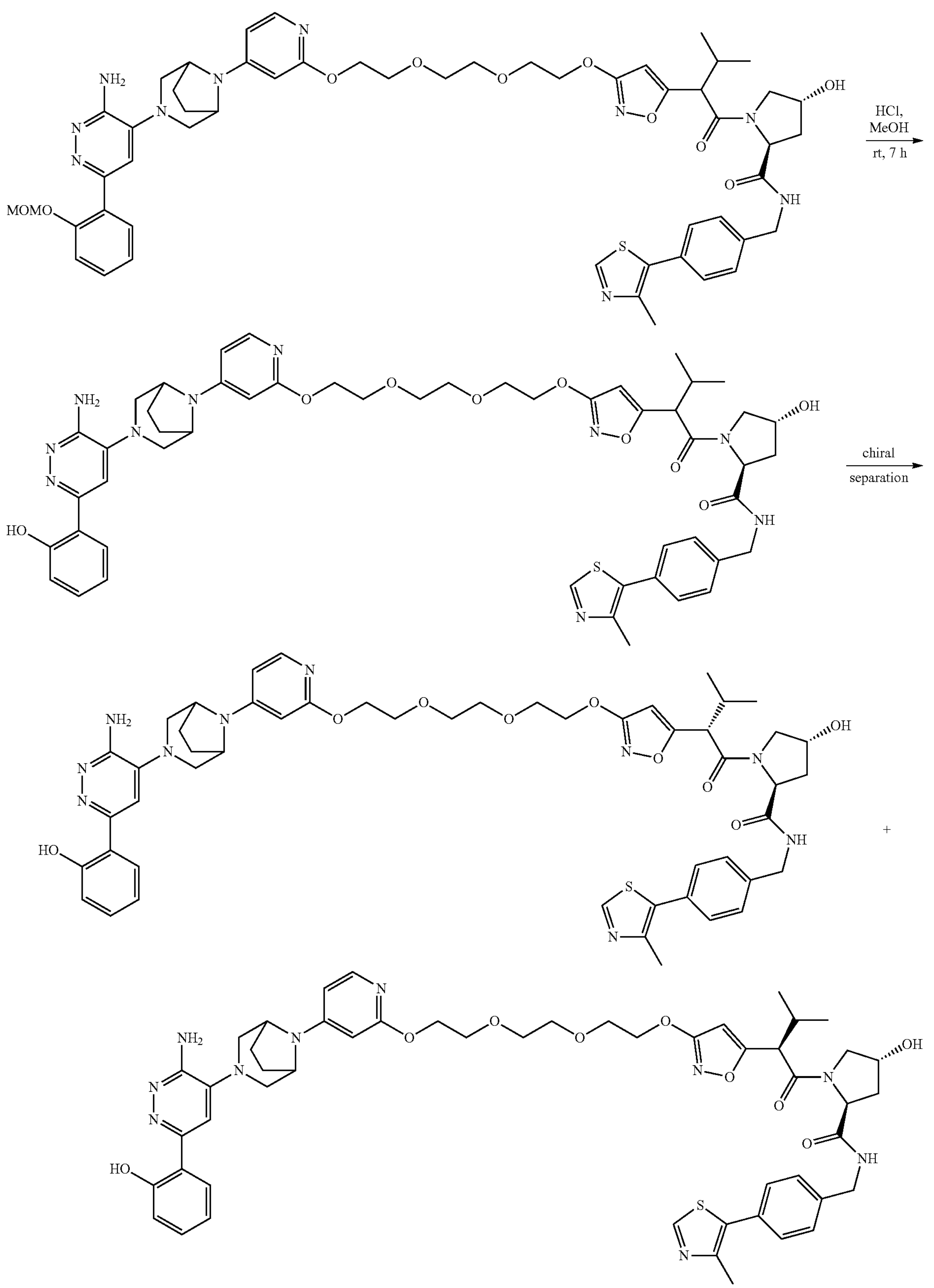

Into a 50 mL round-bottom flask was placed (2S,4R)-1-[2-(3-[2-[2-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethoxy)ethoxy]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide (131 mg, 0.13 mmol, 1.00 equiv), methanol (5 mL), and 1 M HCl in MeOH (1.5 mL). The resulting solution was stirred for 7 hours at room temperature. The resulting solution was diluted with 5 mL of $H_2O$. The pH value of the solution was adjusted to 7 with aqueous $Na_2CO_3$ (2M). The resulting solution was extracted with dichloromethane, and the organic layers combined. The resulting mixture was washed with saturated sodium chloride. The crude product was purified by Prep-HPLC with the following conditions: Column, XBridge Shield RP18 OBD Column, 5 um, 19*150 mm; mobile phase, Water (0.05% $NH_3H_2O$) and acetonitrile (39.0% acetonitrile up to 50.0% in 9 min); Detector, UV 220 nm. This resulted in 60 mg (48%) of (2S,4R)-1-(2-[3-[2-(2-[2-[(4-[3-[3-amino-6-(2-hydroxyphenyl)pyridazin-4-yl]-3,8-diazabicyclo[3.2.1]octan-8-yl]pyridin-2-yl)oxy]ethoxy]ethoxy)ethoxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide as a yellow solid, which was further purified by Chiral-Prep-HPLC with the following conditions: Column, Chiralpak ID-2, 2*25 cm, 5 um; mobile phase, (0.1% DEA) and ethanol (hold 30% ethanol in 30 min); Detector, UV 254/220 nm. This resulted in 13.9 mg (23%) of (2S,4R)-1-[(2S)-2-[3-[2-(2-[2-[(4-[3-[3-amino-6-(2-hydroxyphenyl)pyridazin-4-yl]-3,8-diazabicyclo[3.2.1]octan-8-yl]pyridin-2-yl)oxy]ethoxy]ethoxy)ethoxy]-1,2-oxazol-5-yl]-3-methylbutanoyl]-4-hydroxy-N-[[4-(4-methyl-1,3-thiazol-5-yl)phenyl]methyl]pyrrolidine-2-carboxamide as a white solid[$^1$H NMR (400 MHz, CD3OD): δ 8.85 (m, 1H), 7.78-7.72 (m, 2H), 7.47-7.45 (m, 2H), 7.40-7.34 (m, 3H), 7.23-7.22 (m, 1H), 6.92-6.88 (m, 2H), 6.55-6.53 (m, 1H), 6.23 (s, 1H), 5.97 (s, 1H), 4.64-4.59 (m, 2H), 4.50 (s, 3H), 4.40 (s, 2H), 4.33-4.24 (m, 4H), 3.81-3.79 (m, 2H), 3.75-3.65 (m, 8H), 3.29 (m, 1H), 3.10-3.07 (m, 2H), 2.48-2.46 (m, 3H), 2.23-2.20 (m, 1H), 2.13-2.06 (m, 6H), 1.05 (s, 1H), 0.90-0.89 (d, J=6.8 Hz, 3H), 0.78-0.76 (d, J=8 Hz, 3H)] and 17.9 mg (29%) of (2S,4R)-1-[(2R)-2-[3-[2-(2-[2-[(4-[3-[3-amino-6-(2-hydroxyphenyl)pyridazin-4-yl]-3,8-diazabicyclo[3.2.1]octan-8-yl]pyridin-2-yl)oxy]ethoxy]ethoxy)ethoxy]-1,2-oxazol-5-yl]-3-methylbutanoyl]-4-hydroxy-N-[[4-(4-methyl-1,3-thiazol-5-yl)phenyl]methyl]pyrrolidine-2-carboxamide as a white solid[$^1$H NMR (400 MHz, CD3OD): δ 8.88 (m, 1H), 7.79-7.75 (m, 2H), 7.49-7.39 (m, 5H), 7.24 (m, 1H), 6.92-6.90 (m, 2H), 6.56-6.54 (m, 1H), 6.25-6.24 (M, 1H), 6.00 (s, 1H), 4.53-4.29 (m, 10H), 3.88-3.81 (m, 5H), 3.70-3.63 (m, 6H), 3.33 (m, 2H), 3.14-3.12 (m, 2H), 2.48-2.44 (m, 3H), 2.42-2.29 (m, 1H), 2.25-2.12 (m, 6H), 1.04-1.02 (d, J=6.4 Hz, 3H), 0.88-0.86 (d, J=6.4 Hz, 3H)].

Exemplary Compounds 29 and 30 were prepared using procedures analogous to those described for Exemplary Compounds 27 and 28.

Exemplary Synthesis of Exemplary Compound 31

Step 1

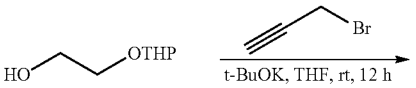

-continued

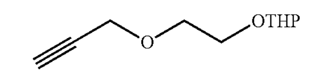

Into a 50 mL round-bottom flask, was placed 2-(oxan-2-yloxy)ethan-1-ol (4.5 g, 30.78 mmol, 1.00 equiv), tetrahydrofuran (10 mL), a solution of t-BuOK (3.6 g, 32.08 mmol, 2.00 equiv) in tetrahydrofuran (60 mL). This was followed by the addition of 3-bromoprop-1-yne (2.61 mL, 1.00 equiv) dropwise with stirring at 0° C. The resulting solution was stirred overnight at room temperature. The reaction was then quenched by the addition of water/ice. The resulting solution was extracted with ethyl acetate, and the organic layers combined. The resulting mixture was washed with saturated sodium chloride. The mixture was dried over anhydrous sodium sulfate. The residue was applied onto a silica gel column eluting with ethyl acetate/petroleum ether (1:5). The collected fractions were combined and concentrated under vacuum. This resulted in 2.8 g (49%) of 2-[2-(prop-2-yn-1-yloxy)ethoxy]oxane as yellow oil.

Step 2

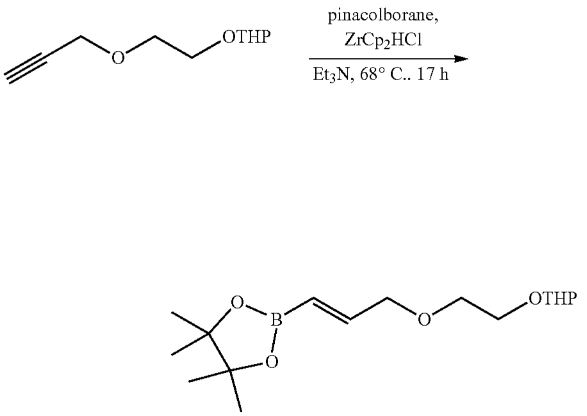

Into a 10-mL microwave tube purged and maintained under an inert atmosphere of nitrogen, was placed 2-[2-(prop-2-yn-1-yloxy)ethoxy]oxane (2.8 g, 15.20 mmol, 1.00 equiv), $ZrCp_2HCl$ (390 mg, 0.10 equiv), triethylamine (153 mg, 1.52 mmol, 0.10 equiv), pinacolborane (2.5 mL). The resulting solution was stirred overnight at 68° C. in an oil bath. The reaction was then quenched by the addition of $NH_4Cl$. The reaction mixture was cooled to 0° C. with a water/ice bath. The resulting solution was extracted with ethyl acetate and the organic layers combined. The resulting mixture was washed with saturated sodium chloride. The mixture was dried over anhydrous sodium sulfate. The residue was applied onto a silica gel column eluting with ethyl acetate/petroleum ether (1:5). The collected fractions were combined and concentrated under vacuum. This resulted in 3.01 g (63%) of 4,4,5,5-tetramethyl-2-[(1E)-3-[2-(oxan-2-yloxy)ethoxy]prop-1-en-1-yl]-1,3,2-dioxaborolane as a yellow liquid.

Step 3

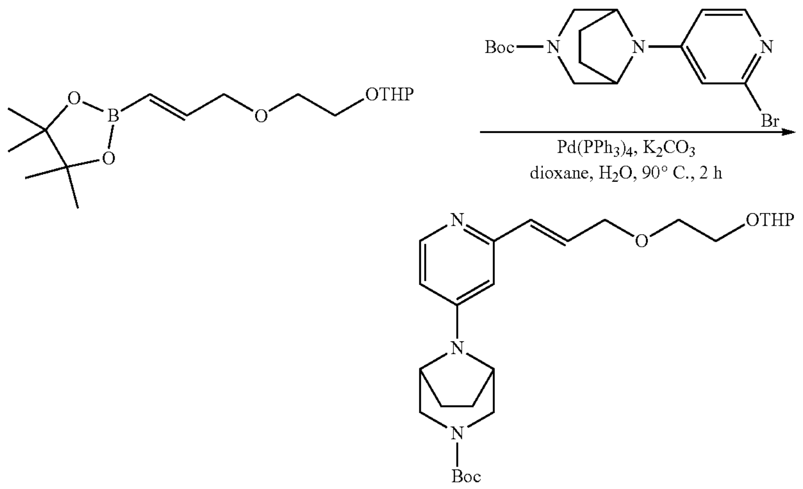

Into a 10-mL microwave tube purged and maintained under an inert atmosphere of nitrogen, was placed 4,4,5,5-tetramethyl-2-[(1E)-3-[2-(oxan-2-yloxy)ethoxy]prop-1-en-1-yl]-1,3,2-dioxaborolane (1 g, 3.20 mmol, 1.00 equiv), $Pd(PPh_3)_4$ (800 mg, 0.69 mmol, 1.00 equiv), potassium carbonate (8 g, 57.88 mmol, 18.07 equiv), dioxane (2 g), tert-butyl 8-(2-bromopyridin-4-yl)-3,8-diazabicyclo[3.2.1]octane-3-carboxylate (902 mg, 2.45 mmol, 3.00 equiv), water (252 mg, 0.10 equiv). The resulting solution was stirred for 1 overnight at 100° C. in an oil bath. The reaction was then quenched by the addition of water. The resulting solution was extracted with ethyl acetate, and the organic layers combined. The resulting mixture was washed with saturate sodium chloride. The mixture was dried over anhydrous sodium sulfate. The residue was applied onto a silica gel column eluting with dichloromethane/methanol (10:1). The collected fractions were combined and concentrated under vacuum. This resulted in 639 mg (42%) of tert-butyl 8-[2-[(1E)-3-[2-(oxan-2-yloxy)ethoxy]prop-1-en-1-yl]pyridin-4-yl]-3,8-diazabicyclo[3.2.1]octane-3-carboxylate as a yellow oil.

Step 4

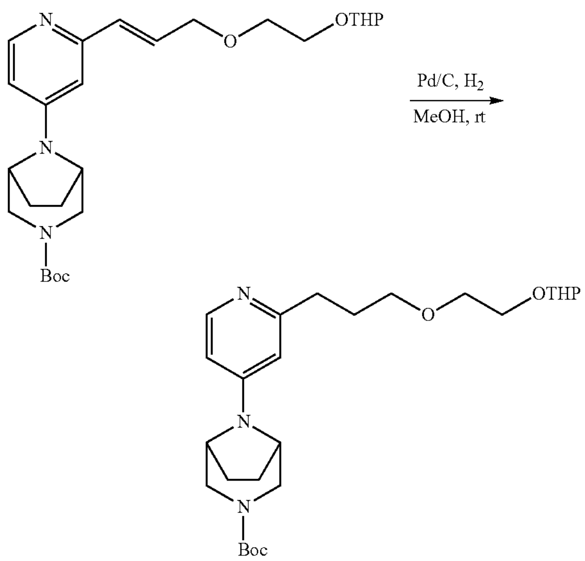

Into a 50-mL round-bottom flask, was placed tert-butyl 8-[2-[(1E)-3-[2-(oxan-2-yloxy)ethoxy]prop-1-en-1-yl]pyridin-4-yl]-3,8-diazabicyclo[3.2.1]octane-3-carboxylate (639 mg, 1.35 mmol, 1.00 equiv), palladium on carbon (200 mg) and methanol (15 mL), and the mixture was stirred under hydrogen atmosphere overnight at room temperature. The solids were filtered off, and the filtrate was concentrated. This resulted in 639 mg (100%) of tert-butyl 8-(2-[3-[2-(oxan-2-yloxy)ethoxy]propyl]pyridin-4-yl)-3,8-diazabicyclo[3.2.1]octane-3-carboxylate as a yellow oil.

Step 5

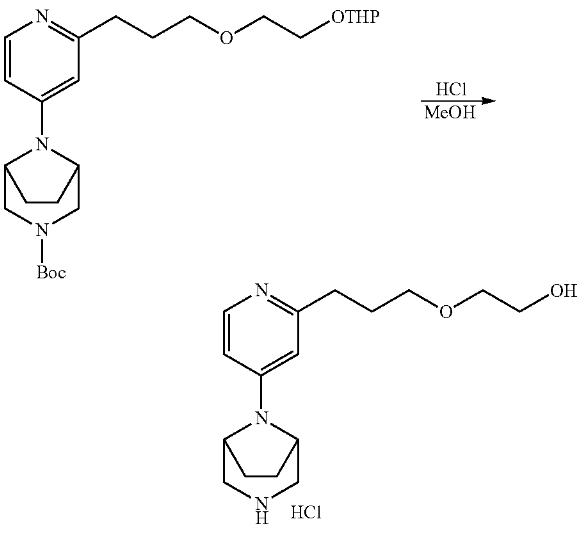

Into a 50-mL round-bottom flask, was placed tert-butyl 8-(2-[3-[2-(oxan-2-yloxy)ethoxy]propyl]pyridin-4-yl)-3,8-diazabicyclo[3.2.1]octane-3-carboxylate (639 mg, 1.34 mmol, 1.00 equiv), methanol (15 mL), and hydrogen chloride gas was bubbled through the solution. The resulting solution was stirred for 3 hours at room temperature. The resulting mixture was concentrated under vacuum. This resulted in 387 mg (100%) of 2-[3-(4-[3,8-diazabicyclo[3.2.1]octan-8-yl]pyridin-2-yl)propoxy]ethan-1-ol as a yellow oil.

Step 6

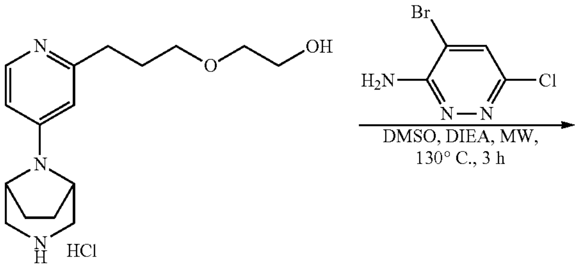

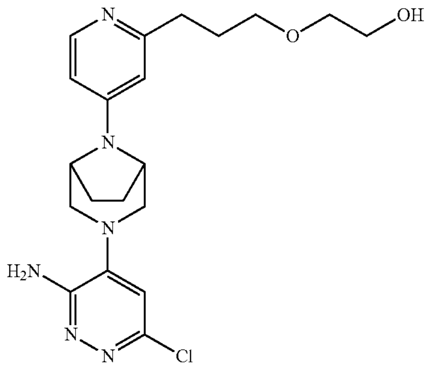

Into a 10-mL microwave tube, was placed 2-[3-(4-[3,8-diazabicyclo[3.2.1]octan-8-yl]pyridin-2-yl)propoxy]ethan-1-ol (387 mg, 1.85 mmol, 1.00 equiv), 4-bromo-6-chloro-pyridazin-3-amine (1.54 g, 7.39 mmol, 4.00 equiv), DMSO (8 mL), DIEA (1.53 mL, 5.00 equiv). The final reaction mixture was irradiated with microwave radiation for 3 hours at 130° C. The reaction was then quenched by the addition of water. The resulting solution was extracted with dichloromethane/MeOH=10:1, and the aqueous layers were combined and concentrated under vacuum. The residue was applied onto a silica gel column with dichloromethane/methanol (7:3). The collected fractions were combined and concentrated under vacuum. This resulted in 519 mg (67%) of 2-(3-[4-[3-(3-amino-6-chloropyridazin-4-yl)-3,8-diazabicyclo[3.2.1]octan-8-yl]pyridin-2-yl]propoxy)ethan-1-ol as a yellow oil.

Step 7

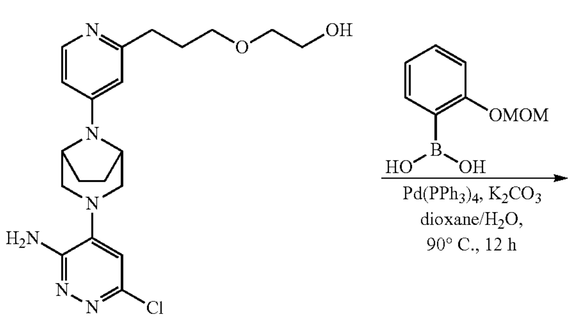

-continued

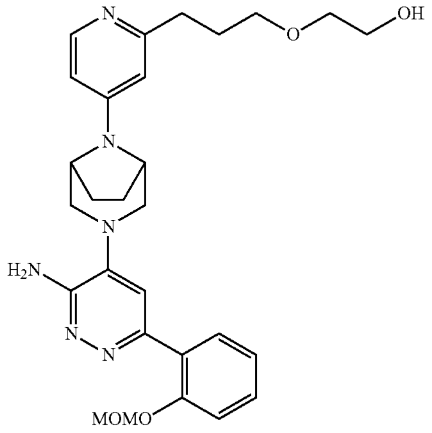

Into a 50-mL round-bottom flask purged and maintained under an inert atmosphere of nitrogen, was placed 2-(3-[4-[3-(3-amino-6-chloropyridazin-4-yl)-3,8-diazabicyclo[3.2.1]octan-8-yl]pyridin-2-yl]propoxy)ethan-1-ol (650 mg, 1.55 mmol, 1.00 equiv), [2-(methoxymethoxy)phenyl]boronic acid (566 mg, 3.11 mmol, 2.00 equiv), dioxane (8 mL), water (2 mL), potassium carbonate (644 mg, 4.66 mmol, 3.00 equiv), $Pd(PPh_3)_4$ (180 mg, 0.16 mmol, 0.10 equiv). The resulting solution was stirred for 3 hours at 100° C. in an oil bath. The resulting mixture was concentrated under vacuum. The residue was applied onto a silica gel column with methanol/H2O (85:15). The collected fractions were combined and concentrated under vacuum. This resulted in 400 mg (50%) of 2-[3-[4-(3-[3-amino-6-[2-(methoxymethoxy)phenyl]pyridazin-4-yl]-3,8-diazabicyclo[3.2.1]octan-8-yl)pyridin-2-yl]propoxy]ethan-1-ol as yellow oil.

Step 8

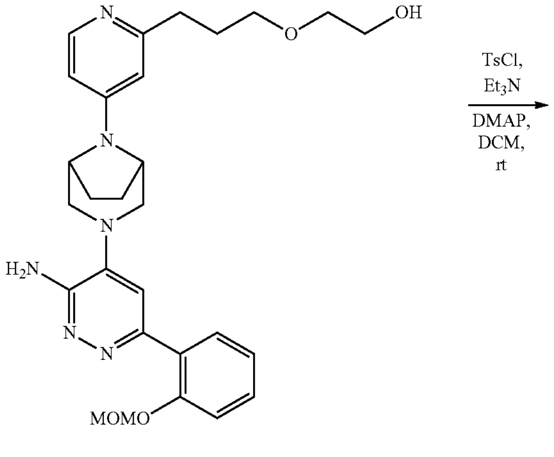

-continued

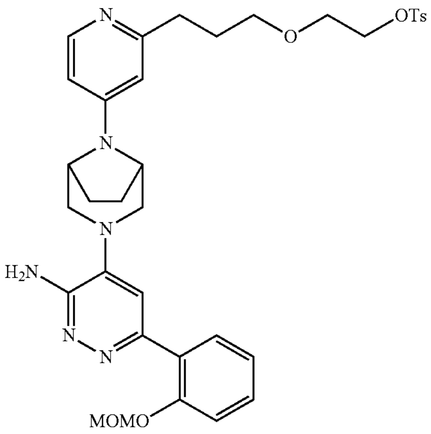

Into a 50-mL round-bottom flask, was placed 2-[3-[4-(3-[3-amino-6-[2-(methoxymethoxy)phenyl]pyridazin-4-yl]-3,8-diazabicyclo[3.2.1]octan-8-yl)pyridin-2-yl]propoxy]ethan-1-ol (400 mg, 0.77 mmol, 1.00 equiv), dichloromethane (15 mL), TsCl (219 mg, 1.15 mmol, 1.50 equiv), triethylamine (155 mg, 1.53 mmol, 2.00 equiv), 4-dimethylaminopyridine (9.4 mg, 0.08 mmol, 0.10 equiv). The resulting solution was stirred overnight at room temperature. The reaction was then quenched by the addition of water. The resulting solution was extracted with dichloromethane, and the organic layers combined. The resulting mixture was washed with saturated sodium chloride. The mixture was dried over anhydrous sodium sulfate. The residue was applied onto a silica gel column eluting with dichloromethane/methanol (10:1). The collected fractions were combined and concentrated under vacuum. This resulted in 330 mg (64%) of 2-[3-[4-(3-[3-amino-6-[2-(methoxymethoxy)phenyl]pyridazin-4-yl]-3,8-diazabicyclo[3.2.1]octan-8-yl)pyridin-2-yl]propoxy]ethyl 4-methylbenzene-1-sulfonate as a yellow solid.

Step 9

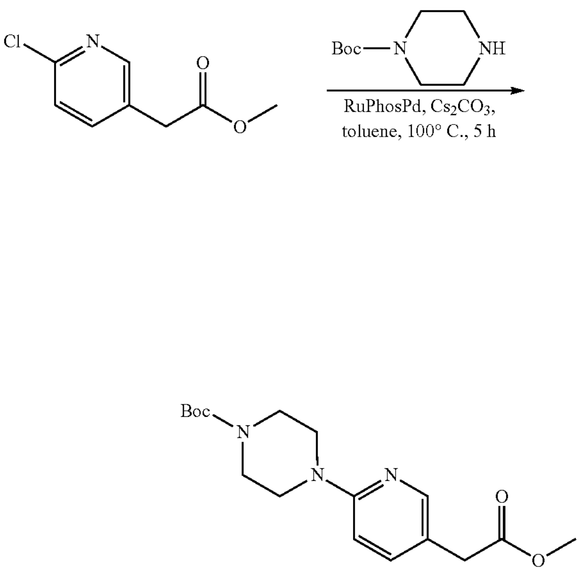

Into a 50-mL round-bottom flask purged and maintained with an inert atmosphere of nitrogen, was placed methyl 2-(6-chloropyridin-3-yl)acetate (500 mg, 2.69 mmol, 1.00 equiv), tert-butyl piperazine-1-carboxylate (502 mg, 2.70 mmol, 1.00 equiv), $Cs_2CO_3$ (2.63 g, 8.07 mmol, 3.00 equiv), toluene (10 mL), RuPhosPd (115 mg, 0.05 equiv). The resulting solution was stirred overnight at 100° C. in an oil bath. The reaction was then quenched by the addition of water. The resulting solution was extracted with ethyl acetate, and the organic layers were combined. The resulting mixture was washed with saturated sodium chloride. The mixture was dried over anhydrous sodium sulfate. The residue was applied onto a silica gel column eluting with ethyl acetate/petroleum ether (1:1). The collected fractions were combined and concentrated under vacuum. This resulted in 319 mg (35%) of tert-butyl 4-[5-(2-methoxy-2-oxoethyl)pyridin-2-yl]piperazine-1-carboxylate as a yellow solid.

Step 10

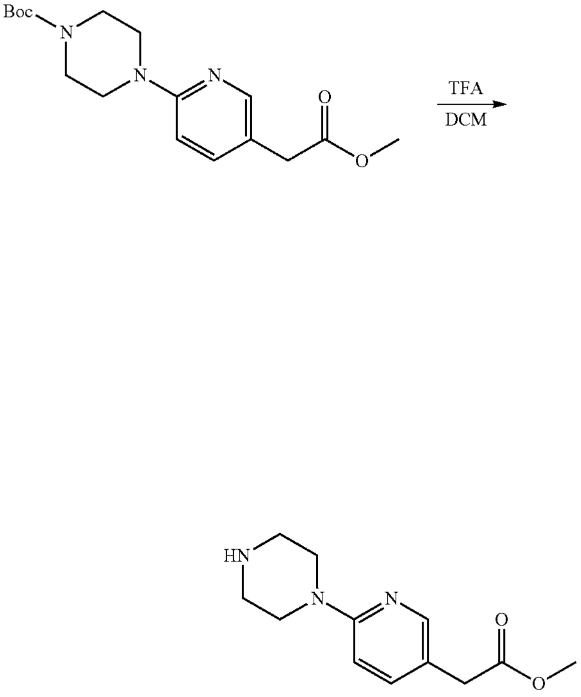

Into a 50-mL round-bottom flask, was placed tert-butyl 4-[5-(2-methoxy-2-oxoethyl)pyridin-2-yl]piperazine-1-carboxylate (319 mg, 0.95 mmol, 1.00 equiv), dichloromethane (8 mL), trifluoroacetic acid (2 mL). The resulting solution was stirred for 2 h at room temperature. The resulting mixture was concentrated under vacuum. This resulted in 223 mg (100%) of methyl 2-[6-(piperazin-1-yl)pyridin-3-yl]acetate as a yellow oil.

Step 11

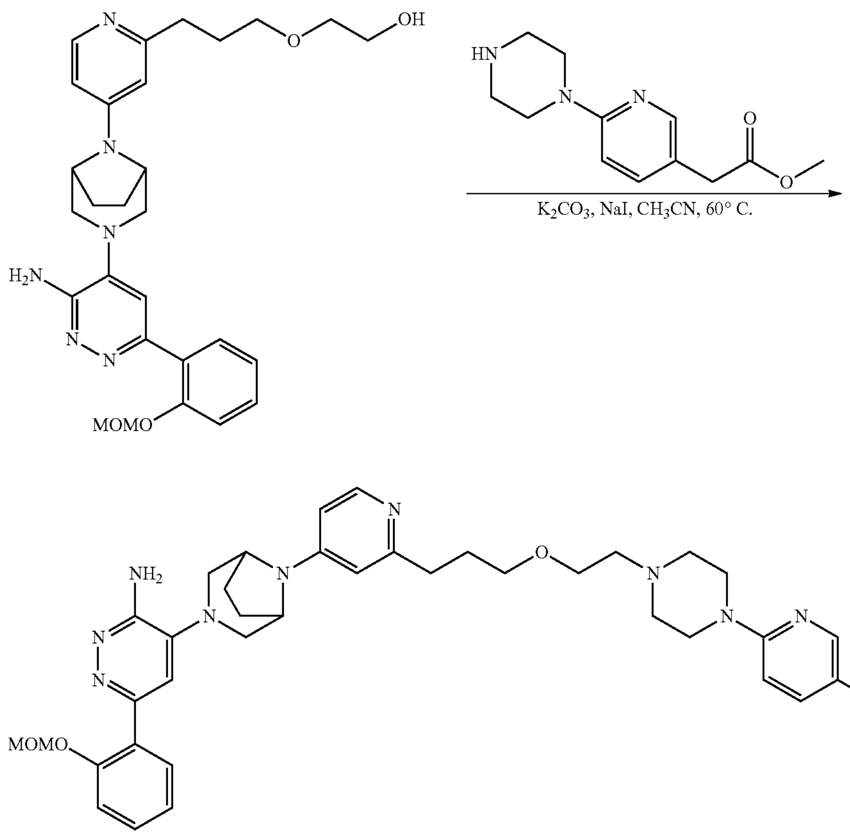

Into a 50-mL round-bottom flask, was placed methyl 2-[6-(piperazin-1-yl)pyridin-3-yl]acetate (101 mg, 0.43 mmol, 1.00 equiv), 2-3-[4-(3-3-amino-6-[2-(methoxymethoxy)phenyl]pyridazin-4-yl-3,8-diazabicyclo[3.2.1]octan-8-yl)pyridin-2-yl]propoxyethyl 4-methylbenzene-1-sulfonate (320 mg, 0.47 mmol, 1.10 equiv), acetonitrile (4 mL), potassium carbonate (298 mg, 2.16 mmol, 5.00 equiv), NaI (193 mg, 3.00 equiv). The resulting solution was stirred overnight at 60° C. The resulting mixture was concentrated under vacuum. The residue was partitioned between dichloromethane and water, organic layer was separated and washed with saturated sodium chloride. The mixture was dried over anhydrous sodium sulfate. The residue was applied onto a silica gel column eluting with dichloromethane/methanol (5:1). The collected fractions were combined and concentrated under vacuum. This resulted in 94 mg (30%) of methyl 2-[6-[4-(2-[3-[4-(3-[3-amino-6-[2-(methoxymethoxy)phenyl]pyridazin-4-yl]-3,8-diazabicyclo[3.2.1]octan-8-yl)pyridin-2-yl]propoxy]ethyl)piperazin-1-yl]pyridin-3-yl]acetate as a yellow solid.

Step 12

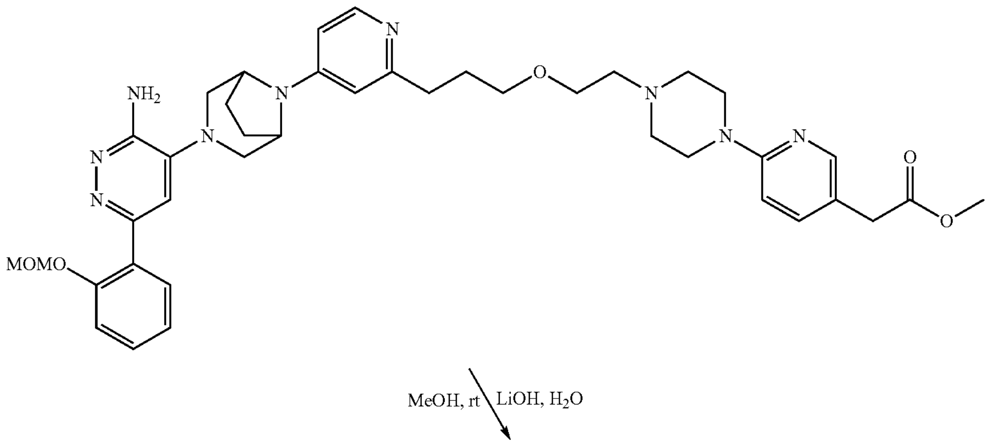

-continued

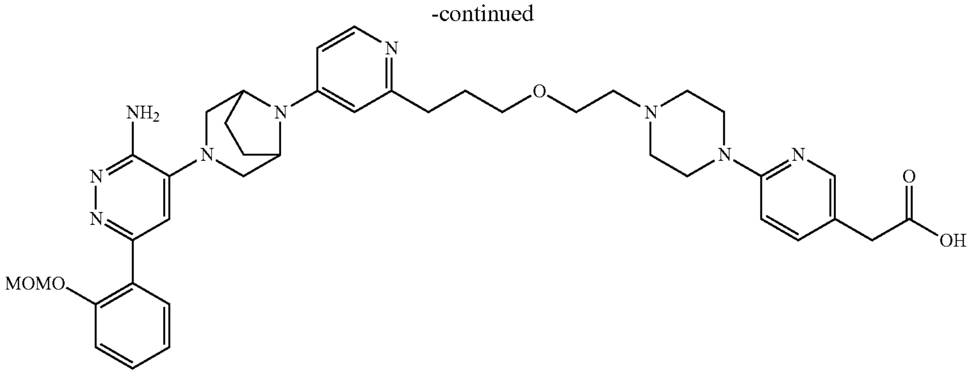

Into a 50-mL round-bottom flask, was placed methyl 2-[6-[4-(2-[3-[4-(3-[3-amino-6-[2-(methoxymethoxy)phenyl]pyridazin-4-yl]-3,8-diazabicyclo[3.2.1]octan-8-yl)pyridin-2-yl]propoxy]ethyl)piperazin-1-yl]pyridin-3-yl]acetate (94 mg, 0.13 mmol, 1.00 equiv), methanol (5 mL), water (2 mL), and LiOH (15 mg, 0.64 mmol, 5.00 equiv). The resulting solution was stirred for 2 days at room temperature. The resulting mixture was concentrated under vacuum. The resulting solution was diluted with 10 mL of $H_2O$. The resulting solution was extracted with dichloromethane, and the aqueous layers were combined and concentrated under vacuum. The residue was dissolved in 10 mL of methanol. The solids were filtered out. The resulting mixture was concentrated under vacuum. This resulted in 72 mg (78%) of 2-[6-[4-(2-[3-[4-(3-[3-amino-6-[2-(methoxymethoxy)phenyl]pyridazin-4-yl]-3,8-diazabicyclo[3.2.1]octan-8-yl)pyridin-2-yl]propoxy]ethyl)piperazin-1-yl]pyridin-3-yl]acetic acid as a yellow solid.

2-[6-[4-(2-[3-[4-(3-[3-Amino-6-[2-(methoxymethoxy)phenyl]pyridazin-4-yl]-3,8-diazabicyclo[3.2.1]octan-8-yl)pyridin-2-yl]propoxy]ethyl)piperazin-1-yl]pyridin-3-yl]acetic acid was converted to the final compound, (2S,4R)-1-((2S)-2-(2-(6-(4-(2-(3-(4-(3-(3-amino-6-(2-hydroxyphenyl)pyridazin-4-yl)-3,8-diazabicyclo[3.2.1]octan-8-yl)pyridin-2-yl)propoxy)ethyl)piperazin-1-yl)pyridin-3-yl)acetamido)-3,3-dimethylbutanoyl)-4-hydroxy-N-(4-(4-methylthiazol-5-yl)benzyl)pyrrolidine-2-carboxamide according to the scheme below and using procedures described above for previous examples.

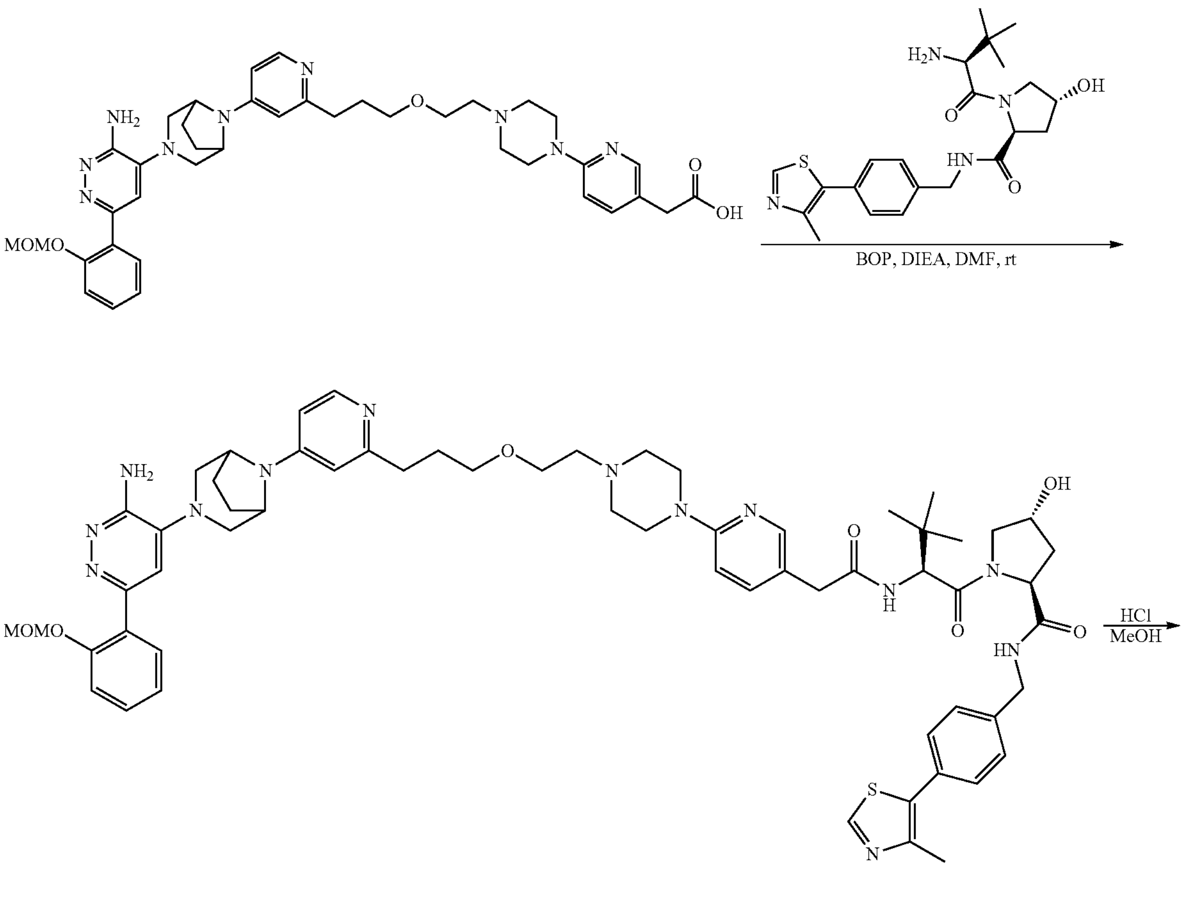

-continued

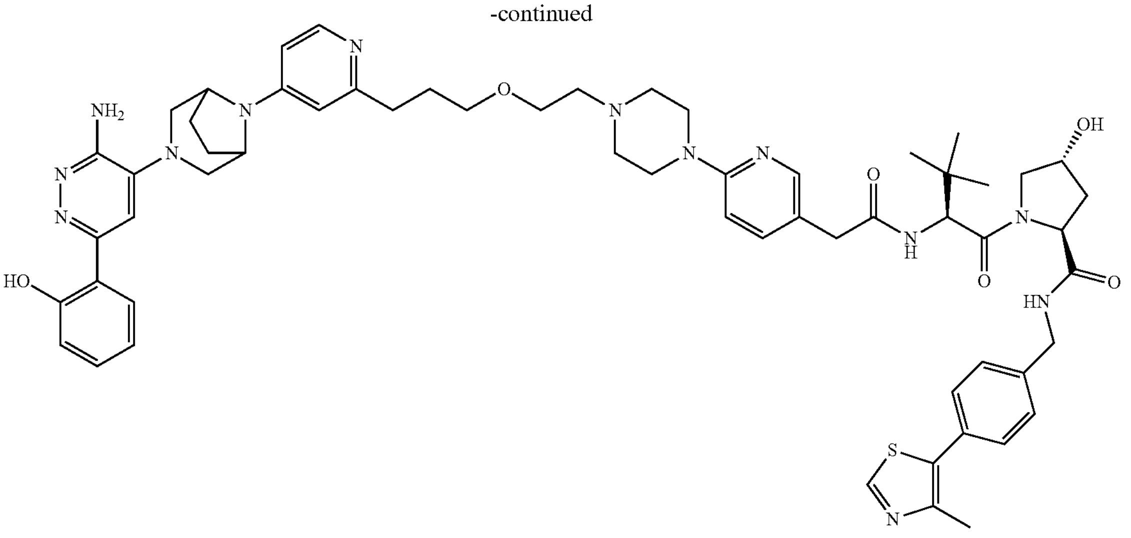

Exemplary Compound 31

Exemplary Compound 50 was prepared using procedures described for Exemplary Compound 31.

Exemplary Synthesis of Exemplary Compound 32

Step 1

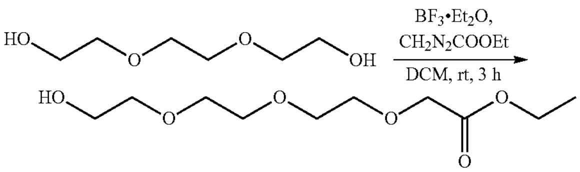

Into a 250-mL round-bottom flask purged and maintained under an inert atmosphere of nitrogen, was placed a solution of 2-[2-(2-hydroxyethoxy)ethoxy]ethan-1-ol (10.0 g, 66.59 mmol, 1.00 equiv) in dichloromethane (100 mL), (diethyloxonio)trifluoroborate (1.9 g, 13.33 mmol, 0.20 equiv), and ethyl 2-diazoacetate (3.8 g, 0.50 equiv). The resulting solution was stirred for 3 hours at room temperature. The reaction was then quenched by the addition of water. The resulting solution was extracted with ethyl acetate and the organic layers were combined. The resulting mixture was washed with brine. The mixture was dried over anhydrous sodium sulfate. The residue was applied onto a silica gel column with ethyl acetate/petroleum ether (1:1). The collected fractions were combined and concentrated under vacuum. This resulted in 3.6 g (23%) of ethyl 2-[2-[2-(2-hydroxyethoxy)ethoxy]ethoxy]acetate as a yellow oil.

Step 2

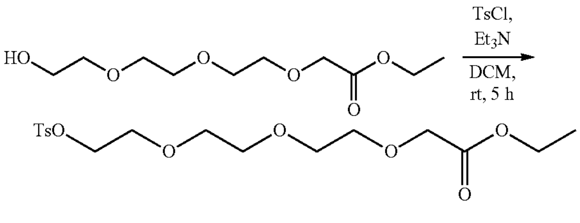

Into a 50-mL round-bottom flask purged and maintained with an inert atmosphere of nitrogen, was placed a solution of ethyl 2-[2-[2-(2-hydroxyethoxy)ethoxy]ethoxy]acetate (1.0 g, 4.23 mmol, 1.00 equiv) in dichloromethane (20 mL), 4-methylbenzene-1-sulfonyl chloride (970 mg, 5.09 mmol, 1.20 equiv), triethylamine (860.0 mg, 8.50 mmol, 2.00 equiv). The resulting solution was stirred for 5 hours at room temperature. The reaction was then quenched by the addition of water. The resulting solution was extracted with ethyl acetate and the organic layers were combined. The resulting mixture was washed with brine. The mixture was dried over anhydrous sodium sulfate. The residue was applied onto a silica gel column with ethyl acetate/petroleum ether (1:1). The collected fractions were combined and concentrated under vacuum. This resulted in 1.1 g (65%) of ethyl 2-[2-[2-(2-[[(4-methylbenzene)sulfonyl]oxy]ethoxy)ethoxy]ethoxy]acetate as a yellow oil.

Step 3

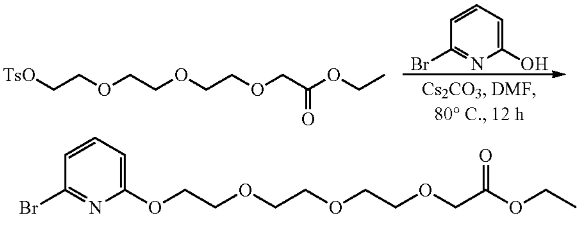

Into a 50-mL round-bottom flask purged and maintained with an inert atmosphere of nitrogen, was placed a solution of ethyl 2-[2-[2-(2-[[(4-methylbenzene)sulfonyl]oxy]ethoxy)ethoxy]ethoxy]acetate (1.0 g, 2.56 mmol, 1.20 equiv) in N,N-dimethylformamide (20 mL), 6-bromopyridin-2-ol (370 mg, 2.13 mmol, 1.00 equiv), $Cs_2CO_3$ (2.1 g, 6.45 mmol, 3.00 equiv). The resulting solution was stirred for 12 hours at 80° C. The reaction was then quenched by the addition of water. The resulting solution was extracted with ethyl acetate and the organic layers combined. The resulting mixture was washed with brine. The mixture was dried over anhydrous sodium sulfate. The residue was applied onto a silica gel column with ethyl acetate/petroleum ether (1:1).

The collected fractions were combined and concentrated under vacuum. This resulted in 800 mg (96%) of ethyl 1-(6-bromopyridin-2-yl)-1,4,7,10-tetraoxadodecan-12-oate as a yellow solid.

Ethyl 1-(6-bromopyridin-2-yl)-1,4,7,10-tetraoxadodecan-12-oate was converted to the final compound, (2S,4R)-1-[(2S)-2-(1-[6-[(1R,4R)-5-[3-amino-6-(2-hydroxyphenyl)pyridazin-4-yl]-2,5-diazabicyclo[2.2.1]heptan-2-yl]pyridin-2-yl]-1,4,7,10-tetraoxadodecan-12-amido)-3,3-dimethylbutanoyl]-4-hydroxy-N-[[4-(4-methyl-1,3-thiazol-5-yl)phenyl]methyl]pyrrolidine-2-carboxamide according to the scheme below and using procedures analogous to those described for other examples above.

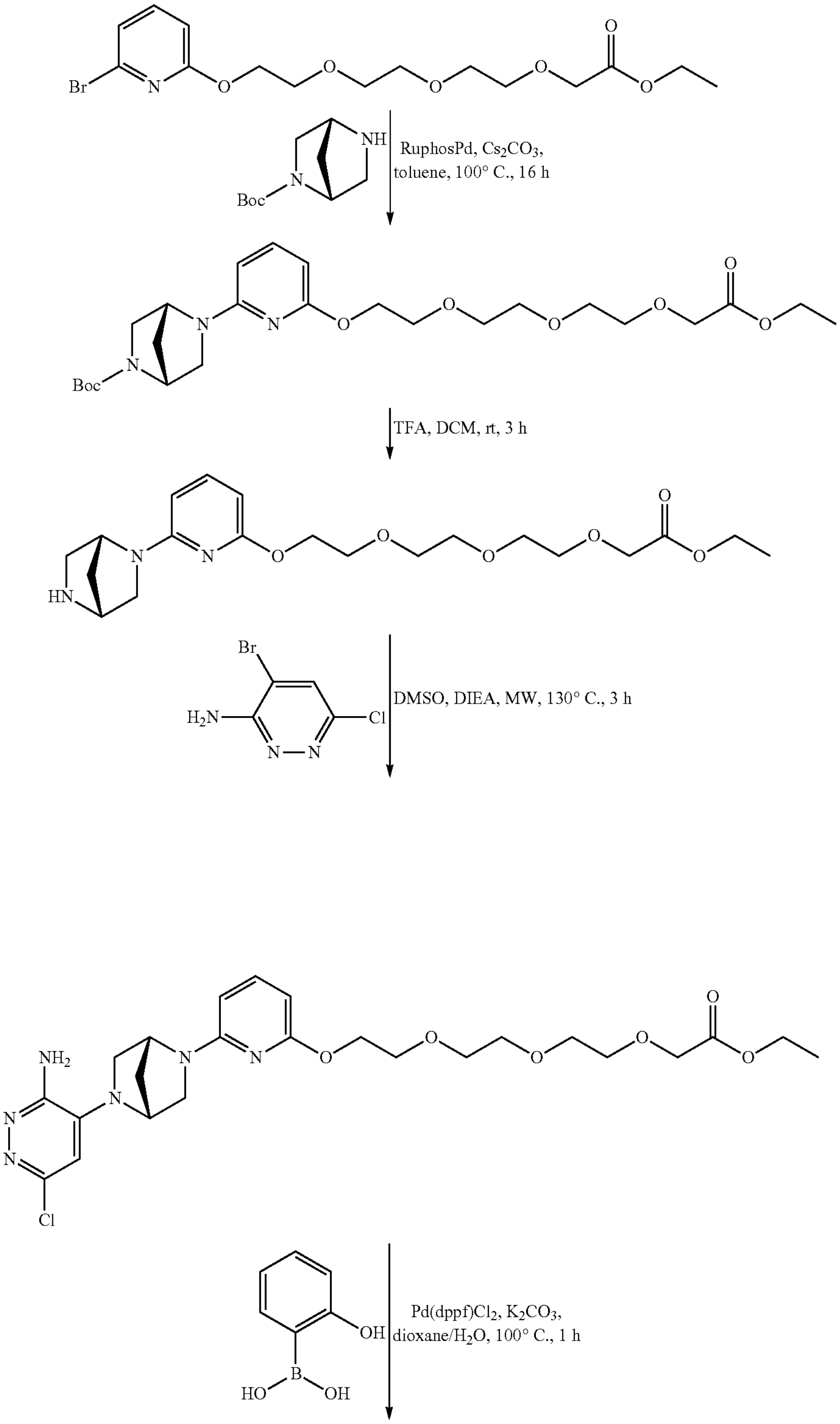

-continued
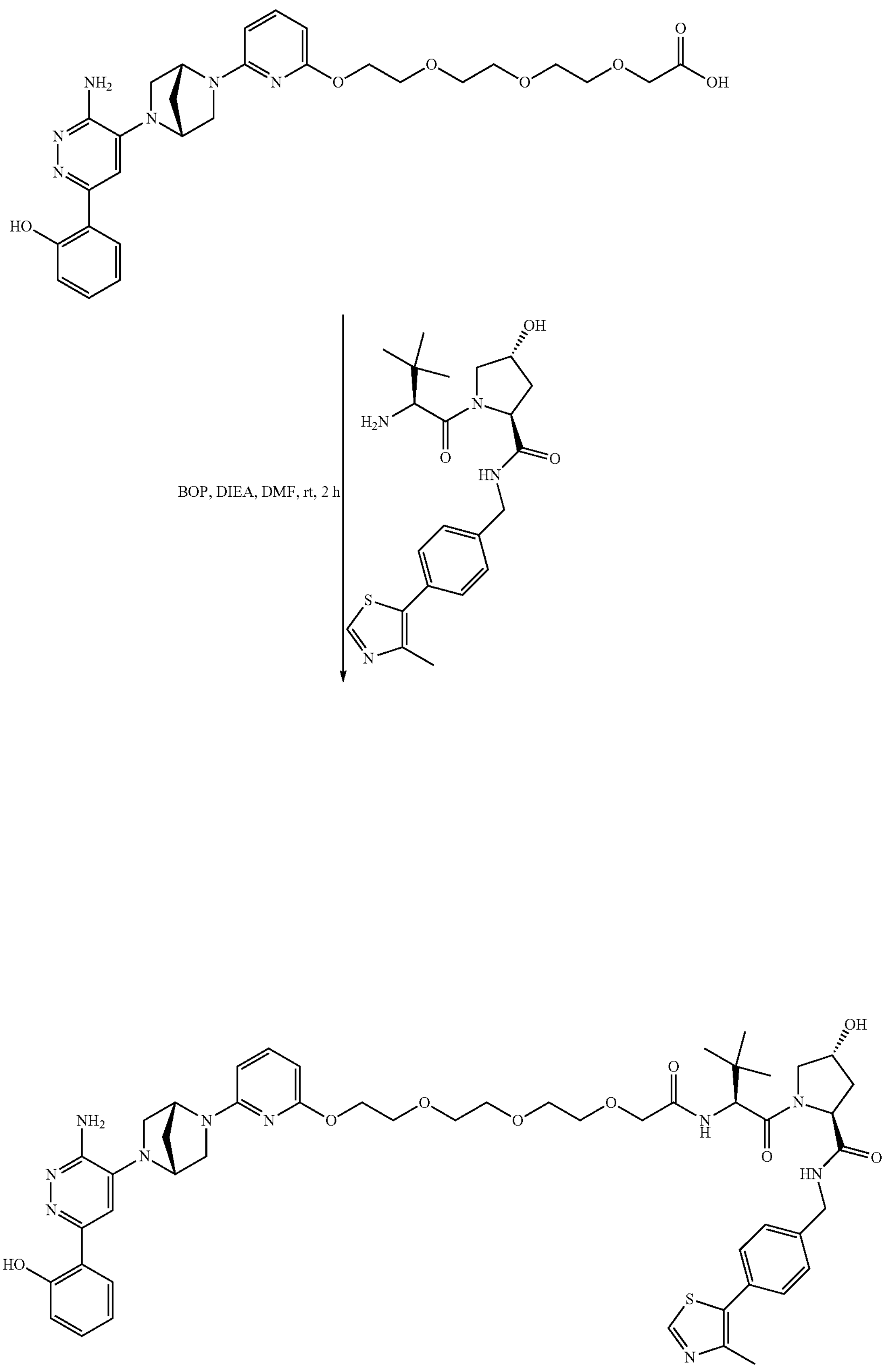
Exemplary Compound 32

Exemplary Synthesis of Exemplary Compound 33

Step 1

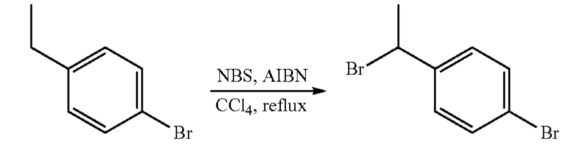

Into a 250-mL round-bottom flask, was placed 1-bromo-4-ethylbenzene (5.5 g, 29.8 mmol, 1.0 equiv), $CCl_4$ (100 mL), AIBN (490 mg, 3.0 mmol, 0.1 equiv), N-Bromosuccinimide (5.34 g, 30.0 mmol, 1.0 equiv). The resulting solution was stirred for 3 hours at 90° C. The resulting mixture was concentrated under vacuum. This resulted in 5.4 g (68%) of 1-bromo-4-(1-bromoethyl)benzene as yellow oil.

Step 2

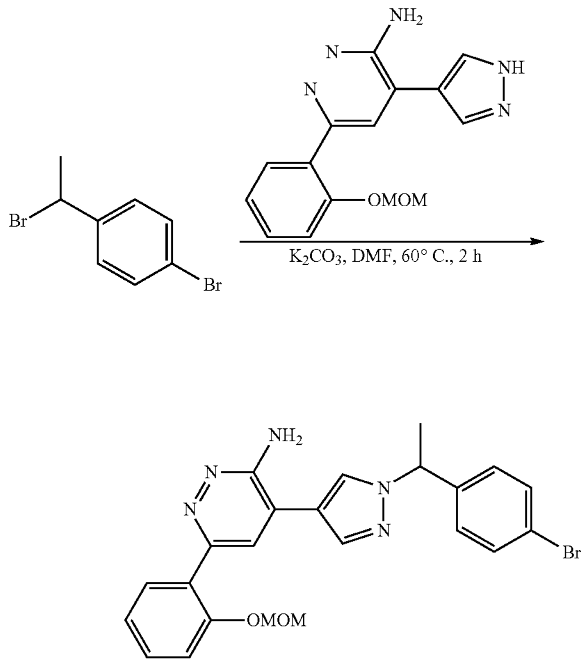

Into a 100-mL round-bottom flask, was placed 6-[2-(methoxymethoxy)phenyl]-4-(1H-pyrazol-4-yl)pyridazin-3-amine (300 mg, 1.0 mmol, 1.0 equiv), N,N-dimethylformamide (5.0 mL), 1-bromo-4-(1-bromoethyl)benzene (400.0 mg, 1.5 mmol, 1.5 equiv), potassium carbonate (414 mg, 3.0 mmol, 3.0 equiv). The resulting solution was stirred for 3 hours at 60° C. The reaction was then quenched by the addition of 10 mL of water. The resulting solution was extracted with ethyl acetate and (20.0 mL×3), the organic layers combined and concentrated under vacuum. The residue was applied onto a silica gel column eluting with dichloromethane/methanol (1:10). This resulted in 300 mg (62%) of 4-[1-[1-(4-bromophenyl)ethyl]-1H-pyrazol-4-yl]-6-[2-(methoxymethoxy)phenyl]pyridazin-3-amine as a brown solid.

Step 3

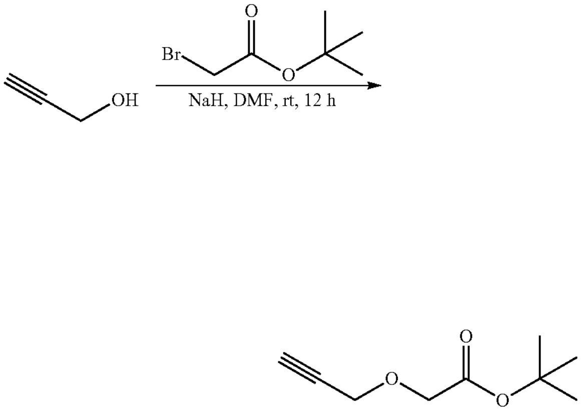

Into a 250-mL round-bottom flask, was placed prop-2-yn-1-ol (10 g, 178.4 mmol, 1.0 equiv), tetrahydrofuran (100.0 mL), sodium hydride (6.4 g, 266.7 mmol, 0.9 equiv), and tert-butyl 2-bromoacetate (28 g, 143.6 mmol, 0.8 equiv). The resulting solution was stirred for 3 hours at room temperature. The reaction was then quenched by the addition of 20 mL of ammonium chloride aqueous solution. The resulting mixture was concentrated under vacuum. The resulting solution was extracted with ethyl acetate (30 mL×3), and the organic layers were combined and concentrated under vacuum. This resulted in 24.0 g (90%) of tert-butyl 2-(prop-2-yn-1-yloxy)acetate as a yellow solid.

Step 4

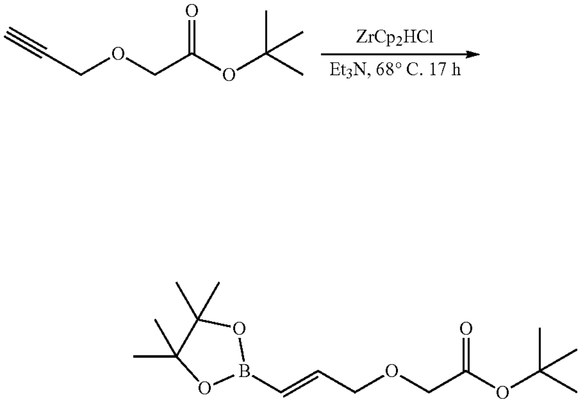

Into a 250-mL round-bottom flask, was placed tert-butyl 2-(prop-2-yn-1-yloxy)acetate (6.6 g, 38.8 mmol, 1.0 equiv), triethylamine (400.0 mg, 3.9 mmol, 0.1 equiv), pinacolborane (20.0 mL), $ZrCp_2HCl$ (1 g, 0.1 equiv). The resulting solution was stirred for 12 minutes at 60° C. The reaction was then quenched by the addition of 10 mL of ice/water. The resulting solution was extracted with ethyl acetate (30 mL×3), and the organic layers were combined. The residue was applied onto a silica gel column eluting with ethyl acetate/petroleum ether (1:5). This resulted in 5.0 g (43%) of tert-butyl 2-[[(2E)-3-(tetramethyl-1,3,2-dioxaborolan-2-yl)prop-2-en-1-yl]oxy]acetate as a yellow oil.

Step 5

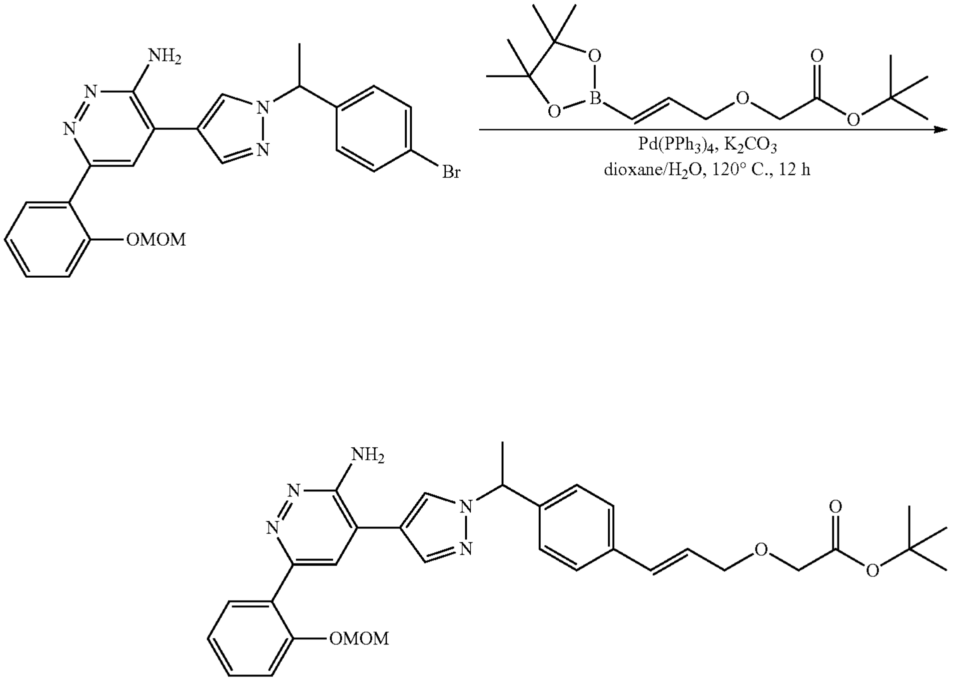

Into a 10-mL sealed tube, was placed 4-[1-[1-(4-bromophenyl)ethyl]-1H-pyrazol-4-yl]-6-[2-(methoxymethoxy)phenyl]pyridazin-3-amine (300 mg, 0.6 mmol, 1.0 equiv), tert-butyl 2-[[(2E)-3-(tetramethyl-1,3,2-dioxaborolan-2-yl)prop-2-en-1-yl]oxy]acetate (279 mg, 0.9 mmol, 1.5 equiv), $Pd(PPh_3)_4$ (72 mg, 0.06 mmol, 0.1 equiv), potassium carbonate (259 mg, 1.9 mmol, 3.0 equiv), dioxane (4.0 mL), and $H_2O$ (1.0 mL). The resulting solution was stirred for 5 hours at 90° C. The resulting mixture was concentrated under vacuum. The residue was applied onto a silica gel column eluting with dichloromethane/methanol (10:1). This resulted in 200 mg (56%) of tert-butyl 2-[[(2E)-3-[4-[1-(4-[3-amino-6-[2-(methoxymethoxy)phenyl]pyridazin-4-yl]-1H-pyrazol-1-yl)ethyl]phenyl]prop-2-en-1-yl]oxy]acetate as a yellow solid.

Step 6

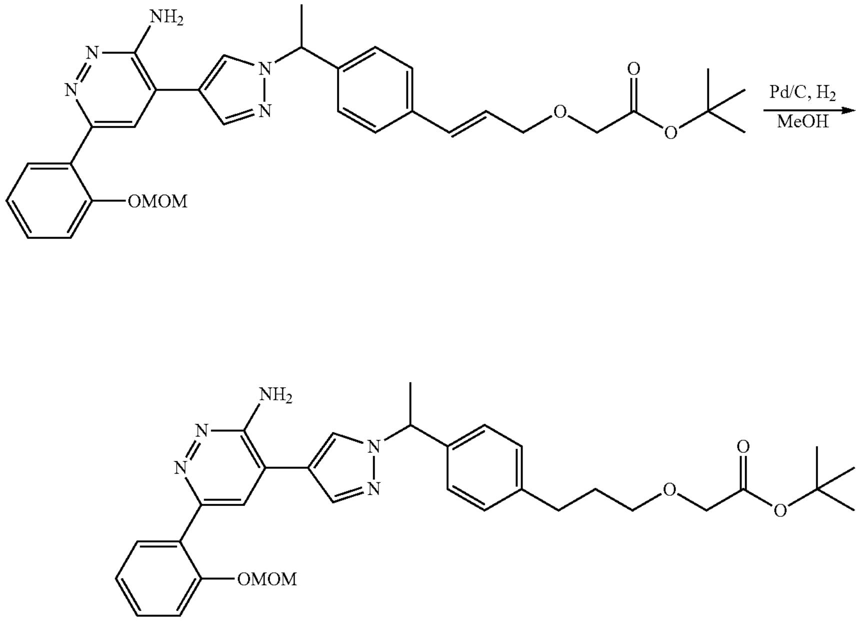

Into a 100-mL round-bottom flask, was placed tert-butyl 2-[[(2E)-3-[4-[1-(4-[3-amino-6-[2-(methoxymethoxy)phenyl]pyridazin-4-yl]-1H-pyrazol-1-yl)ethyl]phenyl]prop-2-en-1-yl]oxy]acetate (93 mg, 0.2 mmol, 1.0 equiv), methanol (5.0 mL), palladium on carbon (100 mg). The resulting solution was stirred under hydrogen atmosphere for 1 hour at room temperature. The solids were filtered off. The resulting mixture was concentrated under vacuum. This resulted in 56 mg (60%) of tert-butyl 2-(3-[4-[1-(4-[3-amino-6-[2-(methoxymethoxy)phenyl]pyridazin-4-yl]-1H-pyrazol-1-yl)ethyl]phenyl]propoxy)acetate as a yellow solid.

Step 7

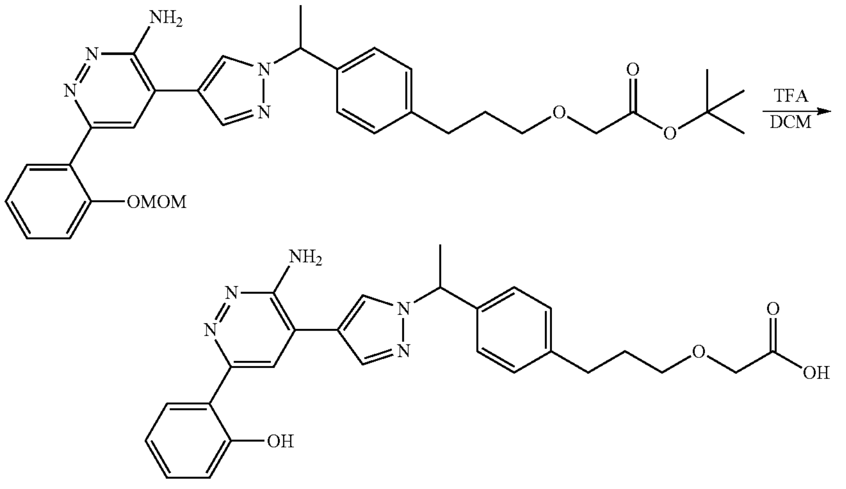

Into a 100-mL round-bottom flask, was placed tert-butyl 2-(3-[4-[1-(4-[3-amino-6-[2-(methoxymethoxy)phenyl] pyridazin-4-yl]-1H-pyrazol-1-yl)ethyl]phenyl]propoxy)acetate (56 mg, 0.1 mmol, 1.0 equiv), dichloromethane (10.0 mg), trifluoroacetic acid (5 mL). The resulting solution was stirred for 2 hours at room temperature. The resulting mixture was concentrated under vacuum. This resulted in 45 mg (90%) of 2-(3-[4-[1-(4-[3-amino-6-[2-(methoxymethoxy) phenyl]pyridazin-4-yl]-1H-pyrazol-1-yl)ethyl]phenyl]propoxy)acetic acid as a brown solid.

Step 8

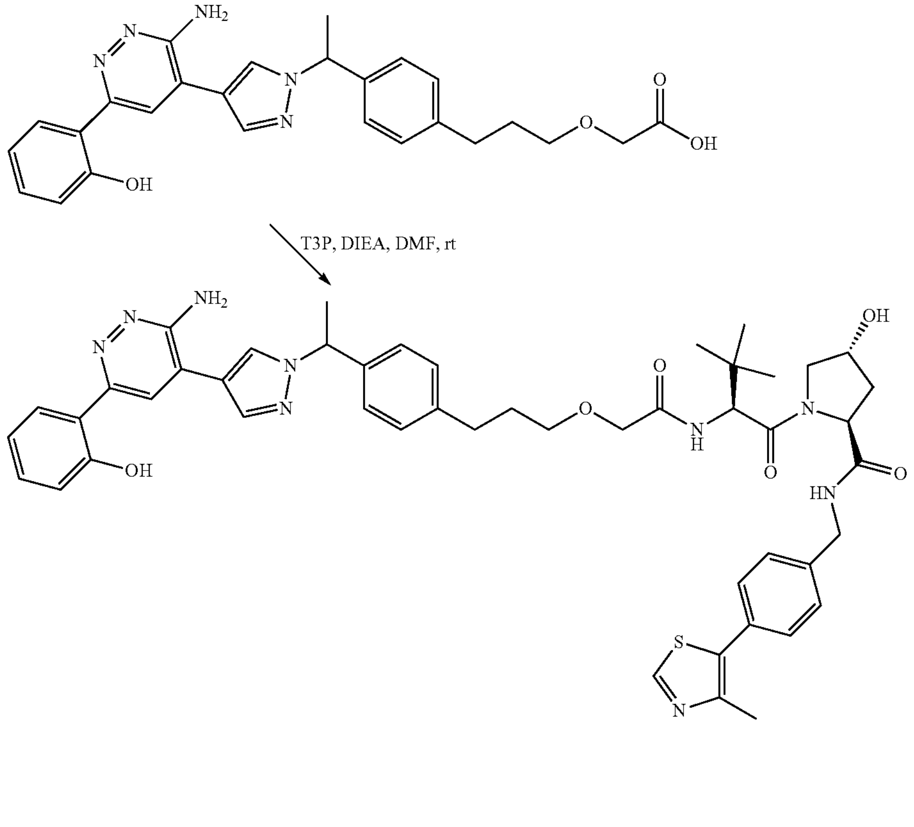

Into a 25-mL round-bottom flask, was placed 2-[3-[4-(1-[4-[3-amino-6-(2-hydroxyphenyl)pyridazin-4-yl]-1H-pyrazol-1-yl]ethyl)phenyl]propoxy]acetic acid (26 mg, 0.06 mmol, 1.0 equiv), N,N-dimethylformamide (5 mL), (2S,4R)-1-[(2S)-2-amino-3,3-dimethylbutanoyl]-4-hydroxy-N-[4-(4-methyl-1,3-thiazol-5-yl)phenyl]methylpyrrolidine-2-carboxamide (30 mg, 0.07 mmol, 1.2 equiv), DIEA (21 mg, 0.2 mmol, 3.0 equiv), T3P (53 mg, 1.2 equiv). The resulting solution was stirred for 1 hour at room temperature. The reaction was then quenched by the addition of 0.5 mL of water. The solids were filtered out. The crude product (5 mL) was purified by Prep-HPLC with the following conditions: Column, XBridge Prep C18 OBD Column, 150 mm 5 um; mobile phase, Water (10 mMOL/L bicarbonate amine) and ACN (45.0% ACN up to 52.0% in 7 min); Detector, UV 254/220 nm. This resulted in 6 mg (12%) of (2S,4R)-1-[(2S)-2-(2-[3-[4-(1-[4-[3-amino-6-(2-hydroxyphenyl)pyridazin-4-yl]-1H-pyrazol-1-yl]ethyl)phenyl]propoxy]acetamido)-3,3-dimethylbutanoyl]-4-hydroxy-N-[[4-(4-methyl-1,3-thiazol-5-yl)phenyl]methyl]pyrrolidine-2-carboxamide as a gray solid.

$^1$H NMR (300 MHz, Methanol-d4) δ 8.79 (s, 1H), 8.35-8.23 (m, 1H), 8.09-7.97 (m, 2H), 7.80 (d, J=7.7 Hz, 1H), 7.43-7.37 (m, 2H), 7.31 (d, J=8.1 Hz, 2H), 7.24 (d, J=8.1 Hz, 1H), 7.20 (s, 4H), 6.89 (t, J=7.6 Hz, 2H), 5.64-5.52 (m, 1H), 4.66 (s, 1H), 4.60-4.44 (m, 3H), 4.27 (d, J=15.5 Hz, 1H), 3.92 (d, J=4.6 Hz, 2H), 3.88-3.74 (m, 2H), 3.52 (d, J=6.2 Hz, 2H), 2.71 (t, J=7.6 Hz, 2H), 2.37 (s, 3H), 2.18 (d, J=7.7 Hz, 1H), 2.07 (dd, J=9.4, 4.2 Hz, 1H), 1.89 (dd, J=7.3, 1.2 Hz, 6H), 1.26 (s, 1H), 1.10-0.95 (d, J=1.6 Hz, 9H), 0.95-0.90 (m, 1H).

Exemplary Synthesis of Exemplary Compound 34

Exemplary Compound 34 was prepared according to the scheme below using procedures described for other examples above, as well as procedures known and appreciated to those skilled in the art.

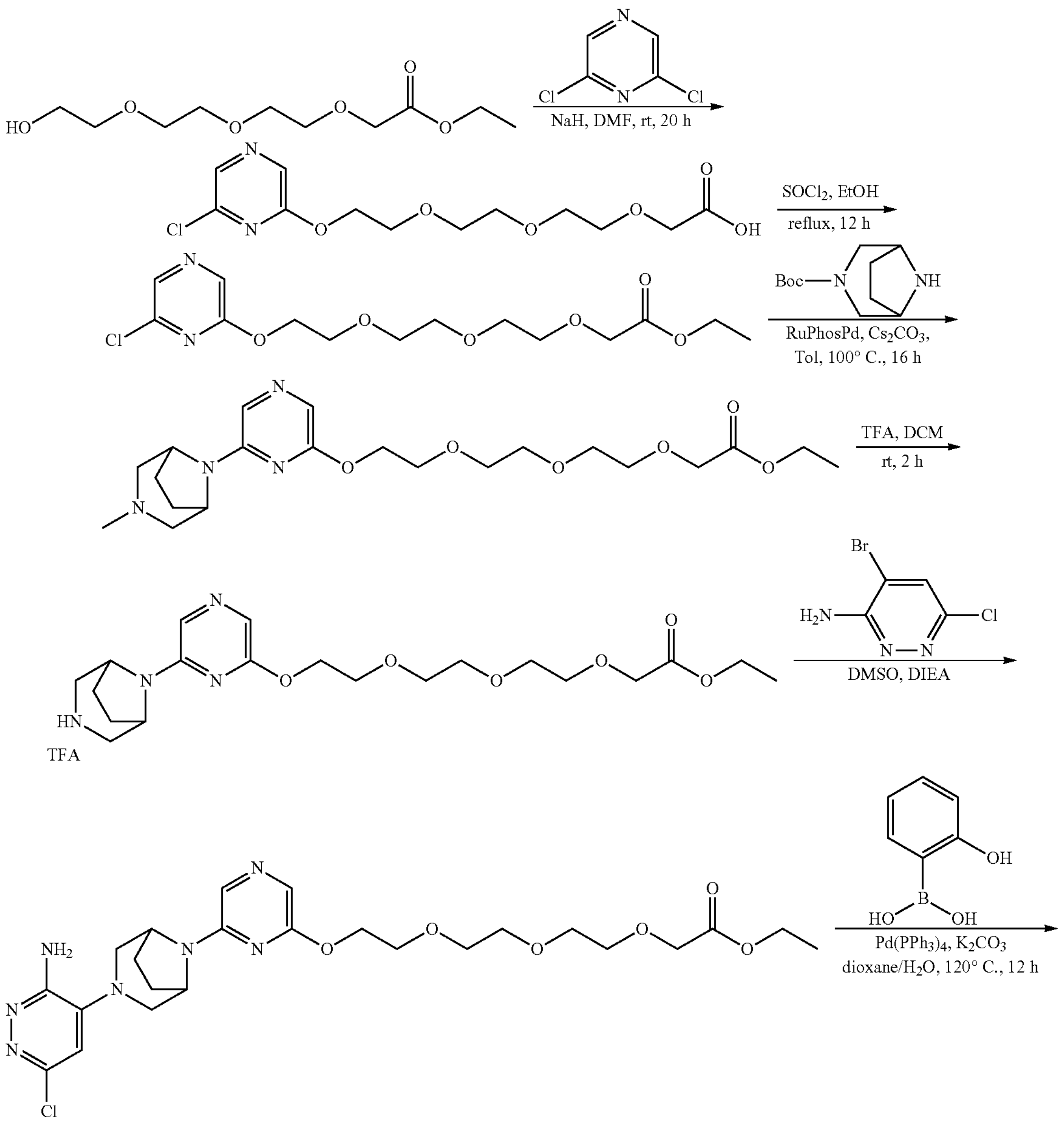

-continued
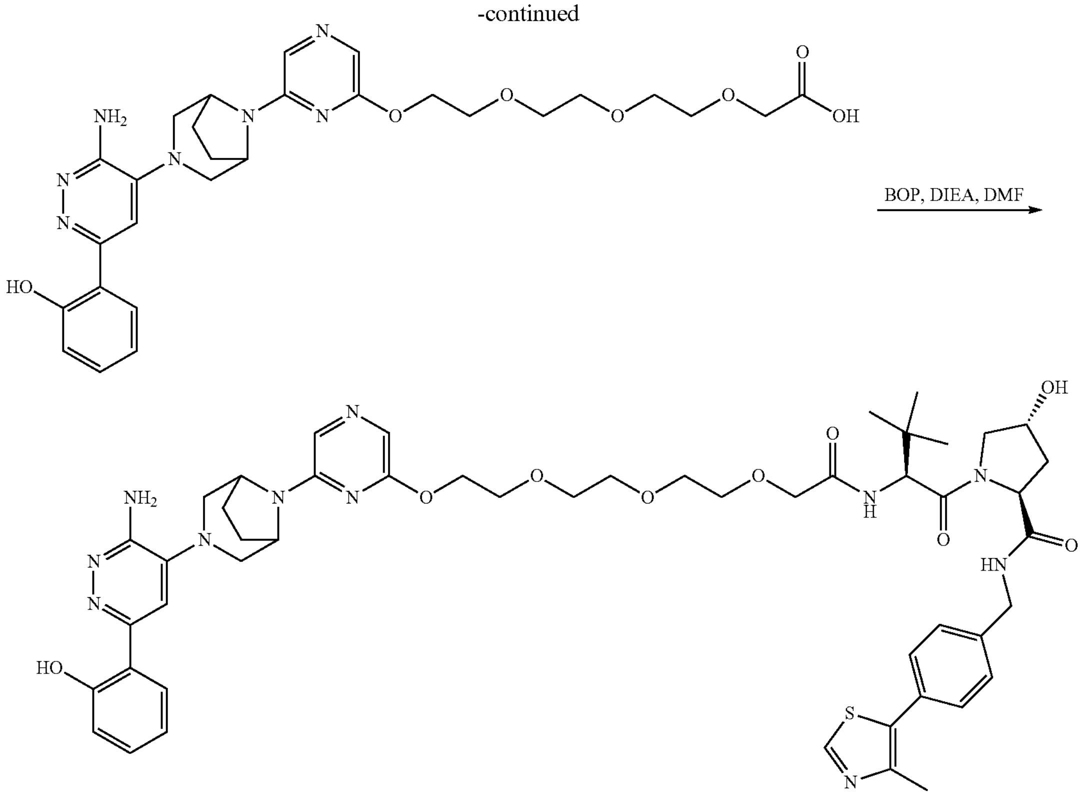
Exemplary Compound 34
Exemplary Synthesis of Exemplary Compound 36 and Exemplary Compound 37
Exemplary Compounds 36 and 37 were prepared according to the scheme below using procedures described for other examples above, as well as as well as procedures known and appreciated to those skilled in the art.
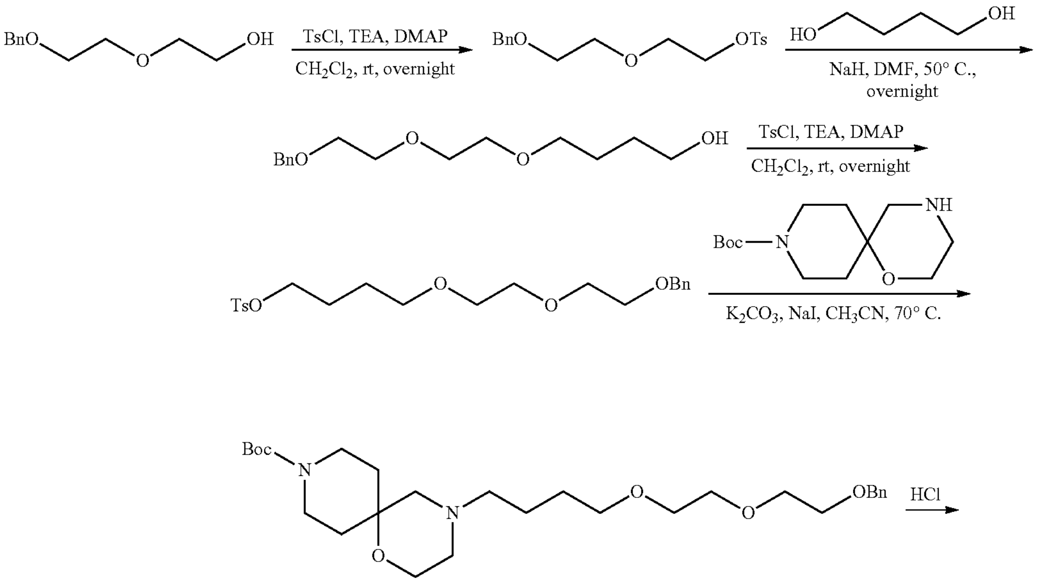

-continued
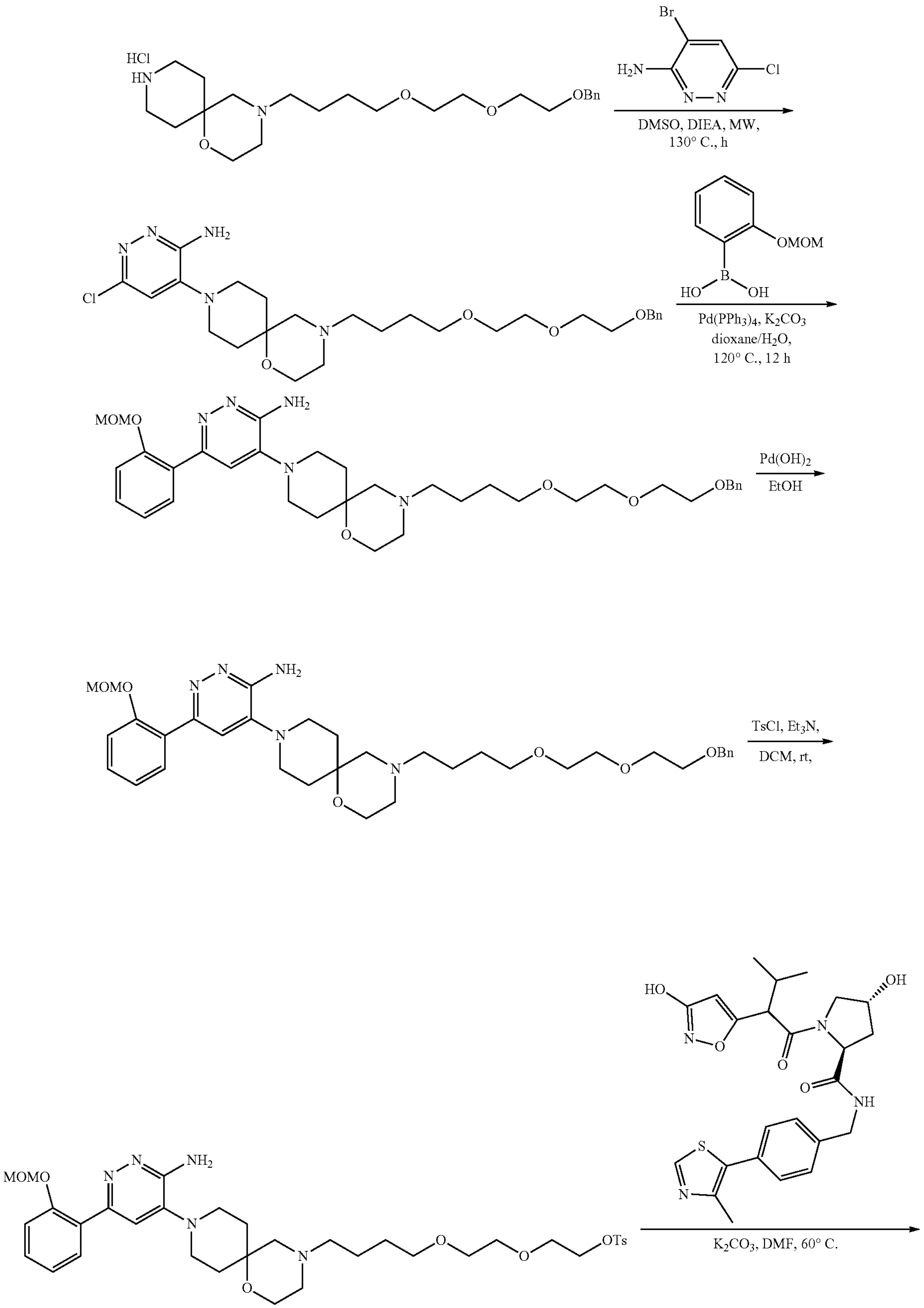

-continued
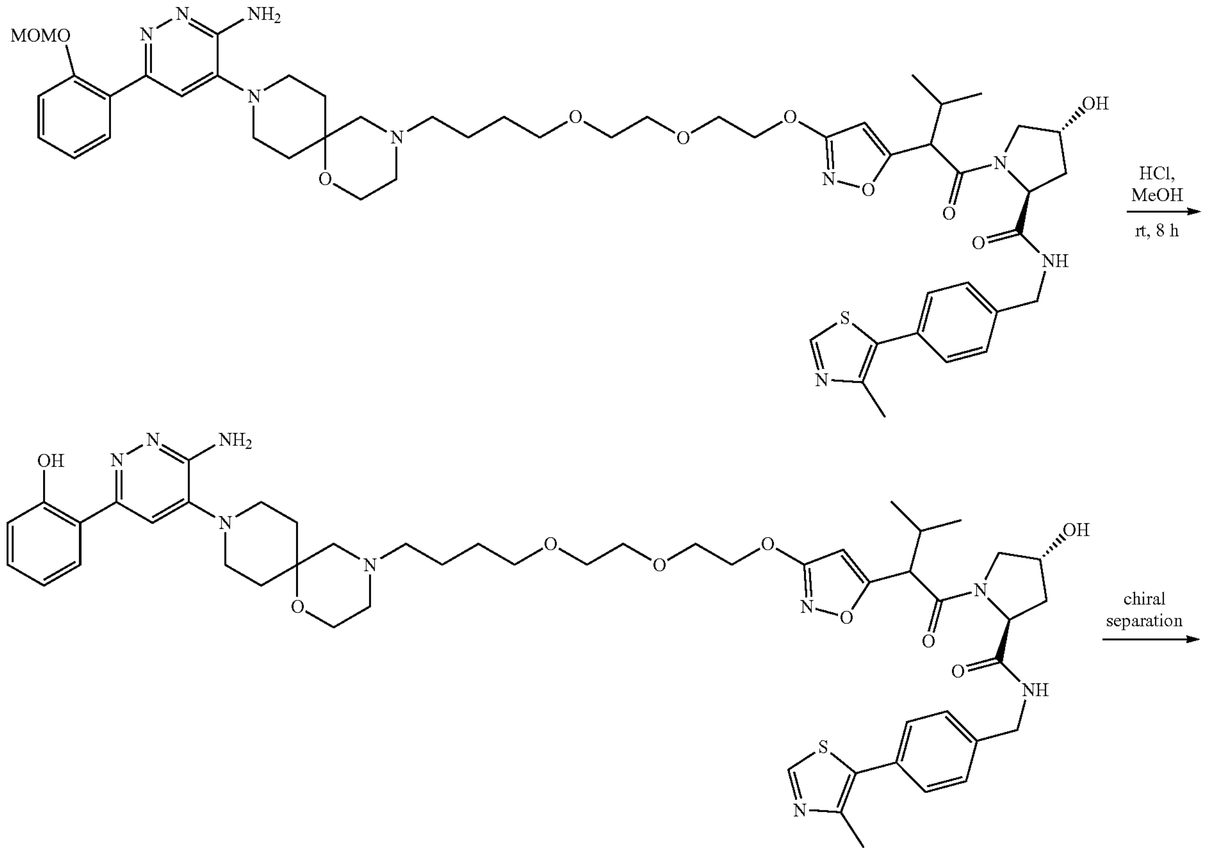
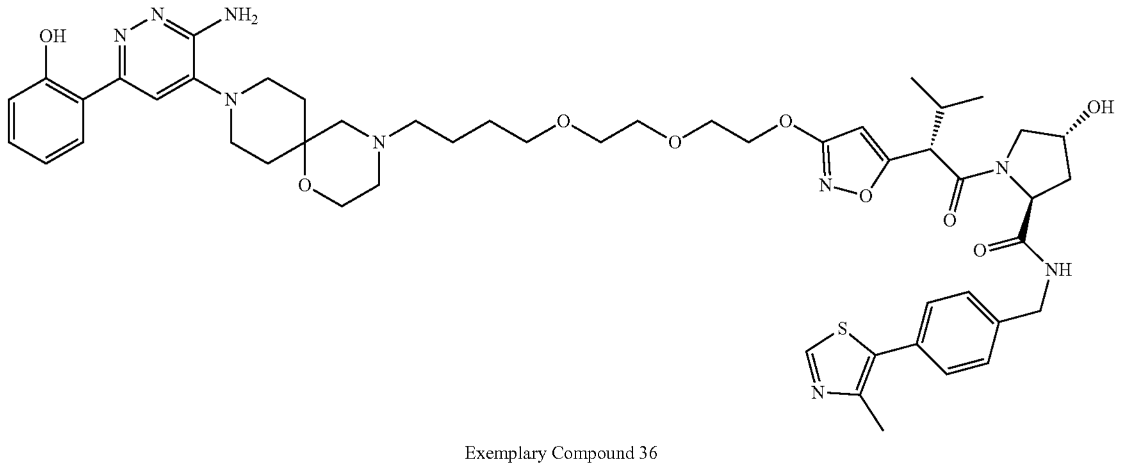
Exemplary Compound 36
+

-continued

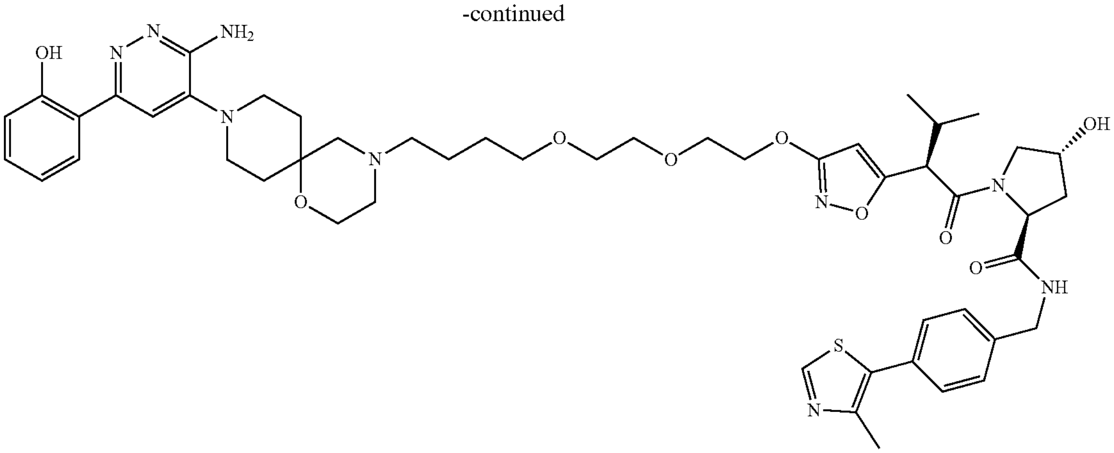

Exemplary Compound 37

Exemplary Synthesis of Exemplary Compound 38 and Exemplary Compound 39

Step 1

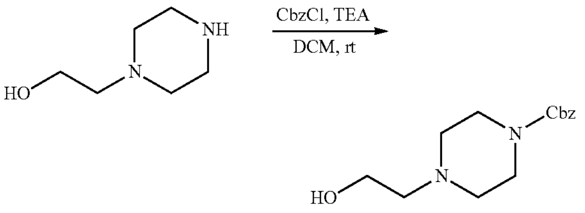

Into a 500-mL round-bottom flask, was placed 2-(piperazin-1-yl)ethan-1-ol (26.0 g, 199.7 mmol, 1.0 equiv), dichloromethane (200.0 mL), triethylamine (40.4 g, 399.3 mmol, 2.0 equiv), benzyl carbonochloridate (40.8 g, 239.2 mmol, 1.2 equiv). The resulting solution was stirred for 2 h at 0° C. The reaction was then quenched by the addition of 10 mL of water. The resulting solution was extracted with dichloromethane (100 mL×3), and the organic layers were combined and concentrated under vacuum. The residue was applied onto a silica gel column eluting with dichloromethane/methanol (10:1). This resulted in 22 g (42%) of benzyl 4-(2-hydroxyethyl)piperazine-1-carboxylate as yellow oil.

Step 2

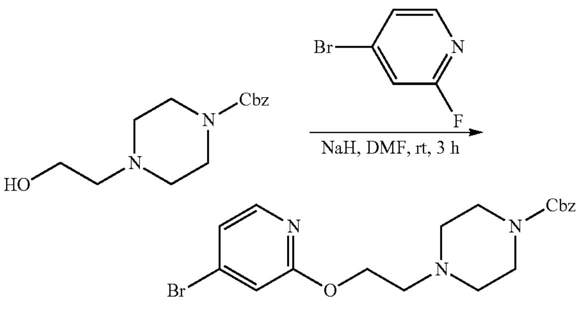

Into a 100-mL round-bottom flask, was placed benzyl 4-(2-hydroxyethyl)piperazine-1-carboxylate (5.3 g, 20.1 mmol, 1.0 equiv) and N,N-dimethylformamide (30.0 mL). This was followed by the addition of sodium hydride (1.6 g, 66.7 mmol, 1.2 equiv) in 5 minutes. To this was added 4-bromo-2-fluoropyridine (3.9 g, 22.2 mmol, 1.1 equiv) in 20 min. The resulting solution was stirred for 4 hours at 0° C. The reaction was then quenched by the addition of 10 mL of ammonium chloride aqueous solution. The resulting solution was extracted with ethyl acetate (50 mL×3), and the organic layers combined and concentrated under vacuum. The residue was applied onto a silica gel column eluting with dichloromethane/methanol (10:1). This resulted in 5.2 g (62%) of benzyl 4-[2-[(4-bromopyridin-2-yl)oxy]ethyl]piperazine-1-carboxylate as yellow oil.

Step 3

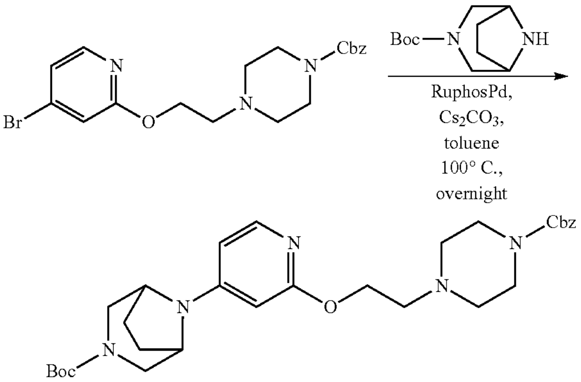

Into a 250-mL round-bottom flask purged and maintained under an inert atmosphere of nitrogen, was placed a solution of benzyl 4-[2-[(4-bromopyridin-2-yl)oxy]ethyl]piperazine-1-carboxylate (2.1 g, 5.0 mmol, 1.0 equiv), RuphosPd II (775.0 mg, 1.0 mmol, 0.2 equiv), and $Cs_2CO_3$ (4.89 g, 15.0 mmol, 3.0 equiv) in PhMe (100 mL). The resulting mixture was stirred overnight at 100° C. in an oil bath. The reaction mixture was quenched by water (100 mL) and extracted with ethyl acetate (100 mL×2). The organic layer was combined and concentrated under reduced pressure, and the residue was applied onto a silica gel column eluting with 100% ethyl acetate. This resulted in 670 mg (32%) of tert-butyl 8-[2-(2-[4-[(benzyloxy)carbonyl]piperazin-1-yl]ethoxy)pyridin-4-yl]-3,8-diazabicyclo[3.2.1]octane-3-carboxylate as a yellow solid.

Step 4

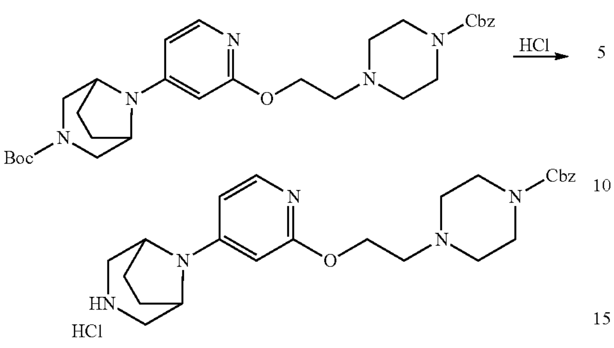

Into a 100-mL round-bottom flask, was placed tert-butyl8-[2-(2-[4-[(benzyloxy)carbonyl]piperazin-1-yl]ethoxy)pyridin-4-yl]-3,8-diazabicyclo[3.2.1]octane-3-carboxylate (670 mg, 1.2 mmol, 1.0 equiv) in methanol (10.0 mL). Then hydrogen chloride in 1,4-dioxane solution (4M, 10 mL) was added. The resulting solution was stirred for 5 hours at room temperature. The resulting mixture was concentrated under vacuum. This resulted in 410 mg (69%) of benzyl 4-[2-[(4-[3,8-diazabicyclo[3.2.1]octan-8-yl]pyridin-2-yl)oxy]ethyl] piperazine-1-carboxylate hydrochloride as a yellow solid.

Step 5

Into a 10-mL sealed tube, was placed benzyl 4-[2-[(4-[3,8-diazabicyclo[3.2.1]octan-8-yl]pyridin-2-yl)oxy]ethyl]piperazine-1-carboxylate hydrochloride (200.0 mg, 0.4 mmol, 1.0 equiv), 4-bromo-6-chloropyridazin-3-amine (137.0 mg, 0.7 mmol, 1.5 equiv), methyl sulfoxide (3.0 mL), and N,N-diisopropylethylamine (1 mL). The final reaction mixture was irradiated with microwave radiation for 6 hours at 130° C. The reaction was then quenched by the addition of 1 mL of water. The resulting solution was extracted with ethyl acetate (20 mL×3), and the organic layers were combined and concentrated under vacuum. The residue was applied onto a silica gel column eluting with dichloromethane/methanol (10:1). This resulted in 100 mg (42%) of benzyl 4-[2-([4-[3-(3-amino-6-chloropyridazin-4-yl)-3,8-diazabicyclo[3.2.1]octan-8-yl]pyridin-2-yl]oxy)ethyl]piperazine-1-carboxylate as a brown solid.

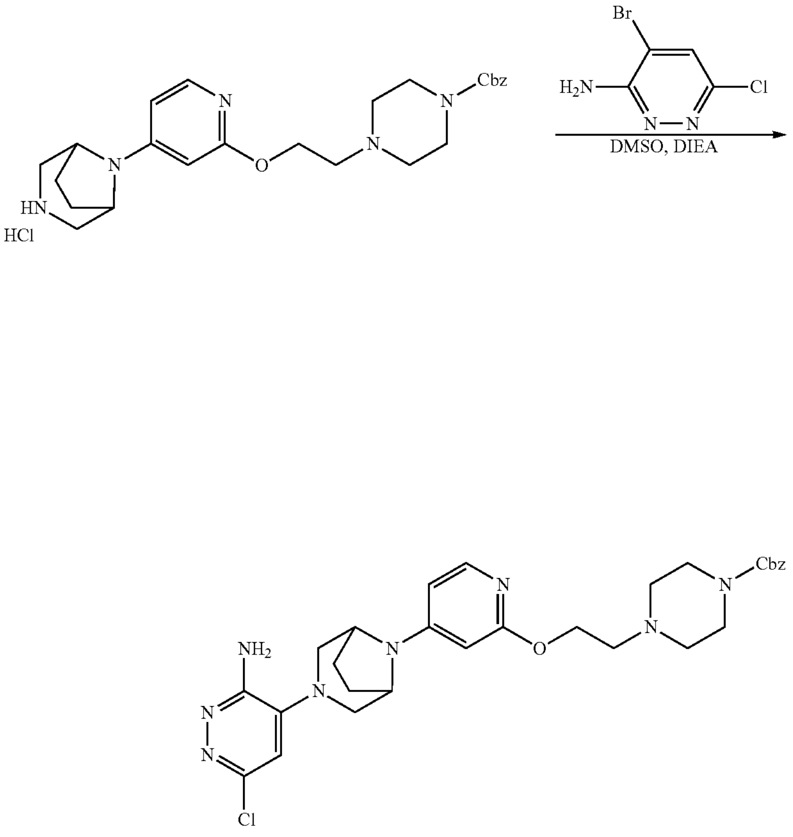

Step 6

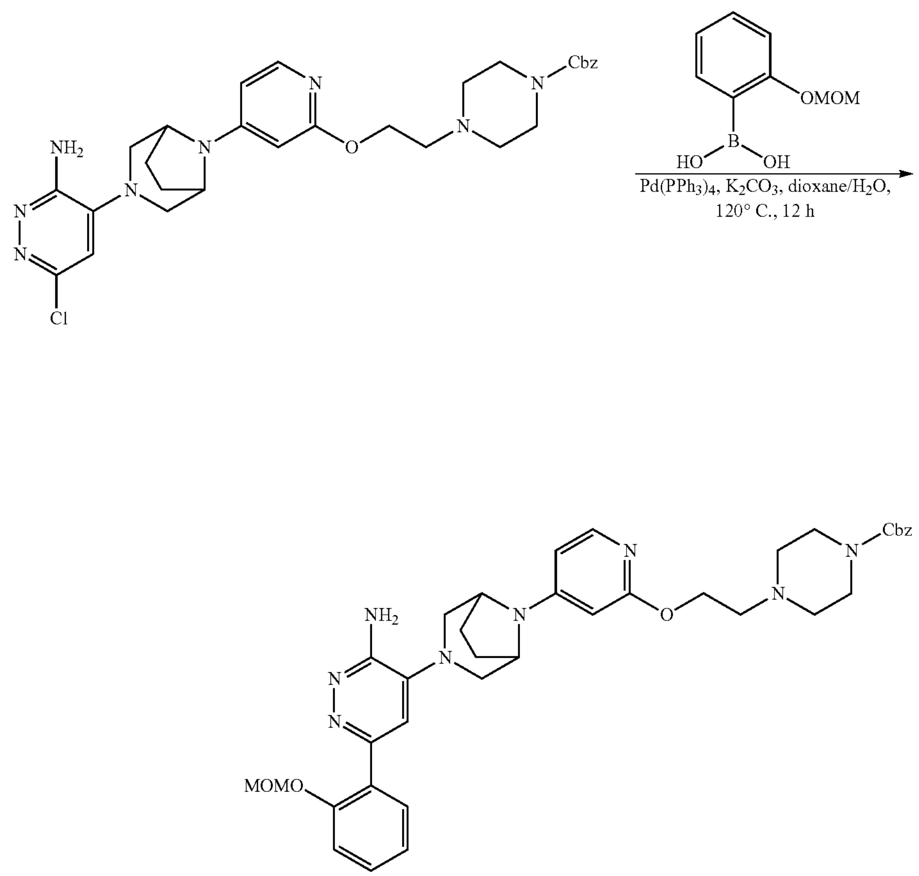

Into a 100-mL round-bottom flask, was placed benzyl 4-[2-([4-[3-(3-amino-6-chloropyridazin-4-yl)-3,8-diazabicyclo[3.2.1]octan-8-yl]pyridin-2-yl]oxy)ethyl]piperazine-1-carboxylate (390 mg, 0.7 mmol, 1.0 equiv), dioxane (8.0 mL), water (2.0 mL), potassium carbonate (279 mg, 2.0 mmol, 3.0 equiv), [2-(methoxymethoxy)phenyl]boronic acid (184.0 mg, 1.0 mmol, 1.50 equiv), $Pd(PPh_3)_4$ (78 mg, 0.07 mmol, 0.1 equiv). The resulting solution was stirred for 2 hours at 100° C. The resulting solution was extracted with ethyl acetate (20 mL×3), and the organic layers combined and concentrated under vacuum. The residue was applied onto a silica gel column eluting with dichloromethane/methanol (10:1). This resulted in 120 mg (26%) of benzyl 4-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethyl)piperazine-1-carboxylate as a brown solid.

Step 7

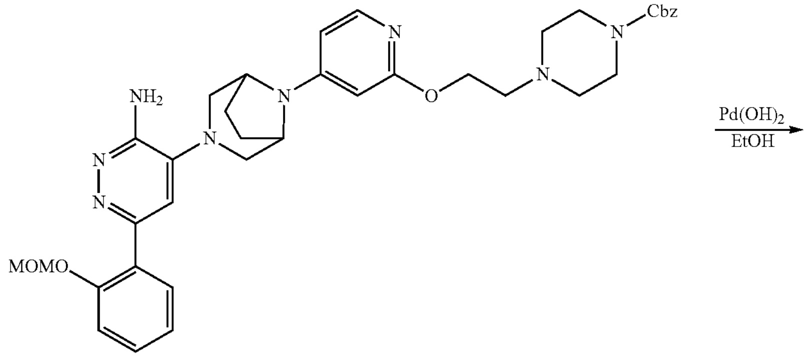

-continued

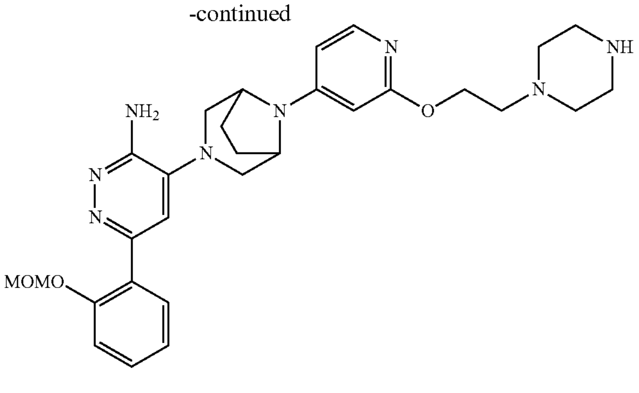

To a solution of benzyl 4-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethyl)piperazine-1-carboxylate (200 mg, 0.29 mmol, 1.00 equiv) in 10 mL of isopropanol was added palladium hydroxide (100 mg, 0.71 mmol, 2.42 equiv) under nitrogen atmosphere in a 100-mL round bottom flask. The flask was then vacuumed and flushed with hydrogen. The resulting solution was stirred for 12 hours at room temperature. The solids were filtered off. The resulting mixture was concentrated under vacuum. This resulted in 70 mg (44%) of 6-[2-(methoxymethoxy)phenyl]-4-(8-[2-[2-(piperazin-1-yl)ethoxy]pyridin-4-yl]-3,8-diazabicyclo[3.2.1]octan-3-yl)pyridazin-3-amine as brown oil.

Step 8

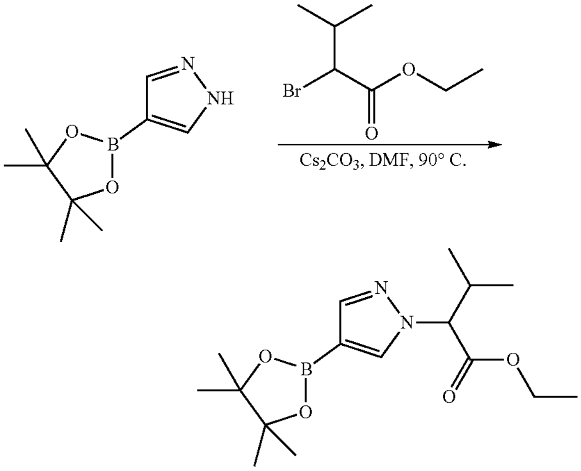

Into a 100-mL round-bottom flask, was placed 4-(tetramethyl-1,3,2-dioxaborolan-2-yl)-1H-pyrazole (1.9 g, 10.0 mmol, 1.00 equiv), N,N-dimethylformamide (30 mL), ethyl 2-bromo-3-methylbutanoate (2.1 g, 10.0 mmol, 1.0 equiv), and cesium carbonate (10.0 g, 30.7 mmol, 3.0 equiv). The resulting solution was stirred for 12 hours at 90° C. The reaction was then quenched by the addition of 10 mL of water. The resulting solution was extracted with ethyl acetate (20 mL×3), and the organic layers combined and concentrated under vacuum. The residue was applied onto a silica gel column eluting with ethyl acetate/petroleum ether (1:6). This resulted in 3.3 g (93%) of ethyl 3-methyl-2-[4-(tetramethyl-1,3,2-dioxaborolan-2-yl)-1H-pyrazol-1-yl]butanoate as a white solid.

Step 9

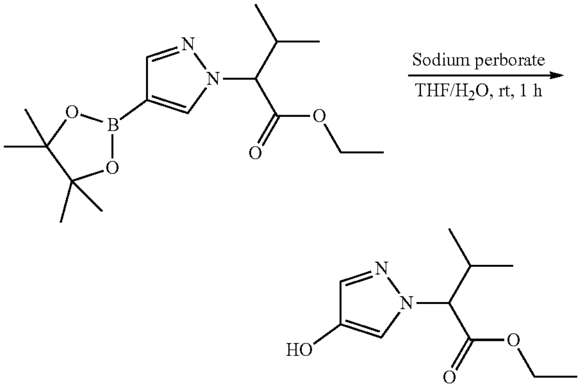

Into a 250-mL round-bottom flask, was placed ethyl 3-methyl-2-[4-(tetramethyl-1,3,2-dioxaborolan-2-yl)-1H-pyrazol-1-yl]butanoate (3.0 g, 9.3 mmol, 1.0 equiv), tetrahydrofuran (30 mL), water (30 mL), sodium perborate (3.5 g, 23.3 mmol, 2.5 equiv). The resulting solution was stirred for 12 hours at room temperature. The resulting mixture was concentrated under vacuum. The resulting solution was extracted with ethyl acetate (20 ml×3), and the organic layers were combined and concentrated under vacuum. The residue was applied onto a silica gel column eluting with ethyl acetate/petroleum ether (1:1). This resulted in 1740 mg (88%) of ethyl 2-(4-hydroxy-1H-pyrazol-1-yl)-3-methylbutanoate as a white solid.

Step 10

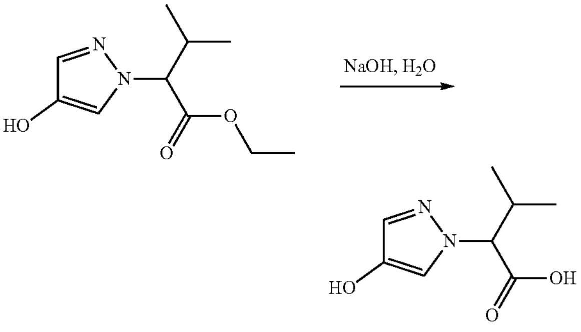

Into a 50-mL round-bottom flask, was placed ethyl 2-(4-hydroxy-1H-pyrazol-1-yl)-3-methylbutanoate (3.5 g, 16.5 mmol, 1.0 equiv), methanol (10 mL), water (10 mL), and sodium hydroxide (2.7 g, 67.5 mmol, 4.0 equiv). The resulting solution was stirred for 12 hours at room temperature. The pH value of the solution was adjusted to 2 with 2M HCl. The crude product was purified by prep-HPLC with the following conditions: Column, XBridge Shield RP18 OBD Column, 5 um, 19*150 mm; mobile phase, Water (0.1% FA) and acetonitrile (0.0% acetonitrile up to 4.0% in 2 min, up to 20.0% in 8 min); Detector, UV 254 nm. This resulted in 1.5 g (49%) of 2-(4-hydroxy-1H-pyrazol-1-yl)-3-methylbutanoic acid as a white oil.

Step 11

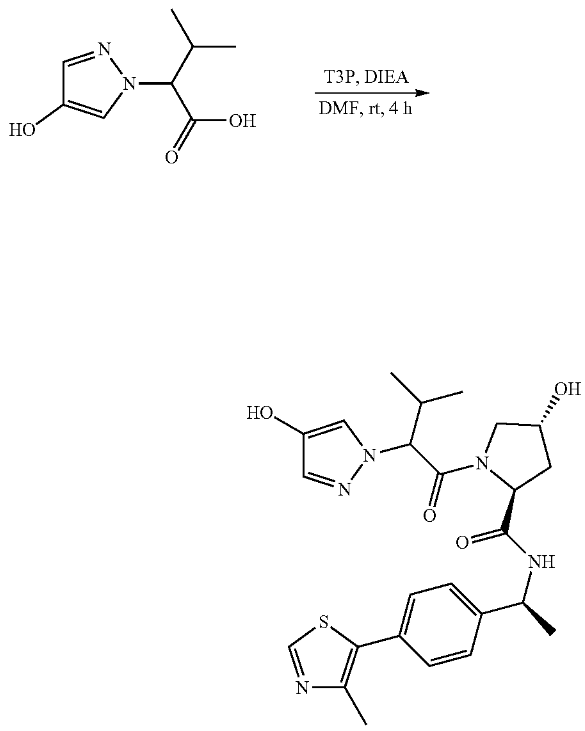 [SMILES: CC(C)C(C(=O)O)n1cc(O)cn1 ; Cc1ncsc1-c1ccc([C@H](C)NC(=O)[C@@H]2C[C@@H](O)CN2C(=O)C(C(C)C)n2cc(O)cn2)cc1]

Into a 100-mL round-bottom flask, was placed 2-(4-hydroxy-1H-pyrazol-1-yl)-3-methylbutanoic acid (500 mg, 2.7 mmol, 1.0 equiv), N,N-dimethylformamide (20 mL), (2S,4R)-4-hydroxy-N-[(1S)-1-[4-(4-methyl-1,3-thiazol-5-yl)phenyl]ethyl]pyrrolidine-2-carboxamide hydrochloride (900 mg, 2.5 mmol, 0.9 equiv), DIEA (1.1 g, 8.5 mmol, 3.0 equiv), T3P (2.6 g, 1.5 equiv). The resulting solution was stirred for 1 hour at room temperature. The reaction was then quenched by the addition of 5 mL of water. The resulting solution was extracted with ethyl acetate (30 mL×3) and the organic layers combined and concentrated under vacuum. The residue was applied onto a silica gel column with dichloromethane/methanol (10:1). This resulted in 800 mg (59%) of (2S,4R)-4-hydroxy-1-[2-(4-hydroxy-1H-pyrazol-1-yl)-3-methylbutanoyl]-N-[(1S)-1-[4-(4-methyl-1,3-thiazol-5-yl)phenyl]ethyl]pyrrolidine-2-carboxamide as a yellow solid.

Step 12

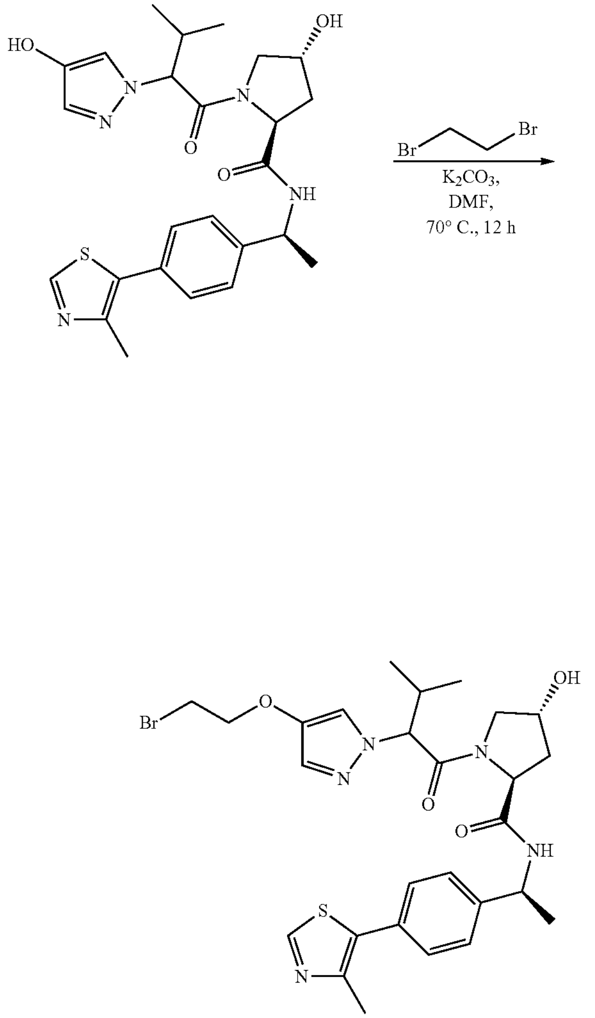

Into a 5-mL sealed tube, was placed (2S,4R)-4-hydroxy-1-[2-(4-hydroxy-1H-pyrazol-1-yl)-3-methylbutanoyl]-N-[(1S)-1-[4-(4-methyl-1,3-thiazol-5-yl)phenyl]ethyl]pyrrolidine-2-carboxamide (300 mg, 0.60 mmol, 1.0 equiv), N,N-dimethylformamide (5.0 mL), 1,2-dibromoethane (222 mg, 1.2 mmol, 2.0 equiv), potassium carbonate (250 mg, 1.8 mmol, 3.0 equiv). The resulting solution was stirred for 12 hours at 70° C. The reaction was then quenched by the addition of 1 mL of water. The crude product was purified by Prep-HPLC with the following conditions: Column, XBridge Shield RP18 OBD Column, 5 um, 19*150 mm; mobile phase, water (10 mmol/L ammonium bicarbonate) and acetonitrile (35.0% acetonitrile up to 47.0% in 8 min); Detector, UV 254 nm. This resulted in 120 mg (33%) of (2S,4R)-1-[2-[4-(2-bromoethoxy)-1H-pyrazol-1-yl]-3-methylbutanoyl]-4-hydroxy-N-[(1S)-1-[4-(4-methyl-1,3-thiazol-5-yl)phenyl]ethyl]pyrrolidine-2-carboxamide as a yellow solid.

Step 13

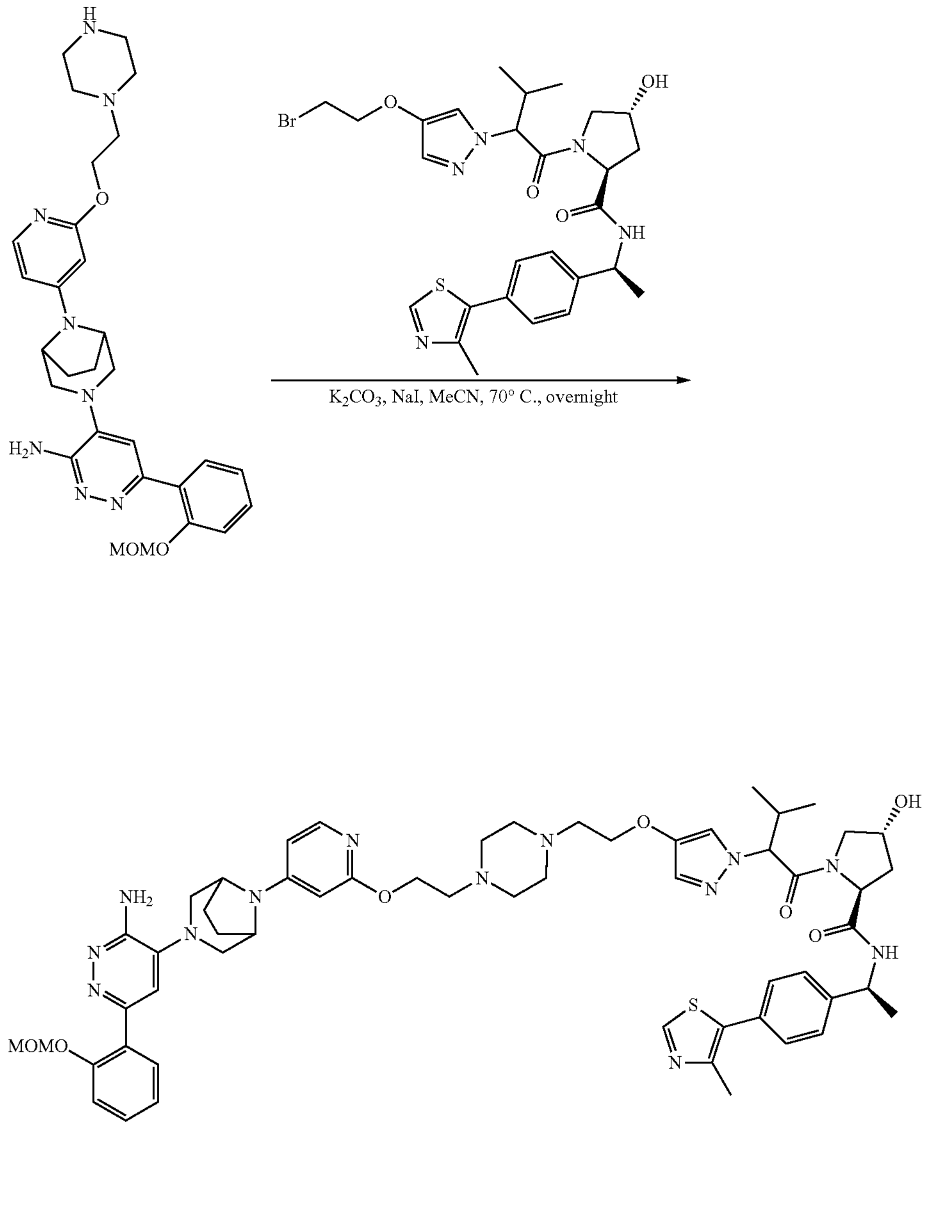

Into a 100-mL round-bottom flask, was placed 6-[2-(methoxymethoxy)phenyl]-4-(8-[2-[2-(piperazin-1-yl) ethoxy]pyridin-4-yl]-3,8-diazabicyclo[3.2.1]octan-3-yl) pyridazin-3-amine (54.6 mg, 0.1 mmol, 1.0 equiv), acetonitrile (10.0 mL), potassium carbonate (41 mg, 0.30 mmol, 3.0 equiv), sodium iodide (18 mg, 0.1 mmol, 1.2 equiv), (2S,4R)-1-2-[4-(2-bromoethoxy)-1H-pyrazol-1-yl]-3-methylbutanoyl-4-hydroxy-N-[(1S)-1-[4-(4-methyl-1,3-thiazol-5-yl)phenyl]ethyl]pyrrolidine-2-carboxamide (60 mg, 0.1 mmol, 1.0 equiv). The resulting solution was stirred for 12 hours at 70° C. The reaction was then quenched by the addition of 3 mL of water. The resulting solution was extracted with ethyl acetate (30 mL×3), and the organic layers were combined and concentrated under vacuum. The residue was applied onto a silica gel column eluting with dichloromethane/methanol (10/1). This resulted in 30 mg (29%) of (2S,4R)-1-(2-[4-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1H-pyrazol-1-yl]-3-methylbutanoyl)-4-hydroxy-N-[(1S)-1-[4-(4-methyl-1,3-thiazol-5-yl)phenyl]ethyl]pyrrolidine-2-carboxamide as a light brown solid.

Step 14
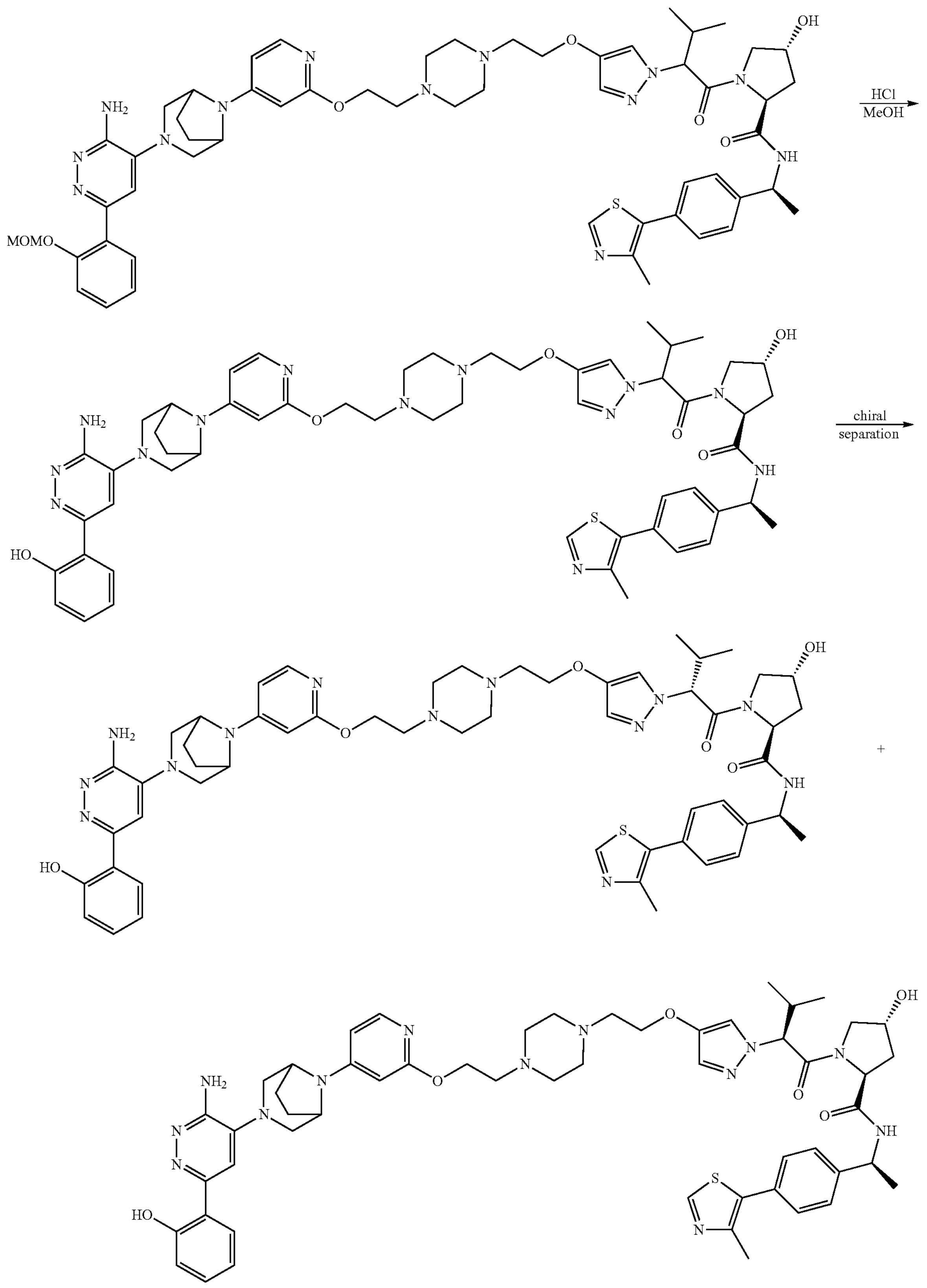

Into a 25-mL round-bottom flask, was placed (2S,4R)-1-[2-(4-[2-[4-(2-[[4-(3-[3-amino-6-[2-(methoxymethoxy)phenyl]pyridazin-4-yl]-3,8-diazabicyclo[3.2.1]octan-8-yl)pyridin-2-yl]oxy]ethyl)piperazin-1-yl]ethoxy]-1H-pyrazol-1-yl)-3-methylbutanoyl]-4-hydroxy-N-[(1S)-1-[4-(4-methyl-1,3-thiazol-5-yl)phenyl]ethyl]pyrrolidine-2-carboxamide (40 mg, 0.04 mmol, 1.0 equiv), methanol (8 mL), hydrogen chloride (150 mL). The resulting solution was stirred for 6 hours at room temperature. The reaction was then quenched by the addition of 1 mL of water. The crude product (5 mL) was purified by Prep-HPLC with the following conditions: Column, XBridge Shield RP18 OBD Column, 5 um, 19*150 mm; mobile phase, Water (0.1% formic acid) and acetonitrile (13.0% acetonitrile up to 27.0% in 8 min); Detector, UV 254 nm. This resulted in 30 mg (78%) of (2S,4R)-1-(2-[4-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1H-pyrazol-1-yl]-3-methylbutanoyl)-4-hydroxy-N-[(1S)-1-[4-(4-methyl-1,3-thiazol-5-yl)phenyl]ethyl]pyrrolidine-2-carboxamide as a white solid.

(2S,4R)-1-(2-[4-[2-(4-[2-[(4-[3-[3-amino-6-(2-hydroxy phenyl)pyridazin-4-yl]-3,8-diazabicyclo[3.2.1]octan-8-yl] pyridin-2-yl)oxy]ethyl]piperazin-1-yl)ethoxy]-1H-pyrazol-1-yl]-3-methylbutanoyl)-4-hydroxy-N-[(1S)-1-[4-(4-methyl-1,3-thiazol-5-yl)phenyl]ethyl]pyrrolidine-2-carboxamide was purified by chiral prep-HPLC with the following conditions: Column, Chiralpak IC, 2*25 cm, 5 um; mobile phase, DCM and methanol (hold 50.0% methanol in 11 min); Detector, UV 220/254 nm. This resulted in 5.6 mg of (2S,4R)-1-[(2R)-2-[4-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1H-pyrazol-1-yl]-3-methylbutanoyl]-4-hydroxy-N-[(1S)-1-[4-(4-methyl-1,3-thiazol-5-yl)phenyl]ethyl]pyrrolidine-2-carboxamide as a white solid[$^1$H NMR (300 MHz, Methanol-d4) δ 8.89 (s, 1H), 7.85-7.72 (m, 2H), 7.56-7.36 (m, 6H), 7.31-7.16 (m, 2H), 6.97-6.85 (m, 2H), 6.58 (dd, J=6.2, 2.2 Hz, 1H), 6.24 (d, J=2.1 Hz, 1H), 5.05 (q, J=6.9 Hz, 1H), 4.67 (d, J=10.6 Hz, 1H), 4.60-4.47 (m, 3H), 4.46 (s, 1H), 4.39 (t, J=5.4 Hz, 2H), 4.06 (t, J=5.3 Hz, 2H), 3.87 (dd, J=10.9, 4.2 Hz, 1H), 3.76 (s, 1H), 3.73-3.55 (m, 2H), 3.19-2.99 (m, 2H), 2.92-2.69 (m, 12H), 2.50 (s, 4H), 2.30-2.14 (m, 5H), 1.98 (ddd, J=13.2, 8.7, 4.6 Hz, 1H), 1.54 (d, J=7.0 Hz, 3H), 1.41-1.26 (m, 4H), 1.20 (t, J=7.0 Hz, 2H), 1.08 (d, J=6.5 Hz, 3H), 0.93 (d, J=4.1 Hz, 1H)] and 8.1 mg of (2S,4R)-1-[(2S)-2-[4-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1H-pyrazol-1-yl]-3-methylbutanoyl]-4-hydroxy-N-[(1S)-1-[4-(4-methyl-1,3-thiazol-5-yl)phenyl]ethyl]pyrrolidine-2-carboxamide as a white solid[1H NMR (300 MHz, Methanol-d4) δ 8.88 (d, J=13.8 Hz, 1H), 7.85-7.69 (m, 2H), 7.59-7.30 (m, 6H), 7.32-7.18 (m, 2H), 6.97-6.84 (m, 2H), 6.57 (dd, J=6.1, 2.1 Hz, 1H), 6.23 (t, J=2.7 Hz, 1H), 4.99 (q, J=7.0 Hz, 1H), 4.78 (d, J=8.8 Hz, 1H), 4.60 (t, J=8.2 Hz, 1H), 4.53 (s, 2H), 4.37 (dd, J=6.8, 4.1 Hz, 3H), 4.04 (t, J=5.3 Hz, 2H), 3.64 (p, J=6.7 Hz, 3H), 3.40-3.24 (m, 1H), 3.11 (dd, J=15.8, 4.6 Hz, 2H), 2.88-2.64 (m, 12H), 2.49 (d, J=13.8 Hz, 4H), 2.34-2.10 (m, 6H), 2.06 (s, 1H), 1.95 (td, J=8.5, 4.2 Hz, 1H), 1.50 (d, J=7.0 Hz, 3H), 1.33 (td, J=7.8, 7.4, 4.4 Hz, 5H), 1.20 (t, J=7.0 Hz, 3H), 1.08 (d, J=6.7 Hz, 3H), 0.93 (q, J=6.8 Hz, 1H), 0.74 (dd, J=19.3, 6.7 Hz, 3H)].

Exemplary Synthesis of Exemplary Compound 43 and Exemplary Compound 44

Step 1

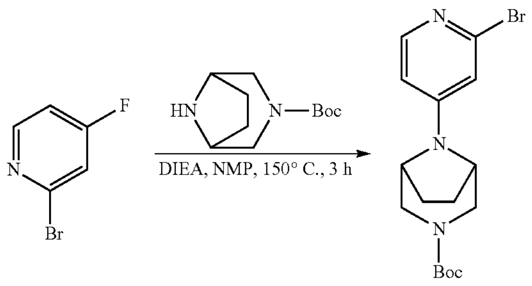 [SMILES: Fc1ccnc(Br)c1 ; CC(C)(C)OC(=O)N1CC2CCC(C1)N2 ; CC(C)(C)OC(=O)N1CC2CCC(C1)N2c1ccnc(Br)c1]

Into a 250-mL round-bottom flask, was placed a solution of 2-bromo-4-fluoropyridine (7.8 g, 44.32 mmol, 1.05 equiv), tert-butyl 3,8-diazabicyclo[3.2.1]octane-3-carboxylate (9 g, 42.4 mmol, 1.00 equiv), DIEA (25 g, 193 mmol, 4.00 equiv) in NMP (120 mL). The resulting solution was stirred for 3 hours at 150° C. The reaction mixture was cooled. The reaction was then quenched by the addition of water (200 mL). The resulting solution was extracted with ethyl acetate (50 mL×3), and the organic layers were combined. The resulting mixture was washed with water (50 mL×1) and brine (50 mL×1). The mixture was dried over anhydrous sodium sulfate and concentrated under vacuum. The residue was applied onto a silica gel column eluting with ethyl acetate/petroleum ether (1:2). This resulted in 11.7 g (75%) of tert-butyl 8-(2-bromopyridin-4-yl)-3,8-diazabicyclo[3.2.1]octane-3-carboxylate as a yellow solid.

Step 2

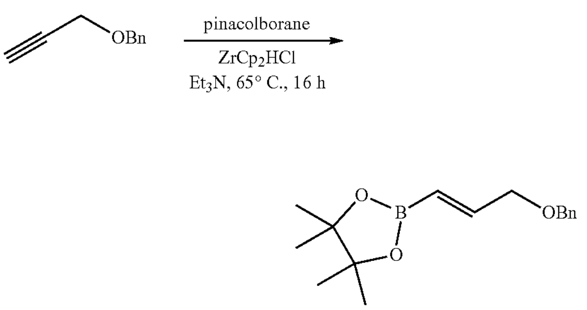

Into a 250-mL round-bottom flask, was placed a mixture of [(prop-2-yn-1-yloxy)methyl]benzene (10 g, 68.4 mmol, 1.00 equiv), pinacolborane (10 mL), $ZrCp_2HCl$ (2 g), triethylamine (850 mg, 8.40 mmol, 0.12 equiv). The resulting solution was stirred for 16 hours at 65° C. in an oil bath. The resulting mixture were quenched with water (30 mL), then was extracted with ethyl acetate (50 mL×3), and the organic layers combined. The resulting mixture was washed with brine (50 mL×1). The resulting mixture was concentrated under vacuum. The residue was applied onto a silica gel column eluting with ethyl acetate/petroleum ether (1:1). This resulted in 12.5 g (67%) of 2-[(1E)-3-(benzyloxy)prop-1-en-1-yl]-4,4,5,5-tetramethyl-1,3,2-dioxaborolane as a yellow solid.

Step 3

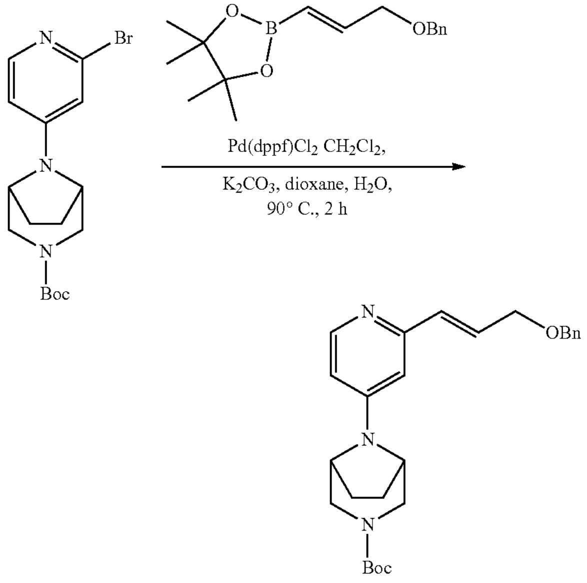

Into a 250-mL round-bottom flask purged and maintained under an inert atmosphere of nitrogen, was placed a solution of tert-butyl 8-(2-bromopyridin-4-yl)-3,8-diazabicyclo[3.2.1]octane-3-carboxylate (4.0 g, 10.9 mmol, 1.00 equiv), 2-[(1E)-3-(benzyloxy)prop-1-en-1-yl]-4,4,5,5-tetramethyl-1,3,2-dioxaborolane (4.48 g, 16.3 mmol, 1.50 equiv), Pd(dppf)$_2$Cl$_2$ dichloromethane (890 mg, 1.09 mmol, 0.10 equiv), and potassium carbonate (4.5 g, 32.6 mmol, 3.00 equiv) in dioxane/$H_2O$ (80/20 mL). The resulting solution was stirred for 2 hours at 90° C. The reaction mixture was cooled to room temperature. The resulting mixture was concentrated under vacuum. The residue was applied onto a silica gel column eluting with ethyl acetate/petroleum ether (1:1). This resulted in 4.55 g (96%) of tert-butyl 8-[2-[(1E)-3-(benzyloxy)prop-1-en-1-yl]pyridin-4-yl]-3,8-diazabicyclo[3.2.1]octane-3-carboxylate as a yellow solid.

Step 4

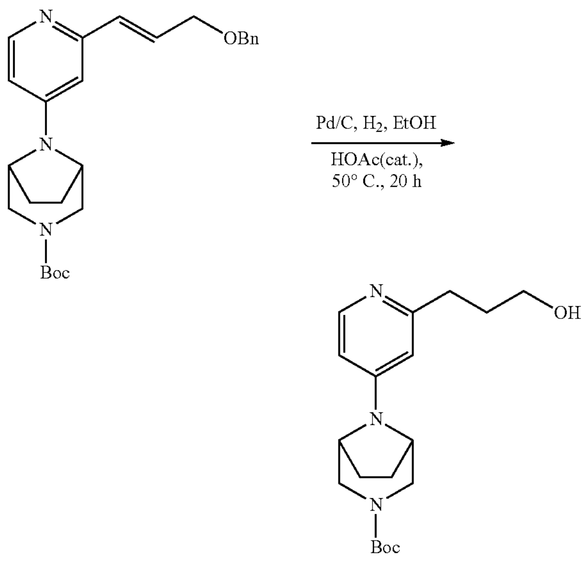

Into a 250-mL round-bottom flask purged and maintained under an inert atmosphere of nitrogen, was placed a solution of tert-butyl 8-[2-[(1E)-3-(benzyloxy)prop-1-en-1-yl]pyridin-4-yl]-3,8-diazabicyclo[3.2.1]octane-3-carboxylate (12.9 g, 29.6 mmol, 1.00 equiv) in methanol/HOAc (200/0.5 mL). Palladium on carbon (6 g) was added under nitrogen atmosphere. The flask was then vacuumed and flushed with hydrogen. The reaction mixture was hydrogenated at 50° C. for 20 hours under hydrogen atmosphere using a hydrogen balloon. The solids were filtered out through a celite pad, and the filtrate was concentrated under reduced pressure. This resulted in 10.2 g (99%) of tert-butyl 8-[2-(3-hydroxypropyl)pyridin-4-yl]-3,8-diazabicyclo[3.2.1]octane-3-carboxylate as a yellow oil.

Step 5

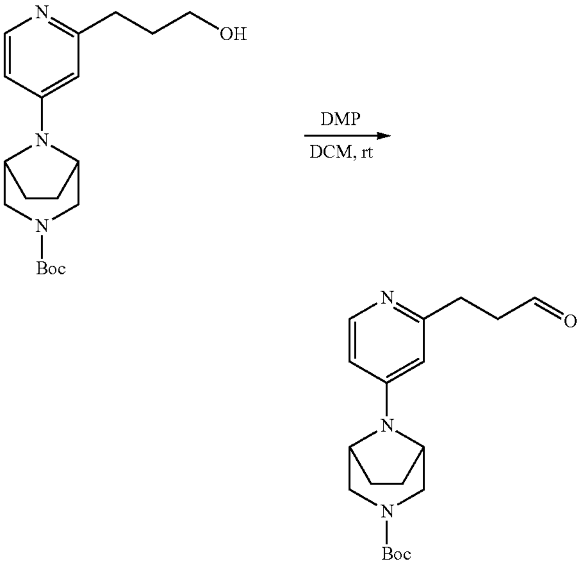

Into a 100-mL round-bottom flask was placed tert-butyl 8-[2-(3-hydroxypropyl)pyridin-4-yl]-3,8-diazabicyclo[3.2.1]octane-3-carboxylate (700 mg, 2.01 mmol, 1.00 equiv) in dichloromethane (30 mL), and Dess-Martin periodinane reagent (1.7 g, 2.00 equiv) was added at 0-5'C. The resulting solution was stirred for 6 hours at room temperature. The resulting mixture was concentrated under vacuum at 15° C. The residue was applied onto a silica gel column eluting with dichloromethane/methanol (5:1). This resulted in 500 mg (72%) of tert-butyl 8-[2-(3-oxopropyl)pyridin-4-yl]-3,8-diazabicyclo[3.2.1]octane-3-carboxylate as a white solid.

Step 6

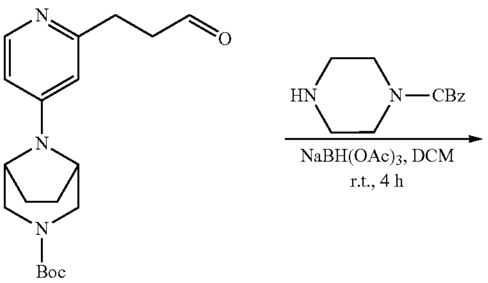

-continued

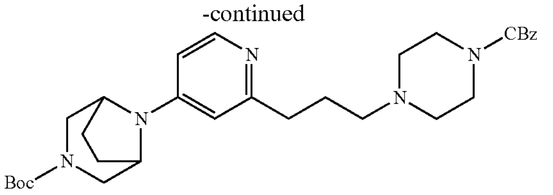

Into a 50-mL round-bottom flask, was placed tert-butyl 8-[2-(3-oxopropyl)pyridin-4-yl]-3,8-diazabicyclo[3.2.1]octane-3-carboxylate (1.4 g, 4.05 mmol, 1.00 equiv), benzyl piperazine-1-carboxylate (1.07 g, 4.86 mmol, 1.20 equiv) in dichloromethane (20 mL). It was stirred for 20 min and $NaBH(OAc)_3$ (2.58 g, 12.2 mmol, 3.00 equiv) was added at 0° C. The resulting solution was stirred for 4 hours at room temperature. The reaction was then quenched by the addition of water/ice (50 mL). The resulting solution was extracted with dichloromethane (50 mL×3) and the organic layers were combined and dried over anhydrous sodium sulfate. The residue was applied onto a silica gel column eluting with dichloromethane/methanol (10/1). This resulted in 2.19 g (98%) of tert-butyl 8-[2-(3-[4-[(benzyloxy)carbonyl]piperazin-1-yl]propyl)pyridin-4-yl]-3,8-diazabicyclo[3.2.1]octane-3-carboxylate as a light yellow oil.

Step 7

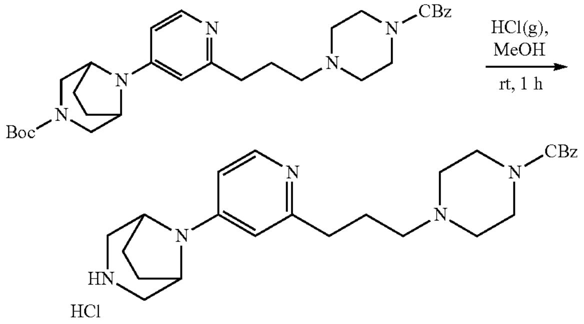

Into a 100-mL round-bottom flask, was placed tert-butyl 8-[2-(3-[4-[(benzyloxy)carbonyl]piperazin-1-yl]propyl)pyridin-4-yl]-3,8-diazabicyclo[3.2.1]octane-3-carboxylate (2.19 g, 3.98 mmol, 1.00 equiv) in methanol (20 mL). Hydrogen chloride gas was bubbled through the resulting solution while stirring for 1 h at room temperature. The resulting mixture was concentrated under vacuum. This resulted in 1.79 g (92%) of benzyl 4-[3-(4-[3,8-diazabicyclo[3.2.1]octan-8-yl]pyridin-2-yl)propyl]piperazine-1-carboxylate hydrochloride as a light yellow solid.

Step 8

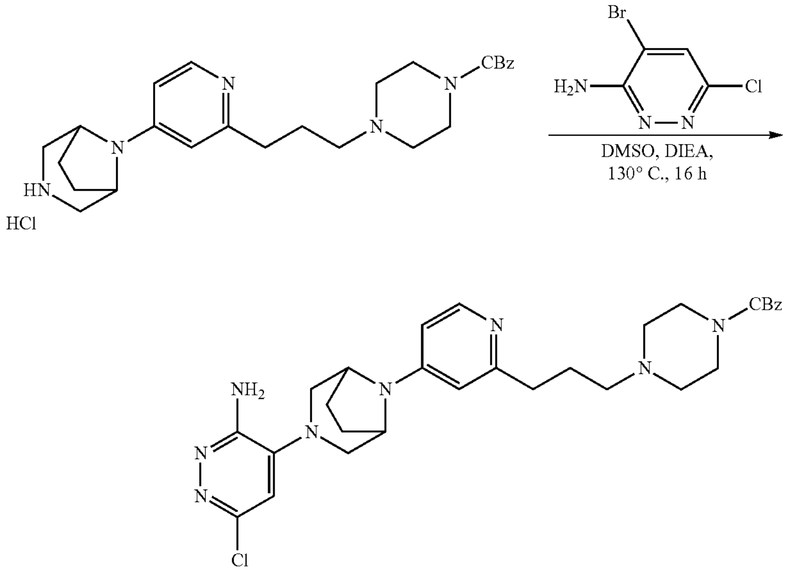

Into a 20-mL microwave tube purged and maintained under an inert atmosphere of nitrogen was placed benzyl 4-[3-(4-[3,8-diazabicyclo[3.2.1]octan-8-yl]pyridin-2-yl)propyl]piperazine-1-carboxylate hydrochloride (1.79 g, 3.68 mmol, 1.00 equiv), 4-bromo-6-chloropyridazin-3-amine (2.47 g, 11.9 mmol, 3.00 equiv), DIEA (5.0 mL) in DMSO (10 mL). The resulting solution was stirred for 16 hours at 130° C. in an oil bath. The reaction was then quenched by the addition of water/ice (50 mL). The resulting solution was extracted with dichloromethane (50 mL×3), and the organic layers were combined and dried over anhydrous sodium sulfate. The residue was applied onto a silica gel column eluting with dichloromethane/methanol (5/1). This resulted in 1.21 g (57%) of benzyl 4-(3-[4-[3-(3-amino-6-chloropyridazin-4-yl)-3,8-diazabicyclo[3.2.1]octan-8-yl]pyridin-2-yl]propyl)piperazine-1-carboxylate as a brown solid. Benzyl 4-(3-[4-[3-(3-amino-6-chloropyridazin-4-yl)-3,8-diazabicyclo[3.2.1]octan-8-yl]pyridin-2-yl]propyl)piperazine-1-carboxylate was converted to 6-[2-(methoxymethoxy)phenyl]-4-(8-[2-[3-(piperazin-1-yl)propyl]pyridin-4-yl]-3,8-diazabicyclo[3.2.1]octan-3-yl)pyridazin-3-amine (used in step 10) according to the scheme below and using procedures described above for other examples.

Step 9

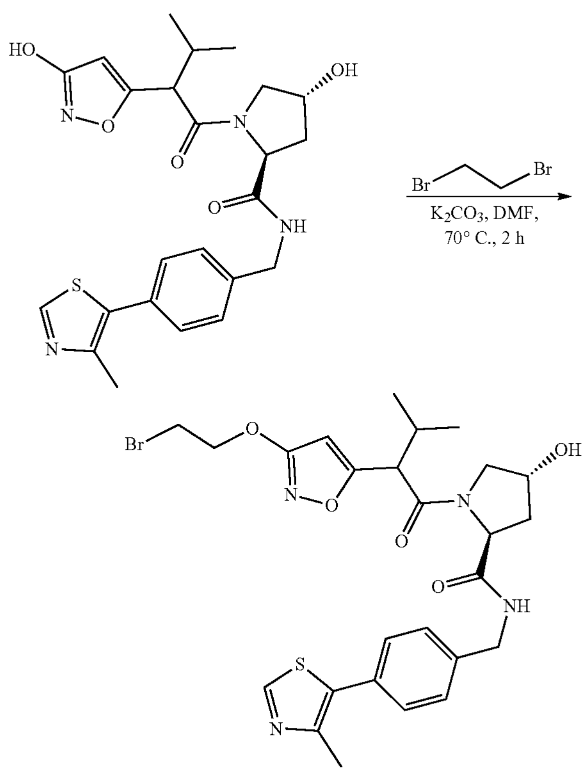

Into a 50-mL round-bottom flask, was placed a solution of (2S,4R)-4-hydroxy-1-[2-(3-hydroxy-1,2-oxazol-5-yl)-3-methylbutanoyl]-N-[[4-(4-methyl-1,3-thiazol-5-yl)phenyl]methyl]pyrrolidine-2-carboxamide (480 mg, 1.0 mmol, 1.0 equiv) in N,N-dimethylformamide (10 mL), potassium carbonate (300 mg, 2.2 mmol, 2.2 equiv) and 1,2-dibromoethane (300 mg, 1.6 mmol, 1.6 equiv). The resulting solution was stirred for 2 hours at 70° C. in an oil bath. The reaction was then quenched by the addition of 20 mL of water. The resulting solution was extracted with of ethyl acetate (3×30 mL), and the organic layers were combined and dried over anhydrous sodium sulfate and concentrated under vacuum. The residue was applied onto a silica gel column eluting with ethyl acetate/petroleum ether (1:0). This resulted in 235 mg (40%) of (2S,4R)-1-[2-[3-(2-bromoethoxy)-1,2-oxazol-5-yl]-3-methylbutanoyl]-4-hydroxy-N-[[4-(4-methyl-1,3-thiazol-5-yl) phenyl]methyl] pyrrolidine-2-carboxamide as a light yellow solid.

Step 10

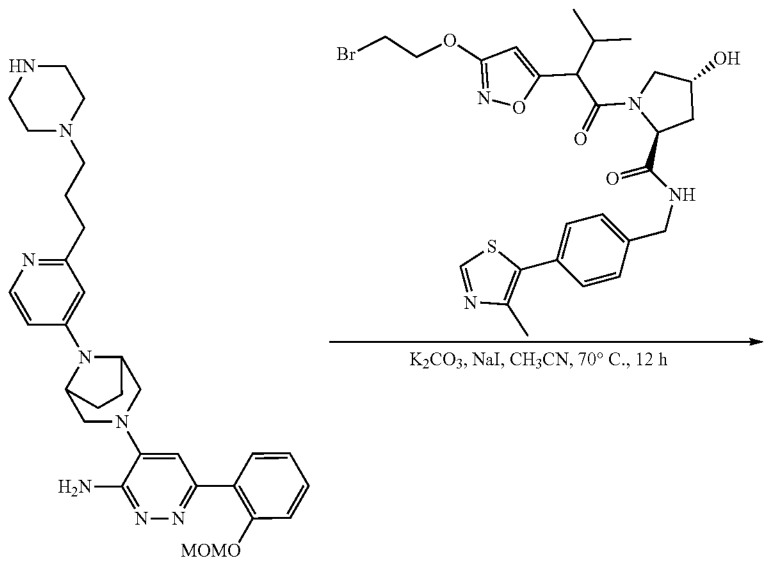

-continued

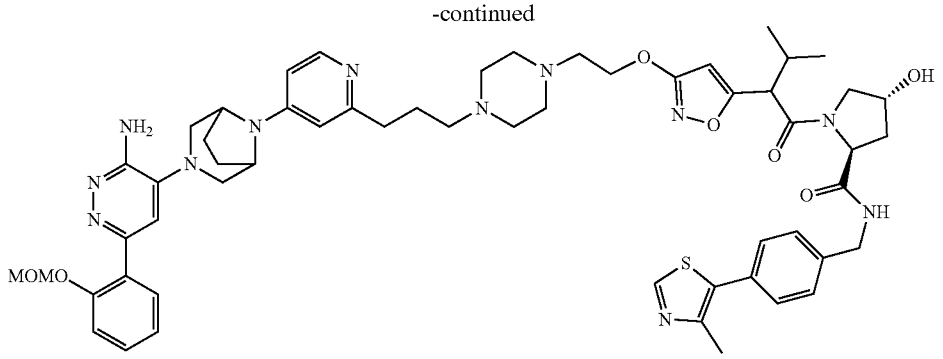

Into a 20-mL microwave tube purged and maintained under an inert atmosphere of nitrogen was placed 6-[2-(methoxymethoxy)phenyl]-4-(8-[2-[3-(piperazin-1-yl)propyl]pyridin-4-yl]-3,8-diazabicyclo[3.2.1]octan-3-yl) pyridazin-3-amine (92 mg, 0.17 mmol, 1.00 equiv) [prepared from benzyl 4-(3-[4-[3-(3-amino-6-chloro-pyridazin-4-yl)-3,8-diazabicyclo[3.2.1]octan-8-yl]pyridin-2-yl]propyl)piperazine-1-carboxylate from step 8 according to the scheme below and using procedures described above for other examples], (2S,4R)-1-2-[3-(2-bromoethoxy)-1,2-oxazol-5-yl]-3-methylbutanoyl-4-hydroxy-N-[4-(4-methyl-1,3-thiazol-5-yl)phenyl]methylpyrrolidine-2-carboxamide (100 mg, 0.17 mmol, 1.00 equiv), potassium carbonate (70 mg, 0.51 mmol, 3.00 equiv), NaI (25 mg, 0.17 mmol, 1.00 equiv) in acetonitrile (10 mL). The resulting mixture was stirred for 12 hours at 70° C. in an oil bath. The resulting solution was extracted with dichloromethane (100 mL) and the organic layers combined. The resulting mixture was washed with brine (30 mL). The mixture was dried over anhydrous sodium sulfate and concentrated under vacuum. This resulted in 180 mg (crude) of (2S,4R)-1-(2-[3-[2-(4-[3-[4-(3-[3-amino-6-[2-(methoxymethoxy)phenyl] pyridazin-4-yl]-3,8-diazabicyclo[3.2.1]octan-8-yl)pyridin-2-yl]propyl]piperazin-1-yl)ethoxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide as a light yellow solid.

(2S,4R)-1-(2-[3-[2-(4-[3-[4-(3-[3-amino-6-[2-(methoxymethoxy)phenyl]pyridazin-4-yl]-3,8-diazabicyclo [3.2.1]octan-8-yl)pyridin-2-yl]propyl]piperazin-1-yl) ethoxy]-1,2-oxazol-5-yl]-3-methylbutanoyl)-4-hydroxy-N-[[4-(4-methyl-1,3-thiazol-5-yl)phenyl]methyl]pyrrolidine-2-carboxamide was converted to the final compounds, (2S, 4R)-1-[(2S)-2-[3-(2-[4-[3-(4-[3-[3-amino-6-(2-hydroxyphenyl)pyridazin-4-yl]-3,8-diazabicyclo[3.2.1] octan-8-yl]pyridin-2-yl)propyl]piperazin-1-yl]ethoxy)-1,2-oxazol-5-yl]-3-methylbutanoyl]-4-hydroxy-N-[[4-(4-methyl-1,3-thiazol-5-yl)phenyl]methyl]pyrrolidine-2-carboxamide and (2S,4R)-1-[(2R)-2-[3-(2-[4-[3-(4-[3-[3-amino-6-(2-hydroxyphenyl)pyridazin-4-yl]-3,8-diazabicyclo[3.2.1]octan-8-yl]pyridin-2-yl)propyl] piperazin-1-yl]ethoxy)-1,2-oxazol-5-yl]-3-methylbutanoyl]-4-hydroxy-N-[[4-(4-methyl-1,3-thiazol-5-yl)phenyl]methyl]pyrrolidine-2-carboxamide according to the scheme below and using procedures analogous to those described above for other examples.

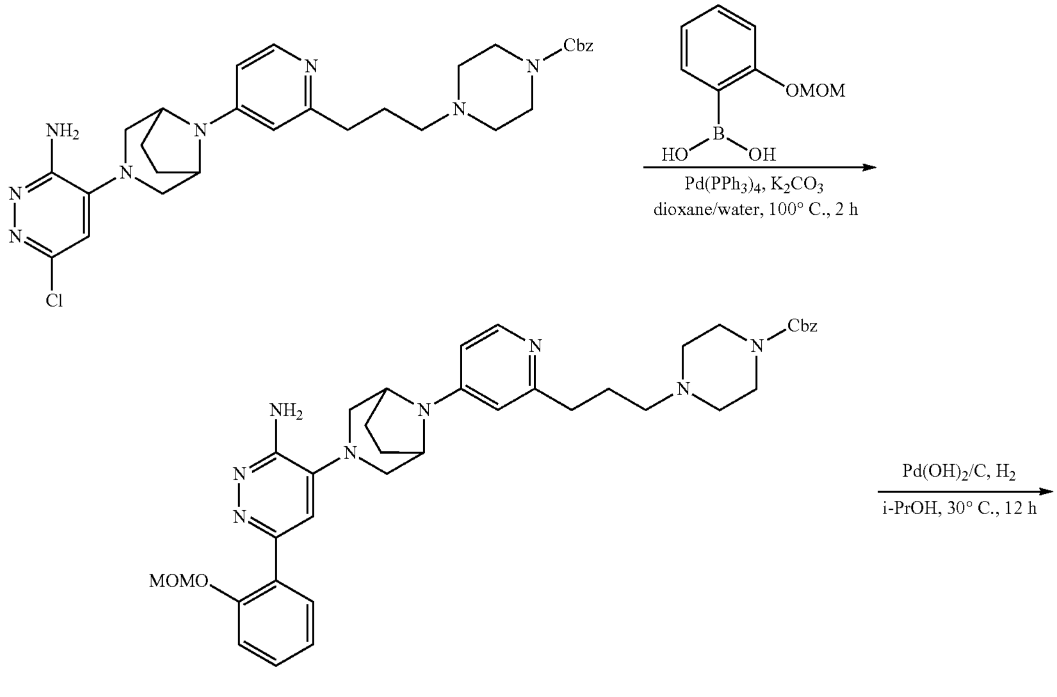

-continued
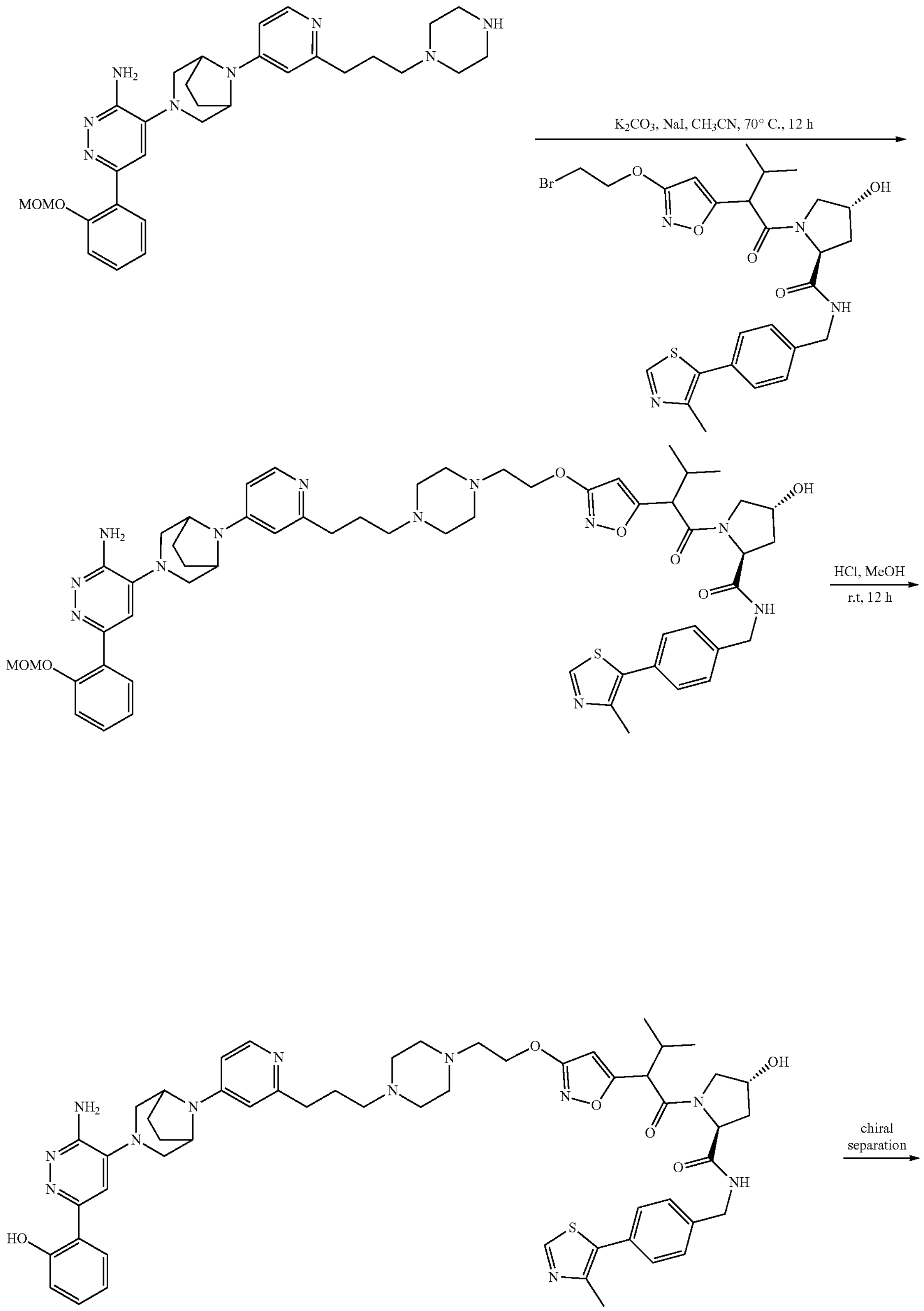

-continued
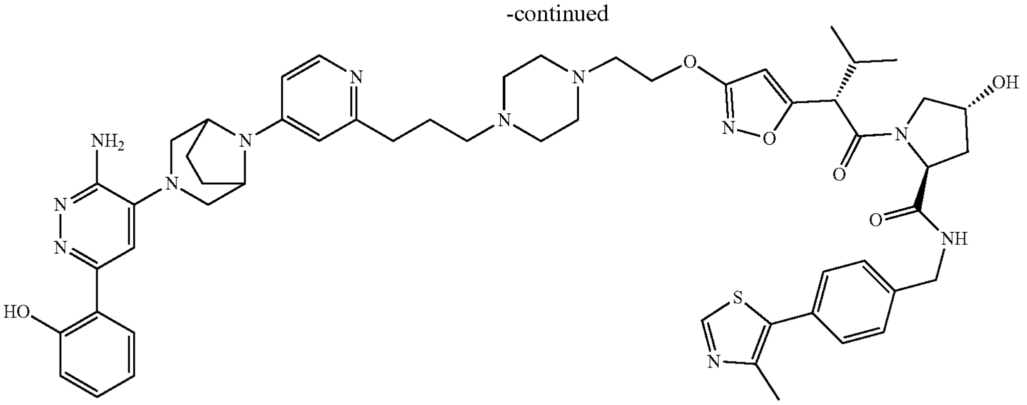
+
Exemplary Compound 43
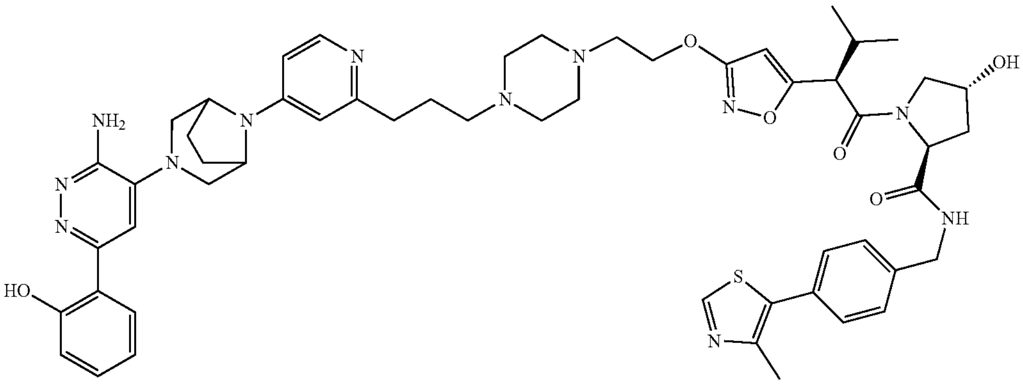
Exemplary Compound 44
Exemplary Synthesis of Exemplary Compound 40
Exemplary Compound 40 was prepared according to the scheme below using procedures described for other examples above as well as procedures appreciated by those skilled in the art.
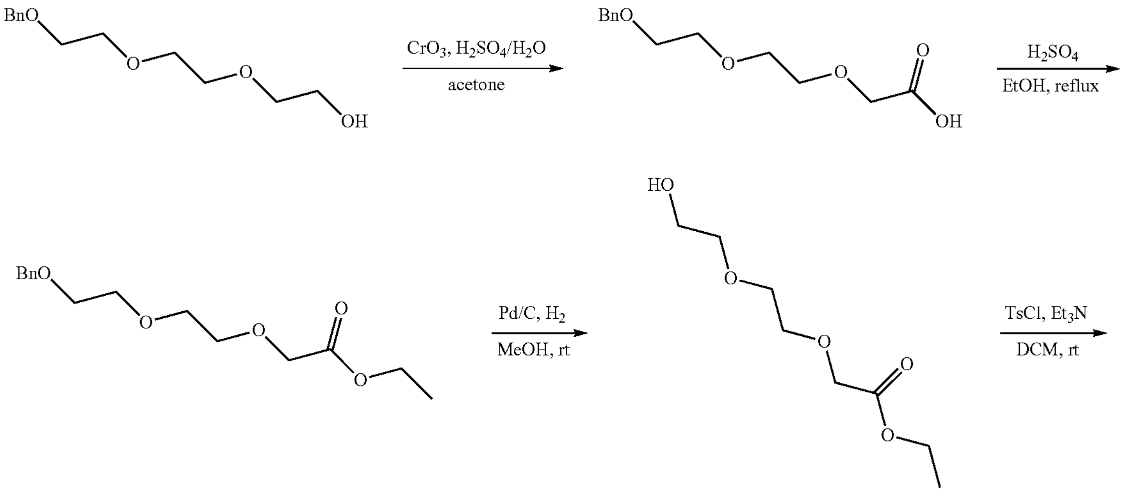

-continued
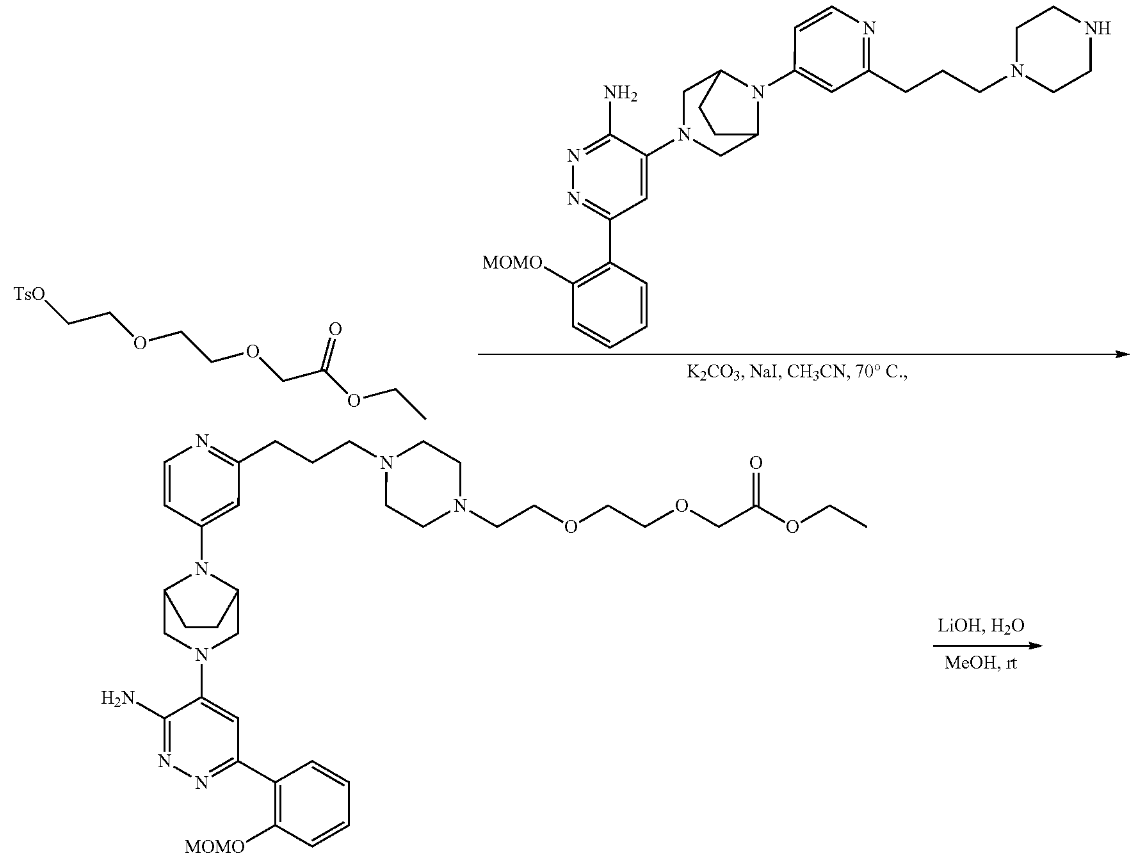
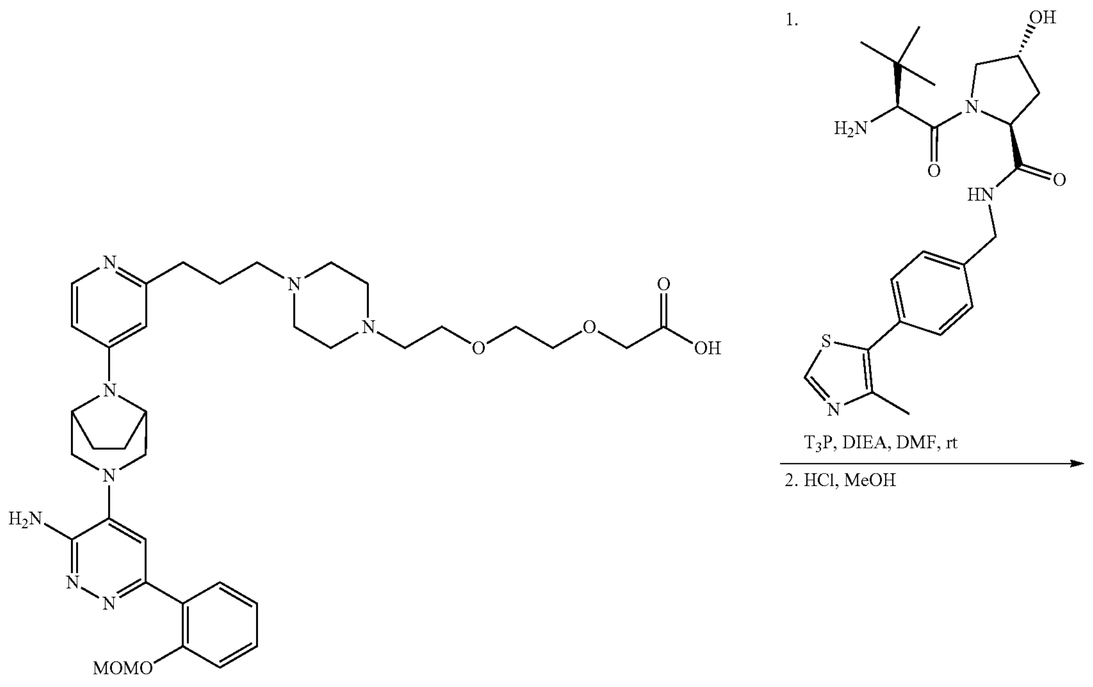

-continued
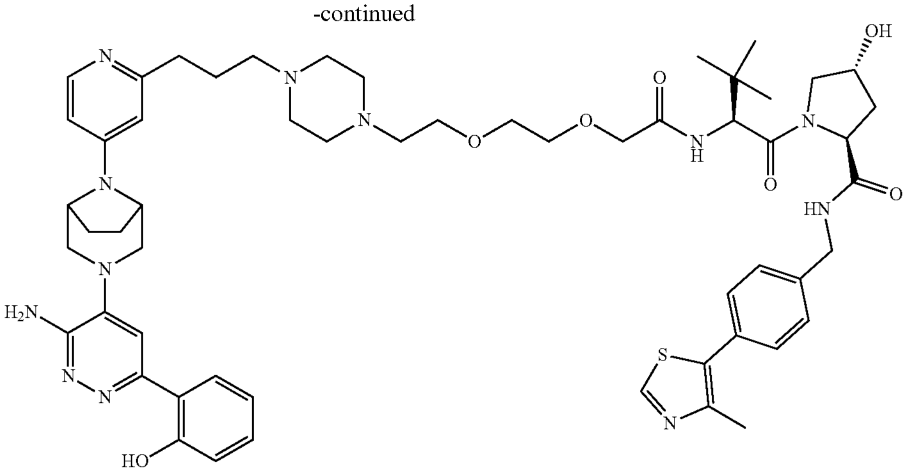
Exemplary Compound 40
Exemplary Synthesis of Exemplary Compound 41 and Exemplar Compound 42
Exemplary Compounds 41 and 42 were prepared according to the scheme below using procedures described above for other exemplary compounds.
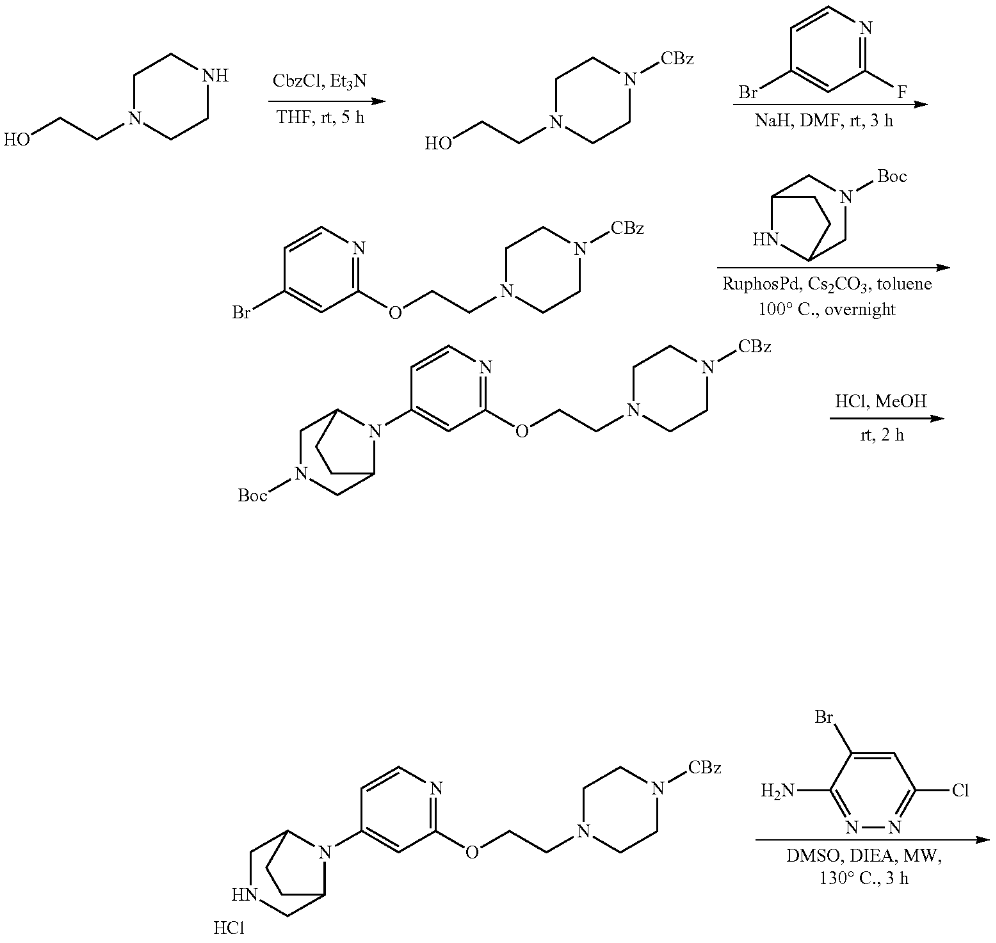

-continued
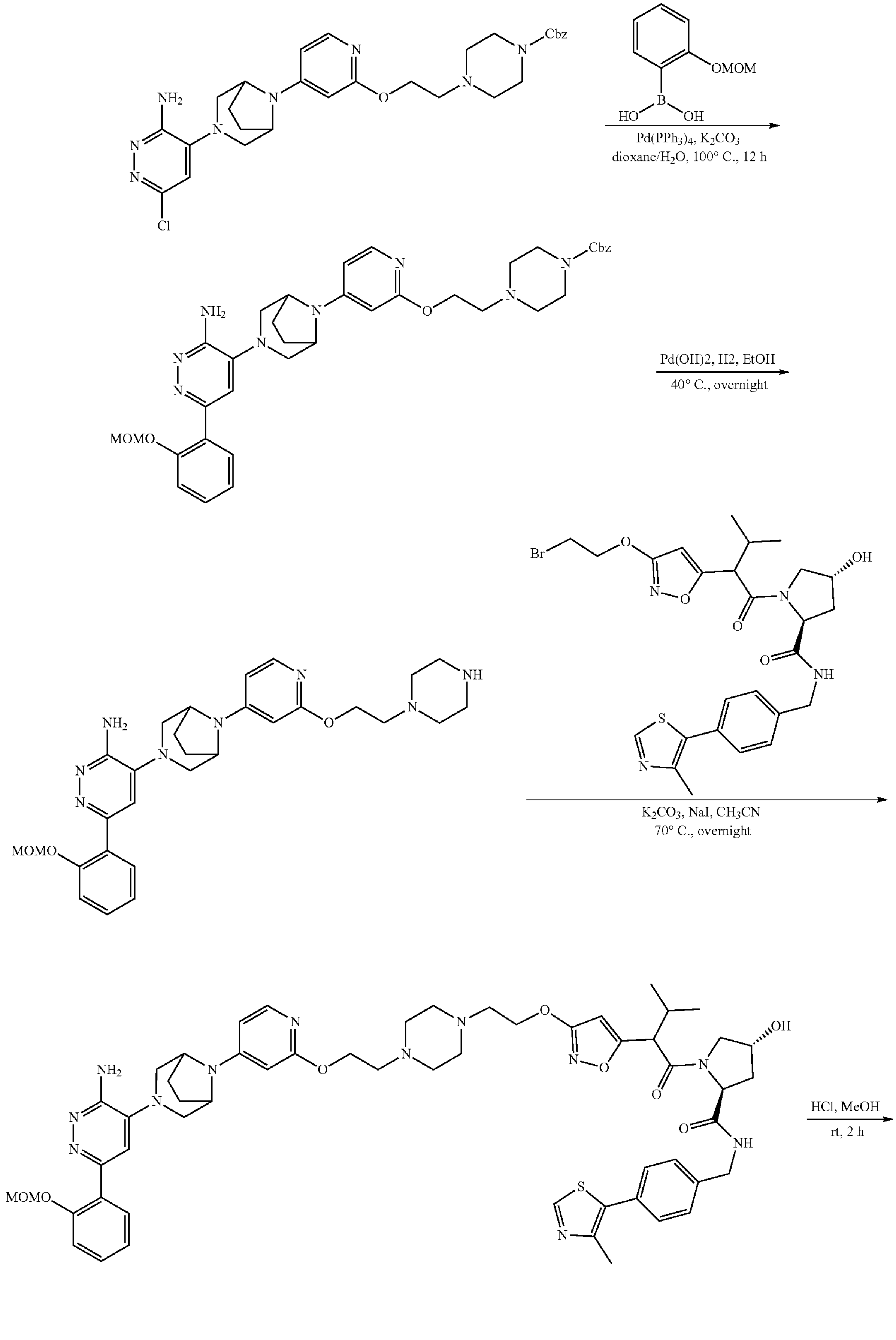

-continued

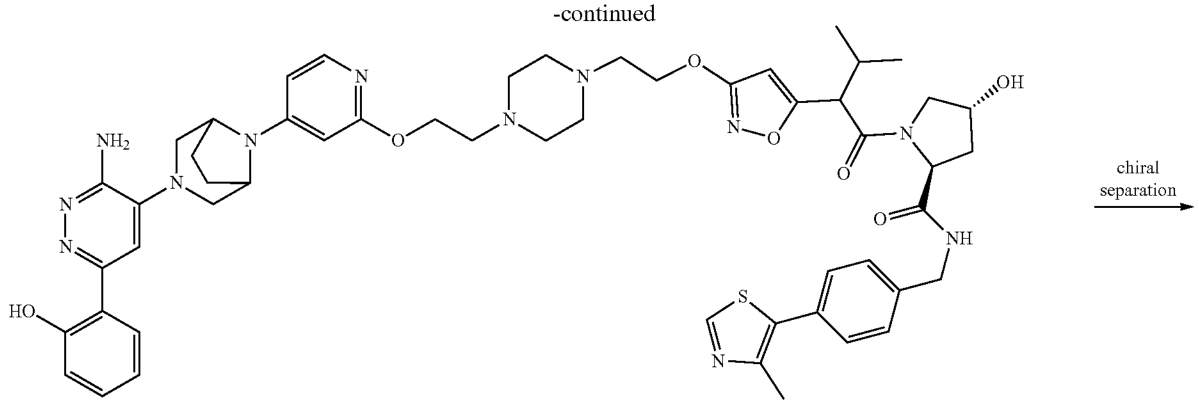

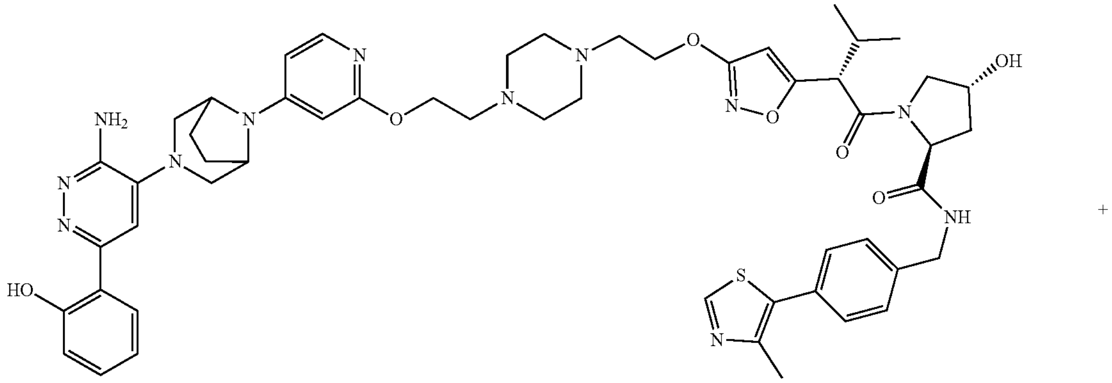

Exemplary Compound 41

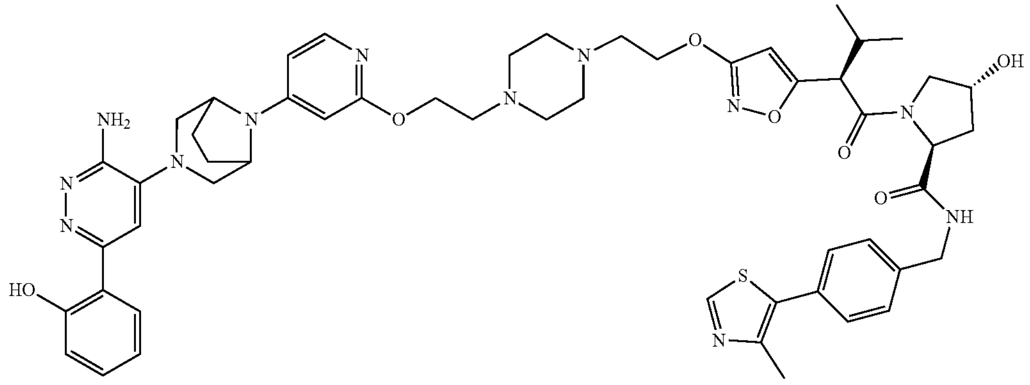

Exemplary Compound 42

Exemplary Synthesis of Exemplary Compound 45

Step 1

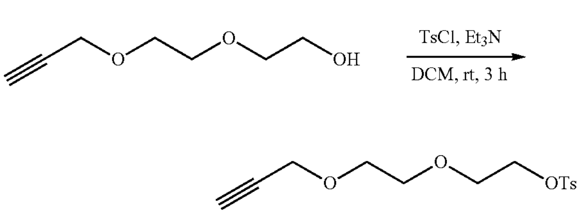

Into a 250-mL round-bottom flask, was placed a solution of 2-[2-(prop-2-yn-1-yloxy)ethoxy]ethan-1-ol (1 g, 6.94 mmol, 1.00 equiv) in dichloromethane (80 mL), triethylamine (2.8 g, 27.67 mmol, 3.00 equiv), 4-dimethylaminopyridine (270 mg, 2.21 mmol, 0.30 equiv), and 4-toluenesulfonyl chloride (1.9 g, 9.97 mmol, 1.50 equiv). The resulting solution was stirred for 12 hours at room temperature. The resulting mixture was concentrated under vacuum. The residue was applied onto a silica gel column eluting with ethyl acetate/petroleum ether (1:2). The collected fractions were combined and concentrated under vacuum. This resulted in 1.4 g (68%) of 2-[2-(prop-2-yn-1-yloxy)ethoxy]ethyl 4-methylbenzene-1-sulfonate as yellow oil.

Step 2

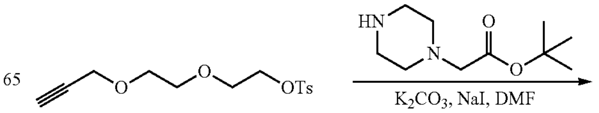

-continued

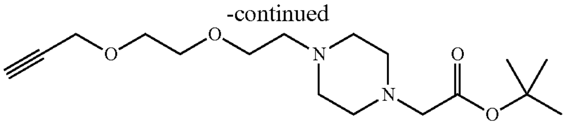

Into a 25-mL sealed tube, was placed a solution of 2-[2-(prop-2-yn-1-yloxy)ethoxy]ethyl 4-methylbenzene-1-sulfonate (1.4 g, 4.69 mmol, 1.00 equiv) in N,N-dimethylformamide (10 mL), potassium carbonate (1.6 g, 11.58 mmol, 3.00 equiv), sodium iodide (280 mg, 0.50 equiv), and tert-butyl 2-(piperazin-1-yl)acetate (898 mg, 4.48 mmol, 1.20 equiv). The resulting solution was stirred for 12 hours at 70° C. in an oil bath. The resulting solution was extracted with ethyl acetate, and organic layers combined. The resulting mixture was washed with brine and concentrated under vacuum. The residue was applied onto a silica gel column eluting with ethyl acetate/petroleum ether (1:1). The collected fractions were combined and concentrated under vacuum. This resulted in 910 mg (59%) of tert-butyl 2-(4-[2-[2-(prop-2-yn-1-yloxy)ethoxy]ethyl]piperazin-1-yl)acetate as a yellow oil.

Step 3

Into a 100-mL round-bottom flask, was placed a solution of tert-butyl 3,8-diazabicyclo[3.2.1]octane-8-carboxylate (2.0 g, 9.42 mmol, 1.00 equiv) in dimethyl sulfoxide (40 mL), N,N-diisopropylethylamine (714.0 mg, 5.52 mmol, 4.00 equiv), 4-bromo-6-chloropyridazin-3-amine (3.0 g, 14.39 mmol, 1.50 equiv). The resulting solution was stirred for 3 hours at 130° C. in an oil bath. The reaction was then quenched by the addition of water (90 mL). The resulting solution was extracted with ethyl acetate (80 mL×3) and the organic layers combined. The resulting mixture was washed with brine (100 mL×1). The mixture was dried over anhydrous sodium sulfate and concentrated under vacuum. The residue was applied onto a silica gel column with dichloromethane/methanol (10/1). The collected fractions were combined and concentrated under vacuum. This resulted in 1.7 g (53%) of tert-butyl 3-(3-amino-6-chloropyridazin-4-yl)-3,8-diazabicyclo[3.2.1]octane-8-carboxylate as a yellow solid.

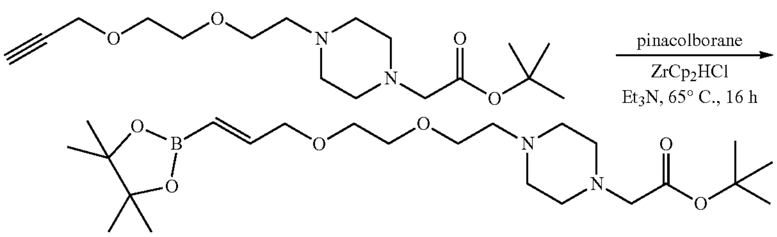

Into a 25-mL sealed tube, was placed a solution of tert-butyl 2-(4-[2-[2-(prop-2-yn-1-yloxy)ethoxy]ethyl]piperazin-1-yl)acetate (910 mg, 2.79 mmol, 1.00 equiv) in tetrahydrofuran (10 mL), pinacolborane (630 mg, 2.00 equiv), $ZrCp_2HCl$ (70 mg, 0.10 equiv), and triethylamine (1 mL, 3.00 equiv). The resulting solution was stirred for 12 hours at 80° C. in an oil bath. The resulting mixture was concentrated under vacuum. The residue was applied onto a silica gel column eluting with dichloromethane/methanol (10:1). The collected fractions were combined and concentrated under vacuum. This resulted in 720 mg (57%) of tert-butyl 2-[4-[2-(2-[[(2E)-3-(tetramethyl-1,3,2-dioxaborolan-2-yl)prop-2-en-1-yl]oxy]ethoxy)ethyl]piperazin-1-yl] acetate as a yellow oil.

Step 4

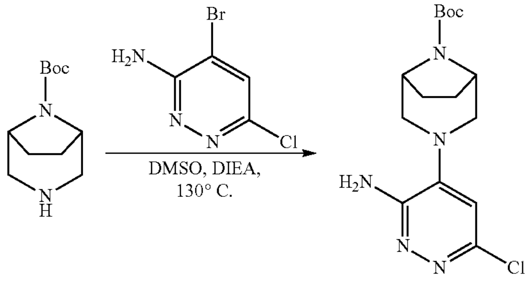 [SMILES: CC(C)(C)OC(=O)N1C2CCC1CNC2 ; Nc1nnc(Cl)cc1Br ; CC(C)(C)OC(=O)N1C2CCC1CN(c1cc(Cl)nnc1N)C2]

Step 5

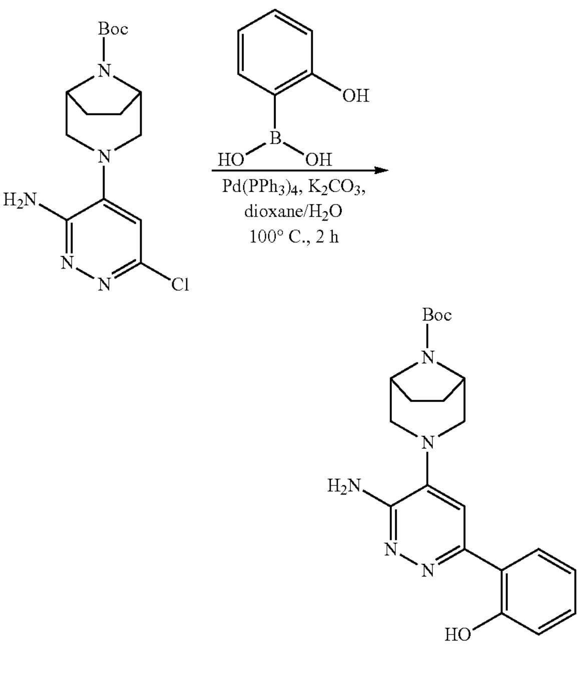

Into a 250-mL 3-necked round-bottom flask purged and maintained with an inert atmosphere of nitrogen, was placed a solution of tert-butyl 3-(3-amino-6-chloropyridazin-4-yl)-3,8-diazabicyclo[3.2.1]octane-8-carboxylate (1.7 g, 5.00 mmol, 1.00 equiv) in dioxane/water (50/10 mL), potassium carbonate (2.1 g, 15.19 mmol, 3.00 equiv), (2-hydroxyphenyl)boronic acid (1.04 g, 7.54 mmol, 1.50 equiv), tetrakis (triphenylphosphine)palladium(0) (578 mg, 0.50 mmol, 0.10 equiv). The resulting solution was stirred for 2 hours at 100° C. in an oil bath. The reaction was then quenched by the addition of water (60 mL). The resulting solution was extracted with ethyl acetate (40 mL×3) and the organic layers combined. The resulting mixture was washed with brine (60 mL×1). The mixture was dried over anhydrous sodium sulfate and concentrated under vacuum. The residue was applied onto a silica gel column eluting with dichloromethane/methanol (10/1). The collected fractions were combined and concentrated under vacuum. This resulted in 1.62 g (81%) of tert-butyl 3-[3-amino-6-(2-hydroxyphenyl) pyridazin-4-yl]-3,8-diazabicyclo[3.2.1]octane-8-carboxylate as a yellow solid.

Step 6

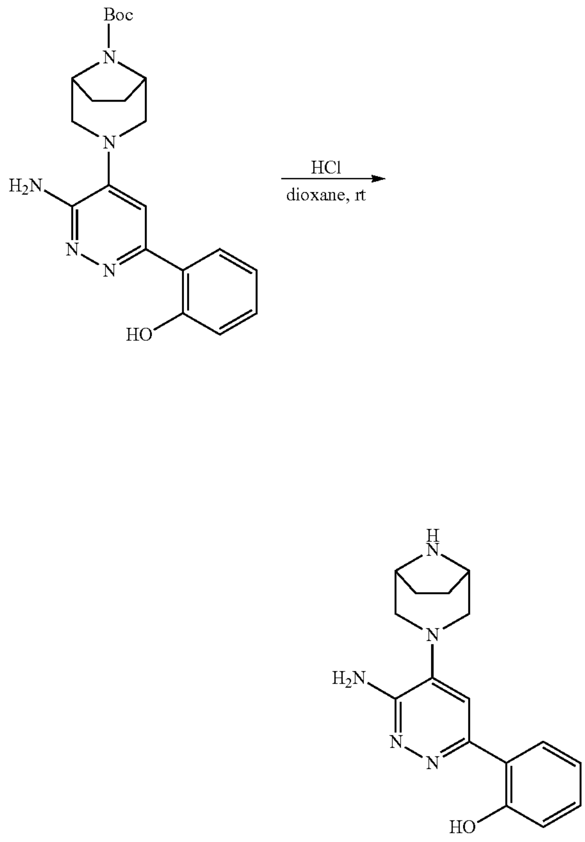

Into a 250-mL round-bottom flask, was placed a solution of tert-butyl 3-[3-amino-6-(2-hydroxyphenyl)pyridazin-4-yl]-3,8-diazabicyclo[3.2.1]octane-8-carboxylate (1.62 g, 4.08 mmol, 1.00 equiv) in dioxane (50 mL). To the above hydrogen chloride (gas) was introduced in. The resulting solution was stirred for 5 hours at room temperature. The resulting mixture was concentrated under vacuum. This resulted in 1.2 g (88%) of 2-(6-amino-5-[3,8-diazabicyclo [3.2.1]octan-3-yl]pyridazin-3-yl)phenol hydrochloride as a yellow solid.

Step 7

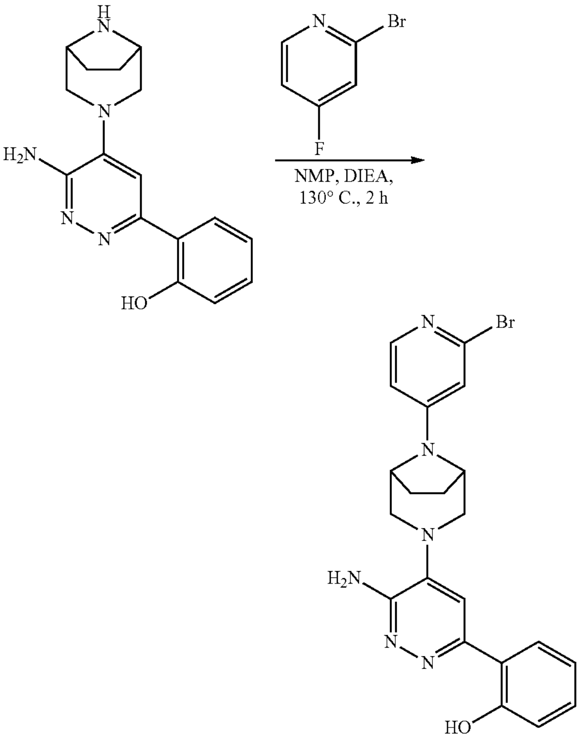

Into a 100-mL round-bottom flask, was placed a solution of 2-(6-amino-5-[3,8-diazabicyclo[3.2.1]octan-3-yl] pyridazin-3-yl)phenol (400 mg, 1.35 mmol, 1.00 equiv) in 1-methyl-2-pyrrolidinone (30 mL), N,N-diisopropylethylamine (693 mg, 5.36 mmol, 4.00 equiv), 2-bromo-4-fluoropyridine (355.0 mg, 2.02 mmol, 1.50 equiv). The resulting solution was stirred for 2 hours at 130° C. in an oil bath. The reaction was then quenched by the addition of water (40 mL). The resulting solution was extracted with ethyl acetate (30 mL×3), and the organic layers were combined. The resulting mixture was washed with brine (40 mL×1). The mixture was dried over anhydrous sodium sulfate and concentrated under vacuum. The residue was applied onto a silica gel column eluting with ethyl acetate/petroleum ether (4/1). The collected fractions were combined and concentrated under vacuum. This resulted in 410 mg (67%) of 2-[6-amino-5-[8-(2-bromopyridin-4-yl)-3,8-diazabicyclo [3.2.1]octan-3-yl]pyridazin-3-yl]phenol as a yellow solid.

Step 8

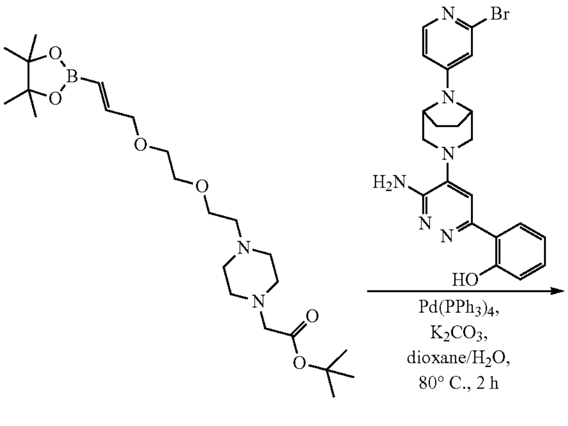

-continued

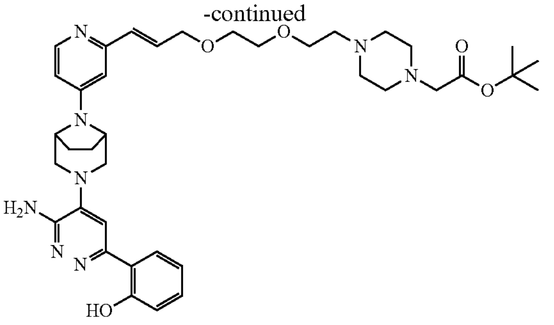

Into a 20-mL sealed tube was placed a solution of tert-butyl 2-[4-[2-(2-[[(2E)-3-(tetramethyl-1,3,2-dioxaborolan-2-yl)prop-2-en-1-yl]oxy]ethoxy)ethyl]piperazin-1-yl]acetate (628 mg, 1.38 mmol, 1.00 equiv) in dioxane/water (5:1 mL), tetrakis(triphenylphosphine)palladium (108 mg, 0.15 mmol, 0.10 equiv), potassium carbonate (286 mg, 2.07 mmol, 1.50 equiv), 2-(6-amino-5-((1R,5S)-8-(2-bromopyridin-4-yl)-3,8-diazabicyclo[3.2.1]octan-3-yl)pyridazin-3-yl)phenol (500 mg, 1.10 mmol, 0.80 equiv). The resulting solution was stirred for 2 hours at 80° C. in an oil bath. The resulting mixture was concentrated under vacuum. The residue was applied onto a silica gel column eluting with dichloromethane/methanol (10:1). The collected fractions were combined and concentrated under vacuum. This resulted in 540 mg (56%) of tert-butyl 2-[4-[2-(2-[[(2E)-3-(4-[3-[3-amino-6-(2-hydroxyphenyl)pyridazin-4-yl]-3,8-diazabicyclo[3.2.1]octan-8-yl]pyridin-2-yl)prop-2-en-1-yl]oxy]ethoxy)ethyl]piperazin-1-yl]acetate as a yellow solid.

Step 9

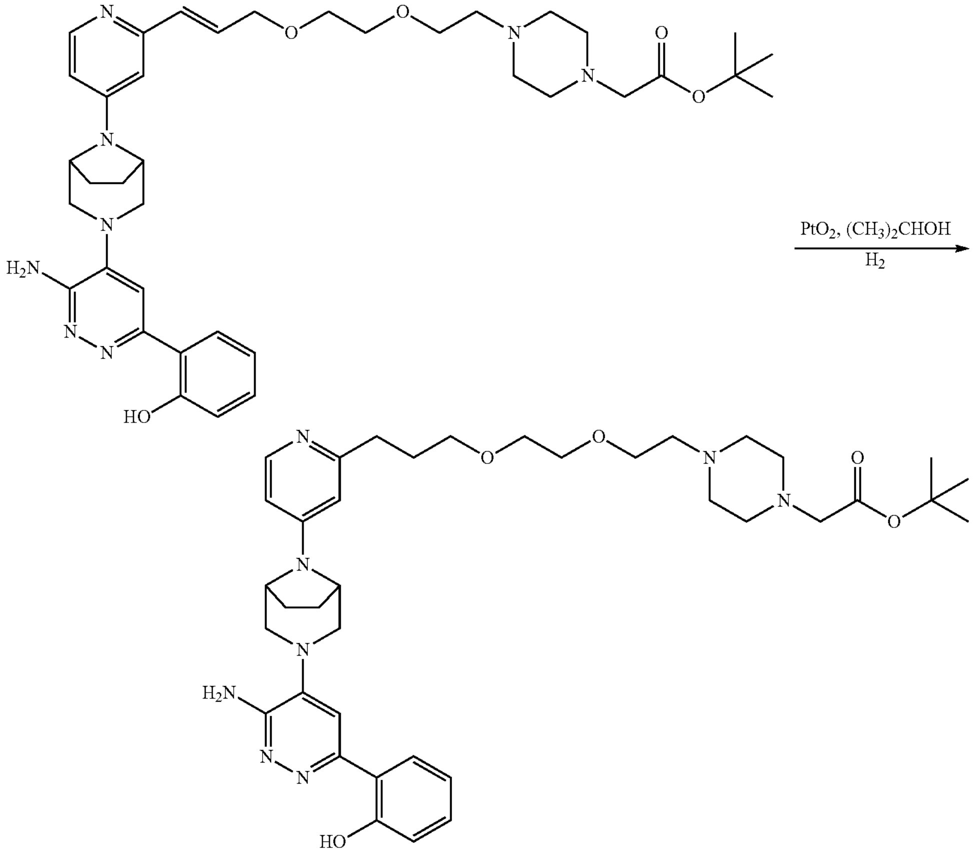

Into a 100-mL round-bottom flask, was placed a solution of tert-butyl 2-[4-[2-(2-[[(2E)-3-(4-[3-[3-amino-6-(2-hydroxyphenyl)pyridazin-4-yl]-3,8-diazabicyclo[3.2.1]octan-8-yl]pyridin-2-yl)prop-2-en-1-yl]oxy]ethoxy)ethyl]piperazin-1-yl]acetate (200 mg, 0.29 mmol, 1.00 equiv) in 2-propanol (30 mL) and $PtO_2$ (10 mg, 0.10 equiv). The resulting solution was stirred under hydrogen atmosphere for 12 hours at room temperature. The resulting solution was diluted with 50 mL of 2-propanol and then concentrated under vacuum. This resulted in 190 mg (95%) of tert-butyl 2-[4-(2-[2-[3-(4-[3-[3-amino-6-(2-hydroxyphenyl)pyridazin-4-yl]-3,8-diazabicyclo[3.2.1]octan-8-yl]pyridin-2-yl)propoxy]ethoxy]ethyl)piperazin-1-yl]acetate as a yellow solid.

Step 10

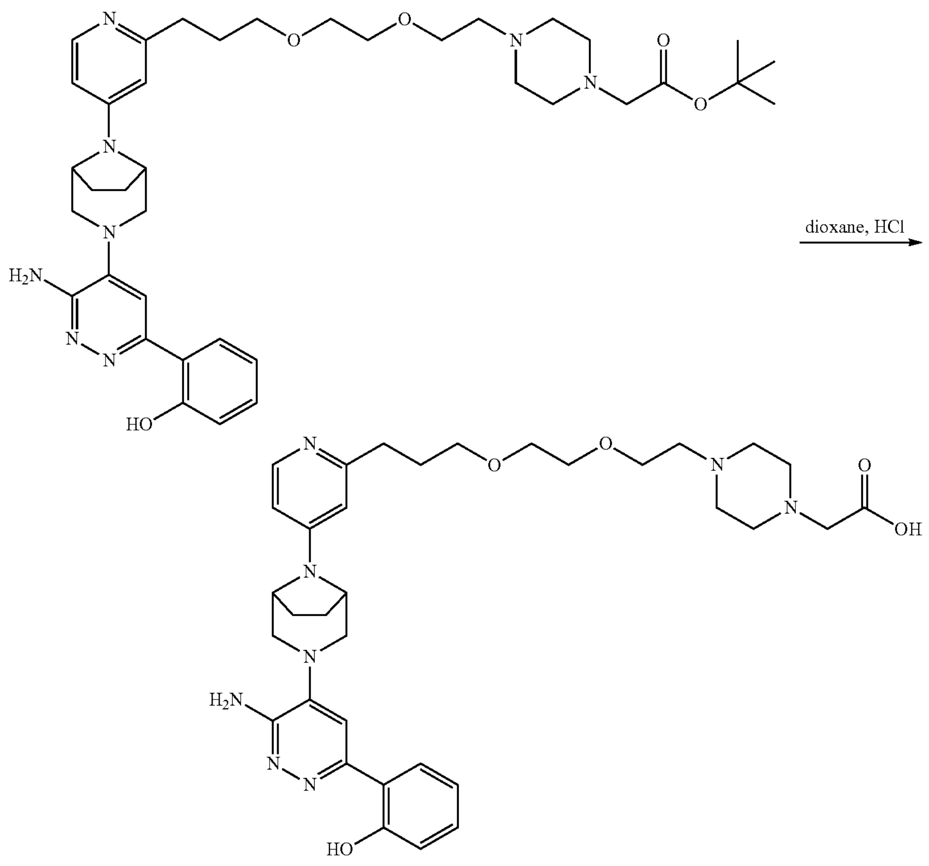

Into a 100-mL round-bottom flask, was placed a solution of tert-butyl 2-[4-(2-[2-[3-(4-[3-[3-amino-6-(2-hydroxyphenyl)pyridazin-4-yl]-3,8-diazabicyclo[3.2.1]octan-8-yl]pyridin-2-yl)propoxy]ethoxy]ethyl)piperazin-1-yl]acetate (190 mg, 0.27 mmol, 1.00 equiv) in dioxane (20 mL). Into the above hydrogen chloride (gas) was introduced. The resulting solution was stirred for 2 hours at room temperature. The resulting mixture was concentrated under vacuum. This resulted in 160 mg (92%) of 2-[4-(2-[2-[3-(4-[3-[3-amino-6-(2-hydroxyphenyl)pyridazin-4-yl]-3,8-diazabicyclo[3.2.1]octan-8-yl]pyridin-2-yl)propoxy]ethoxy]ethyl)piperazin-1-yl]acetic acid as a yellow solid.

Step 11

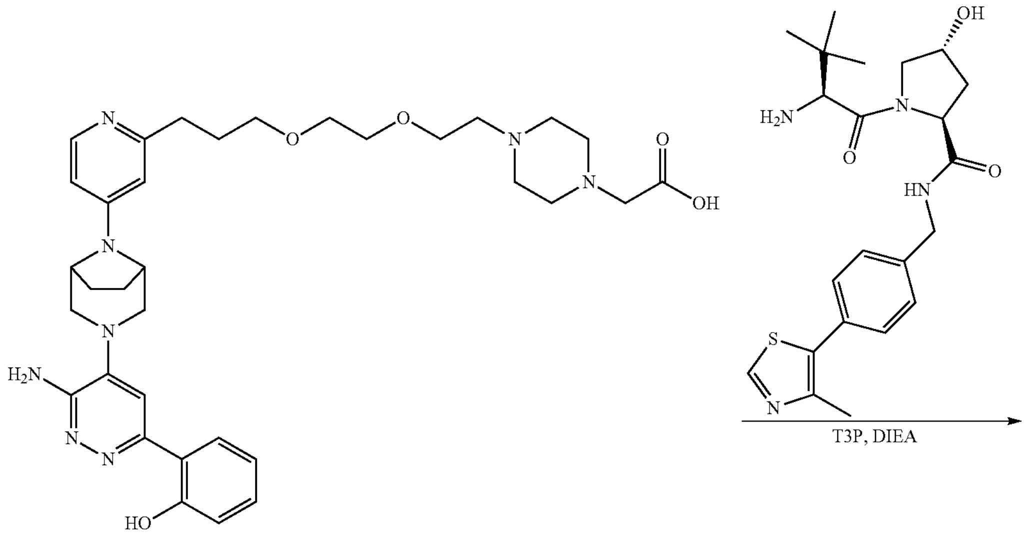

-continued

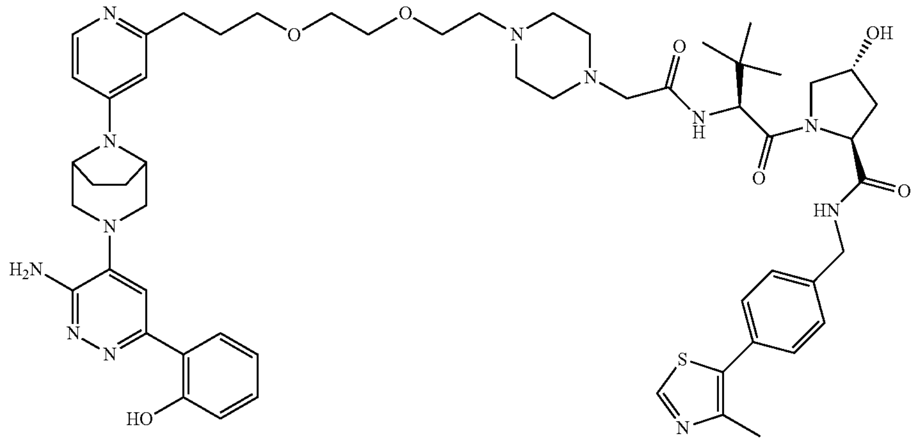

Into a 100-mL round-bottom flask, was placed 2-[4-(2-2-[3-(4-3-[3-amino-6-(2-hydroxyphenyl)pyridazin-4-yl]-3,8-diazabicyclo[3.2.1]octan-8-ylpyridin-2-yl)propoxy]ethoxy-ethyl)piperazin-1-yl]acetic acid (160 mg, 0.25 mmol, 1.00 equiv), N,N-diisopropylethylamine (0.3 mL, 0.30 equiv), a solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (139 mg, 0.30 mmol, 1.20 equiv) in acetonitrile (20 mL), and T3P (188 mg, 3.00 equiv). The resulting solution was stirred for 2 hours at room temperature. The resulting mixture was concentrated under vacuum. The crude product (100 mL) was purified by prep-HPLC with the following conditions: Column, XBridge Prep C18 OBD Column, 5 um, 19*" 150 mm; mobile phase, Water (10 mmol/L ammonium bicarbonate) and acetonitrile (26.0% acetonitrile up to 49.0% in 8 min); Detector, UV 254 nm. This resulted in 28.5 mg (11%) of (2S,4R)-1-[(2S)-2-[2-[4-(2-[2-[3-(4-[3-[3-amino-6-(2-hydroxyphenyl)pyridazin-4-yl]-3,8-diazabicyclo[3.2.1]octan-8-yl]pyridin-2-yl)propoxy]ethoxy]ethyl)piperazin-1-yl]acetamido]-3,3-dimethylbutanoyl]-4-hydroxy-N-[[4-(4-methyl-1,3-thiazol-5-yl)phenyl]methyl]pyrrolidine-2-carboxamide as a white solid.

$^1$H NMR (300 MHz, $CD_3OD$): δ 8.88-8.66 (m, 1H), 8.09-7.88 (m, 1H), 7.76-7.57 (m, 1H), 7.52-7.01 (m, 6H), 6.92-6.62 (m, 4H), 4.66-4.21 (m, 6H), 3.94-3.72 (m, 2H), 3.69-3.33 (m, 12H), 3.14-2.89 (m, 4H), 2.81-2.34 (m, 14H), 2.32-1.78 (m, 8H), 1.32-0.74 (m, 12H).

Exemplary Synthesis of Exemplary Compound 46 and Exemplar Compound 47

Step 1

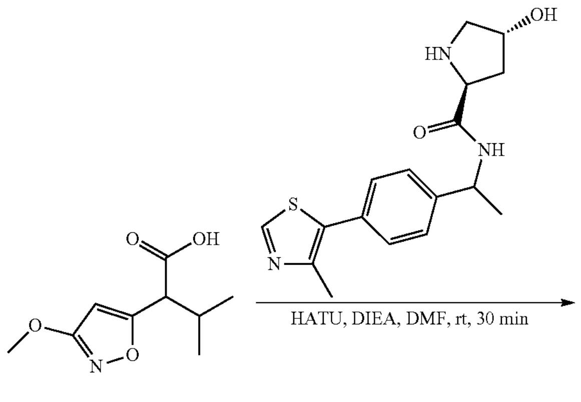

-continued

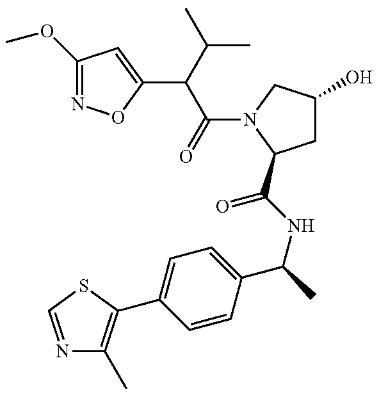

Into a 50-mL round-bottom flask, was placed a solution of 2-(3-methoxy-1,2-oxazol-5-yl)-3-methylbutanoic acid (2.0 g, 10.0 mmol, 1.0 equiv) in N,N-dimethylformamide (20 mL), N,N,N',N'-tetramethyl-O-(7-azabenzotriazol-1-yl)uronium hexafluorophospate (4.1 g, 10.8 mmol, 1.1 equiv), N,N-diisopropylethylamine (6.0 g, 46.4 mmol, 4.6 equiv), and (2S,4R)-4-hydroxy-N-[(1S)-1-[4-(4-methyl-1,3-thiazol-5-yl)phenyl]ethyl]pyrrolidine-2-carboxamide hydrochloride (3.5 g, 9.5 mmol, 1.0 equiv). The resulting solution was stirred for 30 minutes at room temperature. The reaction was then quenched by the addition of 30 mL of water. The resulting solution was extracted with of ethyl acetate (30 mL×3), and the organic layers were combined and concentrated under vacuum. The residue was applied onto a silica gel column eluting with dichloromethane/methanol (10:1). This resulted in 2.1 g (41%) of (2S,4R)-4-hydroxy-1-[2-(3-methoxy-1,2-oxazol-5-yl)-3-methylbutanoyl]-N-[(1S)-1-[4-(4-methyl-1,3-thiazol-5-yl) phenyl]ethyl]pyrrolidine-2-carboxamide as a light yellow solid.

Step 2

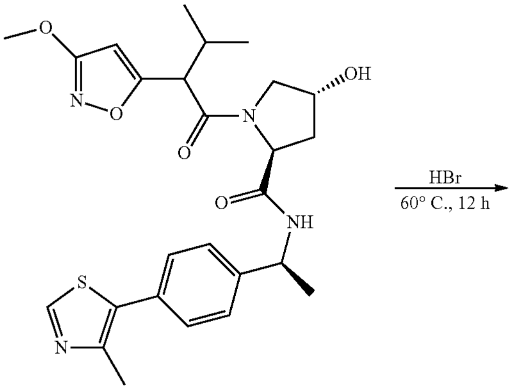

-continued

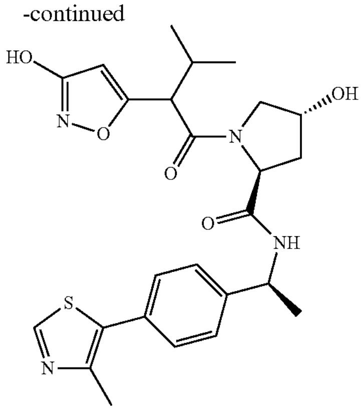

Into a 50-mL round-bottom flask, was placed (2S,4R)-4-hydroxy-1-[2-(3-methoxy-1,2-oxazol-5-yl)-3-methylbutanoyl]-N-[(1S)-1-[4-(4-methyl-1,3-thiazol-5-yl)phenyl]ethyl]pyrrolidine-2-carboxamide (2.1 g, 4.1 mmol, 1.0 equiv) and 48% aqueous hydrogen bromide (15 mL). The resulting solution was stirred overnight at 60° C. in an oil bath. The resulting mixture was concentrated under vacuum to produce 1.9 g of crude product.

Step 3

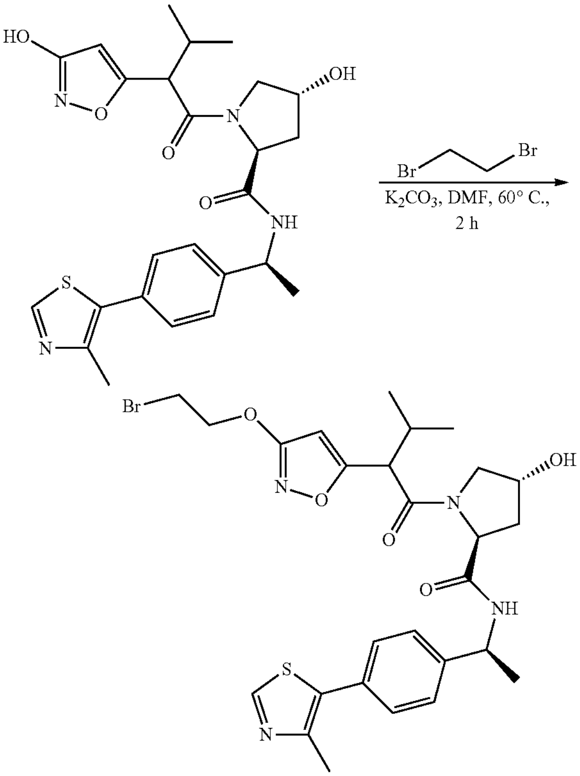

Into a 50-mL round-bottom flask, was placed a solution of (2S,4R)-4-hydroxy-1-[2-(3-hydroxy-1,2-oxazol-5-yl)-3-methylbutanoyl]-N-[(1S)-1-[4-(4-methyl-1,3-thiazol-5-yl) phenyl]ethyl]pyrrolidine-2-carboxamide (1.9 g, 3.8 mmol, 1.0 equiv) in $CH_3CN$ (20 mL), potassium carbonate (3.5 g, 25.3 mmol, 6.6 equiv), sodium iodide (800.0 mg, 5.3 mmol, 1.4 equiv), and 1,2-dibromoethane (1 g, 5.3 mmol, 1.4 equiv). The resulting solution was stirred overnight at 60° C.

in an oil bath. The resulting mixture was concentrated under vacuum. The residue was applied onto a silica gel column eluting with dichloromethane/methanol (10:1). This resulted in 1.1 g (48%) of (2S,4R)-1-[2-[3-(2-bromoethoxy)-1,2-oxazol-5-yl]-3-methylbutanoyl]-4-hydroxy-N-[(1S)-1-[4-(4-methyl-1,3-thiazol-5-yl)phenyl]ethyl]pyrrolidine-2-carboxamide as a white solid.

Step 4

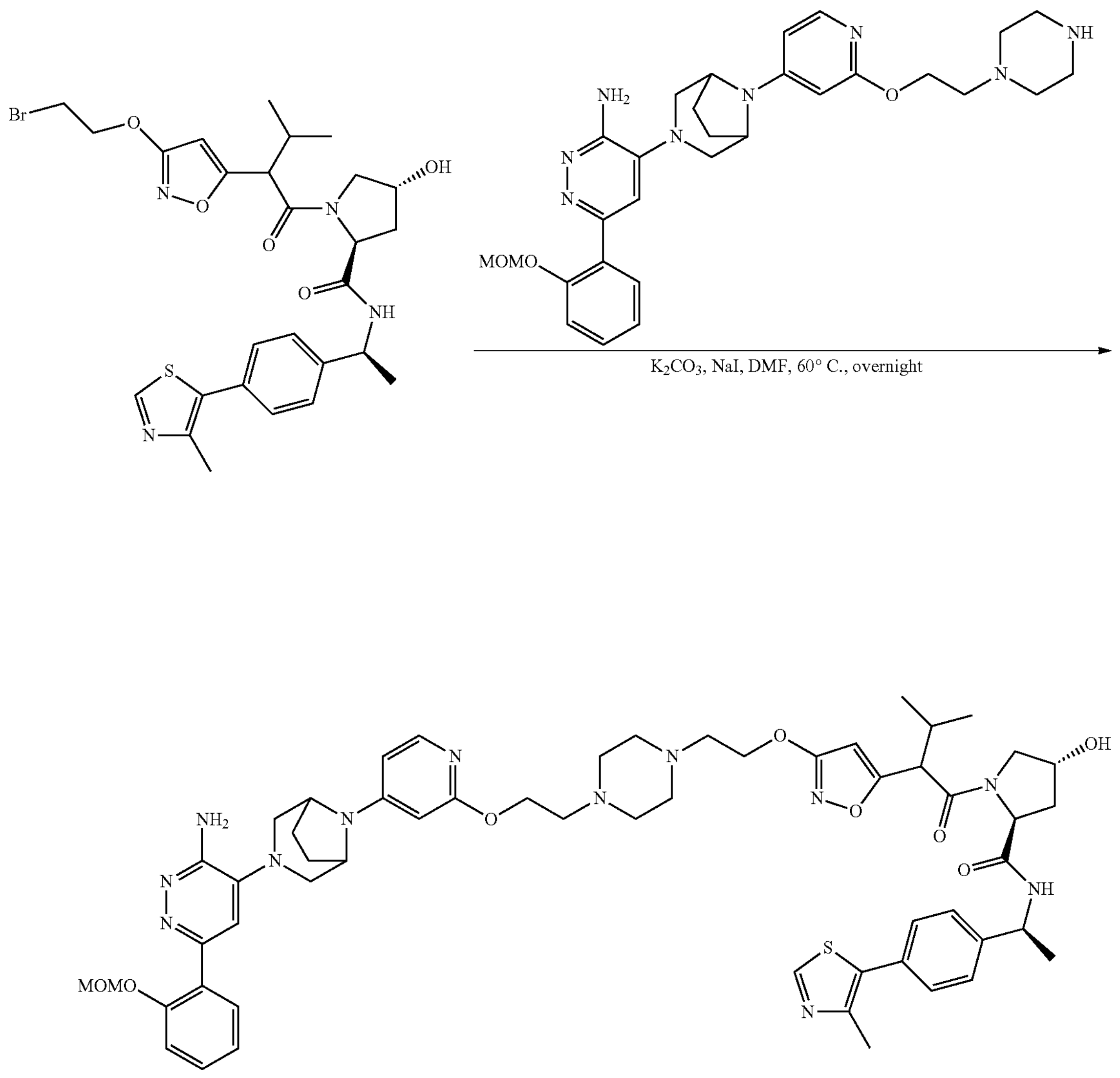

Into a 50-mL round-bottom flask, was placed a solution of (2S,4R)-1-[2-[3-(2-bromoethoxy)-1,2-oxazol-5-yl]-3-methylbutanoyl]-4-hydroxy-N-[(1S)-1-[4-(4-methyl-1,3-thiazol-5-yl)phenyl]ethyl]pyrrolidine-2-carboxamide (200 mg, 0.3 mmol, 1.0 equiv) in $CH_3CN$ (20 mL), potassium carbonate (400 mg, 2.9 mmol, 8.8 equiv), sodium iodide (80 mg, 0.53 mmol, 1.6 equiv), and 6-[2-(methoxymethoxy)phenyl]-4-(8-2-[2-(piperazin-1-yl)ethoxy]pyridin-4-yl-3,8-diazabicyclo[3.2.1]octan-3-yl)pyridazin-3-amine (190 mg, 0.4 mmol, 1.1 equiv) [prepared as described above for other examples]. The resulting solution was stirred overnight at 60° C. in an oil bath. The resulting mixture was concentrated under vacuum. The residue was applied onto a silica gel column eluting with dichloromethane/methanol (5:1). This resulted in 180 mg (51%) of (2S,4R)-1-[2-(3-[2-[4-(2-[[4-(3-[3-amino-6-[2-(methoxymethoxy)phenyl]pyridazin-4-yl]-3,8-diazabicyclo[3.2.1]octan-8-yl) pyridin-2-yl]oxy]ethyl)piperazin-1-yl]ethoxy]-1,2-oxazol-5-yl)-3-methylbutanoyl]-4-hydroxy-N—[(S)-1-[4-(4-methyl-1,3-thiazol-5-yl)phenyl]ethyl]pyrrolidine-2-carboxamide as a light yellow solid.

505 506
Step 5
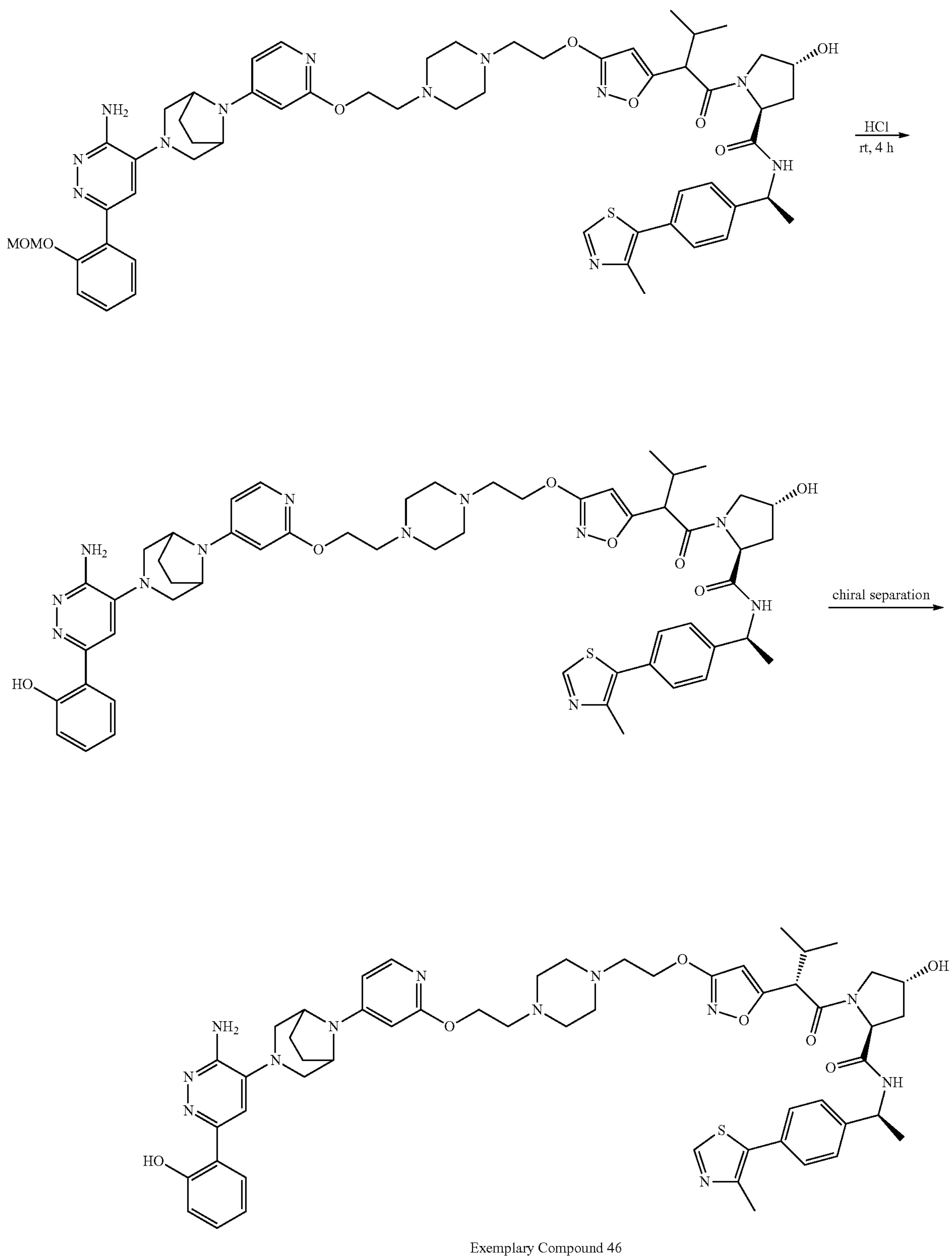
Exemplary Compound 46
+

-continued

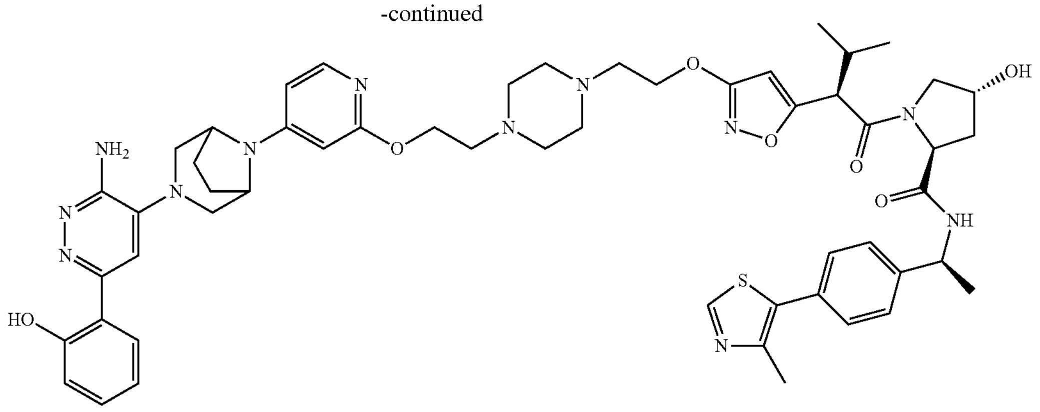

Exemplary Compound 47

Into a 50-mL round-bottom flask was placed a solution of (2S,4R)-1-[2-(3-[2-[4-(2-[[4-(3-[3-amino-6-[2-(methoxymethoxy)phenyl]pyridazin-4-yl]-3,8-diazabicyclo [3.2.1]octan-8-yl) pyridin-2-yl]oxy]ethyl)piperazin-1-yl] ethoxy]-1,2-oxazol-5-yl)-3-methylbutanoyl]-4-hydroxy-N-[(1S)-1-[4-(4-methyl-1,3-thiazol-5-yl)phenyl]ethyl] pyrrolidine-2-carboxamide (180 mg, 0.17 mmol, 1.0 equiv) in methanol (5 mL), and hydrogen chloride (0.068 mL of 4M solution in dioxane, 0.27 mmol, 1.6 equiv). The resulting solution was stirred for 2 hours at room temperature. The resulting mixture was concentrated under vacuum. The crude product was purified by Chiral-Prep-HPLC with the following conditions: Column; mobile phase, Column: CHIRALPAK ID-03, 2.0 cm I.D*25 cm L (5 um); Mobile Phase A:MTBE (0.2% IPA)—HPLC, Mobile Phase B: methanol—HPLC; Flow rate: 18 mL/min; Gradient: 50 B to 50 B in 18 min; 254/220 nm. This resulted in 46.7 mg of (2S,4R)-1-[(2S)-2-[3-[2-(4-[2-[(4-[3-[3-amino-6-(2-hydroxyphenyl) pyridazin-4-yl]-3,8-diazabicyclo[3.2.1]octan-8-yl]pyridin-2-yl)oxy]ethyl]piperazin-1-yl)ethoxy]-1,2-oxazol-5-yl]-3-methylbutanoyl]-4-hydroxy-N-[(1S)-1-[4-(4-methyl-1,3-thiazol-5-yl)phenyl]ethyl]pyrrolidine-2-carboxamide as a white solid[$^1$H NMR (300 MHz, DMSO-$d_6$) δ 14.10 (s, 1H), 8.99-8.83 (m, 1H), 8.25 (d, J=7.8 Hz, 1H), 7.92-7.83 (m, 2H), 7.75-7.12 (m, 6H), 6.81 (td, J=8.4, 2.2 Hz, 2H), 6.49 (dd, J=6.1, 2.0 Hz, 1H), 6.15-5.93 (m, 4H), 5.06 (d, J=3.6 Hz, 1H), 4.98-4.79 (m, 1H), 4.38 (t, J=7.7 Hz, 3H), 4.19 (dt, J=21.0, 5.6 Hz, 5H), 3.98 (m, 1H), 3.71 (d, J=8.6 Hz, 2H), 3.57-3.34 (m, 2H), 3.33-3.15 (m, 2H), 2.97 (d, J=11.6 Hz, 4H), 2.57-2.40 (d, J=8.0 Hz, 11H), 2.31-2.07 (m, 1H), 2.06-1.97 (m, 2H), 1.91-1.66 (m, 3H), 1.42 (d, J=7.0 Hz, 1H), 1.31 (d, J=7.0 Hz, 3H), 0.92-0.67 (m, 6H)] and 54.4 mg of (2S,4R)-1-[(2R)-2-[3-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl) ethoxy]-1,2-oxazol-5-yl]-3-methylbutanoyl]-4-hydroxy-N-[(1S)-1-[4-(4-methyl-1,3-thiazol-5-yl)phenyl]ethyl]pyrrolidine-2-carboxamide as a white solid[$^1$H NMR (300 MHz, DMSO-$d_6$) δ 14.11 (s, 1H), 8.95 (s, 1H), 8.37 (d, J=7.6 Hz, 1H), 7.88-7.75 (d, J=5.9 Hz, 2H), 7.49-7.28 (m, 6H), 7.18 (ddd, J=8.3, 7.0, 1.6 Hz, 1H), 6.88-6.75 (m, 2H), 6.49 (dd, J=6.2, 2.0 Hz, 1H), 6.16-6.02 (m, 2H), 5.93 (s, 2H), 5.05 (d, J=3.7 Hz, 1H), 5.00-4.81 (m, 1H), 4.46 (s, 2H), 4.39-4.13 (m, 6H), 3.72-3.55 (m, 2H), 3.45-3.35 (m, 1H), 3.21 (d, J=11.7 Hz, 2H), 2.98 (d, J=11.6 Hz, 2H), 2.59 (q, J=6.5 Hz, 4H), 2.42 (s, 6H), 2.17 (dd, J=20.0, 8.3 Hz, 3H), 1.94 (s, 4H), 1.75 (t, J=9.6 Hz, 1H), 1.37 (dd, J=20.9, 7.0 Hz, 3H), 1.17 (d, J=14.9 Hz, 1H), 1.05-0.87 (m, 3H), 0.77 (dd, J=10.6, 6.7 Hz, 3H)].

Exemplary Synthesis of Exemplary Compound 48

Step 1

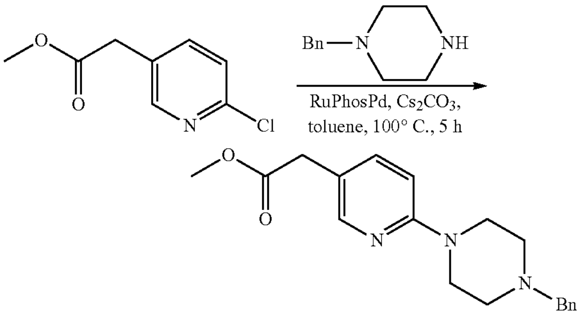

Into a 100-mL round-bottom flask purged and maintained with an inert atmosphere of nitrogen, was placed methyl 2-(6-chloropyridin-3-yl)acetate (1.86 g, 10.0 mmol, 1.00 equiv), toluene (50 mL), $Cs_2CO_3$ (10.0 g, 30.0 mmol, 3.00 equiv), 1-benzylpiperazine (2.11 g, 12.0 mmol, 1.2 equiv), and RuPhosPd (0.39 g, 0.05 equiv). The resulting solution was stirred for 10 hours at 100° C. in an oil bath. The reaction mixture was cooled to room temperature. The reaction was then quenched by the addition of water (50 mL). The resulting solution was extracted with ethyl acetate (100 mL×2), and the organic layers were combined. The resulting mixture was washed with brine. The mixture was dried over anhydrous sodium sulfate and concentrated under vacuum. The residue was applied onto a silica gel column with ethyl acetate/petroleum ether (v:v=1/3). This resulted in 1.1 g (32%) of methyl 2-[6-(4-benzylpiperazin-1-yl) pyridin-3-yl]acetate as a yellow solid.

Step 2

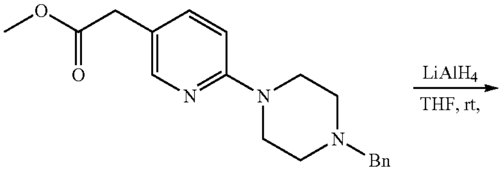

-continued

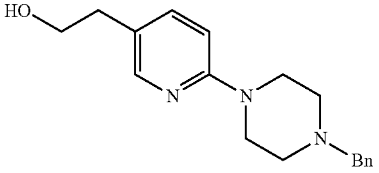

Into a 100-mL 3-necked round-bottom flask purged and maintained with an inert atmosphere of nitrogen, was placed tetrahydrofuran (30 mL), lithium aluminium hydride (0.34 g, 3.00 equiv). This was followed by the addition of a solution of methyl 2-[6-(4-benzylpiperazin-1-yl)pyridin-3-yl]acetate (1.0 g, 3.01 mmol, 1.00 equiv) in tetrahydrofuran (5 mL) dropwise with stirring at 0° C. in 5 minutes. The resulting solution was stirred for 10 hours at 25° C. The reaction was then quenched by the addition of water (3 mL), sodium hydroxide aqueous solution (5%), water (3 mL) with stirring at 0° C. The solids were filtered out. The mixture was dried over anhydrous sodium sulfate and concentrated under vacuum. The residue was applied onto a silica gel column with dichloromethane/methanol (v:v=1:10). This resulted in 750 mg (81%) of 2-[6-(4-benzylpiperazin-1-yl)pyridin-3-yl]ethan-1-ol as a light yellow solid.

Step 3

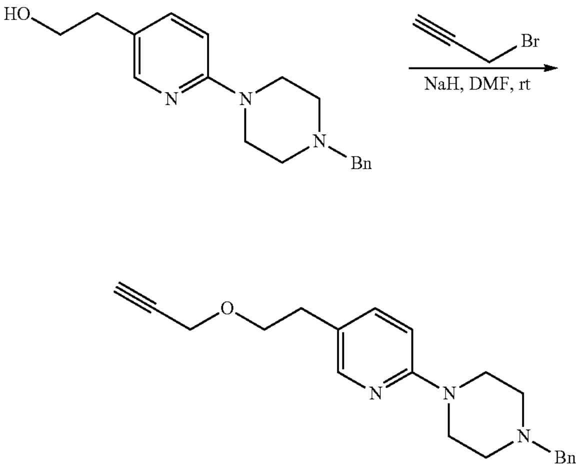

Into a 50-mL round-bottom flask purged and maintained under an inert atmosphere of nitrogen, was placed 2-[6-(4-benzylpiperazin-1-yl)pyridin-3-yl]ethan-1-ol (750 g, 2.5 mmol, 1.00 equiv), N,N-dimethylformamide (20 mL), sodium hydride (60%) (200 mg, 8.4 mmol, 2.00 equiv) at 0° C. The resulting solution was stirred for 0.5 hour at 0° C. This was followed by the addition of 3-bromoprop-1-yne (390 mg, 3.3 mmol, 1.30 equiv) dropwise with stirring at 0° C. The resulting solution was allowed to react with stirring for an additional 12 hours at 25° C. The reaction was then quenched by the addition of water (20 mL) at 0° C. The resulting solution was extracted with ethyl acetate (20 mL×2), and the organic layers combined. The mixture was dried over anhydrous sodium sulfate and concentrated under vacuum. The residue was applied onto a silica gel column eluting with ethyl acetate/petroleum ether (v:v=1:3). This resulted in 602 mg (71%) of 1-benzyl-4-[5-[2-(prop-2-yn-1-yloxy)ethyl]pyridin-2-yl]piperazine as a yellow oil.

Step 4

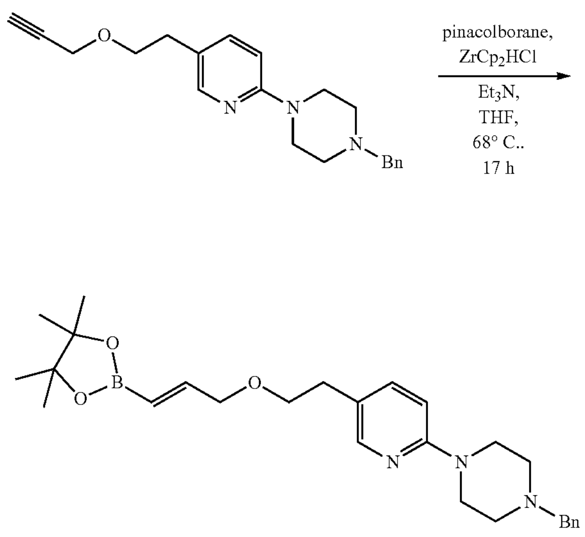 [SMILES: C#CCOCCc1ccc(N2CCN(Cc3ccccc3)CC2)nc1 ; CC1(C)OB(/C=C/COCCc2ccc(N3CCN(Cc4ccccc4)CC3)nc2)OC1(C)C]

Into a 25-mL sealed tube purged and maintained with an inert atmosphere of nitrogen, was placed 1-benzyl-4-[5-[2-(prop-2-yn-1-yloxy)ethyl]pyridin-2-yl]piperazine (1.0 g, 3.00 mmol, 1.00 equiv), tetrahydrofuran (15 mL), pinacolborane (2 mL), $ZrCp_2HCl$ (0.077 g, 0.10 equiv), triethylamine (0.030 g, 0.10 equiv). The resulting solution was stirred for 12 hours at 70° C. in an oil bath. The reaction was then quenched by the addition of water (5 mL). The resulting solution was extracted with ethyl acetate (10 mL×2), and the organic layers combined and dried over anhydrous sodium sulfate and concentrated under vacuum. The residue was applied onto a silica gel column eluting with dichloromethane/methanol (v:v=10:1). This resulted in 1.05 g (75%) of 1-benzyl-4-[5-(2-[[(2E)-3-(tetramethyl-1,3,2-dioxaborolan-2-yl)prop-2-en-1-yl]oxy]ethyl)pyridin-2-yl]piperazine as orange oil.

Step 5

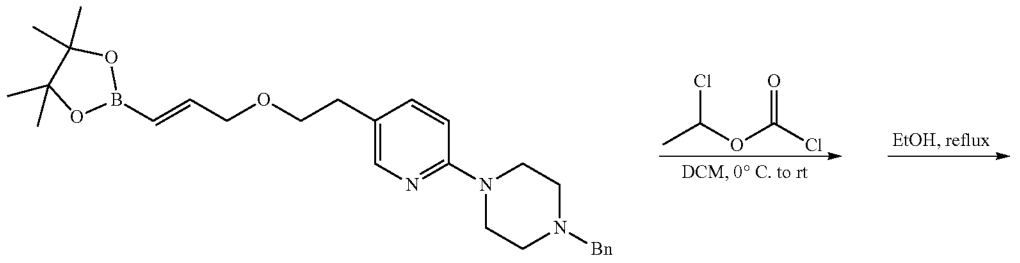

-continued

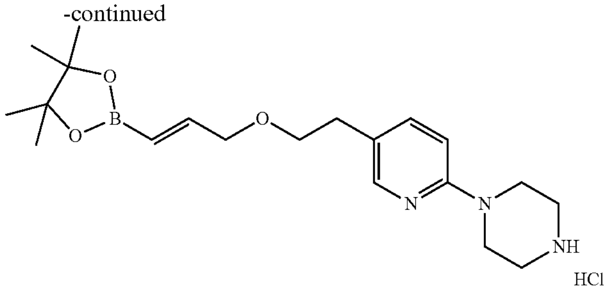

Into a 100-mL round-bottom flask, was placed 1-benzyl-4-[5-(2-[[(2E)-3-(tetramethyl-1,3,2-dioxaborolan-2-yl)prop-2-en-1-yl]oxy]ethyl)pyridin-2-yl]piperazine (928 mg, 2.00 mmol, 1.00 equiv), dichloromethane (25 mL). This was followed by the addition of 1-chloroethyl chloroformate (568.0 mg, 3.97 mmol, 2.00 equiv) dropwise with stirring at 0° C. The resulting solution was stirred for 1 hour at 25° C. The resulting mixture was concentrated under vacuum. Ethyl alcohol (5 mL) was added. The resulting solution was allowed to react with stirring for an additional 2 hours while the temperature was maintained at 80° C. in an oil bath. The resulting mixture was concentrated under vacuum. This resulted in 0.71 g (95%) of 1-[5-(2-[[(2E)-3-(tetramethyl-1,3,2-dioxaborolan-2-yl)prop-2-en-1-yl]oxy]ethyl)pyridin-2-yl]piperazine as yellow oil.

Step 6

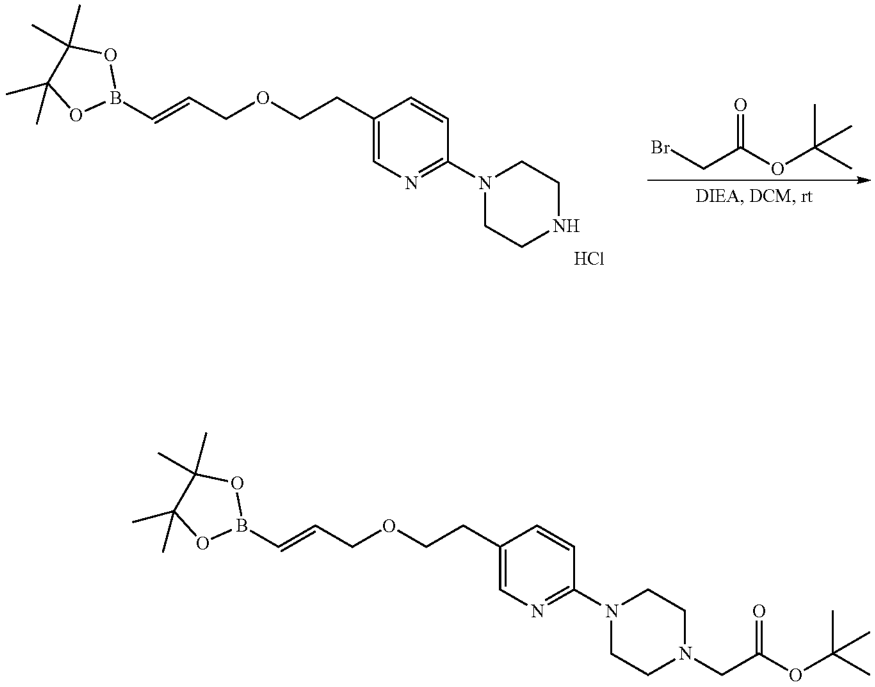

Into a 100-mL 3-neck round-bottom flask purged and maintained under an inert atmosphere of nitrogen was placed N-(2-aminoethyl)-N-(2-chloroethyl)-5-(2-[[(2E)-3-(tetramethyl-1,3,2-dioxaborolan-2-yl)prop-2-en-1-yl]oxy]ethyl)pyridin-2-amine (410 mg, 1.00 mmol, 1.00 equiv) in dichloromethane, N,N-diisopropylethylamine (645 mg, 4.99 mmol, 5.00 equiv), and tert-butyl 2-bromoacetate (585 mg, 3.00 mmol, 3.00 equiv) was added. The resulting solution was stirred for 12 hours at 25° C. The resulting mixture was concentrated under vacuum. The residue was applied onto a silica gel column eluting with dichloromethane/methanol (v:v=10:1). This resulted in 0.32 g (66%) of tert-butyl 2-[4-[5-(2-[[(2E)-3-(tetramethyl-1,3,2-dioxaborolan-2-yl)prop-2-en-1-yl]oxy]ethyl)pyridin-2-yl]piperazin-1-yl]acetate as yellow oil.

Step 7

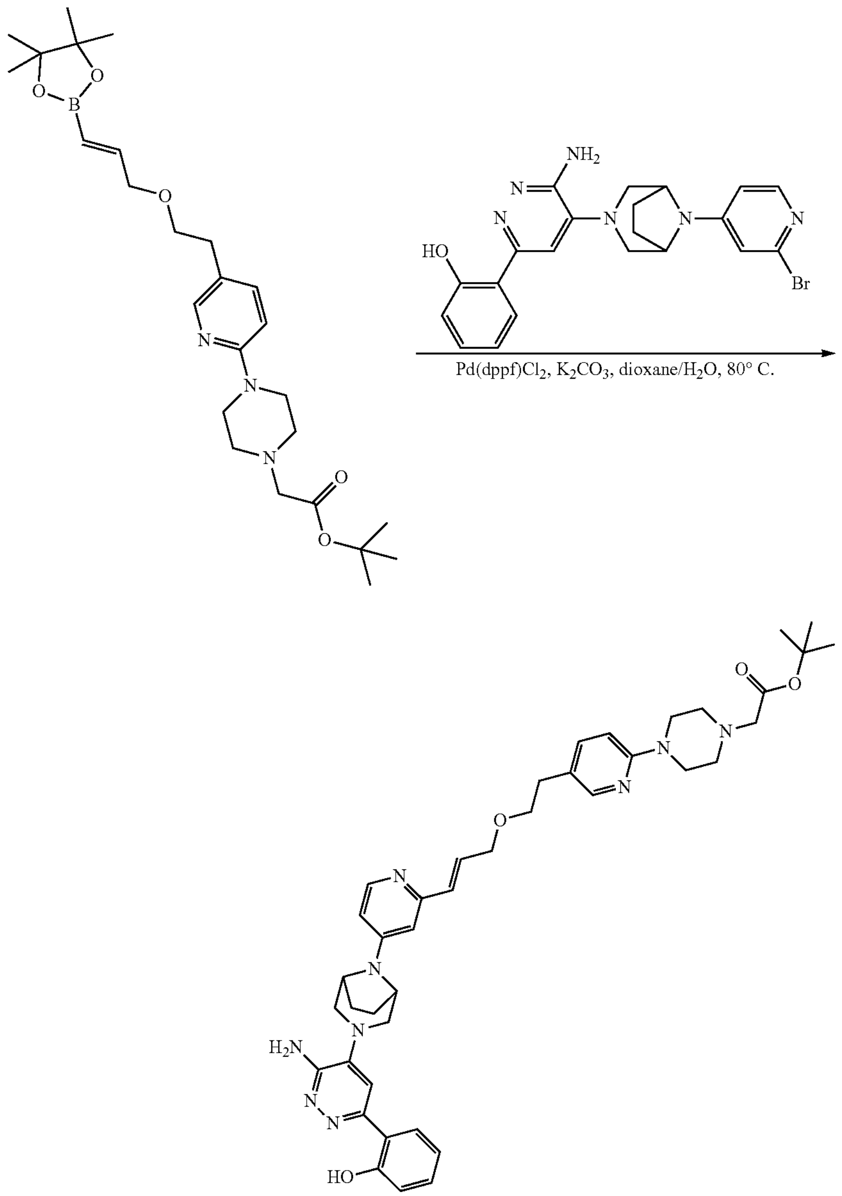

Into a 25-mL sealed tube purged and maintained under an inert atmosphere of nitrogen was placed 2-6-amino-5-[8-(2-bromopyridin-4-yl)-3,8-diazabicyclo[3.2.1]octan-3-yl]pyridazin-3-ylphenol (158 mg, 0.35 mmol, 1.00 equiv) in dioxane/water (v:v=4:1), tert-butyl 2-[4-[5-(2-[[(2E)-3-(tetramethyl-1,3,2-dioxaborolan-2-yl)prop-2-en-1-yl]oxy]ethyl)pyridin-2-yl]piperazin-1-yl]acetate (205 mg, 0.42 mmol, 1.20 equiv), potassium carbonate (145 mg, 1.05 mmol, 3.00 equiv), and Pd(dppf)C12 (12 mg, 0.02 mmol, 0.05 equiv) was added. The resulting solution was stirred for 3 hours at 80° C. in an oil bath. The reaction mixture was cooled to 25° C. The reaction was then quenched by the addition of water (5 mL). The resulting solution was extracted with ethyl acetate (20 mL×2), and the organic layers were combined and dried over anhydrous sodium sulfate and concentrated under vacuum. The residue was applied onto a silica gel column with dichloromethane/methanol (v:v=10:1). This resulted in 0.16 g (63%) of tert-butyl 2-[4-[5-(2-[[(2E)-3-(4-[3-[3-amino-6-(2-hydroxyphenyl)pyridazin-4-yl]-3,8-diazabicyclo[3.2.1]octan-8-yl]pyridin-2-yl)prop-2-en-1-yl]oxy]ethyl)pyridin-2-yl]piperazin-1-yl]acetate as a light yellow solid.

tert-Butyl 2-[4-[5-(2-[[(2E)-3-(4-[3-[3-amino-6-(2-hydroxyphenyl)pyridazin-4-yl]-3,8-diazabicyclo[3.2.1]octan-8-yl]pyridin-2-yl)prop-2-en-1-yl]oxy]ethyl)pyridin-2-yl]piperazin-1-yl]acetate was converted to the final compound, (2S,4R)-1-((2S)-2-(2-(4-(5-(2-(3-(4-(3-(3-amino-6-(2-hydroxyphenyl)pyridazin-4-yl)-3,8-diazabicyclo[3.2.1]octan-8-yl)pyridin-2-yl)propoxy)ethyl)pyridin-2-yl)piperazin-1-yl)acetamido)-3,3-dimethylbutanoyl)-4-hydroxy-N-(4-(4-methylthiazol-5-yl)benzyl)pyrrolidine-2-carboxamide according to the scheme below using procedures described above for other examples as well as procedures appreciated by those skilled in the art.

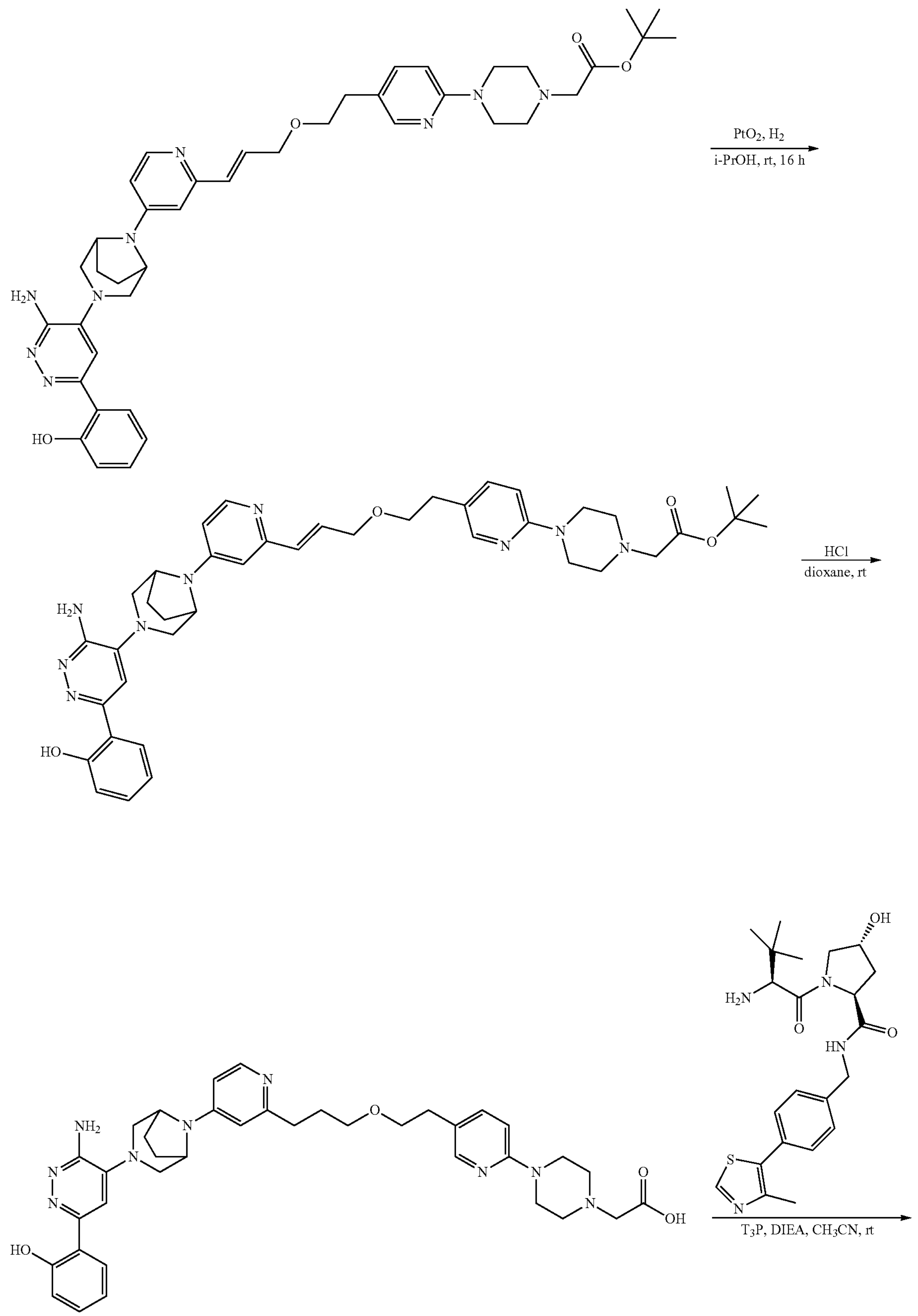
PtO2, H2
i-PrOH, rt, 16 h
HCl
dioxane, rt
T3P, DIEA, CH3CN, rt

-continued

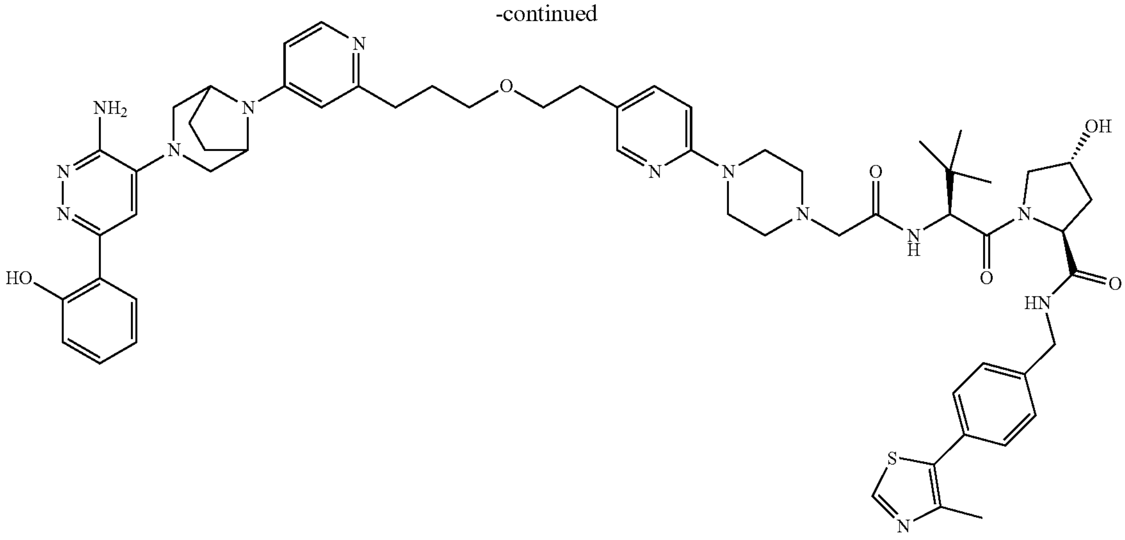

Exemplary Compound 4649

Exemplary Synthesis of Exemplary Compound 49

Step 1

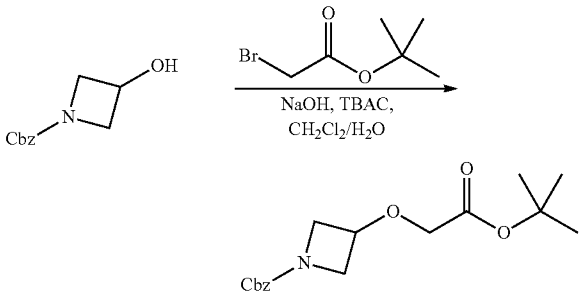

Into a 100-mL round-bottom flask, was placed benzyl 3-hydroxyazetidine-1-carboxylate (3.11 g, 15.01 mmol, 1.00 equiv), dichloromethane (30 mL), tert-butyl 2-bromoacetate (4.37 g, 22.40 mmol, 1.50 equiv), sodium hydroxide (37% aq.) (30 mL), and TBAC (4.17 g, 1.00 equiv) at 0° C. The resulting solution was stirred for 3 hours at 25° C. The resulting solution was extracted with dichloromethane (2×30 mL), and organic layers were combined and dried over anhydrous sodium sulfate and concentrated under vacuum. The residue was applied onto a silica gel column eluting with ethyl acetate/petroleum ether (1/5). This resulted in 3.6 g (75%) of benzyl 3-[2-(tert-butoxy)-2-oxoethoxy]azetidine-1-carboxylate as a colorless oil.

Step 2

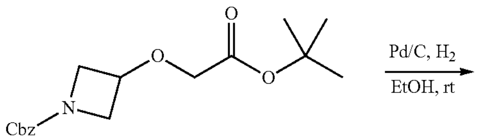

-continued

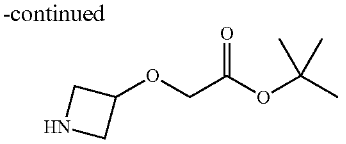

Into a 250-mL round-bottom flask, was placed benzyl 3-[2-(tert-butoxy)-2-oxoethoxy]azetidine-1-carboxylate (3.22 g, 10.02 mmol, 1.00 equiv), ethanol (100 mL), palladium on carbon (0.322 g). The resulting solution was stirred for 12 hours under $H_2$ atmosphere at 25° C. The solids were filtered out. The resulting mixture was concentrated under vacuum. This resulted in 1.75 g (93%) of tert-butyl 2-(azetidin-3-yloxy)acetate as a colorless oil.

Step 3

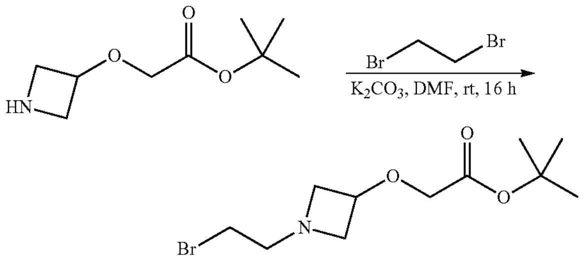

Into a 50-mL round-bottom flask, was placed tert-butyl 2-(azetidin-3-yloxy)acetate (374 mg, 2.00 mmol, 1.00 equiv), N,N-dimethylformamide (15 mL), potassium carbonate (828 mg, 5.99 mmol, 3.00 equiv), and 1,2-dibromoethane (1.86 g, 9.90 mmol, 5.00 equiv). The resulting solution was stirred for 12 hours at 25° C. The reaction was then quenched by the addition of water (10 mL). The resulting solution was extracted with ethyl acetate (2×20 mL), and the organic layers were combined and dried over anhydrous sodium sulfate. The residue was applied onto a silica gel column eluting with ethyl acetate/petroleum ether (1/3). This resulted in 80 mg (14%) of tert-butyl 2-[[1-(2-bromoethyl)azetidin-3-yl]oxy]acetate as a colorless oil.

tert-Butyl 2-[[1-(2-bromoethyl)azetidin-3-yl]oxy]acetate was converted to the final compound, (2S,4R)-1-((2S)-2-(2-((1-(2-(4-(3-(4-(3-(3-amino-6-(2-hydroxyphenyl)pyridazin-4-yl)-3,8-diazabicyclo[3.2.1]octan-8-yl)pyridin-2-yl)propyl)piperazin-1-yl)ethyl)azetidin-3-yl)oxy)acetamido)-3,3-dimethylbutanoyl)-4-hydroxy-N—((S)-1-(4-(4-methylthiazol-5-yl)phenyl)ethyl)pyrrolidine-2-carboxamide, using procedures described above for other examples as well as procedures obvious to those skilled in the art.

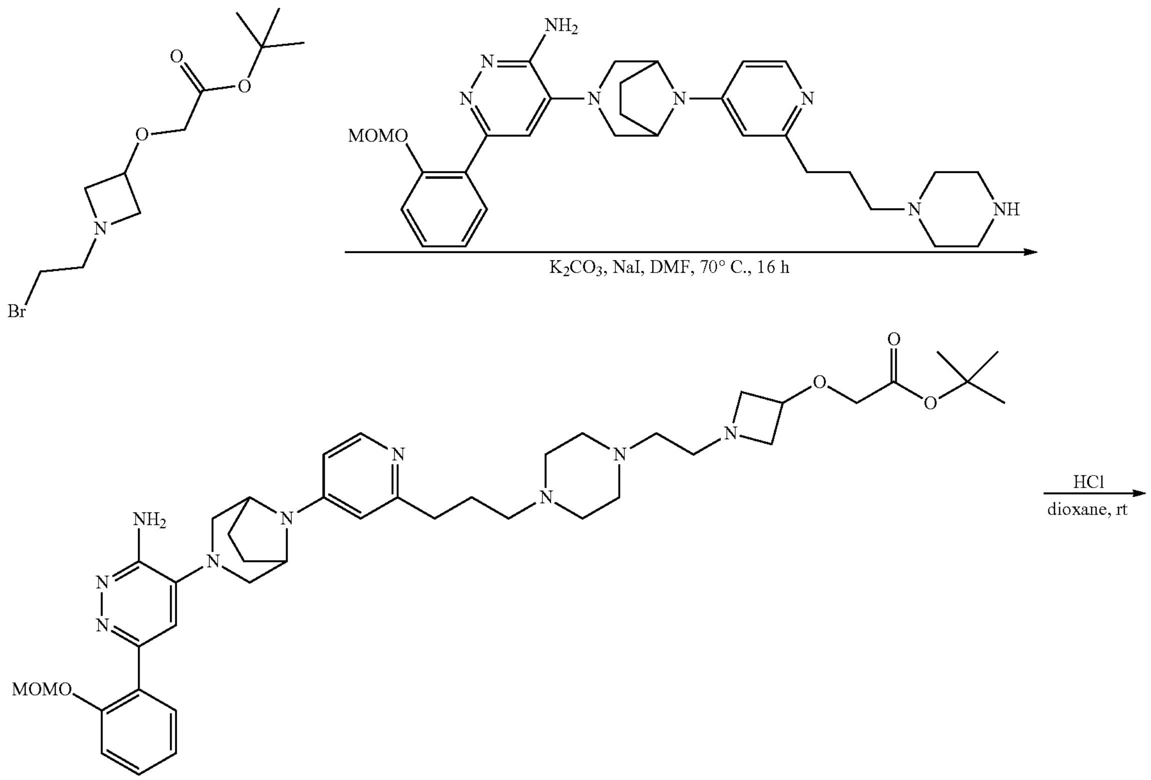

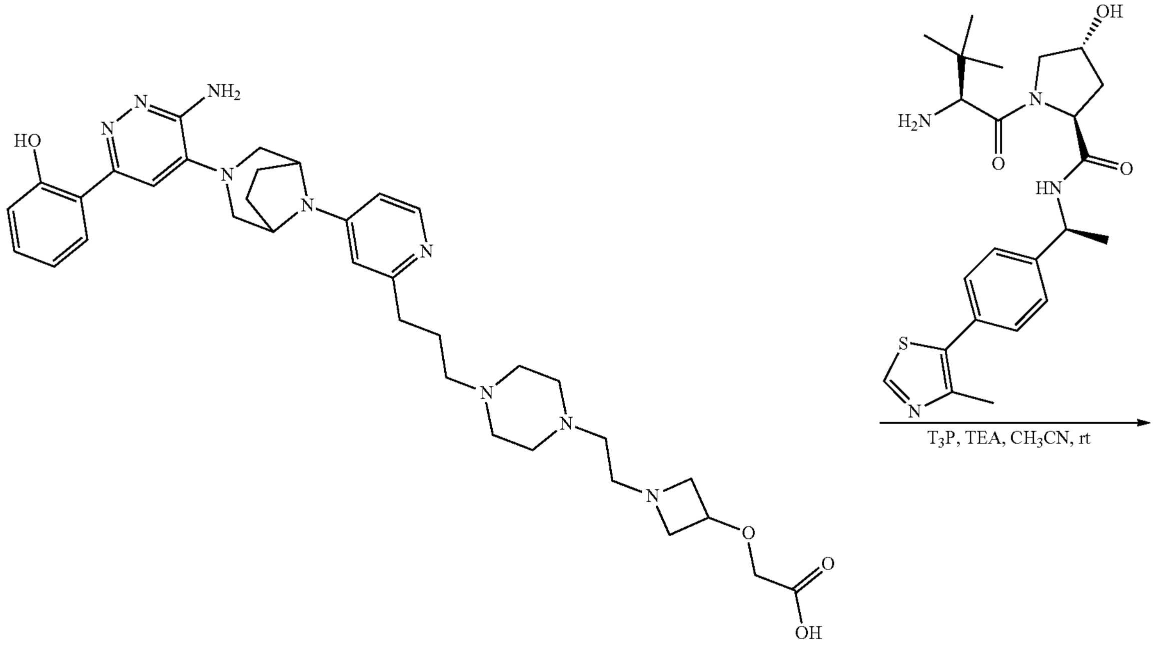

-continued
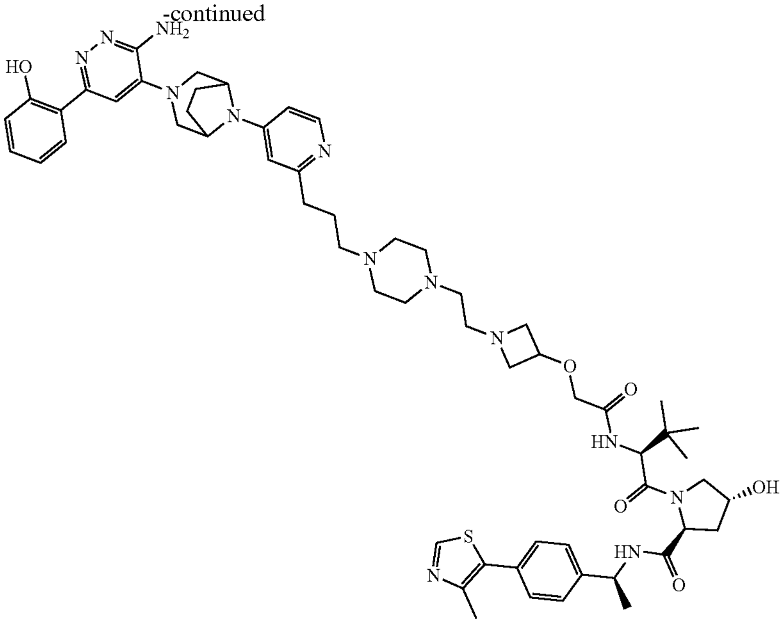
Exemplary Compound 49
Exemplary Synthesis of Exemplary Compound 51
Exemplary Compound 51 was prepared according to the scheme below using procedures from examples described above (e.g., Exemplary Compound 37) and other procedures appreciated by those skilled in the art.
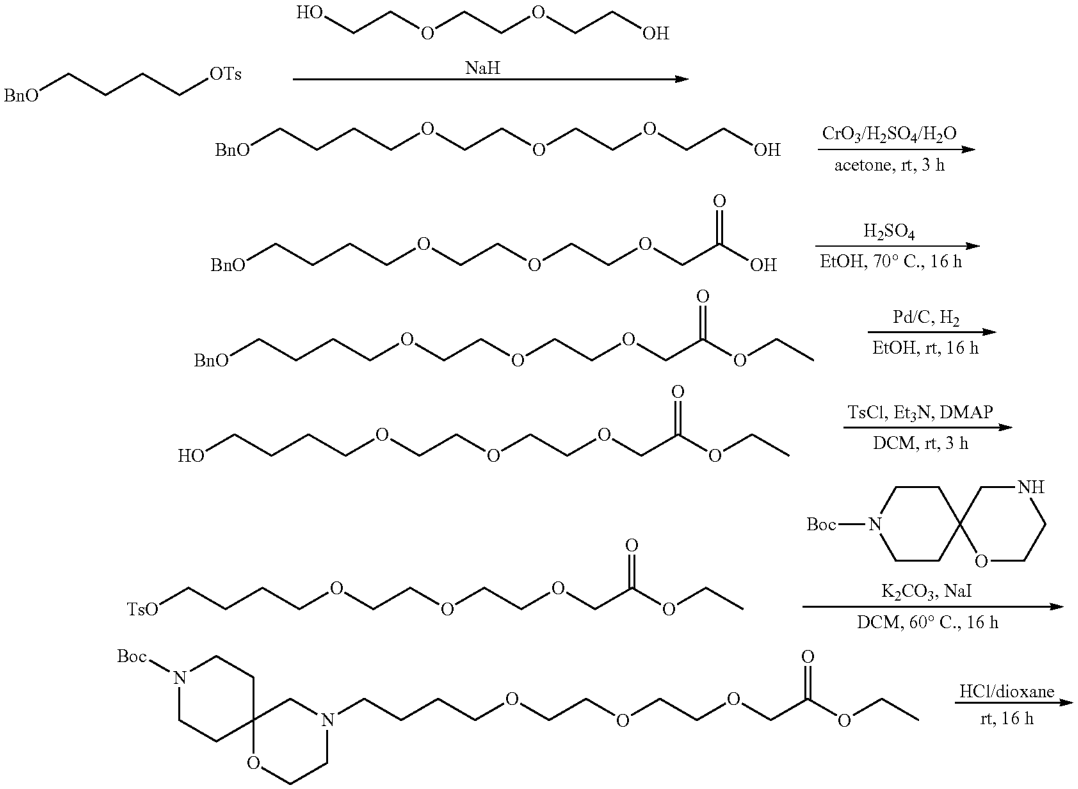

-continued
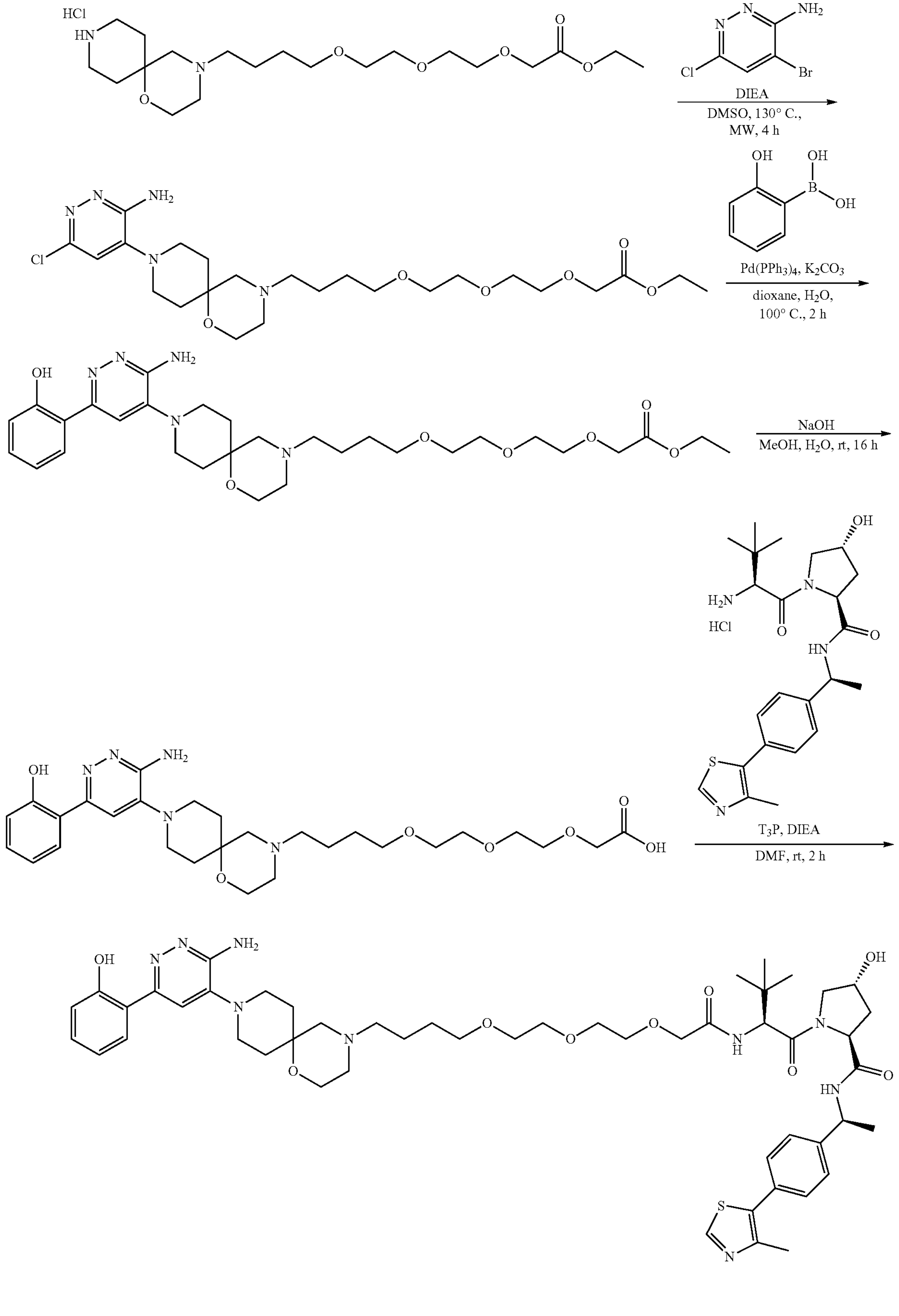

Exemplary Synthesis of Exemplary Compound 52
Exemplary Compound 52 was prepared according to the scheme below.
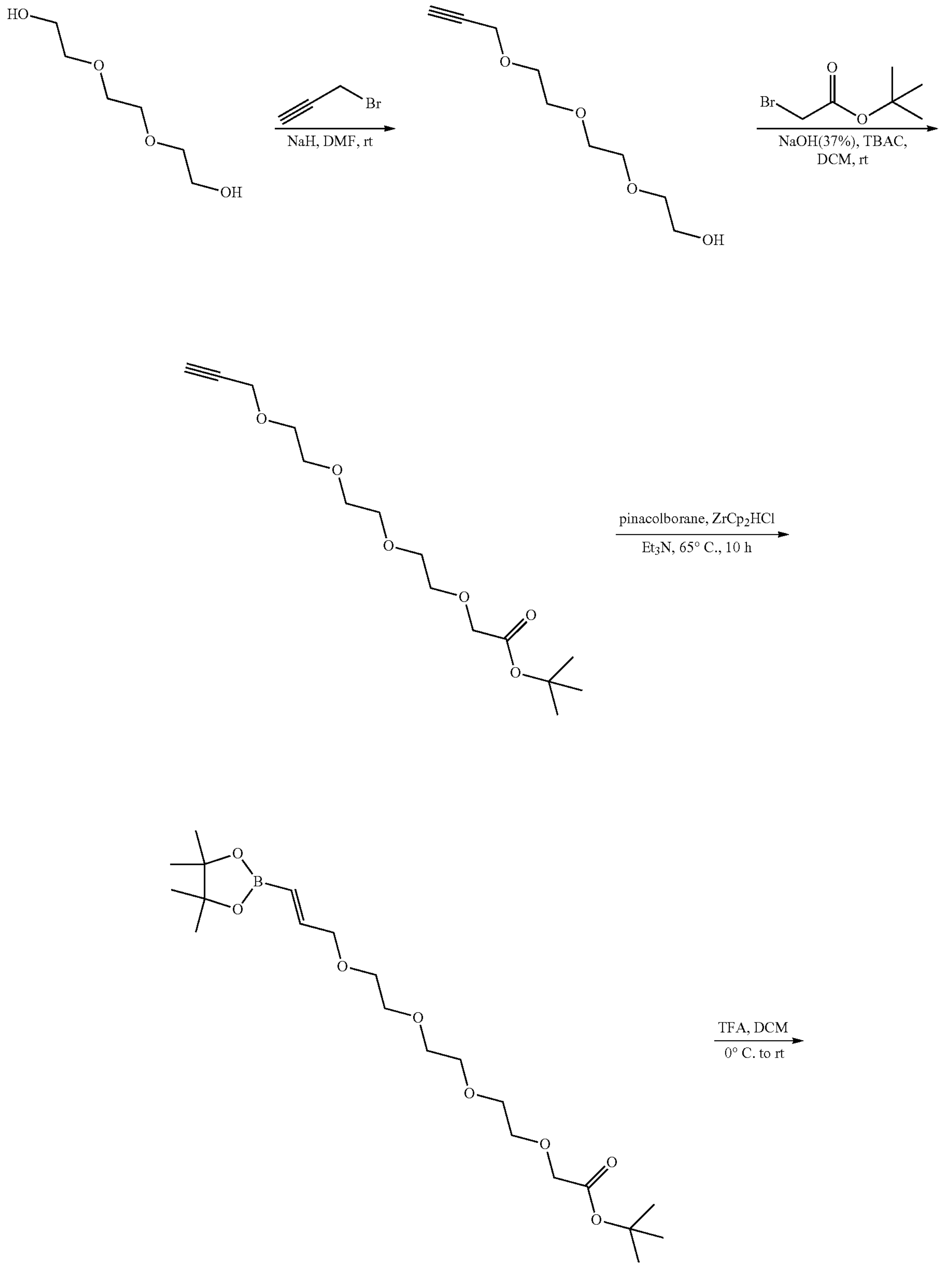

-continued
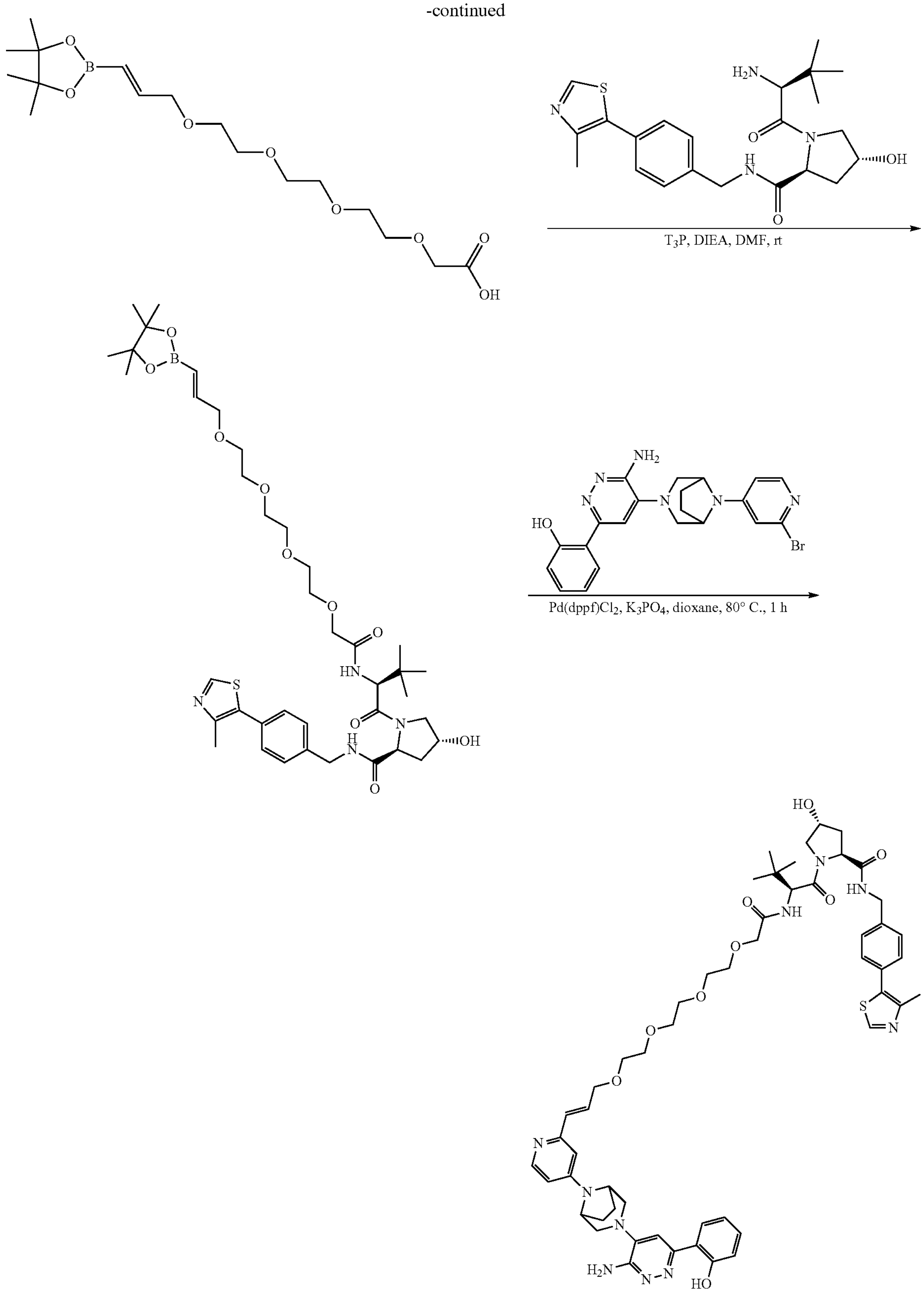
Exemplary Compound 52

Exemplary Synthesis of Exemplary Compound 53

Exemplary Compound 53 was prepared according to the scheme below.

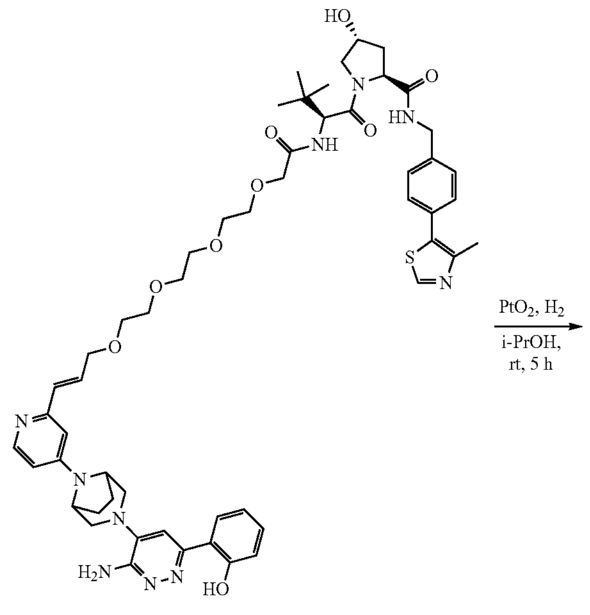

Exemplary Compound 52

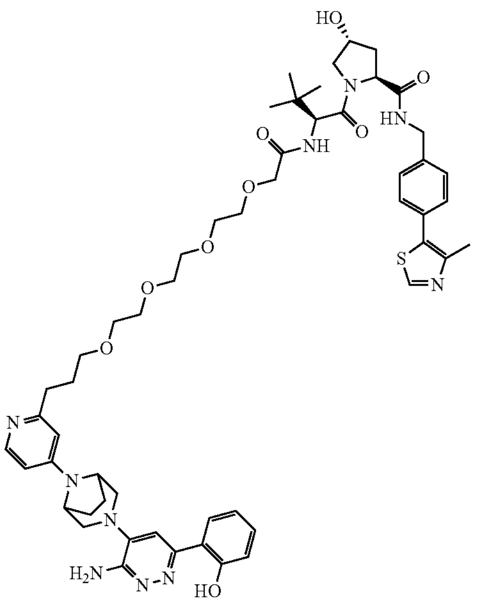

Exemplary Compound 53

Exemplary Synthesis of Exemplary Compound 54 and Exemplary Compound 55

Step 1

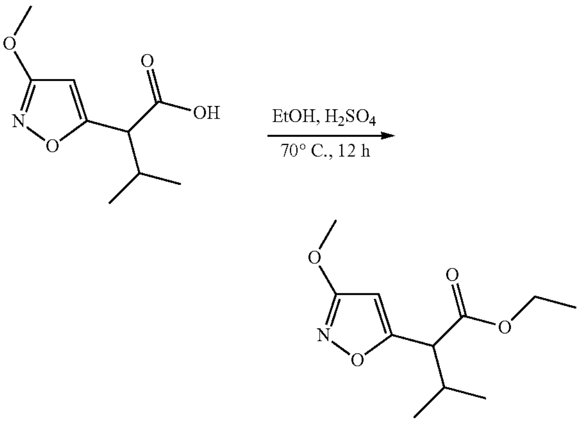

Into a 100-mL round-bottom flask, was placed 2-(3-methoxy-1,2-oxazol-5-yl)-3-methylbutanoic acid (2.1 g, 10.5 mmol, 1.00 equiv), ethanol (20.0 g, 434 mmol, 41.2 equiv), sulfuric acid (2.0 g, 20.4 mmol, 1.9 equiv). The resulting solution was stirred for 12 hours at 70° C. in an oil bath. The resulting mixture was concentrated under vacuum. This resulted in 1.9 g (79%) of ethyl 2-(3-methoxy-1,2-oxazol-5-yl)-3-methylbutanoate as a white solid.

Step 2

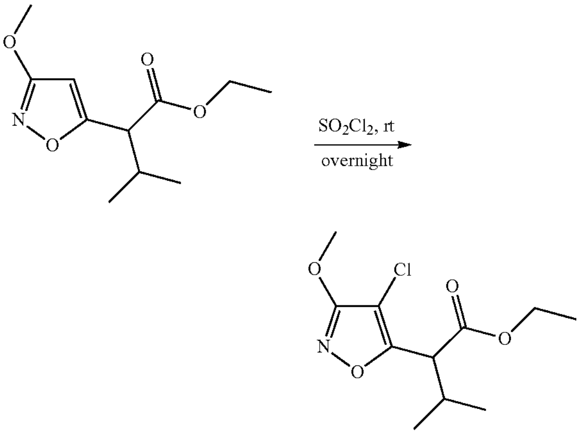

Into a 50-mL round-bottom flask was placed ethyl 2-(3-methoxy-1,2-oxazol-5-yl)-3-methylbutanoate (1.9 g, 8.4 mmol, 1.0 equiv) and sulfuryl chloride (20 mL). The resulting solution was stirred overnight at room temperature. The resulting mixture was concentrated under vacuum. The reaction was then quenched by the addition of 30 mL of water. The resulting solution was extracted with ethyl acetate (30 ml×3), and organic layers were combined. The residue was applied onto a silica gel column eluting with ethyl acetate/petroleum ether (1:1). This resulted in 1.5 g (69%) of ethyl 2-(4-chloro-3-methoxy-1,2-oxazol-5-yl)-3-methylbutanoate as yellow oil.

Step 3

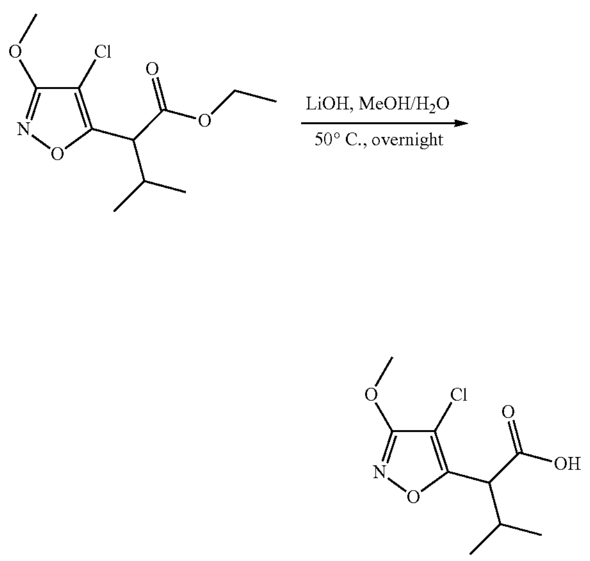

Into a 50-mL round-bottom flask, was placed a solution of ethyl 2-(4-chloro-3-methoxy-1,2-oxazol-5-yl)-3-methylbutanoate (1.5 g, 5.7 mmol, 1.0 equiv) in methanol/H2O (5/5 mL), and lithium hydroxide (300 mg, 12.5 mmol, 2.2 equiv). The resulting solution was stirred overnight at 50° C. in an oil bath. The pH value of the solution was adjusted to 6 with IM HCl. The resulting solution was extracted with ethyl acetate (30 ml×3), and organic layers were combined and concentrated under vacuum. The crude product was purified by prep-HPLC with the following conditions: Column; mobile phase, Column: XBridge Prep C18 OBD Column, 5 um, 19*150 mm; Mobile Phase A: Water (0.1% FA), Mobile Phase B: ACN; Flow rate: 20 mL/min; Gradient: 34% B to 48% B in 8 min; 220 nm. This resulted in 300 mg (22.4%) of 2-(4-chloro-3-methoxy-1,2-oxazol-5-yl)-3-methylbutanoic acid as a white solid.

Step 4

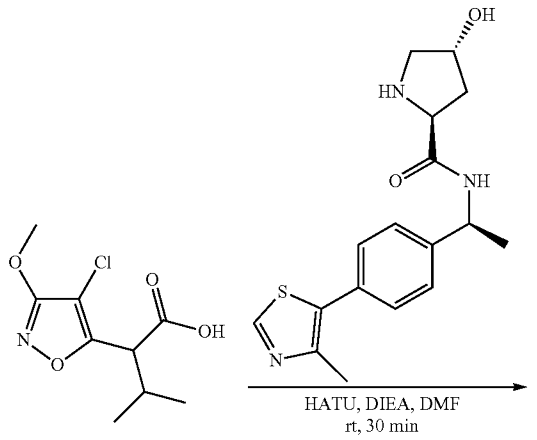

-continued

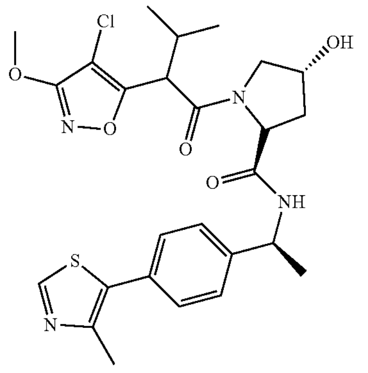

Into a 50-mL round-bottom flask was placed a solution of 2-(4-chloro-3-methoxy-1,2-oxazol-5-yl)-3-methylbutanoic acid (260 mg, 1.1 mmol, 1.0 equiv) in N,N-dimethylformamide (20 mL), N,N,N',N'-tetramethyl-O-(7-azabenzotriazol-1-yl)uronium hexafluorophospate (360 mg, 1.0 mmol, 0.9 equiv), N,N-diisopropylethylamine (350 mg, 2.7 mmol, 2.4 equiv), and (2S,4R)-4-hydroxy-N-[(1S)-1-[4-(4-methyl-1,3-thiazol-5-yl)phenyl]ethyl]pyrrolidine-2-carboxamide (350 mg, 1.1 mmol, 1.0 equiv). The resulting solution was stirred for 30 minutes at room temperature. The reaction was then quenched by the addition of 30 mL of water. The resulting solution was extracted with ethyl acetate (30 ml×3), and the organic layers were combined and dried over anhydrous sodium sulfate and concentrated under vacuum. The residue was applied onto a silica gel column eluting with dichloromethane/methanol (10:1). This resulted in 275 mg (45%) of (2S,4R)-1-[2-(4-chloro-3-methoxy-1,2-oxazol-5-yl)-3-methylbutanoyl]-4-hydroxy-N-[(1S)-1-[4-(4-methyl-1,3-thiazol-5-yl) phenyl]ethyl] pyrrolidine-2-carboxamide as a white solid.

Step 5

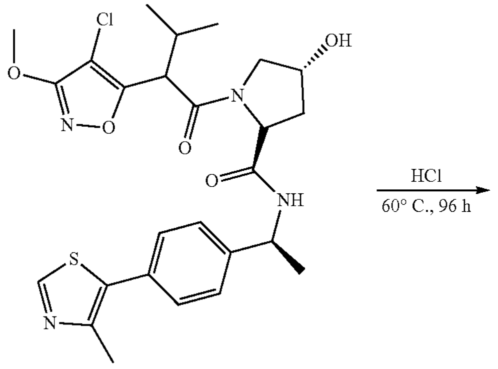

-continued

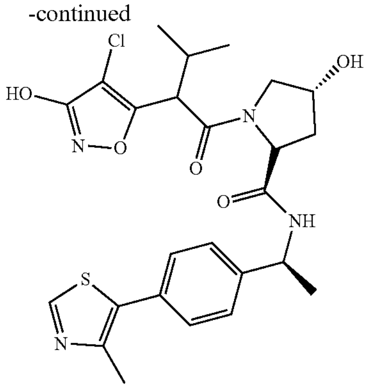

Into a 50-mL round-bottom flask, was placed (2S,4R)-1-[2-(4-chloro-3-methoxy-1,2-oxazol-5-yl)-3-methylbutanoyl]-4-hydroxy-N-[(1 S)-1-[4-(4-methyl-1,3-thiazol-5-yl)phenyl]ethyl]pyrrolidine-2-carboxamide (275 mg, 0.5 mmol, 1.0 equiv) and 4M hydrogen chloride solution in dioxane (25 mL). The resulting solution was stirred for 96 hours at 60° C. in an oil bath. The resulting mixture was concentrated under vacuum. This resulted in 259 mg (97%) of (2S,4R)-1-[2-(4-chloro-3-hydroxy-1,2-oxazol-5-yl)-3-methylbutanoyl]-4-hydroxy-N-[(1S)-1-[4-(4-methyl-1,3-thiazol-5-yl) phenyl]ethyl]pyrrolidine-2-carboxamide as a yellow solid.

(2S,4R)-1-[2-(4-chloro-3-hydroxy-1,2-oxazol-5-yl)-3-methylbutanoyl]-4-hydroxy-N-[(1S)-1-[4-(4-methyl-1,3-thiazol-5-yl) phenyl]ethyl]pyrrolidine-2-carboxamide was converted to the final compounds, (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)-4-chloroisoxazol-5-yl)-3-methylbutanoyl)-4-hydroxy-N—((S)-1-(4-(4-methylthiazol-5-yl)phenyl)ethyl)pyrrolidine-2-carboxamide and (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)-4-chloroisoxazol-5-yl)-3-methylbutanoyl)-4-hydroxy-N—((S)-1-(4-(4-methylthiazol-5-yl)phenyl)ethyl)pyrrolidine-2-carboxamide, according to the scheme below and using procedures described for earlier examples above.

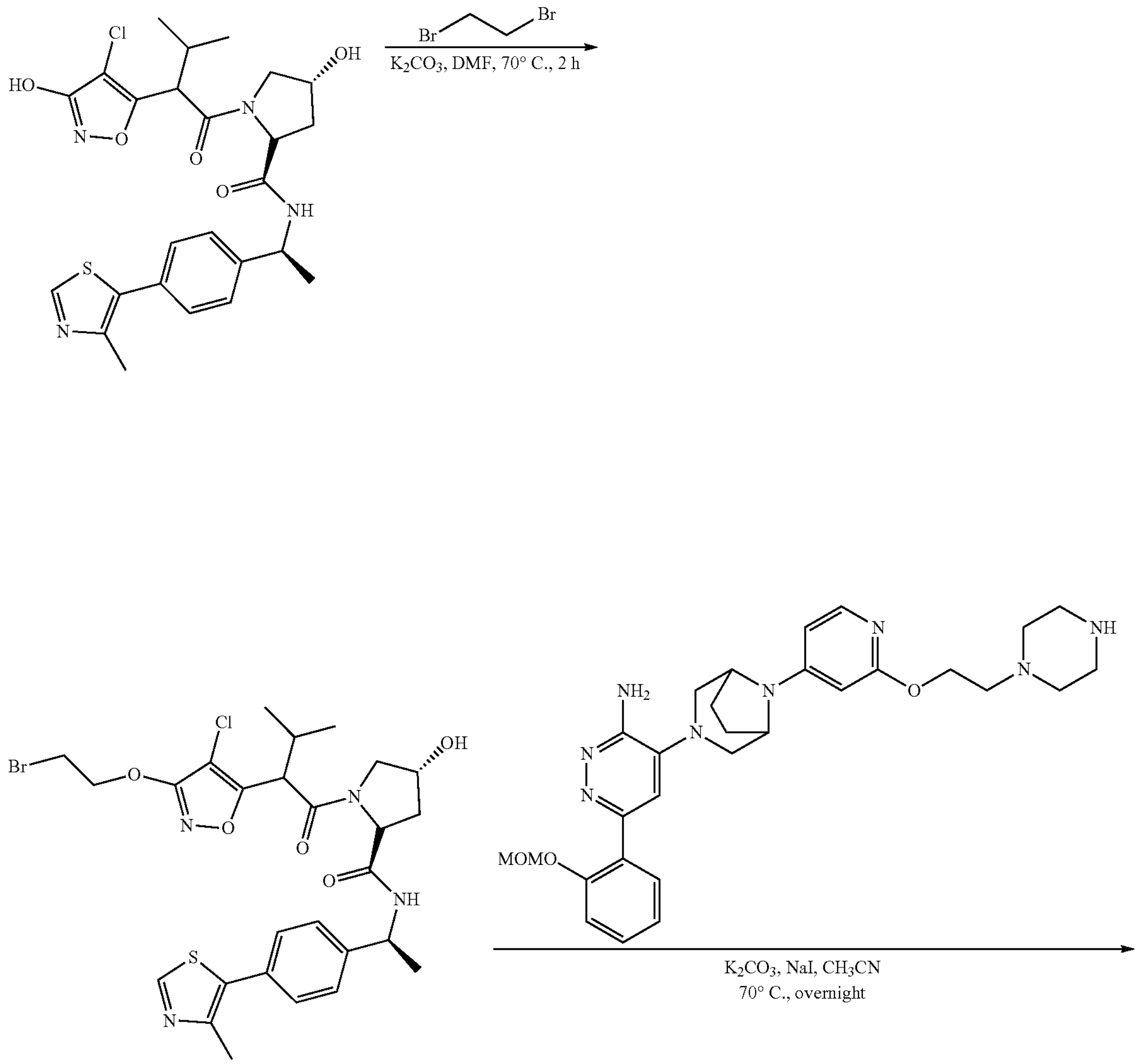

-continued
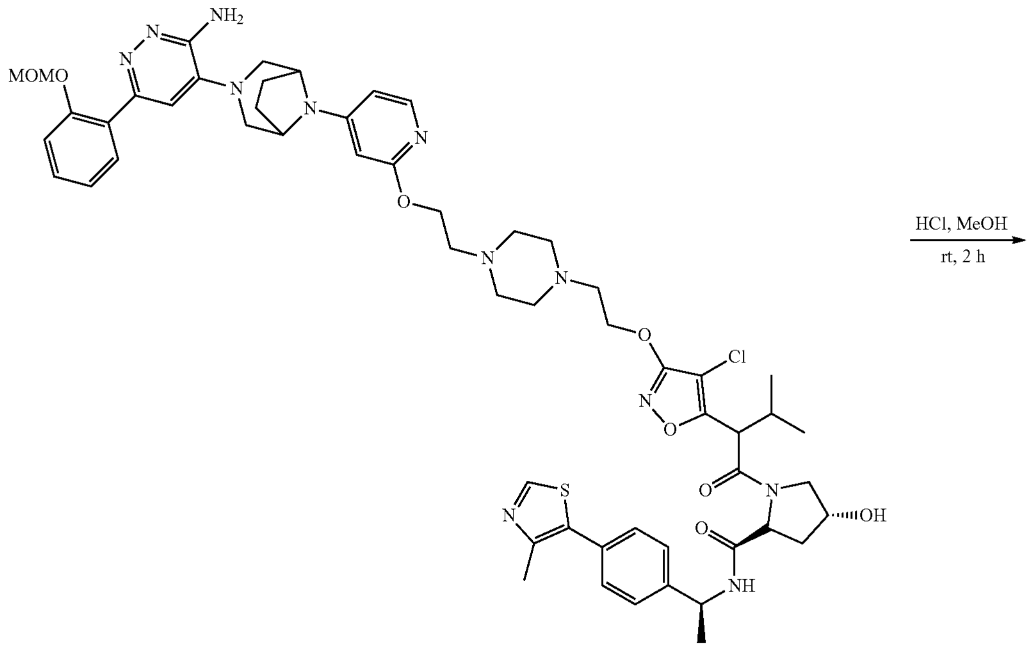
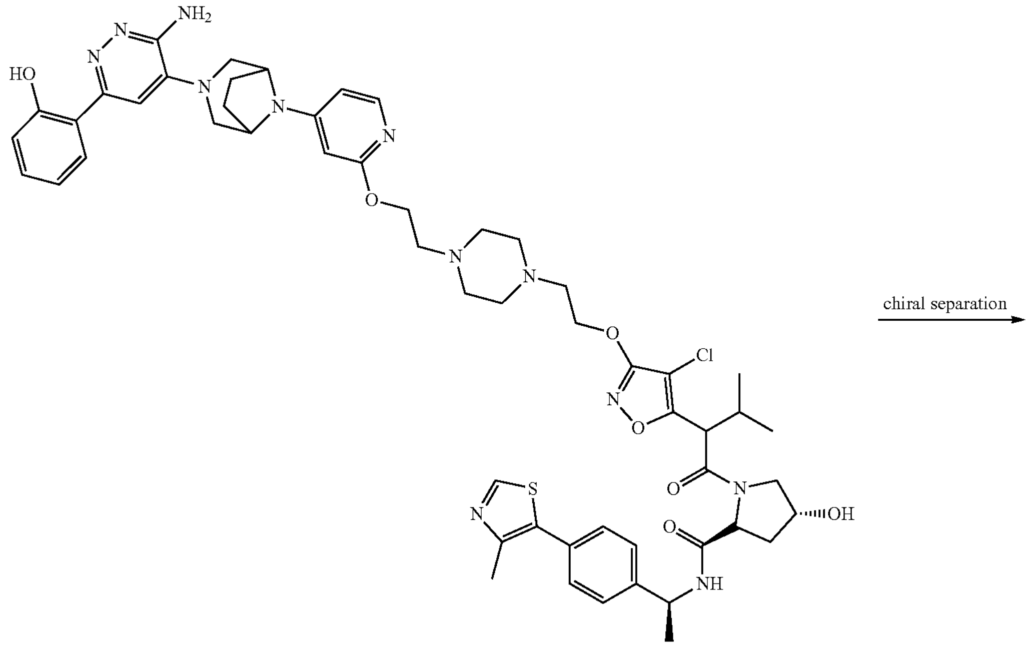

-continued

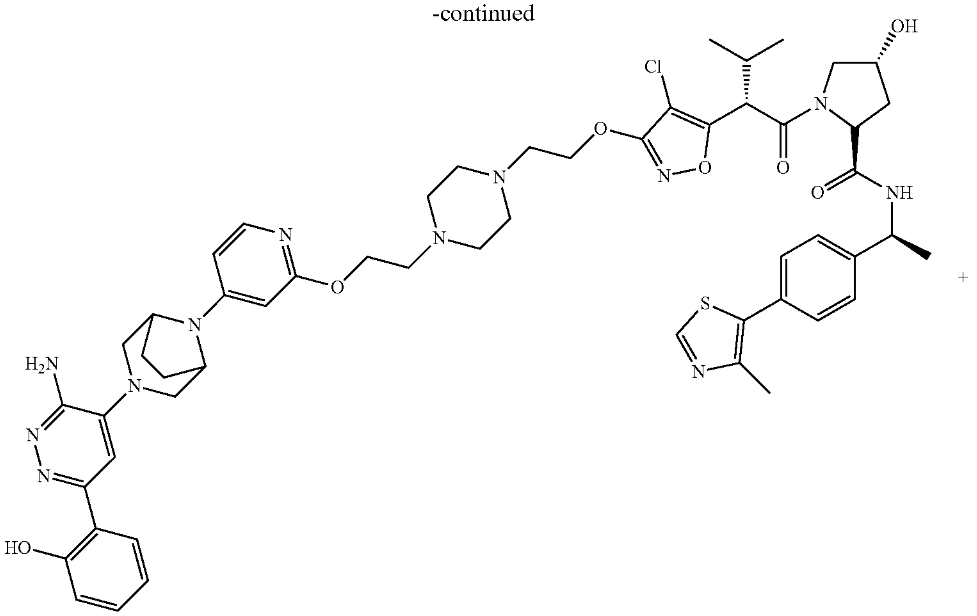

Exemplary Compound 54

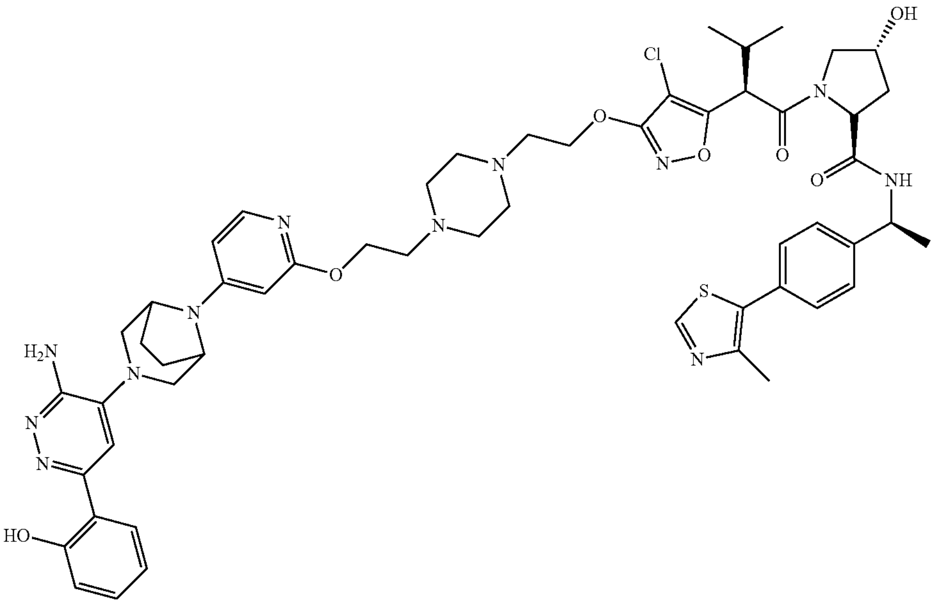

Exemplary Compound 55

Exemplary Synthesis of Exemplary Compound 56

Step 1

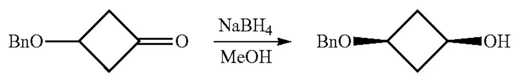

Into a 250-mL round-bottom flask, was placed a solution of 3-(benzyloxy)cyclobutan-1-one (6.0 g, 34.05 mmol, 1.0 equiv) in ethanol (100 mL). This was followed by the addition of sodium borohydride (1.25 g, 33.94 mmol, 1.00 equiv) in several batches at 0° C. The resulting solution was stirred for 3 hours at 0° C. The reaction was then quenched by the addition of water (100 mL). The resulting solution was extracted with ethyl acetate (50 mL×2), and the organic layers were combined, dried over anhydrous sodium sulfate and concentrated under vacuum. This resulted in 6.0 g (99%) of (1s,3s)-3-(benzyloxy)cyclobutan-1-ol as a light yellow oil.

Step 2

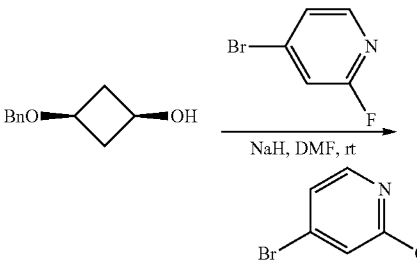

Into a 500-mL round-bottom flask purged and maintained under an inert atmosphere of nitrogen was placed a solution of (1s,3s)-3-(benzyloxy)cyclobutan-1-ol (8.0 g, 44.89 mmol, 1.10 equiv) in N,N-dimethylformamide (100 mL). This was followed by the addition of sodium hydride (60%) (2.15 g, 89.58 mmol, 1.20 equiv) in several batches at 0° C. To this was added 4-bromo-2-fluoropyridine (70.0 g, 39.78 mmol, 1.00 equiv). The resulting solution was stirred overnight at room temperature. The reaction was then quenched by the addition of water/ice. The resulting solution was extracted with ethyl acetate (80 mL×2), and organic layers were combined. The resulting mixture was washed with brine (80 mL×2). The resulting mixture was concentrated under reduced pressure. The residue was applied onto a silica gel column eluting with ethyl acetate/petroleum ether (1:1). This resulted in 7.0 g (53%) of 4-bromo-2-[(1s,3s)-3-(benzyloxy)cyclobutoxy]pyridine as a light yellow oil.

Step 3

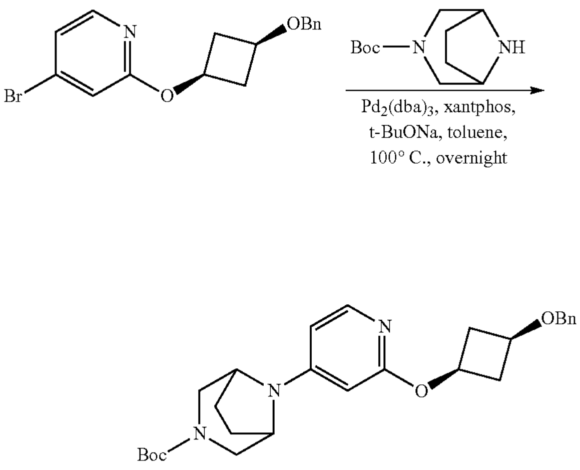

Into a 500-mL round-bottom flask purged and maintained under an inert atmosphere of nitrogen, was placed a solution of 4-bromo-2-[(1s,3s)-3-(benzyloxy)cyclobutoxy]pyridine (8.4 g, 25.13 mmol, 1.30 equiv) in toluene (200 mL), tert-butyl 3,8-diazabicyclo[3.2.1]octane-3-carboxylate (4.11 g, 19.36 mmol, 1.00 equiv), sodium tert-butoxide (3.2 g, 33.2 mmol, 1.5 equiv), xantphos (2.32 g, 4.01 mmol, 0.20 equiv), and $Pd_2(dba)_3CH_2Cl_2$ (430.0 mg, 0.40 mmol, 0.02 equiv). The resulting solution was stirred overnight at 100° C. The reaction was then quenched by the addition of water (100 mL). The resulting solution was extracted with ethyl acetate (80 mL×2), and the organic layers were combined. The resulting mixture was washed with brine (100 mL×2). The mixture was dried over anhydrous sodium sulfate and concentrated under reduced pressure. The residue was applied onto a silica gel column eluting with ethyl acetate/hexane (1:1). This resulted in 8.0 g (89%) of tert-butyl 8-[2-[(1s,3s)-3-(benzyloxy)cyclobutoxy]pyridin-4-yl]-3,8-diazabicyclo[3.2.1]octane-3-carboxylate as a light yellow oil.

Step 4

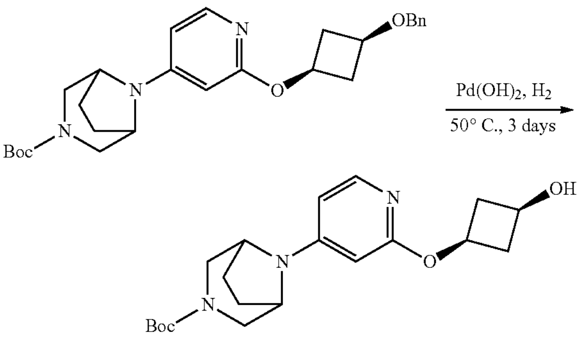

To a solution of tert-butyl 8-[2-[(1s,3s)-3-(benzyloxy)cyclobutoxy]pyridin-4-yl]-3,8-diazabicyclo[3.2.1]octane-3-carboxylate (7.0 g, 15.03 mmol, 1.00 equiv) in 150 mL ethanol was added palladium hydroxide (7.0 g, 49.85 mmol, 3.32 equiv) and acetic acid (2 mL) under nitrogen atmosphere in a 250 ml round bottom flask. The flask was then vacuumed and flushed with hydrogen. The reaction mixture was hydrogenated at 50° C. for 3 days under hydrogen atmosphere using a hydrogen balloon, then filtered through a Celite pad and concentrated under reduced pressure. This resulted in 5.4 g (96%) of tert-butyl 8-[2-[(1s,3s)-3-hydroxycyclobutoxy]pyridin-4-yl]-3,8-diazabicyclo[3.2.1]octane-3-carboxylate as a light yellow oil.

Step 5

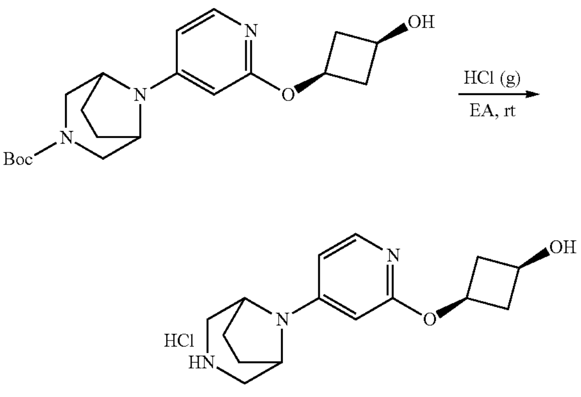

Into a 100-mL round-bottom flask, was placed a solution of tert-butyl 8-[2-[(1s,3s)-3-hydroxycyclobutoxy]pyridin-4-yl]-3,8-diazabicyclo[3.2.1]octane-3-carboxylate (5.0 g, 13.32 mmol, 1.00 equiv) in the mixed solvent of ethyl acetate and methanol (10:1) (50 mL). Hydrogen chloride (gas) was passed through the solution. The resulting mixture was stirred for 3 hours at room temperature and concentrated under reduced pressure. This resulted in 4.0 g (96%) of (1s,3s)-3-[(4-[3,8-diazabicyclo[3.2.1]octan-8-yl]pyridin-2-yl)oxy]cyclobutan-1-ol hydrochloride as an off-white solid.

Step 6

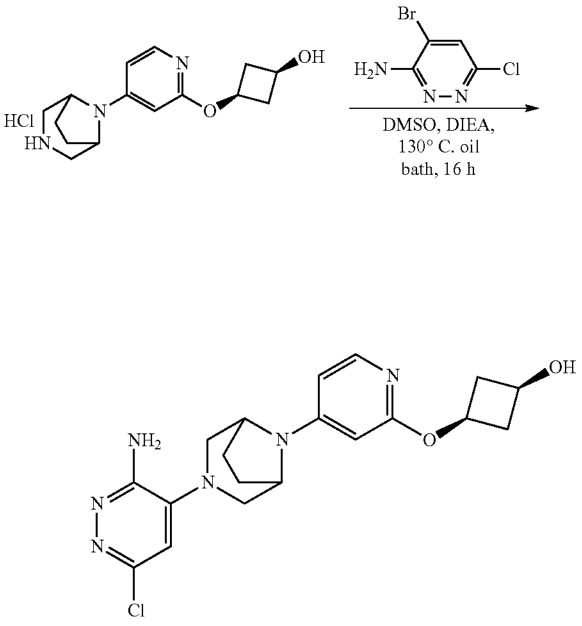

Into a 20-mL pressure tank reactor purged and maintained with an inert atmosphere of nitrogen, was placed a solution of (1s,3s)-3-[(4-[3,8-diazabicyclo[3.2.1]octan-8-yl]pyridin-2-yl)oxy]cyclobutan-1-ol hydrochloride (1.0 g, 3.21 mmol, 1.00 equiv) in dimethyl sulfoxide (10 mL). Then N,N-diisopropylethylamine (5 mL) and 4-bromo-6-chloro-pyridazin-3-amine (3.01 g, 14.44 mmol, 4.00 equiv) were added. The resulting solution was stirred for 16 hours at 130° C. The reaction was then quenched by the addition of water (50 mL). The resulting solution was extracted with ethyl acetate (3×30 mL), and the organic layers combined. The resulting mixture was washed with brine (3×50 mL). The mixture was dried over anhydrous sodium sulfate. The residue was applied onto a silica gel column eluting with dichloromethane/methanol (10:1). This resulted in 490 mg (38%) of (1s,3s)-3-([4-[3-(3-amino-6-chloropyridazin-4-yl)-3,8-diazabicyclo[3.2.1]octan-8-yl]pyridin-2-yl]oxy)cyclobutan-1-ol as a yellow oil.

Step 7

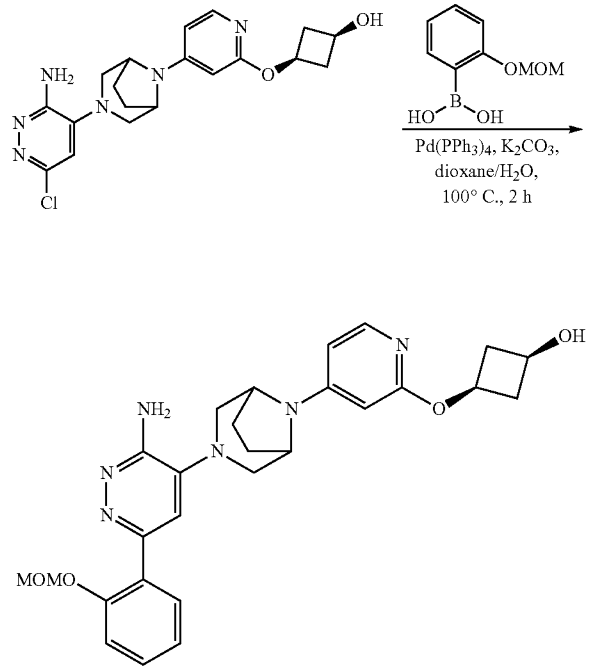

Into a 20-mL pressure tank reactor purged and maintained with an inert atmosphere of nitrogen, was placed a solution of (1s,3s)-3-([4-[3-(3-amino-6-chloropyridazin-4-yl)-3,8-diazabicyclo[3.2.1]octan-8-yl]pyridin-2-yl]oxy)cyclobutan-1-ol (800 mg, 1.99 mmol, 1.00 equiv) in the mixed solvent of dioxane and water (4:1) (15 mL), [2-(methoxymethoxy)phenyl]boronic acid (544 mg, 2.99 mmol, 1.50 equiv), potassium carbonate (824 mg, 6.0 mmol, 3.00 equiv), and $Pd(PPh_3)_4$ (230 mg, 0.20 mmol, 0.10 equiv). The resulting solution was stirred for 2 hours at 90° C. The reaction was then quenched by the addition of water (30 mL). The resulting solution was extracted with ethyl acetate (50 mL×2), and the organic layers combined. The resulting mixture was washed with brine (50 mL×2). The mixture was dried over anhydrous sodium sulfate. The residue was applied onto a silica gel column eluting with dichloromethane/methanol (10:1). This resulted in 820 mg (82%) of (1s,3 s)-3-[[4-(3-[3-amino-6-[2-(methoxymethoxy)phenyl] pyridazin-4-yl]-3,8-diazabicyclo[3.2.1]octan-8-yl)pyridin-2-yl]oxy]cyclobutan-1-ol as a yellow solid.

Step 8

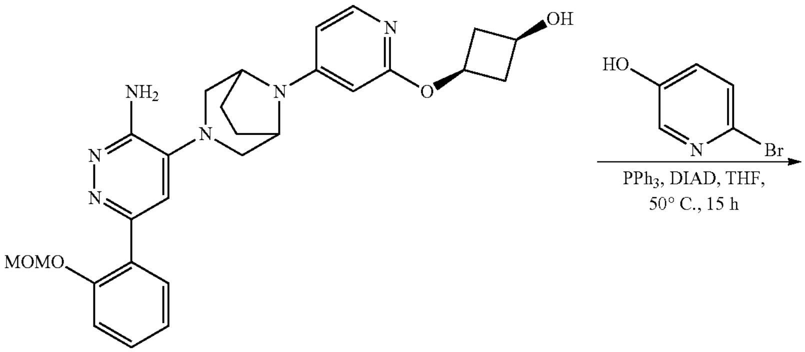

-continued

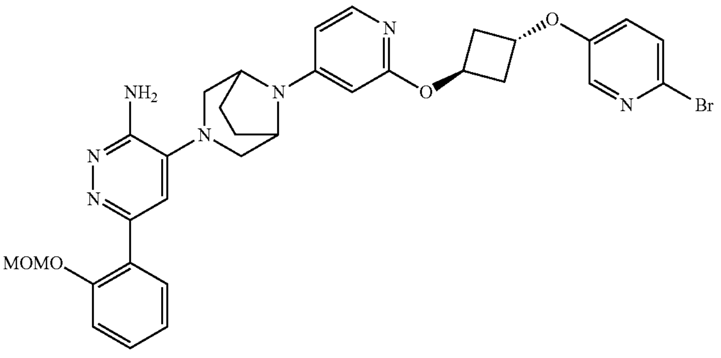

Into a 50-mL 3-necked round-bottom flask purged and maintained with an inert atmosphere of nitrogen was placed a solution of triphenylphosphine (351 mg, 1.34 mmol, 2.00 equiv) in tetrahydrofuran (distilled) (30 mL). This was followed by the addition of diisopropyl azodicarboxylate (270 mg, 1.34 mmol, 2.00 equiv) dropwise with stirring at 0° C. while a white precipitate appeared. To this was added (1s,3s)-3-[[4-(3-[3-amino-6-[2-(methoxymethoxy)phenyl] pyridazin-4-yl]-3,8-diazabicyclo[3.2.1]octan-8-yl)pyridin-2-yl]oxy]cyclobutan-1-ol (338 mg, 0.67 mmol, 1.00 equiv) and 6-bromopyridin-3-ol (232 mg, 1.33 mmol, 1.50 equiv) at 0° C. The resulting solution was stirred overnight at 50° C. The resulting mixture was concentrated under vacuum. The residue was applied onto a silica gel column eluting with dichloromethane/methanol (10:1). This resulted in 389 mg (88%) of 6-[2-(methoxymethoxy)phenyl]-4-(8-[2-[(1r, 3r)-3-[(6-bromopyridin-3-yl)oxy]cyclobutoxy]pyridin-4-yl]-3,8-diazabicyclo[3.2.1]octan-3-yl)pyridazin-3-amine as a yellow solid.

Step 9

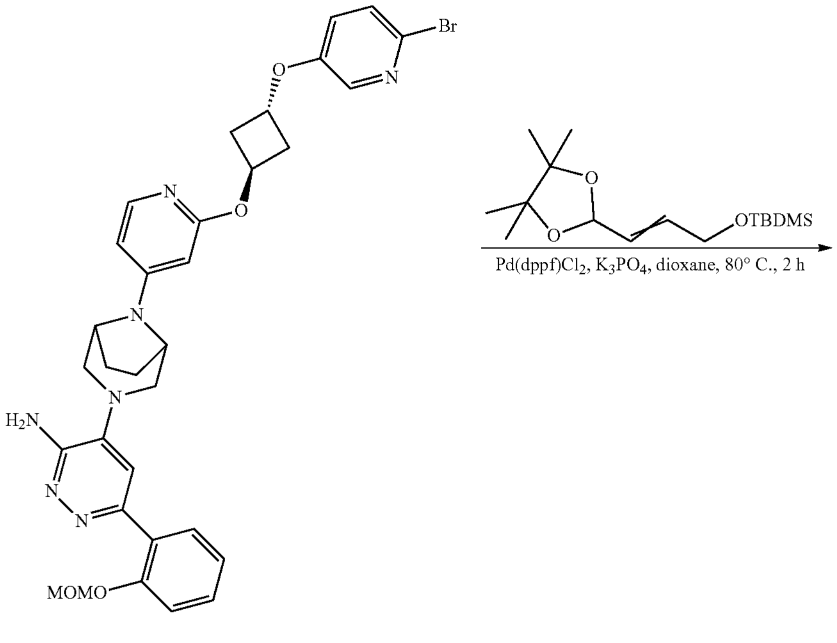

-continued

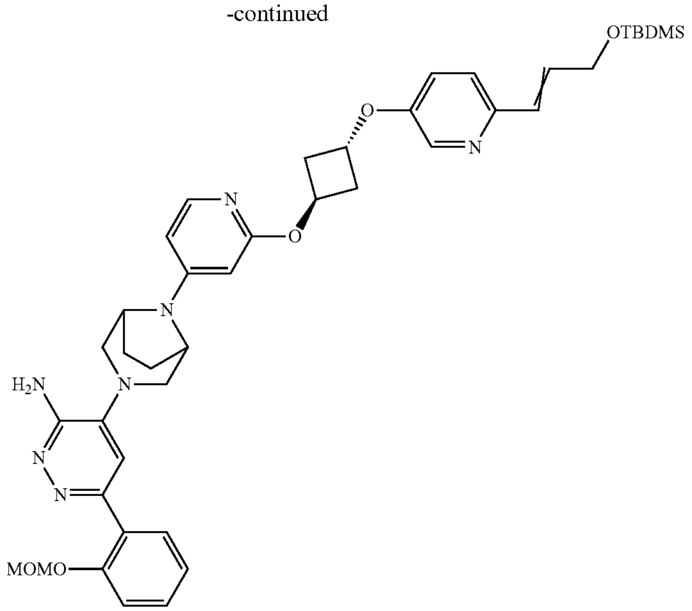

Into a 20-mL pressure tank reactor purged and maintained with an inert atmosphere of nitrogen, was placed a solution of 6-[2-(methoxymethoxy)phenyl]-4-(8-[2-[(1r,3r)-3-[(6-bromopyridin-3-yl)oxy]cyclobutoxy]pyridin-4-yl]-3,8-diazabicyclo[3.2.1]octan-3-yl)pyridazin-3-amine (155 mg, 0.23 mmol, 1.00 equiv) in the mixed solvent of dioxane and water (3:1) (8 mL), tert-butyldimethyl {[3-(tetramethyl-1,3,2-dioxaborolan-2-yl)prop-2-en-1-yl]oxy}silane (140 mg, 0.47 mmol, 2.00 equiv), potassium carbonate (95 mg, 0.69 mmol, 0.15 equiv), $Pd(PPh_3)_4C1_2CH_2Cl_2$ (28 mg, 0.03 mmol, 2.00 equiv). The resulting solution was stirred for 1 hour at 80° C. The reaction was then quenched by the addition of water. The resulting solution was extracted with ethyl acetate (30 mL×3), and the organic layers were combined. The resulting mixture was washed with brine (30 mL×2). The mixture was dried over anhydrous sodium sulfate. The residue was applied onto a silica gel column eluting with dichloromethane/methanol (10:1). This resulted in 130 mg (74%) of 6-[2-(methoxymethoxy)phenyl]-4-(8-[2-[(1r,3r)-3-[(6-[3-[(tert- butyldimethylsilyl)oxy]prop-1-en-1-yl]pyridin-3-yl)oxy]cyclobutoxy]pyridin-4-yl]-3,8-diazabicyclo[3.2.1]octan-3-yl)pyridazin-3-amine as a light yellow oil.

Step 10

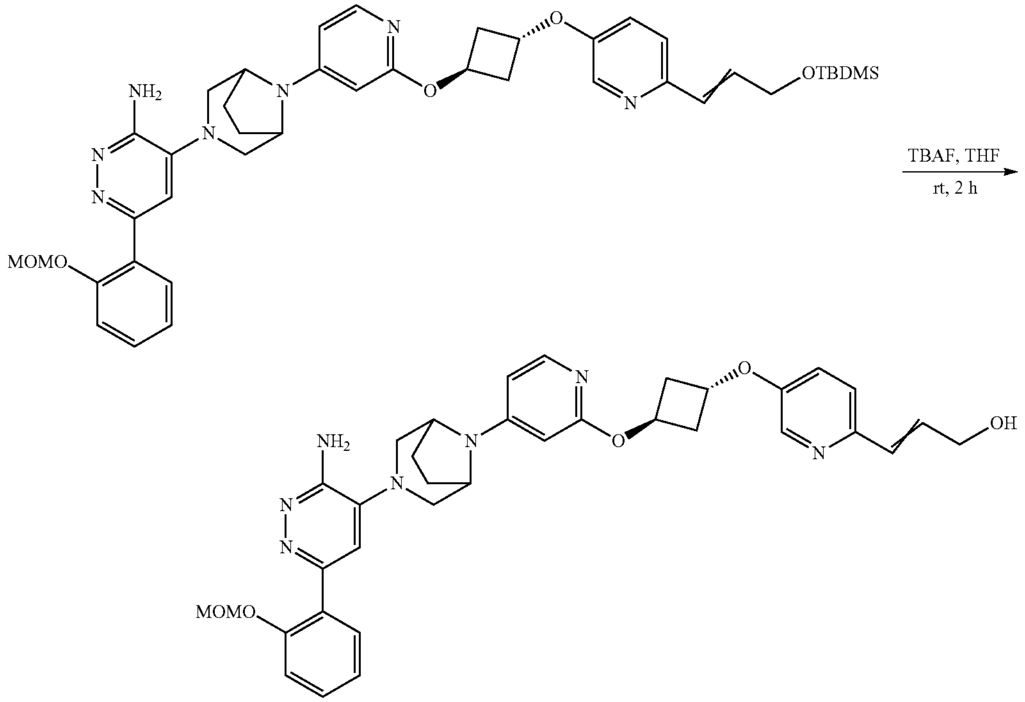

Into a 25-mL round-bottom flask, was placed a solution of 6-[2-(methoxymethoxy)phenyl]-4-(8-[2-[(1r,3r)-3-[(6-[3-[(tert-butyldimethylsilyl)oxy]prop-1-en-1-yl]pyridin-3-yl)oxy]cyclobutoxy]pyridin-4-yl]-3,8-diazabicyclo[3.2.1]octan-3-yl)pyridazin-3-amine (120 mg, 0.16 mmol, 1.00 equiv) in tetrahydrofuran (2 mL), tetrabutylammonium fluoride (1M in tetrahydrofuran) (3.2 mL, 2.00 equiv). The resulting solution was stirred for 2 hours at room temperature. The reaction was then quenched by the addition of water. The resulting solution was extracted with ethyl acetate (30 mL×3), and the organic layers were combined and dried over anhydrous sodium sulfate. The residue was applied onto a silica gel column eluting with dichloromethane/methanol (10:1). The crude product was further purified by Flash-Prep-HPLC with the following conditions (CombiFlash-1): Column, C18 silica gel; mobile phase, ACN in water, 0% ACN increasing to 40% ACN within 30 min; Detector, UV 220 nm. This resulted in 70 mg (69%) of 3-[5-[(1r,3r)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutoxy]pyridin-2-yl]prop-2-en-1-ol as a light yellow solid.

Step 11

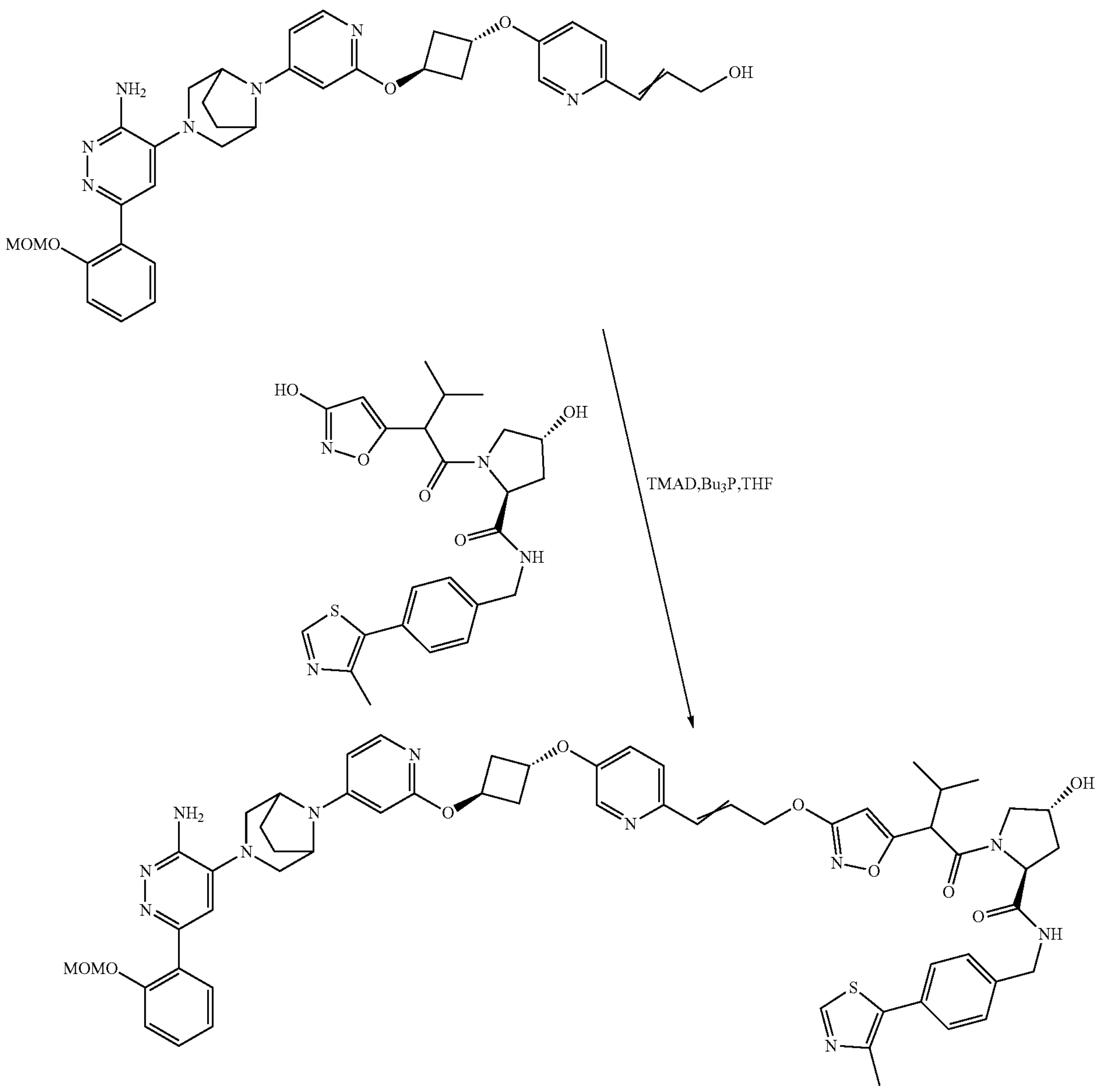

Into a 50-mL 3-necked round-bottom flask purged and maintained with an inert atmosphere of nitrogen, was placed a solution of tributylphosphine (149 mg, 0.74 mmol, 10.00 equiv) in tetrahydrofuran (20 mL). This was followed by the addition of a solution of tetramethylazodicarboxamide (126 mg, 0.73 mmol, 10.00 equiv) in tetrahydrofuran (5 mL) dropwise with stirring at −5° C. To this mixture was added (2S,4R)-4-hydroxy-1-[2-(3-hydroxy-1,2-oxazol-5-yl)-3-methylbutanoyl]-N-[[4-(4-methyl-1,3-thiazol-5-yl)phenyl]methyl]pyrrolidine-2-carboxamide (42 mg, 0.09 mmol, 1.20 equiv), and (2E)-3-[5-[(1r,3r)-3-[[4-(3-[3-amino-6-[2-(methoxymethoxy)phenyl]pyridazin-4-yl]-3,8-diazabicyclo

[3.2.1]octan-8-yl)pyridin-2-yl]oxy]cyclobutoxy]pyridin-2-yl]prop-2-en-1-ol (47 mg, 0.07 mmol, 1.00 equiv). The resulting solution was stirred overnight at 50° C. The reaction was then quenched by the addition of water. The resulting solution was extracted with ethyl acetate (30 mL×3), and the organic layers were combined. The resulting mixture was washed with brine (50 mL). The organic phase was evaporated under reduced pressure and applied onto a silica gel column eluting with dichloromethane/methanol (10:1). This resulted in 32 mg (39%) of (2S,4R)-4-hydroxy-N-[[4-(4-methyl-1,3-thiazol-5-yl)phenyl]methyl]-1-[3-methyl-2-(3-[[(2E)-3-[5-[(1r,3r)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutoxy]pyridin-2-yl]prop-2-en-1-yl]oxy]-1,2-oxazol-5-yl)butanoyl]pyrrolidine-2-carboxamide as a light yellow solid.

Step 12

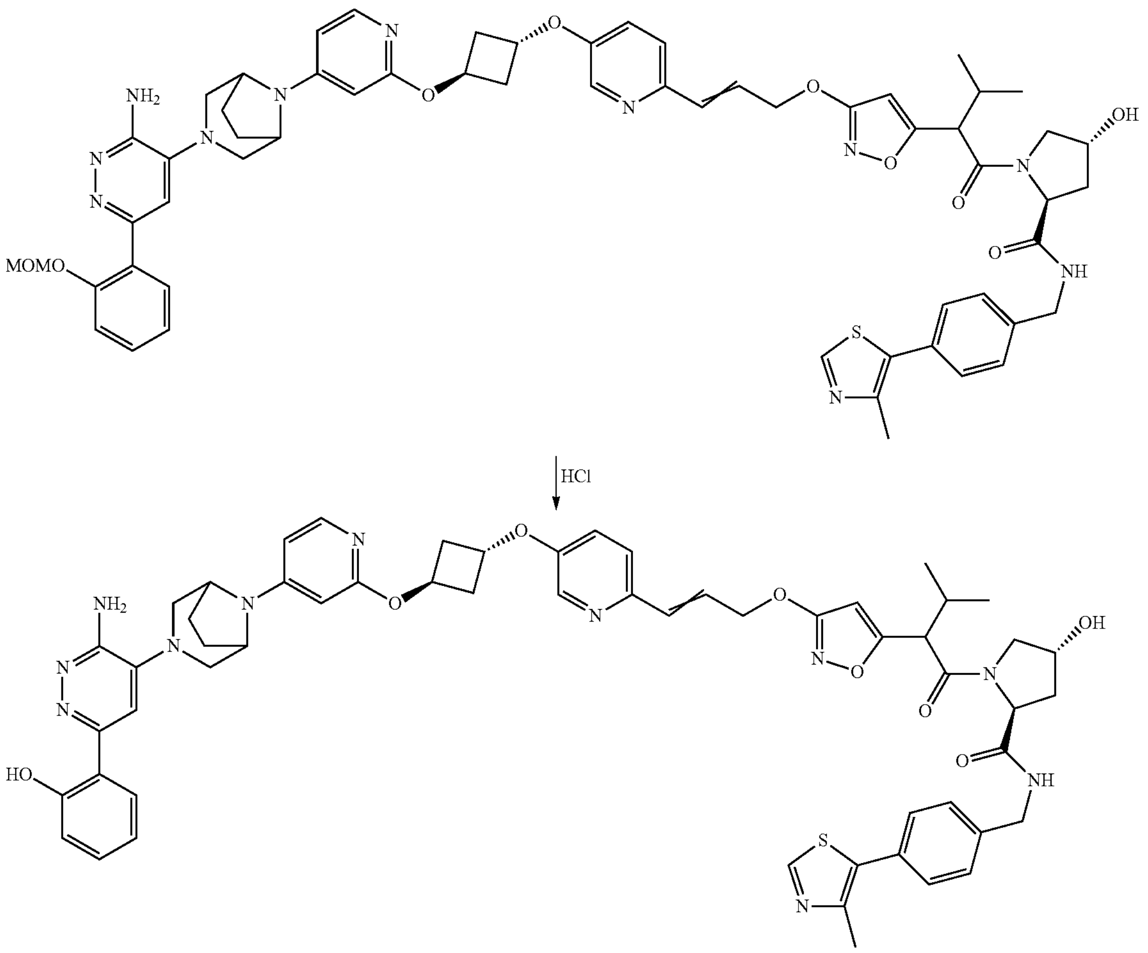

Into a 25-mL round-bottom flask purged and maintained with an inert atmosphere of nitrogen, was placed a solution of (2S,4R)-4-hydroxy-N-[[4-(4-methyl-1,3-thiazol-5-yl)phenyl]methyl]-1-(3-methyl-2-[3-[(3-[5-[(1r,3r)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutoxy]pyridin-2-yl]prop-2-en-1-yl)oxy]-1,2-oxazol-5-yl]butanoyl)pyrrolidine-2-carboxamide (23 mg, 0.02 mmol, 1.00 equiv) in methanol (3 mL) and 37% hydrochloric acid (1.5 mL). The resulting solution was stirred for 2 hours at room temperature. The reaction mixture was cooled to 0° C. with a water/ice bath. The pH value of the solution was adjusted to 7 with $NH_4HCO_3$. The resulting solution was extracted with dichloromethane (30 mL×3), and the organic layers were combined. The resulting mixture was washed with brine (50 mL×3). The mixture was dried over anhydrous sodium sulfate. The crude product was purified by Prep-HPLC with the following conditions: Column, XBridge Prep C18 OBD Column, 5 um, 19*150 mm; mobile phase, Water (10 mmoL/L $NH_4HCO_3$) and ACN (41.0% ACN up to 62.0% in 8 min); Detector, UV 254 nm. This resulted in 8.1 mg (37%) of (2S,4R)-4-hydroxy-N-[[4-(4-methyl-1,3-thiazol-5-yl)phenyl]methyl]-1-(3-methyl-2-[3-[(3-[5-[(1r,3r)-3-[(4-[3-[3-amino-6-(2-hydroxyphenyl)pyridazin-4-yl]-3,8-diazabicyclo[3.2.1]octan-8-yl]pyridin-2-yl)oxy]cyclobutoxy]pyridin-2-yl]prop-2-en-1-yl)oxy]-1,2-oxazol-5-yl]butanoyl)pyrrolidine-2-carboxamide as a light yellow solid.

Exemplary Synthesis of Exemplary Compound 57

Exemplary Compound 57 was prepared according to the scheme below using procedures described above for the production of other exemplary compounds.

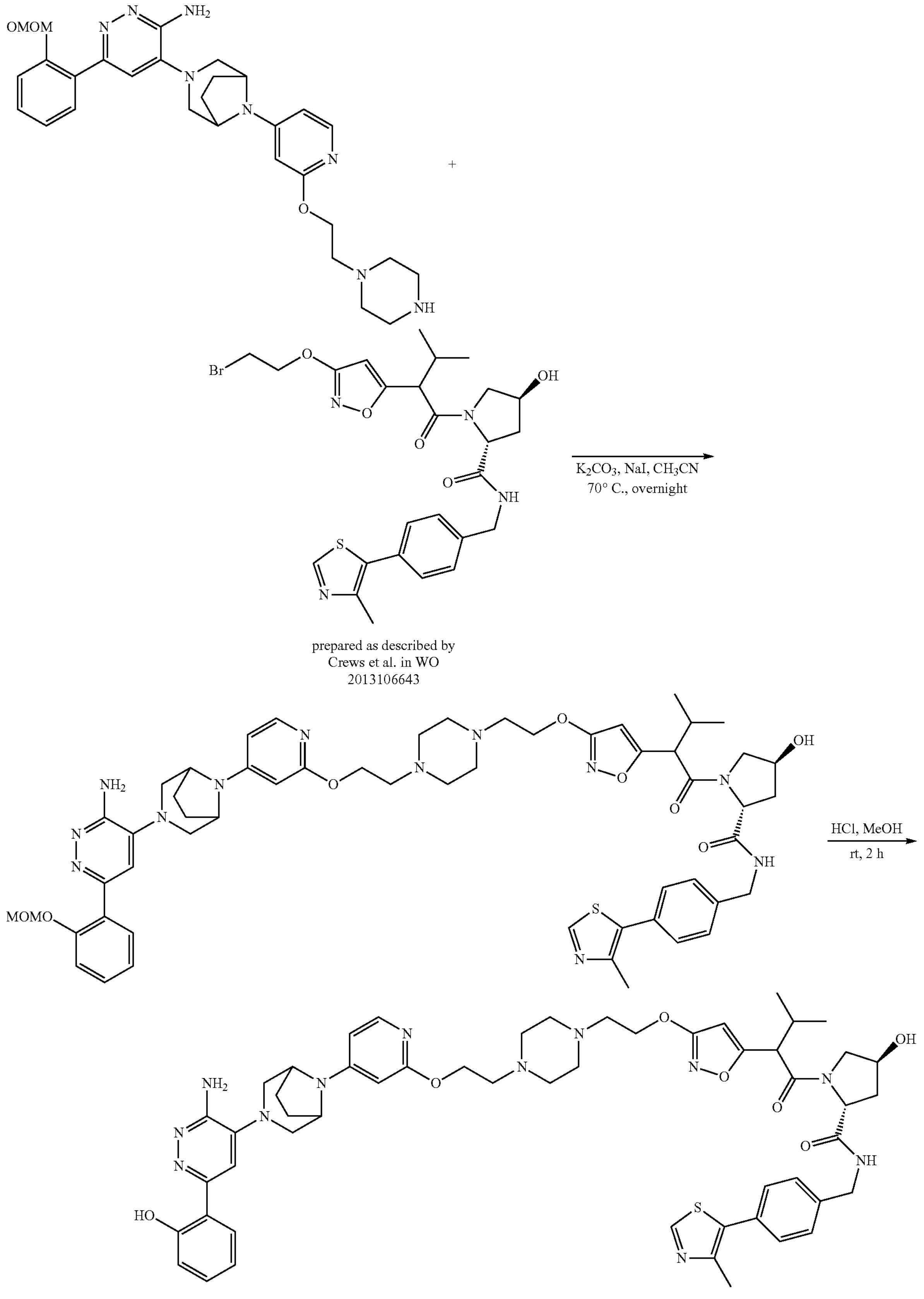
Exemplary Compound 57

Exemplary Synthesis of Exemplary Compound 47

Step 1

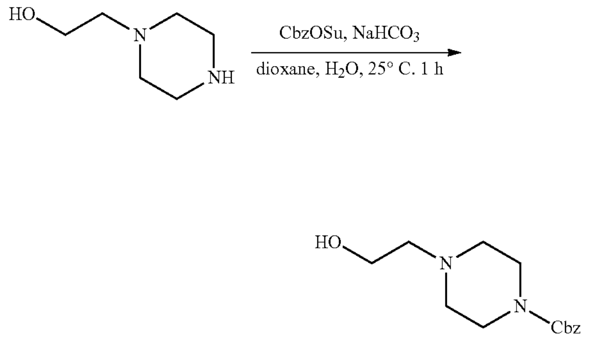

To a solution of 2-piperazin-1-ylethanol (60 g, 460 mmol, 1 eq), sodium bicarbonate (116 g, 1.38 mol, 3 eq) in dioxane (300 mL) and water (300 mL) was added benzyl (2,5-dioxopyrrolidin-1-yl) carbonate (137 g, 553 mmol, 1.2 eq) at 0° C. Then the reaction mixture was stirred at 20° C. for 2 hours. The reaction mixture was diluted with water (300 mL), and then extracted with ethyl acetate (300 mL×3). The combined organic layers were washed with brine (200 mL×3), dried over anhydrous sodium sulfate, filtered and concentrated under reduced pressure to give a residue. The residue was purified by column chromatography (ethyl acetate:methanol=500:1 to 100:1). Compound benzyl 4-(2-hydroxyethyl)piperazine-1-carboxylate (74 g, 279 mmol, 60% yield) was obtained as a light yellow oil.

Step 2

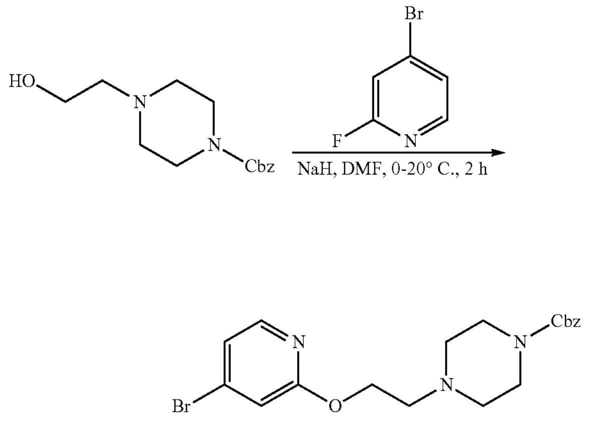

To a solution of sodium hydride (6.26 g, 156 mmol, 1.3 eq) in dimethyl formamide (240 mL) was added benzyl 4-(2-hydroxyethyl)piperazine-1-carboxylate (35 g, 132 mmol, 1.1 eq) at 0° C. for 0.5 hour. Then 4-bromo-2-fluoro-pyridine (21.18 g, 120 mmol, 1 eq) was added into the reaction and stirred at 25° C. for 1 h. The reaction mixture was quenched by the addition of saturated ammonium chloride solution (500 mL), and then extracted with ethyl acetate (300 mL×3). The combined organic layers were washed with brine (200 mL×3), dried over anhydrous sodium sulfate, filtered and concentrated under reduced pressure to give a residue. The residue was purified by column chromatography (dichloromethane:methanol=1:0 to 200:1). Compound benzyl 4-[2-[(4-bromo-2-pyridyl)oxy]ethyl]piperazine-1-carboxylate (39.2 g, 92 mmol, 76% yield) was obtained as a light yellow solid.

Step 3

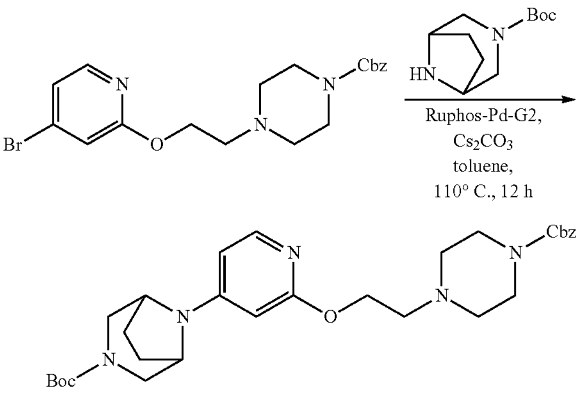 [SMILES: O=C(OCc1ccccc1)N1CCN(CCOc2cc(Br)ccn2)CC1 ; CC(C)(C)OC(=O)N1CC2CCC(C1)N2 ; CC(C)(C)OC(=O)N1CC2CCC(C1)N2c1ccnc(OCCN2CCN(C(=O)OCc3ccccc3)CC2)c1]

A vial was charged with benzyl 4-[2-[(4-bromo-2-pyridyl)oxy]ethyl]piperazine-1-carboxylate (18.15 g, 43 mmol, 1 eq), tert-butyl 3,8-diazabicyclo[3.2.1]octane-3-carboxylate (11 g, 51 mmol, 1.2 eq), [2-(2-aminophenyl)phenyl]-chloro-palladium dicyclohexyl-[2-(2,6-diisopropoxyphenyl)phenyl]phosphane (1.68 g, 2.16 mmol, 0.05 eq), cesium carbonate (28.14 g, 86.36 mmol, 2 eq) was added into toluene (350 mL). The mixture was purged with nitrogen for 5 minutes and then heated to 110° C. for 12 hours. The reaction mixture was diluted with water (200 mL) and extracted with ethyl acetate (300 mL×3). The combined organic layers were washed with brine (200 mL×3), dried over anhydrous sodium sulfate, filtered and concentrated under reduced pressure to give a residue. The residue was purified by column chromatography (petroleum ether/ethyl acetate=10:1 to 0:1). Tert-Butyl 8-[2-[2-(4-benzyloxycarbonylpiperazin-1-yl)ethoxy]-4-pyridyl]-3,8-diazabicyclo[3.2.1]octane-3-carboxylate (18.37 g, 31.30 mmol, 72% yield) was obtained as a pale yellow solid.

Step 4

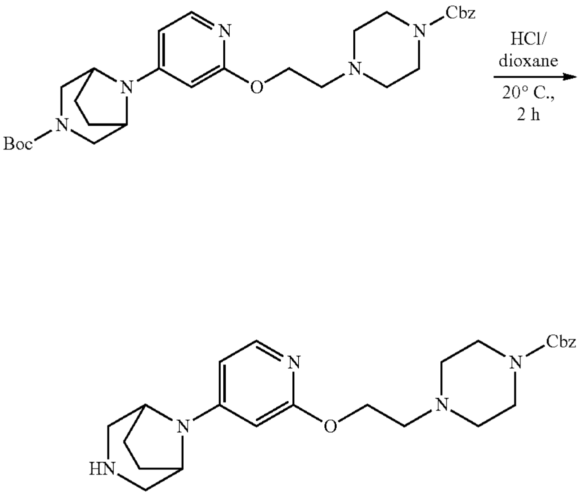

To a mixture of tert-butyl 8-[2-[2-(4-benzyloxycarbonylpiperazin-1-yl)ethoxy]-4-pyridyl]-3,8-diazabicyclo[3.2.1]octane-3-carboxylate (18.3 g, 33.17 mmol, 1 eq) in methanol (150 mL) was added hydrochloric acid/methanol (4 M, 360 mL, 43.41 eq). Then the reaction mixture was stirred at 25° C. for 2 hours. The reaction mixture was concentrated under reduced pressure to give the compound without purification. Compound benzyl 4-[2-[[4-(3,8-diazabicyclo[3.2.1]octan-8-yl)-2-pyridyl]oxy]ethyl]piperazine-1-carboxylate (19 g, crude) was obtained as a yellow solid.

Step 5

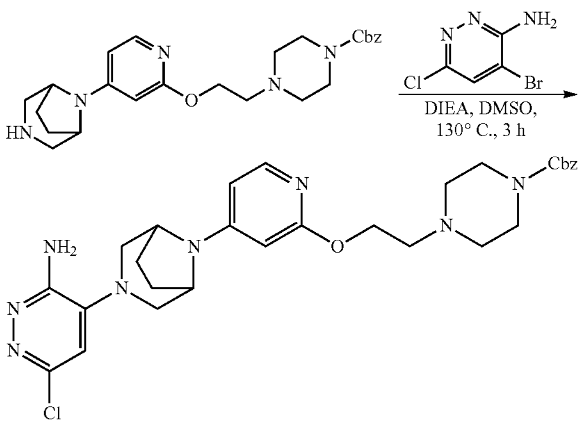

A mixture of benzyl 4-[2-[[4-(3,8-diazabicyclo[3.2.1]octan-8-yl)-2-pyridyl]oxy]ethyl]piperazine-1-carboxylate (19 g, 42.08 mmol, 1 eq), 4-bromo-6-chloro-pyridazin-3-amine (10.52 g, 50.49 mmol, 1.2 eq) in dimethylsulfoxide (190 mL) was added diisopropylethylamine (54.38 g, 420.76 mmol, 10 eq). Then the reaction mixture was stirred at 130° C. for 5 hours. The reaction mixture was quenched by addition water (600 mL), and then diluted with ethyl acetate (150 mL) and extracted with ethyl acetate (300 mL×3). The combined organic layers were washed with brine (150 mL×5), dried over anhydrous sodium sulfate, filtered and concentrated under reduced pressure to give a residue. The residue was purified by column chromatography (Petroleum ether/Ethyl acetate=1:1 to dichloromethane:methanol=50:1). Compound benzyl 4-[2-[[4-[3-(3-amino-6-chloro-pyridazin-4-yl)-3,8-diazabicyclo[3.2.1]octan-8-yl]-2-pyridyl]oxy]ethyl]piperazine-1-carboxylate (12.6 g, 21 mmol, 50% yield) was obtained as a light yellow solid.

Step 6

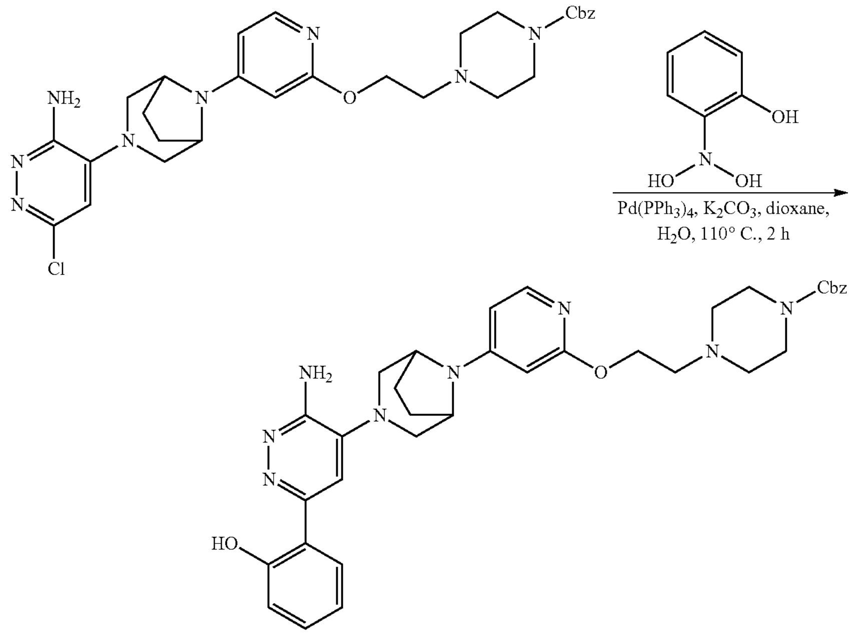

To the mixture of benzyl 4-[2-[[4-[3-(3-amino-6-chloro-pyridazin-4-yl)-3,8-diazabicyclo[3.2.1]octan-8-yl]-2-pyridyl]oxy]ethyl]piperazine-1-carboxylate (10.6 g, 18.30 mmol, 1 eq), (2-hydroxyphenyl)boronic acid (5.05 g, 36.61 mmol, 2 eq) in dioxane (160 mL) and water (25 mL) was added tetrakis[triphenylphosphine]palladium(0) (2.12 g, 1.83 mmol, 0.1 eq) and potassium carbonate (5.06 g, 36.61 mmol, 2 eq). Then the reaction mixture was stirred at 110° C. for 2 hours. The reaction mixture was diluted with water (200 mL), and then extracted with ethyl acetate (200 mL×3). The combined organic layers were washed with brine (150 mL×3), dried over anhydrous sodium sulfate, filtered and concentrated under reduced pressure to give a residue. The residue was purified by prep-HPLC (basic condition: column: Phenomenex Gemini C18 250*50 mm*10 um; mobile phase: [water (0.05% ammonia hydroxide v/v)-acetonitrile]; B %: 50%-80%, 20 MIN 60% min) to give desired compound. Compound benzyl 4-[2-[[4-[3-[3-amino-6-(2-hydroxyphenyl)pyridazin-4-yl]-3,8-diazabicyclo[3.2.1]octan-8-yl]-2-pyridyl]oxy]ethyl]piperazine-1-carboxylate (7 g, 10.22 mmol, 55% yield) was obtained as a yellow solid.

Step 7

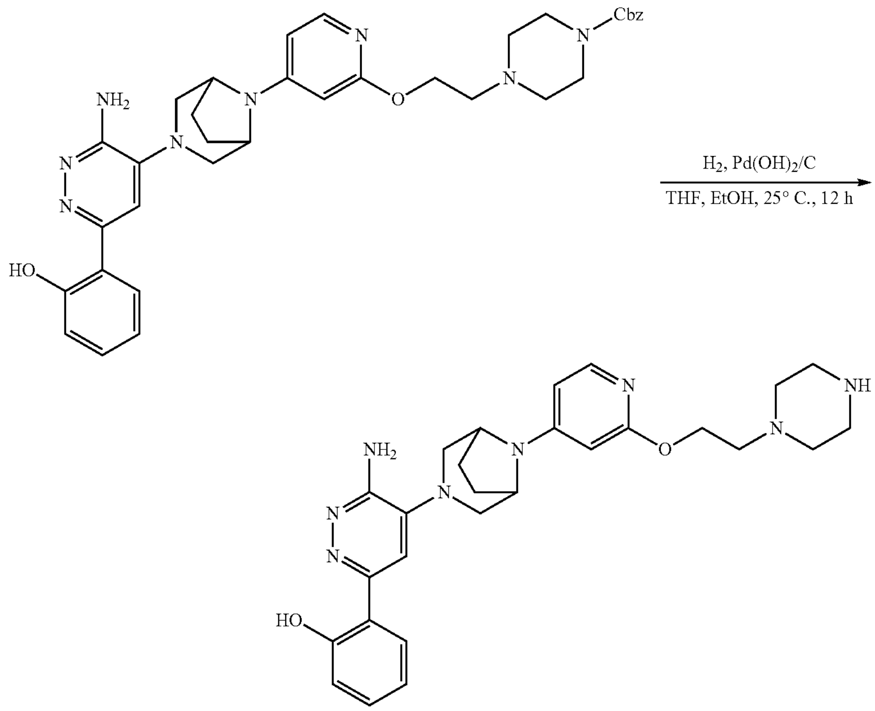

To the solution of benzyl 4-[2-[[4-[3-[3-amino-6-(2-hydroxyphenyl)pyridazin-4-yl]-3,8-diazabicyclo[3.2.1]octan-8-yl]-2-pyridyl]oxy]ethyl]piperazine-1-carboxylate (7 g, 10.99 mmol, 1 eq) in tetrahydrofuran (100 mL) was added palladium hydroxide on activated carbon catalyst (0.7 g, 0.49 mmol, 0.04 eq) under nitrogen. Then the reaction mixture was stirred at 60° C. under hydrogen (50 Psi) for 48 hours. 150 mL of ethyl alcohol was then added to the reaction mixture. The reaction mixture was filtered and concentrated under reduced pressure to give 2-[6-amino-5-[8-[2-(2-piperazin-1-ylethoxy)-4-pyridyl]-3,8-diazabicyclo[3.2.1]octan-3-yl]pyridazin-3-yl]phenol (5 g, 9.68 mmol, 88% yield).

Step 8

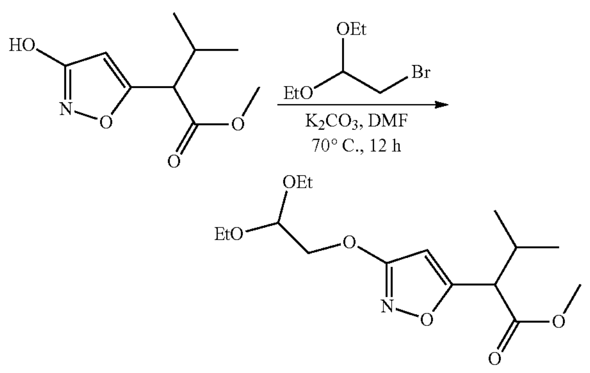

To a solution of methyl 2-(3-hydroxyisoxazol-5-yl)-3-methyl-butanoate (3.5 g, 17.57 mmol, 1 eq) in N,N-dimethylformamide (40 mL) was added 2-bromo-1,1-diethoxyethane (5.19 g, 26.35 mmol, 1.5 eq) and potassium carbonate (4.86 g, 35.14 mmol, 2 eq). The reaction mixture was stirred at 70° C. for 12 hours. The reaction mixture was quenched by the addition water 50 mL, and then diluted with water 100 mL and extracted with ethyl acetate (80 mL×3). The combined organic layers were washed with brine (100 mL×2), dried over anhydrous sodium sulfate, filtered and concentrated under reduced pressure to give a residue. The residue was purified by silica gel chromatography (petroleum ether: ethyl acetate=100:1 to 50:1). The desired compound methyl 2-[3-(2,2-diethoxyethoxy)isoxazol-5-yl]-3-methyl-butanoate (4.38 g, 12.50 mmol, 71% yield) was obtained as a colorless oil.

Step 9

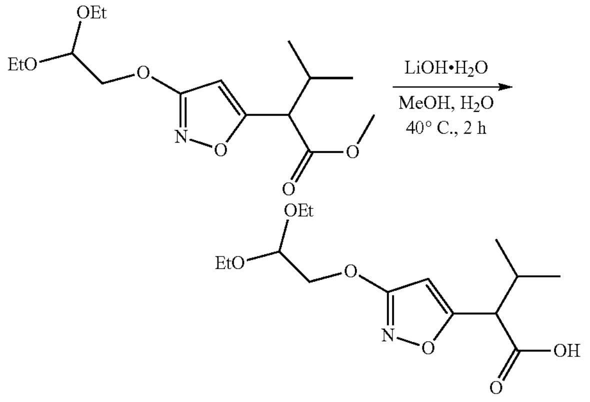

To a solution of methyl 2-[3-(2,2-diethoxyethoxy)isoxazol-5-yl]-3-methyl-butanoate (4.38 g, 12.5 mmol, 1 eq) in methanol (30 mL) and water (15 mL) was added lithium hydroxide monohydrate (2.10 g, 50 mmol, 4 eq). The reaction mixture was stirred at 40° C. for 2 hours. The pH was adjusted to 4-5 with IM hydrogen chloride, and reaction mixture was extracted with ethyl acetate (50 mL×2). The combined organic layers were dried over anhydrous sodium sulfate, filtered and concentrated under reduced pressure to give 2-[3-(2,2-diethoxyethoxy)isoxazol-5-yl]-3-methyl-butanoic acid (4 g, crude) as a colorless oil.

Step 10

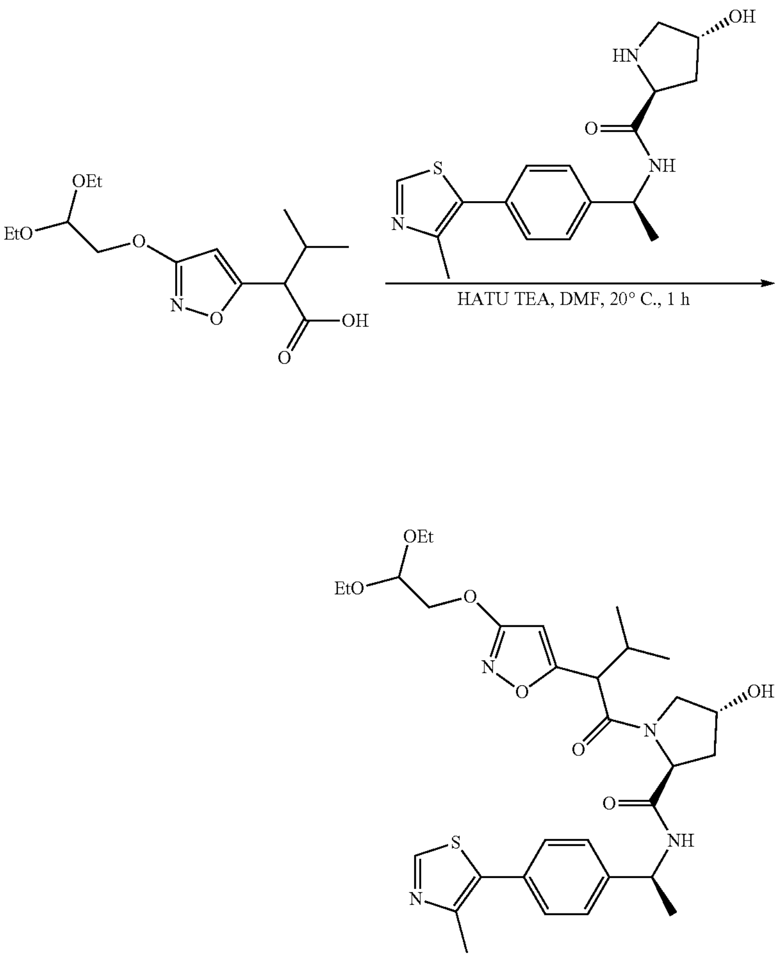

To a solution of 2-[3-(2,2-diethoxyethoxy)isoxazol-5-yl]-3-methyl-butanoic acid (3.84 g, 11.99 mmol, 1 eq) in N,N-dimethylformamide (20 mL) was added O-(7-azabenzotriazol-1-yl)-N,N,N',N'-tetramethyluronium hexafluorophosphate (5.47 g, 14.38 mmol, 1.2 eq). The reaction mixture was stirred at 20° C. for 0.5 hour. Then to the mixture was added a solution of (2S,4R)-4-hydroxy-N-[(1S)-1-[4-(4-methylthiazol-5-yl)phenyl]ethyl]pyrrolidine-2-carboxamide hydrochloride (4.41 g, 11.99 mmol, 1 eq) and triethylamine (3.64 g, 35.96 mmol, 5 mL, 3 eq) in N,N-dimethylformamide (10 mL). The reaction mixture was stirred at 20° C. for 0.15 hour. The reaction mixture was quenched by addition water (30 mL), and then diluted with water (80 mL) and extracted with ethyl acetate (60 mL×3). The combined organic layers were washed with brine (80 mL×2), dried over anhydrous sodium sulfate, filtered and concentrated under reduced pressure to give a residue. The residue was purified by silica gel chromatography (dichloromethane:methanol=100:1 to 50:1). The desired compound (2S,4R)-1-[2-[3-(2,2-diethoxyethoxy)isoxazol-5-yl]-3-methyl-butanoyl]-4-hydroxy-N-[(1S)-1-[4-(4-methylthiazol-5-yl)phenyl]ethyl]pyrrolidine-2-carboxamide (7 g, 10.96 mmol, 91% yield) was obtained as a white solid.

Step 11

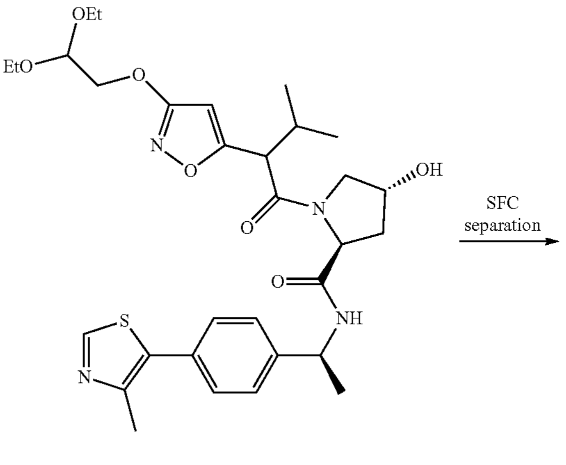

-continued

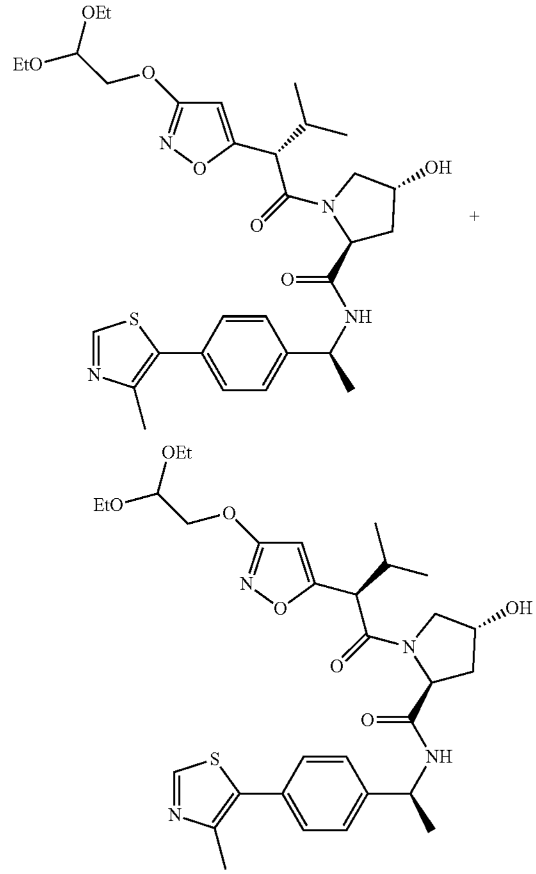

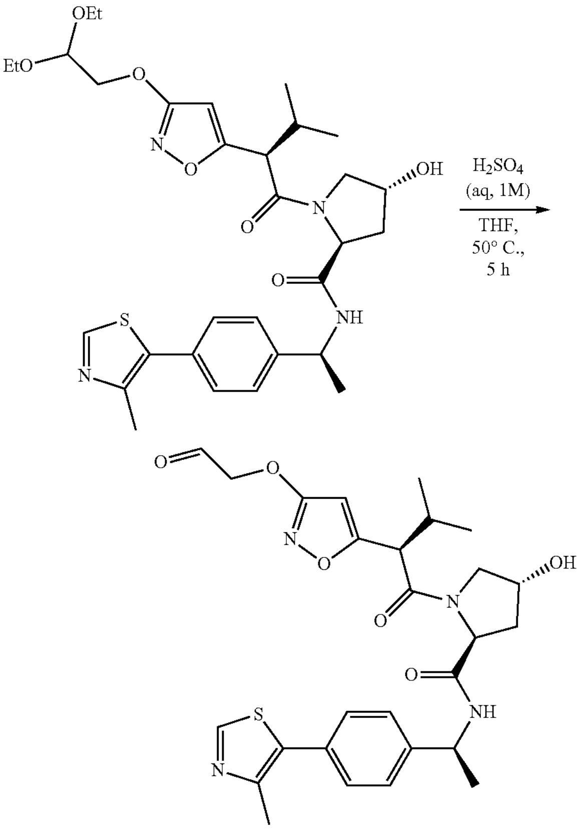

(2S,4R)-1-[2-[3-(2,2-diethoxyethoxy)isoxazol-5-yl]-3-methyl-butanoyl]-4-hydroxy-N-[(1S)-1-[4-(4-methylthiazol-5-yl)phenyl]ethyl]pyrrolidine-2-carboxamide (7 g, 11.39 mmol, 1 eq) was separated by SFC. The condition was column: DAICEL CHIRALPAK AD (250 mm*30 mm, 10 um); mobile phase: [0.1% NH3H2O IPA]; B %: 35%-35%, 2.4 min: 550 min. (2S,4R)-1-[(2S)-2-[3-(2,2-diethoxyethoxy)isoxazol-5-yl]-3-methyl-butanoyl]-4-hydroxy-N-[(1S)-1-[4-(4-methylthiazol-5-yl)phenyl]ethyl]pyrrolidine-2-carboxamide (3.2 g, 5.08 mmol, 89% yield) and (2S,4R)-1-[(2R)-2-[3-(2,2-diethoxyethoxy)isoxazol-5-yl]-3-methyl-butanoyl]-4-hydroxy-N-[(1S)-1-[4-(4-methylthiazol-5-yl)phenyl]ethyl]pyrrolidine-2-carboxamide (2.67 g, 4.17 mmol, 73% yield) were obtained as white solids.

Step 12

To a solution of (2S,4R)-1-[(2R)-2-[3-(2,2-diethoxyethoxy)isoxazol-5-yl]-3-methyl-butanoyl]-4-hydroxy-N-[(1S)-1-[4-(4-methylthiazol-5-yl)phenyl]ethyl]pyrrolidine-2-carboxamide (2 g, 3.25 mmol, 1 eq) in tetrahydrofuran (40 mL) was added sulfuric acid (1 M, 40 mL, 12.3 eq). The solution was heated to 50° C. for 7 h. The solution was cooled to 20° C. and quenched with saturated sodium bicarbonate solution to pH=8. The mixture was extracted with ethyl acetate (30 mL×3). The combined organic layer was washed with brine (50 mL) and dried over sodium sulfate. The mixture was then filtered, and the filtrate was concentrated in vacuum. The crude product was used directly in next step. (2S,4R)-4-hydroxy-1-[(2R)-3-methyl-2-[3-(2-oxoethoxy)isoxazol-5-yl]butanoyl]-N-[(1S)-1-[4-(4-methylthiazol-5-yl)phenyl]ethyl]pyrrolidine-2-carboxamide (1.7 g, 2.52 mmol, 77% yield) was obtained as a white solid.

Step 13

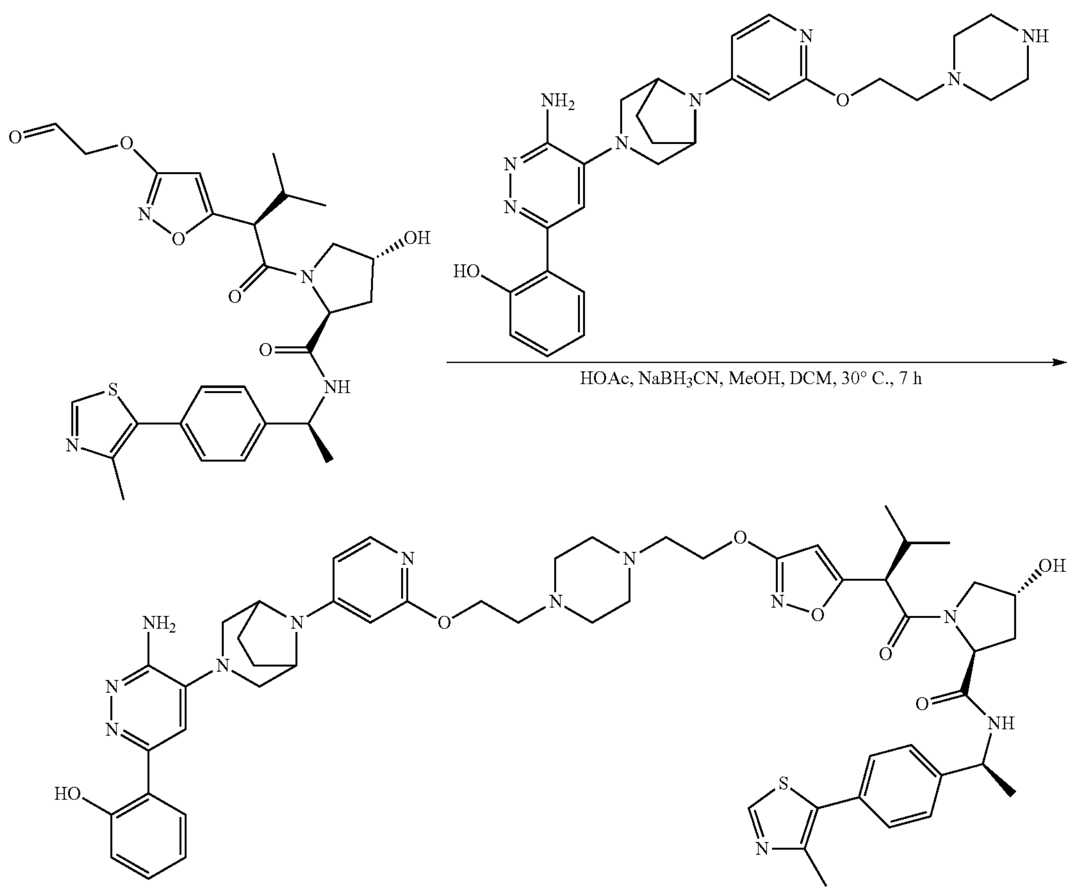

Ex. 47

To a solution of (2S,4R)-4-hydroxy-1-[(2R)-3-methyl-2-[3-(2-oxoethoxy)isoxazol-5-yl]butanoyl]-N-[(1S)-1-[4-(4-methylthiazol-5-yl)phenyl]ethyl]pyrrolidine-2-carboxamide (930 mg, 1.38 mmol, 1 eq) and 2-[6-amino-5-[8-[2-(2-piperazin-1-ylethoxy)-4-pyridyl]-3,8-diazabicyclo[3.2.1]octan-3-yl]pyridazin-3-yl]phenol (691 mg, 1.38 mmol, 1 eq) in methanol (15 mL) and dichloromethane (5 mL) was added acetic acid (82 mg, 1.38 mmol, 1 eq). The solution was stirred at 30° C. for 0.5 hour. Then sodium cyanoborohydride (129 mg, 2.06 mmol, 1.5 eq) was added to the solution and stirred at 30° C. for 7 hours. The solvent was removed in vacuum, and the crude product was purified by prep-HPLC (column: Phenomenex Synergi Max-RP 250*50 mm*10 um; mobile phase: [water (10 mM $NH_4HCO_3$)-ACN]; B %: 45ACN %-75ACN %, 28 min, 78% min). (2S,4R)-1-[(2R)-2-[3-[2-[4-[2-[[4-[3-[3-amino-6-(2-hydroxyphenyl)pyridazin-4-yl]-3,8-diazabicyclo[3.2.1]octan-8-yl]-2-pyridyl]oxy]ethyl]piperazin-1-yl]ethoxy]isoxazol-5-yl]-3-methyl-butanoyl]-4-hydroxy-N-[(1S)-1-[4-(4-methylthiazol-5-yl)phenyl]ethyl]pyrrolidine-2-carboxamide (840 mg, 0.8 mmol, 58% yield, 98% purity) was obtained as a white solid.

Exemplary Synthesis of Exemplary Compounds 59 and 60
Ex. 59
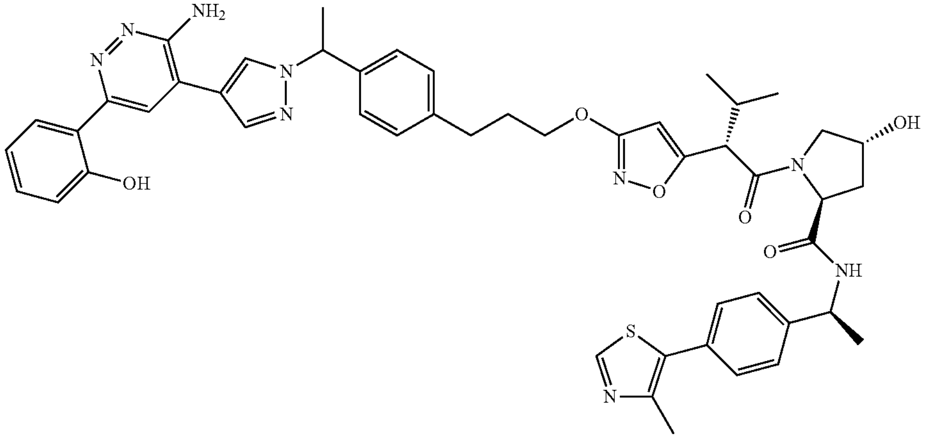
Ex. 60
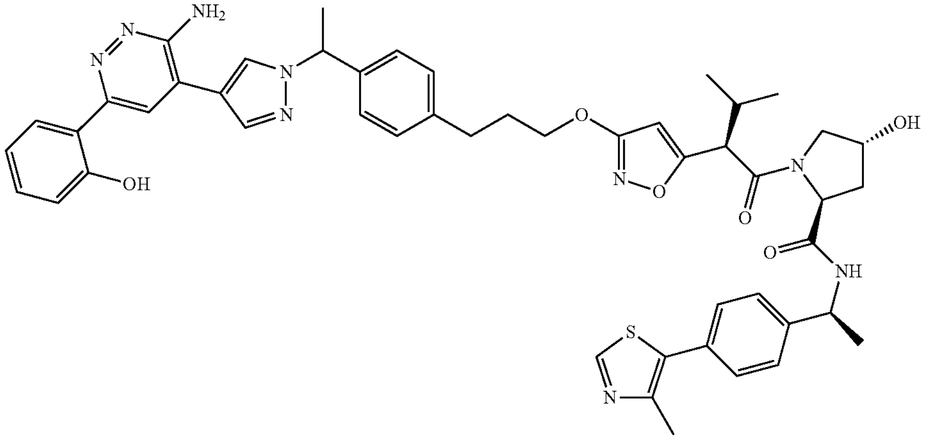
Prepared as described in the scheme below using procedures described above for other examples.
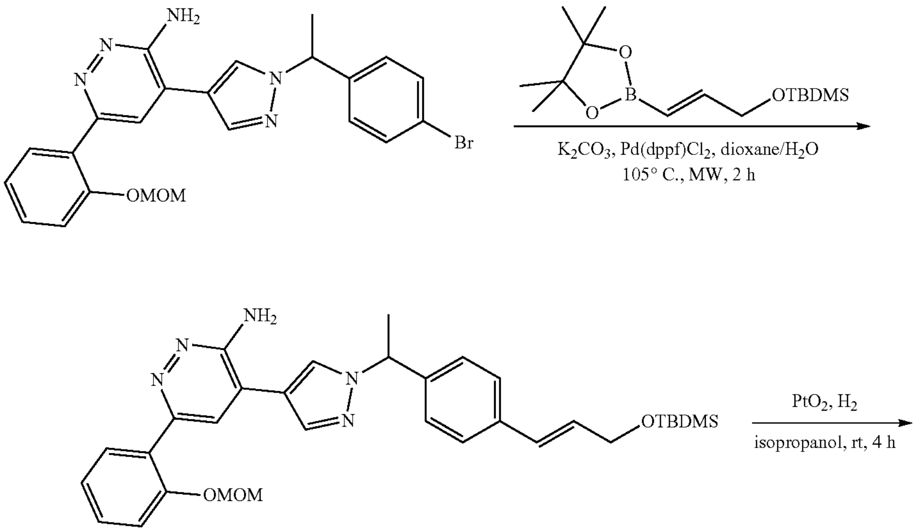

-continued
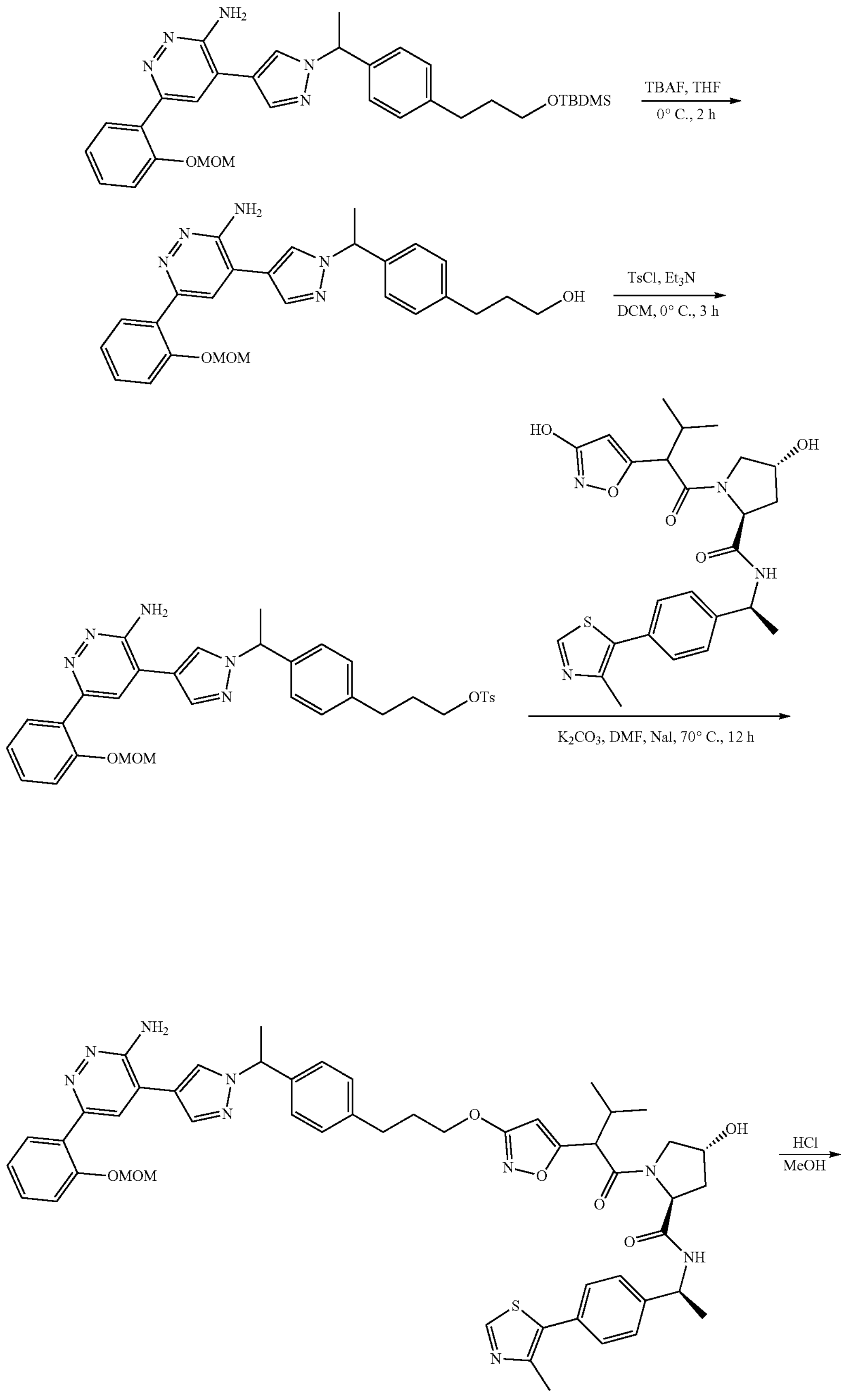

-continued
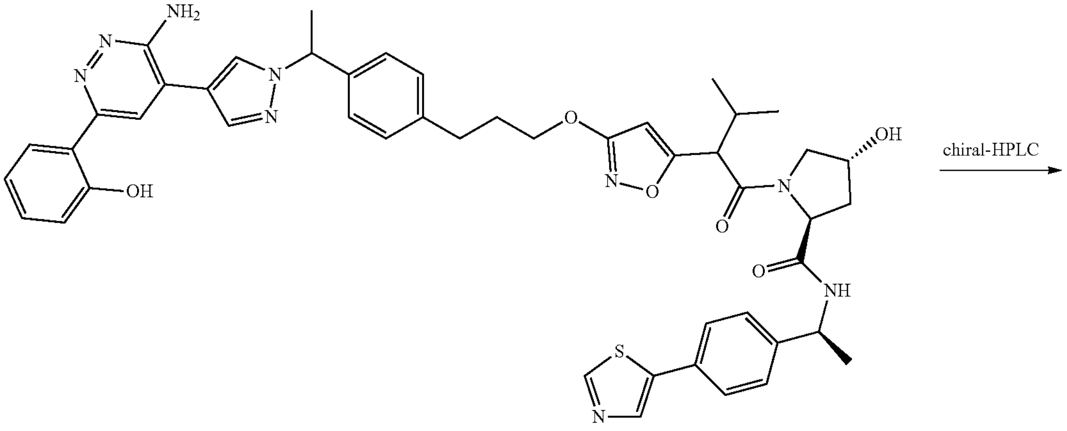
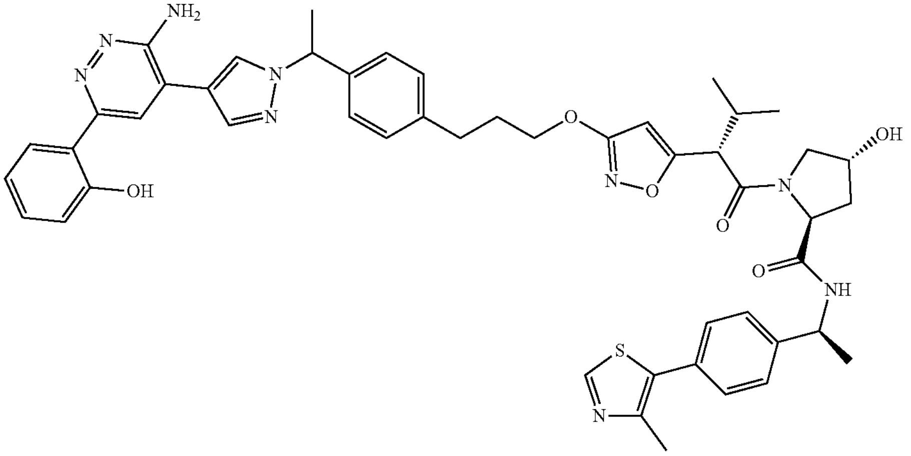
+
Ex. 59
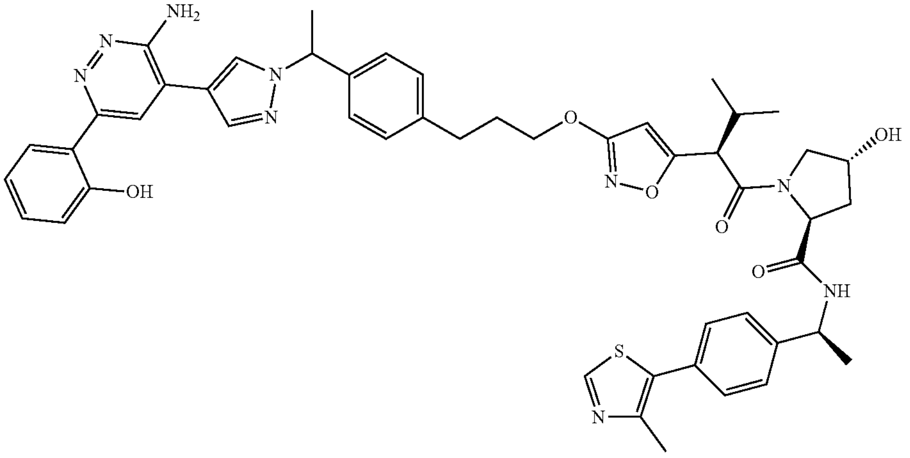
Ex. 60

Exemplary Synthesis of Exemplary Compound 61

Ex. 61

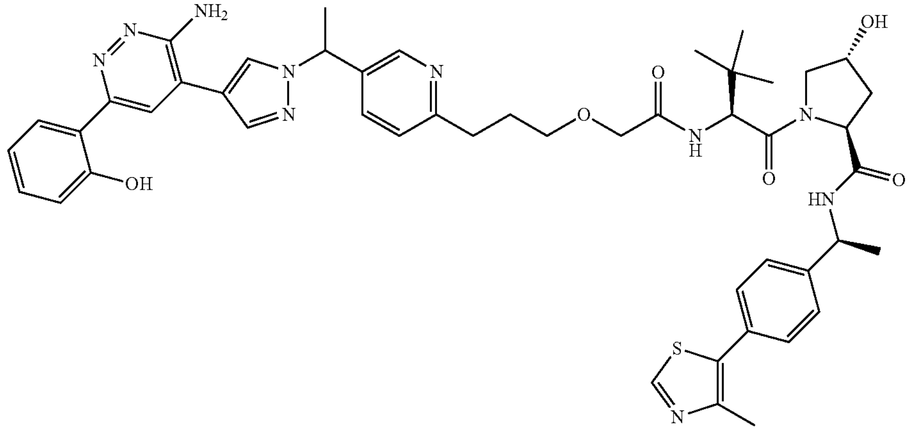

Step 1

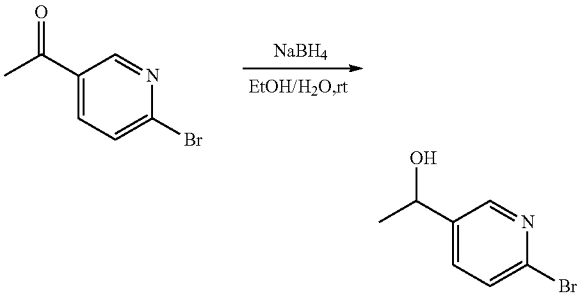

Into a 500 mL round-bottom flask, to a solution of 1-(6-bromopyridin-3-yl)ethan-1-one (10 g, 49.99 mmol, 1 equiv) in EtOH (200 ml) was added sodium borohydride (4 g, 105.73 mmol, 2.11 equiv) in water (80 ml) at room temperature. The resulting mixture was stirred for 30 minutes at room temperature. The mixture was concentrated under vacuum. The residue was purified by silica gel column chromatography, eluted with ethyl acetate/petroleum ether (1:1) to afford 1-(6-bromopyridin-3-yl)ethan-1-ol (9.2 g, 91%) as a yellow oil.

Step 2

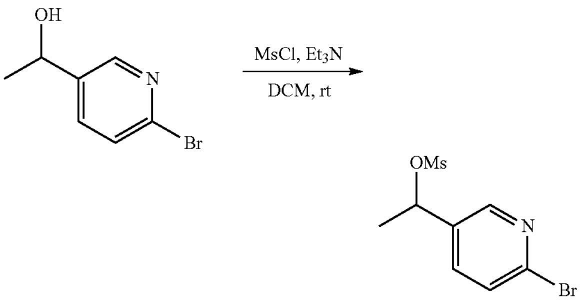

Into a 100 mL round-bottom flask to a solution of 1-(6-bromopyridin-3-yl)ethan-1-ol (2 g, 9.90 mmol, 1 equiv) and triethylamine (3 g, 0.03 mmol) in dichloromethane (30 mL) was added methanesulfonyl chloride (1.3 g, 11.35 mmol, 1.15 equiv) at 0° C. The resulting mixture was stirred for 16 hours at room temperature. The resulting mixture was extracted with dichloromethane (30 mL×3). The combined organic layers were washed with brine (20 mL×1), dried over anhydrous sodium sulfate. After filtration, the filtrate was concentrated under reduced pressure. This resulted in 1-(6-bromopyridin-3-yl)ethyl methanesulfonate (1.6 g, 23%) as a yellow solid.

Step 3

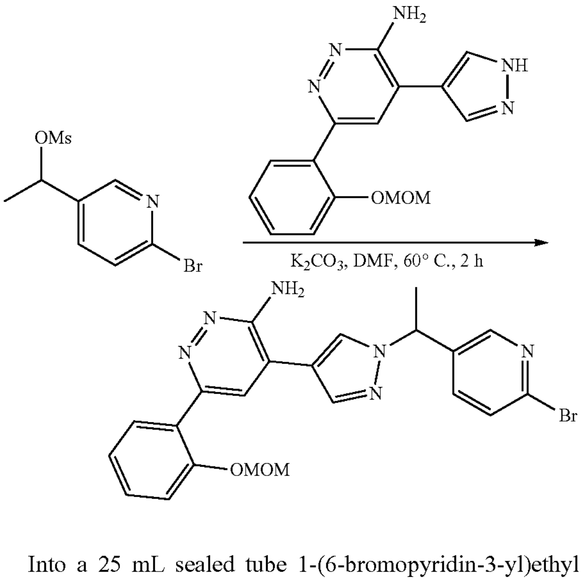

Into a 25 mL sealed tube 1-(6-bromopyridin-3-yl)ethyl methanesulfonate (1.4 g, 1.2 equiv), 6-[2-(methoxymethoxy)phenyl]-4-(1H-pyrazol-4-yl)pyridazin-3-amine (350 mg, 1 equiv), and potassium carbonate (490 mg, 3.0 equiv) were added to N,N-Dimethylformamide (15 mL) at room temperature. The resulting mixture was stirred for 2 h at 60° C. under nitrogen atmosphere. The aqueous layer was extracted with dichloromethane (50 mL×3). The residue was washed with brine (20 mL×1), dried over anhydrous sodium sulfate. After filtration, the filtrate was concentrated under reduced pressure. The residue was purified by silica gel column chromatography, eluted with dichloromethane/methyl alcohol (10:1) to afford 4-[1-[1-(6-bromopyridin-3-yl)ethyl]-1H-pyrazol-4-yl]-6-[2-(methoxymethoxy)phenyl]pyridazin-3-amine (90 mg, 16%) as a yellow solid.

4-[1-[1-(6-bromopyridin-3-yl)ethyl]-1H-pyrazol-4-yl]-6-[2-(methoxymethoxy)phenyl]pyridazin-3-amine was converted to the final compound according to the scheme below using procedures described for other examples above.

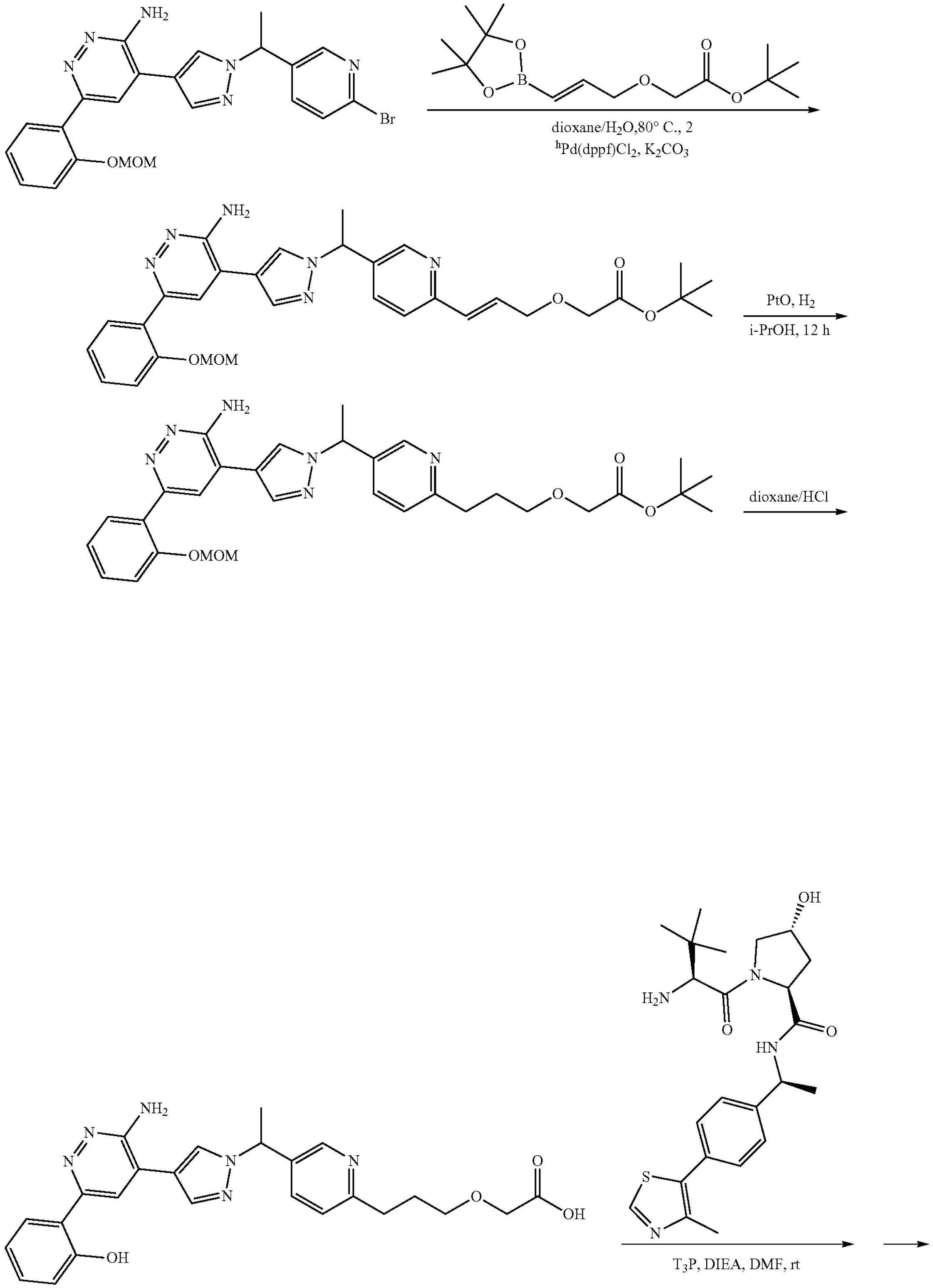

-continued

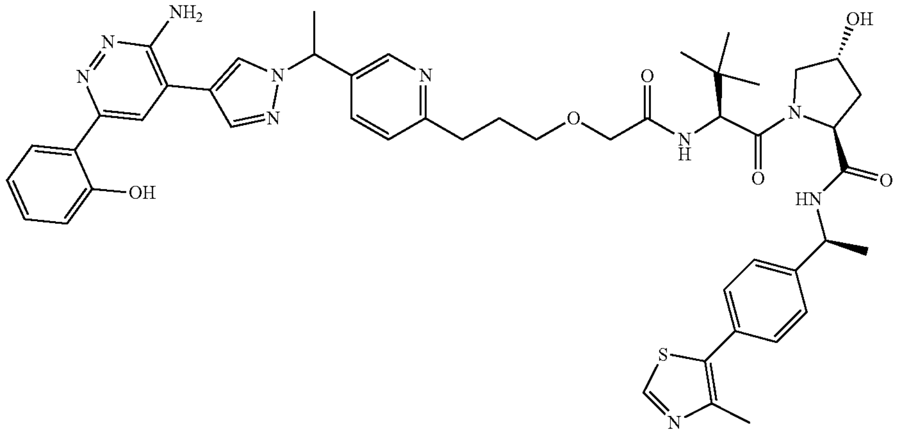

Ex. 61

Exemplary Synthesis of Exemplary Compound 62

Step 1

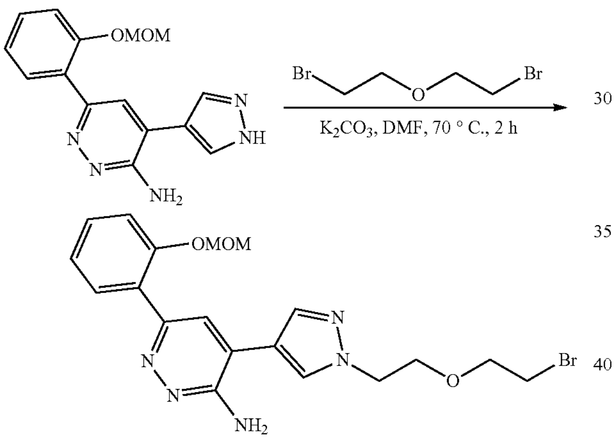

A mixture of 6-[2-(methoxymethoxy)phenyl]-4-(1H-pyrazol-4-yl)pyridazin-3-amine (300 mg, 1.01 mmol, 1 eq), 1-bromo-2-(2-bromoethoxy)ethane (702 mg, 3.03 mmol, 3 eq) in dimethyl formamide (3 mL) was added potassium carbonate (418 mg, 3.03 mmol, 3 eq). Then the reaction mixture was stirred at 70° C. for 2 hours. Water was added (10 mL), and reaction mixture was extracted with ethyl acetate (20 mL×3). The combined organic layers were washed with brine (15 mL×2), dried over anhydrous sodium sulfate, filtered and concentrated under reduced pressure to give a residue. The residue was purified by prep-TLC (dichloromethane:methanol=10:1). 4-[1-[2-(2-Bromoethoxy)ethyl]pyrazol-4-yl]-6-[2-(methoxymethoxy)phenyl]pyridazin-3-amine (100 mg, 0.22 mmol, 22% yield) was obtained as a yellow oil.

Step 2

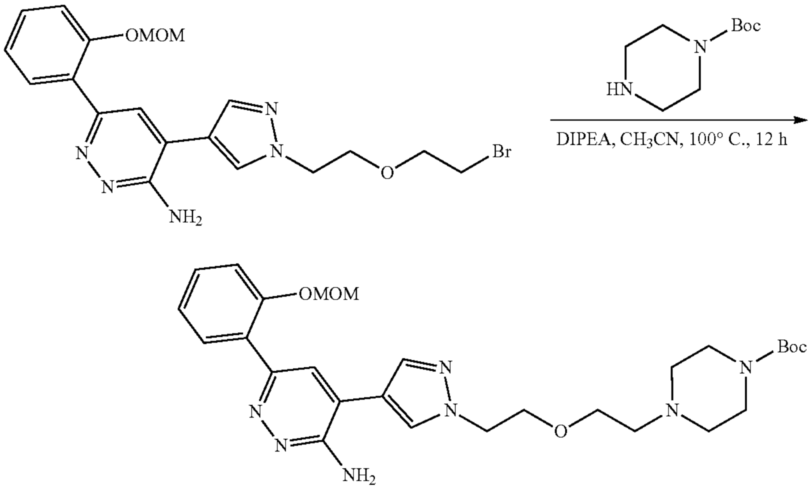

To a solution of 4-[1-[2-(2-bromoethoxy)ethyl]pyrazol-4-yl]-6-[2-(methoxymethoxy)phenyl]pyridazin-3-amine (100 mg, 0.22 mmol, 1 eq) and tert-butyl piperazine-1-carboxylate (83 mg, 0.44 mmol, 2 eq) in acetonitrile (2 mL) was added N,N-diisopropylethylamine (86.49 mg, 0.66 mmol, 3 eq). Then the reaction mixture was stirred at 100° C. for 12 hours. Water was added (5 mL), and reaction mixture was extracted with ethyl acetate (15 mL×3). The combined organic layers were washed with brine (10 mL×3), dried over anhydrous sodium sulfate, filtered and concentrated under reduced pressure to give a residue. The residue was purified by prep-TLC (dichloromethane:methanol=10:1). Compound tert-butyl 4-[2-[2-[4-[3-amino-6-[2-(methoxymethoxy)phenyl]pyridazin-4-yl]pyrazol-1-yl]ethoxy]ethyl]piperazine-1-carboxylate (93 mg, 0.15 mmol, 71% yield) was obtained as a yellow solid.

tert-Butyl 4-[2-[2-[4-[3-amino-6-[2-(methoxymethoxy)phenyl]pyridazin-4-yl]pyrazol-1-yl]ethoxy]ethyl]piperazine-1-carboxylate was converted to the final compound according to the scheme below using procedures described for other examples above.

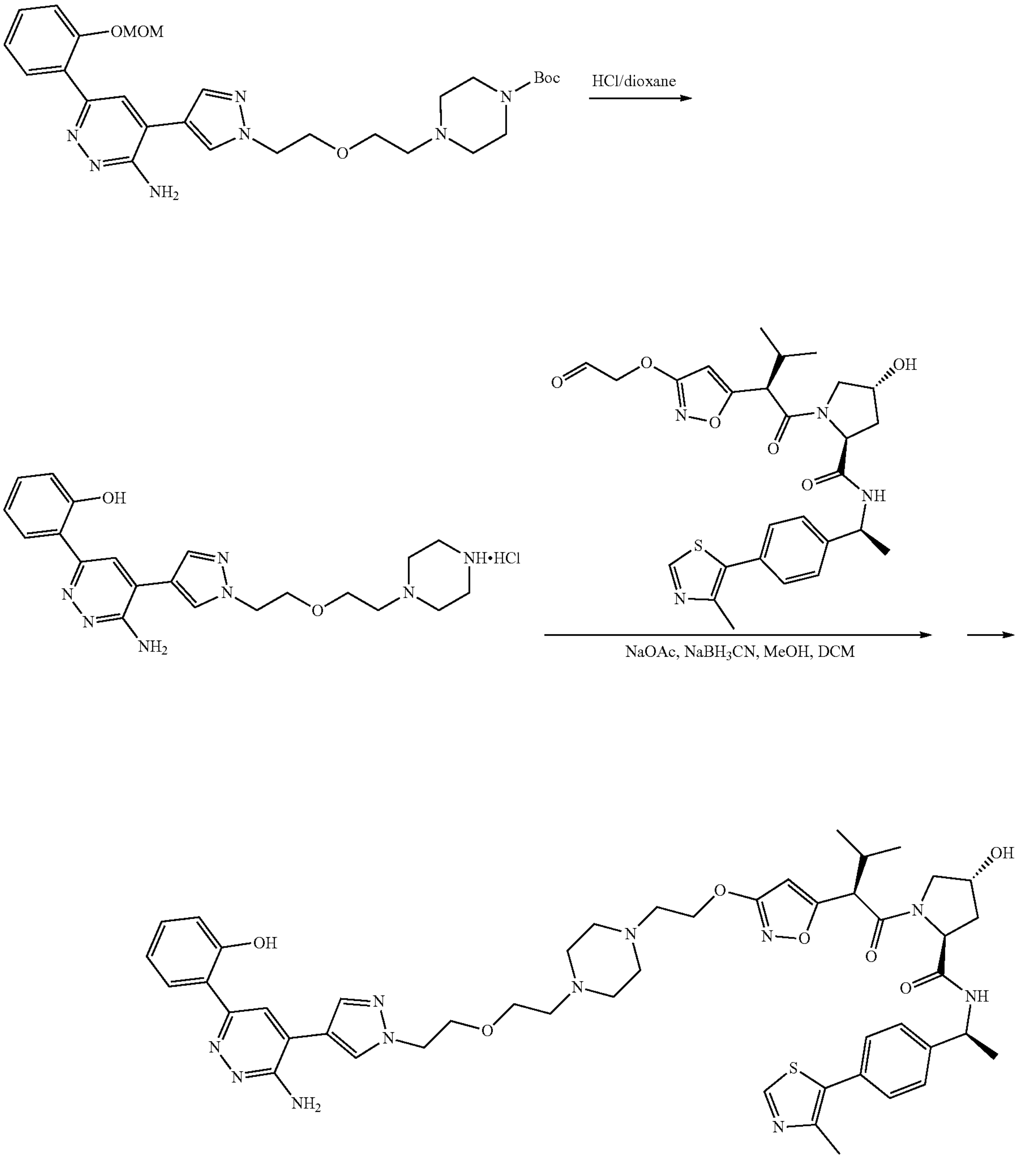

Ex. 62

Exemplary compounds 165 and 124 were prepared using analogous procedures.

Exemplary Synthesis of Exemplary Compound 64

Ex. 64

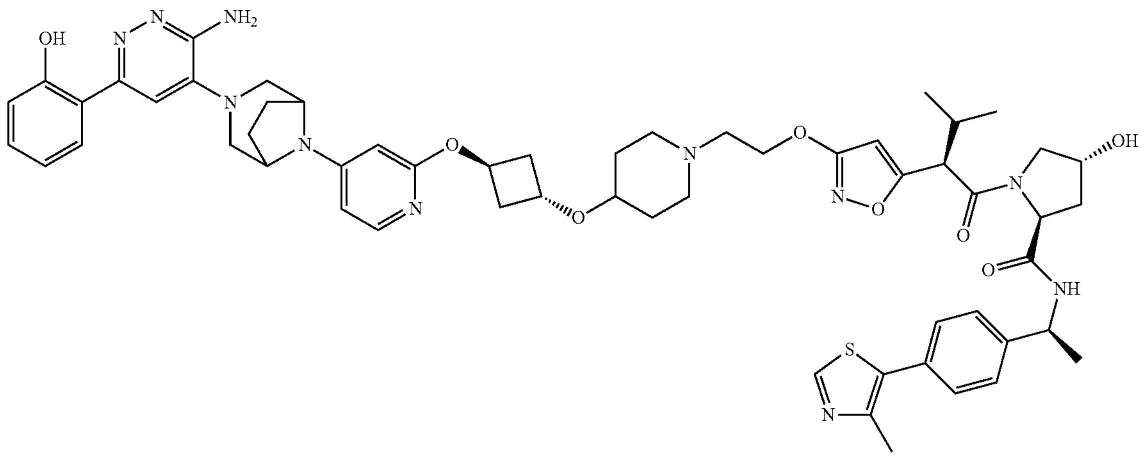

Step 1

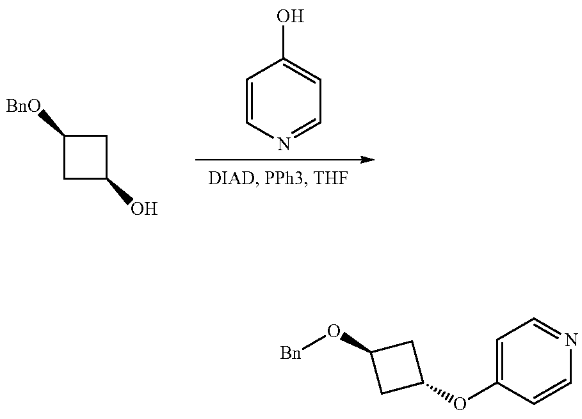

To a solution of pyridin-4-ol (3.20 g, 33.66 mmol, 1.5 eq) and 3-benzyloxycyclobutanol (4 g, 22.44 mmol, 1 eq) in tetrahydrofuran (200 mL) was added triphenylphosphine (7.06 g, 26.93 mmol, 1.2 eq) and diisopropyl azodicarboxylate (5.45 g, 26.93 mmol, 1.2 eq) in one portion at 10° C. under nitrogen. The mixture was stirred at 50° C. for 12 hours. The reaction mixture was concentrated under reduced pressure to remove tetrahydrofuran. Water (50 mL) was poured into the mixture and stirred for 1 minute. The aqueous phase was extracted with dichloromethane (50 mL×3). The combined organic phase was washed with brine (50 mL×2), dried with anhydrous sodium sulfate, filtered and concentrated in vacuum. The residue was purified by silica gel column chromatography (petroleum ether:tetrahydrofuran=20:1, 5:1). The residue was purified by flash C18 column chromatography [acetonitrile: water (0.5% ammonium hydroxide)=5%-50%]. Compound 4-(3-benzyloxycyclobutoxy) pyridine (3.2 g, 12.53 mmol, 55% yield) was obtained as a white solid.

Step 2

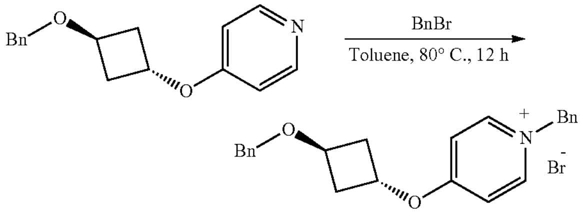

To a solution of 4-(3-benzyloxycyclobutoxy)pyridine (4.2 g, 16.45 mmol, 1 eq) in toluene (65 mL) was added benzyl bromide (2.81 g, 16.45 mmol, 1 eq). The mixture was stirred at 80° C. for 12 hours. The reaction mixture was concentrated under reduced pressure to remove toluene. The crude product was triturated with petroleum ether (80 mL). Compound 1-benzyl-4-(3-benzyloxycyclobutoxy)pyridine-1-ium bromide (6.5 g, 15.25 mmol, 92% yield) was obtained as a white solid.

Step 3

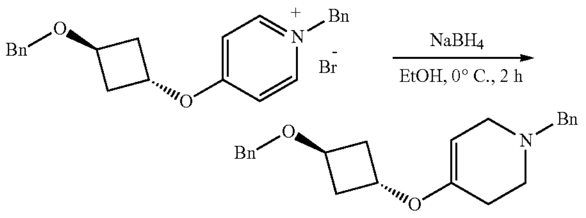

To a solution of 1-benzyl-4-(3-benzyloxycyclobutoxy) pyridine-1-ium bromide (6.5 g, 15.25 mmol, 1 eq) in ethanol (120 mL) was added sodium borohydride (3.46 g, 91.47 mmol, 6 eq) at 0° C. The mixture was stirred at 15° C. for 4 hours. The reaction mixture was concentrated under reduced pressure to remove ethanol. The residue was diluted with water (25 mL) and extracted with ethyl acetate (50 mL×2). The combined organic phase was washed with saturated brine (40 mL×3), dried with anhydrous sodium sulfate, filtered and concentrated in vacuum. Compound 1-benzyl-4-(3-benzyloxycyclobutoxy)-3,6-dihydro-2H-pyridine (4.5 g, 12.88 mmol, 84% yield) was obtained as a colorless oil.

Step 4

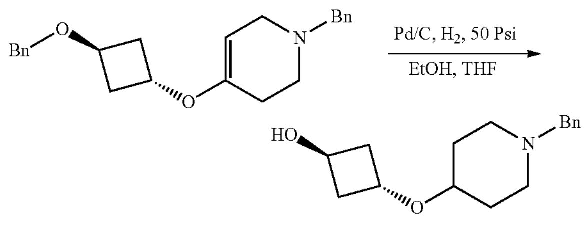

To a solution of 1-benzyl-4-(3-benzyloxycyclobutoxy)-3,6-dihydro-2H-pyridine (4.5 g, 12.88 mmol, 1 eq) in tetrahydrofuran (95 mL) and ethanol (70 mL) was added palladium on activated carbon catalyst (0.5 g, 10% purity) under nitrogen atmosphere. The suspension was degassed and purged with hydrogen for 3 times. The mixture was stirred under hydrogen (50 Psi) at 25° C. for 24 hours and then at 35° C. for 12 hours. The reaction mixture was filtered, and the filtrate was concentrated. The residue was purified by silica gel column chromatography (dichloromethane:methanol:ammonium hydroxide=20:1:0, 10:1:0.1). Compound 3-[(1-benzyl-4-piperidyl)oxy] cyclobutanol (2.8 g, 10.71 mmol, 83% yield) was obtained as a colorless oil.

Step 5

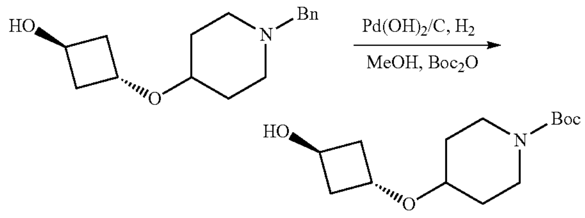

To a solution of 3-[(1-benzyl-4-piperidyl)oxy]cyclobutanol (1.1 g, 4.21 mmol, 1 eq) in methanol (10 mL) was added palladium hydroxide (591 mg) and di-tert-butyl dicarbonate ester (1.84 g, 8.42 mmol, 2 eq) under nitrogen atmosphere. The suspension was degassed and purged with hydrogen for 3 times. The mixture was stirred under hydrogen (50 Psi) at 25° C. for 12 hours. The reaction mixture was filtered and the filter was concentrated. The residue was purified by silica gel chromatography (petroleum ether:ethyl acetate=20:1 to 2:1). Compound tert-butyl 4-(3-hydroxycyclobutoxy)piperidine-1-carboxylate (820 mg, 3.02 mmol, 71% yield) was obtained as a colorless oil.

Step 6

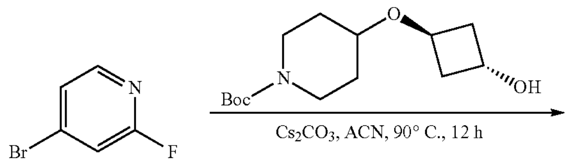

-continued

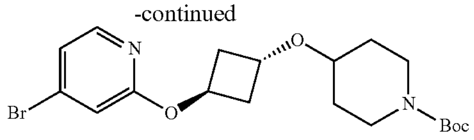

A mixture of tert-butyl 4-(3-hydroxycyclobutoxy)piperidine-1-carboxylate (1 g, 3.69 mmol, 1 eq), 4-bromo-2-fluoro-pyridine (778 mg, 4.42 mmol, 1.2 eq), cesium carbonate (2.40 g, 7.37 mmol, 2 eq) in acetonitrile (10 mL) was degassed and purged with nitrogen for three times, and then the mixture was stirred at 90° C. for 12 hours under nitrogen atmosphere. The reaction mixture was filtered and concentrated to afford crude product. The crude product was purified by silica gel chromatography (petroleum ether:ethyl acetate=1:0 to 10:1). Compound tert-butyl 4-[3-[(4-bromo-2-pyridyl)oxy]cyclobutoxy]piperidine-1-carboxylate (1.36 g, 3.18 mmol, 86% yield) was obtained as colorless oil.

Step 7

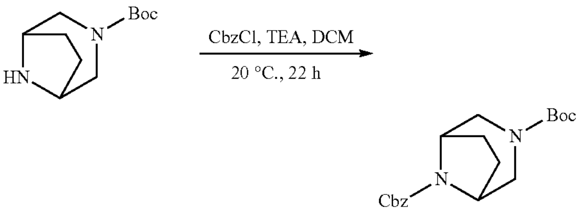

To a solution of tert-butyl 3,8-diazabicyclo[3.2.1]octane-8-carboxylate (10 g, 47.11 mmol, 1 eq) in dichloromethane (140 mL) was added CbzCl (9.64 g, 56.53 mmol, 8.04 mL, 1.2 eq) and triethylamine (8.58 g, 84.79 mmol, 11.80 mL, 1.8 eq). The mixture was stirred at 20° C. for 20 hours. TLC (dichloromethane:methanol=10:1) showed reactant 1 was not consumed completely, so CbzCl (1.61 g, 9.42 mmol, 1.34 mL, 0.2 eq) was added again. The reaction mixture was stirred at 20° C. for 2 hours. The reaction mixture was washed with water (80 mL) two times, the organic layer was dried over anhydrous sodium sulfate, and concentrated to afford the crude product. The crude product was purified by silica gel chromatography (petroleum ether:ethyl acetate=1:0 to 4:1). Compound 8-benzyl 3-(tert-butyl) 3,8-diazabicyclo[3.2.1]octane-3,8-dicarboxylate (11.48 g, 33.14 mmol, 70% yield) was obtained as colorless oil.

Step 8

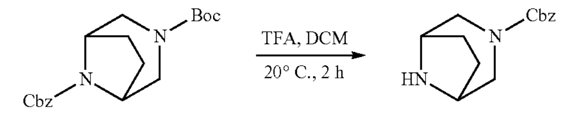 [SMILES: CC(C)(C)OC(=O)N1CC2CCC(C1)N2C(=O)OCc1ccccc1 ; O=C(OCc1ccccc1)N1CC2CCC(C1)N2]

To a solution of 8-benzyl 3-(tert-butyl) 3,8-diazabicyclo[3.2.1]octane-3,8-dicarboxylate (6.20 g, 17.90 mmol, 1 eq) in dichloromethane (80 mL) was added trifluoroacetic acid (12.32 g, 108.05 mmol, 8.00 mL, 6.04 eq). The mixture was stirred at 20° C. for 2 hours. The reaction mixture was adjusted with saturated sodium bicarbonate aqueous solution until pH=8, extracted with chloroform and isopropanol (80 mL×3, 5:1). The combined layers were dried over anhydrous sodium sulfate, concentrated to afford benzyl 3,8-diazabicyclo[3.2.1]octane-3-carboxylate (4.7 g, 17.68 mmol, 98% yield, 92% purity) as a yellow oil.

Step 9

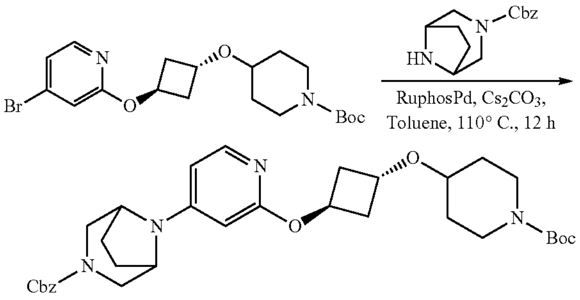

A mixture of benzyl 3,8-diazabicyclo[3.2.1]octane-3-carboxylate (784 mg, 3.18 mmol, 1 eq), tert-butyl 4-[3-[(4-bromo-2-pyridyl)oxy]cyclobutoxy]piperidine-1-carboxylate (1.36 g, 3.18 mmol, 1 eq), [2-(2-aminophenyl)phenyl]-chloropalladium; dicyclohexyl-[2-(2,6-diisopropoxyphenyl)phenyl]phosphane (148 mg, 0.19 mmol, 0.06 eq), and cesium carbonate (2.07 g, 6.37 mmol, 2 eq) in toluene (27 mL) was degassed and purged with nitrogen for three times, and then the mixture was stirred at 110° C. for 12 hours under nitrogen atmosphere. The reaction mixture was diluted with water (30 mL), and extracted with ethyl acetate (40 mL) two times. The combined organic layers were washed with saturated aqueous sodium chloride (30 mL) two times, dried over anhydrous sodium sulfate, filtered and concentrated under reduced pressure to give crude product. The crude product was purified by silica gel chromatography (petroleum ether:ethyl acetate=1:0 to 1:1). Compound benzyl 8-[2-[3-[(1-tert-butoxycarbonyl-4-piperidyl)oxy]cyclobutoxy]-4-pyridyl]-3,8-diazabicyclo[3.2.1]octane-3-carboxylate (1.35 g, 2.28 mmol, 71% yield) was obtained as a colorless oil.

Step 10

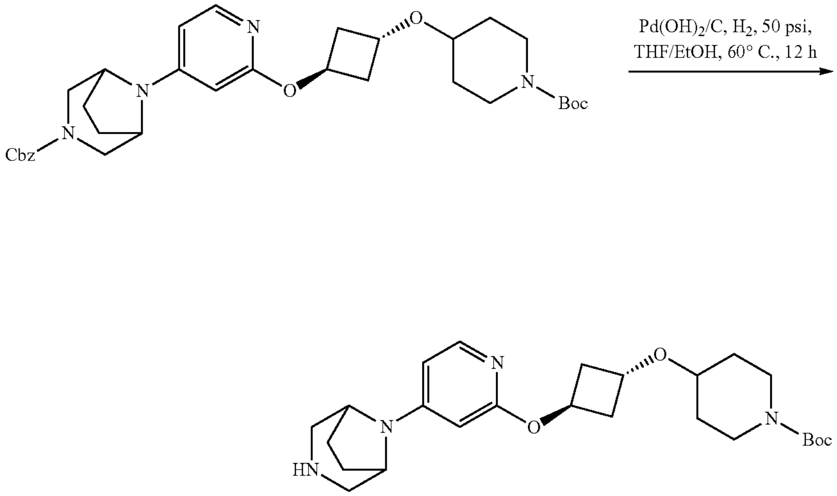

To a solution of benzyl 8-[2-[3-[(1-tert-butoxycarbonyl-4-piperidyl)oxy]cyclobutoxy]-4-pyridyl]-3,8-diazabicyclo[3.2.1]octane-3-carboxylate (1.35 g, 2.28 mmol, 1 eq) in a mixture of tetrahydrofuran (27 mL) and ethanol (27 mL) was added palladium hydroxide on activated carbon catalyst (320 mg, 10% purity) under nitrogen. The suspension was degassed under vacuum and purged with hydrogen several times. The mixture was stirred under hydrogen (50 psi) at 60° C. for 12 hours. The reaction mixture was filtered, and the filtrate was concentrated. Compound tert-butyl 4-[3-[[4-(3,8-diazabicyclo[3.2.1]octan-8-yl)-2-pyridyl]oxy]cyclobutoxy]piperidine-1-carboxylate (932 mg, 2.03 mmol, 89% yield) was obtained as a brown solid.

Step 11

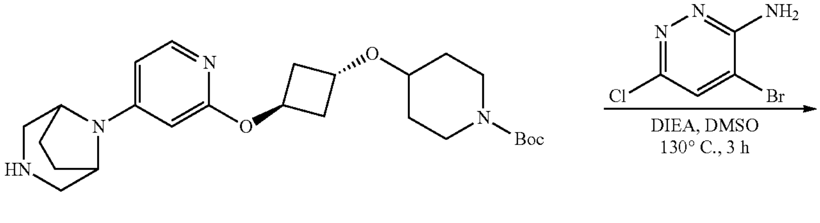

-continued

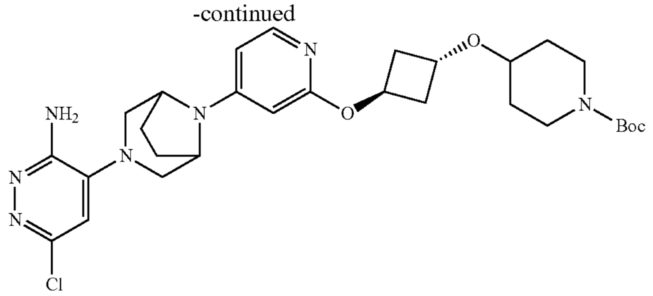

A mixture of tert-butyl 4-[3-[[4-(3,8-diazabicyclo[3.2.1]octan-8-yl)-2-pyridyl]oxy]cyclobutoxy]piperidine-1-carboxylate (932 mg, 2.03 mmol, 1 eq), 4-bromo-6-chloro-pyridazin-3-amine (508 mg, 2.44 mmol, 1.2 eq), N,N-diisopropylethylamine (2.63 g, 20.32 mmol, 3.54 mL, 10 eq) in dimethylsulfoxide (30 mL) was degassed and purged with nitrogen for three times, and then the mixture was stirred at 130° C. for 3 hours under nitrogen atmosphere. The reaction mixture was diluted with water (30 mL) and extracted with ethyl acetate (30 mL) two times. The combined organic layers were washed with saturated aqueous sodium chloride (30 mL) two times, dried over anhydrous sodium sulfate and concentrated to afford crude product. The residue was purified by semi-preparative reverse phase HPLC (column: Phenomenex Gemini C18 250*50 10 um; mobile phase: [water (0.05% ammonia hydroxide v/v)-ACN]; B %: 45%-70%, 24 MIN; 53% min). Compound tert-butyl 4-[3-[[4-[3-(3-amino-6-chloro-pyridazin-4-yl)-3,8-diazabicyclo[3.2.1]octan-8-yl]-2-pyridyl]oxy]cyclobutoxy]piperidine-1-carboxylate (772 mg, 1.32 mmol, 64% yield) was obtained as a yellow oil.

Step 12

A mixture of tert-butyl 4-[3-[[4-[3-(3-amino-6-chloro-pyridazin-4-yl)-3,8-diazabicyclo[3.2.1]octan-8-yl]-2-pyridyl]oxy]cyclobutoxy]piperidine-1-carboxylate (772 mg, 1.32 mmol, 1 eq), (2-hydroxyphenyl)boronic acid (218 mg, 1.58 mmol, 1.2 eq), tetrakis[triphenylphosphine]palladium (0) (152 mg, 0.13 mmol, 0.1 eq), potassium carbonate (364 mg, 2.63 mmol, 2 eq) in a mixture of dioxane (12 mL) and water (2 mL) was degassed and purged with nitrogen for three times, and then the mixture was stirred at 90° C. for 10 hours under nitrogen atmosphere. The reaction mixture was concentrated to afford the crude product. The residue was purified by semi-preparative reverse phase HPLC (column: Kromasil 250*50 mm*10 um; mobile phase: [water (0.1% trifluoroacetic acid)-ACN]; B %: 20ACN %-50ACN %, 20 min). Compound tert-butyl-4-[3-[[4-[3-[3-amino-6-(2-hydroxyphenyl)pyridazin-4-yl]-3,8-diazabicyclo[3.2.1]octan-8-yl]-2-pyridyl]oxy]cyclobutoxy]piperidine-1-carboxylate (500 mg, 0.71 mmol, 54% yield, 91% purity) was obtained as a yellow solid.

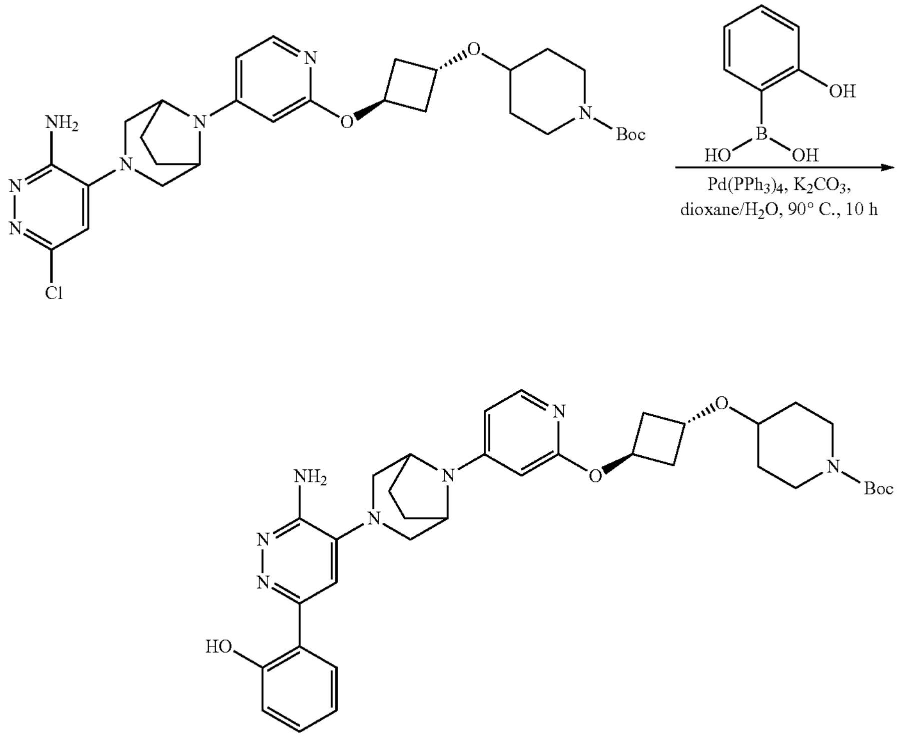 [SMILES: CC(C)(C)OC(=O)N1CCC(O[C@H]2C[C@H](Oc3cc(N4C5CCC4CN(c4cc(Cl)nnc4N)C5)ccn3)C2)CC1 ; OB(O)c1ccccc1O ; CC(C)(C)OC(=O)N1CCC(O[C@H]2C[C@H](Oc3cc(N4C5CCC4CN(c4cc(-c6ccccc6O)nnc4N)C5)ccn3)C2)CC1]

Step 13

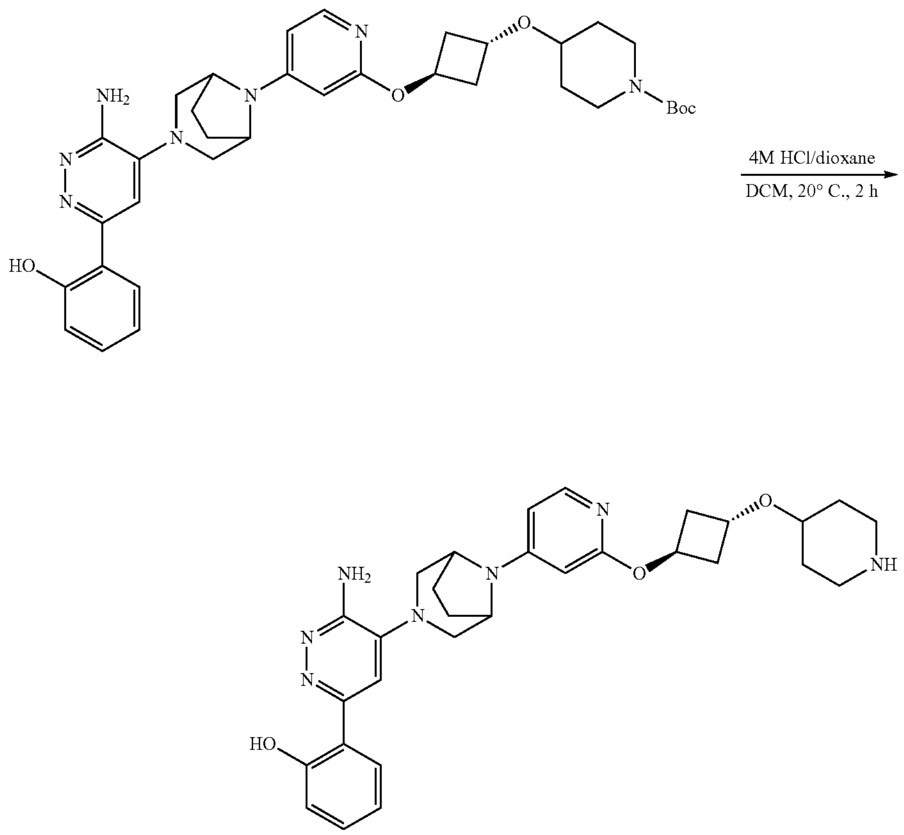 [SMILES: CC(C)(C)OC(=O)N1CCC(O[C@H]2C[C@H](Oc3cc(N4C5CCC4CN(c4cc(-c6ccccc6O)nnc4N)C5)ccn3)C2)CC1 ; Nc1nnc(-c2ccccc2O)cc1N1CC2CCC(C1)N2c1ccnc(O[C@H]2C[C@H](OC3CCNCC3)C2)c1]

To a solution of tert-butyl 4-[3-[[4-[3-[3-amino-6-(2-hydroxyphenyl)pyridazin-4-yl]-3,8-diazabicyclo[3.2.1]octan-8-yl]-2-pyridyl]oxy]cyclobutoxy]piperidine-1-carboxylate (500 mg, 0.78 mmol, 1 eq) in dichloromethane (5 mL) was added hydrochloric acid/dioxane (4 M, 5 mL, 25.75 eq). The mixture was stirred at 20° C. for 2 hours. The mixture was concentrated to afford the crude product. Compound 2-[6-amino-5-[8-[2-[3-(4-piperidyloxy)cyclobutoxy]-4-pyridyl]-3,8-diazabicyclo[3.2.1]octan-3-yl]pyridazin-3-yl]phenol (500 mg, crude, trihydrochloride) was obtained as a yellow solid.

Step 14

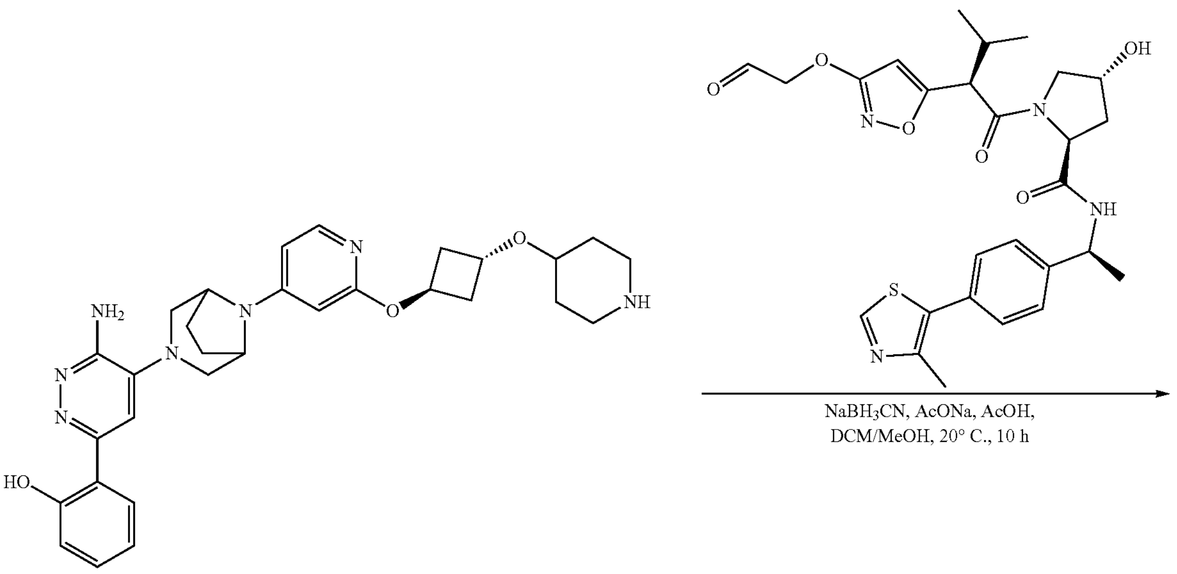

-continued

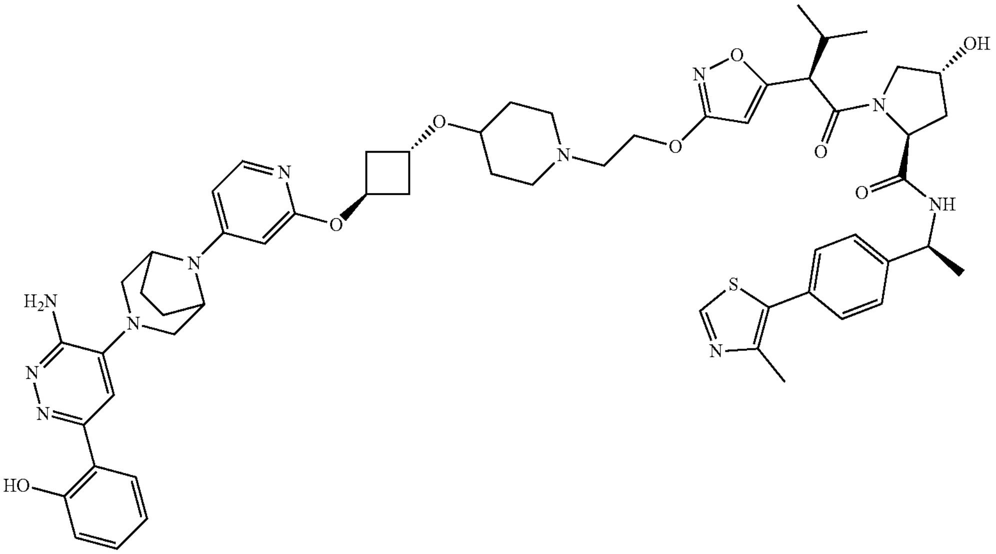

Ex. 64

To a solution of 2-[6-amino-5-[8-[2-[3-(4-piperidyloxy) cyclobutoxy]-4-pyridyl]-3,8-diazabicyclo[3.2.1]octan-3-yl] pyridazin-3-yl]phenol trihydrochloride (400 mg, 612 umol, 1 eq,) and (2S,4R)-4-hydroxy-1-[(2R)-3-methyl-2-[3-(2-oxoethoxy)isoxazol-5-yl]butanoyl]-N-[(1S)-1-[4-(4-methylthiazol-5-yl)phenyl]ethyl]pyrrolidine-2-carboxamide (331 mg, 0.61 mmol, 1 eq) in a mixture of dichloromethane (16 mL) and methanol (16 mL) was added sodium acetate (201 mg, 2.45 mmol, 4 eq), then acetic acid until pH=6, and then sodium cyanoborohydride (192 mg, 3.06 mmol, 5 eq). The mixture was stirred at 20° C. for 10 hours. The reaction mixture was diluted with water (20 mL) and extracted with dichloromethane (20 mL) three times. The combined organic layers were dried over anhydrous sodium sulfate and concentrated to afford the crude product which was purified by semi-preparative reverse phase HPLC (column: Phenomenex Synergi C18 150*25*10 um; mobile phase: [water (0.225% FA)-ACN]; B %: 18%-48%, 9 min). (2S,4R)-1-[(2R)-2-[3-[2-[4-[3-[[4-[3-[3-amino-6-(2- hydroxyphenyl) pyridazin-4-yl]-3,8-diazabicyclo[3.2.1]octan-8-yl]-2-pyridyl]oxy]cyclobutoxy]-1-piperidyl]ethoxy]isoxazol-5-yl]-3-methyl-butanoyl]-4-hydroxy-N-[(1S)-1-[4-(4-methylthiazol-5-yl)phenyl]ethyl]pyrrolidine-2-carboxamide bistrifluoroacetate (321 mg, 0.28 mmol, 45% yield) was obtained as an off-white solid.

Exemplary compound 63 and 146 were prepared using analogous procedures.

Exemplary Synthesis of Exemplary Compound 67 and 68

Ex. 67

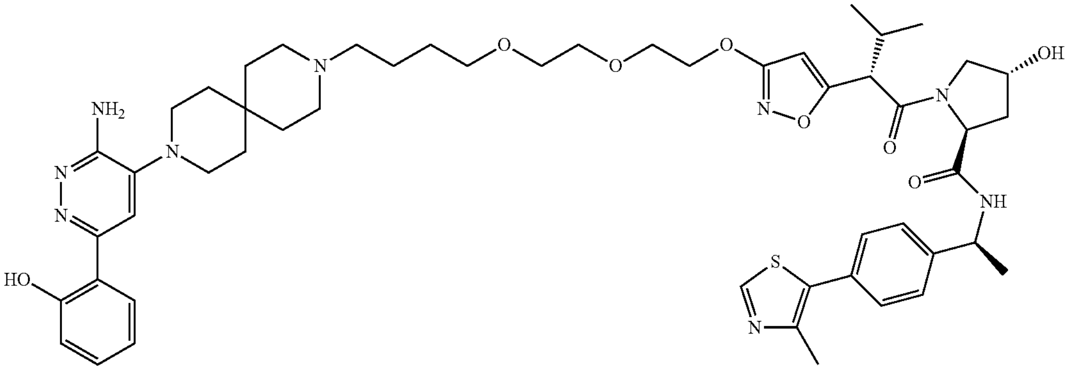

-continued

Ex. 68

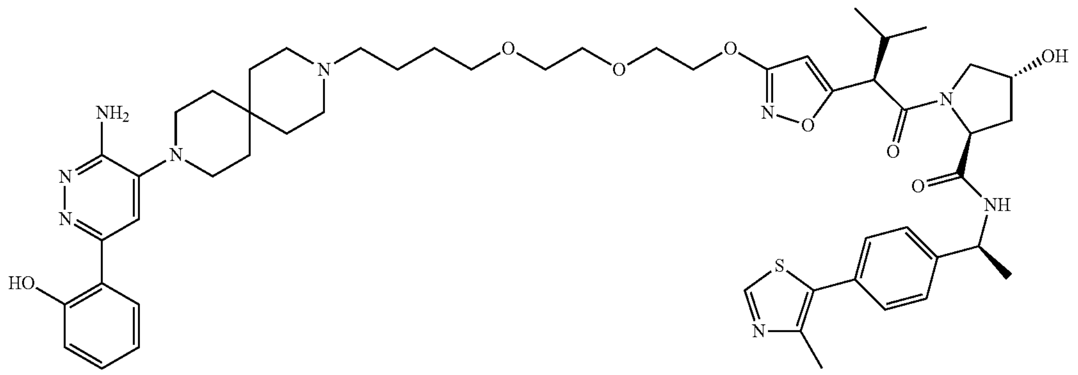

Step 1

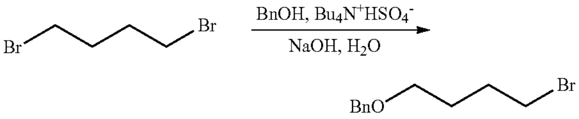

To a stirred solution of NaOH (10 g, 0.250 mol, 2.7 eq.) in water (500 mL) was added benzyl alcohol (10 g, 92.47 mmol, 1 equiv), 1,4-dibromobutane (39.93 g, 184.9 mmol, 2.00 equiv) and $Bu_4NHSO_4$ (0.78 g, 2.297 mmol, 0.02 equiv) at room temperature. The resulting mixture was stirred for 2 hours at 70° C. and then diluted with hexane (100 mL). The resulting mixture was washed with 3×50 mL of water. The organic layer was dried over anhydrous sodium sulfate and concentrated under reduced pressure. The residue was purified by silica gel column chromatography eluting with PE/EtOAc (10:1). This resulted in [(4-bromobutoxy)methyl]benzene (10 g, 44%) as a colorless oil.

Step 2

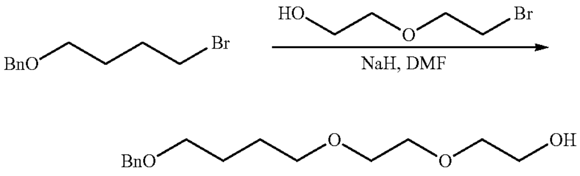

To a solution of 2-(2-hydroxyethoxy)ethan-1-ol (14.18 g, 133.7 mmol, 5 equiv) in DMF (100 mL) was added sodium hydride (60% in oil, 2.15 g, 2.5 eq.) at 0° C. under nitrogen atmosphere. After 15 minutes to the reaction mixture was added [(4-bromobutoxy)methyl]benzene (6.5 g, 26.7 mmol, 1 equiv). The resulting mixture was stirred for 3 h at 25° C. and then quenched by the addition of water (250 mL). The resulting mixture was extracted with EA (3×200 mL). The combined organic layers were washed with brine, dried over anhydrous sodium sulfate and concentrated under reduced pressure. The residue was purified by silica gel column chromatography eluting with PE/EtOAc (60%). This resulted in 2-[2-[4-(benzyloxy)butoxy]ethoxy]ethan-1-ol (4 g, 72%) as a colorless oil.

Step 3

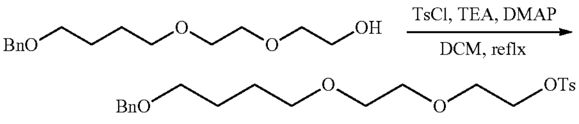

To a stirred solution of 2-[2-[4-(benzyloxy)butoxy]ethoxy]ethan-1-ol (2.4 g, 8.94 mmol, 1 equiv) and DMAP (218 mg, 1.79 mmol, 0.2 equiv) in DCM (50 mL) was added TsCl (5.1 g, 26.83 mmol, 3 equiv) and TEA (2.7 g, 26.83 mmol, 3 equiv) at room temperature. The resulting mixture was stirred overnight at 40° C. The reaction mixture was diluted with DCM (100 mL) and washed with 2×50 mL of brine. The organic layer was dried over anhydrous sodium sulfate and concentrated under reduced pressure. The residue was purified by silica gel column chromatography eluting with PE/EtOAc (3:1). This resulted in 2-[2-[4-(benzyloxy)butoxy]ethoxy]ethyl 4-methylbenzene-1-sulfonate (2.4 g, 64%) as a light yellow solid.

Step 4

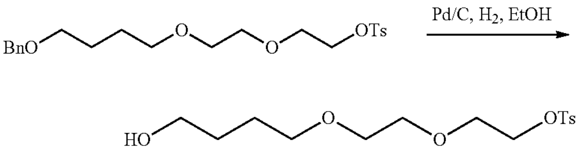

To a solution of 2-[2-[4-(benzyloxy)butoxy]ethoxy]ethyl 4-methylbenzene-1-sulfonate (3.5 g, 8.28 mmol, 1 equiv) in 100 mL EtOH was added 10% Pd/C (3.5 g) and $CH_3COOH$ (0.95 mL, 15.88 mmol, 2.01 equiv) under nitrogen atmosphere. The flask was vacuumed and flushed with hydrogen. The resulting mixture was hydrogenated at 40° C. overnight under hydrogen atmosphere using a hydrogen balloon, then filtered through a Celite pad and concentrated under reduced pressure. The residue was purified by reverse phase column chromatography under the following conditions: column, C18 silica gel; mobile phase, ACN in water, 10% to 50% gradient in 30 min. This resulted in 4-(2-[2-[(4-methylbenzenesulfonyl)oxy]ethoxy]ethoxy)butan-1-ol (2.2 g, 80%) as a colorless oil.

Step 5

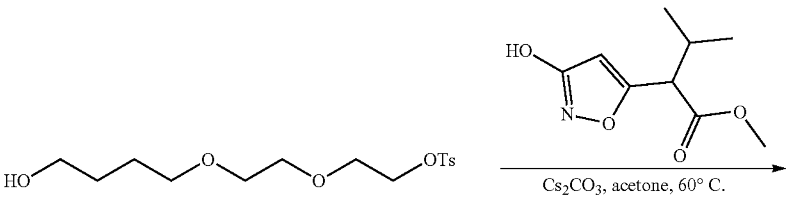

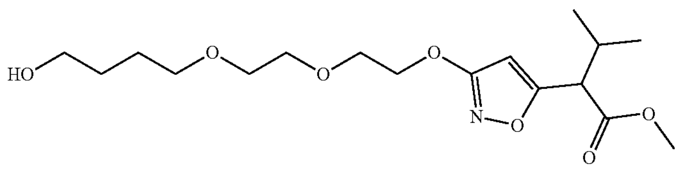

To a stirred solution of methyl 2-(3-hydroxy-1,2-oxazol-5-yl)-3-methylbutanoate (1.5 g, 7.53 mmol, 1 equiv) and 4-(2-[2-[(4-methylbenzenesulfonyl)oxy]ethoxy]ethoxy)butan-1-ol (3.0 g, 9.04 mmol, 1.2 equiv) in acetone (50 mL) was added $Cs_2CO_3$ (4.9 g, 15.04 mmol, 2.00 equiv) at room temperature under nitrogen atmosphere. The resulting mixture was stirred for 4 hours at 60° C. and then concentrated under reduced pressure. The residue was purified by silica gel column chromatography eluting with $CH_2Cl_2$/MeOH (10:1). This resulted in methyl 2-(3-[2-[2-(4-hydroxybutoxy)ethoxy]ethoxy]-1,2-oxazol-5-yl)-3-methylbutanoate (800 mg, 30%) as a light yellow oil.

Step 6

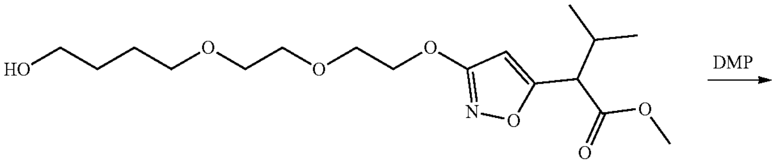

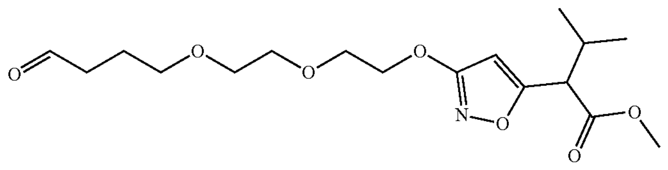

To a stirred solution of methyl 2-(3-[2-[2-(4-hydroxybutoxy)ethoxy]ethoxy]-1,2-oxazol-5-yl)-3-methylbutanoate (550 mg, 1.53 mmol, 1 equiv) in DCM (20 mL) was added Dess-Martin periodinane (1298 mg, 3.06 mmol, 2 equiv) at 0° C. The resulting mixture was stirred for 2 hours at 30° C. and then quenched by the addition of saturated sodium thiosulfate solution. The resulting mixture was extracted with DCM (3x20 mL). The combined organic layers were washed with saturated sodium bicarbonate solution, dried over sodium sulfate and concentrated under reduced pressure. The residue was purified by Prep-TLC ($CH_2Cl_2$/MeOH 10:1) to afford methyl 3-methyl-2-(3-[2-[2-(4-oxobutoxy)ethoxy]ethoxy]-1,2-oxazol-5-yl)butanoate (440 mg, 80%) as a light yellow solid.

Methyl 3-methyl-2-(3-[2-[2-(4-oxobutoxy)ethoxy]ethoxy]-1,2-oxazol-5-yl)butanoate was converted to the final compounds according to the scheme below using procedures analogous to those described for other examples of the series (e.g., exemplary compound 91), as well as obvious to those skilled in the art.

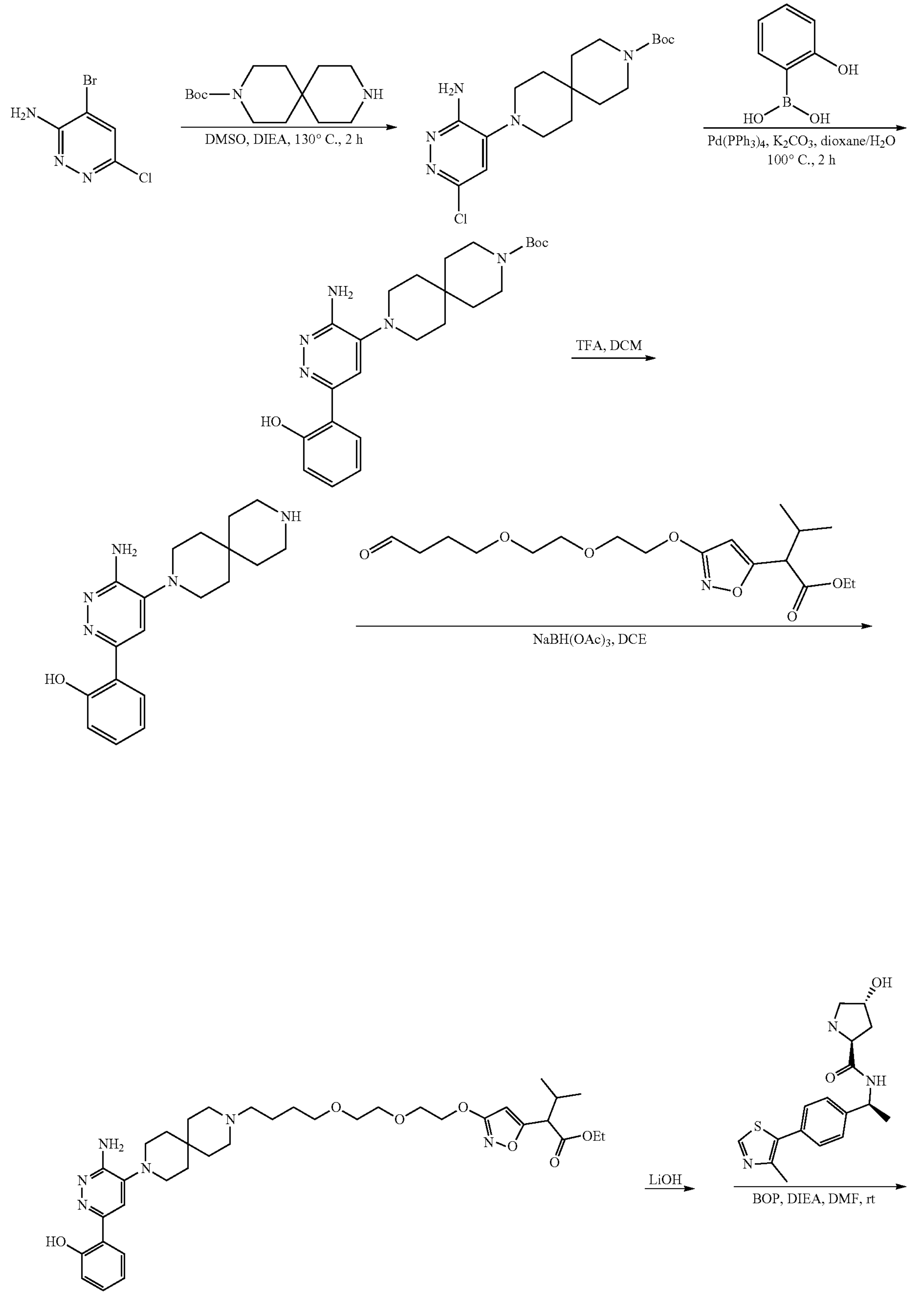
DMSO, DIEA, 130° C., 2 h
Pd(PPh3)4, K2CO3, dioxane/H2O
100° C., 2 h
TFA, DCM
NaBH(OAc)3, DCE
LiOH
BOP, DIEA, DMF, rt -continued
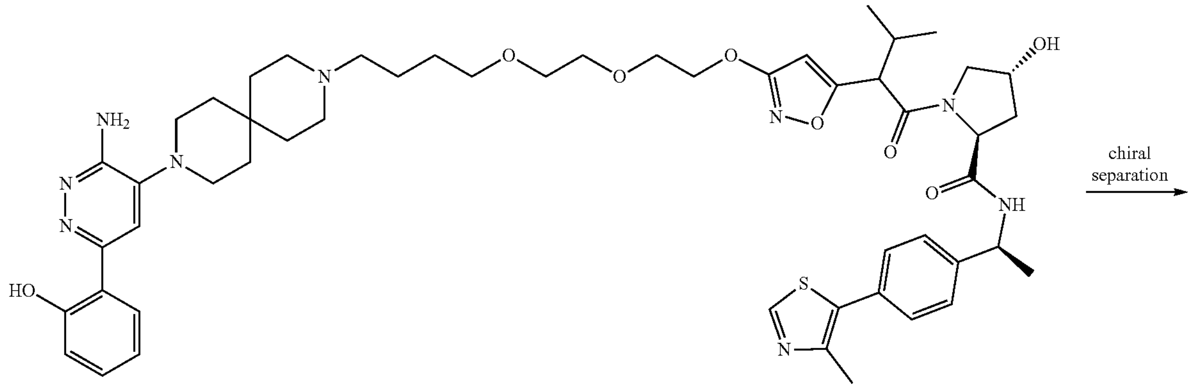
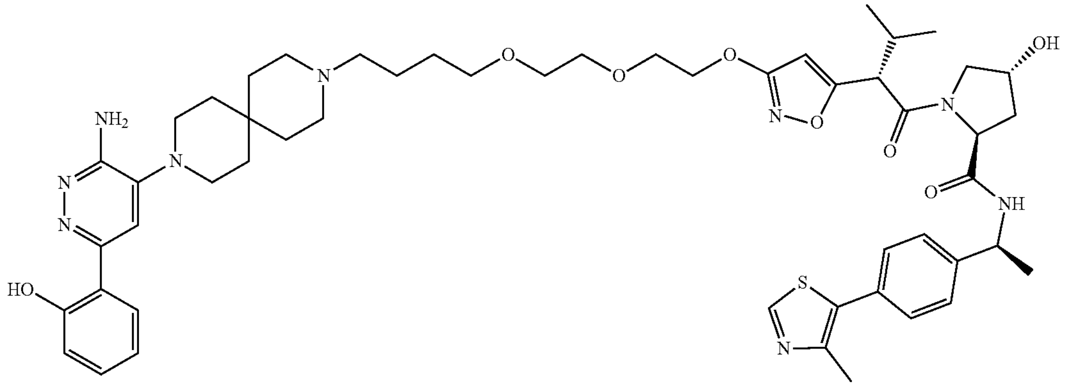
Ex. 67
+
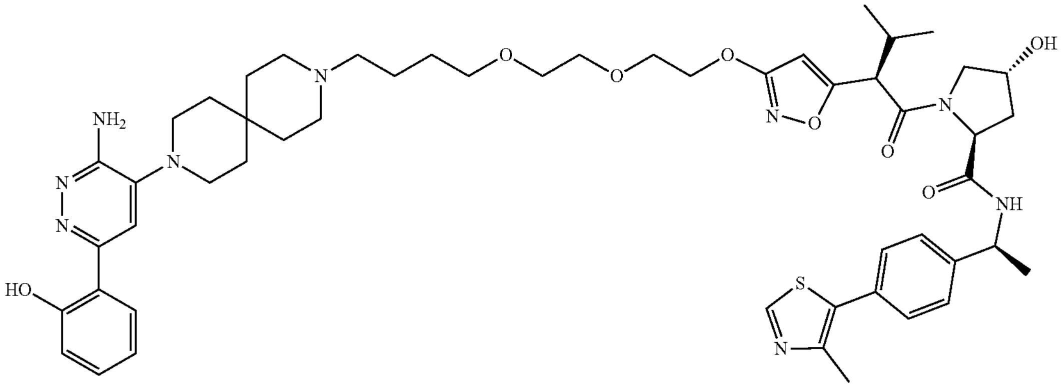
Ex. 68

Exemplary compounds 65, 66, 71, 73, and 74 were prepared using analogous procedures.

Exemplary Synthesis of Exemplary Compound 69 and 70

Ex. 69

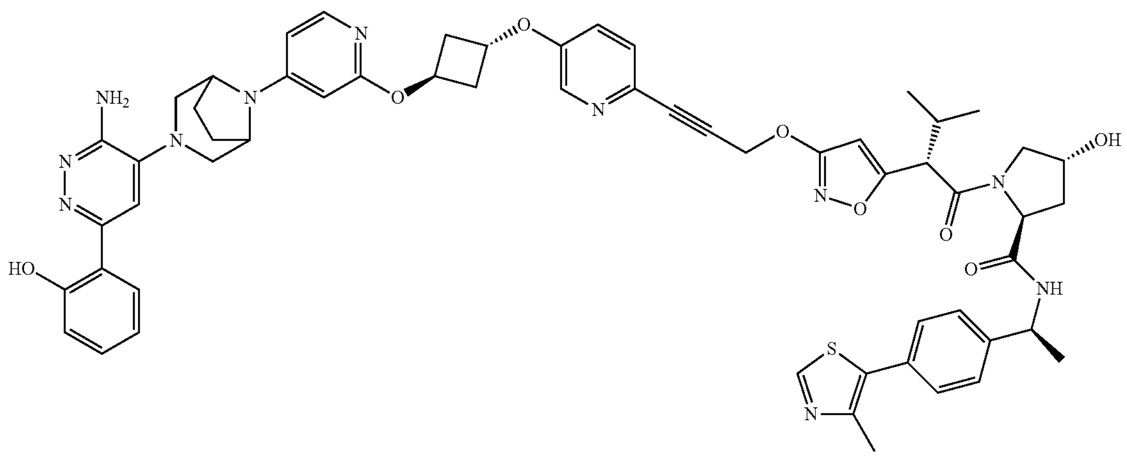

Ex. 70

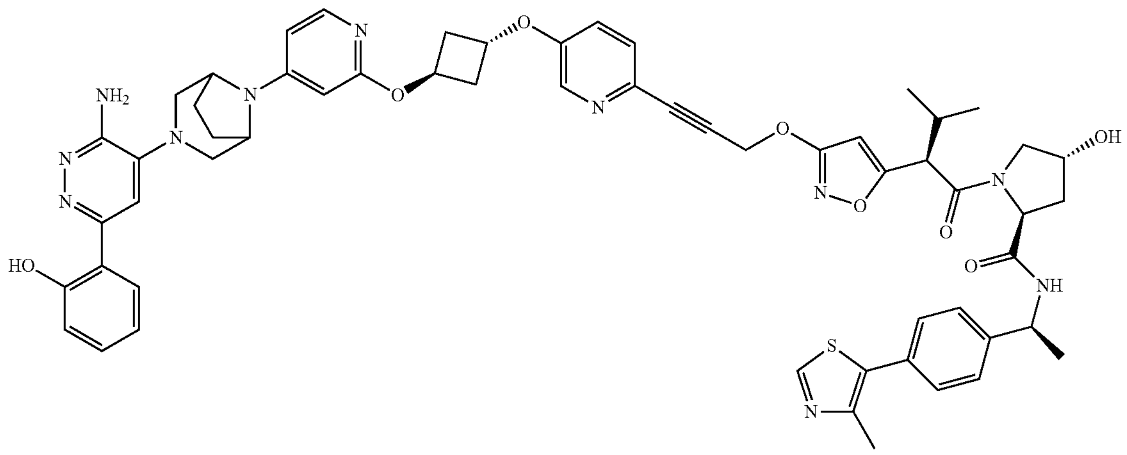

Step 1

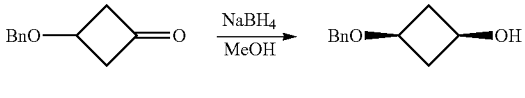

Into a 250-mL round-bottom flask, was placed a solution of 3-(benzyloxy)cyclobutan-1-one (6.0 g, 34.05 mmol, 1.0 equiv) in ethanol (100 mL). This was followed by the addition of sodium borohydride (1.25 g, 33.94 mmol, 1.00 equiv) in several batches at 0° C. The resulting solution was stirred for 3 hours at 0° C. The reaction was then quenched by the addition of water (100 mL). The resulting solution was extracted with ethyl acetate (50 mL×2), and the organic layers combined and dried over anhydrous sodium sulfate and concentrated under vacuum. This resulted in 6.0 g (99%) of (1s,3s)-3-(benzyloxy)cyclobutan-1-ol as a light yellow oil.

Step 2

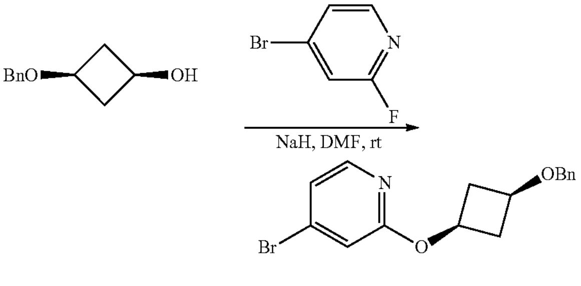

Into a 500-mL round-bottom flask purged and maintained with an inert atmosphere of nitrogen, was placed a solution of (1s,3s)-3-(benzyloxy)cyclobutan-1-ol (8.0 g, 44.89 mmol, 1.10 equiv) in N,N-dimethylformamide (100 mL). This was followed by the addition of sodium hydride (60%) (2.15 g, 89.58 mmol, 1.20 equiv) in several batches at 0° C. To this was added 4-bromo-2-fluoropyridine (70.0 g, 39.78 mmol, 1.00 equiv). The resulting solution was stirred overnight at room temperature. The reaction was then quenched by the addition of water/ice. The resulting solution was extracted with ethyl acetate (80 mL×2) and the organic layers combined. The resulting mixture was washed with brine (80 mL×2). The resulting mixture was concentrated under reduced pressure. The residue was applied onto a silica gel column with ethyl acetate/petroleum ether (1:1). This resulted in 7.0 g (53%) of 4-bromo-2-[(1s,3s)-3-(benzyloxy)cyclobutoxy]pyridine as a light yellow oil.

Step 3

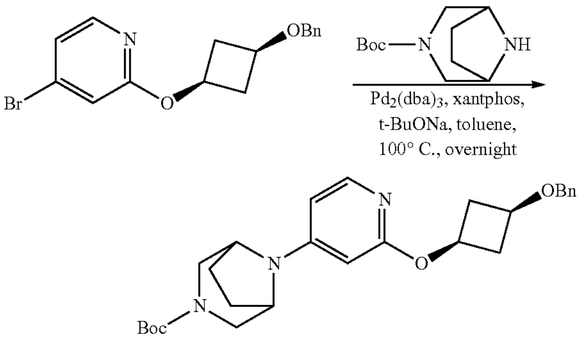

Into a 500-mL round-bottom flask purged and maintained with an inert atmosphere of nitrogen, was placed a solution of 4-bromo-2-[(1 s,3s)-3-(benzyloxy)cyclobutoxy]pyridine (8.4 g, 25.13 mmol, 1.30 equiv) in toluene (200 mL), tert-butyl 3,8-diazabicyclo[3.2.1]octane-3-carboxylate (4.11 g, 19.36 mmol, 1.00 equiv), sodium tert-butoxide (3.2 g, 33.2 mmol, 1.5 equiv), xantphos (2.32 g, 4.01 mmol, 0.20 equiv), $Pd_2(dba)_3CH_2Cl_2$ (430.0 mg, 0.40 mmol, 0.02 equiv). The resulting solution was stirred overnight at 100° C. The reaction was then quenched by the addition of water (100 mL). The resulting solution was extracted with ethyl acetate (80 mL×2), and the organic layers were combined. The resulting mixture was washed with of brine (100 mL×2). The mixture was dried over anhydrous sodium sulfate and concentrated under reduced pressure. The residue was applied onto a silica gel column eluting with ethyl acetate/hexane (1:1). This resulted in 8.0 g (89%) of tert-butyl 8-[2-[(1s,3s)-3-(benzyloxy)cyclobutoxy]pyridin-4-yl]-3,8-diazabicyclo[3.2.1]octane-3-carboxylate as a light yellow oil.

Step 4

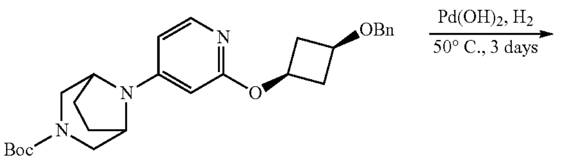

-continued

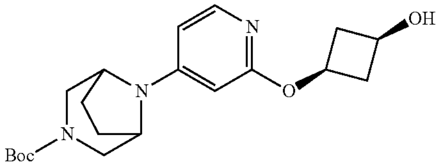

To a solution of tert-butyl 8-[2-[(1s,3s)-3-(benzyloxy)cyclobutoxy]pyridin-4-yl]-3,8-diazabicyclo[3.2.1]octane-3-carboxylate (7.0 g, 15.03 mmol, 1.00 equiv) in 150 mL ethanol was added palladium hydroxide catalyst (7.0 g, 49.85 mmol, 3.32 equiv) and acetic acid (2 mL) under nitrogen atmosphere in a 250 ml round bottom flask. The flask was then vacuumed and flushed with hydrogen. The reaction mixture was hydrogenated at 50° C. for 3 days under hydrogen atmosphere using a hydrogen balloon, then filtered through a Celite pad and concentrated under reduced pressure. This resulted in 5.4 g (96%) of tert-butyl 8-[2-[(1s,3s)-3-hydroxycyclobutoxy]pyridin-4-yl]-3,8-diazabicyclo[3.2.1]octane-3-carboxylate as a light yellow oil.

Step 5

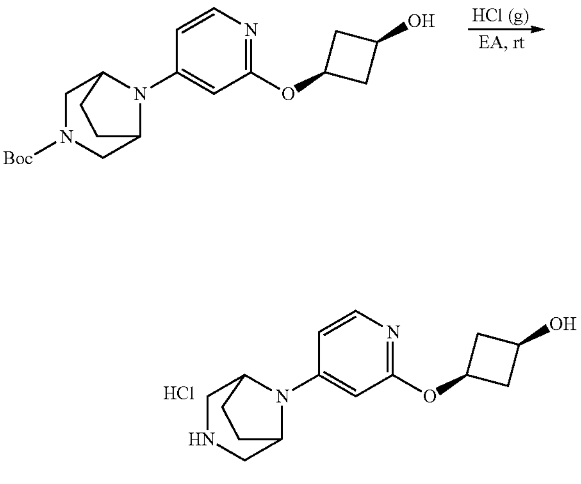

Into a 100-mL round-bottom flask, was placed a solution of tert-butyl 8-[2-[(1s,3s)-3-hydroxycyclobutoxy]pyridin-4-yl]-3,8-diazabicyclo[3.2.1]octane-3-carboxylate (5.0 g, 13.32 mmol, 1.00 equiv) in the mixed solvent of ethyl acetate and methanol (10:1) (50 mL). Hydrogen chloride (g) was passed through. The resulting mixture was stirred for 3 hours at room temperature and concentrated under reduced pressure. This resulted in 4.0 g (96%) of (1s,3s)-3-[(4-[3,8-diazabicyclo[3.2.1]octan-8-yl]pyridin-2-yl)oxy]cyclobutan-1-ol hydrochloride as an off-white solid.

Step 6

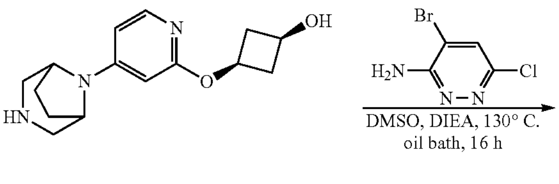

-continued

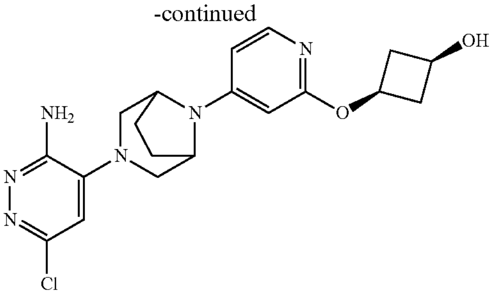

Into a 20-mL pressure tank reactor purged and maintained with an inert atmosphere of nitrogen, was placed a solution of (1s,3s)-3-[(4-[3,8-diazabicyclo[3.2.1]octan-8-yl]pyridin-2-yl)oxy]cyclobutan-1-ol hydrochloride (1.0 g, 3.21 mmol, 1.00 equiv) in dimethyl sulfoxide (10 mL). Then N,N-Diisopropylethylamine (5 mL) and 4-bromo-6-chloro-pyridazin-3-amine (3.01 g, 14.44 mmol, 4.00 equiv) were added. The resulting solution was stirred for 16 hours at 130° C. The reaction was then quenched by the addition of water (50 mL). The resulting solution was extracted with ethyl acetate (3×30 mL) and the organic layers combined. The resulting mixture was washed with brine (3×50 mL). The mixture was dried over anhydrous sodium sulfate. The residue was applied onto a silica gel column with dichloromethane/methanol (10:1). This resulted in 490 mg (38%) of (1 s,3s)-3-([4-[3-(3-amino-6-chloropyridazin-4-yl)-3,8-diazabicyclo[3.2.1]octan-8-yl]pyridin-2-yl]oxy)cyclobutan-1-ol as yellow oil.

Step 7

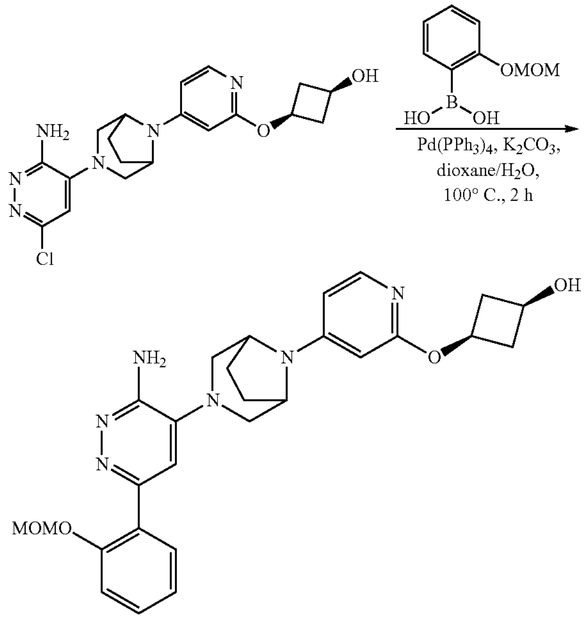

Into a 20-mL pressure tank reactor purged and maintained with an inert atmosphere of nitrogen, was placed a solution of (1s,3s)-3-([4-[3-(3-amino-6-chloropyridazin-4-yl)-3,8-diazabicyclo[3.2.1]octan-8-yl]pyridin-2-yl]oxy)cyclobutan-1-ol (800.0 mg, 1.99 mmol, 1.00 equiv) in the mixed solvent of dioxane and water (4:1) (15 mL), [2-(methoxymethoxy)phenyl]boronic acid (543.5 mg, 2.99 mmol, 1.50 equiv), potassium carbonate (823.9 mg, 6.0 mmol, 3.00 equiv), $Pd(PPh_3)_4$ (230.0 mg, 0.20 mmol, 0.10 equiv). The resulting solution was stirred for 2 hours at 90° C. The reaction was then quenched by the addition of water (30 mL). The resulting solution was extracted with ethyl acetate (50 mL×2) and the organic layers combined. The resulting mixture was washed with brine (50 mL×2). The mixture was dried over anhydrous sodium sulfate. The residue was applied onto a silica gel column with dichloromethane/methanol (10:1). This resulted in 820.0 mg (82%) of (1s,3s)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutan-1-ol as a yellow solid.

Step 8

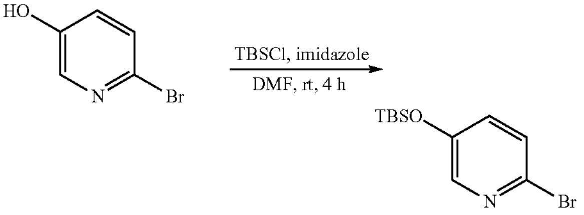

To a stirred solution of 6-bromopyridin-3-ol (12.70 g, 72.9 mmol, 1.00 equiv) and imidazole (7.45 g, 109.5 mmol, 1.50 equiv) in DMF (100 mL) were added TBSCl (16.50 g, 109.47 mmol, 1.50 equiv) in portions at 0° C. under nitrogen atmosphere. The resulting mixture was stirred for 3 hours at room temperature under nitrogen atmosphere. The reaction was quenched with water (100 mL) at room temperature, and the resulting mixture was extracted with EtOAc (50 mL×3). The combined organic layers were washed with brine (100 mL×2), dried over anhydrous sodium sulfate and concentrated under reduced pressure. The residue was purified by silica gel column chromatography, eluted with PE/EtOAc (5:1) to afford 2-bromo-5-[(tert-butyldimethylsilyl)oxy]pyridine (19 g, 90%) as a colorless oil.

Step 9

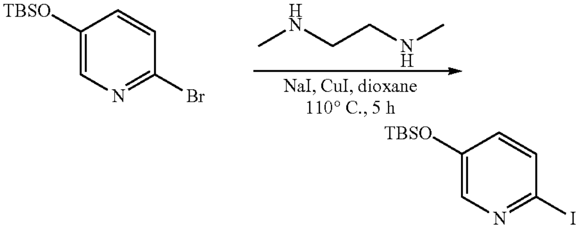

To a stirred mixture of 2-bromo-5-[(tert-butyldimethylsilyl)oxy]pyridine (4.00 g, 13.88 mmol, 1.00 equiv) and NaI (10.40 g, 69.38 mmol, 5.00 equiv) in 1,4-dioxane (20 mL) were added CuI (0.26 g, 1.365 mmol, 0.10 equiv) and methyl[2-(methylamino)ethyl]amine (0.12 g, 1.361 mmol, 0.10 equiv) dropwise at room temperature under nitrogen atmosphere. The resulting mixture was stirred for 5 hours at 110° C. under nitrogen atmosphere. The reaction mixture was filtered, and the filter cake was rinsed with 1,4-dioxane. The filtrate was concentrated under reduced pressure. The residue was purified by silica gel column chromatography eluting with hexane/EtOAc (5:1) to afford 5-[(tert-butyldimethylsilyl)oxy]-2-iodopyridine (4.2 g, 90%) as an off-white solid.

Step 10

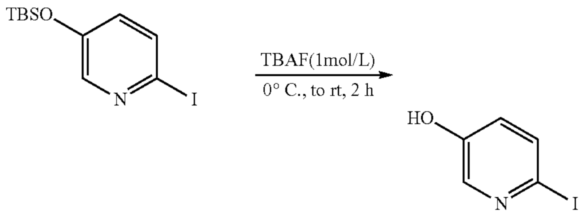

To a stirred solution of 5-[(tert-butyldimethylsilyl)oxy]-2-iodopyridine (4.20 g, 12.53 mmol, 1.00 equiv) in THF (20 mL) were added TBAF (1 mol/L, 27 mL, 27 mmol, 2.00 equiv) dropwise at 0° C. under hydrogen atmosphere. The resulting mixture was stirred for 2 hours at room temperature under nitrogen atmosphere. The reaction was quenched with water (50 mL) at room temperature. The resulting mixture was extracted with EtOAc (50 mL×3). The combined organic layers were washed with brine (50 mL), dried over anhydrous sodium sulfate and concentrated under reduced pressure. The residue was purified by silica gel column chromatography eluting with hexane/EtOAc (2:1) to afford 6-iodopyridin-3-ol (2.3 g, 83%) as a light yellow solid.

Step 11

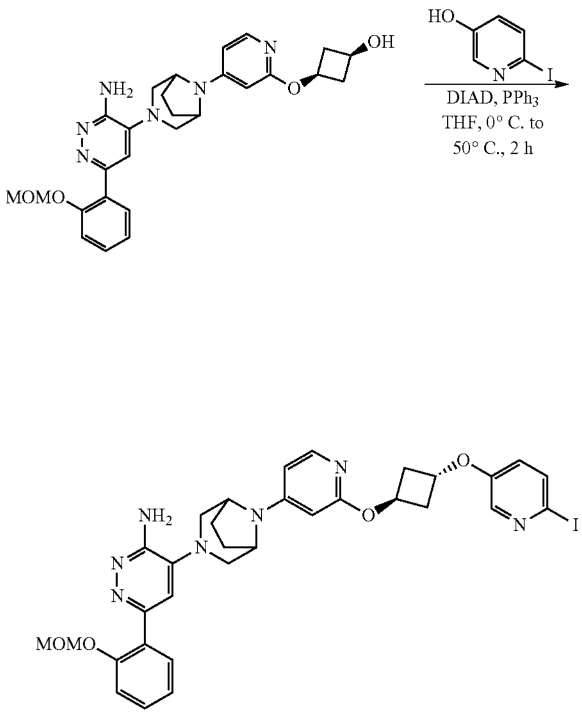

To a solution of $PPh_3$ (523 mg, 2.00 mmol, 2.00 equiv) in THF (10 mL) was added DIAD (403 mg, 2.00 mmol, 2.00 equiv), (1s,3s)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutan-1-ol (504 mg, 1.00 mmol, 1 equiv) and 6-iodopyridin-3-ol (265 mg, 1.20 mmol, 1.20 equiv) at 0° C. under nitrogen atmosphere. The resulting mixture was stirred for 5 minutes at 0° C., heated up to 50° C. and stirred for 2 hours at 50° C. under nitrogen atmosphere. The reaction was quenched by the addition of water (20 mL) at room temperature, and the resulting mixture was extracted with EtOAc (20 mL×3). The combined organic layers were washed with brine (30 mL), dried over anhydrous sodium sulfate and concentrated under reduced pressure. The residue was purified by silica gel column chromatography eluting with dichloromethane/methanol (10:1) to afford 6-[2-(methoxymethoxy)phenyl]-4-(8-[2-[(1r,3r)-3-[(6-iodopyridin-3-yl)oxy]cyclobutoxy]pyridin-4-yl]-3,8-diazabicyclo[3.2.1]octan-3-yl)pyridazin-3-amine (382 mg, 54%) as a light yellow solid.

Step 12

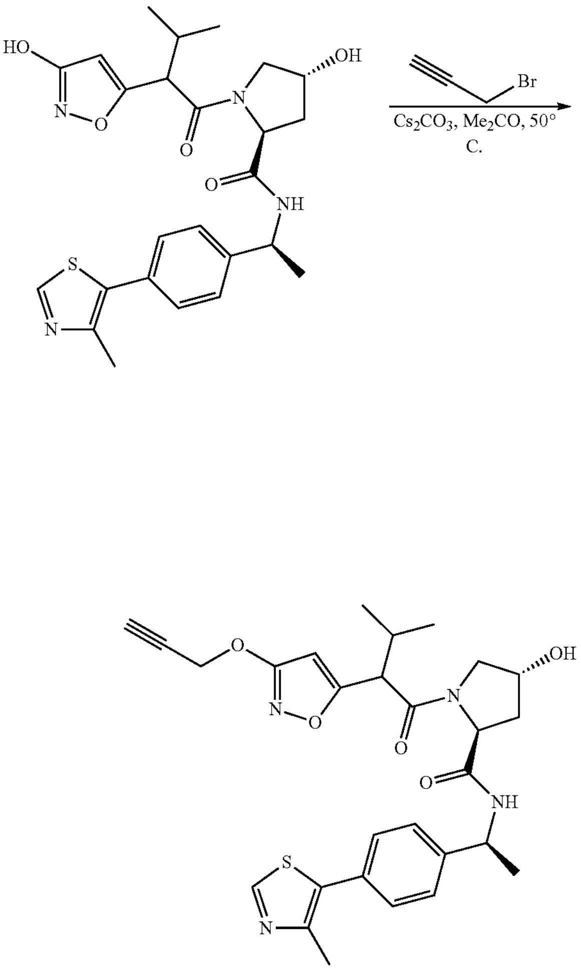

To a solution of (2S,4R)-4-hydroxy-1-[2-(3-hydroxy-1,2-oxazol-5-yl)-3-methylbutanoyl]-N-[(1S)-1-[4-(4-methyl-1,3-thiazol-5-yl)phenyl]ethyl]pyrrolidine-2-carboxamide (780 mg, 1.56 mmol, 1.00 equiv) in acetone (40 mL) was added $Cs_2CO_3$ (1019 mg, 3.13 mmol, 2.00 equiv), and 3-bromoprop-1-yne (558 mg, 4.69 mmol, 3.00 equiv) at room temperature. The resulting mixture was stirred for 3 hours at 50° C. under nitrogen atmosphere. The mixture was filtered, and the filter cake was rinsed with THF (50 mL×2). The filtrate was concentrated under reduced pressure. The residue was purified by silica gel column chromatography eluting with dichloromethane/methanol (10:1) to afford (2S, 4R)-4-hydroxy-N-[(1S)-1-[4-(4-methyl-1,3-thiazol-5-yl) phenyl]ethyl]-1-[3-methyl-2-[3-(prop-2-yn-1-yloxy)-1,2-oxazol-5-yl]butanoyl]pyrrolidine-2-carboxamide (520 mg, 62%) as an off-white solid.

Step 13

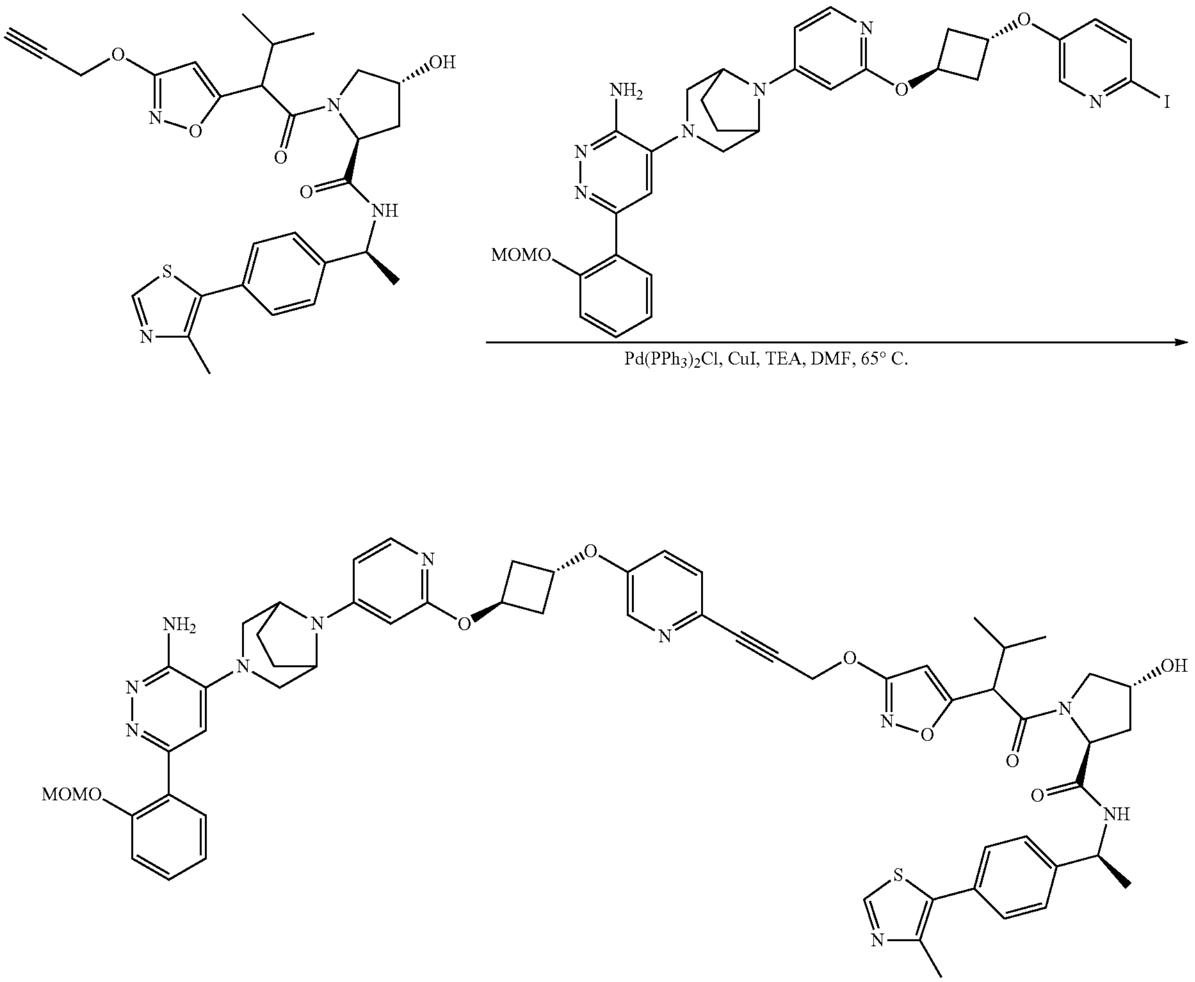

To a stirred mixture of 6-[2-(methoxymethoxy)phenyl]-4-(8-[2-[(1r,3r)-3-[(6-iodopyridin-3-yl)oxy]cyclobutoxy] pyridin-4-yl]-3,8-diazabicyclo[3.2.1]octan-3-yl)pyridazin-3-amine (224 mg, 0.317 mmol, 1.00 equiv) and CuI (6.0 mg, 0.032 mmol, 0.10 equiv) in DMF (5 mL) was added TEA (96 mg, 0.950 mmol, 3.00 equiv), and $Pd(PPh_3)_2Cl_2$ (22.2 mg, 0.032 mmol, 0.10 equiv) at room temperature under nitrogen atmosphere. The resulting mixture was stirred for 5 minutes at room temperature and then was added to the solution of (2S,4R)-4-hydroxy-N-[(1S)-1-[4-(4-methyl-1,3-thiazol-5-yl)phenyl]ethyl]-1-[3-methyl-2-[3-(prop-2-yn-1-yloxy)-1,2-oxazol-5-yl]butanoyl]pyrrolidine-2-carboxamide (170 mg, 0.317 mmol, 1.00 equiv) in DMF (2 mL). The reaction mixture was stirred for 2 hours at 65° C. under nitrogen atmosphere. The reaction was quenched by the addition of water (30 mL). The resulting mixture was extracted with EtOAc (20 mL×3). The combined organic layers were washed with brine (30 mL×3), dried over anhydrous sodium sulfate and concentrated under reduced pressure. The residue was purified by prep-TLC eluting with dichloromethane/methanol (9:1) to afford (2S,4R)-4-hydroxy-N-[(1S)-1-[4-(4-methyl-1,3-thiazol-5-yl)phenyl]ethyl]-1-(3-methyl-2-[3-[(3-[5-[(1r,3r)-3-[[4-(3-[3-amino-6-[2-(methoxymethoxy)phenyl]pyridazin-4-yl]-3,8-diazabicyclo [3.2.1]octan-8-yl)pyridin-2-yl]oxy]cyclobutoxy]pyridin-2-yl]prop-2-yn-1-yl)oxy]-1,2-oxazol-5-yl]butanoyl) pyrrolidine-2-carboxamide (175 mg, 49%) as a light yellow solid.

The two diastereomers of (2S,4R)-4-hydroxy-N-[(1S)-1-[4-(4-methyl-1,3-thiazol-5-yl)phenyl]ethyl]-1-(3-methyl-2-[3-[(3-[5-[(1r,3r)-3-[(4-[3-[3-amino-6-(2-hydroxyphenyl) pyridazin-4-yl]-3,8-diazabicyclo[3.2.1]octan-8-yl]pyridin-2-yl)oxy]cyclobutoxy]pyridin-2-yl]prop-2-yn-1-yl)oxy]-1, 2-oxazol-5-yl]butanoyl)pyrrolidine-2-carboxamide (620 mg) were separated by chiral HPLC with the following conditions: Column: CHIRALPAK IG, 2.0 cm I.D*25 cm (5 um); Mobile Phase A:MeOH (8 mmol/L NH3.MeOH), Mobile Phase B: DCM; Flow rate: 20 mL/min; Gradient: 30% B to 30% B in 17 min; 220/254 nm; RT1: 8.495 min; RT2: 12.854 min. This resulted in 137 mg (22%) of isomer 1 tentatively identified as (2S,4R)-4-hydroxy-N-[(1S)-1-[4-

(4-methyl-1,3-thiazol-5-yl)phenyl]ethyl]-1-[(2S)-3-methyl-2-[3-[(3-[5-[(1r,3r)-3-[(4-[3-[3-amino-6-(2-hydroxyphenyl)pyridazin-4-yl]-3,8-diazabicyclo[3.2.1]octan-8-yl]pyridin-2-yl)oxy] cyclobutoxy]pyridin-2-yl]prop-2-yn-1-yl)oxy]-1,2-oxazol-5-yl]butanoyl]pyrrolidine-2-carboxamide (light-yellow solid), and in 199 mg (32%) of isomer 2 tentatively identified as (2S,4R)-4-hydroxy-N-[(1S)-1-[4-(4-methyl-1,3-thiazol-5-yl)phenyl]ethyl]-1-[(2R)-3-methyl-2-[3-[(3-[5-[(1r,3r)-3-[(4-[3-[3-amino-6-(2-hydroxyphenyl)pyridazin-4-yl]-3,8-diazabicyclo[3.2.1]octan-8-yl]pyridin-2-yl)oxy] cyclobutoxy]pyridin-2-yl]prop-2-yn-1-yl)oxy]-1,2-oxazol-5-yl]butanoyl]pyrrolidine-2-carboxamide (off-white solid).

Exemplary compounds 226, 227, 231, 232, 236, and 237 using analogous procedures.

Exemplary Synthesis of Exemplary Compound 76

Ex. 67

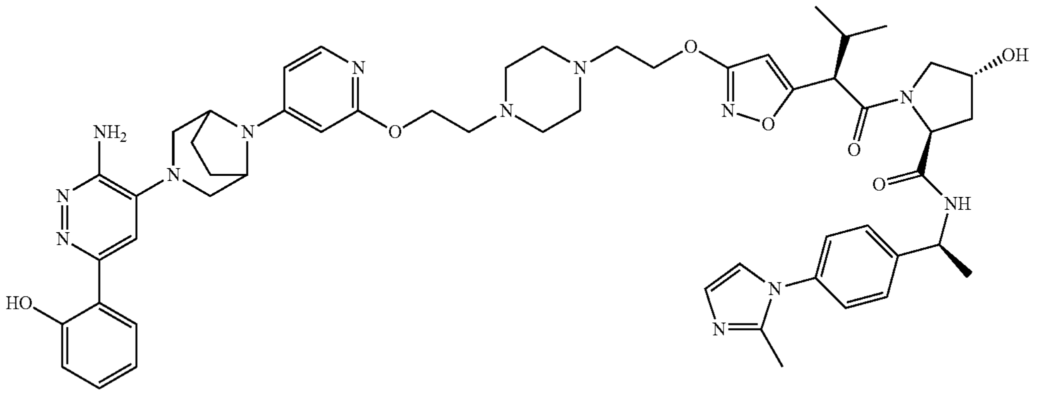

Step 1

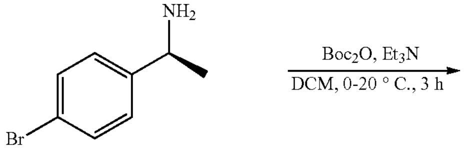

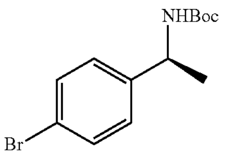

To a solution of (1S)-1-(4-bromophenyl)ethanamine (5 g, 24.99 mmol, 1.0 eq) in dichloromethane (100 mL) was added triethylamine (2.53 g, 24.99 mmol, 1.0 eq) at 0° C. Then the mixture was stirred at 0° C. for 30 minutes. Then di-tert-butyl dicarbonate ester (5.45 g, 24.99 mmol, 1.0 eq) was added, and the mixture and stirred at 0° C. for 30 minutes followed by 20° C. for 2 hours. The mixture was quenched with saturated aqueous sodium bicarbonate (20 mL), diluted with water (50 mL), extracted with dichloromethane (100 mL×2), washed with brine (100 mL), dried over anhydrous sodium sulfate, filtered and concentrated. The residue was stirred with petroleum ether:ethyl acetate (50 mL, v/v=5/1), and then filtered. Tert-butyl N-[(1S)-1-(4-bromophenyl)ethyl]carbamate (6.4 g, 20.68 mmol, 82% yield) was obtained as a white solid.

Step 2

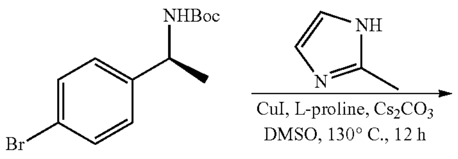

-continued

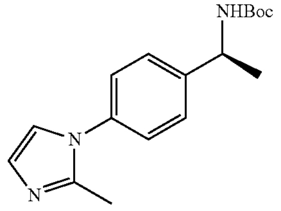

To a solution of tert-butyl N-[(1S)-1-(4-bromophenyl)ethyl]carbamate (3 g, 9.99 mmol, 1.0 eq) and 2-methyl-1H-imidazole (902 mg, 10.99 mmol, 1.1 eq) in dimethylsulfoxide (15 mL) was added L-proline (1.38 g, 11.99 mmol, 1.2 eq), cesium carbonate (9.77 g, 29.98 mmol, 3.0 eq) and copper iodide (2.28 g, 11.99 mmol, 1.2 eq) under nitrogen. Then the mixture was stirred at 130° C. for 12 hours. The mixture was diluted with water (200 mL), filtered and then extracted with ethyl acetate (200 mL×3), washed with brine (200 mL), dried over anhydrous sodium sulfate, filtered and then concentrated. The residue was purified by reversed phase flash chromatography (formic acid). tert-Butyl N-[(1S)-1-[4-(2-methylimidazol-1-yl)phenyl]ethyl]carbamate (250 mg, 0.83 mmol, 8% yield) was obtained as a yellow oil.

tert-Butyl N-[(1S)-1-[4-(2-methylimidazol-1-yl)phenyl]ethyl]carbamate was converted to the final compound as detailed in the schemes below using procedures described above for exemplary compounds 47 and 64.

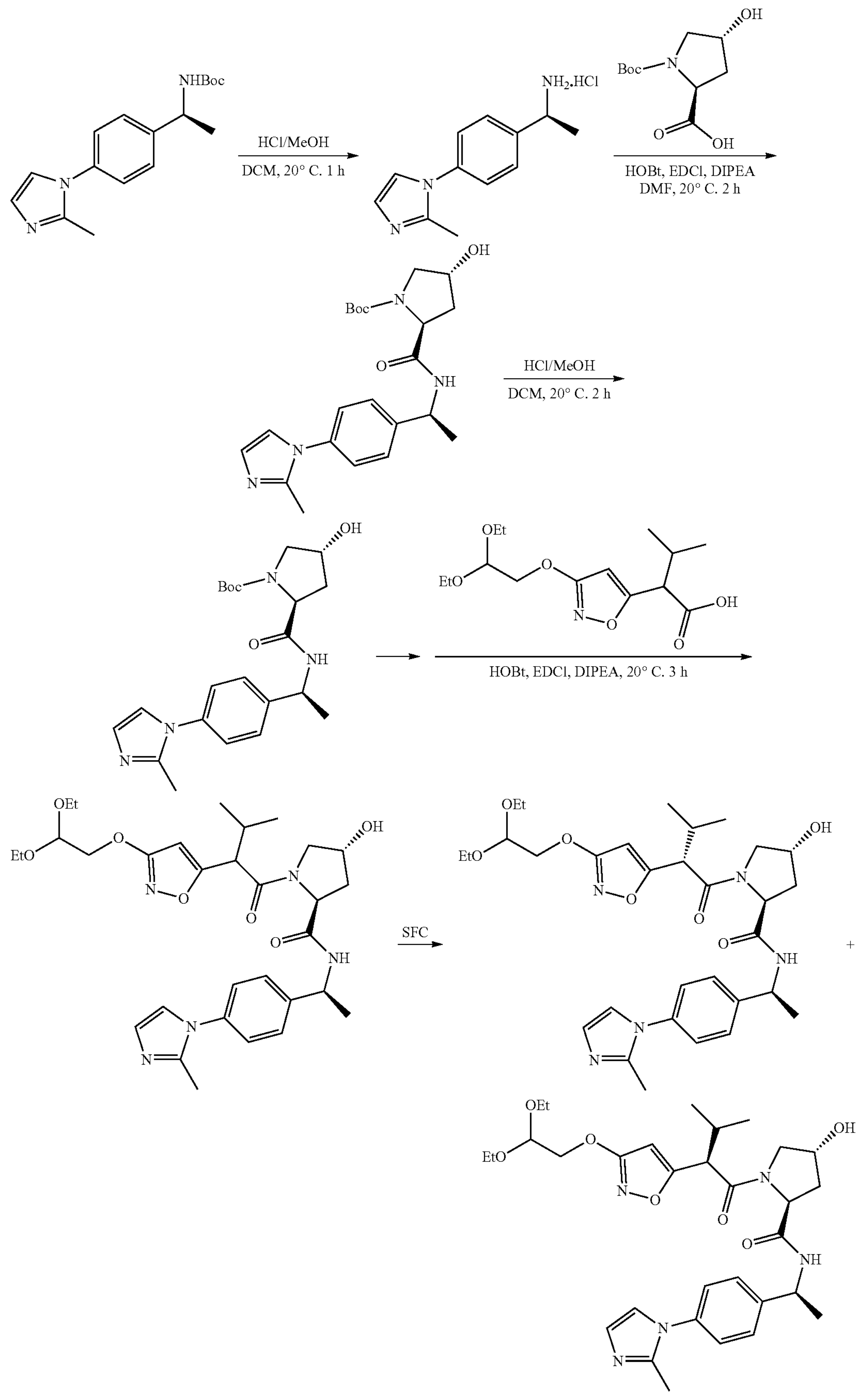
HCl/MeOH
DCM, 20° C. 1 h
HOBt, EDCl, DIPEA
DMF, 20° C. 2 h
HCl/MeOH
DCM, 20° C. 2 h
HOBt, EDCl, DIPEA, 20° C. 3 h
SFC
+

-continued
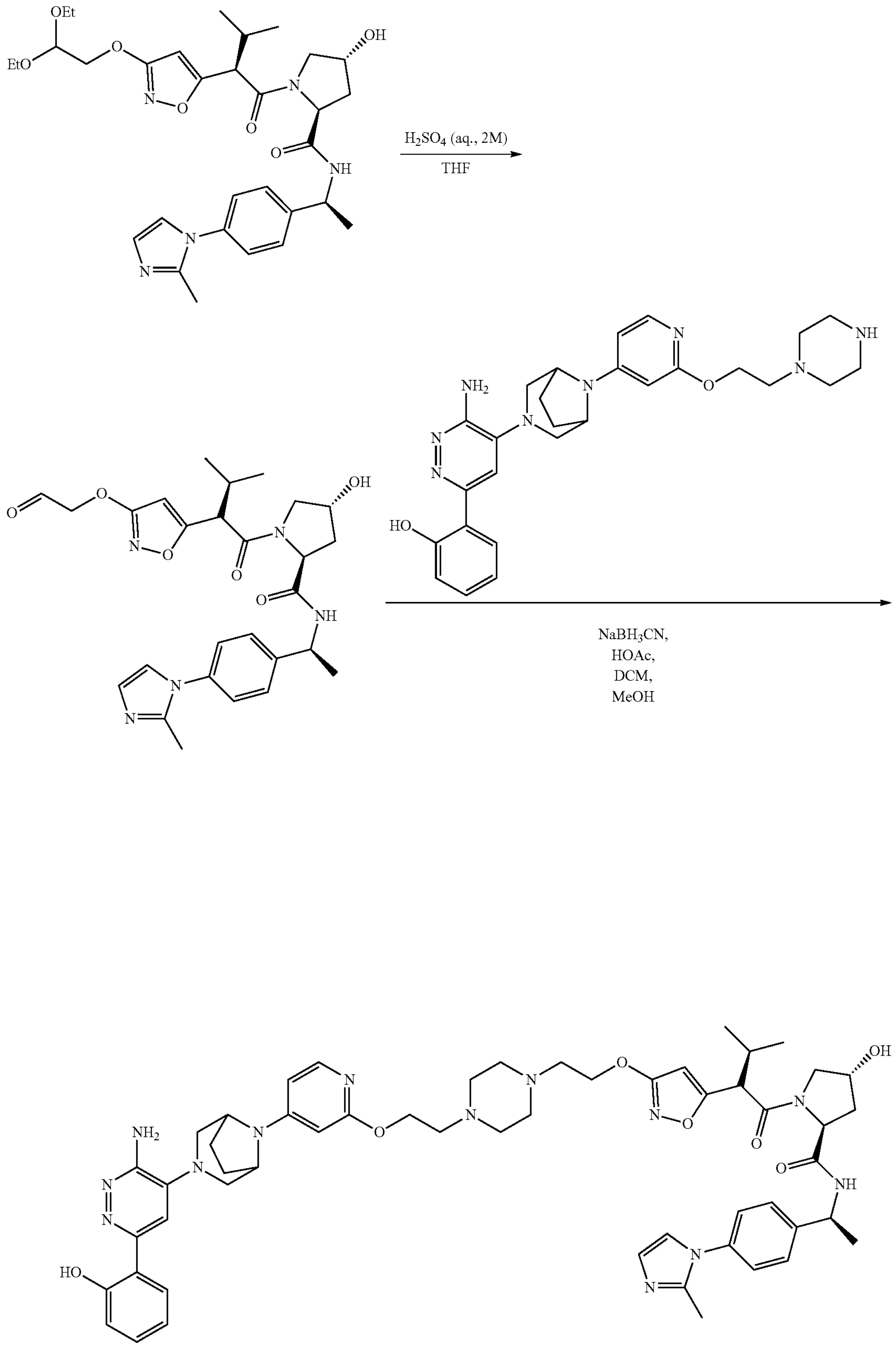
Ex. 76

Exemplary compound 75 was prepared using analogous procedures.

Exemplary Synthesis of Exemplary Compound 116 dried over anhydrous sodium sulfate, filtered and concentrated under reduced pressure to produce the desired compound (R,E)-N-(1-(6-bromopyridin-3-yl)ethylidene)-2-methylpropane-2-sulfinamide (16 g, 43.27 mmol, 87% yield) as a light yellow solid.

Ex. 116

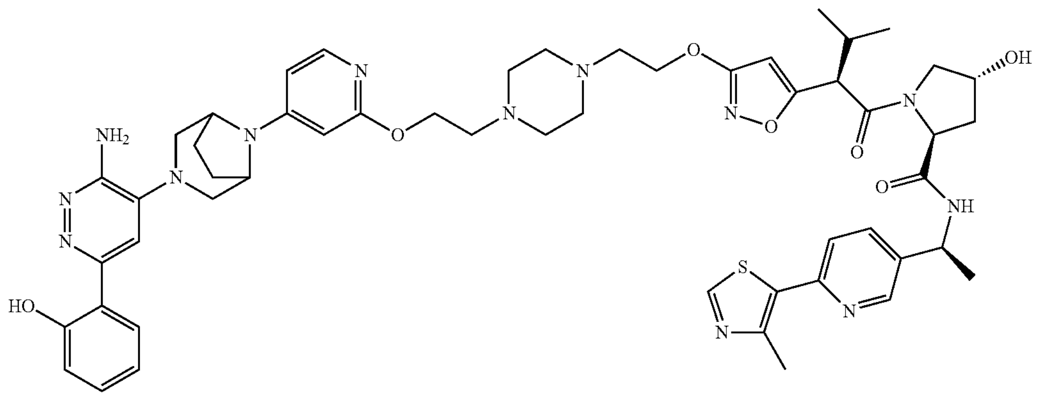

Step 1

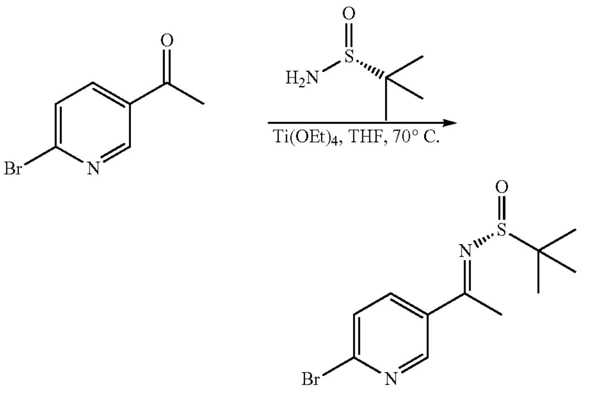

To a solution of 1-(6-bromo-3-pyridyl)ethanone (11.88 g, 59.41 mmol, 1.2 eq) and tetraethoxytitanium (22.58 g, 99.01 mmol, 2 eq) in tetrahydrofuran (50 mL) was added (R)-2-methylpropane-2-sulfinamide (6 g, 49.50 mmol, 1 eq) under nitrogen. The reaction mixture was stirred at 70° C. for 12 hours. The reaction mixture was quenched by addition water (30 mL), and then further diluted with water (100 mL), filtered and extracted with ethyl acetate (80 mL×3). The combined organic layers were washed with brine (100 mL), Step 2

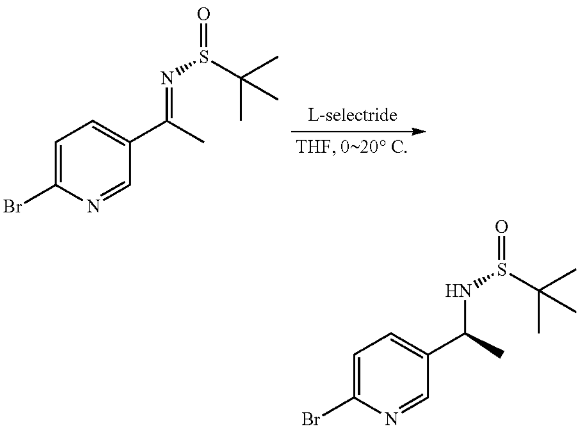

To a solution of (R,E)-N-(1-(6-bromopyridin-3-yl)ethylidene)-2-methylpropane-2-sulfinamide (16 g, 52.77 mmol, 1 eq) in tetrahydrofuran (160 mL) was added L-selectride (1 M, 158 mL, 3 eq) at 0° C. The reaction mixture was warmed up and stirred at 20° C. for 3 hours. The reaction mixture was quenched by addition water (100 mL), and then further diluted with water (100 mL), filtered and extracted with ethyl acetate (100 mL×3). The combined organic layers were washed with brine (100 mL), dried over anhydrous sodium sulfate, filtered and concentrated under reduced pressure to give crude product which was purified by recrystallization from petroleum ether:ethyl acetate=1:1 (10 mL). Then the residue was purified by semi-preparative reverse phase HPLC (FA condition: column: Phenomenex Synergi Max-RP 250*50 mm*10 um; mobile phase: [water (0.225% FA)-ACN]; B %: 20%-55%, 30 min). N-[(1S)-1-(6-bromo-3-pyridyl)ethyl]-2-methyl-propane-2-sulfinamide (4.7 g, 12.89 mmol, 24% yield) was obtained as a white solid.

Step 3

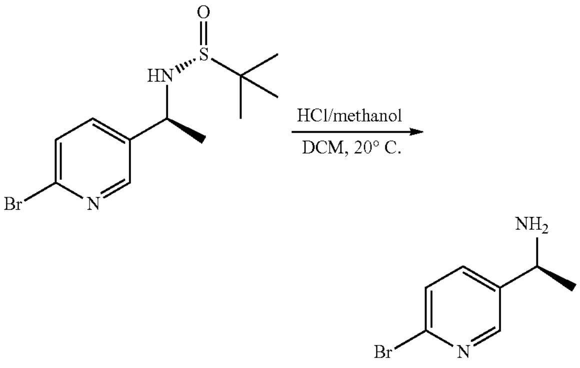

To a solution of N-[(1S)-1-(6-bromo-3-pyridyl)ethyl]-2-methyl-propane-2-sulfinamide (2.6 g, 8.52 mmol, 1 eq) in dichloromethane (20 mL) was added hydrochloric acid/methanol (4 M, 21.3 mL, 10 eq). The reaction mixture was stirred at 20° C. for 0.15 hours. The reaction mixture was concentrated under reduced pressure to give (1S)-1-(6-bromo-3-pyridyl)ethanamine (1.9 g, crude, hydrochloride) as a white solid.

Step 4

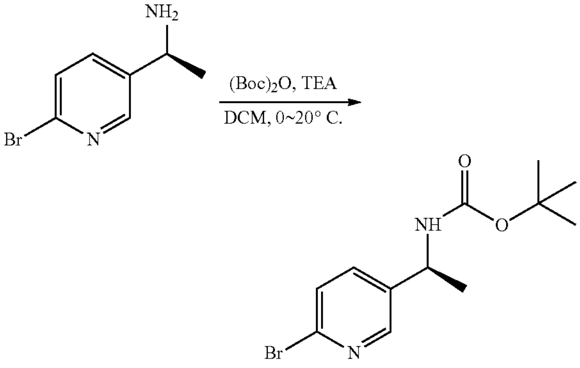

To a solution of (1S)-1-(6-bromo-3-pyridyl)ethanamine hydrochloride (1.9 g, 8.00 mmol, 1 eq,) in dichloromethane (20 mL) was added triethylamine (2.43 g, 24.00 mmol, 3.34 mL, 3 eq) at 0° C. for 0.5 hour followed by di-tert-butyl dicarbonate (2.62 g, 12.00 mmol, 2.76 mL, 1.5 eq) at 0° C. for 0.5 hours. The reaction mixture was stirred at 20° C. for 12 hours. The reaction mixture was quenched by the addition of water (20 mL), and then further diluted with water 60 mL, and extracted with ethyl acetate (80 mL×3). The combined organic layers were washed with brine (100 mL), dried over anhydrous sodium sulfate, filtered and concentrated under reduced pressure to give a residue which was purified by silica gel chromatography (petroleum ether:ethyl acetate=50:1 to 3:1). tert-Butyl N-[(1S)-1-(6-bromo-3-pyridyl)ethyl]carbamate (2.2 g, 7.06 mmol, 88% yield) was obtained as a white solid.

Step 5

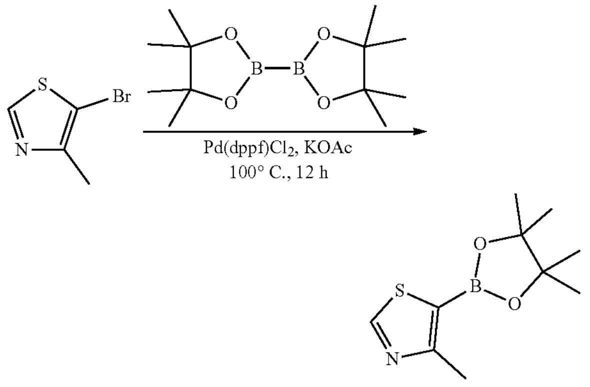

To a solution of 5-bromo-4-methyl-thiazole (800 mg, 4.49 mmol, 1 eq) and 4,4,5,5-tetramethyl-2-(4,4,5,5-tetramethyl-1,3,2-dioxaborolan-2-yl)-1,3,2-dioxaborolane (1.37 g, 5.39 mmol, 1.2 eq) in dioxane (10 mL) was added 1,1'-bis(diphenylphosphino)ferrocene-palladium(II)dichloride (164 mg, 0.22 mmol, 0.05 eq) and potassium acetate (882 mg, 8.99 mmol, 2 eq). The reaction mixture was stirred at 100° C. for 12 h. The reaction mixture was filtered and concentrated under reduced pressure to give 4-methyl-5-(4,4,5,5-tetramethyl-1,3,2-dioxaborolan-2-yl)thiazole (1 g, crude) as a brown oil which was used without purification.

Step 6

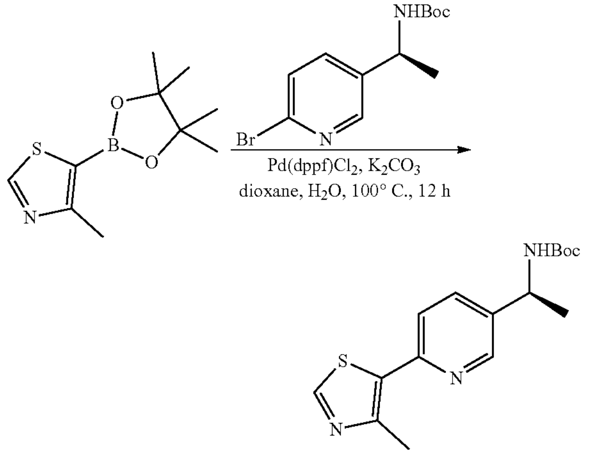

To a solution of 4-methyl-5-(4,4,5,5-tetramethyl-1,3,2-dioxaborolan-2-yl)thiazole (617 mg, 2.74 mmol, 1.5 eq) and tert-butyl N-[(1S)-1-(6-bromo-3-pyridyl)ethyl]carbamate (550 mg, 1.83 mmol, 1 eq) in dioxane (12 mL) and water (2 mL) was added 1,1'-bis(diphenylphosphino)ferrocene-palladium(II)dichloride (134 mg, 0.18 mmol, 0.1 eq) and potassium carbonate (505 mg, 3.65 mmol, 2 eq). The reaction mixture was stirred at 100° C. for 12 hours. The reaction mixture was quenched by addition water (10 mL), and then diluted with water (30 mL), filtered and extracted with ethyl acetate (30 mL×3). The combined organic layers were washed with brine (60 mL), dried over anhydrous sodium sulfate, filtered and concentrated under reduced pressure to give a residue which was purified by prep-TLC (petroleum ether:ethyl acetate=1:1). The desired compound tert-butyl N-[(1S)-1-[6-(4-methylthiazol-5-yl)-3-pyridyl]ethyl]carbamate (200 mg, 0.62 mmol, 34% yield) was obtained as a light yellow solid.

tert-Butyl N-[(1S)-1-[6-(4-methylthiazol-5-yl)-3-pyridyl]ethyl]carbamate was converted to the final compound as described above for exemplary compound 76.

Exemplary compound 160 was prepared using analogous procedures.

Exemplary Synthesis of Exemplary Compound 117

Ex. 117

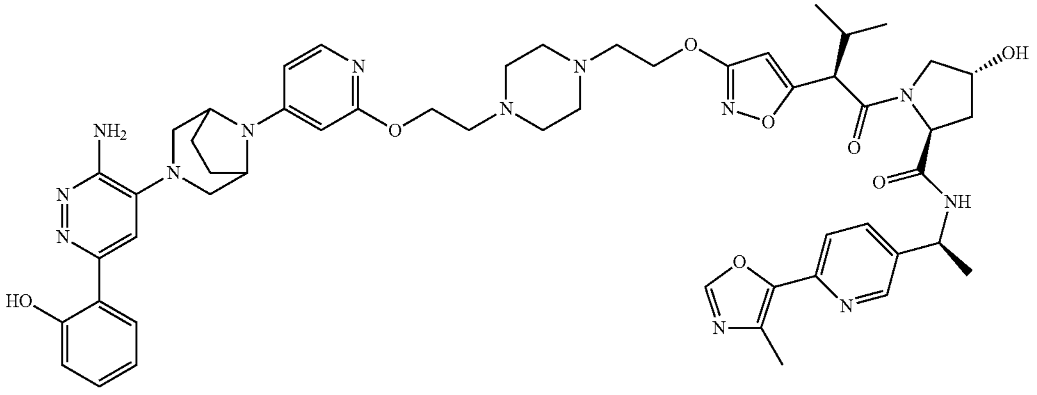

Step 1

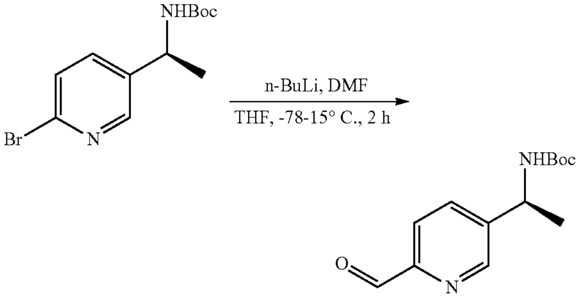

To a solution of tert-butyl N-[(1S)-1-(6-bromo-3-pyridyl)ethyl]carbamate (1 g, 3.32 mmol, 1 eq) in tetrahydrofuran (10 mL) was added n-butyllithium (2.5 M, 2.9 mL, 2.2 eq) at −78° C. The mixture was stirred at −78° C. for 0.5 hours, then to the mixture was added N,N-dimethylformamide (728 mg, 9.96 mmol, 0.8 mL, 3 eq) at −78° C., and the mixture was stirred at −78° C. for 0.5 hour. Then mixture was warmed to 15° C. for 1 hour. The reaction mixture was quenched by the addition of saturated ammonium chloride (10 mL), and then diluted with water (20 mL), filtered and extracted with ethyl acetate (30 mL×3). The combined organic layers were washed with brine (60 mL), dried over anhydrous sodium sulfate, filtered and concentrated under reduced pressure to give a residue. The residue was purified by silica gel chromatography (petroleum ether:ethyl acetate=10:1 to 1:1). The desired compound tert-butyl N-[(1S)-1-(6-formyl-3-pyridyl)ethyl]carbamate (550 mg, 2.20 mmol, 66% yield) was obtained as a light yellow solid.

Step 2

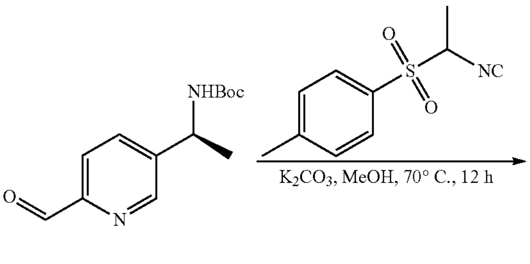

-continued

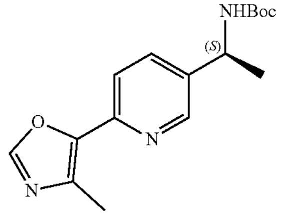

To a solution of tert-butyl N-[(1S)-1-(6-formyl-3-pyridyl)ethyl]carbamate (550 mg, 2.20 mmol, 1 eq) and 1-(1-isocyanoethylsulfonyl)-4-methyl-benzene (506 mg, 2.42 mmol, 1.1 eq) in methanol (10 mL) was added potassium carbonate (607 mg, 4.39 mmol, 2 eq). The reaction mixture was stirred at 70° C. for 12 hours. The reaction mixture was quenched by addition water (20 mL), and then diluted with water (10 mL), filtered and extracted with ethyl acetate (30 mL×3). The combined organic layers were washed with brine (60 mL), dried over sodium sulfate, filtered and concentrated under reduced pressure to give a residue. The residue was purified by silica gel chromatography (petroleum ether:ethyl acetate=50:1 to 1:1). The desired compound tert-butyl N-[(1S)-1-[6-(4-methyloxazol-5-yl)-3-pyridyl]ethyl]carbamate (570 mg, 1.65 mmol, 75% yield, 87% purity) was obtained as a white solid.

tert-Butyl N-[(1S)-1-[6-(4-methyloxazol-5-yl)-3-pyridyl]ethyl]carbamate was converted to the final compound as described for exemplary compound 76.

Exemplary compounds 161, 229, and 230 were prepared using analogous procedures.

Exemplary Synthesis of Exemplary Compound 81

Ex. 81

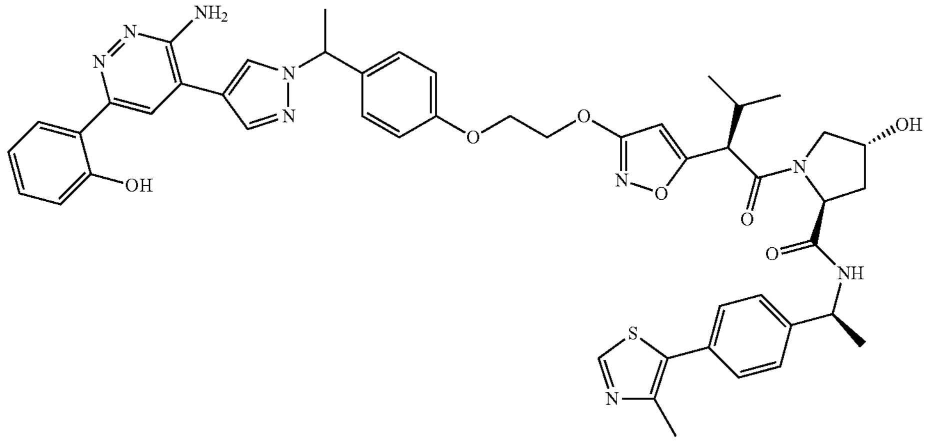

Step 1

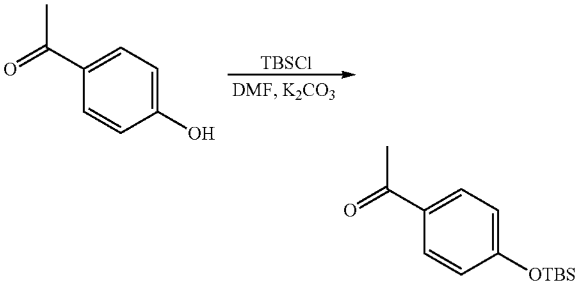

Into a 250-mL round-bottom flask was placed 1-(4-hydroxyphenyl)ethan-1-one (6.0 g, 44.08 mmol, 1 equiv), tert-butyl(chloro)dimethylsilane (10 g, 66.1 mmol, 1.5 equiv), and $K_2CO_3$ (12 g, 88.14 mmol, 2 equiv) in DMF (100 mL). The resulting mixture was stirred overnight at room temperature. The reaction was then quenched by the addition of water (100 mL). The resulting mixture was extracted with dichloromethane (100 mL×3), and the organic layers were combined, dried over anhydrous sodium sulfate and concentrated under reduced pressure. The residue was applied onto a silica gel column eluting with ethyl acetate/petroleum ether (1:10). This resulted in 5.2 g (47%) of 1-[4-[(tert-butyldimethylsilyl)oxy]phenyl]ethan-1-one as off-white solid.

Step 2

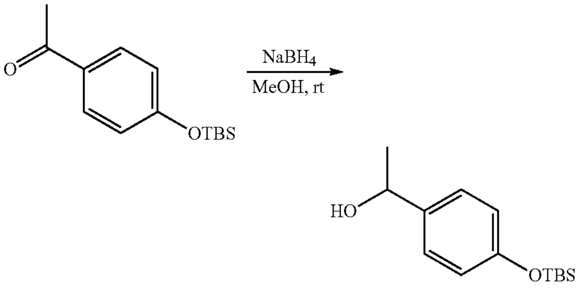

Into a 250-mL round-bottom flask, was placed 1-[4-[(tert-butyldimethylsilyl)oxy]phenyl]ethan-1-one (5 g, 20.0 mmol, 1 equiv) in MeOH (100 mL), to which was added sodium borohydride (1.5 g, 39.94 mmol, 2 equiv) in portions at room temperature. The resulting solution was stirred for 5 h at room temperature, and then concentrated under reduced pressure. The residue was applied onto a silica gel column eluting with ethyl acetate/petroleum ether (1/1). This resulted in 3.8 g (76%) of 1-[4-[(tert-butyldimethylsilyl)oxy]phenyl]ethan-1-ol as a yellow oil.

Step 3

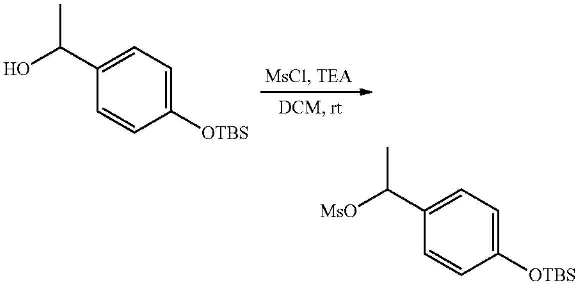

Into a 250-mL round-bottom flask, was placed 1-[4-[(tert-butyldimethylsilyl)oxy]phenyl]ethan-1-ol (3.8 g, 15.05 mmol, 1 equiv) and TEA (6.1 g, 60.21 mmol, 4 equiv) in dichloromethane (100 mL), to which was added methanesulfonyl chloride (2.1 g, 18.07 mmol, 1.20 equiv) slowly at room temperature. The resulting mixture was stirred for 2 hours at room temperature. The mixture was concentrated under reduced pressure. This resulted in 3.6 g of crude 1-[4-[(tert-butyldimethylsilyl)oxy]phenyl]ethyl methanesulfonate as a yellow solid.

Step 4

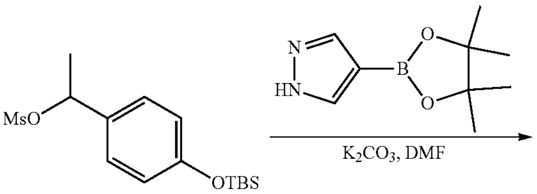

-continued

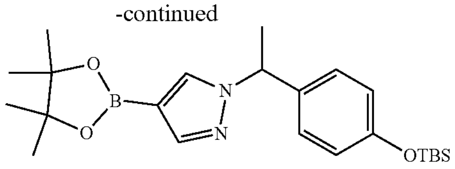

Into a 250-mL round-bottom flask, was placed 1-[4-[(tert-butyldimethylsilyl)oxy]phenyl]ethyl methanesulfonate (5.0 g, 15.13 mmol, 1 equiv), 2-(cyclopenta-1,4-dien-1-yl)-4,4,5,5-tetramethyl-1,3,2-dioxaborolane (3.5 g, 18.17 mmol, 1.20 equiv), and $K_2CO_3$ (6.3 g, 45.38 mmol, 3 equiv) in DMF (150 mL) under nitrogen atmosphere. The resulting mixture was stirred overnight at 90° C. The reaction was then quenched by the addition of water (150 mL). The resulting mixture was extracted with dichloromethane (150 mL×3), and the organic layers were combined, dried over anhydrous sodium sulfate and concentrated under reduced pressure. The residue was applied onto a silica gel column eluting with ethyl acetate/petroleum ether (1:5). This resulted in 600 mg (9%) of 1-(1-[4-[(tert-butyldimethylsilyl)oxy]phenyl]ethyl)-4-(4,4,5,5-tetramethyl-1,3,2-dioxaborolan-2-yl)-1H-pyrazole as a yellow solid.

1-(1-[4-[(tert-Butyldimethylsilyl)oxy]phenyl]ethyl)-4-(4,4,5,5-tetramethyl-1,3,2-dioxaborolan-2-yl)-1H-pyrazole was converted to the final compound according to the scheme below using procedures analogous to those described for other examples.

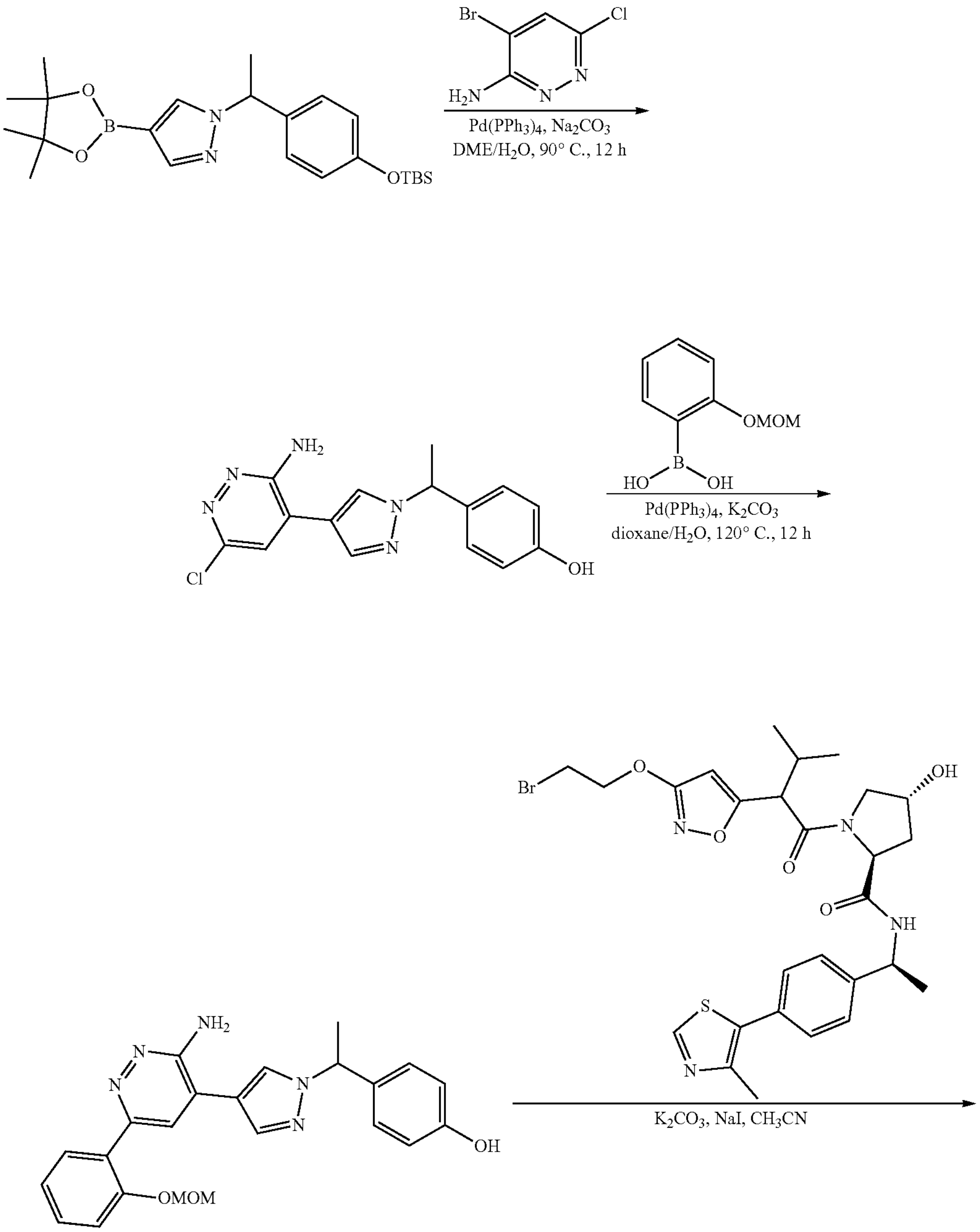

-continued
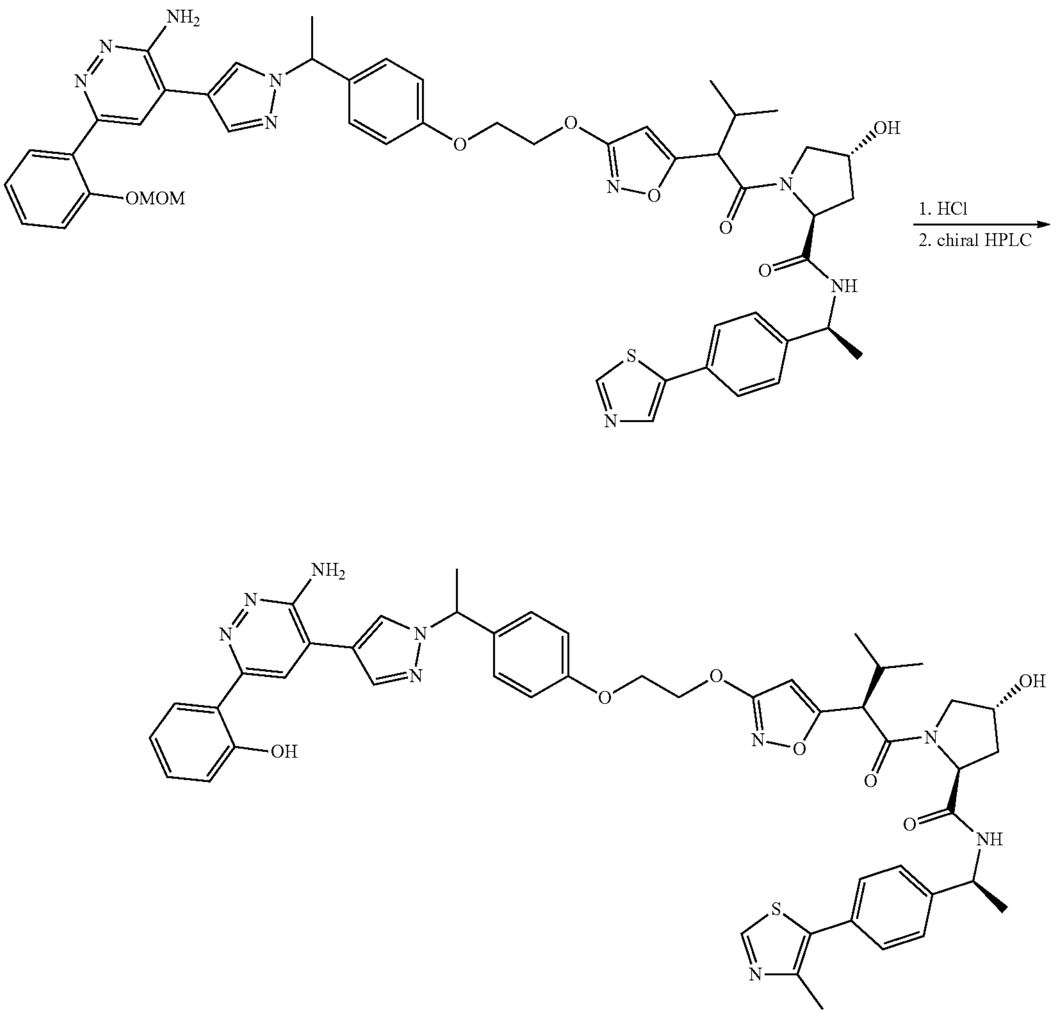
Ex. 81
Exemplary compound 156 was prepared using analogous procedures.
Exemplary Synthesis of Exemplary Compound 162
Ex. 162
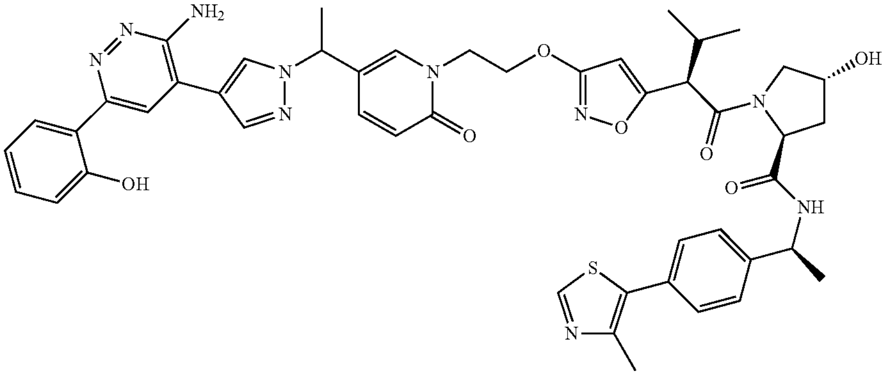

Step 1

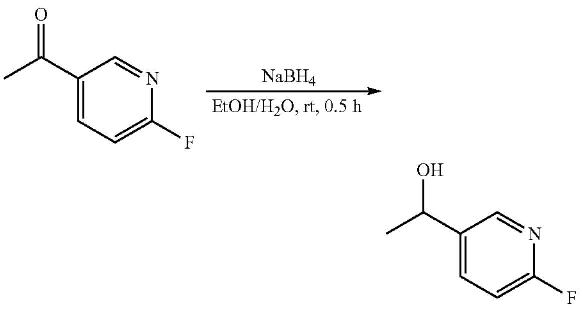

Into a 250-mL round-bottom flask, was placed a solution of 1-(6-fluoropyridin-3-yl)ethan-1-one (4.17 g, 29.97 mmol, 1 equiv) in EtOH (60 mL). The solution was cooled to 0° C. in a water/ice bath, and the solution of sodium borohydride (2.27 g, 61.65 mmol, 2.06 equiv) in $H_2O$ (10 mL) was added dropwise. The resulting mixture was stirred for 0.5 hour at room temperature. The reaction mixture was carefully quenched with water (400 mL) and extracted with ethyl acetate (200 mL×3). The organic layers were combined, dried over anhydrous sodium sulfate and concentrated under vacuum. The residue was applied onto a silica gel column eluting with ethyl acetate/petroleum ether (1:1). This resulted in 3.87 g (91%) of 1-(6-fluoropyridin-3-yl)ethan-1-ol as a light yellow oil.

Step 2

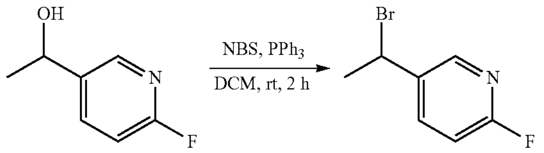

Into a 500-mL 3-necked round-bottom flask purged and maintained under an inert atmosphere of nitrogen, was placed 1-(6-fluoropyridin-3-yl)ethan-1-ol (4.06 g, 28.76 mmol, 1 equiv) in dichloromethane (200 mL). The solution was cooled to 0° C. in water/ice bath, and $PPh_3$ (11.28 g, 43.01 mmol, 1.50 equiv) and NBS (7.66 g, 43.04 mmol, 1.50 equiv) were added sequentially at 0° C. The resulting solution was stirred for 2 h at room temperature. The reaction mixture was concentrated under vacuum. The residue was applied onto a silica gel column eluting with ethyl acetate/petroleum ether (1:9). This resulted in 5.83 g (99%) of 5-(1-bromoethyl)-2-fluoropyridine as a light yellow liquid.

Step 3

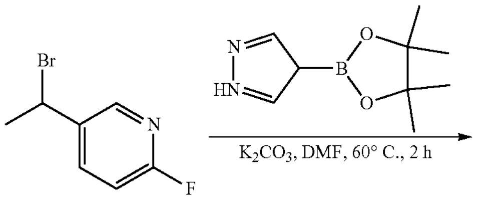

-continued

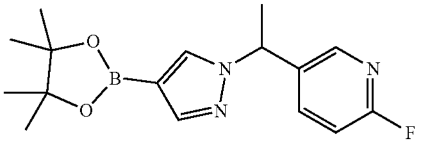

Into a 100-mL round-bottom flask, was placed a solution of 5-(1-bromoethyl)-2-fluoropyridine (3.06 g, 15.00 mmol, 1 equiv), 4-(4,4,5,5-tetramethyl-1,3,2-dioxaborolan-2-yl)-1H-pyrazole (3.20 g, 16.49 mmol, 1.10 equiv), and $K_2CO_3$ (4.15 g, 30.03 mmol, 2.00 equiv) in DMF (50 mL). The resulting mixture was stirred for 2 hours at 60° C. in an oil bath. The reaction mixture was cooled to room temperature and diluted with water (400 mL). The mixture was extracted with ethyl acetate (100 mL×4), and the combined organic layer was washed with brine (300 mL×2), dried over anhydrous sodium sulfate and concentrated under vacuum. This resulted in 3.43 g (72%) of 2-fluoro-5-[1-[4-(4,4,5,5-tetramethyl-1,3,2-dioxaborolan-2-yl)-1H-pyrazol-1-yl]ethyl]pyridine as a light yellow solid.

Step 4

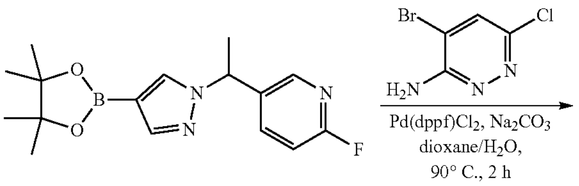

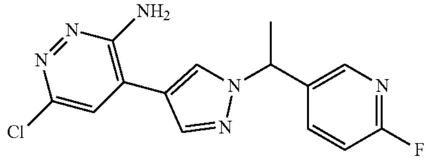

Into a 100-mL round-bottom flask purged and maintained under an inert atmosphere of nitrogen, was placed 2-fluoro-5-[1-[4-(4,4,5,5-tetramethyl-1,3,2-dioxaborolan-2-yl)-1H-pyrazol-1-yl]ethyl]pyridine (2.54 g, 8.01 mmol, 1 equiv, 4-bromo-6-chloropyridazin-3-amine (2.00 g, 9.60 mmol, 1.20 equiv), $Na_2CO_3$ (2.12 g, 20.00 mmol, 2.50 equiv), and $Pd(dppf)Cl_2 \cdot CH_2C12$ (327 mg, 0.40 mmol, 0.05 equiv) in dioxane (50 mL) and $H_2O$ (8 mL). The resulting mixture was stirred for 2 hours at 90° C. in an oil bath. The reaction mixture was cooled to room temperature and diluted with water (200 mL). The mixture was extracted with ethyl acetate (300 mL×2), and the organic layers were combined, dried over anhydrous sodium sulfate and concentrated under vacuum. The residue was applied onto a silica gel column eluting with dichloromethane/methanol (20:1). This resulted in 1.88 g (74%) of 6-chloro-4-[1-[1-(6-fluoropyridin-3-yl)ethyl]-1H-pyrazol-4-yl]pyridazin-3-amine as a brown solid.

Step 5

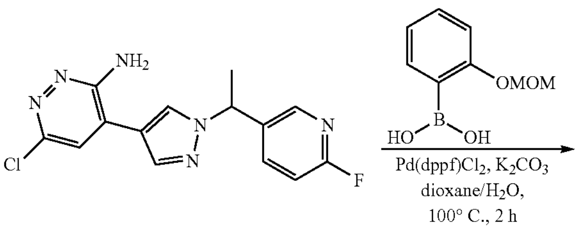

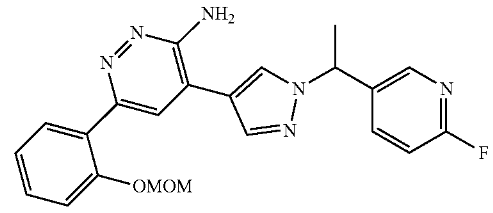

Into a 30-mL sealed tube purged and maintained with an inert atmosphere of nitrogen, was placed 6-chloro-4-[1-[1-(6-fluoropyridin-3-yl)ethyl]-1H-pyrazol-4-yl]pyridazin-3-amine (765 mg, 2.40 mmol, 1 equiv), [2-(methoxymethoxy) phenyl]boronic acid (524 mg, 2.88 mmol, 1.20 equiv), $K_2CO_3$ (829 mg, 6.00 mmol, 2.50 equiv), and Pd(dppf) $Cl_2 \cdot CH_2C12$ (196 mg, 0.24 mmol, 0.10 equiv) in dioxane (18 mL) and $H_2O$ (3 mL). The resulting mixture was stirred for 2 hours at 100° C. in an oil bath. The reaction mixture was cooled to room temperature and concentrated under vacuum. The residue was applied onto a silica gel column eluting with dichloromethane/methanol (20:1). This resulted in 860 mg (85%) of 4-[1-[1-(6-fluoropyridin-3-yl)ethyl]-1H-pyrazol-4-yl]-6-[2-(methoxymethoxy)phenyl]pyridazin-3-amine as a brown solid.

Step 6

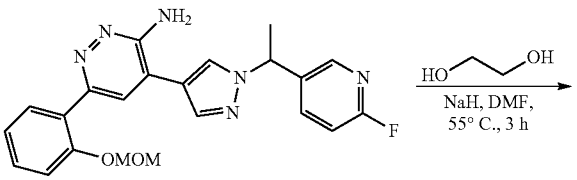

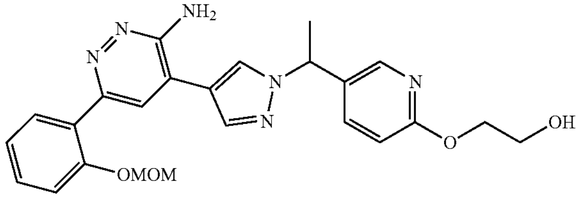

Into a 50-mL round-bottom flask purged and maintained under an inert atmosphere of nitrogen, was placed ethane-1,2-diol (1.48 g, 23.84 mmol, 10.03 equiv) in DMF (15 mL). The solution was cooled to 0° C. in water/ice bath and to this was added NaH (0.76 g, 19.00 mmol, 7.99 equiv, 60%) in portions at 0° C. The resulting mixture was stirred for 1.5 hours at room temperature, after which a solution of 4-[1-[1-(6-fluoropyridin-3-yl)ethyl]-1H-pyrazol-4-yl]-6-[2-(methoxymethoxy)phenyl]pyridazin-3-amine (1.00 g, 2.38 mmol, 1 equiv) in DMF (5 mL) was added dropwise at 0° C. The reaction mixture was stirred for an additional 3 hours while the temperature was maintained at 55° C. in an oil bath. The reaction mixture was cooled to room temperature, and then quenched by the addition of water (200 mL). The resulting mixture was extracted with ethyl acetate (300 mL×2). The combined organic layers were washed with brine (200 mL×2), dried over anhydrous sodium sulfate and concentrated under vacuum. The residue was applied onto a silica gel column eluting with dichloromethane/methanol (15:1). This resulted in 361 mg (33%) of 2-([5-[1-(4-[3-amino-6-[2-(methoxymethoxy)phenyl]pyridazin-4-yl]-1H-pyrazol-1-yl)ethyl]pyridin-2-yl]oxy)ethan-1-ol as a light yellow solid.

Step 7

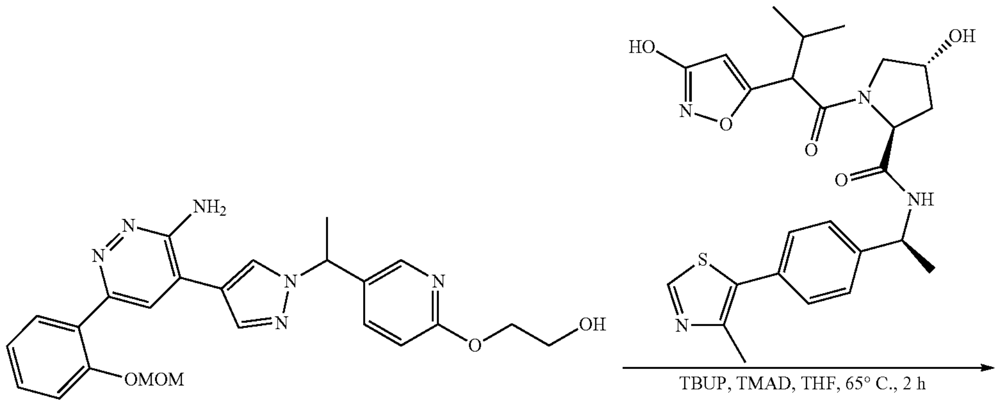

-continued

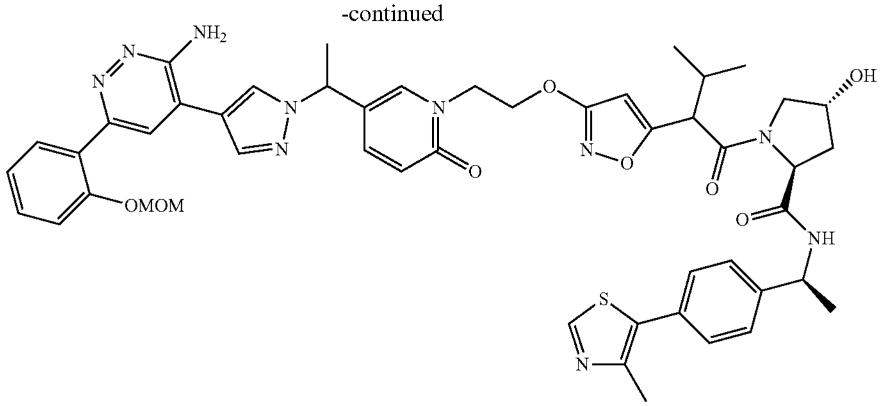

Into a 50-mL round-bottom flask purged and maintained with an inert atmosphere of nitrogen, was placed a solution of tetramethylazodicarboxamide (861 mg, 5.00 mmol, 10.00 equiv) and tributylphosphine (1.01 g, 4.99 mmol, 9.98 equiv) in THF (15 mL) at 0° C. To the mixture was added a mixture of 2-([5-[1-(4-[3-amino-6-[2-(methoxymethoxy) phenyl]pyridazin-4-yl]-1H-pyrazol-1-yl)ethyl]pyridin-2-yl] oxy)ethan-1-ol (231.3 mg, 0.50 mmol, 1 equiv) and (2S, 4R)-4-hydroxy-1-[2-(3-hydroxy-1,2-oxazol-5-yl)-3-methylbutanoyl]-N-[(1S)-1-[4-(4-methyl-1,3-thiazol-5-yl) phenyl]ethyl]pyrrolidine-2-carboxamide (249 mg, 0.50 mmol, 1.00 equiv). The resulting solution was stirred for 10 minutes at 0° C., and then stirred for an additional 2 hours at 50° C. in an oil bath. The reaction mixture was cooled to room temperature and diluted with water (150 mL). The resulting mixture was extracted with ethyl acetate (150 mL), and the organic layer was washed with brine (150 mL×2), dried over anhydrous sodium sulfate and concentrated under vacuum. The residue was applied onto a silica gel column eluting with dichloromethane/methanol (10/1). The obtained product was further purified by Prep-HPLC with the following conditions: Column, XBridge Prep OBD C18 Column, 19×150 mm, 5 um; mobile phase, water (with 10 mmol/L $NH_4HCO_3$) and acetonitrile, 35% ACN up to 53% in 8 min. This resulted in 68 mg (14%) of (2S,4R)-1-(2-(3-(2-(5-(1-(4-(3-amino-6-(2-(methoxymethoxy)phenyl) pyridazin-4-yl)-1H-pyrazol-1-yl)ethyl)-2-oxopyridin-1 (2H)-yl)ethoxy)isoxazol-5-yl)-3-methylbutanoyl)-4-hydroxy-N—((S)-1-(4-(4-methylthiazol-5-yl)phenyl)ethyl) pyrrolidine-2-carboxamide as an off-white solid.

(2S,4R)-1-(2-(3-(2-(5-(1-(4-(3-Amino-6-(2-(methoxymethoxy)phenyl)pyridazin-4-yl)-1H-pyrazol-1-yl) ethyl)-2-oxopyridin-1(2H)-yl)ethoxy)isoxazol-5-yl)-3-methylbutanoyl)-4-hydroxy-N—((S)-1-(4-(4-methylthiazol-5-yl)phenyl)ethyl)pyrrolidine-2-carboxamide was converted to the final compound using procedures analogous to those described for other examples above.

Exemplary compound 157 was preparing using analogous procedures.

Exemplary Synthesis of Exemplary Compound 100

Step 1

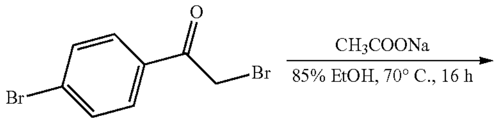

-continued

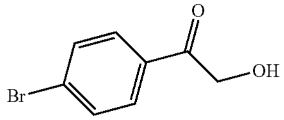

Into a stirred mixture of ethanol (350 mL, 7.60 mmol, 0.04 equiv) and water (60 mL, 3.33 mmol, 0.02 equiv) at room temperature was added anhydrous sodium acetate (18 g, 264.71 mmol, 1.47 equiv) in portions under nitrogen atmosphere. The resulting mixture was stirred for 16 hours at 70° C. under nitrogen atmosphere. The resulting mixture was concentrated under reduced pressure. The resulting mixture was diluted with water (500 mL). The aqueous layer was extracted with ethyl acetate (300 mL×2). The residue was washed with brine (100 mL×2), dried and concentrated under reduced pressure. The residue was purified by silica gel column chromatography eluting with ethyl acetate/petroleum ether (1:5) to afford 1-(4-bromophenyl)-2-hydroxyethan-1-one (32 g, 83%) as a white solid.

Step 2

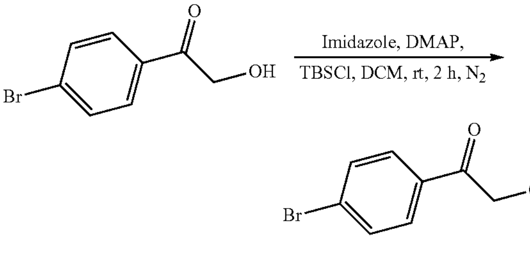

Into a 1 L round-bottom flask were added 1-(4-bromophenyl)-2-hydroxyethan-1-one (32 g, 148.8 mmol, 1 equiv), methylene chloride (500 mL), imidazole (30 g, 440.7 mmol, 2.96 equiv), 4-dimethylaminopyridine (1.8 g, 14.73 mmol, 0.10 equiv) and tert-butyldimethylsilyl chloride (26.8 g, 177.8 mmol, 1.19 equiv) at room temperature under nitrogen atmosphere. The resulting mixture was stirred for 2 hours at room temperature under nitrogen atmosphere. The reaction was quenched with water at room temperature. The resulting mixture was extracted with methylene chloride (200 mL×3). The combined organic layers were washed with brine (100 mL×2), dried over anhydrous sodium sulfate and concentrated under reduced pressure. The residue was purified by silica gel column chromatography eluting with ethyl acetate/ petroleum ether (1:20) to afford 1-(4-bromophenyl)-2-[(tert-butyldimethylsilyl)oxy]ethan-1-one (29 g, 59%) as a light yellow solid.

Step 3

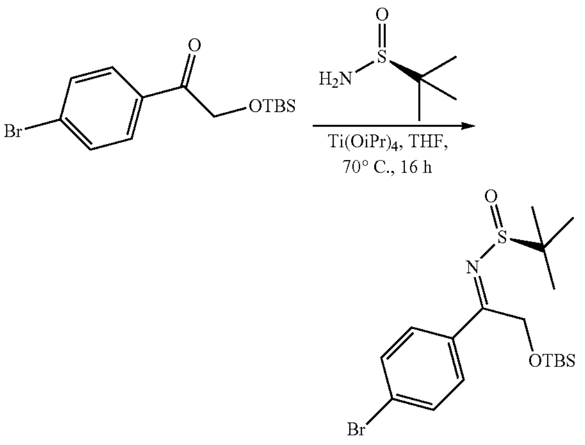

Into a 1 L 3-neck round-bottom flask were added 1-(4-bromophenyl)-2-[(tert-butyldimethylsilyl)oxy]ethan-1-one (27 g, 81.99 mmol, 1 equiv), tetrahydrofuran (500 mL) and (S)-2-methylpropane-2-sulfinamide (19.5 g, 160.9 mmol, 1.96 equiv) at room temperature. To the stirred solution was added Ti(i-PrO)$_4$ (70 g, 246.5 mmol, 3.01 equiv) dropwise at room temperature under nitrogen atmosphere. The resulting mixture was stirred for 16 hours at 70° C. under nitrogen atmosphere. The mixture was allowed to cool down to room temperature. The resulting mixture was filtered, and the filter cake was washed with ethyl acetate (200 mL×2). The combined organic layers were washed with brine (200 mL), dried over anhydrous sodium sulfate and concentrated under reduced pressure. The residue was purified by silica gel column chromatography eluting with ethyl acetate/petroleum ether (1:15) to afford (S)—N-[(1Z)-1-(4-bromophenyl)-2-[(tert-butyldimethylsilyl)oxy]ethylidene]-2-methylpropane-2-sulfinamide (16 g, 45%) as a yellow oil.

Step 4

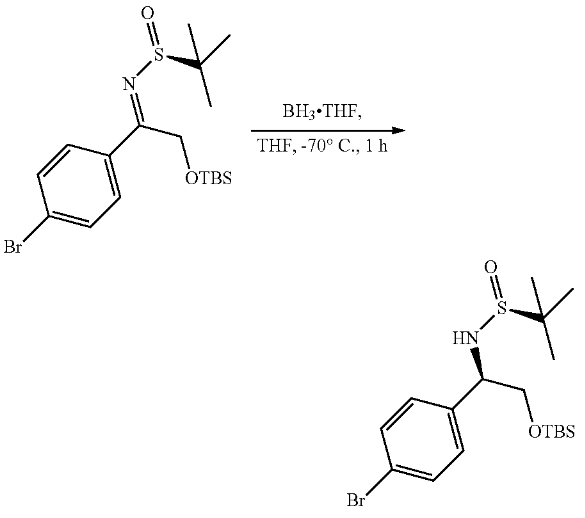

Into a 500 mL 3-neck round-bottom flask were added (S)—N-[(1Z)-1-(4-bromophenyl)-2-[(tert-butyldimethylsilyl)oxy]ethylidene]-2-methylpropane-2-sulfinamide (15 g, 34.68 mmol, 1 equiv) and tetrahydrofuran (150 mL) at room temperature. To the stirred solution was added $BH_3$.THF (52 mL, 52 mmol, 1.5 equiv) dropwise at −70° C. under nitrogen atmosphere. The resulting mixture was stirred for 1 hour at −70° C. under nitrogen atmosphere. The reaction was quenched with methanol at room temperature. The resulting mixture was filtered, and the filter cake was washed with ethyl acetate (100 mL×2). The filtrate was washed with brine (50 mL×2), dried over anhydrous sodium sulfate and concentrated under reduced pressure. The residue was purified by silica gel column chromatography eluting with ethyl acetate/petroleum ether (1:2) to afford (S)—N-[(1R)-1-(4-bromophenyl)-2-[(tert-butyldimethylsilyl)oxy]ethyl]-2-methylpropane-2-sulfinamide (5.6 g, 37%) as a yellow solid.

Step 5

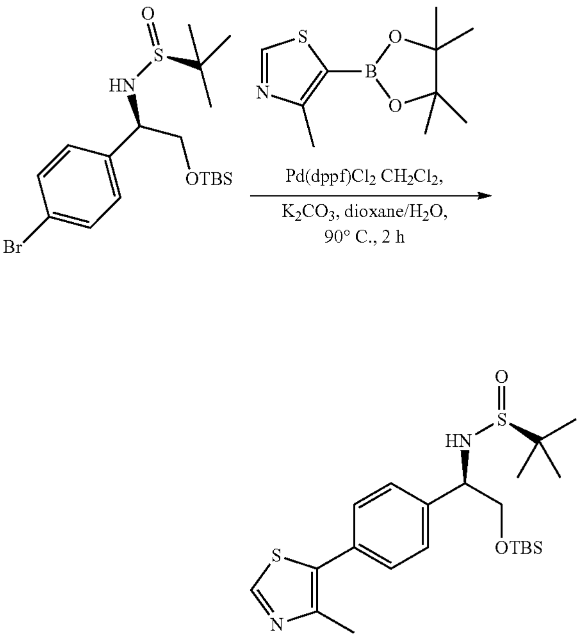

Into a 100-mL round-bottom flask purged and maintained with an inert atmosphere of nitrogen, was placed (S)—N-[(1R)-1-(4-bromophenyl)-2-[(tert-butyldimethylsilyl)oxy]ethyl]-2-methylpropane-2-sulfinamide (2.6 g, 5.98 mmol, 1.00 equiv), dioxane (30 mL), 4-methyl-5-(4,4,5,5-tetramethyl-1,3,2-dioxaborolan-2-yl)-1,3-thiazole (2 g, 8.88 mmol, 1.48 equiv), potassium carbonate (2.5 g, 18.09 mmol, 3.02 equiv), water (5 mL), and Pd(dppf)$Cl_2$·$CH_2$C12 (440 mg, 0.51 mmol, 0.09 equiv). The resulting solution was stirred for 2 hours at 90° C. The solids were filtered out. The filtrate was diluted with water (50 mL) and extracted with ethyl acetate (50 mL×3). The combined organic layers were washed with brine (35 mL×2), dried over anhydrous sodium sulfate and concentrated under vacuum. The residue was applied onto a silica gel column eluting with ethyl acetate/petroleum ether (1:5). This resulted in 2.5 g (92%) of (S)—N-[(1R)-2-[(tert-butyldimethylsilyl)oxy]-1-[4-(4-methyl-1,3-thiazol-5-yl)phenyl]ethyl]-2-methylpropane-2-sulfinamide as an orange oil.

Step 6

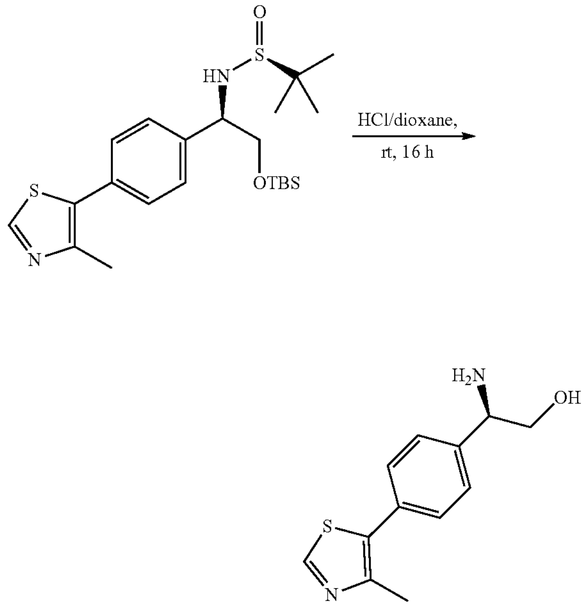

Into a 250-mL round-bottom flask, was placed (S)—N-[(1R)-2-[(tert-butyldimethylsilyl)oxy]-1-[4-(4-methyl-1,3-thiazol-5-yl)phenyl]ethyl]-2-methylpropane-2-sulfinamide (2.6 g, 5.74 mmol, 1.00 equiv) and hydrogen chloride in dioxane (100 mL, 4M). The resulting solution was stirred overnight at room temperature. The resulting mixture was concentrated under vacuum. This resulted in 1.5 g (96%) of (2R)-2-amino-2-[4-(4-methyl-1,3-thiazol-5-yl)phenyl]ethan-1-ol hydrochloride as a yellow oil.

Step 7

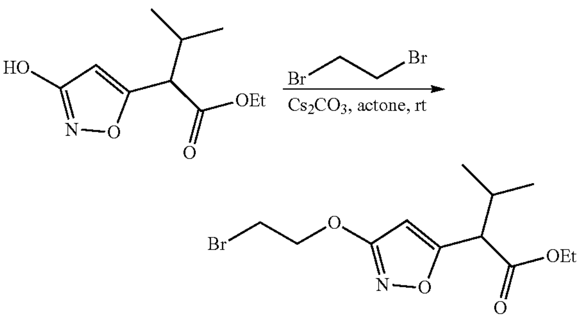

Into a 250-mL round-bottom flask, was placed ethyl 2-(3-hydroxy-1,2-oxazol-5-yl)-3-methylbutanoate (1 g, 4.69 mmol, 1 equiv), $Cs_2CO_3$ (4.5 g, 13.81 mmol, 3.0 equiv), and 1,2-dibromoethane (2.60 g, 13.84 mmol) in acetone (100 mL). The resulting mixture was stirred overnight at room temperature. The reaction was then quenched by water (100 mL). The resulting mixture was extracted with ethyl acetate (100 mL×3, and the organic layers were combined, dried over anhydrous sodium sulfate and concentrated under reduced pressure. The residue was applied onto a silica gel column eluting with ethyl acetate/petroleum ether (3:10). This resulted in 600 mg (40%) of ethyl 2-[3-(2-bromoethoxy)-1,2-oxazol-5-yl]-3-methylbutanoate as a light yellow oil.

(2R)-2-amino-2-[4-(4-methyl-1,3-thiazol-5-yl)phenyl]ethan-1-ol and ethyl 2-[3-(2-bromoethoxy)-1,2-oxazol-5-yl]-3-methylbutanoate were converted to (2S,4R)-1-(2-(3-(2-bromoethoxy)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide according to the scheme below using procedures described for other examples and obvious to those skilled in the art.

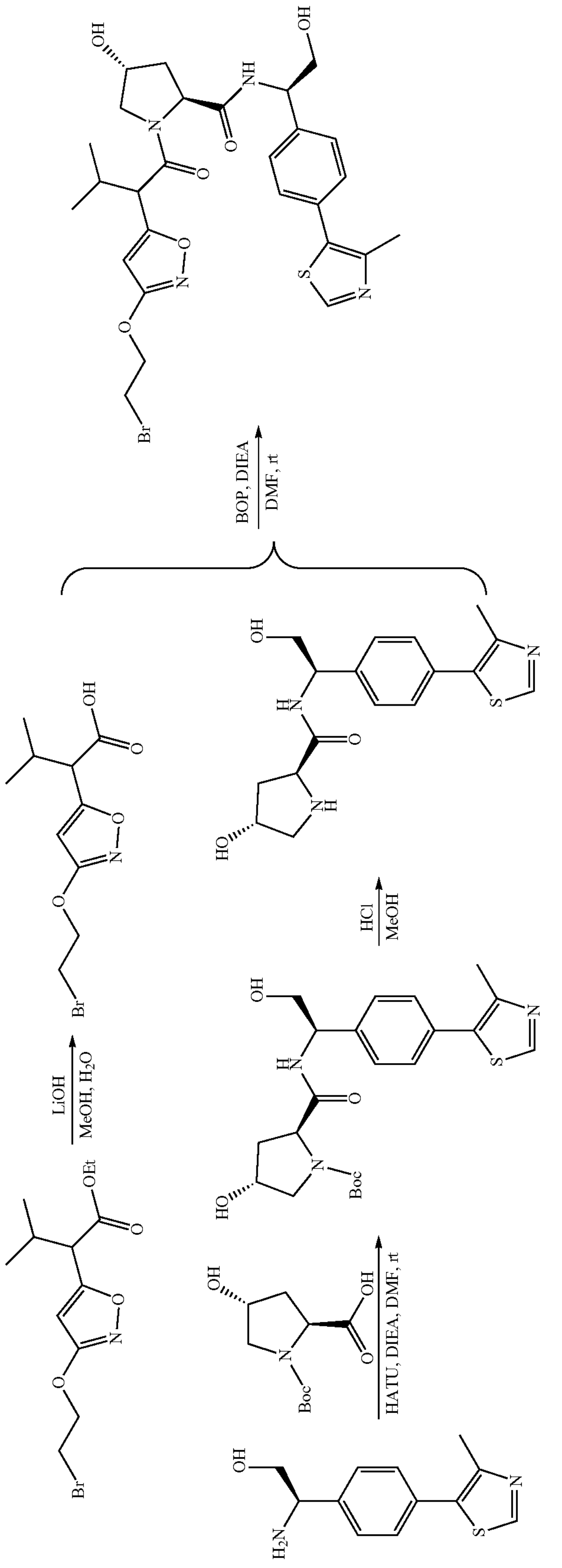
BOP, DIEA
DMF, rt
LiOH
MeOH, $H_2O$
HCl
MeOH
HATU, DIEA, DMF, rt (2S,4R)-1-(2-(3-(2-bromoethoxy)isoxazol-5-yl)-3-methylbutanoyl)-4-hydroxy-N—((R)-2-hydroxy-1-(4-(4-methylthiazol-5-yl)phenyl)ethyl)pyrrolidine-2-carboxamide was converted to the final compound using procedures analogous to those described for example Exemplary compound 47.

Exemplary compound 158 was prepared using analogous procedures.

Exemplary Synthesis of Exemplary Compound 115

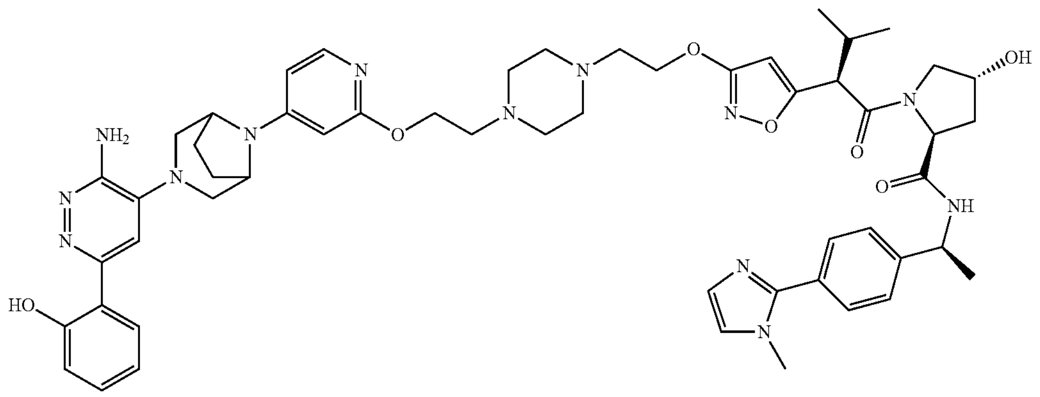 [SMILES: CC(C)[C@@H](C(=O)N1C[C@H](O)C[C@H]1C(=O)N[C@@H](C)c1ccc(-c2nccn2C)cc1)c1cc(OCCN2CCN(CCOc3cc(N4C5CCC4CN(c4cc(-c6ccccc6O)nnc4N)C5)ccn3)CC2)no1]

Step 1

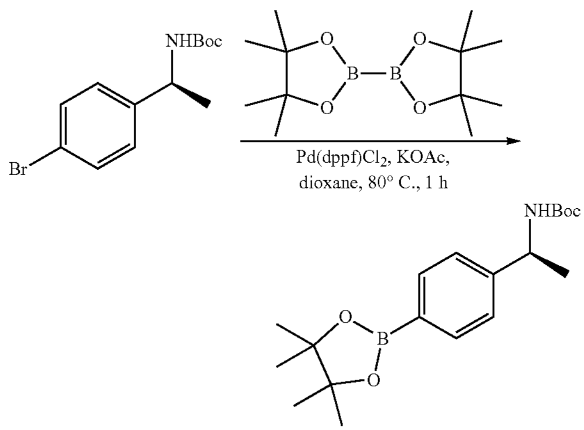

A flask was charged with tert-butyl N-[(1S)-1-(4-bromophenyl)ethyl]carbamate (1.4 g, 4.66 mmol, 1 eq), 4,4,5,5-tetramethyl-2-(4,4,5,5-tetramethyl-1,3,2-dioxaborolan-2-yl)-1,3,2-dioxaborolane (1.42 g, 5.60 mmol, 1.2 eq), (1,1'-bis(diphenylphosphino)ferrocene)palladium(II) dichloride (170 mg, 0.23 mmol, 0.05 eq), potassium acetate (915 mg, 9.33 mmol, 2 eq) and dioxane (30 mL). The mixture was purged with nitrogen for 10 min, then heated to 80° C. for 1 h. The reaction mixture was cooled to 20° C. and filtered through a pad of celite. The filtrate was concentrated in vacuum. The crude product was purified by column (petroleum ether:ethyl acetate=10:1). Tert-butyl N-[(1S)-1-[4-(4,4,5,5-tetramethyl-1,3,2-dioxaborolan-2-yl)phenyl]ethyl]carbamate (1.9 g, crude) was obtained as a colorless oil.

Step 2

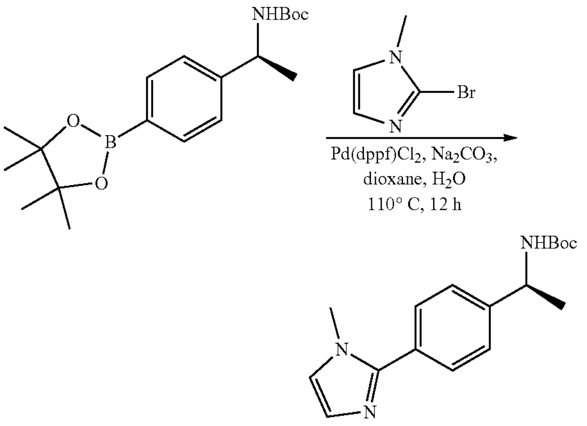

A flask was charged with tert-butyl N-[(1S)-1-[4-(4,4,5,5-tetramethyl-1,3,2-dioxaborolan-2-yl)phenyl]ethyl]carbamate (1.90 g, 5.47 mmol, 1.1 eq), 2-bromo-1-methylimidazole (800 mg, 4.97 mmol, 1 eq), (1,1'-bis(diphenylphosphino)ferrocene) palladium(II) dichloride (181 mg, 0.24 mmol, 0.05 eq), sodium carbonate (1.05 g, 9.94 mmol, 2 eq), dioxane (18 mL) and water (3 mL). The mixture was purged with nitrogen for 5 mins and heated to 110° C. for 12 h. The mixture was diluted with water (50 mL) and extracted with ethyl acetate (20 mL×3). The organic layer was washed with brine (50 mL), dried over sodium sulfate and filtered. The filtrate was concentrated in vacuum. The crude residue was purified by column chromatography (petroleum ether:ethyl acetate=1:0 to 3:1). Tert-butyl N-[(1S)-1-[4-(1-methylimidazol-2-yl)phenyl]ethyl] carbamate (850 mg, 2.82 mmol, 56% yield) was obtained as a grey solid.

Step 3

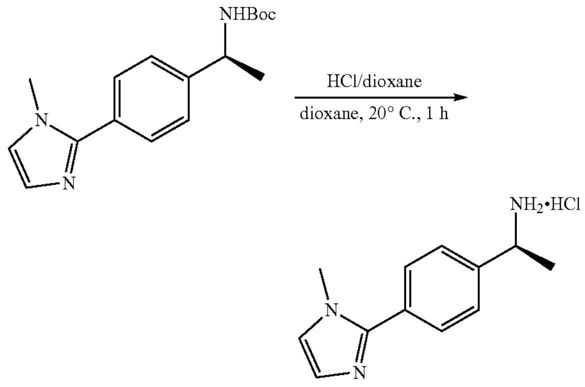

To a solution of tert-butyl N-[(1S)-1-[4-(1-methylimidazol-2-yl)phenyl]ethyl]carbamate (850 mg, 2.82 mmol, 1 eq) in dioxane (2 mL) was added hydrogen chloride solution (4 M in dioxane, 10 mL, 14.18 eq). The solution was stirred at 20° C. for 1 h. The solvent was removed in vacuum. (1S)-1-[4-(1-methylimidazol-2-yl)phenyl]ethanamine (670 mg, crude, hydrochloride) was obtained as a grey solid.

Step 4

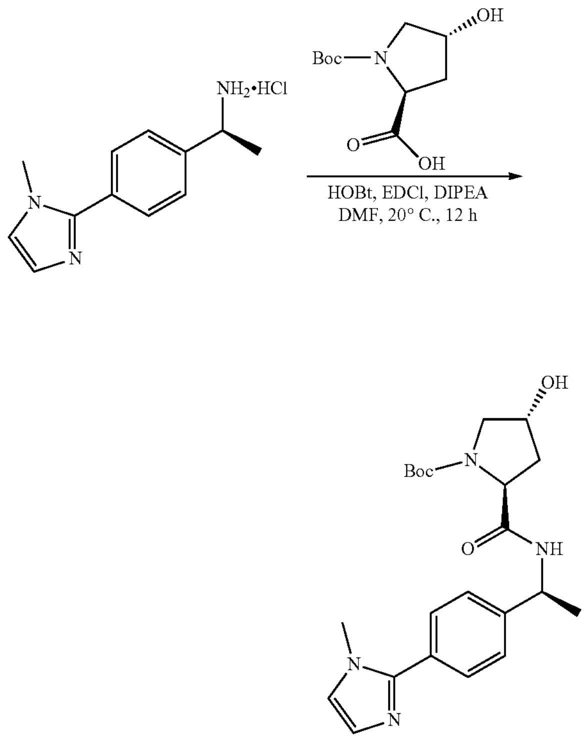

To a solution of (2S,4R)-1-tert-butoxycarbonyl-4-hydroxy-pyrrolidine-2-carboxylic acid (651 mg, 2.82 mmol, 1 eq) in N,N-dimethylformamide (2 mL) was added 1-hydroxybenzotriazole (456 mg, 3.38 mmol, 1.2 eq), 1-(3-dimethylaminopropyl)-3-ethylcarbodiimide hydrochloride (648 mg, 3.38 mmol, 1.2 eq). The solution was stirred at 20° C. for 0.5 h and then a solution of (1S)-1-[4-(1-methylimidazol-2-yl)phenyl]ethanamine (670 mg, 2.82 mmol, 1 eq, hydrochloride) and N,N-diisopropylethylamine (1.09 g, 8.46 mmol, 1.47 mL, 3 eq) in N,N-dimethylformamide (3 mL) was added to the solution and stirred for 11.5 h. The solvent was removed in vacuum. The crude residue was purified by semi-preparative reverse phase HPLC (column: Phenomenex Gemini C18 250*50 10 um; mobile phase: [water (0.05% ammonia hydroxide v/v)-ACN]; B %: 20%-50%, 20 min, 60% min). Tert-butyl (2S,4R)-4-hydroxy-2-[[(1S)-1-[4-(1-methylimidazol-2-yl)phenyl]ethyl]carbamoyl]pyrrolidine-1-carboxylate (800 mg, 1.93 mmol, 68% yield) was obtained as a colorless oil.

Step 5

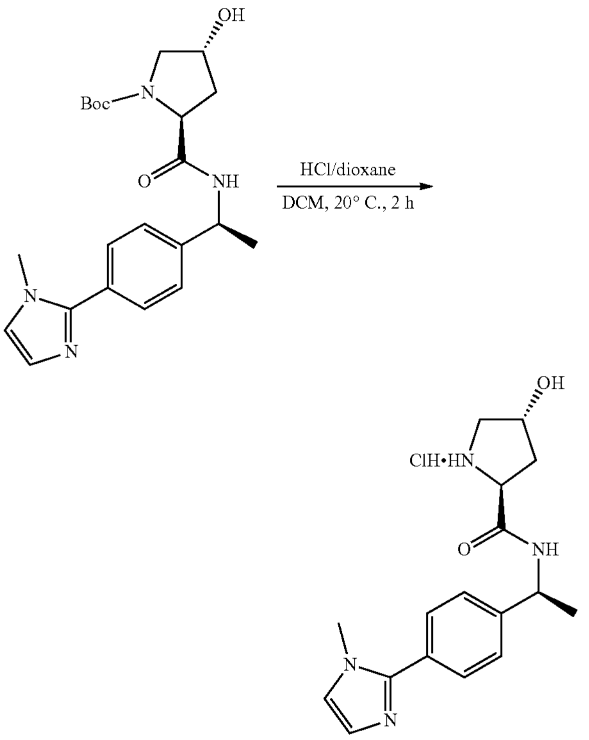

To a solution tert-butyl (2S,4R)-4-hydroxy-2-[[(1S)-1-[4-(1-methylimidazol-2-yl)phenyl]ethyl]carbamoyl]pyrrolidine-1-carboxylate (350 mg, 0.84 mmol, 1 eq) in dichloromethane (3 mL) was added hydrochloric acid/dioxane (4 M in dioxane, 3 mL, 14.21 eq). Then the reaction mixture was stirred at 20° C. for 2 h. The reaction mixture was concentrated under reduced pressure to give (2S,4R)-4-hydroxy-N-[(1S)-1-[4-(1-methylimidazol-2-yl)phenyl] ethyl]pyrrolidine-2-carboxamide (400 mg, crude, hydrochloride) as a light yellow solid.

(2S,4R)-4-hydroxy-N-[(1S)-1-[4-(1-methylimidazol-2-yl)phenyl]ethyl]pyrrolidine-2-carboxamide was converted to the final compound using procedures described for example Exemplary Compound 47.

Compound 159 was prepared using analogous procedures.

Exemplary Synthesis of Exemplary Compound 162

Exemplary Compound 162

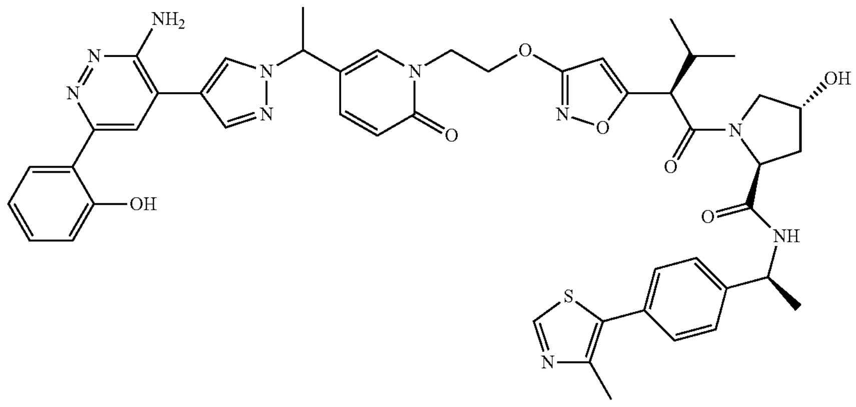

Step 1

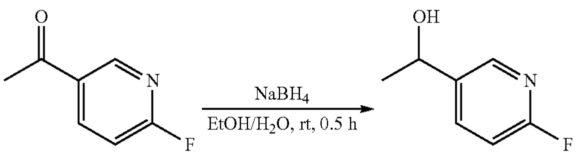

Into a 250-mL round-bottom flask, was placed a solution of 1-(6-fluoropyridin-3-yl)ethan-1-one (4.17 g, 29.97 mmol, 1 equiv) in EtOH (60 mL). The solution was cooled to 0° C. in a water/ice bath, and the solution of sodium borohydride (2.27 g, 61.65 mmol, 2.06 equiv) in $H_2O$ (10 mL) was added dropwise. The resulting mixture was stirred for 0.5 h at room temperature. The reaction mixture was carefully quenched with water (400 mL) and extracted with ethyl acetate (200 mL×3). The organic layers were combined, dried over anhydrous sodium sulfate and concentrated under vacuum. The residue was applied onto a silica gel column eluting with ethyl acetate/petroleum ether (1:1). This resulted in 3.87 g (91%) of 1-(6-fluoropyridin-3-yl)ethan-1-ol as a light yellow oil.

Step 2

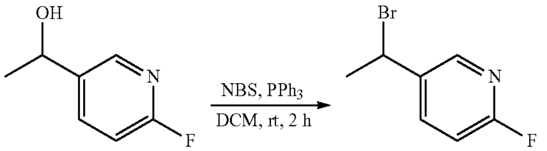

Into a 500-mL 3-necked round-bottom flask purged and maintained under an inert atmosphere of nitrogen, was placed 1-(6-fluoropyridin-3-yl)ethan-1-ol (4.06 g, 28.76 mmol, 1 equiv) in dichloromethane (200 mL). The solution was cooled to 0° C. in water/ice bath, and $PPh_3$ (11.28 g, 43.01 mmol, 1.50 equiv) and NBS (7.66 g, 43.04 mmol, 1.50 equiv) were added sequentially at 0° C. The resulting solution was stirred for 2 h at room temperature. The reaction mixture was concentrated under vacuum. The residue was applied onto a silica gel column eluting with ethyl acetate/petroleum ether (1:9). This resulted in 5.83 g (99%) of 5-(1-bromoethyl)-2-fluoropyridine as a light yellow liquid.

Step 3

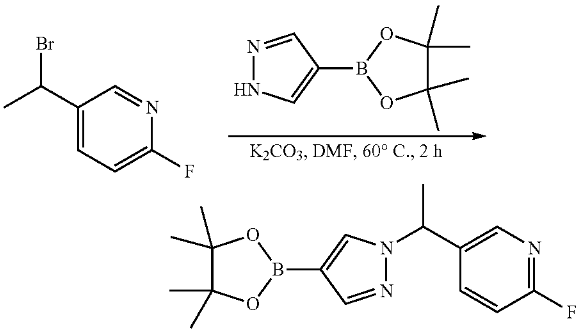

Into a 100-mL round-bottom flask, was placed a solution of 5-(1-bromoethyl)-2-fluoropyridine (3.06 g, 15.00 mmol, 1 equiv), 4-(4,4,5,5-tetramethyl-1,3,2-dioxaborolan-2-yl)-1H-pyrazole (3.20 g, 16.49 mmol, 1.10 equiv), and $K_2CO_3$ (4.15 g, 30.03 mmol, 2.00 equiv) in DMF (50 mL). The resulting mixture was stirred for 2 h at 60° C. in an oil bath. The reaction mixture was cooled to room temperature and diluted with water (400 mL). The mixture was extracted with ethyl acetate (100 mL×4), and the combined organic layer was washed with brine (300 mL×2), dried over anhydrous sodium sulfate and concentrated under vacuum. This resulted in 3.43 g (72%) of 2-fluoro-5-[1-[4-(4,4,5,5-tetramethyl-1,3,2-dioxaborolan-2-yl)-1H-pyrazol-1-yl]ethyl]pyridine as a light yellow solid.

Step 4

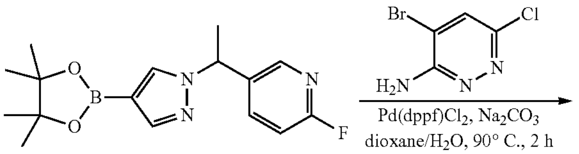

-continued

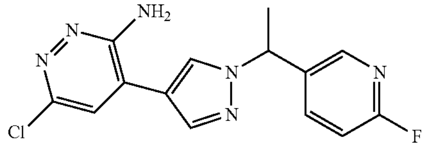

Into a 100-mL round-bottom flask purged and maintained under an inert atmosphere of nitrogen, was placed 2-fluoro-5-[1-[4-(4,4,5,5-tetramethyl-1,3,2-dioxaborolan-2-yl)-1H-pyrazol-1-yl]ethyl]pyridine (2.54 g, 8.01 mmol, 1 equiv, 4-bromo-6-chloropyridazin-3-amine (2.00 g, 9.60 mmol, 1.20 equiv), $Na_2CO_3$ (2.12 g, 20.00 mmol, 2.50 equiv), and $Pd(dppf)Cl_2 \cdot CH_2C12$ (327 mg, 0.40 mmol, 0.05 equiv) in dioxane (50 mL) and $H_2O$ (8 mL). The resulting mixture was stirred for 2 h at 90° C. in an oil bath. The reaction mixture was cooled to room temperature and diluted with water (200 mL). The mixture was extracted with ethyl acetate (300 mL×2), and the organic layers were combined, dried over anhydrous sodium sulfate and concentrated under vacuum. The residue was applied onto a silica gel column eluting with dichloromethane/methanol (20:1). This resulted in 1.88 g (74%) of 6-chloro-4-[1-[1-(6-fluoropyridin-3-yl)ethyl]-1H-pyrazol-4-yl]pyridazin-3-amine as a brown solid.

Step 5

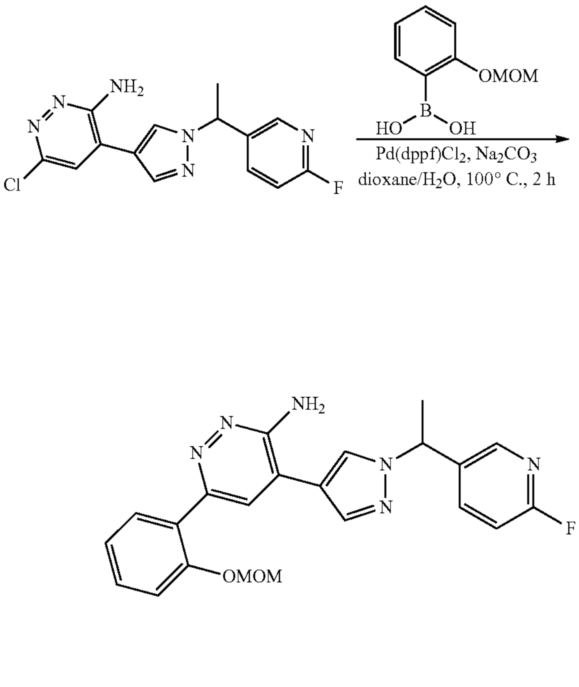

Into a 30-mL sealed tube purged and maintained with an inert atmosphere of nitrogen, was placed 6-chloro-4-[1-[1-(6-fluoropyridin-3-yl)ethyl]-1H-pyrazol-4-yl]pyridazin-3-amine (765 mg, 2.40 mmol, 1 equiv), [2-(methoxymethoxy) phenyl]boronic acid (524 mg, 2.88 mmol, 1.20 equiv), $K_2CO_3$ (829 mg, 6.00 mmol, 2.50 equiv), and Pd(dppf) $Cl_2 \cdot CH_2C12$ (196 mg, 0.24 mmol, 0.10 equiv) in dioxane (18 mL) and $H_2O$ (3 mL). The resulting mixture was stirred for 2 h at 100° C. in an oil bath. The reaction mixture was cooled to room temperature and concentrated under vacuum. The residue was applied onto a silica gel column eluting with dichloromethane/methanol (20:1). This resulted in 860 mg (85%) of 4-[1-[1-(6-fluoropyridin-3-yl)ethyl]-1H-pyrazol-4-yl]-6-[2-(methoxymethoxy)phenyl]pyridazin-3-amine as a brown solid.

Step 6

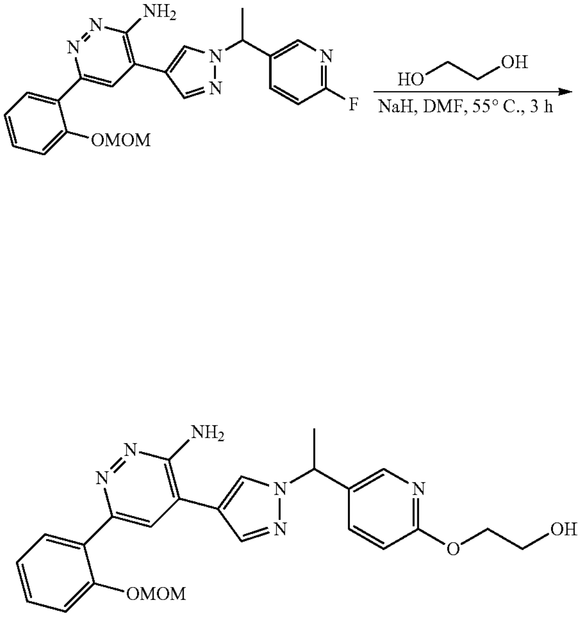

Into a 50-mL round-bottom flask purged and maintained under an inert atmosphere of nitrogen, was placed ethane-1,2-diol (1.48 g, 23.84 mmol, 10.03 equiv) in DMF (15 mL). The solution was cooled to 0° C. in water/ice bath and to this was added NaH (0.76 g, 19.00 mmol, 7.99 equiv, 60%) in portions at 0° C. The resulting mixture was stirred for 1.5 h at room temperature, after which a solution of 4-[1-[1-(6-fluoropyridin-3-yl)ethyl]-1H-pyrazol-4-yl]-6-[2-(methoxymethoxy)phenyl]pyridazin-3-amine (1.00 g, 2.38 mmol, 1 equiv) in DMF (5 mL) was added dropwise at 0° C. The reaction mixture was stirred for an additional 3 h while the temperature was maintained at 55° C. in an oil bath. The reaction mixture was cooled to room temperature, and then quenched by the addition of water (200 mL). The resulting mixture was extracted with ethyl acetate (300 mL×2). The combined organic layers were washed with brine (200 mL×2), dried over anhydrous sodium sulfate and concentrated under vacuum. The residue was applied onto a silica gel column eluting with dichloromethane/methanol (15:1). This resulted in 361 mg (33%) of 2-([5-[1-(4-[3-amino-6-[2-(methoxymethoxy)phenyl]pyridazin-4-yl]-1H-pyrazol-1-yl)ethyl]pyridin-2-yl]oxy)ethan-1-ol as a light yellow solid.

Step 7

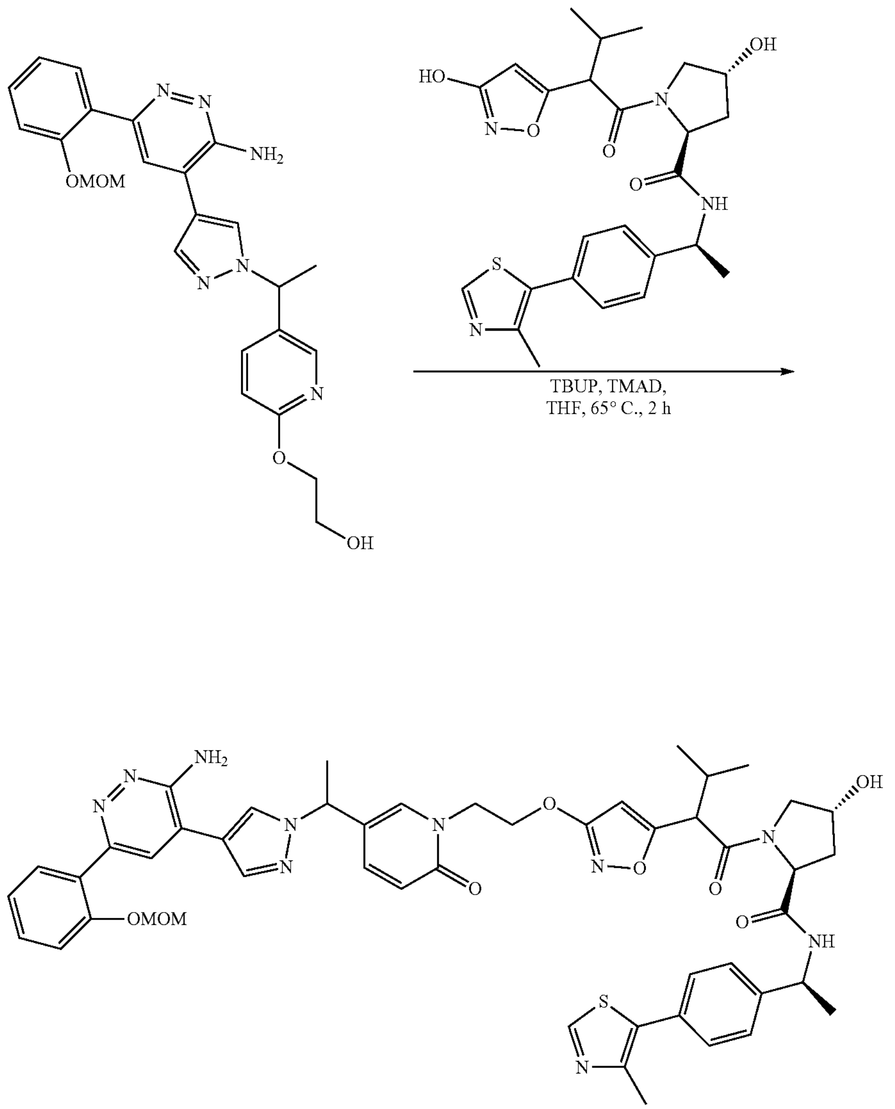

Into a 50-mL round-bottom flask purged and maintained with an inert atmosphere of nitrogen, was placed a solution of tetramethylazodicarboxamide (861 mg, 5.00 mmol, 10.00 equiv) and tributylphosphine (1.01 g, 4.99 mmol, 9.98 equiv) in THF (15 mL) at 0° C. To the mixture was added a mixture of 2-([5-[1-(4-[3-amino-6-[2-(methoxymethoxy) phenyl]pyridazin-4-yl]-1H-pyrazol-1-yl)ethyl]pyridin-2-yl] oxy)ethan-1-ol (231.3 mg, 0.50 mmol, 1 equiv) and (2S, 4R)-4-hydroxy-1-[2-(3-hydroxy-1,2-oxazol-5-yl)-3-methylbutanoyl]-N-[(1S)-1-[4-(4-methyl-1,3-thiazol-5-yl) phenyl]ethyl]pyrrolidine-2-carboxamide (249 mg, 0.50 mmol, 1.00 equiv). The resulting solution was stirred for 10 min at 0° C., and then stirred for an additional 2 h at 50° C. in an oil bath. The reaction mixture was cooled to room temperature and diluted with water (150 mL). The resulting mixture was extracted with ethyl acetate (150 mL), and the organic layer was washed with brine (150 mL×2), dried over anhydrous sodium sulfate and concentrated under vacuum. The residue was applied onto a silica gel column eluting with dichloromethane/methanol (10/1). The obtained product was further purified by Prep-HPLC with the following conditions: Column, XBridge Prep OBD C18 Column, 19×150 mm, 5 um; mobile phase, water (with 10 mmol/L $NH_4HCO_3$) and acetonitrile, 35% ACN up to 53% in 8 min. This resulted in 68 mg (14%) of (2S,4R)-1-(2-(3-(2-(5-(1-(4-(3-amino-6-(2-(methoxymethoxy)phenyl)pyridazin-4-yl)-1H-pyrazol-1-yl)ethyl)-2-oxopyridin-1(2H)-yl)ethoxy) isoxazol-5-yl)-3-methylbutanoyl)-4-hydroxy-N—((S)-1-(4-(4-methylthiazol-5-yl)phenyl)ethyl)pyrrolidine-2-carboxamide as an off-white solid.

(2S,4R)-1-(2-(3-(2-(5-(1-(4-(3-Amino-6-(2-(methoxymethoxy)phenyl)pyridazin-4-yl)-1H-pyrazol-1-yl) ethyl)-2-oxopyridin-1(2H)-yl)ethoxy)isoxazol-5-yl)-3-methylbutanoyl)-4-hydroxy-N—((S)-1-(4-(4-methylthiazol-5-yl)phenyl)ethyl)pyrrolidine-2-carboxamide was converted to the final compound using procedures analogous to those described for other examples above.

Exemplary compound 157 was prepared using analogous procedures.

Exemplary Synthesis of Exemplary Compound 82

Ex. 82

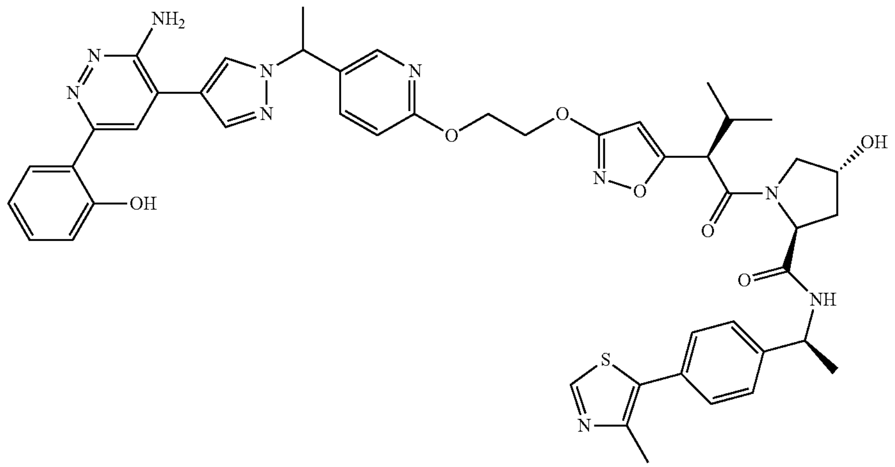

Step 1

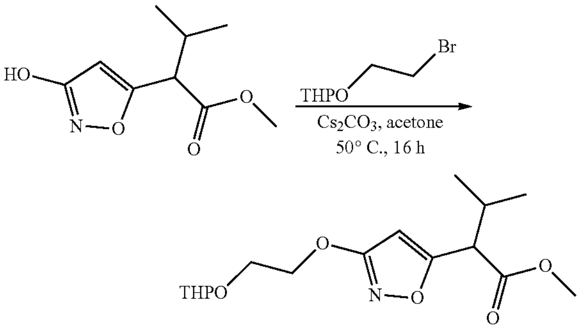

Into a 100-mL round-bottom flask, was placed methyl 2-(3-hydroxy-1,2-oxazol-5-yl)-3-methylbutanoate (498 mg, 2.50 mmol, 1 equiv), 2-(2-bromoethoxy)oxane (627.3 mg, 3.00 mmol, 1.20 equiv), $Cs_2CO_3$ (1.63 g, 5.00 mmol, 2.00 equiv), and NaI (37.5 mg, 0.25 mmol, 0.10 equiv) in acetone (20 mL). The resulting mixture was stirred for 16 hours at 50° C. in an oil bath. The reaction mixture was cooled to room temperature and diluted with water (150 mL). The mixture was extracted with ethyl acetate (100 mL×2), and the organic layers were combined, dried over anhydrous sodium sulfate and concentrated under vacuum. The residue was applied onto a silica gel column eluting with ethyl acetate/petroleum ether (1:9). This resulted in 570 mg (70%) of methyl 3-methyl-2-[3-[2-(oxan-2-yloxy)ethoxy]-1,2-oxazol-5-yl]butanoate as a light yellow oil.

Step 2

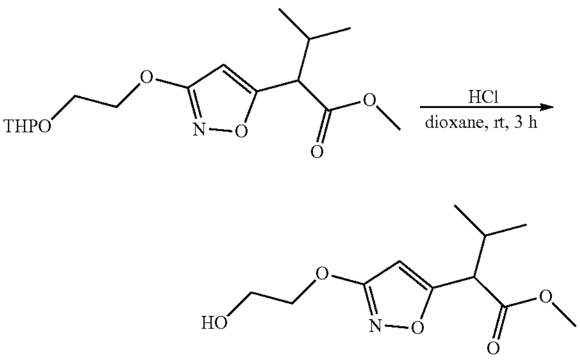

Into a 100-mL round-bottom flask, was placed methyl 3-methyl-2-[3-[2-(oxan-2-yloxy)ethoxy]-1,2-oxazol-5-yl] butanoate (520 mg, 1.59 mmol, 1 equiv) in dioxane (6 mL), to which was added HCl solution (4M in dioxane, 6 mL) at room temperature. The resulting solution was stirred for 3 hours at room temperature. The pH value of the solution was adjusted to 8 with saturated $NaHCO_3$. The resulting mixture was extracted with dichloromethane (100 mL×4), and the organic layers were combined, dried over anhydrous sodium sulfate and concentrated under vacuum. The residue was applied onto a silica gel column eluting with ethyl acetate/petroleum ether (1/1). This resulted in 332 mg (86%) of methyl 2-[3-(2-hydroxyethoxy)-1,2-oxazol-5-yl]-3-methylbutanoate as a light yellow oil.

Step 3

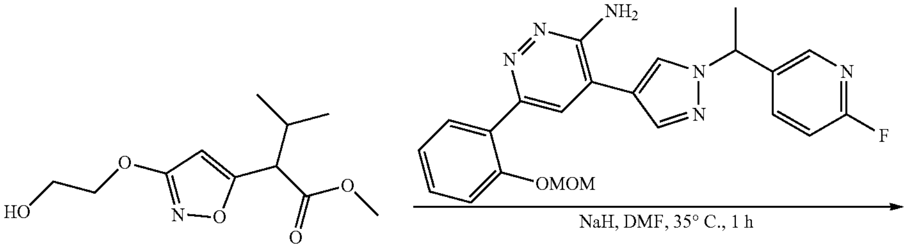

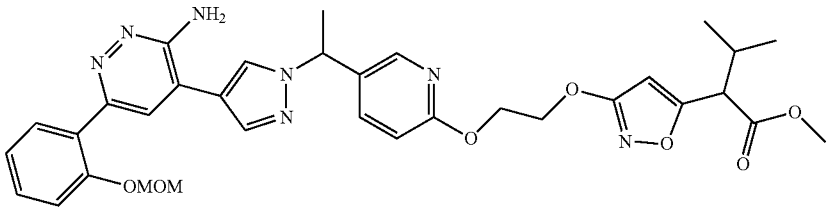

Into a 50-mL round-bottom flask purged and maintained with an inert atmosphere of nitrogen, was placed methyl 2-[3-(2-hydroxyethoxy)-1,2-oxazol-5-yl]-3-methylbutanoate (375 mg, 1.54 mmol, 1.20 equiv) in DMF (6 mL). The solution was cooled to 0° C. in a water/ice bath, and NaH (128.4 mg, 3.21 mmol, 2.50 equiv, 60%) was added. The resulting mixture was stirred for 1 hour at room temperature, and the solution of 4-[1-[1-(6-fluoropyridin-3-yl)ethyl]-1H-pyrazol-4-yl]-6-[2-(methoxymethoxy)phenyl]pyridazin-3-amine (540 mg, 1.28 mmol, 1 equiv) in DMF (4 mL) was added dropwise at 0° C. The resulting mixture was stirred for an additional 1 hour while the temperature was maintained at 35° C. in an oil bath. The reaction mixture was then quenched by the addition of saturated $NH_4Cl$ solution (30 mL), and the pH value of the resulting mixture was adjusted to ~8 with saturated $NaHCO_3$ solution. The mixture was extracted with ethyl acetate (100 mL×2). The organic layers were combined and washed with brine (100 mL×2), dried over anhydrous sodium sulfate and concentrated under vacuum. The residue was applied onto a silica gel column eluting with dichloromethane/methanol (30/1). This resulted in 540 mg (65%) of methyl 2-[3-[2-([5-[1-(4-[3-amino-6-[2-(methoxymethoxy)phenyl]pyridazin-4-yl]-1H-pyrazol-1-yl)ethyl]pyridin-2-yl]oxy)ethoxy]-1,2-oxazol-5-yl]-3-methylbutanoate as a light brown solid.

Methyl 2-[3-[2-([5-[1-(4-[3-amino-6-[2-(methoxymethoxy)phenyl]pyridazin-4-yl]-1H-pyrazol-1-yl)ethyl]pyridin-2-yl]oxy)ethoxy]-1,2-oxazol-5-yl]-3-methylbutanoate was converted to the final compound using procedures analogous to those described for other examples above.

Exemplary compound 163 was prepared using analogous procedures.

Exemplary Synthesis of Exemplary Compound 93 and Exemplary Compound 164

Exemplar Compound 164

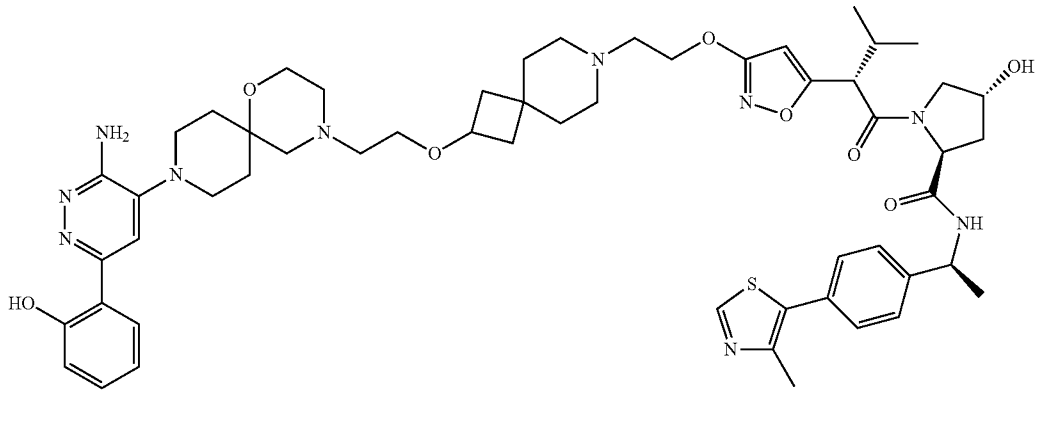

-continued

Exemplary Compound 93

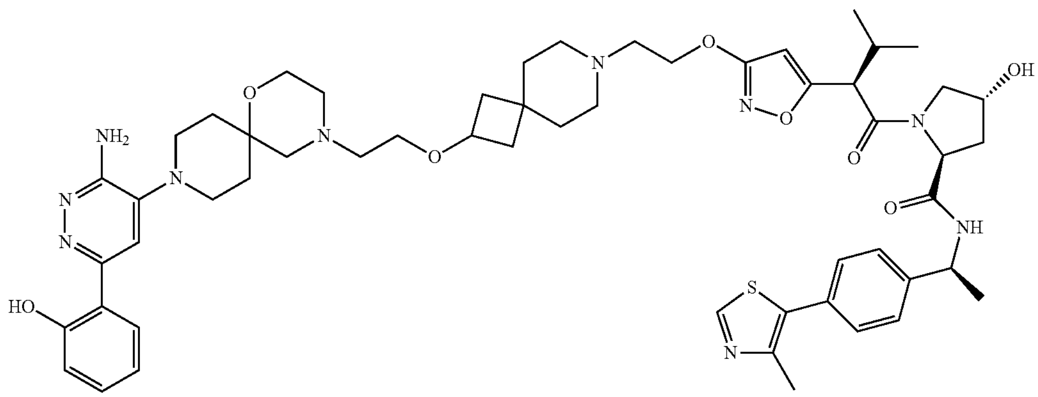

Step 1

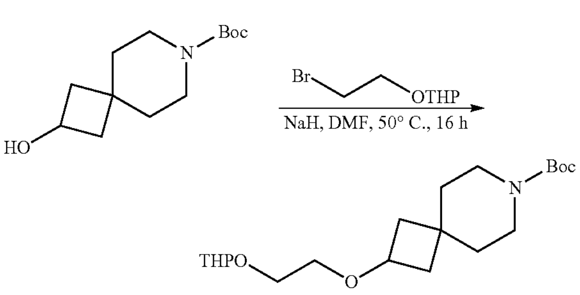

To a solution of tert-butyl 2-hydroxy-7-azaspiro[3.5]nonane-7-carboxylate (1.8 g, 7.46 mmol 1 equiv) in DMF (20 mL) was added sodium hydride (60% in oil, 358 dioxaneg, 14.9 mmol, 2 equiv) at 0° C. The mixture was stirred for 15 min. Then 2-(2-bromoethoxy)oxane (2.3 g, 11.00 mmol, 1.47 equiv) was added and the mixture was allowed to warm to 50° C. and stirred for 16 h. The reaction mixture was quenched by water 100 mL) and extracted with DCM (100 mL×3), washed with water (50 mL×3) and brine (50 mL), dried over anhydrous sodium sulfate and concentrated under reduced pressure. The residue was applied onto a silica gel column with ethyl acetate/petroleum ether (v:v=1:7). This resulted in 1.0 g (36%) of tert-butyl 2-[2-(oxan-2-yloxy)ethoxy]-7-azaspiro[3.5]nonane-7-carboxylate as colorless oil.

Step 2

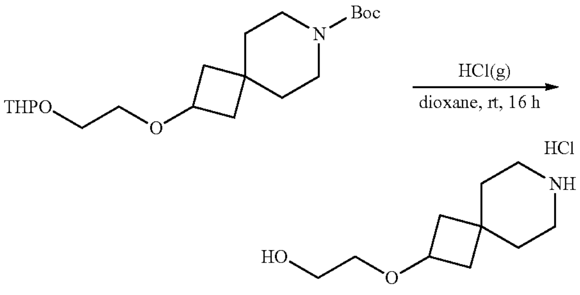

Into a 100-mL round-bottom flask, was placed a solution of tert-butyl 2-[2-(oxan-2-yloxy)ethoxy]-7-azaspiro[3.5]nonane-7-carboxylate (1.0 g, 2.71 mmol, 1 equiv) in dioxane (15 mL), to which was added hydrogen chloride in 1,4-dioxane solution (4.0 M, 15 mL). The resulting solution was stirred for 16 h at room temperature, and then concentrated under reduced pressure. This resulted in 800 mg (53%) of 2-[7-azaspiro[3.5]nonan-2-yloxy]ethan-1-ol as a yellow oil.

Step 3

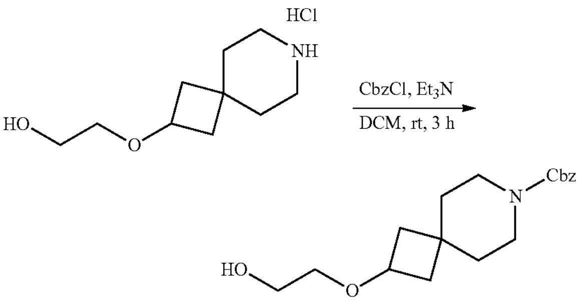

Into a 100-mL round-bottom flask, was placed 2-[7-azaspiro[3.5]nonan-2-yloxy]ethan-1-ol (600 mg, 3.24 mmol, 1 equiv), $Et_3N$ (983 mg, 9.72 mmol, 3 equiv) in DCM (30.0 mL), to which was added CbzCl (663 mg, 3.89 mmol, 1.2 equiv) at room temperature. The resulting mixture was stirred for 16 h at room temperature. The reaction mixture was then diluted with 50 mL water and extracted with ethyl acetate (50 mL×2). The combined organic phase was washed with brine, dried over anhydrous sodium sulfate and concentrated under reduced pressure. The residue was applied onto a silica gel column eluting with dichloromethane/methanol (v:v=10:1). This resulted in 210 mg (20%) of benzyl 2-(2-hydroxyethoxy)-7-azaspiro[3.5]nonane-7-carboxylate as a yellow oil.

Step 4

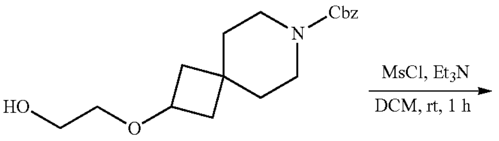

-continued

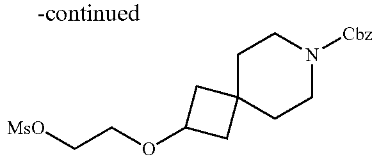

Into a 50-mL round-bottom flask purged and maintained with an inert atmosphere of nitrogen, was placed benzyl 2-(2-hydroxyethoxy)-7-azaspiro[3.5]nonane-7-carboxylate (400 mg, 1.25 mmol, 1 equiv), $Et_3N$ (380 mg, 3.76 mmol, 3 equiv) in DCM (20 mL), to which was added MsCl (287 mg, 2.50 mmol, 2.00 equiv) at 0° C. The resulting mixture was stirred for 1 h at 0° C. in a water/ice bath. The reaction mixture was quenched by the addition of water (30 mL) and extracted with dichloromethane (30 mL×2). The combined organic layer was washed with brine (30 mL), dried over anhydrous sodium sulfate and concentrated. This resulted in 420 mg (85%) of benzyl 2-[2-(methanesulfonyloxy)ethoxy]-7-azaspiro[3.5]nonane-7-carboxylate as a yellow oil.

Step 5

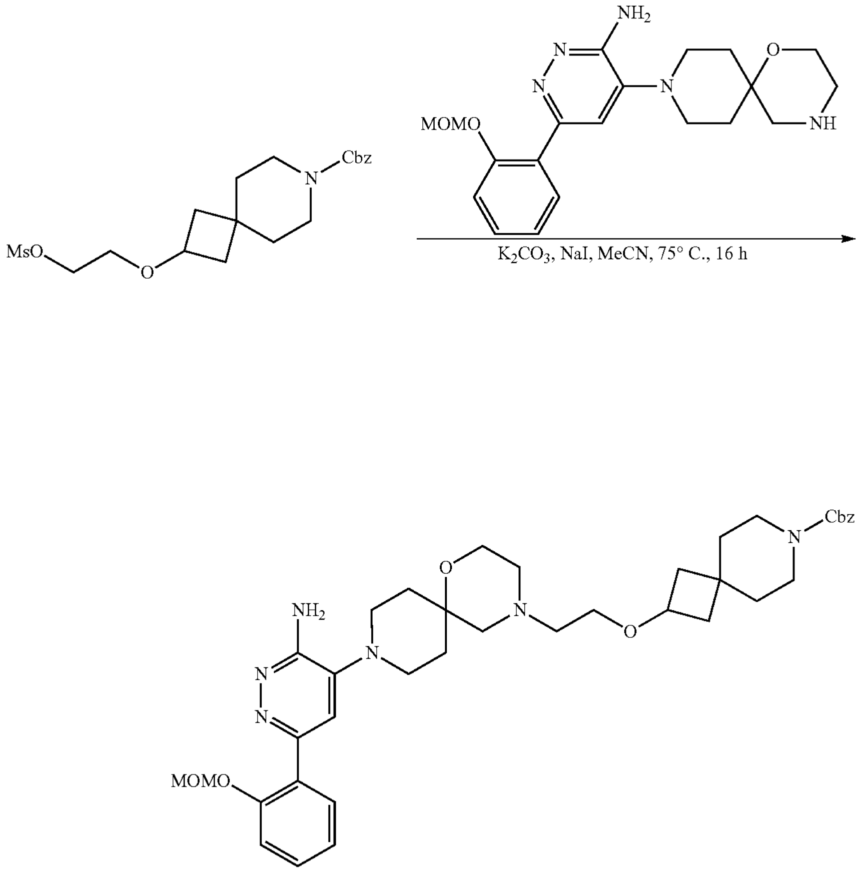

Into a 100-mL round-bottom flask, was placed a solution of benzyl 2-[2-(methanesulfonyloxy)ethoxy]-7-azaspiro[3.5]nonane-7-carboxylate (300 mg, 0.75 mmol, 1 equiv), 6-[2-(methoxymethoxy)phenyl]-4-[1-oxa-4,9-diazaspiro[5.5]undecan-9-yl]pyridazin-3-amine (291 mg, 0.75 mmol, 1 equiv), $K_2CO_3$ (313 mg, 2.26 mmol, 3 equiv), NaI (113 mg, 0.75 mmol, 1 equiv) in MeCN (15 mL). The resulting mixture was stirred for 16 h at 75° C. in an oil bath. The solids were filtered out, and the filtrate was concentrated under reduced pressure. The residue was applied onto a silica gel column eluting with dichloromethane/methanol (v:v=10:1). This resulted in 130 mg (25%) of benzyl 2-[2-(9-[3-amino-6-[2-(methoxymethoxy)phenyl]pyridazin-4-yl]-1-oxa-4,9-diazaspiro[5.5]undecan-4-yl)ethoxy]-7-azaspiro[3.5]nonane-7-carboxylate as a yellow oil.

Step 6

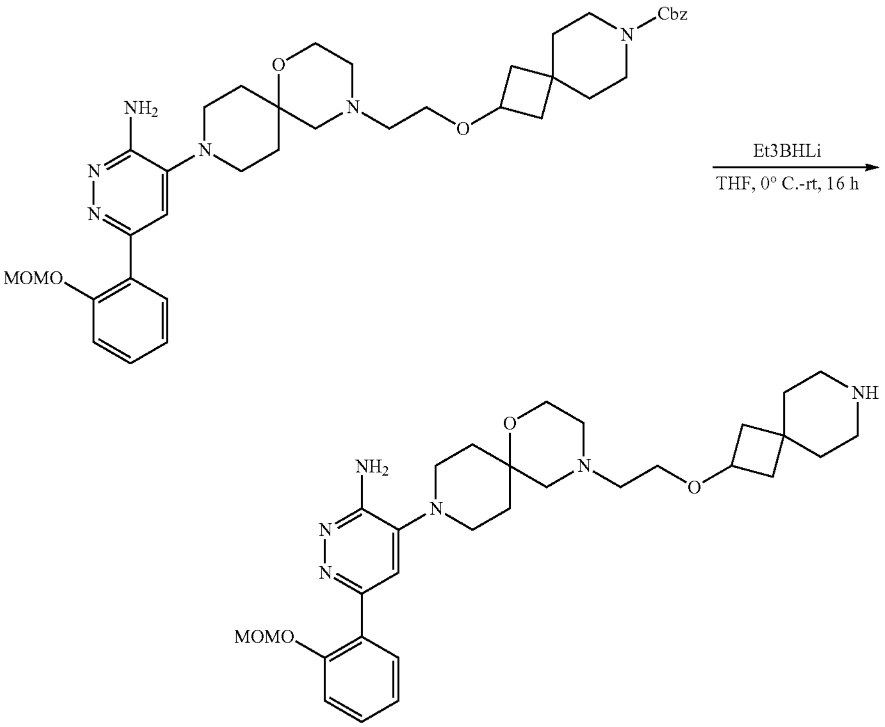

Into a 100-mL round-bottom flask, was placed a solution of benzyl 2-[2-(9-[3-amino-6-[2-(methoxymethoxy)phenyl] pyridazin-4-yl]-1-oxa-4,9-diazaspiro[5.5]undecan-4-yl) ethoxy]-7-azaspiro[3.5]nonane-7-carboxylate (230 mg, 0.33 mmol, 1 equiv) in THF (5 mL), to which was added lithium triethylborohydride (1.0 M in THF, 1.65 mmol, 5.0 eq) at 0° C. The resulting mixture was stirred for 16 hours at room temperature, and then was quenched by water (50 mL) and extracted with dichloromethane (50 mL×3). The combined organic layer was washed with brine (50 mL), dried over anhydrous sodium sulfate and concentrated under reduced pressure. This resulted in 140 mg (76%) of 4-[4-(2-[7-azaspiro[3.5]nonan-2-yloxy]ethyl)-1-oxa-4,9-diazaspiro [5.5]undecan-9-yl]-6-[2-(methoxymethoxy)phenyl] pyridazin-3-amine as a yellow oil.

4-[4-(2-[7-azaspiro[3.5]nonan-2-yloxy]ethyl)-1-oxa-4,9-diazaspiro[5.5]undecan-9-yl]-6-[2-(methoxymethoxy)phenyl]pyridazin-3-amine was converted to the final compounds according to the scheme below using procedures described for other examples above.

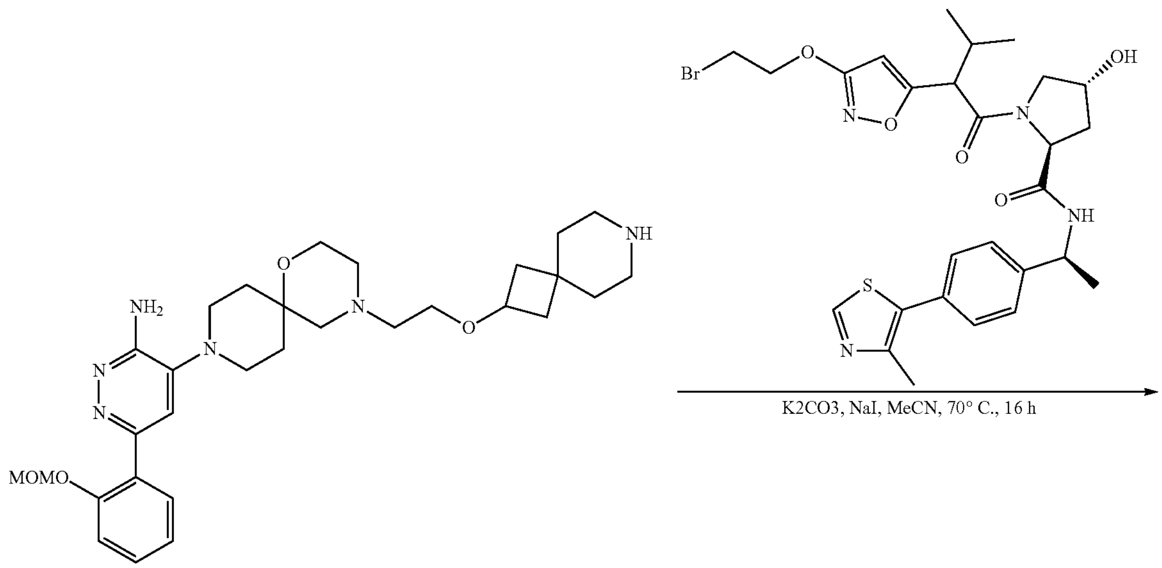

-continued
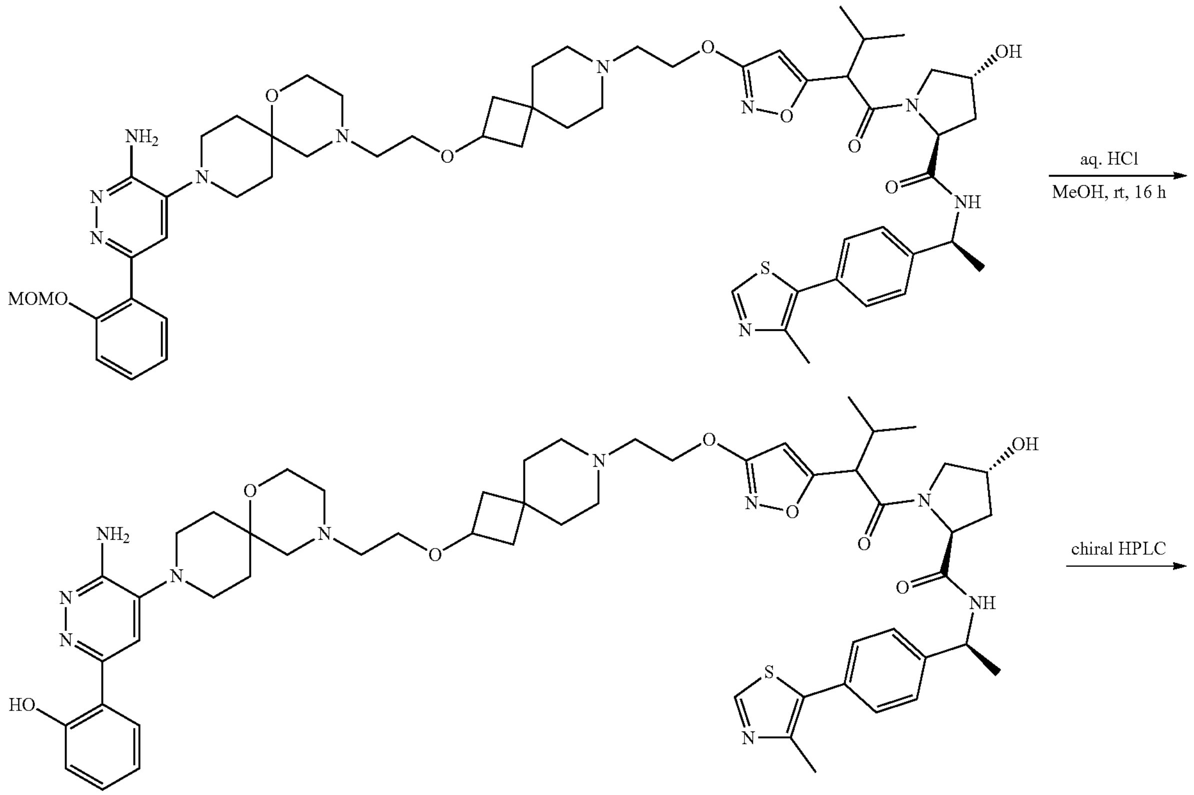
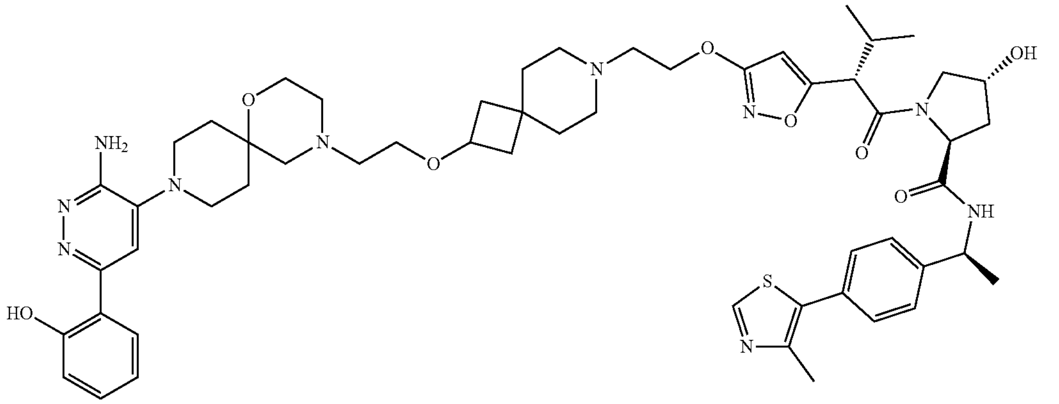
+
Exemplary Compound 164
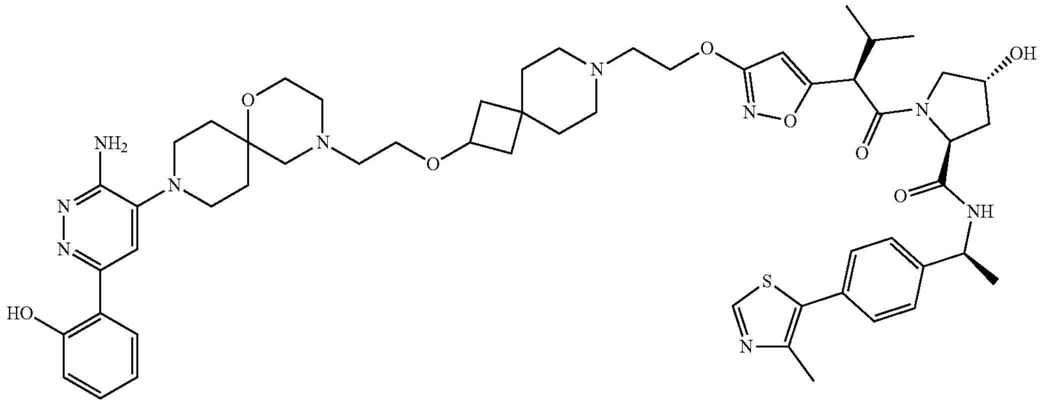
Exemplary Compound 93

Exemplary compound 164 was prepared using analogous procedures.

Exemplary Synthesis of Exemplary Compound 113

Ex. 113

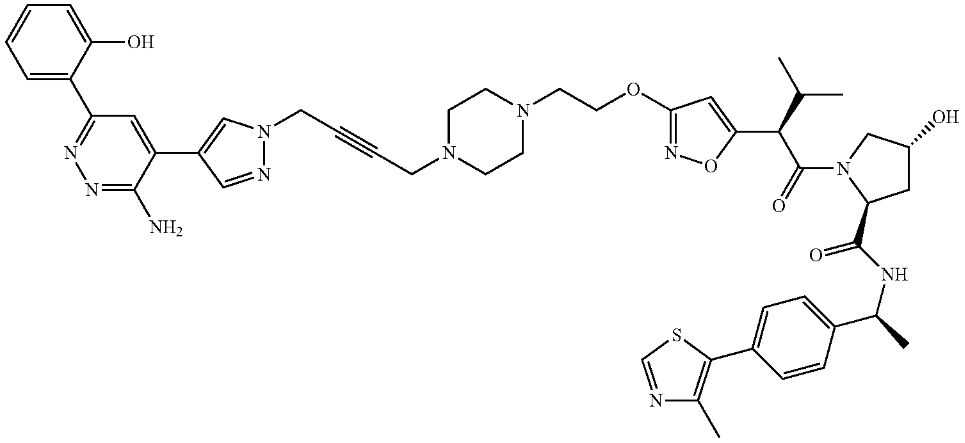

Step 1

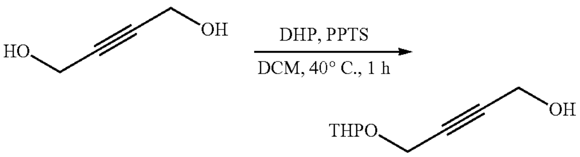

To a solution of but-2-yne-1,4-diol (10 g, 116.16 mmol, 1 eq), 2,3-dihydro-2H-pyran (9.77 g, 116.16 mmol, 10.6 mL, 1 eq) in dichloromethane (200 mL) was added pyridinium p-toluenesulfonate (2.92 g, 11.62 mmol, 0.1 eq). The reaction mixture was stirred at 40° C. for 1 hour. Water (200 mL) was added to the mixture, and the resulting mixture was extracted with dichloromethane (150 mL×2). The combined organic phase was washed with brine (150 mL), dried over sodium sulfate, filtered and concentrated in vacuum. The residue was purified by silica gel chromatography (petroleum ether:ethyl acetate=100:1 to 1:1). 4-tetrahydropyran-2-yloxybut-2-yn-1-ol (10.2 g, 59.93 mmol, 51% yield) was obtained as a light yellow oil.

Step 2

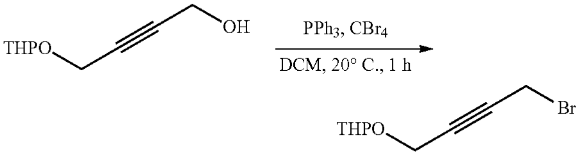

To a solution of 4-tetrahydropyran-2-yloxybut-2-yn-1-ol (5 g, 29.38 mmol, 1 eq), triphenylphosphine (7.70 g, 29.38 mmol, 1 eq) in dichloromethane (100 mL) was added carbon tetrabromide (10.72 g, 32.31 mmol, 1.1 eq) at 0° C. The reaction mixture was stirred at 20° C. for 1 hour. The mixture was concentrated in vacuum. The residue was purified by silica gel chromatography (petroleum ether:ethyl acetate=1:0 to 100:1). 2-(4-bromobut-2-ynoxy)tetrahydropyran (4 g, 17.16 mmol, 58% yield) was obtained as a light yellow oil.

Step 3

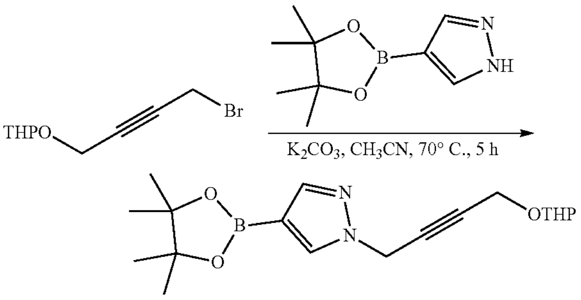

To a solution of 4-(4,4,5,5-tetramethyl-1,3,2-dioxaborolan-2-yl)-1H-pyrazole (3 g, 15.46 mmol, 1 eq), 2-(4-bromobut-2-ynoxy)tetrahydropyran (3.96 g, 17.01 mmol, 1.1 eq) in acetonitrile (30 mL) was added potassium carbonate (2.56 g, 18.55 mmol, 1.2 eq). The reaction mixture was stirred at 70° C. for 12 hours. Water (100 mL) was added to the mixture, and the resulting mixture was extracted with ethyl acetate (30 mL×3). The combined organic phase was washed with brine (50 mL), dried over sodium sulfate, filtered and concentrated in vacuum. The residue was purified by silica gel chromatography (petroleum ether:ethyl acetate=200:1 to 3:1). 1-(4-tetrahydropyran-2-yloxybut-2-ynyl)-4-(4,4,5,5-tetramethyl-1,3,2-dioxaborolan-2-yl)pyrazole (4.5 g, 13.00 mmol, 84% yield) was obtained as a light yellow oil.

Step 4

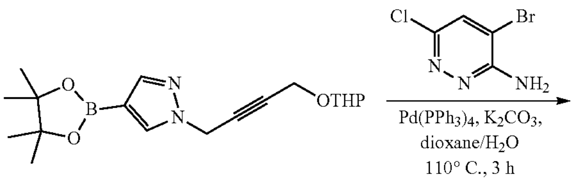

-continued

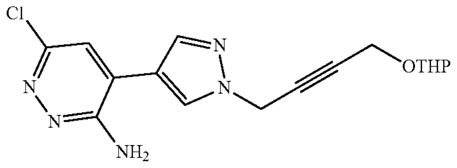

To a solution of 1-(4-tetrahydropyran-2-yloxybut-2-ynyl)-4-(4,4,5,5-tetramethyl-1,3,2-dioxaborolan-2-yl)pyrazole (2 g, 5.78 mmol, 1 eq), 4-bromo-6-chloro-pyridazin-3-amine (1.20 g, 5.78 mmol, 1 eq) in dioxane (60 mL) and water (20 mL) was added sodium carbonate (1.53 g, 14.44 mmol, 2.5 eq) and (1,1'-bis(diphenylphosphino)ferrocene) palladium(II) dichloride (422 mg, 0.58 mmol, 0.1 eq) under nitrogen. The reaction mixture was stirred at 110° C. for 3 hours. Water (200 mL) was added to the mixture, and the resulting mixture was extracted with ethyl acetate (100 mL×3). The combined organic phase was washed with brine (100 mL), dried over sodium sulfate, filtered and concentrated in vacuum. The residue was purified by silica gel chromatography (dichloromethane:methanol=1:0 to 50:1). 6-chloro-4-[1-(4-tetrahydropyran-2-yloxybut-2-ynyl)pyrazol-4-yl]pyridazin-3-amine (1.3 g, 3.40 mmol, 58% yield) was obtained as a yellow solid.

Step 5

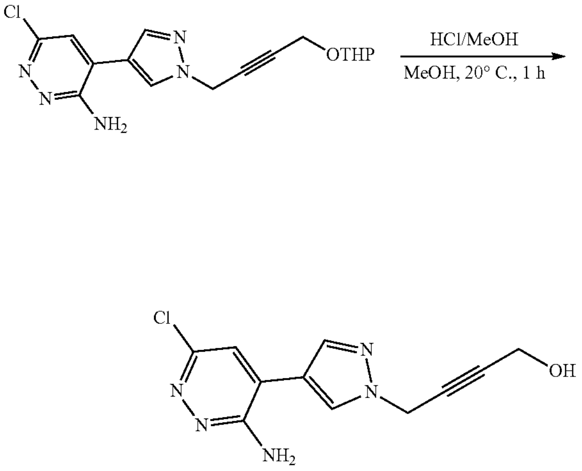

To a solution of 6-chloro-4-[1-(4-tetrahydropyran-2-yloxybut-2-ynyl)pyrazol-4-yl]pyridazin-3-amine (1.6 g, 4.60 mmol, 1 eq) in methanol (15 mL) was added hydrochloric acid solution (4 M in methanol, 15 mL, 13.04 eq). The reaction mixture was stirred at 20° C. for 1 hour. Saturated sodium bicarbonate (50 mL) was added to the mixture to adjust pH to about 6, after which the resulting mixture was extracted with ethyl acetate (30 mL×3). The combined organic phase was washed with brine (30 mL), dried over sodium sulfate, filtered and concentrated in vacuum. 4-[4-(3-amino-6-chloro-pyridazin-4-yl)pyrazol-1-yl]but-2-yn-1-ol (1.0 g, 3.79 mmol, 82% yield) was obtained as a light yellow solid.

Step 6

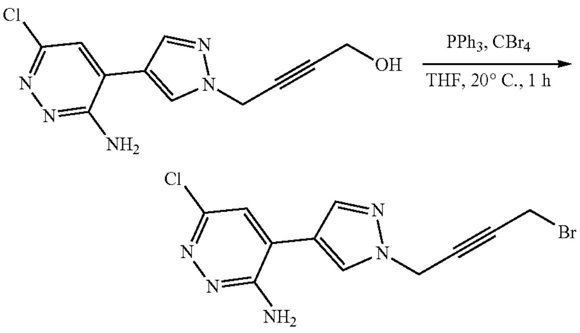

To a solution of 4-[4-(3-amino-6-chloro-pyridazin-4-yl) pyrazol-1-yl]but-2-yn-1-ol (1.0 g, 3.79 mmol, 1 eq), triphenylphosphine (1.19 g, 4.55 mmol, 1.2 eq) in tetrahydrofuran (20 mL) was added carbon tetrabromide (1.51 g, 4.55 mmol, 1.2 eq). The reaction mixture was stirred at 20° C. for 1 hour. The mixture was concentrated in vacuum. The residue was purified by silica gel chromatography (dichloromethane:methanol=1:0 to 50:1). 4-[1-(4-bromobut-2-ynyl)pyrazol-4-yl]-6-chloro-pyridazin-3-amine (1.0 g, 1.87 mmol, 49% yield) was obtained as a light yellow solid.

Step 7

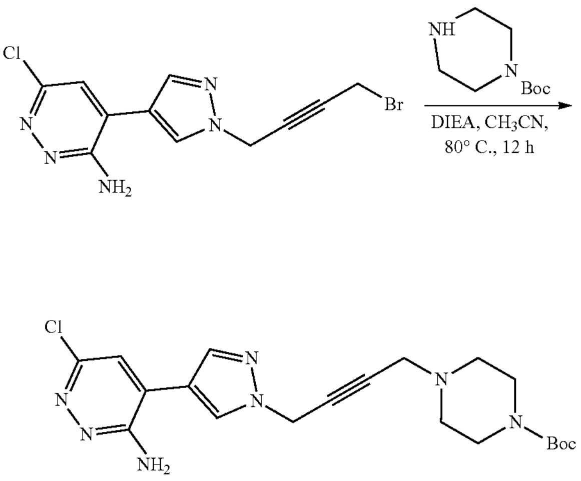

To a solution of 4-[1-(4-bromobut-2-ynyl)pyrazol-4-yl]-6-chloro-pyridazin-3-amine (1 g, 1.87 mmol, 1 eq) and tert-butyl piperazine-1-carboxylate (696 mg, 3.74 mmol, 2 eq) in acetonitrile (10 mL) was added N,N-diisopropylethylamine (724 mg, 5.60 mmol, 1.0 mL, 3 eq). The mixture was stirred at 80° C. for 12 hours. Water (30 mL) was added to the mixture, and the resulting mixture was extracted with ethyl acetate (20 mL×3). The combined organic phase was washed with brine (20 mL), dried over sodium sulfate, filtered and concentrated in vacuum. The residue was purified by silica gel chromatography (dichloromethane:methanol=1:0 to 20:1). Tert-Butyl 4-[4-[4-(3-amino-6-chloro-pyridazin-4-yl)pyrazol-1-yl]but-2-ynyl]piperazine-1-carboxylate (600 mg, 1.34 mmol, 71% yield) was obtained as a brown solid.

Step 8

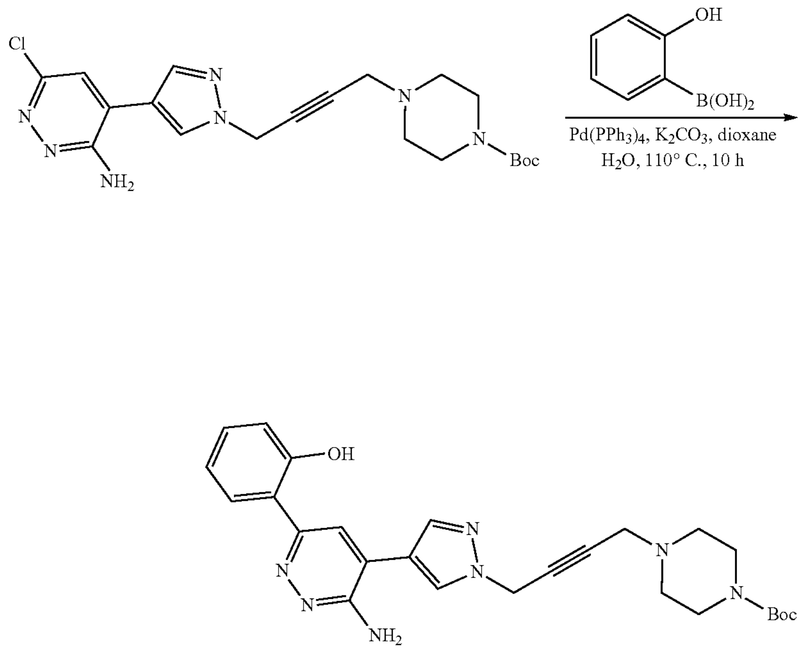

To a solution of tert-butyl 4-[4-[4-(3-amino-6-chloropyridazin-4-yl)pyrazol-1-yl]but-2-ynyl]piperazine-1-carboxylate (500 mg, 1.16 mmol, 1 eq), (2-hydroxyphenyl) boronic acid (192 mg, 1.39 mmol, 1.2 eq) in dioxane (10 mL) and water (2 mL) was added potassium carbonate (400 mg, 2.89 mmol, 2.5 eq) and tetrakis[triphenylphosphine] palladium(0) (134 mg, 0.12 mmol, 0.1 eq) under nitrogen. The reaction mixture was stirred at 110° C. for 10 hours. Water (100 mL) was added to the mixture, and the resulting mixture was extracted with ethyl acetate (50 mL×3). The combined organic phase was washed with brine (50 mL), dried over sodium sulfate, filtered and concentrated in vacuum. The residue was purified by prep thin-layer chromatography (dichloromethane:methanol=10:1). Tert-Butyl 4-[4-[4-[3-amino-6-(2-hydroxyphenyl)pyridazin-4-yl]pyrazol-1-yl]but-2-ynyl]piperazine-1-carboxylate (340 mg, 0.65 mmol, 56% yield) was obtained as a light yellow solid.

Tert-Butyl 4-[4-[4-[3-amino-6-(2-hydroxyphenyl)pyridazin-4-yl]pyrazol-1-yl]but-2-ynyl]piperazine-1-carboxylate was converted to the final compound according to the scheme below using procedures described for other examples above.

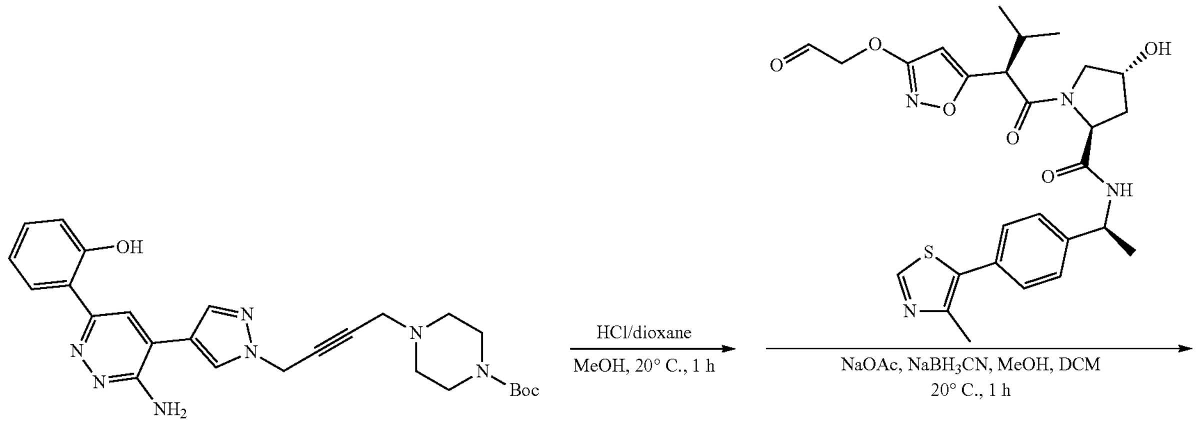

-continued

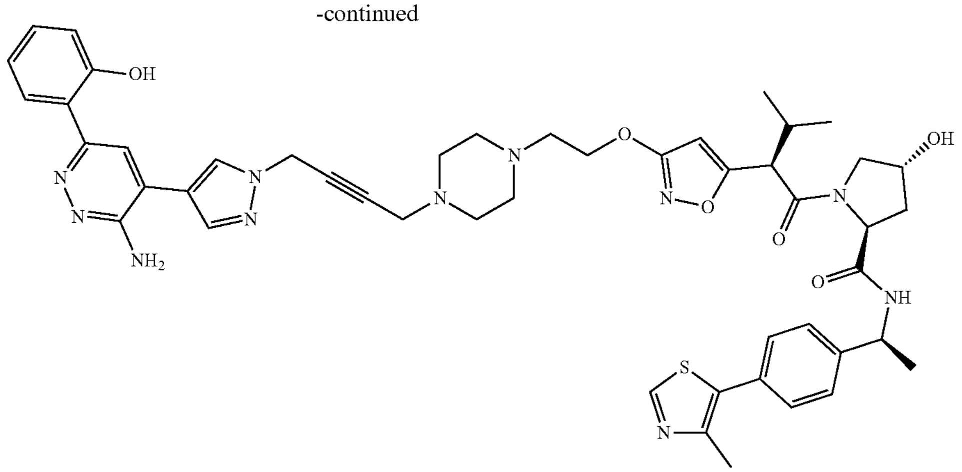

Ex. 113

Exemplary Synthesis of Exemplary Compound 83

Ex. 83

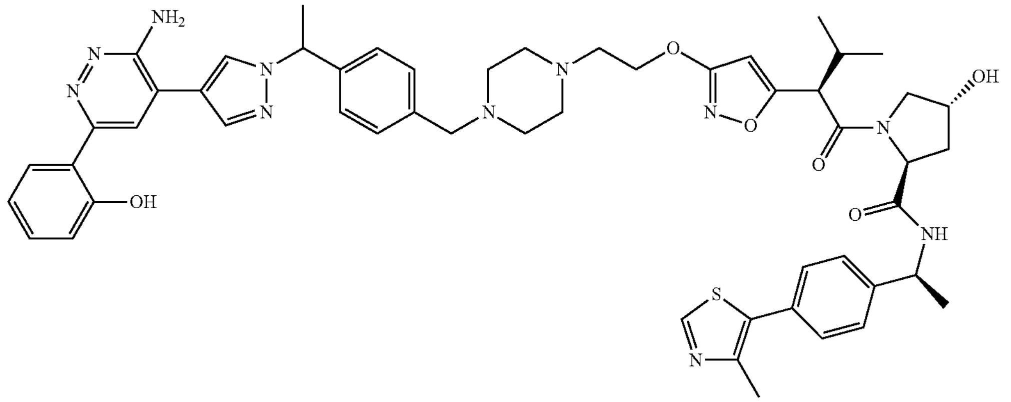

Step 1

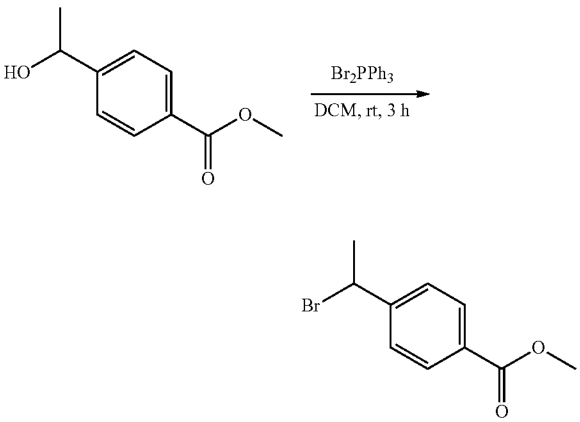

Into a 250-mL round-bottom flask, was placed a solution of methyl 4-(1-hydroxyethyl)benzoate (2.5 g, 13.87 mmol, 1 equiv), triphenylphosphine dibromide (5.9 g, 13.87 mmol, 1 equiv) in DCM (100 mL). The resulting mixture was stirred for 3 hours at room temperature. The reaction mixture was concentrated under reduced pressure, and the residue was applied onto a silica gel column eluting with ethyl acetate/petroleum ether (v:v=1:12). This resulted in 2.3 g (68%) of methyl 4-(1-bromoethyl)benzoate as a colorless oil.

Step 2

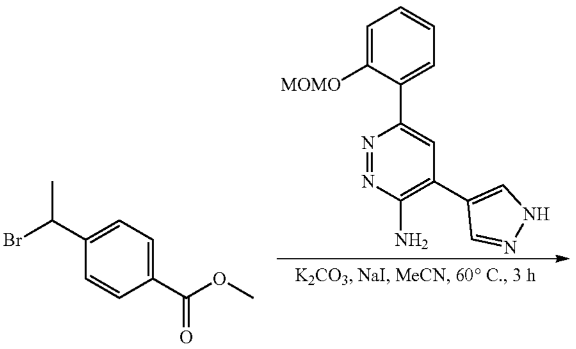

-continued

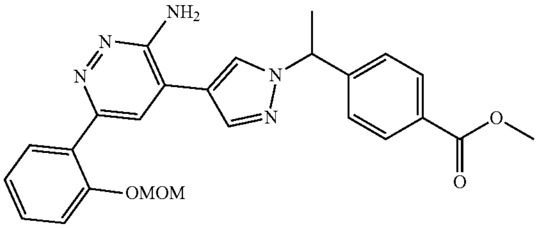

Into a 30-mL vial, was placed methyl 4-(1-bromoethyl) benzoate (1.2 g, 4.94 mmol, 1 equiv), 6-[2-(methoxymethoxy)phenyl]-4-(1H-pyrazol-4-yl)pyridazin-3-amine (1.2 g, 3.95 mmol, 0.80 equiv), $K_2CO_3$ (2.0 g, 14.81 mmol, 3.00 equiv), NaI (739.9 mg, 4.94 mmol, 1.00 equiv) in DMF (15 mL). The resulting mixture was stirred for 3 hours at 60° C. in an oil bath. The reaction mixture was then diluted by water (50 mL) and extracted with dichloromethane (50 mL×3). The combined organic layer was washed with water (50 mL×2) and brine (50 mL), dried over anhydrous sodium sulfate and concentrated under reduced pressure. The residue was applied onto a silica gel column eluting with dichloromethane/methanol (v:v=10:1). This resulted in 600 mg (26%) of methyl 4-[1-(4-[3-amino-6-[2-(methoxymethoxy)phenyl]pyridazin-4-yl]-1H-pyrazol-1-yl) ethyl]benzoate as a yellow oil.

Step 3

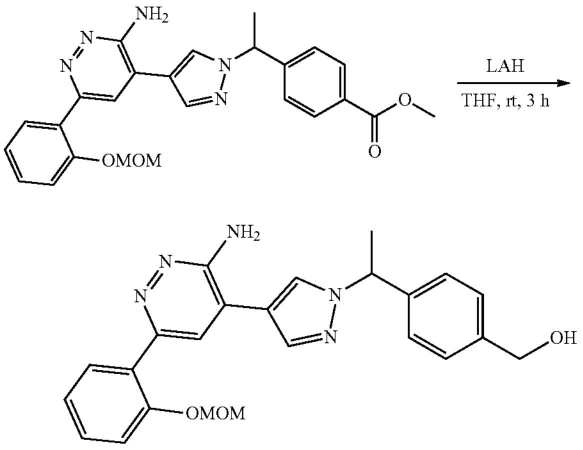

Into a 100-mL round-bottom flask, was placed a solution of methyl 4-[1-(4-[3-amino-6-[2-(methoxymethoxy)phenyl] pyridazin-4-yl]-1H-pyrazol-1-yl)ethyl]benzoate (600 mg, 1.31 mmol, 1 equiv) in THF (20 mL), to which was added $LiAlH_4$ (495.6 mg, 13.06 mmol, 10.00 equiv) at 0° C. The resulting mixture was stirred for 3 hours at room temperature. The reaction was then quenched by the addition of $Na_2SO_4.10H_2O$ (4.8 g, 15.0 mmol). The resulting mixture was stirred for 3 hours at room temperature. The solids in the reaction mixture were filtered out, and the filtrate was concentrated under reduced pressure. The residue was applied onto a silica gel column eluting with dichloromethane/methanol (v:v=10:1). This resulted in 310 mg (55%) of [4-[1-(4-[3-amino-6-[2-(methoxymethoxy)phenyl] pyridazin-4-yl]-1H-pyrazol-1-yl)ethyl]phenyl]methanol as a yellow oil.

Step 4

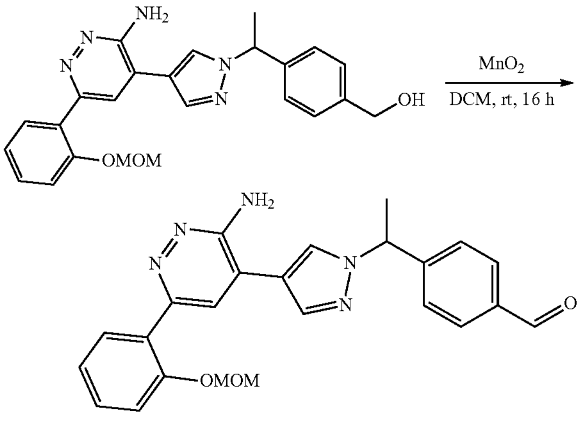

Into a 100-mL round-bottom flask, was placed a solution of [4-[1-(4-[3-amino-6-[2-(methoxymethoxy)phenyl] pyridazin-4-yl]-1H-pyrazol-1-yl)ethyl]phenyl]methanol (310 mg, 0.72 mmol, 1 equiv) in DCM (10.0 mL, 117 mmol, 218 equiv), to which was added manganese dioxide (1.2 g, 14.37 mmol, 20 equiv) at room temperature. The resulting mixture was stirred for 16 hours at room temperature. The solids were filtered off, and the filtrate was concentrated under reduced pressure. This resulted in 286 mg (93%) of 4-[1-(4-[3-amino-6-[2-(methoxymethoxy)phenyl]pyridazin-4-yl]-1H-pyrazol-1-yl)ethyl]benzaldehyde as a yellow solid.

Step 5

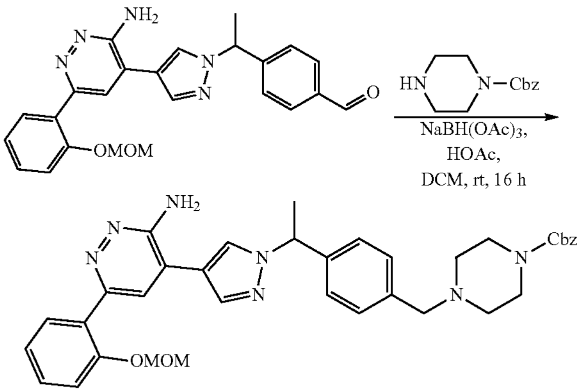

Into a 100-mL round-bottom flask, was placed 4-[1-(4-[3-amino-6-[2-(methoxymethoxy)phenyl]pyridazin-4-yl]-1H-pyrazol-1-yl)ethyl]benzaldehyde (300.0 mg, 0.70 mmol, 1 equiv), benzyl piperazine-1-carboxylate (185 mg, 0.84 mmol, 1.2 equiv), HOAc (0.1 mL, 1.75 mmol, 2.50 equiv) in DCM (10 mL). The resulting mixture was stirred for 0.5 hour, and then $NaBH(OAc)_3$ (444.1 mg, 2.10 mmol, 3 equiv) was added. The resulting mixture was stirred for additional 16 hours at room temperature. The reaction mixture was then quenched by water (20 mL) and extracted with dichloromethane (20 mL×3). The combined organic layer was washed with water (20 mL×2) and brine (20 mL), dried over anhydrous sodium sulfate and concentrated under reduced pressure. The residue was applied onto a silica gel column eluting with dichloromethane/methanol (v:v=10:1). This resulted in 260 mg (59%) of benzyl 4-([4-[1-(4-[3-amino-6-[2-(methoxymethoxy)phenyl]pyridazin-4-yl]-1H-pyrazol-1-yl)ethyl]phenyl]methyl)piperazine-1-carboxylate as a yellow oil.

Step 6

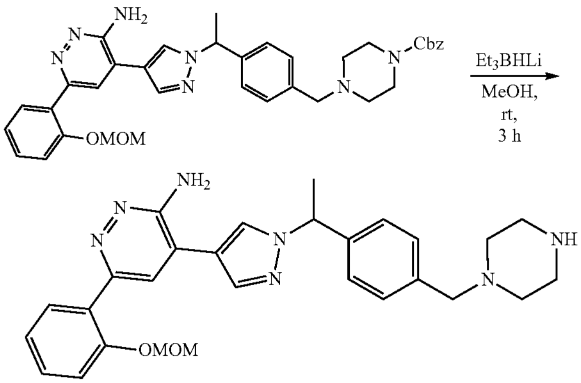

Into a 100-mL round-bottom flask purged and maintained with an inert atmosphere of nitrogen, was placed a solution of benzyl 4-([4-[1-(4-[3-amino-6-[2-(methoxymethoxy)phenyl]pyridazin-4-yl]-1H-pyrazol-1-yl)ethyl]phenyl]methyl) piperazine-1-carboxylate (260.0 mg, 0.41 mmol, 1 equiv) in THF (8 mL), to which lithium triethylborohydride (2.1 mL, 2.05 mmol, 5.00 equiv) was added at 0° C. The reaction mixture was stirred for 16 hours at room temperature. The reaction mixture was then quenched by water (30 mL) and extracted with dichloromethane (30 mL×3). The combined organic layer was washed with brine (30 mL), dried over anhydrous sodium and concentrated. This resulted in 200 mg (98%) of 6-[2-(methoxymethoxy)phenyl]-4-[1-(1-[4-[(piperazin-1-yl)methyl]phenyl]ethyl)-1H-pyrazol-4-yl] pyridazin-3-amine as a yellow oil.

6-[2-(methoxymethoxy)phenyl]-4-[1-(1-[4-[(piperazin-1-yl)methyl]phenyl]ethyl)-1H-pyrazol-4-yl]pyridazin-3-amine was converted to the title compound according to the scheme below using procedures described above for other examples.

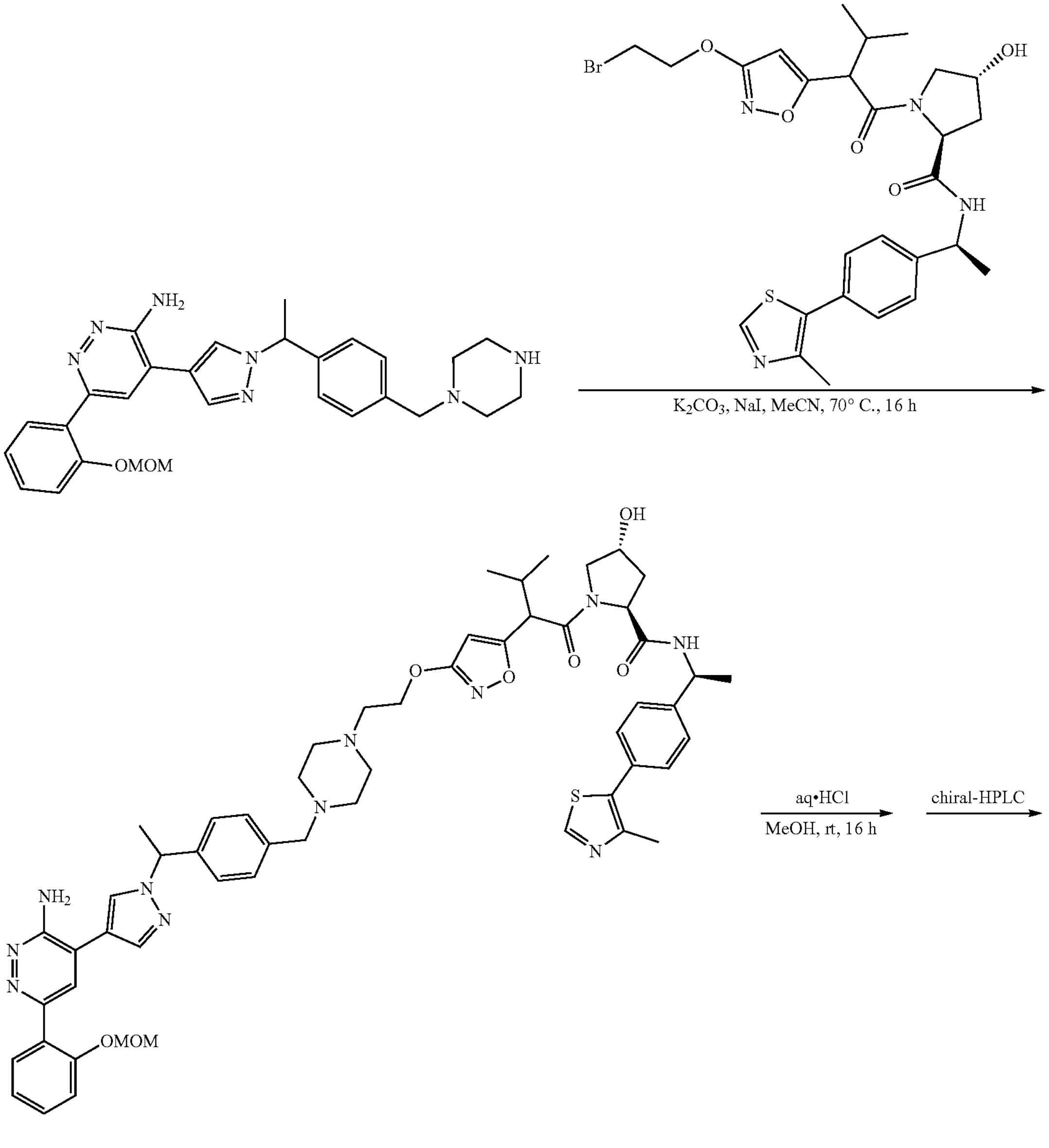

-continued
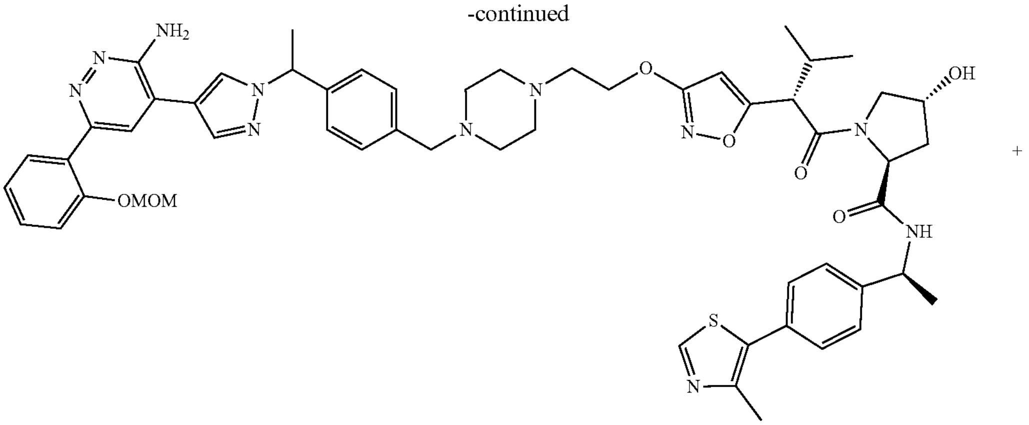
Ex. 166
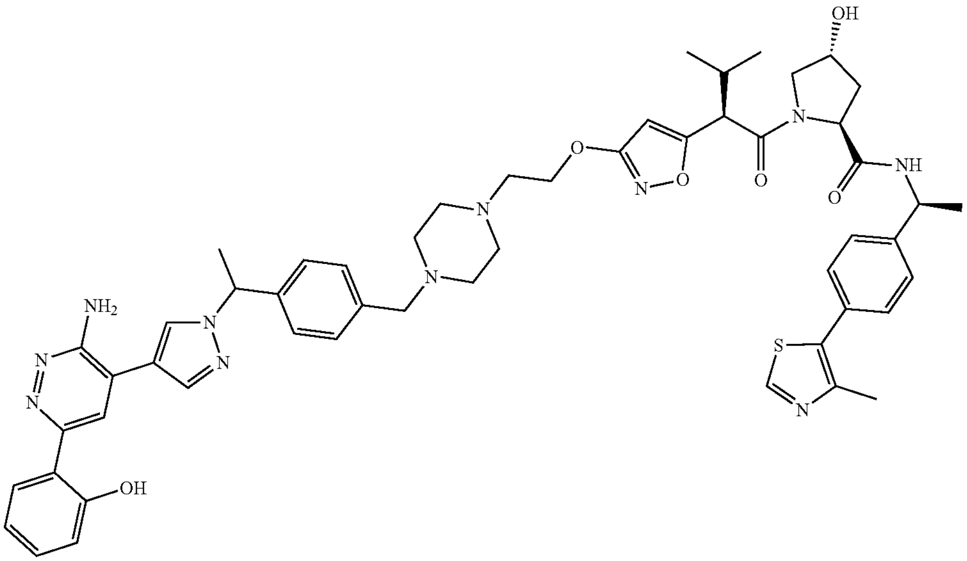
Ex. 83
Exemplary Synthesis of Exemplary Compound 167
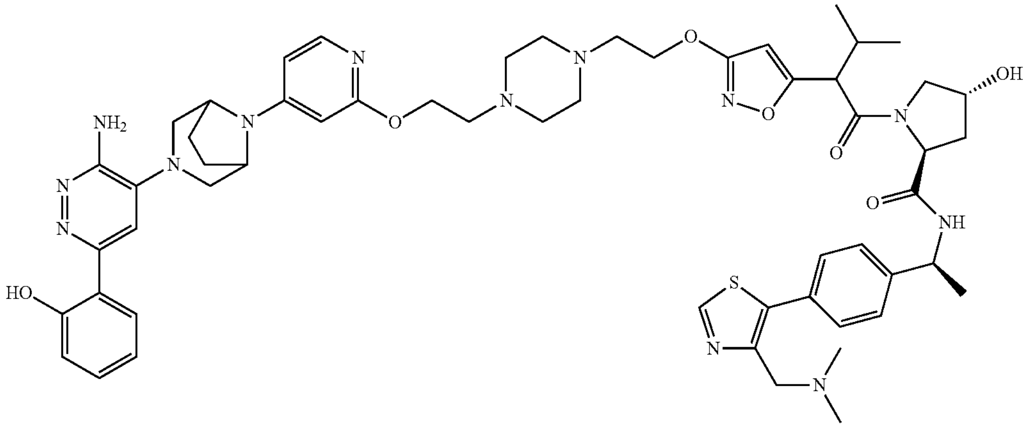
Ex. 167

Step 1

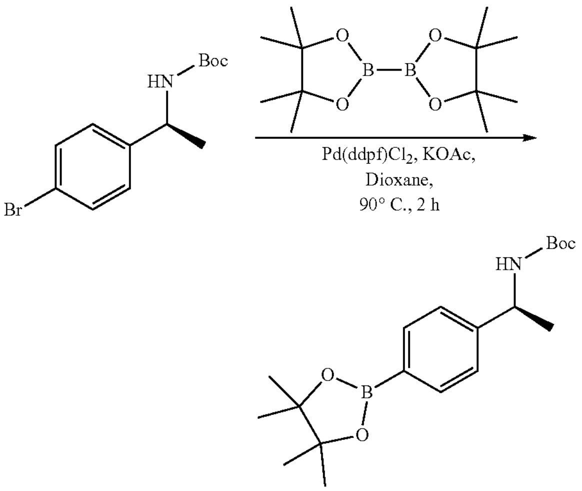

To a solution of tert-butyl N-[(1S)-1-(4-bromophenyl)ethyl]carbamate (5 g, 16.7 mmol, 1 eq) and 4,4,5,5-tetramethyl-2-(4,4,5,5-tetramethyl-1,3,2-dioxaborolan-2-yl)-1,3,2-dioxaborolane (5.08 g, 20.0 mmol, 1.2 eq) in dioxane (100 mL) was added [1,1'-bis(diphenylphosphino)ferrocene]dichloropalladium(II) (975 mg, 1.33 mmol, 0.08 eq) and potassium acetate (3.27 g, 33.31 mmol, 2 eq). The mixture was stirred at 90° C. for 2 hours. The reaction mixture was concentrated to give crude product. The crude product was purified by silica gel chromatography (petroleum ether:ethyl acetate=1:0 to 10:1). Compound tert-butyl N-[(1S)-1-[4-(4,4,5,5-tetramethyl-1,3,2-dioxaborolan-2-yl)phenyl]ethyl]carbamate (8.2 g, 16.44 mmol, 99% yield) was obtained as a yellow oil.

Step 2

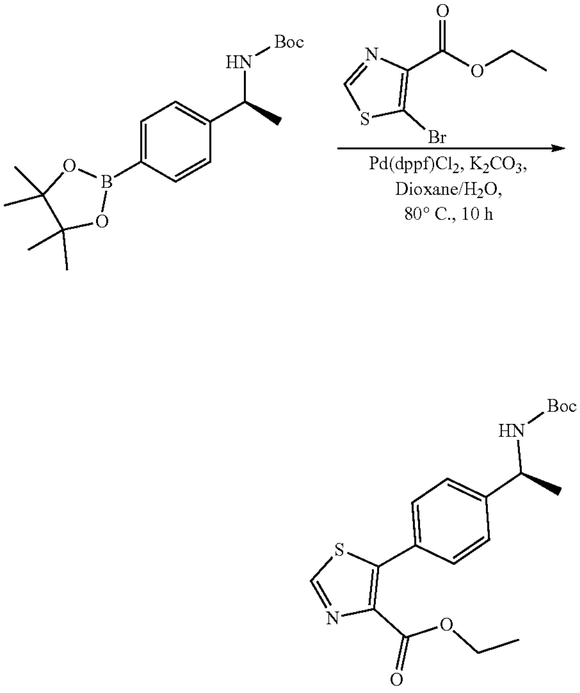

A mixture of ethyl 5-bromothiazole-4-carboxylate (3.49 g, 14.77 mmol, 0.9 eq), tert-butyl N-[(1S)-1-[4-(4,4,5,5-tetramethyl-1,3,2-dioxaborolan-2-yl)phenyl]ethyl]carbamate (5.70 g, 16.41 mmol, 1 eq), [1,1'-bis(diphenylphosphino)ferrocene]dichloropalladium(II) (120 mg, 0.16 mmol, 0.01 eq), potassium carbonate (4.54 g, 32.83 mmol, 2 eq) in mixture of dioxane (130 mL) and water (22 mL) was degassed and purged with nitrogen for three times, and then the mixture was stirred at 80° C. for 10 hours under nitrogen atmosphere. The reaction mixture was concentrated and added water (50 mL), then extracted with ethyl acetate (60 mL) two times. The combined organic layers were washed with saturated aqueous sodium chloride (50 mL) two times, dried over anhydrous sodium sulfate, concentrated to give crude product. The crude product was purified by silica gel chromatography (petroleum ether:ethyl acetate=1:0 to 1:1). Compound ethyl 5-[4-[(1S)-1-(tert-butoxycarbonylamino)ethyl]phenyl]thiazole-4-carboxylate (5.07 g, 13.48 mmol, 82% yield) was obtained as a yellow solid.

Step 3

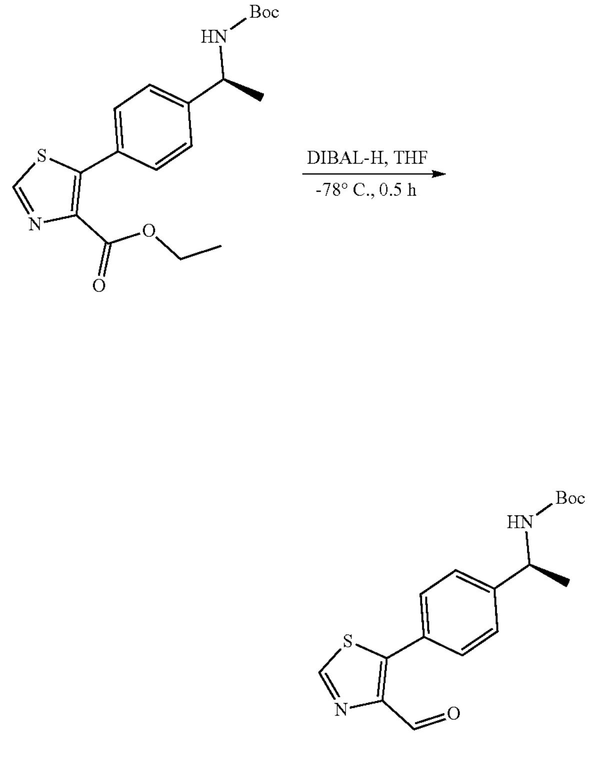

A solution of ethyl 5-[4-[(1S)-1-(tert-butoxycarbonylamino)ethyl]phenyl]thiazole-4-carboxylate (4 g, 10.63 mmol, 1 eq) in tetrahydrofuran (60 mL) was cooled to −78° C. under nitrogen atmosphere. Then diisobutylaluminium hydride THF solution (1 M, 11.69 mL, 1.1 eq) was added dropwise at −78° C. The reaction mixture was stirred at −78° C. for 0.5 hour. Methanol (2 mL) was added to quench the reaction, followed by water (50 mL). The mixture was extracted with ethyl acetate (40 mL×2). The organic layer was dried over sodium sulfate and then concentrated under vacuum to get the residue. The residue was purified by silica gel column chromatography (10-50% ethyl acetate in petroleum ether). Compound tert-butyl N-[(1S)-1-[4-(4-formylthiazol-5-yl)phenyl]ethyl]carbamate (3.2 g, 9.63 mmol, 91% yield) was obtained as a white solid.

tert-Butyl N-[(1S)-1-[4-[4-[(dimethylamino)methyl]thiazol-5-yl]phenyl]ethyl]carbamate was converted to the final product using procedures described for exemplary compound 76.

Exemplary Synthesis of Exemplary Compound 168

Ex. 168

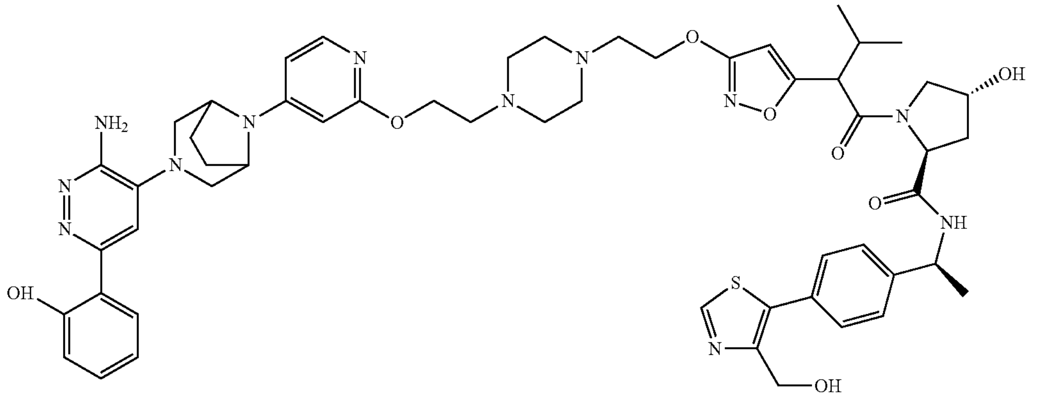

Step 4

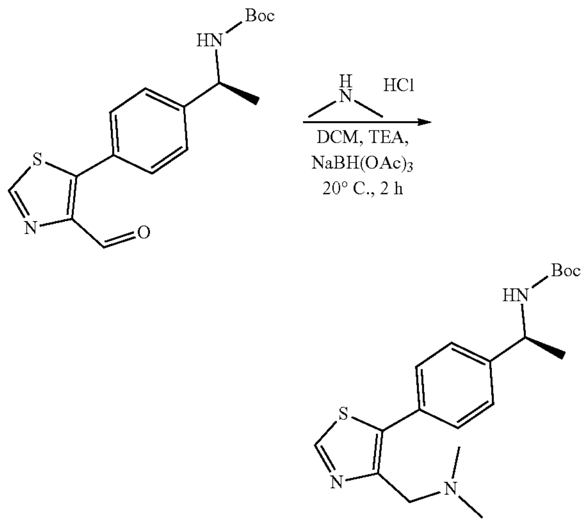

To a solution of dimethylamine hydrochloride (368 mg, 4.51 mmol, 0.41 mL, 3 eq) in dichloromethane (30 mL) was added triethylamine (609 mg, 6.02 mmol, 0.84 mL, 4 eq), a solution of tert-butyl N-[(1S)-1-[4-(4-formylthiazol-5-yl) phenyl]ethyl]carbamate (500 mg, 1.50 mmol, 1 eq) in dichloromethane (10 mL), and sodium triacetoxyborohydride (1.28 g, 6.02 mmol, 4 eq), and the mixture was stirred at 20° C. for 2 hours. The reaction mixture was quenched by addition of water (50 mL), and extracted with dichloromethane (40 mL) two times. The combined organic layers were washed with saturated aqueous sodium chloride (60 mL) two times, dried over anhydrous sodium sulfate and concentrated to give product. The crude product was purified by silica gel chromatography (petroleum ether:ethyl acetate=1:0 to 0:1). Compound tert-butyl N-[(1S)-1-[4-[4-(dimethylamino)methyl]thiazol-5-yl]phenyl]ethyl]carbamate (364 mg, 1.01 mmol, 67% yield) was obtained as a yellow oil.

Step 1

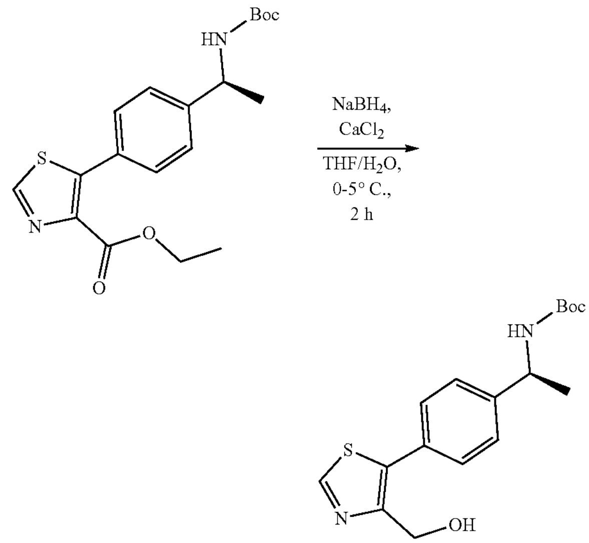

To a mixture of ethyl 5-[4-[(1S)-1-(tert-butoxycarbonylamino)ethyl]phenyl]thiazole-4-carboxylate (900 mg, 2.39 mmol, 1 eq) and calcium chloride (796 mg, 7.17 mmol, 3 eq) in water (40 mL) and tetrahydrofuran (20 mL) was added sodium borohydride (181 mg, 4.78 mmol, 2 eq) at 0° C. under nitrogen. The mixture was warmed to 5° C. and stirred for 2 hours. Hydrochloric acid (5 M, 4.50 mL) and acetone (4.95 mL) were added at 0° C., and the reaction mixture was stirred at 5° C. for another 0.5 hour. The pH was adjusted to 5 with 5 M sodium hydroxide. The aqueous phase was extracted with ethyl acetate (20 mL×4). The combined organic phase was washed with brine (20 mL×2), dried with anhydrous sodium sulfate, filtered and concentrated under vacuum. The residue was purified by semi-preparative reverse phase HPLC (basic condition, column: Waters Xbridge 150*50 10 um; mobile phase: [water (0.05% ammonia hydroxide v/v)-ACN]; B %: 25%-55%, 11.5 min).

Compound tert-butyl N-[(1S)-1-[4-[4-(hydroxymethyl)thiazol-5-yl]phenyl]ethyl]carbamate (400 mg, 1.20 mmol, 50% yield) was obtained as a white solid.

tert-Butyl N-[(1S)-1-[4-[4-(hydroxymethyl)thiazol-5-yl] phenyl]ethyl]carbamate was converted to the final product using procedures described for exemplary compound 76.

Exemplary compounds 211 and 219 are also prepared using procedures analogous to those described above.

Exemplary Synthesis of Exemplary Compound 169

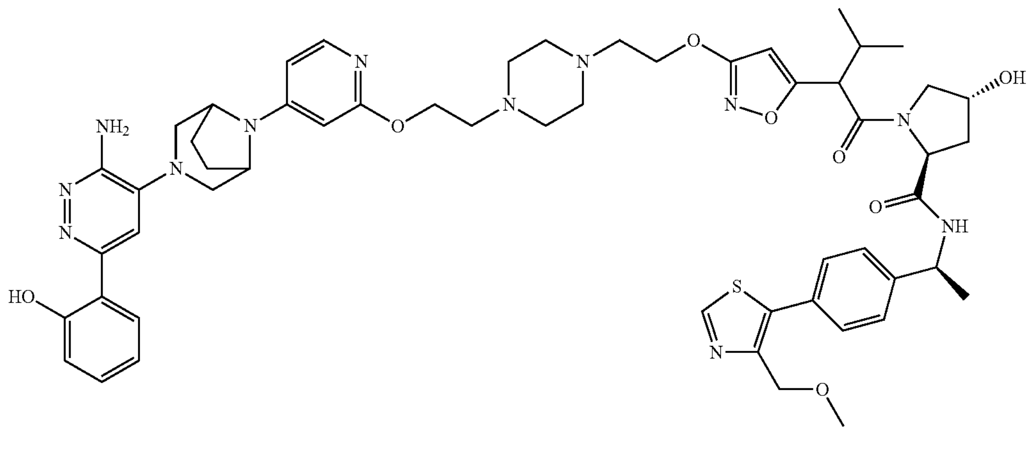

Ex. 168

Step 1

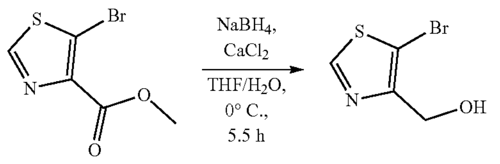

Prepared using procedure described for exemplary compound 168.

Step 2

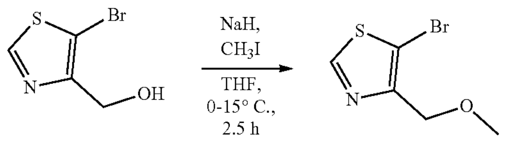

To a solution of (5-bromothiazol-4-yl)methanol (980 mg, 5.05 mmol, 1 eq) in THF (30 mL) was added sodium hydride (404 mg, 10.10 mmol, 2 eq) at 0° C. under nitrogen. The mixture was stirred at 0° C. for 30 minutes, and iodomethane (3.58 g, 25.25 mmol, 1.57 mL, 5 eq) was then added at 0° C. The mixture was stirred at 15° C. for 2 hours under nitrogen. The mixture was cooled to 0° C., quenched by a saturated aqueous solution of ammonium chloride slowly and then extracted with ethyl acetate (50 mL×3). The combined organic phase was washed with brine (25 mL×2), dried with anhydrous sodium sulfate, filtered and concentrated under vacuum. The residue was purified by silica gel chromatography (petroleum ether/ethyl acetate=20/1 to 10/1) to afford 5-bromo-4-(methoxymethyl)thiazole (910 mg, 4.37 mmol, 86% yield) as a yellow solid.

Step 3

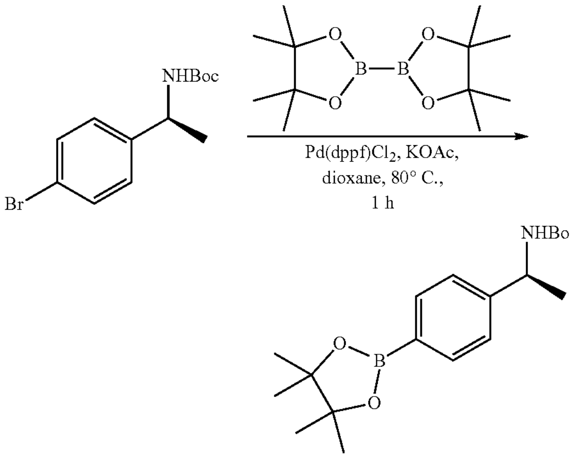

A flask was charged with tert-butyl N-[(1S)-1-(4-bromophenyl)ethyl]carbamate (1.4 g, 4.66 mmol, 1 eq), 4,4,5,5-tetramethyl-2-(4,4,5,5-tetramethyl-1,3,2-dioxaborolan-2-yl)-1,3,2-dioxaborolane (1.42 g, 5.60 mmol, 1.2 eq), (1,1'-bis(diphenylphosphino)ferrocene)palladium(II) dichloride (170 mg, 0.23 mmol, 0.05 eq), potassium acetate (915 mg, 9.33 mmol, 2 eq) and dioxane (30 mL). The mixture was purged with nitrogen for 10 minutes, then heated to 80° C. for 1 hour. The reaction mixture was cooled to 20° C. and filtered through a pad of celite. The filtrate was concentrated in vacuum. The crude product was purified by flash chromatography (petroleum ether:ethyl acetate=10:1). Tert-Butyl N-[(1S)-1-[4-(4,4,5,5-tetramethyl-1,3,2-dioxaborolan-2-yl)phenyl]ethyl]carbamate (1.9 g, crude) was obtained as a colorless oil.

Step 4

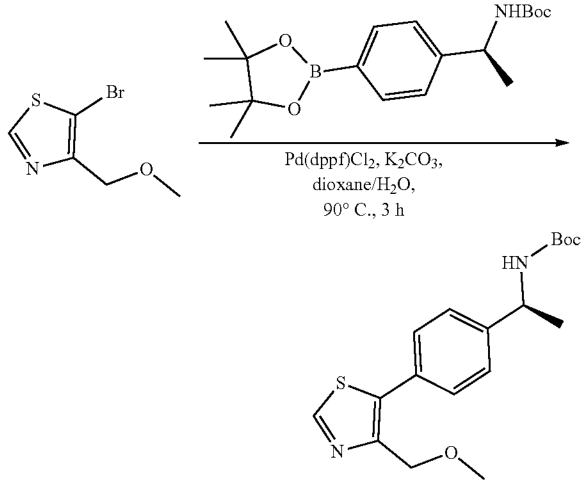

To a mixture of 5-bromo-4-(methoxymethyl)thiazole (900 mg, 4.33 mmol, 1 eq) and tert-butyl N-[(1S)-1-[4-(4,4,5,5-tetramethyl-1,3,2-dioxaborolan-2-yl)phenyl]ethyl]carbamate (2.25 g, 6.49 mmol, 1.5 eq) in dioxane (30 mL) and water (5 mL) was added potassium carbonate (1.20 g, 8.65 mmol, 2 eq) and [1,1'-bis(diphenylphosphino)ferrocene]dichloropalladium(II) (316 mg, 0.43 mmol, 0.1 eq) in one portion at 15° C. under nitrogen. The mixture was stirred at 90° C. for 3 hours. The mixture was cooled to 15° C., filtered and concentrated under vacuum. The residue was purified by silica gel chromatography (petroleum ether/ethyl acetate=10/1 to 1/1) to afford tert-butyl N-[(1S)-1-[4-[4-(methoxymethyl)thiazol-5-yl]phenyl]ethyl]carbamate (1.87 g, crude) as a yellow solid.

tert-Butyl N-[(1S)-1-[4-[4-(methoxymethyl)thiazol-5-yl]phenyl]ethyl]carbamate tert-Butyl N-[(1S)-1-[4-[4-(hydroxymethyl)thiazol-5-yl]phenyl]ethyl]carbamate was converted to the final product using procedures described for exemplary compound 76.

Exemplary compound 184 and 185 were also prepared using procedures analogous to those described above.

Exemplary Synthesis of Exemplary Compound 170 and 134

Ex. 170

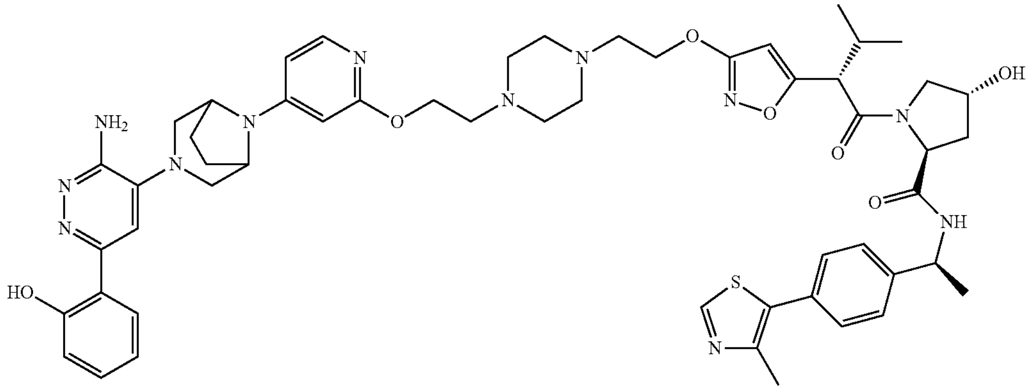

Ex. 134

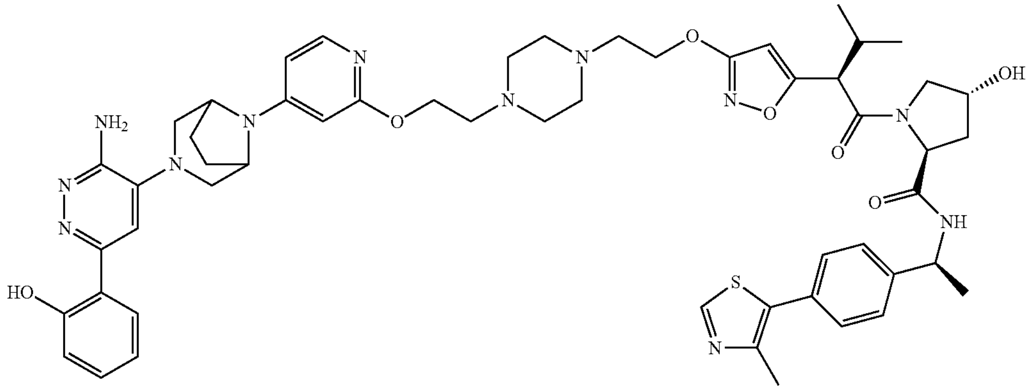

Step 1

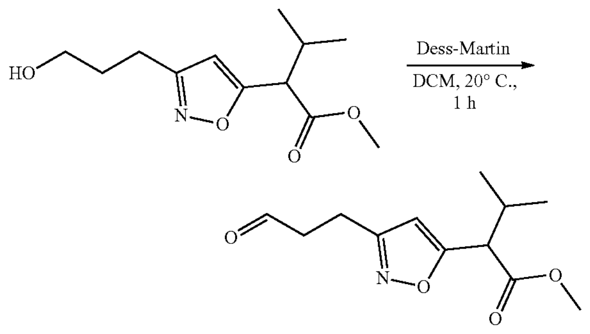

To a solution of methyl 2-[3-(3-hydroxypropyl)isoxazol-5-yl]-3-methyl-butanoate (460 mg, 1.91 mmol, 1 eq) in dichloromethane (5 mL) was added Dess-Martin periodinane (970 mg, 2.29 mmol, 1.2 eq). The reaction mixture was stirred at 20° C. for 1 hour. Ethyl acetate (50 mL) was added to the mixture, and the mixture was filtered, and the filtrate was concentrated in vacuum. The organic phase was washed with water (20 mL) and brine (20 mL), dried over sodium sulfate, filtered and concentrated in vacuum. The residue was purified by silica gel chromatography (petroleum ether: ethyl acetate=100:1 to 50:1). Methyl 3-methyl-2-[3-(3-oxopropyl)isoxazol-5-yl]butanoate (300 mg, 1.25 mmol, 65% yield) was obtained as a colorless oil.

Methyl 3-methyl-2-[3-(3-oxopropyl)isoxazol-5-yl]butanoate was converted to the final compounds according to the scheme below using procedures described above for other examples.

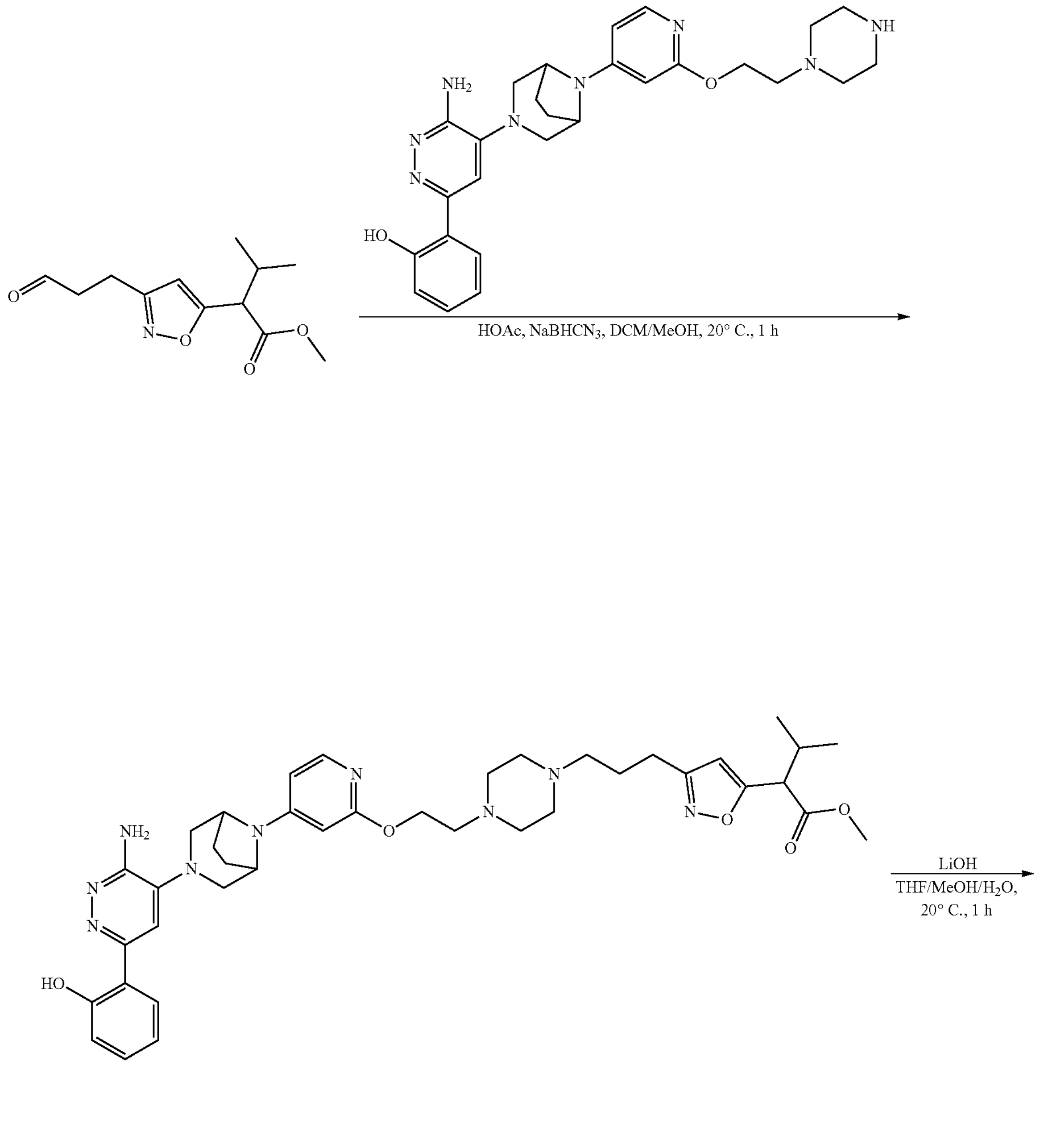

-continued
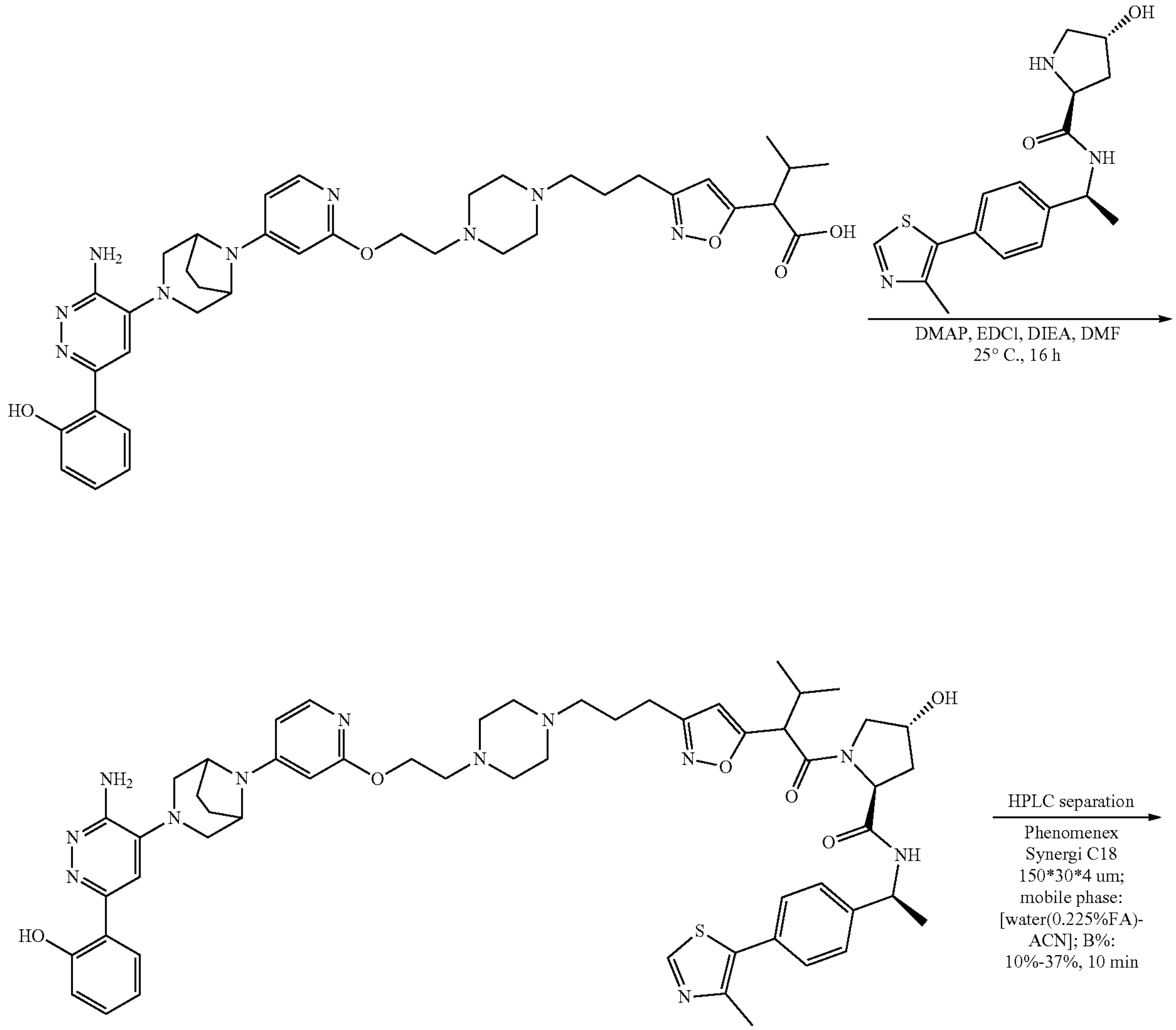
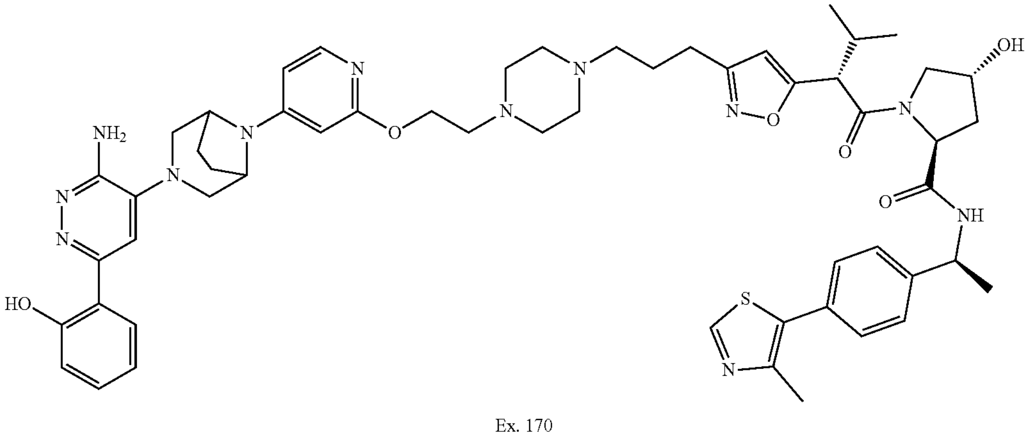
+
Ex. 170

-continued

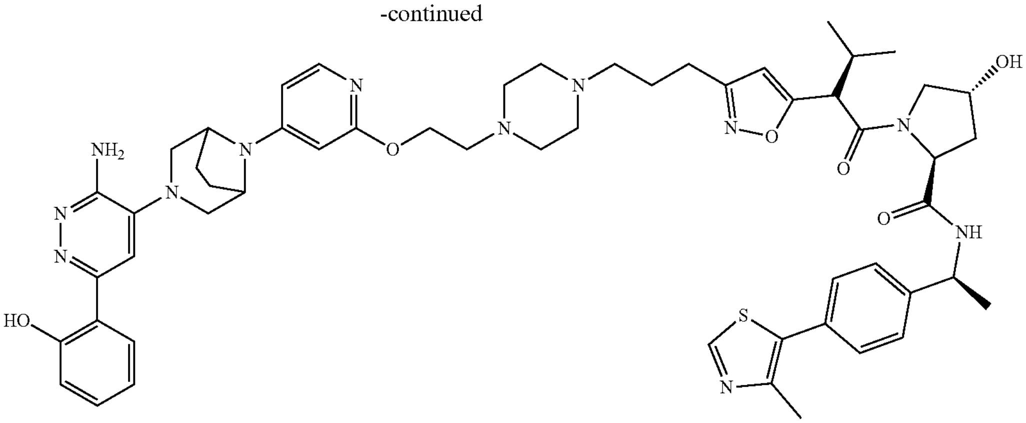

Ex. 134

Exemplary compounds 190 and 191 were preparing using procedures analogous to those described above.

Exemplary Synthesis of Exemplary Compound 112

Step 2

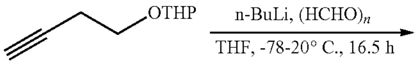

Ex. 112

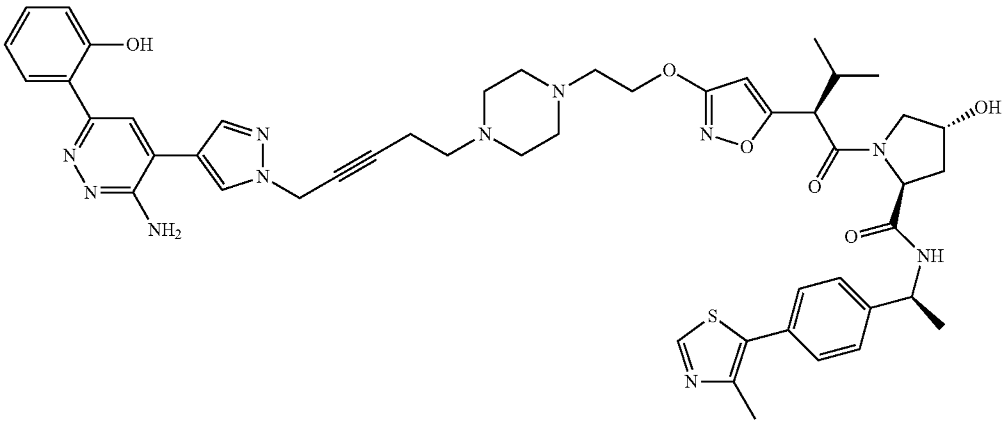

Step 1

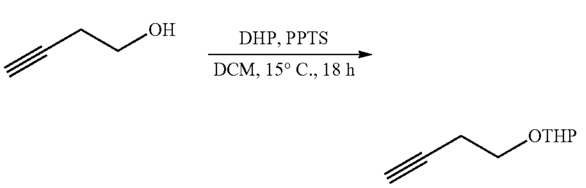

To a solution of but-3-yn-1-ol (5 g, 71.34 mmol, 1 eq) in dichloromethane (150 mL) was added pyridinium p-toluenesulfonate (1.9 g, 7.56 mmol, 0.1 eq) and 3,4-dihydro-2H-pyran (9.48 g, 112.70 mmol, 10.3 mL, 1.58 eq) at 15° C., and the mixture was stirred at 15° C. for 18 hours. The mixture was concentrated to give a residue. The residue was purified by silica gel chromatography (petroleum ether:ethyl acetate=1:0 to 10:1). 2-But-3-ynoxytetrahydropyran (10.6 g, 68.74 mmol, 96% yield) was obtained as a colorless oil.

-continued

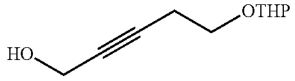

To a solution of 2-but-3-ynoxytetrahydropyran (2 g, 12.97 mmol, 1 eq) in tetrahydrofuran (20 mL) was added n-butyllithium (2.5 M, 5.7 mL, 1.1 eq) at −78° C., and the mixture was stirred at −78° C. for 1 hour. Then paraformaldehyde (2.10 g, 23.35 mmol, 1.8 eq) was added to the mixture and stirred at −78° C. for 30 minutes and at 20° C. for 15 hours. The mixture was quenched with saturated ammonium chloride solution (80 mL) and extracted with ethyl acetate (2×40 mL). The combined organic phase was dried over sodium sulfate and then concentrated to give a residue. The residue was purified by column chromatography (petroleum ether: ethyl acetate=3:1 to 0:1). 5-tetrahydropyran-2-yloxypent-2-yn-1-ol (1.4 g, 7.60 mmol, 58% yield) was obtained as a colorless oil.

Step 3

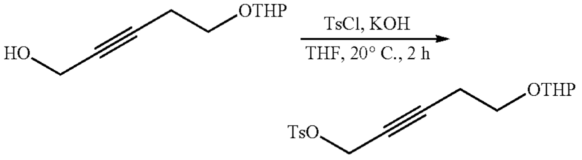

To a mixture of 5-tetrahydropyran-2-yloxypent-2-yn-1-ol (1.4 g, 7.60 mmol, 1 eq) and p-toluensulfonyl chloride (2.90 g, 15.20 mmol, 2 eq) in tetrahydrofuran (15 mL) was added potassium hydroxide (2.13 g, 38.00 mmol, 5 eq). Then the reaction mixture was stirred at 20° C. for 2 hours. The reaction mixture was diluted with water (30 mL), and then extracted with ethyl acetate (30 mL×3). The combined organic layers were washed with brine (20 mL×2), dried over sodium sulfate, filtered and concentrated under reduced pressure to give a residue. The residue was purified by column chromatography (petroleum ether:ethyl acetate=50:1 to 10:1). Compound 5-tetrahydropyran-2-yloxypent-2-ynyl 4-methylbenzenesulfonate (2.5 g, 7.39 mmol, 97% yield) was obtained as a colorless oil.

Step 4

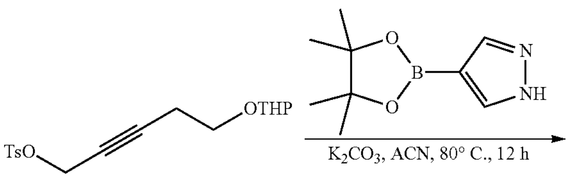

-continued

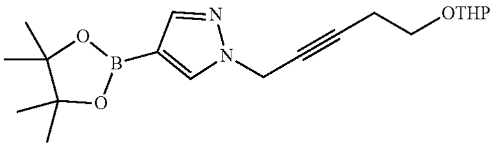

To a solution of 5-tetrahydropyran-2-yloxypent-2-ynyl 4-methylbenzenesulfonate (2.5 g, 7.39 mmol, 1 eq), 4-(4,4,5,5-tetramethyl-1,3,2-dioxaborolan-2-yl)-1H-pyrazole (1.72 g, 8.86 mmol, 1.2 eq) in acetonitrile (20 mL) was added potassium carbonate (2.04 g, 14.77 mmol, 2 eq). Then the reaction mixture was stirred at 80° C. for 12 hours. The reaction mixture was diluted with water (30 mL), and then extracted with ethyl acetate (30 mL×3). The combined organic layers were washed with brine (20 mL×2), dried over sodium sulfate, filtered and concentrated under reduced pressure to give a residue. The residue was purified by column chromatography (petroleum ether:ethyl acetate=50:1 to 10:1). Compound 1-(5-tetrahydropyran-2-yloxypent-2-ynyl)-4-(4,4,5,5-tetramethyl-1,3,2-dioxaborolan-2-yl)pyrazole (2 g, 5.55 mmol, 75% yield) was obtained as a light yellow oil.

1-(5-Tetrahydropyran-2-yloxypent-2-ynyl)-4-(4,4,5,5-tetramethyl-1,3,2-dioxaborolan-2-yl)pyrazole was converted to the final compound according to the scheme below using procedures described above for other examples.

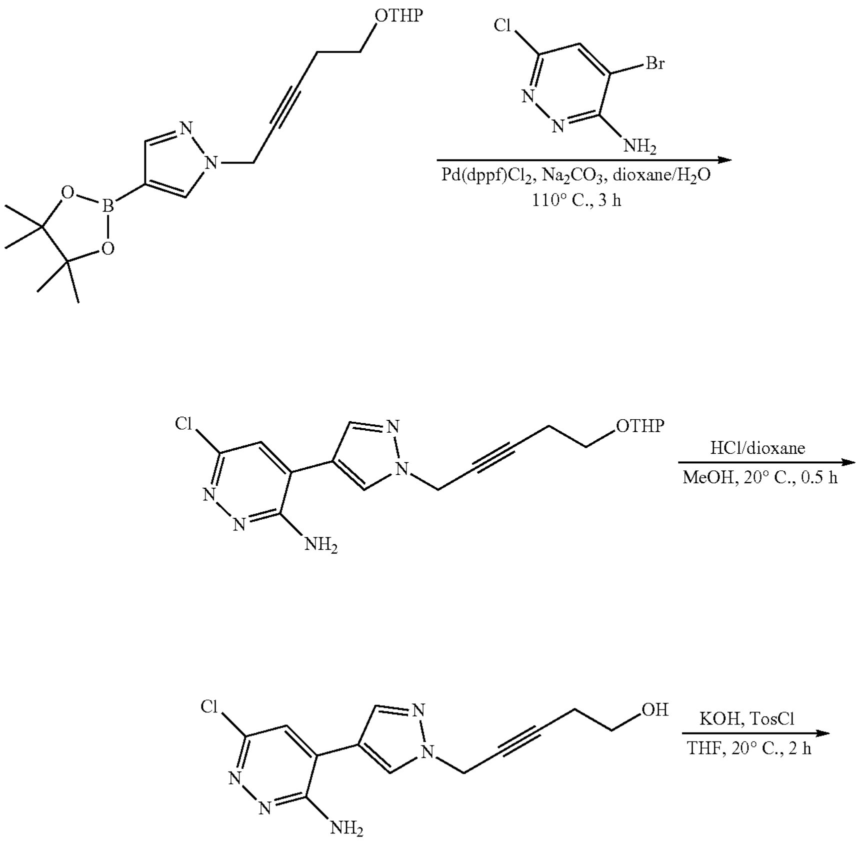

-continued
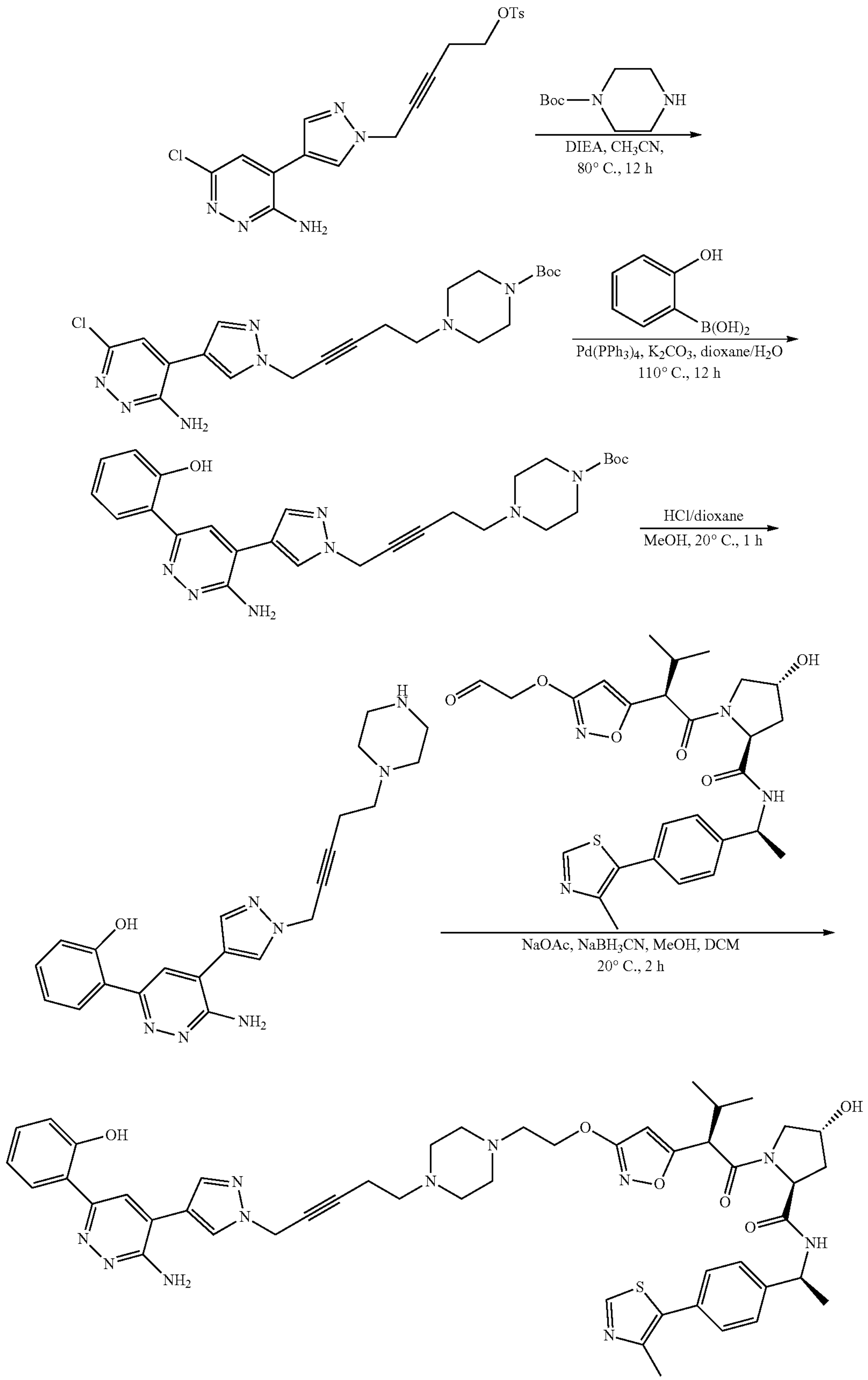
Ex. 112

Exemplary Synthesis of Exemplary Compound 131

Ex. 131

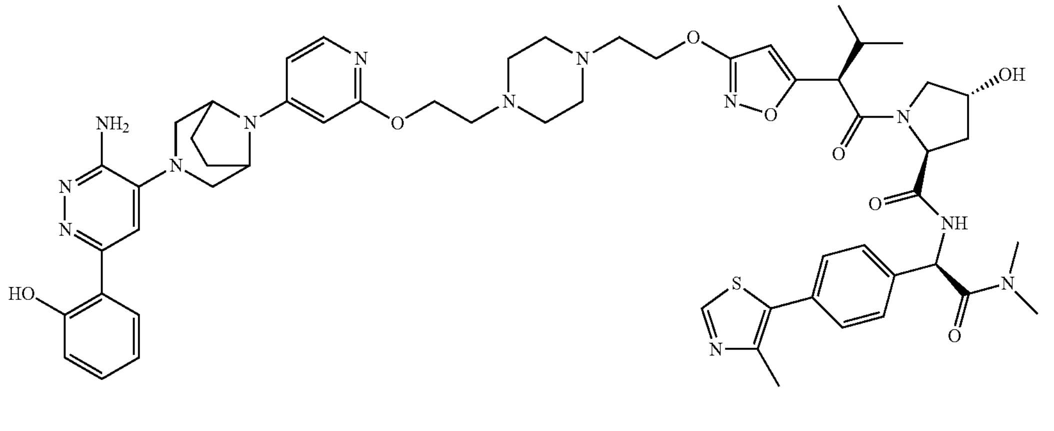

(2S,4R)—N—((R)-2-(dimethylamino)-1-(4-(4-methythiazol-5-yl)phenyl)-2-oxoethyl)-4-hydroxypyrrolidine-2-carboxamide was prepared according to scheme below using procedures described for other examples above and obvious to those skilled in the art.

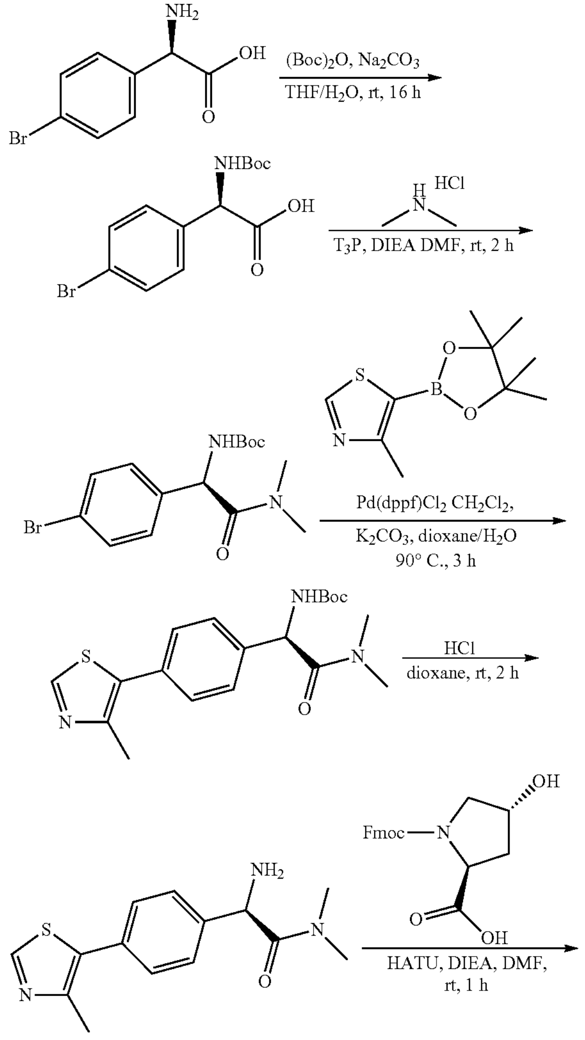

-continued

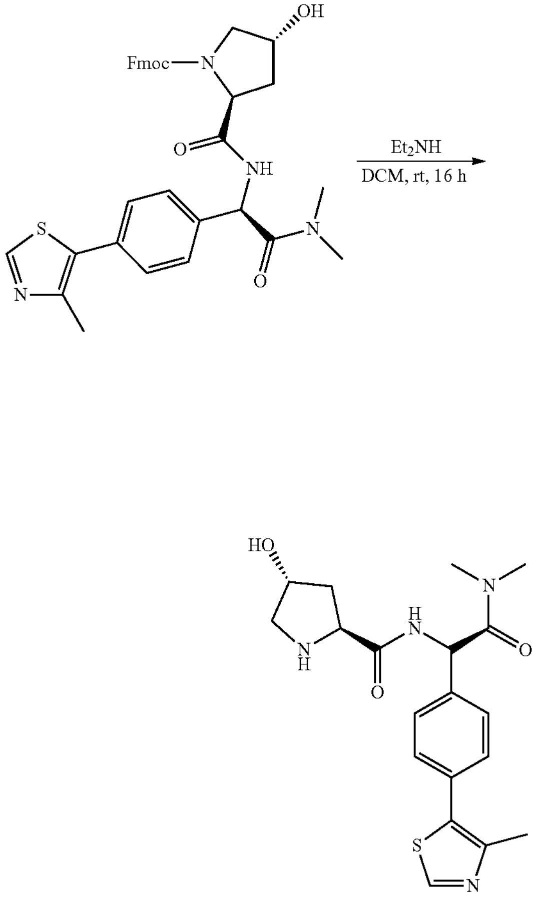

(2S,4R)—N—((R)-2-(dimethylamino)-1-(4-(4-methylthiazol-5-yl)phenyl)-2-oxoethyl)-4-hydroxypyrrolidine-2-carboxamide was converted to the final compound using procedures described for other examples above.

Exemplary compound 171 was prepared using analogous procedures.

Exemplary Synthesis of Exemplary Compound 172

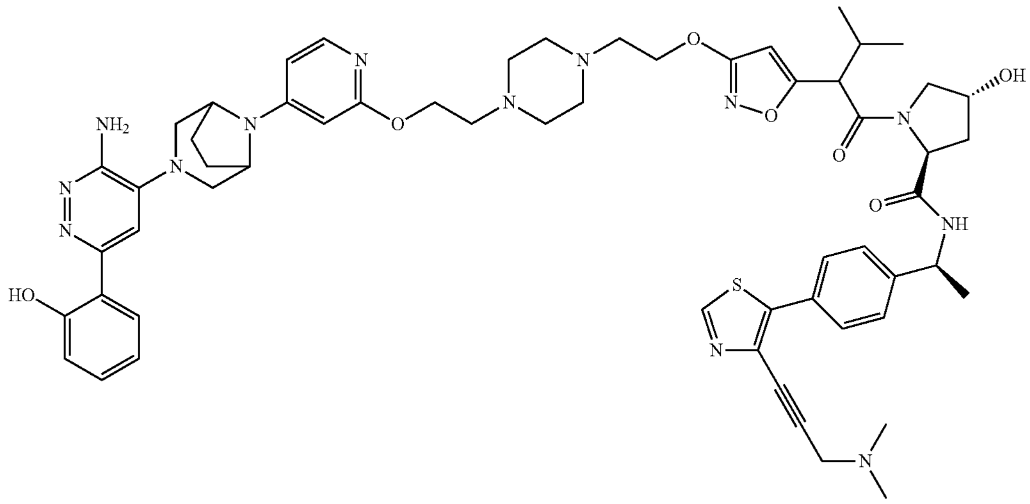

Ex. 172

Step 1

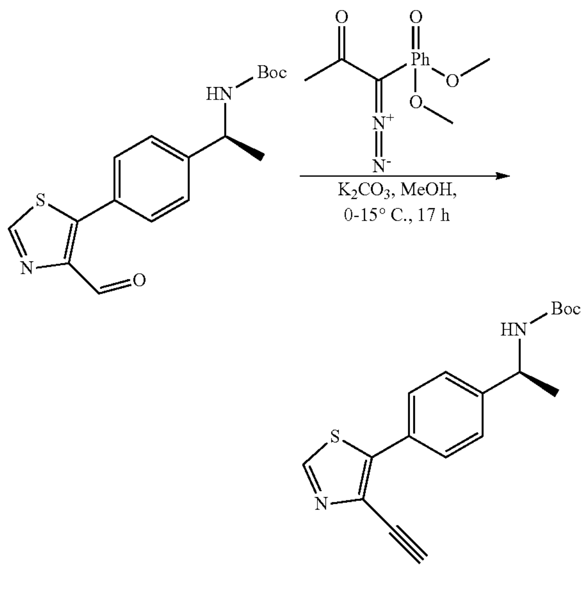

To a solution of tert-butyl N-[(1S)-1-[4-(4-formylthiazol-5-yl)phenyl]ethyl]carbamate (2 g, 6.02 mmol, 1 eq) and 1-diazo-1-dimethoxyphosphoryl-propan-2-one (1.16 g, 6.02 mmol, 1 eq) in methanol (20 mL) was added potassium carbonate (1.66 g, 12.03 mmol, 2 eq) at 0° C. The reaction mixture was stirred at 15° C. for 16 hours. Then 1-diazo-1-dimethoxyphosphoryl-propan-2-one (116 mg, 0.60 mmol, 0.1 eq) was added, and the reaction mixture was stirred at 15° C. for another 1 hour. Ethyl acetate (50 mL) and water (40 mL) were added, and the mixture was separated. The organic layer was dried over sodium sulfate and then concentrated under vacuum to get the residue which was purified by silica gel column chromatography (10-30% ethyl acetate in petroleum ether) to afford tert-butyl N-[(1S)-1-[4-(4-ethynylthiazol-5-yl)phenyl]ethyl]carbamate (1.8 g, 5.48 mmol, 91% yield) as a white solid.

Step 2

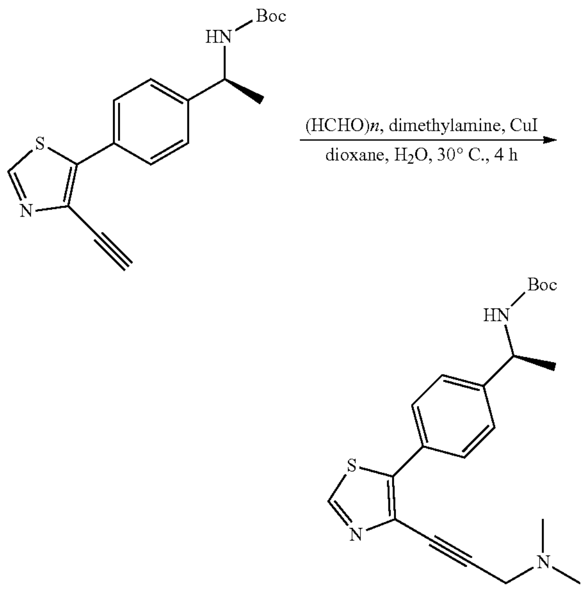

To a solution of tert-butyl N-[(1S)-1-[4-(4-ethynylthiazol-5-yl)phenyl]ethyl]carbamate (400 mg, 1.22 mmol, 1 eq), dimethylamine (1.37 g, 12.18 mmol, 1.54 mL, 10 eq) and triformol (362 mg, 4.02 mmol, 3.3 eq) in dioxane (8 mL) was added cuprous iodide (232 mg, 1.22 mmol, 1 eq) at 0° C. The reaction mixture was degassed and charged with nitrogen for 3 times and then stirred at 30° C. for 4 hours. The reaction solution was concentrated under vacuum to get the residue. The residue was purified by silica gel column chromatography (0-8% methanol in dichloromethane) to obtain tert-butyl N-[(1S)-1-[4-[4-[3-(dimethylamino)prop-1-ynyl]thiazol-5-yl]phenyl]ethyl]carbamate (274 mg, 0.71 mmol, 58% yield) as a light yellow gum.

tert-Butyl N-[(1S)-1-[4-[4-[3-(dimethylamino)prop-1-ynyl]thiazol-5-yl]phenyl]ethyl]carbamate was converted to the final compound using procedures described for exemplary compound 76.

Exemplary Synthesis of Exemplary Compound 132 under vacuum. The residue was purified by silica gel chromatography (petroleum ether) to afford 4-bromo-2-(2,2-diethoxyethoxy)pyridine (22.8 g, 74.7 mmol, 66% yield) as a yellow oil.

Step 2

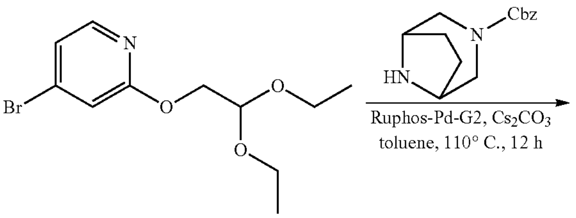

Ex. 132

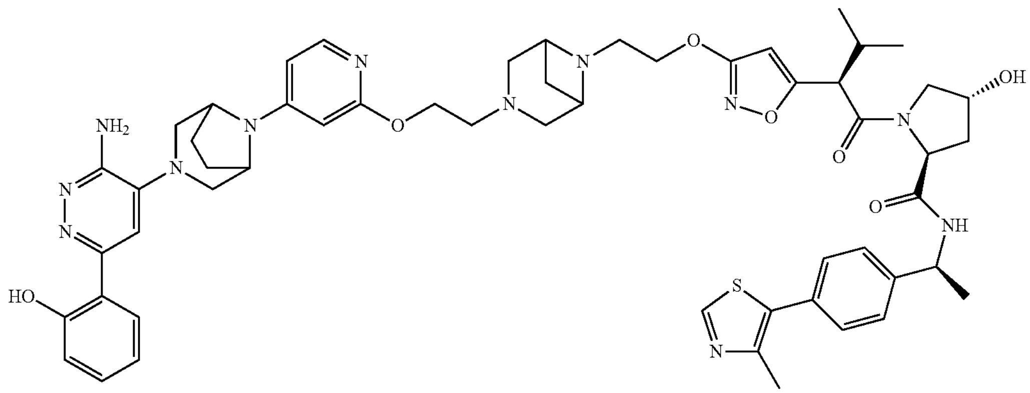

Step 1

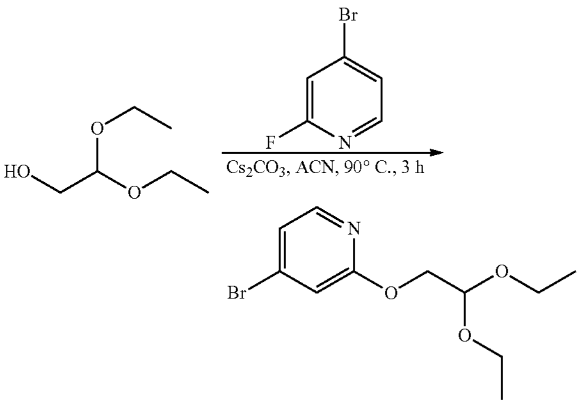

To a mixture of 2,2-diethoxyethanol (22.87 g, 170 mmol, 1.5 eq) and 4-bromo-2-fluoro-pyridine (20 g, 113.65 mmol, 1 eq) in acetonitrile (200 mL) was added cesium carbonate (74.06 g, 227 mmol, 2 eq) in one portion at 15° C. under nitrogen. The mixture was stirred at 90° C. for 3 hours. The mixture was cooled to 20° C. and filtered and concentrated -continued

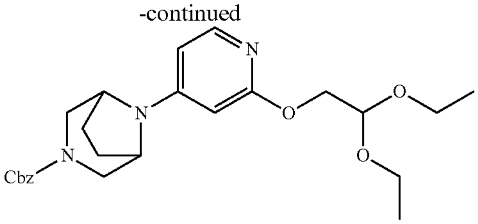

To a mixture of 4-bromo-2-(2,2-diethoxyethoxy)pyridine (10 g, 34.46 mmol, 1 eq) and benzyl 3,8-diazabicyclo[3.2.1]octane-3-carboxylate (8.49 g, 34.46 mmol, 1 eq) in toluene (200 mL) was added cesium carbonate (22.46 g, 68.93 mmol, 2 eq) and [2-(2-aminophenyl)phenyl]-chloro-palladium dicyclohexyl-[2-(2,6-diisopropoxyphenyl)phenyl]phosphane (1.61 g, 2.07 mmol, 0.06 eq) in one portion at 15° C. under nitrogen. The mixture was stirred at 110° C. for 12 hours. The mixture was cooled to 20° C., filtered and concentrated under vacuum. The residue was purified by silica gel chromatography (petroleum ether/ethyl acetate=10/1, 3/1) to afford benzyl 8-[2-(2,2-diethoxyethoxy)-4-pyridyl]-3,8-diazabicyclo[3.2.1]octane-3-carboxylate (12.1 g, 26.6 mmol, 77% yield) as a yellow oil.

Step 3

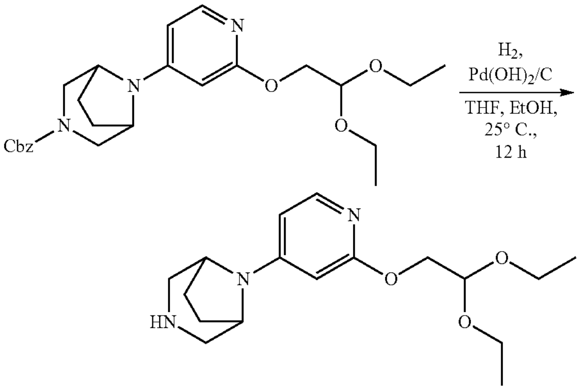

To a solution of benzyl 8-[2-(2,2-diethoxyethoxy)-4-pyridyl]-3,8-diazabicyclo[3.2.1]octane-3-carboxylate (13.1 g, 28.76 mmol, 1 eq) in tetrahydrofuran (300 mL) and ethanol (300 mL) was added 10% palladium hydroxide on carbon (4.04 g, 2.88 mmol, 0.1 eq) under nitrogen. The suspension was degassed under vacuum and purged with hydrogen several times. The mixture was stirred under hydrogen (50 psi) at 60° C. for 12 hours. The reaction mixture was filtered, and the filtrate was concentrated. The crude 8-[2-(2,2-diethoxyethoxy)-4-pyridyl]-3,8-diazabicyclo[3.2.1]octane (8.27 g, 25.73 mmol, 89.47% yield) was obtained as a brown oil.

8-[2-(2,2-diethoxyethoxy)-4-pyridyl]-3,8-diazabicyclo [3.2.1]octane was converted to the final compound according to the scheme below using procedures described for other examples above as well as standard procedures obvious to those skilled in the art.

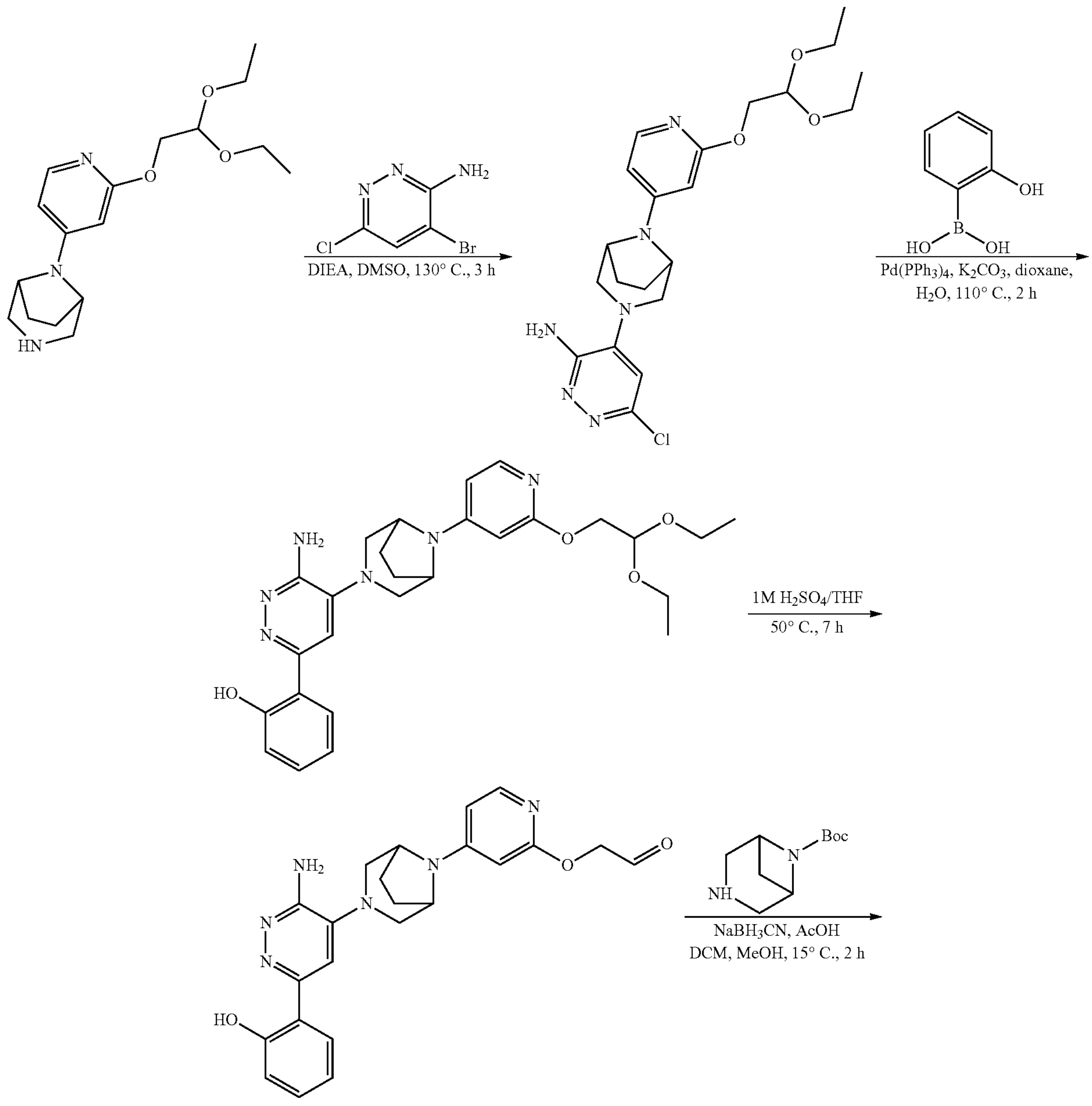

-continued
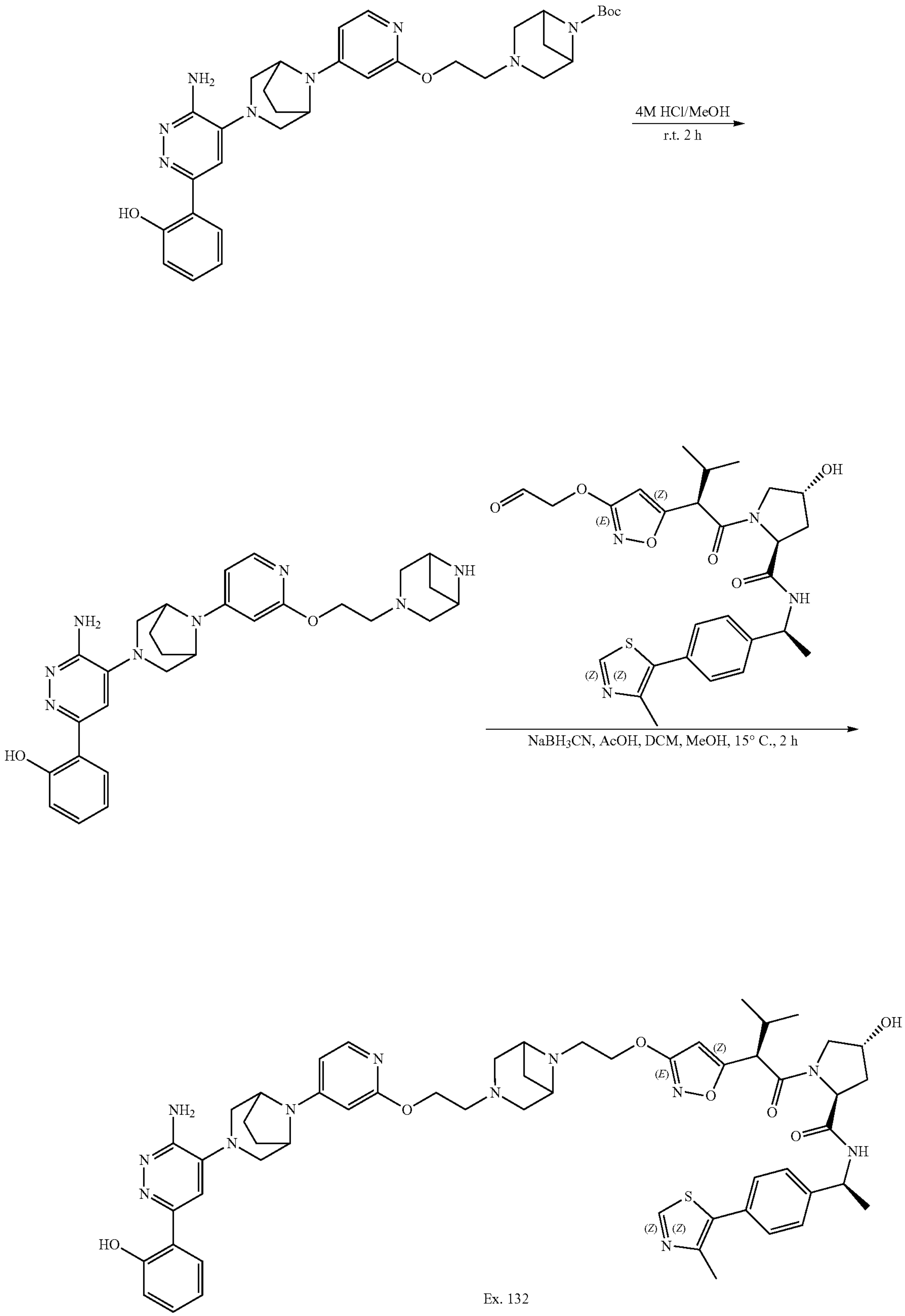
Ex. 132

Using procedures analogous to those described for exemplary compound 132 the following exemplary compounds were prepared: 135, 136, 139, 141, 133, 140, 142, and 210.

Exemplary Synthesis of Exemplary Compounds 173 and 102

Ex. 173

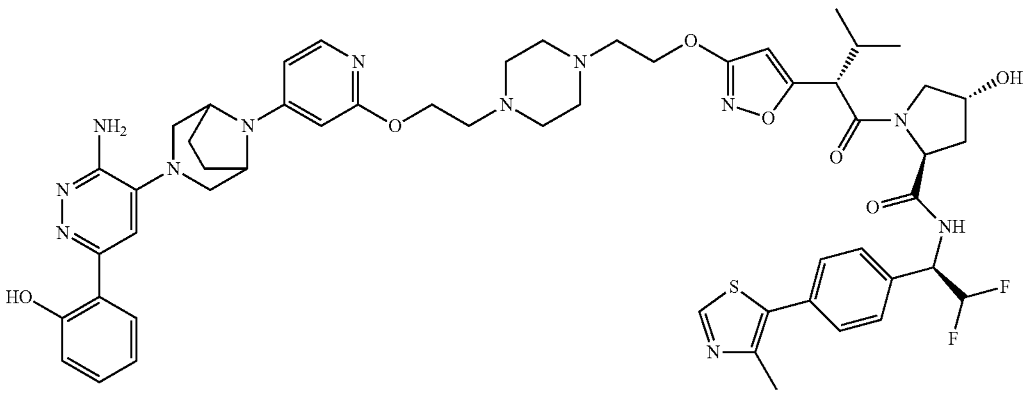

Ex. 102

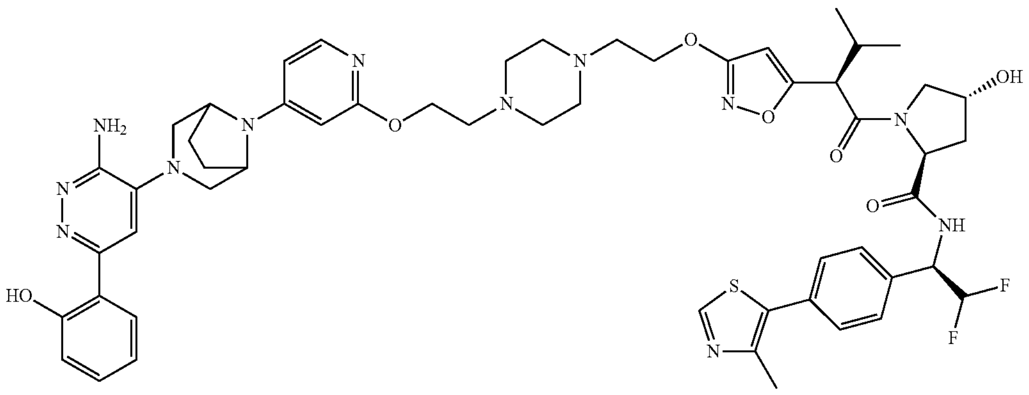

Step 1

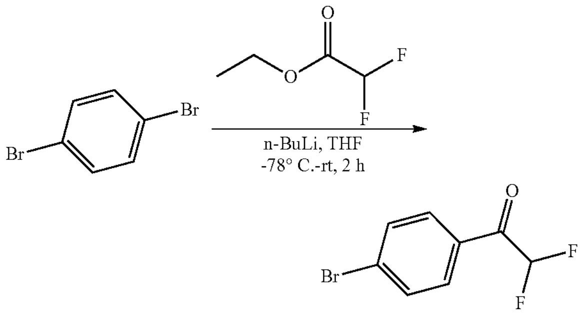

Into a 250-mL 3-neck round-bottom flask purged and maintained with an inert atmosphere of nitrogen, was placed 1,4-dibromobenzene (12.0 g, 50.8 mmol, 1.0 equiv) in THF (150.0 mL) at −78° C. Then n-butyllithium solution (1 M in hexane, 60.9 mL, 60.9 mmol, 1.2 equiv) was added at −78° C. The resulting mixture was stirred for 30 minutes at −78° C., and then ethyl 2,2-difluoroacetate (12.6 g, 101.5 mmol, 2.0 equiv) was added slowly at −78° C. The cooling bath was removed, and the resulting mixture was stirred for an additional 1 hour at room temperature. The reaction was then quenched by the addition of 50 mL water. The resulting mixture was extracted with ethyl acetate (250 mL×3), and the organic layers were combined, washed with brine, dried over anhydrous sodium sulfate and concentrated under reduced pressure. The residue was applied onto a silica gel column eluting with ethyl acetate/petroleum ether (1:10). This resulted in 7.6 g (64%) of 1-(4-bromophenyl)-2,2-difluoroethan-1-one as a light yellow semi-solid.

Step 2

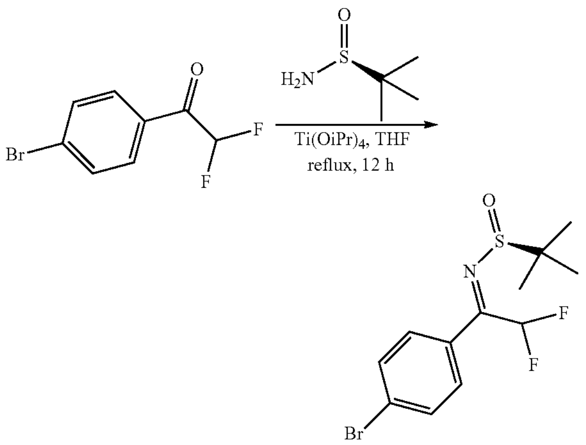

Into a 30-mL sealed tube purged and maintained with an inert atmosphere of nitrogen, was placed 1-(4-bromophenyl)-2,2-difluoroethan-1-one (3.5 g, 14.9 mmol, 1.0 equiv), (S)-2-methylpropane-2-sulfinamide (3.6 g, 29.8 mmol, 2.0 equiv) and tetrakis(propan-2-yloxy)titanium (12.7 g, 44.7 mmol, 3.0 equiv) in THF (10 mL) under nitrogen atmosphere. The resulting mixture was stirred for 14 hours at 80° C. in an oil bath under nitrogen atmosphere. The mixture was concentrated under reduced pressure. The residue was applied onto a silica gel column eluting with ethyl acetate/petroleum ether (1:5). This resulted in 2.8 g (56%) of (S)—N-[(1Z)-1-(4-bromophenyl)-2,2-difluoroethylidene]-2-methylpropane-2-sulfinamide as yellow oil.

Step 3

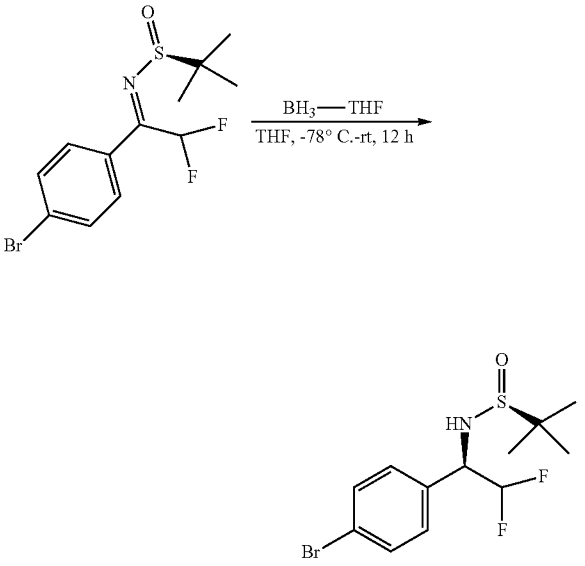

Into a 250-mL 3-neck round-bottom flask purged and maintained with an inert atmosphere of nitrogen, was placed (S)—N-[(1Z)-1-(4-bromophenyl)-2,2-difluoroethylidene]-2-methylpropane-2-sulfinamide (2.8 g, 8.3 mmol, 1 equiv) and a solution of $BH_3$-THF (40.0 mL, 40.0 mmol, 1.0 M, 4.8 equiv) in THF (40.0 mL) at 0° C. The resulting mixture was stirred for 1 h at 0° C., then warmed up to room temperature and stirred for an additional 6 hours at room temperature. The reaction was quenched by the addition of 100 mL water. The resulting mixture was extracted with ethyl acetate (100 mL×2). The organic layers were combined and concentrated under reduced pressure. The residue was applied onto a silica gel column eluting with dichloromethane/petroleum ether (1:1). This resulted in 1.3 g (45%) of (S)—N-[(1R)-1-(4-bromophenyl)-2,2-difluoroethyl]-2-methylpropane-2-sulfinamide as a white solid.

Step 4

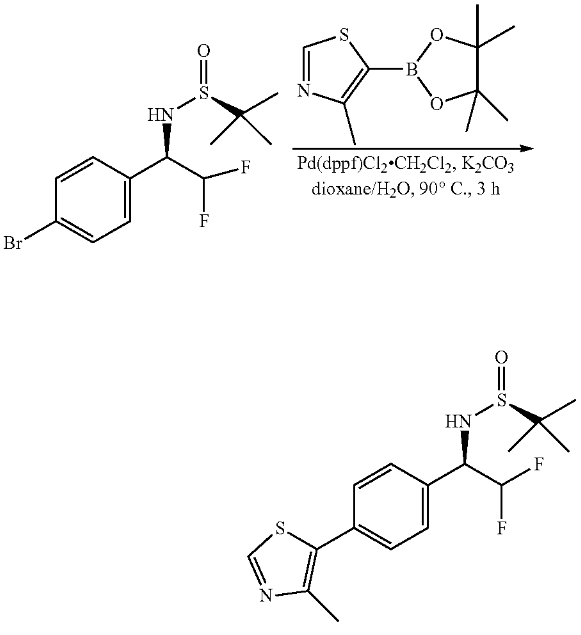

Into a 30-mL sealed tube purged and maintained with an inert atmosphere of nitrogen, was placed (S)—N-[(1R)-1-(4-bromophenyl)-2,2-difluoroethyl]-2-methylpropane-2-sulfinamide (1.3 g, 3.8 mmol, 1.0 equiv), 4-methyl-5-(4,4,5,5-tetramethyl-1,3,2-dioxaborolan-2-yl)-1,3-thiazole (1.25 g, 5.5 mmol, 1.5 equiv), $K_2CO_3$ (1.5 g, 11.3 mmol, 3.0 equiv) and Pd(dppf)C12 $CH_2Cl_2$ (62.0 mg, 0.08 mmol, 0.02 equiv) in dioxane (15.0 mL) and water (3.0 mL) under nitrogen atmosphere. The resulting suspension was stirred for 12 hours at 90° C. in an oil bath under nitrogen atmosphere. The mixture was concentrated under reduced pressure. The residue was applied onto a silica gel column eluting with ethyl acetate/petroleum ether (1:1). This resulted in 750.0 mg (56%) of (S)—N-[(1R)-2,2-difluoro-1-[4-(4-methyl-1,3-thiazol-5-yl)-phenyl]ethyl]-2-methylpropane-2-sulfinamide as a light yellow solid.

(S)—N-[(1R)-2,2-difluoro-1-[4-(4-methyl-1,3-thiazol-5-yl)-phenyl]ethyl]-2-methylpropane-2-sulfinamide was converted to the final compound according to the scheme below using procedures analogous to those described for other examples in this application.

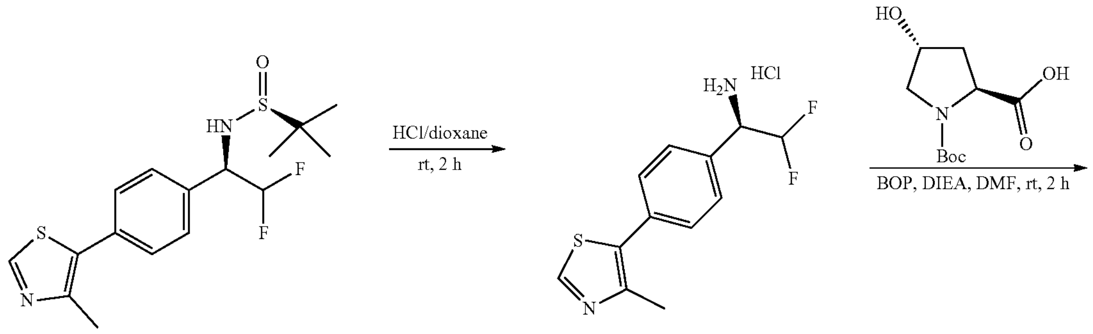

-continued
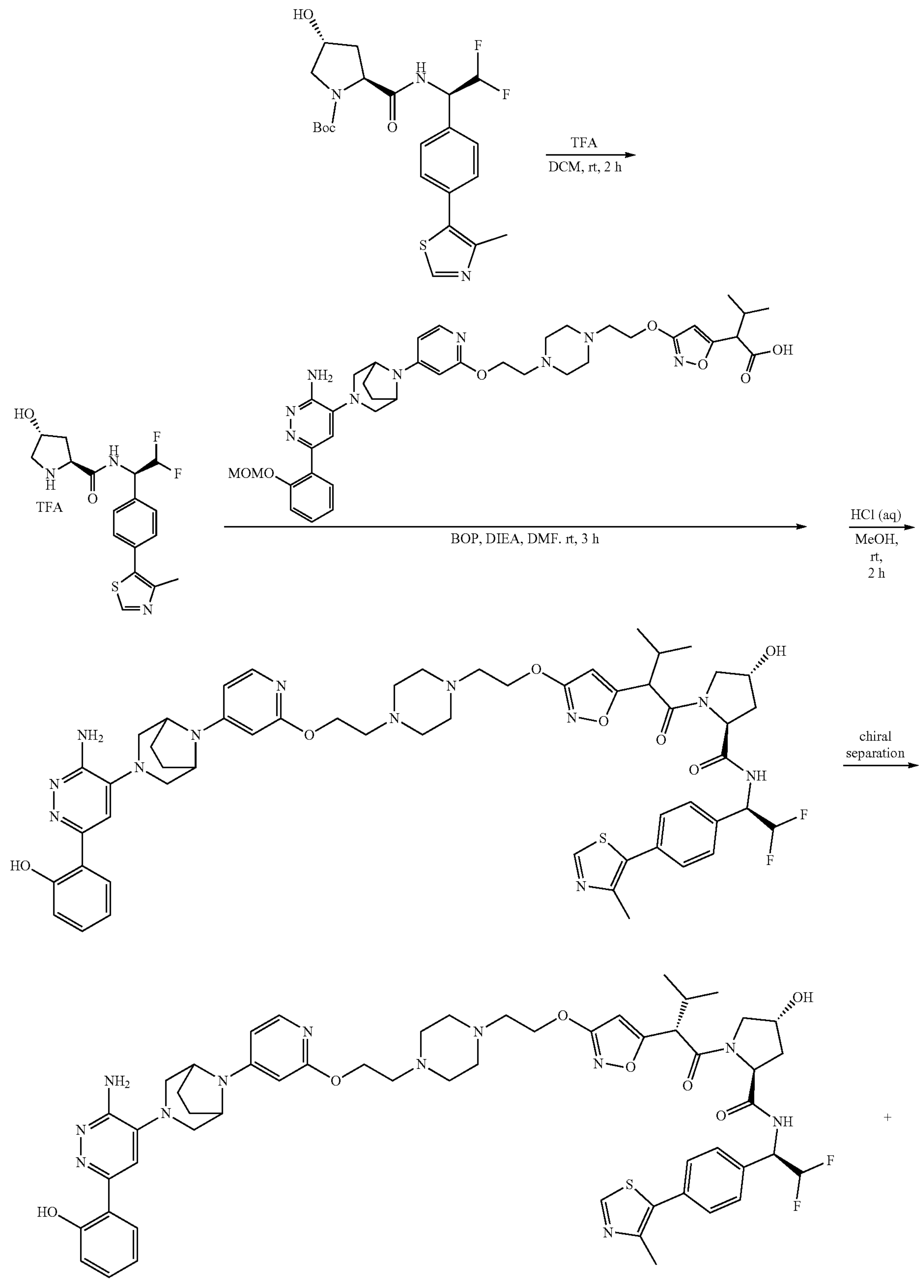
Ex. 173

-continued
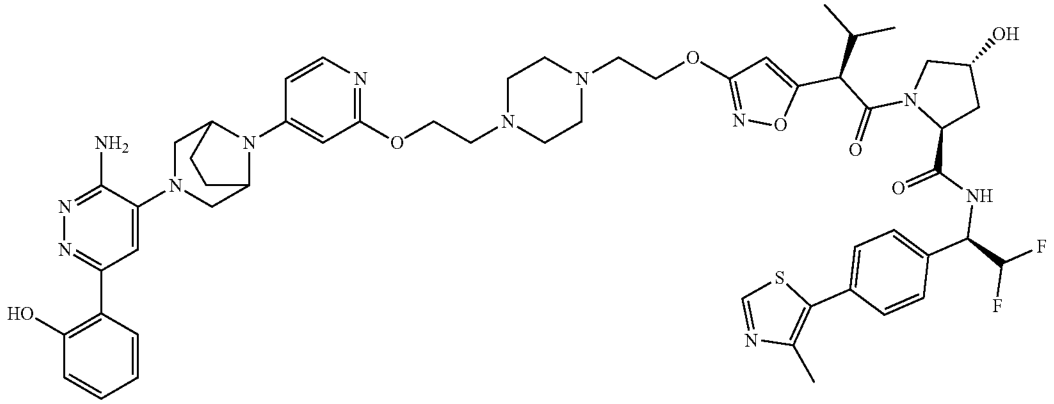
Ex. 102
Exemplary compound 267 and 268 were prepared using analogous procedures.
Exemplary Synthesis of Exemplary Compound 174
Ex. 174
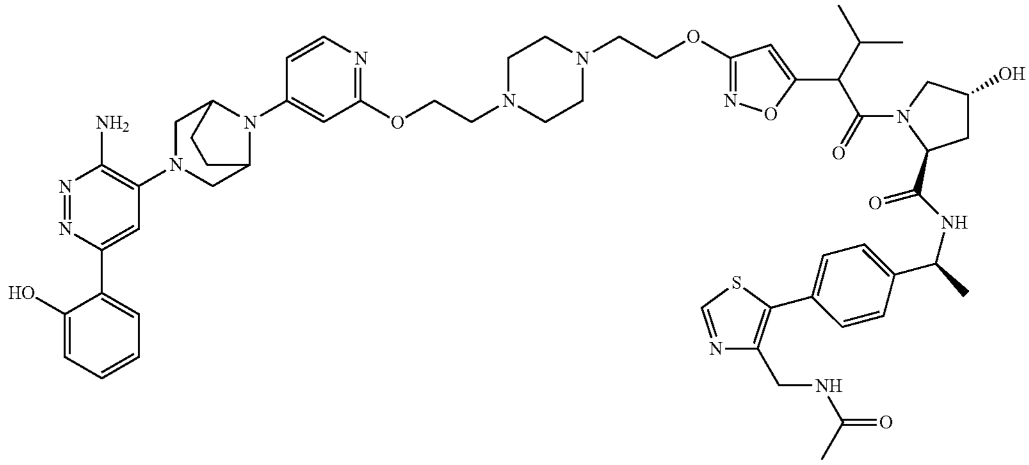
Step 1
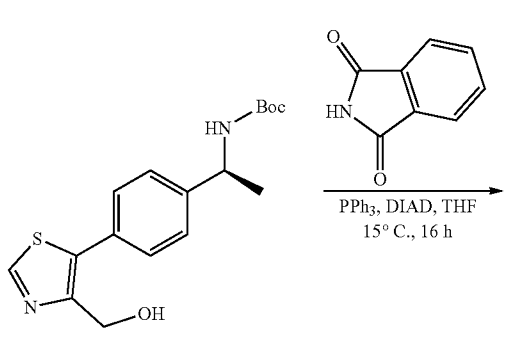
-continued
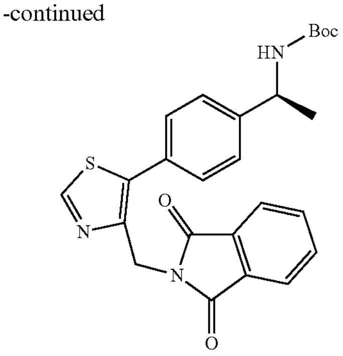
To a solution of tert-butyl N-[(1S)-1-[4-[4-(hydroxymethyl)thiazol-5-yl]phenyl]ethyl]carbamate (400 mg, 1.20 mmol, 1 eq), isoindoline-1,3-dione (352 mg, 2.39 mmol, 2 eq) and triphenylphosphine (471 mg, 1.79 mmol, 1.5 eq) in tetrahydrofuran (8 mL) was added N,N-diisopropyl azodicarboxylate (290 mg, 1.44 mmol, 0.27 mL, 1.2 eq) at 0° C. The mixture was stirred at 15° C. for 16 hours. The reaction mixture was concentrated to afford crude product which was purified by prep-TLC (petroleum ether:ethyl acetate=1:1) to produce tert-butyl N-[(1S)-1-[4-[4-[(1,3-dioxoisoindolin-2-yl)methyl]thiazol-5-yl]phenyl]ethyl]carbamate (560 mg) as a white solid.

Step 2

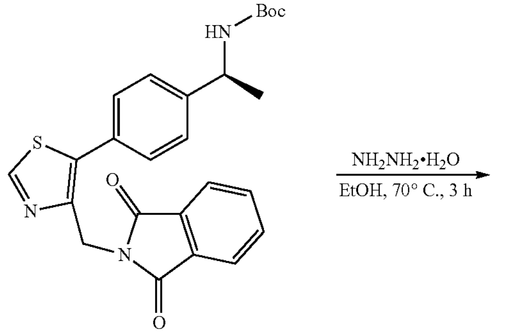

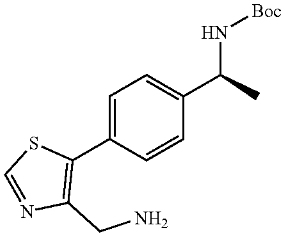

A mixture of tert-butyl N-[(1S)-1-[4-[4-[(1,3-dioxoisoindolin-2-yl)methyl]thiazol-5-yl]phenyl]ethyl]carbamate (600 mg, 1.29 mmol, 1 eq) and hydrazine hydrate (661 mg, 12.94 mmol, 0.64 mL, 98% purity, 10 eq) in ethanol (24 mL) was degassed and purged with nitrogen three times, and then the mixture was stirred at 70° C. for 3 hours under nitrogen atmosphere. The reaction mixture was filtered, and the filter cake was washed with ethanol (30 mL). The filtrate was concentrated to afford crude product. Compound tert-butyl N-[(1S)-1-[4-[4-(aminomethyl)thiazol-5-yl]phenyl]ethyl] carbamate (530 mg, crude) was obtained as a white solid.

Step 3

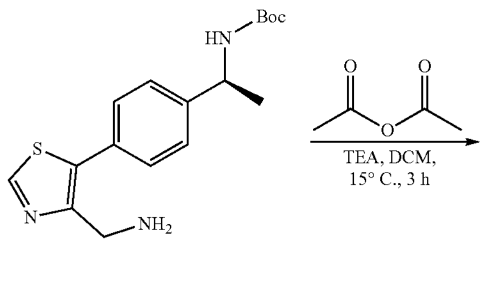

-continued

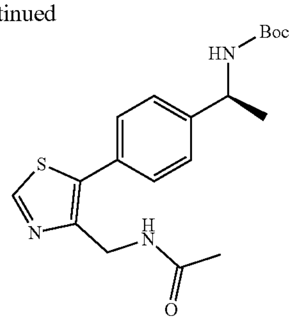

To a solution of tert-butyl N-[(1S)-1-[4-[4-(aminomethyl) thiazol-5-yl]phenyl]ethyl]carbamate (618 mg, 1.85 mmol, 1 eq) and triethylamine (563 mg, 5.56 mmol, 0.77 mL, 3 eq) in dichloromethane (30 mL) was added acetic anhydride (227 mg, 2.22 mmol, 0.21 mL, 1.2 eq) at 0° C. The mixture was stirred at 15° C. for 3 h. The reaction mixture was diluted with water (30 mL), and then the organic layer was concentrated to afford crude product. The crude product was purified by prep-TLC (dichloromethane:methanol=10:1). Compound tert-butyl N-[(1S)-1-[4-[4-(acetamidomethyl) thiazol-5-yl]phenyl]ethyl]carbamate (400 mg, 1.07 mmol, 58% yield) was obtained as a white solid.

tert-Butyl N-[(1S)-1-[4-[4-(acetamidomethyl)thiazol-5-yl]phenyl]ethyl]carbamate was converted to the final compound using procedures described for exemplary compound 76.

Exemplary Synthesis of Exemplary Compound 175

Step 1

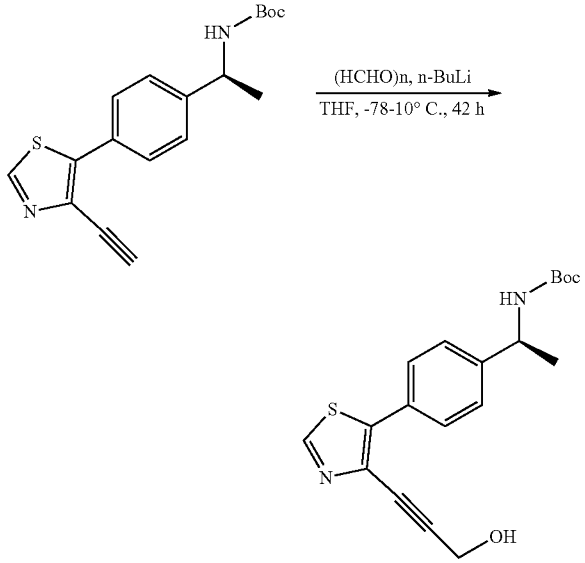

To a solution of tert-butyl N-[(1S)-1-[4-(4-ethynylthiazol-5-yl)phenyl]ethyl]carbamate (1.73 g, 5.27 mmol, 1 eq) in tetrahydrofuran (50 mL) was added n-butyllithium (2.5 M, 4.42 mL, 2.1 eq) at −78° C. under nitrogen. The reaction mixture was stirred at −50° C. for 2 h. Then triformol (474 mg, 5.27 mmol, 1 eq) was added, and the reaction mixture was allowed to warm to 10° C. for 22 h. The reaction mixture was stirred at 10° C. for another 20 h. Water (40 mL)

was added, and the mixture was extracted with ethyl acetate (40 mL). The organic layer was dried over sodium sulfate and then concentrated under vacuum. The residue was purified by silica gel column chromatography (10-80% ethyl acetate in petroleum ether) to get the tert-butyl N-[(1S)-1-[4-[4-(3-hydroxyprop-1-ynyl)thiazol-5-yl]phenyl]ethyl]carbamate (480 mg, 1.34 mmol, 25% yield) as a white solid. 950 mg of the starting material was recovered.

tert-Butyl N-[(1S)-1-[4-[4-(3-hydroxyprop-1-ynyl)thiazol-5-yl]phenyl]ethyl]carbamate was converted to tert-butyl (S)-(1-(4-(4-(3-acetamidoprop-1-yn-1-yl)thiazol-5-yl)phenyl)ethyl)carbamate using procedures described above for exemplary compound 174.

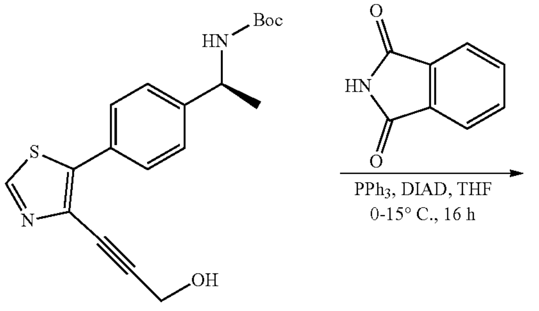

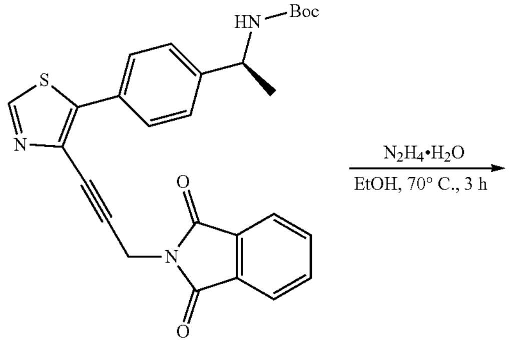

-continued

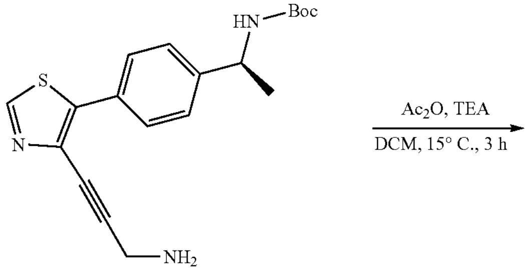

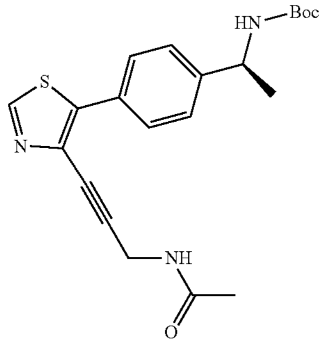

tert-Butyl (S)-(1-(4-(4-(3-acetamidoprop-1-yn-1-yl)thiazol-5-yl)phenyl)ethyl)carbamate was converted to the final compound using procedures analogous to those described for exemplary compound 76.

Exemplary Synthesis of Exemplary Compound 178

Ex. 178

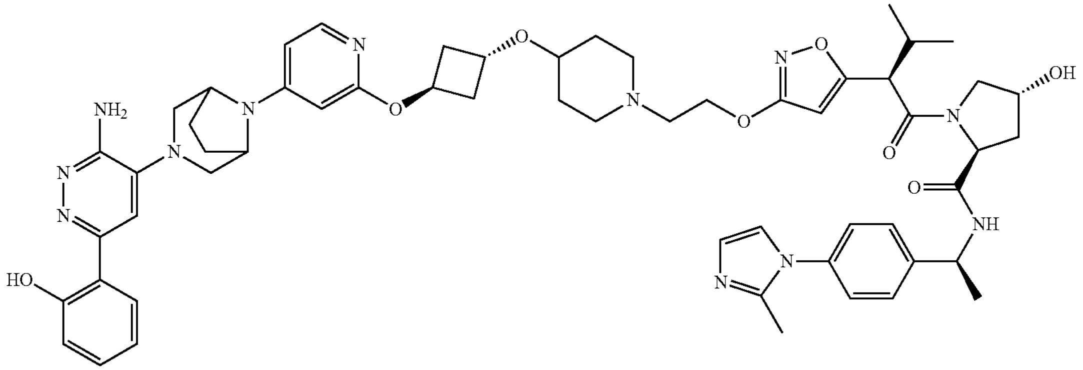

Prepared according to the scheme below using procedures described above.
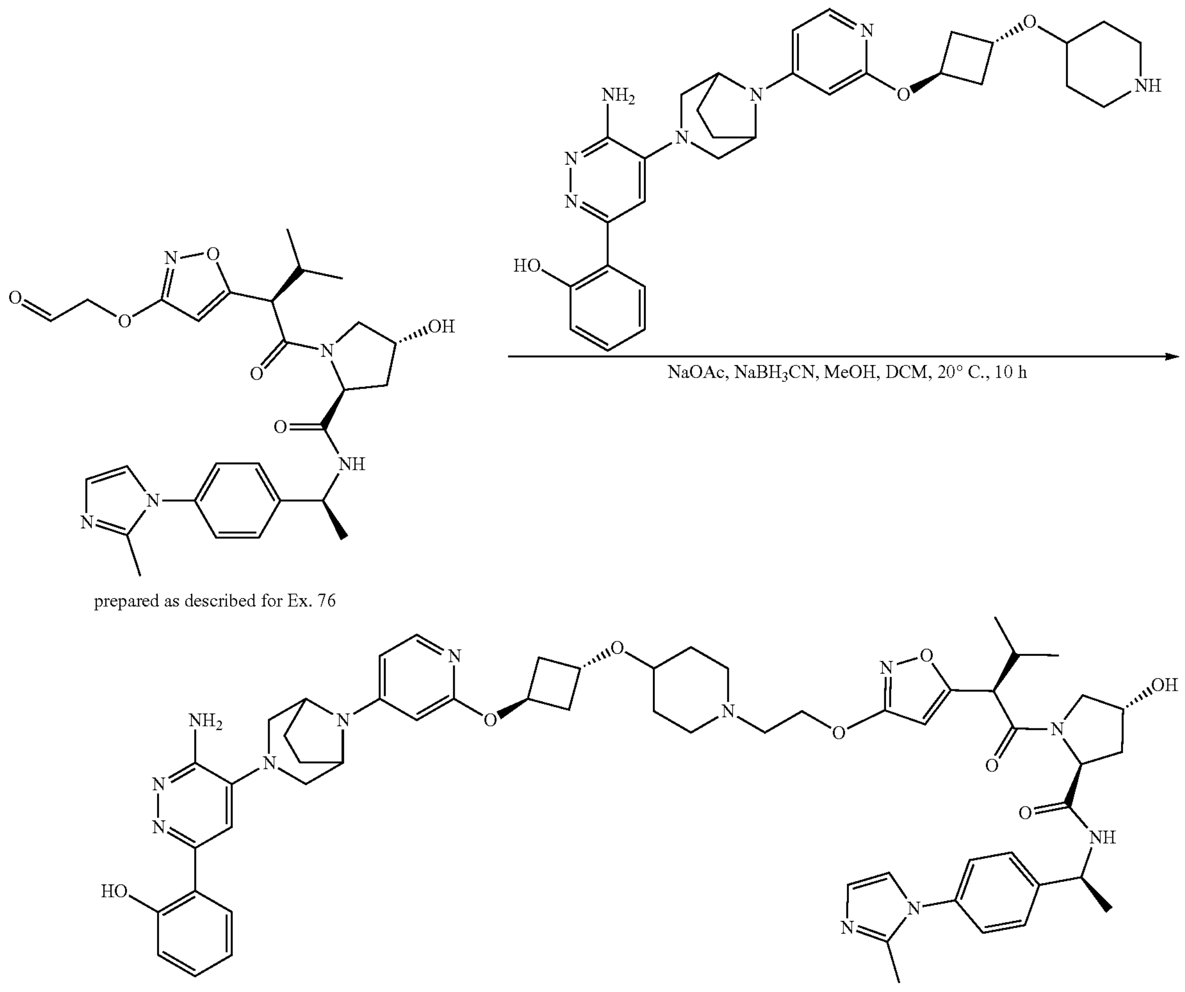
Ex. 178
Exemplar compound 176 was prepared using analogous procedures.
Exemplary Synthesis of Exemplary Compound 180
Ex. 180
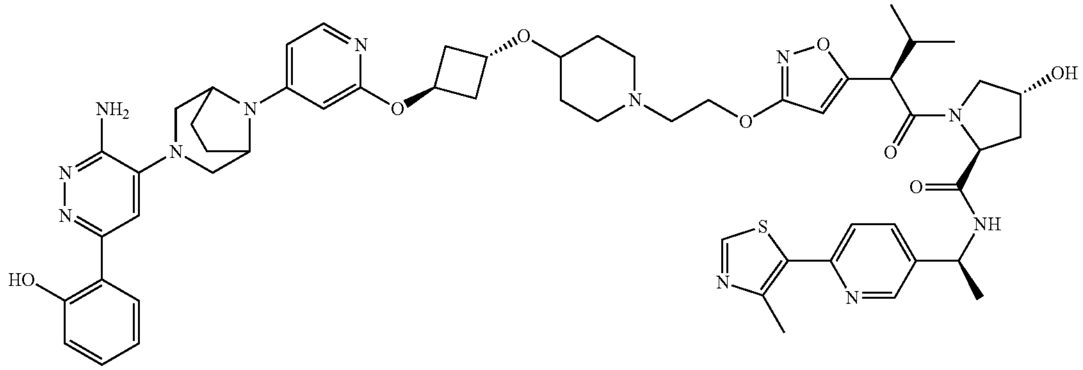

Prepared according to the scheme below using procedures described above.
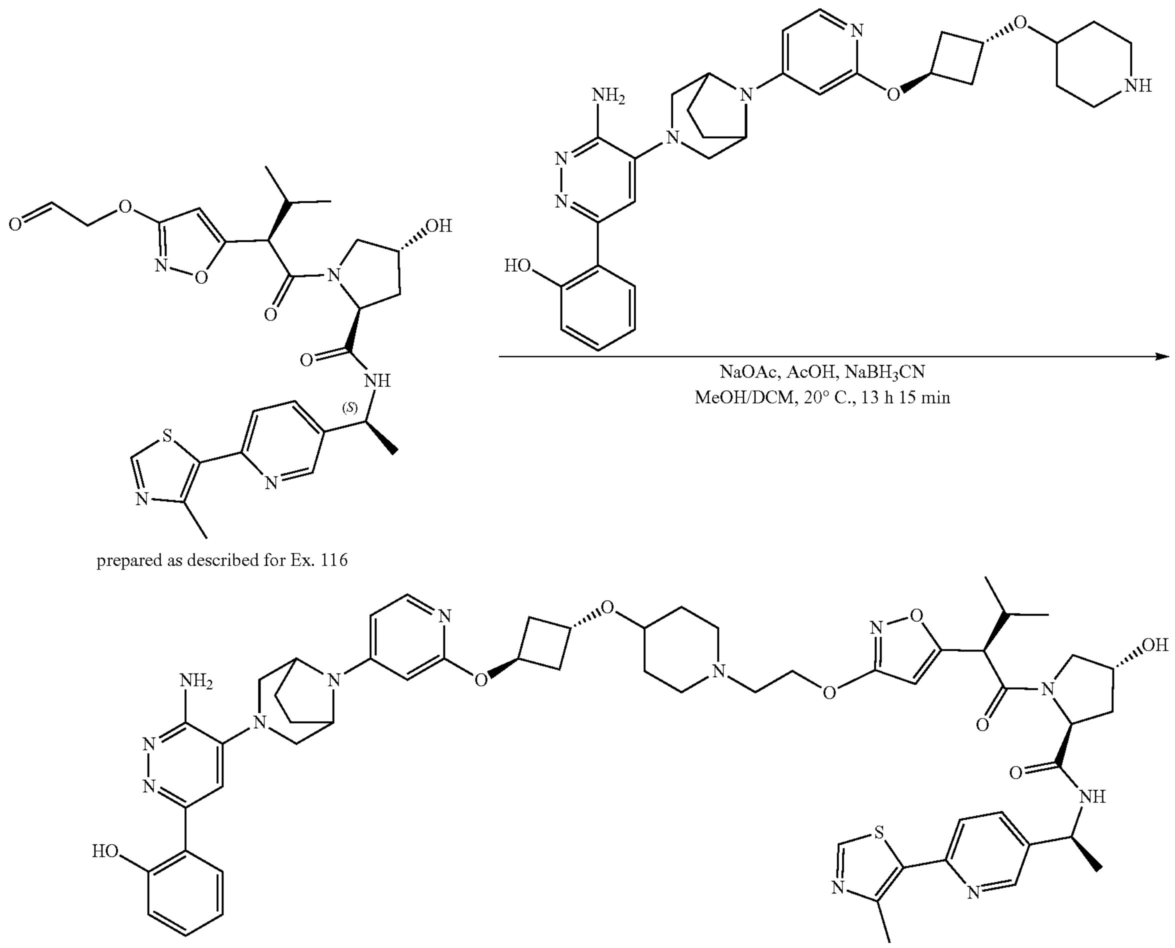
Ex. 180
Exemplary compounds 179 was prepared using analogous procedures.
Exemplary Synthesis of Exemplary Compound 183
Ex. 183
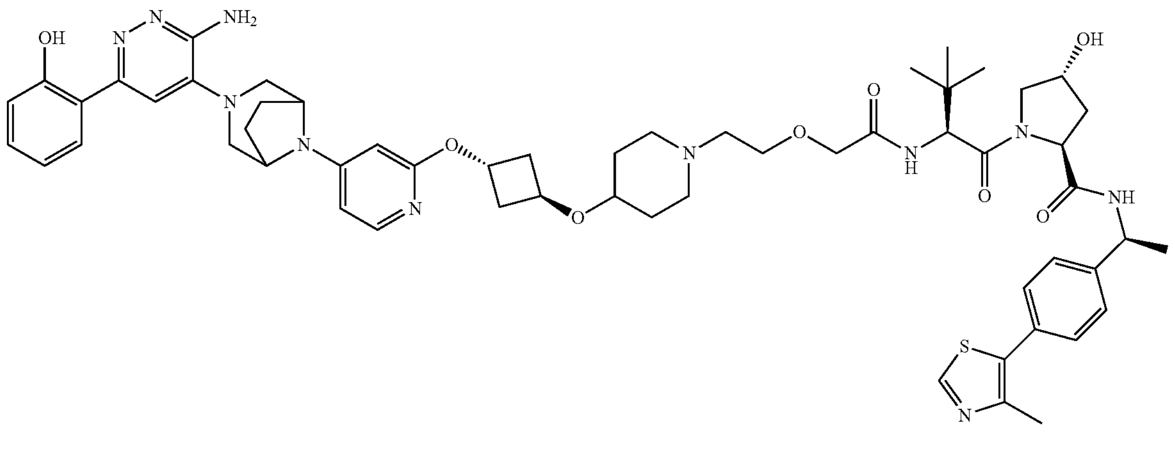

Step 1

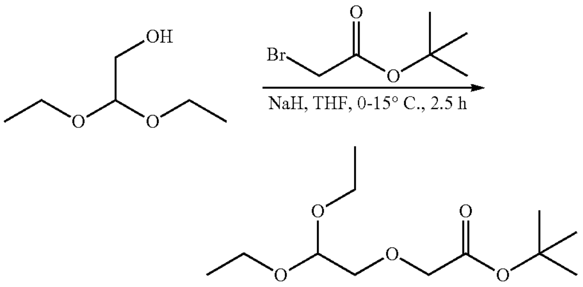

To a solution of 2,2-diethoxyethanol (2.06 g, 15.38 mmol, 1.5 eq) in THF (50 mL) was added sodium hydride (615 mg, 15.38 mmol, 60% purity, 1.5 eq) at 0° C., and the mixture was stirred at 0° C. for 30 minutes. To this was then added a solution of tert-butyl 2-bromoacetate (2 g, 10.25 mmol, 1.52 mL, 1 eq) in THF (50 mL) at 0° C., and the reaction mixture was stirred at 15° C. for 2 hours under nitrogen. The mixture was cooled to 0° C. and quenched by a saturated aqueous solution of ammonium chloride. The aqueous phase was extracted with ethyl acetate (20 mL×3). The combined organic phase was washed with brine (15 mL×2), dried with anhydrous sodium sulfate, filtered and concentrated under vacuum. The residue was purified by silica gel chromatography (petroleum ether/ethyl acetate=50/1 to 20/1) to afford tert-butyl 2-(2,2-diethoxyethoxy)acetate (883 mg, 3.56 mmol, 34% yield) as a yellow oil.

Step 2

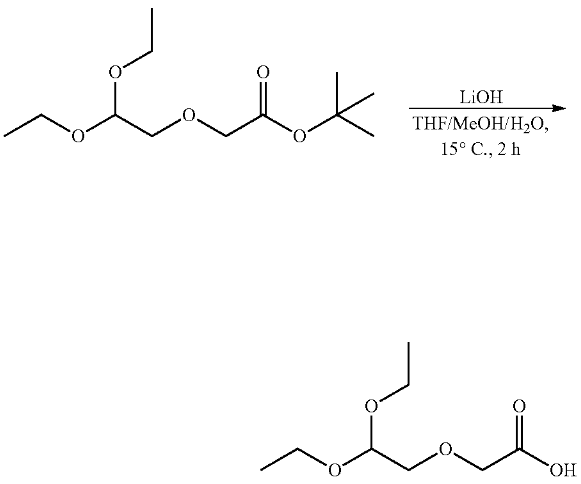

To tert-butyl 2-(2,2-diethoxyethoxy)acetate (0.7 g, 2.82 mmol, 1 eq) in a mixture of THF (3 mL), methanol (3 mL) and water (6 mL) was added lithium hydroxide monohydrate (1.18 g, 28.19 mmol, 10 eq) in one portion at 15° C. under nitrogen. The mixture was stirred at 2 hours. The pH was adjusted to 6 with 1 M hydrochloric acid. The aqueous phase was extracted with ethyl acetate (35 mL×4). The combined organic phase was washed with brine (20 mL×2), dried with anhydrous sodium sulfate, filtered and concentrated under vacuum. The crude product 2-(2,2-diethoxyethoxy)acetic acid (460 mg, crude) was obtained as a yellow oil.

Step 3

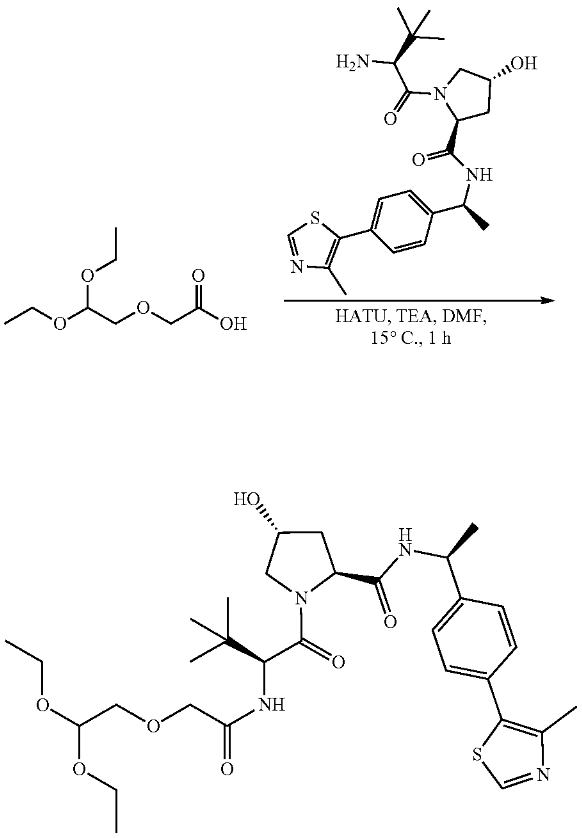

To a mixture of (2S,4R)-1-[(2S)-2-amino-3,3-dimethyl-butanoyl]-4-hydroxy-N-[(1S)-1-[4-(4-methylthiazol-5-yl) phenyl]ethyl]pyrrolidine-2-carboxamide (0.2 g, 0.45 mmol, 1 eq) and 2-(2,2-diethoxyethoxy)acetic acid (87 mg, 0.45 mmol, 1 eq) in N,N-dimethylformamide (10 mL) was added O-(7-azabenzotriazol-1-yl)-N,N,N',N'-tetramethyluronium hexafluorophosphate (222 mg, 0.59 mmol, 1.3 eq) and triethylamine (137 mg, 1.35 mmol, 0.19 mL, 3 eq) in one portion at 15° C. under nitrogen. The mixture was stirred at 15° C. for 1 hour. The mixture was poured into ice-water (w/w=1/1, 20 mL) and stirred for 5 minutes. The aqueous phase was extracted with ethyl acetate (20 mL×4). The combined organic phase was washed with brine (15 mL×2), dried with anhydrous sodium sulfate, filtered and concentrated in vacuum. The residue was purified by semi-preparative reverse phase HPLC (formic acid condition; column: Phenomenex Synergi C18 150*25*10 um mobile phase: [water (0.225% FA)-ACN]; B %: 30%-60%, 9 min). The product (2S,4R)-1-[(2S)-2-[[2-(2,2-diethoxyethoxy)acetyl] amino]-3,3-dimethyl-butanoyl]-4-hydroxy-N-[(1S)-1-[4-(4-methylthiazol-5-yl)phenyl]ethyl]pyrrolidine-2-carboxamide (230 mg, 0.37 mmol, 82% yield) was obtained as a yellow oil.

(2S,4R)-1-[(2S)-2-[[2-(2,2-Diethoxyethoxy)acetyl] amino]-3,3-dimethyl-butanoyl]-4-hydroxy-N-[(1S)-1-[4-(4-methylthiazol-5-yl)phenyl]ethyl]pyrrolidine-2-carboxamide was converted to the final compound according to the scheme below and using procedures described above for other examples.

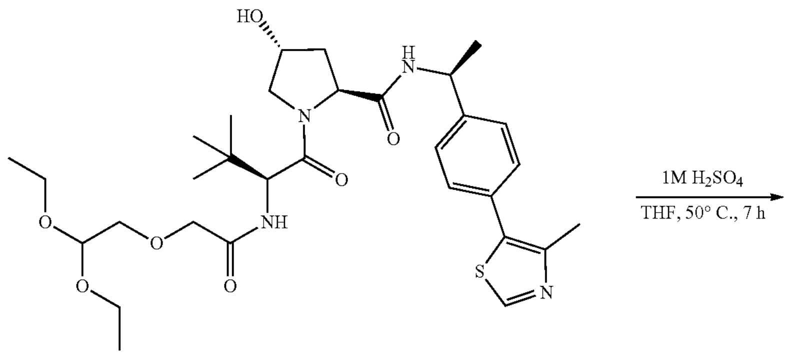
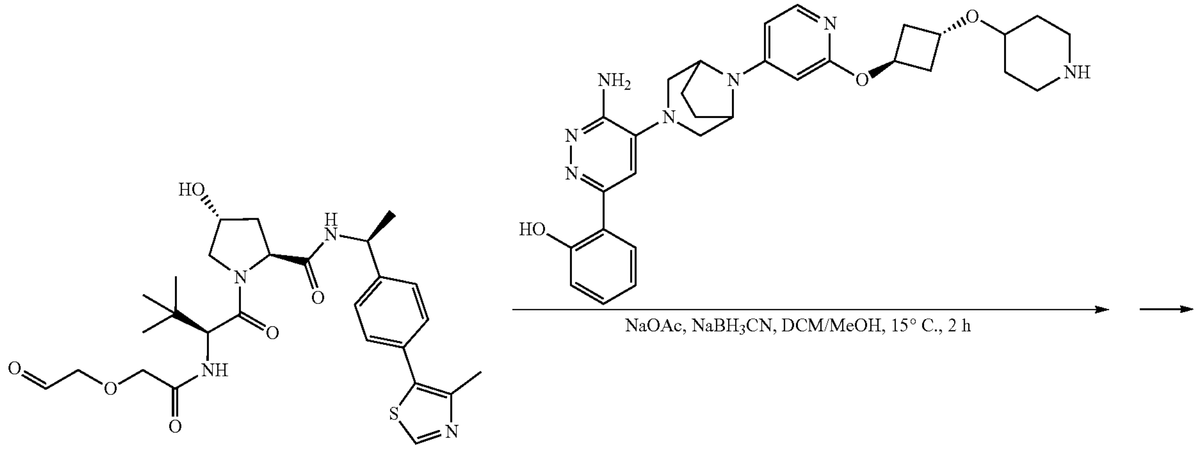
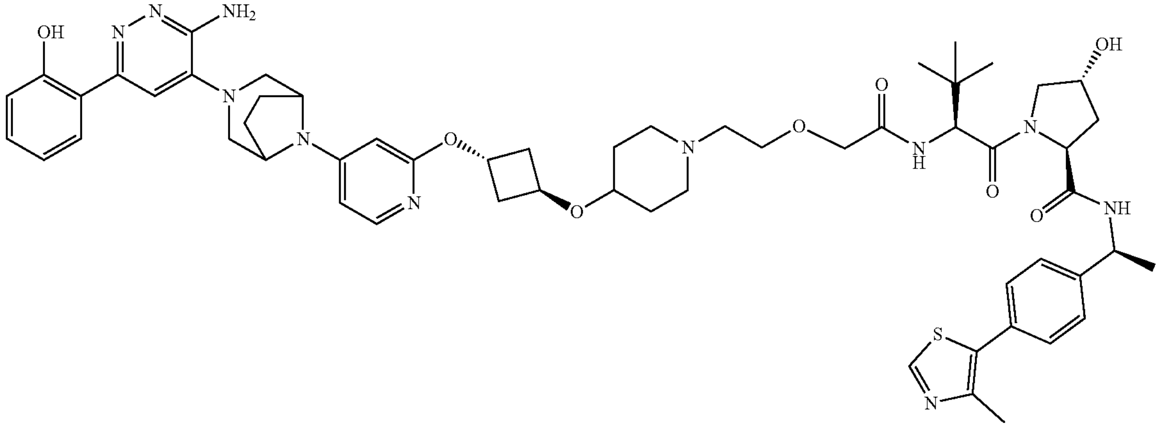
Ext. 183

Exemplary Synthesis of Exemplary Compound 86

Ex. 86

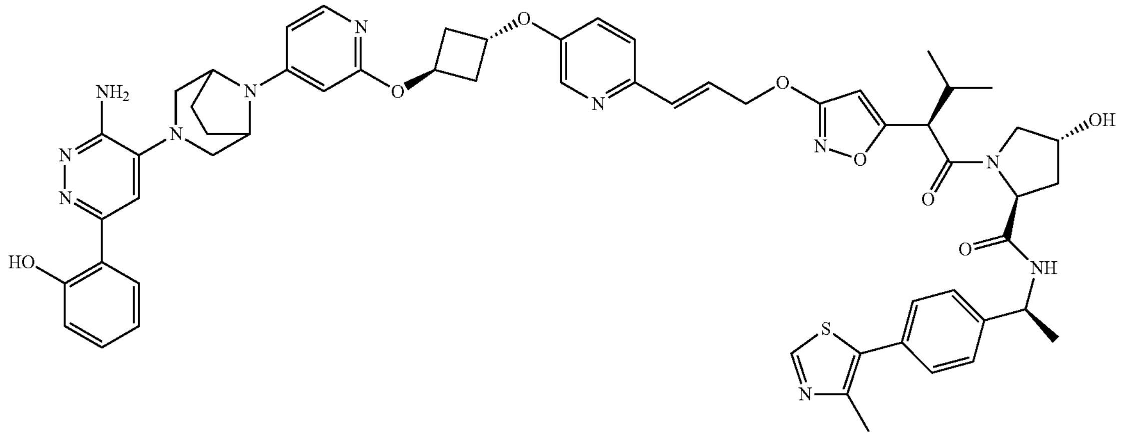

Step 1

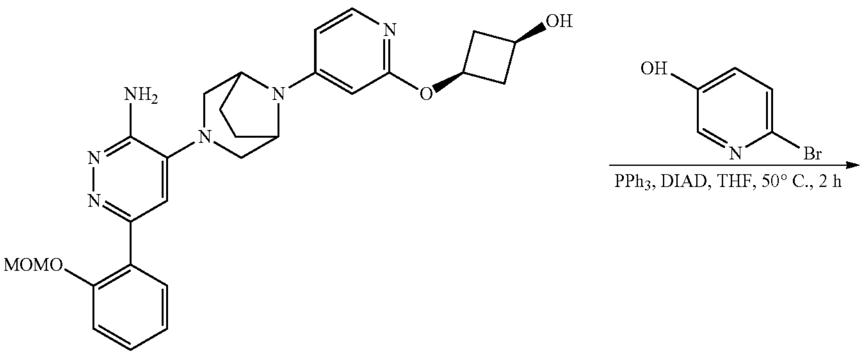

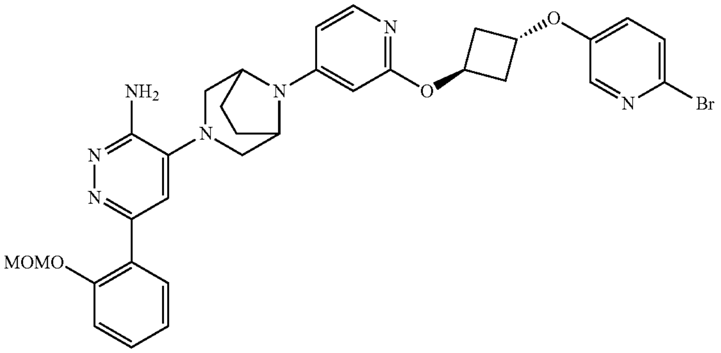

At 0° C., to a solution of $PPh_3$ (4.68 g, 17.836 mmol, 3.0 equiv) in THF (100 mL) was added DIAD (3.61 g, 17.836 mmol, 3.0 equiv), and (1s,3s)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutan-1-ol (3.0 g, 5.945 mmol, 1 equiv) under nitrogen atmosphere. To the above mixture was added 6-bromopyridin-3-ol (2.07 g, 11.891 mmol, 2.0 equiv) dropwise over 5 minutes at 0° C. under nitrogen atmosphere. The resulting mixture was stirred for 5 minutes at 0° C., then heated up to 50° C. and stirred for 2 hours at 50° C. The reaction was quenched with water (25 mL), and the resulting mixture was extracted with EtOAc (50 mL×3). The combined organic layers were washed with brine (50 mL), dried over anhydrous sodium sulfate and concentrated under reduced pressure. The residue was purified by silica gel column chromatography eluting with $CH_2C12$/MeOH (10:1) to afford 6-[2-(methoxymethoxy)phenyl]-4-(8-[2-[(1r,3r)-3-[(6-bromopyridin-3-yl)oxy]cyclobutoxy]pyridin-4-yl]-3,8-diazabicyclo[3.2.1]octan-3-yl)pyridazin-3-amine (2.3 g, 59%) as a light yellow solid.

Step 2

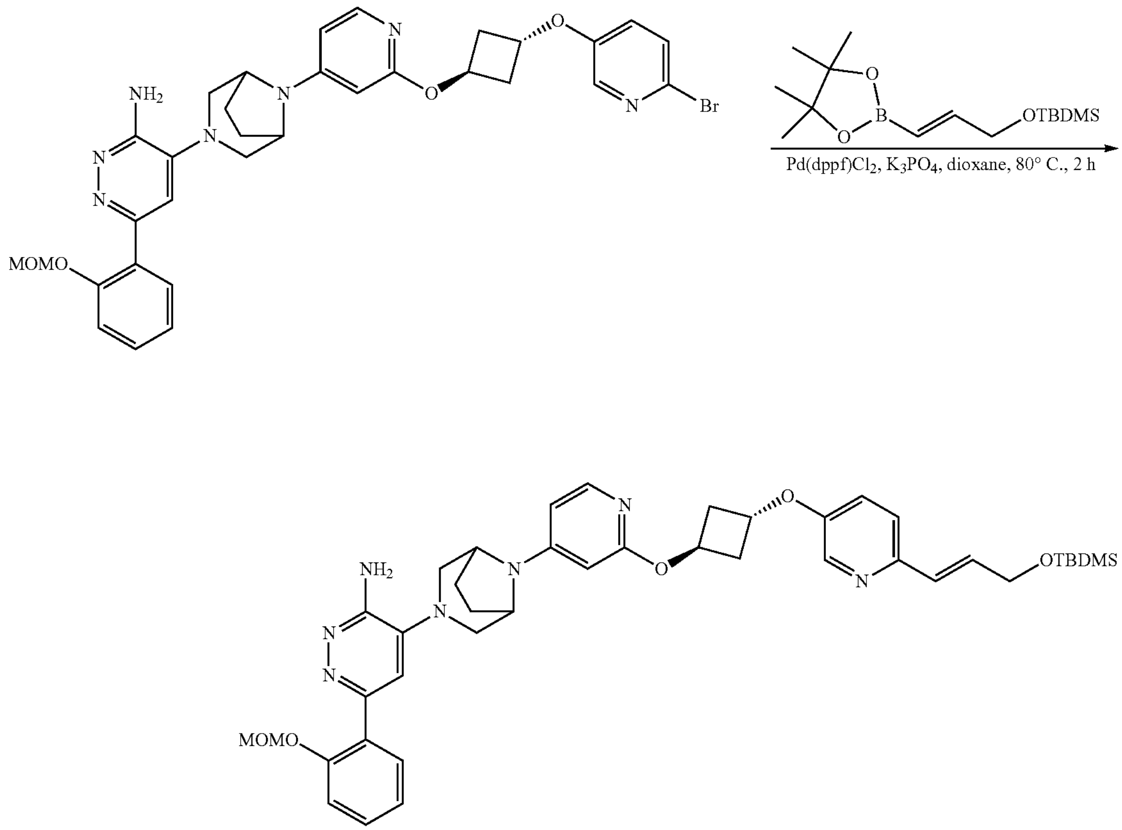

The following reaction was done in 4 parallel equal batches and combined for work-up and purification. In each batch, to a solution of 6-[2-(methoxymethoxy)phenyl]-4-(8-[2-[(1r,3r)-3-[(6-bromopyridin-3-yl)oxy]cyclobutoxy]pyridin-4-yl]-3,8-diazabicyclo[3.2.1]octan-3-yl)pyridazin-3-amine (571 mg, 0.864 mmol, 1.00 equiv) and tert-butyldimethyl[[(2E)-3-(4,4,5,5-tetramethyl-1,3,2-dioxaborolan-2-yl)prop-2-en-1-yl]oxy]silane (387 mg, 1.297 mmol, 1.50 equiv) in 1,4-dioxane (15 mL) and water (5 mL) were added $K_2CO_3$ (1.07 g, 0.008 mmol, 3.0 equiv) and Pd(dppf)C12-$CH_2$C12 (105 mg, 0.130 mmol, 0.15 equiv) at room temperature under nitrogen atmosphere. The resulting mixture was stirred for 2 hours at 80° C. under nitrogen atmosphere. Each reaction was quenched by the addition of water (50 mL) at room temperature, and the resulting mixtures were combined and extracted with EtOAc (90 mL×3). The combined organic layers were washed with brine, dried over anhydrous sodium sulfate and concentrated under reduced pressure. The residue was purified by silica gel column chromatography eluting with $CH_2Cl_2$/MeOH (10:1) to afford 6-[2-(methoxymethoxy)phenyl]-4-(8-[2-[(1r,3r)-3-([6-[(1E)-3-[(tert-butyldimethylsilyl)oxy]prop-1-en-1-yl]pyridin-3-yl]oxy)cyclobutoxy]pyridin-4-yl]-3,8-diazabicyclo[3.2.1]octan-3-yl)pyridazin-3-amine (2.1 g total, 76%) as a light yellow solid.

Step 3

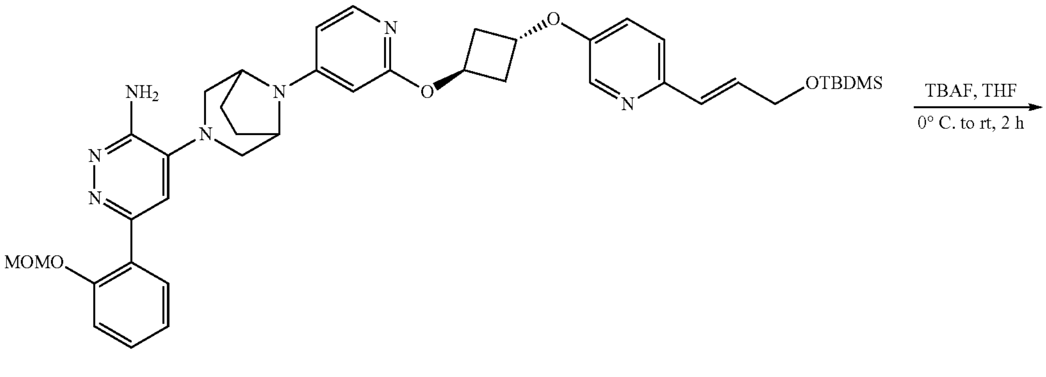

-continued

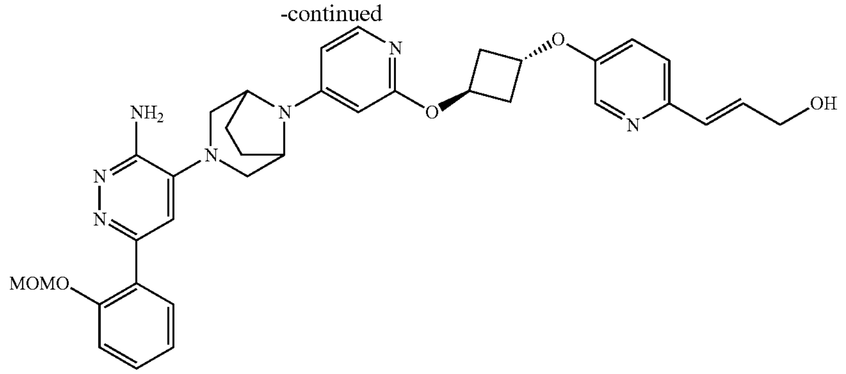

To a stirred solution of 6-[2-(methoxymethoxy)phenyl]-4-(8-[2-[(1r,3r)-3-([6-[(1E)-3-[(tert-butyldimethylsilyl)oxy]prop-1-en-1-yl]pyridin-3-yl]oxy)cyclobutoxy]pyridin-4-yl]-3,8-diazabicyclo[3.2.1]octan-3-yl)pyridazin-3-amine (2.10 g, 2.79 mmol, 1.00 equiv) in THF (20 mL) was added TBAF (1 mol/L, 8.3 mL, 8.3 mmol, 3.0 equiv) dropwise at 0° C. under nitrogen atmosphere. The resulting solution was stirred for 2 hours at room temperature. The reaction was applied onto a silica gel column eluting with dichloromethane/methanol (10:1). This resulted in 3-[5-[(1r,3r)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutoxy]pyridin-2-yl]prop-2-en-1-ol (1.1 g, 62%) as a light yellow solid.

Step 4

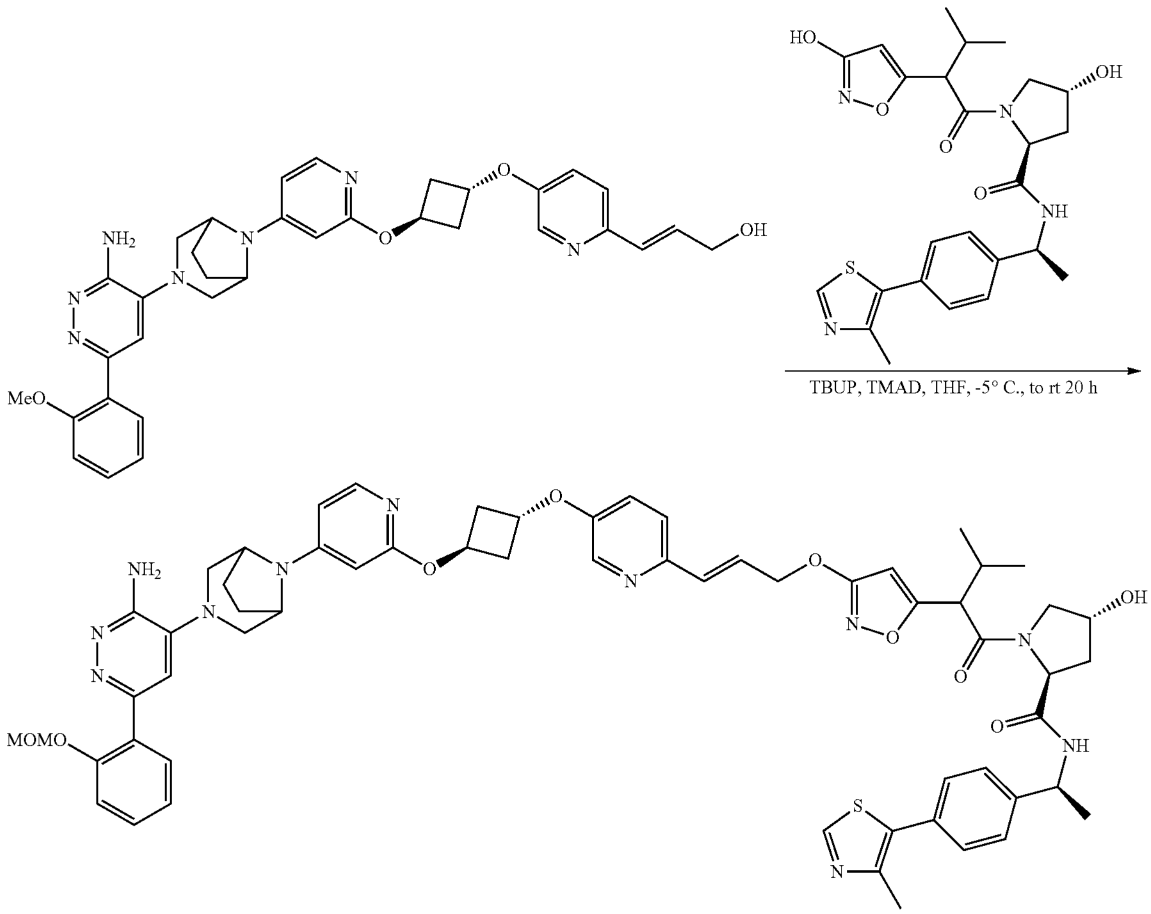

then quenched by the addition of water (25 mL). The resulting mixture was extracted with ethyl acetate (30 mL×3). The organic layers were combined, dried over anhydrous sodium sulfate and concentrated. The residue was To a solution of tributylphosphine (634 mg, 3.14 mmol, 10.00 equiv) and tetramethylazodicarboxamide (588 mg, 3.14 mmol, 10.00 equiv) in THF was added (2S,4R)-4-hydroxy-1-[2-(3-hydroxy-1,2-oxazol-5-yl)-3-methylbutanoyl]-N-[(1S)-1-[4-(4-methyl-1,3-thiazol-5-yl)phenyl]ethyl]pyrrolidine-2-carboxamide (172 mg, 0.345 mmol, 1.10 equiv) and (2E)-3-[5-[(1r,3r)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutoxy]pyridin-2-yl]prop-2-en-1-ol (70 mg, 0.11 mmol, 1 equiv) at −10° C. under nitrogen atmosphere. The resulting mixture was stirred for 16 hours at room temperature under nitrogen atmosphere. The reaction was quenched by the addition of water (50 mL) at room temperature, and the resulting mixture was extracted with EtOAc (30 mL×3). The combined organic layers were washed with brine (50 mL), dried over anhydrous sodium sulfate and concentrated under reduced pressure. The residue was purified by silica gel column chromatography eluting with dichloromethane/methanol (10:1) to afford (2S,4R)-4-hydroxy-N-[(1S)-1-[4-(4-methyl-1,3-thiazol-5-yl)phenyl]ethyl]-1-[3-methyl-2-(3-[[(2E)-3-[5-[(1r,3r)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutoxy]pyridin-2-yl]prop-2-en-1-yl]oxy]-1,2-oxazol-5-yl)butanoyl]pyrrolidine-2-carboxamide (120 mg, 34%) as a light yellow solid.

(2S,4R)-4-hydroxy-N-[(1S)-1-[4-(4-methyl-1,3-thiazol-5-yl)phenyl]ethyl]-1-[3-methyl-2-(3-[[(2E)-3-[5-[(1r,3r)-3-[[4-(3-[3-amino-6-[2-(methoxymethoxy)phenyl]pyridazin-4-yl]-3,8-diazabicyclo[3.2.1]octan-8-yl)pyridin-2-yl]oxy]cyclobutoxy]pyridin-2-yl]prop-2-en-1-yl]oxy]-1,2-oxazol-5-yl)butanoyl]pyrrolidine-2-carboxamide was converted to the final compound using standard procedures described above for other examples.

Exemplar compounds 186, 206, and 207 were preparing using analogous procedures.

Exemplary Synthesis of Exemplary Compounds 189

Ex. 189

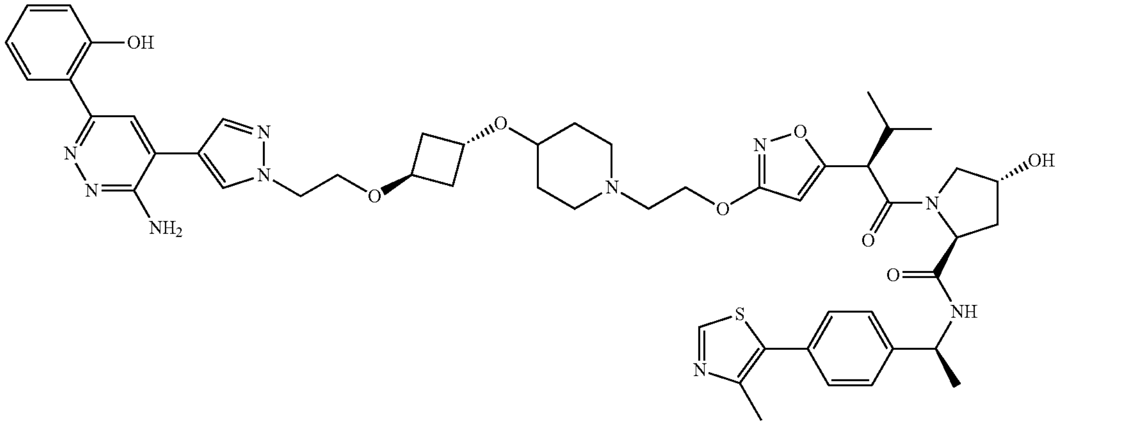

Step 1

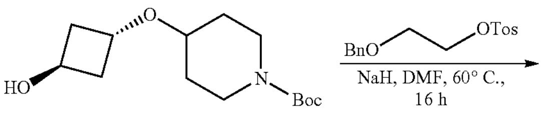

-continued

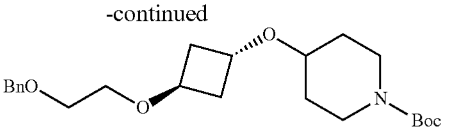

To a solution of tert-butyl 4-(3-hydroxycyclobutoxy)piperidine-1-carboxylate (2 g, 7.37 mmol, 1 eq) in N,N-dimethylformamide (40 mL) was added sodium hydride (353 mg, 8.84 mmol, 60% purity, 1.2 eq) at 0° C. The mixture was stirred at 25° C. for 1 hour. Then 2-benzyloxyethyl 4-methylbenzenesulfonate (3.39 g, 11.06 mmol, 1.5 eq) in N,N-dimethylformamide (2 mL) was added. The mixture was stirred at 60° C. for 15 hours. The reaction mixture was quenched by the addition of water (200 mL) and extracted with ethyl acetate (200 mL×3). The combined organic layers were washed with brine (200 mL×3), dried over anhydrous sodium sulfate, filtered and concentrated under reduced pressure to give a residue. The residue was purified by prep-HPLC (column: Phenomenex Synergi Max-RP 250*50 mm*10 um; mobile phase: [water (0.225% FA)-ACN]; B %: 50ACN %-80ACN %, 26 min, 20% min). Compound tert-butyl 4-[3-(2-benzyloxyethoxy)cyclobutoxy]piperidine-1-carboxylate (2.1 g, 5.18 mmol, 70% yield) was obtained as a colorless oil.

Step 2

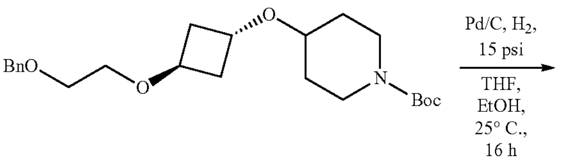

-continued

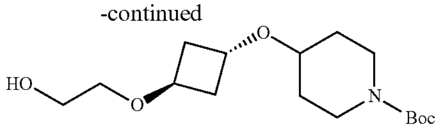

To a solution of tert-butyl 4-[3-(2-benzyloxyethoxy)cyclobutoxy]piperidine-1-carboxylate (2.1 g, 5.18 mmol, 1 eq) in ethanol (20 mL) and tetrahydrofuran (20 mL) was added 5% palladium on activated carbon catalyst (500 mg) under nitrogen. The suspension was degassed under vacuum and purged with hydrogen 3 times. The mixture was stirred under hydrogen (15 Psi) at 25° C. for 16 hours. The reaction mixture was filtered and concentrated under reduced pressure to give a residue. Compound tert-butyl 4-[3-(2-hydroxyethoxy)cyclobutoxy]piperidine-1-carboxylate (1.6 g, 5.07 mmol, 97% yield) was obtained as a colorless oil.

tert-Butyl 4-[3-(2-hydroxyethoxy)cyclobutoxy]piperidine-1-carboxylate was converted to the final compound according to the scheme below using procedures described above for other examples.

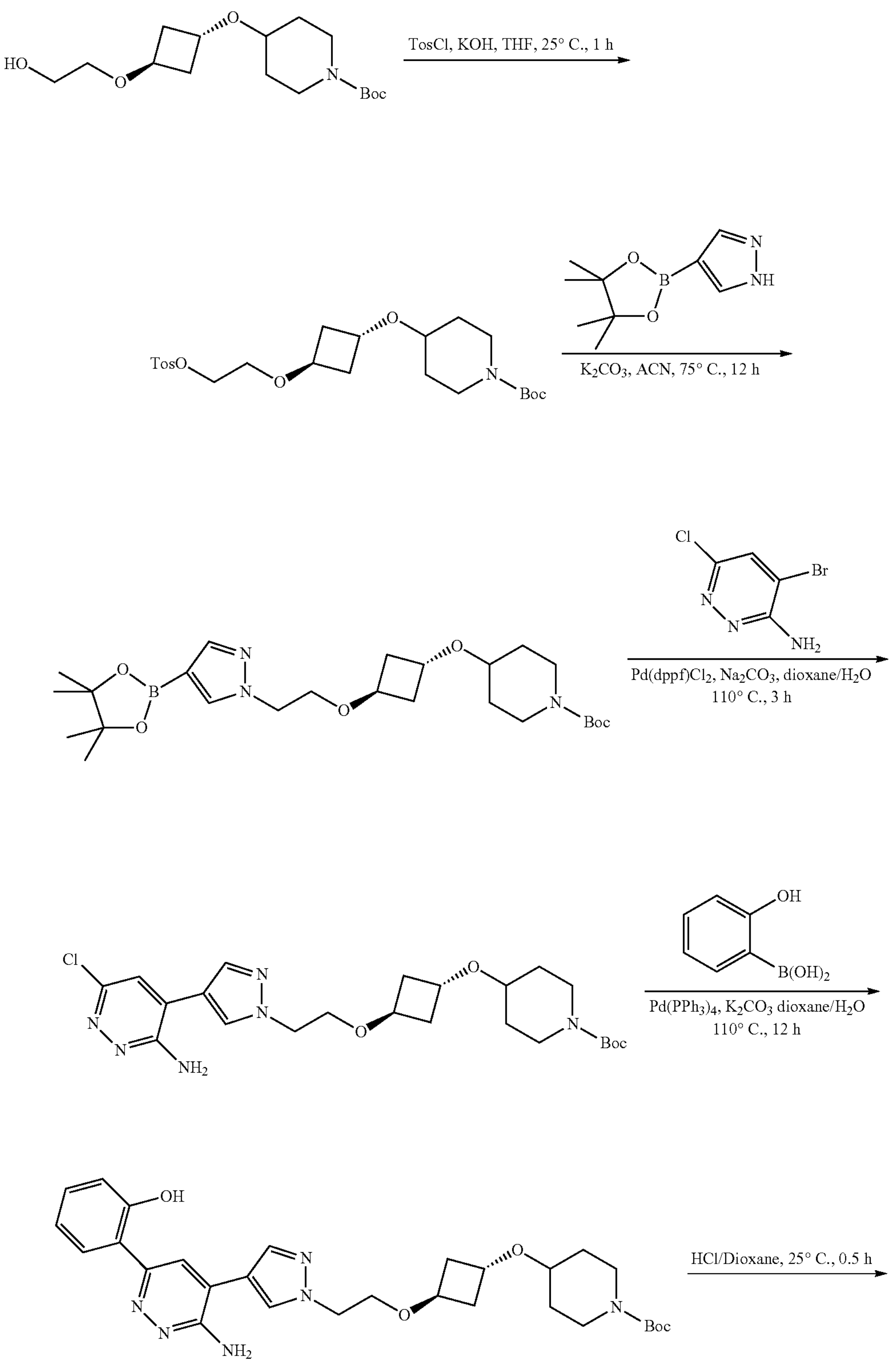

-continued
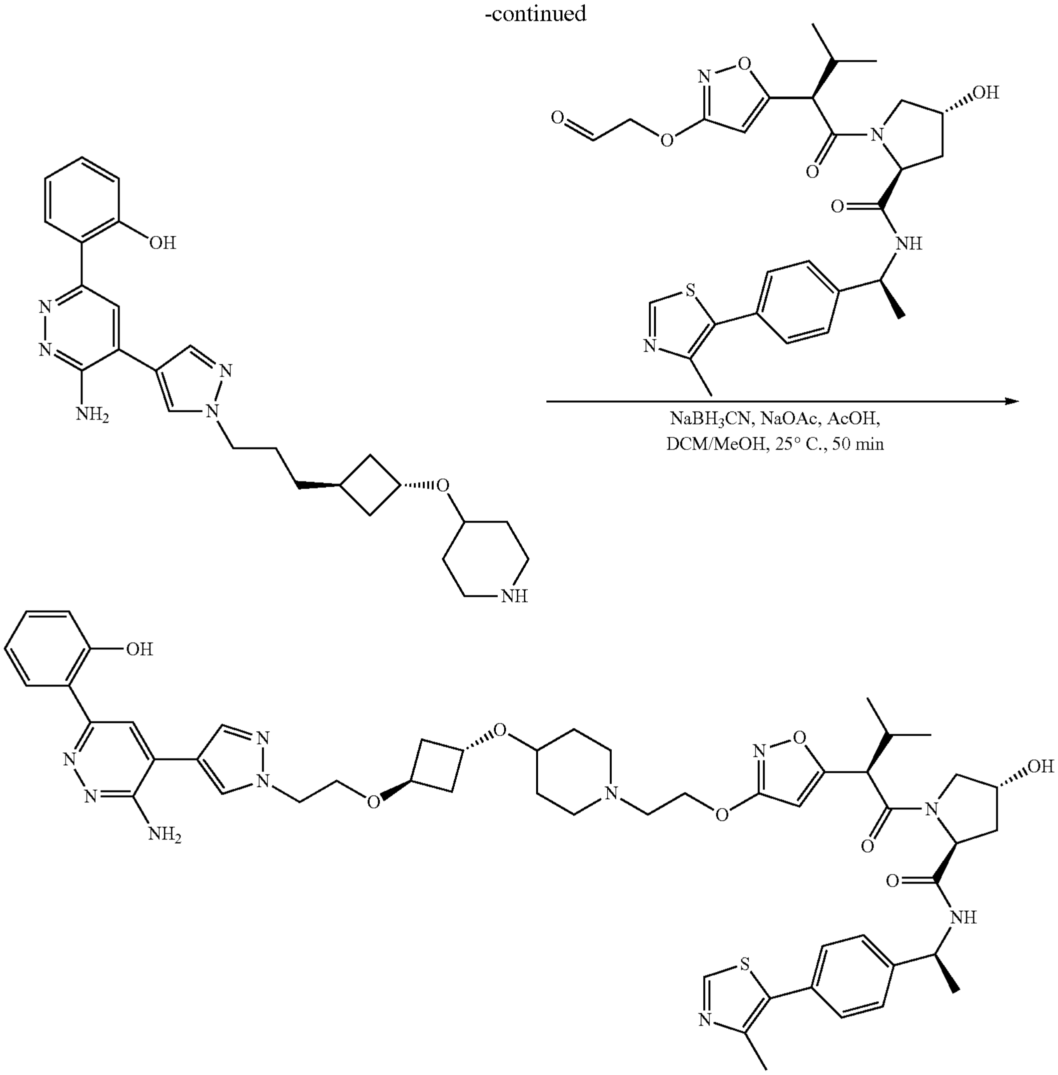
Ex. 189
Exemplary Synthesis of Exemplary Compound 194
Ex. 194
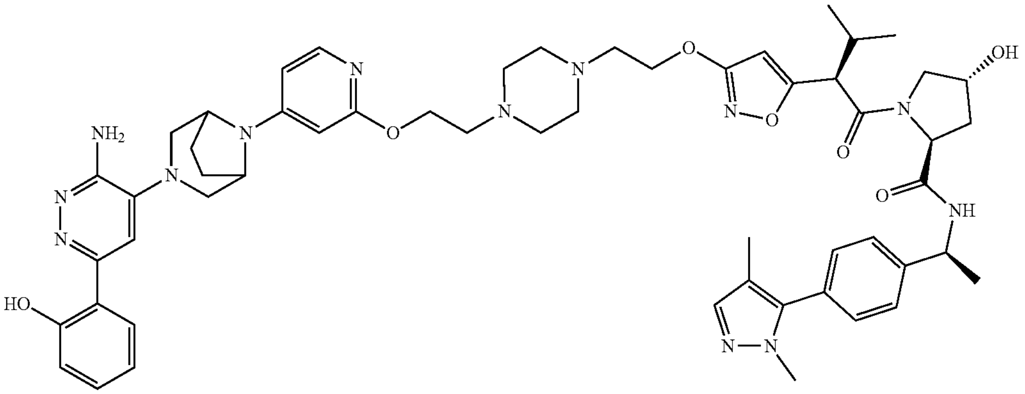

Step 1

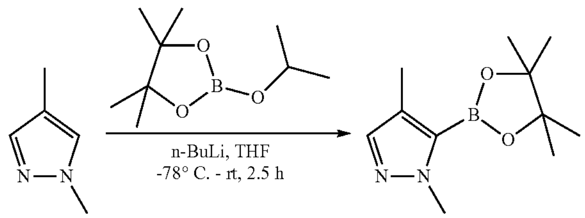

To a solution of 1,4-dimethyl-1H-pyrazole (2.5 g, 26.0 mmol, 1 equiv) in tetrahydrofuran (50 mL) was added n-butyllithium in hexane solution (2.5 M in hexane, 78.0 mmol, 31 mL, 3 equiv) dropwise at 0° C. under nitrogen atmosphere. The resulting solution was stirred at room temperature for 1 h and then cooled to −78° C. 2-iso-propoxy-4,4,5,5-tetramethyl-1,3,2-dioxaborolane (14.52 g, 78.017 mmol, 3 equiv) was added and the reaction mixture was stirred at −78° C. for 0.5 hour, then slowly warmed up to 0° C. The reaction was quenched with brine and extracted with EtOAc (250 mL×3). The combined organic layer was washed with brine, dried over $Na_2SO_4$ and concentrated under reduced pressure. The residue was applied onto a silica gel column eluting with ethyl acetate/petroleum ether (1:5). This resulted in 2.6 g (45%) of 1,4-dimethyl-5-(4,4,5,5-tetramethyl-1,3,2-dioxaborolan-2-yl)-1H-pyrazole as a white solid.

Step 2

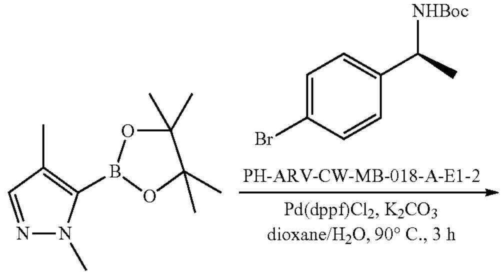

-continued

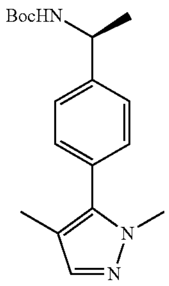

Into a 250-mL round-bottom flask, was placed tert-butyl N-[(1S)-1-(4-bromophenyl)ethyl]carbamate (1.0 g, 3.331 mmol, 1 equiv), 1,4-dimethyl-5-(4,4,5,5-tetramethyl-1,3,2-dioxaborolan-2-yl)-1H-pyrazole (1.48 g, 6.664 mmol, 2.00 equiv), $K_2CO_3$ (1.38 g, 9.963 mmol, 2.99 equiv) and Pd(dppf)C12 (244.0 mg, 0.333 mmol, 0.10 equiv) in dioxane (16 mL) and $H_2O$ (2 mL). The resulting mixture was stirred for 3 hours at 90° C. under nitrogen atmosphere. The mixture was concentrated under reduced pressure. The residue was applied onto a silica gel column eluting with ethyl acetate/petroleum ether (1:1). This resulted in 1.63 g (99%) of benzyl N-[(1S)-1-(4-bromophenyl)ethyl]carbamate as a light yellow solid.

Benzyl N-[(1S)-1-(4-bromophenyl)ethyl]carbamate was converted to the final compound using procedures described above for other examples.

Exemplary compound 193 was prepared using analogous procedures.

Exemplary Synthesis of Exemplary Compound 144

Ex. 144

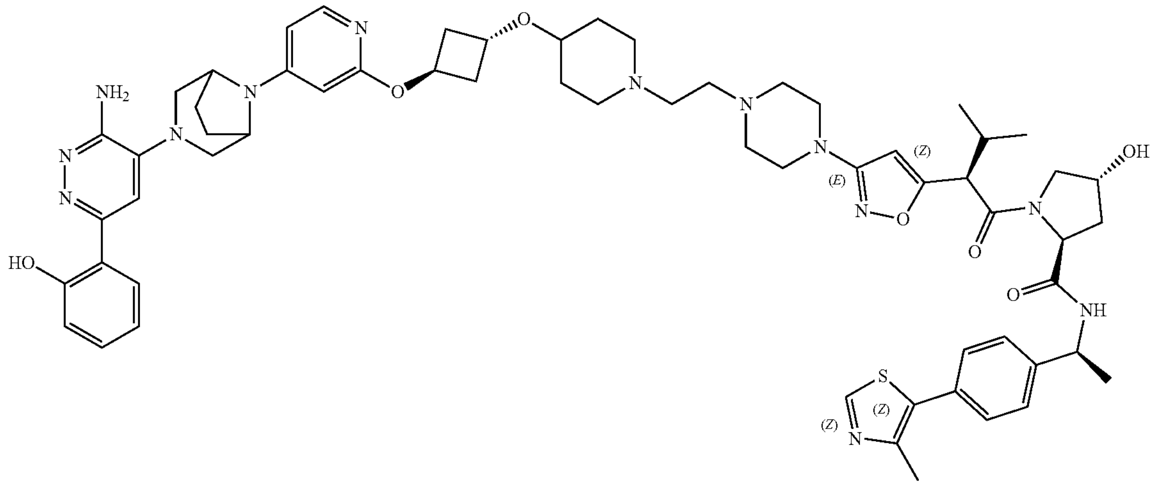

Step 1

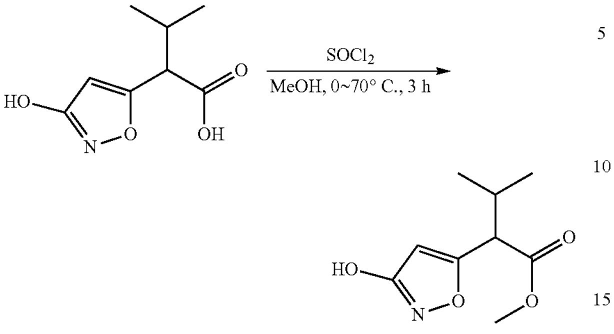

To a solution of 2-(3-hydroxyisoxazol-5-yl)-3-methyl-butanoic acid (1 g, 5.40 mmol, 1 eq) in methanol (10 mL) was added thionyl chloride (2.57 g, 21 mmol, 1.57 mL, 4 eq) at 0° C. The reaction mixture was stirred at 70° C. for 3 hours. The reaction mixture was concentrated under reduced pressure. The residue was diluted with water (50 ml) and extracted with ethyl acetate (30 mL×3). The combined organic layers were washed with brine (80 mL×2), dried over anhydrous sodium sulfate, filtered and concentrated under reduced pressure. Methyl 2-(3-hydroxyisoxazol-5-yl)-3-methyl-butanoate (1 g, 5.02 mmol, 92% yield) was obtained as a yellow oil.

Step 2

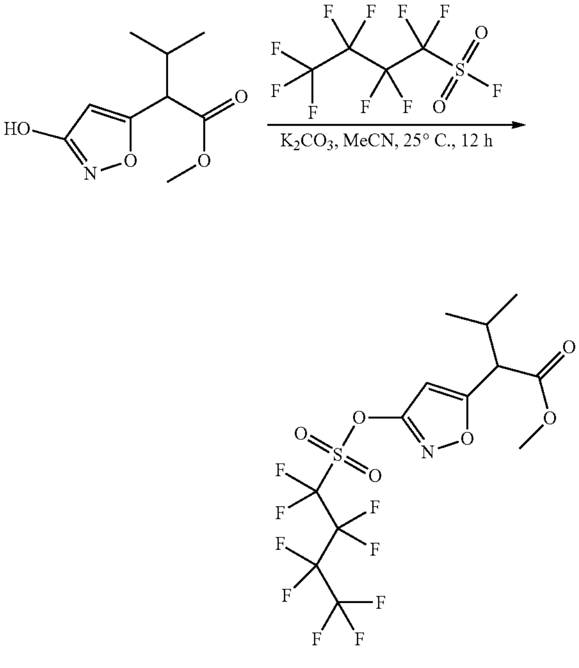

To a solution of methyl 2-(3-hydroxyisoxazol-5-yl)-3-methyl-butanoate (800 mg, 4.02 mmol, 1 eq) in acetonitrile (5 mL) was added potassium carbonate (1.11 g, 8.03 mmol, 2 eq) and perfluorobutyl sulfonyl fluoride (1.46 g, 4.82 mmol, 1.2 eq). The reaction mixture was stirred at 25° C. for 12 hours. The reaction mixture was diluted with water (50 mL) and extracted with ethyl acetate (30 mL×3). The combined organic layers were washed with brine (80 mL×3), dried over anhydrous sodium sulfate, filtered and concentrated under reduced pressure. The residue was purified by silica gel column chromatography (petroleum ether/ethyl acetate=100/1 to 20/1). Methyl 3-methyl-2-[3-(1,1,2,2,3,3,4,4,4-nonafluorobutylsulfonyloxy)isoxazol-5-yl] butanoate (530 mg, 1.10 mmol, 27% yield) was obtained as a colorless oil.

Step 3

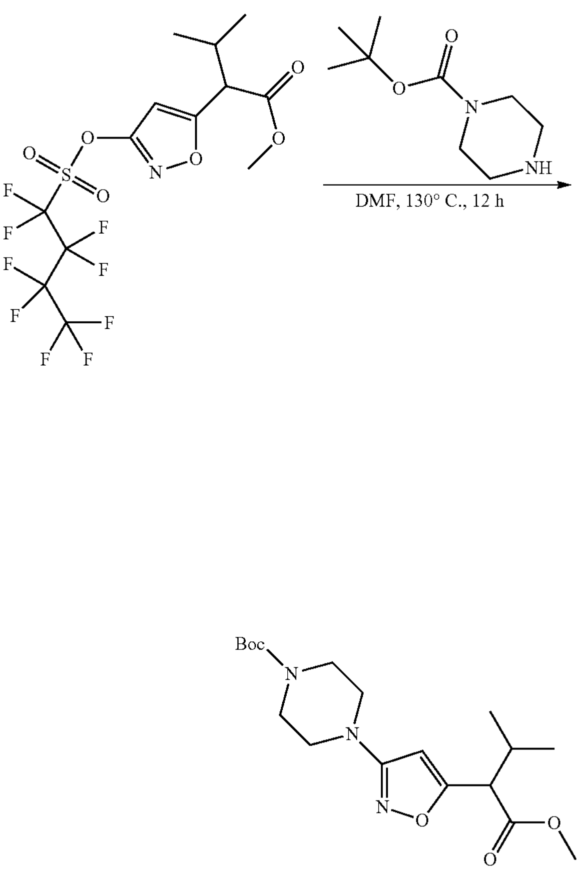

A solution of methyl 3-methyl-2-[3-(1,1,2,2,3,3,4,4,4-nonafluorobutylsulfonyloxy) isoxazol-5-yl]butanoate (400 mg, 0.83 mmol, 1 eq) and tert-butyl piperazine-1-carboxylate (154 mg, 0.83 mmol, 1 eq) in dimethyl formamide (5 mL) was stirred at 130° C. for 12 hours. The reaction mixture was diluted with water (30 mL) and extracted with ethyl acetate (30 mL×3). The combined organic layers were washed with brine (30 mL×3), dried over anhydrous sodium sulfate, filtered and concentrated under reduced pressure. The residue was purified by prep-TLC (petroleum ether: ethyl acetate=3:1). Tert-butyl 4-[5-(1-methoxycarbonyl-2-methyl-propyl)isoxazol-3-yl]piperazine-1-carboxylate (130 mg, 0.35 mmol, 42% yield) was obtained as a colorless oil.

Step 4

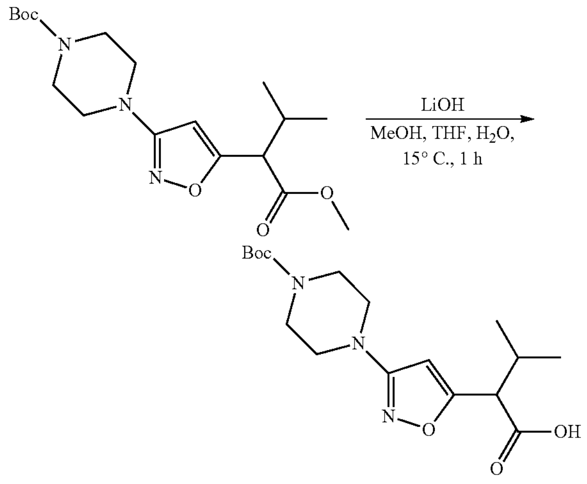

To a solution of tert-butyl 4-[5-(1-methoxycarbonyl-2-methyl-propyl)isoxazol-3-yl]piperazine-1-carboxylate (130 mg, 0.35 mmol, 1 eq) in methanol (2 mL), tetrahydrofuran (2 mL) and water (2 mL) was added lithium hydroxide (44 mg, 1.06 mmol, 3 eq). The reaction mixture was stirred at 15° C. for 1 hour. Water (3 mL) was added. The pH was adjusted to 6 with hydrochloric acid (IM in water), and extracted with ethyl acetate (10 mL×5). The combined organic layers were washed with brine (50 mL×1), dried over anhydrous sodium sulfate, filtered and concentrated under reduced pressure. 2-[3-(4-tert-Butoxycarbonylpiperazin-1-yl) isoxazol-5-yl]-3-methyl-butanoic acid (100 mg, 0.28 mmol, 79% yield) was obtained as a white solid.

Step 5

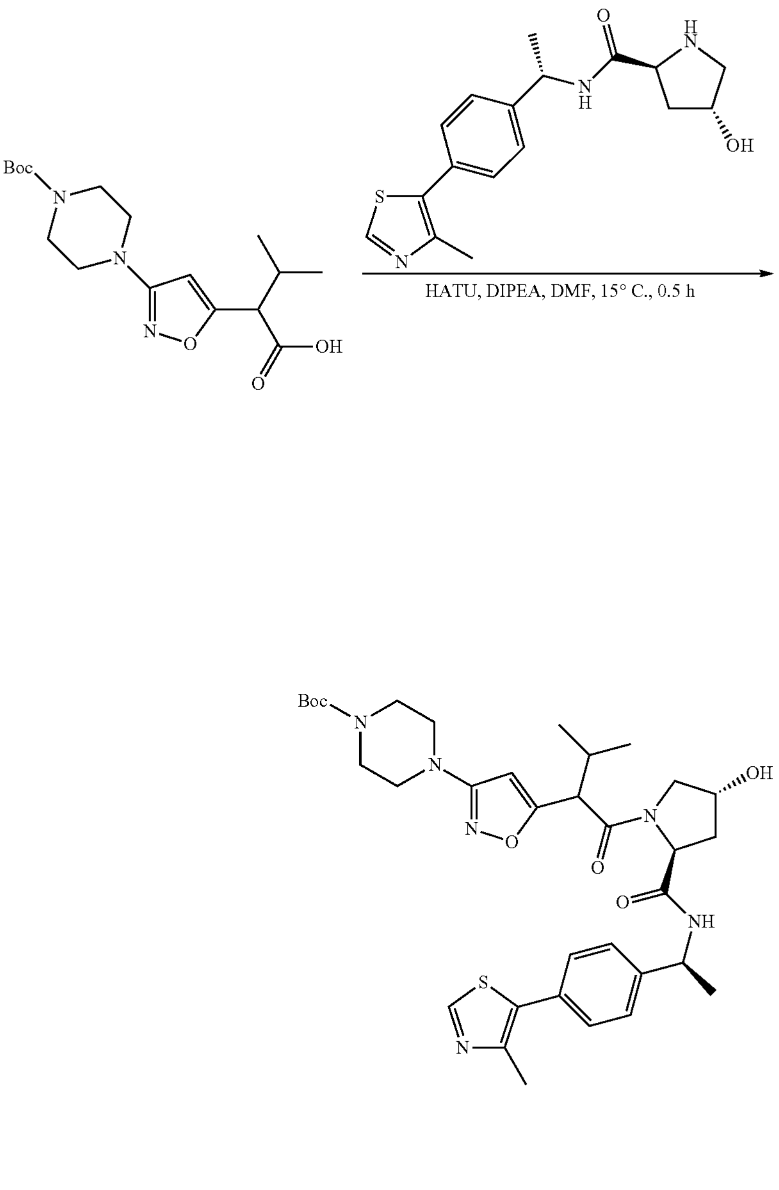

To a solution of 2-[3-(4-tert-butoxycarbonylpiperazin-1-yl)isoxazol-5-yl]-3-methyl-butanoic acid (100 mg, 0.28 mmol, 1 eq) and O-(7-azabenzotriazol-1-yl)-N,N,N',N'-tetramethyluronium hexafluorophosphate (129 mg, 0.33 mmol, 1.2 eq) in dimethyl formamide (5 mL) were added (2S,4R)-4-hydroxy-N-[(1S)-1-[4-(4-methylthiazol-5-yl) phenyl]ethyl]pyrrolidine-2-carboxamide hydrochloride (104 mg, 0.28 mmol, 1 eq) and diisopropyl ethyl amine (109 mg, 0.84 mmol, 3 eq). The reaction mixture was stirred at 15° C. for 0.5 hour. The reaction mixture was poured into water (20 mL), extracted with ethyl acetate (30 mL×3). The combined organic layers were washed with brine (50 mL×3), dried over anhydrous sodium sulfate, filtered and concentrated under reduced pressure. The residue was purified by prep-TLC (dichloromethane:methanol=10:1). tert-Butyl 4-[5-[1-[(2S,4R)-4-hydroxy-2-[[(1S)-1-[4-(4-methylthiazol-5-yl) phenyl]ethyl]carbamoyl]pyrrolidine-1-carbonyl]-2-methyl-propyl]isoxazol-3-yl]piperazine-1-carboxylate (180 mg, 0.26 mmol, 92% yield) was obtained as a colorless oil.

Step 6

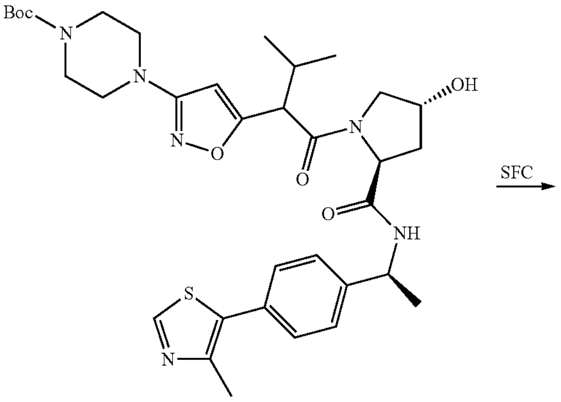

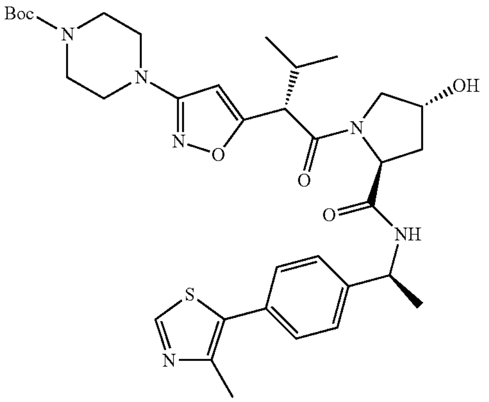

+

-continued

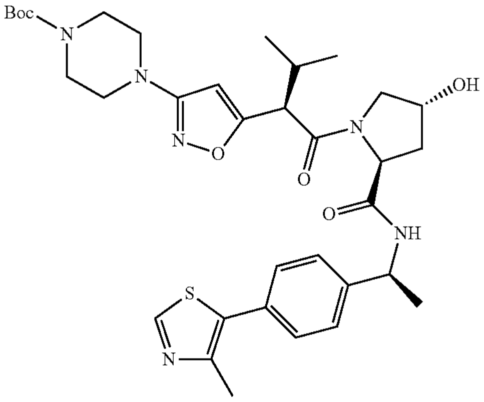

tert-butyl 4-[5-[1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]isoxazol-3-yl]piperazine-1-carboxylate (200 mg, 0.29 mmol, 1 eq) was separated by chiral supercritical fluid chromatography. Instrument: CASWH-Prep-SFC-C, SFC Column: DAICEL Chiralpak AS (250 mm*30 mm, 10 um); Mobile phase: ethanol (0.1% $NH_3$—$H_2O$) in C02 from 25% to 25%; Flow rate: 55 g/min; Wavelength: 220 nm. tert-Butyl 4-[5-[(1S)-1-[(2S,4R)-4-hydroxy-2-[[(1S)-1-[4-(4-methylthiazol-5-yl)phenyl]ethyl] carbamoyl]pyrrolidine-1-carbonyl]-2-methyl-propyl]isoxazol-3-yl]piperazine-1-carboxylate (80 mg, 0.11 mmol, 76% yield, 95% purity) was obtained as a white solid. tert-Butyl 4-[5-[(1R)-1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]isoxazol-3-yl]piperazine-1-carboxylate (70 mg, 0.1 mmol, 68% yield, 98% purity) was obtained as a white solid.

Step 7

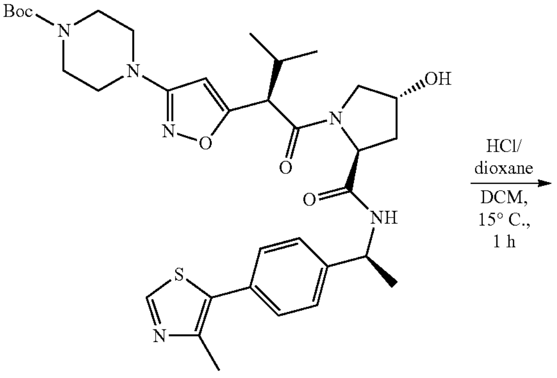

-continued

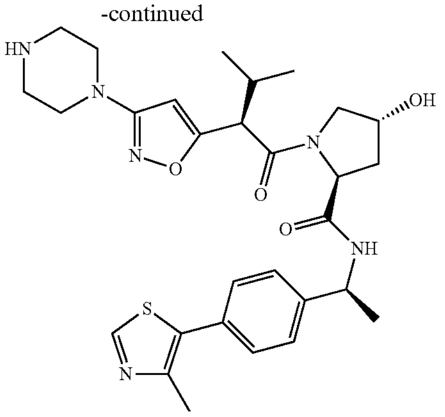

To a solution of tert-butyl 4-[5-[(1R)-1-[(2S,4R)-4-hydroxy-2-[[(1S)-1-[4-(4-methylthiazol-5-yl)phenyl]ethyl]carbamoyl]pyrrolidine-1-carbonyl]-2-methyl-propyl]isoxazol-3-yl]piperazine-1-carboxylate (70 mg, 0.1 mmol, 1 eq) in dichloromethane (2 mL) was added hydrochloric acid (4 M in dioxane, 3 mL). The reaction mixture was stirred at 15° C. for 1 hour. The reaction mixture was concentrated under reduced pressure. (2S,4R)-4-hydroxy-1-[(2R)-3-methyl-2-(3-piperazin-1-ylisoxazol-5-yl)butanoyl]-N-[(1S)-1-[4-(4-methylthiazol-5-yl)phenyl]ethyl]pyrrolidine-2-carboxamide (55 mg, 0.09 mmol, 91% yield) was obtained as a white solid.

Step 8

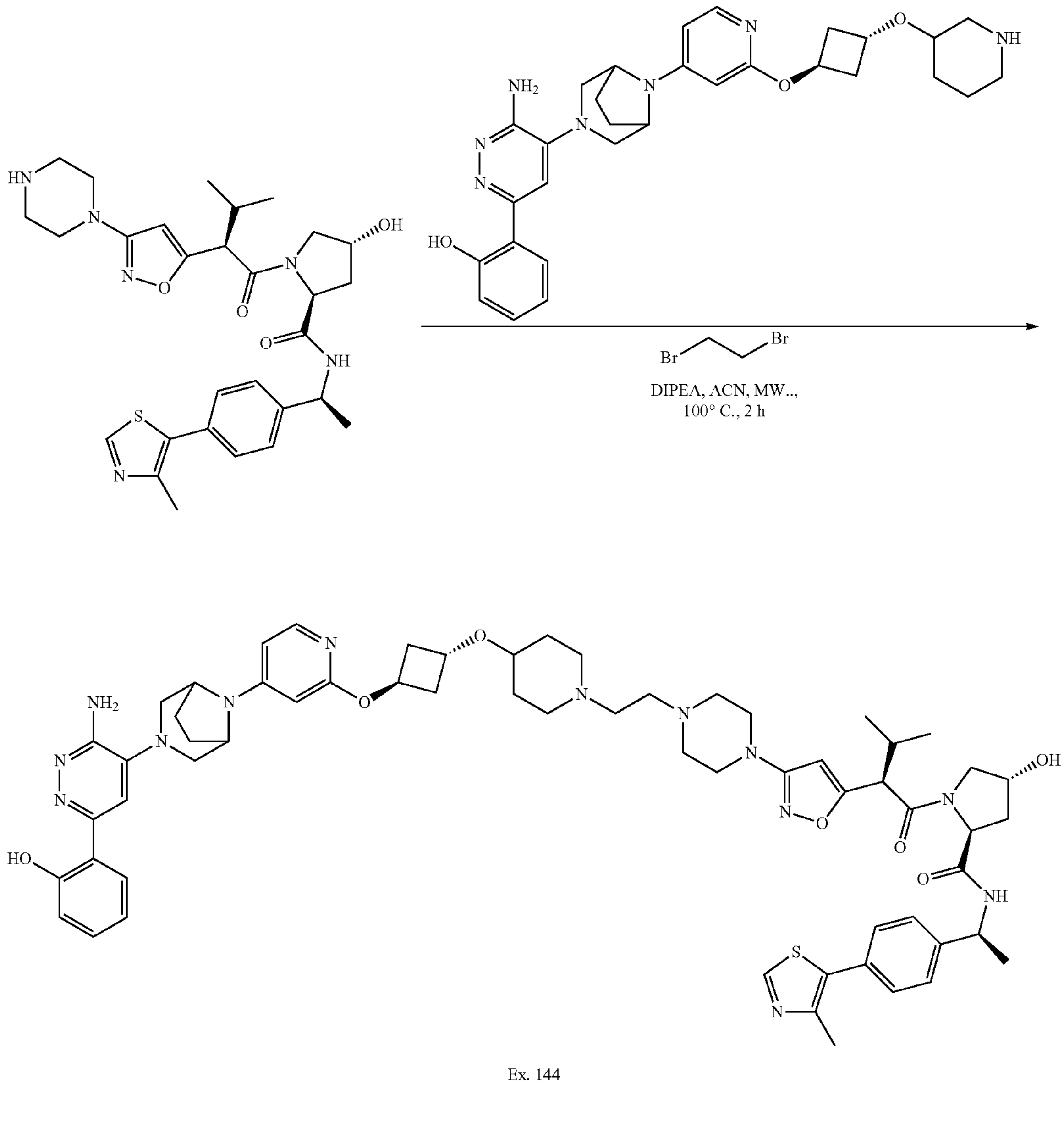

Ex. 144

To a mixture of (2S,4R)-4-hydroxy-1-[(2R)-3-methyl-2-(3-piperazin-1-ylisoxazol-5-yl)butanoyl]-N-[(1S)-1-[4-(4-methylthiazol-5-yl)phenyl]ethyl]pyrrolidine-2-carboxamide (100 mg, 0.16 mmol, 1 eq, hydrochloride), 1,2-dibromoethane (31 mg, 0.16 mmol, 1 eq) and 2-[6-amino-5-[8-[2-[3-(4-piperidyloxy)cyclobutoxy]-4-pyridyl]-3,8-diazabicyclo[3.2.1]octan-3-yl]pyridazin-3-yl]phenol dihydrochloride (102 mg, 0.16 mmol, 1 eq) in acetonitrile (12 mL) was added N,N-diisopropylethylamine (128 mg, 0.99 mmol, 6 eq). The mixture was stirred at 100° C. for 2 h under microwave. The reaction mixture was concentrated under reduced pressure to give a residue. The residue was purified by prep-HPLC (column: Phenomenex Synergi C18 150*25*10 um; mobile phase: [water (0.225% FA)-ACN]; B %: 5%-35%, 10 min). Compound (2S,4R)-1-[(2R)-2-[3-[4-[2-[4-[3-[[4-[3-[3-amino-6-(2-hydroxyphenyl)pyridazin-4- yl]-3,8-diazabicyclo[3.2.1]octan-8-yl]-2-pyridyl]oxy]cyclobutoxy]-1-piperidyl]ethyl]piperazin-1-yl]isoxazol-5-yl]-3-methyl-butanoyl]-4-hydroxy-N-[(1S)-1-[4-(4-methylthiazol-5-yl)phenyl]ethyl]pyrrolidine-2-carboxamide formate (24.6 mg, 0.02 mmol, 12% yield) was obtained as an off-white solid.

Prepared using the analogous procedures as exemplary compound 195.

Exemplary Synthesis of Exemplary Compounds 197 and 352

Ex. 197

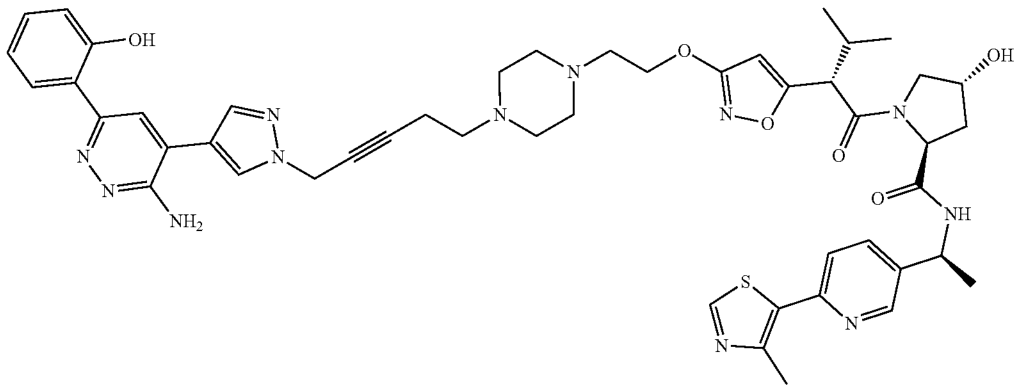

Ex. 352

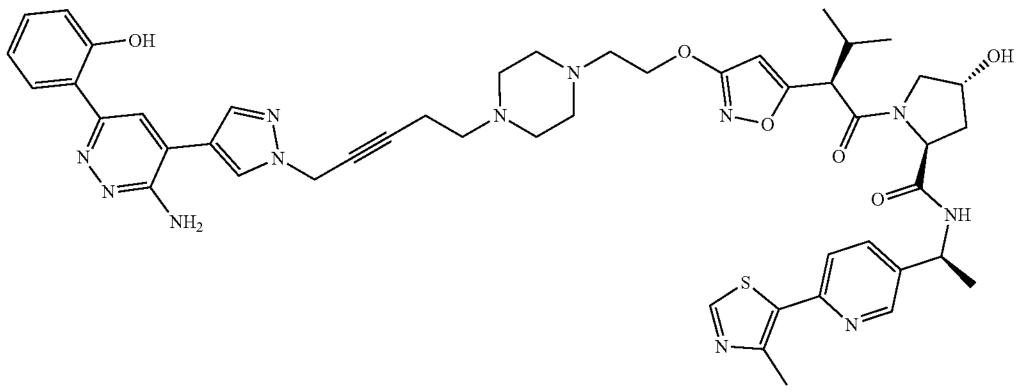

Prepared using procedures analogous to those described for exemplary compounds 112 and 116.

Exemplary Synthesis of Exemplary Compound 114

Ex. 114

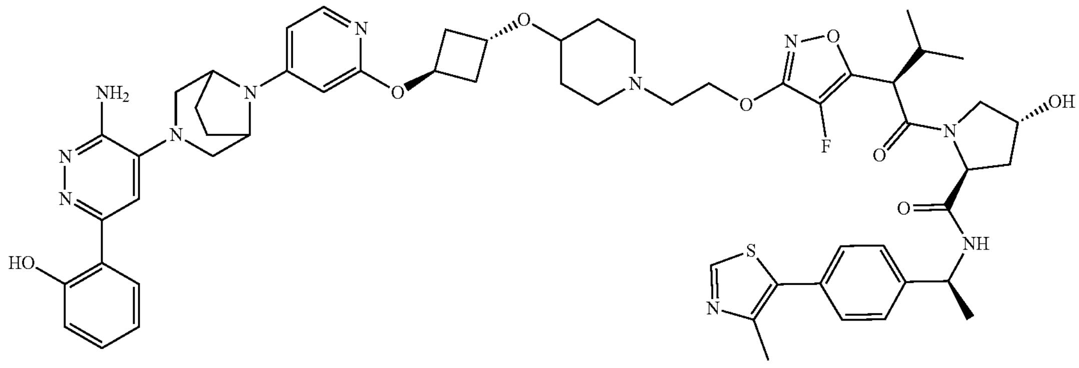

Step 1

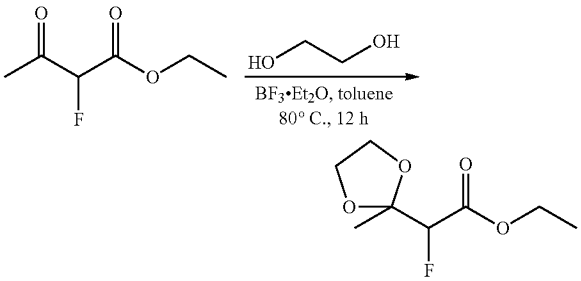

To a solution of ethyl 2-fluoro-3-oxo-butanoate (33.6 g, 226.82 mmol, 28.47 mL, 1 eq) and ethylene glycol (70.39 g, 1.13 mol, 63.42 mL, 5 eq) in toluene (500 mL) was added boron trifluoride ethyl ether (3.36 g, 23.67 mmol, 2.92 mL, 0.1 eq). The mixture was stirred at 80° C. for 12 hours. The reaction mixture was diluted with water (300 mL), and extracted with ethyl acetate (300 mL) two times. The combined organic phases were washed with brine (300 mL) two times, dried over anhydrous sodium sulfate, filtered and concentrated to afford crude product. The residue was purified by silica gel chromatography (petroleum ether:ethyl acetate=100:1 to 10:1). Compound ethyl 2-fluoro-2-(2-methyl-1,3-dioxolan-2-yl)acetate (29.3 g, 152.5 mmol, 67% yield) was obtained as a colorless oil.

Step 2

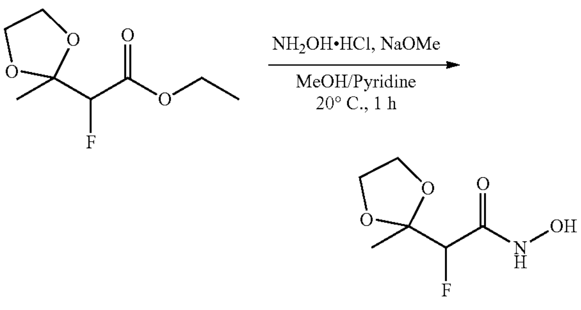

To a solution of ethyl 2-fluoro-2-(2-methyl-1,3-dioxolan-2-yl)acetate (29.3 g, 152.46 mmol, 1 eq) and hydroxylamine hydrochloride (21.19 g, 304.92 mmol, 2 eq) in pyridine (164 mL), sodium methoxide (28%) in methanol (61 mL) was dropwise added at 0° C. over 1 hour. The mixture was stirred at 20° C. for 1 hour. The reaction mixture was filtered, and the filtrate was diluted with tetrahydrofuran (500 mL) and additionally filtered. The filtrate was concentrated to give the crude product which was purified by silica gel chromatography (petroleum ether:ethyl acetate=1:0 to 0:1) to give product. Compound 2-fluoro-2-(2-methyl-1,3-dioxolan-2-yl)ethanehydroxamic acid (10.4 g, 58.1 mmol, 38% yield) was obtained as an orange oil.

Step 3

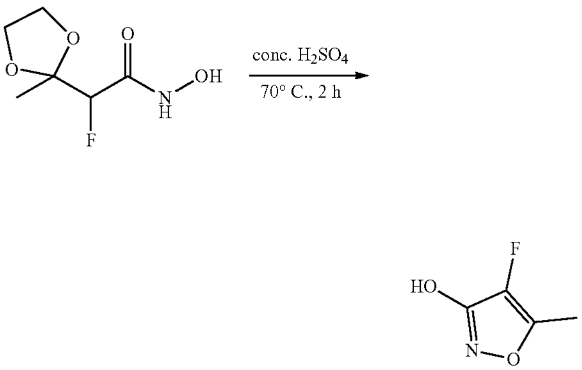

Solution of 2-fluoro-2-(2-methyl-1,3-dioxolan-2-yl)ethanehydroxamic acid (10.35 g, 57.77 mmol, 1 eq) in sulfuric acid (18 M, 50 mL, 15.58 eq) was stirred at 70° C. for 2 hours. The reaction mixture was poured into ice water (250 mL), and then extracted with ethyl acetate (250 mL) two times. The combined organic layers were dried over anhydrous sodium sulfate, concentrated to afford the crude product. The crude product was used directly in the next step without purification. Compound 4-fluoro-5-methyl-isoxazol-3-ol (4.60 g, 39.29 mmol) was obtained as a yellow solid.

Step 4

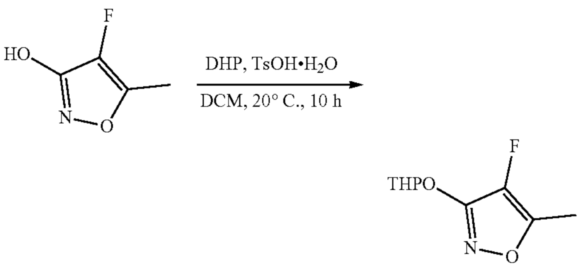

To a solution of 4-fluoro-5-methyl-isoxazol-3-ol (5.7 g, 48.69 mmol, 1 eq) in dichloromethane (228 mL) was added p-toluenesulfonic acid monohydrate (926 mg, 4.87 mmol, 0.1 eq) and 3,4-dihydro-2H-pyran (20.48 g, 243.43 mmol, 22.26 mL, 5 eq). The mixture was stirred at 20° C. for 10 hours. The reaction mixture was poured into water (100 mL), and pH was adjusted to 7 with saturated sodium bicarbonate solution (60 mL). The mixture then was extracted with dichloromethane (200 mL) two times. The combined organic layers were washed with saturated aqueous sodium chloride (200 mL) two times and dried over anhydrous sodium sulfate and filtered. The filtrate was concentrated to give the crude product which was purified by silica gel chromatography (petroleum ether:ethyl acetate=1:0 to 8:1). Compound 4-fluoro-5-methyl-3-tetrahydropyran-2-yloxy-isoxazole (7.94 g, 39.5 mmol, 81% yield) was obtained as a yellow solid.

Step 5

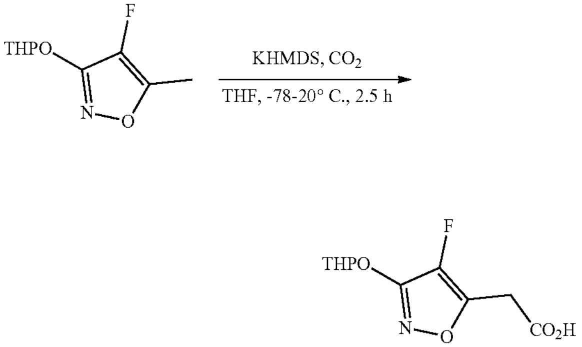

To a solution of 4-fluoro-5-methyl-3-tetrahydropyran-2-yloxy-isoxazole (8.07 g, 40.13 mmol, 1 eq) in tetrahydrofuran (115 mL) was dropwise added potassium bis(trimethylsilyl)amide (1 M, 60.20 mL, 1.5 eq) at −78° C. under nitrogen, and the reaction mixture was stirred at −78° C. for 0.5 hour. Through the reaction mixture was then bubbled carbon dioxide (15 psi) for 1 hour at −78° C., and the mixture was stirred at 20° C. for 1 hour. The reaction mixture was quenched by saturated ammonium chloride aqueous solution (150 mL) and extracted with ethyl acetate (100 mL) two times. The aqueous layer was adjusted by aqueous hydrochloric acid solution (1 M) until pH=3 at 0° C., and then was extracted with chloroform and isopropanol (v/v=5:1, 150 mL, three times). The combined layers were dried over anhydrous sodium sulfate, filtered, and the filtrate was concentrated to give crude product. Compound 2-(4-fluoro-3-tetrahydropyran-2-yloxy-isoxazol-5-yl)acetic acid (8.07 g, 32.91 mmol) was obtained as a yellow solid.

Step 6

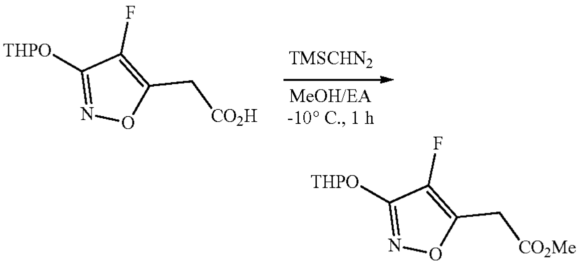

To a solution of 2-(4-fluoro-3-tetrahydropyran-2-yloxy-isoxazol-5-yl)acetic acid (7.87 g, 32.10 mmol, 1 eq) in a mixture of methanol (70 mL) and ethyl acetate (70 mL) was dropwise added trimethylsilyl diazomethane ether solution (2 M, 24.07 mL, 1.5 eq) at −10° C., and the mixture was stirred at −10° C. for 1 hour. The reaction mixture was adjusted with acetic acid until pH=7, and ethyl acetate (150 mL) was added. The organic layer was washed with saturated sodium bicarbonate solution (50 mL) and dried over anhydrous sodium sulfate, filtered, and the filtrate was concentrated to give the crude product. The crude product was purified by silica gel chromatography (petroleum ether: ethyl acetate=1:0 to 5:1). Compound methyl 2-(4-fluoro-3-tetrahydropyran-2-yloxy-isoxazol-5-yl)acetate (4.51 g, 17.40 mmol, 54% yield) was obtained as a colorless oil.

Step 7

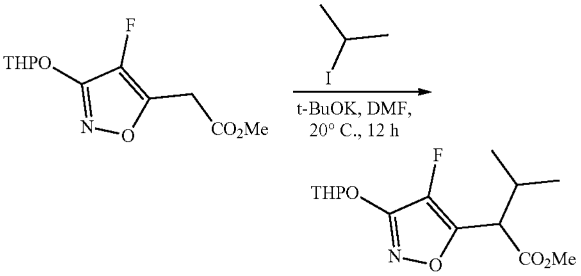

To a solution of methyl 2-(4-fluoro-3-tetrahydropyran-2-yloxy-isoxazol-5-yl)acetate (4.42 g, 17.05 mmol, 1 eq) in dimethylformamide (66 mL) was added potassium tert-butoxide (2.87 g, 25.58 mmol, 1.5 eq) at 0° C., and then 2-iodopropane (3.48 g, 20.46 mmol, 2.05 mL, 1.2 eq). The mixture was stirred at 20° C. for 12 hours. The reaction mixture was diluted with water (60 mL) and extracted with ethyl acetate (80 mL) three times. The combined layers were washed with saturated aqueous sodium chloride (100 mL) two times, dried over anhydrous sodium sulfate and concentrated to afford crude product. The crude product was purified by silica gel chromatography (petroleum ether). Compound methyl 2-(4-fluoro-3-tetrahydropyran-2-yloxy-isoxazol-5-yl)-3-methyl-butanoate (5.25 g) was obtained as a yellow oil.

Step 8

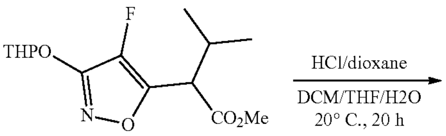

-continued

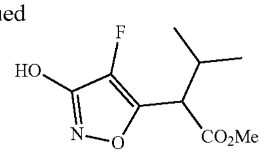

To a solution of methyl 2-(4-fluoro-3-tetrahydropyran-2-yloxy-isoxazol-5-yl)-3-methyl-butanoate (5.48 g, 18.19 mmol, 1 eq) in a mixture of dichloromethane (20 mL) and tetrahydrofuran (5 mL) and water (5 mL) was added hydrochloric acid/dioxane (4 M, 30.00 mL, 6.60 eq). The mixture was stirred at 20° C. for 20 hours. The reaction mixture was poured into saturated sodium carbonate solution (300 mL), and then extracted with methyl tert-butyl ether (100 mL) three times. The water layer pH was adjusted by adding hydrochloric acid solution (3 M) until pH=2. The aqueous layer was extracted with chloroform (150 mL) three times, dried over anhydrous sodium sulfate and concentrated to afford the crude product. The residue was purified by semi-preparative reverse phase (column: Kromasil 250*50 mm*10 um; mobile phase: [water (0.225% FA)-ACN]; B %: 21ACN %-51ACN %, 29 min, 79% min). Compound methyl 2-(4-fluoro-3-hydroxy-isoxazol-5-yl)-3-methyl-butanoate (1.27 g, 5.86 mmol, 32% yield) was obtained as a white solid.

Step 9

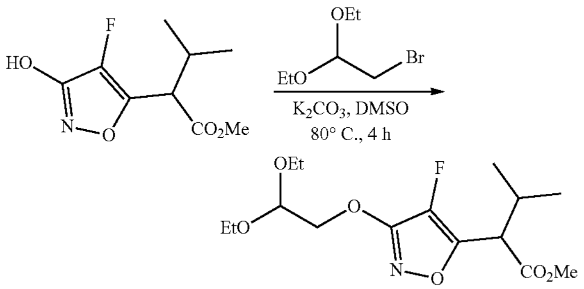

Methyl 2-(4-fluoro-3-hydroxy-isoxazol-5-yl)-3-methyl-butanoate (0.5 g, 2.30 mmol, 1 eq), 2-bromo-1,1-diethoxy-ethane (907 mg, 4.60 mmol, 0.69 mL, 2 eq) and potassium carbonate (636 mg, 4.60 mmol, 2 eq) were taken up in a microwave tube in dimethylsulfoxide (8 mL). The sealed tube was heated at 80° C. for 2 hours under microwave irradiation. After LCMS showed the starting material still remained, the sealed tube was heated at 80° C. for another 2 hours under microwave irradiation. The mixture was filtered and concentrated in vacuum. The residue was purified by semi-preparative reverse phase (column: Phenomenex Synergi C18 150*25*10 um; mobile phase: [water (0.225% FA)-ACN]; B %: 40%-70%, 9 min). Compound methyl 2-[3-(2,2-diethoxyethoxy)-4-fluoro-isoxazol-5-yl]-3-methyl-butanoate (266 mg, 0.80 mmol, 35% yield) was obtained as a yellow oil, and 46 mg of methyl 2-(4-fluoro-3-hydroxy-isoxazol-5-yl)-3-methyl-butanoate was recovered.

Methyl 2-[3-(2,2-diethoxyethoxy)-4-fluoro-isoxazol-5-yl]-3-methyl-butanoate was converted to the final compound using procedures analogous to those described above for exemplary compound 76.

Exemplary compounds 198, 208, 209, 269, and 270 were prepared using analogous procedures.

Exemplary Synthesis of Exemplary Compound 200

Ex. 200

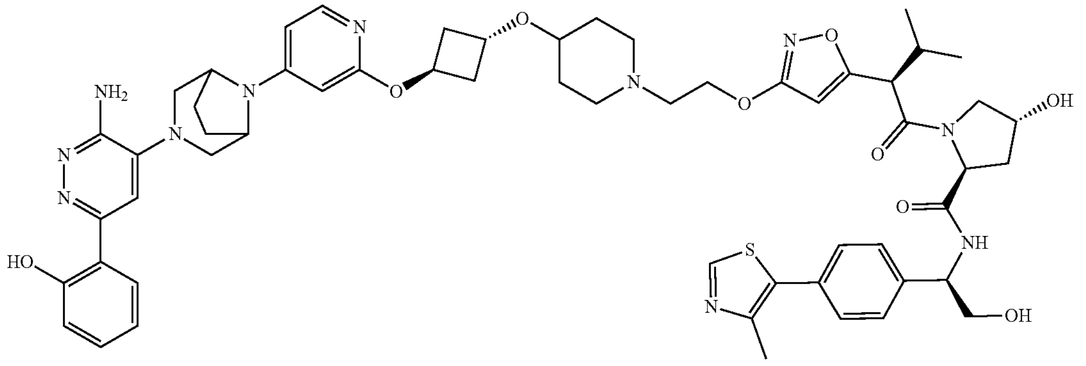

Step 1

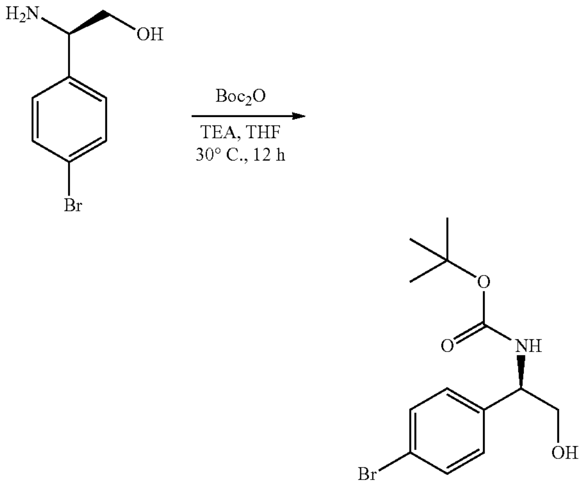

To a solution of (2R)-2-amino-2-(4-bromophenyl)ethanol (1.74 g, 6.89 mmol, 1 eq, hydrochloride) in tetrahydrofuran (25 mL) was added triethylamine (2.79 g, 27.56 mmol, 3.84 mL, 4 eq) and tert-butoxycarbonyl tert-butyl carbonate (1.80 g, 8.27 mmol, 1.90 mL, 1.2 eq). The mixture was stirred at 30° C. for 12 hours. The reaction mixture was concentrated under reduced pressure to remove tetrahydrofuran. The residue was extracted with ethyl acetate (50 mL×2). The combined organic layers were washed with aqueous brine (40 mL×2), dried over anhydrous sodium sulfate, filtered and concentrated under reduced pressure. The crude product was triturated with petroleum ether/ethyl acetate (22 mL, v:v=10:1). Compound tert-butyl N-[(1R)-1-(4-bromophenyl)-2-hydroxy-ethyl]carbamate (2 g, 6.33 mmol, 91% yield) was obtained as a white solid.

Step 2

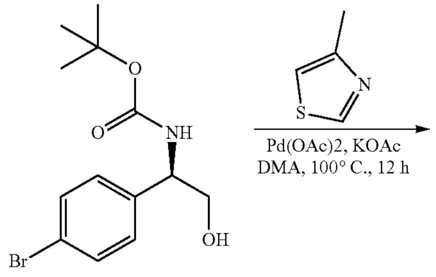

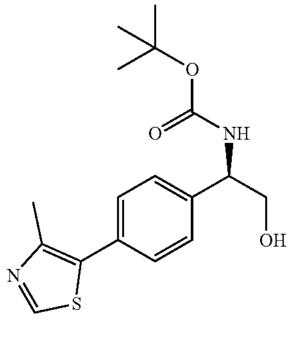

A mixture of tert-butyl N-[(1R)-1-(4-bromophenyl)-2-hydroxy-ethyl]carbamate (2.0 g, 6.33 mmol, 1 eq), 4-methylthiazole (1.25 g, 12.65 mmol, 1.15 mL, 2 eq), potassium acetate (1.24 g, 12.65 mmol, 2 eq) and palladium acetate (142 mg, 0.63 mmol, 0.1 eq) in dimethylacetamide (40 mL) was degassed and purged with nitrogen for 3 times, and then the mixture was stirred at 100° C. for 12 hours under nitrogen atmosphere. The reaction mixture was concentrated under reduced pressure to remove dimethylacetamide. The residue was extracted with ethyl acetate (40 mL×2) and washed with saturated brine (40 mL×2). The combined organic layers were dried over anhydrous sodium sulfate, filtered and concentrated under reduced pressure. The residue was purified by silica gel chromatography (petroleum ether/ethyl acetate=5/1 to 1/2). Compound tert-butyl N-[(1R)-2-hydroxy-1-[4-(4-methylthiazol-5-yl) phenyl]ethyl]carbamate (1.45 g, 3.98 mmol, 63% yield) was obtained as a yellow oil.

tert-Butyl N-[(1R)-2-hydroxy-1-[4-(4-methylthiazol-5-yl) phenyl]ethyl]carbamate was converted to the final compound using procedures analogous to those described for exemplary compound 180 above.

Exemplar compounds 199, 158, and 100 were prepared using analogous procedures.

Exemplary Synthesis of Exemplary Compound 202

Ex. 202

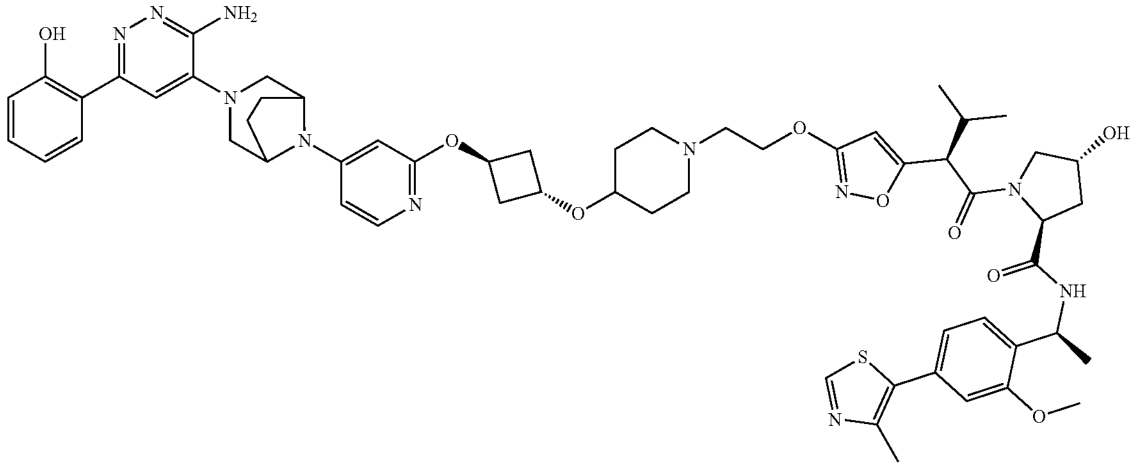

-continued

Step 1

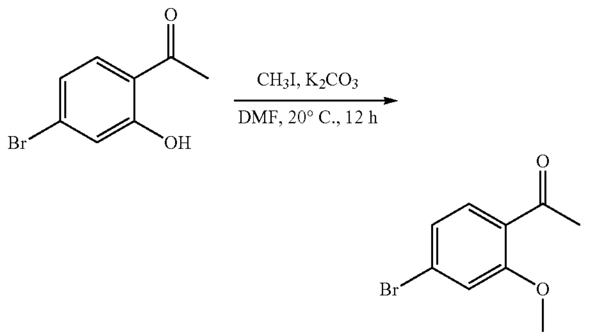

To a solution of 1-(4-bromo-2-hydroxy-phenyl)ethanone (10 g, 46.50 mmol, 1.0 eq) in dimethyl formamide (50 mL) was added potassium carbonate (9.64 g, 69.75 mmol, 1.5 eq). Then iodomethane (13.20 g, 93.00 mmol, 2.0 eq) was added into the mixture at 0° C. Then the mixture was stirred at 20° C. for 12 hours. The mixture was diluted with water (200 mL), extracted with ethyl acetate (100 ml×3), washed with brine (50 mL×2), dried over anhydrous sodium sulfate, filtered and then concentrated. 1-(4-bromo-2-methoxy-phenyl)ethanone (10.5 g, 45.84 mmol, 98% yield) was obtained as a yellow solid.

Step 2

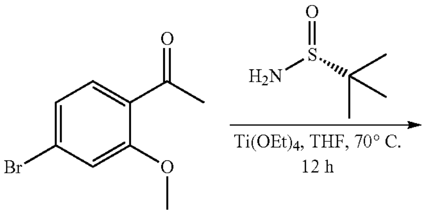

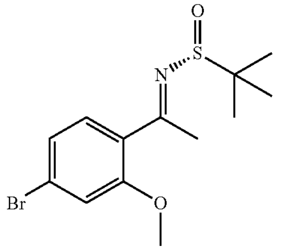

To a solution of 1-(4-bromo-2-methoxy-phenyl)ethanone (10 g, 43.65 mmol, 1.18 eq) in tetrahydrofuran (50 mL) was added titanium tetraethoxide (16.94 g, 74.26 mmol, 2.0 eq). Then 2-methylpropane-2-sulfinamide (4.5 g, 37.13 mmol, 1.0 eq) was added to the mixture, and the mixture was purged with $N_2$ 3 times. The mixture was then stirred at 70° C. for 12 hours. The mixture was quenched with water (100 mL), diluted with water (200 mL), filtered and then extracted with ethyl acetate (200 ml×3), washed with brine (200 mL), dried over anhydrous sodium sulfate, filtered and then concentrated. The residue was purified by silica gel column chromatography (petroleum ether:ethyl acetate=20:1 to 3:1). ((R,E)-N-(1-(4-bromo-2-methoxyphenyl)ethylidene)-2-methylpropane-2-sulfinamide (9 g, 27.09 mmol, 73% yield) was obtained as a yellow oil.

Step 3

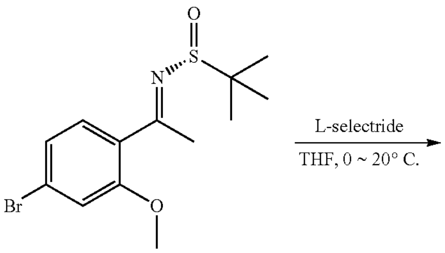

-continued

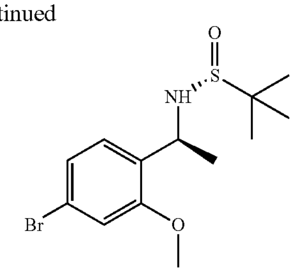

To a solution of ((R,E)-N-(1-(4-bromo-2-methoxyphenyl)ethylidene)-2-methylpropane-2-sulfinamide (9 g, 27.09 mmol, 1.0 eq) in tetrahydrofuran (90 mL) was added L-selectride (1 M, 81.26 mL, 3.0 eq) at 0° C. Then the mixture was stirred at 20° C. for 2 hours. The mixture was quenched with water (100 mL), diluted with water (20 mL), extracted with ethyl acetate (300 mL×3), washed with brine (200 mL), dried over anhydrous sodium sulfate, filtered and then concentrated. The residue was purified by silica gel column chromatography (petroleum ether:ethyl acetate=20:1 to 1:1). N-[(1S)-1-(4-bromo-2-methoxy-phenyl)ethyl]-2-methyl-propane-2-sulfinamide (5.5 g, 16.45 mmol, 60% yield) was obtained as a yellow oil.

Step 4

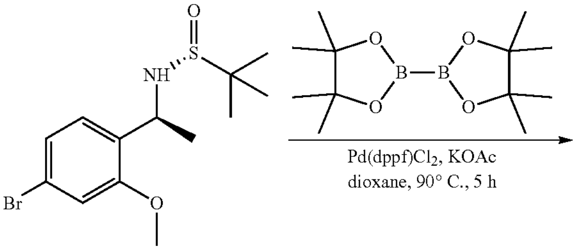

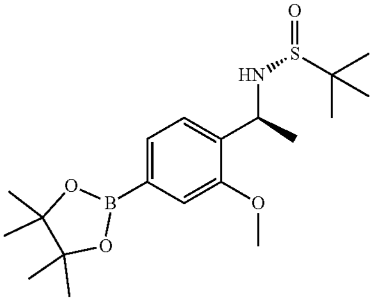

To a solution of N-[(1S)-1-(4-bromo-2-methoxy-phenyl)ethyl]-2-methyl-propane-2-sulfinamide (4.7 g, 14.06 mmol, 1.0 eq) and 4,4,5,5-tetramethyl-2-(4,4,5,5-tetramethyl-1,3,2-dioxaborolan-2-yl)-1,3,2-dioxaborolane (5.36 g, 21.09 mmol, 1.5 eq) in dioxane (12 mL) was added [1,1'-bis(diphenylphosphino)ferrocene]dichloropalladium (ii) (1.03 g, 1.41 mmol, 0.1 eq) and potassium acetate (2.76 g, 28.12 mmol, 2.0 eq). Then the mixture was purged with $N_2$ 3 times. Then the mixture was stirred at 90° C. for 5 hours. The mixture was diluted with water (20 mL), filtered and then extracted with ethyl acetate (50 mL×3), washed with brine (30 mL), dried over anhydrous sodium sulfate, filtered and then concentrated. The residue was purified by silica gel column chromatography (petroleum ether:ethyl acetate=10:1 to 1:1). N-[(1S)-1-[2-methoxy-4-(4,4,5,5-tetramethyl-1,3,2-dioxaborolan-2-yl)phenyl]ethyl]-2-methyl-propane-2-sulfinamide (4.5 g, 11.80 mmol, 84% yield) was obtained as a yellow oil.

N-[(1S)-1-[2-methoxy-4-(4,4,5,5-tetramethyl-1,3,2-dioxaborolan-2-yl)phenyl]ethyl]-2-methyl-propane-2-sulfinamide was converted to (S)-1-(2-methoxy-4-(4-methylthiazol-5-yl)phenyl)ethan-1-amine according to the scheme below.

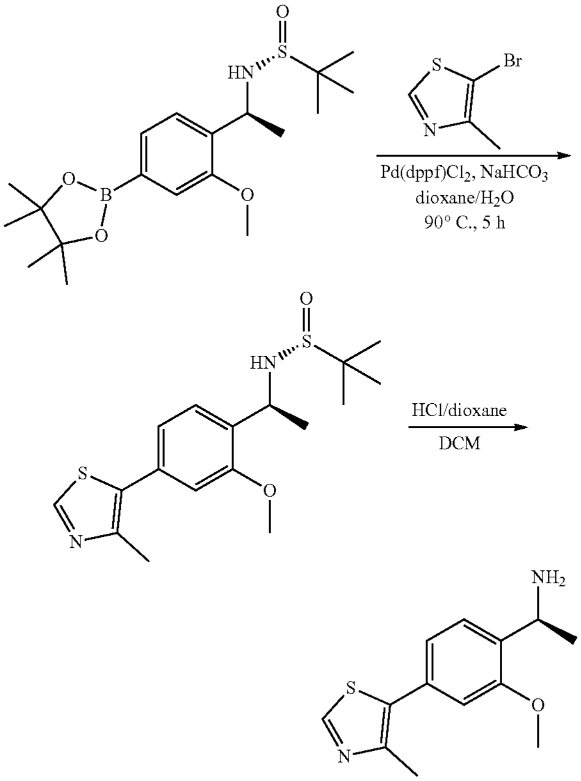

(S)-1-(2-methoxy-4-(4-methylthiazol-5-yl)phenyl)ethan-1-amine was converted to the final compound using procedures analogous to those described for other examples above (e.g., exemplary compound 64).

Exemplary compound 201 was prepared using procedures analogous to those described above.

Exemplary Synthesis of Exemplary Compound 203

Step 1

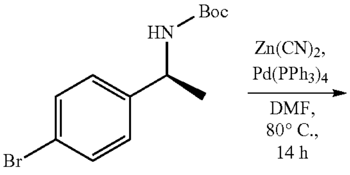

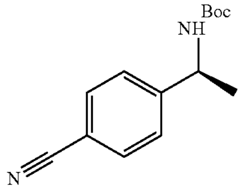

To a solution of tert-butyl N-[(1S)-1-(4-bromophenyl)ethyl]carbamate (2 g, 6.66 mmol, 1 eq) in N,N-dimethylformamide (20 mL) were added palladium tetrakistriphenylphosphine (770 mg, 0.67 mmol, 0.1 eq) and zinc cyanide (782 mg, 6.66 mmol, 0.4 mL, 1 eq). The reaction solution was stirred at 80° C. for 14 h. The solution was quenched with water (80 ml) and extracted with ethyl acetate (50 mL×3). The combined organic layer was washed with brine (20 mL×3). The organic layer was dried over anhydrous sodium sulfate, filtered and concentrated under reduced pressure to give a residue. The residue was purified by silica gel column chromatography (petroleum ether/ethyl acetate=30/1 to 3:1) to get the product. tert-Butyl N-[(1S)-1-(4-cyanophenyl)ethyl]carbamate (1.6 g, 6.50 mmol, 97.50% yield) was obtained as a colorless gum.

tert-Butyl N-[(1S)-1-(4-cyanophenyl)ethyl]carbamate was converted to the final compound using procedures described above.

Exemplary compound 204 was prepared using analogous procedures.

Ex. 203

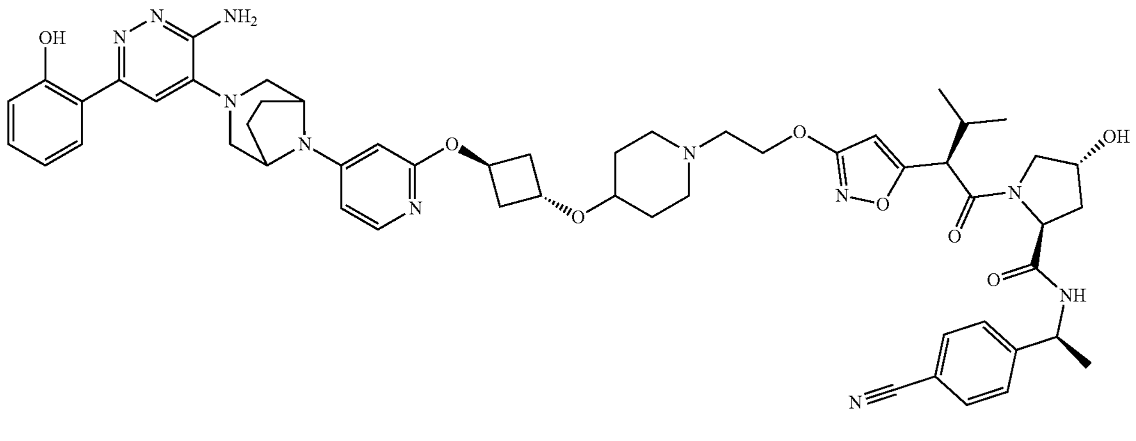

Exemplary Synthesis of Exemplary Compound 91

A9999

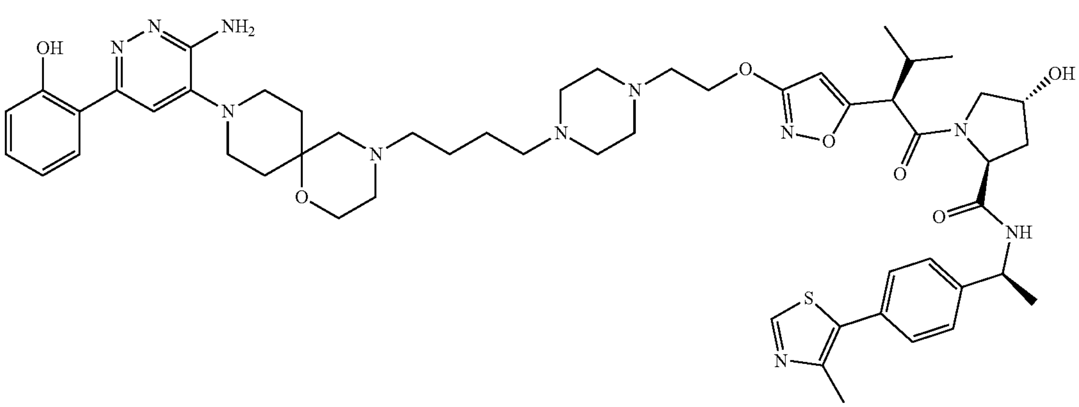

Step 1

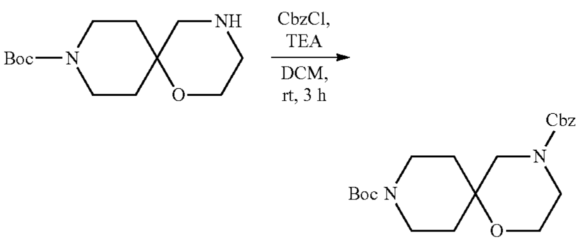 [SMILES: CC(C)(C)OC(=O)N1CCC2(CC1)CNCCO2 ; O=C(OCc1ccccc1)N1CCOC2(CCNCC2)C1 ; "Boc"]

Into a 100 mL round-bottom flask, was placed tert-butyl 1-oxa-4,9-diazaspiro[5.5]undecane-9-carboxylate (3.5 g, 13.7 mmol, 1.0 equiv) and TEA (4.1 g, 0.1 mmol, 3.0 equiv) in DCM (8 mL), to which was added CbzCl (2.8 g, 0.1 mmol, 1.2 equiv) slowly. The resulting mixture was stirred for 12 hours at room temperature. The reaction mixture was then quenched by the addition of 20 mL water and extracted with DCM (20 mL×2). The combined organic layer was dried over anhydrous sodium sulfate and concentrated under reduced pressure. The residue was applied onto a silica gel column eluting with ethyl acetate/petroleum ether (1:0). This resulted in 4.0 g (75%) of 4-benzyl 9-tert-butyl 1-oxa-4,9-diazaspiro[5.5]undecane-4,9-dicarboxylate as a white oil.

Step 2

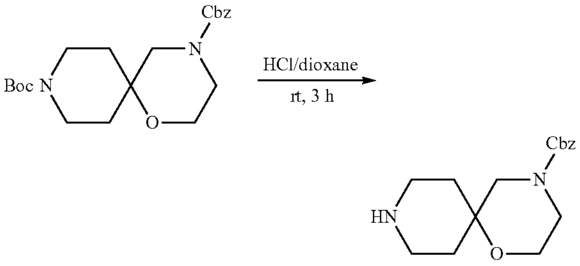 [SMILES: O=C(OCc1ccccc1)N1CCOC2(CCNCC2)C1 ; O=C(OCc1ccccc1)N1CCOC2(CCNCC2)C1 ; "Boc"]

Into a 100 mL round-bottom flask was placed 4-benzyl 9-tert-butyl 1-oxa-4,9-diazaspiro[5.5]undecane-4,9-dicarboxylate (4.0 g, 10.2 mmol, 1.0 equiv) in dioxane (15 mL), and then hydrogen chloride in 1,4-dioxane solution (4.0 M, 4 mL) was added. The resulting mixture was stirred for 3 hours at room temperature and then was concentrated under reduced pressure. This resulted in 2.9 g (87%) of benzyl 1-oxa-4,9-diazaspiro[5.5]undecane-4-carboxylate hydrochloride salt as a solid.

Step 3

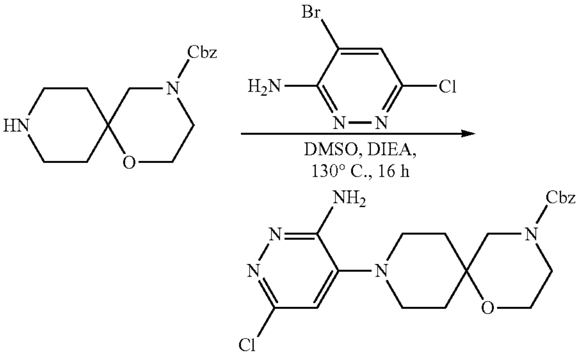

Into a 30 mL sealed tube, was placed benzyl 1-oxa-4,9-diazaspiro[5.5]undecane-4-carboxylate hydrochloride salt (2.9 g, 8.9 mmol, 1.0 equiv), 4-bromo-6-chloropyridazin-3-amine (2.1 g, 0.1 mmol), and DIEA (3.9 g, 0.1 mmol) in DMSO (8 mL). The resulting mixture was stirred for 12 hours at 130° C. in an oil bath. The reaction mixture was then quenched by the addition of 20 mL of water/ice. The resulting mixture was extracted with ethyl acetate (20 mL×2). The combined organic layer was dried over anhydrous sodium sulfate and concentrated under reduced pressure. The residue was applied onto a silica gel column eluting with ethyl acetate/petroleum ether (1:0). This resulted in 3.1 g (84%) of benzyl 9-(3-amino-6-chloropyridazin-4-yl)-1-oxa-4,9-diazaspiro[5.5]undecane-4-carboxylate as a yellow solid.

Step 4

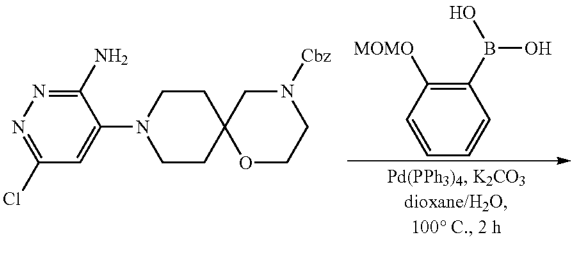

-continued

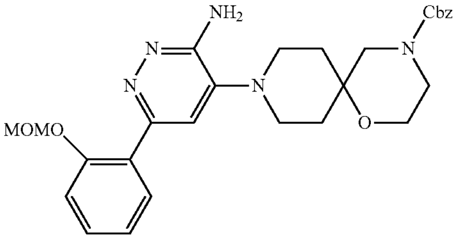

Into a 30-mL sealed tube, was placed benzyl 9-(3-amino-6-chloropyridazin-4-yl)-1-oxa-4,9-diazaspiro[5.5] undecane-4-carboxylate (3.1 g, 7.4 mmol, 1.0 equiv), [2-(methoxymethoxy) phenyl] boronic acid (2.7 g, 0.1 mmol, 2.0 equiv), $Pd(PPh_3)_4$ (859.4 mg, 0.7 mmol, 0.1 equiv), and $K_2CO_3$ (3.1 g, 0.1 mmol, 3.0 equiv) in dioxane (5 mL) and $H_2O$ (1 mL). The resulting mixture was stirred for 12 hours at 100° C. in an oil bath, and then was extracted with ethyl acetate (20 mL×2). The combined organic phase was dried over anhydrous sodium sulfate and concentrated under reduced pressure. The residue was applied onto a silica gel column eluting with dichloromethane/methanol (10:1). This resulted in 3.2 g (83%) of benzyl 9-[3-amino-6-[2-(methoxymethoxy) phenyl] pyridazin-4-yl]-1-oxa-4,9-diazaspiro[5.5] undecane-4-carboxylate as a yellow solid.

Step 5

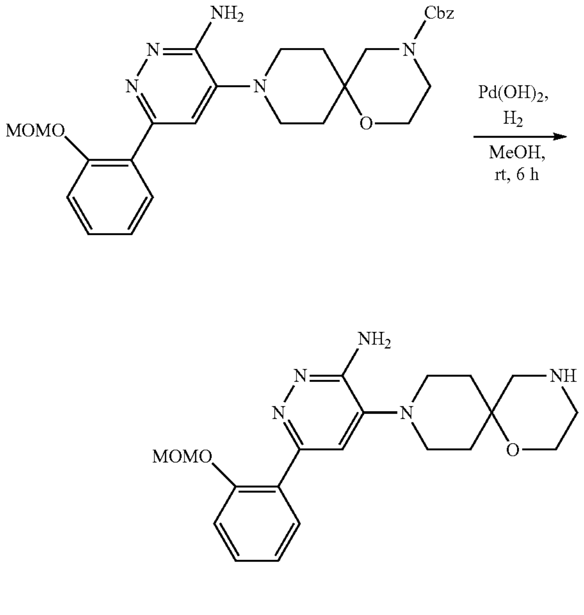

In a 100 ml round bottom flask, to a solution of benzyl 9-[3-amino-6-[2-(methoxymethoxy) phenyl] pyridazin-4-yl]-1-oxa-4,9-diazaspiro[5.5] undecane-4-carboxylate (3.2 g, 6.2 mmol, 1.0 equiv) in methanol (10 mL) was added $Pd(OH)_2/C$ (10%, 500 mg) under nitrogen atmosphere. The flask was then vacuumed and flushed with hydrogen. The reaction mixture was hydrogenated at room temperature for 6 hours under hydrogen atmosphere using a hydrogen balloon, then filtered through a Celite pad and concentrated under reduced pressure. This resulted in 1.8 g (76%) of 6-[2-(methoxymethoxy) phenyl]-4-[1-oxa-4,9-diazaspiro [5.5]undecan-9-yl] pyridazin-3-amine as a yellow solid.

Step 6

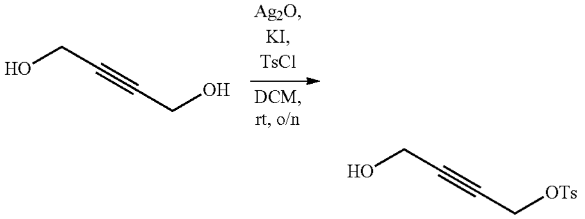 [SMILES: OCC#CCO ; Cc1ccc(S(=O)(=O)OCC#CCO)cc1]

Into a 250-mL round-bottom flask, was placed a solution of but-2-yne-1,4-diol (2.58 g, 30.00 mmol, 1.00 equiv), silver oxide (10.35 g, 45.00 mmol, 1.50 equiv), and potassium iodide (498 mg, 3.00 mmol, 0.10 equiv) in dichloromethane (80 mL). Then 4-methylbenzenesulfonyl chloride (5.70 g, 30.00 mmol, 1.00 equiv) was added. The reaction mixture was stirred overnight at room temperature. The insoluble solids were filtered out, and the filtrate was concentrated. The residue was applied onto a silica gel column eluting with ethyl acetate/petroleum ether (1:2). This resulted in 6.13 g (85%) of 4-hydroxybut-2-yn-1-yl 4-methylbenzenesulfonate as a yellow oil.

Step 7

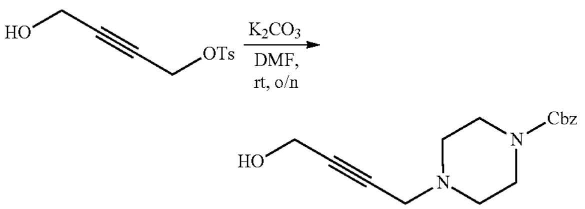

Into a 250-mL round-bottom flask, was placed a solution of 4-hydroxybut-2-yn-1-yl 4-methylbenzenesulfonate (6.13 g, 25.54 mmol, 1.10 equiv), benzyl piperazine-1-carboxylate (5.11 g, 23.22 mmol, 1.00 equiv) and potassium carbonate (12.82 g, 92.88 mmol, 4.00 equiv) in DMF (40 mL). The resulting mixture was stirred overnight at room temperature. The reaction mixture was then quenched by water (400 mL) and extracted with ethyl acetate (200 mL×2). The combined organic phase was dried over sodium sulfate and concentrated. The residue was applied onto a silica gel column eluting with ethyl acetate/petroleum ether (1:1). This resulted in 2.01 g (30%) of benzyl 4-(4-hydroxybut-2-yn-1-yl)piperazine-1-carboxylate as a yellow oil.

Step 8

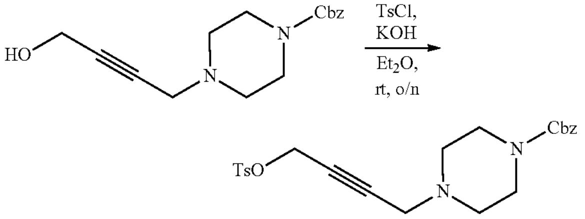 [SMILES: O=C(OCc1ccccc1)N1CCN(CC#CCO)CC1 ; Cc1ccc(S(=O)(=O)OCC#CCN2CCN(C(=O)OCc3ccccc3)CC2)cc1]

Into a 250-mL round-bottom flask, was placed a solution of benzyl 4-(4-hydroxybut-2-yn-1-yl)piperazine-1-carboxylate (2.01 g, 6.98 mmol, 1.00 equiv) and potassium hydroxide (3.91 g, 69.80 mmol, 10.00 equiv) in diethyl ether (100 mL). Then 4-methylbenzenesulfonyl chloride (1.99 g, 10.47 mmol, 1.50 equiv) was added. The reaction mixture was stirred overnight at room temperature. The insoluble solids were filtered out. The filtrate was washed with water (100 ml), dried over anhydrous sodium sulfate and concentrated under vacuum. This resulted in 1.80 g (59%) benzyl 4-(4-(tosyloxy)but-2-yn-1-yl)piperazine-1-carboxylate as a yellow oil.

Step 9

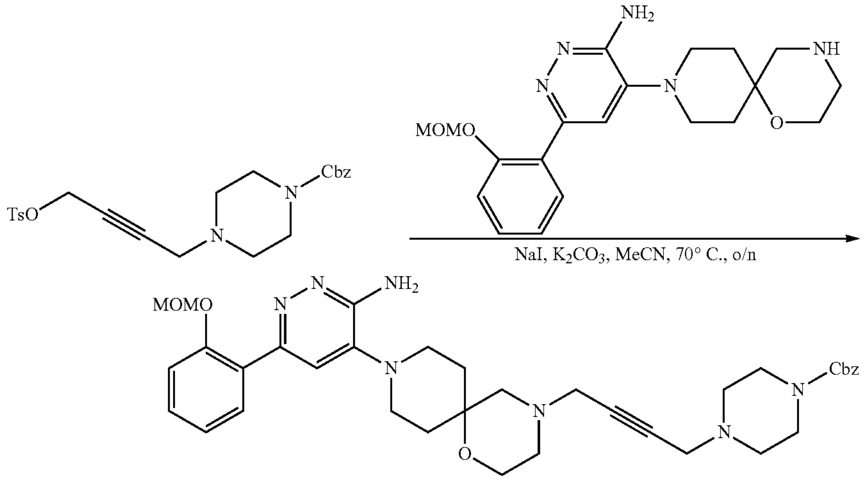

Into a 250-mL round-bottom flask, was placed a solution of benzyl 4-(4-(tosyloxy)but-2-yn-1-yl)piperazine-1-carboxylate (1.80 g, 4.07 mmol, 2.50 equiv), 6-(2-(methoxymethoxy)phenyl)-4-(1-oxa-4,9-diazaspiro[5.5]undecan-9-yl)pyridazin-3-amine (627 mg, 1.63 mmol, 1.00 equiv), sodium iodide (366 mg, 2.44 mmol, 1.50 equiv), potassium carbonate (900 mg, 6.52 mmol, 4.0 equiv) in acetonitrile (70 mL). The resulting mixture was stirred overnight at 70° C. The reaction mixture was diluted with water (100 mL), extracted with ethyl acetate (200 mL×2). The combined organic phase was concentrated, and the residue was applied onto a silica gel column eluting with methanol/dichloromethane (1:10). This resulted in 180 mg (17%) of benzyl 4-(4-(9-(3-amino-6-(2-(methoxymethoxy)phenyl)pyridazin-4-yl)-1-oxa-4,9-diazaspiro[5.5]undecan-4-yl)but-2-yn-1-yl)piperazine-1-carboxylate as a brown solid.

Step 10

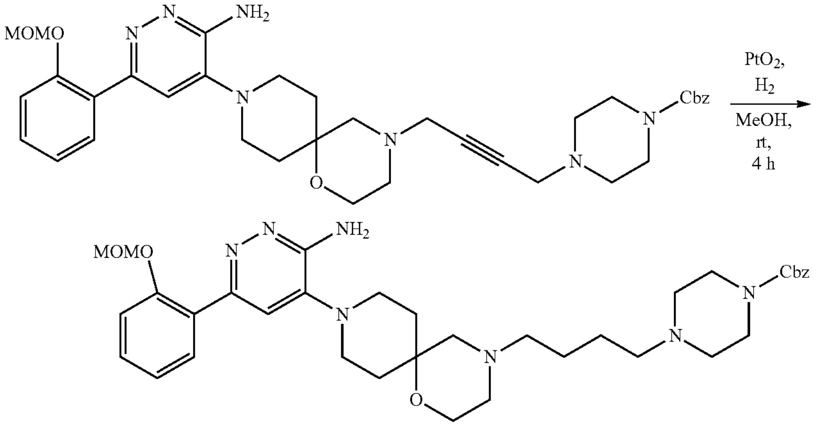

In a 100-mL round-bottom flask to a solution of benzyl 4-(4-(9-(3-amino-6-(2-(methoxymethoxy)phenyl)pyridazin-4-yl)-1-oxa-4,9-diazaspiro[5.5] undecan-4-yl)but-2-yn-1-yl)piperazine-1-carboxylate (1.60 g, 2.44 mmol, 1.00 equiv) in methanol (40 mL) was added platinum dioxide (221.8 mg, 0.98 mmol, 0.40 equiv) under nitrogen atmosphere. The flask was vacuumed and flushed with hydrogen. The reaction mixture was hydrogenated for 4 h at room temperature under hydrogen atmosphere using a hydrogen balloon. The mixture was filtered through a celite pad, and the filtrate was concentrated under reduced pressure. The residue was applied onto a silica gel column eluting with methanol/dichloromethane (1:10). This resulted in 444.0 mg (28%) of benzyl 4-(4-(9-(3-amino-6-(2-(methoxymethoxy)phenyl)pyridazin-4-yl)-1-oxa-4,9-diazaspiro[5.5]undecan-4-yl)butyl)piperazine-1-carboxylate as a brown solid.

Step 11

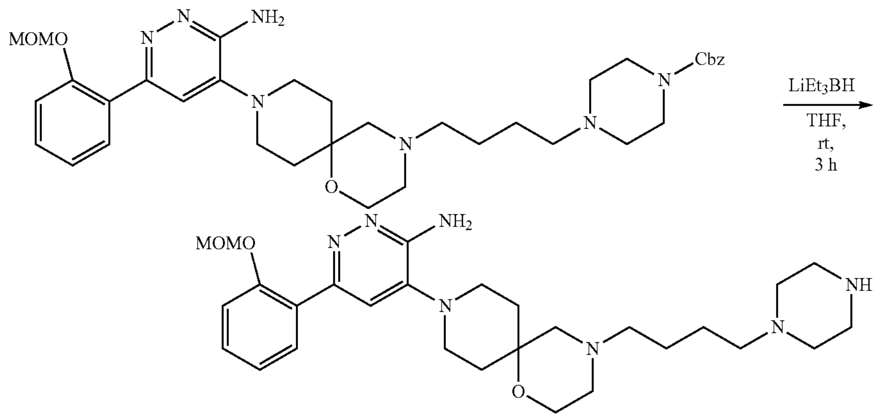

Into a 100-mL round-bottom flask, was placed a solution of benzyl 4-(4-(9-(3-amino-6-(2-(methoxymethoxy)phenyl)pyridazin-4-yl)-1-oxa-4,9-diazaspiro[5.5]undecan-4-yl)butyl)piperazine-1-carboxylate (444 mg, 0.67 mmol, 1.00 equiv) in THF (8 mL), to which was added a solution of lithium triethylborohydride in THF (1.0 M, 8 mL). The resulting solution was stirred for 3 hours at room temperature. The reaction mixture was quenched by saturated $NH_4Cl$ solution (30 mL) and extracted with dichloromethane (30 mL×2). The combined organic phase was dried over sodium sulfate and concentrated under reduced pressure. This resulted in 292 mg (83%) of 6-(2-(methoxymethoxy)phenyl)-4-(4-(4-(piperazin-1-yl)butyl)-1-oxa-4,9-diazaspiro[5.5]undecan-9-yl)pyridazin-3-amine as a brown oil.

6-(2-(Methoxymethoxy)phenyl)-4-(4-(4-(piperazin-1-yl)butyl)-1-oxa-4,9-diazaspiro[5.5]undecan-9-yl)pyridazin-3-amine was converted to the final compound according to the scheme below using procedures analogous to those described above for other examples.

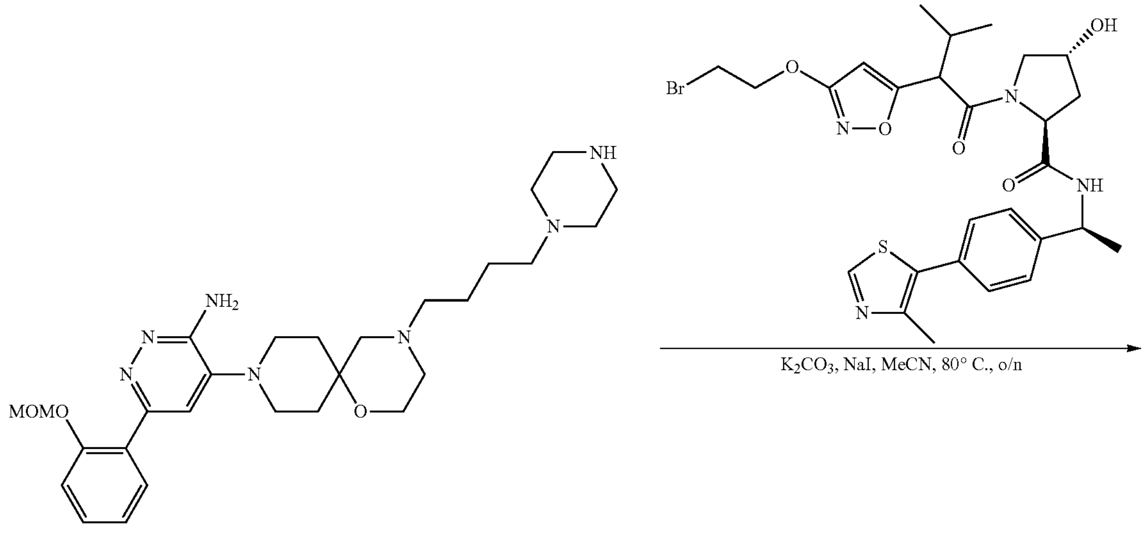

-continued
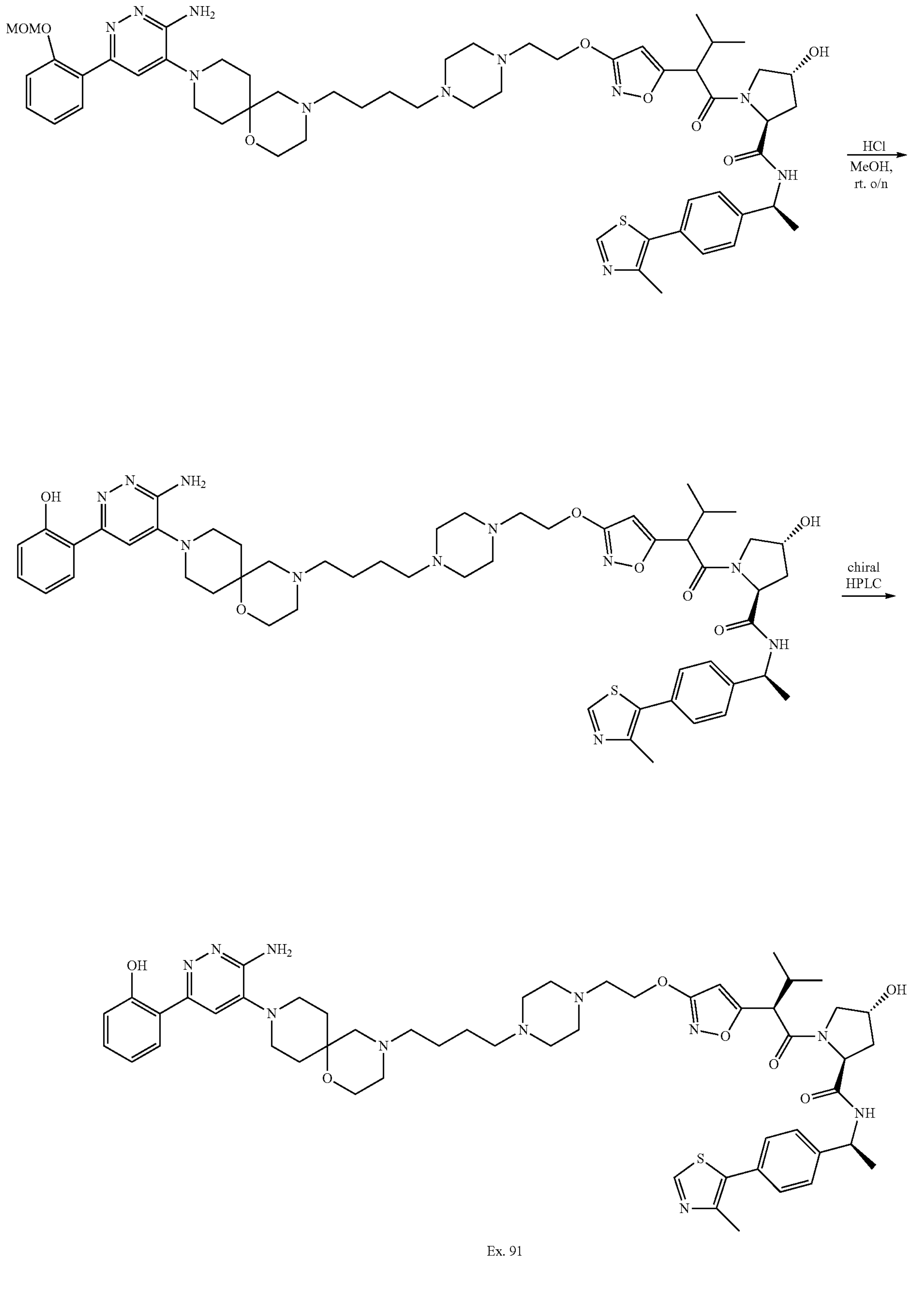
Ex. 91

Exemplary compound 205 was prepared using analogous procedures.
Exemplary Synthesis of Exemplary Compound 188
Ex. 188
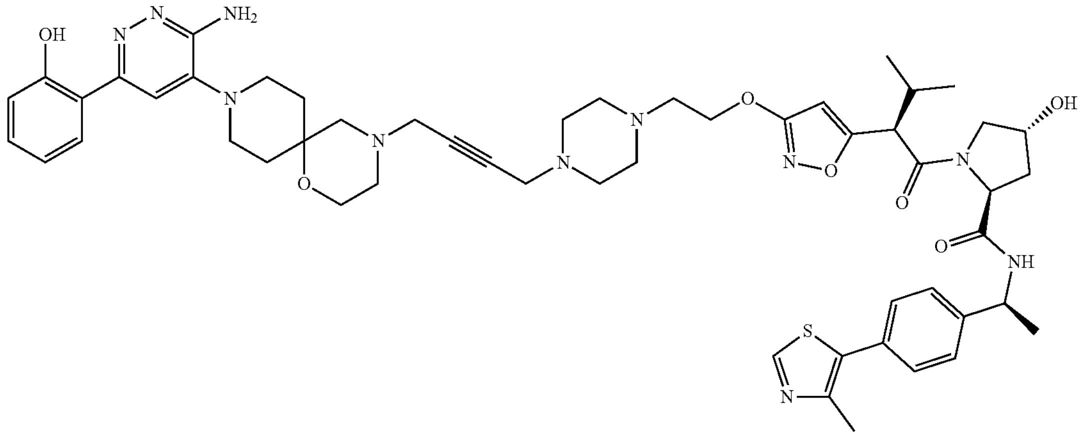
Prepared according to the scheme below using procedures analogous to those described above for exemplary compound 91.
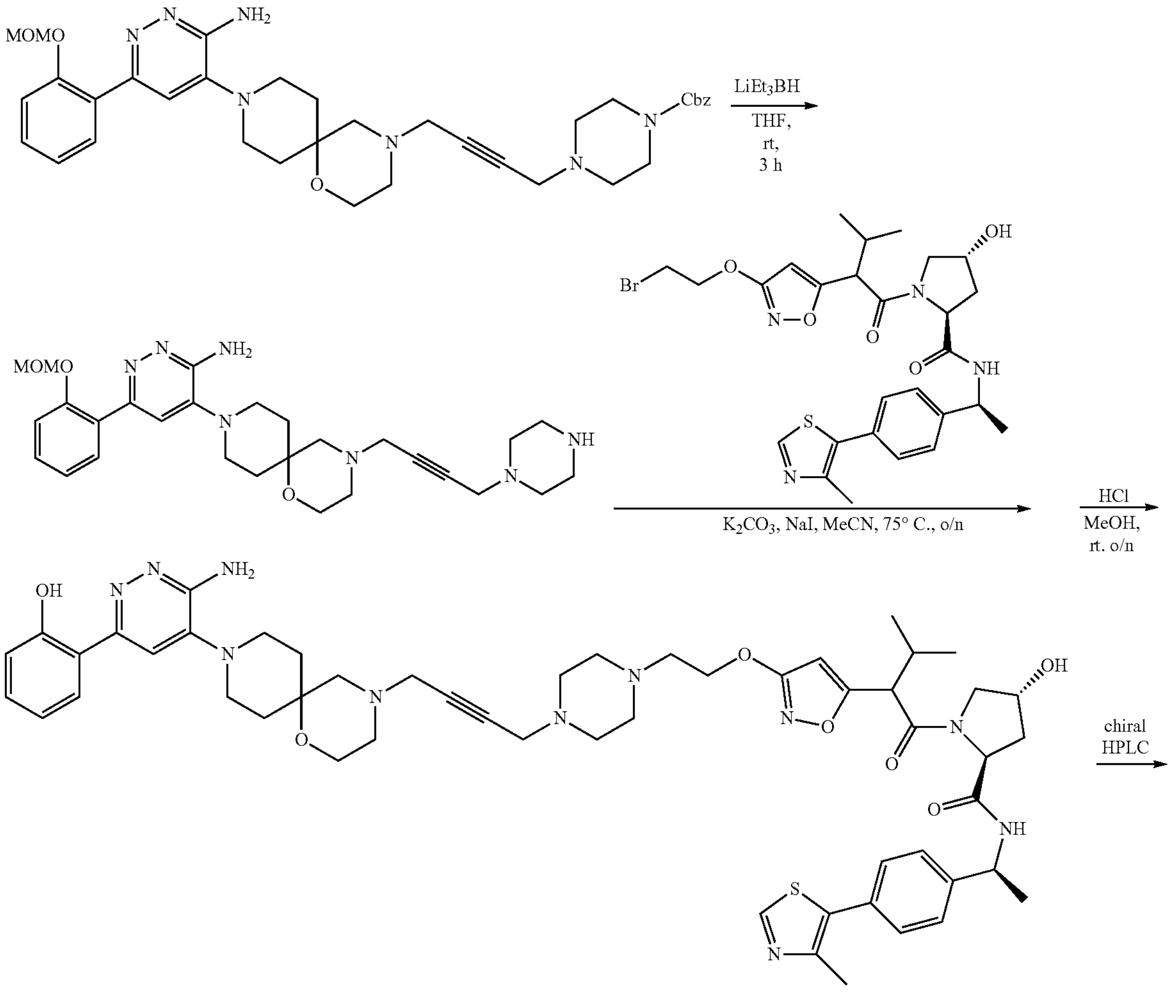

-continued

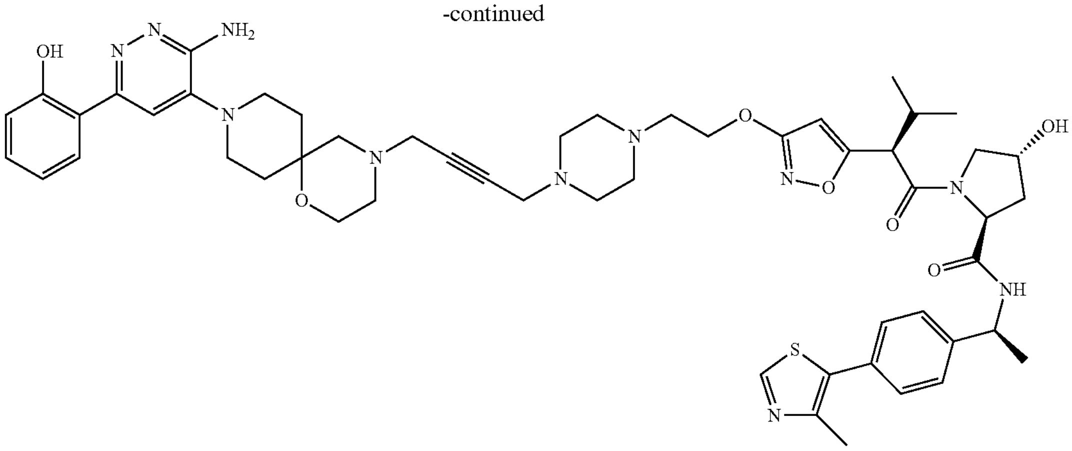

Ex. 188

Exemplary compound 187 was prepared using analogous procedures.

Exemplary Synthesis of Exemplary Compound 192

Ex. 192

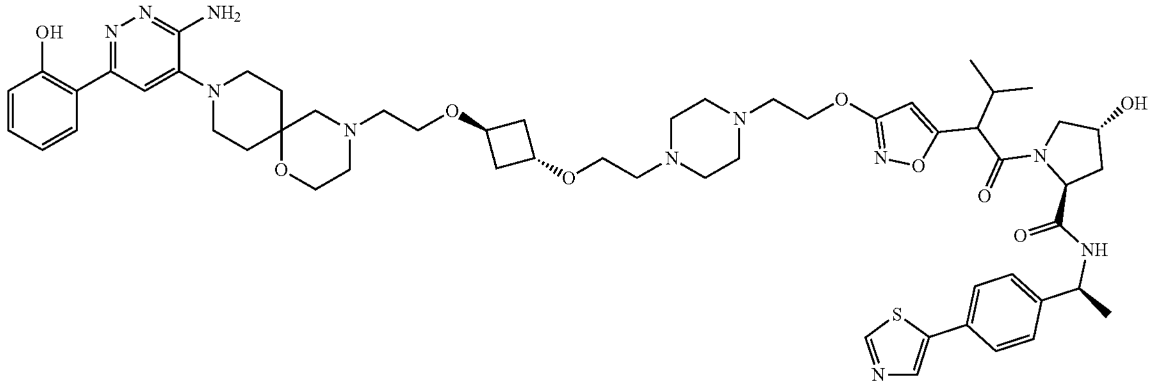

Benzyl 4-(2-((1r,3r)-3-(2-(9-(3-amino-6-(2-(methoxymethoxy)phenyl)pyridazin-4-yl)-1-oxa-4,9-diazaspiro[5.5]undecan-4-yl)ethoxy)cyclobutoxy)ethyl)piperazine-1-carboxylate was prepared according to the scheme below using procedures described for other examples, as well as procedures obvious to those skilled in the art.

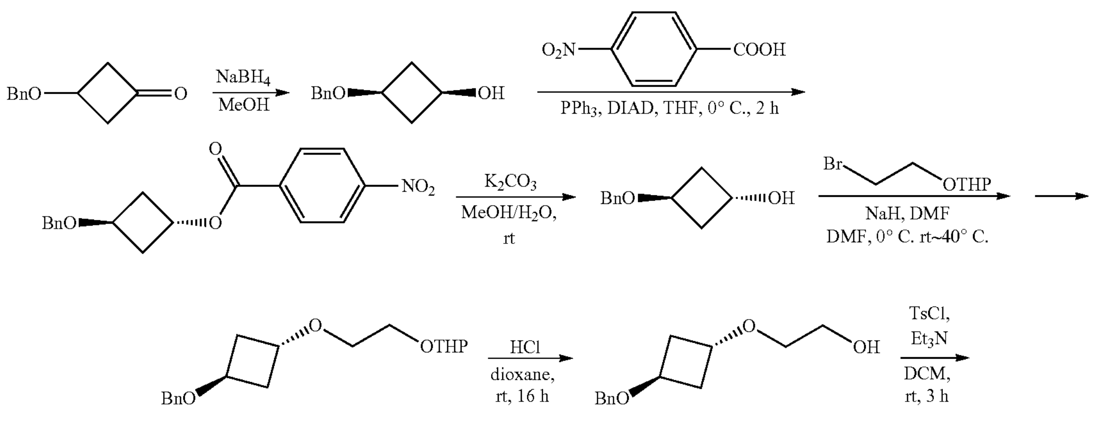

-continued
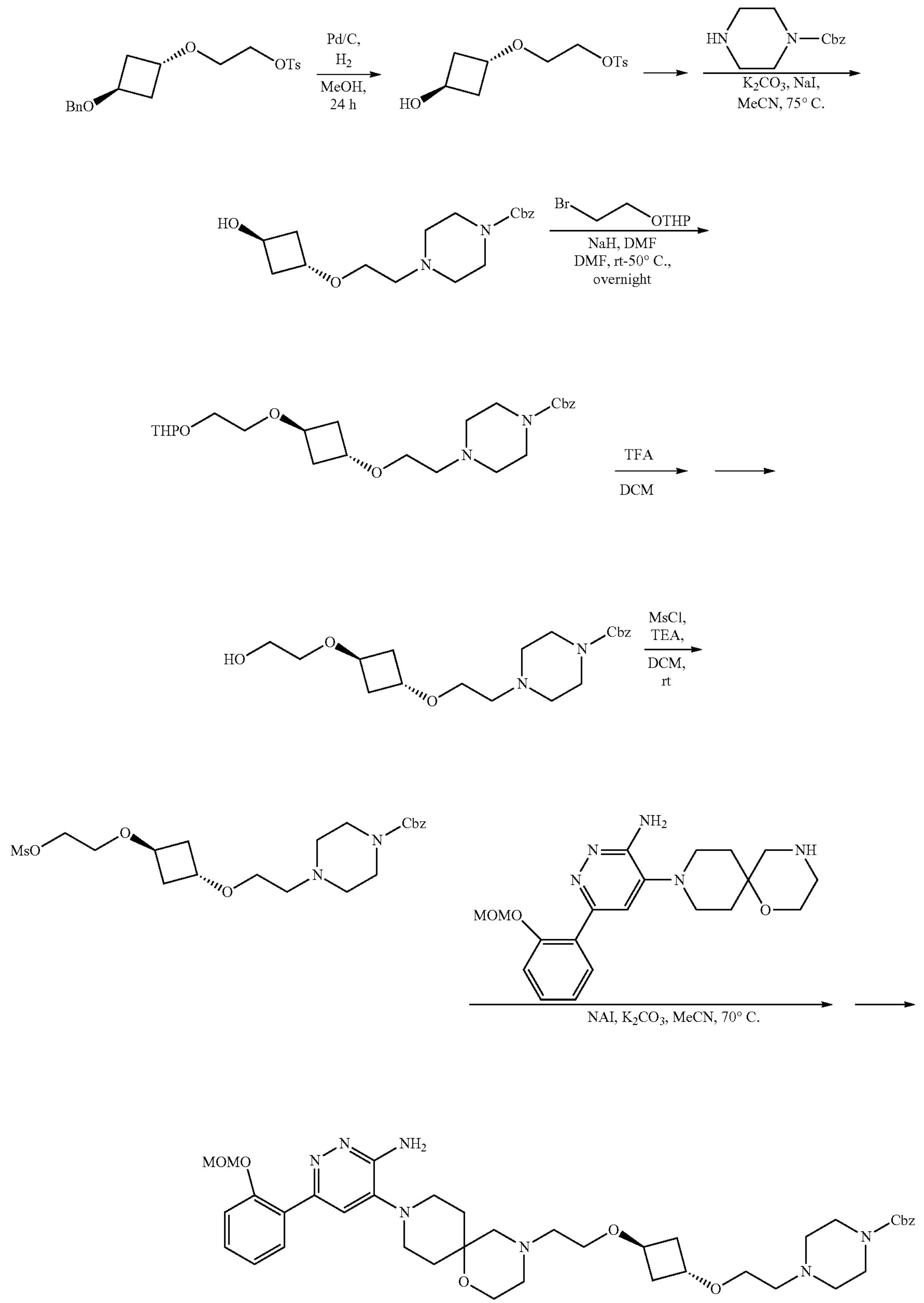
Benzyl 4-(2-((1r,3r)-3-(2-(9-(3-amino-6-(2-(methoxymethoxy)phenyl)pyridazin-4-yl)-1-oxa-4,9-diazaspiro[5.5]undecan-4-yl)ethoxy)cyclobutoxy)ethyl)piperazine-1-carboxylate was converted to the final compound using procedures analogous to those described for exemplary compound 91.

Exemplary Synthesis of Exemplary Compounds 212 and 213
Ex. 212
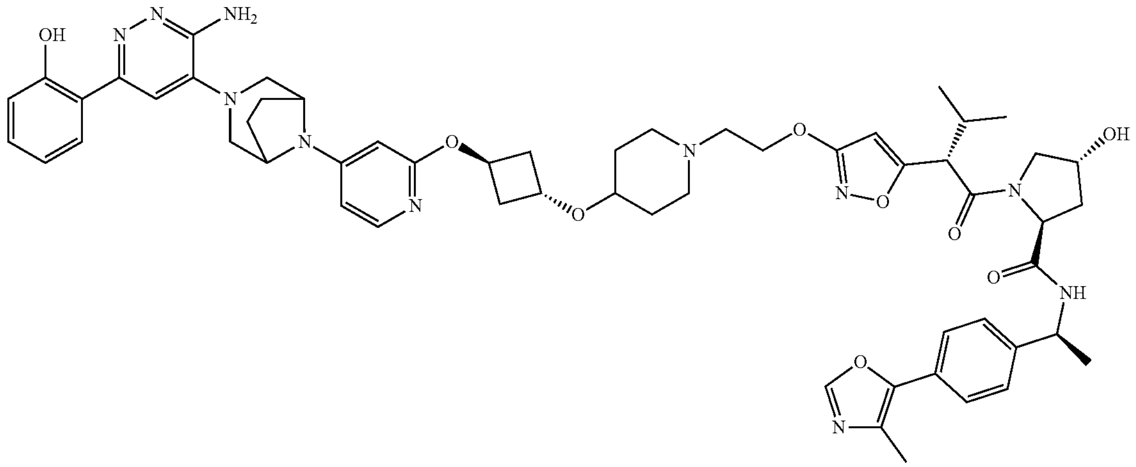
Ex. 213
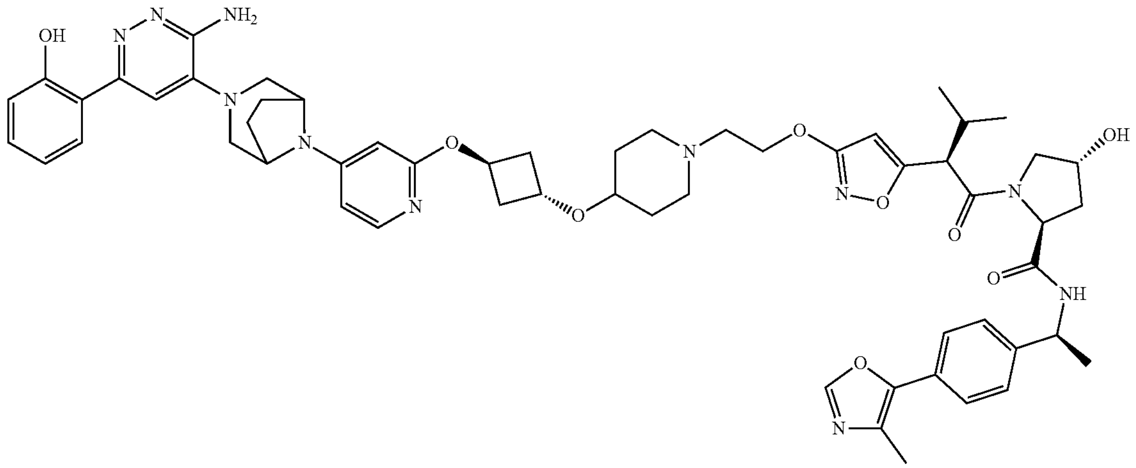

Prepared using procedures analogous to those described in steps 1 and 2 of exemplary compound 117, followed by steps described for exemplary compound 180.

Exemplary Synthesis of Exemplary Compounds 214 and 215

Ex. 214

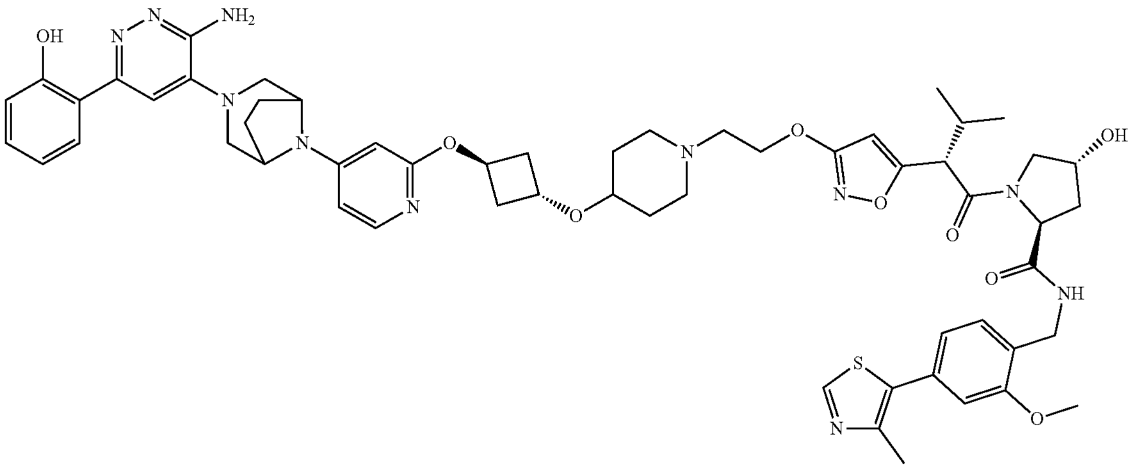

Ex. 215

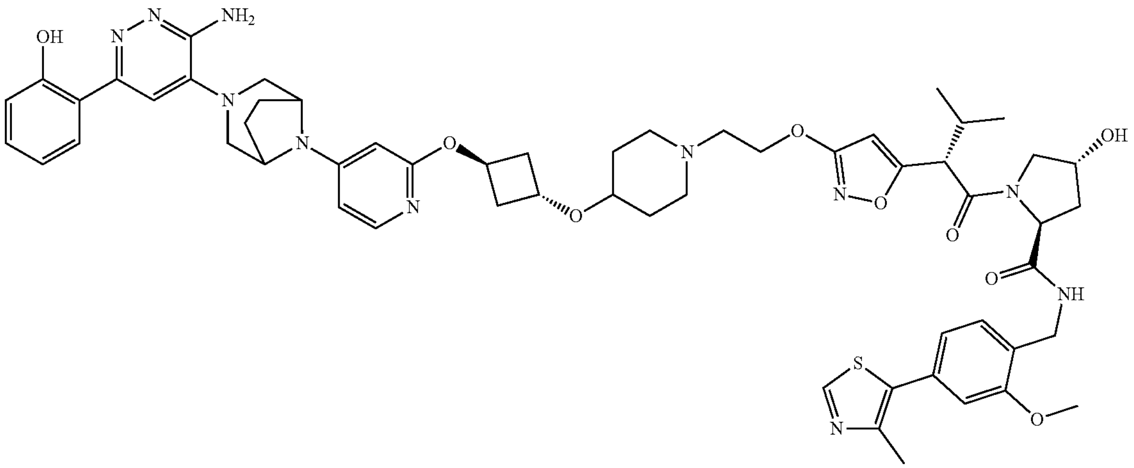

tert-Butyl (2S,4R)-4-hydroxy-2-((2-methoxy-4-(4-methylthiazol-5-yl)benzyl)carbamoyl)pyrrolidine-1-carboxylate was prepared according to the scheme below using standard procedures obvious to those skilled in the art.

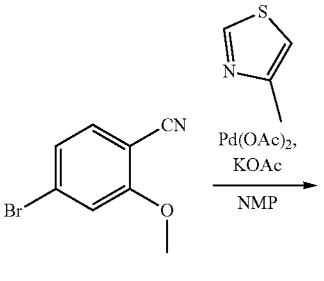

-continued

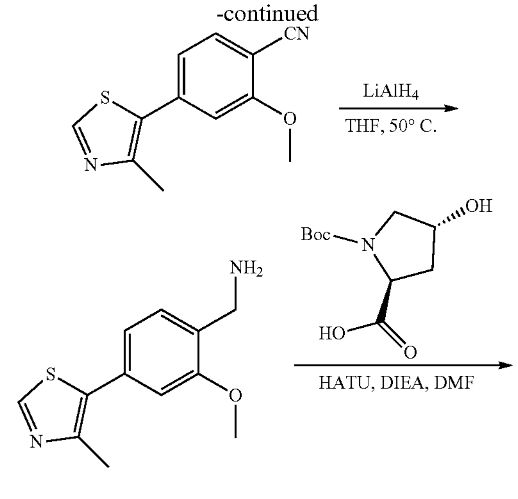

-continued

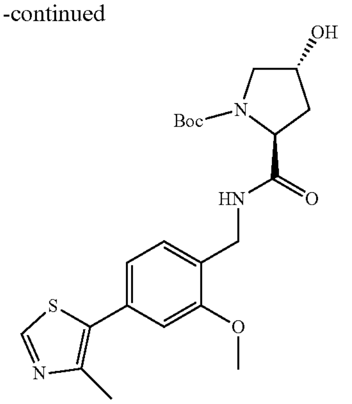

tert-Butyl (2S,4R)-4-hydroxy-2-((2-methoxy-4-(4-methylthiazol-5-yl)benzyl)carbamoyl)pyrrolidine-1-carboxylate was converted to the final compounds using standard procedures described for other examples above.

Exemplary Synthesis of Exemplary Compound 238

Ex. 238

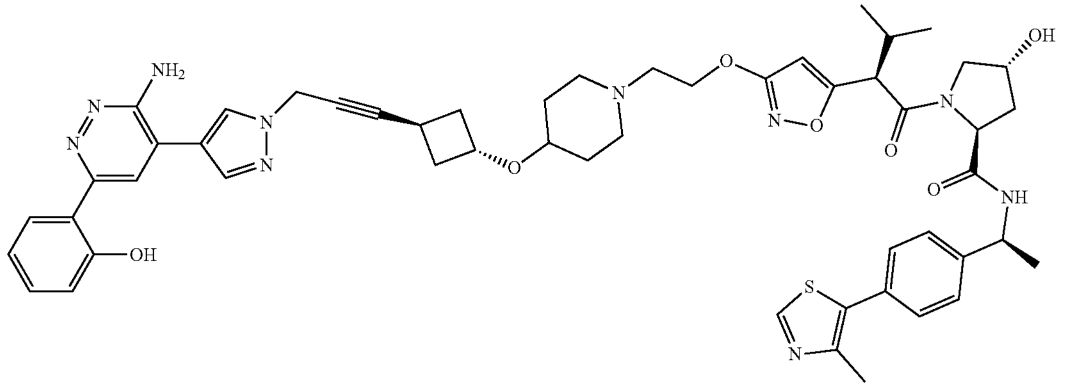

Step 1

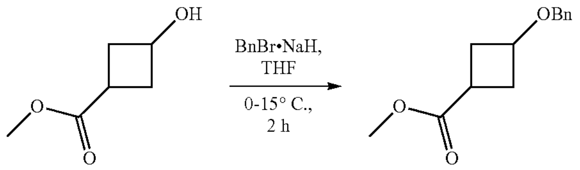

To a solution of methyl 3-hydroxycyclobutanecarboxylate (14.2 g, 109.11 mmol, 1.00 eq) in DMF (150 mL) was added sodium hydride (5.24 g, 130.93 mmol, 60% purity, 1.20 eq), and the mixture was stirred for 0.5 hour at 0° C. Following that, benzyl bromide (20.53 g, 120.02 mmol, 14.26 mL, 1.1 eq) was added, and the mixture was stirred at 25° C. for 2 hours. The reaction mixture was quenched by saturated ammonium chloride solution (200 mL) at 25° C., and then diluted with water (100 mL) and extracted with ethyl acetate (80 mL×3). The combined organic layers were washed with brine (150 mL×2), dried over anhydrous sodium sulfate, filtered and concentrated under reduced pressure to give a residue. The residue was purified by flash silica gel chromatography (0-20% ethyl acetate/petroleum ether gradient). Compound methyl 3-benzyloxycyclobutanecarboxylate (8.9 g, 40.41 mmol, 37% yield) was obtained as a light yellow oil.

Step 2

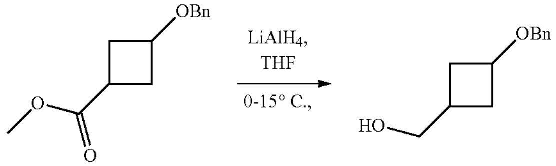 [SMILES: COC(=O)C1CC(OCc2ccccc2)C1 ; OCC1CC(OCc2ccccc2)C1]

To a solution of lithium aluminum hydride (1.53 g, 40.41 mmol, 1.00 eq) in tetrahydrofuran (80 mL) was added methyl 3-benzyloxycyclobutanecarboxylate (8.90 g, 40.41 mmol, 1.00 eq) at 0° C., and the mixture was stirred at 25° C. for 2 hours. The reaction mixture was quenched by water (1 mL), sodium hydroxide solution (15%, 2 mL) and water (3 mL) at 25° C., and then diluted with ethyl acetate (80 mL) and extracted with ethyl acetate (15 mL×3). The combined organic layers were washed with brine (50 mL×2), dried over anhydrous sodium sulfate, filtered and concentrated under reduced pressure to give a residue. The residue was purified by flash silica gel chromatography (0-50% ethyl acetate/petroleum ether). Compound (3-benzyloxycyclobutyl)methanol (7.4 g, 38.5 mmol, 95% yield) was obtained as a colorless oil.

Step 3

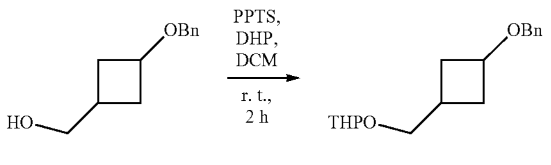

To a solution of (3-benzyloxycyclobutyl)methanol (7.4 g, 38.49 mmol, 1.00 eq) and 3,4-dihydro-2H-pyran (16.19 g, 192.5 mmol, 17.6 mL, 5.00 eq) in dichloromethane (125 mL) was added pyridinium p-toluenesulfonate (967 mg, 3.85 mmol, 0.10 eq), and the mixture was stirred at 25° C. for 12 hours. Water (200 mL) was added to the mixture, and the resulting mixture was extracted with dichloromethane (100 mL×2). Then combined organic layers were washed with brine (150 mL×2), dried over anhydrous sodium sulfate, filtered and concentrated under reduced pressure to give a residue. The residue was purified by column chromatography (SiO2, petroleum ether:ethyl acetate=1:0 to 20:1). Compound 2-[(3-benzyloxycyclobutyl)methoxy]tetrahydropyran (10.20 g, 36.9 mmol, 95% yield) was obtained as a colorless oil.

Step 4

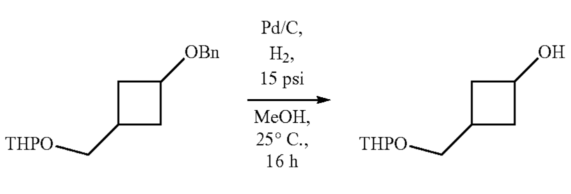

To a solution of 2-[(3-benzyloxycyclobutyl)methoxy]tetrahydropyran (10.20 g, 36.9 mmol, 1.00 eq) in methanol (100 mL) was added 10% palladium on carbon (2 g, 36.91 mmol) under nitrogen. The suspension was degassed under vacuum and purged with hydrogen several times. The mixture was stirred under hydrogen (15 psi) at 25° C. for 16 hours. The reaction was filtered and concentrated under reduced pressure to give a residue. Compound 3-(tetrahydropyran-2-yloxymethyl)cyclobutanol (6.28 g, 33.7 mmol, 91% yield) was obtained as a colorless oil.

Step 5

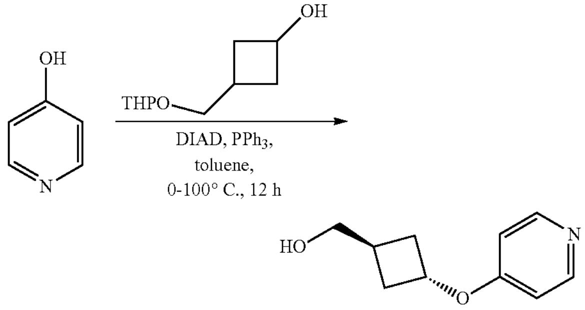

To a solution of pyridin-4-ol (4 g, 42.06 mmol, 1 eq), 3-(tetrahydropyran-2-yloxymethyl) cyclobutanol (8.62 g, 46.27 mmol, 1.1 eq), and triphenylphosphine (33.10 g, 126.18 mmol, 3 eq) in toluene (40 mL) was added diisopropyl azodicarboxylate (25.52 g, 126.18 mmol, 24.5 mL, 3 eq) in toluene (20 mL) dropwise at 0° C. under nitrogen. The reaction mixture was stirred at 100° C. for 12 hours. The mixture was concentrated in vacuum to remove most of toluene. Water (150 mL) and ethyl acetate (100 mL) were added to the mixture, hydrochloric acid solution (2M) was added to the mixture to adjust pH to about 3, and the resulting mixture was extracted with ethyl acetate (100 mL×2). Saturated sodium bicarbonate was added to the aqueous phase to adjust pH about 8, and the resulting mixture was extracted with ethyl acetate (150 mL×5). The combined organic phase was washed with brine (150 mL), dried over sodium sulfate, filtered and concentrated in vacuum. The crude product was purified by preparative HPLC (column: Kromasil Eternity XT 250*80 mm*10 um; mobile phase: [water (0.05% ammonia hydroxide v/v)-ACN]; B %: 5%-30%, 31 min). ((1r,3r)-3-(Pyridin-4-yloxy) cyclobutyl)methanol (4.2 g, 23.0 mmol, 54% yield) was obtained as a light yellow oil.

Step 6

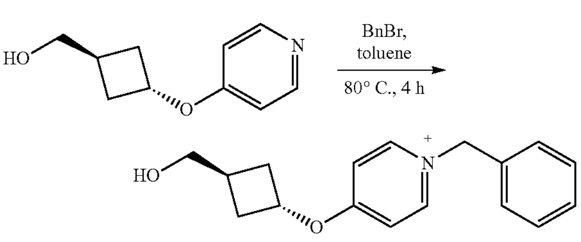

To a solution of ((1r,3r)-3-(pyridin-4-yloxy)cyclobutyl) methanol (4.2 g, 23.44 mmol, 1 eq) in toluene (40 mL) was added benzyl bromide (4.41 g, 25.78 mmol, 3.1 mL, 1.1 eq). The reaction mixture was stirred at 80° C. for 4 h. The mixture was concentrated in vacuum. The residue was triturated with petroleum ether and ethyl acetate (40 mL, V/V=1/1). 1-Benzyl-4-((1r,3r)-3-(hydroxymethyl)cyclobutoxy)pyridin-1-ium (8 g, 22.8 mmol, 97% yield) was obtained as a white solid.

Step 7

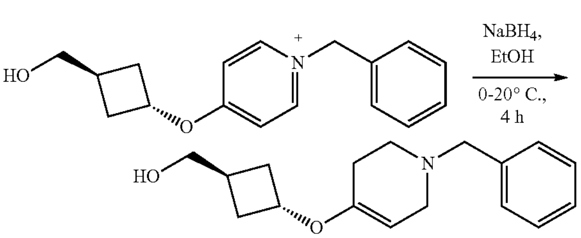

To a solution of 1-benzyl-4-((1r,3r)-3-(hydroxymethyl) cyclobutoxy)pyridin-1-ium (8 g, 22.84 mmol, 1 eq) in ethanol (100 mL) was added sodium borohydride (1.73 g, 45.68 mmol, 2 eq) at 0° C. The reaction mixture was stirred at 20° C. for 4 hours. Water (100 mL) was added to the mixture to quench the reaction. The resulting mixture was extracted with ethyl acetate (100 mL×3). The combined organic phase was washed with brine (100 mL), dried over sodium sulfate, filtered and concentrated in vacuum. The residue was purified by silica gel chromatography (petroleum ether:ethyl acetate=50:1 to 0:1). ((1r,3r)-3-((1-Benzyl-1,2,3,6-tetrahydropyridin-4-yl)oxy)cyclobutyl)methanol (5.2 g, 19.02 mmol, 83% yield) was obtained as a light yellow oil.

Step 8

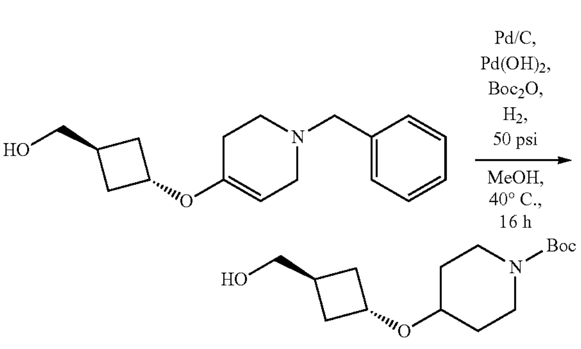

To a solution of [3-[(1-benzyl-3,6-dihydro-2H-pyridin-4-yl)oxy]cyclobutyl]methanol (5.2 g, 19.02 mmol, 1 eq) and di-tert-butyl dicarbonate (8.30 g, 38.04 mmol, 8.7 mL, 2 eq) in methanol (100 mL) was added 10% palladium on activated carbon catalyst (0.7 g) and palladium hydroxide 20% on carbon (0.7 g) under nitrogen. The reaction mixture was stirred at 40° C. under hydrogen (50 psi) for 16 hours. The mixture was filtered through a Celite pad, and the filtrate was concentrated to give crude product. The residue was purified by silica gel chromatography (petroleum ether:ethyl acetate=100:1 to 0:1). tert-Butyl 4-((1r,3r)-3-(hydroxymethyl)cyclobutoxy)piperidine-1-carboxylate (4.5 g, 15.77 mmol, 83% yield) was obtained as a colorless oil.

Step 9

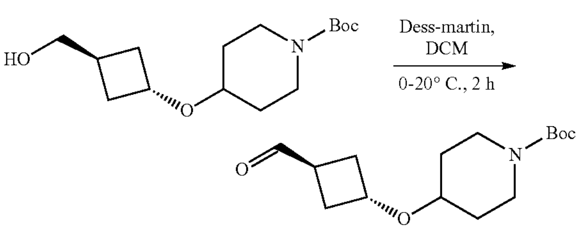

To a solution of tert-butyl 4-((1r,3r)-3-(hydroxymethyl) cyclobutoxy)piperidine-1-carboxylate (2.5 g, 8.76 mmol, 1 eq) in dichloromethane (25 mL) was added Dess-Martin periodinane (4.46 g, 10.51 mmol, 1.2 eq) at 0° C. The reaction mixture was stirred at 20° C. for 2 hours. The mixture was filtered, and saturated sodium bicarbonate (50 mL) was added to the mixture. The aqueous phase was extracted with ethyl acetate (50 mL×3). The combined organic phase was washed with brine (80 mL), dried over sodium sulfate, filtered and concentrated in vacuum. The residue was purified by silica gel chromatography (petroleum ether:ethyl acetate=1:0 to 5:1). tert-Butyl 4-((1r,3r)-3-formylcyclobutoxy)piperidine-1-carboxylate (2.0 g, 7.06 mmol, 80% yield) was obtained as a colorless oil.

Step 10

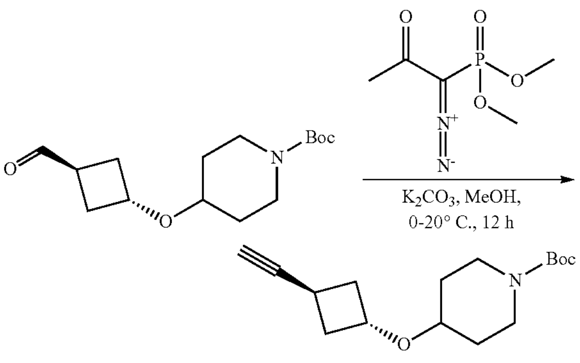

To a solution of tert-butyl 4-((1r,3r)-3-formylcyclobutoxy)piperidine-1-carboxylate (2.0 g, 7.06 mmol, 1 eq) in methanol (20 mL) was added potassium carbonate (1.95 g, 14.12 mmol, 2 eq) and 1-diazo-1-dimethoxyphosphoryl-propan-2-one (1.42 g, 7.41 mmol, 1.05 eq) at 0° C. The reaction mixture was stirred at 20° C. for 12 hours. Water (100 mL) was added to the mixture, the resulting mixture was extracted with ethyl acetate (50 mL×3). The combined organic phase was washed with brine (50 mL), dried over sodium sulfate, filtered and concentrated in vacuum. The residue was purified by silica gel chromatography (petroleum ether:ethyl acetate=1:0 to 20:1). tert-Butyl 4-((1r,3r)-3-ethynylcyclobutoxy)piperidine-1-carboxylate (1.3 g, 4.65 mmol, 66% yield) was obtained as a colorless oil.

Step 11

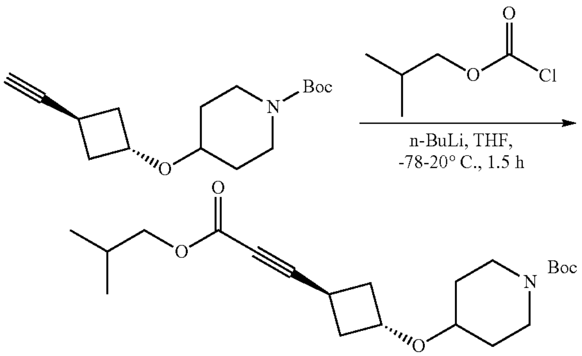

To a solution of tert-butyl 4-((1r,3r)-3-ethynylcyclobutoxy)piperidine-1-carboxylate (1.7 g, 6.09 mmol, 1 eq) in tetrahydrofuran (17 mL) was added n-butyllithium (2.5 M, 3.6 mL, 1.5 eq) at −78° C. The mixture was stirred at −78° C. for 0.5 hour. Then isobutyl chloroformate (1.66 g, 12.17 mmol, 1.6 mL, 2 eq) was added to the mixture, and the reaction mixture was stirred at −78° C. for 0.5 hour and at 20° C. for 1 hour. Saturated ammonium chloride (80 mL) was added to the mixture, and the resulting mixture was extracted with ethyl acetate (80 mL×3). The combined organic phase was washed with brine (100 mL), dried over sodium sulfate, filtered and concentrated in vacuum. The residue was purified by silica gel chromatography (petroleum ether:ethyl acetate=1:0 to 5:1). tert-Butyl 4-((1r,3r)-3-(3-isobutoxy-3-oxoprop-1-yn-1-yl)cyclobutoxy)piperidine-1-carboxylate (2 g, 5.27 mmol, 86% yield) was obtained as a light yellow oil.

Step 12

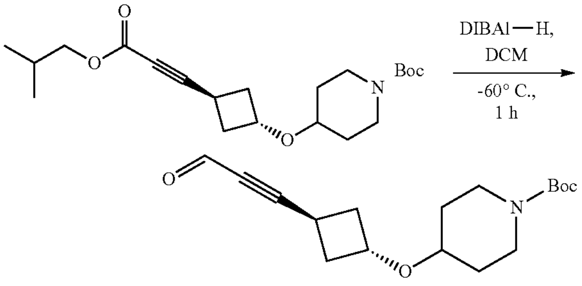

To a solution of tert-butyl 4-[3-(3-isobutoxy-3-oxo-prop-1-ynyl)cyclobutoxy]piperidine-1-carboxylate (2 g, 5.27 mmol, 1 eq) in dichloromethane (20 mL) was added dropwise diisobutylaluminum hydride solution in DCM (1 M, 6.3 mL, 1.2 eq) at −78° C. The reaction mixture was stirred at −78° C. for 1 hour. Saturated sodium bicarbonate (10 mL) was added to the mixture, and ethyl acetate (100 mL) was added to the mixture. The mixture was filtered through a Celite pad, and was extracted with ethyl acetate (50 mL×3). The combined organic phase was washed with brine (70 mL), dried over sodium sulfate, filtered and concentrated in vacuum. The residue was purified by silica gel chromatography (petroleum ether:ethyl acetate=1:0 to 5:1). tert-Butyl 4-((1r,3r)-3-(3-oxoprop-1-yn-1-yl)cyclobutoxy)piperidine-1-carboxylate (1.2 g, 3.90 mmol, 74% yield) was obtained as a colorless oil.

Step 13

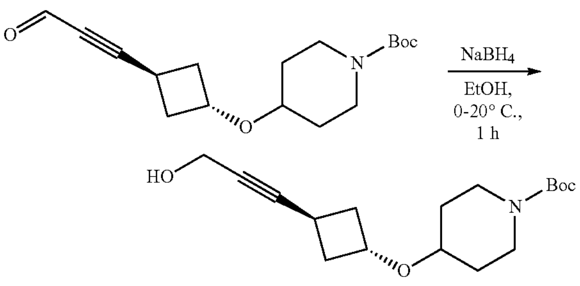

To a solution of tert-butyl 4-[3-(3-oxoprop-1-ynyl)cyclobutoxy]piperidine-1-carboxylate (1.2 g, 3.90 mmol, 1 eq) in ethanol (10 mL) was added sodium borohydride (177 mg, 4.68 mmol, 1.2 eq) in three portions at 0° C. The reaction mixture was stirred at 20° C. for 1 hour. Water (100 mL) was added to the mixture, and the resulting mixture was extracted with ethyl acetate (50 mL×3). The combined organic phase was washed with brine (50 mL), dried over sodium sulfate, filtered and concentrated in vacuum. The residue was purified by silica gel chromatography (petroleum ether:ethyl acetate=50:1 to 1:1). tert-Butyl 4-((1r,3r)-3-(3-hydroxyprop-1-yn-1-yl)cyclobutoxy)piperidine-1-carboxylate (1.06 g, 3.43 mmol, 87% yield) was obtained as a colorless oil.

Step 14

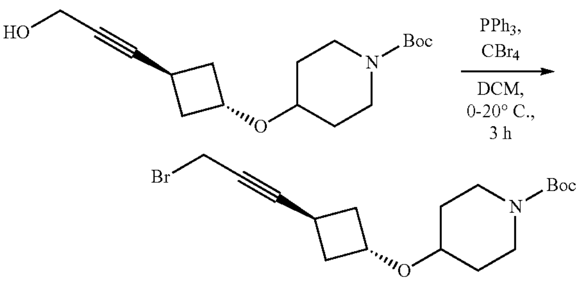

To a solution of tert-butyl 4-((1r,3r)-3-(3-hydroxyprop-1-yn-1-yl)cyclobutoxy)piperidine-1-carboxylate (1.06 g, 3.43 mmol, 1 eq) in dichloromethane (10 mL) was added triphenylphosphine (1.08 g, 4.11 mmol, 1.2 eq) and carbon tetrabromide (1.36 g, 4.11 mmol, 1.2 eq) at 0° C. The reaction mixture was stirred at 20° C. for 3 hours. The mixture was concentrated in vacuum. The residue was purified by silica gel chromatography (petroleum ether:ethyl acetate=1:0 to 20:1). tert-Butyl 4-[3-(3-bromoprop-1-ynyl)cyclobutoxy] piperidine-1-carboxylate (1 g, 2.69 mmol, 78% yield) was obtained as a light yellow oil.

tert-Butyl 4-((1r,3r)-3-(3-hydroxyprop-1-yn-1-yl)cyclobutoxy)piperidine-1-carboxylate was converted to the final compound according to the scheme below using procedures described for other examples above.

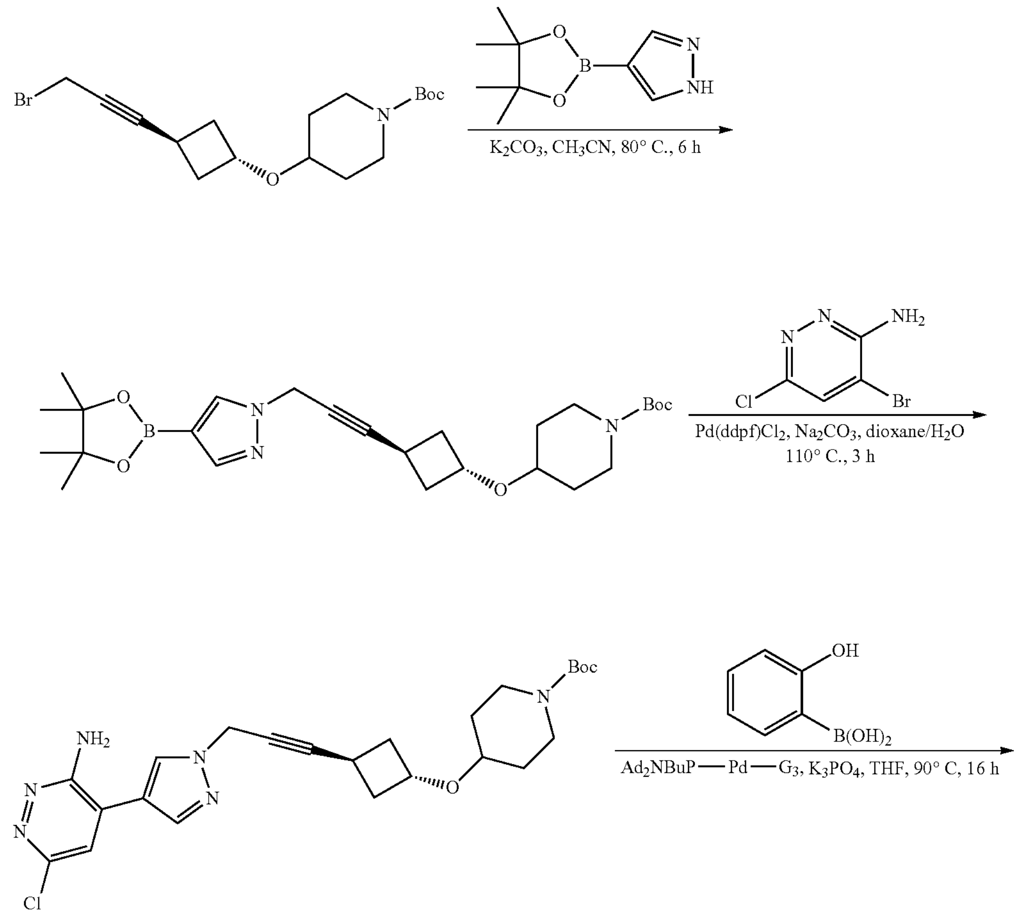

-continued
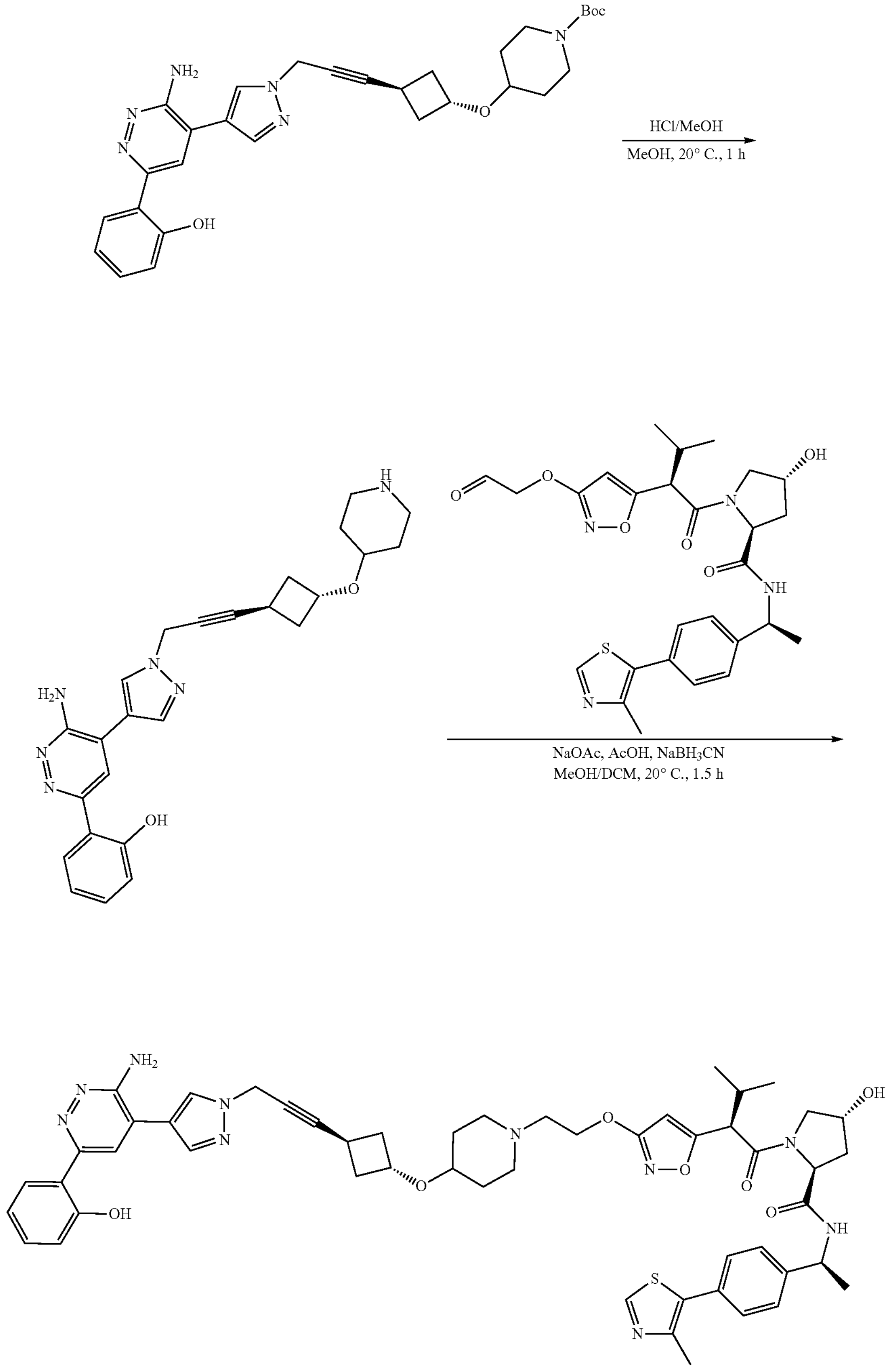
Ex. 238

Exemplary Synthesis of Exemplary Compound 216

Ex. 216

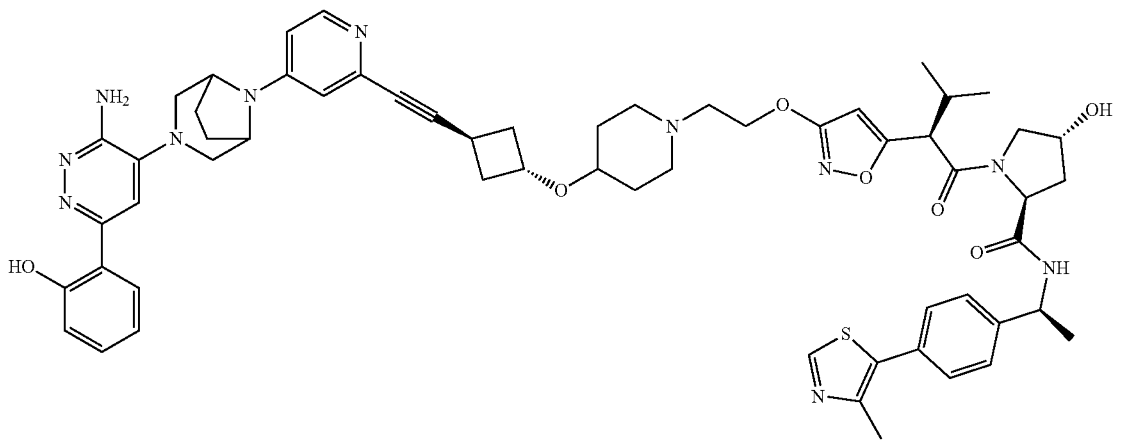

Step 1

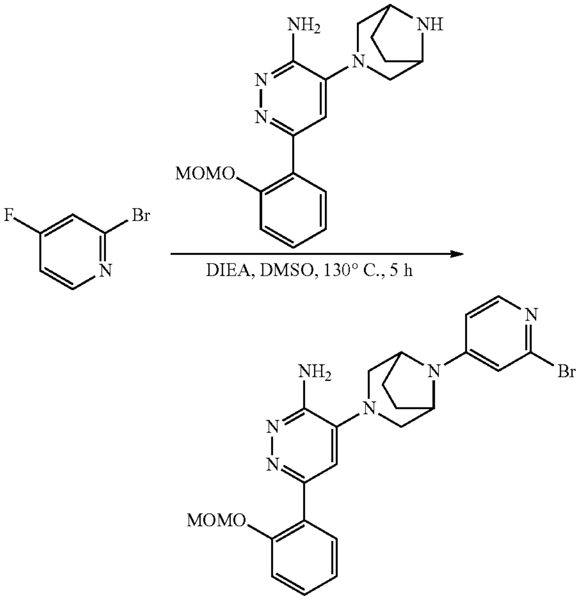

A mixture of 2-bromo-4-fluoro-pyridine (310 mg, 1.76 mmol, 1.2 eq), 4-(3,8-diazabicyclo[3.2.1]octan-3-yl)-6-[2-(methoxymethoxy)phenyl]pyridazin-3-amine (500 mg, 1.46 mmol, 1 eq), and diisopropylethylamine (2.27 g, 17.57 mmol, 3 mL, 12 eq) in dimethylsulfoxide (30 mL) was degassed and purged with nitrogen for three times, and then the mixture was stirred at 130° C. for 5 hours under nitrogen atmosphere. The reaction mixture was diluted with water (50 mL) and extracted with ethyl acetate (50 mL) three times. The combined organic layers were dried over anhydrous sodium sulfate and concentrated to give the crude product. The residue was purified by semi-preparative reverse phase chromatography (column: Phenomenex Synergi C18 150*30 mm*4 um; mobile phase: [water (0.225% FA)-ACN]; B %: 15%-45%, 10 min). 4-[8-(2-Bromo-4-pyridyl)-3,8-diazabicyclo[3.2.1]octan-3-yl]-6-[2-(methoxymethoxy)phenyl]pyridazin-3-amine (562 mg, 1.13 mmol, 77% yield) was obtained as a yellow solid.

Step 2

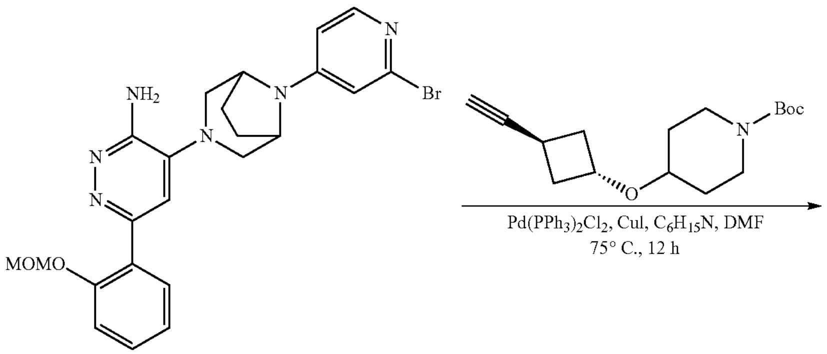

-continued

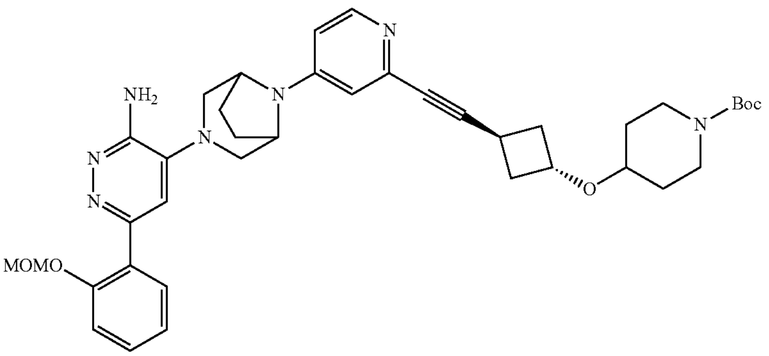

A mixture of 4-[8-(2-bromo-4-pyridyl)-3,8-diazabicyclo [3.2.1]octan-3-yl]-6-[2-(methoxymethoxy)phenyl] pyridazin-3-amine (568 mg, 1.14 mmol, 1 eq), tert-butyl 4-((1r,3r)-3-ethynylcyclobutoxy)piperidine-1-carboxylate (479 mg, 1.71 mmol, 1.5 eq), bis(triphenylphosphine)palladium(II) dichloride (80 mg, 0.1 mmol, 0.1 eq), copper iodide (22 mg, 0.1 mmol, 0.1 eq) and N-isopropylpropan-2-amine (8.13 g, 80.38 mmol, 11.36 mL, 70.39 eq) in dimethylformamide (35 mL) was degassed and purged with nitrogen three times, and then the mixture was stirred at 75° C. for 12 hours under nitrogen atmosphere. The reaction mixture was diluted with water (30 mL) and extracted with ethyl acetate (60 mL) three times. The combined organic layers were washed with brine (50 mL) two times, dried over anhydrous sodium sulfate and concentrated to afford crude product. The residue was purified by semi-preparative reverse phase chromatography (column: Phenomenex luna C18 250*50 mm*10 um; mobile phase: [water (0.225% FA)–ACN]; B %: 15%-45%, 25 min). tert-Butyl 4-((1r,3r)-3-((4-(3-(3-amino-6-(2-(methoxymethoxy)phenyl)pyridazin-4-yl)-3,8-diazabicyclo[3.2.1]octan-8-yl)pyridin-2-yl)ethynyl)cyclobutoxy)piperidine-1-carboxylate (581 mg, 0.8 mmol, 73% yield) was obtained as a yellow solid.

tert-Butyl 4-((1r,3r)-3-((4-(3-(3-amino-6-(2-(methoxymethoxy)phenyl)pyridazin-4-yl)-3,8-diazabicyclo [3.2.1]octan-8-yl)pyridin-2-yl)ethynyl)cyclobutoxy)piperidine-1-carboxylate was converted to the final compound as described for other examples above.

Exemplary Synthesis of Exemplary Compound 217 and 218

Ex. 217

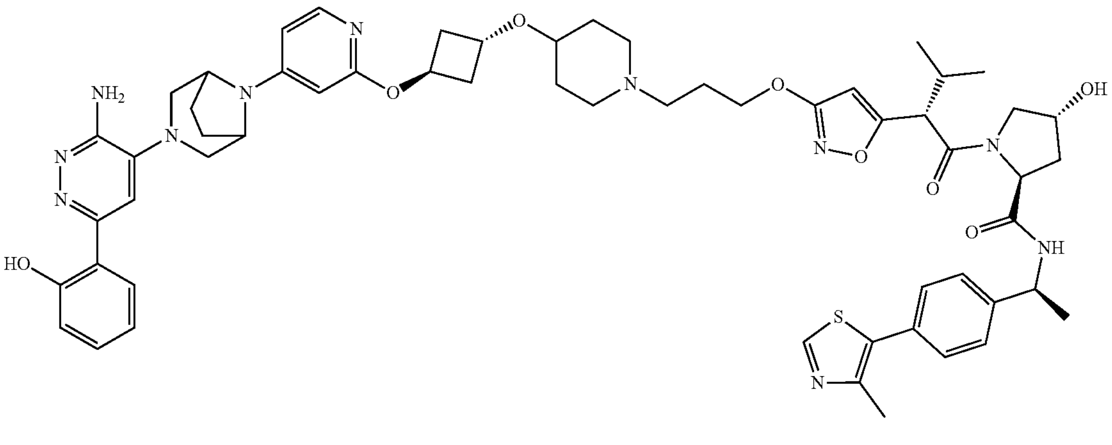

-continued

Ex. 218

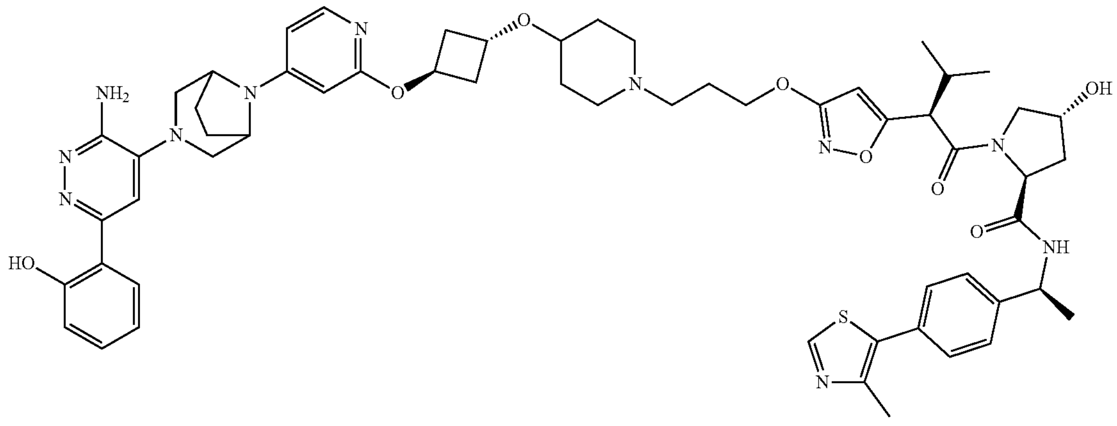

Step 1

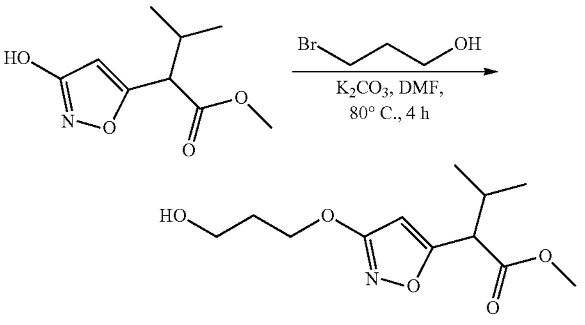

To a solution of methyl 2-(3-hydroxyisoxazol-5-yl)-3-methyl-butanoate (500 mg, 2.51 mmol, 1 eq) and 3-bromopropan-1-ol (523 mg, 3.77 mmol, 0.34 mL, 1.5 eq) in N,N-dimethylformamide (5 mL) was added potassium carbonate (693 mg, 5.02 mmol, 2 eq) at 20° C., and the mixture was stirred at 80° C. for 4 hours. The reaction mixture was quenched by water (20 mL), then was extracted with ethyl acetate (10 mL×3). The combined organic layers were washed with brine (10 mL), dried over anhydrous sodium sulfate, filtered and concentrated under reduced pressure to give a residue. The residue was purified by silica gel column chromatography (petroleum ether/ethyl acetate=20:1 to 4:1). Methyl 2-[3-(3-hydroxypropoxy)isoxazol-5-yl]-3-methyl-butanoate (370 mg, 1.44 mmol, 57% yield) was obtained as a colorless oil.

Step 2

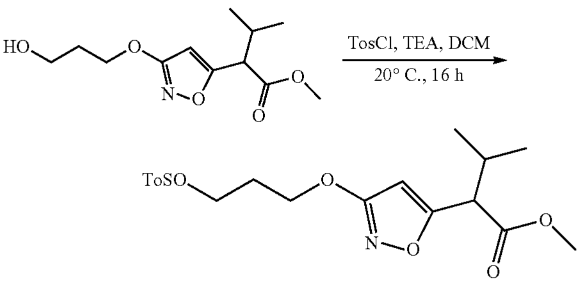

To a solution of methyl 2-[3-(3-hydroxypropoxy)isoxazol-5-yl]-3-methyl-butanoate (370 mg, 1.44 mmol, 1 eq) in dichloromethane (5 mL) was added triethylamine (291 mg, 2.88 mmol, 0.40 mL, 2 eq) and p-toluenesulfonyl chloride (411 mg, 2.16 mmol, 1.5 eq) sequentially at 20° C. and then stirred at 20° C. for 16 h. The reaction mixture was concentrated to give a residue. The residue was purified by prep-TLC (petroleum ether/ethyl acetate=3/1). Methyl 3-methyl-2-[3-[3-(p-tolylsulfonyloxy)propoxy]isoxazol-5-yl]butanoate (438 mg, 1.06 mmol, 74% yield) was obtained as a colorless oil.

Step 3

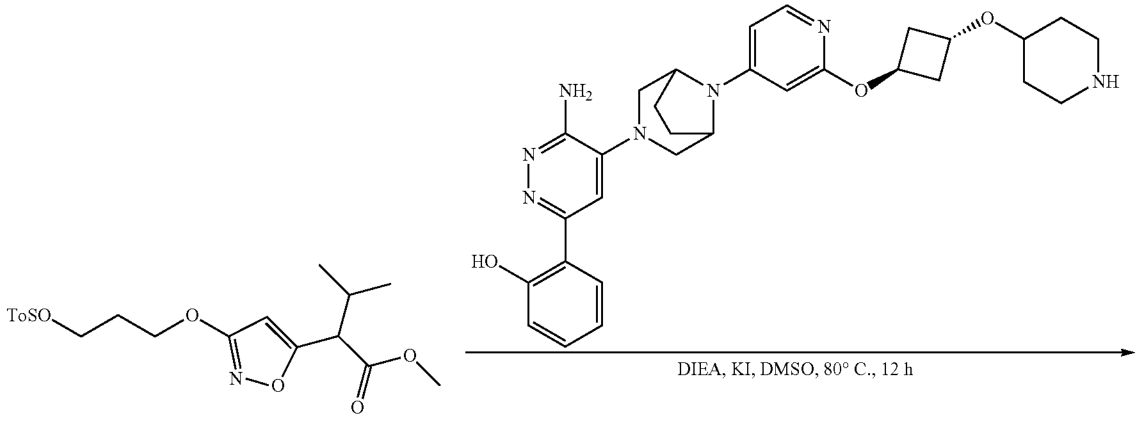

-continued

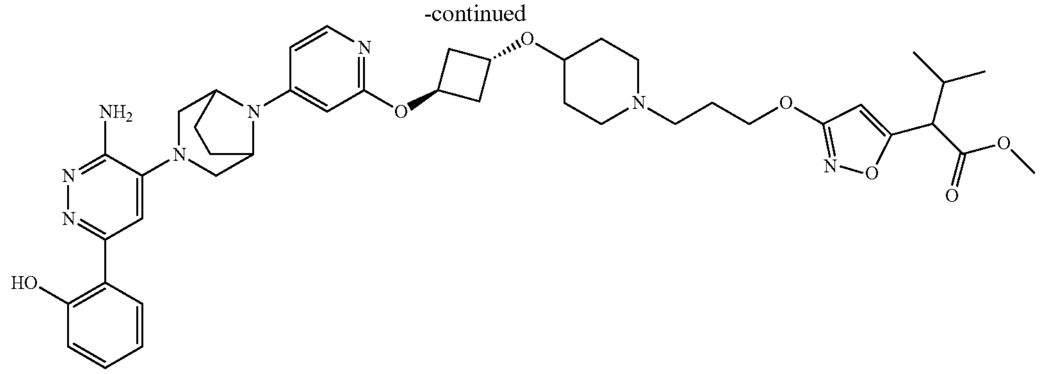

To a solution of methyl 3-methyl-2-[3-[3-(p-tolylsulfonyloxy)propoxy]isoxazol-5-yl]butanoate (250 mg, 0.61 mmol, 1 eq) and 2-[6-amino-5-[8-[2-[3-(4-piperidyloxy)cyclobutoxy]-4-pyridyl]-3,8-diazabicyclo[3.2.1]octan-3-yl]pyridazin-3-yl]phenol (386 mg, 0.61 mmol, 1 eq, 2trifluoroacetate) in dimethyl sulfoxide (3 mL) was added N,N-diisopropylethylamine (314 mg, 2.43 mmol, 0.42 mL, 4 eq) and potassium iodide (10 mg, 0.06 mmol, 0.1 eq) at 20° C., and the mixture was stirred at 80° C. for 12 hours. The reaction mixture was diluted with water (20 mL), then was extracted with ethyl acetate (10 mL×3). The combined organic layers were washed with brine (10 mL), dried over anhydrous sodium sulfate, filtered and concentrated under reduced pressure to give a residue. The residue was purified by silica gel column chromatography (dichloromethane/methanol=10/1). Methyl 2-[3-[3-[4-[3-[[4-[3-[3-amino-6-(2-hydroxyphenyl)pyridazin-4-yl]-3,8-diazabicyclo[3.2.1]octan-8-yl]-2-pyridyl] oxy] cyclobutoxy]-1-piperidyl]propoxy]isoxazol-5-yl]-3-methyl-butanoate (90 mg, 0.11 mmol, 17% yield) was obtained as a yellow oil.

Methyl 2-[3-[3-[4-[3-[[4-[3-[3-amino-6-(2-hydroxyphenyl)pyridazin-4-yl]-3,8-diazabicyclo[3.2.1]octan-8-yl]-2-pyridyl]oxy]cyclobutoxy]-1-piperidyl]propoxy]isoxazol-5-yl]-3-methyl-butanoate was converted to the final compound according to the scheme below using procedures described for other examples above.

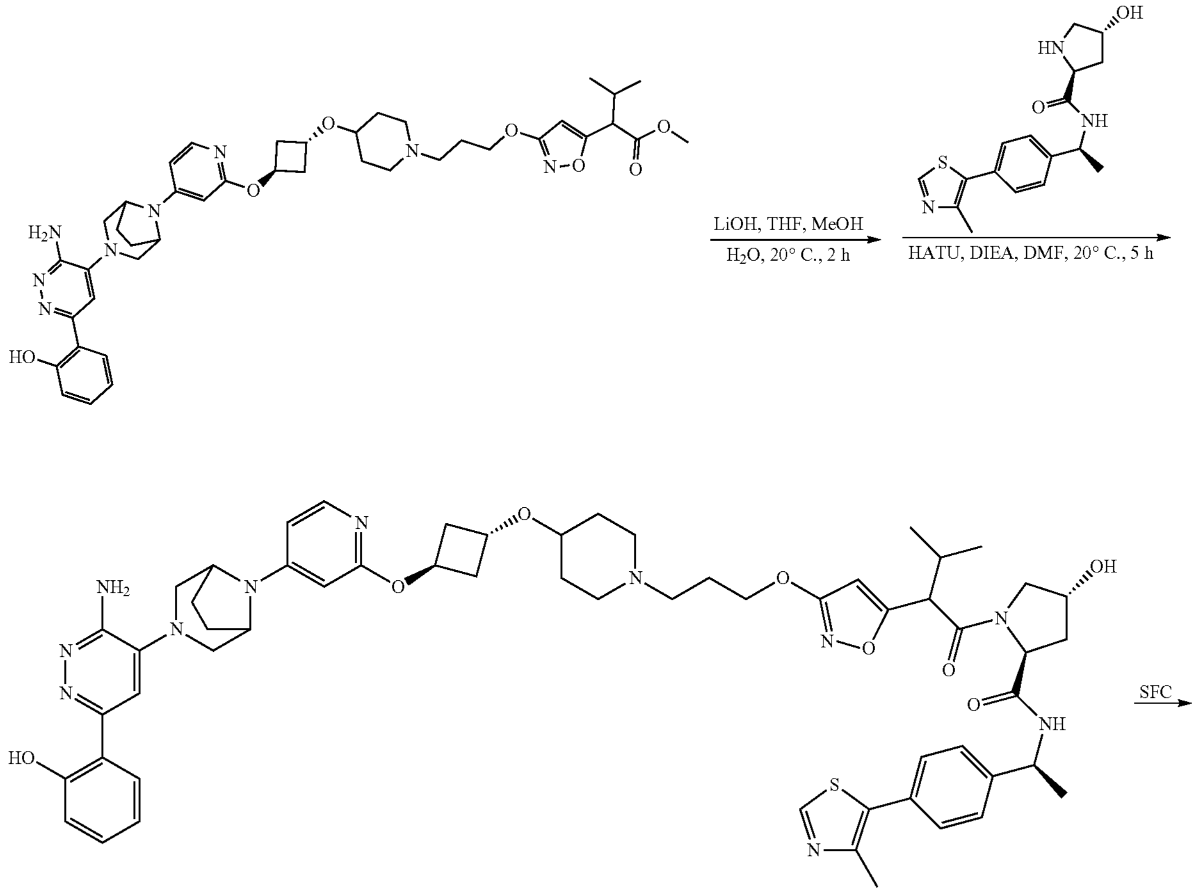

-continued
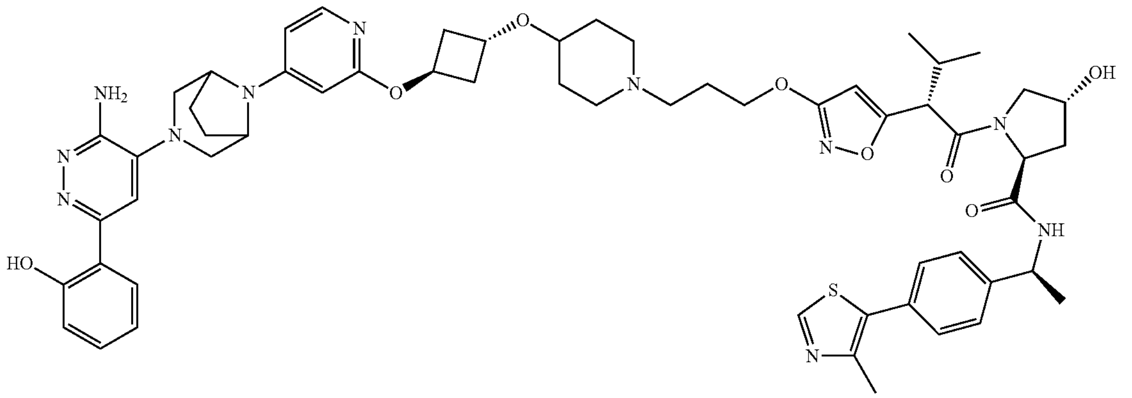
+
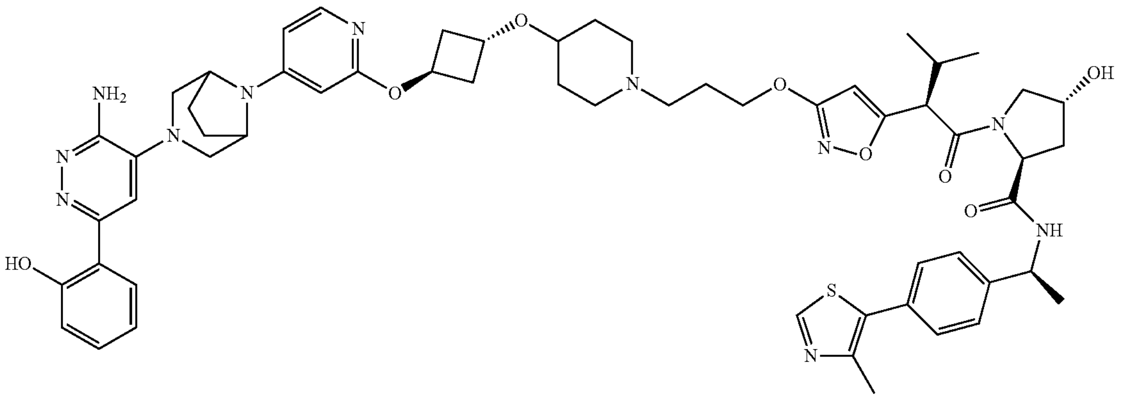
Ex. 218
Exemplary Synthesis of Exemplary Compound 223
Ex/ 223
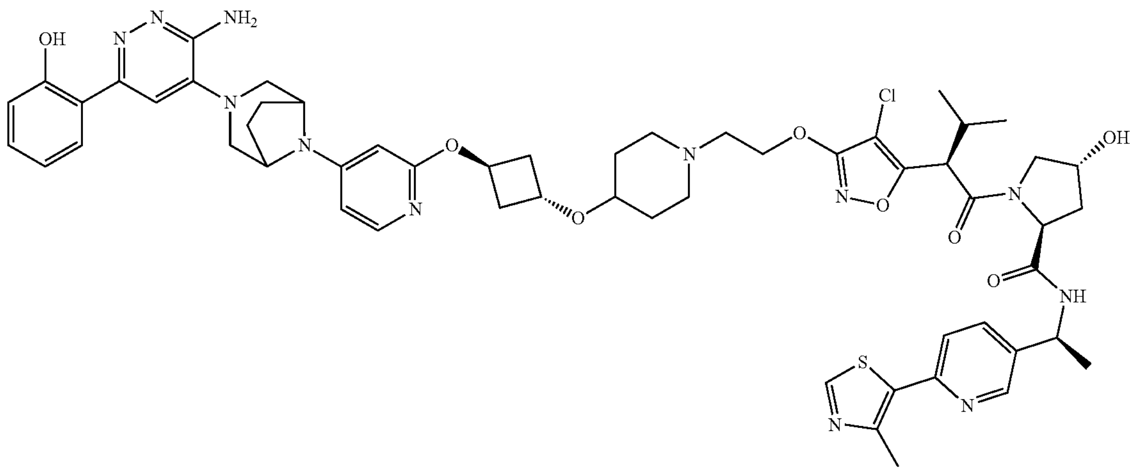

Step 1

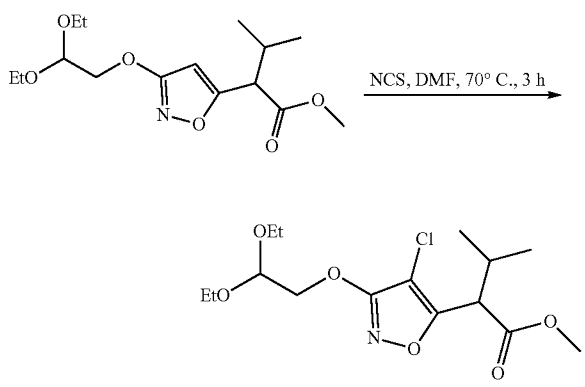

To a solution of methyl 2-[3-(2,2-diethoxyethoxy)isoxazol-5-yl]-3-methyl-butanoate (500 mg, 1.59 mmol, 1 eq) in N,N-dimethylformamide (10 mL) was added N-chlorosuccinimide (423 mg, 3.17 mmol, 2 eq). The reaction mixture was stirred at 70° C. for 3 hours. The reaction mixture was diluted with water (50 mL), and extracted with ethyl acetate (60 mL×3). The combined organic layer was washed with brine (20 mL×2). The organic layer was dried over anhydrous sodium sulfate, filtered and concentrated under vacuum to get the residue. The residue was purified by prep-HPLC (column: Phenomenex Synergi C18 150*25*10 um; mobile phase: [water (0.225% FA)-ACN]; B %: 65%-95%, 9 min) to get methyl 2-[4-chloro-3-(2,2-diethoxyethoxy)isoxazol-5-yl]-3-methyl-butanoate (337 mg, 0.965 mmol, 61% yield) as a colorless oil.

Step 2

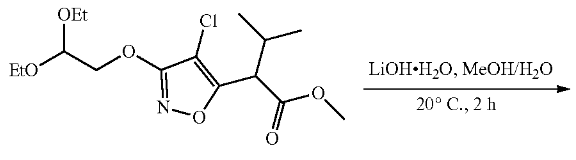

-continued

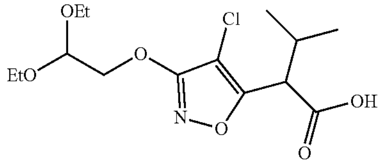

To a solution of methyl 2-[4-chloro-3-(2,2-diethoxyethoxy)isoxazol-5-yl]-3-methyl-butanoate (377 mg, 1.08 mmol, 1 eq) in methanol (2 mL) and water (1 mL) was added lithium hydroxide monohydrate (181 mg, 4.31 mmol, 4 eq). The reaction mixture was stirred at 20° C. for 2 hours. The mixture was cooled to 0° C. and the pH was adjusted to 6 with IM hydrogen chloride, then the solution was concentrated under vacuum to get the residue. The residue was purified by prep-HPLC (column: Phenomenex luna C18 150*25 10 um; mobile phase: [water (0.225% FA)-ACN]; B %: 54%-74%, 7.8 min) to get the product. 2-[4-chloro-3-(2,2-diethoxyethoxy)isoxazol-5-yl]-3-methyl-butanoic acid (229 mg, 0.68 mmol, 63% yield) was obtained as a white solid.

2-[4-Chloro-3-(2,2-diethoxyethoxy)isoxazol-5-yl]-3-methyl-butanoic acid was converted to the final compound using procedures described for other examples above.

Exemplary compound 222 was prepared using analogous procedures.

Exemplary Synthesis of Exemplary Compound 225

Ex. 225

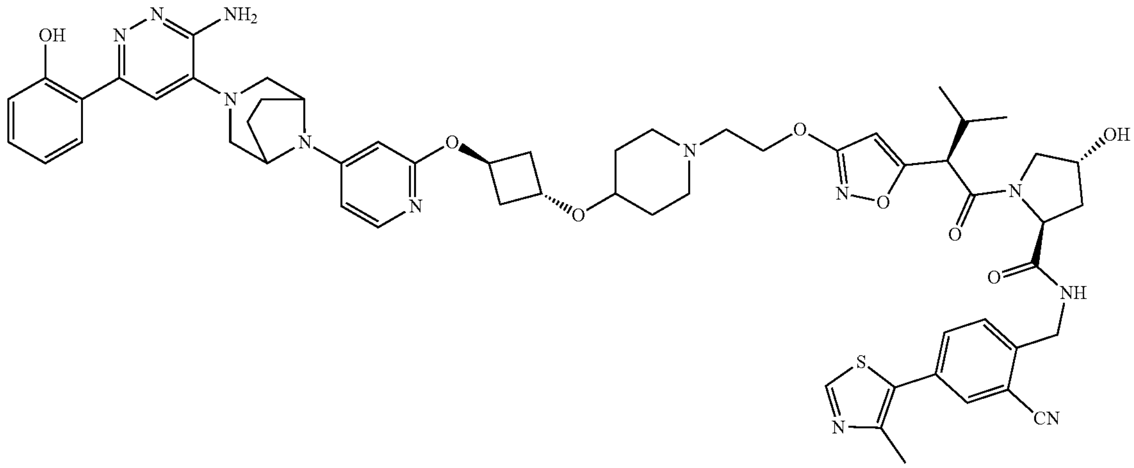

Step 1

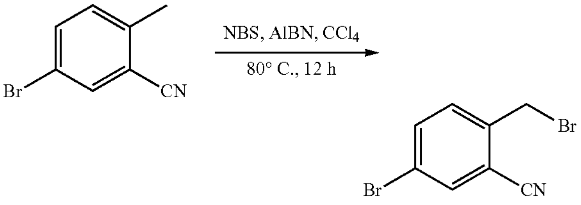

To a solution of 5-bromo-2-methyl-benzonitrile (5 g, 25.50 mmol, 1 eq) in carbon tetrachloride (50 mL) was added N-bromosuccinimide (4.77 g, 26.78 mmol, 1.05 eq)

and 2,2-azobis(2-methylpropionitrile) (419 mg, 2.55 mmol, 0.1 eq) under nitrogen. The reaction mixture was stirred at 80° C. for 16 h. The mixture was filtered, and the filtrate was concentrated in vacuum. The residue was purified by silica gel chromatography (petroleum ether:ethyl acetate=1:0 to 10:1). 5-Bromo-2-(bromomethyl)benzonitrile (4.5 g, 16.37 mmol, 64% yield) was obtained as a light yellow solid.

Step 2

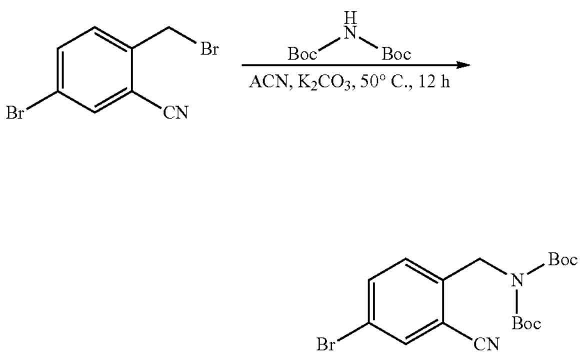

To a solution of 5-bromo-2-(bromomethyl)benzonitrile (4.4 g, 16.00 mmol, 1 eq) and tert-butyl N-tert-butoxycarbonylcarbamate (4.17 g, 19.20 mmol, 1.2 eq) in acetonitrile (50 mL) was added potassium carbonate (4.42 g, 32.01 mmol, 2 eq). The reaction mixture was stirred at 50° C. for 12 hours. LCMS showed most of 5-bromo-2-(bromomethyl) benzonitrile was consumed. Water (100 mL) was added to the mixture, and the resulting mixture was extracted with ethyl acetate (50 mL×3). The combined organic phase was washed with brine (50 mL), dried over sodium sulfate, filtered and concentrated in vacuum. The residue was purified by silica gel chromatography (petroleum ether:ethyl acetate=100:1 to 5:1). tert-Butyl N-[(4-bromo-2-cyano-phenyl)methyl]-N-tert-butoxycarbonyl-carbamate (6.4 g, 15.56 mmol, 97% yield) was obtained as a colorless oil.

Step 3

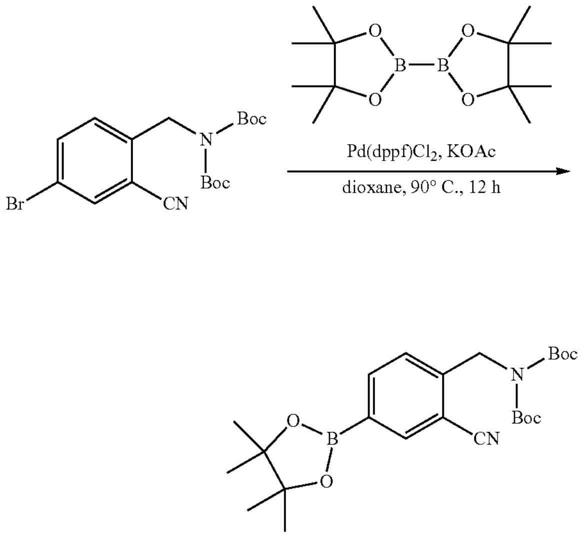

To a solution of tert-butyl N-[(4-bromo-2-cyano-phenyl) methyl]-N-tert-butoxycarbonyl-carbamate (2 g, 4.86 mmol, 1 eq), 4,4,5,5-tetramethyl-2-(4,4,5,5-tetramethyl-1,3,2-dioxaborolan-2-yl)-1,3,2-dioxaborolane (1.36 g, 5.35 mmol, 1.1 eq) in dioxane (20 mL) was added potassium acetate (1.19 g, 12.16 mmol, 2.5 eq) and (1,1'-bis(diphenylphosphino) ferrocene)palladium(II) dichloride (356 mg, 0.49 mmol, 0.1 eq) under nitrogen. The reaction mixture was stirred at 90° C. for 12 hours. The mixture was filtered through a Celite pad, and the filtrate was concentrated to give tert-butyl N-tert-butoxycarbonyl-N-[[2-cyano-4-(4,4,5,5-tetramethyl-1,3,2-dioxaborolan-2-yl)phenyl]methyl]carbamate (2.2 g, crude) as a black oil.

Step 4

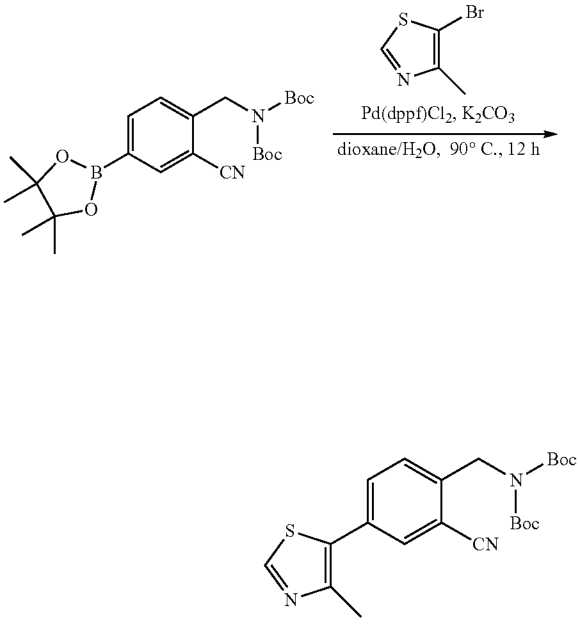

To a solution of tert-butyl N-tert-butoxycarbonyl-N-[[2-cyano-4-(4,4,5,5-tetramethyl-1,3,2-dioxaborolan-2-yl)phenyl]methyl]carbamate (2.2 g, 4.80 mmol, 1 eq), 5-bromo-4-methyl-thiazole (940 mg, 5.28 mmol, 1.1 eq) in dioxane (20 mL) and water (4 mL) was added potassium carbonate (1.66 g, 12.00 mmol, 2.5 eq) and (1,1'-bis(diphenylphosphino)ferrocene)palladium(II) dichloride (351 mg, 0.48 mmol, 0.1 eq) under nitrogen. The reaction mixture was stirred at 100° C. for 12 hours. Water (100 mL) was added to the mixture, the resulting mixture was extracted with ethyl acetate (50 mL×3). The combined organic phase was washed with brine (50 mL), dried over sodium sulfate, filtered and concentrated in vacuum. The residue was purified by silica gel chromatography (petroleum ether:ethyl acetate=100:1 to 1:1). tert-Butyl N-tert-butoxycarbonyl-N-[[2-cyano-4-(4-methylthiazol-5-yl)phenyl] methyl]carbamate (1.7 g, 3.96 mmol, 82% yield) was obtained as a light yellow solid.

tert-Butyl N-tert-butoxycarbonyl-N-[[2-cyano-4-(4-methylthiazol-5-yl)phenyl]methyl]carbamate was converted to the final compound as described above for other examples.

Exemplary compound 224 was prepared using analogous procedures.

Exemplary Synthesis of Exemplary Compound 126

Ex. 126

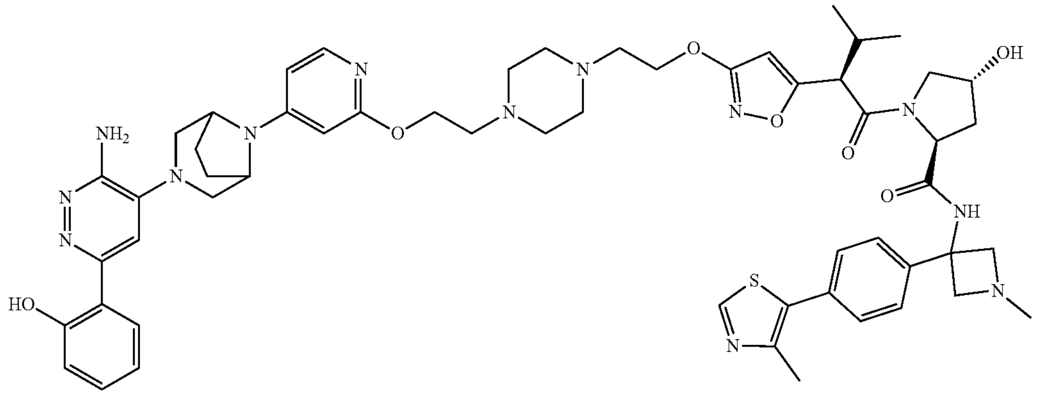

Step 1

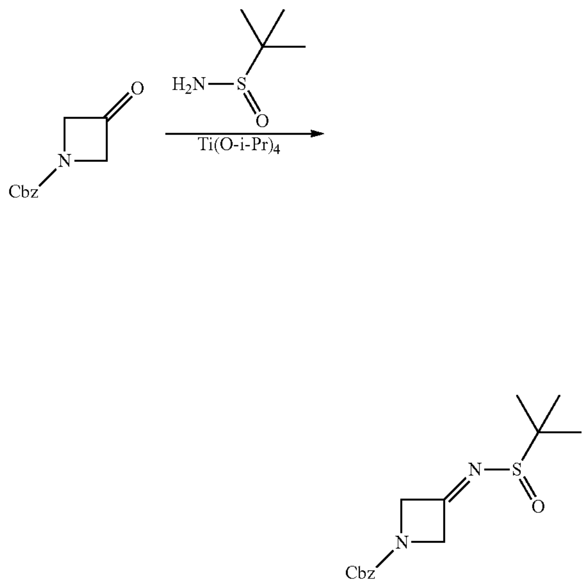

To a mixture of benzyl 3-oxoazetidine-1-carboxylate (25 g, 122 mmol, 1 eq) and 2-methylpropane-2-sulfinamide (14.8 g, 122 mmol, 1 eq) in THF (250 mL) was added titanium(IV) isopropylate (38.9 g, 171 mmol, 35.4 mL, 1.4 eq) in one portion at 15° C. under nitrogen. The mixture was stirred at 60° C. for 2 hours. The mixture was poured into ethyl acetate and ice-water (1000 mL) and stirred for 20 minutes, filtered. The aqueous phase was extracted with ethyl acetate (500 mL×3). The combined organic phase was washed with brine (200 mL×3), dried with anhydrous sodium sulfate, filtered and concentrated in vacuum. The residue was purified by silica gel chromatography (petroleum ether/ethyl acetate=30/1 to 8/1) to afford benzyl 3-tert-butylsulfinyliminoazetidine-1-carboxylate (39 g, crude) as a yellow solid.

Step 2

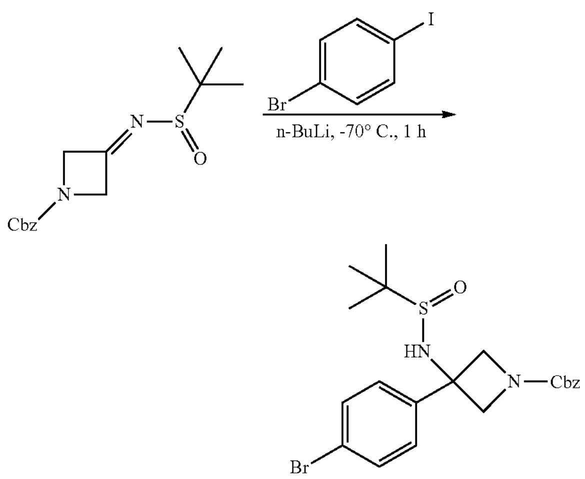

To a solution of 1-bromo-4-iodo-benzene (35.78 g, 126 mmol, 1 eq) in THF (350 mL) was added n-butyllithium (2.5 M, 50.6 mL, 1 eq) dropwise at −70° C. under nitrogen, and the mixture was stirred at this temperature for 30 minutes. Then solution of benzyl 3-tert-butylsulfinyliminoazetidine-1-carboxylate (39 g, 126.46 mmol, 1 eq) in THF (70 mL) was added dropwise under nitrogen. The reaction mixture was stirred at −70° C. for 1 hour. The mixture was quenched with ice water (200 mL). The aqueous phase was extracted with ethyl acetate (500 mL×3). The combined organic phase was washed with brine (200 mL×2), dried with anhydrous sodium sulfate, filtered and concentrated in vacuum. The residue was purified by silica gel chromatography (petroleum ether/ethyl acetate=3/1 to 1/1). Then the crude product was purified by semi-preparative reverse phase HPLC (column: Phenomenex luna c18 250 mm*100 mm*10 um; mobile phase: [water (0.1% TFA)-ACN]; B %: 40ACN %-70ACN %, 45 min) to afford benzyl 3-(4-bromophenyl)-3-(tert-butylsulfinylamino)azetidine-1-carboxylate (4.62 g, 9.93 mmol, 7% yield) as a yellow oil. In addition, 4.16 g of somewhat impure product (purity 86%) was collected as a yellow oil.

Step 3

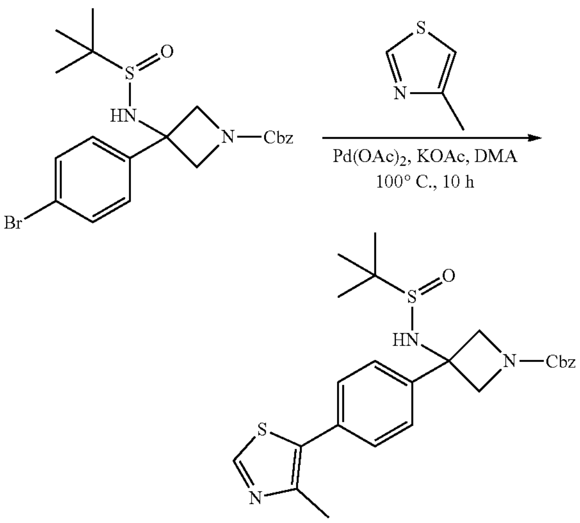

To a mixture of benzyl 3-(4-bromophenyl)-3-(tert-butylsulfinylamino)azetidine-1-carboxylate (4.62 g, 9.93 mmol, 1 eq), potassium acetate (1.95 g, 19.85 mmol, 2 eq) and 4-methylthiazole (1.97 g, 19.85 mmol, 1.8 mL, 2 eq) in dimethylacetamide (60 mL) was added palladium(II) acetate (223 mg, 0.99 mmol, 0.1 eq) in one portion at 20° C. under nitrogen. The mixture was stirred at 100° C. for 16 hours. The mixture was cooled to 20° C., poured into ice-water (w/w=1/1, 100 mL) and stirred for 5 minutes. The aqueous phase was extracted with ethyl acetate (50 mL×4). The combined organic phase was washed with brine (30 mL×2), dried with anhydrous sodium sulfate, filtered and concentrated in vacuum. The residue was purified by semi-preparative reverse phase HPLC (formic acid condition; column: Phenomenex Synergi Max-RP 250*50 mm*10 um; mobile phase: [water (0.225% FA)-ACN]; B %: 45ACN %-75ACN %, 29 min) to afford benzyl 3-(tert-butylsulfinylamino)-3-[4-(4-methylthiazol-5-yl)phenyl]azetidine-1-carboxylate (2.3 g, 4.76 mmol, 48% yield) as a yellow solid.

Step 4

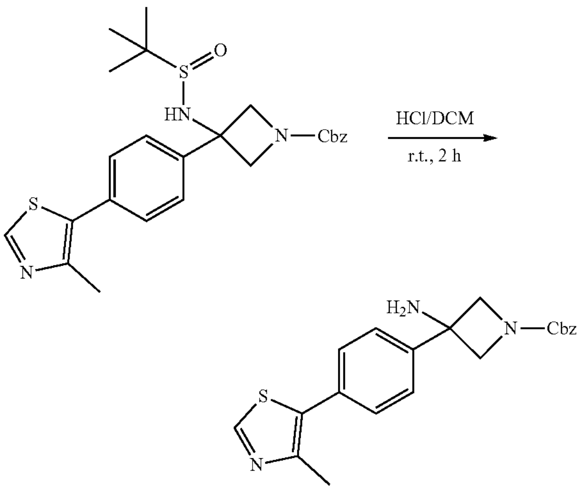

A solution of benzyl 3-(tert-butylsulfinylamino)-3-[4-(4-methylthiazol-5-yl)phenyl]azetidine-1-carboxylate (3.4 g, 7.03 mmol, 1 eq) and hydrochloric acid/methanol (4 M, 30 mL, 17.07 eq) in dichloromethane (5 mL) was stirred at 25° C. for 2 h. Compound benzyl 3-amino-3-[4-(4-methylthiazol-5-yl)phenyl]azetidine-1-carboxylate hydrochloride (3 g, crude) was obtained as a white solid.

Step 5

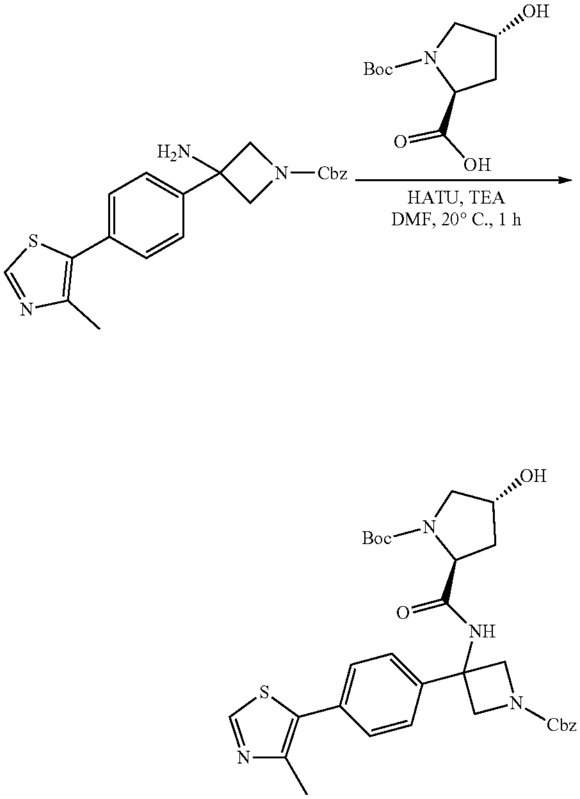

To a mixture of benzyl 3-amino-3-[4-(4-methylthiazol-5-yl)phenyl]azetidine-1-carboxylate hydrochloride (3 g, 7.21 mmol, 1 eq), O-(7-azabenzotriazol-1-yl)-N,N,N',N'-tetramethyluronium hexafluorophosphate (4.11 g, 10.82 mmol, 1.5 eq) and (2S,4R)-1-tert-butoxycarbonyl-4-hydroxy-pyrrolidine-2-carboxylic acid (1.67 g, 7.21 mmol, 1 eq) in N,N-dimethylformamide (40 mL) was added triethylamine (2.19 g, 21.64 mmol, 3.0 mL, 3 eq) in one portion at 15° C. under nitrogen. The mixture was stirred at 15° C. for 1 h. The mixture was poured into ice-water (w/w=1/1, 100 mL) and stirred for 5 min. The aqueous phase was extracted with ethyl acetate (60 mL×3). The combined organic phase was washed with brine (30 mL×2), dried with anhydrous sodium sulfate, filtered and concentrated under vacuum. The residue was purified by semi-preparative reverse phase HPLC (column: Phenomenex Synergi Max-RP 250*80 mm*10 um; mobile phase: [water (0.225% FA)-ACN]; B %: 30%-60%, 30 min). Compound tert-butyl (2S,4R)-2-[[1-benzyloxycarbonyl-3-[4-(4-methylthiazol-5-yl)phenyl]azetidin-3-yl]carbamoyl]-4-hydroxy-pyrrolidine-1-carboxylate (3.32 g, 5.60 mmol, 77% yield) was obtained as a white solid.

Step 6

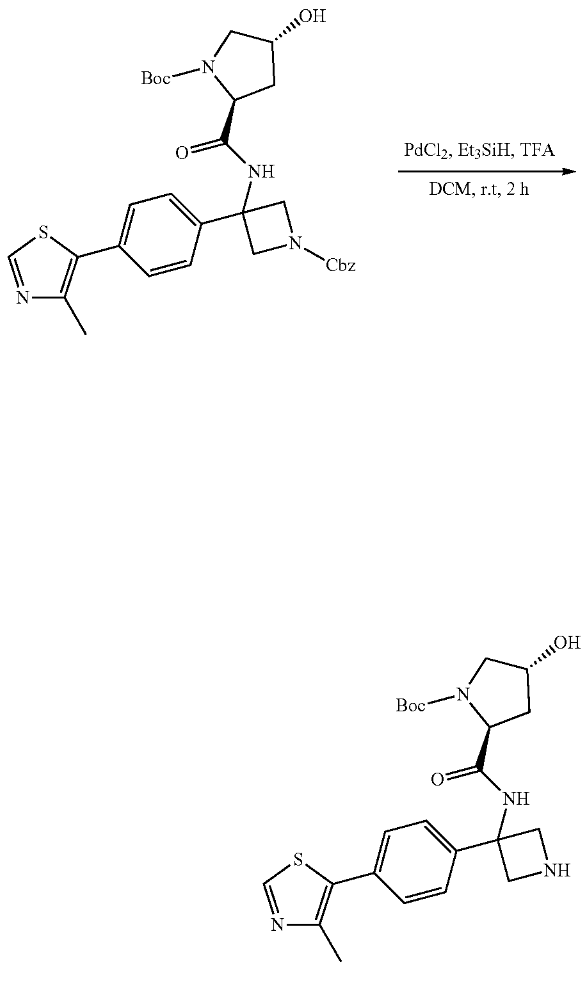

Step 7

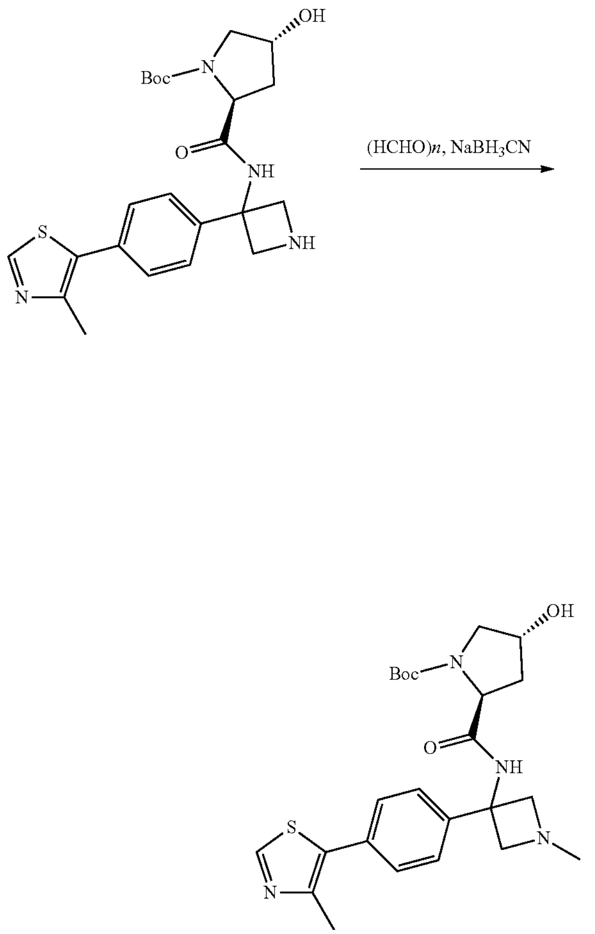

To a mixture of tert-butyl (2S,4R)-2-[[1-benzyloxycarbonyl-3-[4-(4-methylthiazol-5-yl) phenyl]azetidin-3-yl]carbamoyl]-4-hydroxy-pyrrolidine-1-carboxylate (1.1 g, 1.86 mmol, 1 eq) and triethylamine (666 mg, 6.59 mmol, 0.9 mL, 3.55 eq) in dichloromethane (100 mL) was added palladium (ii) chloride (329.10 mg, 1.86 mmol, 1 eq) in one portion at 0° C. under nitrogen. Triethylsilane (2.81 g, 24.13 mmol, 3.8 mL, 13 eq) was added, and the reaction mixture was stirred at 20° C. for 2 hours. To the reaction was added trifluoroacetic acid (4.23 g, 37.14 mmol, 2.75 mL, 20.01 eq), and the mixture was stirred at 20° C. for an additional 1 hour. The mixture was filtered and concentrated under reduced pressure at 40° C. The residue was purified by semi-preparative reverse phase HPLC (formic acid condition; column: Kromasil 250*50 mm*10 um; mobile phase: [water (0.225% FA)–ACN]; B %: 26ACN %-56ACN %, 28 min). tert-butyl (2S,4R)-4-hydroxy-2-[[3-[4-(4-methylthiazol-5-yl)phenyl] azetidin-3-yl]carbamoyl]pyrrolidine-1-carboxylate (336 mg, 0.73 mmol, 39% yield) was obtained as a white solid.

A mixture of tert-butyl (2S,4R)-4-hydroxy-2-[[3-[4-(4-methylthiazol-5-yl)phenyl]azetidin-3-yl]carbamoyl]pyrrolidine-1-carboxylate (390 mg, 0.85 mmol, 1 eq) and formaldehyde (138 mg, 1.70 mmol, 0.1 mL, 37% purity, 2 eq) in dichloromethane (15 mL) was stirred at 20° C. for 30 minutes. Acetic acid (51 mg, 0.85 mmol, 1 eq) and sodium triacetoxyborohydride (901 mg, 4.25 mmol, 5 eq) were added, and the mixture was stirred at 20° C. for 5 hours. The mixture was concentrated under reduced pressure at 40° C. The residue was purified by semi-preparative reverse phase HPLC (formic acid condition; column: Phenomenex Synergi C18 150*25*10 um; mobile phase: [water (0.225% FA)–ACN]; B %: 0% -30%, 10 min). tert-Butyl (2S,4R)-4-hydroxy-2-[[1-methyl-3-[4-(4-methylthiazol-5-yl)phenyl] azetidin-3-yl]carbamoyl]pyrrolidine-1-carboxylate (300 mg, 0.63 mmol, 74% yield) was obtained as a yellow oil.

tert-Butyl (2S,4R)-4-hydroxy-2-[[1-methyl-3-[4-(4-methylthiazol-5-yl)phenyl]azetidin-3-yl]carbamoyl]pyrrolidine-1-carboxylate was converted to the final compound using procedures analogous to those described for examples above.

Exemplary compound 228 was prepared using analogous procedures.

Ex. 233
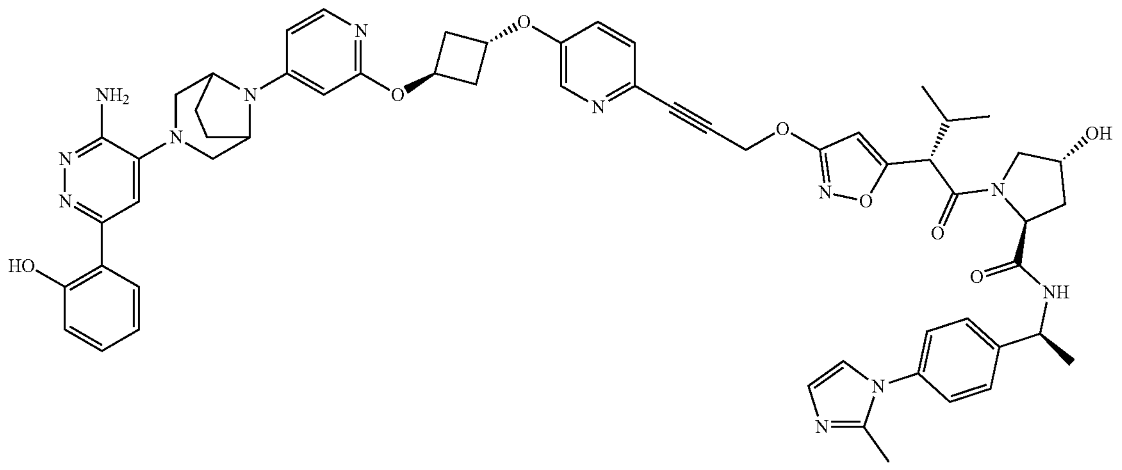
Ex. 234
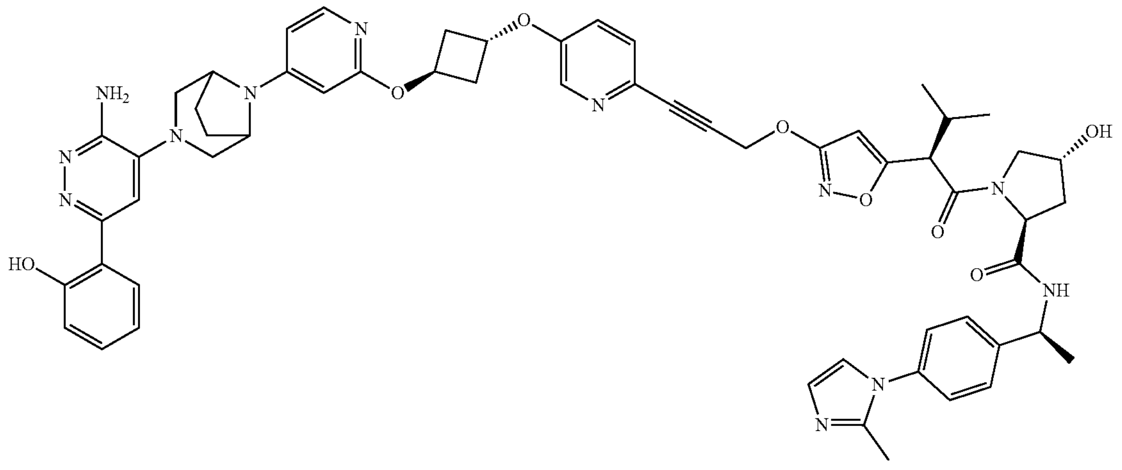
Prepared according to the scheme below using procedures analogous to those described for exemplary compounds 76 and 70.
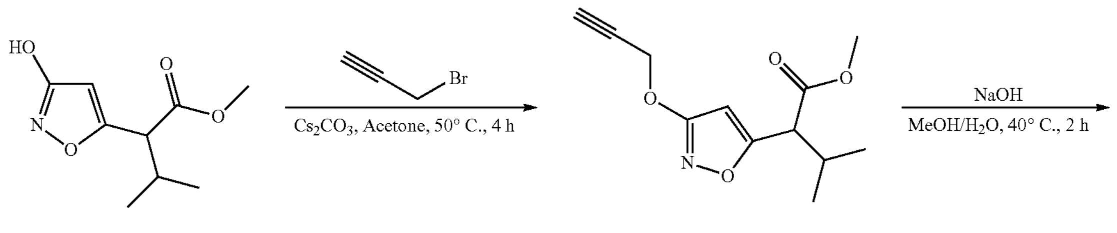

-continued
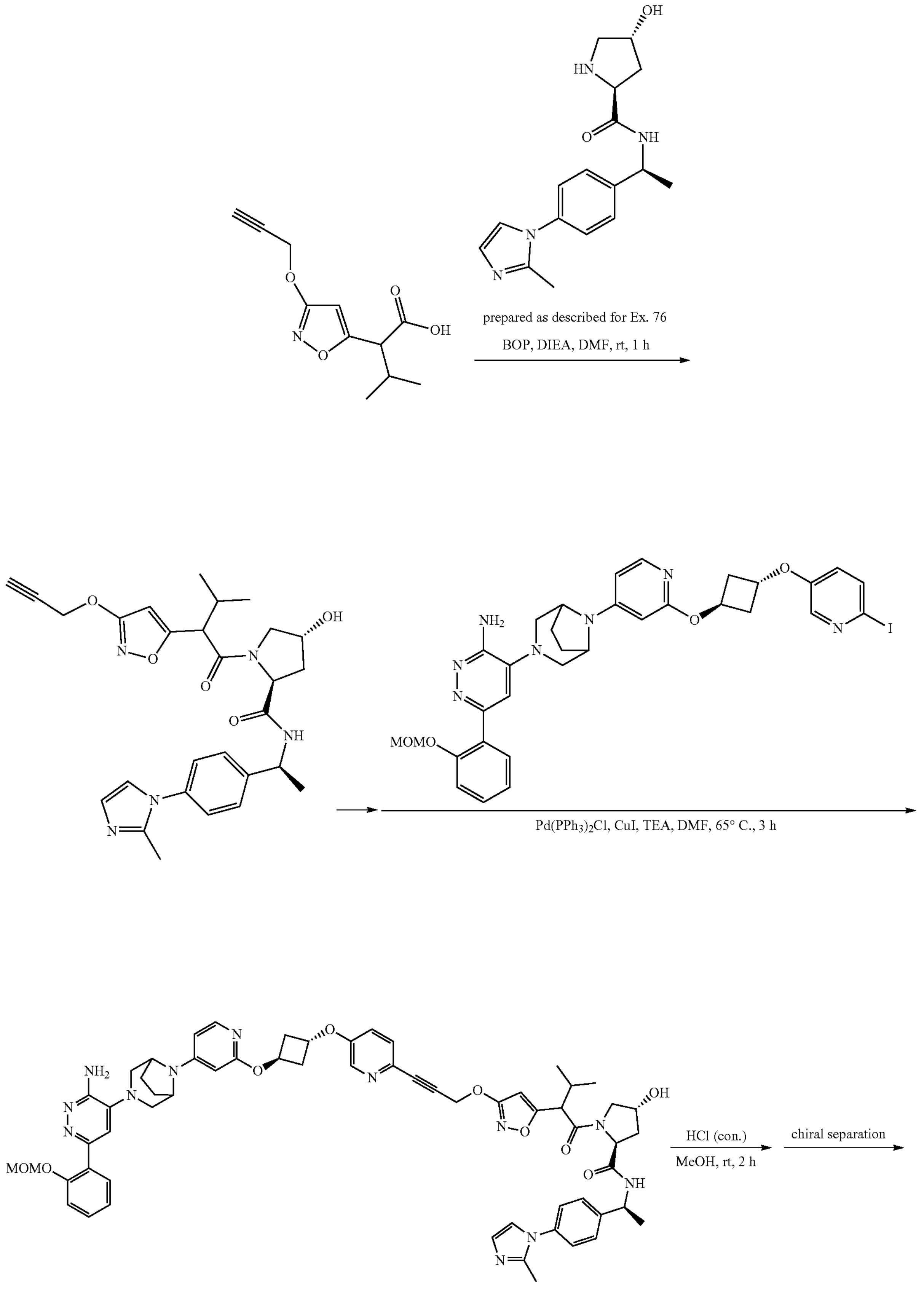

-continued
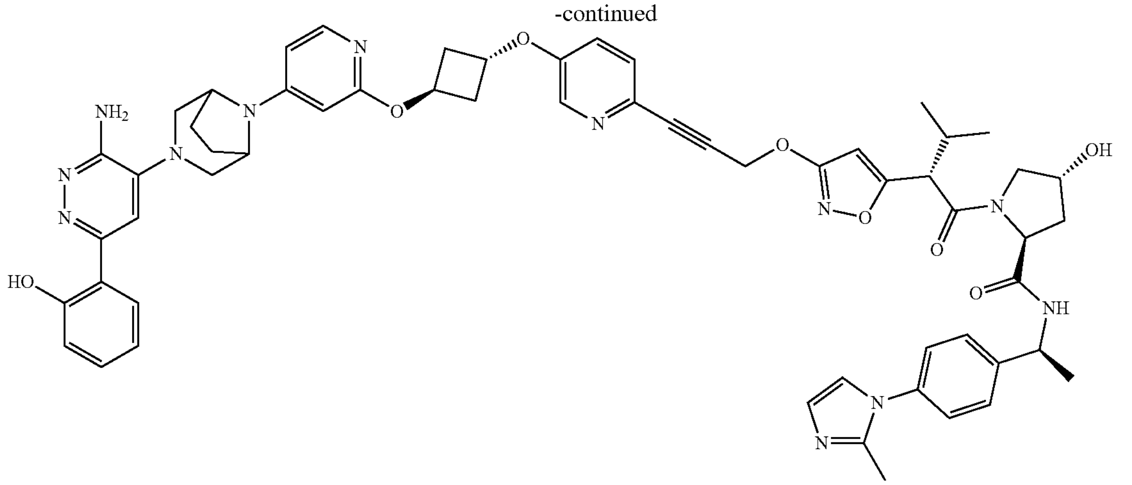
+
Ex. 233
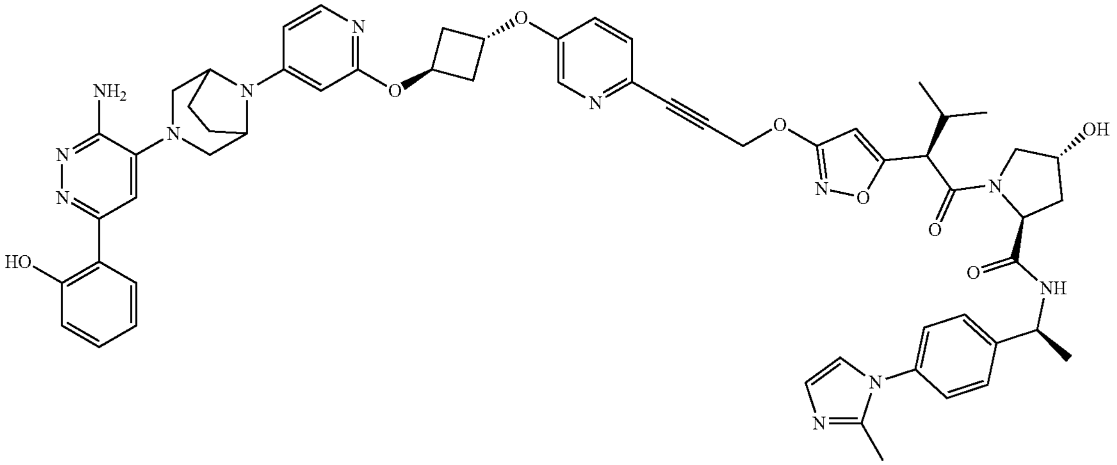
Ex. 234
Exemplary Synthesis of Exemplary Compound 127
Ex. 127
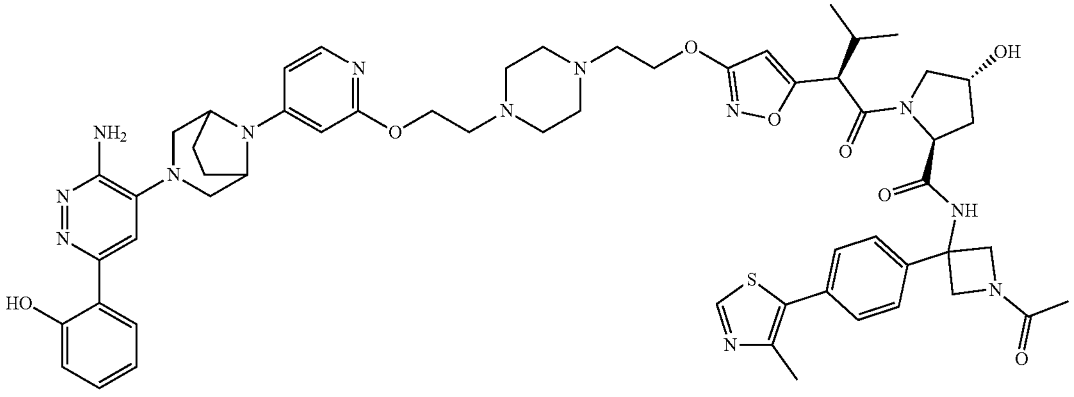

Step 1

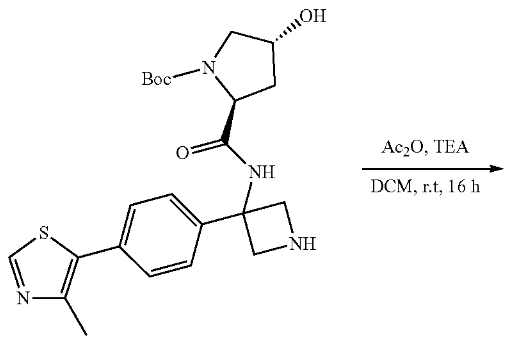

-continued

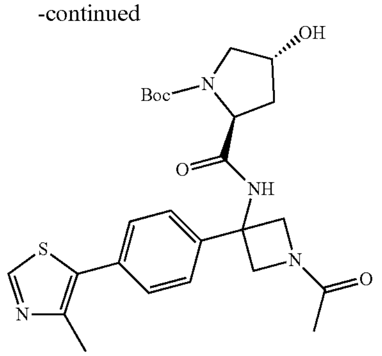

To a mixture of tert-butyl (2S,4R)-4-hydroxy-2-[[3-[4-(4-methylthiazol-5-yl)phenyl]azetidin-3-yl]carbamoyl]pyrrolidine-1-carboxylate (300 mg, 0.65 mmol, 1 eq) and triethylamine (198 mg, 1.96 mmol, 3 eq) in dichloromethane (60 mL) was added acetic anhydride (100.18 mg, 0.98 mmol, 91.9 uL, 1.5 eq) in one portion at 25° C. under nitrogen. The mixture was stirred at 25° C. for 16 h. The mixture was concentrated under reduced pressure at 45° C. The residue was purified by semi-preparative reverse phase HPLC (basic conditions, column: Waters Xbridge 150*25 5 um; mobile phase: [water (0.05% ammonia hydroxide v/v)-ACN]; B %: 10%-40%, 10 min). The crude product tert-butyl (2S,4R)-2-[[1-acetyl-3-[4-(4-methylthiazol-5-yl)phenyl]azetidin-3-yl]carbamoyl]-4-hydroxy-pyrrolidine-1-carboxylate (232 mg, 0.46 mmol, 71% yield) was obtained as a yellow oil.

tert-Butyl (2S,4R)-2-[[1-acetyl-3-[4-(4-methylthiazol-5-yl)phenyl]azetidin-3-yl]carbamoyl]-4-hydroxy-pyrrolidine-1-carboxylate was converted to the final product using procedures described for examples above.

Exemplar compound 235 was prepared using analogous procedures.

Exemplary Synthesis of Exemplary Compound 240

Ex. 240

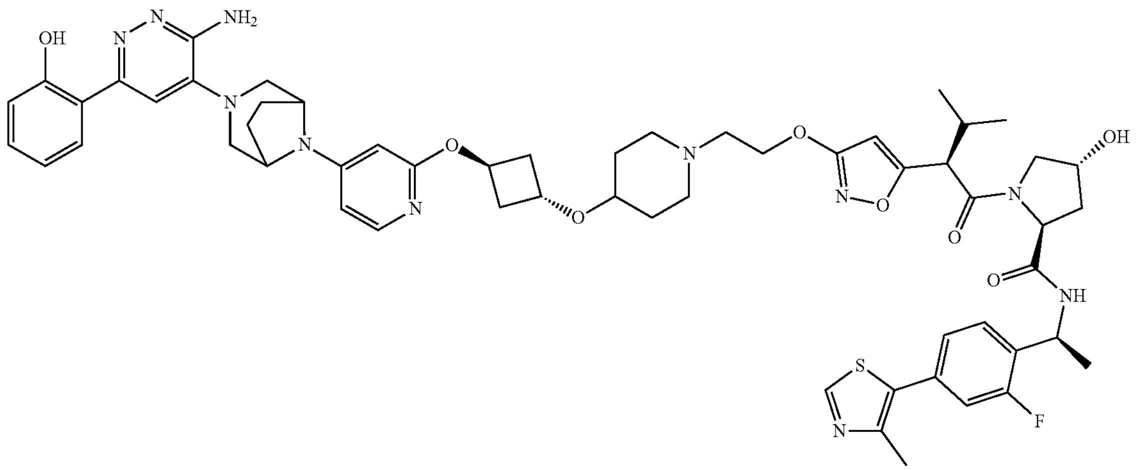

tert-Butyl (S)-(1-(2-fluoro-4-(4-methylthiazol-5-yl)phenyl)ethyl)carbamate was prepared according to the scheme below using procedures analogous to those described for exemplary compound 202.

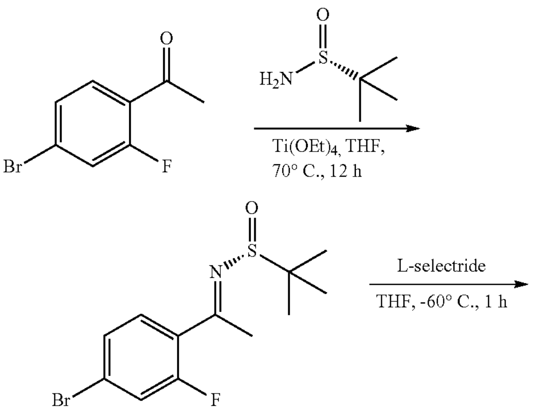

-continued
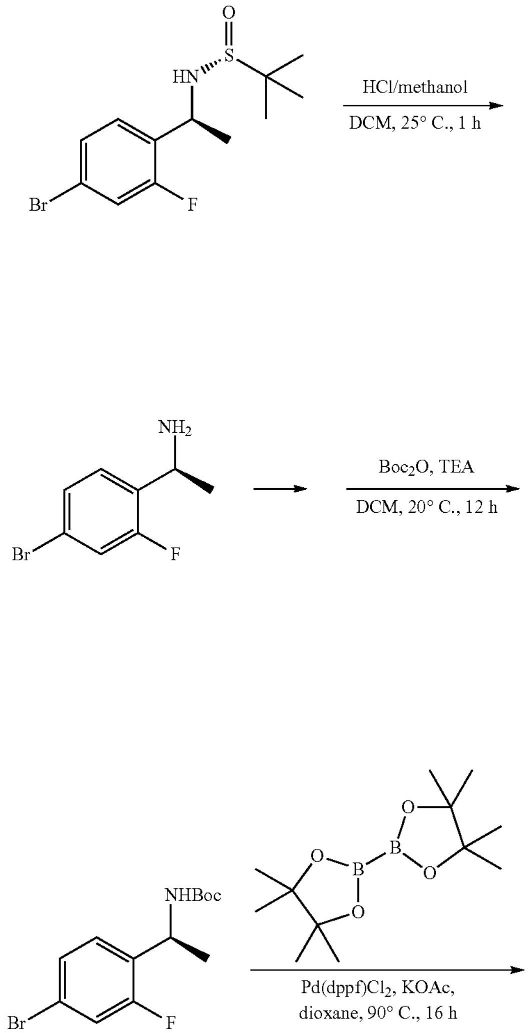
-continued
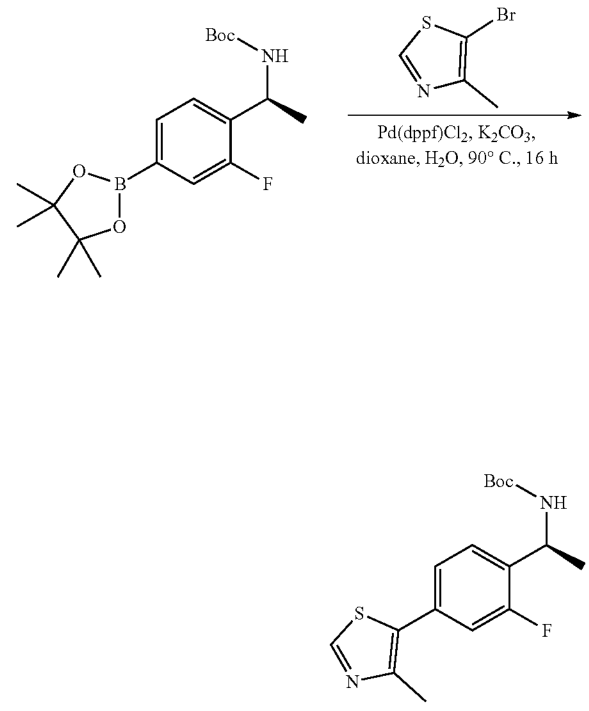
tert-Butyl (S)-(1-(2-fluoro-4-(4-methylthiazol-5-yl)phenyl)ethyl)carbamate was converted to the final compound using procedures analogous to those described for other examples.
Exemplary compound 239 was prepared using analogous procedures.
Exemplary Synthesis of Exemplary Compound 243 and 244
Ex. 243
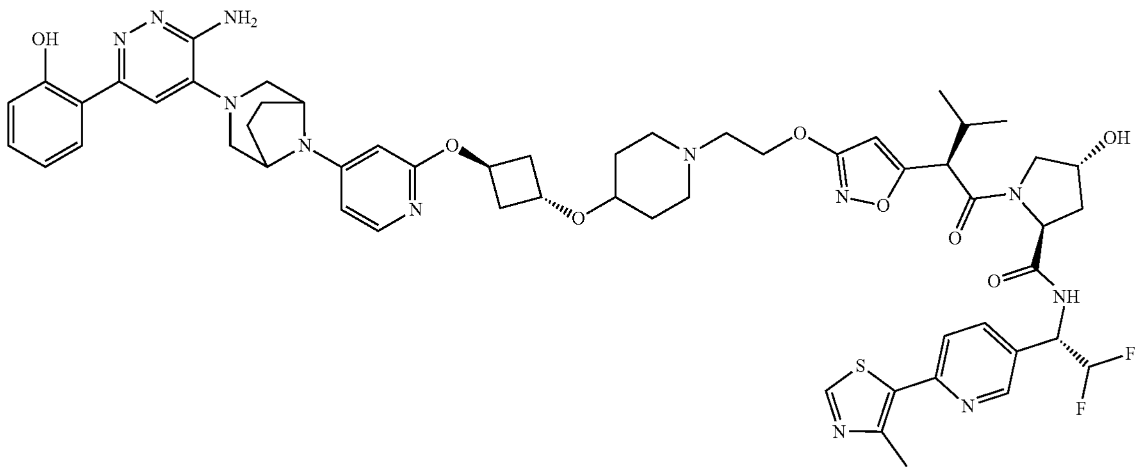

-continued

Ex. 244

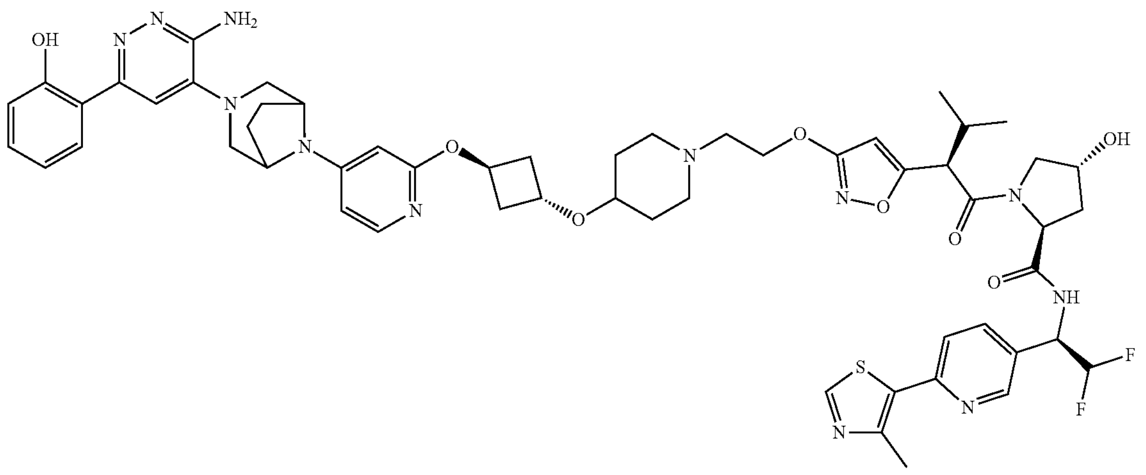

Step 1

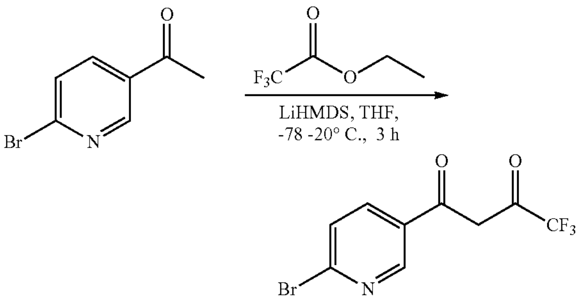

To a solution of ethyl trifluoroacetate (21.31 g, 150 mmol, 20.7 mL, 1.5 eq) in tetrahydrofuran (300 mL) was added lithium bis(trimethylsilyl)amide (1 M, 120 mL, 1.2 eq) at −78° C. The mixture was stirred at −78° C. for 1 hour. Then 1-(6-bromo-3-pyridyl)ethanone (20 g, 100 mmol, 1 eq) in tetrahydrofuran (20 mL) was added dropwise to the mixture at −78° C. The reaction mixture was stirred at 20° C. for 2 hours. Saturated ammonium chloride (200 mL) was added to quench the reaction, water (500 mL) was added to the mixture. The resulting mixture was extracted with ethyl acetate (300 mL×3). The combined organic phase was washed with brine (500 mL), dried over sodium sulfate, filtered and concentrated in vacuum. The residue was triturated with petroleum ether and ethyl acetate (255 mL, petroleum ether:ethyl acetate=50:1) and filtered to afford a light yellow solid. The filtrate was concentrated in vacuum. The residue was purified by silica gel chromatography (petroleum ether:ethyl acetate=10:1 to 0:1). 1-(6-Bromo-3-pyridyl)-4,4,4-trifluoro-butane-1,3-dione (28 g, 94.6 mmol, 94% yield) was obtained as a yellow solid.

Step 2

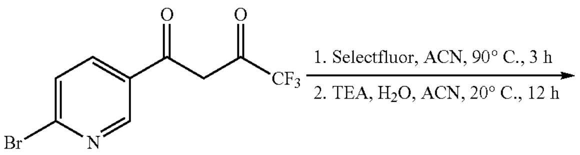

-continued

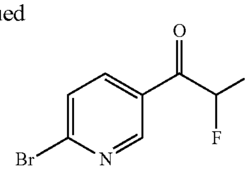

To a solution of 1-(6-bromo-3-pyridyl)-4,4,4-trifluoro-butane-1,3-dione (15 g, 50.67 mmol, 1 eq) in acetonitrile (150 mL) was added 1-(chloromethyl)-4-fluoro-1,4-diazoniabicyclo[2.2.2]octane; ditetrafluoroborate (44.87 g, 126.7 mmol, 2.5 eq). The reaction mixture was stirred at 90° C. for 3 h. Then water (1.83 g, 101.3 mmol, 1.8 mL, 2 eq) was added to the mixture, and the reaction mixture was stirred at 90° C. for 15 minutes. Then triethylamine (25.64 g, 253.3 mmol, 35.2 mL, 5 eq) was added to the mixture at 20° C., and the reaction mixture was stirred at 20° C. for 16 hours. Water (300 mL) was added to the mixture. The resulting mixture was extracted with ethyl acetate (300 mL×3). The combined organic phase was washed with brine (500 mL), dried over sodium sulfate, filtered and concentrated in vacuum. The residue was purified by silica gel chromatography (dichloromethane:methanol=1:0 to 10:1). 1-(6-Bromo-3-pyridyl)-2,2-difluoro-ethanone (7.9 g, crude) was obtained as a brown oil.

Step 3

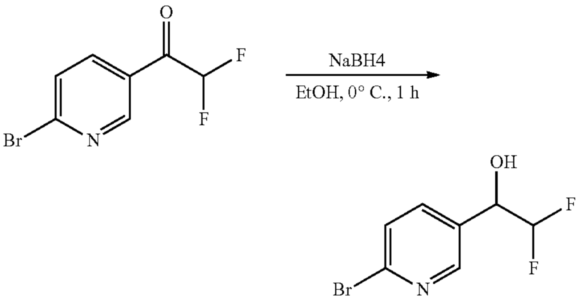

To a solution of 1-(6-bromo-3-pyridyl)-2,2-difluoro-ethanone (7.9 g, 33.47 mmol, 1 eq) in ethanol (80 mL) was added sodium borohydride (1.27 g, 33.47 mmol, 1 eq) in three portions at 0° C. The reaction mixture was stirred at 0° C. for 1 hour. Water (200 mL) was added to the mixture, and the resulting mixture was extracted with ethyl acetate (100 mL×3). The combined organic phase was washed with brine (150 mL), dried over sodium sulfate, filtered and concentrated in vacuum. The residue was purified by silica gel chromatography (petroleum ether:ethyl acetate=100:1 to 1:1). 1-(6-Bromo-3-pyridyl)-2,2-difluoro-ethanol (5.3 g, 21.20 mmol, 63% yield) was obtained as a light yellow oil.

Step 4

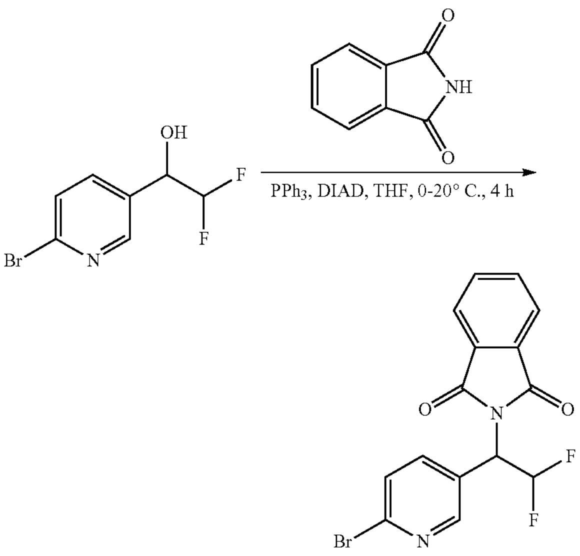

To a solution of 1-(6-bromo-3-pyridyl)-2,2-difluoro-ethanol (3.3 g, 13.86 mmol, 1 eq) and isoindoline-1,3-dione (2.45 g, 16.64 mmol, 1.2 eq) in tetrahydrofuran (30 mL) was added triphenylphosphine (4.36 g, 16.64 mmol, 1.2 eq) followed by, dropwise, diisopropyl azodicarboxylate (3.36 g, 16.64 mmol, 3.2 mL, 1.2 eq) in tetrahydrofuran (5 mL) under nitrogen at 0° C. The reaction mixture was stirred at 20° C. for 12 hours. The mixture was concentrated in vacuum. The residue was purified by silica gel chromatography (petroleum ether:ethyl acetate=1:0 to 5:1). 2-[1-(6-Bromo-3-pyridyl)-2,2-difluoro-ethyl]isoindoline-1,3-dione (2.8 g, 6.89 mmol, 49% yield) was obtained as a light yellow solid.

Step 5

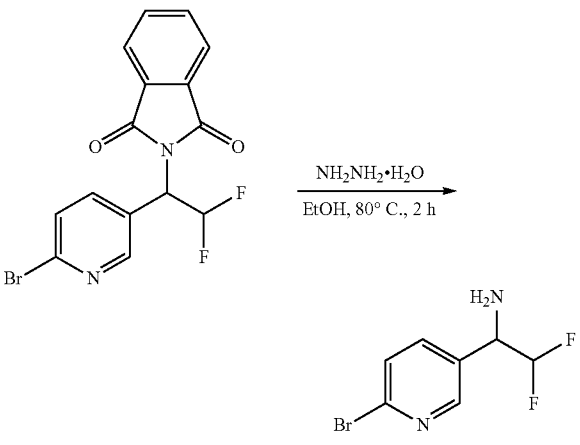

To a solution of 2-[1-(6-bromo-3-pyridyl)-2,2-difluoro-ethyl]isoindoline-1,3-dione (2 g, 5.45 mmol, 1 eq) in ethanol (20 mL) was added hydrazine hydrate (1.36 g, 27.24 mmol, 1.3 mL, 5 eq). The reaction mixture was stirred at 80° C. for 2 hours. Ethanol (30 mL) was added to the mixture, the mixture was filtered, and the filtrate was concentrated in vacuum. The residue was used in the next step directly. 1-(6-Bromo-3-pyridyl)-2,2-difluoro-ethanamine (1.2 g, crude) was obtained as a light yellow solid.

Step 6

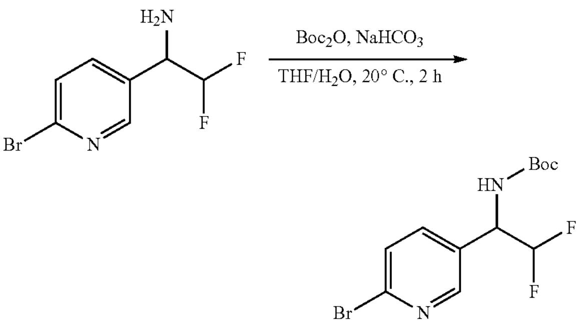

To a solution of 1-(6-bromo-3-pyridyl)-2,2-difluoro-ethanamine (1.2 g, 5.06 mmol, 1 eq) and sodium bicarbonate (850 mg, 10.12 mmol, 2 eq) in tetrahydrofuran (5 mL) and water (5 mL) was added di-tert-butyldicarbonate (2.21 g, 10.12 mmol, 2.3 mL, 2 eq). The reaction mixture was stirred at 20° C. for 2 hours. Water (100 mL) was added to the mixture, and the resulting mixture was extracted with ethyl acetate (50 mL×3). The combined organic phase was washed with brine (60 mL), dried over sodium sulfate, filtered and concentrated in vacuum. The residue was purified by silica gel chromatography (petroleum ether:ethyl acetate=3:1). The crude product was purified by preparative High Performance Liquid (column: Phenomenex Gemini C18 250*50 mm*10 um; mobile phase: [water (0.05% ammonia hydroxide v/v)-ACN]; B %: 40%-65%, 22 min). tert-Butyl N-[1-(6-bromo-3-pyridyl)-2,2-difluoro-ethyl]carbamate (1.4 g, 4.15 mmol, 82% yield) was obtained as a light yellow solid.

Step 7

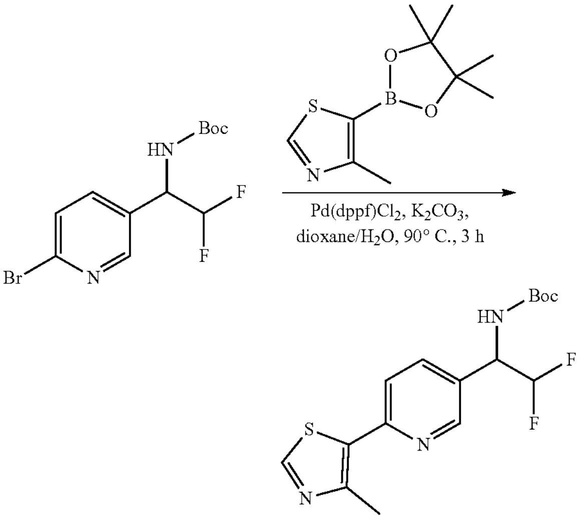

To a solution of tert-butyl N-[1-(6-bromo-3-pyridyl)-2,2-difluoro-ethyl]carbamate (2 g, 5.93 mmol, 1 eq), 4-methyl-5-(4,4,5,5-tetramethyl-1,3,2-dioxaborolan-2-yl)thiazole (3.34 g, 14.83 mmol, 2.5 eq) in dioxane (50 mL) and water (10 mL) was added potassium carbonate (2.05 g, 14.83 mmol, 2.5 eq) and (1,1'-bis(diphenylphosphino)ferrocene) palladium(II) dichloride (434 mg, 0.59 mmol, 0.1 eq) under nitrogen. The reaction mixture was stirred at 100° C. for 12 hours. Water (150 mL) was added to the mixture, and the resulting mixture was extracted with ethyl acetate (50 mL×3). The combined organic phase was washed with brine (80 mL), dried over sodium sulfate, filtered and concentrated in vacuum. The residue was purified by silica gel chromatography (petroleum ether:ethyl acetate=100:1 to 1:1). The residue was then additionally purified by preparative HPLC (column: Phenomenex Synergi C18 150*30 mm*4 um; mobile phase: [water (0.225% FA)-ACN]; B %: 35%-65%, 10 min). tert-Butyl N-[2,2-difluoro-1-[6-(4-methylthiazol-5-yl)-3-pyridyl]ethyl]carbamate (480 mg, 1.33 mmol, 22% yield) was obtained as a light yellow solid.

Step 8

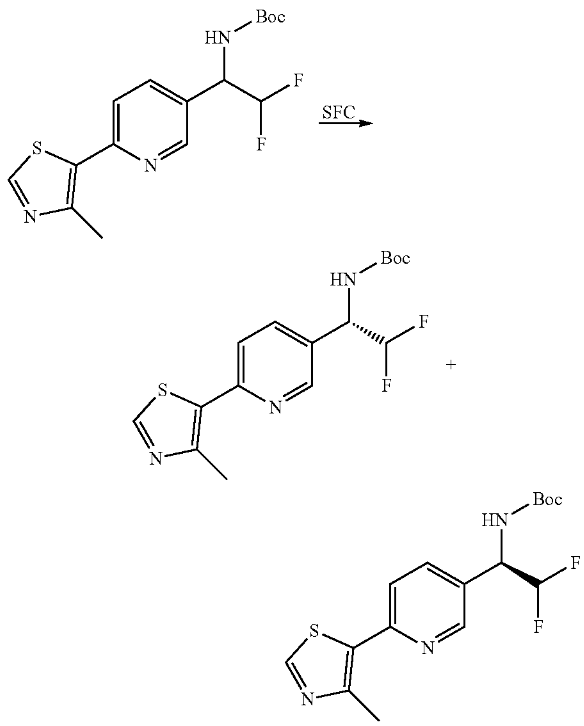

tert-Butyl N-[2,2-difluoro-1-[6-(4-methylthiazol-5-yl)-3-pyridyl]ethyl] carbamate (480 mg, 1.35 mmol, 1 eq) was purified by prep-SFC (SFC Column: DAICEL CHIRALPAK AY 250×50 mm, I.D., 10 um; Mobile phase: ethyl alcohol in C02 from 30% to 30%; Flow rate: 60 g/min; Wavelength: 220 nm). Isomer 1 (tentatively designated as tert-butyl N-[(1S)-2,2-difluoro-1-[6-(4-methylthiazol-5-yl)-3-pyridyl]ethyl] carbamate; 200 mg, 0.56 mmol, 82% yield) was obtained as a light yellow solid. Isomer 2 (tentatively designated as tert-butyl N-[(1R)-2,2-difluoro-1-[6-(4-methylthiazol-5-yl)-3-pyridyl] ethyl]carbamate; 210 mg, 0.59 mmol, 87% yield) was obtained as a light yellow solid.

Step 9

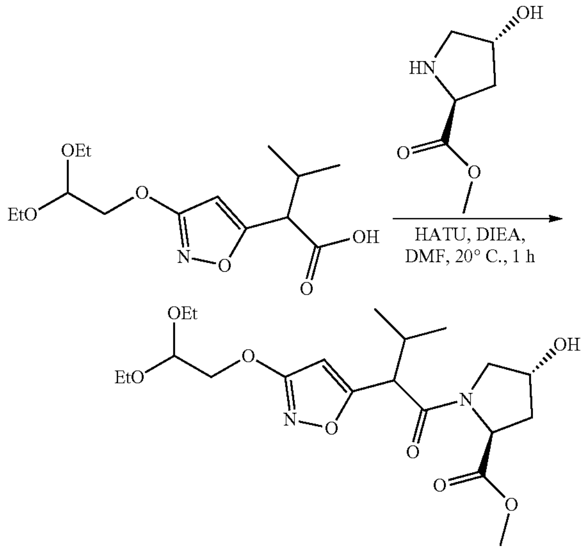

To a solution of 2-[3-(2,2-diethoxyethoxy)isoxazol-5-yl]-3-methyl-butanoic acid (400 mg, 1.33 mmol, 1 eq) and methyl (2S,4R)-4-hydroxypyrrolidine-2-carboxylate (241 mg, 1.33 mmol, 1 eq, hydrochloride) in N,N-dimethylformamide (5 mL) was added N,N-diisopropylethylamine (686 mg, 5.31 mmol, 0.9 mL, 4 eq) and O-(7-Azabenzotriazol-1-yl)-N,N,N',N'-tetramethyluronium hexafluorophosphate (605 mg, 1.59 mmol, 1.2 eq) at 0° C. The reaction mixture was stirred at 20° C. for 1 hour. Water (50 mL) was added to the mixture, and the resulting mixture was extracted with ethyl acetate (20 mL×3). The combined organic phase was washed with brine (30 mL×2), dried over sodium sulfate, filtered and concentrated in vacuum. The residue was purified by preparative HPLC (column: Phenomenex Synergi C18 150*25*10 um; mobile phase: [water (0.225% FA)-ACN]; B %: 36%-66%, 10 min). Methyl (2S,4R)-1-[2-[3-(2,2-diethoxyethoxy)isoxazol-5-yl]-3-methyl-butanoyl]-4-hydroxy-pyrrolidine-2-carboxylate (450 mg, 1.05 mmol, 78% yield) was obtained as a colorless oil.

Step 10

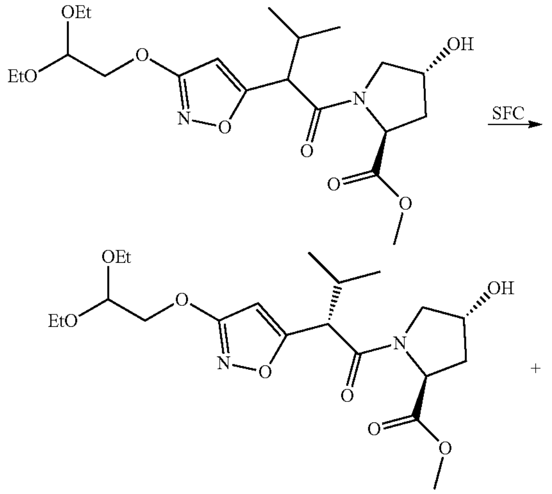

-continued

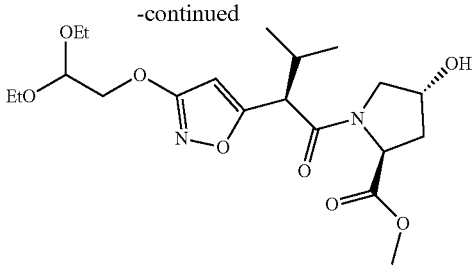

The mixture was purified by prep-SFC (SFC Column: DAICEL CHIRALPAK IC 250×30 mm, I.D., 10 um; Mobile phase: methanol (0.1% $NH_4OH$) in C02 from 30% to 30%; Flow rate: 50 g/min; Wavelength: 220 nm). Methyl (2S,4R)-1-[(2S)-2-[3-(2,2-diethoxyethoxy)isoxazol-5-yl]-3-methyl-butanoyl]-4-hydroxy-pyrrolidine-2-carboxylate (180 mg, 0.36 mmol, 69% yield) was obtained as a colorless oil. Methyl (2S,4R)-1-[(2R)-2-[3-(2,2-diethoxyethoxy)isoxazol-5-yl]-3-methyl-butanoyl]-4-hydroxy-pyrrolidine-2-carboxylate (220 mg, 0.51 mmol, 96% yield) was obtained as a colorless oil.

Methyl (2S,4R)-1-[(2R)-2-[3-(2,2-diethoxyethoxy)isoxazol-5-yl]-3-methyl-butanoyl]-4-hydroxy-pyrrolidine-2-carboxylate was converted to the final compound according to the scheme below using procedures analogous to those described above for other examples.

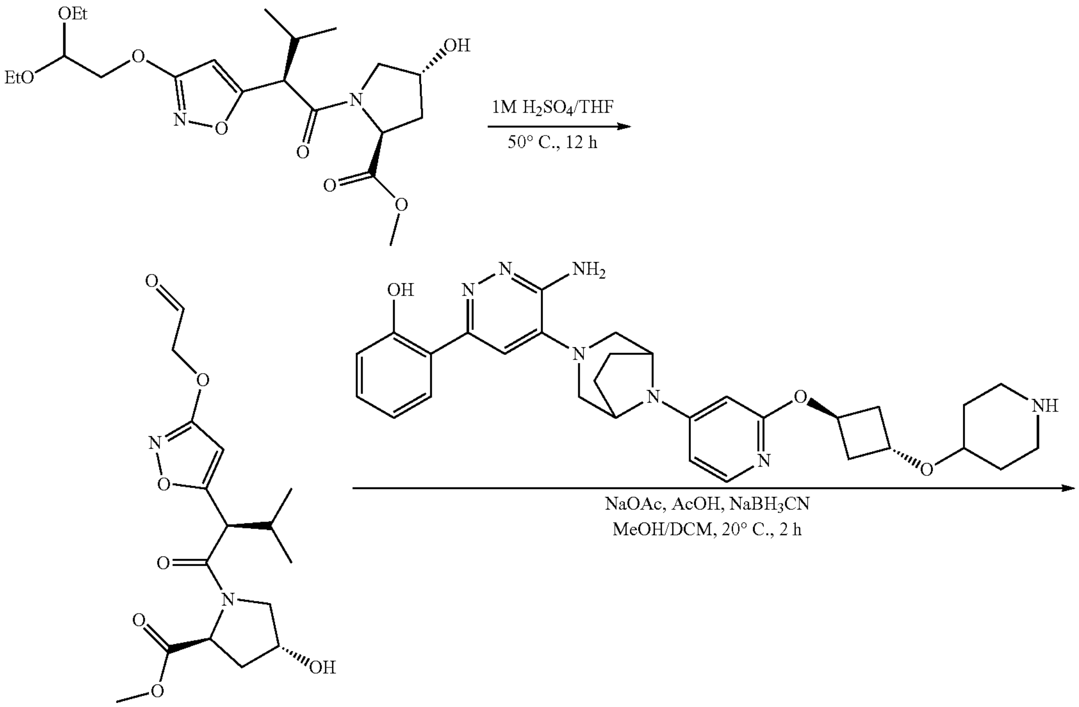

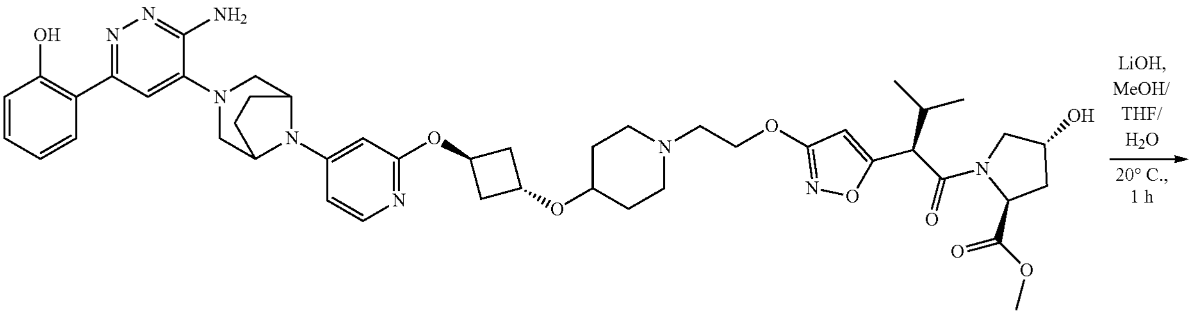

-continued
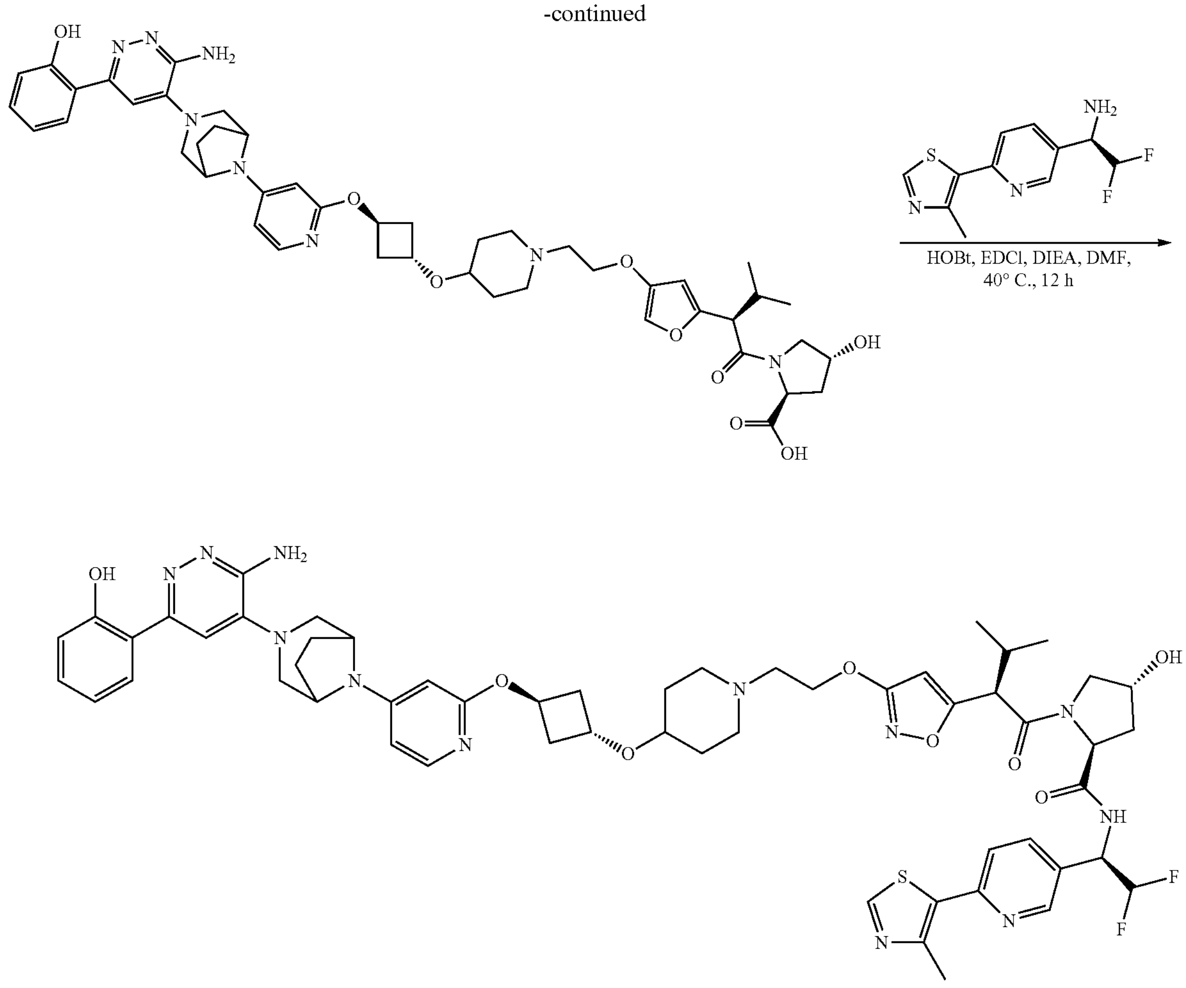
Ex. 244
Exemplary compound 243 was prepared using analogous procedures.
Exemplary Synthesis of Exemplary Compound 246
Ex. 246
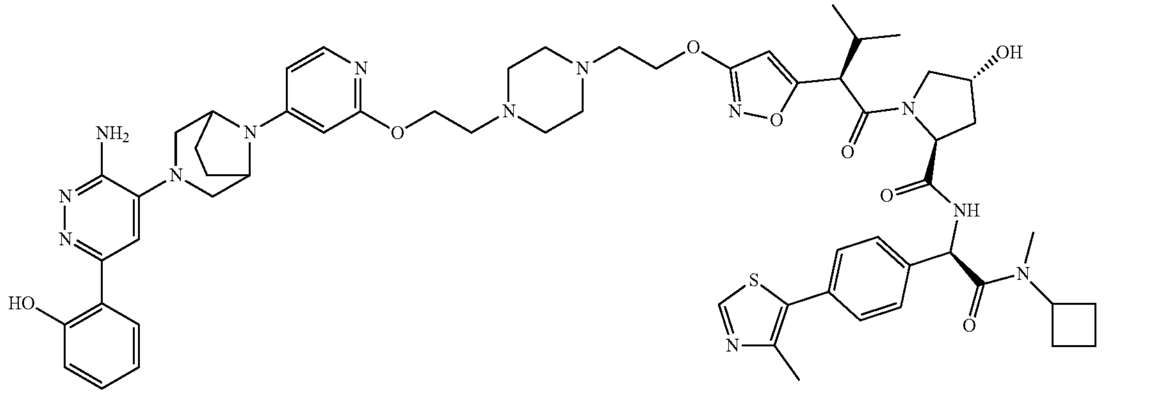

Step 1

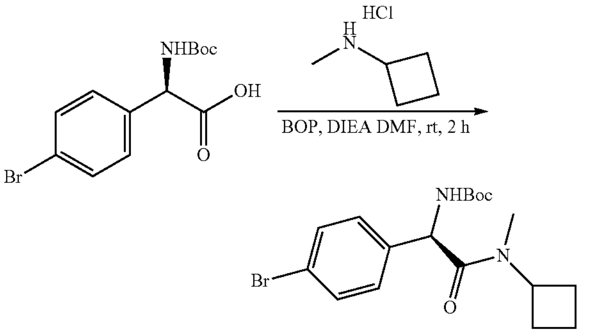

Into a 50-mL round-bottom flask, was placed (2R)-2-(4-bromophenyl)-2-[[(tert-butoxy)carbonyl]amino]acetic acid (1 g, 3.029 mmol, 1 equiv) in DMF (15 mL), to which was added diisopropylethylamine (1.57 g, 12.115 mmol, 4 equiv), N-methylcyclobutanamine hydrochloride (368 mg, 3.03 mmol, 1 equiv), and BOP (1.61 g, 3.63 mmol, 1.2 equiv) in sequence. The resulting solution was stirred for 2 hours at room temperature. The reaction was then quenched by the addition of water (10 mL). The resulting mixture was extracted with ethyl acetate (4x30 mL), and the combined organic layer was washed with brine (2x10 mL), dried over anhydrous sodium sulfate and concentrated. The residue was applied onto a silica gel column eluting with ethyl acetate/petroleum ether (1/1). This resulted in 1.1 g (91%) of tert-Butyl N—[(R)-(4-bromophenyl)[cyclobutyl(methyl)carbamoyl]methyl]carbamate as a yellow solid.

-continued

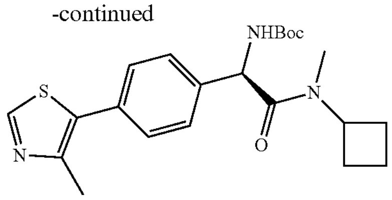

Into a 100-mL round-bottom flask, was placed tert-butyl N—[(R)-(4-bromophenyl) [cyclobutyl(methyl)carbamoyl]methyl]carbamate (1 g, 2.52 mmol, 1 equiv), $K_2CO_3$ (1.04 g, 7.55 mmol, 3 equiv), 4-methyl-5-(4,4,5,5-tetramethyl-1,3,2-dioxaborolan-2-yl)-1,3-thiazole (850 mg, 3.78 mmol, 1.5 equiv), and Pd(dppf)C12 (184 mg, 0.25 mmol, 0.1 equiv) in dioxane (10 mL) and $H_2O$ (2 mL) under nitrogen atmosphere. The resulting mixture was stirred for 3 hours at 90° C. in an oil bath under nitrogen atmosphere. The mixture was concentrated, and the residue was applied onto a silica gel column eluting with ethyl acetate/petroleum ether (1/1). This resulted in 480 mg (46%) of tert-butyl N—[(R)-[cyclobutyl(methyl)carbamoyl][4-(4-methyl-1,3-thiazol-5-yl)phenyl]methyl]carbamate as a yellow solid.

tert-Butyl N—[(R)-[cyclobutyl(methyl)carbamoyl] [4-(4-methyl-1,3-thiazol-5-yl)phenyl]methyl]carbamate was converted to the final compound using procedures analogous to those described above for other examples.

Exemplary compound 245 was prepared using analogous procedures.

Exemplary Synthesis of Exemplary Compound 248

Ex. 248

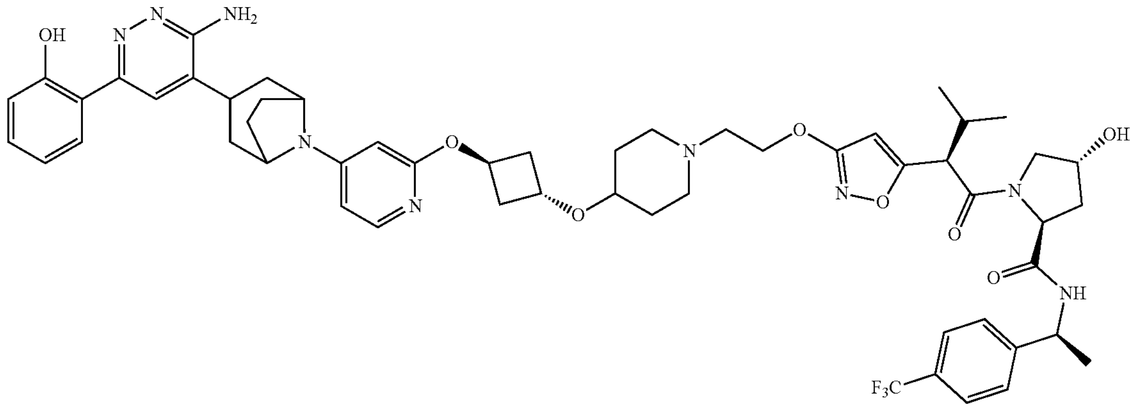

Step 2

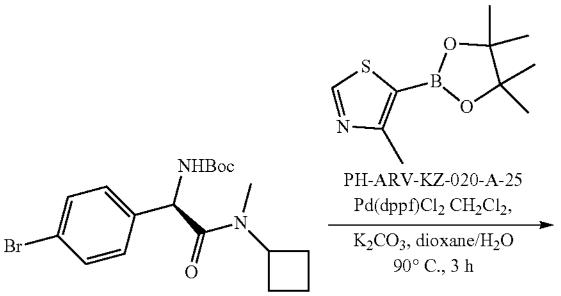

Step 1

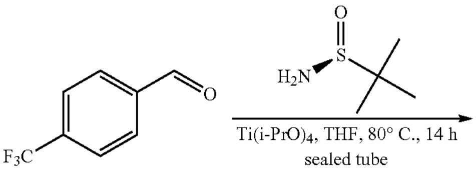

-continued

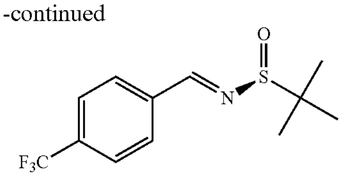

Into a 250-mL round-bottom flask, was placed a solution of 4-(trifluoromethyl)benzaldehyde (3.0 g, 17.2 mmol, 1.0 equiv), (S)-2-methylpropane-2-sulfinamide (4.2 g, 0.035 mmol, 2.0 equiv), and titanium isopropoxide (14.9 g, 0.052 mmol, 3.0 equiv) in THF (50 mL). The resulting solution was stirred for 16 hours at 80° C. in an oil bath. The reaction was then quenched by the addition of 200 mL water, and the mixture was extracted with ethyl acetate (100 mL×3). The combined organic phase was washed with brine, dried over sodium sulfate and concentrated under reduced pressure. The residue was applied onto a silica gel column eluting with ethyl acetate/petroleum ether (1:1). This resulted in 3.1 g (65%) of (S)-2-methyl-N-[[4-(trifluoromethyl)phenyl]methylidene]propane-2-sulfinamide as a yellow oil.

Step 2

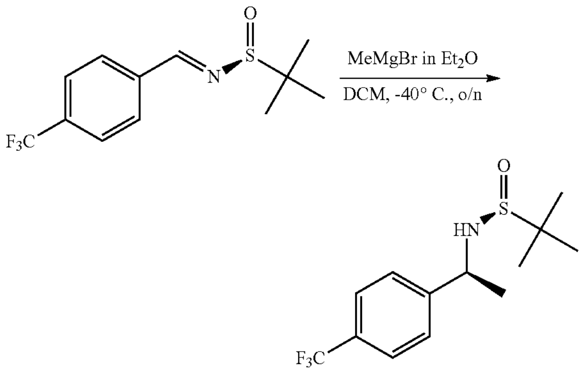

To a solution of (S)-2-methyl-N-[[4-(trifluoromethyl)phenyl]methylidene]propane-2-sulfinamide (3.1 g, 11.2 mmol, 1.0 equiv) in DCM (20 mL) was added methylmagnesium chloride solution (3.0 M in ether, 5 mL) dropwise over 20 minutes period at −48° C. under nitrogen atmosphere. The resulting mixture was then stirred for 2 hours at room temperature. The reaction mixture was then quenched by the addition of 50 mL saturated $NH_4Cl$ solution and extracted with dichloromethane (50 mL×3). The combined organic phase was washed with brine, dried over sodium sulfate and concentrated under reduced pressure. The residue was applied onto a silica gel column eluting with ethyl acetate/petroleum ether (1:1). This resulted in 1.83 g (56%) of (S)-2-methyl-N-[(1S)-1-[4-(trifluoromethyl)phenyl]ethyl]propane-2-sulfinamide as a white solid.

Step 3

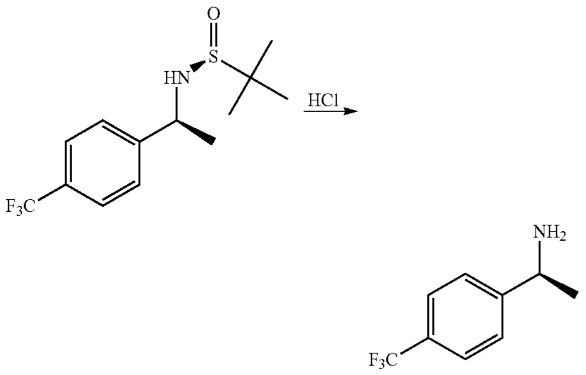

Into a 100 mL round-bottom flask, was placed (S)-2-methyl-N-[(1S)-1-[4-(trifluoromethyl) phenyl]ethyl]propane-2-sulfinamide (1.8 g, 6.2 mmol, 1.0 equiv) in methanol (10 mL). This was followed by the addition of hydrogen chloride aqueous solution (37%, 5 mL). The resulting solution was stirred for 2 hours at room temperature, and then was concentrated under reduced pressure. This resulted in 970 mg (82%) of (1S)-1-[4-(trifluoromethyl)phenyl]ethan-1-amine as a white solid.

(1S)-1-[4-(trifluoromethyl)phenyl]ethan-1-amine was converted to the final compound using procedures analogous to those described above for other examples.

Example compound 247 was prepared using analogous procedures.

Exemplary Synthesis of Exemplary Compound 404

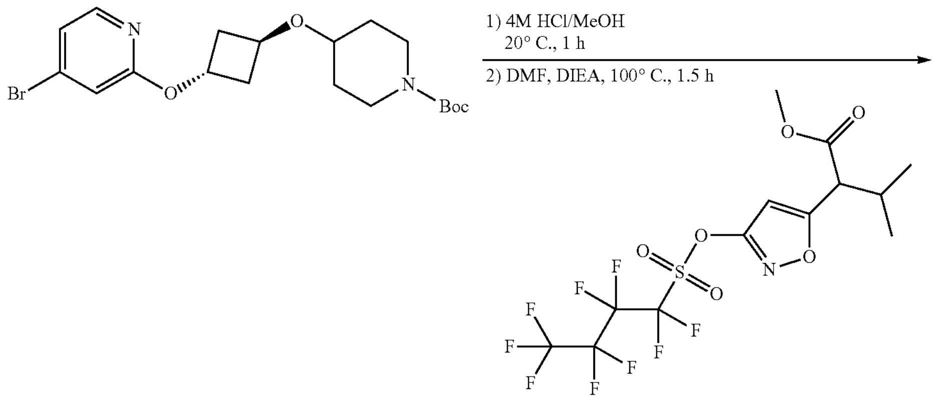

-continued
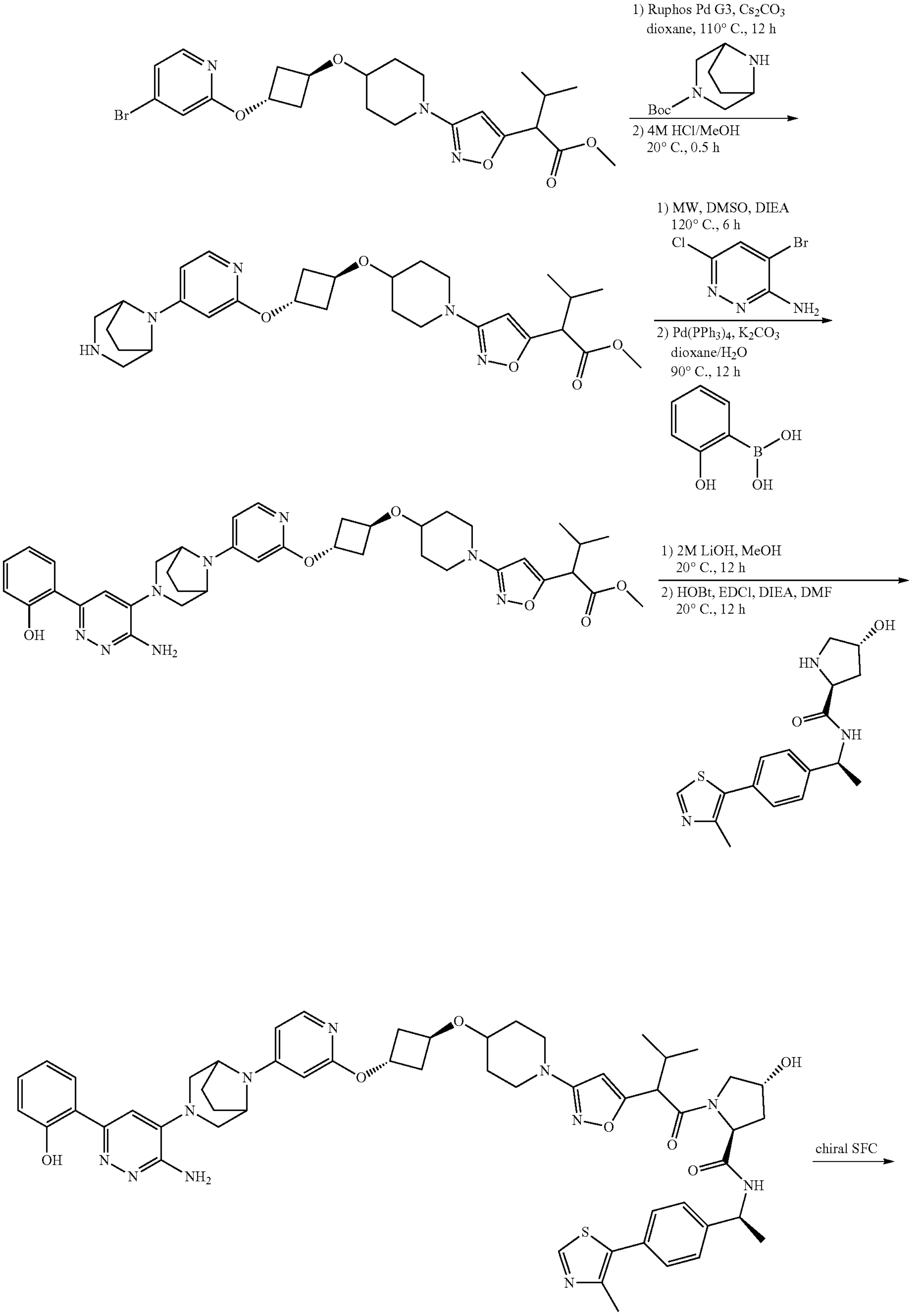

-continued

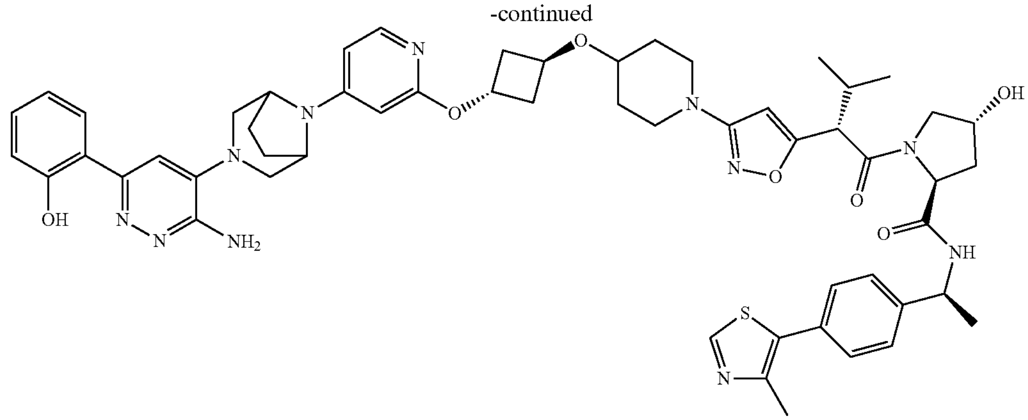

+

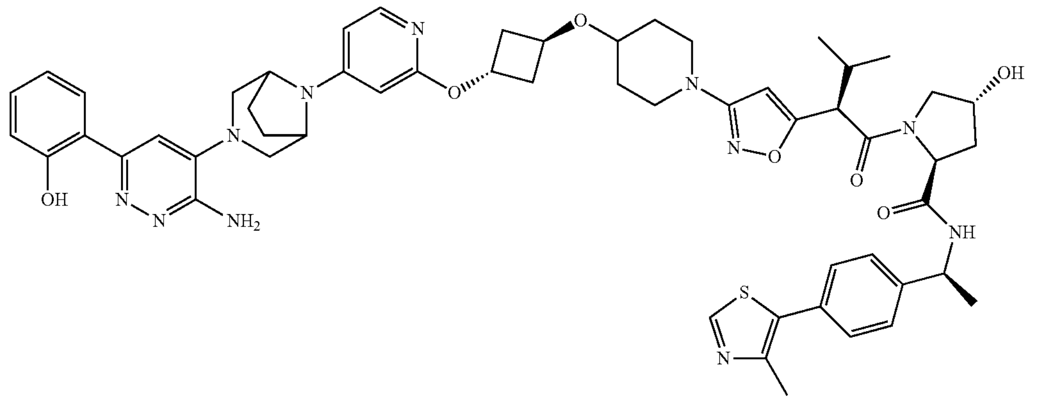

As shown in the scheme above, tert-butyl 4-((1R,3R)-3-((4-bromopyridin-2-yl)oxy)cyclobutoxy)piperidine-1-carboxylate was deprotected under acidic conditions, and the resulting free cyclic amine reacted with the activated isoxazole derivative to form methyl 3-methyl-2-(3-(((perfluorobutyl)sulfonyl)oxy)isoxazol-5-yl)butanoate as a coupling product. A palladium catalyzed reaction of the pyridyl bromide fragment in the product with tert-butyl 3,8-diazabicyclo[3.2.1]octane-3-carboxylate followed by the cleavage of the tert-butyloxycarbonyl (Boc) protecting group yielded a free amine, which underwent a nucleophilic coupling reaction with 4-bromo-6-chloropyridazin-3-amine under heating in DMSO in the presence of an amine. A Suzuki coupling reaction of the pyridazine bromide with (2-hydroxyphenyl)boronic acid completed the assembly of the PTM binding moiety. Ester hydrolysis followed by condensation with (2S,4R)-4-hydroxy-N—((S)-1-(4-(4-methylthiazol-5-yl)phenyl)ethyl)pyrrolidine-2-carboxamide furnished the desired final product as a mixture of diastereomers, which were separated by supercritical fluid chromatography (SFC).

Exemplary Synthesis of Exemplary Compound 411

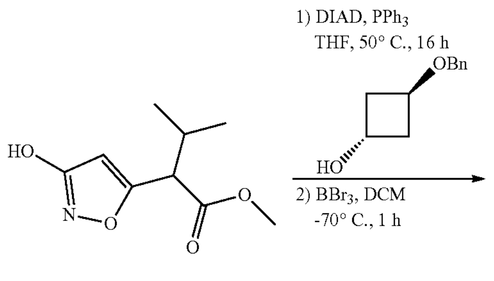

-continued

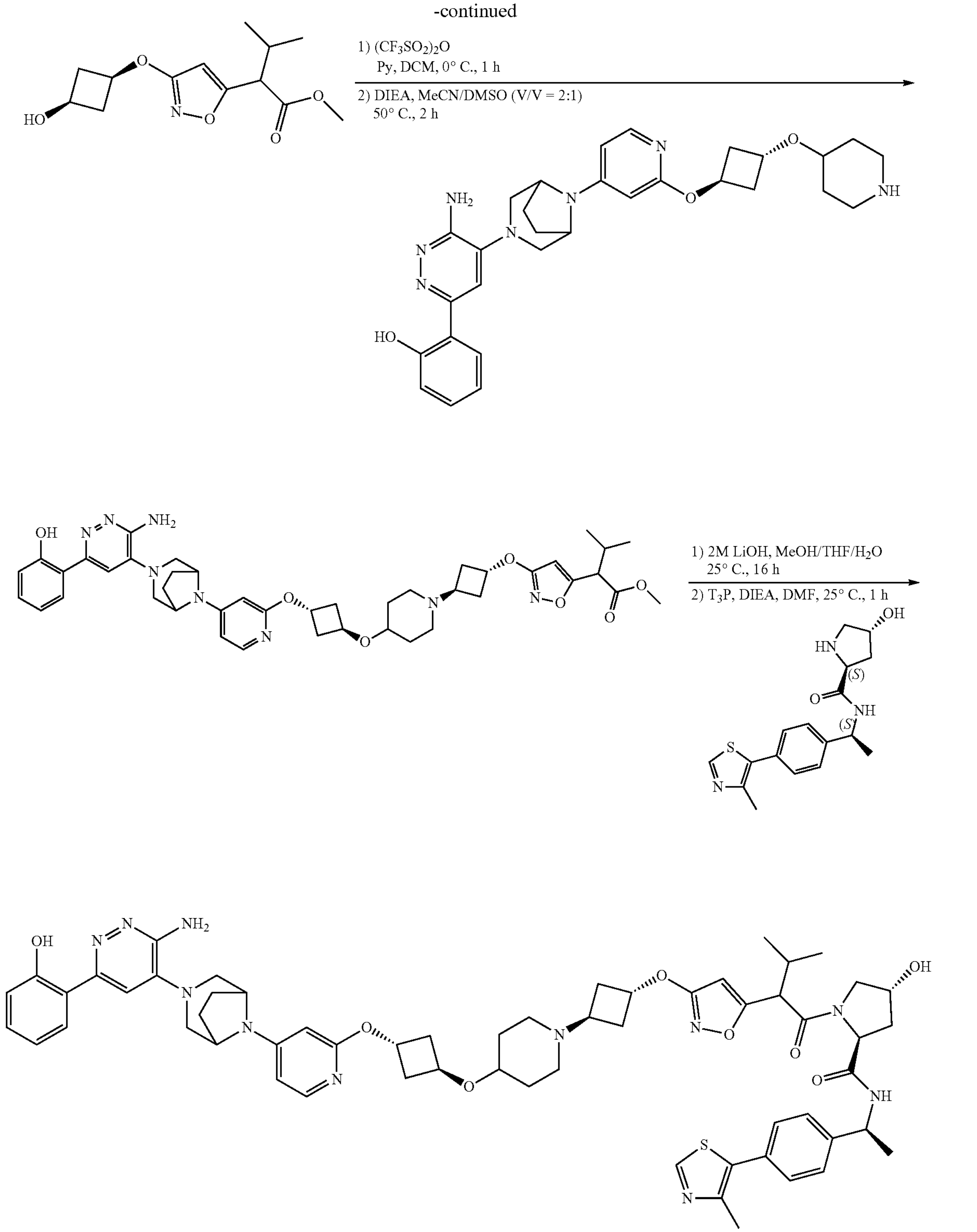

As shown in the scheme above, a Mitsunobu reaction between methyl 2-(3-hydroxyisoxazol-5-yl)-3-methylbutanoate and (1R,3R)-3-(benzyloxy)cyclobutanol followed by the benzyloxy group cleavage provided methyl 2-(3-((1S,3S)-3-hydroxycyclobutoxy)isoxazol-5-yl)-3-methylbutanoate. Activation of the hydroxyl group with triflic anhydride followed by the triflate displacement with the cyclic amine including the $W_{PTM5}$-$W_{PTM3}$-$W_{PTM2}$-$W_{PTM1}$ fragment afforded the coupling product which included the linking group L. Ester hydrolysis followed by condensation with (2S,4R)-4-hydroxy-N—((S)-1-(4-(4-methylthiazol-5-yl)phenyl)ethyl)pyrrolidine-2-carboxamide furnished the desired final product.

Exemplary Synthesis of Exemplary Compound 428

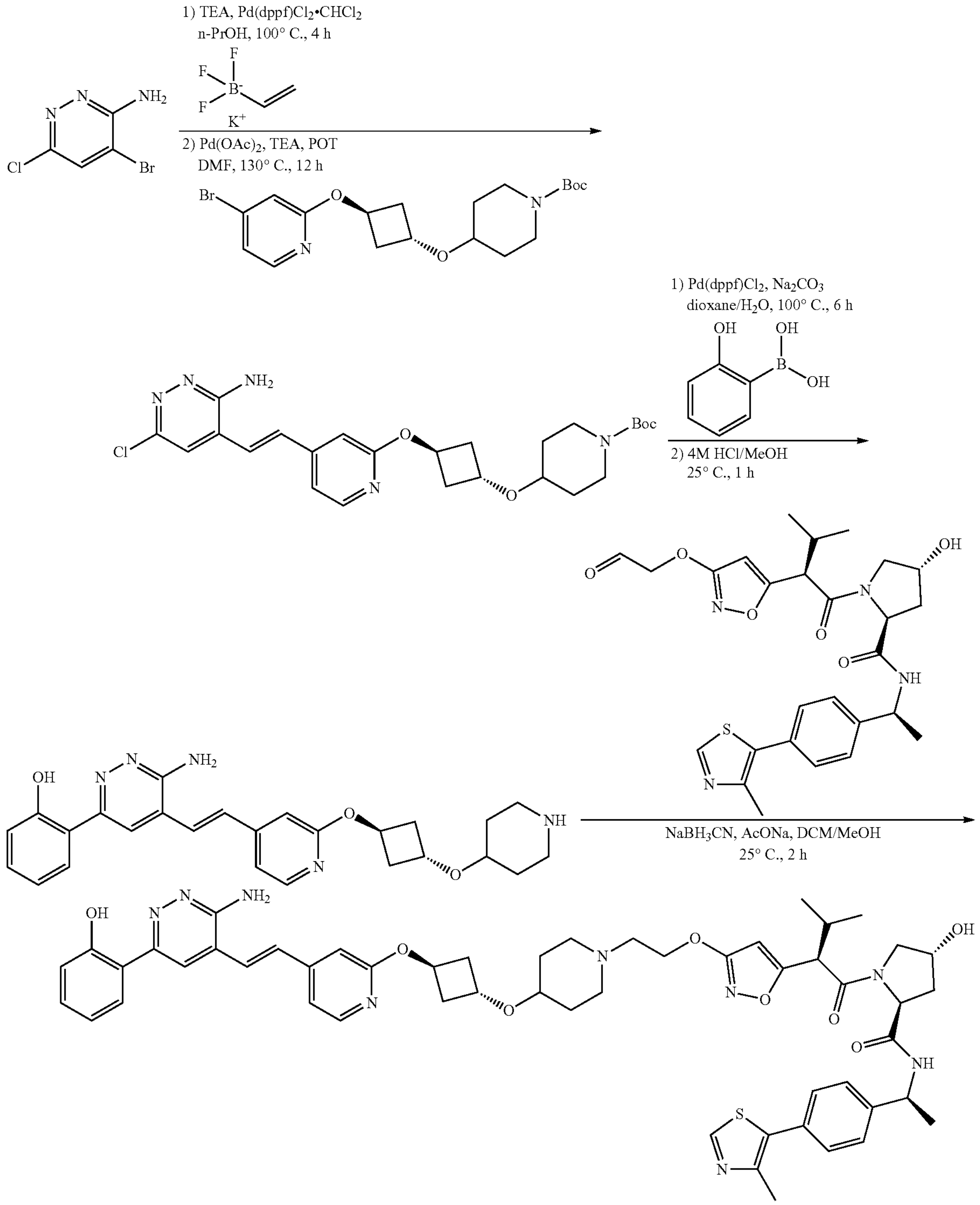

As shown in the scheme above, 4-bromo-6-chloro-pyridazin-3-amine was converted to a 4-vinyl derivative, which underwent a Heck coupling reaction with tert-butyl 4-((1R,3R)-3-((4-bromopyridin-2-yl)oxy)cyclobutoxy)piperidine-1-carboxylate to produce a coupling product. The 6-chloropyridazine moiety in the product then reacted with (2-hydroxyphenyl)boronic acid under Suzuki conditions to assemble the $W_{PTM5}$-$W_{PTM3}$ fragment. Subsequent Boc-deprotection followed by a reductive amination with (2S, 4R)-4-hydroxy-1-((R)-3-methyl-2-(3-(2-oxoethoxy)isoxazol-5-yl)butanoyl)-N—((S)-1-(4-(4-methylthiazol-5-yl)phenyl)ethyl)pyrrolidine-2-carboxamide provided the desired final product.

Exemplary Synthesis of Exemplary Compound 445
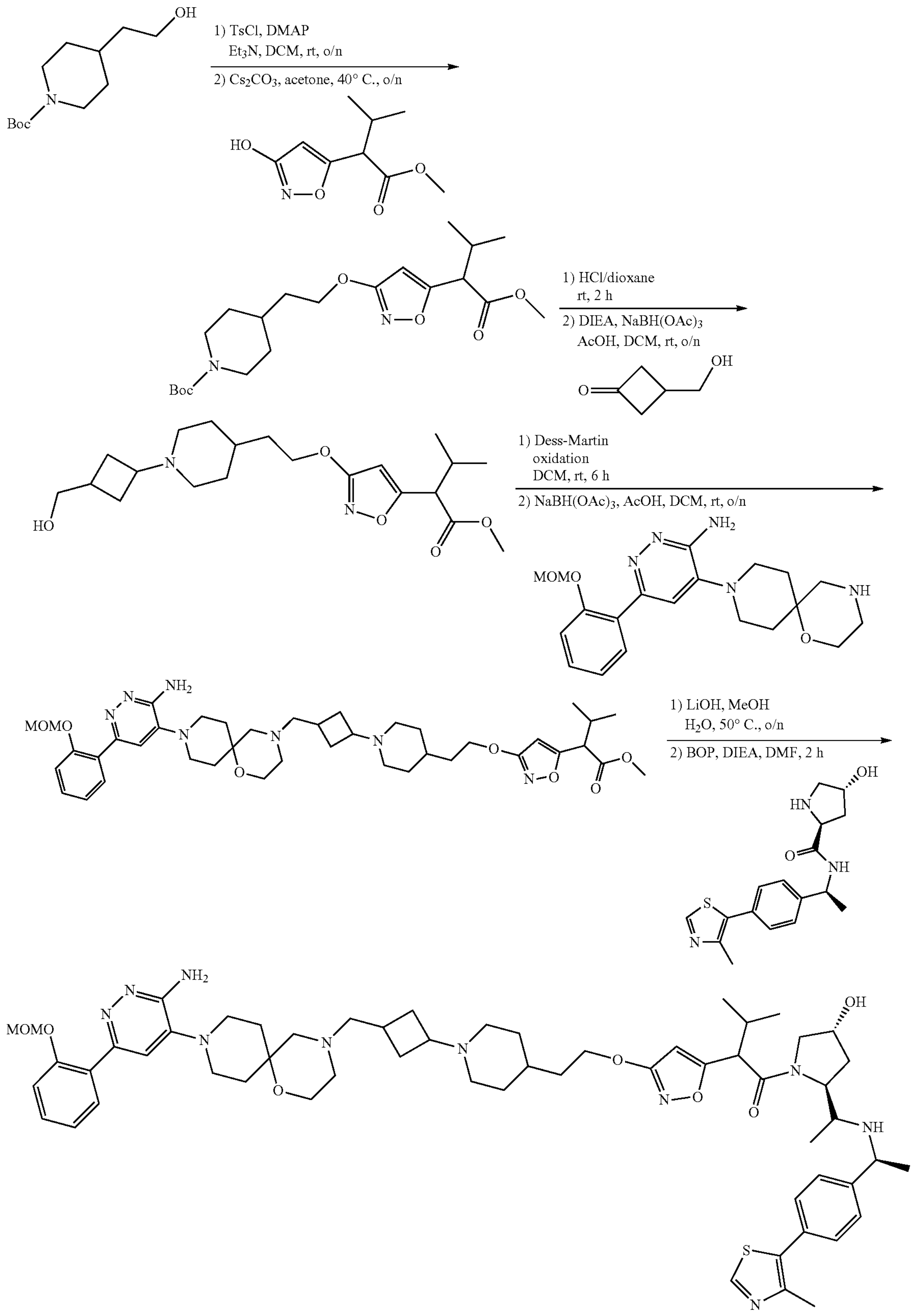

As shown in the scheme above, the hydroxyl group in tert-butyl 4-(2-hydroxyethyl)piperidine-1-carboxylate was activated with tosyl chloride, and the resulting tosylate underwent nucleophilic displacement with methyl 2-(3-hydroxyisoxazol-5-yl)-3-methylbutanoate. The Boc-group in the product was cleaved and the free cyclic amine reacted with 3-(hydroxymethyl)cyclobutanone and sodium triacetoxyborohydride to form methyl 2-(3-(2-(1-(3-(hydroxymethyl)cyclobutyl)piperidin-4-yl)ethoxy)isoxazol5-yl)-3-methylbutanoate. Dess-Martin oxidation of the hydroxyl group followed reductive amination of the resulting aldehyde with a spiro-amine gave a coupling product which combined the PTM binding moiety and the linking group L. Ester hydrolysis followed by condensation with (2S,4R)-4-hydroxy-N—((S)-1-(4-(4-methylthiazol-5-yl)phenyl)ethyl) pyrrolidine-2-carboxamide furnished the desired final product.

Exemplary Synthesis of Exemplary Compound 449-456

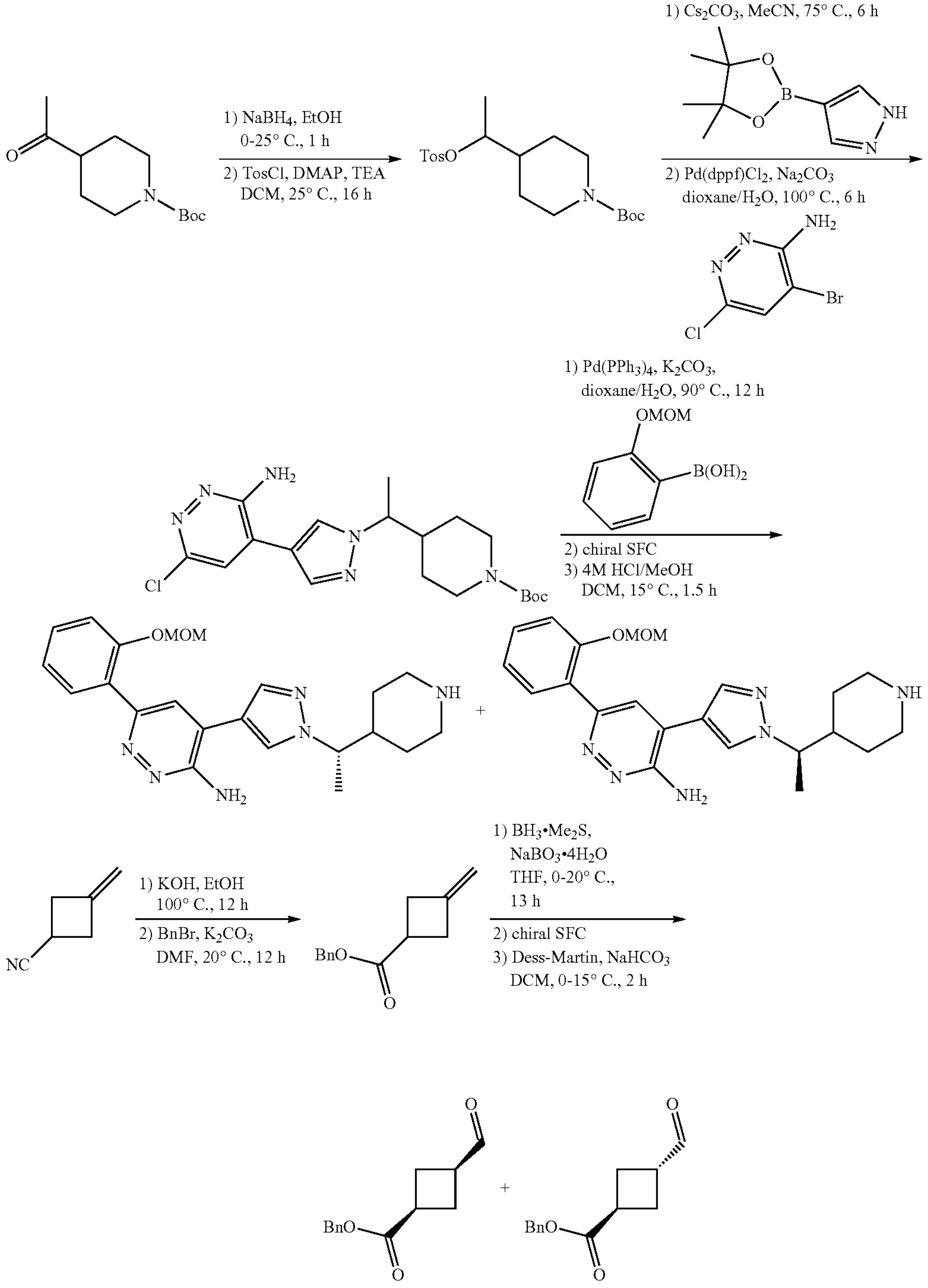

-continued

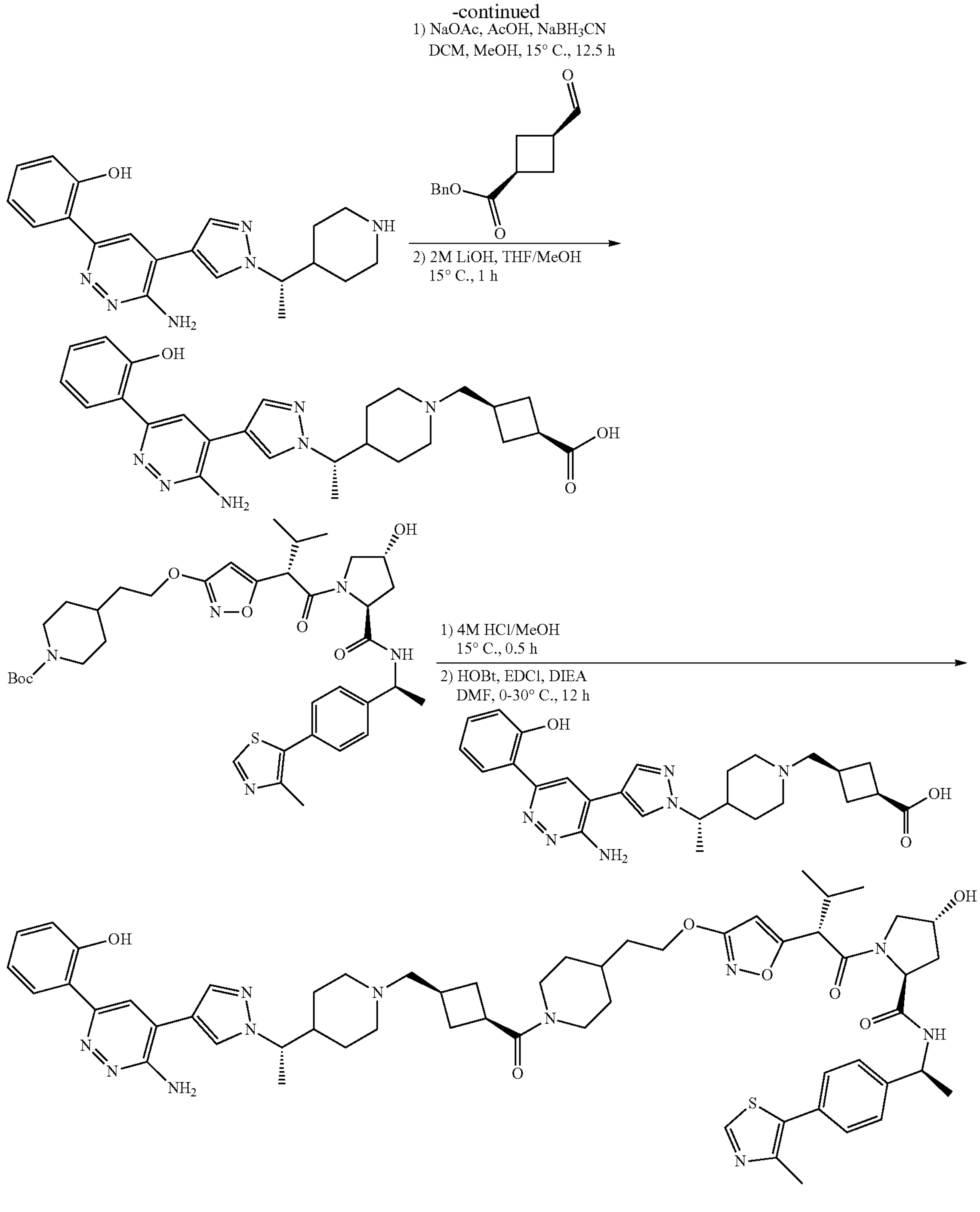

As shown in the scheme above, the assembly of the first coupling fragment started with tert-butyl 4-acetylpiperidine-1-carboxylate, which was reduced to the alcohol and converted to the tosylate. The tosyl group was displaced with 4-(4,4,5,5-tetramethyl-1,3,2-dioxaborolan-2-yl)-1H-pyrazole, and the product was coupled with 4-bromo-6-chloropyridazin-3-amine under Suzuki conditions to afford a racemic mixture of tert-butyl 4-(1-(4-(3-amino-6-(2-(methoxymethoxy)phenyl)pyridazin-4-yl)-1H-pyrazol-1-yl)ethyl)piperidine-1-carboxylates, which were separated by using chiral supercritical fluid chromatography (SFC). Subsequent Boc-deprotection provided the desired first coupling fragments in enantiomerically pure state.

The formation of the second coupling fragment started with 3-methylenecyclobutanecarbonitrile, which was hydrolyzed to the carboxylic acid and protected as a benzyl ester. Hydroboration of the endo-double bond followed by oxidation provided a diastereomeric mixture of alcohols, which was separated by using supercritical fluid chromatography (SFC). The individual alcohols were oxidized with a Dess-Martin periodinane to provide the desired isomeric aldehydes.

Reductive amination of the first and second coupling fragments with sodium borohydride followed by basic hydrolysis afforded (1R,3S)-3-((4-((S)-1-(4-(3-amino-6-(2-hydroxyphenyl)pyridazin-4-yl)-1H-pyrazol-1-yl)ethyl)piperidin-1-yl)methyl)cyclobutanecarboxylic acid, which underwent condensation with (2S,4R)-4-hydroxy-1-((S)-3-methyl-2-(3-(2-(piperidin-4-yl)ethoxy)isoxazol-5-yl)butanoyl)-N—((S)-1-(4-(4-methylthiazol-5-yl)phenyl)ethyl) pyrrolidine-2-carboxamide to provide the desired product. This method can be conveniently used to synthesize all enantiomerically pure isomers of the desired product by implementing reagents and intermediates having appropriate stereochemistry.

Exemplary Synthesis of Exemplary Compound 458

As shown in the scheme above, tert-butyl 4-formylpiperidine-1-carboxylate underwent reductive amination with (2S,4R)-4-hydroxy-1-((S)-3-methyl-2-(3-(piperazin-1-yl) isoxazol-5-yl)butanoyl)-N—((S)-1-(4-(4-methylthiazol-5-yl)phenyl)ethyl)pyrrolidine-2-carboxamide and sodium cyanoborohydride to produce (2S,4R)-4-hydroxy-1-((S)-3-methyl-2-(3-(4-(piperidin-4-ylmethyl)piperazin-1-yl) isoxazol-5-yl)butanoyl)-N—((S)-1-(4-(4-methylthiazol-5-yl)phenyl)ethyl)pyrrolidine-2-carboxamide after Boc-deprotection. Subsequent reductive amination of the resulting compound with (1R,3R)-3-((4-(3-(3-amino-6-(2-hydroxyphenyl)pyridazin-4-yl)-3,8-diazabicyclo[3.2.1]oc-

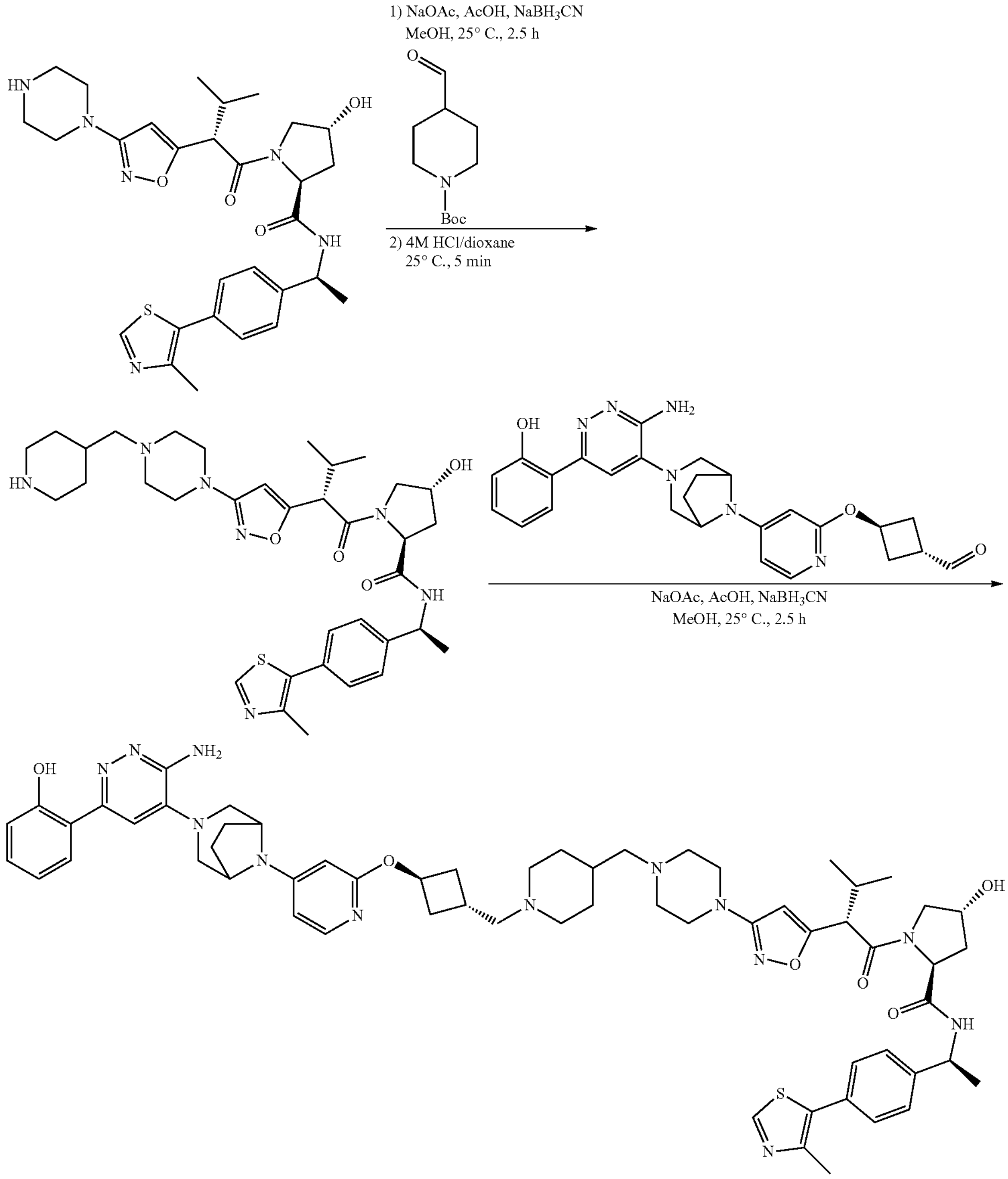

tan-8-yl)pyridin-2-yl)oxy)cyclobutanecarbaldehyde under similar conditions provided the desired final product.
Exemplary Synthesis of Exemplary Compound 474
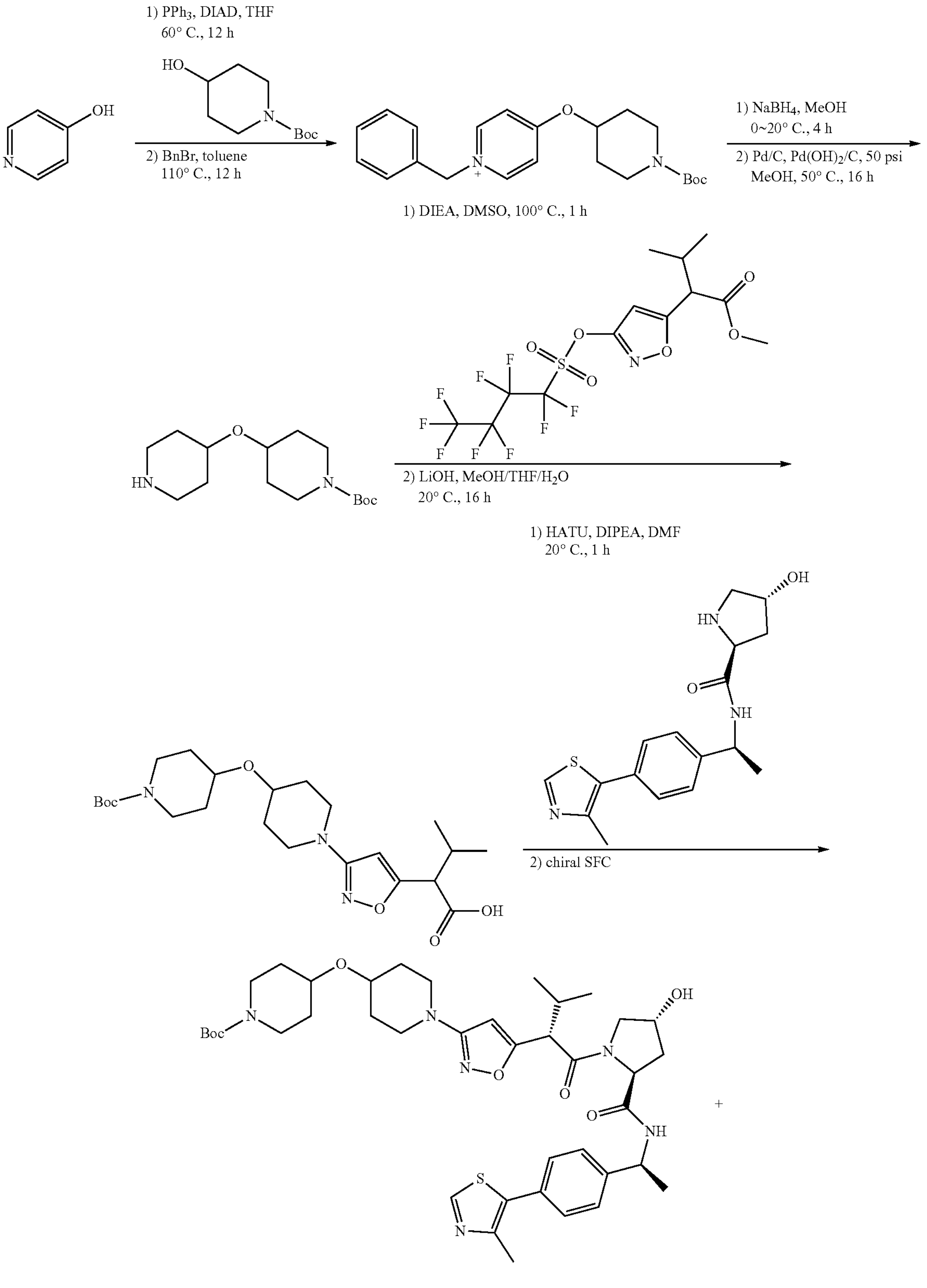

-continued

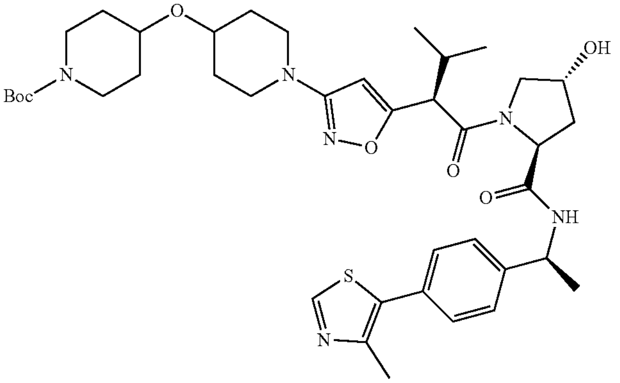 [SMILES: Cc1ncsc1-c1ccc([C@H](C)NC(=O)[C@@H]2C[C@@H](O)CN2C(=O)[C@@H](c2cc(N3CCC(OC4CCN(C(=O)OC(C)(C)C)CC4)CC3)no2)C(C)C)cc1]

As shown in the scheme above, a Mitsunobu reaction between 4-hydroxypyridine and tert-butyl 4-hydroxypiperidine-1-carboxylate provided tert-butyl 4-(pyridin-4-yloxy) piperidine-1-carboxylate, which was converted to a salt by alkylation of the pyridine nitrogen with benzyl bromide. The pyridine ring was subsequently reduced by a two-step procedure to form the double piperidine derivative, which reacted with methyl 3-methyl-2-(3-(((perfluorobutyl)sulfonyl)oxy)isoxazol-5-yl)butanoate under heteroaromatic nucleophilic substitution conditions to form a coupling product. Ester hydrolysis followed by condensation of the resulting acid with (2S,4R)-4-hydroxy-N—((S)-1-(4-(4-methythiazol-5-yl)phenyl)ethyl)pyrrolidine-2-carboxamide provided a diastereomeric final products, which were separated by supercritical fluid chromatography (SFC).

Exemplary Synthesis of Exemplary Compound 494, 495

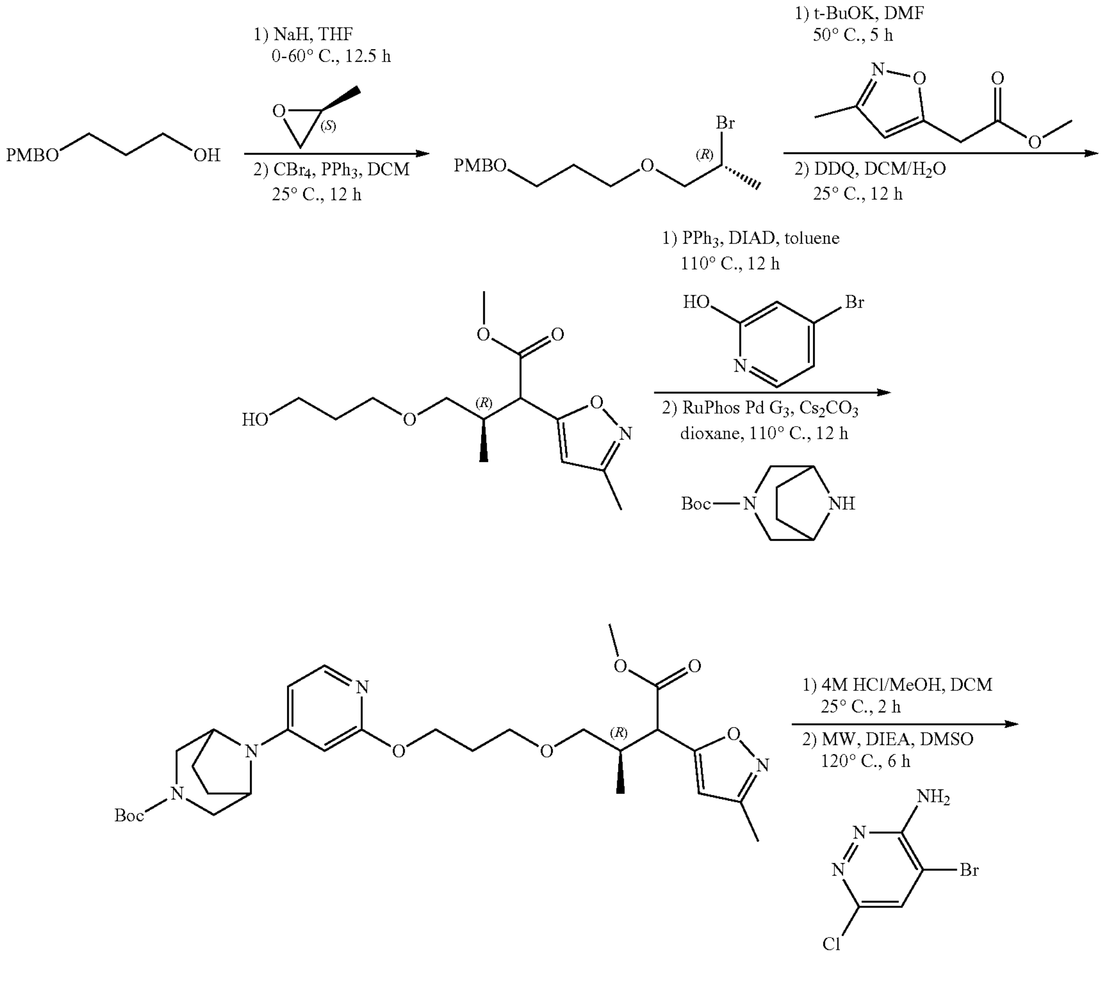

-continued
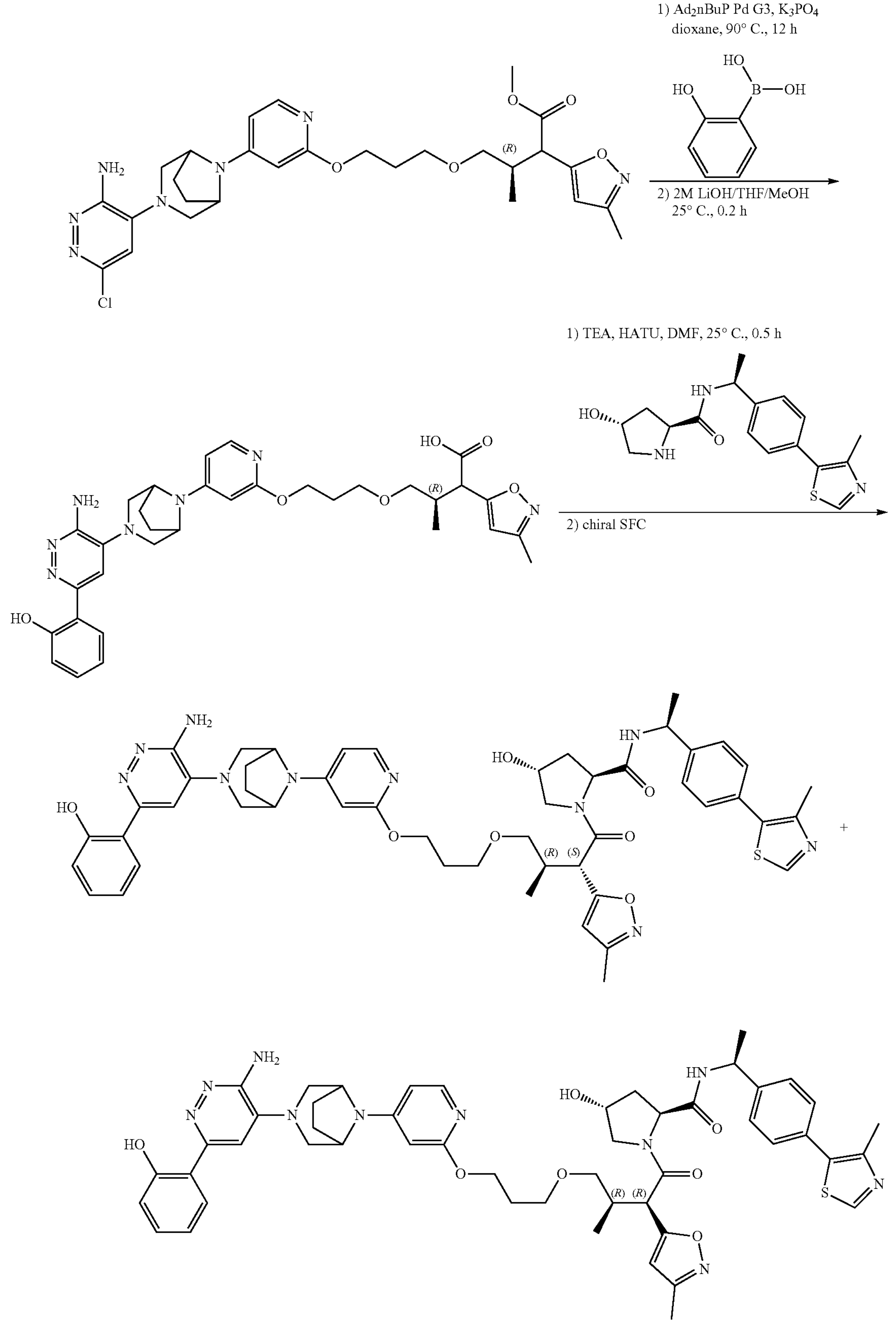

As shown in the scheme above, the synthesis of the PTM binding moiety started with 3-((4-methoxybenzyl)oxy)propan-1-ol which was treated with sodium hydride to open (S)-2-methyloxirane. Bromination of the resulting alcohol followed by bromide displacement with the enolate derived from methyl 2-(3-methylisoxazol-5-yl)acetate provided (3R)-methyl 4-(3-hydroxypropoxy)-3-methyl-2-(3-methylisoxazol-5-yl)butanoate. A Mitsunobu reaction of the product with 4-bromopyridin-2-ol followed by a palladium-catalyzed coupling of the pyridyl bromide moiety with mono-Boc-protected 3,8-diazabicyclo[3.2.1]octane afforded tert-butyl 8-(2-(3-((2R)-4-methoxy-2-methyl-3-(3-methylisoxazol-5-yl)-4-oxobutoxy)propoxy)pyridin-4-yl)-3,8-diazabicyclo[3.2.1]octane-3-carboxylate. Subsequent Boc-group cleavage provided a free amine, which underwent a nucleophilic coupling reaction with 4-bromo-6-chloropyridazin-3-amine by heating in the aprotic bipolar solvent (DMSO) in the presence of the amine (DIEA). A Suzuki coupling reaction of the pyridazine bromide with (2-hydroxyphenyl)boronic acid completed the assembly of the PTM binding moiety. Ester hydrolysis followed by condensation with (2S,4R)-4-hydroxy-N—((S)-1-(4-(4-methylthiazol-5-yl)phenyl)ethyl)pyrrolidine-2-carboxamide furnished the desired final product as a mixture of diastereomers, which were separated by supercritical fluid chromatography (SFC).

Exemplary Synthesis of Exemplary Compound 496, 497

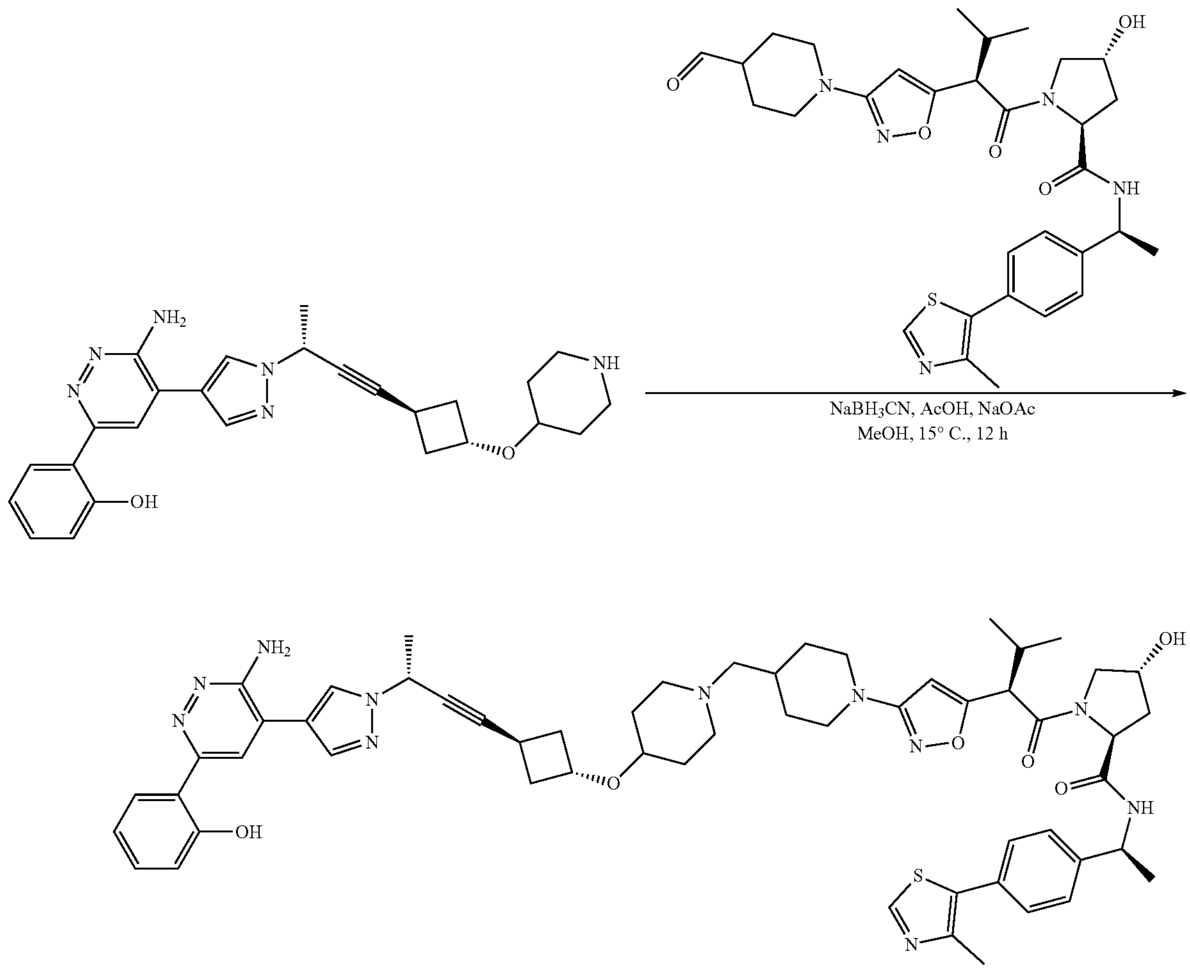

As shown in the scheme above, the desired product was obtained by a reductive amination of (2S,4R)-1-((R)-2-(3-(4-formylpiperidin-1-yl)isoxazol-5-yl)-3-methylbutanoyl)-4-hydroxy-N—((S)-1-(4-(4-methylthiazol-5-yl)phenyl)ethyl)pyrrolidine-2-carboxamide with 2-(6-amino-5-(1-((R)-4-((1r,3R)-3-(piperidin-4-yloxy)cyclobutyl)but-3-yn-2-yl)-1H-pyrazol-4-yl)pyridazin-3-yl)phenol in the presence of sodium cyanoborohydride. This method can be conveniently used to synthesize all enantiomerically pure isomers of the desired product by implementing the coupling counterparts having appropriate stereochemistry.

Exemplary Synthesis of Exemplary Compound 499
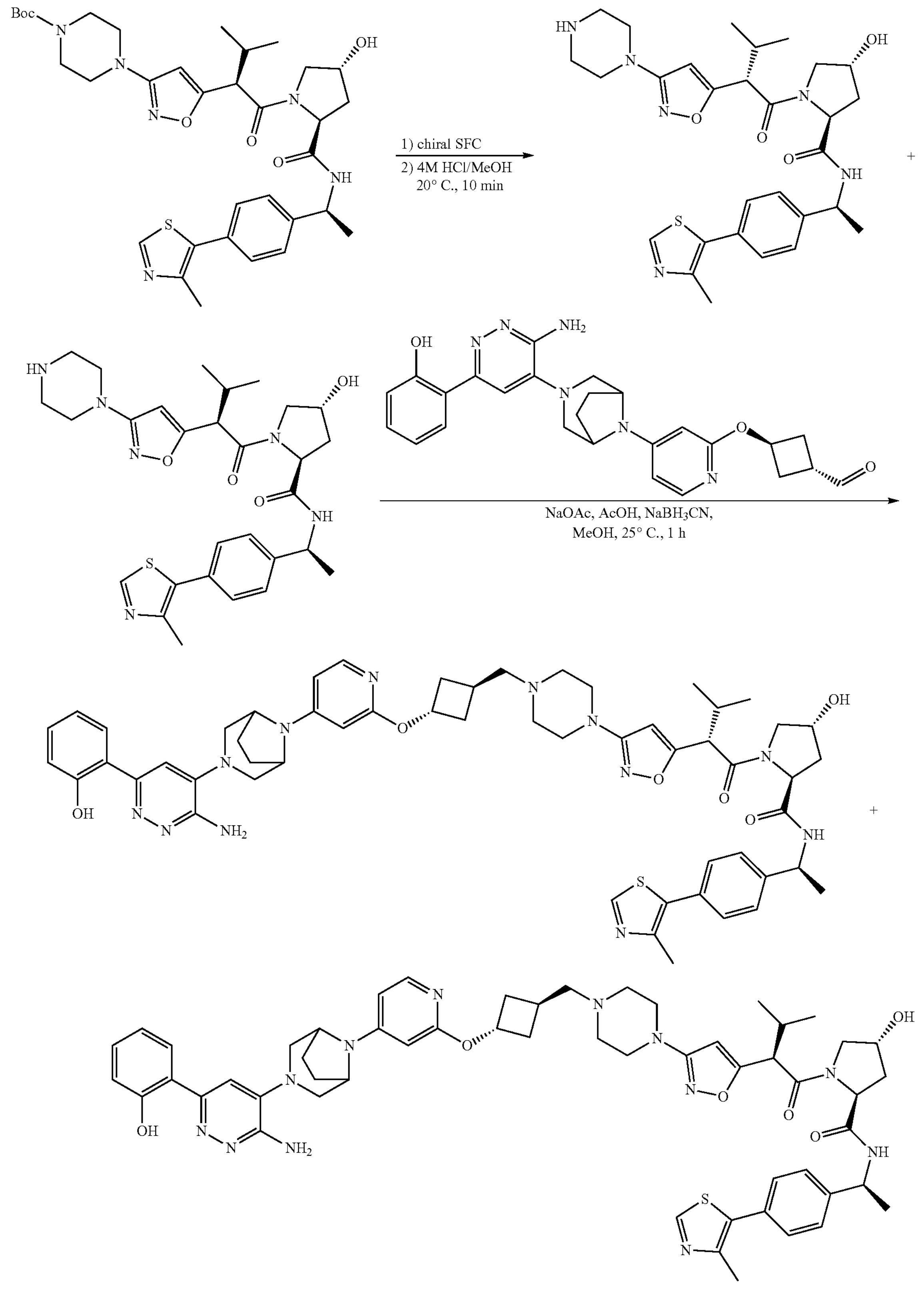

As shown in the scheme above, tert-butyl 4-(5-(1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)isoxazol-3-yl)piperazine-1-carboxylate as a diastereomeric mixture was separated into the individual isomers. Each of these isomers then reacted with (1R,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutanecarbaldehyde to provide the desired final product in an enantiomerically pure form. This method can be conveniently used to synthesize all enantiomerically pure isomers of the desired product by implementing the coupling counterparts having appropriate stereochemistry.

Exemplary Synthesis of Exemplary Compound 143

Step 1

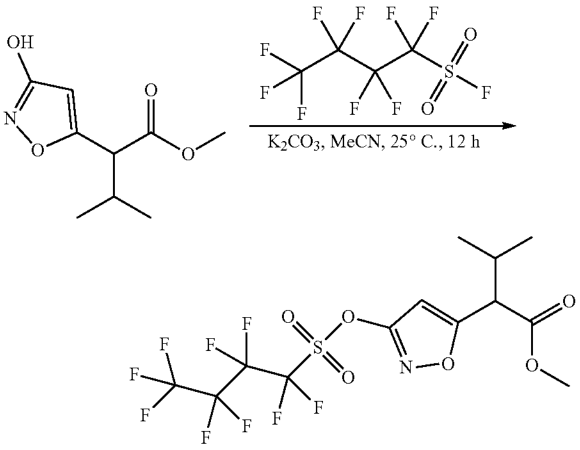

To a solution of methyl 2-(3-hydroxyisoxazol-5-yl)-3-methylbutanoate (265 g, 1.33 mol) [prepared as described for exemplary compound 144] in MeCN (1.6 L) was added $K_2CO_3$ (367.71 g, 2.66 mol) and 1,1,2,2,3,3,4,4,4-nonafluorobutane-1-sulfonyl fluoride (482.25 g, 1.60 mol, 280.38 mL). The reaction mixture was stirred at 25° C. for 12 hours. The reaction mixture was concentrated under reduced pressure to remove MeCN. The residue was diluted with water (1.5 L) and extracted with ethyl acetate (500 mL×3). The combined organic layers were washed with brine (200 mL) and dried over $Na_2SO_4$, filtered and concentrated under reduced pressure to give methyl 3-methyl-2-(3-(((perfluorobutyl)sulfonyl)oxy)isoxazol-5-yl)butanoate (458 g, 886.42 mmol) as a brown oil.

Step 2

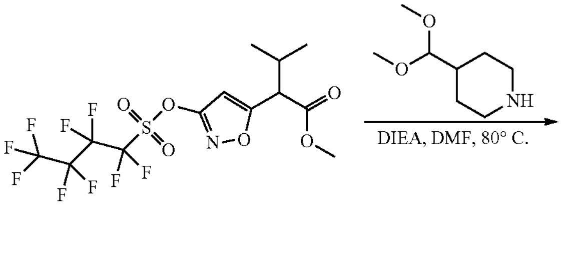

-continued

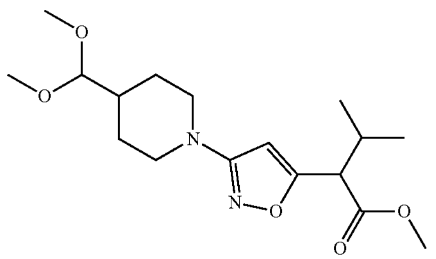

To the mixture of methyl 3-methyl-2-(3-(((perfluorobutyl)sulfonyl)oxy)isoxazol-5-yl)butanoate (160 g, 332.44 mmol) and 4-(dimethoxymethyl)piperidine (79.40 g, 498.66 mmol) in DMF (1.6 L) were added DIEA (128.90 g, 997.32 mmol, 173.72 mL) at 25° C. in one portion under nitrogen. The mixture was stirred at 80° C. for 12 hours. The mixture was cooled to 25° C. and poured into ice-water (w:w=1:1) (3 L) and stirred for 15 minutes. The aqueous phase was extracted with ethyl acetate (1 L×5). The combined organic phase was washed with brine (300 mL×3), dried with anhydrous sodium sulfate, filtered and concentrated in vacuum. The mixture was dissolved in EtOAc (70 mL) and filtered to remove the insoluble material. The residue was purified by column chromatography (petroleum ether/ethyl acetate=80:1 to 0:1) to give (34 g, 100 mmol) of methyl 2-(3-(4-(dimethoxymethyl)piperidin-1-yl)isoxazol-5-yl)-3-methylbutanoate as an orange syrup.

Step 3

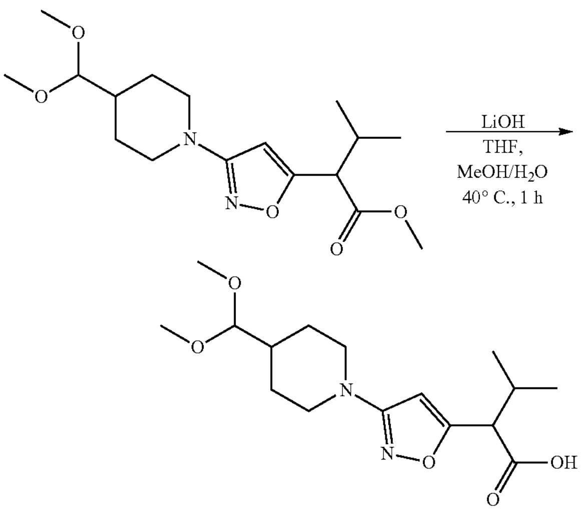

To the mixture of methyl 2-[3-[4-(dimethoxymethyl)-1-piperidyl]isoxazol-5-yl]-3-methyl-butanoate (350 mg, 1.03 mmol, 1 eq) in tetrahydrofuran (1 mL) and methanol (1 mL) was added lithium hydroxide (2 M, 1 mL, 1.95 eq) in one portion under nitrogen. The mixture was stirred at 25° C. for 1 hour. The pH was adjusted to 5-6 with trifluoroacetic acid and concentrated under reduced pressure at 45° C. The mixture was purified by preparative HPLC (column: Phenomenex Synergi C18 150*25*10 um; mobile phase: [water (0.225% FA)-ACN]; B %: 40%-70%, 9 min) to afford 2-[3-[4-(dimethoxymethyl)-1-piperidyl]isoxazol-5-yl]-3-methyl-butanoic acid (190 mg) as a yellow oil.

Step 4

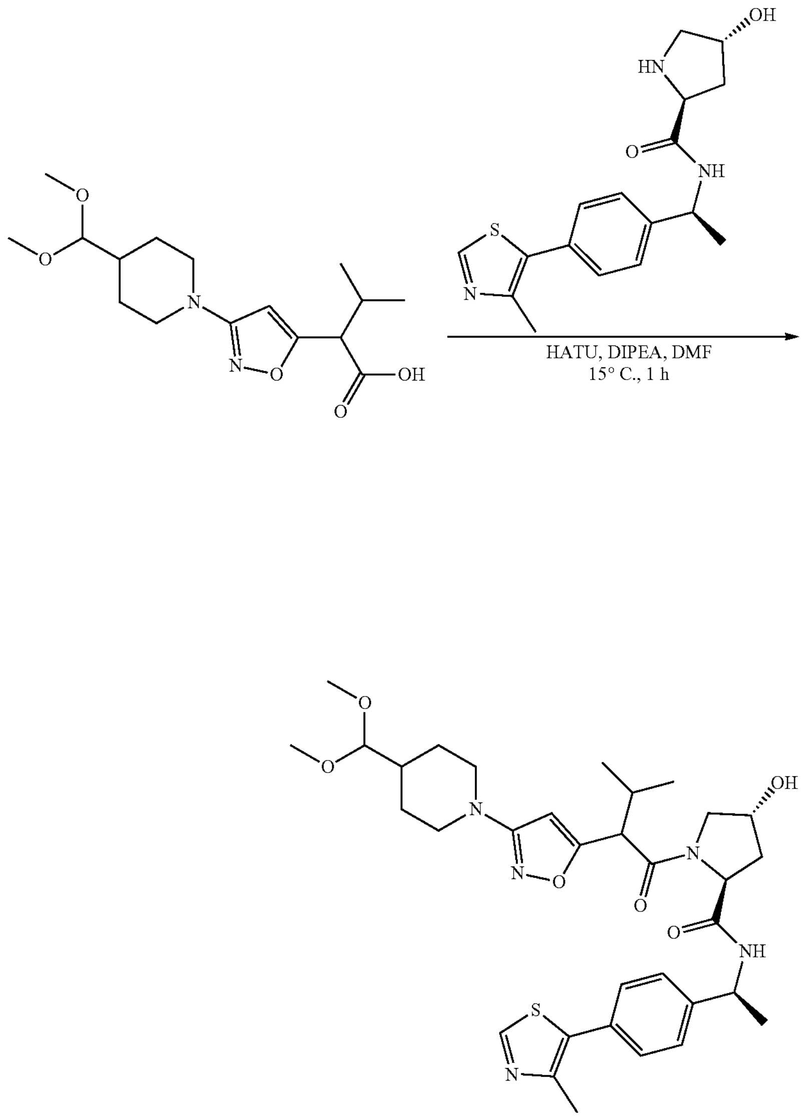

To a mixture of 2-[3-[4-(dimethoxymethyl)-1-piperidyl] isoxazol-5-yl]-3-methyl-butanoic acid (190 mg, 0.58 mmol, 1 eq), N,N-diisopropylethylamine (225 mg, 1.75 mmol, 0.3 mL, 3 eq) and (2S,4R)-4-hydroxy-N-[(1S)-1-[4-(4-methylthiazol-5-yl)phenyl]ethyl]pyrrolidine-2-carboxamide (257 mg, 0.70 mmol, 1.2 eq, hydrochloride) in N,N-dimethylformamide (10 mL) was added O-(7-azabenzotriazol-1-yl)-N,N,N,N-tetramethyl uronium hexafluorophosphate (288 mg, 0.76 mmol, 1.3 eq) in one portion at 0° C. under nitrogen. The mixture was stirred at 25° C. for 1 hour. The mixture was poured into ice-water (w/w=1/1) (30 mL) and stirred for 15 minutes. The aqueous phase was extracted with ethyl acetate (30 mL×3). The combined organic phase was washed with brine (30 mL×3), dried with sodium sulfate, filtered and concentrated in vacuum. The residue was purified by silica gel chromatography (dichloromethane: methanol=10/1) to afford (2S,4R)-1-[2-[3-[4-(dimethoxymethyl)-1-piperidyl] isoxazol-5-yl]-3-methyl-butanoyl]-4-hydroxy-N—[(S)-1-[4-(4-methylthiazol-5-yl)phenyl]ethyl] pyrrolidine-2-carboxamide (208 mg) as a yellow oil.

Step 5

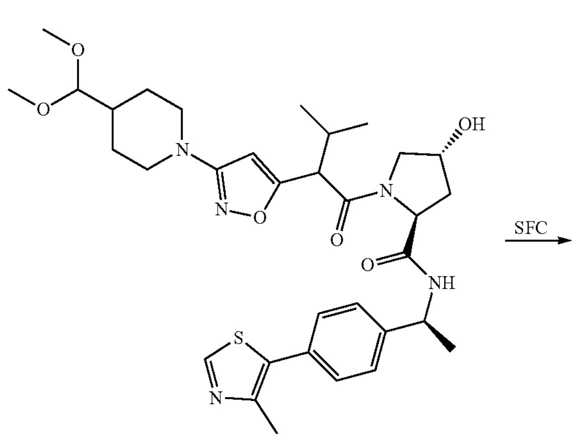

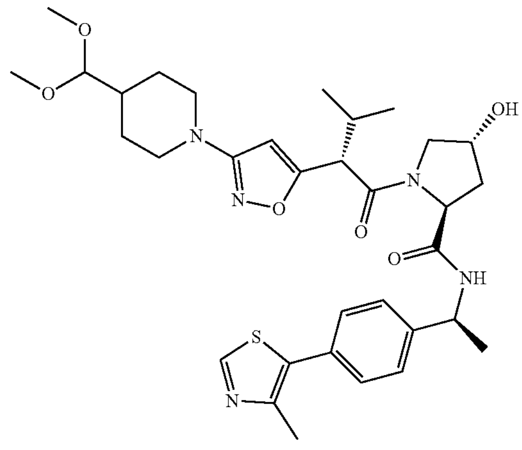

(2S,4R)-1-[2-[3-[4-(dimethoxymethyl)-1-piperidyl] isoxazol-5-yl]-3-methyl-butanoyl]-4-hydroxy-N-[(1S)-1-[4-(4-methylthiazol-5-yl)phenyl] ethyl] pyrrolidine-2-carboxamide (200 mg, 0.31 mmol, 1 eq) was purified by SFC (column: DAICEL CHIRALPAK AD (250 mm*30 mm, 10 um); mobile phase: [0.1% NH3H2O IPA]; B %: 45%-45%, 3.0 min; 65 min). The mixture was concentrated under reduced pressure at 45° C.

(2S,4R)-1-[(2S)-2-[3-[4-(dimethoxymethyl)-1-piperidyl] isoxazol-5-yl]-3-methyl-butanoyl]-4-hydroxy-N-[(1S)-1-[4-(4-methylthiazol-5-yl)phenyl] ethyl]pyrrolidine-2-carboxamide (90 mg) (retention time: 1.884 min in chiral SFC) was obtained as a yellow oil.

(2S,4R)-1-[(2S)-2-[3-[4-(dimethoxymethyl)-1-piperidyl] isoxazol-5-yl]-3-methyl-butanoyl]-4-hydroxy-N-[(1S)-1-[4-(4-methylthiazol-5-yl)phenyl] ethyl]pyrrolidine-2-carboxamide (90 mg, 0.13 mmol, 42% yield, 94% purity) (retention time: 2.230 min in chiral SFC) was obtained as a yellow oil.

Step 6

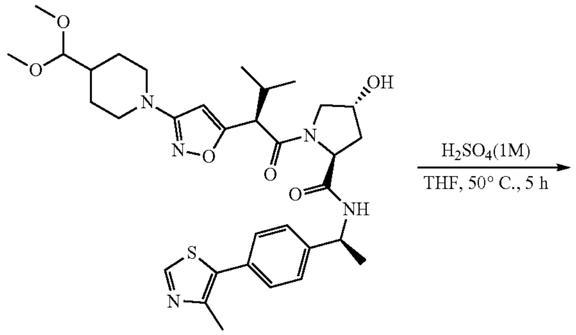

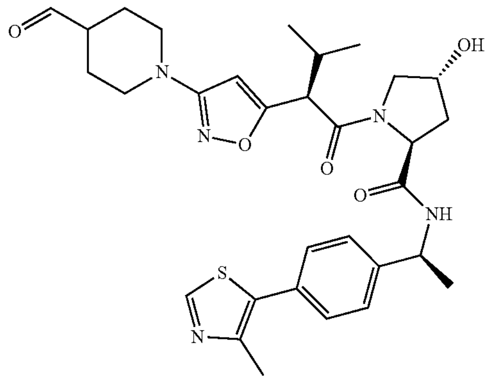

To a solution of (2S,4R)-1-[(2R)-2-[3-[4-(dimethoxymethyl)-1-piperidyl]isoxazol-5-yl]-3-methyl-butanoyl]-4-hydroxy-N-[(1S)-1-[4-(4-methylthiazol-5-yl)phenyl]ethyl] pyrrolidine-2-carboxamide (80 mg, 0.13 mmol, 1 eq) in tetrahydrofuran (2 mL) was added sulfuric acid solution (1 M, 2 mL, 16.00 eq). The reaction mixture was stirred at 50° C. for 5 hours. The mixture was added to the saturated sodium bicarbonate (10 mL), the mixture was extracted with ethyl acetate (20 mL×3). The combined organic phase was washed with brine (30 mL), dried over sodium sulfate, filtered, concentrated in vacuum, and used directly in the next step. Crude (2S,4R)-1-[(2R)-2-[3-(4-formyl-1-piperidyl)isoxazol-5-yl]-3-methyl-butanoyl]-4-hydroxy-N-[(1S)-1-[4-(4-methylthiazol-5-yl)phenyl] ethyl]pyrrolidine-2-carboxamide (68 mg) was obtained as a light yellow solid and used directly in the next step.

Step 7

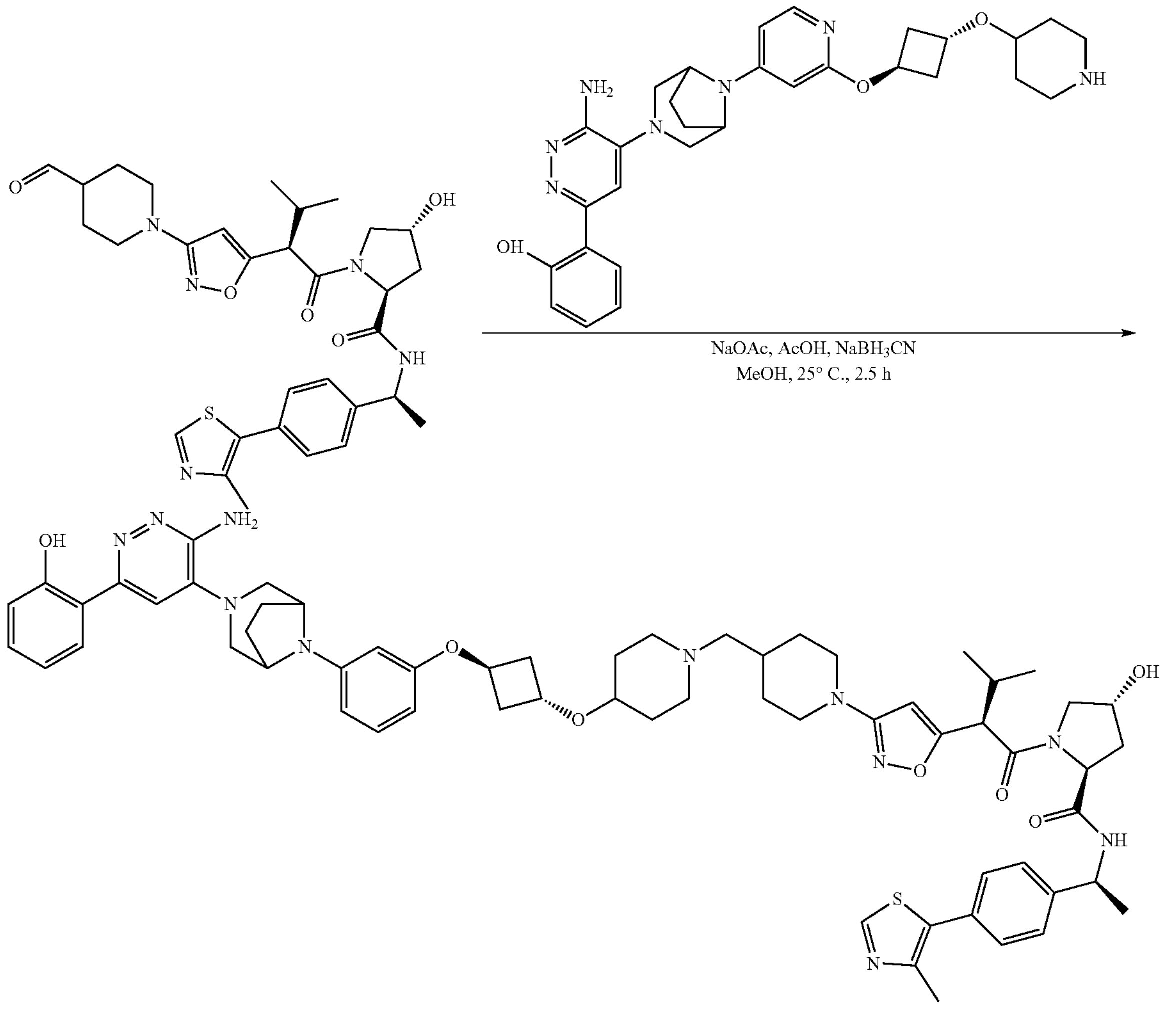

Compound 143

To a solution of 2-[6-amino-5-[8-[2-[3-(4-piperidyloxy) cyclobutoxy]-4-pyridyl]-3,8-diazabicyclo[3.2.1]octan-3-yl] pyridazin-3-yl]phenol dihydrochloride (2.08 g, 3.37 mmol, 1 eq) in methanol (40 mL) was added sodium acetate (829 mg, 10.11 mmol, 3 eq), then the mixture was added (2S, 4R)-1-[(2R)-2-[3-(4-formyl-1-piperidyl)isoxazol-5-yl]-3-methyl-butanoyl]-4-hydroxy-N-[(1S)-1-[4-(4-methylthiazol-5-yl)phenyl] ethyl]pyrrolidine-2-carboxamide (2 g, 3.37 mmol, 1 eq) and acetic acid (23 mg, 0.33 mmol, 0.1 eq). The mixture was stirred at 25° C. for 0.5 hours, and then to the mixture was added sodium cyanoborohydride (1.06 g, 16.84 mmol, 5 eq). The mixture was stirred at 25° C. for 2 hours. The reaction mixture was concentrated under reduced pressure. The residue was purified by prep-HPLC (column: Phenomenex luna C18 250*50 mm*10 um; mobile phase: [water (0.225% FA)-ACN]; B %: 10%-40%, 22 min). (2S, 4R)-1-[(2R)-2-[3-[4-[[4-[3-[[4-[3-[[4-3-3-Amino-6-(2-hydroxyphenyl)pyridazin-4-yl]-3,8-diazabicyclo[3.2.1]octan-8-yl]-2-pyridyl]oxy]cyclobutoxy]-1-piperidyl]methyl]-1-piperidyl]isoxazol-5-yl]-3-methyl-butanoyl]-4-hydroxy-N-[(1S)-1-[4-(4-methylthiazol-5-yl)phenyl]ethyl]pyrrolidine-2-carboxamide formate (1196 mg, 1.02 mmol) was obtained as a white solid.

Exemplary Synthesis of Exemplary Compound 143

Step 1

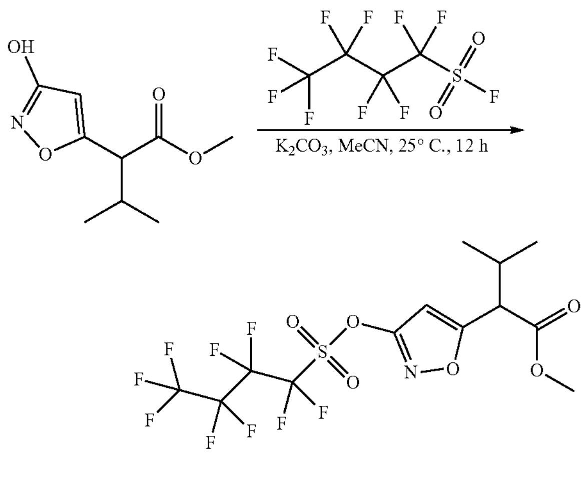

To a solution of methyl 2-(3-hydroxyisoxazol-5-yl)-3-methylbutanoate (265 g, 1.33 mol) [prepared as described for exemplary compound 144] in MeCN (1.6 L) was added $K_2CO_3$ (367.71 g, 2.66 mol) and 1,1,2,2,3,3,4,4,4-nonafluorobutane-1-sulfonyl fluoride (482.25 g, 1.60 mol, 280.38 mL). The reaction mixture was stirred at 25° C. for 12 hours. The reaction mixture was concentrated under reduced pressure to remove MeCN. The residue was diluted with water (1.5 L) and extracted with ethyl acetate (500 mL×3). The combined organic layers were washed with brine (200 mL) and dried over $Na_2SO_4$, filtered and concentrated under reduced pressure to give methyl 3-methyl-2-(3-(((perfluorobutyl)sulfonyl)oxy)isoxazol-5-yl)butanoate (458 g, 886.42 mmol) as a brown oil.

Step 2

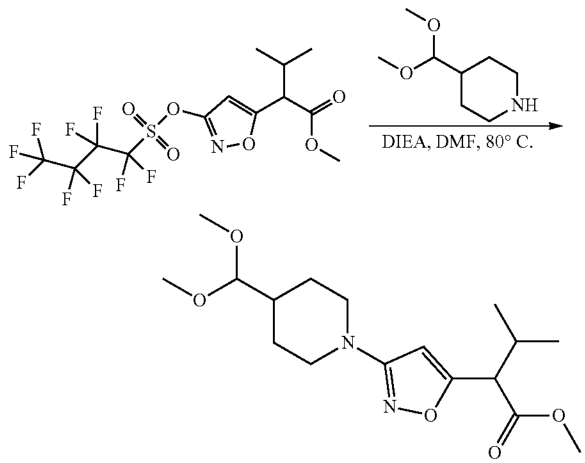

To the mixture of methyl 3-methyl-2-(3-(((perfluorobutyl)sulfonyl)oxy)isoxazol-5-yl)butanoate (160 g, 332.44 mmol) and 4-(dimethoxymethyl)piperidine (79.40 g, 498.66 mmol) in DMF (1.6 L) were added DIEA (128.90 g, 997.32 mmol, 173.72 mL) at 25° C. in one portion under nitrogen. The mixture was stirred at 80° C. for 12 hours. The mixture was cooled to 25° C. and poured into ice-water (w:w=1:1) (3 L) and stirred for 15 minutes. The aqueous phase was extracted with ethyl acetate (1 L×5). The combined organic phase was washed with brine (300 mL×3), dried with anhydrous sodium sulfate, filtered and concentrated in vacuum. The mixture was dissolved in EtOAc (70 mL) and filtered to remove the insoluble material. The residue was purified by column chromatography (petroleum ether/ethyl acetate=80:1 to 0:1) to give (34 g, 100 mmol) of methyl 2-(3-(4-(dimethoxymethyl)piperidin-1-yl)isoxazol-5-yl)-3-methylbutanoate as an orange syrup.

Step 3

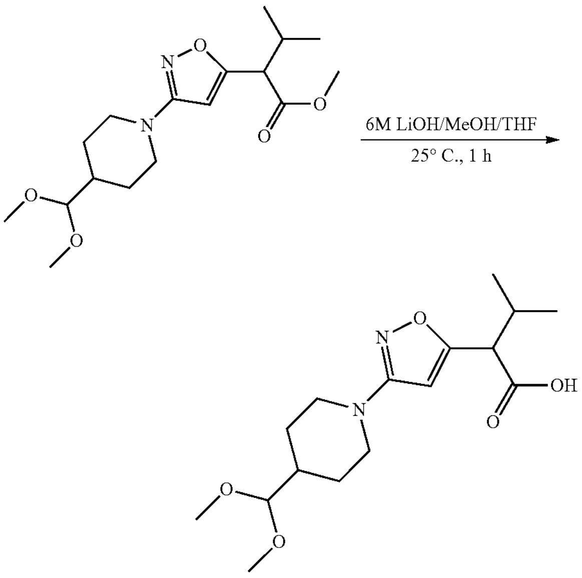

To a solution of methyl 2-[3-[4-(dimethoxymethyl)-1-piperidyl]isoxazol-5-yl]-3-methyl-butanoate (10 g, 29.38 mmol, 1 eq) in MeOH (30 mL) was added aqueous LiOH solution (6 M, 30.00 mL, 6.13 eq) and THF (30 mL). The mixture was stirred at 25° C. for 1 hour. The reaction mixture pH was adjusted by 1 M HCl (200 mL), diluted with water (200 mL), and extracted with EtOAc (200 mL×3). The combined organic layers were washed with brine (200 mL), dried over anhydrous $Na_2SO_4$, filtered and concentrated under reduced pressure. Crude 2-[3-[4-(dimethoxymethyl)-1-piperidyl]isoxazol-5-yl]-3-methyl-butanoic acid (9.5 g, 29.11 mmol) was obtained as a yellow oil.

Step 4

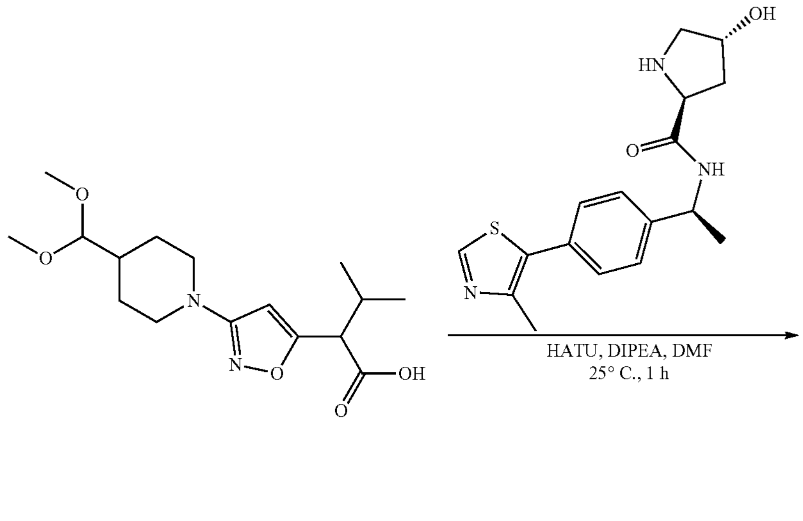

-continued

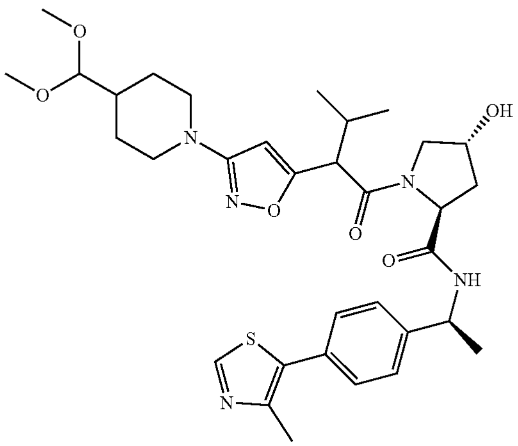

To a solution of (2S,4R)-4-hydroxy-N-[(1S)-1-[4-(4-methylthiazol-5-yl)phenyl]ethyl] pyrrolidine-2-carboxamide hydrochloride (10.71 g, 29.11 mmol, 1 eq), DIPEA (11.29 g, 87.32 mmol, 15.21 mL, 3 eq) and 2-[3-[4-(dimethoxymethyl)-1-piperidyl]isoxazol-5-yl]-3-methyl-butanoic acid (9.5 g, 29.11 mmol, 1 eq) in DMF (100 mL) was added HATU (16.60 g, 43.66 mmol, 1.5 eq) at 0° C. under nitrogen. The mixture was warmed to 25° C. and stirred for 1 hour. The reaction mixture was diluted with water (300 mL) and extracted with EtOAc (150 mL×3). The combined organic layers were washed with brine (100 mL), dried over anhydrous $Na_2SO_4$, filtered and concentrated under reduced pressure to produce a residue. The residue was purified by prep-HPLC (column: Phenomenex luna C18 250*50 mm*10 um; mobile phase: [water (0.225% FA)-MeCN]; B %: 30%-60%, 15 min). (2S,4R)-1-[2-[3-[4-(dimethoxymethyl)-1-piperidyl]isoxazol-5-yl]-3-methyl-butanoyl]-4-hydroxy-N-[(1S)-1-[4-(4-methylthiazol-5-yl)phenyl]ethyl] pyrrolidine-2-carboxamide (18 g, 27.57 mmol) was obtained as a white solid.

Step 5

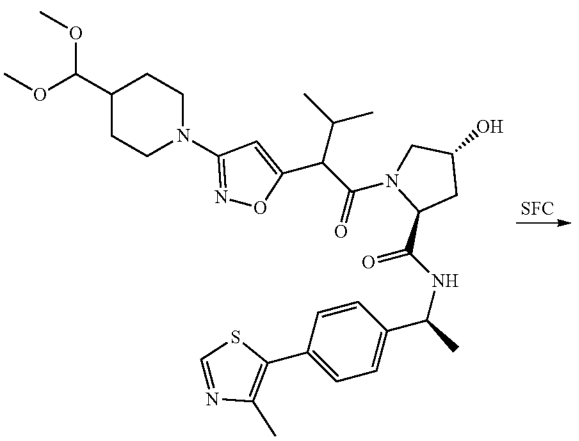

-continued

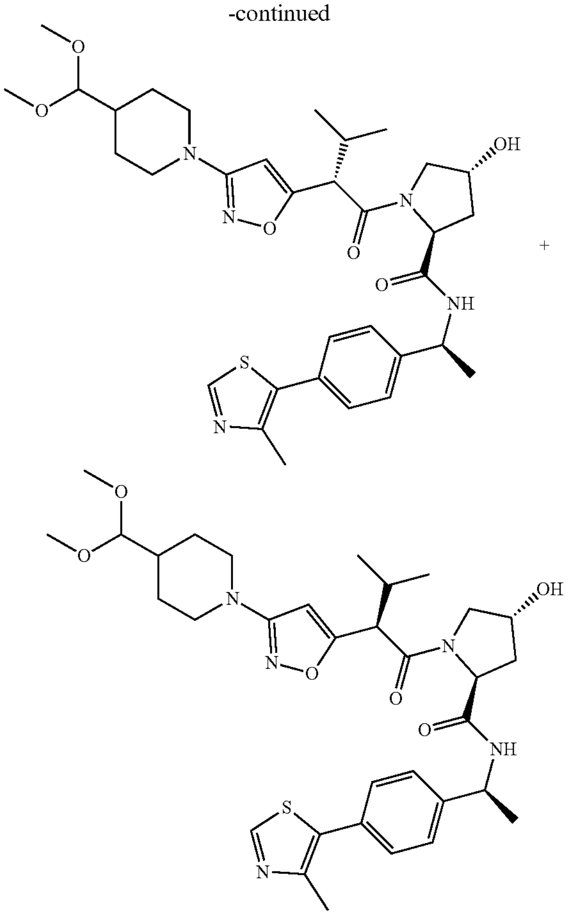

(2S,4R)-1-[2-[3-[4-(dimethoxymethyl)-1-piperidyl]isoxazol-5-yl]-3-methyl-butanoyl]-4-hydroxy-N-[(1S)-1-[4-(4-methylthiazol-5-yl)phenyl] ethyl]pyrrolidine-2-carboxamide (5 g, 7.81 mmol, 1 eq) was separated by prep-SFC twice (column: DAICEL CHIRALPAK AD-H 250 mm×30 mm, I.D., 5 um; Mobile phase: isopropanol (0.1% NH3H$_2$O) in $CO_2$ from 40%-40%; Flow rate: 70 g/min; Wavelength: 220 nm) and (column: DAICEL CHIRALPAK AD 250 mm×30 mm, I.D., 10 um; Mobile phase: isopropanol (0. % NH3H$_2$O) in $CO_2$ from 40%-40%; Flow rate: 70 g/min; Wavelength: 220 nm).

Compound (2S,4R)-1-[(2S)-2-[3-[4-(dimethoxymethyl)-1-piperidyl]isoxazol-5-yl]-3-methyl-butanoyl]-4-hydroxy-N-[(1S)-1-[4-(4-methylthiazol-5-yl)phenyl]ethyl]pyrrolidine-2-carboxamide (2.5 g, 3.91 mmol) was obtained as a white solid.

Compound (2S,4R)-1-[(2R)-2-[3-[4-(dimethoxymethyl)-1-piperidyl]isoxazol-5-yl]-3-methyl-butanoyl]-4-hydroxy-N-[(1S)-1-[4-(4-methylthiazol-5-yl)phenyl]ethyl]pyrrolidine-2-carboxamide (2.4 g, 3.68 mmol) was obtained as a white solid.

Step 6

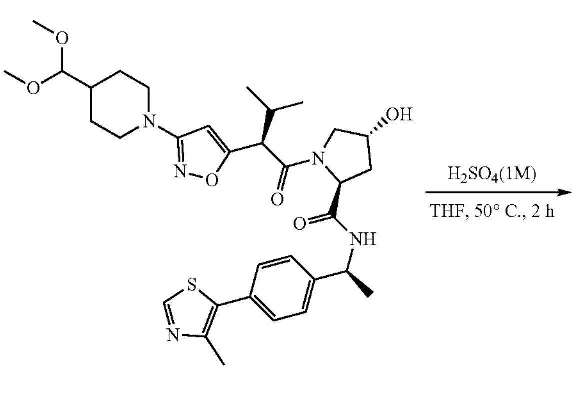

-continued

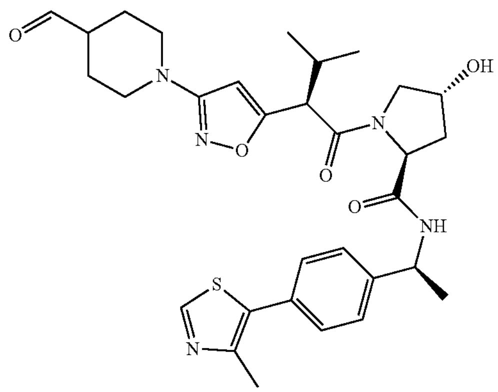

To a solution of (2S,4R)-1-[(2R)-2-[3-[4-(dimethoxymethyl)-1-piperidyl]isoxazol-5-yl]-3-methyl-butanoyl]-4-hydroxy-N-[(1S)-1-[4-(4-methylthiazol-5-yl)phenyl]ethyl]pyrrolidine-2-carboxamide (1.2 g, 1.88 mmol, 1 eq) in THF (15 mL) was added $H_2SO_4$ (1 M, 13.85 mL, 7.38 eq). The mixture was stirred at 50° C. for 2 hr. The reaction mixture was quenched by addition sat·$NaHCO_3$ (30 mL), and then diluted with water (30 mL) and extracted with brine (50 mL×3). The combined organic layers were washed with brine (30 mL), dried over anhydrous $Na_2SO_4$, filtered and concentrated under reduced pressure to give a residue. Crude (2S,4R)-1-[(2R)-2-[3-(4-formyl-1-piperidyl)isoxazol-5-yl]-3-methyl-butanoyl]-4-hydroxy-N-[(1S)-1-[4-(4-methylthiazol-5-yl)phenyl]ethyl]pyrrolidine-2-carboxamide (1.05 g, 1.77 mmol) was obtained as a white solid.

Step 7

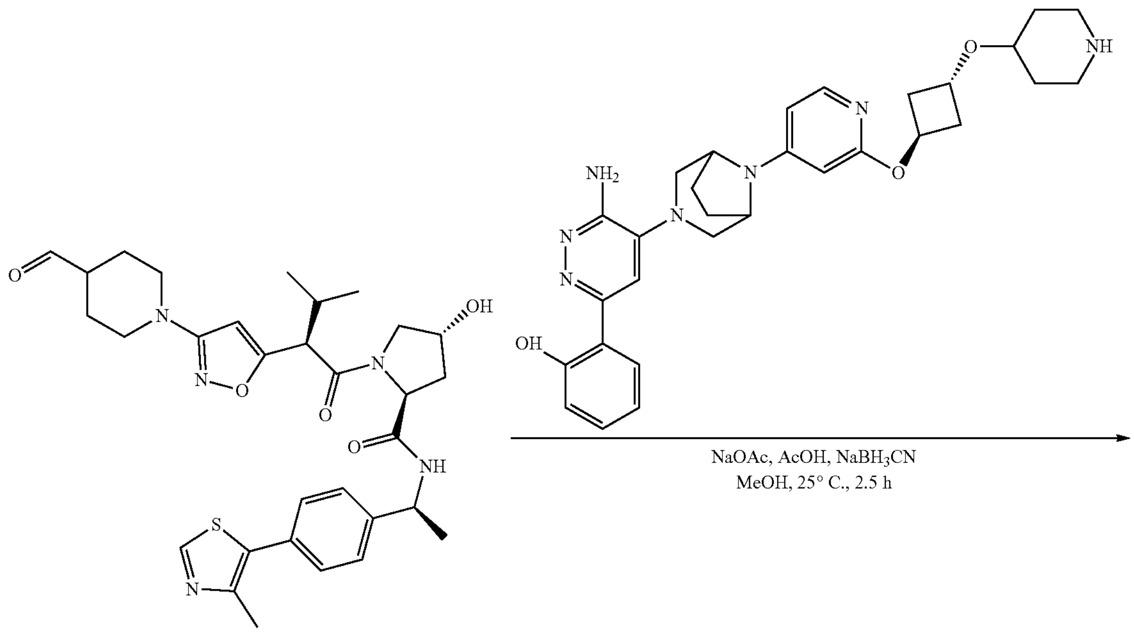

-continued

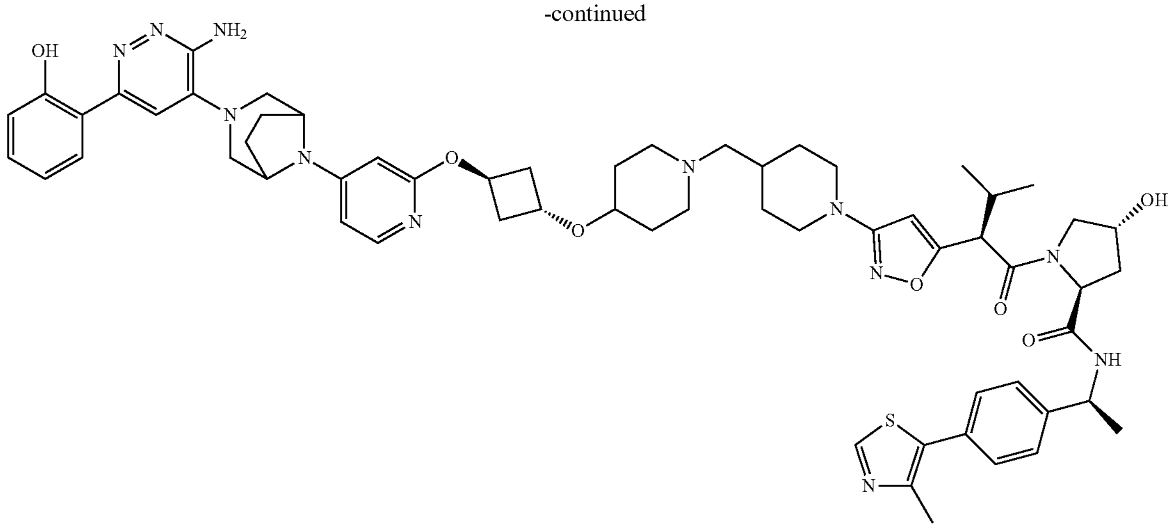

Exemplary Compound 143

To a solution of 2-[6-amino-5-[8-[2-[3-(4-piperidyloxy) cyclobutoxy]-4-pyridyl]-3,8-diazabicyclo[3.2.1]octan-3-yl] pyridazin-3-yl]phenol dihydrochloride (2.08 g, 3.37 mmol, 1 eq) in methanol (40 mL) was added sodium acetate (829 mg, 10.11 mmol, 3 eq), then the mixture was added (2S, 4R)-1-[(2R)-2-[3-(4-formyl-1-piperidyl)isoxazol-5-yl]-3-methyl-butanoyl]-4-hydroxy-N-[(1S)-1-[4-(4-methylthiazol-5-yl)phenyl] ethyl]pyrrolidine-2-carboxamide (2 g, 3.37 mmol, 1 eq) and acetic acid (23 mg, 0.33 mmol, 0.1 eq). The mixture was stirred at 25° C. for 0.5 h, and then to the mixture was added sodium cyanoborohydride (1.06 g, 16.84 mmol, 5 eq). The mixture was stirred at 25° C. for 2 hours. The reaction mixture was concentrated under reduced pressure. The residue was purified by prep-HPLC (column: Phenomenex luna C18 250*50 mm*10 um; mobile phase: [water (0.225% FA)-ACN]; B %: 10%-40%, 22 min). (2S, 4R)-1-[(2R)-2-[3-[4-[[4-[3-[[4-[3-[3-Amino-6-(2- hydroxyphenyl)pyridazin-4-yl]-3,8-diazabicyclo[3.2.1]octan-8-yl]-2-pyridyl]oxy]cyclobutoxy]-1-piperidyl]methyl]-1-piperidyl]isoxazol-5-yl]-3-methyl-butanoyl]-4-hydroxy-N-[(1S)-1-[4-(4-methylthiazol-5-yl)phenyl]ethyl]pyrrolidine-2-carboxamide formate (1196 mg, 1.02 mmol) was obtained as a white solid.

Exemplary Synthesis of Exemplary Compound 594

Prepared according to the schemes below using procedures analogous to those described for other examples above.

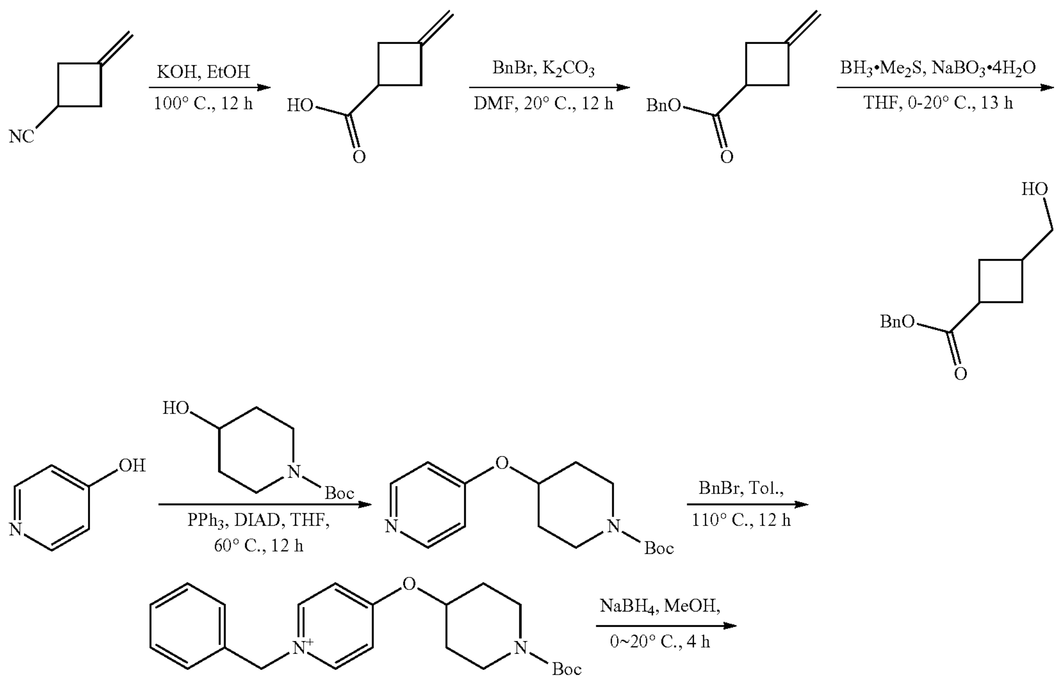

-continued
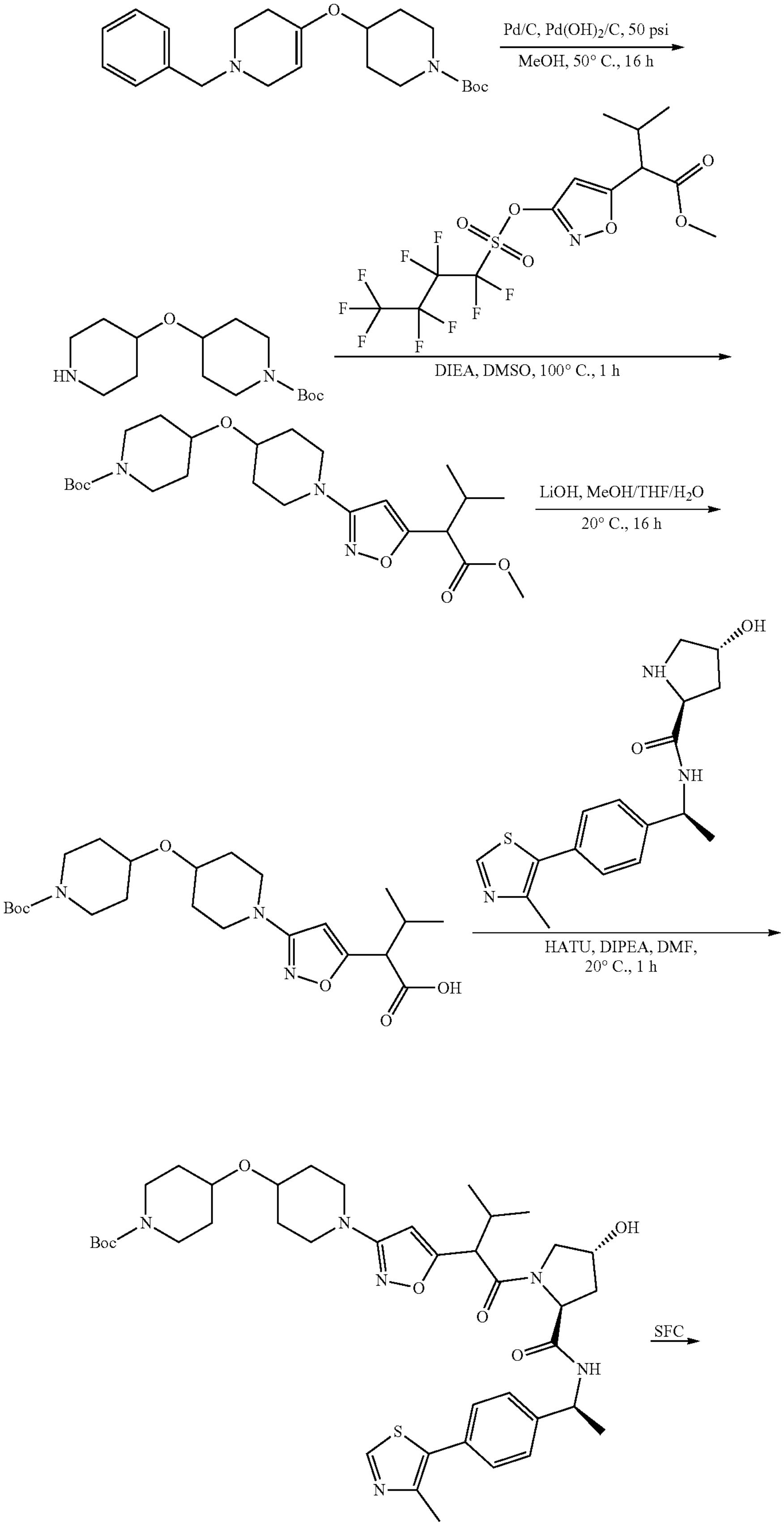

-continued
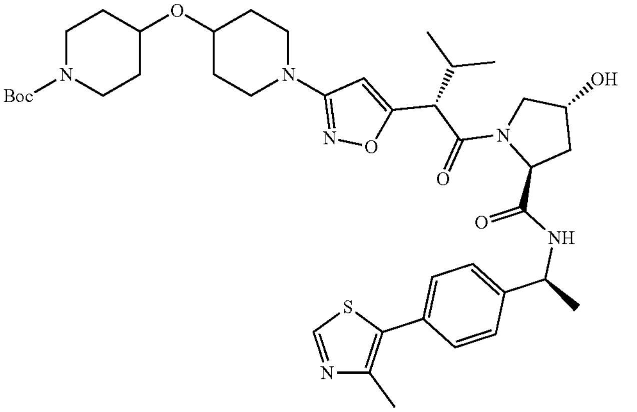
+
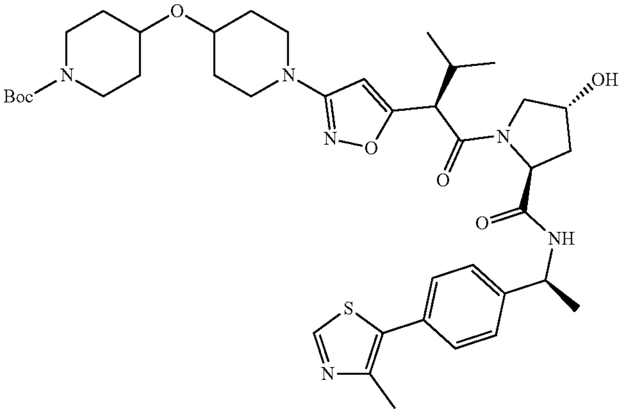
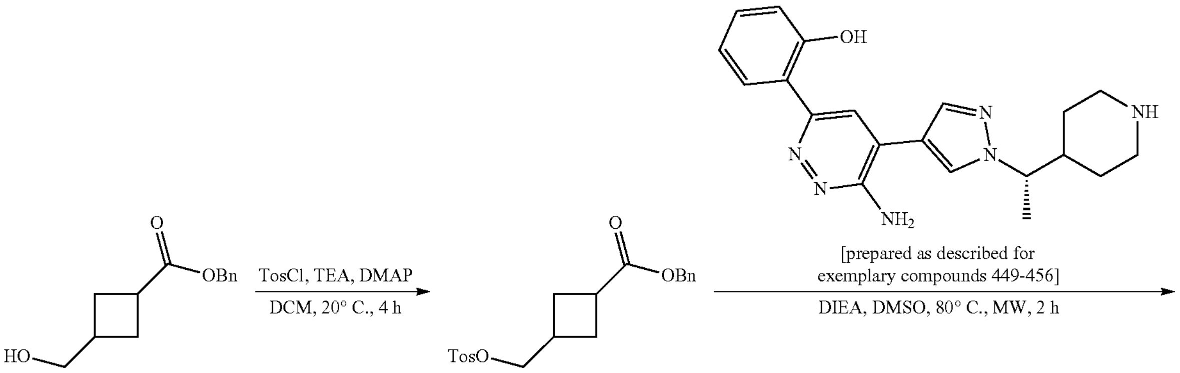
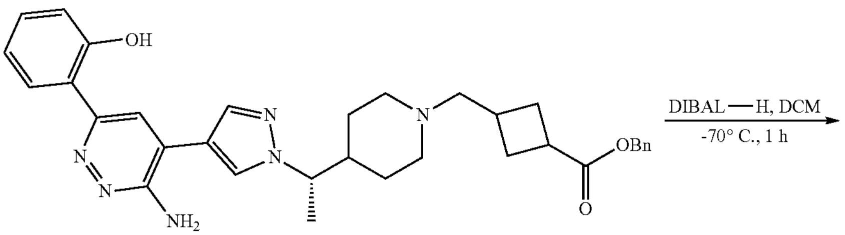

-continued
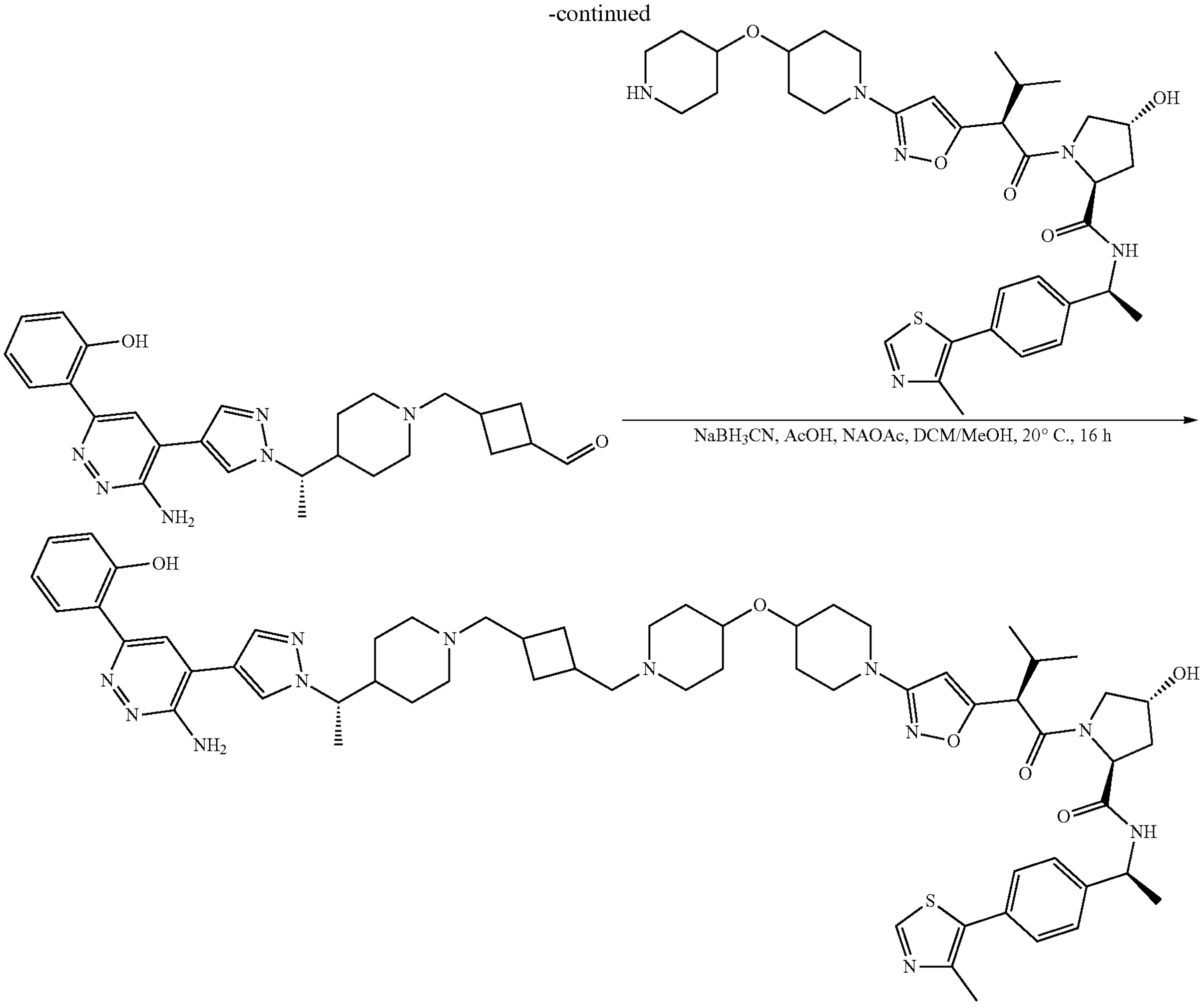
Exemplary Compound 594
Exemplary Compound 596 can be prepared using analogous procedures.
Exemplary Synthesis of Exemplary Compound 602
Prepared according to the scheme below using procedures analogous to those described for exemplary compound 143.
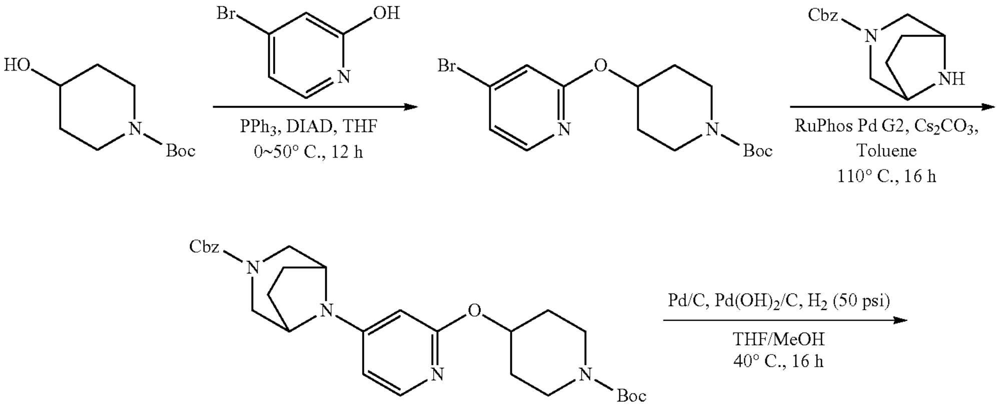

-continued
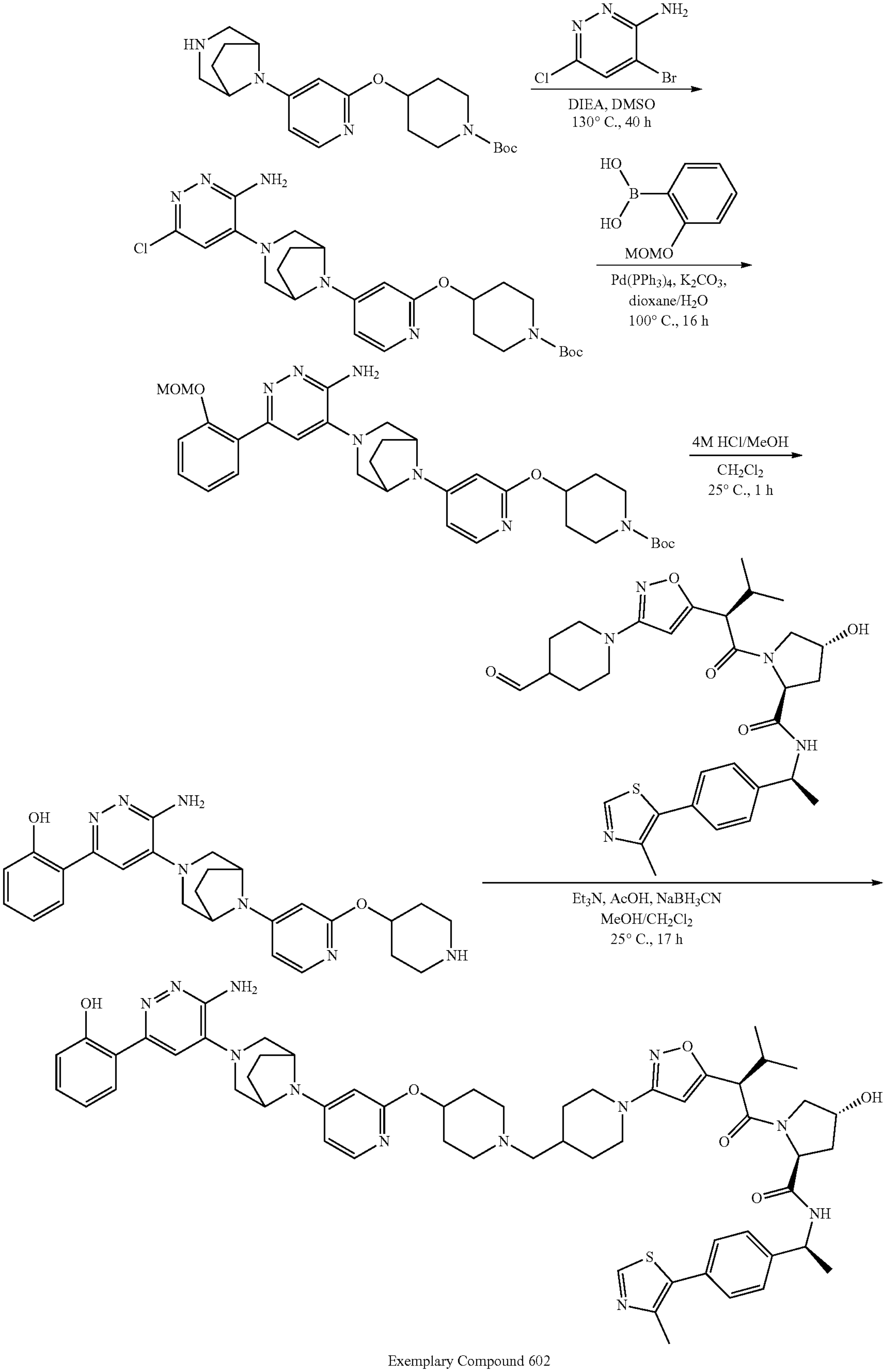
Exemplary Compound 602

Exemplary Synthesis of Exemplary Compound 607
Prepared using procedures as described for exemplary compound 143 and exemplary compound 178.
Exemplary Synthesis of Exemplary Compound 610
Prepared according to the scheme below using procedures analogous to those described for exemplary compound 143 and exemplary compound 188, and other examples above.
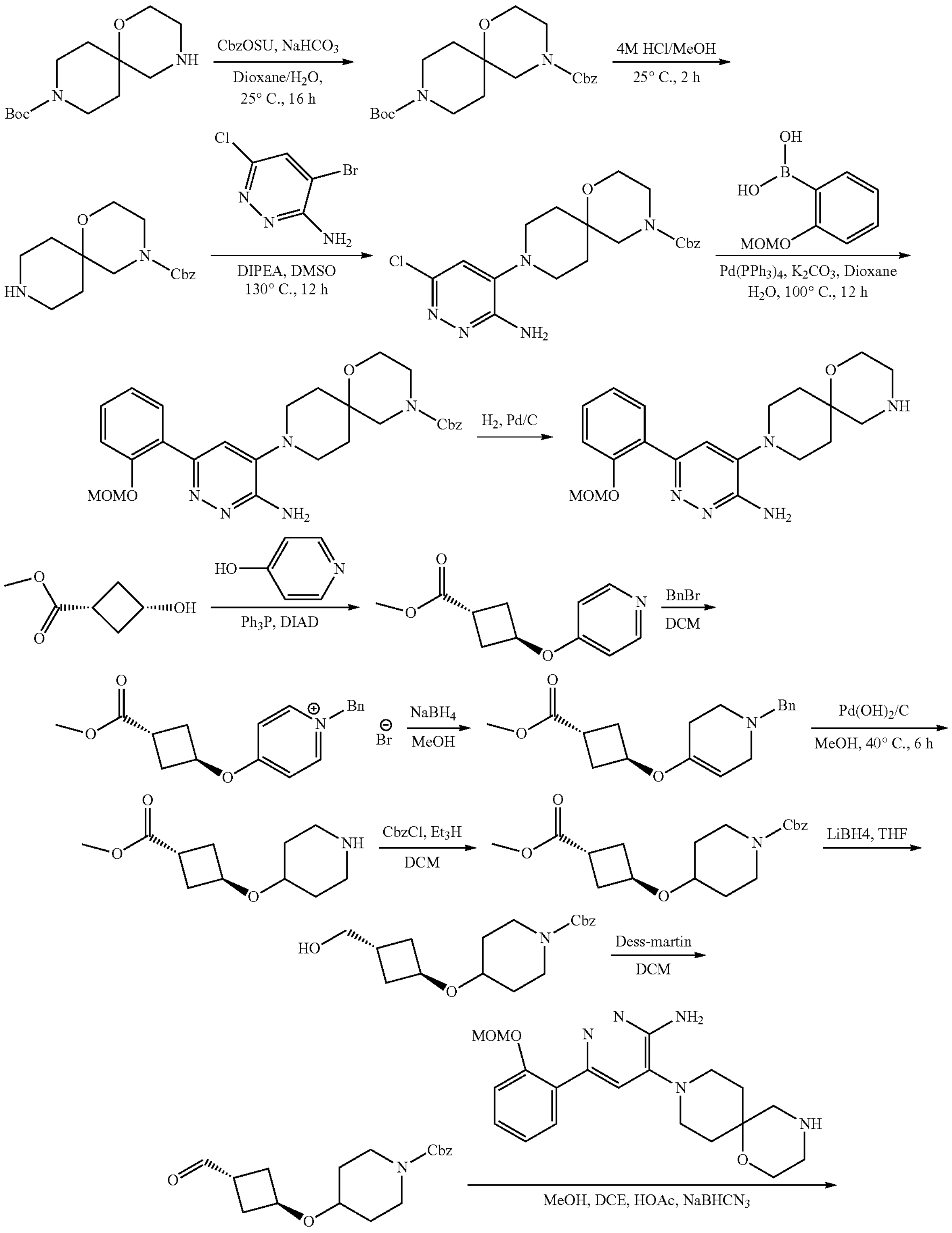

-continued
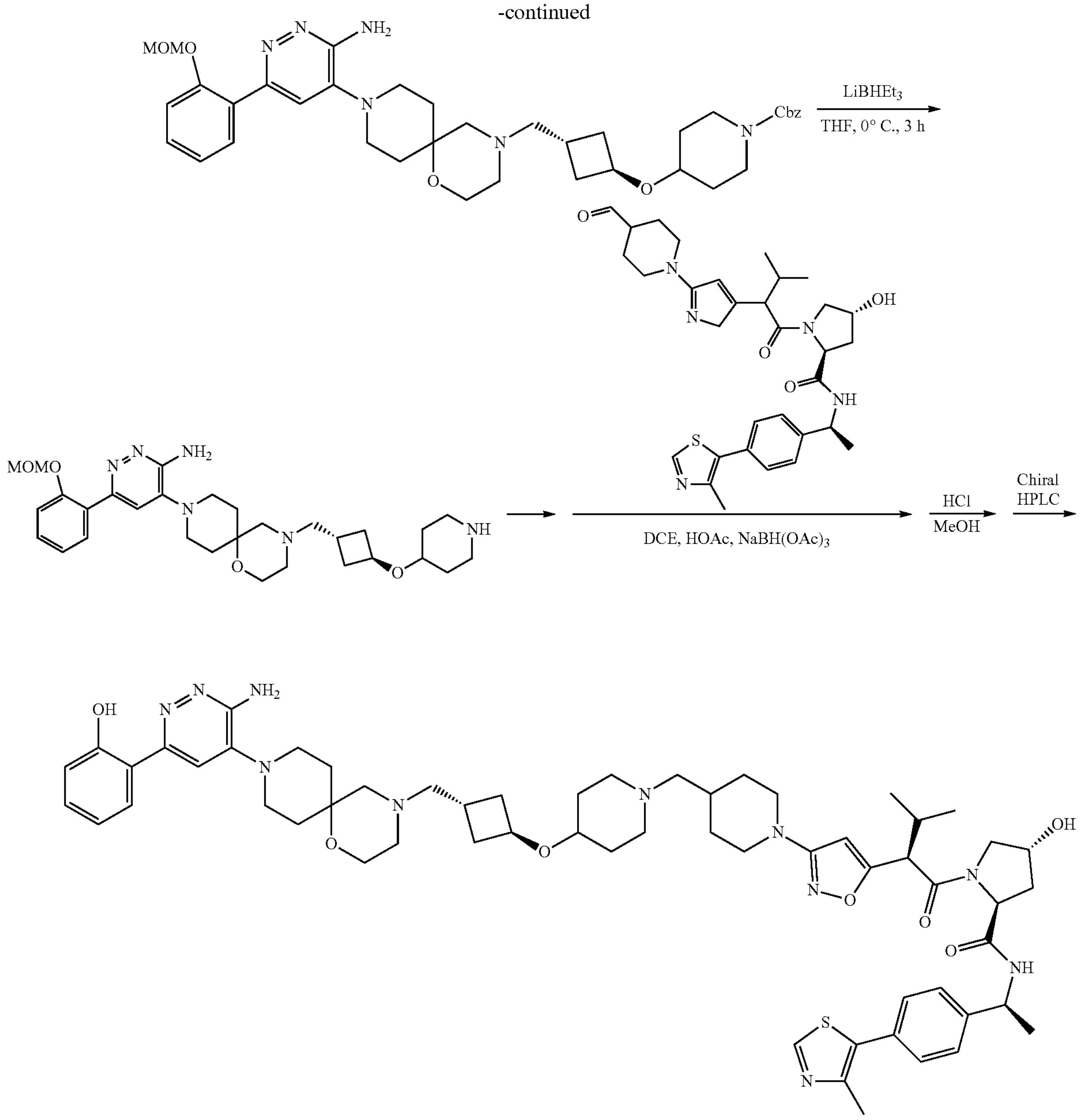
Exemplary Compound 610
Exemplary Synthesis of Exemplary Compound 616
Prepared according to the scheme below using procedures analogous to those described for examples above.
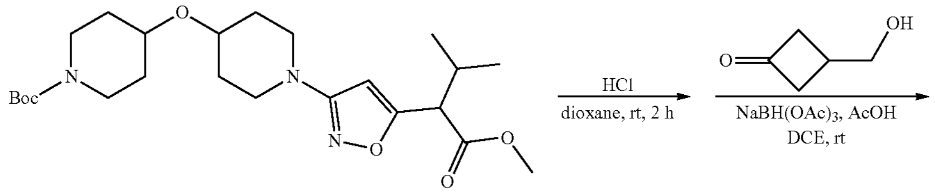
[prepared as described for exemplary compound 594]

-continued
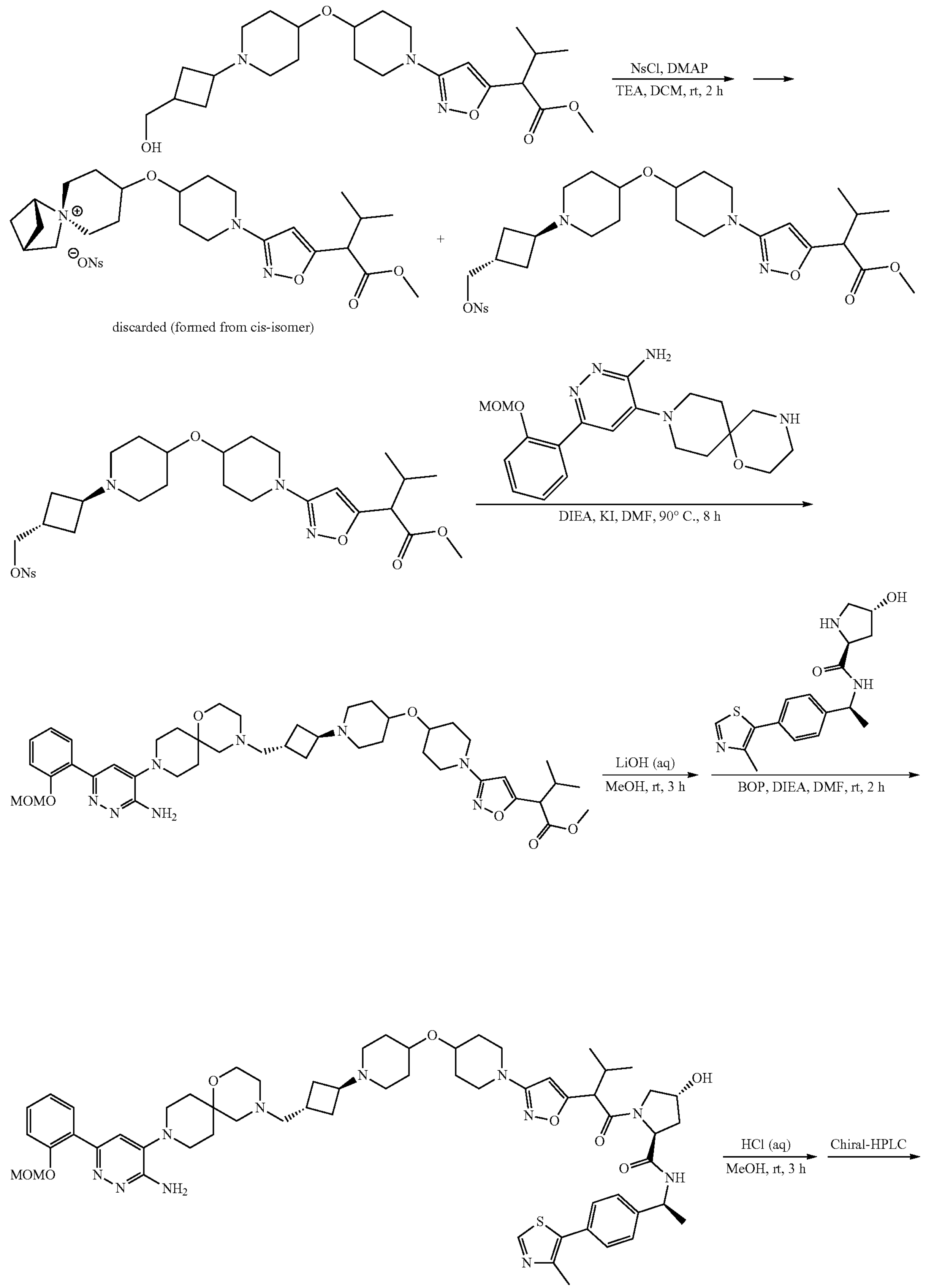

-continued
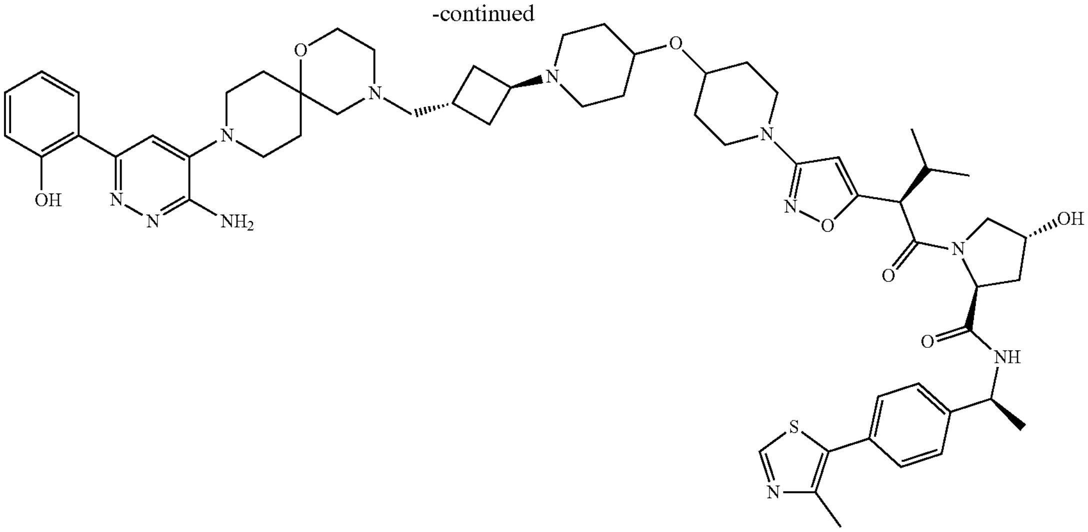
Exemplary Compound 616
Exemplary Synthesis of Exemplary Compound 618
Prepared according to the scheme below using procedures described for exemplary compound 610, exemplary compound 143, and other examples above.
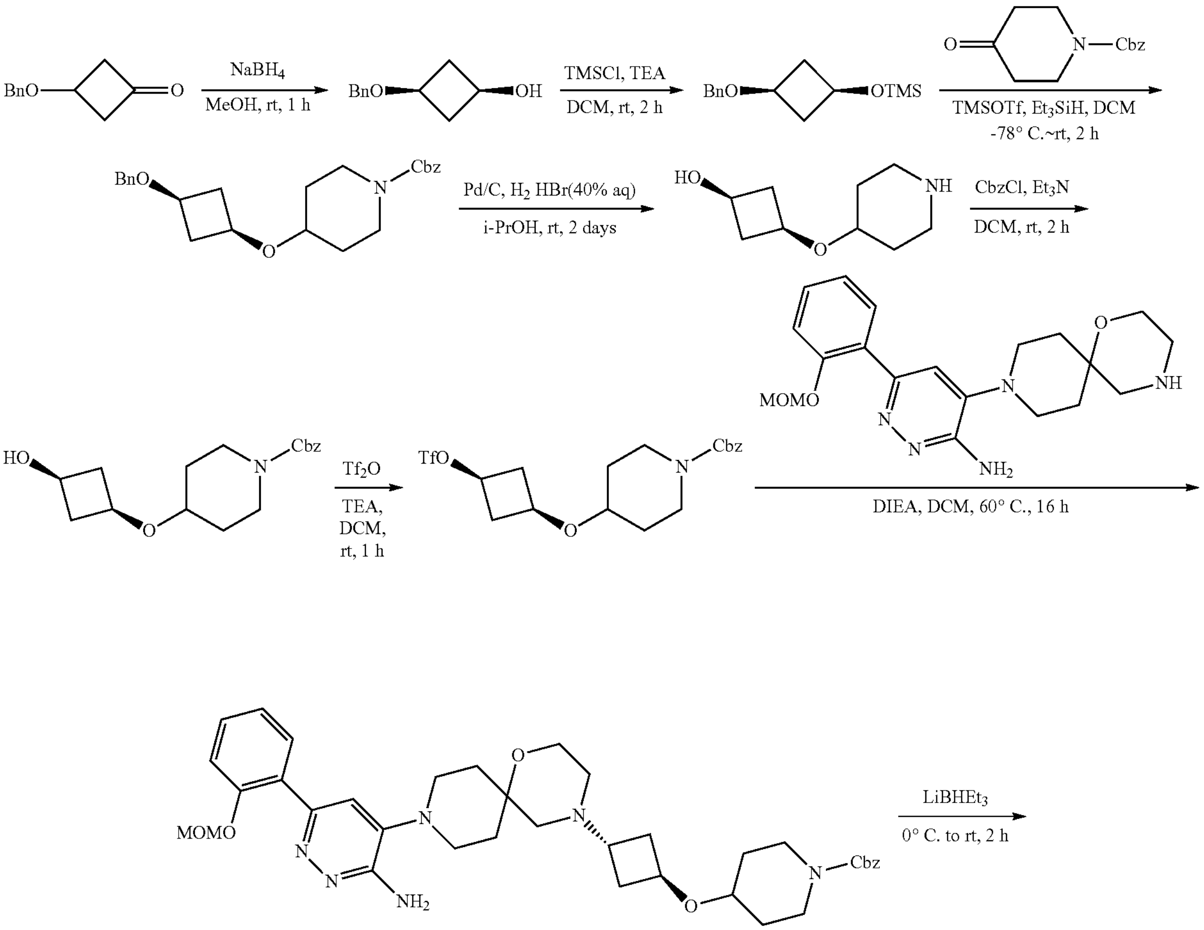

-continued
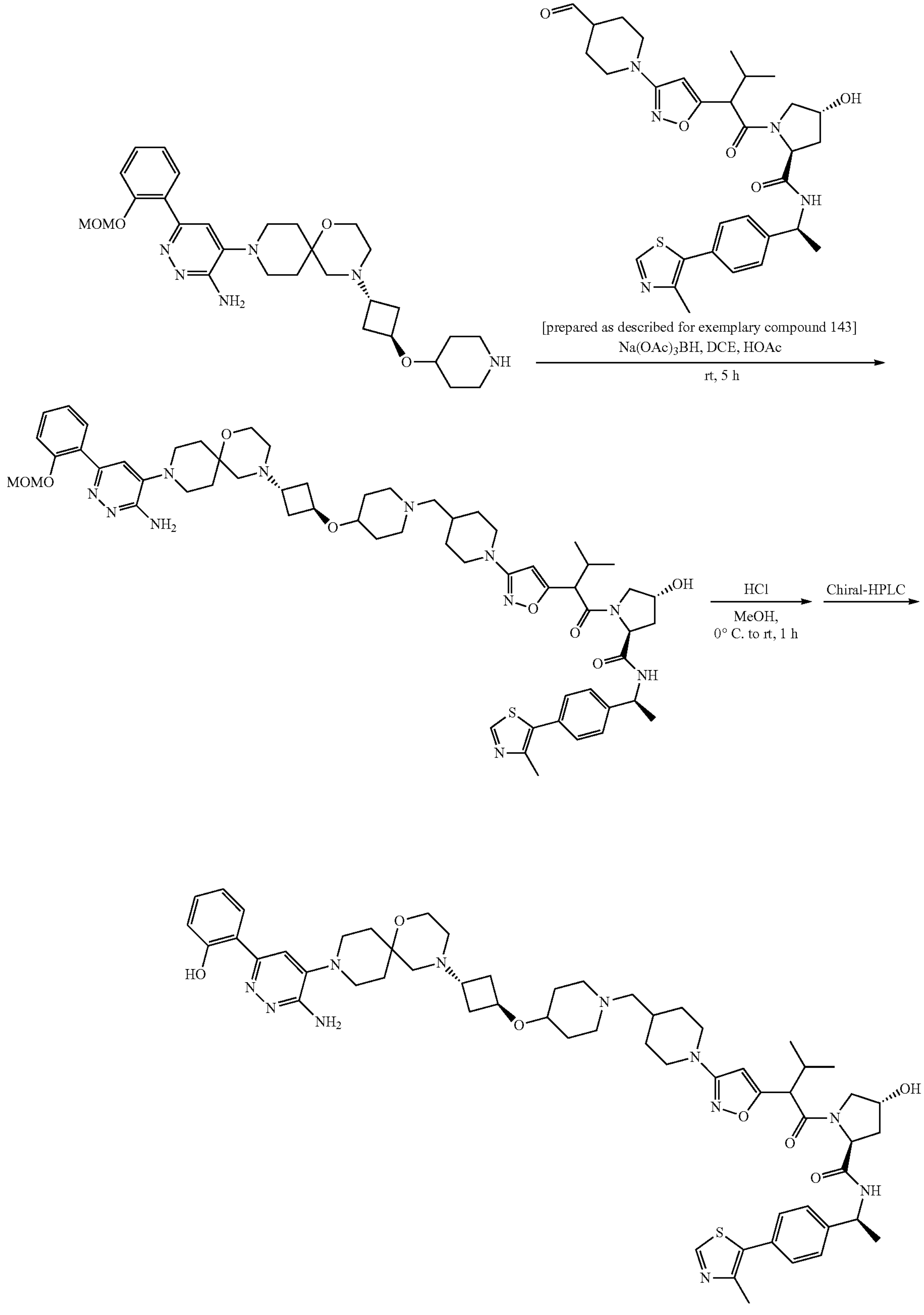
Exemplary Compound 616

Exemplary Synthesis of Exemplary Compound 626

Step 1

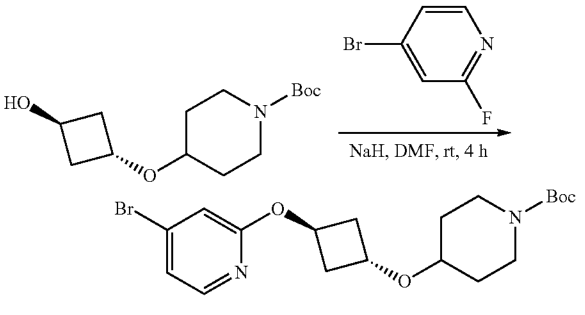

Into a 250-mL round-bottom flask purged and maintained with an inert atmosphere of nitrogen, was placed tert-butyl 4-[(1r,3r)-3-hydroxycyclobutoxy]piperidine-1-carboxylate (5 g, 18.43 mmol, 1.0 equiv), DMF (100 mL), was added NaH (2.22 g, 55.42 mmol, 3.0 equiv, 60% in oil) at 0° C. It was reacted 15 minutes at room temperature. This was followed by the addition of 4-bromo-2-fluoropyridine (3.57 g, 20.27 mmol, 1.1 equiv). The resulting solution was stirred for 4 hours at room temperature. The reaction was then quenched by the addition of 100 mL of water/ice. The resulting solution was extracted with (100 mL×3) of ethyl acetate and the organic layers combined. The resulting mixture was washed with (100 mL×1) of brine. The mixture was dried over anhydrous sodium sulfate. The residue was applied onto a silica gel column eluting with ethyl acetate/petroleum ether (1/2). The collected fractions were combined and concentrated under vacuum. This resulted in 6.3 g (80%) of tert-butyl 4-[(1r,3r)-3-[(4-bromopyridin-2-yl)oxy]cyclobutoxy]piperidine-1-carboxylate as a yellow oil.

Step 2

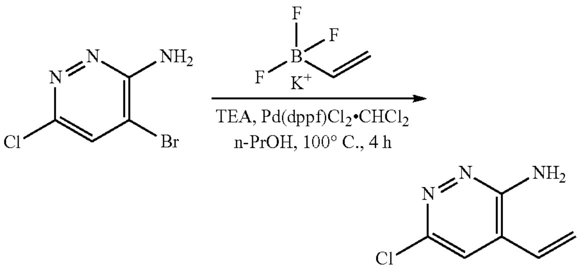

Into a 250-mL round-bottom flask purged and maintained with an inert atmosphere of nitrogen, was placed 4-bromo-6-chloropyridazin-3-amine (5 g, 24.0 mmol, 1.0 equiv), n-propanol (100 mL), TEA (7.28 g, 72.0 mmol, 3 equiv), potassium trifluorovinylborate (2.39 g, 25.0 mmol, 1.05 equiv), and Pd(dppf)$Cl_2$·$CH_2$C12 (1.96 g, 2.39 mmol, 0.10 equiv). The resulting solution was stirred for 4 hours at 100° C. in an oil bath. The solids were filtered out. The residue was applied onto a silica gel column with ethyl acetate/petroleum ether (1/1). The collected fractions were combined and concentrated under vacuum. This resulted in 2.3 g (62%) of 6-chloro-4-ethenylpyridazin-3-amine as a yellow solid.

Step 3

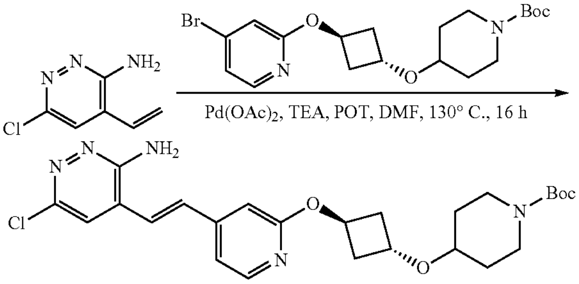

Into a 20-mL sealed tube purged and maintained with an inert atmosphere of nitrogen, was placed 6-chloro-4-ethenylpyridazin-3-amine (910 mg, 5.84 mmol, 1.0 equiv), DMF (14 mL), TEA (1775 mg, 17.5 mmol, 3.0 equiv), tert-butyl 4-[(1r,3r)-3-[(4-bromopyridin-2-yl)oxy]cyclobutoxy]piperidine-1-carboxylate (2.50 g, 5.849 mmol, 1.0 equiv), tri-o-tolylphosphine (1780 mg, 5.85 mmol, 1.0 equiv), Pd(OAc)$_2$ (131 mg, 0.585 mmol, 0.10 equiv). The resulting solution was stirred for 16 hours at 130° C. in an oil bath. The reaction was then quenched by the addition of 30 mL of water. The resulting solution was extracted with (20 mL×3) of ethyl acetate, and the organic layers combined. The resulting mixture was washed with (20 mL×3) of brine. The mixture was dried over anhydrous sodium sulfate. The residue was applied onto a silica gel column eluting with dichloromethane/methanol (10/1). The collected fractions were combined and concentrated under vacuum. This resulted in 625 mg (21%) of tert-butyl 4-[(1r,3r)-3-([4-[(E)-2-(3-amino-6-chloropyridazin-4-yl)ethenyl]pyridin-2-yl]oxy)cyclobutoxy]piperidine-1-carboxylate as a brown solid.

tert-butyl 4-[(1r,3r)-3-([4-[(E)-2-(3-amino-6-chloropyridazin-4-yl)ethenyl]pyridin-2-yl]oxy)cyclobutoxy]piperidine-1-carboxylate was converted to the final compound using procedures described for exemplary compound 143 and other examples above.

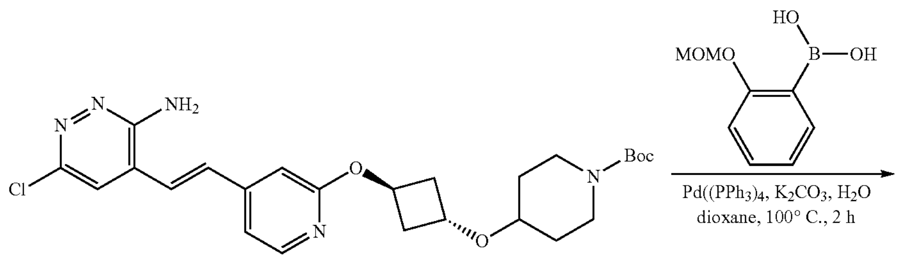

-continued

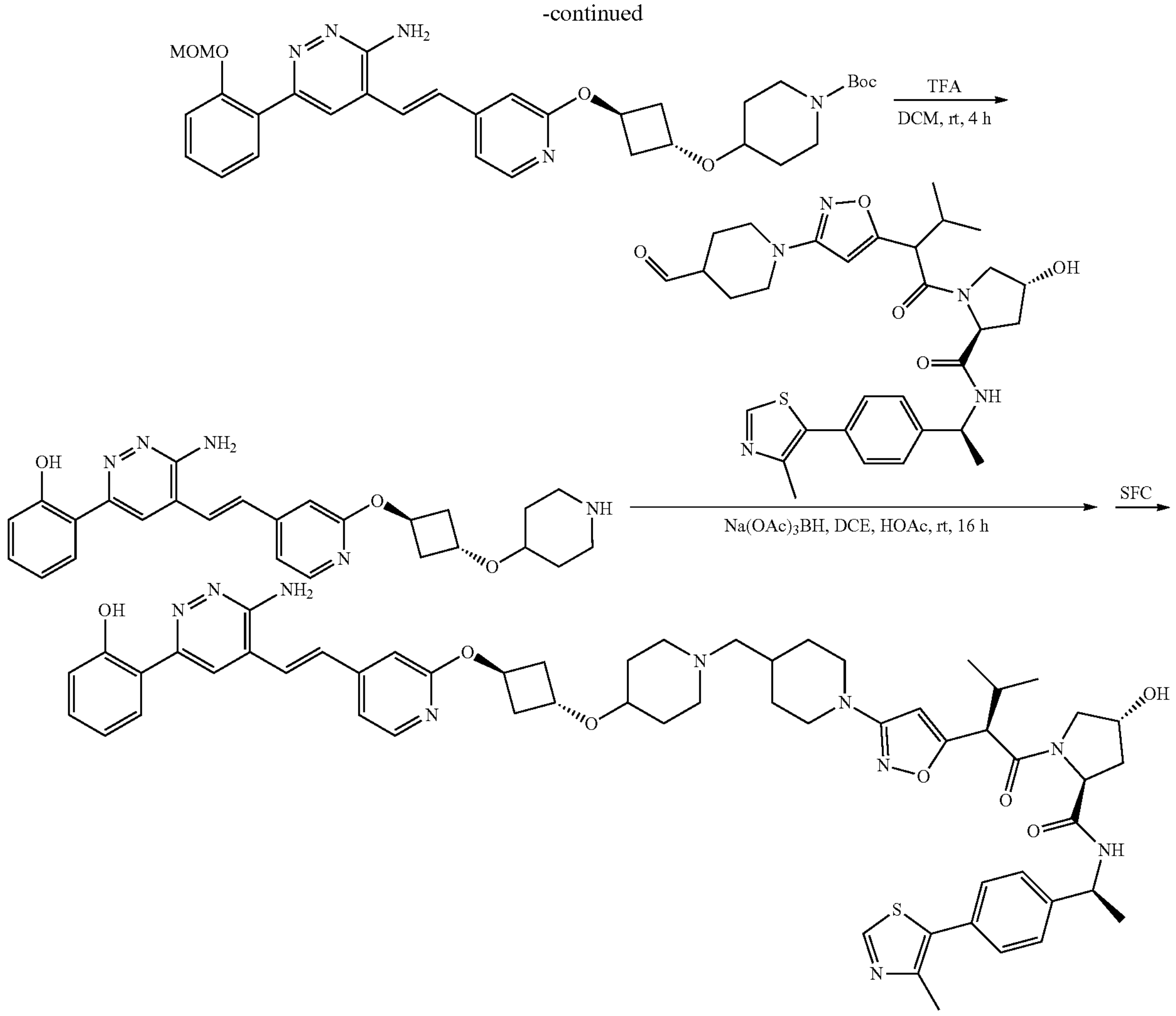

Exemplary Compound 626

Exemplary Synthesis of Exemplary Compound 630

Step 1

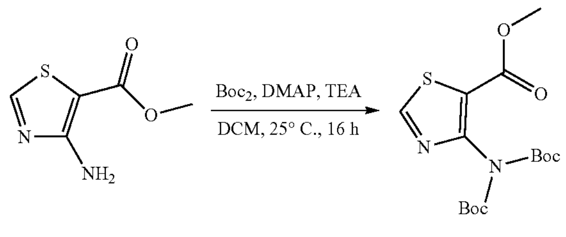

To a solution of methyl 4-aminothiazole-5-carboxylate (0.4 g, 2.53 mmol, 1 eq) and triethylamine (512 mg, 5.06 mmol, 0.7 mL, 2 eq) in dichloromethane (30 mL) was added di-tert-butyl dicarbonate (1.10 g, 5.06 mmol, 1.2 mL, 2 eq) and 4-dimethylaminopyridine (62 mg, 0.50 mmol, 0.2 eq) in one portion at 25° C. under nitrogen. The mixture was stirred at 25° C. for 16 hours. The mixture was concentrated under reduced pressure at 45° C. The residue was purified by silica gel column chromatography (petroleum ether/ethyl acetate=20/1 to 8/1) to afford methyl 4-[bis(tert-butoxycarbonyl)amino]thiazole-5-carboxylate (850 mg) as a yellow oil.

Step 2

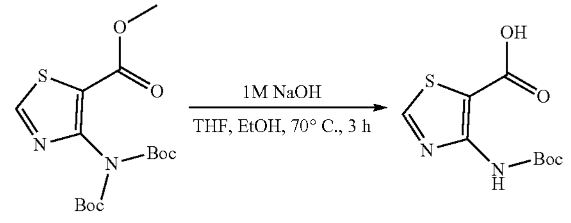

To a solution of methyl 4-[bis(tert-butoxycarbonyl)amino]thiazole-5-carboxylate (850 mg, 2.37 mmol, 1 eq) in ethanol (20 mL) and tetrahydrofuran (10 mL) was added sodium hydroxide in water (1 M, 30 mL) at 25° C., and the mixture was stirred at 70° C. for 3 hours. The reaction mixture was cooled to 25° C., and the pH was adjusted to 4-5 with 2 M hydrochloric acid, and the aqueous phase was extracted with ethyl acetate (30 mL×3). The combined organic phase was washed with brine (20 mL×2), dried with anhydrous sodium sulfate, filtered and concentrated under vacuum. Compound 4-(tert-butoxycarbonylamino)thiazole-5-carboxylic acid (620 mg, crude) was obtained as a white solid.

Step 3

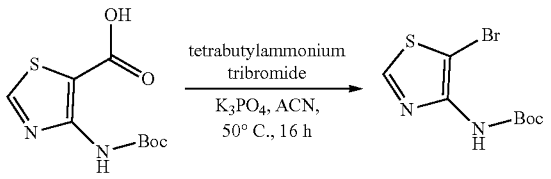 [SMILES: CC(C)(C)OC(=O)Nc1ncsc1C(=O)O ; CC(C)(C)OC(=O)Nc1ncsc1Br]

To a mixture of 4-(tert-butoxycarbonylamino)thiazole-5-carboxylic acid (600 mg, 2.46 mmol, 1 eq) and potassium phosphate (521 mg, 2.46 mmol, 1 eq) in acetonitrile (30 mL) was added tetrabuthylammonium tribromide (2.37 g, 4.91 mmol, 2 eq) in one portion at 30° C. under nitrogen. The mixture was stirred at 50° C. for 16 hours. The mixture was cooled to 20° C. and poured into a mixture of saturated aqueous solution of sodium thiosulfate (20 mL) and saturated aqueous solution of sodium carbonate (20 mL). The aqueous phase was extracted with ethyl acetate (40 mL×2). The combined organic phase was washed with brine (30 mL), dried with anhydrous sodium sulfate, filtered and concentrated in vacuum. The residue was purified by silica gel column chromatography (petroleum ether/ethyl acetate=30/1 to 8/1) to afford tert-butyl N-(5-bromothiazol-4-yl)carbamate (460 mg) as a yellow oil.

Step 4

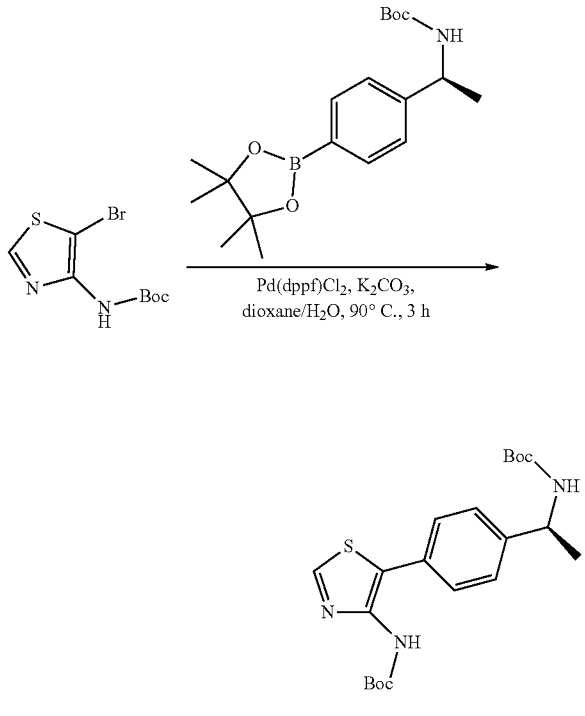

To a mixture of tert-butyl N-[(1R)-1-[4-(4,4,5,5-tetramethyl-1,3,2-dioxaborolan-2-yl)phenyl]ethyl]carbamate (572 mg, 1.65 mmol, 1 eq), potassium carbonate (455 mg, 3.30 mmol, 2 eq) and tert-butyl N-(5-bromothiazol-4-yl)carbamate (460 mg, 1.65 mmol, 1 eq) in Water (3 mL) and dioxane (18 mL) was added [1,1'-bis(diphenylphosphino)ferrocene] dichloropalladium] (96 mg, 0.13 mmol, 0.08 eq) in one portion at 20° C. under nitrogen. The mixture was stirred at 90° C. for 2 hours. The mixture was cooled to 20° C. and poured into ice-water (w/w=1/1, 20 mL) and stirred for 10 minutes. The aqueous phase was extracted with ethyl acetate (30 mL×3). The combined organic phase was washed with brine (10 mL×2), dried with anhydrous sodium sulfate, filtered and concentrated in vacuum. The residue was purified by silica gel chromatography (petroleum ether/ethyl acetate=30/1 to 5/1) to afford tert-butyl N-[5-[4-[(1S)-1-(tert-butoxycarbonylamino)ethyl]phenyl]thiazol-4-yl]carbamate (620 mg, crude) as a yellow solid.

Step 5

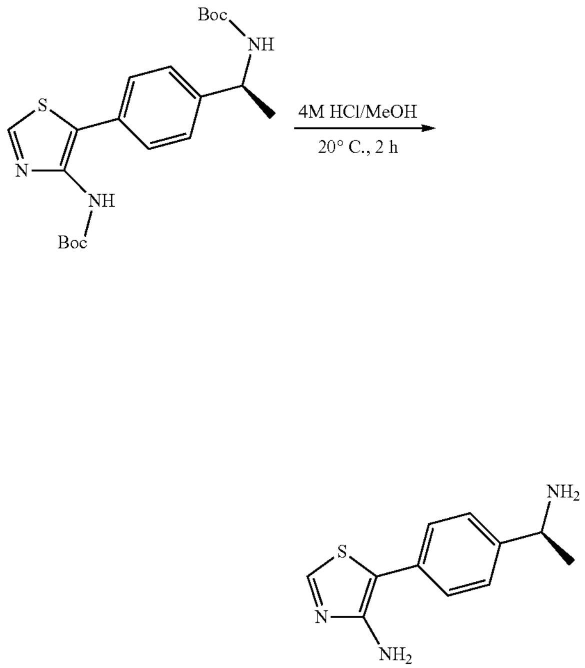

A solution of tert-butyl N-[5-[4-[(1S)-1-(tert-butoxycarbonylamino)ethyl]phenyl]thiazol-4-yl]carbamate (620 mg, 1.48 mmol, 1 eq) in hydrochloric acid/methanol (4 M, 10 mL) was stirred at 20° C. for 2 h. The mixture was concentrated under reduced pressure at 45° C. The crude product 5-[4-[(1S)-1-aminoethyl]phenyl]thiazol-4-amine hydrochloride (406 mg, crude) was obtained as a yellow solid.

5-[4-[(1S)-1-aminoethyl]phenyl]thiazol-4-amine was converted to the title compound according to the scheme below using procedures described for other examples above.

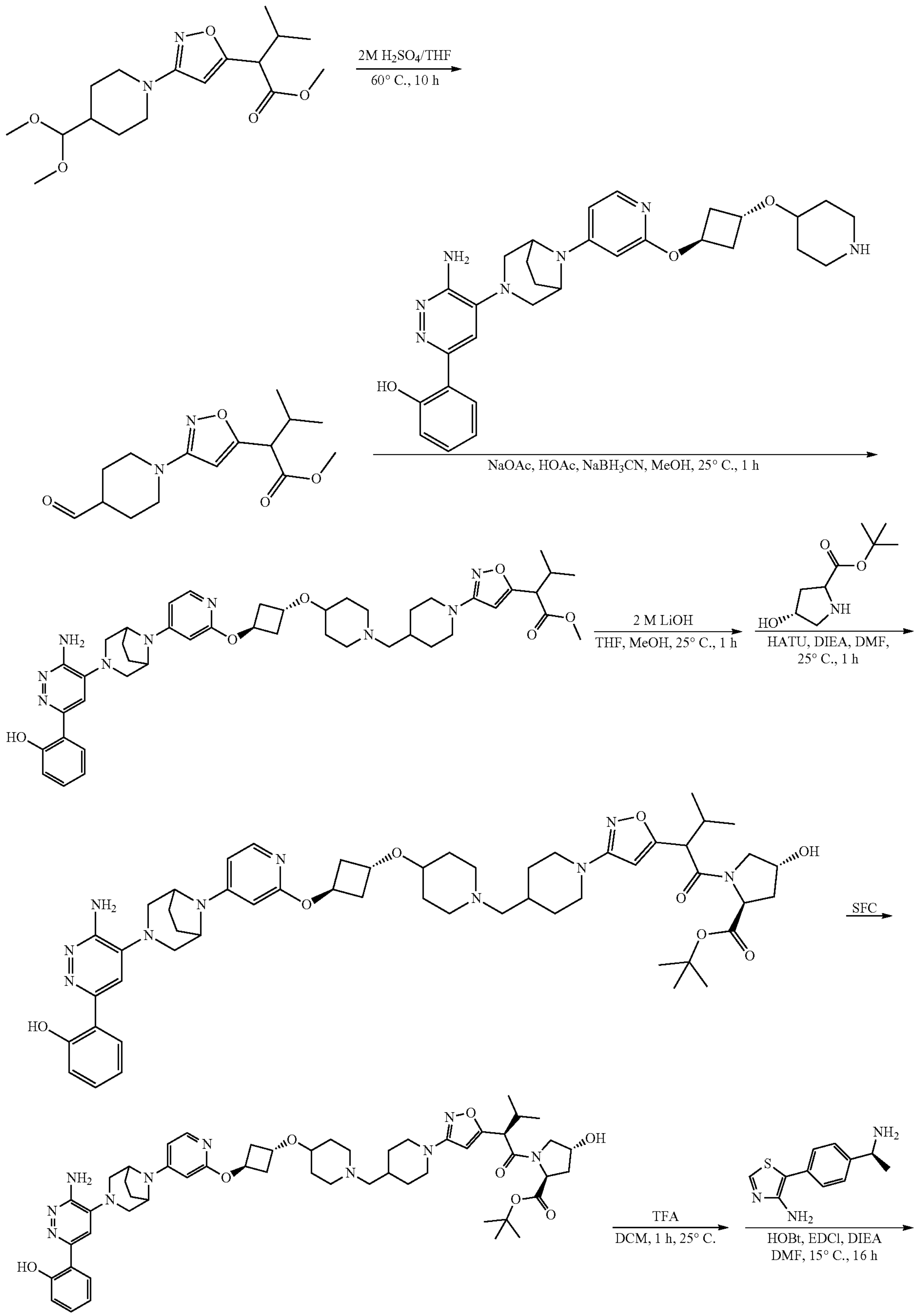
2M $H_2SO_4$/THF
60° C., 10 h
NaOAc, HOAc, $NaBH_3CN$, MeOH, 25° C., 1 h
2 M LiOH
THF, MeOH, 25° C., 1 h
HATU, DIEA, DMF,
25° C., 1 h
SFC
TFA
DCM, 1 h, 25° C.
HOBt, EDCl, DIEA
DMF, 15° C., 16 h -continued
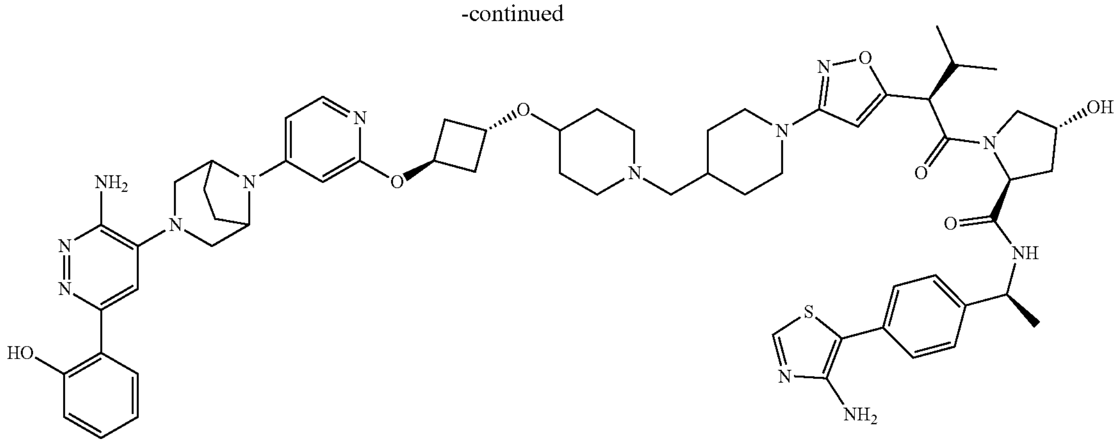
Exemplary Compound 630
Exemplary Synthesis of Exemplary Compound 638
Prepared according to the schemes below using procedures analogous to those described for other examples above (in particular, exemplary compound 238 and Exemplary compound 607).
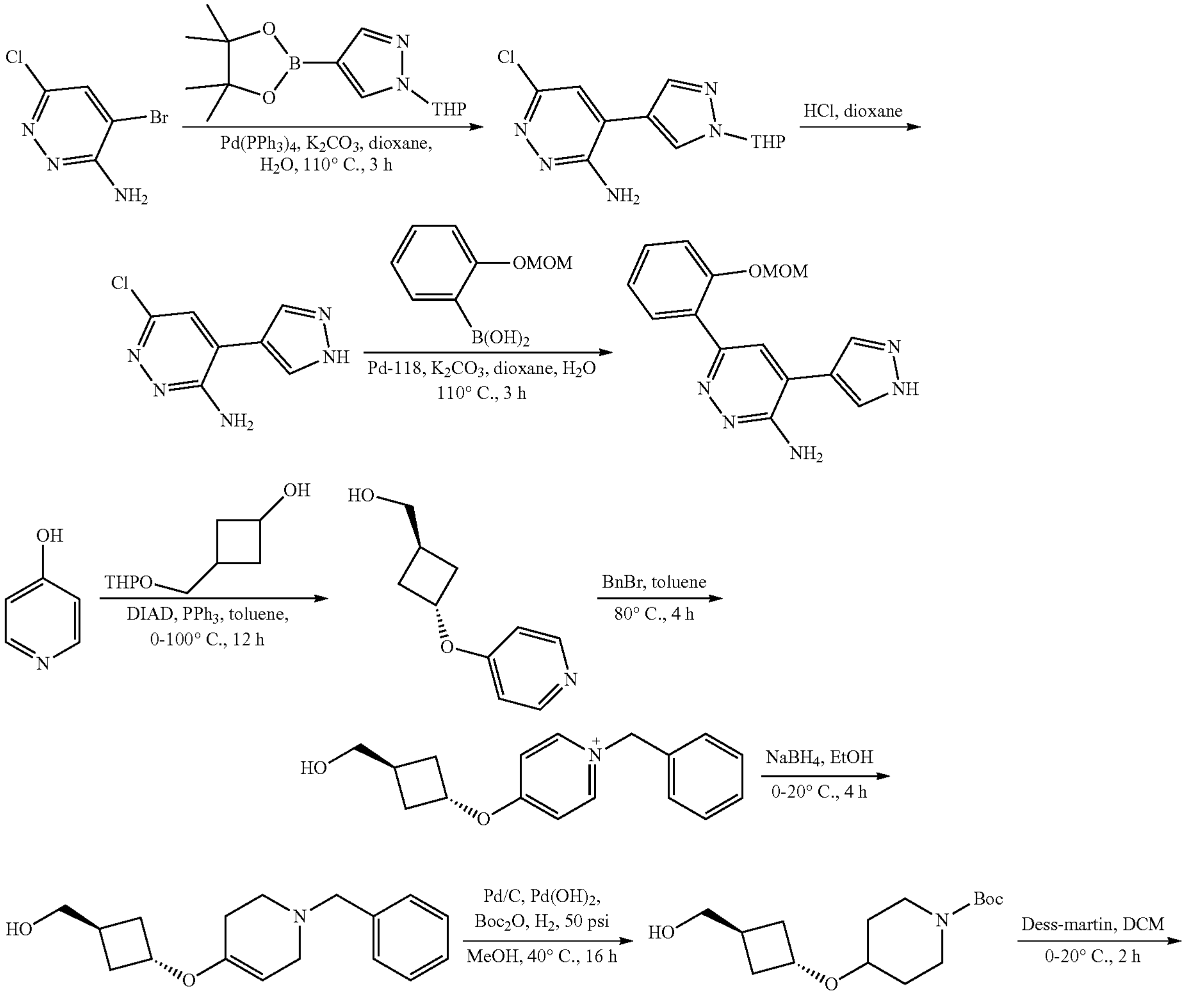

-continued
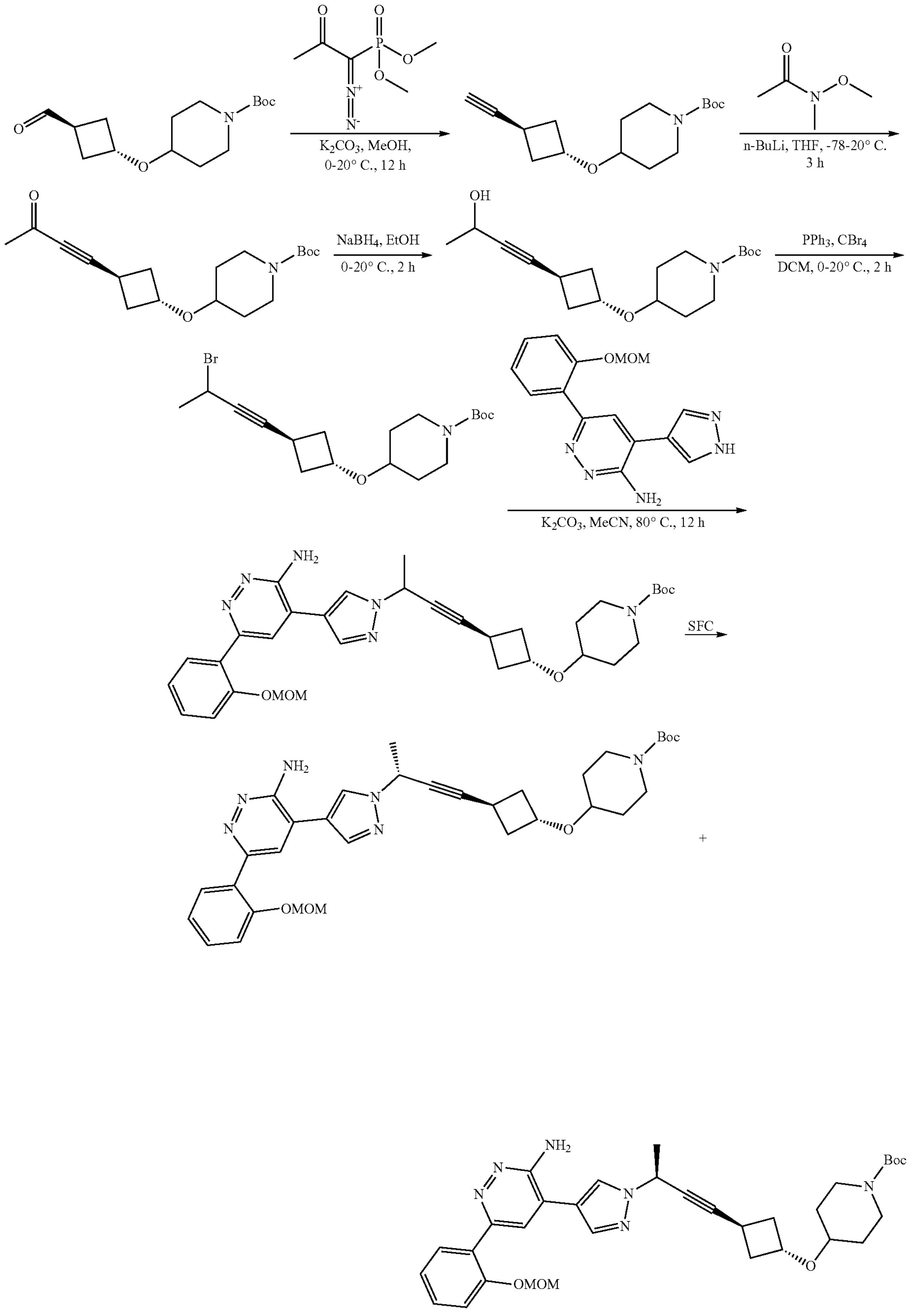

-continued
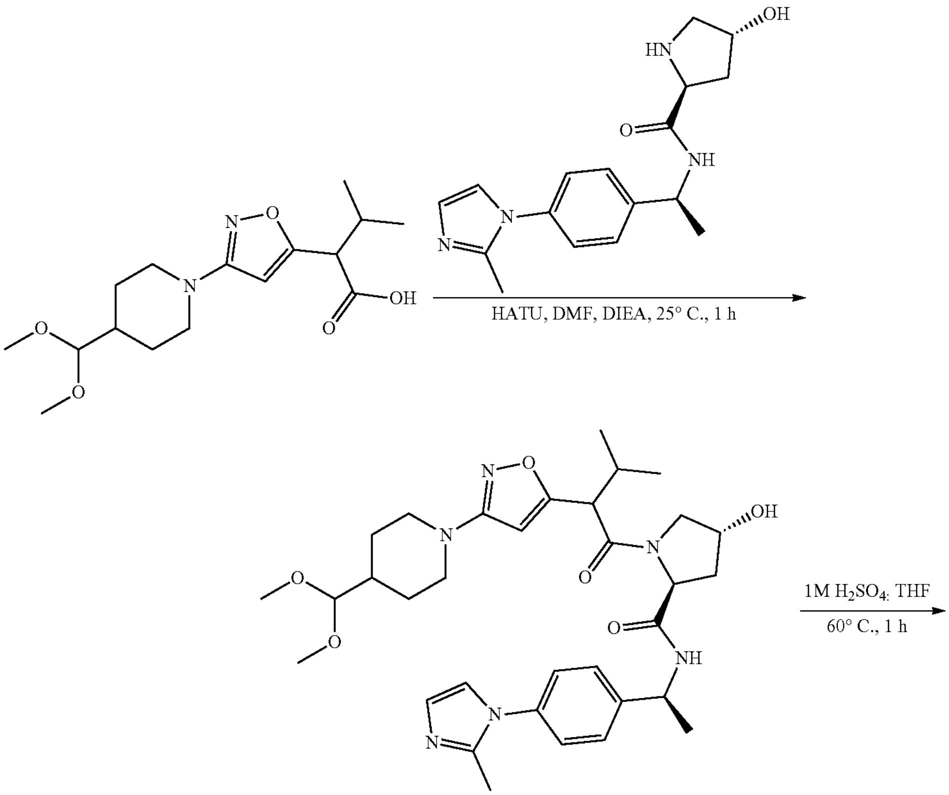
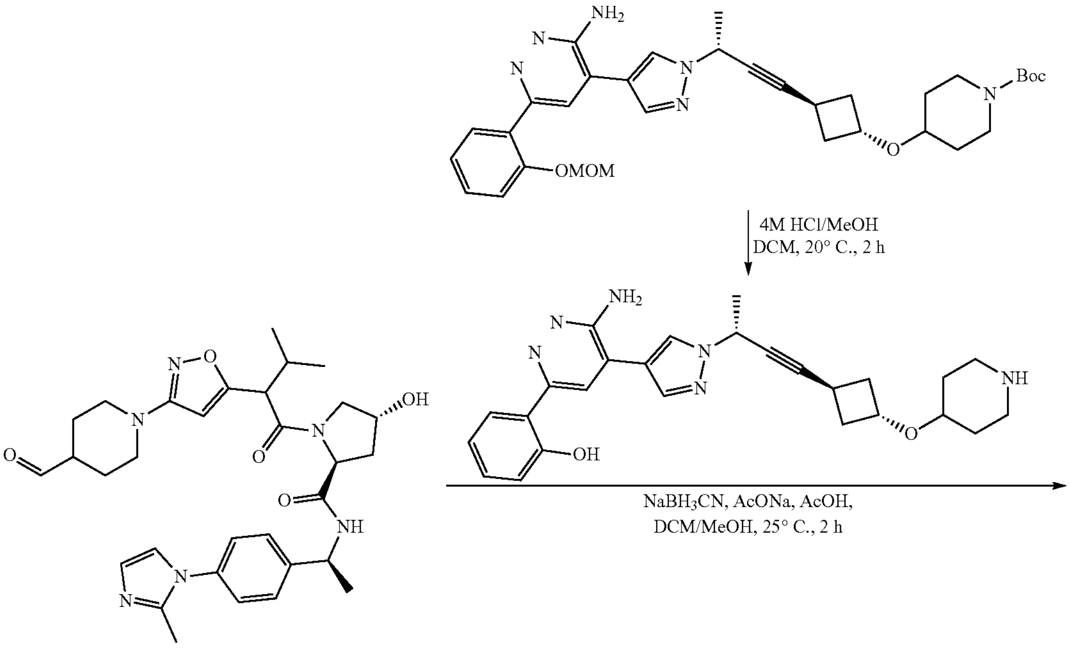

-continued
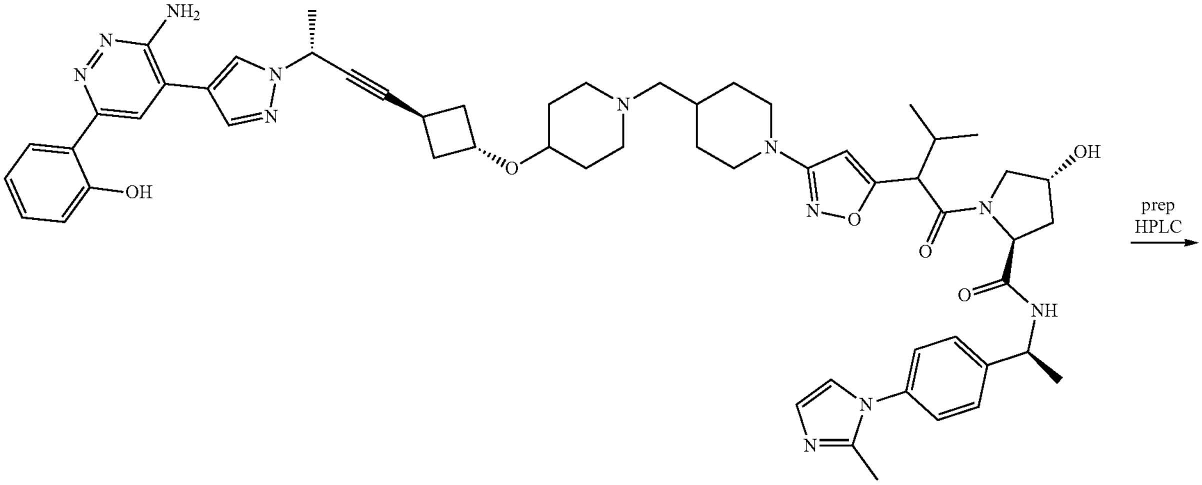
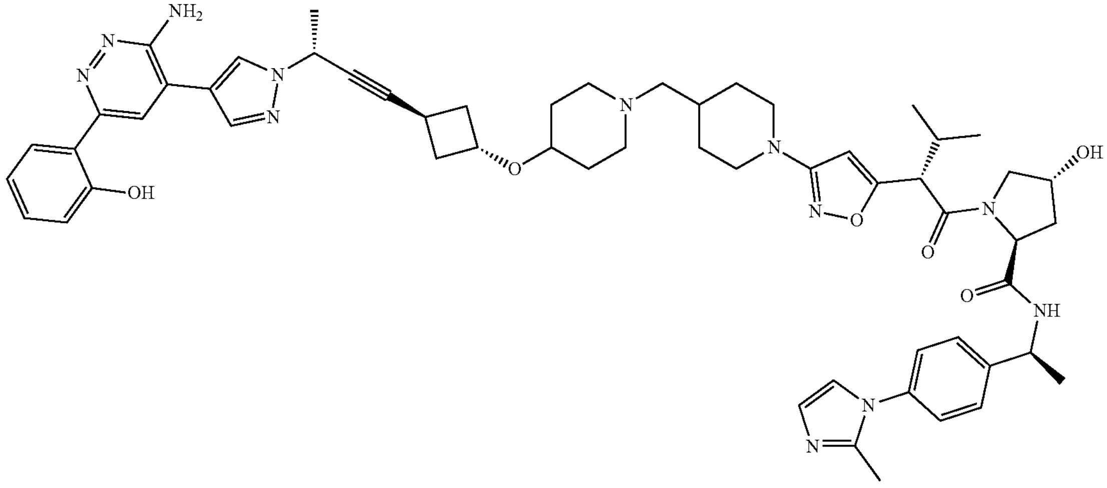
+
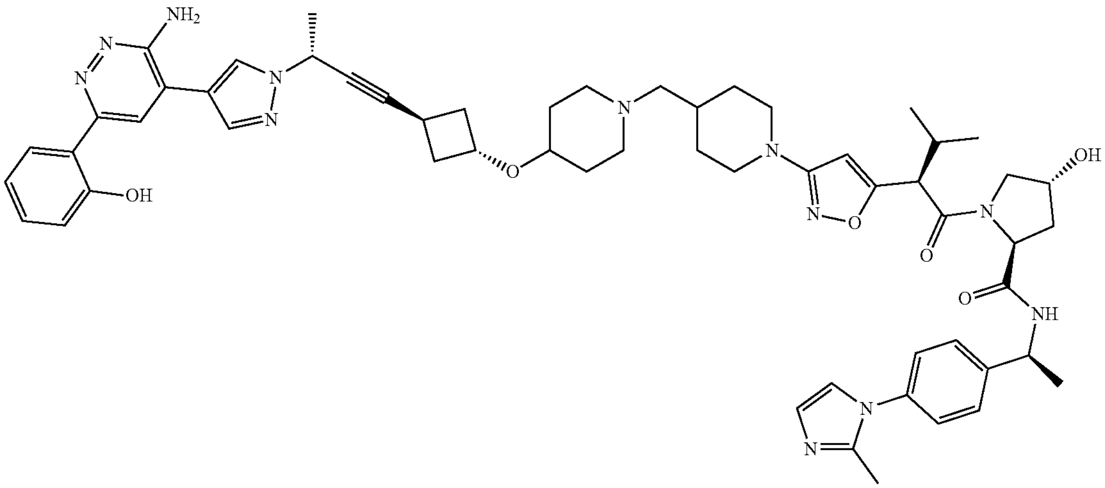
Exemplary Compound 638

Exemplary Synthesis of Exemplary Compound 640
Prepared according to the schemes below using procedures described for exemplary compound 203, exemplary compound 143, and other examples above.
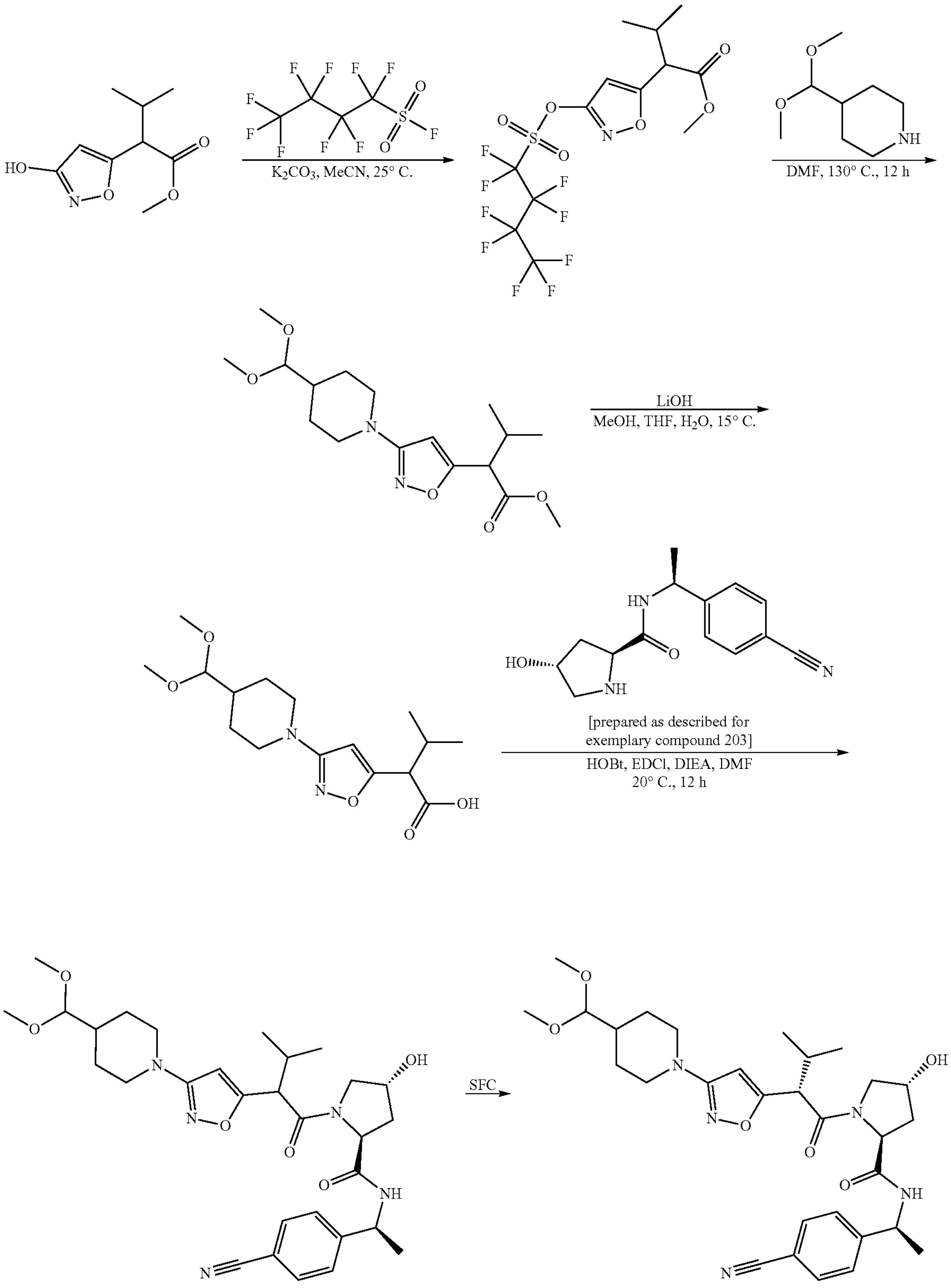
+

-continued
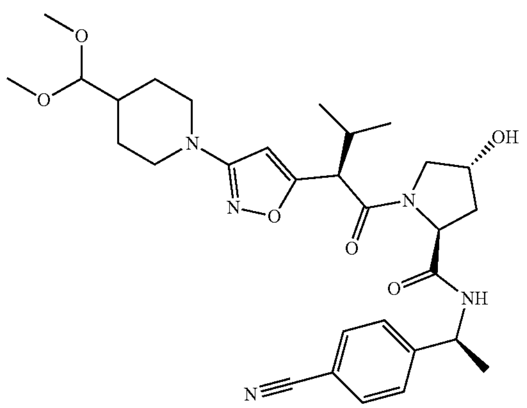
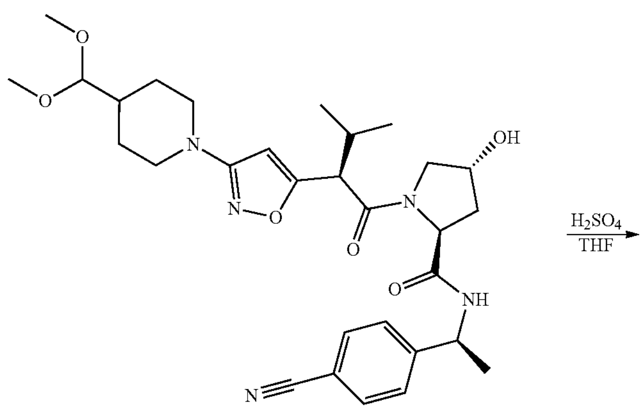
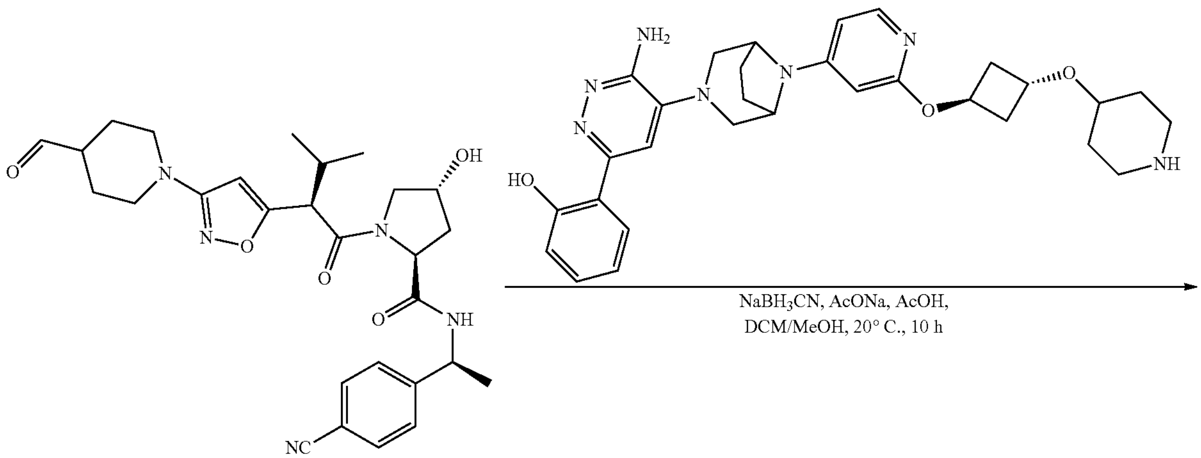

-continued
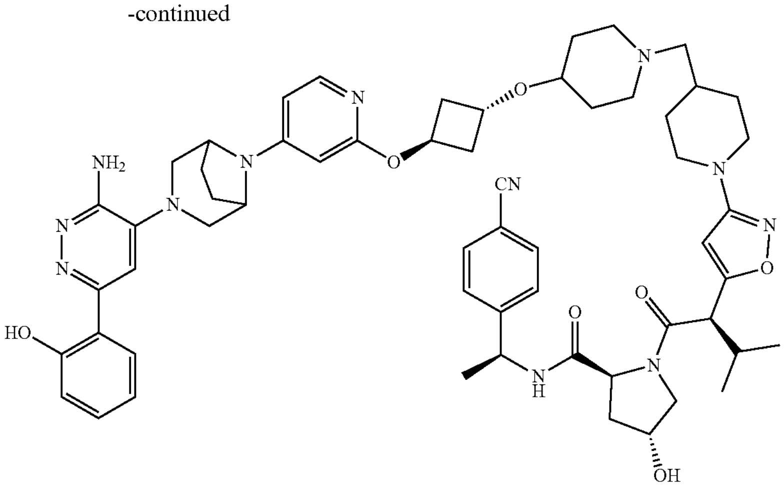
Exemplary Compound 640
Exemplary Synthesis of Exemplary Compound 642
Prepared according to the scheme below using procedures described for exemplary compound 143 and other examples above.
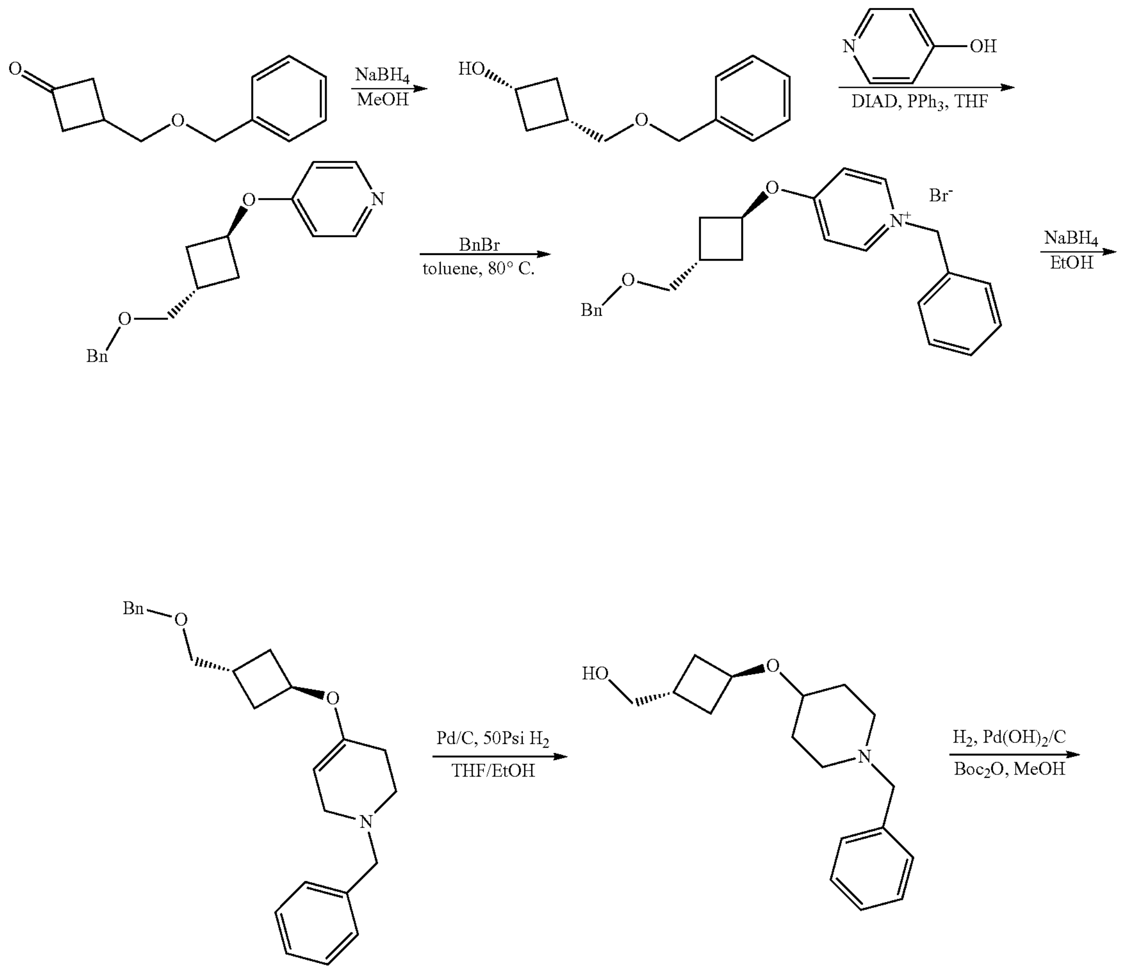

-continued
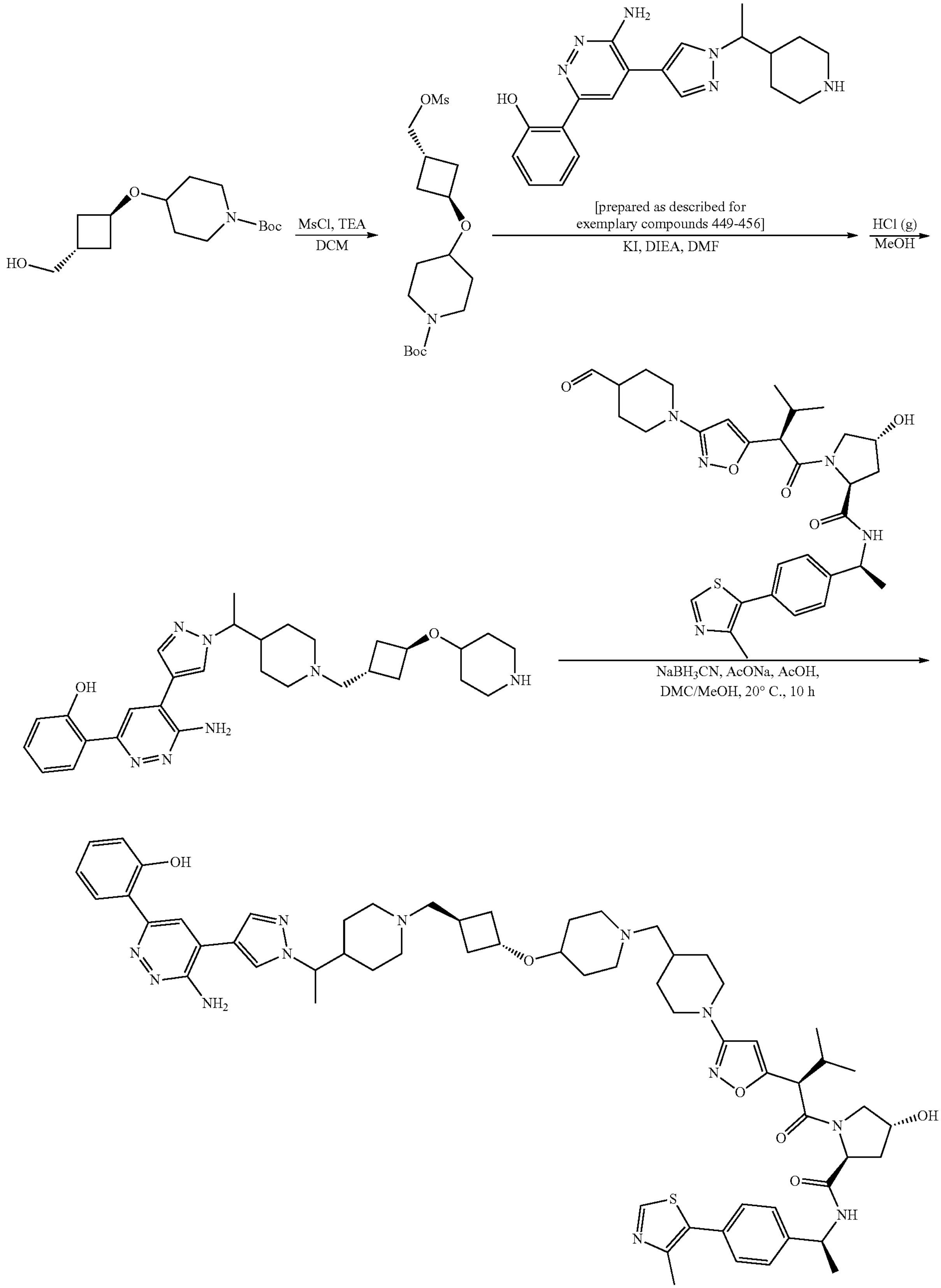
Exemplary Compound 642

Exemplary Synthesis of Exemplary Compound 664

Intermediate 2-(6-amino-5-(1-(1-(1-(((1s,3s)-3-(piperidin-4-yloxy)cyclobutyl)methyl)piperidin-4-yl)ethyl)-1H-pyrazol-4-yl)pyridazin-3-yl)phenol was prepared according to the scheme below using procedures analogous to those described for other examples above.

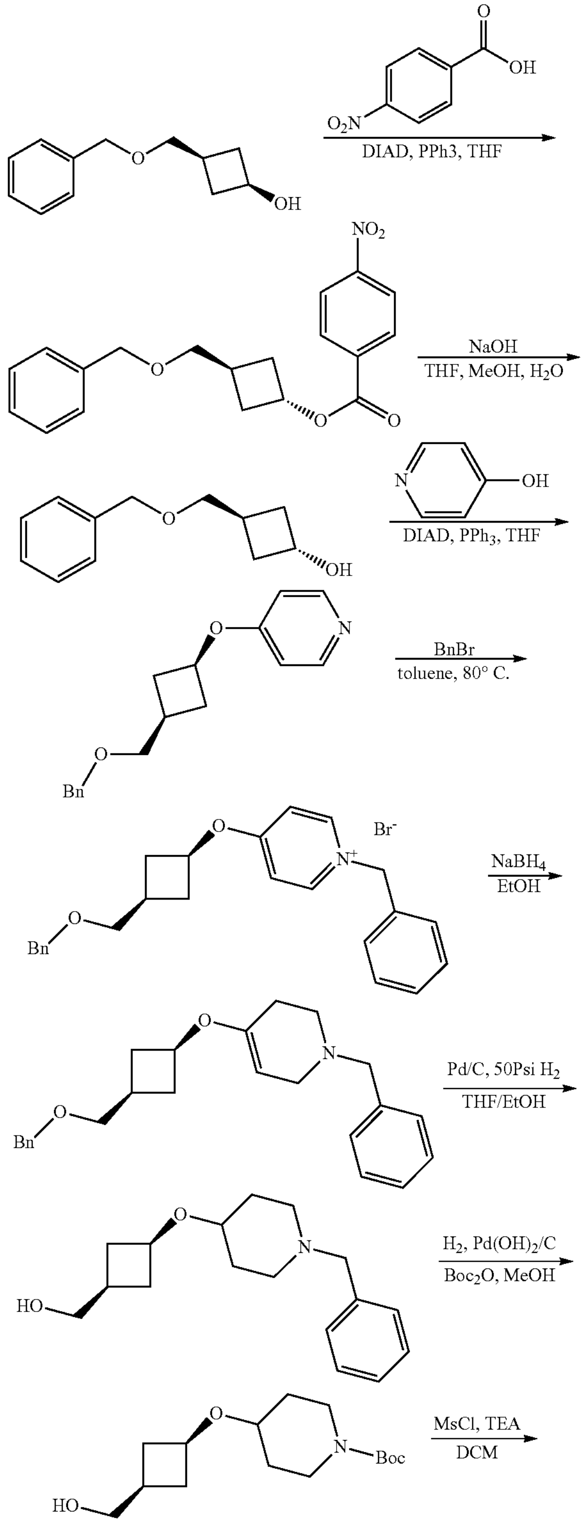

-continued

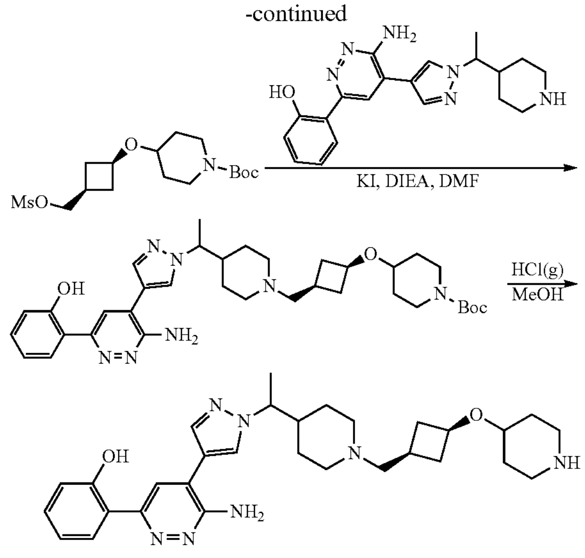

2-(6-amino-5-(1-(1-(1-(((1s,3s)-3-(piperidin-4-yloxy)cyclobutyl)methyl)piperidin-4-yl)ethyl)-1H-pyrazol-4-yl)pyridazin-3-yl)phenol was converted to the title compound as described for exemplary compound 143 and other examples above.

Exemplary Synthesis of Exemplary Compound 665

Intermediate 2-(6-amino-5-(1-(1-(1-((1s,3s)-3-(piperidin-4-yloxy)cyclobutyl)piperidin-4-yl)ethyl)-1H-pyrazol-4-yl)pyridazin-3-yl)phenol was prepared according to the scheme below.

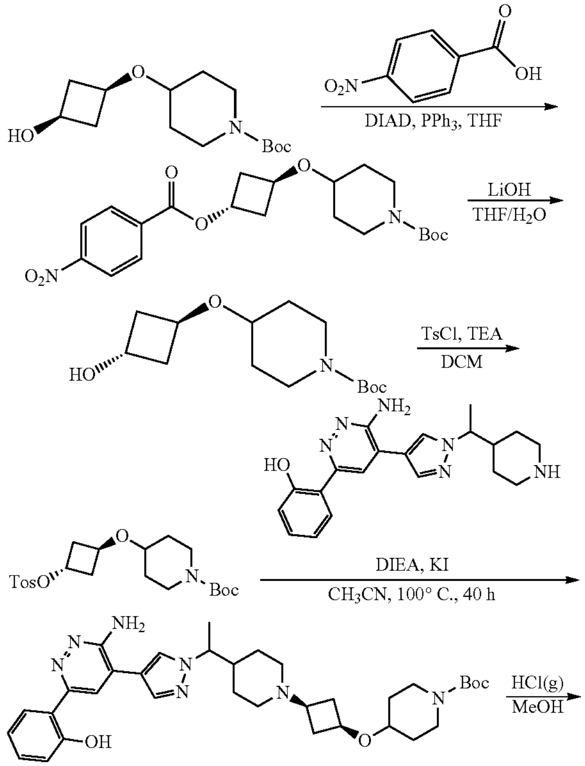

-continued

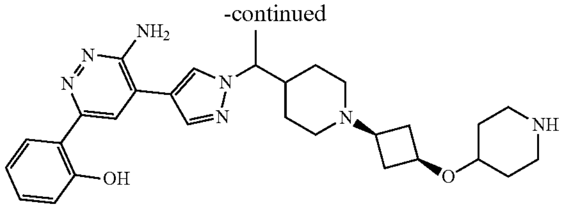

2-(6-amino-5-(1-(1-(1-((1s,3s)-3-(piperidin-4-yloxy)cyclobutyl)piperidin-4-yl)ethyl)-1H-pyrazol-4-yl)pyridazin-3-yl)phenol was converted to the title compound as described for exemplary compound 143 and other examples above.

Exemplary Synthesis of Exemplary Compound 678

Intermediate (2S,4R)—N—((S)-1-(4-ethynylphenyl)ethyl)-1-((R)-2-(3-(4-formylpiperidin-1-yl)isoxazol-5-yl)-3-methylbutanoyl)-4-hydroxypyrrolidine-2-carboxamide was prepared according to the scheme below.

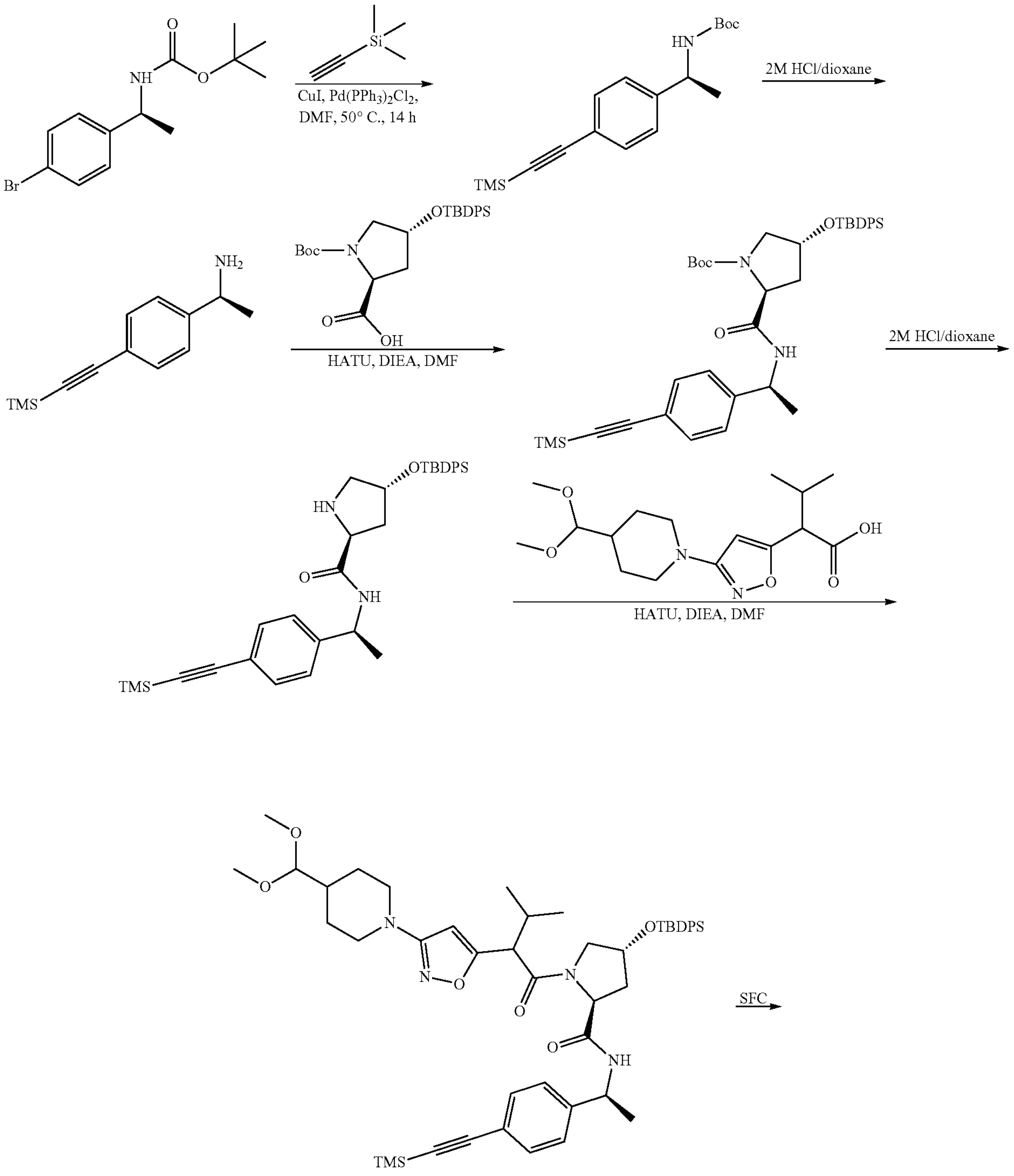

-continued
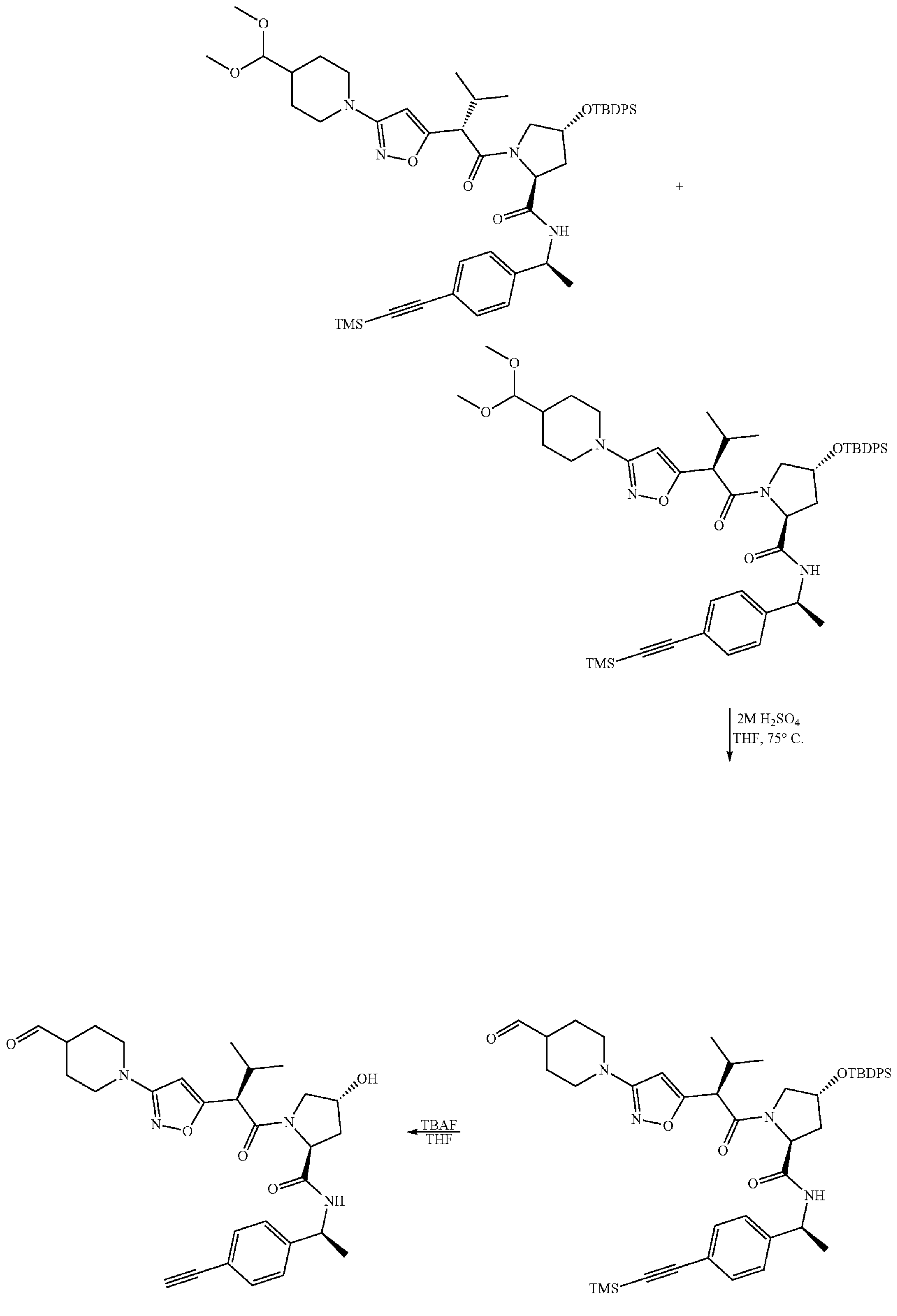

(2S,4R)—N—((S)-1-(4-ethynylphenyl)ethyl)-1-((R)-2-(3-(4-formylpiperidin-1-yl)isoxazol-5-yl)-3-methylbutanoyl)-4-hydroxypyrrolidine-2-carboxamide was converted to the title compound using procedures described for exemplary compound 143 above.

Exemplary Synthesis of Exemplary Compound 692

Step 1

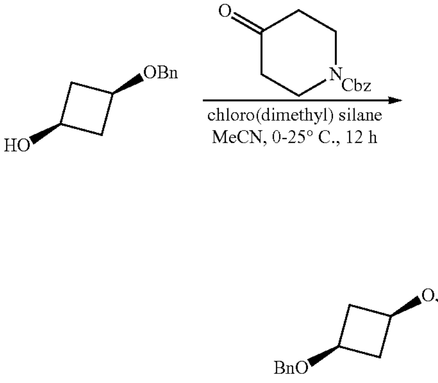

A mixture of 3-benzyloxycyclobutanol (100 g, 561.08 mmol, 1 eq) and benzyl 4-oxopiperidine-1-carboxylate (143.97 g, 617.19 mmol, 123.1 mL, 1.1 eq) in acetonitrile (2000 mL) was degassed and purged with nitrogen for 3 times. To the mixture was then added chloro(dimethyl)silane (53.09 g, 561.08 mmol, 1 eq) at 0° C. The mixture was stirred at 25° C. for 12 hours under nitrogen atmosphere. The reaction mixture was diluted with water (2 L). The organic layer was extracted with ethyl acetate (1 L×2). The combined organic layer was washed with brine (500 mL). The organic layer was dried over anhydrous sodium sulfate, filtered and concentrated under vacuum to get the residue. The residue was purified by silica gel chromatography (petroleum ether/ethyl acetate=30/1 to 20/1) to get the product. Benzyl 4-(3-benzyloxycyclobutoxy)piperidine-1-carboxylate (89 g, 225.04 mmol) was obtained as a colorless oil.

Step 2

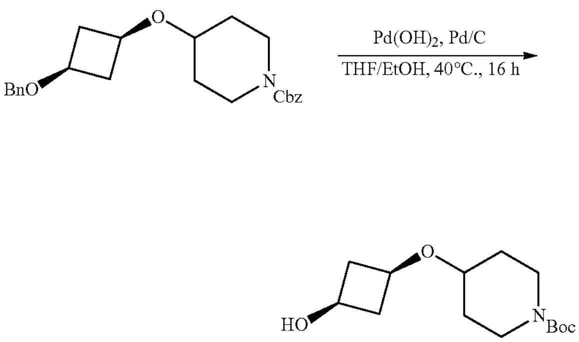

To a solution of benzyl 4-(3-benzyloxycyclobutoxy)piperidine-1-carboxylate (65 g, 164.35 mmol, 1 eq) in ethanol (300 mL) and tetrahydrofuran (300 mL) was added palladium on activated carbon catalyst (6 g, 1.44 mmol, 10% purity), palladium hydroxide on activated carbon catalyst (6 g, 8.54 mmol, 20% purity) and di-tert-butyl dicarbonate (53.80 g, 246.53 mmol, 56.6 mL, 1.5 eq) under nitrogen atmosphere. The suspension was degassed and purged with hydrogen three times. The mixture was stirred under hydrogen (50 Psi) at 40° C. for 16 hours. The reaction mixture was filtered and concentrated under reduced pressure to give a residue. The crude product was purified by silica gel chromatography (petroleum ether/ethyl acetate=50/1, 0/1). The crude product tert-butyl 4-(3-hydroxycyclobutoxy)piperidine-1-carboxylate (30.8 g, 113.5 mmol) was obtained as a white solid.

Step 3

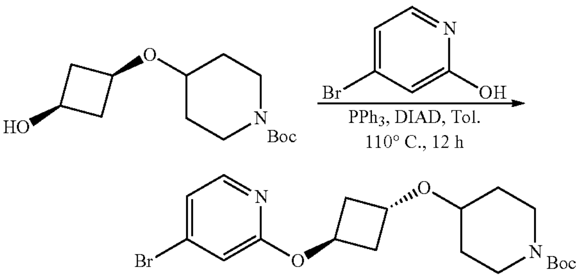

A mixture of tert-butyl 4-(3-hydroxycyclobutoxy)piperidine-1-carboxylate (5 g, 18.43 mmol, 1 eq), 4-bromopyridin-2-ol (3.85 g, 22.11 mmol, 1.2 eq), triphenylphosphine (7.25 g, 27.64 mmol, 1.5 eq), and diisopropylazodicarboxylate (5.59 g, 27.64 mmol, 5.4 mL, 1.5 eq) in toluene (40 mL) was degassed and purged with nitrogen for 3 times, and then the mixture was stirred at 110° C. for 12 hours under nitrogen atmosphere. The reaction mixture was cooled to 20° C., then filtered and concentrated under reduced pressure to give a residue. The residue was purified by silica gel chromatography (petroleum ether/ethyl acetate=50/1 to 10/1) to get the product. tert-bButyl 4-[3-[(4-bromo-2-pyridyl)oxy]cyclobutoxy]piperidine-1-carboxylate (7 g, 16.38 mmol) was obtained as a light yellow oil.

Step 4

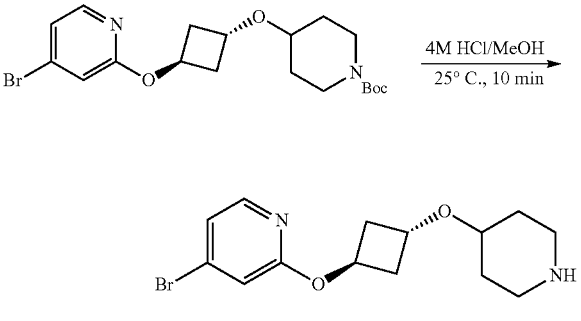

To a solution of tert-butyl 4-[3-[(4-bromo-2-pyridyl)oxy] cyclobutoxy]piperidine-1-carboxylate (4 g, 9.36 mmol, 1 eq) in hydrochloride/methanol (4 M, 25 mL, 10.68 eq) was stirred at 25° C. for 10 min. The reaction solution was concentrated under vacuum to get the crude product. The crude product was used into next step directly without any further purification. 4-Bromo-2-[3-(4-piperidyloxy)cyclobutoxy]pyridine hydrochloride (3.2 g, 8.80 mmol) was obtained as a light yellow oil.

Step 5

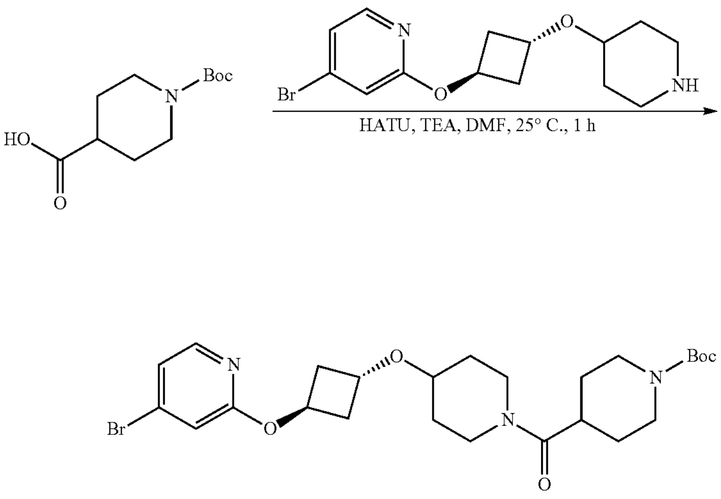

To a solution of 4-bromo-2-[3-(4-piperidyloxy)cyclobutoxy]pyridine (3.2 g, 8.80 mmol, 1 eq, hydrochloride) in N,N-dimethylformamide (40 mL) was added triethylamine (5.34 g, 52.79 mmol, 7.4 mL, 6 eq) and 1-tert-butoxycarbonylpiperidine-4-carboxylic acid (2.42 g, 10.56 mmol, 1.2 eq). After addition, the mixture was stirred at 20° C. for 2 minutes. Then to the mixture was added O-(7-azabenzotriazol-1-yl)-N,N,N',N'-tetramethyluronium hexafluorophosphate (4.01 g, 10.56 mmol, 1.2 eq) at 0° C., and the mixture was stirred at 20° C. for 1 hour under nitrogen atmosphere. The reaction mixture was diluted with water (40 mL) and extracted with ethyl acetate (100 mL×2). The combined organic phase was washed with saturated brine (100 mL), dried with anhydrous sodium sulfate, filtered and concentrated in vacuum. The residue was purified by prep-HPLC (column: Phenomenex luna c18 250 mm*100 mm*10 um; mobile phase: [water (0.225% FA)–ACN]; B %: 40%-70%, 20 min). Compound tert-butyl 4-[4-[3-[(4-bromo-2-pyridyl)oxy]cyclobutoxy]piperidine-1-carbonyl] piperidine-1-carboxylate (4.5 g, 8.36 mmol) was obtained as a white solid.

Step 6

To a solution of tert-butyl 4-[4-[3-[(4-bromo-2-pyridyl)oxy]cyclobutoxy]piperidine-1-carbonyl]piperidine-1-carboxylate (3.5 g, 6.50 mmol, 1 eq) in tetrahydrofuran (70 mL) was added zirconium(IV) chloride (3.03 g, 13.0 mmol, 1.1 mL, 2 eq) at −20° C., and the mixture was stirred at −20° C. for 1 hour. Then methylmagnesium bromide (3 M, 13 mL, 6 eq) was added into the mixture dropwise at −10° C. The mixture was stirred at 30° C. for 12 hours. The reaction mixture was diluted with saturated ammonium chloride solution (100 mL) and extracted with ethyl acetate (200 mL×2). The combined organic phase was washed with saturated brine (100 mL), dried with anhydrous sodium sulfate, filtered and concentrated in vacuum. The residue was purified by prep-HPLC (column: Phenomenex Synergi Max-RP 250*50 mm*10 um; mobile phase: [water (0.1% TFA)–ACN]; B %: 25%-50%, 20 min). Compound tert-butyl 4-[1-[4-[3-[(4-bromo-2-pyridyl)oxy]cyclobutoxy]-1-piperidyl]-1-methyl-ethyl]piperidine-1-carboxylate (1 g, 1.81 mmol, 27% yield) was obtained as a light yellow oil.

tert-Butyl 4-[1-[4-[3-[(4-bromo-2-pyridyl)oxy]cyclobutoxy]-1-piperidyl]-1-methyl-ethyl]piperidine-1-carboxylate

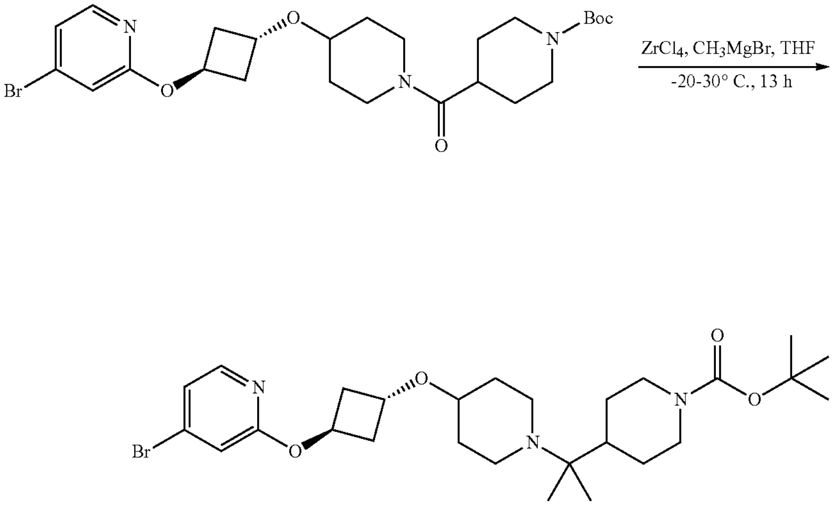

was converted to the title compound according to the scheme below using procedures analogous to those described for exemplary compound 143, exemplary compound 616, and other examples.
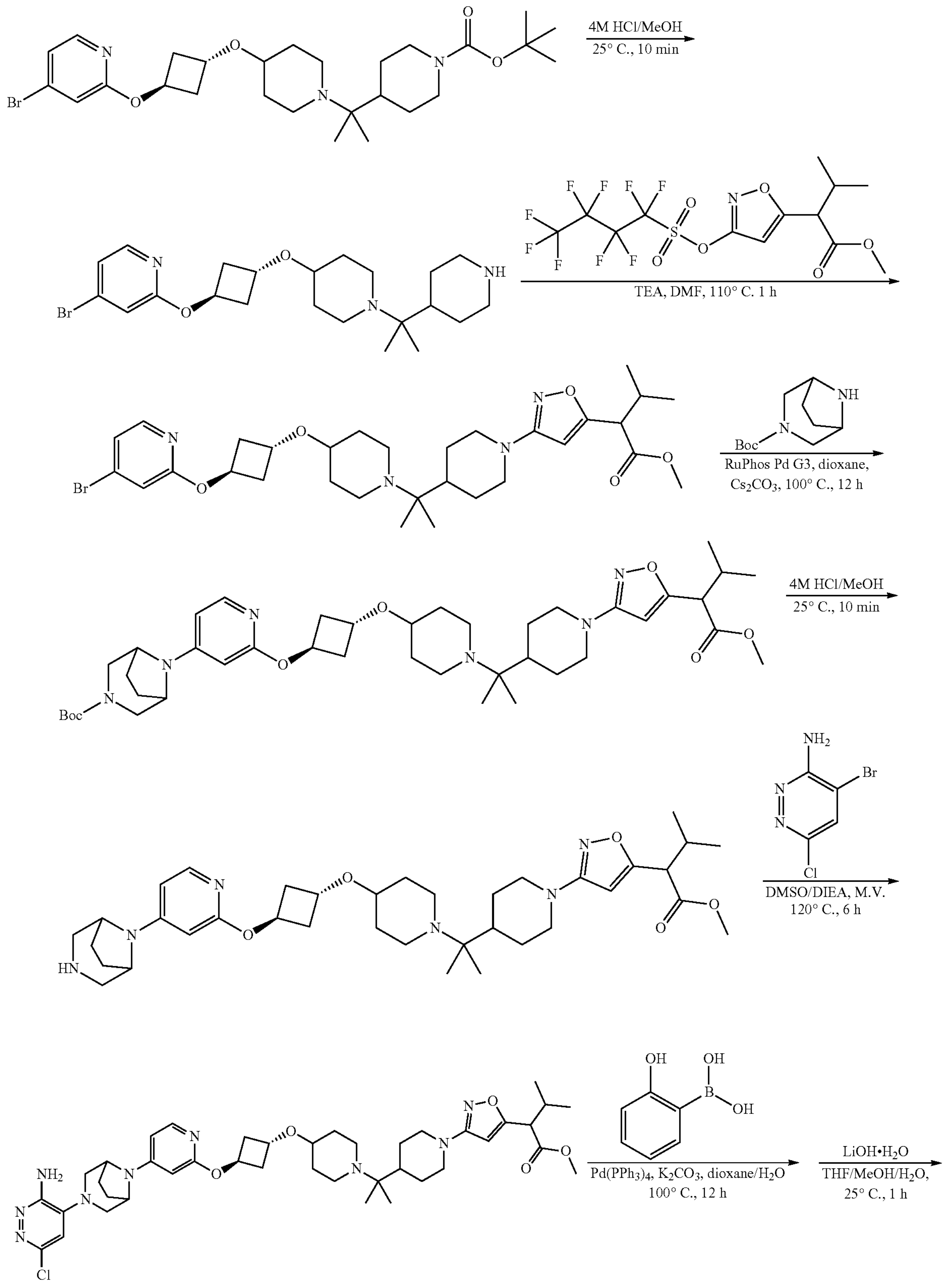

-continued
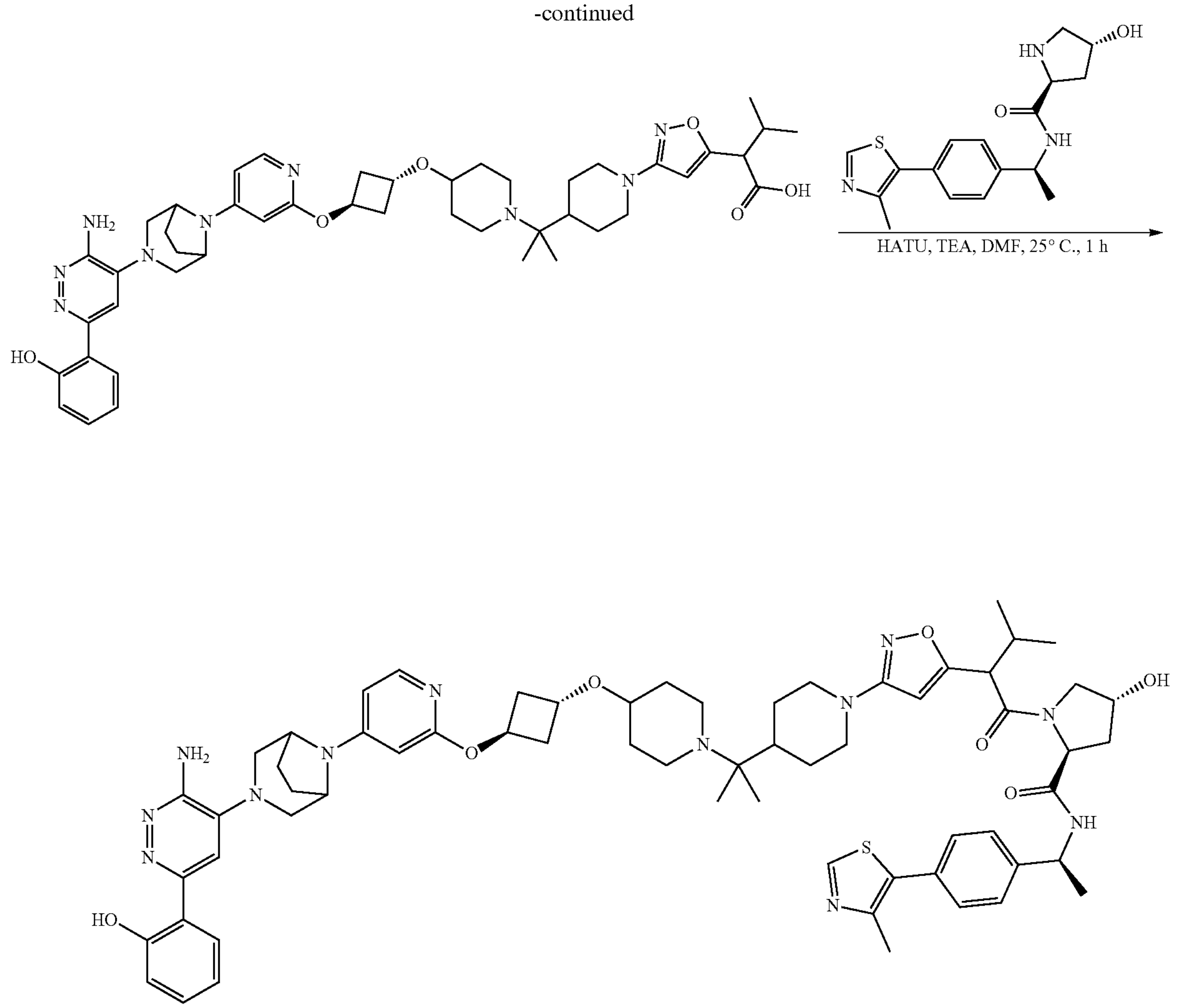
Exemplary Compound 692
Exemplary Synthesis of Exemplary Compound 698
Prepared according to the scheme below using procedures analogous to those described in exemplary compound 638 and exemplary compound 640.
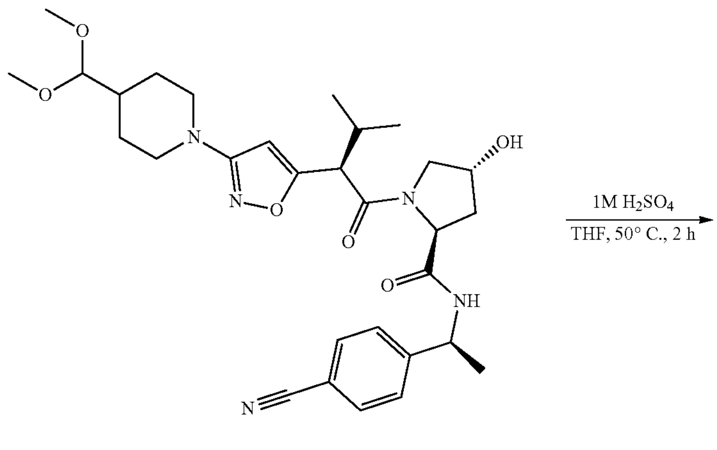

-continued
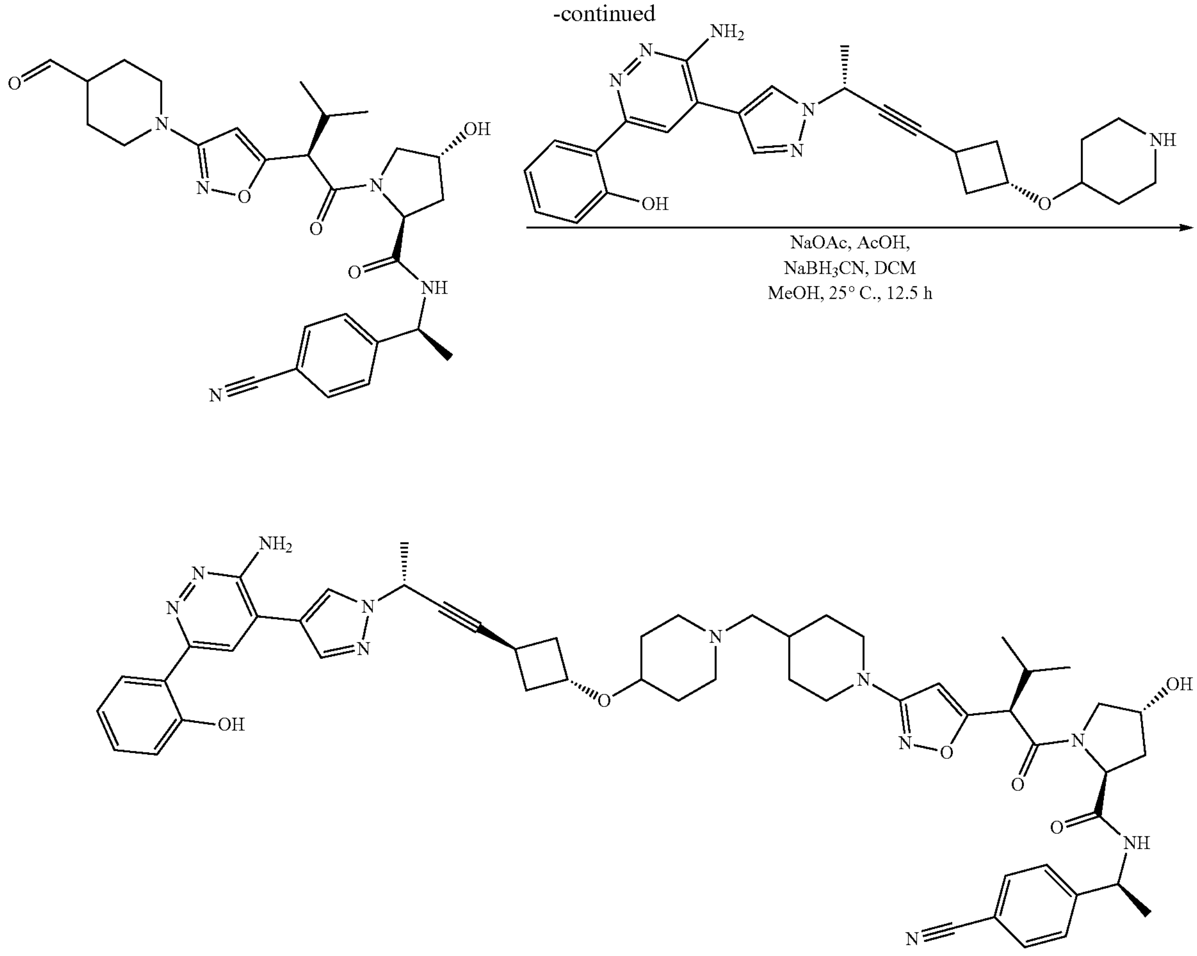
Exemplary Compound 698
Exemplary Synthesis of Exemplary Compound 707
Prepared according to the scheme below using procedures described for other examples above.
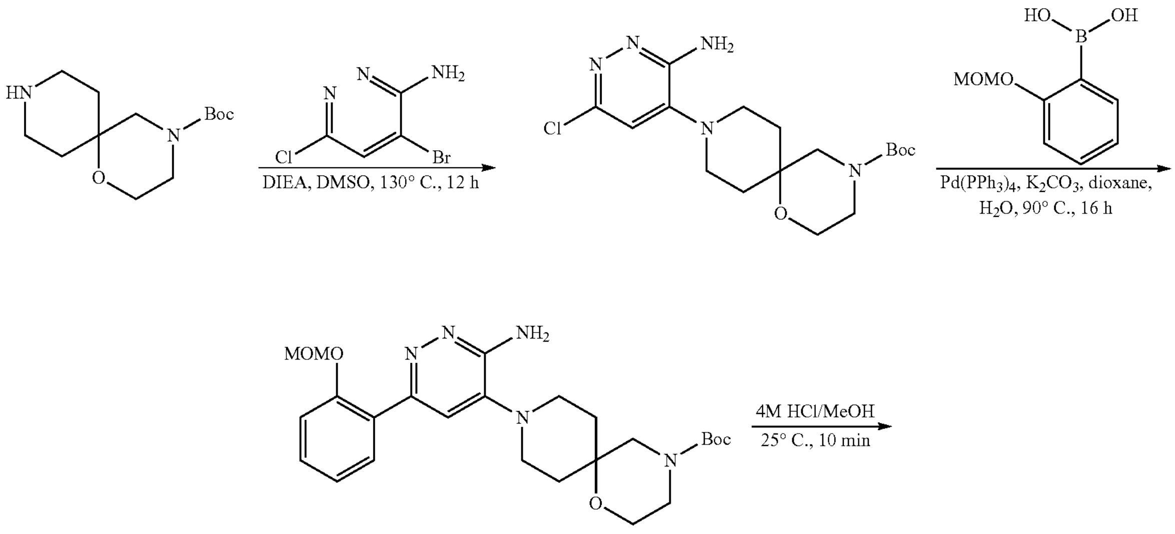

-continued
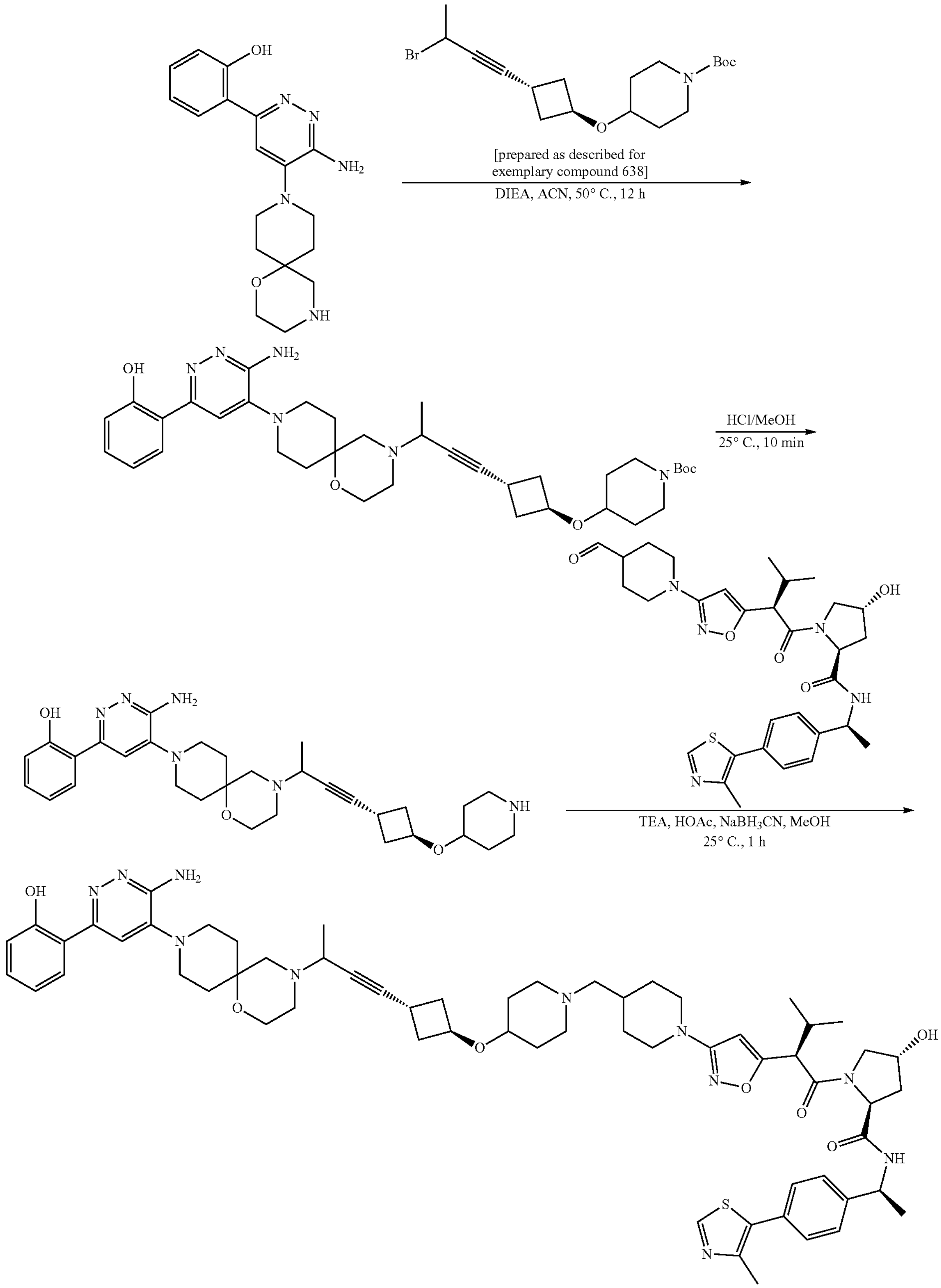
Exmeplary Compound 707

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

Specific Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative (e.g., an eighth embodiment may include the features recited in a first embodiment, as recited, and/or the features of any of the second through seventh embodiments).

In certain embodiments, the description provides the following exemplary SMARCA2 (i.e., BRAHMA or BRM) PROTAC molecules (compounds 1-765 of Table 1A, Table 1B, Table 1C, Table 1D, Table 2A, Table 2B, Table 2C, and Table 2D), including salts, prodrugs, polymorphs, analogs, derivatives, and deuterated forms thereof. In certain embodiment, the description provides bifunctional compounds having the chemical structure: PTM-L-ULM, or a pharmaceutically acceptable salt, enantiomer, stereoisomer, solvate, polymorph or prodrug thereof, wherein: the ULM is a small molecule E3 ubiquitin ligase binding moiety that binds a Von Hippel-Lindau E3 ubiquitin ligase; the L is a bond or a chemical linking moiety connecting the ULM and the PTM; and the PTM is a small molecule comprising a SMARCA2 protein targeting moiety having a chemical structure represented by Formula I, II, III, IVa, or IVb:

(I)

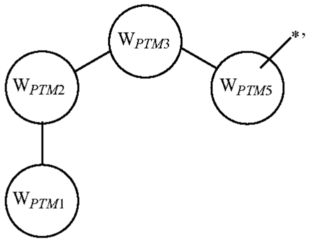

(II)

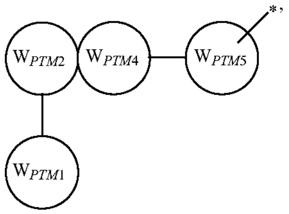

-continued (III)

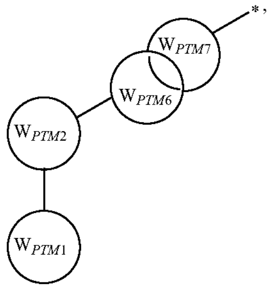

(IVa)

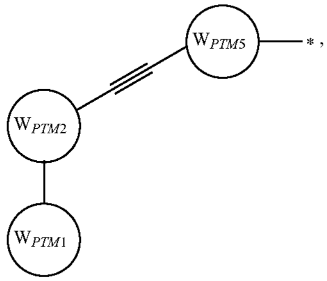

or (IVb)

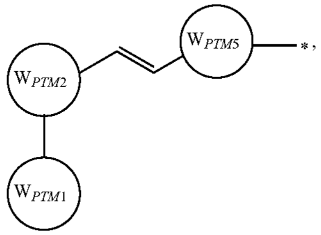

(VI)

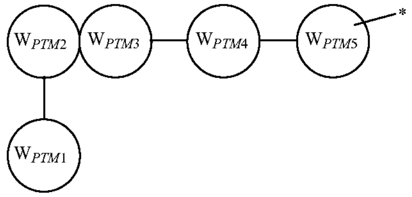

wherein:

$W_{PTM1}$ is an optionally substituted 5-6-membered aryl or heteroaryl ring (e.g., a 5-6 member aryl or heteroaryl substituted with 0, 1, 2, or 3 substituents selected from hydroxy, halogen, alkoxy, alkyl, haloalkyl, amino, alkylamino and cyano);

$W_{PTM2}$ is an optionally substituted 5-6-membered aryl or heteroaryl ring (e.g., a 5-6 membered aryl or heteroaryl substituted with 0, 1, 2, or 3 substituents selected from hydroxy, halogen, alkoxy, alkyl, haloalkyl, amino, alkylamino and cyano);

$W_{PTM3}$ is absent or an optionally substituted 5-6-membered aryl or heteroaryl ring (e.g., a 5-6 membered aryl or heteroaryl substituted with 0, 1, 2, or 3 substituents selected from hydroxy, halogen, alkoxy, alkyl, haloalkyl, amino, alkylamino and cyano), or an optionally substituted 4-9 cycloalkyl or heterocyclyl, an optionally substituted bridged bicycloalkyl and bridged biheterocyclyl (e.g. a 4-9 cycloalkyl or heterocyclyl substituted with 0, 1, or 2 substituents selected from hydroxy, halogen, alkoxy, alkyl, haloalkyl, amino, alkylamino and cyano);

$W_{PTM4}$ is an optionally substitute 5-7 cycloalkyl or heterocyclyl (e.g., 5-7 cycloalkyl or heterocyclyl substituted with 0, 1, 2, or 3 substituents selected from hydroxy, halogen, alkoxy, alkyl, haloalkyl, amino, alkylamino and cyano) that is fused with the $W_{PTM2}$ ring;

$W_{PTM5}$ is absent or an optionally substituted 5-6-membered aryl or heteroaryl ring (e.g. a 5-6 membered aryl or heteroaryl substituted with 0, 1, or 2 substituents selected from hydroxy, halogen, alkoxy, alkyl, haloalkyl, amino, alkylamino and cyano);

$W_{PTM6}$ and $W_{PTM7}$ are independently an optionally 4-7 cycloalkyl or heterocyclyl (e.g., each is independently a 4-7 cycloalkyl or heterocyclyl substituted with 0, 1, or 2 substituents selected from hydroxy, halogen, alkoxy, alkyl, haloalkyl, amino, alkylamino and cyano), and the rings of $W_{PTM6}$ and $W_{PTM7}$ are fused or linked via a spiro connection; and

 is the attachment point to the, linker, ULM group, ULM' group, VLM group, VLM' group.

In any of the aspects for embodiments described herein, the PTM is represented by Formula I:

(I)

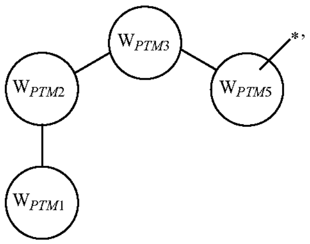

or a pharmaceutically acceptable salt thereof, wherein:

$W_{PTM1}$ is an optionally substituted phenyl or a pyridyl (e.g., substituted as described herein, such as a phenyl substituted with a hydroxy substituent with or without an additional optional substituent selected as described herein);

$W_{PTM2}$ is an optionally substituted 6-membered heteroaryl ring (e.g., substituted as described herein, such as a pyridazine substituted with amino group);

$W_{PTM3}$ is absent an optionally substituted 5-6-membered heteroaryl (e.g., a pyrazole, pyrrole, imidazole, oxazole, oxadiazole, or triazole) or an optionally substituted 4-9 cycloalkyl or heterocyclyl ring, an optionally substituted bridged bicycloalkyl and bridged biheterocyclyl ring.

In any of the aspects or embodiments described herein, the PTM is represented by the formula:

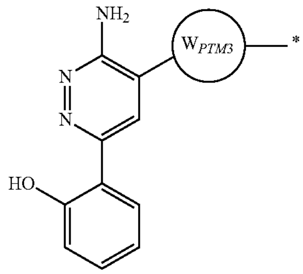

or

-continued

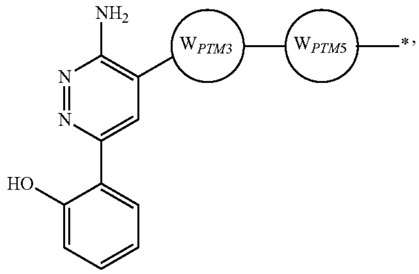

or a pharmaceutically acceptable salt thereof, wherein:

$W_{PTM3}$ is absent or an optionally substituted 5-6-membered heteroaryl, an optionally substituted 4-9 cycloalkyl or heterocyclyl ring, an optionally substituted bridged bicycloalkyl and bridged biheterocyclyl ring; and $W_{PTM5}$ is an optionally substituted 5-6-membered heteroaryl.

In any of the aspects or embodiments described herein, the PTM is represented by the formula:

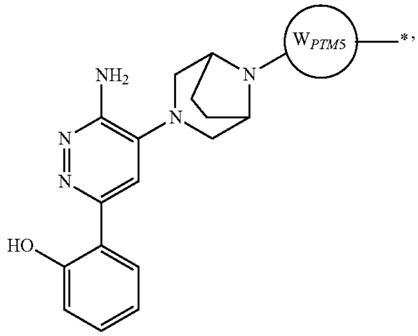

or a pharmaceutically acceptable salt thereof, wherein:

$W_{PTM5}$ is phenyl or pyridinyl.

In any of the aspects or embodiments described herein, the PTM is represented by the formula:

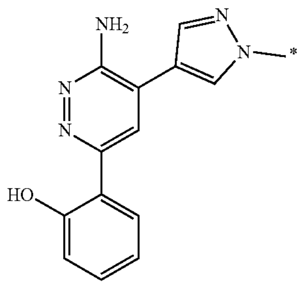

or

-continued

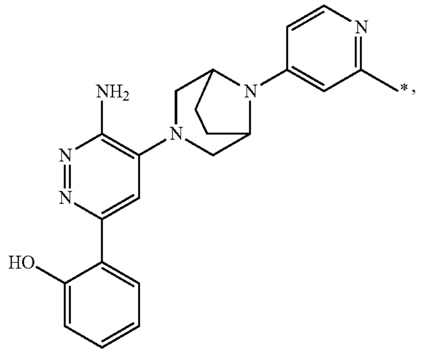

or a pharmaceutically acceptable salt thereof.

In any of the aspects or embodiments described herein, the PTM is represented by Formula III:

(III)

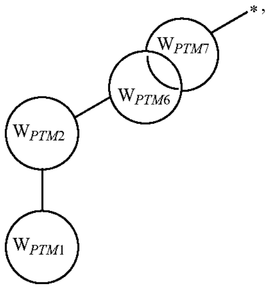

or a pharmaceutically acceptable salt thereof, wherein:

$W_{PTM1}$ is a phenyl substituted with a hydroxy substituent with or without an additional optional substituent;

$W_{PTM2}$ is a pyridazine substituted with amino group; and $W_{PTM6}$ and $W_{PTM7}$ are a spirocyclic ring system (e.g., a spirocyclic ring selected from:

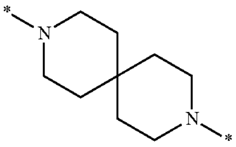

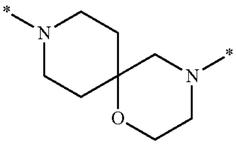

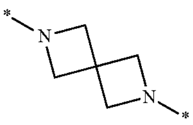

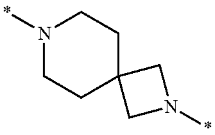

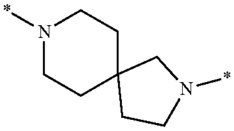

).

In any of the aspects or embodiments described herein, the PTM is represented by Formula IVa or IVb:

(IVa)

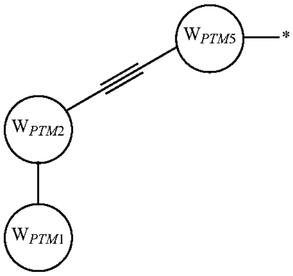

or (IVb)

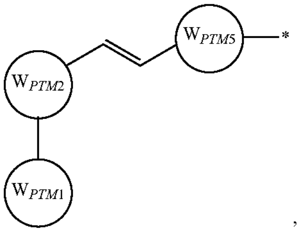

, or a pharmaceutically acceptable salt thereof, wherein:

$W_{PTM1}$ is a phenyl substituted with a hydroxy substituent with or without an additional optional substituent selected as described herein;

$W_{PTM2}$ is a pyridazine substituted with amino group;

$W_{PTM5}$ is absent, a pyrazole ring, or a pyridine ring.

In any of the aspects or embodiments described herein, the PTM is selected from the group consisting of:

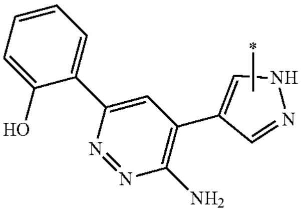

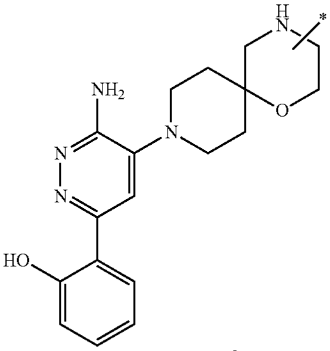

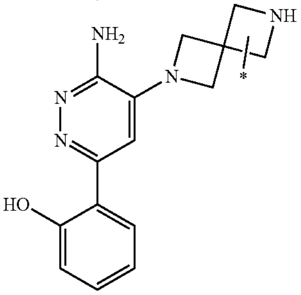

-continued
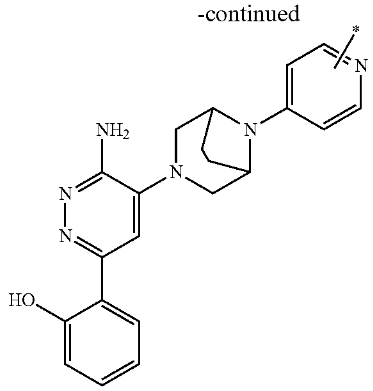
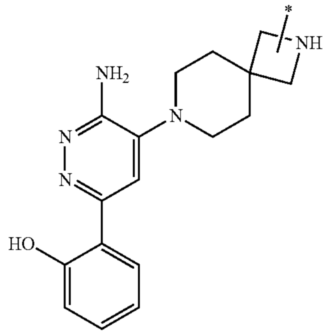
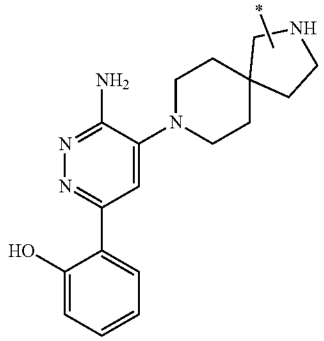
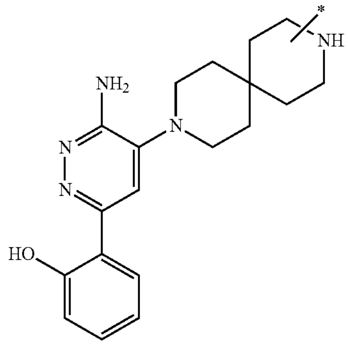
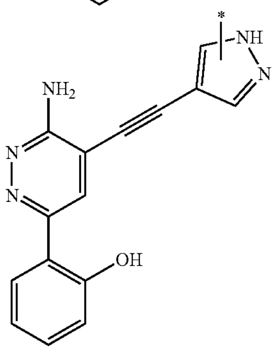
-continued
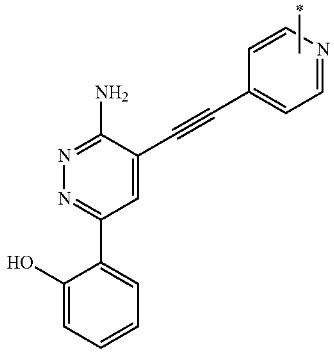
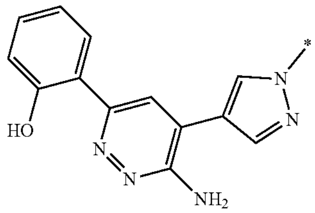
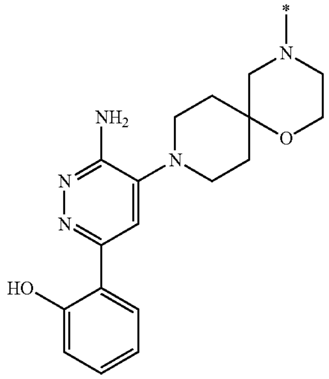
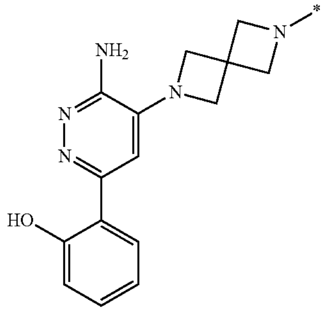
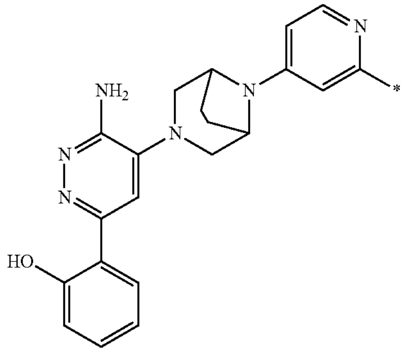

-continued
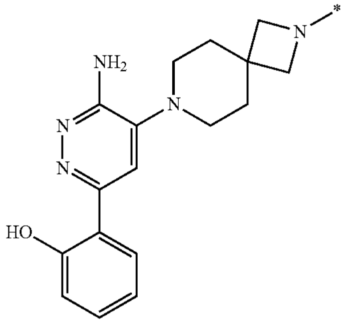
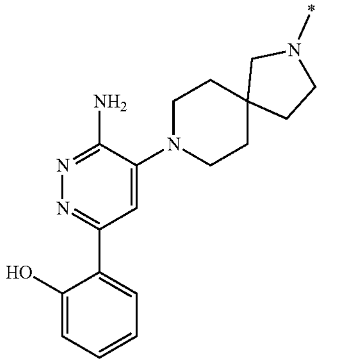
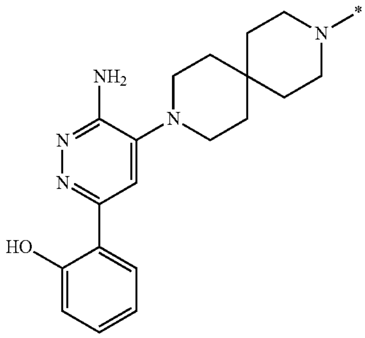
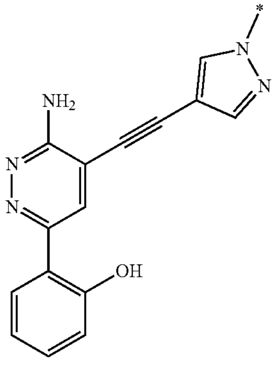
-continued
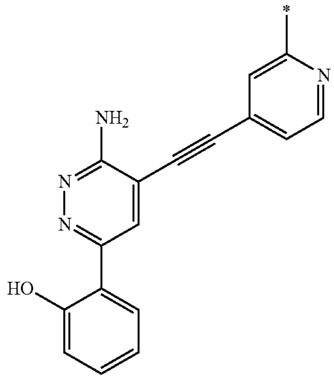
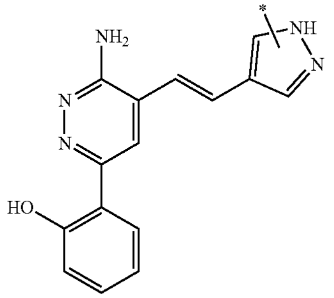
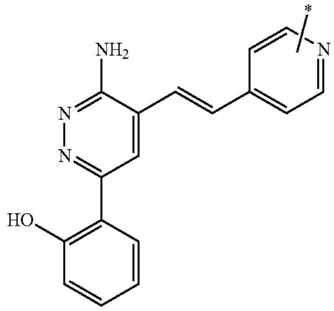
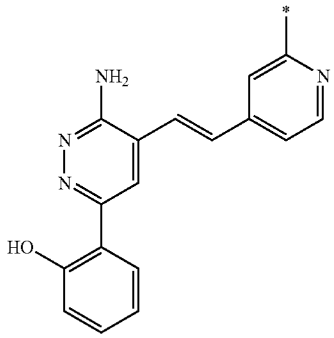
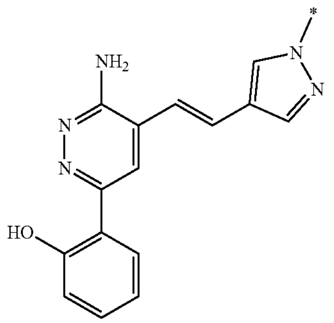

-continued

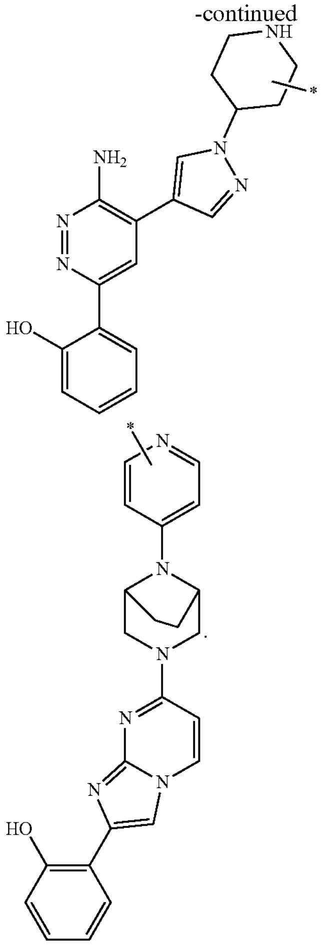

In any of the aspects or embodiments described herein, the ULM is a chemical structure represented by:

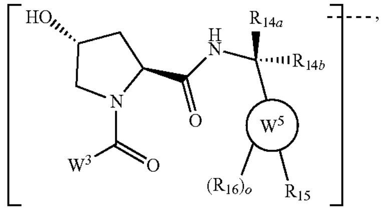

wherein:

$W^3$ is selected from the group of an optionally substituted aryl, optionally substituted heteroaryl, or

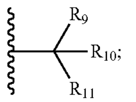

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ is selected from the group of an optionally substituted heterocyclyl, optionally substituted alkoxy, optionally substituted heteroaryl, optionally substituted aryl,

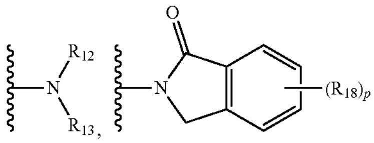

,

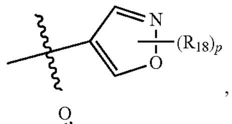

,

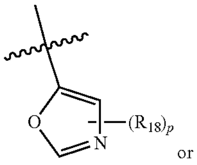

or

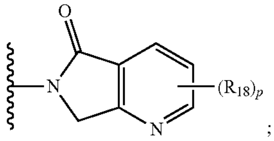

;

$R_{12}$ is selected from the group of H or optionally substituted alkyl;

$R_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, are each independently selected from the group of H, haloalkyl (e.g., fluoroalkyl), optionally substituted alkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine;

$W^5$ is optionally substituted phenyl, optionally substituted napthyl, or an optionally substituted 5-10 membered heteroaryl;

$R_{15}$ is selected from the group of H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}SO_2R_{27b}$, optionally substituted alkyl, optionally substituted haloalkyl (e.g., optionally substituted fluoroalkyl), optionally substituted haloalkoxy; optionally substituted aryl; optionally substituted heteroaryl; optionally substituted cycloalkyl; or optionally substituted heterocyclyl;

each $R_{16}$ is independently selected from the group of halo, CN, optionally substituted alkyl, optionally substituted haloalkyl, hydroxy, or optionally substituted haloalkoxy;

o is 0, 1, 2, 3, or 4;

$R_{18}$ is independently selected from the group of H, halo, optionally substituted alkoxy, cyano, optionally substituted alkyl, haloalkyl, haloalkoxy or a linker;

each $R_{26}$ is independently selected from H, optionally substituted alkyl or $NR_{27a}R_{27b}$;

each $R_{27a}$ and $R_{27b}$ is independently H, optionally substituted alkyl, optionally substituted cycloalkyl (e.g., optionally substituted 3-5 member cycloalkyl), or $R_{27a}$ and $R_{27b}$ together with the nitrogen atom to which they are attached form a 4-6 membered heterocyclyl; and p is 0, 1, 2, 3, or 4, and wherein the dashed line indicates the site of attachment of at least one PTM, another ULM (ULM') or a chemical linker moiety coupling at least one PTM or a ULM' or both to ULM.

In any of the aspects or embodiments described herein, the ULM has a chemical structure selected from the group of:

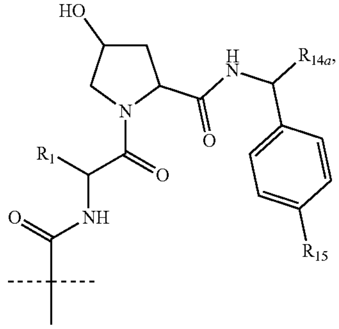

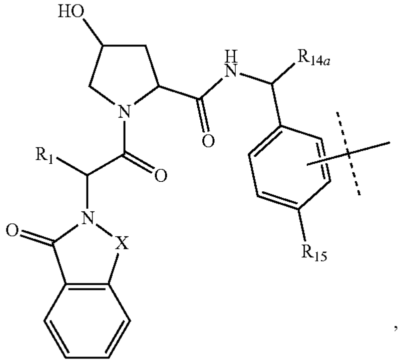

, and

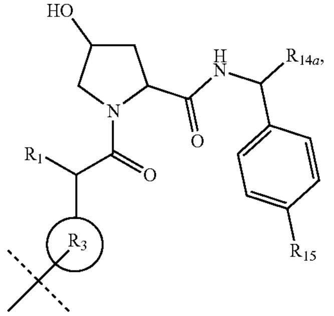

wherein:

$R_1$ is H, optionally substituted alkyl, optionally substituted cycloalkyl, optionally substituted hydroxyalkyl, optionally substituted heteroaryl, or haloalkyl;

$R_{14a}$ is H, haloalkyl, optionally substituted alkyl, methyl, fluoromethyl, hydroxymethyl, ethyl, isopropyl, or cyclopropyl;

$R_{15}$ is selected from the group consisting of H, halogen, CN, OH, $NO_2$, optionally substituted heteroaryl, optionally substituted aryl, optionally substituted alkyl (e.g. optionally substituted haloalkyl), optionally substituted haloalkyl, optionally substituted haloalkoxy, optionally substituted cycloalkyl, or optionally substituted heterocyclyl;

X is C, $CH_2$, or C═O;

$R_3$ is absent or an optionally substituted 5 or 6 membered heteroaryl; and the dashed line indicates the site of attachment of at least one PTM, another ULM (ULM') or a chemical linker moiety coupling at least one PTM or a ULM' or both to the ULM.

In any of the aspects or embodiments described herein, the ULM comprises a group according to the chemical structure:

ULM-g

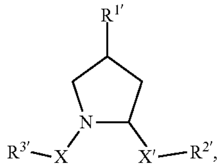

or a pharmaceutically acceptable salt thereof, wherein:

$R^{1'}$ of ULM-g is an optionally substituted $C_1$-$C_6$ alkyl group, an optionally substituted $-(CH_2)_nOH$, an optionally substituted $-(CH_2)_nSH$, an optionally substituted $(CH_2)_n-O-(C_1$-$C_6)$alkyl group, an optionally substituted $(CH_2)_n-WCOCW-(C_0$-$C_6)$alkyl group containing an epoxide moiety WCOCW where each W is independently H or a $C_1$-$C_3$ alkyl group, an optionally substituted $-(CH_2)_nCOOH$, an optionally substituted $-(CH_2)_nC(O)-(C_1$-$C_6$ alkyl), an optionally substituted $-(CH_2)_nNHC(O)-R''$, an optionally substituted $-(CH_2)_nC(O)-N(R'')_2$, an optionally substituted $-(CH_2)_nOC(O)-N(R'')_2$, $-(CH_2O)_nH$, an optionally substituted $-(CH_2)_nOC(O)-(C_1$-$C_6$ alkyl), an optionally substituted $-(CH_2)_nC(O)-O-(C_1$-$C_6$ alkyl), an optionally substituted $-(CH_2O)_nCOOH$, an optionally substituted $-(OCH_2)_nO-(C_1$-$C_6$ alkyl), an optionally substituted $-(CH_2O)_nC(O)-(C_1$-$C_6$ alkyl), an optionally substituted $-(OCH_2)_nNHC(O)-R''$, an optionally substituted $-(CH_2O)_nC(O)-N(R'')_2$, $-(CH_2CH_2O)_nH$, an optionally substituted $-(CH_2CH_2O)_nCOOH$, an optionally substituted $-(OCH_2CH_2)_nO-(C_1$-$C_6$ alkyl), an optionally substituted $-(CH_2CH_2O)_nC(O)-(C_1$-$C_6$ alkyl), an optionally substituted $-(OCH_2CH_2)_nNHC(O)-R''$, an optionally substituted $-(CH_2CH_2O)_nC(O)-N(R'')_2$, an optionally substituted $-SO_2R_S$, an optionally substituted $S(O)R_S$, $NO_2$, CN or halogen (F, Cl, Br, I, preferably F or Cl);

each R'' of ULM-g is independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocyclyl group or a $-(CH_2)_m N(R'')_2$ group;

X and X' of ULM-g are each independently C═O, C═S, —S(O), $S(O)_2$, (preferably X and X' are both C═O);

$R^{2'}$ of ULM-g is an optionally substituted $-(CH_2)_n-(C{=}O)_u(NR'')_v(SO_2)_w$alkyl group, an optionally substituted $-(CH_2)_n-(C{=}O)_u(NR'')_v(SO_2)_wN_{1N}R_{2N}$ group, an optionally substituted $-(CH_2)-(C{=}O)_u(NR'')_v(SO_2)_w$-Aryl, an optionally substituted —$(CH_2)_n$—$(C{=}O)_u(NR'')_v(SO_2)_w$-Heteroaryl, an optionally substituted —$(CH_2)$—$(C{=}O)_vNR''$ $(SO_2)_w$-Heterocyclyl, an optionally substituted —NR''—$(CH_2)$—$C(O)_u(NR'')_v(SO_2)_w$-alkyl, an optionally substituted —NR''—$(CH_2)$—$C(O)_u(NR'')_v(SO_2)_w$—$NR_{1N}R_{2N}$, an optionally substituted —NR''—$(CH_2)_n$—$C(O)_u(NR'')_v(SO_2)_w$—NR''C(O)$R_{1N}$, an optionally substituted —NR''—$(CH_2)_n$—$(C{=}O)_u(NR'')_v(SO_2)_w$-Aryl, an optionally substituted —NR''—$(CH_2)$—$(C{=}O)_u(NR'')_v(SO_2)_w$-Heteroaryl or an optionally substituted —NR''—$(CH_2)_n$—$(C{=}O)_vNR''$ $(SO_2)_w$-Heterocyclyl, an optionally substituted —$X^{R2'}$-alkyl group; an optionally substituted —$X^{R2'}$— Aryl group; an optionally substituted —$X^{R2'}$— Heteroaryl group; an optionally substituted —$X^{R2'}$— Heterocyclyl group;

$R^{3'}$ of ULM-g is an optionally substituted alkyl, an optionally substituted —$(CH_2)_n$—$(O)_u(NR'')_v(SO_2)_w$-alkyl, an optionally substituted —$(CH_2)$—$C(O)_u$ $(NR'')_v(SO_2)_w$—$NR_{1N}R_{2N}$, an optionally substituted —$(CH_2)_n$—$C(O)_u(NR'')_v(SO_2)_w$—NR''C(O)$R_{1N}$, an optionally substituted —$(CH_2)_n$—$C(O)_u(NR'')_v$ $(SO_2)_w$—$C(O)(R'')_2$, an optionally substituted —$(CH_2)_n$—$C(O)_u(NR'')_v(SO_2)_w$-Aryl, an optionally substituted —$(CH_2)_n$—$C(O)_u(NR'')_v(SO_2)_w$-Heteroaryl, an optionally substituted —$(CH_2)_n$—$C(O)_u$ $(NR'')_v(SO_2)_w$-Heterocyclyl, an optionally substituted —NR''—$(CH_2)_n$—$C(O)_u(NR'')_v(SO_2)_w$-alkyl, an optionally substituted —NR''—$(CH_2)_n$—$C(O)_u(NR'')_v$ $(SO_2)_w$—$NR_{1N}R_{2N}$, an optionally substituted —NR''—$(CH_2)_n$—$C(O)_u(NR'')(SO_2)_w$—NR''C(O)$R_{1N}$, an optionally substituted —NR''—$(CH_2)$—$C(O)_u(NR'')_v$ $(SO_2)_w$-Aryl, an optionally substituted —NR''—$(CH_2)$—$C(O)_u(NR'')_v(SO_2)_w$-Heteroaryl, an optionally substituted —$NR^1$—$(CH_2)_n$—$C(O)_u(NR'')_v(SO_2)_w$-Heterocyclyl, an optionally substituted —O—$(CH_2)_n$—$(C{=}O)_u(NR'')_v(SO_2)_w$-alkyl, an optionally substituted —O—$(CH_2)_n$—$(C{=}O)(NR'')_v(SO_2)_w$—$NR_{1N}R_{2N}$, an optionally substituted —O—$(CH_2)_n$—$(C{=}O)_u(NR'')_v(SO_2)_w$—NR''C(O)$R_{1N}$, an optionally substituted —O—$(CH_2)_n$—$(C{=}O)_u(NR'')_v(SO_2)_w$-Aryl, an optionally substituted —O—$(CH_2)$—$(C{=}O)_u(NR'')_v(SO_2)_w$-Heteroaryl or an optionally substituted —O—$(CH_2)_n$—$(C{=}O)_u(NR'')_v(SO_2)_w$-Heterocyclyl; —$(CH_2)_n$—$(V)_{n'}$—$(CH_2)_n$—$(V)_{n'}$-alkyl group, an optionally substituted —$(CH_2)_n$—$(V)_n$'—$(CH_2)_n$—$(V)_{n'}$-Aryl group, an optionally substituted —$(CH_2)$—$(V)_{n'}$—$(CH_2)$—$(V)_{n'}$-Heteroaryl group, an optionally substituted —$(CH_2)_n$—$(V)$—$(CH_2)_n$—$(V)_{n'}$-Heterocyclyl group, an optionally substituted —$(CH_2)_n$—$N(R_{1'})(C{=}O)_m$'—$(V)_{n'}$-alkyl group, an optionally substituted —$(CH_2)_n$—$N(R_{1'})(C{=}O)_{m'}$—$(V)_{n'}$-Aryl group, an optionally substituted —$(CH_2)_n$—$N(R_{1'})(C{=}O)_m$'—$(V)_{n'}$-Heteroaryl group, an optionally substituted —$(CH_2)_n$—$N(R_{1'})(C{=}O)_{m'}$—$(V)_{n'}$-Heterocyclyl group, an optionally substituted —$X^{R3'}$— alkyl group; an optionally substituted —$X^{R3'}$— Aryl group; an optionally substituted —$X^{R3'}$— Heteroaryl group; an optionally substituted —$X^{R3'}$-Heterocyclyl group;

$R_{1N}$ and $R_{2N}$ of ULM-g are each independently H, $C_1$-$C_6$ alkyl which is optionally substituted with one or two hydroxyl groups and up to three halogen groups or an optionally substituted —$(CH_2)$-Aryl, —$(CH_2)$-Heteroaryl or —$(CH_2)_n$-Heterocyclyl group;

V of ULM-g is O, S or $NR_1$;

each $R_{1'}$ of ULM-g is independently H or a $C_1$-$C_3$ alkyl group;

$X^{R2'}$ and $X^{R3'}$ of ULM-g are each independently an optionally substituted —$CH_2)_n$—, —$CH_2)_n$—$CH(X_v)$=$CH(X_v)$— (cis or trans), —$CH_2)_n$—CH≡CH—, —$(CH_2CH_2O)_n$— or a $C_3$-$C_6$ cycloalkyl group, where $X_v$ is H, a halo or a $C_1$-$C_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group thereof.

In any of the aspects or embodiments described herein, the ULM is of the formula:

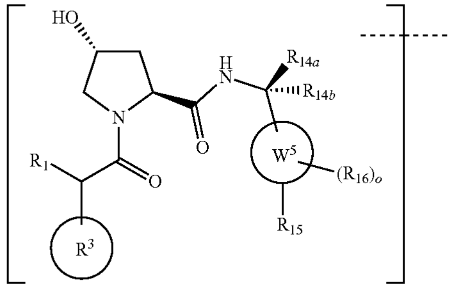

or

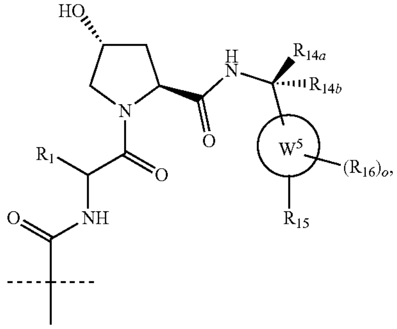

or a pharmaceutically acceptable salt thereof, wherein:

$R_1$ is H, optionally substituted alkyl or optionally substituted cycloalkyl;

$R_3$ is an optionally substituted 5-6 membered heteroaryl;

$W^5$ is optionally substituted phenyl, optionally substituted napthyl or optionally substituted pyridinyl;

one of $R_{14a}$ and $R_{14b}$ is H, optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine;

$R_{15}$ is CN, optionally substituted fluoroalkyl,

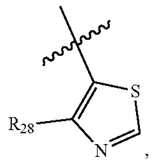, 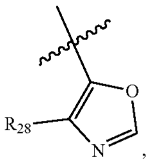, 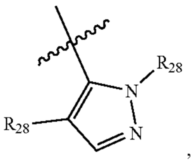,

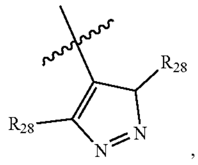, optionally substitute

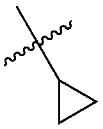 (e.g., 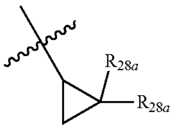 or 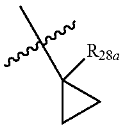, wherein $R_{28a}$ is halo, optionally substituted alkyl or fluoroalkyl) or

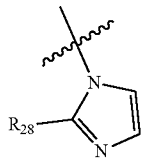;

each $R_{16}$ is independently selected from halo, CN, optionally substituted alkyl, optionally substituted haloalkyl, hydroxy, or haloalkoxy;

each $R_{26}$ is independently H, optionally substituted alkyl or $NR_{27a}R_{27b}$;

each $R_{27a}$ and $R_{27b}$ is independently H, optionally substituted alkyl, optionally substituted cycloalkyl (e.g., optionally substituted 3-5 member cycloalkyl), or $R_{27a}$ and $R_{27b}$ together with the nitrogen atom to which they are attached form a 4-6 membered heterocyclyl;

$R_{28}$ is H, optionally substituted alkyl, optionally substituted alkoxy, optionally substituted heteroalkyl, optionally substituted alkylamine, optionally substituted hydroxyalkyl, amine, optionally substituted alkynyl, or optionally substituted cycloalkyl; and o is 0, 1 or 2.

In any of the aspects or embodiments described herein, the ULM is of the formula:

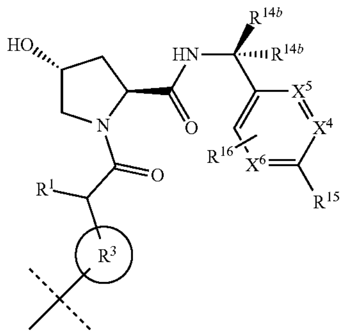

or

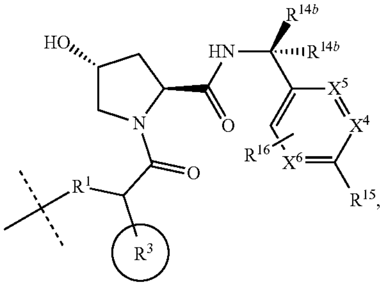

wherein:

each of $X^4$, $X^5$, and $X^6$ is selected from CH and N, wherein no more than 2 are N;

$R^1$ is $C_{1-6}$ alkyl;

one of $R^{14a}$ and $R^{14b}$ is H, optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H; or $R^{14a}$ and $R^{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine;

each $R_{27a}$ and $R_{27b}$ is independently H or $C_{1-6}$ alkyl or cycloalkyl (e.g., 3-5 member cycloalkyl);

q is 1, 2, 3 or 4;

$R^{15}$ is,

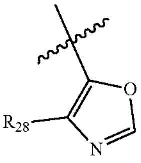, 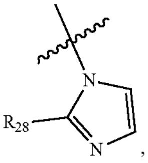, 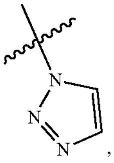,

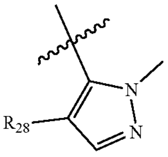, or CN;

$R^{28}$ is H, methyl, $CH_2N(Me)_2$, $CH_2OH$, $CH_2O(C_{1-4}alkyl)$, $CH_2NHC(O)C_{1-4}alkyl$, $NH_2$,

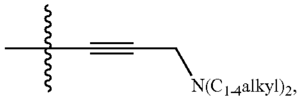

or

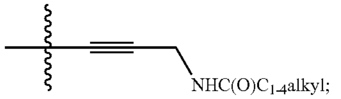

$R^{28c}$ is H, methyl, fluoro, or chloro; and $R^{16}$ is H, $C_{1-4}alkyl$, fluoro, chloro, CN, or $C_{1-4}alkoxy$.

In any aspect or embodiment described herein, $R^{14a}$ and $R^{14b}$ are selected from: H, $C_{1-4}$ alkyl, $C_{1-4}$ cycloalkyl, $C_{1-4}$ haloalkyl, $C_{1-4}$ hydroxyalkyl, $C_{1-4}$ alkyloxyalkyl, $C_{1-4}$ alkyl-$NR_{27a}R_{27b}$ and $CONR_{27a}R_{27b}$.

In any aspect or embodiment described herein, at least one of $R^{14a}$ and $R^{14b}$ is H (e.g., both $R^{14a}$ and $R^{14b}$ are H).

In any aspect or embodiment described herein, at least one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$. Alternatively, in any aspect or embodiment described herein, one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H.

In any aspect or embodiment described herein, $R^{14a}$ and $R^{14b}$ together with the carbon atom to which they are attached form

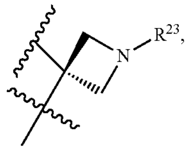

wherein $R^{23}$ is selected from H, $C_{1-4}alkyl$, —$C(O)C_{1-4}alkyl$.

In any of the aspects or embodiments described herein, the ULM is of the formula:

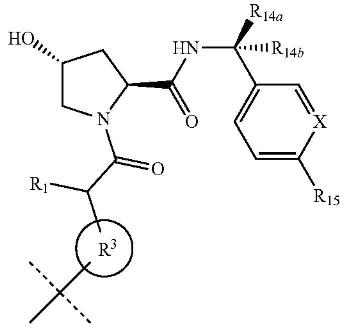

or

-continued

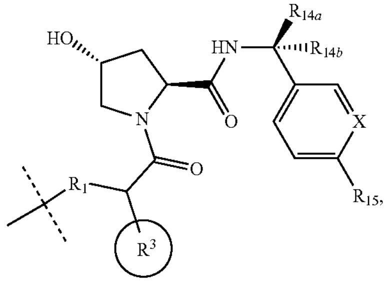

or a pharmaceutically acceptable salt thereof, wherein $R_1$, $R_3$, $R_{14a}$, $R_{14b}$, and $R_{15}$ of ULM-q and ULM-r are as described herein; and X is CH or N.

In any of the aspects or embodiments described herein, $R_1$ is $C_{1-6}$ alkyl.

In any of the aspects or embodiments described herein, one of $R_{14a}$ and $R_{14b}$ is H, $C_{1-6}$ alkyl, $C_{1-6}$ haloalkyl, optionally substitute $C_{1-4}$ alkylamine, $C_{1-6}$ alkoxy, $(CH_2)_qC_{1-6}$ alkoxy, $(CH_2)_qC_{1-6}$ alkoxy-$C_3$-$C_7$ heterocycloalkyl, $(CH_2)_qOH$, $(CH_2)_qNR_{27a}R_{27b}$, $(CH_2)_qNHCOC_{1-6}$ alkyl, $C_{3-6}$ cycloalkyl, or $NR_{27a}R_{27b}$; each $R_{26}$ is independently H, $C_{1-6}$ alkyl or $NR_{27a}R_{27b}$; each $R_{27a}$ and $R_{27b}$ is independently H or $C_{1-6}$ alkyl; and q is 1, 2, 3 or 4.

In any of the aspects or embodiments described herein, one of $R_{14a}$ and $R_{14b}$ is H, $C_{1-4}$ alkyl, $C_{1-4}$ haloalkyl, $C_{1-4}$ alkoxy, optionally substituted $C_{1-4}$ alkylamine, $(CH_2)_qC_{1-6}$ alkoxy, $(CH_2)_qC_{1-6}$ alkoxy-C3-$C_7$ heterocycloalkyl, $(CH_2)_qOH$, $(CH_2)_qNR_{27a}R_{27b}$, $(CH_2)_qNHCOC_{1-6}$ alkyl, $C_{3-6}$ cycloalkyl, or $NR_{27a}R_{27b}$; each $R_{26}$ is independently H, $C_{1-4}$ alkyl or $NR_{27a}R_{27b}$; each $R_{27a}$ and $R_{27b}$ is independently H or $C_{1-4}$ alkyl; and q is 1 or 2.

In any of the aspects or embodiments described herein, $R_{28}$ is $C_{1-6}$ alkyl, $C_{3-6}$ cycloalkyl, $C_{1-6}$ haloalkyl, $(CH_2)_qOC_{1-6}alkyl$, $(CH_2)_qOH$, $(CH_2)_qNR_{27a}R_{27b}$, $(CH_2)_qNHCOC_{1-6}$ alkyl, or

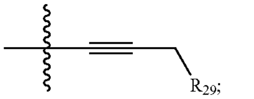

$R_{29}$ is H, $C_{1-6}$ alkyl, $NR_{27a}R_{27b}$ or ${}_qNHCOC_{1-6}$ alkyl; and wherein q is 1 or 2.

In any of the aspects or embodiments described herein, $R^3$ is isoxazolyl, 4-chloroisoxazolyl, 4-fluoroisoxazolyl, or pyrazolyl. In any of the aspects or embodiments described herein, X is CH.

In any aspect or embodiment described herein, the ULM is according to the formula:
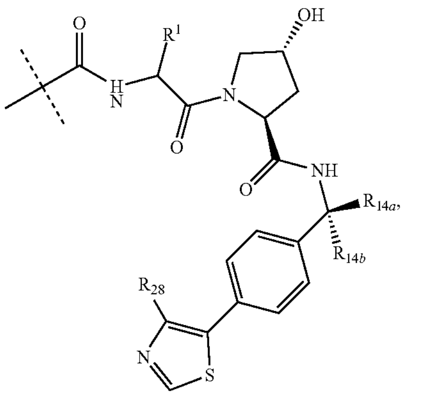
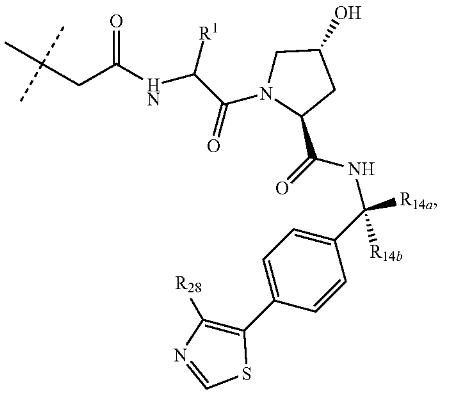
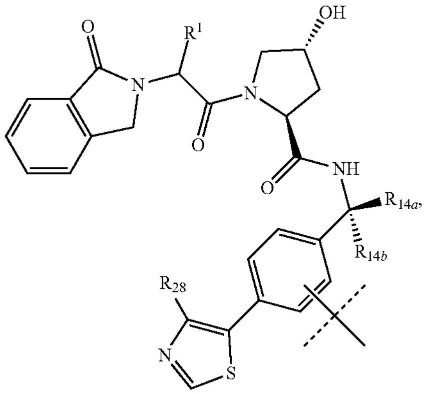
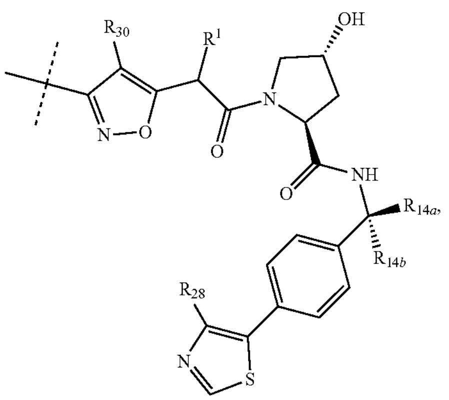
-continued
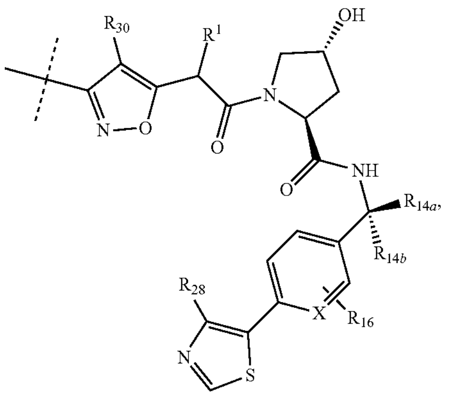
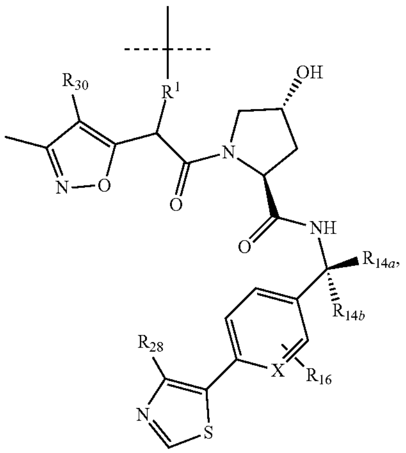
or a pharmaceutically acceptable salt thereof,
wherein:
$R_1$, $R_{14a}$ and $R_{14b}$ are as described herein;
X is CH or N;
$R_{30}$ is H, F or Cl;
$R^{16}$ is H, $C_{1-4}$ alkyl, fluoro, chloro, CN, or $C_{1-4}$ alkoxy; and
$R_{28}$ is H, methyl, $CH_2N(Me)_2$, $CH_2OH$, $CH_2O(C_{1-4}alkyl)$, $CH_2NHC(O)C_{1-4}alkyl$, $NH_2$,
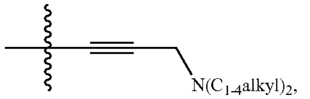
or
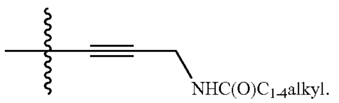

In any of the aspects or embodiments described herein, the ULM is according to the formula:

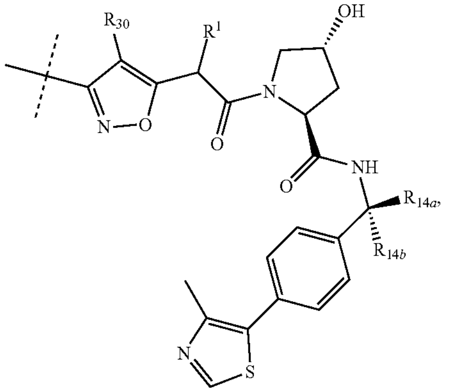

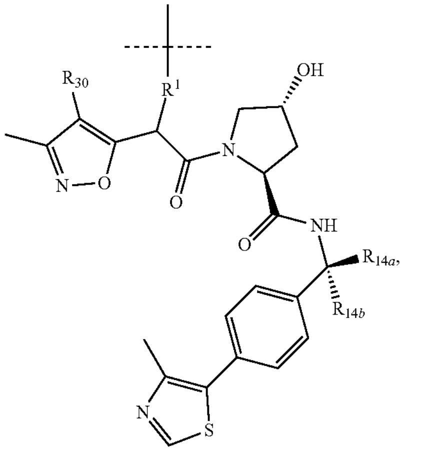

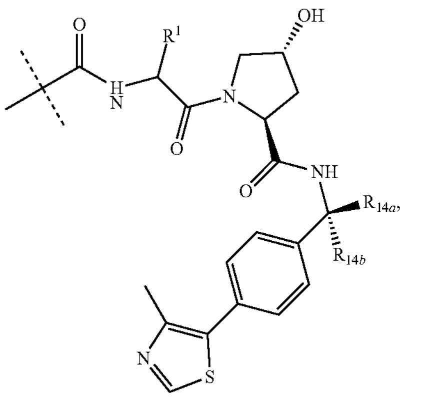

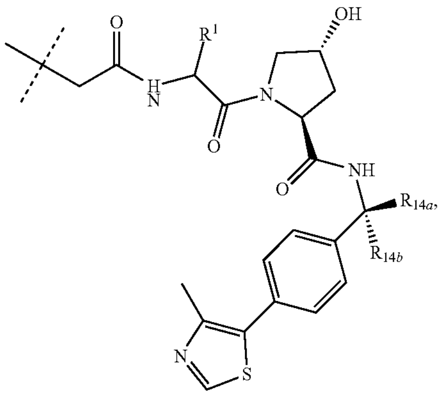

-continued

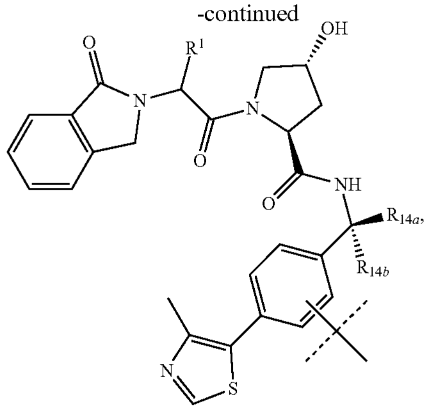

or a pharmaceutically acceptable salt thereof, wherein $R_1$, $R_{14a}$ and $R_{14b}$ are as described herein; and $R_{30}$ is H, F or Cl.

In any of the aspects or embodiments described herein, the ULM is a ULM as provided in Table 1A, Table 1B, Table 1C, Table 1D, Table 2A, Table 2B, Table 2C, or Table 2D.

In any of the aspects or embodiments described herein, the compound includes a Linker (L) as described herein.

In any of the aspects or embodiments described herein, the linker (L) is a polyethylenoxy group optionally substituted with aryl or phenyl comprising from 1 to 10 ethylene glycol units.

In any of the aspects or embodiments described herein, the compound is selected from the compounds of Table 1A, Table 1B, Table 1C, Table 1D, Table 2A, Table 2B, Table 2C, and Table 2D (e.g., selected from compounds 1-765).

In any of the aspects or embodiments described herein, the compound has a $D_max$ greater than or equal to 80%.

In an additional aspect, the description provides a composition comprising an effective amount of a bifunctional compound as described herein, and a pharmaceutically acceptable carrier.

In any of the aspects or embodiments described herein, the composition as described herein further comprises at least one of: an additional bioactive agent or another bifunctional compound described herein.

In any of the aspects or embodiments described herein, the additional bioactive agent is anti-cancer agent.

In any of the aspects or embodiments described herein, the composition as described herein comprises a pharmaceutically acceptable carrier and an effective amount of at least one compound as described herein for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with SMARCA1, BRAHMA or BRM accumulation and aggregation. In any aspect or embodiment described herein, the disease or disorder is cancer. In any aspect or embodiment described herein, the cancer is a SWI/SNF associated cancer or a cancer with a SMARCA4 mutation (e.g., lung cancer or non-small cell lung cancer). In any aspect or embodiment described herein, the cancer is a SMARCA4-deficient cancer or a cancer with decreased expression of SMARCA4 relative to normal SMARCA4 expression (e.g., relative to the expression of non-mutated SMARCA4 or SMARCA4 in a similarly situated non-cancerous cell with a wildtype SMARCA4), such as lung cancer or non-small cell lung cancer.

EXAMPLES

Assays and Degradation Data

Western Blot Screen of BRM Degradation in SW1573 Cells

To assess BRM degradation ($D_{max}$ and $DC_{50}$) cells were seeded at 8000/well in 96-well black/clear-bottom plates in 180 μL DMEM growth media (containing 1% pen-strep, 1% HEPES and 10% FBS) per well. Plates were incubated overnight to allow adhesion. The next morning cells were treated by adding 20 μL of 10× target compound concentration (1% DMSO) to appropriate wells and returned to incubator for overnight (18-20 hours). The final DMSO concentration was 0.1%.

For lysing, adherent cells were washed once with 100 μL of DPBS. Cells were lysed in 40 μL of 1×RIPA+HALT protease inhibitor on ice for 10 minutes and frozen until use at −80° C. Thawed lysates were cleaned by filtration in 1.2 μm filter plates, or alternatively, were spun clean at 2300 g at 4° C. for 30 minutes.

For blotting, for each Western sample 30 μL of lysate was added to 10 μL of 4×LDS sample buffer, then denatured at 95° C. for 5 minutes in the thermal cycler and placed on ice. Samples were loaded on 4-15% Tris/Glycine gels and run for 25 minutes at 250 constant volts in 1×Tris/Glycine buffer with 4 μL of ladder and 12 μL of each sample loaded for each blot. Protein was transferred from gels to NC with BioRad Turbo dry-transfer unit with the Turbo/midi default program. All blots were rinsed with ddH2O and blocked for 1 hour at room temperature in 5% BSA in TBST (0.1%) on rocker. Blots were exposed to primary antibody in 5% BSA in TBST (0.1%) overnight at 4° C. on rocker (1:1000 for BRM (Cell Signaling Tech. cat #11966) and 1:2000 for alpha-tubulin (Cell Signaling Tech. cat #3873), a control protein. Blot was washed with TBST (0.1%) three times for 5 minutes on rocker at room temperature. Secondary antibody was added, and blots were incubated on a room temperature rocker for 1 hour with 1:18,000 anti-rabbit-HRP and/or anti-mouse-HRP in 5% BSA in TBST (0.1%). Blots were washed three times in TBST (0.1%) for 5 minutes at room temperature on the rocker. Signal was developed with Femto Maximum Sensitivity substrate for 4 minutes and blots read on Chemi-Doc™.

In-Cell Western Screen of BRM Degradation in SW1573 Cells

To assess BRM degradation ($D_{max}$ and $DC_{50}$), cells were seeded at 8000/well in 96-well black/clear-bottom plates in 180 μL DMEM growth media (containing 1% pen-strep, 1% HEPES and 10% FBS) per well. Plates were incubated overnight to allow adhesion. The next morning cells were treated by adding 20 μL of 10× compound (1% DMSO) to appropriate wells and returned to incubator for overnight (18-20 hours). The final DMSO concentration was 0.1%.

For processing, the plates were removed from incubator, the media was removed, and immediately 200 μL of cold (4° C.) DPBS was added to all wells. DPBS was then removed, and 50 μL of 4% paraformaldehyde (PFA) in DPBS (4° C.) was added to all wells, and the plates were incubated at room temperature for 20 minutes. PFA was then removed, and 200 μL of TBS-T containing 0.5% Triton X-100 was added to all wells, and the plates were incubated at room temperature for 30 minutes. TBS-T containing 0.5% Triton X-100 was then removed, and 50 μL of Li-Cor blocking solution was added, and the plates were incubated at room temperature for a minimum of one hour. The blocking solution was removed, and 50 μL of Li-Cor blocking solution containing primary antibody cocktail was added (1:1000 for BRM (Cell Signaling Tech. cat #11966) and 1:2000 for alpha-tubulin (Sigma cat #T6074), a control protein. Plates were then placed in cold room until the next day.

The next day plates were washed three times with TBS-T, 200 μL per well. Fifty (50) μL of secondary antibody cocktail in LI-COR blocking solution (anti-rabbit_800 nm and anti-mouse_680 nm) was added to all wells (diluted 1:5000). The plates were incubated at room temperature for at least one hour while protected from light. The plates were washed twice with TBS-T, 200 μL per well.

To read each plate TBS-T was removed, and each plate was inverted tapped on a paper towel. The plates were read on the LI-COR Odyssey with default intensity settings of 5.0 for both channels. LI-COR images were analyzed with the in-cell Western feature of Image Studio Lite.

The following compounds demonstrated target protein degradation when tested under the conditions described above:

TABLE 1A

Exemplary bifunctional degradation compounds of the present disclosure

| Ex. # | Structure | Compound Name |
| --- | --- | --- |
| 1 | 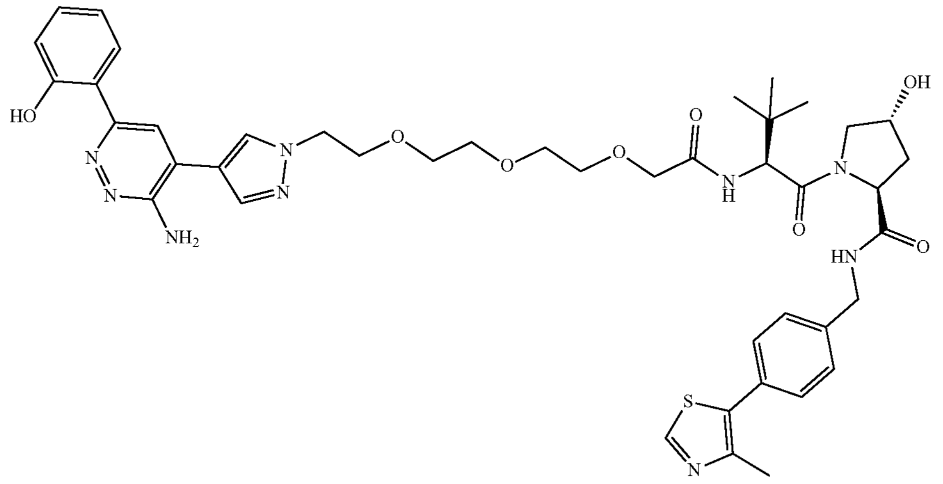 [SMILES: Cc1ncsc1-c1ccc(CNC(=O)[C@@H]2C[C@@H](O)CN2C(=O)[C@@H](NC(=O)COCCOCCOCCn2cc(-c3cc(-c4ccccc4O)nnc3N)cn2)C(C)(C)C)cc1] | (2S,4R)-1-((S)-14-(4-(3-amino-6-(2-hydroxyphenyl)pyridazin-4-yl)-1H-pyrazol-1-yl)-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide |
| 2 | 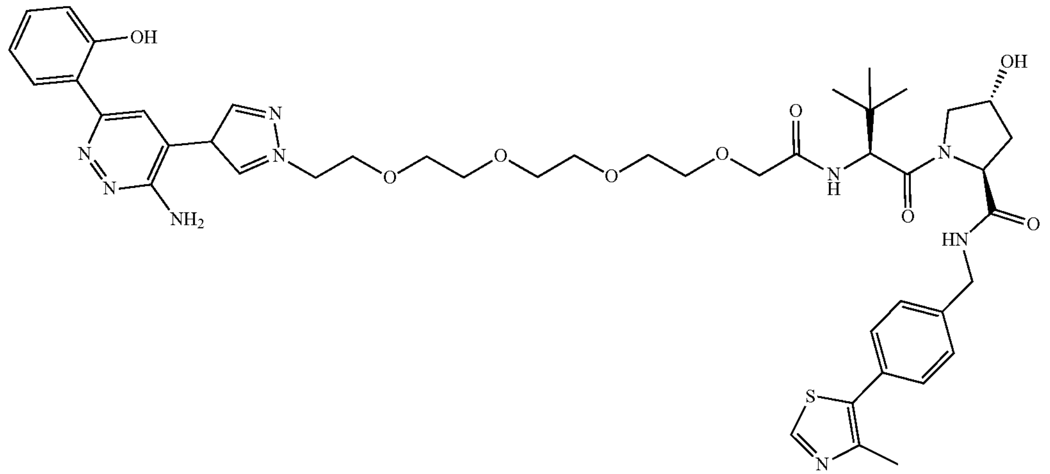 | (2S,4R)-1-((S)-17-(4-(3-amino-6-(2-hydroxyphenyl)pyridazin-4-yl)-1H-pyrazol-1-yl)-2-(tert-butyl)-4-oxo-6,9,12,15-tetraoxa-3-azaheptadecanoyl)-4-hydroxy-N-(4-(4-methylthiazol-5-yl)benzyl)pyrrolidine-2-carboxamide |

TABLE 1A-continued

| Exemplary bifunctional degradation compounds of the present disclosure | | |
|---|---|---|
| Ex. # | Structure | Compound Name |
| 3 | 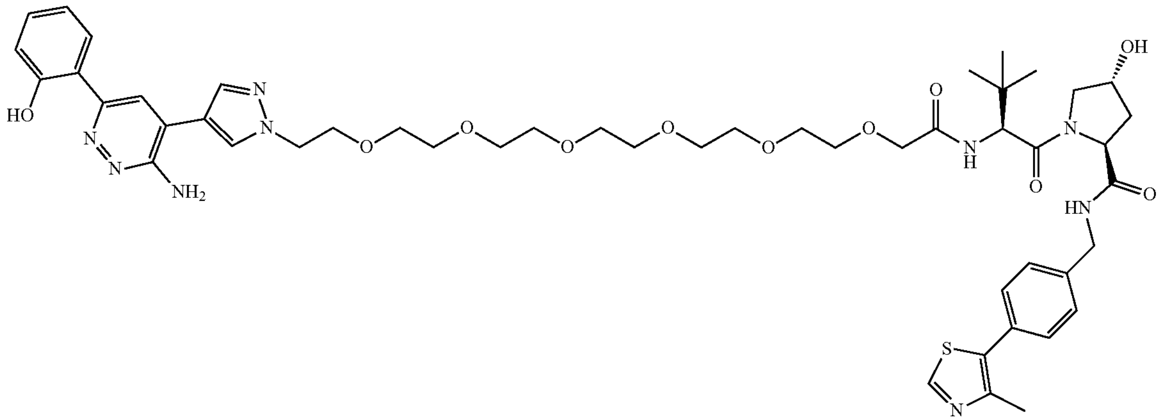 [SMILES: Cc1ncsc1-c1ccc(CNC(=O)[C@@H]2C[C@@H](O)CN2C(=O)[C@@H](NC(=O)COCCOCCOCCOCCOCCOCCn2cc(-c3cc(-c4ccccc4O)nnc3N)cn2)C(C)(C)C)cc1] | (2S,4R)-1-((S)-23-(4-(3-amino-6-(2-hydroxyphenyl)pyridazin-4-yl)-1H-pyrazol-1-yl)-2-(tert-butyl)-4-oxo-6,9,12,15,18,21-hexaoxa-3-azatricosanoyl)-4-hydroxy-N-(4-(4-methylthiazol-5-yl)benzyl)pyrrolidine-2-carboxamide |
| 4 | 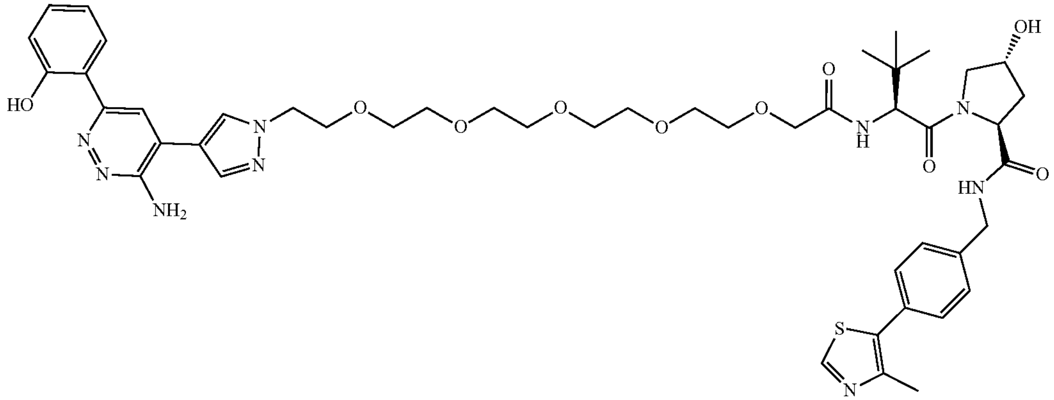 [SMILES: Cc1ncsc1-c1ccc(CNC(=O)[C@@H]2C[C@@H](O)CN2C(=O)[C@@H](NC(=O)COCCOCCOCCOCCOCCn2cc(-c3cc(-c4ccccc4O)nnc3N)cn2)C(C)(C)C)cc1] | (2S,4R)-1-((S)-20-(4-(3-amino-6-(2-hydroxyphenyl)pyridazin-4-yl)-1H-pyrazol-1-yl)-2-(tert-butyl)-4-oxo-6,9,12,15,18-pentaoxa-3-azaicosanoyl)-4-hydroxy-N-(4-(4-methylthiazol-5-yl)benzyl)pyrrolidine-2-carboxamide |

TABLE 1A-continued

| Exemplary bifunctional degradation compounds of the present disclosure | | |
|---|---|---|
| Ex. # | Structure | Compound Name |
| 5 | 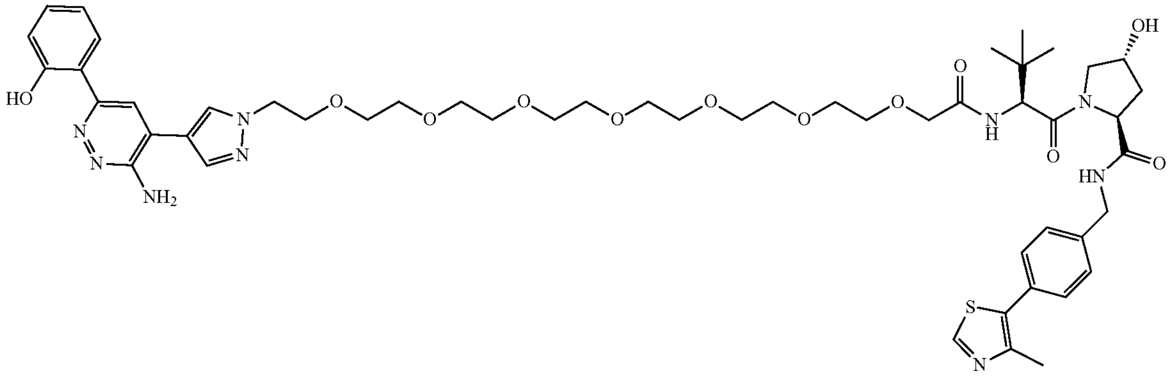 [SMILES: Cc1ncsc1-c1ccc(CNC(=O)[C@@H]2C[C@@H](O)CN2C(=O)[C@@H](NC(=O)COCCOCCOCCOCCOCCOCCOCCn2cc(-c3cc(-c4ccccc4O)nnc3N)cn2)C(C)(C)C)cc1] | (2S,4R)-1-((S)-26-(4-(3-amino-6-(2-hydroxyphenyl)pyridazin-4-yl)-1H-pyrazol-1-yl)-2-(tert-butyl)-4-oxo-6,9,12,15,18,21,24-heptaoxa-3-azahexacosanoyl)-4-hydroxy-N-(4-(4-methylthiazol-5-yl)benzyl)pyrrolidine-2-carboxamide |
| 6 | 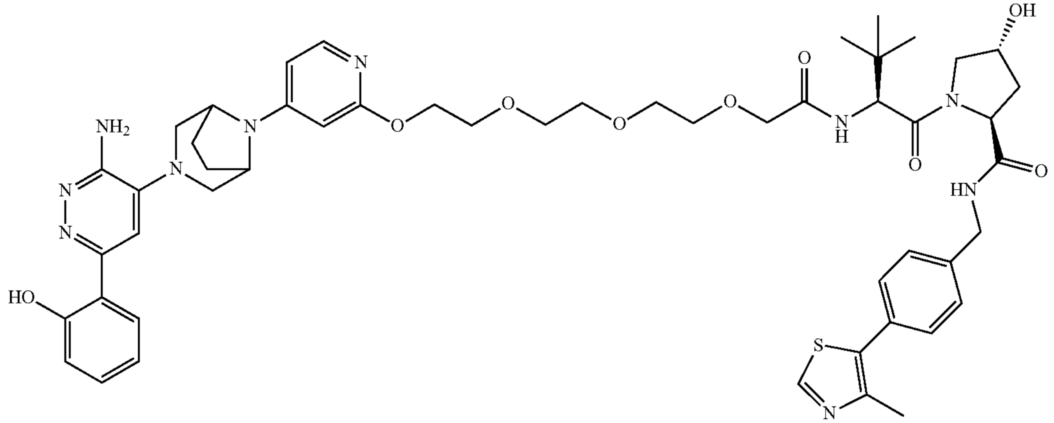 [SMILES: Cc1ncsc1-c1ccc(CNC(=O)[C@@H]2C[C@@H](O)CN2C(=O)[C@@H](NC(=O)COCCOCCOCCOc2cc(N3C4CCC3CN(c3cc(-c5ccccc5O)nnc3N)C4)ccn2)C(C)(C)C)cc1] | (2S,4R)-1-((2S)-14-((4-(3-(3-amino-6-(2-hydroxyphenyl)pyridazin-4-yl)-3,8-diazabicyclo[2.1]octan-8-yl)pyridin-2-yl)oxy)-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide |

TABLE 1A-continued

| Exemplary bifunctional degradation compounds of the present disclosure | | |
|---|---|---|
| Ex. # | Structure | Compound Name |
| 7 | 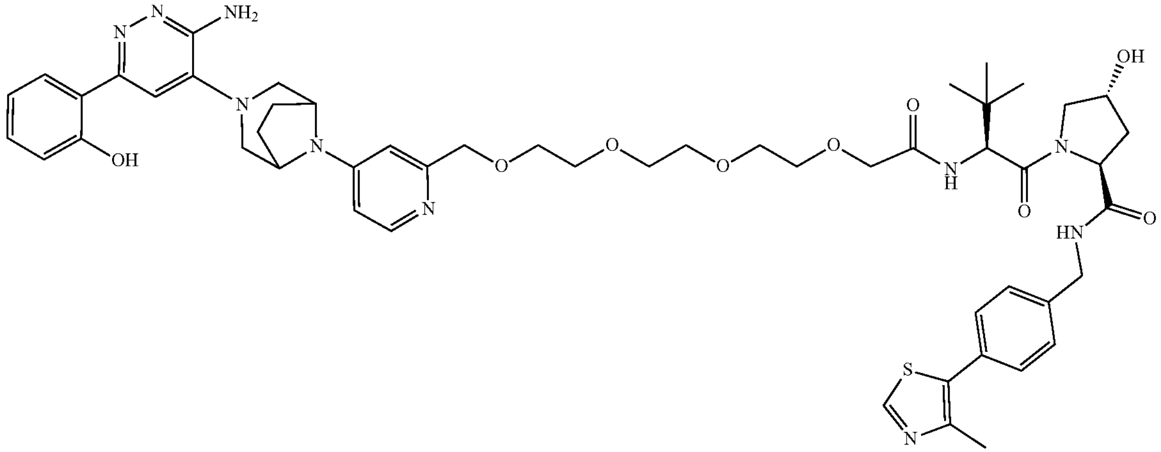 [SMILES: Cc1ncsc1-c1ccc(CNC(=O)[C@@H]2C[C@@H](O)CN2C(=O)[C@@H](NC(=O)COCCOCCOCCOCc2cc(N3C4CCC3CN(c3cc(-c5ccccc5O)nnc3N)C4)ccn2)C(C)(C)C)cc1] | (2S,4R)-1-((2S)-17-((4-(3-(3-amino-6-(2-hydroxyphenyl)pyridazin-4-yl)-3,8-diazabicyclo[3.2.1]octan-8-yl)pyridin-2-yl)oxy)-2-(tert-butyl)-4-oxo-6,9,12,15-tetraoxa-3-azaheptadecanoyl)-4-hydroxy-N-(4-(4-methylthiazol-5-yl)benzyl)pyrrolidine-2-carboxamide |
| 8 | 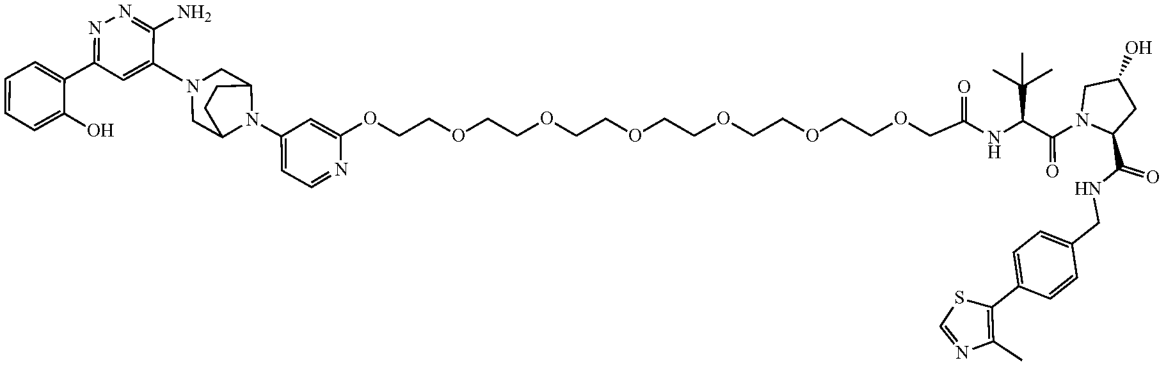 [SMILES: Cc1ncsc1-c1ccc(CNC(=O)[C@@H]2C[C@@H](O)CN2C(=O)[C@@H](NC(=O)COCCOCCOCCOCCOCCOCCOc2cc(N3C4CCC3CN(c3cc(-c5ccccc5O)nnc3N)C4)ccn2)C(C)(C)C)cc1] | (2S,4R)-1-((2S)-23-((4-(3-(3-amino-6-(2-hydroxyphenyl)pyridazin-4-yl)-3,8-diazabicyclo[3.2.1]octan-8-yl)pyridin-2-yl)oxy)-2-(tert-butyl)-4-oxo-6,9,12,15,18,21-hexaoxa-3-azatricosanoyl)-4-hydroxy-N-(4-(4-methylthiazol-5-yl)benzyl)pyrrolidine-2-carboxamide |

TABLE 1A-continued

| Ex. # | Structure | Compound Name |
|---|---|---|
| | Exemplary bifunctional degradation compounds of the present disclosure | |
| 9 | 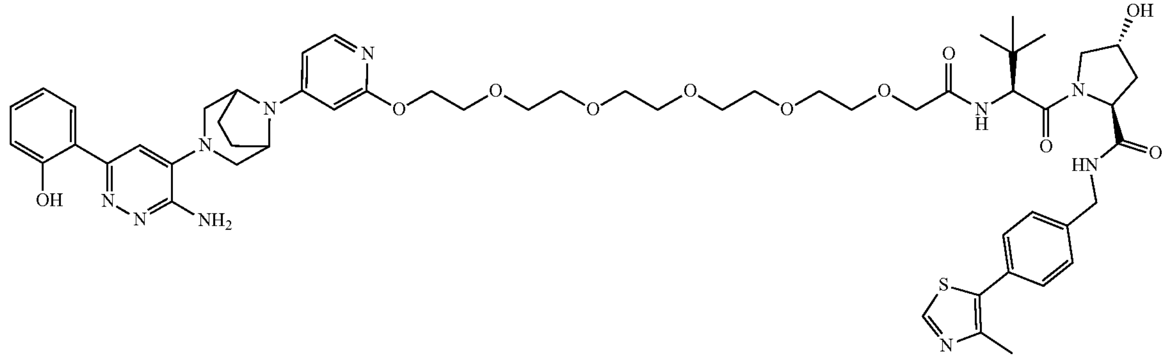 [SMILES: Cc1ncsc1-c1ccc(CNC(=O)[C@@H]2C[C@@H](O)CN2C(=O)[C@@H](NC(=O)COCCOCCOCCOCCOCCOc2cc(N3C4CCC3CN(c3cc(-c5ccccc5O)nnc3N)C4)ccn2)C(C)(C)C)cc1] | (2S,4R)-1-((S)-20-((4-((1R,5S)-3-(3-amino-6-(2-hydroxyphenyl)pyridazin-4-yl)-3,8-diazabicyclo[3.2.1]octan-8-yl)pyridin-2-yl)oxy)-2-(tert-butyl)-4-oxo-6,9,12,15,18-pentaoxa-3-azaicosanoyl)-4-hydroxy-N-(4-(4-methylthiazol-5-yl)benzyl)pyrrolidine-2-carboxamide |
| 10 | 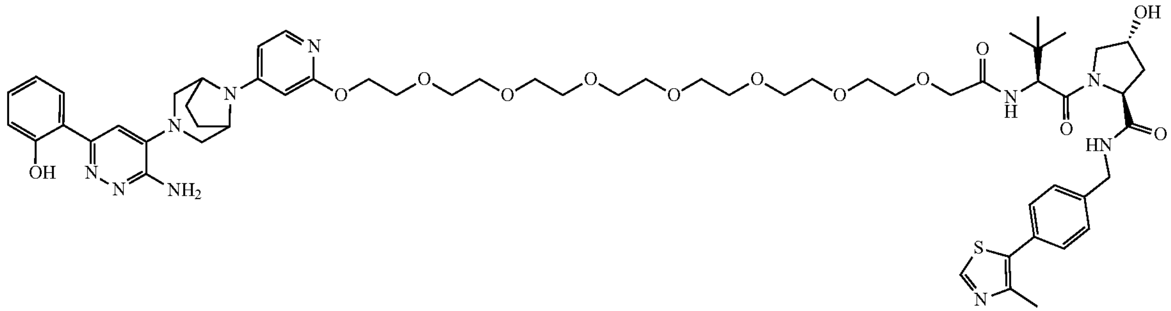 [SMILES: Cc1ncsc1-c1ccc(CNC(=O)[C@@H]2C[C@@H](O)CN2C(=O)[C@@H](NC(=O)COCCOCCOCCOCCOCCOCCOCCOc2cc(N3C4CCC3CN(c3cc(-c5ccccc5O)nnc3N)C4)ccn2)C(C)(C)C)cc1] | (2S,4R)-1-((2S)-26-((4-(3-(3-amino-6-(2-hydroxyphenyl)pyridazin-4-yl)-3,8-diazabicyclo[3.2.1]octan-8-yl)pyridin-2-yl)oxy)-2-(tert-butyl)-4-oxo-6,9,12,15,18,21,24-heptaoxa-3-azahexacosanoyl)-4-hydroxy-N-(4-(4-methylthiazol-5-yl)benzyl)pyrrolidine-2-carboxamide |

TABLE 1A-continued

| Exemplary bifunctional degradation compounds of the present disclosure | | |
|---|---|---|
| Ex. # | Structure | Compound Name |
| 11 | 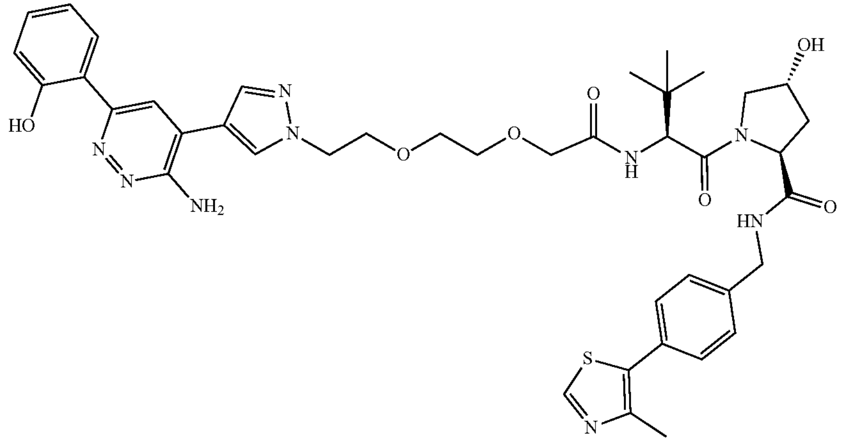 [SMILES: Cc1ncsc1-c1ccc(CNC(=O)[C@@H]2C[C@@H](O)CN2C(=O)[C@@H](NC(=O)COCCOCCn2cc(-c3cc(-c4ccccc4O)nnc3N)cn2)C(C)(C)C)cc1] | (2S,4R)-1-((S)-2-(2-(2-(2-(4-(3-amino-6-(2-hydroxyphenyl)pyridazin-4-yl)-1H-pyrazol-1-yl)ethoxy)ethoxy)acetamido)-3,3-dimethylbutanoyl)-4-hydroxy-N-(4-(4-methylthiazol-5-yl)benzyl)pyrrolidine-2-carboxamide |
| 12 | 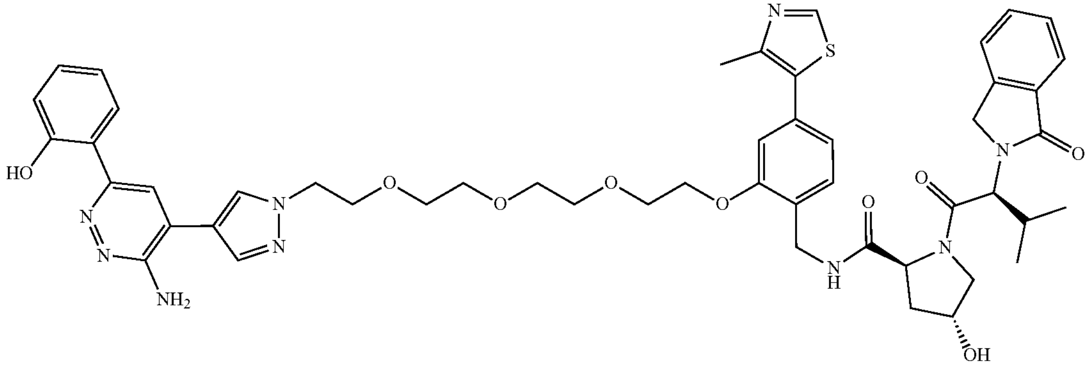 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCn2cc(-c3cc(-c4ccccc4O)nnc3N)cn2)c1] | (2S,4R)-N-(2-(2-(2-(2-(2-(4-(3-amino-6-(2-hydroxyphenyl)pyridazin-4-yl)-1H-pyrazol-1-yl)ethoxy)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide |

TABLE 1A-continued

| Exemplary bifunctional degradation compounds of the present disclosure | | |
|---|---|---|
| Ex. # | Structure | Compound Name |
| 13 | 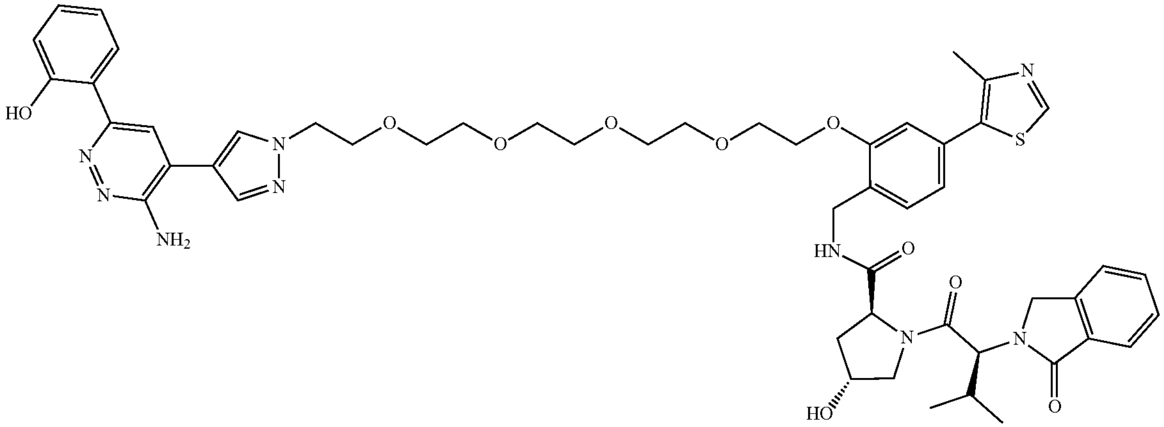 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOCCn2cc(-c3cc(-c4ccccc4O)nnc3N)cn2)c1] | (2S,4R)-N-(2-((14-(4-(3-amino-6-(2-hydroxyphenyl)pyridazin-4-yl)-1H-pyrazol-1-yl)-3,6,9,12-tetraoxatetradecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide |
| 14 | 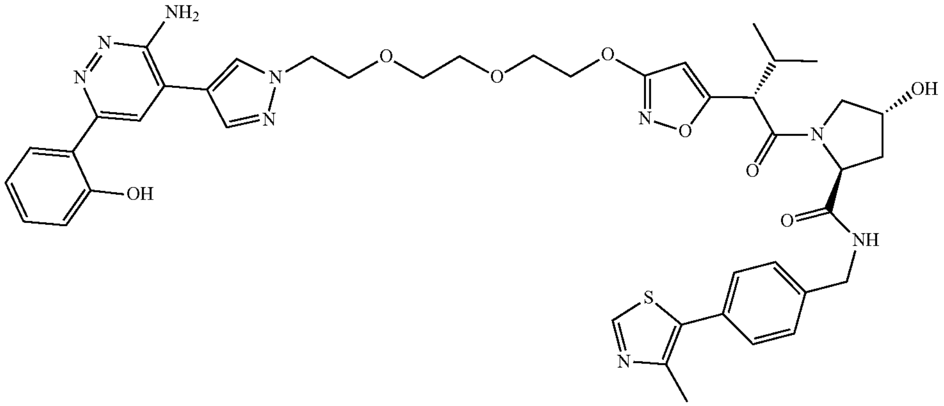 [SMILES: Cc1ncsc1-c1ccc(CNC(=O)[C@@H]2C[C@@H](O)CN2C(=O)[C@H](c2cc(OCCOCCOCCn3cc(-c4cc(-c5ccccc5O)nnc4N)cn3)no2)C(C)C)cc1] | (2S,4R)-1-[(2S)-2-(3-[2-[2-(2-[4-[3-amino-6-(2-hydroxyphenyl)pyridazin-4-yl]-1H-pyrazol-1-yl]ethoxy)ethoxy]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 15 | 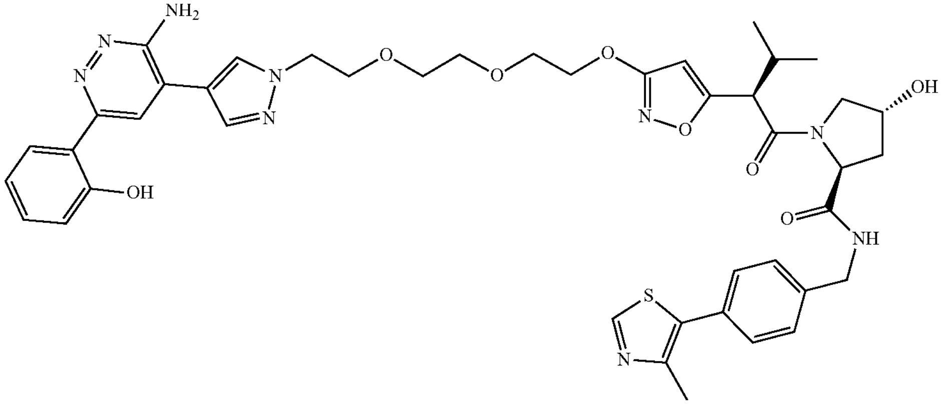 [SMILES: Cc1ncsc1-c1ccc(CNC(=O)[C@@H]2C[C@@H](O)CN2C(=O)[C@@H](c2cc(OCCOCCOCCn3cc(-c4cc(-c5ccccc5O)nnc4N)cn3)no2)C(C)C)cc1] | (2S,4R)-1-[(2R)-2-(3-[2-[2-(2-[4-[3-amino-6-(2-hydroxyphenyl)pyridazin-4-yl]-1H-pyrazol-1-yl]ethoxy)ethoxy]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide |
| 16 | 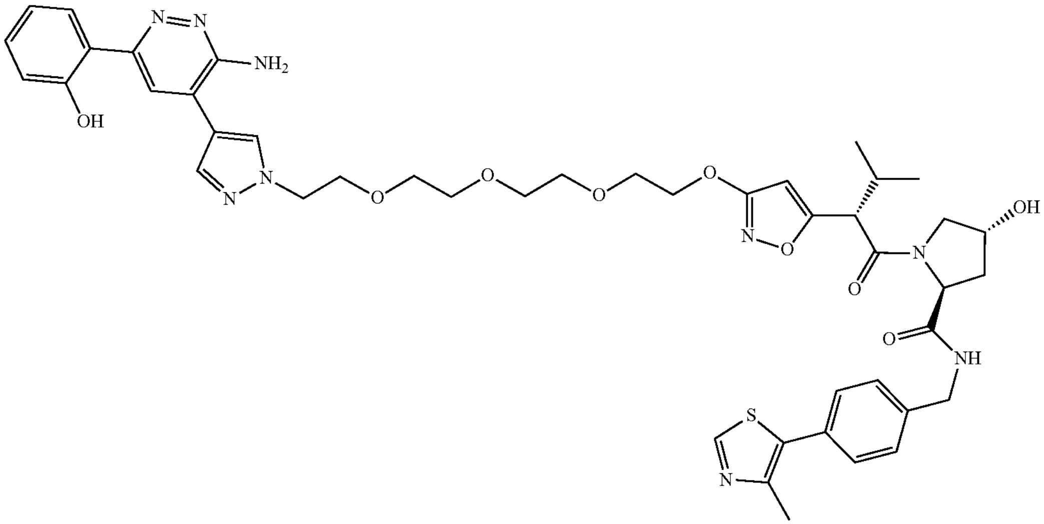 [SMILES: Cc1ncsc1-c1ccc(CNC(=O)[C@@H]2C[C@@H](O)CN2C(=O)[C@H](c2cc(OCCOCCOCCOCCn3cc(-c4cc(-c5ccccc5O)nnc4N)cn3)no2)C(C)C)cc1] | (2S,4R)-1-((S)-2-(3-(2-(2-(2-(2-(4-(3-amino-6-(2-hydroxyphenyl)pyridazin-4-yl)-1H-pyrazol-1-yl)ethoxy)ethoxy)ethoxy)ethoxy)isoxazol-5-yl)-3-methylbutanoyl)-4-hydroxy-N-(4-(4-methylthiazol-5-yl)benzyl)pyrrolidine-2-carboxamide |

TABLE 1A-continued

| Exemplary bifunctional degradation compounds of the present disclosure | | |
|---|---|---|
| Ex. # | Structure | Compound Name |
| 17 | 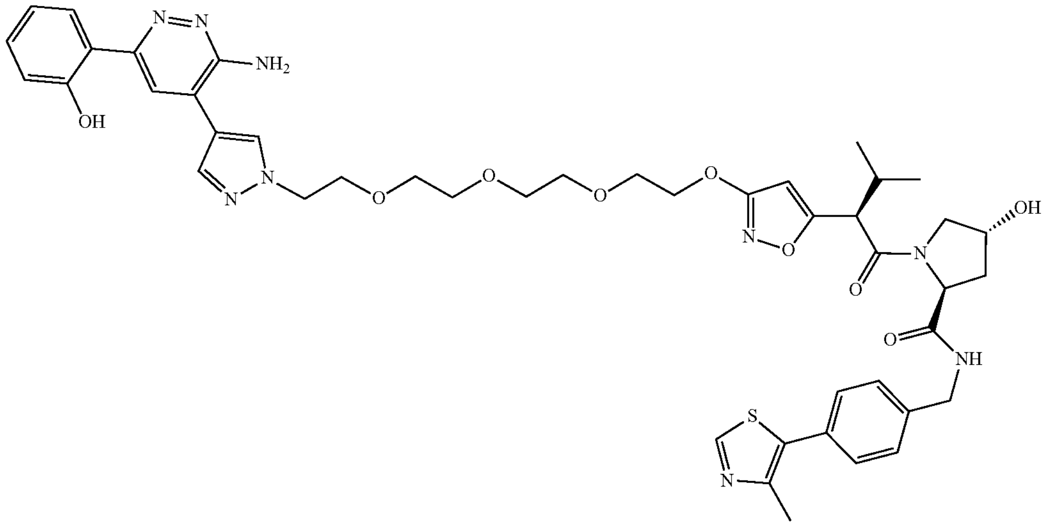 [SMILES: Cc1ncsc1-c1ccc(CNC(=O)[C@@H]2C[C@@H](O)CN2C(=O)[C@@H](c2cc(OCCOCCOCCOCCn3cc(-c4cc(-c5ccccc5O)nnc4N)cn3)no2)C(C)C)cc1] | (2S,4R)-1-((R)-2-(3-(2-(2-(2-(2-(4-(3-amino-6-(2-hydroxyphenyl)pyridazin-4-yl)-1H-pyrazol-1-yl)ethoxy)ethoxy)ethoxy)ethoxy)isoxazol-5-yl)-3-methylbutanoyl)-4-hydroxy-N-(4-(4-methylthiazol-5-yl)benzyl)pyrrolidine-2-carboxamide |
| 18 | 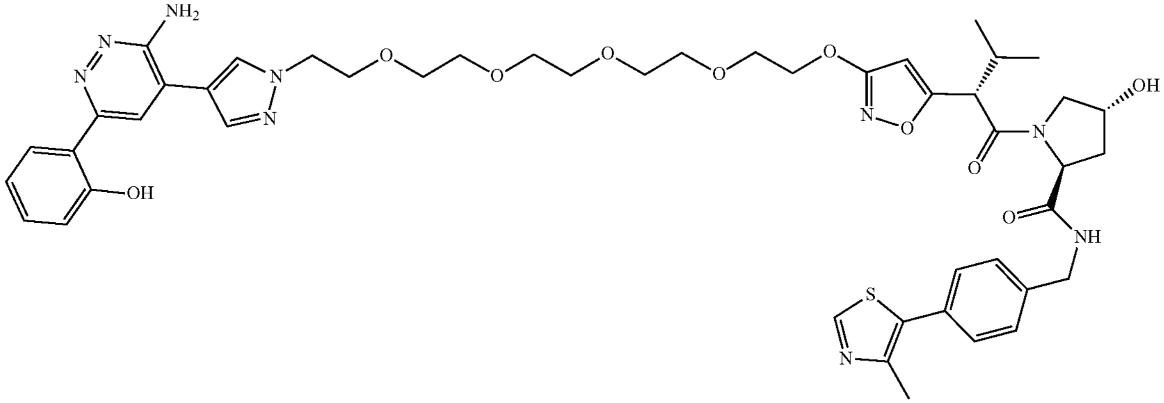 [SMILES: Cc1ncsc1-c1ccc(CNC(=O)[C@@H]2C[C@@H](O)CN2C(=O)[C@H](c2cc(OCCOCCOCCOCCOCCn3cc(-c4cc(-c5ccccc5O)nnc4N)cn3)no2)C(C)C)cc1] | (2S,4R)-1-[(2S)-2-[3-[(14-[4-[3-amino-6-(2-hydroxyphenyl)pyridazin-4-yl]-1H-pyrazol-1-yl]-3,6,9,12-tetraoxatetradecan-1-yl)oxy]-1,2-oxazol-5-yl]-3-methylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 19 | 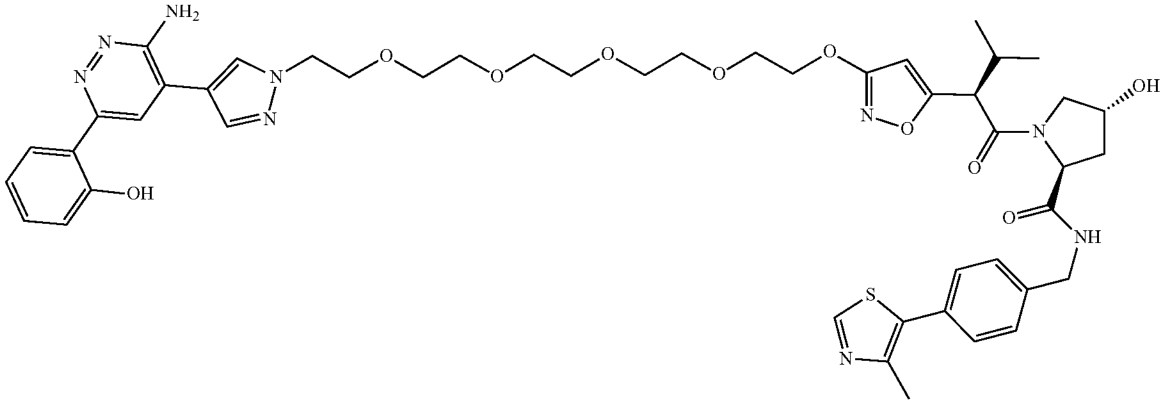 [SMILES: Cc1ncsc1-c1ccc(CNC(=O)[C@@H]2C[C@@H](O)CN2C(=O)[C@@H](c2cc(OCCOCCOCCOCCOCCn3cc(-c4cc(-c5ccccc5O)nnc4N)cn3)no2)C(C)C)cc1] | (2S,4R)-1-[(2R)-2-[3-[(14-[4-[3-amino-6-(2-hydroxyphenyl)pyridazin-4-yl]-1H-pyrazol-1-yl]-3,6,9,12-tetraoxatetradecan-1-yl)oxy]-1,2-oxazol-5-yl]-3-methylbutanoyl]-4-hydroxy-N-[[4-(4-methyl-1,3-thiazol-5-yl)phenyl]methyl]pyrrolidine-2-carboxamide |
| 20 | 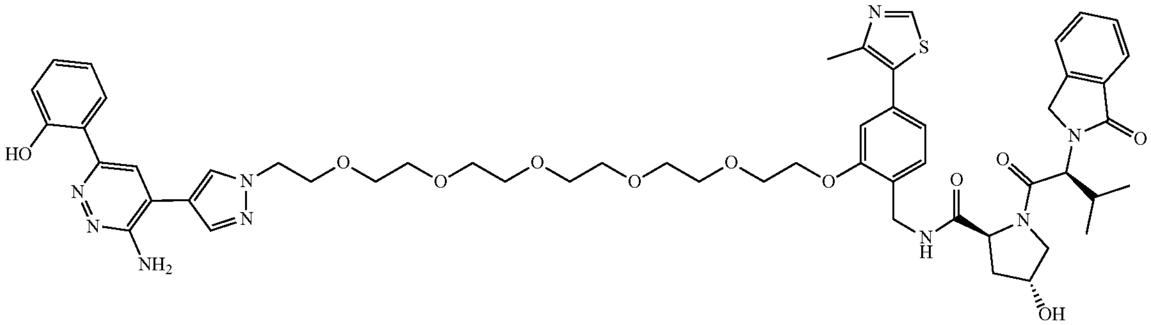 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOCCOCCn2cc(-c3cc(-c4ccccc4O)nnc3N)cn2)c1] | (2S,4R)-N-(2-((17-(4-(3-amino-6-(2-hydroxyphenyl)pyridazin-4-yl)-1H-pyrazol-1-yl)-3,6,9,12,15-pentaoxaheptadecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide |

TABLE 1A-continued

| Exemplary bifunctional degradation compounds of the present disclosure | | |
|---|---|---|
| Ex. # | Structure | Compound Name |
| 21 | 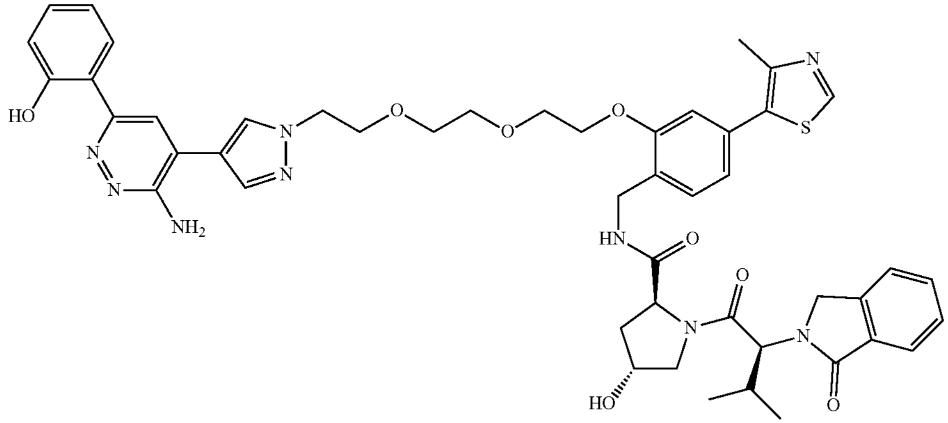 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCn2cc(-c3cc(-c4ccccc4O)nnc3N)cn2)c1] | (2S,4R)-N-(2-(2-(2-(2-(4-(3-amino-6-(2-hydroxyphenyl)pyridazin-4-yl)-1H-pyrazol-1-yl)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide |
| 22 | 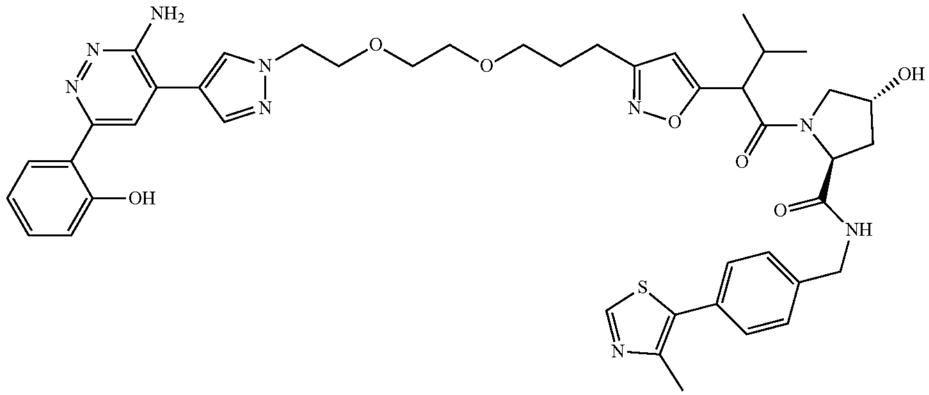 [SMILES: Cc1ncsc1-c1ccc(CNC(=O)[C@@H]2C[C@@H](O)CN2C(=O)C(c2cc(CCCOCCOCCn3cc(-c4cc(-c5ccccc5O)nnc4N)cn3)no2)C(C)C)cc1] | (2S,4R)-1-(2-(3-(3-(2-(2-(4-(3-amino-6-(2-hydroxyphenyl)pyridazin-4-yl)-1H-pyrazol-1-yl)ethoxy)ethoxy)propyl)isoxazol-5-yl)-3-methylbutanoyl)-4-hydroxy-N-(4-(4-methylthiazol-5-yl)benzyl)pyrrolidine-2-carboxamide |

TABLE 1A-continued
| Exemplary bifunctional degradation compounds of the present disclosure | | |
|---|---|---|
| Ex. # | Structure | Compound Name |
| 23 | 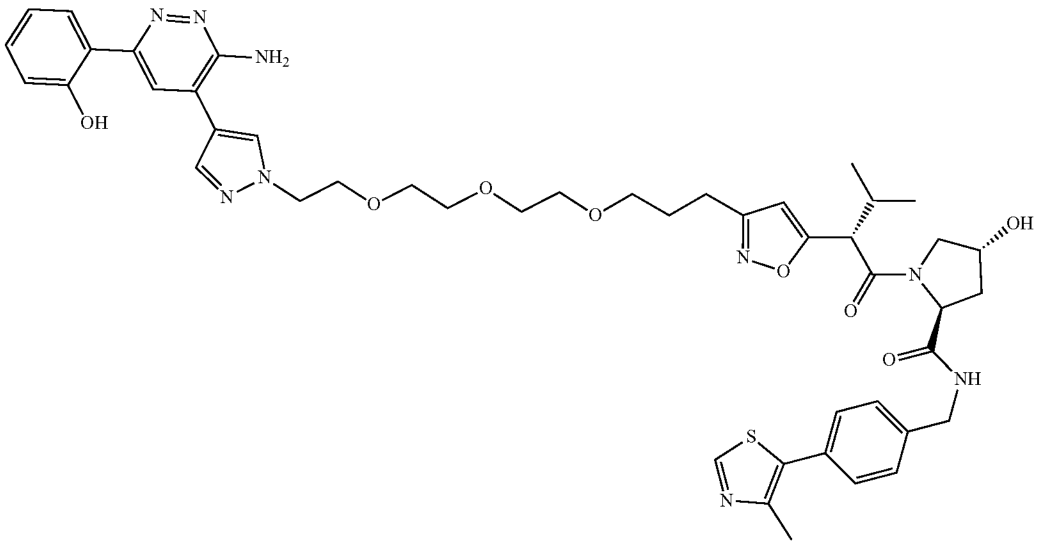 [SMILES: Cc1ncsc1-c1ccc(CNC(=O)[C@@H]2C[C@@H](O)CN2C(=O)[C@H](c2cc(CCCOCCOCCOCCn3cc(-c4cc(-c5ccccc5O)nnc4N)cn3)no2)C(C)C)cc1] | (2S,4R)-1-[(2S)-2-[3-(3-[2-[2-(2-[4-[3-amino-6-(2-hydroxyphenyl)pyridazin-4-yl]-1H-pyrazol-1-yl]ethoxy)ethoxy]ethoxy]propyl)-1,2-oxazol-5-yl]-3-methylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 24 | 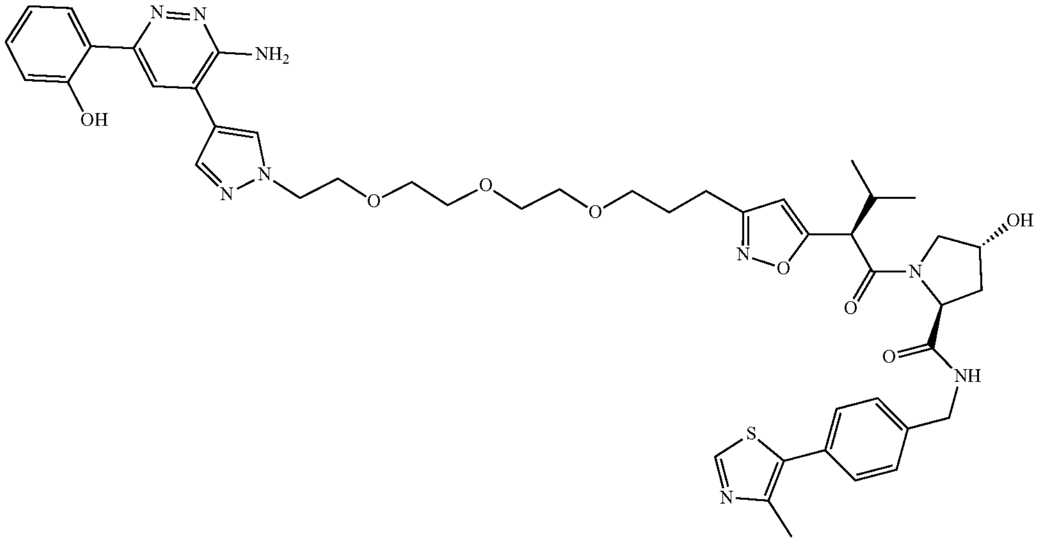 [SMILES: Cc1ncsc1-c1ccc(CNC(=O)[C@@H]2C[C@@H](O)CN2C(=O)[C@@H](c2cc(CCCOCCOCCOCCn3cc(-c4cc(-c5ccccc5O)nnc4N)cn3)no2)C(C)C)cc1] | (2S,4R)-1-[(2R)-2-[3-(3-[2-[2-(2-[4-[3-amino-6-(2-hydroxyphenyl)pyridazin-4-yl]-1H-pyrazol-1-yl]ethoxy)ethoxy]ethoxy]propyl)-1,2-oxazol-5-yl]-3-methylbutanoyl]-4-hydroxy-N-[[4-(4-methyl-1,3-thiazol-5-yl)phenyl]methyl]pyrrolidine-2-carboxamide |
| 25 | 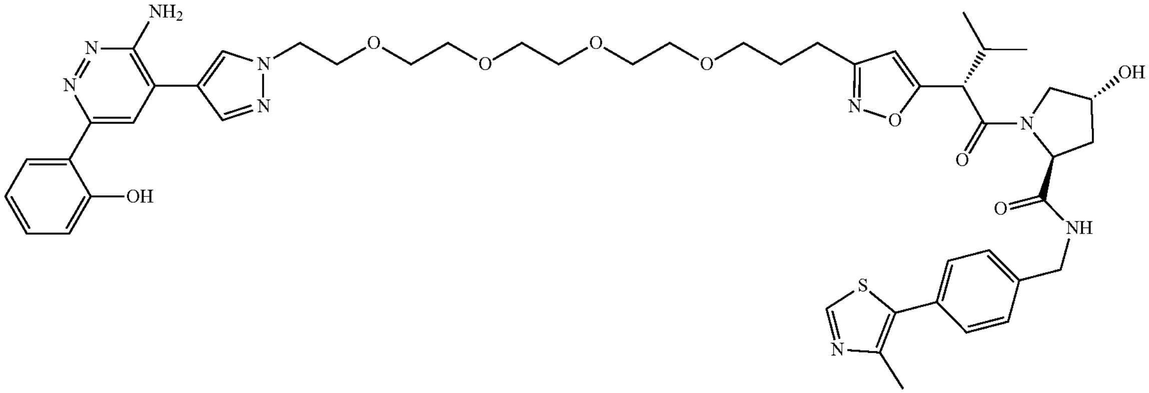 [SMILES: Cc1ncsc1-c1ccc(CNC(=O)[C@@H]2C[C@@H](O)CN2C(=O)[C@H](c2cc(CCCOCCOCCOCCOCCn3cc(-c4cc(-c5ccccc5O)nnc4N)cn3)no2)C(C)C)cc1] | (2S,4R)-1-[(2S)-2-[3-(1-[4-[3-amino-6-(2-hydroxyphenyl)pyridazin-4-yl]-1H-pyrazol-1-yl]-3,6,9,12-tetraoxapentadecan-15-yl)-1,2-oxazol-5-yl]-3-methylbutanoyl]-4-hydroxy-N-[4-(4-methyl-1,3-thiazol-5-yl)phenyl]methyl]pyrrolidine-2-carboxamide |

TABLE 1A-continued

Exemplary bifunctional degradation compounds of the present disclosure

| Ex. # | Structure | Compound Name |
|---|---|---|
| 26 | 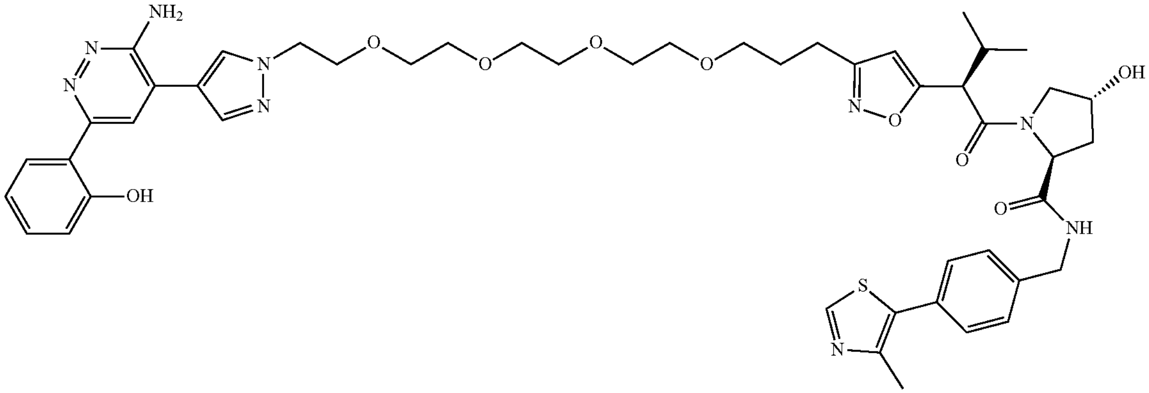 [SMILES: Cc1ncsc1-c1ccc(CNC(=O)[C@@H]2C[C@@H](O)CN2C(=O)[C@@H](c2cc(CCCOCCOCCOCCOCCn3cc(-c4cc(-c5ccccc5O)nnc4N)cn3)no2)C(C)C)cc1] | (2S,4R)-1-[(2R)-2-[3-(1-[4-[3-amino-6-(2-hydroxyphenyl)pyridazin-4-yl]-1H-pyrazol-1-yl]-3,6,9,12-tetraoxapentadecan-15-yl)-1,2-oxazol-5-yl]-3-methylbutanoyl]-4-hydroxy-N-[[4-(4-methyl-1,3-thiazol-5-yl)phenyl]methyl]pyrrolidine-2-carboxamide |
| 27 | 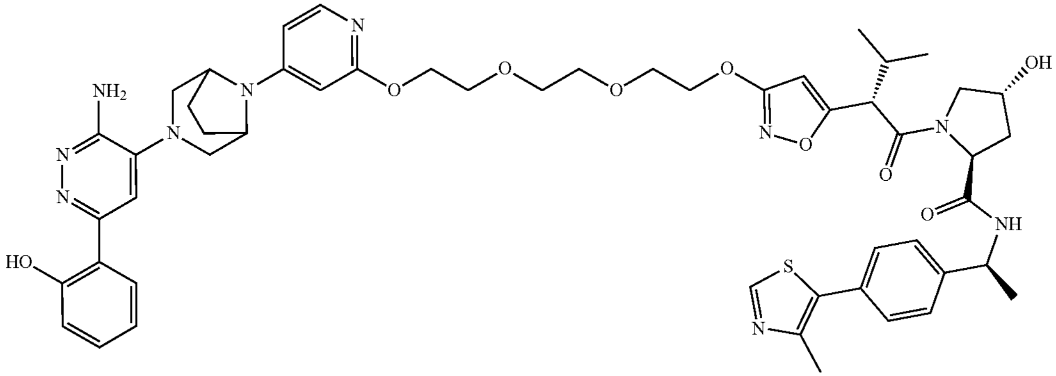 [SMILES: Cc1ncsc1-c1ccc([C@H](C)NC(=O)[C@@H]2C[C@@H](O)CN2C(=O)[C@H](c2cc(OCCOCCOCCOc3cc(N4C5CCC4CN(c4cc(-c6ccccc6O)nnc4N)C5)ccn3)no2)C(C)C)cc1] | (2S,4R)-1-[(2S)-2-[3-[2-(2-[2-[(4-[3-[3-amino-6-(2-hydroxyphenyl)pyridazin-4-yl]-3,8-diazabicyclo[3.2.1]octan-8-yl]pyridin-2-yl)oxy]ethoxy]ethoxy)ethoxy]-1,2-oxazol-5-yl]-3-methylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 28 | 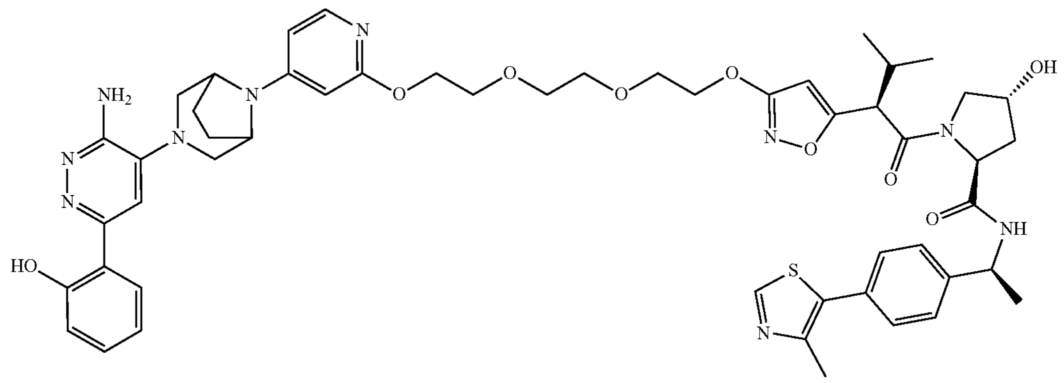 [SMILES: Cc1ncsc1-c1ccc([C@H](C)NC(=O)[C@@H]2C[C@@H](O)CN2C(=O)[C@@H](c2cc(OCCOCCOCCOc3cc(N4C5CCC4CN(c4cc(-c6ccccc6O)nnc4N)C5)ccn3)no2)C(C)C)cc1] | (2S,4R)-1-[(2R)-2-[3-[2-(2-[2-[(4-[3-[3-amino-6-(2-hydroxyphenyl)pyridazin-4-yl]-3,8-diazabicyclo[3.2.1]octan-8-yl]pyridin-2-yl)oxy]ethoxy]ethoxy)ethoxy]-1,2-oxazol-5-yl]-3-methylbutanoyl]-4-hydroxy-N-[[4-(4-methyl-1,3-thiazol-5-yl)phenyl]methyl]pyrrolidine-2-carboxamide |
| 29 | 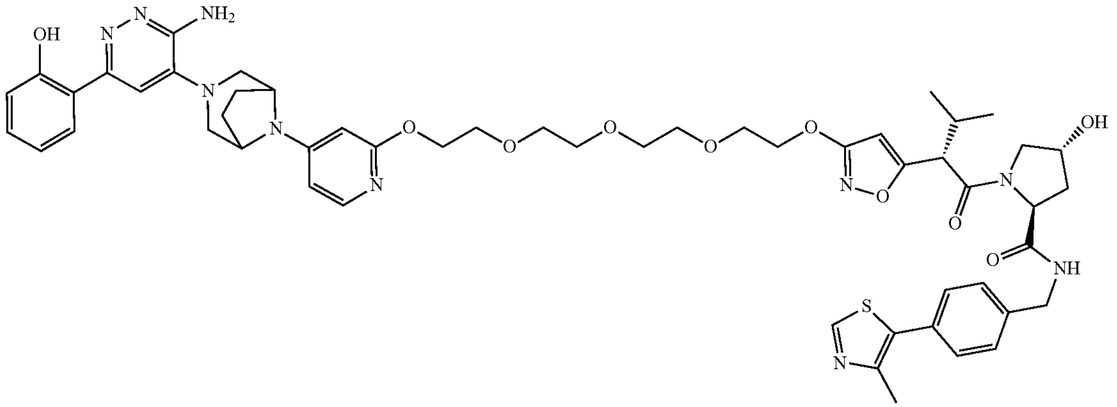 [SMILES: Cc1ncsc1-c1ccc(CNC(=O)[C@@H]2C[C@@H](O)CN2C(=O)[C@H](c2cc(OCCOCCOCCOCCOc3cc(N4C5CCC4CN(c4cc(-c6ccccc6O)nnc4N)C5)ccn3)no2)C(C)C)cc1] | (2S,4R)-1-[(2S)-2-(3-[[1-(4-[3-[3-amino-6-(2-hydroxyphenyl)pyridazin-4-yl]-3,8-diazabicyclo[3.2.1]octan-8-yl]pyridin-2-yl)-1,4,7,10-tetraoxadodecan-12-yl]oxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 30 | 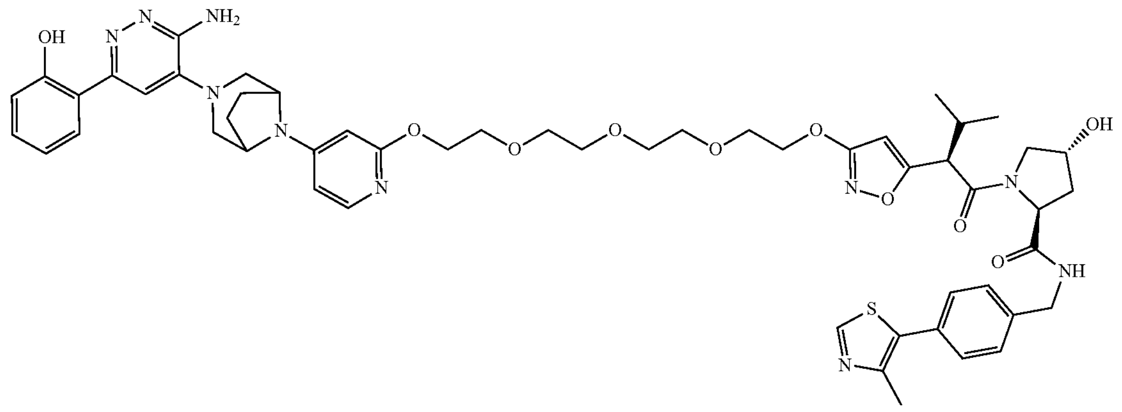 [SMILES: Cc1ncsc1-c1ccc(CNC(=O)[C@@H]2C[C@@H](O)CN2C(=O)[C@@H](c2cc(OCCOCCOCCOCCOc3cc(N4C5CCC4CN(c4cc(-c6ccccc6O)nnc4N)C5)ccn3)no2)C(C)C)cc1] | (2S,4R)-1-[(2R)-2-(3-[[1-(4-[3-[3-amino-6-(2-hydroxyphenyl)pyridazin-4-yl]-3,8-diazabicyclo[3.2.1]octan-8-yl]pyridin-2-yl)-1,4,7,10-tetraoxadodecan-12-yl]oxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide |
| 31 | 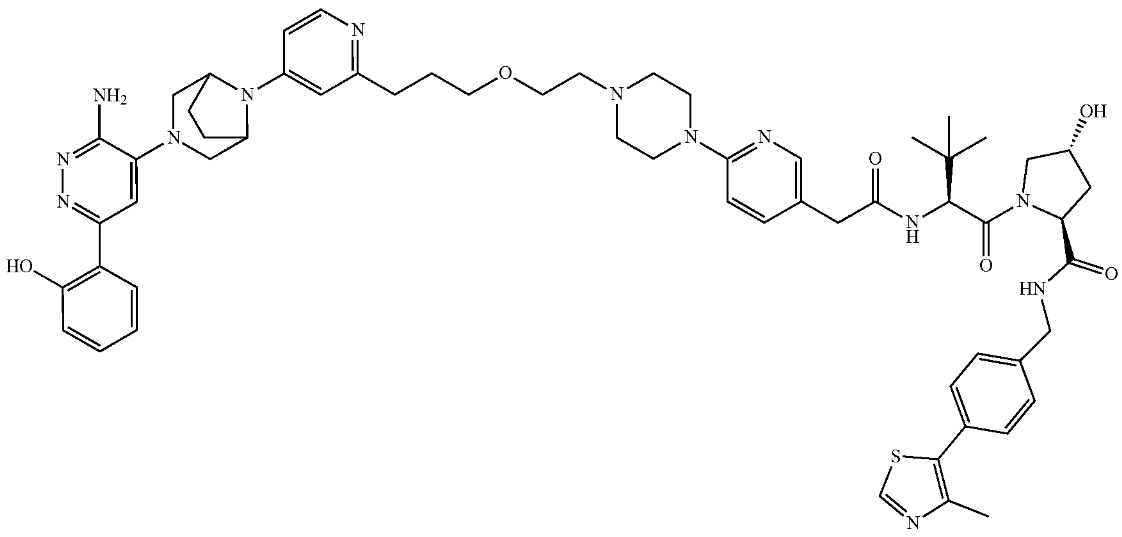 [SMILES: Cc1ncsc1-c1ccc(CNC(=O)[C@@H]2C[C@@H](O)CN2C(=O)[C@@H](NC(=O)Cc2ccc(N3CCN(CCOCCCc4cc(N5C6CCC5CN(c5cc(-c7ccccc7O)nnc5N)C6)ccn4)CC3)nc2)C(C)(C)C)cc1] | (2S,4R)-1-((2S)-2-(2-(6-(4-(2-(3-(4-(3-(3-amino-6-(2-hydroxyphenyl)pyridazin-4-yl)-3,8-diazabicyclo[3.2.1]octan-8-yl)pyridin-2-yl)propoxy)ethyl)piperazin-1-yl)pyridin-3-yl)acetamido)-3,3-dimethylbutanoyl)-4-hydroxy-N-(4-(4-methylthiazol-5-yl)benzyl)pyrrolidine-2-carboxamide |

TABLE 1A-continued

| Exemplary bifunctional degradation compounds of the present disclosure | | |
|---|---|---|
| Ex. # | Structure | Compound Name |
| 32 | 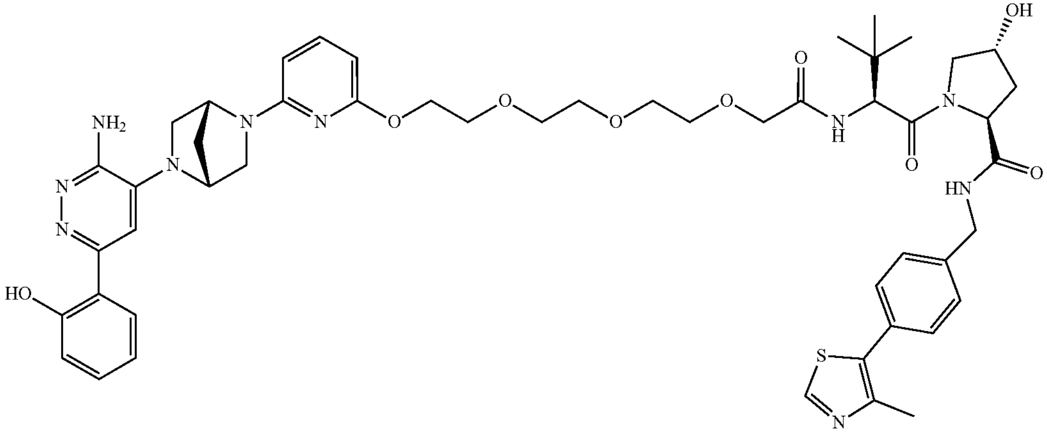 [SMILES: Cc1ncsc1-c1ccc(CNC(=O)[C@@H]2C[C@@H](O)CN2C(=O)[C@@H](NC(=O)COCCOCCOCCOc2cccc(N3C[C@H]4C[C@@H]3CN4c3cc(-c4ccccc4O)nnc3N)n2)C(C)(C)C)cc1] | (2S,4R)-1-[(2S)-2-(1-[6-[(1R,4R)-5-[3-amino-6-(2-hydroxyphenyl)pyridazin-4-yl]-2,5-diazabicyclo[2.2.1]heptan-2-yl]pyridin-2-yl]-1,4,7,10-tetraoxadodecan-12-amido)-3,3-dimethylbutanoyl]-4-hydroxy-N-[[4-(4-methyl-1,3-thiazol-5-yl)phenyl]methyl]pyrrolidine-2-carboxamide |
| 33 | 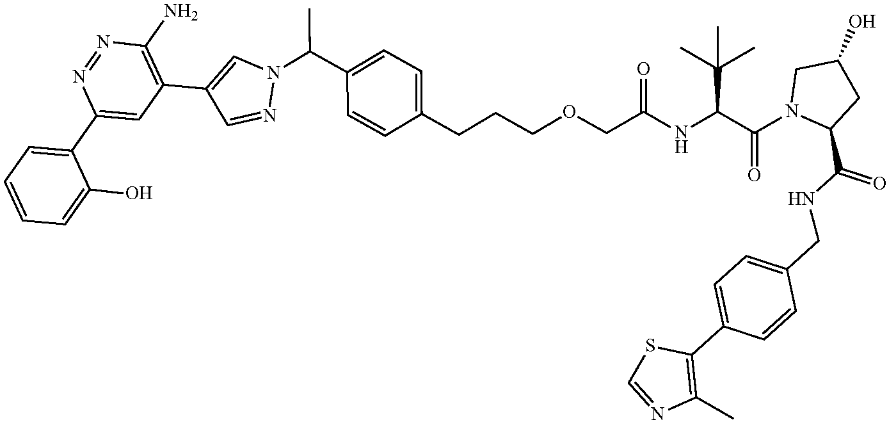 [SMILES: Cc1ncsc1-c1ccc(CNC(=O)[C@@H]2C[C@@H](O)CN2C(=O)[C@@H](NC(=O)COCCCc2ccc(C(C)n3cc(-c4cc(-c5ccccc5O)nnc4N)cn3)cc2)C(C)(C)C)cc1] | (2S,4R)-1-[(2S)-2-(2-[3-[4-(1-[4-[3-amino-6-(2-hydroxyphenyl)pyridazin-4-yl]-1H-pyrazol-1-yl]ethyl)phenyl]propoxy]acetamido)-3,3-dimethylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 34 | 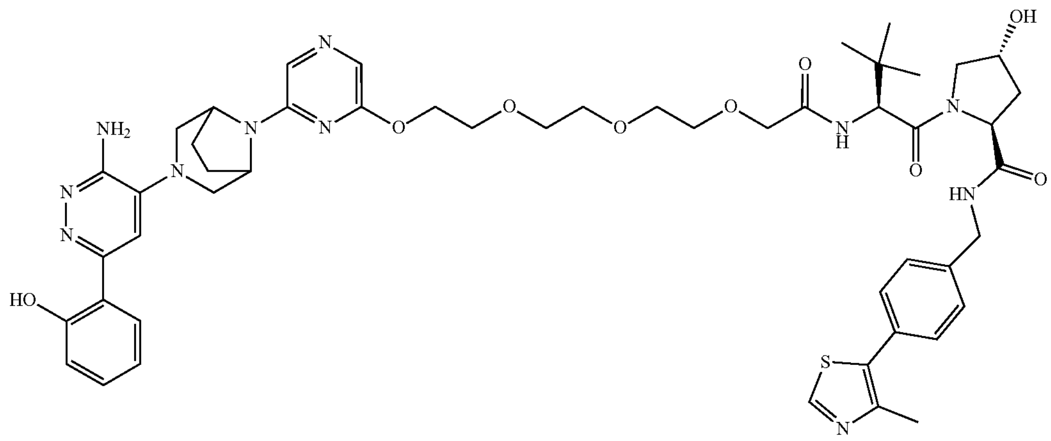 [SMILES: Cc1ncsc1-c1ccc(CNC(=O)[C@@H]2C[C@@H](O)CN2C(=O)[C@@H](NC(=O)COCCOCCOCCOc2cncc(N3C4CCC3CN(c3cc(-c5ccccc5O)nnc3N)C4)n2)C(C)(C)C)cc1] | (2S,4R)-1-[(2S)-2-[1-(6-[3-[3-amino-6-(2-hydroxyphenyl)pyridazin-4-yl]-3,8-diazabicyclo[3.2.1]octan-8-yl]pyrazin-2-yl)-1,4,7,10-tetraoxadodecan-12-amido]-3,3-dimethylbutanoyl]-4-hydroxy-N-[[4-(4-methyl-1,3-thiazol-5-yl)phenyl]methyl]pyrrolidine-2-carboxamide |
| 35 | 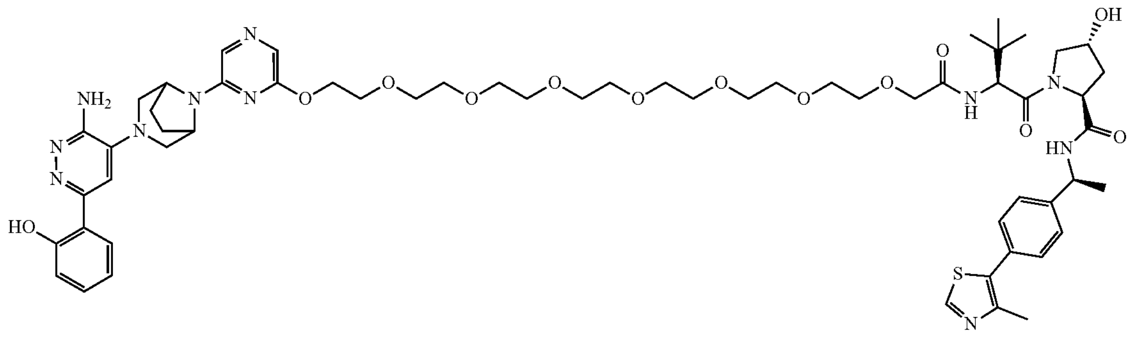 [SMILES: Cc1ncsc1-c1ccc([C@H](C)NC(=O)[C@@H]2C[C@@H](O)CN2C(=O)[C@@H](NC(=O)COCCOCCOCCOCCOCCOCCOCCOc2cncc(N3C4CCC3CN(c3cc(-c5ccccc5O)nnc3N)C4)n2)C(C)(C)C)cc1] | (2S,4R)-1-[(2S)-2-[1-(4-[3-[3-amino-6-(2-hydroxyphenyl)pyridazin-4-yl]-3,8-diazabicyclo[3.2.1]octan-8-yl]pyridin-2-yl)-1,4,7,10,13,16,19,22-octaoxatetracosan-24-amido]-3,3-dimethylbutanoyl]-4-hydroxy-N-[(1S)-1-[4-(4-methyl-1,3-thiazol-5-yl)phenyl]ethyl]pyrrolidine-2-carboxamide |

TABLE 1A-continued

| Ex. # | Structure | Compound Name |
|---|---|---|
| | Exemplary bifunctional degradation compounds of the present disclosure | |
| 36 | 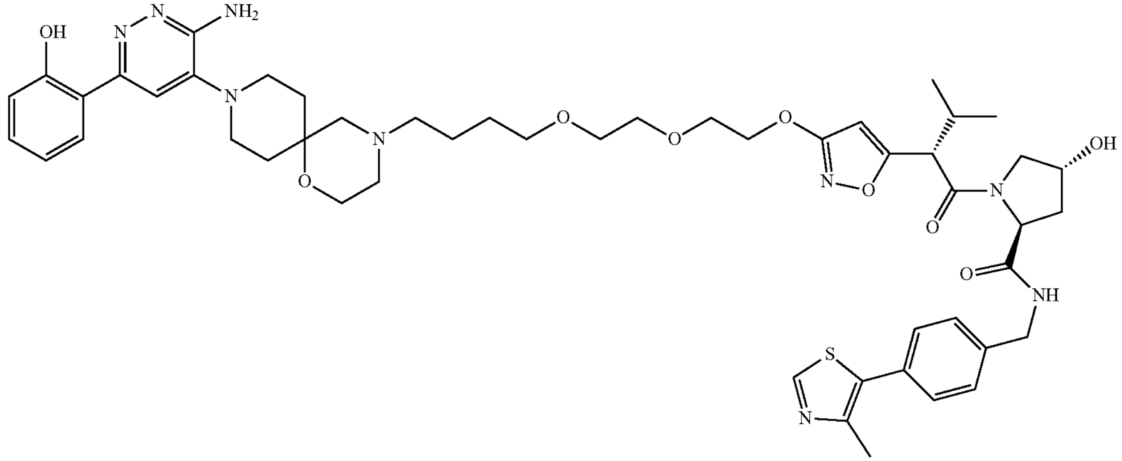 [SMILES: Cc1ncsc1-c1ccc(CNC(=O)[C@@H]2C[C@@H](O)CN2C(=O)[C@H](c2cc(OCCOCCOCCCCN3CCOC4(CCN(c5cc(-c6ccccc6O)nnc5N)CC4)C3)no2)C(C)C)cc1] | (2S,4R)-1-[(2S)-2-(3-[2-[2-(4-[9-[3-amino-6-(2-hydroxyphenyl)pyridazin-4-yl]-1-oxa-4,9-diazaspiro[5.5]undecan-4-yl]butoxy)ethoxy]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide |
| 37 | 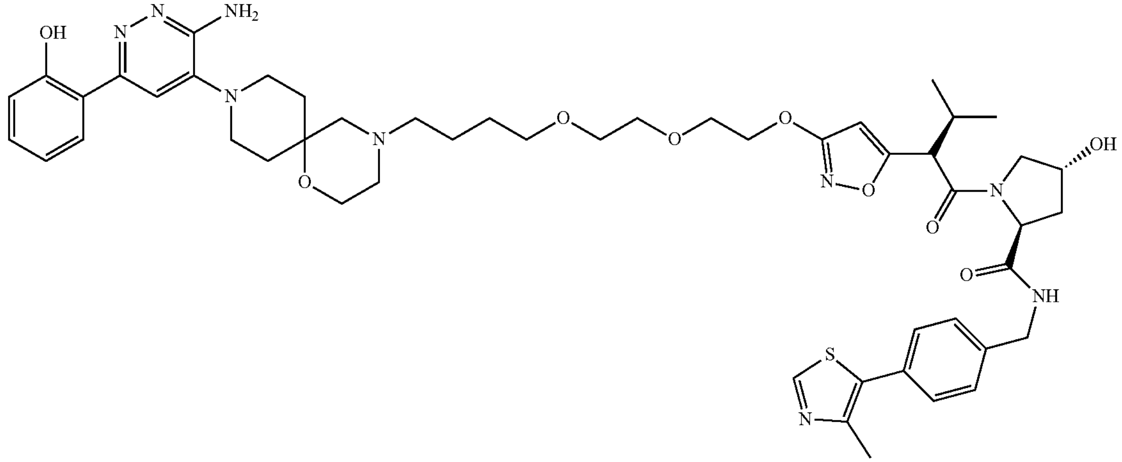 | (2S,4R)-1-((R)-2-(3-(2-(2-(4-(9-(3-amino-6-(2-hydroxyphenyl)pyridazin-4-yl)-1-oxa-4,9-diazaspiro[5.5]undecan-4-yl)butoxy)ethoxy)ethoxy)isoxazol-5-yl)-3-methylbutanoyl)-4-hydroxy-N-(4-(4-methylthiazol-5-yl)benzyl)pyrrolidine-2-carboxamide |

TABLE 1A-continued

| Ex. # | Structure | Compound Name |
|---|---|---|
| | Exemplary bifunctional degradation compounds of the present disclosure | |
| 38 | 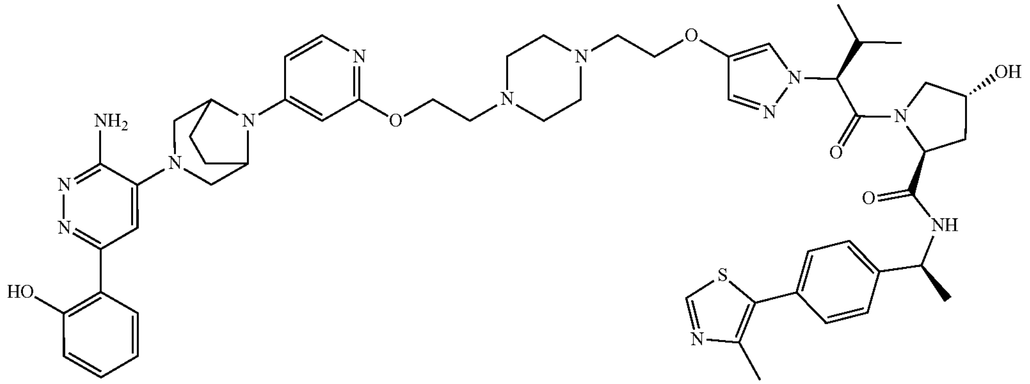 [SMILES: Cc1ncsc1-c1ccc([C@H](C)NC(=O)[C@@H]2C[C@@H](O)CN2C(=O)[C@H](C(C)C)n2cc(OCCN3CCN(CCOc4cc(N5C6CCC5CN(c5cc(-c7ccccc7O)nnc5N)C6)ccn4)CC3)cn2)cc1] | (2S,4R)-1-[(2R)-2-[4-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1H-pyrazol-1-yl]-3-methylbutanoyl]-4-hydroxy-N-[(1S)-1-[4-(4-methyl-1,3-thiazol-5-yl)phenyl]ethyl]pyrrolidine-2-carboxamide |
| 39 | 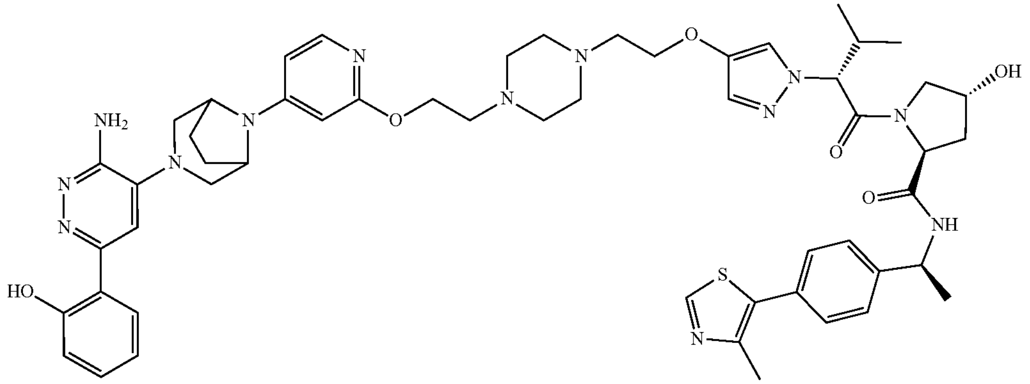 [SMILES: Cc1ncsc1-c1ccc([C@H](C)NC(=O)[C@@H]2C[C@@H](O)CN2C(=O)[C@@H](C(C)C)n2cc(OCCN3CCN(CCOc4cc(N5C6CCC5CN(c5cc(-c7ccccc7O)nnc5N)C6)ccn4)CC3)cn2)cc1] | (2S,4R)-1-[(2S)-2-[4-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1H-pyrazol-1-yl]-3-methylbutanoyl]-4-hydroxy-N-[(1S)-1-[4-(4-methyl-1,3-thiazol-5-yl)phenyl]ethyl]pyrrolidine-2-carboxamide |

TABLE 1A-continued

| Ex. # | Structure | Compound Name |
|---|---|---|
| | Exemplary bifunctional degradation compounds of the present disclosure | |
| 40 | 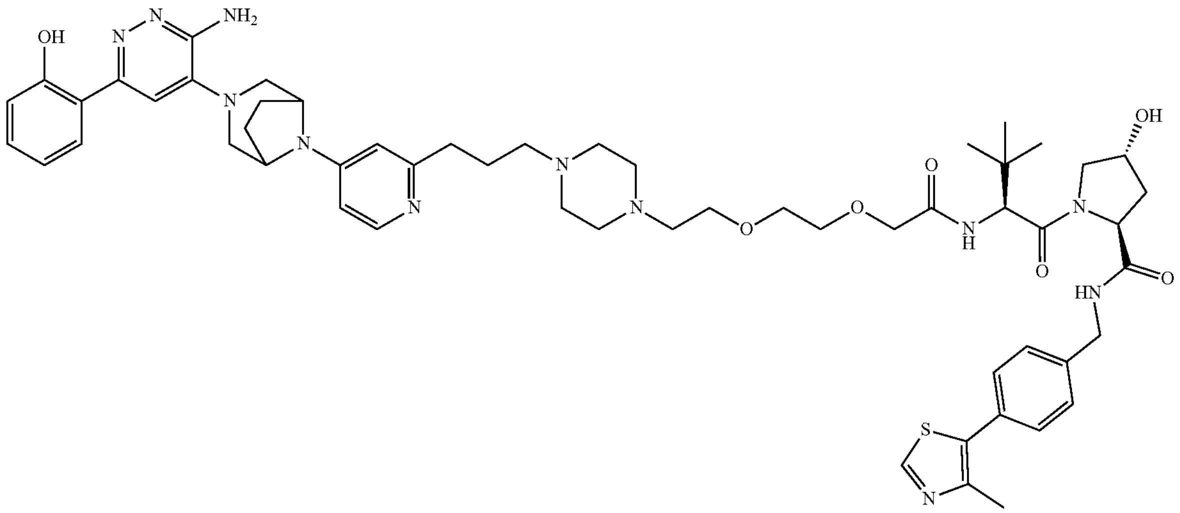 [SMILES: Cc1ncsc1-c1ccc(CNC(=O)[C@@H]2C[C@@H](O)CN2C(=O)[C@@H](NC(=O)COCCOCCN2CCN(CCCc3cc(N4C5CCC4CN(c4cc(-c6ccccc6O)nnc4N)C5)ccn3)CC2)C(C)(C)C)cc1] | (2S,4R)-1-[(2S)-2-[2-[2-(2-[4-[3-(4-[3-[3-amino-6-(2-hydroxyphenyl)pyridazin-4-yl]-3,8-diazabicyclo[3.2.1]octan-8-yl]pyridin-2-yl)propyl]piperazin-1-yl]ethoxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide |
| 41 | 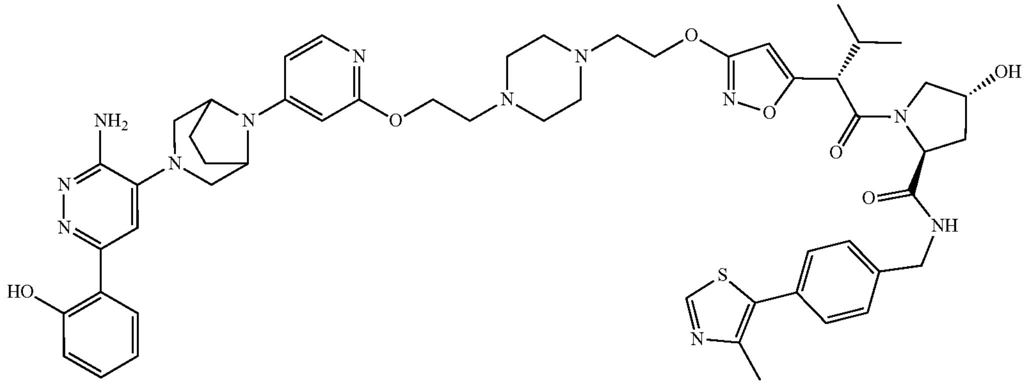 [SMILES: Cc1ncsc1-c1ccc(CNC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-[(2S)-2-[3-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1,2-oxazol-5-yl]-3-methylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 42 | 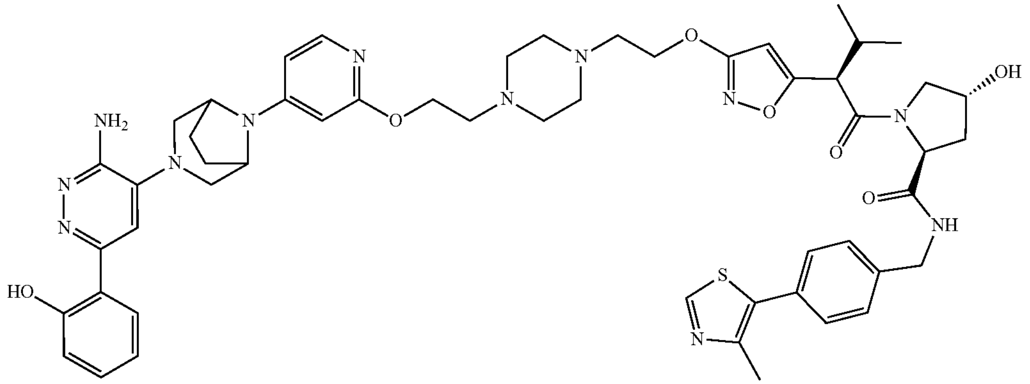 [SMILES: Cc1ncsc1-c1ccc(CNC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-[(2R)-2-[3-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1,2-oxazol-5-yl]-3-methylbutanoyl]-4-hydroxy-N-[[4-(4-methyl-1,3-thiazol-5-yl)phenyl]methyl]pyrrolidine-2-carboxamide |
| 43 | 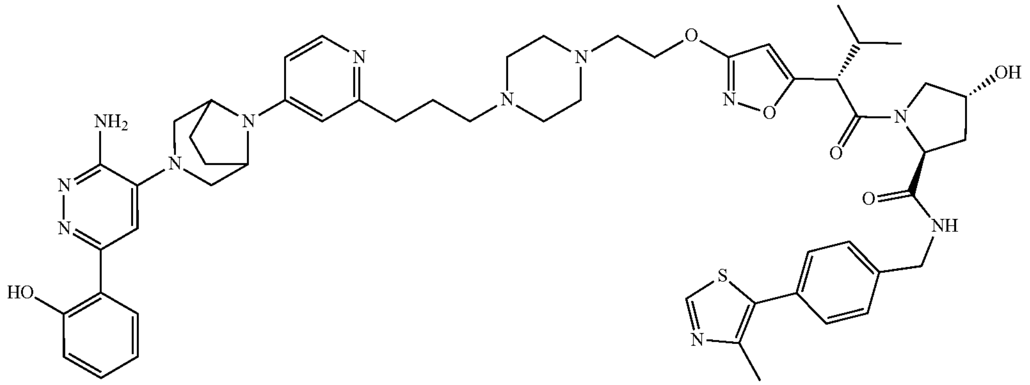 [SMILES: Cc1ncsc1-c1ccc(CNC(=O)[C@@H]2C[C@@H](O)CN2C(=O)[C@H](c2cc(OCCN3CCN(CCCc4cc(N5C6CCC5CN(c5cc(-c7ccccc7O)nnc5N)C6)ccn4)CC3)no2)C(C)C)cc1] | (2S,4R)-1-[(2S)-2-[3-(2-[4-[3-(4-[3-[3-amino-6-(2-hydroxyphenyl)pyridazin-4-yl]-3,8-diazabicyclo[3.2.1]octan-8-yl]pyridin-2-yl)propyl]piperazin-1-yl]ethoxy)-1,2-oxazol-5-yl]-3-methylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 44 | 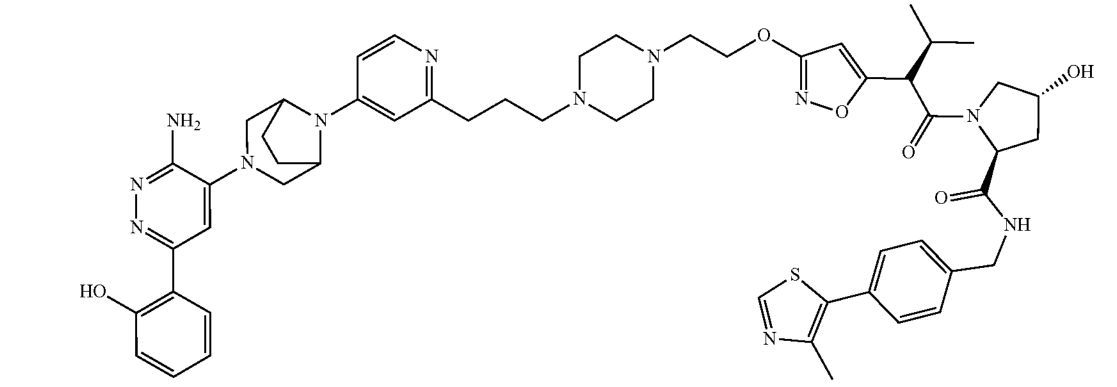 | (2S,4R)-1-[(2R)-2-[3-(2-[4-[3-(4-[3-[3-amino-6-(2-hydroxyphenyl)pyridazin-4-yl]-3,8-diazabicyclo[3.2.1]octan-8-yl]pyridin-2-yl)propyl]piperazin-1-yl]ethoxy)-1,2-oxazol-5-yl]-3-methylbutanoyl]-4-hydroxy-N-[[4-(4-methyl-1,3-thiazol-5-yl)phenyl]methyl]pyrrolidine-2-carboxamide |
| 45 | 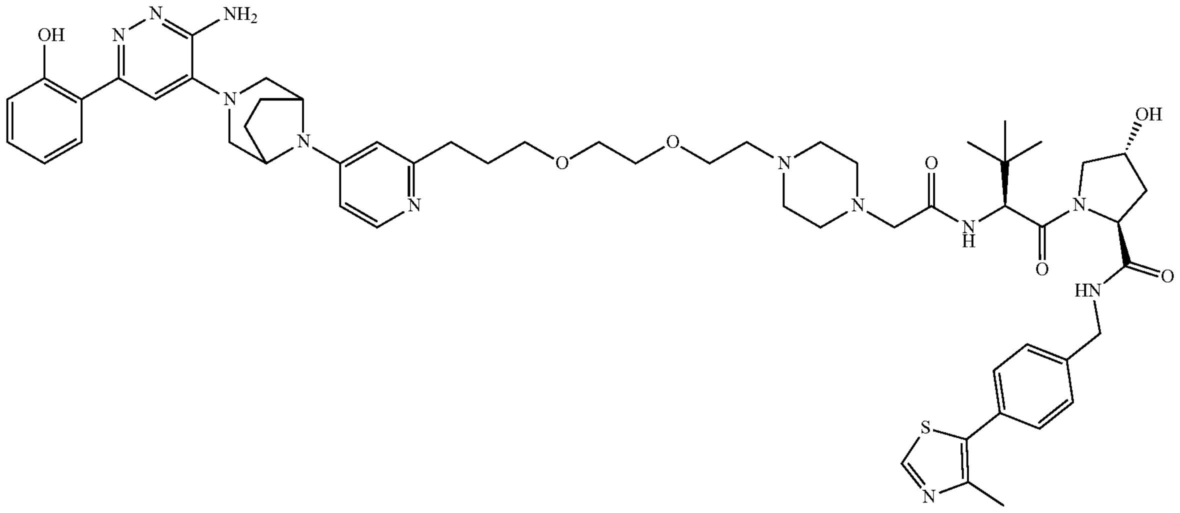 [SMILES: Cc1ncsc1-c1ccc(CNC(=O)[C@@H]2C[C@@H](O)CN2C(=O)[C@@H](NC(=O)CN2CCN(CCOCCOCCCc3cc(N4C5CCC4CN(c4cc(-c6ccccc6O)nnc4N)C5)ccn3)CC2)C(C)(C)C)cc1] | (2S,4R)-1-[(2S)-2-[2-[4-(2-[2-[3-(4-[3-[3-amino-6-(2-hydroxyphenyl)pyridazin-4-yl]-3,8-diazabicyclo[3.2.1]octan-8-yl]pyridin-2-yl)propoxy]ethoxy]ethyl)piperazin-1-yl]acetamido]-3,3-dimethylbutanoyl]-4-hydroxy-N-[[4-(4-methyl-1,3-thiazol-5-yl)phenyl]methyl]pyrrolidine-2-carboxamide |

TABLE 1A-continued

| Exemplary bifunctional degradation compounds of the present disclosure | | |
|---|---|---|
| Ex. # | Structure | Compound Name |
| 46 | 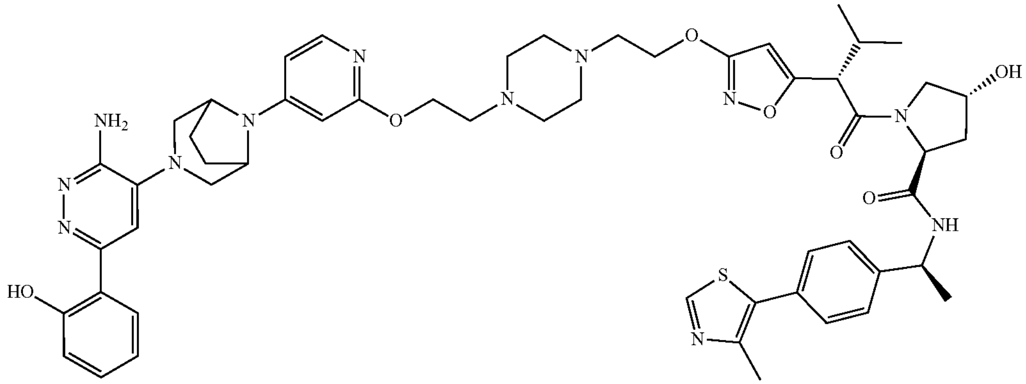 [SMILES: Cc1ncsc1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-[(2S)-2-[3-[2-(4-[2-[(4-[3-[3-amino-6-(2-hydroxyphenyl)pyridazin-4-yl]-3,8-diazabicyclo[3.2.1]octan-8-yl]pyridin-2-yl)oxy]ethyl]piperazin-1-yl)ethoxy]-1,2-oxazol-5-yl]-3-methylbutanoyl]-4-hydroxy-N-[(1S)-1-[4-(4-methyl-1,3-thiazol-5-yl)phenyl]ethyl]pyrrolidine-2-carboxamide |
| 47 | 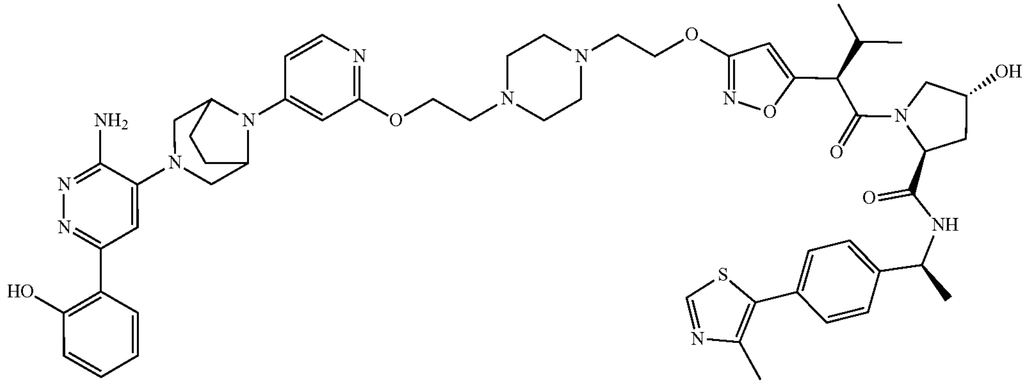 [SMILES: Cc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | $^1$H NMR (300 MHz, DMSO-$d_6$) δ 14.11 (s, 1H), 8.95 (s, 1H), 8.37 (d, J = 7.6 Hz, 1H), 7.88-7.75 (d, J = 5.9 Hz, 2H), 7.49-7.28 (m, 6H), 7.18 (ddd, J = 8.3, 7.0, 1.6 Hz, 1H), 6.88-6.75 (m, 2H), 6.49 (dd, J = 6.2, 2.0 Hz, 1H), 6.16-6.02 (m, 2H), 5.93 (s, 2H), 5.05 (d, J = 3.7 Hz, 1H), 5.00-4.81 (m, 1H), 4.46 (s, 2H), 4.39-4.13 (m, 6H), 3.72-3.55 (m, 2H), 3.45-3.35 (m, 1H), 3.21 (d, J = 11.7 Hz, 2H), 2.98 (d, J = 11.6 Hz, 2H), 2.59 (q, J = 6.5 Hz, 4H), 2.42 (s, 6H), 2.17 (dd, J = 20.0, 8.3 Hz, 3H), 1.94 (s, 4H), 1.75 (t, J = 9.6 Hz, 1H), 1.37 (dd, J = 20.9, 7.0 Hz, 3H), 1.17 (d, J = 14.9 Hz, 1H), 1.05-0.87 (m, 3H), 0.77 (dd, J = 10.6, 6.7 Hz, 3H). |

TABLE 1A-continued

| Exemplary bifunctional degradation compounds of the present disclosure | | |
|---|---|---|
| Ex. # | Structure | Compound Name |
| 48 | 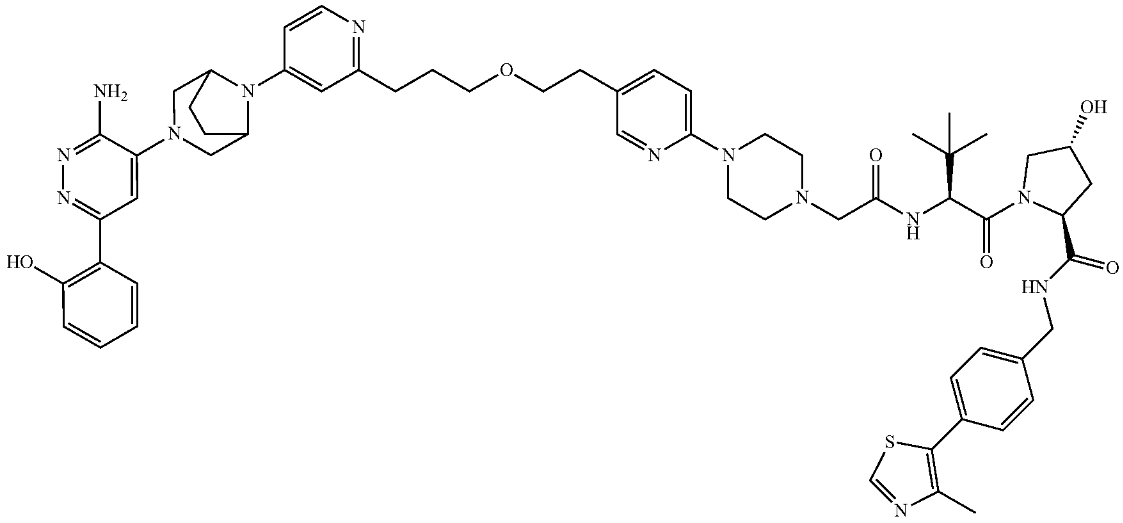 [SMILES: Cc1ncsc1-c1ccc(CNC(=O)[C@@H]2C[C@@H](O)CN2C(=O)[C@@H](NC(=O)CN2CCN(c3ccc(CCOCCCc4cc(N5C6CCC5CN(c5cc(-c7ccccc7O)nnc5N)C6)ccn4)cn3)CC2)C(C)(C)C)cc1] | (2S,4R)-1-((2S)-2-(2-(4-(5-(2-(3-(4-(3-(3-amino-6-(2-hydroxyphenyl)pyridazin-4-yl)-3,8-diazabicyclo[3.2.1]octan-8-yl)pyridin-2-yl)propoxy)ethyl)pyridin-2-yl)piperazin-1-yl)acetamido)-3,3-dimethylbutanoyl)-4-hydroxy-N-(4-(4-methylthiazol-5-yl)benzyl)pyrrolidine-2-carboxamide |
| 49 | 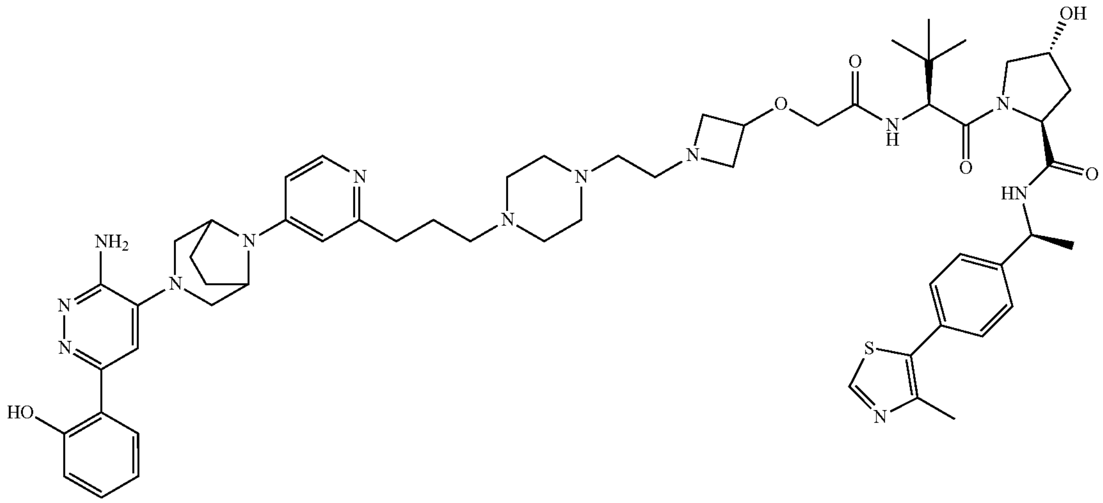 [SMILES: Cc1ncsc1-c1ccc([C@H](C)NC(=O)[C@@H]2C[C@@H](O)CN2C(=O)[C@@H](NC(=O)COC2CN(CCN3CCN(CCCc4cc(N5C6CCC5CN(c5cc(-c7ccccc7O)nnc5N)C6)ccn4)CC3)C2)C(C)(C)C)cc1] | (2S,4R)-1-((2S)-2-(2-((1-(2-(4-(3-(4-(3-(3-amino-6-(2-hydroxyphenyl)pyridazin-4-yl)-3,8-diazabicyclo[3.2.1]octan-8-yl)pyridin-2-yl)propyl)piperazin-1-yl)ethyl)azetidin-3-yl)oxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 50 | 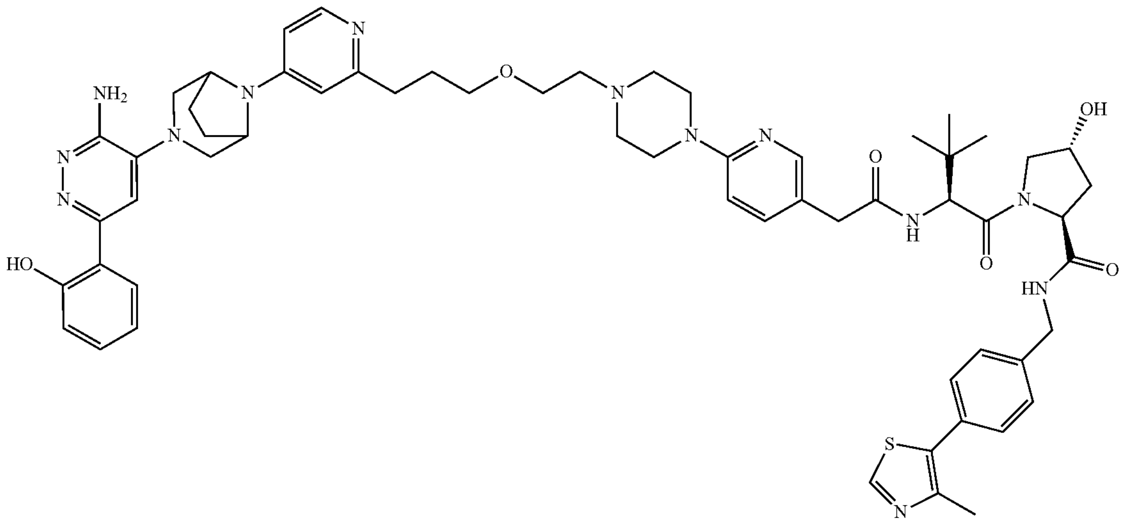 [SMILES: Cc1ncsc1-c1ccc(CNC(=O)[C@@H]2C[C@@H](O)CN2C(=O)[C@@H](NC(=O)Cc2ccc(N3CCN(CCOCCCc4cc(N5C6CCC5CN(c5cc(-c7ccccc7O)nnc5N)C6)ccn4)CC3)nc2)C(C)(C)C)cc1] | (2S,4R)-1-[(2S)-2-[2-[6-(4-[2-[3-(4-[3-[3-amino-6-(2-hydroxyphenyl)pyridazin-4-yl]-3,8-diazabicyclo[3.2.1]octan-8-yl]pyridin-2-yl)propoxy]ethyl]piperazin-1-yl)pyridin-3-yl]acetamido]-3,3-dimethylbutanoyl]-4-hydroxy-N-[(1S)-1-[4-(4-methyl-1,3-thiazol-5-yl)phenyl]ethyl]pyrrolidine-2-carboxamide |
| 51 | 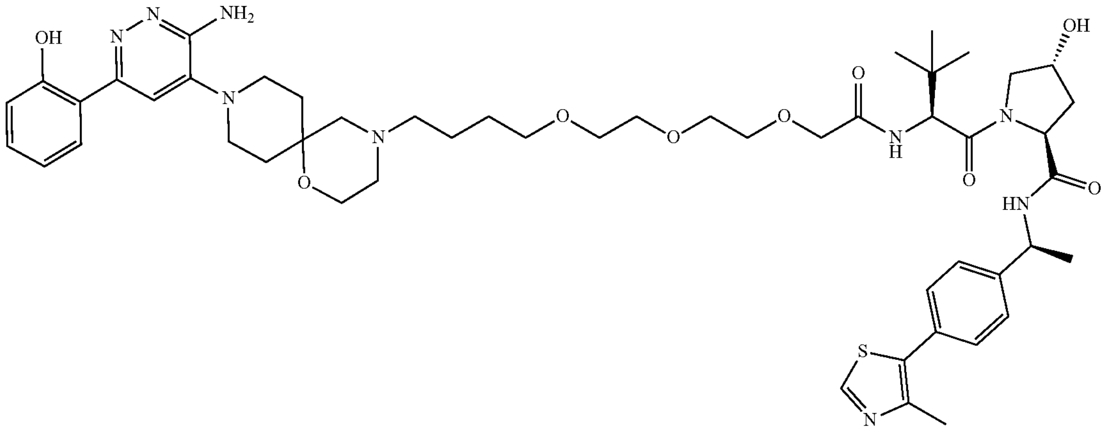 [SMILES: Cc1ncsc1-c1ccc([C@H](C)NC(=O)[C@@H]2C[C@@H](O)CN2C(=O)[C@@H](NC(=O)COCCOCCOCCCCN2CCOC3(CCN(c4cc(-c5ccccc5O)nnc4N)CC3)C2)C(C)(C)C)cc1] | (2S,4R)-1-[(2S)-2-(2-[2-[2-(4-[9-[3-amino-6-(2-hydroxyphenyl)pyridazin-4-yl]-1-oxa-4,9-diazaspiro[5.5]undecan-4-yl]butoxy)ethoxy]ethoxy]acetamido)-3,3-dimethylbutanoyl]-4-hydroxy-N-[(1S)-1-[4-(4-methyl-1,3-thiazol-5-yl)phenyl]ethyl]pyrrolidine-2-carboxamide |

TABLE 1A-continued

| Exemplary bifunctional degradation compounds of the present disclosure | | |
|---|---|---|
| Ex. # | Structure | Compound Name |
| 52 | 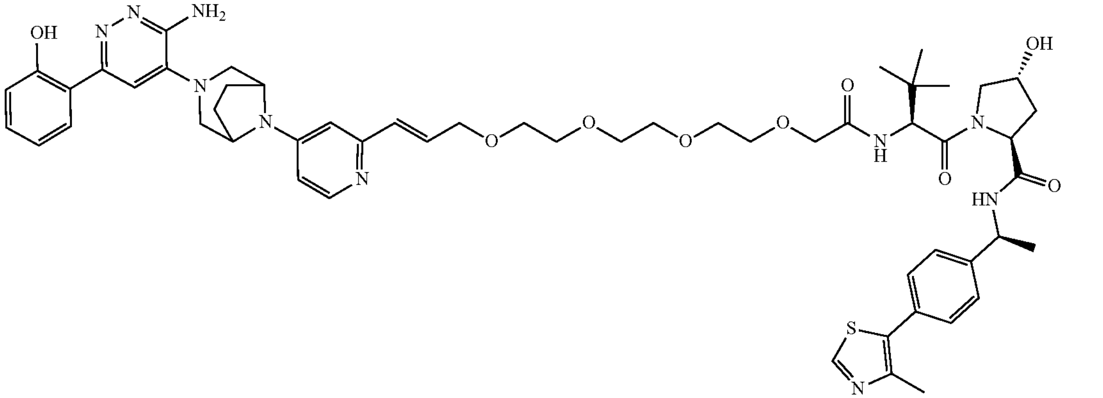 [SMILES: Cc1ncsc1-c1ccc([C@H](C)NC(=O)[C@@H]2C[C@@H](O)CN2C(=O)[C@@H](NC(=O)COCCOCCOCCOC/C=C/c2cc(N3C4CCC3CN(c3cc(-c5ccccc5O)nnc3N)C4)ccn2)C(C)(C)C)cc1] | (2S,4R)-1-((S,E)-18-(4-(3-(3-amino-6-(2-hydroxyphenyl)pyridazin-4-yl)-3,8-diaza-bicyclo[3.2.1]octan-8-yl)pyridin-2-yl)-2-tert-butyl-4-oxo-6,9,12,15-tetraoxa-3-azaoctadec-17-en-1-oyl)-4-hydroxy-N-(4-(4-methylthiazol-5-yl)benzyl)pyrrolidine-2-carboxamide |
| 53 | 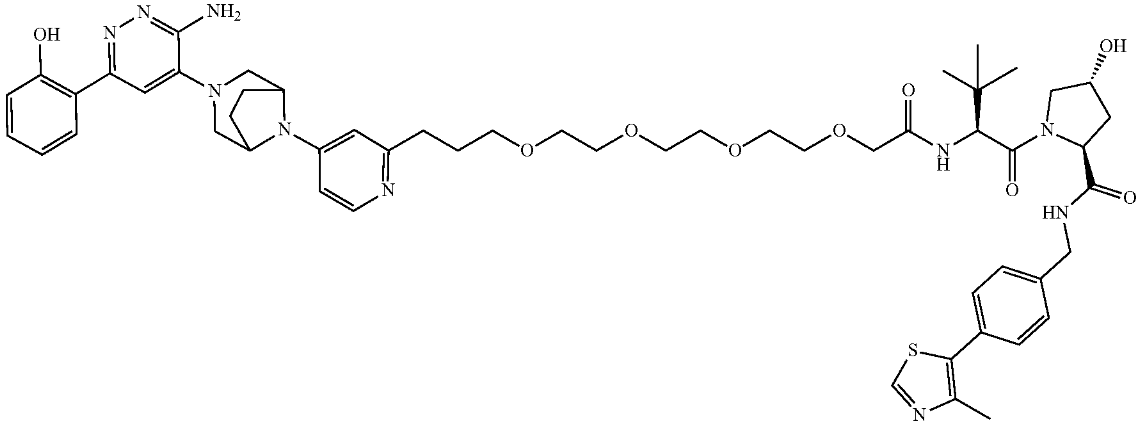 [SMILES: Cc1ncsc1-c1ccc(CNC(=O)[C@@H]2C[C@@H](O)CN2C(=O)[C@@H](NC(=O)COCCOCCOCCOCCCc2cc(N3C4CCC3CN(c3cc(-c5ccccc5O)nnc3N)C4)ccn2)C(C)(C)C)cc1] | (2S,4R)-1-((S)-18-(4-(3-(3-amino-6-(2-hydroxyphenyl)pyridazin-4-yl)-3,8-diaza-bicyclo[3.2.1]octan-8-yl)pyridin-2-yl)-2-tert-butyl-4-oxo-6,9,12,15-tetraoxa-3-azaoctadecan-1-oyl)-4-hydroxy-N-(4-(4-methylthiazol-5-yl)benzyl)pyrrolidine-2-carboxamide |

TABLE 1A-continued

| Exemplary bifunctional degradation compounds of the present disclosure | | |
|---|---|---|
| Ex. # | Structure | Compound Name |
| 54 | 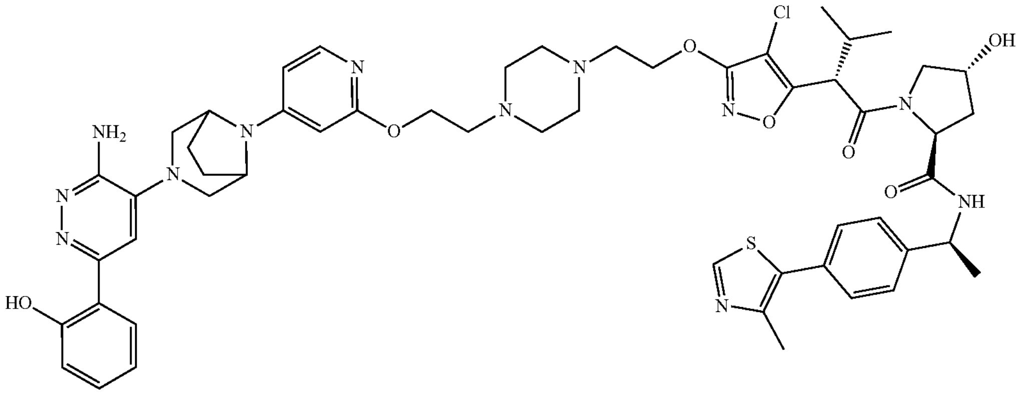 [SMILES: Cc1ncsc1-c1ccc([C@H](C)NC(=O)[C@@H]2C[C@@H](O)CN2C(=O)[C@H](c2onc(OCCN3CCN(CCOc4cc(N5C6CCC5CN(c5cc(-c7ccccc7O)nnc5N)C6)ccn4)CC3)c2Cl)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)-4-chloroisoxazol-5-yl)-3-methylbutanoyl)-4-hydroxy-N-((S)-1-(4-(4-methylthiazol-5-yl)phenyl)ethyl)pyrrolidine-2-carboxamide |
| 55 | 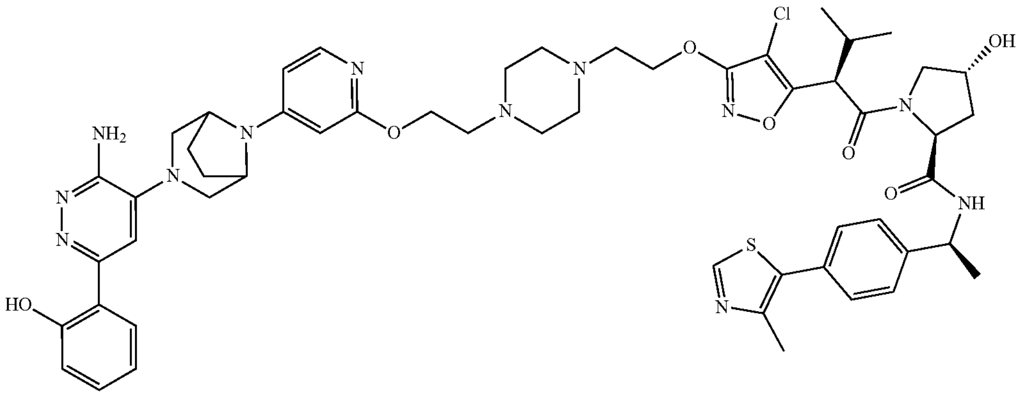 [SMILES: Cc1ncsc1-c1ccc([C@H](C)NC(=O)[C@@H]2C[C@@H](O)CN2C(=O)[C@@H](c2onc(OCCN3CCN(CCOc4cc(N5C6CCC5CN(c5cc(-c7ccccc7O)nnc5N)C6)ccn4)CC3)c2Cl)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)-4-chloroisoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 56 | 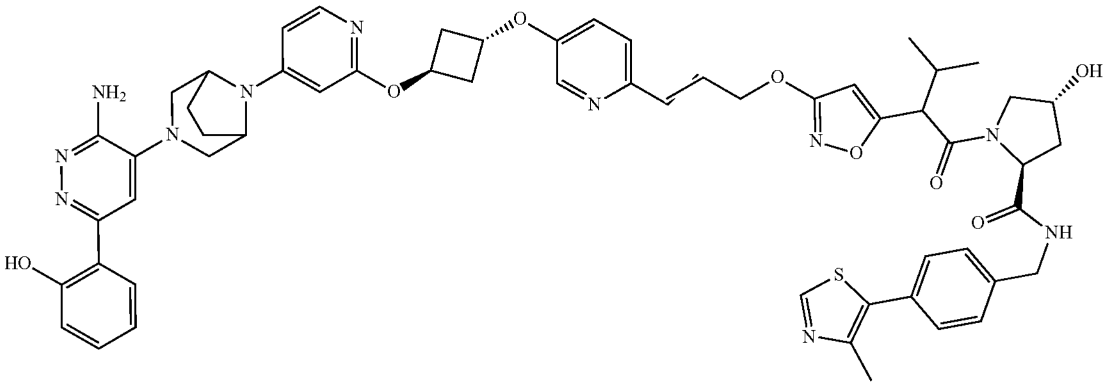 | (2S,4R)-1-(2-(3-((3-(5-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)allyl)oxy)isoxazol-5-yl)-3-methylbutanoyl)-4-hydroxy-N-(4-(4-methylthiazol-5-yl)benzyl)pyrrolidine-2-carboxamide |
| 57 | 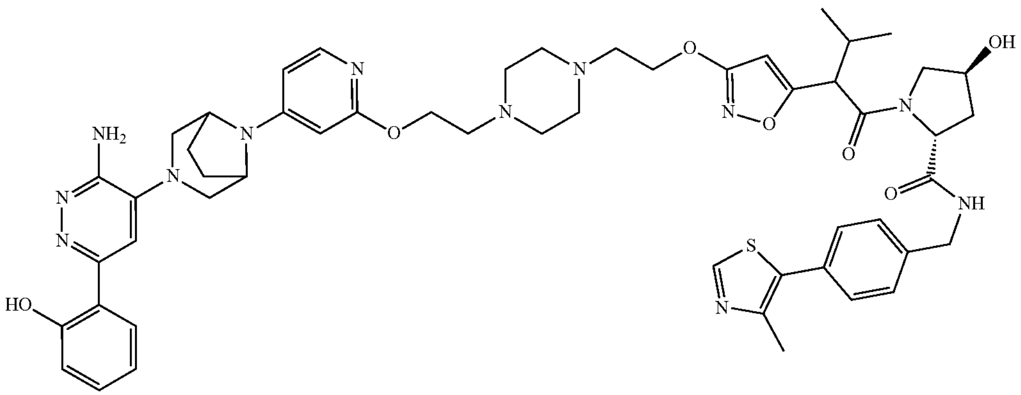 [SMILES: Cc1ncsc1-c1ccc(CNC(=O)[C@H]2C[C@H](O)CN2C(=O)C(c2cc(OCCN3CCN(CCOc4cc(N5C6CCC5CN(c5cc(-c7ccccc7O)nnc5N)C6)ccn4)CC3)no2)C(C)C)cc1] | (2R,4S)-1-(2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide |

TABLE 1A-continued

| Exemplary bifunctional degradation compounds of the present disclosure | | |
|---|---|---|
| Ex. # | Structure | Compound Name |
| 58 | 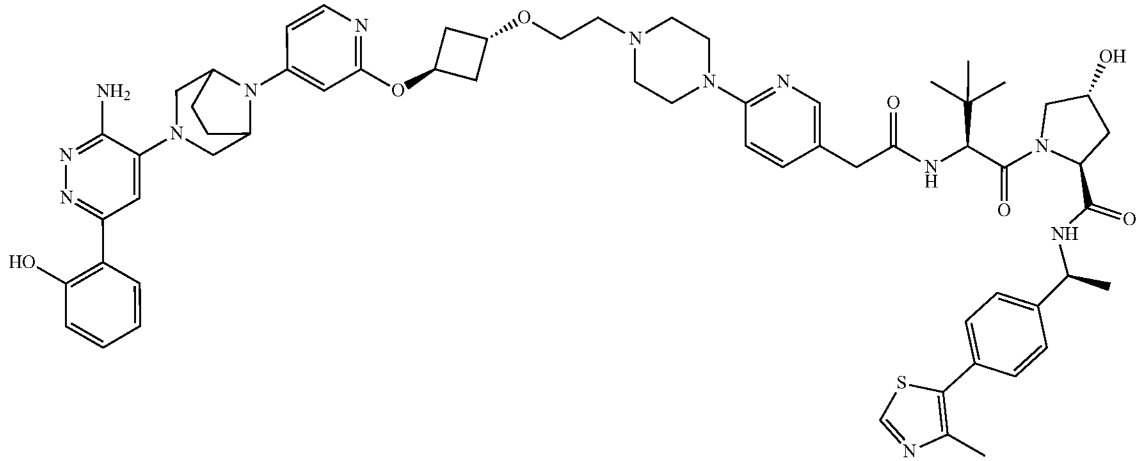 [SMILES: Cc1ncsc1-c1ccc([C@H](C)NC(=O)[C@@H]2C[C@@H](O)CN2C(=O)[C@@H](NC(=O)Cc2ccc(N3CCN(CCO[C@H]4C[C@H](Oc5cc(N6C7CCC6CN(c6cc(-c8ccccc8O)nnc6N)C7)ccn5)C4)CC3)nc2)C(C)(C)C)cc1] | (2S,4R)-1-((2S)-2-(2-(6-(4-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)piperazin-1-yl)pyridin-3-yl)acetamido)-3,3-dimethylbutanoyl)-4-hydroxy-N-((S)-1-(4-(4-methylthiazol-5-yl)phenyl)ethyl)pyrrolidine-2-carboxamide |
| 59 | 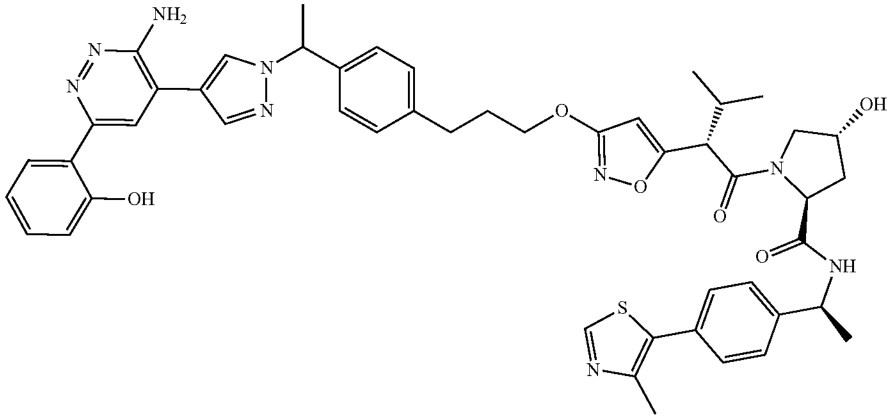 [SMILES: Cc1ncsc1-c1ccc([C@H](C)NC(=O)[C@@H]2C[C@@H](O)CN2C(=O)[C@H](c2cc(OCCCc3ccc(C(C)n4cc(-c5cc(-c6ccccc6O)nnc5N)cn4)cc3)no2)C(C)C)cc1] | (2S,4R)-1-((2S)-2-(3-(3-(4-(1-(4-(3-amino-6-(2-hydroxyphenyl)pyridazin-4-yl)-1H-pyrazol-1-yl)ethyl)phenyl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 60 | 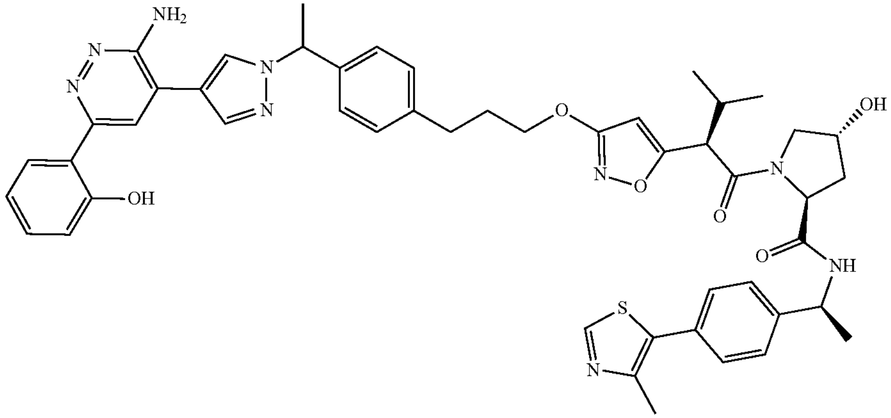 [SMILES: Cc1ncsc1-c1ccc([C@H](C)NC(=O)[C@@H]2C[C@@H](O)CN2C(=O)[C@@H](c2cc(OCCCc3ccc(C(C)n4cc(-c5cc(-c6ccccc6O)nnc5N)cn4)cc3)no2)C(C)C)cc1] | (2S,4R)-1-((2R)-2-(3-(3-(4-(1-(4-(3-amino-6-(2-hydroxyphenyl)pyridazin-4-yl)-1H-pyrazol-1-yl)ethyl)phenyl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 61 | 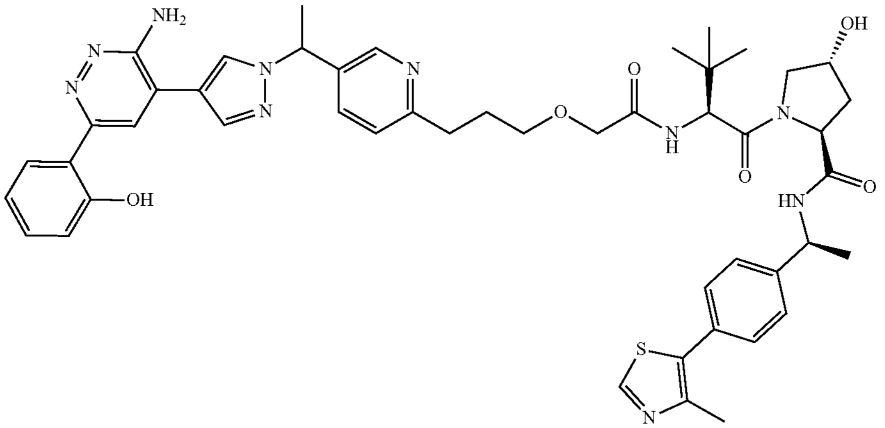 [SMILES: Cc1ncsc1-c1ccc([C@H](C)NC(=O)[C@@H]2C[C@@H](O)CN2C(=O)[C@@H](NC(=O)COCCCc2ccc(C(C)n3cc(-c4cc(-c5ccccc5O)nnc4N)cn3)cn2)C(C)(C)C)cc1] | (2S,4R)-1-((2S)-2-(2-(3-(5-(1-(4-(3-amino-6-(2-hydroxyphenyl)pyridazin-4-yl)-1H-pyrazol-1-yl)ethyl)pyridin-2-yl)propoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 62 | 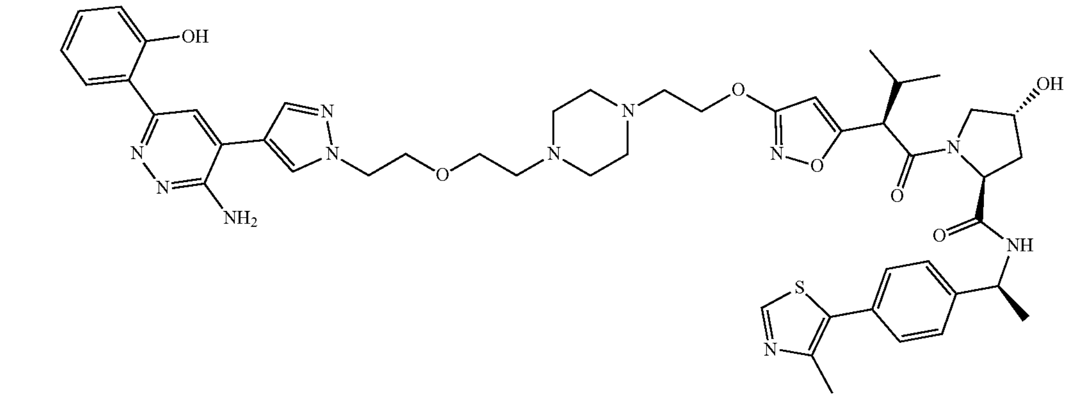 [SMILES: Cc1ncsc1-c1ccc([C@H](C)NC(=O)[C@@H]2C[C@@H](O)CN2C(=O)[C@@H](c2cc(OCCN3CCN(CCOCCn4cc(-c5cc(-c6ccccc6O)nnc5N)cn4)CC3)no2)C(C)C)cc1] | (2S,4R)-1-((R)-2-(3-(2-(4-(2-(2-(4-(3-amino-6-(2-hydroxyphenyl)pyridazin-4-yl)-1H-pyrazol-1-yl)ethoxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 63 | 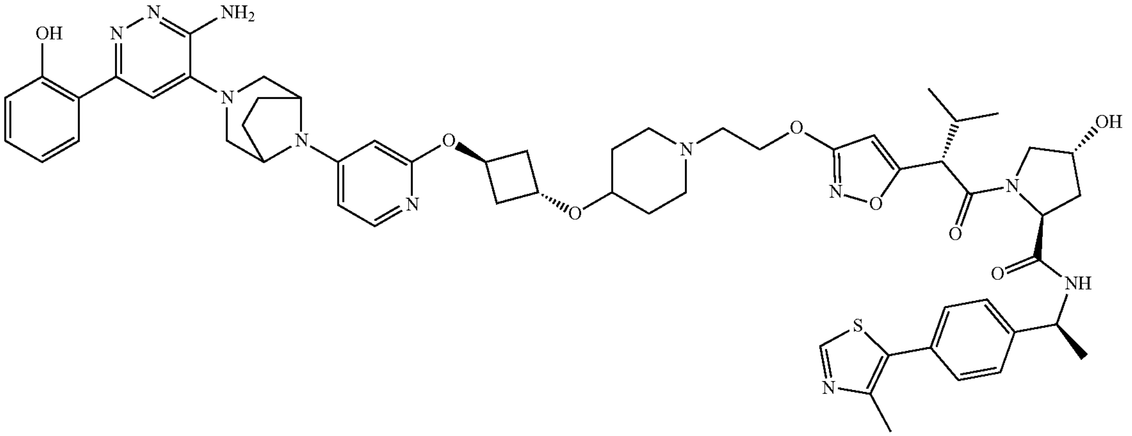 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 64 | 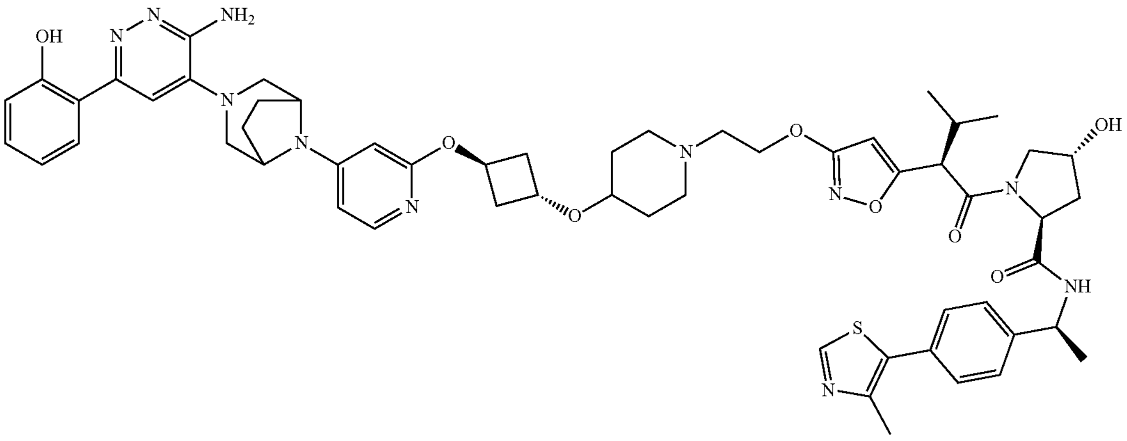 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 65 | 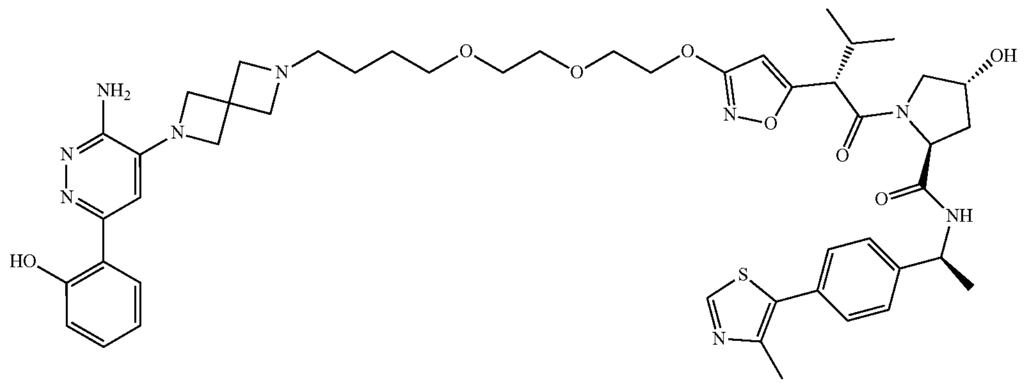 [SMILES: Cc1ncsc1-c1ccc([C@H](C)NC(=O)[C@@H]2C[C@@H](O)CN2C(=O)[C@H](c2cc(OCCOCCOCCCCN3CC4(C3)CN(c3cc(-c5ccccc5O)nnc3N)C4)no2)C(C)C)cc1] | (2S,4R)-1-((S)-2-(3-(2-(2-(4-(6-(3-amino-6-(2-hydroxyphenyl)pyridazin-4-yl)-2,6-diazaspiro[3.3]heptan-2-yl)butoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 66 | 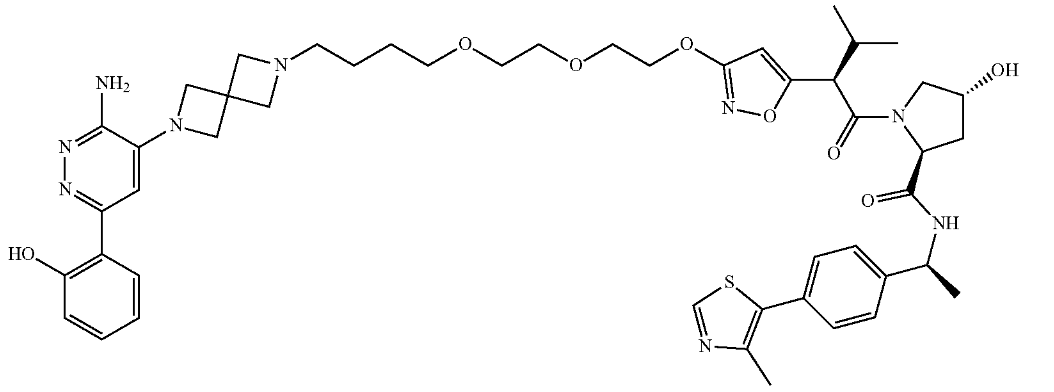 [SMILES: Cc1ncsc1-c1ccc([C@H](C)NC(=O)[C@@H]2C[C@@H](O)CN2C(=O)[C@@H](c2cc(OCCOCCOCCCCN3CC4(C3)CN(c3cc(-c5ccccc5O)nnc3N)C4)no2)C(C)C)cc1] | (2S,4R)-1-((R)-2-(3-(2-(2-(4-(6-(3-amino-6-(2-hydroxyphenyl)pyridazin-4-yl)-2,6-diazaspiro[3.3]heptan-2-yl)butoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 67 | 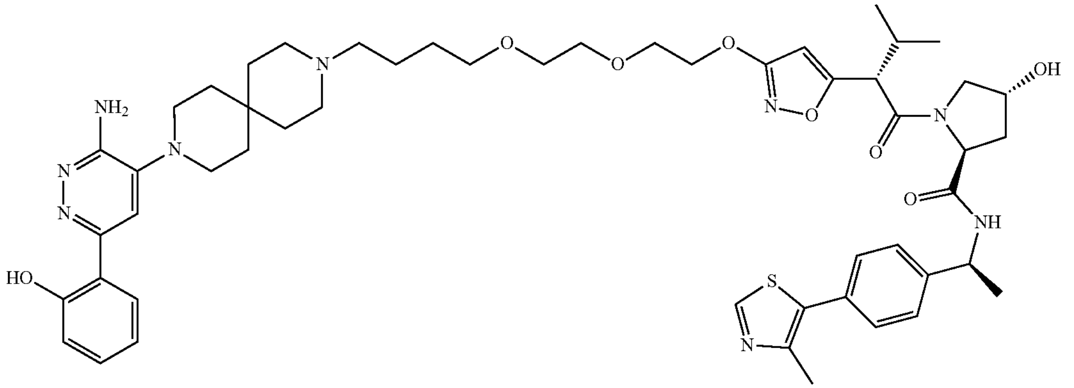 [SMILES: Cc1ncsc1-c1ccc([C@H](C)NC(=O)[C@@H]2C[C@@H](O)CN2C(=O)[C@H](c2cc(OCCOCCOCCCCN3CCC4(CC3)CCN(c3cc(-c5ccccc5O)nnc3N)CC4)no2)C(C)C)cc1] | (2S,4R)-1-((S)-2-(3-(2-(2-(4-(9-(3-amino-6-(2-hydroxyphenyl)pyridazin-4-yl)-3,9-diazaspiro[5.5]undecan-3-yl)butoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 68 | 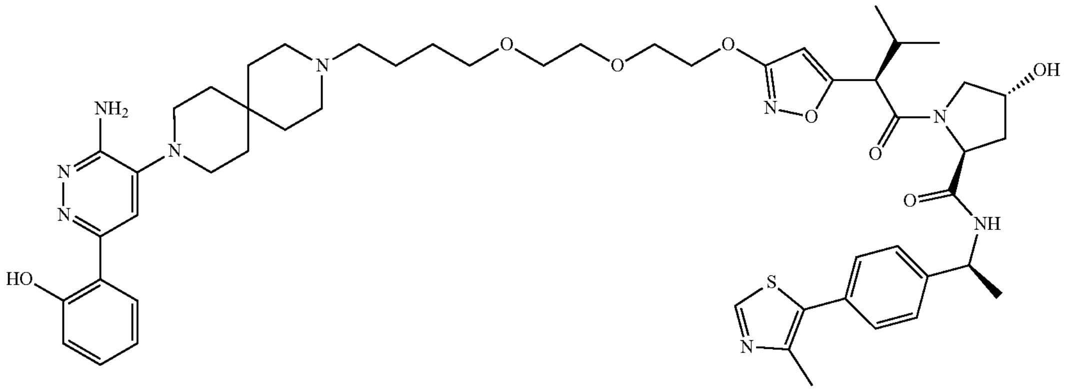 [SMILES: Cc1ncsc1-c1ccc([C@H](C)NC(=O)[C@@H]2C[C@@H](O)CN2C(=O)[C@@H](c2cc(OCCOCCOCCCCN3CCC4(CC3)CCN(c3cc(-c5ccccc5O)nnc3N)CC4)no2)C(C)C)cc1] | (2S,4R)-1-((R)-2-(3-(2-(2-(4-(9-(3-amino-6-(2-hydroxyphenyl)pyridazin-4-yl)-3,9-diazaspiro[5.5]undecan-3-yl)butoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 69 | 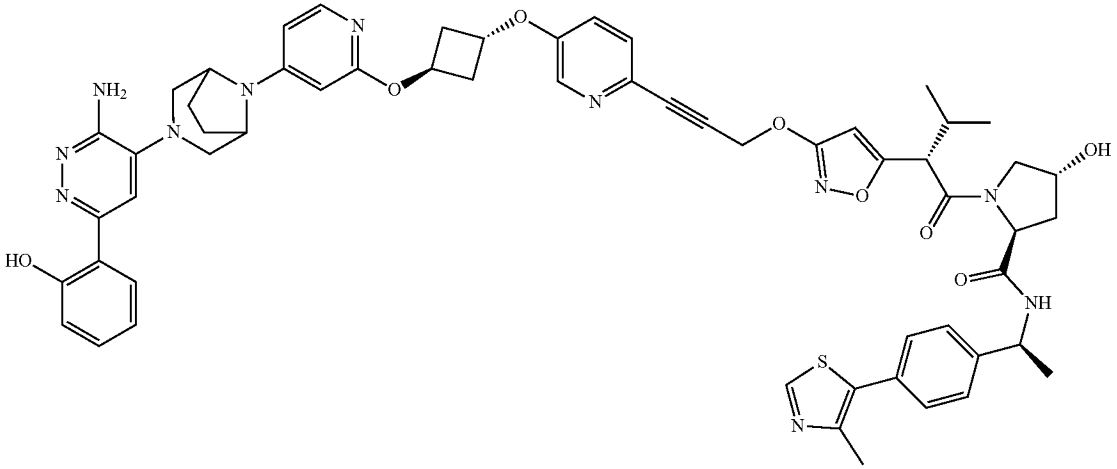 [SMILES: Cc1ncsc1-c1ccc([C@H](C)NC(=O)[C@@H]2C[C@@H](O)CN2C(=O)[C@H](c2cc(OCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 70 | 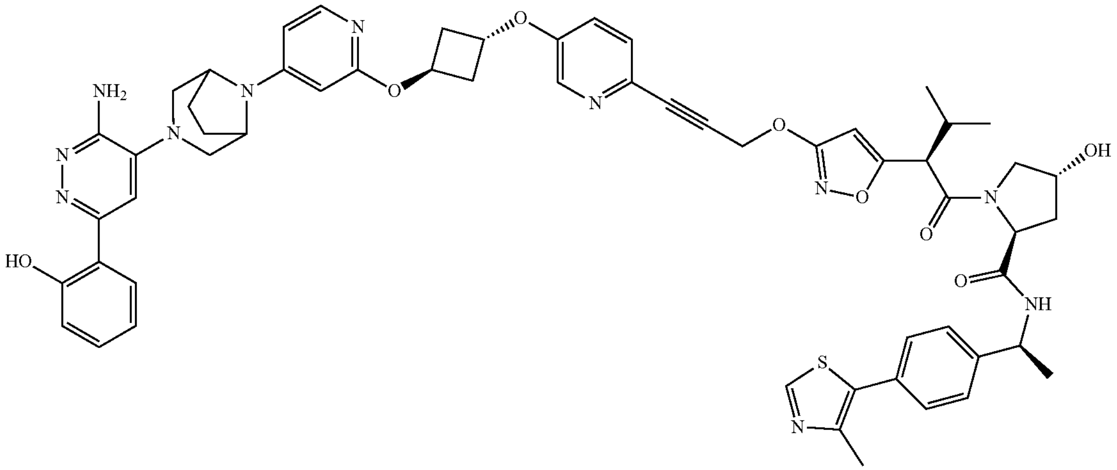 [SMILES: Cc1ncsc1-c1ccc([C@H](C)NC(=O)[C@@H]2C[C@@H](O)CN2C(=O)[C@@H](c2cc(OCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 71 | 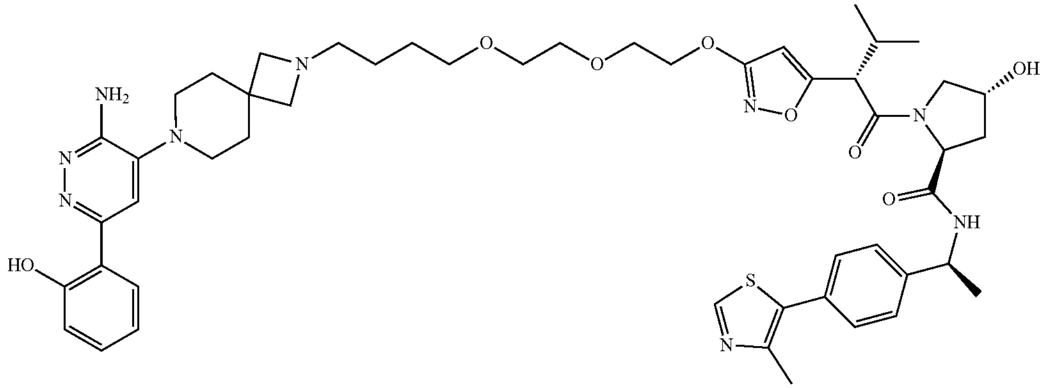 [SMILES: Cc1ncsc1-c1ccc([C@H](C)NC(=O)[C@@H]2C[C@@H](O)CN2C(=O)[C@H](c2cc(OCCOCCOCCCCN3CC4(CCN(c5cc(-c6ccccc6O)nnc5N)CC4)C3)no2)C(C)C)cc1] | (2S,4R)-1-((S)-2-(3-(2-(2-(4-(7-(3-amino-6-(2-hydroxyphenyl)pyridazin-4-yl)-2,7-diazaspiro[3.5]nonan-2-yl)butoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 72 | 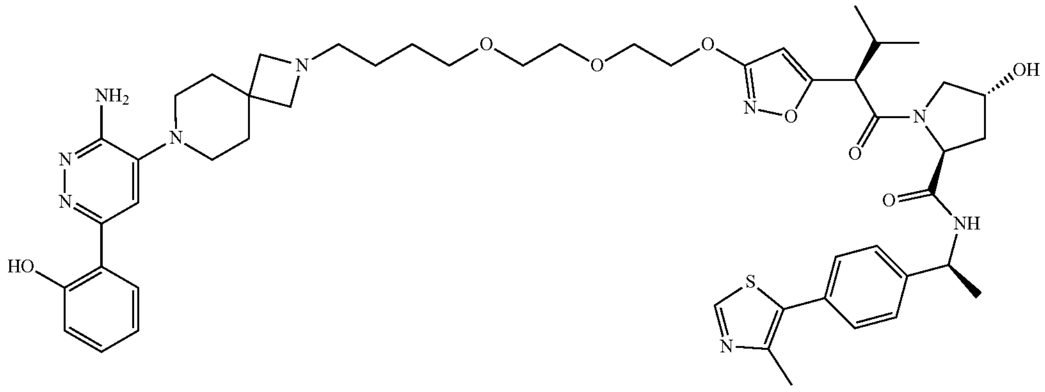 [SMILES: Cc1ncsc1-c1ccc([C@H](C)NC(=O)[C@@H]2C[C@@H](O)CN2C(=O)[C@@H](c2cc(OCCOCCOCCCCN3CC4(CCN(c5cc(-c6ccccc6O)nnc5N)CC4)C3)no2)C(C)C)cc1] | (2S,4R)-1-((R)-2-(3-(2-(2-(4-(7-(3-amino-6-(2-hydroxyphenyl)pyridazin-4-yl)-2,7-diazaspiro[3.5]nonan-2-yl)butoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 73 | 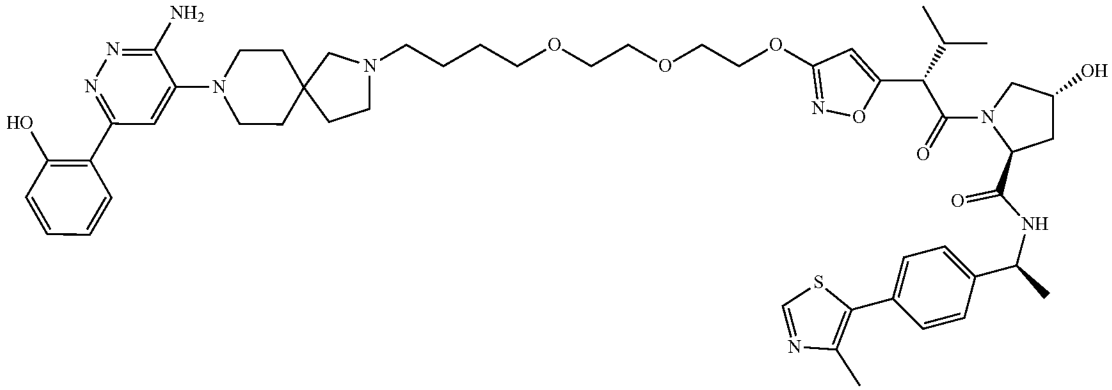 [SMILES: Cc1ncsc1-c1ccc([C@H](C)NC(=O)[C@@H]2C[C@@H](O)CN2C(=O)[C@H](c2cc(OCCOCCOCCCCN3CCC4(CCN(c5cc(-c6ccccc6O)nnc5N)CC4)C3)no2)C(C)C)cc1] | (2S,4R)-1-((S)-2-(3-(2-(2-(4-(8-(3-amino-6-(2-hydroxyphenyl)pyridazin-4-yl)-2,8-diazaspiro[4.5]decan-2-yl)butoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 74 | 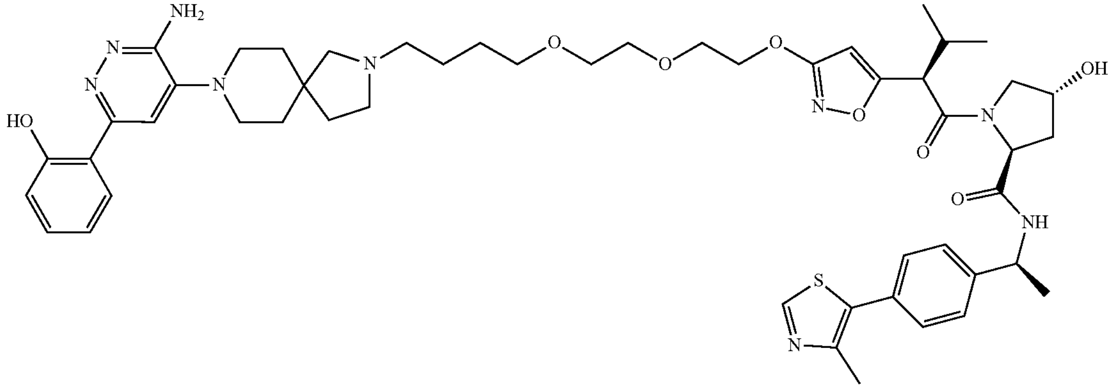 [SMILES: Cc1ncsc1-c1ccc([C@H](C)NC(=O)[C@@H]2C[C@@H](O)CN2C(=O)[C@@H](c2cc(OCCOCCOCCCCN3CCC4(CCN(c5cc(-c6ccccc6O)nnc5N)CC4)C3)no2)C(C)C)cc1] | (2S,4R)-1-((R)-2-(3-(2-(2-(4-(8-(3-amino-6-(2-hydroxyphenyl)pyridazin-4-yl)-2,8-diazaspiro[4.5]decan-2-yl)butoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 75 | 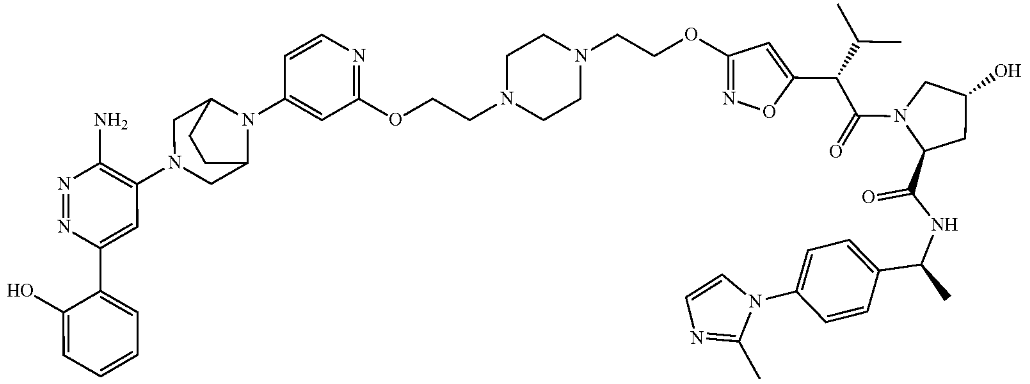 [SMILES: Cc1nccn1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 76 | 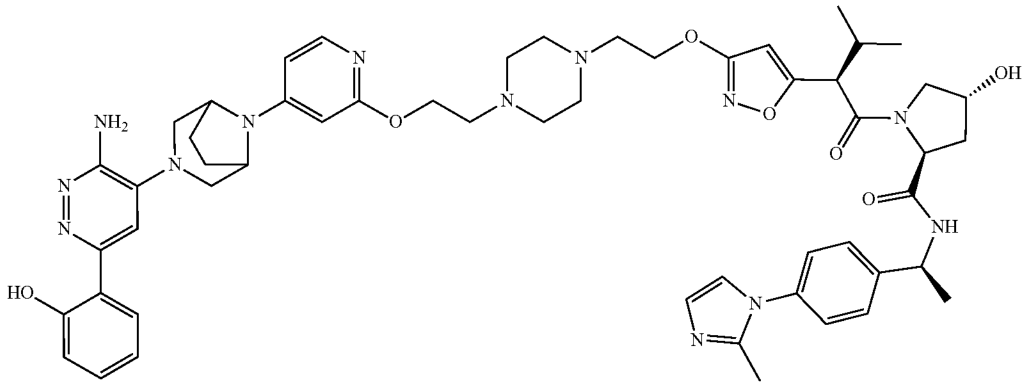 [SMILES: Cc1nccn1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |
| 77 | 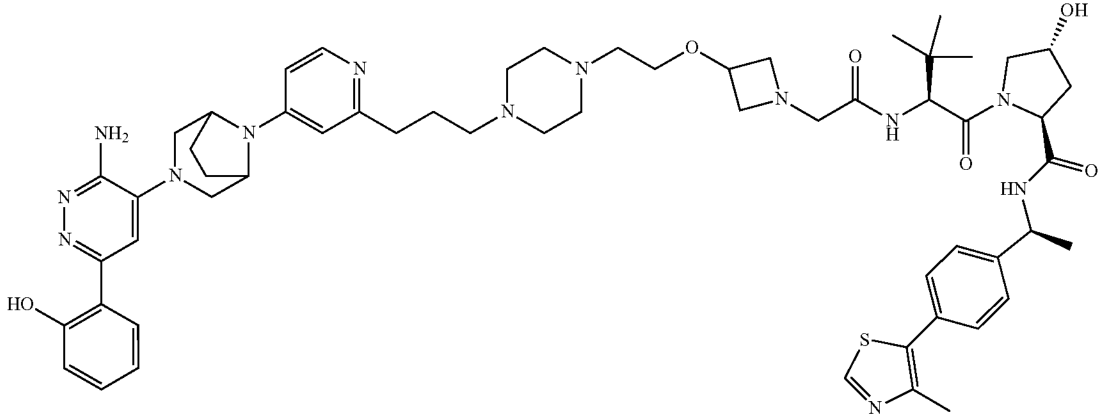 [SMILES: Cc1ncsc1-c1ccc([C@H](C)NC(=O)[C@@H]2C[C@@H](O)CN2C(=O)[C@@H](NC(=O)CN2CC(OCCN3CCN(CCCc4cc(N5C6CCC5CN(c5cc(-c7ccccc7O)nnc5N)C6)ccn4)CC3)C2)C(C)(C)C)cc1] | (2S,4R)-1-((2S)-2-(2-(3-(2-(4-(3-(4-(3-(3-amino-6-(2-hydroxyphenyl)pyridazin-4-yl)-3,8-diazabicyclo[3.2.1]octan-8-yl)pyridin-2-yl)propyl)piperazin-1-yl)ethoxy)azetidin-1-yl)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 78 | 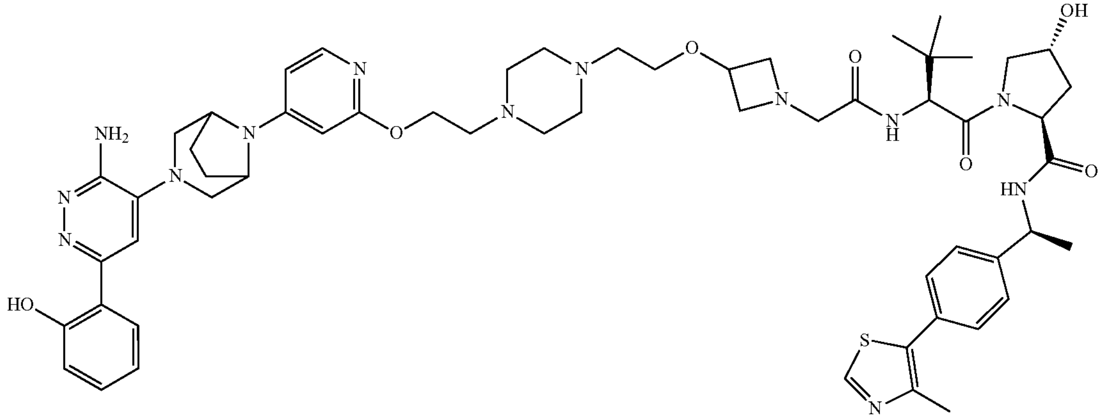 [SMILES: Cc1ncsc1-c1ccc([C@H](C)NC(=O)[C@@H]2C[C@@H](O)CN2C(=O)[C@@H](NC(=O)CN2CC(OCCN3CCN(CCOc4cc(N5C6CCC5CN(c5cc(-c7ccccc7O)nnc5N)C6)ccn4)CC3)C2)C(C)(C)C)cc1] | (2S,4R)-1-((2S)-2-(2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)azetidin-1-yl)acetamido)-3,3-dimethylbutanoyl)-4-hydroxy-N-((S)-1-(4-(4-methylthiazol-5-yl)phenyl)ethyl)pyrrolidine-2-carboxamide |
| 79 | 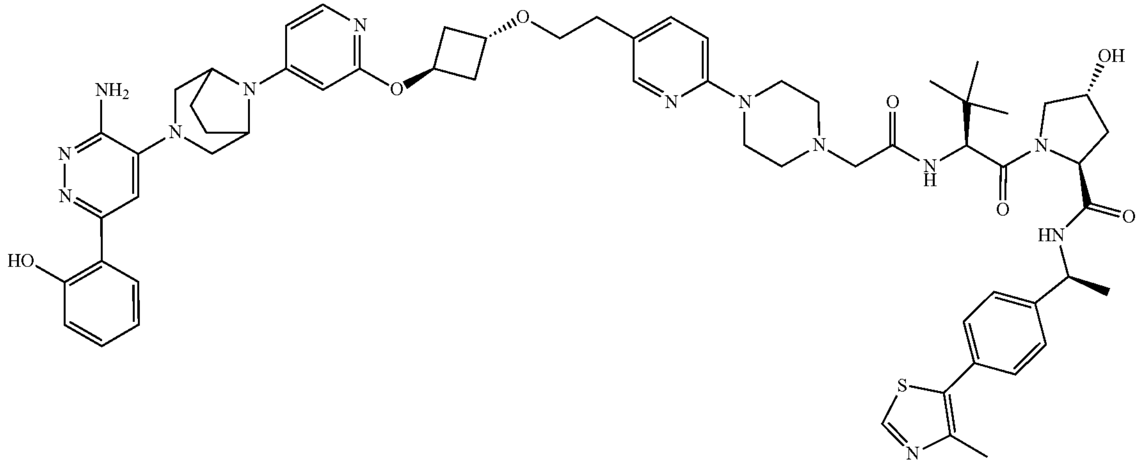 [SMILES: Cc1ncsc1-c1ccc([C@H](C)NC(=O)[C@@H]2C[C@@H](O)CN2C(=O)[C@@H](NC(=O)CN2CCN(c3ccc(CCO[C@H]4C[C@H](Oc5cc(N6C7CCC6CN(c6cc(-c8ccccc8O)nnc6N)C7)ccn5)C4)cn3)CC2)C(C)(C)C)cc1] | (2S,4R)-1-((2S)-2-(2-(4-(5-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)pyridin-2-yl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 80 | 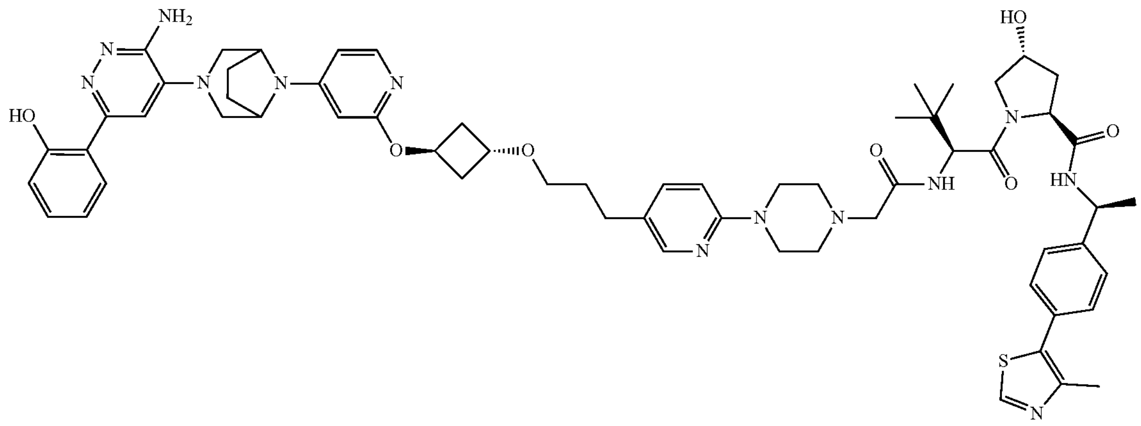 [SMILES: Cc1ncsc1-c1ccc([C@H](C)NC(=O)[C@@H]2C[C@@H](O)CN2C(=O)[C@@H](NC(=O)CN2CCN(c3ccc(CCCO[C@H]4C[C@H](Oc5cc(N6C7CCC6CN(c6cc(-c8ccccc8O)nnc6N)C7)ccn5)C4)cn3)CC2)C(C)(C)C)cc1] | (2S,4R)-1-((2S)-2-(2-(4-(5-(3-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)propyl)pyridin-2-yl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide |
| 81 | 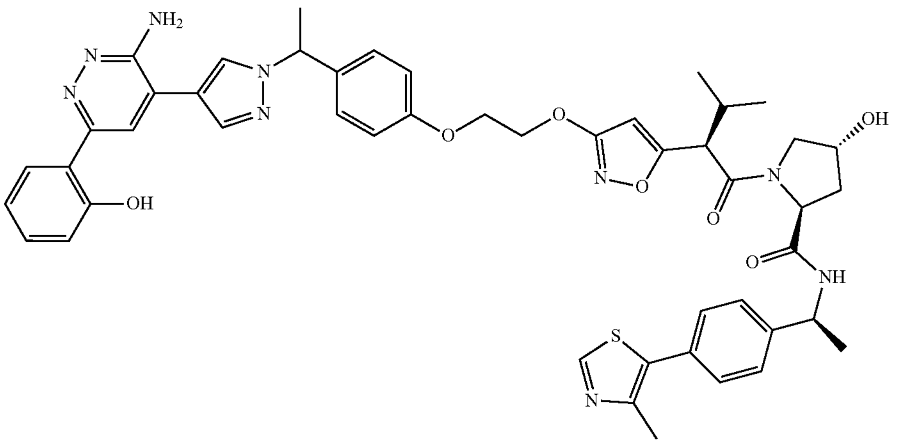 [SMILES: Cc1ncsc1-c1ccc([C@H](C)NC(=O)[C@@H]2C[C@@H](O)CN2C(=O)[C@@H](c2cc(OCCOc3ccc(C(C)n4cc(-c5cc(-c6ccccc6O)nnc5N)cn4)cc3)no2)C(C)C)cc1] | (2S,4R)-1-((2R)-2-(3-(2-(4-(1-(4-(3-amino-6-(2-hydroxyphenyl)pyridazin-4-yl)-1H-pyrazol-1-yl)ethyl)phenoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

Exemplary bifunctional degradation compounds of the present disclosure

| Ex. # | Structure | Compound Name |
| --- | --- | --- |
| 82 | 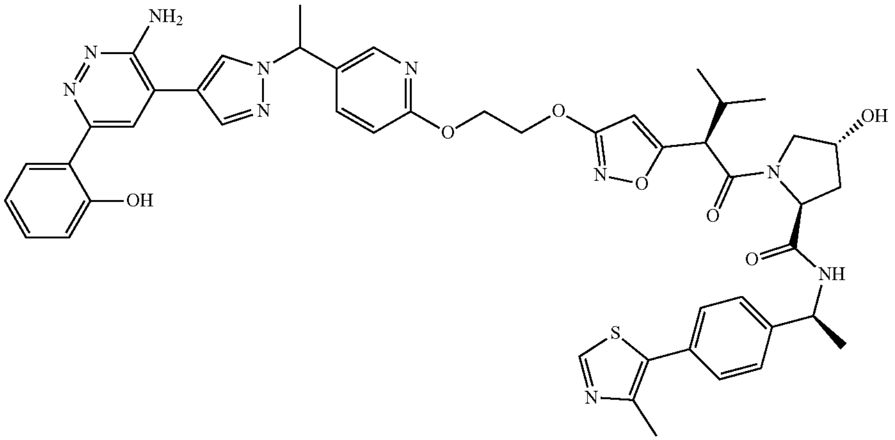 [SMILES: Cc1ncsc1-c1ccc([C@H](C)NC(=O)[C@@H]2C[C@@H](O)CN2C(=O)[C@@H](c2cc(OCCOc3ccc(C(C)n4cc(-c5cc(-c6ccccc6O)nnc5N)cn4)cn3)no2)C(C)C)cc1] | (2S,4R)-1-((2R)-2-(3-(2-((5-(1-(4-(3-amino-6-(2-hydroxyphenyl)pyridazin-4-yl)-1H-pyrazol-1-yl)ethyl)pyridin-2-yl)oxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 83 | 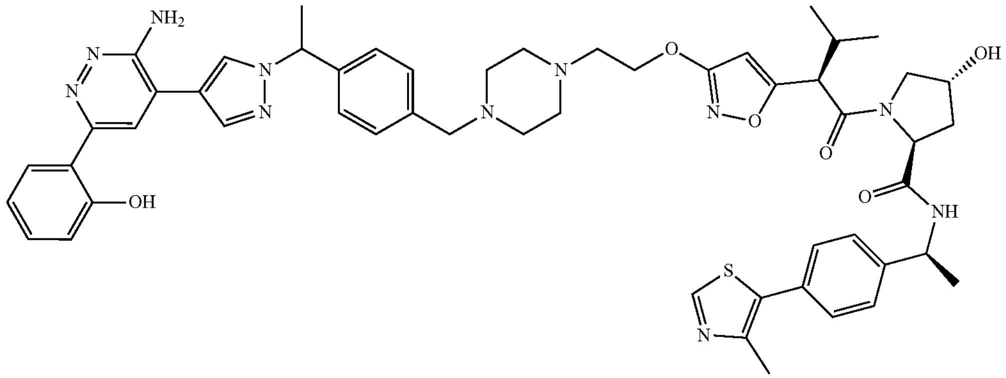 [SMILES: Cc1ncsc1-c1ccc([C@H](C)NC(=O)[C@@H]2C[C@@H](O)CN2C(=O)[C@@H](c2cc(OCCN3CCN(Cc4ccc(C(C)n5cc(-c6cc(-c7ccccc7O)nnc6N)cn5)cc4)CC3)no2)C(C)C)cc1] | (2S,4R)-1-((2R)-2-(3-(2-(4-(4-(1-(4-(3-amino-6-(2-hydroxyphenyl)pyridazin-4-yl)-1H-pyrazol-1-yl)ethyl)benzyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 84 | 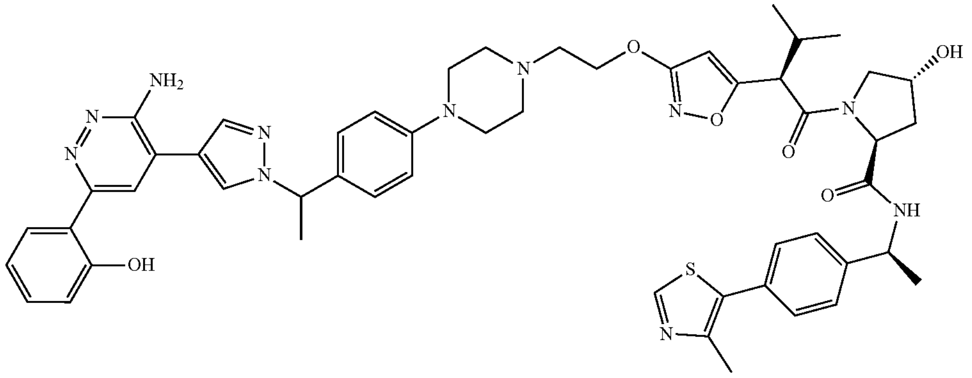 [SMILES: Cc1ncsc1-c1ccc([C@H](C)NC(=O)[C@@H]2C[C@@H](O)CN2C(=O)[C@@H](c2cc(OCCN3CCN(c4ccc(C(C)n5cc(-c6cc(-c7ccccc7O)nnc6N)cn5)cc4)CC3)no2)C(C)C)cc1] | (2S,4R)-1-((2R)-2-(3-(2-(4-(4-(1-(4-(3-amino-6-(2-hydroxyphenyl)pyridazin-4-yl)-1H-pyrazol-1-yl)ethyl)phenyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 85 | 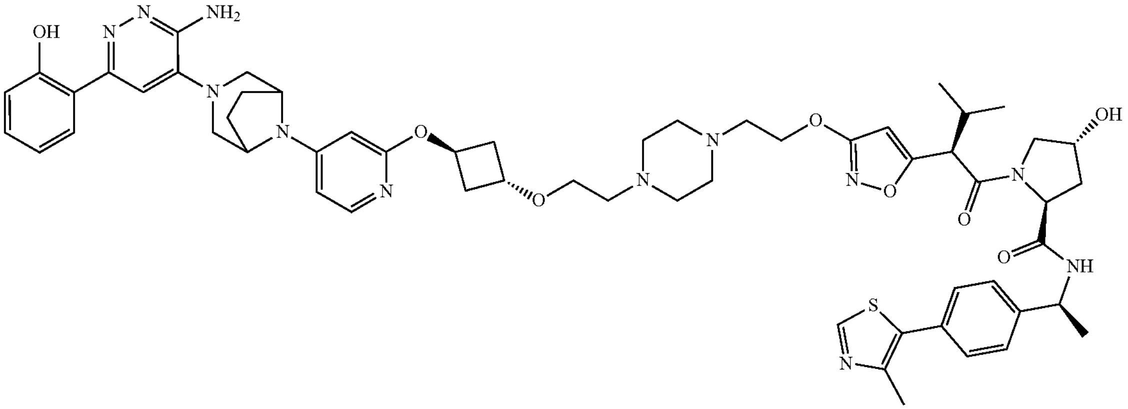 [SMILES: Cc1ncsc1-c1ccc([C@H](C)NC(=O)[C@@H]2C[C@@H](O)CN2C(=O)[C@@H](c2cc(OCCN3CCN(CCO[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 86 | 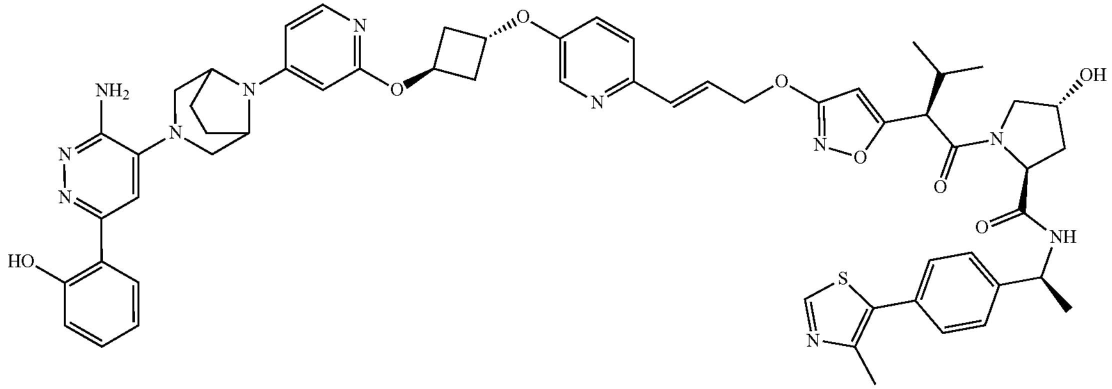 [SMILES: Cc1ncsc1-c1ccc([C@H](C)NC(=O)[C@@H]2C[C@@H](O)CN2C(=O)[C@@H](c2cc(OC/C=C/c3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-(((E)-3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)allyl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 87 | 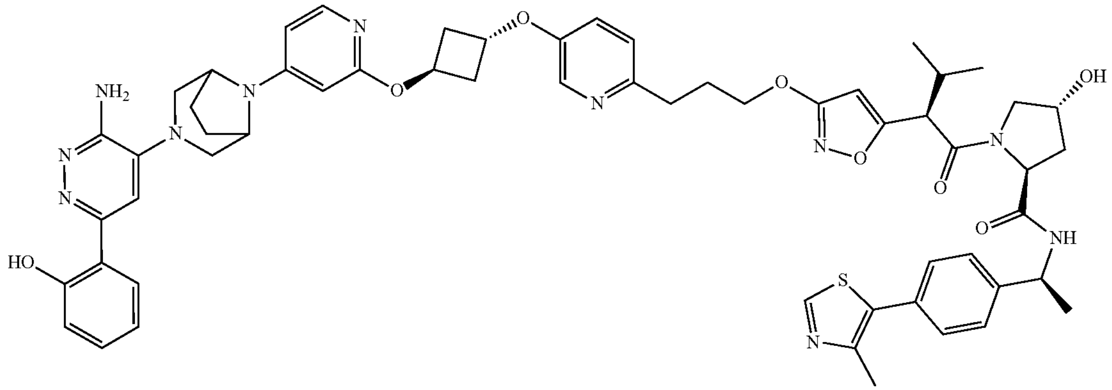 [SMILES: Cc1ncsc1-c1ccc([C@H](C)NC(=O)[C@@H]2C[C@@H](O)CN2C(=O)[C@@H](c2cc(OCCCc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-(3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 88 | 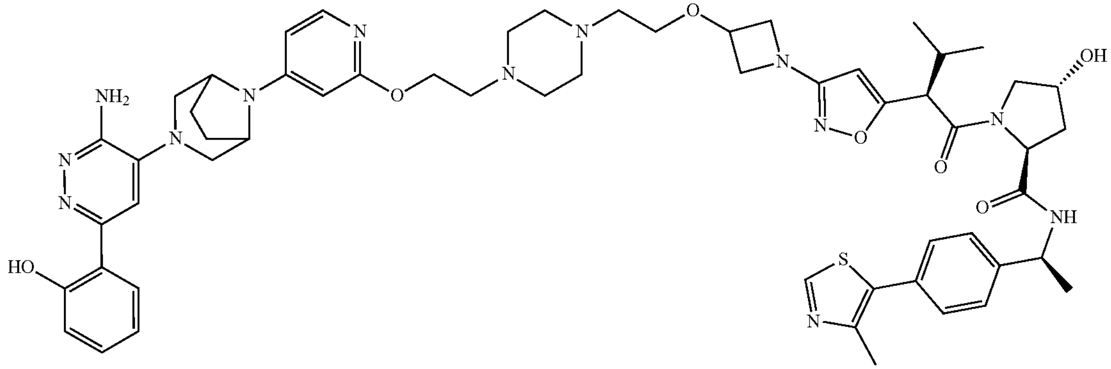 [SMILES: Cc1ncsc1-c1ccc([C@H](C)NC(=O)[C@@H]2C[C@@H](O)CN2C(=O)[C@@H](c2cc(N3CC(OCCN4CCN(CCOc5cc(N6C7CCC6CN(c6cc(-c8ccccc8O)nnc6N)C7)ccn5)CC4)C3)no2)C(C)C)cc1] | (2S,4R)-1-((2R)-2-(3-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)azetidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 89 | 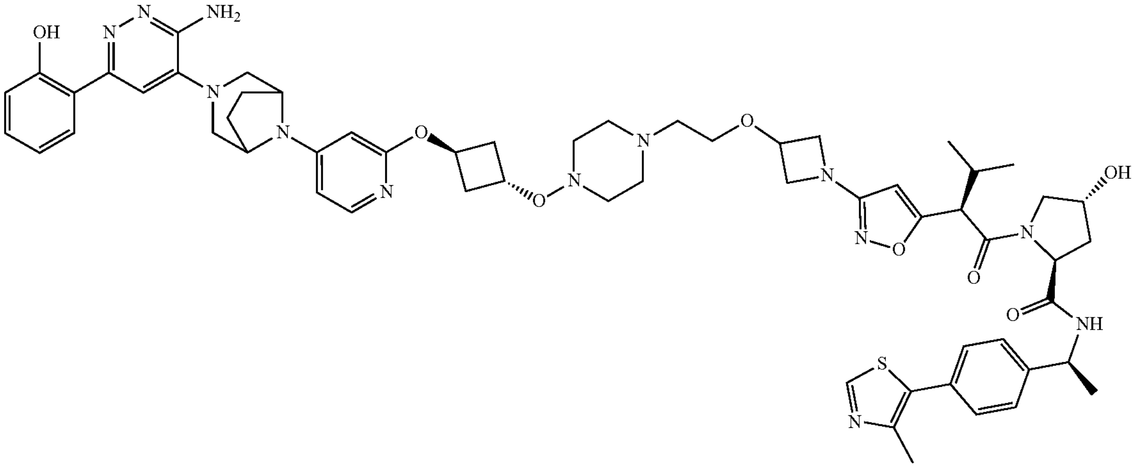 [SMILES: Cc1ncsc1-c1ccc([C@H](C)NC(=O)[C@@H]2C[C@@H](O)CN2C(=O)[C@@H](c2cc(N3CC(OCCN4CCN(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2R)-2-(3-(3-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)azetidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 90 | 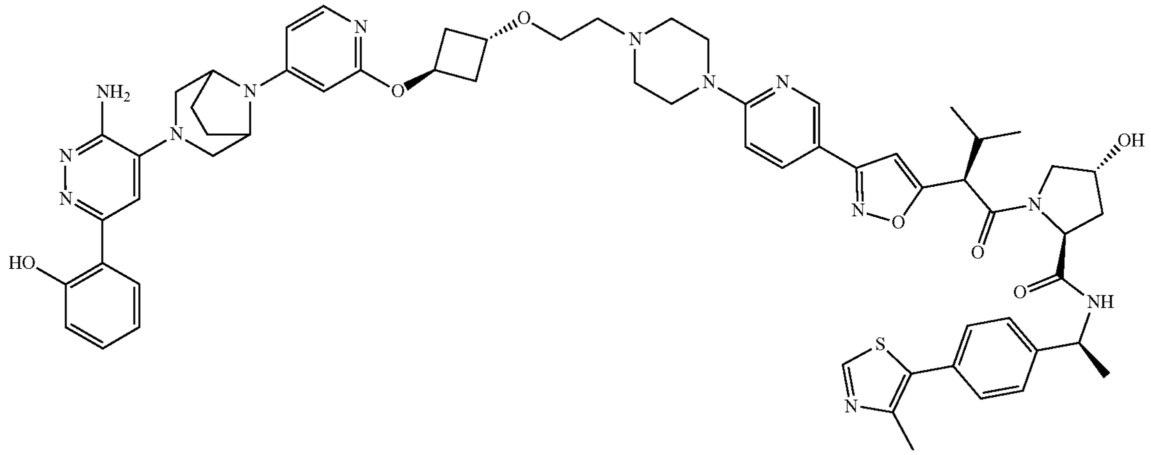 [SMILES: Cc1ncsc1-c1ccc([C@H](C)NC(=O)[C@@H]2C[C@@H](O)CN2C(=O)[C@@H](c2cc(-c3ccc(N4CCN(CCO[C@H]5C[C@H](Oc6cc(N7C8CCC7CN(c7cc(-c9ccccc9O)nnc7N)C8)ccn6)C5)CC4)nc3)no2)C(C)C)cc1] | (2S,4R)-1-((2R)-2-(3-(6-(4-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)piperazin-1-yl)pyridin-3-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 91 | 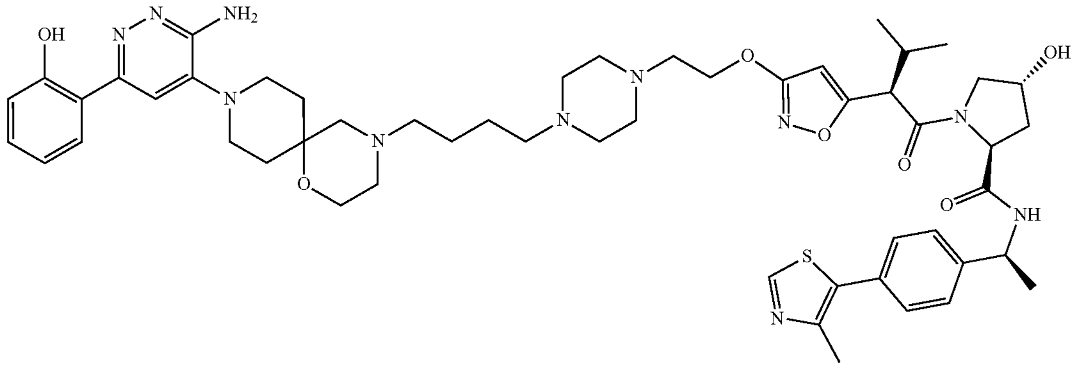 [SMILES: Cc1ncsc1-c1ccc([C@H](C)NC(=O)[C@@H]2C[C@@H](O)CN2C(=O)[C@@H](c2cc(OCCN3CCN(CCCCN4CCOC5(CCN(c6cc(-c7ccccc7O)nnc6N)CC5)C4)CC3)no2)C(C)C)cc1] | (2S,4R)-1-((R)-2-(3-(2-(4-(4-(9-(3-amino-6-(2-hydroxyphenyl)pyridazin-4-yl)-1-oxa-4,9-diazaspiro[5.5]undecan-4-yl)butyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 92 | 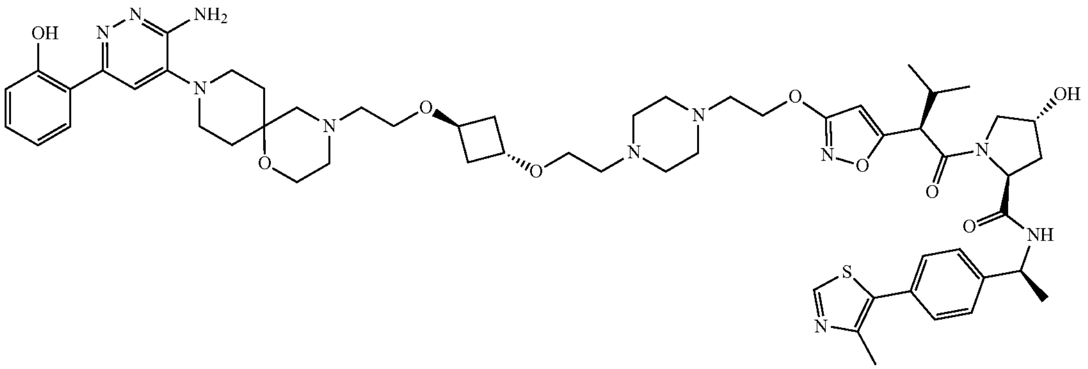 [SMILES: Cc1ncsc1-c1ccc([C@H](C)NC(=O)[C@@H]2C[C@@H](O)CN2C(=O)[C@@H](c2cc(OCCN3CCN(CCO[C@H]4C[C@H](OCCN5CCOC6(CCN(c7cc(-c8ccccc8O)nnc7N)CC6)C5)C4)CC3)no2)C(C)C)cc1] | (2S,4R)-1-((R)-2-(3-(2-(4-(2-((1r,3r)-3-(2-(9-(3-amino-6-(2-hydroxyphenyl)pyridazin-4-yl)-1-oxa-4,9-diazaspiro[5.5]undecan-4-yl)ethoxy)cyclobutoxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 93 | 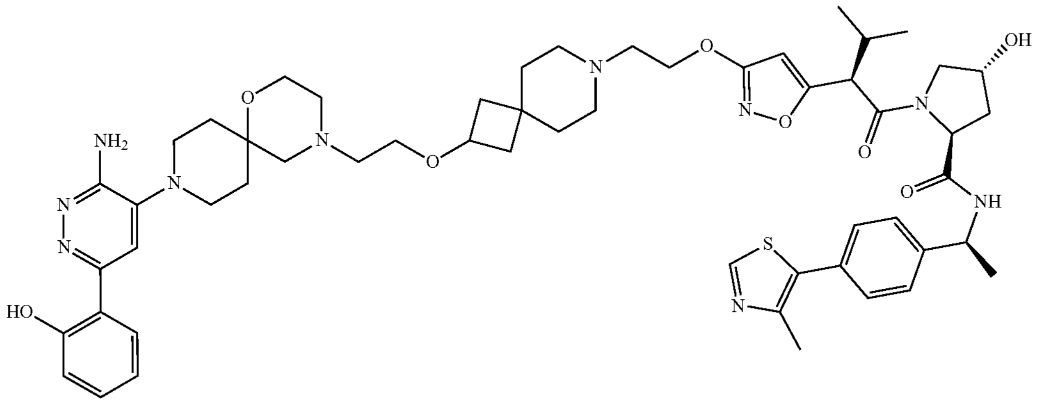 [SMILES: Cc1ncsc1-c1ccc([C@H](C)NC(=O)[C@@H]2C[C@@H](O)CN2C(=O)[C@@H](c2cc(OCCN3CCC4(CC3)CC(OCCN3CCOC5(CCN(c6cc(-c7ccccc7O)nnc6N)CC5)C3)C4)no2)C(C)C)cc1] | (2S,4R)-1-((R)-2-(3-(2-(2-(2-(9-(3-amino-6-(2-hydroxyphenyl)pyridazin-4-yl)-1-oxa-4,9-diazaspiro[5.5]undecan-4-yl)ethoxy)-7-azaspiro[3.5]nonan-7-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 94 | 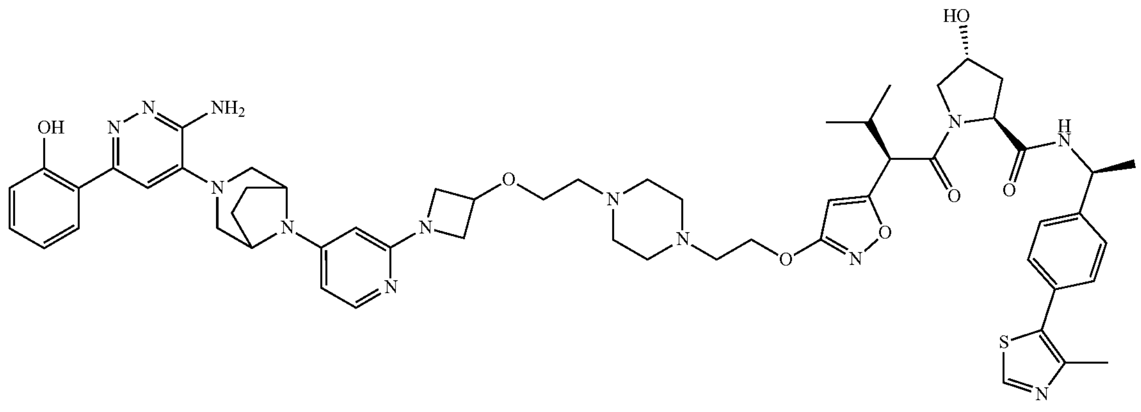 [SMILES: Cc1ncsc1-c1ccc([C@H](C)NC(=O)[C@@H]2C[C@@H](O)CN2C(=O)[C@@H](c2cc(OCCN3CCN(CCOC4CN(c5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-(2-((1-(4-(3-(3-amino-6-(2-hydroxyphenyl)pyridazin-4-yl)-3,8-diazabicyclo[3.2.1]octan-8-yl)pyridin-2-yl)azetidin-3-yl)oxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 95 | 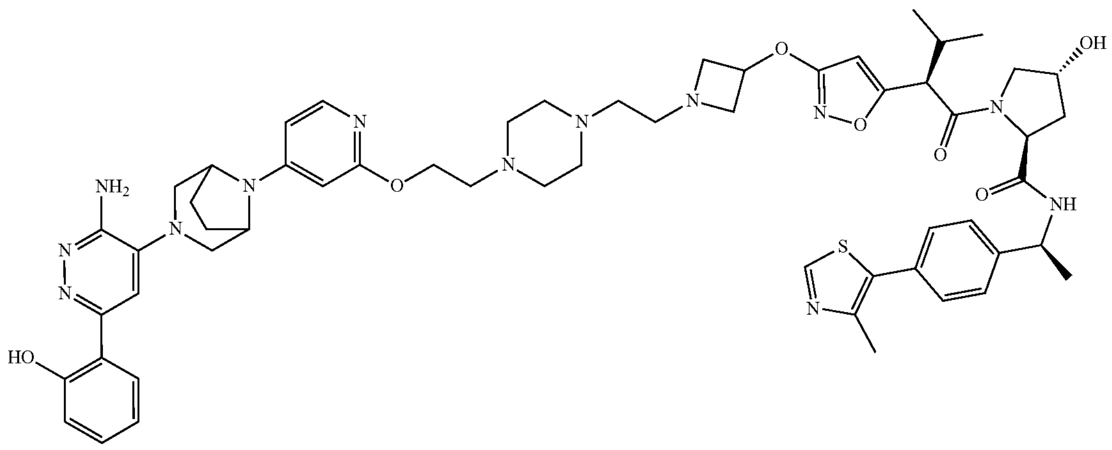 [SMILES: Cc1ncsc1-c1ccc([C@H](C)NC(=O)[C@@H]2C[C@@H](O)CN2C(=O)[C@@H](c2cc(OC3CN(CCN4CCN(CCOc5cc(N6C7CCC6CN(c6cc(-c8ccccc8O)nnc6N)C7)ccn5)CC4)C3)no2)C(C)C)cc1] | (2S,4R)-1-((2R)-2-(3-((1-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethyl)azetidin-3-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 96 | 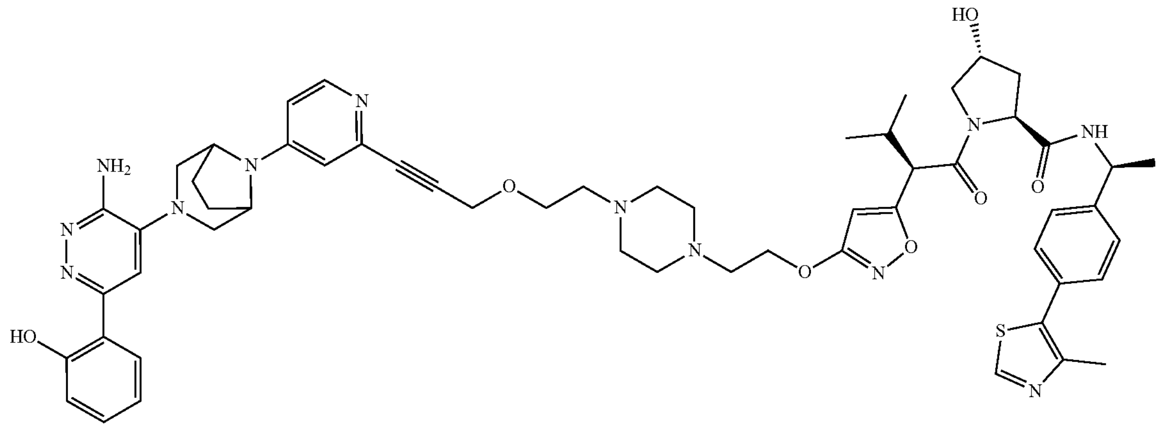 [SMILES: Cc1ncsc1-c1ccc([C@H](C)NC(=O)[C@@H]2C[C@@H](O)CN2C(=O)[C@@H](c2cc(OCCN3CCN(CCOCC#Cc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)oxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 97 | 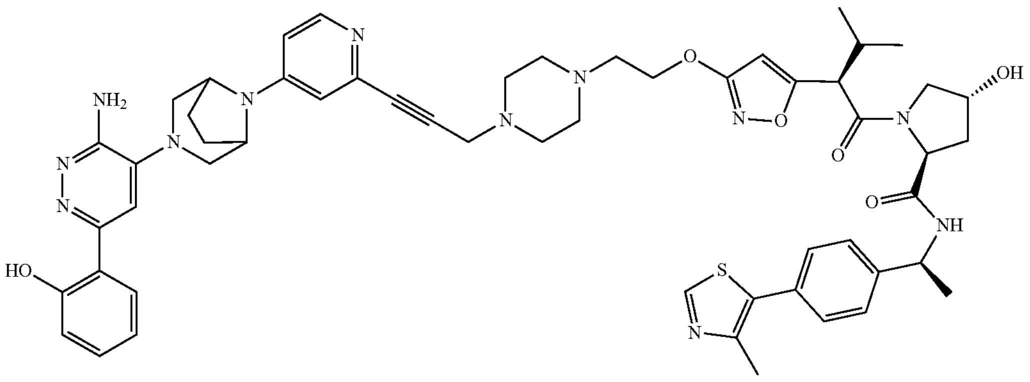 [SMILES: Cc1ncsc1-c1ccc([C@H](C)NC(=O)[C@@H]2C[C@@H](O)CN2C(=O)[C@@H](c2cc(OCCN3CCN(CC#Cc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 98 | 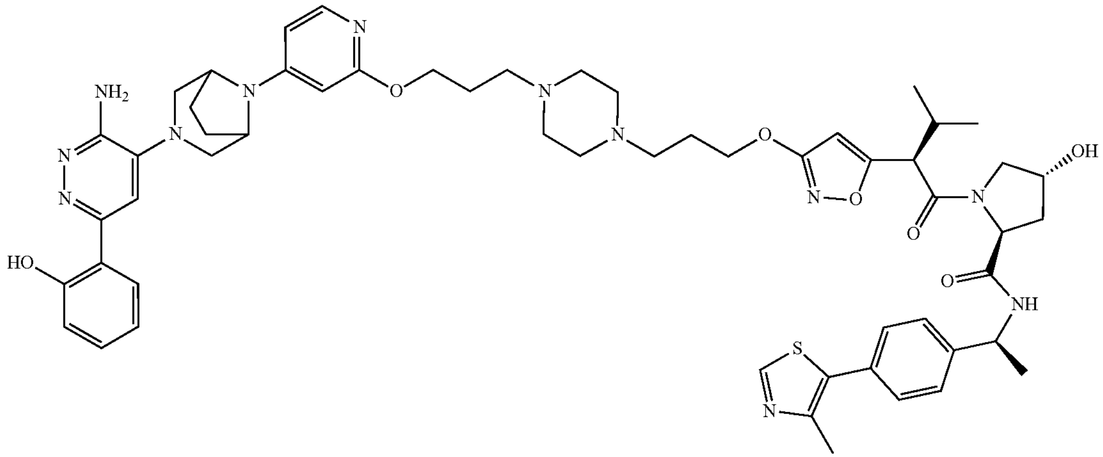 [SMILES: Cc1ncsc1-c1ccc([C@H](C)NC(=O)[C@@H]2C[C@@H](O)CN2C(=O)[C@@H](c2cc(OCCCN3CCN(CCCOc4cc(N5C6CCC5CN(c5cc(-c7ccccc7O)nnc5N)C6)ccn4)CC3)no2)C(C)C)cc1] | (2S,4R)-1-((2R)-2-(3-(3-(4-(3-((4-(3-(3-amino-6-(2-hydroxyphenyl)pyridazin-4-yl)-3,8-diazabicyclo[3.2.1]octan-8-yl)pyridin-2-yl)oxy)propyl)piperazin-1-yl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 99 | 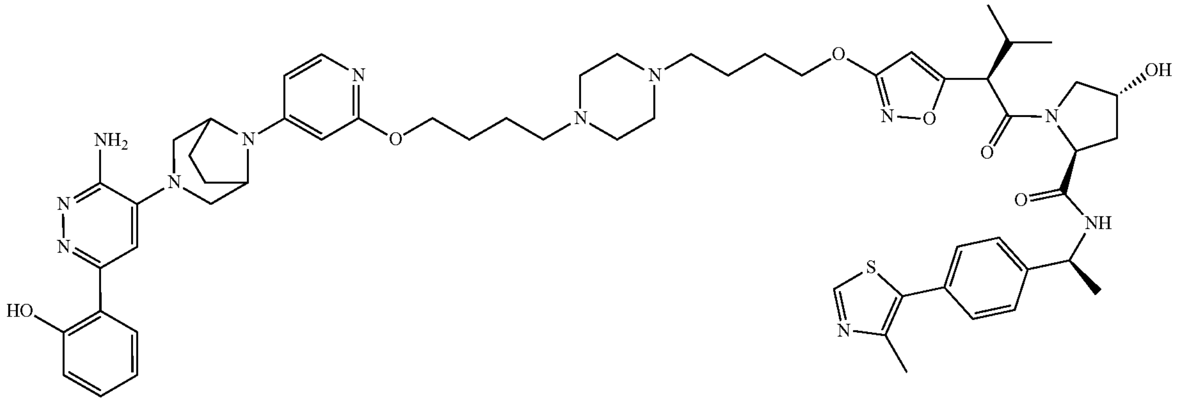 [SMILES: Cc1ncsc1-c1ccc([C@H](C)NC(=O)[C@@H]2C[C@@H](O)CN2C(=O)[C@@H](c2cc(OCCCCN3CCN(CCCCOc4cc(N5C6CCC5CN(c5cc(-c7ccccc7O)nnc5N)C6)ccn4)CC3)no2)C(C)C)cc1] | (2S,4R)-1-((2R)-2-(3-(4-(4-(4-((4-(3-(3-amino-6-(2-hydroxyphenyl)pyridazin-4-yl)-3,8-diazabicyclo[3.2.1]octan-8-yl)pyridin-2-yl)oxy)butyl)piperazin-1-yl)butoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 100 | 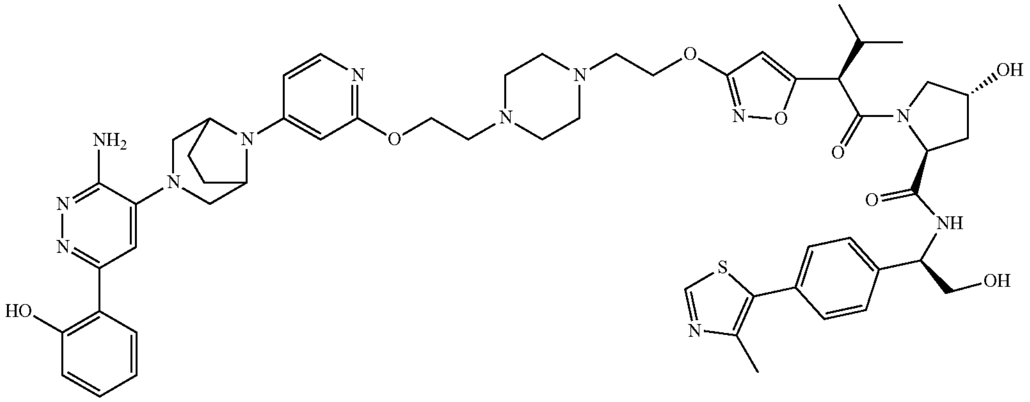 [SMILES: Cc1ncsc1-c1ccc([C@H](CO)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide |
| 101 | 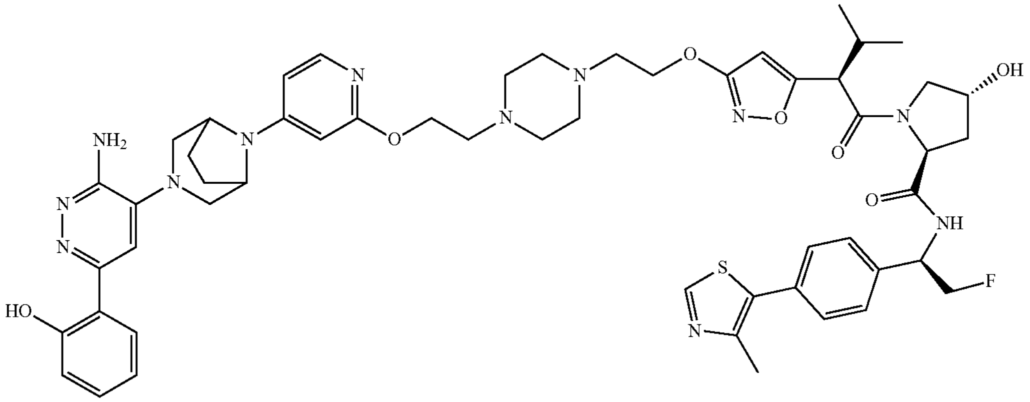 [SMILES: Cc1ncsc1-c1ccc([C@H](CF)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-fluoro-1-(4-(4-methylthiazol-5-yl)phenyl)ethyl)-4-hydroxypyrrolidine-2-carboxamide |

TABLE 1A-continued

| Exemplary bifunctional degradation compounds of the present disclosure | | |
|---|---|---|
| Ex. # | Structure | Compound Name |
| 102 | 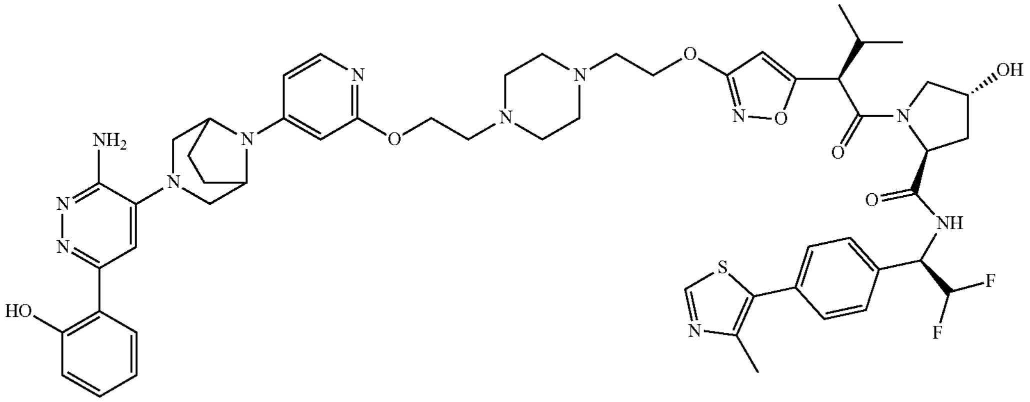 [SMILES: Cc1ncsc1-c1ccc([C@@H](NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)C(F)F)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2,2-difluoro-1-(4-(4-methylthiazol-5-yl)phenyl)ethyl)-4-hydroxypyrrolidine-2-carboxamide |
| 103 | 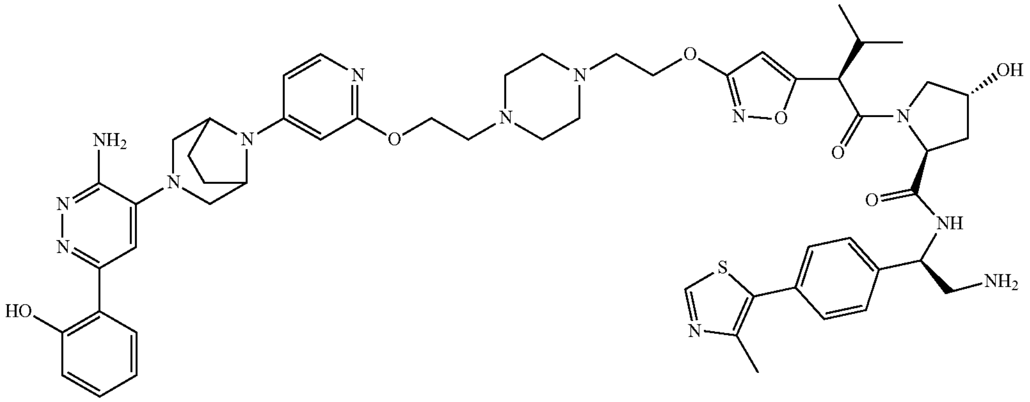 [SMILES: Cc1ncsc1-c1ccc([C@H](CN)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-N-((R)-2-amino-1-(4-(4-methylthiazol-5-yl)phenyl)ethyl)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |

TABLE 1A-continued

| Exemplary bifunctional degradation compounds of the present disclosure | | |
|---|---|---|
| Ex. # | Structure | Compound Name |
| 104 | 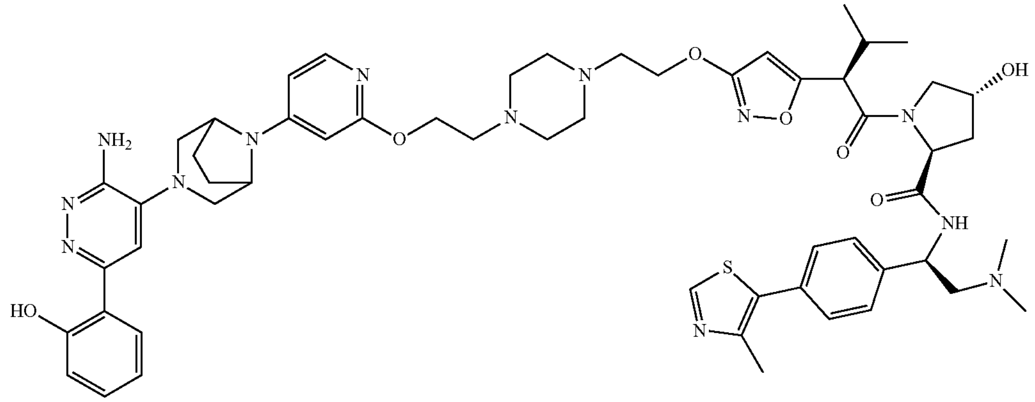 [SMILES: Cc1ncsc1-c1ccc([C@H](CN(C)C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-(dimethylamino)-1-(4-(4-methylthiazol-5-yl)phenyl)ethyl)-4-hydroxypyrrolidine-2-carboxamide |
| 105 | 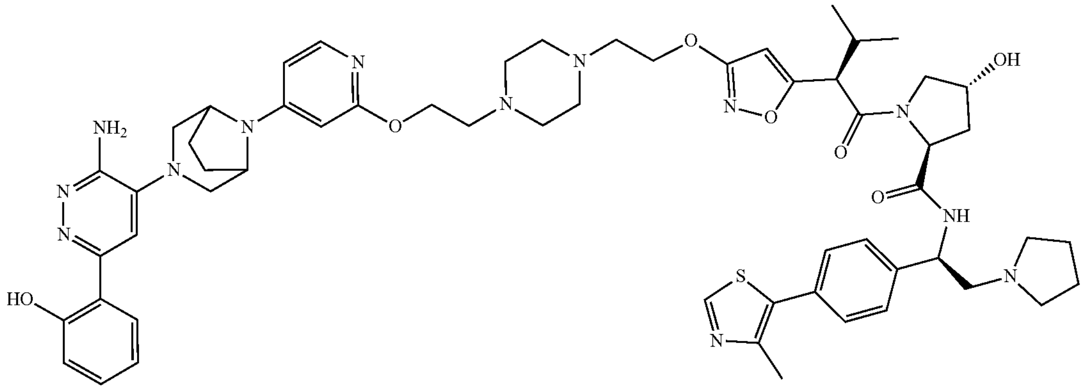 [SMILES: Cc1ncsc1-c1ccc([C@H](CN2CCCC2)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-1-(4-(4-methylthiazol-5-yl)phenyl)-2-(pyrrolidin-1-yl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 106 | 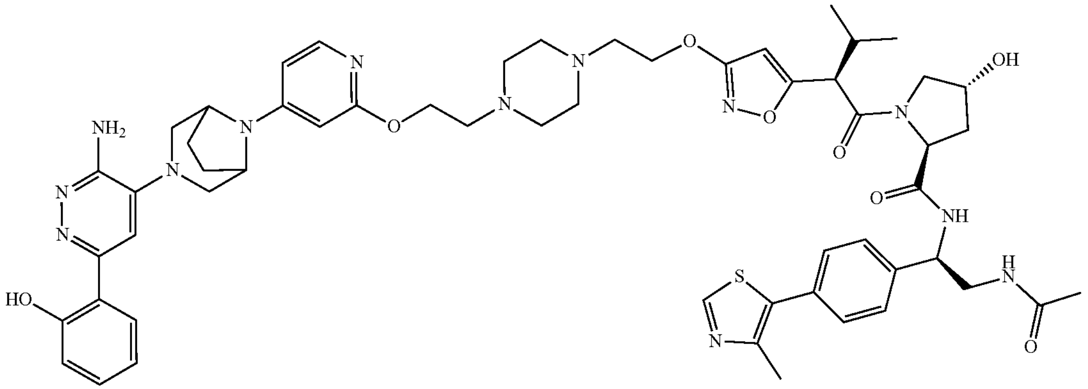 [SMILES: CC(=O)NC[C@H](NC(=O)[C@@H]1C[C@@H](O)CN1C(=O)[C@@H](c1cc(OCCN2CCN(CCOc3cc(N4C5CCC4CN(c4cc(-c6ccccc6O)nnc4N)C5)ccn3)CC2)no1)C(C)C)c1ccc(-c2scnc2C)cc1] | (2S,4R)-N-((R)-2-acetamido-1-(4-(4-methylthiazol-5-yl)phenyl)ethyl)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |
| 107 | 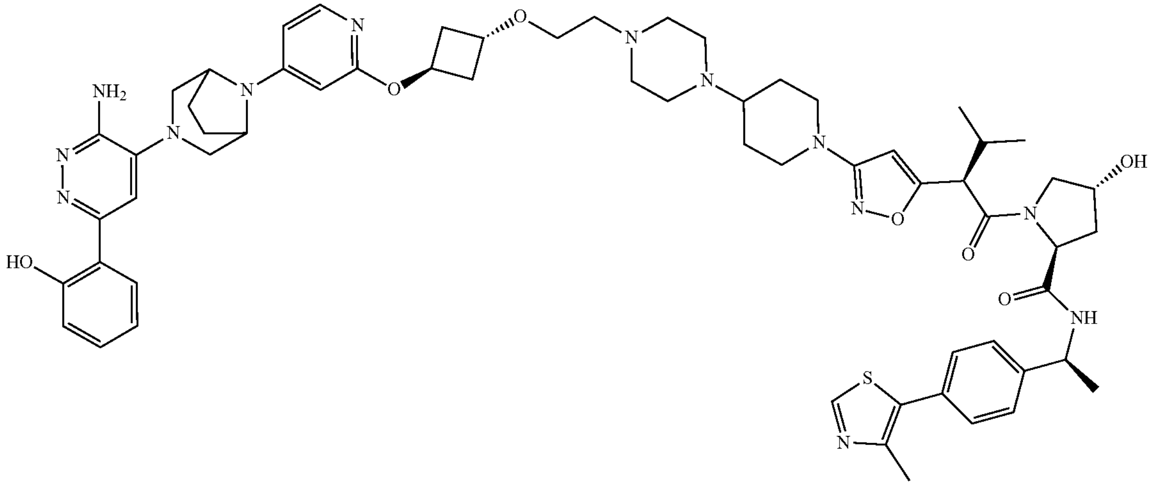 [SMILES: Cc1ncsc1-c1ccc([C@H](C)NC(=O)[C@@H]2C[C@@H](O)CN2C(=O)[C@@H](c2cc(N3CCC(N4CCN(CCO[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-(4-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)piperazin-1-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 108 | 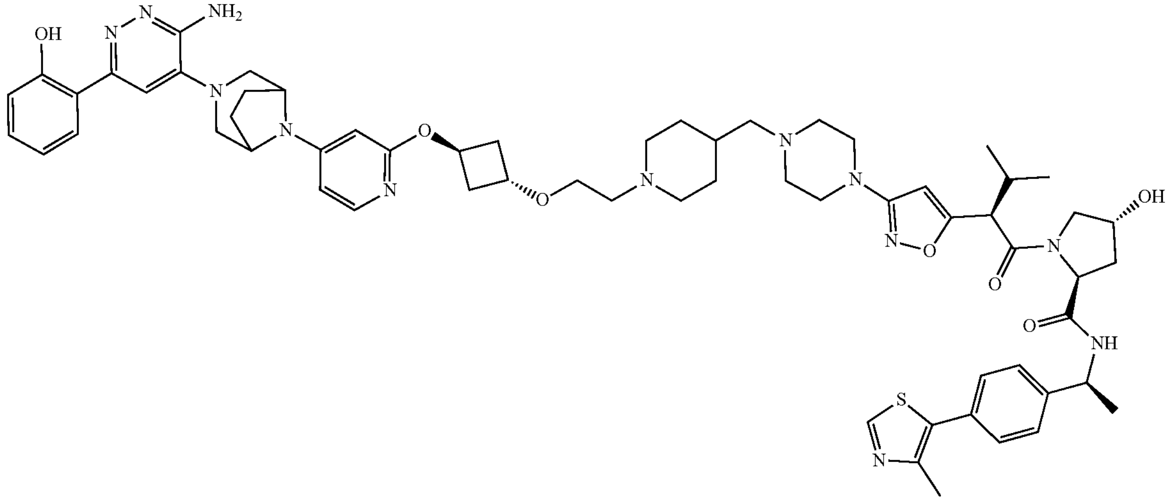 [SMILES: Cc1ncsc1-c1ccc([C@H](C)NC(=O)[C@@H]2C[C@@H](O)CN2C(=O)[C@@H](c2cc(N3CCN(CC4CCN(CCO[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((1-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 109 | 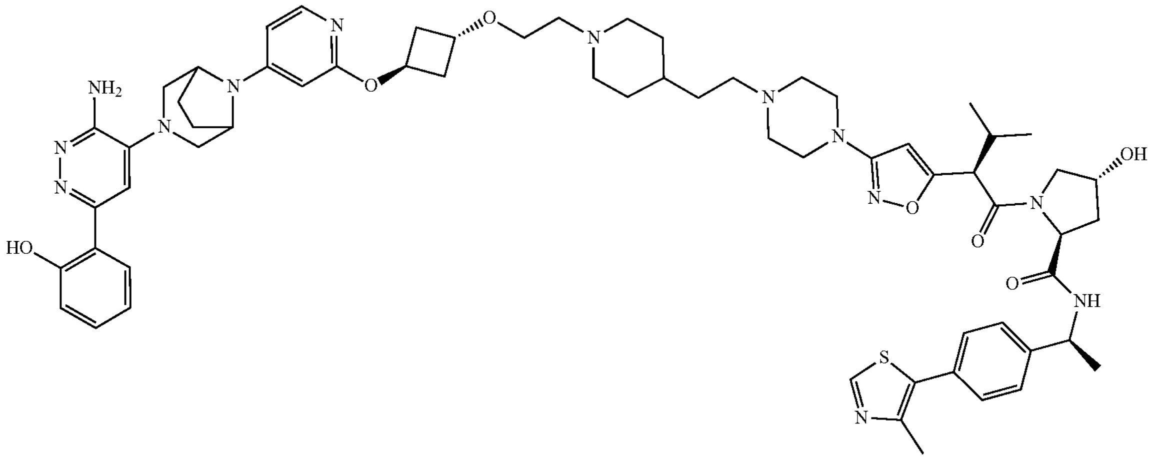 [SMILES: Cc1ncsc1-c1ccc([C@H](C)NC(=O)[C@@H]2C[C@@H](O)CN2C(=O)[C@@H](c2cc(N3CCN(CCC4CCN(CCO[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-(2-(1-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)piperidin-4-yl)ethyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 110 | 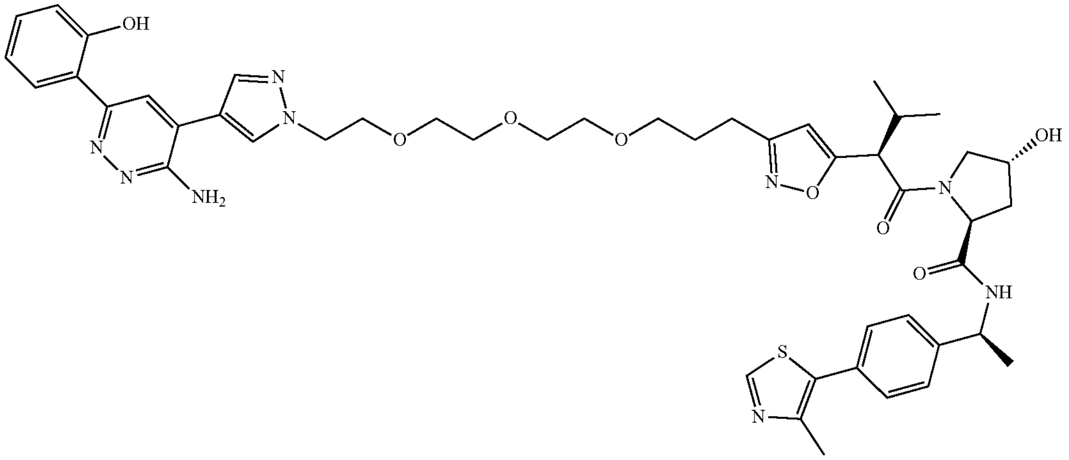 [SMILES: Cc1ncsc1-c1ccc([C@H](C)NC(=O)[C@@H]2C[C@@H](O)CN2C(=O)[C@@H](c2cc(CCCOCCOCCOCCn3cc(-c4cc(-c5ccccc5O)nnc4N)cn3)no2)C(C)C)cc1] | (2S,4R)-1-((R)-2-(3-(3-(2-(2-(2-(4-(3-amino-6-(2-hydroxyphenyl)pyridazin-4-yl)-1H-pyrazol-1-yl)ethoxy)ethoxy)ethoxy)propyl) isoxazol-5-yl)-3-methylbutanoyl)-4-hydroxy-N-((S)-1-(4-(4-methylthiazol-5-yl)phenyl)ethyl)pyrrolidine-2-carboxamide |
| 111 | 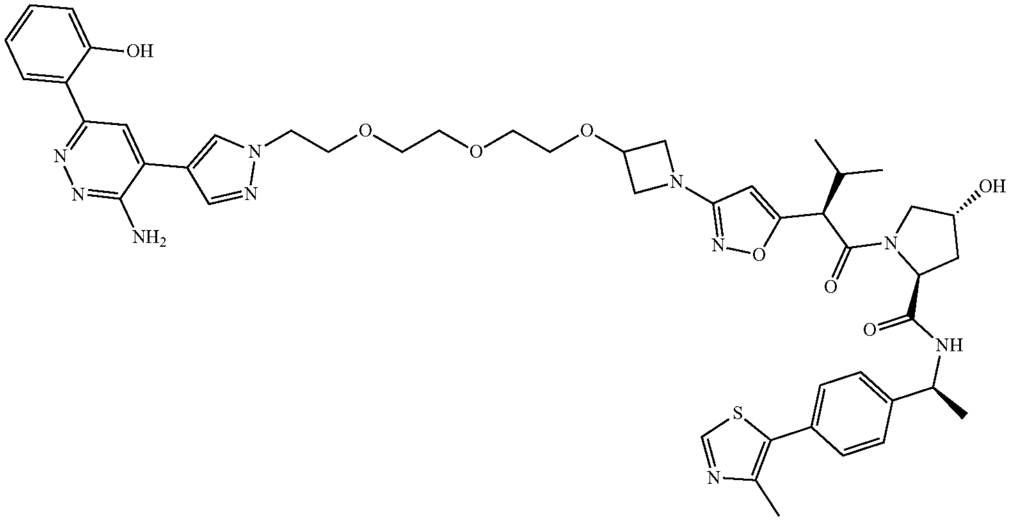 [SMILES: Cc1ncsc1-c1ccc([C@H](C)NC(=O)[C@@H]2C[C@@H](O)CN2C(=O)[C@@H](c2cc(N3CC(OCCOCCOCCn4cc(-c5cc(-c6ccccc6O)nnc5N)cn4)C3)no2)C(C)C)cc1] | (2S,4R)-1-((R)-2-(3-(3-(2-(2-(2-(4-(3-amino-6-(2-hydroxyphenyl)pyridazin-4-yl)-1H-pyrazol-1-yl)ethoxy)ethoxy)ethoxy)azetidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

Exemplary bifunctional degradation compounds of the present disclosure

| Ex. # | Structure | Compound Name |
| --- | --- | --- |
| 112 | 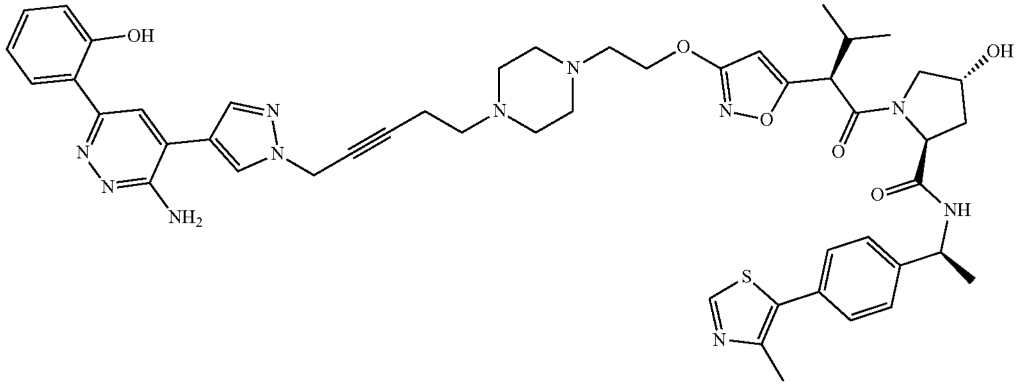 [SMILES: Cc1ncsc1-c1ccc([C@H](C)NC(=O)[C@@H]2C[C@@H](O)CN2C(=O)[C@@H](c2cc(OCCN3CCN(CCC#CCn4cc(-c5cc(-c6ccccc6O)nnc5N)cn4)CC3)no2)C(C)C)cc1] | (2S,4R)-1-((R)-2-(3-(2-(4-(5-(4-(3-amino-6-(2-hydroxyphenyl)pyridazin-4-yl)-1H-pyrazol-1-yl)pent-3-yn-1-yl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 113 | 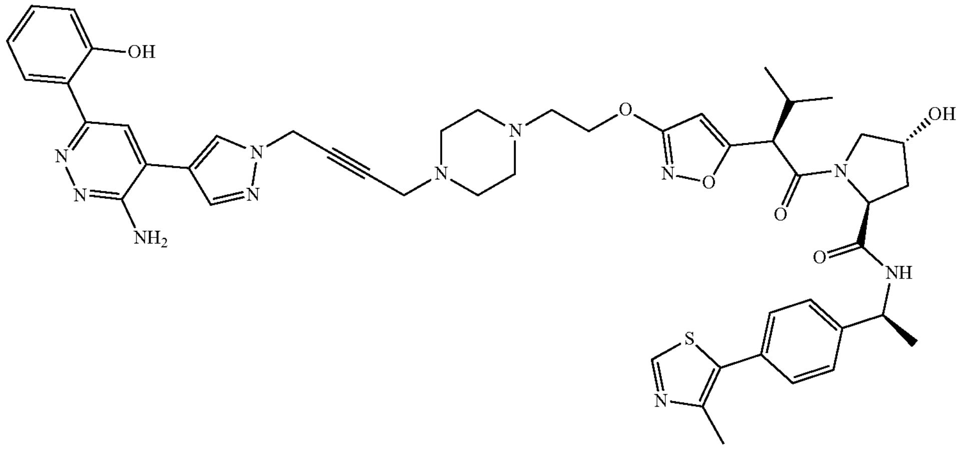 [SMILES: Cc1ncsc1-c1ccc([C@H](C)NC(=O)[C@@H]2C[C@@H](O)CN2C(=O)[C@@H](c2cc(OCCN3CCN(CC#CCn4cc(-c5cc(-c6ccccc6O)nnc5N)cn4)CC3)no2)C(C)C)cc1] | (2S,4R)-1-((R)-2-(3-(2-(4-(4-(4-(3-amino-6-(2-hydroxyphenyl)pyridazin-4-yl)-1H-pyrazol-1-yl)but-2-yn-1-yl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 114 | 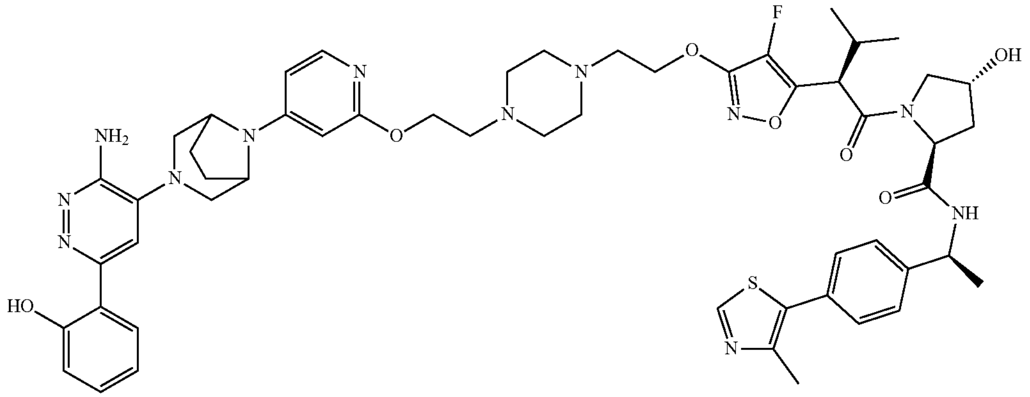 [SMILES: Cc1ncsc1-c1ccc([C@H](C)NC(=O)[C@@H]2C[C@@H](O)CN2C(=O)[C@@H](c2onc(OCCN3CCN(CCOc4cc(N5C6CCC5CN(c5cc(-c7ccccc7O)nnc5N)C6)ccn4)CC3)c2F)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)-4-fluoroisoxazol-5-yl)-3-methylbutanoyl)-4-hydroxy-N-((S)-1-(4-(4-methylthiazol-5-yl)phenyl)ethyl)pyrrolidine-2-carboxamide |
| 115 | 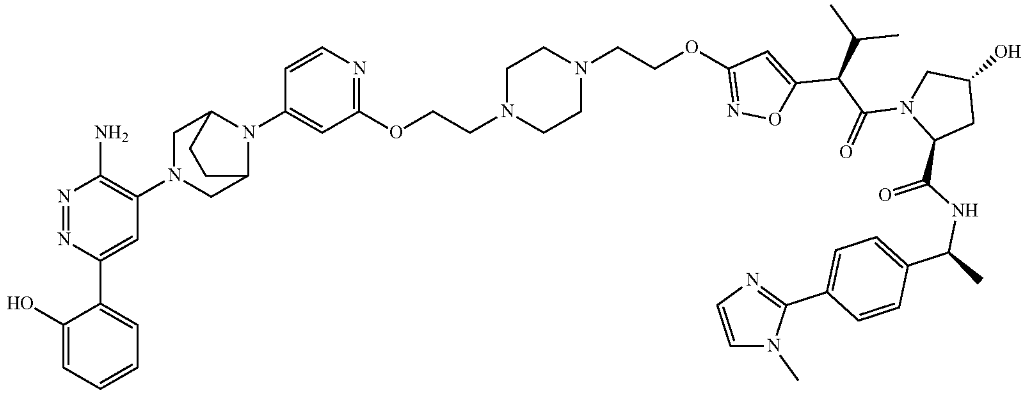 [SMILES: CC(C)[C@@H](C(=O)N1C[C@H](O)C[C@H]1C(=O)N[C@@H](C)c1ccc(-c2nccn2C)cc1)c1cc(OCCN2CCN(CCOc3cc(N4C5CCC4CN(c4cc(-c6ccccc6O)nnc4N)C5)ccn3)CC2)no1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(1-methyl-1H-imidazol-2-yl)phenyl)ethyl)pyrrolidine-2-carboxamide |

TABLE 1A-continued

Exemplary bifunctional degradation compounds of the present disclosure

| Ex. # | Structure | Compound Name |
| --- | --- | --- |
| 116 | 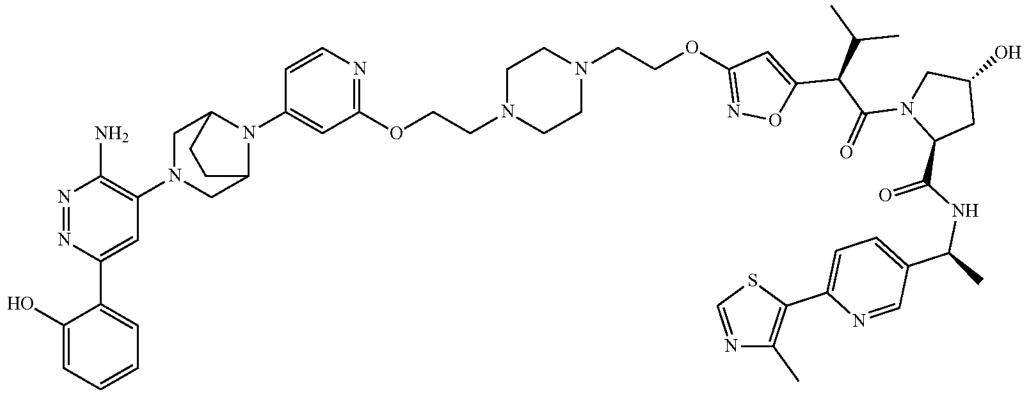 [SMILES: Cc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cn1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 117 | 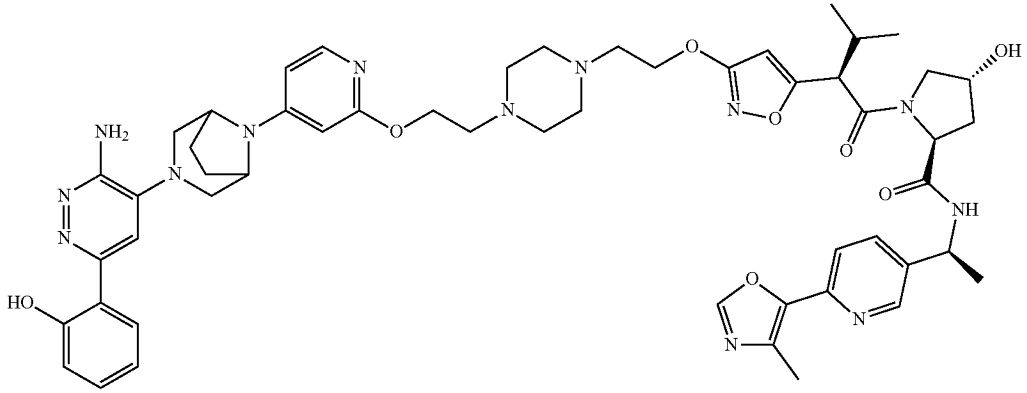 [SMILES: Cc1ncoc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cn1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(6-(4-methyloxazol-5-yl)pyridin-3-yl)ethyl)pyrrolidine-2-carboxamide |

TABLE 1A-continued

| Ex. # | Structure | Compound Name |
|---|---|---|
| | Exemplary bifunctional degradation compounds of the present disclosure | |
| 118 | 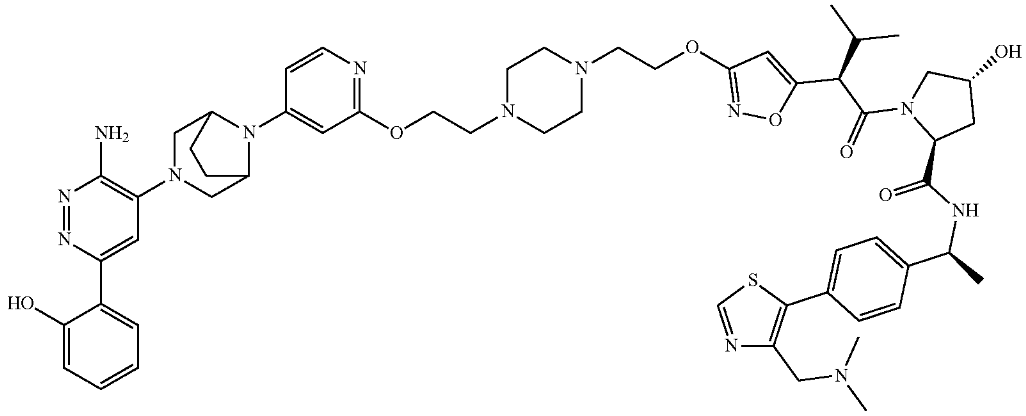 [SMILES: CC(C)[C@@H](C(=O)N1C[C@H](O)C[C@H]1C(=O)N[C@@H](C)c1ccc(-c2scnc2CN(C)C)cc1)c1cc(OCCN2CCN(CCOc3cc(N4C5CCC4CN(c4cc(-c6ccccc6O)nnc4N)C5)ccn3)CC2)no1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-((dimethylamino)methyl)thiazol-5-yl)phenyl)ethyl)-4-hydroxypyrrolidine-2-carboxamide |
| 119 | 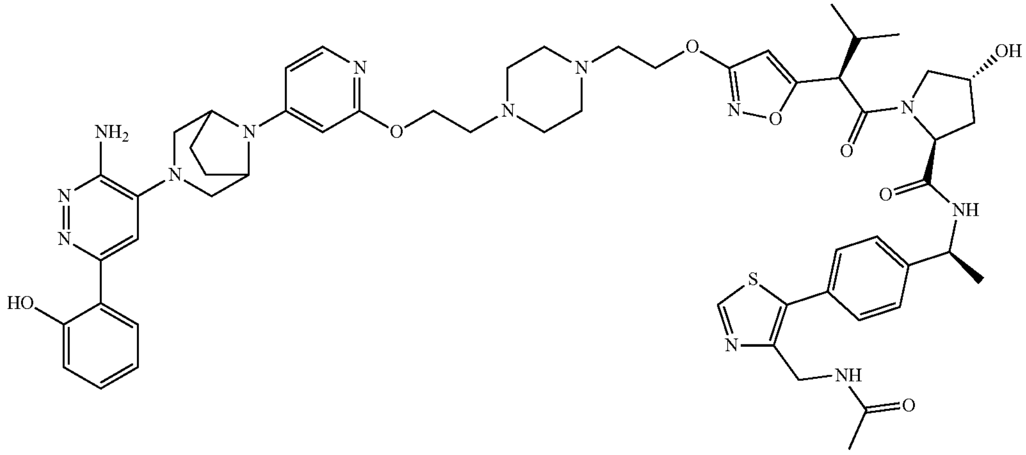 [SMILES: CC(=O)NCc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-N-((S)-1-(4-(4-(acetamidomethyl)thiazol-5-yl)phenyl)ethyl)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |

TABLE 1A-continued

| Ex. # | Structure | Compound Name |
|---|---|---|
| | Exemplary bifunctional degradation compounds of the present disclosure | |
| 120 | 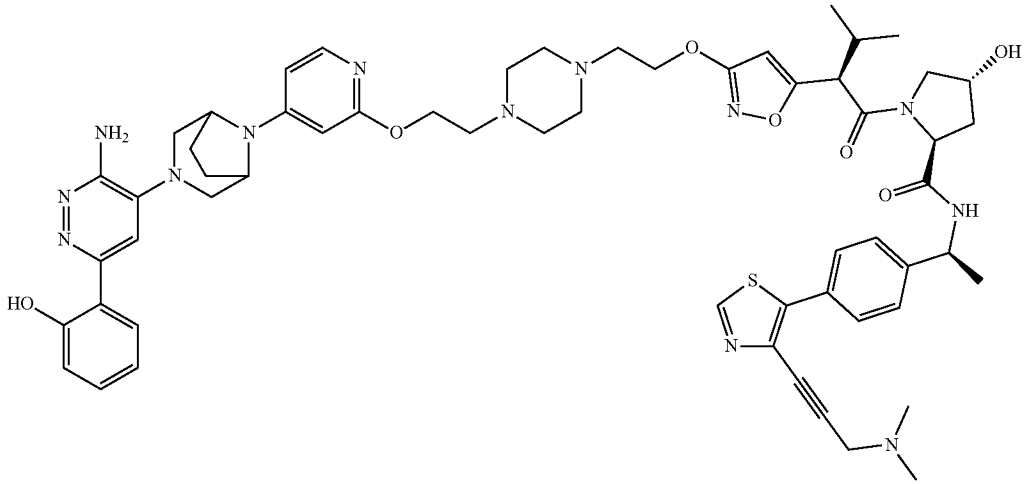 [SMILES: CC(C)[C@@H](C(=O)N1C[C@H](O)C[C@H]1C(=O)N[C@@H](C)c1ccc(-c2scnc2C#CCN(C)C)cc1)c1cc(OCCN2CCN(CCOc3cc(N4C5CCC4CN(c4cc(-c6ccccc6O)nnc4N)C5)ccn3)CC2)no1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-(3-(dimethylamino)prop-1-yn-1-yl)thiazol-5-yl)phenyl)ethyl)-4-hydroxypyrrolidine-2-carboxamide |
| 121 | 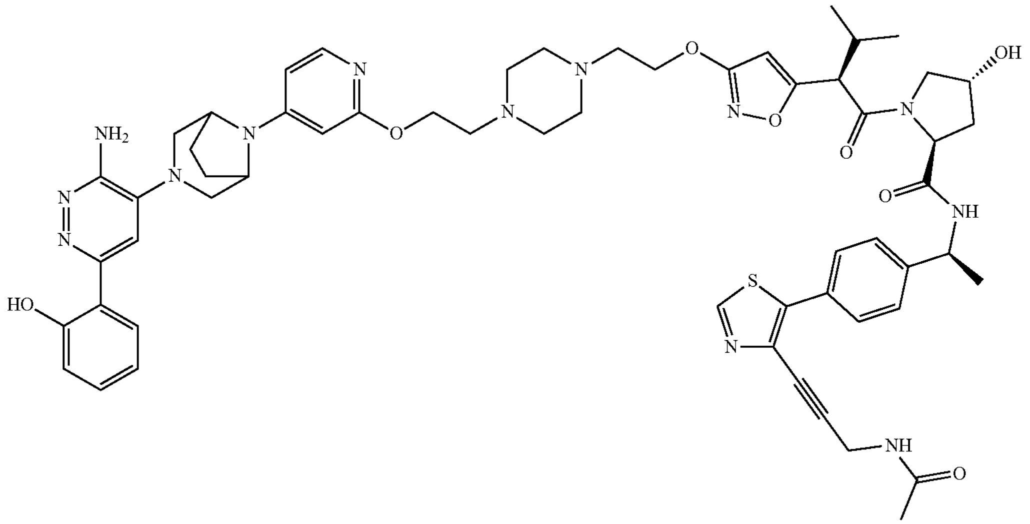 [SMILES: CC(=O)NCC#Cc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-N-((S)-1-(4-(4-(3-acetamidoprop-1-yn-1-yl)thiazol-5-yl)phenyl)ethyl)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |

TABLE 1A-continued

| Exemplary bifunctional degradation compounds of the present disclosure | | |
|---|---|---|
| Ex. # | Structure | Compound Name |
| 122 | 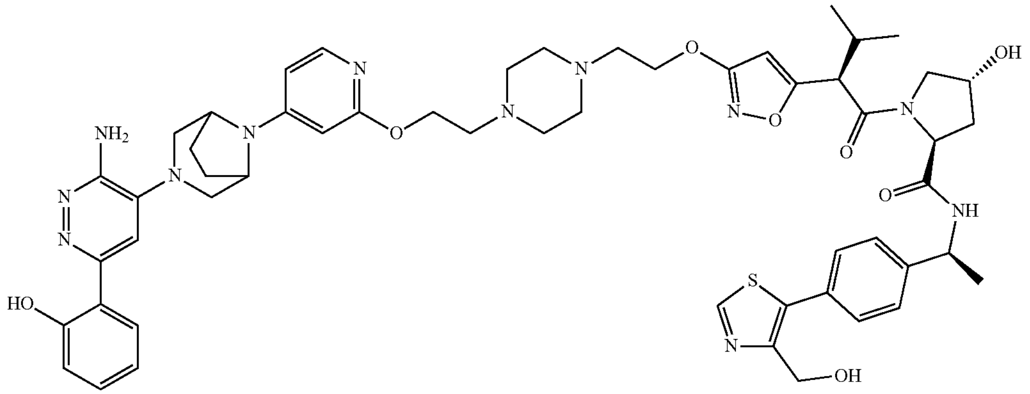 [SMILES: CC(C)[C@@H](C(=O)N1C[C@H](O)C[C@H]1C(=O)N[C@@H](C)c1ccc(-c2scnc2CO)cc1)c1cc(OCCN2CCN(CCOc3cc(N4C5CCC4CN(c4cc(-c6ccccc6O)nnc4N)C5)ccn3)CC2)no1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-(hydroxymethyl)thiazol-5-yl)phenyl)ethyl)pyrrolidine-2-carboxamide |
| 123 | 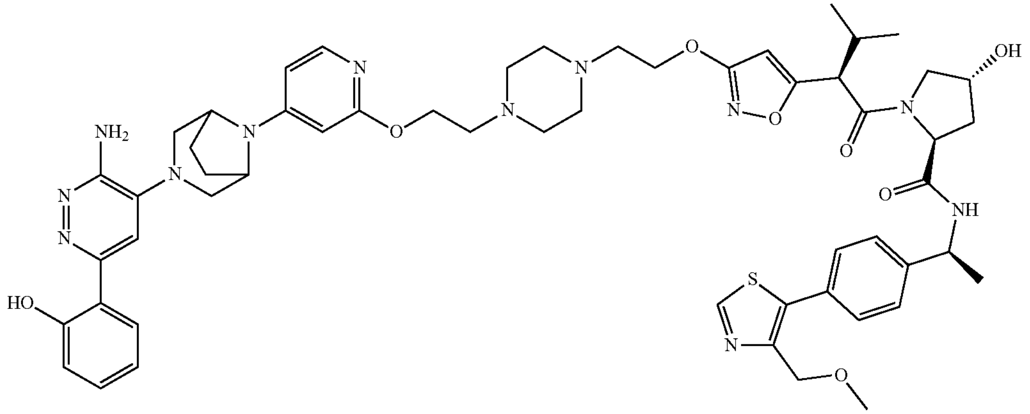 [SMILES: COCc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-(methoxymethyl)thiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 124 | 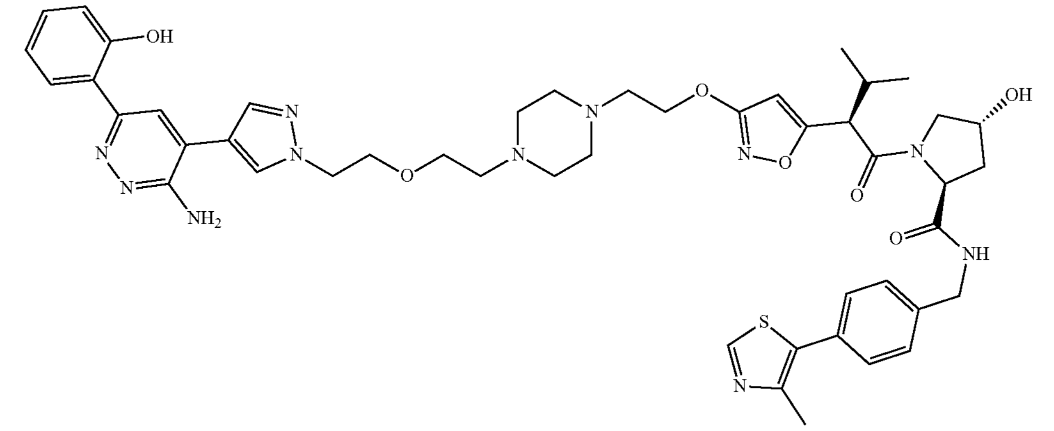 [SMILES: Cc1ncsc1-c1ccc(CNC(=O)[C@@H]2C[C@@H](O)CN2C(=O)[C@@H](c2cc(OCCN3CCN(CCOCCn4cc(-c5cc(-c6ccccc6O)nnc5N)cn4)CC3)no2)C(C)C)cc1] | (2S,4R)-1-((R)-2-(3-(2-(4-(2-(2-(4-(3-amino-6-(2-hydroxyphenyl)pyridazin-4-yl)-1H-pyrazol-1-yl)ethoxy)ethyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide |
| 125 | 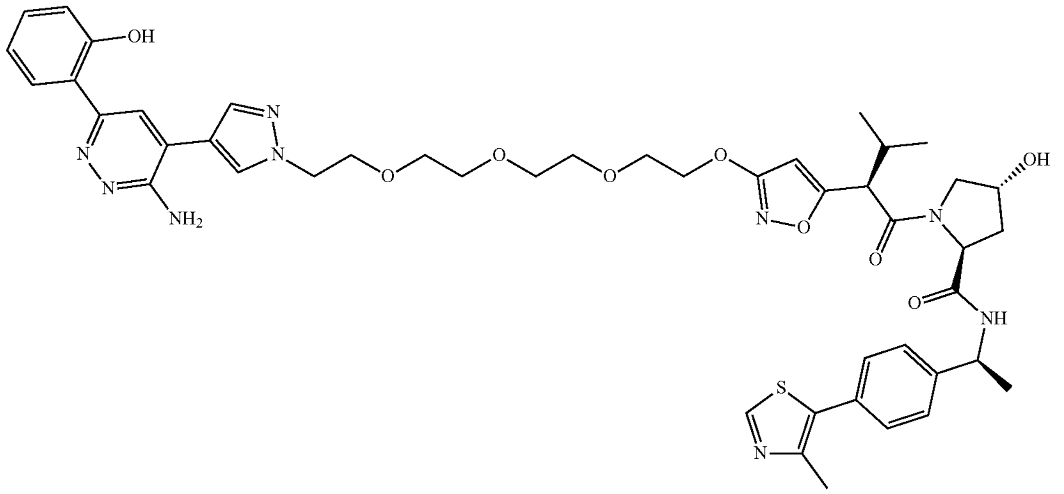 [SMILES: Cc1ncsc1-c1ccc([C@H](C)NC(=O)[C@@H]2C[C@@H](O)CN2C(=O)[C@@H](c2cc(OCCOCCOCCOCCn3cc(-c4cc(-c5ccccc5O)nnc4N)cn3)no2)C(C)C)cc1] | (2S,4R)-1-((R)-2-(3-(2-(2-(2-(2-(4-(3-amino-6-(2-hydroxyphenyl)pyridazin-4-yl)-1H-pyrazol-1-yl)ethoxy)ethoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 126 | 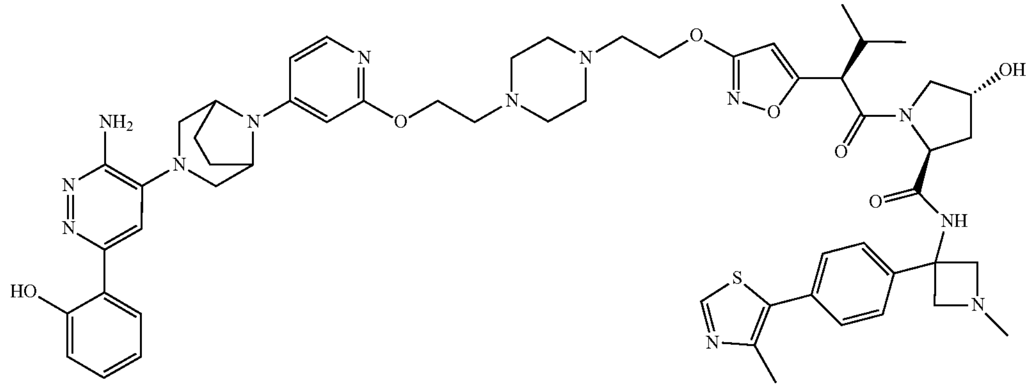 [SMILES: Cc1ncsc1-c1ccc(C2(NC(=O)[C@@H]3C[C@@H](O)CN3C(=O)[C@@H](c3cc(OCCN4CCN(CCOc5cc(N6C7CCC6CN(c6cc(-c8ccccc8O)nnc6N)C7)ccn5)CC4)no3)C(C)C)CN(C)C2)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-(1-methyl-3-(4-(4-methylthiazol-5-yl)phenyl)azetidin-3-yl)pyrrolidine-2-carboxamide |
| 127 | 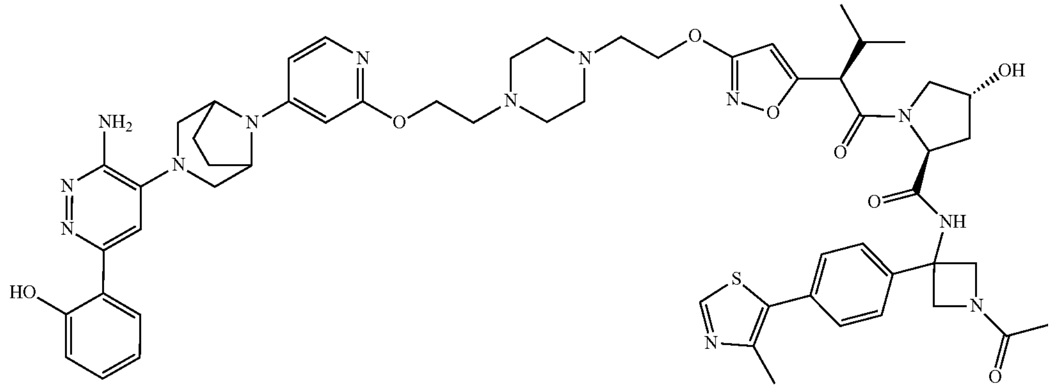 [SMILES: CC(=O)N1CC(NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)(c2ccc(-c3scnc3C)cc2)C1] | (2S,4R)-N-(1-acetyl-3-(4-(4-methylthiazol-5-yl)phenyl)azetidin-3-yl)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |

TABLE 1A-continued

| Exemplary bifunctional degradation compounds of the present disclosure | | |
|---|---|---|
| Ex. # | Structure | Compound Name |
| 128 | 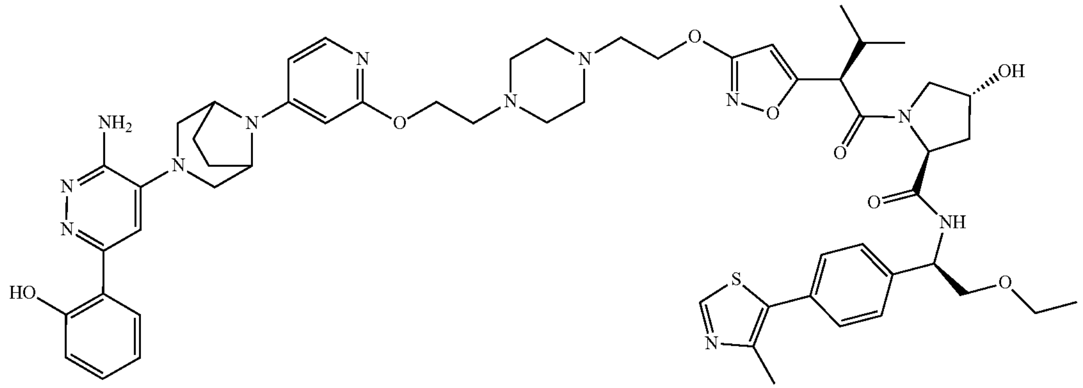 [SMILES: CCOC[C@H](NC(=O)[C@@H]1C[C@@H](O)CN1C(=O)[C@@H](c1cc(OCCN2CCN(CCOc3cc(N4C5CCC4CN(c4cc(-c6ccccc6O)nnc4N)C5)ccn3)CC2)no1)C(C)C)c1ccc(-c2scnc2C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-ethoxy-1-(4-(4-methylthiazol-5-yl)phenyl)ethyl)-4-hydroxypyrrolidine-2-carboxamide |
| 129 | 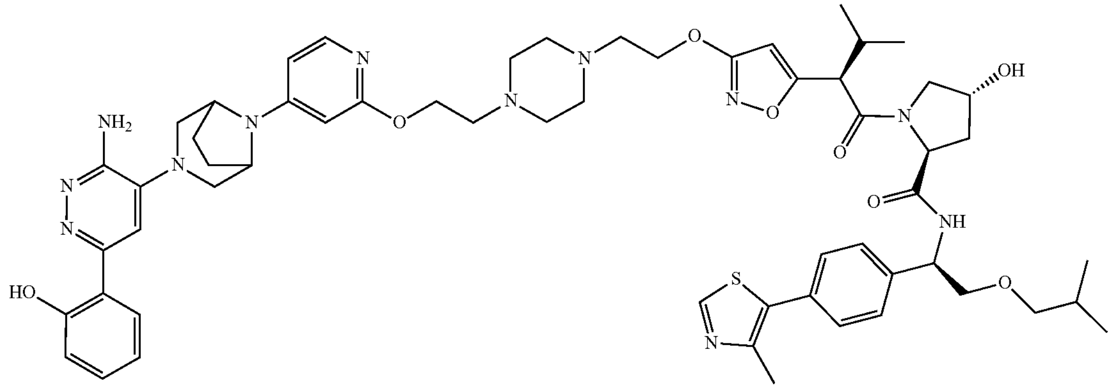 [SMILES: Cc1ncsc1-c1ccc([C@H](COCC(C)C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-2-isobutoxy-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 130 | 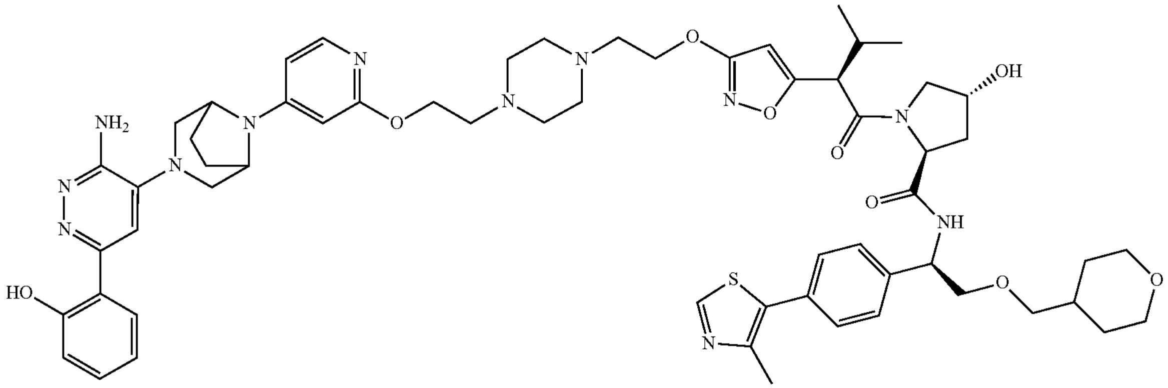 [SMILES: Cc1ncsc1-c1ccc([C@H](COCC2CCOCC2)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-1-(4-(4-methylthiazol-5-yl)phenyl)-2-((tetrahydro-2H-pyran-4-yl)methoxy)ethyl)pyrrolidine-2-carboxamide |
| 131 | 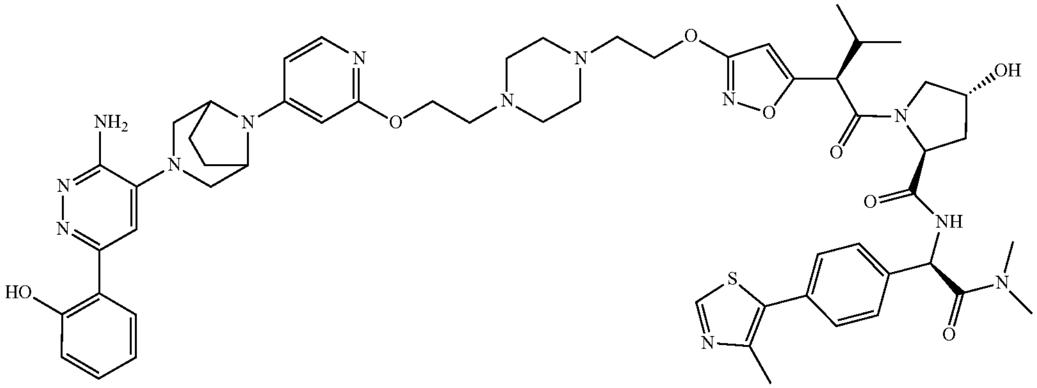 [SMILES: Cc1ncsc1-c1ccc([C@@H](NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)C(=O)N(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-(dimethylamino)-1-(4-(4-methylthiazol-5-yl)phenyl)-2-oxoethyl)-4-hydroxypyrrolidine-2-carboxamide |

TABLE 1A-continued

| Exemplary bifunctional degradation compounds of the present disclosure | | |
|---|---|---|
| Ex. # | Structure | Compound Name |
| 132 | 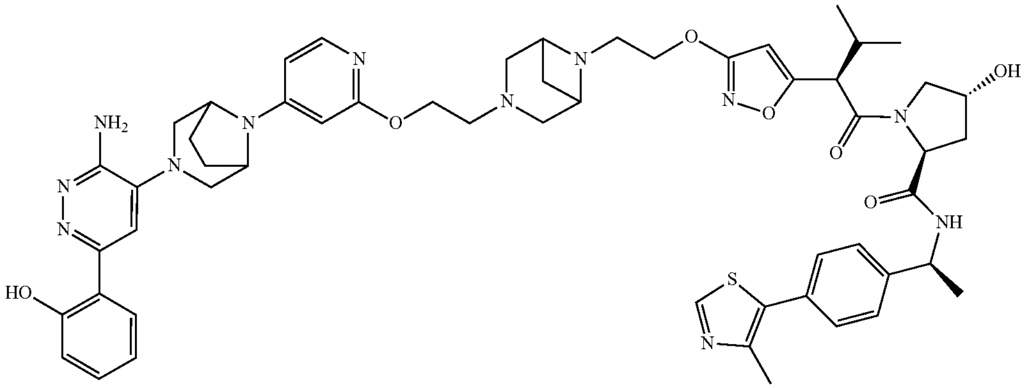 [SMILES: Cc1ncsc1-c1ccc([C@H](C)NC(=O)[C@@H]2C[C@@H](O)CN2C(=O)[C@@H](c2cc(OCCN3C4CC3CN(CCOc3cc(N5C6CCC5CN(c5cc(-c7ccccc7O)nnc5N)C6)ccn3)C4)no2)C(C)C)cc1] | (2S,4R)-1-((2R)-2-(3-(2-(3-(2-((4-(3-(3-amino-6-(2-hydroxyphenyl)pyridazin-4-yl)-3,8-diazabicyclo[3.2.1]octan-8-yl)pyridin-2-yl)oxy)ethyl)-3,6-diazabicyclo[3.1.1]heptan-6-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 133 | 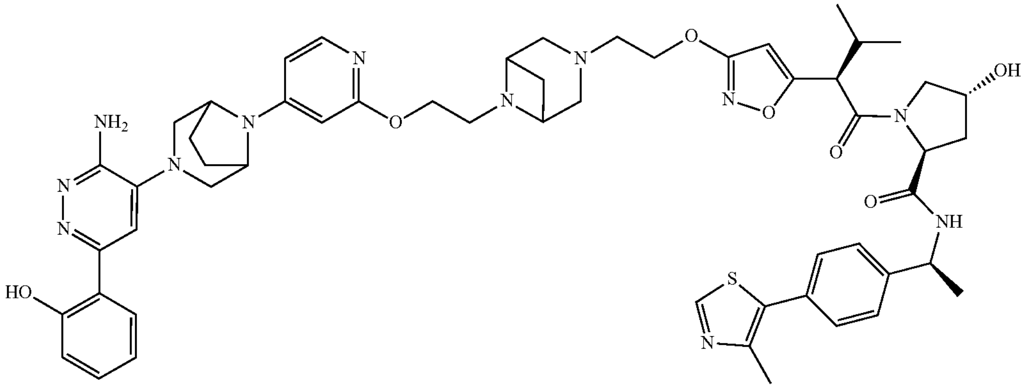 [SMILES: Cc1ncsc1-c1ccc([C@H](C)NC(=O)[C@@H]2C[C@@H](O)CN2C(=O)[C@@H](c2cc(OCCN3CC4CC(C3)N4CCOc3cc(N4C5CCC4CN(c4cc(-c6ccccc6O)nnc4N)C5)ccn3)no2)C(C)C)cc1] | (2S,4R)-1-((2R)-2-(3-(2-(6-(2-((4-(3-(3-amino-6-(2-hydroxyphenyl)pyridazin-4-yl)-3,8-diazabicyclo[3.2.1]octan-8-yl)pyridin-2-yl)oxy)ethyl)-3,6-diazabicyclo[3.1.1]heptan-3-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 134 | 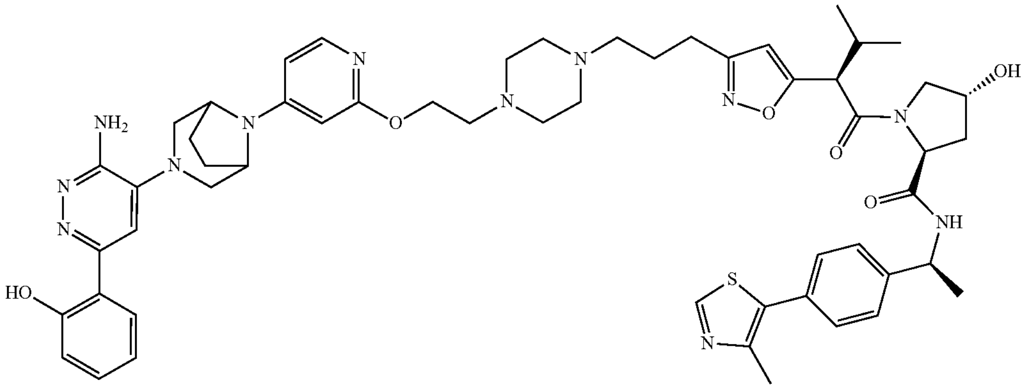 [SMILES: Cc1ncsc1-c1ccc([C@H](C)NC(=O)[C@@H]2C[C@@H](O)CN2C(=O)[C@@H](c2cc(CCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(3-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)propyl)isoxazol-5-yl)-3-methylbutanoyl)-4-hydroxy-N-((S)-1-(4-(4-methylthiazol-5-yl)phenyl)ethyl)pyrrolidine-2-carboxamide |
| 135 | 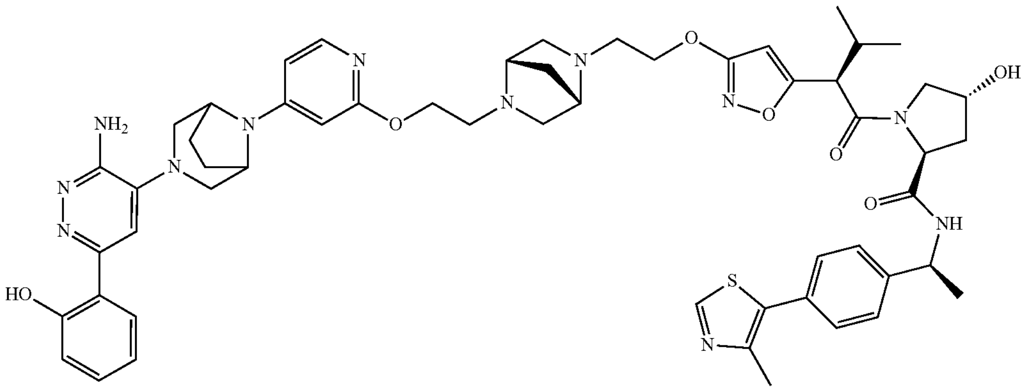 [SMILES: Cc1ncsc1-c1ccc([C@H](C)NC(=O)[C@@H]2C[C@@H](O)CN2C(=O)[C@@H](c2cc(OCCN3C[C@@H]4C[C@H]3CN4CCOc3cc(N4C5CCC4CN(c4cc(-c6ccccc6O)nnc4N)C5)ccn3)no2)C(C)C)cc1] | (2S,4R)-1-((2R)-2-(3-(2-((1S,4S)-5-(2-((4-(3-(3-amino-6-(2-hydroxyphenyl)pyridazin-4-yl)-3,8-diazabicyclo[3.2.1]octan-8-yl)pyridin-2-yl)oxy)ethyl)-2,5-diazabicyclo[2.2.1]heptan-2-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 136 | 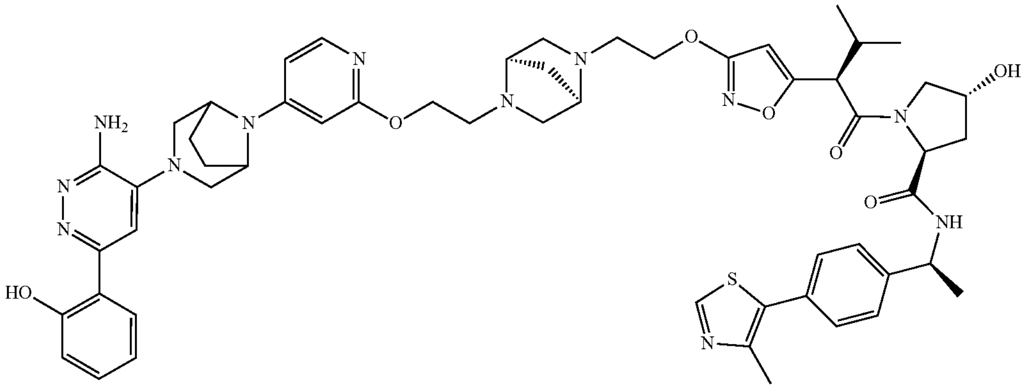 [SMILES: Cc1ncsc1-c1ccc([C@H](C)NC(=O)[C@@H]2C[C@@H](O)CN2C(=O)[C@@H](c2cc(OCCN3C[C@H]4C[C@@H]3CN4CCOc3cc(N4C5CCC4CN(c4cc(-c6ccccc6O)nnc4N)C5)ccn3)no2)C(C)C)cc1] | (2S,4R)-1-((2R)-2-(3-(2-((1R,4R)-5-(2-((4-(3-(3-amino-6-(2-hydroxyphenyl)pyridazin-4-yl)-3,8-diazabicyclo[3.2.1]octan-8-yl)pyridin-2-yl)oxy)ethyl)-2,5-diazabicyclo[2.2.1]heptan-2-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 137 | 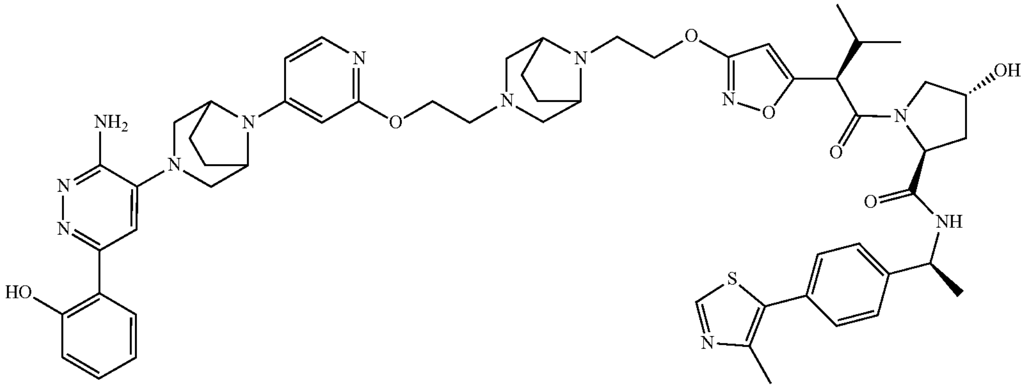 [SMILES: Cc1ncsc1-c1ccc([C@H](C)NC(=O)[C@@H]2C[C@@H](O)CN2C(=O)[C@@H](c2cc(OCCN3C4CCC3CN(CCOc3cc(N5C6CCC5CN(c5cc(-c7ccccc7O)nnc5N)C6)ccn3)C4)no2)C(C)C)cc1] | (2S,4R)-1-((2R)-2-(3-(2-(3-(2-((4-(3-(3-amino-6-(2-hydroxyphenyl)pyridazin-4-yl)-3,8-diazabicyclo[3.2.1]octan-8-yl)pyridin-2-yl)oxy)ethyl)-3,8-diazabicyclo[3.2.1]octan-8-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 138 | 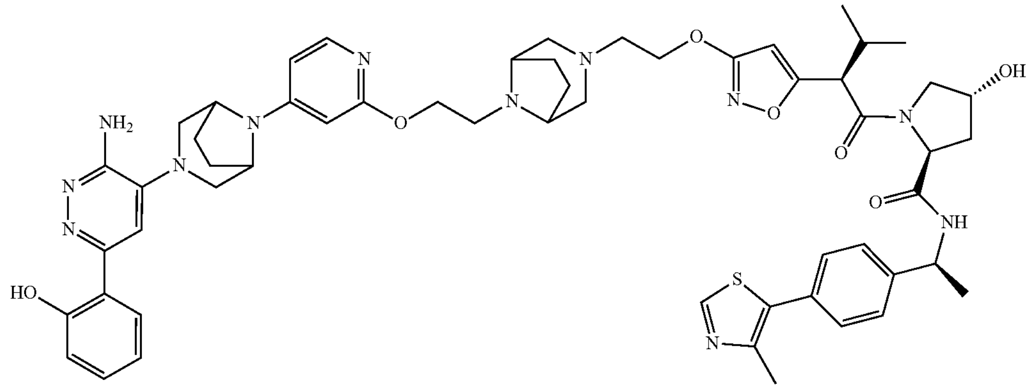 [SMILES: Cc1ncsc1-c1ccc([C@H](C)NC(=O)[C@@H]2C[C@@H](O)CN2C(=O)[C@@H](c2cc(OCCN3CC4CCC(C3)N4CCOc3cc(N4C5CCC4CN(c4cc(-c6ccccc6O)nnc4N)C5)ccn3)no2)C(C)C)cc1] | (2S,4R)-1-((2R)-2-(3-(2-(8-(2-((4-(3-(3-amino-6-(2-hydroxyphenyl)pyridazin-4-yl)-3,8-diazabicyclo[3.2.1]octan-8-yl)pyridin-2-yl)oxy)ethyl)-3,8-diazabicyclo[3.2.1]octan-3-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 139 | 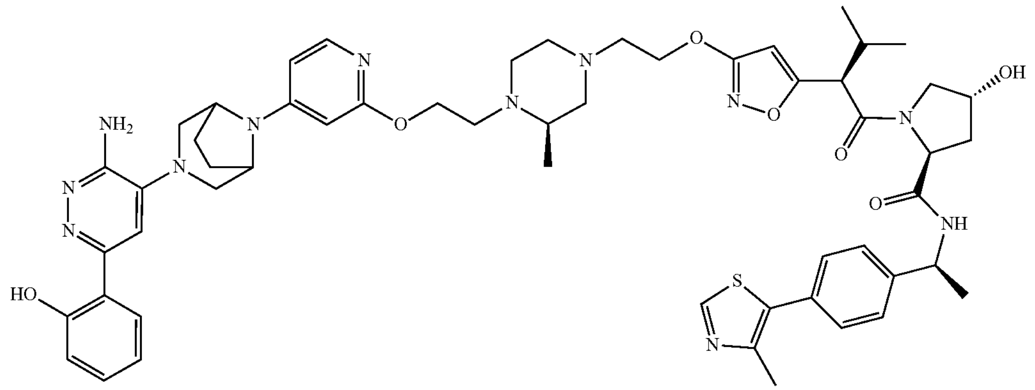 [SMILES: Cc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)[C@H](C)C3)no2)C(C)C)cc1] | (2S,4R)-1-((2R)-2-(3-(2-((3R)-4-(2-((4-(3-(3-amino-6-(2-hydroxyphenyl)pyridazin-4-yl)-3,8-diazabicyclo[3.2.1]octan-8-yl)pyridin-2-yl)oxy)ethyl)-3-methylpiperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 140 | 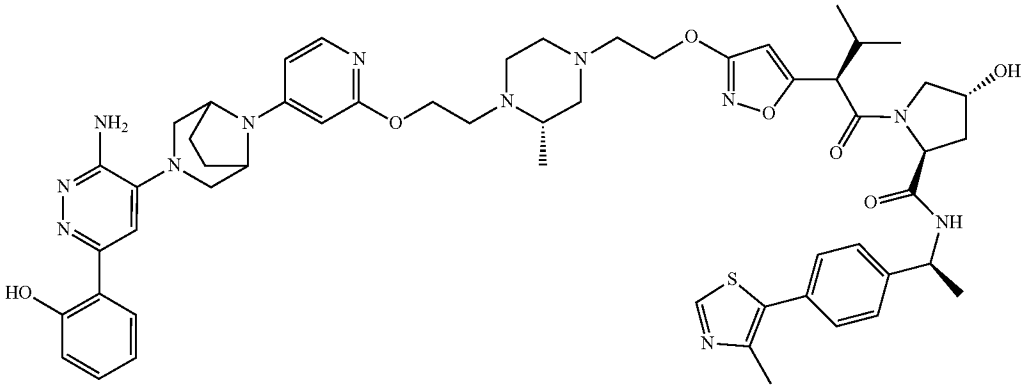 [SMILES: Cc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)[C@@H](C)C3)no2)C(C)C)cc1] | (2S,4R)-1-((2R)-2-(3-(2-((3S)-4-(2-((4-(3-(3-amino-6-(2-hydroxyphenyl)pyridazin-4-yl)-3,8-diazabicyclo[3.2.1]octan-8-yl)pyridin-2-yl)oxy)ethyl)-3-methylpiperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 141 | 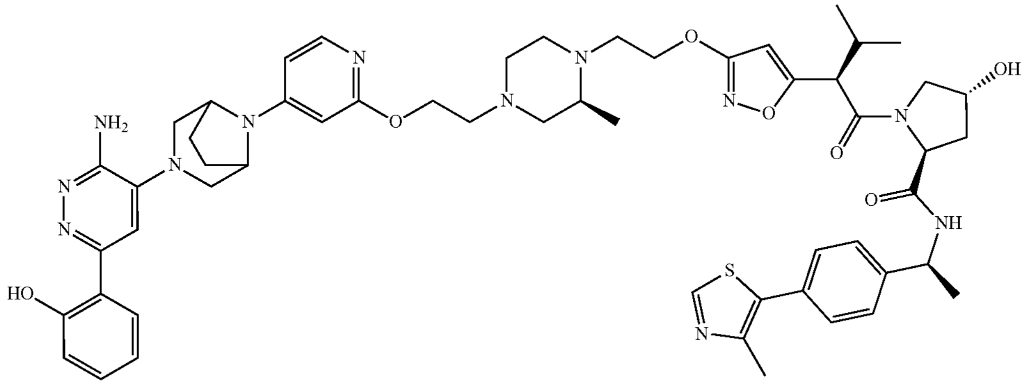 [SMILES: Cc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)C[C@@H]3C)no2)C(C)C)cc1] | (2S,4R)-1-((2R)-2-(3-(2-((2S)-4-(2-((4-(3-(3-amino-6-(2-hydroxyphenyl)pyridazin-4-yl)-3,8-diazabicyclo[3.2.1]octan-8-yl)pyridin-2-yl)oxy)ethyl)-2-methylpiperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 142 | 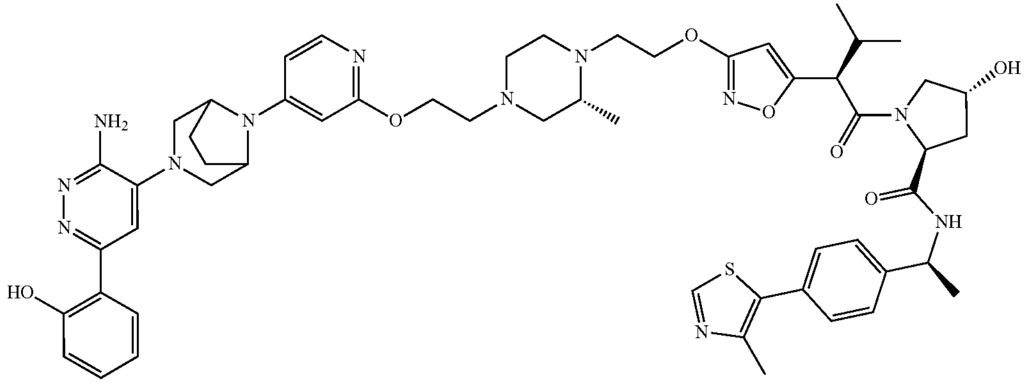 [SMILES: Cc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)C[C@H]3C)no2)C(C)C)cc1] | (2S,4R)-1-((2R)-2-(3-(2-((2R)-4-(2-((4-(3-(3-amino-6-(2-hydroxyphenyl)pyridazin-4-yl)-3,8-diazabicyclo[3.2.1]octan-8-yl)pyridin-2-yl)oxy)ethyl)-2-methylpiperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 143 | 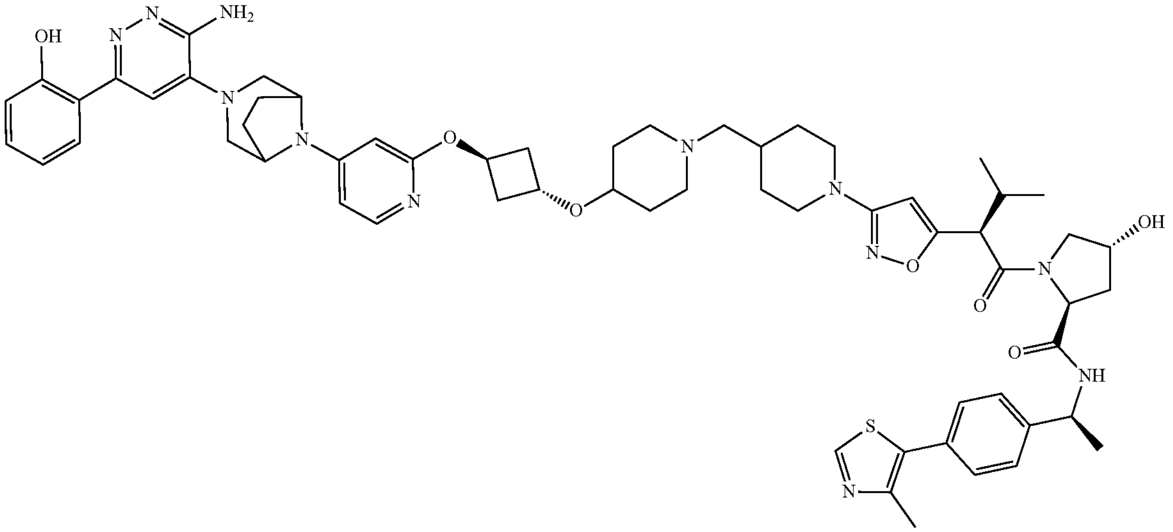 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 144 | 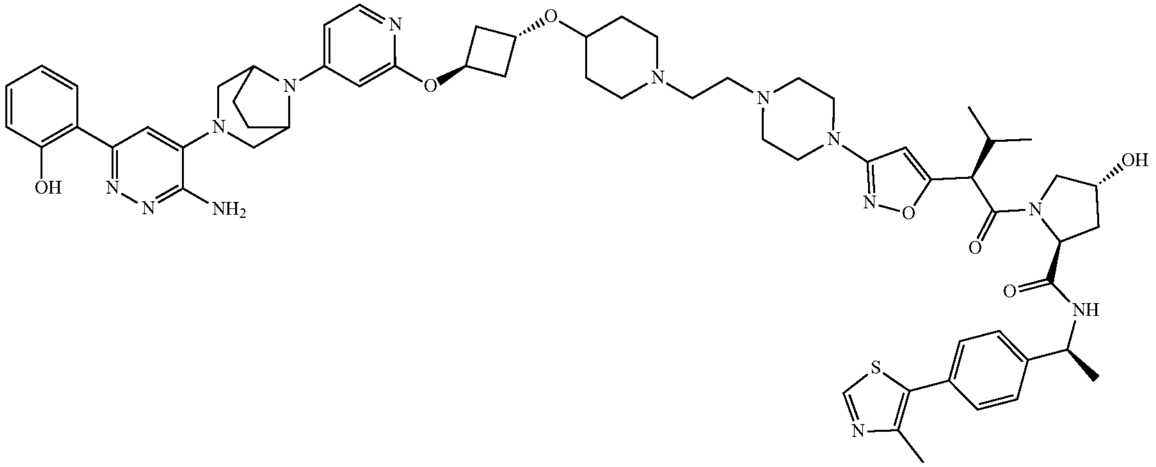 [SMILES: Cc1ncsc1-c1ccc([C@H](C)NC(=O)[C@@H]2C[C@@H](O)CN2C(=O)[C@@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 145 | 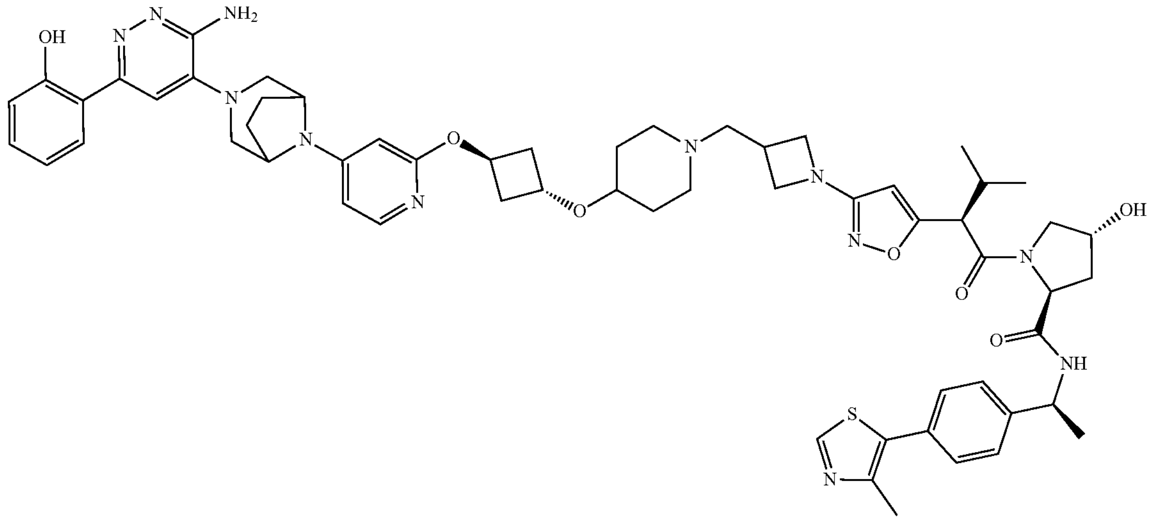 [SMILES: Cc1ncsc1-c1ccc([C@H](C)NC(=O)[C@@H]2C[C@@H](O)CN2C(=O)[C@@H](c2cc(N3CC(CN4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2R)-2-(3-(3-((4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)azetidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 146 | 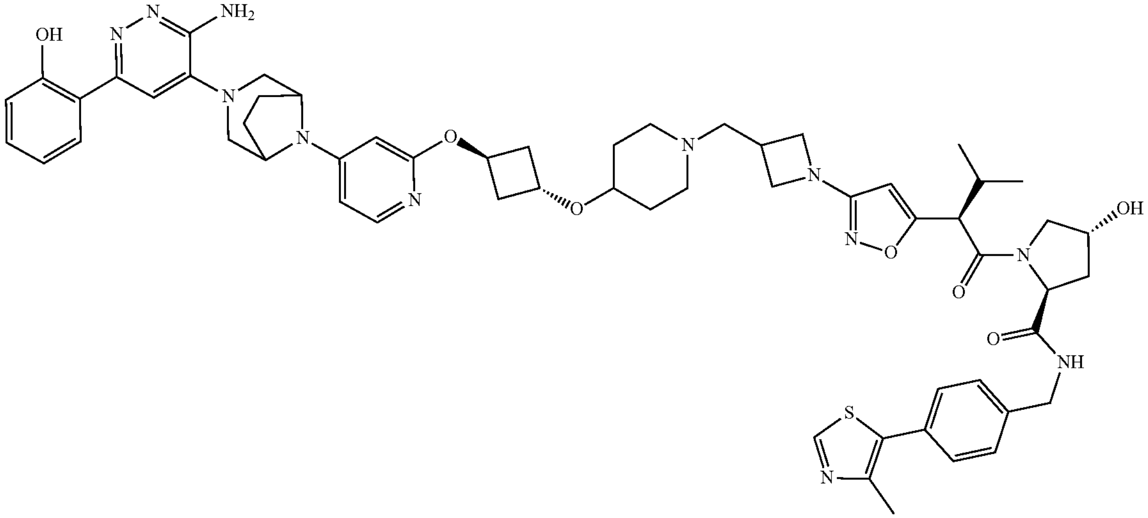 [SMILES: Cc1ncsc1-c1ccc(CNC(=O)[C@@H]2C[C@@H](O)CN2C(=O)[C@@H](c2cc(N3CC(CN4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-(4-(4-methylthiazol-5-yl)benzyl)pyrrolidine-2-carboxamide |
| 147 | 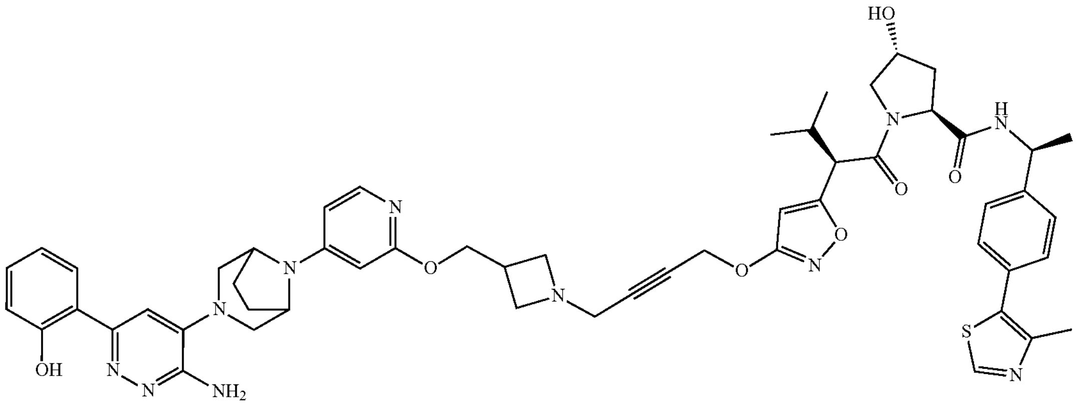 [SMILES: Cc1ncsc1-c1ccc([C@H](C)NC(=O)[C@@H]2C[C@@H](O)CN2C(=O)[C@@H](c2cc(OCC#CCN3CC(COc4cc(N5C6CCC5CN(c5cc(-c7ccccc7O)nnc5N)C6)ccn4)C3)no2)C(C)C)cc1] | (2S,4R)-1-((2R)-2-(3-((4-(3-(((4-(3-(3-amino-6-(2-hydroxyphenyl)pyridazin-4-yl)-3,8-diazabicyclo[3.2.1]octan-8-yl)pyridin-2-yl)oxy)methyl)azetidin-1-yl)but-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 148 | 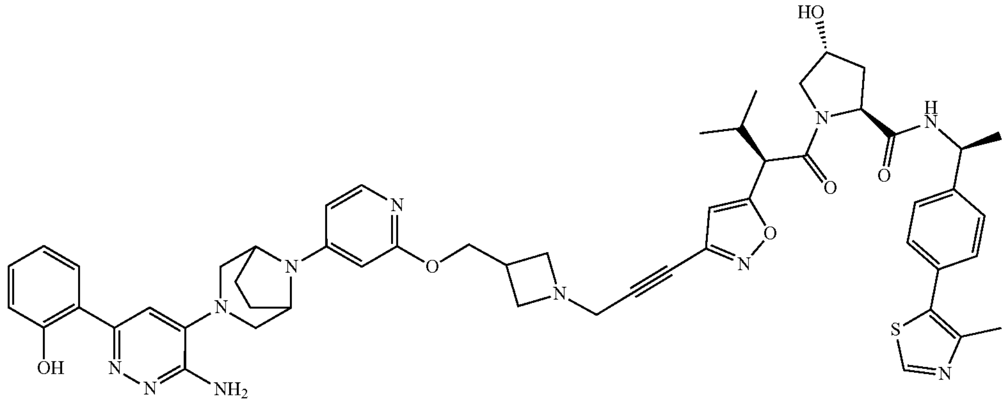 [SMILES: Cc1ncsc1-c1ccc([C@H](C)NC(=O)[C@@H]2C[C@@H](O)CN2C(=O)[C@@H](c2cc(C#CCN3CC(COc4cc(N5C6CCC5CN(c5cc(-c7ccccc7O)nnc5N)C6)ccn4)C3)no2)C(C)C)cc1] | (2S,4R)-1-((2R)-2-(3-(3-(3-(((4-(3-(3-amino-6-(2-hydroxyphenyl)pyridazin-4-yl)-3,8-diazabicyclo[3.2.1]octan-8-yl)pyridin-2-yl)oxy)methyl)azetidin-1-yl)prop-1-yn-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 149 | 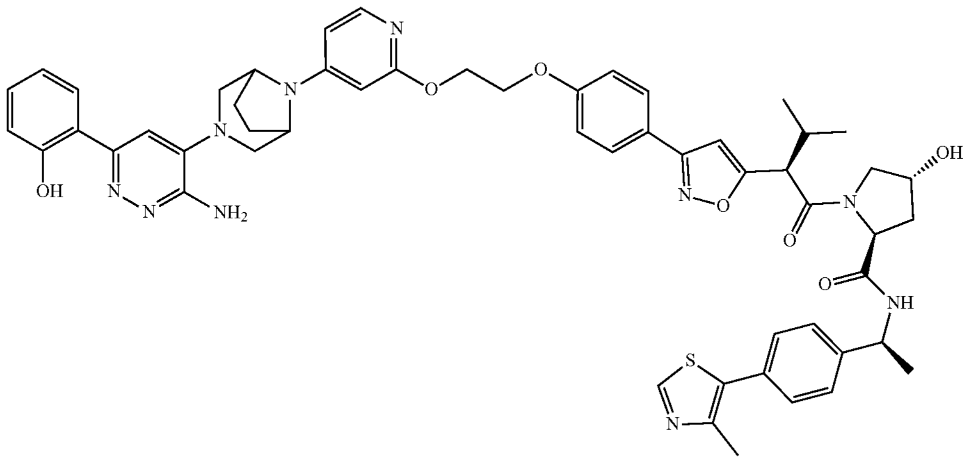 [SMILES: Cc1ncsc1-c1ccc([C@H](C)NC(=O)[C@@H]2C[C@@H](O)CN2C(=O)[C@@H](c2cc(-c3ccc(OCCOc4cc(N5C6CCC5CN(c5cc(-c7ccccc7O)nnc5N)C6)ccn4)cc3)no2)C(C)C)cc1] | (2S,4R)-1-((2R)-2-(3-(4-(2-((4-(3-(3-amino-6-(2-hydroxyphenyl)pyridazin-4-yl)-3,8-diazabicyclo[3.2.1]octan-8-yl)pyridin-2-yl)oxy)ethoxy)phenyl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued
| Exemplary bifunctional degradation compounds of the present disclosure | | |
|---|---|---|
| Ex. # | Structure | Compound Name |
| 150 | 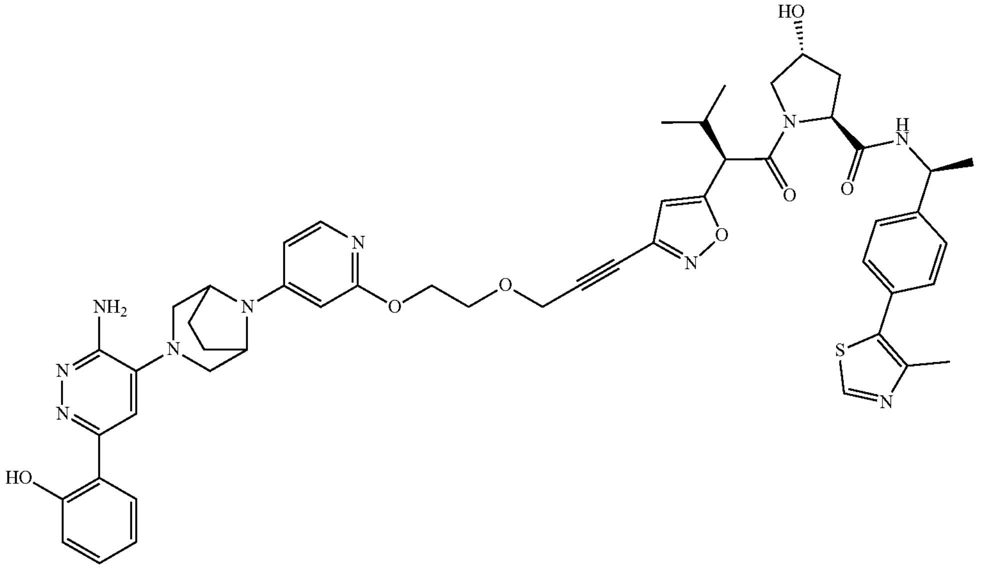 [SMILES: Cc1ncsc1-c1ccc([C@H](C)NC(=O)[C@@H]2C[C@@H](O)CN2C(=O)[C@@H](c2cc(C#CCOCCOc3cc(N4C5CCC4CN(c4cc(-c6ccccc6O)nnc4N)C5)ccn3)no2)C(C)C)cc1] | (2S,4R)-1-((2R)-2-(3-(3-(2-((4-(3-(3-amino-6-(2-hydroxyphenyl)pyridazin-4-yl)-3,8-diazabicyclo[3.2.1]octan-8-yl)pyridin-2-yl)oxy)ethoxy)prop-1-yn-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued
| Exemplary bifunctional degradation compounds of the present disclosure | | |
|---|---|---|
| Ex. # | Structure | Compound Name |
| 151 | 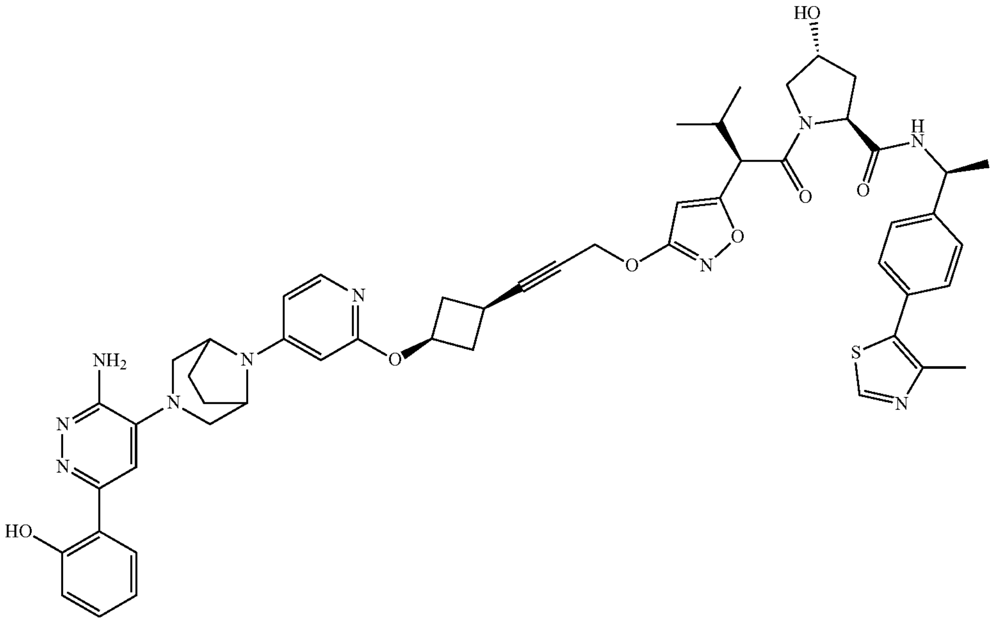 [SMILES: Cc1ncsc1-c1ccc([C@H](C)NC(=O)[C@@H]2C[C@@H](O)CN2C(=O)[C@@H](c2cc(OCC#C[C@H]3C[C@@H](Oc4cc(N5C6CCC5CN(c5cc(-c7ccccc7O)nnc5N)C6)ccn4)C3)no2)C(C)C)cc1] | (2S,4R)-1-((2R)-2-(3-((3-((1s,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 152 | 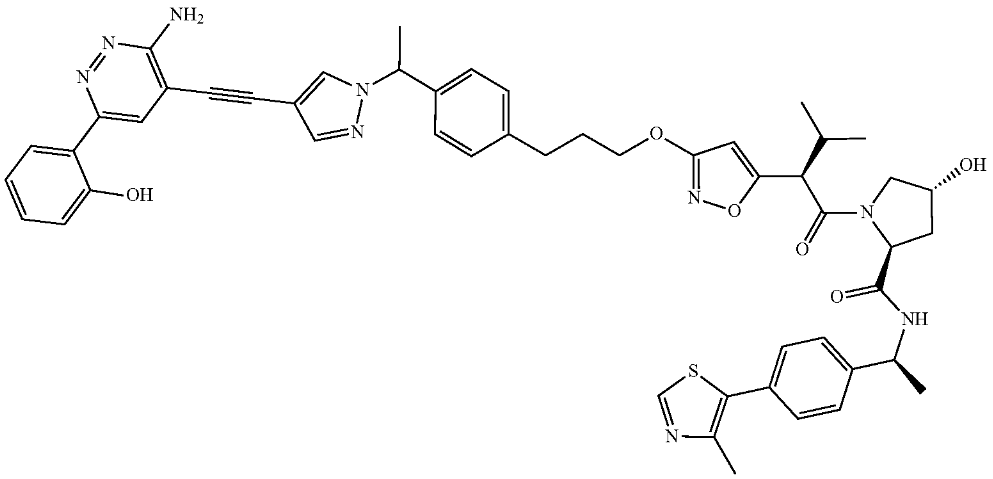 [SMILES: Cc1ncsc1-c1ccc([C@H](C)NC(=O)[C@@H]2C[C@@H](O)CN2C(=O)[C@@H](c2cc(OCCCc3ccc(C(C)n4cc(C#Cc5cc(-c6ccccc6O)nnc5N)cn4)cc3)no2)C(C)C)cc1] | (2S,4R)-1-((2R)-2-(3-(3-(4-(1-(4-((3-amino-6-(2-hydroxyphenyl)pyridazin-4-yl)ethynyl)-1H-pyrazol-1-yl)ethyl)phenyl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 153 | 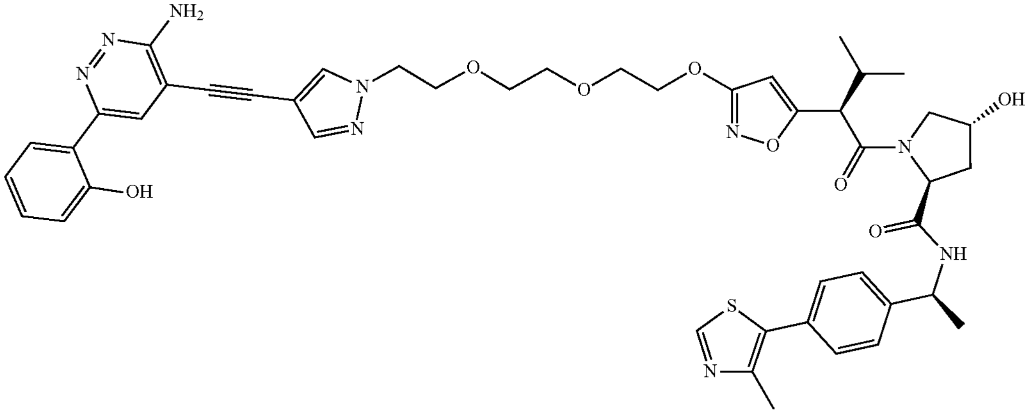 [SMILES: Cc1ncsc1-c1ccc([C@H](C)NC(=O)[C@@H]2C[C@@H](O)CN2C(=O)[C@@H](c2cc(OCCOCCOCCn3cc(C#Cc4cc(-c5ccccc5O)nnc4N)cn3)no2)C(C)C)cc1] | (2S,4R)-1-((R)-2-(3-(2-(2-(2-(4-((3-amino-6-(2-hydroxyphenyl)pyridazin-4-yl)ethynyl)-1H-pyrazol-1-yl)ethoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1A-continued

| Exemplary bifunctional degradation compounds of the present disclosure | | |
|---|---|---|
| Ex. # | Structure | Compound Name |
| 154 | 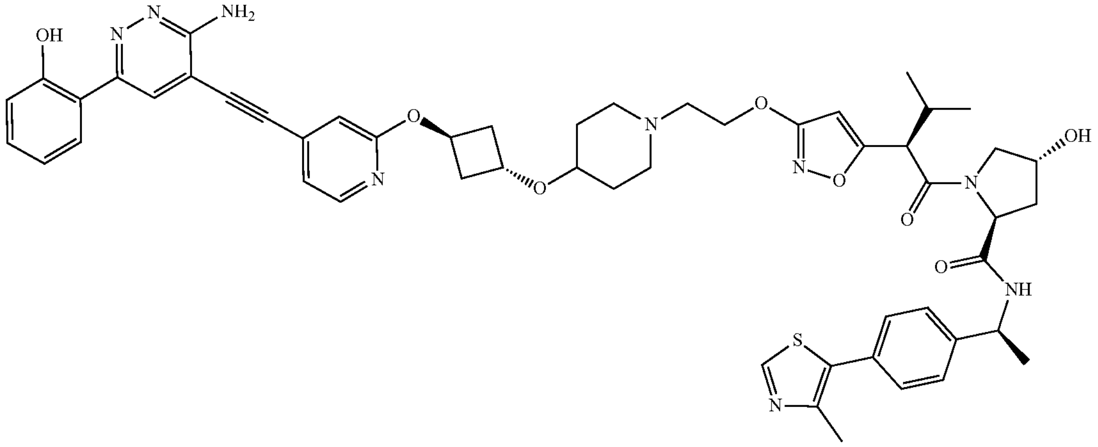 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(C#Cc6cc(-c7ccccc7O)nnc6N)ccn5)C4)CC3)no2)C(C)C)cc1] | (2S,4R)-1-((R)-2-(3-(2-(4-((1r,3R)-3-((4-((3-amino-6-(2-hydroxyphenyl)pyridazin-4-yl)ethynyl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 155 | 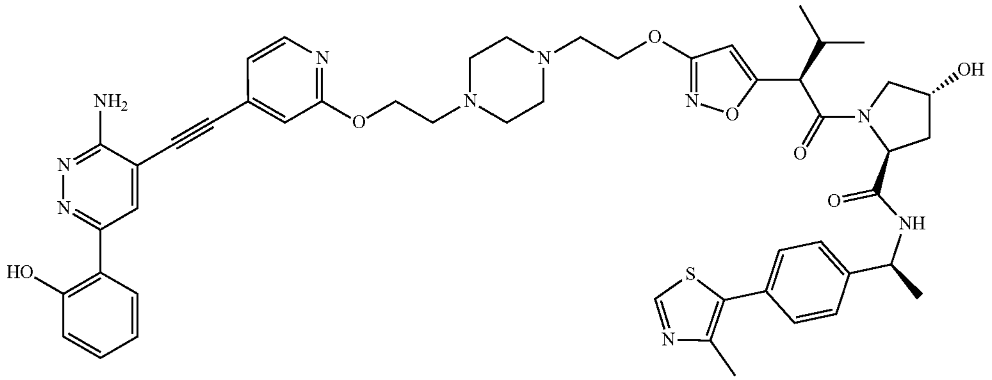 [SMILES: Cc1ncsc1-c1ccc([C@H](C)NC(=O)[C@@H]2C[C@@H](O)CN2C(=O)[C@@H](c2cc(OCCN3CCN(CCOc4cc(C#Cc5cc(-c6ccccc6O)nnc5N)ccn4)CC3)no2)C(C)C)cc1] | (2S,4R)-1-((R)-2-(3-(2-(4-(2-((4-((3-amino-6-(2-hydroxyphenyl)pyridazin-4-yl)ethynyl)pyridin-2-yl)oxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B

]Exemplary bifunctional degradation compounds of the present disclosure

| Ex. # | Structure | Compound Name |
|---|---|---|
| 156 | 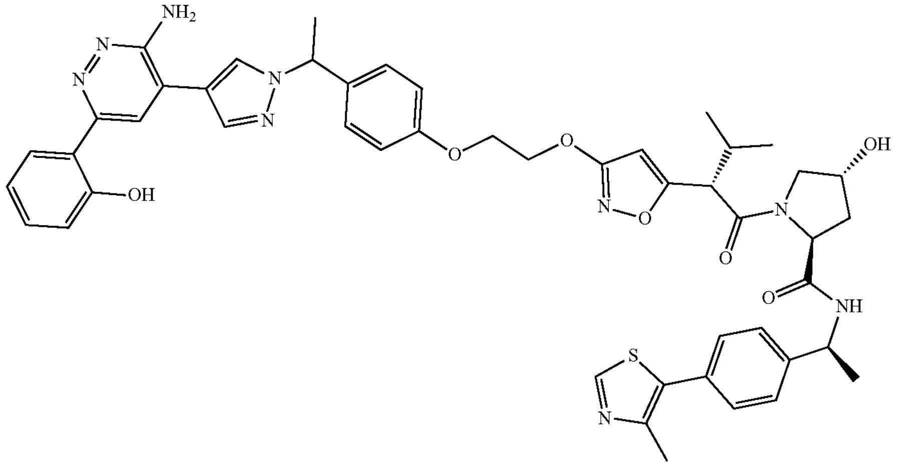 [SMILES: Cc1ncsc1-c1ccc([C@H](C)NC(=O)[C@@H]2C[C@@H](O)CN2C(=O)[C@H](c2cc(OCCOc3ccc(C(C)n4cc(-c5cc(-c6ccccc6O)nnc5N)cn4)cc3)no2)C(C)C)cc1] | (2S,4R)-1-((2S)-2-(3-(2-(4-(1-(4-(3-amino-6-(2-hydroxyphenyl)pyridazin-4-yl)-1H-pyrazol-1-yl)ethyl)phenoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 157 | 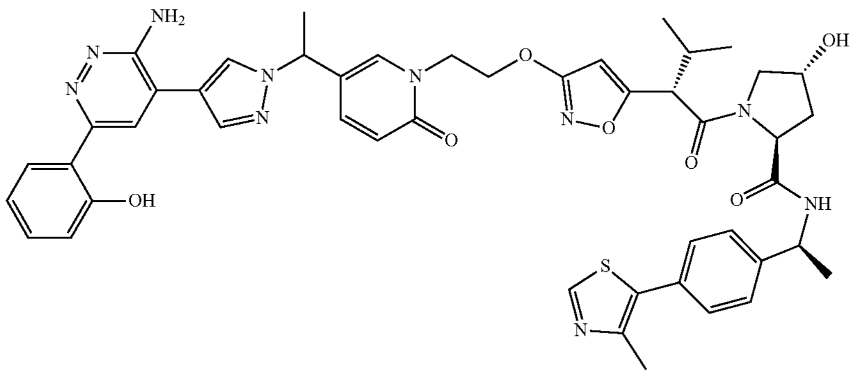 [SMILES: Cc1ncsc1-c1ccc([C@H](C)NC(=O)[C@@H]2C[C@@H](O)CN2C(=O)[C@H](c2cc(OCCn3cc(C(C)n4cc(-c5cc(-c6ccccc6O)nnc5N)cn4)ccc3=O)no2)C(C)C)cc1] | (2S,4R)-1-((2S)-2-(3-(2-(5-(1-(4-(3-amino-6-(2-hydroxyphenyl)pyridazin-4-yl)-1H-pyrazol-1-yl)ethyl)-2-oxopyridin-1(2H)-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 158 | 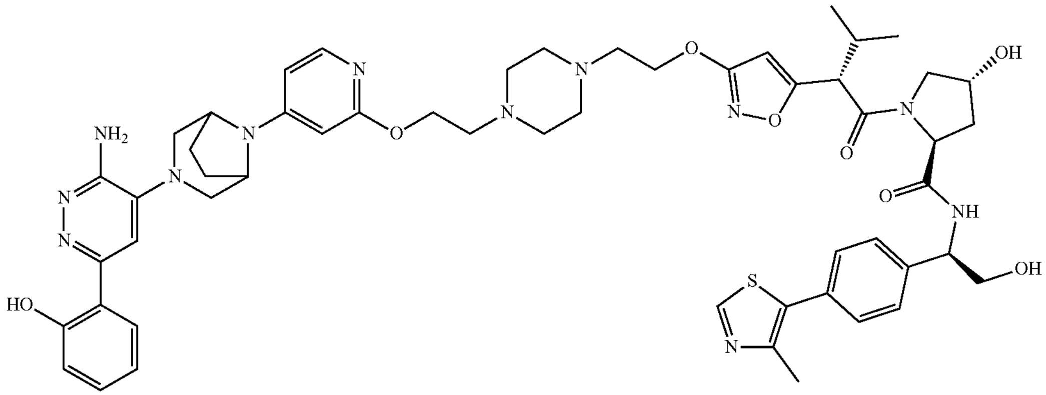 [SMILES: Cc1ncsc1-c1ccc([C@H](CO)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide |
| 159 | 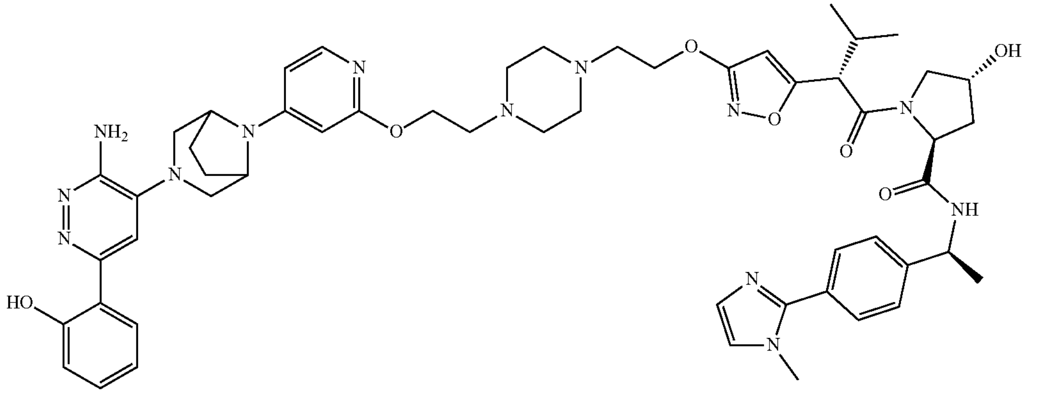 [SMILES: CC(C)[C@H](C(=O)N1C[C@H](O)C[C@H]1C(=O)N[C@@H](C)c1ccc(-c2nccn2C)cc1)c1cc(OCCN2CCN(CCOc3cc(N4C5CCC4CN(c4cc(-c6ccccc6O)nnc4N)C5)ccn3)CC2)no1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(1-methyl-1H-imidazol-2-yl)phenyl)ethyl)pyrrolidine-2-carboxamide |

TABLE 1B-continued

| Ex. # | Structure | Compound Name |
|---|---|---|
| | ]Exemplary bifunctional degradation compounds of the present disclosure | |
| 160 | 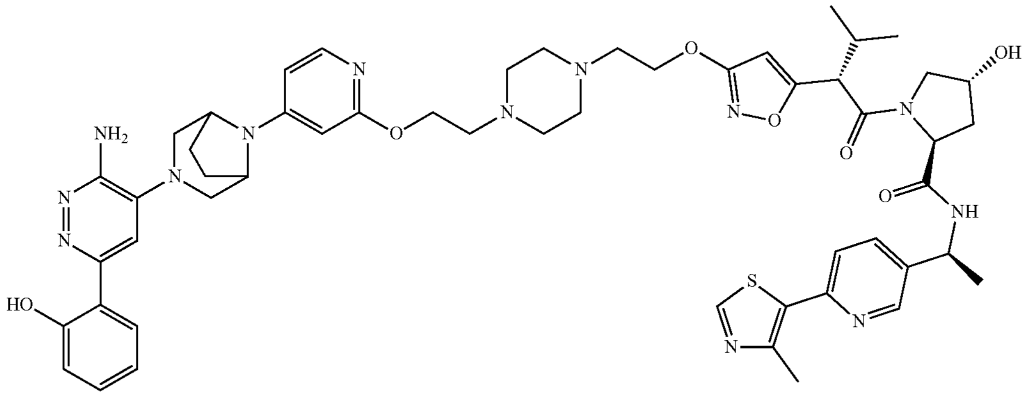 [SMILES: Cc1ncsc1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cn1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 161 | 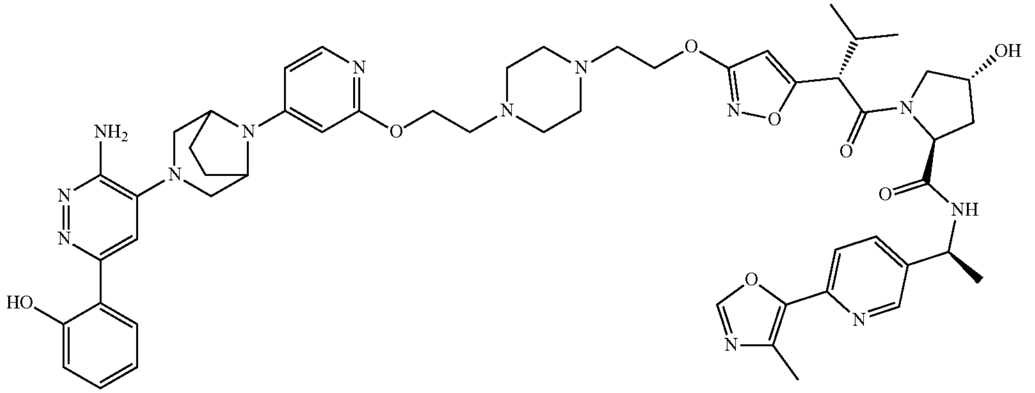 [SMILES: Cc1ncoc1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cn1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(6-(4-methyloxazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
|---|---|---|
| 162 | 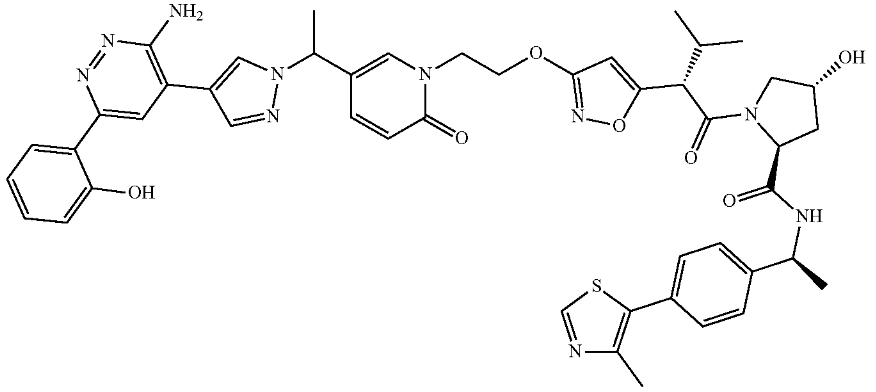 [SMILES: Cc1ncsc1-c1ccc([C@H](C)NC(=O)[C@@H]2C[C@@H](O)CN2C(=O)[C@H](c2cc(OCCn3cc(C(C)n4cc(-c5cc(-c6ccccc6O)nnc5N)cn4)ccc3=O)no2)C(C)C)cc1] | (2S,4R)-1-((2R)-2-(3-(2-(5-(1-(4-(3-amino-6-(2-hydroxyphenyl)pyridazin-4-yl)-1H-pyrazol-1-yl)ethyl)-2-oxopyridin-1(2H)-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 163 | 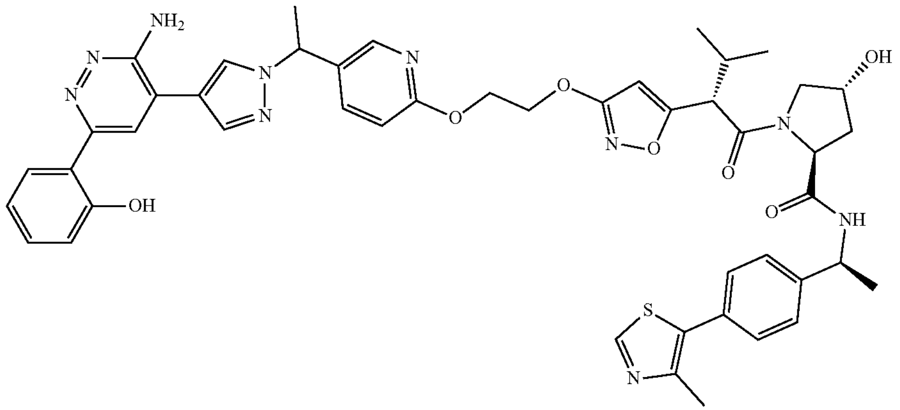 [SMILES: Cc1ncsc1-c1ccc([C@H](C)NC(=O)[C@@H]2C[C@@H](O)CN2C(=O)[C@H](c2cc(OCCOc3ccc(C(C)n4cc(-c5cc(-c6ccccc6O)nnc5N)cn4)cn3)no2)C(C)C)cc1] | (2S,4R)-1-((2S)-2-(3-(2-((5-(1-(4-(3-amino-6-(2-hydroxyphenyl)pyridazin-4-yl)-1H-pyrazol-1-yl)ethyl)pyridin-2-yl)oxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 164 | 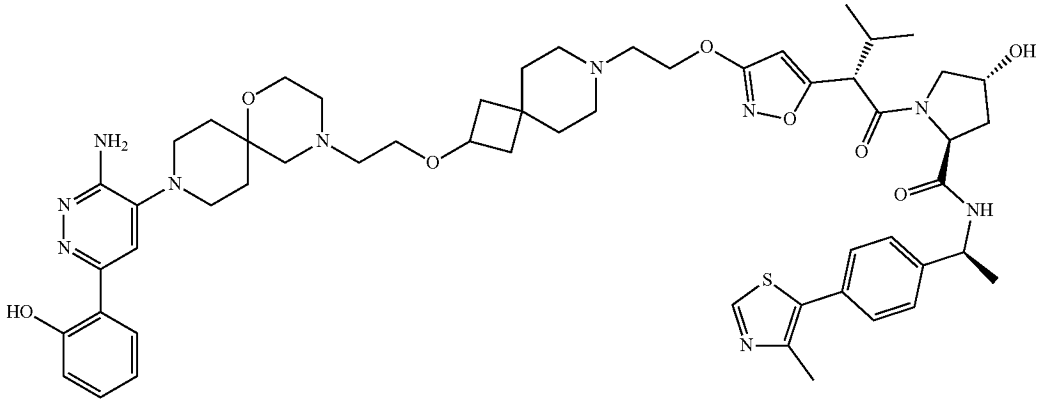 [SMILES: Cc1ncsc1-c1ccc([C@H](C)NC(=O)[C@@H]2C[C@@H](O)CN2C(=O)[C@H](c2cc(OCCN3CCC4(CC3)CC(OCCN3CCOC5(CCN(c6cc(-c7ccccc7O)nnc6N)CC5)C3)C4)no2)C(C)C)cc1] | (2S,4R)-1-((S)-2-(3-(2-(2-(2-(9-(3-amino-6-(2-hydroxyphenyl)pyridazin-4-yl)-1-oxa-4,9-diazaspiro[5.5]undecan-4-yl)ethoxy)-7-azaspiro[3.5]nonan-7-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 65 | 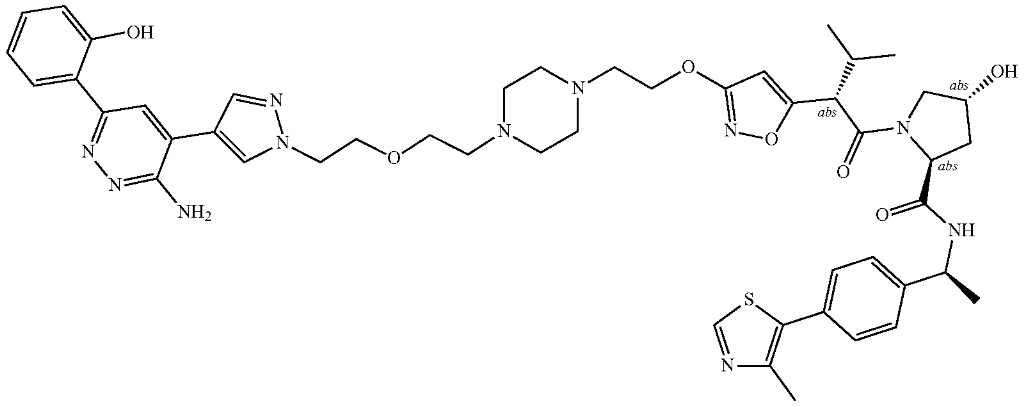 [SMILES: Cc1ncsc1-c1ccc([C@H](C)NC(=O)[C@@H]2C[C@@H](O)CN2C(=O)[C@H](c2cc(OCCN3CCN(CCOCCn4cc(-c5cc(-c6ccccc6O)nnc5N)cn4)CC3)no2)C(C)C)cc1] | (2S,4R)-1-((S)-2-(3-(2-(4-(2-(2-(4-(3-amino-6-(2-hydroxyphenyl)pyridazin-4-yl)-1H-pyrazol-1-yl)ethoxy)ethyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide |

TABLE 1B-continued

]Exemplary bifunctional degradation compounds of the present disclosure

| Ex. # | Structure | Compound Name |
| --- | --- | --- |
| 166 | 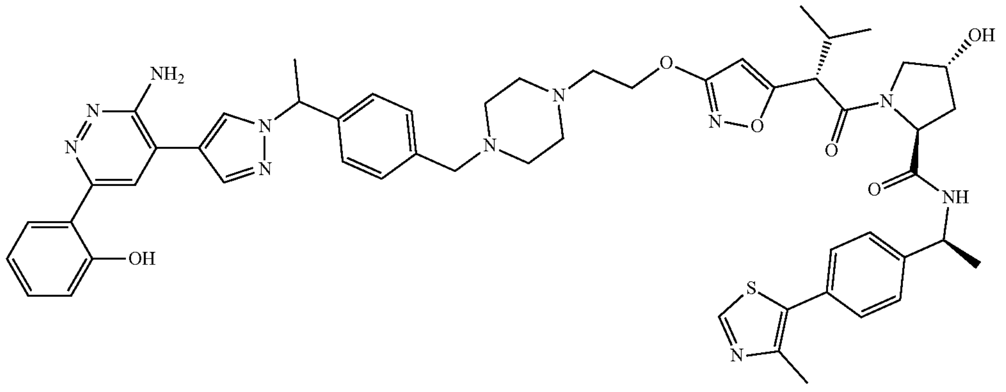 [SMILES: Cc1ncsc1-c1ccc([C@H](C)NC(=O)[C@@H]2C[C@@H](O)CN2C(=O)[C@H](c2cc(OCCN3CCN(Cc4ccc(C(C)n5cc(-c6cc(-c7ccccc7O)nnc6N)cn5)cc4)CC3)no2)C(C)C)cc1] | (2S,4R)-1-((2S)-2-(3-(2-(4-(4-(1-(4-(3-amino-6-(2-hydroxyphenyl)pyridazin-4-yl)-1H-pyrazol-1-yl)ethyl)benzyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 167 | 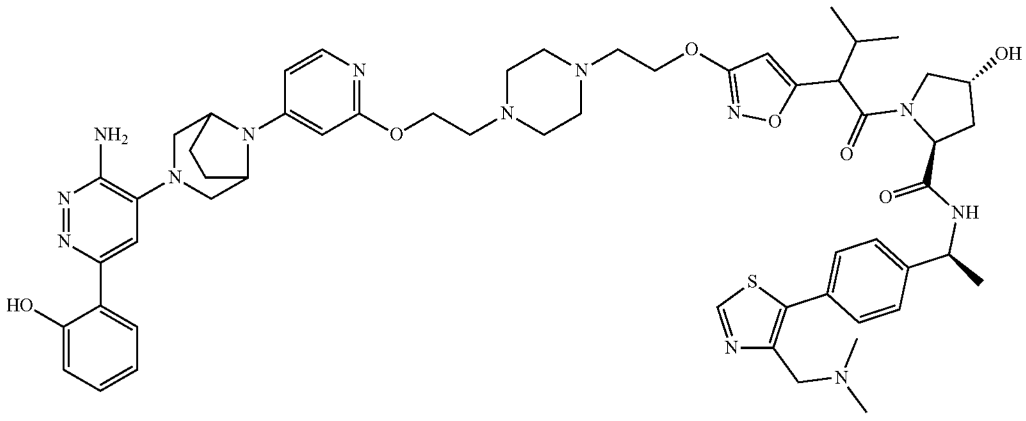 [SMILES: CC(C)C(C(=O)N1C[C@H](O)C[C@H]1C(=O)N[C@@H](C)c1ccc(-c2scnc2CN(C)C)cc1)c1cc(OCCN2CCN(CCOc3cc(N4C5CCC4CN(c4cc(-c6ccccc6O)nnc4N)C5)ccn3)CC2)no1] | (2S,4R)-1-(2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-((dimethylamino)methyl)thiazol-5-yl)phenyl)ethyl)-4-hydroxypyrrolidine-2-carboxamide |

TABLE 1B-continued

| ]Exemplary bifunctional degradation compounds of the present disclosure | | |
|---|---|---|
| Ex. # | Structure | Compound Name |
| 168 | 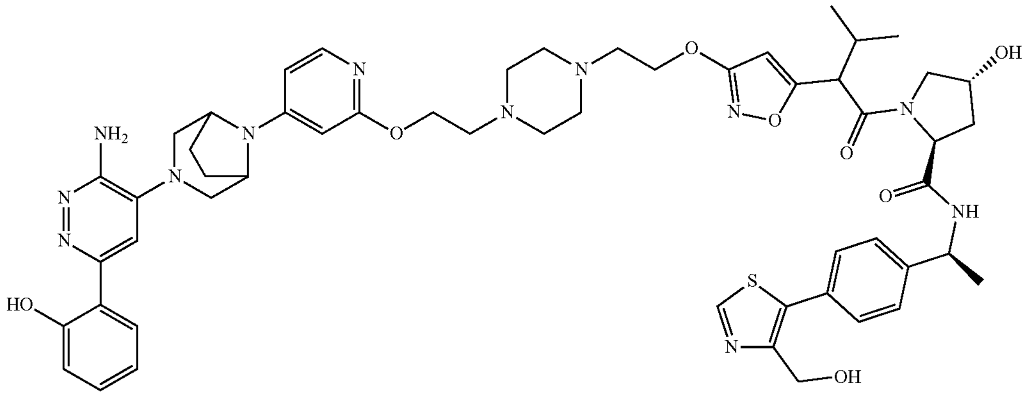 [SMILES: CC(C)C(C(=O)N1C[C@H](O)C[C@H]1C(=O)N[C@@H](C)c1ccc(-c2scnc2CO)cc1)c1cc(OCCN2CCN(CCOc3cc(N4C5CCC4CN(c4cc(-c6ccccc6O)nnc4N)C5)ccn3)CC2)no1] | (2S,4R)-1-(2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-(hydroxymethyl)thiazol-5-yl)phenyl)ethyl)pyrrolidine-2-carboxamide |
| 169 | 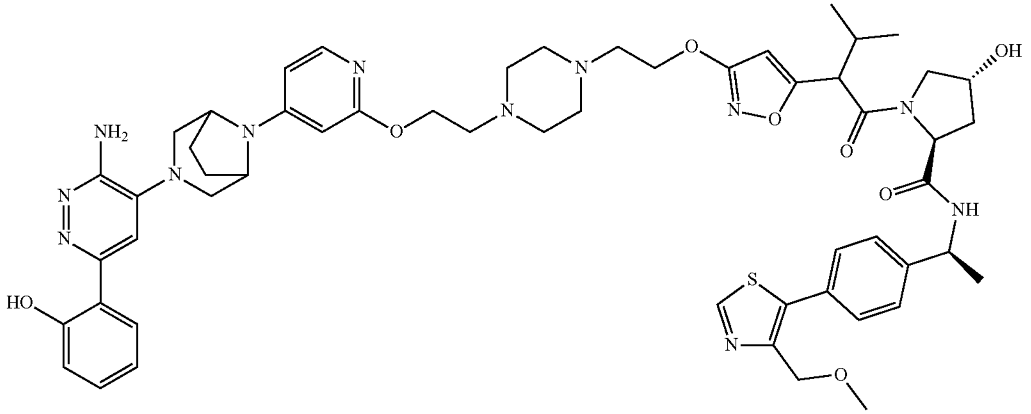 [SMILES: COCc1ncsc1-c1ccc([C@H](C)NC(=O)[C@@H]2C[C@@H](O)CN2C(=O)C(c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-(2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-(methoxymethyl)thiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 170 | 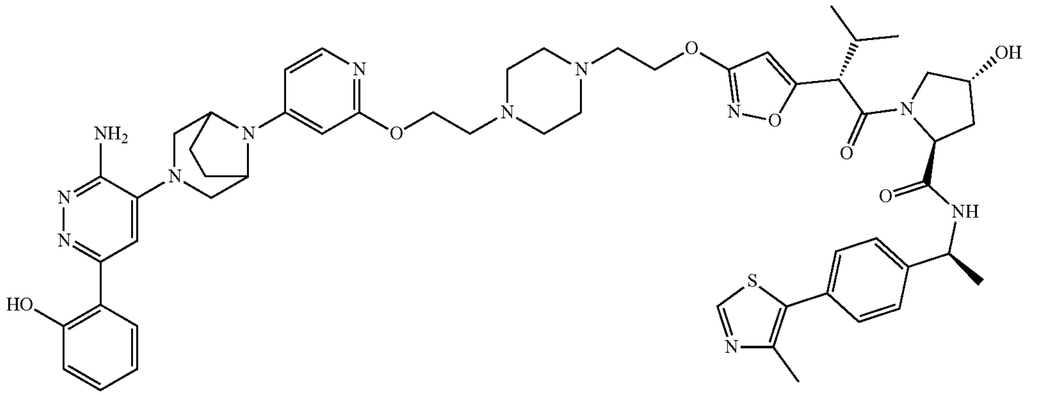 [SMILES: Cc1ncsc1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(3-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)propyl)isoxazol-5-yl)-3-methylbutanoyl)-4-hydroxy-N-((S)-1-(4-(4-methylthiazol-5-yl)phenyl)ethyl)pyrrolidine-2-carboxamide |
| 171 | 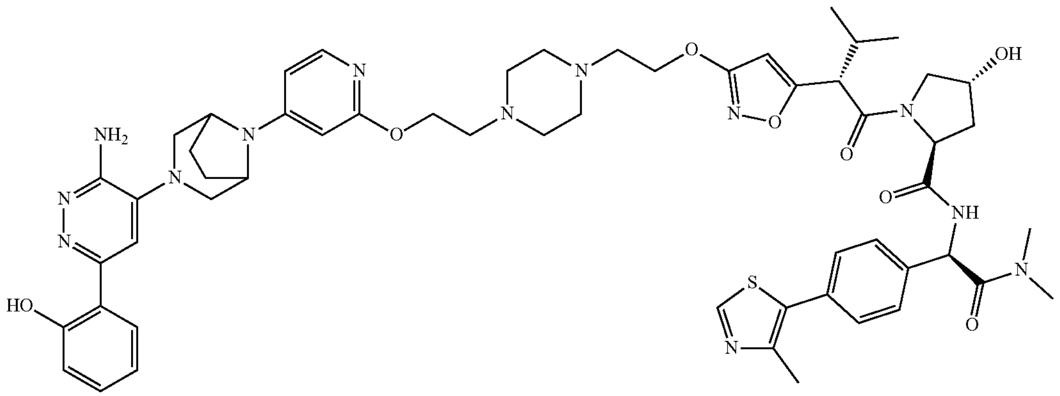 [SMILES: Cc1ncsc1-c1ccc([C@@H](NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)C(=O)N(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-(dimethylamino)-1-(4-(4-methylthiazol-5-yl)phenyl)-2-oxoethyl)-4-hydroxypyrrolidine-2-carboxamide |

TABLE 1B-continued

]Exemplary bifunctional degradation compounds of the present disclosure

| Ex. # | Structure | Compound Name |
|---|---|---|
| 172 | 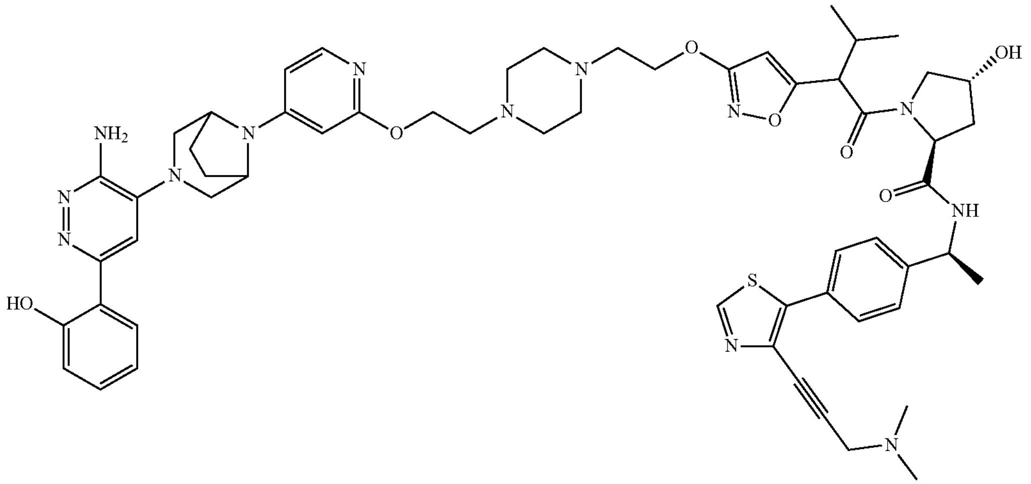 [SMILES: CC(C)C(C(=O)N1C[C@H](O)C[C@H]1C(=O)N[C@@H](C)c1ccc(-c2scnc2C#CCN(C)C)cc1)c1cc(OCCN2CCN(CCOc3cc(N4C5CCC4CN(c4cc(-c6ccccc6O)nnc4N)C5)ccn3)CC2)no1] | (2S,4R)-1-(2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-(3-(dimethylamino)prop-1-yn-1-yl)thiazol-5-yl)phenyl)ethyl)-4-hydroxypyrrolidine-2-carboxamide |
| 173 | 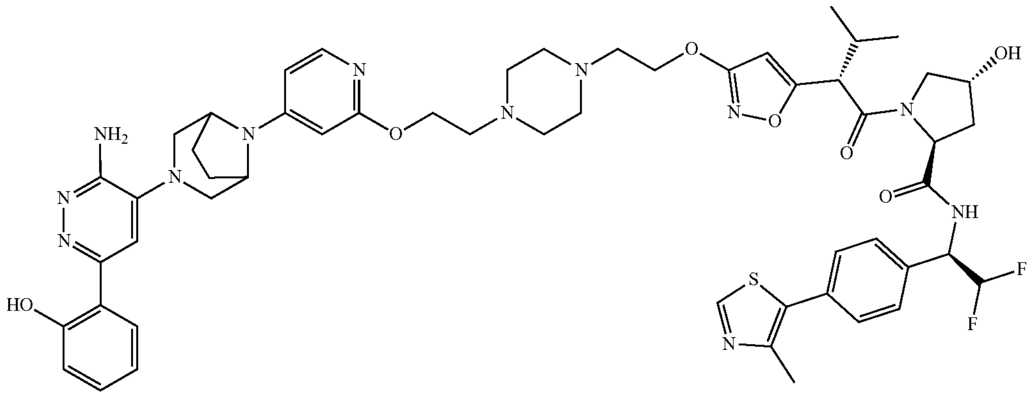 [SMILES: Cc1ncsc1-c1ccc([C@@H](NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)C(F)F)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2,2-difluoro-1-(4-(4-methylthiazol-5-yl)phenyl)ethyl)-4-hydroxypyrrolidine-2-carboxamide |

TABLE 1B-continued

| ]Exemplary bifunctional degradation compounds of the present disclosure | | |
|---|---|---|
| Ex. # | Structure | Compound Name |
| 174 | 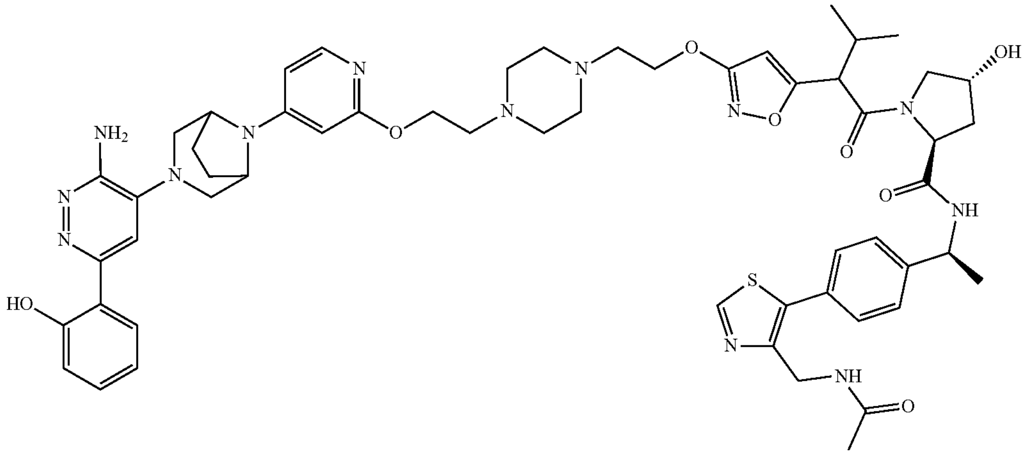 [SMILES: CC(=O)NCc1ncsc1-c1ccc([C@H](C)NC(=O)[C@@H]2C[C@@H](O)CN2C(=O)C(c2cc(OCCN3CCN(CCOc4cc(N5C6CCC5CN(c5cc(-c7ccccc7O)nnc5N)C6)ccn4)CC3)no2)C(C)C)cc1] | (2S,4R)-N-((S)-1-(4-(4-(acetamidomethyl)thiazol-5-yl)phenyl)ethyl)-1-(2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |
| 175 | 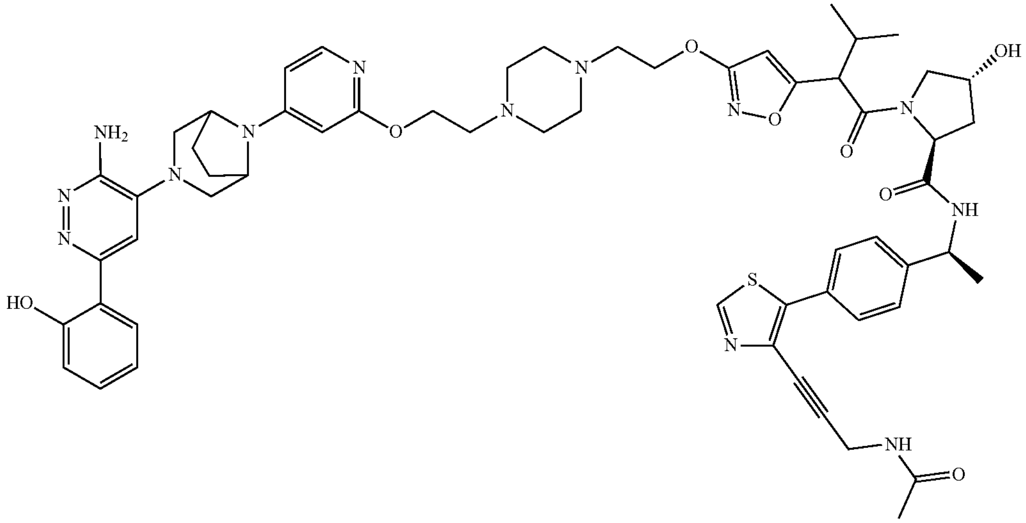 [SMILES: CC(=O)NCC#Cc1ncsc1-c1ccc([C@H](C)NC(=O)[C@@H]2C[C@@H](O)CN2C(=O)C(c2cc(OCCN3CCN(CCOc4cc(N5C6CCC5CN(c5cc(-c7ccccc7O)nnc5N)C6)ccn4)CC3)no2)C(C)C)cc1] | (2S,4R)-N-((S)-1-(4-(4-(3-acetamidoprop-1-yn-1-yl)thiazol-5-yl)phenyl)ethyl)-1-(2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |

TABLE 1B-continued

| ]Exemplary bifunctional degradation compounds of the present disclosure | | |
|---|---|---|
| Ex. # | Structure | Compound Name |
| 176 | 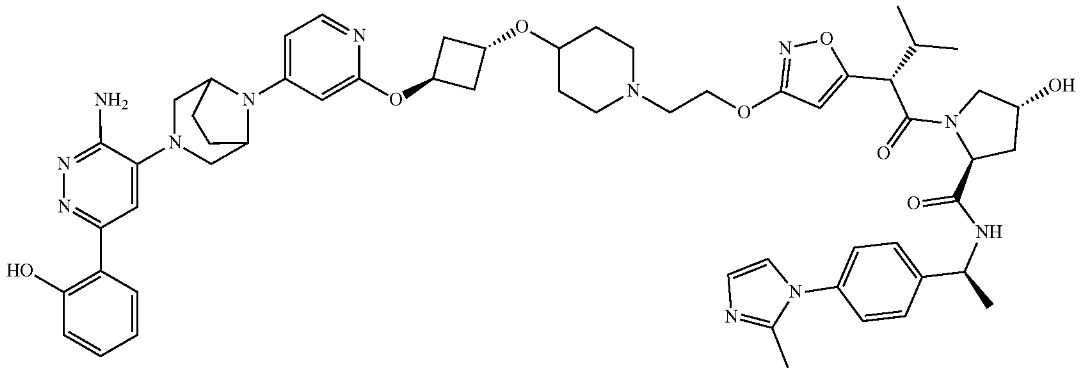 [SMILES: Cc1nccn1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |
| 178 | 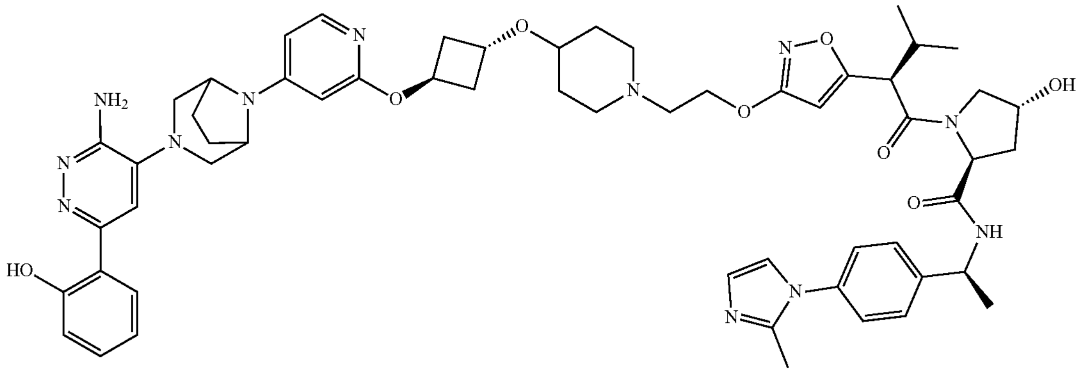 [SMILES: Cc1nccn1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 179 | 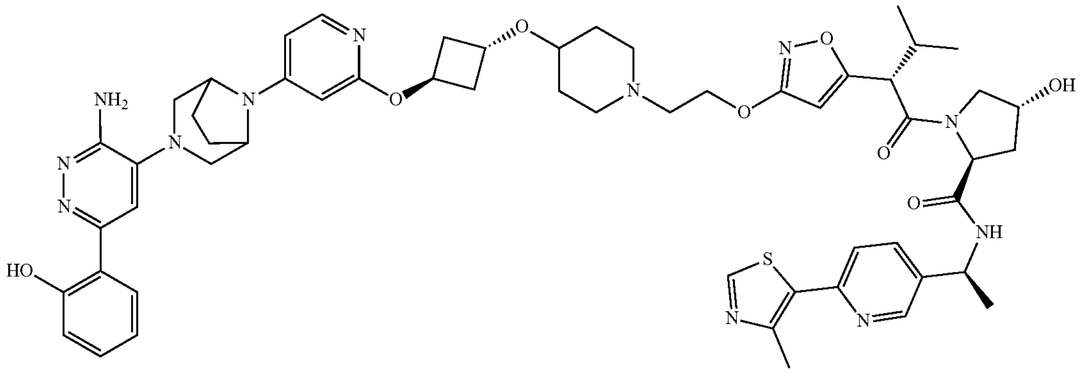 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 180 | 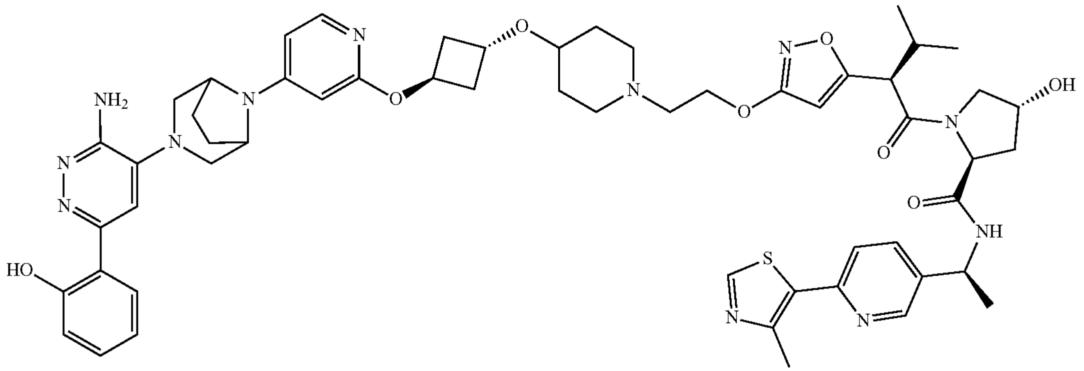 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 181 | 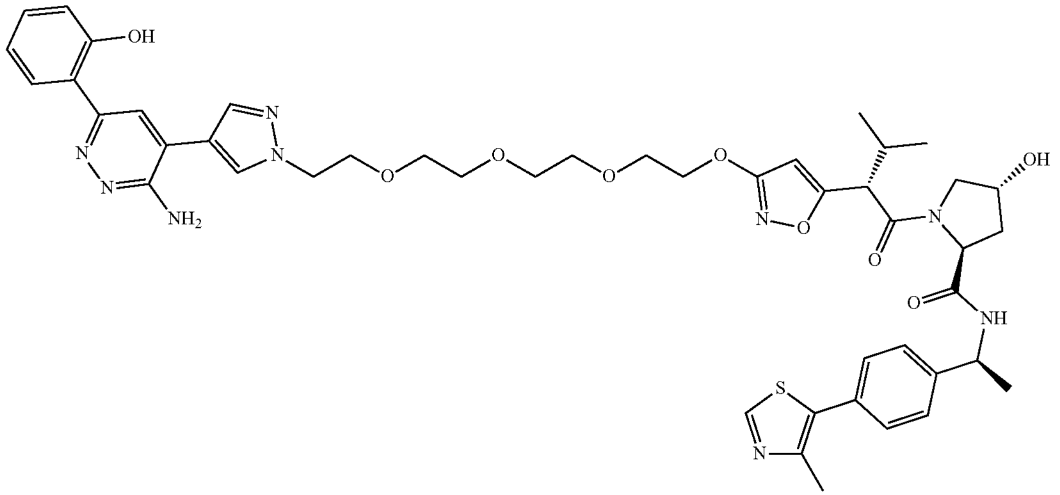 [SMILES: Cc1ncsc1-c1ccc([C@H](C)NC(=O)[C@@H]2C[C@@H](O)CN2C(=O)[C@H](c2cc(OCCOCCOCCOCCn3cc(-c4cc(-c5ccccc5O)nnc4N)cn3)no2)C(C)C)cc1] | (2S,4R)-1-((S)-2-(3-(2-(2-(2-(2-(4-(3-amino-6-(2-hydroxyphenyl)pyridazin-4-yl)-1H-pyrazol-1-yl)ethoxy)ethoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 182 | 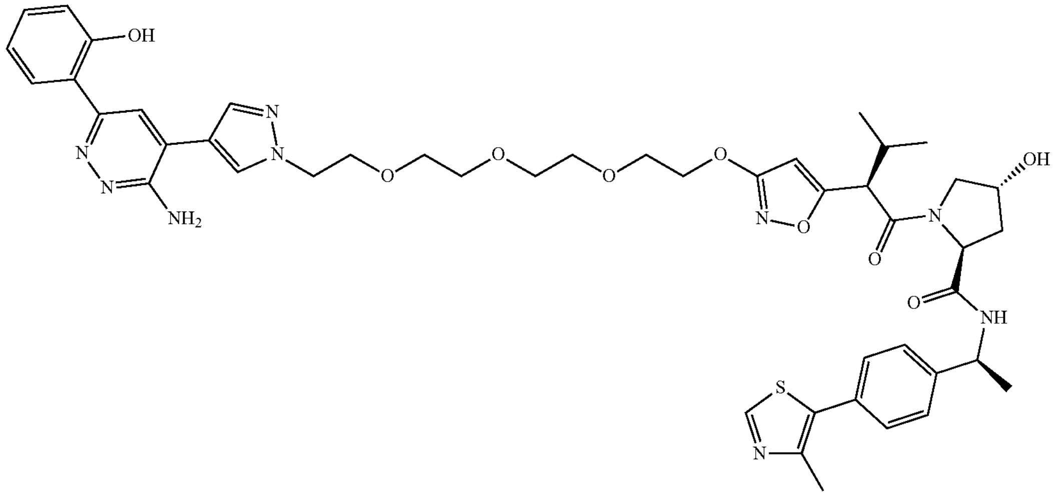 [SMILES: Cc1ncsc1-c1ccc([C@H](C)NC(=O)[C@@H]2C[C@@H](O)CN2C(=O)[C@@H](c2cc(OCCOCCOCCOCCn3cc(-c4cc(-c5ccccc5O)nnc4N)cn3)no2)C(C)C)cc1] | (2S,4R)-1-((R)-2-(3-(2-(2-(2-(2-(4-(3-amino-6-(2-hydroxyphenyl)pyridazin-4-yl)-1H-pyrazol-1-yl)ethoxy)ethoxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 183 | 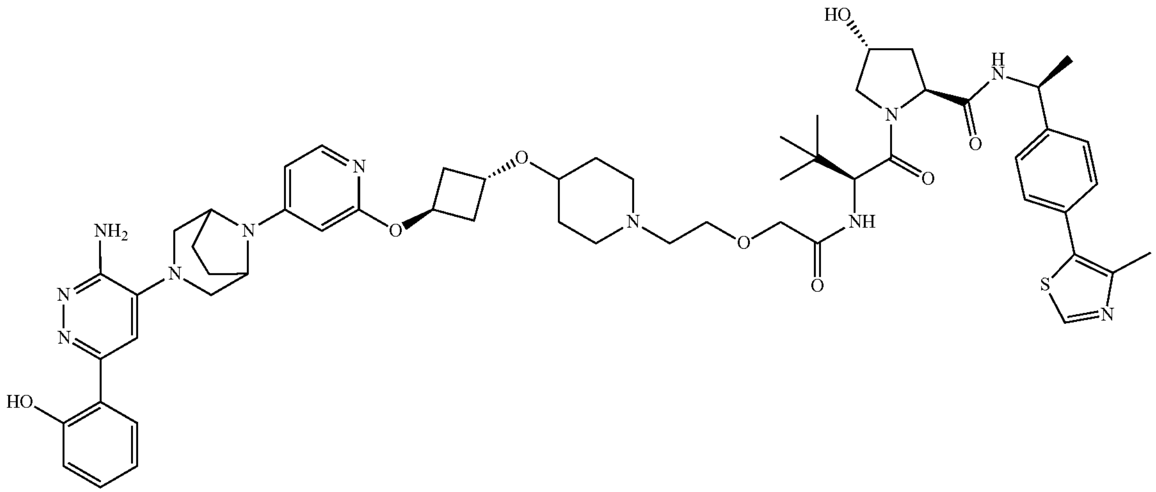 [SMILES: Cc1ncsc1-c1ccc([C@H](C)NC(=O)[C@@H]2C[C@@H](O)CN2C(=O)[C@@H](NC(=O)COCCN2CCC(O[C@H]3C[C@H](Oc4cc(N5C6CCC5CN(c5cc(-c7ccccc7O)nnc5N)C6)ccn4)C3)CC2)C(C)(C)C)cc1] | (2S,4R)-1-((2S)-2-(2-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 184 | 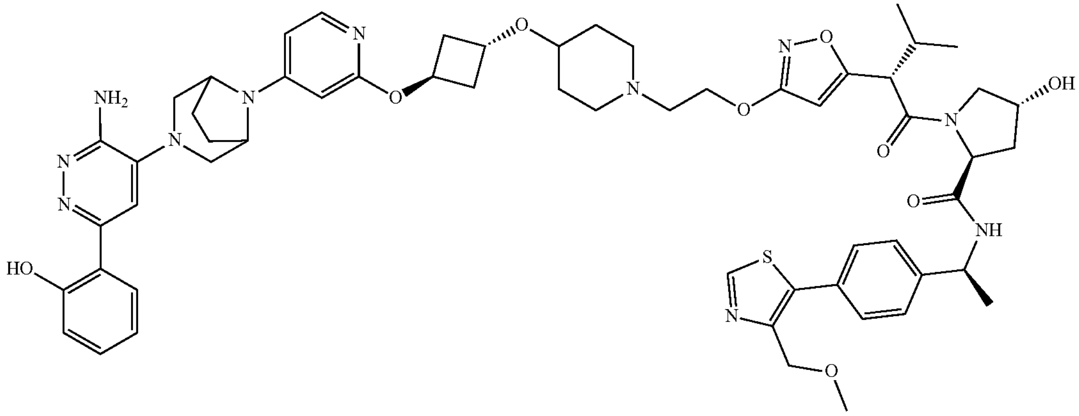 [SMILES: COCc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-(methoxymethyl)thiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 185 | 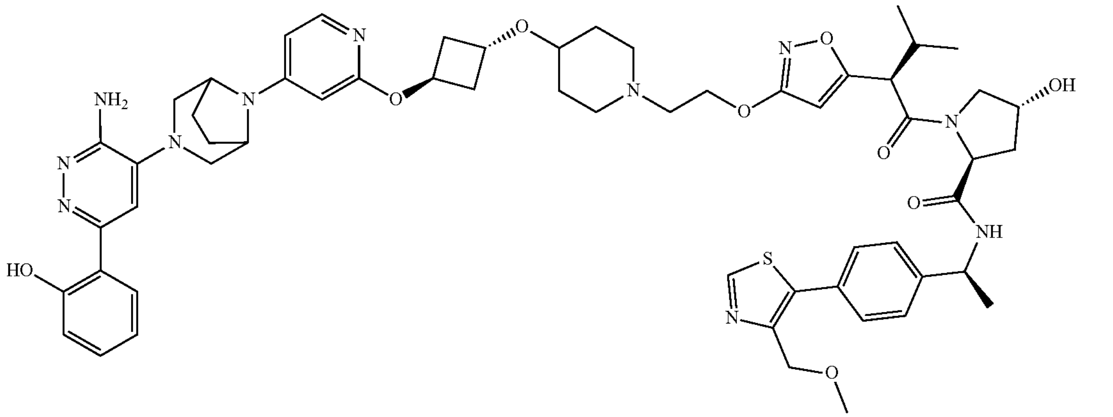 [SMILES: COCc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-(methoxymethyl)thiazol-5-yl)phenyl)ethyl)pyrrolidine-2-carboxamide |
| 186 | 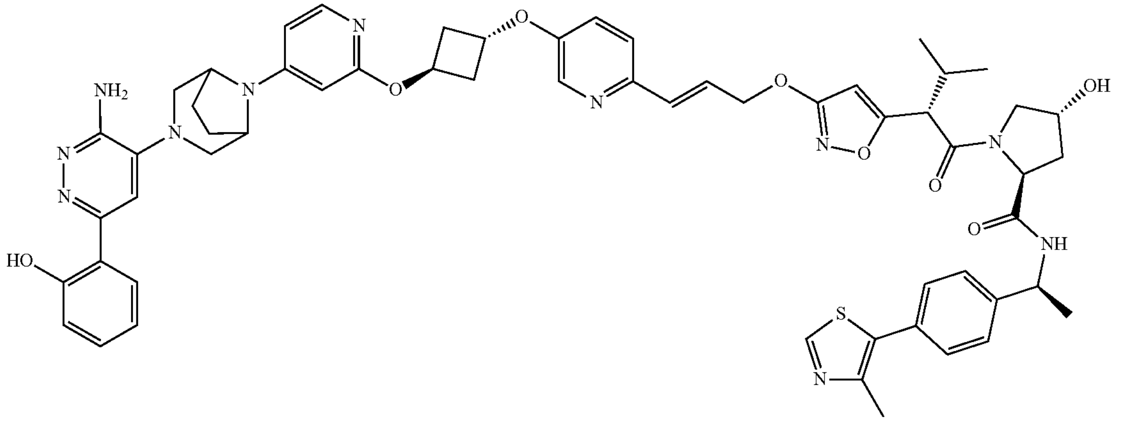 [SMILES: Cc1ncsc1-c1ccc([C@H](C)NC(=O)[C@@H]2C[C@@H](O)CN2C(=O)[C@H](c2cc(OC/C=C/c3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2S)-2-(3-(((E)-3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)allyl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 187 | 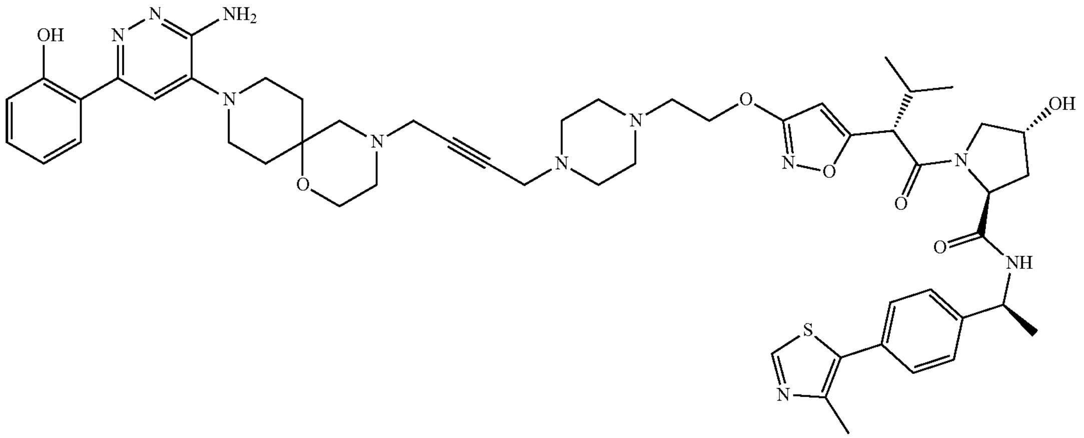 [SMILES: Cc1ncsc1-c1ccc([C@H](C)NC(=O)[C@@H]2C[C@@H](O)CN2C(=O)[C@H](c2cc(OCCN3CCN(CC#CCN4CCOC5(CCN(c6cc(-c7ccccc7O)nnc6N)CC5)C4)CC3)no2)C(C)C)cc1] | (2S,4R)-1-((S)-2-(3-(2-(4-(4-(9-(3-amino-6-(2-hydroxyphenyl)pyridazin-4-yl)-1-oxa-4,9-diazaspiro[5.5]undecan-4-yl)but-2-yn-1-yl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 188 | 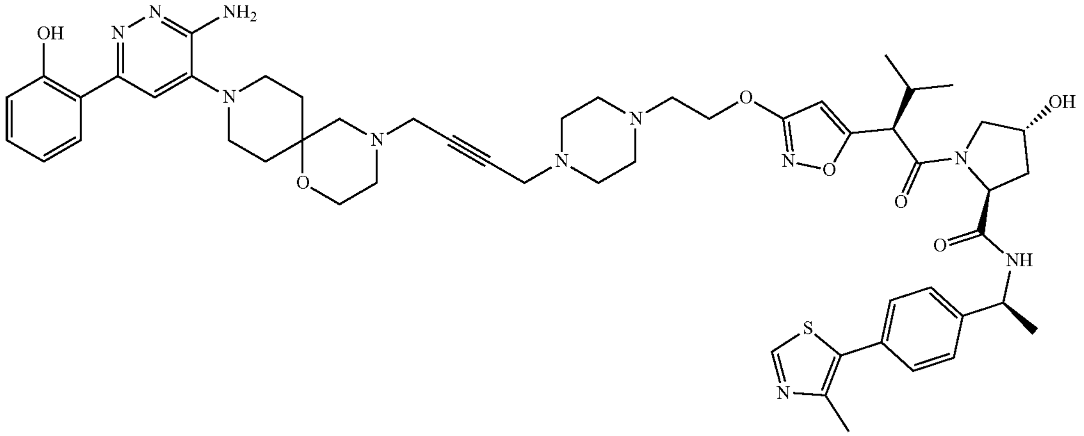 [SMILES: Cc1ncsc1-c1ccc([C@H](C)NC(=O)[C@@H]2C[C@@H](O)CN2C(=O)[C@@H](c2cc(OCCN3CCN(CC#CCN4CCOC5(CCN(c6cc(-c7ccccc7O)nnc6N)CC5)C4)CC3)no2)C(C)C)cc1] | (2S,4R)-1-((R)-2-(3-(2-(4-(4-(9-(3-amino-6-(2-hydroxyphenyl)pyridazin-4-yl)-1-oxa-4,9-diazaspiro[5.5]undecan-4-yl)but-2-yn-1-yl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 189 | 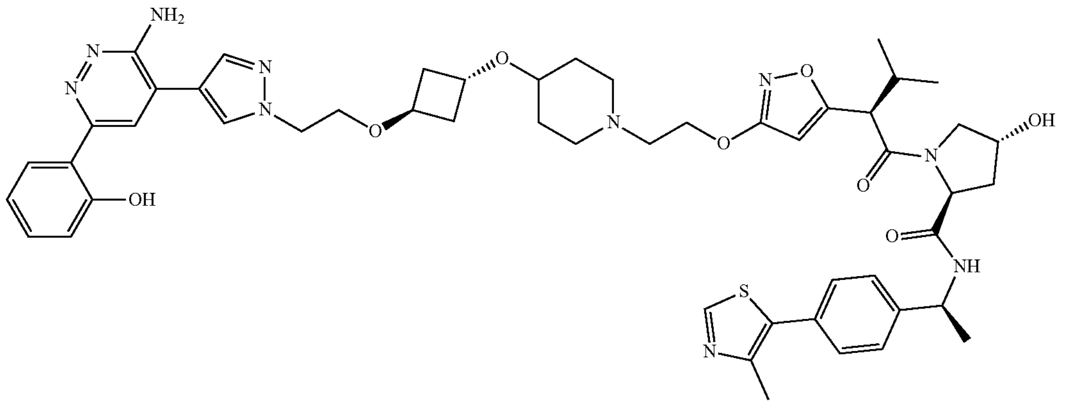 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](OCCn5cc(-c6cc(-c7ccccc7O)nnc6N)cn5)C4)CC3)no2)C(C)C)cc1] | (2S,4R)-1-((R)-2-(3-(2-(4-((1r,3R)-3-(2-(4-(3-amino-6-(2-hydroxyphenyl)pyridazin-4-yl)-1H-pyrazol-1-yl)ethoxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 190 | 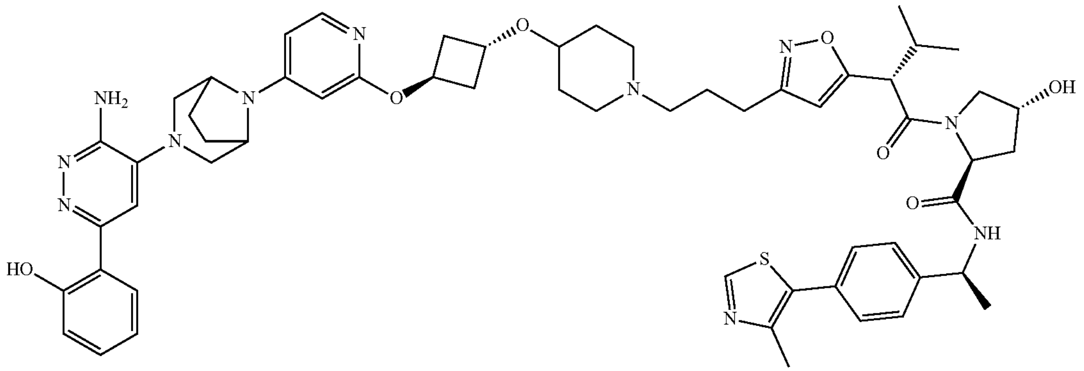 [SMILES: Cc1ncsc1-c1ccc([C@H](C)NC(=O)[C@@H]2C[C@@H](O)CN2C(=O)[C@H](c2cc(CCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(3-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)propyl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 191 | 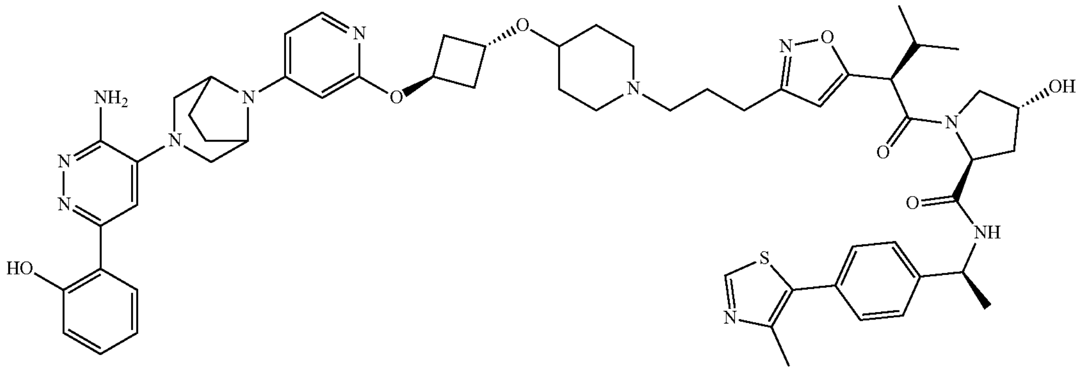 [SMILES: Cc1ncsc1-c1ccc([C@H](C)NC(=O)[C@@H]2C[C@@H](O)CN2C(=O)[C@@H](c2cc(CCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)propyl)isoxazol-5-yl)-3-methylbutanoyl)-4-hydroxy-N-((S)-1-(4-(4-methylthiazol-5-yl)phenyl)ethyl)pyrrolidine-2-carboxamide |
| 192 | 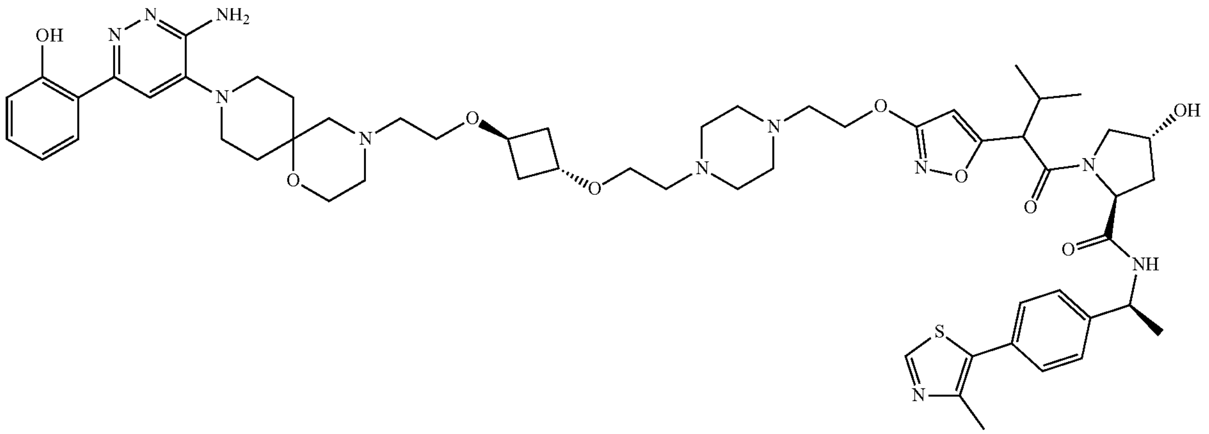 [SMILES: Cc1ncsc1-c1ccc([C@H](C)NC(=O)[C@@H]2C[C@@H](O)CN2C(=O)C(c2cc(OCCN3CCN(CCO[C@H]4C[C@H](OCCN5CCOC6(CCN(c7cc(-c8ccccc8O)nnc7N)CC6)C5)C4)CC3)no2)C(C)C)cc1] | (2S,4R)-1-(2-(3-(2-(4-(2-((1r,3r)-3-(2-(9-(3-amino-6-(2-hydroxyphenyl)pyridazin-4-yl)-1-oxa-4,9-diazaspiro[5.5]undecan-4-yl)ethoxy)cyclobutoxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 193 | 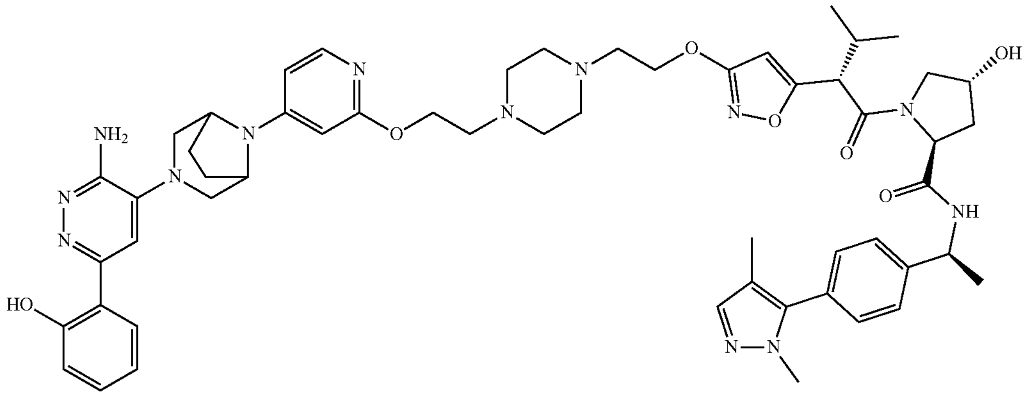 [SMILES: Cc1cnn(C)c1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(1,4-dimethyl-1H-pyrazol-5-yl)phenyl)ethyl)-4-hydroxypyrrolidine-2-carboxamide |
| 194 | 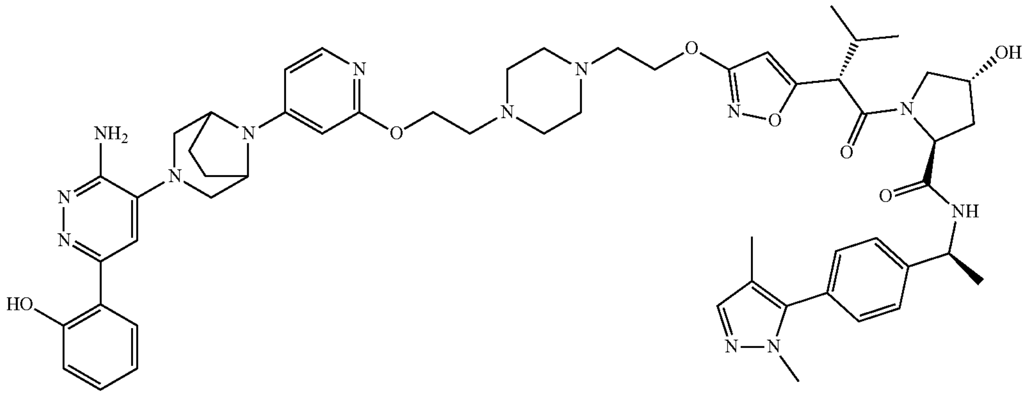 [SMILES: Cc1cnn(C)c1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(1,4-dimethyl-1H-pyrazol-5-yl)phenyl)ethyl)-4-hydroxypyrrolidine-2-carboxamide |

TABLE 1B-continued

]Exemplary bifunctional degradation compounds of the present disclosure

| Ex. # | Structure | Compound Name |
| --- | --- | --- |
| 195 | 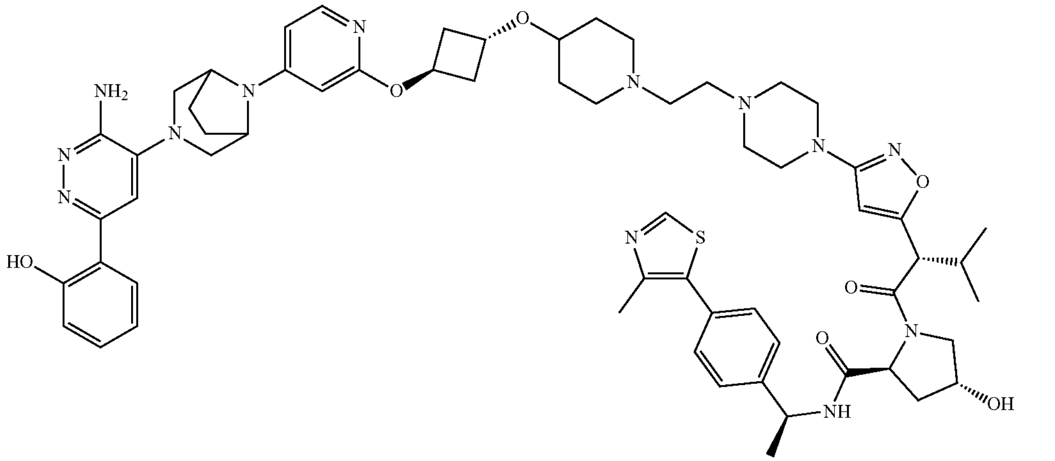 [SMILES: Cc1ncsc1-c1ccc([C@H](C)NC(=O)[C@@H]2C[C@@H](O)CN2C(=O)[C@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 196 | 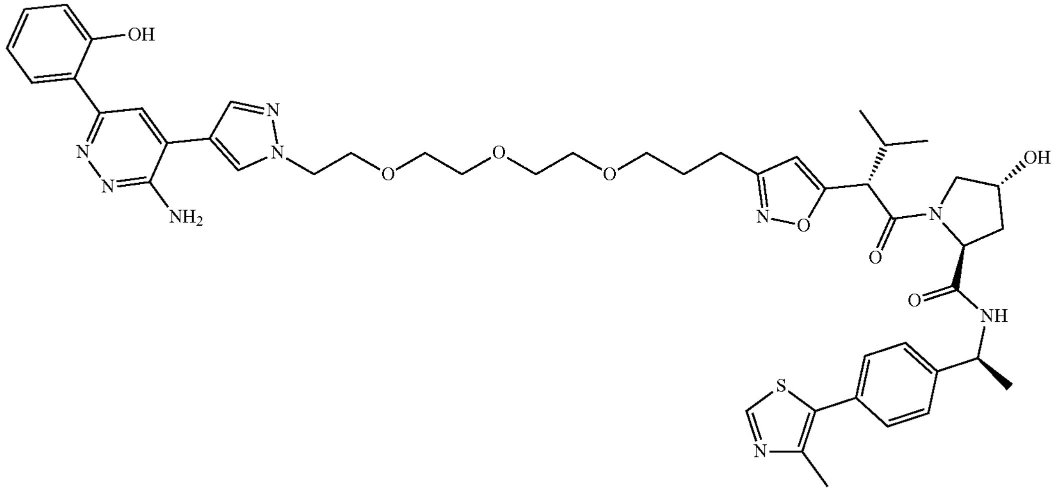 [SMILES: Cc1ncsc1-c1ccc([C@H](C)NC(=O)[C@@H]2C[C@@H](O)CN2C(=O)[C@H](c2cc(CCCOCCOCCOCCn3cc(-c4cc(-c5ccccc5O)nnc4N)cn3)no2)C(C)C)cc1] | (2S,4R)-1-((S)-2-(3-(3-(2-(2-(2-(4-(3-amino-6-(2-hydroxyphenyl)pyridazin-4-yl)-1H-pyrazol-1-yl)ethoxy)ethoxy)ethoxy)propyl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 197 | 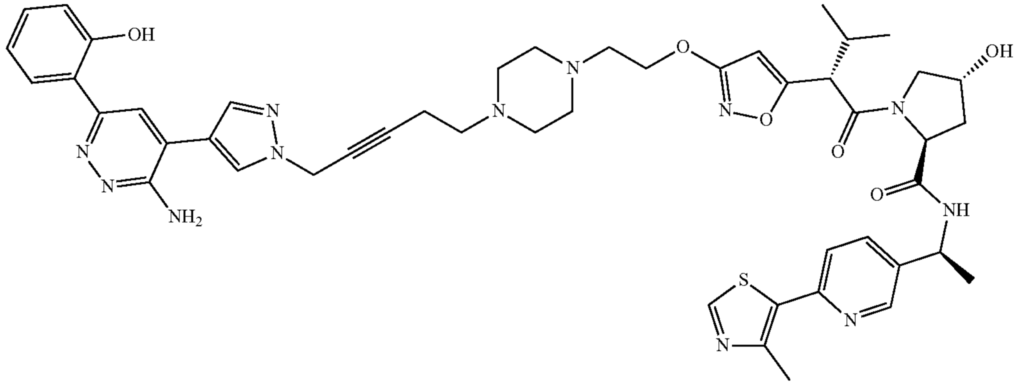 [SMILES: Cc1ncsc1-c1ccc([C@H](C)NC(=O)[C@@H]2C[C@@H](O)CN2C(=O)[C@H](c2cc(OCCN3CCN(CCC#CCn4cc(-c5cc(-c6ccccc6O)nnc5N)cn4)CC3)no2)C(C)C)cn1] | (2S,4R)-1-((S)-2-(3-(2-(4-(5-(4-(3-amino-6-(2-hydroxyphenyl)pyridazin-4-yl)-1H-pyrazol-1-yl)pent-3-yn-1-yl)piperazin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 198 | 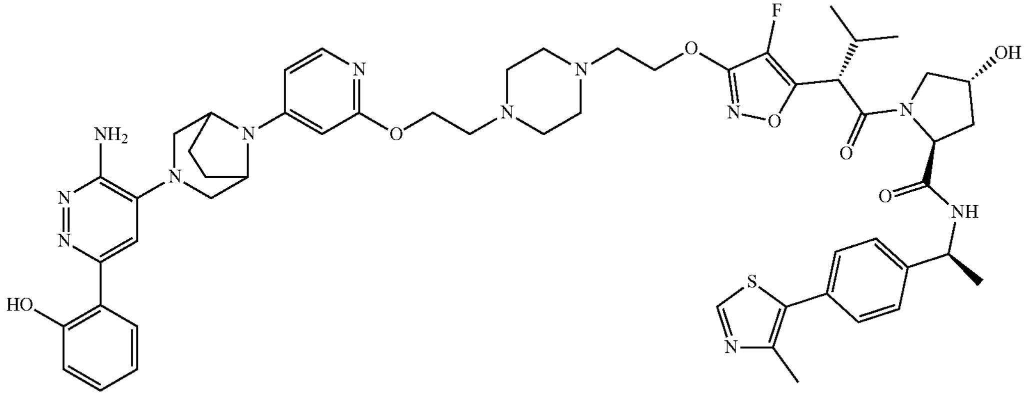 [SMILES: Cc1ncsc1-c1ccc([C@H](C)NC(=O)[C@@H]2C[C@@H](O)CN2C(=O)[C@H](c2onc(OCCN3CCN(CCOc4cc(N5C6CCC5CN(c5cc(-c7ccccc7O)nnc5N)C6)ccn4)CC3)c2F)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)-4-fluoroisoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 199 | 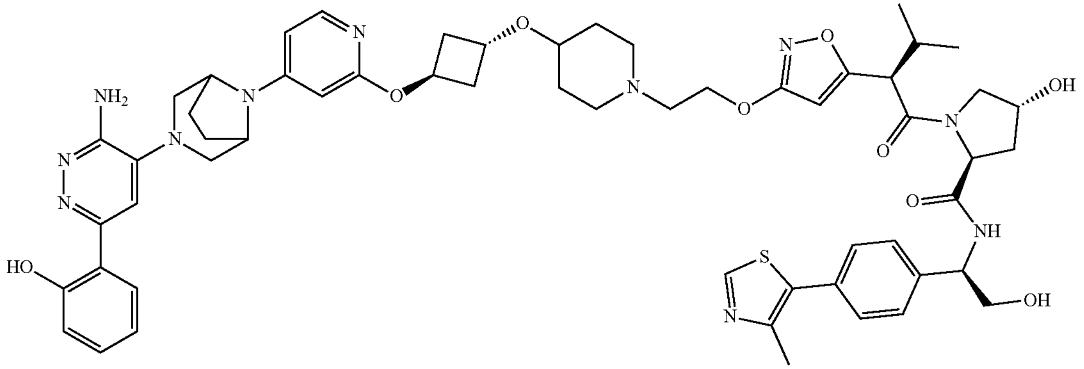 [SMILES: Cc1ncsc1-c1ccc([C@H](CO)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide |
| 200 | 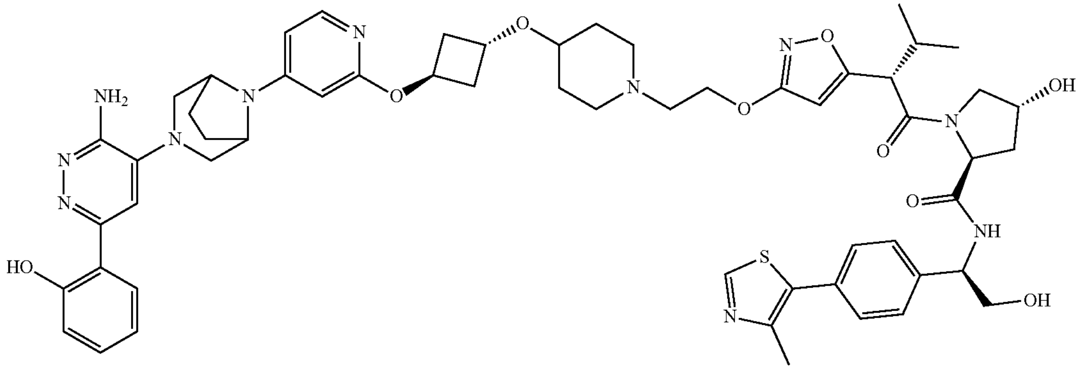 [SMILES: Cc1ncsc1-c1ccc([C@H](CO)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 201 | 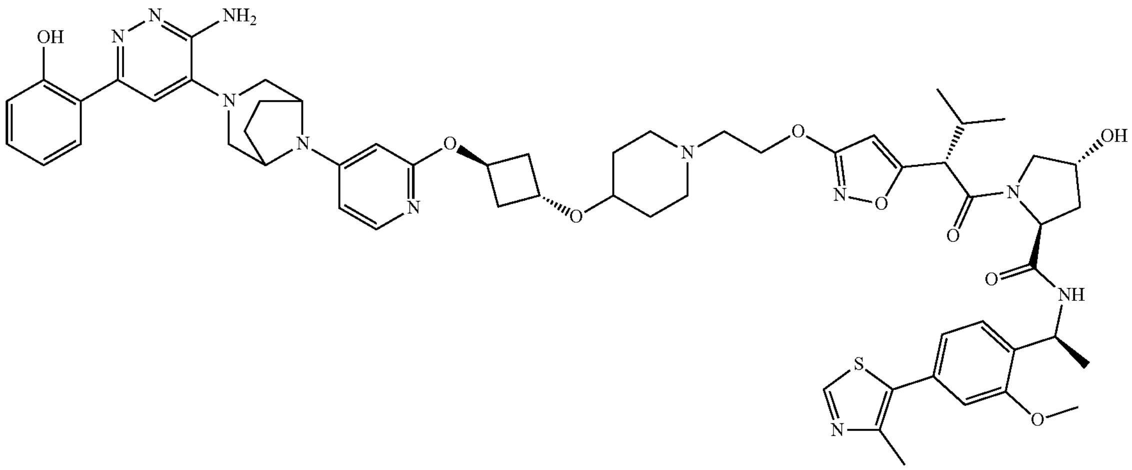 [SMILES: COc1cc(-c2scnc2C)ccc1[C@H](C)NC(=O)[C@@H]1C[C@@H](O)CN1C(=O)[C@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide |
| 202 | 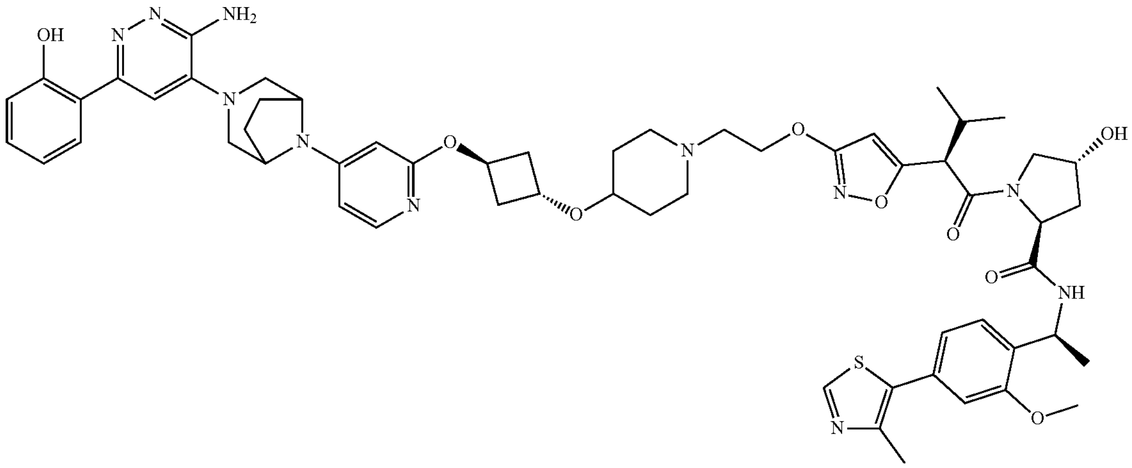 [SMILES: COc1cc(-c2scnc2C)ccc1[C@H](C)NC(=O)[C@@H]1C[C@@H](O)CN1C(=O)[C@@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(2-methoxy-4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 203 | 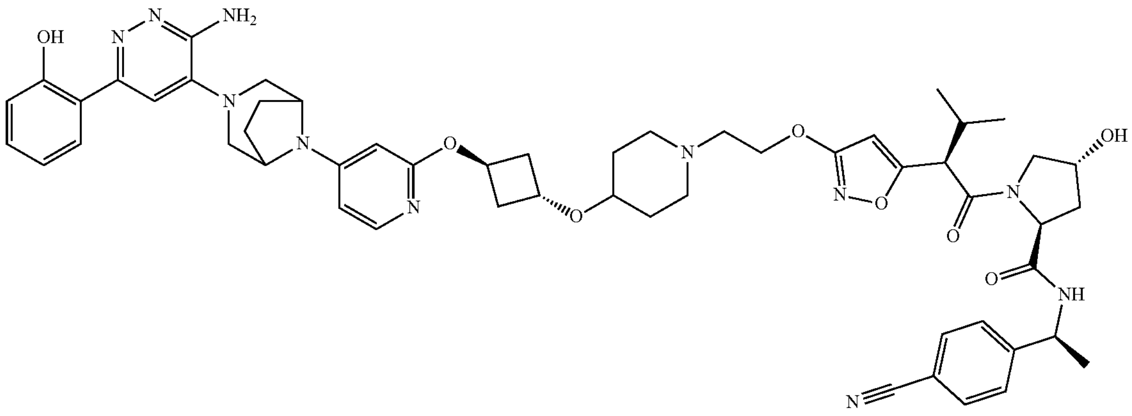 [SMILES: CC(C)[C@@H](C(=O)N1C[C@H](O)C[C@H]1C(=O)N[C@@H](C)c1ccc(C#N)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-cyanophenyl)ethyl)-4-hydroxypyrrolidine-2-carboxamide |
| 204 | 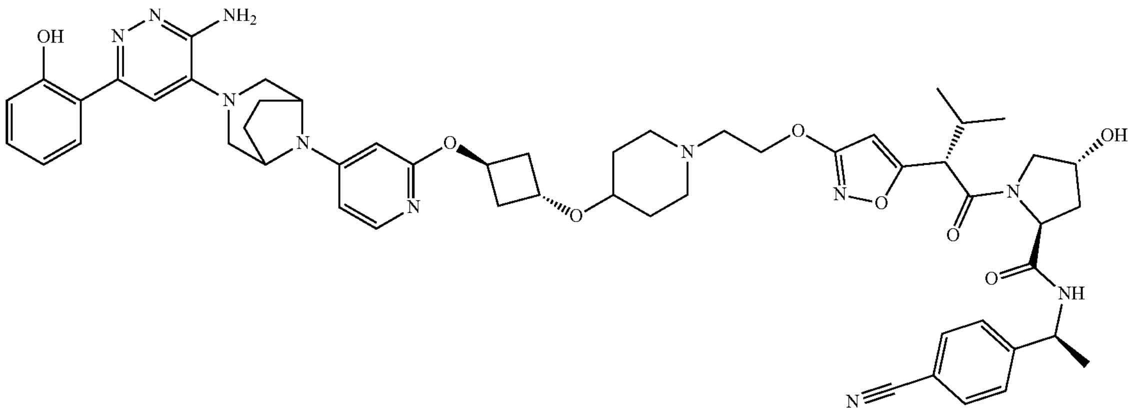 [SMILES: CC(C)[C@H](C(=O)N1C[C@H](O)C[C@H]1C(=O)N[C@@H](C)c1ccc(C#N)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-cyanophenyl)ethyl)-4-hydroxypyrrolidine-2-carboxamide |

TABLE 1B-continued

]Exemplary bifunctional degradation compounds of the present disclosure

| Ex. # | Structure | Compound Name |
| --- | --- | --- |
| 205 | 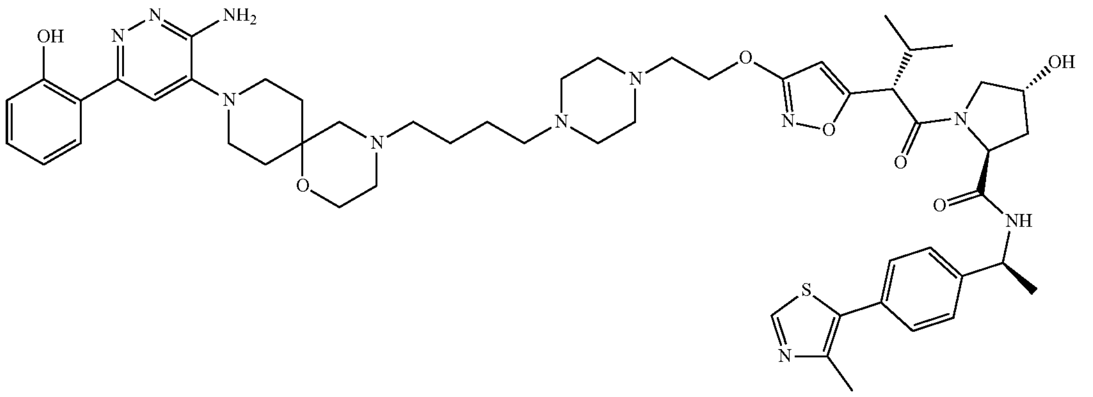 [SMILES: Cc1ncsc1-c1ccc([C@H](C)NC(=O)[C@@H]2C[C@@H](O)CN2C(=O)[C@H](c2cc(OCCN3CCN(CCCCN4CCOC5(CCN(c6cc(-c7ccccc7O)nnc6N)CC5)C4)CC3)no2)C(C)C)cc1] | (2S,4R)-1-((S)-2-(3-(2-(4-(4-(9-(3-amino-6-(2-hydroxyphenyl)pyridazin-4-yl)-1-oxa-4,9-diazaspiro[5.5]undecan-4-yl)butyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 206 | 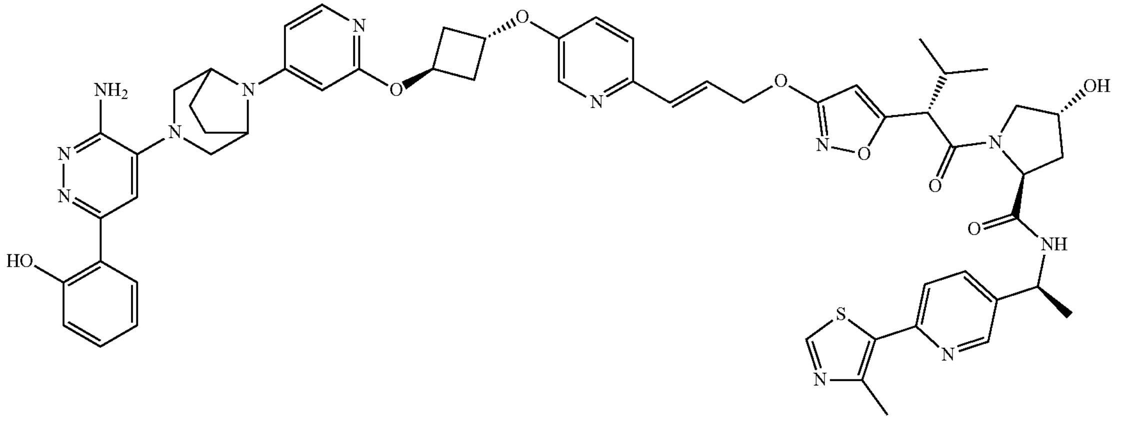 [SMILES: Cc1ncsc1-c1ccc([C@H](C)NC(=O)[C@@H]2C[C@@H](O)CN2C(=O)[C@H](c2cc(OC/C=C/c3ccc(O[C@H]4C[C@H](Oc5cc(N6C7CCC6CN(c6cc(-c8ccccc8O)nnc6N)C7)ccn5)C4)cn3)no2)C(C)C)cn1] | (2S,4R)-1-((2S)-2-(3-(((E)-3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)allyl)oxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 207 | 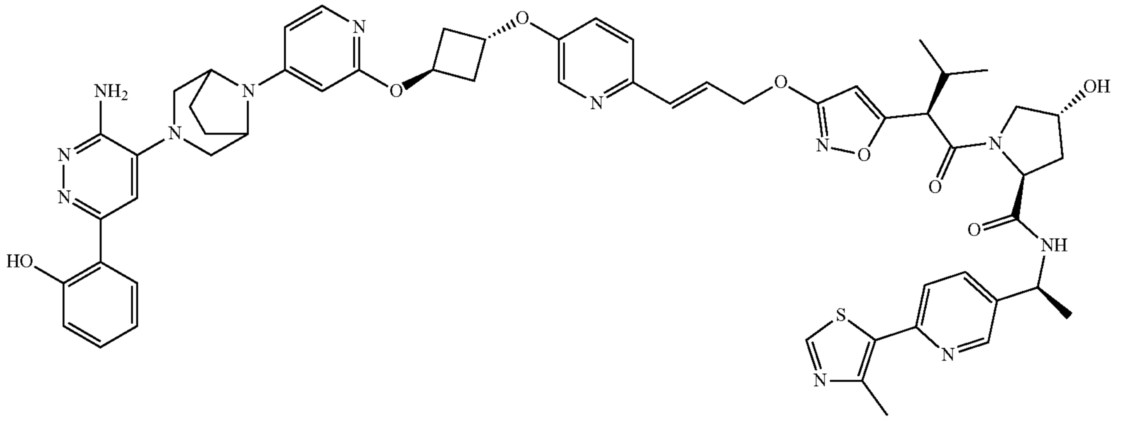 [SMILES: Cc1ncsc1-c1ccc([C@H](C)NC(=O)[C@@H]2C[C@@H](O)CN2C(=O)[C@@H](c2cc(OC/C=C/c3ccc(O[C@H]4C[C@H](Oc5cc(N6C7CCC6CN(c6cc(-c8ccccc8O)nnc6N)C7)ccn5)C4)cn3)no2)C(C)C)cn1] | (2S,4R)-1-((2R)-2-(3-(((E)-3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)allyl)oxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 208 | 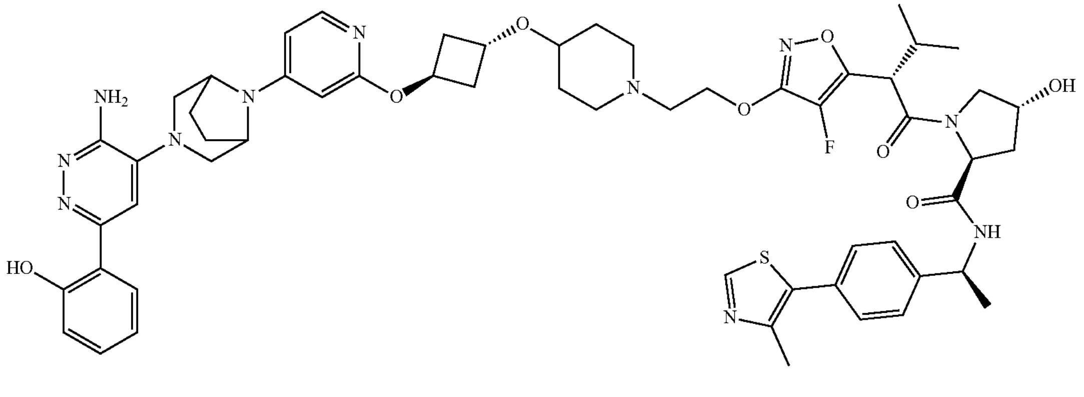 [SMILES: Cc1ncsc1-c1ccc([C@H](C)NC(=O)[C@@H]2C[C@@H](O)CN2C(=O)[C@H](c2onc(OCCN3CCC(O[C@H]4C[C@H](Oc5cc(N6C7CCC6CN(c6cc(-c8ccccc8O)nnc6N)C7)ccn5)C4)CC3)c2F)C(C)C)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-fluoroisoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

| Ex. # | Structure | Compound Name |
|---|---|---|
| | ]Exemplary bifunctional degradation compounds of the present disclosure | |
| 209 | 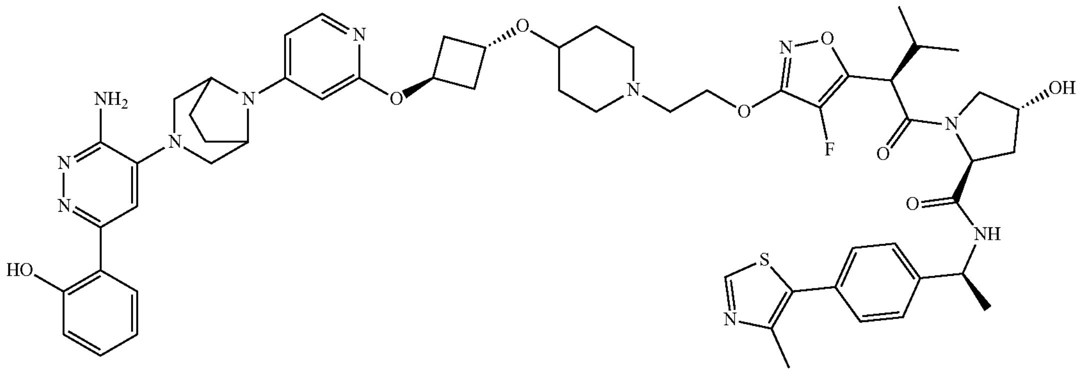 [SMILES: Cc1ncsc1-c1ccc([C@H](C)NC(=O)[C@@H]2C[C@@H](O)CN2C(=O)[C@@H](c2onc(OCCN3CCC(O[C@H]4C[C@H](Oc5cc(N6C7CCC6CN(c6cc(-c8ccccc8O)nnc6N)C7)ccn5)C4)CC3)c2F)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-fluoroisoxazol-5-yl)-3-methylbutanoyl)-4-hydroxy-N-((S)-1-(4-(4-methylthiazol-5-yl)phenyl)ethyl)pyrrolidine-2-carboxamide |
| 210 | 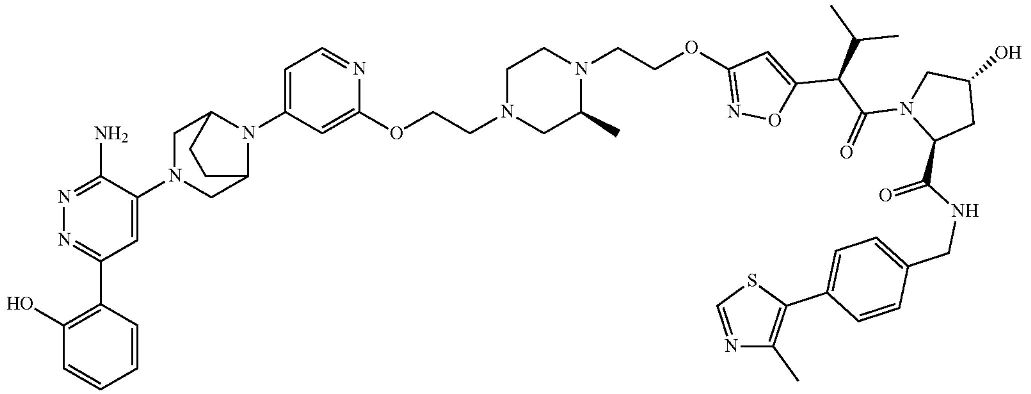 [SMILES: Cc1ncsc1-c1ccc(CNC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)C[C@@H]3C)no2)C(C)C)cc1] | (2S,4R)-1-((2R)-2-(3-(2-((2S)-4-(2-((4-(3-(3-amino-6-(2-hydroxyphenyl)pyridazin-4-yl)-3,8-diazabicyclo[3.2.1]octan-8-yl)pyridin-2-yl)oxy)ethyl)-2-methylpiperazin-1-yl)ethoxy)isoxazol-5-yl)-3-methylbutanoyl)-4-hydroxy-N-(4-(4-methylthiazol-5-yl)benzyl)pyrrolidine-2-carboxamide |

TABLE 1B-continued

]Exemplary bifunctional degradation compounds of the present disclosure

| Ex. # | Structure | Compound Name |
|---|---|---|
| 211 | 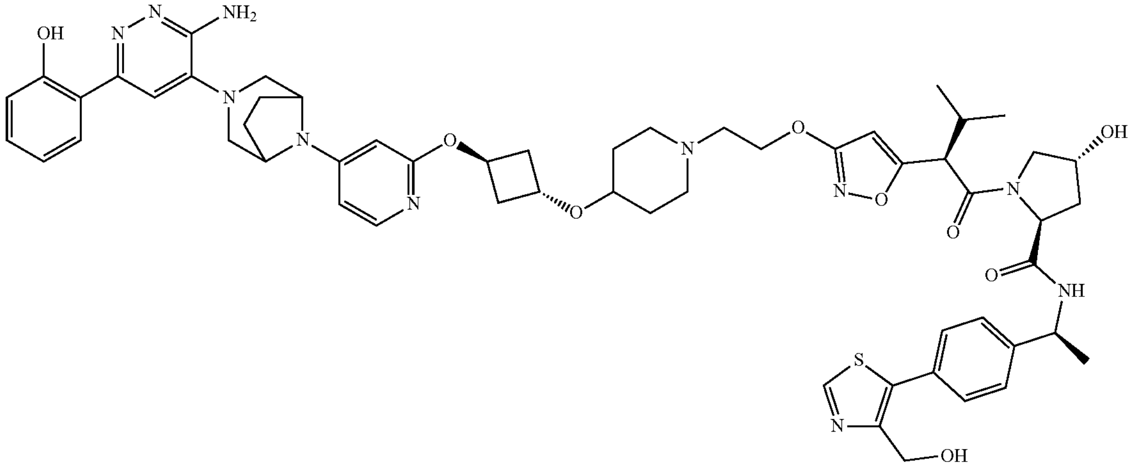 [SMILES: CC(C)[C@@H](C(=O)N1C[C@H](O)C[C@H]1C(=O)N[C@@H](C)c1ccc(-c2scnc2CO)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-(hydroxymethyl)thiazol-5-yl)phenyl)ethyl)pyrrolidine-2-carboxamide |
| 212 | 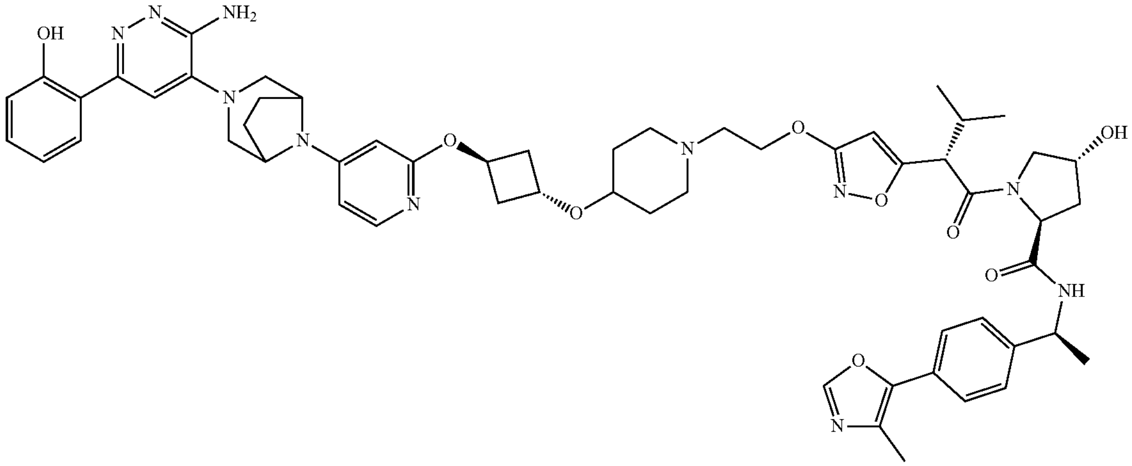 [SMILES: Cc1ncoc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methyloxazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 213 | 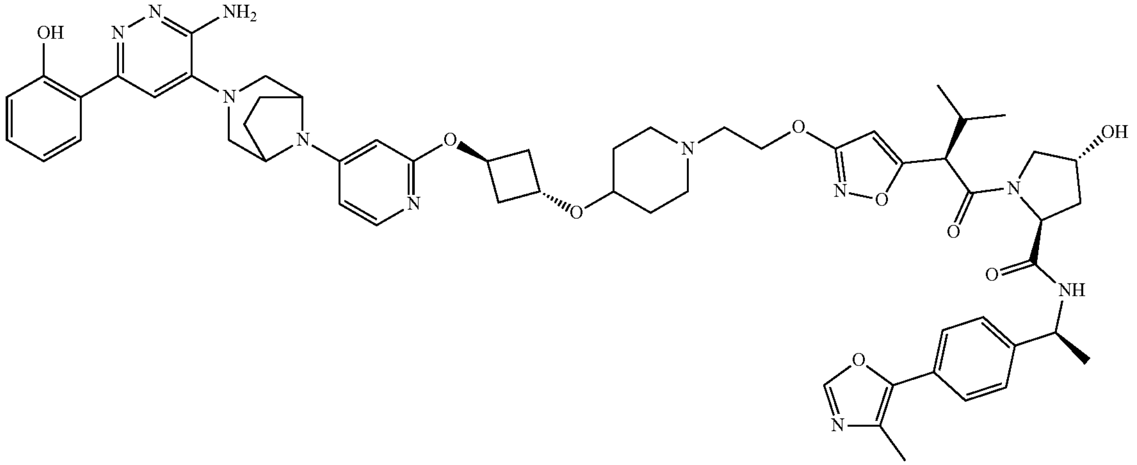 [SMILES: Cc1ncoc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methyloxazol-5-yl)phenyl)ethyl)pyrrolidine-2-carboxamide |
| 214 | 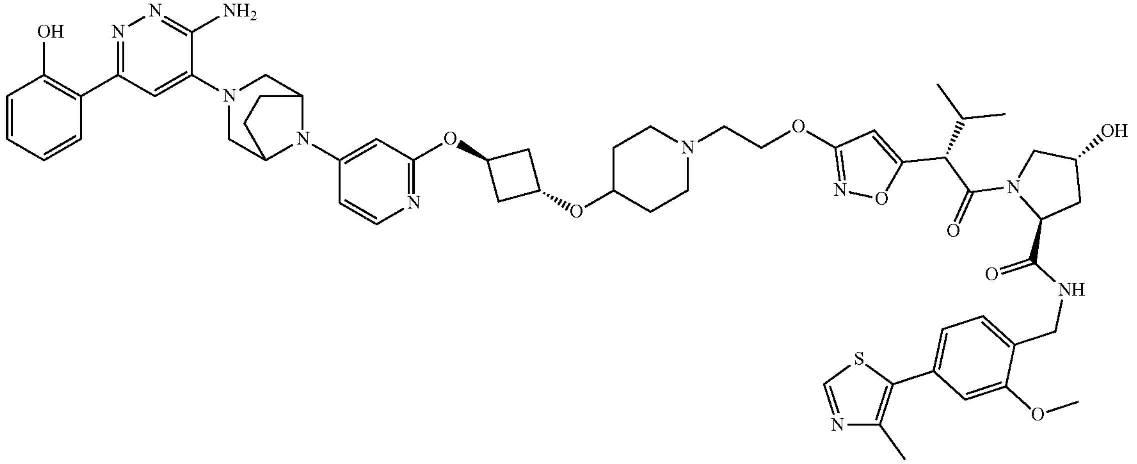 [SMILES: COc1cc(-c2scnc2C)ccc1CNC(=O)[C@@H]1C[C@@H](O)CN1C(=O)[C@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-(2-methoxy-4-(4-methylthiazol-5-yl)benzyl)pyrrolidine-2-carboxamide |

TABLE 1B-continued

]Exemplary bifunctional degradation compounds of the present disclosure

| Ex. # | Structure | Compound Name |
|---|---|---|
| 215 | 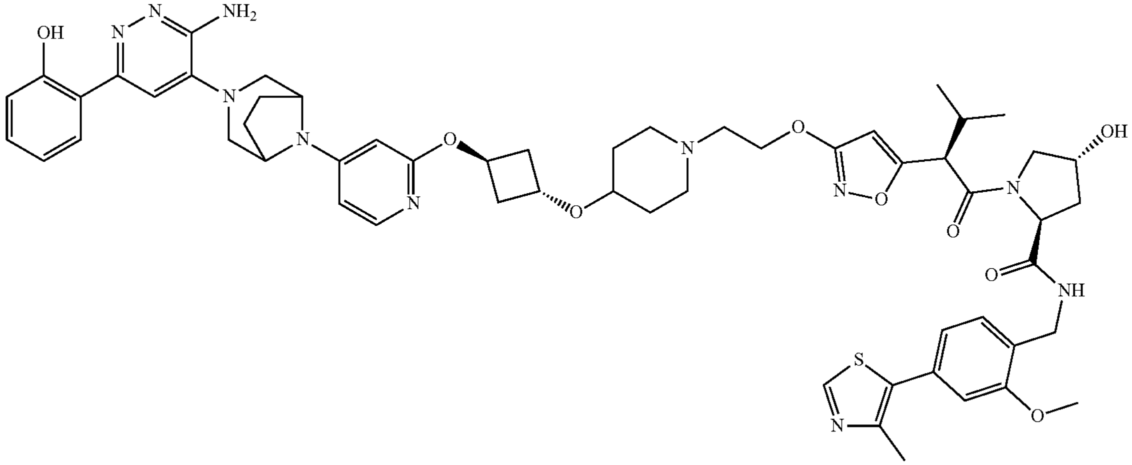 [SMILES: COc1cc(-c2scnc2C)ccc1CNC(=O)[C@@H]1C[C@@H](O)CN1C(=O)[C@@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-(2-methoxy-4-(4-methylthiazol-5-yl)benzyl)pyrrolidine-2-carboxamide |
| 216 | 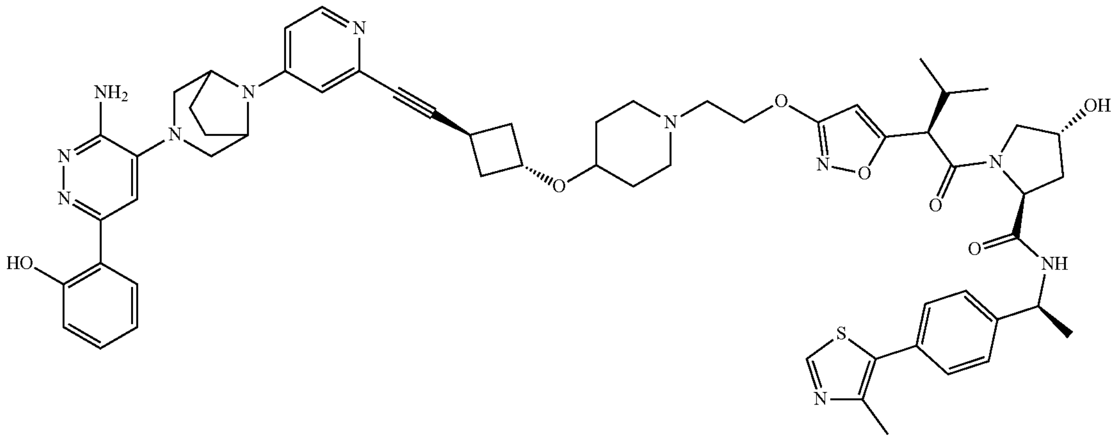 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](C#Cc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)ethynyl)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued
]Exemplary bifunctional degradation compounds of the present disclosure
| Ex. # | Structure | Compound Name |
| --- | --- | --- |
| 217 | 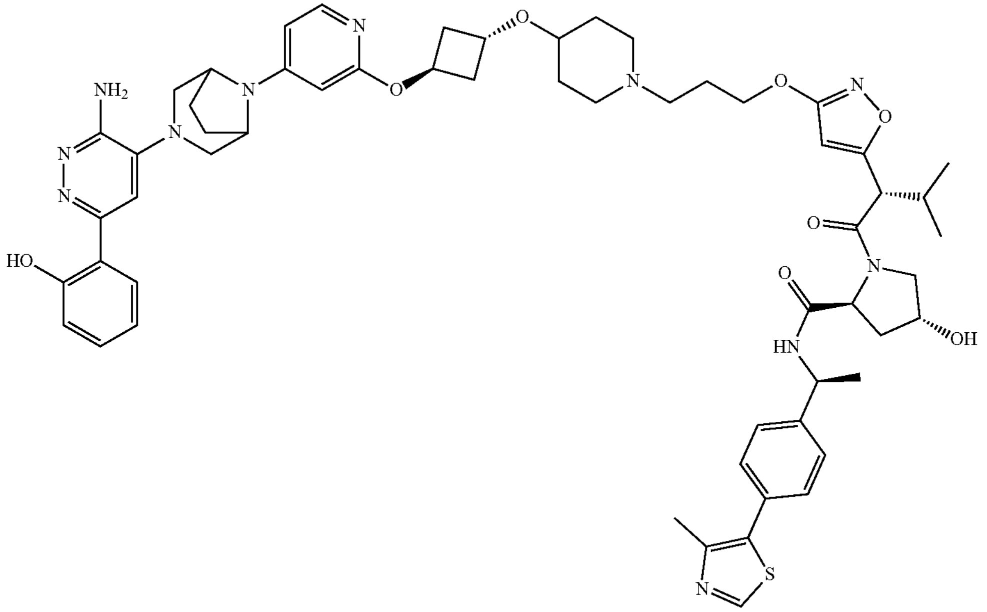 [SMILES: Cc1ncsc1-c1ccc([C@H](C)NC(=O)[C@@H]2C[C@@H](O)CN2C(=O)[C@H](c2cc(OCCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(3-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued
]Exemplary bifunctional degradation compounds of the present disclosure
| Ex. # | Structure | Compound Name |
|---|---|---|
| 218 | 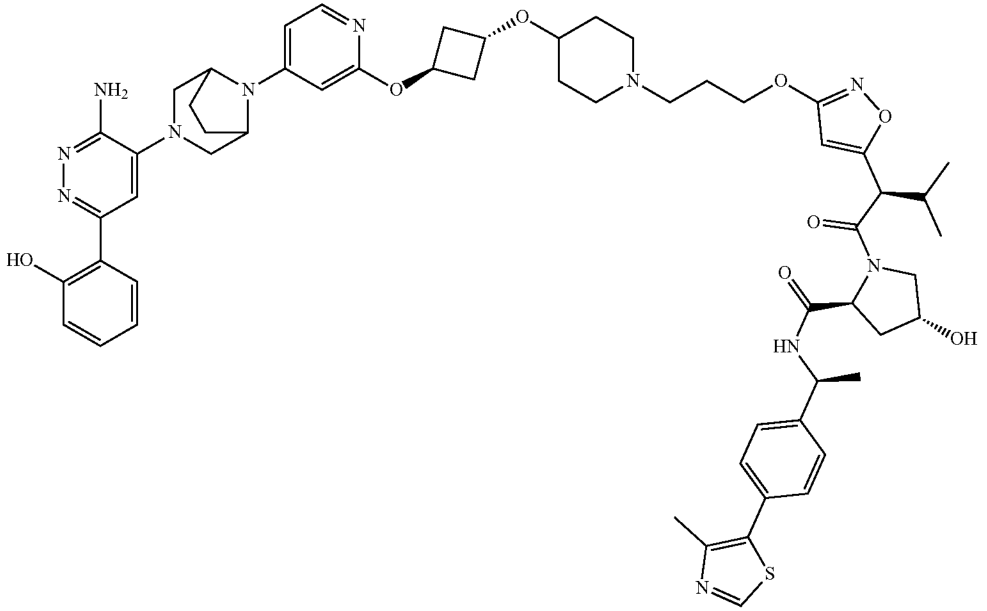 [SMILES: Cc1ncsc1-c1ccc([C@H](C)NC(=O)[C@@H]2C[C@@H](O)CN2C(=O)[C@@H](c2cc(OCCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

| Ex. # | Structure | Compound Name |
|---|---|---|
| ]Exemplary bifunctional degradation compounds of the present disclosure | | |
| 219 | 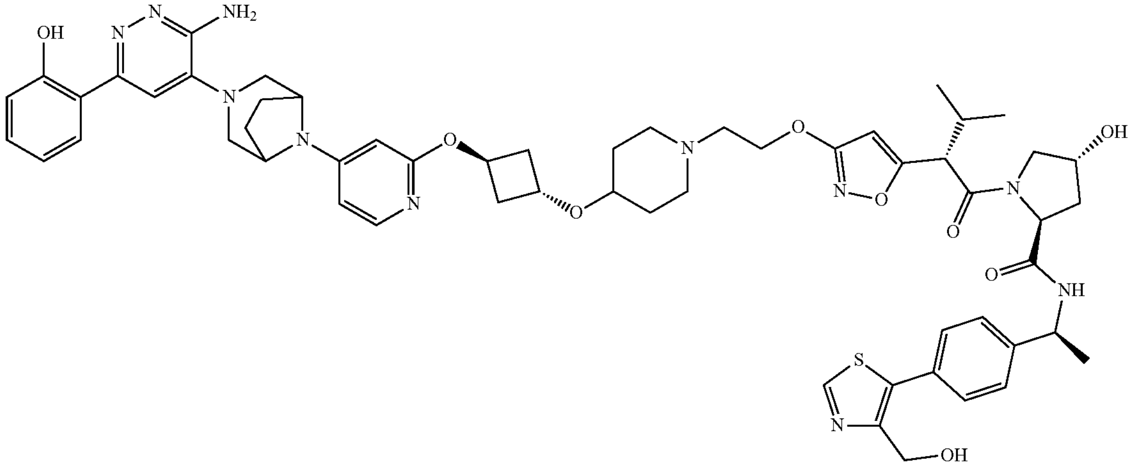 [SMILES: CC(C)[C@H](C(=O)N1C[C@H](O)C[C@H]1C(=O)N[C@@H](C)c1ccc(-c2scnc2CO)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-(hydroxymethyl)thiazol-5-yl)phenyl)ethyl)pyrrolidine-2-carboxamide |
| 220 | 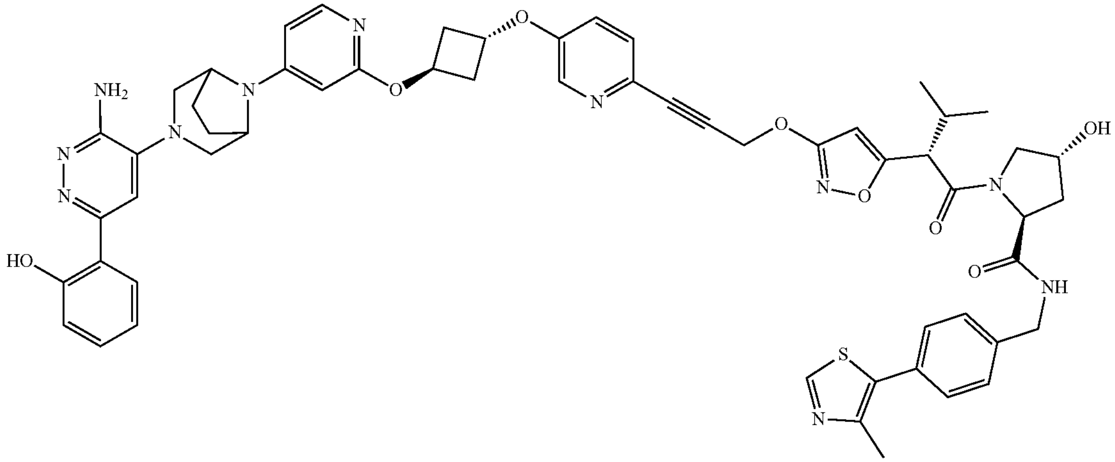 [SMILES: Cc1ncsc1-c1ccc(CNC(=O)[C@@H]2C[C@@H](O)CN2C(=O)[C@H](c2cc(OCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-(4-(4-methylthiazol-5-yl)benzyl)pyrrolidine-2-carboxamide |

TABLE 1B-continued

]Exemplary bifunctional degradation compounds of the present disclosure

| Ex. # | Structure | Compound Name |
|---|---|---|
| 221 | 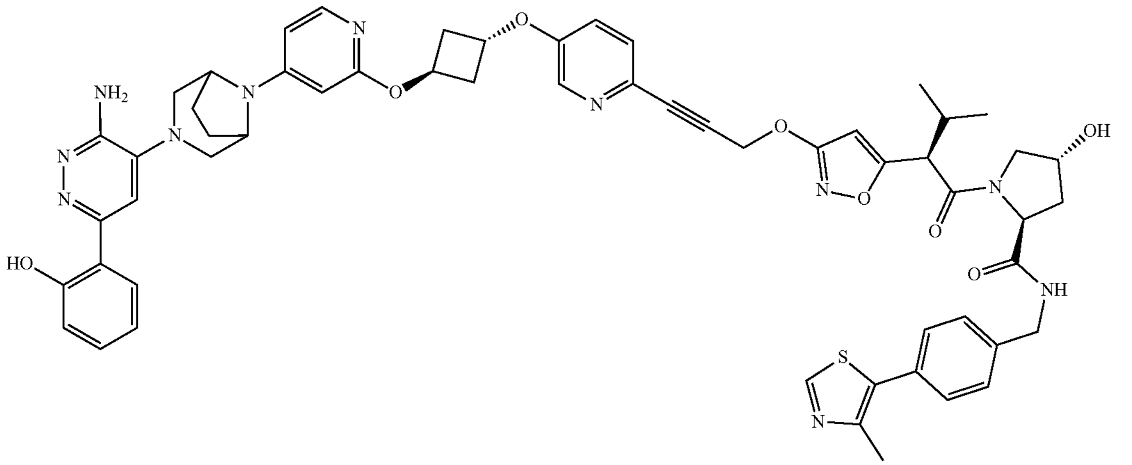 [SMILES: Cc1ncsc1-c1ccc(CNC(=O)[C@@H]2C[C@@H](O)CN2C(=O)[C@@H](c2cc(OCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-(4-(4-methylthiazol-5-yl)benzyl)pyrrolidine-2-carboxamide |
| 222 | 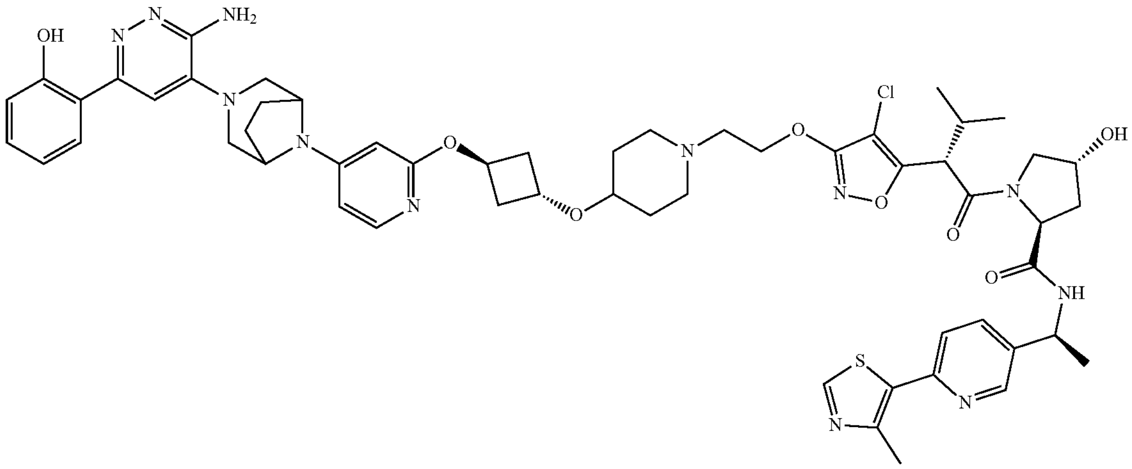 [SMILES: Cc1ncsc1-c1ccc([C@H](C)NC(=O)[C@@H]2C[C@@H](O)CN2C(=O)[C@H](c2onc(OCCN3CCC(O[C@H]4C[C@H](Oc5cc(N6C7CCC6CN(c6cc(-c8ccccc8O)nnc6N)C7)ccn5)C4)CC3)c2Cl)C(C)C)cn1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-chloroisoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 223 | 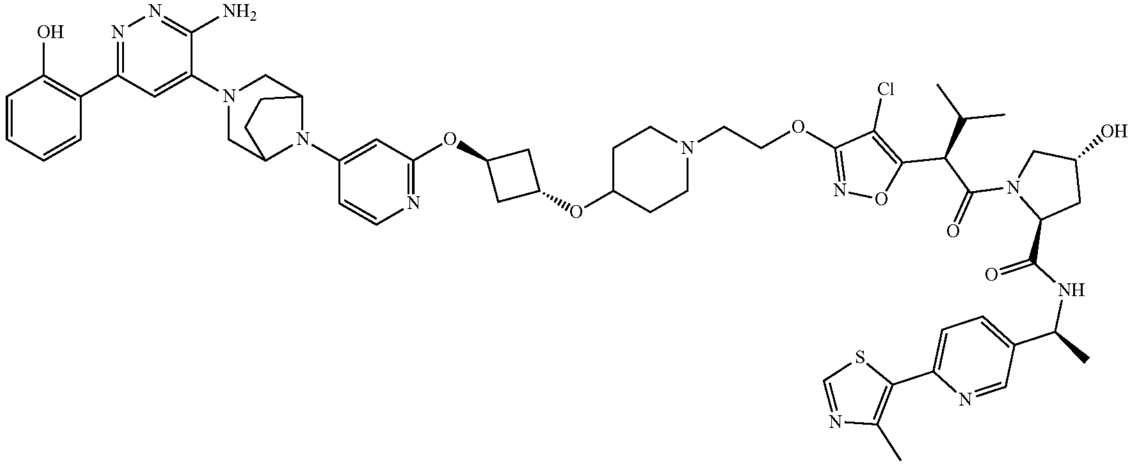 [SMILES: Cc1ncsc1-c1ccc([C@H](C)NC(=O)[C@@H]2C[C@@H](O)CN2C(=O)[C@@H](c2onc(OCCN3CCC(O[C@H]4C[C@H](Oc5cc(N6C7CCC6CN(c6cc(-c8ccccc8O)nnc6N)C7)ccn5)C4)CC3)c2Cl)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-chloroisoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 224 | 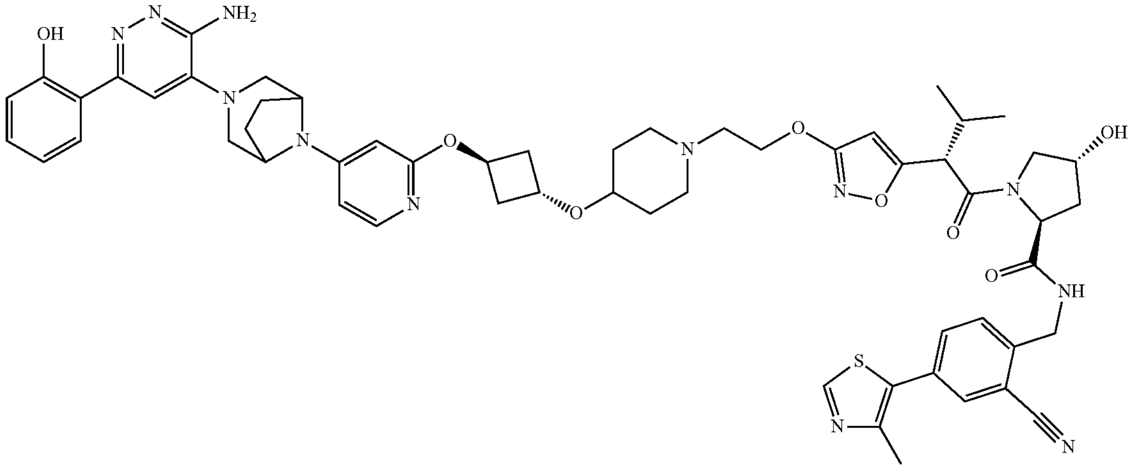 [SMILES: Cc1ncsc1-c1ccc(CNC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)c(C#N)c1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-(2-cyano-4-(4-methylthiazol-5-yl)benzyl)-4-hydroxypyrrolidine-2-carboxamide |

TABLE 1B-continued

]Exemplary bifunctional degradation compounds of the present disclosure

| Ex. # | Structure | Compound Name |
|---|---|---|
| 225 | 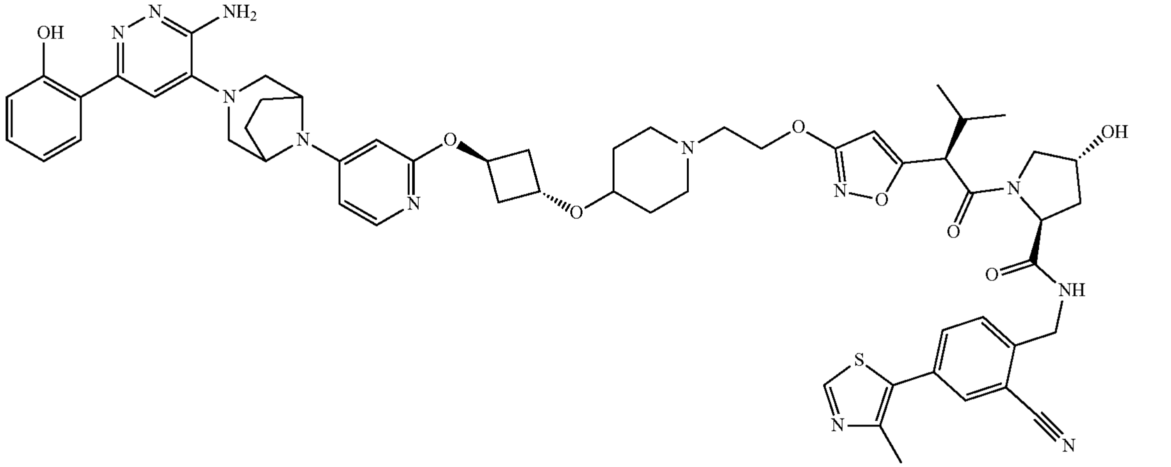 [SMILES: Cc1ncsc1-c1ccc(CNC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)c(C#N)c1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-(2-cyano-4-(4-methylthiazol-5-yl)benzyl)-4-hydroxypyrrolidine-2-carboxamide |
| 226 | 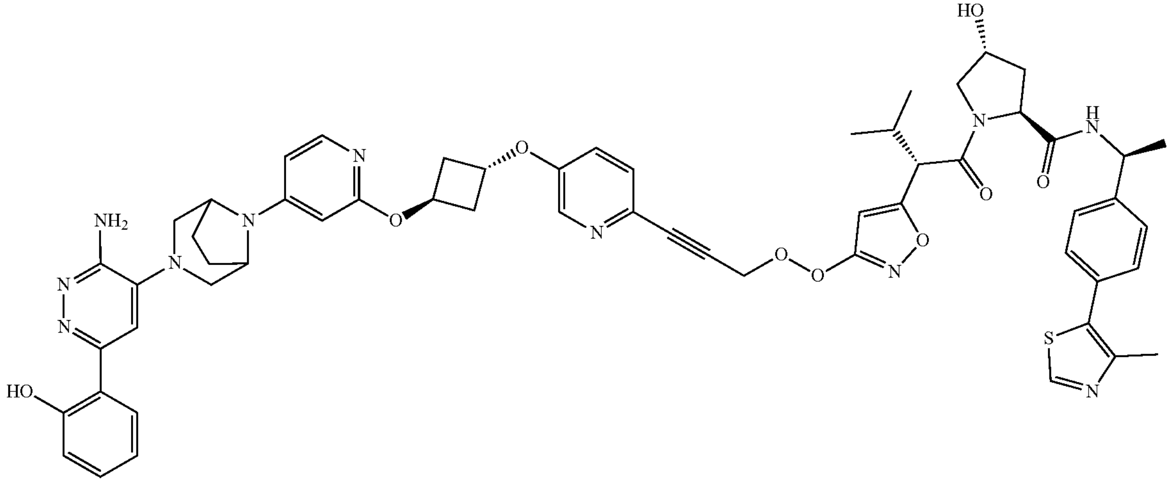 [SMILES: Cc1ncsc1-c1ccc([C@H](C)NC(=O)[C@@H]2C[C@@H](O)CN2C(=O)[C@H](c2cc(OOCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2S)-2-(3-((4-(5-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)but-3-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 227 | 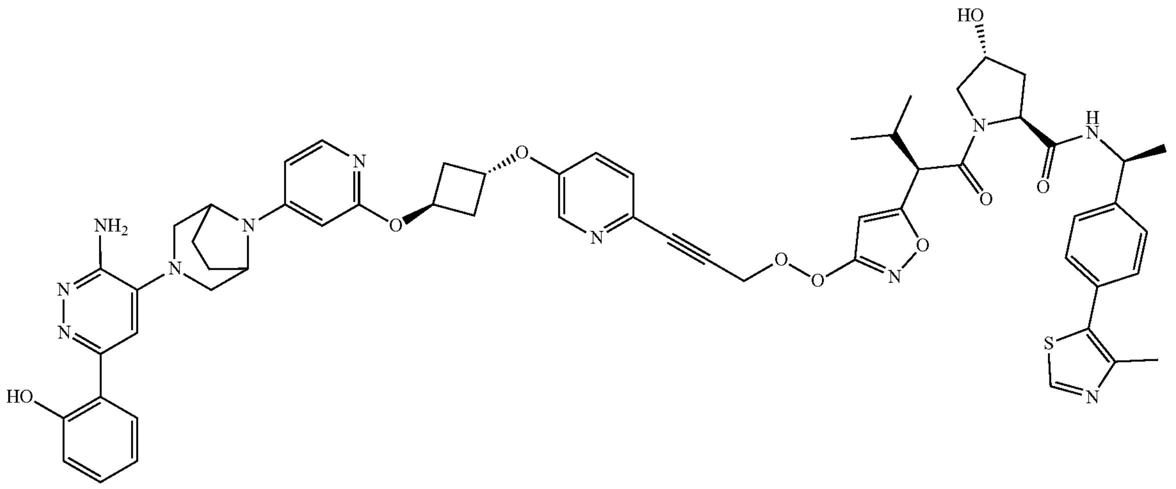 [SMILES: Cc1ncsc1-c1ccc([C@H](C)NC(=O)[C@@H]2C[C@@H](O)CN2C(=O)[C@@H](c2cc(OOCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-((4-(5-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)but-3-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 228 | 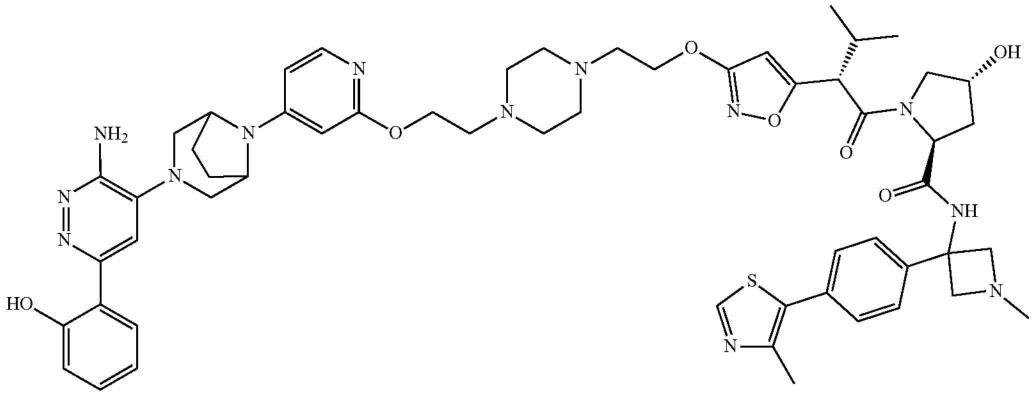 [SMILES: Cc1ncsc1-c1ccc(C2(NC(=O)[C@@H]3C[C@@H](O)CN3C(=O)[C@H](c3cc(OCCN4CCN(CCOc5cc(N6C7CCC6CN(c6cc(-c8ccccc8O)nnc6N)C7)ccn5)CC4)no3)C(C)C)CN(C)C2)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-(1-methyl-3-(4-(4-methylthiazol-5-yl)phenyl)azetidin-3-yl)pyrrolidine-2-carboxamide |

TABLE 1B-continued

| ]Exemplary bifunctional degradation compounds of the present disclosure | | |
|---|---|---|
| Ex. # | Structure | Compound Name |
| 229 | 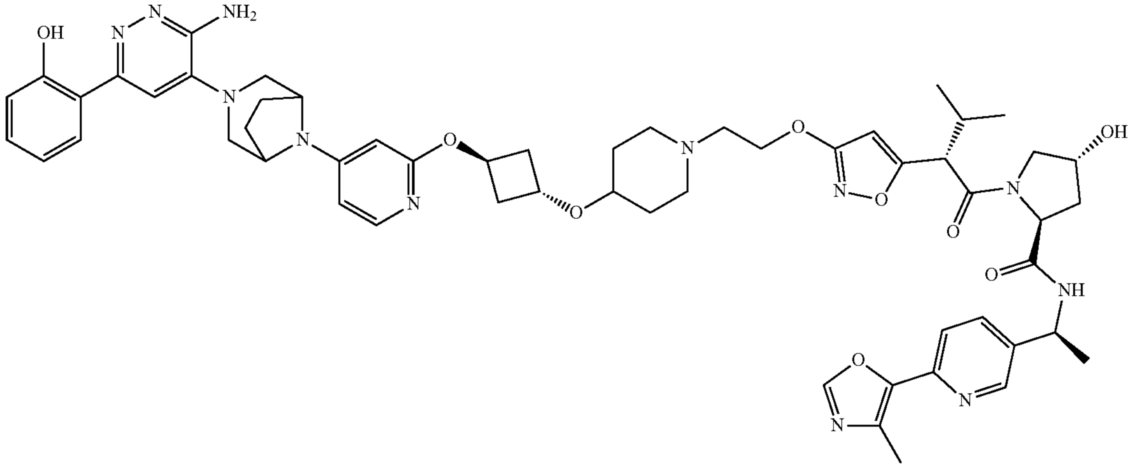 [SMILES: Cc1ncoc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(4-methyloxazol-5-yl)pyridin-3-yl)ethyl)pyrrolidine-2-carboxamide |
| 230 | 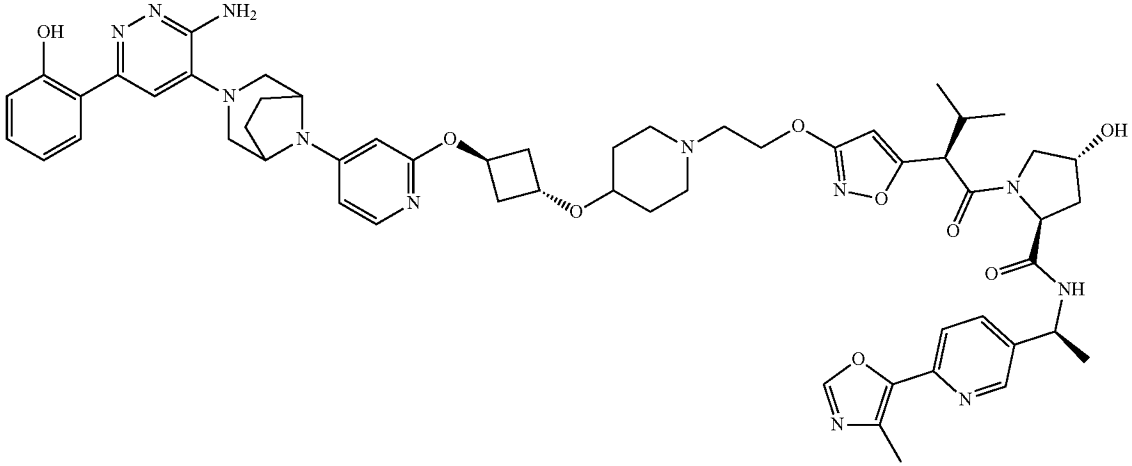 [SMILES: Cc1ncoc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(4-methyloxazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 231 | 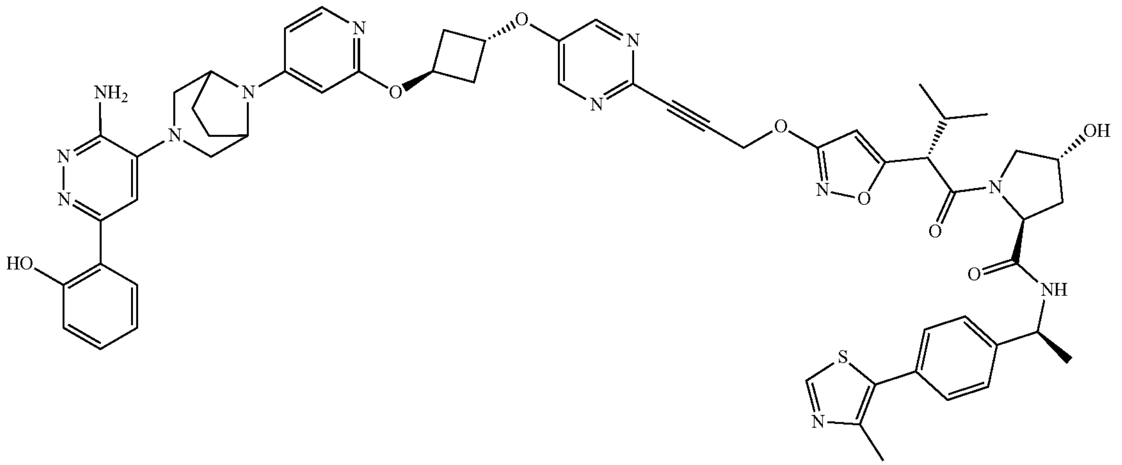 [SMILES: Cc1ncsc1-c1ccc([C@H](C)NC(=O)[C@@H]2C[C@@H](O)CN2C(=O)[C@H](c2cc(OCC#Cc3ncc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 232 | 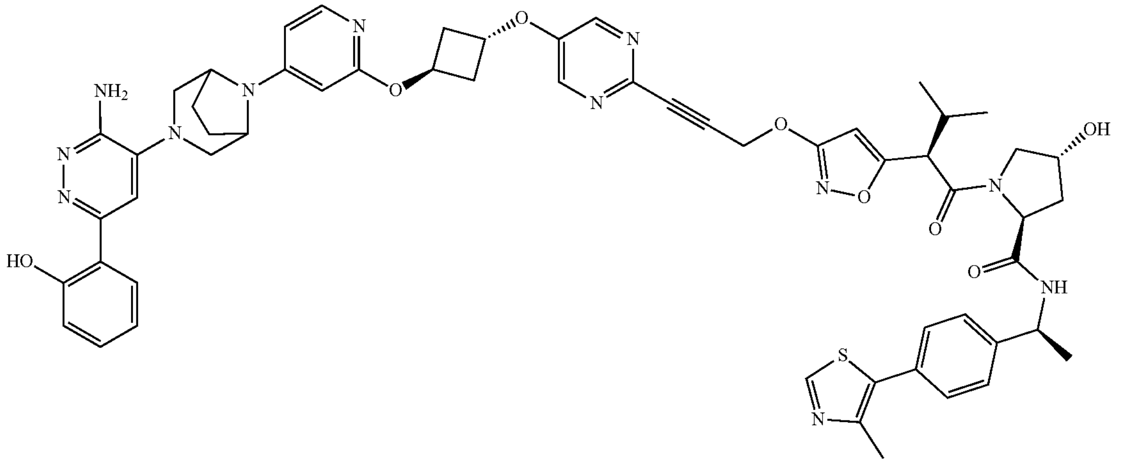 [SMILES: Cc1ncsc1-c1ccc([C@H](C)NC(=O)[C@@H]2C[C@@H](O)CN2C(=O)[C@@H](c2cc(OCC#Cc3ncc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 233 | 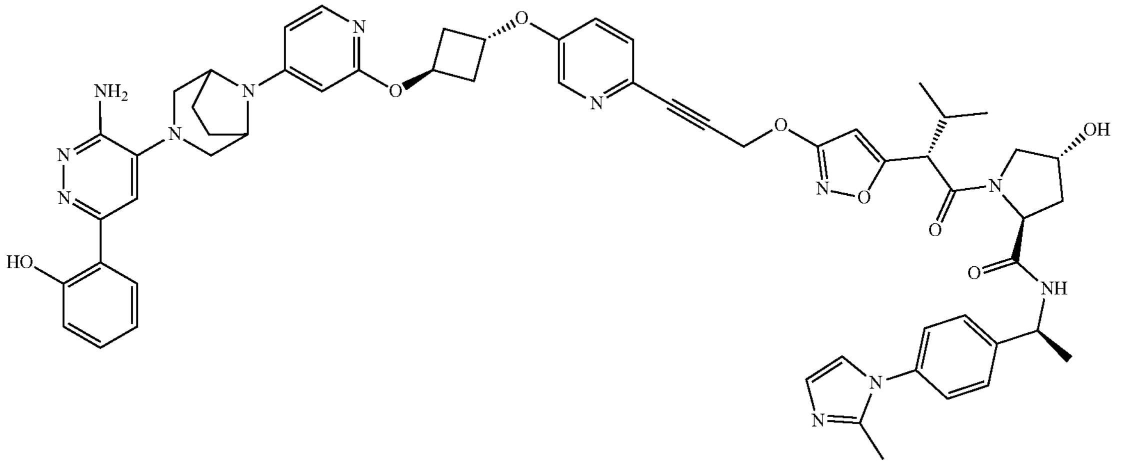 [SMILES: Cc1nccn1-c1ccc([C@H](C)NC(=O)[C@@H]2C[C@@H](O)CN2C(=O)[C@H](c2cc(OCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |
| 234 | 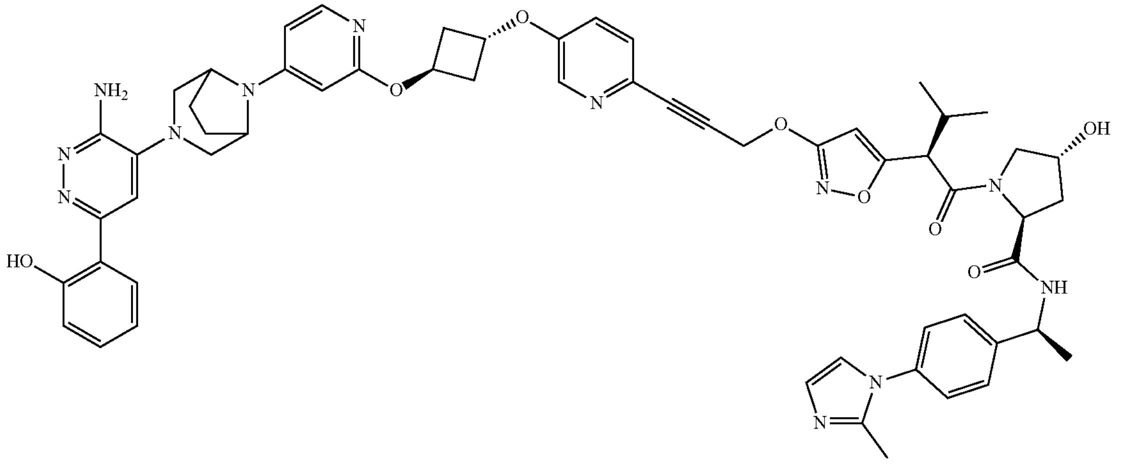 [SMILES: Cc1nccn1-c1ccc([C@H](C)NC(=O)[C@@H]2C[C@@H](O)CN2C(=O)[C@@H](c2cc(OCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 235 | 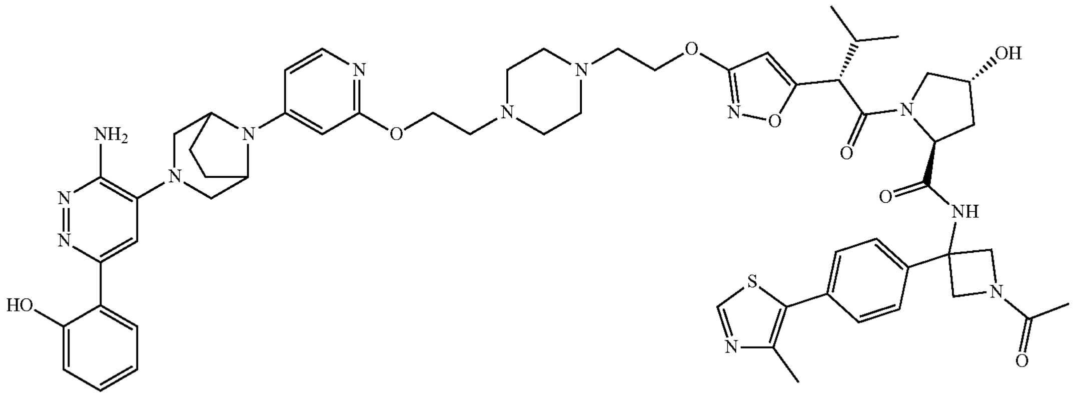 [SMILES: CC(=O)N1CC(NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)(c2ccc(-c3scnc3C)cc2)C1] | (2S,4R)-N-(1-acetyl-3-(4-(4-methylthiazol-5-yl)phenyl)azetidin-3-yl)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |
| 236 | 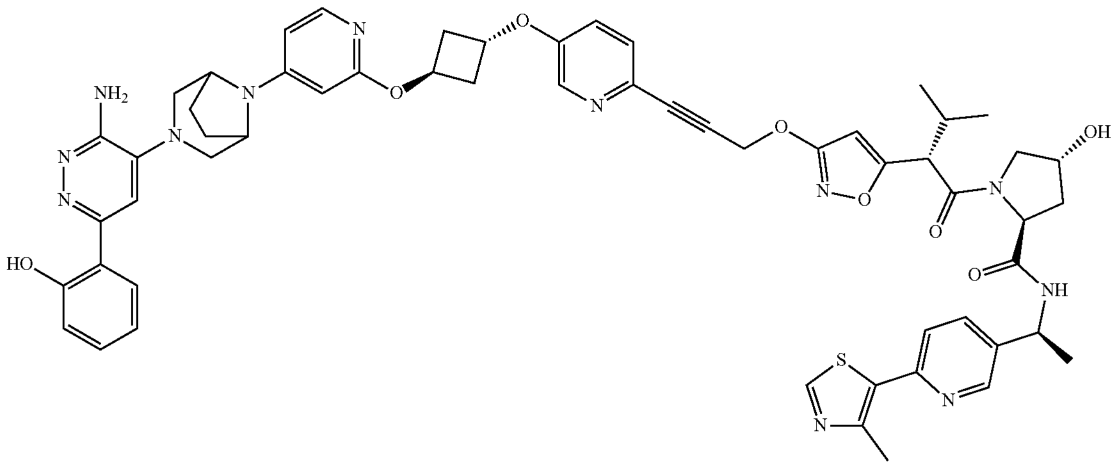 [SMILES: Cc1ncsc1-c1ccc([C@H](C)NC(=O)[C@@H]2C[C@@H](O)CN2C(=O)[C@H](c2cc(OCC#Cc3ccc(O[C@H]4C[C@H](Oc5cc(N6C7CCC6CN(c6cc(-c8ccccc8O)nnc6N)C7)ccn5)C4)cn3)no2)C(C)C)cn1] | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
|---|---|---|
| 237 | 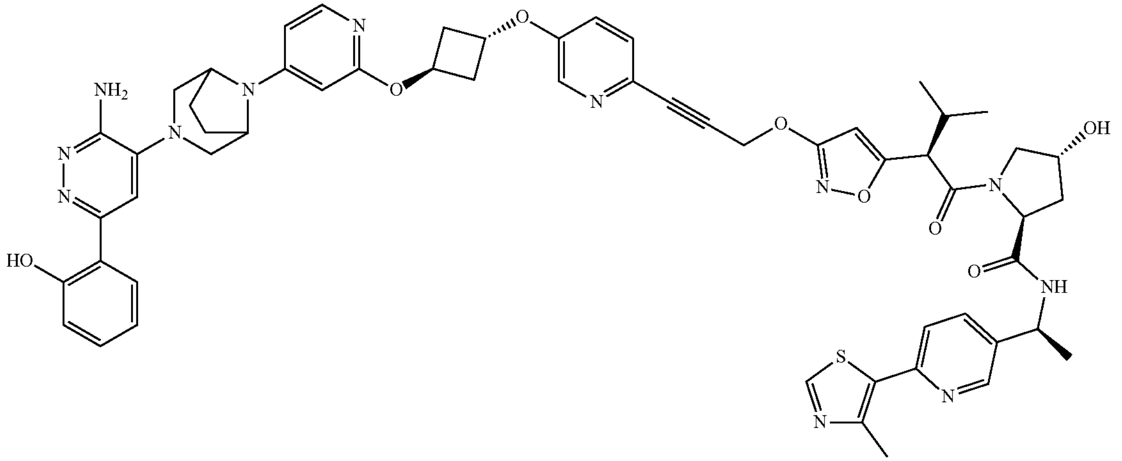 [SMILES: Cc1ncsc1-c1ccc([C@H](C)NC(=O)[C@@H]2C[C@@H](O)CN2C(=O)[C@@H](c2cc(OCC#Cc3ccc(O[C@H]4C[C@H](Oc5cc(N6C7CCC6CN(c6cc(-c8ccccc8O)nnc6N)C7)ccn5)C4)cn3)no2)C(C)C)cn1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 238 | 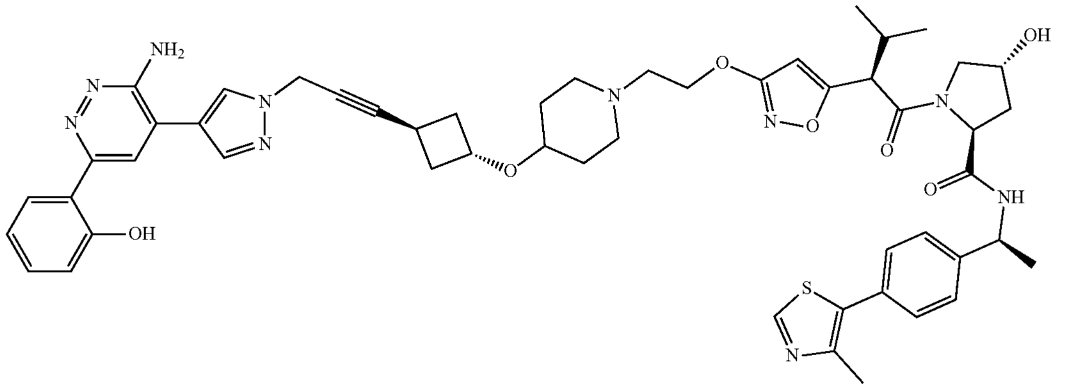 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](C#CCn5cc(-c6cc(-c7ccccc7O)nnc6N)cn5)C4)CC3)no2)C(C)C)cc1] | (2S,4R)-1-((R)-2-(3-(2-(4-((1r,3R)-3-(3-(4-(3-amino-6-(2-hydroxyphenyl)pyridazin-4-yl)-1H-pyrazol-1-yl)prop-1-yn-1-yl)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 239 | 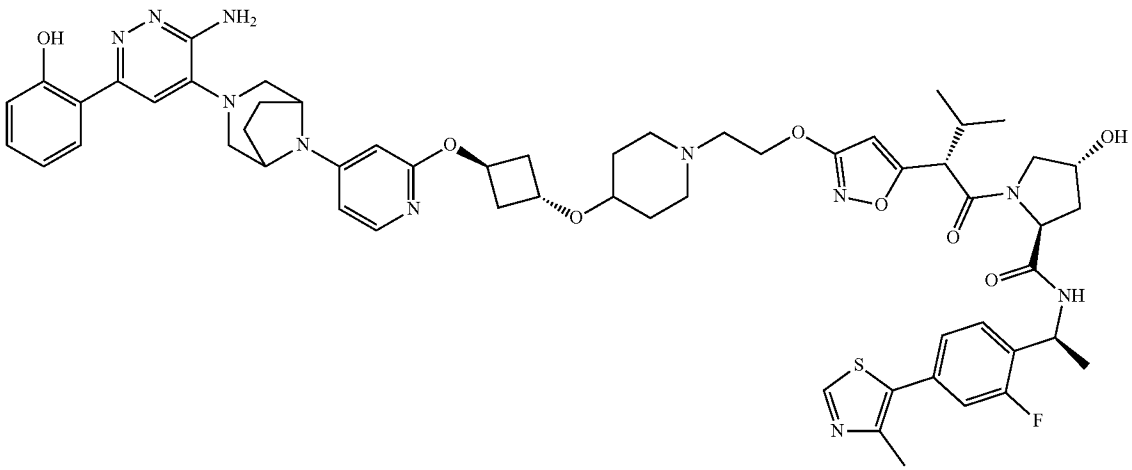 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)c(F)c1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(2-fluoro-4-(4-methylthiazol-5-yl)phenyl)ethyl)-4-hydroxypyrrolidine-2-carboxamide |
| 240 | 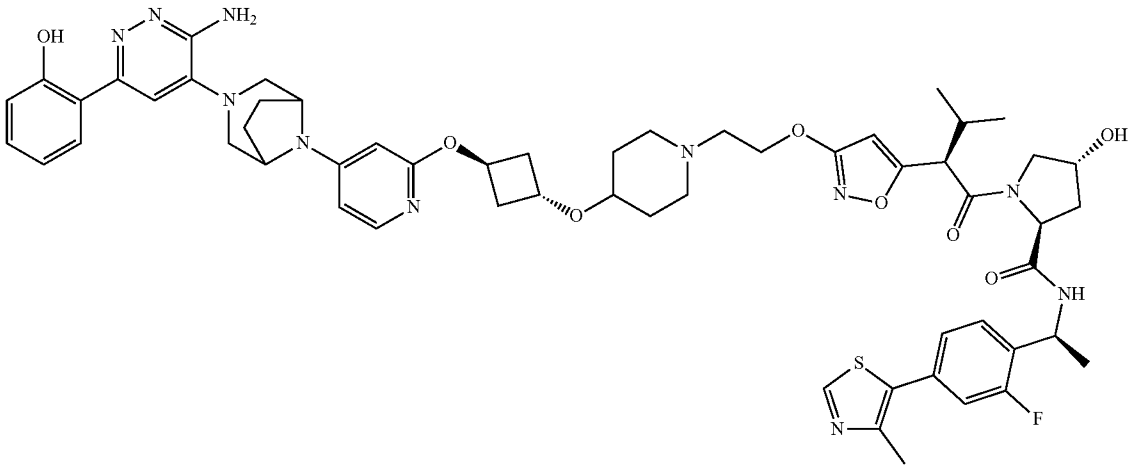 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)c(F)c1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(2-fluoro-4-(4-methylthiazol-5-yl)phenyl)ethyl)-4-hydroxypyrrolidine-2-carboxamide |

TABLE 1B-continued

| ]Exemplary bifunctional degradation compounds of the present disclosure | | |
|---|---|---|
| Ex. # | Structure | Compound Name |
| 241 | 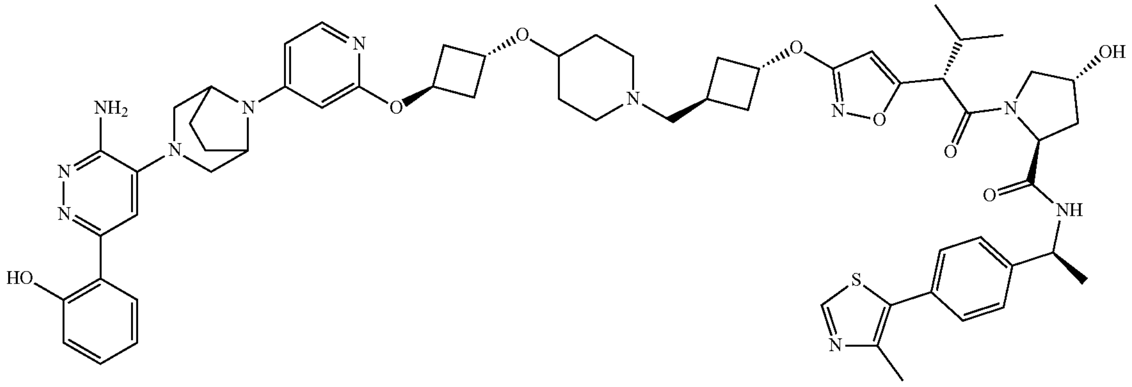 [SMILES: Cc1ncsc1-c1ccc([C@H](C)NC(=O)[C@@H]2C[C@@H](O)CN2C(=O)[C@H](c2cc(O[C@H]3C[C@H](CN4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2S)-2-(3-((1R,3S)-3-((4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)cyclobutoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 242 | 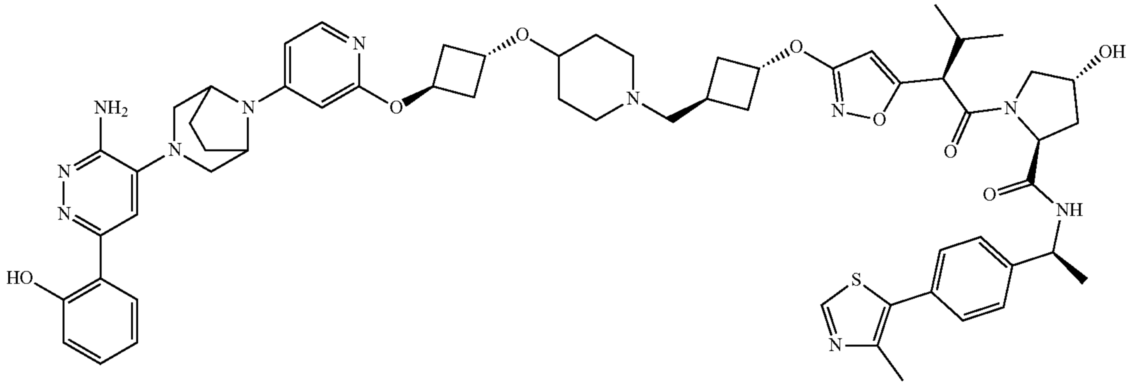 [SMILES: Cc1ncsc1-c1ccc([C@H](C)NC(=O)[C@@H]2C[C@@H](O)CN2C(=O)[C@@H](c2cc(O[C@H]3C[C@H](CN4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2R)-2-(3-((1R,3R)-3-((4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)cyclobutoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 243 | 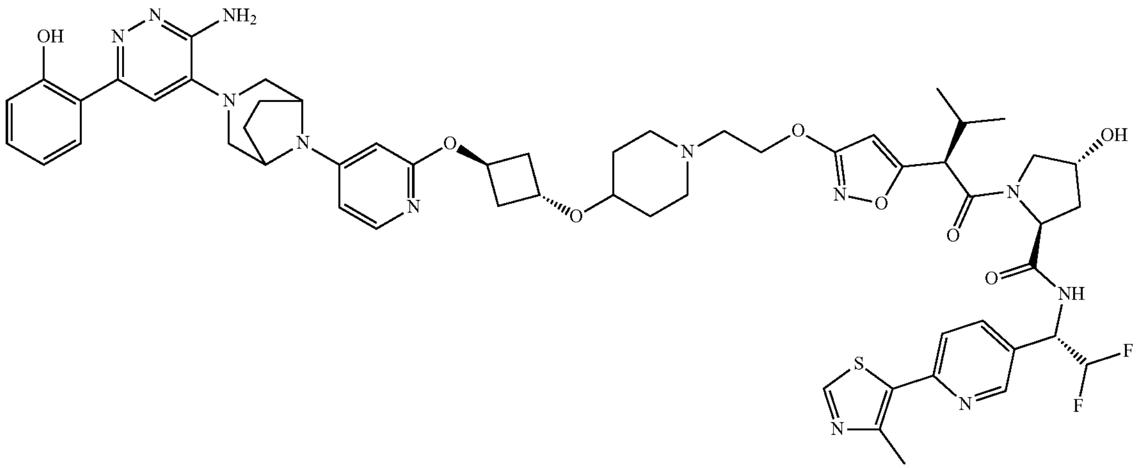 [SMILES: Cc1ncsc1-c1ccc([C@H](NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)C(F)F)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-2,2-difluoro-1-(6-(4-methylthiazol-5-yl)pyridin-3-yl)ethyl)-4-hydroxypyrrolidine-2-carboxamide |
| 244 | 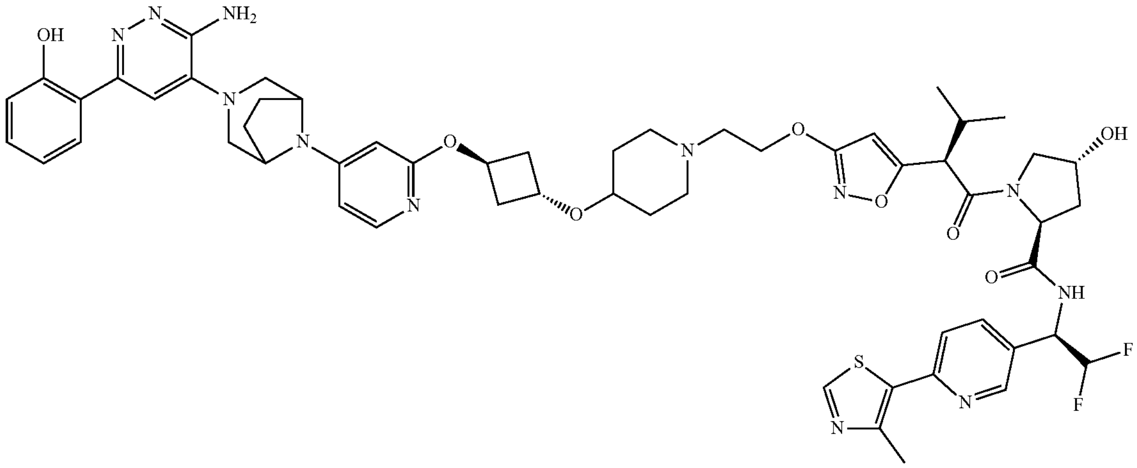 [SMILES: Cc1ncsc1-c1ccc([C@@H](NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)C(F)F)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-2,2-difluoro-1-(6-(4-methylthiazol-5-yl)pyridin-3-yl)ethyl)-4-hydroxypyrrolidine-2-carboxamide |

TABLE 1B-continued

]Exemplary bifunctional degradation compounds of the present disclosure

| Ex. # | Structure | Compound Name |
|---|---|---|
| 245 | 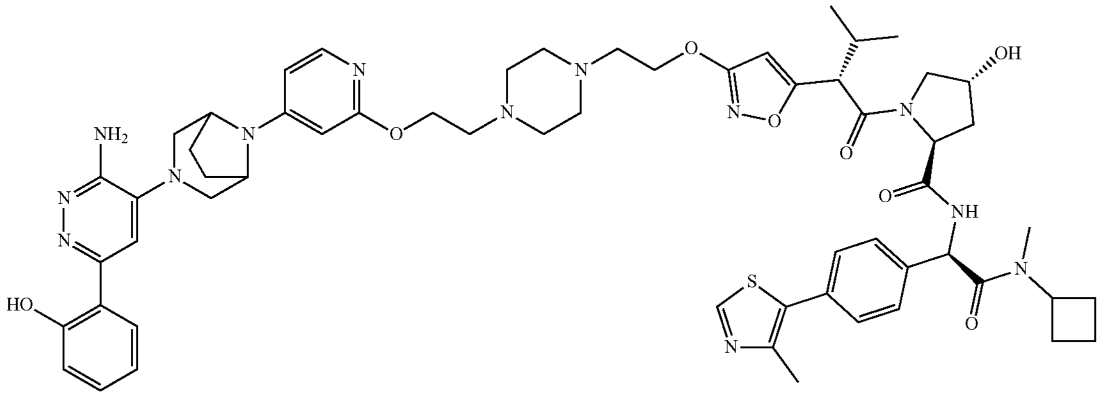 [SMILES: Cc1ncsc1-c1ccc([C@@H](NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)C(=O)N(C)C2CCC2)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-(cyclobutyl(methyl)amino)-1-(4-(4-methylthiazol-5-yl)phenyl)-2-oxoethyl)-4-hydroxypyrrolidine-2-carboxamide |
| 246 | 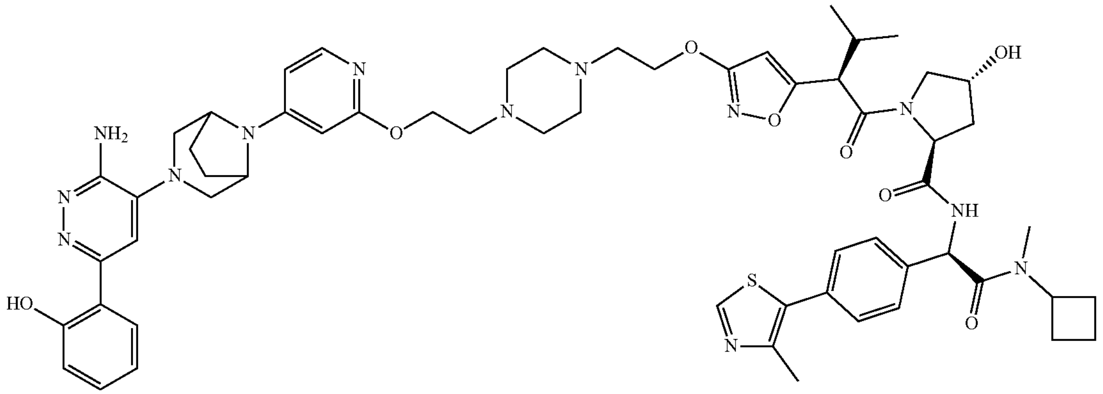 [SMILES: Cc1ncsc1-c1ccc([C@@H](NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)C(=O)N(C)C2CCC2)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-(cyclobutyl(methyl)amino)-1-(4-(4-methylthiazol-5-yl)phenyl)-2-oxoethyl)-4-hydroxypyrrolidine-2-carboxamide |

TABLE 1B-continued

| ]Exemplary bifunctional degradation compounds of the present disclosure | | |
|---|---|---|
| Ex. # | Structure | Compound Name |
| 247 | 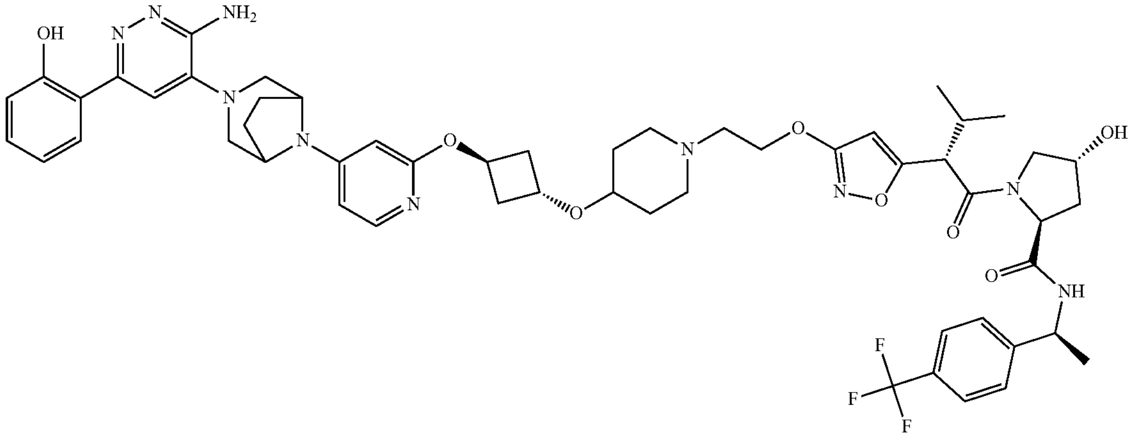 [SMILES: CC(C)[C@H](C(=O)N1C[C@H](O)C[C@H]1C(=O)N[C@@H](C)c1ccc(C(F)(F)F)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(trifluoromethyl)phenyl)ethyl) pyrrolidine-2-carboxamide |
| 248 | 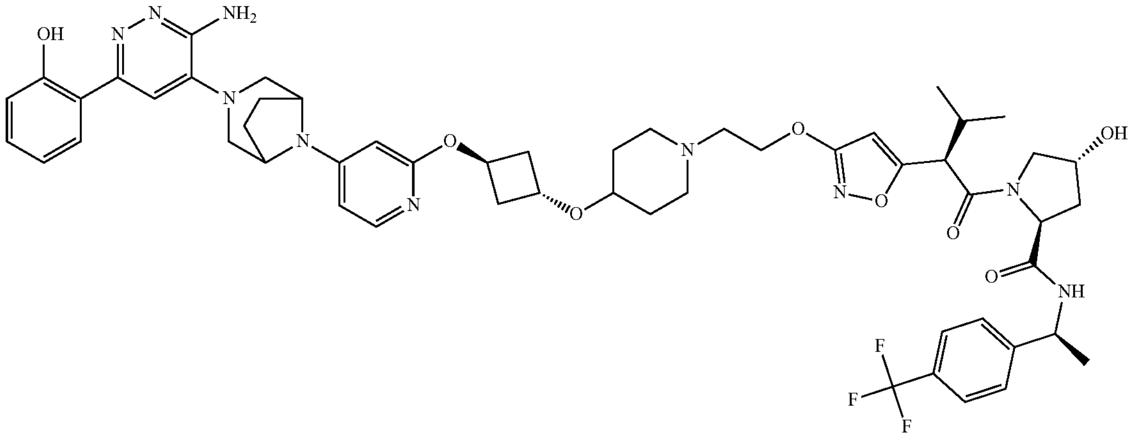 [SMILES: CC(C)[C@@H](C(=O)N1C[C@H](O)C[C@H]1C(=O)N[C@@H](C)c1ccc(C(F)(F)F)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(trifluoromethyl)phenyl)ethyl) pyrrolidine-2-carboxamide |

TABLE 1B-continued

| ]Exemplary bifunctional degradation compounds of the present disclosure | | |
|---|---|---|
| Ex. # | Structure | Compound Name |
| 249 | 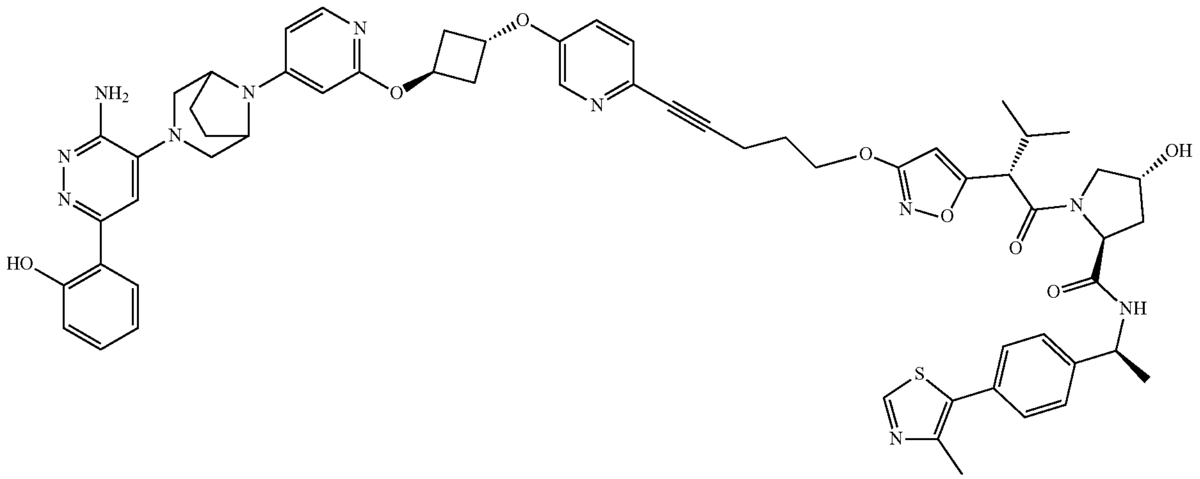 [SMILES: Cc1ncsc1-c1ccc([C@H](C)NC(=O)[C@@H]2C[C@@H](O)CN2C(=O)[C@H](c2cc(OCCCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2S)-2-(3-((5-(5-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)pent-4-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 250 | 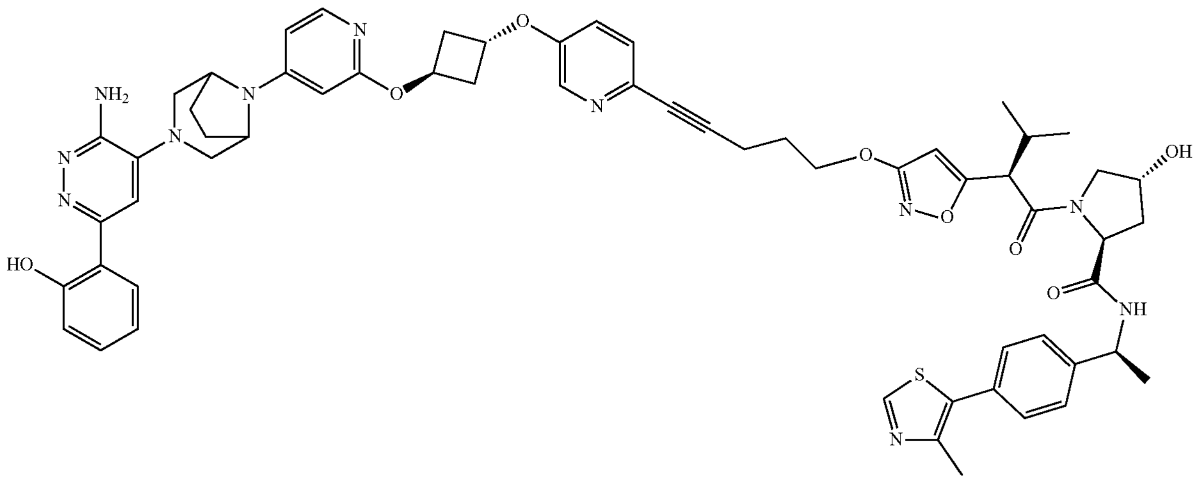 [SMILES: Cc1ncsc1-c1ccc([C@H](C)NC(=O)[C@@H]2C[C@@H](O)CN2C(=O)[C@@H](c2cc(OCCCC#Cc3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-((5-(5-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)pent-4-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 251 | 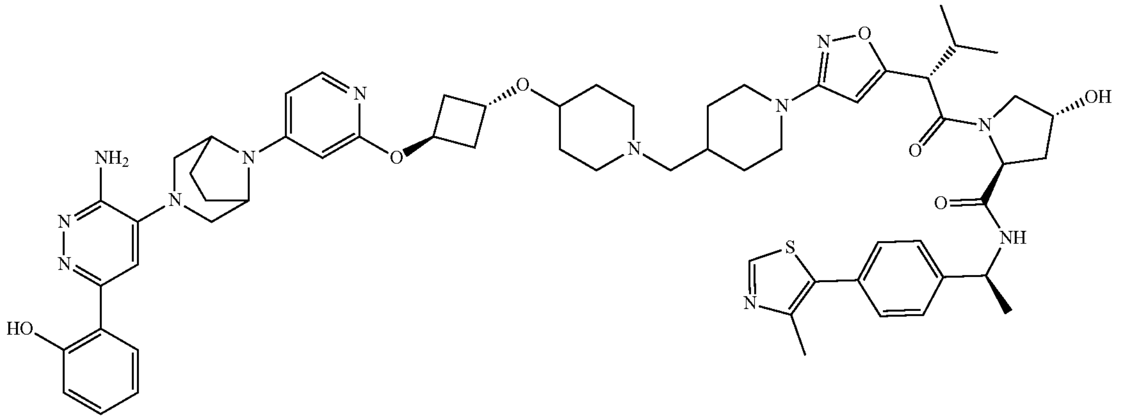 [SMILES: Cc1ncsc1-c1ccc([C@H](C)NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 252 | 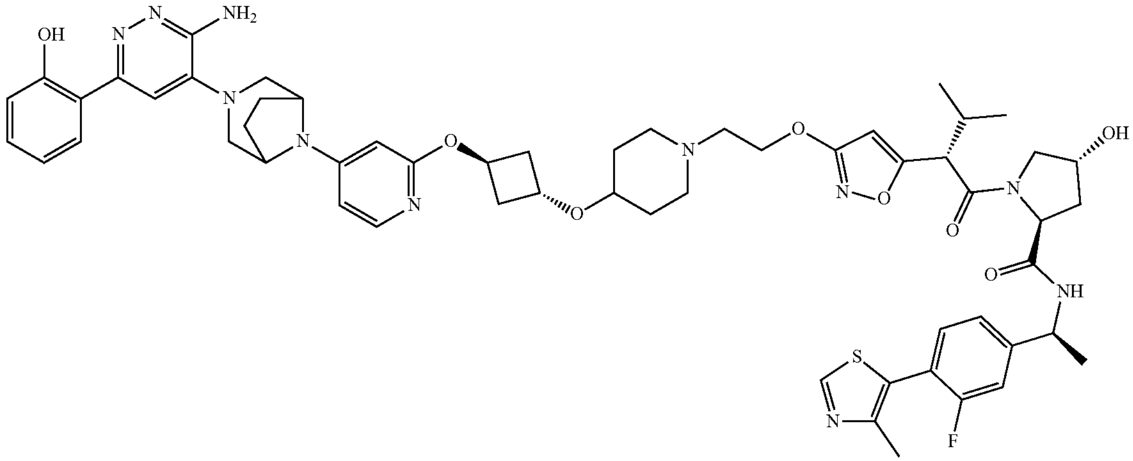 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1F] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(3-fluoro-4-(4-methylthiazol-5-yl)phenyl)ethyl)-4-hydroxypyrrolidine-2-carboxamide |

TABLE 1B-continued

]Exemplary bifunctional degradation compounds of the present disclosure

| Ex. # | Structure | Compound Name |
|---|---|---|
| 253 | 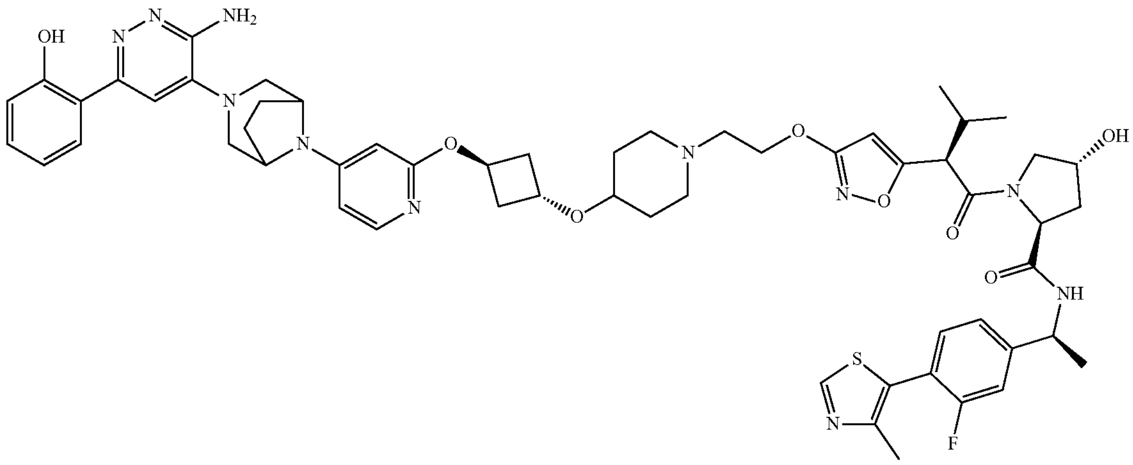 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1F] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(3-fluoro-4-(4-methylthiazol-5-yl)phenyl)ethyl)-4-hydroxypyrrolidine-2-carboxamide |
| 254 | 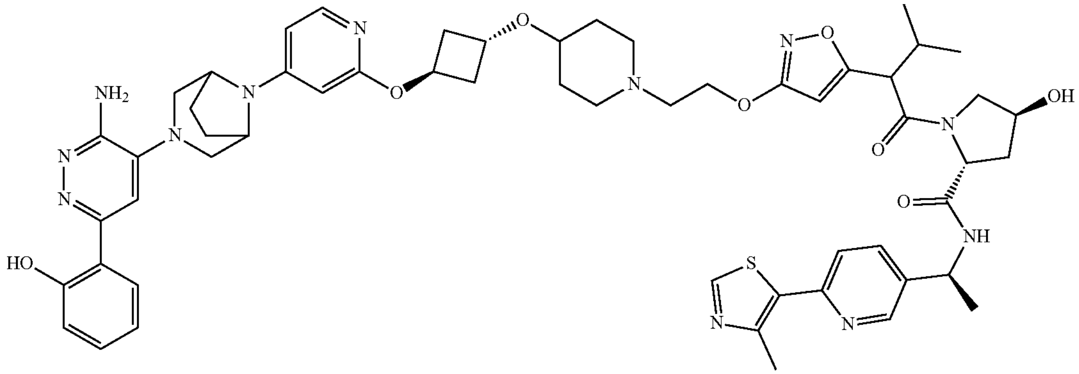 [SMILES: Cc1ncsc1-c1ccc([C@H](C)NC(=O)[C@H]2C[C@H](O)CN2C(=O)C(c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2R,4S)-1-(2-(3-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 255 | 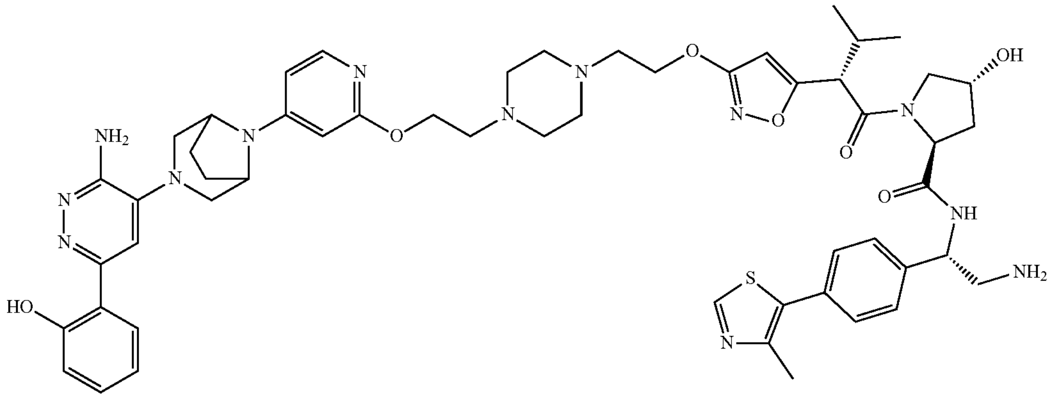 [SMILES: Cc1ncsc1-c1ccc([C@@H](CN)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-N-((S)-2-amino-1-(4-(4-methylthiazol-5-yl)phenyl)ethyl)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |
| 256 | 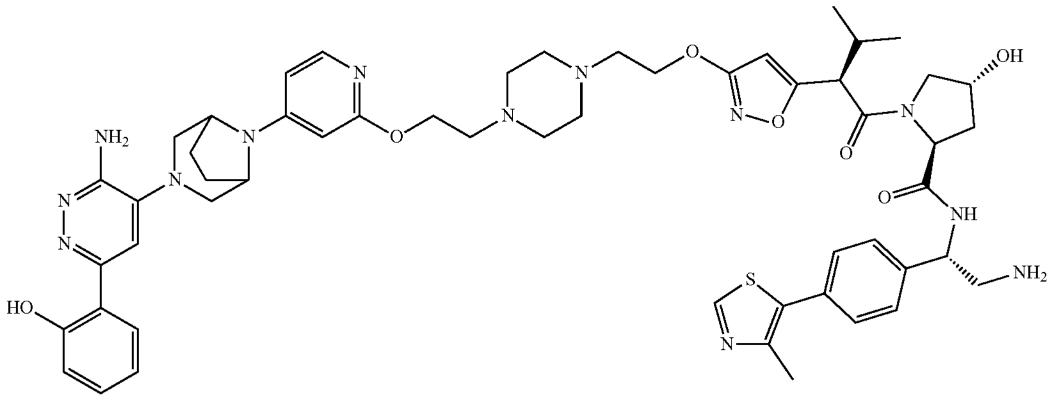 [SMILES: Cc1ncsc1-c1ccc([C@@H](CN)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-N-((S)-2-amino-1-(4-(4-methylthiazol-5-yl)phenyl)ethyl)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |

TABLE 1B-continued

| Ex. # | Structure | Compound Name |
|---|---|---|
| | ]Exemplary bifunctional degradation compounds of the present disclosure | |
| 257 | 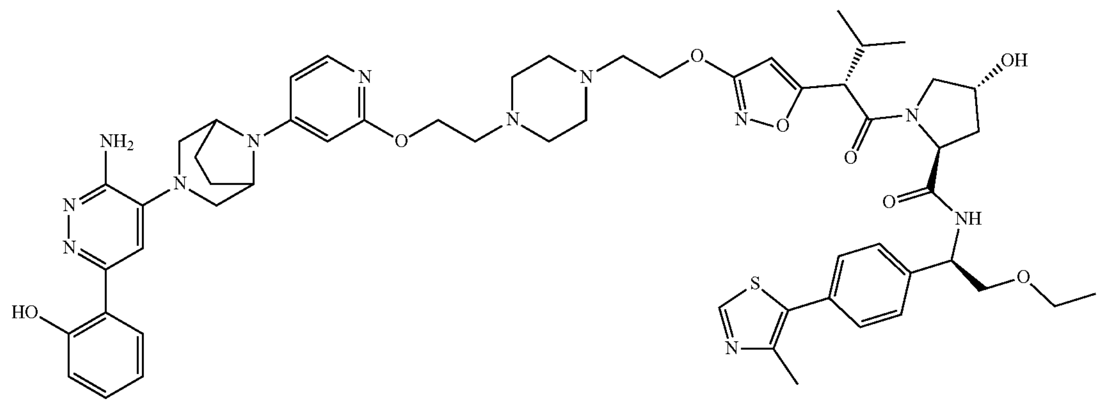 [SMILES: CCOC[C@H](NC(=O)[C@@H]1C[C@@H](O)CN1C(=O)[C@H](c1cc(OCCN2CCN(CCOc3cc(N4C5CCC4CN(c4cc(-c6ccccc6O)nnc4N)C5)ccn3)CC2)no1)C(C)C)c1ccc(-c2scnc2C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-ethoxy-1-(4-(4-methylthiazol-5-yl)phenyl)ethyl)-4-hydroxypyrrolidine-2-carboxamide |
| 258 | 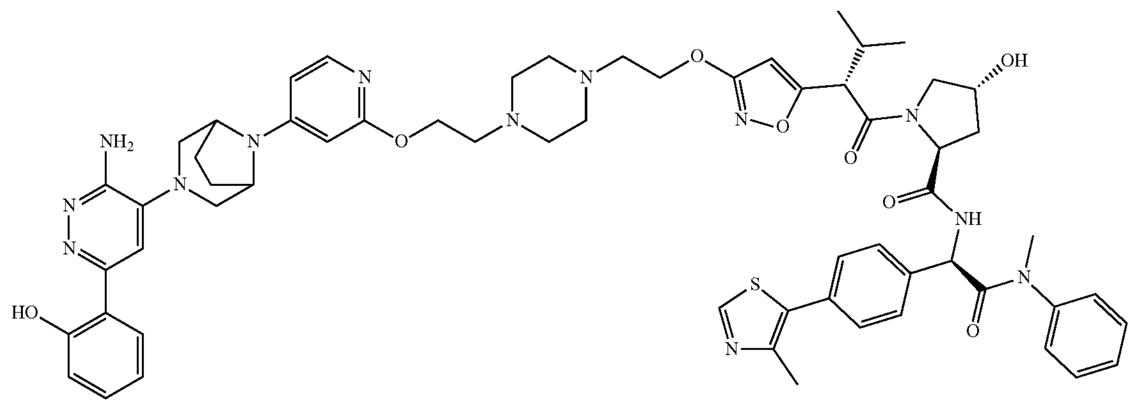 [SMILES: Cc1ncsc1-c1ccc([C@@H](NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)C(=O)N(C)c2ccccc2)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-2-(methyl(phenyl)amino)-1-(4-(4-methylthiazol-5-yl)phenyl)-2-oxoethyl)pyrrolidine-2-carboxamide |

TABLE 1B-continued

| Ex. # | Structure | Compound Name |
|---|---|---|
| | ]Exemplary bifunctional degradation compounds of the present disclosure | |
| 259 | 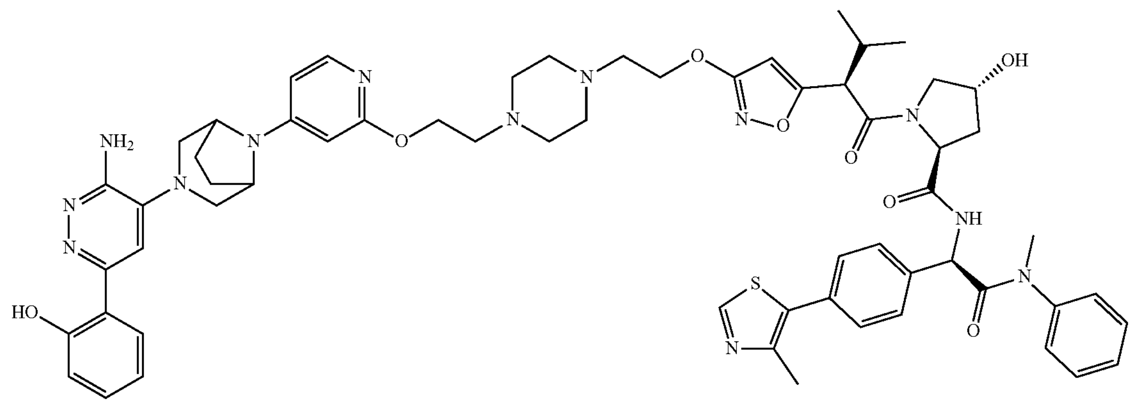 [SMILES: Cc1ncsc1-c1ccc([C@@H](NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)C(=O)N(C)c2ccccc2)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-2-(methyl(phenyl)amino)-1-(4-(4-methylthiazol-5-yl)phenyl)-2-oxoethyl)pyrrolidine-2-carboxamide |
| 260 | 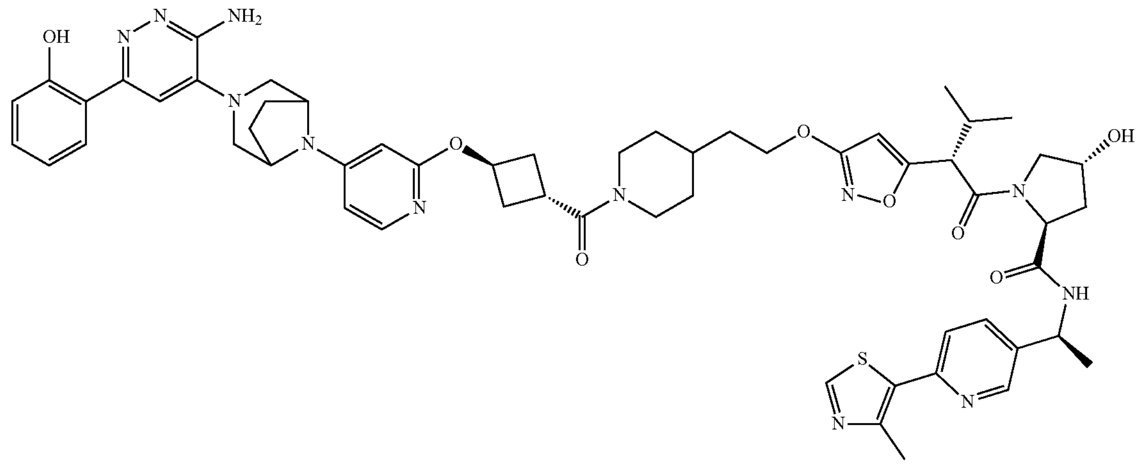 [SMILES: Cc1ncsc1-c1ccc([C@H](C)NC(=O)[C@@H]2C[C@@H](O)CN2C(=O)[C@H](c2cc(OCCC3CCN(C(=O)[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2S)-2-(3-(2-(1-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutane-1-carbonyl)piperidin-4-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
|---|---|---|
| 261 | 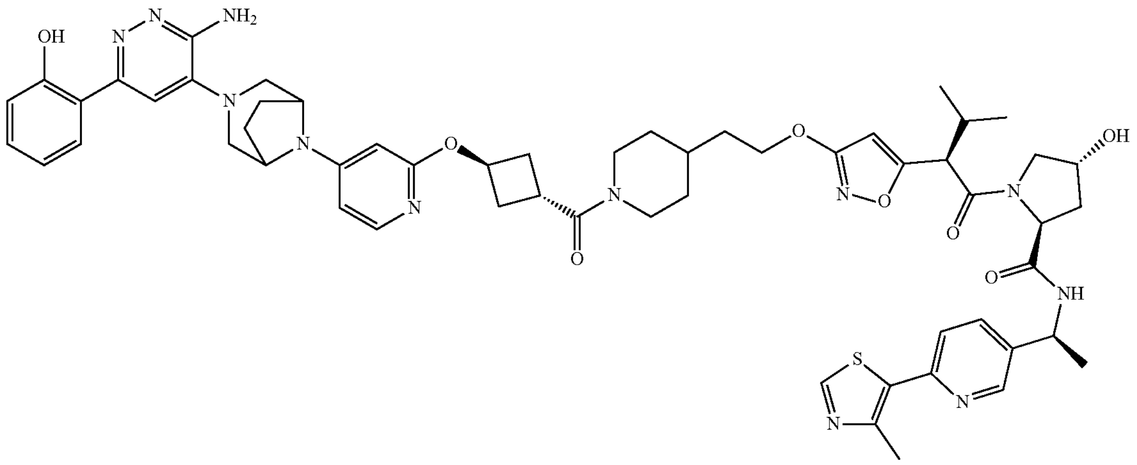 [SMILES: Cc1ncsc1-c1ccc([C@H](C)NC(=O)[C@@H]2C[C@@H](O)CN2C(=O)[C@@H](c2cc(OCCC3CCN(C(=O)[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(1-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutane-1-carbonyl)piperidin-4-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 262 | 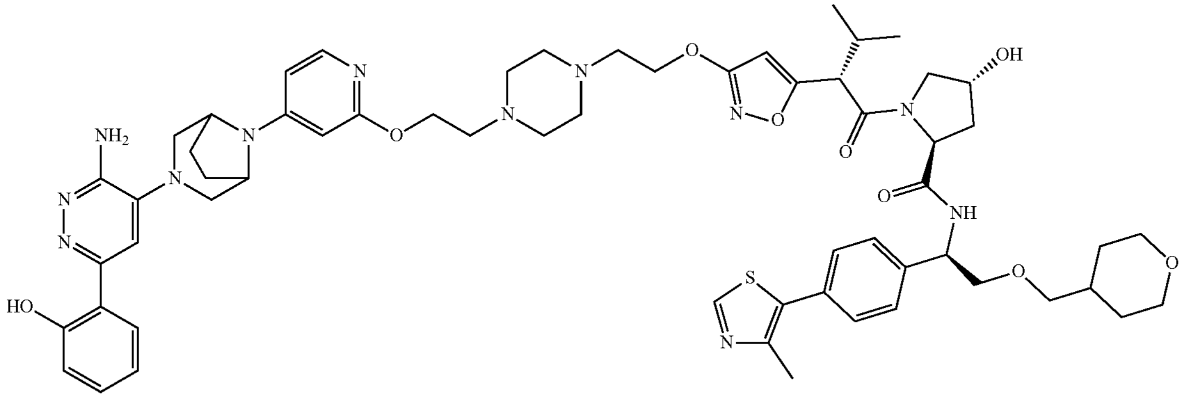 [SMILES: Cc1ncsc1-c1ccc([C@H](COCC2CCOCC2)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-1-(4-(4-methylthiazol-5-yl)phenyl)-2-((tetrahydro-2H-pyran-4-yl)methoxy)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 263 | 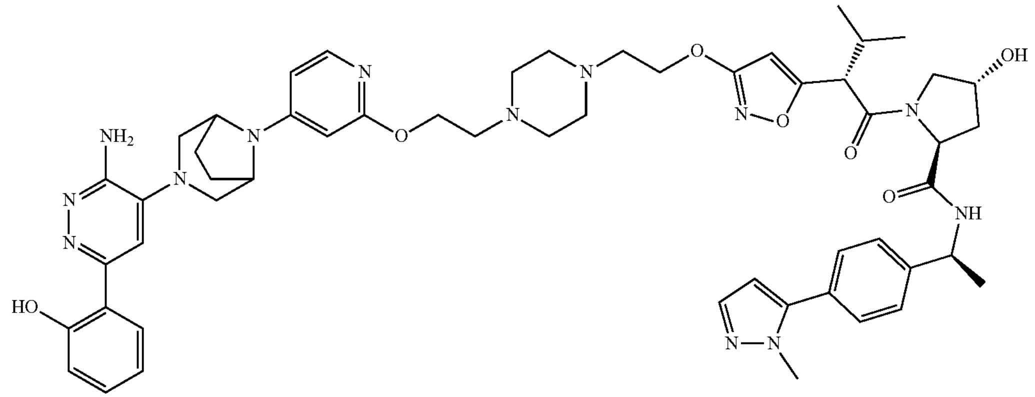 [SMILES: CC(C)[C@H](C(=O)N1C[C@H](O)C[C@H]1C(=O)N[C@@H](C)c1ccc(-c2ccnn2C)cc1)c1cc(OCCN2CCN(CCOc3cc(N4C5CCC4CN(c4cc(-c6ccccc6O)nnc4N)C5)ccn3)CC2)no1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(1-methyl-1H-pyrazol-5-yl)phenyl)ethyl)pyrrolidine-2-carboxamide |
| 264 | 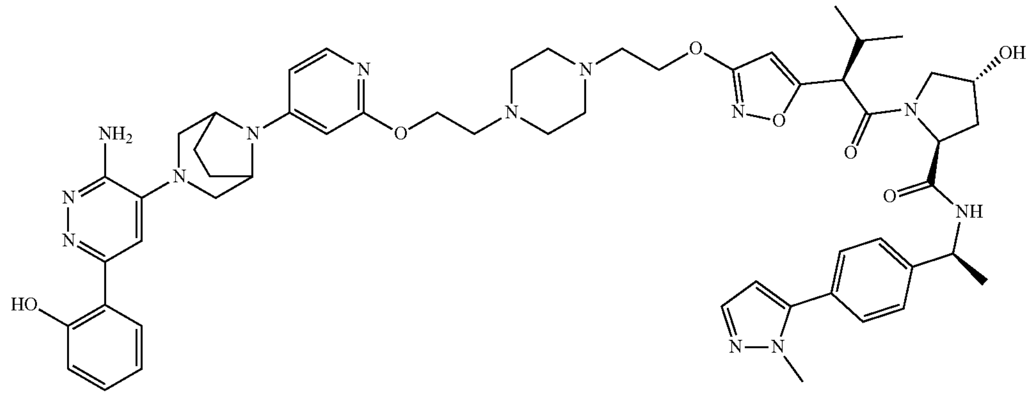 [SMILES: CC(C)[C@@H](C(=O)N1C[C@H](O)C[C@H]1C(=O)N[C@@H](C)c1ccc(-c2ccnn2C)cc1)c1cc(OCCN2CCN(CCOc3cc(N4C5CCC4CN(c4cc(-c6ccccc6O)nnc4N)C5)ccn3)CC2)no1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(1-methyl-1H-pyrazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 265 | 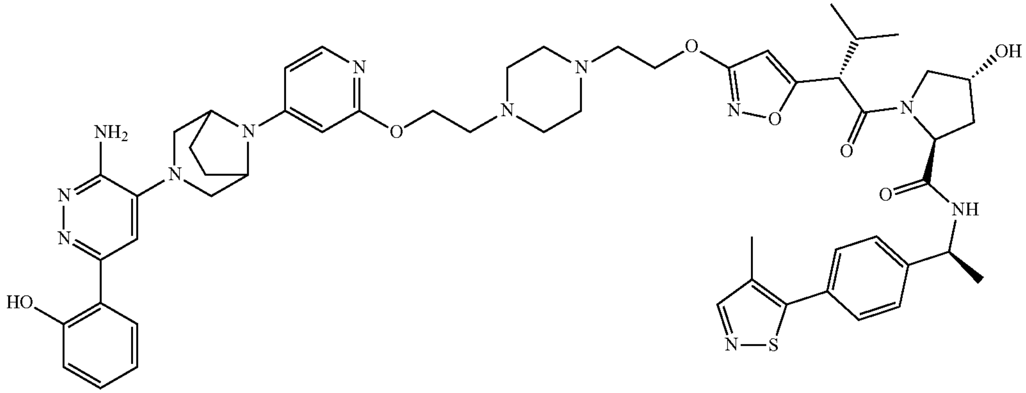 [SMILES: Cc1cnsc1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-methylisothiazol-5-yl)phenyl)ethyl)pyrrolidine-2-carboxamide |
| 266 | 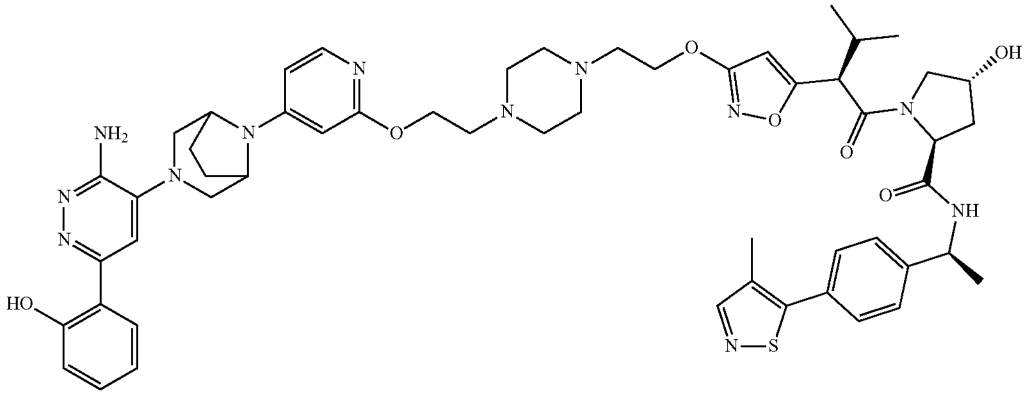 [SMILES: Cc1cnsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-methylisothiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 267 | 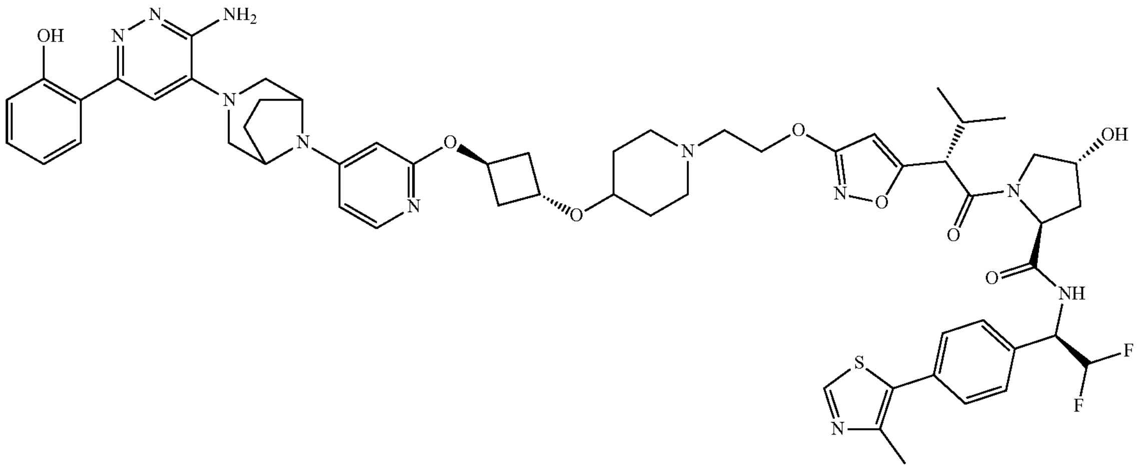 [SMILES: Cc1ncsc1-c1ccc([C@@H](NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)C(F)F)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-2,2-difluoro-1-(4-(4-methylthiazol-5-yl)phenyl)ethyl)-4-hydroxypyrrolidine-2-carboxamide |
| 268 | 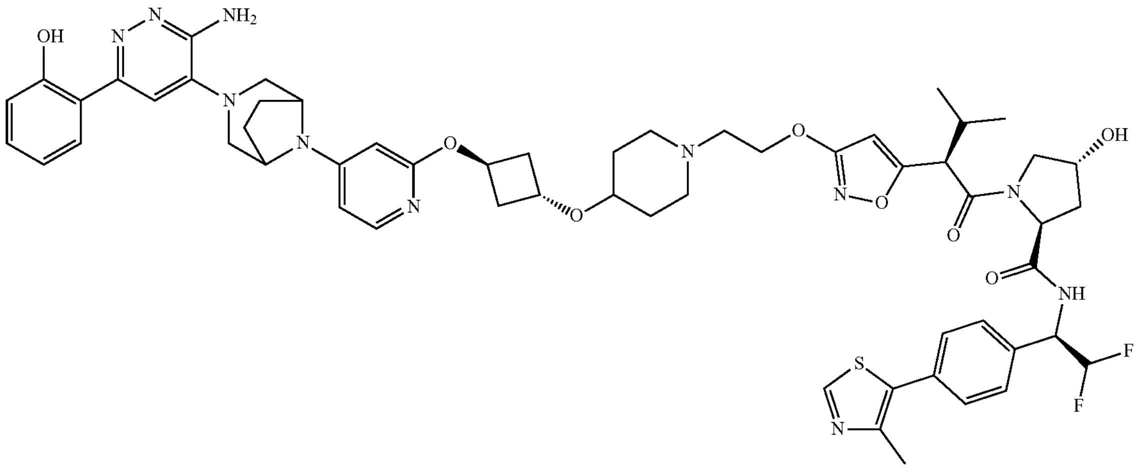 [SMILES: Cc1ncsc1-c1ccc([C@@H](NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)C(F)F)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-2,2-difluoro-1-(4-(4-methylthiazol-5-yl)phenyl)ethyl)-4-hydroxypyrrolidine-2-carboxamide |

TABLE 1B-continued

]Exemplary bifunctional degradation compounds of the present disclosure

| Ex. # | Structure | Compound Name |
| --- | --- | --- |
| 269 | 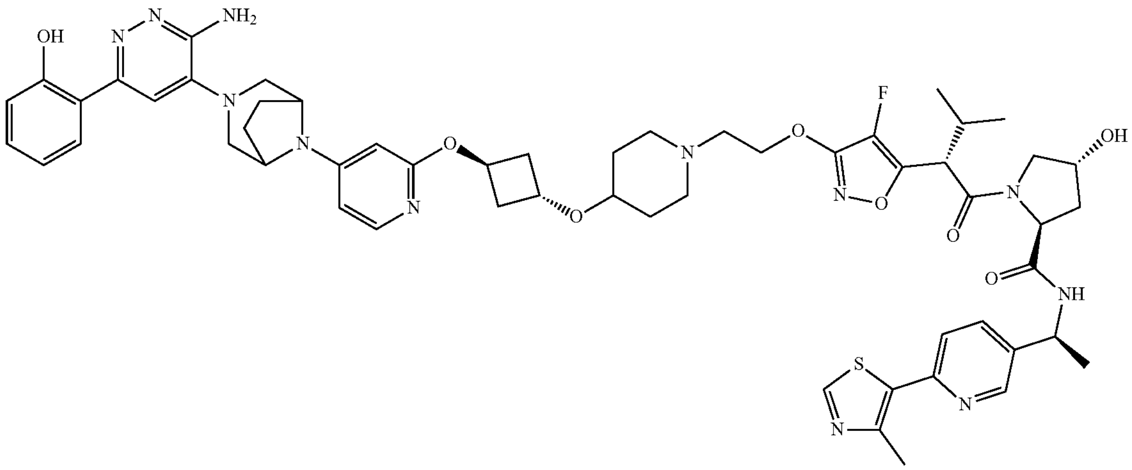 [SMILES: Cc1ncsc1-c1ccc([C@H](C)NC(=O)[C@@H]2C[C@@H](O)CN2C(=O)[C@H](c2onc(OCCN3CCC(O[C@H]4C[C@H](Oc5cc(N6C7CCC6CN(c6cc(-c8ccccc8O)nnc6N)C7)ccn5)C4)CC3)c2F)C(C)C)cn1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-fluoroisoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 270 | 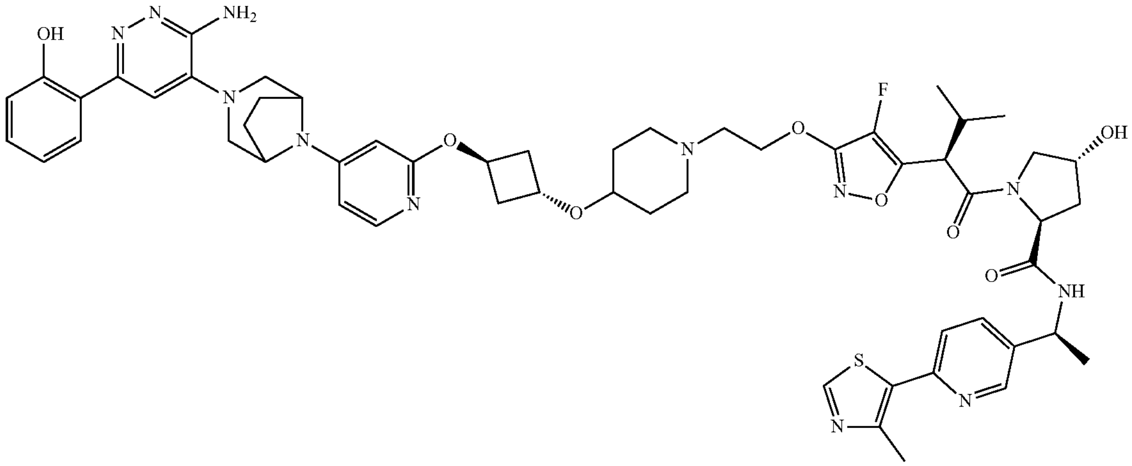 [SMILES: Cc1ncsc1-c1ccc([C@H](C)NC(=O)[C@@H]2C[C@@H](O)CN2C(=O)[C@@H](c2onc(OCCN3CCC(O[C@H]4C[C@H](Oc5cc(N6C7CCC6CN(c6cc(-c8ccccc8O)nnc6N)C7)ccn5)C4)CC3)c2F)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-fluoroisoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 271 | 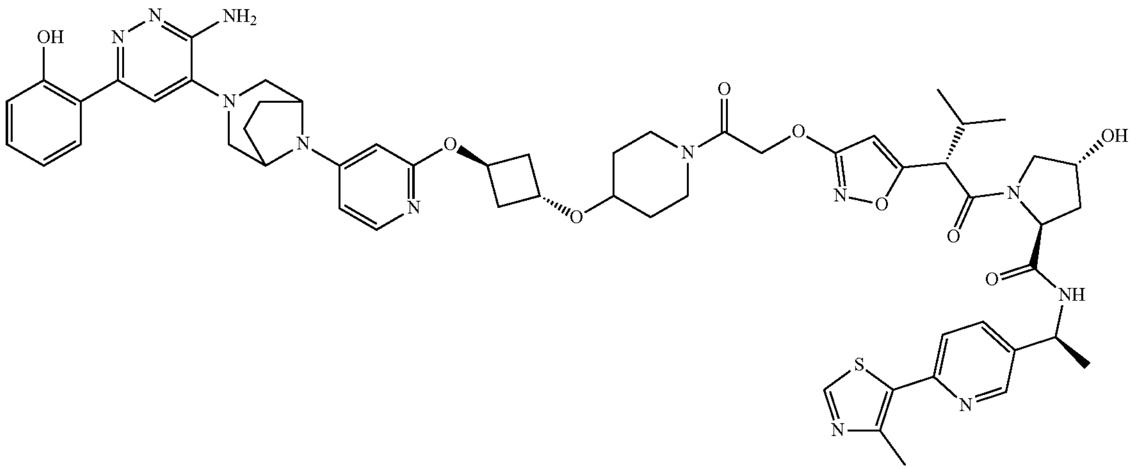 [SMILES: Cc1ncsc1-c1ccc([C@H](C)NC(=O)[C@@H]2C[C@@H](O)CN2C(=O)[C@H](c2cc(OCC(=O)N3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-2-oxoethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 272 | 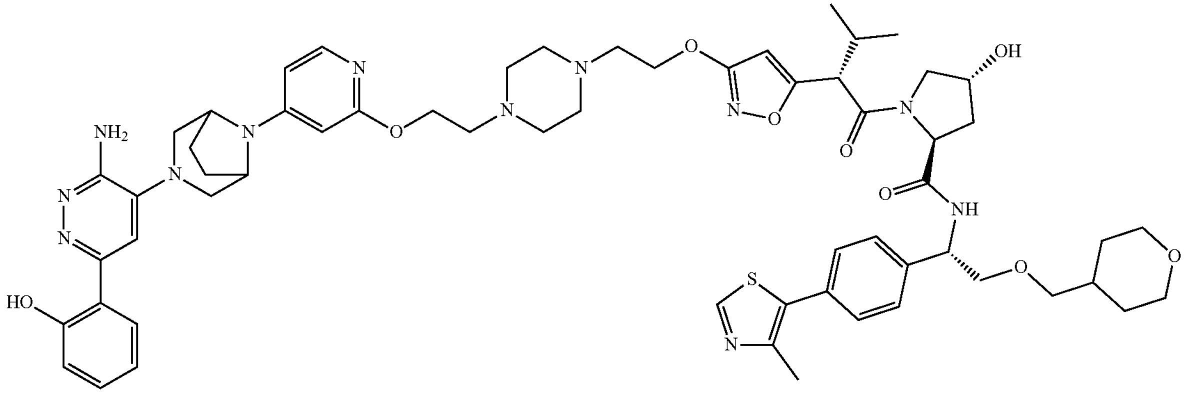 [SMILES: Cc1ncsc1-c1ccc([C@@H](COCC2CCOCC2)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-methylthiazol-5-yl)phenyl)-2-((tetrahydro-2H-pyran-4-yl)methoxy)ethyl)pyrrolidine-2-carboxamide |

TABLE 1B-continued

]Exemplary bifunctional degradation compounds of the present disclosure

| Ex. # | Structure | Compound Name |
|---|---|---|
| 273 | 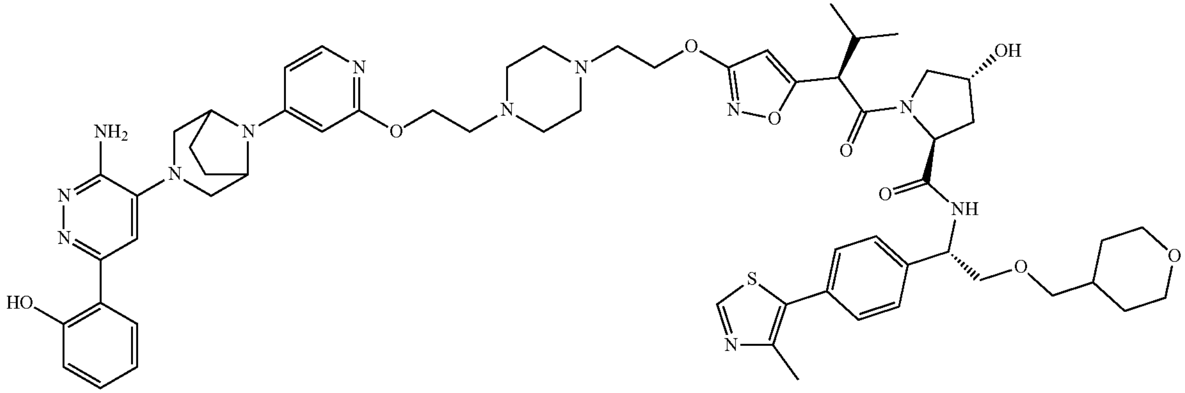 | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-methylthiazol-5-yl)phenyl)-2-((tetrahydro-2H-pyran-4-yl)methoxy)ethyl)pyrrolidine-2-carboxamide |
| 274 | 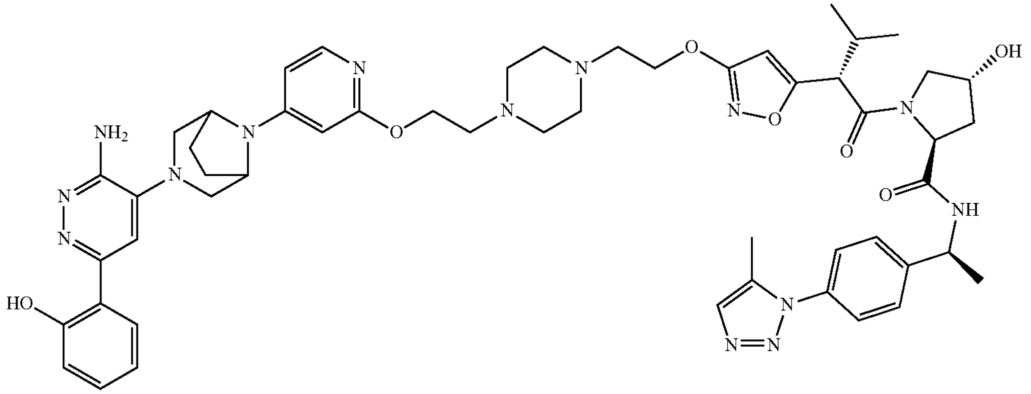 [SMILES: Cc1cnnn1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(5-methyl-1H-1,2,3-triazol-1-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 275 | 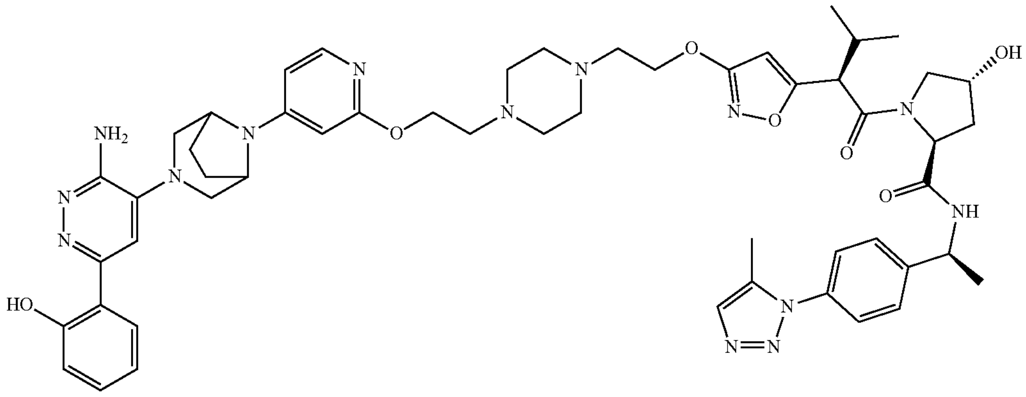 [SMILES: Cc1cnnn1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(5-methyl-1H-1,2,3-triazol-1-yl)phenyl)ethyl)pyrrolidine-2-carboxamide |
| 276 | 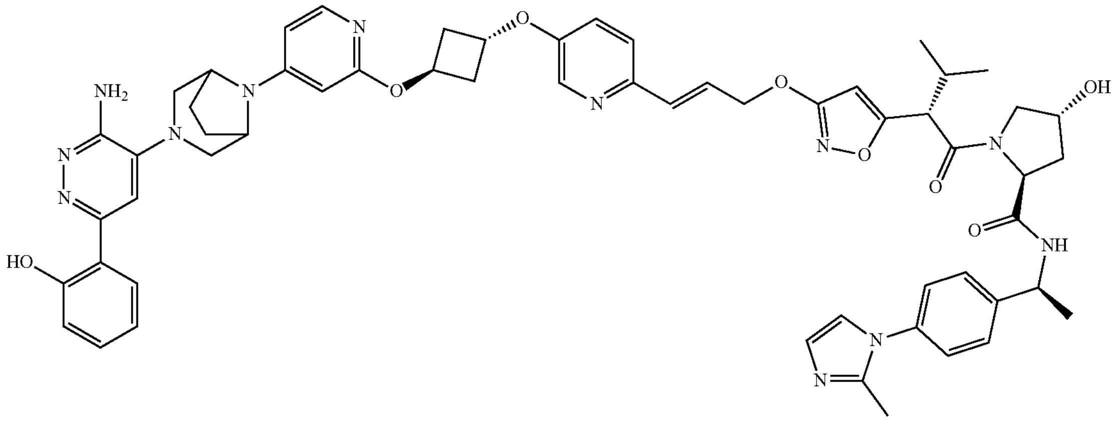 [SMILES: Cc1nccn1-c1ccc([C@H](C)NC(=O)[C@@H]2C[C@@H](O)CN2C(=O)[C@H](c2cc(OC/C=C/c3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2S)-2-(3-(((E)-3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)allyl)oxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 277 | 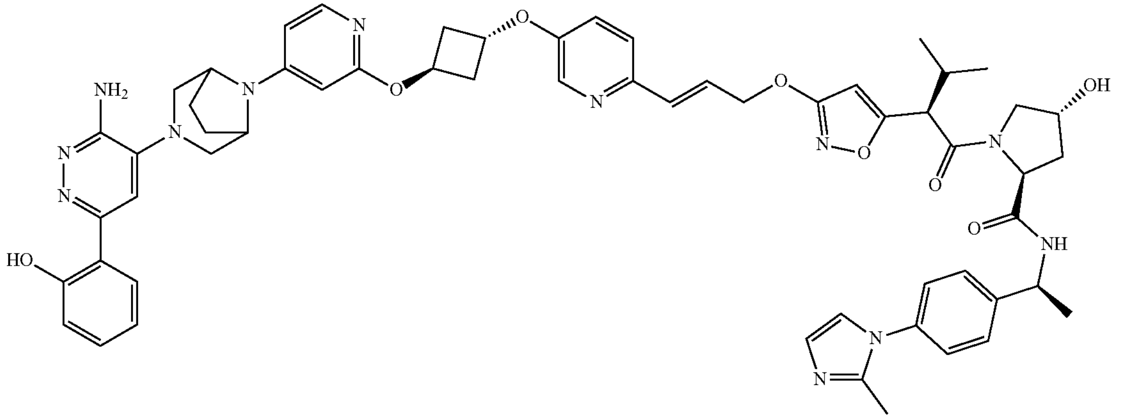 [SMILES: Cc1nccn1-c1ccc([C@H](C)NC(=O)[C@@H]2C[C@@H](O)CN2C(=O)[C@@H](c2cc(OC/C=C/c3ccc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-(((E)-3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)allyl)oxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |
| 278 | 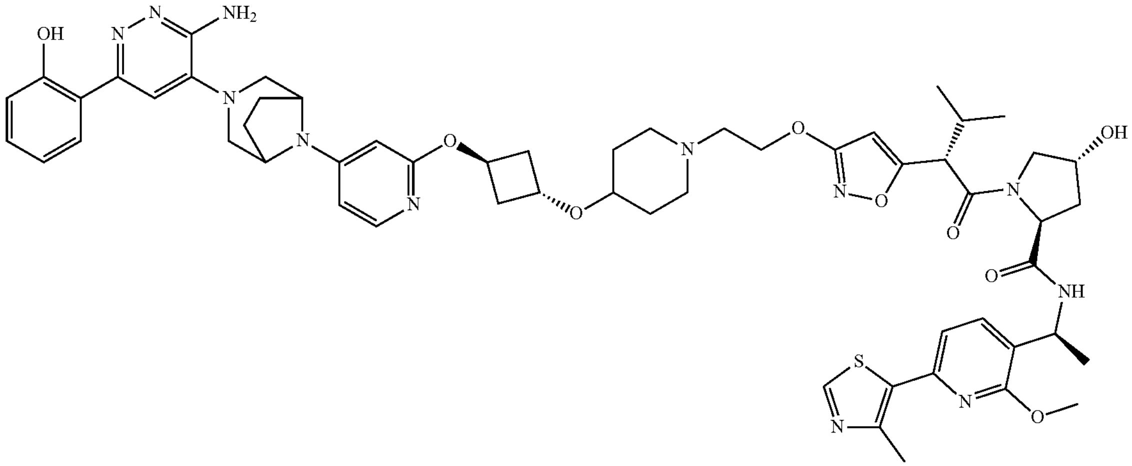 [SMILES: COc1nc(-c2scnc2C)ccc1[C@H](C)NC(=O)[C@@H]1C[C@@H](O)CN1C(=O)[C@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(2-methoxy-6-(4-methylthiazol-5-yl)pyridin-3-yl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 279 | 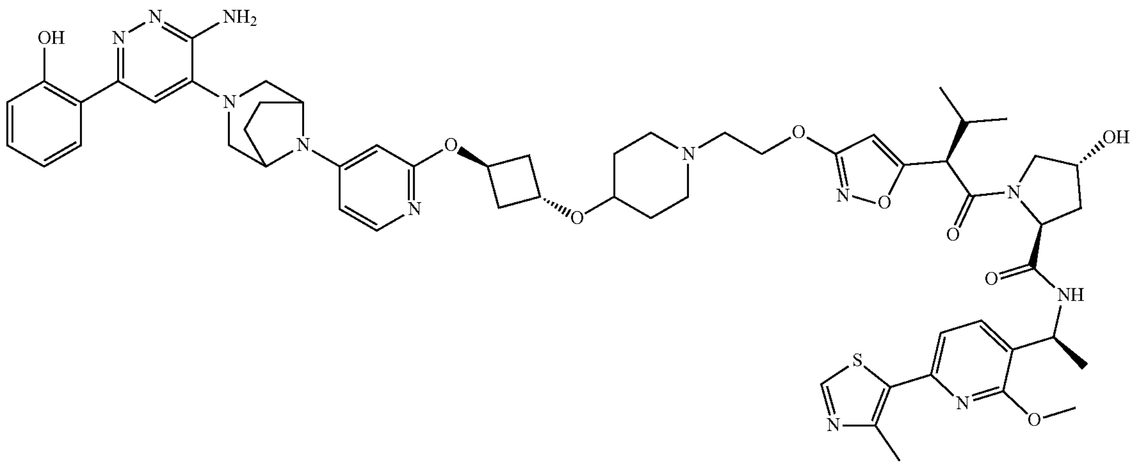 [SMILES: COc1nc(-c2scnc2C)ccc1[C@H](C)NC(=O)[C@@H]1C[C@@H](O)CN1C(=O)[C@@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(2-methoxy-6-(4-methylthiazol-5-yl)pyridin-3-yl)ethyl)pyrrolidine-2-carboxamide |
| 280 | 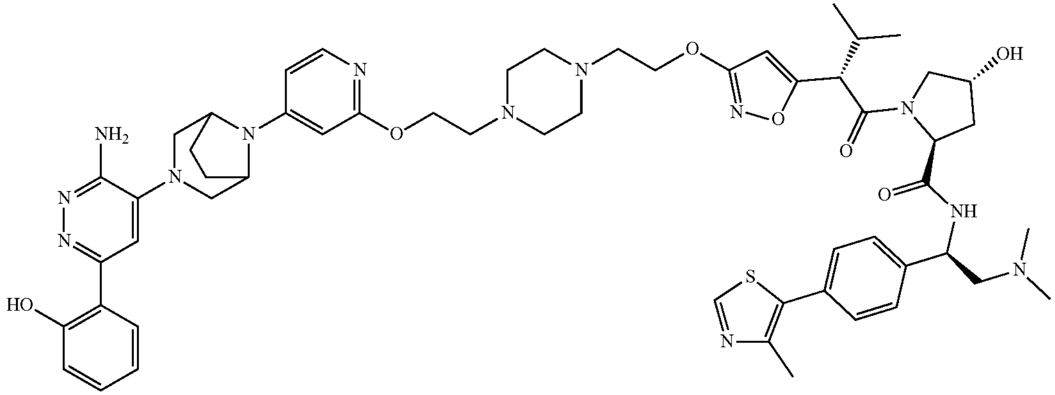 [SMILES: Cc1ncsc1-c1ccc([C@H](CN(C)C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-(dimethylamino)-1-(4-(4-methylthiazol-5-yl)phenyl)ethyl)-4-hydroxypyrrolidine-2-carboxamide |

TABLE 1B-continued

]Exemplary bifunctional degradation compounds of the present disclosure

| Ex. # | Structure | Compound Name |
|---|---|---|
| 281 | 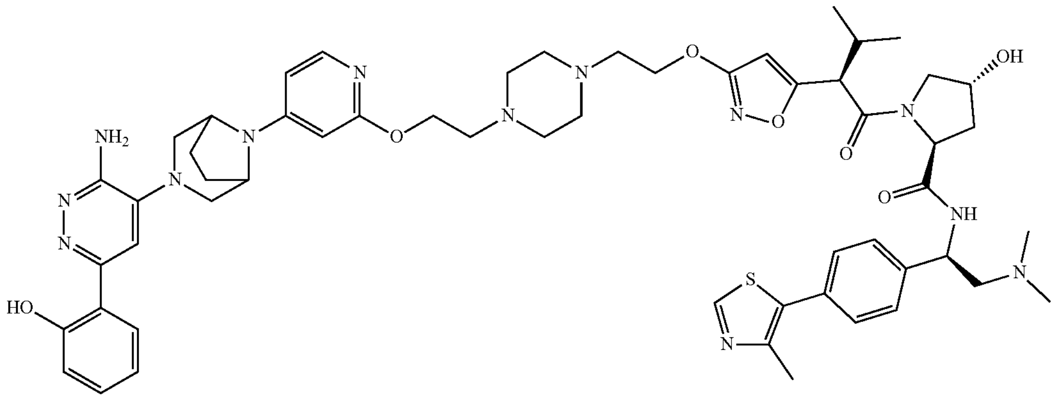 [SMILES: Cc1ncsc1-c1ccc([C@H](CN(C)C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((R)-2-(dimethylamino)-1-(4-(4-methylthiazol-5-yl)phenyl)ethyl)-4-hydroxypyrrolidine-2-carboxamide |
| 282 | 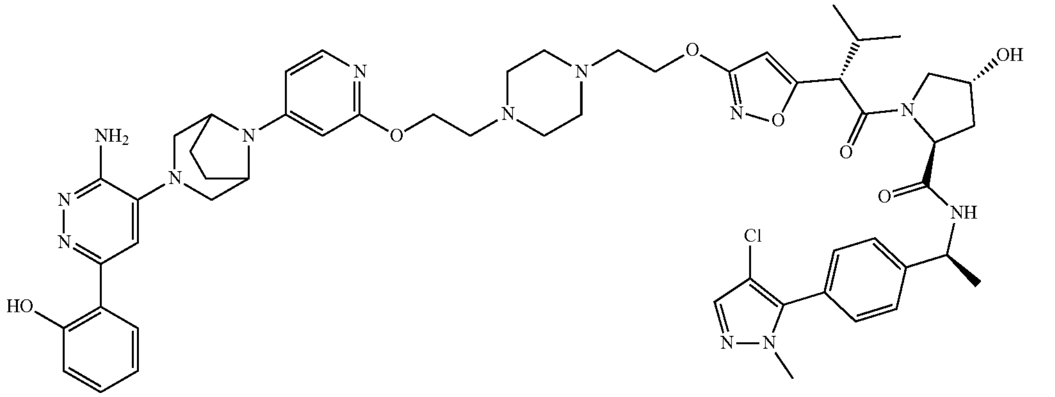 [SMILES: CC(C)[C@H](C(=O)N1C[C@H](O)C[C@H]1C(=O)N[C@@H](C)c1ccc(-c2c(Cl)cnn2C)cc1)c1cc(OCCN2CCN(CCOc3cc(N4C5CCC4CN(c4cc(-c6ccccc6O)nnc4N)C5)ccn3)CC2)no1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-chloro-1-methyl-1H-pyrazol-5-yl)phenyl)ethyl)-4-hydroxypyrrolidine-2-carboxamide |

TABLE 1B-continued

| ]Exemplary bifunctional degradation compounds of the present disclosure | | |
|---|---|---|
| Ex. # | Structure | Compound Name |
| 283 | 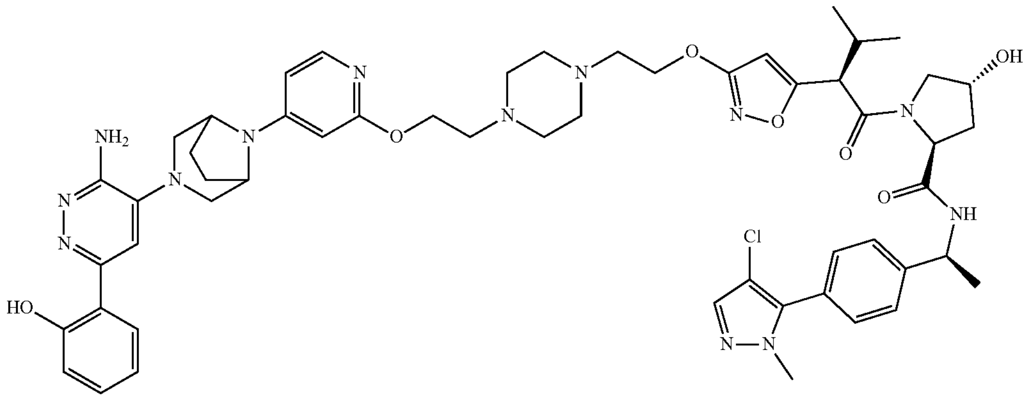 [SMILES: CC(C)[C@@H](C(=O)N1C[C@H](O)C[C@H]1C(=O)N[C@@H](C)c1ccc(-c2c(Cl)cnn2C)cc1)c1cc(OCCN2CCN(CCOc3cc(N4C5CCC4CN(c4cc(-c6ccccc6O)nnc4N)C5)ccn3)CC2)no1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-chloro-1-methyl-1H-pyrazol-5-yl)phenyl)ethyl)-4-hydroxypyrrolidine-2-carboxamide |
| 284 | 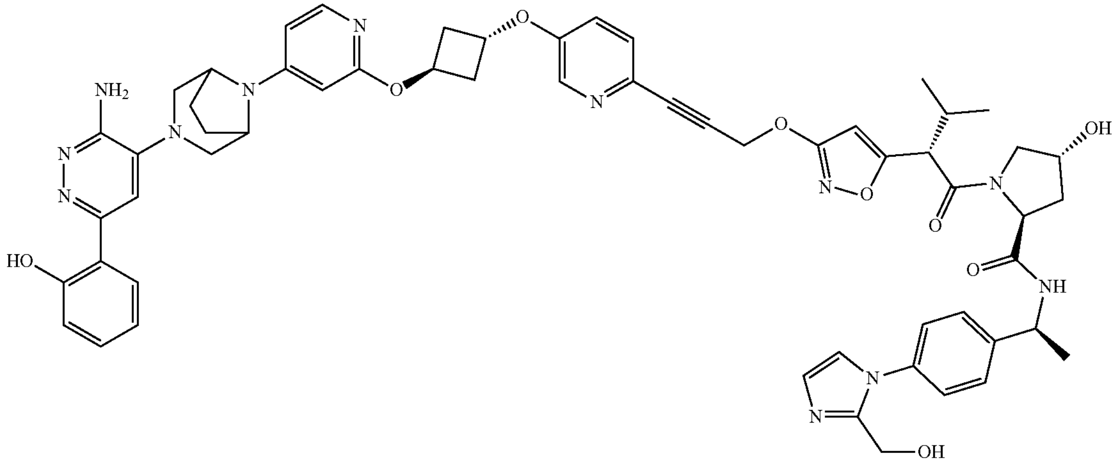 [SMILES: CC(C)[C@H](C(=O)N1C[C@H](O)C[C@H]1C(=O)N[C@@H](C)c1ccc(-n2ccnc2CO)cc1)c1cc(OCC#Cc2ccc(O[C@H]3C[C@H](Oc4cc(N5C6CCC5CN(c5cc(-c7ccccc7O)nnc5N)C6)ccn4)C3)cn2)no1] | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-((S)-1-(4-(2-(hydroxymethyl)-1H-imidazol-1-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 285 | 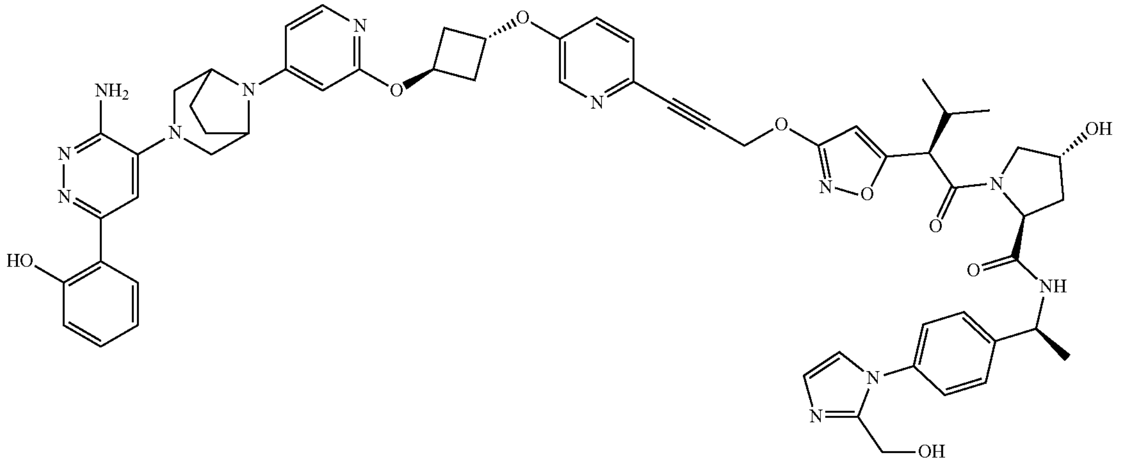 [SMILES: CC(C)[C@@H](C(=O)N1C[C@H](O)C[C@H]1C(=O)N[C@@H](C)c1ccc(-n2ccnc2CO)cc1)c1cc(OCC#Cc2ccc(O[C@H]3C[C@H](Oc4cc(N5C6CCC5CN(c5cc(-c7ccccc7O)nnc5N)C6)ccn4)C3)cn2)no1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)prop-2-yn-1-yl)oxy)isoxazol-5-yl)-3-methylbutanoyl)-4-hydroxy-N-((S)-1-(4-(2-(hydroxymethyl)-1H-imidazol-1-yl)phenyl)ethyl)pyrrolidine-2-carboxamide |
| 286 | 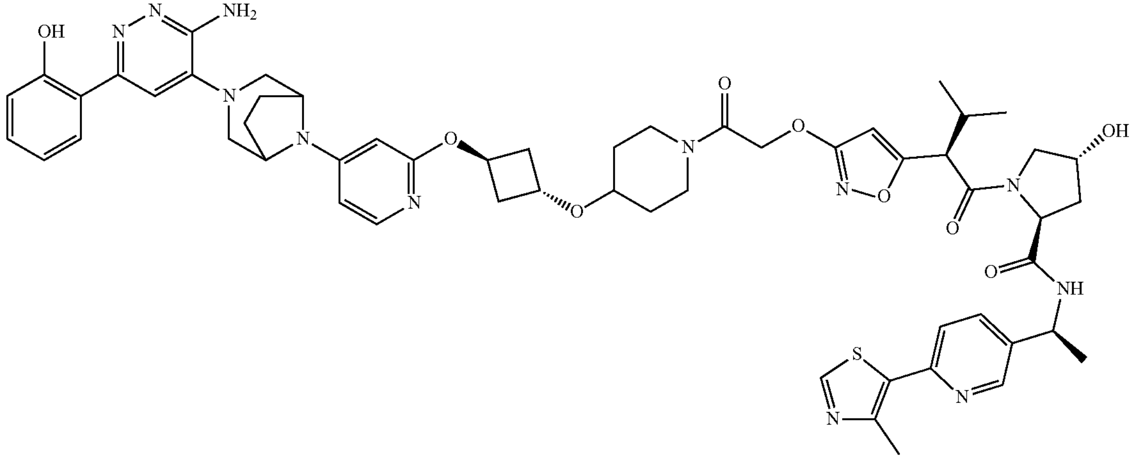 [SMILES: Cc1ncsc1-c1ccc([C@H](C)NC(=O)[C@@H]2C[C@@H](O)CN2C(=O)[C@@H](c2cc(OCC(=O)N3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-2-oxoethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 287 | 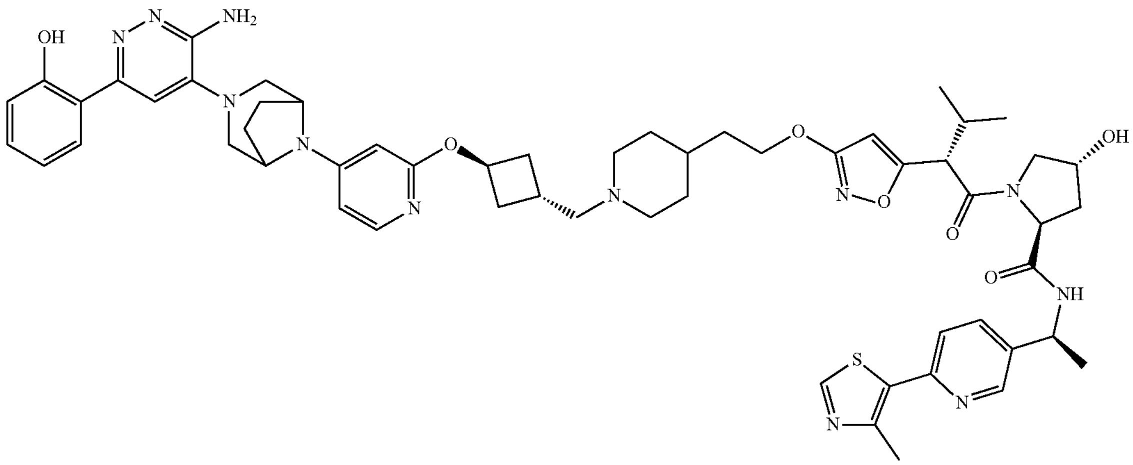 [SMILES: Cc1ncsc1-c1ccc([C@H](C)NC(=O)[C@@H]2C[C@@H](O)CN2C(=O)[C@H](c2cc(OCCC3CCN(C[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2S)-2-(3-(2-(1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 288 | 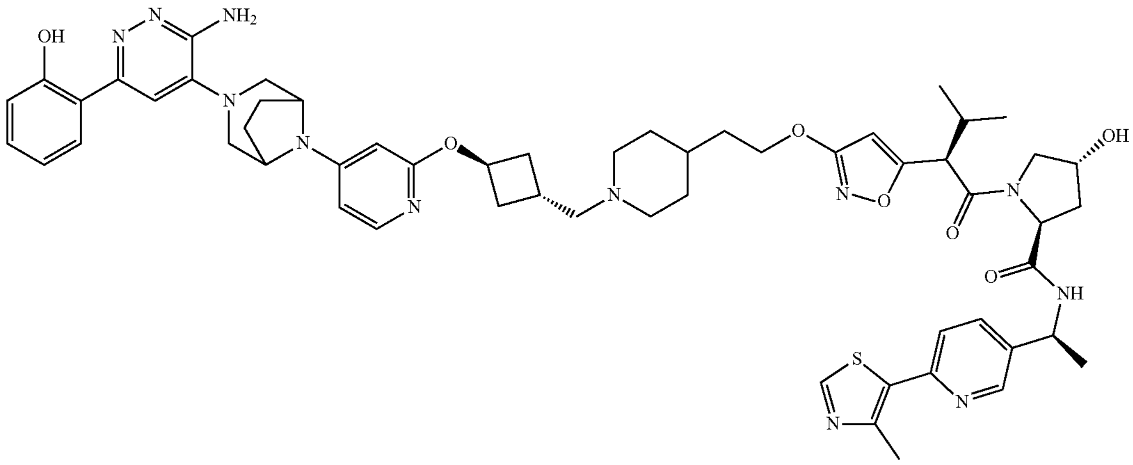 [SMILES: Cc1ncsc1-c1ccc([C@H](C)NC(=O)[C@@H]2C[C@@H](O)CN2C(=O)[C@@H](c2cc(OCCC3CCN(C[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
|---|---|---|
| 289 | 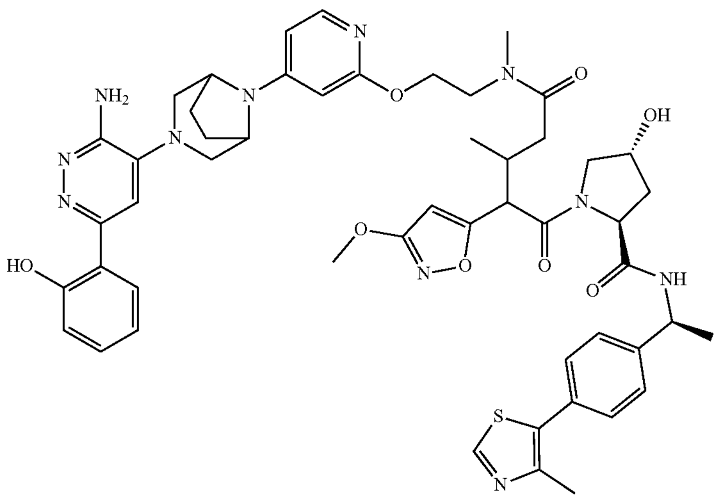 [SMILES: COc1cc(C(C(=O)N2C[C@H](O)C[C@H]2C(=O)N[C@@H](C)c2ccc(-c3scnc3C)cc2)C(C)CC(=O)N(C)CCOc2cc(N3C4CCC3CN(c3cc(-c5ccccc5O)nnc3N)C4)ccn2)on1] | (2S,4R)-1-(5-((2-((4-(3-(3-amino-6-(2-hydroxyphenyl)pyridazin-4-yl)-3,8-diazabicyclo[3.2.1]octan-8-yl)pyridin-2-yl)oxy)ethyl)(methyl)amino)-2-(3-methoxyisoxazol-5-yl)-3-methyl-5-oxopentanoyl)-4-hydroxy-N-((S)-1-(4-(4-methylthiazol-5-yl)phenyl)ethyl)pyrrolidine-2-carboxamide |
| 290 | 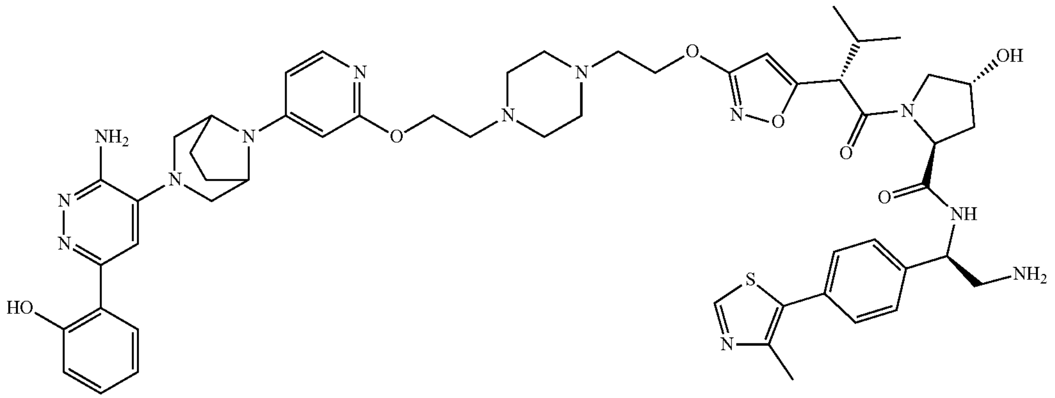 [SMILES: Cc1ncsc1-c1ccc([C@H](CN)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-N-((R)-2-amino-1-(4-(4-methylthiazol-5-yl)phenyl)ethyl)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |

TABLE 1B-continued

]Exemplary bifunctional degradation compounds of the present disclosure

| Ex. # | Structure | Compound Name |
|---|---|---|
| 291 | 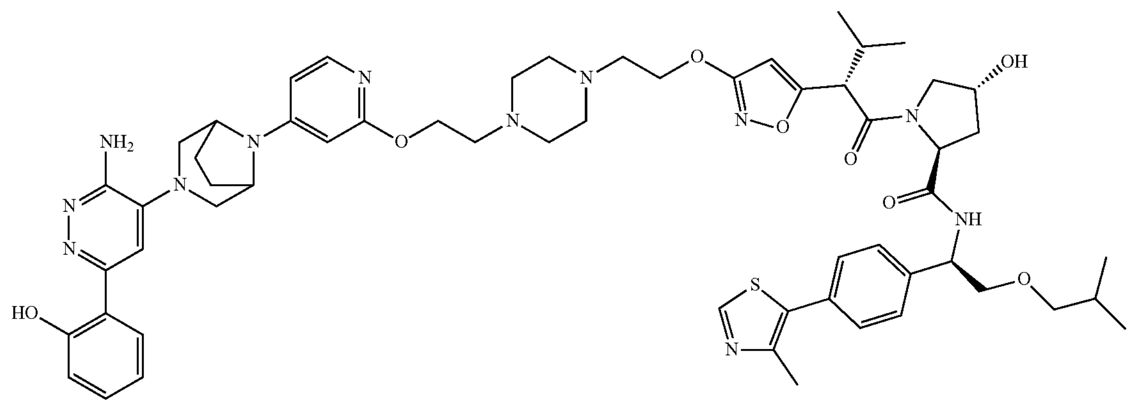 [SMILES: Cc1ncsc1-c1ccc([C@H](COCC(C)C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((R)-2-isobutoxy-1-(4-(4-methylthiazol-5-yl)phenyl)ethyl)pyrrolidine-2-carboxamide |
| 292 | 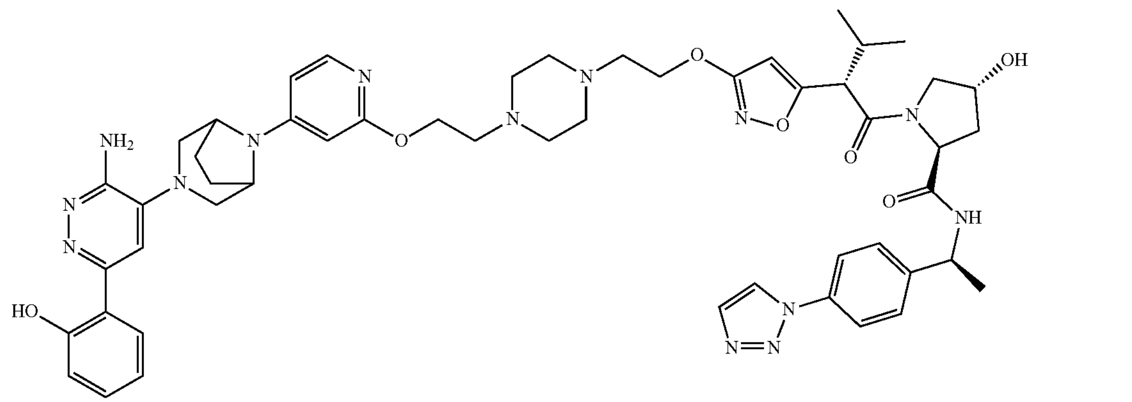 [SMILES: CC(C)[C@H](C(=O)N1C[C@H](O)C[C@H]1C(=O)N[C@@H](C)c1ccc(-n2ccnn2)cc1)c1cc(OCCN2CCN(CCOc3cc(N4C5CCC4CN(c4cc(-c6ccccc6O)nnc4N)C5)ccn3)CC2)no1] | (2S,4R)-N-((S)-1-(4-(1H-1,2,3-triazol-1-yl)phenyl)ethyl)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |

TABLE 1B-continued

]Exemplary bifunctional degradation compounds of the present disclosure

| Ex. # | Structure | Compound Name |
|---|---|---|
| 293 | 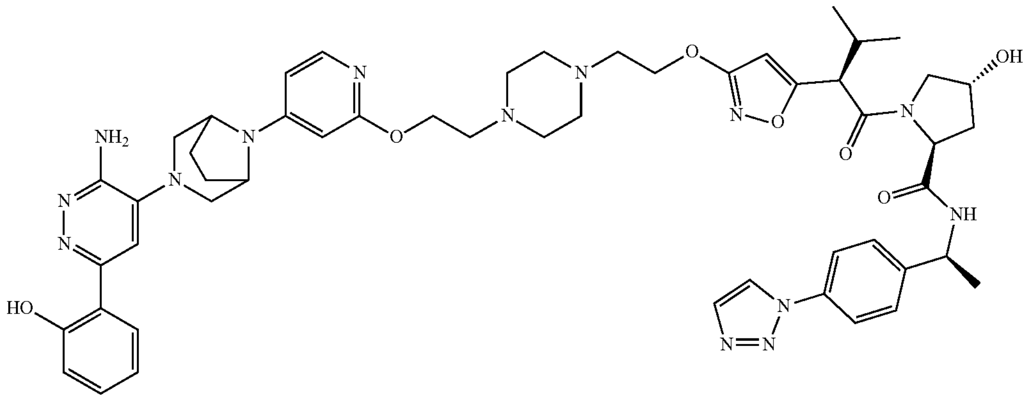 [SMILES: CC(C)[C@@H](C(=O)N1C[C@H](O)C[C@H]1C(=O)N[C@@H](C)c1ccc(-n2ccnn2)cc1)c1cc(OCCN2CCN(CCOc3cc(N4C5CCC4CN(c4cc(-c6ccccc6O)nnc4N)C5)ccn3)CC2)no1] | (2S,4R)-N-((S)-1-(4-(1H-1,2,3-triazol-1-yl)phenyl)ethyl)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxypyrrolidine-2-carboxamide |
| 294 | 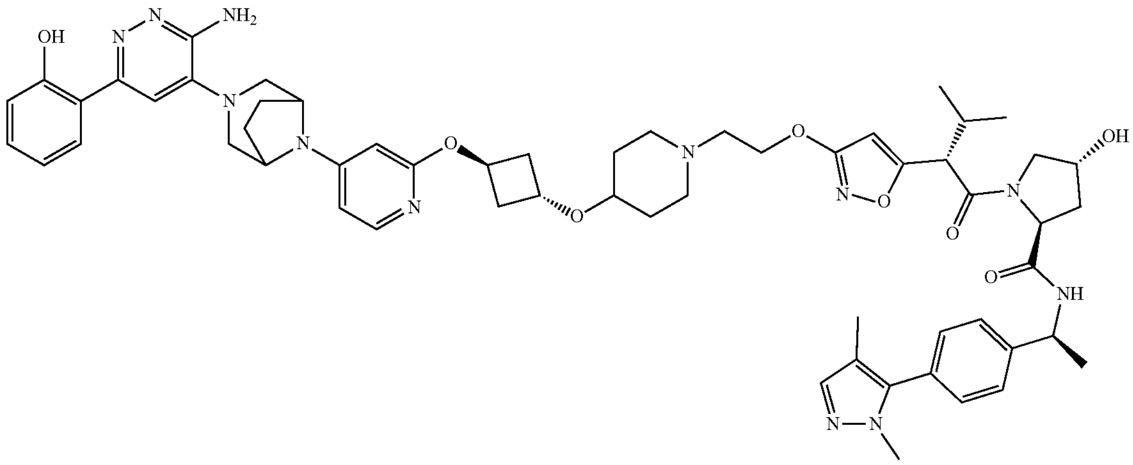 [SMILES: Cc1cnn(C)c1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(1,4-dimethyl-1H-pyrazol-5-yl)phenyl)ethyl)-4-hydroxypyrrolidine-2-carboxamide |

TABLE 1B-continued

| ]Exemplary bifunctional degradation compounds of the present disclosure | | |
|---|---|---|
| Ex. # | Structure | Compound Name |
| 295 | 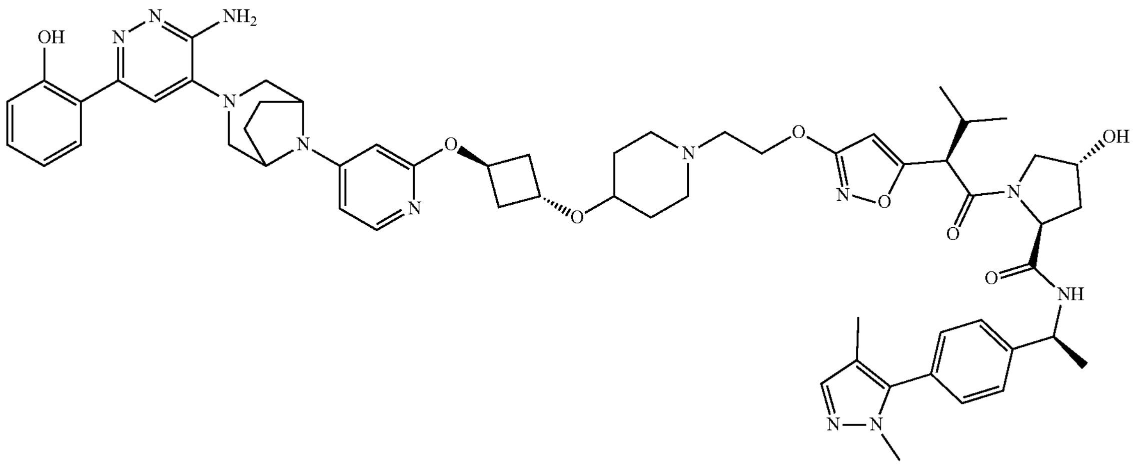 [SMILES: Cc1cnn(C)c1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(1,4-dimethyl-1H-pyrazol-5-yl)phenyl)ethyl)-4-hydroxypyrrolidine-2-carboxamide |
| 296 | 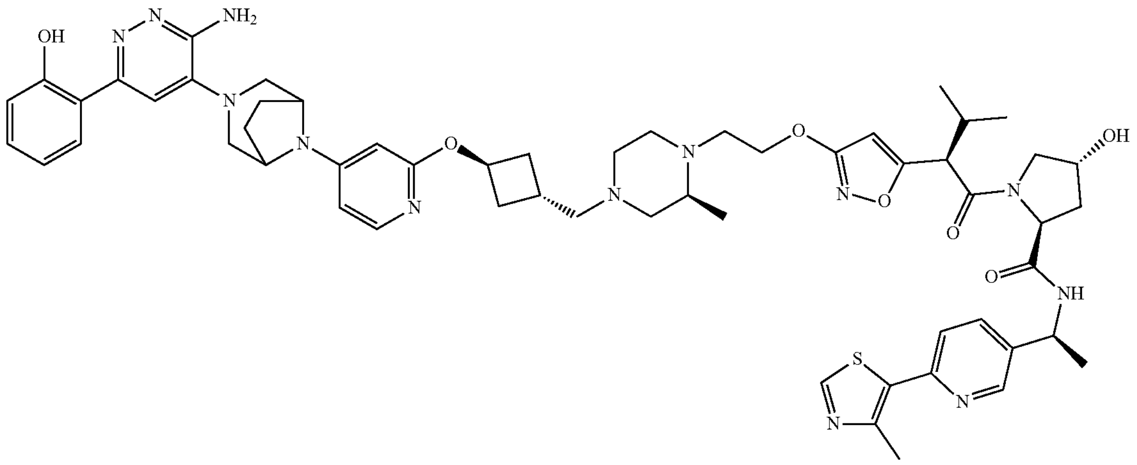 [SMILES: Cc1ncsc1-c1ccc([C@H](C)NC(=O)[C@@H]2C[C@@H](O)CN2C(=O)[C@@H](c2cc(OCCN3CCN(C[C@H]4C[C@H](Oc5cc(N6C7CCC6CN(c6cc(-c8ccccc8O)nnc6N)C7)ccn5)C4)C[C@@H]3C)no2)C(C)C)cn1] | (2S,4R)-1-((2R)-2-(3-(2-((2S)-4-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperazin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 297 | 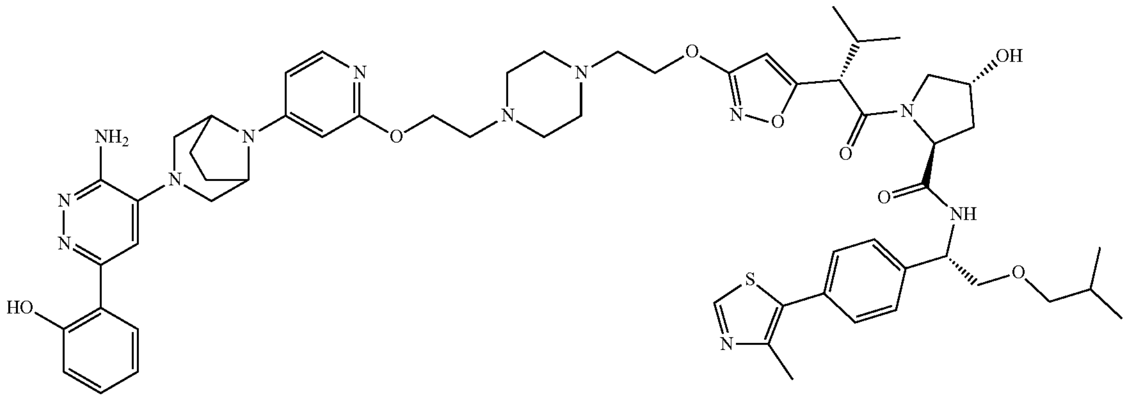 [SMILES: Cc1ncsc1-c1ccc([C@@H](COCC(C)C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(4-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)azet-2-yl)-3-methylbutanoyl)-4-hydroxy-N-((S)-2-isobutoxy-1-(4-(4-methylthiazol-5-yl)phenyl)ethyl)pyrrolidine-2-carboxamide |
| 298 | 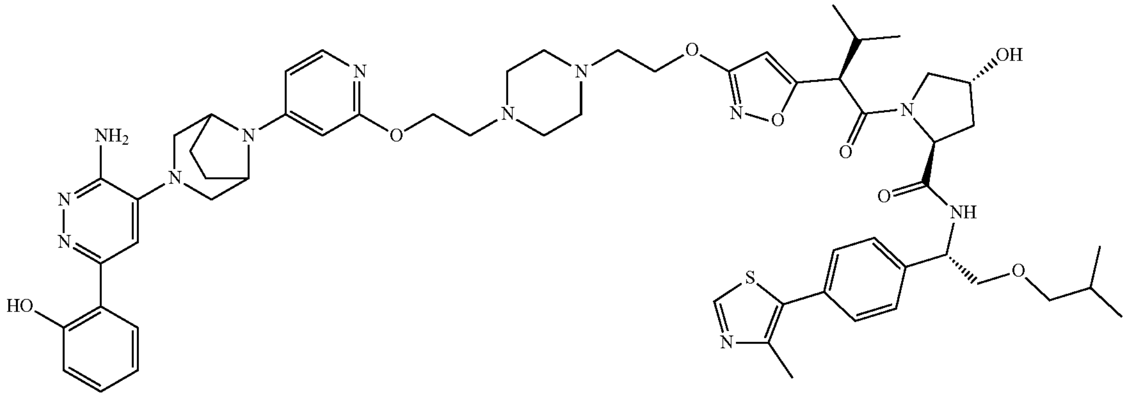 [SMILES: Cc1ncsc1-c1ccc([C@@H](COCC(C)C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-2-isobutoxy-1-(4-(4-methylthiazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 299 | 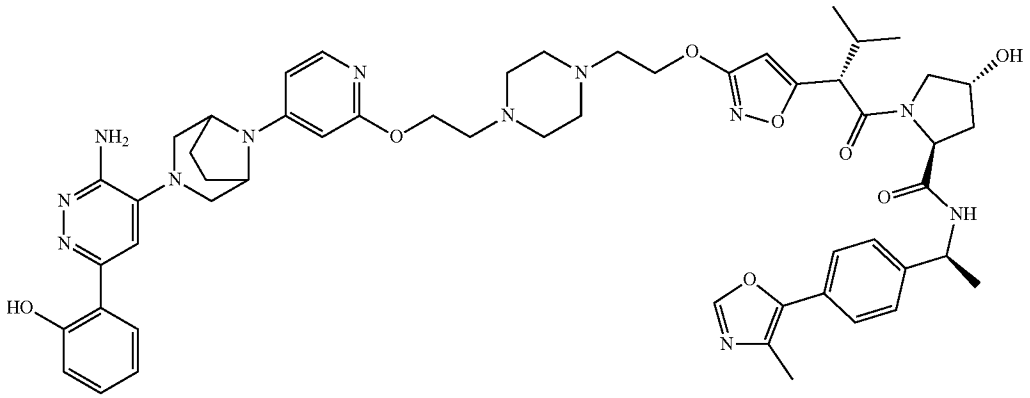 [SMILES: Cc1ncoc1-c1ccc([C@H](C)NC(=O)[C@@H]2C[C@@H](O)CN2C(=O)[C@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-methyloxazol-5-yl)phenyl)ethyl)pyrrolidine-2-carboxamide |
| 300 | 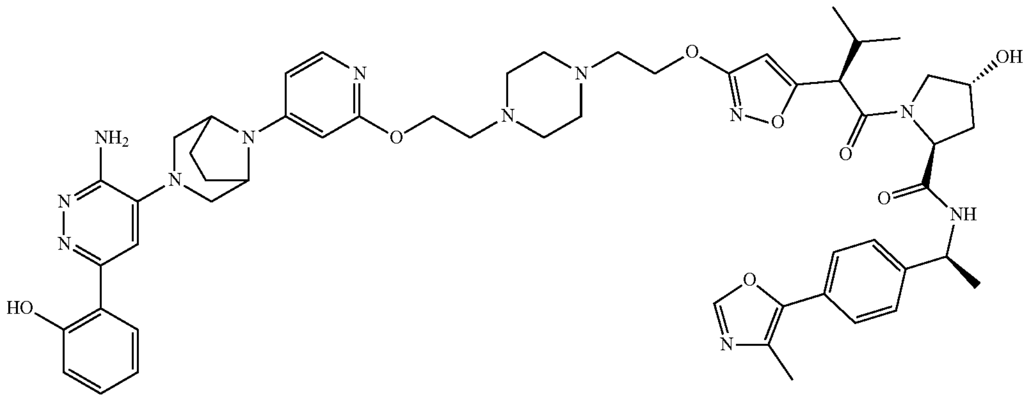 [SMILES: Cc1ncoc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-4-hydroxy-N-((S)-1-(4-(4-methyloxazol-5-yl)phenyl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 301 | 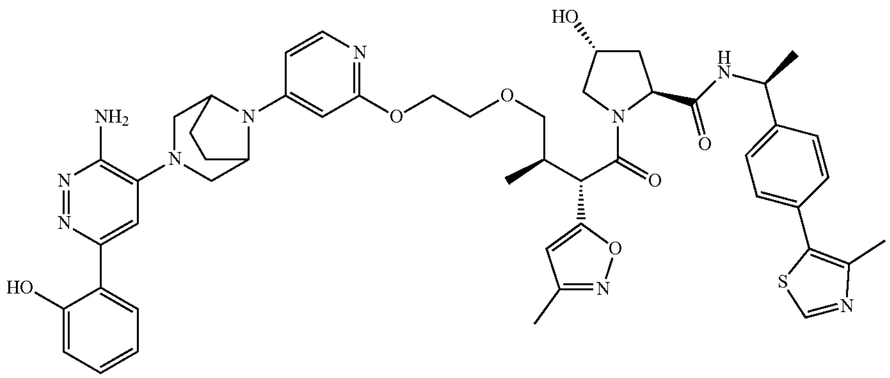 [SMILES: Cc1cc([C@@H](C(=O)N2C[C@H](O)C[C@H]2C(=O)N[C@@H](C)c2ccc(-c3scnc3C)cc2)[C@@H](C)COCCOc2cc(N3C4CCC3CN(c3cc(-c5ccccc5O)nnc3N)C4)ccn2)on1] | (2S,4R)-1-((2S,3R)-4-(2-((4-(3-(3-amino-6-(2-hydroxyphenyl)pyridazin-4-yl)-3,8-diazabicyclo[3.2.1]octan-8-yl)pyridin-2-yl)oxy)ethoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide |
| 302 | 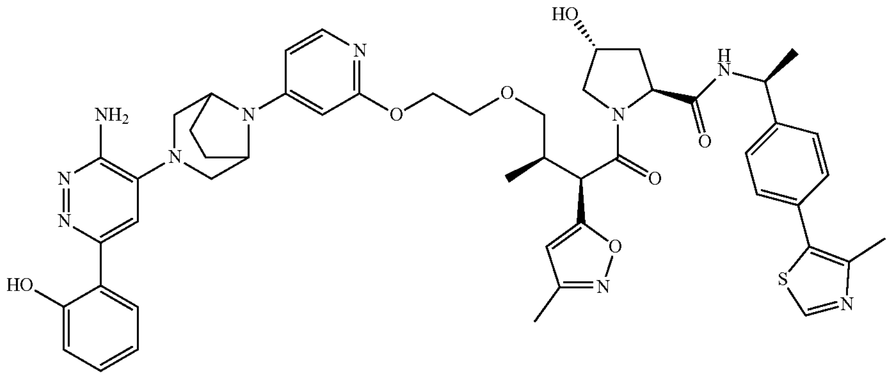 [SMILES: Cc1cc([C@H](C(=O)N2C[C@H](O)C[C@H]2C(=O)N[C@@H](C)c2ccc(-c3scnc3C)cc2)[C@@H](C)COCCOc2cc(N3C4CCC3CN(c3cc(-c5ccccc5O)nnc3N)C4)ccn2)on1] | (2S,4R)-1-((2R,3R)-4-(2-((4-(3-(3-amino-6-(2-hydroxyphenyl)pyridazin-4-yl)-3,8-diazabicyclo[3.2.1]octan-8-yl)pyridin-2-yl)oxy)ethoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide |

TABLE 1B-continued

| Ex. # | Structure | Compound Name |
| --- | --- | --- |
| ]Exemplary bifunctional degradation compounds of the present disclosure | | |
| 303 | 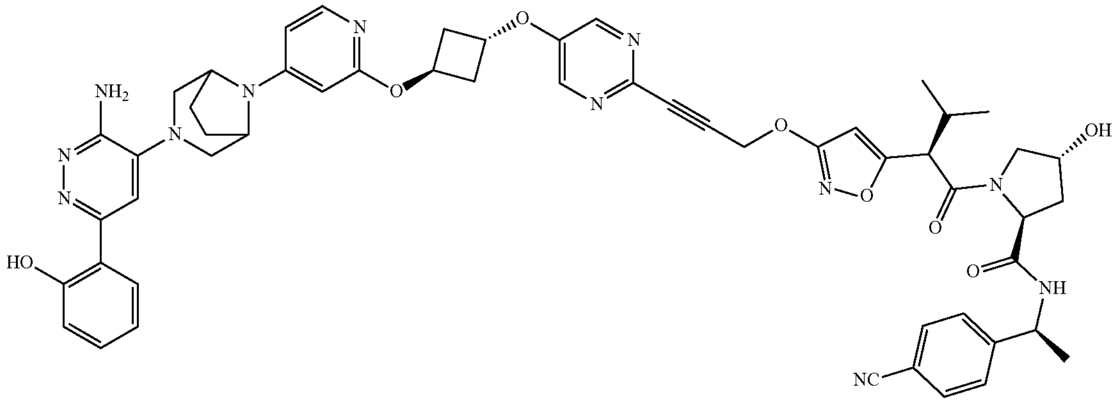 [SMILES: CC(C)[C@@H](C(=O)N1C[C@H](O)C[C@H]1C(=O)N[C@@H](C)c1ccc(C#N)cc1)c1cc(OCC#Cc2ncc(O[C@H]3C[C@H](Oc4cc(N5C6CCC5CN(c5cc(-c7ccccc7O)nnc5N)C6)ccn4)C3)cn2)no1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-N-((S)-1-(4-cyanophenyl)ethyl)-4-hydroxypyrrolidine-2-carboxamide |
| 304 | 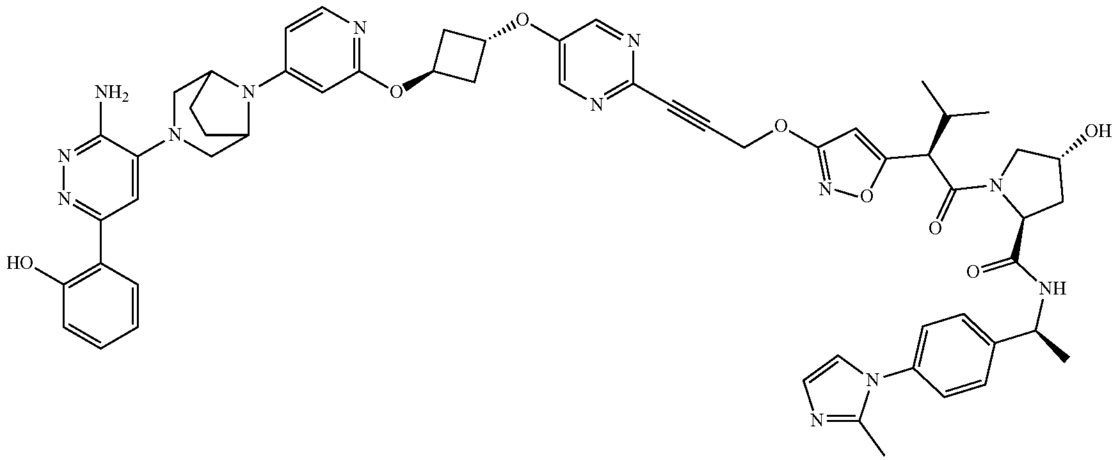 [SMILES: Cc1nccn1-c1ccc([C@H](C)NC(=O)[C@@H]2C[C@@H](O)CN2C(=O)[C@@H](c2cc(OCC#Cc3ncc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 305 | 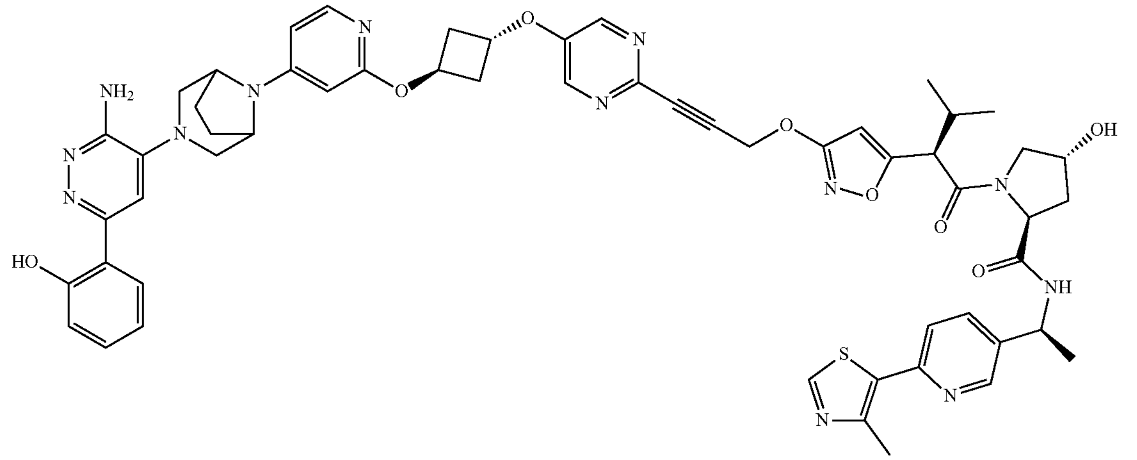 [SMILES: Cc1ncsc1-c1ccc([C@H](C)NC(=O)[C@@H]2C[C@@H](O)CN2C(=O)[C@@H](c2cc(OCC#Cc3ncc(O[C@H]4C[C@H](Oc5cc(N6C7CCC6CN(c6cc(-c8ccccc8O)nnc6N)C7)ccn5)C4)cn3)no2)C(C)C)cn1] | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 306 | 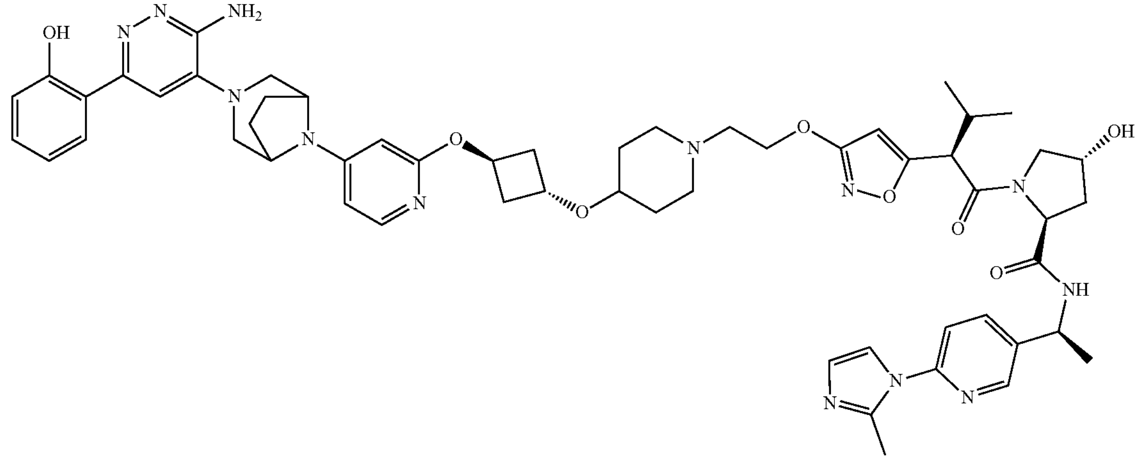 [SMILES: Cc1nccn1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(2-methyl-1H-imidazol-1-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 307 | 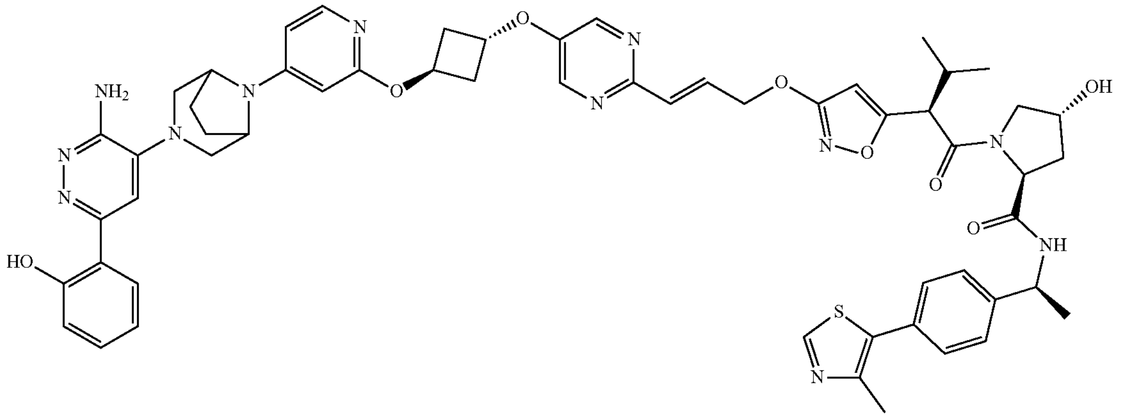 [SMILES: Cc1ncsc1-c1ccc([C@H](C)NC(=O)[C@@H]2C[C@@H](O)CN2C(=O)[C@@H](c2cc(OC/C=C/c3ncc(O[C@H]4C[C@H](Oc5cc(N6C7CCC6CN(c6cc(-c8ccccc8O)nnc6N)C7)ccn5)C4)cn3)no2)C(C)C)cc1] | (2S,4R)-1-((2R)-2-(3-(((E)-3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)allyl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 308 | 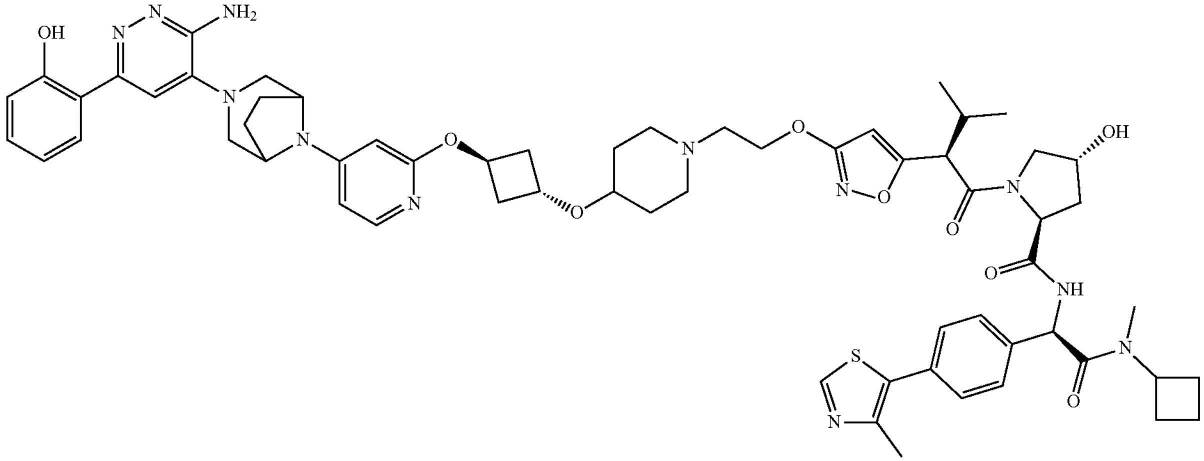 [SMILES: Cc1ncsc1-c1ccc([C@@H](NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)C(=O)N(C)C2CCC2)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-2-(cyclobutyl(methyl)amino)-1-(4-(4-methylthiazol-5-yl)phenyl)-2-oxoethyl)-4-hydroxypyrrolidine-2-carboxamide |

TABLE 1B-continued

| Ex. # | Structure | Compound Name |
|---|---|---|
| ]Exemplary bifunctional degradation compounds of the present disclosure | | |
| 309 | 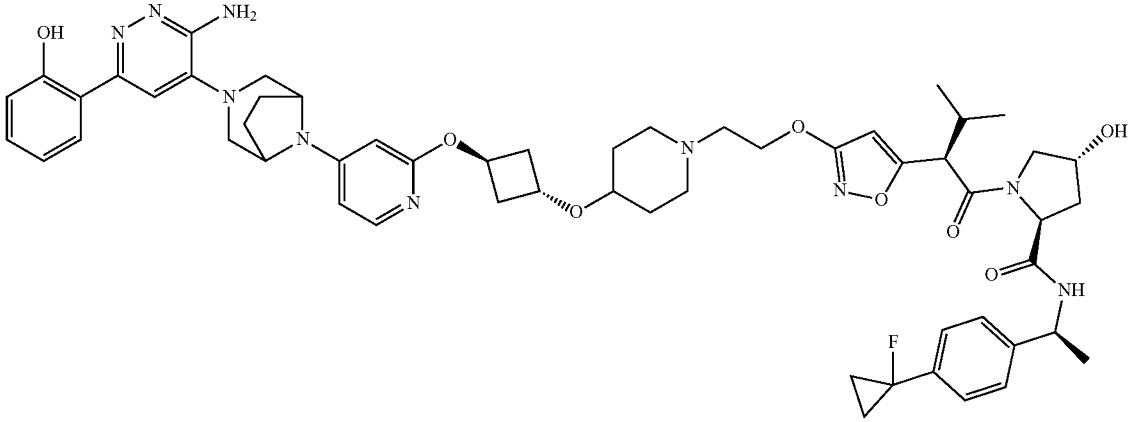 [SMILES: CC(C)[C@@H](C(=O)N1C[C@H](O)C[C@H]1C(=O)N[C@@H](C)c1ccc(C2(F)CC2)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(oxetan-3-yl)phenyl)ethyl)pyrrolidine-2-carboxamide |
| 310 | 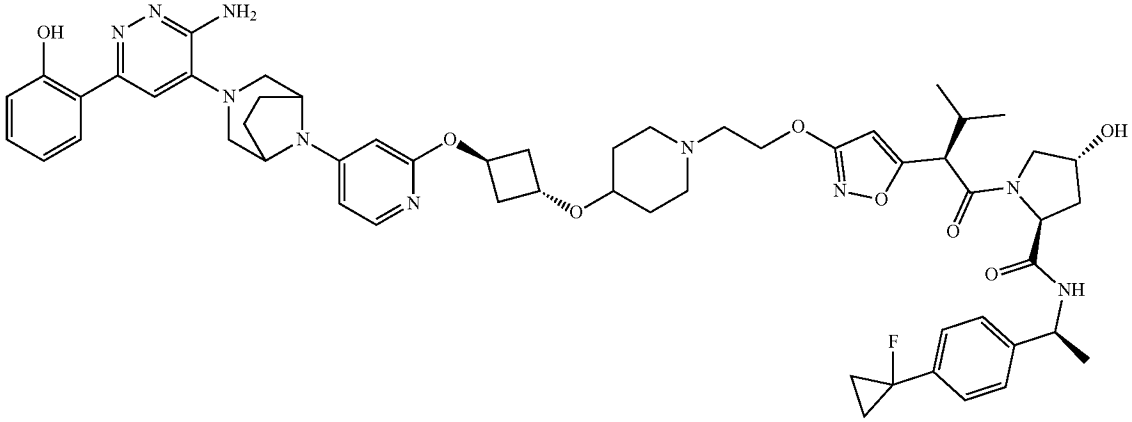 [SMILES: CC(C)[C@@H](C(=O)N1C[C@H](O)C[C@H]1C(=O)N[C@@H](C)c1ccc(C2(F)CC2)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(1-fluorocyclopropyl)phenyl)ethyl)-4-hydroxypyrrolidine-2-carboxamide |

TABLE 1B-continued

]Exemplary bifunctional degradation compounds of the present disclosure

| Ex. # | Structure | Compound Name |
|---|---|---|
| 311 | 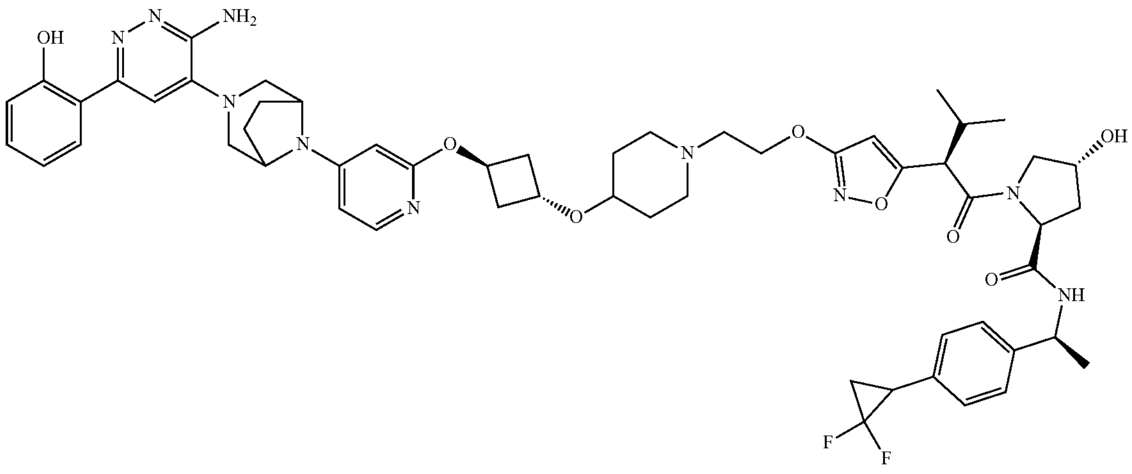 [SMILES: CC(C)[C@@H](C(=O)N1C[C@H](O)C[C@H]1C(=O)N[C@@H](C)c1ccc(C2CC2(F)F)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((1S)-1-(4-(2,2-difluorocyclopropyl)phenyl)ethyl)-4-hydroxypyrrolidine-2-carboxamide |
| 312 | 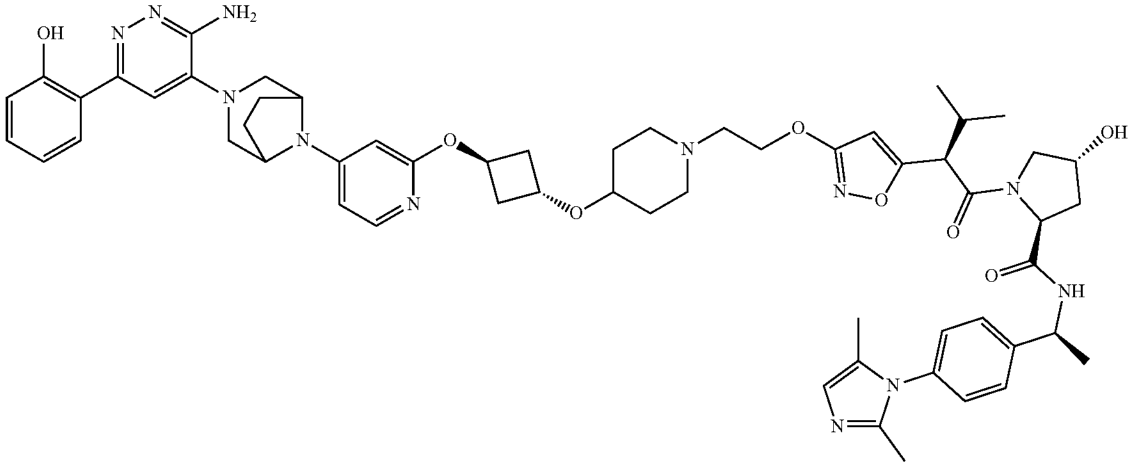 [SMILES: Cc1cnc(C)n1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(2,5-dimethyl-1H-imidazol-1-yl)phenyl)ethyl)-4-hydroxypyrrolidine-2-carboxamide |

TABLE 1B-continued

]Exemplary bifunctional degradation compounds of the present disclosure

| Ex. # | Structure | Compound Name |
| --- | --- | --- |
| 313 | 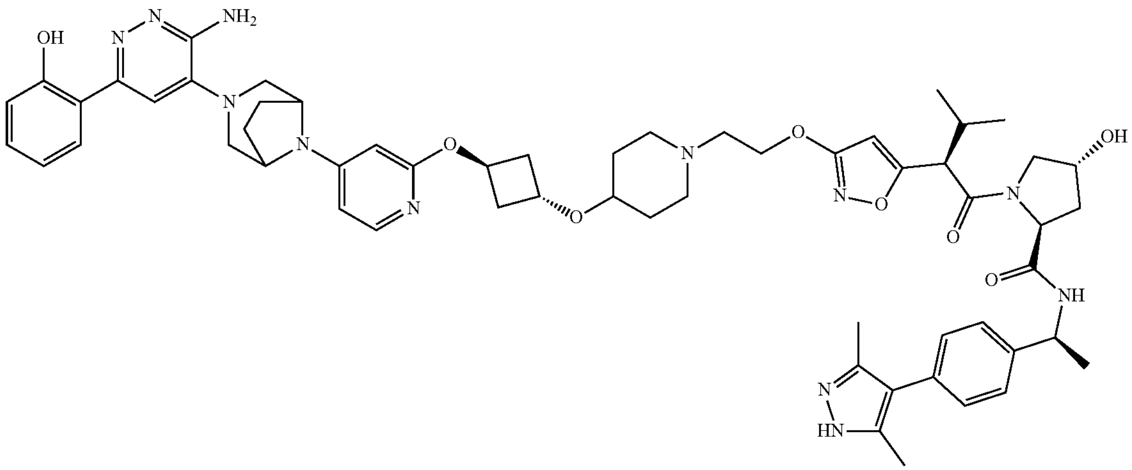 [SMILES: Cc1n[nH]c(C)c1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(1,4-dimethyl-1H-imidazol-5-yl)phenyl)ethyl)-4-hydroxypyrrolidine-2-carboxamide |
| 314 | 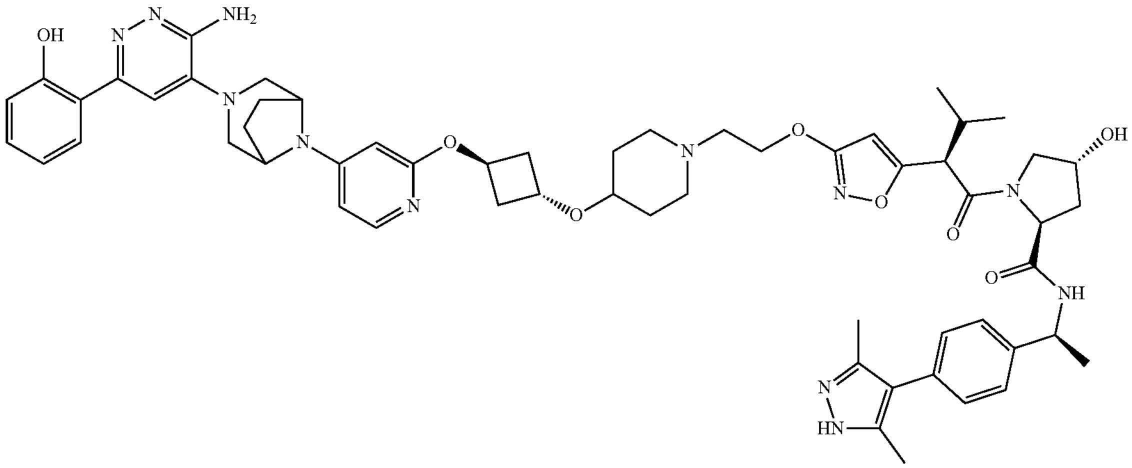 [SMILES: Cc1n[nH]c(C)c1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(3,5-dimethyl-1H-pyrazol-4-yl)phenyl)ethyl)-4-hydroxypyrrolidine-2-carboxamide |

TABLE 1B-continued

| ]Exemplary bifunctional degradation compounds of the present disclosure | | |
|---|---|---|
| Ex. # | Structure | Compound Name |
| 315 | 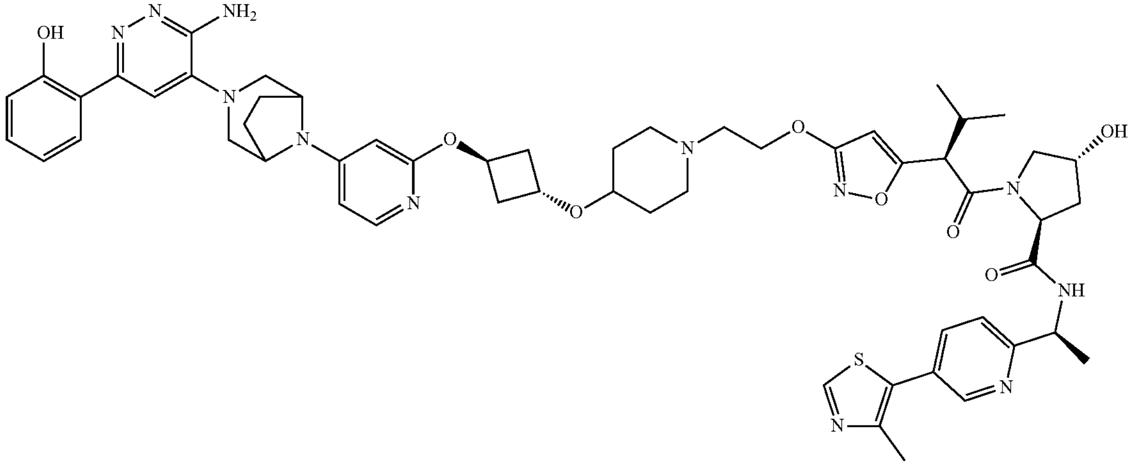 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)nc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(5-(4-methylthiazol-5-yl)pyridin-2-yl)ethyl)pyrrolidine-2-carboxamide |
| 316 | 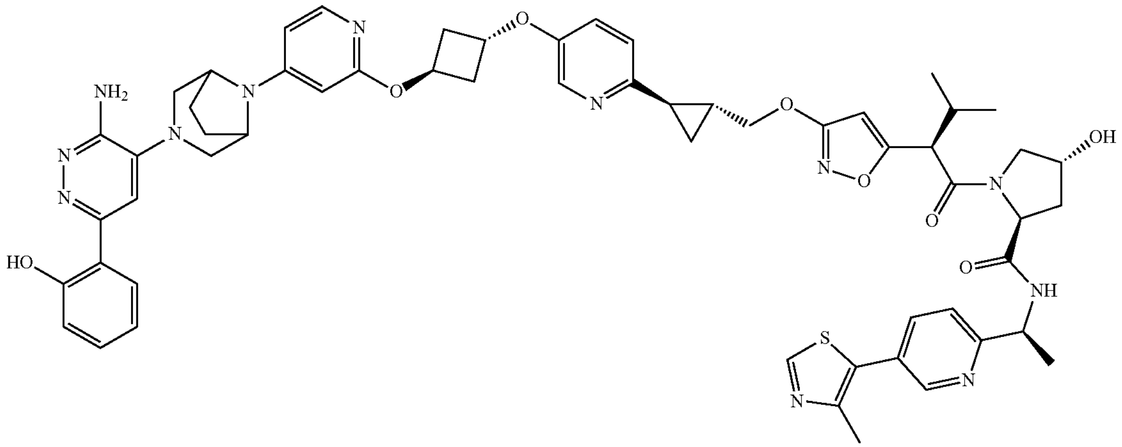 [SMILES: Cc1ncsc1-c1ccc([C@H](C)NC(=O)[C@@H]2C[C@@H](O)CN2C(=O)[C@@H](c2cc(OC[C@@H]3C[C@H]3c3ccc(O[C@H]4C[C@H](Oc5cc(N6C7CCC6CN(c6cc(-c8ccccc8O)nnc6N)C7)ccn5)C4)cn3)no2)C(C)C)nc1] | (2S,4R)-1-((2R)-2-(3-(((1R,2R)-2-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)cyclopropyl)methoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 317 | 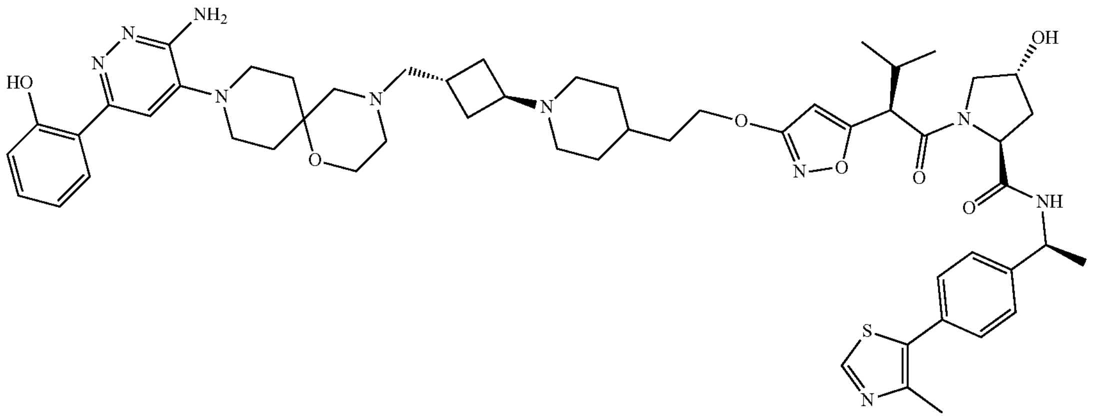 [SMILES: Cc1ncsc1-c1ccc([C@H](C)NC(=O)[C@@H]2C[C@@H](O)CN2C(=O)[C@@H](c2cc(OCCC3CCN([C@H]4C[C@H](CN5CCOC6(CCN(c7cc(-c8ccccc8O)nnc7N)CC6)C5)C4)CC3)no2)C(C)C)cc1] | (2S,4R)-1-((R)-2-(3-(2-(1-(((1r,3R)-3-((9-(3-amino-6-(2-hydroxyphenyl)pyridazin-4-yl)-1-oxa-4,9-diazaspiro[5.5]undecan-4-yl)methyl)cyclobutyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 318 | 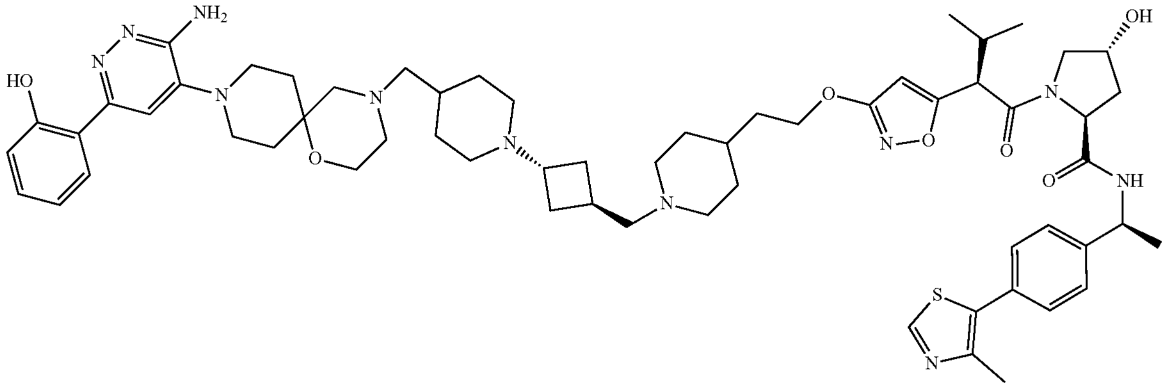 [SMILES: Cc1ncsc1-c1ccc([C@H](C)NC(=O)[C@@H]2C[C@@H](O)CN2C(=O)[C@@H](c2cc(OCCC3CCN(C[C@H]4C[C@H](N5CCC(CN6CCOC7(CCN(c8cc(-c9ccccc9O)nnc8N)CC7)C6)CC5)C4)CC3)no2)C(C)C)cc1] | (2S,4R)-1-((R)-2-(3-(2-(1-(((1r,3R)-3-(4-((9-(3-amino-6-(2-hydroxyphenyl)pyridazin-4-yl)-1-oxa-4,9-diazaspiro[5.5]undecan-4-yl)methyl)piperidin-1-yl)cyclobutyl)methyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

| Ex. # | Structure | Compound Name |
| --- | --- | --- |
| 319 | 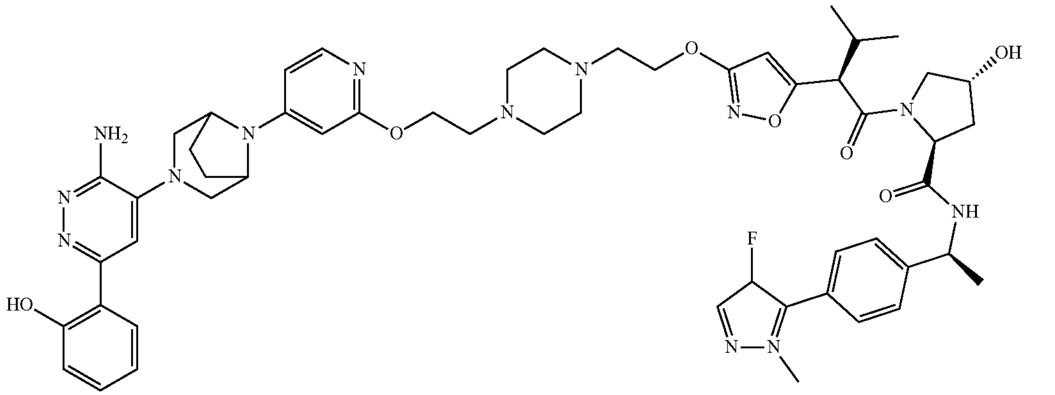 | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-fluoro-1-methyl-1H-pyrazol-5-yl)phenyl)ethyl)-4-hydroxypyrrolidine-2-carboxamide |
| 320 | 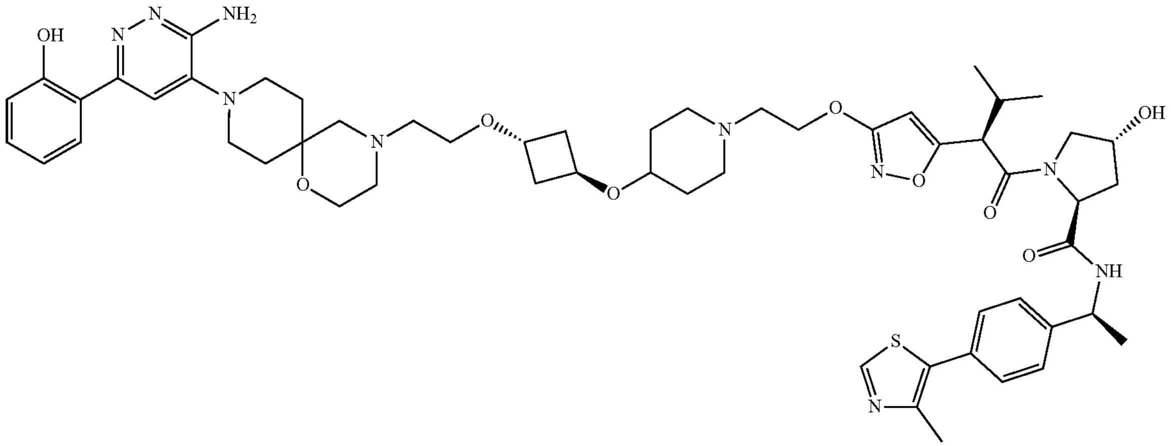 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](OCCN5CCOC6(CCN(c7cc(-c8ccccc8O)nnc7N)CC6)C5)C4)CC3)no2)C(C)C)cc1] | (2S,4R)-1-((R)-2-(3-(2-(4-((1r,3R)-3-(2-(9-(3-amino-6-(2-hydroxyphenyl)pyridazin-4-yl)-1-oxa-4,9-diazaspiro[5.5]undecan-4-yl)ethoxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

]Exemplary bifunctional degradation compounds of the present disclosure TABLE 1B-continued ]Exemplary bifunctional degradation compounds of the present disclosure

| Ex. # | Structure | Compound Name |
|---|---|---|
| 321 | 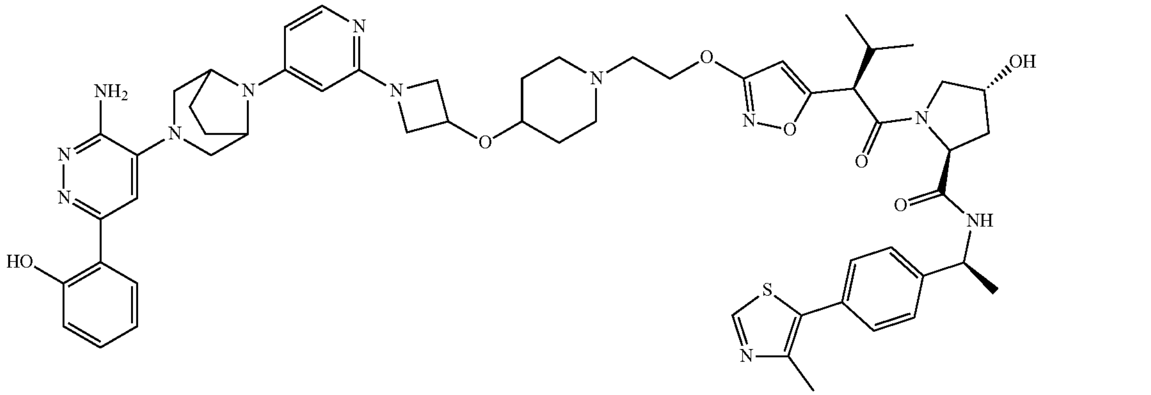 [SMILES: Cc1ncsc1-c1ccc([C@H](C)NC(=O)[C@@H]2C[C@@H](O)CN2C(=O)[C@@H](c2cc(OCCN3CCC(OC4CN(c5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-((1-(4-(3-(3-amino-6-(2-hydroxyphenyl)pyridazin-4-yl)-3,8-diazabicyclo[3.2.1]octan-8-yl)pyridin-2-yl)azetidin-3-yl)oxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 322 | 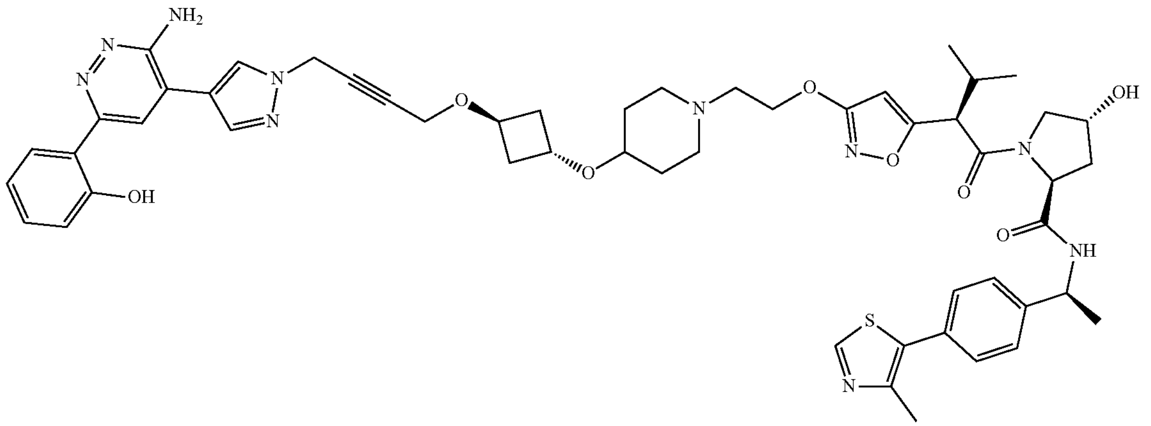 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](OCC#CCn5cc(-c6cc(-c7ccccc7O)nnc6N)cn5)C4)CC3)no2)C(C)C)cc1] | (2S,4R)-1-((R)-2-(3-(2-(4-((1r,3R)-3-((4-(4-(3-amino-6-(2-hydroxyphenyl)pyridazin-4-yl)-1H-pyrazol-1-yl)but-2-yn-1-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 323 | 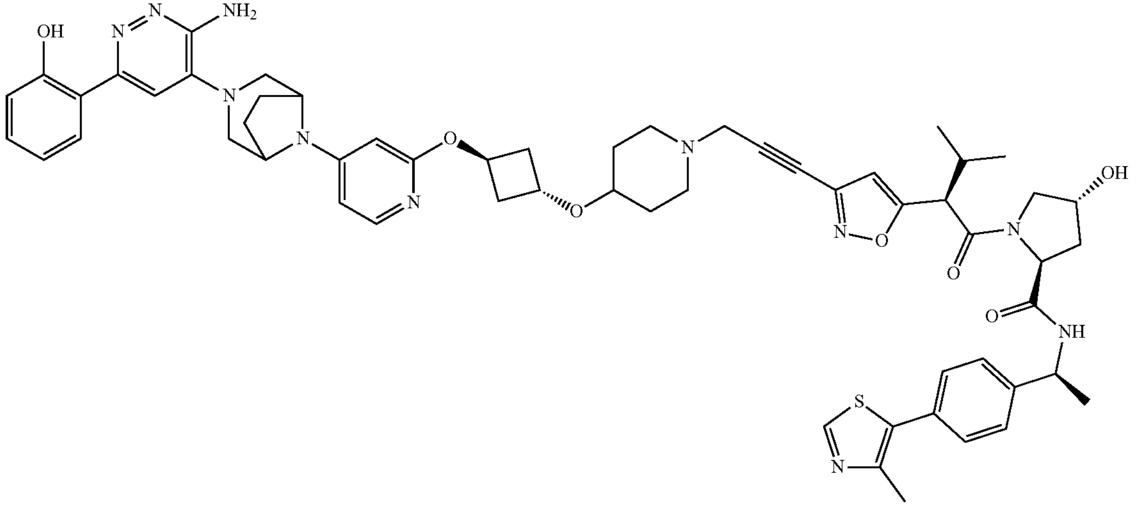 [SMILES: Cc1ncsc1-c1ccc([C@H](C)NC(=O)[C@@H]2C[C@@H](O)CN2C(=O)[C@@H](c2cc(C#CCN3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)prop-1-yn-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 324 | 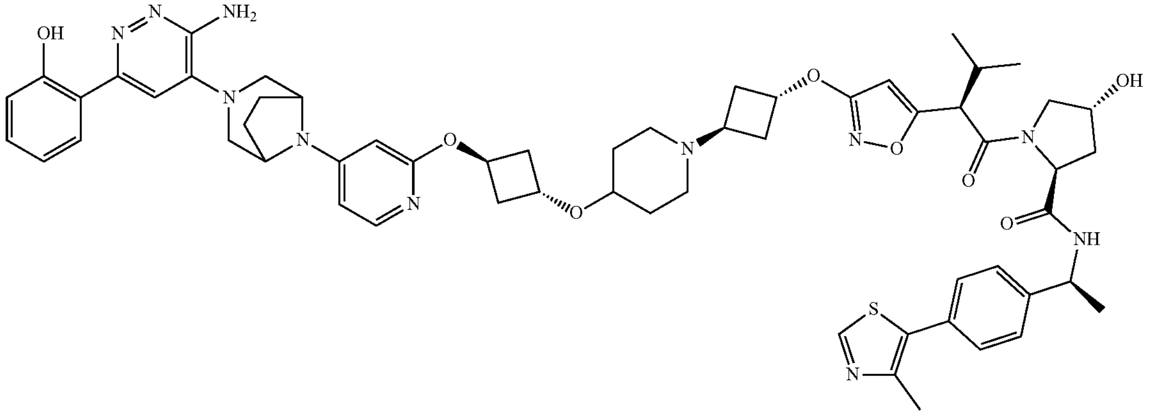 [SMILES: Cc1ncsc1-c1ccc([C@H](C)NC(=O)[C@@H]2C[C@@H](O)CN2C(=O)[C@@H](c2cc(O[C@H]3C[C@H](N4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2R)-2-(3-((1R,3R)-3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)cyclobutoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 325 | 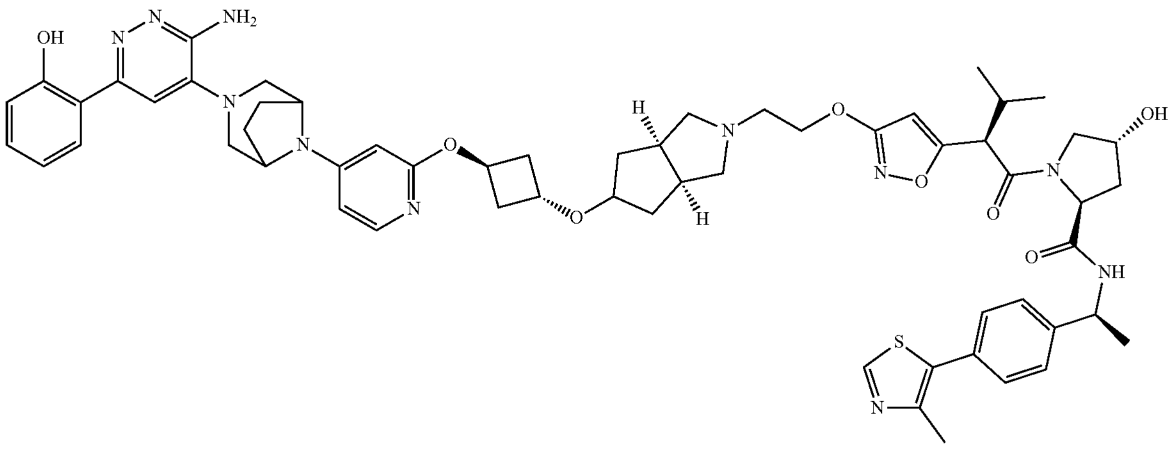 [SMILES: Cc1ncsc1-c1ccc([C@H](C)NC(=O)[C@@H]2C[C@@H](O)CN2C(=O)[C@@H](c2cc(OCCN3C[C@H]4CC(O[C@H]5C[C@H](Oc6cc(N7C8CCC7CN(c7cc(-c9ccccc9O)nnc7N)C8)ccn6)C5)C[C@H]4C3)no2)C(C)C)cc1] | (2S,4R)-1-((2R)-2-(3-(2-((3aR,6aS)-5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)hexahydrocyclopenta[c]pyrrol-2(1H)-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 326 | 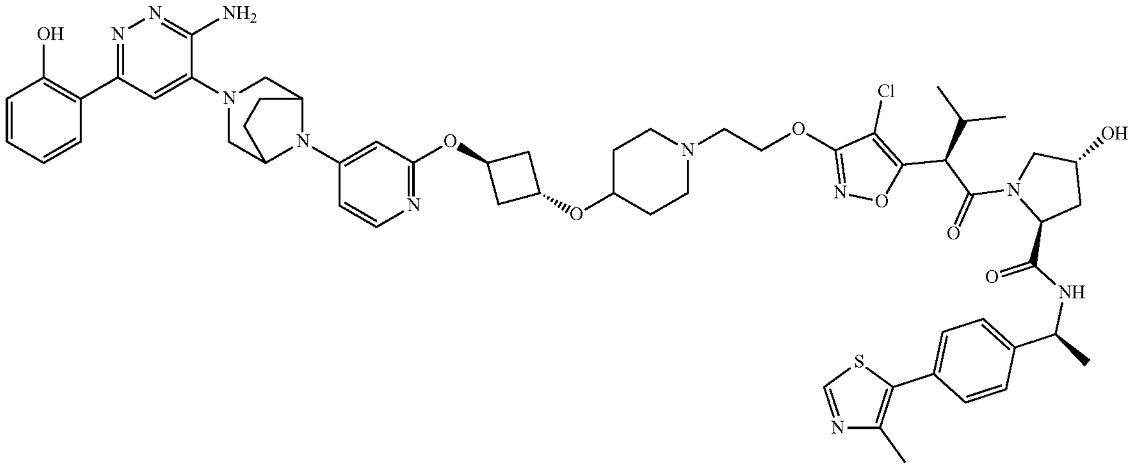 [SMILES: Cc1ncsc1-c1ccc([C@H](C)NC(=O)[C@@H]2C[C@@H](O)CN2C(=O)[C@@H](c2onc(OCCN3CCC(O[C@H]4C[C@H](Oc5cc(N6C7CCC6CN(c6cc(-c8ccccc8O)nnc6N)C7)ccn5)C4)CC3)c2Cl)C(C)C)cc1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-chloroisoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued
]Exemplary bifunctional degradation compounds of the present disclosure
| Ex. # | Structure | Compound Name |
| --- | --- | --- |
| 327 | 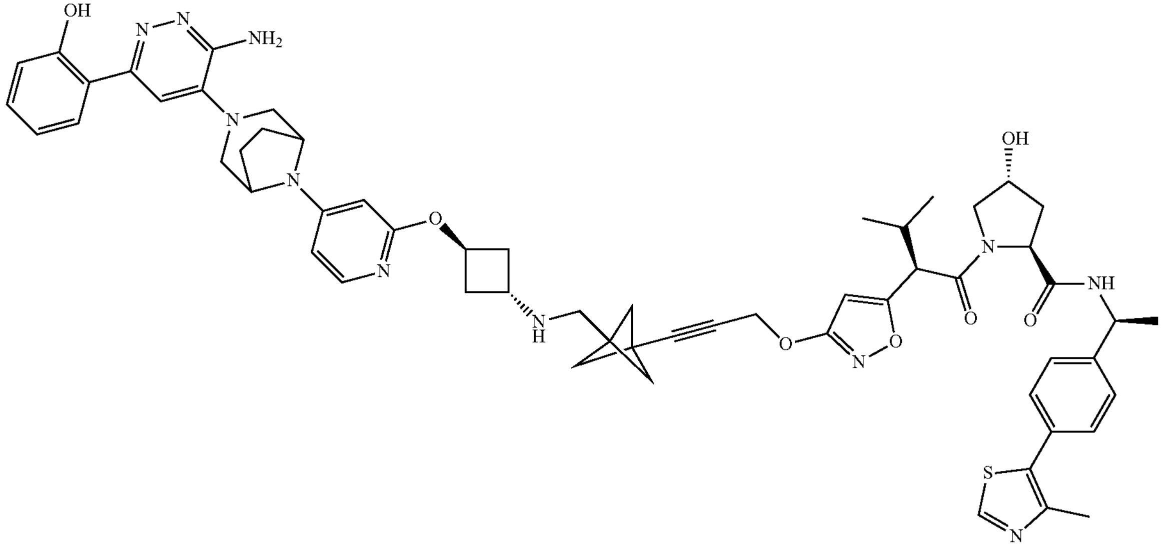 [SMILES: Cc1ncsc1-c1ccc([C@H](C)NC(=O)[C@@H]2C[C@@H](O)CN2C(=O)[C@@H](c2cc(OCC#CC34CC(CN[C@H]5C[C@H](Oc6cc(N7C8CCC7CN(c7cc(-c9ccccc9O)nnc7N)C8)ccn6)C5)(C3)C4)no2)C(C)C)cc1] | (2S,4R)-1-((2R)-2-(3-((3-(3-((((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)amino)methyl)bicyclo[1.1.1]pentan-1-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued
]Exemplary bifunctional degradation compounds of the present disclosure
| Ex. # | Structure | Compound Name |
| --- | --- | --- |
| 328 | 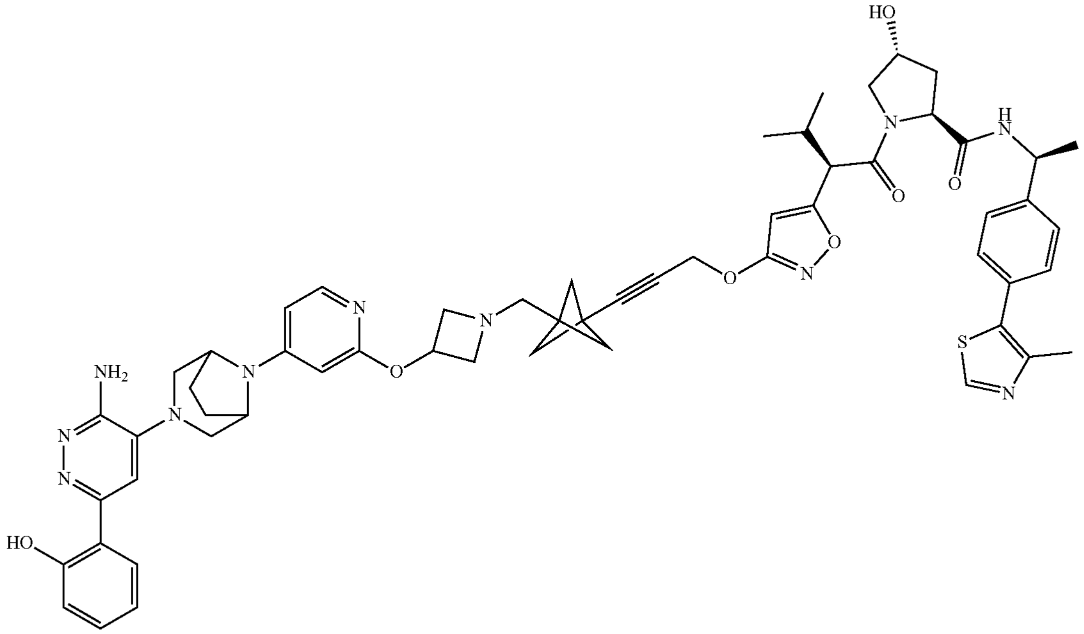 [SMILES: Cc1ncsc1-c1ccc([C@H](C)NC(=O)[C@@H]2C[C@@H](O)CN2C(=O)[C@@H](c2cc(OCC#CC34CC(CN5CC(Oc6cc(N7C8CCC7CN(c7cc(-c9ccccc9O)nnc7N)C8)ccn6)C5)(C3)C4)no2)C(C)C)cc1] | (2S,4R)-1-((2R)-2-(3-((3-(3-((3-((4-(3-(3-amino-6-(2-hydroxyphenyl)pyridazin-4-yl)-3,8-diazabicyclo[3.2.1]octan-8-yl)pyridin-2-yl)oxy)azetidin-1-yl)methyl)bicyclo[1.1.1]pentan-1-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 329 | 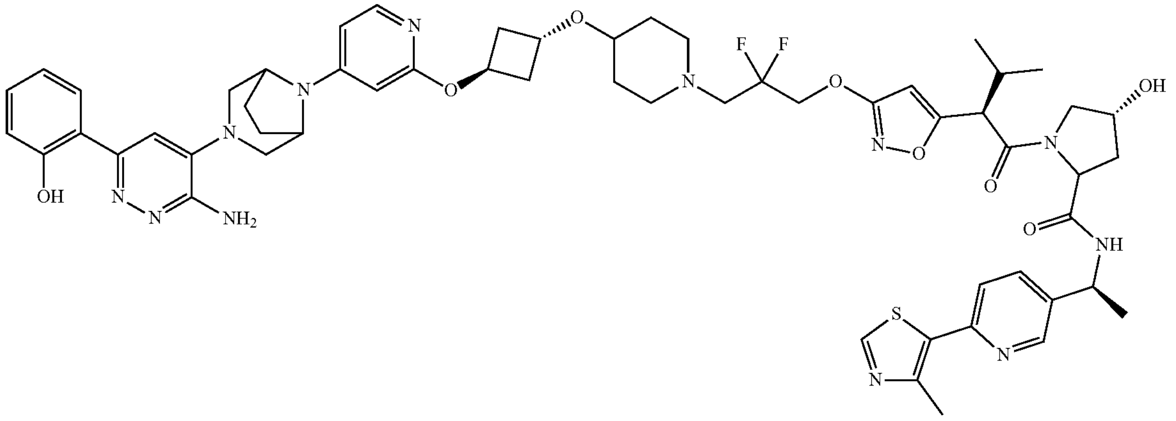 [SMILES: Cc1ncsc1-c1ccc([C@H](C)NC(=O)C2C[C@@H](O)CN2C(=O)[C@@H](c2cc(OCC(F)(F)CN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-2,2-difluoropropoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 330 | 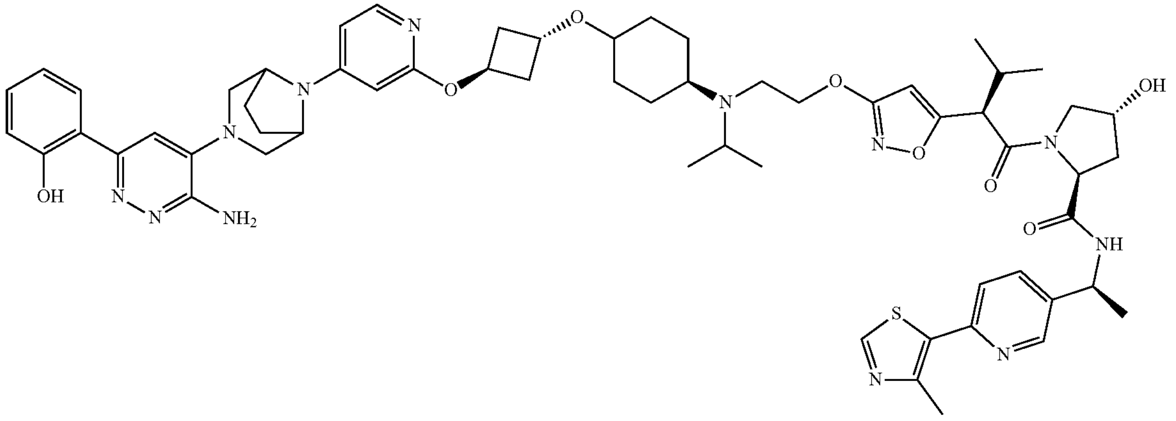 | (2S,4R)-1-((2R)-2-(3-(2-(((1R,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)(isopropyl)amino)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 331 | 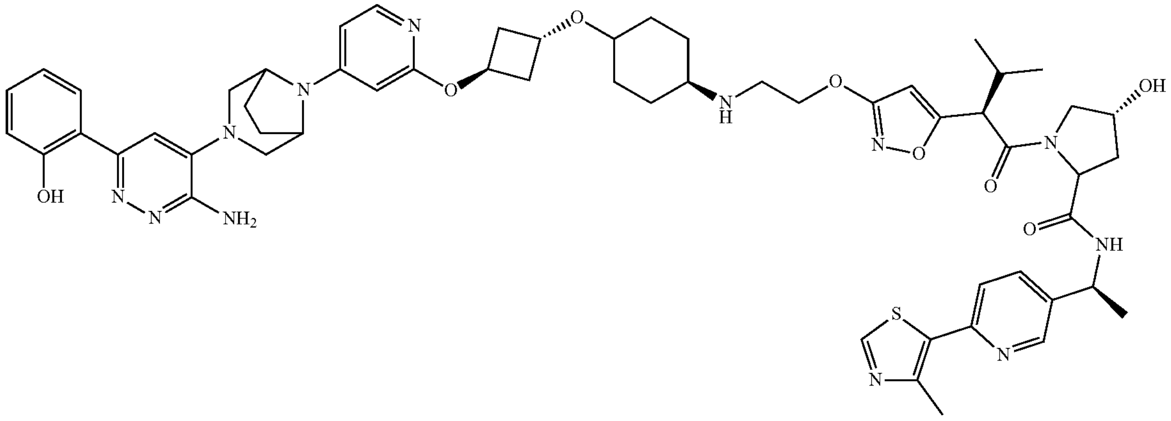 | (2S,4R)-1-((2R)-2-(3-(2-(((1R,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)amino)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 332 | 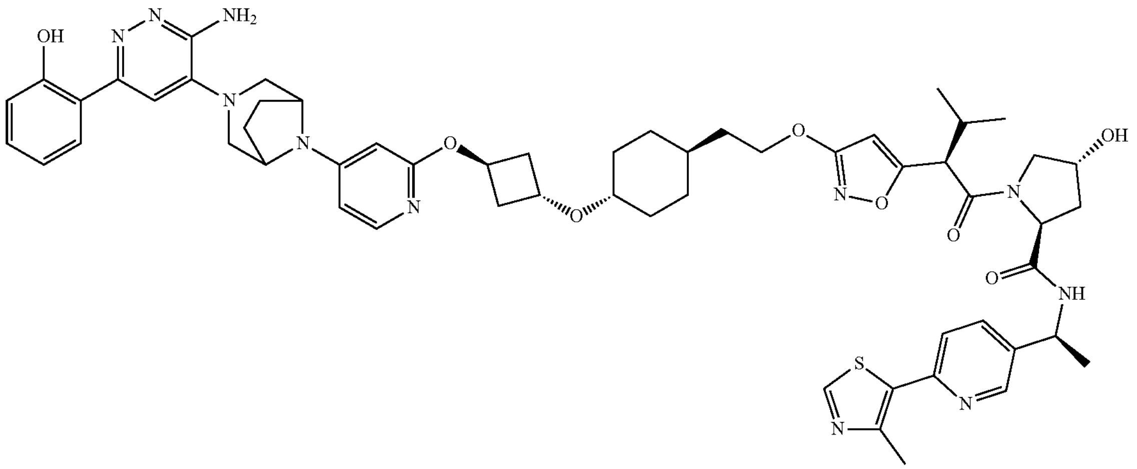 [SMILES: Cc1ncsc1-c1ccc([C@H](C)NC(=O)[C@@H]2C[C@@H](O)CN2C(=O)[C@@H](c2cc(OCC[C@H]3CC[C@H](O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-((1R,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

| Ex. # | Structure | Compound Name |
|---|---|---|
| ]Exemplary bifunctional degradation compounds of the present disclosure | | |
| 333 | 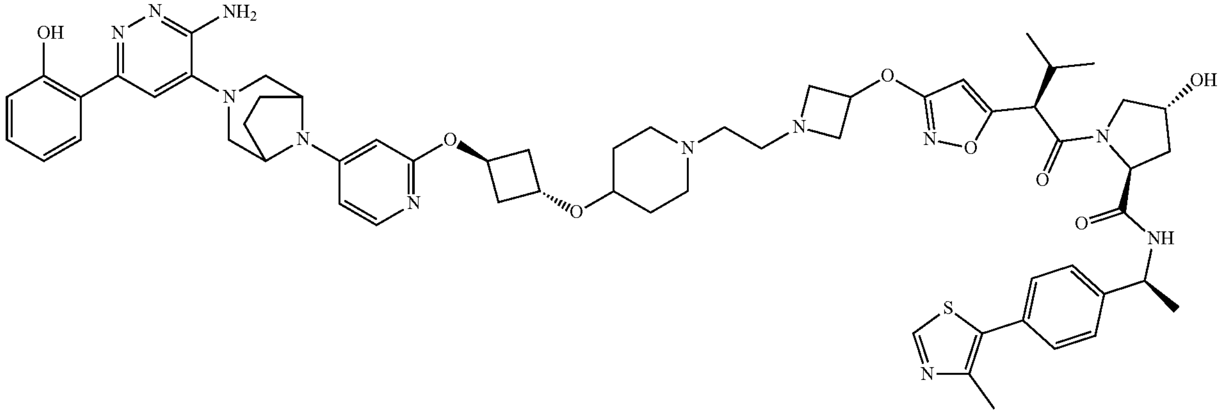 [SMILES: Cc1ncsc1-c1ccc([C@H](C)NC(=O)[C@@H]2C[C@@H](O)CN2C(=O)[C@@H](c2cc(OC3CN(CCN4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2R)-2-(3-((1-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)azetidin-3-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 334 | 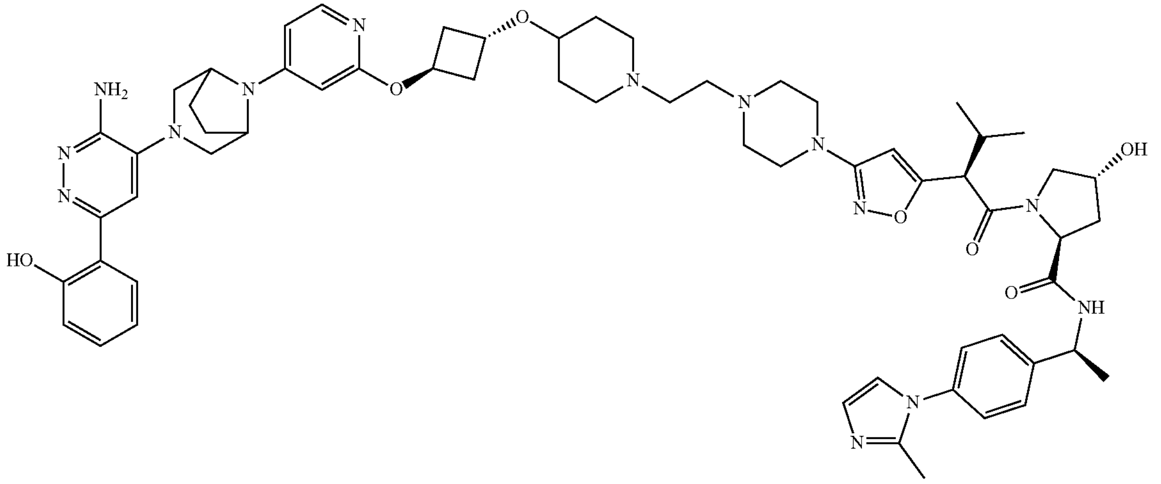 [SMILES: Cc1nccn1-c1ccc([C@H](C)NC(=O)[C@@H]2C[C@@H](O)CN2C(=O)[C@@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 335 | 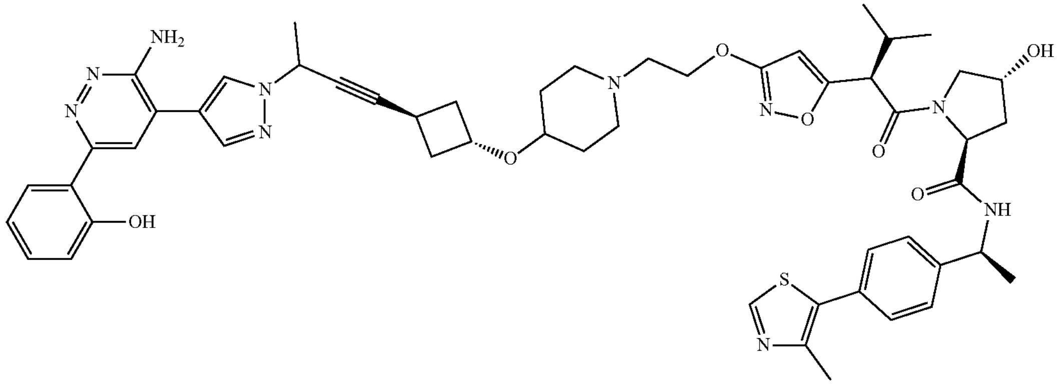 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](C#CC(C)n5cc(-c6cc(-c7ccccc7O)nnc6N)cn5)C4)CC3)no2)C(C)C)cc1] | (2S,4R)-1-((2R)-2-(3-(2-(4-((1r,3R)-3-(3-(4-(3-amino-6-(2-hydroxyphenyl)pyridazin-4-yl)-1H-pyrazol-1-yl)but-1-yn-1-yl)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 336 | 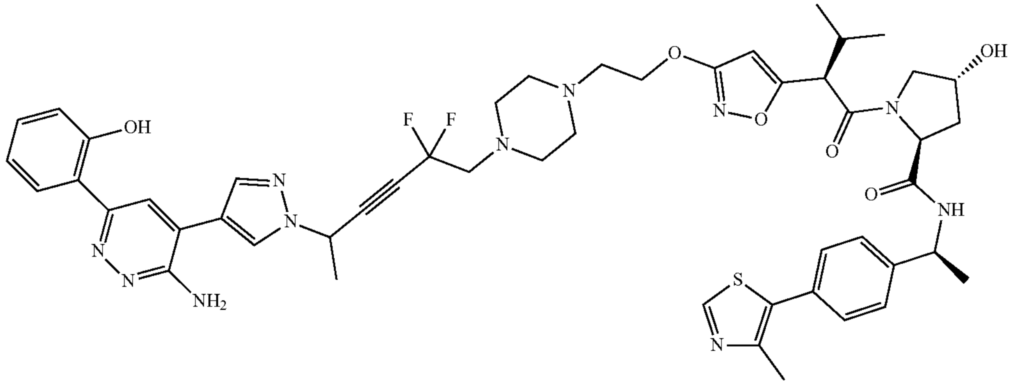 [SMILES: Cc1ncsc1-c1ccc([C@H](C)NC(=O)[C@@H]2C[C@@H](O)CN2C(=O)[C@@H](c2cc(OCCN3CCN(CC(F)(F)C#CC(C)n4cc(-c5cc(-c6ccccc6O)nnc5N)cn4)CC3)no2)C(C)C)cc1] | (2S,4R)-1-((2R)-2-(3-(2-(4-(5-(4-(3-amino-6-(2-hydroxyphenyl)pyridazin-4-yl)-1H-pyrazol-1-yl)-2,2-difluorohex-3-yn-1-yl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 337 | 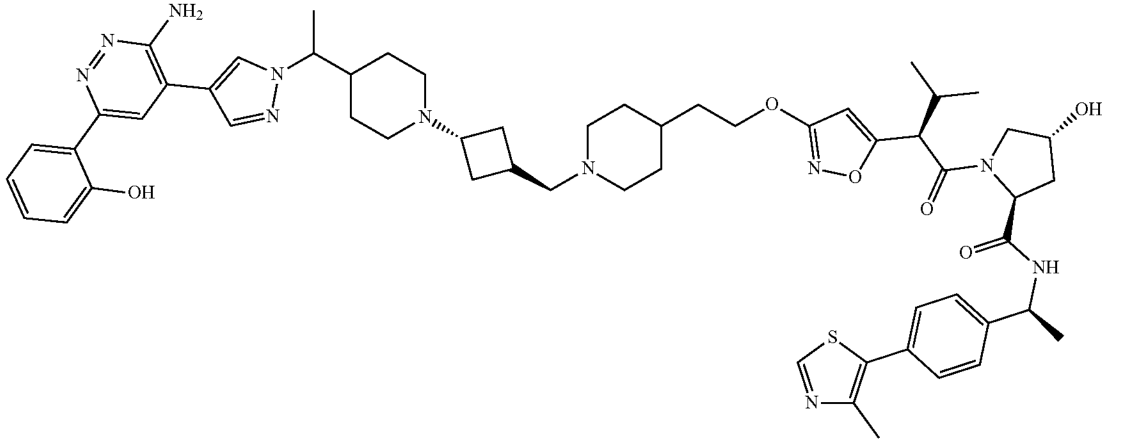 | (2S,4R)-1-((2R)-2-(3-(2-(1-(((1r,3R)-3-(4-(1-(4-(3-amino-6-(2-hydroxyphenyl)pyridazin-4-yl)-1H-pyrazol-1-yl)ethyl)piperidin-1-yl)cyclobutyl)methyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 338 | 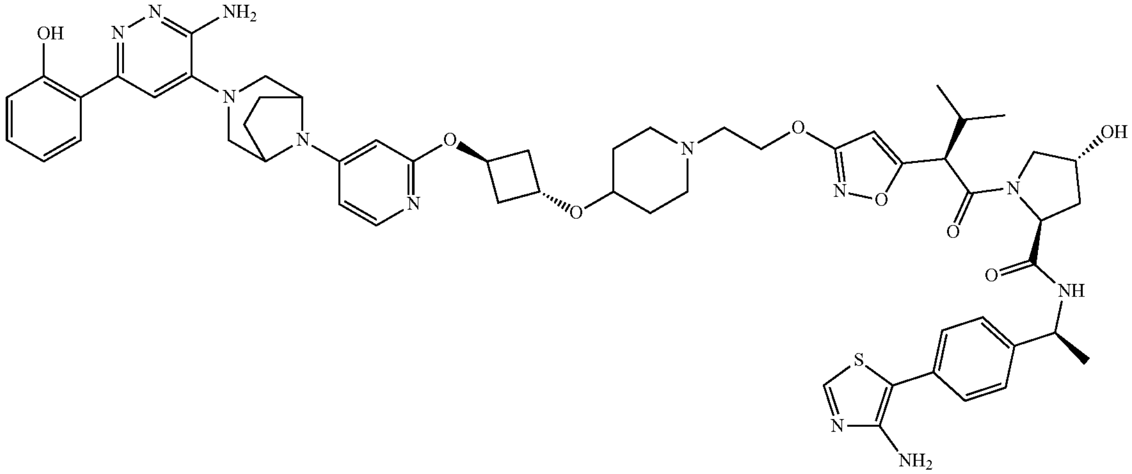 [SMILES: CC(C)[C@@H](C(=O)N1C[C@H](O)C[C@H]1C(=O)N[C@@H](C)c1ccc(-c2scnc2N)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(4-aminothiazol-5-yl)phenyl)ethyl)-4-hydroxypyrrolidine-2-carboxamide |

TABLE 1B-continued

]Exemplary bifunctional degradation compounds of the present disclosure

| Ex. # | Structure | Compound Name |
| --- | --- | --- |
| 339 | 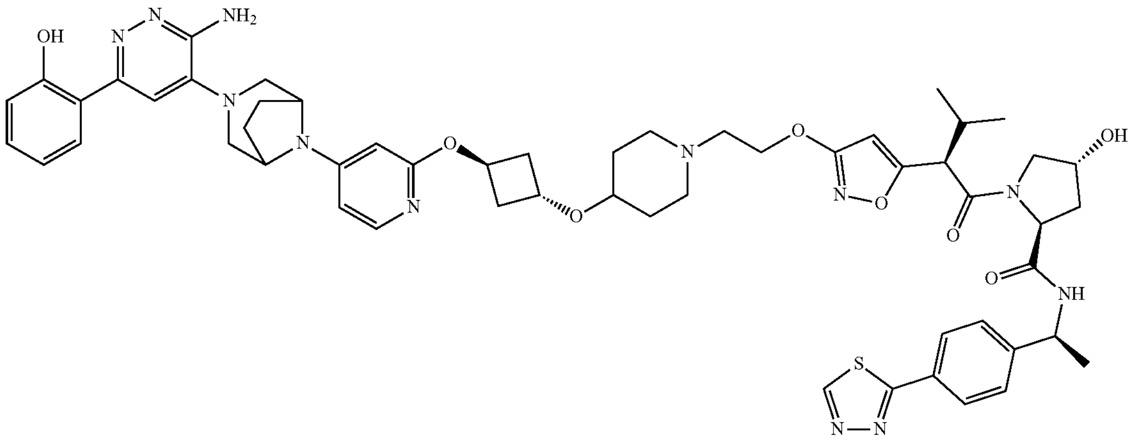 [SMILES: CC(C)[C@@H](C(=O)N1C[C@H](O)C[C@H]1C(=O)N[C@@H](C)c1ccc(-c2nncs2)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-N-((S)-1-(4-(1,3,4-thiadiazol-2-yl)phenyl)ethyl)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamide |
| 340 | 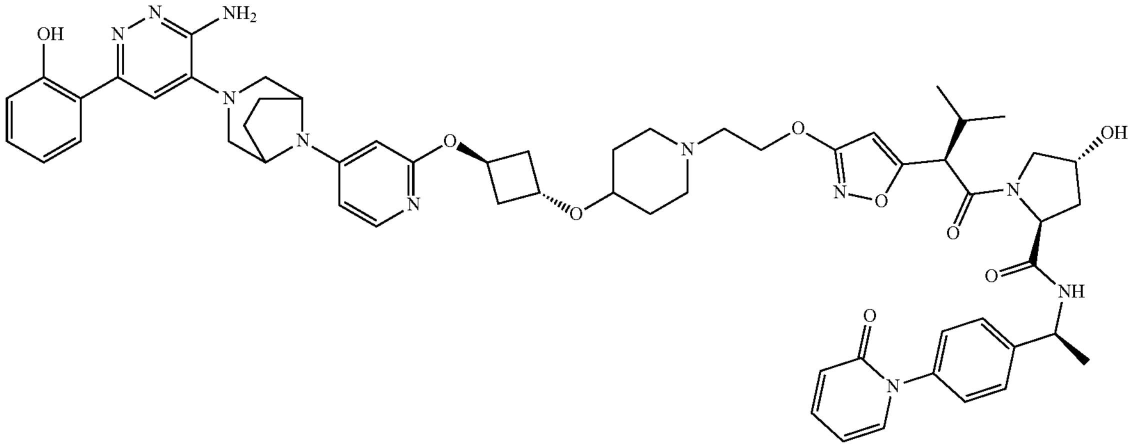 [SMILES: CC(C)[C@@H](C(=O)N1C[C@H](O)C[C@H]1C(=O)N[C@@H](C)c1ccc(-n2ccccc2=O)cc1)c1cc(OCCN2CCC(O[C@H]3C[C@H](Oc4cc(N5C6CCC5CN(c5cc(-c7ccccc7O)nnc5N)C6)ccn4)C3)CC2)no1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(2-oxopyridin-1(2H)-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 341 | 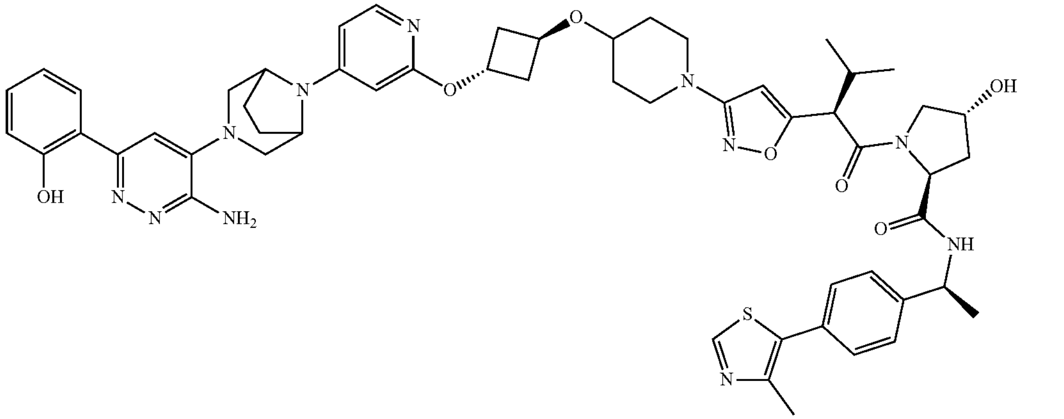 [SMILES: Cc1ncsc1-c1ccc([C@H](C)NC(=O)[C@@H]2C[C@@H](O)CN2C(=O)[C@@H](c2cc(N3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 342 | 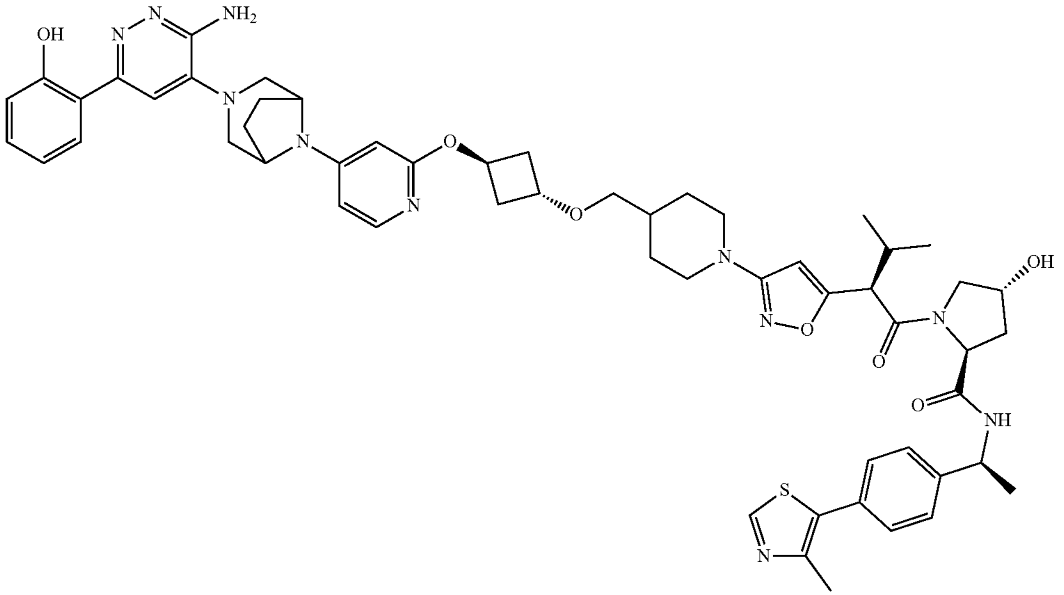 [SMILES: Cc1ncsc1-c1ccc([C@H](C)NC(=O)[C@@H]2C[C@@H](O)CN2C(=O)[C@@H](c2cc(N3CCC(CO[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(4-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)methyl) piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
|---|---|---|
| 343 | 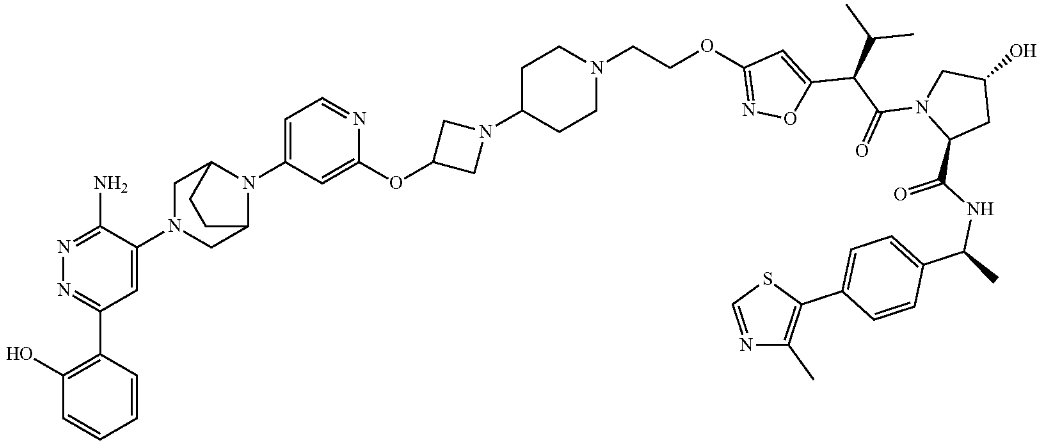 [SMILES: Cc1ncsc1-c1ccc([C@H](C)NC(=O)[C@@H]2C[C@@H](O)CN2C(=O)[C@@H](c2cc(OCCN3CCC(N4CC(Oc5cc(N6C7CCC6CN(c6cc(-c8ccccc8O)nnc6N)C7)ccn5)C4)CC3)no2)C(C)C)cc1] | (2S,4R)-1-((2R)-2-(3-(2-(4-(3-((4-(3-(3-amino-6-(2-hydroxyphenyl)pyridazin-4-yl)-3,8-diazabicyclo[3.2.1]octan-8-yl)pyridin-2-yl)oxy)azetidin-1-yl)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 344 | 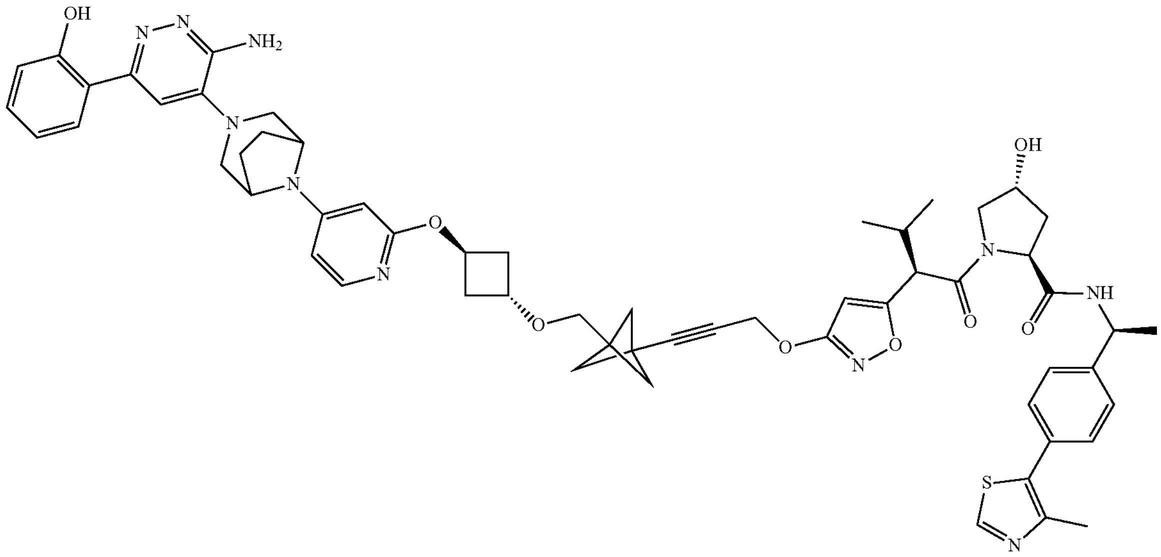 [SMILES: Cc1ncsc1-c1ccc([C@H](C)NC(=O)[C@@H]2C[C@@H](O)CN2C(=O)[C@@H](c2cc(OCC#CC34CC(CO[C@H]5C[C@H](Oc6cc(N7C8CCC7CN(c7cc(-c9ccccc9O)nnc7N)C8)ccn6)C5)(C3)C4)no2)C(C)C)cc1] | (2S,4R)-1-((2R)-2-(3-((3-(3-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)methyl)bicyclo[1.1.1]pentan-1-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1B-continued

]Exemplary bifunctional degradation compounds of the present disclosure

| Ex. # | Structure | Compound Name |
| --- | --- | --- |
| 345 | 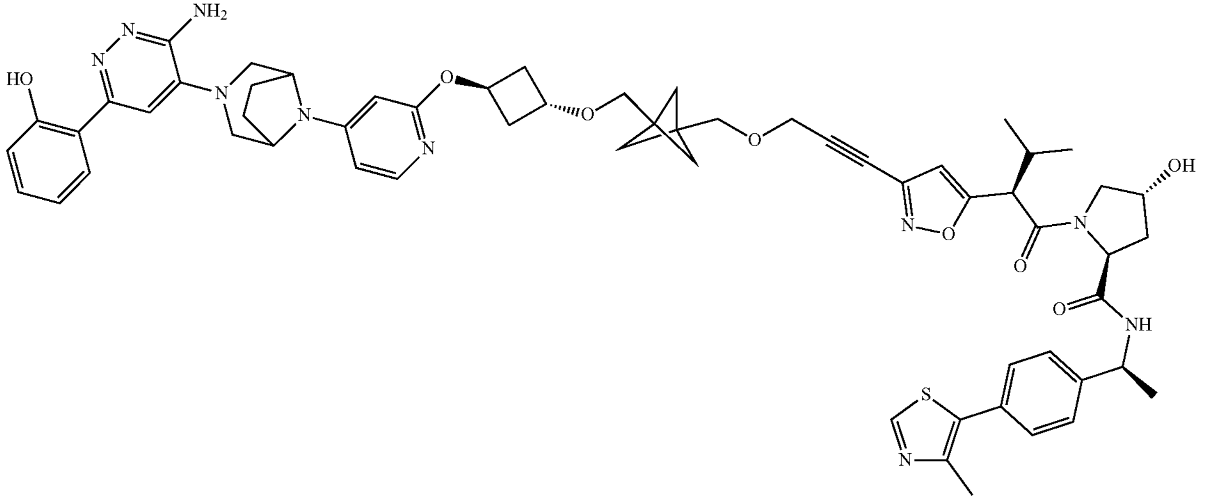 [SMILES: Cc1ncsc1-c1ccc([C@H](C)NC(=O)[C@@H]2C[C@@H](O)CN2C(=O)[C@@H](c2cc(C#CCOCC34CC(CO[C@H]5C[C@H](Oc6cc(N7C8CCC7CN(c7cc(-c9ccccc9O)nnc7N)C8)ccn6)C5)(C3)C4)no2)C(C)C)cc1] | (2S,4R)-1-((2R)-2-(3-(3-((3-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)methyl)bicyclo[1.1.1]pentan-1-yl)methoxy)prop-1-yn-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 346 | 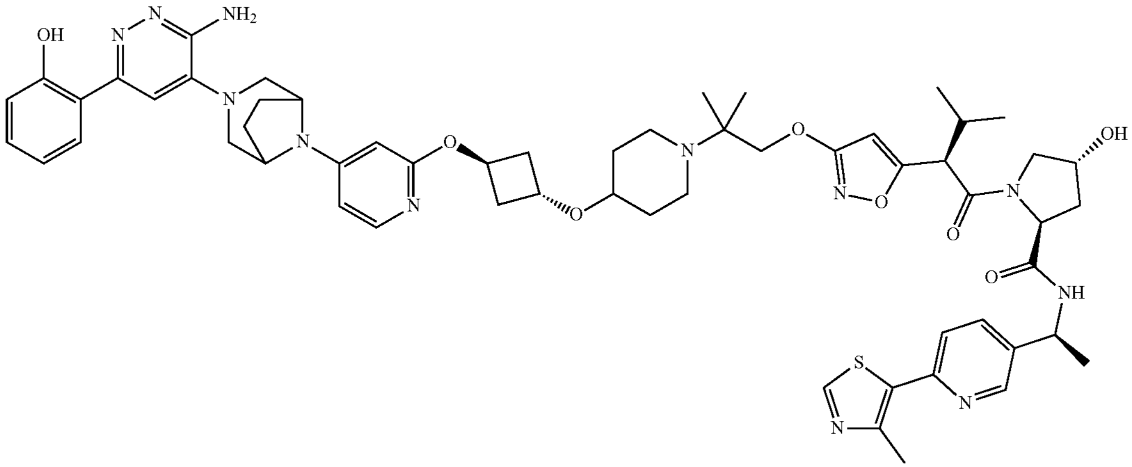 [SMILES: Cc1ncsc1-c1ccc([C@H](C)NC(=O)[C@@H]2C[C@@H](O)CN2C(=O)[C@@H](c2cc(OCC(C)(C)N3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-2-methylpropoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

]Exemplary bifunctional degradation compounds of the present disclosure

| Ex. # | Structure | Compound Name |
|---|---|---|
| 347 | 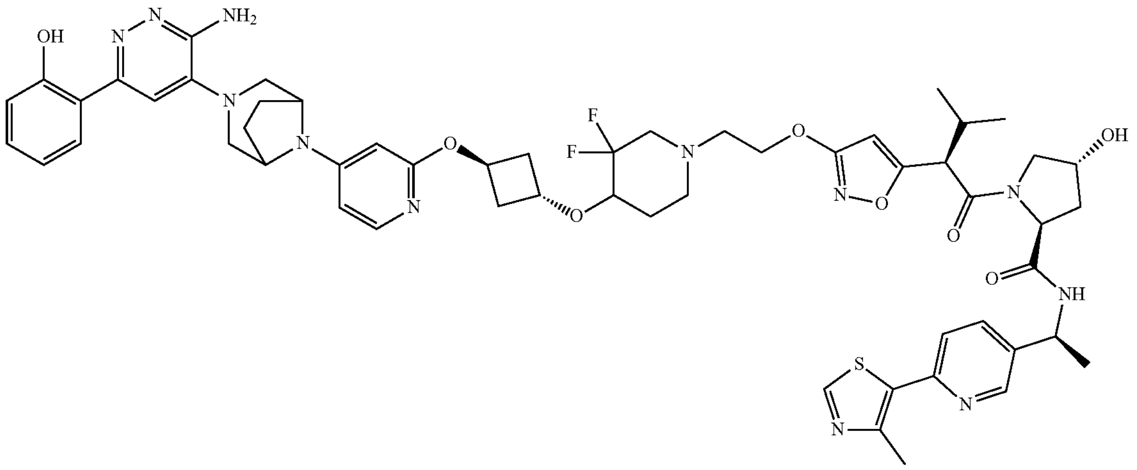 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)C(F)(F)C3)no2)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-3,3-difluoropiperidin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 348 | 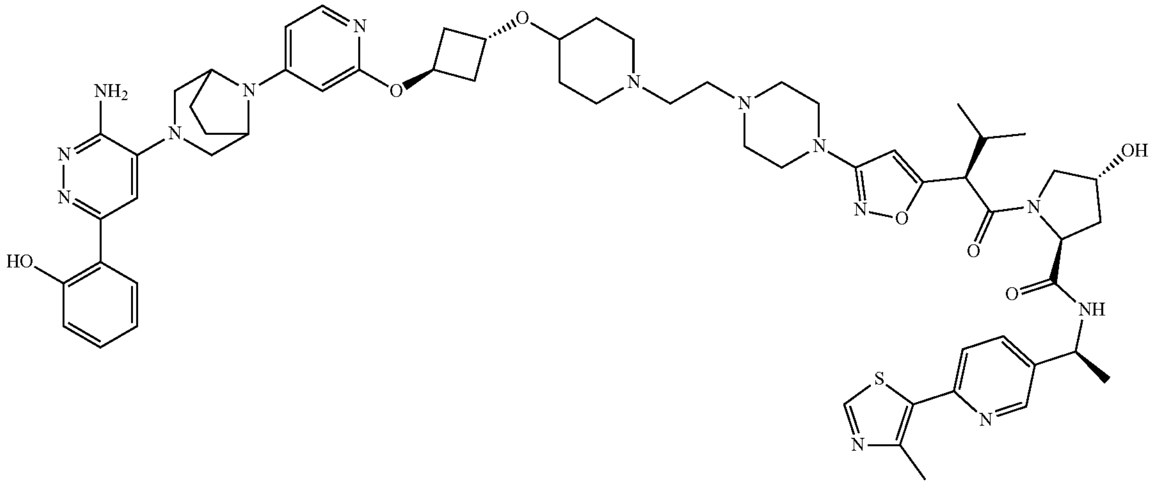 [SMILES: Cc1ncsc1-c1ccc([C@H](C)NC(=O)[C@@H]2C[C@@H](O)CN2C(=O)[C@@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cn1] | (2S,4R)-1-((2R)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued

| ]Exemplary bifunctional degradation compounds of the present disclosure | | |
|---|---|---|
| Ex. # | Structure | Compound Name |
| 349 | 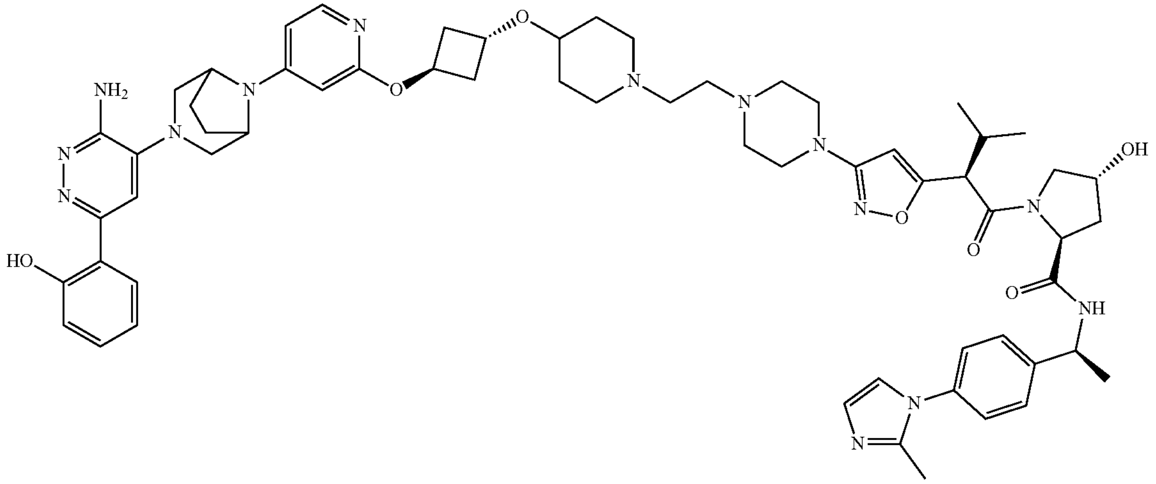 [SMILES: Cc1nccn1-c1ccc([C@H](C)NC(=O)[C@@H]2C[C@@H](O)CN2C(=O)[C@@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |
| 350 | 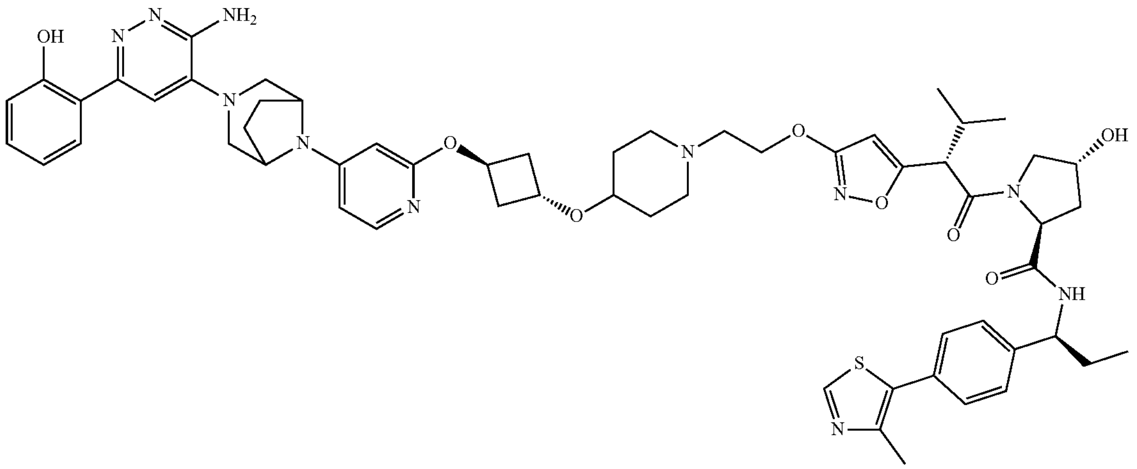 [SMILES: CC[C@H](NC(=O)[C@@H]1C[C@@H](O)CN1C(=O)[C@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C)c1ccc(-c2scnc2C)cc1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)propyl)pyrrolidine-2-carboxamide |

TABLE 1B-continued

]Exemplary bifunctional degradation compounds of the present disclosure

| Ex. # | Structure | Compound Name |
|---|---|---|
| 351 | 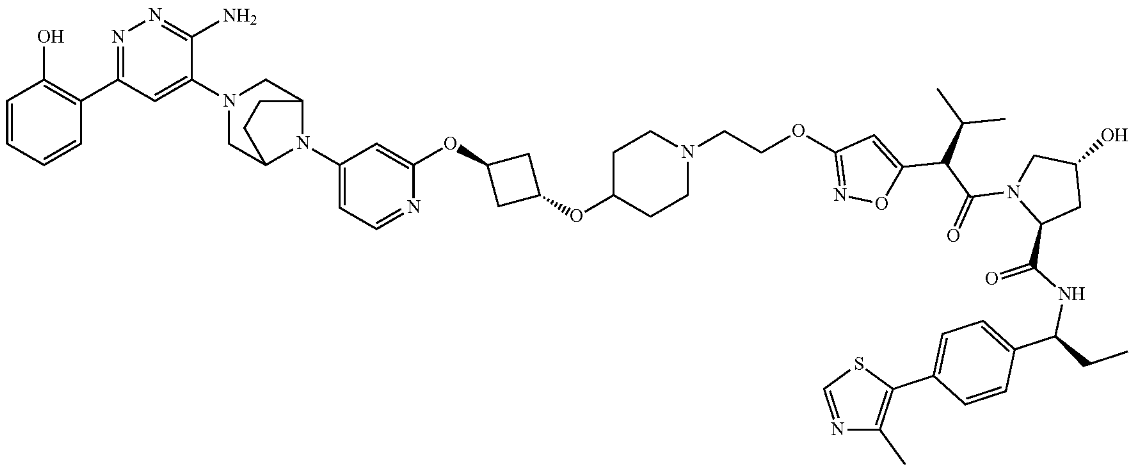 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)propyl)pyrrolidine-2-carboxamide |
| 352 | 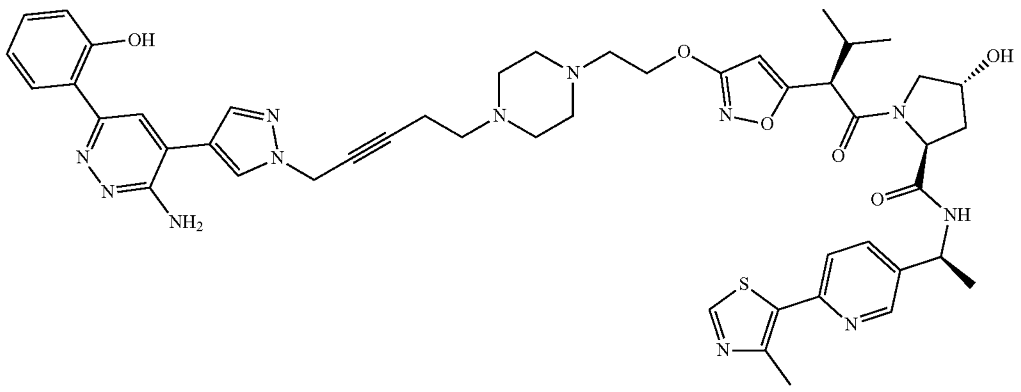 [SMILES: Cc1ncsc1-c1ccc([C@H](C)NC(=O)[C@@H]2C[C@@H](O)CN2C(=O)[C@@H](c2cc(OCCN3CCN(CCC#CCn4cc(-c5cc(-c6ccccc6O)nnc5N)cn4)CC3)no2)C(C)C)cn1] | (2S,4R)-1-((R)-2-(3-(2-(4-(5-(4-(3-amino-6-(2-hydroxyphenyl)pyridazin-4-yl)-1H-pyrazol-1-yl)pent-3-yn-1-yl)piperazin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1B-continued
| ]Exemplary bifunctional degradation compounds of the present disclosure | | |
|---|---|---|
| Ex. # | Structure | Compound Name |
| 353 | 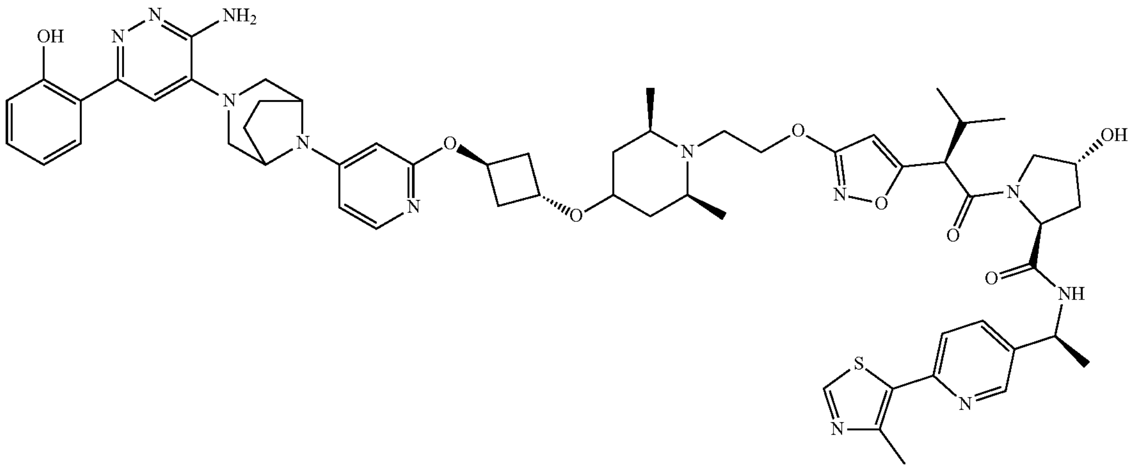 [SMILES: Cc1ncsc1-c1ccc([C@H](C)NC(=O)[C@@H]2C[C@@H](O)CN2C(=O)[C@@H](c2cc(OCCN3[C@H](C)CC(O[C@H]4C[C@H](Oc5cc(N6C7CCC6CN(c6cc(-c8ccccc8O)nnc6N)C7)ccn5)C4)C[C@@H]3C)no2)C(C)C)cn1] | (2S,4R)-1-((2R)-2-(3-(2-((2S,6R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-2,6-dimethylpiperidin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |

TABLE 1C
| Exemplary bifunctional degradation compounds of the present disclosure | | |
|---|---|---|
| Ex. # | Compound Name | Structure |
| 354 | (2S,4R)-1-((2S)-2-(3-(2-(4-((1-(4-(3-(3-amino-6-(2-hydroxyphenyl)pyridazin-4-yl)-3,8-diazabicyclo[3.2.1]octan-8-yl)pyridin-2-yl)azetidin-3-yl)oxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 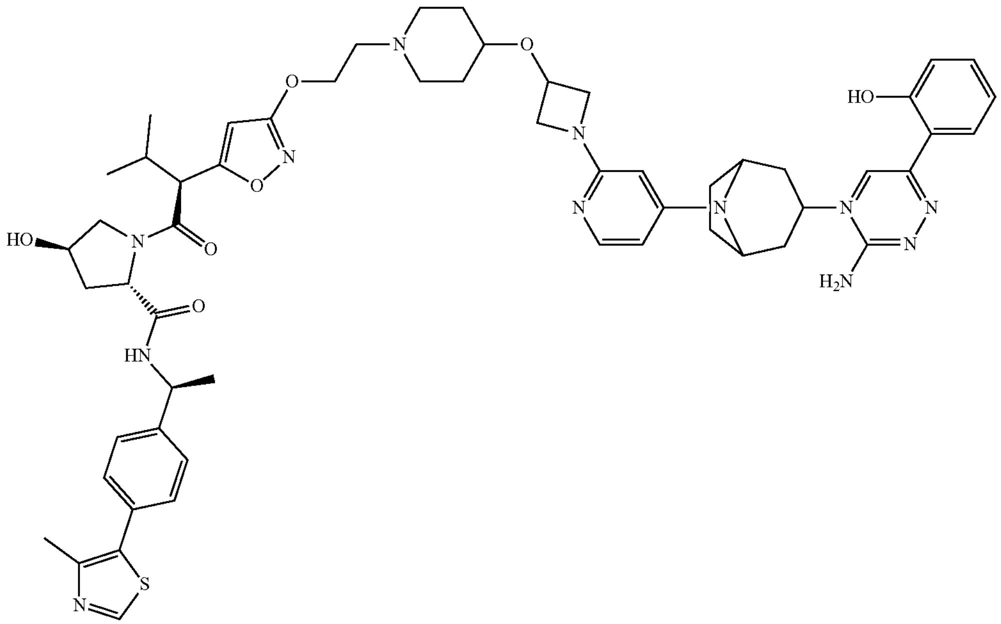 |

TABLE 1C-continued
| Exemplary bifunctional degradation compounds of the present disclosure | | |
|---|---|---|
| Ex. # | Compound Name | Structure |
| 355 | (2S,4R)-1-((2R)-2-(3-(2-(4-((1-(4-(3-(3-amino-6-(2-hydroxyphenyl)pyridazin-4-yl)-3,8-diazabicyclo[3.2.1]octan-8-yl)pyridin-2-yl)azetidin-3-yl)oxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 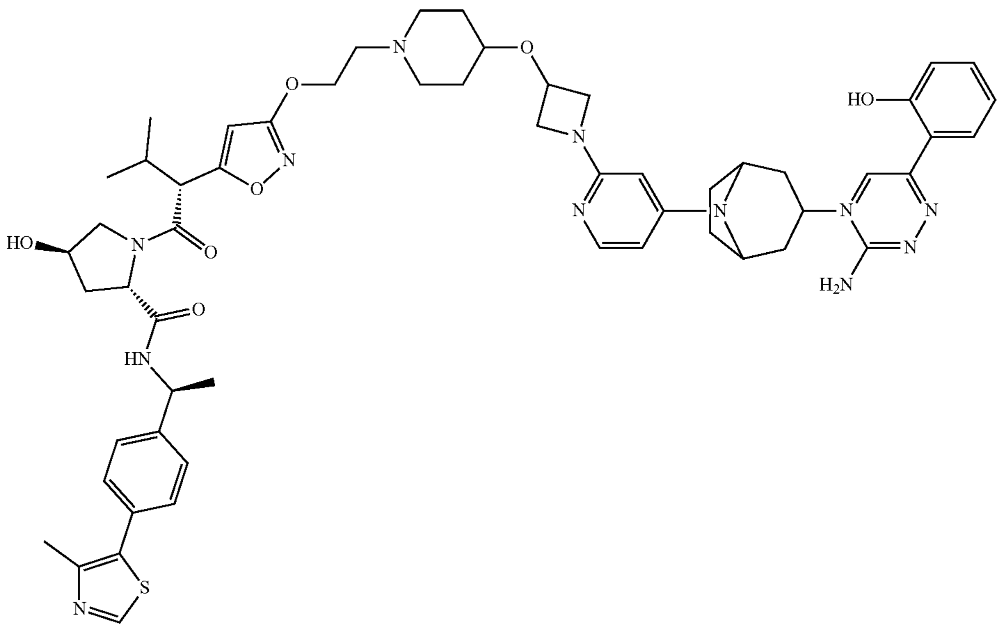 |

TABLE 1C-continued

| Ex. # | Compound Name | Structure |
|---|---|---|
| | Exemplary bifunctional degradation compounds of the present disclosure | |
| 356 | (2S,4R)-1-((2S)-2-(3-(2-(2-((4-(3-(3-amino-6-(2-hydroxyphenyl)pyridazin-4-yl)-3,8-diazabicyclo[3.2.1]octan-8-yl)pyridin-2-yl)oxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 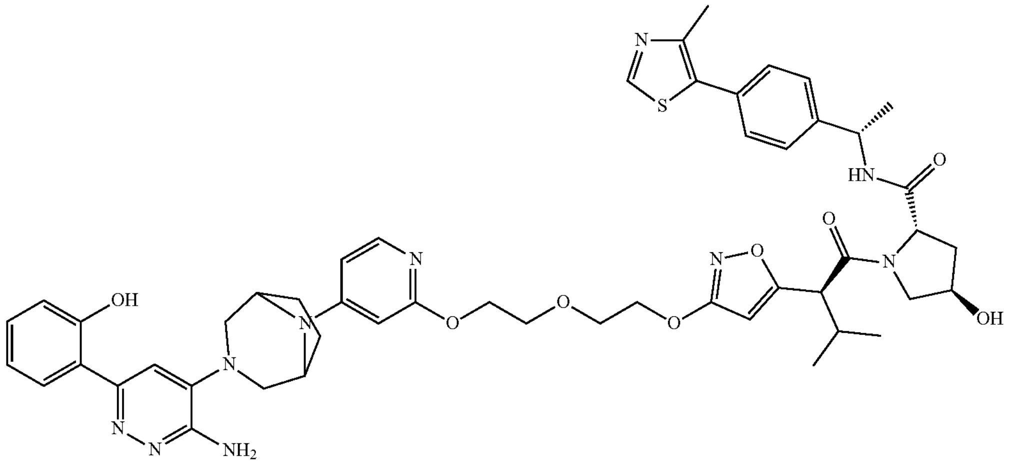 [SMILES: Cc1ncsc1-c1ccc([C@H](C)NC(=O)[C@@H]2C[C@@H](O)CN2C(=O)[C@H](c2cc(OCCOCCOc3cc(N4C5CCC4CN(c4cc(-c6ccccc6O)nnc4N)C5)ccn3)no2)C(C)C)cc1] |
| 357 | (2S,4R)-1-((2R)-2-(3-(2-(2-((4-(3-(3-amino-6-(2-hydroxyphenyl)pyridazin-4-yl)-3,8-diazabicyclo[3.2.1]octan-8-yl)pyridin-2-yl)oxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 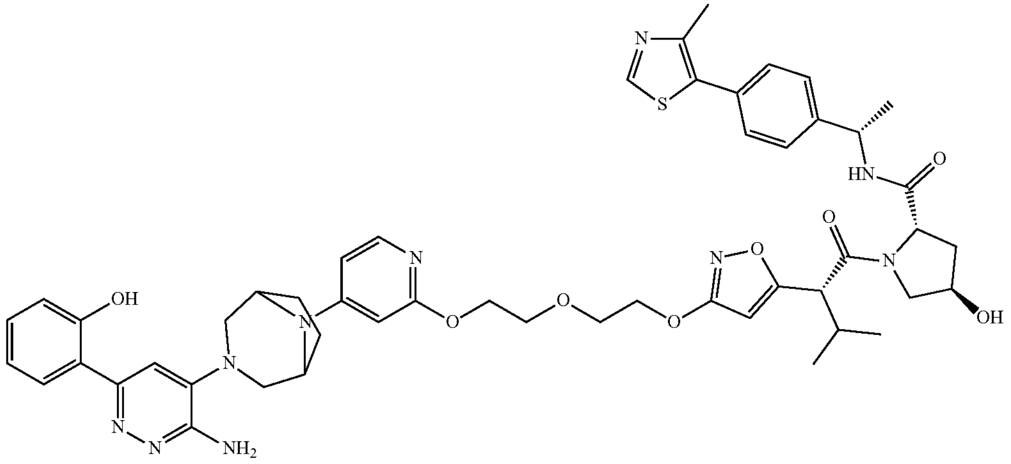 [SMILES: Cc1ncsc1-c1ccc([C@H](C)NC(=O)[C@@H]2C[C@@H](O)CN2C(=O)[C@@H](c2cc(OCCOCCOc3cc(N4C5CCC4CN(c4cc(-c6ccccc6O)nnc4N)C5)ccn3)no2)C(C)C)cc1] |

TABLE 1C-continued

| Exemplary bifunctional degradation compounds of the present disclosure | | |
|---|---|---|
| Ex. # | Compound Name | Structure |
| 358 | (2S,4R)-1-((S)-2-(3-(2-(4-((1r,3S)-3-(2-(9-(3-amino-6-(2-hydroxyphenyl)pyridazin-4-yl)-1-oxa-4,9-diazaspiro[5.5]undecan-4-yl)ethoxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 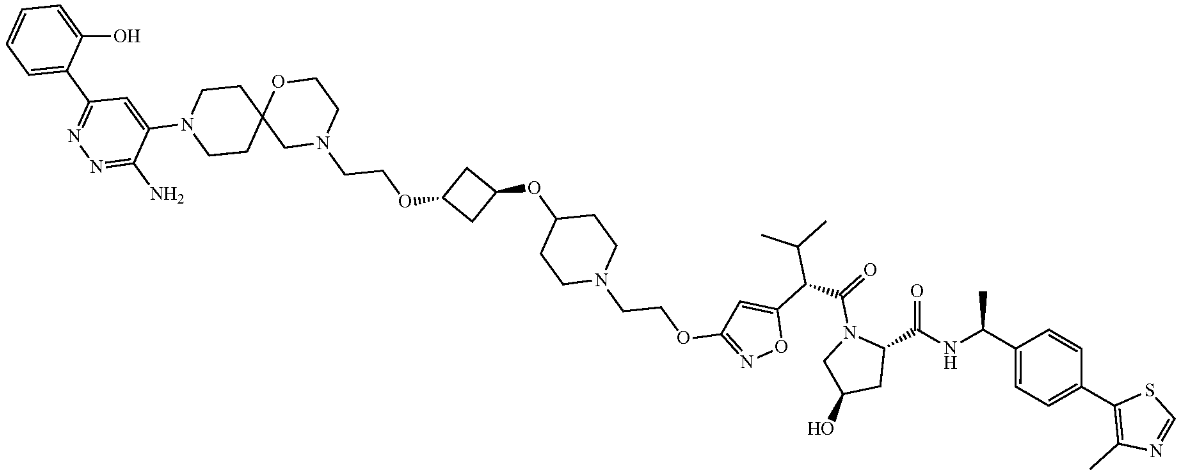 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](OCCN5CCOC6(CCN(c7cc(-c8ccccc8O)nnc7N)CC6)C5)C4)CC3)no2)C(C)C)cc1] |
| 359 | (2S,4R)-1-((R)-2-(3-(2-(4-((1r,3R)-3-(2-(9-(3-amino-6-(2-hydroxyphenyl)pyridazin-4-yl)-1-oxa-4,9-diazaspiro[5.5]undecan-4-yl)ethoxy)cyclobutoxy)piperidin-1-yl)cthoxy)isoxazol-5-yl)-3-methylbutanoyl)-4-hydroxy-N-((S)-1-(4-(4-methylthiazol-5-yl)phenyl)ethyl)pyrrolidine-2-carboxamide | 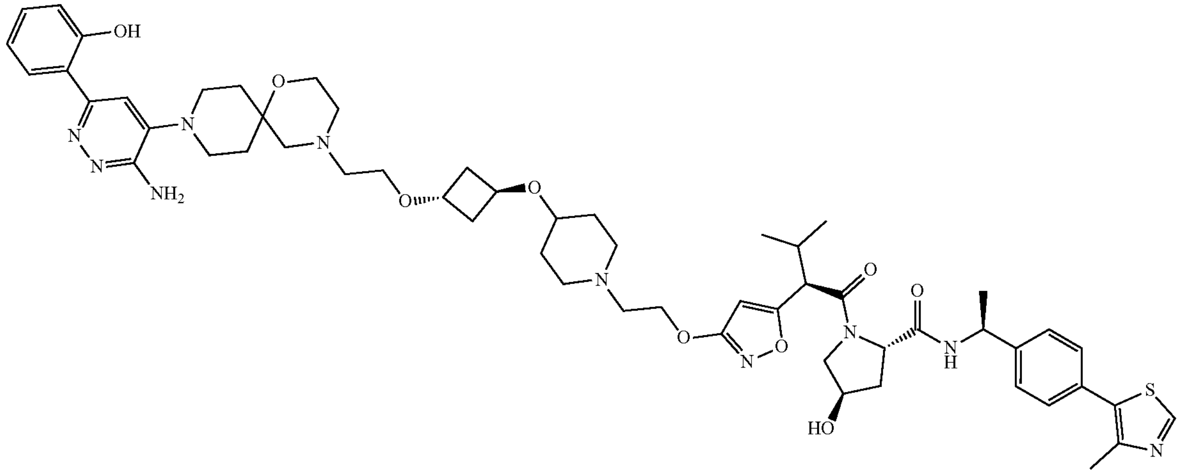 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](OCCN5CCOC6(CCN(c7cc(-c8ccccc8O)nnc7N)CC6)C5)C4)CC3)no2)C(C)C)cc1] |

TABLE 1C-continued

Exemplary bifunctional degradation compounds of the present disclosure

| Ex. # | Compound Name | Structure |
|---|---|---|
| 360 | (2S,4R)-1-((2R)-2-(3-(2-((3aR,5R,6aS)-5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)hexahydrocyclopenta[c]pyrrol-2(1H)-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 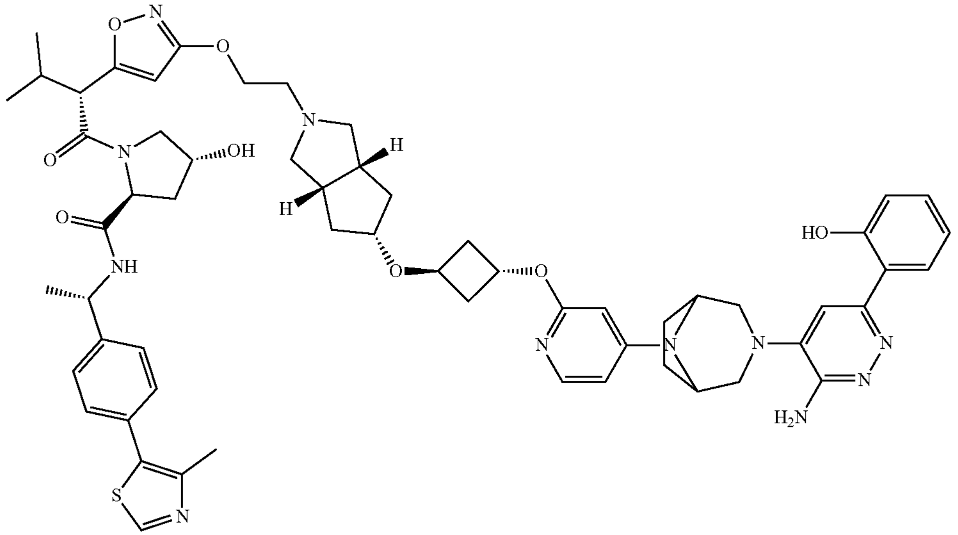 [SMILES: Cc1ncsc1-c1ccc([C@H](C)NC(=O)[C@@H]2C[C@@H](O)CN2C(=O)[C@@H](c2cc(OCCN3C[C@H]4C[C@@H](O[C@H]5C[C@H](Oc6cc(N7C8CCC7CN(c7cc(-c9ccccc9O)nnc7N)C8)ccn6)C5)C[C@H]4C3)no2)C(C)C)cc1] |
| 361 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-chloroisoxazol-5-yl)-3-methylbutanoyl)-4-hydroxy-N-((S)-1-(4-(4-methylthiazol-5-yl)phenyl)ethyl)pyrrolidine-2-carboxamide | 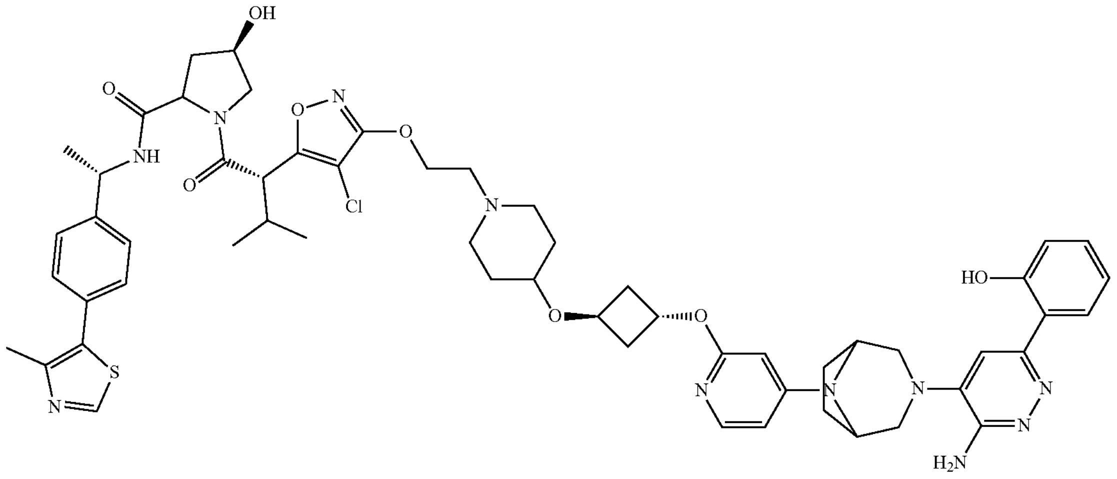 [SMILES: Cc1ncsc1-c1ccc([C@H](C)NC(=O)C2C[C@@H](O)CN2C(=O)[C@H](c2onc(OCCN3CCC(O[C@H]4C[C@H](Oc5cc(N6C7CCC6CN(c6cc(-c8ccccc8O)nnc6N)C7)ccn5)C4)CC3)c2Cl)C(C)C)cc1] |

TABLE 1C-continued

| Ex. # | Compound Name | Structure |
|---|---|---|
| | Exemplary bifunctional degradation compounds of the present disclosure | |
| 362 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)-4-chloroisoxazol-5-yl)-3-methylbutanoyl)-4-hydroxy-N-((S)-1-(4-(4-methylthiazol-5-yl)phenyl)ethyl)pyrrolidine-2-carboxamide | 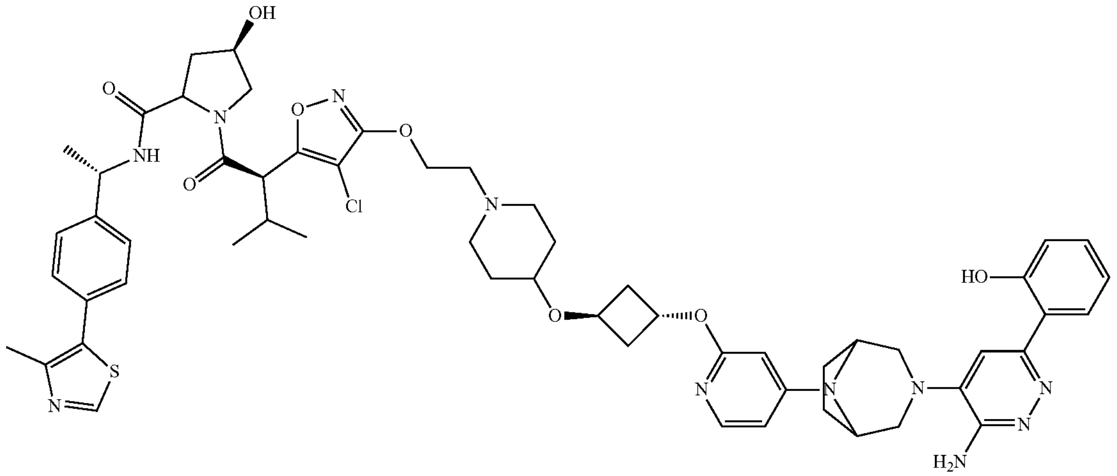 [SMILES: Cc1ncsc1-c1ccc([C@H](C)NC(=O)C2C[C@@H](O)CN2C(=O)[C@@H](c2onc(OCCN3CCC(O[C@H]4C[C@H](Oc5cc(N6C7CCC6CN(c6cc(-c8ccccc8O)nnc6N)C7)ccn5)C4)CC3)c2Cl)C(C)C)cc1] |
| 363 | (2S,4R)-N-((S)-1-(4-(1,3,4-thiadiazol-2-yl)phenyl)ethyl)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamide | 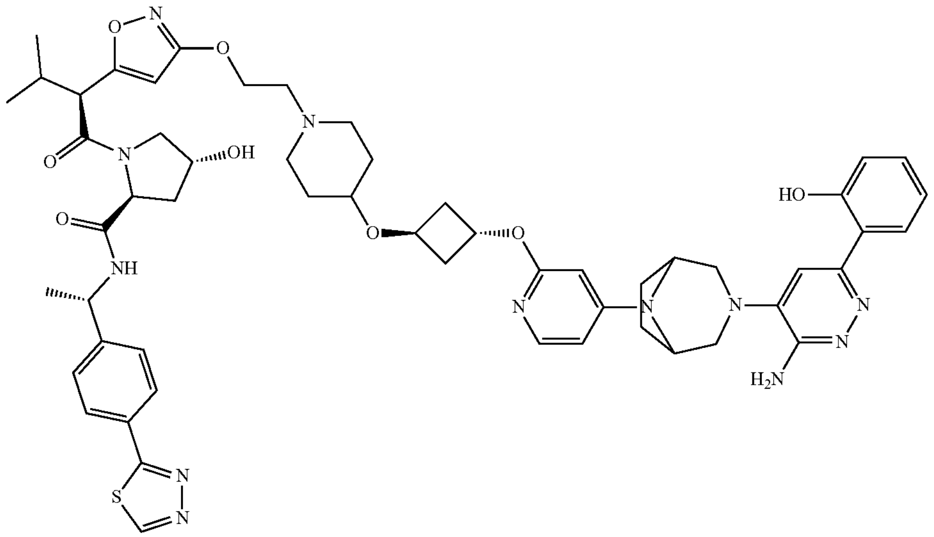 [SMILES: CC(C)[C@H](C(=O)N1C[C@H](O)C[C@H]1C(=O)N[C@@H](C)c1ccc(-c2nncs2)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued
| Exemplary bifunctional degradation compounds of the present disclosure | | |
|---|---|---|
| Ex. # | Compound Name | Structure |
| 364 | (2S,4R)-N-((S)-1-(4-(1,3,4-thiadiazol-2-yl)phenyl)ethyl)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamide | 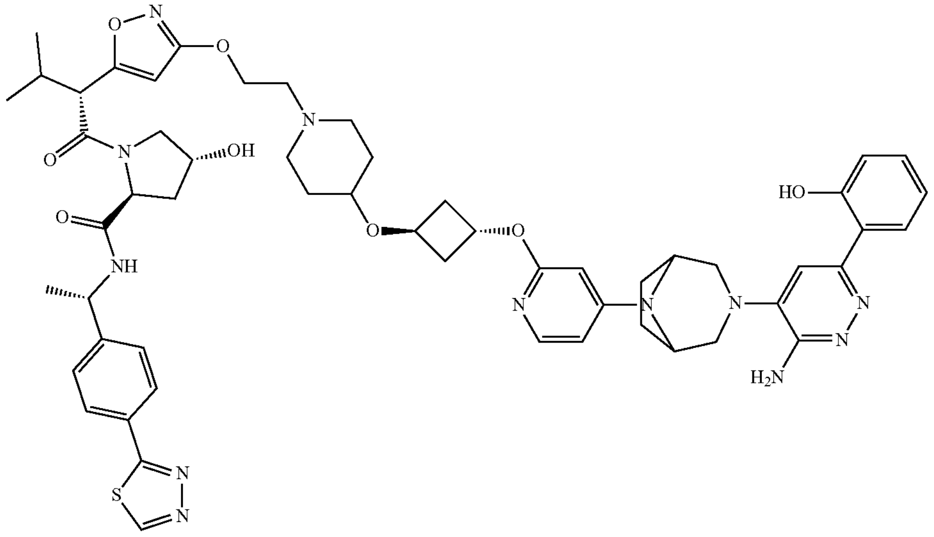 [SMILES: CC(C)[C@@H](C(=O)N1C[C@H](O)C[C@H]1C(=O)N[C@@H](C)c1ccc(-c2nncs2)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued
| Exemplary bifunctional degradation compounds of the present disclosure | | |
|---|---|---|
| Ex. # | Compound Name | Structure |
| 365 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(1,4-dimethyl-1H-imidazol-5-yl)phenyl)ethyl)-4-hydroxypyrrolidine-2-carboxamide | 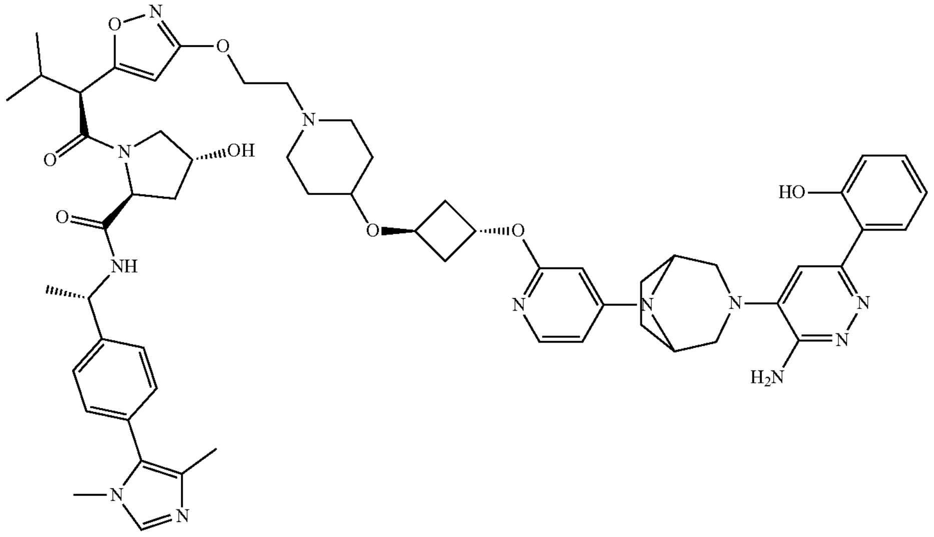 [SMILES: Cc1ncn(C)c1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 366 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(1,4-dimethyl-1H-imidazol-5-yl)phenyl)ethyl)-4-hydroxypyrrolidine-2-carboxamide | 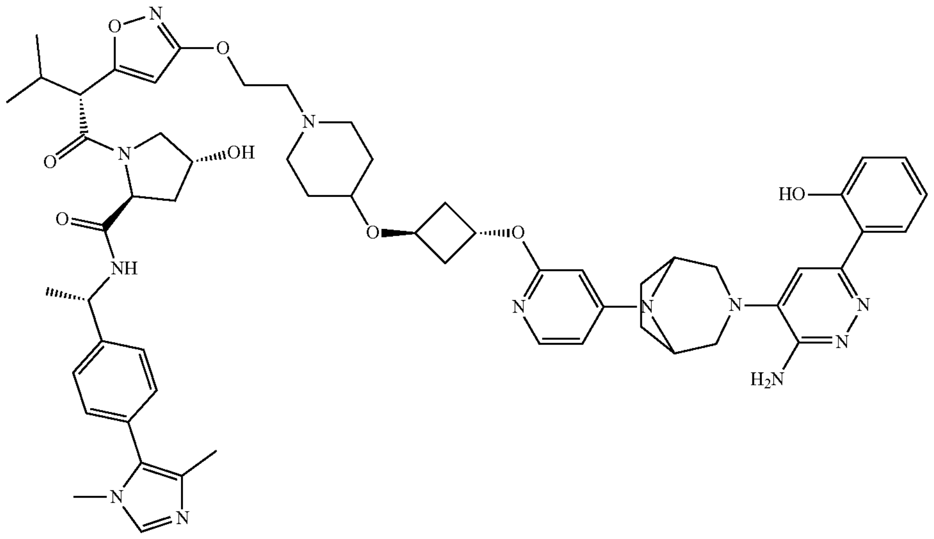 [SMILES: Cc1ncn(C)c1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 367 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(5-(4-methylthiazol-5-yl)pyridin-2-yl)ethyl)pyrrolidine-2-carboxamide | 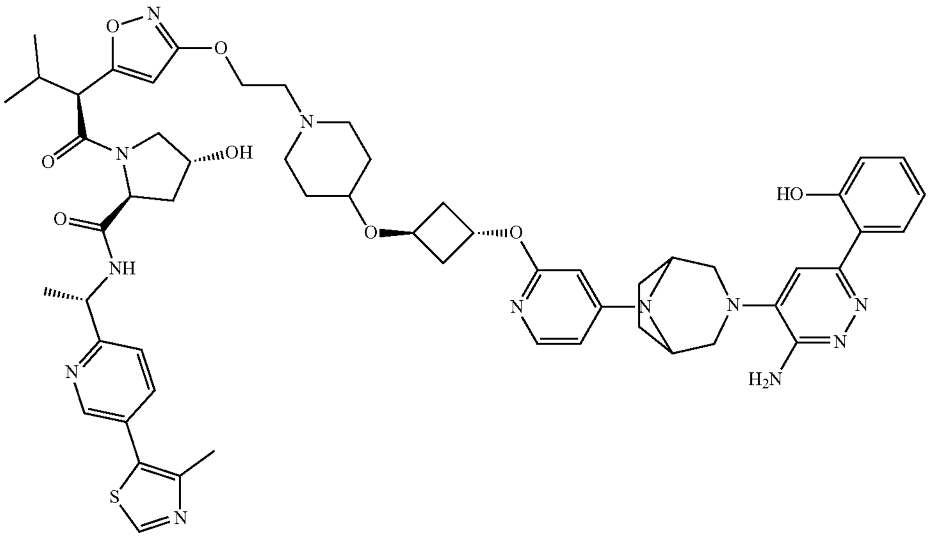 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)nc1] |

TABLE 1C-continued

| Exemplary bifunctional degradation compounds of the present disclosure | | |
|---|---|---|
| Ex. # | Compound Name | Structure |
| 368 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(5-(4-methylthiazol-5-yl)pyridin-2-yl)ethyl)pyrrolidine-2-carboxamide | 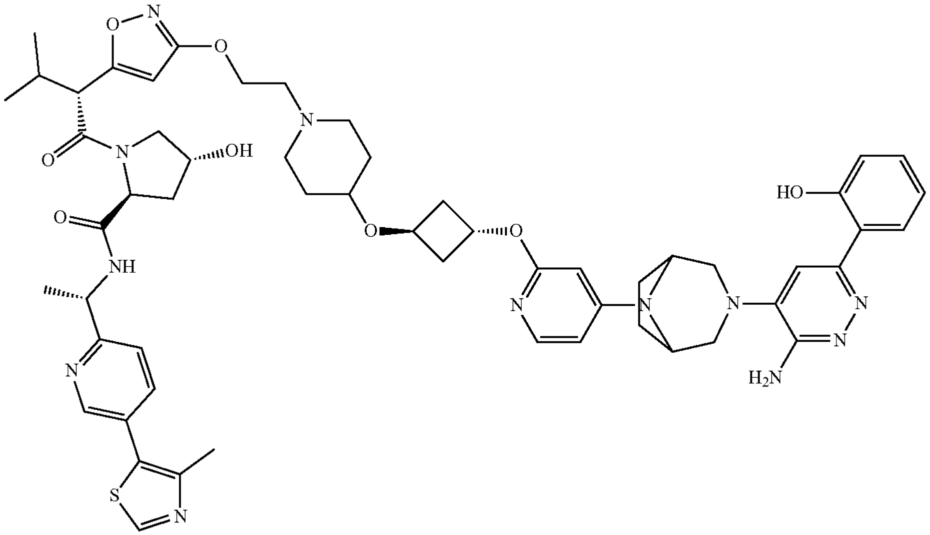 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)nc1] |
| 369 | (2S,4R)-1-((2S)-2-(3-((3-(3-((3-((4-(3-(3-amino-6-(2-hydroxyphenyl)pyridazin-4-yl)-3,8-diazabicyclo[3.2.1]octan-8-yl)pyridin-2-yl)oxy)azetidin-1-yl)methyl)bicyclo[1.1.1]pentan-1-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 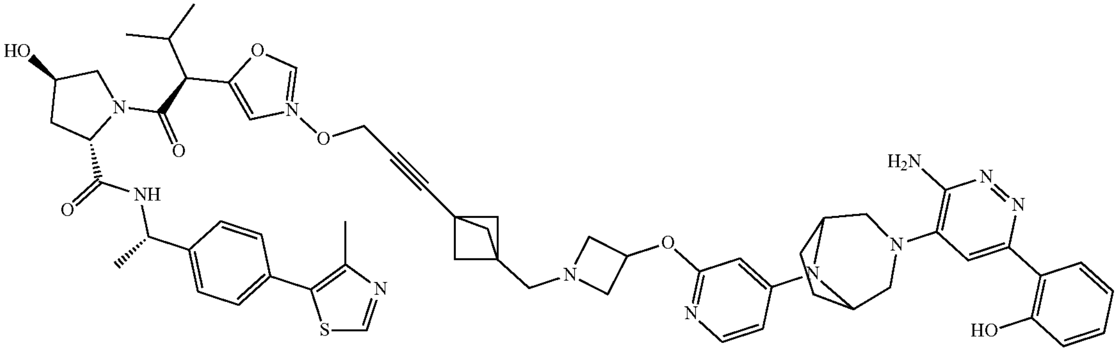 |

TABLE 1C-continued
Exemplary bifunctional degradation compounds of the present disclosure
| Ex. # | Compound Name | Structure |
| --- | --- | --- |
| 370 | (2S,4R)-1-((2S)-2-(3-((1-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)azetidin-3-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 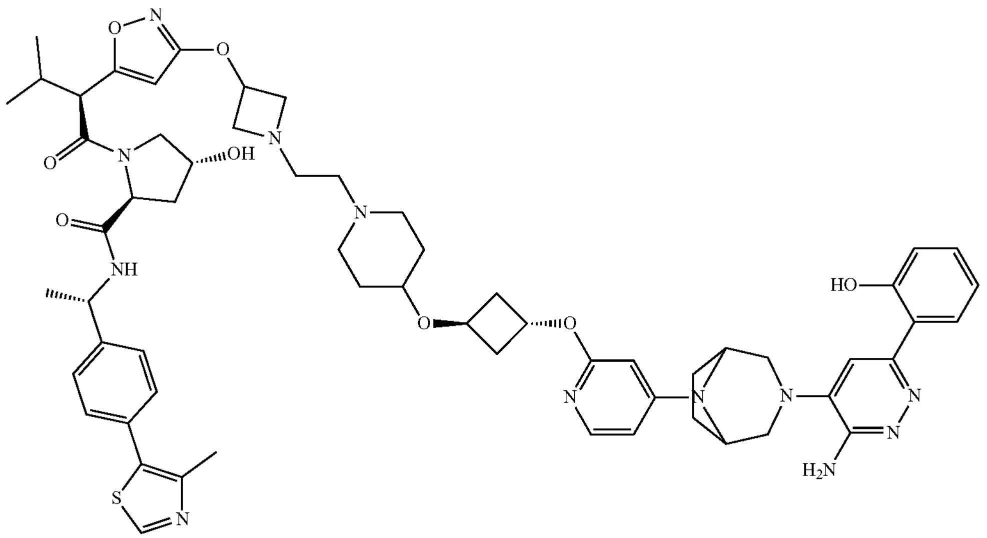 [SMILES: Cc1ncsc1-c1ccc([C@H](C)NC(=O)[C@@H]2C[C@@H](O)CN2C(=O)[C@H](c2cc(OC3CN(CCN4CCC(O[C@H]5C[C@H](Oc6cc(N7C8CCC7CN(c7cc(-c9ccccc9O)nnc7N)C8)ccn6)C5)CC4)C3)no2)C(C)C)cc1] |

TABLE 1C-continued
| Exemplary bifunctional degradation compounds of the present disclosure | | |
|---|---|---|
| Ex. # | Compound Name | Structure |
| 371 | (2S,4R)-1-((2R)-2-(3-((1-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)azetidin-3-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 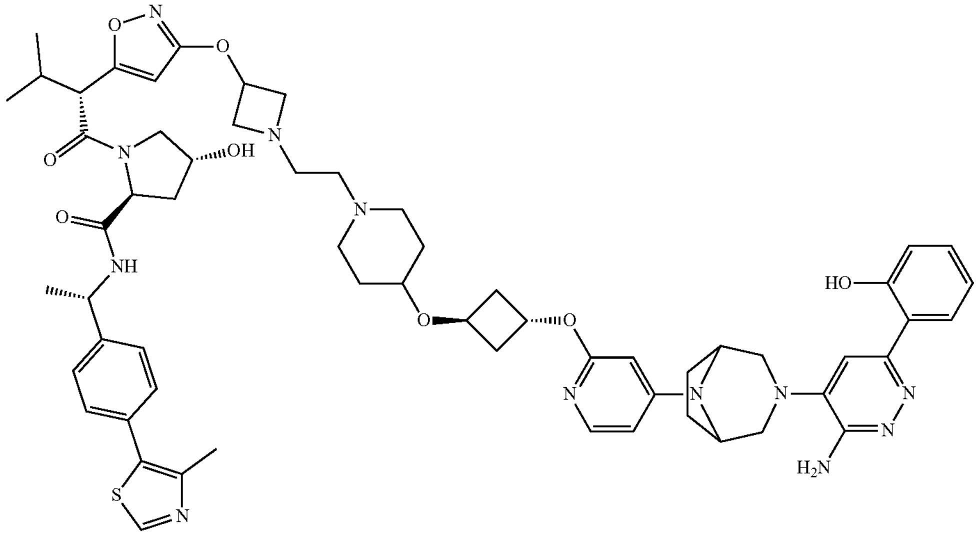 [SMILES: Cc1ncsc1-c1ccc([C@H](C)NC(=O)[C@@H]2C[C@@H](O)CN2C(=O)[C@@H](c2cc(OC3CN(CCN4CCC(O[C@H]5C[C@H](Oc6cc(N7C8CCC7CN(c7cc(-c9ccccc9O)nnc7N)C8)ccn6)C5)CC4)C3)no2)C(C)C)cc1] |

TABLE 1C-continued
| Exemplary bifunctional degradation compounds of the present disclosure | | |
|---|---|---|
| Ex. # | Compound Name | Structure |
| 372 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(2-oxopyridin-1(2H)-yl)phenyl)ethyl)pyrrolidine-2-carboxamide | 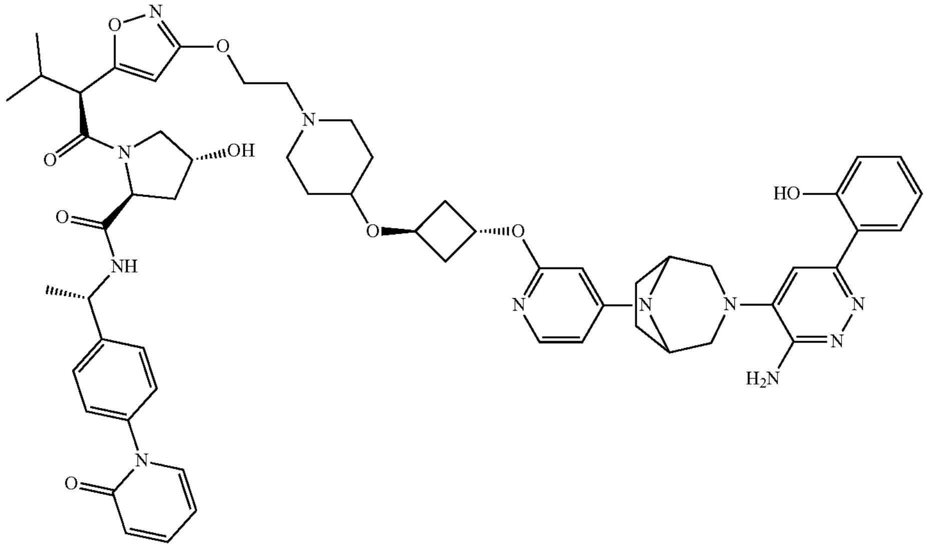 [SMILES: CC(C)[C@H](C(=O)N1C[C@H](O)C[C@H]1C(=O)N[C@@H](C)c1ccc(-n2ccccc2=O)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued
| Exemplary bifunctional degradation compounds of the present disclosure | | |
|---|---|---|
| Ex. # | Compound Name | Structure |
| 373 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(2-oxopyridin-1(2H)-yl)phenyl)ethyl)pyrrolidine-2-carboxamide | 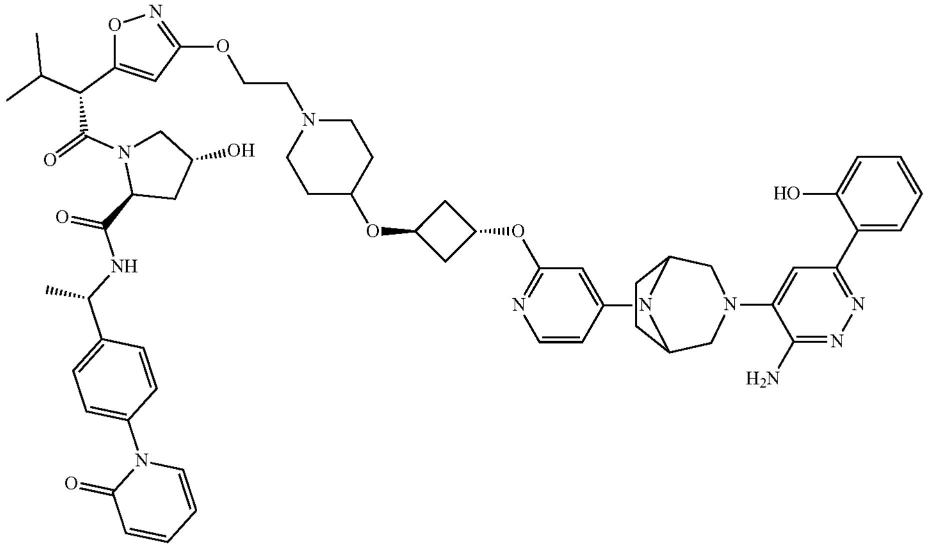 [SMILES: CC(C)[C@@H](C(=O)N1C[C@H](O)C[C@H]1C(=O)N[C@@H](C)c1ccc(-n2ccccc2=O)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued
| Exemplary bifunctional degradation compounds of the present disclosure | | |
|---|---|---|
| Ex. # | Compound Name | Structure |
| 374 | (2S,4R)-1-((2R)-2-(3-(2-(4-(3-((4-(3-(3-amino-6-(2-hydroxyphenyl)pyridazin-4-yl)-3,8-diazabicyclo[3.2.1]octan-8-yl)pyridin-2-yl)oxy)azetidin-1-yl)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 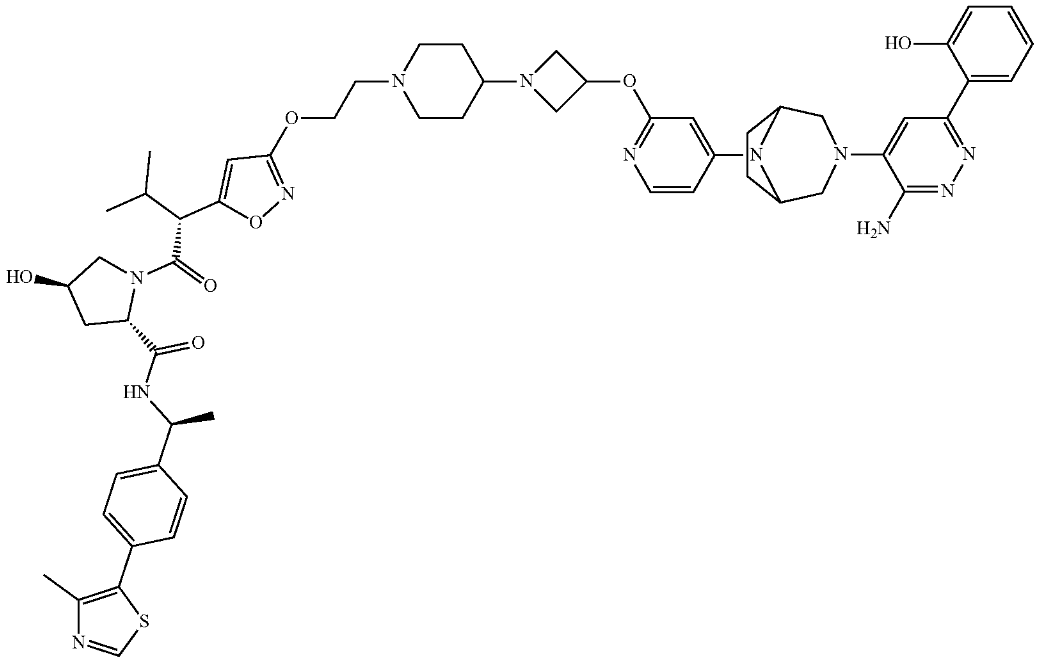 [SMILES: Cc1ncsc1-c1ccc([C@H](C)NC(=O)[C@@H]2C[C@@H](O)CN2C(=O)[C@@H](c2cc(OCCN3CCC(N4CC(Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 375 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(2,5-dimethyl-1H-imidazol-1-yl)phenyl)ethyl)-4-hydroxypyrrolidine-2-carboxamide | 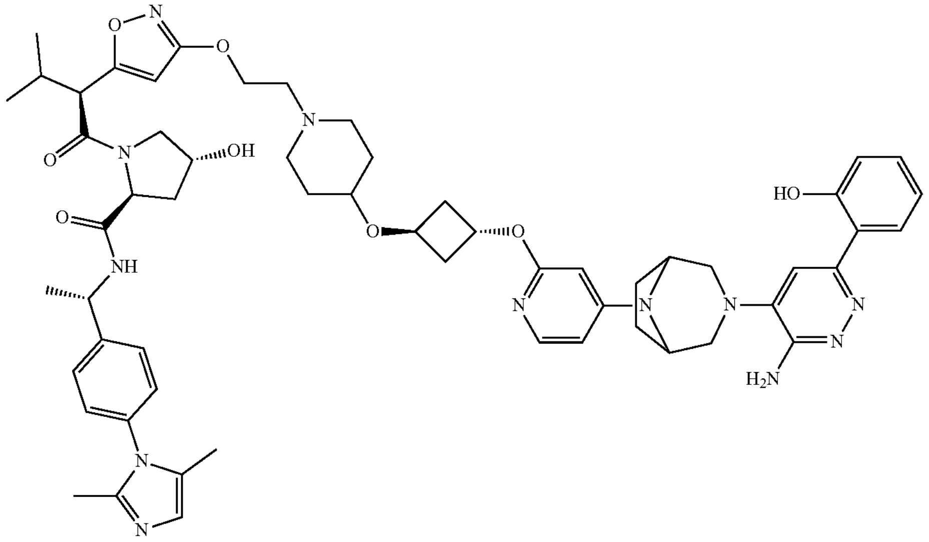 [SMILES: Cc1cnc(C)n1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 376 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(2,5-dimethyl-1H-imidazol-1-yl)phenyl)ethyl)-4-hydroxypyrrolidine-2-carboxamide | 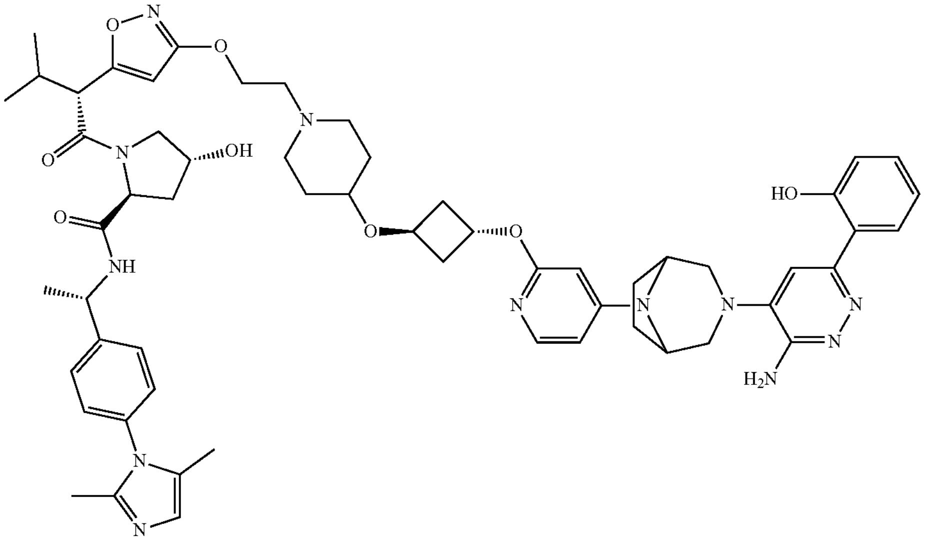 [SMILES: Cc1cnc(C)n1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 377 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(3,5-dimethyl-1H-pyrazol-4-yl)phenyl)ethyl)-4-hydroxypyrrolidine-2-carboxamide | 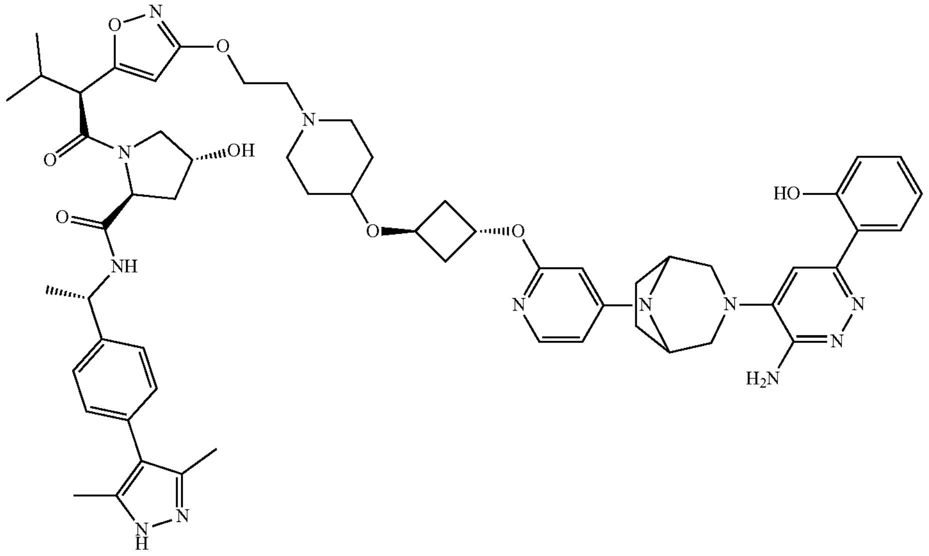 [SMILES: Cc1n[nH]c(C)c1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 378 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(3,5-dimethyl-1H-pyrazol-4-yl)phenyl)ethyl)-4-hydroxypyrrolidine-2-carboxamide | 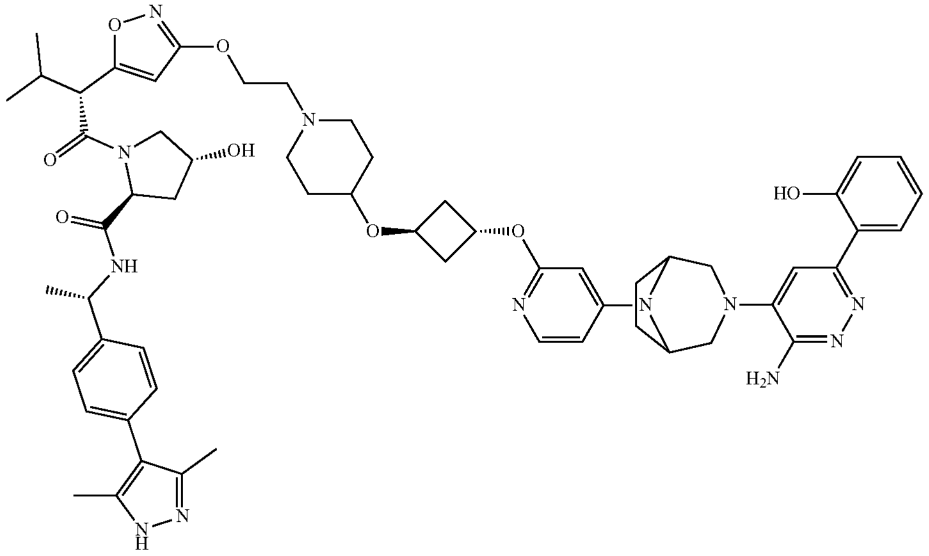 [SMILES: Cc1n[nH]c(C)c1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 379 | (2S,4R)-1-((2S)-2-(3-(3-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)prop-1-yn-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 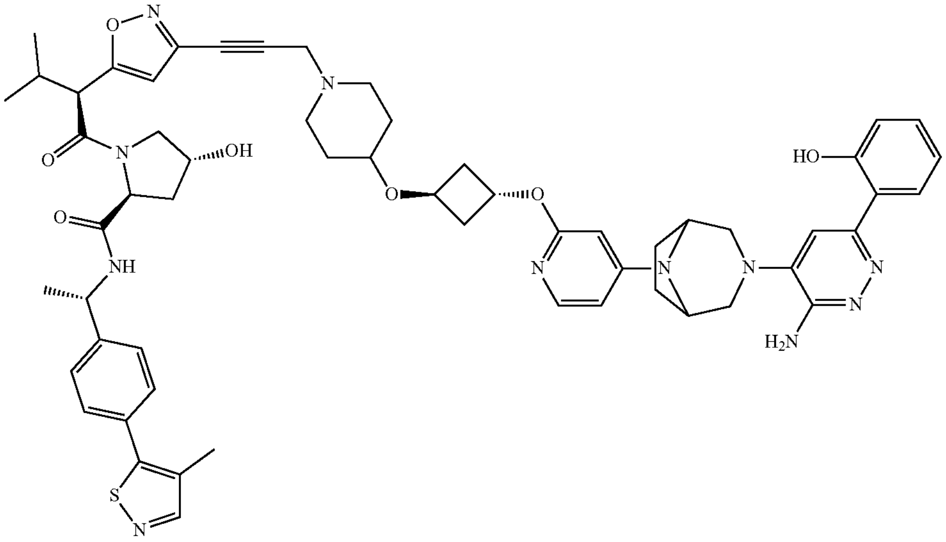 [SMILES: Cc1cnsc1-c1ccc([C@H](C)NC(=O)[C@@H]2C[C@@H](O)CN2C(=O)[C@H](c2cc(C#CCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 380 | (2S,4R)-1-((2R)-2-(3-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)prop-1-yn-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 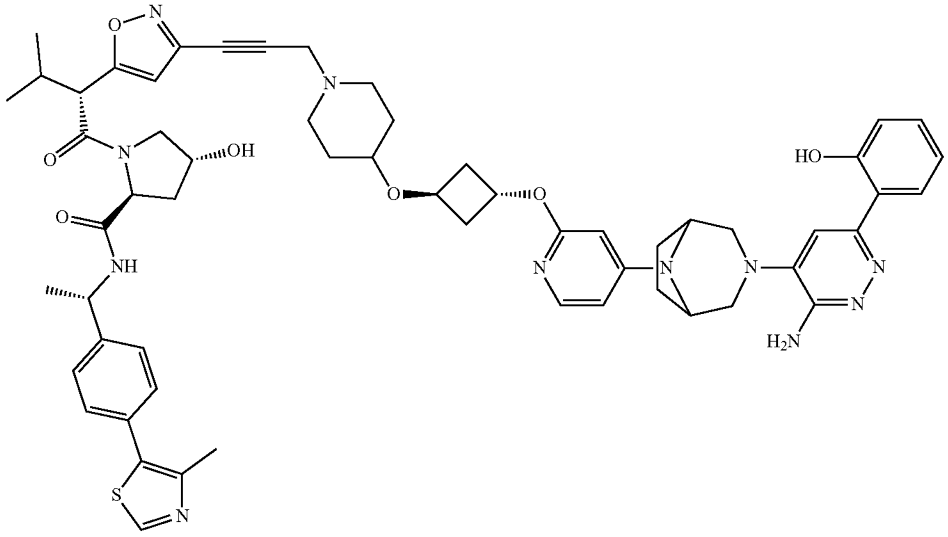 [SMILES: Cc1ncsc1-c1ccc([C@H](C)NC(=O)[C@@H]2C[C@@H](O)CN2C(=O)[C@@H](c2cc(C#CCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
Exemplary bifunctional degradation compounds of the present disclosure
| Ex. # | Compound Name | Structure |
| --- | --- | --- |
| 381 | (2S,4R)-1-((2S)-2-(3-((3-(3-((((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)amino)methyl)bicyclo[1.1.1]pentan-1-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 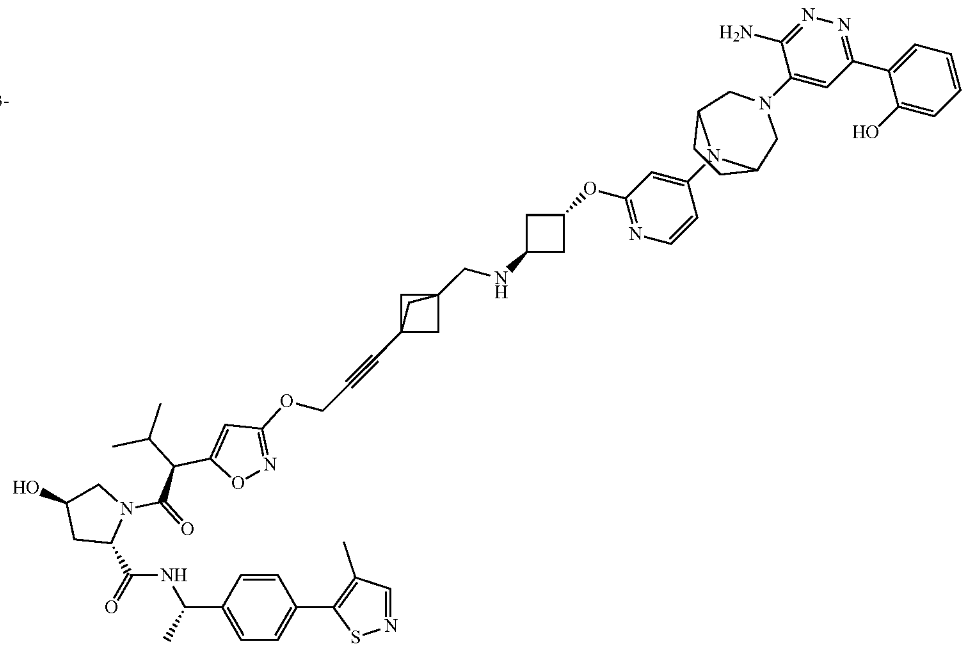 |

TABLE 1C-continued

| Exemplary bifunctional degradation compounds of the present disclosure | | |
|---|---|---|
| Ex. # | Compound Name | Structure |
| 382 | (2S,4R)-1-((2R)-2-(3-((3-(3-((((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)amino)methyl)bicyclo[1.1.1]pentan-1-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 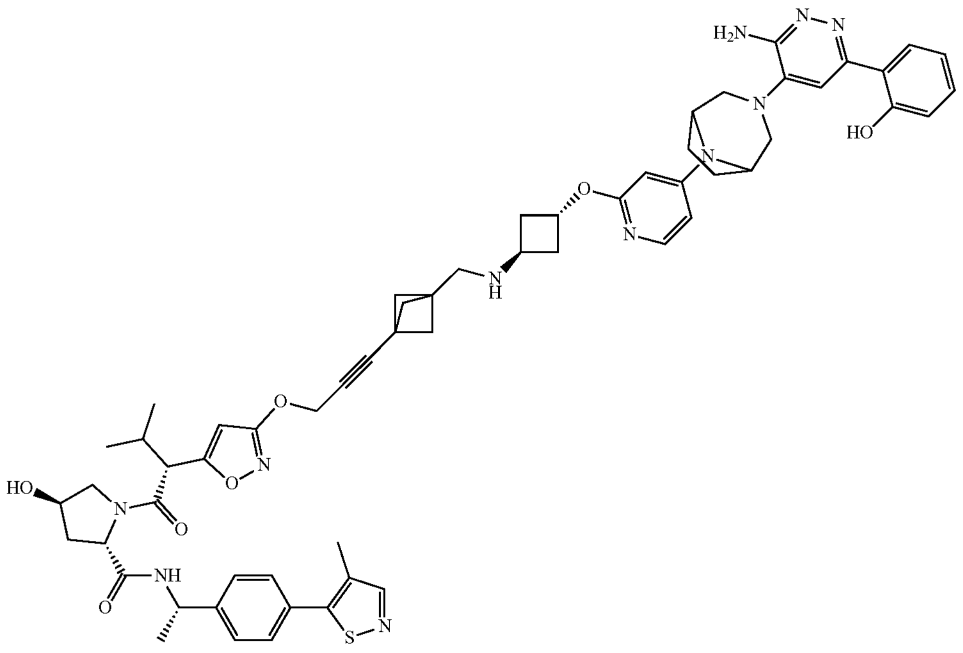 [SMILES: Cc1cnsc1-c1ccc([C@H](C)NC(=O)[C@@H]2C[C@@H](O)CN2C(=O)[C@@H](c2cc(OCC#CC34CC(CN[C@H]5C[C@H](Oc6cc(N7C8CCC7CN(c7cc(-c9ccccc9O)nnc7N)C8)ccn6)C5)(C3)C4)no2)C(C)C)cc1] |
| 383 | (2S,4R)-1-((2R)-2-(3-((3-(3-((3-((4-(3-(3-amino-6-(2-hydroxyphenyl)pyridazin-4-yl)-3,8-diazabicyclo[3.2.1]octan-8-yl)pyridin-2-yl)oxy)azetidin-1-yl)methyl)bicyclo[1.1.1]pentan-1-yl)prop-2-yn-1-yl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 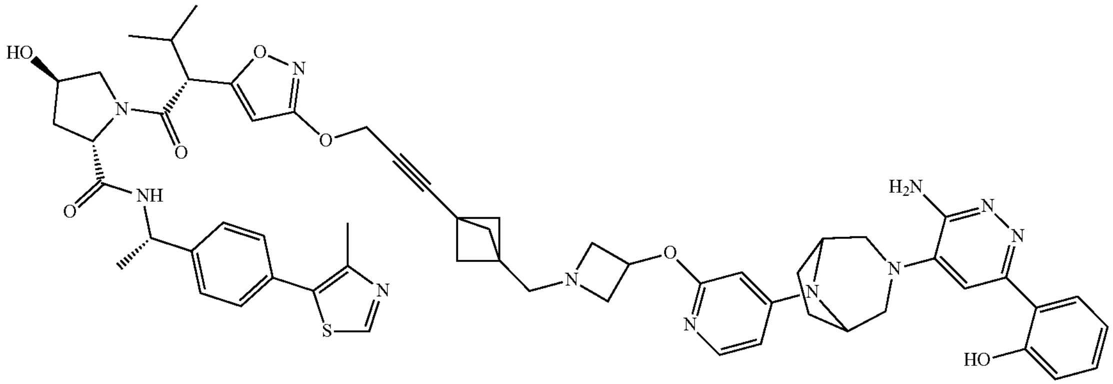 [SMILES: Cc1ncsc1-c1ccc([C@H](C)NC(=O)[C@@H]2C[C@@H](O)CN2C(=O)[C@@H](c2cc(OCC#CC34CC(CN5CC(Oc6cc(N7C8CCC7CN(c7cc(-c9ccccc9O)nnc7N)C8)ccn6)C5)(C3)C4)no2)C(C)C)cc1] |

TABLE 1C-continued
| Exemplary bifunctional degradation compounds of the present disclosure | | |
|---|---|---|
| Ex. # | Compound Name | Structure |
| 384 | (2S,4R)-1-((2S)-2-(3-(3-(4-(3-((4-(3-(3-amino-6-(2-hydroxyphenyl)pyridazin-4-yl)-3,8-diazabicyclo[3.2.1]octan-8-yl)pyridin-2-yl)oxy)propyl)piperazin-1-yl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide | 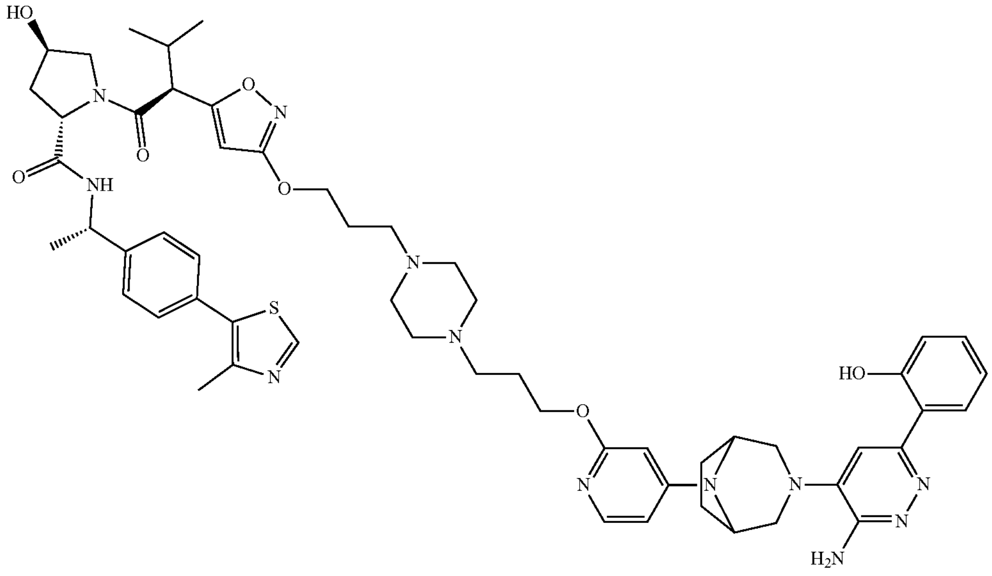 [SMILES: Cc1ncsc1-c1ccc([C@H](C)NC(=O)[C@@H]2C[C@@H](O)CN2C(=O)[C@H](c2cc(OCCCN3CCN(CCCOc4cc(N5C6CCC5CN(c5cc(-c7ccccc7O)nnc5N)C6)ccn4)CC3)no2)C(C)C)cc1] |

TABLE 1C-continued
Exemplary bifunctional degradation compounds of the present disclosure
| Ex. # | Compound Name | Structure |
|---|---|---|
| 385 | (2S,4R)-1-((2R)-2-(3-(3-(4-(3-((4-(3-(3-amino-6-(2-hydroxyphenyl)pyridazin-4-yl)-3,8-diazabicyclo[3.2.1]octan-8-yl)pyridin-2-yl)oxy)propyl)piperazin-1-yl)propoxy)isoxazol-5-yl)-3-methylbutanoyl)-4-hydroxy-N-((S)-1-(4-(4-methylthiazol-5-yl)phenyl)ethyl)pyrrolidine-2-carboxamide | 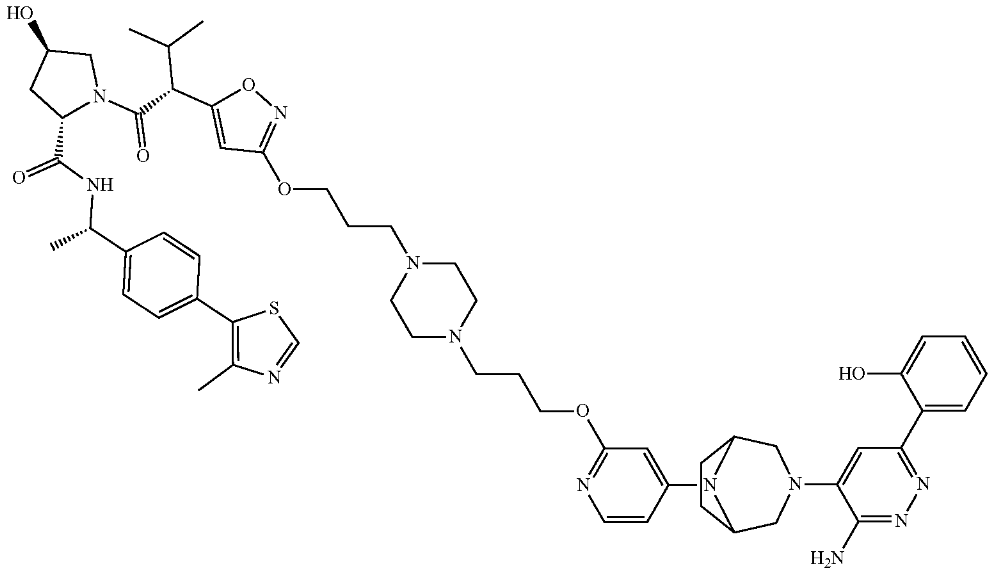 [SMILES: Cc1ncsc1-c1ccc([C@H](C)NC(=O)[C@@H]2C[C@@H](O)CN2C(=O)[C@@H](c2cc(OCCCN3CCN(CCCOc4cc(N5C6CCC5CN(c5cc(-c7ccccc7O)nnc5N)C6)ccn4)CC3)no2)C(C)C)cc1] |

TABLE 1C-continued
| Exemplary bifunctional degradation compounds of the present disclosure | | |
|---|---|---|
| Ex. # | Compound Name | Structure |
| 386 | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-N-((S)-1-(4-cyanophenyl)ethyl)-4-hydroxypyrrolidine-2-carboxamide | 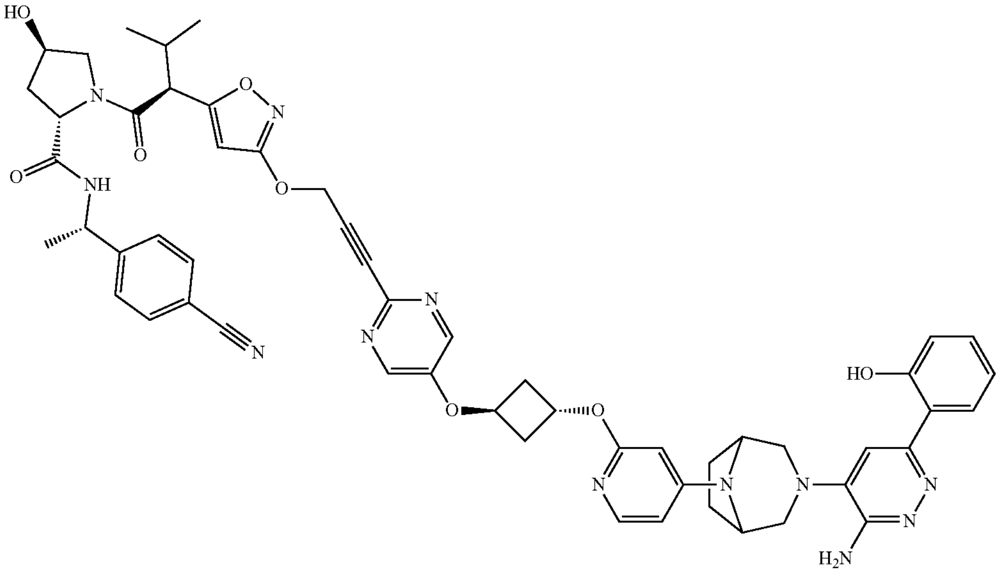 [SMILES: CC(C)[C@H](C(=O)N1C[C@H](O)C[C@H]1C(=O)N[C@@H](C)c1ccc(C#N)cc1)c1cc(OCC#Cc2ncc(O[C@H]3C[C@H](Oc4cc(N5C6CCC5CN(c5cc(-c7ccccc7O)nnc5N)C6)ccn4)C3)cn2)no1] |

TABLE 1C-continued
| Exemplary bifunctional degradation compounds of the present disclosure | | |
|---|---|---|
| Ex. # | Compound Name | Structure |
| 387 | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-N-((S)-1-(4-cyanophenyl)ethyl)-4-hydroxypyrrolidine-2-carboxamide | 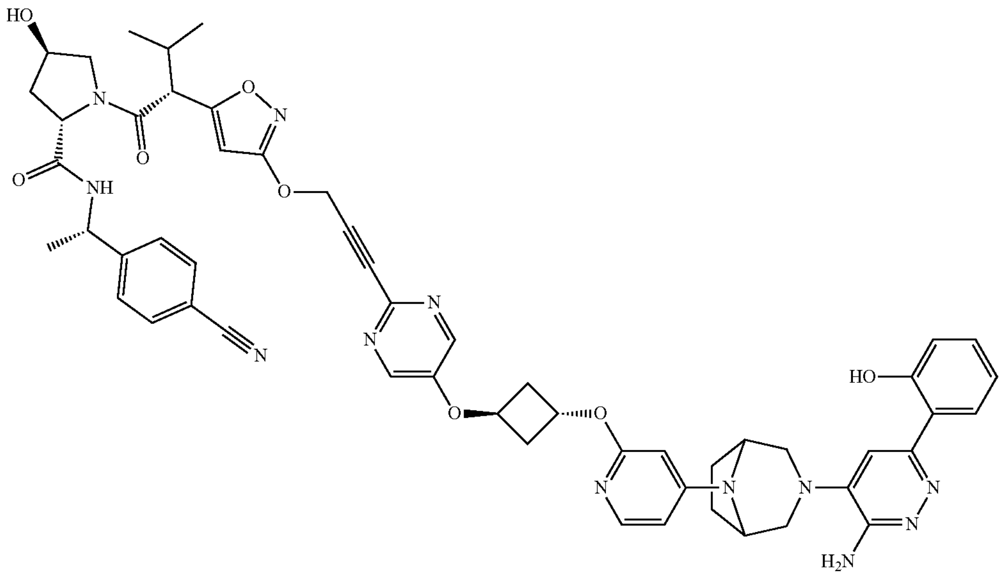 [SMILES: CC(C)[C@@H](C(=O)N1C[C@H](O)C[C@H]1C(=O)N[C@@H](C)c1ccc(C#N)cc1)c1cc(OCC#Cc2ncc(O[C@H]3C[C@H](Oc4cc(N5C6CCC5CN(c5cc(-c7ccccc7O)nnc5N)C6)ccn4)C3)cn2)no1] |

TABLE 1C-continued

| Exemplary bifunctional degradation compounds of the present disclosure | | |
|---|---|---|
| Ex. # | Compound Name | Structure |
| 388 | (2S,4R)-1-((2R)-2-(3-(2-(((1S,4S)-4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)amino)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 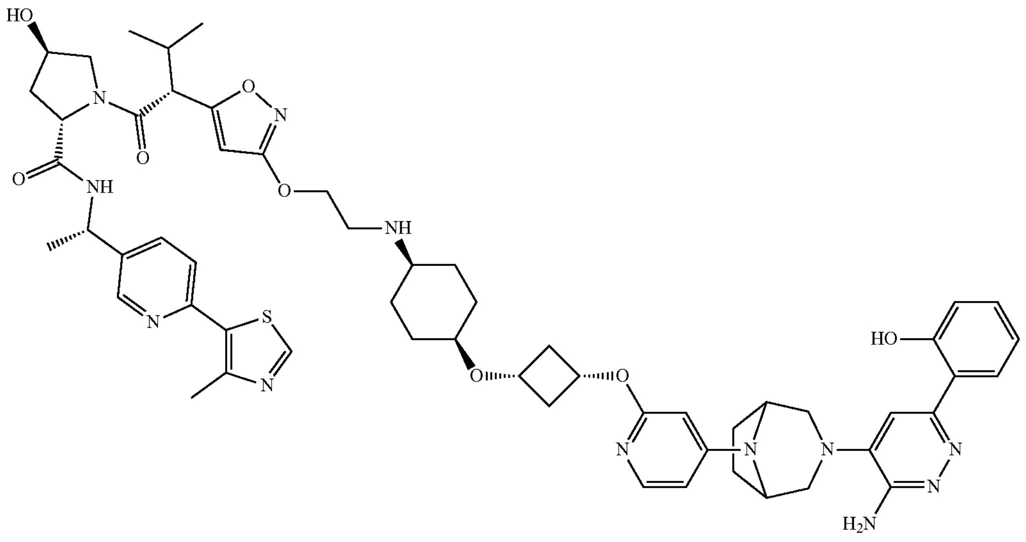 [SMILES: Cc1ncsc1-c1ccc([C@H](C)NC(=O)[C@@H]2C[C@@H](O)CN2C(=O)[C@@H](c2cc(OCCN[C@H]3CC[C@@H](O[C@H]4C[C@@H](Oc5cc(N6C7CCC6CN(c6cc(-c8ccccc8O)nnc6N)C7)ccn5)C4)CC3)no2)C(C)C)cn1] |
| 389 | (2S,4R)-1-((2S)-2-(3-(4-(4-(4-((4-(3-(3-amino-6-(2-hydroxyphenyl)pyridazin-4-yl)-3,8-diazabicyclo[3.2.1]octan-8-yl)pyridin-2-yl)oxy)butyl)piperazin-1-yl)butoxy)isoxazol-5-yl)-3-methylbutanoyl)-4-hydroxy-N-((S)-1-(4-(4-methylthiazol-5-yl)phenyl)ethyl)pyrrolidine-2-carboxamide | 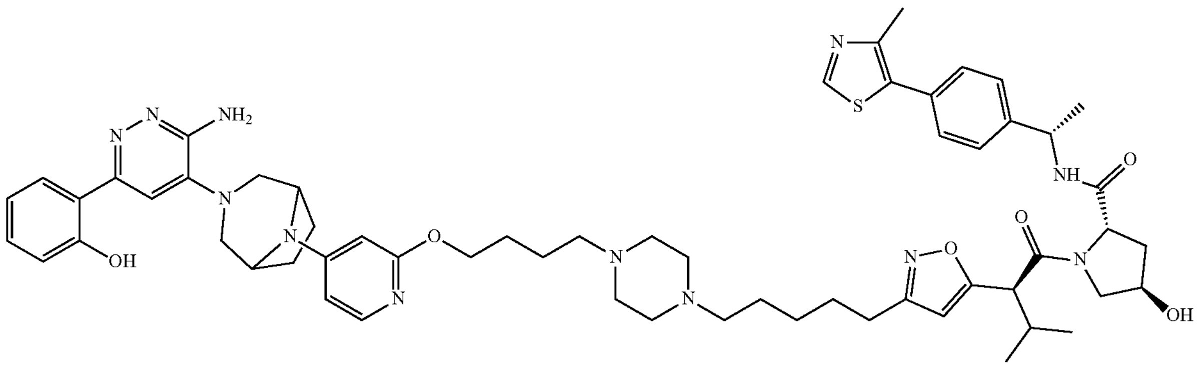 [SMILES: Cc1ncsc1-c1ccc([C@H](C)NC(=O)[C@@H]2C[C@@H](O)CN2C(=O)[C@H](c2cc(CCCCCN3CCN(CCCCOc4cc(N5C6CCC5CN(c5cc(-c7ccccc7O)nnc5N)C6)ccn4)CC3)no2)C(C)C)cc1] |

TABLE 1C-continued

| Ex. # | Compound Name | Structure |
|---|---|---|
| | Exemplary bifunctional degradation compounds of the present disclosure | |
| 390 | (2S,4R)-1-((2R)-2-(3-(4-(4-(4-((4-(3-(3-amino-6-(2-hydroxyphenyl)pyridazin-4-yl)-3,8-diazabicyclo[3.2.1]octan-8-yl)pyridin-2-yl)oxy)butyl)piperazin-1-yl)butoxy)isoxazol-5-yl)-3-methylbutanoyl)-4-hydroxy-N-((S)-1-(4-(4-methylthiazol-5-yl)phenyl)ethyl)pyrrolidine-2-carboxamide | 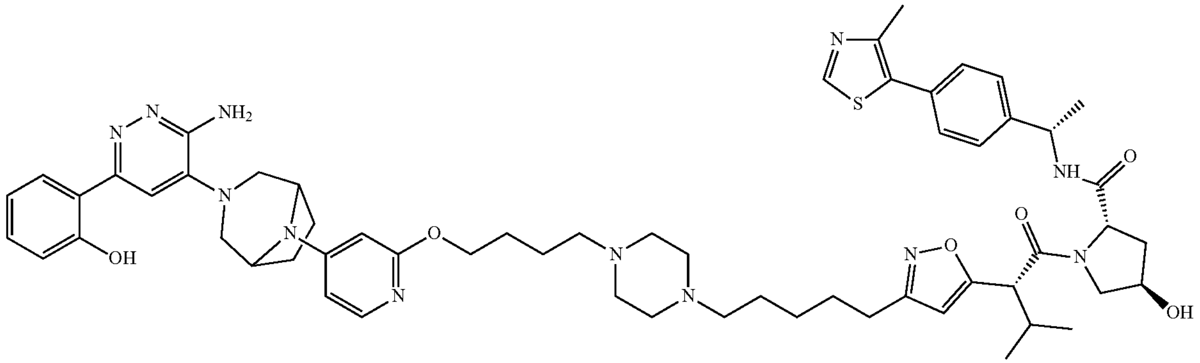 [SMILES: Cc1ncsc1-c1ccc([C@H](C)NC(=O)[C@@H]2C[C@@H](O)CN2C(=O)[C@@H](c2cc(CCCCCN3CCN(CCCCOc4cc(N5C6CCC5CN(c5cc(-c7ccccc7O)nnc5N)C6)ccn4)CC3)no2)C(C)C)cc1] |
| 391 | (2S,4R)-1-((2S)-2-(3-(((E)-3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)allyl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 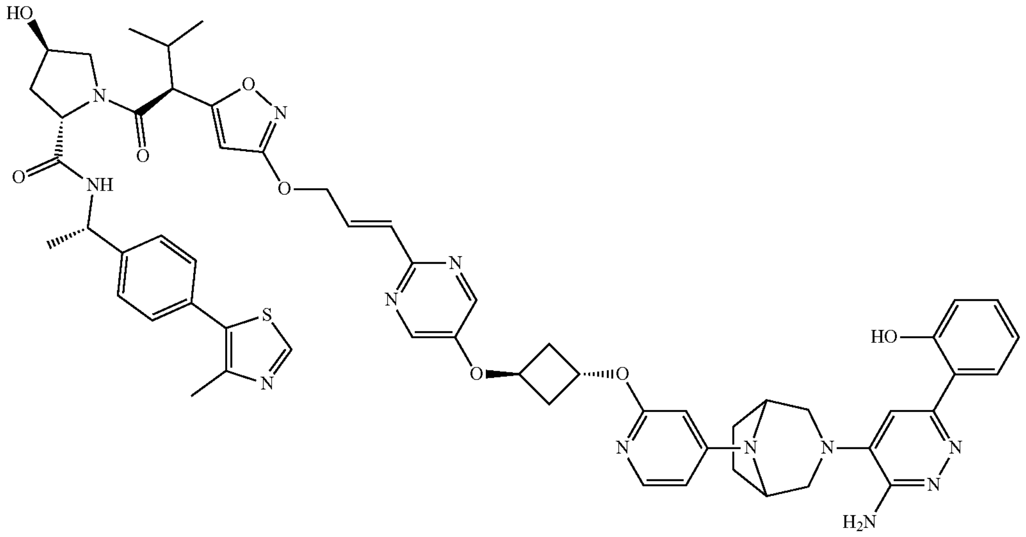 [SMILES: Cc1ncsc1-c1ccc([C@H](C)NC(=O)[C@@H]2C[C@@H](O)CN2C(=O)[C@H](c2cc(OC/C=C/c3ncc(O[C@H]4C[C@H](Oc5cc(N6C7CCC6CN(c6cc(-c8ccccc8O)nnc6N)C7)ccn5)C4)cn3)no2)C(C)C)cc1] |

TABLE 1C-continued
| Exemplary bifunctional degradation compounds of the present disclosure | | |
|---|---|---|
| Ex. # | Compound Name | Structure |
| 392 | (2S,4R)-1-((2R)-2-(3-(((E)-3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)allyl)oxy)isoxazol-5-yl)-3-methylbutanoyl)-4-hydroxy-N-((S)-1-(4-(4-methylthiazol-5-yl)phenyl)ethyl)pyrrolidine-2-carboxamide | 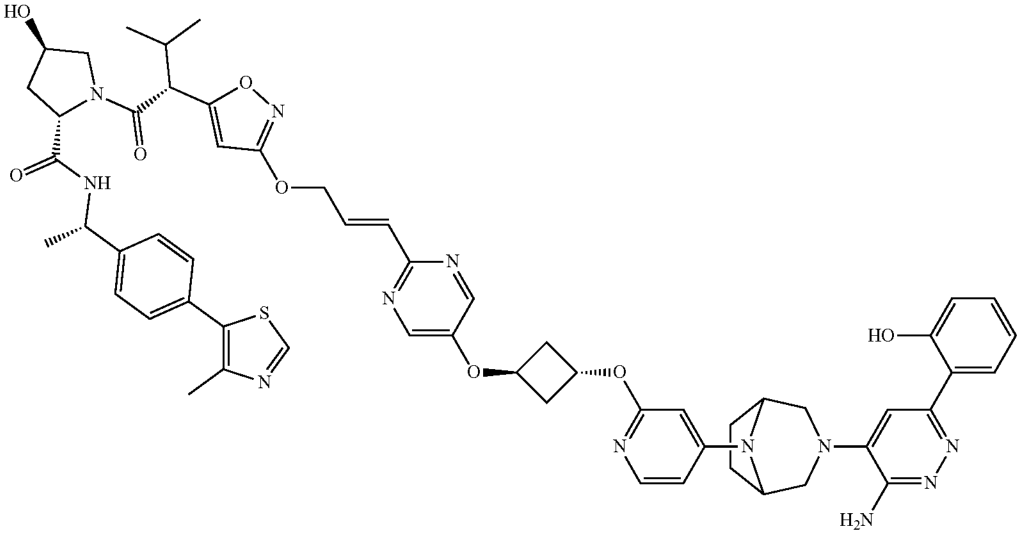 [SMILES: Cc1ncsc1-c1ccc([C@H](C)NC(=O)[C@@H]2C[C@@H](O)CN2C(=O)[C@@H](c2cc(OC/C=C/c3ncc(O[C@H]4C[C@H](Oc5cc(N6C7CCC6CN(c6cc(-c8ccccc8O)nnc6N)C7)ccn5)C4)cn3)no2)C(C)C)cc1] |

TABLE 1C-continued
| Exemplary bifunctional degradation compounds of the present disclosure | | |
|---|---|---|
| Ex. # | Compound Name | Structure |
| 393 | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide | 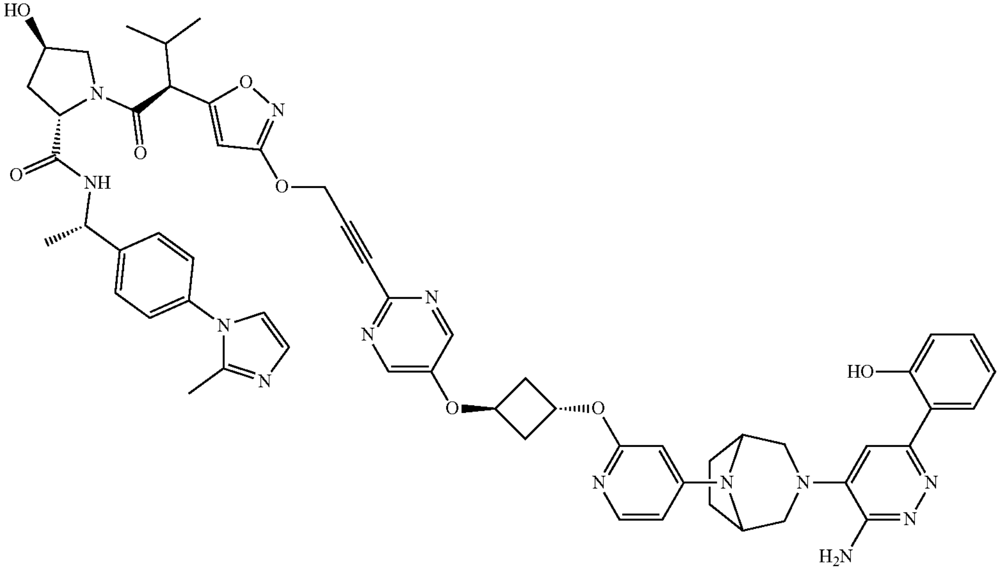 [SMILES: Cc1nccn1-c1ccc([C@H](C)NC(=O)[C@@H]2C[C@@H](O)CN2C(=O)[C@H](c2cc(OCC#Cc3ncc(O[C@H]4C[C@H](Oc5cc(N6C7CCC6CN(c6cc(-c8ccccc8O)nnc6N)C7)ccn5)C4)cn3)no2)C(C)C)cc1] |

TABLE 1C-continued

| Ex. # | Compound Name | Structure |
|---|---|---|
| | Exemplary bifunctional degradation compounds of the present disclosure | |
| 394 | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(4-(2-methyl-1H-imidazol-1-yl)phenyl)ethyl)pyrrolidine-2-carboxamide | 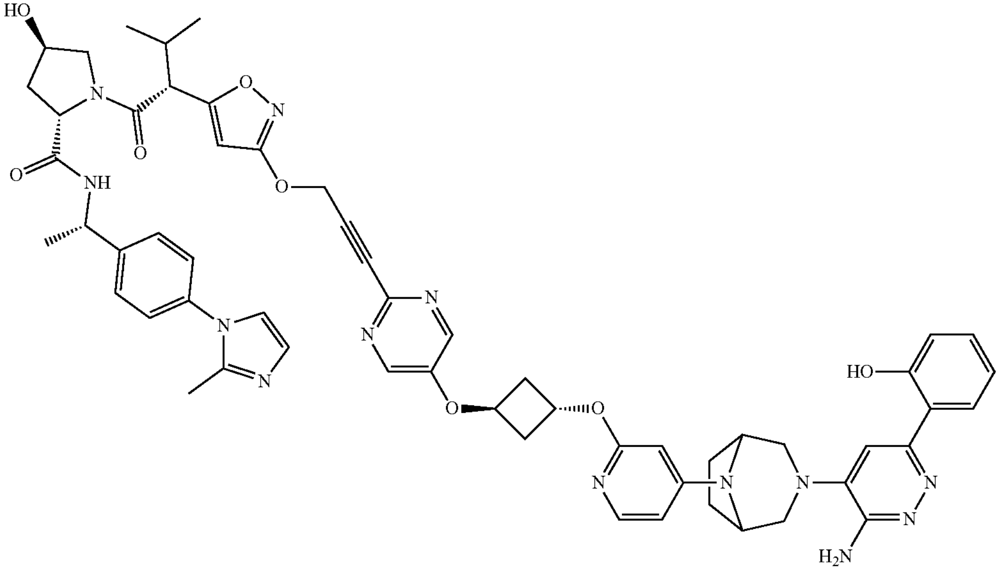 [SMILES: Cc1nccn1-c1ccc([C@H](C)NC(=O)[C@@H]2C[C@@H](O)CN2C(=O)[C@@H](c2cc(OCC#Cc3ncc(O[C@H]4C[C@H](Oc5cc(N6C7CCC6CN(c6cc(-c8ccccc8O)nnc6N)C7)ccn5)C4)cn3)no2)C(C)C)cc1] |
| 395 | (2S,4R)-1-((R)-2-(3-(2-(4-((1r,3R)-3-((4-(4-(3-amino-6-(2-hydroxyphenyl)pyridazin-4-yl)-1H-pyrazol-1-yl)but-2-yn-1-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 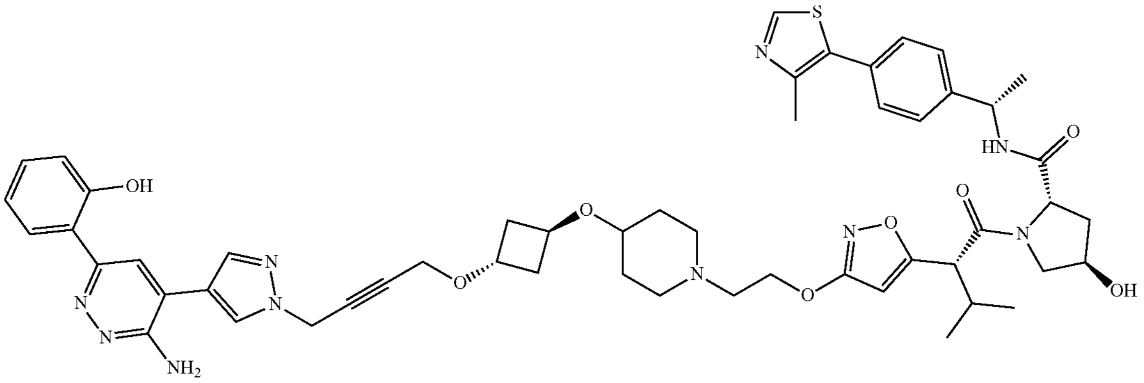 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](OCC#CCn5cc(-c6cc(-c7ccccc7O)nnc6N)cn5)C4)CC3)no2)C(C)C)cc1] |

TABLE 1C-continued
Exemplary bifunctional degradation compounds of the present disclosure
| Ex. # | Compound Name | Structure |
|---|---|---|
| 396 | (2S,4R)-1-((2R)-2-(3-(2-(((1R,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)amino)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 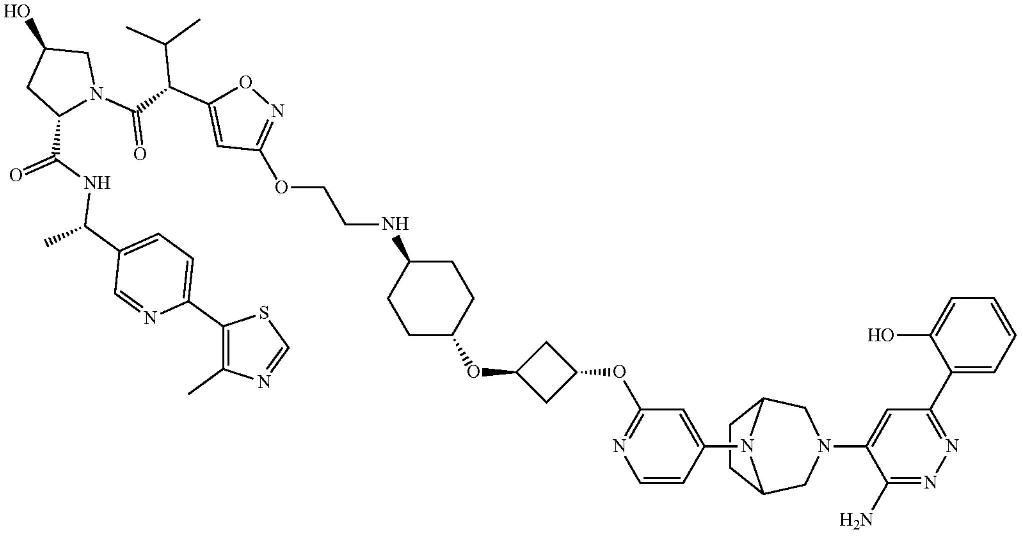 [SMILES: Cc1ncsc1-c1ccc([C@H](C)NC(=O)[C@@H]2C[C@@H](O)CN2C(=O)[C@@H](c2cc(OCCN[C@H]3CC[C@H](O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 397 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)cthoxy)isoxazol-5-yl)-3-methylbutanoyl)-4-hydroxy-N-((S)-1-(6-(2-methyl-1H-imidazol-1-yl)pyridin-3-yl)ethyl)pyrrolidine-2-carboxamide | 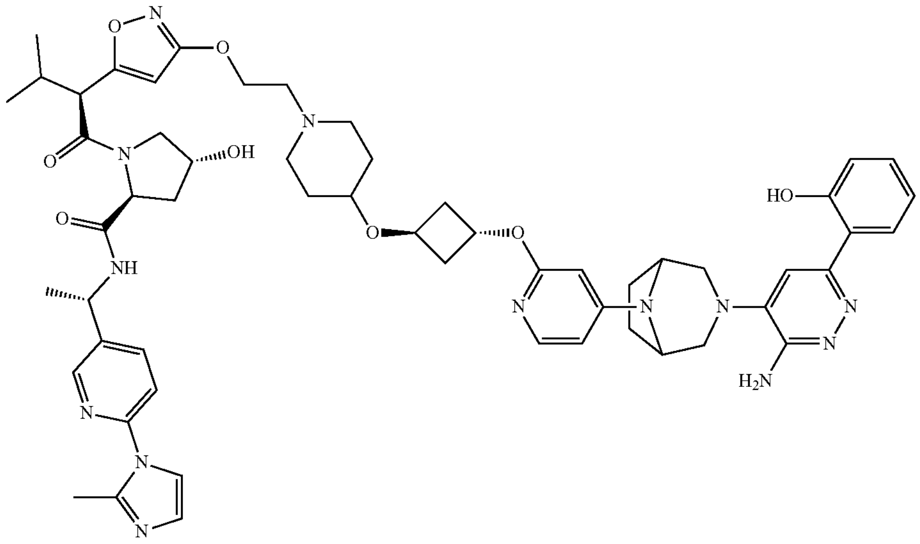 [SMILES: Cc1nccn1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 398 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(2-methyl-1H-imidazol-1-yl)pyridin-3-yl)ethyl)pyrrolidine-2-carboxamide | 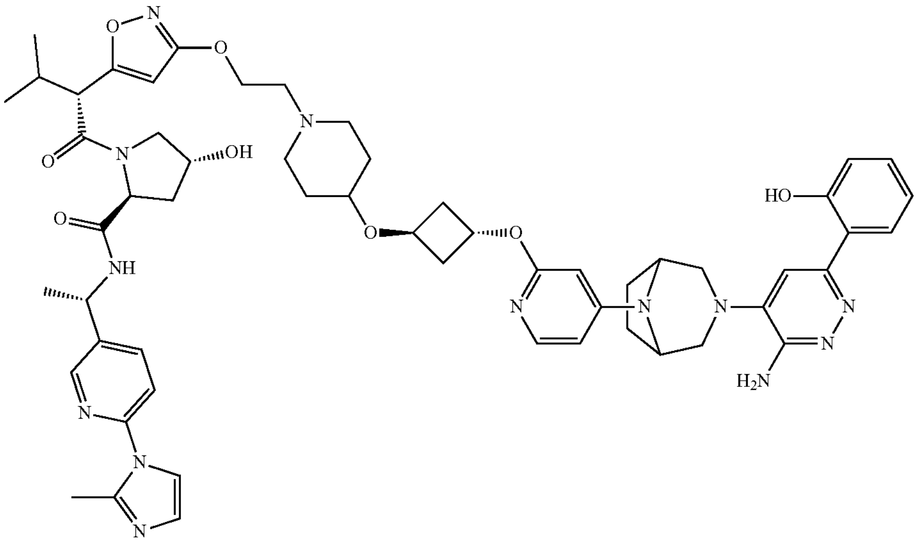 [SMILES: Cc1nccn1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 399 | (2S,4R)-1-((2S)-2-(3-((3-(5-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 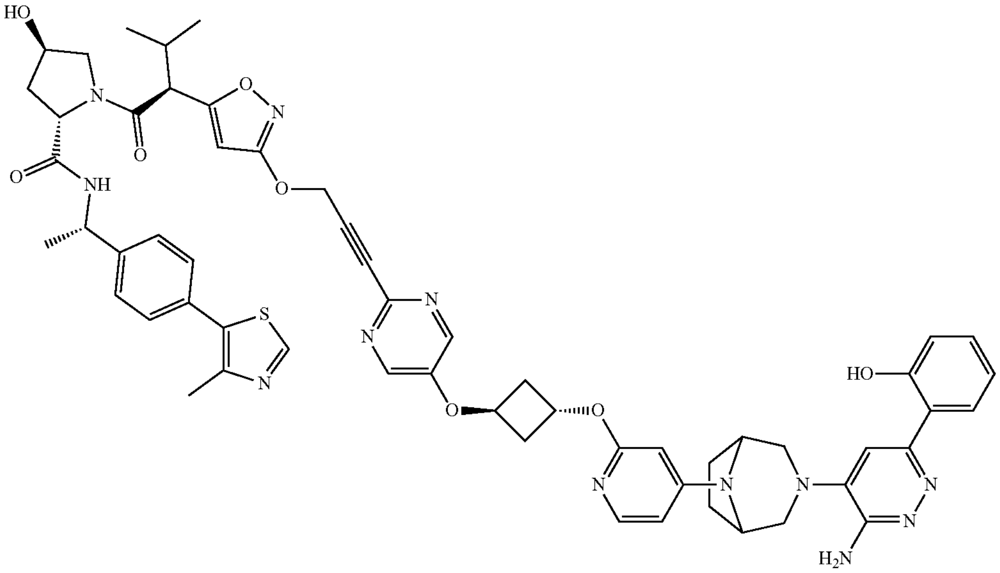 [SMILES: Cc1ncsc1-c1ccc([C@H](C)NC(=O)[C@@H]2C[C@@H](O)CN2C(=O)[C@H](c2cc(OCC#Cc3ncc(O[C@H]4C[C@H](Oc5cc(N6C7CCC6CN(c6cc(-c8ccccc8O)nnc6N)C7)ccn5)C4)cn3)no2)C(C)C)cc1] |

TABLE 1C-continued
| Exemplary bifunctional degradation compounds of the present disclosure | | |
|---|---|---|
| Ex. # | Compound Name | Structure |
| 400 | (2S,4R)-1-((2R)-2-(3-((3-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 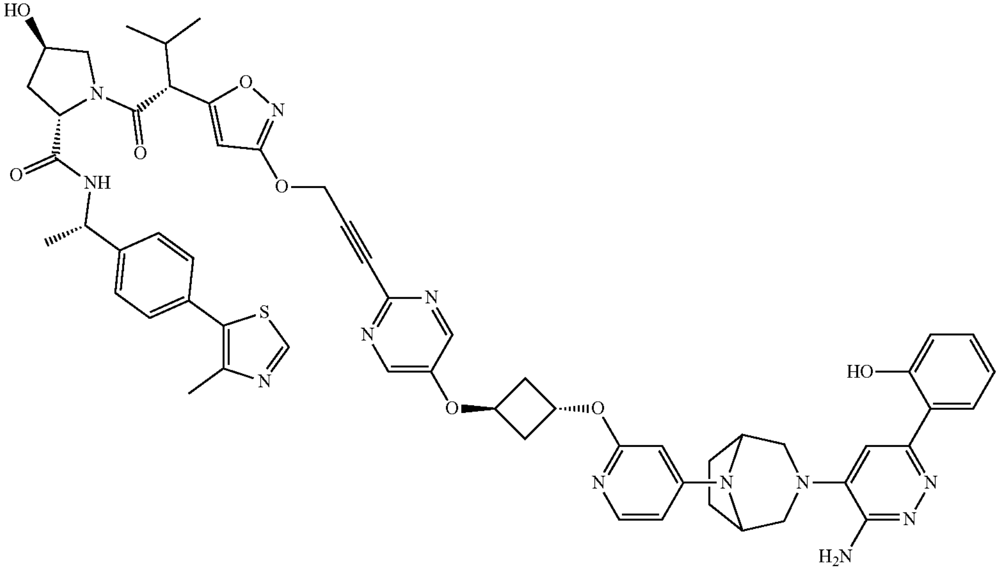 [SMILES: Cc1ncsc1-c1ccc([C@H](C)NC(=O)[C@@H]2C[C@@H](O)CN2C(=O)[C@@H](c2cc(OCC#Cc3ncc(O[C@H]4C[C@H](Oc5cc(N6C7CCC6CN(c6cc(-c8ccccc8O)nnc6N)C7)ccn5)C4)cn3)no2)C(C)C)cc1] |

TABLE 1C-continued
| Exemplary bifunctional degradation compounds of the present disclosure | | |
|---|---|---|
| Ex. # | Compound Name | Structure |
| 401 | (2S,4R)-1-((2S)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 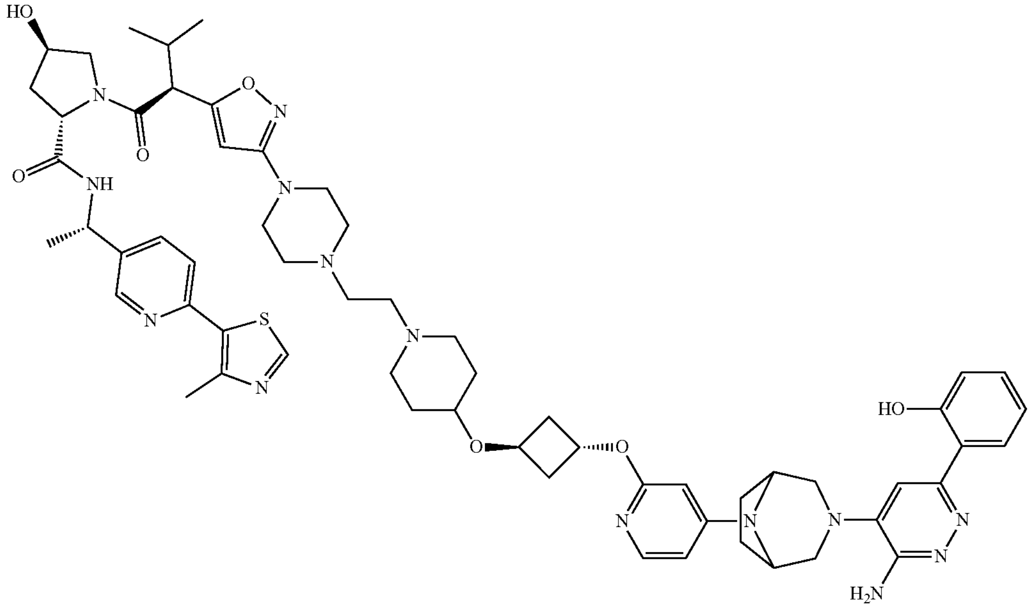 [SMILES: Cc1ncsc1-c1ccc([C@H](C)NC(=O)[C@@H]2C[C@@H](O)CN2C(=O)[C@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cn1] |

TABLE 1C-continued
| Exemplary bifunctional degradation compounds of the present disclosure | | |
|---|---|---|
| Ex. # | Compound Name | Structure |
| 402 | (2S,4R)-1-((2R)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 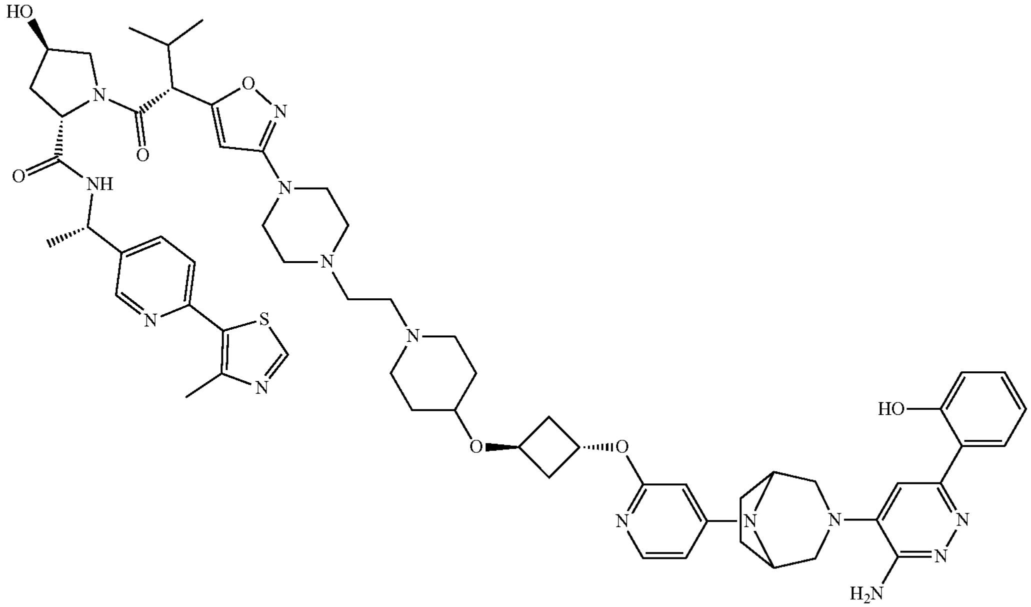 [SMILES: Cc1ncsc1-c1ccc([C@H](C)NC(=O)[C@@H]2C[C@@H](O)CN2C(=O)[C@@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cn1] |

TABLE 1C-continued

| Exemplary bifunctional degradation compounds of the present disclosure | | |
|---|---|---|
| Ex. # | Compound Name | Structure |
| 403 | (2S,4R)-1-((2S)-2-(3-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 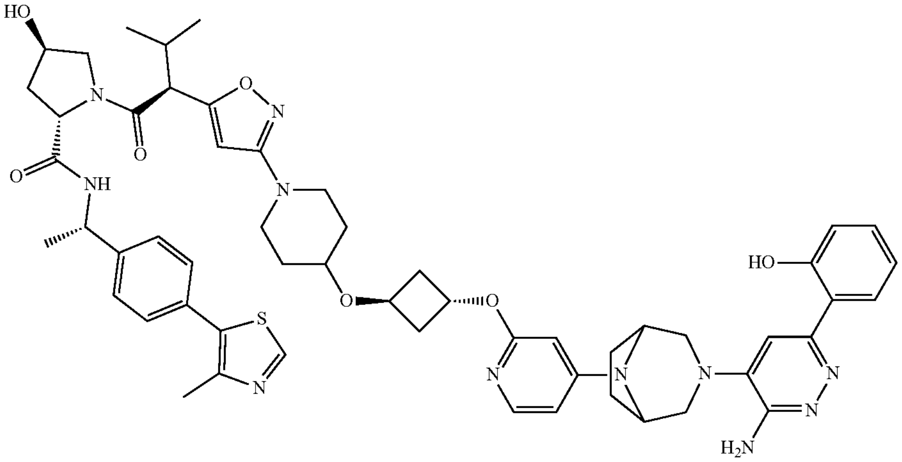 [SMILES: Cc1ncsc1-c1ccc([C@H](C)NC(=O)[C@@H]2C[C@@H](O)CN2C(=O)[C@H](c2cc(N3CCC(O[C@H]4C[C@H](Oc5cc(N6C7CCC6CN(c6cc(-c8ccccc8O)nnc6N)C7)ccn5)C4)CC3)no2)C(C)C)cc1] |
| 404 | (2S,4R)-1-((2R)-2-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 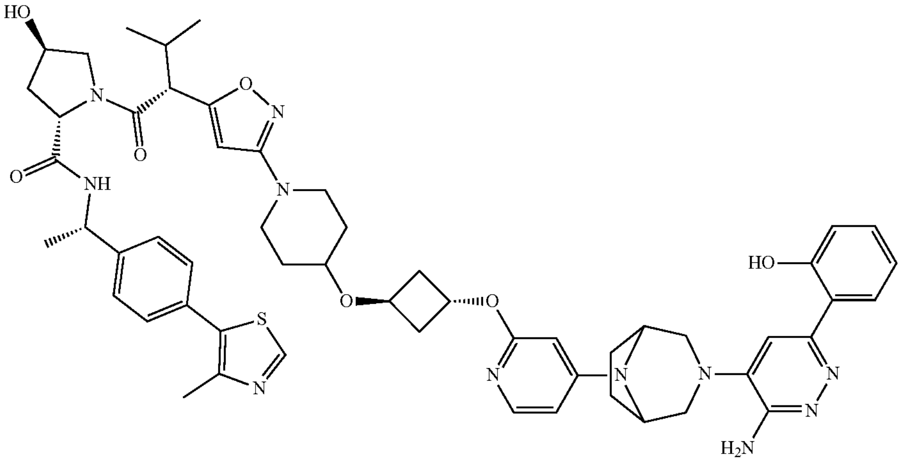 [SMILES: Cc1ncsc1-c1ccc([C@H](C)NC(=O)[C@@H]2C[C@@H](O)CN2C(=O)[C@@H](c2cc(N3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 405 | (2S,4R)-1-((2R)-2-(3-(2-(4-(3-((4-(3-(3-amino-6-(2-hydroxyphenyl)pyridazin-4-yl)-3,8-diazabicyclo[3.2.1]octan-8-yl)pyridin-2-yl)oxy)azetidine-1-carbonyl)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 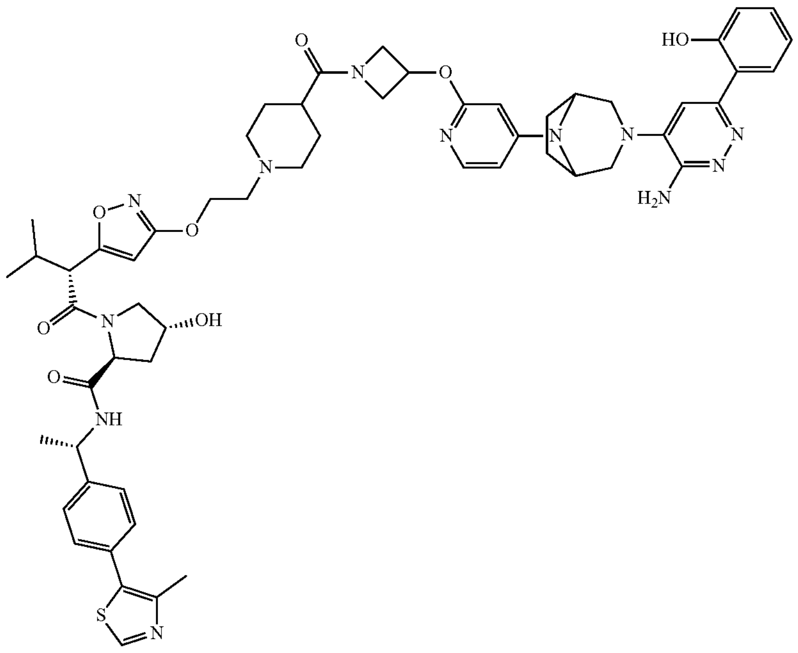 [SMILES: Cc1ncsc1-c1ccc([C@H](C)NC(=O)[C@@H]2C[C@@H](O)CN2C(=O)[C@@H](c2cc(OCCN3CCC(C(=O)N4CC(Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 406 | (2S,4R)-1-((2R)-2-(3-(2-(4-((3-((4-(3-(3-amino-6-(2-hydroxyphenyl)pyridazin-4-yl)-3,8-diazabicyclo[3.2.1]octan-8-yl)pyridin-2-yl)oxy)azetidin-1-yl)methyl)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 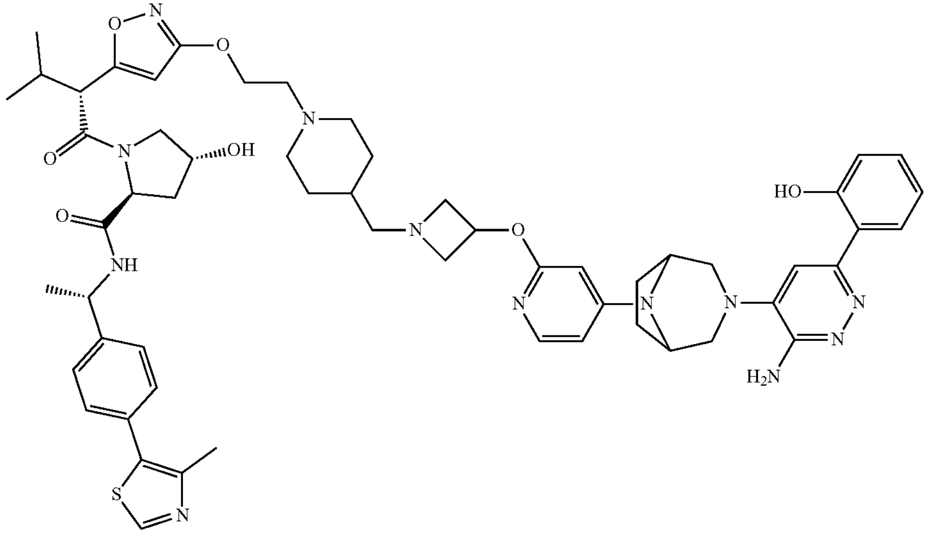 [SMILES: Cc1ncsc1-c1ccc([C@H](C)NC(=O)[C@@H]2C[C@@H](O)CN2C(=O)[C@@H](c2cc(OCCN3CCC(CN4CC(Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 407 | (2S,4R)-1-((2S)-2-(3-(2-(4-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 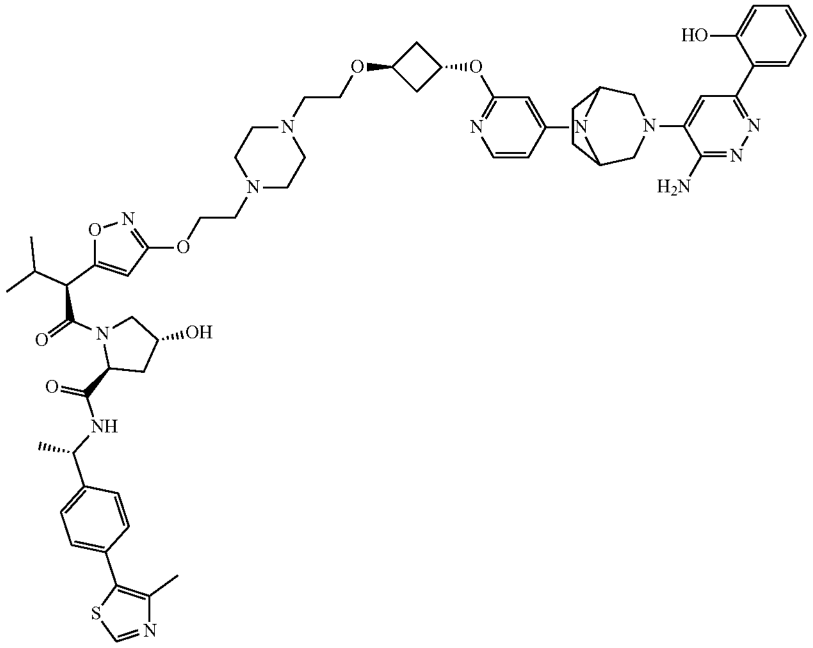 [SMILES: Cc1ncsc1-c1ccc([C@H](C)NC(=O)[C@@H]2C[C@@H](O)CN2C(=O)[C@H](c2cc(OCCN3CCN(CCO[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
Exemplary bifunctional degradation compounds of the present disclosure
| Ex. # | Compound Name | Structure |
|---|---|---|
| 408 | (2S,4R)-1-((2R)-2-(3-(2-(4-(2-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)ethyl)piperazin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 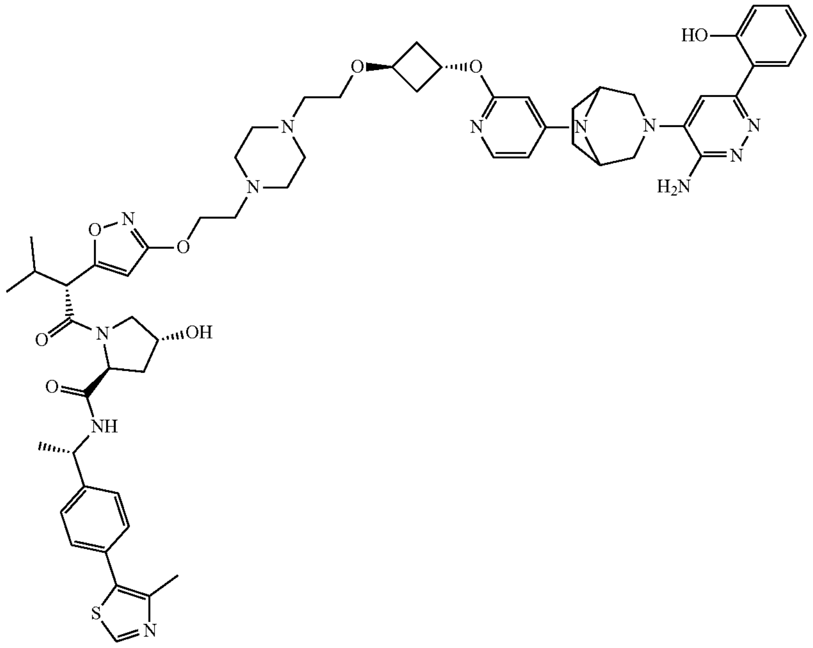 [SMILES: Cc1ncsc1-c1ccc([C@H](C)NC(=O)[C@@H]2C[C@@H](O)CN2C(=O)[C@@H](c2cc(OCCN3CCN(CCO[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 409 | (2S,4R)-1-((2S)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-fluoro-1-methyl-1H-pyrazol-5-yl)phenyl)ethyl)-4-hydroxypyrrolidine-2-carboxamide | 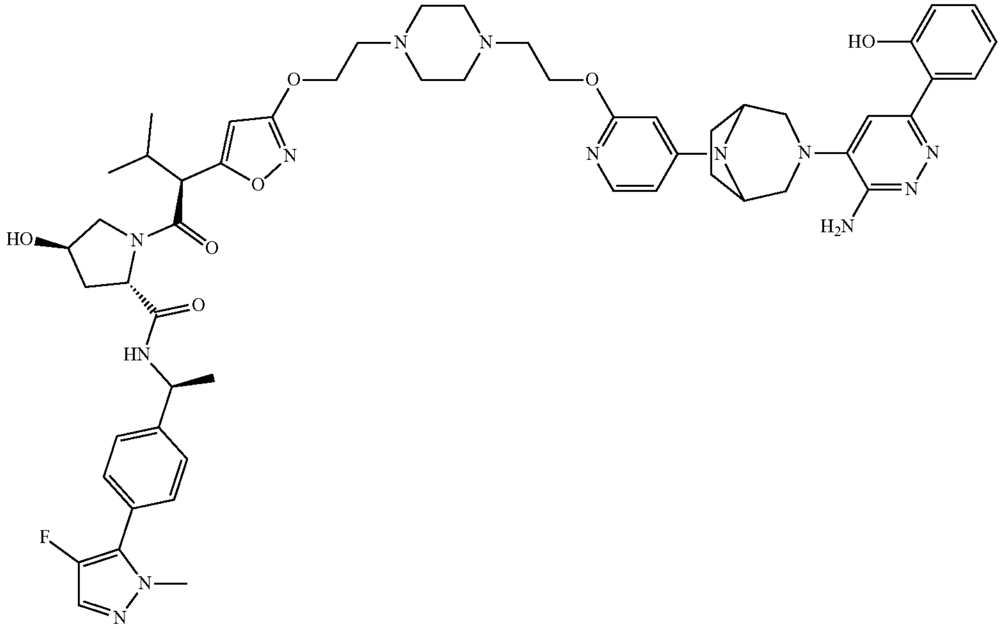 [SMILES: CC(C)[C@H](C(=O)N1C[C@H](O)C[C@H]1C(=O)N[C@@H](C)c1ccc(-c2c(F)cnn2C)cc1)c1cc(OCCN2CCN(CCOc3cc(N4C5CCC4CN(c4cc(-c6ccccc6O)nnc4N)C5)ccn3)CC2)no1] |

TABLE 1C-continued
| Exemplary bifunctional degradation compounds of the present disclosure | | |
|---|---|---|
| Ex. # | Compound Name | Structure |
| 410 | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)ethoxy)isoxazol-5-yl)-3-methylbutanoyl)-N-((S)-1-(4-(4-fluoro-1-methyl-1H-pyrazol-5-yl)phenyl)ethyl)-4-hydroxypyrrolidine-2-carboxamide | 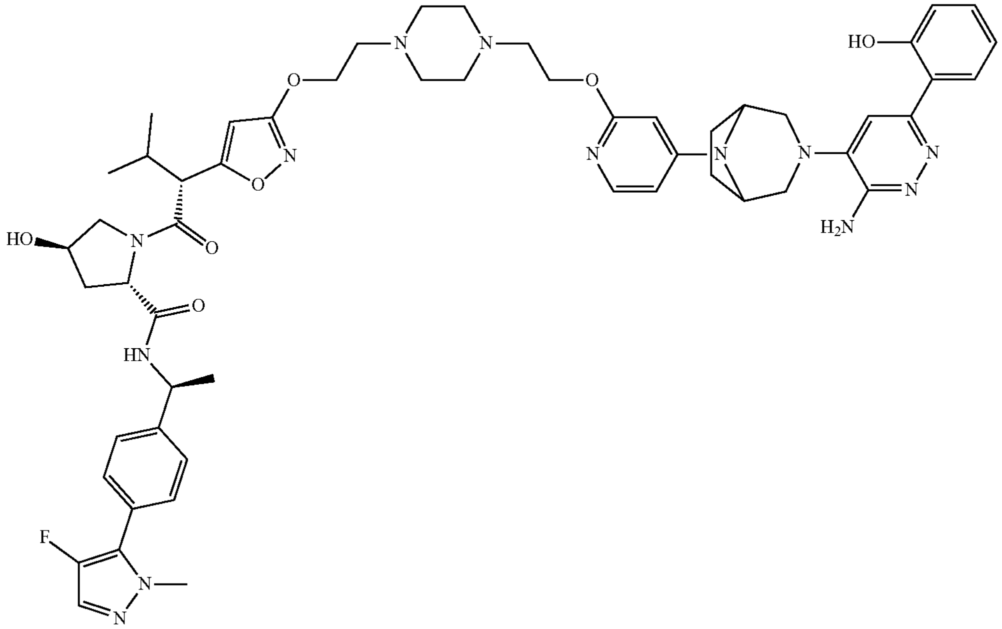 [SMILES: CC(C)[C@@H](C(=O)N1C[C@H](O)C[C@H]1C(=O)N[C@@H](C)c1ccc(-c2c(F)cnn2C)cc1)c1cc(OCCN2CCN(CCOc3cc(N4C5CCC4CN(c4cc(-c6ccccc6O)nnc4N)C5)ccn3)CC2)no1] |

TABLE 1C-continued
| Exemplary bifunctional degradation compounds of the present disclosure | | |
|---|---|---|
| Ex. # | Compound Name | Structure |
| 411 | (2S,4R)-1-(2-(3-((1R,3S)-3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)cyclobutoxy)isoxazol-5-yl)-3-methylbutanoyl)-4-hydroxy-N-((S)-1-(4-(4-methylthiazol-5-yl)phenyl)ethyl)pyrrolidine-2-carboxamide | 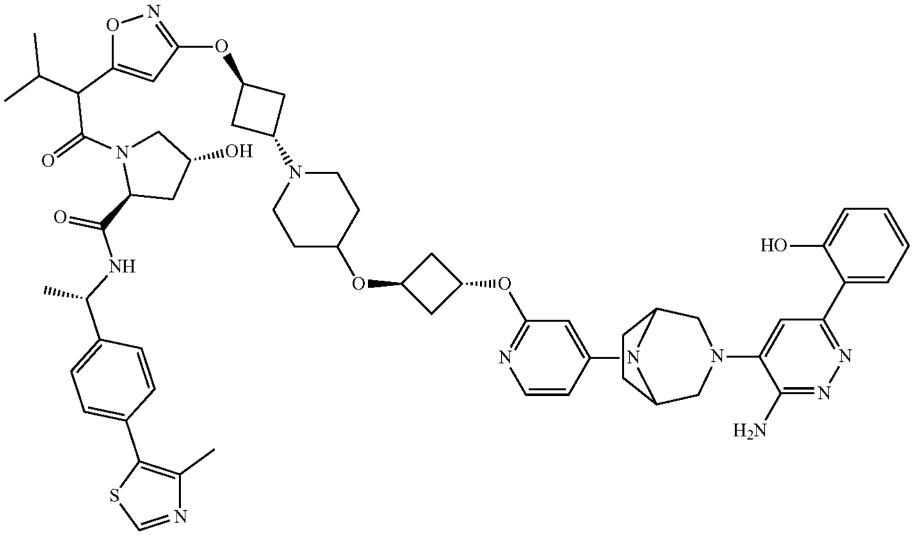 [SMILES: Cc1ncsc1-c1ccc([C@H](C)NC(=O)[C@@H]2C[C@@H](O)CN2C(=O)C(c2cc(O[C@H]3C[C@H](N4CCC(O[C@H]5C[C@H](Oc6cc(N7C8CCC7CN(c7cc(-c9ccccc9O)nnc7N)C8)ccn6)C5)CC4)C3)no2)C(C)C)cc1] |

TABLE 1C-continued
| Exemplary bifunctional degradation compounds of the present disclosure | | |
|---|---|---|
| Ex. # | Compound Name | Structure |
| 412 | (2S,4R)-1-((2S)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(4-(2-methyl-1 H-imidazol-1-yl)phenyl)ethyl)pyrrolidine-2-carboxamide | 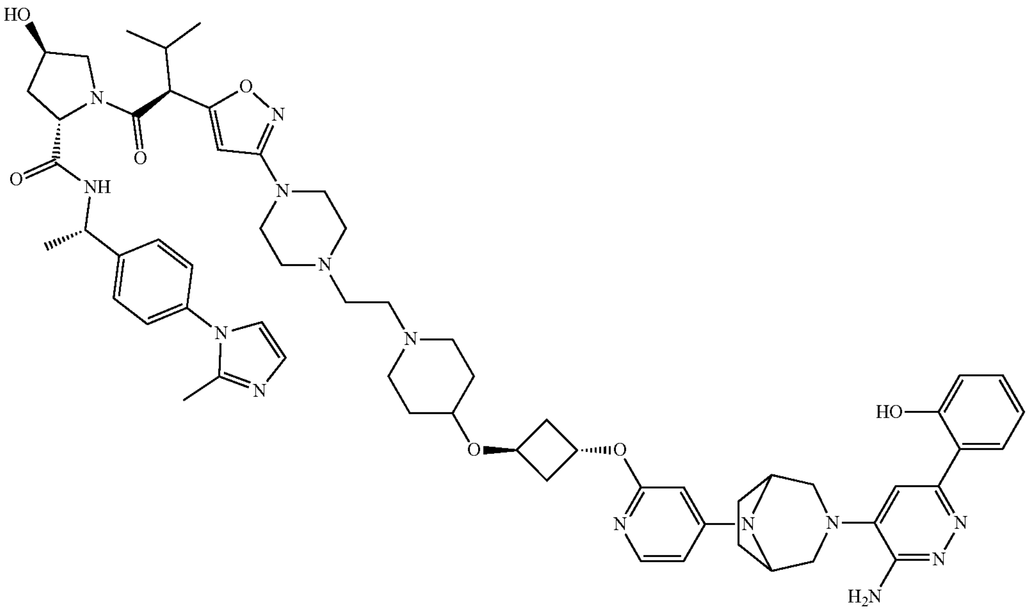 [SMILES: Cc1nccn1-c1ccc([C@H](C)NC(=O)[C@@H]2C[C@@H](O)CN2C(=O)[C@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 413 | (2S,4R)-1-((2R)-2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperazin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide | 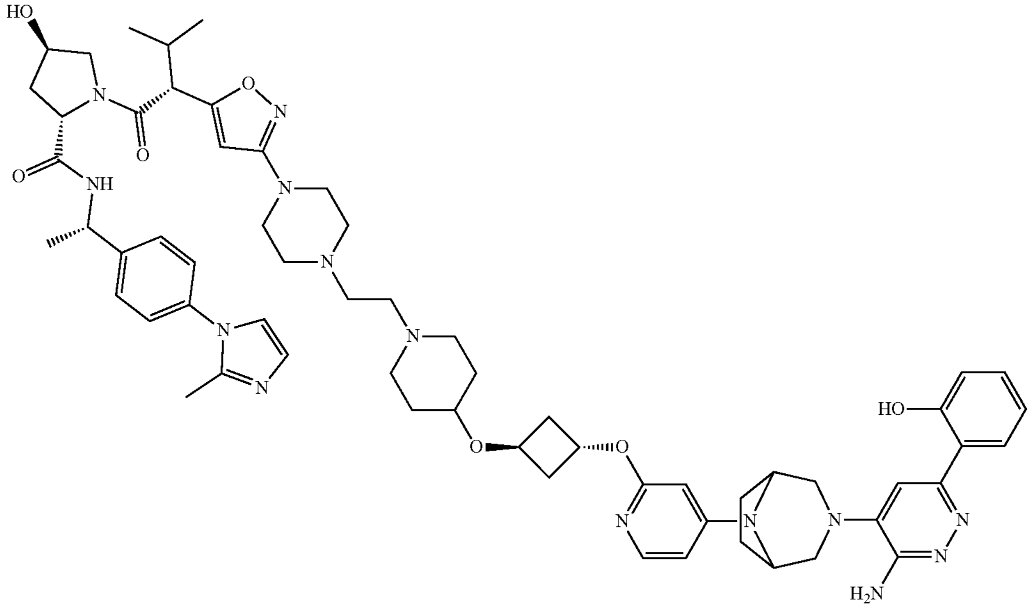 [SMILES: Cc1nccn1-c1ccc([C@H](C)NC(=O)[C@@H]2C[C@@H](O)CN2C(=O)[C@@H](c2cc(N3CCN(CCN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 414 | (2S,4R)-1-((R)-2-(3-(2-(4-((1R,3R)-3-((R)-3-(4-(3-amino-6-(2-hydroxyphenyl)pyridazin-4-yl)-1 H-pyrazol-1-yl)but-1-yn-1-yl)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 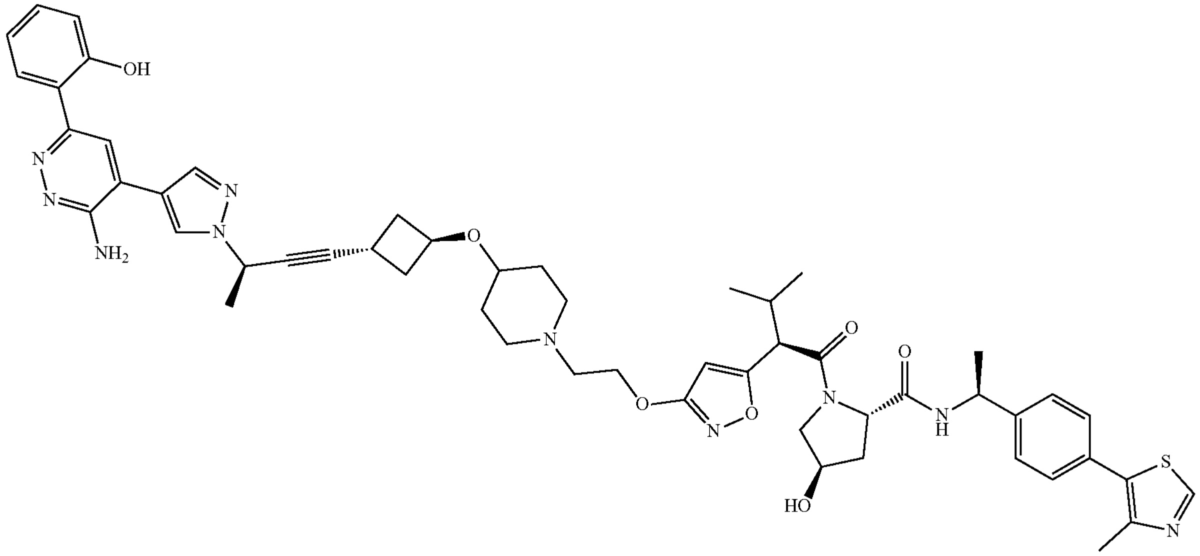 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](C#C[C@@H](C)n5cc(-c6cc(-c7ccccc7O)nnc6N)cn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 415 | (2S,4R)-1-((R)-2-(3-(2-(4-((1S,3R)-3-((S)-3-(4-(3-amino-6-(2-hydroxyphenyl)pyridazin-4-yl)-1H-pyrazol-1-yl)but-1-yn-1-yl)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 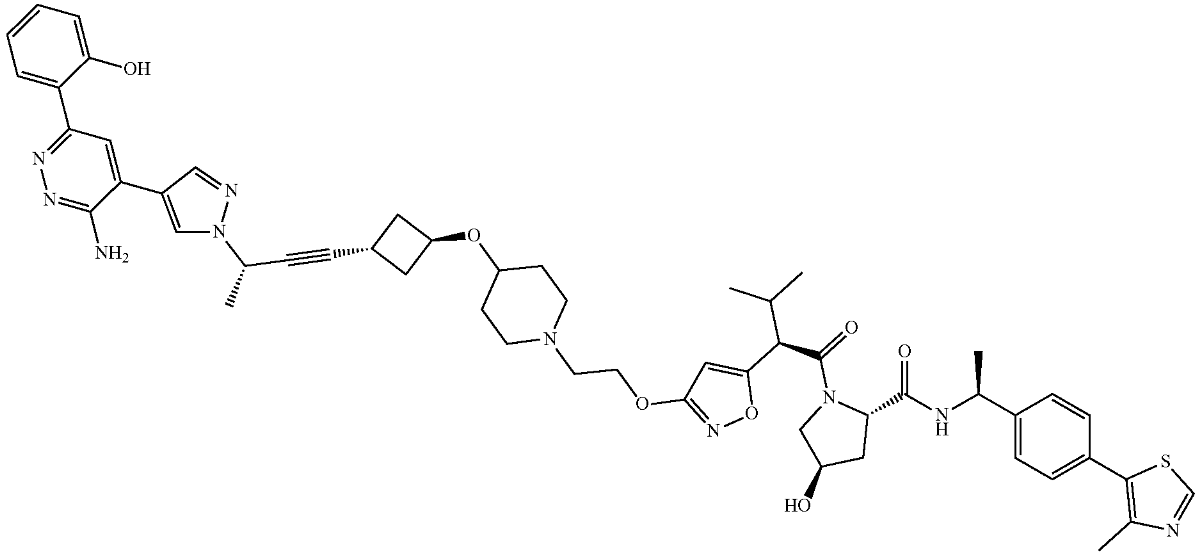 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](C#C[C@H](C)n5cc(-c6cc(-c7ccccc7O)nnc6N)cn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 416 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(4-aminothiazol-5-yl)phenyl)ethyl)-4-hydroxypyrrolidine-2-carboxamide | 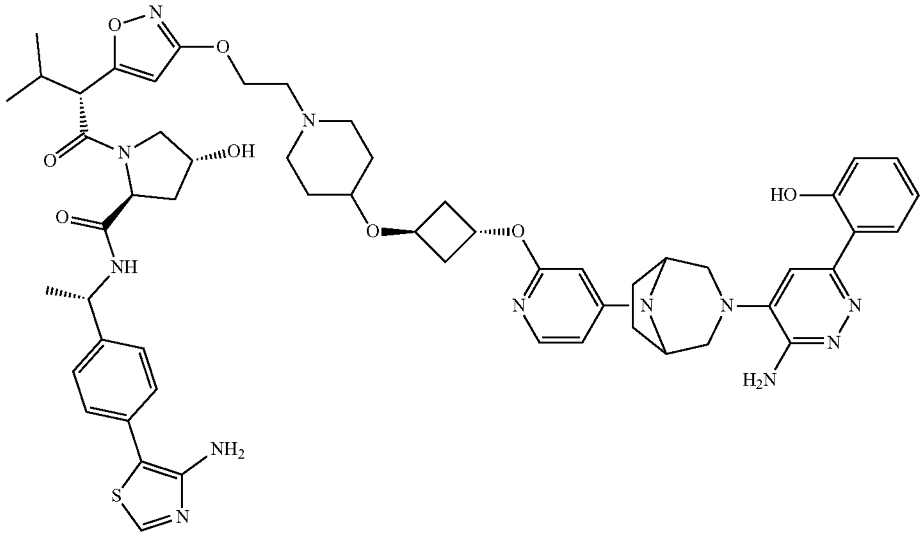 [SMILES: CC(C)[C@@H](C(=O)N1C[C@H](O)C[C@H]1C(=O)N[C@@H](C)c1ccc(-c2scnc2N)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued

| Exemplary bifunctional degradation compounds of the present disclosure | | |
|---|---|---|
| Ex. # | Compound Name | Structure |
| 417 | (2S,4R)-1-((2R)-2-(3-(2-(1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 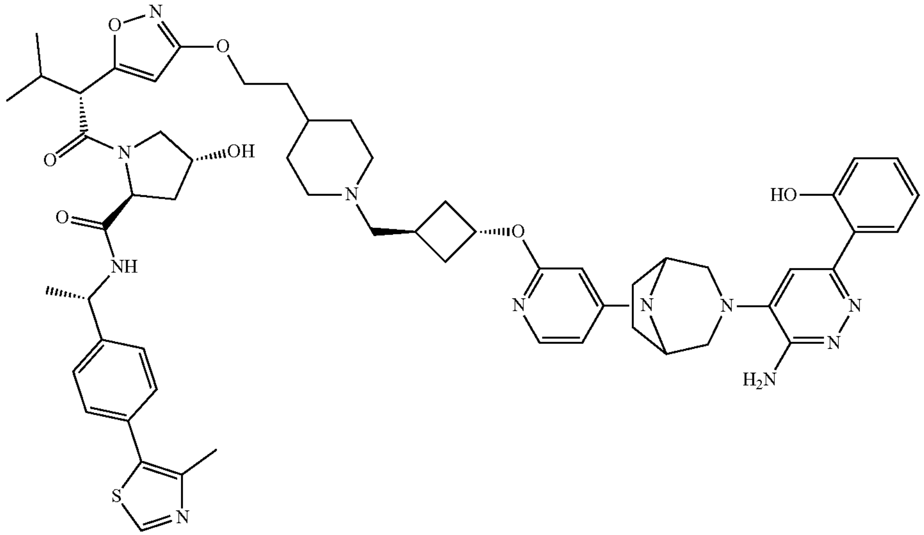 [SMILES: Cc1ncsc1-c1ccc([C@H](C)NC(=O)[C@@H]2C[C@@H](O)CN2C(=O)[C@@H](c2cc(OCCC3CCN(C[C@H]4C[C@H](Oc5cc(N6C7CCC6CN(c6cc(-c8ccccc8O)nnc6N)C7)ccn5)C4)CC3)no2)C(C)C)cc1] |
| 418 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-(4-(1-fluorocyclopropyl)benzyl)-4-hydroxypyrrolidine-2-carboxamide | 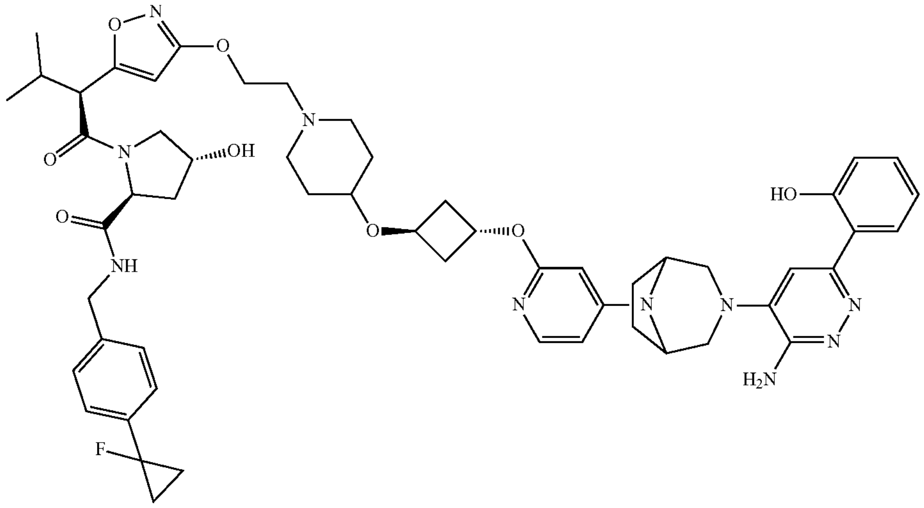 [SMILES: CC(C)[C@H](C(=O)N1C[C@H](O)C[C@H]1C(=O)NCc1ccc(C2(F)CC2)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued
| Exemplary bifunctional degradation compounds of the present disclosure | | |
|---|---|---|
| Ex. # | Compound Name | Structure |
| 419 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-(4-(1-fluorocyclopropyl)benzyl)-4-hydroxypyrrolidine-2-carboxamide | 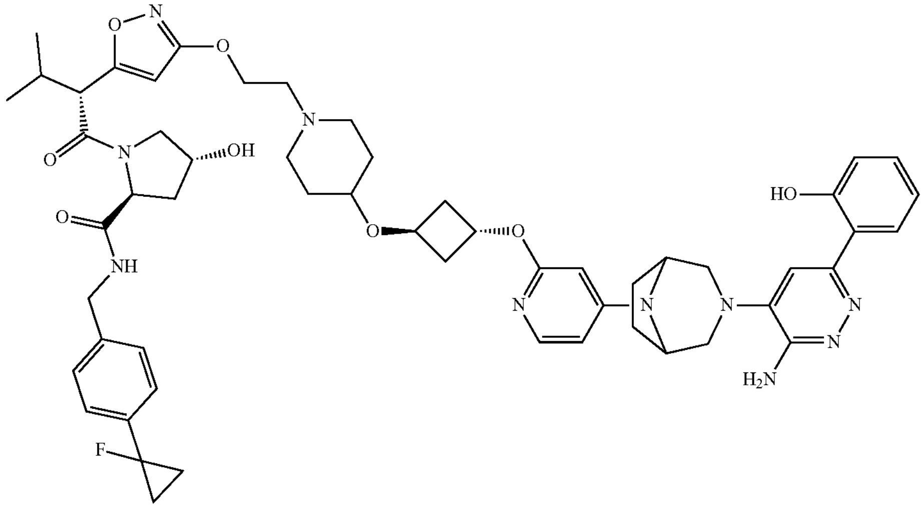 [SMILES: CC(C)[C@@H](C(=O)N1C[C@H](O)C[C@H]1C(=O)NCc1ccc(C2(F)CC2)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued
| Exemplary bifunctional degradation compounds of the present disclosure | | |
|---|---|---|
| Ex. # | Compound Name | Structure |
| 420 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-2-(cyclobutyl(methyl)amino)-1-(4-(4-methylthiazol-5-yl)phenyl)-2-oxoethyl)-4-hydroxypyrrolidine-2-carboxamide | 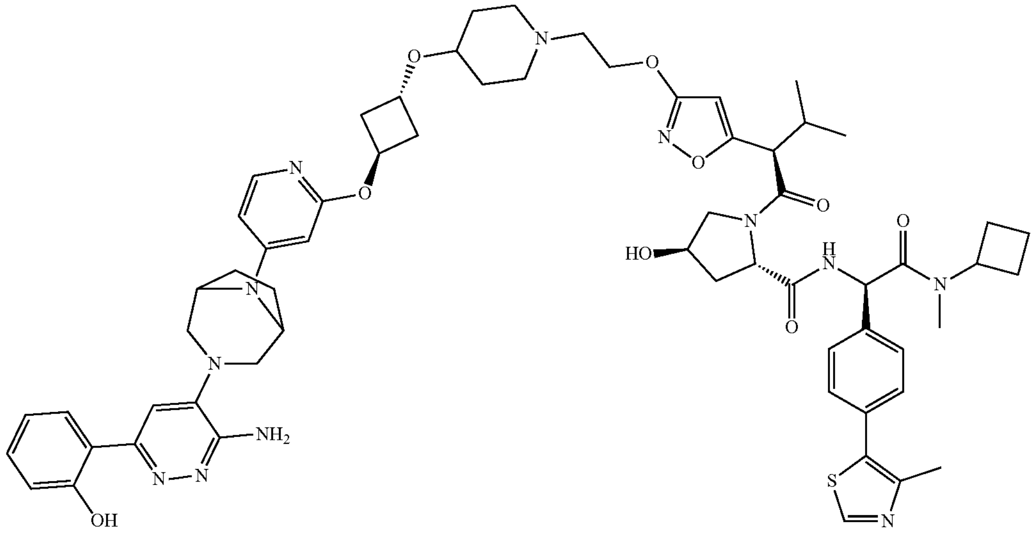 [SMILES: Cc1ncsc1-c1ccc([C@@H](NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)C(=O)N(C)C2CCC2)cc1] |

TABLE 1C-continued
| Exemplary bifunctional degradation compounds of the present disclosure | | |
|---|---|---|
| Ex. # | Compound Name | Structure |
| 421 | (2S,4R)-1-((2S)-2-(3-(3-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-2,2-difluoropropoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 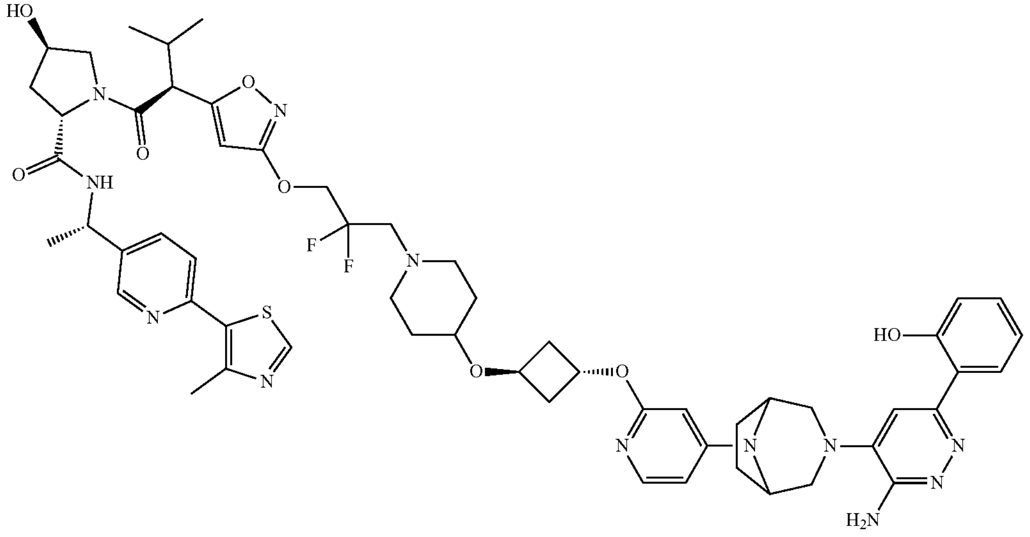 [SMILES: Cc1ncsc1-c1ccc([C@H](C)NC(=O)[C@@H]2C[C@@H](O)CN2C(=O)[C@H](c2cc(OCC(F)(F)CN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 422 | (2S,4R)-1-((2R)-2-(3-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-2,2-difluoropropoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 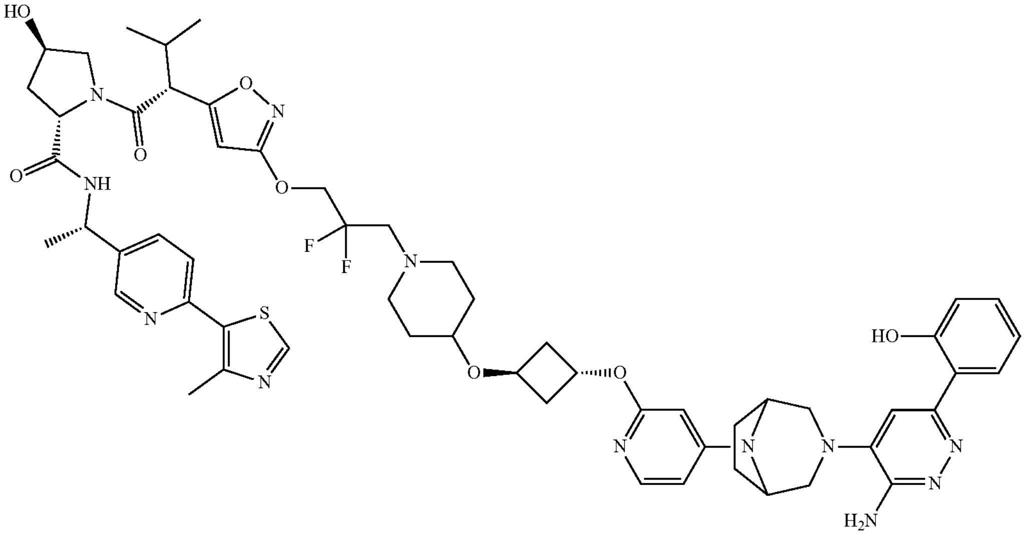 [SMILES: Cc1ncsc1-c1ccc([C@H](C)NC(=O)[C@@H]2C[C@@H](O)CN2C(=O)[C@@H](c2cc(OCC(F)(F)CN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued

| Exemplary bifunctional degradation compounds of the present disclosure | | |
|---|---|---|
| Ex. # | Compound Name | Structure |
| 423 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-2-(cyclobutyl(methyl)amino)-1-(4-(4-methylthiazol-5-yl)phenyl)-2-oxoethyl)-4-hydroxypyrrolidine-2-carboxamide | 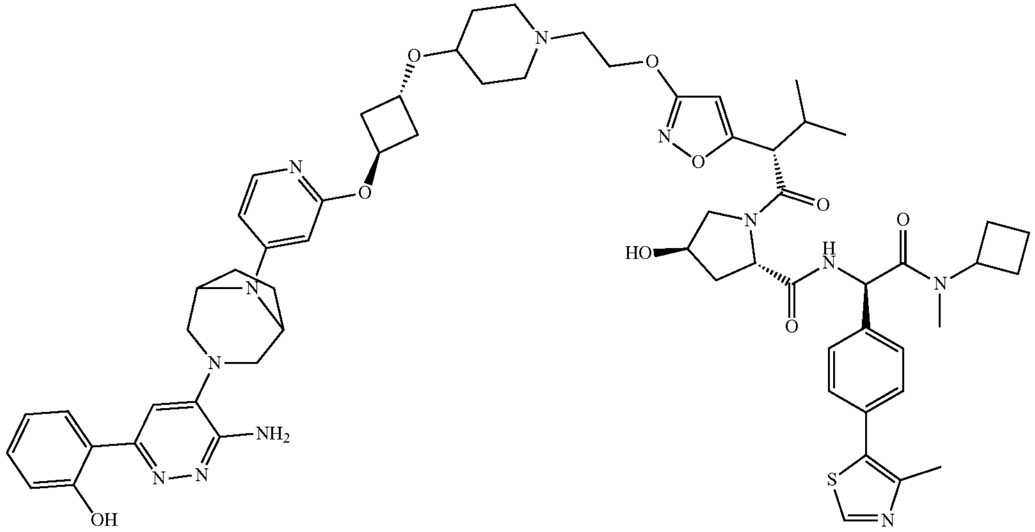 [SMILES: Cc1ncsc1-c1ccc([C@@H](NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)C(=O)N(C)C2CCC2)cc1] |
| 424 | (2S,4R)-1-((2S,3S)-4-(4-(3-(3-amino-6-(2-hydroxyphenyl)pyridazin-4-yl)-3,8-diazabicyclo[3.2.1]octan-8-yl)butoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 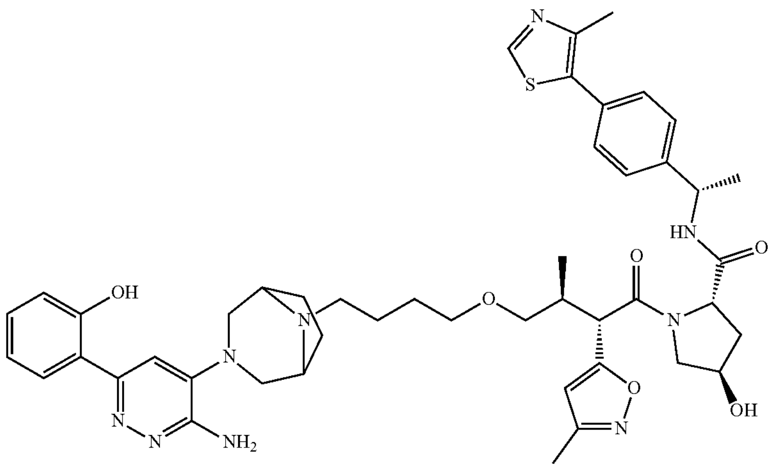 [SMILES: Cc1cc([C@@H](C(=O)N2C[C@H](O)C[C@H]2C(=O)N[C@@H](C)c2ccc(-c3scnc3C)cc2)[C@H](C)COCCCCN2C3CCC2CN(c2cc(-c4ccccc4O)nnc2N)C3)on1] |

TABLE 1C-continued

| Exemplary bifunctional degradation compounds of the present disclosure | | |
|---|---|---|
| Ex. # | Compound Name | Structure |
| 425 | (2S,4R)-1-((2R,3S)-4-(4-(3-(3-amino-6-(2-hydroxyphenyl)pyridazin-4-yl)-3,8-diazabicyclo[3.2.1]octan-8-yl)butoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 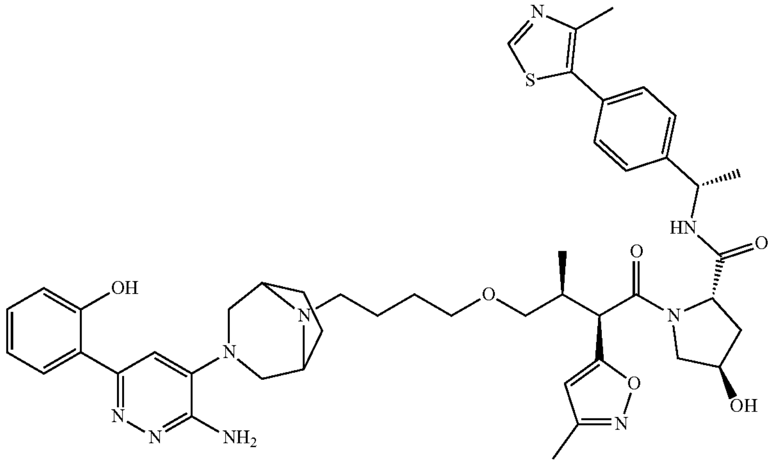 [SMILES: Cc1cc([C@H](C(=O)N2C[C@H](O)C[C@H]2C(=O)N[C@@H](C)c2ccc(-c3scnc3C)cc2)[C@H](C)COCCCCN2C3CCC2CN(c2cc(-c4ccccc4O)nnc2N)C3)on1] |
| 426 | (2S,4R)-1-((2S)-2-(3-(4-((1-(((1l,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)piperazin-1-yl)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 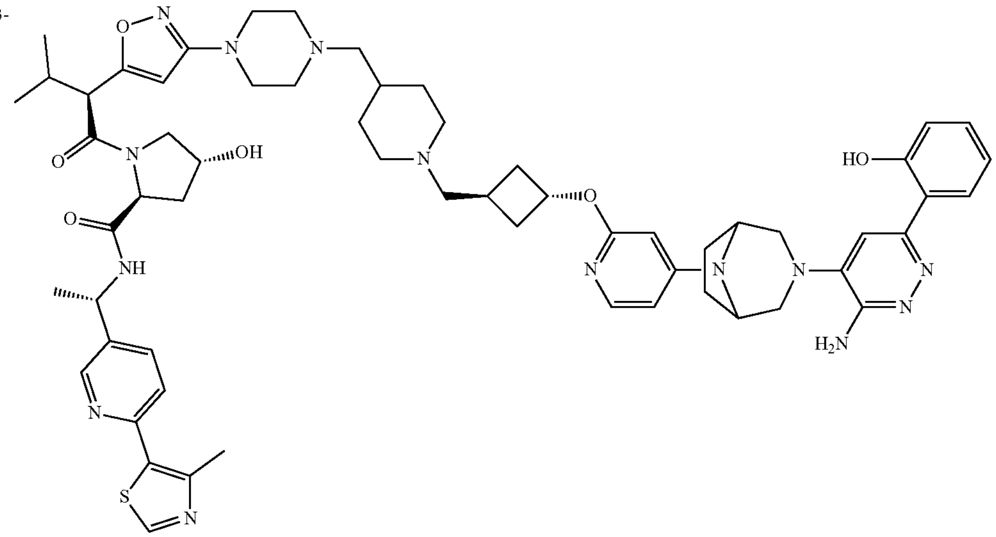 |

TABLE 1C-continued
| Exemplary bifunctional degradation compounds of the present disclosure | | |
|---|---|---|
| Ex. # | Compound Name | Structure |
| 427 | (2S,4R)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)piperazin-1-yl)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 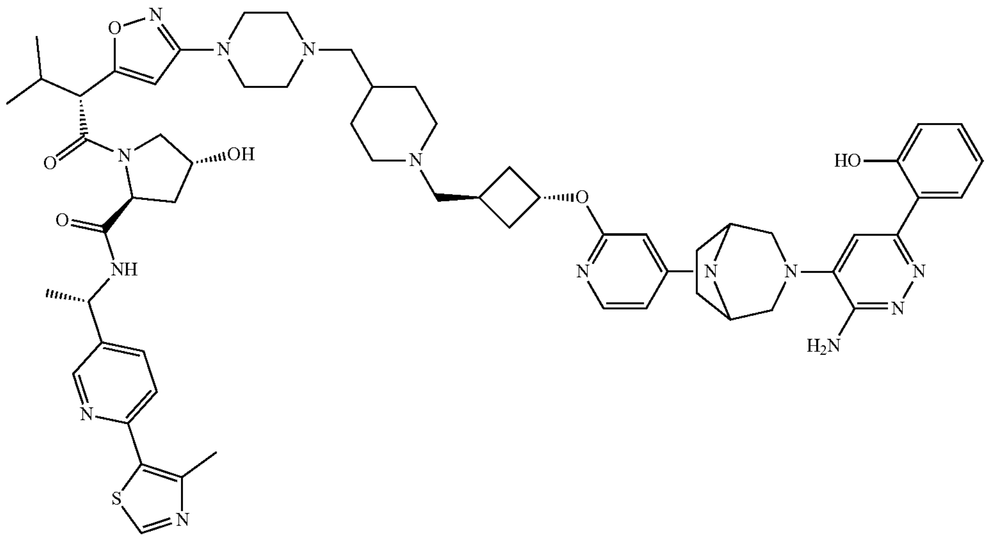 [SMILES: Cc1ncsc1-c1ccc([C@H](C)NC(=O)[C@@H]2C[C@@H](O)CN2C(=O)[C@@H](c2cc(N3CCN(CC4CCN(C[C@H]5C[C@H](Oc6cc(N7C8CCC7CN(c7cc(-c9ccccc9O)nnc7N)C8)ccn6)C5)CC4)CC3)no2)C(C)C)cn1] |

TABLE 1C-continued
Exemplary bifunctional degradation compounds of the present disclosure
| Ex. # | Compound Name | Structure |
| --- | --- | --- |
| 428 | (2S,4R)-1-((R)-2-(3-(2-(4-((1r,3R)-3-((4-((E)-2-(3-amino-6-(2-hydroxyphenyl)pyridazin-4-yl)vinyl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 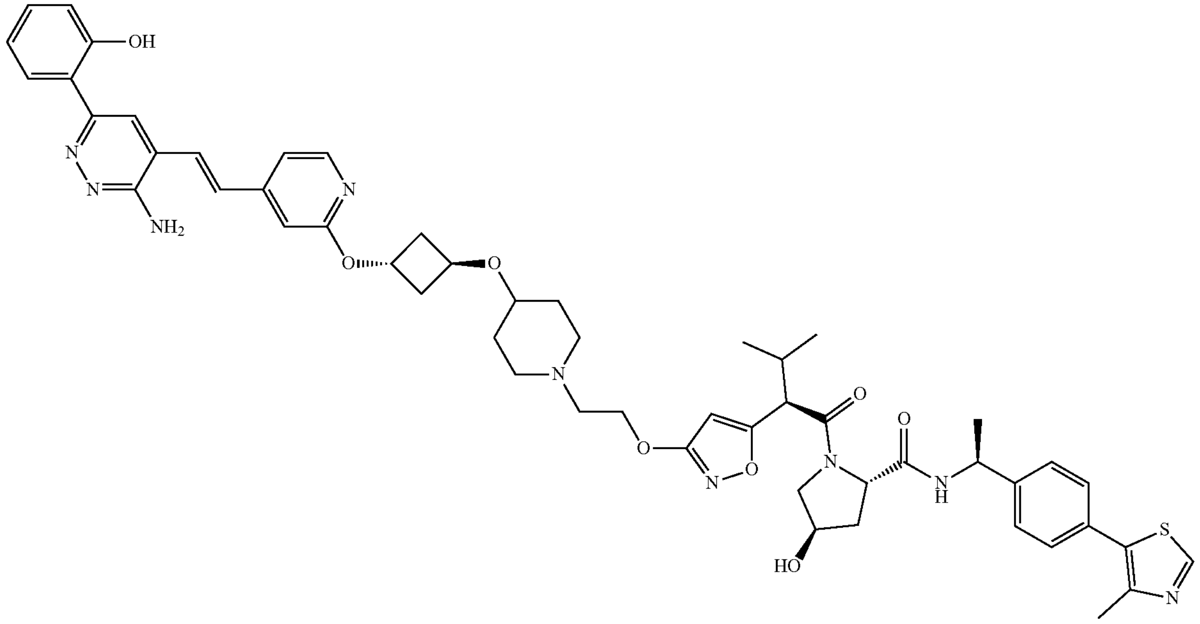 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(/C=C/c6cc(-c7ccccc7O)nnc6N)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 429 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(2-(4-methylthiazol-5-yl)pyrimidin-5-yl)ethyl)pyrrolidine-2-carboxamide | 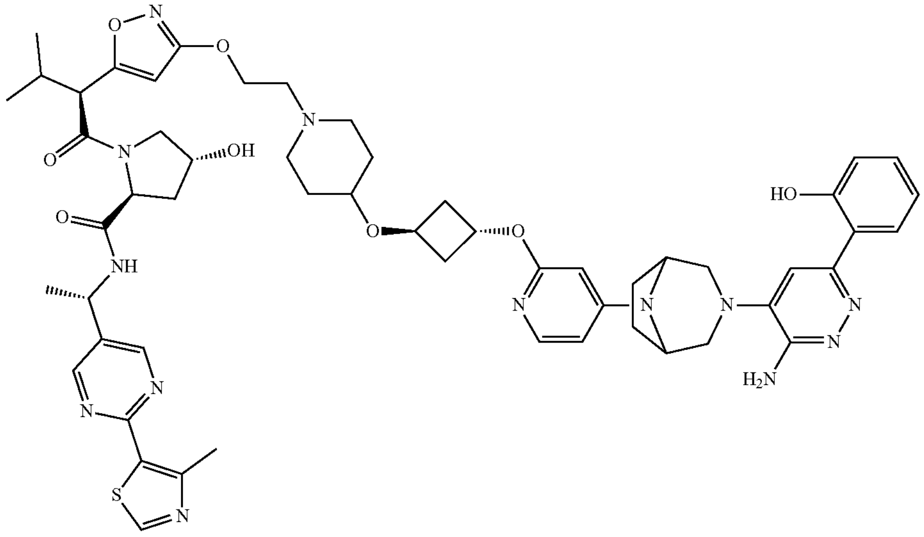 [SMILES: Cc1ncsc1-c1ncc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued

| Ex. # | Compound Name | Structure |
|---|---|---|
| | Exemplary bifunctional degradation compounds of the present disclosure | |
| 430 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(2-(4-methylthiazol-5-yl)pyrimidin-5-yl)ethyl)pyrrolidine-2-carboxamide | 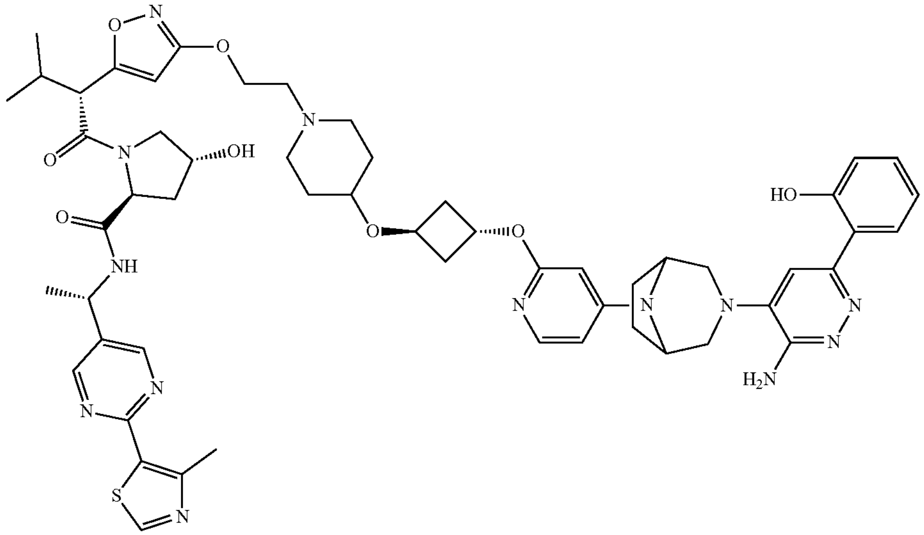 [SMILES: Cc1ncsc1-c1ncc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] |
| 431 | (2S,4R)-1-((2S,3R)-4-(4-((4-(3-(3-amino-6-(2-hydroxyphenyl)pyridazin-4-yl)-3,8-diazabicyclo[3.2.1]octan-8-yl)pyridin-2-yl)oxy)butoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 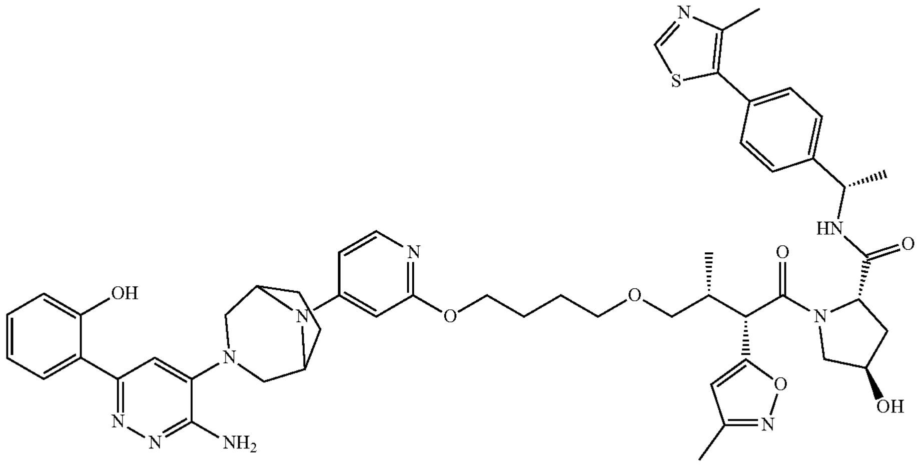 [SMILES: Cc1cc([C@@H](C(=O)N2C[C@H](O)C[C@H]2C(=O)N[C@@H](C)c2ccc(-c3scnc3C)cc2)[C@@H](C)COCCCCOc2cc(N3C4CCC3CN(c3cc(-c5ccccc5O)nnc3N)C4)ccn2)on1] |

TABLE 1C-continued
| Exemplary bifunctional degradation compounds of the present disclosure | | |
|---|---|---|
| Ex. # | Compound Name | Structure |
| 432 | (2S,4R)-1-((2R,3R)-4-(4-((4-(3-(3-amino-6-(2-hydroxyphenyl)pyridazin-4-yl)-3,8-diazabicyclo[3.2.1]octan-8-yl)pyridin-2-yl)oxy)butoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 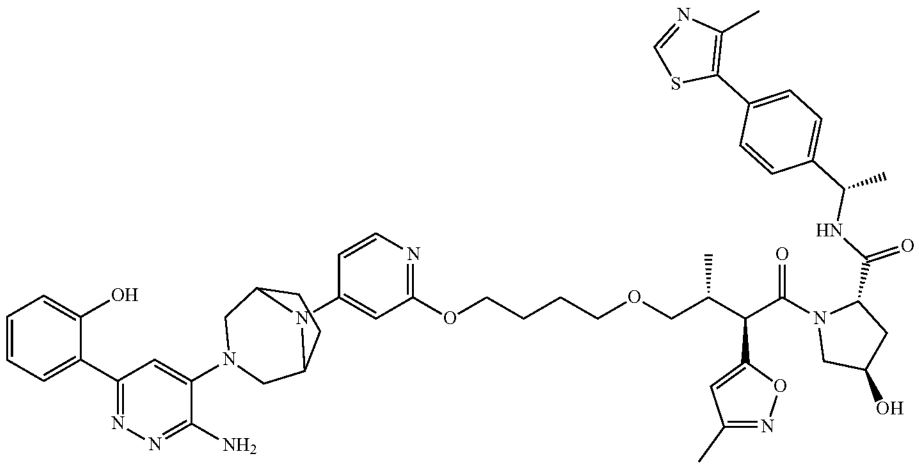 [SMILES: Cc1cc([C@H](C(=O)N2C[C@H](O)C[C@H]2C(=O)N[C@@H](C)c2ccc(-c3scnc3C)cc2)[C@@H](C)COCCCCOc2cc(N3C4CCC3CN(c3cc(-c5ccccc5O)nnc3N)C4)ccn2)on1] |

TABLE 1C-continued
| Exemplary bifunctional degradation compounds of the present disclosure | | |
|---|---|---|
| Ex. # | Compound Name | Structure |
| 433 | (2S,4R)-1-((2S)-2-(3-(4-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 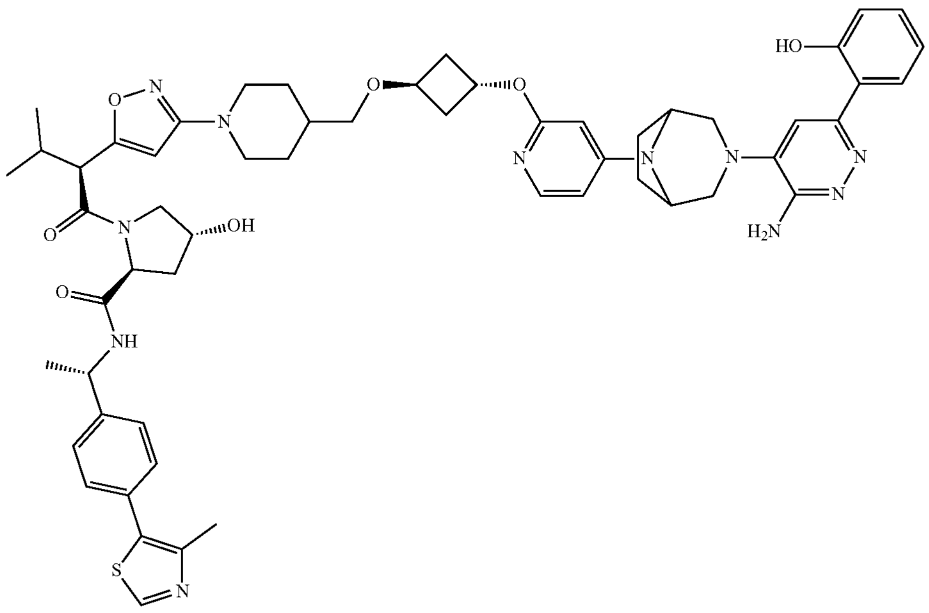 [SMILES: Cc1ncsc1-c1ccc([C@H](C)NC(=O)[C@@H]2C[C@@H](O)CN2C(=O)[C@H](c2cc(N3CCC(CO[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 434 | (2S,4R)-1-((2R)-2-(3-(4-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 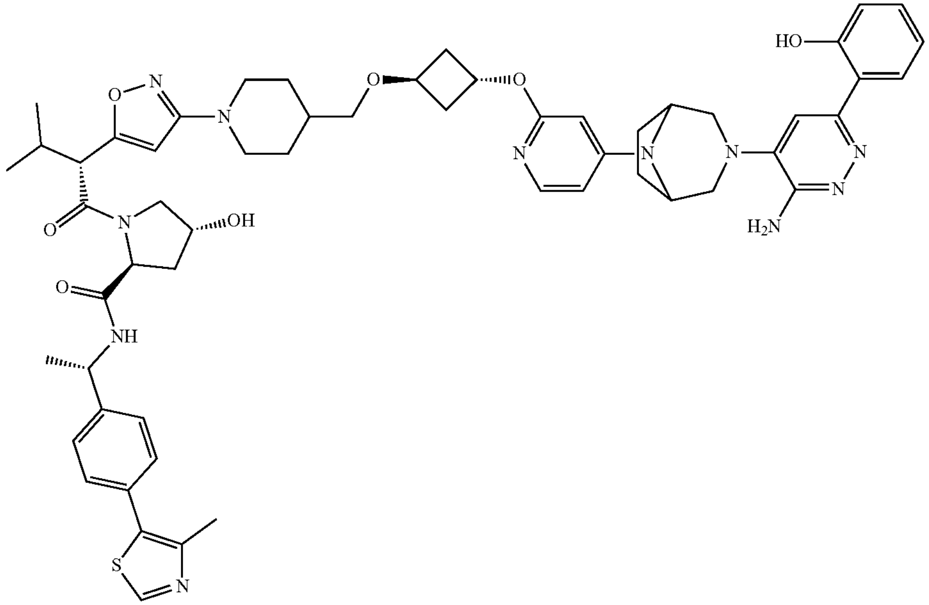 [SMILES: Cc1ncsc1-c1ccc([C@H](C)NC(=O)[C@@H]2C[C@@H](O)CN2C(=O)[C@@H](c2cc(N3CCC(CO[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 435 | (2S,4R)-1-((2S)-2-(3-(2-(1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-4-hydroxypiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 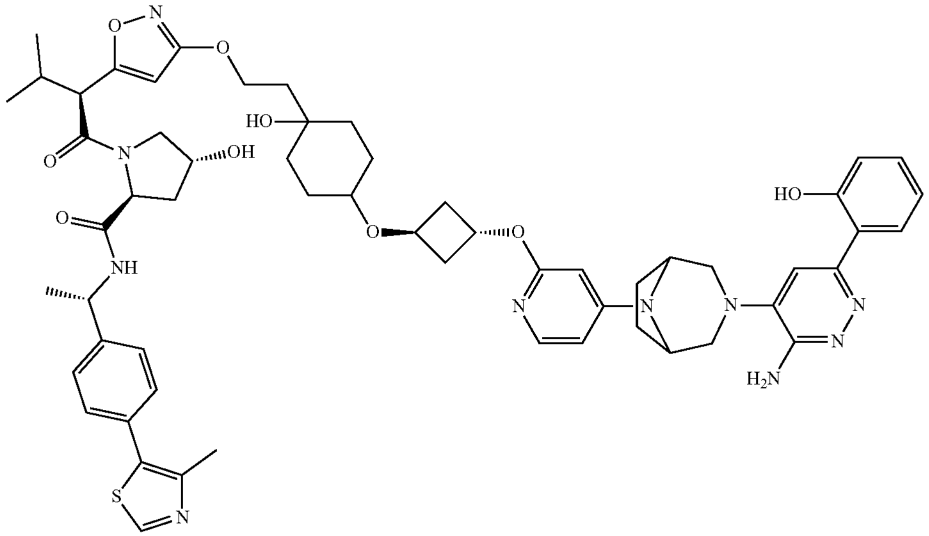 [SMILES: Cc1ncsc1-c1ccc([C@H](C)NC(=O)[C@@H]2C[C@@H](O)CN2C(=O)[C@H](c2cc(OCCC3(O)CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 436 | (2S,4R)-1-((2R)-2-(3-(2-(1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-4-hydroxypiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 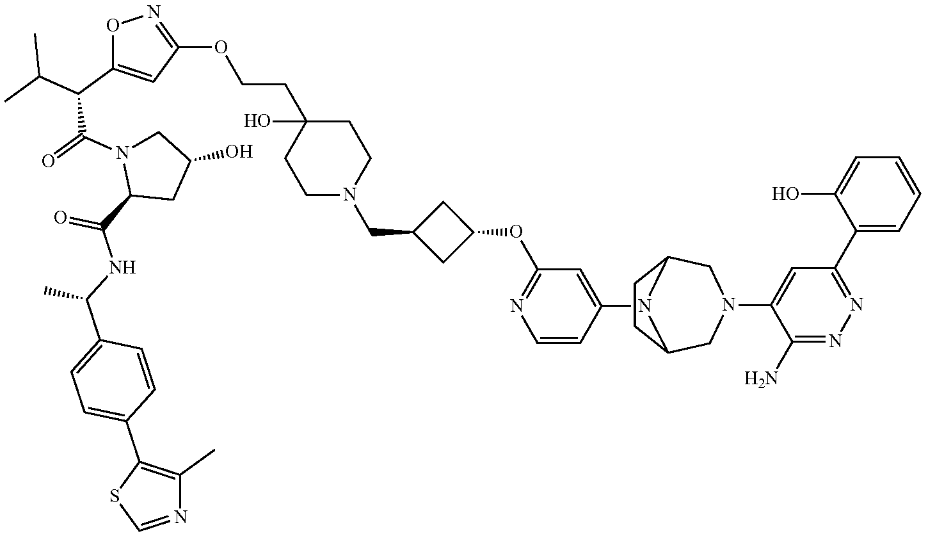 [SMILES: Cc1ncsc1-c1ccc([C@H](C)NC(=O)[C@@H]2C[C@@H](O)CN2C(=O)[C@@H](c2cc(OCCC3(O)CCN(C[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 437 | (2S,4R)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)piperazin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide | 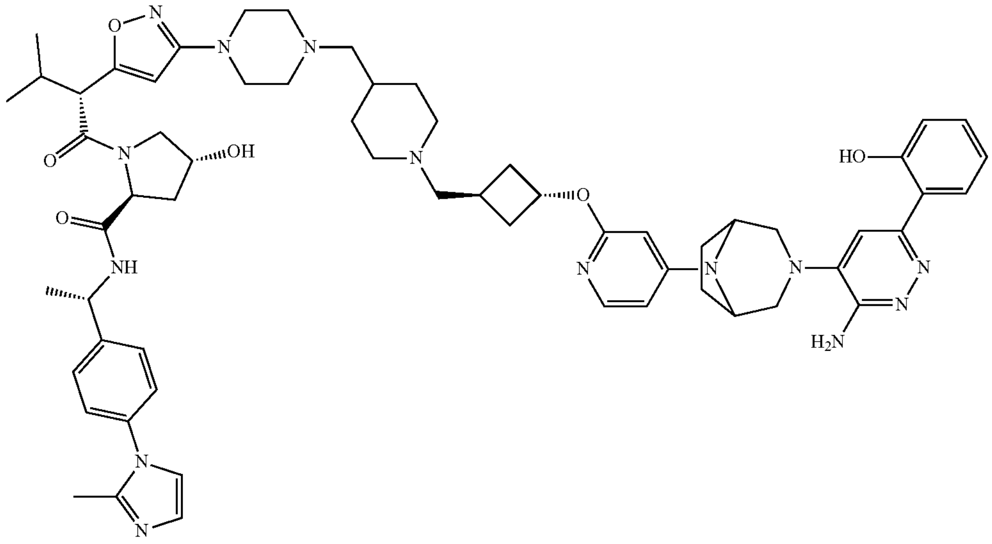 [SMILES: Cc1nccn1-c1ccc([C@H](C)NC(=O)[C@@H]2C[C@@H](O)CN2C(=O)[C@@H](c2cc(N3CCN(CC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Ex. # | Compound Name | Structure |
|---|---|---|
| | Exemplary bifunctional degradation compounds of the present disclosure | |
| 438 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((1S)-1-(4-(2,2-difluorocyclopropyl)phenyl)ethyl)-4-hydroxypyrrolidine-2-carboxamide | 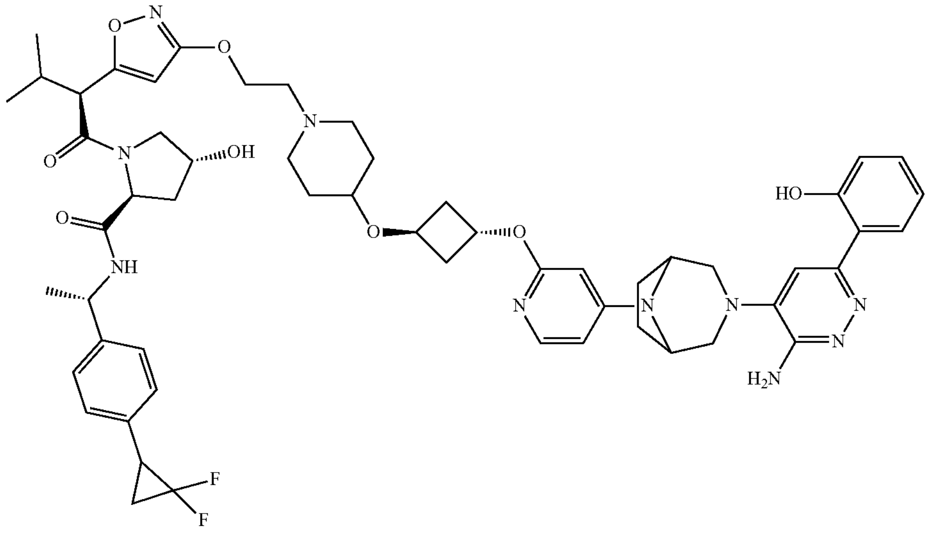 [SMILES: CC(C)[C@H](C(=O)N1C[C@H](O)C[C@H]1C(=O)N[C@@H](C)c1ccc(C2CC2(F)F)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued
| Exemplary bifunctional degradation compounds of the present disclosure | | |
|---|---|---|
| Ex. # | Compound Name | Structure |
| 439 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((1S)-1-(4-(2,2-difluorocyclopropyl)phenyl)ethyl)-4-hydroxypyrrolidine-2-carboxamide | 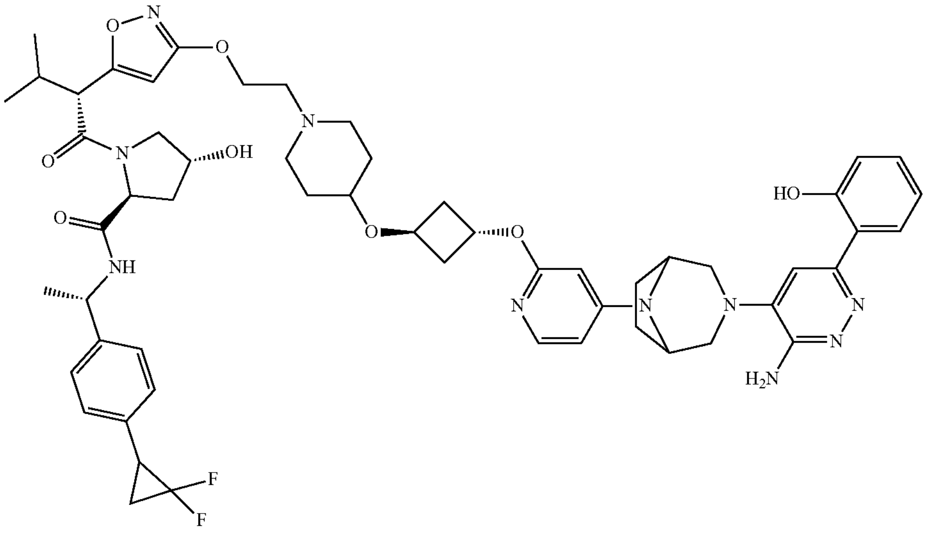 [SMILES: CC(C)[C@@H](C(=O)N1C[C@H](O)C[C@H]1C(=O)N[C@@H](C)c1ccc(C2CC2(F)F)cc1)c1cc(OCCN2CCC(O[C@H]3C[C@H](Oc4cc(N5C6CCC5CN(c5cc(-c7ccccc7O)nnc5N)C6)ccn4)C3)CC2)no1] |

TABLE 1C-continued
| Exemplary bifunctional degradation compounds of the present disclosure | | |
|---|---|---|
| Ex. # | Compound Name | Structure |
| 440 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((R)-1-(5-(4-methylthiazol-5-yl)pyrazin-2-yl)ethyl)pyrrolidine-2-carboxamide | 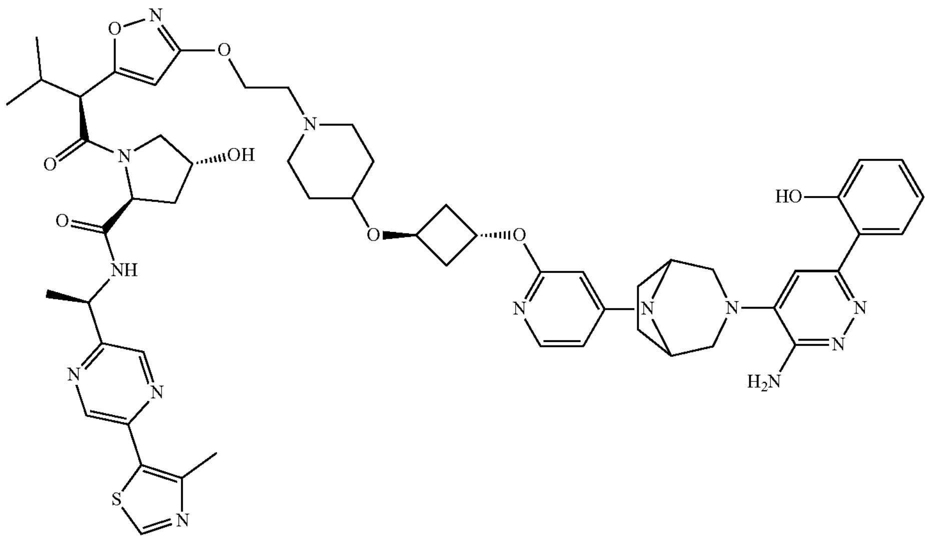 [SMILES: Cc1ncsc1-c1cnc([C@@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 441 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((R)-1-(5-(4-methylthiazol-5-yl)pyrazin-2-yl)ethyl)pyrrolidine-2-carboxamide | 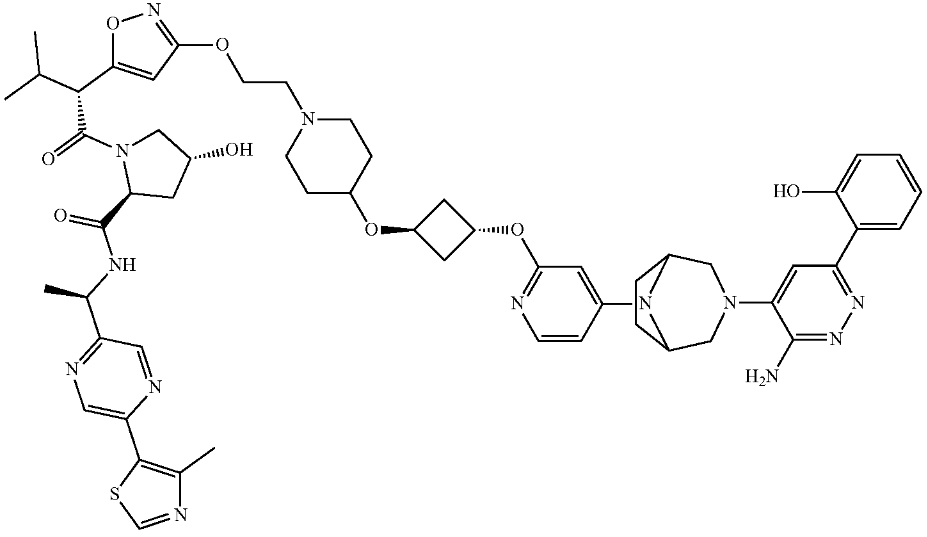 [SMILES: Cc1ncsc1-c1cnc([C@@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 442 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((R)-1-(6-(4-methylthiazol-5-yl)pyridazin-3-yl)ethyl)pyrrolidine-2-carboxamide | 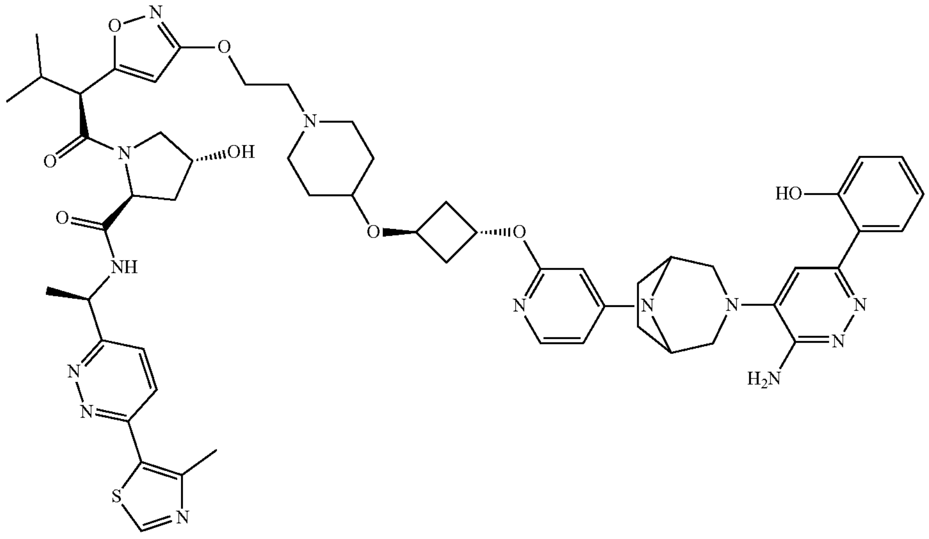 [SMILES: Cc1ncsc1-c1ccc([C@@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)nn1] |

TABLE 1C-continued
| Exemplary bifunctional degradation compounds of the present disclosure | | |
|---|---|---|
| Ex. # | Compound Name | Structure |
| 443 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((R)-1-(6-(4-methylthiazol-5-yl)pyridazin-3-yl)ethyl)pyrrolidine-2-carboxamide | 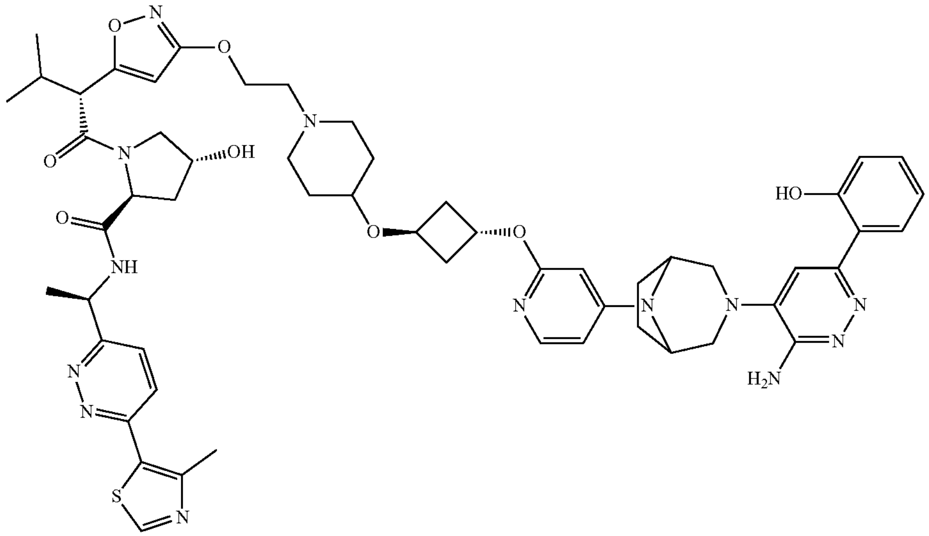 [SMILES: Cc1ncsc1-c1ccc([C@@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)nn1] |

TABLE 1C-continued
| Exemplary bifunctional degradation compounds of the present disclosure | | |
|---|---|---|
| Ex. # | Compound Name | Structure |
| 444 | (2S,4R)-1-((S)-2-(3-(2-(1-((1r,3S)-3-((9-(3-amino-6-(2-hydroxyphenyl)pyridazin-4-yl)-1-oxa-4,9-diazaspiro[5.5]undecan-4-yl)methyl)cyclobutyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 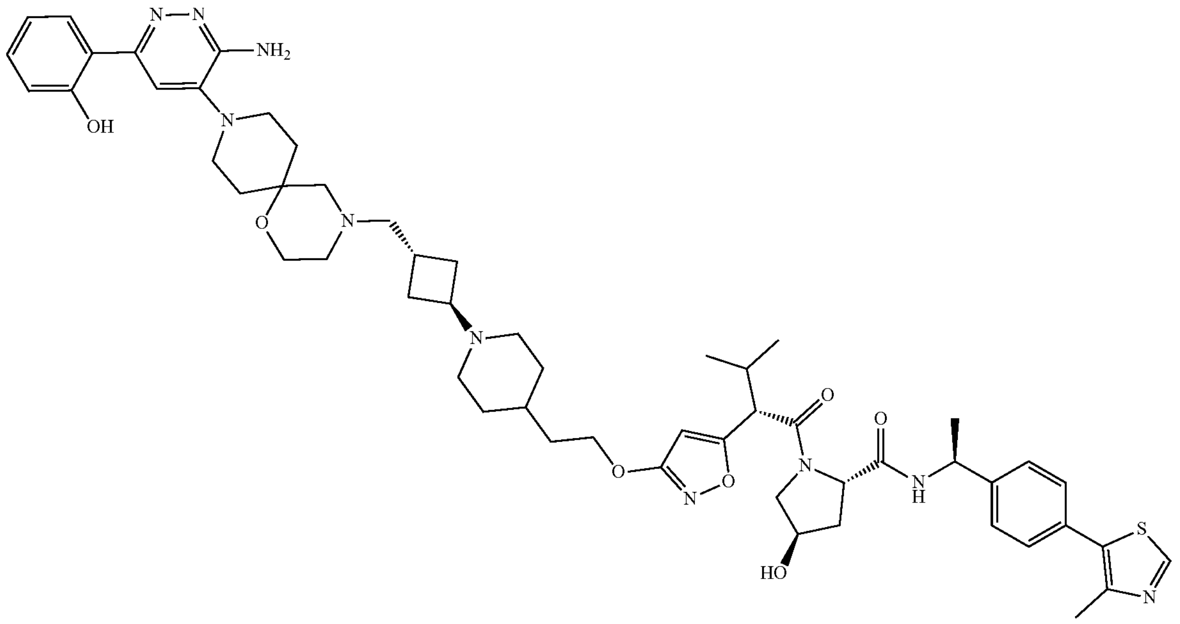 [SMILES: Cc1ncsc1-c1ccc([C@H](C)NC(=O)[C@@H]2C[C@@H](O)CN2C(=O)[C@H](c2cc(OCCC3CCN([C@H]4C[C@H](CN5CCOC6(CCN(c7cc(-c8ccccc8O)nnc7N)CC6)C5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 445 | (2S,4R)-1-((R)-2-(3-(2-(1-((1r,3R)-3-((9-(3-amino-6-(2-hydroxyphenyl)pyridazin-4-yl)-1-oxa-4,9-diazaspiro[5.5]undecan-4-yl)methyl)cyclobutyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 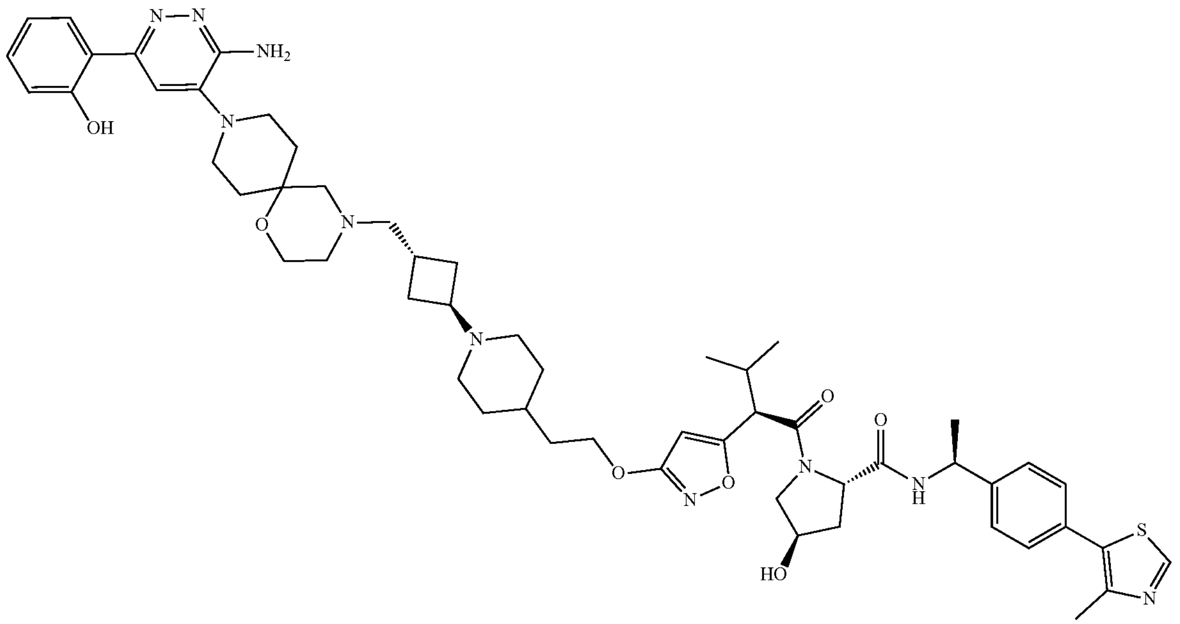 [SMILES: Cc1ncsc1-c1ccc([C@H](C)NC(=O)[C@@H]2C[C@@H](O)CN2C(=O)[C@@H](c2cc(OCCC3CCN([C@H]4C[C@H](CN5CCOC6(CCN(c7cc(-c8ccccc8O)nnc7N)CC6)C5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 446 | rac-(2R,4S)-1-((2S)-2-(3-(2-(4-((3-((4-(3-(3-amino-6-(2-hydroxyphenyl)pyridazin-4-yl)-3,8-diazabicyclo[3.2.1]octan-8-yl)pyridin-2-yl)oxy)azetidin-1-yl)methyl)-4-hydroxypiperidin-1-yl)ethoxy)isoxazol-5-yl)-3-methylbutanoyl)-4-hydroxy-N-((R)-1-(4-(4-methylthiazol-5-yl)phenyl)ethyl)pyrrolidine-2-carboxamide | 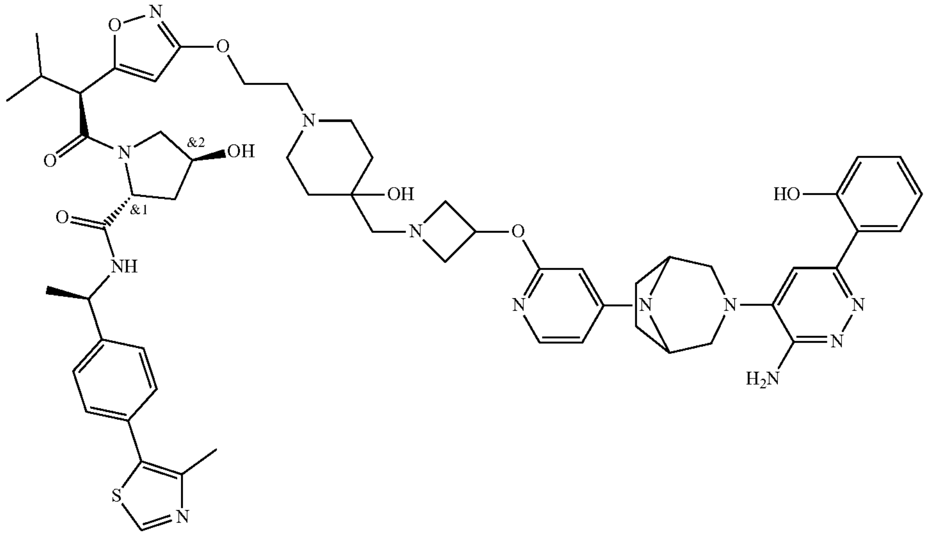 [SMILES: Cc1ncsc1-c1ccc([C@@H](C)NC(=O)[C@H]2C[C@H](O)CN2C(=O)[C@H](c2cc(OCCN3CCC(O)(CN4CC(Oc5cc(N6C7CCC6CN(c6cc(-c8ccccc8O)nnc6N)C7)ccn5)C4)CC3)no2)C(C)C)cc1] |

TABLE 1C-continued

| Exemplary bifunctional degradation compounds of the present disclosure | | |
|---|---|---|
| Ex. # | Compound Name | Structure |
| 447 | rac-(2R,4S)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)piperazin-1-yl)isoxazol-5-yl)-3-methylbutanoyl)-4-hydroxy-N-((R)-1-(4-(2-methyl-1H-imidazol-1-yl)phenyl)ethyl)pyrrolidine-2-carboxamide | 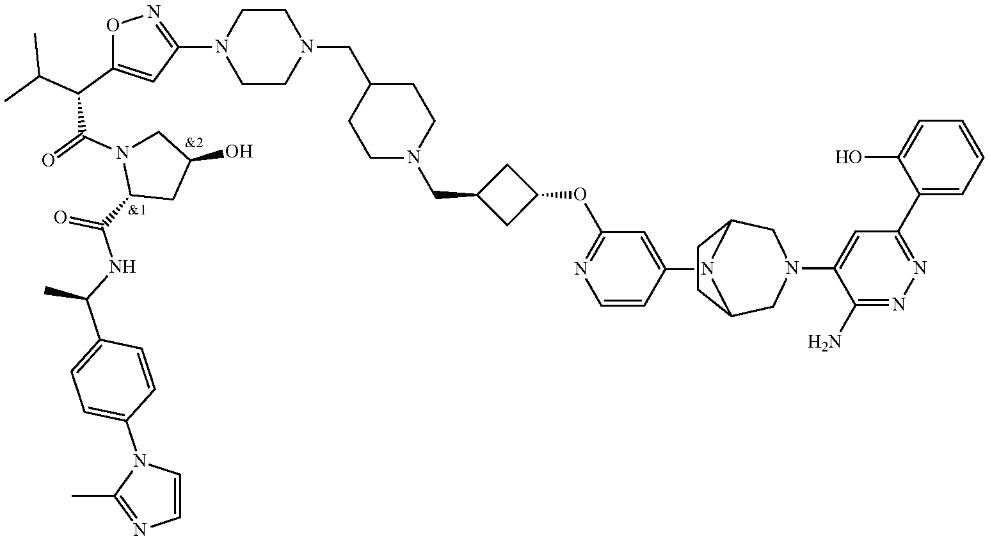 [SMILES: Cc1nccn1-c1ccc([C@@H](C)NC(=O)[C@H]2C[C@H](O)CN2C(=O)[C@@H](c2cc(N3CCN(CC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |
| 448 | (2S,4R)-1-(2-(3-(2-((2S,4S,6R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-2,6-dimethylpiperidin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 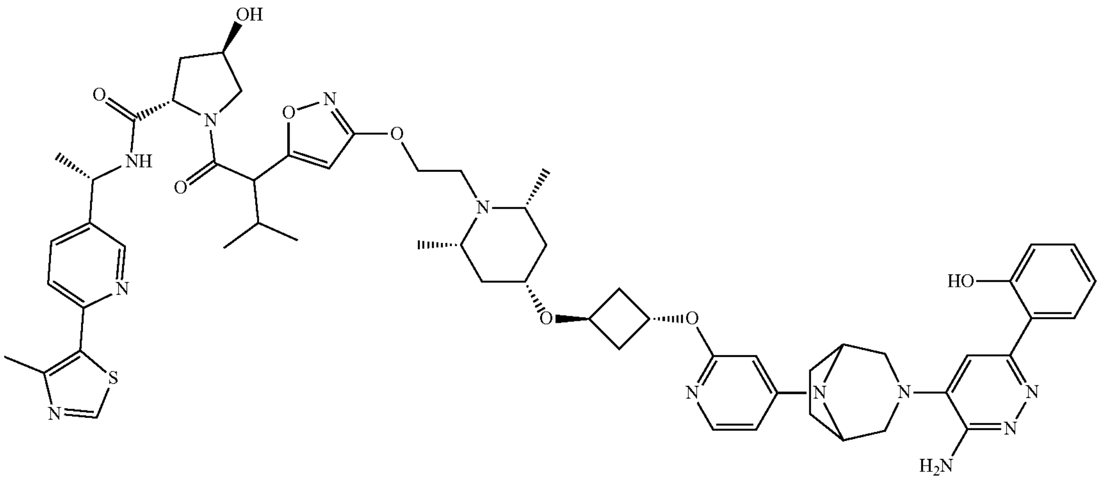 [SMILES: Cc1ncsc1-c1ccc([C@H](C)NC(=O)[C@@H]2C[C@@H](O)CN2C(=O)C(c2cc(OCCN3[C@H](C)C[C@H](O[C@H]4C[C@H](Oc5cc(N6C7CCC6CN(c6cc(-c8ccccc8O)nnc6N)C7)ccn5)C4)C[C@@H]3C)no2)C(C)C)cn1] |

TABLE 1C-continued
| Exemplary bifunctional degradation compounds of the present disclosure | | |
|---|---|---|
| Ex. # | Compound Name | Structure |
| 449 | (2S,4R)-1-((S)-2-(3-(2-(1-((1R,3R)-3-((4-((S)-1-(4-(3-amino-6-(2-hydroxyphenyl)pyridazin-4-yl)-1H-pyrazol-1-yl)ethyl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 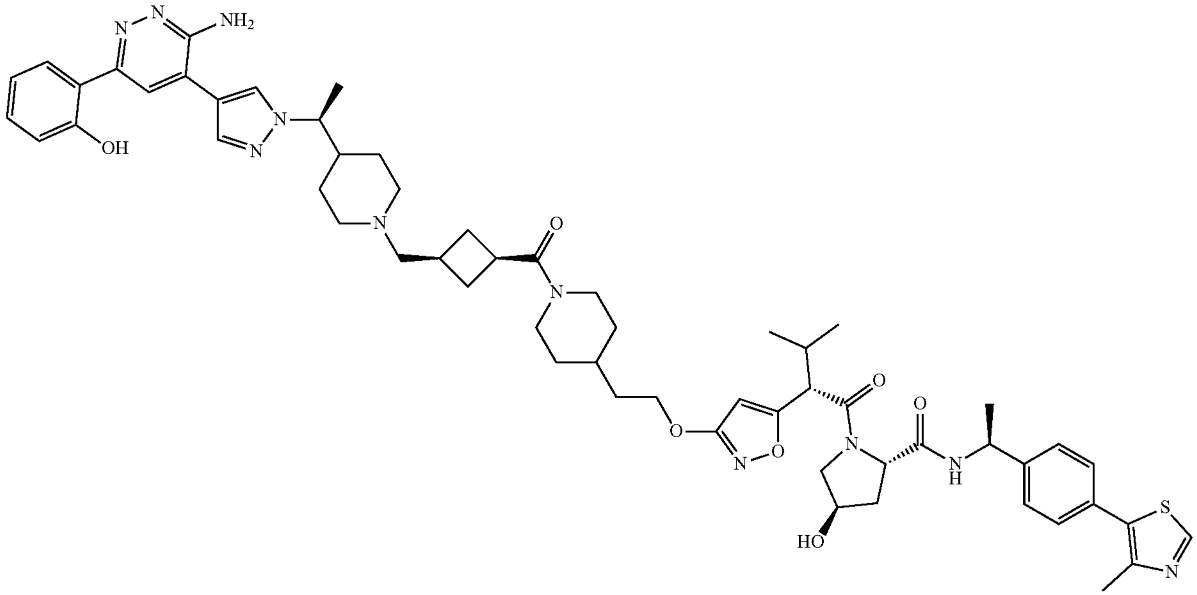 [SMILES: Cc1ncsc1-c1ccc([C@H](C)NC(=O)[C@@H]2C[C@@H](O)CN2C(=O)[C@H](c2cc(OCCC3CCN(C(=O)[C@H]4C[C@@H](CN5CCC([C@H](C)n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 450 | (2S,4R)-1-((R)-2-(3-(2-(1-((1R,3S)-3-((4-((S)-1-(4-(3-amino-6-(2-hydroxyphenyl)pyridazin-4-yl)-1H-pyrazol-1-yl)ethyl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 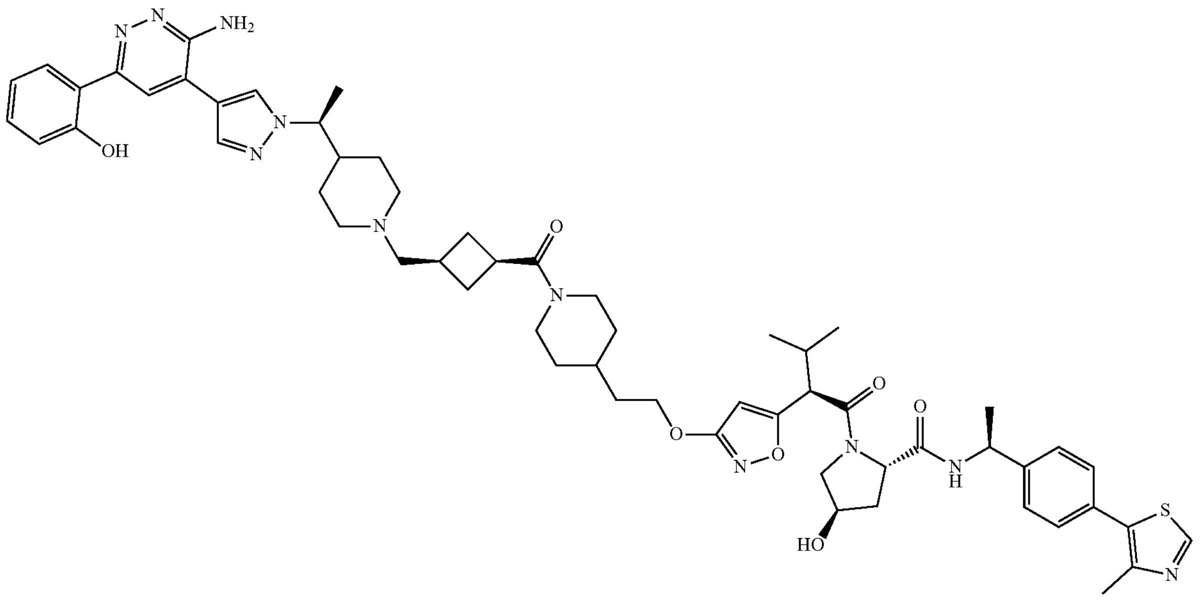 [SMILES: Cc1ncsc1-c1ccc([C@H](C)NC(=O)[C@@H]2C[C@@H](O)CN2C(=O)[C@@H](c2cc(OCCC3CCN(C(=O)[C@H]4C[C@@H](CN5CCC([C@H](C)n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 451 | (2S,4R)-1-((S)-2-(3-(2-(1-((1S,3R)-3-((4-((R)-1-(4-(3-amino-6-(2-hydroxyphenyl)pyridazin-4-yl)-1 H-pyrazol-1-yl)ethyl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 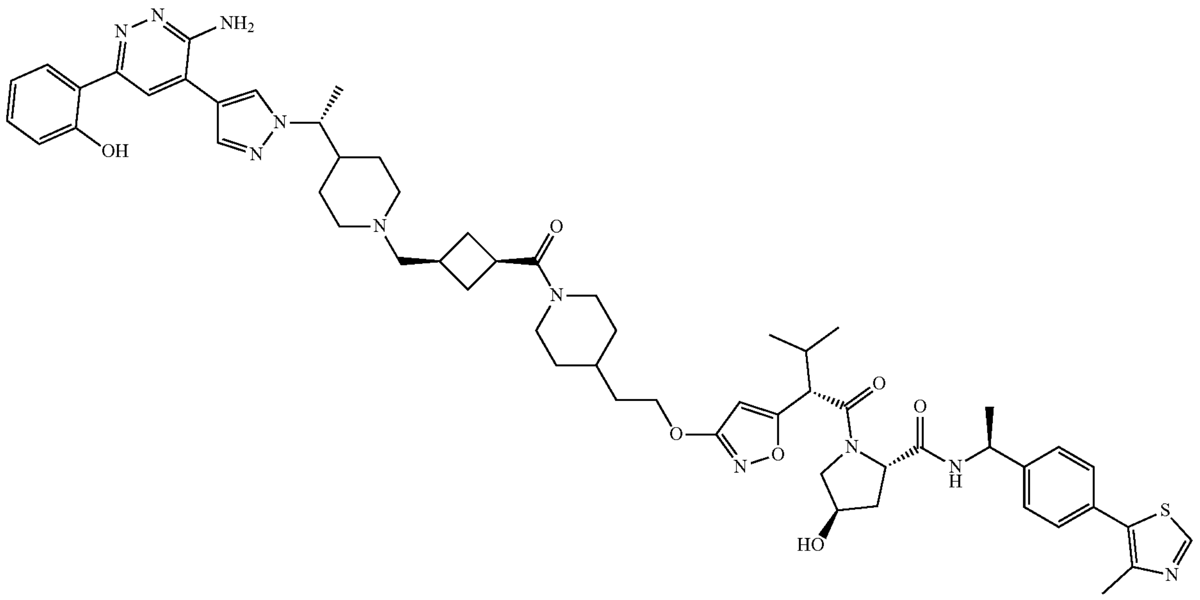 [SMILES: Cc1ncsc1-c1ccc([C@H](C)NC(=O)[C@@H]2C[C@@H](O)CN2C(=O)[C@H](c2cc(OCCC3CCN(C(=O)[C@H]4C[C@@H](CN5CCC([C@@H](C)n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 452 | (2S,4R)-1-((R)-2-(3-(2-(1-((1S,3S)-3-((4-((R)-1-(4-(3-amino-6-(2-hydroxyphenyl)pyridazin-4-yl)-1H-pyrazol-1-yl)ethyl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 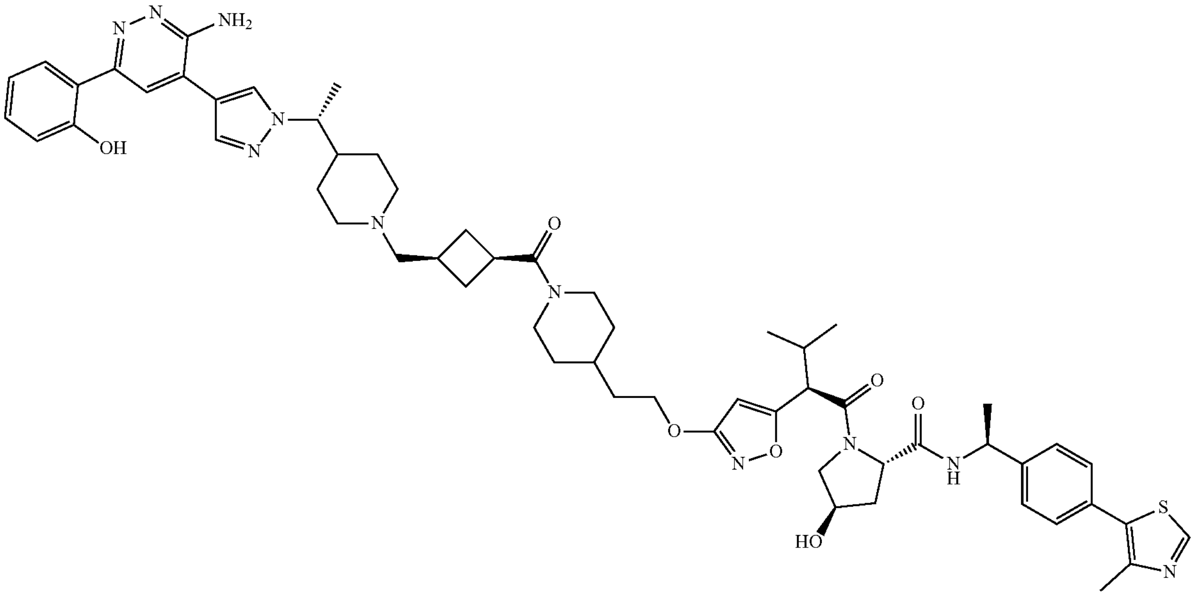 [SMILES: Cc1ncsc1-c1ccc([C@H](C)NC(=O)[C@@H]2C[C@@H](O)CN2C(=O)[C@@H](c2cc(OCCC3CCN(C(=O)[C@H]4C[C@@H](CN5CCC([C@@H](C)n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 453 | (2S,4R)-1-((S)-2-(3-(2-(1-((1S,3S)-3-((4-((S)-1-(4-(3-amino-6-(2-hydroxyphenyl)pyridazin-4-yl)-1H-pyrazol-1-yl)ethyl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 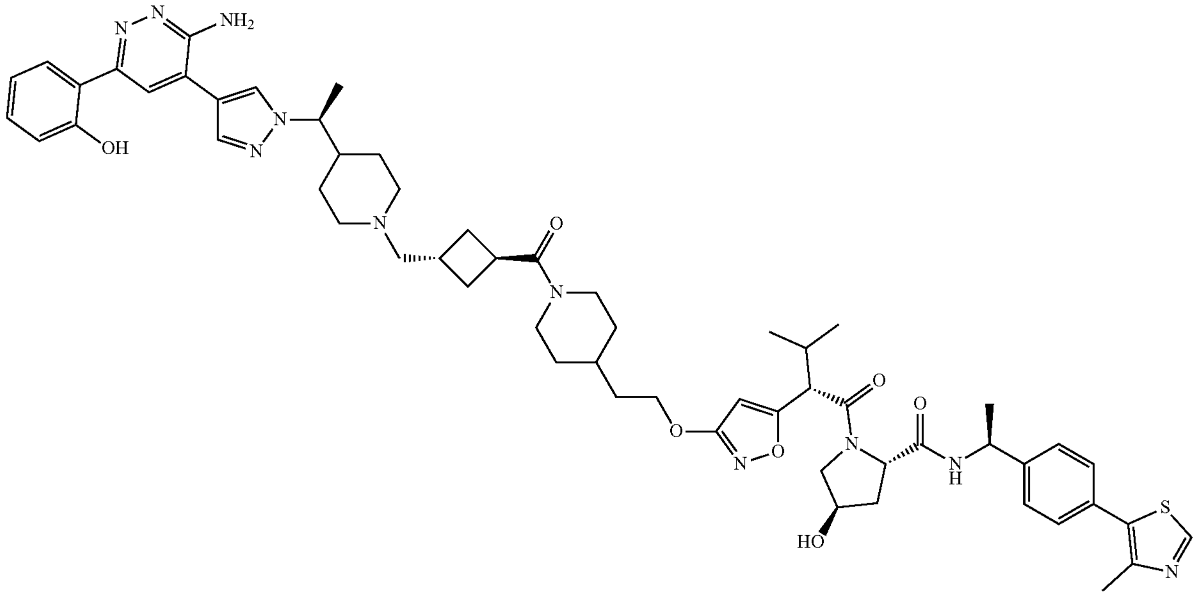 [SMILES: Cc1ncsc1-c1ccc([C@H](C)NC(=O)[C@@H]2C[C@@H](O)CN2C(=O)[C@H](c2cc(OCCC3CCN(C(=O)[C@H]4C[C@H](CN5CCC([C@H](C)n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 454 | (2S,4R)-1-((R)-2-(3-(2-(1-((1S,3R)-3-((4-((S)-1-(4-(3-amino-6-(2-hydroxyphenyl)pyridazin-4-yl)-1H-pyrazol-1-yl)ethyl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 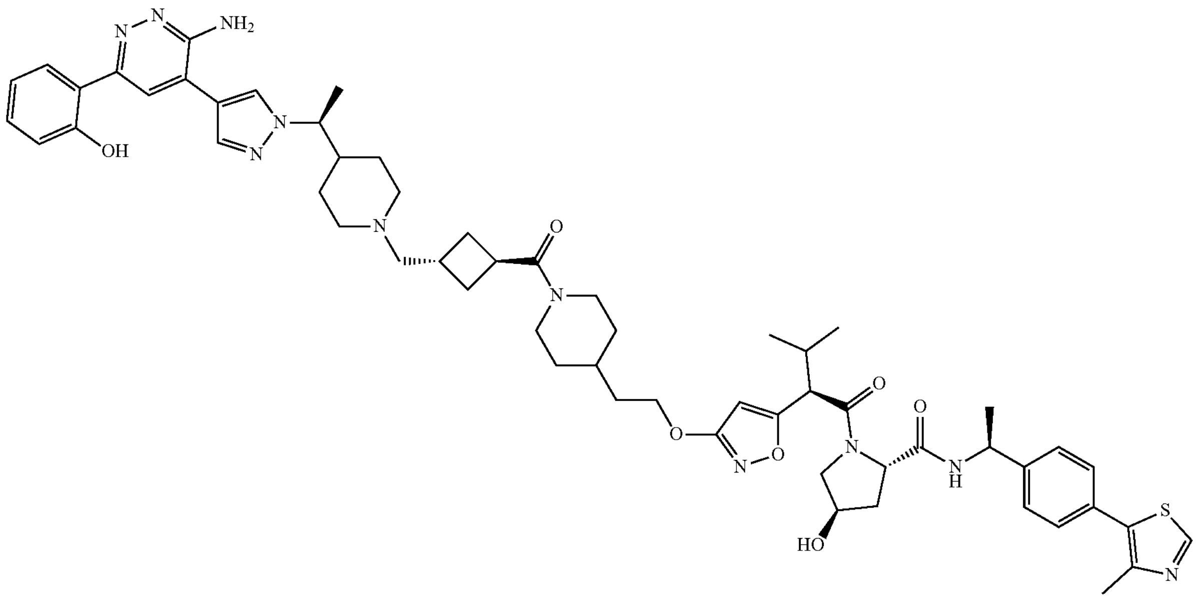 [SMILES: Cc1ncsc1-c1ccc([C@H](C)NC(=O)[C@@H]2C[C@@H](O)CN2C(=O)[C@@H](c2cc(OCCC3CCN(C(=O)[C@H]4C[C@H](CN5CCC([C@H](C)n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 455 | (2S,4R)-1-((S)-2-(3-(2-(1-((1R,3S)-3-((4-((R)-1-(4-(3-amino-6-(2-hydroxyphenyl)pyridazin-4-yl)-1H-pyrazol-1-yl)ethyl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 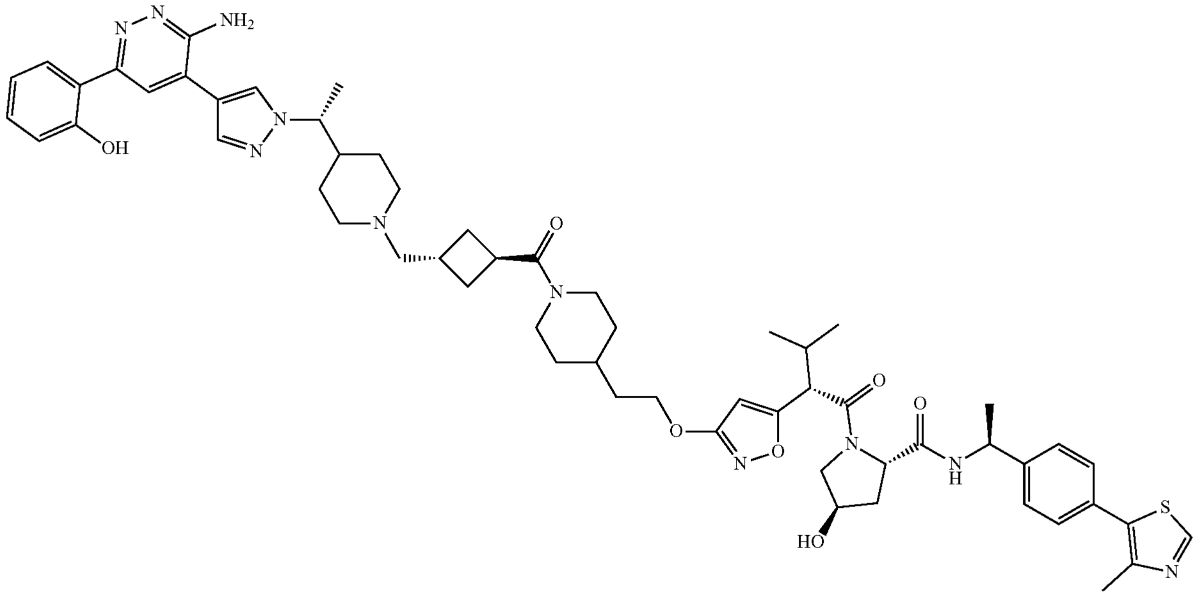 [SMILES: Cc1ncsc1-c1ccc([C@H](C)NC(=O)[C@@H]2C[C@@H](O)CN2C(=O)[C@H](c2cc(OCCC3CCN(C(=O)[C@H]4C[C@H](CN5CCC([C@@H](C)n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
| --- | --- | --- |
| Ex. # | Compound Name | Structure |
| 456 | (2S,4R)-1-((R)-2-(3-(2-(1-((1R,3R)-3-((4-((R)-1-(4-(3-amino-6-(2-hydroxyphenyl)pyridazin-4-yl)-1H-pyrazol-1-yl)ethyl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 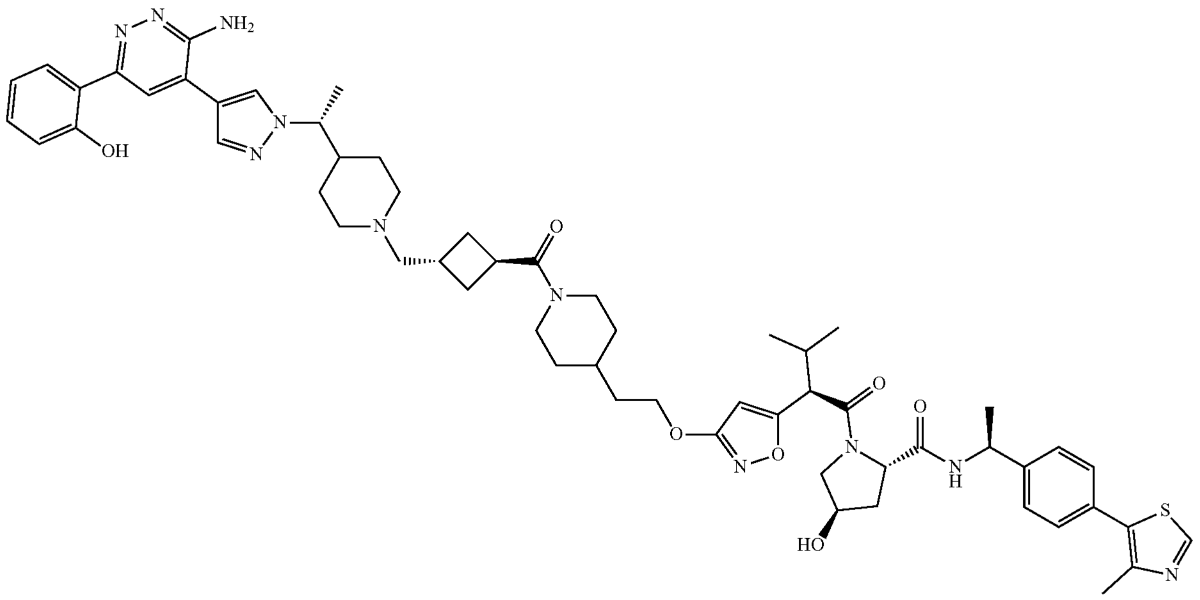 [SMILES: Cc1ncsc1-c1ccc([C@H](C)NC(=O)[C@@H]2C[C@@H](O)CN2C(=O)[C@@H](c2cc(OCCC3CCN(C(=O)[C@H]4C[C@H](CN5CCC([C@@H](C)n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 457 | (2S,4R)-1-((2S)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 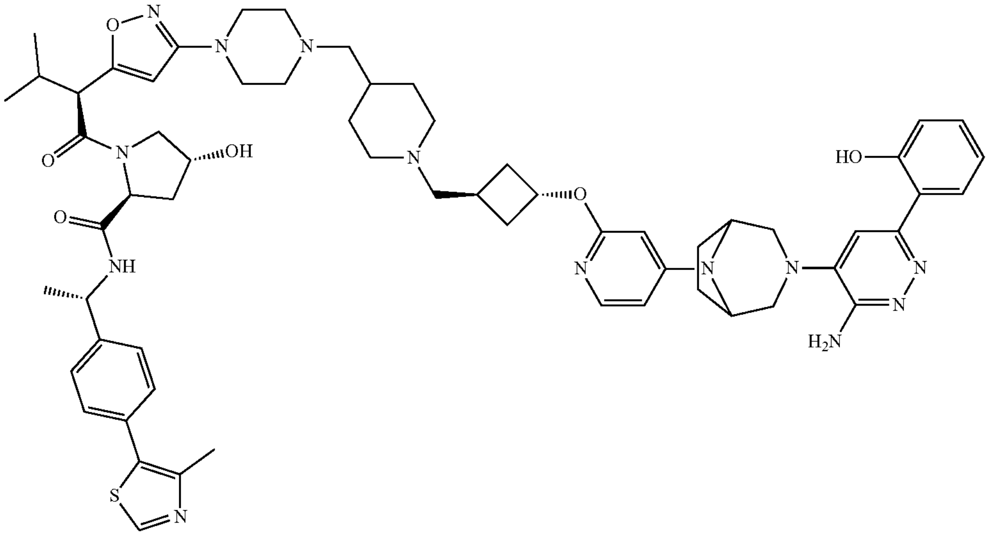 [SMILES: Cc1ncsc1-c1ccc([C@H](C)NC(=O)[C@@H]2C[C@@H](O)CN2C(=O)[C@H](c2cc(N3CCN(CC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 458 | (2S,4R)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 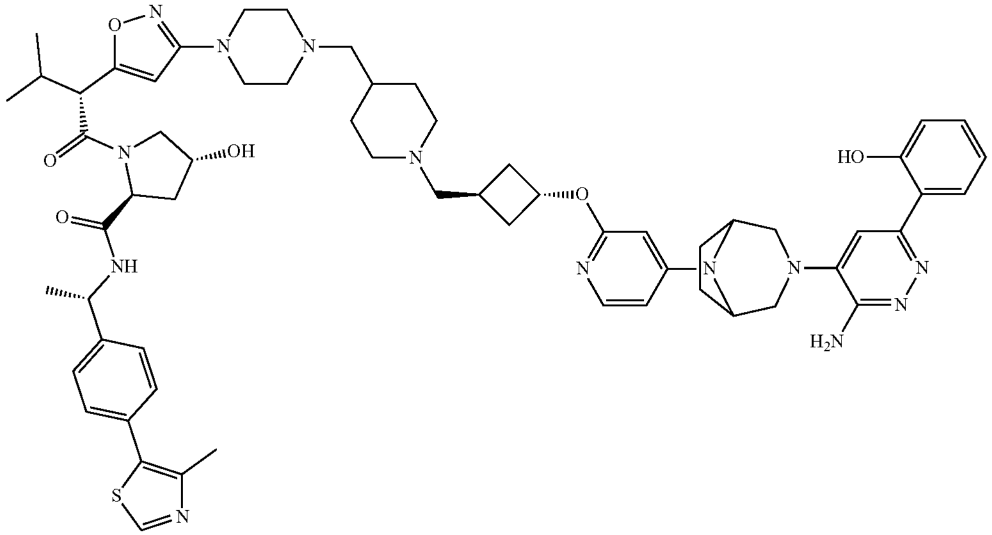 [SMILES: Cc1ncsc1-c1ccc([C@H](C)NC(=O)[C@@H]2C[C@@H](O)CN2C(=O)[C@@H](c2cc(N3CCN(CC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 459 | (3R,5S)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl dihydrogen phosphate | 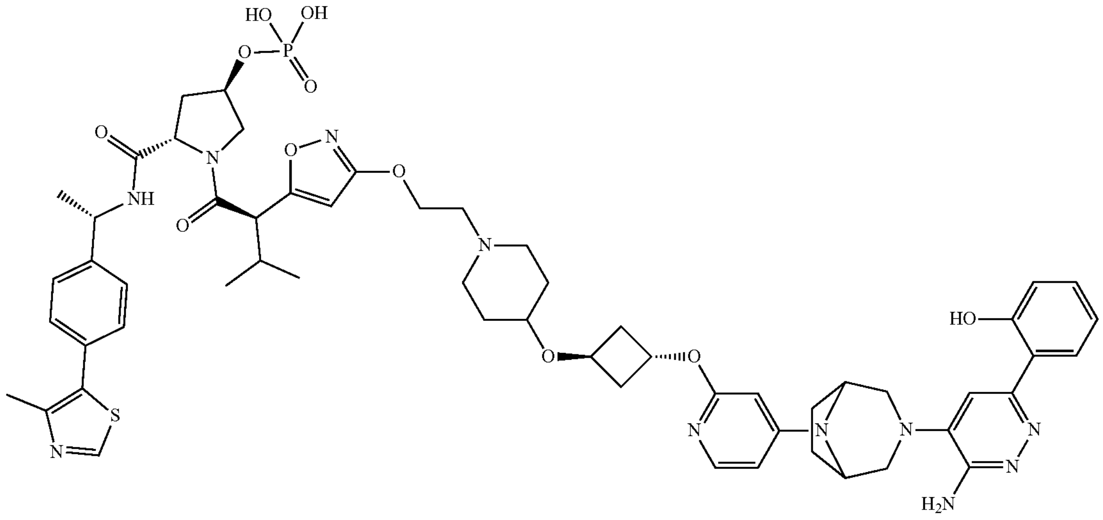 [SMILES: Cc1ncsc1-c1ccc([C@H](C)NC(=O)[C@@H]2C[C@@H](OP(=O)(O)O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 461 | (2S,4R)-1-((2S)-2-(3-(2-(4-((1r,3S)-3-(3-(3-amino-6-(2-hydroxyphenyl)pyridazin-4-yl)-3,8-diazabicyclo[3.2.1]octan-8-yl)phenoxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 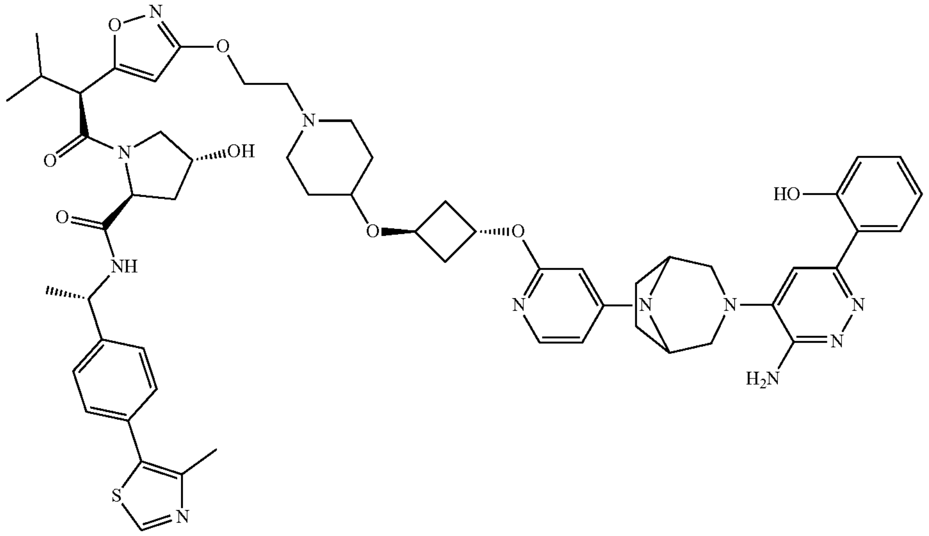 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 462 | (2S,4R)-1-((2R)-2-(3-(2-(4-((1r,3R)-3-(3-(3-amino-6-(2-hydroxyphenyl)pyridazin-4-yl)-3,8-diazabicyclo[3.2.1]octan-8-yl)phenoxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 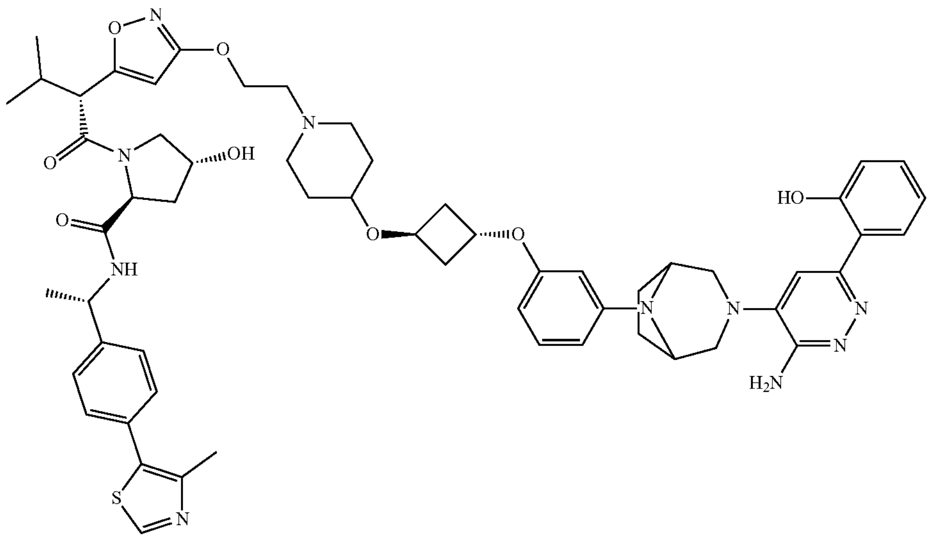 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cccc(N6C7CCC6CN(c6cc(-c8ccccc8O)nnc6N)C7)c5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 463 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyrimidin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 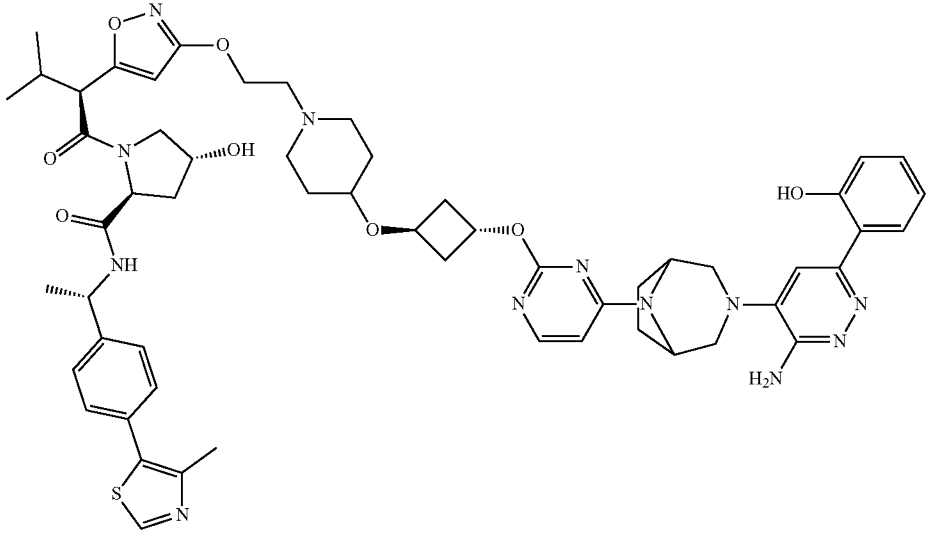 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5nccc(N6C7CCC6CN(c6cc(-c8ccccc8O)nnc6N)C7)n5)C4)CC3)no2)C(C)C)cc1] |

TABLE 1C-continued
Exemplary bifunctional degradation compounds of the present disclosure
| Ex. # | Compound Name | Structure |
| --- | --- | --- |
| 464 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyrimidin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 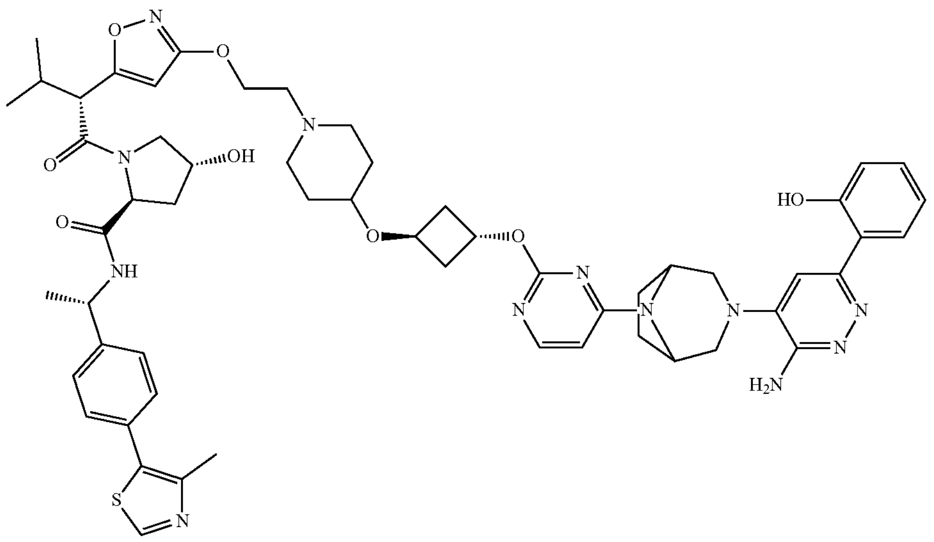 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5nccc(N6C7CCC6CN(c6cc(-c8ccccc8O)nnc6N)C7)n5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 465 | (2S,4R)-1-((S)-2-(3-(2-(1-((1s,3R)-3-((4-(4-(3-amino-6-(2-hydroxyphenyl)pyridazin-4-yl)-1H-pyrazol-1-yl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 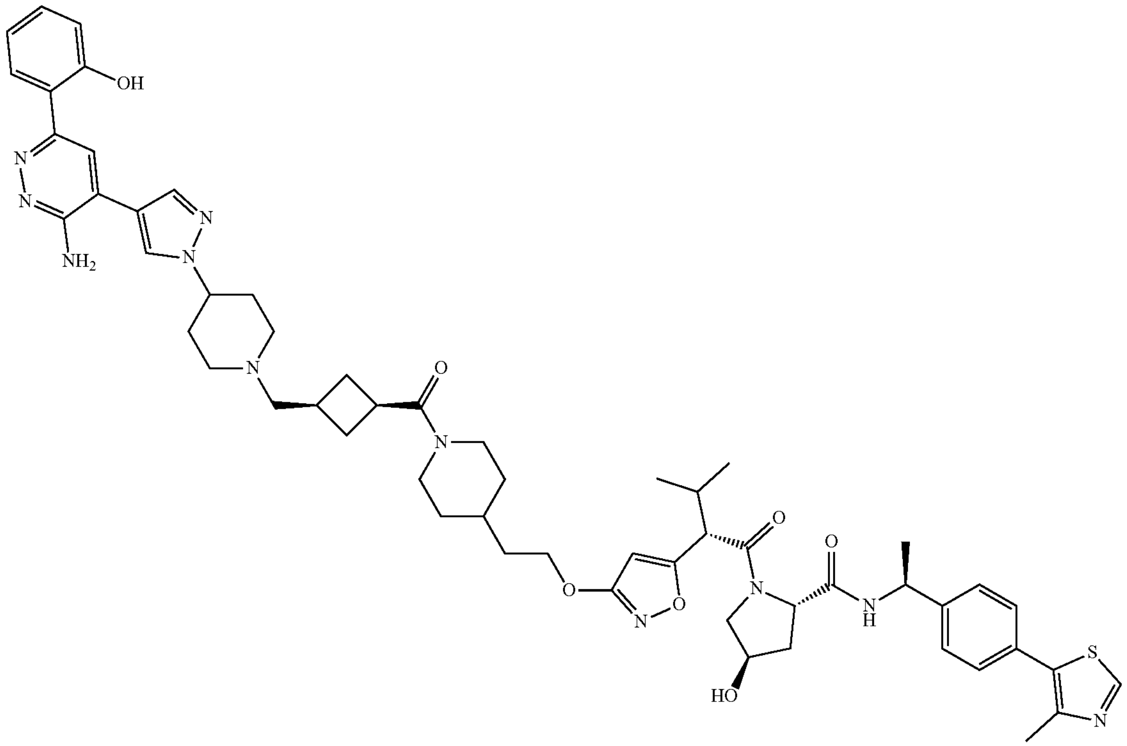 [SMILES: Cc1ncsc1-c1ccc([C@H](C)NC(=O)[C@@H]2C[C@@H](O)CN2C(=O)[C@H](c2cc(OCCC3CCN(C(=O)[C@H]4C[C@@H](CN5CCC(n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 466 | (2S,4R)-1-((R)-2-(3-(2-(1-((1s,3S)-3-((4-(4-(3-amino-6-(2-hydroxyphenyl)pyridazin-4-yl)-1H-pyrazol-1-yl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 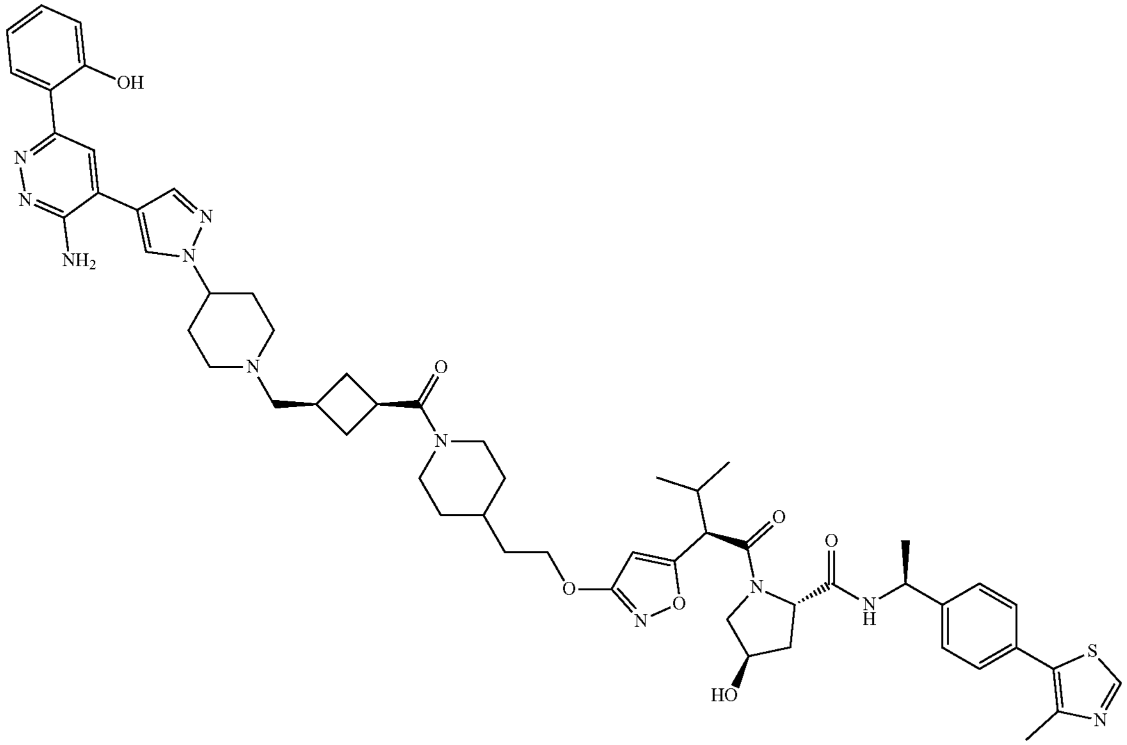 [SMILES: Cc1ncsc1-c1ccc([C@H](C)NC(=O)[C@@H]2C[C@@H](O)CN2C(=O)[C@@H](c2cc(OCCC3CCN(C(=O)[C@H]4C[C@@H](CN5CCC(n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 467 | (2S,4R)-1-((S)-2-(3-(2-(1-((1r,3S)-3-((4-(4-(3-amino-6-(2-hydroxyphenyl)pyridazin-4-yl)-1H-pyrazol-1-yl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 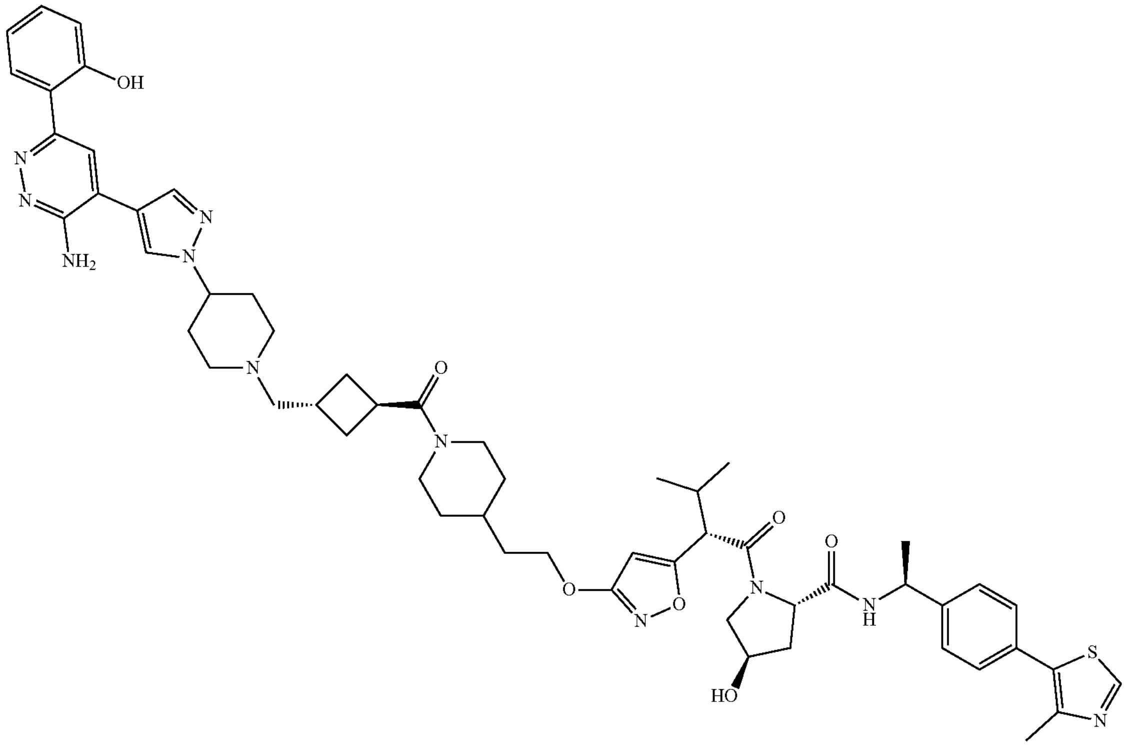 [SMILES: Cc1ncsc1-c1ccc([C@H](C)NC(=O)[C@@H]2C[C@@H](O)CN2C(=O)[C@H](c2cc(OCCC3CCN(C(=O)[C@H]4C[C@H](CN5CCC(n6cc(-c7cc(-c8ccccc8O)nnc7N)cn6)CC5)C4)CC3)no2)C(C)C)cc1] |

TABLE 1C-continued
Exemplary bifunctional degradation compounds of the present disclosure
| Ex. # | Compound Name | Structure |
|---|---|---|
| 468 | (2S,4R)-1-((R)-2-(3-(2-(1-((1r,3R)-3-((4-(4-(3-amino-6-(2-hydroxyphenyl)pyridazin-4-yl)-1H-pyrazol-1-yl)piperidin-1-yl)methyl)cyclobutane-1-carbonyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 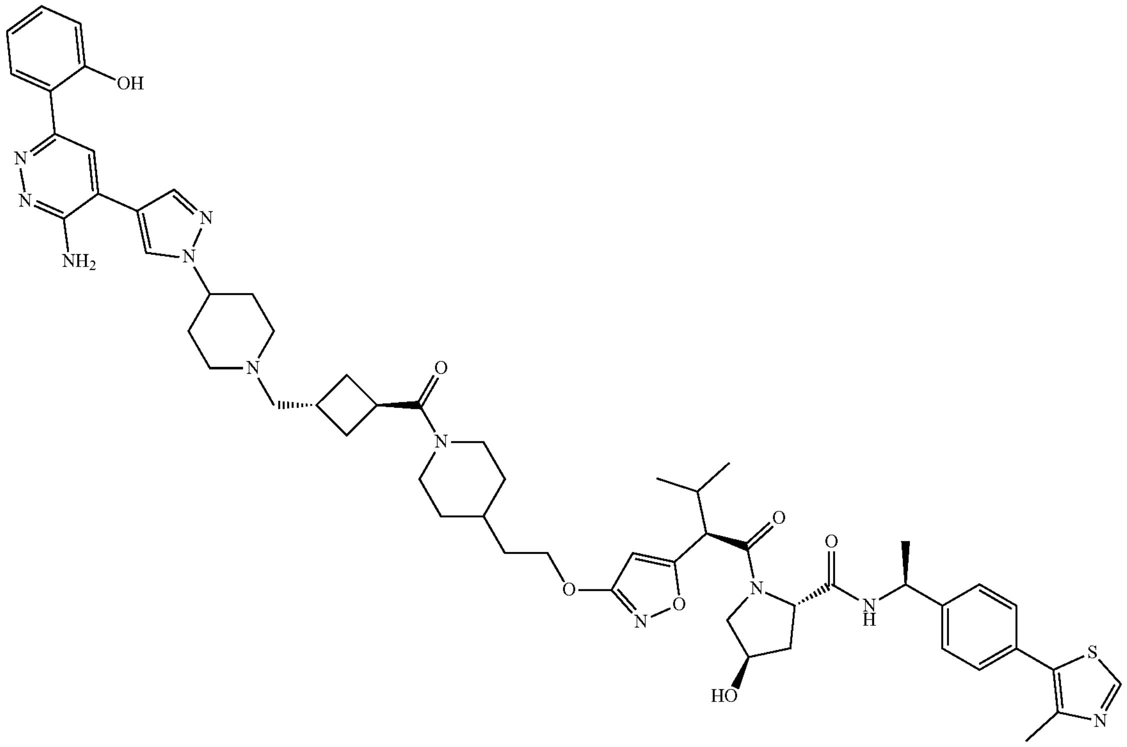 [SMILES: Cc1ncsc1-c1ccc([C@H](C)NC(=O)[C@@H]2C[C@@H](O)CN2C(=O)[C@@H](c2cc(OCCC3CCN(C(=O)[C@H]4C[C@H](CN5CCC(n6cc(-c7cc(-c8ccccc8O)nnc7N)cn6)CC5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 469 | (2S,4R)-1-((2S)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)oxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 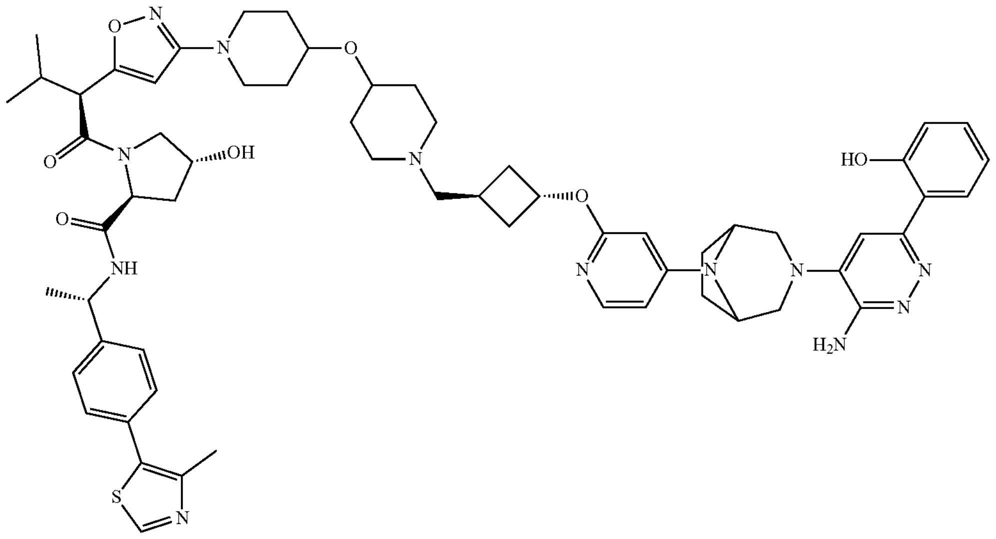 [SMILES: Cc1ncsc1-c1ccc([C@H](C)NC(=O)[C@@H]2C[C@@H](O)CN2C(=O)[C@H](c2cc(N3CCC(OC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 470 | (2S,4R)-1-((2S)-2-(3-(2-(4-((1r,3S)-3-((6-(3-(3-amino-6-(2-hydroxyphenyl)pyridazin-4-yl)-3,8-diazabicyclo[3.2.1]octan-8-yl)pyridazin-4-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 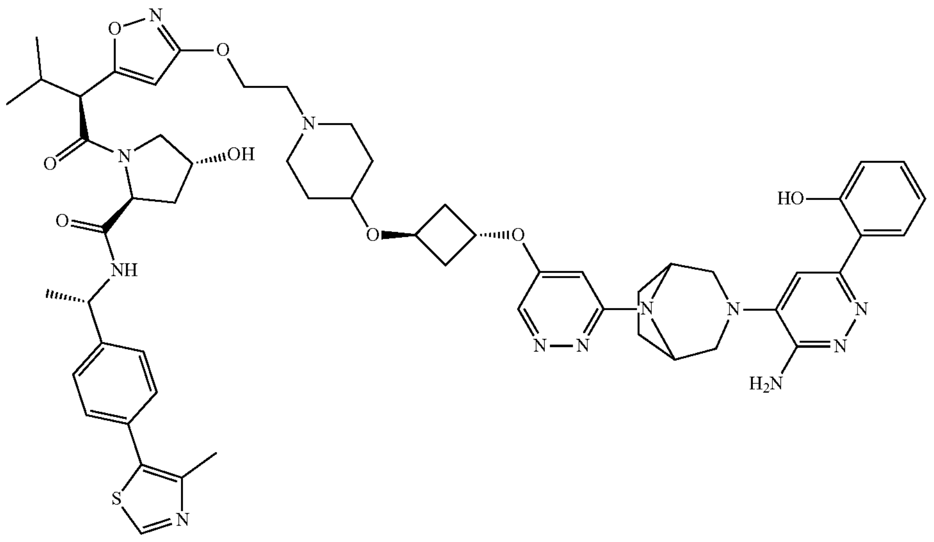 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cnnc(N6C7CCC6CN(c6cc(-c8ccccc8O)nnc6N)C7)c5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 471 | (2S,4R)-1-((2R)-2-(3-(2-(4-((1r,3R)-3-((6-(3-(3-amino-6-(2-hydroxyphenyl)pyridazin-4-yl)-3,8-diazabicyclo[3.2.1]octan-8-yl)pyridazin-4-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 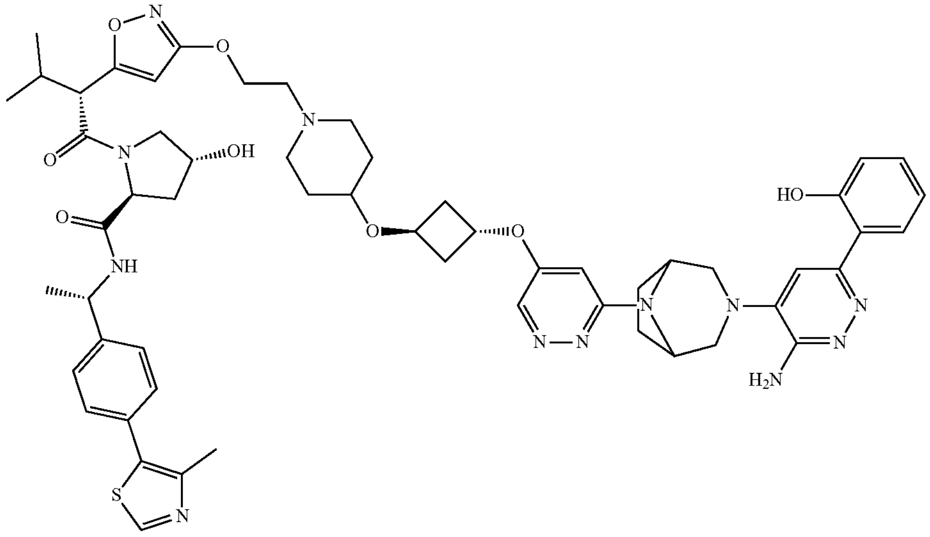 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cnnc(N6C7CCC6CN(c6cc(-c8ccccc8O)nnc6N)C7)c5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 472 | (2S,4R)-1-((2S)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 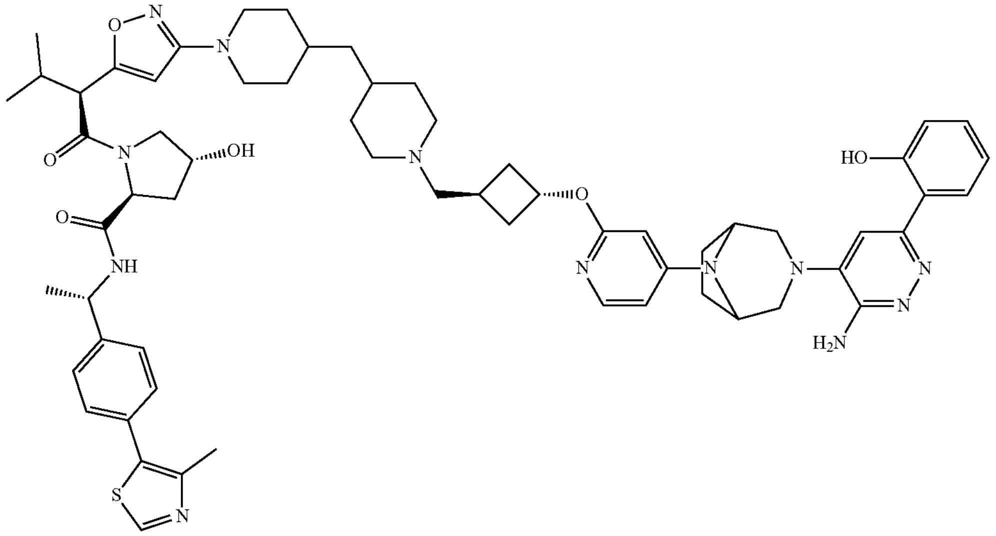 [SMILES: Cc1ncsc1-c1ccc([C@H](C)NC(=O)[C@@H]2C[C@@H](O)CN2C(=O)[C@H](c2cc(N3CCC(CC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 473 | (2S,4R)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 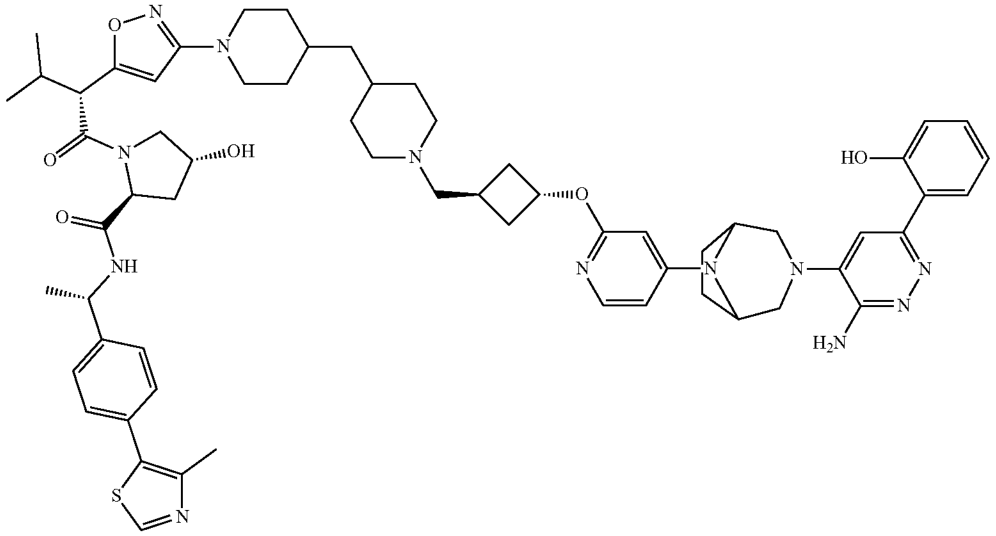 [SMILES: Cc1ncsc1-c1ccc([C@H](C)NC(=O)[C@@H]2C[C@@H](O)CN2C(=O)[C@@H](c2cc(N3CCC(CC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 474 | (2S,4R)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)oxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 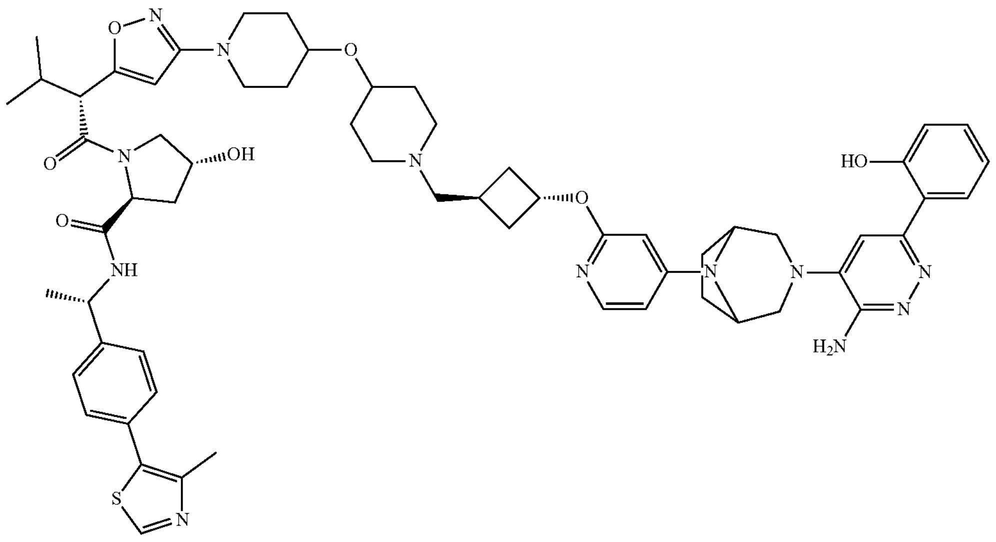 [SMILES: Cc1ncsc1-c1ccc([C@H](C)NC(=O)[C@@H]2C[C@@H](O)CN2C(=O)[C@@H](c2cc(N3CCC(OC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 475 | (2S,4R)-1-((2S)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)oxy)piperidin-1-yl)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 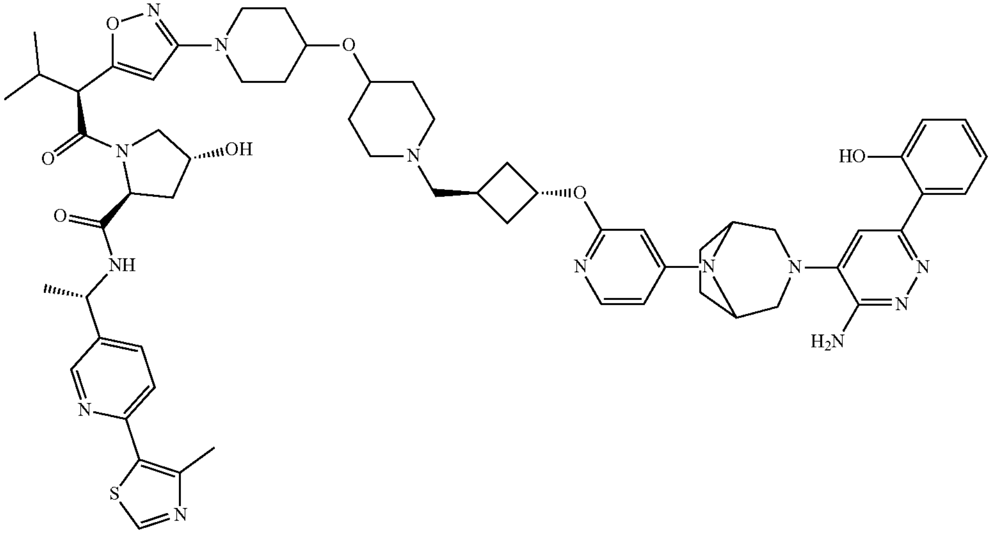 [SMILES: Cc1ncsc1-c1ccc([C@H](C)NC(=O)[C@@H]2C[C@@H](O)CN2C(=O)[C@H](c2cc(N3CCC(OC4CCN(C[C@H]5C[C@H](Oc6cc(N7C8CCC7CN(c7cc(-c9ccccc9O)nnc7N)C8)ccn6)C5)CC4)CC3)no2)C(C)C)cn1] |

TABLE 1C-continued
| Exemplary bifunctional degradation compounds of the present disclosure | | |
|---|---|---|
| Ex. # | Compound Name | Structure |
| 476 | (2S,4R)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)oxy)piperidin-1-yl)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 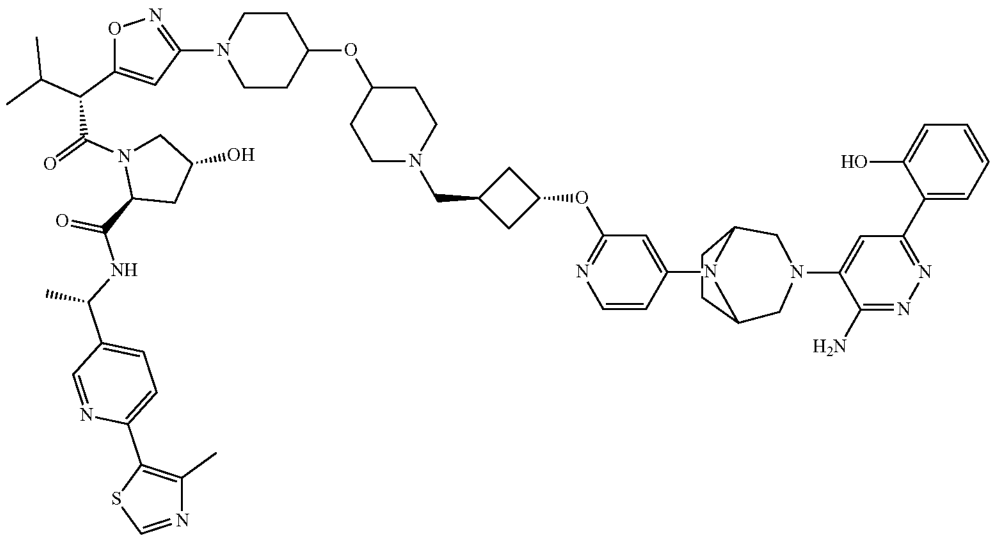 [SMILES: Cc1ncsc1-c1ccc([C@H](C)NC(=O)[C@@H]2C[C@@H](O)CN2C(=O)[C@@H](c2cc(N3CCC(OC4CCN(C[C@H]5C[C@H](Oc6cc(N7C8CCC7CN(c7cc(-c9ccccc9O)nnc7N)C8)ccn6)C5)CC4)CC3)no2)C(C)C)cn1] |

TABLE 1C-continued
| Exemplary bifunctional degradation compounds of the present disclosure | | |
|---|---|---|
| Ex. # | Compound Name | Structure |
| 477 | (2S,4R)-1-((2S)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)oxy)piperidin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide | 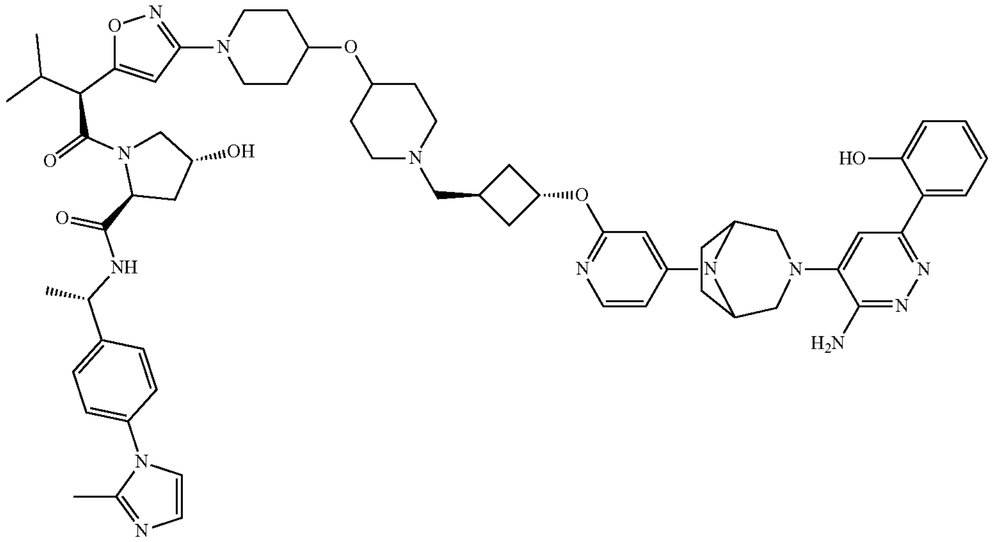 [SMILES: Cc1nccn1-c1ccc([C@H](C)NC(=O)[C@@H]2C[C@@H](O)CN2C(=O)[C@H](c2cc(N3CCC(OC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
| Exemplary bifunctional degradation compounds of the present disclosure | | |
|---|---|---|
| Ex. # | Compound Name | Structure |
| 478 | (2S,4R)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)oxy)piperidin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide | 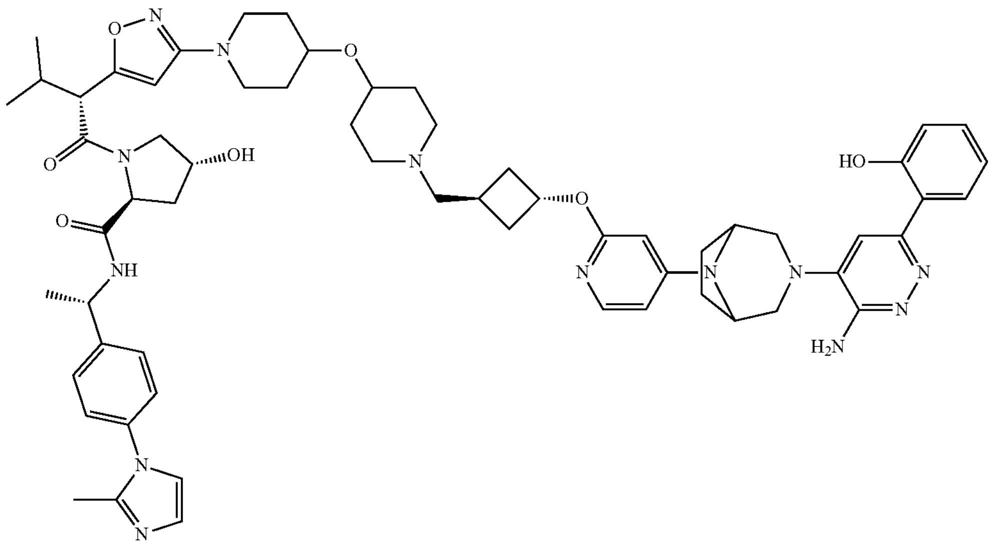 [SMILES: Cc1nccn1-c1ccc([C@H](C)NC(=O)[C@@H]2C[C@@H](O)CN2C(=O)[C@@H](c2cc(N3CCC(OC4CCN(C[C@H]5C[C@H](Oc6cc(N7C8CCC7CN(c7cc(-c9ccccc9O)nnc7N)C8)ccn6)C5)CC4)CC3)no2)C(C)C)cc1] |

TABLE 1C-continued
Exemplary bifunctional degradation compounds of the present disclosure
| Ex. # | Compound Name | Structure |
| --- | --- | --- |
| 479 | (2S,4R)-1-((2S)-2-(3-(((1R,2R)-2-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)cyclopropyl)methoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 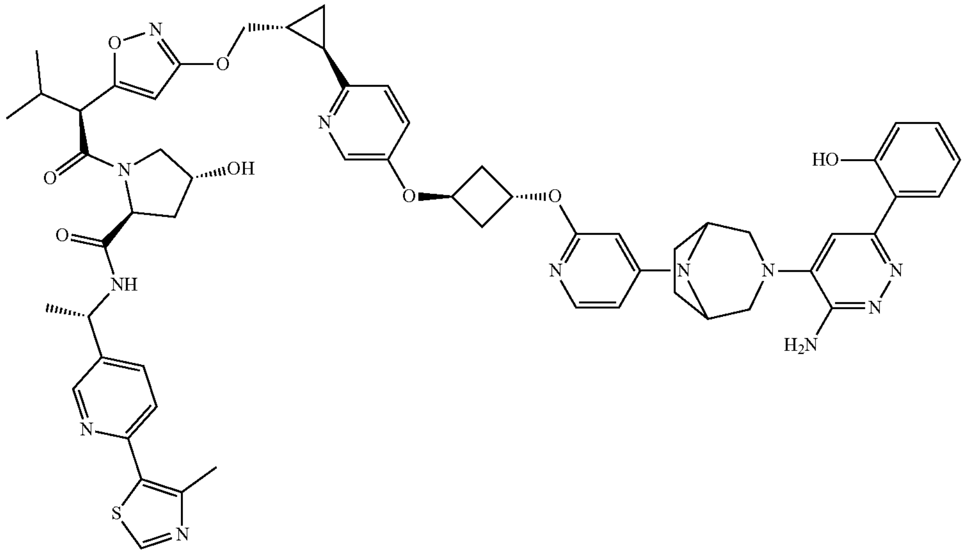 [SMILES: Cc1ncsc1-c1ccc([C@H](C)NC(=O)[C@@H]2C[C@@H](O)CN2C(=O)[C@H](c2cc(OC[C@@H]3C[C@H]3c3ccc(O[C@H]4C[C@H](Oc5cc(N6C7CCC6CN(c6cc(-c8ccccc8O)nnc6N)C7)ccn5)C4)cn3)no2)C(C)C)cn1] |

TABLE 1C-continued
| Exemplary bifunctional degradation compounds of the present disclosure | | |
|---|---|---|
| Ex. # | Compound Name | Structure |
| 480 | (2S,4R)-1-((2R)-2-(3-(((1R,2R)-2-(5-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyridin-2-yl)cyclopropyl)methoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 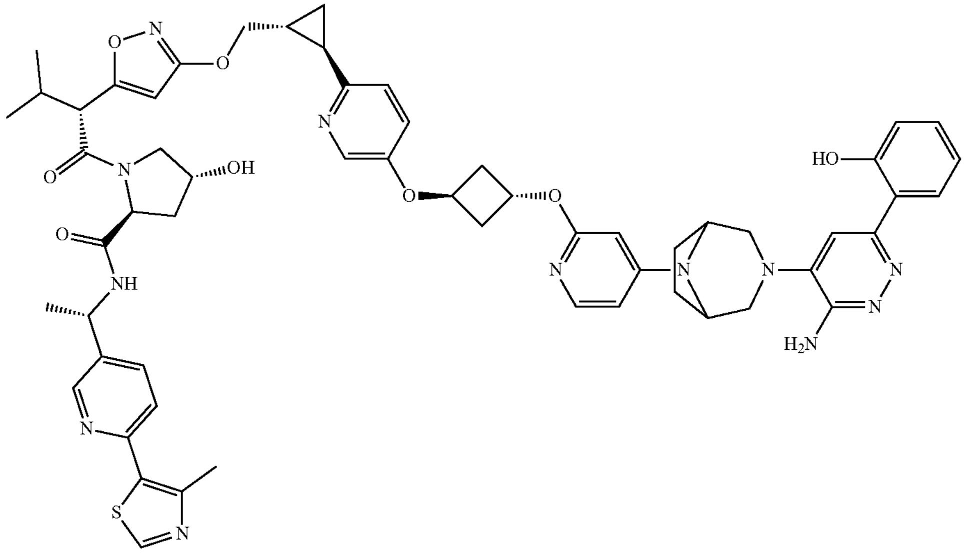 [SMILES: Cc1ncsc1-c1ccc([C@H](C)NC(=O)[C@@H]2C[C@@H](O)CN2C(=O)[C@@H](c2cc(OC[C@@H]3C[C@H]3c3ccc(O[C@H]4C[C@H](Oc5cc(N6C7CCC6CN(c6cc(-c8ccccc8O)nnc6N)C7)ccn5)C4)cn3)no2)C(C)C)cn1] |

TABLE 1C-continued

| Exemplary bifunctional degradation compounds of the present disclosure | | |
|---|---|---|
| Ex. # | Compound Name | Structure |
| 481 | (2S,4R)-1-((2S,3R)-4-((1s,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 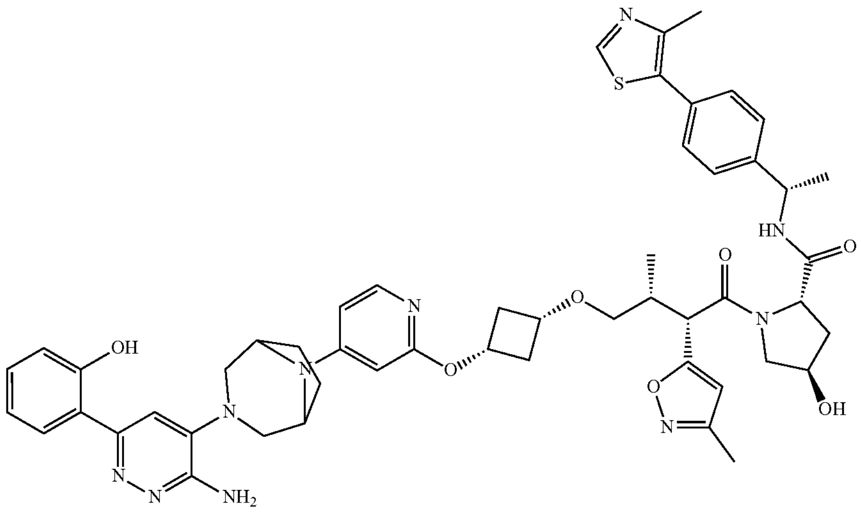 [SMILES: Cc1cc([C@@H](C(=O)N2C[C@H](O)C[C@H]2C(=O)N[C@@H](C)c2ccc(-c3scnc3C)cc2)[C@@H](C)CO[C@H]2C[C@@H](Oc3cc(N4C5CCC4CN(c4cc(-c6ccccc6O)nnc4N)C5)ccn3)C2)on1] |
| 482 | (2S,4R)-1-((2R,3R)-4-((1s,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 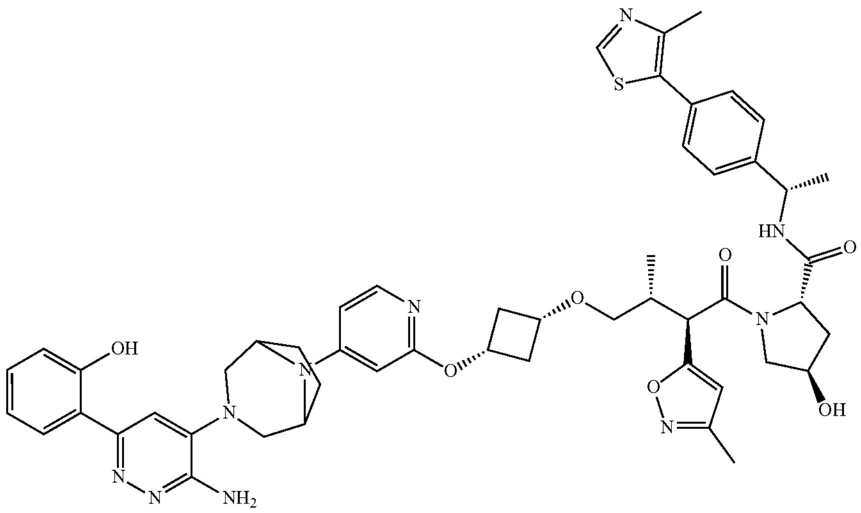 [SMILES: Cc1cc([C@H](C(=O)N2C[C@H](O)C[C@H]2C(=O)N[C@@H](C)c2ccc(-c3scnc3C)cc2)[C@@H](C)CO[C@H]2C[C@@H](Oc3cc(N4C5CCC4CN(c4cc(-c6ccccc6O)nnc4N)C5)ccn3)C2)on1] |

TABLE 1C-continued
| Exemplary bifunctional degradation compounds of the present disclosure | | |
|---|---|---|
| Ex. # | Compound Name | Structure |
| 483 | (2S,4R)-1-((2S)-2-(3-(3-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-2,2-difluoropropoxy)isoxazol-5-yl)-3-methylbutanoyl)-4-hydroxy-N-((S)-1-(4-(4-methylthiazol-5-yl)phenyl)ethyl)pyrrolidine-2-carboxamide | 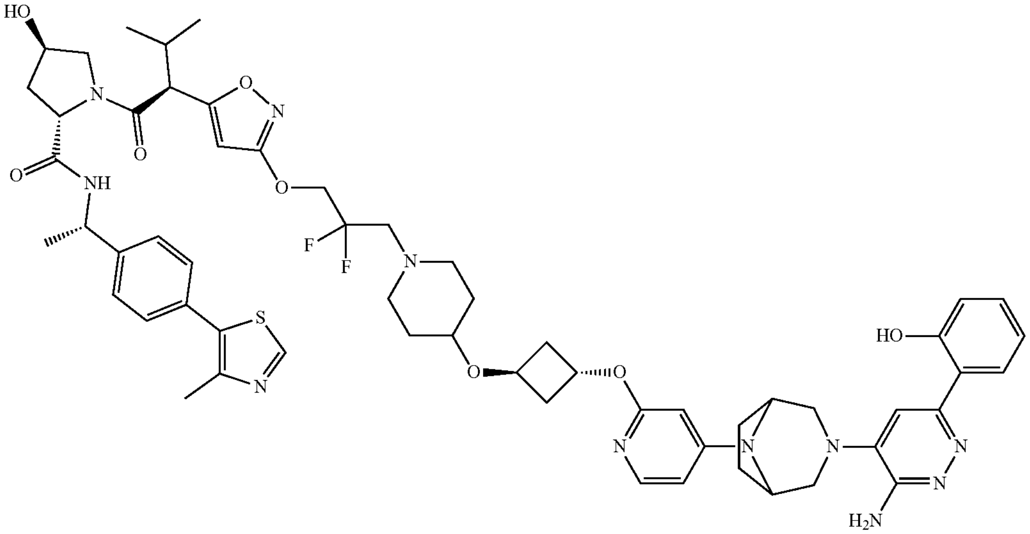 |

TABLE 1C-continued
| Exemplary bifunctional degradation compounds of the present disclosure | | |
|---|---|---|
| Ex. # | Compound Name | Structure |
| 484 | (2S,4R)-1-((2R)-2-(3-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-2,2-difluoropropoxy)isoxazol-5-yl)-3-methylbutanoyl)-4-hydroxy-N-((S)-1-(4-(4-methylthiazol-5-yl)phenyl)ethyl)pyrrolidine-2-carboxamide | 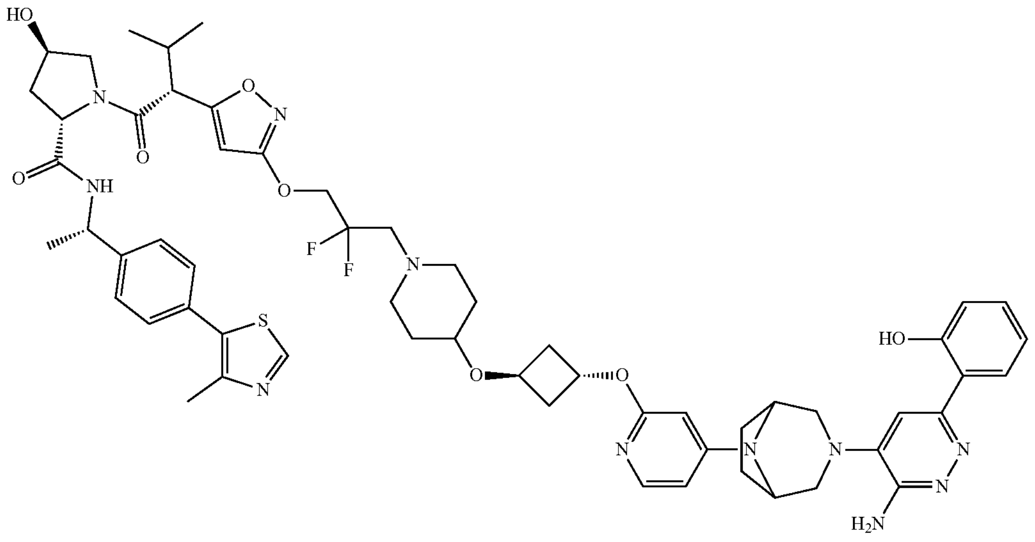 [SMILES: Cc1ncsc1-c1ccc([C@H](C)NC(=O)[C@@H]2C[C@@H](O)CN2C(=O)[C@@H](c2cc(OCC(F)(F)CN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 485 | (2S,4R)-1-((2S)-2-(3-(2-((1R,4S)-4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 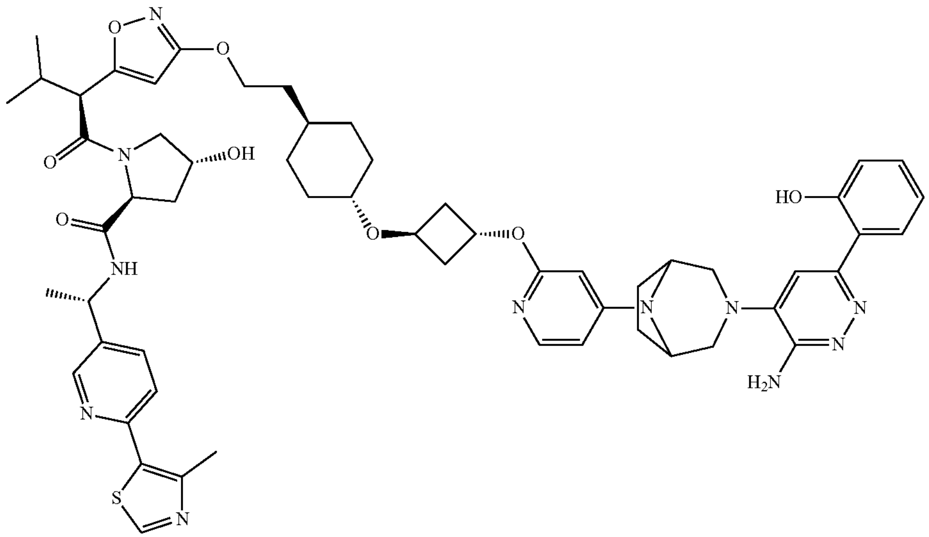 [SMILES: Cc1ncsc1-c1ccc([C@H](C)NC(=O)[C@@H]2C[C@@H](O)CN2C(=O)[C@H](c2cc(OCC[C@H]3CC[C@H](O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 486 | (2S,4R)-1-((2R)-2-(3-(2-((1R,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 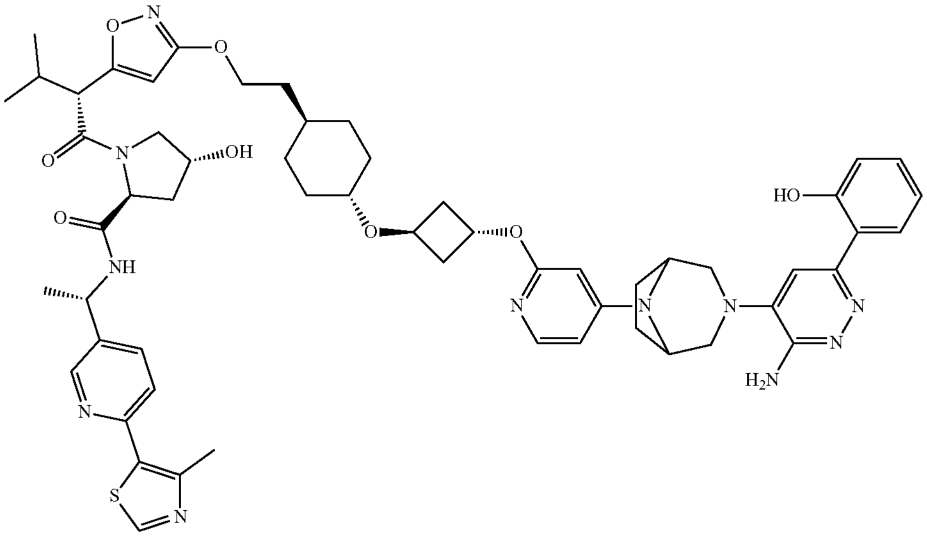 [SMILES: Cc1ncsc1-c1ccc([C@H](C)NC(=O)[C@@H]2C[C@@H](O)CN2C(=O)[C@@H](c2cc(OCC[C@H]3CC[C@H](O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
Exemplary bifunctional degradation compounds of the present disclosure
| Ex. # | Compound Name | Structure |
|---|---|---|
| 487 | (2S,4R)-1-((2S)-2-(3-(2-((1R,4S)-4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 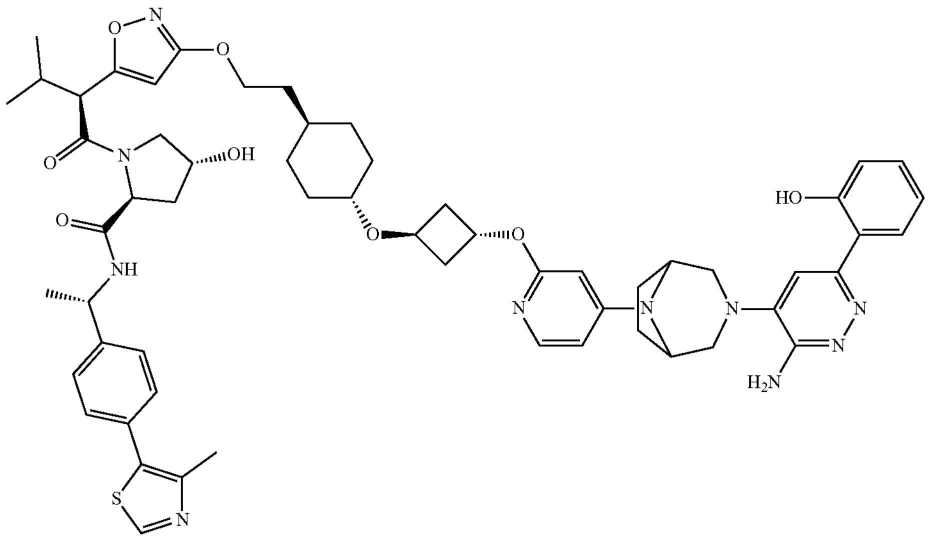 [SMILES: Cc1ncsc1-c1ccc([C@H](C)NC(=O)[C@@H]2C[C@@H](O)CN2C(=O)[C@H](c2cc(OCC[C@H]3CC[C@H](O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 488 | (2S,4R)-1-((2R)-2-(3-(2-((1R,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 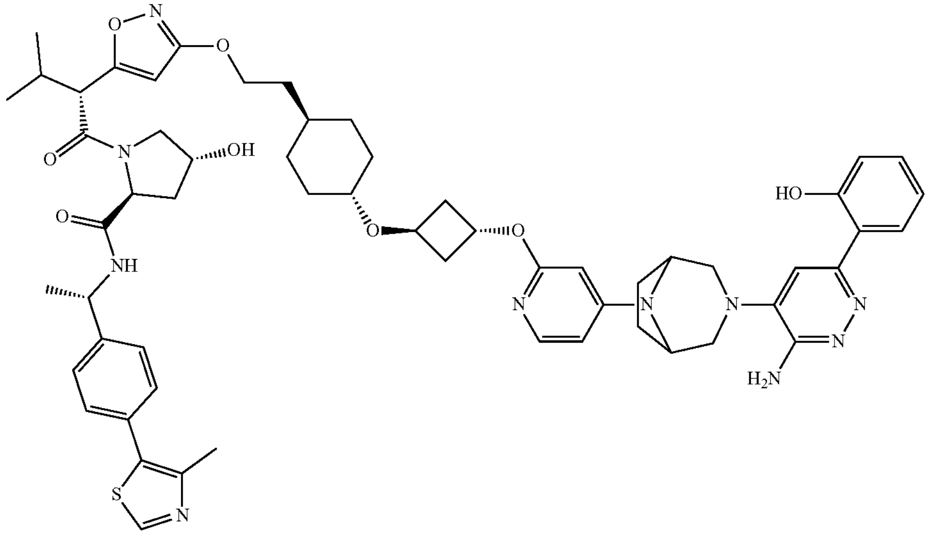 [SMILES: Cc1ncsc1-c1ccc([C@H](C)NC(=O)[C@@H]2C[C@@H](O)CN2C(=O)[C@@H](c2cc(OCC[C@H]3CC[C@H](O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 489 | (2S,4R)-4-hydroxy-1-((2R)-2-(3-(2-(4-((1r,3R)-3-((4-(3-(2-(2-hydroxyphenyl)imidazo[1,2-a]pyrimidin-7-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 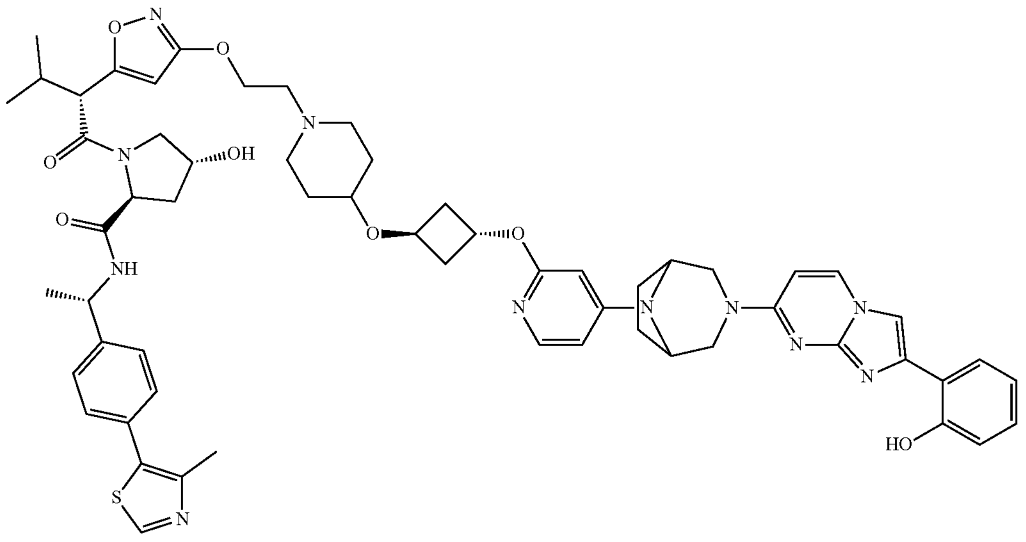 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6ccn8cc(-c9ccccc9O)nc8n6)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 490 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(5-(4-methylthiazol-5-yl)pyrazin-2-yl)ethyl)pyrrolidine-2-carboxamide | 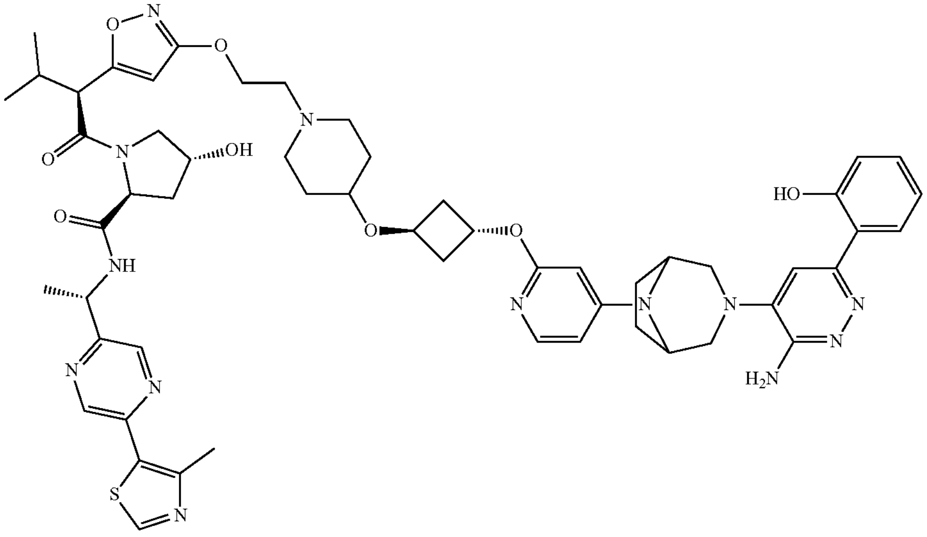 [SMILES: Cc1ncsc1-c1cnc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 491 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(5-(4-methylthiazol-5-yl)pyrazin-2-yl)ethyl)pyrrolidine-2-carboxamide | 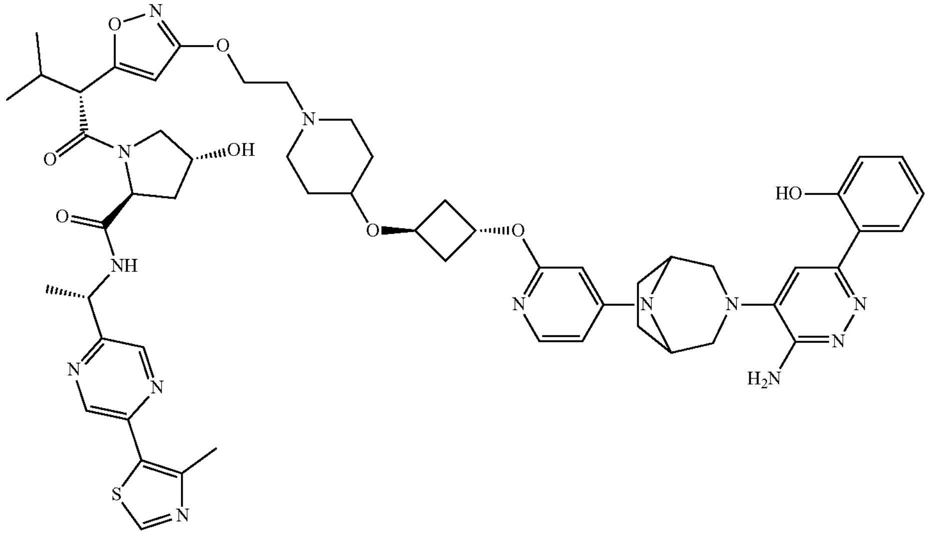 [SMILES: Cc1ncsc1-c1cnc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
Exemplary bifunctional degradation compounds of the present disclosure
| Ex. # | Compound Name | Structure |
| --- | --- | --- |
| 492 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)amino)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 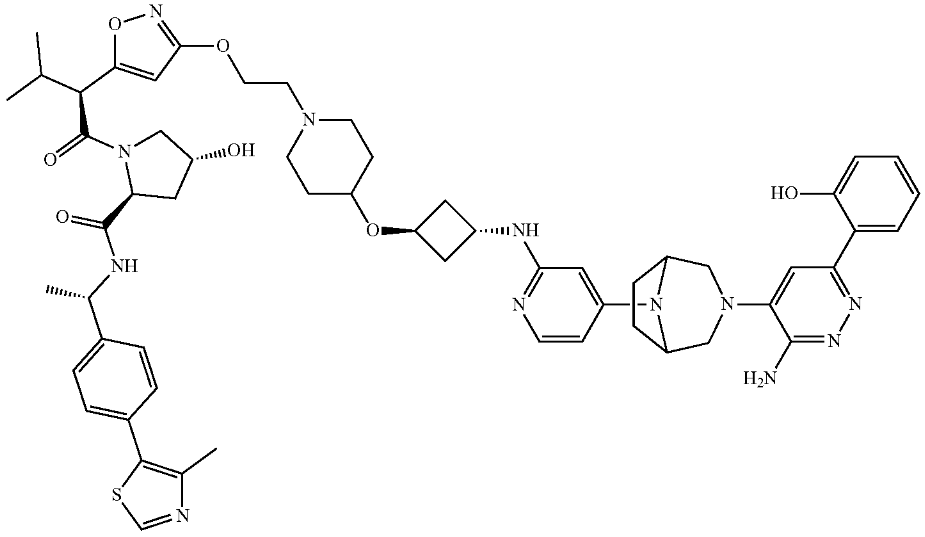 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Nc5cc(N6C7CCC6CN(c6cc(-c8ccccc8O)nnc6N)C7)ccn5)C4)CC3)no2)C(C)C)cc1] |

TABLE 1C-continued

| Exemplary bifunctional degradation compounds of the present disclosure | | |
|---|---|---|
| Ex. # | Compound Name | Structure |
| 493 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)amino)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 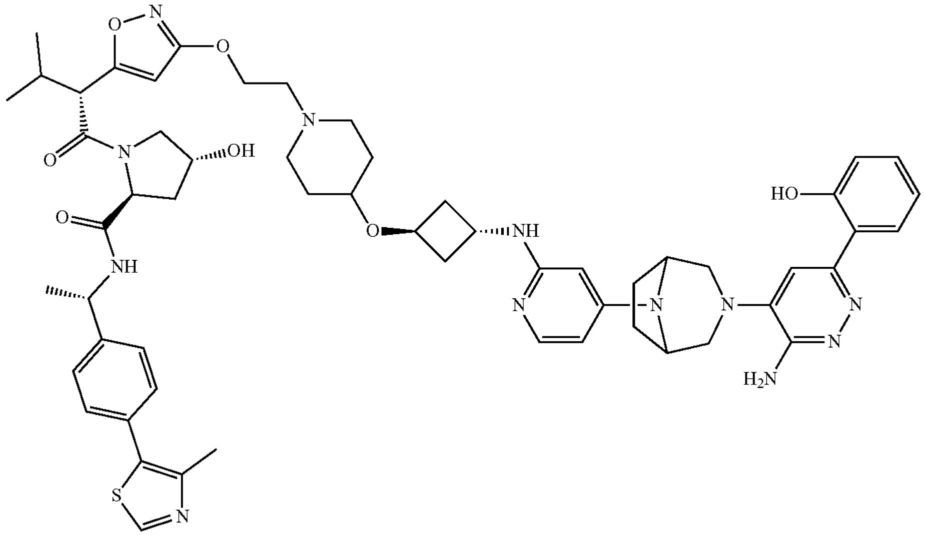 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Nc5cc(N6C7CCC6CN(c6cc(-c8ccccc8O)nnc6N)C7)ccn5)C4)CC3)no2)C(C)C)cc1] |
| 494 | (2S,4R)-1-((2S,3R)-4-(3-((4-(3-(3-amino-6-(2-hydroxyphenyl)pyridazin-4-yl)-3,8-diazabicyclo[3.2.1]octan-8-yl)pyridin-2-yl)oxy)propoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 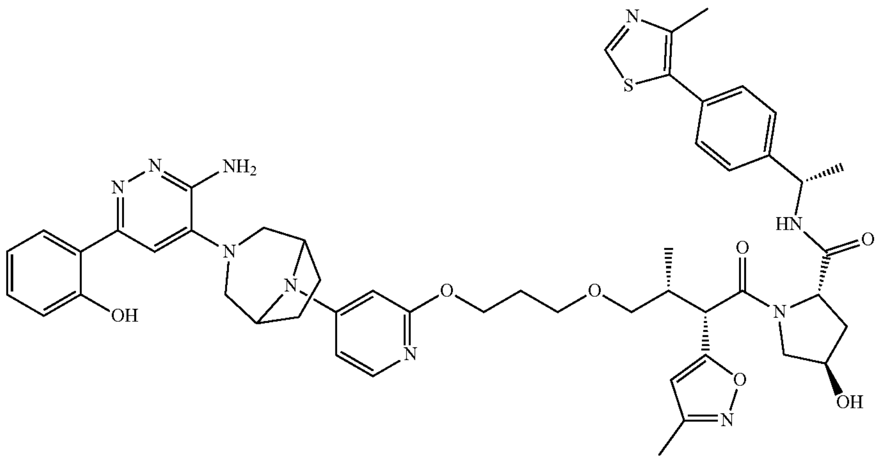 [SMILES: Cc1cc([C@@H](C(=O)N2C[C@H](O)C[C@H]2C(=O)N[C@@H](C)c2ccc(-c3scnc3C)cc2)[C@@H](C)COCCCOc2cc(N3C4CCC3CN(c3cc(-c5ccccc5O)nnc3N)C4)ccn2)on1] |

TABLE 1C-continued

Exemplary bifunctional degradation compounds of the present disclosure

| Ex. # | Compound Name | Structure |
|---|---|---|
| 495 | (2S,4R)-1-((2R,3R)-4-(3-((4-(3-(3-amino-6-(2-hydroxyphenyl)pyridazin-4-yl)-3,8-diazabicyclo[3.2.1]octan-8-yl)pyridin-2-yl)oxy)propoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 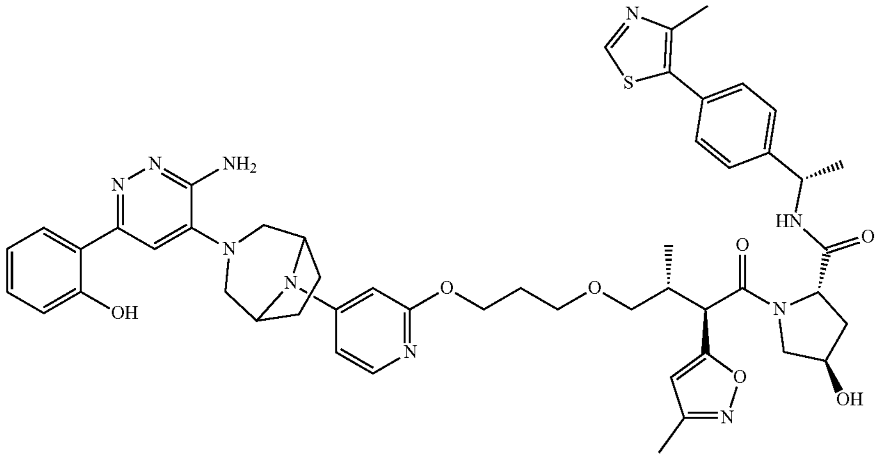 [SMILES: Cc1cc([C@H](C(=O)N2C[C@H](O)C[C@H]2C(=O)N[C@@H](C)c2ccc(-c3scnc3C)cc2)[C@@H](C)COCCCOc2cc(N3C4CCC3CN(c3cc(-c5ccccc5O)nnc3N)C4)ccn2)on1] |
| 496 | (2S,4R)-1-((R)-2-(3-(4-((4-((1R,3r)-3-((R)-3-(4-(3-amino-6-(2-hydroxyphenyl)pyridazin-4-yl)-1H-pyrazol-1-yl)but-1-yn-1-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 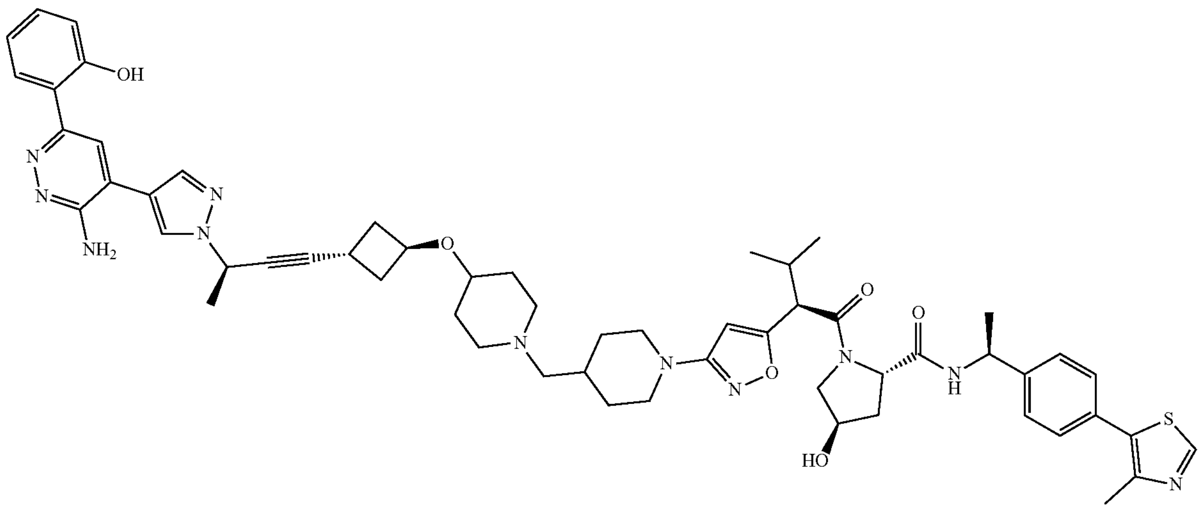 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](C#C[C@@H](C)n6cc(-c7cc(-c8ccccc8O)nnc7N)cn6)C5)CC4)CC3)no2)C(C)C)cc1] |

TABLE 1C-continued

| Ex. # | Compound Name | Structure |
|---|---|---|
| | Exemplary bifunctional degradation compounds of the present disclosure | |
| 497 | (2S,4R)-1-((R)-2-(3-(4-((4-((1S,3r)-3-((S)-3-(4-(3-amino-6-(2-hydroxyphenyl)pyridazin-4-yl)-1H-pyrazol-1-yl)but-1-yn-1-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 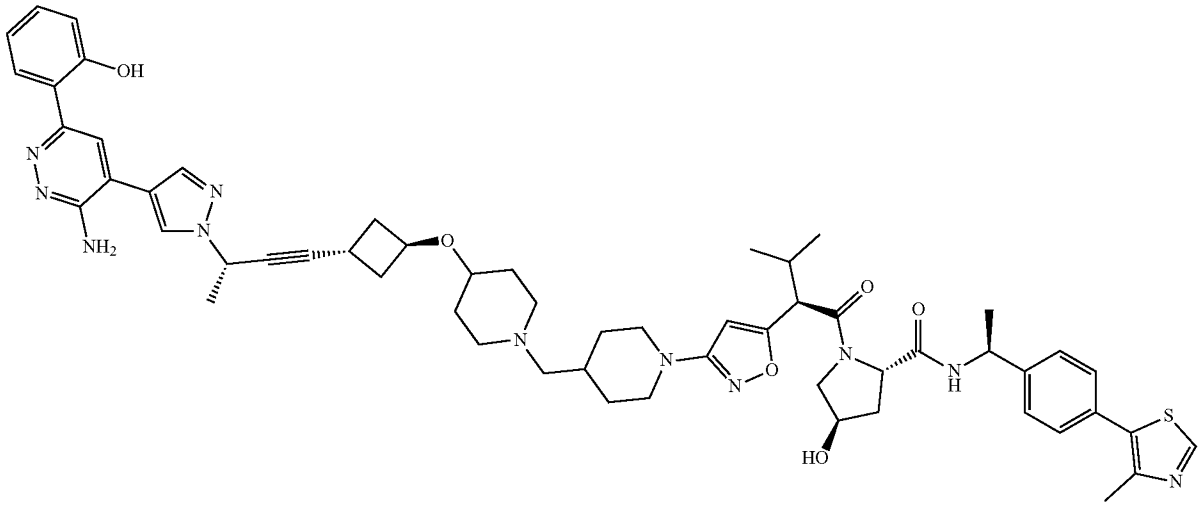 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](C#C[C@H](C)n6cc(-c7cc(-c8ccccc8O)nnc7N)cn6)C5)CC4)CC3)no2)C(C)C)cc1] |
| 498 | (2S,4R)-1-((2S)-2-(3-(4-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 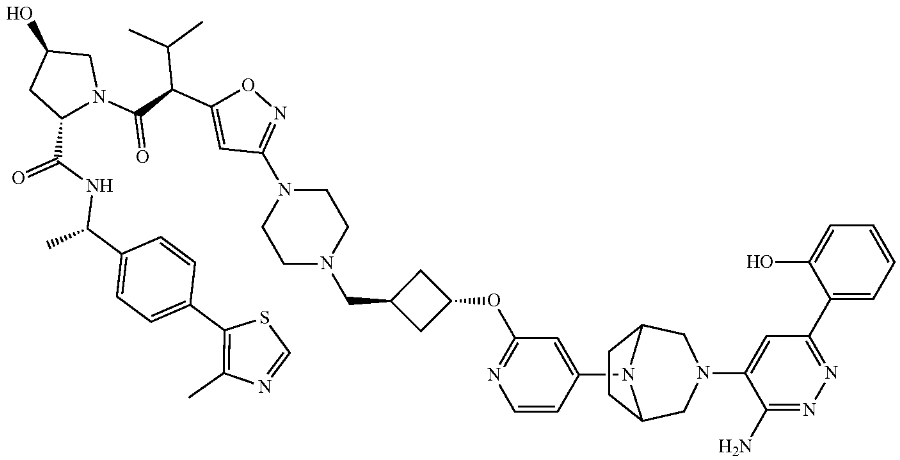 |

TABLE 1C-continued

| Ex. # | Compound Name | Structure |
|---|---|---|
| | Exemplary bifunctional degradation compounds of the present disclosure | |
| 499 | (2S,4R)-1-((2R)-2-(3-(4-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 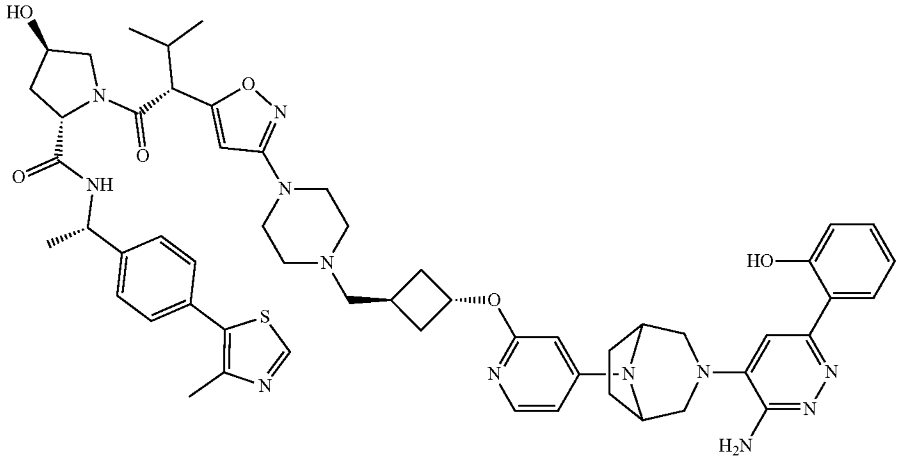 |
| 500 | (2S,4R)-1-(2-(3-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(5-fluoro-6-(4-methylthiazol-5-yl)pyridin-3-yl)ethyl)-4-hydroxypyrrolidine-2-carboxamide | 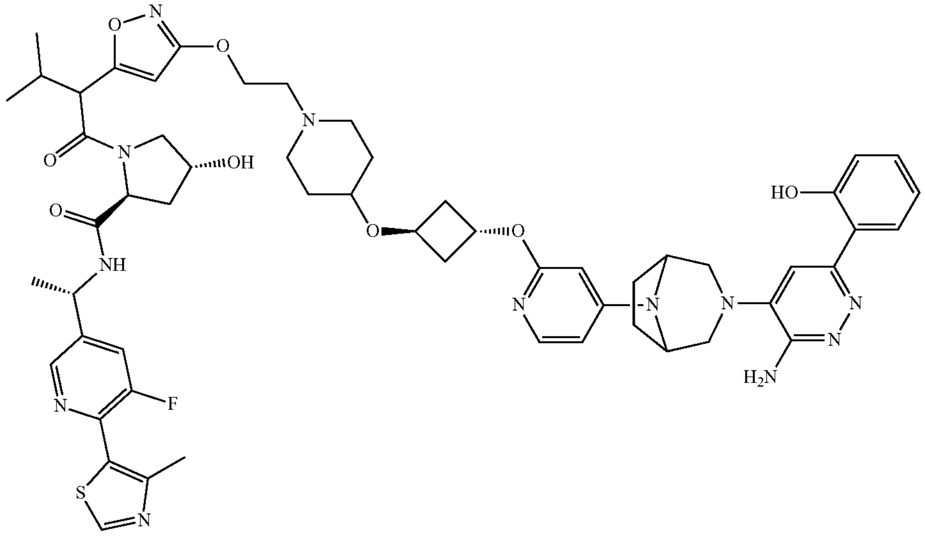 [SMILES: Cc1ncsc1-c1ncc([C@H](C)NC(=O)[C@@H]2C[C@@H](O)CN2C(=O)C(c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1F] |

TABLE 1C-continued
| Exemplary bifunctional degradation compounds of the present disclosure | | |
|---|---|---|
| Ex. # | Compound Name | Structure |
| 501 | (2S,4R)-1-(2-(3-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-1-(5-fluoro-6-(4-methylthiazol-5-yl)pyridin-3-yl)ethyl)-4-hydroxypyrrolidine-2-carboxamide | 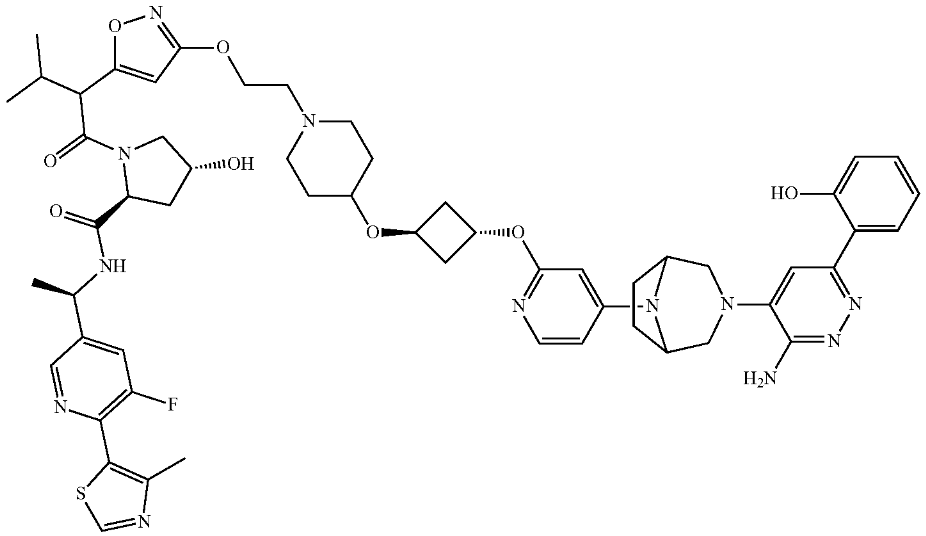 [SMILES: Cc1ncsc1-c1ncc([C@@H](C)NC(=O)[C@@H]2C[C@@H](O)CN2C(=O)C(c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1F] |

TABLE 1C-continued
Exemplary bifunctional degradation compounds of the present disclosure
| Ex. # | Compound Name | Structure |
| --- | --- | --- |
| 502 | (2S,4R)-1-((2R)-2-(3-(2-(4-((1r,3R)-3-((4-(3-(3-amino-6-(5-fluoro-2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 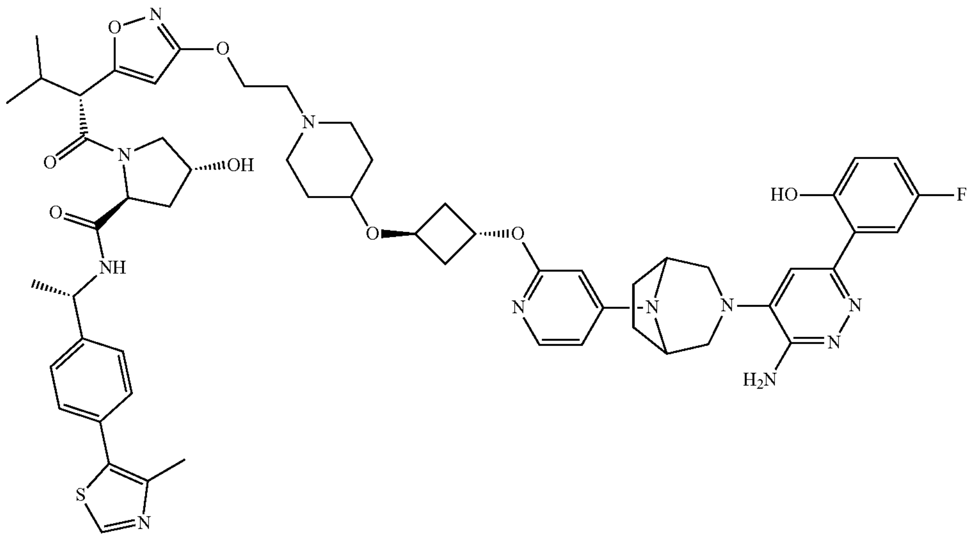 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8cc(F)ccc8O)nnc6N)C7)ccn5)C4)CC3)no2)C(C)C)cc1] |

TABLE 1C-continued
Exemplary bifunctional degradation compounds of the present disclosure
| Ex. # | Compound Name | Structure |
|---|---|---|
| 503 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(4-methylthiazol-5-yl)pyridazin-3-yl)ethyl)pyrrolidine-2-carboxamide | 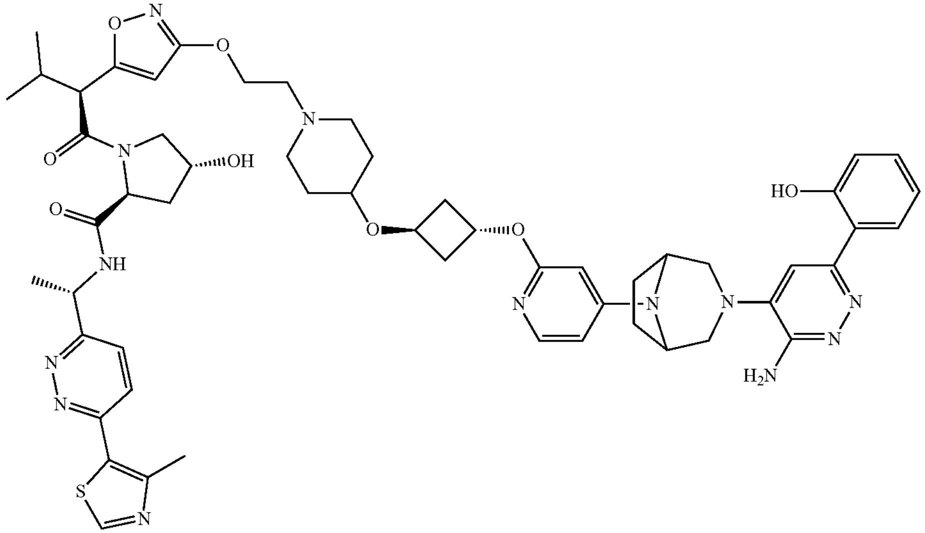 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)nn1] |

TABLE 1C-continued
| Exemplary bifunctional degradation compounds of the present disclosure | | |
|---|---|---|
| Ex. # | Compound Name | Structure |
| 504 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(6-(4-methylthiazol-5-yl)pyridazin-3-yl)ethyl)pyrrolidine-2-carboxamide | 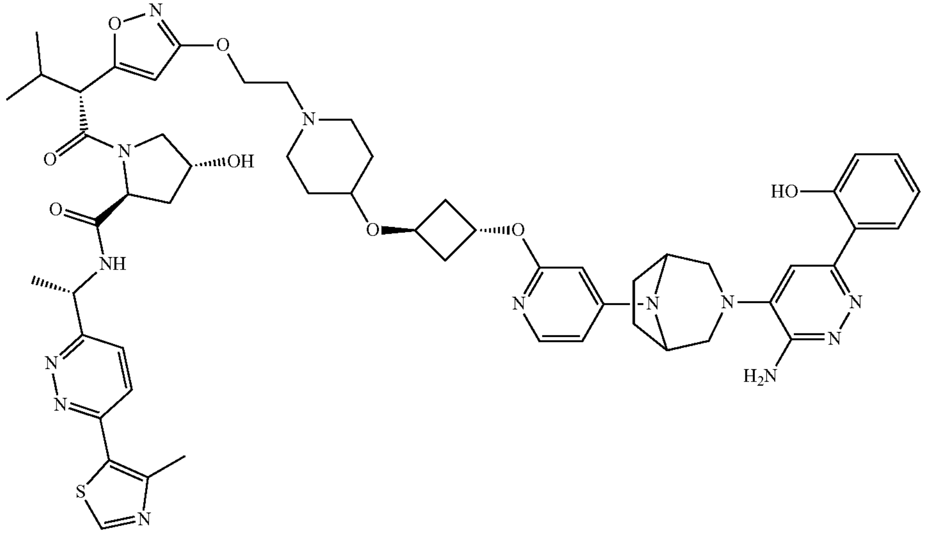 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)nn1] |

TABLE 1C-continued
| Exemplary bifunctional degradation compounds of the present disclosure | | |
|---|---|---|
| Ex. # | Compound Name | Structure |
| 505 | (2S,4R)-1-((2R)-2-(3-(2-(((1R,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)(isopropyl)amin0)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 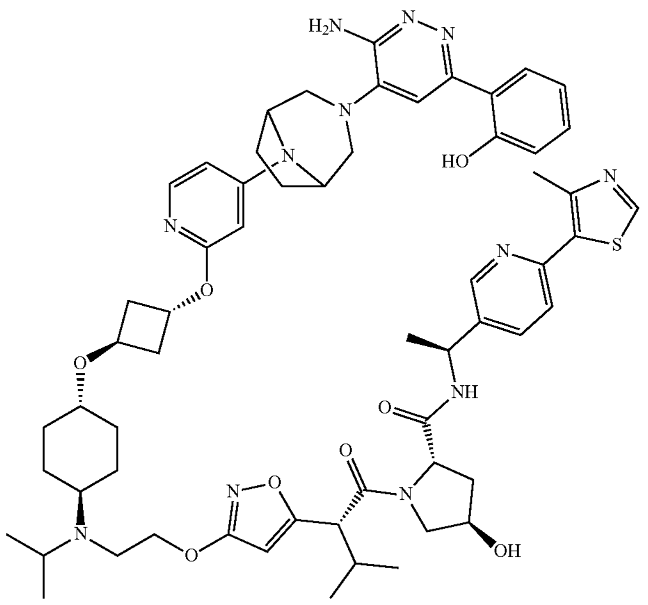 [SMILES: Cc1ncsc1-c1ccc([C@H](C)NC(=O)[C@@H]2C[C@@H](O)CN2C(=O)[C@@H](c2cc(OCCN(C(C)C)[C@H]3CC[C@H](O[C@H]4C[C@H](Oc5cc(N6C7CCC6CN(c6cc(-c8ccccc8O)nnc6N)C7)ccn5)C4)CC3)no2)C(C)C)cn1] |

TABLE 1C-continued
| Exemplary bifunctional degradation compounds of the present disclosure | | |
|---|---|---|
| Ex. # | Compound Name | Structure |
| 506 | 2-(6-amino-5-(8-(2-((1R,3r)-3-((1-(2-((5-((R)-1-((2S,4R)-4-hydroxy-2-(((S)-1-(4-(4-methylthiazol-5-yl)phenyl)ethyl)carbamoyl)pyrrolidin-1-yl)-3-methyl-1-oxobutan-2-yl)isoxazol-3-yl)oxy)ethyl)piperidin-4-yl)oxy)cyclobutoxy)pyridin-4-yl)-3,8-diazabicyclo[3.2.1]octan-3-yl)pyridazin-3-yl)phenyl dihydrogen phosphate | 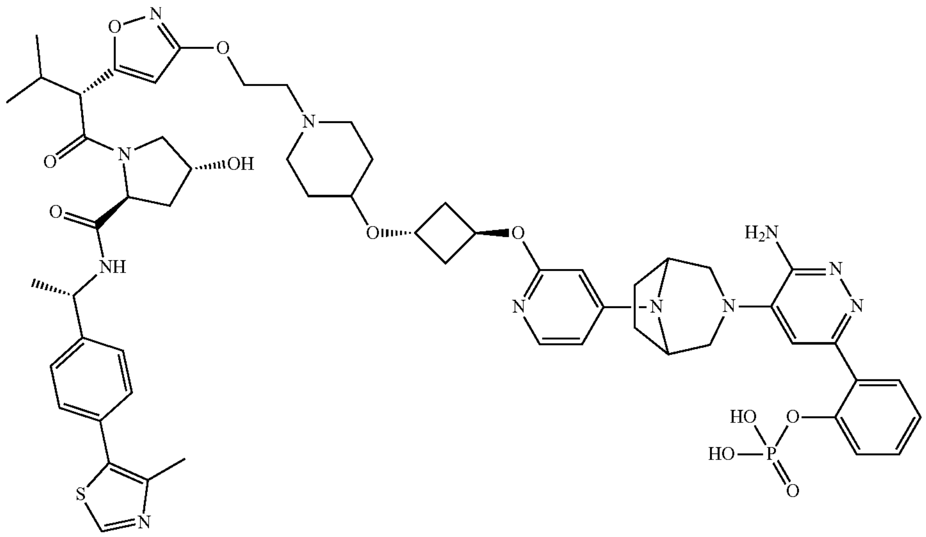 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8OP(=O)(O)O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 507 | (2S,4S)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 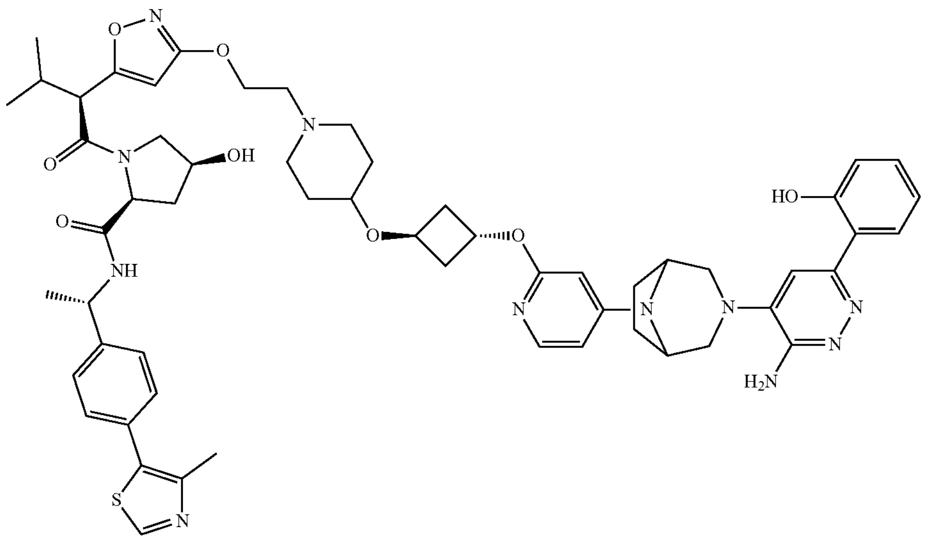 [SMILES: Cc1ncsc1-c1ccc([C@H](C)NC(=O)[C@@H]2C[C@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 508 | (2S,4S)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 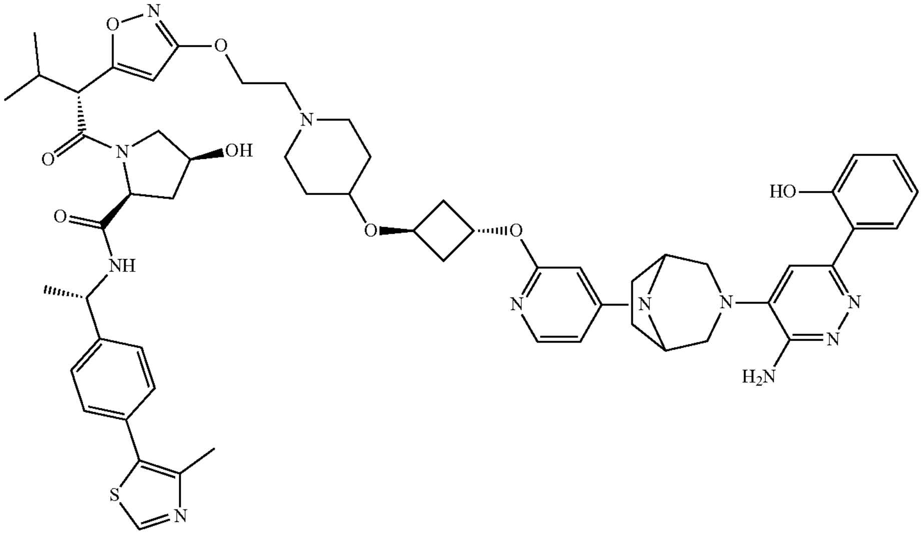 [SMILES: Cc1ncsc1-c1ccc([C@H](C)NC(=O)[C@@H]2C[C@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 509 | (2S,4R)-1-((2R)-2-(3-(2-((2S)-4-(2-((4-(3-(3-amino-6-(2-hydroxyphenyl)pyridazin-4-yl)-3,8-diazabicyclo[3.2.1]octan-8-yl)pyridin-2-yl)oxy)ethyl)-2-methylpiperazin-1-yl)ethoxy)isoxazol-5-yl)-3-methylbutanoyl)-4-hydroxy-N-((S)-1-(6-(4-methylthiazol-5-yl)pyridin-3-yl)ethyl)pyrrolidine-2-carboxamide | 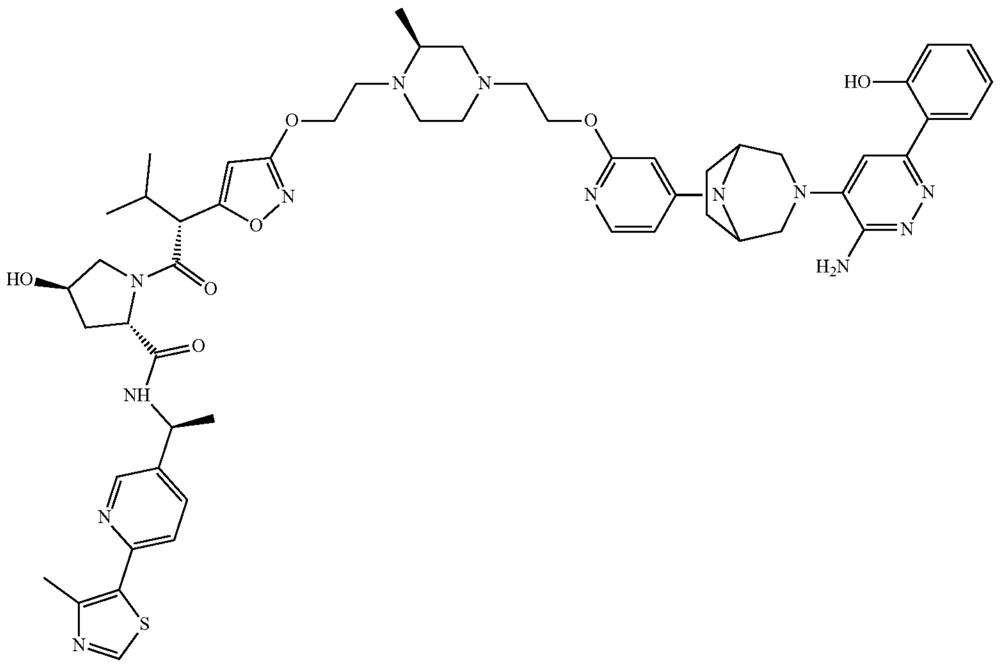 [SMILES: Cc1ncsc1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)C[C@@H]3C)no2)C(C)C)cn1] |

TABLE 1C-continued
| Exemplary bifunctional degradation compounds of the present disclosure | | |
|---|---|---|
| Ex. # | Compound Name | Structure |
| 510 | (2S,4R)-1-((2S)-2-(3-(2-(1-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 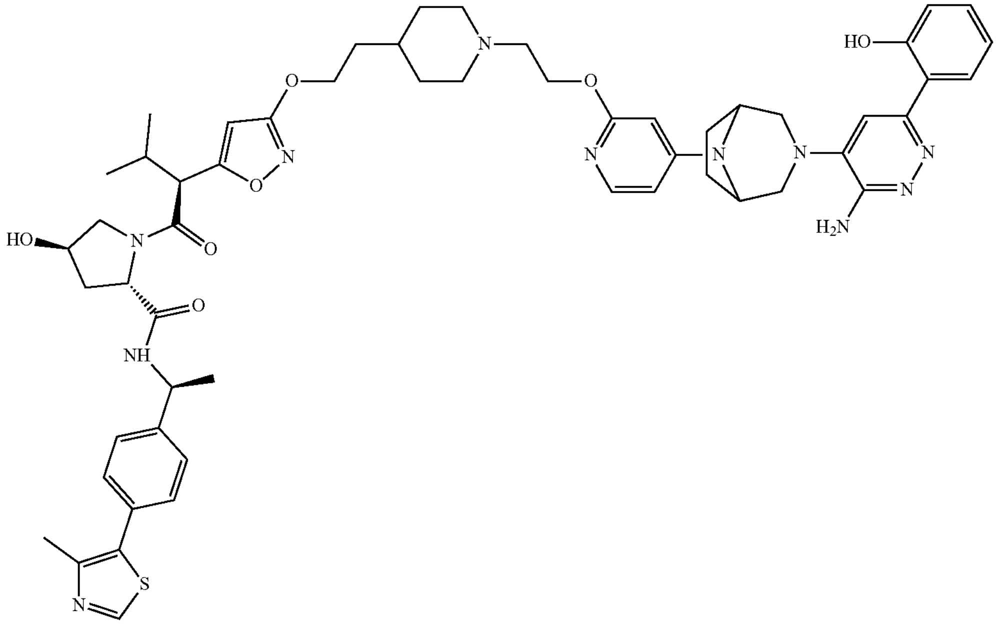 [SMILES: Cc1ncsc1-c1ccc([C@H](C)NC(=O)[C@@H]2C[C@@H](O)CN2C(=O)[C@H](c2cc(OCCC3CCN(CCOc4cc(N5C6CCC5CN(c5cc(-c7ccccc7O)nnc5N)C6)ccn4)CC3)no2)C(C)C)cc1] |

TABLE 1C-continued
| Exemplary bifunctional degradation compounds of the present disclosure | | |
|---|---|---|
| Ex. # | Compound Name | Structure |
| 511 | (2S,4R)-1-((2R)-2-(3-(2-(1-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 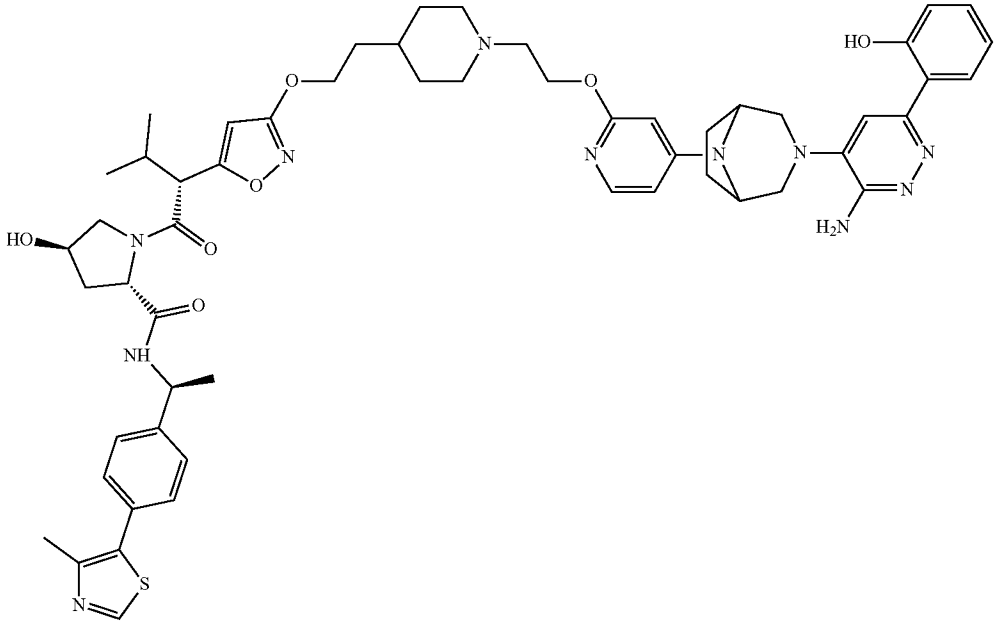 [SMILES: Cc1ncsc1-c1ccc([C@H](C)NC(=O)[C@@H]2C[C@@H](O)CN2C(=O)[C@@H](c2cc(OCCC3CCN(CCOc4cc(N5C6CCC5CN(c5cc(-c7ccccc7O)nnc5N)C6)ccn4)CC3)no2)C(C)C)cc1] |

TABLE 1C-continued

Exemplary bifunctional degradation compounds of the present disclosure

| Ex. # | Compound Name | Structure |
|---|---|---|
| 512 | (2S,4R)-1-((2S)-2-(2-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 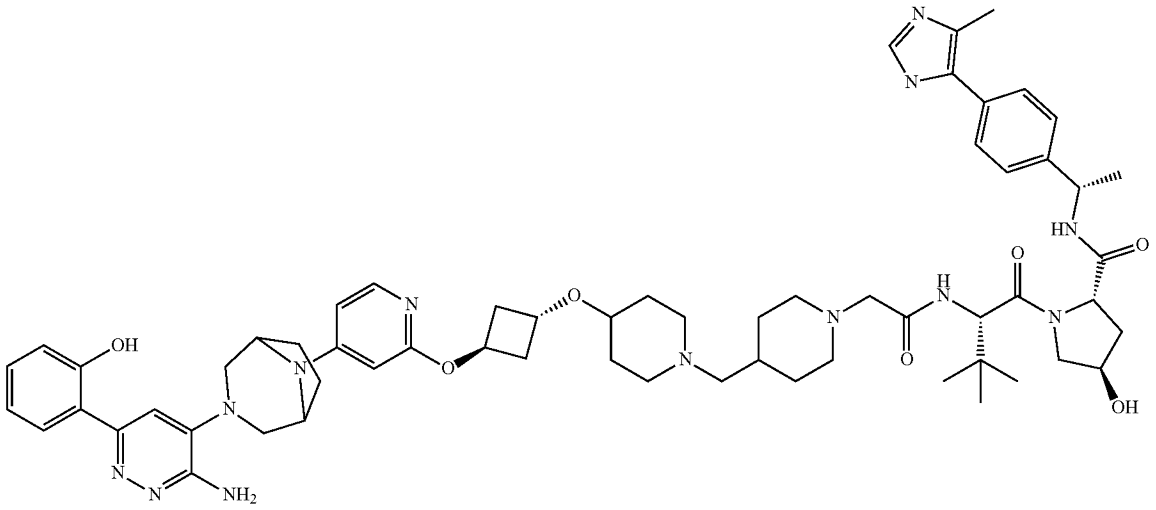 [SMILES: Cc1nc[nH]c1-c1ccc([C@H](C)NC(=O)[C@@H]2C[C@@H](O)CN2C(=O)[C@@H](NC(=O)CN2CCC(CN3CCC(O[C@H]4C[C@H](Oc5cc(N6C7CCC6CN(c6cc(-c8ccccc8O)nnc6N)C7)ccn5)C4)CC3)CC2)C(C)(C)C)cc1] |
| 513 | (2S,4R)-1-((2S,3S)-4-(2-((4-(3-(3-amino-6-(2-hydroxyphenyl)pyridazin-4-yl)-3,8-diazabicyclo[3.2.1]octan-8-yl)pyridin-2-yl)oxy)ethoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 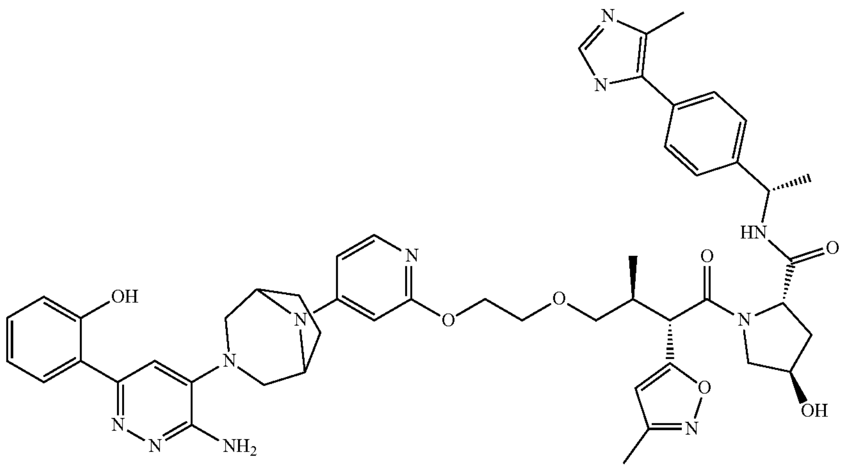 [SMILES: Cc1cc([C@@H](C(=O)N2C[C@H](O)C[C@H]2C(=O)N[C@@H](C)c2ccc(-c3[nH]cnc3C)cc2)[C@H](C)COCCOc2cc(N3C4CCC3CN(c3cc(-c5ccccc5O)nnc3N)C4)ccn2)on1] |

TABLE 1C-continued

| Ex. # | Compound Name | Structure |
|---|---|---|
| | Exemplary bifunctional degradation compounds of the present disclosure | |
| 514 | (2S,4R)-1-((2R,3S)-4-(2-((4-(3-(3-amino-6-(2-hydroxyphenyl)pyridazin-4-yl)-3,8-diazabicyclo[3.2.1]octan-8-yl)pyridin-2-yl)oxy)ethoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 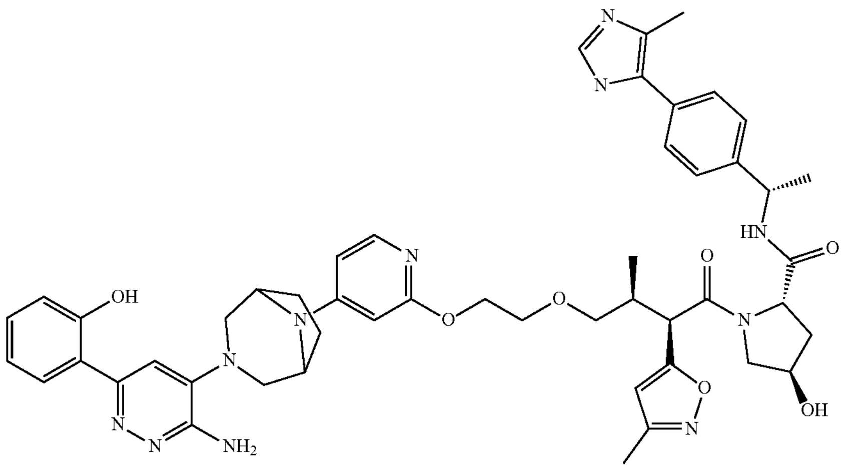 [SMILES: Cc1cc([C@H](C(=O)N2C[C@H](O)C[C@H]2C(=O)N[C@@H](C)c2ccc(-c3[nH]cnc3C)cc2)[C@H](C)COCCOc2cc(N3C4CCC3CN(c3cc(-c5ccccc5O)nnc3N)C4)ccn2)on1] |
| 515 | (2S,4R)-4-hydroxy-1-((2R)-2-(3-(2-(4-((1r,3R)-3-((4-(3-(2-(2-hydroxyphenyl)imidazo[1,2-a]pyrimidin-5-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-(4-methylthiazol-5-yl)phenyl)ethyl)pyrrolidine-2-carboxamide | 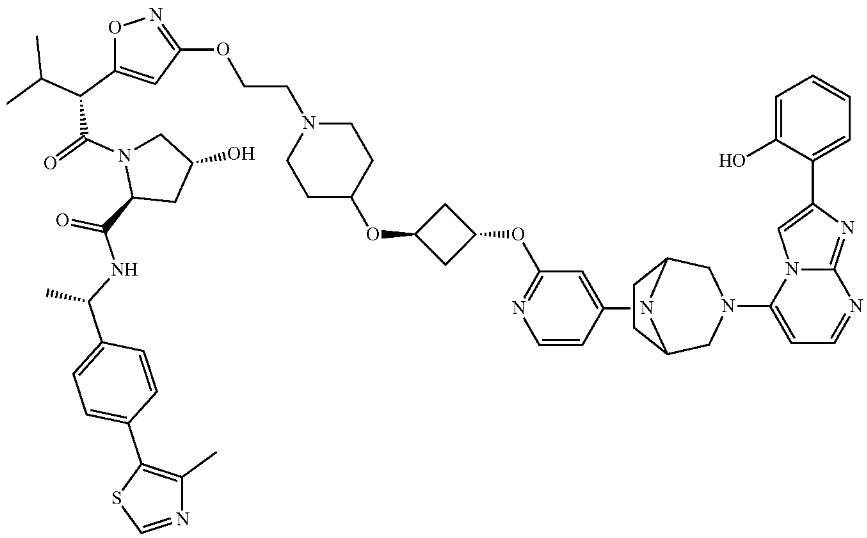 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6ccnc8nc(-c9ccccc9O)cn68)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 516 | (2S,4R)-1-((2R)-2-(3-(2-(4-((1r,3R)-3-((4-(3-(7-amino-2-(2-hydroxyphenyl)imidazo[1,2-a]pyrimidin-5-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 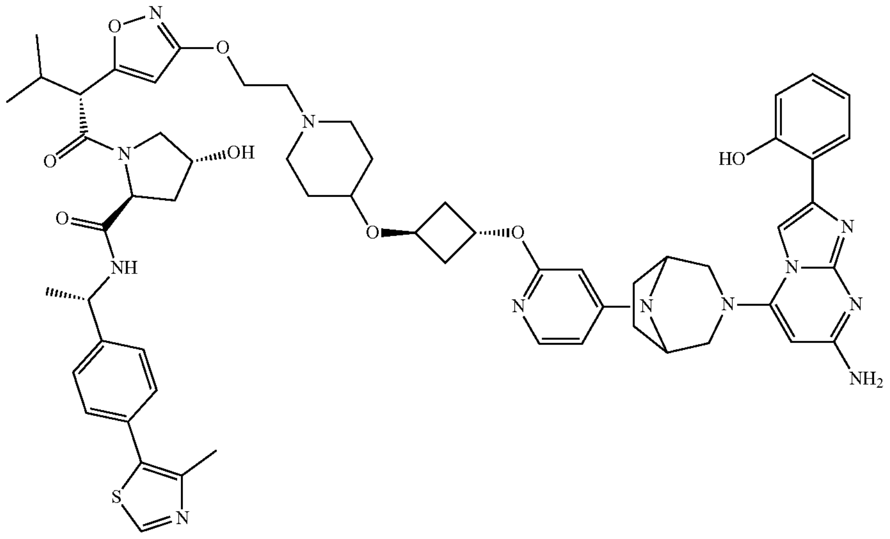 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(N)nc8nc(-c9ccccc9O)cn68)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 517 | (3R,5S)-1-((2R)-2-(3-(2-(4-((1r,3R)-3-((4-(3-(3-amino-6-(2-(phosphonooxy)phenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-5-(((S)-1-(4-(4-methylthiazol-5-yl)phenyl)ethyl)carbamoyl)pyrrolidin-3-yl dihydrogen phosphate | 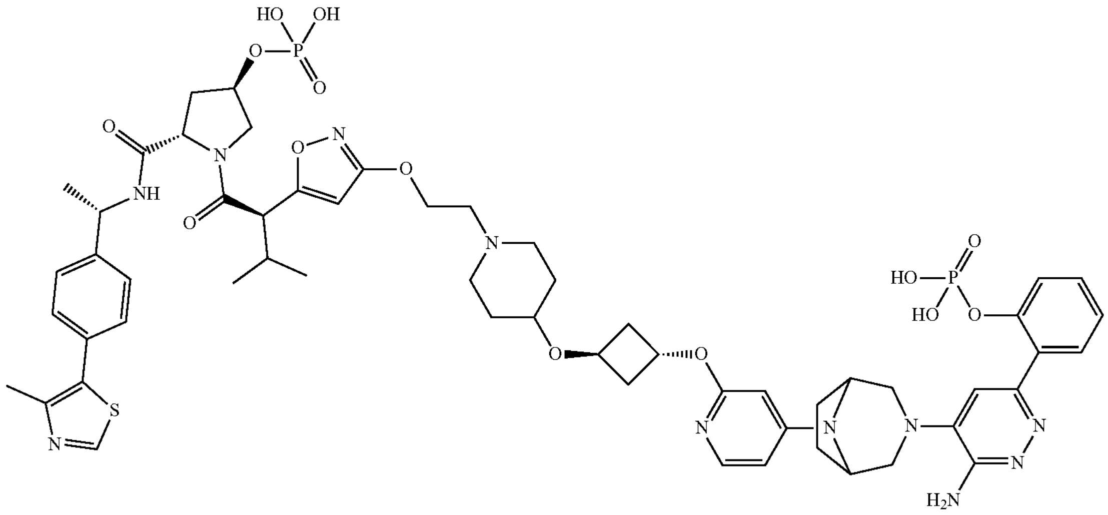 [SMILES: Cc1ncsc1-c1ccc([C@H](C)NC(=O)[C@@H]2C[C@@H](OP(=O)(O)O)CN2C(=O)[C@@H](c2cc(OCCN3CCC(O[C@H]4C[C@H](Oc5cc(N6C7CCC6CN(c6cc(-c8ccccc8OP(=O)(O)O)nnc6N)C7)ccn5)C4)CC3)no2)C(C)C)cc1] |

TABLE 1C-continued
| Exemplary bifunctional degradation compounds of the present disclosure | | |
|---|---|---|
| Ex. # | Compound Name | Structure |
| 518 | (2S,4R)-1-((2S)-2-(3-(3-((3-(((4-(3-(3-amino-6-(2-hydroxyphenyl)pyridazin-4-yl)-3,8-diazabicyclo[3.2.1]octan-8-yl)pyridin-2-yl)oxy)methyl)azetidin-1-yl)methyl)azetidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 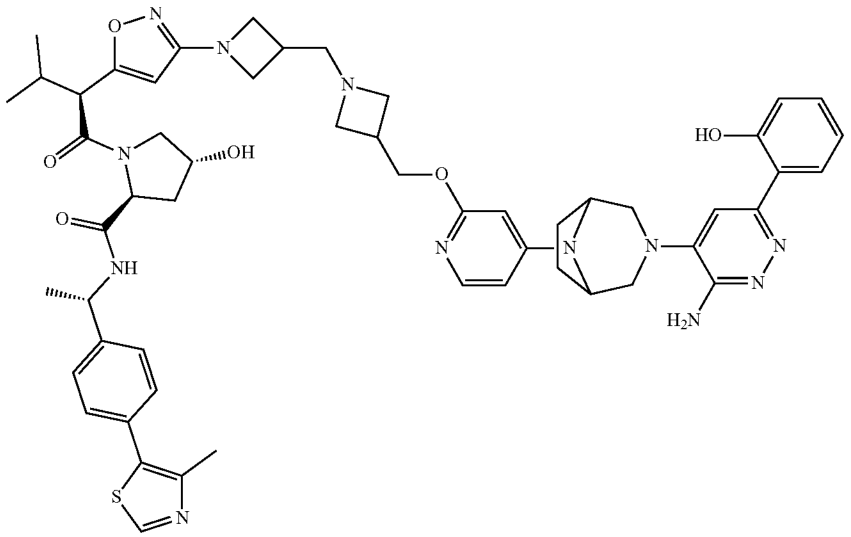 [SMILES: Cc1ncsc1-c1ccc([C@H](C)NC(=O)[C@@H]2C[C@@H](O)CN2C(=O)[C@H](c2cc(N3CC(CN4CC(COc5cc(N6C7CCC6CN(c6cc(-c8ccccc8O)nnc6N)C7)ccn5)C4)C3)no2)C(C)C)cc1] |

TABLE 1C-continued

Exemplary bifunctional degradation compounds of the present disclosure

| Ex. # | Compound Name | Structure |
|---|---|---|
| 519 | (2S,4R)-1-((2R)-2-(3-(3-((3-(((4-(3-(3-amino-6-(2-hydroxyphenyl)pyridazin-4-yl)-3,8-diazabicyclo[3.2.1]octan-8-yl)pyridin-2-yl)oxy)methyl)azetidin-1-yl)methyl)azetidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 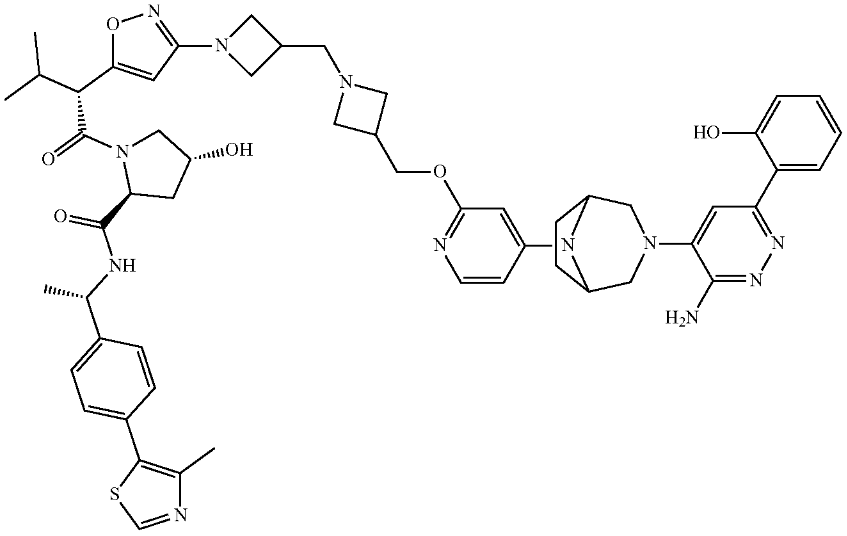 [SMILES: Cc1ncsc1-c1ccc([C@H](C)NC(=O)[C@@H]2C[C@@H](O)CN2C(=O)[C@@H](c2cc(N3CC(CN4CC(COc5cc(N6C7CCC6CN(c6cc(-c8ccccc8O)nnc6N)C7)ccn5)C4)C3)no2)C(C)C)cc1] |
| 520 | (2S,4R)-1-((2S)-2-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 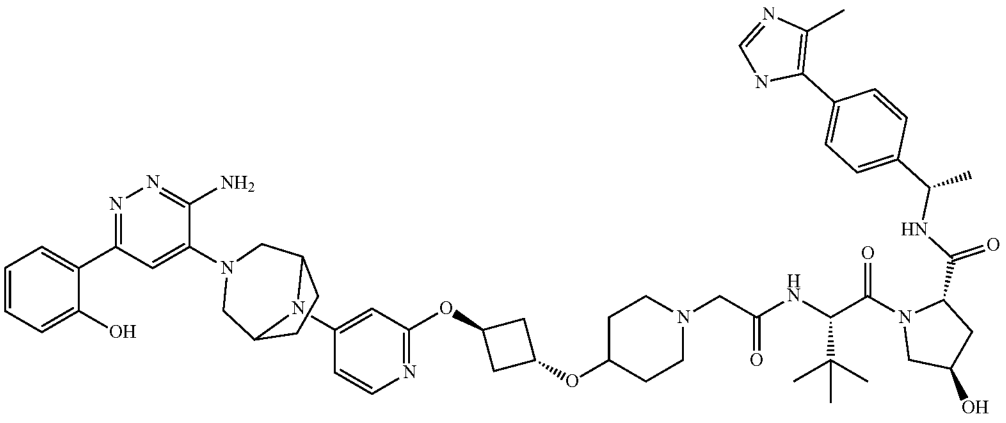 [SMILES: Cc1nc[nH]c1-c1ccc([C@H](C)NC(=O)[C@@H]2C[C@@H](O)CN2C(=O)[C@@H](NC(=O)CN2CCC(O[C@H]3C[C@H](Oc4cc(N5C6CCC5CN(c5cc(-c7ccccc7O)nnc5N)C6)ccn4)C3)CC2)C(C)(C)C)cc1] |

TABLE 1C-continued
| Exemplary bifunctional degradation compounds of the present disclosure | | |
|---|---|---|
| Ex. # | Compound Name | Structure |
| 521 | (2S,4R)-1-((2S)-2-(3-(4-(3-(5-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 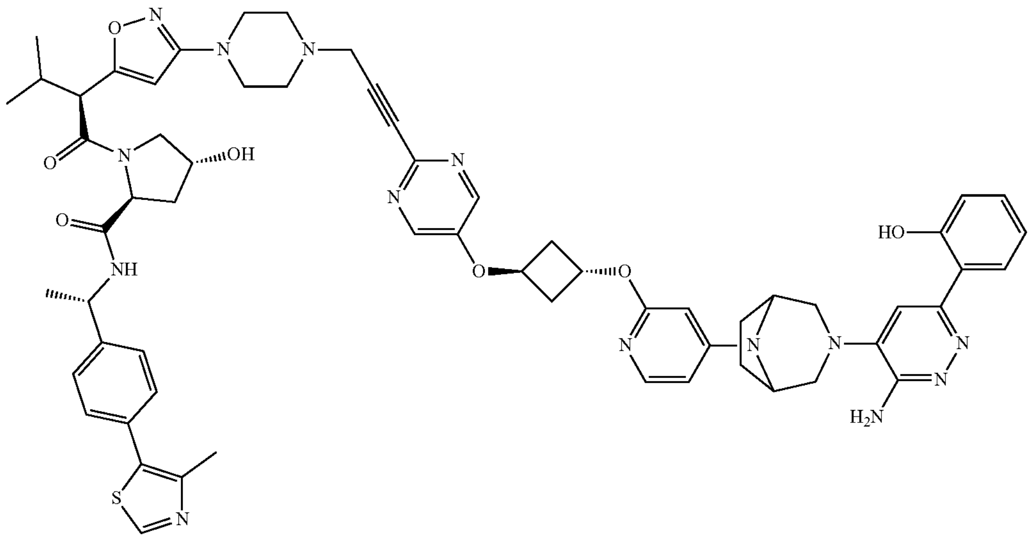 [SMILES: Cc1ncsc1-c1ccc([C@H](C)NC(=O)[C@@H]2C[C@@H](O)CN2C(=O)[C@H](c2cc(N3CCN(CC#Cc4ncc(O[C@H]5C[C@H](Oc6cc(N7C8CCC7CN(c7cc(-c9ccccc9O)nnc7N)C8)ccn6)C5)cn4)CC3)no2)C(C)C)cc1] |

TABLE 1C-continued

| Ex. # | Compound Name | Structure |
|---|---|---|
| | Exemplary bifunctional degradation compounds of the present disclosure | |
| 522 | (2S,4R)-1-((2R)-2-(3-(4-(3-(5-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)pyrimidin-2-yl)prop-2-yn-1-yl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide | 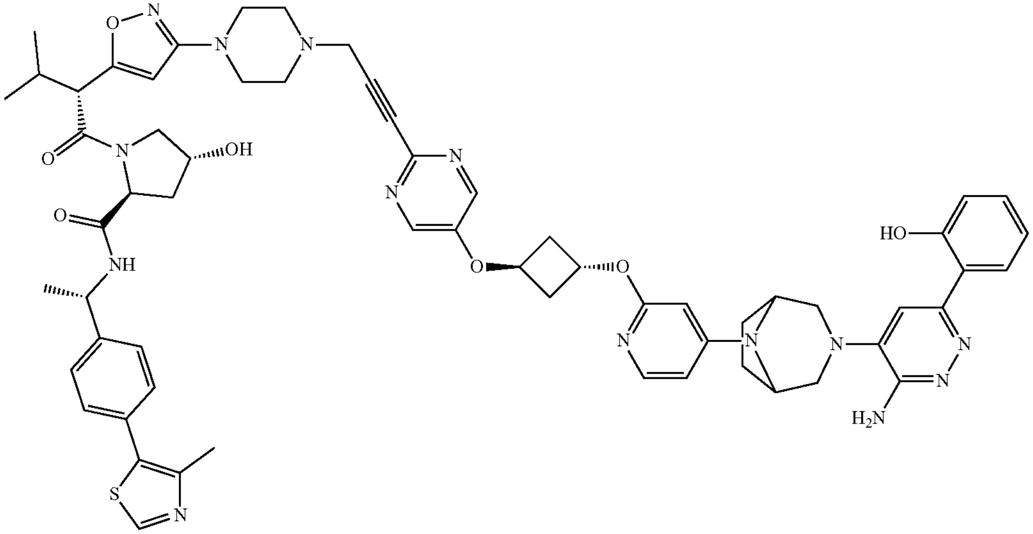 [SMILES: Cc1ncsc1-c1ccc([C@H](C)NC(=O)[C@@H]2C[C@@H](O)CN2C(=O)[C@@H](c2cc(N3CCN(CC#Cc4ncc(O[C@H]5C[C@H](Oc6cc(N7C8CCC7CN(c7cc(-c9ccccc9O)nnc7N)C8)ccn6)C5)cn4)CC3)no2)C(C)C)cc1] |
| 523 | (2S,4R)-4-hydroxy-N-((S)-2-(2-(2-((6-(2-hydroxyphenyl)pyridazin-3-yl)amino)ethoxy)ethoxy)-1-(4-(4-methylthiazol-5-yl)phenyl)ethyl)-1-((S)-3-methyl-2-(3-methylisoxazol-5-yl)butanoyl)pyrrolidine-2-carboxamide | 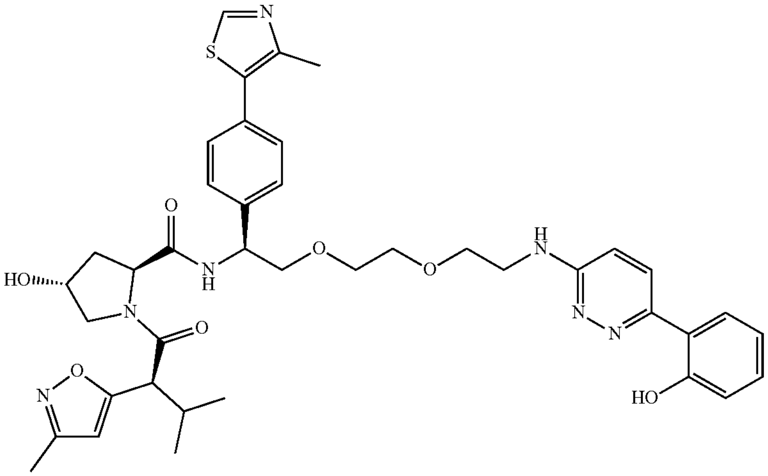 [SMILES: Cc1cc([C@@H](C(=O)N2C[C@H](O)C[C@H]2C(=O)N[C@H](COCCOCCNc2ccc(-c3ccccc3O)nn2)c2ccc(-c3scnc3C)cc2)C(C)C)on1] |

TABLE 1C-continued

| Exemplary bifunctional degradation compounds of the present disclosure | | |
|---|---|---|
| Ex. # | Compound Name | Structure |
| 524 | (2S,4R)-4-hydroxy-N-((S)-2-(2-(2-((6-(2-hydroxyphenyl)pyridazin-3-yl)amino)ethoxy)ethoxy)-1-(4-(4-methylthiazol-5-yl)phenyl)ethyl)-1-((R)-3-methyl-2-(3-methylisoxazol-5-yl)butanoyl)pyrrolidine-2-carboxamide | 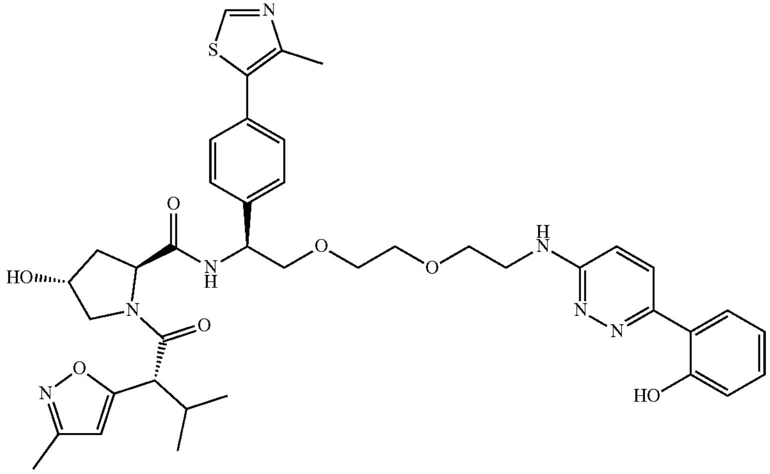 [SMILES: Cc1cc([C@H](C(=O)N2C[C@H](O)C[C@H]2C(=O)N[C@H](COCCOCCNc2ccc(-c3ccccc3O)nn2)c2ccc(-c3scnc3C)cc2)C(C)C)on1] |
| 525 | (2S,4R)-4-hydroxy-N-((R)-2-(2-(2-((6-(2-hydroxyphenyl)pyridazin-3-yl)amino)ethoxy)ethoxy)-1-(4-(4-methylthiazol-5-yl)phenyl)ethyl)-1-((S)-3-methyl-2-(3-methylisoxazol-5-yl)butanoyl)pyrrolidine-2-carboxamide | 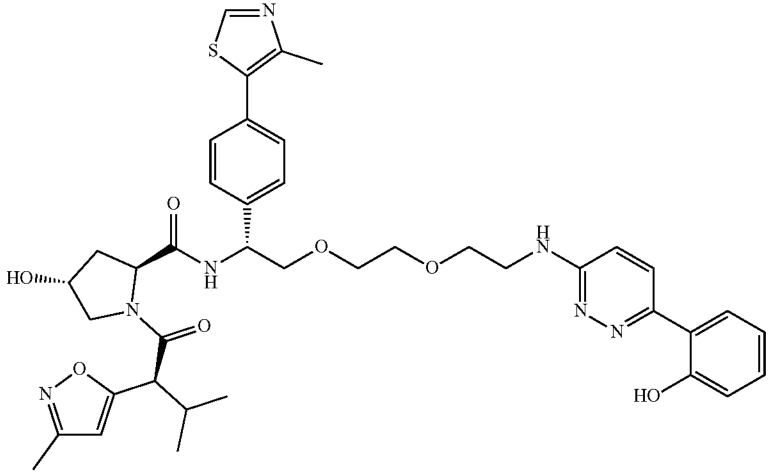 [SMILES: Cc1cc([C@@H](C(=O)N2C[C@H](O)C[C@H]2C(=O)N[C@@H](COCCOCCNc2ccc(-c3ccccc3O)nn2)c2ccc(-c3scnc3C)cc2)C(C)C)on1] |

TABLE 1C-continued

| Exemplary bifunctional degradation compounds of the present disclosure | | |
|---|---|---|
| Ex. # | Compound Name | Structure |
| 526 | (2S,4R)-4-hydroxy-N-((R)-2-(2-(2-((6-(2-hydroxyphenyl)pyridazin-3-yl)amino)ethoxy)ethoxy)-1-(4-(4-methylthiazol-5-yl)phenyl)ethyl)-1-((R)-3-methyl-2-(3-methylisoxazol-5-yl)butanoyl)pyrrolidine-2-carboxamide | 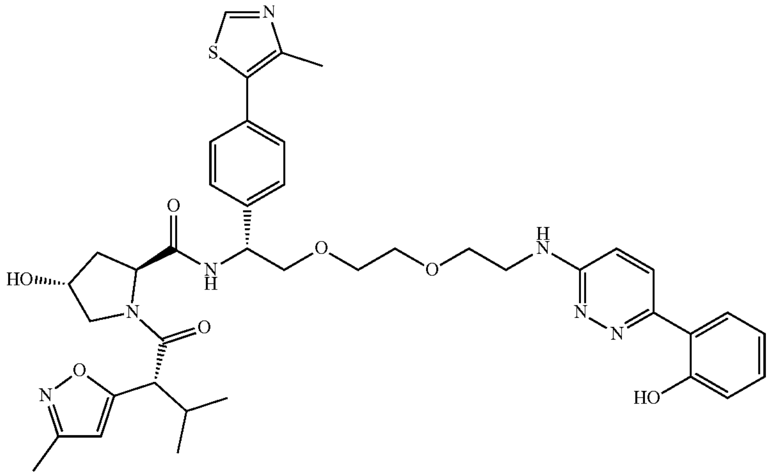 [SMILES: Cc1cc([C@H](C(=O)N2C[C@H](O)C[C@H]2C(=O)N[C@@H](COCCOCCNc2ccc(-c3ccccc3O)nn2)c2ccc(-c3scnc3C)cc2)C(C)C)on1] |
| 527 | (2S,4R)-N-((S)-2-((5-(3-amino-6-(2-hydroxyphenyl)pyridazin-4-yl)pentyl)oxy)-1-(4-(4-methylthiazol-5-yl)phenyl)ethyl)-4-hydroxy-1-((S)-3-methyl-2-(3-methylisoxazol-5-yl)butanoyl)pyrrolidine-2-carboxamide | 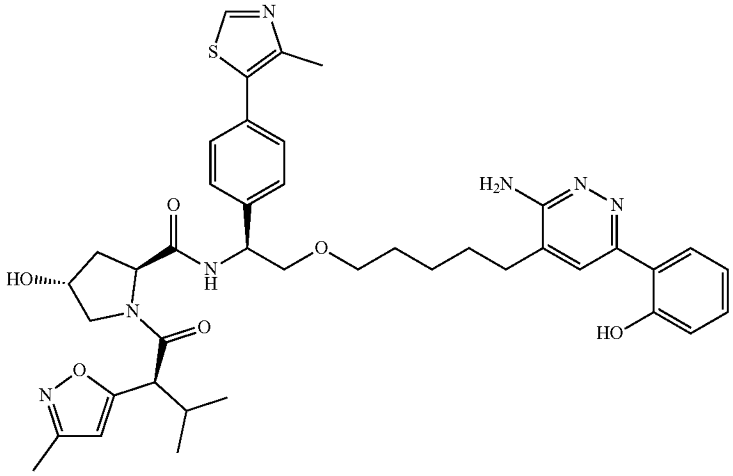 [SMILES: Cc1cc([C@@H](C(=O)N2C[C@H](O)C[C@H]2C(=O)N[C@H](COCCCCCc2cc(-c3ccccc3O)nnc2N)c2ccc(-c3scnc3C)cc2)C(C)C)on1] |

TABLE 1C-continued

| Exemplary bifunctional degradation compounds of the present disclosure | | |
|---|---|---|
| Ex. # | Compound Name | Structure |
| 528 | (2S,4R)-N-((S)-2-((5-(3-amino-6-(2-hydroxyphenyl)pyridazin-4-yl)pentyl)oxy)-1-(4-(4-methylthiazol-5-yl)phenyl)ethyl)-4-hydroxy-1-((R)-3-methyl-2-(3-methylisoxazol-5-yl)butanoyl)pyrrolidine-2-carboxamide | 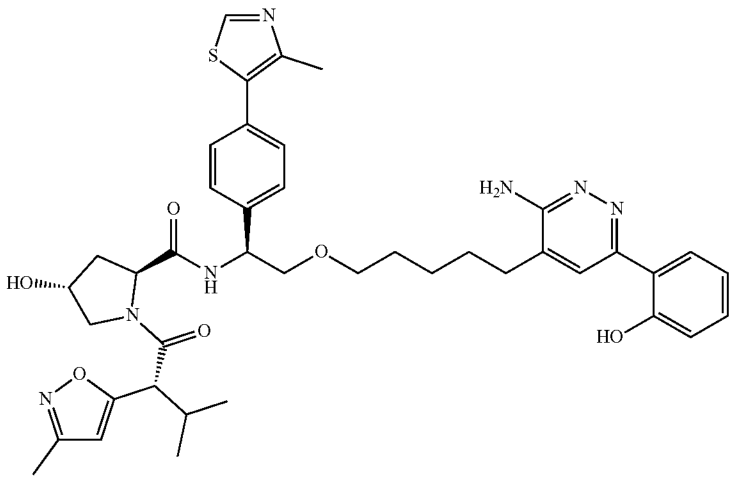 [SMILES: Cc1cc([C@H](C(=O)N2C[C@H](O)C[C@H]2C(=O)N[C@H](COCCCCCc2cc(-c3ccccc3O)nnc2N)c2ccc(-c3scnc3C)cc2)C(C)C)on1] |
| 529 | (2S,4R)-N-((R)-2-((5-(3-amino-6-(2-hydroxyphenyl)pyridazin-4-yl)pentyl)oxy)-1-(4-(4-methylthiazol-5-yl)phenyl)ethyl)-4-hydroxy-1-((S)-3-methyl-2-(3-methylisoxazol-5-yl)butanoyl)pyrrolidine-2-carboxamide | 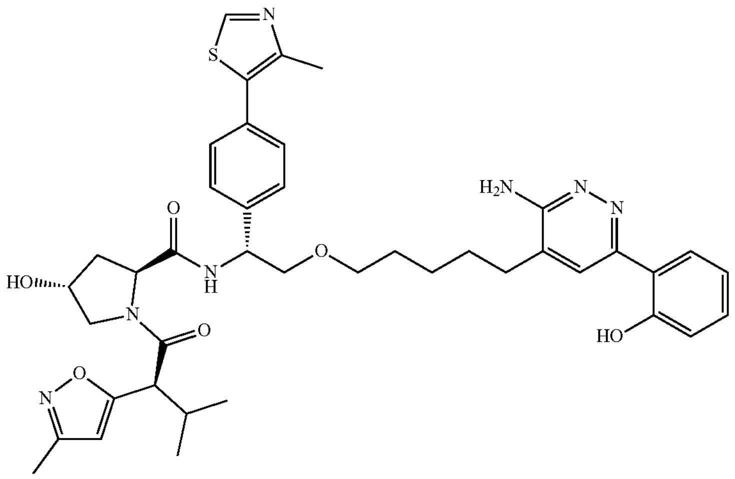 [SMILES: Cc1cc([C@@H](C(=O)N2C[C@H](O)C[C@H]2C(=O)N[C@@H](COCCCCCc2cc(-c3ccccc3O)nnc2N)c2ccc(-c3scnc3C)cc2)C(C)C)on1] |

TABLE 1C-continued

| Exemplary bifunctional degradation compounds of the present disclosure | | |
|---|---|---|
| Ex. # | Compound Name | Structure |
| 530 | (2S,4R)-N-((R)-2-((5-(3-amino-6-(2-hydroxyphenyl)pyridazin-4-yl)pentyl)oxy)-1-(4-(4-methylthiazol-5-yl)phenyl)ethyl)-4-hydroxy-1-((R)-3-methyl-2-(3-methylisoxazol-5-yl)butanoyl)pyrrolidine-2-carboxamide | 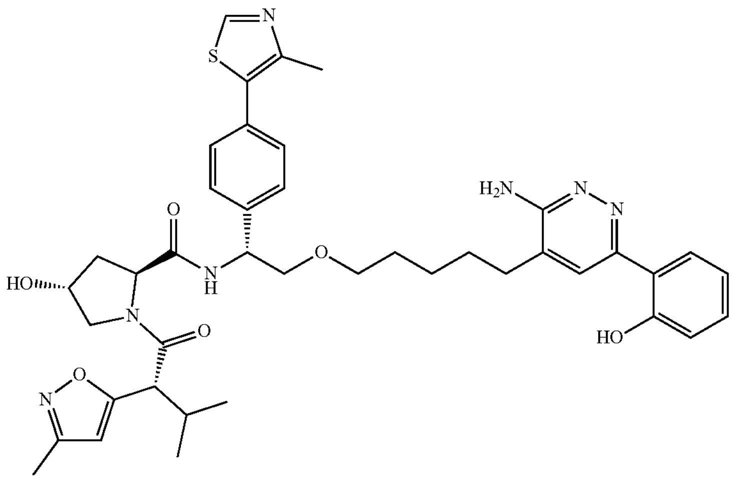 [SMILES: Cc1cc([C@H](C(=O)N2C[C@H](O)C[C@H]2C(=O)N[C@@H](COCCCCCc2cc(-c3ccccc3O)nnc2N)c2ccc(-c3scnc3C)cc2)C(C)C)on1] |
| 531 | (2S,4R)-1-((2S)-2-(3-(2-((2R,4S)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 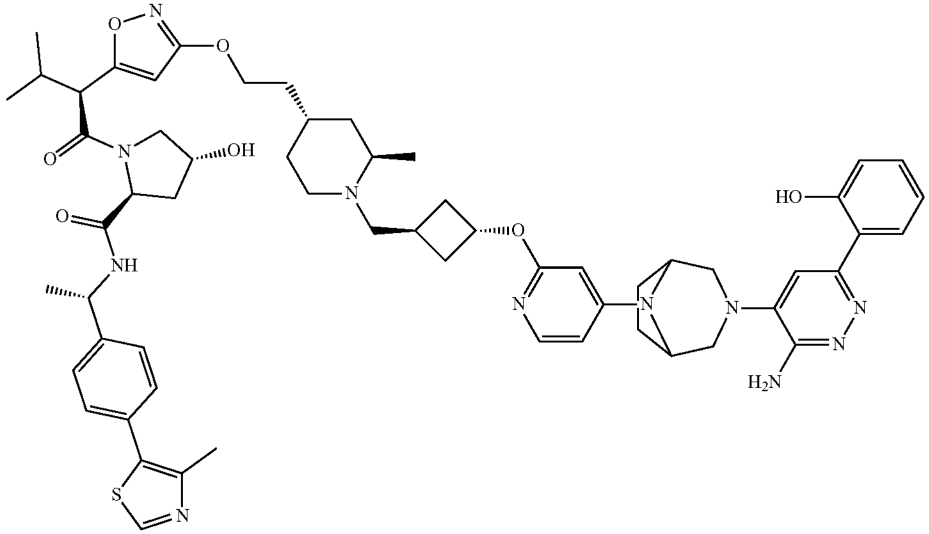 [SMILES: Cc1ncsc1-c1ccc([C@H](C)NC(=O)[C@@H]2C[C@@H](O)CN2C(=O)[C@H](c2cc(OCC[C@H]3CCN(C[C@H]4C[C@H](Oc5cc(N6C7CCC6CN(c6cc(-c8ccccc8O)nnc6N)C7)ccn5)C4)[C@H](C)C3)no2)C(C)C)cc1] |

TABLE 1C-continued
| Exemplary bifunctional degradation compounds of the present disclosure | | |
|---|---|---|
| Ex. # | Compound Name | Structure |
| 532 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-3-cyano-1-(4-(4-methylthiazol-5-yl)phenyl)propyl)-4-hydroxypyrrolidine-2-carboxamide | 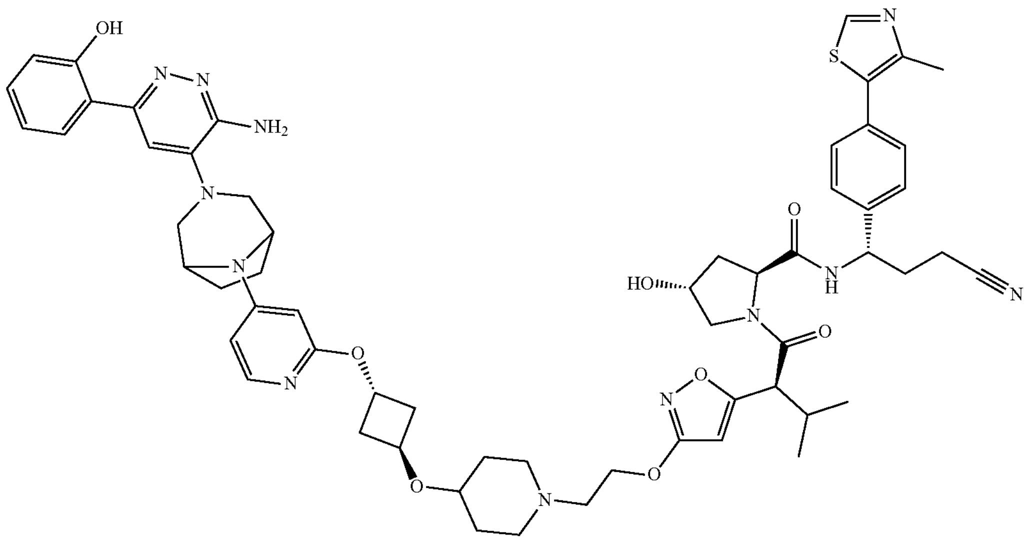 [SMILES: Cc1ncsc1-c1ccc([C@H](CCC#N)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |

TABLE 1C-continued

| Exemplary bifunctional degradation compounds of the present disclosure | | |
|---|---|---|
| Ex. # | Compound Name | Structure |
| 533 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-3-cyano-1-(4-(4-methylthiazol-5-yl)phenyl)propyl)-4-hydroxypyrrolidine-2-carboxamide | 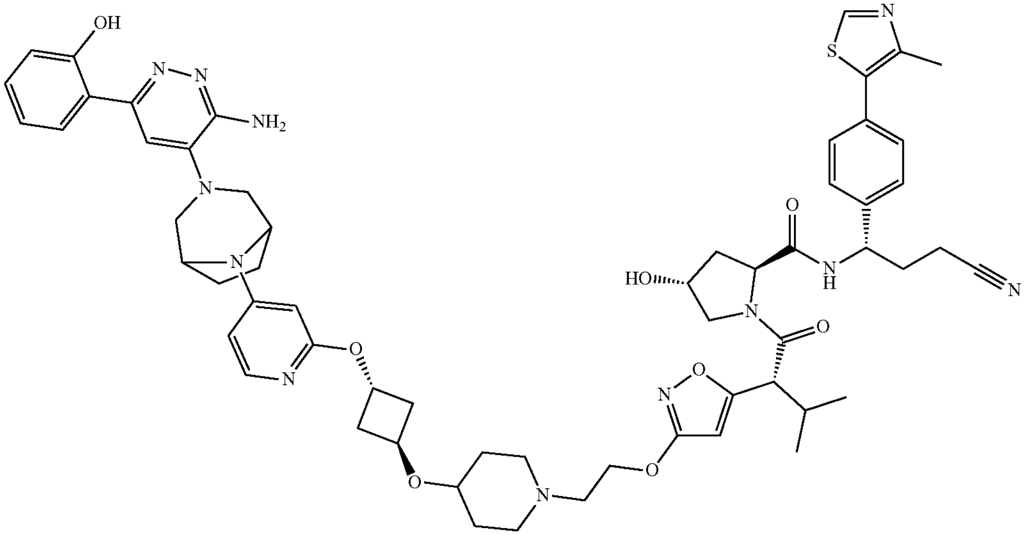 [SMILES: Cc1ncsc1-c1ccc([C@H](CCC#N)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] |
| 534 | (2S,4R)-1-((2S,3S)-4-(2-(4-(3-amino-6-(2-hydroxyphenyl)pyridazin-4-yl)-1 H-pyrazol-1-yl)ethoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide | 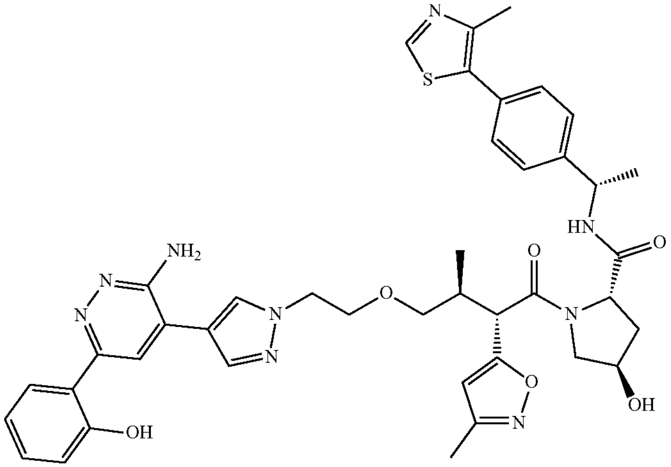 [SMILES: Cc1cc([C@@H](C(=O)N2C[C@H](O)C[C@H]2C(=O)N[C@@H](C)c2ccc(-c3scnc3C)cc2)[C@H](C)COCCn2cc(-c3cc(-c4ccccc4O)nnc3N)cn2)on1] |

TABLE 1C-continued
| Exemplary bifunctional degradation compounds of the present disclosure | | |
|---|---|---|
| Ex. # | Compound Name | Structure |
| 535 | (2S,4R)-1-((2R)-2-(3-(2-((2R,4S)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide | 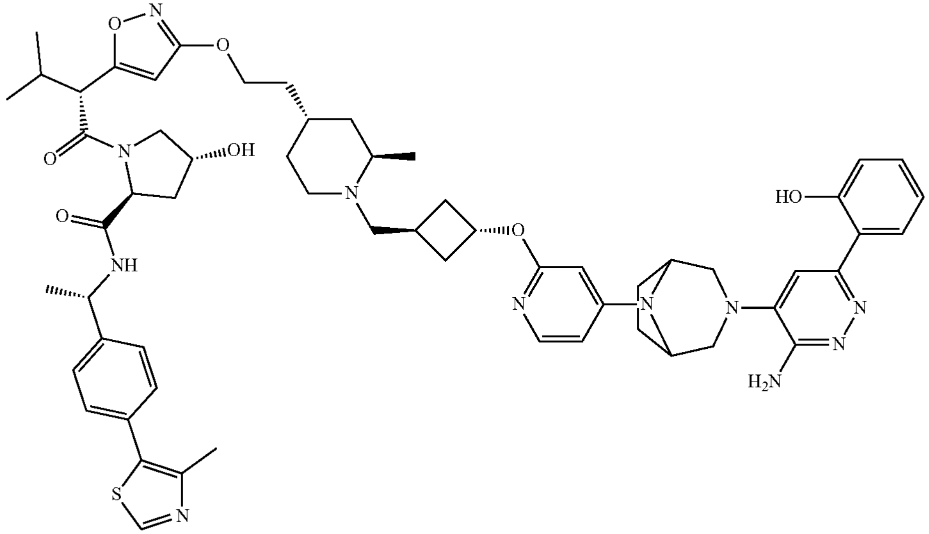 [SMILES: Cc1ncsc1-c1ccc([C@H](C)NC(=O)[C@@H]2C[C@@H](O)CN2C(=O)[C@@H](c2cc(OCC[C@H]3CCN(C[C@H]4C[C@H](Oc5cc(N6C7CCC6CN(c6cc(-c8ccccc8O)nnc6N)C7)ccn5)C4)[C@H](C)C3)no2)C(C)C)cc1] |

TABLE 1C-continued

| Exemplary bifunctional degradation compounds of the present disclosure | | |
|---|---|---|
| Ex. # | Compound Name | Structure |
| 460 | (3R,5S)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-5-(((S)-1-(4-(4-methylthiazol-5-yl)phenyl)ethyl)carbamoyl) pyrrolidin-3-yl (2,5,8,11,14,17,20,23,26,29,32,35,38,41,44,47,50,53,56,59,62,65-docosaoxaheptahexacontan-67-yl) succinate | 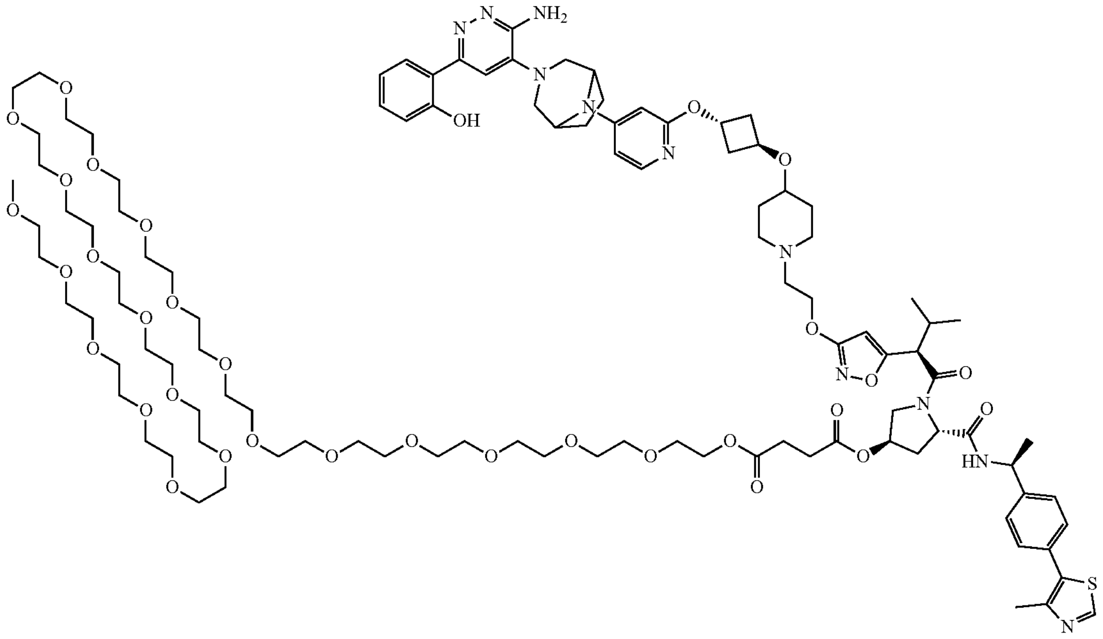 [SMILES: COCCOCCOCCOCCOCCOCCOCCOCCOCCOCCOCCOCCOCCOCCOCCOCCOCCOCCOCCOCCOCCOCCOC(=O)CCC(=O)O[C@@H]1C[C@@H](C(=O)N[C@@H](C)c2ccc(-c3scnc3C)cc2)N(C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)C1] |

[]Exemplary bifunctional degradation compounds of the present disclosure

| Ex No | Structure | Name |
|---|---|---|
| 536 | 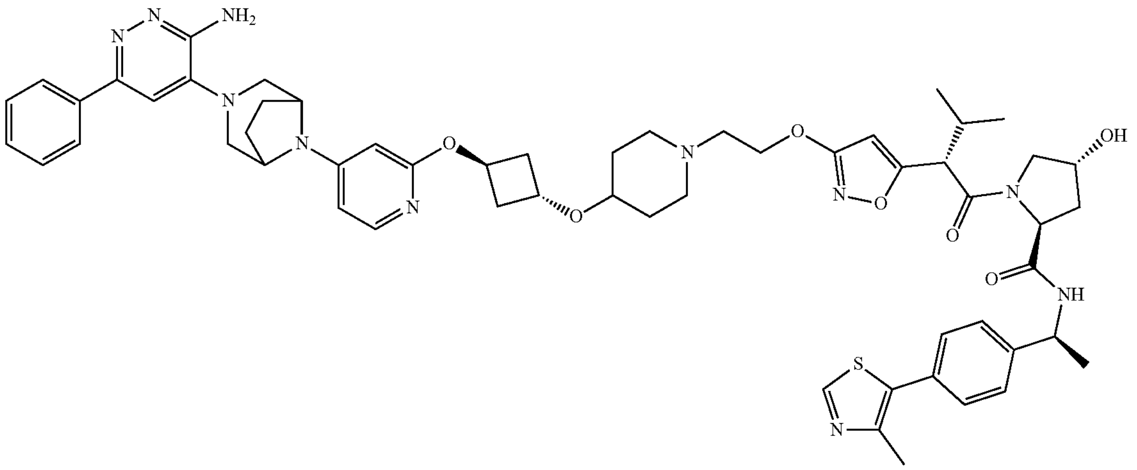 [SMILES: Cc1ncsc1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8)nnc6N)C7)ccn5)C4)CC3)no2)C(C)C)cc1] | (2S,4R)-1-((2S)-2-(3-(2-(4-((1r,3S)-3-((4-(3-(3-amino-6-phenylpyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 537 | 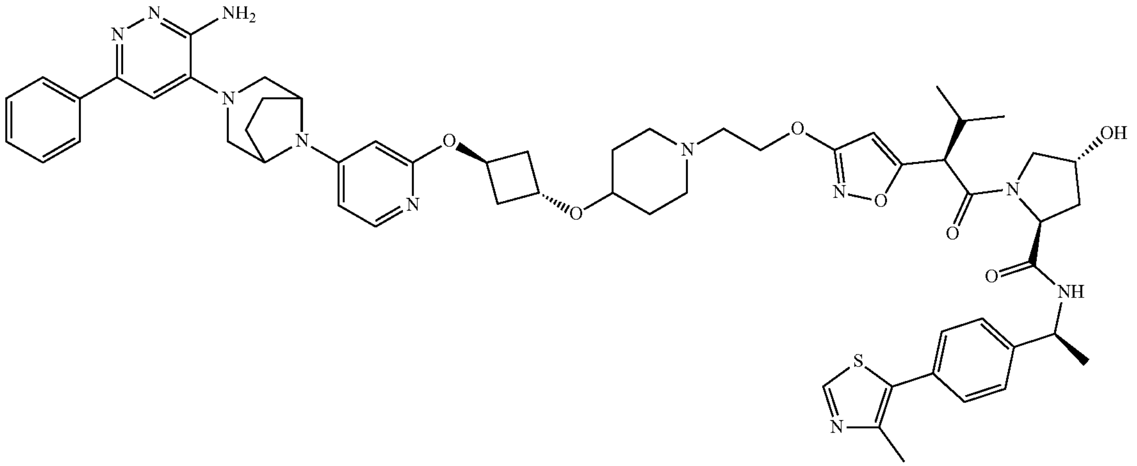 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8)nnc6N)C7)ccn5)C4)CC3)no2)C(C)C)cc1] | (2S,4R)-1-((2R)-2-(3-(2-(4-((1r,3R)-3-((4-(3-(3-amino-6-phenylpyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 538 | 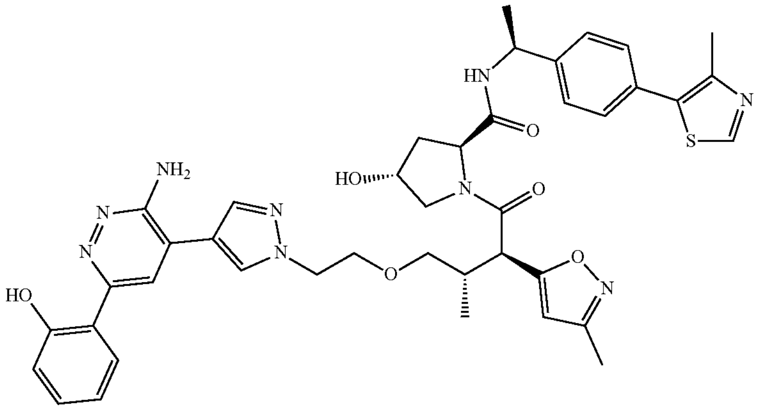 [SMILES: Cc1cc([C@H](C(=O)N2C[C@H](O)C[C@H]2C(=O)N[C@@H](C)c2ccc(-c3scnc3C)cc2)[C@H](C)COCCn2cc(-c3cc(-c4ccccc4O)nnc3N)cn2)on1] | (2S,4R)-1-((2R,3S)-4-(2-(4-(3-amino-6-(2-hydroxyphenyl)pyridazin-4-yl)-1H-pyrazol-1-yl)ethoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide |
| 539 | 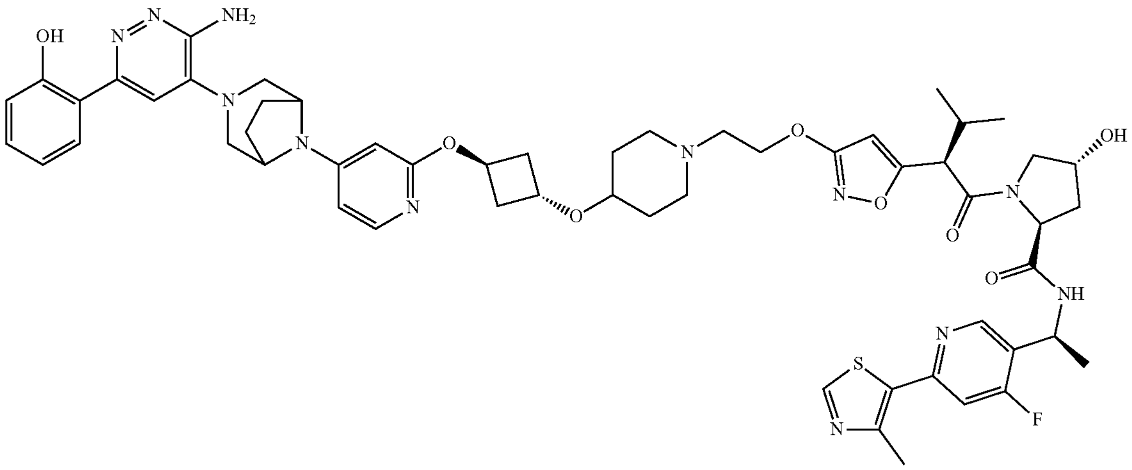 [SMILES: Cc1ncsc1-c1cc(F)c([C@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-fluoro-6-(4-methylthiazol-5-yl)pyridin-3-yl)ethyl)-4-hydroxypyrrolidine-2-carboxamide |

-continued

| []Exemplary bifunctional degradation compounds of the present disclosure | | |
|---|---|---|
| Ex No | Structure | Name |
| 540 | 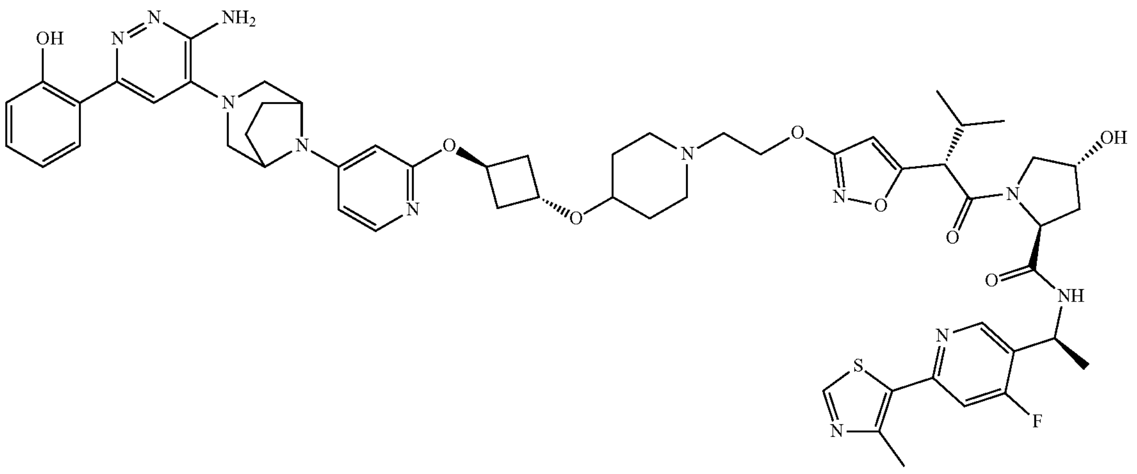 [SMILES: Cc1ncsc1-c1cc(F)c([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(4-fluoro-6-(4-methylthiazol-5-yl)pyridin-3-yl)ethyl)-4-hydroxypyrrolidine-2-carboxamide |
| 541 | 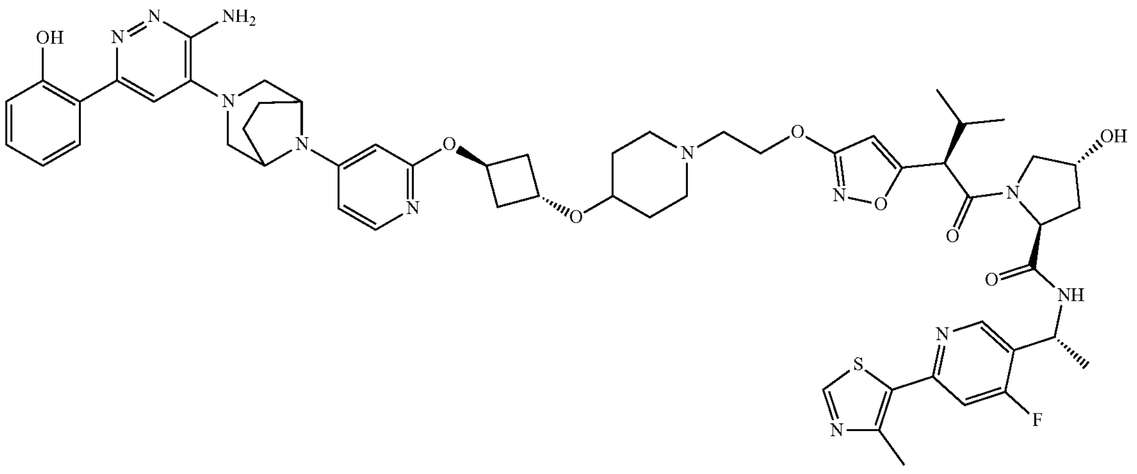 [SMILES: Cc1ncsc1-c1cc(F)c([C@@H](C)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-1-(4-fluoro-6-(4-methylthiazol-5-yl)pyridin-3-yl)ethyl)-4-hydroxypyrrolidine-2-carboxamide |

-continued

| []Exemplary bifunctional degradation compounds of the present disclosure | | |
|---|---|---|
| Ex No | Structure | Name |
| 542 | 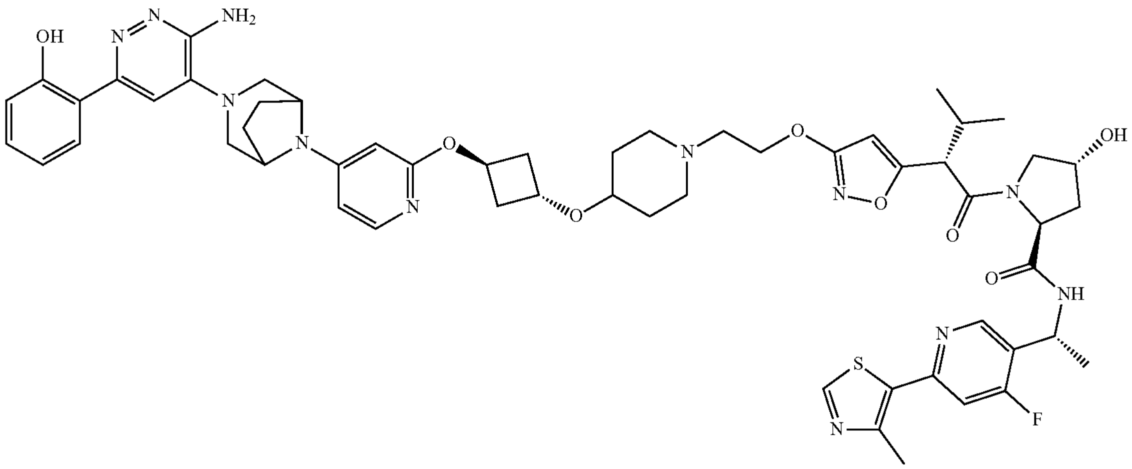 [SMILES: Cc1ncsc1-c1cc(F)c([C@@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-1-(4-fluoro-6-(4-methylthiazol-5-yl)pyridin-3-yl)ethyl)-4-hydroxypyrrolidine-2-carboxamide |
| 543 | 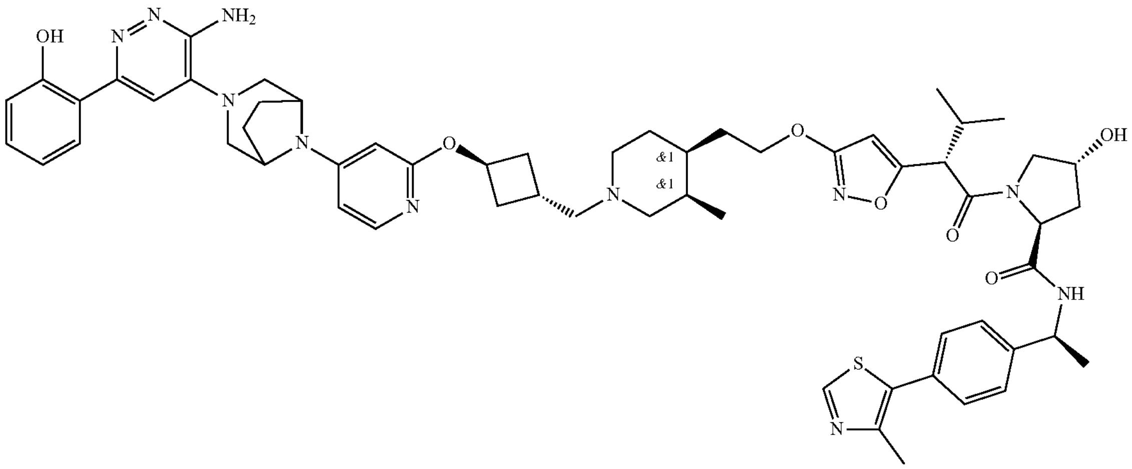 [SMILES: Cc1ncsc1-c1ccc([C@H](C)NC(=O)[C@@H]2C[C@@H](O)CN2C(=O)[C@H](c2cc(OCC[C@@H]3CCN(C[C@H]4C[C@H](Oc5cc(N6C7CCC6CN(c6cc(-c8ccccc8O)nnc6N)C7)ccn5)C4)C[C@@H]3C)no2)C(C)C)cc1] | (2S,4R)-1-((2S)-2-(3-(2-((3R,4S)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 544 | 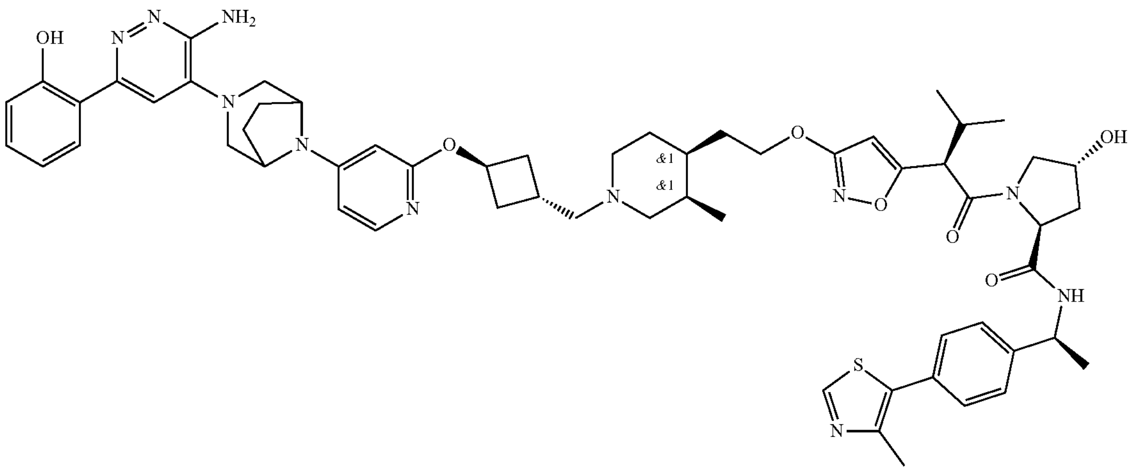 [SMILES: Cc1ncsc1-c1ccc([C@H](C)NC(=O)[C@@H]2C[C@@H](O)CN2C(=O)[C@@H](c2cc(OCC[C@@H]3CCN(C[C@H]4C[C@H](Oc5cc(N6C7CCC6CN(c6cc(-c8ccccc8O)nnc6N)C7)ccn5)C4)C[C@@H]3C)no2)C(C)C)cc1] | (2S,4R)-1-((2R)-2-(3-(2-((3R,4S)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 545 | 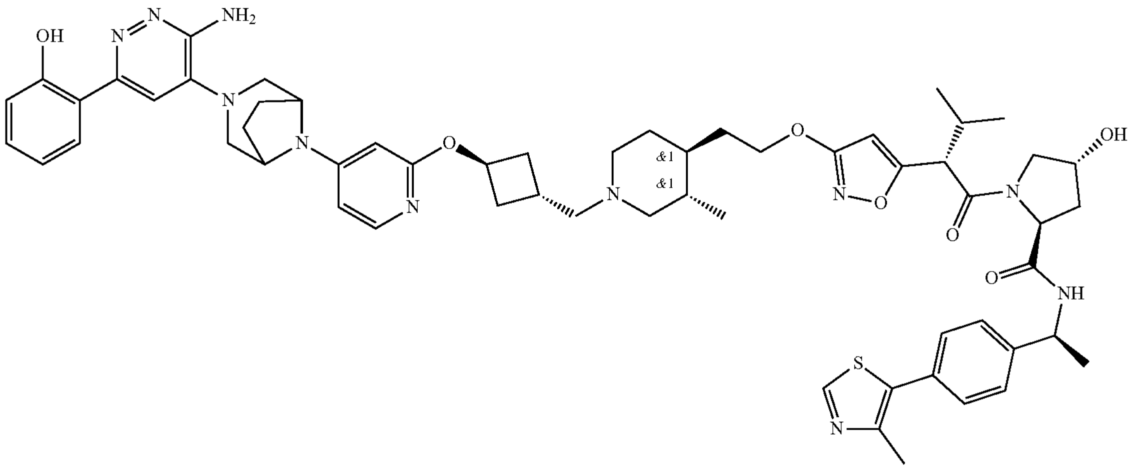 [SMILES: Cc1ncsc1-c1ccc([C@H](C)NC(=O)[C@@H]2C[C@@H](O)CN2C(=O)[C@H](c2cc(OCC[C@@H]3CCN(C[C@H]4C[C@H](Oc5cc(N6C7CCC6CN(c6cc(-c8ccccc8O)nnc6N)C7)ccn5)C4)C[C@H]3C)no2)C(C)C)cc1] | (2S,4R)-1-((2S)-2-(3-(2-((3S,4S)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 546 | 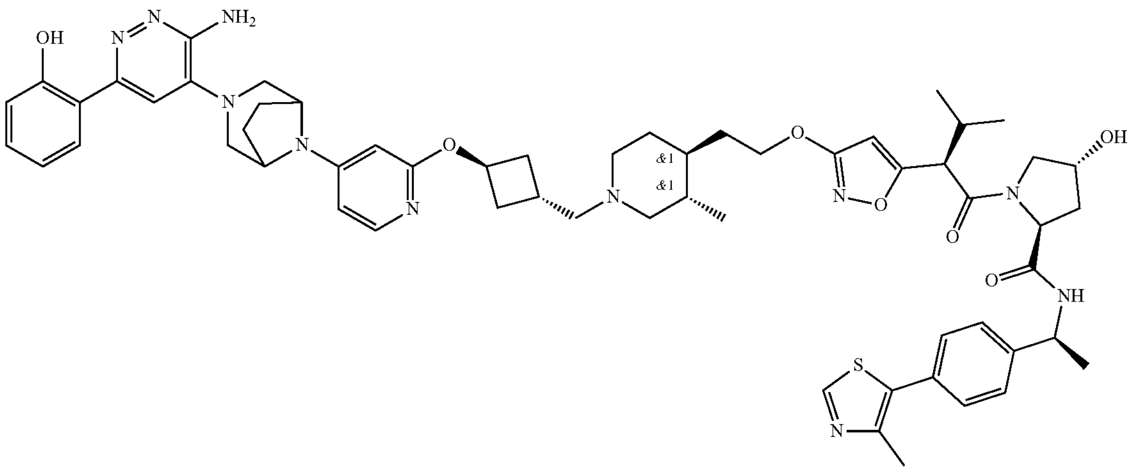 [SMILES: Cc1ncsc1-c1ccc([C@H](C)NC(=O)[C@@H]2C[C@@H](O)CN2C(=O)[C@@H](c2cc(OCC[C@@H]3CCN(C[C@H]4C[C@H](Oc5cc(N6C7CCC6CN(c6cc(-c8ccccc8O)nnc6N)C7)ccn5)C4)C[C@H]3C)no2)C(C)C)cc1] | (2S,4R)-1-((2R)-2-(3-(2-((3S,4S)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 547 | 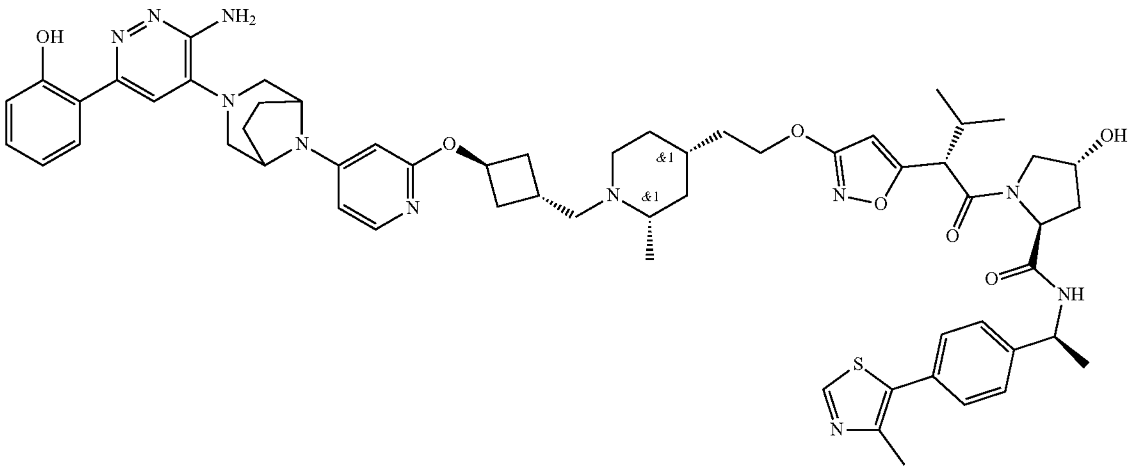 [SMILES: Cc1ncsc1-c1ccc([C@H](C)NC(=O)[C@@H]2C[C@@H](O)CN2C(=O)[C@H](c2cc(OCC[C@H]3CCN(C[C@H]4C[C@H](Oc5cc(N6C7CCC6CN(c6cc(-c8ccccc8O)nnc6N)C7)ccn5)C4)[C@@H](C)C3)no2)C(C)C)cc1] | (2S,4R)-1-((2S)-2-(3-(2-((2S,4S)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 548 | 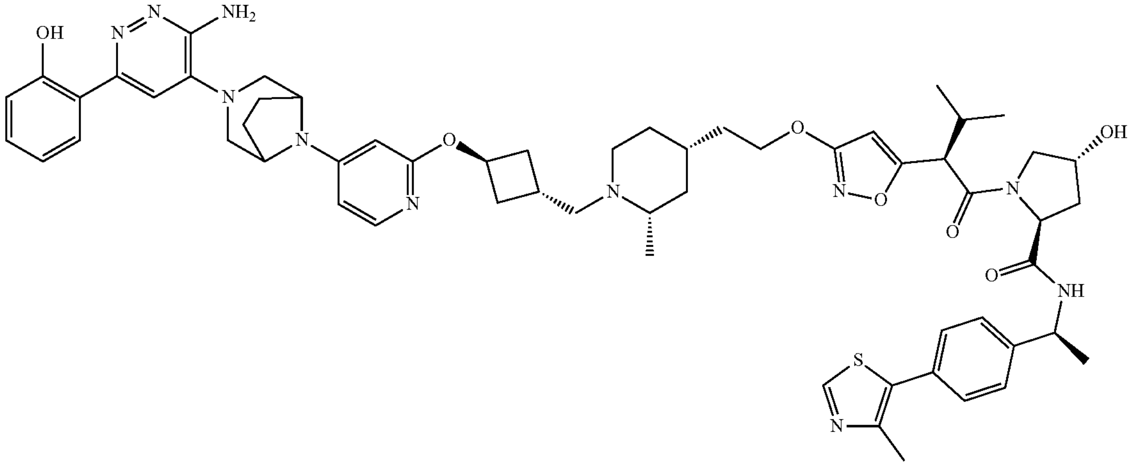 [SMILES: Cc1ncsc1-c1ccc([C@H](C)NC(=O)[C@@H]2C[C@@H](O)CN2C(=O)[C@@H](c2cc(OCC[C@H]3CCN(C[C@H]4C[C@H](Oc5cc(N6C7CCC6CN(c6cc(-c8ccccc8O)nnc6N)C7)ccn5)C4)[C@@H](C)C3)no2)C(C)C)cc1] | (2S,4R)-1-((2R)-2-(3-(2-((2S,4S)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 549 | 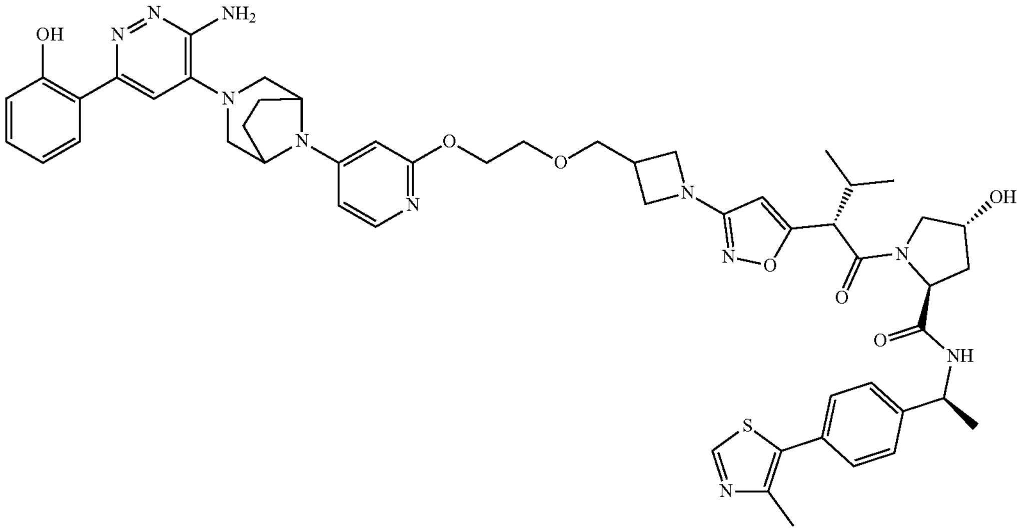 [SMILES: Cc1ncsc1-c1ccc([C@H](C)NC(=O)[C@@H]2C[C@@H](O)CN2C(=O)[C@H](c2cc(N3CC(COCCOc4cc(N5C6CCC5CN(c5cc(-c7ccccc7O)nnc5N)C6)ccn4)C3)no2)C(C)C)cc1] | (2S,4R)-1-((2S)-2-(3-(3-((2-((4-(3-(3-amino-6-(2-hydroxyphenyl)pyridazin-4-yl)-3,8-diazabicyclo[3.2.1]octan-8-yl)pyridin-2-yl)oxy)ethoxy)methyl)azetidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 550 | 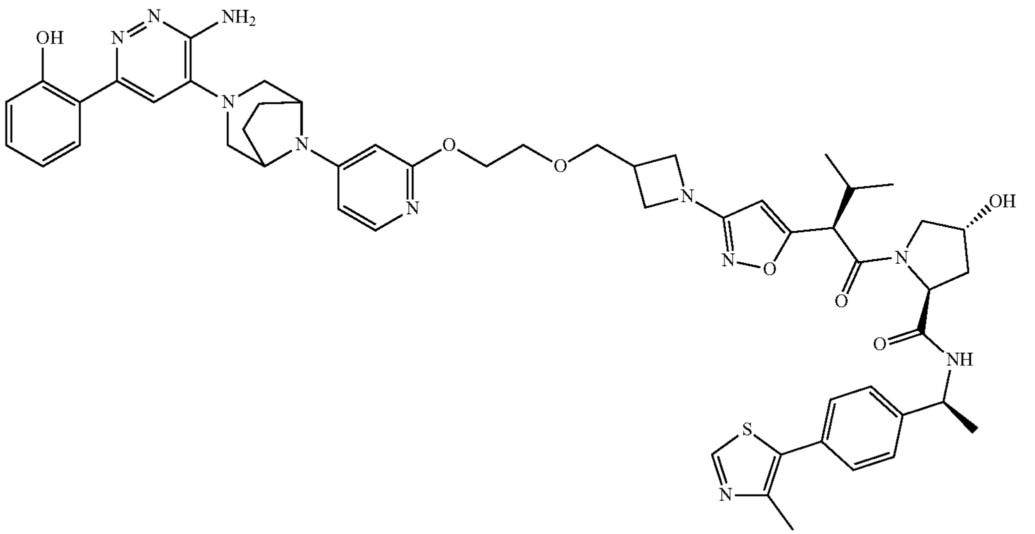 [SMILES: Cc1ncsc1-c1ccc([C@H](C)NC(=O)[C@@H]2C[C@@H](O)CN2C(=O)[C@@H](c2cc(N3CC(COCCOc4cc(N5C6CCC5CN(c5cc(-c7ccccc7O)nnc5N)C6)ccn4)C3)no2)C(C)C)cc1] | (2S,4R)-1-((2R)-2-(3-(3-((2-((4-(3-(3-amino-6-(2-hydroxyphenyl)pyridazin-4-yl)-3,8-diazabicyclo[3.2.1]octan-8-yl)pyridin-2-yl)oxy)ethoxy)methyl)azetidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 551 | 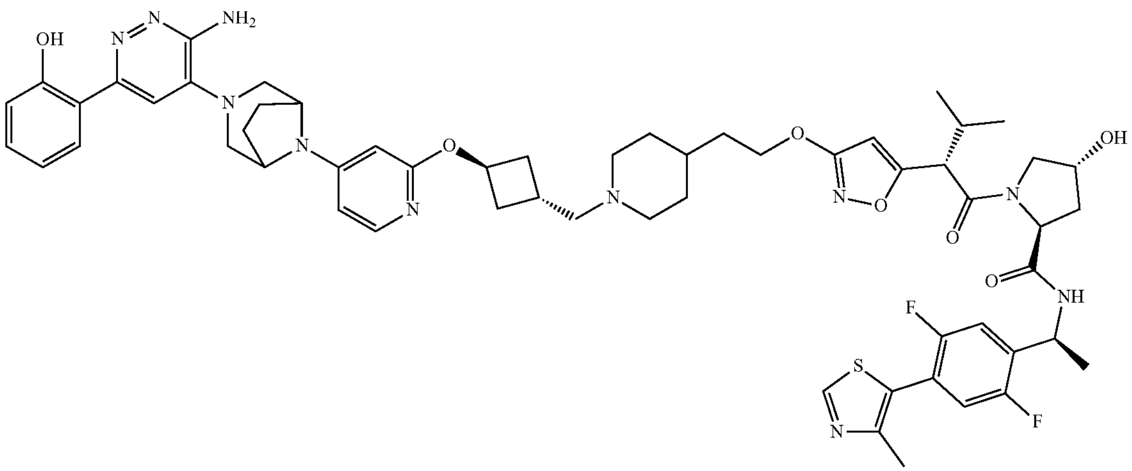 [SMILES: Cc1ncsc1-c1cc(F)c([C@H](C)NC(=O)[C@@H]2C[C@@H](O)CN2C(=O)[C@H](c2cc(OCCC3CCN(C[C@H]4C[C@H](Oc5cc(N6C7CCC6CN(c6cc(-c8ccccc8O)nnc6N)C7)ccn5)C4)CC3)no2)C(C)C)cc1F] | (2S,4R)-1-((2S)-2-(3-(2-(1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)ethoxy)isoxazol-5-yl)-3-methylbutanoyl)-N-((S)-1-(2,5-difluoro-4-(4-methylthiazol-5-yl)phenyl)ethyl)-4-hydroxypyrrolidine-2-carboxamide |

-continued

| []Exemplary bifunctional degradation compounds of the present disclosure | | |
|---|---|---|
| Ex No | Structure | Name |
| 552 | 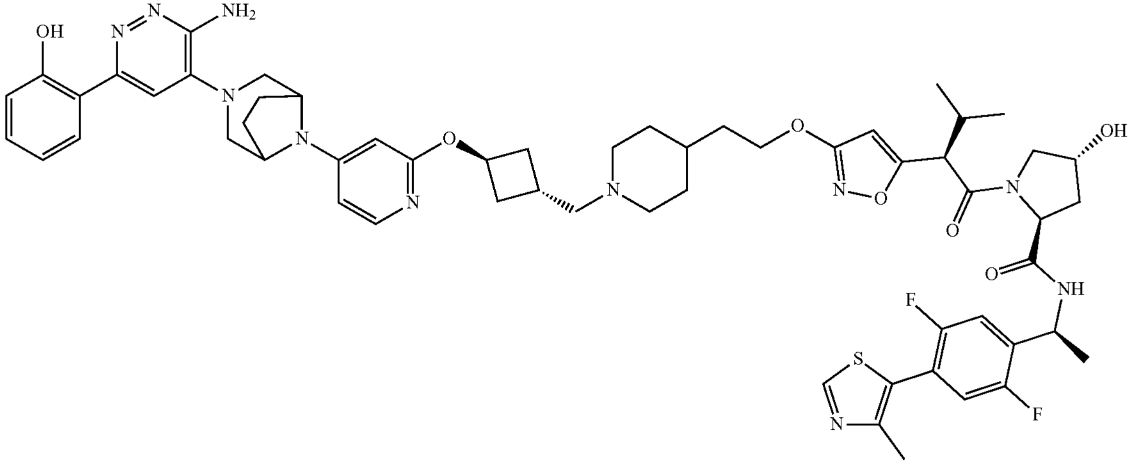 [SMILES: Cc1ncsc1-c1cc(F)c([C@H](C)NC(=O)[C@@H]2C[C@@H](O)CN2C(=O)[C@@H](c2cc(OCCC3CCN(C[C@H]4C[C@H](Oc5cc(N6C7CCC6CN(c6cc(-c8ccccc8O)nnc6N)C7)ccn5)C4)CC3)no2)C(C)C)cc1F] | (2S,4R)-1-((2R)-2-(3-(2-(1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)ethoxy)isoxazol-5-yl)-3-methylbutanoyl)-N-((S)-1-(2,5-difluoro-4-(4-methylthiazol-5-yl)phenyl)ethyl)-4-hydroxypyrrolidine-2-carboxamide |
| 553 | 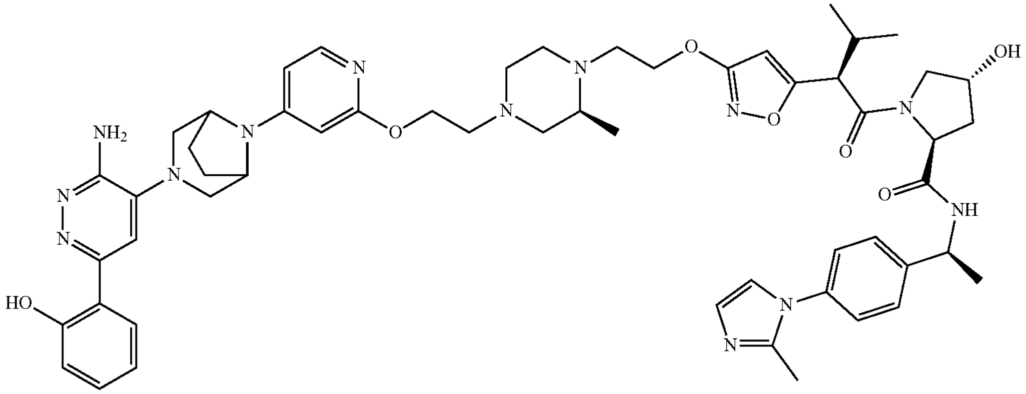 [SMILES: Cc1nccn1-c1ccc([C@H](C)NC(=O)[C@@H]2C[C@@H](O)CN2C(=O)[C@@H](c2cc(OCCN3CCN(CCOc4cc(N5C6CCC5CN(c5cc(-c7ccccc7O)nnc5N)C6)ccn4)C[C@@H]3C)no2)C(C)C)cc1] | (2S,4R)-1-((2R)-2-(3-(2-((2S)-4-(2-((4-(3-(3-amino-6-(2-hydroxyphenyl)pyridazin-4-yl)-3,8-diazabicyclo[3.2.1]octan-8-yl)pyridin-2-yl)oxy)ethyl)-2-methylpiperazin-1-yl)ethoxy)isoxazol-5-yl)-3-methylbutanoyl)-4-hydroxy-N-((S)-1-(4-(2-methyl-1H-imidazol-1-yl)phenyl)ethyl) pyrrolidine-2-carboxamide |

-continued

[]Exemplary bifunctional degradation compounds of the present disclosure

| Ex No | Structure | Name |
|---|---|---|
| 554 | 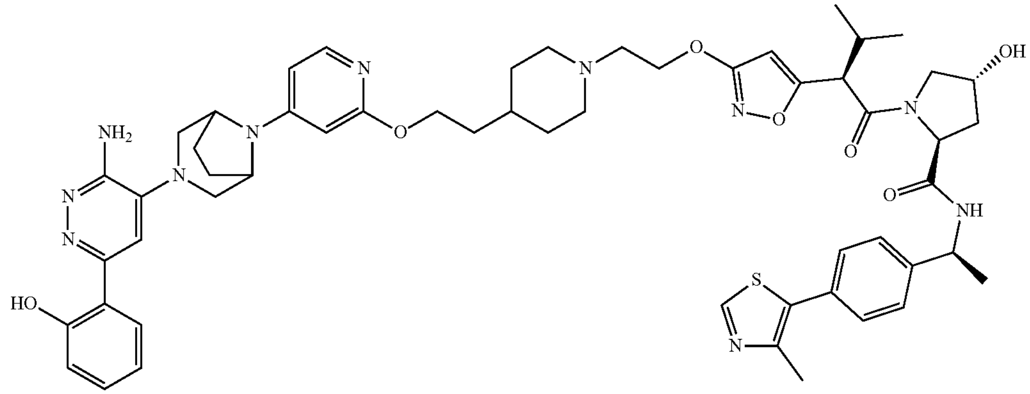 [SMILES: Cc1ncsc1-c1ccc([C@H](C)NC(=O)[C@@H]2C[C@@H](O)CN2C(=O)[C@@H](c2cc(OCCN3CCC(CCOc4cc(N5C6CCC5CN(c5cc(-c7ccccc7O)nnc5N)C6)ccn4)CC3)no2)C(C)C)cc1] | (2S,4R)-1-((2R)-2-(3-(2-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 555 | 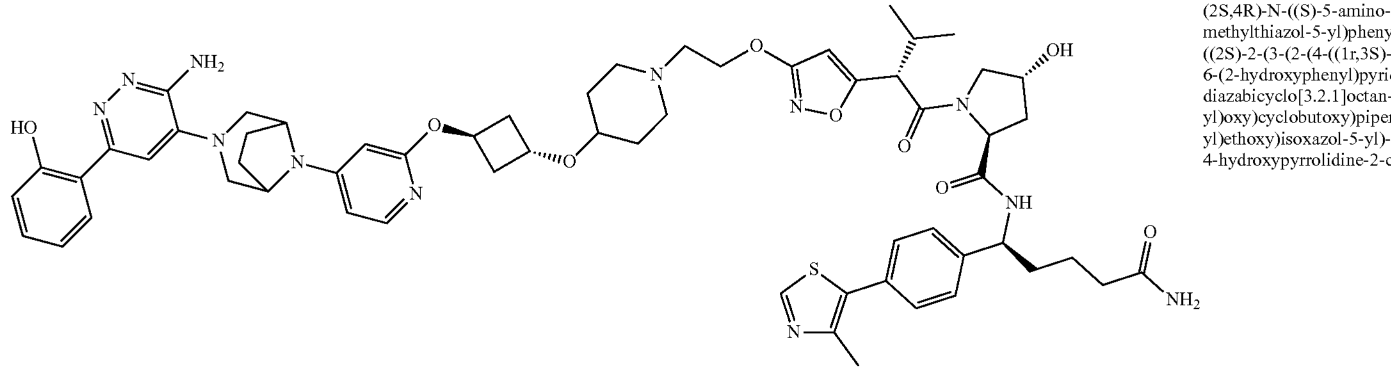 | (2S,4R)-N-((S)-5-amino-1-(4-(4-methylthiazol-5-yl)phenyl)-5-oxopentyl)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamide |

-continued

[]Exemplary bifunctional degradation compounds of the present disclosure

| Ex No | Structure | Name |
|---|---|---|
| 556 | 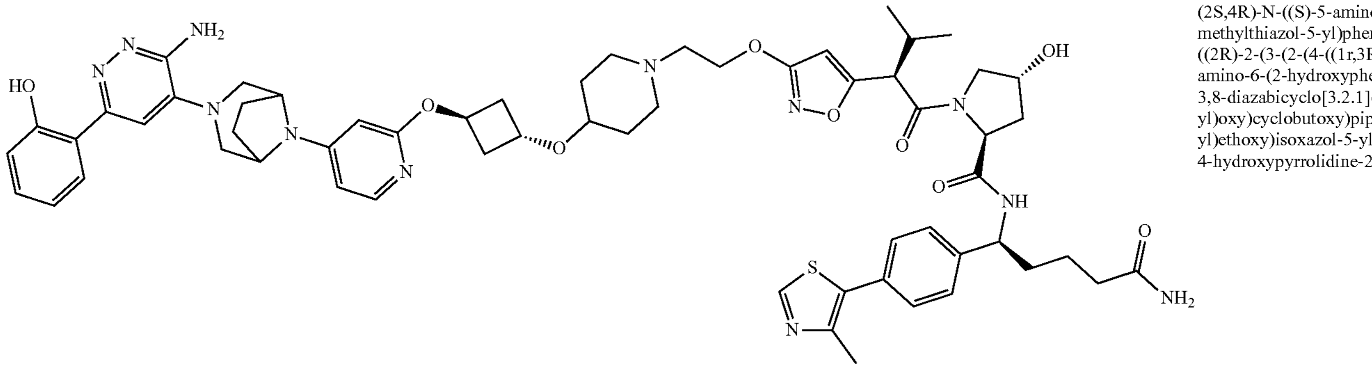 | (2S,4R)-N-((S)-5-amino-1-(4-(4-methylthiazol-5-yl)phenyl)-5-oxopentyl)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamide |
| 557 | 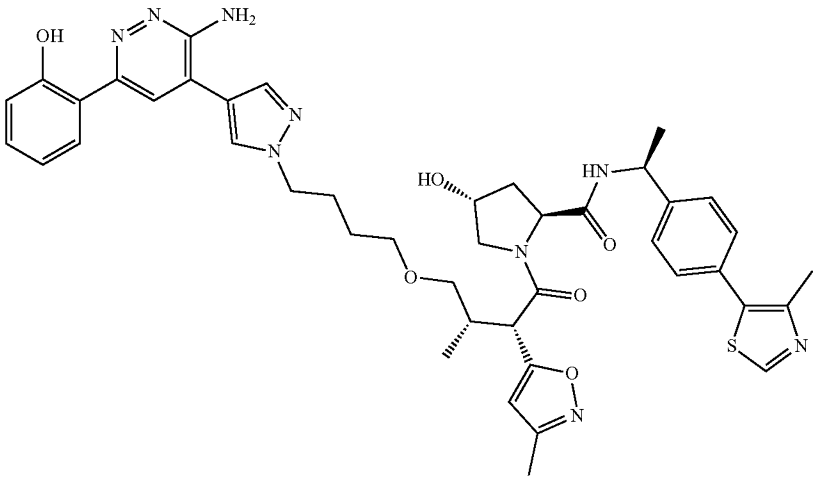 [SMILES: Cc1cc([C@@H](C(=O)N2C[C@H](O)C[C@H]2C(=O)N[C@@H](C)c2ccc(-c3scnc3C)cc2)[C@H](C)COCCCCn2cc(-c3cc(-c4ccccc4O)nnc3N)cn2)on1] | (2S,4R)-1-((2S,3S)-4-(4-(4-(3-amino-6-(2-hydroxyphenyl)pyridazin-4-yl)-1H-pyrazol-1-yl)butoxy)-3-methyl-2-(3-methylisoxazol-5-yl)butanoyl)-4-hydroxy-N-((S)-1-(4-(4-methylthiazol-5-yl)phenyl)ethyl) pyrrolidine-2-carboxamide |

-continued
| []Exemplary bifunctional degradation compounds of the present disclosure | | |
| --- | --- | --- |
| Ex No | Structure | Name |
| 558 | 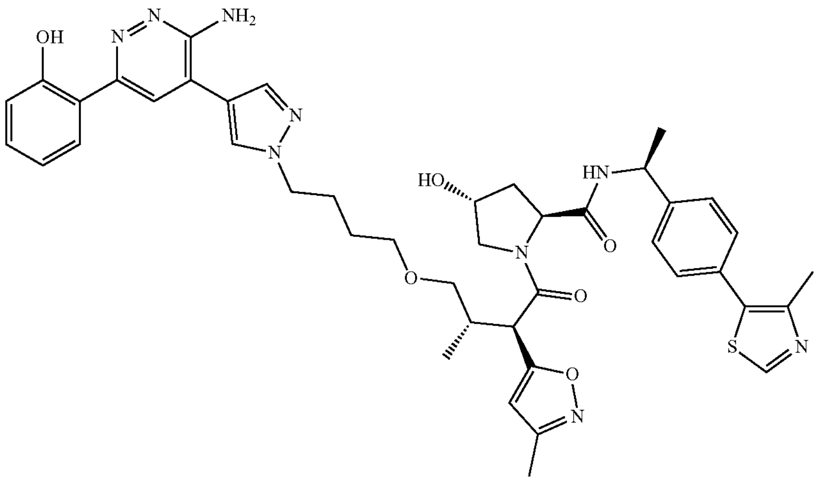 [SMILES: Cc1cc([C@H](C(=O)N2C[C@H](O)C[C@H]2C(=O)N[C@@H](C)c2ccc(-c3scnc3C)cc2)[C@H](C)COCCCCn2cc(-c3cc(-c4ccccc4O)nnc3N)cn2)on1] | (2S,4R)-1-((2R,3S)-4-(4-(4-(3-amino-6-(2-hydroxyphenyl)pyridazin-4-yl)-1H-pyrazol-1-yl)butoxy)-3-methyl-2-(3-methylisoxazol-5-yl)butanoyl)-4-hydroxy-N-((S)-1-(4-(4-methylthiazol-5-yl)phenyl)ethyl) pyrrolidine-2-carboxamide |

-continued
| []Exemplary bifunctional degradation compounds of the present disclosure | | |
|---|---|---|
| Ex No | Structure | Name |
| 559 | 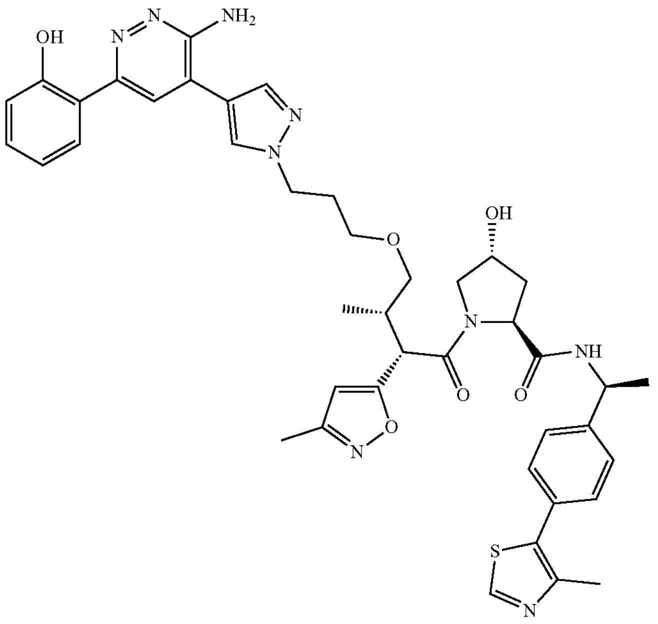 [SMILES: Cc1cc([C@@H](C(=O)N2C[C@H](O)C[C@H]2C(=O)N[C@@H](C)c2ccc(-c3scnc3C)cc2)[C@H](C)COCCCn2cc(-c3cc(-c4ccccc4O)nnc3N)cn2)on1] | (2S,4R)-1-((2S,3S)-4-(3-(4-(3-amino-6-(2-hydroxyphenyl)pyridazin-4-yl)-1H-pyrazol-1-yl)propoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide |

-continued
| []Exemplary bifunctional degradation compounds of the present disclosure | | |
|---|---|---|
| Ex No | Structure | Name |
| 560 | 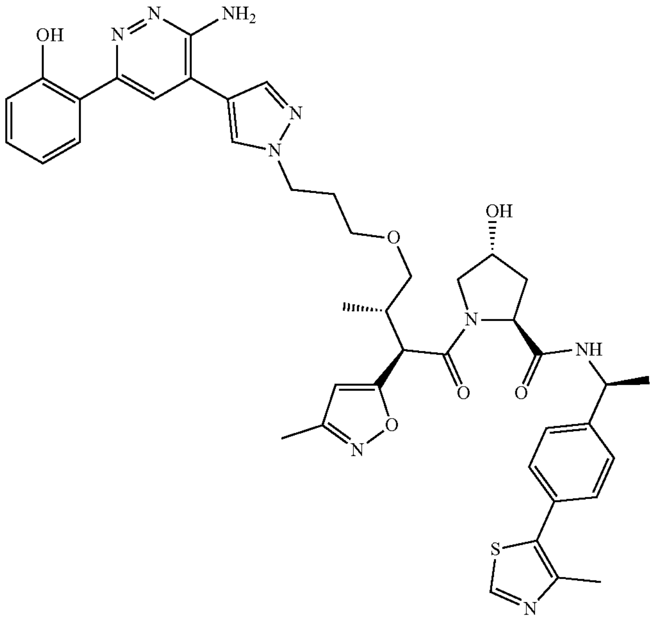 [SMILES: Cc1cc([C@H](C(=O)N2C[C@H](O)C[C@H]2C(=O)N[C@@H](C)c2ccc(-c3scnc3C)cc2)[C@H](C)COCCCn2cc(-c3cc(-c4ccccc4O)nnc3N)cn2)on1] | (2S,4R)-1-((2R,3S)-4-(3-(4-(3-amino-6-(2-hydroxyphenyl)pyridazin-4-yl)-1H-pyrazol-1-yl)propoxy)-3-methyl-2-(3-methylisoxazol-5-yl)butanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 561 | 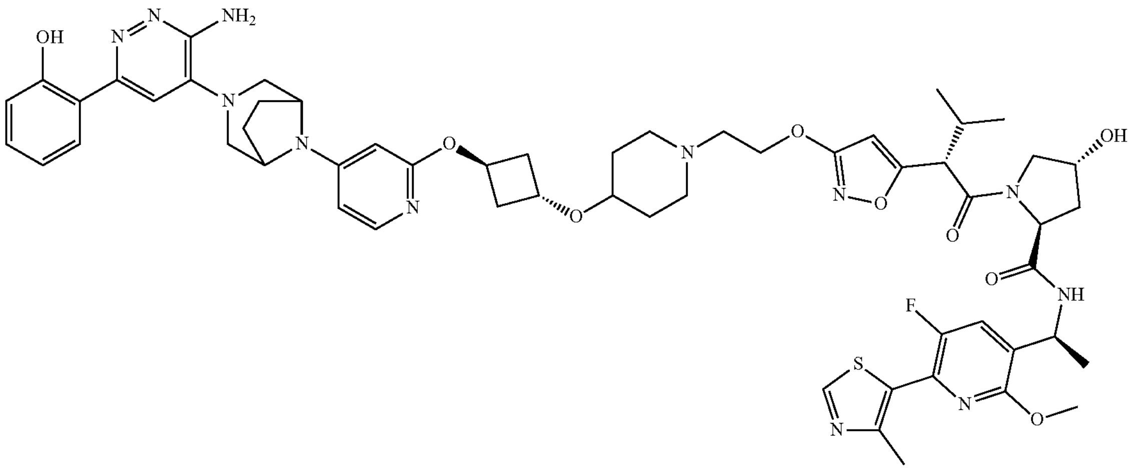 [SMILES: COc1nc(-c2scnc2C)c(F)cc1[C@H](C)NC(=O)[C@@H]1C[C@@H](O)CN1C(=O)[C@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(5-fluoro-2-methoxy-6-(4-methylthiazol-5-yl)pyridin-3-yl)ethyl)-4-hydroxypyrrolidine-2-carboxamide |
| 562 | 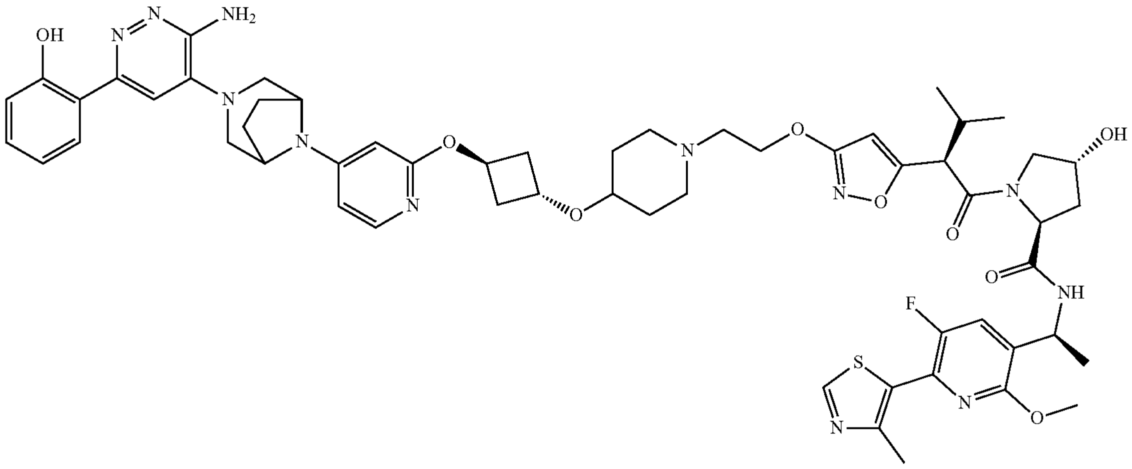 [SMILES: COc1nc(-c2scnc2C)c(F)cc1[C@H](C)NC(=O)[C@@H]1C[C@@H](O)CN1C(=O)[C@@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((S)-1-(5-fluoro-2-methoxy-6-(4-methylthiazol-5-yl)pyridin-3-yl)ethyl)-4-hydroxypyrrolidine-2-carboxamide |

-continued

[]Exemplary bifunctional degradation compounds of the present disclosure

| Ex No | Structure | Name |
|---|---|---|
| 563 | 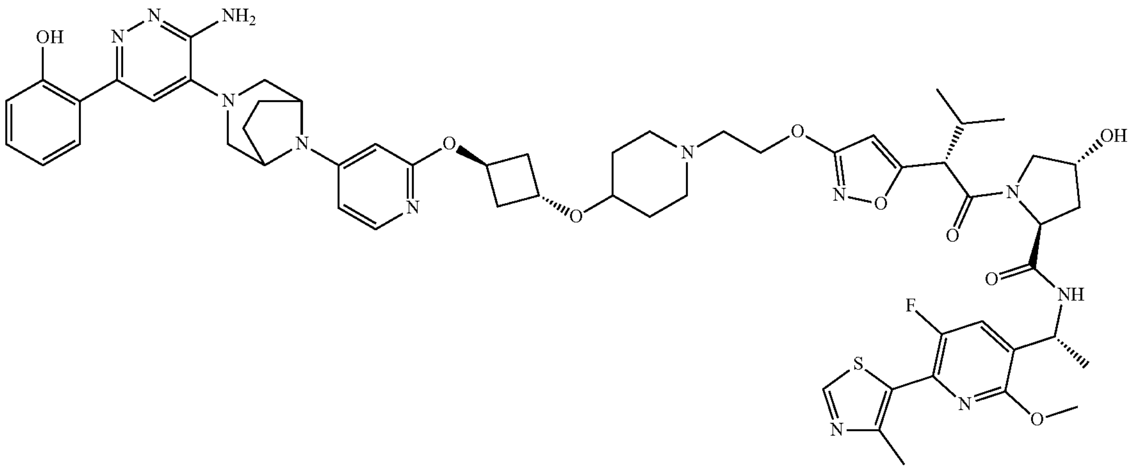 [SMILES: COc1nc(-c2scnc2C)c(F)cc1[C@@H](C)NC(=O)[C@@H]1C[C@@H](O)CN1C(=O)[C@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-1-(5-fluoro-2-methoxy-6-(4-methylthiazol-5-yl)pyridin-3-yl)ethyl)-4-hydroxypyrrolidine-2-carboxamide |
| 564 | 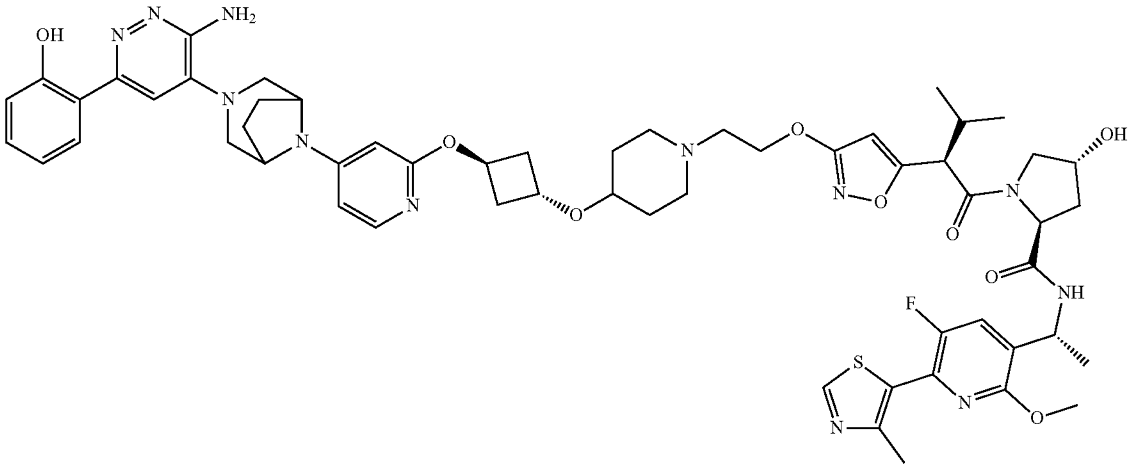 [SMILES: COc1nc(-c2scnc2C)c(F)cc1[C@@H](C)NC(=O)[C@@H]1C[C@@H](O)CN1C(=O)[C@@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C] | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-N-((R)-1-(5-fluoro-2-methoxy-6-(4-methylthiazol-5-yl)pyridin-3-yl)ethyl)-4-hydroxypyrrolidine-2-carboxamide |

-continued

| Ex No | Structure | Name |
| --- | --- | --- |
| | []Exemplary bifunctional degradation compounds of the present disclosure | |
| 565 | 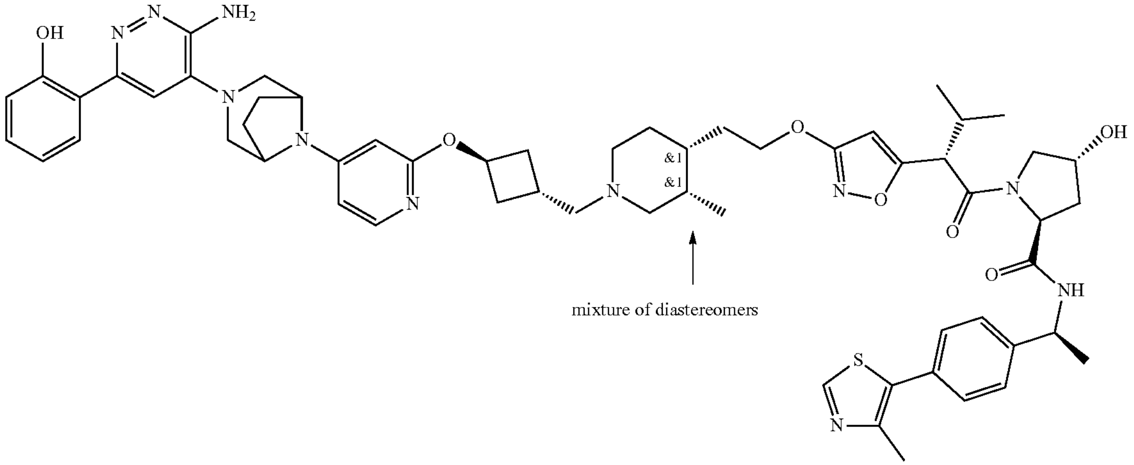 [SMILES: Cc1ncsc1-c1ccc([C@H](C)NC(=O)[C@@H]2C[C@@H](O)CN2C(=O)[C@H](c2cc(OCC[C@H]3CCN(C[C@H]4C[C@H](Oc5cc(N6C7CCC6CN(c6cc(-c8ccccc8O)nnc6N)C7)ccn5)C4)C[C@H]3C)no2)C(C)C)cc1] | (2S,4R)-1-((2S)-2-(3-(2-((3S,4R)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 566 | 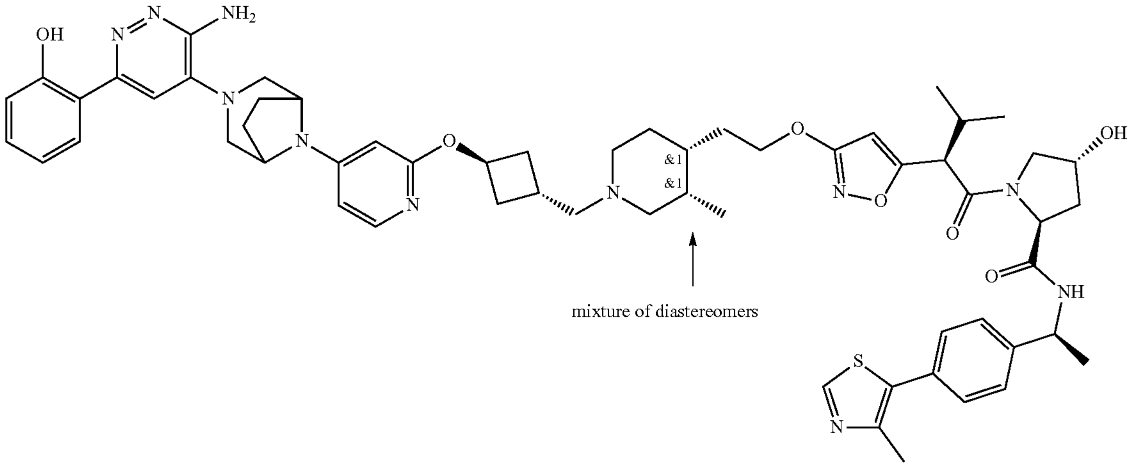 [SMILES: Cc1ncsc1-c1ccc([C@H](C)NC(=O)[C@@H]2C[C@@H](O)CN2C(=O)[C@@H](c2cc(OCC[C@H]3CCN(C[C@H]4C[C@H](Oc5cc(N6C7CCC6CN(c6cc(-c8ccccc8O)nnc6N)C7)ccn5)C4)C[C@H]3C)no2)C(C)C)cc1] | (2S,4R)-1-((2R)-2-(3-(2-((3S,4R)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
| --- | --- | --- |
| | []Exemplary bifunctional degradation compounds of the present disclosure | |
| 567 | 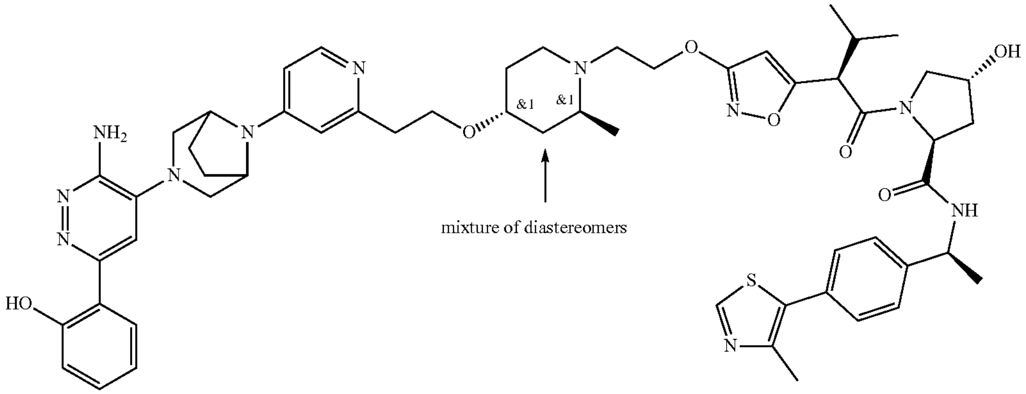 [SMILES: Cc1ncsc1-c1ccc([C@H](C)NC(=O)[C@@H]2C[C@@H](O)CN2C(=O)[C@@H](c2cc(OCCN3CC[C@@H](OCCc4cc(N5C6CCC5CN(c5cc(-c7ccccc7O)nnc5N)C6)ccn4)C[C@@H]3C)no2)C(C)C)cc1] | (2S,4R)-1-((2R)-2-(3-(2-((2S,4R)-4-(2-(4-(3-(3-amino-6-(2-hydroxyphenyl)pyridazin-4-yl)-3,8-diazabicyclo[3.2.1]octan-8-yl)pyridin-2-yl)ethoxy)-2-methylpiperidin-1-yl)ethoxy)isoxazol-5-yl)-3-methylbutanoyl)-4-hydroxy-N-((S)-1-(4-(4-methylthiazol-5-yl)phenyl)ethyl) pyrrolidine-2-carboxamide |
| 568 | 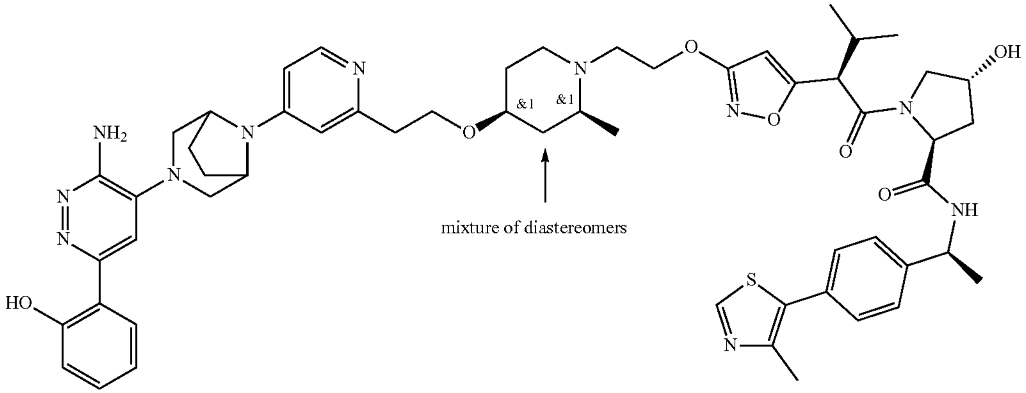 [SMILES: Cc1ncsc1-c1ccc([C@H](C)NC(=O)[C@@H]2C[C@@H](O)CN2C(=O)[C@@H](c2cc(OCCN3CC[C@H](OCCc4cc(N5C6CCC5CN(c5cc(-c7ccccc7O)nnc5N)C6)ccn4)C[C@@H]3C)no2)C(C)C)cc1] | (2S,4R)-1-((2R)-2-(3-(2-((2S,4S)-4-(2-(4-(3-(3-amino-6-(2-hydroxyphenyl)pyridazin-4-yl)-3,8-diazabicyclo[3.2.1]octan-8-yl)pyridin-2-yl)ethoxy)-2-methylpiperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 569 | 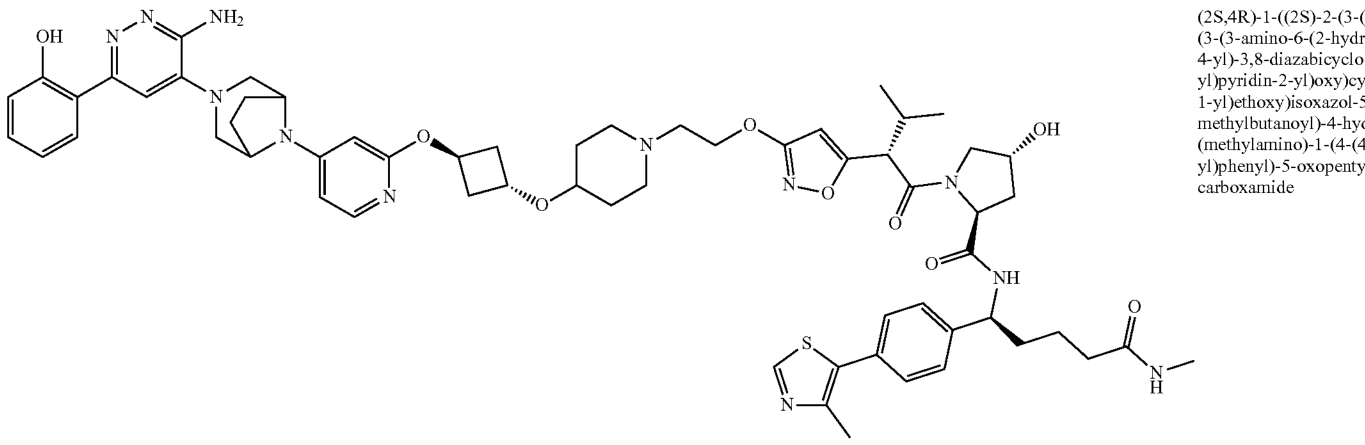 | (2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-5-(methylamino)-1-(4-(4-methylthiazol-5-yl)phenyl)-5-oxopentyl)pyrrolidine-2-carboxamide |
| 570 | 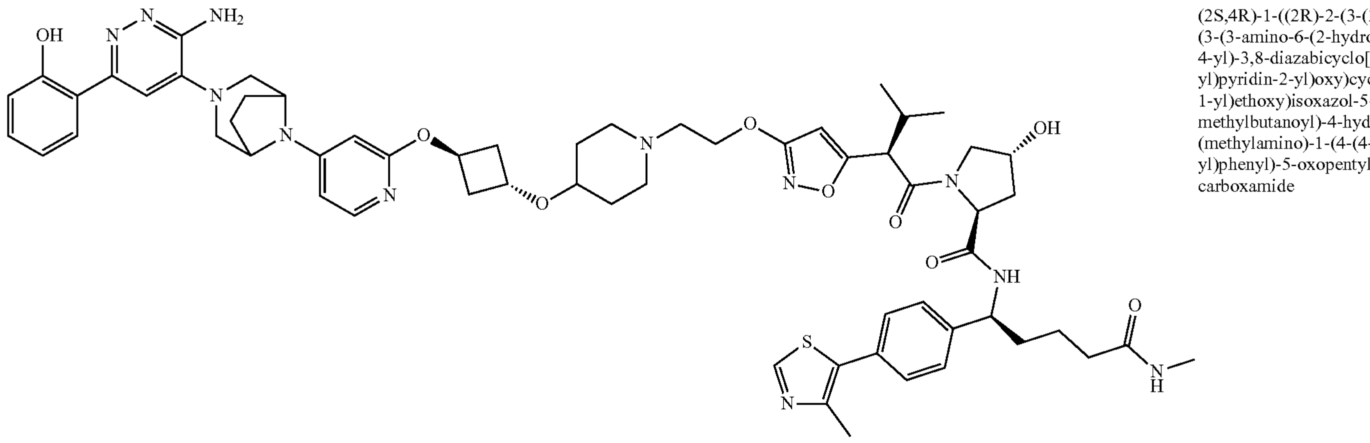 | (2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxy-N-((S)-5-(methylamino)-1-(4-(4-methylthiazol-5-yl)phenyl)-5-oxopentyl)pyrrolidine-2-carboxamide |

-continued

| []Exemplary bifunctional degradation compounds of the present disclosure | | |
|---|---|---|
| Ex No | Structure | Name |
| 571 | 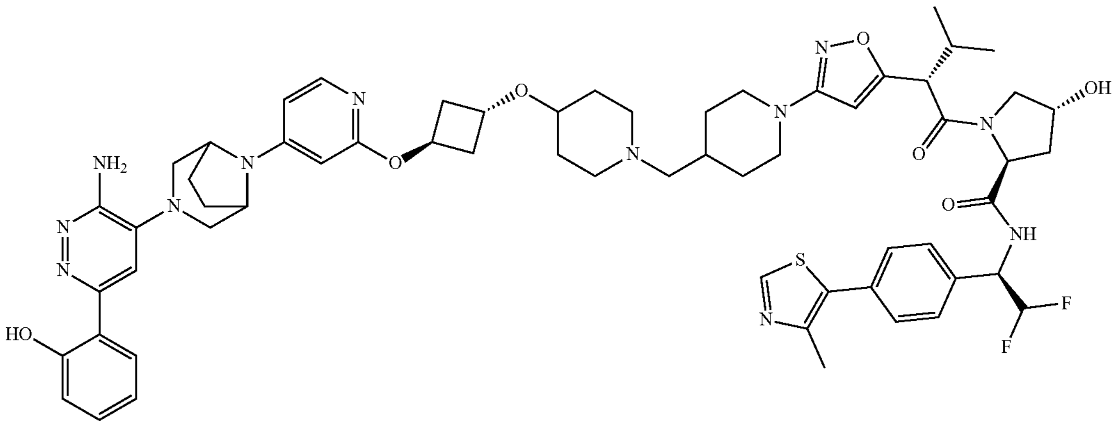 [SMILES: Cc1ncsc1-c1ccc([C@@H](NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)C(F)F)cc1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((R)-2,2-difluoro-1-(4-(4-methylthiazol-5-yl)phenyl)ethyl)-4-hydroxypyrrolidine-2-carboxamide |
| 572 | 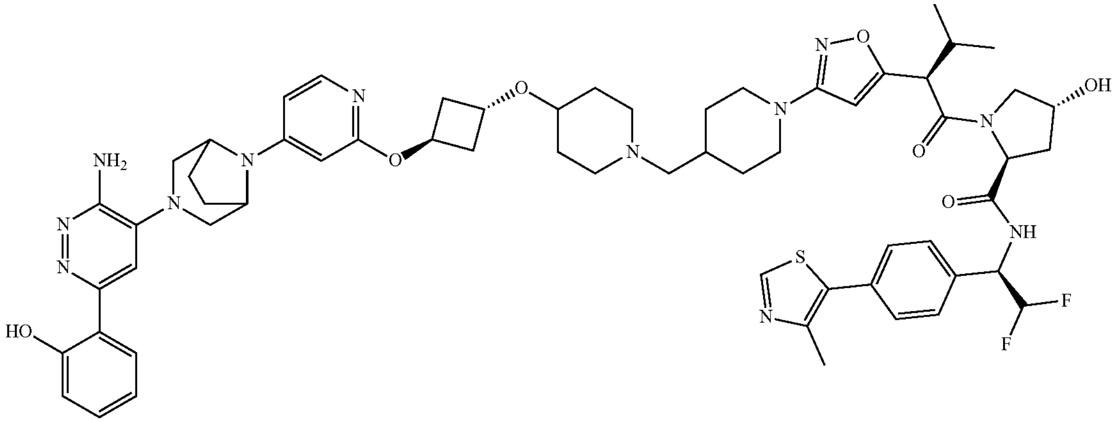 [SMILES: Cc1ncsc1-c1ccc([C@@H](NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)C(F)F)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((R)-2,2-difluoro-1-(4-(4-methylthiazol-5-yl)phenyl)ethyl)-4-hydroxypyrrolidine-2-carboxamide |

-continued

| []Exemplary bifunctional degradation compounds of the present disclosure | | |
|---|---|---|
| Ex No | Structure | Name |
| 573 | 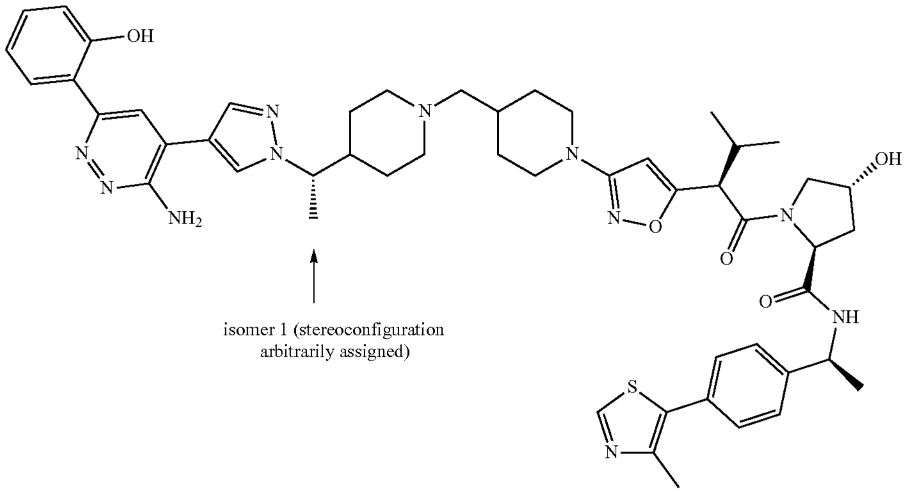 [SMILES: Cc1ncsc1-c1ccc([C@H](C)NC(=O)[C@@H]2C[C@@H](O)CN2C(=O)[C@@H](c2cc(N3CCC(CN4CCC([C@H](C)n5cc(-c6cc(-c7ccccc7O)nnc6N)cn5)CC4)CC3)no2)C(C)C)cc1] isomer 1 (stereoconfiguration arbitrarily assigned) | (2S,4R)-1-((R)-2-(3-(4-((4-((S)-1-(4-(3-amino-6-(2-hydroxyphenyl)pyridazin-4-yl)-1H-pyrazol-1-yl)ethyl)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 574 | 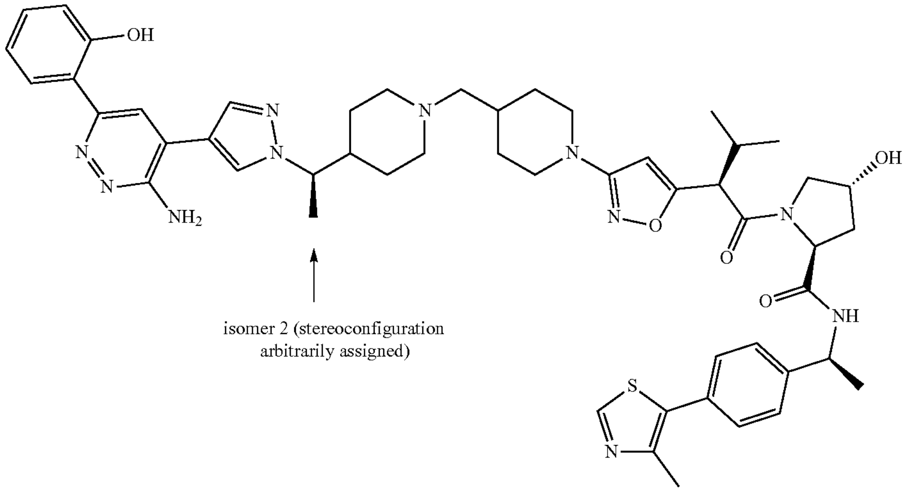 [SMILES: Cc1ncsc1-c1ccc([C@H](C)NC(=O)[C@@H]2C[C@@H](O)CN2C(=O)[C@@H](c2cc(N3CCC(CN4CCC([C@@H](C)n5cc(-c6cc(-c7ccccc7O)nnc6N)cn5)CC4)CC3)no2)C(C)C)cc1] isomer 2 (stereoconfiguration arbitrarily assigned) | (2S,4R)-1-((R)-2-(3-(4-((4-((R)-1-(4-(3-amino-6-(2-hydroxyphenyl)pyridazin-4-yl)-1H-pyrazol-1-yl)ethyl)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 575 | 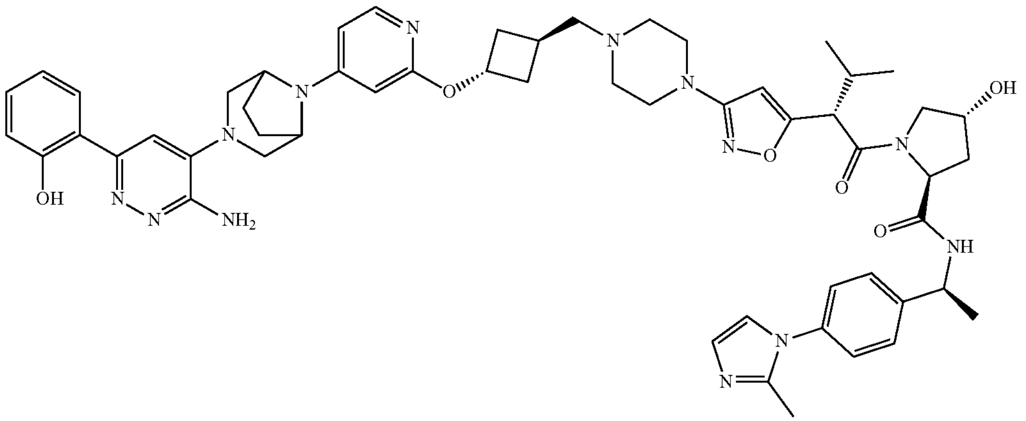 [SMILES: Cc1nccn1-c1ccc([C@H](C)NC(=O)[C@@H]2C[C@@H](O)CN2C(=O)[C@H](c2cc(N3CCN(C[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(4-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperazin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |
| 576 | 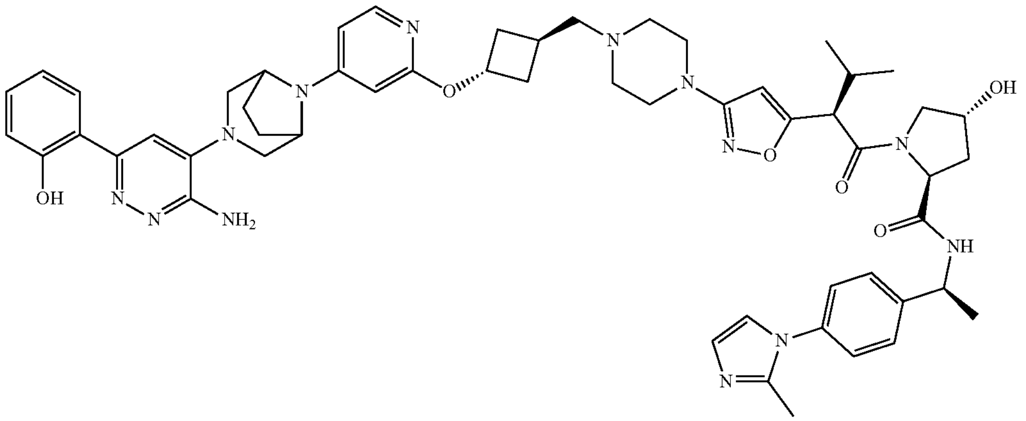 | (2S,4R)-1-((2R)-2-(3-(4-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperazin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

-continued

| []Exemplary bifunctional degradation compounds of the present disclosure | | |
|---|---|---|
| Ex No | Structure | Name |
| 577 | 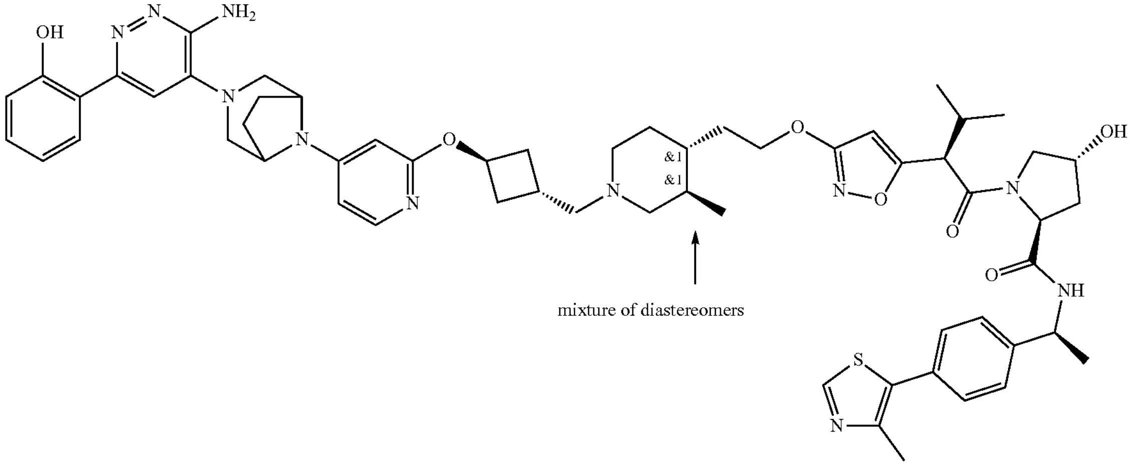 [SMILES: Cc1ncsc1-c1ccc([C@H](C)NC(=O)[C@@H]2C[C@@H](O)CN2C(=O)[C@@H](c2cc(OCC[C@H]3CCN(C[C@H]4C[C@H](Oc5cc(N6C7CCC6CN(c6cc(-c8ccccc8O)nnc6N)C7)ccn5)C4)C[C@@H]3C)no2)C(C)C)cc1] | (2S,4R)-1-((2R)-2-(3-(2-((3R,4R)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 578 | 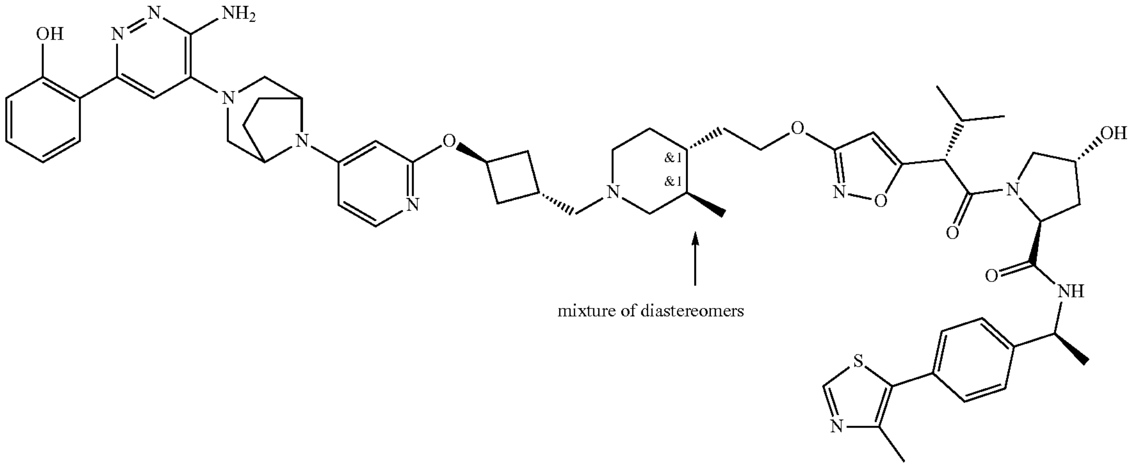 [SMILES: Cc1ncsc1-c1ccc([C@H](C)NC(=O)[C@@H]2C[C@@H](O)CN2C(=O)[C@H](c2cc(OCC[C@H]3CCN(C[C@H]4C[C@H](Oc5cc(N6C7CCC6CN(c6cc(-c8ccccc8O)nnc6N)C7)ccn5)C4)C[C@@H]3C)no2)C(C)C)cc1] | (2S,4R)-1-((2S)-2-(3-(2-((3R,4R)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 579 | 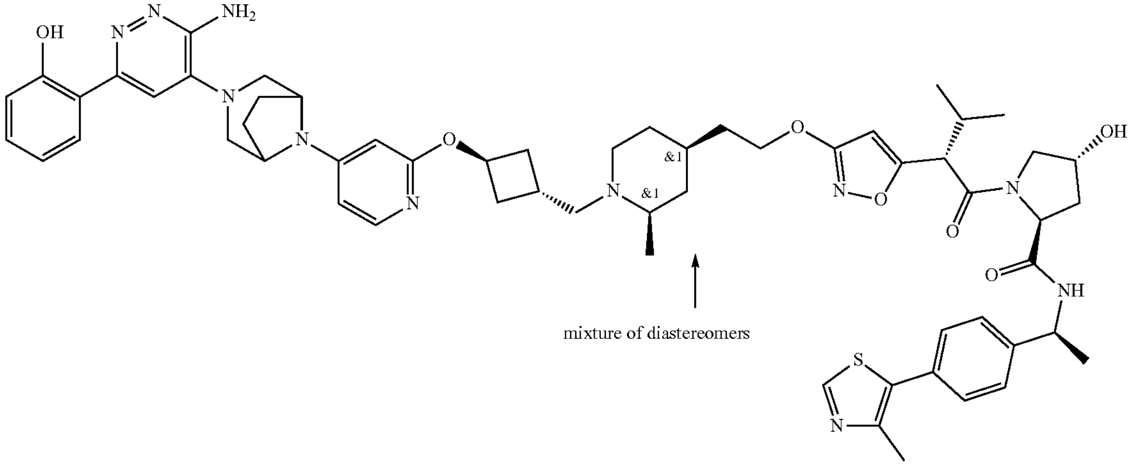 [SMILES: Cc1ncsc1-c1ccc([C@H](C)NC(=O)[C@@H]2C[C@@H](O)CN2C(=O)[C@H](c2cc(OCC[C@@H]3CCN(C[C@H]4C[C@H](Oc5cc(N6C7CCC6CN(c6cc(-c8ccccc8O)nnc6N)C7)ccn5)C4)[C@H](C)C3)no2)C(C)C)cc1] mixture of diastereomers | (2S,4R)-1-((2S)-2-(3-(2-((2R,4R)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 580 | 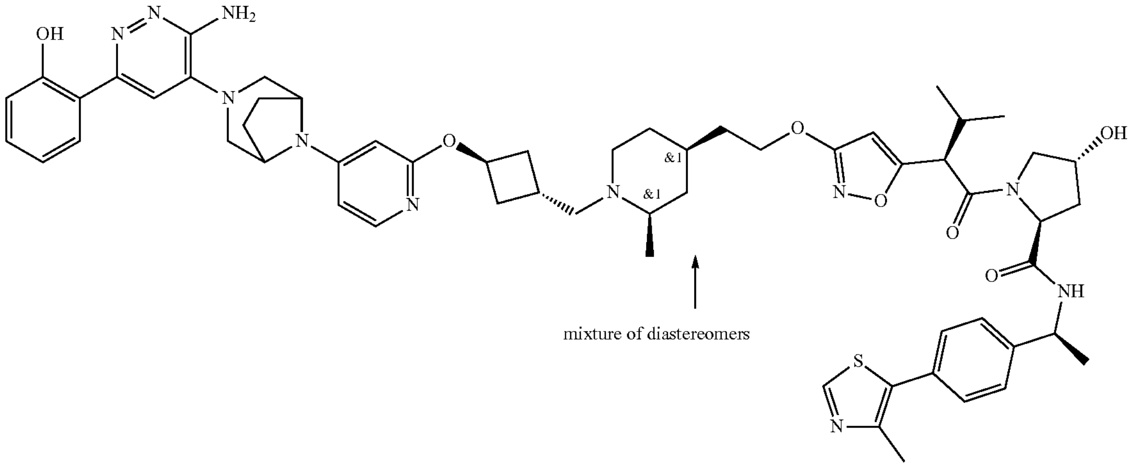 [SMILES: Cc1ncsc1-c1ccc([C@H](C)NC(=O)[C@@H]2C[C@@H](O)CN2C(=O)[C@@H](c2cc(OCC[C@@H]3CCN(C[C@H]4C[C@H](Oc5cc(N6C7CCC6CN(c6cc(-c8ccccc8O)nnc6N)C7)ccn5)C4)[C@H](C)C3)no2)C(C)C)cc1] mixture of diastereomers | (2S,4R)-1-((2R)-2-(3-(2-((2R,4R)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 581 | 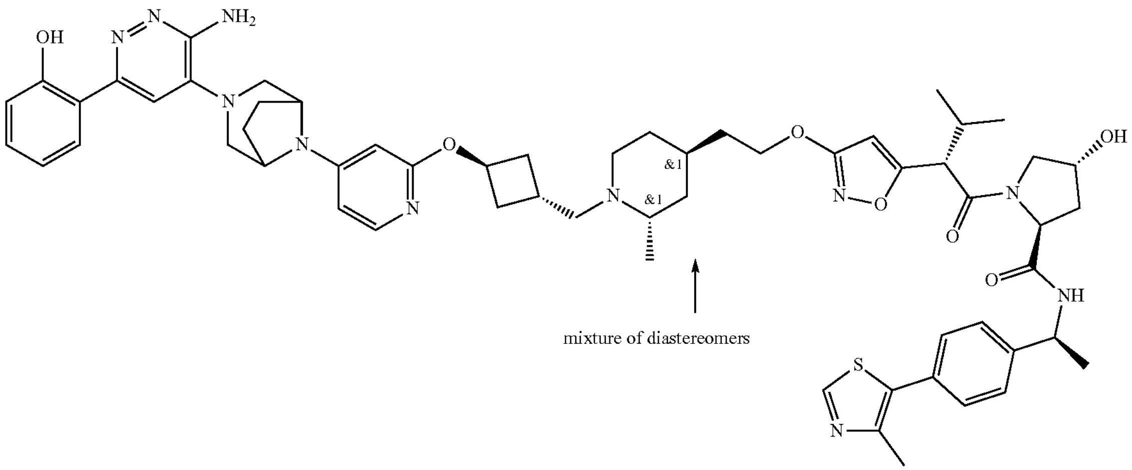 [SMILES: Cc1ncsc1-c1ccc([C@H](C)NC(=O)[C@@H]2C[C@@H](O)CN2C(=O)[C@H](c2cc(OCC[C@@H]3CCN(C[C@H]4C[C@H](Oc5cc(N6C7CCC6CN(c6cc(-c8ccccc8O)nnc6N)C7)ccn5)C4)[C@@H](C)C3)no2)C(C)C)cc1] | (2S,4R)-1-((2S)-2-(3-(2-((2S,4R)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 582 | 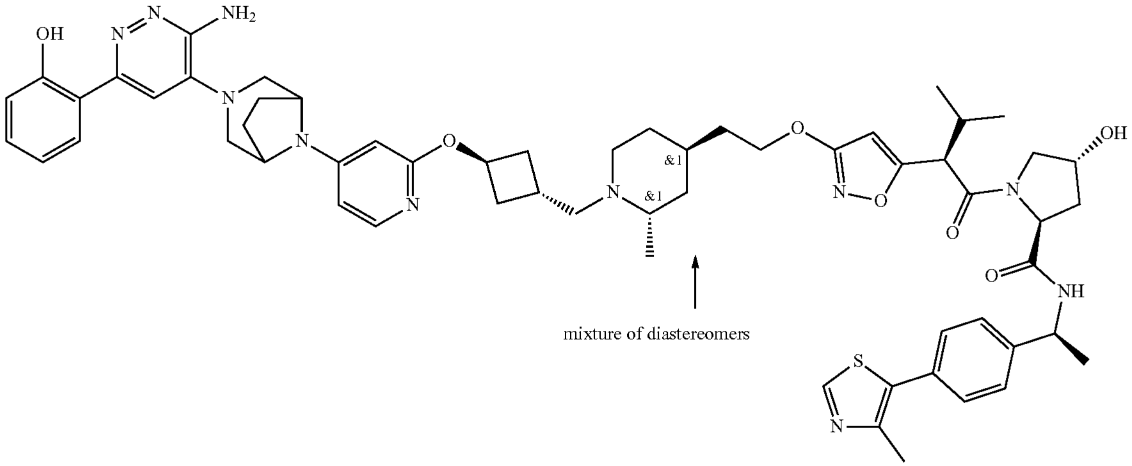 [SMILES: Cc1ncsc1-c1ccc([C@H](C)NC(=O)[C@@H]2C[C@@H](O)CN2C(=O)[C@@H](c2cc(OCC[C@@H]3CCN(C[C@H]4C[C@H](Oc5cc(N6C7CCC6CN(c6cc(-c8ccccc8O)nnc6N)C7)ccn5)C4)[C@@H](C)C3)no2)C(C)C)cc1] | (2S,4R)-1-((2R)-2-(3-(2-((2S,4R)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-methylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 583 | 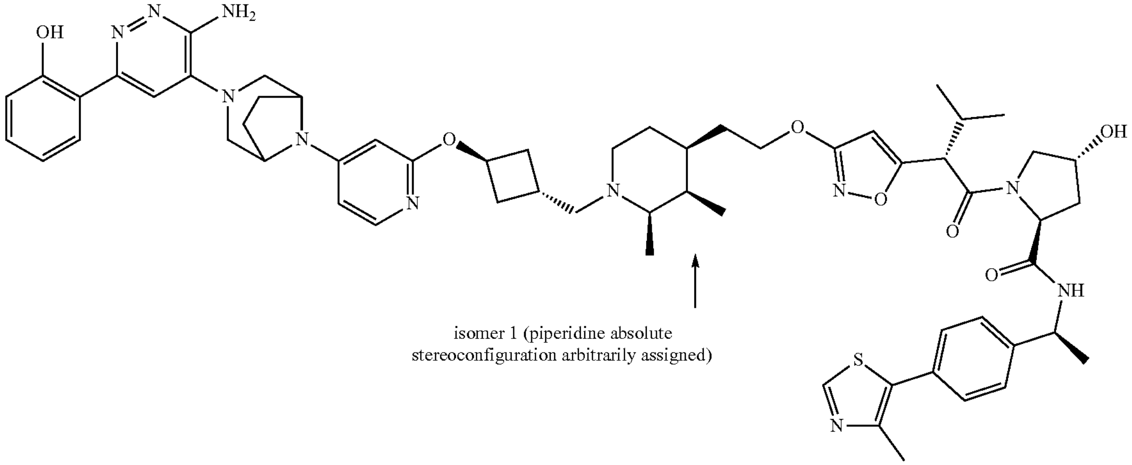 [SMILES: Cc1ncsc1-c1ccc([C@H](C)NC(=O)[C@@H]2C[C@@H](O)CN2C(=O)[C@H](c2cc(OCC[C@@H]3CCN(C[C@H]4C[C@H](Oc5cc(N6C7CCC6CN(c6cc(-c8ccccc8O)nnc6N)C7)ccn5)C4)[C@H](C)[C@@H]3C)no2)C(C)C)cc1] isomer 1 (piperidine absolute stereoconfiguration arbitrarily assigned) | (2S,4R)-1-((2S)-2-(3-(2-((2R,3R,4S)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,3-dimethylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 584 | 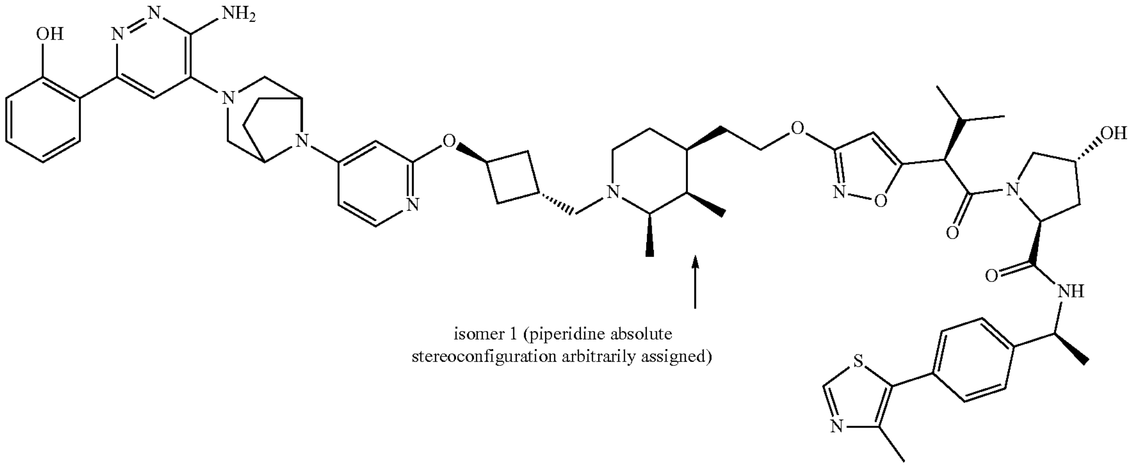 [SMILES: Cc1ncsc1-c1ccc([C@H](C)NC(=O)[C@@H]2C[C@@H](O)CN2C(=O)[C@@H](c2cc(OCC[C@@H]3CCN(C[C@H]4C[C@H](Oc5cc(N6C7CCC6CN(c6cc(-c8ccccc8O)nnc6N)C7)ccn5)C4)[C@H](C)[C@@H]3C)no2)C(C)C)cc1] isomer 1 (piperidine absolute stereoconfiguration arbitrarily assigned) | (2S,4R)-1-((2R)-2-(3-(2-((2R,3R,4S)-1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,3-dimethylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 585 | 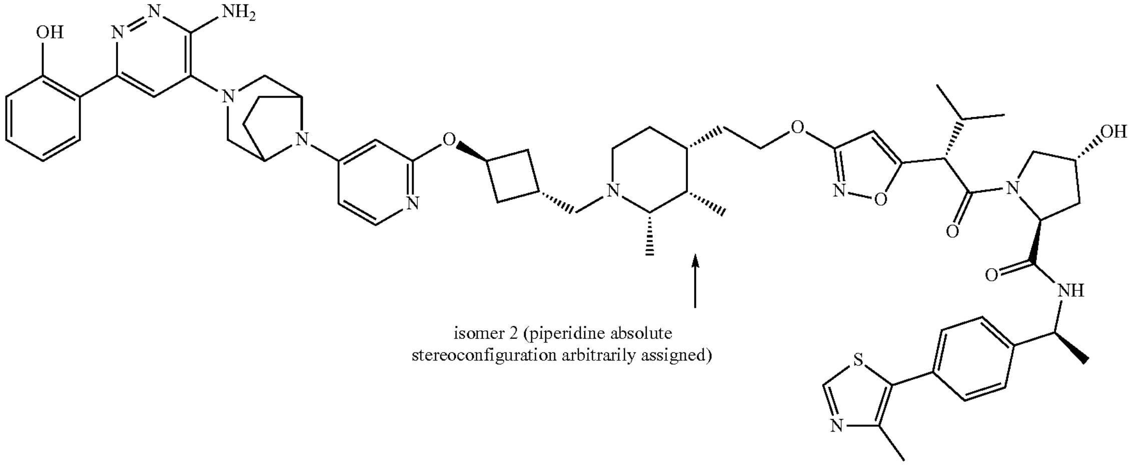 [SMILES: Cc1ncsc1-c1ccc([C@H](C)NC(=O)[C@@H]2C[C@@H](O)CN2C(=O)[C@H](c2cc(OCC[C@H]3CCN(C[C@H]4C[C@H](Oc5cc(N6C7CCC6CN(c6cc(-c8ccccc8O)nnc6N)C7)ccn5)C4)[C@@H](C)[C@H]3C)no2)C(C)C)cc1] isomer 2 (piperidine absolute stereoconfiguration arbitrarily assigned) | (2S,4R)-1-((2S)-2-(3-(2-((2S,3S,4R)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,3-dimethylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 586 | 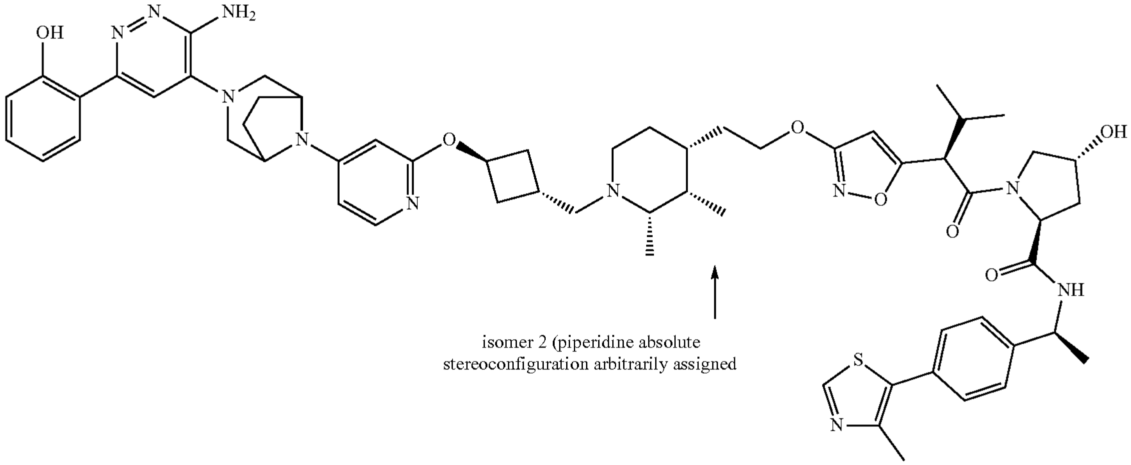 [SMILES: Cc1ncsc1-c1ccc([C@H](C)NC(=O)[C@@H]2C[C@@H](O)CN2C(=O)[C@@H](c2cc(OCC[C@H]3CCN(C[C@H]4C[C@H](Oc5cc(N6C7CCC6CN(c6cc(-c8ccccc8O)nnc6N)C7)ccn5)C4)[C@@H](C)[C@H]3C)no2)C(C)C)cc1] isomer 2 (piperidine absolute stereoconfiguration arbitrarily assigned | (2S,4R)-1-((2R)-2-(3-(2-((2S,3S,4R)-1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,3-dimethylpiperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 587 | 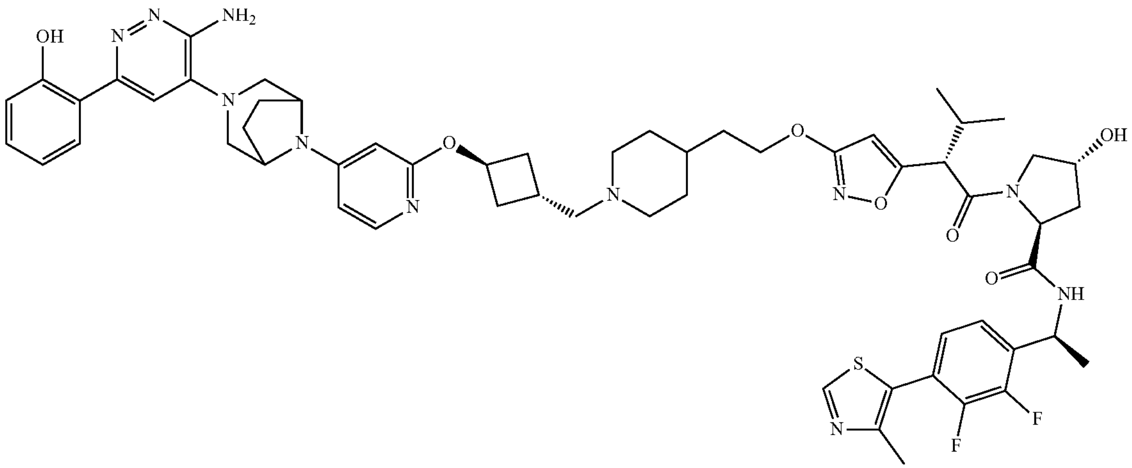 [SMILES: Cc1ncsc1-c1ccc([C@H](C)NC(=O)[C@@H]2C[C@@H](O)CN2C(=O)[C@H](c2cc(OCCC3CCN(C[C@H]4C[C@H](Oc5cc(N6C7CCC6CN(c6cc(-c8ccccc8O)nnc6N)C7)ccn5)C4)CC3)no2)C(C)C)c(F)c1F] | (2S,4R)-1-((2S)-2-(3-(2-(1-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)ethoxy)isoxazol-5-yl)-3-methylbutanoyl)-N-((S)-1-(2,3-difluoro-4-(4-methylthiazol-5-yl)phenyl)ethyl)-4-hydroxypyrrolidine-2-carboxamide |
| 588 | 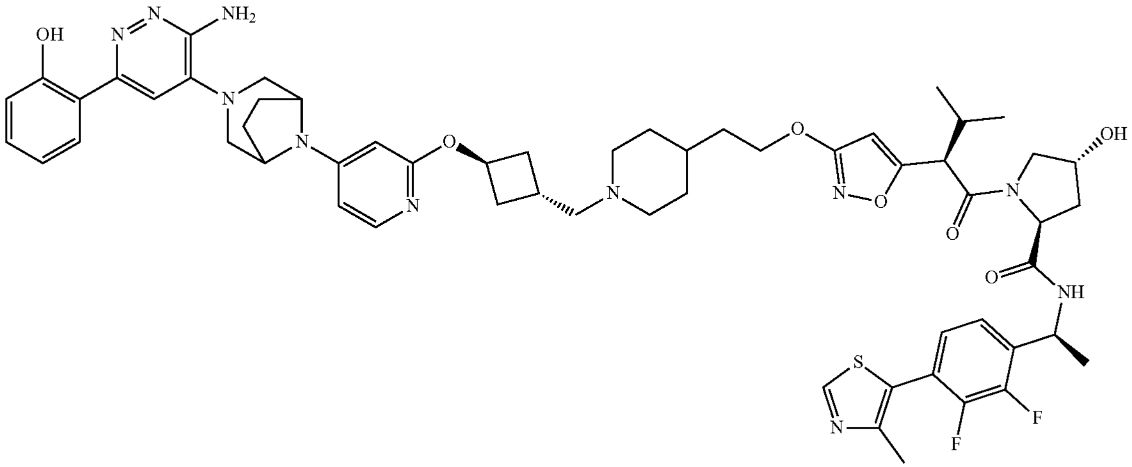 [SMILES: Cc1ncsc1-c1ccc([C@H](C)NC(=O)[C@@H]2C[C@@H](O)CN2C(=O)[C@@H](c2cc(OCCC3CCN(C[C@H]4C[C@H](Oc5cc(N6C7CCC6CN(c6cc(-c8ccccc8O)nnc6N)C7)ccn5)C4)CC3)no2)C(C)C)c(F)c1F] | (2S,4R)-1-((2R)-2-(3-(2-(1-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)ethoxy)isoxazol-5-yl)-3-methylbutanoyl)-N-((S)-1-(2,3-difluoro-4-(4-methylthiazol-5-yl)phenyl)ethyl)-4-hydroxypyrrolidine-2-carboxamide |

-continued
| []Exemplary bifunctional degradation compounds of the present disclosure | | |
|---|---|---|
| Ex No | Structure | Name |
| 589 | 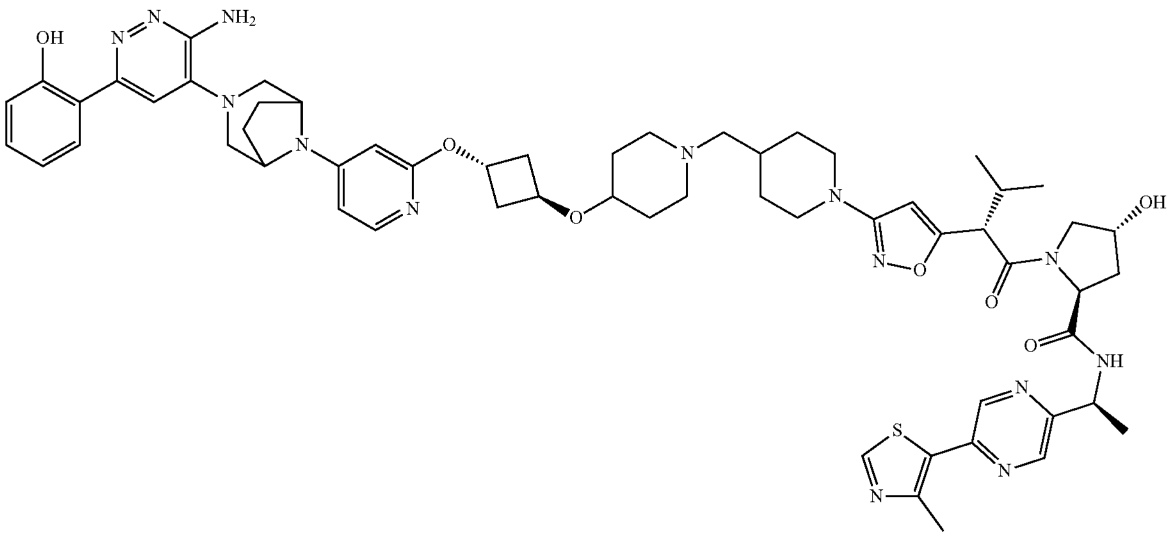 [SMILES: Cc1ncsc1-c1cnc([C@H](C)NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cn1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(5-(4-methylthiazol-5-yl)pyrazin-2-yl)ethyl)pyrrolidine-2-carboxamide |

-continued
| []Exemplary bifunctional degradation compounds of the present disclosure | | |
|---|---|---|
| Ex No | Structure | Name |
| 590 | 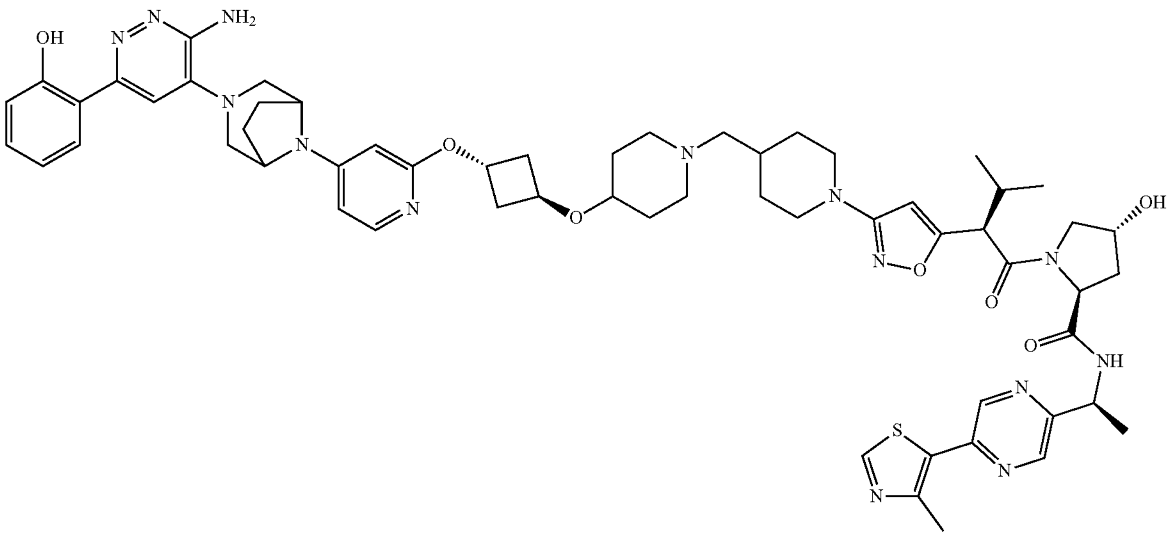 [SMILES: Cc1ncsc1-c1cnc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cn1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(5-(4-methylthiazol-5-yl)pyrazin-2-yl)ethyl)pyrrolidine-2-carboxamide |

-continued
| []Exemplary bifunctional degradation compounds of the present disclosure | | |
|---|---|---|
| Ex No | Structure | Name |
| 591 | 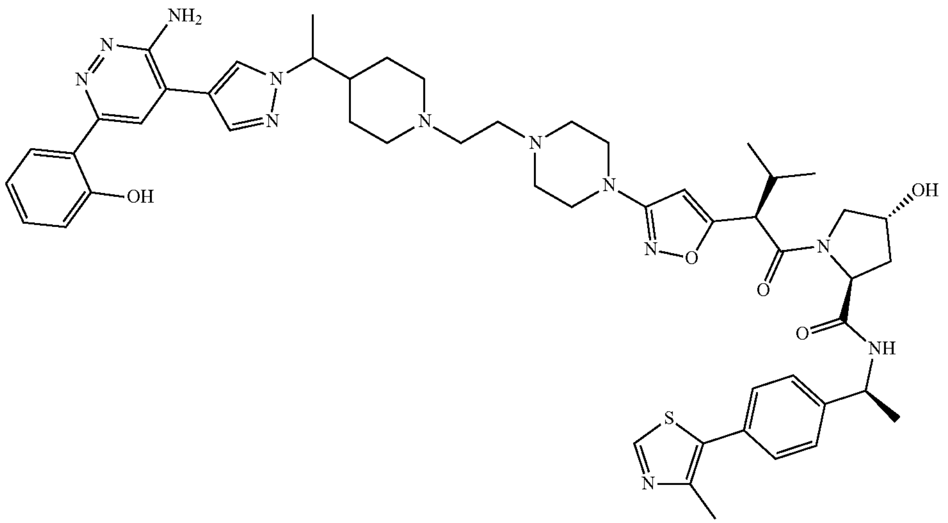 [SMILES: Cc1ncsc1-c1ccc([C@H](C)NC(=O)[C@@H]2C[C@@H](O)CN2C(=O)[C@@H](c2cc(N3CCN(CCN4CCC(C(C)n5cc(-c6cc(-c7ccccc7O)nnc6N)cn5)CC4)CC3)no2)C(C)C)cc1] | (2S,4R)-1-((2R)-2-(3-(4-(2-(4-(1-(4-(3-amino-6-(2-hydroxyphenyl)pyridazin-4-yl)-1H-pyrazol-1-yl)ethyl)piperidin-1-yl)ethyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 592 | 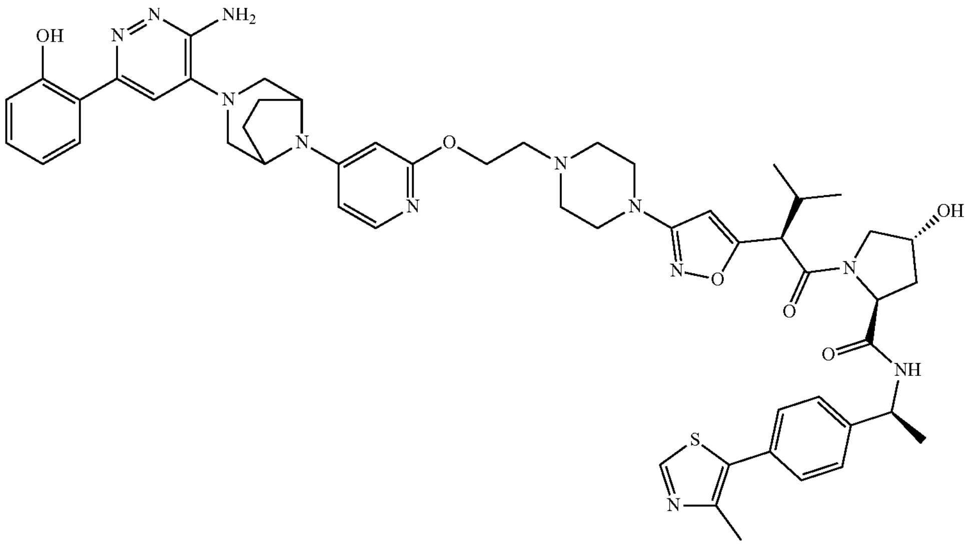 [SMILES: Cc1ncsc1-c1ccc([C@H](C)NC(=O)[C@@H]2C[C@@H](O)CN2C(=O)[C@@H](c2cc(N3CCN(CCOc4cc(N5C6CCC5CN(c5cc(-c7ccccc7O)nnc5N)C6)ccn4)CC3)no2)C(C)C)cc1] | (2S,4R)-1-((2R)-2-(3-(4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperazin-1-yl)isoxazol-5-yl)-3-methylbutanoyl)-4-hydroxy-N-((S)-1-(4-(4-methylthiazol-5-yl)phenyl)ethyl) pyrrolidine-2-carboxamide |
| 593 | 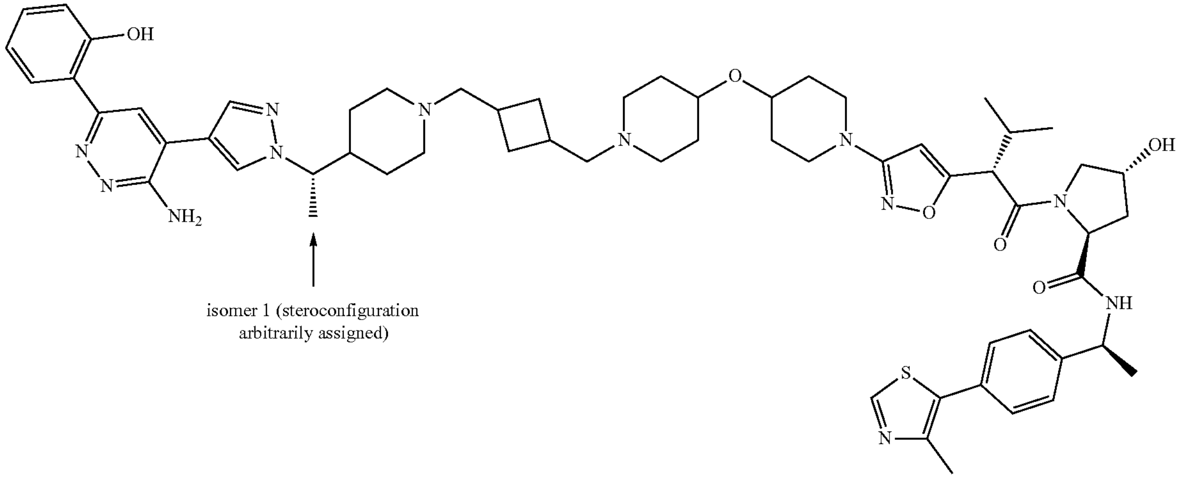 [SMILES: Cc1ncsc1-c1ccc([C@H](C)NC(=O)[C@@H]2C[C@@H](O)CN2C(=O)[C@H](c2cc(N3CCC(OC4CCN(CC5CC(CN6CCC([C@H](C)n7cc(-c8cc(-c9ccccc9O)nnc8N)cn7)CC6)C5)CC4)CC3)no2)C(C)C)cc1] | (2S,4R)-1-((S)-2-(3-(4-((1-((3-((4-((S)-1-(4-(3-amino-6-(2-hydroxyphenyl)pyridazin-4-yl)-1H-pyrazol-1-yl)ethyl)piperidin-1-yl)methyl)cyclobutyl)methyl)piperidin-4-yl)oxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 594 | 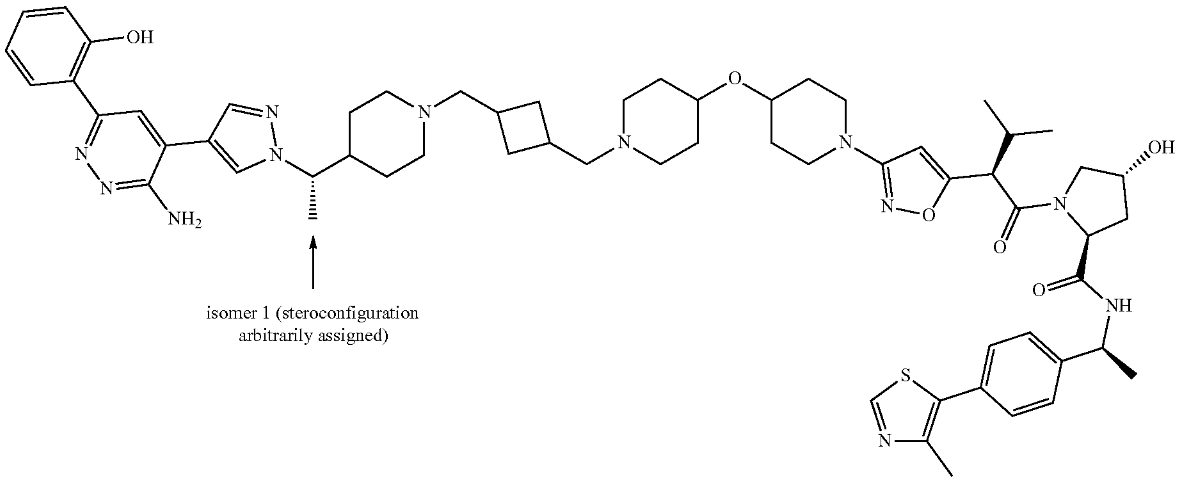 [SMILES: Cc1ncsc1-c1ccc([C@H](C)NC(=O)[C@@H]2C[C@@H](O)CN2C(=O)[C@@H](c2cc(N3CCC(OC4CCN(CC5CC(CN6CCC([C@H](C)n7cc(-c8cc(-c9ccccc9O)nnc8N)cn7)CC6)C5)CC4)CC3)no2)C(C)C)cc1] isomer 1 (stereoconfiguration arbitrarily assigned) | (2S,4R)-1-((R)-2-(3-(4-((1-((3-((4-((S)-1-(4-(3-amino-6-(2-hydroxyphenyl)pyridazin-4-yl)-1H-pyrazol-1-yl)ethyl)piperidin-1-yl)methyl)cyclobutyl)methyl)piperidin-4-yl)oxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 595 | 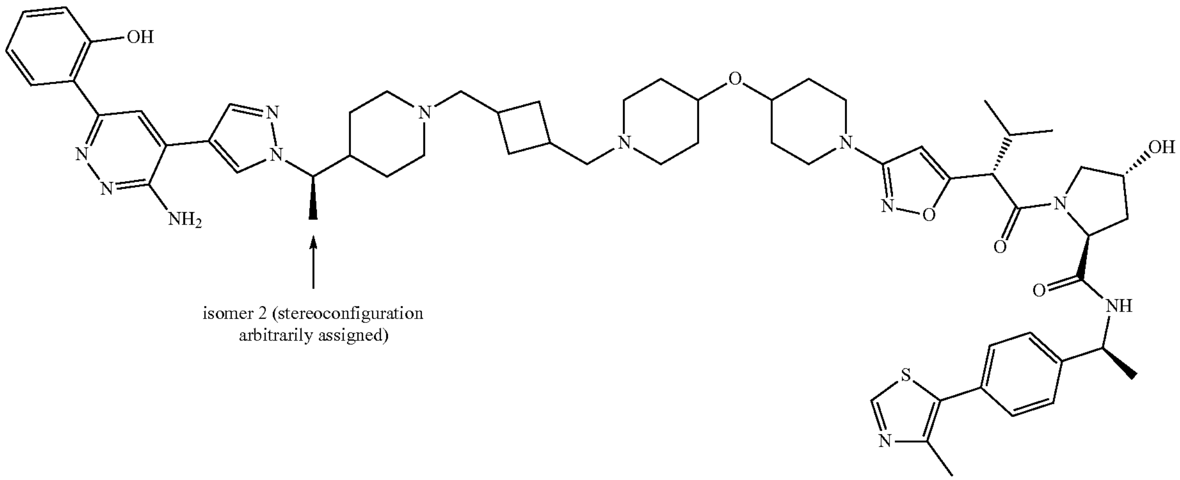 [SMILES: Cc1ncsc1-c1ccc([C@H](C)NC(=O)[C@@H]2C[C@@H](O)CN2C(=O)[C@H](c2cc(N3CCC(OC4CCN(CC5CC(CN6CCC([C@@H](C)n7cc(-c8cc(-c9ccccc9O)nnc8N)cn7)CC6)C5)CC4)CC3)no2)C(C)C)cc1] isomer 2 (stereoconfiguration arbitrarily assigned) | (2S,4R)-1-((S)-2-(3-(4-((1-((3-((4-((R)-1-(4-(3-amino-6-(2-hydroxyphenyl)pyridazin-4-yl)-1H-pyrazol-1-yl)ethyl)piperidin-1-yl)methyl)cyclobutyl)methyl)piperidin-4-yl)oxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
| --- | --- | --- |
| []Exemplary bifunctional degradation compounds of the present disclosure | | |
| 596 | 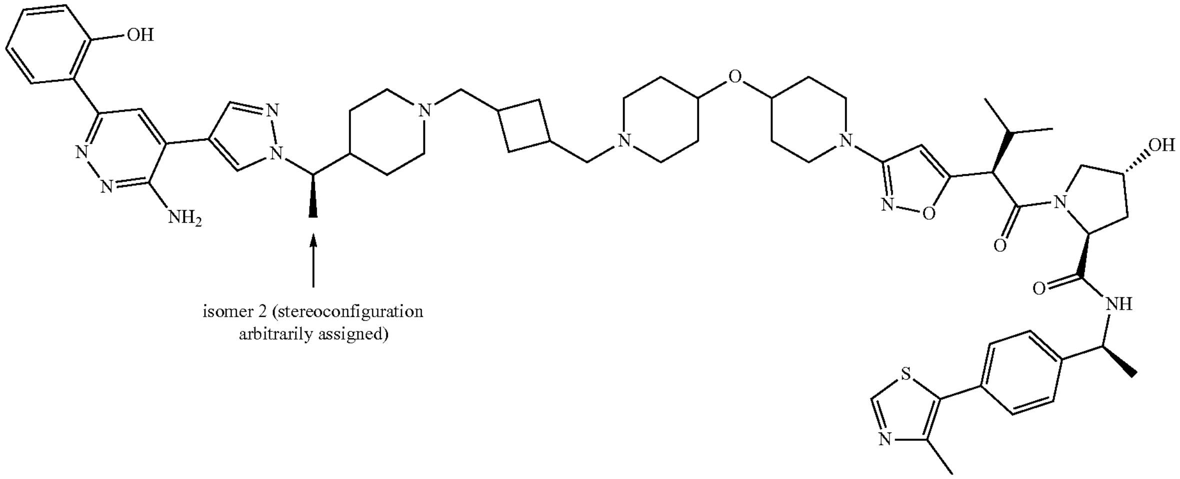 [SMILES: Cc1ncsc1-c1ccc([C@H](C)NC(=O)[C@@H]2C[C@@H](O)CN2C(=O)[C@@H](c2cc(N3CCC(OC4CCN(CC5CC(CN6CCC([C@@H](C)n7cc(-c8cc(-c9ccccc9O)nnc8N)cn7)CC6)C5)CC4)CC3)no2)C(C)C)cc1] isomer 2 (stereoconfiguration arbitrarily assigned) | (2S,4R)-1-((R)-2-(3-(4-((1-((3-((4-((R)-1-(4-(3-amino-6-(2-hydroxyphenyl)pyridazin-4-yl)-1H-pyrazol-1-yl)ethyl)piperidin-1-yl)methyl)cyclobutyl)methyl)piperidin-4-yl)oxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 597 | 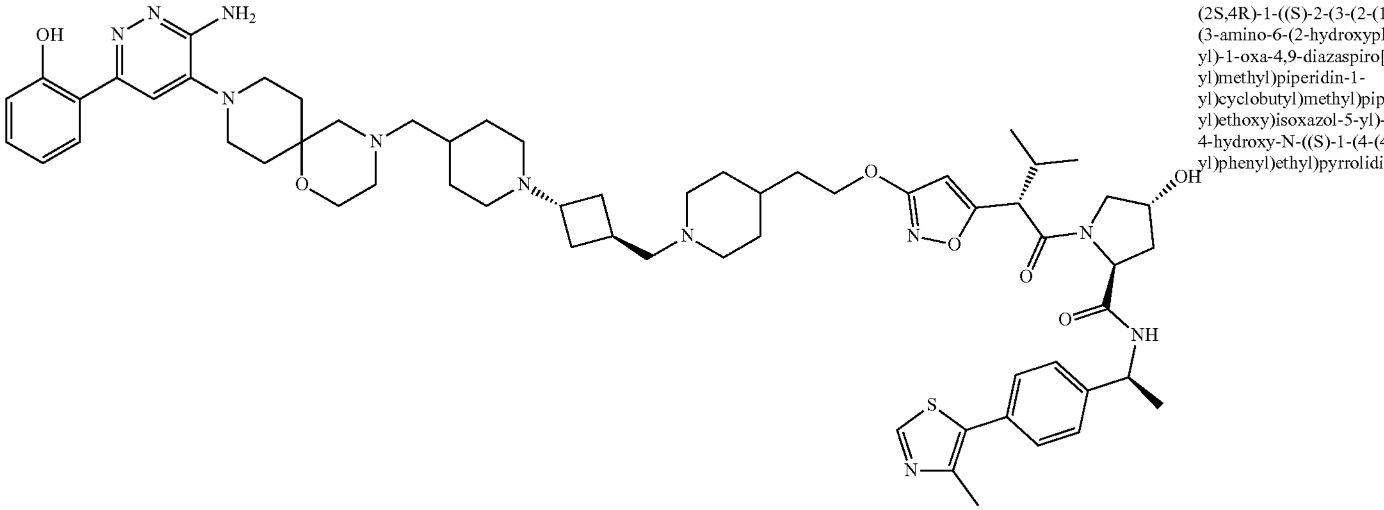 | (2S,4R)-1-((S)-2-(3-(2-(1-(((1r,3S)-3-(4-((9-(3-amino-6-(2-hydroxyphenyl)pyridazin-4-yl)-1-oxa-4,9-diazaspiro[5.5]undecan-4-yl)methyl)piperidin-1-yl)cyclobutyl)methyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 598 | 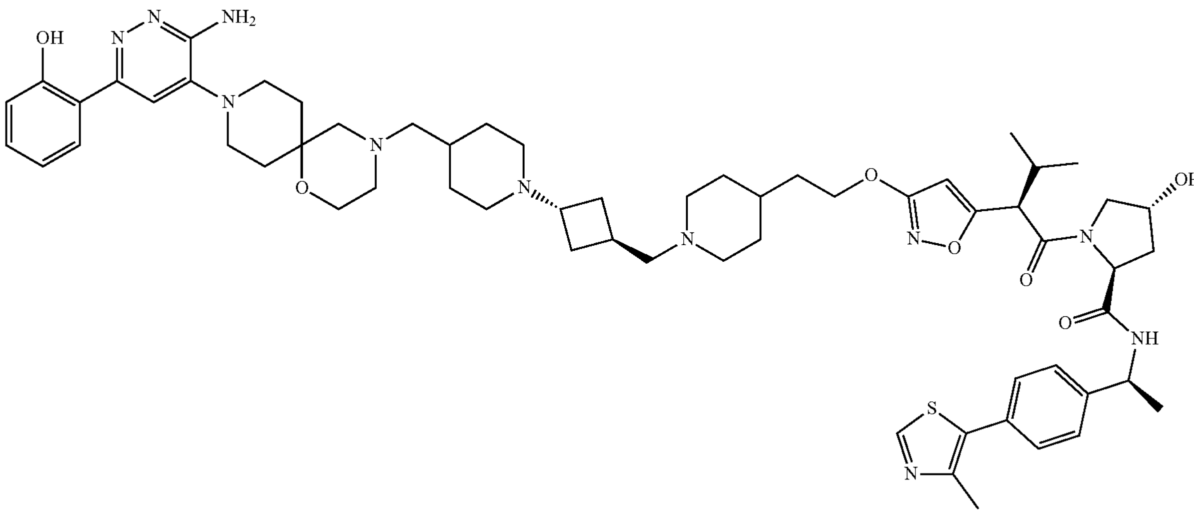 [SMILES: Cc1ncsc1-c1ccc([C@H](C)NC(=O)[C@@H]2C[C@@H](O)CN2C(=O)[C@@H](c2cc(OCCC3CCN(C[C@H]4C[C@H](N5CCC(CN6CCOC7(CCN(c8cc(-c9ccccc9O)nnc8N)CC7)C6)CC5)C4)CC3)no2)C(C)C)cc1] | (2S,4R)-1-((R)-2-(3-(2-(1-(((1r,3R)-3-(4-((9-(3-amino-6-(2-hydroxyphenyl)pyridazin-4-yl)-1-oxa-4,9-diazaspiro[5.5]undecan-4-yl)methyl)piperidin-1-yl)cyclobutyl)methyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 599 | 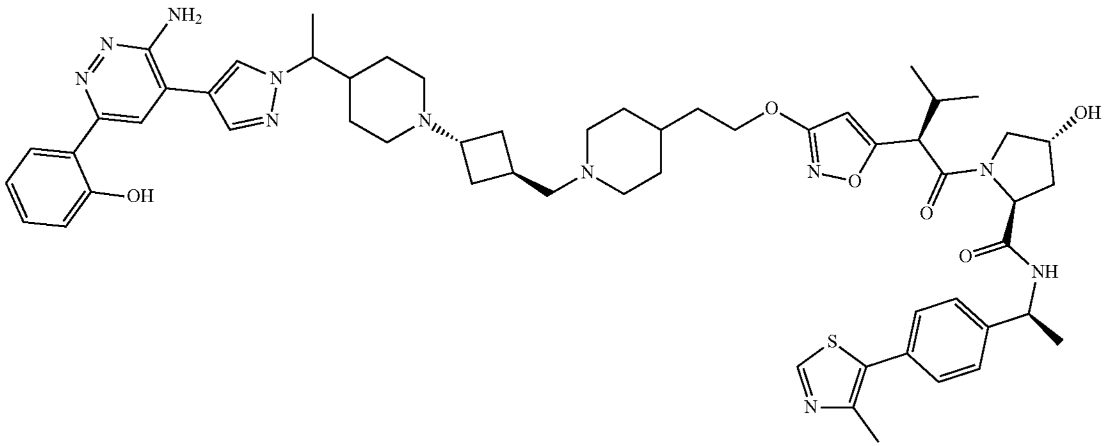 [SMILES: Cc1ncsc1-c1ccc([C@H](C)NC(=O)[C@@H]2C[C@@H](O)CN2C(=O)[C@@H](c2cc(OCCC3CCN(C[C@H]4C[C@H](N5CCC(C(C)n6cc(-c7cc(-c8ccccc8O)nnc7N)cn6)CC5)C4)CC3)no2)C(C)C)cc1] | (2S,4R)-1-((2R)-2-(3-(2-(1-(((1r,3R)-3-(4-(1-(4-(3-amino-6-(2-hydroxyphenyl)pyridazin-4-yl)-1H-pyrazol-1-yl)ethyl)piperidin-1-yl)cyclobutyl)methyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 600 | 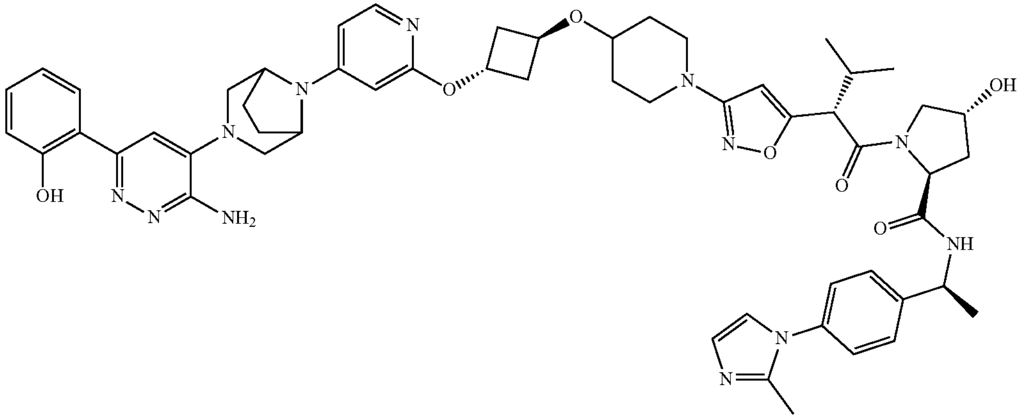 [SMILES: Cc1nccn1-c1ccc([C@H](C)NC(=O)[C@@H]2C[C@@H](O)CN2C(=O)[C@H](c2cc(N3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |
| 601 | 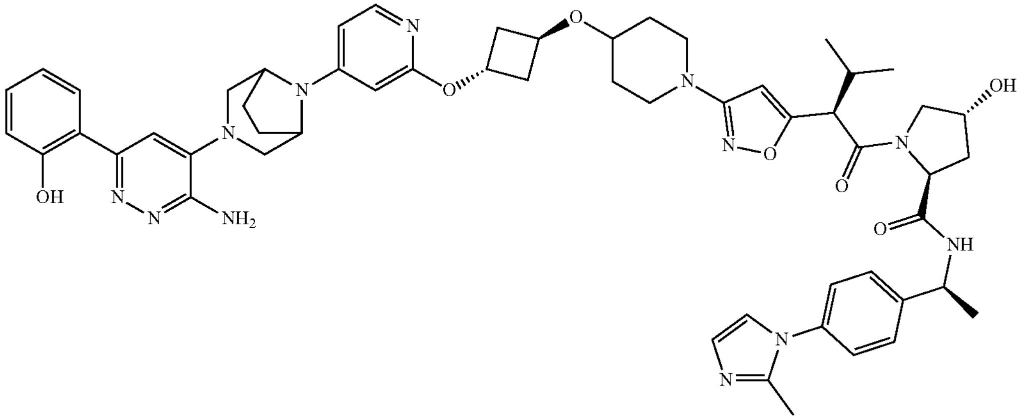 [SMILES: Cc1nccn1-c1ccc([C@H](C)NC(=O)[C@@H]2C[C@@H](O)CN2C(=O)[C@@H](c2cc(N3CCC(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

-continued

| []Exemplary bifunctional degradation compounds of the present disclosure | | |
|---|---|---|
| Ex No | Structure | Name |
| 602 | 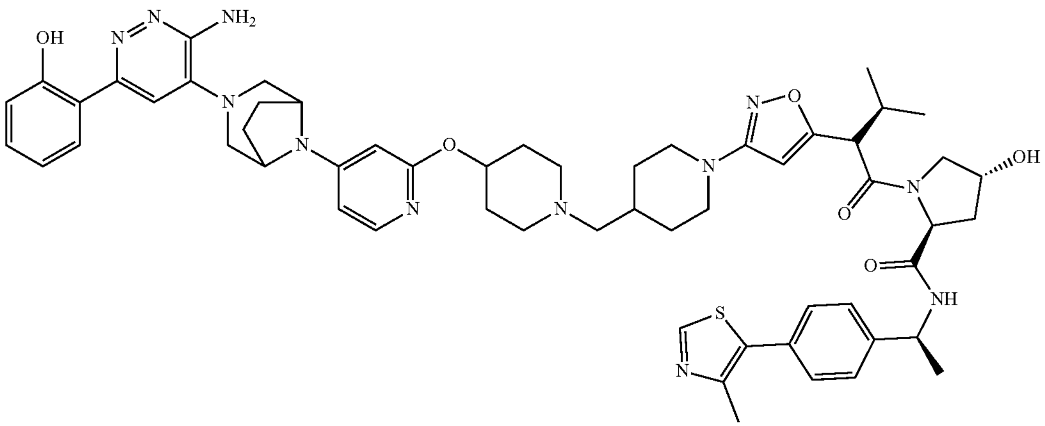 | (2S,4R)-1-((2R)-2-(3-(4-((4-((4-(3-(3-amino-6-(2-hydroxyphenyl)pyridazin-4-yl)-3,8-diazabicyclo[3.2.1]octan-8-yl)pyridin-2-yl)oxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 603 | 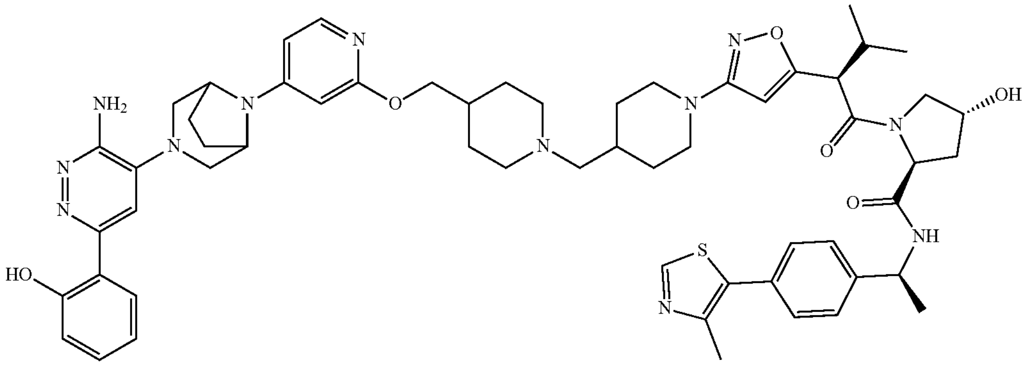 [SMILES: Cc1ncsc1-c1ccc([C@H](C)NC(=O)[C@@H]2C[C@@H](O)CN2C(=O)[C@@H](c2cc(N3CCC(CN4CCC(COc5cc(N6C7CCC6CN(c6cc(-c8ccccc8O)nnc6N)C7)ccn5)CC4)CC3)no2)C(C)C)cc1] | (2S,4R)-1-((2R)-2-(3-(4-((4-(((4-(3-(3-amino-6-(2-hydroxyphenyl)pyridazin-4-yl)-3,8-diazabicyclo[3.2.1]octan-8-yl)pyridin-2-yl)oxy)methyl)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 604 | 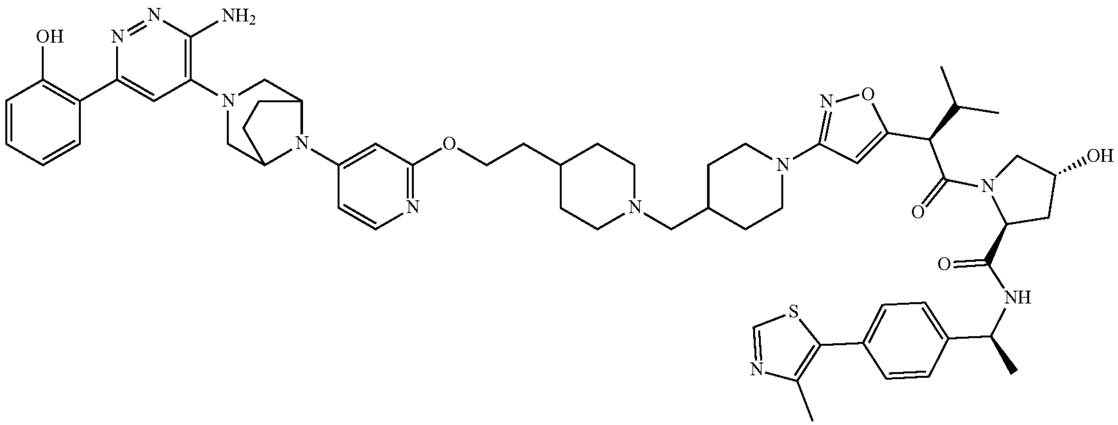 [SMILES: Cc1ncsc1-c1ccc([C@H](C)NC(=O)[C@@H]2C[C@@H](O)CN2C(=O)[C@@H](c2cc(N3CCC(CN4CCC(CCOc5cc(N6C7CCC6CN(c6cc(-c8ccccc8O)nnc6N)C7)ccn5)CC4)CC3)no2)C(C)C)cc1] | (2S,4R)-1-((2R)-2-(3-(4-((4-(2-((4-(3-(3-amino-6-(2-hydroxyphenyl)pyridazin-4-yl)-3,8-diazabicyclo[3.2.1]octan-8-yl)pyridin-2-yl)oxy)ethyl)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 605 | 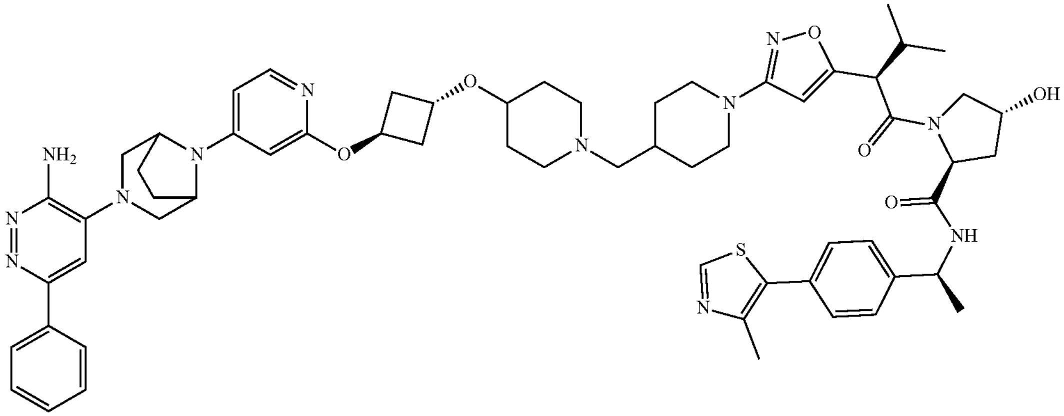 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-phenylpyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 606 | 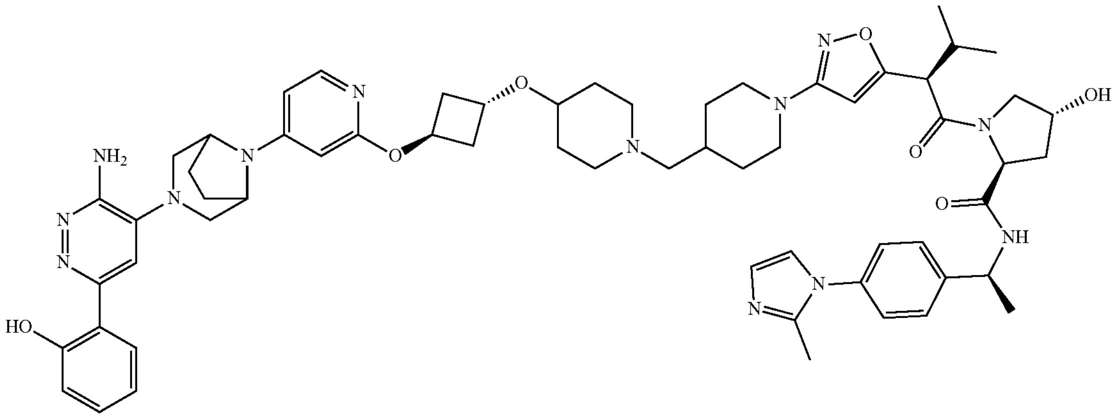 [SMILES: Cc1nccn1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |
| 607 | 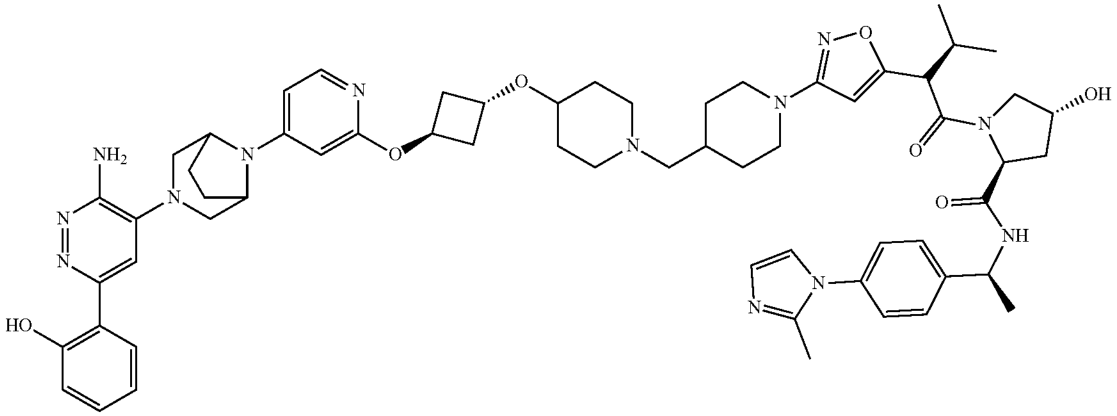 | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

-continued

[]Exemplary bifunctional degradation compounds of the present disclosure

| Ex No | Structure | Name |
|---|---|---|
| 608 | 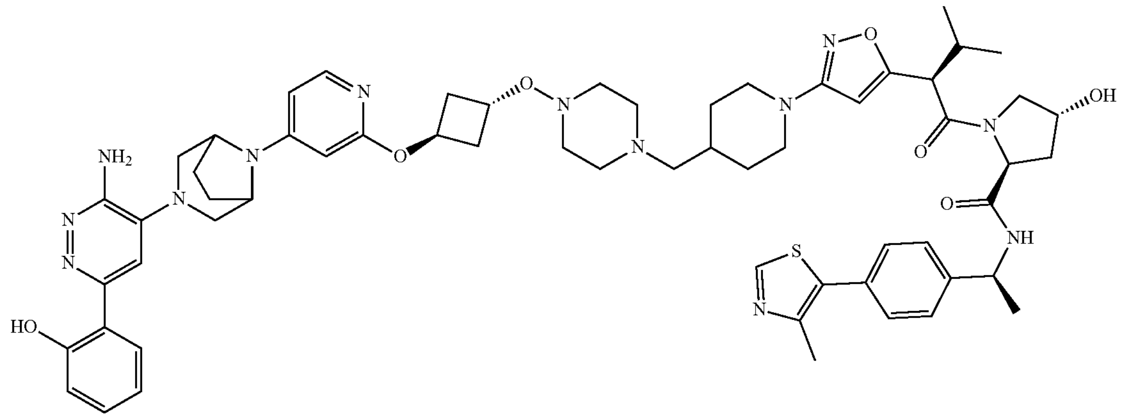 [SMILES: Cc1ncsc1-c1ccc([C@H](C)NC(=O)[C@@H]2C[C@@H](O)CN2C(=O)[C@@H](c2cc(N3CCC(CN4CCN(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperazin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 609 | 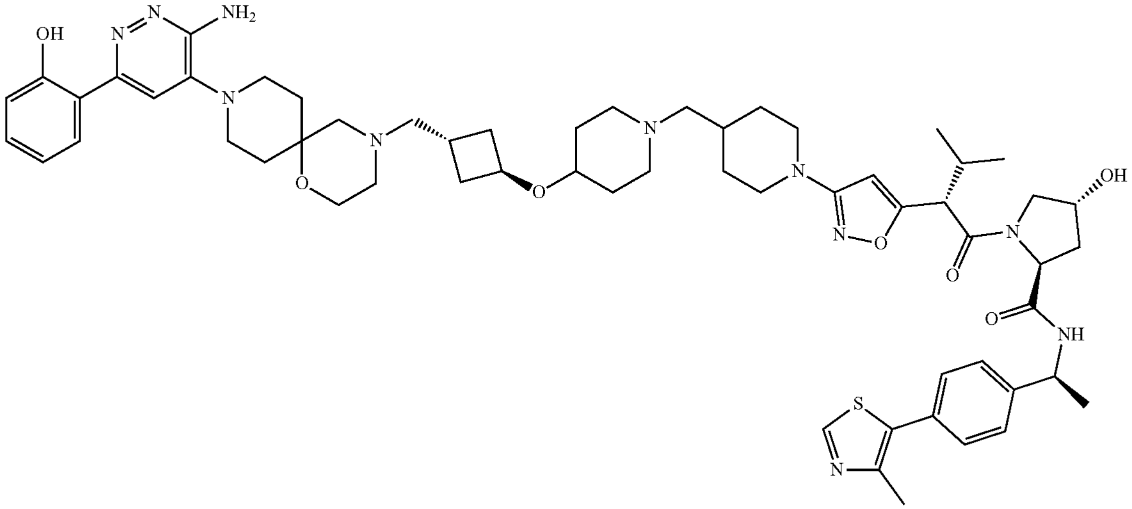 [SMILES: Cc1ncsc1-c1ccc([C@H](C)NC(=O)[C@@H]2C[C@@H](O)CN2C(=O)[C@H](c2cc(N3CCC(CN4CCC(O[C@H]5C[C@H](CN6CCOC7(CCN(c8cc(-c9ccccc9O)nnc8N)CC7)C6)C5)CC4)CC3)no2)C(C)C)cc1] | (2S,4R)-1-((S)-2-(3-(4-((4-((1r,3r)-3-((9-(3-amino-6-(2-hydroxyphenyl)pyridazin-4-yl)-1-oxa-4,9-diazaspiro[5.5]undecan-4-yl)methyl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
| --- | --- | --- |
| []Exemplary bifunctional degradation compounds of the present disclosure | | |
| 610 | 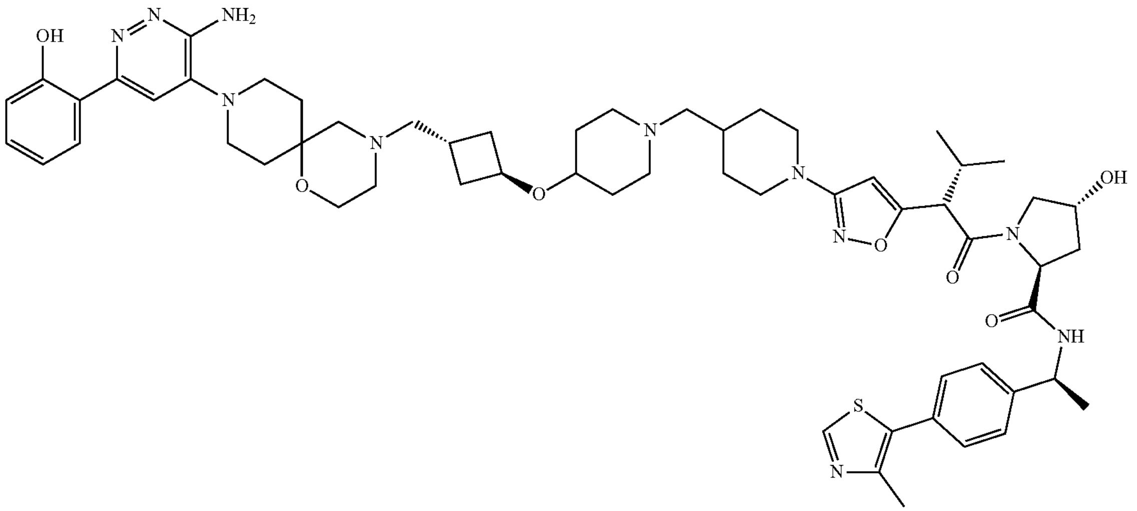 | (2S,4R)-1-((R)-2-(3-(4-((4-((1r,3r)-3-((9-(3-amino-6-(2-hydroxyphenyl)pyridazin-4-yl)-1-oxa-4,9-diazaspiro[5.5]undecan-4-yl)methyl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 611 | 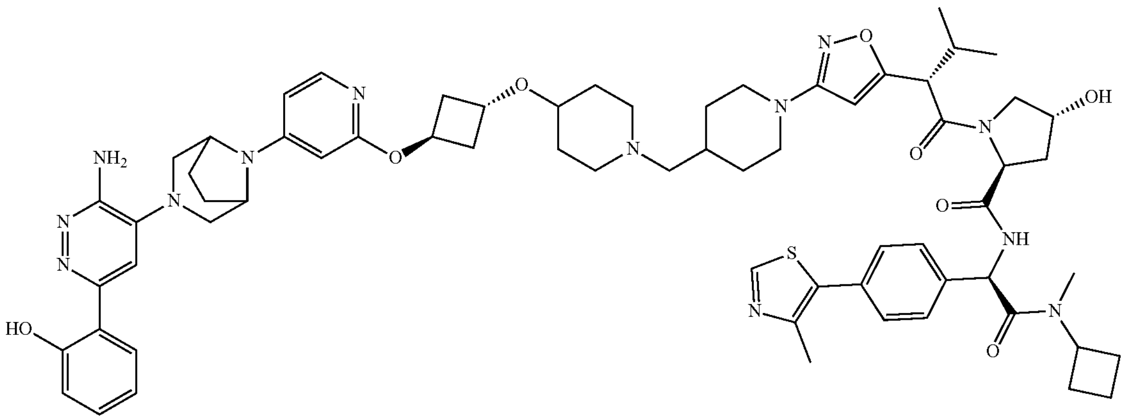 [SMILES: Cc1ncsc1-c1ccc([C@@H](NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)C(=O)N(C)C2CCC2)cc1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((R)-2-(cyclobutyl(methyl)amino)-1-(4-(4-methylthiazol-5-yl)phenyl)-2-oxoethyl)-4-hydroxypyrrolidine-2-carboxamide |

-continued

[]Exemplary bifunctional degradation compounds of the present disclosure

| Ex No | Structure | Name |
|---|---|---|
| 612 | 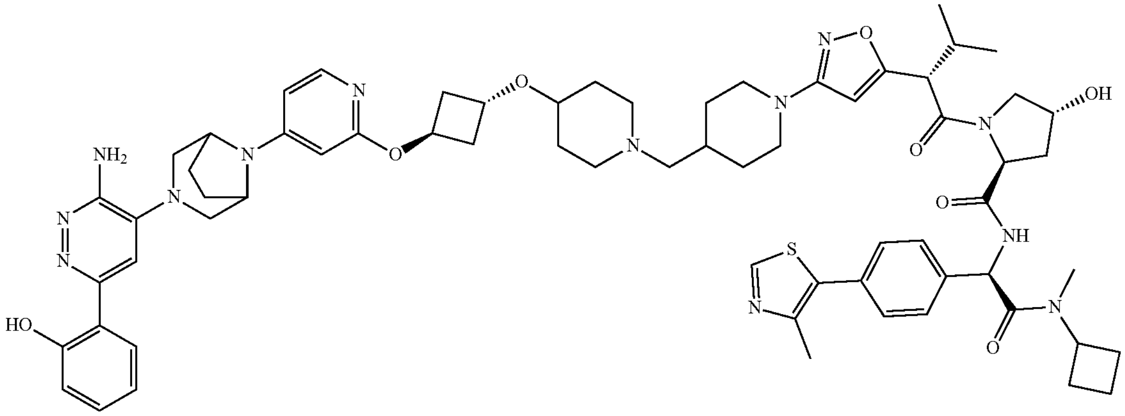 [SMILES: Cc1ncsc1-c1ccc([C@@H](NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)C(=O)N(C)C2CCC2)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((R)-2-(cyclobutyl(methyl)amino)-1-(4-(4-methylthiazol-5-yl)phenyl)-2-oxoethyl)-4-hydroxypyrrolidine-2-carboxamide |
| 613 | 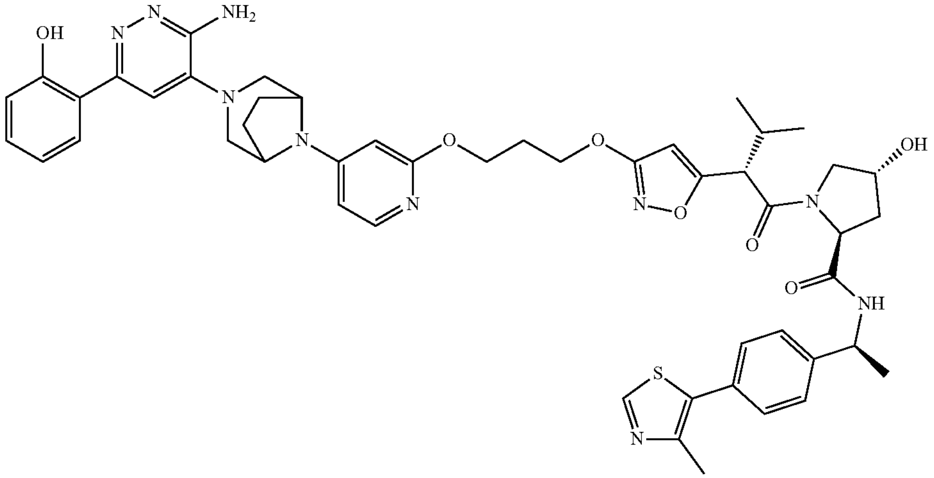 [SMILES: Cc1ncsc1-c1ccc([C@H](C)NC(=O)[C@@H]2C[C@@H](O)CN2C(=O)[C@H](c2cc(OCCCOc3cc(N4C5CCC4CN(c4cc(-c6ccccc6O)nnc4N)C5)ccn3)no2)C(C)C)cc1] | (2S,4R)-1-((2S)-2-(3-(3-((4-(3-(3-amino-6-(2-hydroxyphenyl)pyridazin-4-yl)-3,8-diazabicyclo[3.2.1]octan-8-yl)pyridin-2-yl)oxy)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 614 | 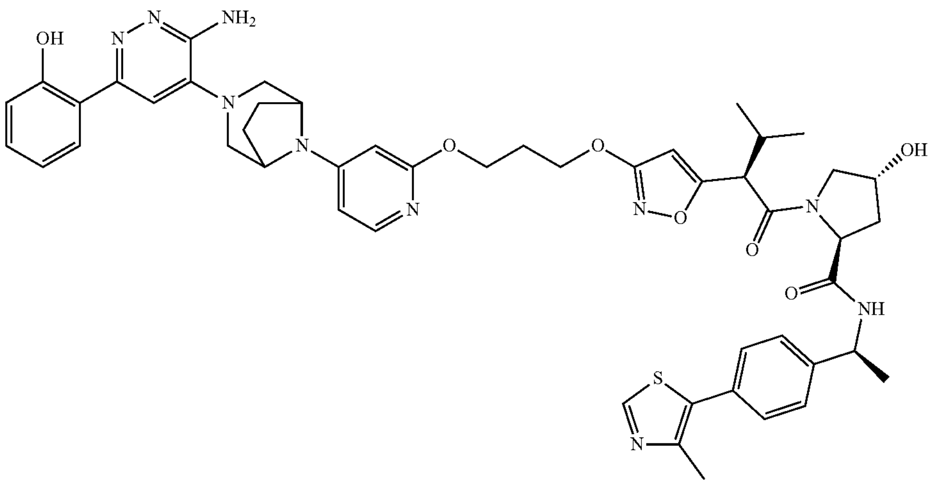 [SMILES: Cc1ncsc1-c1ccc([C@H](C)NC(=O)[C@@H]2C[C@@H](O)CN2C(=O)[C@@H](c2cc(OCCCOc3cc(N4C5CCC4CN(c4cc(-c6ccccc6O)nnc4N)C5)ccn3)no2)C(C)C)cc1] | (2S,4R)-1-((2R)-2-(3-(3-((4-(3-(3-amino-6-(2-hydroxyphenyl)pyridazin-4-yl)-3,8-diazabicyclo[3.2.1]octan-8-yl)pyridin-2-yl)oxy)propoxy)isoxazol-5-y1)-3-methylbutanoyl)-4-hydroxy-N-((S)-1-(4-(4-methylthiazol-5-yl)phenyl)ethyl)pyrrolidine-2-carboxamide |
| 615 | 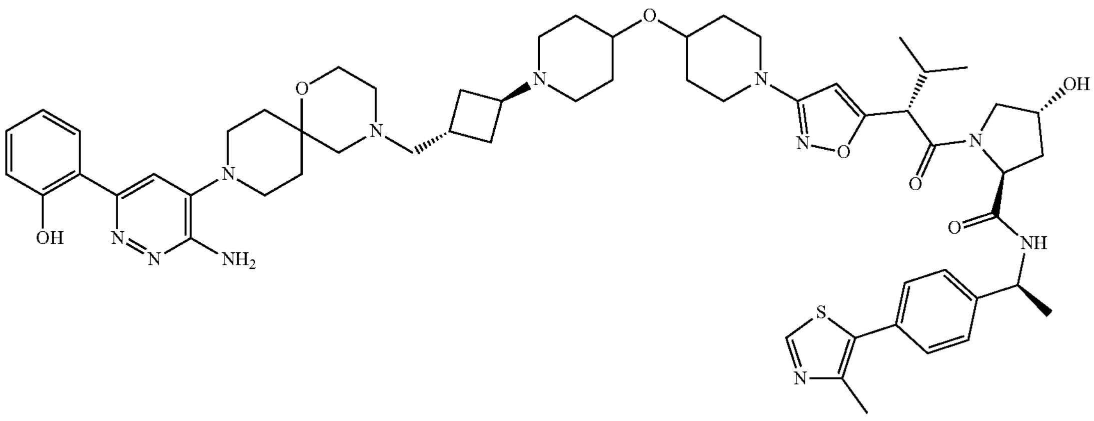 [SMILES: Cc1ncsc1-c1ccc([C@H](C)NC(=O)[C@@H]2C[C@@H](O)CN2C(=O)[C@H](c2cc(N3CCC(OC4CCN([C@H]5C[C@H](CN6CCOC7(CCN(c8cc(-c9ccccc9O)nnc8N)CC7)C6)C5)CC4)CC3)no2)C(C)C)cc1] | (2S,4R)-1-((S)-2-(3-(4-((1-((1r,3S)-3-((9-(3-amino-6-(2-hydroxyphenyl)pyridazin-4-yl)-1-oxa-4,9-diazaspiro[5.5]undecan-4-yl)methyl)cyclobutyl)piperidin-4-yl)oxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 616 | 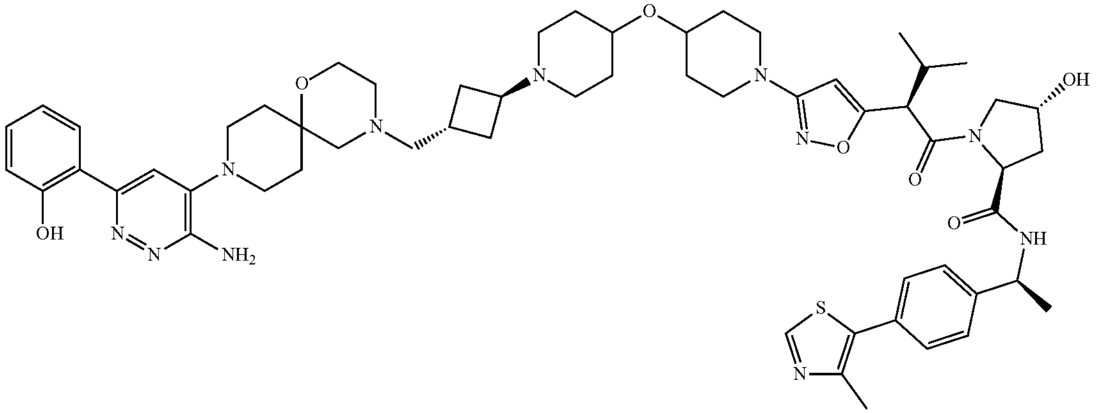 [SMILES: Cc1ncsc1-c1ccc([C@H](C)NC(=O)[C@@H]2C[C@@H](O)CN2C(=O)[C@@H](c2cc(N3CCC(OC4CCN([C@H]5C[C@H](CN6CCOC7(CCN(c8cc(-c9ccccc9O)nnc8N)CC7)C6)C5)CC4)CC3)no2)C(C)C)cc1] | (2S,4R)-1-((R)-2-(3-(4-((1-((1r,3R)-3-((9-(3-amino-6-(2-hydroxyphenyl)pyridazin-4-yl)-1-oxa-4,9-diazaspiro[5.5]undecan-4-yl)methyl)cyclobutyl)piperidin-4-yl)oxy)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 617 | 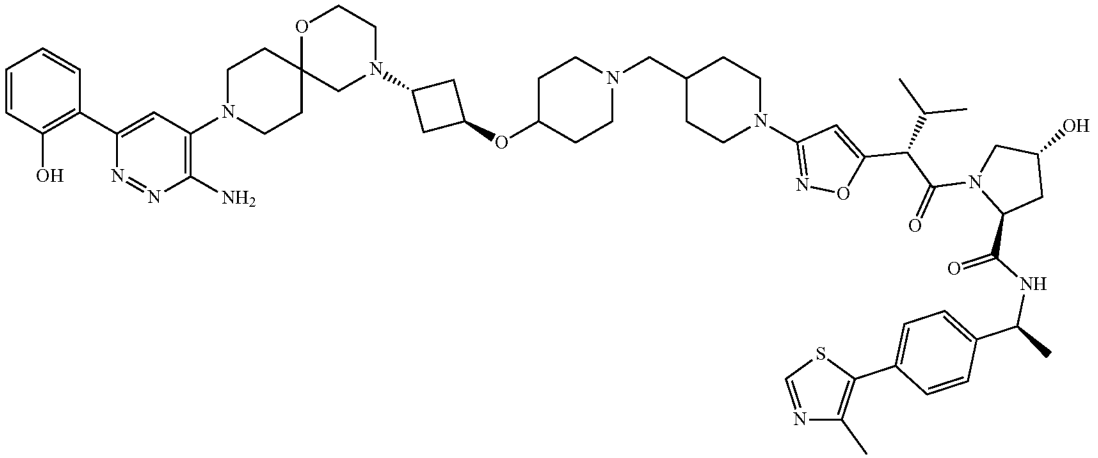 [SMILES: Cc1ncsc1-c1ccc([C@H](C)NC(=O)[C@@H]2C[C@@H](O)CN2C(=O)[C@H](c2cc(N3CCC(CN4CCC(O[C@H]5C[C@H](N6CCOC7(CCN(c8cc(-c9ccccc9O)nnc8N)CC7)C6)C5)CC4)CC3)no2)C(C)C)cc1] | (2S,4R)-1-((S)-2-(3-(4-((4-((1r,3r)-3-(9-(3-amino-6-(2-hydroxyphenyl)pyridazin-4-yl)-1-oxa-4,9-diazaspiro[5.5]undecan-4-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 618 | 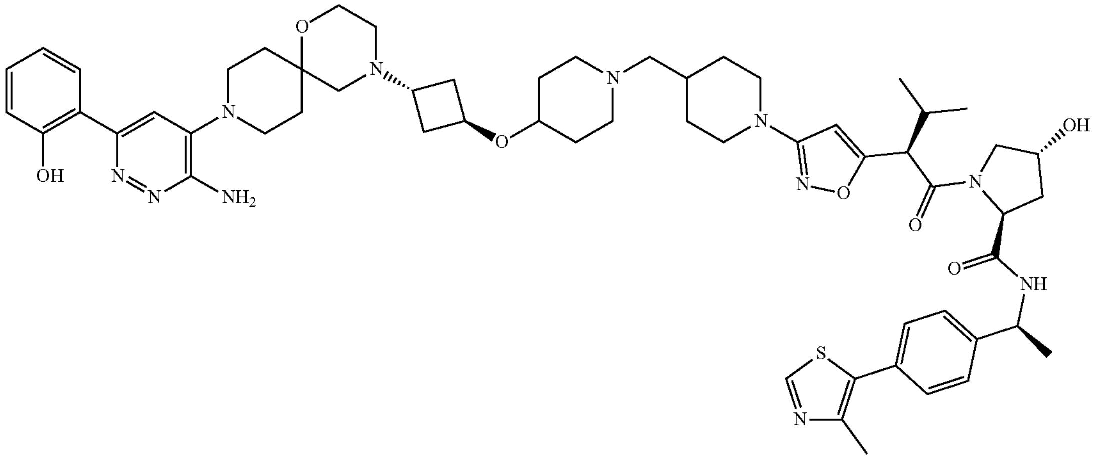 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](N6CCOC7(CCN(c8cc(-c9ccccc9O)nnc8N)CC7)C6)C5)CC4)CC3)no2)C(C)C)cc1] | (2S,4R)-1-((R)-2-(3-(4-((4-((1r,3r)-3-(9-(3-amino-6-(2-hydroxyphenyl)pyridazin-4-yl)-1-oxa-4,9-diazaspiro[5.5]undecan-4-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 619 | 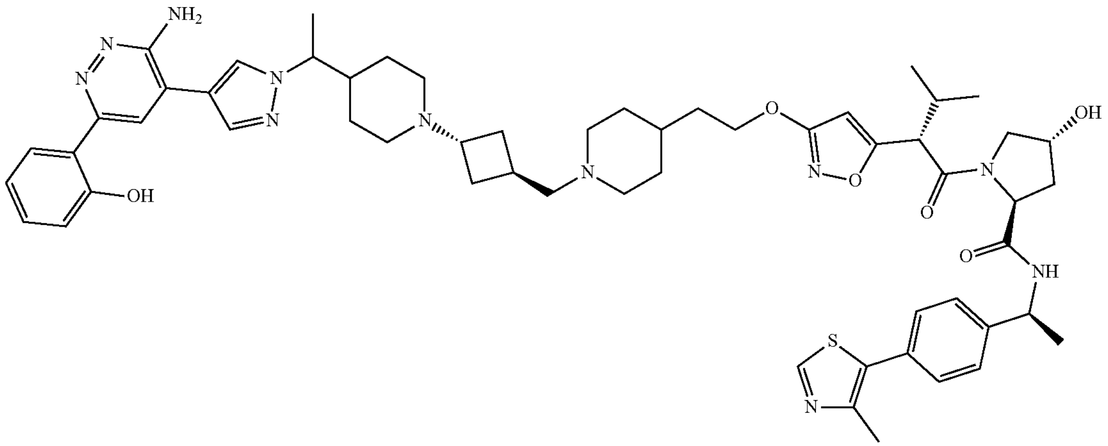 [SMILES: Cc1ncsc1-c1ccc([C@H](C)NC(=O)[C@@H]2C[C@@H](O)CN2C(=O)[C@H](c2cc(OCCC3CCN(C[C@H]4C[C@H](N5CCC(C(C)n6cc(-c7cc(-c8ccccc8O)nnc7N)cn6)CC5)C4)CC3)no2)C(C)C)cc1] | (2S,4R)-1-((2S)-2-(3-(2-(1-(((1r,3S)-3-(4-(1-(4-(3-amino-6-(2-hydroxyphenyl)pyridazin-4-yl)-1H-pyrazol-1-yl)ethyl)piperidin-1-yl)cyclobutyl)methyl)piperidin-4-yl)ethoxy)isoxazol-5-yl)-3-methylbutanoyl)-4-hydr oxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 620 | 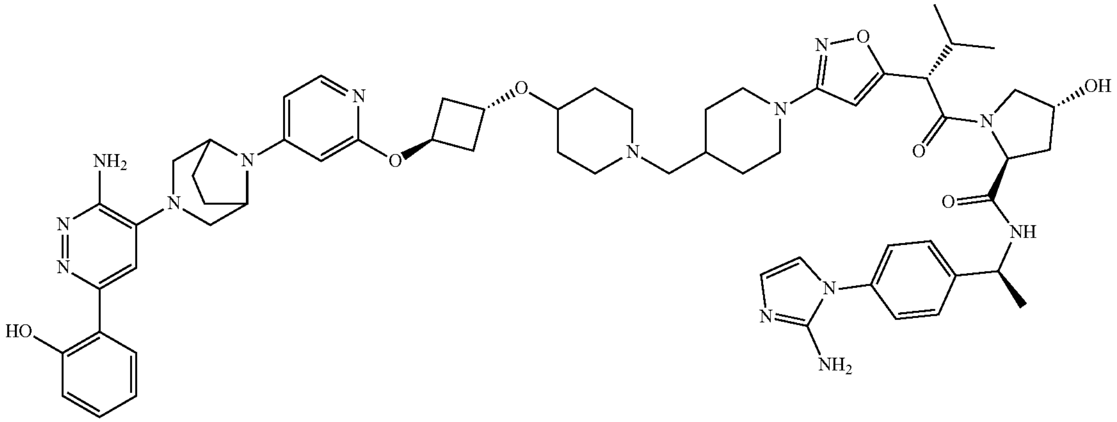 [SMILES: CC(C)[C@H](C(=O)N1C[C@H](O)C[C@H]1C(=O)N[C@@H](C)c1ccc(-n2ccnc2N)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-N-((S)-1-(4-(2-amino-1H-imidazol-1-yl)phenyl)ethyl)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxypyrrolidine-2-carboxamide |
| 621 | 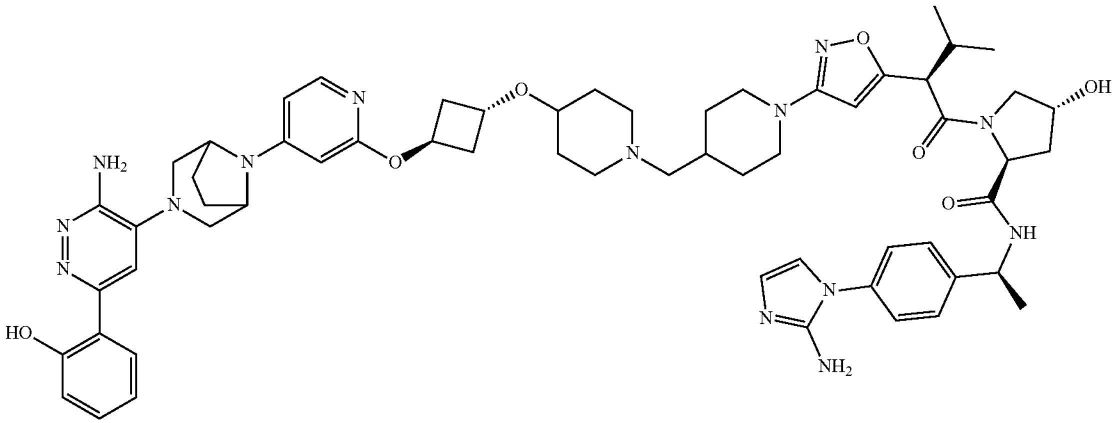 [SMILES: CC(C)[C@@H](C(=O)N1C[C@H](O)C[C@H]1C(=O)N[C@@H](C)c1ccc(-n2ccnc2N)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-N-((S)-1-(4-(2-amino-1H-imidazol-1-yl)phenyl)ethyl)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxypyrrolidine-2-carboxamide |

-continued

[]Exemplary bifunctional degradation compounds of the present disclosure

| Ex No | Structure | Name |
|---|---|---|
| 622 | 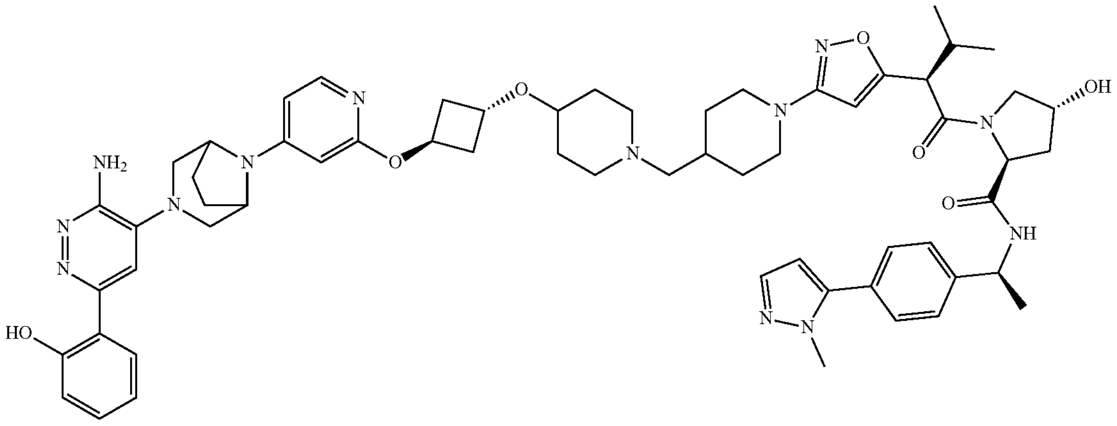 [SMILES: CC(C)[C@@H](C(=O)N1C[C@H](O)C[C@H]1C(=O)N[C@@H](C)c1ccc(-c2ccnn2C)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(1-methyl-1H-pyrazol-5-yl)phenyl)ethyl)pyrrolidine-2-carboxamide |
| 623 | 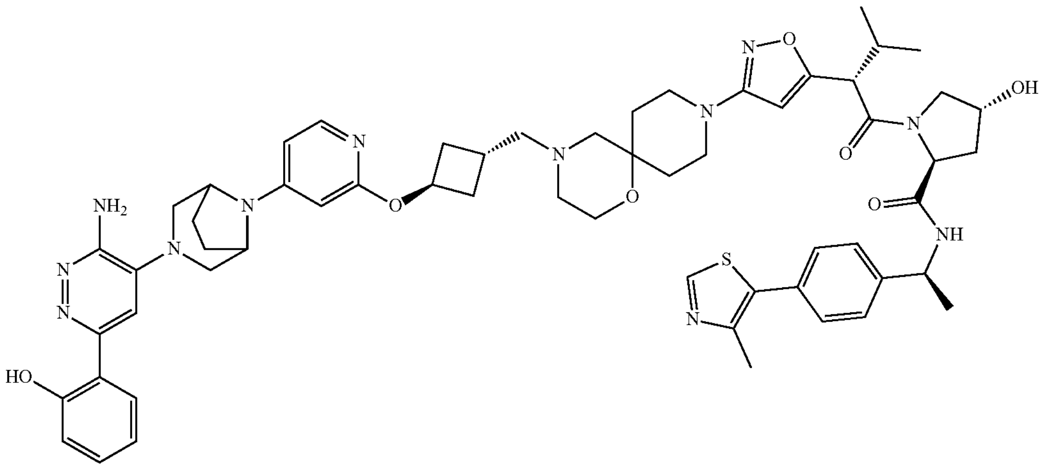 [SMILES: Cc1ncsc1-c1ccc([C@H](C)NC(=O)[C@@H]2C[C@@H](O)CN2C(=O)[C@H](c2cc(N3CCC4(CC3)CN(C[C@H]3C[C@H](Oc5cc(N6C7CCC6CN(c6cc(-c8ccccc8O)nnc6N)C7)ccn5)C3)CCO4)no2)C(C)C)cc1] | (2S,4R)-1-((2S)-2-(3-(4-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-1-oxa-4,9-diazaspiro[5.5]undecan-9-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 624 | 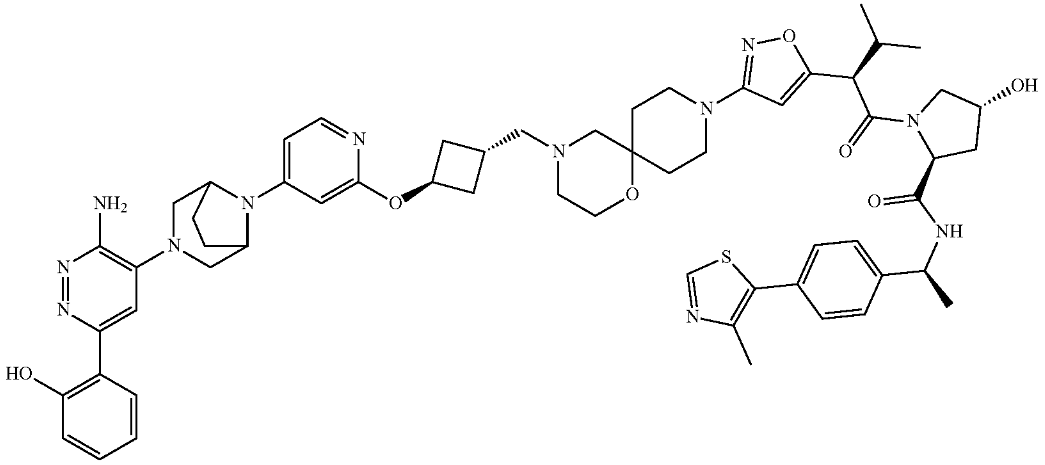 [SMILES: Cc1ncsc1-c1ccc([C@H](C)NC(=O)[C@@H]2C[C@@H](O)CN2C(=O)[C@@H](c2cc(N3CCC4(CC3)CN(C[C@H]3C[C@H](Oc5cc(N6C7CCC6CN(c6cc(-c8ccccc8O)nnc6N)C7)ccn5)C3)CCO4)no2)C(C)C)cc1] | (2S,4R)-1-((2R)-2-(3-(4-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-1-oxa-4,9-diazaspiro[5.5]undecan-9-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 625 | 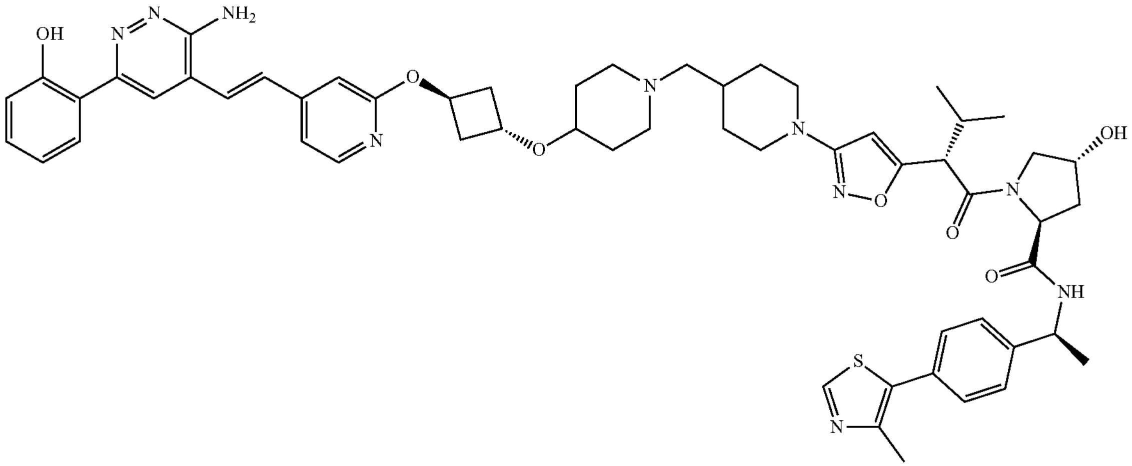 [SMILES: Cc1ncsc1-c1ccc([C@H](C)NC(=O)[C@@H]2C[C@@H](O)CN2C(=O)[C@H](c2cc(N3CCC(CN4CCC(O[C@H]5C[C@H](Oc6cc(/C=C/c7cc(-c8ccccc8O)nnc7N)ccn6)C5)CC4)CC3)no2)C(C)C)cc1] | (2S,4R)-1-((S)-2-(3-(4-((4-((1r,3r)-3-((4-((E)-2-(3-amino-6-(2-hydroxyphenyl) pyridazin-4-yl)vinyl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
|---|---|---|
| []Exemplary bifunctional degradation compounds of the present disclosure | | |
| 626 | 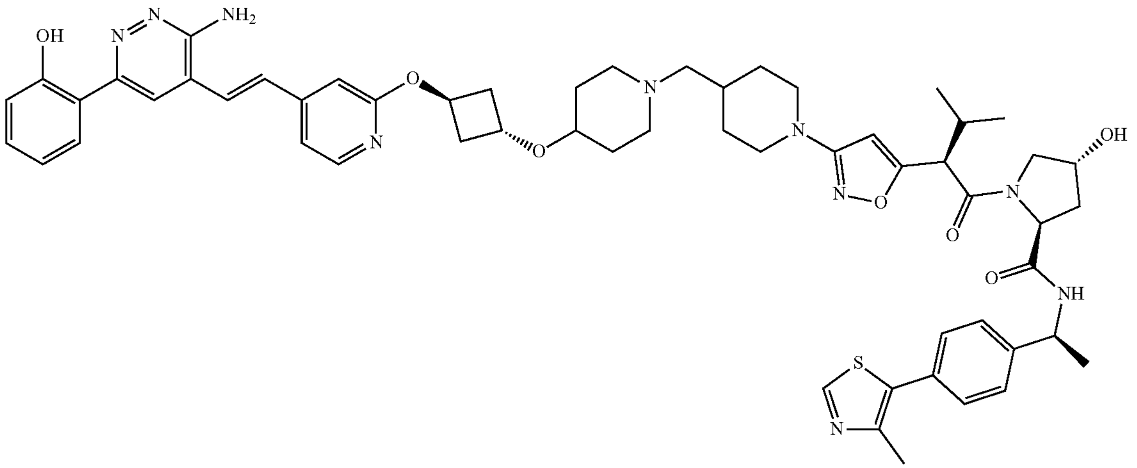 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(/C=C/c7cc(-c8ccccc8O)nnc7N)ccn6)C5)CC4)CC3)no2)C(C)C)cc1] | (2S,4R)-1-((R)-2-(3-(4-((4-((1r,3r)-3-((4-((E)-2-(3-amino-6-(2-hydroxyphenyl)pyridazin-4-yl)vinyl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 627 | 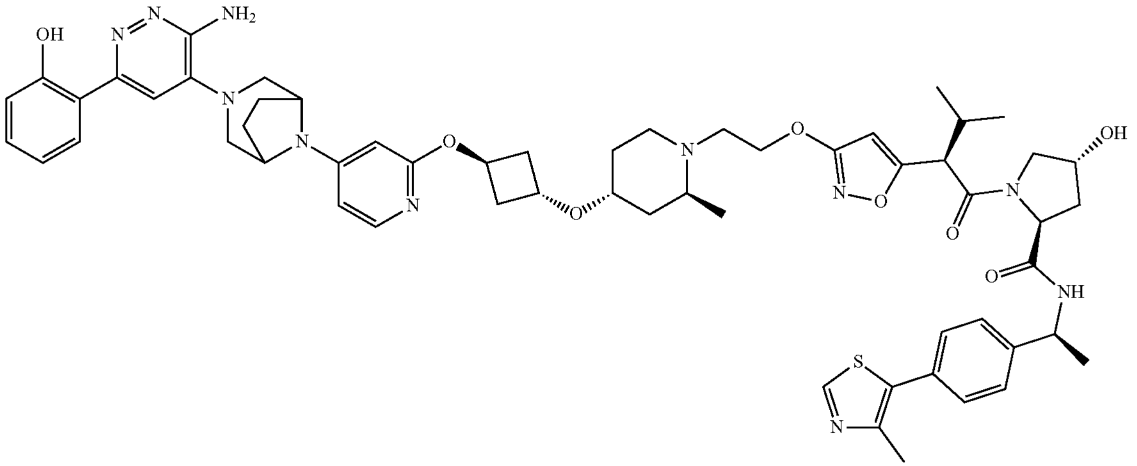 [SMILES: Cc1ncsc1-c1ccc([C@H](C)NC(=O)[C@@H]2C[C@@H](O)CN2C(=O)[C@@H](c2cc(OCCN3CC[C@@H](O[C@H]4C[C@H](Oc5cc(N6C7CCC6CN(c6cc(-c8ccccc8O)nnc6N)C7)ccn5)C4)C[C@@H]3C)no2)C(C)C)cc1] | (2S,4R)-1-((2R)-2-(3-(2-((2S,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-2-methylpiperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 628 | 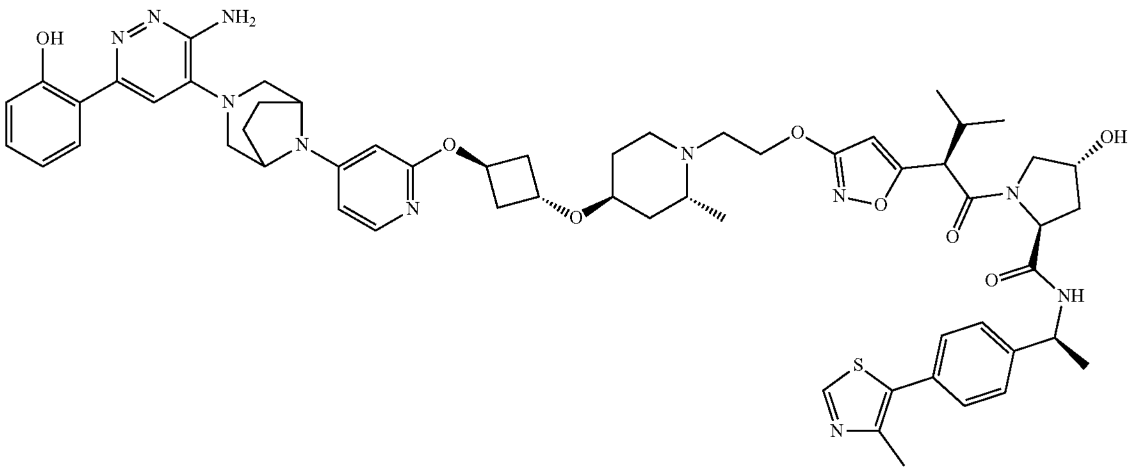 [SMILES: Cc1ncsc1-c1ccc([C@H](C)NC(=O)[C@@H]2C[C@@H](O)CN2C(=O)[C@@H](c2cc(OCCN3CC[C@H](O[C@H]4C[C@H](Oc5cc(N6C7CCC6CN(c6cc(-c8ccccc8O)nnc6N)C7)ccn5)C4)C[C@H]3C)no2)C(C)C)cc1] | (2S,4R)-1-((2R)-2-(3-(2-((2R,4S)-4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-2-methylpiperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 629 | 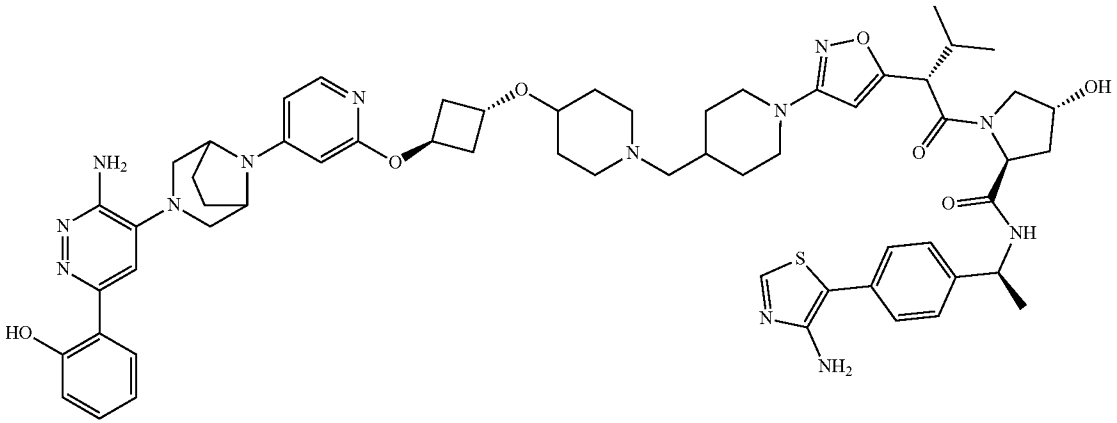 [SMILES: CC(C)[C@H](C(=O)N1C[C@H](O)C[C@H]1C(=O)N[C@@H](C)c1ccc(-c2scnc2N)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-(4-aminothiazol-5-yl)phenyl)ethyl)-4-hydroxypyrrolidine-2-carboxamide |

-continued

| []Exemplary bifunctional degradation compounds of the present disclosure | | |
|---|---|---|
| Ex No | Structure | Name |
| 630 | 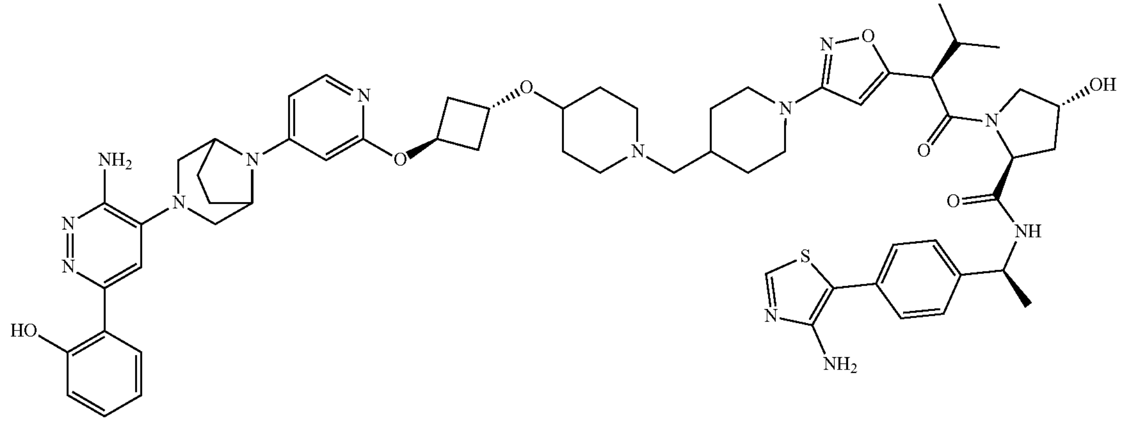 [SMILES: CC(C)[C@@H](C(=O)N1C[C@H](O)C[C@H]1C(=O)N[C@@H](C)c1ccc(-c2scnc2N)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-(4-aminothiazol-5-yl)phenyl)ethyl)-4-hydroxypyrrolidine-2-carboxamide |
| 631 | 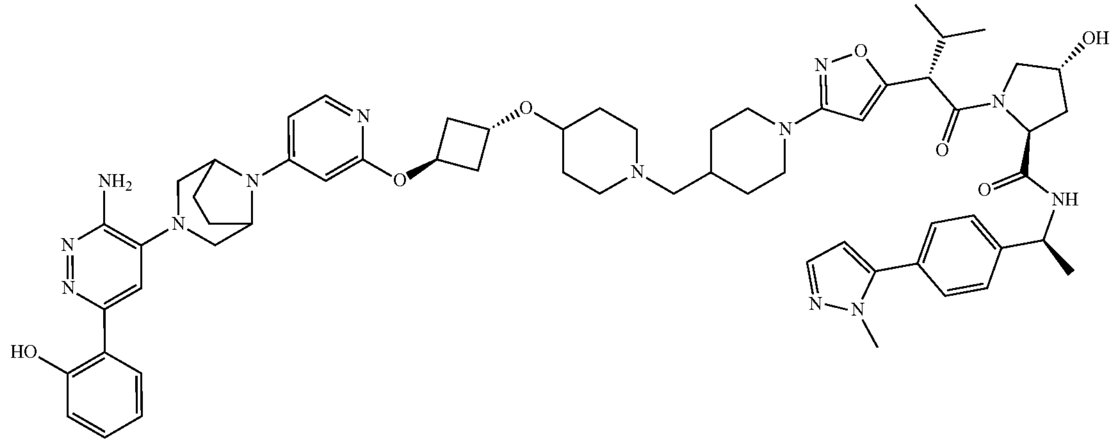 [SMILES: CC(C)[C@H](C(=O)N1C[C@H](O)C[C@H]1C(=O)N[C@@H](C)c1ccc(-c2ccnn2C)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(1-methyl-1H-pyrazol-5-yl)phenyl)ethyl)pyrrolidine-2-carboxamide |

-continued

[]Exemplary bifunctional degradation compounds of the present disclosure

| Ex No | Structure | Name |
|---|---|---|
| 632 | 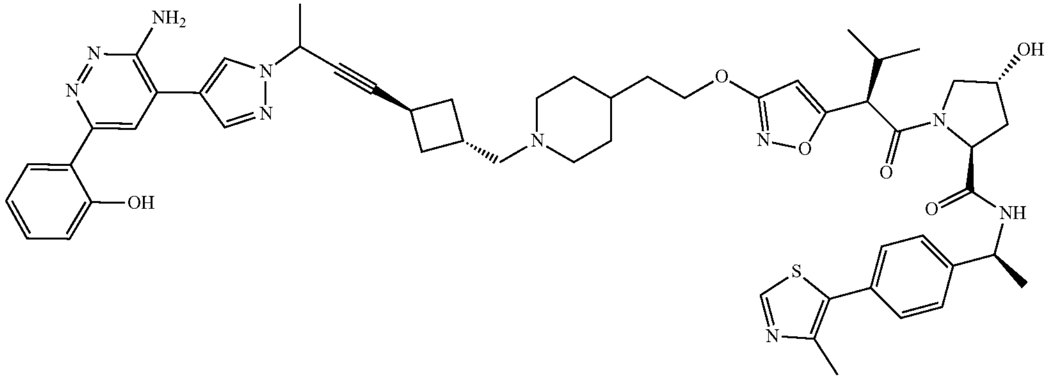 [SMILES: Cc1ncsc1-c1ccc([C@H](C)NC(=O)[C@@H]2C[C@@H](O)CN2C(=O)[C@@H](c2cc(OCCC3CCN(C[C@H]4C[C@H](C#CC(C)n5cc(-c6cc(-c7ccccc7O)nnc6N)cn5)C4)CC3)no2)C(C)C)cc1] | (2S,4R)-1-((2S)-2-(3-(2-(1-(((1r,3S)-3-(3-(4-(3-amino-6-(2-hydroxyphenyl)pyridazin-4-yl)-1H-pyrazol-1-yl)but-1-yn-1-yl)cyclobutyl)methyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 633 | 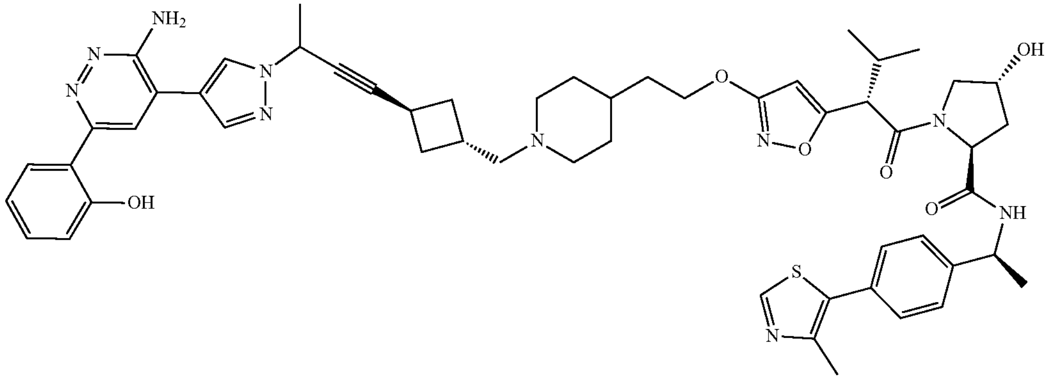 [SMILES: Cc1ncsc1-c1ccc([C@H](C)NC(=O)[C@@H]2C[C@@H](O)CN2C(=O)[C@H](c2cc(OCCC3CCN(C[C@H]4C[C@H](C#CC(C)n5cc(-c6cc(-c7ccccc7O)nnc6N)cn5)C4)CC3)no2)C(C)C)cc1] | (2S,4R)-1-((2R)-2-(3-(2-(1-(((1r,3R)-3-(3-(4-(3-amino-6-(2-hydroxyphenyl)pyridazin-4-yl)-1H-pyrazol-1-yl)but-1-yn-1-yl)cyclobutyl)methyl)piperidin-4-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
| --- | --- | --- |
| | []Exemplary bifunctional degradation compounds of the present disclosure | |
| 634 | 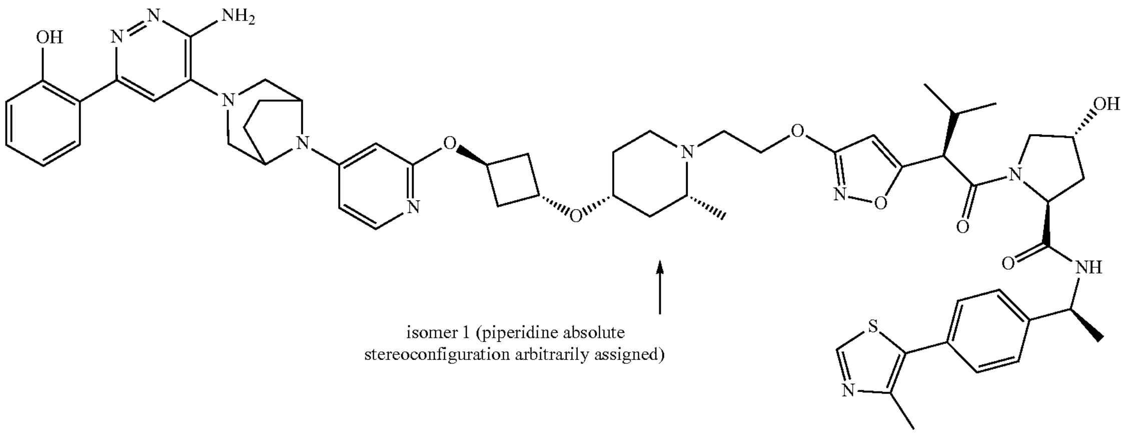 [SMILES: Cc1ncsc1-c1ccc([C@H](C)NC(=O)[C@@H]2C[C@@H](O)CN2C(=O)[C@@H](c2cc(OCCN3CC[C@@H](O[C@H]4C[C@H](Oc5cc(N6C7CCC6CN(c6cc(-c8ccccc8O)nnc6N)C7)ccn5)C4)C[C@H]3C)no2)C(C)C)cc1] | (2S,4R)-1-((2R)-2-(3-(2-((2R,4R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-2-methylpiperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 635 | 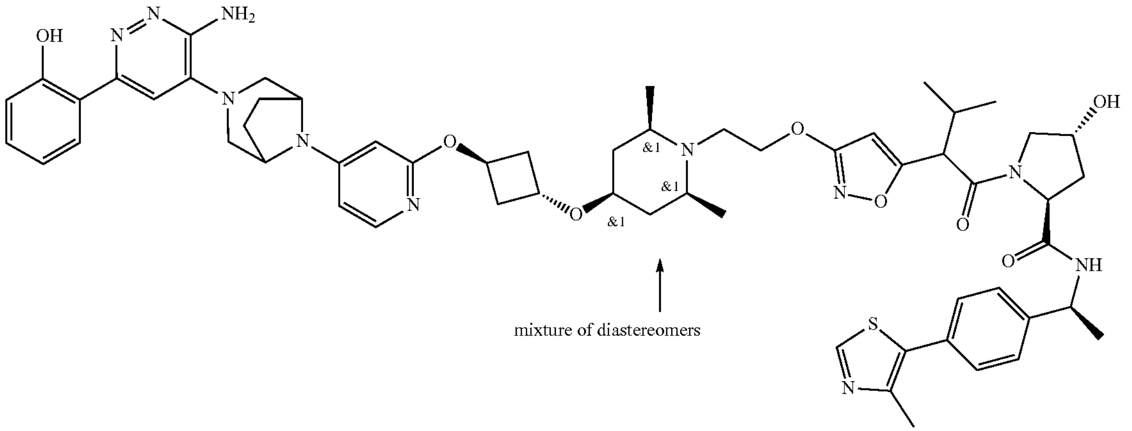 [SMILES: Cc1ncsc1-c1ccc([C@H](C)NC(=O)[C@@H]2C[C@@H](O)CN2C(=O)C(c2cc(OCCN3[C@H](C)C[C@H](O[C@H]4C[C@H](Oc5cc(N6C7CCC6CN(c6cc(-c8ccccc8O)nnc6N)C7)ccn5)C4)C[C@@H]3C)no2)C(C)C)cc1] | (2S,4R)-1-(2-(3-(2-((2S,4S,6R)-4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-2,6-dimethylpiperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 636 | 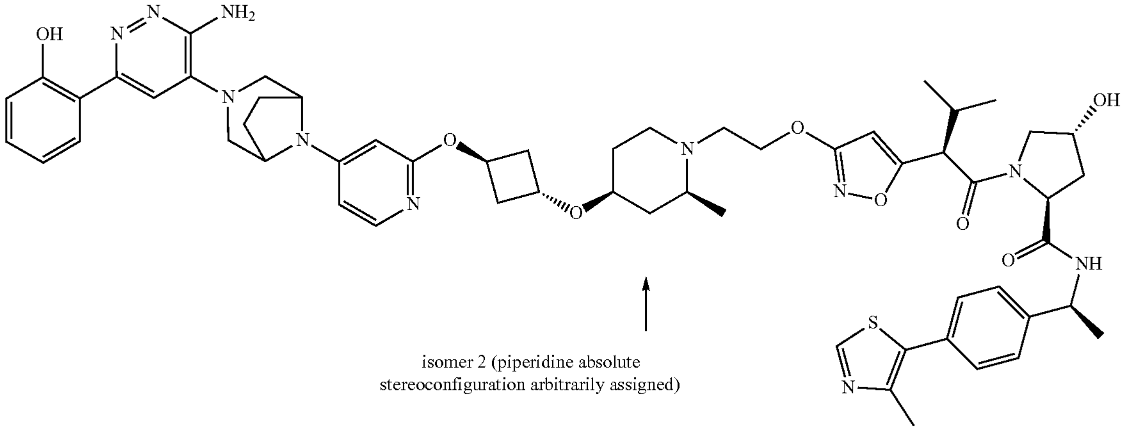 [SMILES: Cc1ncsc1-c1ccc([C@H](C)NC(=O)[C@@H]2C[C@@H](O)CN2C(=O)[C@@H](c2cc(OCCN3CC[C@H](O[C@H]4C[C@H](Oc5cc(N6C7CCC6CN(c6cc(-c8ccccc8O)nnc6N)C7)ccn5)C4)C[C@@H]3C)no2)C(C)C)cc1] isomer 2 (piperidine absolute stereoconfiguration arbitrarily assigned) | (2S,4R)-1-((2R)-2-(3-(2-((2S,4S)-4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-2-methylpiperidin-1-yl)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 637 | stereocorriguration arbitrarily assigned 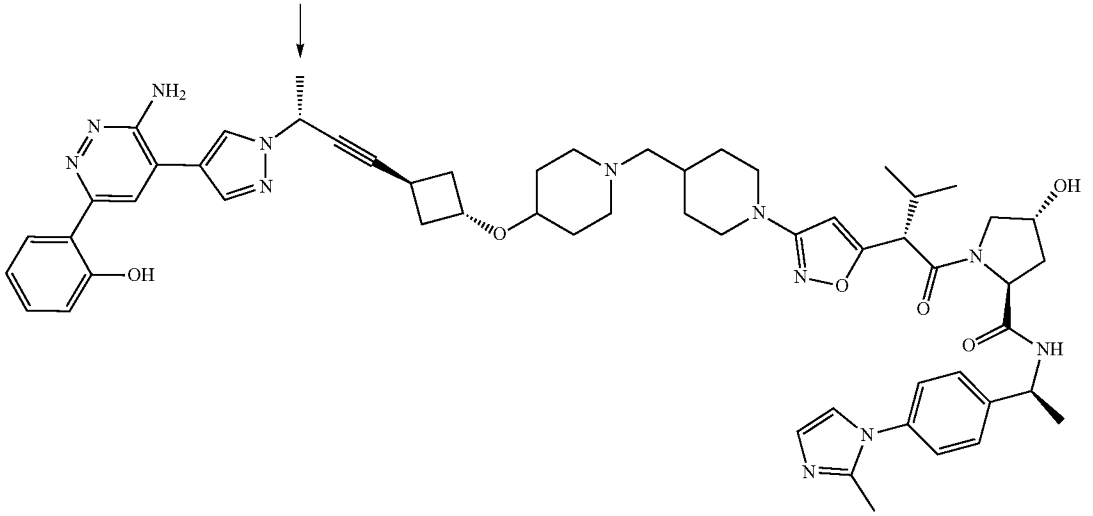 | (2S,4R)-1-((S)-2-(3-(4-((4-((1R,3r)-3-((R)-3-(4-(3-amino-6-(2-hydroxyphenyl)pyridazin-4-yl)-1H-pyrazol-1-yl)but-1-yn-1-yl)cyclobutoxy)piperidin-1-yl)methyl)piperidin-1-yl)isoxazol-5-yl)-3-methylbutanoyl)-4-hydroxy-N-((S)-1-(4-(2-methyl-1H-imidazol-1-yl)phenyl)ethyl)pyrrolidine-2-carboxamide |

-continued

[]Exemplary bifunctional degradation compounds of the present disclosure

| Ex No | Structure | Name |
|---|---|---|
| 638 | stereocorriguration arbitrarily assigned 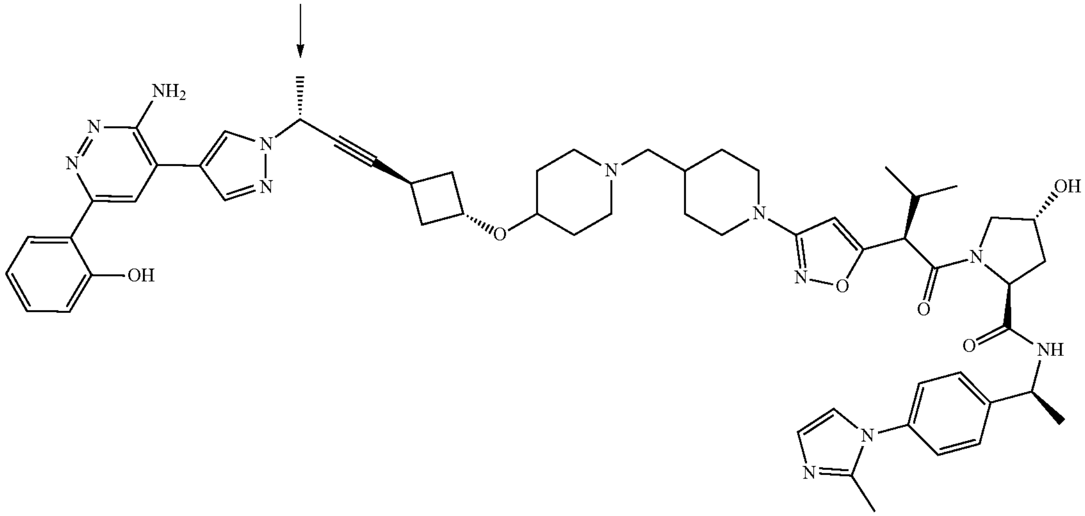 | (2S,4R)-1-((R)-2-(3-(4-((4-((1R,3r)-3-((R)-3-(4-(3-amino-6-(2-hydroxyphenyl)pyridazin-4-yl)-1H-pyrazol-1-yl)but-1-yn-1-yl)cyclobutoxy)piperidin-1-yl)methyl)piperidin-1-yl)isoxazol-5-yl)-3-methylbutanoyl)-4-hydroxy-N-((S)-1-(4-(2-methyl-1H-imidazol-1-yl)phenyl)ethyl) pyrrolidine-2-carboxamide |
| 639 | 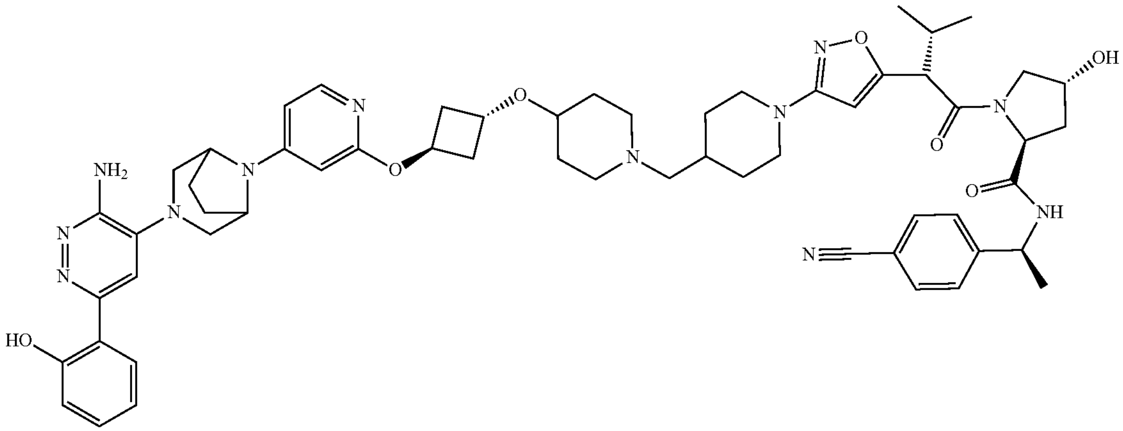 | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-cyanophenyl)ethyl)-4-hydroxypyrrolidine-2-carboxamide |

-continued

[]Exemplary bifunctional degradation compounds of the present disclosure

| Ex No | Structure | Name |
| --- | --- | --- |
| 640 | 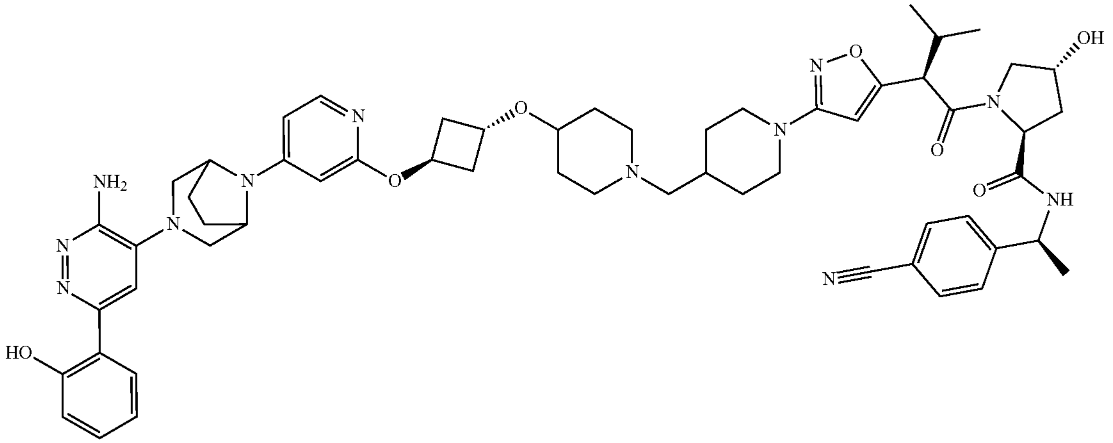 [SMILES: CC(C)[C@@H](C(=O)N1C[C@H](O)C[C@H]1C(=O)N[C@@H](C)c1ccc(C#N)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-cyanophenyl)ethyl)-4-hydroxypyrrolidine-2-carboxamide |
| 641 | 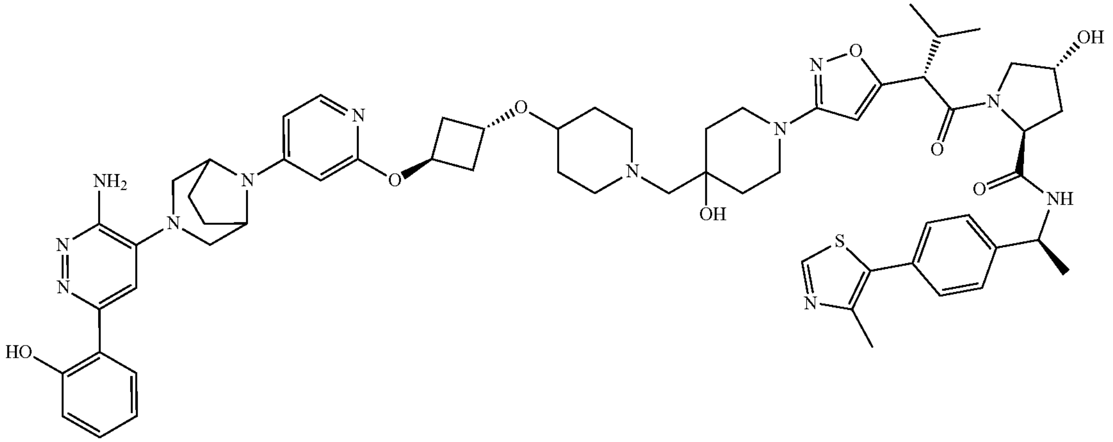 [SMILES: Cc1ncsc1-c1ccc([C@H](C)NC(=O)[C@@H]2C[C@@H](O)CN2C(=O)[C@H](c2cc(N3CCC(O)(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-4-hydroxypiperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
|---|---|---|
| []Exemplary bifunctional degradation compounds of the present disclosure | | |
| 642 | 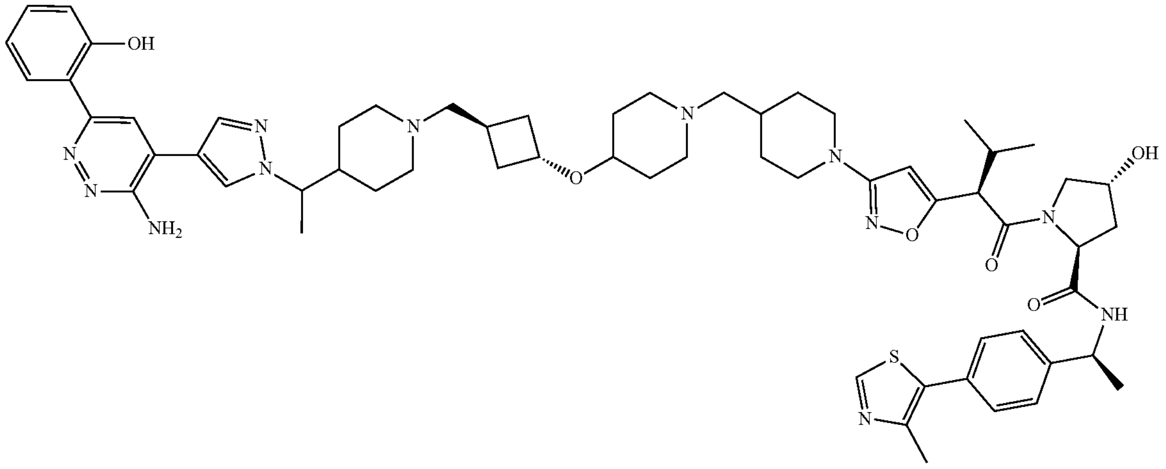 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](CN6CCC(C(C)n7cc(-c8cc(-c9ccccc9O)nnc8N)cn7)CC6)C5)CC4)CC3)no2)C(C)C)cc1] | (2S,4R)-1-((2R)-2-(3-(4-((4-((1r,3r)-3-((4-(1-(4-(3-amino-6-(2-hydroxyphenyl)pyridazin-4-yl)-1H-pyrazol-1-yl)ethyl)piperidin-1-yl)methyl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 643 | 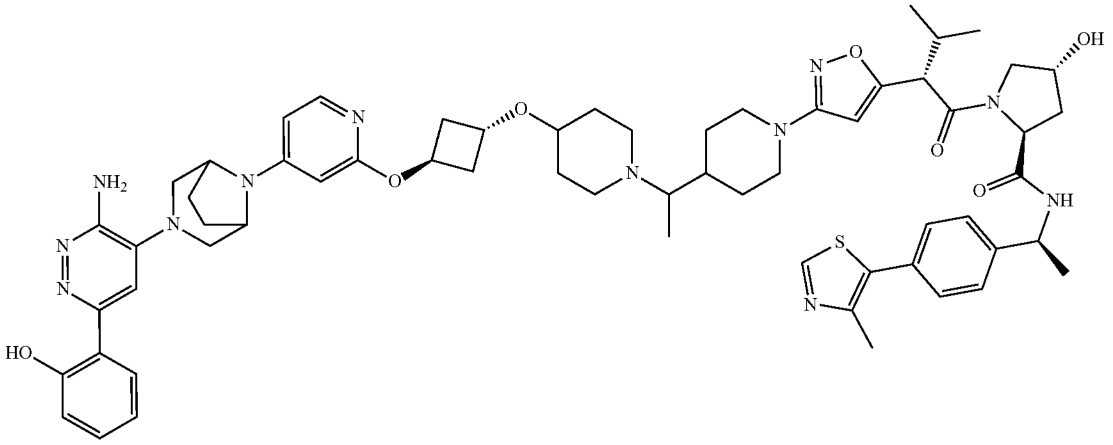 [SMILES: Cc1ncsc1-c1ccc([C@H](C)NC(=O)[C@@H]2C[C@@H](O)CN2C(=O)[C@H](c2cc(N3CCC(C(C)N4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-(1-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 644 | 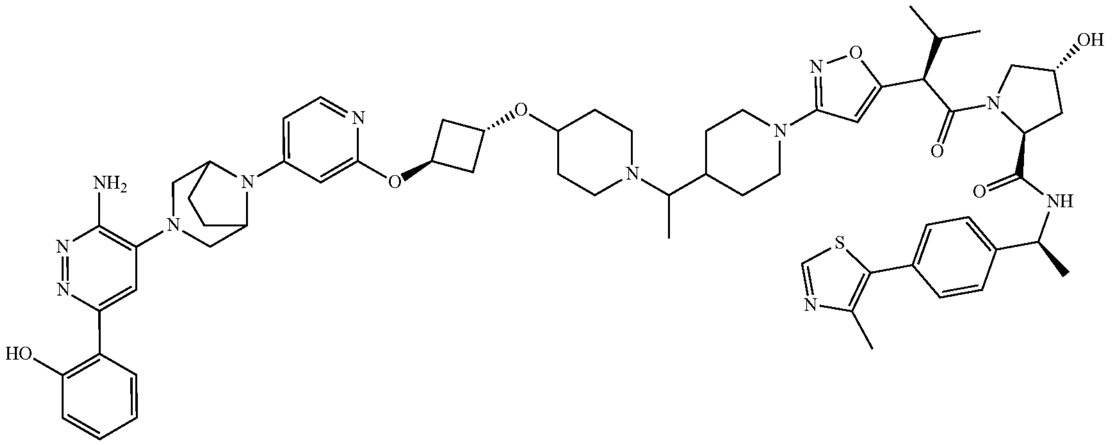 [SMILES: Cc1ncsc1-c1ccc([C@H](C)NC(=O)[C@@H]2C[C@@H](O)CN2C(=O)[C@@H](c2cc(N3CCC(C(C)N4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-(1-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 645 | 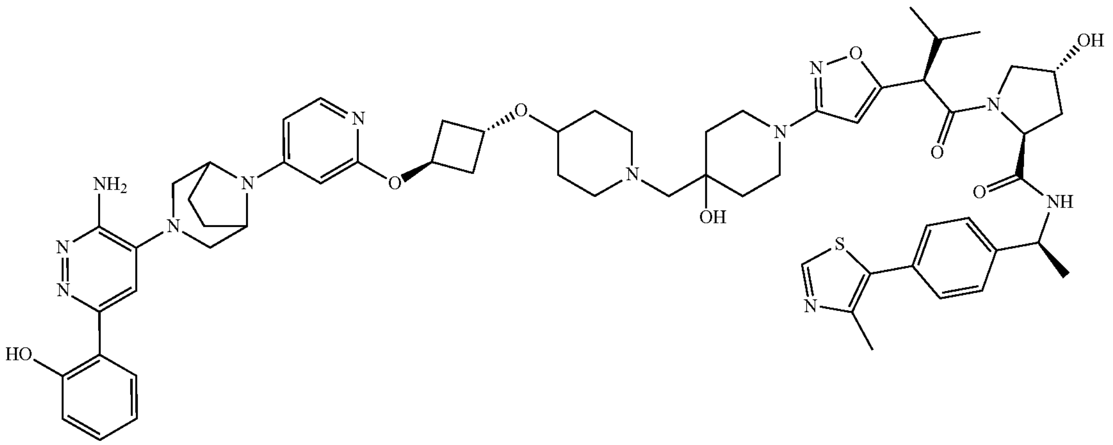 [SMILES: Cc1ncsc1-c1ccc([C@H](C)NC(=O)[C@@H]2C[C@@H](O)CN2C(=O)[C@@H](c2cc(N3CCC(O)(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-4-hydroxypiperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 646 | 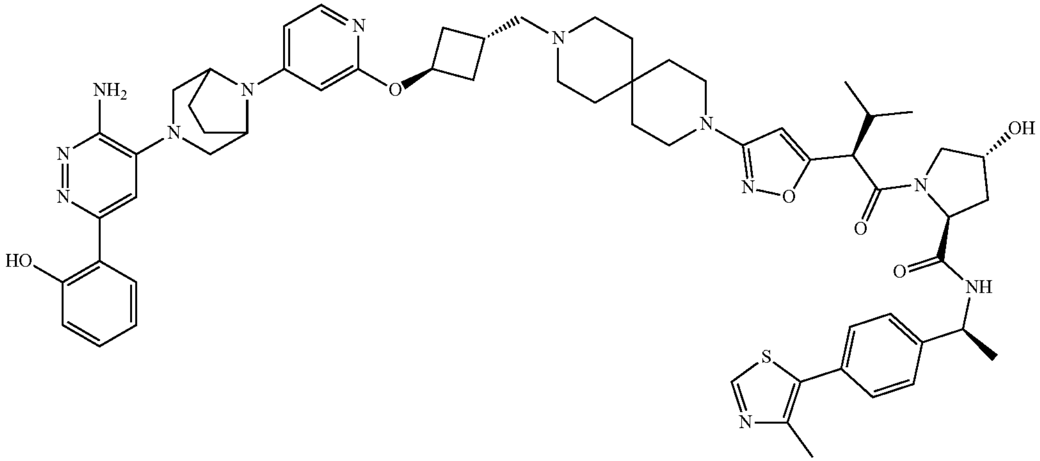 [SMILES: Cc1ncsc1-c1ccc([C@H](C)NC(=O)[C@@H]2C[C@@H](O)CN2C(=O)[C@@H](c2cc(N3CCC4(CCN(C[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(9-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3,9-diazaspiro[5.5]undecan-3-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 647 | 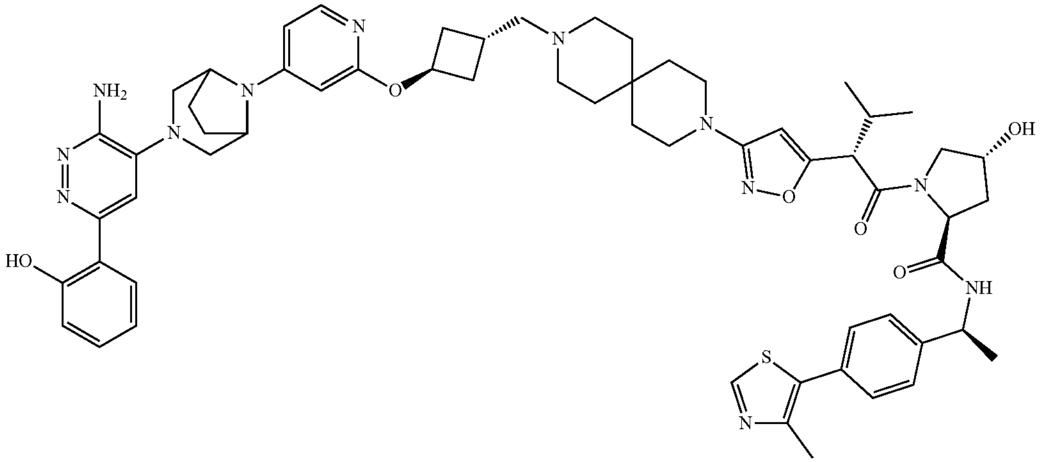 [SMILES: Cc1ncsc1-c1ccc([C@H](C)NC(=O)[C@@H]2C[C@@H](O)CN2C(=O)[C@H](c2cc(N3CCC4(CCN(C[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(9-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3,9-diazaspiro[5.5]undecan-3-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued
| []Exemplary bifunctional degradation compounds of the present disclosure | | |
|---|---|---|
| Ex No | Structure | Name |
| 648 | 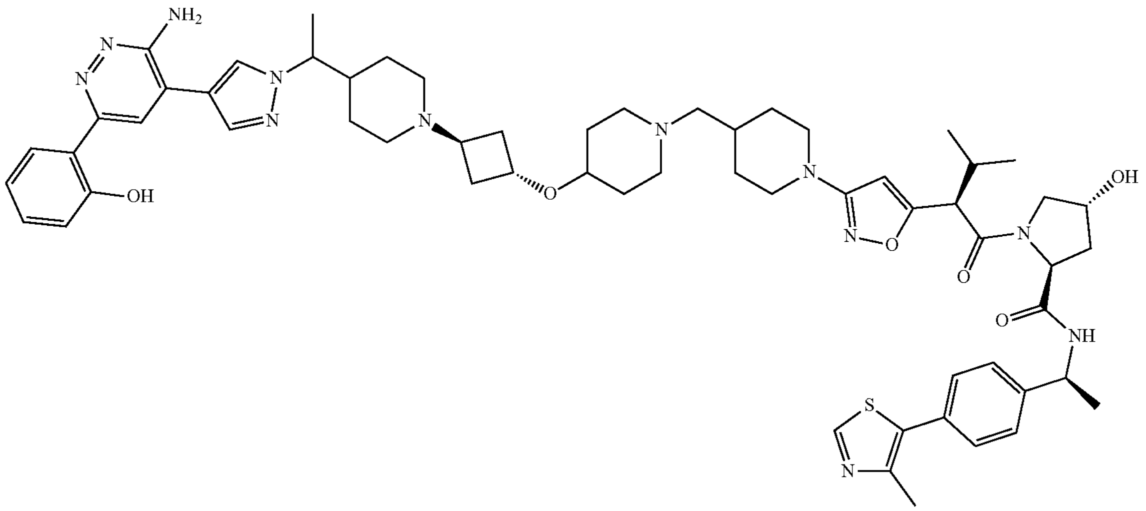 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](N6CCC(C(C)n7cc(-c8cc(-c9ccccc9O)nnc8N)cn7)CC6)C5)CC4)CC3)no2)C(C)C)cc1] | (2S,4R)-1-((2R)-2-(3-(4-((4-((1r,3r)-3-(4-(1-(4-(3-amino-6-(2-hydroxyphenyl)pyridazin-4-yl)-1H-pyrazol-1-yl)ethyl)piperidin-1-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued
| []Exemplary bifunctional degradation compounds of the present disclosure | | |
|---|---|---|
| Ex No | Structure | Name |
| 649 | 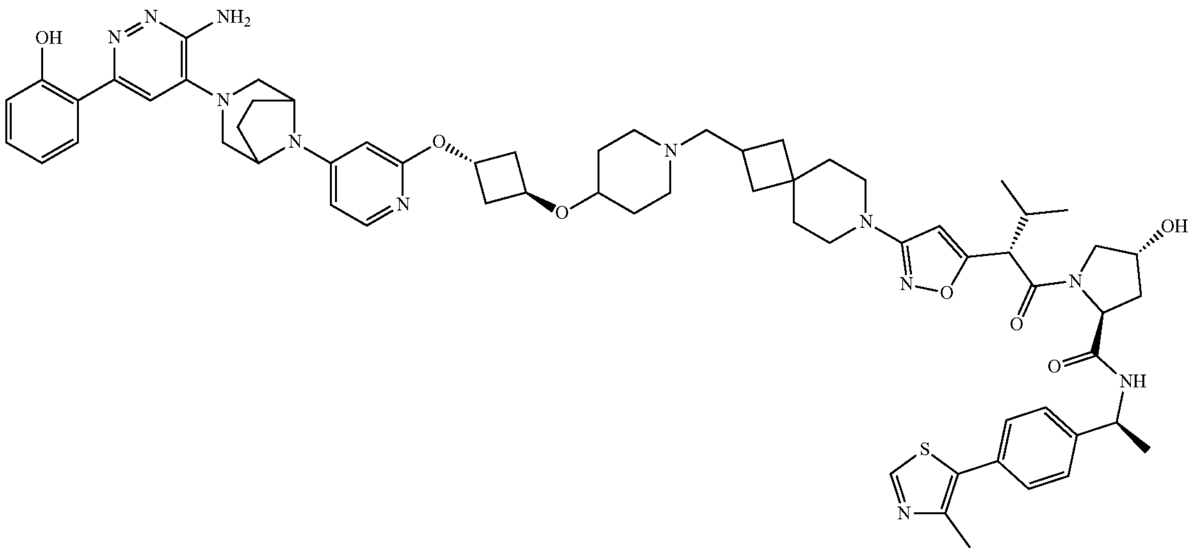 | (2S,4R)-1-((2S)-2-(3-(2-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-7-azaspiro[3.5]nonan-7-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
|---|---|---|
| | []Exemplary bifunctional degradation compounds of the present disclosure | |
| 650 | 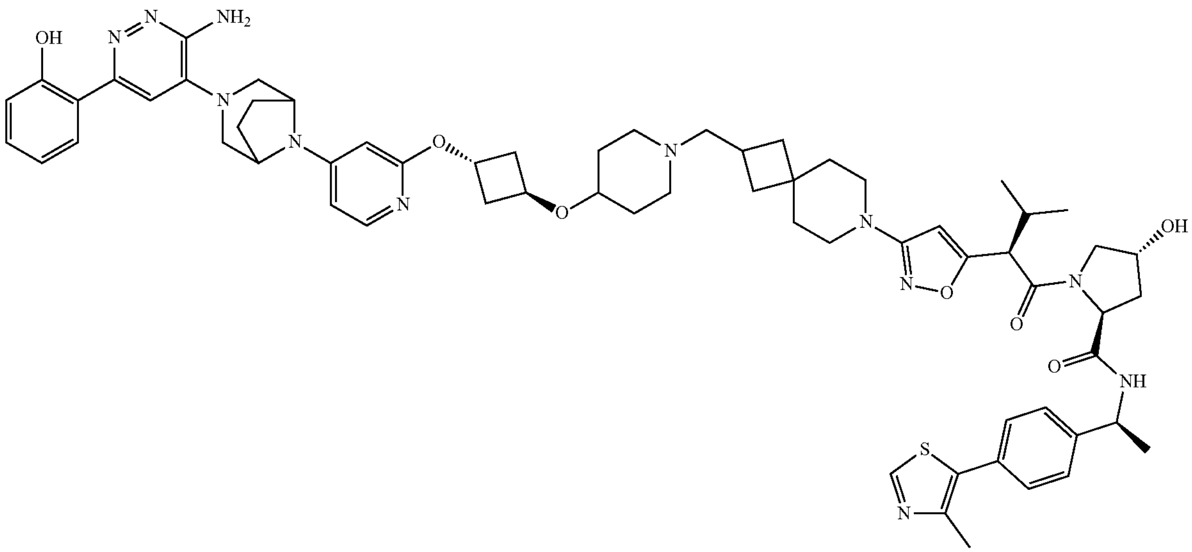 [SMILES: Cc1ncsc1-c1ccc([C@H](C)NC(=O)[C@@H]2C[C@@H](O)CN2C(=O)[C@@H](c2cc(N3CCC4(CC3)CC(CN3CCC(O[C@H]5C[C@H](Oc6cc(N7C8CCC7CN(c7cc(-c9ccccc9O)nnc7N)C8)ccn6)C5)CC3)C4)no2)C(C)C)cc1] | (2S,4R)-1-((2R)-2-(3-(2-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-7-azaspiro[3.5]nonan-7-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 651 | 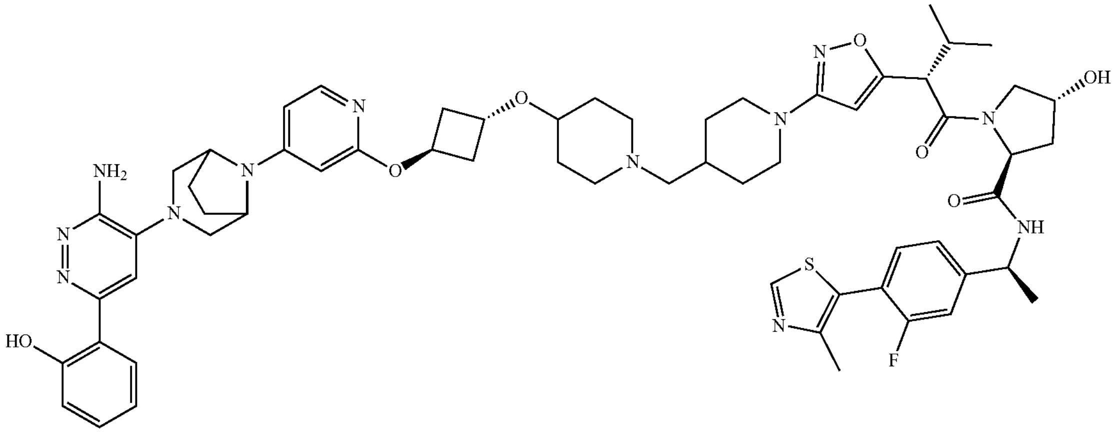 [SMILES: Cc1ncsc1-c1ccc([C@H](C)NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1F] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(3-fluoro-4-(4-methylthiazol-5-yl)phenyl)ethyl)-4-hydroxypyrrolidine-2-carboxamide |

-continued

[]Exemplary bifunctional degradation compounds of the present disclosure

| Ex No | Structure | Name |
| --- | --- | --- |
| 652 | 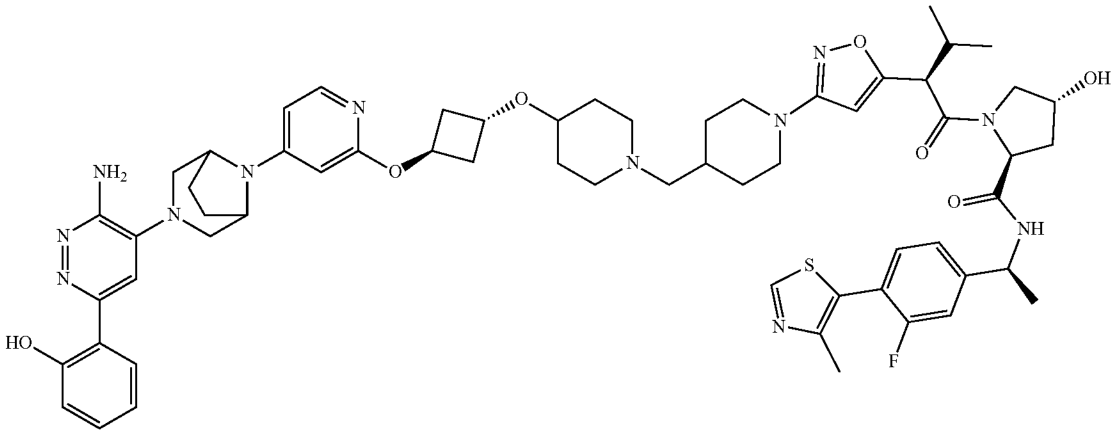 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1F] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(3-fluoro-4-(4-methylthiazol-5-yl)phenyl)ethyl)-4-hydroxypyrrolidine-2-carboxamide |
| 653 | 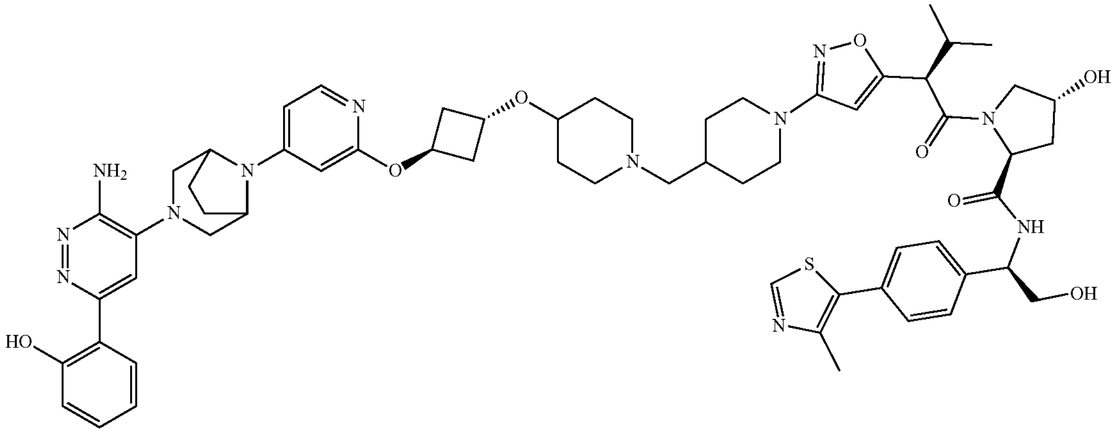 [SMILES: Cc1ncsc1-c1ccc([C@H](CO)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((R)-2-hydroxy-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 654 | 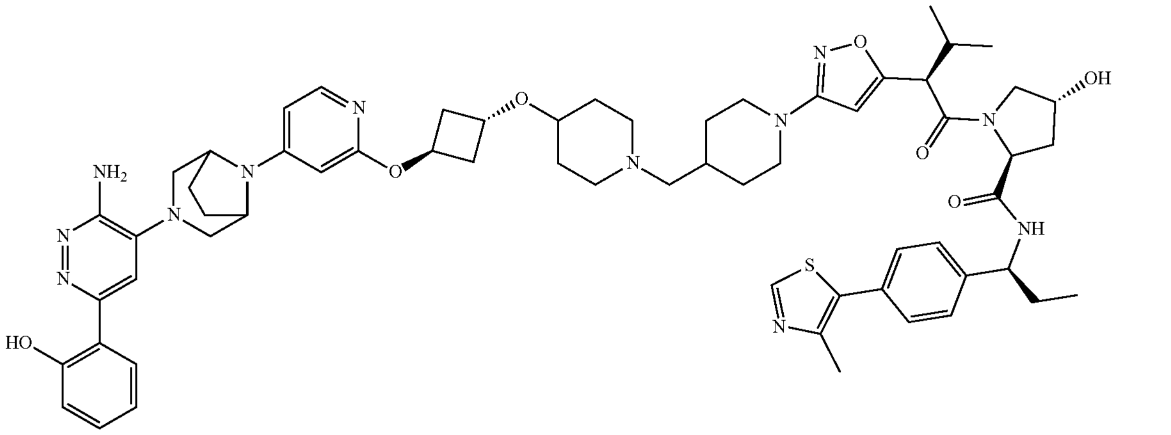 [SMILES: CC[C@H](NC(=O)[C@@H]1C[C@@H](O)CN1C(=O)[C@@H](c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1)C(C)C)c1ccc(-c2scnc2C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)propyl)pyrrolidine-2-carboxamide |
| 655 | 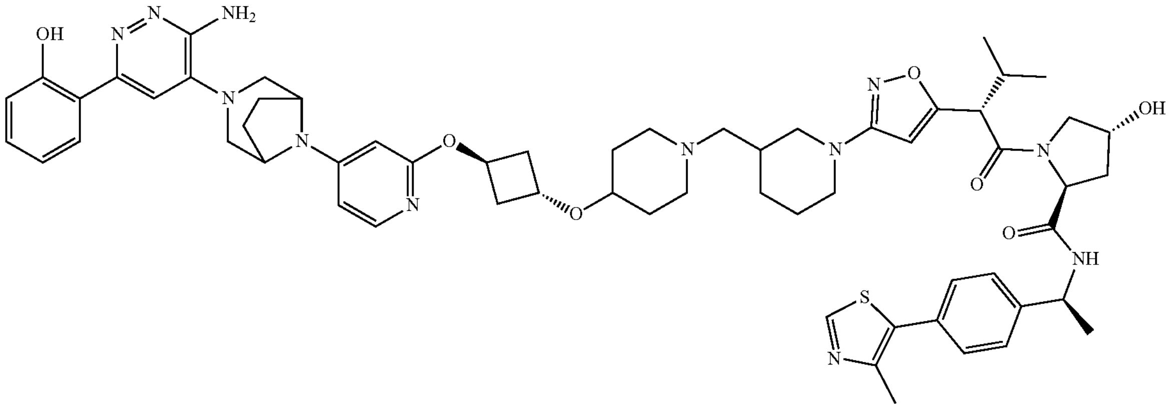 [SMILES: Cc1ncsc1-c1ccc([C@H](C)NC(=O)[C@@H]2C[C@@H](O)CN2C(=O)[C@H](c2cc(N3CCCC(CN4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2S)-2-(3-(3-((4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 656 | isomer 1 (absolute stereoconfiguration arbitrarily assigned) 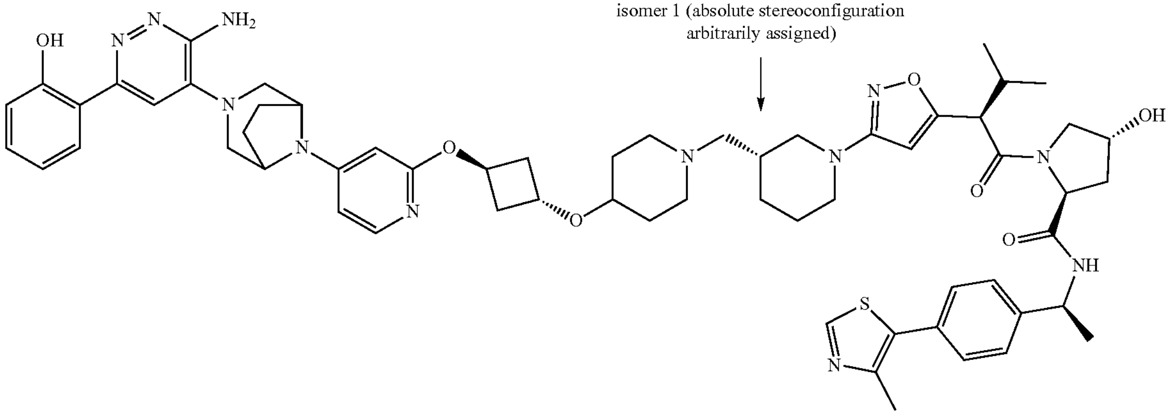 [SMILES: Cc1ncsc1-c1ccc([C@H](C)NC(=O)[C@@H]2C[C@@H](O)CN2C(=O)[C@@H](c2cc(N3CCC[C@H](CN4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2R)-2-(3-((3R)-3-((4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 657 | isomer 2 (absolute stereoconfiguration arbitrarily assigned) 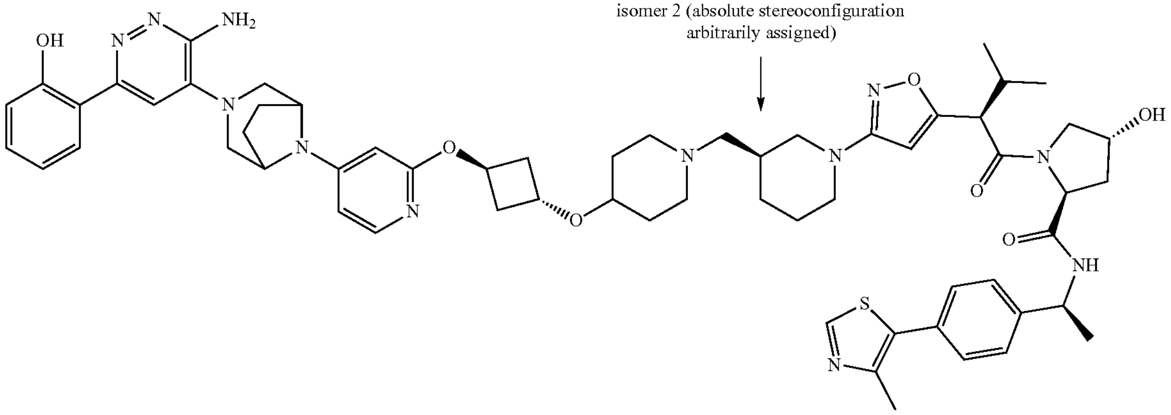 [SMILES: Cc1ncsc1-c1ccc([C@H](C)NC(=O)[C@@H]2C[C@@H](O)CN2C(=O)[C@@H](c2cc(N3CCC[C@@H](CN4CCC(O[C@H]5C[C@H](Oc6cc(N7C8CCC7CN(c7cc(-c9ccccc9O)nnc7N)C8)ccn6)C5)CC4)C3)no2)C(C)C)cc1] | (2S,4R)-1-((2R)-2-(3-((3S)-3-((4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued
| []Exemplary bifunctional degradation compounds of the present disclosure | | |
|---|---|---|
| Ex No | Structure | Name |
| 658 | 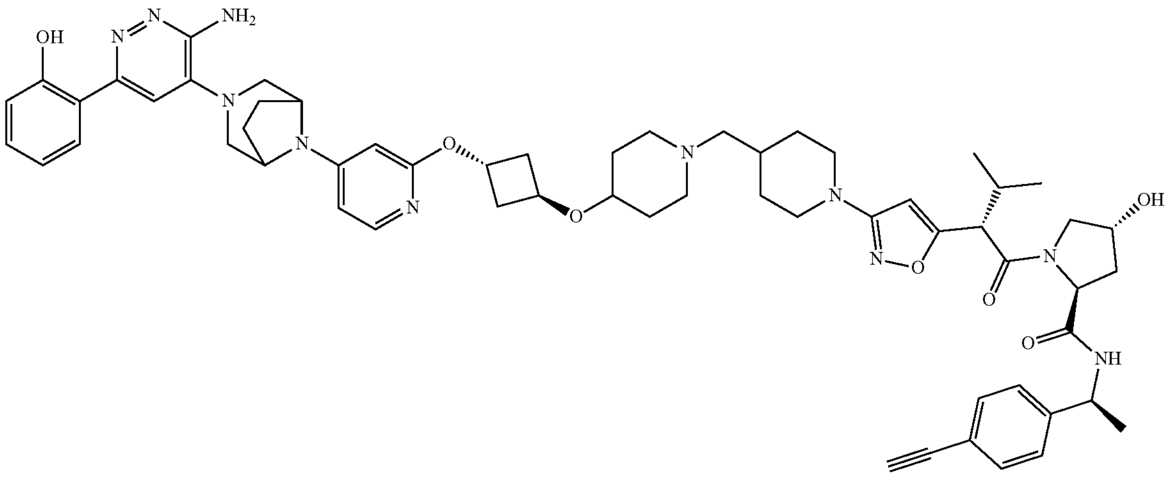 [SMILES: C#Cc1ccc([C@H](C)NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-ethynylphenyl)ethyl)-4-hydroxypyrrolidine-2-carboxamide |

-continued
| Ex No | Structure | Name |
|---|---|---|
| | []Exemplary bifunctional degradation compounds of the present disclosure | |
| 659 | 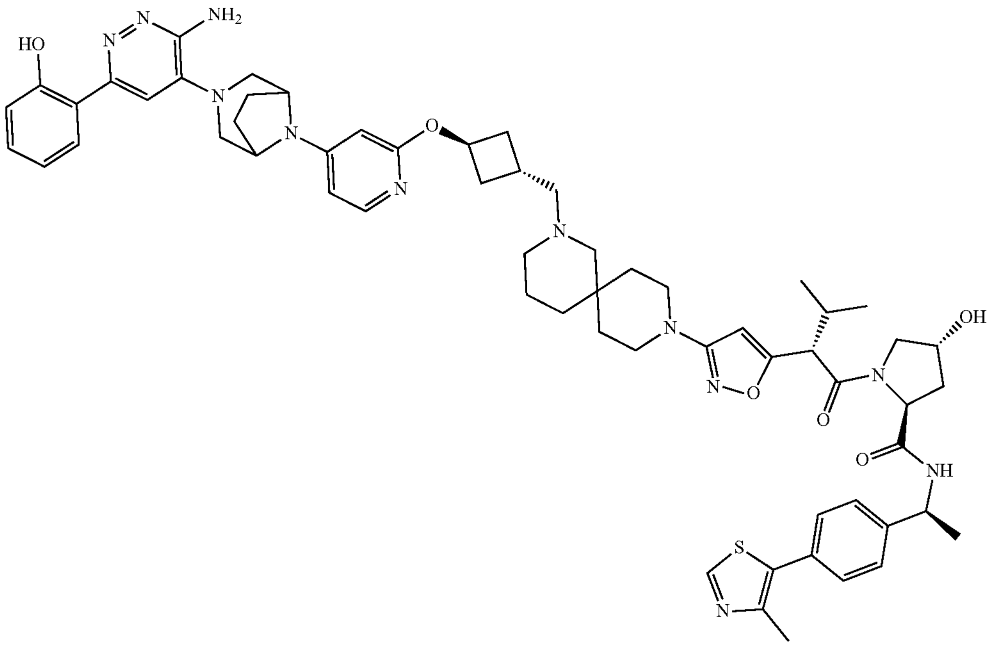 [SMILES: Cc1ncsc1-c1ccc([C@H](C)NC(=O)[C@@H]2C[C@@H](O)CN2C(=O)[C@H](c2cc(N3CCC4(CCCN(C[C@H]5C[C@H](Oc6cc(N7C8CCC7CN(c7cc(-c9ccccc9O)nnc7N)C8)ccn6)C5)C4)CC3)no2)C(C)C)cc1] | (2S,4R)-1-((2S)-2-(3-(2-(((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,9-diazaspiro[5.5]undecan-9-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued
| []Exemplary bifunctional degradation compounds of the present disclosure | | |
|---|---|---|
| Ex No | Structure | Name |
| 660 | 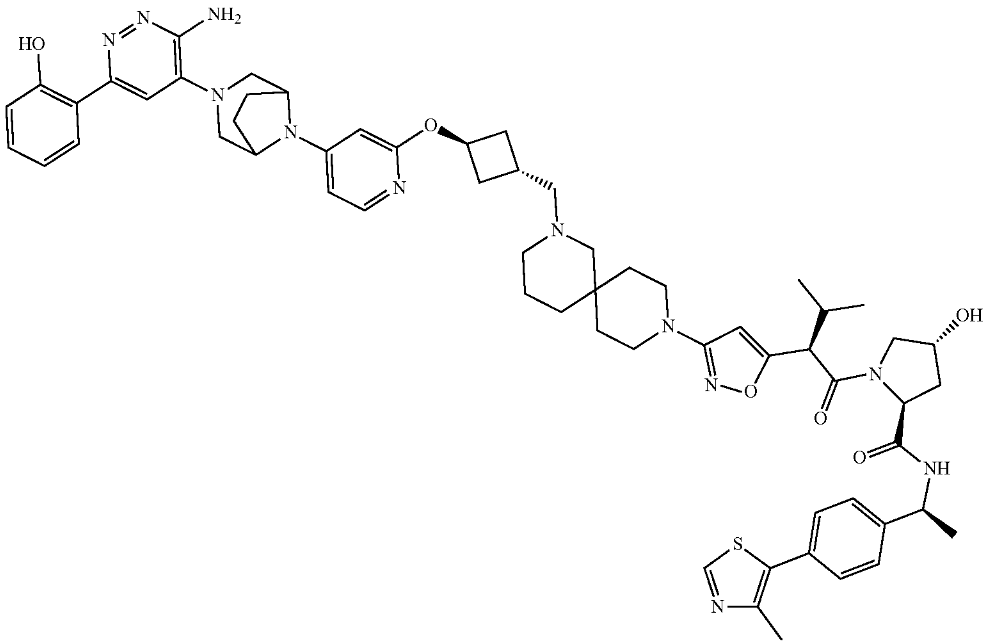 [SMILES: Cc1ncsc1-c1ccc([C@H](C)NC(=O)[C@@H]2C[C@@H](O)CN2C(=O)[C@@H](c2cc(N3CCC4(CCCN(C[C@H]5C[C@H](Oc6cc(N7C8CCC7CN(c7cc(-c9ccccc9O)nnc7N)C8)ccn6)C5)C4)CC3)no2)C(C)C)cc1] | (2S,4R)-1-((2R)-2-(3-(2-(((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,9-diazaspiro[5.5]undecan-9-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 661 | 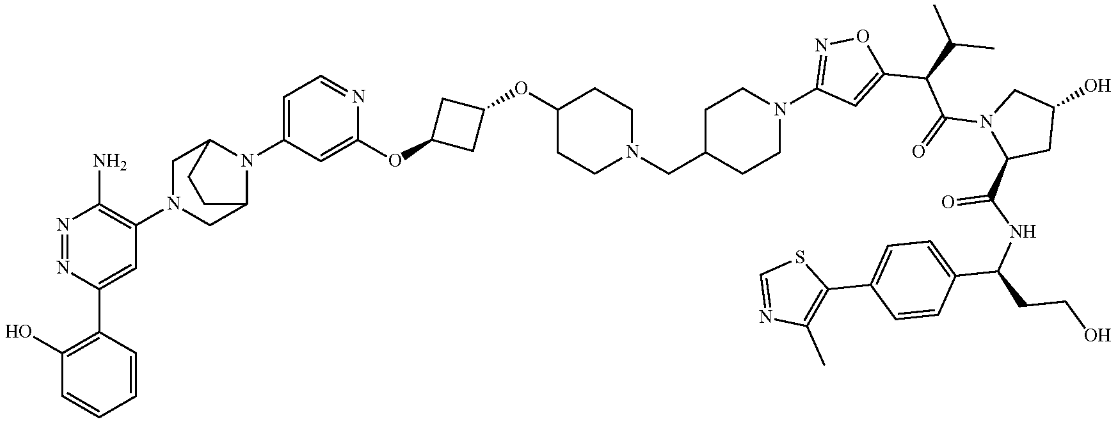 [SMILES: Cc1ncsc1-c1ccc([C@H](CCO)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-3-hydroxy-1-(4-(4-methylthiazol-5-yl)phenyl)propyl)pyrrolidine-2-carboxamide |
| 662 | 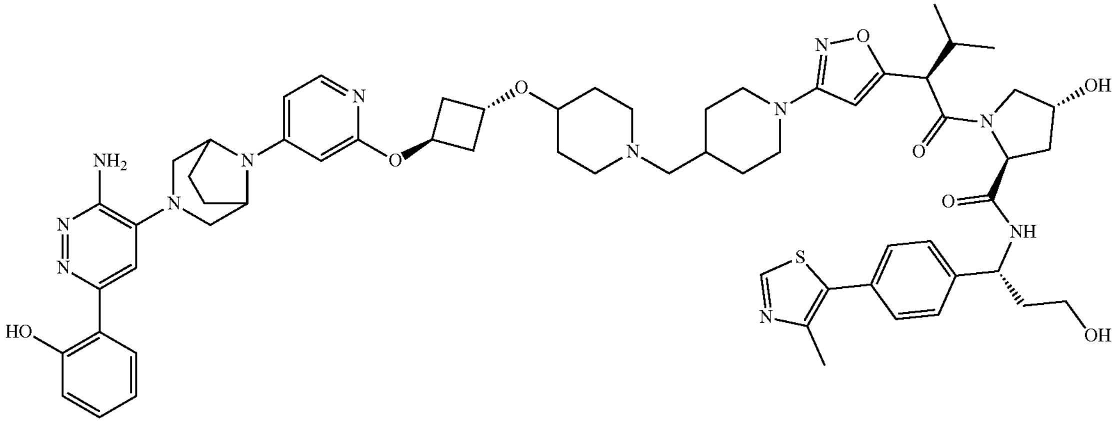 [SMILES: Cc1ncsc1-c1ccc([C@@H](CCO)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((R)-3-hydroxy-1-(4-(4-methylthiazol-5-yl)phenyl)propyl)pyrrolidine-2-carboxamide |

-continued

| []Exemplary bifunctional degradation compounds of the present disclosure | | |
|---|---|---|
| Ex No | Structure | Name |
| 663 | 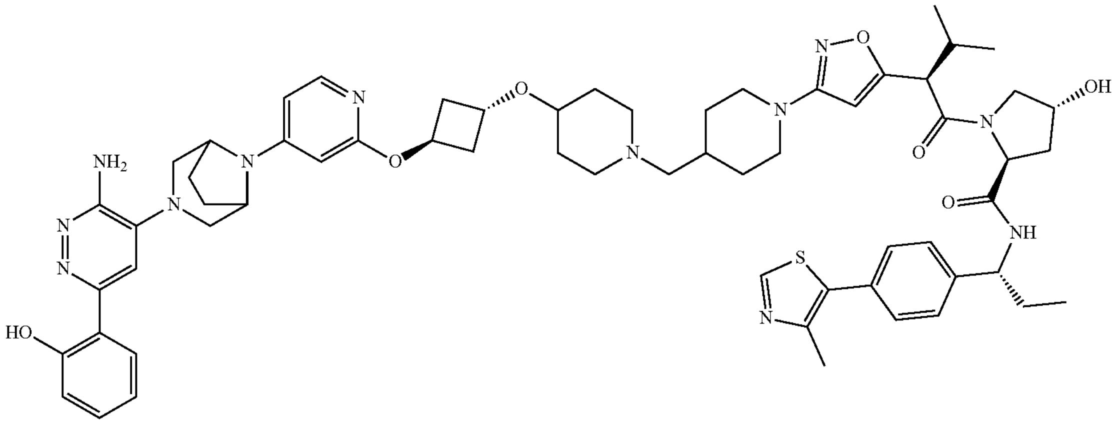 [SMILES: CC[C@@H](NC(=O)[C@@H]1C[C@@H](O)CN1C(=O)[C@@H](c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1)C(C)C)c1ccc(-c2scnc2C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((R)-1-(4-(4-methylthiazol-5-yl)phenyl)propyl)pyrrolidine-2-carboxamide |
| 664 | 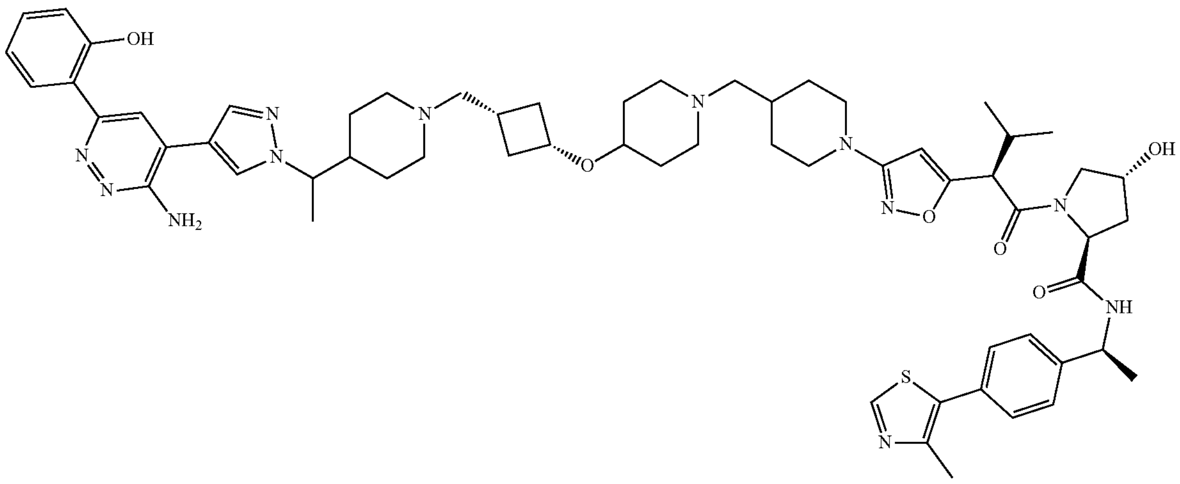 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@@H](CN6CCC(C(C)n7cc(-c8cc(-c9ccccc9O)nnc8N)cn7)CC6)C5)CC4)CC3)no2)C(C)C)cc1] | (2S,4R)-1-((2R)-2-(3-(4-((4-((1s,3s)-3-((4-(1-(4-(3-amino-6-(2-hydroxyphenyl)pyridazin-4-yl)-1H-pyrazol-1-yl)ethyl)piperidin-1-yl)methyl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 665 | 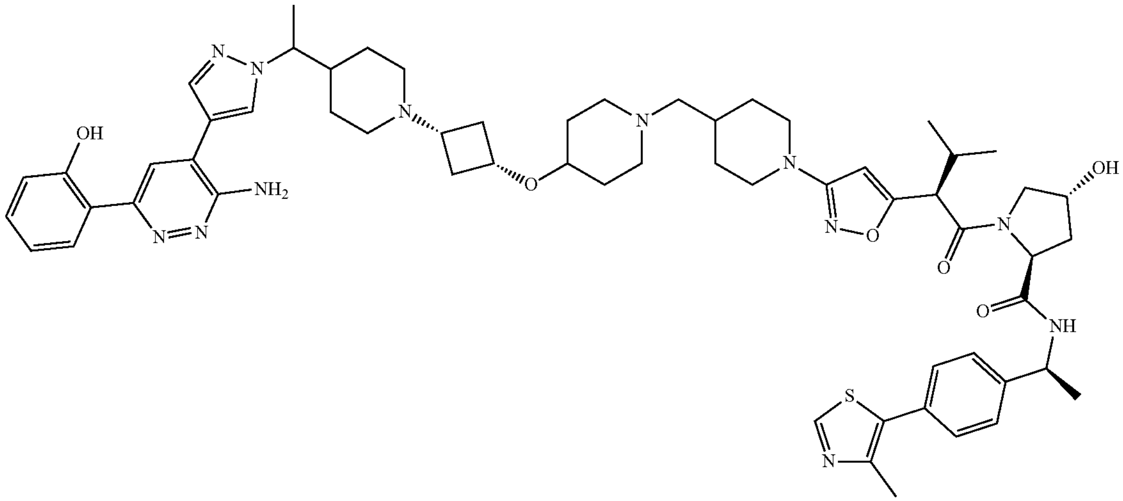 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@@H](N6CCC(C(C)n7cc(-c8cc(-c9ccccc9O)nnc8N)cn7)CC6)C5)CC4)CC3)no2)C(C)C)cc1] | (2S,4R)-1-((2R)-2-(3-(4-((4-((1s,3s)-3-(4-(1-(4-(3-amino-6-(2-hydroxyphenyl)pyridazin-4-yl)-1H-pyrazol-1-yl)ethyl)piperidin-1-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 666 | 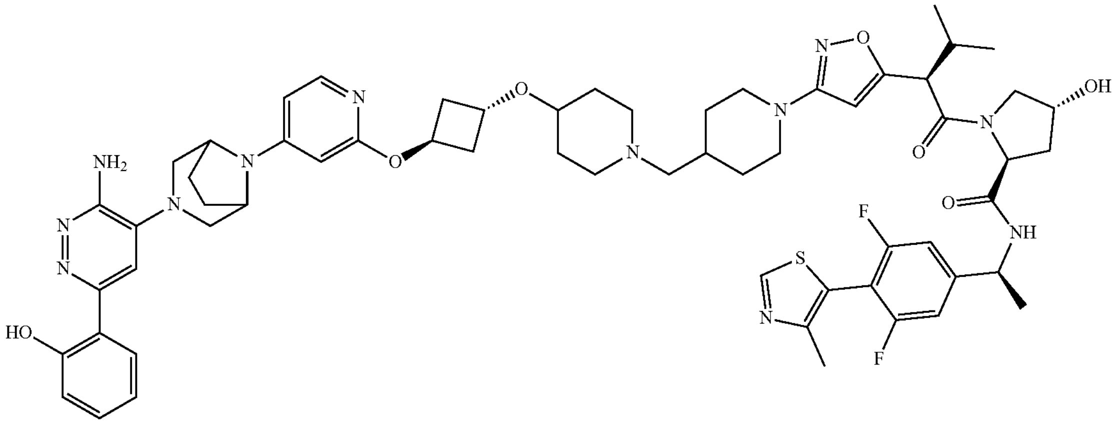 [SMILES: Cc1ncsc1-c1c(F)cc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1F] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-y1)-3-methylbutanoyl)-N-((S)-1-(3,5-difluoro-4-(4-methylthiazol-5-yl)phenyl)ethyl)-4-hydroxypyrrolidine-2-carboxamide |

-continued

| []Exemplary bifunctional degradation compounds of the present disclosure | | |
|---|---|---|
| Ex No | Structure | Name |
| 667 | 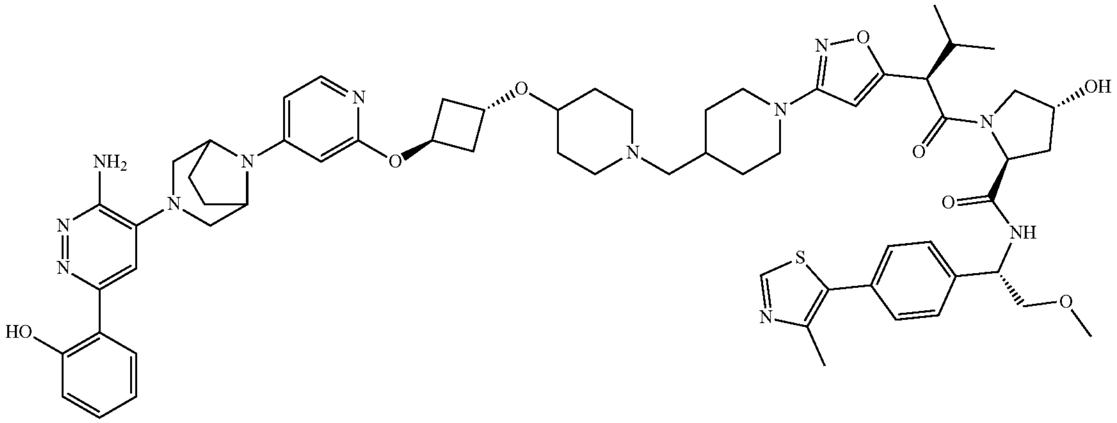 [SMILES: COC[C@@H](NC(=O)[C@@H]1C[C@@H](O)CN1C(=O)[C@@H](c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1)C(C)C)c1ccc(-c2scnc2C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-2-methoxy-1-(4-(4-methylthiazol-5-yl)phenyl)ethyl)pyrrolidine-2-carboxamide |
| 668 | 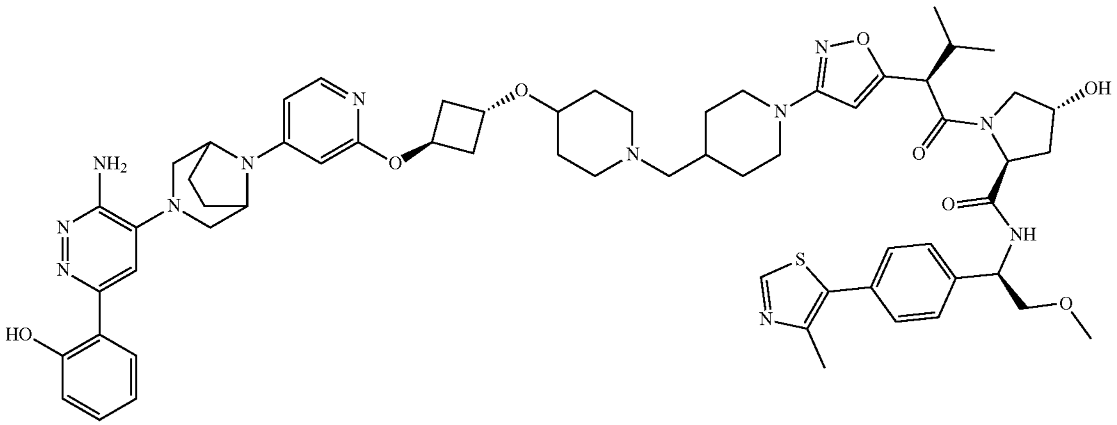 [SMILES: COC[C@H](NC(=O)[C@@H]1C[C@@H](O)CN1C(=O)[C@@H](c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1)C(C)C)c1ccc(-c2scnc2C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((R)-2-methoxy-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 669 | 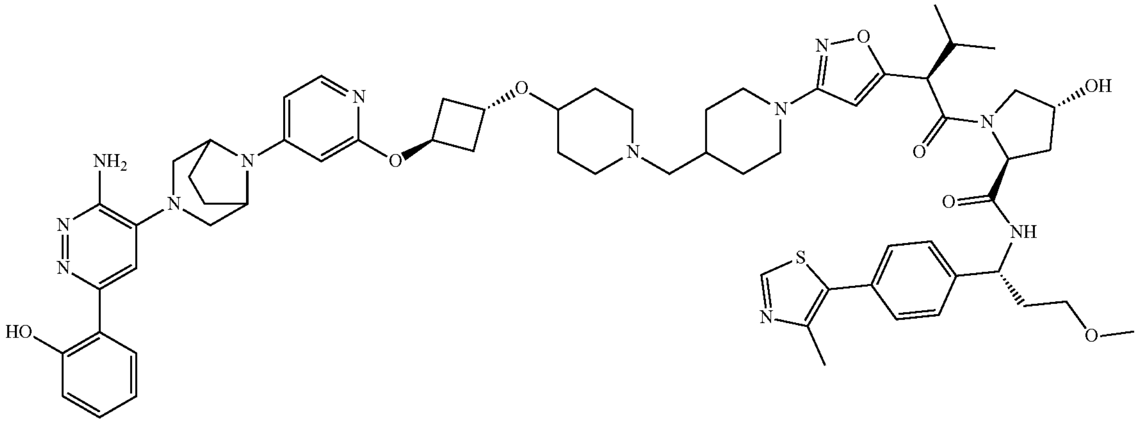 [SMILES: COCC[C@@H](NC(=O)[C@@H]1C[C@@H](O)CN1C(=O)[C@@H](c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1)C(C)C)c1ccc(-c2scnc2C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((R)-3-methoxy-1-(4-(4-methylthiazol-5-yl)phenyl)propyl)pyrrolidine-2-carboxamide |
| 670 | 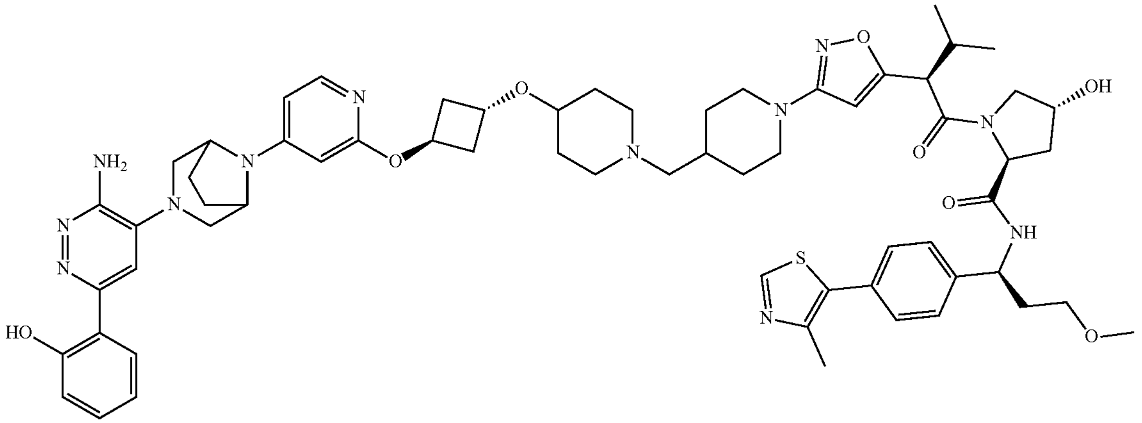 [SMILES: COCC[C@H](NC(=O)[C@@H]1C[C@@H](O)CN1C(=O)[C@@H](c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1)C(C)C)c1ccc(-c2scnc2C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-3-methoxy-1-(4-(4-methylthiazol-5-yl)phenyl)propyl)pyrrolidine-2-carboxamide |

-continued

[]Exemplary bifunctional degradation compounds of the present disclosure

| Ex No | Structure | Name |
|---|---|---|
| 671 | 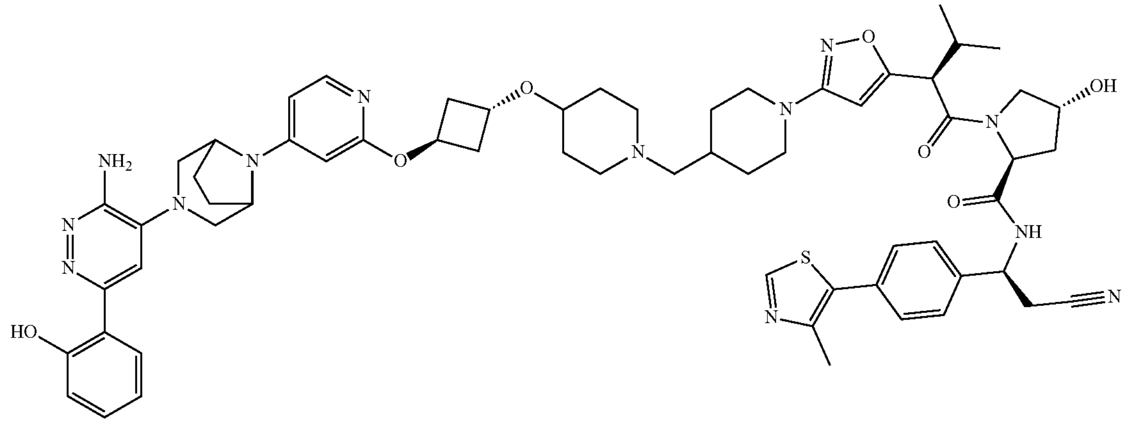 [SMILES: Cc1ncsc1-c1ccc([C@H](CC#N)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-2-cyano-1-(4-(4-methylthiazol-5-yl)phenyl)ethyl)-4-hydroxypyrrolidine-2-carboxamide |
| 672 | 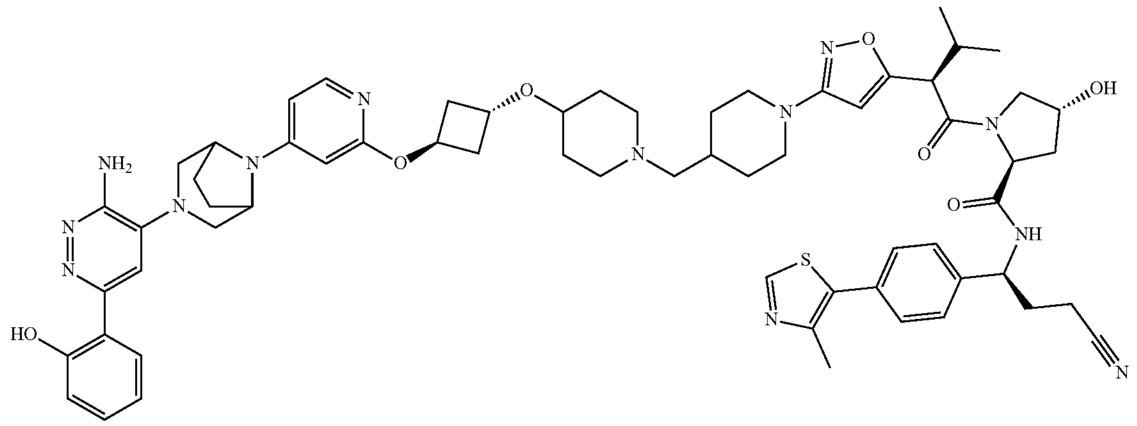 [SMILES: Cc1ncsc1-c1ccc([C@H](CCC#N)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-3-cyano-1-(4-(4-methylthiazol-5-yl)phenyl)propyl)-4-hydroxypyrrolidine-2-carboxamide |

-continued

[]Exemplary bifunctional degradation compounds of the present disclosure

| Ex No | Structure | Name |
|---|---|---|
| 673 | 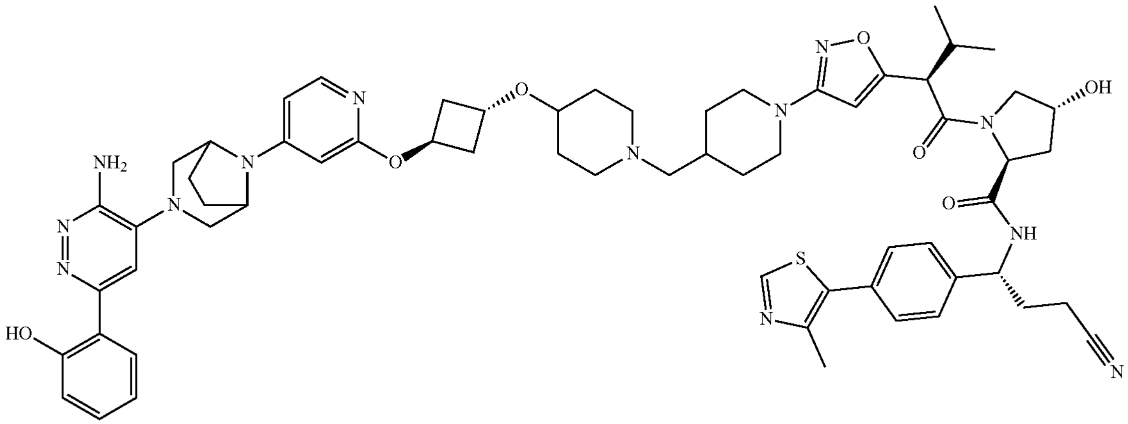 [SMILES: Cc1ncsc1-c1ccc([C@@H](CCC#N)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((R)-3-cyano-1-(4-(4-methylthiazol-5-yl)phenyl)propyl)-4-hydroxypyrrolidine-2-carboxamide |
| 674 | 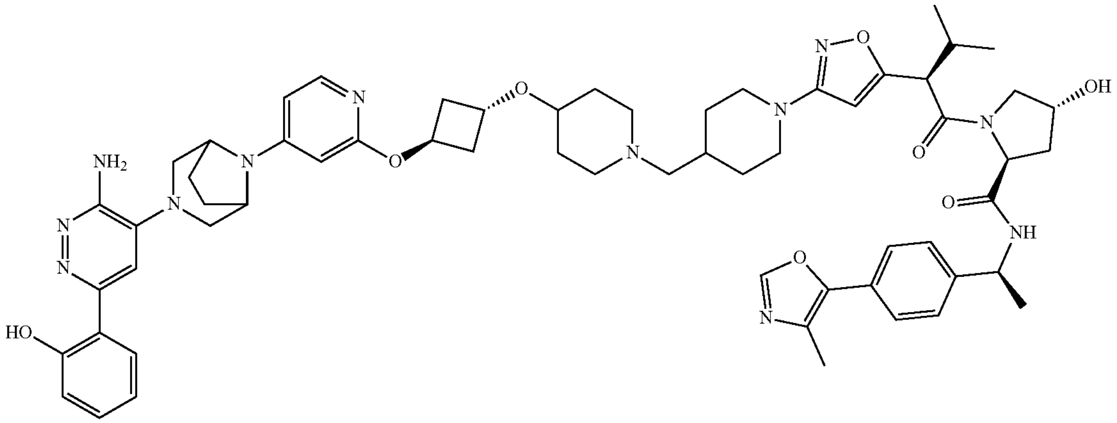 [SMILES: Cc1ncoc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methyloxazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 675 | 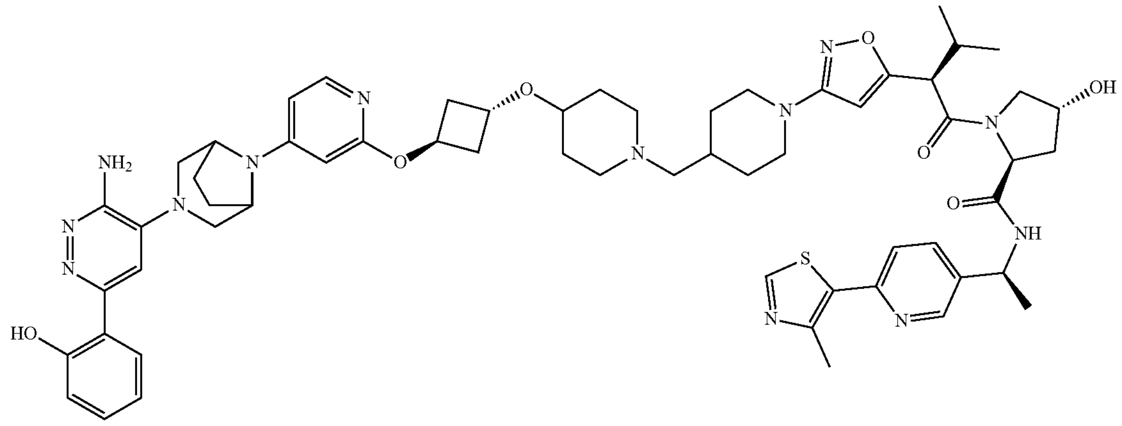 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cn1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(6-(4-methylthiazol-5-yl)pyridin-3-yl)ethyl)pyrrolidine-2-carboxamide |
| 676 | 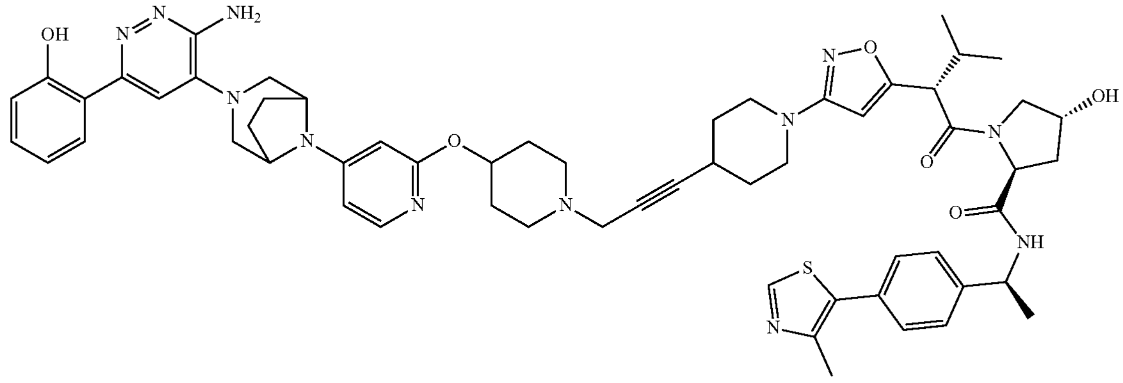 [SMILES: Cc1ncsc1-c1ccc([C@H](C)NC(=O)[C@@H]2C[C@@H](O)CN2C(=O)[C@H](c2cc(N3CCC(C#CCN4CCC(Oc5cc(N6C7CCC6CN(c6cc(-c8ccccc8O)nnc6N)C7)ccn5)CC4)CC3)no2)C(C)C)cc1] | (2S,4R)-1-((2S)-2-(3-(4-(3-(4-((4-(3-(3-amino-6-(2-hydroxyphenyl)pyridazin-4-yl)-3,8-diazabicyclo[3.2.1]octan-8-yl)pyridin-2-yl)oxy)piperidin-1-yl)prop-1-yn-1-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 677 | 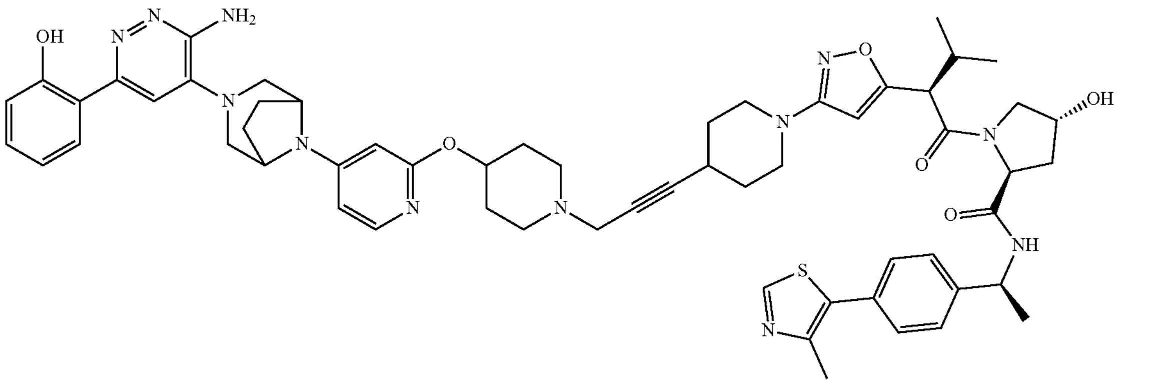 [SMILES: Cc1ncsc1-c1ccc([C@H](C)NC(=O)[C@@H]2C[C@@H](O)CN2C(=O)[C@@H](c2cc(N3CCC(C#CCN4CCC(Oc5cc(N6C7CCC6CN(c6cc(-c8ccccc8O)nnc6N)C7)ccn5)CC4)CC3)no2)C(C)C)cc1] | (2S,4R)-1-((2R)-2-(3-(4-(3-(4-((4-(3-(3-amino-6-(2-hydroxyphenyl)pyridazin-4-yl)-3,8-diazabicyclo[3.2.1]octan-8-yl)pyridin-2-yl)oxy)piperidin-1-yl)prop-1-yn-1-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 678 | 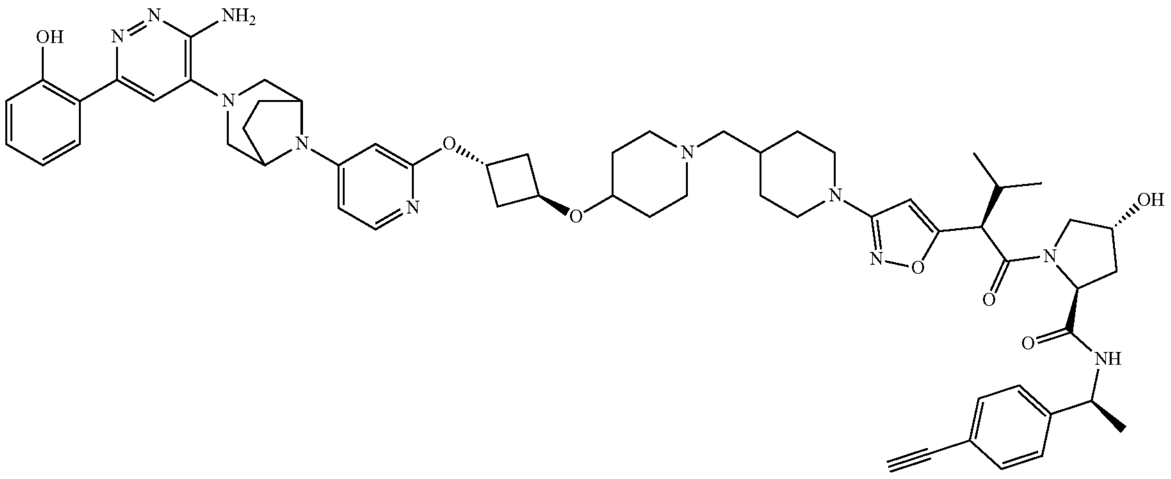 [SMILES: C#Cc1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-ethynylphenyl)ethyl)-4-hydroxypyrrolidine-2-carboxamide |

-continued

[]Exemplary bifunctional degradation compounds of the present disclosure

| Ex No | Structure | Name |
|---|---|---|
| 679 | 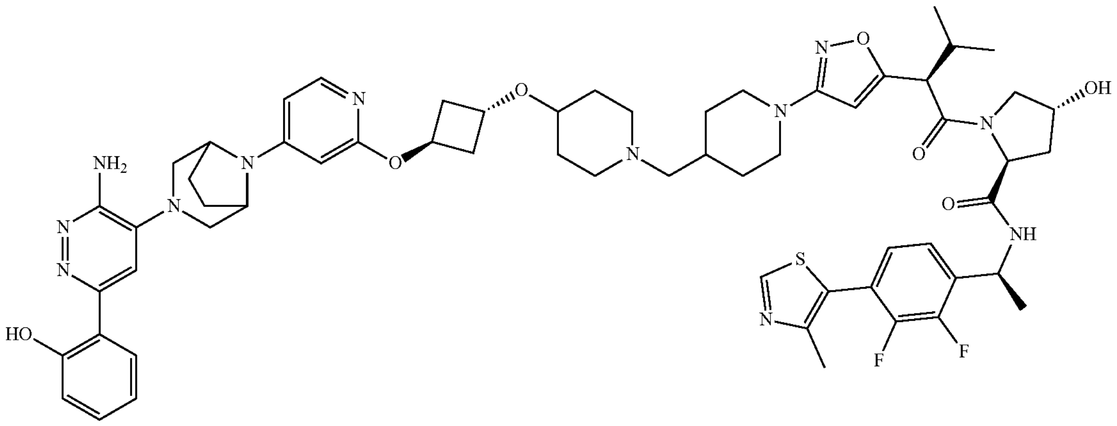 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)c(F)c1F] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(2,3-difluoro-4-(4-methylthiazol-5-yl)phenyl)ethyl)-4-hydroxypyrrolidine-2-carboxamide |
| 680 | 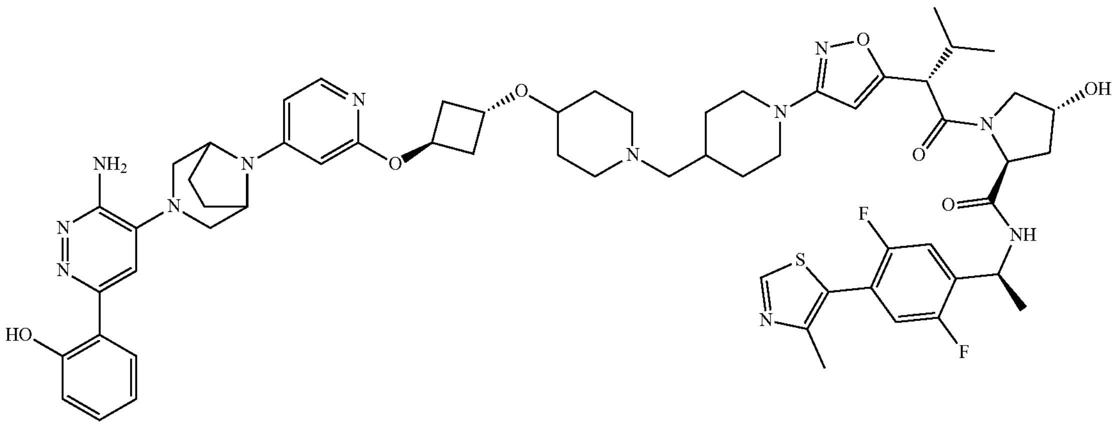 [SMILES: Cc1ncsc1-c1cc(F)c([C@H](C)NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1F] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(2,5-difluoro-4-(4-methylthiazol-5-yl)phenyl)ethyl)-4-hydroxypyrrolidine-2-carboxamide |

-continued

| []Exemplary bifunctional degradation compounds of the present disclosure | | |
|---|---|---|
| Ex No | Structure | Name |
| 681 | 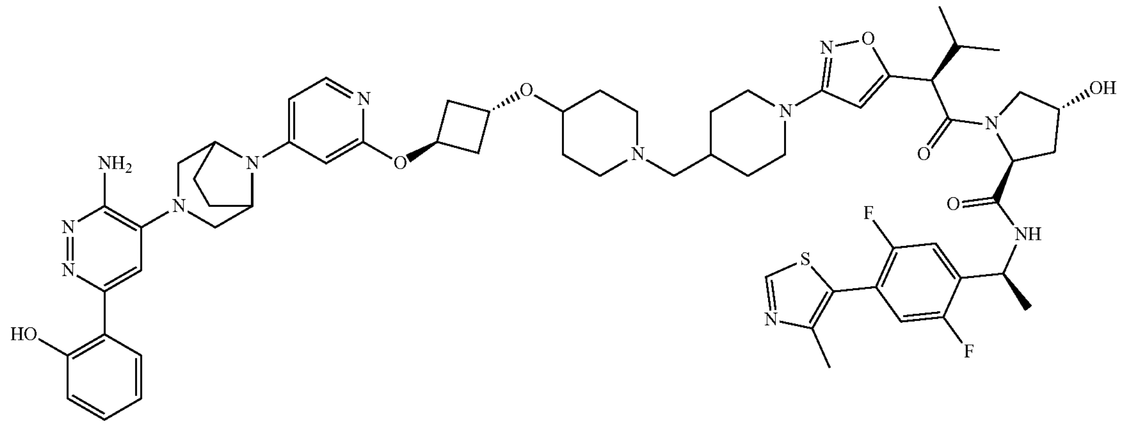 [SMILES: Cc1ncsc1-c1cc(F)c([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1F] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(2,5-difluoro-4-(4-methylthiazol-5-yl)phenyl)ethyl)-4-hydroxypyrrolidine-2-carboxamide |
| 682 | 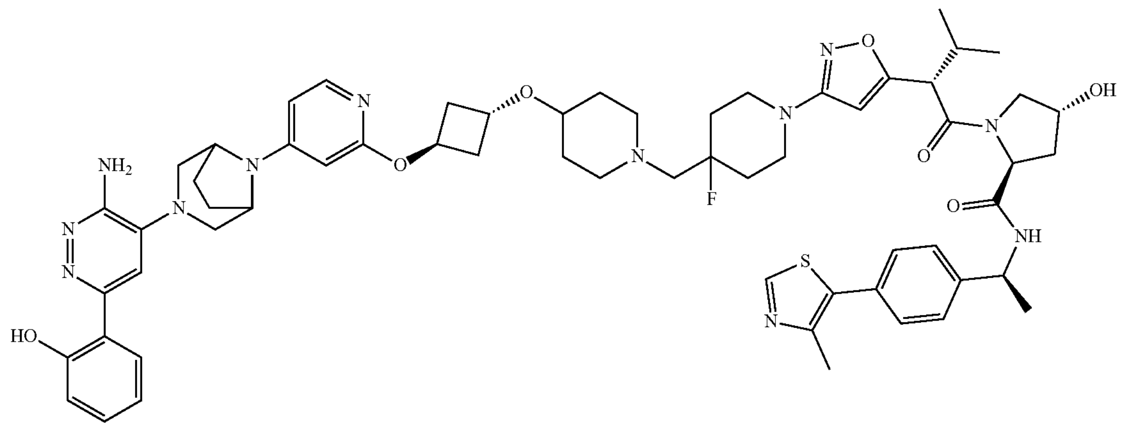 [SMILES: Cc1ncsc1-c1ccc([C@H](C)NC(=O)[C@@H]2C[C@@H](O)CN2C(=O)[C@H](c2cc(N3CCC(F)(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-4-fluoropiperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 683 | 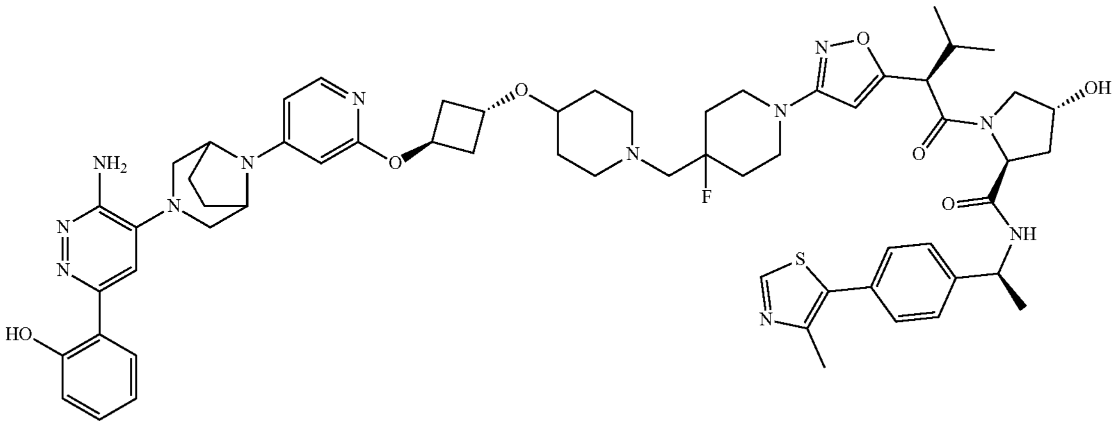 [SMILES: Cc1ncsc1-c1ccc([C@H](C)NC(=O)[C@@H]2C[C@@H](O)CN2C(=O)[C@@H](c2cc(N3CCC(F)(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-4-fluoropiperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 684 | 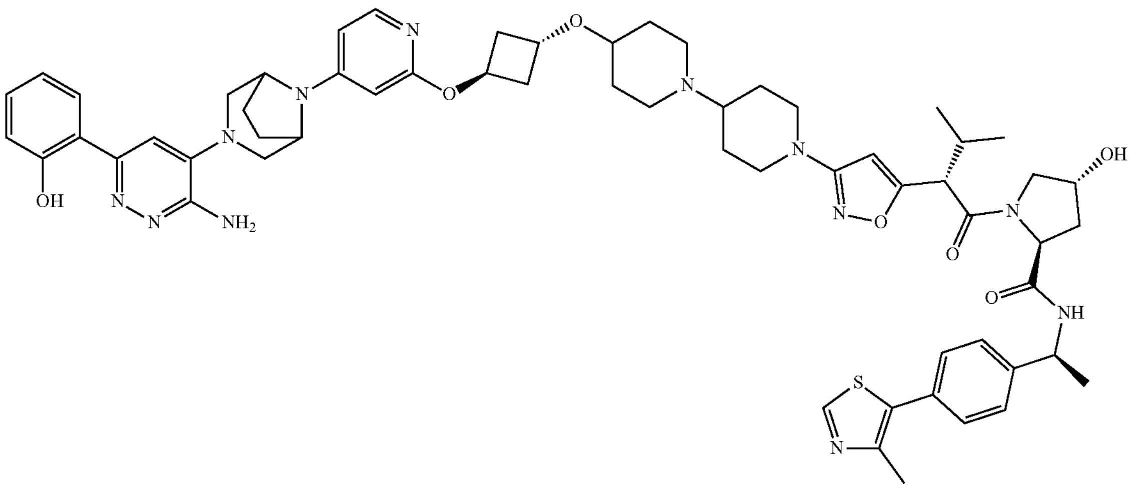 [SMILES: Cc1ncsc1-c1ccc([C@H](C)NC(=O)[C@@H]2C[C@@H](O)CN2C(=O)[C@H](c2cc(N3CCC(N4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-[1,4'-bipiperidin]-1'-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 685 | 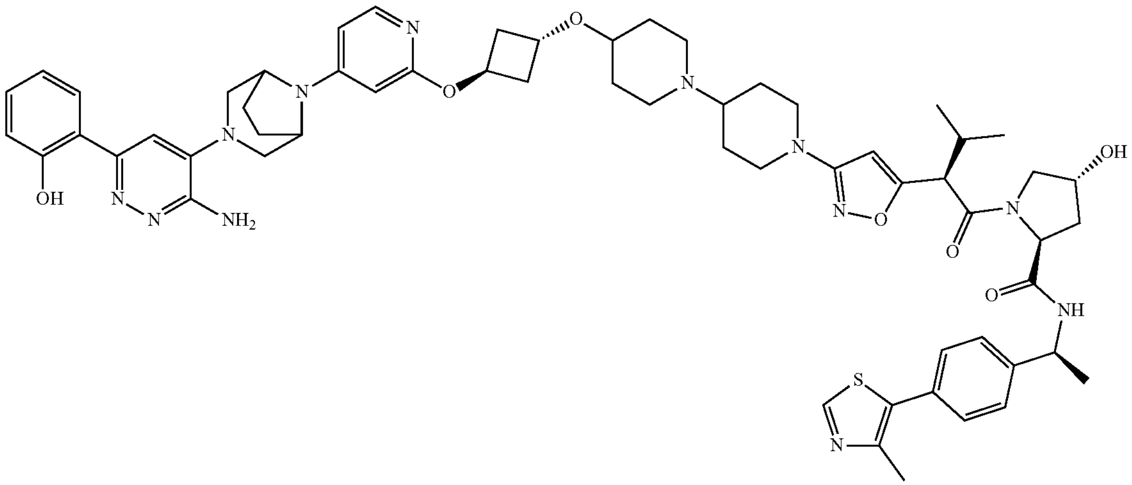 [SMILES: Cc1ncsc1-c1ccc([C@H](C)NC(=O)[C@@H]2C[C@@H](O)CN2C(=O)[C@@H](c2cc(N3CCC(N4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-[1,4'-bipiperidin]-1'-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 686 | 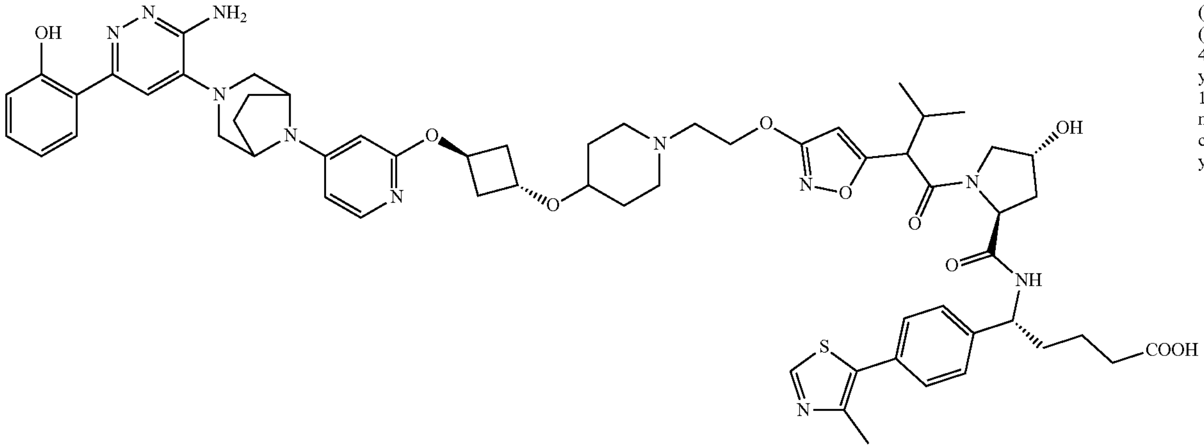 [SMILES: Cc1ncsc1-c1ccc([C@@H](CCCC(=O)O)NC(=O)[C@@H]2C[C@@H](O)CN2C(=O)C(c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (5R)-5-((2S,4R)-1-(2-(3-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamido)-5-(4-(4-methylthiazol-5-yl)phenyl)pentanoic acid |

-continued

| []Exemplary bifunctional degradation compounds of the present disclosure | | |
|---|---|---|
| Ex No | Structure | Name |
| 687 | 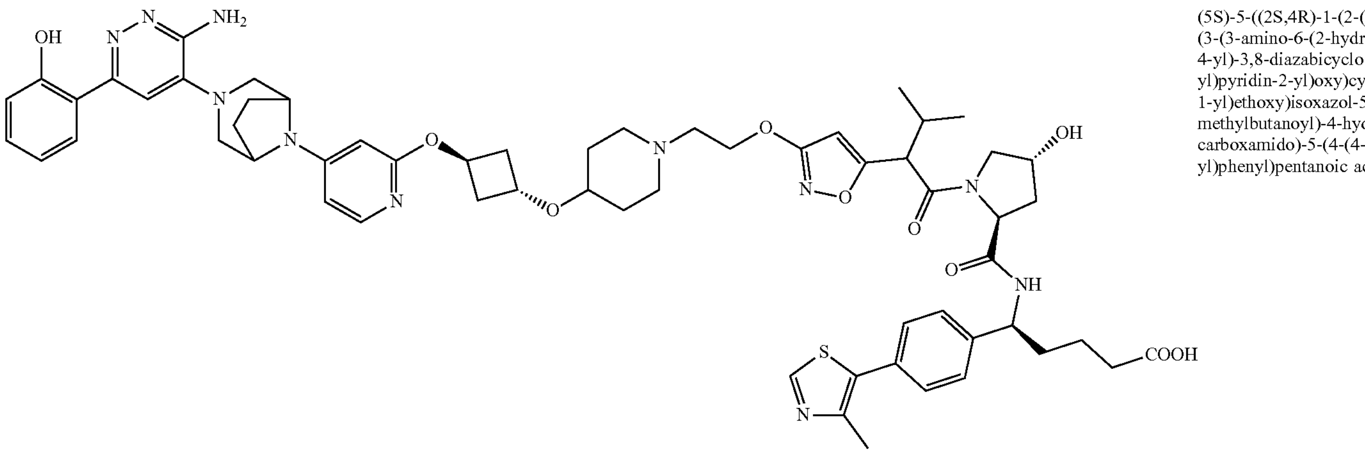 | (5S)-5-((2S,4R)-1-(2-(3-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamido)-5-(4-(4-methylthiazol-5-yl)phenyl)pentanoic acid |
| 688 | 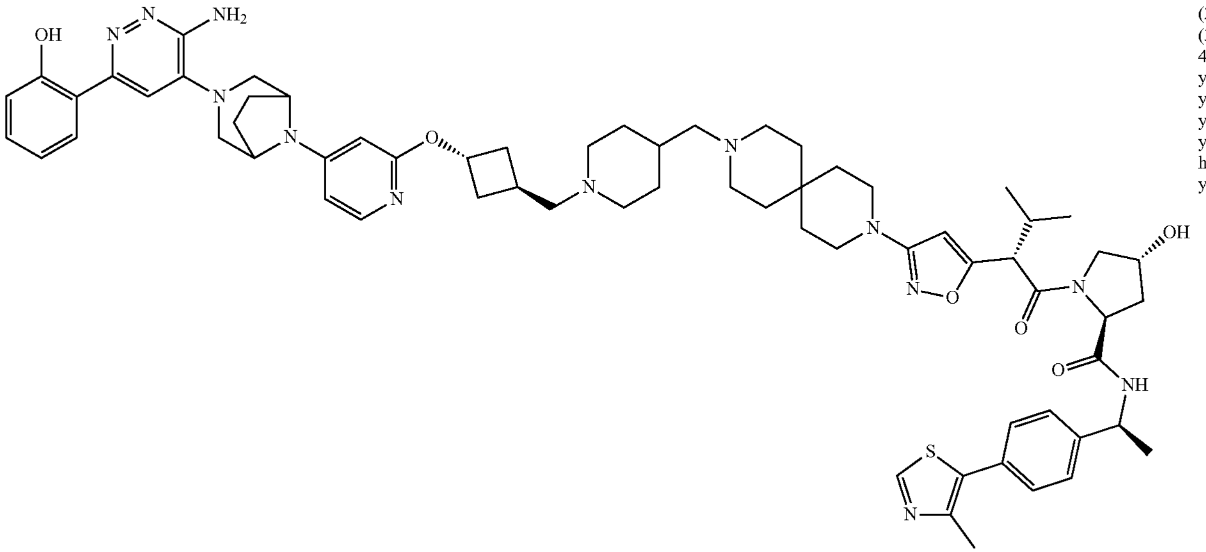 | (2S,4R)-1-((2S)-2-(3-(9-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)-3,9-diazaspiro[5.5]undecan-3-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
| --- | --- | --- |
| 689 | 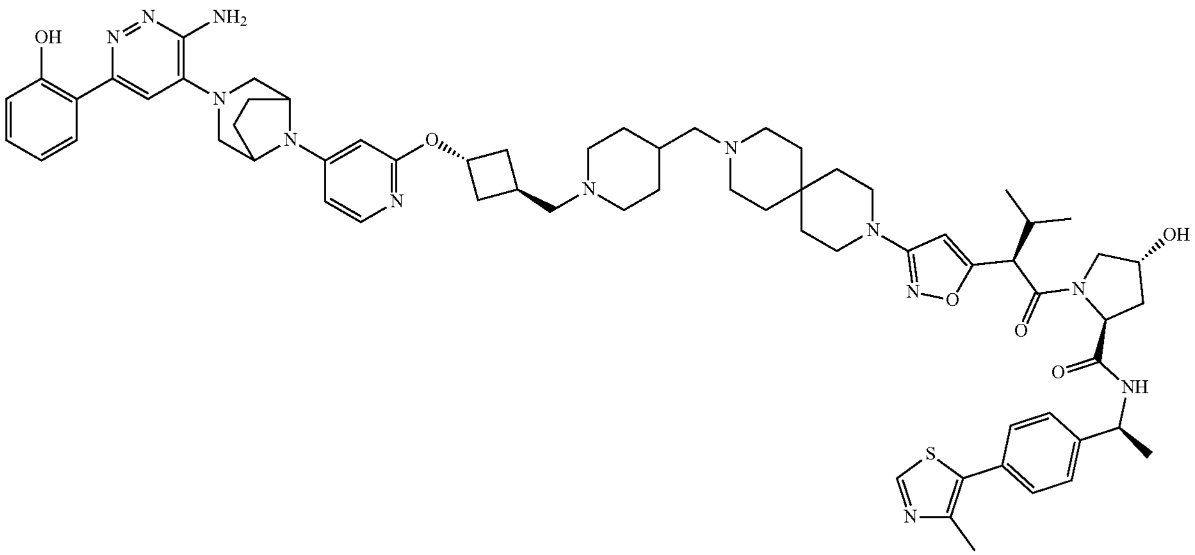 [SMILES: Cc1ncsc1-c1ccc([C@H](C)NC(=O)[C@@H]2C[C@@H](O)CN2C(=O)[C@@H](c2cc(N3CCC4(CCN(CC5CCN(C[C@H]6C[C@H](Oc7cc(N8C9CCC8CN(c8cc(-c%10ccccc%10O)nnc8N)C9)ccn7)C6)CC5)CC4)CC3)no2)C(C)C)cc1] | (2S,4R)-1-((2R)-2-(3-(9-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)-3,9-diazaspiro[5.5]undecan-3-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 690 | 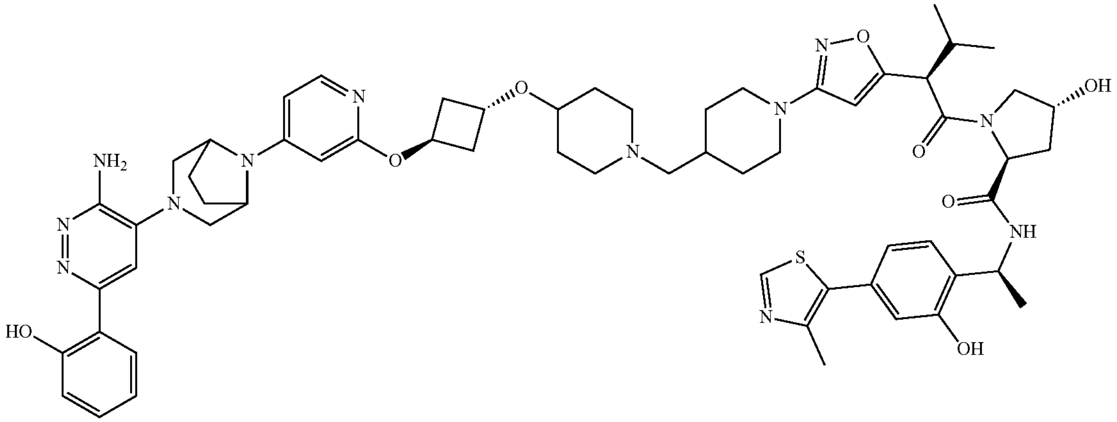 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)c(O)c1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(2-hydroxy-4-(4-methylthiazol-5-yl)phenyl)ethyl)pyrrolidine-2-carboxamide |

-continued

| Ex No | Structure | Name |
|---|---|---|
| []Exemplary bifunctional degradation compounds of the present disclosure | | |
| 691 | 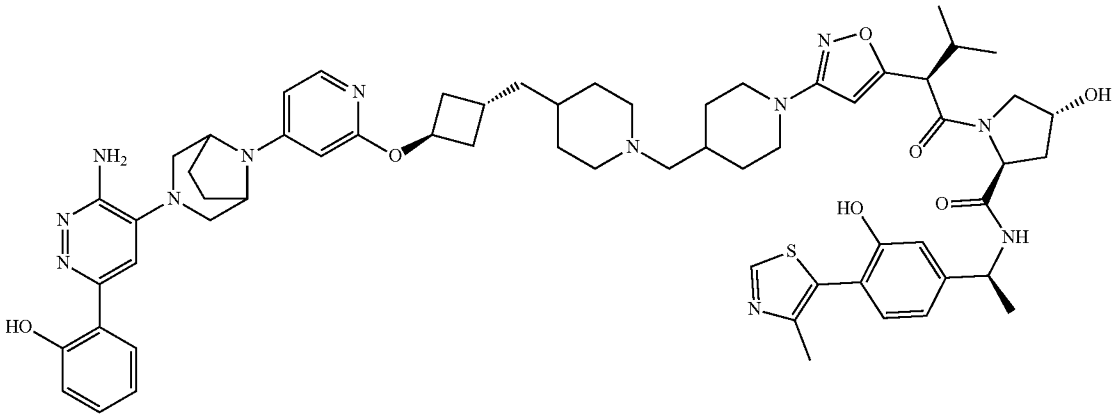 [SMILES: Cc1ncsc1-c1ccc([C@H](C)NC(=O)[C@@H]2C[C@@H](O)CN2C(=O)[C@@H](c2cc(N3CCC(CN4CCC(C[C@H]5C[C@H](Oc6cc(N7C8CCC7CN(c7cc(-c9ccccc9O)nnc7N)C8)ccn6)C5)CC4)CC3)no2)C(C)C)cc1O] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(3-hydroxy-4-(4-methylthiazol-5-yl)phenyl)ethyl)pyrrolidine-2-carboxamide |
| 692 | 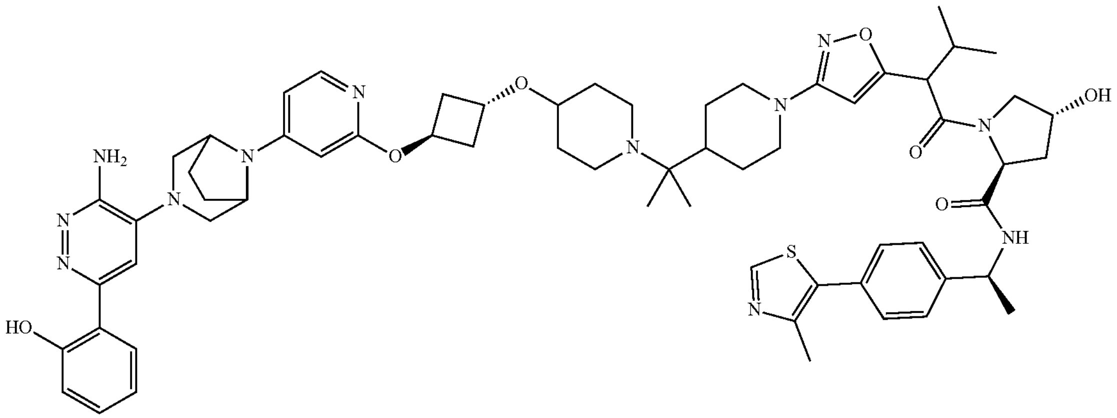 [SMILES: Cc1ncsc1-c1ccc([C@H](C)NC(=O)[C@@H]2C[C@@H](O)CN2C(=O)C(c2cc(N3CCC(C(C)(C)N4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-(2-(3-(4-(2-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)propan-2-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 693 | 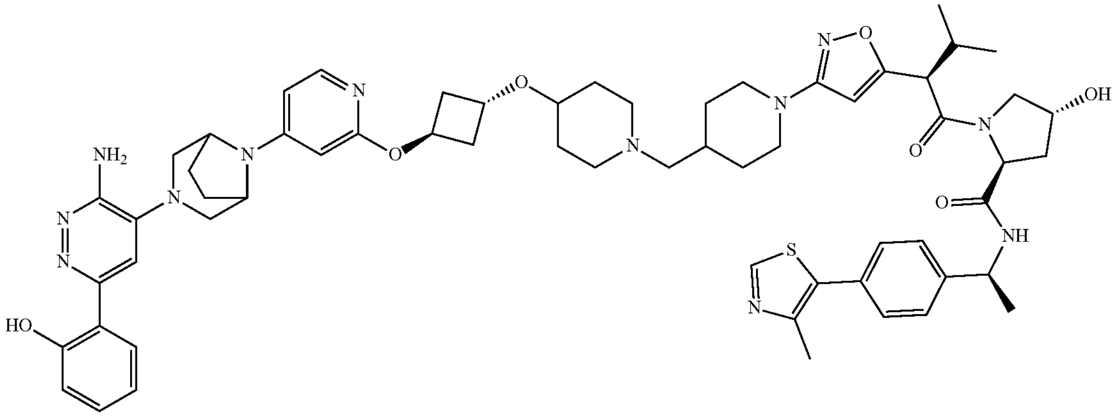 | (2S,4R)-1-((R)-2-(3-(4-((4-((1r,3r)-3-((4-(4-(3-amino-6-(2-hydroxyphenyl)pyridazin-4-yl)piperazin-1-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 694 | 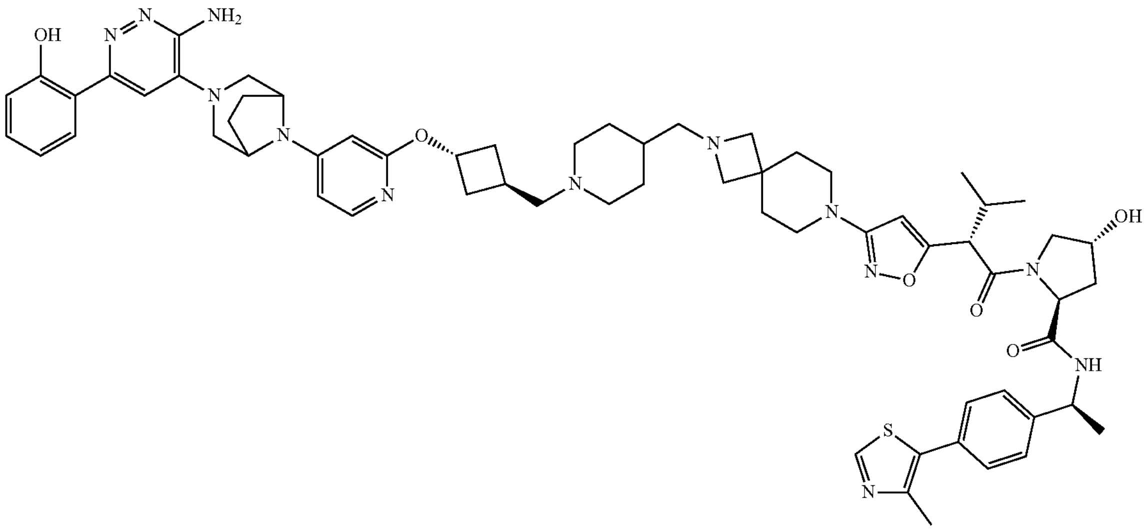 [SMILES: Cc1ncsc1-c1ccc([C@H](C)NC(=O)[C@@H]2C[C@@H](O)CN2C(=O)[C@H](c2cc(N3CCC4(CC3)CN(CC3CCN(C[C@H]5C[C@H](Oc6cc(N7C8CCC7CN(c7cc(-c9ccccc9O)nnc7N)C8)ccn6)C5)CC3)C4)no2)C(C)C)cc1] | (2S,4R)-1-((2S)-2-(3-(2-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)-2,7-diazaspiro[3.5]nonan-7-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 695 | 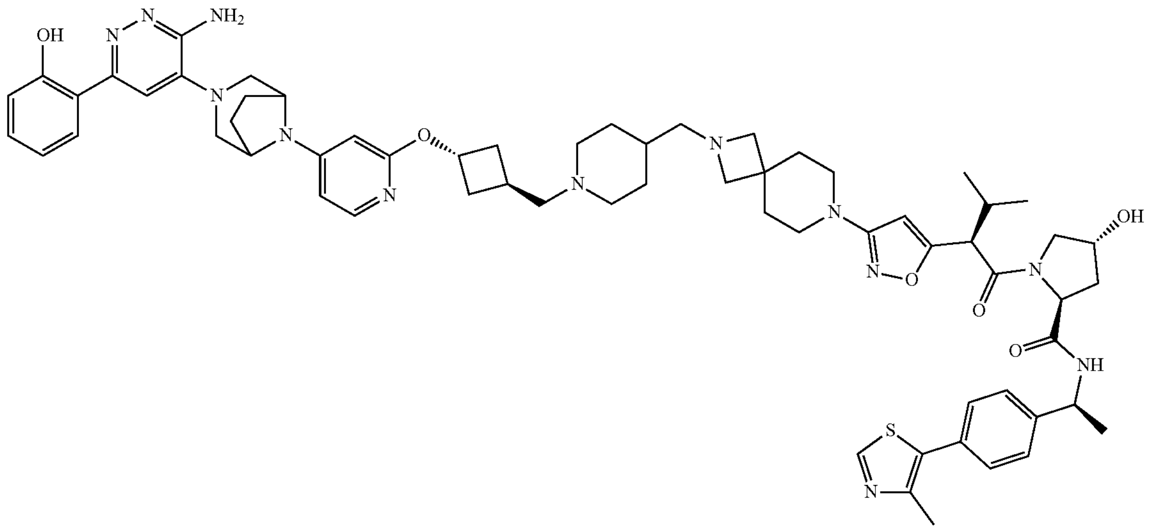 [SMILES: Cc1ncsc1-c1ccc([C@H](C)NC(=O)[C@@H]2C[C@@H](O)CN2C(=O)[C@@H](c2cc(N3CCC4(CC3)CN(CC3CCN(C[C@H]5C[C@H](Oc6cc(N7C8CCC7CN(c7cc(-c9ccccc9O)nnc7N)C8)ccn6)C5)CC3)C4)no2)C(C)C)cc1] | (2S,4R)-1-((2R)-2-(3-(2-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)-2,7-diazaspiro[3.5]nonan-7-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 696 | 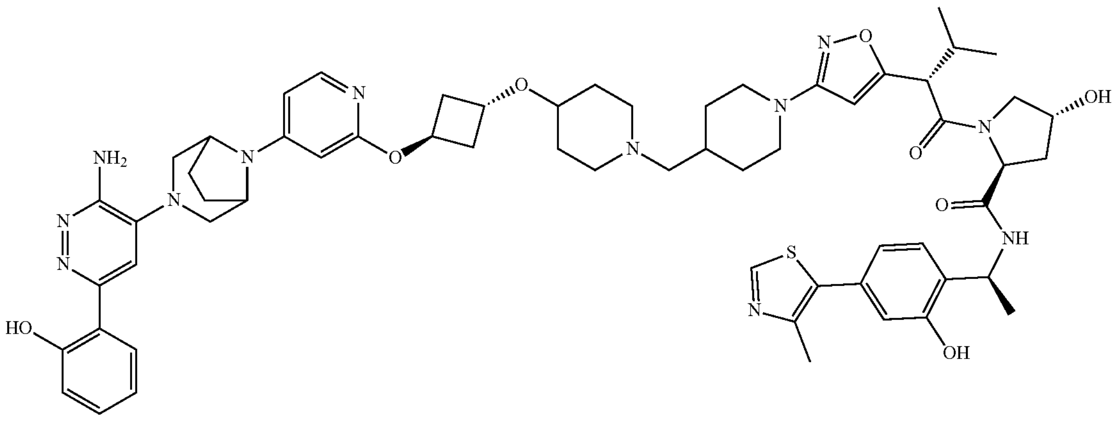 [SMILES: Cc1ncsc1-c1ccc([C@H](C)NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)c(O)c1] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-y1)-3-methylbutanoyl)-4-hydroxy-N-((S)-1-(2-hydroxy-4-(4-methylthiazol-5-yl)phenyl)ethyl)pyrrolidine-2-carboxamide |

-continued
| []Exemplary bifunctional degradation compounds of the present disclosure | | |
|---|---|---|
| Ex No | Structure | Name |
| 697 | stereoconfiguration arbitrarily assigned 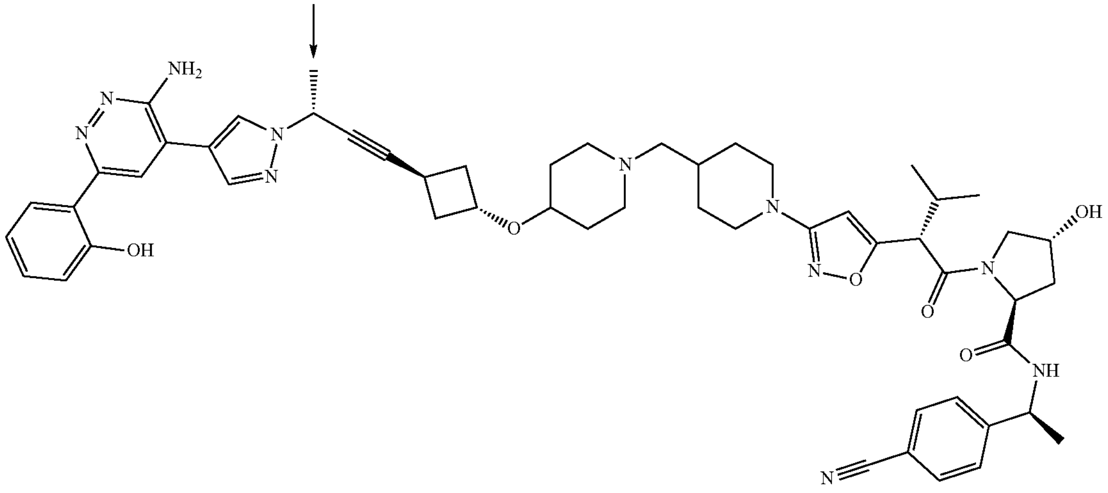 | (2S,4R)-1-((S)-2-(3-(4-((4-((1R,3r)-3-((R)-3-(4-(3-amino-6-(2-hydroxyphenyl)pyridazin-4-yl)-1H-pyrazol-1-yl)but-1-yn-1-yl)cyclobutoxy)piperidin-1-yl)methyl)piperidin-1-yl)isoxazol-5-yl)-3-methylbutanoyl)-N-((S)-1-(4-cyanophenyl)ethyl)-4-hydroxypyrrolidine-2-carboxamide |

-continued

[]Exemplary bifunctional degradation compounds of the present disclosure

| Ex No | Structure | Name |
| --- | --- | --- |
| 698 | 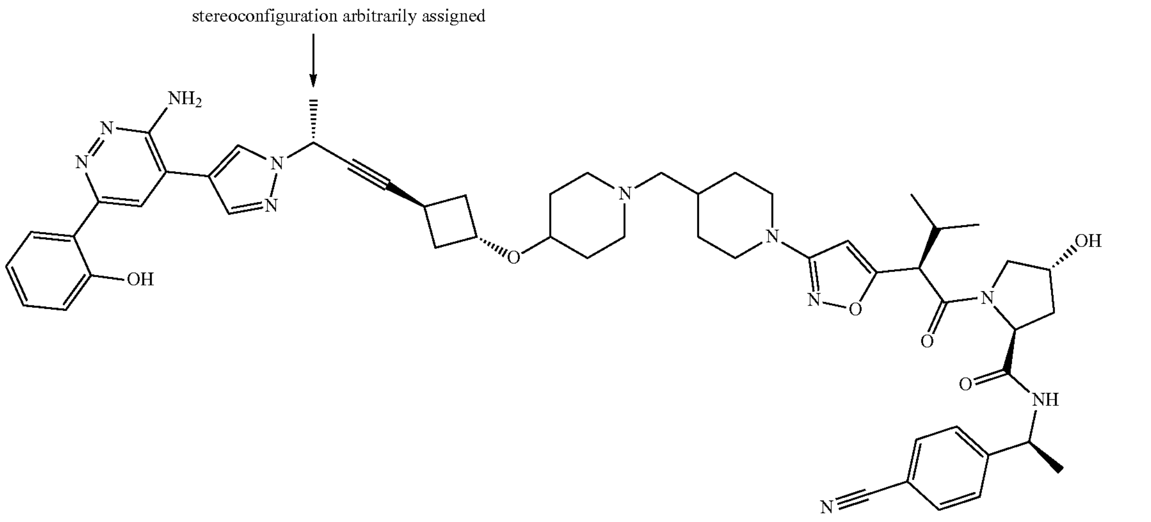 [SMILES: CC(C)[C@@H](C(=O)N1C[C@H](O)C[C@H]1C(=O)N[C@@H](C)c1ccc(C#N)cc1)c1cc(N2CCC(CN3CCC(O[C@H]4C[C@H](C#C[C@@H](C)n5cc(-c6cc(-c7ccccc7O)nnc6N)cn5)C4)CC3)CC2)no1] | (2S,4R)-1-((R)-2-(3-(4-((4-((1R,3r)-3-((R)-3-(4-(3-amino-6-(2-hydroxyphenyl)pyridazin-4-yl)-1H-pyrazol-1-yl)but-1-yn-1-yl)cyclobutoxy)piperidin-1-yl)methyl)piperidin-1-yl)isoxazol-5-yl)-3-methylbutanoyl)-N-((S)-1-(4-cyanophenyl)ethyl)-4-hydroxypyrrolidine-2-carboxamide |
| 699 | 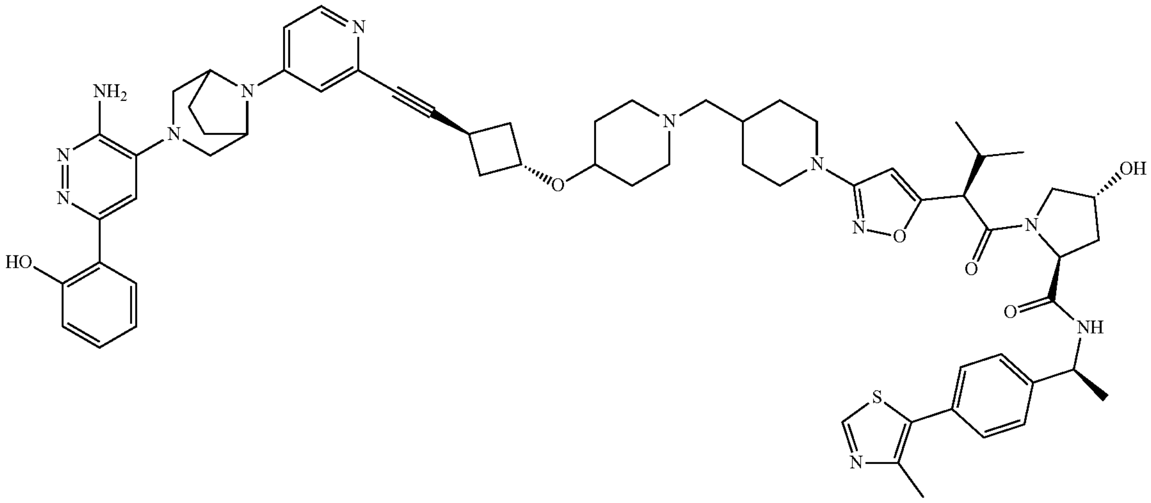 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](C#Cc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)ethynyl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 700 | 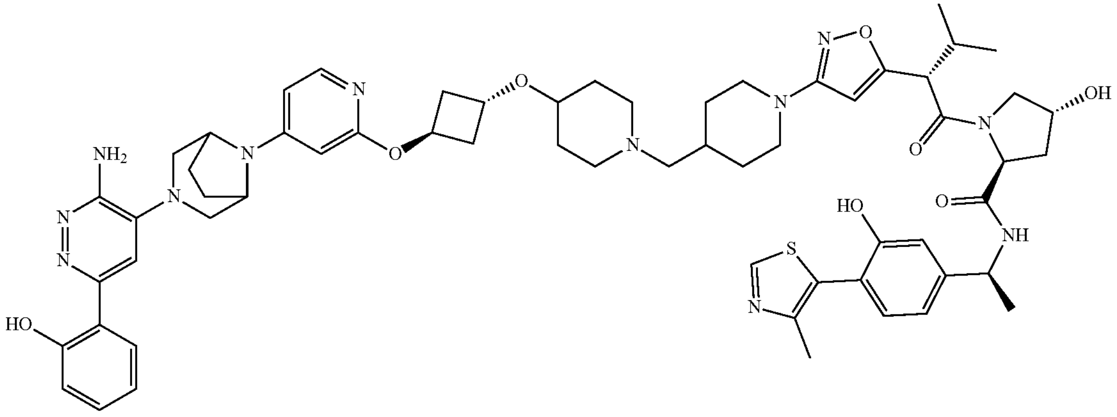 [SMILES: Cc1ncsc1-c1ccc([C@H](C)NC(=O)[C@@H]2C[C@@H](O)CN2C(=O)[C@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1O] | (2S,4R)-1-((2S)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(3-hydroxy-4-(4-methylthiazol-5-yl)phenyl)ethyl)pyrrolidine-2-carboxamide |
| 701 | 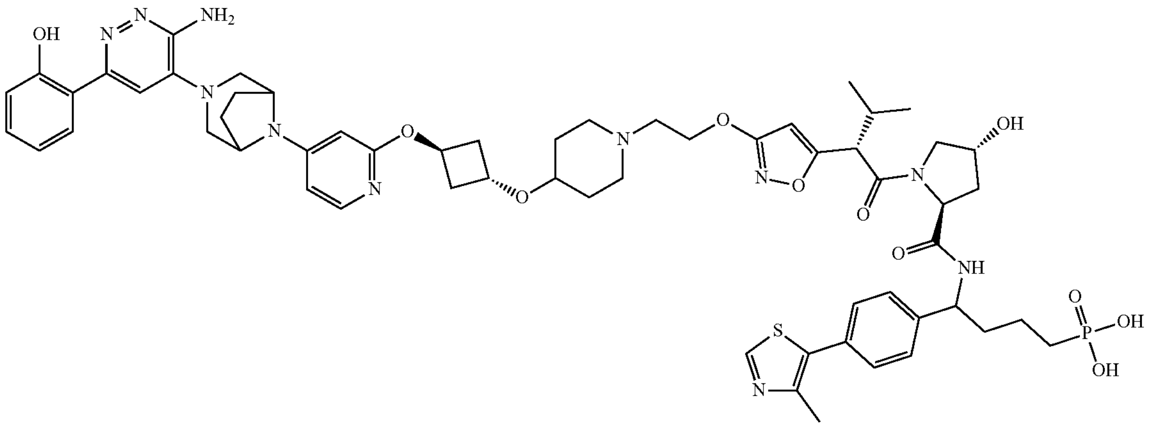 [SMILES: Cc1ncsc1-c1ccc(C(CCCP(=O)(O)O)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (4-((2S,4R)-1-((2S)-2-(3-(2-(4-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamido)-4-(4-(4-methylthiazol-5-yl)phenyl)butyl)phosphonic acid |

-continued

[]Exemplary bifunctional degradation compounds of the present disclosure

| Ex No | Structure | Name |
|---|---|---|
| 702 | 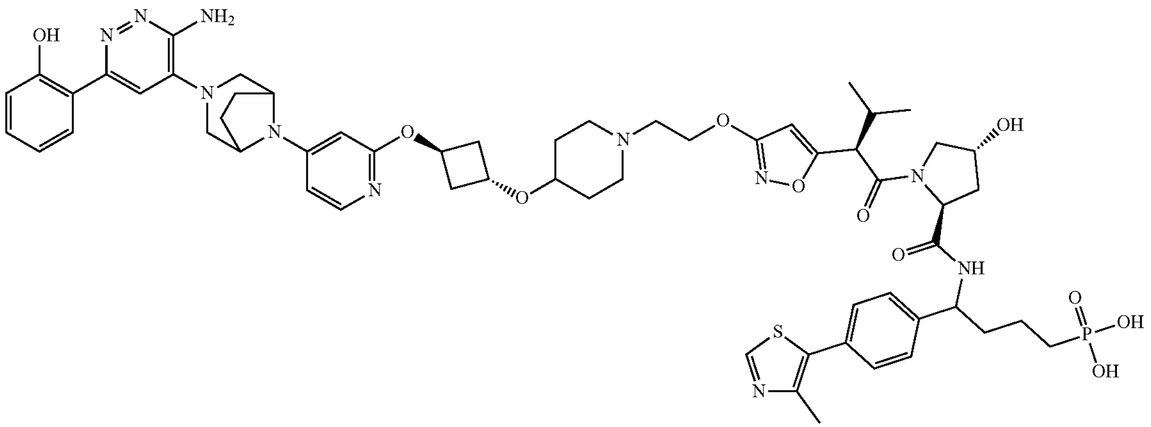 [SMILES: Cc1ncsc1-c1ccc(C(CCCP(=O)(O)O)NC(=O)[C@@H]2C[C@@H](O)CN2C(=O)[C@@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1] | (4-((2S,4R)-1-((2R)-2-(3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)ethoxy)isoxazol-5-yl)-3-methylbutanoyl)-4-hydroxypyrrolidine-2-carboxamido)-4-(4-(4-methylthiazol-5-yl)phenyl)butyl)phosphonic acid |
| 703 | 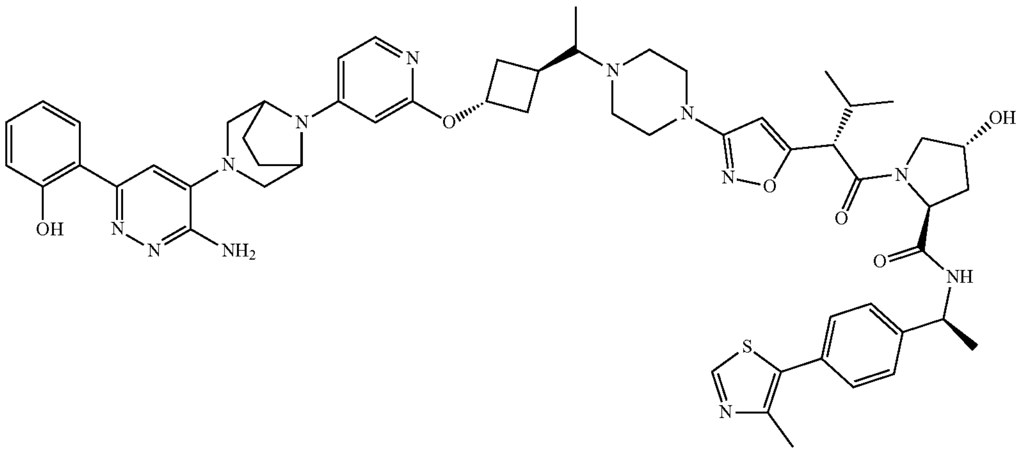 [SMILES: Cc1ncsc1-c1ccc([C@H](C)NC(=O)[C@@H]2C[C@@H](O)CN2C(=O)[C@H](c2cc(N3CCN(C(C)[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2S)-2-(3-(4-((1S)-1-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)ethyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 704 | 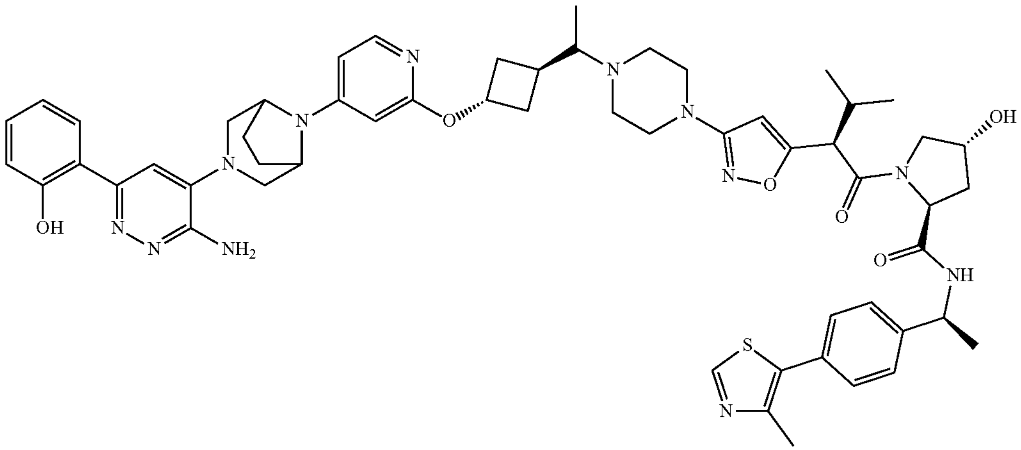 [SMILES: Cc1ncsc1-c1ccc([C@H](C)NC(=O)[C@@H]2C[C@@H](O)CN2C(=O)[C@@H](c2cc(N3CCN(C(C)[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(4-((1S)-1-((1r,3S)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)ethyl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 705 | 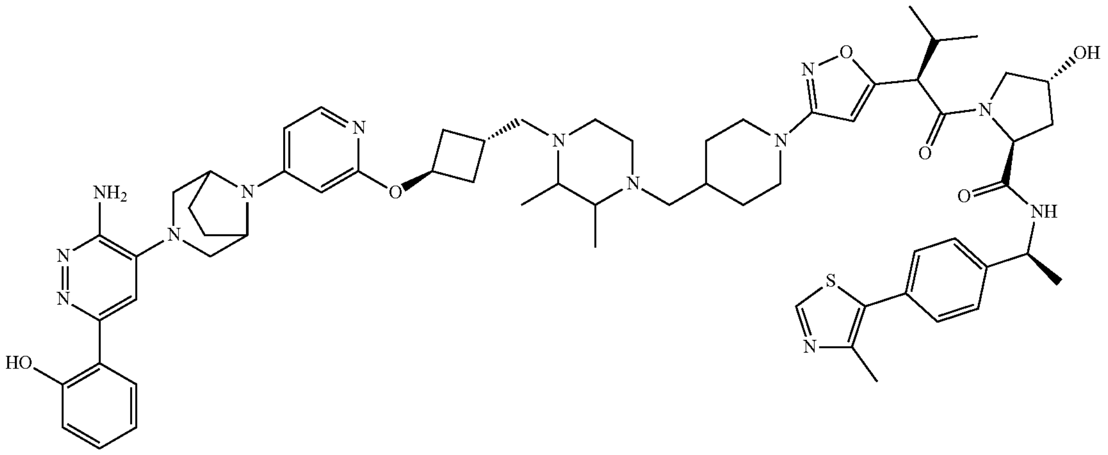 [SMILES: Cc1ncsc1-c1ccc([C@H](C)NC(=O)[C@@H]2C[C@@H](O)CN2C(=O)[C@@H](c2cc(N3CCC(CN4CCN(C[C@H]5C[C@H](Oc6cc(N7C8CCC7CN(c7cc(-c9ccccc9O)nnc7N)C8)ccn6)C5)C(C)C4C)CC3)no2)C(C)C)cc1] | (2S,4R)-1-((2R)-2-(3-(4-((4-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,3-dimethylpiperazin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 706 | 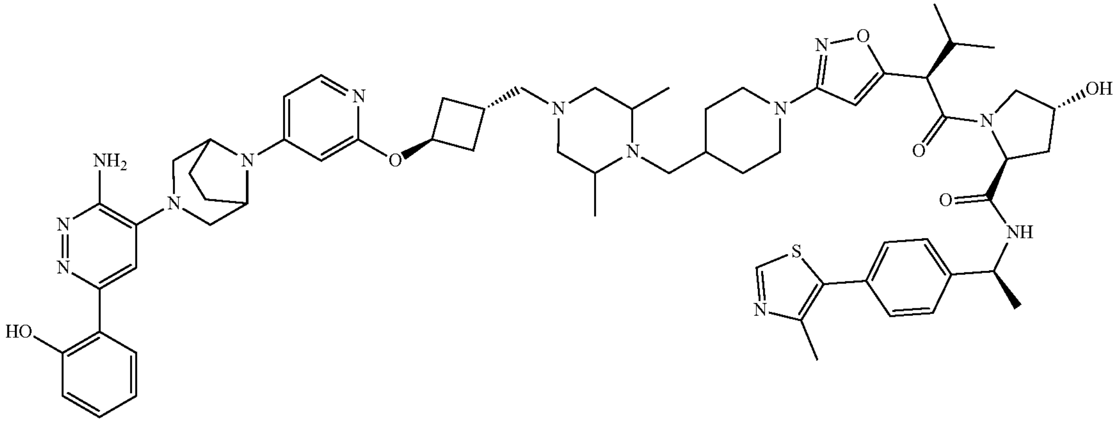 [SMILES: Cc1ncsc1-c1ccc([C@H](C)NC(=O)[C@@H]2C[C@@H](O)CN2C(=O)[C@@H](c2cc(N3CCC(CN4C(C)CN(C[C@H]5C[C@H](Oc6cc(N7C8CCC7CN(c7cc(-c9ccccc9O)nnc7N)C8)ccn6)C5)CC4C)CC3)no2)C(C)C)cc1] | (2S,4R)-1-((2R)-2-(3-(4-((4-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,6-dimethylpiperazin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 707 | 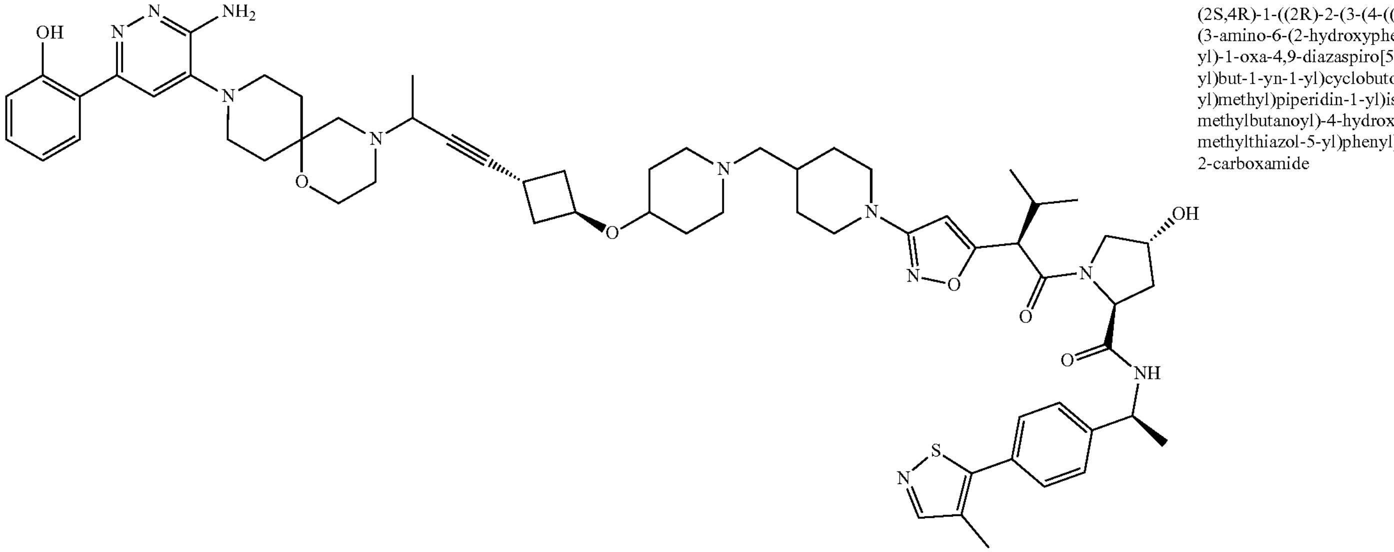 | (2S,4R)-1-((2R)-2-(3-(4-((4-((1r,3r)-3-(3-(9-(3-amino-6-(2-hydroxyphenyl)pyridazin-4-yl)-1-oxa-4,9-diazaspiro[5.5]undecan-4-yl)but-1-yn-1-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 708 | 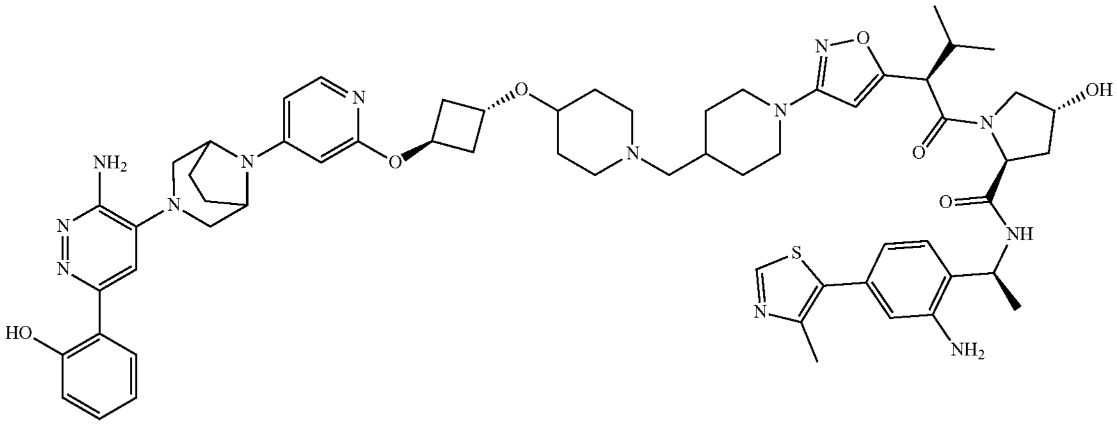 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)c(N)c1] | (2S,4R)-N-((S)-1-(2-amino-4-(4-methylthiazol-5-yl)phenyl)ethyl)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxypyrrolidine-2-carboxamide |
| 709 | 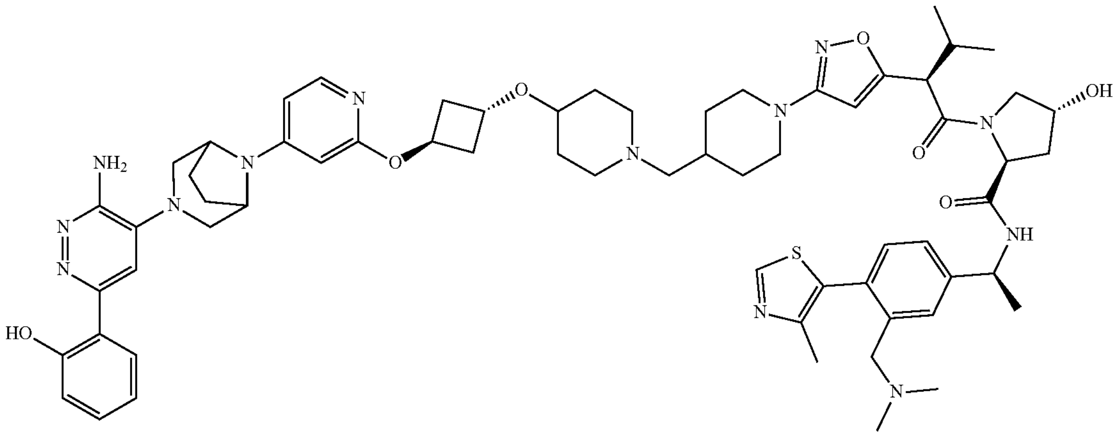 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1CN(C)C] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-(1-(3-((dimethylamino)methyl)-4-(4-methylthiazol-5-yl)phenyl)ethyl)-4-hydroxypyrrolidine-2-carboxamide |

-continued

| []Exemplary bifunctional degradation compounds of the present disclosure | | |
|---|---|---|
| Ex No | Structure | Name |
| 710 | 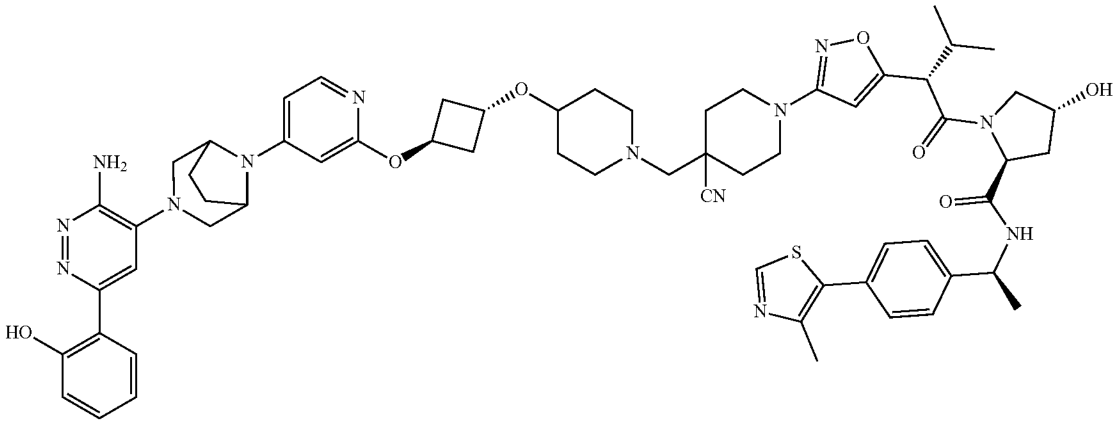 [SMILES: Cc1ncsc1-c1ccc([C@H](C)NC(=O)[C@@H]2C[C@@H](O)CN2C(=O)[C@H](c2cc(N3CCC(C#N)(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-4-cyanopiperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 711 | 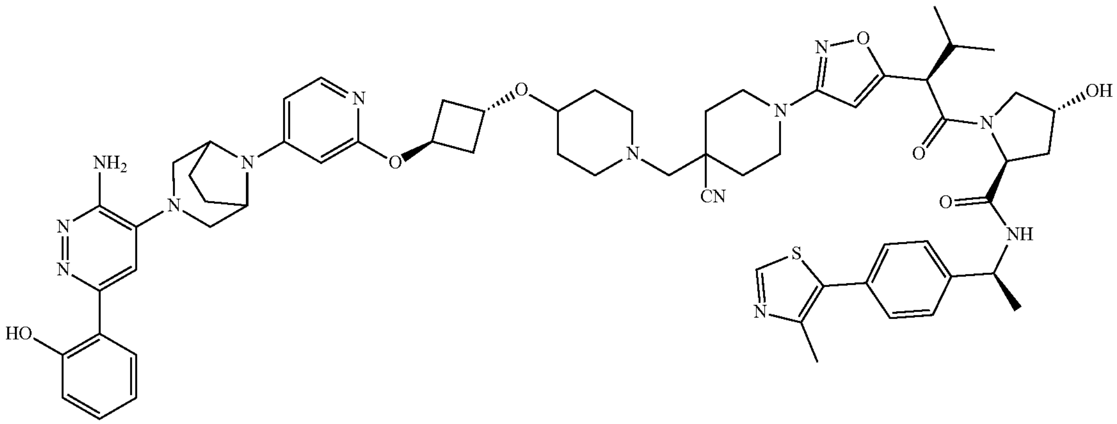 [SMILES: Cc1ncsc1-c1ccc([C@H](C)NC(=O)[C@@H]2C[C@@H](O)CN2C(=O)[C@@H](c2cc(N3CCC(C#N)(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-4-cyanopiperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 712 | 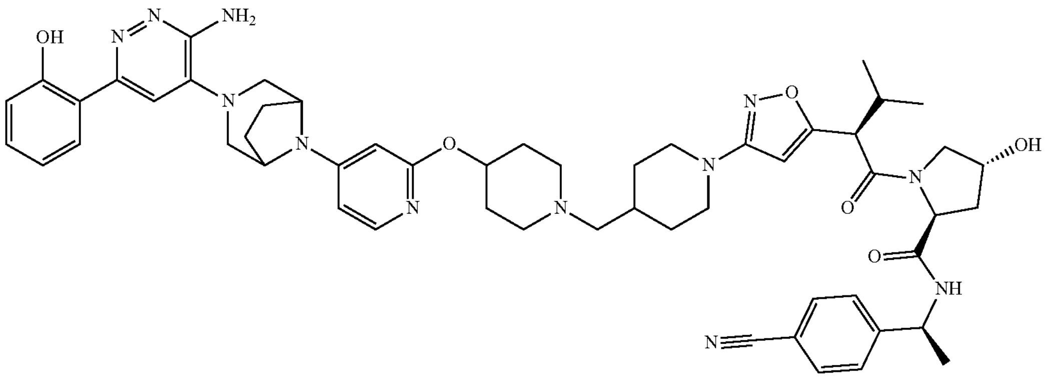 [SMILES: CC(C)[C@@H](C(=O)N1C[C@H](O)C[C@H]1C(=O)N[C@@H](C)c1ccc(C#N)cc1)c1cc(N2CCC(CN3CCC(Oc4cc(N5C6CCC5CN(c5cc(-c7ccccc7O)nnc5N)C6)ccn4)CC3)CC2)no1] | (2S,4R)-1-((2R)-2-(3-(4-((4-((4-(3-(3-amino-6-(2-hydroxyphenyl)pyridazin-4-yl)-3,8-diazabicyclo[3.2.1]octan-8-yl)pyridin-2-yl)oxy)piperidin-1-yl)methyl)piperidin-1-yl)isoxazol-5-yl)-3-methylbutanoyl)-N-((S)-1-(4-cyanophenyl)ethyl)-4-hydroxypyrrolidine-2-carboxamide |
| 713 | 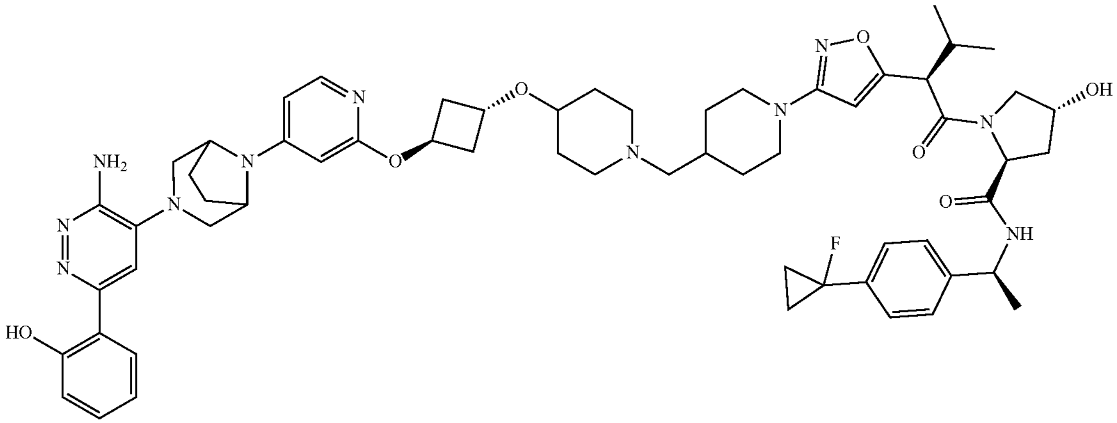 [SMILES: CC(C)[C@@H](C(=O)N1C[C@H](O)C[C@H]1C(=O)N[C@@H](C)c1ccc(C2(F)CC2)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-(1-fluorocyclopropyl)phenyl)ethyl)-4-hydroxypyrrolidine-2-carboxamide |

-continued

| []Exemplary bifunctional degradation compounds of the present disclosure | | |
|---|---|---|
| Ex No | Structure | Name |
| 714 | 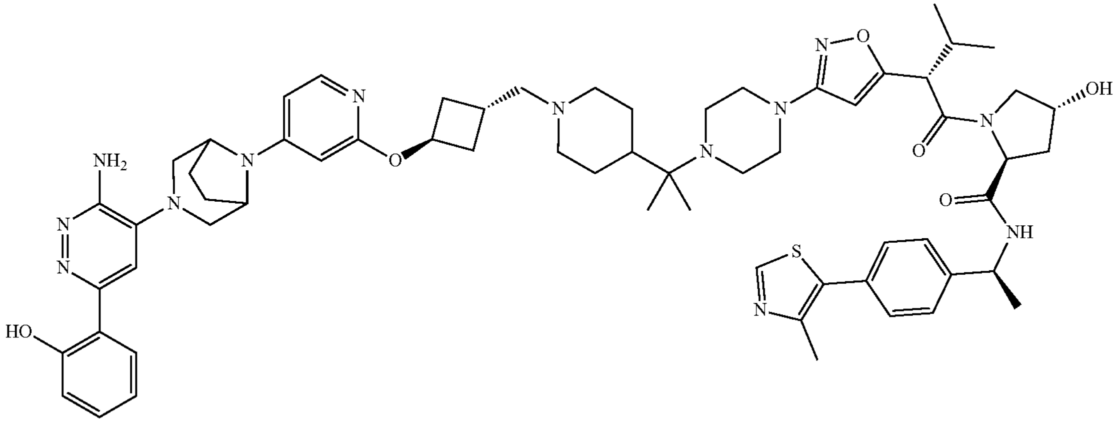 [SMILES: Cc1ncsc1-c1ccc([C@H](C)NC(=O)[C@@H]2C[C@@H](O)CN2C(=O)[C@H](c2cc(N3CCN(C(C)(C)C4CCN(C[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2S)-2-(3-(4-(2-(1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)propan-2-yl)piperazin-1-yl)isoxazol-5-yl)-3-methylbutanoyl)-4-hydroxy-N-((S)-1-(4-(4-methylthiazol-5-yl)phenyl)ethyl) pyrrolidine-2-carboxamide |
| 715 | 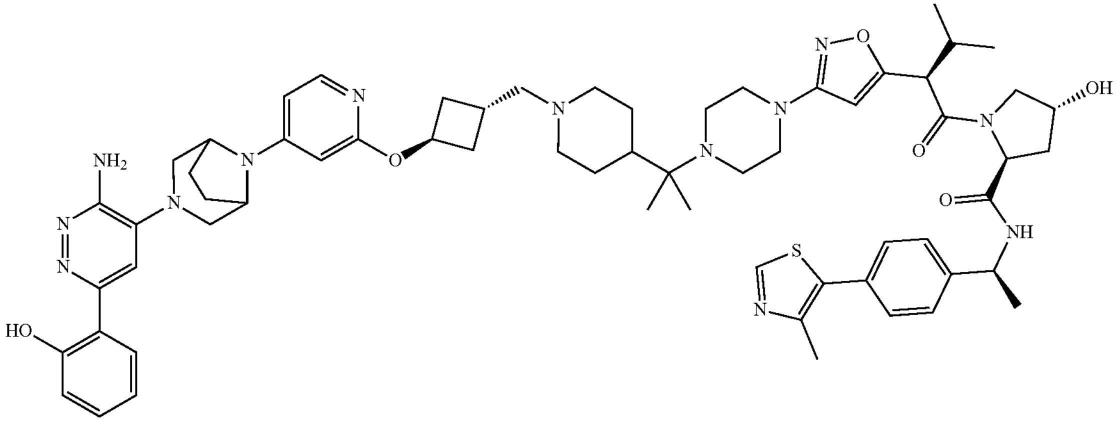 [SMILES: Cc1ncsc1-c1ccc([C@H](C)NC(=O)[C@@H]2C[C@@H](O)CN2C(=O)[C@@H](c2cc(N3CCN(C(C)(C)C4CCN(C[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-(2-(1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)propan-2-yl)piperazin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 716 | 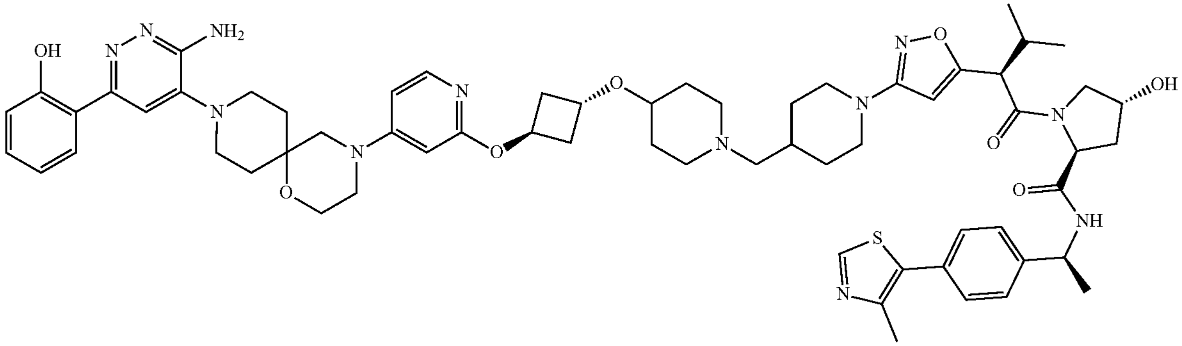 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7CCOC8(CCN(c9cc(-c%10ccccc%10O)nnc9N)CC8)C7)ccn6)C5)CC4)CC3)no2)C(C)C)cc1] | (2S,4R)-1-((R)-2-(3-(4-((4-((1r,3r)-3-((4-(9-(3-amino-6-(2-hydroxyphenyl)pyridazin-4-yl)-1-oxa-4,9-diazaspiro[5.5]undecan-4-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 717 | 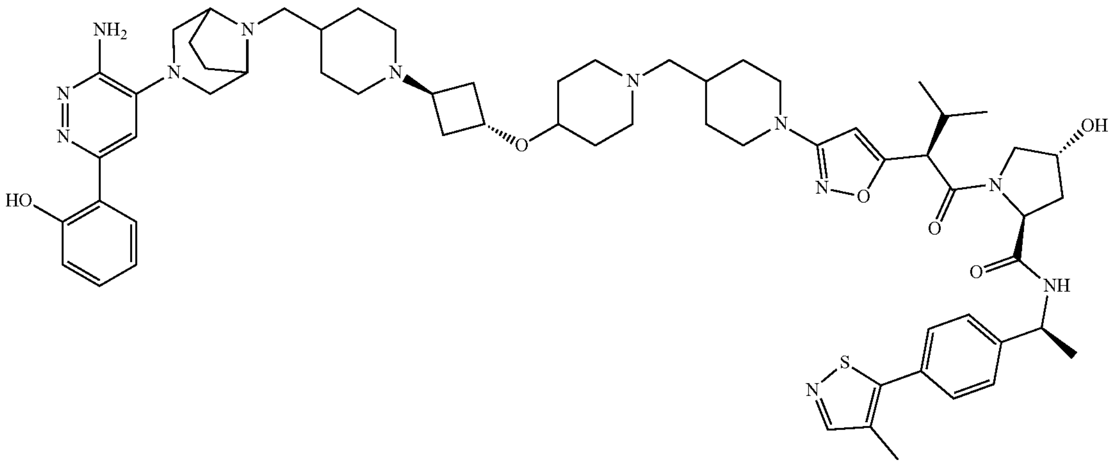 [SMILES: Cc1cnsc1-c1ccc([C@H](C)NC(=O)[C@@H]2C[C@@H](O)CN2C(=O)[C@@H](c2cc(N3CCC(CN4CCC(O[C@H]5C[C@H](N6CCC(CN7C8CCC7CN(c7cc(-c9ccccc9O)nnc7N)C8)CC6)C5)CC4)CC3)no2)C(C)C)cc1] | (2S,4R)-1-((2R)-2-(3-(4-((4-((1r,3r)-3-(4-((3-(3-amino-6-(2-hydroxyphenyl)pyridazin-4-yl)-3,8-diazabicyclo[3.2.1]octan-8-yl)methyl)piperidin-1-yl)cyclobutoxy)piperidin-1-yl)methyl)piperidin-1-yl)isoxazol-5-yl)-3-methylbutanoyl)-4-hydroxy-N-((S)-1-(4-(4-methylisothiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 718 | 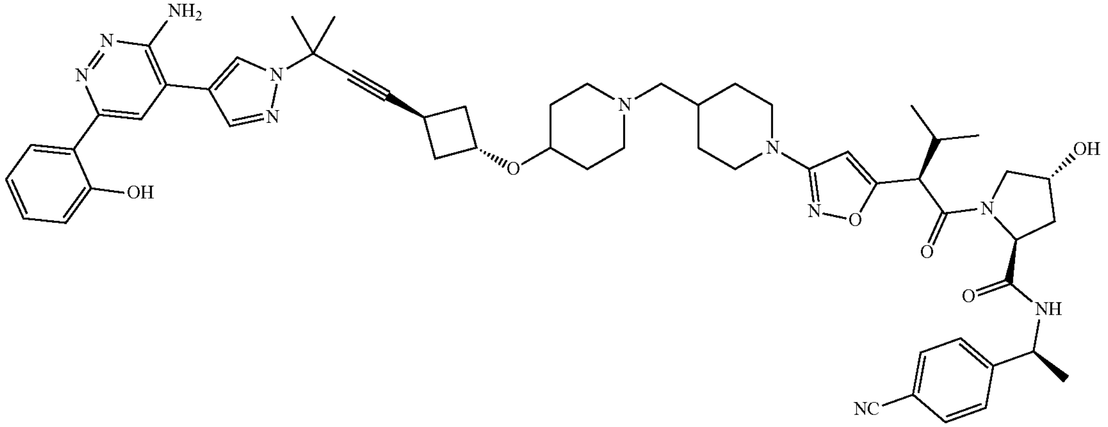 [SMILES: CC(C)[C@@H](C(=O)N1C[C@H](O)C[C@H]1C(=O)N[C@@H](C)c1ccc(C#N)cc1)c1cc(N2CCC(CN3CCC(O[C@H]4C[C@H](C#CC(C)(C)n5cc(-c6cc(-c7ccccc7O)nnc6N)cn5)C4)CC3)CC2)no1] | (2S,4R)-1-((R)-2-(3-(4-((4-((1r,3r)-3-(3-(4-(3-amino-6-(2-hydroxyphenyl)pyridazin-4-yl)-1H-pyrazol-1-yl)-3-methylbut-1-yn-1-yl)cyclobutoxy)piperidin-1-yl)methyl)piperidin-1-yl)isoxazol-5-yl)-3-methylbutanoyl)-N-((S)-1-(4-cyanophenyl)ethyl)-4-hydroxypyrrolidine-2-carboxamide |
| 719 | 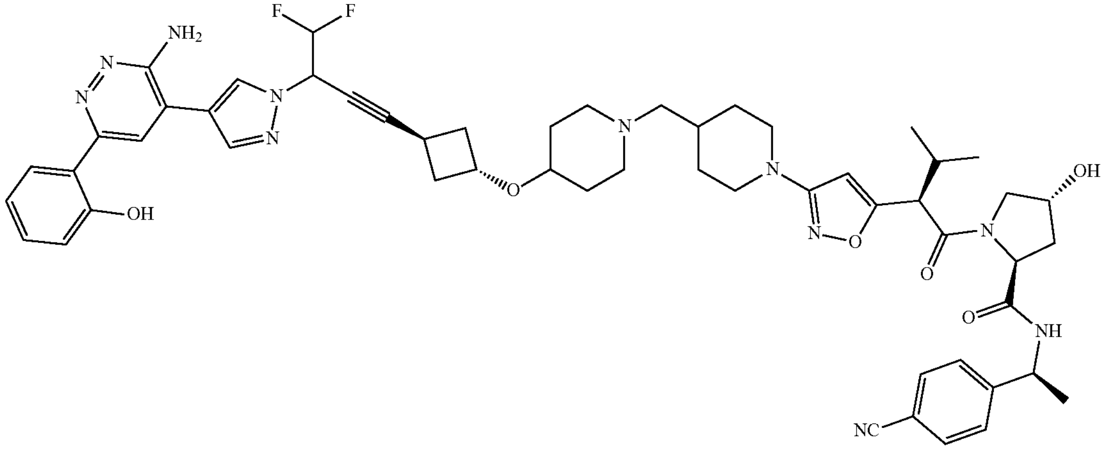 [SMILES: CC(C)[C@@H](C(=O)N1C[C@H](O)C[C@H]1C(=O)N[C@@H](C)c1ccc(C#N)cc1)c1cc(N2CCC(CN3CCC(O[C@H]4C[C@H](C#CC(C(F)F)n5cc(-c6cc(-c7ccccc7O)nnc6N)cn5)C4)CC3)CC2)no1] | (2S,4R)-1-((2R)-2-(3-(4-((4-((1r,3r)-3-(3-(4-(3-amino-6-(2-hydroxyphenyl)pyridazin-4-yl)-1H-pyrazol-1-yl)-4,4-difluorobut-1-yn-1-yl)cyclobutoxy)piperidin-1-yl)methyl)piperidin-1-yl)isoxazol-5-yl)-3-methylbutanoyl)-N-((S)-1-(4-cyanophenyl)ethyl)-4-hydroxypyrrolidine-2-carboxamide |

-continued

[]Exemplary bifunctional degradation compounds of the present disclosure

| Ex No | Structure | Name |
|---|---|---|
| 720 | 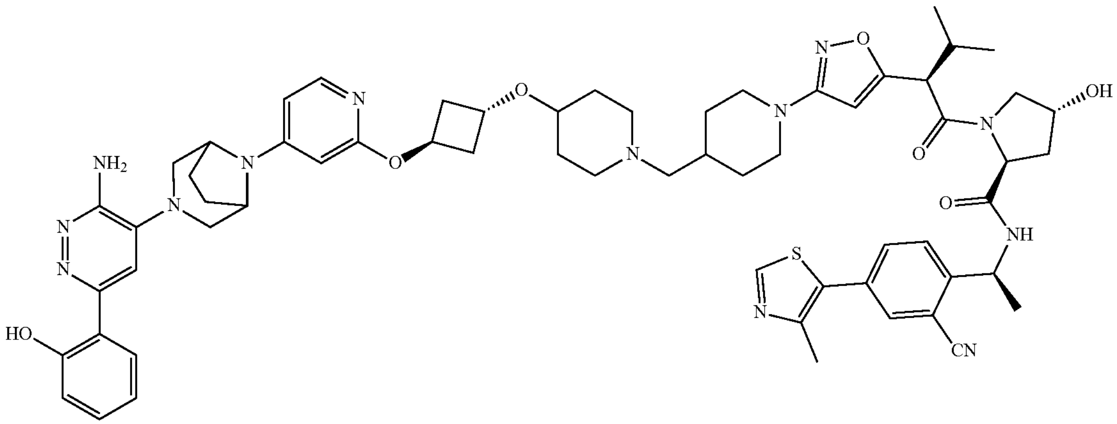 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)c(C#N)c1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(2-cyano-4-(4-methylthiazol-5-yl)phenyl)ethyl)-4-hydroxypyrrolidine-2-carboxamide |
| 721 | 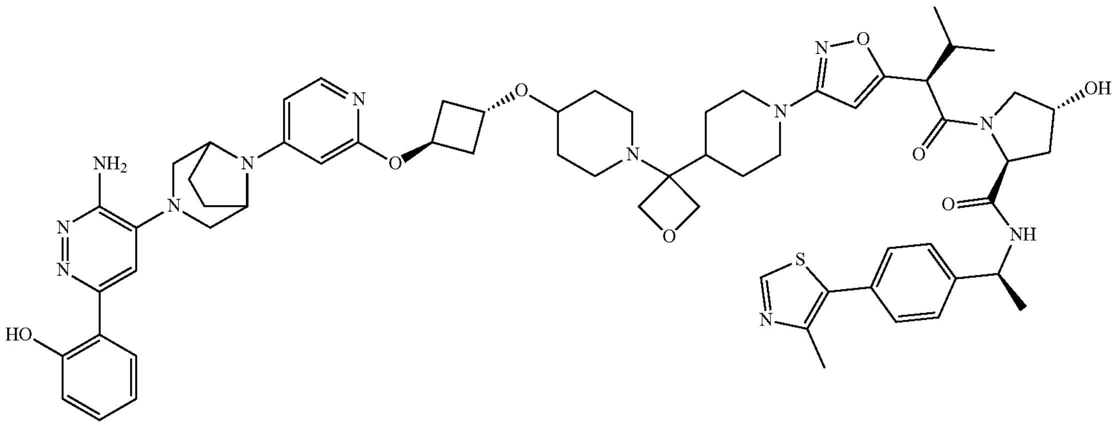 [SMILES: Cc1ncsc1-c1ccc([C@H](C)NC(=O)[C@@H]2C[C@@H](O)CN2C(=O)[C@@H](c2cc(N3CCC(C4(N5CCC(O[C@H]6C[C@H](Oc7cc(N8C9CCC8CN(c8cc(-c%10ccccc%10O)nnc8N)C9)ccn7)C6)CC5)COC4)CC3)no2)C(C)C)cc1] | (2S,4R)-1-((2R)-2-(3-(4-(3-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)oxetan-3-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 722 | 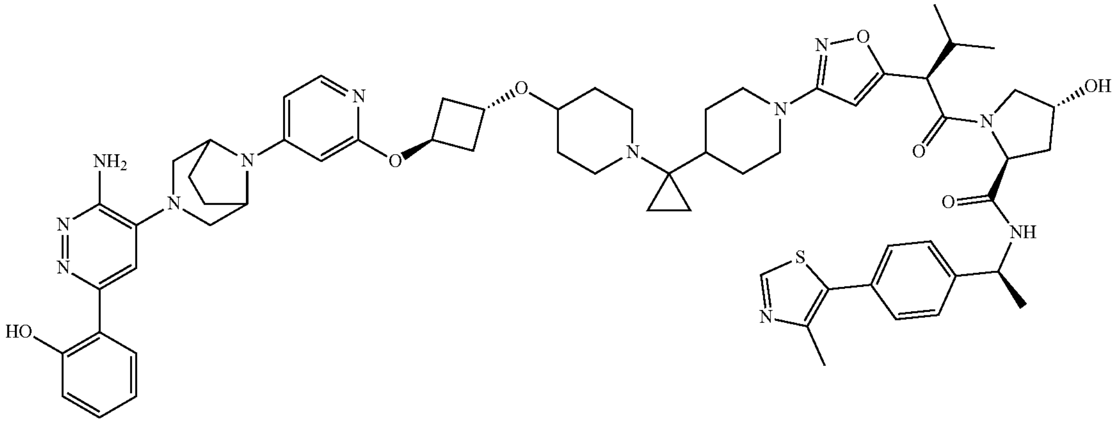 [SMILES: Cc1ncsc1-c1ccc([C@H](C)NC(=O)[C@@H]2C[C@@H](O)CN2C(=O)[C@@H](c2cc(N3CCC(C4(N5CCC(O[C@H]6C[C@H](Oc7cc(N8C9CCC8CN(c8cc(-c%10ccccc%10O)nnc8N)C9)ccn7)C6)CC5)CC4)CC3)no2)C(C)C)cc1] | (2S,4R)-1-((2R)-2-(3-(4-(1-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)cyclopropyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 723 | 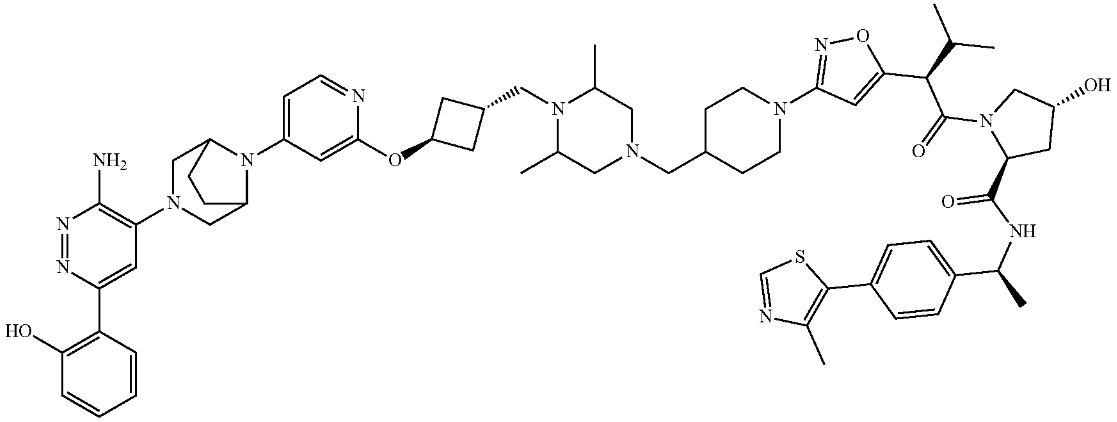 [SMILES: Cc1ncsc1-c1ccc([C@H](C)NC(=O)[C@@H]2C[C@@H](O)CN2C(=O)[C@@H](c2cc(N3CCC(CN4CC(C)N(C[C@H]5C[C@H](Oc6cc(N7C8CCC7CN(c7cc(-c9ccccc9O)nnc7N)C8)ccn6)C5)C(C)C4)CC3)no2)C(C)C)cc1] | (2S,4R)-1-((2R)-2-(3-(4-((4-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-3,5-dimethylpiperazin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 724 | 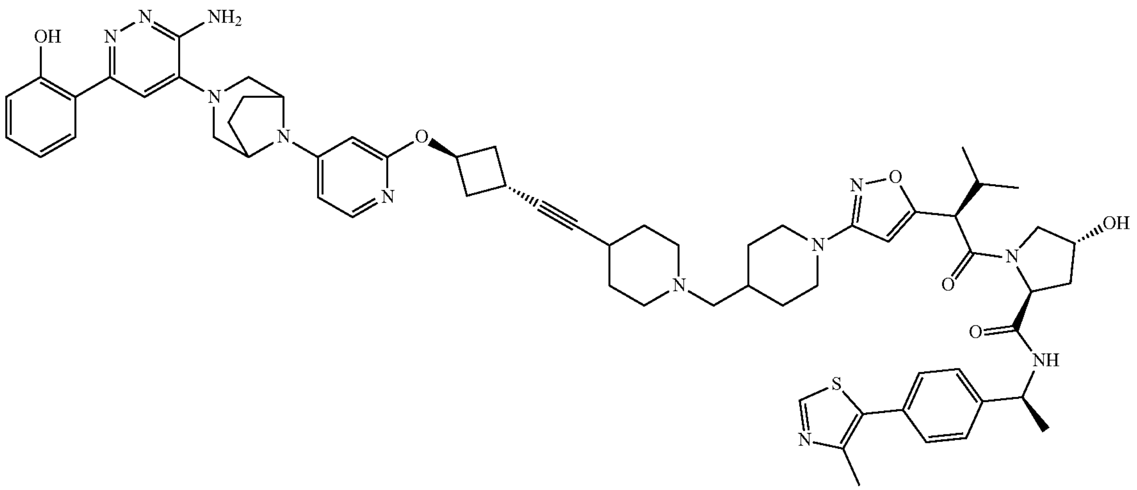 [SMILES: Cc1ncsc1-c1ccc([C@H](C)NC(=O)[C@@H]2C[C@@H](O)CN2C(=O)[C@@H](c2cc(N3CCC(CN4CCC(C#C[C@H]5C[C@H](Oc6cc(N7C8CCC7CN(c7cc(-c9ccccc9O)nnc7N)C8)ccn6)C5)CC4)CC3)no2)C(C)C)cc1] | (2S,4R)-1-((2R)-2-(3-(4-((4-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)ethynyl)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 725 | 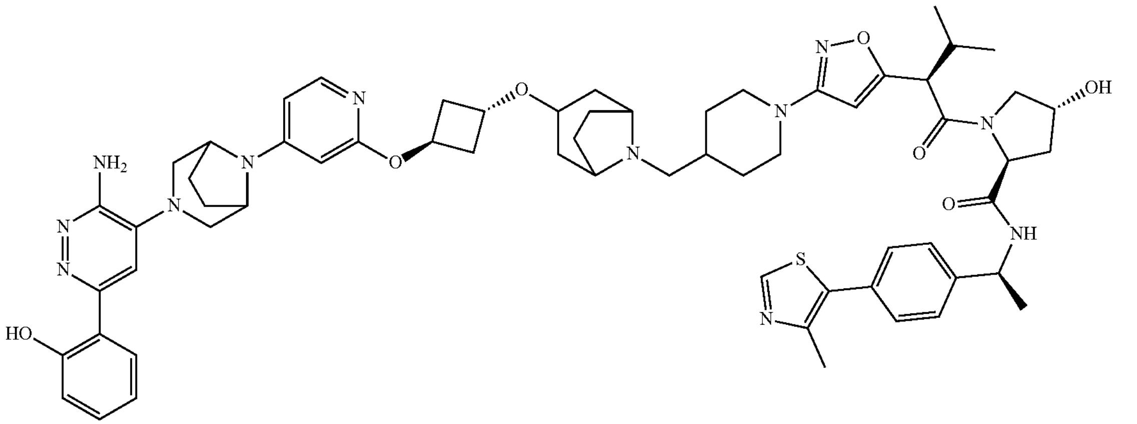 [SMILES: Cc1ncsc1-c1ccc([C@H](C)NC(=O)[C@@H]2C[C@@H](O)CN2C(=O)[C@@H](c2cc(N3CCC(CN4C5CCC4CC(O[C@H]4C[C@H](Oc6cc(N7C8CCC7CN(c7cc(-c9ccccc9O)nnc7N)C8)ccn6)C4)C5)CC3)no2)C(C)C)cc1] | (2S,4R)-1-((2R)-2-(3-(4-((3-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)-8-azabicyclo[3.2.1]octan-8-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 726 | 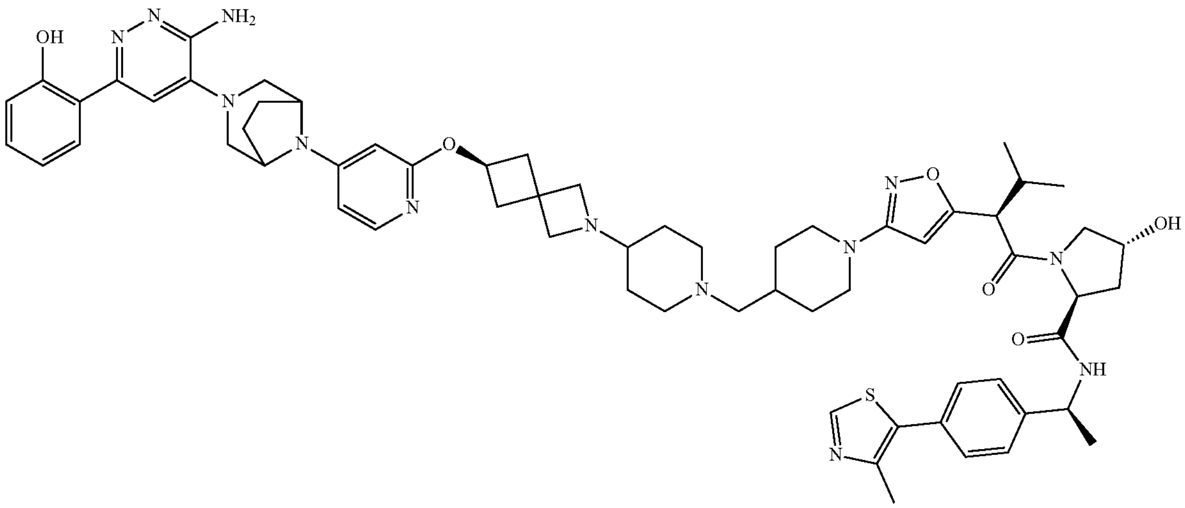 | (2S,4R)-1-((2R)-2-(3-(4-((4-(6-((4-(3-(3-amino-6-(2-hydroxyphenyl)pyridazin-4-yl)-3,8-diazabicyclo[3.2.1]octan-8-yl)pyridin-2-yl)oxy)-2-azaspiro[3.3]heptan-2-yl)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 727 | 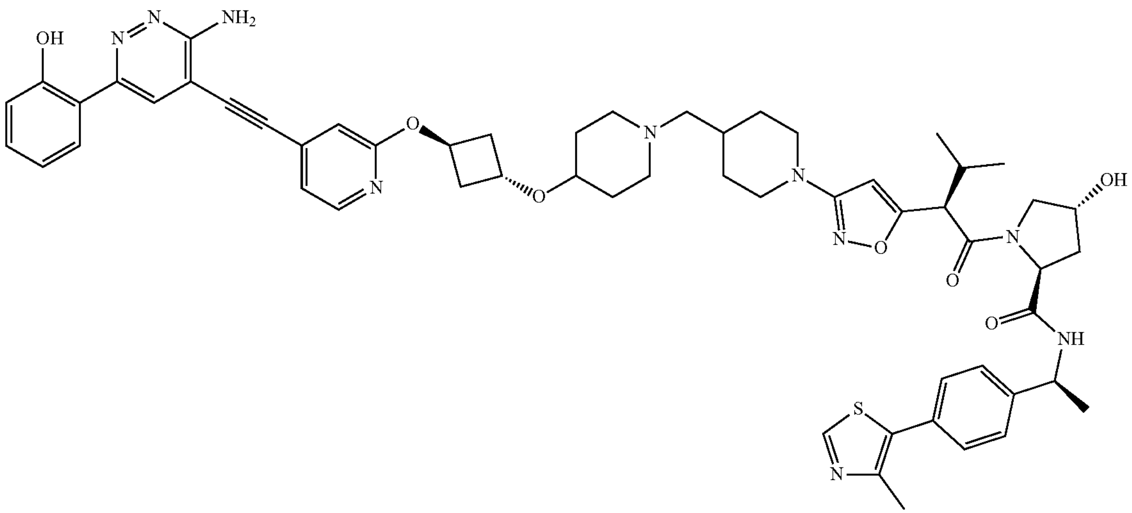 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(C#Cc7cc(-c8ccccc8O)nnc7N)ccn6)C5)CC4)CC3)no2)C(C)C)cc1] | (2S,4R)-1-((R)-2-(3-(4-((4-((1r,3r)-3-((4-((3-amino-6-(2-hydroxyphenyl)pyridazin-4-yl)ethynyl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 728 | 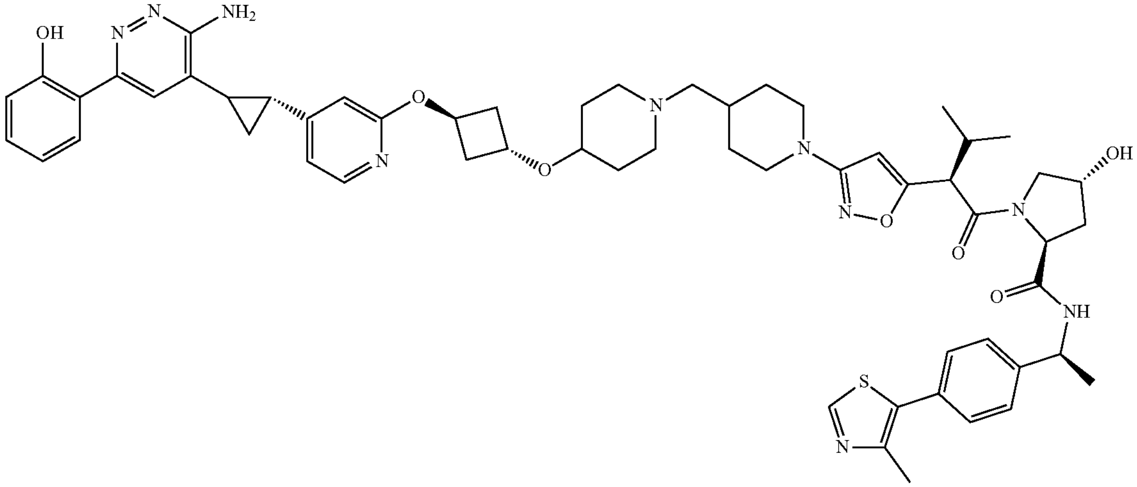 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc([C@@H]7CC7c7cc(-c8ccccc8O)nnc7N)ccn6)C5)CC4)CC3)no2)C(C)C)cc1] | (2S,4R)-1-((R)-2-(3-(4-((4-((1R,3r)-3-((4-((1R,2R)-2-(3-amino-6-(2-hydroxyphenyl)pyridazin-4-yl)cyclopropyl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 729 | 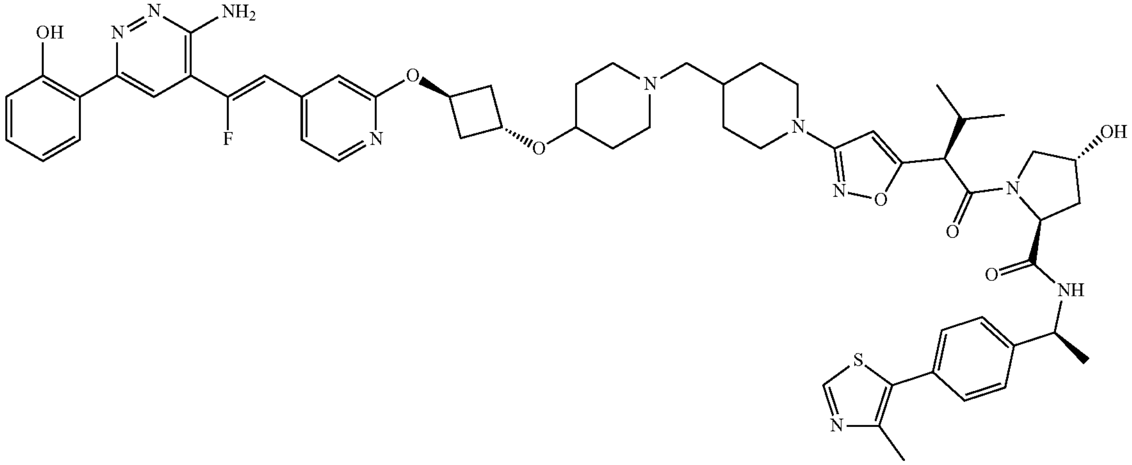 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(/C=C(\F)c7cc(-c8ccccc8O)nnc7N)ccn6)C5)CC4)CC3)no2)C(C)C)cc1] | (2S,4R)-1-((R)-2-(3-(4-((4-((1r,3r)-3-((4-((Z)-2-(3-amino-6-(2-hydroxyphenyl)pyridazin-4-yl)-2-fluorovinyl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 730 | 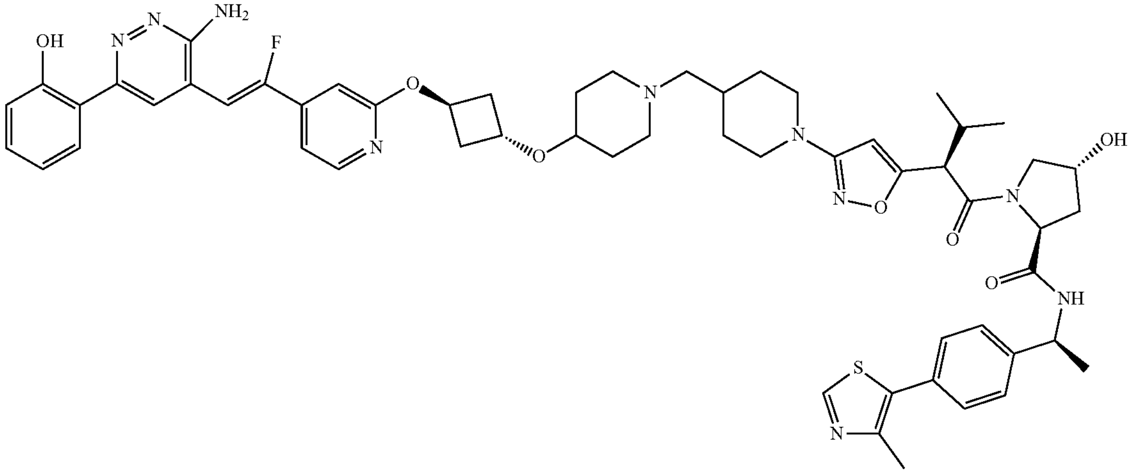 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(/C(F)=C/c7cc(-c8ccccc8O)nnc7N)ccn6)C5)CC4)CC3)no2)C(C)C)cc1] | (2S,4R)-1-((R)-2-(3-(4-((4-((1r,3r)-3-((4-((Z)-2-(3-amino-6-(2-hydroxyphenyl)pyridazin-4-yl)-1-fluorovinyl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 731 | 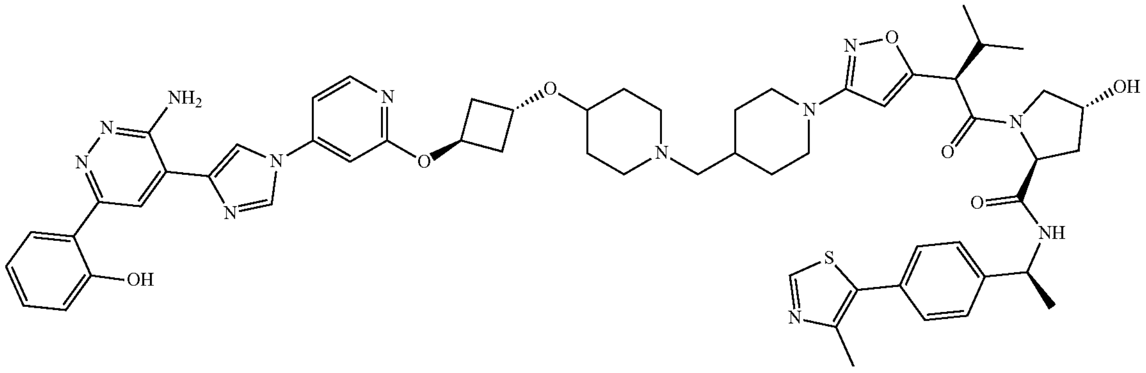 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(-n7cnc(-c8cc(-c9ccccc9O)nnc8N)c7)ccn6)C5)CC4)CC3)no2)C(C)C)cc1] | (2S,4R)-1-((R)-2-(3-(4-((4-((1r,3r)-3-((4-(4-(3-amino-6-(2-hydroxyphenyl)pyridazin-4-yl)-1H-imidazol-1-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 732 | 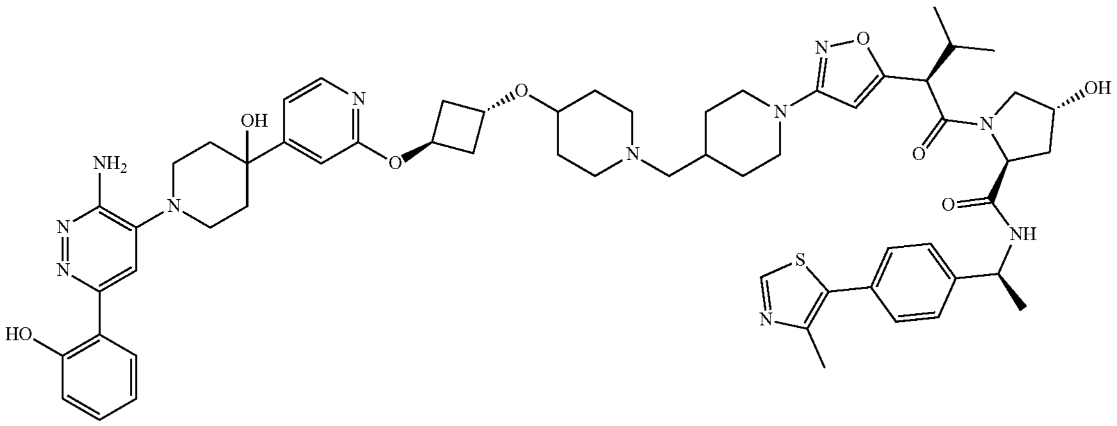 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(C7(O)CCN(c8cc(-c9ccccc9O)nnc8N)CC7)ccn6)C5)CC4)CC3)no2)C(C)C)cc1] | (2S,4R)-1-((R)-2-(3-(4-((4-((1r,3r)-3-((4-(1-(3-amino-6-(2-hydroxyphenyl)pyridazin-4-yl)-4-hydroxypiperidin-4-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 733 | 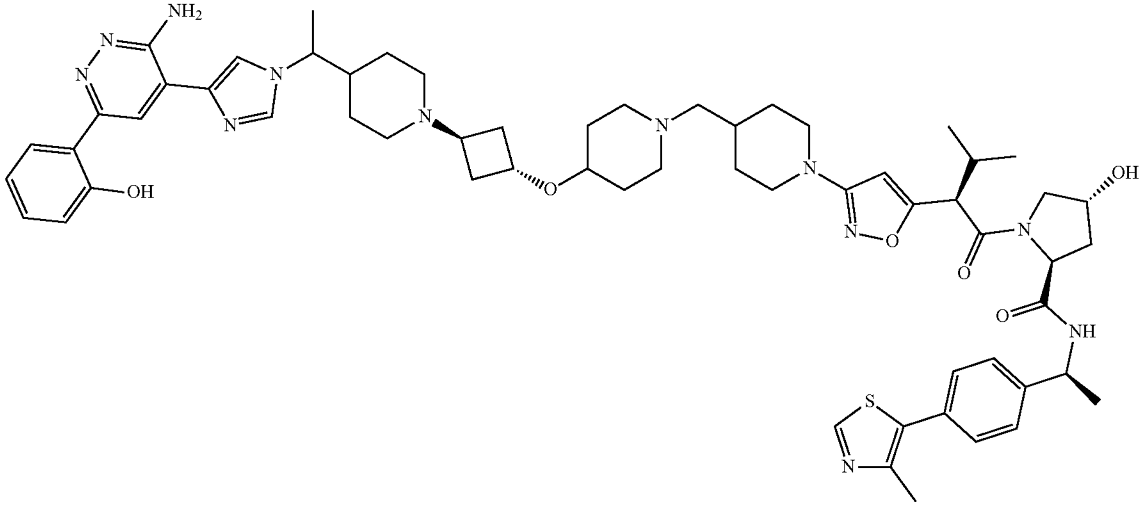 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](N6CCC(C(C)n7cnc(-c8cc(-c9ccccc9O)nnc8N)c7)CC6)C5)CC4)CC3)no2)C(C)C)cc1] | (2S,4R)-1-((2R)-2-(3-(4-((4-((1r,3r)-3-(4-(1-(4-(3-amino-6-(2-hydroxyphenyl)pyridazin-4-yl)-1H-imidazol-1-yl)ethyl)piperidin-1-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 734 | 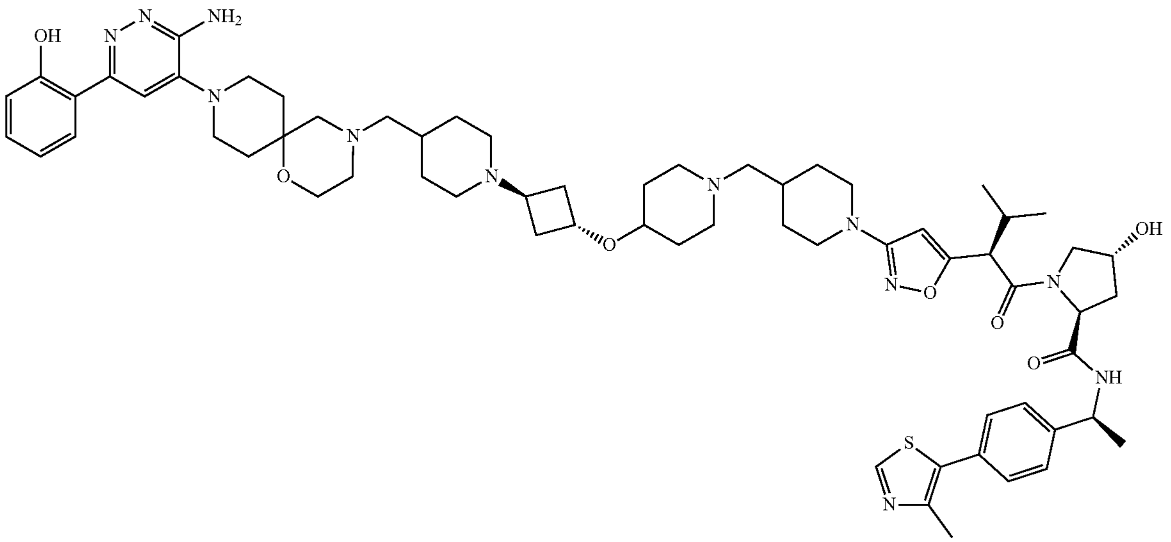 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](N6CCC(CN7CCOC8(CCN(c9cc(-c%10ccccc%10O)nnc9N)CC8)C7)CC6)C5)CC4)CC3)no2)C(C)C)cc1] | (2S,4R)-1-((R)-2-(3-(4-((4-((1r,3r)-3-(4-((9-(3-amino-6-(2-hydroxyphenyl)pyridazin-4-yl)-1-oxa-4,9-diazaspiro[5.5]undecan-4-yl)methyl)piperidin-1-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 735 | 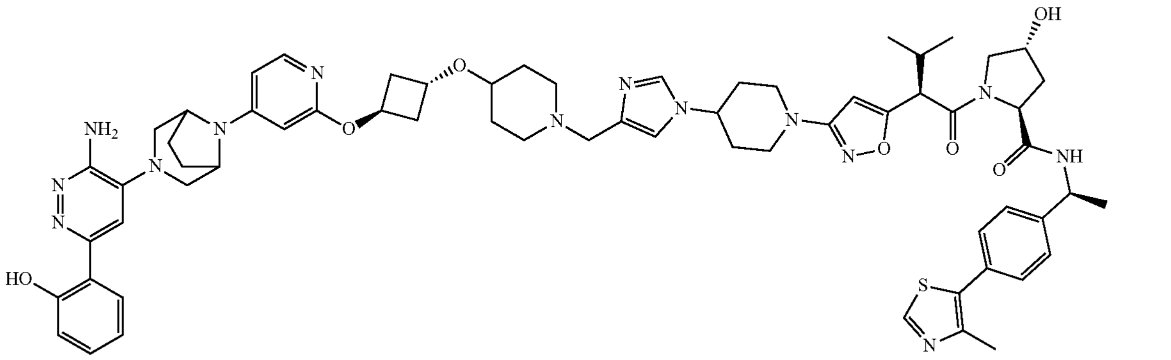 [SMILES: Cc1ncsc1-c1ccc([C@H](C)NC(=O)[C@@H]2C[C@@H](O)CN2C(=O)[C@@H](c2cc(N3CCC(n4cnc(CN5CCC(O[C@H]6C[C@H](Oc7cc(N8C9CCC8CN(c8cc(-c%10ccccc%10O)nnc8N)C9)ccn7)C6)CC5)c4)CC3)no2)C(C)C)cc1] | (2S,4R)-1-((2R)-2-(3-(4-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-1H-imidazol-1-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
| --- | --- | --- |
| []Exemplary bifunctional degradation compounds of the present disclosure | | |
| 736 | 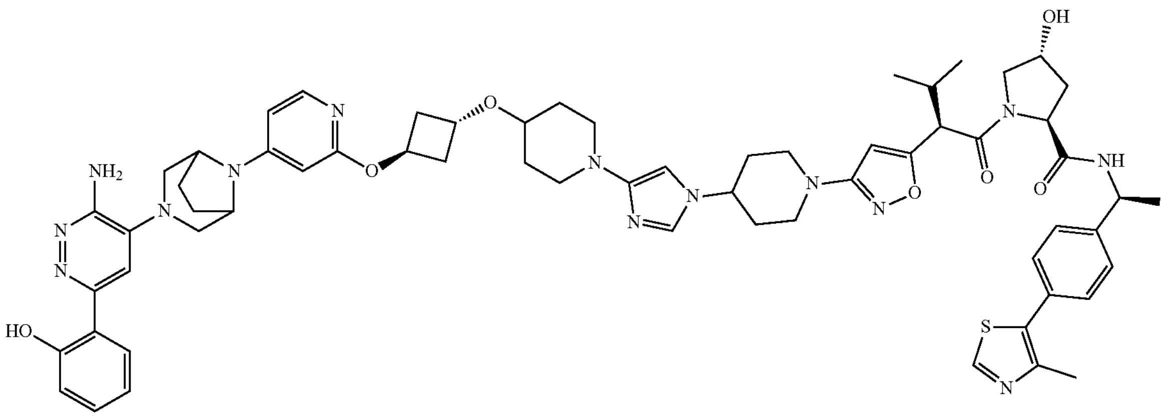 [SMILES: Cc1ncsc1-c1ccc([C@H](C)NC(=O)[C@@H]2C[C@@H](O)CN2C(=O)[C@@H](c2cc(N3CCC(n4cnc(N5CCC(O[C@H]6C[C@H](Oc7cc(N8C9CCC8CN(c8cc(-c%10ccccc%10O)nnc8N)C9)ccn7)C6)CC5)c4)CC3)no2)C(C)C)cc1] | (2S,4R)-1-((2R)-2-(3-(4-(4-(4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)-1H-imidazol-1-yl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 737 | 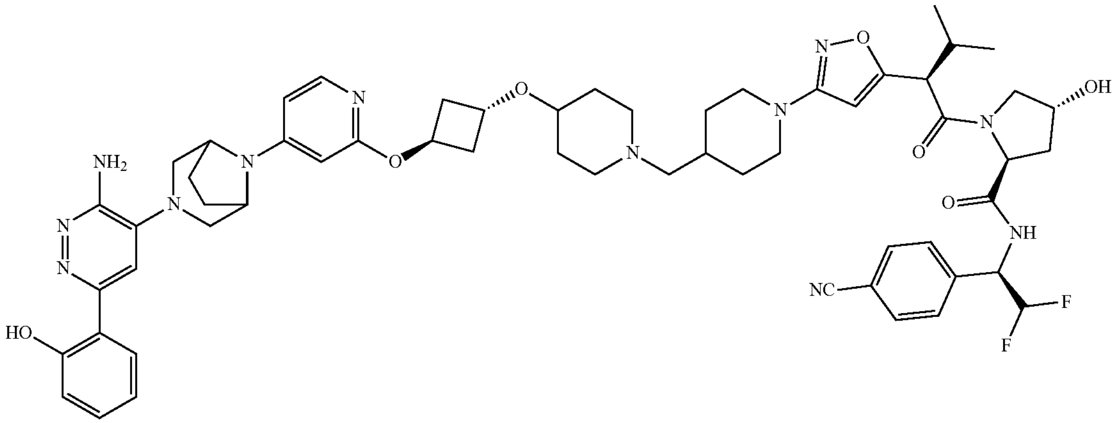 [SMILES: CC(C)[C@@H](C(=O)N1C[C@H](O)C[C@H]1C(=O)N[C@H](c1ccc(C#N)cc1)C(F)F)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((R)-1-(4-cyanophenyl)-2,2-difluoroethyl)-4-hydroxypyrrolidine-2-carboxamide |

-continued

[]Exemplary bifunctional degradation compounds of the present disclosure

| Ex No | Structure | Name |
|---|---|---|
| 738 | 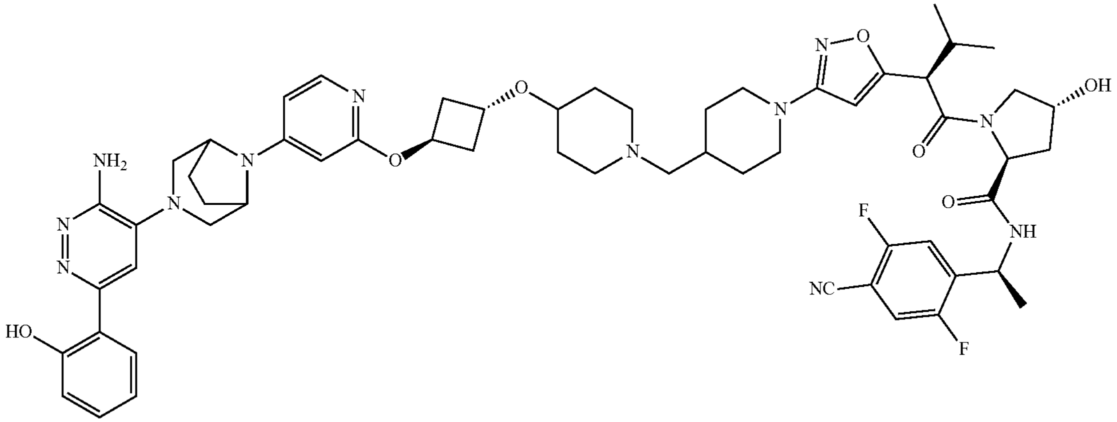 [SMILES: CC(C)[C@@H](C(=O)N1C[C@H](O)C[C@H]1C(=O)N[C@@H](C)c1cc(F)c(C#N)cc1F)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-cyano-2,5-difluorophenyl)ethyl)-4-hydroxypyrrolidine-2-carboxamide |
| 739 | 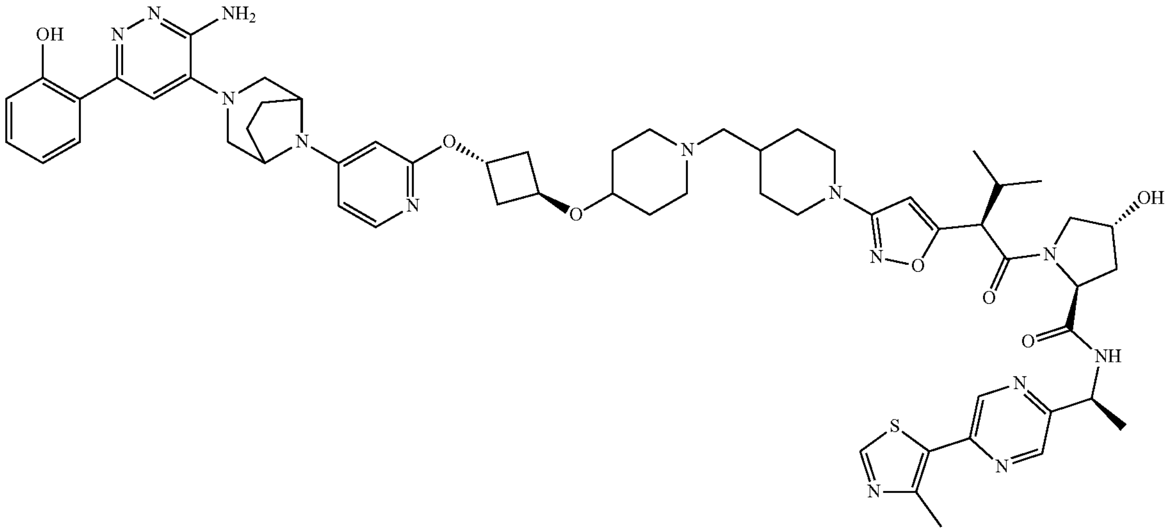 [SMILES: Cc1ncsc1-c1cnc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cn1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(5-(4-methylthiazol-5-yl)pyrazin-2-yl)ethyl)pyrrolidine-2-carboxamide |

-continued

[]Exemplary bifunctional degradation compounds of the present disclosure

| Ex No | Structure | Name |
| --- | --- | --- |
| 740 | 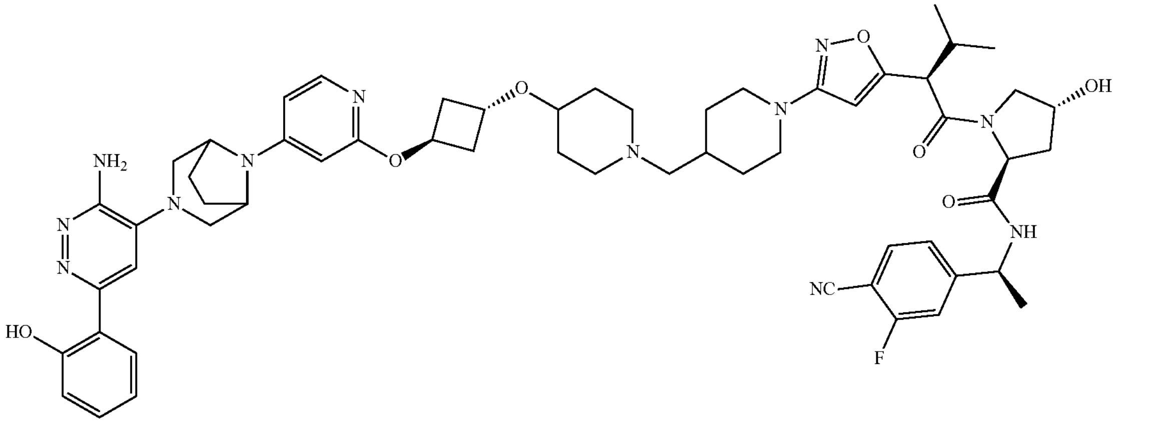 [SMILES: CC(C)[C@@H](C(=O)N1C[C@H](O)C[C@H]1C(=O)N[C@@H](C)c1ccc(C#N)c(F)c1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-cyano-3-fluorophenyl)ethyl)-4-hydroxypyrrolidine-2-carboxamide |
| 741 | 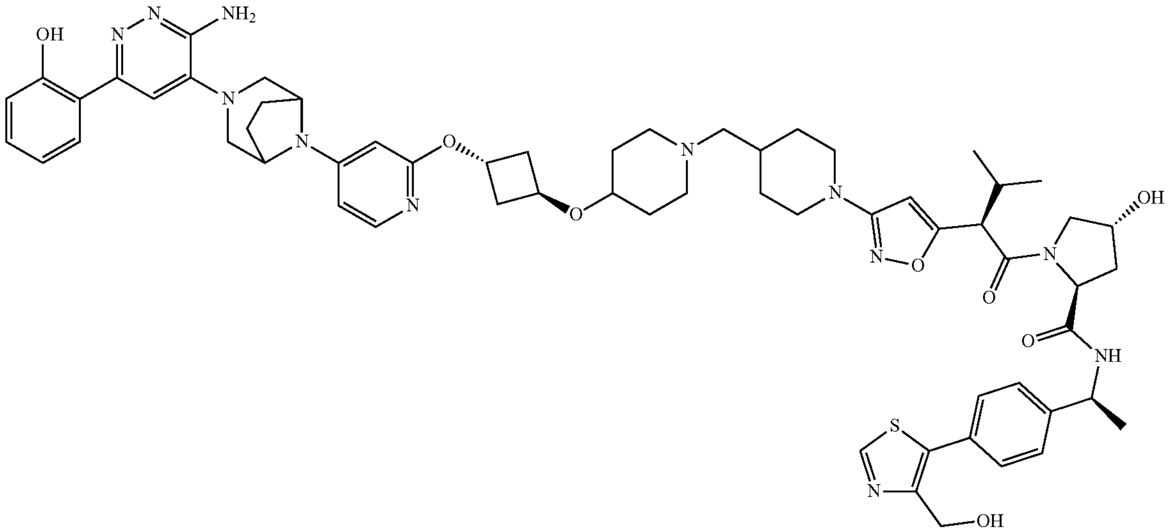 [SMILES: CC(C)[C@@H](C(=O)N1C[C@H](O)C[C@H]1C(=O)N[C@@H](C)c1ccc(-c2scnc2CO)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(4-(hydroxymethyl)thiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 742 | 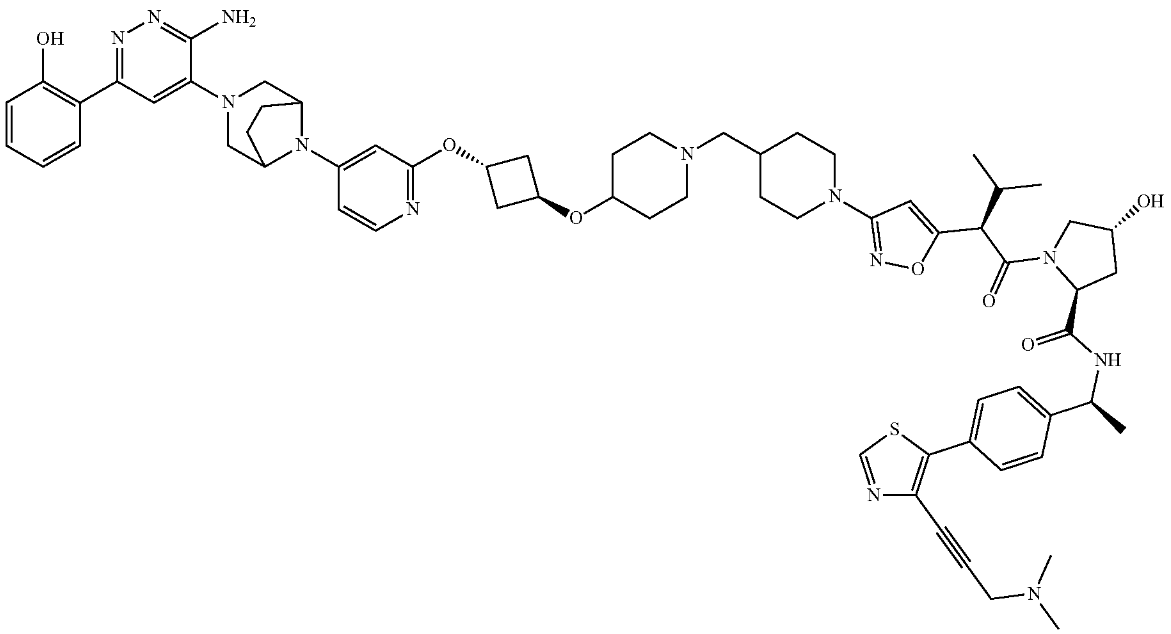 [SMILES: CC(C)[C@@H](C(=O)N1C[C@H](O)C[C@H]1C(=O)N[C@@H](C)c1ccc(-c2scnc2C#CCN(C)C)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-N-((S)-1-(4-(4-(3-(dimethylamino)prop-1-yn-1-yl)thiazol-5-yl)phenyl)ethyl)-4-hydroxypyrrolidine-2-carboxamide |
| 743 | 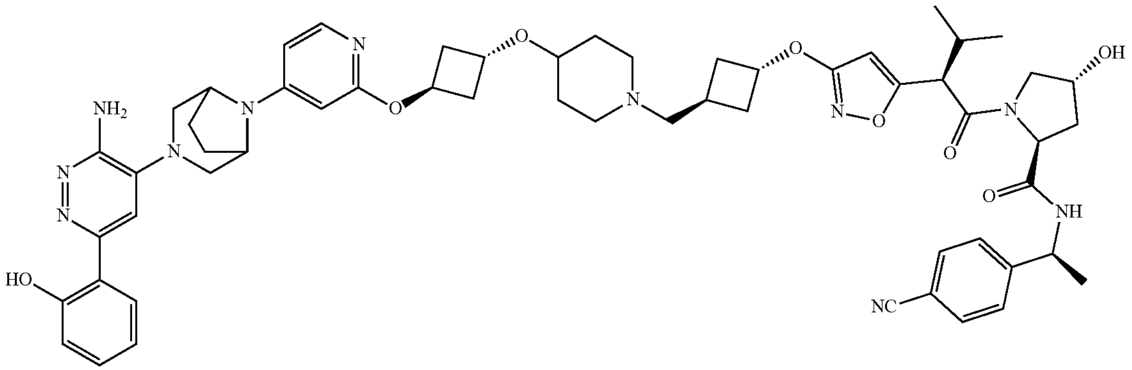 [SMILES: CC(C)[C@@H](C(=O)N1C[C@H](O)C[C@H]1C(=O)N[C@@H](C)c1ccc(C#N)cc1)c1cc(O[C@H]2C[C@H](CN3CCC(O[C@H]4C[C@H](Oc5cc(N6C7CCC6CN(c6cc(-c8ccccc8O)nnc6N)C7)ccn5)C4)CC3)C2)no1] | (2S,4R)-1-((2R)-2-(3-((1R,3R)-3-((4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)cyclobutoxy)isoxazol-5-yl)-3-methylbutanoyl)-N-((S)-1-(4-cyanophenyl)ethyl)-4-hydroxypyrrolidine-2-carboxamide |

-continued

| []Exemplary bifunctional degradation compounds of the present disclosure | | |
|---|---|---|
| Ex No | Structure | Name |
| 744 | 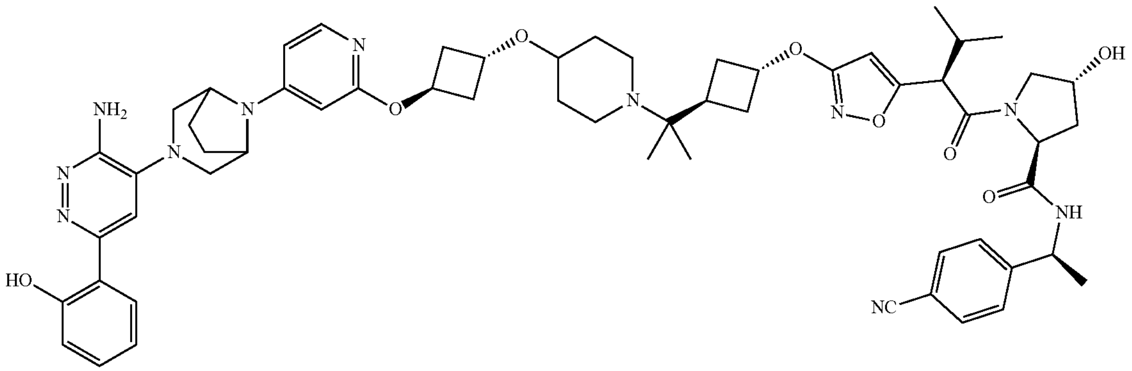 [SMILES: CC(C)[C@@H](C(=O)N1C[C@H](O)C[C@H]1C(=O)N[C@@H](C)c1ccc(C#N)cc1)c1cc(O[C@H]2C[C@H](C(C)(C)N3CCC(O[C@H]4C[C@H](Oc5cc(N6C7CCC6CN(c6cc(-c8ccccc8O)nnc6N)C7)ccn5)C4)CC3)C2)no1] | (2S,4R)-1-((2R)-2-(3-((1R,3R)-3-(2-(4-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)propan-2-yl)cyclobutoxy)isoxazol-5-yl)-3-methylbutanoyl)-N-((S)-1-(4-cyanophenyl)ethyl)-4-hydroxypyrrolidine-2-carboxamide |
| 745 | 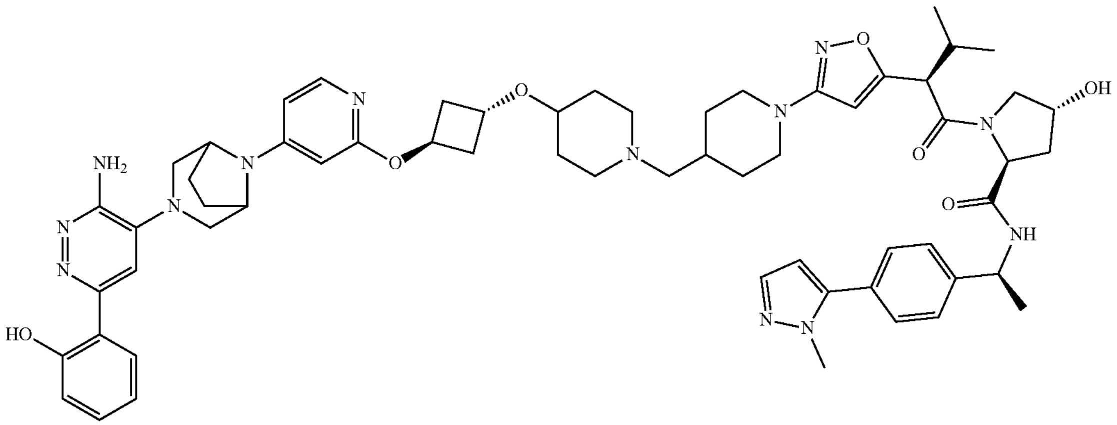 [SMILES: CC(C)[C@@H](C(=O)N1C[C@H](O)C[C@H]1C(=O)N[C@@H](C)c1ccc(-c2ccnn2C)cc1)c1cc(N2CCC(CN3CCC(O[C@H]4C[C@H](Oc5cc(N6C7CCC6CN(c6cc(-c8ccccc8O)nnc6N)C7)ccn5)C4)CC3)CC2)no1] | (2S,4R)-1-((R)-2-(3-(4-((4-((1r,3r)-3-((4-(4-(3-amino-6-(2-hydroxyphenyl)pyridazin-4-yl)piperazin-1-yl)pyridin-2-yl)oxy)cyclobutoxy)piperidin-1-yl)methyl)piperidin-1-yl)isoxazol-5-yl)-3-methylbutanoyl)-4-hydroxy-N-((S)-1-(4-(1-methyl-1H-pyrazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 746 | 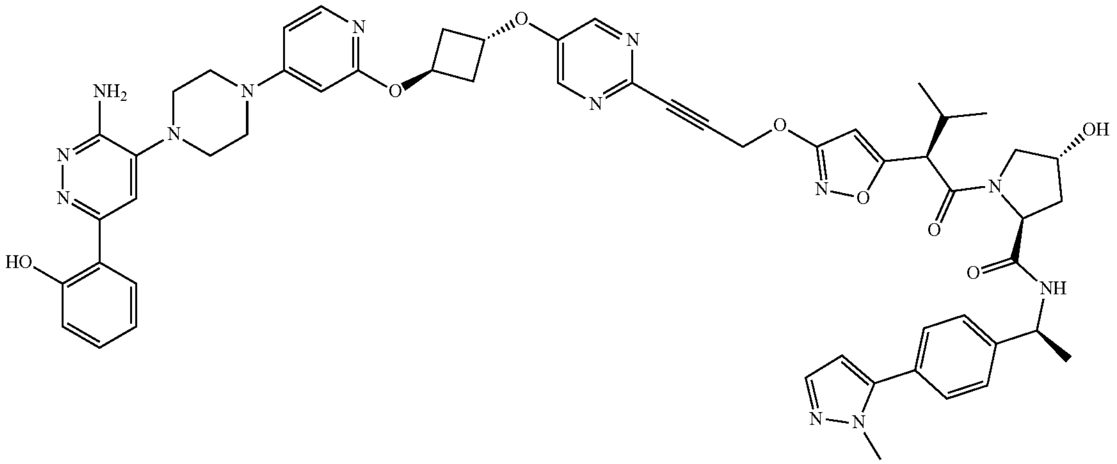 [SMILES: CC(C)[C@@H](C(=O)N1C[C@H](O)C[C@H]1C(=O)N[C@@H](C)c1ccc(-c2ccnn2C)cc1)c1cc(OCC#Cc2ncc(O[C@H]3C[C@H](Oc4cc(N5CCN(c6cc(-c7ccccc7O)nnc6N)CC5)ccn4)C3)cn2)no1] | (2S,4R)-1-((R)-2-(3-((3-(5-((1r,3R)-3-((4-(4-(3-amino-6-(2-hydroxyphenyl)pyridazin-4-yl)piperazin-1-yl)pyridin-2-yl)oxy)cyclobutoxy)pyrimidin-2-yl)prop-2-yn-1-yl)oxy)isoxazol-5-yl)-3-methylbutanoyl)-4-hydroxy-N-((S)-1-(4-(1-methyl-1H-pyrazol-5-yl)phenyl)ethyl)pyrrolidine-2-carboxamide |
| 747 | 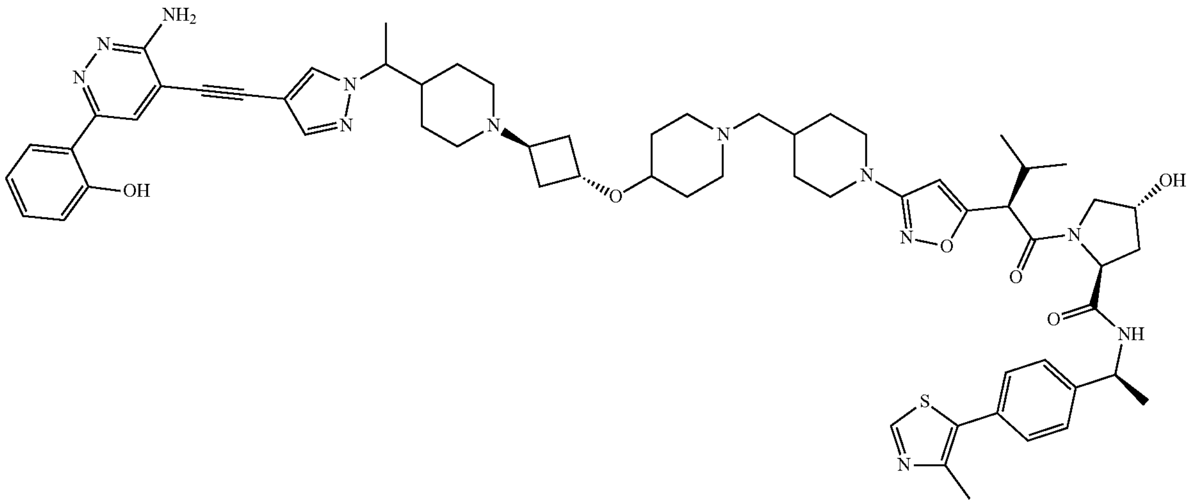 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](N6CCC(C(C)n7cc(C#Cc8cc(-c9ccccc9O)nnc8N)cn7)CC6)C5)CC4)CC3)no2)C(C)C)cc1] | (2S,4R)-1-((2R)-2-(3-(4-((4-((1r,3r)-3-(4-(1-(4-((3-amino-6-(2-hydroxyphenyl)pyridazin-4-yl)ethynyl)-1H-pyrazol-1-yl)ethyl)piperidin-1-yl)cyclobutoxy)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 748 | 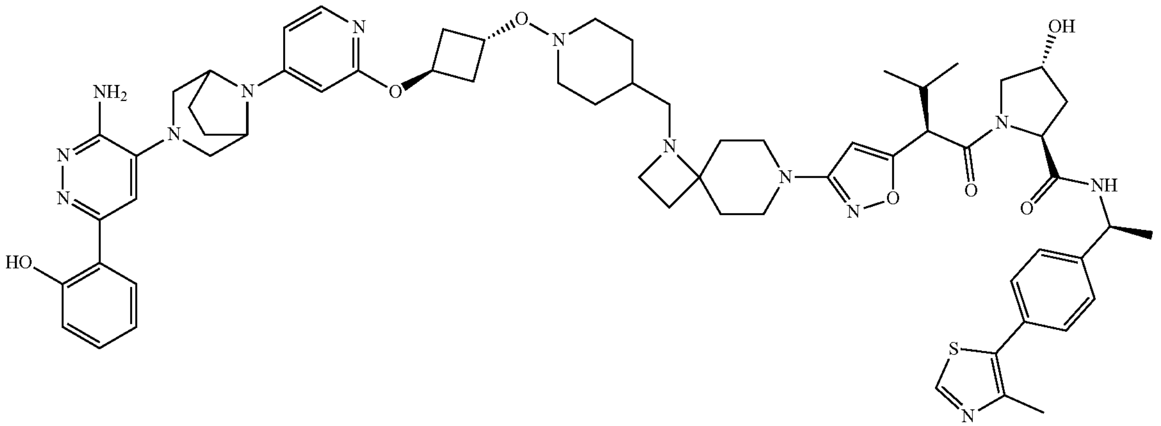 [SMILES: Cc1ncsc1-c1ccc([C@H](C)NC(=O)[C@@H]2C[C@@H](O)CN2C(=O)[C@@H](c2cc(N3CCC4(CC3)CCN4CC3CCN(O[C@H]4C[C@H](Oc5cc(N6C7CCC6CN(c6cc(-c8ccccc8O)nnc6N)C7)ccn5)C4)CC3)no2)C(C)C)cc1] | (2S,4R)-1-((2R)-2-(3-(1-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)piperidin-4-yl)methyl)-1,7-diazaspiro[3.5]nonan-7-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 749 | 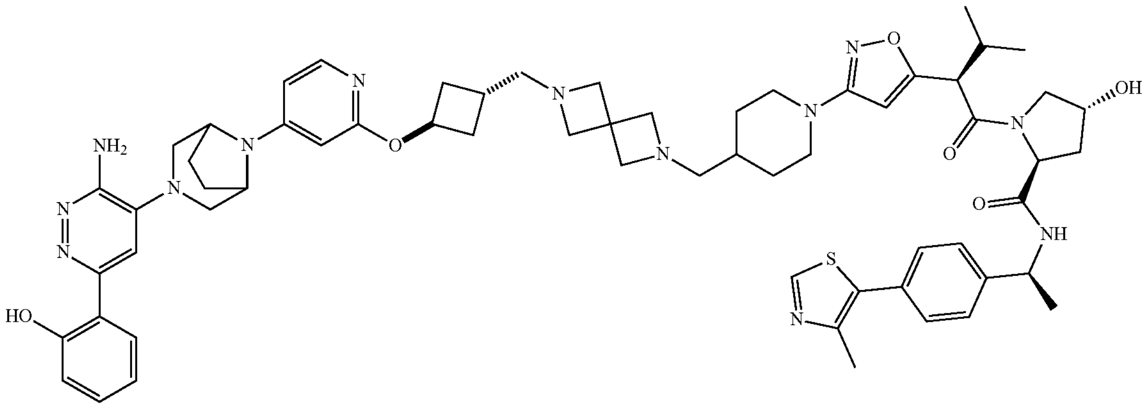 | (2S,4R)-1-((2R)-2-(3-(4-((6-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2,6-diazaspiro[3.3]heptan-2-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 750 | 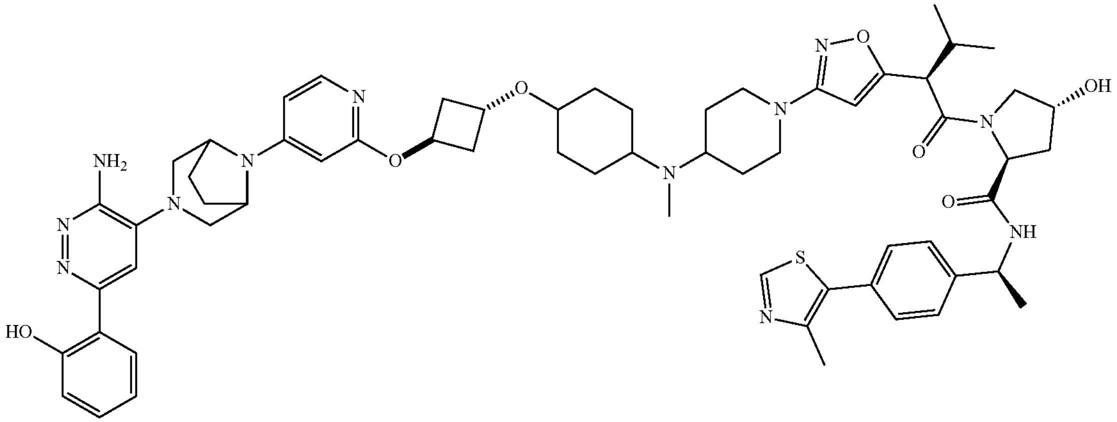 | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)(methyl)amino)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 751 | 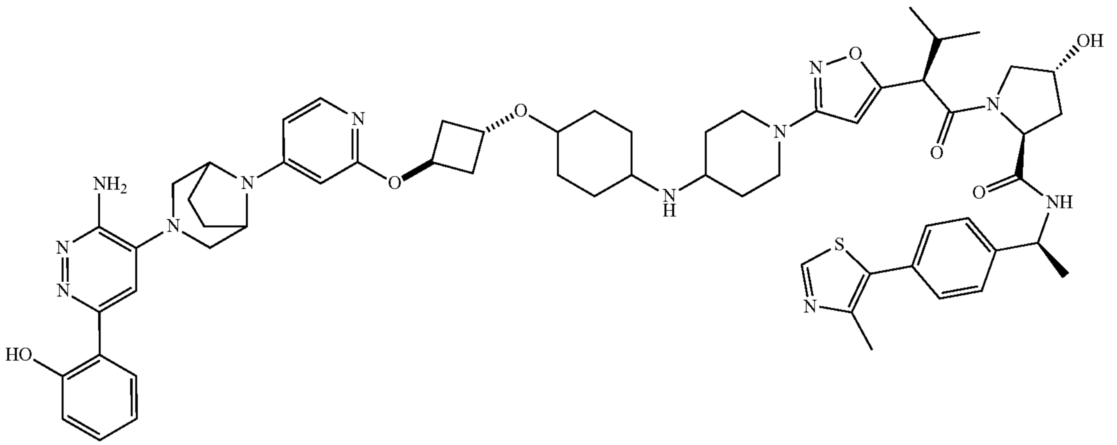 | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)cyclohexyl)amino)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 752 | 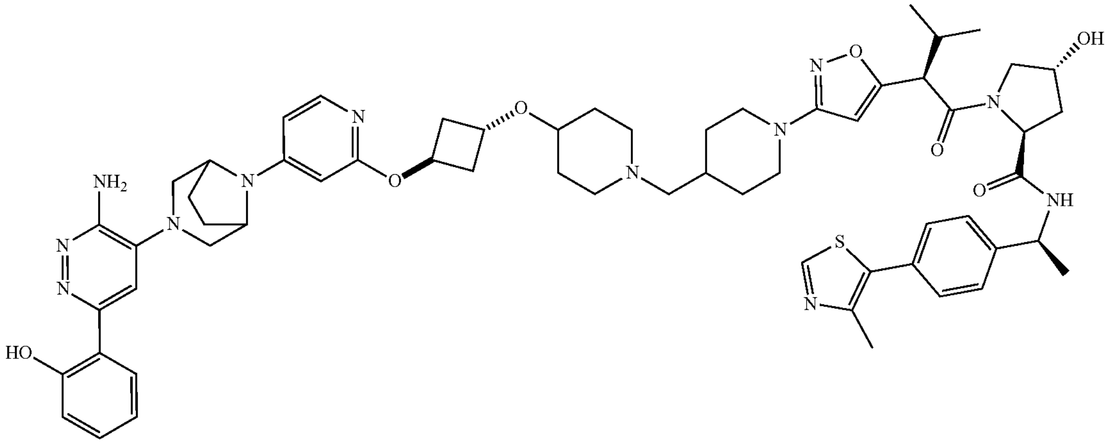 | (2S,4R)-1-((2R)-2-(3-(3-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)-8-azabicyclo[3.2.1]octan-8-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 753 | 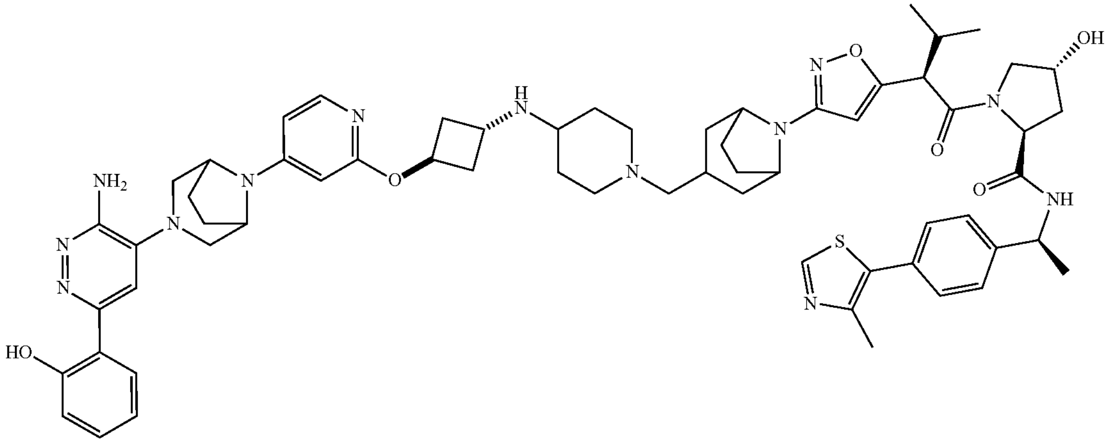 | (2S,4R)-1-((2R)-2-(3-(4-((4-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)amino)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 754 | 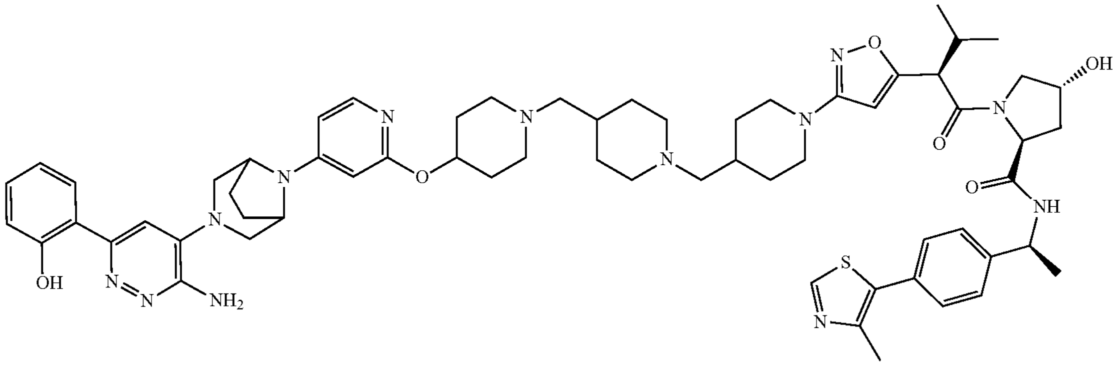 [SMILES: Cc1ncsc1-c1ccc([C@H](C)NC(=O)[C@@H]2C[C@@H](O)CN2C(=O)[C@@H](c2cc(N3CCC(CN4CCC(CN5CCC(Oc6cc(N7C8CCC7CN(c7cc(-c9ccccc9O)nnc7N)C8)ccn6)CC5)CC4)CC3)no2)C(C)C)cc1] | (2S,4R)-1-((2R)-2-(3-(4-((4-((4-((4-(3-(3-amino-6-(2-hydroxyphenyl)pyridazin-4-yl)-3,8-diazabicyclo[3.2.1]octan-8-yl)pyridin-2-yl)oxy)piperidin-1-yl)methyl)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 755 | 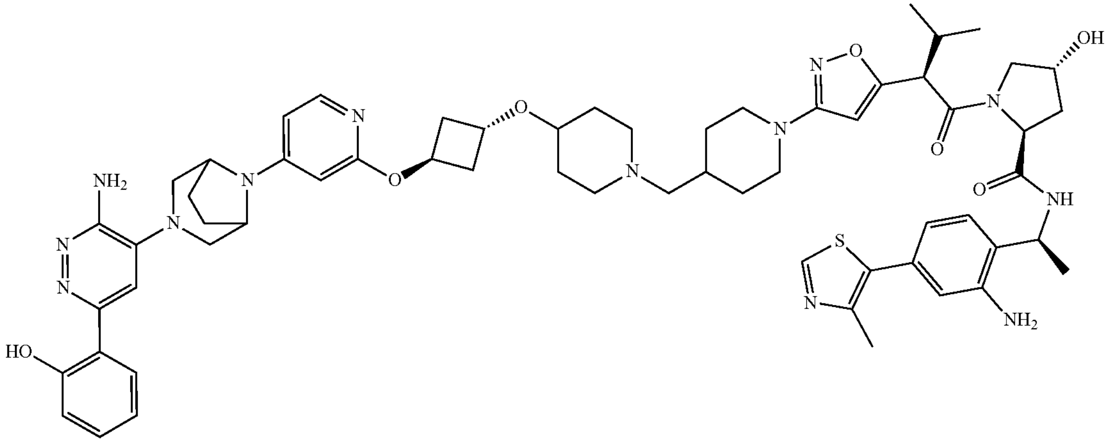 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)c(N)c1] | (2S,4R)-N-((S)-1-(2-amino-4-(4-methylthiazol-5-yl)phenyl)ethyl)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxypyrrolidine-2-carboxamide |

-continued

| Ex No | Structure | Name |
|---|---|---|
| []Exemplary bifunctional degradation compounds of the present disclosure | | |
| 756 | 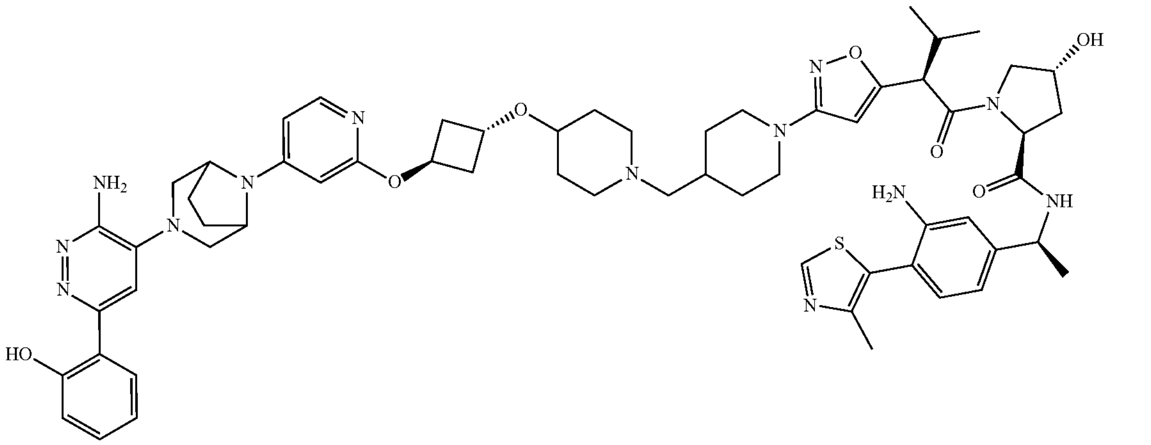 [SMILES: Cc1ncsc1-c1ccc([C@H](C)NC(=O)[C@@H]2C[C@@H](O)CN2C(=O)[C@@H](c2cc(N3CCC(CN4CCC(O[C@H]5C[C@H](Oc6cc(N7C8CCC7CN(c7cc(-c9ccccc9O)nnc7N)C8)ccn6)C5)CC4)CC3)no2)C(C)C)cc1N] | (2S,4R)-N-((S)-1-(3-amino-4-(4-methylthiazol-5-yl)phenyl)ethyl)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutoxy)piperidin-1-yl)methyl)piperidin-1-yl)isoxazol-5-yl)-3-methylbutanoyl)-4-hydroxypyrrolidine-2-carboxamide |
| 757 | 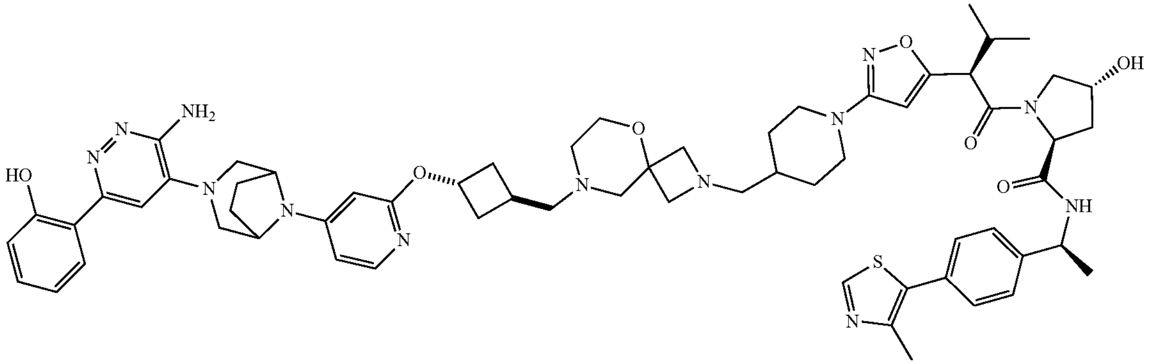 | (2S,4R)-1-((2R)-2-(3-(4-((8-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-5-oxa-2,8-diazaspiro[3.5]nonan-2-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 758 | 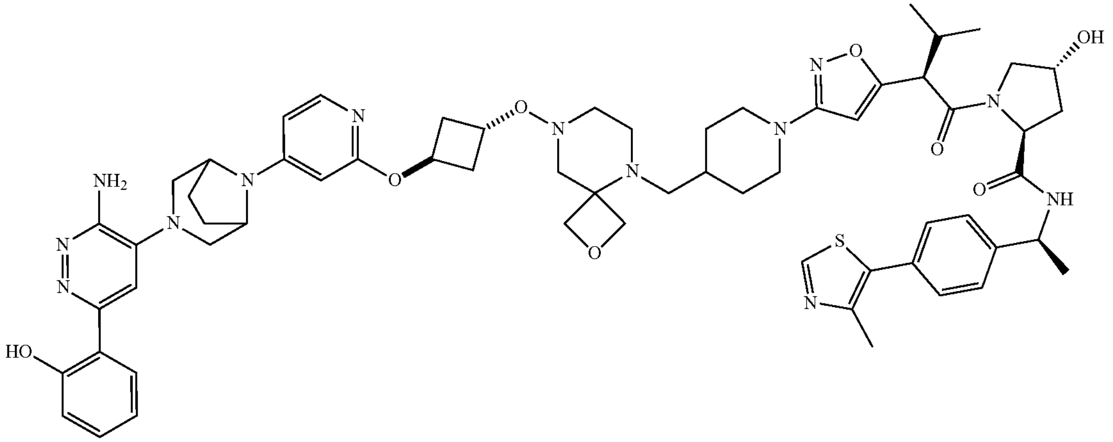 | (2S,4R)-1-((2R)-2-(3-(4-((8-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-oxa-5,8-diazaspiro[3.5]nonan-5-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 759 | 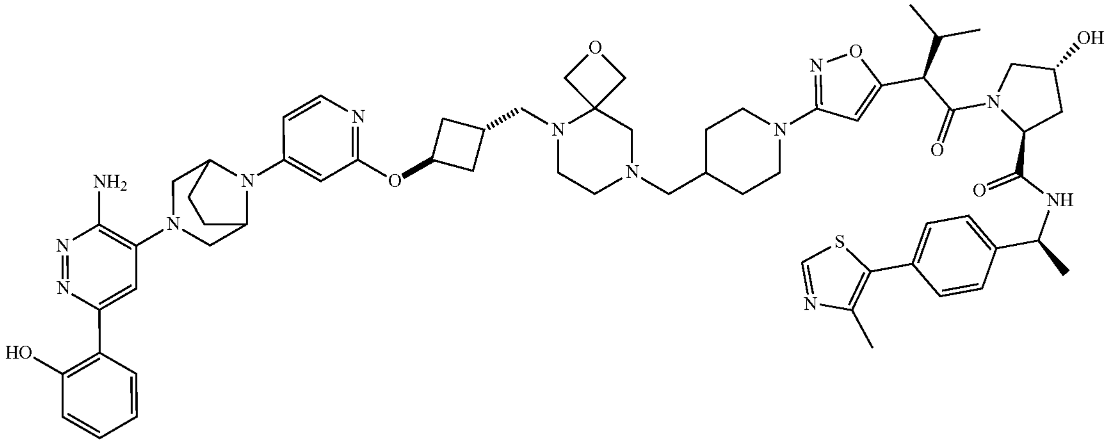 | (2S,4R)-1-((2R)-2-(3-(4-((5-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-2-oxa-5,8-diazaspiro[3.5]nonan-8-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| []Exemplary bifunctional degradation compounds of the present disclosure | | |
|---|---|---|
| Ex No | Structure | Name |
| 760 | 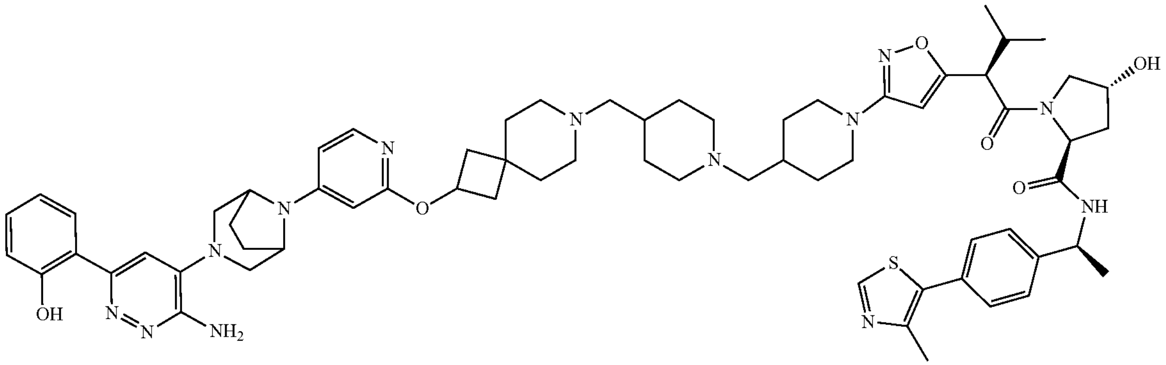 [SMILES: Cc1ncsc1-c1ccc([C@H](C)NC(=O)[C@@H]2C[C@@H](O)CN2C(=O)[C@@H](c2cc(N3CCC(CN4CCC(CN5CCC6(CC5)CC(Oc5cc(N7C8CCC7CN(c7cc(-c9ccccc9O)nnc7N)C8)ccn5)C6)CC4)CC3)no2)C(C)C)cc1] | (2S,4R)-1-((2R)-2-(3-(4-((4-((2-((4-(3-(3-amino-6-(2-hydroxyphenyl)pyridazin-4-yl)-3,8-diazabicyclo[3.2.1]octan-8-yl)pyridin-2-yl)oxy)-7-azaspiro[3.5]nonan-7-yl)methyl)piperidin-1-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 761 | 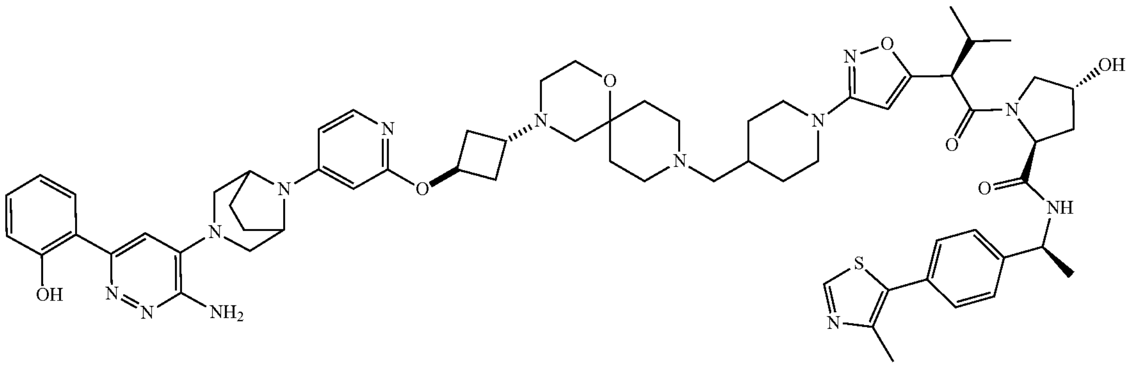 | (2S,4R)-1-((2R)-2-(3-(4-((4-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)-1-oxa-4,9-diazaspiro[5.5]undecan-9-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |

-continued

| Ex No | Structure | Name |
|---|---|---|
| []Exemplary bifunctional degradation compounds of the present disclosure | | |
| 762 | 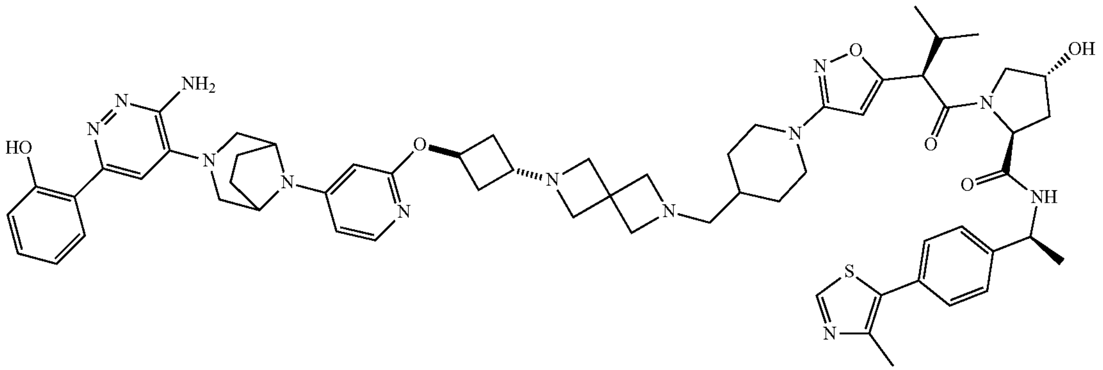 | (2S,4R)-1-((2R)-2-(3-(4-((6-((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)-2,6-diazaspiro[3.3]heptan-2-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 763 | 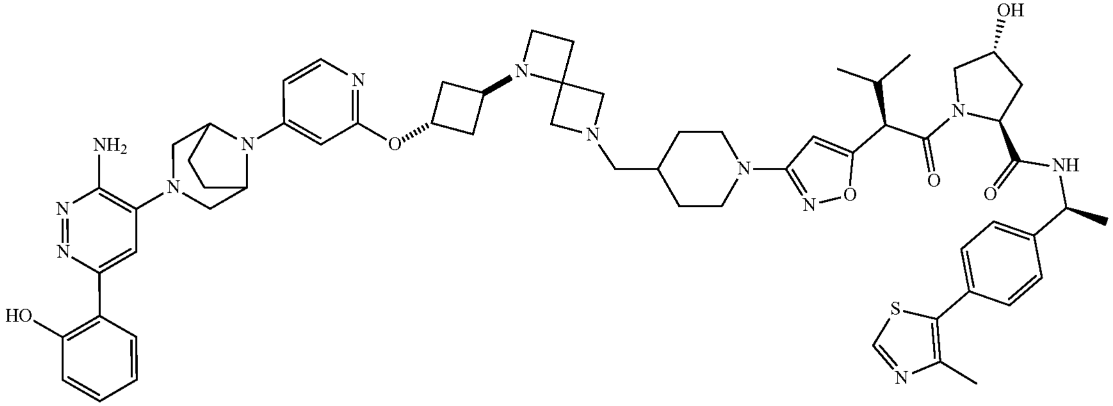 | (2S,4R)-1-((2R)-2-(3-(4-((1-((1r,3R)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)-1,6-diazaspiro[3.3]heptan-6-yl)methyl)piperidin-1-yl)isoxazol-5-yl)-3-methylbutanoyl)-4-hydroxy-N-((1S)-1-(4-(4-methyl-4,5-dihydrothiazol-5-yl)phenyl)ethyl)pyrrolidine-2-carboxamide |

-continued

[]Exemplary bifunctional degradation compounds of the present disclosure

| Ex No | Structure | Name |
|---|---|---|
| 764 | 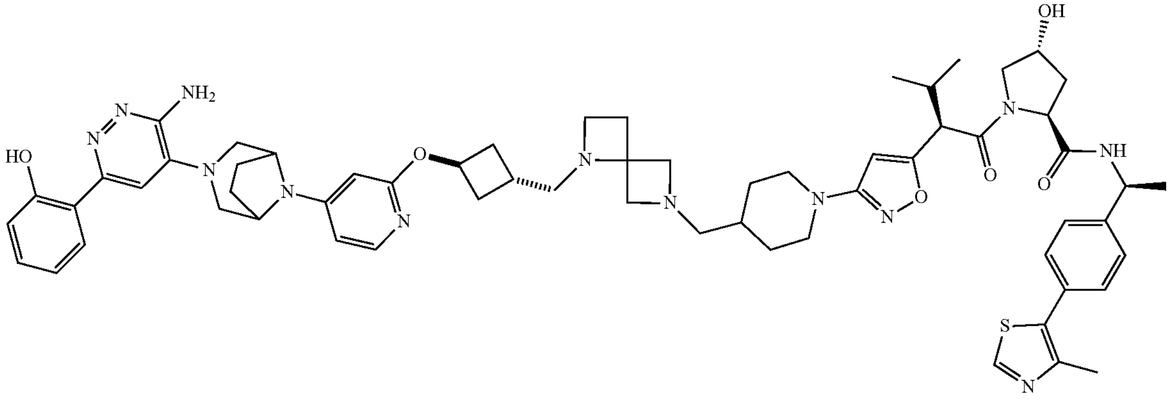 | (2S,4R)-1-((2R)-2-(3-(4-((1-(((1r,3r)-3-((4-(3-(3-amino-6-(2-hydroxyphenyl)pyridazin-4-yl)-3,8-diazabicyclo[3.2.1]octan-8-yl)pyridin-2-yl)oxy)cyclobutyl)methyl)-1,6-diazaspiro[3.3]heptan-6-yl)methyl)piperidin-1-yl)isoxazol-5-yl)-3-methylbutanoyl)-4-hydroxy-N-((S)-1-(4-(4-methylthiazol-5-yl)phenyl)ethyl)pyrrolidine-2-carboxamide |
| 765 | 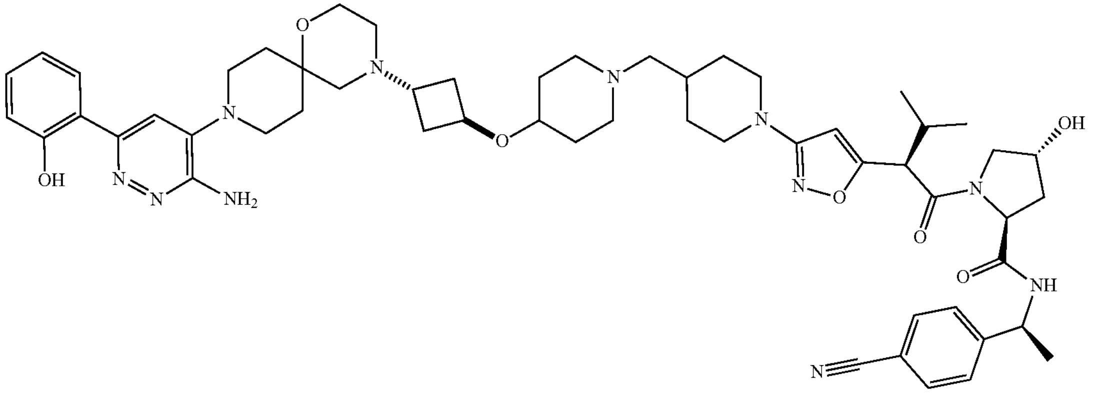 | (2S,4R)-1-((R)-2-(3-(4-((-((1r,3r)-3-(9-(3-amino-6-(2-hydroxyphenyl)pyridazin-4-yl)-1-oxa-4,9-diazaspiro[5.5]undecan-4-yl)cyclobutoxy)piperidin-1-yl)methyl)piperidin-1-yl)isoxazol-5-yl)-3-methylbutanoyl)-N-((S)-1-(4-cyanophenyl)ethyl)-4-hydroxypyrrolidine-2-carboxamide |

&1 stereochemical flag indicates the same relative configuration - as drawn - among the marked atoms, but with an equal amount of the opposite stereoisomer present (opposite absolute configurations at the marked atoms).

TABLE 2A

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| 1 | D | A | 856.5 | $^1$H NMR (400 MHZ, MeOD): δ 9.12 (s, 1H), 8.38-8.32 (m, 2H), 8.06 (s, 1H), 7.69 (d, J = 6.4 Hz, 1H), 7.48-7.45 (m, 5H), 7.07-7.03 (m, 2H), 4.86-4.35 (m, 7H), 4.00-3.80 (m, 6H), 3.60 (s, 9H), 2.50 (s, 3H), 2.30-2.20 (m, 1H), 2.18-2.03 (m, 1H), 1.04 (s, 9H). |
| 2 | D | A | 900.5 | $^1$H NMR (400 MHZ, CDCl3): δ 8.58 (s, 1H), 8.00 (s, 1H), 7.76 (s, 1H), 7.68 (s, 1H), 7.64(s, 1H), 7.55(d, J = 2.4 Hz, 1H), 7.24-7.54(m, 4H), 6.93(d, J = 8.4 Hz, 1H), 6.83(t, J = 7.9 Hz, 1H), 5.49(s, 1H), 4.69(t, J = 7.2 Hz, 1H), 4.48-4.51(m, 3H), 4.28-4.31(m, 3H), 3.8-3.98(m, 4H), 3.59-3.65(m, 16H), 2.43(s, 3H), 2.12-2.18(m, 1H), 1.39-1.43(m, 4H), 0.90(s, 9H). |
| 3 | D | A | 988.6 | $^1$H NMR (400 MHZ, $CDCl_3$): δ 8.64 (s, 1H), 8.03 (s, 1H), 7.79 (s, 1H), 7.72 (s, 1H), 7.54-7.58 (m, 2H), 7.19-7.26 (m, 4H), 6.95 (d, J = 7.6 Hz, 1H), 6.84 (t, J = 6.8 Hz, 1H), 5.42 (s, 2H), 4.65-4.67 (m, 1H), 4.44-4.48 (m, 3H), 4.32-4.38 (m, 3H), 3.81-3.99 (m, 5H), 3.49-3.51 (m, 22H), 2.42-2.49 (m, 4H), 2.10-2.15 (m, 1H), 0.89 (s, 9H). |
| 4 | D | A | 944.6 | $^1$H NMR (400 MHZ, CDCl3): δ 8.84 (s, 1H), 8.31 (s, 1H), 8.09 (s, 1H), 8.04 (s, 1H), 7.84(d, J = 7.6 Hz, 1H), 7.37-7.45(m, 4H), 7.26(d, J = 7.2 Hz, 1H), 6.93(d, J = 8.0 Hz, 2H), 4.67(s, 1H), 4.49-4.59(m, 3H), 4.31-4.42(m, 3H), 3.98(d, J = 6.0 Hz, 1H), 3.79-3.89(m, 3H), 3.52-3.61(m, 17H), 2.46(s, 3H), 2.08-2.21(m, 2H), 1.02(s, 9H). |
| 5 | D | A | 1032.6 | $^1$H NMR (400 MHZ, CD3OD): δ 8.85 (s, 1H), 8.59 (s, 1H), 8.31 (s, 1H), 8.09 (s, 1H), 8.05 (s, 1H), 7.84 (d, J = 7.6 Hz, 1H), 7.64 (d, J = 7.2 Hz, 1H),7.37-7.45 (m, 4H), 7.26 (m, 1H), 6.93-6.95 (m, 2H), 4.68 (d, J = 9.2 Hz, 1H), 4.55-4.60 (m, 1H), 4.45-4.59 (s, 2H), 4.41 (m, 2H), 4.30-4.36 (m, 1H), 4.00 (m, 2H), 3.90 (m, 3H), 3.82 (m, 1H), 3.55 (m, 25H), 2.45 (s, 3H), 2.23 (m,1H), 2.10 (m, 1H), 1.03 (s, 9H). |
| 6 | C | A | 993.6 | $^1$H NMR (400 MHZ, MeOD): δ§ 8.82 (s, 1H), 7.76-7.74 (m, 2H), 7.42-7.34 (m, 5H), 7.22-7.18 (m, 1H), 6.89-6.86 (m, 2H), 6.53-6.52 (m, 1H), 6.16 (s, 1H), 4.66-4.28 (m, 9H), 4.01-4.00 (m, 2H), 3.82-3.60 (m, 12H), 3.31-3.29 (m, 1H), 3.10-3.08 (m, 2H), 2.51-2.50 (m, 1H), 2.49 (s, 3H), 2.29-2.05 (m, 6H), 2.42-2.29 (m, 2H), 1.01 (s, 9H). |
| 7 | B | A | 1037.6 | $^1$H NMR (400 MHZ, MeOD): δ 8.83 (s, 1H), 7.77-7.76 (m, 2H), 7.44-7.35 (m, 5H), 7.28-7.20 (m, 1H), 6.90-6.88 (m, 2H), 6.57-6.50 (m, 1H), 6.19 (s, 1H), 4.84-4.25 (m, 9H), 4.01-3.98 (m, 2H), 3.89-3.70 (m, 4H), 3.65-3.61 (m, 12H), 3.30-3.28 (m, 2H, 3.10-3.00 (m, 2H), 2.35 (s, 3H), 2.18-1.99 (m, 6H), 1.02 (s, 9H). |
| 8 | C | A | 1125.5 | $^1$H NMR (400 MHZ, MeOD): δ 8.84 (s, 1H), 7.76-7.75 (m, 2H), 7.44-7.35 (m, 5H), 7.29-7.20 (m, 1H), 6.91-6.88 (m, 2H), 6.58-6.50 (m, 1H), 6.20 (s, 1H), 4.70-4.25 (m, 9H), 4.02-3.99 (m, 2H), 3.90-3.71 (m, 4H), 3.65-3.61 (m, 21H), 3.10-3.00 (m, 2H) , 2.45 (s, 3H), 2.23-2.00 (m, 6H), 1.02 (s, 9H). |
| 9 | B | A | 1081.5 | $^1$H NMR (400 MHZ, MeOD): δ 8.74 (s, 1H), 7.68-7.66 (m, 2H), 7.34-7.28 (m, 5H), 7.18-7.10 (m, 1H), 6.80-6.78 (m, 2H), 6.43-6.40 (m, 1H), 6.10 (s, 1H), 4.60-4.20 (m, 9H), 3.92-3.89 (m, 2H), 3.80-3.64 (m, 4H), 3.71-3.45 (m, 16H), 3.10-3.00 (m, 1H), 3.00-2.90 (m, 2H), 2.37-2.34 (m, 1H), 2.35 (s, 3H), 2.18-1.99 (m, 6H), 0.92 (s, 9H). |
| 10 | B | A | 1169.6 | $^1$H NMR (400 MHZ, MeOD): δ 8.84 (s, 1H), 7.77-7.76 (m, 2H), 7.44-7.38 (m, 5H), 7.29-7.20 (m, 1H), 6.91-6.89 (m, 2H), 6.58-6.50 (m, 1H), 6.18 (s, 1H), 4.70-4.25 (m, 9H), 4.02-3.99 (m, 2H), 3.90-3.71 (m, 4H), 3.65-3.61 (m, 25H), 3.10-3.00 (m, 2H), 2.45 (s, 3H), 2.24-2.00 (m, 6H), 1.02 (s, 9H). |
| 11 | D | A | 812.1 | 1H NMR (400 MHZ, MeOD) : δ 8.83 (s, 1H), 8.32 (s, 1H), 8.04 (d, J = 9.6 Hz, 2H), 7.78 (d, J = 7.6 Hz, 1H), 7.65 (d, J = 10.0 Hz, 1H), 7.39 (d, J = 8.0 Hz, 2H), 7.32-7.34 (m, 2H), 7.28 (m, 1H), 6.95 (d, J = 7.6 Hz 2H), 4.69 (d, J = 9.6 Hz 1H), 4.44-4.57 (m, 6H), 4.25-4.35 (m, 1H), 3.60-3.99 (m, 11H), 2.46 (s, 3H), 2.23 (m, 1H), 2.08 (m, 1H), 1.01 (s, 9H). |
| 12 | D | B | 960.4 | 1HNMR (400 MHZ, MeOD): δ§ 8.83 (s, 1H), 8.27 (s, 1H), 8.01 (d, J = 10.0 Hz, 2H), 7.75-7.77 (m, 2H), 7.48-7.59 (m, 4H), 7.36 (d, J = 7.6 Hz, 1H), 7.18-7.22 (m, 1H), 6.89-7.00(m, 4H), 4.36-4.58 (m, 9H), 4.15-4.16 (m, 2H), 3.83-3.96 (m, 6H), 3.46-3.56 (m, 8H), 2.45 (s, 3H), 2.43-2.44 (m, 1H), 2.22-2.23 (m, 1H), 2.10-2.11 (m, 1H), 1.02 (d, J = 6.8 Hz, 3H), 0.81 (d, J = 6.4 Hz, 3H). |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| 13 | D | A | 1004.4 | $^1$H NMR (400 MHZ, MeOD): δ 8.84 (s, 1H), 8.27 (s, 1H), 8.03(d, J = 13.2 Hz, 2H), 7.75-7.86 (m, 2H), 7.45-7.62 (m, 3H), 7.35-7.41 (m, 1H), 7.19-7.26 (m, 1H), 6.86-7.01 (m, 4H), 4.34-4.62 (m, 9H), 4.09-4.17 (m, 2H), 3.92-4.00 (m, 1H), 3.78-3.90 (m, 5H), 3.62(d, J = 8.0 Hz, 2H), 3.56(m, 10H), 2.46 (s, 4H), 2.12-2.21 (m, 1H), 1.98-2.09 (m, 1H), 1.03 (d, J = 6.4 Hz, 3H), 0.82(d, J = 6.4 Hz, 3H). |
| 14 | | C | 852.3 | $^1$H NMR (300 MHZ, $CD_3OD$): δ 8.82 (d, J = 11.1 Hz, 1H), 8.29-8.18 (m, 1H), 8.11-7.89 (m, 2H), 7.80 (d, J = 8.2 Hz, 1H), 7.48-7.41 (m, 1H), 7.37-7.30 (m, 3H), 7.30-7.19 (m, 1H), 6.95-6.83 (m, 2H), 5.89 (s, 1H), 4.59-4.41 (m, 2H), 4.40-4.30 (m, 4H), 4.27-4.11 (m, 2H), 3.86 (q, J = 5.3 Hz, 2H), 3.75-3.59 (m, 6H), 3.56 (s, 3H), 2.42 (d, J = 5.0 Hz, 3H), 2.36-2.10 (m, 2H), 2.04-2.01 (m, J = 13.1, 8.1, 4.7 Hz, 1H), 1.26 (s, 1H), 0.99 (d, J = 6.6 Hz, 3H), 0.83 (d, J = 6.8 Hz, 3H) |
| 15 | C | A | 852.3 | $^1$H NMR (300 MHZ, $CD_3OD$): δ 8.82 (d, J = 6.6 Hz, 1H), 8.26 (dd, J = 3.1, 0.8 Hz, 1H), 8.10-7.96 (m, 2H), 7.86-7.75 (m, 1H), 7.45-7.30 (m, 4H), 7.25-7.22 (m, 1H), 6.96-6.84 (m, 2H), 5.88 (s, 1H), 4.70-4.42 (m, 3H), 4.41-4.33 (m, 3H), 4.28-4.17 (m, 2H), 3.87 (t, J = 5.0 Hz, 3H), 3.85-3.63 (m, 2H), 3.59-3.57 (m, 6H), 2.41 (d, J = 12.2 Hz, 3H), 2.38-2.33(m, 1H), 2.25-2.12 (m, 1H), 2.06-2.02 (m, 1H), 1.26 (s, 1H), 0.97 (dd, J = 6.6, 1.8 Hz, 3H), 0.80 (dd, J = 6.6, 1.8 Hz, 3H). |
| 16 | D | B | 896.3 | $^1$H NMR (300 MHZ, Methanol-d4) δ 8.83 (d, J = 9.2 Hz, 2H), 8.32-8.23 (m, 2H), 8.10-7.96 (m, 4H), 7.85-7.75 (m, 2H), 7.44 (s, 1H), 7.40-7.17 (m, 8H), 6.96-6.84 (m, 4H), 5.89 (s, 2H), 4.50-4.48 (m, 5H), 4.41-4.31 (m, 7H), 4.19-4.09 (m, 3H), 3.86-3.84 (m, 4H), 3.75-3.49 (m, 25H), 2.43 (d, J = 4.1 Hz, 6H), 2.18 (d, J = 11.3 Hz, 1H), 2.10-1.95 (m, 1H), 1.00 (d, J = 6.6 Hz, 5H), 0.85 (d, J = 6.7 Hz, 5H). |
| 17 | B | A | 896.3 | $^1$H NMR (300 MHZ, Methanol-d4) δ 8.83 (d, J = 4.8 Hz, 1H), 8.28 (d, J = 5.2 Hz, 1H), 8.10-7.96 (m, 2H), 7.87-7.78 (m, 1H), 7.40 (s, 4H), 7.23-7.21 (m, 1H), 6.96-6.84 (m, 2H), 5.87 (s, 1H), 4.55-4.32 (m, 6H), 4.24-4.14 (m, 2H), 3.91-3.79 (m, 3H), 3.73-3.52 (m, 12H), 2.42 (d, J = 9.1 Hz, 3H), 2.33-2.31 (m, 1H), 2.21-1.99 (m, 2H), 0.98-0.96 (m, 3H), 0.81 (d, J = 6.7 Hz, 3H). |
| 18 | D | B | 940.3 | $^1$H NMR (300 MHZ, $CD_3OD$): δ 8.82-8.81 (m, 1H), 8.30-8.26 (m, 1H), 8.08-7.99 (m, 2H), 7.82-7.80 (m, 1H), 7.44-7.30 (m, 4H), 7.26-7.19 (m, 1H), 6.92-6.87 (m, 2H), 5.91-5.89 (m, 1H), 4.58-4.49 (m, 1H), 4.48-4.41 (m, 1H), 4.40-4.31 (m, 4H), 4.20-4.11 (m, 2H), 3.88-3.82 (m, 2H), 3.73-3.60 (m, 5H), 3.60-3.54 (m, 4H), 3.54-3.43 (m, 8H), 2.43 (s, 3H), 2.37-2.14 (m, 2H), 2.08-1.98 (m, 1H), 1.01-0.84 (m, 6H) |
| 19 | C | A | 940.3 | $^1$H NMR (300 MHZ, $CD_3OD$): δ 8.83 (s, 1H), 8.28 (s, 1H), 8.07-8.05 (m, 2H), 8.01-7.99 (m, 1H), 7.40-7.38 (m, 4H), 7.23-7.20 (m, 1H), 6.92-6.90 (m, 2H), 5.91-5.87 (m, 1H), 4.50-4.36 (m, 6H), 4.21-4.18 (m, 2H) , 3.88-3.83 (m, 3H), 3.71-3.65 (m, 2H), 3.62-3.52 (m, 14H), 2.44 (s, 3H), 2.38-2.26 (m, 1H), 2.23-2.13 (m, 1H), 2.10-2.00 (m, 1H), 1.00-0.98 (m, 3H), 0.83-0.81 (m, 3H) |
| 20 | D | B | 1048.4 | $^1$H NMR (400 MHZ, MeOD): δ§ 8.84 (s, 1H), 8.28 (s, 1H), 8.05 (d, J = 12.4 Hz, 2H), 7.38-7.81 (m, 6H), 7.36-7.37 (m, 1H), 6.98-7.00(m, 2H), 6.92 (d, J = 7.6 Hz, 2H), 4.37-4.59 (m, 9H), 4.15-4.16 (m, 2H), 3.83-3.96 (m, 6H), 3.46-3.56 (m, 16H), 2.46 (s, 3H), 2.44-2.45 (m, 1H), 2.21-2.22 (m, 1H), 2.09-2.10 (m, 1H), 1.03 (d, J = 6.4 Hz, 3H), 0.82 (d, J = 6.4 Hz, 3H). |
| 21 | | C | 916.4 | $^1$H NMR (400 MHZ, MeOD): δ 8.79 (s, 1H), 8.25 (s, 1H), 7.98 (s, 2H), 7.75 (t, J = 16.0 Hz, 2H), 7.46-7.57 (m, 3H), 7.32 (d, J = 8.0 Hz, 1H), 7.22 (t, J = 7.2 Hz, 1H), 6.90-6.94 (m, 4H), 4.38-4.56 (m, 9H), 4.12-4.13 (m, 2H), 3.97 (s, 1H), 3.84-3.90 (m, 5H), 3.65-3.71(m, 4H), 2.42(m, 4H), 2.13-2.21 (m, 1H), 1.98-2.09 (m, 1H), 1.02 (d, J = 6.8 Hz, 3H), 0.80 (d, J = 6.8 Hz, 3H). |
| 22 | D | A | 850.3 | $^1$H-NMR: (400 MHZ, $CD_3OD$ ) 88.89-8.83 (m, 1H), 8.31-8.26 (m, 1H), 8.08-8.03 (m, 2H), 7.85-7.81 (m, 1H), 7.46-7.21 (m, 5H), 6.96-6.87 (m, 2H), 6.15 (s, 1H), 4.52-4.44 (m, 5H), 4.41-4.31 (m, 3H), 3.91-3.80 (m, 2H), 3.72-3.65 (m, 1H), 3.61-3.35 (m, 6H), 2.62-2.51 (m, 2H), 2.45-2.33 (m, 3H), 2.22-2.15 (m, 1H), 2.10-2.01 (m, 1H), 1.84-1.72 (m, 2H), 1.30-1.24 (m, 1H), 1.03-0.97 (m, 3H), 0.91-0.75 (m, 3H). |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| 23 | D | A | 894.6 | $^1$H-NMR: (400 MHZ, $CD_3OD$ ) δ 8.89-8.83 (m, 1H), 8.31-8.26 (m, 1H), 8.08-8.03 (m, 2H), 7.85-7.81 (m, 1H), 7.46-7.21 (m, 5H), 6.96-6.87 (m, 2H), 6.15 (s, 1H), 4.52-4.31 (m, 6H), 3.91-3.80 (m, 3H), 3.72-3.65 (m, 2H), 3.61-3.40 (m, 9H), 2.62-2.51 (m, 2H), 2.45-2.33 (m, 4H), 2.22-2.15 (m, 1H), 2.10-2.01 (m, 1H), 1.84-1.72 (m, 2H), 1.28-1.25 (m, 1H), 1.05-1.00 (m, 3H), 0.88-0.83 (m, 3H). |
| 24 | B | A | 894.6 | 8.88 (s, 1H), 8.37 (s, 1H), 8.31 (s, 1H), 8.04 (s, 1H), 7.69-7.67 (d, J = 8.1Hz, ppm), 7.43-7.39 (m, 5H), 7.03-6.99 (m, 2H), 6.21-6.00 (m, 1H), 4.53-4.48 (m, 3H), 4.44-4.40 (m, 3H), 3.92-3.89 (m, 3H), 3.79-3.76 (m, 1H), 3.62-3.54 (m, 7H), 3.50-3.48 (m, 2H), 3.42-3.40 (m, 2H), 2.64-2.61 (m, 2H), 2.46-2.44 (m, 4H), 2.26-2.18 (m, 1H), 2.13-2.04 (m, 1H), 1.82-1.78 (m, 2H), 1.05-1.02 (d, J = 6.6 Hz, 3H), 0.85-0.82 (d, J = 6.9Hz, 3H) |
| 25 | D | A | 938.4 | $^1$H NMR: (400 MHZ, $CD_3OD$ ) 88.89-8.86 (m, 1H), 8.33-8.29 (m, 1H), 8.11-8.04 (m, 2H), 7.89-7.83 (m, 1H), 7.49-7.23 (m, 5H), 6.99-6.91 (m, 2H), 6.22 (s, 1H), 4.62-4.59 (m, 3H), 4.50-4.37 (m, 5H), 3.95-3.88 (m, 3H), 3.73-3.68 (m, 2H), 3.64-3.41 (m, 13H), 3.34-3.31 (m, 2H), 2.62-2.54 (m, 2H), 2.41-2.21 (m, 2H), 2.09-2.02 (m, 1H), 1.82-1.74 (m, 2H), 1.09-1.02 (m, 3H), 0.91-0.85 (m, 3H) |
| 26 | C | A | 938.4 | $^1$H NMR: (400 MHZ, $CD_3OD$ ) 88.89 (s, 1H), 8.31 (s, 1H), 8.14-8.06 (m, 2H), 7.89-7.85 (m, 1H), 7.49-7.41 (m, 4H), 7.29-7.23 (m, 1H), 6.99-6.92 (m, 2H), 6.23 (s, 1H), 4.62-4.47 (m, 4H), 4.42-4.37 (m, 3H), 3.94-3.91 (m, 3H), 3.79-3.73 (m, 1H), 3.64-3.42 (m, 13H), 3.41-3.35 (m, 2H), 2.68-2.61 (m, 2H), 2.46 (s, 3H), 2.23-2.16 (m, 1H), 2.11-2.02 (m, 1H), 1.86-1.78 (m, 2H), 1.08-1.02 (m, 3H), 0.88-0.83 (m, 3H) |
| 27 | D | A | 989.3 | $^1$H NMR (400 MHZ, CD3OD): δ 8.85 (m, 1H), 7.78-7.72(m, 2H), 7.47-7.45(m, 2H), 7.40-7.34 (m, 3H), 7.23-7.22 (m, 1H), 6.92-6.88 (m, 2H), 6.55-6.53(m, 1H), 6.23 (s, 1H), 5.97 (s, 1H), 4.64-4.59(m, 2H), 4.50(s, 3H), 4.40(s, 2H), 4.33-4.24 (m, 4H), 3.81-3.79 (m, 2H), 3.75-3.65(m, 8H), 3.29 (m, 1H), 3.10-3.07(m, 2H), 2.48-2.46(m, 3H), 2.23-2.20(m,1H),2.13-2.06(m, 6H), 1.05(s, 1H), 0.90-0.89 (d, J = 6.8Hz, 3H), 0.78-0.76 (d, J = 8Hz,3H) |
| 28 | A | A | 989.3 | $^1$H NMR (400 MHZ, CD3OD): δ 8.88 (m, 1H), 7.79-7.75(m, 2H), 7.49-7.39(m, 5H), 7.24(m, 1H), 6.92-6.90 (m, 2H), 6.56-6.54(m, 1H), 6.25-6.24 (M, 1H), 6.00 (s, 1H), 4.53-4.29(m, 10H), 3.88-3.81 (m, 5H), 3.70-3.63(m, 6H), 3.33(m, 2H), 3.14-3.12(m, 2H), 2.48-2.44(m, 3H), 2.42-2.29(m,1H),2.25-2.12(m, 6H), 1.04-1.02 (d, J = 6.4Hz, 3H), 0.88-0.86 (d, J = 6.4Hz, 3H) |
| 29 | C | A | 1033.4 | $^1$H NMR (400 MHZ, $CD_3OD$): δ 8.85 (m, 1H), 7.76-7.74 (m, 2H), 7.45-7.42 (m, 2H), 7.38-7.32 (m, 3H), 7.23-7.22 (m, 1H), 6.90-6.87 (m, 2H), 6.55-6.53 (m, 1H), 6.24 (s, 1H), 5.96 (s, 1H), 4.72-4.46 (m, 4H), 4.41-4.31 (m, 4H), 4.20-4.16 (m, 2H), 3.81-3.78 (m, 2H), 3.74-3.69 (m, 5H), 3.66-3.57 (m, 9H), 3.09-3.06 (m, 2H), 2.45-2.44 (m, 3H), 2.40-2.30 (m, 1H), 2.22-2.20 (m, 3H), 2.18-2.06 (m, 3H), 1.28-1.24 (m, 1H), 1.03-1.02 (d, J = 6.8Hz,3H), 0.88-0.87 (d, J = 6.4Hz, 3H) |
| 30 | A | A | 1033.4 | $^1$H NMR (400 MHZ, $CD_3OD$): δ 8.85 (m, 1H), 7.78-7.66 (m, 2H), 7.53 (s, 1H), 7.42-7.39 (m, 4H), 7.32-7.27 (m, 1H), 6.94-6.87 (m, 2H), 6.79-6.74 (m, 1H), 6.51-6.50 (m, 1H), 5.98 (s, 1H), 4.85-4.79 (m, 3H), 4.56-4.41 (m, 5H), 4.30-4.24 (m, 2H), 3.88-3.86 (m, 4H), 3.77-3.58 (m, 12H), 3.18-3.11 (m, 2H), 2.45-2.42 (m, 3H), 2.31-2.29 (m, 3H), 2.29-2.20 (m, 3H), 2.16-2.00 (m, 1H), 1.29 (m, 1H), 1.03-1.01 (d, J = 6.4Hz, 3H), 0.86-0.84 (d, J = 6.8Hz, 3H) |
| 31 | C | A | 1092.4 | $^1$H NMR (400 MHZ, CD3OD): δ 8.87 (s, 1H), 8.20-8.70(b, 1H), 8.05-8.00(m, 2H), 7.74-7.71(m, 1H), 7.53-7.32(m, 5H), 7.28-7.17(m, 1H), 7.09-7.00 (m, 2H), 6.91-6.87 (m, 2H), 6.76-6.74(m, 1H), 4.63-4.47(m, 4H), 4.36-4.32(m, 1H), 3.85-3.62(m, 5H), 3.57-3.41(m, 10H), 3.14-3.07(m, 2H), 2.90-2.88 (m, 2H), 2.77-2.62(m, 6H), 2.46(s, 3H), 2.38-2.24(m, 2H), 2.23-2.11(m, 3H), 2.08-1.96(m, 3H), 1.28(m, 1H), 1.00-0.98(m, 9H) |
| 32 | D | A | 979.3 | $^1$H NMR: (400 MHZ, $CD_3OD$ ) δ 8.00 (s, 1H), 7.77-7.76 (d, J = 7.2 Hz, 1H), 7.43-7.32 (m, 5H), 7.23 (s, 1H), 7.15 (s, 1H), 6.91-6.87 (t, J = 14.4 Hz, 2H), 6.00-5.91 (q, J = 18.8 Hz, 2H), 4.79 (s, 1H), 4.67 (s, 1H), 4.56-4.50 (t, J = 24.8 Hz, 3H), 4.36-4.30 (m, 3H), 4.02-3.99 (t, J = 11.2 Hz, 2H), 3.89-3.85 (q, J = 15.2 Hz, 2H), 3.80-3.72 (m, 3H), 3.63-3.59 (t, J = 17.2 Hz, 10H), 3.47-3.45 (d, J = 9.2 Hz, 2H), 2.45-2.44 (d, J = 6.4 Hz, 3H), 2.11-2.08 (m, 4H), 1.02-0.99 (d, J = 9.6 Hz, 9H) |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| 33 | B | A | 886.3 | $^1$H NMR (300 MHZ, Methanol-d4) δ 8.79 (s, 1H), 8.35-8.23 (m, 1H), 8.09-7.97 (m, 2H), 7.80 (d, J = 7.7 Hz, 1H), 7.43-7.37 (m, 2H), 7.31 (d, J = 8.1 Hz, 2H), 7.24 (d, J = 8.1 Hz, 1H), 7.20 (s, 4H), 6.89 (t, J = 7.6 Hz, 2H), 5.64-5.52 (m, 1H), 4.66 (s, 1H), 4.60-4.44 (m, 3H), 4.27 (d, J = 15.5 Hz, 1H), 3.92 (d, J = 4.6 Hz, 2H), 3.88-3.74 (m, 2H), 3.52 (d, J = 6.2 Hz, 2H), 2.71 (t, J = 7.6 Hz, 2H), 2.37 (s, 3H), 2.18 (d, J = 7.7 Hz, 1H), 2.07 (dd, J = 9.4, 4.2 Hz, 1H), 1.89 (dd, J = 7.3, 1.2 Hz, 6H), 1.26 (s, 1H), 1.10-0.95 (d, J = 1.6 Hz, 9H), 0.95-0.90 (m, 1H). |
| 34 | D | A | 944.4 | $^1$H NMR: (400 MHz, $CD_3OD$ ) δ 8.85 (s, 1H), 7.82-7.80 (d, J = 8.4 Hz, 1H), 7.64 (s, 1H), 7.49-7.39 (m, 6H), 7.27-7.25 (m, 1H), 6.96-6.93 (m, 2H), 4.70 (s, 1H), 4.60-4.50 (m, 4H), 4.46-4.44 (m, 4H), 4.36-4.32 (m, 1H), 4.10-4.04 (m, 4H), 3.90-3.82 (m, 4H), 3.72-3.68 (m, 7H), 2.47 (m, 3H), 2.21-2.15 (m, 1H), 2.13-2.05 (m, 3H), 1.93-1.90 (m, 2H), 1.31 (s, 2H) 1.05 (s, 9H) |
| 35 | B | A | 1183.6 | $^1$H NMR: (300 MHz, $CD_3OD$, ppm) δ 8.86 (s, 1H), 7.79-7.73 (m, 2H), 7.48-7.41 (m, 5H), 7.23-7.20 (m, 1H), 6.91-6.89 (m, 2H), 6.58-6.55 (m, 1H), 6.24 (s, 1H), 5.01-4.99 (m, 1H), 4.68 (s, 1 H), 4.57-4.53 (m, 3H), 4.44-4.33 (m, 3H), 4.03 (s, 2H), 3.83-3.80 (m, 3H), 3.76-3.59 (m, 27H), 3.13-3.09 (m, 2H), 2.46 (s, 3H), 2.46-2.16 (m, 5H), 2.03-1.91 (m, 1H), 1.51-1.49 (m, 3H), 1.04 (s, 9H). |
| 36 | D | B | 968.4 | $^1$H NMR (400 MHZ, $CD_3OD$) δ 8.88 (d, J = 1.7 Hz, 1H), 7.79 (dd, J = 8.3, 1.6 Hz, 1H), 7.56-7.36 (m, 6H), 7.26 (ddd, J = 8.6, 7.3, 1.5 Hz, 1H), 6.98-6.89 (m, 2H), 6.01 (s, 1H), 4.64-4.44 (m, 4H), 4.30 (tq, J = 11.0, 6.8, 5.5 Hz, 2H), 3.86-3.47 (m, 12H), 3.25 (m, 2H), 3.07 (t, J = 11.0 Hz, 2H), 2.49 (d, J = 4.4 Hz, 2H), 2.42-2.19 (m, 8H), 2.18-2.03 (m, 4H), 1.89-1.78 (m, 2H), 1.66-1.58 (m, 4H), 1.30 (d, J = 10.2 Hz, 1H), 1.06 (d, J = 6.6 Hz, 3H), 0.92 (d, J = 6.7 Hz, 3H) |
| 37 | B | A | 968.4 | $^1$H NMR (400 MHZ, $CD_3OD$) δ 8.88 (d, J = 1.7 Hz, 1H), 7.79 (dd, J = 8.3, 1.6 Hz, 1H), 7.56-7.36 (m, 6H), 7.26 (ddd, J = 8.6, 7.3, 1.5 Hz, 1H), 6.98-6.89 (m, 2H), 6.01 (s, 1H), 4.64-4.44 (m, 4H), 4.30 (tq, J = 11.0, 6.8, 5.5 Hz, 2H), 3.86-3.47 (m, 12H), 3.25 (m, 2H), 3.07 (t, J = 11.0 Hz, 2H), 2.49 (d, J = 4.4 Hz, 2H), 2.42-2.19 (m, 8H), 2.18-2.03 (m, 4H), 1.89-1.78 (m, 2H), 1.66-1.58 (m, 4H), 1.30 (d, J = 10.2 Hz, 1H), 1.06 (d, J = 6.6 Hz, 3H), 0.92 (d, J = 6.7 Hz, 3H) |
| 38 | C | A | 1026.5 | $^1$H NMR (300 MHZ, Methanol-d4) δ 8.89 (s, 1H), 7.85-7.72 (m, 2H), 7.56-7.36 (m, 6H), 7.31-7.16 (m, 2H), 6.97-6.85 (m, 2H), 6.58 (dd, J = 6.2, 2.2 Hz, 1H), 6.24 (d, J = 2.1 Hz, 1H), 5.05 (q, J = 6.9 Hz, 1H), 4.67 (d, J = 10.6 Hz, 1H), 4.60-4.47 (m, 3H), 4.46 (s, 1H), 4.39 (t, J = 5.4 Hz, 2H), 4.06 (t, J = 5.3 Hz, 2H), 3.87 (dd, J = 10.9, 4.2 Hz, 1H), 3.76 (s, 1H), 3.73-3.55 (m, 2H), 3.19-2.99 (m, 2H), 2.92-2.69 (m, 12H), 2.50 (s, 4H), 2.30-2.14 (m, 5H), 1.98 (ddd, J = 13.2, 8.7, 4.6 Hz, 1H), 1.54 (d, J = 7.0 Hz, 3H), 1.41-1.26 (m, 4H), 1.20 (t, J = 7.0 Hz, 2H), 1.08 (d, J = 6.5 Hz, 3H), 0.93 (d, J = 4.1 Hz, 1H) |
| 39 | D | A | 1026.5 | $^1$H NMR (300 MHz, Methanol-d4) δ 8.88 (d, J = 13.8 Hz, 1H), 7.85-7.69 (m, 2H), 7.59-7.30 (m, 6H), 7.32-7.18 (m, 2H), 6.97-6.84 (m, 2H), 6.57 (dd, J = 6.1, 2.1 Hz, 1H), 6.23 (t, J = 2.7 Hz, 1H), 4.99 (q, J = 7.0 Hz, 1H), 4.78 (d, J = 8.8 Hz, 1H), 4.60 (t, J = 8.2 Hz, 1H), 4.53 (s, 2H), 4.37 (dd, J = 6.8, 4.1 Hz, 3H), 4.04 (t, J = 5.3 Hz, 2H), 3.64 (p, J = 6.7 Hz, 3H), 3.40-3.24 (m, 1H), 3.11 (dd, J = 15.8, 4.6 Hz, 2H), 2.88-2.64 (m, 12H), 2.49 (d, J = 13.8 Hz, 4H), 2.34-2.10 (m, 6H), 2.06 (s, 1H), 1.95 (td, J = 8.5, 4.2 Hz, 1H), 1.50 (d, J = 7.0 Hz, 3H), 1.33 (td, J = 7.8, 7.4, 4.4 Hz, 5H), 1.20 (t, J = 7.0 Hz, 3H), 1.08 (d, J = 6.7 Hz, 3H), 0.93 (q, J = 6.8 Hz, 1H), 0.74 (dd, J = 19.3, 6.7 Hz, 3H) |
| 40 | D | C | 1059.4 | $^1$H NMR (300 MHz, CD3OD): δ 8.86 (s, 1H), 8.06 (d, J = 6.1 Hz, 1H), 7.73 (dd, J = 7.9, 1.6 Hz, 1H), 7.50 0-7.37 (m, 5H), 7.24 (ddd, J = 8.3, 7.2, 1.5 Hz, 1H), 6.95-6.85 (m, 2H), 6.82-6.71 (m, 2H), 4.71 (s, 1H), 4.64-4.45 (m, 5H), 4.37 (d, J = 15.5 Hz, 1H), 4.12-3.98 (m, 2H), 3.91-3.76 (m, 2H), 3.76-3.60 (m, 6H), 3.43-3.33 (m, 3H), 3.11 (d, J = 11.6 Hz, 2H), 2.69 (t, J = 7.4 Hz, 2H), 2.61 (t, J = 5.7 Hz, 3H), 2.54 (s, 7H), 2.41 (dd, J = 9.4, 6.2 Hz, 3H), 2.32-2.05 (m, 6H), 1.91 (td, J = 14.8, 7.2 Hz, 2H), 1.05 (s, 9H) |
| 41 | C | A | 1013.6 | $^1$H NMR (300 MHz, DMSO-$d_6$) δ 14.11 (s, 1H), 8.94 (d, J = 2.6 Hz, 1H), 8.42 (d, J = 6.0 Hz, 1H), 7.88 (d, J = 8.0 Hz, 1H), 7.75 (d, J = 5.9 Hz, 1H), 7.49-7.12 (m, 6H), 6.81 (dd, J = 10.7, 7.9 Hz, 2H), 6.49 (d, J = 5.9 Hz, 1H), 6.12 (s, 1H), 6.03-5.93 (m, 3H), 5.09 (d, J = 3.7 Hz, 1H), 4.49-4.31 (m, 3H), 4.29-4.07 (m, 6H), 3.72 (d, J = 8.6 Hz, 1H), 3.38 (s, 6H), 3.18 (s, 2H), 2.98 (d, J = |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| | | | | 11.6 Hz, 2H), 2.64-2.50 (m, 3H), 2.45-2.33 (m, 11H), 2.14-1.93 (s, 8H), 1.18 (d, J = 15.2 Hz, 1H), 1.07 (d, J = 1.3 Hz, 1H), 0.93-0.63 (d, J = 6.6 Hz, 6H) |
| 42 | A | A | 1013.6 | $^1$H NMR (300 MHz, DMSO-$d_6$) δ 14.11 (s, 1H), 8.94 (d, J = 3.6 Hz, 1H), 8.48 (t, J = 5.9 Hz, 1H), 8.10-7.75 (d, J = 6.0 Hz, 2H), 7.49-7.12 (m, 6H), 6.87-6.75 (m, 2H), 6.49 (dd, J = 6.2, 1.9 Hz, 1H), 6.15-6.03 (m, 2H), 5.93 (s, 2H), 5.07 (d, J = 3.6 Hz, 1H), 4.46 (s, 3H), 4.39-4.29 (m, 7H), 4.19 (m, 1H), 3.89 (m, 1H), 3.79-3.57 (m, 2H), 3.24 (d, J = 28.1 Hz, 3H), 2.98 (d, J = 11.6 Hz, 2H), 2.58 (dq, J = 11.3, 5.5 Hz, 4H), 2.41 (d, J = 3.4 Hz, 10H), 2.30-2.11 (m,3H), 2.07-1.81 (m, 4H), 1.01-0.76 (d, J = 6.7 Hz, 6H). |
| 43 | | C | 1011.5 | $^1$H NMR (400 MHZ, $CD_3OD$): δ 8.84 (s, 1H), 8.04-8.03 (d, J = 6.0Hz, 1H), 7.71-7.69 (d, J = 6.8Hz, 1H), 7.46-7.34 (m, 5H), 7.21-7.18 (m, 1H), 6.89-6.74 (m, 4H), 5.97 (s, 1H), 4.61-4.50 (m, 3H), 4.48 (s, 1H), 4.39-4.38(d, J = 2.4 Hz, 2H), 4.24 (s, 2H), 3.77-3.70 (m, 2H), 3.38-3.31 (m, 2H), 3.09-3.07 (m, 2H), 2.71-2.03 (m, 24H), 1.90-1.85 (m, 2H), 1.05-1.03 (d, J = 6.4Hz, 3H), 0.91-0.89 (d, J = 6.4Hz, 3H) |
| 44 | C | A | 1011.5 | $^1$H NMR (400 MHZ, $CD_3OD$): δ 8.86 (s, 1H), 8.04-8.03 (d, J = 6.0 Hz, 1H), 7.71-7.69 (d, J = 6.8Hz, 1H), 7.46-7.41 (m, 5H), 7.22-7.18 (m, 1H), 6.89-6.72 (m, 4H), 5.99 (s, 1H), 4.59-4.50 (m, 2H), 4.48-4.43 (m, 4H), 4.31-4.28 (m, 2H), 3.88-3.81 (m, 1H), 3.68-3.66 (m, 2H), 3.37-3.31 (m, 2H), 3.11-3.08 (m, 2H), 2.77-2.74 (m, 2H),2.69-2.66 (m, 3H), 2.56-2.38 (m, 13 H), 2.26-2.14 (m, 7H), 1.89-1.85 (m, 2H), 1.05-1.03 (d, J = 6.4Hz, 3H), 0.91-0.89 (d, J = 6.4Hz, 3H) |
| 45 | D | A | 1059.1 | $^1$H NMR (300 MHz, $CD_3OD$) : δ 8.88-8.66 (m, 1H), 8.09-7.88 (m, 1H),7.76-7.57 (m,1H), 7.52-7.01 (m, 6H), 6.92-6.62(m, 4H), 4.66-4.21(m, 6H), 3.94-3.72 (m, 2H),3.69-3.33 (m, 12H), 3.14-2.89 (m, 4H), 2.81-2.34 (m, 14H), 2.32-1.78 (m, 8H), 1.32-0.74 (m, 12H). |
| 46 | D | B | 1027.6 | $^1$H NMR (300 MHz, DMSO-$d_6$) δ 14.10 (s, 1H), 8.99-8.83 (m, 1H), 8.25 (d, J = 7.8 Hz, 1H), 7.92-7.83 (m, 2H), 7.75-7.12 (m, 6H), 6.81 (td, J = 8.4, 2.2 Hz, 2H), 6.49 (dd, J = 6.1, 2.0 Hz, 1H), 6.15-5.93 (m, 4H), 5.06 (d, J = 3.6 Hz, 1H), 4.98-4.79 (m, 1H), 4.38 (t, J = 7.7 Hz, 3H), 4.19 (dt, J = 21.0, 5.6 Hz, 5H), 3.98 (m, 1H),3.71 (d, J = 8.6 Hz, 2H), 3.57-3.34 (m, 2H), 3.33-3.15 (m, 2H), 2.97 (d, J = 11.6 Hz, 4H), 2.57-2.40 (d, J = 8.0 Hz, 11H), 2.31-2.07 (m, 1H), 2.06-1.97 (m, 2H), 1.91-1.66 (m, 3H), 1.42 (d, J = 7.0 Hz, 1H), 1.31 (d, J = 7.0 Hz, 3H), 0.92-0.67 (m, 6H). |
| 47 | A | A | 1027.7 | $^1$H NMR (300 MHz, DMSO-$d_6$) δ 14.11 (s, 1H), 8.95 (s, 1H), 8.37 (d, J = 7.6 Hz, 1H), 7.88-7.75 (d, J = 5.9 Hz, 2H), 7.49-7.28 (m, 6H), 7.18 (ddd, J = 8.3, 7.0, 1.6 Hz, 1H), 6.88-6.75 (m, 2H), 6.49 (dd, J = 6.2, 2.0 Hz, 1H), 6.16-6.02 (m, 2H), 5.93 (s, 2H), 5.05 (d, J = 3.7 Hz, 1H), 5.00-4.81 (m, 1H), 4.46 (s, 2H), 4.39-4.13 (m, 6H), 3.72-3.55 (m, 2H), 3.45-3.35 (m, 1H), 3.21 (d, J = 11.7 Hz, 2H), 2.98 (d, J = 11.6 Hz, 2H), 2.59 (q, J = 6.5 Hz, 4H), 2.42 (s, 6H), 2.17 (dd, J = 20.0, 8.3 Hz, 3H), 1.94 (s, 4H), 1.75 (t, J = 9.6 Hz, 1H), 1.37 (dd, J = 20.9, 7.0 Hz, 3H), 1.17 (d, J = 14.9 Hz, 1H), 1.05-0.87 (m, 3H), 0.77 (dd, J = 10.6, 6.7 Hz, 3H). |
| 48 | D | A | 1092.9 | $^1$H NMR (300 MHz, $CD_3OD$,ppm): δ 8.80 (s, 1H), 8.04 (d, J = 6.1 Hz, 1H), 7.96 (d, J = 2.3 Hz, 1H), 7.67 (dd, J = 7.9, 1.6 Hz, 1H), 7.49-7.40 (m, 4H), 7.35 (d, J = 8.4 Hz, 2H), 7.22 (ddd, J = 8.5, 7.3, 1.5 Hz, 1H), 6.95-6.80 (m, 2H), 6.71 (dd, J = 8.4, 5.0 Hz, 2H), 6.60 (d, J = 2.4 Hz, 1H), 4.68-4.55 (m, 2H), 4.50 (d, J = 8.3 Hz, 4H), 4.32 (d, J = 15.4 Hz, 1H), 3.89 (d, J = 11.2 Hz, 1H), 3.80 (dd, J = 10.9, 3.7 Hz, 1H), 3.65-3.41 (m, 8H), 3.28 (s, 3H), 3.07 (t, J = 3.5 Hz, 3H), 3.02 (d, J = 3.2 Hz, 1H), 2.76-2.57 (m, 8H), 2.41 (s, 3H), 2.22 (q, J = 5.3, 4.2 Hz, 3H), 2.11 (dt, J = 7.8, 3.8 Hz, 3H), 1.93 (p, J = 6.5 Hz, 2H), 1.03 (d, J = 8.4 Hz, 9H), 0.89 (s, 1H). |
| 49 | D | B | 1084.9 | $^1$H NMR (300 MHZ, $CD_3OD$)8 8.84 (s, 1H), 8.02 (d, J = 6.0 Hz, 1H), 7.71 (d, J = 7.7 Hz, 1H), 7.47-7.33 (m, 5H), 7.21 (t, J = 7.6 Hz, 1H), 6.86 (t, J = 8.0 Hz, 2H), 6.77-6.64 (m, 2H), 4.66 (s, 1H), 4.54 (m, 3H), 4.41 (s, 1H), 4.22 (s, 1H), 3.98-3.69 (m, 2H), 3.70 (t, J = 7.3 Hz, 2H),3.5(m, 2H) ,3.33 (d, J = 11.8 Hz, 3H), 3.08 (d, J = 11.4 Hz, 4H), 2.62 (dt, J = 13.2, 7.3 Hz, 4H), 2.48-2.10 (m, 7H), 2.30 (m, 5H), 2.20-2.02 (m, 5H), 1.88 (s, 3H), 1.51 (dd, J = 16.3, 7.1 Hz, 3H), 1.26 (s, 3H), 1.00 (d, J = 5.7 Hz, 9H), 0.87 (s, 1H). |
| 50 | C | A | 1106.9 | $^1$H NMR (300 MHz, $CD_3OD$): δ 8.85 (s, 1H), 8.10-8.00 (m, 2H), 7.80-7.10 (m, 8H), 6.90-6.75 (m, 5H), 5.00 (m, 1H), 4.60-4.30 (m, |

TABLE 2A-continued

| Target protein degradation via exemplary bifunctional degradation compounds of Table 1A | | | | |
|---|---|---|---|---|
| Ex. # | *$DC_{50}$ (nM) | **$D_{max}$ (%)† | MH+ | NMR transcript |
| | | | | 5H), 3.90-3.30 (m, 14H), 3.10-3.00 (m, 2H), 2.80-2.40 (m, 11H), 2.30-1.90 (m, 8H), 1.50-1.40 (m, 3H), 1.30-1.40 (s, 1H), 1.02 (m, 9H) |
| 51 | C | A | 986.8 | $^1$H NMR (300 MHZ, $CD_3OD$): δ 8.85 (s, 1H), 7.78-7.75 (m, 1H), 7.51 (s, 1H), 7.41-7.35 (m, 4H), 7.27-7.20 (m, 1H), 6.92-6.90 (m, 2H), 5.13-4.98 (m, 1H), 4.68 (s, 1H), 4.60-4.53 (m, 1H), 4.55-4.34 (m, 1H), 4.10-4.00 (m, 2H), 3.86-3.82 (m, 1H), 3.80-3.74 (m, 2H), 3.73-3.64 (m, 6H), 3.64-3.59 (m, 2H), 3.52-3.49 (m, 2H), 3.29-3.20 (m, 2H), 3.11-3.01 (m, 2H), 2.46 (s, 3H), 2.42 (s, 2H), 2.38-2.30 (m, 4H), 2.21-2.10 (m, 3H), 2.01-1.91 (m, 1H), 2.86-2.78 (m, 2H), 2.70-2.53 (m, 5H), 1.50 (d, J = 5.1 Hz, 3H), 1.05 (s, 9H) |
| 52 | C | A | 1033.8 | $^1$H NMR (300 MHz, CD3OD): δ 8.83 (s, 1H), 8.11-8.05(m, 1H), 7.75-7.71(m, 1H), 7.48-7.38(m, 5H), 7.28-7.17(m, 1H), 6.94-6.86 (m, 3H), 6.77-6.63 (m, 3H), 4.82(s, 1H), 4.67-4.53(m, 3H), 4.50-4.42(m, 2H), 4.38-4.27(m, 1H), 4.23-4.17(m, 2H), 4.05-3.99(m, 2H), 3.85-3.72(m, 2H), 3.72-3.59(m, 12H), 3.39-3.35(m, 1H), 3.14-3.06(m, 2H), 2.45(s, 3H), 2.28-2.02 (m, 6H), 1.29(m, 1H), 1.04-0.98(m, 9H) |
| 53 | B | A | 1035.8 | $^1$H NMR (300 MHz, CD3OD): δ 8.84 (s, 1H), 8.13-8.03(m, 1H), 7.75-7.71(m, 1H), 7.48-7.37(m, 5H), 7.28-7.13(m, 1H), 6.93-6.66 (m, 4H), 4.83(s, 1H), 4.67-4.50(m, 3H), 4.50-4.35(m, 1H), 4.38-4.29(m, 1H), 4.05-3.99(m, 1H), 3.86-3.78(m, 2H), 3.70-3.52(m, 11H), 3.51-3.40(m, 2H), 3.14-3.05(m, 2H), 2.88-2.79(m, 1H), 2.78-2.64(m, 2H), 2.45(s, 2H), 2.28-2.02 (m, 5H), 1.98-1.87(m, 2H), 1.49-1.20(m, 6H), 1.08-0.98(m, 9H), 0.96-0.88(m, 1H) |
| 54 | D | A | 1061.7<br>1063.7 | $^1$H NMR (300 MHZ, DMSO-$d_6$) δ 14.11 (s, 1H), 8.94 (d, J = 5.9 Hz, 1H), 8.22 (d, J = 7.7 Hz, 1H), 7.88 (d, J = 8.0 Hz, 1H), 7.75 (d, J = 5.9 Hz, 1H), 7.49-7.33 (m, 5H), 7.31-7.12 (m, 1H), 6.81 (dd, J = 10.2, 7.8 Hz, 2H), 6.49 (d, J = 6.2 Hz, 1H), 6.12 (d, J = 1.9 Hz, 1H), 5.93 (s, 2H), 5.08 (d, J = 3.5 Hz, 1H), 4.80 (t, J = 7.2 Hz, 1H), 4.49-4.33 (m, 3H), 4.24 (q, J = 7.0, 6.0 Hz, 5H), 3.98 (d, J = 10.0 Hz, 1H), 3.58 (d, J = 11.0 Hz, 1H), 3.50-3.33 (m, 2H), 3.21 (d, J = 11.7 Hz, 2H), 2.97 (d, J = 11.7 Hz, 2H), 2.61 (dt, J = 21.6, 6.2 Hz, 4H), 2.61 (dt, J = 21.6, 6.2 Hz, 3H), 2.41 (d, J = 4.0 Hz, 8H), 2.18-2.07 (m, 6H), 1.93 (s, 3H), 1.230.65 (m, 6H) |
| 55 | A | A | 1061.7<br>1063.7 | $^1$H NMR (300 MHz, DMSO-$d_6$) δ 14.10 (s, 1H), 8.95 (s, 1H), 8.37 (d, J = 7.7 Hz, 1H), 7.93-7.83 (m, 1H), 7.75 (d, J = 6.0 Hz, 1H), 7.49-7.28 (m, 5H), 7.18 (t, J = 8.1 Hz, 1H), 6.81 (t, J = 9.0 Hz, 2H), 6.50 (dd, J = 6.2, 2.1 Hz, 1H), 6.12 (d, J = 1.9 Hz, 1H), 5.94 (s, 2H), 5.08 (d, J = 3.9 Hz, 1H), 4.86 (q, J = 8.0, 7.6 Hz, 1H), 4.46 (s, 2H), 4.38-4.18 (m, 6H), 3.91 (t, J = 10.8 Hz, 2H), 3.71 (t, J = 10.8 Hz, 2H), 3.21 (d, J = 11.5 Hz, 2H), 2.98 (d, J = 11.6 Hz, 5H), 2.63 (dt, J = 24.3, 5.9 Hz, 3H), 2.43 (d, J = 4.6 Hz, 8H), 2.14 (d, J = 7.4 Hz, 2H), 1.93 (s, 3H), 1.80 (s, 1H), 1.34 (d, J = 7.0 Hz, 3H), 1.20 (s, 1H), 0.95 (d, J = 6.4 Hz, 3H), 0.74 (d, J = 6.7 Hz, 3H). |
| 56 | A | A | 1060.7 | $^1$H NMR (300 MHz, Methanol-d4): δ 8.84 (d, J = 19.7 Hz, 1H), 8.10 (t, J = 3.3 Hz, 1H), 7.76 (dd, J = 10.9, 6.9 Hz, 2H), 7.58-7.32 (m, 6H), 7.30-7.18 (m, 2H), 6.95-6.83 (m, 2H), 6.83-6.50 (m, 3H), 6.18 (d, J = 2.0 Hz, 1H), 6.05 (d, J = 7.4 Hz, 1H), 5.33-5.23 (m, 1H), 5.05-4.95 (m, 1H), 4.88-4.83 (m, 2H), 4.65-4.40 (m, 3H), 4.40-4.30 (m, 1H), 3.96-3.59 (m, 3H), 3.36 (s, 1H), 3.12 (d, J = 11.6 Hz, 2H), 2.66 (t, J = 5.8 Hz, 4H), 2.47 (d, J = 7.8 Hz, 4H), 2.29-1.99 (m,6H), 1.32 (d, J = 13.0 Hz, 2H), 1.05 (t, J = 6.0 Hz, 3H), 0.91 (t, J = 7.5 Hz, 3H). |
| 57 | | C | 1013.7 | $^1$H NMR (300 MHZ, DMSO-$d_6$)δ14.17 (s, 1H), 8.99 (d, J = 3.6 Hz, 1H), 8.52 (d, J = 15.4 Hz, 1H), 7.93 (d, J = 8.1 Hz, 1H), 7.79 (d, J = 5.9 Hz, 1H), 7.51-7.03 (t, J = 7.8 Hz, 6H), 6.92-6.79 (m, 2H), 6.54 (d, J = 6.1 Hz, 1H), 6.20-6.04 (m, 2H), 5.99 (s, 2H), 5.14 (t, J = 4.2 Hz, 1H), 4.71-4.14 (m, 10H), 3.82 (dd, J = 29.2, 9.3 Hz, 2H), 3.57-3.25 (d, J = 11.4 Hz, 2H), 3.02 (d, J = 11.7 Hz, 2H), 2.60-2.43 (m, 4H), 2.39 (d, J = 7.1 Hz, 10H), 2.18 (s, 4H), 2.05 (s, 4H), 0.96 (t, J = 6.3 Hz, 3H), 0.82-0.67 (d, J = 6.7 Hz, 3H), 0.58 (d, J = 6.8 Hz, 1H). |
| 58 | D | B | 1134.8 | |
| 59 | D | A | 896.6 | 1H NMR (300 MHz, DMSO-D6): δ 13.84 (s, 1H), 9.04-8.86 (m, 1H), 8.61 (s, 1H), 8.30 (d, J = 7.9 Hz, 1H), 8.21 (d, J = 10.8 Hz, 2H), 8.07-7.97 (m, 1H), 7.54-7.37 (m, 3H), 7.37-7.12 (m, 7H), 6.94 (d, J = 7.6 Hz, 2H), 6.51 (s, 2H), 6.12-6.10 (m, 1H), 5.70-5.56 (m, 1H), 5.21-4.79 (m, 2H), 4.56-4.38 (m, 1H), 4.28 (s, 1H), |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| | | | | 4.20-4.10 (m, 2H), 3.76 (d, J = 8.5 Hz, 1H), 3.60-3.35 (m, 2H), 2.66 (t, J = 8.1 Hz, 2H), 2.47-2.40 (m, 3H), 2.37-2.13 (m, 1H), 2.13-1.91 (m, 3H), 1.92-1.74 (m, 4H), 1.50-1.41 (m, 3H), 0.97 (d, J = 6.6 Hz, 2H), 0.84 (d, J = 6.6 Hz, 3H), 0.77 (d, J = 6.7 Hz, 1H). |
| 60 | A | A | 896.6 | 1H NMR (300 MHz, DMSO-D6): δ 13.84 (brs, 1H), 9.04-8.86 (m, 1H), 8.61 (s, 1H), 8.35-8.45 (m, 1H), 8.25-8.15 (m, 2H), 8.07-7.97 (m, 1H), 7.54-7.40 (m, 2H), 7.40-7.30 (m, 2H), 7.30-7.15 (m, 5H),6.95-6.85(m, 2H), 6.51 (s, 2H), 6.15-5.80 (m, 1H), 5.75-5.65 (m,1H), 5.15-5.05 (m, 1H), 5.05-4.85 (m, 1H), 4.56-4.20 (m, 2H), 4.20-4.05 (m, 2H), 3.80-3.55 (m, 2H), 3.60-3.35 (m, 1H), 2.75-2.60 (m, 2H), 2.45-2.35 (m, 3H), 2.30-2.13 (m, 1H), 2.10-1.95 (m, 3H), 1.95-1.70 (m, 4H),1.50-1.30(m, 3H), 1.30-1.20(m, 1H), 1.00-0.90(m, 3H), 0.90-0.70(m, 3H). |
| 61 | C | A | 901.6 | 1H NMR (400 MHz, CD3OD): δ 8.85 (s, 1H), 8.47-8.42 (m, 2H), 8.12 (d, J = 4.9 Hz, 2H), 7.83 (d, J = 7.9 Hz, 1H), 7.78 (dd, J = 8.2, 2.5 Hz, 1H), 7.42 (dt, J = 14.0, 8.0 Hz, 5H), 7.34-7.25 (m, 1H), 6.92 (t, J = 7.8 Hz, 2H), 5.75 (d, J = 7.3 Hz, 1H), 4.98-4.86 (m, 1H), 4.69 (s, 1H), 4.66-4.55 (m, 1H), 4.45 (s, 1H), 4.01-3.91 (m, 2H), 3.81-3.75 (m, 1H), 3.73-3.60 (m, 1H), 3.65-3.56 (m, 2H), 2.94 (t, J = 7.6 Hz, 2H), 2.46 (s, 3H), 2.19-2.06 (m, 1H), 2.12-1.98 (m, 5H), 1.57-1.49 (m, 3H), 1.33 (d, J = 17.4 Hz, 1H), 1.04 (s, 9H) |
| 62 | B | A | 934.7 | 1H NMR (400 MHz, DMSO-D6): δ 9.05-8.77 (m, 1H), 8.50-8.37 (m, 2H), 8.27 (s, 1H), 8.20-8.18 (m, 2H), 8.07-7.93 (m, 1H), 7.51-7.41 (m, 2H), 7.41-7.33 (m, 2H), 7.31-7.21 (m, 1H), 6.98-6.86 (m, 2H), 6.49 (s, 2H), 6.12-5.84 (m, 1H), 4.98-4.85 (m, 1H), 4.43-4.31 (m, 3H), 4.29 (s, 1H), 4.15-4.12 (m, 2H), 3.83-3.80 (m, 2H), 3.72-3.70 (m, 3H), 3.67-3.65 (m, 4H), 2.43-2.40 (m, 3H), 2.38-2.29 (, 7H), 2.27-2.20 (m, 2H), 2.11-1.98 (m, 1H), 1.82-1.75 (m, 1H), 1.48-1.33 (m, 3H), 1.01-0.91 (m, 3H), 0.87-0.75 (m, 3H). |
| 63 | B | A | 1068.8 | 1H NMR (300 MHz, CD3OD): δ 8.84 (s, 1H), 7.76-7.70 (m, 2H), 7.45-7.33 (m, 5H), 7.21-7.15 (m, 1H), 6.89-6.87 (m, 2H), 6.52-6.51 (m, 1H), 6.11-6.02 (m, 2H), 5.10-5.00 (m, 1H), 4.99-4.97 (m, 1H), 4.56-4.42 (m, 3H), 4.37-4.27 (m, 4H), 3.77-3.66 (m, 3H), 3.40-3.31 (m, 3H), 3.11-3.07 (m, 2H), 2.81-2.72 (m, 4H), 2.48 (s, 3H), 2.45-2.14 (m, 12H), 2.00-1.82 (m, 3H), 1.59-1.50 (m, 3H), 1.47 (d, J = 6.9Hz, 2H), 1.04 (d, J = 6.6Hz, 3H), 0.90 (d, J = 6.9Hz, 3H) |
| 64 | A | A | 1068.8 | 1H NMR (300 MHz, CD3OD): δ 8.86 (s, 1H), 7.76-7.71 (m, 2H), 7.46-7.38 (m, 5H), 7.22-7.15 (m, 1H), 6.90-6.88 (m, 2H), 6.53-6.51 (m, 1H), 6.12-6.00 (m, 2H), 5.11-4.97 (m, 2H), 4.54-4.43 (m, 3H), 4.39-4.30 (m, 4H), 3.80-3.61 (m, 3H), 3.40-3.35 (m, 2H), 3.12-3.09 (m, 2H), 2.82-2.72 (m, 4H), 2.48 (s, 3H), 2.47-2.15 (m, 12H), 2.00-1.82 (m, 4H), 1.62-1.50 (m, 5H), 1.04 (d, J = 6.6Hz, 3H), 0.90 (d, J = 6.9Hz, 3H) |
| 65 | D | NA | 924.7 | 1H NMR (300 MHz, CD3OD): δ 8.88 (d, J = 8.0 Hz, 1H), 7.77 (d, J = 7.5 Hz, 1H), 7.49-7.40 (m, 2H), 7.37 (d, J = 8.2 Hz, 2H), 7.25 (t, J = 8.0 Hz, 1H), 6.91 (d, J = 7.9 Hz, 3H), 6.05 (s, 1H), 5.00 (d, J = 6.9 Hz, 1H), 4.57 (t, J = 8.0 Hz, 1H), 4.43 (s, 1H), 4.36-4.26 (m, 6H), 3.81 (t, J = 4.6 Hz, 2H), 3.75 (d, J = 9.2 Hz, 1H), 3.70-3.63 (m, 4H), 3.60 (s, 1H), 3.59 (s, 5H), 3.51 (d, J = 6.2 Hz, 2H), 3.36 (s, 2H), 2.61 (s, 2H), 2.49 (d, J = 6.2 Hz, 3H), 2.20 (d, J = 7.6 Hz, 1H), 1.59 (d, J = 7.4 Hz, 4H), 1.49 (d, J = 7.0 Hz, 3H), 1.33 (d, J = 16.4 Hz, 7H), 1.05 (d, J = 6.6 Hz, 3H), 0.98-0.82 (m, 4H). |
| 66 | D | A | 924.7 | 1H NMR (300 MHz, CD3OD): δ 8.88 (d, J = 3.3 Hz, 1H), 7.78 (d, J = 8.4 Hz, 1H), 7.48-7.35 (m, 4H), 7.25 (t, J = 8.2 Hz, 1H), 6.96 -6.87 (m, 3H), 6.01 (d, J = 16.6 Hz, 1H), 5.04 (d, J = 7.1 Hz, 1H), 4.52 (t, J = 8.2 Hz, 1H), 4.44 (s, 1H), 4.34 (s, 1H), 4.34 (d, J = 9.3 Hz, 1H), 4.29 (d, J = 6.0 Hz, 4H), 3.87-3.79 (m, 3H), 3.72-3.58 (m, 5H), 3.56 (s, 6H), 3.52 (d, J = 6.0 Hz, 1H), 3.36 (s, 1H), 3.22 (s, 2H), 2.60 (s, 2H), 2.48 (d, J = 2.7 Hz, 3H), 2.17 (d, J = 10.3 Hz, 1H), 1.97 (ddd, J = 13.7, 8.8, 4.8 Hz, 1H), 1.59 (d, J = 7.1 Hz, 1H), 1.52 (d, J = 7.0 Hz, 3H), 1.49 (s, 2H), 1.35 (s, 1H), 1.31 (s, 1H), 1.20 (s, 7H), 1.05 (d, J = 6.5 Hz, 3H), 0.90 (dd, J = 10.9, 6.7 Hz, 3H). |
| 67 | D | NA | 980.7 | 1H NMR (300 MHz, CD3OD): δ 8.88 (d, J = 5.1 Hz, 1H), 7.84-7.75 (m, 1H), 7.53 (s, 1H), 7.50-7.34 (m, 4H), 7.26 (t, J = 7.1 Hz, 1H), 6.98-6.88 (m, 2H), 6.02 (d, J = 13.4 Hz, 1H), 5.01 (q, J = 6.8 Hz, 1H), 4.58 (t, J = 7.9 Hz, 1H), 4.43 (s, 1H), 4.36-4.28 (m, 1H), 3.89-3.71 (m, 3H), 3.67 (d, J = 3.8 Hz, 4H), 3.68-3.49 (m, 5H), 3.37 (s, OH), 3.13 (s, 5H), 2.58-2.35 (m, 11H), 2.20 (d, J = 7.9 Hz, 1H), 2.04-1.92 (m, 1H), 1.74 (s, 4H), 1.64 (d, J = |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| | | | | 16.5 Hz, 10H), 1.50 (d, J = 7.0 Hz, 3H), 1.31 (s, 2H), 1.06 (d, J = 6.6 Hz, 3H), 1.02-0.82 (m, 4H). |
| 68 | B | A | 980.7 | $^{1}$H NMR (300 MHz, CD3OD): δ 8.88 (s, 1H), 7.80 (dd, J = 8.1, 1.6 Hz, 1H), 7.53 (d, J = 5.0 Hz, 1H), 7.49-7.34 (m, 4H), 7.31-7.20 (m, 1H), 6.93 (ddd, J = 7.3, 3.8, 2.6 Hz, 2H), 6.03 (s, 1H), 5.04 (q, J = 6.9 Hz, 1H), 4.53 (t, J = 8.1 Hz, 1H), 4.42 (d, J = 16.8 Hz, 1H), 4.37-4.29 (m, 2H), 3.88-3.74 (m, 3H), 3.73-3.45 (m, 8H), 3.37 (s, OH), 3.14 (t, J = 5.4 Hz, 5H), 2.55 (s, 4H), 2.49 (s, 6H), 2.08-1.90 (m, 1H), 1.75 (s, 4H), 1.70-1.48 (m, 13H), 1.33 (d, J = 12.4 Hz, 4H), 1.06 (d, J = 6.5 Hz, 3H), 0.91 (t, J = 7.2 Hz, 4H). |
| 69 | C | A | 1072.7 | 1H NMR (400 MHz, DMSO-D6): δ 14.14 (s, 1H), 8.97 (d, J = 12.9 Hz, 1H), 8.33 (d, J = 7.8 Hz, 1H), 8.20 (s, 1H), 7.91 (d, J = = 7.9 Hz, 1H), 7.77 (d, J = 5.8 Hz, 1H), 7.48-7.34 (d, J = 8.1 Hz, 4H), 7.32-7.17 (m, 3H), 6.85 (m, 2H), 6.54 (d, J = 6.1 Hz, 1H), 6.18 (d, J = 5.0 Hz, 2H), 5.98 (s, 2H), 5.45-4.72 (m, 6H), 4.60-4.11 (m, 4H), 3.78 (d, J = 8.6 Hz, 1H), 3.57 (s, 1H), 3.23 (s, 2H), 3.01 (d, J = 11.8 Hz, 2H), 2.60 (m, 4H), 2.50 (m, 3H), 2.26-1.75 (m, 8H), 1.45-1.22 (m, 4H), 0.96-0.76 (m, 6H). |
| 70 | A | A | 1072.7 | 1H NMR (400 MHz, DMSO-D6): δ 14.14 (s, 1H), 8.98 (s, 1H), 8.43 (d, J = 7.6 Hz, 1H), 8.21 (d, J = 2.9 Hz, 1H), 7.91 (d, J = 7.9 Hz, 1H), 7.77 (d, J = 5.9 Hz, 1H), 7.50-7.19 (m, 7H), 6.85 (m, 2H), 6.58-6.51 (m, 1H), 6.19 (d, J = 11.0 Hz, 2H), 5.98 (s, 2H), 5.31 (t, J = 6.1 Hz, 1H), 5.13 (d, J = 10.0 Hz, 2H), 5.06-4.98 (m, 1H), 4.95-4.86 (m, 1H), 4.50 (s, 2H), 4.37 (t, J = 7.9 Hz, 1H), 4.28 (s, 1H), 3.69 (d, J = 9.3 Hz, 2H), 3.52 (m,1H), 3.23 (m, 2H), 3.01 (d, J = 11.6 Hz, 2H), 2.56 (s, 4H), 2.45 (s, 3H), 2.31-1.71 (m, 7H), 1.44-1.30 (d, J = 7.0 Hz, 3H), 1.23 (s, 2H), 0.96 (d, J = 6.3 Hz, 3H), 0.82 (d, J = 12.3, 6.6 Hz, 3H). |
| 71 | D | NA | 952.7 | 1H NMR (300 MHz, CD3OD): δ 8.90 (d, J = 5.5 Hz, 1H), 7.85-7.76 (m, 1H), 7.55-7.34 (m, 5H), 7.33-7.21 (m, 1H), 6.99-6.88 (m, 2H), 6.05 (s, 1H), 5.52 (s, OH), 5.02 (q, J = 7.1 Hz, 1H), 4.59 (t, J = 8.0 Hz, 1H), 4.44 (s, 1H), 4.33 (q, J = 3.9 Hz, 1H), 3.90-3.75 (m, 2H), 3.69 (s, 2H), 3.71-3.64 (m, 2H), 3.62 (d, J = 2.7 Hz, 2H), 3.63-3.46 (m, 3H), 3.21 (s, 5H), 3.08 (s, 4H), 2.60 (s, 2H), 2.50 (d, J = 4.0 Hz, 3H), 2.46-2.32 (m, 1H), 2.23 (dd, J = 14.3, 7.2 Hz, 1H), 2.00 (s, 5H), 2.01-1.89 (m, 1H), 1.61 (d, J = 7.1 Hz, 2H), 1.51 (d, J = 7.0 Hz, 3H), 1.34 (d, J = 13.0 Hz, 3H), 1.11-0.83 (m, 6H). |
| 72 | C | A | 952.7 | 1H NMR (300 MHz, CD3OD): δ 8.89 (d, J = 2.4 Hz, 1H), 7.81 (d, J = 8.1 Hz, 1H), 7.53 (d, J = 5.1 Hz, 1H), 7.50-7.35 (m, 4H), 7.27 (t, J = 7.6 Hz, 1H), 7.00-6.90 (m, 2H), 6.02 (d, J = 13.3 Hz, 1H), 5.04 (t, J = 7.3 Hz, 1H), 4.53 (t, J = 8.2 Hz, 1H), 4.46 (s, 1H), 4.35 (s, 2H), 4.35 (d, J = 9.3 Hz, 1H), 3.85 (d, J = 9.1 Hz, 1H), 3.85 (s, 2H), 3.74-3.58 (m, 5H), 3.53 (t, J = 6.1 Hz, 1H), 3.24 (d, J = 3.7 Hz, 4H), 3.10 (s, 5H), 2.64 (s, 2H), 2.50 (d, J = 1.4 Hz, 3H), 2.39 (s, 2H), 2.25-2.14 (m, 1H), 2.07-1.95 (m, 4H), 1.57 (dd, J = 19.3, 7.0 Hz, 6H), 1.34 (d, J = 12.2 Hz, 4H), 1.22 (s, 1H), 1.07 (d, J = 6.6 Hz, 3H), 0.90 (d, J = 6.7 Hz, 3H). |
| 73 | D | NA | 966.7 | 1H NMR (300 MHz, CD3OD): δ 8.86 (d, J = 5.7 Hz, 1H), 7.78 (d, J = 7.8 Hz, 1H), 7.51 (s, 1H), 7.40 (p, J = 8.1 Hz, 3H), 7.24 (t, J = 7.9 Hz, 1H), 6.92 (d, J = 8.5 Hz, 2H), 6.00 (d, J = 14.1 Hz, 1H), 5.49 (s, 1H), 4.99 (d, J = 7.1 Hz, 1H), 4.56 (t, J = 7.8 Hz, 1H), 4.42 (s, 1H), 3.84-3.70 (m, 2H), 3.69-3.57 (m, 1H), 3.51 (s, 1H), 3.11 (s, 5H), 2.74 (s, 2H), 2.59 (d, J = 17.9 Hz, 4H), 2.48 (d, J = 4.2 Hz, 3H), 2.18 (d, J = 7.8 Hz, 1H), 1.82 (s, 6H), 1.62 (s, 4H), 1.48 (d, J = 7.0 Hz, 2H), 1.29 (s, 3H), 1.04 (d, J = 6.6 Hz, 2H), 0.90 (d, J = 6.7 Hz, 3H). |
| 74 | C | A | 966.7 | 1H NMR (300 MHz, CD3OD): δ 8.86 (s, 1H), 7.79 (d, J = 7.8 Hz, 1H), 7.52 (d, J = 5.0 Hz, 1H), 7.48-7.35 (m, 4H), 7.24 (t, J = 7.5 Hz, 1H), 6.96-6.87 (m, 1H), 5.98 (d, J = 12.9 Hz, 1H), 5.49 (s, 1H), 5.01 (t, J = 7.2 Hz, 1H), 4.51 (t, J = 8.1 Hz, 1H), 4.43 (s, 1H), 4.32 (s, 2H), 4.32 (d, J = 9.2 Hz, 1H), 3.82 (t, J = 4.8 Hz, 3H), 3.71-3.57 (m, 5H), 3.12 (s, 5H), 2.73 (s, 2H), 2.60 (s, 2H), 2.54 (s, 2H), 2.47 (d, J = 1.9 Hz, 3H), 2.01 (s, 2H), 1.82 (t, J = 6.8 Hz, 7H), 1.63 (s, 5H), 1.54 (dd, J = 18.6, 6.9 Hz, 3H), 1.31 (d, J = 12.4 Hz, 7H), 1.04 (d, J = 6.6 Hz, 3H), 0.88 (d, J = 6.8 Hz, 5H). |
| 75 | C | A | 1010.8 | |
| 76 | A | A | 1010.8 | 1H NMR (400 MHz, DMSO-D6): δ 8.83 (d, J = 7.6 Hz, 1H), 8.17 (s, 3H), 7.91 (d, J = 7.6 Hz, 1H), 7.79 (d, J = 6.0 Hz, 1H), 7.50 (s, 1H), 7.45-7.35 (m, 4H), 7.27-7.19 (m, 2H), 6.97-6.80 (m, 3H), 6.53 (d, J = 6.0 Hz, 1H), 6.20-5.89 (m, 4H), 5.02-4.90 (m, 1H), 4.56-4.18 (m, 7H), 3.75-3.37 (m, 16H), 3.26 (d, J = 11.6 Hz, 2H), 3.02 (d, J = 11.6 Hz, 2H), 2.71-2.65 (m, 3H), 2.28 (s, 3H), |

TABLE 2A-continued

| Target protein degradation via exemplary bifunctional degradation compounds of Table 1A | | | | |
|---|---|---|---|---|
| Ex. # | *$DC_{50}$ (nM) | **$D_{max}$ (%)† | MH+ | NMR transcript |
| | | | | 2.17-1.92 (m, 4H), 1.85-1.74 (m, 1H), 1.39 (d, J = 7.2 Hz, 2H), 1.03-0.69 (m, 6H). |
| 81 | A | A | 898.6 | 1H NMR (300 MHz, CD3OD): δ 8.78 (s, 1H), 8.35 (s, 1H), 8.25-8.12 (m, 1H), 8.12-8.05 (m, 1H), 7.95-7.78 (m, 1H), 7.54-7.24 (m, 7H), 7.08-6.88 (m, 4H), 6.12-5.94 (m, 1H), 5.80-5.57 (m, 1 H), 5.12-4.96 (m, 1H), 4.61-4.50 (m, 3H), 4.50-4.37 (m, 1H), 4.37-4.30 (m, 2H), 4.02-3.78 (m,1H), 3.78-3.45 (m, 2H), 2.51 (s, 3H), 2.45-2.30 (m, 1H), 2.27-2.13 (m,1H),2.02-1.90 (m, 4H), 1.68-1.50 (m, 3H) , 1.10-1.00 (m, 3H), 0.98-0.84 (m, 3H). |
| 82 | A | A | 899.7 | 1H NMR (300 MHz, CD3OD): δ 8.88-8.84 (m, 1H), 8.37-8.35 (m, 1H), 8.15-8.14 (m, 1H), 8.08-8.05 (m, 2H), 7.85-7.82 (m, 1H), 7.74-7.70 (m, 1H), 7.45-7.22 (m, 5H), 6.94-6.89 (m, 2H), 6.81-6.78 (m, 1H), 5.99-5.93 (m, 1H), 5.72-5.65 (m, 1H), 5.05-4.96 (m, 1H), 4.62-4.58 (m, 2H), 4.53-4.47 (m, 3H), 4.42-4.37 (m, 1H), 3.85-3.80 (m, 1H), 3.70-3.58 (m, 2H), 2.47-2.45 (m, 3H), 2.39-2.32 (m, 1H), 2.21-2.13 (m, 1H), 1.99-1.90 (m, 4H), 1.57-1.49 (m, 3H), 1.05-0.95 (m, 3H), 0.91-0.85 (m, 3H). |
| 83 | A | A | 980.8 | 1H NMR (300 MHz, CD3OD): δ 8.88 (s, 1H), 8.38 (s, 1H), 8.11-8.09 (m, 2H), 7.86 (d, J = 7.8 Hz, 1H), 7.49-7.39 (m, 4H), 7.39-7.22 (m, 5H), 6.99-6.90 (m, 2H), 6.00 (s, 1H), 5.72-5.65 (m, 1H), 5.10-4.99 (m, 1H), 4.58-4.49 (m, 1H), 4.49-4.39 (m, 1H), 4.37-4.29 (m, 2H), 3.89-3.75 (m, 1H), 2.72-3.59 (m, 2H), 3.57-3.50 (m, 2H), 3.40-3.36 (m, 1H), 2.82-2.73 (m, 2H), 2.69-2.43 (m, 10H), 2.43-2.25 (m, 1H), 2.25-2.11 (m, 1H), 2.08-1.90 (m, 4H), 2.61-2.48 (m, 3H), 1.10-1.00 (m, 3H), 0.93-0.80 (m, 3H). |
| 86 | A | A | 1074.7 | 1H NMR (400 MHZ, CD3OD): δ 8.87 (d, J = 12.3 Hz, 1H), 8.11 (t, J = 2.9 Hz, 1H), 7.77 (m, 2H), 7.52-7.38 (m, 6H), 7.36-7.20 (m, 2H), 6.94-6.85 (m, 2H), 6.84-6.64 (m, 2H), 6.56 (m, 1H), 6.19 (d, J = 2.2 Hz, 1H), 6.06 (s, 1H), 5.35-5.25 (m, 1H), 5.09-5.00 (m, 2H), 4.93-4.87 (m, 2H), 4.53 (t, J = 8.0 Hz, 3H), 4.45 (s, 1H), 3.85 (m, 1H), 3.79-3.63 (m, 2H), 3.63-3.49 (m, 1H), 3.13 (d, J = 11.3 Hz, 2H), 2.67 (q, J = 5.1, 4.4 Hz, 4H), 2.48 (d, J = 6.1 Hz, 3H), 2.46-2.33 (m, 1H), 2.24-2.17 (s, 5H), 2.08-1.92 (m, 1H), 1.56 (m, 3H), 1.30 (s, 1H), 1.07 (d, J = 6.5 Hz, 3H), 0.92 (m, 3H). |
| 91 | A | A | 1006.9 | 1H NMR (400 MHZ, CD3OD): δ 8.88 (s, 1H), 7.79 (d, J = 7.9 Hz, 1H), 7.56-7.35 (m, 5H), 7.26 (t, J = 7.7 Hz, 1H), 6.94-6.85 (m, 2H), 6.08-5.95 (m, 1H), 5.10-5.02 (m, 1H), 4.65-4.52 (m, 3H), 4.45 (s, 1H), 4.35-4.31 (m, 2H), 3.91-3.75 (m, 3H), 3.75-3.58 (m, 2H), 3.30-3.21 (m, 2H), 3.09 (t, J = 11.7 Hz, 2H), 2.82-2.75 (m, 2H), 2.81-2.64 (m, 6H), 2.51-2.40 (m, 6H), 2.41-2.35 (m, 5H), 2.25-2.07 (m, 3H), 2.05-1.95 (m, 1H), 1.83 (t, J = 12.6 Hz, 2H), 1.65-1.48 (m, 7H), 1.20 (s, 1H), 1.06 (d, J = 6.5 Hz, 3H), 0.91 (dd, J = 9.5, 6.7 Hz, 3H) |
| 93 | A | A | 1033.9 | $^{1}$H NMR (300 MHz, CD3OD): δ 8.89 (s, 1H), 7.82-7.77 (m, 1H), 7.54 (s, 1H), 7.50-7.38 (m, 4H), 7.30-7.21 (m, 1H), 6.98-6.90 (m, 2H), 6.02 (m, 1H), 5.10-5.00 (m, 1H), 4.57-4.50 (m, 1H), 4.50-4.39 (m, 1H), 4.37-4.28 (m, 2H), 4.10-3.95 (m, 1H), 3.90-3.75 (m, 3H), 3.70-3.59 (m, 2H), 3.54-3.46 (m, 2H), 3.30-3.19 (m, 2H), 3.19-3.07 (m, 2H), 2.79-2.69 (m, 2H), 2.60-2.30 (m, 14H), 2.27-2.10 (m, 5H), 2.05-1.93 (m, 1H), 1.92-1.80 (m, 2H), 1.73-1.50 (m, 9H), 1.10-1.01 (m, 3H), 0.98-0.85 (m, 3H). |
| 100 | A | A | 1043.7 | 1H NMR (300 MHz, $CD_3OD$-$d_6$): 8.85 (s, 1H), 7.97-7.80 (m, 1H), 7.80-7.63 (m, 1H), 7.60-7.40 (m, 5H), 7.40-7.18 (m, 1H), 7.03-6.90 (m, 2H), 6.78-6.62 (m, 1H), 6.48-6.34 (m, 1H), 6.04 (s, 1H), 5.09-5.01 (m, 1H), 4.70-4.62 (m, 2H), 4.62-4.50 (m, 3H), 4.50-4.35 (m, 3H), 3.98-3.81 (m, 3H), 3.81-3.60 (m, 3H), 3.60-3.48 (m, 3H), 3.28-2.98 (m, 11H), 2.67-1.92 (m, 10H), 1.41-1.25 (m, 4H),1.18-1.03 (m, 3H), 0.97-0.87 (m, 3H) |
| 102 | A | A | 1063.8 | 1H NMR (300 MHz, DMSO-D6): δ 14.14 (s, 1H), 9.10-8.90 (m, 2H), 7.90-7.80 (m, 1H), 7.80-7.70 (m, 1H), 7.70-7.40 (m, 5H), 7.30-7.20 (m, 1H), 6.90-6.78 (m, 2H), 6.60-6.50 (m, 1H), 6.25-5.90 (m, 5H), 5.50-5.35 (m, 1H), 5.20-5.00 (m, 1H), 4.60-4.40 (m, 3H), 4.35-4.20 (m, 5H), 3.80-3.70 (m, 2H), 3.65-3.40 (m, 2H), 3.30-3.20 (m, 3H), 3.10-3.00 (m, 2H), 2.70-60 (m, 4H), 2.50-2.40 (m, 8H), 2.25-2.15 (m, 4H), 2.15-1.95 (m, 3H), 1.80-1.70(m, 1H), 1.00-0.90 (m, 3H), 1.85-1.70(m, 3H). |
| 103 | B | A | 1042.3 | $^{1}$H NMR (400 MHZ,$CD_3OD$) δ 8.91 (s, 1H), 7.83-7.73 (m, 2H), 7.57-7.36 (m, 5H), 7.29-7.20 (m, 1H), 6.95-6.86 (m, 2H), 6.57 (m, 1H), 6.23 (m, 1H), 6.02 (s, 1H), 5.10 (m, 1H), 4.59-4.46 (m, 4H), 4.35 (m, 4H), 3.87 (m, 1H), 3.68 (m, 2H), 3.39-3.34 (m, 1H), 3.17-3.10 (m, 2H), 3.10-3.01 (m, 1H), 2.96 (m, 1H), 2.81 (m, 4H), 2.66 (s, 9H), 2.50 (s, 3H), 2.46-2.33 (m, 1H), 2.31-2.12 (m, 5H), 2.02 (m, 1H), 1.33 (m, 2H), 1.06 (m, 3H), 0.92 (s, 1H), 0.90 (m, 3H). |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| 110 | A | A | 908.8 | 1H NMR (400 MHZ, DMSO-D6): δ 13.74 (s, 1H), 8.97 (s, 1H), 8.44-8.38 (m, 2H), 8.18 (d, J = 12.4 Hz, 2H), 7.99 (d, J = 3.6 Hz, 1H), 7.49-7.24 (m, 5H), 6.93-6.90 (m, 2H), 6.50 (s, 2H), 6.23-6.13 (m, 1H), 5.08-4.87 (m, 2H), 4.38-4.28 (m, 4H), 3.86-3.68 (m, 4H), 3.53-3.42 (m, 10H), 2.63-2.55 (m, 2H), 2.45 (s, 3H), 2.30-2.16 (m, 1H), 2.04-1.97 (m, 1H), 1.94-1.72 (m, 3H), 1.45-1.37 (m, 3H), 0.96-0.75 (m, 6H). |
| 112 | A | A | 928.8 | 1H NMR (400 MHZ, DMSO-D6): δ 8.99 (s, 1H), 8.48-8.42 (m, 2H), 8.21-8.17 (m, 3H), 8.01 (dd, J = 2.0, 8.0 Hz, 1H), 7.47-7.42 (m, 2H), 7.39-7.35 (m, 2H), 7.28-7.24 (m, 1H), 6.93-6.90 (m, 2H), 6.51 (s, 2H), 6.08-5.91 (m, 1H), 5.07 (s, 2H), 4.92-4.88 (m, 1H), 4.36 (t, J = 8.0 Hz, 1H), 4.28-4.17 (m, 3H), 3.71-3.55 (m, 2H), 3.45-3.43 (m, 2H), 2.60 (t, J = 5.6 Hz, 2H), 2.45-2.35 (m, 15H), 2.29-2.18 (m, 1H), 2.05-2.00 (m, 1H), 1.80-1.74 (m, 1H), 1.45-1.36 (m, 3H), 0.97-0.94 (m, 3H), 0.83-0.78 (m, 3H). |
| 113 | A | A | 914.8 | 1H NMR (400 MHZ, DMSO-D6): δ 8.98 (s, 1H), 8.49 (s, 1H), 8.41 (d, J = 7.6 Hz, 1H), 8.21-8.19 (m, 3H), 8.02-8.00 (m, 1H), 7.47-7.42 (m, 2H), 7.38-7.35 (m, 2H), 7.28-7.23 (m, 1H), 6.94-6.90 (m, 2H), 6.49 (s, 2H), 6.09-5.93 (m, 1H), 5.16 (m, 2H), 4.95-4.87 (m, 1H), 4.39-4.35 (m, 1H), 4.28-4.21 (m, 3H), 3.71-3.58 (m, 2H), 3.48-3.14 (m, 5H), 2.67-2.64 (m, 2H), 2.46-2.42 (m, 8H), 2.25-2.16 (m, 2H), 2.05-2.00 (m, 1H), 1.81-1.74 (m, 1H), 1.46-1.37 (m, 3H), 0.97-0.94 (m, 3H), 0.83-0.76 (m, 3H). |
| 114 | A | A | 1045.9 | 1H NMR (400 MHz, DMSO-D6): δ 8.99 (s, 1H), 8.42 (d, J = 7.5 Hz, 1H), 8.21 (s, 2H), 7.92 (d, J = 8.1 Hz, 1H), 7.82-7.76 (m, 1H), 7.50 (s, 1H), 7.47-7.42 (m, 2H), 7.40-7.34 (m, 2H), 7.25-7.20 (m, 1H), 6.90-6.81 (m, 2H), 6.56-6.51 (m, 1H), 6.16 (d, J = 1.6 Hz, 1H), 5.96 (s, 2H), 4.91 (br t, J = 7.4 Hz, 1H), 4.50 (br s, 2H), 4.41-4.36 (m, 1H), 4.33 (br t, J = 5.3 Hz, 2H), 4.31-4.24 (m, 3H), 3.82-3.63 (m, 2H), 3.35-3.21 (m, 2H), 3.02 (br d, J = 11.4 Hz, 2H), 2.74-2.66 (m, 2H), 2.63 (t, J = 5.8 Hz, 2H), 2.46 (s, 12H), 2.31-2.11 (m, 3H), 2.09-1.92 (m, 3H), 1.84-1.74 (m, 1H), 1.47-1.35 (m, 3H), 1.05-0.95 (m, 3H), 0.88-0.79 (m, 3H). |
| 115 | D | B | 1010.8 | 1HNMR (400 MHz, CD3OD): δ 8.42 (d, J = 8.0 Hz, 1H), 8.17 (s, 3H), 7.91 (d, J = 7.6 Hz, 1H), 7.79 (d, J = 6.0 Hz, 1H), 7.67-7.58 (m, 2H), 7.49 (s, 1H), 7.37-7.35 (m, 2H), 7.28-7.18 (m, 2H), 6.96 (s, 1H), 6.90-6.81 (m, 2H), 6.54-6.52 (m, 1H), 6.16 (s, 1H), 6.09 (s, 1H), 6.02-5.91 (m, 2H), 4.99-4.86 (m, 1H), 4.49 (s, 4H), 4.39-4.37 (m, 2H), 4.33-4.18 (m, 8H), 3.77-3.68 (m, 5H), 3.64-3.57 (m, 1H), 3.59-3.39 (m, 2H), 3.37-3.14 (m, 3H), 3.02-2.99 (m, 2H), 2.68 (s, 4H), 2.30-2.09 (m, 4H), 2.01-1.93 (m, 2H), 1.85-1.72 (m, 1H), 1.49-1.21 (m, 4H), 0.96-0.94 (m, 3H), 0.85-0.76 (m, 3H). |
| 116 | A | A | 1028.7 | 1H NMR (400 MHZ, DMSO-D6): δ 9.00 (s, 1H), 8.55-8.45 (m, 2H), 8.14 (s, 2H), 7.91 (br d, J = 7.8 Hz, 1H), 7.81-7.75 (m, 2H), 7.73-7.66 (m, 1H), 7.49 (s, 1H), 7.40 (t, J = 7.8 Hz, 1H), 7.43-7.17 (m, 1H), 6.89-6.79 (m, 2H), 6.53 (br d, J = 4.6 Hz, 1H), 6.16 (s, 1H), 6.09 (s, 1H), 6.01-5.90 (m, 2H), 4.97-4.87 (m, 1H), 4.50 (br s, 2H), 4.35 (t, J = 7.9 Hz, 1H), 4.30-4.17 (m, 6H), 3.73-3.60 (m, 2H), 3.56 (br d, J = 13.1 Hz, 1H), 3.44 (br d, J = 10.0 Hz, 4H), 3.25 (br d, J = 11.0 Hz, 2H), 3.01 (br d, J = 11.2 Hz, 2H), 2.69-2.62 (m, 8H), 2.29-2.14 (m, 4H), 2.06-1.89 (m, 4H), 1.79-1.69 (m, 1H), 1.50-1.38 (m, 3H), 0.98-0.92 (m, 3H), 0.84-0.77 (m, 3H). |
| 117 | B | A | 1012.8 | 1H NMR (400 MHZ, DMSO-D6): δ 8.56-8.55 (m, 1H), 8.45-8.37 (m, 2H), 8.14 (s, 1H), 7.91-7.89 (s, 1H), 7.81-7.77 (m, 2H), 7.66-7.62 (m, 1H), 7.49 (s, 1H), 7.24-7.20 (m, 1H), 6.88-6.83 (m, 2H), 6.57-6.50 (m, 2H), 6.17 (d, J = 1.6 Hz, 1H), 6.09 (s, 1H), 5.97-5.93 (m, 2H), 5.08-4.91 (m, 2H), 4.50 (s, 2H), 4.36-4.26 (m, 6H), 3.71-3.63 (m, 2H), 3.50-3.42 (m, 3H), 3.28 -3.25 (m, 4H), 3.02-2.68 (m, 10H), 2.27-1.95 (m, 7H), 1.78-1.72 (m, 1H), 1.49-1.40 (m, 3H), 0.97-0.92 (m, 3H), 0.84-0.78 (m, 3H). |
| 124 | D | A | 920.8 | 1H NMR (400 MHZ, DMSO-D6): δ 9.02-8.96 (m, 1H), 8.54-8.51 (m, 1H), 8.44 (s, 1H), 8.22-8.14 (m, 3H), 8.02-7.99 (m, 1H), 7.49-7.32 (m, 4H), 7.31-7.21 (m, 1H), 6.96-6.88 (m, 2H), 6.49 (s, 2H), 6.11-5.65 (m, 1H), 4.41-4.26 (m, 6H), 4.16-4.12 (m, 2H), 3.85-3.73 (m, 4H), 3.68-3.65 (m, 2H), 3.54-3.52 (m, 3H), 3.48-3.41 (m, 2H), 2.46-2.33 (m, 11H), 2.32-2.14 (m, 3H), 2.13-1.97 (m, 1H), 1.94-1.89 (m, 1H), 0.95 (d, J = 6.4 Hz, 3H), 0.80 (d, J = 6.8 Hz, 3H). |
| 126 | B | A | 1068.9 | 1H NMR (400 MHZ, DMSO-D6): δ 9.49-9.37 (m, 1H), 9.04 (s, 1H), 7.96 (d, J = 6.8 Hz, 1H), 7.77-7.63 (m, 2H), 7.60-7.45 (m, |

TABLE 2A-continued

| Ex. # | *$DC_{50}$ (nM) | **$D_{max}$ (%)† | MH+ | NMR transcript |
|---|---|---|---|---|
| Target protein degradation via exemplary bifunctional degradation compounds of Table 1A | | | | |
| | | | | 5H), 7.39 (t, J = 7.9 Hz, 1H), 7.09-6.95 (m, 4H), 6.85 (br d, J = 6.4 Hz, 1H), 6.51 (br s, 1H), 6.15 (s, 1H), 4.81 (br s, 2H), 4.72 (br s, 1H), 4.58-4.24 (m, 11H), 3.79-3.61 (m, 4H), 3.47 (br d, J = 9.2 Hz, 1H), 3.34-3.15 (m, 9H), 3.06 (br s, 3H), 2.96 (br s, 3H), 2.47 (s, 3H), 2.36-2.17 (m, 4H), 2.14-1.92 (m, 5H), 0.98-0.85 (m, 3H), 0.80 (br s, 3H). |
| 127 | C | A | 1096.7 | 1H NMR (400 MHZ, CD3OD): δ 8.94-8.86 (m, 1H), 8.37 (br s, 2H), 7.89-7.81 (m, 1H), 7.78-7.63 (m, 3H), 7.53 (d, J = 8.6 Hz, 2H), 7.50-7.44 (m, 1H), 7.29-7.22 (m, 1H), 6.96-6.88 (m, 2H), 6.63 (dd, J = 2.0, 6.2 Hz, 1H), 6.28 (d, J = 1.8 Hz, 1H), 6.05 (d, J = 2.6 Hz, 1H), 4.65-4.46 (m, 8H), 4.41-4.33 (m, 3H), 4.32-4.24 (m, 1H), 3.91-3.82 (m, 1H), 3.74-3.61 (m, 2H), 3.43-3.35 (m, 2H), 3.21-3.02 (m, 8H), 2.97-2.91 (m, 2H), 2.85 (br s, 4H), 2.55-2.47 (m, 3H), 2.45-2.35 (m, 1H), 2.27 (br d, J = 7.5 Hz, 3H), 2.22-2.03 (m, 4H), 2.02-1.96 (m, 3H), 1.10-0.96 (m, 3H), 0.96-0.86 (m, 3H). |
| 128 | A | A | 1071.9 | 1H NMR (400 MHz, CD3OD): δ 8.89 (s, 1H), 7.98-7.89 (m, 2H), 7.76 (s, 1H), 7.46-7.34 (m, 5H), 7.00-6.99 (m, 2H), 6.88-6.78 (m, 2H), 6.07 (s, 1H), 5.11 (s, 1H), 4.66-4.57 (m, 1H), 4.43-4.35 (m, 5H), 3.84-3.35 (m, 11H), 3.18-3.10 (m, 2H), 2.86-2.83 (m, 5H), 2.69-2.60 (m, 7H), 2.50 (s, 3H), 2.40 (s, 1H), 2.21-2.20 (m, 1H), 2.01-1.81 (m, 5H), 1.42 (s, 3H), 1.32-1.21 (m, 3H), 1.19-1.06 (m, 3H), 0.93-0.89 (m, 3H). |
| 129 | D | NA | 1099.4 | 1H NMR (300 MHZ, CD3OD) δ 8.87-8.83 (m, 1H), 7.80-7.67 (m, 2H), 7.56-7.53 (m, 2H), 7.50-7.37 (m, 3H), 7.25-7.19 (m, 1H), 6.90-6.83 (m, 2H), 6.55-6.53 (m, 1H), 6.21-6.20 (m, 1H), 5.99 (s, 1H), 5.15-5.01 (m, 1H), 4.78-4.59 (m, 1H), 4.50-4.42 (m, 3H), 4.35-4.29 (m, 3H), 3.89-3.48 (m, 5H), 3.28-3.18 (m, 4H), 3.12-3.04 (m, 2H), 2.82-2.76 (m, 4H), 2.64-2.52 (m, 7H), 2.48-2.47 (m, 3H), 2.38-2.30 (m, 2H), 2.24-2.08 (m, 6H), 1.88-1.79 (m, 1H), 1.29-1.22 (m, 1H), 1.04-1.02 (m, 1H), 0.94-0.82 (m, 11H). |
| 130 | B | A | 1142.0 | 1H NMR (300 MHz, CD3OD): δ 88.87 (s, 1H), 7.93-7.85 (m, 2H), 7.71 (s, 1H), 7.55-7.42 (m, 4H), 7.34-7.28 (m, 1H), 6.98-6.94 (m, 2H), 6.86-6.80 (m, 2H), 6.00 (s, 1H), 5.14-5.08 (m, 2H), 4.64-4.13 (m, 6H), 3.93-3.83 (m, 3H), 3.71-3.57 (m, 7H), 3.42-3.35 (m, 5H), 3.01-2.97 (m, 2H), 2.82-2.76 (m, 4H), 2.63-2.53 (m, 6H), 2.47-2.28 (m, 5H), 2.19-2.11 (m, 2H), 1.81 (s, 5H), 1.62-1.57 (m, 2H), 1.35-1.27 (m, 2H), 1.04-0.82 (m, 6H). |
| 131 | A | A | 1084.9 | 1H NMR (300 MHz, CD3OD): δ 8.85 (s, 1H), 7.79-7.75 (m, 2H), 7.48-7.42 (m, 5H), 7.25-7.19 (m, 1H), 6.90-6.87(m, 2H), 6.53-6.50 (m, 1H), 6.21-6.20 (m, 1H), 5.97-5.92 (m, 2H), 4.54-4.52 (m, 3H), 4.37-4.32 (m, 5H), 3.88-3.50 (m, 3H), 3.12-3.02 (m, 8H), 2.86-2.66 (m, 11H), 2.48-2.15 (m, 9H), 2.12-1.90 (m, 1H), 1.28-0.84 (m, 10H). |
| 132 | B | A | 1039.9 | 1H NMR (400 MHZ, DMSO-D6): δ 9.02-8.98 (m, 1H), 8.39 (d, J = 7.7 Hz, 1H), 7.96 (d, J = 7.1 Hz, 1H), 7.56 (br d, J = 7.7 Hz, 1H), 7.51 (s, 1H), 7.48-7.43 (m, 2H), 7.42-7.36 (m, 3H), 7.05 (br d, J = 8.1 Hz, 2H), 6.97 (t, J = 7.6 Hz, 1H), 6.88 (br d, J = 7.6 Hz, 1H), 6.58 (s, 1H), 6.14 (s, 1H), 4.97-4.86 (m, 4H), 4.53-4.27 (m, 9H), 3.82-3.55 (m, 5H), 3.53-3.27 (m, 6H), 3.25-3.14 (m, 4H), 2.46 (s, 3H), 2.32-1.85 (m, 7H), 1.51-1.34 (m, 3H), 1.03-0.93 (m, 3H), 0.87-0.77 (m, 3H). |
| 133 | A | A | 1039.9 | 1H NMR (400 MHZ, CD3OD): δ 9.02-8.95 (m, 1H), 7.91-7.83 (m, 1H), 7.61-7.55 (m, 2H), 7.49-7.38 (m, 5H), 7.08-7.02 (m, 2H), 6.93-6.86 (m, 1H), 6.58 (d, J = 2.0 Hz, 1H), 6.07-5.96 (m, 1H), 5.08-4.98 (m, 1H), 4.84-4.75 (m, 1H), 4.69 (br d, J = 4.4 Hz, 2H), 4.55-4.37 (m, 6H), 3.92-3.82 (m, 3H), 3.81-3.69 (m, 3H), 3.64 (br d, J = 10.9 Hz, 1H), 3.60-3.47 (m, 4H), 3.33-3.21 (m, 5H), 3.16-3.03 (m, 1H), 2.52-2.49 (m, 3H), 2.43-2.18 (m, 7H), 2.07-1.93 (m, 1H), 1.64-1.50 (m, 3H), 1.06 (d, J = 6.5 Hz, 3H), 0.95-0.87 (m, 3H). |
| 134 | A | A | 1025.9 | 1H NMR (400 MHZ, DMSO-D6): δ 8.98 (s, 1H), 8.38 (d, J = 7.6 Hz, 1H), 8.25 (s, 2H), 7.92-7.90 (m, 1H), 7.79-7.77 (m, 2H), 7.49-7.36 (m, 5H), 7.24-7.20 (m, 1H), 6.87-6.82 (m, 2H), 6.54-6.52 (m, 1H), 6.25 (s, 1H), 6.15-6.13 (m, 1H), 5.95 (s, 2H), 4.93-6.90 (m, 1H), 4.49 (s, 2H), 4.38-4.25 (m, 4H), 3.74-3.70 (m, 1H), 3.44-3.42 (m, 3H), 3.26-3.23 (m, 2H), 3.03-3.00 (m, 2H), 2.63-2.56 (m, 4H), 2.45-2.42 (m, 7H), 2.34-2.16 (m, 7H), 2.04-1.95 (m, 3H), 1.82-1.70 (m, 3H), 1.45-1.37 (m, 3H), 0.98-0.95 (m, 3H), 0.81-0.76 (m, 3H). |
| 135 | A | A | 1039.9 | 1H NMR (400 MHZ, DMSO-D6): δ 8.97 (s, 1H), 8.38 (d, J = 7.7 Hz, 1H), 8.17 (s, 3H), 7.90 (d, J = 7.9 Hz, 1H), 7.79 (d, J = 6.0 Hz, 1H), 7.53-7.40 (m, 3H), 7.39-7.32 (m, 2H), 7.21 (t, J = 7.6 Hz, 1H), 6.91-6.80 (m, 2H), 6.54 (br d, J = 5.9 Hz, 1H), 6.15 (s, 1H), |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| | | | | 6.07 (s, 1H), 5.99-5.91 (m, 2H), 4.97-4.85 (m, 1H), 4.49 (br s, 2H), 4.36 (br t, J = 7.8 Hz, 1H), 4.25 (br s, 4H), 4.16 (br s, 2H), 3.74-3.60 (m, 2H), 3.47-3.40 (m, 4H), 3.25 (br d, J = 11.0 Hz, 2H), 3.01 (br d, J = 11.5 Hz, 2H), 2.95-2.73 (m, 8H), 2.45 (s, 3H), 2.23-2.16 (m, 2H), 2.02-1.94 (m, 2H), 1.78 (ddd, J = 5.2, 8.0, 12.9 Hz, 1H), 1.67 (br s, 2H), 1.46-1.34 (m, 3H), 1.01-0.87 (m, 3H), 0.84-0.73 (m, 3H). |
| 136 | A | A | 1039.9 | 1H NMR (400 MHZ, CD3OD): δ 8.99-8.88 (m, 1H), 7.89-7.78 (m, 1H), 7.60-7.52 (m, 2H), 7.49-7.38 (m, 5H), 7.07-6.98 (m, 2H), 6.87 (dd, J = 2.1, 7.4 Hz, 1H), 6.55 (d, J = 2.1 Hz, 1H), 6.12-5.97 (m, 1H), 5.02 (dt, J = 7.0, 13.9 Hz, 1H), 4.81-4.74 (m, 1H), 4.63-4.39 (m, 7H), 4.30-4.21 (m, 1H), 3.90-3.77 (m, 4H), 3.73-3.37 (m, 10H), 3.29 ( s, 1H), 2.50-2.46 (m, 3H), 2.43-2.14 (m, 9H), 2.05-1.90 (m, 1H), 1.62-1.48 (m, 3H), 1.08-1.02 (m, 3H), 0.94-0.86 (m, 3H). |
| 139 | A | A | 1041.9 | 1H NMR (400 MHz, DMSO-D6): δ 8.98 (s, 1H), 8.45-8.34 (m, 1H), 8.18 (s, 3H), 7.91 (d, J = 7.9 Hz, 1H), 7.79 (d, J = 6.0 Hz, 1H), 7.51-7.46 (m, 1H), 7.44 (d, J = 8.1 Hz, 2H), 7.40-7.34 (m, 2H), 7.22 (t, J = 7.7 Hz, 1H), 6.90-6.82 (m, 2H), 6.53 (dd, J = 1.9, 6.1 Hz, 1H), 6.14 (d, J = 1.7 Hz, 1H), 6.09 (s, 1H), 5.99-5.90 (m, 2H), 4.96-4.88 (m, 1H), 4.49 (br s, 3H), 4.37 (br t, J = 7.8 Hz, 1H), 4.29-4.25 (m, 3H), 4.22 (br t, J = 5.5 Hz, 3H), 3.70 (br dd, J = 4.3, 10.5 Hz, 1H), 3.64 (d, J = 9.7 Hz, 1H), 3.48-3.41 (m, 1H), 3.25 (br d, J = 11.5 Hz, 2H), 3.05-2.95 (m, 3H), 2.83 (br d, J = 11.6 Hz, 1H), 2.68 (br d, J = 8.8 Hz, 2H), 2.62 (br t, J = 5.5 Hz, 2H), 2.46 (s, 3H), 2.44-2.33 (m, 2H), 2.18 (br d, J = 7.3 Hz, 3H), 2.05-1.89 (m, 4H), 1.79 (ddd, J = 4.8, 7.9, 12.8 Hz, 1H), 1.46-1.35 (m, 3H), 0.97 (dd, J = 6.4, 11.1 Hz, 6H), 0.86-0.76 (m, 3H). |
| 140 | A | A | 1041.9 | 1H NMR (400 MHZ, CD3OD): δ 8.95 (d, J = 3.7 Hz, 1H), 7.86-7.81 (m, 1H), 7.58-7.54 (m, 2H), 7.48-7.38 (m, 5H), 7.07-7.01 (m, 2H), 6.87 (dd, J = 2.0, 7.2 Hz, 1H), 6.55 (s, 1H), 6.07-6.00 (m, 1H), 5.02 (td, J = 7.1, 14.3 Hz, 3H), 4.83-4.75 (m, 1H), 4.64-4.36 (m, 6H), 3.92-3.80 (m, 3H), 3.76-3.68 (m, 1H), 3.62 (d, J = 10.9 Hz, 1H), 3.55-3.37 (m, 6H), 3.29 (s, 1H), 3.24-2.98 (m, 4H), 2.84 (s, 1H), 2.50-2.47 (m, 3H), 2.42-2.27 (m, 3H), 2.24-2.15 (m, 3H), 2.06-1.91 (m, 1H), 1.62-1.47 (m, 3H), 1.32 (d, J = 5.3 Hz, 3H), 1.07-1.04 (m, 3H), 0.93-0.86 (m, 3H). |
| 141 | A | A | 1041.9 | 1H NMR (400 MHZ, CD3OD): δ 9.02-8.97 (m, 1H), 7.87-7.82 (m, 1H), 7.62-7.55 (m, 2H), 7.49-7.40 (m, 5H), 7.08-7.03 (m, 2H), 6.88 (d, J = 6.8 Hz, 1H), 6.57 (d, J = 2.0 Hz, 1H), 6.09 (s, 1H), 5.14-4.95 (m, 1H), 4.81-4.72 (m, 2H), 4.64-4.41 (m, 6H), 3.91-3.70 (m, 5H), 3.64 (br d, J = 11.1 Hz, 2H), 3.56-3.37 (m, 3H), 3.29 (br s, 4H), 3.17 (br s, 2H), 2.95 (br d, J = 9.3 Hz, 1H), 2.77 (br d, J = 9.8 Hz, 1H), 2.52-2.49 (m, 3H), 2.44-2.27 (m, 6H), 2.08-1.94 (m, 1H), 1.54-1.42 (m, 3H), 1.45-1.35 (m, 3H), 1.10-1.04 (m, 3H), 0.95-0.87 (m, 3H). |
| 142 | A | A | 1041.9 | 1H NMR (400 MHZ, CD3OD): δ 8.91-8.82 (m, 1H), 8.30 (br s, 2H), 7.84-7.76 (m, 1H), 7.75-7.65 (m, 1H), 7.47-7.35 (m, 5H), 7.24 (t, J = 7.8 Hz, 1H), 6.96-6.83 (m, 2H), 6.62 (br d, J = 6.4 Hz, 1H), 6.31-6.21 (m, 1H), 6.04-5.96 (m, 1H), 5.02 (quin, J = 6.9 Hz, 1H), 4.60-4.31 (m, 9H), 3.83 (dd, J = 4.2, 10.8 Hz, 1H), 3.77-3.66 (m, 1H), 3.61 (br d, J = 11.2 Hz, 1H), 3.42-3.34 (m, 2H), 3.26-3.20 (m, 2H), 3.16 (br s, 2H), 3.10 (br d, J = 11.7 Hz, 2H), 2.95-2.74 (m, 3H), 2.75-2.74 (m, 1H), 2.55 (br t, J = 11.4 Hz, 1H), 2.50-2.43 (m, 3H), 2.42-2.07 (m, 7H), 2.05-1.92 (m, 1H), 1.62-1.47 (m, 3H), 1.24-1.15 (m, 3H), 1.05 (d, J = 6.5 Hz, 3H), 0.93-0.85 (m, 3H). |
| 143 | A | A | 1122.0 | $^1$H NMR (400 MHZ, CD3OD): δ: 8.88 (s, 1H), 8.52 (s, 1H), 7.83-7.71 (m, 2H), 7.51-7.37 (m, 5H), 7.24 (t, J = 7.0 Hz, 1H), 6.93-6.85 (m, 1H), 6.93-6.85 (m, 1H), 6.56 (dd, J = 2.0, 6.1 Hz, 1H), 6.16-6.04 (m, 2H), 5.15 (t, J = 3.7 Hz, 1H), 5.08-5.00 (m, 1H), 4.76 (t, J = 8.0 Hz, 1H), 4.60-4.39 (m, 6H), 3.85 (dd, J = 4.2, 10.8 Hz, 1H), 3.77-3.55 (m, 5H), 3.38-3.34 (m, 2H), 3.11 (d, J = 11.7 Hz, 4H), 2.92-2.71 (m, 5H), 2.50-2.12 (m, 14H), 1.97 (ddd, J = 4.8, 8.6, 13.0 Hz, 4H), 1.82 (d, J = 11.2 Hz, 4H), 1.61-1.48 (m, 3H), 1.33 (d, J = 8.6 Hz, 2H), 1.06 (d, J = 6.5 Hz, 3H), 0.95-0.86 (m, 3H). |
| 144 | A | A | 1137.0 | 1H NMR (400 MHZ, DMSO-D6): δ 8.99 (s, 1H), 8.42 (d, J = 7.6 Hz, 1H), 8.27 (s, 2H), 7.93 (d, J = 7.3 Hz, 1H), 7.77 (d, J = 6.0 Hz, 1H), 7.50 (s, 1H), 7.46-7.41 (m, 2H), 7.41-7.34 (m, 2H), 7.23 (t, J = 7.2 Hz, 1H), 6.90-6.82 (m, 2H), 6.53 (dd, J = 1.7, 6.0 Hz, 1H), 6.14 (s, 2H), 6.06-5.91 (m, 2H), 5.31-5.05 (m, 1H), 4.96-4.80 (m, 1H), 4.50 (br s, 2H), 4.40-4.34 (m, 1H), 4.32-4.26 (m, 2H),3.71 (br dd, J = 4.3, 10.1 Hz, 5H), 3.29-3.21 (m, 5H), 3.16- |

TABLE 2A-continued

Target protein degradation via exemplary bifunctional degradation compounds of Table 1A

| Ex. # | *$DC_{50}$ (nM) | **$D_{max}$ (%)† | MH+ | NMR transcript |
|---|---|---|---|---|
| | | | | 3.11 (m, 5H), 3.02 (br d, J = 11.4 Hz, 2H), 2.86-2.70 (m, 3H), 2.46 (s, 5H), 2.42 (s, 3H), 2.31-2.24 (m, 3H), 2.22-2.14 (m, 3H), 2.07-1.93 (m, 5H), 1.82-1.76 (m, 2H), 1.46 (br d, J = 7.1 Hz, 2H), 1.38 (br d, J = 6.8 Hz, 3H), 0.95 (d, J = 6.4 Hz, 3H), 0.79 (d, J = 6.8 Hz, 3H). |
| 146 | A | A | 1054.9 | $^1$H NMR (400 MHZ, DMSO-D6): δ 8.99 (s, 1H), 8.53 (t, J = 5.6 Hz, 1H), 8.21 (s, 2H), 7.92-7.90 (m, 1H), 7.77-7.76 (m, 1H), 7.49-7.36 (m, 5H), 7.24-7.20 (m, 1H), 6.92-6.82 (m, 2H), 6.53-6.51 (m, 1H), 6.14-6.10 (m, 2H), 5.98-5.70 (m, 2H), 5.20-5.16 (m, 1H), 4.49 (s, 2H), 4.38-4.15 (m, 7H), 3.80-3.74 (m, 2H), 3.66 (d, J = 9.6 Hz, 2H), 3.49-3.41 (m, 2H), 3.29-3.16 (m, 4H), 3.01 (d, J = 11.2 Hz, 1H), 2.76-2.63 (m, 2H), 2.45-2.42 (m, 3H), 2.35-1.90 (m, 12H), 1.78-1.75 (m, 2H), 1.48-1.36 (m, 2H), 0.94 (d, J = 6.8 Hz, 3H), 0.79 (d, J = 6.8 Hz, 3H). |

†when tested at the top concentration of between 0.3 and 10 μM
*$DC_{50}$ (nM)
A < 2.5
2.5 ≤ B < 10
10 ≤ C < 30
D ≥ 30
**$D_{max}$ (% degraded)
A > 75
50 < B ≤ 75
C ≤ 50

TABLE 2B

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| 156 | D | A | 898.6 | 1H NMR (300 MHz, CD3OD): δ 8.81 (s, 1H), 8.51-8.20 (s, 1H), 8.14-8.00 (m, 2H), 7.97-7.74 (m, 1H), 7.58-7.15 (m, 7H), 7.08-6.73 (m, 4H), 6.12-5.95 (m, 1H), 5.75-5.54 (m, 1H), 5.22-4.97 (m, 1 H), 4.62-4.38 (m, 4H), 4.37-4.24 (m, 2H), 3.87-3.75 (m, 1H), 3.75-3.58 (m, 2H), 2.55-2.46 (m, 3H), 2.44-2.33 (m, 1H), 2.30-2.22 (m, 1H), 2.02-1.88 (m, 4H), 1.63-1.427 (m, 3H), 1.41-1.28 (m, 1H), 1.11-0.80 (m, 6H). |
| 157 | C | A | 899.6 | 1H NMR (300 MHz, CD3OD): δ 8.91-8.68 (m, 1H), 8.35-8.29 (m, 1H), 8.13-8.01 (m, 2H), 7.84-7.83 (m, 1H), 7.70-7.67 (m, 1H), 7.63-7.57 (m, 1H), 7.43-7.23 (m, 5H), 6.93-6.87 (m, 2H), 6.53-6.50 (m, 1H), 5.97-5.93 (m, 1H), 5.55-5.48 (m, 1H), 5.02-4.94 (m, 1H), 4.56-4.34 (m, 6H), 3.81-3.75 (m, 1H), 3.63-3.42 (m, 3H), 2.45-2.36 (m, 3H), 2.31-2.12 (m, 2H), 1.99-1.81 (m, 4H), 1.56-1.52 (m, 1H), 1.48-1.45 (m, 2H), 1.31-1.25 (m, 1H), 1.01-0.88 (m, 3H), 0.86-0.79 (m, 3H). |
| 158 | D | A | 1043.7 | $^1$H NMR (300 MHZ, $CD_3OD-d_6$): 8.84 (s, 1H), 7.94-7.78 (m, 1H), 7.78-7.67 (m, 1H), 7.52-7.32 (m, 5H), 7.32-7.18 (m, 1H), 7.00-6.82 (m, 2H), 6.72-6.61 (m, 1H), 6.41-6.24 (m, 1H), 6.05 (s, 1H), 5.03-4.97 (m, 1H), 4.73-4.60 (m, 1H), 4.60-4.51 (m, 2H), 4.51-4.42 (m, 3H), 4.42-4.28 (m, 2H), 3.92-3.58 (m, 5H), 3.43-3.36 (m, 2H), 3.26-3.21 (m, 2H), 3.17-3.07 (m, 5H), 3.02-2.80 (m, 6H), 2.54-2.46 (m, 3H), 2.46-2.32 (m, 1H), 2.31-2.20 (m, 3H), 2.20-2.12 (m, 2H), 2.07-1.98 (m, 1H), 1.36-1.31 (m, 1H), 1.14-0.97 (m, 3H), 0.97-0.84(m, 3H). |
| 159 | D | C | 1010.8 | 1H NMR (400 MHZ, DMSO-D6): δ 8.33 (d, J = 7.6 Hz, 1H), 8.17 (s, 4H), 7.92 (d, J = 7.6 Hz, 1H), 7.79 (d, J = 6.0 Hz, 1H), 7.69-7.57 (m, 2H), 7.50 (s, 1H), 7.45-7.29 (m, 2H), 7.27-7.17 (m, 2H), 7.01-6.92 (m, 1H), 6.90-6.81 (m, 2H), 6.54 (d, J = 6.0 Hz, 1H), 6.16 (s, 1H), 6.09 (s, 1H), 5.98 (s, 2H), 4.94-4.86 (m, 1H), 4.59-4.35 (m, 6H), 4.33-4.13 (m, 8H), 3.79-3.68 (m, 5H), 3.57-3.54 (m, 1H), 3.51-3.38 (m, 2H), 3.26-3.23 (m, 3H), 3.02-2.99 (m, 2H), 2.67-2.66 (m, 4H), 2.30-2.12 (m, 4H), 1.96 (s, 2H), 1.85-1.72 (m, 1H), 1.55-1.23 (m, 4H), 0.97 (d, J = 6.4 Hz, 3H), 0.83 (d, J = 6.4 Hz, 3H). |
| 160 | D | A | 1028.7 | 1H NMR (400 MHZ, DMSO-D6): δ 9.03-8.97 (m, 1H), 8.60-8.47 (m, 1H), 8.37 (d, J = 7.5 Hz, 1H), 8.16 (s, 2H), 7.92 (d, J = 8.1 Hz, 1H), 7.87-7.77 (m, 1H), 7.76-7.64 (m, 2H), 7.50 (s, 1H), 7.25-7.17 (m, 1H), 6.89-6.79 (m, 2H), 6.57-6.49 (m, 1H), 6.19-6.12 (m, 1H), 6.08 (s, 1H), 5.97 (s, 2H), 5.07-4.85 (m, 1H), 4.50 (br s, 2H), 4.40 (t, J = 7.8 Hz, 1H), 4.32-4.16 (m, 6H), 3.74 (d, J = 8.6 Hz, 1H), 3.59-3.53 (m, 1H), 3.46 (br dd, J = 4.2, 10.6 Hz, 2H), 3.26 (br s, 2H), 3.01 (br d, J = 11.1 Hz, 2H), 2.70-2.58 (m, 8H), 2.43 (br s, 4H), 2.29-2.12 (m, 4H), 2.09-2.01 (m, 1H), |

TABLE 2B-continued

| Target protein degradation via exemplary bifunctional degradation compounds of Table 1B | | | | |
|---|---|---|---|---|
| Ex. # | *$DC_{50}$ (nM) | **$D_{max}$ (%) | MH+ | NMR transcript |
| | | | | 2.00-1.90 (m, 2H), 1.80-1.67 (m, 1H), 1.51-1.35 (m, 3H), 0.96 (d, J = 6.6 Hz, 3H), 0.85-0.78 (m, 3H), 0.75 (d, J = 6.7 Hz, 1H). |
| 161 | D | C | 1012.7 | 1H NMR (400 MHz, DMSO-D6): δ 8.62-8.53 (m, 1H), 8.38-8.33 (m, 2H), 8.15 (s, 1H), 7.91-7.83 (s, 1H), 7.78 (d, J = 6.0 Hz, 1H), 7.73-7.66 (m, 1H), 7.60 (d, J = 8.0 Hz, 1H), 7.49 (s, 1H), 7.21 (d, J = 8.0 Hz, 1H), 6.87-6.82 (m, 2H), 6.54-6.52 (m, 1H), 6.15-6.13 (m, 1H), 6.07 (s, 1H), 5.95 (s, 2H), 5.05-4.87 (m, 2H), 4.49-4.19 (m, 8H), 3.74 (d, J = 8.8 Hz, 1H), 3.56-3.43 (m, 6H), 3.32-3.17 (m, 8H), 3.01 (d, J = 11.2 Hz, 2H), 2.67-2.59 (m, 4H), 2.35-2.22 (m, 2H), 2.04-1.71 (m, 4H), 1.49-1.37 (m, 3H), 0.97-0.74 (m, 6H). |
| 162 | D | A | 899.7 | 1H NMR (300 MHz, CD3OD): δ 8.87-8.81 (m, 1H), 8.37-8.34 (m, 1H), 8.19-8.11 (m, 2H), 7.85-7.77 (m, 1H), 7.71-7.59 (m, 2H), 7.45-7.42 (m, 1H), 7.35-7.23 (m, 5H), 6.95-6.89 (m, 2H), 6.54-6.51 (m, 1H), 6.01-5.95 (m, 1H), 5.52-5.47 (m, 1H), 4.94-4.91 (m, 1H), 4.60-4.37 (m, 6H), 3.72-3.55 (m, 3H), 2.48-2.41 (m, 3H), 2.34-2.17 (m, 2H), 2.04-1.85 (m, 5H), 1.58-1.56 (m, 1H), 1.47-1.39 (m, 3H), 1.33-1.26 (m, 1H), 1.02-0.91 (m, 3H), 0.86-0.77 (m, 3H). |
| 163 | A | A | 899.7 | 1H NMR (300 MHz, CD3OD): δ 88.87-8.81 (m, 1H), 8.37 (s, 1H), 8.14-8.13 (m, 1H), 8.07-8.05 (m, 2H), 7.84-7.80 (m, 1H), 7.73-7.68 (m, 1H), 7.45-7.21 (m, 5H), 6.93-6.87 (m, 2H), 6.80-6.73 (m, 1H), 6.00-5.97 (m, 1H), 5.70-5.63 (m, 1H), 4.99-4.92 (m, 1H), 4.59-4.41 (m, 6H), 3.75-3.58 (m, 3H), 2.47-2.43 (m, 3H), 2.39-2.30 (m, 1H), 2.23-2.15 (m, 1H), 1.97-1.87 (m, 4H), 1.58-1.43 (m, 3H), 1.04-0.94 (m, 3H), 0.92-0.81 (m, 3H). |
| 164 | C | B | 1033.9 | 1H NMR (300 MHz, CD3OD): δ 8.88 (s, 1H), 7.82-7.76 (m, 1H), 7.53 (s, 1H), 7.50-7.35 (m, 4H), 7.30-7.21 (m, 1H), 6.98-6.89 (m, 2H), 6.04 (s, 1H), 5.06-4.95 (m, 1H), 4.62-4.55 (m, 1H), 4.50-4.40 (m, 1H), 4.35-4.23 (m, 2H), 4.10-3.95 (m, 1H), 3.81-3.72 (m, 3H), 3.72-3.60 (m, 2H), 3.60-3.45 (m, 2H), 3.29-3.19 (m, 2H), 3.19-3.05 (m, 2H), 2.78-2.68 (m, 2H), 2.58-2.31 (m, 14H), 2.30-2.02 (m, 5H), 2.02-1.78 (m, 3H), 1.72-1.55 (m, 6H), 1.53-1.44 (m, 3H), 1.10-0.82 (m, 6H). |
| 165 | D | C | 920.8 | 1H NMR (400 MHz, DMSO-D6): δ 9.02-8.96 (m, 1H), 8.53-8.41 (m, 2H), 8.22-8.15 (m, 4H), 8.01-7.99 (m, 1H), 7.47-7.39 (m, 2.5H), 7.35-7.30 (m, 1.5H), 7.27-7.23 (m, 1H), 6.96-6.88 (m, 2H), 6.49 (s, 2H), 6.09-6.02 (m, 1H), 4.46-4.42 (m, 2H), 4.38-4.23 (m, 6H), 4.18-4.06 (m, 3H), 3.87-3.72 (m, 4H), 3.63-3.41 (m, 4H), 2.46-2.33 (m, 11H), 2.29-2.13 (m, 3H), 2.11-1.98 (m, 2H), 1.95-1.83 (m, 1H), 0.98-0.96 (m, 3H), 0.84-0.82 (m, 3H). |
| 166 | B | A | 980.2 | 1H NMR (300 MHz, CD3OD): δ 8.86 (s, 1H), 8.39 (s, 1H), 8.10 (s, 2H), 7.85 (d, J = 6.9 Hz, 1H), 7.50-7.31 (m, 8H), 7.31-7.22 (m, 1H), 7.00-6.90 (m, 2H), 6.03 (s, 1H), 5.77-5.65 (m, 1H), 5.05-4.94 (m, 1H), 4.62-4.53 (m, 1H), 4.49-4.40 (m, 1H), 4.00-4.29 (m, 2H), 3.80-3.55 (m, 5H), 3.41-3.39 (m, 1H), 2.90-2.80 (m, 2H), 2.80-2.52 (m, 7H), 2.51-2.43 (m, 3H), 2.43-2.30 (m, 1H), 2.30-2.15 (m, 1H), 2.10-2.89 (m, 4H), 2.61-2.42 (m, 3H), 1.10-0.80 (m, 6H). |
| 167 | C | A | 1070.9 | 1H NMR (400 MHZ, DMSO-D6): δ 10.08 (s, 1H), 9.35-9.27 (m, 1H), 8.47 (d, J = 7.6 Hz, 1H), 7.95 (d, J = 7.2 Hz, 1H), 7.56 (d, J = 7.6 Hz, 1H), 7.50-7.36 (m, 6H), 7.05-6.94 (m, 4H), 6.85 (d, J = 5.6 Hz, 1H), 6.52 (s, 1H), 6.12-6.00 (m, 1H), 4.96-4.87 (m, 1H), 4.81-4.70 (m, 2H), 4.50 (s, 4H), 4.43-4.35 (m, 3H), 4.30 (s, 1H), 3.79-3.56 (m, 4H), 3.46 (d, J = 11.2 Hz, 1H), 3.29 (d, J = 8.0 Hz, 2H), 3.20-2.94 (m, 10H), 2.76 (s, 6H), 2.53-2.51 (m, 2H), 2.33-2.16 (m, 4H), 2.07-2.00 (m, 3H), 1.81-1.75 (m, 1H), 1.48-1.37 (m, 3H), 0.99-0.95 (m, 3H), 0.85-0.79 (m, 3H). |
| 168 | A | A | 1043.9 | 1H NMR (400 MHZ, DMSO-D6): δ 9.04-8.89 (m, 1H), 7.88-7.76 (m, 1H), 7.60-7.50 (m, 4H), 7.48-7.34 (m, 3H), 7.09-6.97 (m, 2H), 6.90-6.80 (m, 1H), 6.90-6.80 (m, 1H), 6.55 (d, J = 2.2 Hz, 1H), 6.10-5.94 (m, 1H), 5.09-4.96 (m, 1H), 4.92-4.89 (m, 2H), 4.83-4.74 (m, 1H), 4.70-4.64 (m, 2H), 4.61-4.37 (m, 6H), 3.90-3.75 (m, 3H), 3.70 (d, J = 9.9 Hz, 1H), 3.66-3.57 (m, 1H), 3.53-3.44 (m, 2H), 3.35 (br s, 4H), 3.31-3.27 (m, 2H), 3.26-3.06 (m, 6H), 2.44-2.14 (m, 6H), 2.06-1.89 (m, 1H), 1.64-1.45 (m, 3H), 1.05 (d, J = 6.5 Hz, 3H), 0.93-0.84 (m, 3H). |
| 169 | A | A | 1057.9 | 1H NMR (400 MHZ, DMSO-D6): δ 8.99-8.89 (m, 1H), 7.88-7.78 (m, 1H), 7.60-7.48 (m, 4H), 7.46-7.35 (m, 3H), 7.08-6.97 (m, 2H), 6.90-6.81 (m, 1H), 6.58-6.49 (m, 1H), 6.11-5.93 (m, 1H), 5.09-4.96 (m, 1H), 4.89 (br s, 2H), 4.81-4.73 (m, 1H), 4.61-4.48 (m, 7H), 4.47-4.36 (m, 1H), 3.89-3.75 (m, 3H), 3.71 (d, J = 9.7 Hz, 1H), 3.66-3.58 (m, 1H), 3.54-3.41 (m, 3H), 3.41-3.38 (m, 3H), 3.36-3.33 (m, 2H), 3.30-3.27 (m, 2H), 3.23-2.99 (m, 6H), 2.41-2.15 (m, 6H), 2.06-1.89 (m, 1H), 1.62-1.46 (m, 3H), 1.05 (d, J = 6.5 Hz, 3H), 0.94-0.85 (m, 3H). |
| 170 | B | A | 1025.9 | 1H NMR (400 MHZ, DMSO-D6): δ 8.99-8.97 (m, 1H), 8.30-8.25 (m, 3H), 7.92-7.90 (m, 1H), 7.79-7.77 (m, 1H), 7.49-7.39 (m, 4H), 7.32-7.20 (m, 4H), 6.87-6.82 (m, 2H), 6.53-6.51 (m, 1H), 6.30-6.27 (m, 1H), 6.15-6.14 (m, 1H), 5.97 (s, 2H), 4.89-6.85 (m, 1H), 4.49-4.40 (m, 4H), 4.27-4.24 (m, 4H), 3.83 (d, J = 8.8 Hz, 1H), 3.57-3.52 (m, 2H), 3.48-3.41 (m, 1H), 3.25-3.22 (m, 2H), 3.00 (d, J = 11.6 Hz, 2H), 2.61- |

TABLE 2B-continued

| Ex. # | *DC$_{50}$ (nM) | **D$_{max}$ (%) | MH+ | NMR transcript |
|---|---|---|---|---|
| | | | | Target protein degradation via exemplary bifunctional degradation compounds of Table 1B |
| | | | | 2.55 (m, 3H), 2.46-2.42 (m, 6H), 2.29-2.13 (m, 4H), 2.04-1.92 (m, 3H), 1.79-1.67 (m, 3H), 1.46 (d, J = 7.2 Hz, 1H), 1.34 (d, J = 7.2 Hz, 3H), 0.96 (d, J = 6.8 Hz, 3H), 0.83-0.71 (m, 3H). |
| 171 | D | B | 1084.9 | 1H NMR (300 MHz, CD3OD): δ 8.85 (s, 1H), 7.78-7.53 (m, 2H), 7.46-7.41 (m, 5H), 7.22-7.19 (m, 1H), 6.89-6.87(m, 2H), 6.52-6.50 (m, 1H), 6.20-6.19 (m, 1H), 6.09-5.90 (m, 2H), 4.59-4.29 (m, 8H), 3.76-3.66 (m, 3H), 3.33-3.30 (m, 1H), 3.11-3.01 (m, 2H), 2.99-2.96 (m, 6H), 2.80-2.48 (m, 15H), 2.46-1.90 (m, 8H), 1.29-1.26 (m, 1H), 1.03-0.89 (m, 2H), 0.88-0.85 (m, 4H). |
| 172 | A | A | 1094.9 | 1H NMR (400 MHZ, DMSO-D6): δ 9.01 (s, 1H), 8.12 (s, 2H), 8.00-7.67 (m, 5H), 7.58-7.46 (m, 1H), 7.43-7.34 (m, 2H), 7.22 (br t, J = 7.2 Hz, 1H), 6.95-6.82 (m, 2H), 6.57-6.50 (m, 1H), 6.18-6.03 (m, 3H), 5.94-5.67 (m, 2H), 4.97-4.89 (m, 1H), 4.49 (br s, 2H), 4.45-4.31 (m, 3H), 4.27 (br t, J = 5.2 Hz, 2H), 3.74 (br dd, J = 4.8, 10.4 Hz, 1H), 3.66 (br d, J = 9.2 Hz, 1H), 3.57 (br d, J = 4.0 Hz, 2H), 3.54-3.50 (m, 1H), 3.46-3.35 (m, 2H), 3.30 (br d, J = 11.2 Hz, 2H), 3.23 (br d, J = 11.2 Hz, 2H), 3.06 (br d, J = 11.6 Hz, 2H), 2.83-2.81 (m, 2H), 2.67 (br s, 4H), 2.61 (br s, 4H), 2.31-2.25 (m, 6H), 2.21-2.07 (m, 3H), 2.02-1.78 (m, 4H), 1.50-1.34 (m, 3H), 0.98 (br d, J = 6.5 Hz, 3H), 0.91-0.82 (m, 3H). |
| 173 | D | A | 1063.8 | 1H NMR (300 MHz, DMSO-D6): δ 14.14 (s, 1H), 9.01 (d, J = 5.7 Hz, 1H), 8.83 (d, J = 8.9 Hz, 1H), 7.91 (d, J = 7.6 Hz, 1H), 7.78 (d, J = 6.0 Hz, 1H), 7.70-7.40 (m, 5H), 7.30-7.20 (m, 1H), 6.90-6.78 (m, 2H), 6.60-6.50 (m, 1H), 6.25-6.20 (m, 1H), 6.20-6.10 (m, 1H), 6.10-6.00 (m, 2H), 5.20-5.00 (m, 1H), 4.60-4.40 (m, 3H), 4.35-4.20 (m, 5H), 3.80-3.70 (m, 1H), 3.65-3.40 (m, 2H), 3.30-3.20 (m, 2H), 3.01 (d, J = 11.7 Hz, 2H), 2.70-60 (m, 4H), 2.50-2.40 (m, 12H), 2.25-2.15 (m, 3H), 2.15-2.10 (m, 1H), 2.10-1.95 (m, 2H), 1.80-1.70(m, 1H), 1.00-0.70 (m, 6H). |
| 174 | C | A | 1084.9 | 1H NMR (400 MHz, DMSO-D6): δ 8.99-8.91 (m, 1H), 7.88-7.81 (m, 1H), 7.58-7.53 (m, 2H), 7.51-7.34 (m, 5H), 7.07-7.00 (m, 2H), 6.89-6.84 (m, 1H), 6.55 (s, 1H), 6.09-6.00 (m, 1H), 5.06-4.94 (m, 2H), 4.80-4.76 (m, 2H), 4.61-4.37 (m, 8H), 3.89-3.75 (m, 3H), 3.75-3.57 (m, 2H), 3.53-3.46 (m, 2H), 3.34 (s, 3H), 3.29 (s, 2H), 3.22-3.03 (m, 6H), 2.40-2.10 (m, 6H), 1.93-1.89 (m, 3H), 1.63-1.42 (m, 4H), 1.05 (d, J = 6.4 Hz, 3H), 0.95-0.84 (m, 3H). |
| 175 | B | A | 1108.9 | 1H NMR (400 MHZ, CD3OD): δ 8.90-8.83 (m, 1H), 7.84-7.69 (m, 4H), 7.49-7.31 (m, 3H), 7.22 (br t, J = 7.6 Hz, 1H), 6.93-6.86 (m, 2H), 6.55 (br d, J = 4.0 Hz, 1H), 6.21 (s, 1H), 6.04-5.93 (m, 1H), 5.07-4.94 (m, 1H), 4.82-4.72 (m, 1H), 4.66-4.47 (m, 4H), 4.46-4.27 (m, 5H), 4.25-4.16 (m, 2H), 3.86-3.45 (m, 3H), 3.34 (br s, 1H), 3.23-3.06 (m, 2H), 2.95-2.49 (m, 12H), 2.44-2.30 (m, 1H), 2.27-2.18 (m, 3H), 2.14 (br d, J = 5.6 Hz, 2H), 2.02-1.90 (m, 4H), 1.61-1.45 (m, 3H), 1.04 (br d, J = 6.5 Hz, 3H), 0.93-0.85 (m, 3H). |
| 176 | D | C | 1051.9 | 1H NMR (400 MHZ, DMSO-D6): δ 10.02 (br s, 1H), 8.54 (d, J = 7.6 Hz, 1H), 7.95 (d, J = 7.1 Hz, 1H), 7.88-7.82 (m, 1H), 7.80-7.72 (m, 1H), 7.65-7.53 (m, 4H), 7.51-7.45 (m, 3H), 7.37 (t, J = 7.8 Hz, 1H), 7.07-6.93 (m, 4H), 6.85 (br d, J = 6.8 Hz, 1H), 6.27 (s, 1H), 6.13 (s, 1H), 5.22 (br s, 1H), 4.92 (td, J = 7.2, 14.5 Hz, 1H), 4.83 (br s, 2H), 4.51 (br s, 2H), 4.45 (br t, J = 7.8 Hz, 2H), 4.34 (br s, 2H), 4.26 (br s, 2H), 3.79 (br d, J = 8.7 Hz, 2H), 3.64-3.54 (m, 6H), 3.46-3.34 (m, 2H), 3.22-2.99 (m, 5H), 2.43 (br s, 2H), 2.29-2.15 (m, 4H), 2.09-1.83 (m, 5H), 1.77-1.57 (m, 2H), 1.50-1.32 (m, 4H), 0.97 (d, J = 6.6 Hz, 3H), 0.83 (d, J = 6.7 Hz, 4H). |
| 178 | A | A | 1051.9 | 1H NMR (400 MHZ, DMSO-D6): δ 8.47-8.40 (m, 1H), 8.15 (s, 3H), 7.92 (d, J = 7.0 Hz, 1H), 7.77 (d, J = 6.1 Hz, 1H), 7.49 (s, 1H), 7.43-7.34 (m, 5H), 7.26-7.17 (m, 2H), 6.92-6.80 (m, 3H), 6.52 (d, J = 6.0 Hz, 1H), 6.13 (s, 1H), 6.09 (s, 1H), 5.98 (s, 2H), 5.18 (br s, 1H), 4.99-4.89 (m, 1H), 4.49 (br s, 2H), 4.36 (t, J = 8.1 Hz, 1H), 4.28 (br s, 2H), 4.21 (br t, J = 5.6 Hz, 2H), 3.75-3.67 (m, 2H), 3.64 (br d, J = 9.7 Hz, 2H), 3.28-3.26 (m, 6H), 3.01 (br d, J = 11.5 Hz, 2H), 2.74 (br s, 2H), 2.27 (s, 7H), 2.20-2.09 (m, 4H), 2.05-1.92 (m, 3H), 1.81-1.70 (m, 3H), 1.48-1.34 (m, 5H), 0.99-0.92 (m, 3H), 0.84-0.76 (m, 3H). |
| 179 | D | NA | 1069.9 | 1H NMR (400 MHz, DMSO-D6): δ 9.01-8.98 (m, 1H), 8.59-8.37 (m, 2H), 8.18 (s, 3H), 7.91 (d, J = 7.6 Hz, 1H), 7.77-7.68 (m, 3H), 7.49 (s, 1H), 7.22 (t, J = 8.0 Hz, 1H), 6.87-6.84 (m, 2H), (dd, J = 2.0, 6.0 Hz, 1H), 6.16-6.05 (m, 2H), 5.97 (s, 2H), 5.24-5.13 (m, 1H), 4.90 (quin, J = 7.2 Hz, 1H), 4.48 (br s, 2H), 4.40 (br t, J = 7.8 Hz, 1H), 4.30-4.15 (m, 4H), 3.74 (br d, J = 8.8 Hz, 1H), 3.55 (br d, J = 10.4 Hz, 2H), 3.46 (br dd, J = 4.0, 10.4 Hz, 2H), 3.32-3.20 (m, 4H), 3.01 (br d, J = 11.6 Hz, 2H), 2.77-2.66 (m, 2H), 2.66-2.64 (m, 3H), 2.63-2.61 (m, 1H), 2.34-2.24 (m, 5H), 2.19-2.05 (m, 5H), 1.99-1.91 (m, 2H), 1.80-1.68 (m, 3H), 1.50-1.32 (m, 5H), 0.96 (d, J = 6.8 Hz, 2H), 0.84-0.72 (m, 4H). |
| 180 | A | A | 1069.9 | 1H NMR (400 MHz, DMSO-D6): δ 9.00 (s, 1H), 8.56-8.46 (m, 2H), 8.19 (s, 2H), 7.91 (d, J = 7.2 Hz, 1H), 7.82-7.75 (m, 2H), 7.73-7.66 (m, 1H), 7.49 (s, 1H), 7.25-7.18 (m, 1H), 6.89-6.81 (m, 2H), 6.55-6.49 (m, 1H), |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| | | | | 6.13 (d, J = 1.6 Hz, 1H), 6.09 (s, 1H), 6.02-5.90 (m, 2H), 5.23-5.12 (m, 1H), 4.93 (quin, J = 7.2 Hz, 1H), 4.49 (br s, 2H), 4.35 (t, J = 8.0 Hz, 1H), 4.31-4.25 (m, 2H), 4.21 (br t, J = 5.2 Hz, 2H), 3.70 (br d, J = 4.4 Hz, 1H), 3.68 (br d, J = 4.0 Hz, 1H), 3.64 (br d, J = 9.8 Hz, 2H), 3.57-3.55 (m, 1H), 3.44 (br d, J = 10.0 Hz, 1H), 3.36-3.19 (m, 3H), 3.01 (br d, J = 11.2 Hz, 2H), 2.75 (br d, J = 11.6 Hz, 2H), 2.67-2.63 (m, 4H), 2.35-2.08 (m, 10H), 2.07-1.91 (m, 3H), 1.81-1.69 (m, 3H), 1.49-1.43 (m, 1H), 1.40 (d, J = 7.2 Hz, 3H), 0.98-0.91 (m, 3H), 0.84-0.76 (m, 3H). |
| 181 | D | NA | 910.7 | 1H NMR (400 MHZ, DMSO-D6): δ 13.81 (s, 1H), 8.93-9.03 (m, 1H), 8.43 (s, 1H), 8.34 (d, J = 8.0 Hz, 1H), 8.13-8.23 (m, 2H), 7.96-8.05 (m, 1H), 7.20-7.50 (m, 5H), 6.87-6.95 (m, 2H), 6.47 (s, 2H), 6.04-6.15 (m, 1H), 5.12 (d, J = 2.4 Hz, 1H), 4.83-5.06 (m, 1H), 4.39-4.56 (m, 1H), 4.30-4.37 (m, 2H), 4.14-4.29 (m, 3H), 3.79-3.89 (m, 2H), 3.74 (d, J = 8.4 Hz, 1H), 3.60-3.69 (m, 2H), 3.39-3.58 (m, 10H), 2.40-2.47 (m, 3H), 1.97-2.31 (m, 2H), 1.71-1.96 (m, 1H), 1.29-1.48 (m, 3H), 0.71-1.07 (m, 6H). |
| 182 | B | A | 910.7 | 1H NMR (400 MHZ, DMSO-D6): δ 13.81 (s, 1H), 8.79-9.02 (m, 1H), 8.40-8.47 (m, 2H), 8.19 (d, J = 11.2 Hz, 2H), 8.00 (d, J = 7.6 Hz, 1H), 7.32-7.48 (m, 4H), 7.26 (t, J = 7.2 Hz, 1H), 6.86-6.97 (m, 2H), 6.48 (s, 2H), 5.88-6.11 (m, 1H), 4.98-5.16 (m, 1H), 4.84-4.95 (m, 1H), 4.31-4.41 (m, 3H), 4.18-4.30 (m, 3H), 3.84 (t, J = 5.2 Hz, 2H), 3.60-3.74 (m, 3H), 3.38-3.59 (m, 10H), 2.45 (s, 3H), 2.14-2.28 (m, 1H), 1.87-2.10 (m, 1H), 1.70-1.84 (m, 1H), 1.32-1.50 (m, 3H), 0.93-1.05 (m, 3H), 0.74-0.84 (m, 3H). |
| 183 | A | A | 1072.9 | 1H NMR (400 MHZ, CD3OD): δ 8.96-8.91 (m, 1H), 7.84 (d, J = 7.4 Hz, 1H), 7.60-7.55 (m, 2H), 7.48-7.39 (m, 5H), 7.08-7.02 (m, 2H), 6.87 (br d, J = 7.4 Hz, 1H), 6.27 (br d, J = 5.5 Hz, 1H), 5.24 (br d, J = 3.4 Hz, 1H), 5.03 (q, J = 6.5 Hz, 1H), 4.86-4.77 (m, 2H), 4.71-4.65 (m, 1H), 4.62-4.54 (m, 1H), 4.53-4.37 (m, 2H), 4.26-4.05 (m, 2H), 3.95-3.60 (m, 8H), 3.58-3.35 (m, 4H), 3.29 (br s, 2H), 3.16-3.05 (m, 1H), 2.71-2.54 (m, 4H), 2.50 (s, 3H), 2.36-2.16 (m, 6H), 2.14-2.05 (m, 2H), 2.03-1.94 (m, 1H), 1.83 (br d, J = 9.9 Hz, 1H), 1.63-1.49 (m, 3H), 1.12-1.01 (m, 9H). |
| 184 | D | NA | 1098.9 | 1H NMR (400 MHZ, CD3OD): δ 8.99-8.94 (m, 1H), 8.65 (d, J = 7.3 Hz, 1H), 7.85 (d, J = 7.3 Hz, 1H), 7.60-7.56 (m, 2H), 7.55-7.49 (m, 2H), 7.49-7.38 (m, 3H), 7.09-7.02 (m, 2H), 6.87 (dd, J = 2.1, 7.4 Hz, 1H), 6.27 (br s, 1H), 6.15-6.07 (m, 1H), 5.23 (br s, 1H), 5.07-4.93 (m, 4H), 4.67-4.57 (m, 3H), 4.55-4.38 (m, 4H), 3.87 (br d, J = 12.2 Hz, 2H), 3.83-3.58 (m, 7H), 3.56-3.49 (m, 1H), 3.43-3.40 (m, 3H), 3.38-3.34 (m, 1H), 3.29 (br s, 1H), 3.22-3.06 (m, 1H), 2.60 (br d, J = 3.8 Hz, 4H), 2.40 (qd, J = 6.6, 15.8 Hz, 1H), 2.34-2.18 (m, 6H), 2.14-1.70 (m, 4H), 1.63-1.49 (m, 3H), 1.08 (d, J = 6.6 Hz, 3H), 0.99-0.91 (m, 3H). |
| 185 | A | A | 1098.9 | 1H NMR (400 MHz, CD3OD): δ 9.09-8.95 (m, 1H), 8.65 (d, J = 7.3 Hz, 1H), 7.85 (d, J = 7.3 Hz, 1H), 7.62-7.51 (m, 4H), 7.49-7.39 (m, 3H), 7.09-7.02 (m, 2H), 6.87 (dd, J = 2.0, 7.5 Hz, 1H), 6.27 (br s, 1H), 6.16-6.01 (m, 1H), 5.24 (br s, 1H), 5.11-4.95 (m, 2H), 4.80 (br t, J = 7.9 Hz, 1H), 4.61 (br s, 2H), 4.56-4.36 (m, 5H), 3.92-3.56 (m, 9H), 3.56-3.45 (m, 2H), 3.44-3.41 (m, 3H), 3.37 (s, 1H), 3.29 (s, 1H), 2.61 (br s, 4H), 2.47-1.93 (m, 11H), 1.81 (br s, 1H), 1.66-1.50 (m, 3H), 1.08 (d, J = 6.6 Hz, 3H), 0.97-0.85 (m, 3H) |
| 186 | C | A | 1074.7 | 1H NMR (400 MHZ, CD3OD): δ 8.84 (s, 1H), 8.10 (d, J = 3.1 Hz, 1H), 7.81-7.72 (m, 2H), 7.51- 7.33 (m, 6H), 7.24 (m, 2H), 6.90 (t, J = 8.3 Hz, 2H), 6.76- 6.60 (m, 2H), 6.56 (m, 1H), 6.19 (d, J = 2.0 Hz, 1H), 6.08 (s, 1H), 5.29 (t, J = 5.7 Hz, 1H), 5.01 (m, 3H), 4.58-4.53 (m, 3H), 4.43 (s, 1H), 3.79 (d, J = 9.2 Hz, 1H), 3.75-3.63 (m, 2H), 3.36 (m, 2H), 3.13 (d, J = 11.7 Hz, 2H), 2.67 (t, J = 5.6 Hz, 4H), 2.48 (m, 4H), 2.25-2.15 (m, 5H), 1.95 (m, 1H), 1.70-1.49 (m, 3H), 1.30 (s, 1H), 1.07- 0.84 (m, 6H). |
| 187 | D | NA | 1002.9 | 1H NMR (400 MHZ, CD3OD): δ 8.88 (s, 1H), 7.77 (d, J = 7.8 Hz, 1H), 7.52 (d, J = 7.5 Hz, 1H), 7.48-7.34 (m, 4H), 7.26 (t, J = 7.7 Hz, 1H), 6.93-6.87 (m, 1H), 6.08-6.01 (m, 1H), 5.05-4.96 (m, 2H), 4.58 (t, J = 8.0 Hz, 1H), 4.49-4.27 (m, 3H), 3.89-3.57 (m, 6H), 3.39-3.32 (m, 2H), 3.29-3.18 (m, 2H), 3.11-3.05 (m, 2H), 2.83-2.76 (m, 2H), 2.75- 2.69 (m, 7H), 2.65-2.55 (m, 2H), 2.54-2.44 (m, 4H), 2.38-2.32 (m, 1H), 2.25-2.17 (m, 3H), 2.01-1.91(m, 1H), 1.85-1.76 (m, 2H), 1.64-1.44 (m, 3H), 1.30 (s, 1H), 1.20 (s, 1H), 1.06 (d, J = 6.6 Hz, 3H), 0.99-0.82 (m, 3H). |
| 188 | A | A | 1002.7 | 1H NMR (400 MHZ, CD3OD): δ 8.88 (s, 1H), 7.79 (d, J = 7.9 Hz, 1H), 7.59- 7.34 (m, 5H), 7.26 (t, J = 7.8 Hz, 1H), 6.97-6.91 (m, 2H), 6.12-5.95 (m, 1H), 5.05-4.96 (m, 1H), 4.54-5.49 (m, 1H), 4.45-4.40 (m, 1H), 4.39-4.31(m, 2H), 3.85-3.72 (m, 3H), 3.65-3.61 (m, 2H), 3.39 (s, 2H), 3.30-3.18 (m, 2H), 3.11 (t, J = 10.9 Hz, 2H), 2.84-2.79 (m, 3H), 2.70 (brs, 7H), 2.60-2.44 (m, 7H), 2.38-2.31 (m, 2H), 2.17-2.10 (m, 3H), 1.97-1.90 (m, 1H), 1.91-1.77 (m, 2H), 1.56-1.50 (m, 3H), 1.37-1.18 (m, 1H), 1.06 (d, J = 6.5 Hz, 3H), 0.90-0.81 (m, 3H). |

TABLE 2B-continued

| Target protein degradation via exemplary bifunctional degradation compounds of Table 1B | | | | |
|---|---|---|---|---|
| Ex. # | *$DC_{50}$ (nM) | **$D_{max}$ (%) | MH+ | NMR transcript |
| 189 | A | A | 975.8 | 1H NMR (400 MHZ, DMSO-D6): δ 8.99 (s, 1H), 8.47 (s, 1H), 8.43-8.41 (d, J = 6.8 Hz, 1H), 8.25-8.21 (d, J = 6 Hz, 2H), 8.18 (s, 1H), 8.03 (d, J = 6.8 Hz, 1H), 7.44-7.35 (m, 4H), 7.27 (t, J = 7.7 Hz, 1H), 6.95-6.90 (m, 2H), 6.50 (s, 2H), 6.09 (s, 1H), 4.91 (br t, J = 7.3 Hz, 1H), 4.40-4.34 (m, 1H), 4.33-4.25 (m, 3H), 4.20-4.12 (m, 2H), 4.11-4.02 (m, 2H), 3.72-3.68 (m, 3H), 3.42-3.41 (m, 1H), 3.17-3.06 (m, 1H), 2.69-2.62 (m, 2H), 2.57-2.53 (m, 2H), 2.45 (s, 3H), 2.30-2.14 (m, 2H), 2.08-1.92 (m, 7H), 1.78 (ddd, J = 4.6, 7.9, 12.8 Hz, 1H), 1.65 (br d, J = 10.5 Hz, 2H), 1.47-1.36 (m, 3H), 1.35-1.24 (m, 2H), 1.02-0.90 (m, 3H), 0.89-0.70 (m, 3H). |
| 190 | D | NA | 1066.9 | 1H NMR (400 MHZ, DMSO-D6): δ 8.99-8.93 (m, 1H), 8.26 (d, J = 7.6 Hz, 1H), 8.21 (s, 2H), 7.92-7.90 (m, 1H), 7.76 (d, J = 6.0 Hz, 1H), 7.49-7.30 (m, 5H), 7.24-7.20 (m, 1H), 6.87-6.82 (m, 2H), 6.53-6.51 (m, 1H), 6.30-6.28 (m, 1H), 6.13 (d, J = 1.6 Hz, 1H), 5.96 (s, 2H), 5.20-5.17 (m, 1H), 4.89-4.85 (m, 1H), 4.53-4.51 (m, 3H), 4.30-4.20 (m, 2H), 3.83 (d, J = 8.4 Hz, 1H), 3.57-3.54 (m, 1H), 3.49-3.41 (m, 3H), 3.26-3.28 (m, 2H), 3.02-2.99 (m, 2H), 2.72-2.66 (m, 2H), 2.60-2.53 (m, 2H), 2.46-2.44 (m, 3H), 2.33-2.15 (m, 9H), 2.07-1.91 (m, 5H), 1.81-1.67 (m, 5H), 1.47-1.36 (m, 5H), 0.96 (d, J = 6.8 Hz, 2H), 0.83-0.71 (m, 4H). |
| 191 | A | A | 1066.9 | 1H NMR (400 MHZ, DMSO-D6): δ 8.98 (s, 1H), 8.40 (d, J = 7.2 Hz, 1H), 8.22 (s, 2H), 7.92-7.91 (m, 1H), 7.77 (d, J = 6.0 Hz, 1H), 7.49-7.35 (m, 5H), 7.24-7.20 (m, 1H), 6.87-6.82 (m, 2H), 6.53-6.51 (m, 1H), 6.26 (s, 1H), 6.14-6.13 (m, 1H), 5.97 (s, 2H), 5.21-5.16 (m, 1H), 4.93-4.89 (m, 1H), 4.49 (s, 2H), 4.38-4.28 (m, 3H), 3.74-3.69 (m, 2H), 3.59-3.54 (m, 1H), 3.44-3.41 (m, 1H), 3.26-3.23 (m, 3H), 2.84-3.01 (m, 2H), 2.74-2.67 (m, 2H), 2.60-2.55 (m, 2H), 2.45 (s, 3H), 2.33-2.17 (m, 9H), 2.04-1.92 (m, 5H), 1.81-1.71 (m, 5H), 1.45-1.37 (m, 5H), 0.98-0.95 (m, 3H), 0.81-0.76 (m, 3H). |
| 192 | A | A | 1093.0 | 1H NMR (300 MHz, DMSO-D6): δ 9.00 (s, 1H), 8.49-8.25 (m, 1H), 8.00-7.94 (m, 1H), 7.57-7.49 (m, 1H), 7.45-7.19(m, 4H), 6.89-6.82 (m, 2H), 6.25 (s, 1H), 6.19-6.06 (m, 1H), 5.12 (s, 1H), 5.06- 4.85 (m, 1H), 4.53-4.31 (m, 1H), 4.29-4.10 (m, 3H), 4.09-3.89 (m, 2H), 3.87-3.60 (m, 3H), 3.58-3.33 (m, 5H), 3.30-3.05 (m, 5H), 3.02-2.90 (m, 2H), 2.79-2.52 (m, 3H), 2.50-2.45 (m, 5H), 2.42-2.30 (m, 13H), 2.20-1.91 (m, 7H), 1.82-1.70 (m, 3H), 1.45-1.41 (m, 1H), 1.40-1.32 (m, 2H), 1.30-1.25 (m, 1H), 0.93-0.73 (m, 6H) |
| 193 | D | A | 1024.9 | 1H NMR (300 MHz, DMSO-D6): δ 14.2 (brs, 1H), 8.29 (s, 1H), 7.89 (s, 1H), 7.76 (s, 1H), 7.60-7.45 (m, 2H), 7.35-7.27 (m, 4H), 7.23-7.18 (m, 1H), 6.91-6.84 (m, 2H), 6.60-6.51 (m, 1H), 6.20-5.90 (m, 3H), 5.20-4.81 (m, 2H), 4.60-4.47 (m, 3H), 4.26-4.17 (m, 5H), 3.75-3.63 (m, 4H), 3.56-3.41 (m, 3H), 3.22-3.14 (m, 3H), 3.10-2.95 (m, 2H), 2.70-2.59 (s, 4H), 2.58-2.40 (m, 6H), 2.31-2.11 (m, 4H), 2.08-1.93 (m, 5H), 1.90-1.78 (m, 1H), 1.50-1.45 (m, 1H), 1.41-1.35 (m, 2H), 1.31-1.22 (m, 1H), 0.95-0.72 (m, 6H). |
| 194 | A | A | 1024.9 | 1H NMR (300 MHz, DMSO-D6): δ 14.34-13.88 (m, 1H), 8.45-8.35 (m, 1H), 7.89 (s, 1H), 7.76 (s, 1H), 7.47 (s, 1H), 7.41-7.28 (m, 5H), 7.18 (s, 1H), 6.83 (s, 2H), 6.52 (s, 1H), 6.14-5.94 (m, 3H), 5.01 (s, 2H), 4.48 (s, 2H), 4.41-4.11 (m, 5H), 3.70-3.62 (m, 4H), 3.64-3.34 (m, 3H), 3.21 (s, 2H), 2.99 (s, 2H), 2.71-2.53 (m, 5H), 2.43 (s, 7H), 2.26-2.05 (m, 3H), 2.05-1.79 (m, 6H), 1.79 (s, 1H), 1.41 (s, 3H), 1.21 (s, 1H), 0.93 (s, 3H), 0.77 (s, 3H). |
| 195 | D | A | 1137.0 | 1H NMR (400 MHZ, CDC13): δ 8.60 (s, 1H), 7.83 (d, J = 6.0 Hz, 1H), 7.46 (d, J = 6.8 Hz, 1H), 7.33-7.23 (m, 5H), 7.22-7.19 (m, 1H), 7.18 (s, 1H), 6.96 (d, J = 8.4 Hz, 1H), 6.81 (t, J = 7.3 Hz, 1H), 6.26 (dd, J = 2.0, 6.1 Hz, 1H), 5.93 (d, J = 2.0 Hz, 1H), 5.82 (s, 1H), 5.27-5.18 (m, 1H), 4.94-4.86 (m, 1H), 4.77-4.69 (m, 3H), 4.59-4.53 (m, 1H), 4.34-4.22 (m, 3H), 3.64 (dd, J = 5.6, 10.8 Hz, 1H), 3.54-3.42 (m, 2H), 3.31 (br s, 1H), 3.21-3.05 (m, 8H), 2.79 (br s, 2H), 2.57-2.49 (m, 4H), 2.45-2.43 (m, 3H), 2.40-2.33 (m, 5H), 2.19-2.10 (m, 3H), 2.07-1.99 (m, 3H), 1.98-1.81 (m, 5H), 1.65-1.50 (m, 2H), 1.35-1.26 (m, 3H), 1.25-1.13 (m, 2H), 0.97 (d, J = 6.5 Hz, 3H), 0.85 (d, J = 6.8 Hz, 3H). |
| 196 | D | A | 908.8 | 1H NMR (400 MHz, DMSO-D6): δ 13.80 (s, 1H), 8.99-8.90 (m, 1H), 8.43 (s, 1H), 8.26 (d, J = 8.0 Hz, 1H), 8.17 (d, J = 11.2 Hz, 2H), 7.99 (d, J = 8.0 Hz, 1H), 7.49-7.24 (m, 5H), 6.93-6.89 (m, 2H), 6.45 (s, 2H), 6.27-6.24 (m, 1H), 5.10-4.85 (m, 2H), 4.53-4.26 (m, 4H), 3.84-3.81 (m, 3H), 3.56-3.39 (m, 11H), 2.60-2.53 (m, 2H), 2.46-2.44 (m, 3H), 2.33-2.22 (m, 1H), 2.07-1.91 (m, 1H), 1.81-1.69 (m, 3H), 1.46-1.30 (m, 3H), 0.97-0.71(m, 6H). |
| 197 | D | NA | 929.8 | 1H NMR (400 MHz, DMSO-D6): δ 9.05-9.00 (m, 1H), 8.61-8.46 (m, 3H), 8.26 (s, 1H), 8.15 (s, 1H), 7.94-7.63 (m, 5H), 7.37 (t, J = 7.8 Hz, 1H), 7.05-6.95 (m, 2H), 6.16-6.09 (m, 1H), 5.14 (br s, 2H), 4.90-4.84 (m, 1H), 4.55-4.32 (m, 4H), 4.26 (br s, 1H), 3.81-3.71 (m, 1H), 3.57 (br d, J = 9.9 Hz, 1H), 3.49-3.31 (m, 2H), 3.28-2.84 (m, 10H), 2.70-2.61 |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| | | | | (m, 5H), 2.33-2.21 (m, 1H), 2.19-2.02 (m, 1H), 1.97-1.66 (m, 1H), 1.52-1.33 (m, 3H), 1.03-0.69 (m, 6H). |
| 198 | C | A | 1045.9 | 1H NMR (400 MHZ, DMSO-D6): δ 9.01-8.95 (m, 1H), 8.27 (d, J = 7.8 Hz, 1H), 8.18 (s, 2H), 7.96-7.88 (m, 1H), 7.79 (d, J = 6.0 Hz, 1H), 7.50-7.46 (m, 1H), 7.44-7.39 (m, 2H), 7.30 (d, J = 8.3 Hz, 1H), 7.22 (t, J = 7.7 Hz, 1H), 6.89-6.82 (m, 2H), 6.56-6.50 (m, 1H), 6.16 (d, J = 1.3 Hz, 1H), 5.96 (s, 2H), 4.85 (quin, J = 7.2 Hz, 1H), 4.50 (br s, 2H), 4.43 (br t, J = 7.8 Hz, 1H), 4.37-4.24 (m, 6H), 3.85-3.70 (m, 2H), 3.45-3.30 (m, 4H), 3.27-2.27 (m, 2H), 3.03-3.00 (m, 2H), 2.74-2.60 (m, 4H), 2.48-2.44 (m, 8H), 2.23-1.73 (m, 6H), 1.46-1.30 (m, 3H), 0.98 (d, J = 6.6 Hz, 2.5H), 0.85 (d, J = 6.7 Hz, 3H), 0.79 (br d, J = 6.7 Hz, 0.5H). |
| 199 | A | A | 1084.9 | 1H NMR (400 MHz, DMSO-D6): δ 8.98 (s, 1H), 8.38 (d, J = 8.0 Hz, 1H), 8.15 (s, 2H), 7.92-7.90 (m, 2H), 7.76 (d, J = 6.0 Hz, 1H), 7.49-7.37 (m, 5H), 7.24-7.20 (m, 1H), 6.87-6.82 (m, 2H), 6.53-6.51 (m, 1H), 6.14-6.09 (m, 2H), 5.97-5.96 (m, 2H), 5.21-5.17 (m, 1H), 4.89-4.75 (m, 2H), 4.53-4.51 (m, 3H), 4.49-4.40 (m, 3H), 4.31-4.20 (m, 4H), 3.73-3.56 (m, 5H), 3.27-3.23 (m, 2H), 3.02-2.99 (m, 1H), 2.77-2.61 (m, 3H), 2.46 (s, 3H), 2.34-2.12 (m, 10H), 2.07-1.76 (m, 6H), 1.45-1.37 (m, 2H), 0.98-0.94 (m, 3H), 0.82-0.80 (m, 3H). |
| 200 | B | A | 1084.9 | 1H NMR (400 MHz, DMSO-D6): δ 8.99-8.98 (m, 1H), 8.26-8.15 (m, 3H), 7.92-7.90 (m, 1H), 7.76 (d, J = 6.0 Hz, 1H), 7.49-7.40 (m, 4H), 7.33-7.31 (m, 1H), 7.24-7.20 (m, 1H), 6.87-6.82 (m, 2H), 6.53-6.51 (m, 1H), 6.18-6.07 (m, 2H), 5.97 (m, 2H), 5.19-5.17 (m, 1H), 4.97-4.80 (m, 2H), 4.59-4.42 (m, 4H), 4.31-4.12 (m, 4H), 3.77-3.75 (m, 4H), 3.26-3.23 (m, 2H), 3.02-2.99 (m, 2H), 2.76-2.65 (m, 3H), 2.46-2.45 (m, 3H), 2.38-2.01 (m, 10H), 1.97-1.67 (m, 6H), 1.44-1.32 (m, 2H), 0.97-0.71 (m, 6H). |
| 201 | C | A | 1098.9 | 1H NMR (400 MHZ, DMSO-D6): δ 8.99-8.96 (m, 1H), 8.85-8.20 (m, 1H), 8.15 (s, 2H), 7.91 (d, J = 7.0 Hz, 1H), 7.77 (d, J = 6.0 Hz, 1H), 7.49 (s, 1H), 7.36-7.17 (m, 2H), 7.11-6.97 (m, 2H), 6.90-6.80 (m, 2H), 6.52 (dd, J = 1.7, 6.0 Hz, 1H), 6.17-6.06 (m, 2H), 5.96 (s, 2H), 5.28-4.94 (m, 3H), 4.59-4.37 (m, 3H), 4.35-4.15 (m, 5H), 3.90-3.82 (m, 3H), 3.74 (br d, J = 8.6 Hz, 1H), 3.01 (br d, J = 11.5 Hz, 2H), 2.78-2.62 (m, 4H), 2.47 (s, 3H), 2.37-2.22 (m, 6H), 2.20-1.92 (m, 8H), 1.83-1.69 (m, 3H), 1.45-6.7 Hz, 3H), 0.76 (d, J = 6.6 Hz, 1H). |
| 202 | A | A | 1098.9 | 1H NMR (400 MHz, DMSO-D6): δ 9.01-8.97 (m, 1H), 8.35 (d, J = 7.9 Hz, 1H), 8.22 (s, 2H), 7.91 (d, J = 7.0 Hz, 1H), 7.77 (d, J = 6.0 Hz, 1H), 7.50 (s, 1H), 7.32-7.17 (m, 2H), 7.09-6.99 (m, 2H), 6.90-6.80 (m, 2H), 6.52 (br d, J = 6.1 Hz, 1H), 6.16-6.07 (m, 2H), 5.99-5.90 (m, 2H), 5.22-5.11 (m, 2H), 4.49 (br s, 2H), 4.40 (t, J = 7.7 Hz, 1H), 4.33-4.26 (m, 2H), 4.21 (br t, J = 5.5 Hz, 2H), 3.86 (s, 3H), 3.74-3.62 (m, 1H), 3.31-3.20 (m, 2H), 3.02 (br d, J = 11.5 Hz, 2H), 2.75 (br d, J = 11.1 Hz, 2H), 2.68-2.62 (m, 2H), 2.48 (s, 2H), 2.37-2.23 (m, 6H), 2.21-2.08 (m, 5H), 2.05-1.92 (m, 3H), 1.83-1.69 (m, 3H), 1.49-1.34 (m, 3H), 1.30 (d, J = 7.0 Hz, 3H), 1.00-0.92 (m, 3H), 0.84-0.76 (m, 3H). |
| 203 | A | A | 996.9 | 1H NMR (400 MHZ, DMSO-D6): δ 8.49 (d, J = 7.2 Hz, 1H), 8.27 (s, 2H), 7.91 (d, J = 6.8 Hz, 1H), 7.81-7.74 (m, 3H), 7.52-7.43 (m, 3H), 7.22 (t, J = 7.6 Hz, 1H), 6.90-6.81 (m, 2H), 6.52 (dd, J = 1.9, 6.1 Hz, 1H), 6.14 (d, J = 1.5 Hz, 1H), 6.08 (s, 1H), 5.96 (s, 2H), 5.25-5.15 (m, 1H), 4.91 (quin, J = 7.2 Hz, 1H), 4.49 (br s, 2H), 4.35 (t, J = 7.9 Hz, 1H), 4.31-4.25 (m, 2H), 4.21 (br t, J = 5.6 Hz, 2H), 3.72-3.60 (m, 1H), 3.25 (br d, J = 10.6 Hz, 4H), 3.01 (br d, J = 11.4 Hz, 2H), 2.74 (br d, J = 10.1 Hz, 2H), 2.68-2.60 (m, 2H), 2.35-2.23 (m, 5H), 2.22-2.09 (m, 5H), 2.05-1.90 (m, 3H), 1.81-1.70 (m, 3H), 1.47-1.39 (m, 2H), 1.35 (d, J = 7.1 Hz, 3H), 0.98-0.90 (m, 3H), 0.84-0.75 (m, 3H). |
| 204 | D | A | 996.9 | 1H NMR (400 MHz, DMSO-D6): δ 8.40 (br d, J = 7.1 Hz, 1H), 8.13 (s, 2H), 7.91 (d, J = 7.1 Hz, 1H), 7.78-7.73 (m, 3H), 7.54-7.41 (m, 3H), 7.22 (t, J = 7.0 Hz, 1H), 6.89-6.81 (m, 2H), 6.55-6.50 (m, 1H), 6.15-6.12 (m, 1H), 6.08 (s, 1H), 5.96 (s, 2H), 5.26-5.16 (m, 1H), 5.10 (d, J = 3.2 Hz, 1H), 4.87 (quin, J = 7.1 Hz, 1H), 4.49-4.45 (m, 2H), 4.4-4.38 (m, 1H), 4.34-4.11 (m, 4H), 3.75 (d, J = 8.6 Hz, 1H), 3.62-3.50 (m, 1H), 3.45-3.42 (m, 3H), 3.31-3.23 (m, 4H), 3.07-2.81 (m, 4H), 2.38-2.23 (m, 5H), 2.24-2.11 (m, 2H), 2.07-2.01 (m, 1H), 1.97-1.95 (m, 2H), 1.90-1.85 (m, 2H), 1.75-1.68 (m, 1H), 1.51 (br s, 2H), 1.33 (d, J = 7.1 Hz, 3H), 0.96 (d, J = 6.7 Hz, 3H), 0.85-0.72 (m, 3H). |
| 205 | D | A | 1006.9 | 1H NMR (400 MHZ, CD3OD): δ 8.88 (d, J = 7.0 Hz, 1H), 7.78-7.83 (m, 1H), 7.57-7.32 (m, 5H), 7.35-7.15 (m, 1H), 6.99-6.86 (m, 2H), 6.08-5.98 (m, 1H), 4.68-4.50 (m, 3H), 4.46-4.44 (m, 1H), 4.40-4.33 (m, 2H), 3.85-3.74 (m, 3H), 3.74-3.60 (m, 2H), 3.29-3.17 (m, 2H), 3.16-3.02 (m, 2H), 2.81-2.77 (m, 5.3 Hz, 2H), 2.71-2.61 (m, 7H), 2.52-2.40 (m, 8H), 2.38-2.32 (m, 4H), 2.26-2.10 (m, 3H), 2.01-1.90 (m, 1H), 1.90-1.78 (m, 2H), 1.69-1.53 (m, 4H), 1.50 (d, J = 7.0 Hz, 2H), 1.20 (s, 1H), 1.06 (d, J = 6.6 Hz, 3H), 0.99-0.81 (m, 3H) |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| 206 | C | A | 1075.8 | 1H NMR (400 MHZ, DMSO-D6): δ 14.13 (s, 1H), 8.99 (d, J = 14.4 Hz, 1H), 8.49 (s, 1H), 8.38 (d, J = 7.5 Hz, 1H), 8.18 (d, J = 3.0 Hz, 1H), 7.91 (d, J = 7.9 Hz, 1H), 7.85-7.66 (m, 3H), 7.50 (s, 1H), 7.47-7.31 (m, 1H), 7.22 (t, J = 7.4 Hz, 2H), 6.85- 6.63 (m, 3H), 6.58-6.51 (m, 1H), 6.18-6.12 (m, 2H), 5.97 (s, 2H), 5.31 (t, J = 6.1 Hz, 1H), 5.11-4.81 (m, 4H), 4.50 (s, 2H), 4.41 (t, J = 7.8 Hz, 1H), 4.25 (s, 1H), 3.76 (d, J = 8.6 Hz, 1H), 3.56 (d, J = 10.5 Hz, 1H), 3.52-3.37 (m, 2H), 3.34(m, 1H), 3.36-3.25 (m, 3H), 3.02 (d, J = 11.6 Hz, 2H), 2.64 (d, J = 9.2 Hz, 3H), 2.56 (s, 4H), 2.26-2.18 (m, 3H), 2.04-1.97 (m, 3H), 1.75 (m, 1H), 1.49-1.21 (d, J = 7.0 Hz, 3H), 0.97 (d, J = 6.6 Hz, 2H), 0.83- 0.76 (m, 3H). |
| 207 | A | A | 1075.8 | 1H NMR (400 MHZ, DMSO-D6): δ 14.13 (s, 1H), 9.01 (s, 1H), 8.50 (s, 2H), 8.18 (s, 1H), 7.91 (s, 1H), 7.77 (m, 3H), 7.69-7.38 (m, 2H), 7.32-7.15 (m, 2H), 6.90-6.66 (m, 4H), 6.65-6.42 (s, 1H), 6.14 (d, J = 17.2 Hz, 2H), 5.96 (s, 2H), 5.31 (s, 1H), 5.10 (s, 1H), 5.02-4.80 (m, 4H), 4.49 (s, 2H), 4.40- 4.17 (m, 2H), 3.67 (s, 2H), 3.23(m, 2H), 3.01 (s, 2H), 2.70-2.65 (m, 4H), 2.50-2.41(m, 3H), 2.30-2.15(m, 3H), 2.01-1.96 (s, 3H), 1.75 (s, 1H), 1.40 (m, 4H), 0.95 (s, 3H), 0.80 (s, 3H). |
| 208 | D | A | 1086.9 | 1H NMR (400 MHz, DMSO-D6): δ 9.90 (s, 1H), 9.00-8.95 (m, 1H), 8.42 (d, J = 7.6 Hz, 1H), 7.94 (d, J = 4.8 Hz, 1H), 7.56 (d, J = 6.8 Hz, 1H), 7.52-7.30 (m, 7H), 7.07-6.78 (m, 5H), 6.27 (s, 1H), 5.21 (s, 1H), 4.89-4.76 (m, 4H), 4.61 (s, 3H), 4.50-4.24 (m, 5H), 4.20-4.04 (m, 2H), 3.90 (d, J = 10.0 Hz, 1H), 3.21-3.03 (m, 7H), 2.46-2.41 (m, 6H), 2.22-1.60 (m, 12H), 1.34 (d, J = 7.2 Hz, 3H), 0.98 (d, J = 6.4 Hz, 3H), 0.85 (d, J = 6.4 Hz, 3H). |
| 209 | A | A | 1086.9 | 1H NMR (400 MHz, DMSO-D6): δ 9.80 (s, 1H), 8.99 (s, 1H), 8.41 (d, J = 7.6 Hz, 1H), 7.95 (s, 1H), 7.57 (s, 1H), 7.50-7.42 (m, 3H), 7.40-7.34 (m, 3H), 7.06-6.80 (m, 4H), 6.27 (s, 1H), 5.22 (s, 1H), 4.97-4.78 (m, 3H), 4.62 (s, 2H), 4.40-4.26 (m, 3H), 4.07-3.76 (m, 7H), 3.17-3.14 (m, 7H), 2.45 (s, 6H), 2.29-1.56 (m, 12H), 1.37 (d, J = 7.2 Hz, 3H), 1.04-0.93 (m, 3H), 0.85 (d, J = 6.4 Hz, 3H). |
| 210 | A | A | 1027.9 | 1H NMR (400 MHZ, DMSO-D6): δ 8.97-8.96 (m, 1H), 8.51 (t, J = 6.0 Hz, 1H), 8.31 (s, 1H), 7.91-7.89 (m, 1H), 7.78 (d, J = 6.0 Hz, 1H), 7.48-7.33 (m, 5H), 7.23-7.20 (m, 1H), 6.87-6.82 (m, 2H), 6.53-6.51 (m, 1H), 6.14 (d, J = 1.6 Hz, 1H), 6.08 (m, 1H), 5.95 (m, 2H), 4.48-4.42 (m, 2H), 4.38-4.12 (m, 8H), 3.78-3.74 (m, 1H), 3.65 (d, J = 8.8 Hz, 1H), 3.26-3.23 (m, 1H), 3.02-2.97 (m, 4H), 2.80-2.70 (m, 2H), 2.63-2.55 (m, 4H), 2.44-2.41 (m, 5H), 2.29-2.16 (m, 5H), 2.09-1.83 (m, 5H), 0.97-0.92 (m, 6H), 0.80-0.78 (m, 3H). |
| 211 | A | A | 1084.9 | 1H NMR (400 MHZ, DMSO-D6): δ 9.75 (br s, 1H), 9.11-8.98 (m, 1H), 8.40 (d, J = 7.8 Hz, 1H), 8.91 (d, J = 7.3 Hz, 1H), 7.95 (d, J = 7.0 Hz, 1H), 7.62-7.47 (m, 4H), 7.42-7.33 (m, 3H), 7.07-6.80 (m, 5H), 6.28 (s, 1H), 6.19-6.02 (m, 1H), 5.23 (br s, 1H), 4.92 (br t, J = 6.9 Hz, 1H), 4.84 (br s, 2H), 4.52 (s, 4H), 4.42-4.23 (m, 4H), 3.70 (br d, J = 9.8 Hz, 8H), 3.25-3.02 (m, 8H), 2.29-1.87 (m, 10H), 1.84-1.74 (m, 1H), 1.64 (br d, J = 12.1 Hz, 1H), 1.49-1.34 (m, 3H), 0.98 (br d, J = 6.2 Hz, 3H), 0.87-0.75 (m, 3H). |
| 212 | D | A | 1052.9 | 1H NMR (400 MHZ, DMSO-D6): δ 8.93-8.27 (m, 2H), 8.14 (s, 2H), 7.91 (d, J = 8.1 Hz, 1H), 7.77 (d, J = 6.0 Hz, 1H), 7.62-7.43 (m, 3H), 7.34 (d, J = 8.3 Hz, 2H), 7.26-7.15 (m, 1H), 6.89-6.81 (m, 2H), 6.52 (dd, J = 1.8, 6.0 Hz, 1H), 6.16-6.08 (m, 2H), 5.96 (s, 1H), 5.22-5.14 (m, 1H), 5.03-4.82 (m, 1H), 4.55-4.39 (m, 3H), 4.30-4.18 (m, 4H), 3.74 (d, J = 8.6 Hz, 1H), 3.57-3.10 (m, 9H), 3.01 (d, J = 11.6 Hz, 2H), 2.82-2.66 (m, 4H), 2.37-2.33 (m, 3H), 2.32-2.25 (m, 4H), 2.23-2.14 (m, 3H), 2.09-1.72 (m, 6H), 1.47-1.30 (m, 5H), 0.96 (d, J = 6.7 Hz, 2H), 0.84-0.72 (m, 4H). |
| 213 | A | A | 1052.9 | 1H NMR (400 MHZ, DMSO-D6): δ 8.39 (d, J = 7.7 Hz, 1H), 8.30 (s, 1H), 8.15 (s, 2H), 7.91 (d, J = 6.7 Hz, 1H), 7.76 (d, J = 6.0 Hz, 1H), 7.60-7.52 (m, 3H), 7.49 (s, 1H), 7.38 (d, J = 8.3 Hz, 2H), 7.25-7.18 (m, 1H), 6.89-6.80 (m, 2H), 6.54-6.49 (m, 1H), 6.13-6.08 (m, 1H), 5.96-5.91 (m, 1H), 5.23-5.14 (m, 1H), 4.90 ( J = 7.2 Hz, 1H), 4.48 (s, 2H), 4.40-4.18 (m, 6H), 3.04-2.98 (m, 1H), 2.80-2.63 (m, 5H), 2.36-1.71 (m, 23H), 1.46-1.34 (m, 6H), 0.98-0.93 (m, 3H), 0.84-0.78 (m, 3H). |
| 214 | D | NA | 1084.9 | 1H NMR (400 MHz, CDC13): δ 8.73-8.67 (m, 1H), 8.19 (s, 2H), 7.93-7.86 (m, 1H), 7.54 (d, J = 6.2 Hz, 1H), 7.42-7.28 (m, 2H), 7.22 ( d, J = 7.7 Hz, 1H), 7.06-6.85 (m, 4H), 6.35 (dd, J = 2.0, 6.1 Hz, 1H), 6.04-5.95 (m, 1H), 5.87-5.76 (m, 1H), 5.29 ( t, J = 4.6 Hz, 1H), 5.01 ( s, 1H), 4.73-4.20 (m, 10H), 3.89 (s, 3H), 3.69-3.43 (m, 4H), 3.38-2.75 (m, 11H), 2.55-2.53 (m, 3H), 2.46-2.38 (m, 4H), 2.04-1.77 (m, 10H), 1.04 (d, J = 6.6 Hz, 2.5H), 0.92 (d, J = 6.7 Hz, 2.5H), 0.76 (d, J = 6.5 Hz, 0.5H), 0.61 (d, J = 7.0 Hz, 0.5H). |
| 215 | A | A | 1084.9 | 1H NMR (400 MHz, CDC13): δ 8.69 (s, 1H), 8.21 (s, 2H), 7.90 (d, J = 6.1 Hz, 1H), 7.53 (d, J = 6.7 Hz, 1H), 7.35-7.28 (m, 3H), 7.07-6.94 (m, 2H), 6.91-6.85 (m, 2H), 6.39-6.27 (m, 1H), 6.02-5.88 (m, 2H), 5.34-5.24 (m, 1H), 5.04 ( s, 1H), 4.69-4.29 (m, 10H), 3.89 (s, 3H), 3.73-3.66 (m, 1H), 3.63-3.54 (m, 2H), 3.43 (d, J = 9.7 Hz, 1H), 3.34-3.05 (m, 11H), |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| | | | | 2.54 (s, 7H), 2.27-2.02 (m, 7H), 1.89-1.81 (m, 3H), 0.91 (d, J = 6.5 Hz, 3H), 0.87 (d, J = 6.6 Hz, 3H). |
| 216 | A | A | 1076.9 | 1H NMR (400 MHZ, DMSO-D6): δ 8.98 (s, 1H), 8.42 (d, J = 7.6 Hz, 1H), 8.21 (s, 2H), 8.07 (d, J = 6.0 Hz, 1H), 7.91 (d, J = 7.6 Hz, 1H), 7.51 (s, 1H), 7.43 (d, J = 8.0 Hz, 2H), 7.39-7.33 (m, 2H), 7.22 (t, J = 7.6 Hz, 1H), 6.95-6.81 (m, 3H), 6.77 (d, J = 4.0 Hz, 1H), 6.09 (s, 1H), 5.99 (s, 2H), 4.91 (t, J = 7.2 Hz, 1H), 4.56 (s, 2H), 4.40-4.18 (m, 6H), 3.74-3.60 (m, 4H), 3.44 (d, J = 10.4 Hz, 1H), 3.18 (s, 1H), 3.00 (d, J = 11.2 Hz, 2H), 2.73 (s, 2H), 2.67-2.60 (m, 2H), 2.45 (s, 3H), 2.36-2.27 (m, 3H), 2.24-2.08 (m, 6H), 2.04-1.92 (m, 3H), 1.76 (d, J = 8.4 Hz, 3H), 1.44-1.32 (m, 5H), 0.95 (d, J = 6.4 Hz, 3H), 0.84-0.76 (m, 3H). |
| 217 | B | A | 1082.9 | 1H NMR (400 MHZ, CD3OD): δ 8.92-8.82 (m, 1H), 8.46 (br s, 2H), 7.82-7.69 (m, 2H), 7.51-7.34 (m, 5H), 7.23 (t, J = 7.7 Hz, 1H), 6.95-6.83 (m, 2H), 6.55 (br d, J = 6.0 Hz, 1H), 6.13 (s, 1H), 6.06-5.97 (m, 1H), 5.14 (br s, 1H), 4.97-4.94 (m, 1H), 4.65-4.51 (m, 6H), 4.46-4.35 (m, 2H), 4.33-4.23 (m, 2H), 3.82-3.54 (m, 4H), 3.24 (br s, 2H), 3.10 (br d, J = 11.1 Hz, 5H), 2.75 (br s, 2H), 2.48-2.38 (m, 7H), 2.26-2.08 (m, 6H), 2.02-1.75 (m, 5H), 1.62-1.44 (m, 3H), 1.05 (d, J = 6.6 Hz, 3H), 0.96-0.86 (m, 3H). |
| 218 | A | A | 1082.9 | 1H NMR (400 MHz, CD3OD): δ 8.87 (s, 1H), 8.45 (br s, 2H), 7.83-7.68 (m, 2H), 7.52-7.35 (m, 5H), 7.23 (t, J = 7.6 Hz, 1H), 6.96-6.85 (m, 2H), 6.55 (br d, J = 4.6 Hz, 1H), 6.13 (s, 1H), 6.06-5.91 (m, 1H), 5.15 (br s, 1H), 5.06-5.01 (m, 1H), 4.62-4.50 (m, 7H), 4.47-4.34 (m, 2H), 4.29 (br t, J = 5.9 Hz, 2H), 3.90-3.55 (m, 4H), 3.36 (br s, 1H), 3.11 (br d, J = 11.6 Hz, 5H), 2.76 (br s, 1H), 2.51-2.39 (m, 7H), 2.29-2.11 (m, 7H), 2.07-1.74 (m, 5H), 1.62-1.48 (m, 3H), 1.05 (br d, J = 6.4 Hz, 3H), 0.94-0.85 (m, 3H). |
| 219 | D | NA | 1084.9 | 1H NMR (400 MHz, CD3OD): δ 9.00-8.88 (m, 1H), 7.85 (d, J = 7.5 Hz, 1H), 7.67-7.53 (m, 4H), 7.51-7.36 (m, 3H), 7.10-6.96 (m, 2H), 6.87 (br d, J = 7.3 Hz, 1H), 6.26 (br s, 1H), 6.14-6.05 (m, 1H), 5.23 (br s, 1H), 5.03-4.96 (m, 3H), 4.71-4.65 (m, 2H), 4.64-4.56 (m, 3H), 4.45 (br s, 2H), 3.89-3.57 (m, 8H), 3.28 (br s, 2H), 2.81 (br s, 1H), 2.60 (br s, 5H), 2.46-2.15 (m, 8H), 2.12-1.87 (m, 4H), 1.79 (br s, 1H), 1.56-1.46 (m, 3H), 1.08 (d, J = 6.5 Hz, 3H), 0.98-0.91 (m, 3H). |
| 220 | C | A | 1058.8 | 1H NMR (300 MHz, CD3OD): δ 8.26 (s, 1H), 8.09 (s, 1H), 7.77-7.71 (m, 2H), 7.46-7.34 (m, 6H), 7.24-7.19 (m, 2H), 6.69-6.87 (m, 2H), 6.55-6.53 (m, 1H), 6.10 (s, 1H) , 6.06 (s, 1H), 5.26-5.23 (m, 1H), 5.00-4.86 (m, 4H), 4.59-4.51 (m, 6H), 4.38 (s, 2H), 3.80-3.73 (m, 2H), 3.34 (s, 1H), 3.12-3.08 (m, 2H), 2.46-2.38 (m, 4H), 2.35 (s, 3H), 2.24-2.05 (m, 6H), 1.06-1.04 (m, 3H), 0.94-0.92 (m, 3H). |
| 221 | A | A | 1058.8 | 1H NMR (300 MHz, CD3OD): δ 8.87 (s, 1H), 8.12 (s, 1H), 7.78-7.72 (m, 2H), 7.50-7.33 (m, 6H), 7.28-7.20 (m, 2H), 6.91-6.88 (m, 2H), 6.56-6.55 (m, 1H), 6.17 (s, 1H) , 6.10 (s, 1H), 5.29-5.25 (m, 1H), 5.10 (s, 4H), 4.88 (s, 6H), 4.60-4.44 (m, 2H), 3.89-3.88 (m, 1H), 3.80-3.73 (m, 2H), 3.73-3.62 (m, 1H), 3.35-3.31 (m, 2H), 2.46-2.38 (m, 3H), 2.35 (s, 3H), 2.24-2.05 (m, 6H), 1.06-1.04 (m, 3H), 0.94-0.92 (m, 3H). |
| 222 | D | NA | 1103.9 | 1H NMR (400 MHZ, CD3OD): δ 8.89 (s, 1H), 8.50 (br s, 1H), 8.30 (br s, 2H), 7.88-7.76 (m, 2H), 7.73-7.53 (m, 2H), 7.49-7.32 (m, 1H), 7.23 (t, J = 7.2 Hz, 1H), 7.04-6.84 (m, 2H), 6.58 (br d, J = 5.9 Hz, 1H), 6.18-6.07 (m, 1H), 5.26-4.94 (m, 2H), 4.60-4.36 (m, 7H), 3.88 (d, J = 10.3 Hz, 1H), 3.81-3.73 (m, 1H), 3.70-3.46 (m, 3H), 3.38 (br s, 3H), 3.28-2.96 (m, 6H), 2.67-2.59 (m, 4H), 2.44 (br s, 4H), 2.28-2.12 (m, 5H), 2.05-1.79 (m, 5H), 1.52 (br d, J = 7.1 Hz, 3H), 1.08 (d, J = 6.5 Hz, 3H), 0.87 (d, J = 6.6 Hz, 3H). |
| 223 | B | A | 1103.9 | 1H NMR (400 MHZ, CD3OD): δ 8.92 (s, 1H), 8.56 (s, 1H), 8.32 (s, 2H), 7.84 (br d, J = 8.1 Hz, 1H), 7.82-7.61 (m, 3H), 7.57-7.45 (m, 1H), 7.41-7.19 (m, 1H), 7.09-6.81 (m, 2H), 6.58 (br d, J = 5.3 Hz, 1H), 6.26-6.09 (m, 1H), 5.21-4.98 (m, 2H), 4.63-4.32 (m, 7H), 3.96-3.72 (m, 2H), 3.67-3.41 (m, 3H), 3.40-3.35 (m, 3H), 3.31-3.09 (m, 6H), 2.70-2.55 (m, 4H), 2.51-2.39 (m, 4H), 2.33-2.11 (m, 5H), 2.10-1.90 (m, 5H), 1.55 (br d, J = 7.1 Hz, 3H), 1.08 (br d, J = 6.6 Hz, 3H), 0.93-0.81 (m, 3H). |
| 224 | D | NA | 1079.9 | 1H NMR (400 MHz, DMSO-D6): δ 9.06 (s, 1H), 8.68 (t, J = 6.0 Hz, 1H), 8.17 (s, 2H), 7.99-7.90 (m, 2H), 7.77-7.72 (m, 2H), 7.57 (d, J = 8.4 Hz, 1H), 7.47 (s, 1H), 7.22 (t, J = 8.0 Hz, 1H), 6.87-6.82 (m, 2H), 6.53-6.51 (m, 1H), 6.13-6.10 (m, 2H), 6.02-5.97 (m, 2H), 5.17-5.16 (m, 1H), 4.51-4.11 (m, 10H), 3.76 (d, J = 8.8 Hz, 2H), 3.60-3.52 (m, 4H), 3.26-3.23 (m, 2H), 3.02-2.99 (m, 2H), 2.56 (t, J = 5.2 Hz, 2H), 2.46-2.45 (m, 3H), 2.33-1.89 (m, 13H), 1.75-1.70 (m, 2H), 1.39-1.34 (m, 2H), 0.96 (d, J = 6.4 Hz, 2H), 0.83 (d, J = 6.4 Hz, 2H), 0.63-0.57 (m, 1H). |
| 225 | A | A | 1079.9 | 1H NMR (400 MHZ, DMSO-D6): δ 9.06 (s, 1H), 8.75 (t, J = 6.0 Hz, 1H), 8.25 (s, 2H), 7.96-7.91 (m, 2H), 7.78-7.76 (m, 2H), 7.66 (d, J = 8.4 Hz, 1H), 7.49 (s, 1H), 7.22 (t, J = 8.0 Hz, 1H), 6.87-6.82 (m, 1H), 6.53-6.51 (m, 1H), 6.13-6.11 (m, 2H), 5.97 (m, 1H), 5.19-5.17 (m, 1H), 4.52-4.13 (m, 10H), 3.77-3.63 (m, 6H), 3.26-3.23 (m, 2H), 3.05-2.97 (m, 2H), 2.76-2.69 (m, 2H), 2.46-2.44 (m, 3H), 2.33-1.89 (m, 13H), 1.77- |

TABLE 2B-continued

| Target protein degradation via exemplary bifunctional degradation compounds of Table 1B | | | | |
|---|---|---|---|---|
| Ex. # | *$DC_{50}$ (nM) | **$D_{max}$ (%) | MH+ | NMR transcript |
| | | | | 1.75 (m, 2H), 1.43-1.36 (m, 2H), 0.95-0.90 (m, 3H), 0.81-0.78 (m, 3H) |
| 226 | C | A | 1086.8 | 1H NMR (300 MHz, CD3OD): δ 8.87 (s, 1H), 8.08 (s, 1H) 7.82-7.73 (m, 2H), 7.51-7.16 (m, 8H), 6.93 (d, J = 9Hz, 2H), 6.85-6.83 (m, 1H), 6.24 (s, 1H), 6.06 (s, 1H), 5.05-4.90 (m, 1H), 4.94-4.91 (m, 2H), 4.74-4.71 (m, 2H), 4.59-4.56 (m, 1H), 4.38-4.33 (m, 3H), 3.80-3.69 (m, 3H), 3.53-3.33 (m, 2H), 3.13 (d, J = 3Hz, 2H), 2.94-2.89 (m, 2H), 2.79-2.75 (m, 3H, 2.49-2.27 (m, 9H), 1.99-1.95 (m, 1H), 1.49 (d, J = 7.2Hz, 3H), 1.06 (d, J = 6.6Hz, 1H), 0.92 (d, J = 6.6Hz, 6H). |
| 227 | A | A | 1086.8 | 1H NMR (300 MHz, CD3OD): δ 8 8.87 (s, 1H), 8.08 (s, 1H) 7.82-7.73 (m, 2H), 7.73-7.15 (m, 8H), 6.93 (d, J = 7.8Hz, 2H), 6.73 (d, J = 7.8 Hz, 1H), 6.24 (s, 1H), 6.06 (s, 1H), 5.35-5.33 (m, 1H), 5.02-4.99 (m, 2H), 4.74-4.71 (m, 2H), 4.62-4.59 (m, 1H), 4.38-4.33 (m, 3H), 3.80-3.69 (m, 3H), 3.53-3.49 (m, 2H), 3.14-3.12 (m, 2H), 2.94-2.89 (m, 2H), 2.79-2.75 (m, 3H), 2.47 (s, 3H), 2.46-2.15 (m, 6H), 1.96-1.93 (m, 1H), 1.48 (d, J = 7.2Hz, 3H), 1.36-1.23 (m, 1H), 1.06 (d, J = 6.6Hz, 3H), 0.92 (d, J = 6.6Hz, 3H). |
| 228 | D | NA | 1068.9 | 1H NMR (400 MHZ, DMSO-D6): δ : 9.02-8.93 (m, 1H), 8.85 (s, 1H), 8.21 (s, 2H), 7.91 (d, J = 7.9 Hz, 1H), 7.79 (d, J = 6.0 Hz, 1H), 7.69 (d, J = 8.3 Hz, 1H), 7.59 (d, J = 8.2 Hz, 1H), 7.74-7.54 (m, 1H), 7.53-7.44 (m, 1H), 7.53-7.35 (m, 1H), 7.39 (d, J = 8.3 Hz, 1H), 7.22 (t, J = 7.8 Hz, 1H), 6.91-6.81 (m, 2H), 6.54 (br d, J = 6.2 Hz, 1H), 6.19-6.09 (m, 1H), 5.99 (d, J = 16.0 Hz, 2H), 6.19 (s, 1H), 4.54-4.33 (m, 5H), 4.32-4.19 (m, 3H), 4.12 (br t, J = 5.4 Hz, 2H), 3.77-3.74 (m, 1H), 3.63(m, 1H), 3.47-3.40 (m, 2H), 3.35 (br d, J = 10.4 Hz, 1H), 3.32-3.28 (m, 2H), 3.25 (br d, J = 11.0 Hz, 2H), 3.09-2.96 (m, 2H), 2.71-2.54 (m, 3H), 2.47-2.46 (m, 3H), 2.39 (br s, 4H), 2.34 (s, 3H), 2.30-2.24 (m, 1H), 2.20-2.03 (m, 4H), 2.01-1.89 (m, 3H), 0.98 (d, J = 6.6 Hz, 2H), 0.85 (d, J = 6.6 Hz, 3H), 0.60 (dd, J = 6.5, 12.9 Hz, 2H). |
| 229 | D | NA | 1053.9 | 1H NMR (400 MHz, CD3OD): δ 8.67-8.50 (m, 1H), 8.24-8.17 (m, 1H), 7.82-7.73 (m, 3H), 7.67 (d, J = 8.1 Hz, 1H), 7.52-7.45 (m, 1H), 7.30-7.19 (m, 1H), 6.96-6.85 (m, 2H), 6.55 (dd, J = 2.0, 6.2 Hz, 1H), 6.15 (d, J = 2.0 Hz, 1H), 6.08-5.97 (m, 1H), 5.17-5.09 (m, 1H), 5.02 (q, J = 7.0 Hz, 1H), 4.60-4.56 (m, 1H), 4.56-4.51 (m, 2H), 4.46-4.28 (m, 4H), 3.81-3.63 (m, 3H), 3.43-3.35 (m, 2H), 3.13 (br d, J = 11.9 Hz, 2H), 2.90-2.73 (m, 4H), 2.60-2.54 (m, 3H), 2.49-2.08 (m, 13H), 2.00-1.80 (m, 3H), 1.67-1.56 (m, 2H), 1.53 (d, J = 7.1 Hz, 3H), 1.11-0.96 (m, 3H), 0.95-0.84 (m, 3H). |
| 230 | A | A | 1053.9 | 1H NMR (400 MHZ, CD3OD): δ 8.65-8.54 (m, 1H), 8.25-8.16 (m, 1H), 7.91-7.64 (m, 4H), 7.50 (s, 1H), 7.30-7.20 (m, 1H), 6.97-6.86 (m, 2H), 6.55 (dd, J = 2.0, 6.2 Hz, 1H), 6.15 (d, J = 2.0 Hz, 1H), 6.07-5.93 (m, 1H), 5.20-5.02 (m, 2H), 4.59-4.29 (m, 7H), 3.89-3.72 (m, 1H), 3.71-3.35 (m, 4H), 3.13 (br d, J = 11.4 Hz, 2H), 2.92-2.75 (m, 4H), 2.60-2.54 (m, 3H), 2.49-2.11 (m, 13H), 2.00-1.85 (m, 3H), 1.70-1.54 (m, 5H), 1.06 (d, J = 6.5 Hz, 3H), 0.95-0.85 (m, 3H). |
| 231 | A | A | 1073.8 | 1H NMR (300 MHz, CD3OD): δ 8.88 (s, 1H), 8.39-8.38 (d, J = 5.1 Hz, 2H), 7.80-7.74 (m, 2H), 7.49-7.36 (m, 5H), 7.25 (s, 1H), 6.93-6.90 (d, J = 7.8 Hz, 2H), 6.58-6.56 (d, J = 4.5 Hz, 1H), 6.19 (s, 1H), 6.12 (s, 1H), 5.31-5.11 (m, 4H), 4.62-4.44 (m, 8H), 3.82-3.69 (m, 3H), 3.14-3.11 (d, J = 11.1 Hz, 2H), 2.73-2.71(d, J = 5.7 Hz, 3H), 2.69-2.2.48 (m, 4H), 2.27-2.14 (m, 5H), 2.03 (s, 1H), 1.50-1.48 (d, J = 6.9 Hz, 3H), 1.08-1.06 (d, J = 6.6 Hz, 2H), 0.99-0.87 (m, 4H). |
| 232 | A | A | 1073.8 | 1H NMR (300 MHz, CD3OD): δ 8.89 (s, 1H), 8.39-8.36 (d, J = 8.1 Hz, 2H), 7.80-7.72 (m, 2H), 7.49-7.41 (m, 5H), 7.25 (s, 1H), 6.93-6.91 (d, J = 7.8 Hz, 2H), 6.61 (s, 1H), 6.20 (s, 1H), 6.11 (s, 1H), 5.41-5.12 (m, 4H), 4.62-4.53 (m, 8H), 3.91-3.66 (m, 3H), 3.40-3.32 (m, 2H), 3.15-3.11 (d, J = 11.4 Hz, 2H), 2.49-2.48 (d, J = 3.3 Hz, 3H), 2.28-2.18 (m, 6H), 2.03 (s, 1H), 1.58-1.52 (m, 3H), 1.08-1.06 (d, J = 6.6 Hz, 3H), 0.95-0.90 (m, 4H). |
| 233 | C | A | 1055.9 | 1H NMR (300 MHz, CD3OD): δ 8.11-8.10 (m, 1H), 7.77-7.71 (m, 2H), 7.53-7.40 (m, 3H), 7.36-7.29 (m, 3H), 7.25-7.18 (m, 2H), 7.14-7.12 (m, 1H), 6.95-6.84 (m, 3H), 6.55-6.52 (m, 1H), 6.16-6.15 (m, 1H), 6.09-6.06 (m, 1H), 5.30-5.22 (m, 1H), 5.14-4.97 (m, 4H), 4.59-4.50 (m, 3H), 4.47-4.36 (m, 1H), 3.80-3.59 (m, 3H), 3.39-3.34 (m, 2H), 3.12-3.08 (m, 2H), 2.67-2.63 (m, 4H), 2.44-2.34 (m, 1H), 2.31-2.29 (m, 3H), 2.24-2.11 (m, 5H), 1.98-1.89 (m, 1H), 1.60-1.46 (m, 3H), 1.06-0.95 (m, 3H), 0.92-0.85 (m, 3H). |
| 234 | A | A | 1055.9 | 1H NMR (300 MHz, CD3OD): δ 8.12-8.10 (m, 1H), 7.77-7.72 (m, 2H), 7.54-7.46 (m, 4H), 7.41-7.32 (m, 2H), 7.29-7.19 (m, 2H), 7.13-7.12 (m, 1H), 6.95-6.85 (m, 3H), 6.55-6.53 (m, 1H), 6.17-6.16 (m, 1H), 6.08-6.01 (m, 1H), 5.31-5.23 (m, 1H), 5.11-4.99 (m, 4H), 4.54-4.43 (m, 4H), 3.86-3.81 (m, 1H), 3.75-3.61 (m, 2H), 3.55-3.48 (m, 1H), 3.35 (s, 1H), 3.12-3.08 (m, 2H), 2.68-2.62 (m, 4H), 2.42-2.29 (m, 4H), 2.25-2.12 (m, 5H), 1.99-1.89 (m, 1H), 1.59-1.48 (m, 3H), 1.06-1.04 (m, 3H), 0.92-0.88 (m, 3H). |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| 235 | D | NA | 1096.9 | 1H NMR (400 MHZ, CD3OD): δ 8.87 (s, 1H), 8.45 (br s, 2H), 7.82 (d, J = 6.1 Hz, 1H), 7.76-7.69 (m, 1H), 7.66-7.57 (m, 2H), 7.52-7.43 (m, 3H), 7.24 (t, J = 7.7 Hz, 1H), 6.96-6.85 (m, 2H), 6.61 (dd, J = 2.0, 6.2 Hz, 1H), 6.26 (d, J = 1.8 Hz, 1H), 5.95 (d, J = 1.3 Hz, 1H), 4.67 (dt, J = 2.8, 8.0 Hz, 1H), 4.59-4.49 (m, 5H), 4.43 (br s, 2H), 4.37-4.22 (m, 4H), 3.81-3.62 (m, 3H), 3.37 (br s, 1H), 3.17-3.08 (m, 2H), 3.04 (br d, J = 4.8 Hz, 2H), 2.94-2.67 (m, 10H), 2.49 (s, 3H), 2.40 (br dd, J = 6.7, 13.6 Hz, 1H), 2.33-2.02 (m, 7H), 1.98 (d, J = 7.9 Hz, 3H), 1.08 (d, J = 6.6 Hz, 3H), 0.93 (d, J = 6.6 Hz, 3H). |
| 236 | D | A | 1073.8 | 1H NMR (400 MHZ, DMSO-D6): δ 14.13 (s, 1H), 9.0(m, 1H)8.60-8.46 (m, 1H), 8.39 (d, J = 7.5 Hz, 1H), 8.21(m, 1H), 7.91(d, J = 7.9 Hz, 1H), 7.81 (m, 1H) 7.80-7.74 (m, 2H), 7.68-7.43 (m, 2H), 7.32-7.18 (m, 2H), 6.90-6.80 (m, 2H), 6.58-6.51 (m, 1H), 6.23-6.15 (m, 2H), 5.97 (s, 2H), 5.34-5.27 (m, 1H), 5.18-5.11 (m, 2H), 5.10-4.86 (m, 2H), 4.50 (s, 2H), 4.41 (t, J = 7.8 Hz, 1H), 4.25 (s, 1H), 3.79 (d, J = 8.6 Hz, 1H), 3.57-3.53 (m, 2H), 3.25 (d, J = 11.5 Hz, 2H), 3.02 (d, J = 11.6 Hz, 2H), 2.65 (d, J = 5.2 Hz, 3H), 2.60-2.50(m, 3H), 2.31(m, 1H), 2.26-2.18 (m, 2H), 2.07 (s, 1H), 2.00-1.96 (s, 2H), 1.74(m, 1H), 1.48 (d, J = 7.1 Hz, 1H), 1.37 (d, J = 7.0 Hz, 2H), 1.23 (s, 1H), 0.97 (d, J = 6.6 Hz, 3H), 0.83 (d, J = 6.5 Hz, 4H). |
| 237 | A | A | 1073.8 | 1H NMR (400 MHz, DMSO-D6): δ 14.14 (s, 1H), 8.99 (d, J = 1.7 Hz, 1H), 8.55-8.46 (m, 2H), 8.22 (d, J = 3.0 Hz, 1H), 7.91 (d, J = 7.9 Hz, 1H), 7.81-7.69 (m, 3H), 7.50 (t, J = 4.4 Hz, 2H), 7.29-7.22 (m, 2H), 6.85 (m, 2H), 6.54 (d, J = 6.2 Hz, 1H), 6.23-6.15 (m, 2H), 5.97 (s, 2H), 5.31 (t, J = 6.2 Hz, 1H), 5.13 (d, J = 16.5 Hz, 2H), 5.02 (s, 1H), 4.93 (t, J = 7.1 Hz, 1H), 4.50 (s, 2H), 4.37 (t, J = 7.9 Hz, 1H), 4.28 (s, 1H), 3.73-3.66 (m, 2H), 3.46 (d, J = 10.6 Hz, 1H), 3.25 (d, J = 11.7 Hz, 2H), 3.02 (d, J = 11.5 Hz, 2H), 2.65 (s, 3H), 2.59-2.53(m, 4H), 2.23 (d, J = 8.3 Hz, 1H), 2.18 (d, J = 7.5 Hz, 2H), 1.97 (s, 3H), 1.75 (m, 1H), 1.48-1.35 (m, 3H), 1.23 (s, 1H), 0.96 (d, J = 6.5 Hz, 3H), 0.82 (m, 3H). |
| 238 | A | A | 969.8 | 1H NMR (400 MHZ, DMSO-D6): δ 8.99-8.98 (m, 1H), 8.47-8.46 (m, 1H), 8.40 (d, J = 7.6 Hz, 1H), 8.22-8.21 (m, 2H), 8.18 (m, 1H), 8.01 (dd, J = 1.6, 8.0 Hz, 1H), 7.47-7.42 (m, 2H), 7.37-7.35 (m, 2H), 7.28-7.24 (m, 1H), 6.94-6.90 (m, 2H), 6.49 (s, 2H), 6.08-5.91 (m, 1H), 5.11 (d, J = 2.0 Hz, 2H), 4.92-4.89 (m, 1H), 4.38-4.18 (m, 5H), 3.72-3.63 (m, 2H), 3.46-3.43 (m, 2H), 3.05-3.00 (m, 1H), 2.73-2.69 (m, 2H), 2.61 (t, J = 6.0 Hz, 2H), 2.45 (s, 3H), 2.28-1.99 (m, 9H), 1.81-1.72 (m, 3H), 1.45-1.34 (m, 5H), 0.97-0.94 (m, 3H), 0.83-0.78 (m, 3H). |
| 239 | D | A | 1086.9 | 1H NMR (400 MHZ, CD3OD): δ 8.91 (s, 1H), 7.44 (t, J = 8.1 Hz, 1H), 7.34-7.16 (m, 2H), 6.09-5.93 (m, 1H), 5.34-5.13 (m, 2H), 4.61-4.37 (m, 2H), 3.87-3.79 (m, 1H), 3.70-3.58 (m, 2H), 2.50 (s, 3H), 2.37 (s, 1H), 2.24-2.13 (m, 1H), 2.00-1.90 (m, 1H), 1.64-1.49 (m, 3H), 1.29 (s, 1H), 1.06 (d, J = 6.5 Hz, 3H), 0.89 (d, J = 6.7 Hz, 3H), 0.10 (d, J = 2.9 Hz, 1H). |
| 240 | A | A | 1086.9 | 1H NMR (400 MHZ, DMSO-D6): δ 9.77 (s, 1H), 9.06-8.96 (m, 1H), 8.50 (d, J = 7.5 Hz, 1H), 7.94 (d, J = 7.0 Hz, 1H), 7.57 (d, J = 7.7 Hz, 1H), 7.49 (s, 1H), 7.45-7.36 (m, 1H), 7.43-7.28 (m, 1H), 7.02 (d, J = 8.3 Hz, 1H), 6.99-6.83 (m, 3H), 6.27 (s, 1H), 6.17-6.00 (m, 1H), 5.22 (s, 1H), 5.14-5.04 (m, 1H), 4.83 (s, 2H), 4.51 (s, 2H), 4.40-4.22 (m, 4H), 3.72-3.68 (m, 1H), 3.68 (s, 1H), 3.37-3.27 (m, 1H), 3.24-2.93 (m, 9H), 2.46 (s, 3H), 2.46-2.34 (m, 4H), 2.28-2.18 (m, 3H), 2.13-1.96 (m, 4H), 1.90 (s, 2H), 1.80-1.56 (m, 2H), 1.50-1.35 (m, 3H), 0.97 (d, J = 6.5 Hz, 3H), 0.86-0.74 (m, 3H). |
| 241 | B | A | 1108.9 | |
| 242 | A | A | 1108.9 | |
| 243 | A | A | 1105.9 | 1H NMR (400 MHZ, DMSO-D6): δ 9.03-8.99 (m, 2H), 8.72 (d, J = 2.0 Hz, 1H), 8.25 (s, 2H), 8.04-7.98 (m, 1H), 7.92-7.90 (m, 1H), 7.79-7.71 (m, 2H), 7.49 (s, 1H), 7.24-7.20 (m, 1H), 6.87-6.82 (m, 2H), 6.52 (dd, J = 2.0, 6.0 Hz, 1H), 6.46-6.18 (s, 1H), 6.13-6.12 (m, 1H), 6.07 (s, 1H), 5.95 (s, 2H), 5.47-5.39 (m, 1H), 5.21-5.15 (m, 1H), 4.53-4.49 (m, 3H), 4.36-4.17 (m, 4H), 3.77-3.74 (m, 1H), 3.64 (d, J = 9.6 Hz, 2H), 3.02-2.99 (m, 2H), 2.76-2.58 (m, 7H), 2.29-2.24 (m, 4H), 2.21-2.06 (m, 8H), 1.99-1.88 (m, 4H), 1.78-1.70 (m, 3H), 1.43-1.36 (m, 2H), 0.95-0.86 (m, 3H), 0.79-0.74 (m, 3H). |
| 244 | A | A | 1105.9 | 1H NMR (400 MHZ, DMSO-D6): δ 9.03-9.01 (m, 2H), 8.66-8.64 (m, 1H), 8.20 (s, 2H), 7.95-7.90 (m, 2H), 7.82-7.76 (m, 2H), 7.49 (m, 1H), 7.24-7.20 (m, 1H), 6.87-6.82 (m, 2H), 6.52 (dd, J = 2.0, 6.0 Hz, 1H), 6.41-6.27 (s, 1H), 6.13-6.12 (m, 1H), 6.09 (s, 1H), 5.95 (s, 2H), 5.41-5.37 (m, 1H), 5.20-5.16 (m, 1H), 4.48-4.46 (m, 3H), 4.31-4.17 (m, 4H), 3.73-3.70 (m, 1H), 3.65 (d, J = 9.6 Hz, 2H), 3.02-2.99 (m, 2H), 2.76-2.67 (m, 8H), 2.32-2.21 (m, 7H), 2.20-1.91 (m, 9H), 1.77-1.71 (m, 3H), 1.44-1.36 (m, 2H), 0.98-0.94 (m, 3H), 0.82-0.79 (m, 3H). |
| 245 | B | A | 1124.9 | 1H NMR (400 MHZ, CD3OD): δ 8.91-8.89 (d, J = 10.8 Hz, 1H), 7.81-7.79 (m, 2H), 7.55-7.42 (m, 5H), 7.25 (s, 1H), 6.93-6.91 (d, J = 7.6 Hz, 2H), 6.58-6.57 (d, J = 6.0 Hz, 1H), 6.23 (s, 1H), 6.16 (s, 1H), 4.63 (s, 4H), 4.53 (s, 3H), 4.37-4.33 (m, 5H), 3.70-3.43 (m, 4H), 3.14-3.11 (m, 2H), |

TABLE 2B-continued

| Target protein degradation via exemplary bifunctional degradation compounds of Table 1B | | | | |
|---|---|---|---|---|
| Ex. # | *$DC_{50}$ (nM) | **$D_{max}$ (%) | MH+ | NMR transcript |
| | | | | 3.02-2.94 (m, 4H), 2.83-2.66 (m, 11H), 2.50-2.48 (m, 2H), 2.26-2.15 (m, 9H), 1.79-1.41 (m, 3H), 1.05-1.01 (m, 3H), 0.90-0.87 (m, 4H). |
| 246 | A | A | 1124.9 | 1H NMR (400 MHz, CD3OD): δ 8.91 (s, 1H), 7.81-7.75 (m, 2H), 7.50-7.47 (d, J = 9.2 Hz, 5H), 7.25 (s, 1H), 6.93-6.91 (m, 2H), 6.58-6.57 (d, J = 6.4 Hz, 1H), 6.24 (s, 1H), 6.10 (s, 1H), 4.63-4.54 (m, 6H), 4.43-4.33 (m, 5H), 3.95-3.84 (m, 1H), 3.70-3.42 (m, 2H), 3.15-3.11 (m, 2H), 3.02-2.99 (m, 3H), 2.86-2.68 (m, 11H), 2.51-2.49 (m, 3H), 2.37-2.33 (m, 5H), 2.27-2.15 (m, 5H), 2.11 (s, 1H), 1.78-1.41 (m, 3H), 1.07-1.01 (m, 3H), 0.92-0.87 (m, 4H). |
| 247 | D | NA | 1039.9 | 1H NMR (400 MHZ, DMSO-D6): δ 14.15 (s, 1H), 9.12-8.21 (m, 1H), 8.00-7.85 (m, 1H), 7.84-7.76 (m, 1H), 7.75-7.62 (m, 1H), 7.61-7.52 (m, 3H), 7.51-7.43 (m, 1H), 7.31-7.12 (m, 1H), 7.00-6.73 (m, 2H), 6.59-6.43(m, 1H), 6.21-6.02 (m, 1H), 6.01-5.86 (m, 2H), 5.23-5.11 (m, 1H), 5.10-5.07 (m, 1H), 5.02- 4.89 (m, 1H), 4.88-4.72 (m, 1H), 4.55-4.46 (m, 2H), 4.41-4.31(m, 1H), 4.30-4.18 (m, 2H), 4.17-4.00 (m, 1H), 3.81-3.65 (m, 1H), 3.61-3.42 (m, 2H), 3.27-3.25 (m, 1H), 3.24-3.20 (m, 1H), 3.09-2.97 (m, 2H), 2.82-2.71 (m, 2H), 2.70-2.61 (m, 2H), 2.32-2.25 (m, 5H), 2.23-2.05 (m, 5H), 2.04-1.85 (m, 4H), 1.83-1.71 (m, 2H), 1.51-1.29 (m, 5H), 1.25-1.23 (m, 1H), 1.15-0.65 (m, 6H). |
| 248 | D | NA | 1039.9 | 1H NMR (400 MHz, DMSO-D6): δ 14.15 (s, 1H), 9.00-8.38 (m, 1H), 8.01-7.82 (m, 1H), 7.81-7.73 (m, 1H), 7.72-7.59 (m, 3H), 7.58-7.40 (m, 1H), 7.35-7.10 (m, 1H), 6.98-6.75 (m, 2H), 6.62-6.41 (m, 1H), 6.18-6.10 (m, 1H), 6.00-5.95 (m, 1H), 5.32-5.13 (m, 1H), 5.12-5.00 (m, 1H), 4.99-4.76 (m, 1H), 4.61-4.43 (m, 2H), 4.42-4.30 (m, 2H), 4.29-4.23 (m, 1H), 4.22-4.03 (m, 2H), 3.90-3.71 (m, 1H), 3.70-3.52 (m, 1H), 3.48-3.39(m, 1H), 3.30-3.26 (m, 1H), 3.25-3.23 (m, 1H), 3.22-3.21(m, 1H), 3.11-2.90 (m, 2H), 2.80-2.71 (m, 2H), 2.70-2.60 (m, 2H), 2.40-2.05 (m, 10H), 2.04-1.85 (m, 4H), 1.84-1.68 (m, 2H), 1.50-1.28 (m, 5H), 1.27-1.09(m, 2H), 0.99-0.61 (m, 6H). |
| 249 | D | A | 1100.9 | 1H NMR (400 MHZ, CD3OD): δ 8.87 (s, 1H), 8.06 (s, 1H), 7.80-7.74 (m, 2H), 7.49-7.41 (m, 2H), 7.37 (d, J = 8.4 Hz, 5H), 7.25 (d, J = 7.6 Hz, 2H), 6.92 (d, J = 8.4 Hz, 2H), 6.60 (d, J = 6.0 Hz, 1H), 6.20 (s, 1H), 6.06 (s, 1H), 5.00 (d, J = 6.8 Hz, 1H), 4.36-4.34 (m, 2H), 3.79-3.70 (m, 3H), 3.14-3.11 (m, 2H), 2.70-2.59 (m, 6H), 2.50-2.48 (m, 3H), 2.35 (s, 1H), 2.27-2.21 (m, 5H), 2.17-2.04 (m, 4H), 1.63 (s, 1H), 1.50-1.49 (d, J = 6.8 Hz, 3H), 1.35-1.29 (m, 2H), 1.08-1.06 (d, J = 6.4 Hz, 3H), 0.93-0.87 (m, 6H). |
| 250 | A | A | 1100.9 | 1H NMR (400 MHZ, MeOD): δ 8.87 (s, 1H), 7.79-7.72 (m, 2H), 7.46-7.39 (m, 7H), 7.26-7.24 (d, J = 6.9 Hz, 2H), 6.92-6.90 (d, J = 7.8 Hz, 2H), 6.57-6.54 (d, J = 6.9 Hz, 1H), 6.18 (s, 1H), 6.03 (s, 1H), 5.28 (s, 1H), 5.05-5.00 (m, 4H), 4.88-4.80 (m, 3H), 3.69-3.64 (m, 2H), 3.13-3.09 (d, J = 11.4 Hz, 2H), 2.68-2.59 (m, 7H), 2.48-2.46 (d, J = 5.4 Hz, 3H), 2.35 (s, 1H), 2.25-2.05 (m, 8H), 2.04-1.89 (m, 1H), 1.63 (s, 1H), 1.58-1.51 (m, 3H), 1.29-1.27 (d, J = 5.1 Hz, 2H), 1.06-1.04 (d, J = 6.3 Hz, 3H), 0.92-0.87 (m, 4H). |
| 251 | C | A | 1122.0 | 1H NMR (400 MHZ, CD3OD): δ 8.91-8.84 (m, 1H), 8.47 (s, 1H), 7.79-7.70 (m, 2H), 7.49-7.33 (m, 5H), 7.26-7.16 (m, 1H), 6.92-6.83 (m, 2H), 6.54 (dd, J = 1.9, 6.2 Hz, 1H), 6.16-6.06 (m, 2H), 5.18-5.08 (m, 1H), 4.98 (q, J = 6.9 Hz, 1H), 4.63-4.49 (m, 5H), 4.46-4.33 (m, 2H), 3.75-3.58 (m, 6H), 3.42-3.32 (m, 2H), 3.23 (s, 2H), 3.10 (d, J = 11.5 Hz, 2H), 2.99 (s, 1H), 2.91-2.72 (m, 4H), 2.49-2.06 (m, 14H), 2.04-1.88 (m, 4H), 1.78 (d, J = 12.2 Hz, 4H), 1.60-1.46 (m, 3H), 1.38-1.22 (m, 2H), 1.05 (d, J = 6.6 Hz, 3H), 0.95-0.89 (m, 3H), 0.84 (d, J = 6.4 Hz, 1H). |
| 252 | D | A | 1086.9 | $^1$H NMR (400 MHZ, CD3OD): δ 9.06-8.66 (m, 1H), 7.83 (d, J = 7.2 Hz, 1H), 7.64-7.53 (m, 2H), 7.42 (td, J = 7.6, 15.2 Hz, 2H), 7.30-7.14 (m, 2H), 7.08-6.99 (m, 2H), 6.86 (dd, J = 2.0, 7.2 Hz, 1H), 6.25 (s, 1H), 6.15-6.07 (m, 1H), 5.23 (s, 1H), 5.03-4.92 (m, 2H), 4.90-4.82 (m, 2H), 4.59 (t, J = 7.6 Hz, 3H), 4.44 (s, 2H), 3.92-3.42 (m, 10H), 3.29-3.09 (m, 1H), 3.23-3.03 (m, 1H), 2.59 (s, 4H), 2.47-2.34 (m, 4H), 2.34-2.15 (m, 6H), 2.15-1.87 (m, 4H), 1.77 (s, 1H), 1.63-1.46 (m, 3H), 1.07 (d, J = 6.8 Hz, 3H), 0.97-0.89 (m, 3H). |
| 253 | A | A | 1086.9 | $^1$H NMR (400 MHZ, CD3OD): δ 9.13-8.54 (m, 1H), 7.82 (d, J = 7.6 Hz, 1H), 7.59-7.52 (m, 2H), 7.42 (td, J = 7.6, 12.0 Hz, 2H), 7.27-7.13 (m, 2H), 7.08-6.98 (m, 2H), 6.91-6.80 (m, 1H), 6.25 (s, 1H), 6.14-6.00 (m, 1H), 5.22 (s, 1H), 5.11-4.92 (m, 2H), 4.77 (s, 1H), 4.59 (s, 2H), 4.53-4.36 (m, 3H), 3.92-3.67 (m, 5H), 3.66-3.57 (m, 3H), 3.56-3.34 (m, 2H), 3.27 (s, 2H), 3.13 (s, 1H), 2.59 (s, 4H), 2.44-2.33 (m, 4H), 2.31-2.12 (m, 6H), 2.12-1.88 (m, 4H), 1.85-1.67 (m, 1H), 1.62-1.48 (m, 3H), 1.05 (d, J = 6.5 Hz, 3H), 0.93-0.83 (m, 3H). |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| 254 | D | NA | 1069.9 | $^1$H NMR (400 MHZ, CD3OD): δ 8.93 (d, J = 1.5 Hz, 1H), 8.73-8.58 (m, 1H), 8.33 (s, 2H), 8.04-7.65 (m, 4H), 7.48 (d, J = 5.0 Hz, 1H), 7.25 (t, J = 7.8 Hz, 1H), 7.00-6.84 (m, 2H), 6.66-6.54 (m, 1H), 6.16 (s, 1H), 6.11-5.90 (m, 1H), 5.24-5.12 (m, 1H), 5.10-4.97 (m, 1H), 4.59-4.49 (m, 4H), 4.46-4.34 (m, 2H), 3.92-3.57 (m, 4H), 3.38 (d, J = 11.6 Hz, 3H), 3.32-3.21 (m, 4H), 3.15-3.01 (m, 3H), 2.71-2.62 (m, 3H), 2.54-1.75 (m, 16H), 1.61-1.49 (m, 3H), 1.12-0.99 (m, 2H), 0.95-0.82 (m, 4H). |
| 255 | D | NA | 1042.9 | 1H NMR (300 MHz, CD3OD): δ 8.87 (s, 1H), 7.94-7.92 (m, 2H), 7.72 (s, 1H), 7.59-7.47 (m, 1H), 7.45 (s, 3H), 7.37-7.26 (m, 1H), 7.02-6.91 (m, 2H), 6.90-6.79 (m, 2H), 5.86 (s, 1H), 4.65 (t, J = 7.8 Hz, 1H), 4.49 (d, J = 4.6 Hz, 1H), 4.44- 4.28 (m, 3H), 4.22 (t, J = 5.3 Hz, 2H), 3.75- 3.68 (m, 5H), 3.41-3.31 (m, 3H), 3.06-2.96 (m, 4H), 2.83-2.73 (m, 3H), 2.70-2.51 (m, 9H), 2.47 (s, 3H), 2.43- 2.32 (m, 1H), 2.28- 2.06 (m, 2H), 1.83-1.81 (m, 4H), 1.04 (d, J = 6.6 Hz, 3H), 0.89 (d, J = 6.7 Hz, 3H). |
| 256 | D | NA | 1042.9 | 1H NMR (300 MHz, CD3OD): δ 8.87 (s, 1H), 7.94-7.92 (m, 2H), 7.72 (s, 1H), 7.59-7.45 (m, 4H), 7.37-7.32 (m, 1H), 7.02-6.91 (m, 2H), 6.90-6.79 (m, 2H), 6.00 (s, 1H), 4.65-4.49 (m, 5H), 4.22-4.12 (m, 1H), 3.85-3.81 (m, 1H), 3.65-3.59 (m, 4H), 3.41-3.31 (m, 6H), 3.06-2.96 (m, 4H), 2.83-2.73 (m, 8H), 2.47 (s, 3H), 2.43- 2.32-2.06 (m, 3H), 1.83-1.81 (m, 4H), 1.03-0.91 (m, 1H), 0.91-0.82 (m, 6H). |
| 257 | B | A | 1071.9 | 1H NMR (400 MHZ, CD3OD): δ 8.89 (s, 1H), 7.98-7.90 (m, 2H), 7.80 (s, 1H), 7.49-7.34 (m, 5H), 7.01-7.00 (m, 2H), 6.89-6.83 (m, 2H), 6.07 (s, 1H), 5.04 (s, 1H), 4.64-4.62 (m, 1H), 4.45-4.33 (m, 5H), 4.06 (s, 2H), 3.82-3.35 (m, 9H), 3.33-3.19 (m, 3H), 2.93 (s, 2H), 2.82-2.70 (m, 10H), 2.50-2.49 (m, 4H), 2.30-2.20 (m, 1H), 2.04-2.01 (m, 5H), 1.13-1.16 (m, 5H), 0.98-0.86 (m, 3H). |
| 258 | D | NA | 1146.9 | 1H NMR (400 MHZ, DMSO-D6): § 13.63 (s, 1H), 9.15-9.00 (m, 1H), 8.70 (d, J = 9.0 Hz, 1H), 8.08-8.01 (m, 1H), 7.91 (d, J = 5.8 Hz, 1H), 7.68 (s, 1H), 7.48-7.29 (m, 6H), 7.27-7.13 (m, 3H), 7.03-6.95 (m, 3H), 6.80-6.78 (m, 1H), 6.49 (d, J = 1.9 Hz, 1H), 6.27-6.10 (m, 1H), 5.54-5.45 (m, 1H), 5.10-4.93 (m, 1H), 4.63-4.55 (m, 1H), 4.33-4.23 (m, 5H), 3.76 (d, J = 8.5 Hz, 1H), 3.52 (s, 1H), 3.46 (d, J = 8.6 Hz, 1H), 3.38-3.35 (m, 4H), 3.24-3.12 (m, 3H), 2.91 (d, J = 11.1 Hz, 2H), 2.71-2.56 (m, 4H), 2.47-2.34 (m, 10H), 2.07-1.70(m, 3H), 1.59-1.53 (m, 4H), 1.01-0.93 (m, 2H), 0.90- 0.86 (m, 4H). |
| 259 | A | A | 1146.9 | 1H NMR (400 MHz, DMSO-D6): δ 13.64 (s, 1H), 9.00-8.69 (m, 3H), 8.05 (d, J = 8.0 Hz, 1H), 7.91 (d, J = 5.8 Hz, 1H), 7.69 (s, 1H), 7.47-7.20 (m, 8H), 7.11-7.01 (m, 2H), 6.96 (d, J = 7.9 Hz, 2H), 6.78 (d, J = 6.0 Hz, 1H), 6.49 (s, 1H), 6.14-5.91 (m, 1H), 5.68-5.47 (m, 1H), 5.09 (s, 1H), 5.00-4.42 (m, 1H), 4.40-4.26 (m, 2H), 4.23-4.14 (m, 3H), 3.73-3.63 (m, 2H), 3.57-3.37(m, 7H), 3.26-3.06 (m, 3H), 2.91 (d, J = 11.1 Hz, 2H), 2.69-2.57 (m, 5H), 2.47-2.37 (m, 7H), 2.35-2.18(m, 2H), 2.03-1.91 (m, 1H), 1.88-1.65 (m, 1H), 1.59 (s, 4H), 1.00-0.95 (m, 3H), 0.84 (dd, J = 15.9, 6.6 Hz, 3H). |
| 260 | D | NA | 1081.9 | $^1$H NMR (400 MHZ, DMSO-$d_6$): δ 9.03-8.98 (m, 1H), 8.59 (d, J = 2.1 Hz, 1H), 8.37 (d, J = 7.7 Hz, 1H), 8.19 (s, 1H), 7.92 (d, J = 8.2 Hz, 1H), 7.80-7.64 (m, 3H), 7.50 (s, 1H), 7.23 (t, J = 7.8 Hz, 1H), 6.90-6.81 (m, 2H), 6.53 (d, J = 4.4 Hz, 1H), 6.15 (s, 1H), 6.07 (s, 1H), 5.97 (s, 2H), 5.12-5.03 (m, 1H), 4.91 (t, J = 7.0 Hz, 1H), 4.50 (s, 2H), 4.45-4.32 (m, 2H), 4.27 (s, 1H), 4.19-4.12 (m, 1H), 3.75 (d, J = 8.6 Hz, 1H), 3.69-3.53 (m, 3H), 3.51-3.45 (m, 2H), 3.25 (d, J = 12.1 Hz, 6H), 3.02 (br d, J = 11.4 Hz, 2H), 2.89 (t, J = 13.1 Hz, 1H), 2.67-2.64 (m, 3H), 2.53 (d, J = 2.0 Hz, 3H), 2.31-2.12 (m, 6H), 2.06 (t, J = 9.5 Hz, 1H), 2.00-1.91 (m, 2H), 1.70-1.58 (m, 5H), 1.49 (d, J = 6.8 Hz, 0.7H), 1.39 (d, J = 7.0 Hz, 2.4H), 0.97 (d, J = 6.6 Hz, 3H), 0.83 (d, J = 6.7 Hz, 2.5H), 0.76 (d, J = 6.7 Hz, 0.6H). |
| 261 | A | A | 1081.9 | $^1$H NMR (400 MHZ, DMSO-$d_6$): δ 9.00 (s, 1H), 8.52 (s, 1H), 8.48 (d, J = 7.5 Hz, 1H), 8.18 (s, 1H), 7.91 (d, J = 8.1 Hz, 1H), 7.80-7.74 (m, 2H), 7.73-7.66 (m, 1H), 7.49 (s, 1H), 7.22 (t, J = 7.6 Hz, 1H), 6.89-6.80 (m, 2H), 6.52 (d, J = 4.6 Hz, 1H), 6.14 (s, 1H), 6.07 (s, 1H), 5.99-5.87 (m, 2H), 5.08 (quin, J = 6.6 Hz, 1H), 4.98-4.87 (m, 1H), 4.49 (s, 2H), 4.42-4.31 (m, 2H), 4.27 (s, 1H), 4.22-4.13 (m, 2H), 3.73-3.59 (m, 2H), 3.31-3.27 (m, 6H), 3.06-2.87 (m, 3H), 2.64 (s, 3H), 2.55 (s, 2H), 2.52 (s, 3H), 2.31-2.10 (m, 6H), 2.08-1.91 (m, 3H), 1.80-1.62 (m, 6H), 1.47 (d, J = 6.8 Hz, 0.5H), 1.40 (d, J = 7.0 Hz, 2.6H), 0.98-0.91 (m, 3H), 0.84-0.76 (m, 3H). |
| 262 | D | NA | 1142.0 | 1H NMR (300 MHz, CD3OD): δ 8.86 (s, 1H), 7.94-7.85 (m, 2H), 7.71 (s, 1H), 7.64-7.26 (m, 5H), 6.98-6.82 (m, 4H), 5.93-5.87 (m, 1H), 5.21-5.02 (m, 2H), 4.73-4.68 (m, 1H), 4.57-4.31 (m, 4H), 4.23-4.20 (m, 1H), 3.92-3.87 (m, 2H), 3.74-3.57 (m, 7H), 3.43-3.37 (m, 6H), 3.01-2.97 (m, 2H), 2.80-2.55 (m, 11H), 2.47-2.45 (m, 3H), 2.39-2.31 (m, 1H), 2.18-2.14 (m, 2H), 1.82 (s, 5H), 1.61-1.57 (m, 2H), 1.33-1.20 (m, 2H), 1.05-0.41 (m, 6H) |
| 263 | B | A | 1010.9 | 1H NMR (400 MHZ, CD3OD): δ 7.95 (s, 1H), 7.93 (s, 1H) 7.73 (s, 1H), 7.49-7.48 (d, J = 4Hz, 2H), 7.38-7.44 (m, 4H), 7.34 (s, 1H), 6.99-6.98 (d, J = 4Hz, 2H), 6.97-6.83 (m, 2H), 6.35-6.34 (d, J = 4Hz, 1H), 6.05 (s, 1H), 5.02-5.00 (d, J = 8Hz, 2H), 4.89 (s, 1 H), 4.58 (s, 3H), 4.44-4.31 (m, 2H), |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| | | | | 3.88-3.86 (d, J = 8Hz, 3H), 3.79-3.71 ( d, J = 4Hz, 1H), 3.70-3.64 (m, 1H), 3.44-3.34 (m 3H), 3.33-3.32 (m, 3H), 3.05-3.02 ( d, J = 12Hz, 2H), 2.83 (s, 5H), 2.82 (s, 8H), 2.81 (s, 1H), 2.79-2.77 (m, 1H), 2.64 (s, 1H), 1.86 (s, 4H), 1.49 (s, 3H), 1.31(s, 2H), 1.08 (s, 3H), 1.06 (s, 1H), 0.93-0.92 (d, J = 4Hz, 3H), 0.03 (s, 1H). |
| 264 | A | A | 1010.9 | 1H NMR (400 MHZ, CD3OD): δ 7.95-7.94 (d, J = 4Hz, 2H), 7.90-7.88 (d, J = 8Hz, 1H) 7.74 (s, 5H), 7.50-7.43 (m, 1H), 7.33-7.32 (d, J = 4Hz, 2H), 7.00-6.98 (d, J = 8Hz, 2H), 6.88-6.83 (s, 1H), 6.36-6.35 (d, J = 4Hz, 1H), 6.02 (s, 1H), 5.07 (s, 1H), 5.05-4.55 (m, 5H), 4.53-4.43 (m, 4H), 4.42-4.36 (m, 4H), 4.35-3.84 (m, 3H), 3.83-3.62 (m, 2H), 3.48-3.41 ( m, 4H), 3.41-3.32 (m, 7H), 3.04-3.02 (m 1H), 2.83-2.82 (d, J = 4Hz, 1H), 2.67 ( s, 1H), 1.97 (s, 4H), 1.85-1.83 (m, 3H), 1.31 (s, 2H), 1.08-1.06 (m, 3H), 0.93-0.89 (m, 3H). |
| 265 | D | NA | 1027.9 | 1H NMR (300 MHz, DMSO-D6): δ 13.62 (s, 1H), 9.00-8.65 (m, 1H), 8.55-8.24 (m, 2H), 8.17-8.00 (m, 1H), 7.98-7.86 (m, 1H), 7.78-7.62 (m, 1H), 7.55-7.31 (m, 4H), 7.02-6.87 (m, 2H), 6.85-6.72 (m, 1H), 6.67-6.42 (m, 1H), 6.21-6.00 (m, 1H), 5.26-5.01 (m, 1H), 4.98-4.81 (m, 1H), 4.55-4.11 (m, 5H), 3.80-3.62 (m, 1H), 3.60-3.42 (m, 5H), 3.30-3.12 (m, 3H), 3.02-2.89 (m, 1H), 2.75-2.56 (m, 3H), 2.43-2.35 (m, 5H), 2.33-2.30 (m, 3H), 2.29-1.96 (m, 4H), 1.94-1.57 (m, 5H), 1.52-1.40 (m, 1H), 1.39-1.13 (m, 5H), 1.01-0.72 (m, 6H). |
| 266 | A | A | 1027.9 | 1H NMR (300 MHz, DMSO-D6): δ 13.63 (s, 1H), 8.73 (s, 1H), 8.52-8.35 (m, 1H), 8.17-7.81 (m, 2H), 7.80-7.62 (m, 1H), 7.52-7.44 (m, 2H), 7.41-7.33 (m, 2H), 7.31-7.26 (m, 1H), 7.01-6.92(m, 2H), 6.81-6.76 (m, 1H), 6.63-6.43 (m, 1H), 6.22-5.86 (m, 1H), 5.51-5.02(m, 1H), 4.98-4.85 (m, 1H), 4.43-4.12 (m, 4H), 3.78-3.54 (m, 1H), 3.48-3.40 (m, 3H), 3.38-3.22 (m, 3H), 3.01-2.87 (m, 1H), 2.75-2.56 (m, 3H), 2.53-2.50 (m, 2H), 2.45-2.41 (m, 7H), 2.35-2.31 (m, 3H), 2.28-2.11 (m, 2H), 2.09-1.72 (m, 3H), 1.70-1.56 (m, 3H), 1.45-1.33 (m, 3H), 1.31-1.01 (m, 3H), 1.00-0.75 (m, 6H). |
| 267 | B | A | 1104.9 | $^{1}$H NMR (400 MHZ, DMSO-$d_6$): δ 14.15 (s, 1H), 9.49-8.86 (m, 2H), 7.95-7.75 (m, 2H), 7.62-7.43 (m, 5H), 7.26-7.20 (m, 1H), 6.90-6.81 (m, 2H), 6.53 (s, 1H), 6.40-5.95 (m, 5H), 5.39-5.13 (m, 3H), 4.57-4.47 (m, 3H), 4.31-4.26 (m, 3H), 3.78-3.64 (m, 1H), 3.62-3.44 (m, 4H), 3.43-3.25 (m, 3H), 3.06- 2.69 (m, 6H), 2.47 (s, 3H), 2.34-2.25 (m, 5H), 2.22-2.04 (m, 4H), 2.05-1.70 (m, 5H), 1.62-1.47 (m, 2H), 0.97 (s, 2H), 0.90- 0.70 (m, 4H). |
| 268 | A | A | 1104.9 | $^{1}$H NMR (400 MHZ, DMSO-$d_6$): δ 14.15 (s, 1H), 9.62-8.86 (m, 2H), 7.96-7.74 (m, 2H), 7.60-7.51 (m, 5H), 7.26-7.20 (m, 1H), 6.89-6.82 (m, 2H), 6.53 (s, 1H), 6.30-6.20 (m, 1H), 6.16-5.89 (m, 4H), 5.42-5.26 (m, 1H), 5.23-5.05 (m, 2H), 4.55-4.48 (m, 3H), 4.32-4.18 (m, 3H), 3.80-3.73 (m, 1H), 3.70-3.67 (m, 1H), 3.62- 3.39 (m, 3H), 3.31- 3.25 (m, 2H), 3.05-3.00 (m, 3H), 2.82-2.64 (m, 4H), 2.60-2.48 (m, 3H), 2.41-2.28 (m, 5H), 2.20-2.15 (m, 3H), 2.10-1.92 (m, 4H), 1.81-1.67 (m, 3H), 1.50-1.43 (m, 2H), 0.98 (s, 3H), 0.82 (s, 3H). |
| 269 | D | NA | 1087.9 | $^{1}$H NMR (400 MHZ, DMSO-$d_6$): δ 9.02-8.95 (m, 1H), 8.47 (d, J = 1.6 Hz, 1H), 8.34 (d, J = 7.2 Hz, 1H), 8.14 (s, 2H), 7.91 (d, J = 8.0 Hz, 1H), 7.80-7.63 (m, 3H), 7.49 (s, 1H), 7.22 (t, J = 7.6 Hz, 1H), 6.89-6.80 (m, 2H), 6.52 (dd, J1=1.6 Hz, J2=6.0 Hz, 1H), 6.13 (d, J = 1.6 Hz, 1H), 5.96 (s, 2H), 5.22-5.13 (m, 1H), 4.90-4.79 (m, 1H), 4.48 (s, 2H), 4.39-4.22 (m, 5H), 3.92-3.58 (m, 2H), 3.24 (d, J = 12.0 Hz, 1H), 3.01 (d, J = 11.2 Hz, 2H), 2.87-2.54 (m, 9H), 2.41-2.24 (m, 6H), 2.17 (d, J = 7.2 Hz, 4H), 2.08-1.89 (m, 3H), 1.80-1.65 (m, 3H), 1.49-1.32 (m, 5H), 0.97 (d, J = 6.4 Hz, 3H), 0.83 (d, J = 6.8 Hz, 3H). |
| 270 | A | A | 1087.9 | $^{1}$H NMR (400 MHZ, DMSO-$d_6$): δ 8.99 (s, 1H), 8.54-8.47 (m, 2H), 8.16 (s, 1H), 7.91 (d, J = 8.0 Hz, 1H), 7.80-7.67 (m, 3H), 7.49 (s, 1H), 7.25-7.17 (m, 1H), 6.91-6.79 (m, 2H), 6.52 (d, J = 6.0 Hz, 1H), 6.13 (d, J = 1.6 Hz, 1H), 5.96 (s, 2H), 5.23-5.13 (m, 1H), 4.92 (t, J = 7.2 Hz, 1H), 4.48 (s, 2H), 4.39-4.20 (m, 5H), 3.81-3.64 (m, 2H), 3.27-3.17 (m, 1H), 3.01 (d, J = 11.6 Hz, 3H), 2.79-2.59 (m, 8H), 2.42-2.23 (m, 6H), 2.21-2.10 (m, 4H), 2.07-1.92 (m, 3H), 1.81-1.70 (m, 3H), 1.47-1.35 (m, 5H), 1.02-0.93 (m, 3H), 0.83 (d, J = 6.8 Hz, 3H). |
| 271 | D | NA | 1083.9 | $^{1}$H NMR (400 MHZ, DMSO-$d_6$): δ 0.77-0.88 (m, 3 H), 0.96 (d, J = 6.60 Hz, 3 H), 1.30 (s, 1 H), 1.38 (d, J = 7.2 Hz, 3 H), 1.48 ( d, J = 7.2 Hz, 1 H), 1.58-1.89 (m, 4 H), 1.90-2.09 (m, 4 H), 2.11-2.30 (m, 4 H), 2.33 (d, J = 2.0 Hz, 1 H), 2.44 (s, 4 H), 2.62-2.67 (m, 3 H), 3.15 (d, J = 12.0 Hz, 4 H), 3.75 (d, J = 8.8 Hz, 3 H), 3.85 (s, 1 H), 4.20-4.38 (m, 3 H), 4.41 (m, J = 7.60 Hz, 1 H), 4.84 ( s, 2 H), 4.88-4.98 (m, 3 H), 5.21 ( d, J = 3.42 Hz, 1 H), 6.13 (s, 1 H), 6.27 (s, 1 H), 6.85 ( d, J = 6.0 Hz, 3 H), 6.96 (t, J = 7.60 Hz, 1 H), 7.01 (d, J = 8.44 Hz, 1 H), 7.37 (t, J = 7.6 Hz, 1 H), 7.49 (s, 1 H), 7.58 ( d, J = 7.6 Hz, 1 H), 7.66-7.71 (m, 1 H), 7.71-7.77 (m, 1 H), 7.94 (d, J = 7.2 Hz, 1 H), 8.43 (d, J = 7.6 Hz, 1 H), 8.49 (d, J = 1.6 Hz, 1 H), 8.98-9.01 (m, 1 H). |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| 272 | D | NA | 1142.0 | 1H NMR (300 MHz, CD3OD): δ 8.88-8.84 (m, 1H), 7.93-7.85 (m, 2H), 7.70 (s, 1H), 7.46-7.28 (m, 5H), 6.98-6.93 (m, 2H), 6.86-6.83 (m, 2H), 6.06-5.98 (m, 1H), 5.08-5.04 (m, 1H), 4.64-4.59 (m, 1H), 4.40-4.28 (m, 5H), 3.90-3.85 (m, 2H), 3.79-3.76 (m, 1H), 3.72-3.62 (m, 4H), 3.56 (s, 2H), 3.39-3.35 (m, 4H), 3.27-3.24 (m, 1H), 3.01-2.97 (m, 2H), 2.89-2.73 (m, 5H), 2.60 (s, 7H), 2.48-2.45 (m, 3H), 2.42-1.95 (m, 4H), 1.82-1.69 (m, 5H), 1.60-1.53 (m, 2H), 1.32-1.17 (m, 2H), 1.06-0.83 (m, 6H). |
| 273 | A | A | 1142.0 | 1H NMR (300 MHz, CD3OD): δ 8.87 (s, 1H), 7.94-7.86 (m, 2H), 7.71 (s, 1H), 7.44-7.41 (m, 4H), 7.38-7.29 (m, 1H), 6.98-6.94 (m, 2H), 6.87-6.81 (m, 2H), 6.00 (s, 1H), 5.12-5.09 (m, 1H), 4.59-4.53 (m, 1H), 4.42-4.31 (m, 5H), 3.90-3.79 (m, 3H), 3.76-3.65 (m, 3H), 3.61-3.57 (m, 3H), 3.50-3.35 (m, 6H), 3.01-2.97 (m, 2H), 2.83-2.76 (m, 4H), 2.64 (s, 8H), 2.47-2.46 (m, 3H), 2.41-2.34 (m, 1H), 2.22-2.15 (m, 1H), 2.01-1.93 (m, 1H), 1.88-1.81 (m, 5H), 1.62-1.55 (m, 2H), 1.32-1.19 (m, 2H), 1.06-1.03 (m, 3H), 0.92-0.87 (m, 3H). |
| 274 | D | NA | 1011.9 | |
| 275 | C | A | 1011.9 | |
| 276 | D | NA | 1057.9 | |
| 277 | A | A | 1057.9 | |
| 278 | D | NA | 1099.9 | |
| 279 | A | A | 1099.9 | |
| 280 | D | NA | 1070.7 | 1H NMR (400 MHZ, CD3OD): δ 8.9 (s, 1H), 7.96-7.89 (m, 2H), 7.74 (s, 1H), 7.48-7.42 (m, 2H), 7.36-7.34 (m, 3H) 7.00-6.97 (m, 2H), 6.89-6.85 (m, 2H), 6.07 (s, 1H), 5.00-4.89 (m, 1H), 4.65-4.59 (m, 1H), 4.42-4.31 (m, 5H), 3.83-3.82 (m, 1H), 3.74(s, 1H), 3.59 (s, 2H), 3.42-3.32 (m, 3H), 3.03-3.01 (m, 2H), 2.82-2.78 (m, 6H), 2.77-2.60 (m, 7H), 2.50 (s, 4H), 2.49-2.37 (m, 2H), 2.32-2.32 (m, 6H), 2.10-2.00 (m, 1H), 1.08-1.06 (m, 4H), 1.13-1.16 (m, 2H), 1.08-1.06 (m, 3H). |
| 281 | A | A | 1070.7 | 1H NMR (400 MHZ, CD3OD): δ 8.9 (s, 1H), 7.96-7.89 (m, 2H), 7.74 (s, 1H), 7.47-7.45 (m, 3H), 7.41-7.34 (m, 2H), 7.00-6.98 (m, 2H), 6.88-6.82 (m, 2H), 6.03 (s, 1H), 5.10-5.07 (m, 1H), 4.60-4.54 (m, 1H), 4.42-4.34 (m, 5H), 3.90-3.80 (m, 1H), 3.70-3.67(m, 1H), 3.59 (s, 3H), 3.43-3.40 (m, 1H), 3.33-3.32 (m, 2H), 3.04-3.01 (m, 2H), 2.84-2.80 (m, 4H), 2.77-2.66 (m, 8H), 2.50 (s, 3H), 2.37-2.35 (m, 7H), 2.20-2.10 (m, 1H), 2.09-1.90 (m, 1H), 1.84 (s, 4H), 1.08-1.06 (m, 3H), 0.95-0.89 (m, 3H). |
| 282 | ND | ND | 1044.6 | |
| 283 | A | A | 1044.7 | |
| 284 | C | A | 1071.6 | |
| 285 | A | A | 1071.6 | |
| 286 | B | A | 1083.6 | |
| 287 | D | NA | 1067.7 | |
| 288 | A | A | 1067.7 | |
| 289 | D | NA | 986.6 | |
| 290 | D | NA | 1042.3 | |
| 291 | D | NA | 1099.4 | |
| 292 | D | NA | 997.2 | 1H NMR (300 MHz, DMSO-D6): δ 13.26 (s, 1H), 9.40-9.00(m, 2H), 8.95-8370 (m, 2H), 8.85-8.76 (m, 1H), 8.20-7.80 (m, 5H), 7.60-7.30 (m, 2H), 7.20-6.50 (m, 3H), 6.20-6.00 (m, 1H), 5.20-4.80 (m, 2H), 4.81-4.10( m, 7H), 3.70-3.40 (m, 7H), 3.40-3.36 (m, 4H), 3.36-3.30 (m, 2H), 3.30-3.20 (m, 3H), 2.90-2.70 (m, 3H), 2.40-2.00 (m, 3H), 2.00-1.80 (m, 4H), 1.80-1.70 (m, 1H), 1.60-1.10 (m, 3H), 1.00-0.60 (m, 6H). |
| 293 | B | A | 997.2 | 1H NMR (300 MHz, DMSO-D6): δ 13.26 (s, 1H), 8.85-8.70 (m, 2H), 8.60-8.50 (m, 1H), 8.20-7.80 (m, 5H), 7.80-7.71 (m, 1H), 7.60-7.45 (m, 2H), 7.45-7.35 (m, 1H), 7.10-6.85 (m, 2H), 6.80-6.73 (m, 1H), 6.60-6.42 (m, 1H), 6.11 (s, 1H), 5.20-4.80 (m, 2H), 4.61-4.10( m, 6H), 3.80-3.60 (m, 2H), 3.60-3.46 (m, 4H), 2.90-2.80 (m, 2H), 2.75-2.60 (m, 5H), 2.50-2.40 (m, 6H), 2.35-2.10 (m, 2H), 2.05-1.90 (m, 1H), 1.85-1.70 (m, 1H), 1.70-1.30 (m, 7H), 1.30-1.20 (m, 1H), 1.10-0.90 (m, 3H), 0.90-0.70 (m, 3H). |
| 294 | B | A | 1065.3 | |
| 295 | A | A | 1065.3 | |
| 296 | A | A | 1082.3 | |
| 297 | D | NA | 1099.4 | 1H NMR (300 MHz, CD3OD): δ 8.91 (s, 1H), 8.06-8.04 (m, 1H), 7.91 (s, 1H), 7.81-7.80 (m, 1H), 7.47-7.41 (m, 5H), 7.08-7.03 (m, 4H), 6.06 (s, 1H), 5.06-5.04 (m, 1H), 4.88-4.63 (m, 3H), 4.63-4.60 (m, 3H), 4.42-4.23 (m, 2H), 3.90-3.80 (m, 2H), 3.68-3.67 (m, 8H), 3.36-3.33 (m, 12H), 2.47 (s, 3H), 2.43-2.16 (m, 6H), 1.92-1.76 (m, 2H), 1.06-1.03 (m, 3H), 0.83-0.82 (m, 10H). |
| 298 | A | A | 1099.4 | 1H NMR (400 MHZ, CD3OD): δ 8 8.96 (s, 1H), 8.07-8.05 (m, 1H), 7.90 (s, 1 H), 7.88-7.85 (m, 1H), 7.47-7.46 (m, 5H), 7.14-7.08 (m, 1H), 7.13-7.07 (m, 4H), 6.03 (s, 1H), 5.13-5.10 (m, 1H), 4.62- 4.43 (m, 7H), 4.24-4.22 (m, 2H), 3.93-3.57 (m, 6H), 3.56-3.45 (m, 4H), 3.33-3.21 (m, 11H), 2.47 (s, 3H), 2.33-2.21 (m, 1H), 2.13-2.11 (m, 5H), 1.91-1.89 (m, 2H), 0.87-0.84 (m, 12H). |

TABLE 2B-continued

Target protein degradation via exemplary bifunctional degradation compounds of Table 1B

| Ex. # | *$DC_{50}$ (nM) | **$D_{max}$ (%) | MH+ | NMR transcript |
|---|---|---|---|---|
| 299 | D | NA | 1011.2 | 1H NMR (400 MHz, DMSO-D6): δ 13.62 (s, 1H), 8.95-8.71 (m, 1H), 8.32-8.21(m, 1H), 8.04-8.00 (m, 1H), 8.85-7.91 (m, 1H), 7.71-7.62 (m, 1H), 7.60-7.51 (m, 3H), 7.38-7.33 (m, 3H), 6.98-6.91 (m, 2H), 6.83-6.78 (m, 1H), 6.49 (s, 1H), 6.13-6.08 (m, 1H), 5.11 (s, 1H), 5.04-4.84 (m, 1H), 4.54-4.40 (m, 1H), 4.43-4.22 (m, 5H), 3.74 (s, 1H), 4.61-3.53 (m, 2H), 2.91-2.82 (m, 2H), 2.69-2.56 (m, 5H), 2.49-2.39 (m, 7H), 2.38-2.20 (m, 6H), 2.08-2.00 (m, 1H), 1.96-1.68 (m, 2H), 1.71-1.59 (m, 4H), 1.47-1.28 (m, 4H), 0.96 (s, 3H), 0.82-0.71 (m, 4H). |
| 300 | A | A | 1011.2 | 1H NMR (400 MHz, DMSO-D6): δ 13.53 (s, 1H), 8.73 (s, 1H), 8.46-8.41 (m, 1H), 8.31 (s, 1H), 8.06-8.01 (m, 1H), 8.94-8.91 (m, 1H), 7.71 (s, 1H), 7.56-8.47 (m, 2H), 7.40-7.36 (m, 3H), 6.99-6.92 (m, 2H), 6.80-6.74 (m, 1H), 6.51 (s, 1H), 6.09 (s, 1H), 5.09-5.04 (m, 1H), 4.94-4.86 (m, 1H), 4.48-4.03 (m, 7H), 3.77-3.50 (m, 4H), 3.48-3.43 (m, 3H), 2.98-2.94 (m, 2H), 2.73-2.54 (m, 5H), 2.48-2.36 (m, 6H), 2.35 (s, 3H), 2.30-2.23 (m, 1H), 2.08-2.00 (m, 1H), 1.81-1.73 (m, 1H), 1.71-1.66 (m, 4H), 1.40-1.33 (m, 3H), 1.24-1.20 (m, 1H), 0.95 (s, 3H), 0.81 (s, 3H). |
| 301 | B | A | 929.1 | |
| 302 | C | A | 929.1 | |
| 350 | D | NA | 1082.9 | |
| 351 | A | A | 1082.9 | |
| 352 | A | A | 929.8 | 1H NMR (400 MHz, DMSO-D6): δ 9.00 (s, 1H), 8.56-8.47 (m, 3H), 8.23 - 8.16 (m, 3H), 8.01 (dd, J = 1.4, 8.4 Hz, 1H), 7.82-7.76 (m, 1H), 7.74-7.68 (m, 1H), 7.32-7.22 (m, 1H), 6.96-6.88 (m, 2H), 6.49 (s, 2H), 6.11-5.88 (m, 1H), 5.08 (s, 2H), 4.98-4.90 (m, 1H), 4.36 (t, J = 7.9 Hz, 1H), 4.28 (br s, 1H), 4.19 (br t, J = 5.4 Hz, 2H), 3.72-3.61 (m, 4H), 2.69-2.58 (m, 5H), 2.49-2.35 (m, 11H), 2.25 (td, J = 6.8, 9.6 Hz, 1H), 2.09-1.97 (m, 1H), 1.92-1.71 (m, 1H), 1.51-1.38 (m, 3H), 1.01-0.90 (m, 3H), 0.85-0.75 (m, 3H). |

†when tested at the top concentration of between 0.3 and 10 μM
*DC50 (nM)
A < 2.5
2.5 ≤ B <10
10 ≤ C < 30
D ≥ 30
NA not calculated/no curve fit
**Dmax (% degraded)
A > 75
50 < B ≤ 75
C ≤ 50
NA not calculated/no curve fit

TABLE 2C

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| 354 | B | A | D | NA | 1053.81 | 1H-NMR (400 MHz, CD3OD, ppm) δ 8.86 (s, 1H), 7.85 (s, 2H), 7.69 (s, 1H), 7.47-7.30 (m, 5H), 6.98-6.94 (m, 2H), 6.57(s, 1H), 6.47 (s, 1H), 6.05 (s, 1H), 5.01-4.89 (m, 1H), 4.60-4.54 (m, 2H), 4.44 (s, 1H), 4.30 (s, 2H), 4.23-4.19 (m, 2H), 3.81-3.77 (m, 3H), 3.71-3.68 (m, 2H), 3.59 (s, 2H), 3.46 (s, 1H), 3.36-3.33 (m, 1H), 3.01-2.98 (m, 2H), 2.83-2.76 (m, 4H), 2.50 (s, 3H), 2.48-2.30 (m, 4H), 1.97-1.87 (m, 7H), 1.63-1.59 (m, 2H), 1.50-1.48 (m, 3H), |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 1.08-1.06 (m, 3H), 0.98-0.92 (m, 4H). |
| 355 | A | A | B | A | 1053.66 | 1H-NMR: (300 MHz, CD3OD, ppm) δ 8.88 (s, 1H), 7.88-7.84 (m, 2H), 7.71 (s, 1H), 7.47-7.43 (m, 4H), 7.41-7.32 (m, 1H), 6.99-6.97 (d, J = 6 Hz, 2H), 6.57-6.56 (m, 1H), 6.47 (s, 1H), 6.02 (s, 1H), 5.05-5.04 (m, 1H), 4.56-4.53 (m, 2H), 4.45 (s, 1H), 4.35-4.32 (m, 2H), 4.24-4.21 (m, 2H), 3.83-3.80 (m, 3H) 3.67-3.64 (d, J = 9 Hz, 1H), 3.59 (s, 3H), 3.48-3.35 (m, 1H), 3.33 (s, 2H), 3.02-2.99 (m, 2H), 2.88-2.81 (m, 2H), 2.79-2.78 (m, 2H), 2.48 (s, 3H), 2.36-2.34 (m, 3H), 2.23-2.15 (m, 1H), 1.94-1.87 (m, 7H), 1.66-1.61 (m, 2H), 1.54-1.42 (m, 3H), 1.08-1.06 (m, 3H), 0.91-0.89 (m, 3H). |
| 356 | D | NA | D | NA | 959.56 | 1H NMR (400 MHz, DMSO-d6): δ 14.11 (s, 1H), 9.01-8.90 (m, 1H), 8.54 (d, J = 7.8 Hz, 1H), 7.98-7.79 (dd, J = 6.1, 2.5 Hz, 2H), 7.51-7.45 (m, 1H), 7.39 (d, J = 8.3 Hz, 2H), 7.26-7.17 (m, 1H), 7.11-6.79 (m, 1H), 6.75 (d, J = 6.0 Hz, 2H), 6.51 (s, 1H), 6.29 (s, 1H), 6.09 (s, 1H), 5.99 (s, 2H), 5.13 (d, J = 3.5 Hz, 1H), 4.86 (p, J = 7.3 Hz, 1H), 4.52 (s, 2H), 4.41 (t, J = 7.7 Hz, 1H), 4.34-4.20 (m, 5H), 3.77-3.60 (m, 5H), 3.42 (s, 2H), 3.01 (d, J = 11.7 Hz, 2H), 2.44 (d, J = 10.7 Hz, 3H), 2.25 (dt, J = 14.5, 6.7 Hz, 3H), 2.16-1.96 (m, 3H), 1.75 (ddd, J = 12.5, 7.7, 4.8 Hz, 1H), 1.44 (d, J = 7.0 Hz, 1H), 1.33 (d, J = 7.0 Hz, 2H), 1.24 (d, J = 7.7 Hz, 2H), 1.20-0.95 (d, J = 6.6 Hz, 3H), 0.81 (d, J = 6.7 Hz, 3H). |
| 357 | A | A | A | A | 959.56 | 1H NMR (400 MHz, DMSO-d6, ppm): δ 14.11 (s, 1H), 8.98 (s, 1H), 8.42 (d, J = 7.6 Hz, 1H), 7.90 (d, J = 7.9 Hz, 1H), 7.79 (d, J = 6.0 Hz, 1H), 7.49 (s, 1H), 7.47-7.40 (m, 2H), 7.36 (d, J = 8.2 Hz, 2H), 7.26-7.18 (m, 1H), 6.85-6.80 (m, 2H), 6.58-6.52 (m, 1H), 6.21 (s, 1H), 6.10 (s, 1H), 5.99-5.90 (m, 2H), 5.13-5.08 (m, 1H), 4.95-4.87 (m, 1H), 4.58-4.52 (m, 2H), |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 4.40-4.26 (m, 5H), 3.82-3.65 (m, 5H), 3.42-3.23 (m, 4H), 3.10-302 (m, 2H), 2.45-2.41 (m, 2H), 2.27-2.10 (m, 3H), 2.05-1.91 (m, 3H), 1.77-1.70 (m, 1H), 1.44 (d, J = 7.0 Hz, 3H), 1.32-1.21 (m, 2H), 1.01-0.92 (m, 3H), 0.89-0.72 (m, 3H). |
| 358 | D | NA | A | NA | 1063.70 | 1H-NMR (400 MHz, CD3OD, ppm) δ 8.85 (s, 1H), 7.77-7.75 (d, J = 8.0 Hz, 1H), 7.49-7.34 (m, 5H), 7.25-7.21 (m, 1H), 6.92-6.90 (d, J = 8.0 Hz, 2H), 6.02 (s, 1H), 4.99-4.95 (m, 2H), 4.58-4.54 (m, 2H), 4.42-4.36 (m, 1H), 4.28-4.19 (m, 3H), 4.10 (s, 1H), 3.76-3.63 (m, 6H), 3.48 (s, 2H), 3.30-3.07 (m, 5H), 2.82-2.76 (m, 5H), 2.51-2.34 (m, 11H), 2.28-2.03 (m, 2H), 1.94-1.82 (m, 6H), 1.56-1.46 (m, 6H), 1.05-1.03 (d, J = 8.0 Hz, 3H), 0.91-0.89 (d, J = 8.0 Hz, 3H) |
| 359 | A | A | B | A | 1063.70 | 1H-NMR (400 MHz, CD3OD, ppm) δ 8.89 (s, 1H), 7.80-7.78 (d, J = 8.0 Hz, 1H), 7.52-7.40 (m, 5H), 7.26-7.21 (m, 1H), 6.94-6.92 (d, J = 8.0 Hz, 2H), 6.03 (s, 1H), 5.20-5.05 (m, 2H), 4.78-4.46 (m, 3H), 4.34-4.20 (m, 1H), 4.14-4.05 (m, 1H), 3.94-3.79 (m, 4H), 3.68-3.62 (m, 2H), 3.52 (s, 3H), 3.34-3.07 (m, 5H), 2.92-2.81 (m, 5H), 2.65-2.45 (m, 11H), 2.26-2.03 (m, 3H), 1.99-1.86 (m, 6H), 1.56-1.46 (m, 6H), 1.05-1.03 (d, J = 8.0 Hz, 3H), 0.91-0.89 (d, J = 8.0 Hz, 3H) |
| 360 | A | A | C | A | 1094.68 | 1H NMR (400 MHz, METHANOL-d4) δ: 9.07-8.92 (m, 1H), 8.48-8.34 (m, 1H), 8.23-8.17 (m, 2H), 7.96-7.84 (m, 1H), 7.79-7.71 (m, 1H), 7.51-7.41 (m, 3H), 7.38-7.32 (m, 2H), 7.26-7.17 (m, 1H), 6.93-6.77 (m, 2H), 6.56-6.47 (m, 1H), 6.16-6.12 (m, 1H), 6.12-6.07 (m, 1H), 5.93 (s, 2H), 5.17-5.09 (m, 1H), 4.98-4.85 (m, 1H), 4.56-4.45 (m, 2H), 4.41-4.32 (m, 1H), 4.30-4.13 (m, 5H), 3.75-3.63 (m, 3H), 3.71-3.67 (m, 2H), 3.19-3.16 (m, 2H), 3.02-2.99 (m, 2H), 2.75-2.67 (m, 3H), |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 2.37-2.33 (m, 4H), 2.33-2.27 (m, 6H), 2.20-2.16 (m, 3H), 2.03-1.94 (m, 6H), 1.77-1.75 (m, 1H), 1.45-1.23 (m, 6H), 0.97-0.94 (m, 3H), 0.82 (s, 3H) |
| 361 | D | NA | D | NA | 1102.63 (1104.63) | 1H NMR (400 MHz, DMSO-d6) δ: 9.01-8.94 (m, 1H), 9.02-8.93 (m, 1H), 8.17 (s, 2H), 7.91-7.90 (m, 1H), 7.77-7.75 (m, 1H), 7.49-7.47 (m, 1H), 7.45-7.28 (m, 4H), 7.25-7.18 (m, 1H), 6.87-6.82 (m, 2H), 6.52-6.51 (m, 1H), 6.16-6.13 (m, 1H), 5.97 (s, 2H), 5.19-5.16 (m, 1H), 4.85-4.81 (m, 1H), 4.45 (s, 2H), 4.42-4.24 (m, 6H), 3.80-3.78 (m, 1H), 3.17-3.15 (m, 1H), 3.07-2.99 (m, 3H), 2.71-2.52 (m, 5H), 2.46-2.43 (m, 4H), 2.32-2.30 (m, 5H), 2.28-1.95 (m, 9H), 1.78-1.73 (m, 3H), 1.45-1.32 (m, 5H), 0.99-0.84 (m, 3H), 0.79-0.71 (m, 3H) |
| 362 | A | A | D | A | 1102.63 (1104.63) | 1H NMR (400 MHz, DMSO-d6) δ: 8.98 (s, 1H), 8.49-8.37 (m, 1H), 8.21 (s, 2H), 7.97-7.86 (m, 1H), 7.80-7.74 (m, 1H), 7.57-7.47 (m, 1H), 7.46-7.32 (m, 4H), 7.27-7.16 (m, 1H), 6.95-6.78 (m, 2H), 6.61-6.45 (m, 1H), 6.22-6.08 (m, 1H), 6.04-5.89 (m, 2H), 5.30-5.06 (m, 1H), 4.98-4.82 (m, 1H), 4.49 (s, 2H), 4.40-4.23 (m, 6H), 3.78-3.71 (m, 2H), 3.36 (d, J = 11.2 Hz, 1H), 3.24-3.21 (m, 1H), 3.08-2.95 (m, 2H), 2.78-2.64 (m, 5H), 2.45 (s, 4H), 2.32-2.25 (m, 4H), 2.21-2.08 (m, 5H), 2.07-1.91 (m, 4H), 1.82-1.72 (m, 3H), 1.44-1.36 (m, 5H), 1.04-0.95 (m, 3H), 0.80-0.72 (m, 3H) |
| 363 | D | NA | D | NA | 1055.78 | 1H NMR (400 MHz, DMSO-d6) δ: 9.65-9.59 (m, 1H), 8.41-8.36 (m, 1H), 8.18-8.12 (m, 1H), 8.02-7.89 (m, 3H), 7.80-7.75 (m, 1H), 7.53-7.38 (m, 3H), 7.27-7.18 (m, 1H), 6.90-6.81 (m, 2H), 6.56-6.50 (m, 1H), 6.18-6.12 (m, 1H), 6.11-6.08 (m, 1H), 6.01-5.96 (m, 2H), 5.24-5.07 (m, 2H), 4.96-4.85 (m, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 1H), 4.54-4.47 (m, 2H), 4.45-4.38 (m, 1H), 4.31-4.20 (m, 4H), 3.80-3.70 (m, 1H), 3.59-3.53 (m, 2H), 3.23 (br s, 2H), 3.05-2.95 (m, 2H), 2.85-2.77 (m, 2H), 2.76-2.63 (m, 3H), 2.35-2.17 (m, 10H), 2.04-1.87 (m, 3H), 1.80-1.1.71 (m, 3H), 1.47-1.34 (m, 5H), 0.96 (d, J = 6.60 Hz, 3H), 0.83 (d, J = 6.72 Hz, 3H) |
| 364 | D | A | D | NA | 1055.78 | 1H NMR (400 MHz, DMSO-d6) δ ppm 9.62 (s, 1H), 8.48 (d, J = 7.50 Hz, 1H), 8.16 (s, 1H), 8.01-7.89 (m, 3H), 7.77 (d, J = 6.00 Hz, 1H), 7.52-7.43 (m, 3H), 7.23 (t, J = 7.74 Hz, 1H), 6.91-6.82 (m, 2H), 6.53 (m, 1H), 6.23-6.12 (m, 1H), 6.12-6.07 (m, 1H), 5.98 (s, 2H), 5.19 (br d, J = 3.88 Hz, 2H), 4.93 (br t, J = 7.25 Hz, 1H), 4.50 (br s, 2H), 4.37 (t, J = 8.00 Hz, 1H), 4.33-4.17 (m, 4H), 3.72-3.62 (m, 2H), 3.48-3.45 (m, 1H), 3.25-3.22 (m, 2H), 3.06-2.97 (m, 2H), 2.80-2.72 (m, 2H), 2.69-2.64 (m, 3H), 2.35-2.10 (m, 10H), 2.10-1.89 (m, 3H), 1.82-1.73 (m, 3H), 1.48-1.35 (m, 5H), 0.99- 0.93 (m, 3H), 0.85-0.77 (m, 3H) |
| 365 | D | NA | D | NA | 1065.87 | 1H NMR (400 MHz, DMSO-d6) δ (ppm): 14.15 (s, 1H), 8.30 (d, J = 8.0 Hz, 1H), 7.92 (dd, J = 8.1, 1.6 Hz, 1H), 7.76 (d, J = 6.0 Hz, 1H), 7.58-7.47 (m, 2H), 7.45-7.26 (m, 4H), 7.26-7.17 (m, 1H), 6.90-6.80 (m, 2H), 6.56-6.49 (m, 1H), 6.16-6.05 (m, 2H), 5.98 (brs, 2H), 5.20-5.11 (m, 2H), 4.99-4.85 (m, 1H), 4.55-4.38 (m, 3H), 4.33-4.14 (m, 4H), 3.75 (d, J = 8.6 Hz, 1H), 3.57-3.38 (m, 5H), 3.31-3.21 (m, 3H), 3.17-2.82 (m, 3H), 2.80-2.56 (m, 4H), 2.37-2.01 (m, 12H), 2.01-1.69 (m, 6H), 1.47 (d, J = 7.0 Hz, 1H), 1.36 (d, J = 7.0 Hz, 4H), 0.96 (d, J = 6.6 Hz, 2H), 0.79 (d, 6.7 Hz, 3H). |
| 366 | B | A | D | NA | 1065.87 | 1H NMR (400 MHz, DMSO-d6) δ (ppm): 14.15 (s, 1H), 8.40 (d, J = 7.9 Hz, 1H), 7.92 (dd, J = 8.1, 1.6 Hz, 1H), 7.77 (d, J = 6.0 Hz, 1H), 7.52 (d, J = 22.0 Hz, 2H), 7.41-7.28 |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | (m, 4H), 7.26-7.18 (m, 1H), 6.90-6.80 (m, 2H), 6.52 (dd, J = 6.1, 2.1 Hz, 1H), 6.16-6.07 (m, 2H), 5.98 (brs, 2H), 5.21-5.15 (m, 1H), 5.10 (d, J = 3.6 Hz, 1H), 4.94 (q, J = 6.9 Hz, 1H), 4.49 (brs, 2H), 4.37 (t, J = 7.9 Hz, 1H), 4.31-4.25 (m, 2H), 4.20 (t, J = 5.6 Hz, 2H), 3.75-3.61 (m, 2H), 3.51-3.42 (m, 2H), 3.29-3.21 (m, 3H), 3.01 (d, J = 11.4 Hz, 2H), 2.79-2.61 (m, 4H), 2.36-2.06 (m, 12H), 2.06-1.90 (m, 3H), 1.85-1.73 (m, 3H), 1.47-1.38 (m, 3H), 0.96 (t, J = 6.0 Hz, 3H), 0.81 (d, J = 6.6 Hz, 3H). |
| 367 | D | A | D | NA | 1069.81 | 1H NMR (300 MHz, methanol-d4): δ 9.01-8.99 (m, 1H), 8.61-8.57 (m, 1H), 7.99-7.86 (m, 1H), 7.82 (d, J = 7.0 Hz, 1H), 7.72 (d, J = 8.3 Hz, 1H), 7.55 (s, 1H), 7.72 (d, J = 8.2 Hz, 1H), 7.35-7.24 (m, 1H), 6.99-6.88 (m, 2H), 6.86-6.77 (m, 1H), 6.25 (d, J = 2.2 Hz, 1H), 6.18-6.10 (m, 1H), 5.30-5.23 (m, 1H), 5.10-4.97 (m, 2H), 4.85-4.79 (m, 4H), 4.71-4.59 (m, 3H), 4.58-4.51 (m, 1H), 4.49-4.39 (m, 1H), 3.85-3.70 (m, 3H), 3.70-3.58 (m, 5H), 3.57-3.35 (m, 3H), 3.22-3.12 (m, 2H), 2.69-2.51 (m, 7H), 2.46-2.13 (m, 6H), 2.11-1.87 (m, 4H), 1.61-1.51 (m, 2H), 1.18-0.9 (m, 3H). |
| 368 | A | A | D | NA | 1069.81 | 1H NMR (300 MHz, methanol-d4): δ 8.97 (s, 1H), 8.61 (s, 1H), 7.90 (d, J = 8.2 Hz, 1H), 7.83-7.69 (m, 2H), 7.48 (d, J = 7.5 Hz, 2H), 7.30-7.21 (m, 1H), 6.95-6.81 (m, 2H), 6.64 (d, J = 6.4 Hz, 1H), 6.17 (s, 1H), 6.10 (s, 1H), 5.29-4.92 (m, 3H), 4.69-4.51 (m, 5H), 4.48-4.31 (m, 2H), 3.92-3.80--- (m, 1H), 3.78-3.61 (m, 3H), 3.58-3.48 (m, 3H), 3.42 (d, J = 11.5 Hz, 4H), 3.12 (d, J = 11.6 Hz, 3H), 2.50 (s, 7H), 2.33-2.11 (m, 6H), 2.09-2.01 (m, 3H), 1.99-1.82 (m, 2H), 1.64-1.59 (m, 1H), 1.58 (d, J = 7.2 Hz, 4H), 1.066 (d, J = 6.1 Hz, 3H), 0.98-0.87 (m, 3H). |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| 369 | D | NA | D | NA | 1060.78 | 1H NMR (400 MHz, DMSO-d6) δ 9.01-8.96 (m, 1H), 8.41-8.34 (m, 2H), 8.16 (br d, J = 7.1 Hz, 1H), 7.87 (br dd, J = 4.4, 7.0 Hz, 1H), 7.52 (br d, J = 7.8 Hz, 1H), 7.45-7.38 (m, 2H), 7.35-7.28 (m, 2H), 7.23 (br t, J = 7.5 Hz, 1H), 6.96 (br d, J = 6.1 Hz, 1H), 6.92-6.83 (m, 2H), 6.69 (br s, 1H), 6.14-6.06 (m, 3H), 5.30-5.18 (m, 1H), 4.93-4.73 (m, 5H), 4.64-4.50 (m, 1H), 4.42 (br t, J = 7.8 Hz, 1H), 4.38-4.22 (m, 2H), 3.77 (br d, J = 7.0 Hz, 1H), 3.55 (br s, 3H), 3.09-2.96 (m, 2H), 2.95-2.83 (m, 3H), 2.56 (br s, 1H), 2.45 (d, J = 5.0 Hz, 3H), 2.37-2.18 (m, 5H), 2.09-1.96 (m, 3H), 1.95-1.82 (m, 7H), 1.81-1.71 (m, 1H), 1.35 (br d, J = 7.0 Hz, 3H), 0.96 (br d, J = 6.6 Hz, 3H), 0.82 (br d, J = 6.6 Hz, 3H) |
| 370 | C | A | D | NA | 1123.86 | 1H NMR (400 MHz, DMSO-d6) δ 9.03-8.96 (m, 1H), 8.30 (d, J = 7.9 Hz, 1H), 7.96-7.88 (m, 1H), 7.77 (d, J = 6.0 Hz, 1H), 7.50 (s, 1H), 7.45-7.40 (m, 2H), 7.36-7.29 (m, 2H), 7.27-7.20 (m, 1H), 6.93-6.81 (m, 2H), 6.53 (dd, J = 1.8, 6.1 Hz, 1H), 6.19-6.08 (m, 2H), 5.98 (s, 2H), 5.22-5.15 (m, 1H), 5.12 (d, J = 3.4 Hz, 1H), 5.00-4.82 (m, 2H), 4.50 (br s, 2H), 4.46-4.38 (m, 1H), 4.27 (br t, J = 4.8 Hz, 2H), 3.76 (d, J = 8.7 Hz, 1H), 3.68-3.42 (m, 5H), 3.25 (br d, J = 10.5 Hz, 4H), 3.06-2.93 (m, 4H), 2.71-2.66 (m, 2H), 2.46 (s, 3H), 2.31-2.15 (m, 10H), 2.09-1.94 (m, 5H), 1.83-1.64 (m, 4H), 1.46 (d, J = 6.8 Hz, 1H), 1.36 (br d, J = 7.1 Hz, 3H), 0.96 (d, J = 6.7 Hz, 3H), 0.83 (d, J = 6.6 Hz, 3H) |
| 371 | A | A | B | A | 1123.86 | 1H NMR (400 MHz, DMSO-d6) δ 9.01 (br d, J = 1.3 Hz, 1H), 8.42 (d, J = 7.8 Hz, 1H), 8.16 (s, 2H), 7.91 (d, J = 8.1 Hz, 1H), 7.77 (d, J = 5.9 Hz, 1H), 7.50 (s, 1H), 7.46-7.42 (m, 2H), 7.39-7.35 (m, 2H), 7.25-7.19 (m, 1H), 6.90-6.82 (m, 2H), 6.53 (dd, J = |

TABLE 2C-continued

| Ex. # | *BRM DC$_{50}$ (nM) | **BRM $D_{max}$ (%)† | *BRG1 DC$_{50}$ (nM) | **BRG1 $D_{max}$ (%)† | Observed Mass (2nd Observed Mass) | HNMR |
|---|---|---|---|---|---|---|
| Target protein degradation via exemplary bifunctional degradation compounds of Table 1C | | | | | | |
| | | | | | | 1.5, 5.9 Hz, 1H), 6.16-6.08 (m, 2H), 5.97 (s, 2H), 5.23-5.15 (m, 1H), 4.91 (br t, J = 5.9 Hz, 2H), 4.49 (br s, 3H), 4.37 (t, J = 7.9 Hz, 1H), 4.25 (br s, 2H), 3.70-3.63 (m, 8H), 3.11-2.98 (m, 5H), 2.78-2.72 (m, 2H), 2.62-2.55 (m, 4H), 2.46 (s, 2H), 2.38-2.10 (m, 11H), 2.08-1.92 (m, 3H), 1.84-1.73 (m, 3H), 1.40-1.38 (m, 3H), 1.01-0.92 (m, 3H), 0.85-0.75 (m, 3H) |
| 372 | D | A | D | NA | 532.95 | 1H NMR (400 MHz, DMSO-d6) δ 9.01 (br d, J = 1.3 Hz, 1H), 8.42 (d, J = 7.8 Hz, 1H), 8.16 (s, 2H), 7.91 (d, J = 8.1 Hz, 1H), 7.77 (d, J = 5.9 Hz, 1H), 7.50 (s, 1H), 7.46-7.42 (m, 2H), 7.39-7.35 (m, 2H), 7.25-7.19 (m, 1H), 6.90-6.82 (m, 2H), 6.53 (dd, J = 1.5, 5.9 Hz, 1H), 6.16-6.08 (m, 2H), 5.97 (s, 2H), 5.23-5.15 (m, 1H), 4.91 (br t, J = 5.9 Hz, 2H), 4.49 (br s, 3H), 4.37 (t, J = 7.9 Hz, 1H), 4.25 (br s, 2H), 3.70-3.63 (m, 8H), 3.11-2.98 (m, 5H), 2.78-2.72 (m, 2H), 2.62-2.55 (m, 4H), 2.46 (s, 2H), 2.38-2.10 (m, 11H), 2.08-1.92 (m, 3H), 1.84-1.73 (m, 3H), 1.40-1.38 (m, 3H), 1.01-0.92 (m, 3H), 0.85-0.75 (m, 3H) |
| 373 | D | NA | D | NA | 532.95 | 1H NMR: (400 MHz, DMSO-d6) δ 8.46 (d, J = 7.7 Hz, 1H), 8.15 (s, 2H), 8.06-7.89 (m, 1H), 7.81-7.75 (m, 1H), 7.66-7.58 (m, 1H), 7.54-7.47 (m, 2H), 7.42-7.32 (m, 4H), 7.28-7.18 (m, 1H), 6.96-6.82 (m, 2H), 6.57-6.51 (m, 1H), 6.47 (d, J = 9.0 Hz, 1H), 6.30 (dt, J = 1.2, 6.7 Hz, 1H), 6.18-6.10 (m, 2H), 6.03-5.93 (m, 2H), 5.24-5.16 (m, 1H), 5.00-4.91 (m, 1H), 4.50 (br s, 2H), 4.38 (br t, J = 7.9 Hz, 1H), 4.31-4.25 (m, 4H), 3.73-3.69 (m, 3H), 3.37-3.30 (m, 3H), 3.25 (br d, J = 11.2 Hz, 2H), 3.01 (br d, J = 11.5 Hz, 2H), 2.92-2.77 (m, 5H), 2.36-2.24 (m, 7H), 2.21-2.14 (m, 2H), 2.07-1.93 (m, 3H), 1.85-1.74 (m, 3H), 1.52-1.44 (m, 2H), 1.39 (d, J = 7.0 |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | Hz, 3H), 0.99-0.95 (m, 3H), 0.85-0.79 (m, 3H) |
| 374 | D | A | D | NA | 527.44 | 1H NMR (400 MHz, DMSO-d6) δ: 9.00-8.96 (m, 1H), 8.40 (d, J = 7.6 Hz, 1H), 8.32 (s, 3H), 8.17 (br d, J = 7.5 Hz, 1H), 7.88 (br d, J = 7.8 Hz, 1H), 7.53 (br d, J = 4.3 Hz, 1H), 7.45-7.42 (m, 2H), 7.38-7.35 (m, 2H), 7.26-7.21 (m, 1H), 6.97 (br d, J = 7.1 Hz, 1H), 6.91-6.86 (m, 2H), 6.69 (d, J = 1.7 Hz, 1H), 6.11-6.05 (m, 3H), 5.24 (br s, 1H), 4.95-4.88 (m, 1H), 4.85 (br s, 1H), 4.78 (br s, 1H), 4.62-4.53 (m, 2H), 4.37 (br t, J = 7.8 Hz, 3H), 4.28 (br s, 3H), 4.21 (br d, J = 5.0 Hz, 3H), 4.17-4.14 (m, 2H), 3.70 (br dd, J = 4.1, 10.3 Hz, 1H), 3.64 (br dd, J = 2.3, 9.5 Hz, 1H), 3.48-3.37 (m, 3H), 3.03-2.89 (m, 4H), 2.80 (br s, 1H), 2.65-2.56 (m, 1H), 2.45 (s, 3H), 2.29 (br d, J = 8.2 Hz, 2H), 2.01 (br d, J = 8.4 Hz, 4H), 1.82-1.68 (m, 3H), 1.38 (d, J = 7.0 Hz, 3H), 1.27-1.13 (m, 2H), 0.95 (br d, J = 6.2 Hz, 3H), 0.85-0.75 (m, 3H) |
| 375 | D | NA | D | NA | 1065.88 | 1H NMR (400 MHz, DMSO-d6) δ (ppm): 14.14 (s, 1H), 8.31 (d, J = 8.2 Hz, 1H), 7.91 (d, J = 8.0 Hz, 1H), 7.77 (d, J = 6.0 Hz, 1H), 7.53-7.37 (m, 3H), 7.36-7.17 (m, 3H), 6.85 (dd, J = 12.6, 7.6 Hz, 2H), 6.62 (d, J = 6.1 Hz, 1H), 6.55-6.49 (m, 1H), 6.17-6.06 (m, 2H), 5.97 (brs, 2H), 5.24-5.04 (m, 2H), 5.01-4.93 (m, 1H), 4.55-4.38 (m, 3H), 4.30-4.16 (m, 4H), 3.75 (d, J = 8.5 Hz, 1H), 3.60-3.43 (m, 2H), 3.29-3.23 (m, 3H), 3.01 (d, J = 11.7 Hz, 2H), 2.81-2.56 (m, 5H), 2.39-2.11 (m, 8H), 2.12-2.03 (m, 6H), 1.99-1.91 (m, 5H), 1.82-1.72 (m, 3H), 1.49-1.34 (m, 5H), 1.24 (s, 1H), 0.96 (d, J = 6.6 Hz, 2H), 0.84-0.74 (m, 4H). |
| 376 | C | A | D | NA | 1065.88 | 1H NMR (400 MHz, DMSO-d6) δ (ppm): 14.12 (brs, 1H), 8.42 (d, J = 7.9 Hz, 1H), 7.95-7.88 (m, 1H), 7.77 (d, J = 6.0 Hz, 1H), 7.55-7.40 (m, 3H), 7.34-7.17 (m, 3H), 6.90-6.80 (m, 2H), 6.66- |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 6.48 (m, 2H), 6.16-6.07 (m, 2H), 5.97 (brs, 2H), 5.21-5.16 (m, 1H), 5.13-4.91 (m, 2H), 4.49 (brs, 2H), 4.37 (t, J = 7.8 Hz, 1H), 4.32-4.24 (m, 2H), 4.23-4.20 (m, 2H), 3.74-3.60 (m, 2H), 3.45 (d, J = 10.4 Hz, 1H), 3.25 (d, J = 11.6 Hz, 3H), 3.01 (d, J = 11.6 Hz, 2H), 2.78-2.72 (m, 2H), 2.69-2.64 (m, 2H), 2.33-2.24 (m, 5H), 2.11-2.20 (m, 8H), 2.00-1.91 (m, 5H), 1.83-1.73 (m, 3H), 1.50-1.36 (m, 5H), 0.98-0.95 (m, 3H), 0.84-0.79 (m, 3H). |
| 377 | C | A | D | NA | 1065.88 | 1H NMR (300 MHz, DMSO-d6) δ: 14.15 (brs, 1H), 12.20 (brs, 1H), 8.90-8.21 (m, 1H), 8.00-7.90 (m, 1H), 7.80-7.72 (m, 1H), 7.58-7.46 (m, 1H), 7.40-7.15 (m, 5H), 6.90-6.81 (m, 2H), 6.60-6.46 (m, 1H), 6.20-6.05 (m, 2H), 6.04-5.89 (m, 2H), 5.22-5.15 (m, 1H), 5.14-5.06 (m, 1H), 5.04-4.82 (m, 1H), 4.55-4.40(m, 3H), 4.33-4.15 (m, 4H), 3.80-3.70(m, 1H), 3.60-3.41 (m, 2H), 3.30-3.20 (m, 3H), 3.11-3.00(m, 2H), 2.80-2.61 (m, 4H), 2.35-2.21 (m, 6H), 2.19-2.17 (m, 6H), 2.10-2.08 (m, 1H), 2.05-1.92 (m, 3H), 1.85-1.70(m, 3H), 1.51-1.32 (m, 5H), 1.28-1.12 (m, 2H), 1.00-0.95 (m, 2H), 0.90-0.75 (m, 4H) |
| 378 | A | A | D | A | 1065.88 | 1H NMR (300 MHz, DMSO-d6) δ: 14.30 (brs, 1H), 12.31 (brs, 1H), 8.80-8.20 (m, 1H), 8.00-7.89 (m, 1H), 7.81-7.72 (m, 1H), 7.55-7.43 (m, 1H), 7.32-7.20 (m, 4H), 6.90-6.80 (m, 2H), 6.58-6.45 (m, 1H), 6.21-6.01 (m, 2H), 6.00-5.86 (m, 2H), 5.25-5.13 (m, 1H), 5.12-5.00 (m, 1H), 4.99-4.85 (m, 1H), 4.55-4.46(m, 2H), 4.40-4.35(m, 1H), 4.34-4.25(m, 2H), 4.15-3.80(m, 2H), 3.79-3.40 (m, 3H), 3.30-3.15(m, 4H), 3.10-2.92 (m, 2H), 2.80-2.67 (m, 2H), 2.66-2.60 (m, 2H), 2.32-2.21 (m, 4H), 2.20-2.10 (m, 9H), 2.09-1.90 (m, 3H), 1.88-1.70 (m, 3H), 1.53-1.30 (m, 5H), 1.29-1.20 (m, 1H), 1.02-0.72 (m, 6H); |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| 379 | D | NA | D | NA | 531.94 | 1H NMR (400 MHz, DMSO-d6) δ = 9.01-8.93 (m, 1H), 8.32 (d, J = 7.7 Hz, 1H), 7.91 (d, J = 8.0 Hz, 1H), 7.76 (d, J = 6.0 Hz, 1H), 7.49 (s, 1H), 7.48-7.25 (m, 4H), 7.21 (t, J = 7.6 Hz, 1H), 6.90-6.80 (m, 2H), 6.55 (s, 1H), 6.52 (d, J = 6.0 Hz, 1H), 6.14 (d, J = 1.6 Hz, 1H), 5.97 (s, 2H), 5.21-5.13 (m, 1H), 4.88 (t, J = 7.2 Hz, 1H), 4.49 (s, 2H), 4.41 (t, J = 8.0 Hz, 1H), 4.31-4.21 (m, 2H), 3.95 (d, J = 8.8 Hz, 1H), 3.60-3.43 (m, 7H), 3.24 (d, J = 11.2 Hz, 2H), 3.00 (d, J = 11.2 Hz, 2H), 2.77-2.76 (m, 2H), 2.75-2.64 (m, 2H), 2.34-2.19 (m, 8H), 2.17 (d, J = 7.2 Hz, 2H), 2.05-1.91 (m, 3H), 1.86-1.71 (m, 3H), 1.50-1.31 (m, 5H), 0.99-0.81 (m, 3H), 0.81-0.67 (m, 3H). |
| 380 | A | A | B | A | 531.94 | 1H NMR (400 MHz, DMSO-d6) δ = 8.98 (s, 1H), 8.43 (d, J = 7.6 Hz, 1H), 8.22 (s, 1H), 7.92 (d, J = 7.2 Hz, 1H), 7.77 (d, J = 6.0 Hz, 1H), 7.50 (s, 1H), 7.47-7.41 (m, 2H), 7.39-7.33 (m, 2H), 7.26-7.18 (m, 1H), 6.89-6.80 (m, 2H), 6.60-6.49 (m, 2H), 6.14 (s, 1H), 5.98 (s, 2H), 5.25-5.14 (m, 1H), 4.91 (t, J = 7.2 Hz, 1H), 4.49 (s, 2H), 4.40-4.22 (m, 3H), 3.85 (d, J = 9.6 Hz, 1H), 3.69 (dd, J1 = 4.0 Hz, J2 = 10.8 Hz, 1H), 3.62-3.44 (m, 6H), 3.23 (s, 2H), 3.01 (d, J = 11.6 Hz, 2H), 2.74 (d, J = 12.2 Hz, 2H), 2.45 (s, 2H), 2.35-2.23 (m, 8H), 2.17 (d, J = 7.6 Hz, 2H), 2.08-1.90 (m, 3H), 1.86-1.71 (m, 3H), 1.49-1.35 (m, 5H), 0.97 (d, J = 6.4 Hz, 3H), 0.82-0.71 (m, 3H) |
| 381 | C | A | D | NA | 537.94 | 1H NMR (400 MHz, DMSO-d6) δ: 9.03-8.96 (m, 1H), 8.38-8.31 (m, 1H), 8.23-8.18 (m, 1H), 7.96-7.88 (m, 1H), 7.79-7.71 (m, 1H), 7.51-7.46 (m, 1H), 7.44-7.39 (m, 2H), 7.35-7.29 (m, 2H), 7.25-7.18 (m, 1H), 6.90-6.80 (m, 2H), 6.55-6.49 (m, 1H), 6.20-6.10 (m, 2H), 6.01-5.93 (m, 2H), 5.26-5.16 (m, 1H), 4.95- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 4.82 (m, 3H), 4.52-4.45 (m, 2H), 4.45-4.38 (m, 1H), 4.33-4.21 (m, 1H), 3.82-3.74 (m, 1H), 3.59-3.53 (m, 2H), 3.51-3.47 (m, 2H), 3.27-3.20 (m, 4H), 3.04-2.96 (m, 2H), 2.47-2.45 (m, 4H), 2.27-2.09 (m, 8H), 2.08-2.01 (m, 1H), 1.97-1.90 (m, 8H), 1.81-1.71 (m, 1H), 1.48-1.32 (m, 3H), 0.99-0.92 (m, 2H), 0.85-0.79 (m, 3H), 0.78-0.73 (m, 1H) |
| 382 | A | A | A | 91 | 537.94 | 1H NMR (400 MHz, DMSO-d6) δ: 9.03-8.95 (m, 1H), 8.48-8.38 (m, 1H), 8.23-8.16 (m, 1H), 7.95-7.87 (m, 1H), 7.81-7.73 (m, 1H), 7.51-7.41 (m, 3H), 7.40-7.33 (m, 2H), 7.26-7.18 (m, 1H), 6.90-6.81 (m, 2H), 6.55-6.49 (m, 1H), 6.23-6.07 (m, 2H), 6.03-5.86 (m, 2H), 5.28-5.17 (m, 1H), 4.97-4.83 (m, 3H), 4.53-4.45 (m, 2H), 4.40-4.33 (m, 1H), 4.32-4.24 (m, 1H), 3.73-3.65 (m, 3H), 3.42-3.37 (m, 2H), 3.28-3.21 (m, 3H), 3.04-2.98 (m, 2H), 2.57-2.54 (m, 1H), 2.45 (s, 3H), 2.30-2.11 (m, 8H), 2.09-1.99 (m, 2H), 1.99-1.92 (m, 8H), 1.83-1.73 (m, 1H), 1.48-1.33 (m, 3H), 1.00-0.92 (m, 3H), 0.85-0.75 (m, 3H) |
| 383 | D | A | D | NA | 1060.80 | 1H NMR (400 MHz, DMSO-d6) δ = 8.99 (s, 1H), 8.47-8.40 (m, 1H), 8.37 (s, 2H), 8.17 (br d, J = 6.5 Hz, 1H), 7.88 (br d, J = 6.5 Hz, 1H), 7.53 (br d, J = 7.2 Hz, 1H), 7.49-7.41 (m, 2H), 7.41-7.34 (m, 2H), 7.24 (t, J = 7.7 Hz, 1H), 6.98 (br d, J = 7.3 Hz, 1H), 6.92-6.85 (m, 2H), 6.71 (br s, 1H), 6.16-6.06 (m, 3H), 5.25 (br d, J = 2.7 Hz, 1H), 4.94-4.85 (m, 3H), 4.79 (br s, 2H), 4.62-4.55 (m, 1H), 4.42-4.25 (m, 4H), 3.75-3.64 (m, 2H), 3.52-3.36 (m, 4H), 3.03 (br dd, J = 12.0, 17.2 Hz, 1H), 2.97-2.84 (m, 3H), 2.60-2.56 (m, 1H), 2.46 (s, 3H), 2.35-2.19 (m, 4H), 2.08-1.95 (m, 3H), 1.89 (br d, J = 12.3 Hz, 6H), 1.79 (ddd, J = 4.8, 7.9, 12.8 Hz, 1H), 1.38 (d, J = 7.0 Hz, 3H), 1.01-0.92 |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | (m, 3H), 0.83-0.76 (m, 3H) |
| 384 | B | A | D | NA | 1055.83 | 1H NMR (400 MHz, CD3OD ): δ 8.86 (s, 1H), 7.79-7.73 (m, 2H), 7.48-7.36 (m, 5H), 7.23 (s, 1H), 6.91-6.89 (m, 2H), 6.54 (d, J = 6.4 Hz, 1H), 6.20 (s, 1H), 6.02 (s, 1H), 5.01-4.99 (m, 1H), 4.58 (s, 1H), 4.52-4.41 (m, 3H), 4.24-4.21 (m, 4H), 3.78-3.67 (m, 3H), 3.13-3.10 (d, J = 11.6 Hz, 2H), 2.58-2.47 (m, 15H), 2.25-2.14 (m, 5H), 1.99-1.93 (m, 5H), 1.61 (s, 1H), 1.50-1.49 (d, J = 6.8 Hz, 3H), 1.29 (s, 1H), 1.07-1.06 (d, J = 6.8 Hz, 3H), 0.93-0.92 (d, J = 6.8 Hz, 4H). |
| 385 | A | A | A | A | 1055.83 | 1H NMR (300 MHz, CD3OD): δ 8.87 (s, 1H), 7.79-7.71 (m, 2H), 7.46-7.34 (m, 5H), 7.21 (s, 1H), 6.89-6.87 (m, J = 8.2 Hz, 2H), 6.53-6.52 (d, J = 6.2 Hz, 1H), 6.18 (s, 1H), 5.97 (s, 1H), 4.99-4.97 (d, J = 6.6 Hz, 1H), 4.65-4.37 (m, 5H), 4.24-4.21 (m, 4H), 3.85-3.50 (m, 3H), 3.31 (s, 1H), 3.09-3.06 (d, J = 9.9 Hz, 2H), 2.69-2.38 (m, 15H), 2.25-2.14 (m, 5H), 1.99-1.89 (m, 5H), 1.59-1.46 (m, 3H), 1.06-1.04 (d, J = 6.6 Hz, 3H), 0.89-0.87 (d, J = 6.6 Hz, 4H). |
| 386 | C | A | B | A | 1001.73 | 1H NMR (400 MHz, Methanol-d4) δ: 8.42 (s, 2H), 7.81-7.69 (m, 2H), 7.69-7.63 (m, 2H), 7.56-7.40 (m, 3H), 7.24-7.21 (m, 1H), 6.91-6.89 (m, 2H), 6.53-6.49 (m, 1H), 6.19 (d, J = 2.1 Hz, 1H), 6.10-6.07 (m, 1H), 5.31-5.26 (m, 1H), 5.13-5.10 (m, 3H), 5.02-4.98 (m, 1H), 4.61-4.51 (m, 3H), 4.42 (s, 1H), 3.79 (d, J = 9.2 Hz, 1H), 3.75-3.62 (m, 2H), 3.36-3.13 (m, 2H), 2.76-2.65(m, 3H), 2.47-2.33(m, 1H), 2.32-2.21 (m, 2H), 2.20-2.07(m, 3H), 1.97-1.94 (m, 1H), 1.53-1.40 (m, 3H), 1.39-1.24 (m, 3H), 1.11-1.02 (m, 2H), 0.99-0.84 (m, 4H) |
| 387 | A | A | C | B | 1001.73 | 1H NMR (400 MHz, Methanol-d4) δ: 8.42-8.39 (m, 2H), 7.81-7.72 (m, 2H), 7.72-7.63 (m, 2H), 7.50-7.48 (m, 3H), 7.24-7.21 (m, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 1H), 6.93-6.90 (m, 2H), 6.60-6.56 (m, 1H), 6.19 (d, J = 2.1 Hz, 1H), 6.09 (s, 1H), 5.34-5.30 (m, 1H), 5.18-5.09 (m, 3H), 5.03-5.00 (m, 1H), 4.61-4.59 (m, 1H), 4.56-4.51 (m, 3H), 4.50-4.46 (m, 1H), 3.83-3.80 (m, 1H), 3.74-3.70 (m, 1H), 3.68-3.63 (m, 1H), 3.15-3.07 (m, 2H), 2.76-2.63 (m, 4H), 2.46-2.32 (m, 1H), 2.26-2.23 (m, 2H), 2.20-2.06 (m, 3H), 1.96-1.92 (m, 1H), 1.59-1.47 (m, 2H), 1.38-1.25 (m, 2H), 1.09-1.01 (m, 3H), 0.96-0.83 (m, 4H) |
| 388 | B | A | B | A | 1083.83 | 1H NMR (400 MHz, DMSO-d6) δ: 9.00 (s, 1H), 8.54-8.59 (m, 2H), 8.20 (s, 1H), 7.93-7.91 (m, 1H), 7.79-7.69 (m, 3H), 7.49 (m, 1H), 7.24-7.20 (m, 1H), 6.87-6.82 (m, 2H), 6.54-6.52 (m, 1H), 6.14 (d, J = 2.0 Hz, 1H), 6.09 (s, 1H), 5.98-5.93 (m, 1H), 5.21-5.19 (m, 1H), 4.94-4.91 (m, 1H), 4.49 (s, 2H), 4.34 (t, J = 8.0 Hz, 1H), 4.29-4.20 (m, 4H), 3.71-3.64 (m, 2H), 3.26-3.23 (m, 4H), 3.02-2.97 (m, 4H), 2.67-3.65 (m, 4H), 2.33-2.17 (m, 9H), 2.03-1.95 (m, 3H), 1.78-1.69 (m, 3H), 1.60-1.57 (m, 2H), 1.49-1.38 (m, 6H), 0.98-0.94 (m, 3H), 0.84-0.70 (m, 3H) |
| 389 | C | A | D | NA | 1083.86 | 1H NMR (300 MHz, CD3OD, ppm): δ 8.86 (s, 1H), 7.79-7.77 (m, 2H), 7.47-7.43 (m, 5H), 7.40-7.38 (m, 1H), 6.92-6.90 (m, 2H), 6.49 (s, 1H), 6.19 (s, 1H), 6.01 (s, 1H), 4.97-4.95 (m, 1H), 4.75 (s, 1H), 4.59-4.52 (m, 3H), 4.20-4.18 (m, 4H), 3.73-3.68 (m, 3H), 3.09-3.07 (m, 2H), 2.43-2.40 (m, 13H), 2.26-2.15 (m, 5H), 1.75-1.71 (m, 9H), 1.49 (d, J = 7.2 Hz, 3H), 1.35-1.33 (m, 3H), 1.08 (d, J = 7.2 Hz, 3H), 0.93 (d, J = 7.2 Hz, 3H). |
| 390 | A | A | A | A | 1083.85 | 1H NMR (300 MHz, CD3OD, ppm) δ 8.87 (s, 1H), 7.79-7.77 (m, 2H), 7.47-7.43 (m, 5H), 7.30-7.18 (m, 1H), 6.91-6.88 (m, 2H), 6.49 (s, 1H), 6.00 (s, 1H), 4.97-4.94 (m, 1H), 4.75 (s, 1H), 4.53-4.52 (m, 4H), 4.22- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 4.19 (m, 4H), 3.70-3.64 (m, 1H), 3.53-3.51 (m, 2H), 3.08-3.01 (m, 2H), 2.47-2.41 (m, 12H), 2.24-2.15 (m, 6H), 2.04-1.95 (m, 1H), 1.75-1.62 (m, 12H), 1.52 (d, J = 7.2 Hz, 3H), 1.35-1.33 (m, 3H), 1.06 (d, J = 7.2 Hz, 3H), 0.91-0.88 (m, 4H). |
| 391 | D | NA | D | NA | 1075.75 | 1H NMR (400 MHz, DMSO-d6.ppm): δ 14.14 (s, 1H), 8.98 (d, J = 13.1 Hz, 1H), 8.44 (d, J = 2.7 Hz, 2H), 8.32 (d, J = 7.8 Hz, 1H), 7.92 (d, J = 8.4 Hz, 1H), 7.79 (d, J = 5.9 Hz, 1H), 7.54-7.50(m, 2H), 7.33 (m, 1H), 7.23 (t, J = 7.5 Hz, 1H), 7.07-6.92 (m, 1H), 6.92-6.70 (m, 3H), 6.56 (d, J = 7.3 Hz, 1H), 6.24-6.13 (m, 2H), 5.98 (s, 2H), 5.38-5.28 (m, 1H), 5.11 (d, J = 3.7 Hz, 2H), 4.99-4.84 (m, 3H), 4.54-4.44(m, 2H), 4.37 (m, 1H), 4.27 (s, 1H), 3.78 (d, J = 8.7 Hz, 1H), 3.58-3.44 (m, 2H), 3.28 (m, 2H), 3.03 (d, J =11.5 Hz, 2H), 2.60 (t, J = 5.8 Hz, 4H), 2.46 (d, J = 7.5 Hz, 3H), 2.34-2.19 (m, 4H), 2.03-1.97 (m, 3H), 1.88(m, 1H), 1.47 (d, J = 7.0 Hz, 1H), 1.35 (d, J = 7.0 Hz, 3H), 1.24 (s, 1H), 0.98 (d, J = 6.6 Hz, 2H), 0.81 (m, 4H). |
| 392 | A | A | B | A | 1075.75 | 1H NMR (400 MHz, DMSO-d6.ppm): δ 14.13 (s, 1H), 9.01-8.89 (m, 1H), 8.43 (d, J = 3.6 Hz, 2H), 8.30 (d, J = 7.8 Hz, 1H), 7.95-7.88 (m, 1H), 7.78 (d, J = 6.0 Hz, 1H), 7.52 (m, 1H), 7.37 (m, 2H), 7.32 (d, J = 8.2 Hz, 2H), 7.26-7.18 (m, 2H), 7.04-6.93 (m, 1H), 6.90-6.84 (m, 1H), 6.88-6.71 (m, 3H), 6.58-6.52 (m, 1H), 6.23-6.13 (m, 2H), 5.97 (s, 2H), 5.33 (m, 1H), 5.10 (d, J = 3.5 Hz, 2H), 4.98-4.89 (m, 3H), 4.5-4.42 (m, 1H), 4.26 (s, 1H), 3.77 (d, J = 8.7 Hz, 1H), 3.59-3.44 (m, 2H), 3.31-3.22 (m, 2H), 3.02 (d, J = 11.6 Hz, 2H), 2.59-2.45 (m, 3H), 2.23-2.04 (m, 4H), 1.97-1.87 (m, 3H), 1.83-1.72 (m, 1H), 1.46 (d, J = 6.9 Hz, 1H), 1.35 (d, J = 7.0 Hz, 2H), 1.23 (s, 1H), 0.97 (d, J = 6.6 Hz, 2H), 0.83 (d, J = 6.8 Hz, 4H). |

TABLE 2C-continued

| Ex. # | *BRM DC$_{50}$ (nM) | **BRM D$_{max}$ (%)† | *BRG1 DC$_{50}$ (nM) | **BRG1 D$_{max}$ (%)† | Observed Mass (2nd Observed Mass) | HNMR |
|---|---|---|---|---|---|---|
| Target protein degradation via exemplary bifunctional degradation compounds of Table 1C | | | | | | |
| 393 | D | A | D | NA | 1056.78 | 1H NMR (400 MHz, DMSO-d6, ppm): δ 14.11 (s, 1H), 8.45-8.33 (m, 2H), 7.93-7.81 (m, 1H), 7.50-7.42 (m, 1H), 7.51-7.29 (m, 3H), 7.28-7.18 (m, 2H), 6.92-6.80 (m, 2H), 6.58-6.51 (m, 1H), 6.27-6.13 (m, 1H), 5.96 (s, 1H), 5.35-5.30 (m, 1H), 5.21-5.09 (m, 3H), 5.06-4.82 (m, 1H), 4.61-4.50 (m, 2H), 4.31-4.26 (m, 1H), 3.89-3.55 (m, 3H), 3.33-3.11 (m, 3H), 3.01 (t, J = 5.9 Hz, 1H), 2.98-2.68 (m, 3H), 2.59-2.30 (m, 3H), 2.20-2.13 (m, 2H), 2.07-1.90 (m, 2H), 1.89-1.66 (m, 1H), 1.57-1.52 (m, 2H), 1.23-1.17 (m, 2H), 0.96-0.91 (m, 2H), 0.86-0.80 (m, 3H). |
| 394 | A | A | C | A | 1056.78 | 1H NMR (400 MHz, DMSO-d6, ppm): δ 14.12 (s, 1H), 8.49-8.41 (m, 2H), 7.91-7.77 (m, 2H), 7.49-7.39 (m, 4H), 7.27-7.15 (m, 2H), 6.91-6.55 (m, 3H), 6.25-6.15 (m, 2H), 5.96 (s, 2H), 5.35-5.30 (m, 1H), 5.20-5.14 (m, 3H), 5.04-4.89 (m, 1H), 4.71-4.38 (m, 2H), 4.28 (m, 2H), 3.75-3.68 (m, 2H), 3.65-3.45 (m, 4H), 3.31-3.24 (m, 2H), 3.06-3.01 (m, 2H), 2.63-2.56 (m, 4H), 2.27-2.18 (m, 5H), 2.07-1.78 (m, 4H), 1.56-1.03 (m, 5H), 0.97-0.92 (m, 3H), 0.82-0.76 (m, 3H). |
| 395 | A | A | C | A | 500.40 | 1H NMR (400 MHz, DMSO-d6) δ = 9.03-8.93 (m, 1H), 8.49 (s, 1H), 8.42 (d, J = 7.6 Hz, 1H), 8.25-8.16 (m, 3H), 8.05-7.97 (m, 1H), 7.49-7.40 (m, 2H), 7.40-7.32 (m, 2H), 7.31-7.22 (m, 1H), 6.97-6.89 (m, 2H), 6.50 (s, 2H), 6.08 (s, 1H), 5.18 (s, 2H), 4.94-4.87 (m, 1H), 4.36 (t, J = 7.6 Hz, 1H), 4.28 (s, 1H), 4.22-4.14 (m, 4H), 4.12 (s, 2H), 3.73-3.53 (m, 2H), 3.50-3.40 (m, 2H), 3.24-3.16 (m, 1H), 2.73-2.66 (m, 2H), 2.61 (t, J = 5.6 Hz, 2H), 2.45 (s, 3H), 2.25-2.14 (m, 3H), 2.12-1.99 (m, 5H), 1.81-1.69 (m, 3H), 1.43-1.29 (m, 5H), 0.99-0.91 (m, 3H), 0.83-0.76 (m, 3H). |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| 396 | B | A | D | NA | 542.44 | 1H NMR (400 MHz, DMSO-d6) δ: 9.00 (s, 1H), 8.52 (d, J = 2.0 Hz, 1H), 8.48 (d, J = 6.8 Hz, 1H), 8.21 (s, 3H), 7.91 (d, J = 8.0 Hz, 1H), 7.81-7.75 (m, 2H), 7.74-7.67 (m, 1H), 7.49 (s, 1H), 7.22 (t, J = 7.60 Hz, 1H), 6.81-6.89 (m, 2 H), 6.55-6.50 (m, 1H), 6.13 (d, J = 2.0 Hz, 1H), 6.07 (s, 1H), 5.97 (s, 2H), 5.17 (d, J = 4.8 Hz, 1H), 4.93 (m, J = 7.2 Hz, 1H), 4.49 (s, 2H), 4.35 (m, J = 8.0 Hz, 1H), 4.27 (s, 2H), 4.16 (m, J = 6.0 Hz, 2H), 3.64 (d, J = 10.0 Hz, 2H), 3.02 (s, 1H), 3.00 (s, 1H), 2.90 (s, 2H), 2.68-2.66 (m, 2H), 2.65 (s, 3H), 2.34-2.31 (m, 3H), 2.28 (s, 5H), 2.17 (d, J = 7.2 Hz, 2H), 2.07-1.93 (m, 4H), 1.87 (s, 5H), 1.80-1.70 (m, 1H), 1.48 (d, J = 6.8 Hz, 1H), 1.41 (d, J = 7.2 Hz, 3H), 1.16 (d, J = 14.0 Hz, 2H), 1.03 (d, J = 10.4 Hz, 2H), 0.98-0.91 (m, 3H), 0.79 (d, J = 6.8 Hz, 3H) |
| 397 | D | NA | D | NA | 1052.83 | 1H NMR (300 MHz, CD3OD): δ 8.46 (s, 1H), 7.92-7.74 (m, 3H), 7.48-7.40 (m, 3H), 7.22 (s, 1H), 6.95-6.87 (m, 3H), 6.52 (s, 1H), 6.12-6.03 (m, 2H), 5.18-5.04 (m, 2H), 4.55-4.26 (m, 7H), 3.75-3.66 (m, 3H), 3.41 (s, 2H), 3.12-3.08 (d, J = 11.7 Hz, 2H), 2.86-2.80 (m, 4H), 2.53-2.50 (d, J = 7.5 Hz, 2H), 3.40-2.12 (m, 11H), 1.88-1.85 (d, J = 10.2 Hz, 3H), 1.64-1.51 (m, 6H), 1.28 (s, 4H), 1.06-1.04 (d, J = 6.3 Hz, 3H), 0.94-0.84 (m, 6H). |
| 398 | A | A | D | A | 1052.83 | 1H NMR (300 MHz, MeOD): δ 8.53 (s, 1H), 7.79-7.77 (d, J = 6.3 Hz, 1H), 7.54-7.51 (d, J = 8.4 Hz, 2H), 7.48-7.42 (m, 3H), 7.24 (s, 1H), 6.98-6.90 (m, 3H), 6.53 (s, 1H), 6.15-6.03 (m, 2H), 5.21-5.08 (m, 2H), 4.59-4.33 (m, 7H), 3.90-3.79 (m, 1H), 3.71-3.61 (m, 2H), 3.58-3.40 (m, 2H), 3.14-3.11 (d, J = 11.7 Hz, 2H), 2.87-2.82 (m, 4H), 2.53 (s, 3H), 2.42-2.37 (m, 7H), 2.26-2.17 (m, 6H), 1.99-1.85 (m, 3H), 1.67-1.57 (m, 5H), 1.07-1.05 (d, J = 6.3 Hz, 3H), |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 0.91-0.89 (d, J = 6.6 Hz, 3H). |
| 399 | D | NA | D | NA | 1074.73 | 1H NMR (300 MHz, DMSO-d6): δ 14.15 (s, 1H), 9.02-8.95 (m, 1H), 8.62-8.33 (m, 3H), 8.00-7.81 (m, 1H), 7.80-7.62 (m, 2H), 7.60-7.52 (m, 1H), 7.40-7.15 (m, 1H), 6.93-6.80 (m, 2H), 6.59-6.50 (m, 1H), 6.25-6.13 (m, 2H), 6.05-5.90 (m, 2H), 5.40-5.31 (m, 1H), 5.22-5.05 (m, 3H), 5.04-4.81 (m, 1H), 4.60-4.45(m, 2H), 4.44-4.35 (m, 1H), 4.40-4.30(m, 1H), 3.85-3.76 (m, 1H), 3.62-3.45 (m, 2H), 3.24-3.22(m, 2H), 3.03-2.98 (m, 1H), 2.68-2.60 (m, 3H), 2.59-2.52 (m, 3H), 2.40-2.11 (m, 4H), 2.10-1.85 (m, 3H), 1.80-1.70(m, 1H), 1.53-1.48 (m, 1H), 1.40-1.35 (m, 2H), 1.30-1.15 (m, 2H), 1.10-0.85 (m, 3H), 0.84-0.76 (m, 3H). |
| 400 | A | A | C | A | 1074.73 | 1H NMR (300 MHz, DMSO-d6): δ 14.15 (s, 1H), 9.05-8.85 (m, 1H), 8.55-8.40 (m, 4H), 8.00-7.90 (m, 1H), 7.88-7.70 (m, 2H), 7.69-7.65 (m, 1H), 7.55-7.48 (m, 1H), 7.30-7.15 (m, 1H), 6.98-6.78 (m, 2H), 6.60-6.50 (m, 1H), 6.23-6.15 (m, 2H), 6.08-5.90 (m, 2H), 5.40-5.25 (m, 1H), 5.20-5.11 (m, 4H), 5.00-4.87(m, 1H), 4.59-4.45 (m, 2H), 4.40-4.21(m, 2H), 3.50-3.41 (m, 1H), 3.25-3.20 (m, 2H), 3.05-3.00(m, 2H), 2.68-2.66 (m, 3H), 2.65-2.64 (m, 3H), 2.35-2.15 (m, 4H), 2.05-2.00 (m, 1H), 1.99-1.97 (m, 2H), 1.82-1.70(m, 1H), 1.50-1.41 (m, 3H), 1.30-1.18 (m, 2H), 1.00-0.91 (m, 3H), 0.87-0.80 (m, 3H). |
| 401 | D | NA | D | NA | 1137.88 | 1H NMR (400 MHz, DMSO-d6) δ: 9.03-8.97 (m, 1H), 8.50 (d, J = 1.6 Hz, 1H), 8.27 (d, J = 7.6 Hz, 1H), 7.92-7.60 (m, 4H), 7.50 (s, 1H), 7.23 (t, J = 7.6 Hz, 1H), 6.90-6.83 (m, 2H), 6.53 (br d, J = 6.0 Hz, 1H), 6.14 (s, 2H), 5.96 (s, 2H), 5.22-5.11 (m, 1H), 5.08-4.86 (m, 1H), 4.50 (br s, 2H), 4.41 (t, J = 7.6 Hz, 1H), 4.33-4.22 (m, 2H), 3.69 (d, J = 8.8 Hz, 1H), 3.65-3.38 (m, 4H), 3.33- |

TABLE 2C-continued

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| Target protein degradation via exemplary bifunctional degradation compounds of Table 1C | | | | | | |
| | | | | | | 3.21 (m, 6H), 3.18-2.95 (m, 6H), 2.73-2.68 (m, 2H), 2.42-2.12 (m, 15H), 2.10-1.92 (m, 5H), 1.86-1.66 (m, 3H), 1.53-1.29 (m, 5H), 0.96 (d, J = 6.8 Hz, 3H), 0.83-0.73 (m, 3H) |
| 402 | A | A | D | A | 1137.88 | 1H NMR (400 MHz, DMSO-d6) δ: 9.00 (s, 1H), 8.53 (s, 1H), 8.47 (br d, J = 7.2 Hz, 1H), 7.92 (br d, J = 8.0 Hz, 1H), 7.82-7.74 (m, 2H), 7.72-7.65 (m, 1H), 7.50 (s, 1H), 7.23 (t, J = 7.6 Hz, 1H), 6.91-6.82 (m, 2H), 6.53 (br d, J = 4.8 Hz, 1H), 6.13 (s, 2H), 6.01-5.92 (m, 2H), 5.29-5.07 (m, 1H), 5.07-4.88 (m, 1H), 4.50 (br s, 2H), 4.39-4.30 (m, 1H), 4.29-4.22 (m, 2H), 3.71 (br dd, J = 4.4, 10.4 Hz, 1H), 3.57 (br d, J = 10.0 Hz, 1H), 3.49-3.36 (m, 4H), 3.31-3.20 (m, 5H), 3.14 (br s, 4H), 3.02 (br d, J = 11.6 Hz, 2H), 2.75-2.62 (m, 2H), 2.48-2.37 (m, 7H), 2.37-2.14 (m, 8H), 2.09-1.93 (m, 5H), 1.84-1.69 (m, 3H), 1.55-1.28 (m, 5H), 1.01-0.89 (m, 3H), 0.89-0.70 (m, 3H) |
| 403 | B | A | D | NA | 1024.76 (1024.63) | 1H NMR (400 MHz, METHANOL-d4) δ: 8.95-8.78 (m, 1H), 8.47 (br s, 1H), 7.84-7.63 (m, 2H), 7.50-7.34 (m, 5H), 7.28-7.20 (m, 1H), 6.94-6.85 (m, 2H), 6.56 (dd, J = 2.0, 6.4 Hz, 1H), 6.18-6.05 (m, 2H), 5.13 (td, J = 3.2, 6.8 Hz, 1H), 5.02-4.98 (m, 1H), 4.55 (br s, 3H), 4.43 (br s, 2H), 3.77-3.64 (m, 3H), 3.58-3.46 (m, 3H), 3.41-3.34 (m, 3H), 3.12 (br d, J = 11.2 Hz, 4H), 2.48-2.36 (m, 7H), 2.29-2.12 (m, 5H), 2.01-1.83 (m, 3H), 1.63-1.44 (m, 5H), 1.06 (d, J = 6.8 Hz, 3H), 0.86 (br d, J = 6.8 Hz, 3H) |
| 404 | A | A | A | A | 1024.76 (1024.63) | 1H NMR (400 MHz, METHANOL-d4) δ: 8.93-8.82 (m, 1H), 8.41 (s, 1H), 7.83-7.71 (m, 2H), 7.53-7.32 (m, 5H), 7.23 (dt, J = 1.6, 8.0 Hz, 1H), 7.07-6.76 (m, 2H), 6.57 (dd, J = 2.0, 6.4 Hz, 1H), 6.19-5.98 (m, 2H), 5.19-5.09 (m, 1H), 5.08-4.99 (m, 1H), 4.58-4.48 (m, 3H), 4.46-4.35 (m, 2H), 3.84 (dd, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | J = 4.4, 10.8 Hz, 1H), 3.65-3.60 (m, 1H), 3.60-3.43 (m, 4H), 3.36 (br d, J = 11.6 Hz, 2H), 3.16-2.90 (m, 4H), 2.52-2.32 (m, 8H), 2.31-2.09 (m, 5H), 1.99-1.84 (m, 3H), 1.68-1.47 (m, 5H), 1.05 (d, J = 6.6 Hz, 3H), 0.93-0.83 (m, 3H) |
| 405 | A | A | C | A | 1081.80 | 1H NMR (400 MHz, DMSO-d6) δ: 8.99 (s, 1H), 8.41 (d, J = 7.6 Hz, 1H), 8.19 (s, 1H), 7.91 (d, J = 7.6 Hz, 1H), 7.78 (d, J = 6.0 Hz, 1H), 7.50 (s, 1H), 7.47-7.42 (m, 2H), 7.40-7.36 (m, 2H), 7.26-7.20 (m, 1H), 6.90-6.83 (m, 2H), 6.62-6.57 (m, 1H), 6.25 (d, J = 1.6 Hz, 1H), 6.09 (s, 1H), 5.97 (s, 2H), 5.27 (br dd, J = 6.8, 2.8 Hz, 1H), 4.92 (br t, J = 7.2 Hz, 1H), 4.52 (br s, 3H), 4.42-4.34 (m, 1H), 4.29 (br d, J = 2.0 Hz, 1H), 4.21 (br d, J = 5.6 Hz, 3H), 4.13-4.03 (m, 1H), 3.79-3.68 (m, 3H), 3.65 (br d, J = 10.0 Hz, 2H), 3.25-3.24 (m, 2H), 3.02 (br dd, J = 11.2, 3.6 Hz, 3H), 2.89 (br d, J = 2.8 Hz, 2H), 2.69-2.66 (m, 1H), 2.46 (s, 3H), 2.19 (br d, J = 7.6 Hz, 4H), 2.09-1.91 (m, 5H), 1.85-1.72 (m, 1H), 1.64-1.43 (m, 5H), 1.38 (d, J = 6.8 Hz, 3H), 0.96 (d, J = 6.4 Hz, 3H), 0.80 (d, J = 6.8 Hz, 3H) |
| 406 | D | NA | D | NA | 1067.82 | 1H NMR (400 MHz, DMSO-d6) δ: 8.90 (s, 1H), 8.33 (s, 3H), 8.09 (br d, J = 2.8 Hz, 1H), 7.79 (br d, J = 6.8 Hz, 1H), 7.44 (br d, J = 7.6 Hz, 1H), 7.35 (d, J = 8.4 Hz, 2H), 7.27 (d, J = 8.4 Hz, 2H), 7.14 (br d, J = 7.2 Hz, 1H), 6.93-6.86 (m, 1H), 6.82-6.73 (m, 2H), 6.65 (br s, 1H), 6.06-5.94 (m, 2H), 5.26-5.15 (m, 1H), 4.86-4.68 (m, 3H), 4.62-4.45 (m, 1H), 4.26 (br t, J = 7.6 Hz, 1H), 4.22-4.06 (m, 3H), 3.64-3.51 (m, 3H), 2.94-2.75 (m, 7H), 2.37-2.26 (m, 10H), 2.22-2.01 (m, 5H), 2.00-1.83 (m, 4H), 1.81-1.32 (m, 6H), 1.27 (d, J = 7.00 Hz, 2H), 1.00-0.91 (m, 1H), 0.90-0.82 (m, 3H), 0.76-0.64 (m, 3H) |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| 407 | D | NA | D | NA | 1097.83 | 1H NMR (300 MHz, DMSO-d6, ppm): δ 13.59 (s, 1H), 8.99-8.83 (m, 1H), 8.68 (s, 1H), 8.30-8.14 (m, 1H), 8.09-7.98 (m, 1H), 7.90-7.82 (m, 1H), 7.65 (s, 1H), 7.51-7.41(m, 3H), 7.40-7.20 (m, 3H), 6.98-6.85 (m, 2H), 6.75-6.70 (m, 1H), 6.46 (s, 1H), 6.10-6.01 (m, 1H), 5.26-5.19 (m, 1H), 5.10-4.82 (m, 2H), 4.49-4.41 (m, 1H), 4.27-4.11 (m, 4H), 3.81-3.72 (m, 1H), 3.62-3.49 (m, 1H), 3.42-3.33 (m, 6H), 2.93-2.88 (m, 2H), 2.80-2.60 (m, 2H), 2.38-2.16 (m, 18H), 2.16-2.01 (m, 1H), 1.98-1.87 (m, 1H), 1.61-1.52 (m, 4H), 1.51-1.43 (m, 1H), 1.41-1.32 (m, 2H), 1.11(s, 1H), 1.09-0.91 (m, 3H), 0.94-0.75 (m, 3H) |
| 408 | A | A | A | A | 1097.83 | 1H NMR (300 MHz, DMSO-d6, ppm): δ 8.94 (s, 1H), 8.75-8.29 (m, 1H), 8.05-7.99 (m, 1H), 7.91-7.86 (m, 1H), 7.65 (s, 1H), 7.44-7.29 (m, 5H), 7.02-6.90 (m, 2H), 6.80-6.67 (m, 1H), 6.45 (s, 1H), 6.05-5.82 (m, 1H), 5.25-4.86 (m, 2H), 4.38-4.08 (m, 5H), 3.70-3.63 (m, 2H), 3.44-3.35 (m, 7H), 2.93-2.84 (m, 2H), 2.75-2.61 (m, 3H), 2.41-2.15 (m, 19H), 2.11-1.98 (m, 1H), 1.75 (s, 1H), 1.55 (s, 3H), 1.41-1.20 (m, 3H), 0.92 (s, 3H), 0.76 (s, 3H) |
| 409 | D | NA | D | NA | 1028.89 | 1H NMR (400 MHz, CD3OD): δ 7.95-7.89 (m, 2H), 7.73 (s, 1H), 7.46-7.32 (m, 6H), 7.00-6.97 (m, 2H), 6.89-6.83 (m, 2H), 6.05 (s, 1H), 5.03 (s, 1H), 4.61-4.33 (m, 6H), 3.83-3.68 (m, 6H), 3.59 (s, 2H), 3.42-3.40 (d, J = 10.4 Hz, 2H), 3.03-3.01 (d, J = 11.2 Hz, 2H), 3.83-2.77 (m, 4H), 2.65 (s, 7H), 2.45-2.19 (m, 2H), 1.97 (s, 1H), 1.84 (s, 4H), 1.51-1.50 (d, J = 7.2 Hz, 3H), 1.08-1.06 (d, J = 6.8 Hz, 3H), 0.94-0.92 (m, 4H). |
| 410 | A | A | A | A | 1028.89 | 1H NMR (400 MHz, CD3OD): δ 7.96-7.90 (m, 2H), 7.74 (s, 1H), 7.48-7.33 (m, 6H), 7.01-6.98 (m, 2H), 6.89-6.80 (m, 2H), 6.04 (s, 1H), 5.06 (s, 1H), 4.64-4.35 (m, 8H), 3.87-3.82 (m, 4H), 3.70- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 3.61 (m, 4H), 3.44-3.41 (d, J = 11.2 Hz, 2H), 3.05-3.02 (d, J = 11.6 Hz, 2H), 2.84-2.83 (d, J = 4.8 Hz, 4H), 2.68 (s, 7H), 2.41-2.15 (m, 2H), 2.02 (s, 1H), 1.84 (s, 4H), 1.63-1.54 (m, 2H), 1.08-1.06 (d, J = 6.0 Hz, 3H), 0.94-0.89 (m, 3H). |
| 411 | A | A | B | A | 1094.82 | 1H NMR (400 MHz, DMSO-d6) δ: 8.98 (s, 1H), 8.29-8.40 (d, J = 7.60 Hz, 1H), 7.92 (d, J = 7.20, 1H), 7.77 (d, J = 7.60, 1H), 7.50-7.21 (m, 6H), 6.88-6.83 (m, 2H), 6.54-6.52 (m, 1H), 6.14 (s, 1H), 6.07 (s, 1H), 5.96 (s, 2H), 5.20-4.82 (m, 4H), 4.50 (s, 2H), 4.43-4.37 (m, 1H), 4.28 (s, 2H), 3.76-3.63 (m, 1H), 3.57-3.43 (m, 2H), 3.25 (d, J = 11.2 Hz, 2H), 3.02 (d, J = 11.2 Hz, 2H), 2.91-2.81 (m, 1H), 2.65-2.60 (m, 2H), 2.46 (s, 3H), 2.34-2.22 (m, 8H), 2.19-2.04 (m, 5H), 1.98-1.96 (m, 2H), 1.88-1.76 (m, 5H), 1.47-1.35 (m, 4H), 1.32-1.24 (m, 1H), 1.08-1.04 (m, 1H), 0.97-0.96 (m, 3H), 0.84-0.75 (m, 3H) |
| 412 | D | NA | D | NA | 1119.94 | 1H NMR (400 MHz, METHANOL-d4) δ: 7.83-7.71 (m, 2H), 7.50 (s, 1H), 7.45 (d, J = 8.4 Hz, 2H), 7.34 (d, J = 8.4 Hz, 2H), 7.29-7.21 (m, 1H), 7.18-7.12 (m, 1H), 7.02-6.96 (m, 1H), 6.95-6.87 (m, 2H), 6.55 (br d, J = 6.0 Hz, 1H), 6.21-6.05 (m, 2H), 5.21-5.10 (m, 2H), 5.04 (br d, J = 7.2 Hz, 1H), 4.61-4.56 (m, 3H), 4.53 (br s, 2H), 4.47-4.36 (m, 2H), 3.78-3.64 (m, 3H), 3.37 (br s, 2H), 3.30-3.23 (m, 4H), 3.13 (br d, J = 11.6 Hz, 2H), 2.98-2.86 (m, 2H), 2.69-2.54 (m, 8H), 2.49-2.37 (m, 6H), 2.34 (s, 3H), 2.28-2.13 (m, 5H), 2.03-1.87 (m, 3H), 1.71-1.49 (m, 1H), 1.52 (d, J = 7.2 Hz, 2H), 1.30 (s, 1H), 1.07 (d, J = 6.4 Hz, 3H), 0.93 (d, J = 6.8 Hz, 3H) |
| 413 | A | A | D | A | 1119.93 | 1H NMR (400 MHz, DMSO-d6) δ: 8.43 (d, J = 7.6 Hz, 1H), 8.20 (s, 2H), 7.92 (dd, J = 1.2, 8.0 Hz, 1H), 7.77 (d, J = 6.0 Hz, 1H), 7.50 (s, 1H), 7.44-7.40 |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | (m, 2H), 7.39 (s, 2H), 7.28-7.18 (m, 2H), 6.92-6.89 (m, 1H), 6.89-6.82 (m, 2H), 6.53 (dd, J = 2.0, 6.0 Hz, 1H), 6.14 (s, 2H), 5.97 (s, 2H), 5.25-5.13 (m, 1H), 4.96 (br t, J = 7.2 Hz, 1H), 4.49 (br s, 2H), 4.37 (t, J = 7.6 Hz, 1H), 4.29 (br d, J = 5.2 Hz, 2H), 3.72 (br dd, J = 4.4, 10.4 Hz, 2H), 3.29-3.20 (m, 5H), 3.15 (br s, 5H), 3.08-2.97 (m, 3H), 2.90 (s, 1H), 2.84-2.72 (m, 2H), 2.47 (br s, 7H), 2.28 (s, 7H), 2.18 (br d, J = 7.2 Hz, 4H), 2.06-1.90 (m, 3H), 1.84-1.73 (m, 3H), 1.49-1.35 (m, 5H), 0.95 (br d, J = 6.8 Hz, 3H), 0.79 (d, J = 6.8 Hz, 3H) |
| 414 | A | A | B | A | 983.73 | 1H NMR (400 MHz, DMSO-d6) δ: 9.00-8.75 (m, 1H), 8.52 (s, 1H), 8.41 (d, J = 7.6 Hz, 1H), 8.23-8.17 (m, 2H), 8.01 (dd, J = 1.2, 8.4 Hz, 1H), 7.48-7.34 (m, 4H), 7.32-7.22 (m, 1H), 7.00-6.87 (m, 2H), 6.51 (s, 2H), 6.12-5.90 (m, 1H), 5.42 (dd, J = 2.0, 6.8 Hz, 1H), 5.17-5.06 (m, 1H), 4.90 (t, J = 7.2 Hz, 1H), 4.36 (t, J = 7.6 Hz, 1H), 4.28 (br t, J = 6.4 Hz, 2H), 4.19 (br t, J = 5.6 Hz, 2H), 3.74-3.54 (m, 4H), 3.08-2.96 (m, 2H), 2.75-2.65 (m, 3H), 2.64-2.59 (m, 2H), 2.45 (s, 3H), 2.30-1.95 (m, 9H), 1.82-1.65 (m, 6H), 1.46-1.33 (m, 5H), 1.03-0.91 (m, 3H), 0.85-0.73 (m, 3H) |
| 415 | A | A | B | A | 983.73 | 1H NMR (400 MHz, DMSO-d6) δ: 9.02-8.77 (m, 1H), 8.53 (s, 1H), 8.42 (d, J = 7.6 Hz, 1H), 8.27-8.18 (m, 3H), 8.02 (dd, J = 1.6, 8.4 Hz, 1H), 7.48-7.42 (m, 2H), 7.39-7.34 (m, 2H), 7.31-7.22 (m, 1H), 6.97-6.87 (m, 2H), 6.52 (s, 2H), 6.12-5.87 (m, 1H), 5.42 (dd, J = 2.0, 6.8 Hz, 1H), 4.91 (s, 1H), 4.37 (s, 1H), 4.28 (br t, J = 6.4 Hz, 2H), 4.20 (br t, J = 5.6 Hz, 2H), 3.73-3.62 (m, 4H), 3.11-2.98 (m, 2H), 2.77-2.70 (m, 2H), 2.63 (br t, J = 5.6 Hz, 3H), 2.46 (s, 3H), 2.29-1.97 (m, 9H), 1.70 (br d, J = 6.8 Hz, 6H), 1.45-1.35 (m, 5H), |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 0.99-0.92 (m, 3H), 0.86-0.77 (m, 3H) |
| 416 | A | A | B | A | 1069.80 | 1H NMR (400 MHz, DMSO-d6) δ 8.71 (s, 1H), 8.37 (d, J = 7.6 Hz, 1H), 7.92 (d, J = 7.2 Hz, 1H), 7.78 (d, J = 6.0 Hz, 1H), 7.52-7.40 (m, 3H), 7.29 (d, J = 8.4 Hz, 2H), 7.23 (t, J = 7.6 Hz, 1H), 6.90-6.82 (m, 2H), 6.53 (br d, J = 6.0 Hz, 1H), 6.14 (s, 1H), 6.09 (s, 1H), 6.00-5.92 (m, 2H), 5.59-5.53 (m, 2H), 5.23-5.16 (m, 1H), 5.13-4.99 (m, 1H), 4.88 (br t, J = 7.2 Hz, 1H), 4.50 (br s, 2H), 4.37 (t, J = 7.6 Hz, 1H), 4.33-4.25 (m, 2H), 4.21 (t, J = 5.6 Hz, 2H), 3.76-3.52 (m, 2H), 3.48-3.41 (m, 1H), 3.28-3.22 (m, 4H), 3.02 (br d, J = 11.2 Hz, 2H), 2.75 (br d, J = 11.2 Hz, 2H), 2.66-2.62 (m, 2H), 2.31-2.08 (m, 9H), 2.05-1.92 (m, 3H), 1.82-1.72 (m, 3H), 1.46-1.34 (m, 5H), 0.96 (br d, J = 6.4 Hz, 3H), 0.87-0.77 (m, 3H) |
| 417 | A | A | A | A | 1066.82 | 1H NMR (400 MHz, DMSO-d6) δ: 8.99 (s, 1H), 8.42 (d, J = 7.6 Hz, 1H), 7.92 (d, J = 7.6 Hz, 1H), 7.76 (d, J = 6.0 Hz, 1H), 7.50 (s, 1H), 7.44 (d, J = 8.4 Hz, 2H), 7.40-7.34 (m, 2H), 7.23 (t, J = 7.6 Hz, 1H), 6.90-6.82 (m, 2H), 6.51 (br d, J = 5.6 Hz, 1H), 6.15-6.06 (m, 2H), 5.99-5.90 (m, 2H), 5.17 (br t, J = 6.4 Hz, 1H), 5.11 (d, J = 3.6 Hz, 1H), 4.92 (br d, J = 7.2 Hz, 1H), 4.49 (br s, 2H), 4.37 (t, J = 7.6 Hz, 1H), 4.29 (br s, 1H), 4.17 (br t, J = 6.0 Hz, 2H), 3.70 (br dd, J = 4.0, 10.4 Hz, 1H), 3.64 (d, J = 9.6 Hz, 1H), 3.50-3.41 (m, 2H), 3.24 (br s, 3H), 3.02 (br d, J = 11.6 Hz, 2H), 2.79 (br d, J = 10.4 Hz, 2H), 2.46 (s, 4H), 2.39-2.31 (m, 2H), 2.23 (br s, 1H), 2.18 (br d, J = 7.2 Hz, 2H), 2.13 (br d, J = 6.4 Hz, 3H), 2.05 (br d, J = 18.8 Hz, 1H), 2.01-1.91 (m, 2H), 1.91-1.74 (m, 3H), 1.64 (br d, J = 6.4 Hz, 4H), 1.47-1.32 (m, 4H), 1.16 (br d, J = 12.0 Hz, 2H), 1.01-0.89 (m, 3H), 0.80 (br d, J = 6.8 Hz, 3H) |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| 418 | D | NA | D | NA | 1015.80 | 1H NMR (400 MHz, DMSO-d6) δ 14.13 (s, 1H), 9.0-8.33 (m, 1H), 7.91 (d, J = 7.9 Hz, 1H), 7.76 (d, J = 5.9 Hz, 1H), 7.49 (s, 1H), 7.27-7.14 (m, 5H), 6.94-6.77 (m, 2H), 6.52 (dd, J = 6.0, 2.1 Hz, 1H), 6.13-6.06 (m, 2H), 5.96 (s, 2H), 5.23-5.14 (m, 1H), 5.13-5.08 (m, 1H), 4.49-4.40(m, 3H), 4.31-4.18 (m, 6H), 3.81-3.70 (m, 1H), 3.63-3.47 (m, 2H), 3.27-.18 (m, 4H), 3.07-2.97 (m, 2H), 2.77-2.69 (m, 2H), 2.64-2.59 (m, 2H), 2.37-2.21(m, 5H), 2.20-2.04 (m, 4H), 2.02-1.82 (m, 4H), 1.79-1.65 (m, 2H), 1.53-1.32 (m, 4H), 1.28-1.03 (m, 2H), 1.02-0.93 (m, 2H), 0.88-0.77 (m, 2H), 0.71-0.54(m, 1H). |
| 419 | B | A | D | NA | 1015.80 | 1H NMR (400 MHz, DMSO-d6) δ 14.13 (s, 1H), 8.46 (t, J = 6.0 Hz, 1H), 7.91 (d, J = 7.9 Hz, 1H), 7.76 (d, J = 5.9 Hz, 1H), 7.49 (s, 1H), 7.31-7.19 (m, 5H), 6.96-6.78 (m, 2H), 6.59-6.45 (m, 1H), 6.16-6.07 (m, 2H), 5.96 (s, 2H), 5.27-4.99 (m, 2H), 4.51-4.46 (m, 2H), 4.38-4.15 (m, 7H), 3.75 (dd, J = 10.5, 4.5 Hz, 1H), 3.65 (d, J = 9.6 Hz, 1H), 3.24 (d, J = 11.5 Hz, 3H), 3.08-2.96 (m, 2H), 2.78-2.71 (m, 2H), 2.70-2.58 (m, 2H), 2.33-2.20 (m, 5H), 2.19-2.09(m, 4H), 2.07-1.82 (m, 4H), 1.81-1.71 (m, 2H), 1.54-1.30 (m, 4H), 1.29-1.03 (m, 3H), 0.94 (d, J = 6.2 Hz, 3H), 0.79 (d, J = 6.6 Hz, 3H) |
| 420 | A | A | C | A | 1165.87 | 1H NMR (400 MHz, Methanol-d4) δ (ppm): 8.91 (s, 1H), 7.81-7.72 (m, 2H), 7.49 (s, 5H), 7.24 (s, 1H), 6.91 (s, 2H), 6.57 (s, 1H), 6.15 (s, 1H), 6.07 (s, 1H), 5.94 (s, 1H), 5.15 (s, 1H), 4.56 (s, 4H), 4.50-4.36 (m, 4H), 3.87 (s, 1H), 3.75-3.67 (m, 1H), 3.60 (s, 3H), 3.19 (s, 3H), 3.12 (s, 1H), 3.01 (s, 3H), 2.54-2.39 (m, 8H), 2.26 (s, 5H), 2.16 (s, 5H), 1.97 (s, 4H), 1.78 (s, 5H), 1.30 (s, 3H), 1.04 (s, 3H), 0.90 (s, 4H) |
| 421 | D | NA | D | NA | 1119.80 | 1H NMR (400 MHz, DMSO-d6) δ: 9.05-8.97 (m, 1H), 8.52-8.43 (m, 2H), 7.99- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 7.93 (m, 1H), 7.77-7.72 (m, 1H), 7.71-7.66 (m, 1H), 7.57 (br d, J = 7.2 Hz, 1H), 7.50 (s, 1H), 7.42-7.35 (m, 1H), 7.04 (d, J = 8.0 Hz, 1H), 6.97 (br t, J = 7.6 Hz, 3H), 6.86 (br d, J = 6.4 Hz, 1H), 6.28 (s, 1H), 6.24-6.20 (m, 1H), 5.22 (br d, J = 4.0 Hz, 1H), 4.93-4.82 (m, 3H), 4.67-4.56 (m, 3H), 4.43 (br t, J = 7.6 Hz, 2H), 4.36-4.32 (m, 2H), 4.27 (br s, 2H), 3.81 (br d, J = 8.8 Hz, 1H), 3.69-3.56 (m, 4H), 3.51-3.39 (m, 3H), 3.24-3.08 (m, 4H), 2.67-2.63 (m, 3H), 2.45-2.39 (m, 2H), 2.32-2.20 (m, 3H), 2.11-1.97 (m, 3H), 1.96-1.86 (m, 2H), 1.79-1.55 (m, 3H), 1.51-1.37 (m, 3H), 0.98 (d, J = 6.8 Hz, 3H), 0.88-0.80 (m, 3H) |
| 422 | A | A | D | A | 1119.80 | 1H NMR (400 MHz, DMSO-d6) δ: 9.01 (s, 1H), 8.57-8.45 (m, 2H), 7.97 (d, J = 7.2 Hz, 1H), 7.79 (br dd, J = 2.0, 8.4 Hz, 1H), 7.75-7.68 (m, 1H), 7.55 (br d, J = 7.6 Hz, 1H), 7.51 (s, 1H), 7.40 (br t, J = 7.6 Hz, 1H), 7.05 (br d, J = 8.0 Hz, 2H), 6.98 (br t, J = 7.56 Hz, 1H), 6.89 (br d, J = 6.0 Hz, 1H), 6.30 (s, 1H), 6.24 (s, 1H), 5.23 (br s, 2H), 4.98-4.85 (m, 6H), 4.67-4.59 (m, 3H), 4.40-4.24 (m, 4H), 3.77-3.63 (m, 5H), 3.55-3.44 (m, 2H), 3.33-3.15 (m, 4H), 3.12-2.98 (m, 1H), 2.66 (s, 3H), 2.45 (br d, J = 7.2 Hz, 2H), 2.29 (br s, 3H), 2.10-1.93 (m, 5H), 1.83-1.65 (m, 2H), 1.54-1.38 (m, 3H), 1.04-0.94 (m, 3H), 0.89-0.78 (m, 3H) |
| 423 | D | NA | D | NA | 1165.72 | 1H NMR (300 MHz, Methanol-d4) δ (ppm): 8.89 (s, 1H), 7.75 (s, 2H), 7.58-7.33 (m, 5H), 7.23 (s, 1H), 6.89 (s, 2H), 6.53 (s, 1H), 6.20-5.78 (m, 3H), 5.12 (s, 1H), 4.60 (s, 1H), 4.51 (s, 2H), 4.35 (s, 4H), 3.76 (s, 1H), 3.67 (s, 2H), 3.37 (s, 2H), 3.12 (s, 2H), 3.04-2.91 (m, 3H), 2.90-2.67 (m, 4H), 2.51-2.01 (m, 21H), 1.85 (s, 2H), 1.60 (s, 5H), 1.30 (s, 1H), 1.03 (s, 2H), 0.89 (s, 4H). |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| 424 | D | NA | D | NA | 864.67 | 1H NMR (400 MHz, DMSO-d6) δ: 8.99-8.93 (m, 1H), 8.41 (d, J = 7.6 Hz, 1H), 7.91 (d, J = 7.6 Hz, 1H), 7.57-7.15 (m, 7H), 6.87 (d, J = 7.2 Hz, 2H), 6.26 (s, 1H), 5.85 (s, 2H), 4.99-4.87 (m, 1H), 4.41-4.23 (m, 2H), 4.01 (d, J = 9.2 Hz, 1H), 3.82-3.68 (m, 1H), 3.52-3.35 (m, 4H), 3.28-3.16 (m, 5H), 2.94-2.85 (m, 2H), 2.44 (s, 3H), 2.35-2.32 (m, 3H), 2.22-2.17 (m, 3H), 2.07-1.97 (m, 1H), 1.90-1.80 (m, 5H), 1.64-1.42 (m, 5H), 1.38 (d, J = 7.2 Hz, 3H), 0.81 (d, J = 7.2 Hz, 3H) |
| 425 | D | NA | D | NA | 864.67 | 1H NMR (400 MHz, DMSO-d6) δ: 8.98 (s, 1H), 8.30 (d, J = 7.6 Hz, 1H), 7.97-7.87 (m, 1H), 7.60-7.08 (m, 7H), 6.87 (d, J = 8.0 Hz, 2H), 6.25 (s, 1H), 5.87 (s, 2H), 5.01-4.85 (m, 1H), 4.54-4.41 (m, 1H), 4.31-4.20 (m, 1H), 4.05 (d, J = 8.4 Hz, 1H), 3.58-3.40 (m, 2H), 3.29-3.19 (m, 7H), 3.09 (dd, J1 = 6.4 Hz, J2 = 9.6 Hz, 1H), 2.90 (d, J = 10.8 Hz, 2H), 2.45-2.44 (m, 3H), 2.36-2.30 (m, 3H), 2.17 (s, 3H), 2.09-2.00 (m, 1H), 1.88 (s, 4H), 1.81-1.75 (m, 1H), 1.59-1.43 (m, 5H), 1.35 (d, J = 7.2 Hz, 3H), 1.03-0.88 (m, 3H) |
| 426 | D | NA | D | NA | 1121.88 | 1HNMR (400 MHz, DMSO-d6) δ: 9.12-8.90 (m, 1H), 8.67-8.43 (m, 1H), 8.25 (d, J = 7.6 Hz, 1H), 7.96-7.82 (m, 1H), 7.79-7.71 (m, 2H), 7.70-7.64 (m, 1H), 7.50 (s, 1H), 7.26-7.18 (m, 1H), 6.95-6.79 (m, 2H), 6.52 (dd, J = 1.6, 6.0 Hz, 1H), 6.14 (s, 2H), 5.97 (s, 2H), 5.17 (br t, J = 6.8 Hz, 1H), 4.90 (br t, J = 7.2 Hz, 1H), 4.49 (br s, 2H), 4.41 (s, 1H), 4.28 (br s, 1H), 3.69 (d, J = 8.8 Hz, 1H), 3.59-3.52 (m, 1H), 3.50-3.37 (m, 2H), 3.25 (br d, J = 11.2 Hz, 3H), 3.16 (br s, 1H), 3.10 (br s, 3H), 3.02 (br d, J = 11.2 Hz, 2H), 2.86-2.71 (m, 2H), 2.69-2.63 (m, 3H), 2.45-2.36 (m, 4H), 2.35-2.30 (m, 3H), 2.27 (br dd, J = 6.8, 8.8 Hz, 1H), 2.22- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 2.00 (m, 9H), 2.00-1.91 (m, 2H), 1.85 (br s, 3H), 1.62 (br d, J = 11.6 Hz, 2H), 1.49 (br d, J = 7.2 Hz, 1H), 1.39 (d, J = 7.2 Hz, 3H), 1.06 (br d, J = 9.2 Hz, 2H), 0.96 (d, J = 6.8 Hz, 2H), 0.87-0.79 (m, 3H), 0.76 (d, J = 6.8 Hz, 1H) |
| 427 | A | A | C | B | 1121.88 | 1HNMR (400 MHz, DMSO-d6) δ: 9.01 (s, 1H), 8.53 (d, J = 2.4 Hz, 1H), 8.47 (d, J = 7.2 Hz, 1H), 7.92 (dd, J = 1.2, 8.0 Hz, 1H), 7.83-7.74 (m, 2H), 7.74-7.66 (m, 1H), 7.50 (s, 1H), 7.28-7.17 (m, 1H), 6.94-6.80 (m, 2H), 6.52 (dd, J = 1.6, 6.0 Hz, 1H), 6.13 (s, 2H), 6.04-5.92 (m, 2H), 5.18 (br t, J = 6.8 Hz, 2H), 4.94 (br t, J = 7.2 Hz, 1H), 4.49 (br s, 2H), 4.35 (t, J = 8.0 Hz, 1H), 4.28 (br s, 1H), 3.71 (br dd, J = 4.4, 10.4 Hz, 1H), 3.57 (d, J = 10.0 Hz, 1H), 3.46-3.40 (m, 1H), 3.25 (br d, J = 11.2 Hz, 3H), 3.15 (br s, 4H), 3.02 (br d, J = 11.6 Hz, 2H), 2.80 (br d, J = 10.4 Hz, 2H), 2.66 (s, 3H), 2.43-2.35 (m, 7H), 2.18 (br d, J = 7.2 Hz, 3H), 2.13 (br d, J = 6.4 Hz, 6H), 2.06-1.92 (m, 3H), 1.86 (br t, J = 10.8 Hz, 2H), 1.77 (dt, J = 4.0, 8.4 Hz, 1H), 1.65 (br d, J = 11.6 Hz, 2H), 1.49 (br d, J = 7.2 Hz, 1H), 1.42 (d, J = 7.2 Hz, 3H), 1.17-1.01 (m, 2H), 1.00-0.91 (m, 3H), 0.79 (d, J = 6.8 Hz, 3H) |
| 428 | A 1 | A | D | A | 984.71 | 1H NMR (400 MHz, DMSO-d6) δ: 8.98 (s, 1H), 8.40 (s, 2H), 8.23 (s, 1H), 8.19 (d, J = 5.2 Hz, 1H), 8.02 (d, J = 8.4 Hz, 1H), 7.74-7.66 (m, 1H), 7.61-7.54 (m, 1H), 7.48-7.41 (m, 2H), 7.40-7.34 (m, 2H), 7.31-7.23 (m, 2H), 7.14 (s, 1H), 7.01 (s, 2H), 6.98-6.90 (m, 2H), 6.09 (s, 1H), 5.27 (s, 1H), 4.96-4.87 (m, 1H), 4.40-4.32 (m, 2H), 4.28 (s, 1H), 4.22 (m, J = 5.6 Hz, 2H), 3.70 (dd, J = 10.0, 4.4 Hz, 1H), 3.64 (d, J = 9.6 Hz, 1H), 3.44 (d, J = 9.2 Hz, 1H), 2.76 (d, J = 12.0 Hz, 2H), 2.69-2.63 (m, 3H), 2.45 (s, 3H), 2.40-2.31 (m, 5H), 2.25 (dd, J = 16.0, 6.4 Hz, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 1H), 2.13 (m, J = 10.0 Hz, 2H), 2.03 (m, J = 8.8 Hz, 1H), 1.79 (d, J = 8.0 Hz, 3H), 1.49-1.34 (m, 5H), 0.96 (d, J = 6.4 Hz, 3H), 0.85-0.77 (m, 3H) |
| 429 | D | NA | D | NA | 1070.64 (1070.65) | 1H NMR (300 MHz, DMSO-d6, ppm): δ 14.20 (s, 1H), 9.10-8.93 (m, 1H), 8.88-8.65 (m, 2H), 8.42-8.30 (m, 1H), 7.95-7.89 (m, 1H), 7.80-7.71 (m, 1H), 7.55-7.42 (m, 1H), 7.26-7.15(m, 1H), 6.90-6.78 (m, 2H), 6.58-6.45 (m, 1H), 6.20-6.01 (m, 2H), 6.00-5.85 (m, 2H), 5.23-5.05 (m, 1H), 5.00-4.81(m, 1H), 4.55-4.46 (m, 2H), 4.45-4.36 (m, 1H), 4.32-4.00 (m, 2H), 4.19-4.11 (m, 2H), 3.80-3.71 (m, 1H), 3.60-3.42 (m, 2H), 3.28-3.20 (m, 3H), 3.08-3.00 (m, 2H), 2.87-2.80 (m, 3H), 2.78-2.65 (m, 2H), 2.60-2.57(m, 1H), 2.32-2.23 (m, 4H), 2.20-2.14 (m, 2H), 2.12-2.01 (m, 2H), 2.00-1.91(m, 2H), 1.80-1.70 (m, 2H), 1.55-1.46 (m, 1H), 1.44-1.38 (m, 4H), 1.28-1.13 (m, 2H), 1.05-1.02 (m, 2H), 1.00-0.90(m, 3H), 0.88-0.62(m, 3H). |
| 430 | B | A | D | NA | 1070.64 (1070.65) | 1H NMR (300 MHz, DMSO-d6, ppm): δ 14.20 (s, 1H), 9.12-9.00 (m, 1H), 8.90-8.69 (m, 2H), 8.55-8.42 (m, 1H), 8.00-7.89 (m, 1H), 7.80-7.72 (m, 1H), 7.56-7.45 (m, 1H), 7.28-7.16(m, 1H), 6.90-6.79 (m, 2H), 6.58-6.47 (m, 1H), 6.20-6.02 (m, 2H), 6.00-5.87 (m, 2H), 5.26-5.15 (m, 1H), 5.13-5.00(m, 1H), 4.98-4.87 (m, 1H), 4.57-4.43 (m, 2H), 4.32-4.28 (m, 2H), 4.23-4.12 (m, 2H), 3.73-3.61 (m, 2H), 3.60-3.50 (m, 1H), 3.49-3.40 (m, 1H), 3.05-3.00 (m, 2H), 2.86-2.80 (m, 3H), 2.78-2.70 (m, 2H), 2.692.58 (m, 2H), 2.32-2.25(m, 4H), 2.21-2.10 (m, 3H), 2.08-2.00 (m, 1H), 1.99-1.95 (m, 2H), 1.83-1.50 (m, 4H), 1.49-1.40 (m, 4H), 1.26-1.21 (m, 1H), 1.20-1.10 (m, 3H), 1.00-0.92 (m, 3H), 0.85-0.77 (m, 3H). |
| 431 | A | A | C | A | 957.57 | 1H NMR (400 MHz, DMSO-d6) δ: 8.97 (s, 1H), 8.41 (br d, J = 7.6 Hz, 1H), 7.90 (br |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | d, J = 7.6 Hz, 1H), 7.78 (d, J = 6.0 Hz, 1H), 7.55-7.28 (m, 5H), 7.21 (br t, J = 7.6 Hz, 1H), 6.90-6.77 (m, 2H), 6.51 (br d, J = 4.4 Hz, 1H), 6.22 (s, 1H), 6.16-6.06 (m, 1H), 5.96 (br s, 2H), 5.09 (br d, J = 3.2 Hz, 1H), 4.96-4.82 (m, 1H), 4.56-4.43 (m, 2H), 4.36 (br t, J = 7.6 Hz, 1H), 4.27 (br s, 1H), 4.16 (br t, J = 6.0 Hz, 2H), 3.96 (br d, J = 9.6 Hz, 1H), 3.83-3.50 (m, 3H), 3.27-3.18 (m, 4H), 3.11-2.93 (m, 4H), 2.47-2.41 (m, 4H), 2.24-2.12 (m, 5H), 2.04-1.90 (m, 3H), 1.85-1.74 (m, 1H), 1.73-1.63 (m, 2H), 1.62-1.49 (m, 2H), 1.46-1.32 (m, 3H), 0.98 (br d, J = 6.4 Hz, 3H) |
| 432 | C | A | D | A | 957.57 | 1H NMR (400 MHz, DMSO-d6) δ: 8.98 (s, 1H), 8.29 (d, J = 7.6 Hz, 1H), 7.97-7.86 (m, 1H), 7.78 (d, J = 6.0 Hz, 1H), 7.54-7.28 (m, 5H), 7.24-7.14 (m, 1H), 6.92-6.76 (m, 2H), 6.52 (dd, J = 2.0, 6.0 Hz, 1H), 6.36-6.22 (m, 1H), 6.15 (d, J = 1.6 Hz, 1H), 5.97 (br s, 2H), 5.04-4.78 (m, 1H), 4.55-4.38 (m, 3H), 4.32-4.15 (m, 3H), 4.09 (d, J = 7.2 Hz, 1H), 3.52-3.37 (m, 4H), 3.29-3.16 (m, 4H), 3.05-2.90 (m, 2H), 2.44 (s, 5H), 2.23-2.13 (m, 5H), 2.10-1.88 (m, 4H), 1.82-1.56 (m, 5H), 1.46-1.25 (m, 3H), 0.84-0.68 (m, 3H) |
| 433 | B | A | D | A | 1038.64 | 1H NMR (400 MHz, DMSO-d6) δ: 9.00-8.96 (m, 1H), 8.40 (s, 1H), 8.19 (d, J = 7.6 Hz, 1H), 7.94-7.88 (m, 1H), 7.77 (d, J = 6.0 Hz, 1H), 7.51-7.46 (m, 2H), 7.44-7.38 (m, 2H), 7.33-7.30 (m, 1H), 7.22 (t, J = 7.6 Hz, 1H), 6.90-6.81 (m, 2H), 6.52 (br d, J = 6.0 Hz, 1H), 6.14 (d, J = 2.8 Hz, 2H), 5.96 (s, 2H), 5.26-5.17 (m, 1H), 5.07-4.82 (m, 1H), 4.54-4.46 (m, 2H), 4.44-4.38 (m, 1H), 4.32-4.23 (m, 1H), 4.17-4.06 (m, 1H), 3.71-3.65 (m, 1H), 3.60-3.53 (m, 3H), 3.26 (br s, 3H), 3.19-3.11 (m, 3H), 3.04-2.98 (m, 2H), 2.80-2.67 (m, 2H), 2.44 (s, 3H), 2.30-2.11 (m, 7H), 2.08-1.91 (m, 4H), |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 1.85-1.63 (m, 4H), 1.46 (d, J = 7.2 Hz, 1H), 1.35 (d, J = 7.2 Hz, 2H), 1.23-1.09 (m, 2H), 0.96 (d, J = 6.8 Hz, 2H), 0.82 (br d, J = 6.8 Hz, 3H), 0.75 (d, J = 6.8 Hz, 1H) |
| 434 | A | A | B | A | 1038.64 | 1H NMR (400 MHz, DMSO-d6) δ: 8.98 (s, 1H), 8.38 (d, J = 7.6 Hz, 1H), 8.32 (s, 1H), 7.95-7.88 (m, 1H), 7.77 (d, J = 6.0 Hz, 1H), 7.49 (s, 1H), 7.43 (d, J = 8.0 Hz, 2H), 7.39-7.34 (m, 2H), 7.25-7.19 (m, 1H), 6.90-6.81 (m, 2H), 6.56-6.48 (m, 1H), 6.17-6.09 (m, 2H), 6.01-5.92 (m, 2H), 5.27-5.17 (m, 1H), 4.91 (quin, J = 6.8 Hz, 1H), 4.49 (br s, 2H), 4.36 (t, J = 8.0 Hz, 1H), 4.28 (br s, 1H), 4.16-4.08 (m, 1H), 3.71 (br dd, J = 4.4, 10.4 Hz, 1H), 3.63 (br d, J = 12.8 Hz, 2H), 3.25 (br d, J = 11.2 Hz, 2H), 3.17 (br d, J = 5.6 Hz, 2H), 3.01 (br d, J = 11.6 Hz, 2H), 2.74 (br t, J = 11.6 Hz, 2H), 2.45 (s, 2H), 2.35-2.30 (m, 3H), 2.27-2.15 (m, 6H), 2.05-1.90 (m, 4H), 1.83-1.61 (m, 5H), 1.46-1.36 (m, 3H), 1.27-1.11 (m, 3H), 0.99-0.92 (m, 3H), 0.83-0.76 (m, 3H) |
| 435 | A | A | D | NA | 1082.67 | 1H NMR (400 MHz, DMSO-d6) δ: 9.00-8.93 (m, 1H), 8.33 (br d, J = 7.2 Hz, 1H), 7.91 (d, J = 7.6 Hz, 1H), 7.76 (d, J = 6.0 Hz, 1H), 7.51-7.29 (m, 5H), 7.23 (t, J = 8.0 Hz, 1H), 6.89-6.82 (m, 2H), 6.52 (br d, J = 4.4 Hz, 1H), 6.16-6.10 (m, 1H), 6.06 (s, 1H), 5.97 (s, 2H), 5.21-5.10 (m, 1H), 5.06-4.80 (m, 2H), 4.52 (s, 2H), 4.46-4.39 (m, 1H), 4.27 (br s, 3H), 3.75 (d, J = 8.4 Hz, 1H), 3.59-3.52 (m, 1H), 3.50-3.43 (m, 1H), 3.26 (br d, J = 11.2 Hz, 2H), 3.01 (br d, J = 11.5 Hz, 2H), 2.55-2.53 (m, 4H), 2.47-2.41 (m, 4H), 2.32-2.07 (m, 8H), 2.05-1.73 (m, 8H), 1.67-1.22 (m, 8H), 0.97 (d, J = 6.8 Hz, 3H), 0.83 (br d, J = 6.8 Hz, 3H) |
| 436 | A | A | C | A | 1082.67 | 1H NMR (400 MHz, DMSO-d6) δ: 8.99 (s, 1H), 8.40 (d, J = 7.6 Hz, 1H), 7.92 (d, J = 8.0 Hz, 1H), 7.76 (d, |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | J = 6.0 Hz, 1H), 7.50 (s, 1H), 7.47-7.35 (m, 4H), 7.22 (t, J = 7.6 Hz, 1H), 6.89-6.82 (m, 2H), 6.51 (br d, J = 6.0 Hz, 1H), 6.16-6.10 (m, 1H), 6.05 (s, 1H), 5.96 (s, 2H), 5.18 (quin, J = 6.4 Hz, 1H), 4.90-4.87 (m, 1H), 4.49 (br s, 2H), 4.38 (t, J = 7.6 Hz, 1H), 4.32-4.19 (m, 4H), 3.74-3.68 (m, 1H), 3.65-3.56 (m, 1H), 3.49-3.41 (m, 1H), 3.28-3.20 (m, 2H), 3.02 (br d, J = 11.6 Hz, 2H), 2.46 (s, 3H), 2.45-1.90 (m, 18H), 1.86-1.75 (m, 3H), 1.69-1.33 (m, 8H), 1.01-0.92 (m, 3H), 0.90-0.72 (m, 3H) |
| 437 | A | A | C | A | 1103.77 | 1H NMR: (400 MHz, DMSO-d6) δ: 8.44 (d, J = 7.6 Hz, 1H), 7.95-7.87 (m, 1H), 7.76 (d, J = 6.0 Hz, 1H), 7.50 (s, 1H), 7.40 (d, J = 7.6 Hz, 4H), 7.30-7.19 (m, 2H), 6.93-6.81 (m, 3H), 6.52 (dd, J = 2.0, 6.0 Hz, 1H), 6.14 (s, 2H), 5.98 (s, 2H), 5.23-5.13 (m, 1H), 4.96 (br t, J = 7.2 Hz, 1H), 4.49 (br s, 2H), 4.37 (t, J = 7.6 Hz, 1H), 4.29 (br s, 1H), 3.79-3.65 (m, 1H), 3.58 (d, J = 10.0 Hz, 1H), 3.49-3.39 (m, 1H), 3.32 (br s, 2H), 3.25 (br d, J = 11.6 Hz, 2H), 3.15 (br s, 3H), 3.02 (br d, J = 11.2 Hz, 2H), 2.80 (br d, J = 10.0 Hz, 1H), 2.53 (br s, 1H), 2.45-2.35 (m, 8H), 2.28 (s, 3H), 2.24-2.06 (m, 9H), 2.05-1.93 (m, 3H), 1.90-1.75 (m, 3H), 1.70-1.60 (m, 2H), 1.53-1.33 (m, 4H), 1.15-1.01 (m, 2H), 0.95 (br d, J = 6.4 Hz, 3H), 0.79 (d, J = 6.8 Hz, 3H) |
| 438 | D | NA | D | NA | 1047.66 | 1H NMR (400 MHz, DMSO-d6, ppm): δ 14.13 (s, 1H), 8.31-8.22 (m, 1H), 7.91-7.74 (m, 2H), 7.49 (s, 1H), 7.32-7.20 (m, 5H), 6.90-6.80 (m, 2H), 6.52-6.43 (m, 1H), 6.18-6.05 (m, 2H), 5.96 (s, 2H), 5.23-5.18 (m, 1H), 4.98-4.75 (m, 1H), 4.49-4.41(m, 3H), 4.32-4.15 (m, 4H), 3.75-3.66 (m, 1H), 6.61-3.50 (m, 2H), 3.49-3.22 (m, 3H), 3.10-2.85 (m, 3H), 2.80-2.60 (m, 4H), 2.28-2.12 (m, 9H), 2.05-1.82 (m, 5H), 1.80-1.68 (m, 2H), |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 1.46-1.32 (m, 6H), 1.30-0.95 (m, 3H), 0.95-0.71 (m, 4H). |
| 439 | D | NA | D | NA | 1047.66 | 1H NMR (400 MHz, DMSO-d6, ppm): δ 14.13 (s, 1H), 8.36-8.30 (m, 1H), 7.95-8.85(m, 1H), 7.80-7.72 (m, 1H), 7.49 (s, 1H), 7.28-7.16 (m, 4H), 6.90-6.80 (m, 2H), 6.55-6.52 (m, 1H), 6.18-6.06 (m, 2H), 5.98-5.90 (m, 2H), 5.25-5.07 (m, 2H), 4.90-4.81 (m, 2H), 4.70-4.51 (m, 2H), 4.39-4.18(m, 4H), 3.73-3.60 (m, 2H), 3.51-3.401 (m, 2H), 3.10-2.89 (m, 4H), 2.74-2.55 (m, 5H), 2.28-2.15 (m, 9H), 2.04-1.94 (m, 5H), 1.88-1.72 (m, 3H), 1.46-1.30 (m, 4H), 1.25-1.06 (m, 2H), 0.95 (s, 3H), 0.81 (s, 3H). |
| 440 | D | NA | D | NA | 1070.64 | 1H NMR (300 MHz, DMSO-d6) δ14.25 (s, 1H), 9.20-9.01 (m, 1H), 9.0-8.85 (m, 2H), 8.79-8.60 (m, 1H), 7.90 (m, 1H), 7.75 (m, 1H), 7.45 (s, 1H), 7.20 (m, 1H), 7.00-6.80(m, 2H), 6.50(m, 1H), 6.20-5.85 (m, 4H), 5.20-5.00 (m, 2H), 4.99-4.80 (m, 1H), 4.60-4.35 (m, 3H), 4.34-4.10(m, 4H), 3.80-3.40 (m, 3H), 3.30-3.20 (m, 4H), 3.10-2.90 (m, 2H), 2.72-2.58 (m, 5H), 2.42-2.33 (m, 5H), 2.23-2.13 (m, 3H), 2.12-2.00 (m, 2H), 2.00-1.90 (m, 3H), 1.80-1.62 (m, 2H), 1.50-1.30 (m, 5H), 1.28-1.20 (m, 1H), 1.10-0.90 (d, 3H), 0.85-0.70 (d, 3H). |
| 441 | B | A | D | NA | 1070.64 | 1H NMR (300 MHz, DMSO-d6) δ14.25 (s, 1H), 9.15-9.00 (m, 1H), 8.95(m, 1H), 8.85 (m, 1H), 8.70-8.50(m, 1H), 7.90 (m, 1H), 7.75 (m, 1H), 7.50 (s, 1H), 7.20 (m, 1H), 7.00-6.80(m, 2H), 6.50(m, 1H), 6.20-6.10 (m, 2H), 6.00-5.85 (m, 2H), 5.20-5.15(m, 2H), 5.10-4.90 (m, 1H), 4.50-4.35 (m, 4H), 4.34-4.10(m, 3H), 3.80-3.60 (m, 2H), 3.50-3.40 (m, 1H), 3.30-3.20(m, 3H), 3.10-2.90 (m, 2H), 2.72-2.58 (m, 5H), 2.30-2.15 (m, 9H), 2.12-1.90 (m, 4H), 1.90-1.78(m, 2H), 1.50-1.32 (m, 5H), 1.30-1.20 (m, 2H), 1.00-0.85 (m, 3H), 0.85-0.70 (m, 3H). |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| 442 | D | NA | D | NA | 1070.63 | 1H NMR (400 MHz, Methanol-d4) δ (ppm): 9.06-8.99 (m, 1H), 8.06-7.99 (m, 1H), 7.81-7.65 (m, 3H), 7.49 (s, 1H), 7.28-7.20 (m, 1H), 6.90 s, 2H), 6.55 (s, 1H), 6.15 (s, 1H), 6.03 (s, 1H), 5.24 (s, 1H), 5.14 (s, 1H), 4.66-4.51 (m, 3H), 4.47-4.29 (m, 4H), 3.68 (s, 4H), 3.37 (s, 3H), 3.13 (s, 2H), 2.98-2.79 (m, 4H), 2.72 (s, 3H), 2.41 (s, 7H), 2.32-1.99 (m, 7H), 1.88 (s, 2H), 1.65 (s, 5H), 1.31 (s, 2H), 1.05 (s, 2H), 0.97-0.79 (m, 5H). |
| 443 | D | NA | D | NA | 1070.64 | 1H NMR (400 MHz, Methanol-d4) δ (ppm): 9.02 (s, 1H), 8.12-7.95 (m, 2H), 7.81-7.72 (m, 2H), 7.49 (s, 1H), 7.29-7.20 (m, 1H), 6.95-6.86 (m, 2H), 6.55 (s, 1H), 6.14 (s, 1H), 6.04 (s, 1H), 5.24 (s, 1H), 5.14 (s, 1H), 4.56 (s, 4H), 4.37 (s, 3H), 3.87 (s, 1H), 3.71-3.53 (m, 2H), 3.47-3.35 (m, 4H), 3.13 (s, 2H), 2.83 (s, 4H), 2.72 (s, 3H), 2.41 (s, 7H), 2.26 (s, 7H), 1.90 (s, 2H), 1.63 (s, 5H), 1.31 (s, 1H), 1.05 (s, 1H), 0.95-0.84 (m, 6H). |
| 444 | A | A | B | A | 1017.67 | 1H NMR (400 MHz, DMSO-d6) δ (ppm): 14.29 (s, 1H), 9.01-8.96 (m, 1H), 8.33 (dd, J = 51.5, 7.6 Hz, 1H), 7.98-7.88 (m, 1H), 7.55-7.18 (m, 6H), 6.91-6.83 (m, 2H), 6.21 (s, 2H), 6.06 (s, 1H), 5.09 (m, 1H), 5.03-4.84 (m, 1H), 4.46-4.34 (m, 1H), 4.27 (brs, 1H), 4.22-4.09 (m, 2H), 3.78-3.39 (m, 5H), 3.14 (m, 2H), 2.99 (m, 2H), 2.73 (m, 2H), 2.46 (m, 2H), 2.37-2.18 (m, 7H), 2.17-1.90 (m, 8H), 1.85-1.71 (m, 4H), 1.60 (m, 7H), 1.49-1.28 (m, 7H), 1.27-1.03 (m, 4H), 0.96 (m, 3H), 0.89-0.72 (m, 4H). |
| 445 | A | A | B | A | 1017.67 | 1H NMR (400 MHz, DMSO-d6) δ (ppm): 14.30 (s, 1H), 8.98 (s, 1H), 8.40-8.25 (m, 1H), 7.93 (d, J = 7.7 Hz, 1H), 7.58-7.18 (m, 7H), 6.88 (d, J = 7.8 Hz, 2H), 6.21 (s, 2H), 6.06 (s, 1H), 5.16-4.85 (m, 3H), 4.44-4.09 (m, 5H), 3.83-3.39 (m, 6H), 3.13 (m, 2H), 2.98 (m, 2H), 2.72 (m, 3H), 2.46 (m, 2H), 2.22 (m, 2H), 2.07-1.84 (m, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 5H), 1.77 (m, 4H), 1.62 (m, 5H), 1.48-1.32 (m, 5H), 1.24 (m, 6H), 0.96 (m, 3H), 0.88-0.73 (m, 3H) |
| 446 | D | NA | D | NA | 1083.68 | 1H NMR (400 MHz, MeOD-d4) δ: 8.80 (s, 1H), 8.36 (s, 3H), 7.91 (br d, J = 7.2 Hz, 1H), 7.68 (br s, 1H), 7.44 (s, 1H), 7.42-7.31 (m, 4H), 7.18 (t, J = 7.6 Hz, 1H), 6.97-6.81 (m, 3H), 6.54-6.49 (m, 1H), 6.02-5.87 (m, 1H), 5.27 (br s, 1H), 4.96 (q, J = 7.2 Hz, 1H), 4.73-4.27 (m, 8H), 3.77 (dd, J = 4.0, 10.8 Hz, 1H), 3.72-3.53 (m, 2H), 3.52-3.38 (m, 2H), 3.35-3.26 (m, 1H), 3.21-2.82 (m, 9H), 2.62 (br d, J = 10.8 Hz, 2H), 2.41 (s, 3H), 2.27 (br s, 3H), 2.19-2.02 (m, 3H), 2.03-1.86 (m, 1H), 1.82-1.57 (m, 4H), 1.53-1.40 (m, 3H), 0.99 (br d, J = 6.4 Hz, 3H), 0.87-0.78 (m, 3H). |
| 447 | D | NA | D | NA | 1103.78 | 1HNMR (400 MHz, DMSO-d6) δ: 8.25 (d, J = 7.6 Hz, 1H), 7.92 (d, J = 7.2 Hz, 1H), 7.76 (d, J = 6.0 Hz, 1H), 7.51-7.40 (m, 2H), 7.36 (d, J = 2.0 Hz, 3H), 7.28-7.19 (m, 2H), 6.96-6.80 (m, 3H), 6.59-6.46 (m, 1H), 6.15 (d, J = 10.8 Hz, 2H), 5.97 (s, 2H), 5.23-5.01 (m, 2H), 5.01-4.87 (m, 1H), 4.49 (br s, 2H), 4.42 (t, J = 7.6 Hz, 1H), 4.29 (br d, J = 2.8 Hz, 1H), 3.70 (d, J = 8.8 Hz, 1H), 3.56 (br s, 1H), 3.25 (br d, J = 11.6 Hz, 3H), 3.19-3.08 (m, 4H), 3.02 (br d, J = 11.6 Hz, 2H), 2.79 (br d, J = 10.8 Hz, 2H), 2.42-2.31 (m, 7H), 2.30-2.24 (m, 4H), 2.23-2.02 (m, 10H), 1.99-1.93 (m, 2H), 1.90-1.75 (m, 3H), 1.64 (br d, J = 10.4 Hz, 2H), 1.47 (br d, J = 7.2 Hz, 2H), 1.36 (d, J = 7.2 Hz, 2H), 1.07 (br dd, J = 2.4, 9.2 Hz, 2H), 0.96 (d, J = 6.4 Hz, 2H), 0.82 (d, J = 6.8 Hz, 4H) |
| 448 | A | A | D | A | 1097.69 | 1H NMR (400 MHz, DMSO-d6) δ: 14.12 (s, 1H), 9.01-8.99 (m, 1H), 8.52-8.46 (m, 2H), 7.91 (d, J = 8.0 Hz, 1H), 7.79-7.75 (m, 1H), 7.72-7.65 (m, 1H), 7.49 (m, 1H), 7.22 (d, J = 7.2 Hz, 1H), 6.87-6.82 |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | (m, 2H), 6.52 (dd, J = 2.0, 6.0 Hz, 1H), 6.13 (d, J = 2.0 Hz, 1H), 6.04 (s, 1H), 5.95 (m, 2H), 5.20-5.09 (m, 2H), 4.96-4.88 (m, 1H), 4.49 (s, 2H), 4.42-4.25 (m, 3H), 4.11-4.04 (m, 2H), 3.75-3.62 (m, 1H), 3.49-3.38 (m, 2H), 3.26-3.23 (m, 3H), 3.01 (d, J = 11.6 Hz, 2H), 2.89-2.80 (m, 2H), 2.66-3.65 (m, 3H), 2.27-2.09 (m, 7H), 2.05-1.95 (m, 3H), 1.79-1.72 (m, 3H), 1.49-1.37 (m, 2H), 1.08-0.90 (m, 11H), 0.83-0.74 (m, 3H). |
| 449 | A | A | B | A | 1068.69 | 1H NMR (400 MHz, DMSO-d6) δ: 9.06-8.79 (m, 1H), 8.45 (s, 1H), 8.43 (d, J = 7.6 Hz, 1H), 8.22 (d, J = 7.6 Hz, 2H), 8.18 (s, 1H), 8.02 (dd, J = 1.6, 8.4 Hz, 1H), 7.48-7.40 (m, 2H), 7.39-7.33 (m, 2H), 7.27 (s, 1H), 6.99-6.85 (m, 2H), 6.49 (s, 2H), 6.10-5.88 (m, 1H), 4.98-4.83 (m, 1H), 4.39-4.24 (m, 3H), 4.22-4.13 (m, 3H), 3.68-3.62 (m, 4H), 3.12 (td, J = 9.2, 17.6 Hz, 2H), 2.93-2.81 (m, 2H), 2.75 (br d, J = 9.6 Hz, 1H), 2.46 (s, 3H), 2.40-2.35 (m, 1H), 2.29-2.10 (m, 5H), 2.07-1.97 (m, 1H), 1.89 (br s, 1H), 1.84-1.57 (m, 12H), 1.52-1.43 (m, 4H), 1.38 (d, J = 7.2 Hz, 3H), 1.30-1.08 (m, 3H), 1.02-0.91 (m, 5H), 0.85-0.73 (m, 3H) |
| 450 | C | A | D | NA | 1068.69 | 1H NMR (400 MHz, DMSO-d6) δ: 9.03-8.93 (m, 1H), 8.45 (s, 1H), 8.32 (d, J = 8.0 Hz, 1H), 8.26-8.16 (m, 3H), 8.01 (dd, J = 1.6, 8.4 Hz, 1H), 7.48-7.23 (m, 5H), 6.97-6.86 (m, 2H), 6.48 (s, 2H), 6.18-6.03 (m, 1H), 4.88 (br t, J = 7.2 Hz, 1H), 4.56-4.39 (m, 1H), 4.35-4.09 (m, 6H), 3.74 (br d, J = 8.8 Hz, 2H), 3.20-3.03 (m, 2H), 2.89-2.70 (m, 4H), 2.44 (s, 3H), 2.40-2.35 (m, 1H), 2.25 (br d, J = 4.4 Hz, 3H), 2.19-2.11 (m, 2H), 2.08-2.00 (m, 1H), 1.88 (br t, J = 11.6 Hz, 1H), 1.82-1.55 (m, 12H), 1.51-1.43 (m, 4H), 1.34 (d, J = 7.2 Hz, 3H), 1.25-1.05 |

TABLE 2C-continued

| Ex. # | *BRM DC$_{50}$ (nM) | **BRM D$_{max}$ (%)† | *BRG1 DC$_{50}$ (nM) | **BRG1 D$_{max}$ (%)† | Observed Mass (2nd Observed Mass) | HNMR |
|---|---|---|---|---|---|---|
| Target protein degradation via exemplary bifunctional degradation compounds of Table 1C | | | | | | |
| | | | | | | (m, 3H), 0.96 (br d, J = 6.8 Hz, 5H), 0.82 (d, J = 6.8 Hz, 3H) |
| 451 | A | A | B | A | 1068.69 | 1H NMR (400 MHz, DMSO-d6) δ: 8.98 (s, 1H), 8.52-8.38 (m, 2H), 8.29-8.13 (m, 3H), 8.01 (br d, J = 8.2 Hz, 1H), 7.51-7.32 (m, 4H), 7.26 (br t, J = 7.6 Hz, 1H), 6.96-6.84 (m, 2H), 6.48 (br s, 2H), 6.07 (s, 1H), 4.96-4.87 (m, 1H), 4.67 (br s, 1H), 4.36-4.26 (m, 3H), 4.17 (br s, 3H), 3.68 (br d, J = 3.2 Hz, 2H), 3.12 (br s, 2H), 2.91-2.81 (m, 3H), 2.79-2.70 (m, 3H), 2.45 (s, 3H), 2.38-2.34 (m, 1H), 2.28-2.14 (m, 4H), 2.06-1.98 (m, 1H), 1.93-1.86 (m, 1H), 1.81-1.51 (m, 12H), 1.49-1.31 (m, 6H), 1.25-1.06 (m, 3H), 1.04-0.88 (m, 5H), 0.84-0.73 (m, 3H) |
| 452 | C | A | D | NA | 1068.69 | 1H NMR (400 MHz, DMSO-d6) δ: 9.05-8.90 (m, 1H), 8.45 (s, 1H), 8.31 (br d, J = 7.6 Hz, 1H), 8.26-8.15 (m, 3H), 8.01 (dd, J = 1.6, 8.4 Hz, 1H), 7.51-7.26 (m, 5H), 6.99-6.83 (m, 2H), 6.48 (s, 2H), 6.17-6.01 (m, 1H), 5.05-4.83 (m, 1H), 4.41 (br t, J = 7.6 Hz, 1H), 4.31-4.10 (m, 6H), 3.74 (br d, J = 8.8 Hz, 2H), 3.15-3.05 (m, 2H), 2.85-2.71 (m, 4H), 2.44 (s, 3H), 2.39-2.35 (m, 1H), 2.30-2.20 (m, 3H), 2.19-2.10 (m, 2H), 2.09-1.99 (m, 1H), 1.97-1.83 (m, 2H), 1.81-1.55 (m, 12H), 1.51-1.43 (m, 4H), 1.34 (d, J = 7.2 Hz, 2H), 1.25-1.05 (m, 3H), 0.96 (br d, J = 6.8 Hz, 5H), 0.83-0.73 (m, 3H) |
| 453 | A | A | B | A | 1068.69 | 1H NMR (400 MHz, DMSO-d6) δ: 9.03-8.77 (m, 1H), 8.45 (s, 1H), 8.44-8.39 (m, 1H), 8.21 (s, 1H), 8.18 (s, 2H), 8.01 (dd, J = 1.2, 8.4 Hz, 1H), 7.49-7.41 (m, 2H), 7.39-7.33 (m, 2H), 7.31-7.23 (m, 1H), 7.01-6.87 (m, 2H), 6.49 (s, 2H), 6.11-5.86 (m, 1H), 4.90 (br t, J = 7.2 Hz, 1H), 4.46-4.24 (m, 3H), 4.17 (br t, J = 6.0 Hz, 3H), 3.69-3.61 (m, 4H), 3.19-3.08 (m, 2H), 2.89 (br d, J = 10.4 Hz, 2H), 2.79 (br d, J = |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 10.4 Hz, 1H), 2.45 (s, 3H), 2.42 (br s, 1H), 2.33-2.05 (m, 5H), 2.05-1.92 (m, 2H), 1.91-1.56 (m, 12H), 1.50-1.40 (m, 4H), 1.37 (d, J = 7.2 Hz, 3H), 1.28-1.07 (m, 3H), 1.05-0.90 (m, 5H), 0.84-0.76 (m, 3H) |
| 454 | D | NA | D | NA | 1068.69 | 1H NMR (400 MHz, DMSO-d6) δ: 9.03-8.89 (m, 1H), 8.45 (s, 1H), 8.30 (br d, J = 7.6 Hz, 1H), 8.24-8.14 (m, 3H), 8.01 (br d, J = 7.2 Hz, 1H), 7.50-7.21 (m, 5H), 6.98-6.86 (m, 2H), 6.47 (s, 2H), 6.16-6.01 (m, 1H), 4.89 (br t, J = 7.2 Hz, 1H), 4.53-4.41 (m, 1H), 4.36-4.12 (m, 6H), 3.75 (br d, J = 8.8 Hz, 2H), 3.67-3.47 (m, 4H), 3.34-3.05 (m, 2H), 2.94-2.74 (m, 3H), 2.45 (s, 3H), 2.26-2.13 (m, 3H), 2.10-1.96 (m, 2H), 1.91-1.55 (m, 12H), 1.53-1.44 (m, 4H), 1.42-1.31 (m, 3H), 1.29-1.09 (m, 3H), 0.96 (br d, J = 6.8 Hz, 5H), 0.84-0.74 (m, 3H) |
| 455 | A | A | B | A | 1068.69 | 1H NMR (400 MHz, DMSO-d6) δ: 9.02-8.77 (m, 1H), 8.49-8.38 (m, 2H), 8.24-8.15 (m, 3H), 8.07-7.96 (m, 1H), 7.47-7.34 (m, 4H), 7.32-7.24 (m, 1H), 7.00-6.87 (m, 2H), 6.47 (s, 2H), 6.10-5.86 (m, 1H), 4.91 (br t, J = 7.2 Hz, 1H), 4.42-4.25 (m, 3H), 4.23-4.14 (m, 3H), 3.74-3.69 (m, 1H), 3.64 (br d, J = 9.6 Hz, 2H), 3.56 (br d, J = 12.4 Hz, 2H), 3.42 (br s, 1H), 3.30-3.22 (m, 2H), 3.14 (br dd, J = 8.8, 17.2 Hz, 1H), 2.94-2.75 (m, 3H), 2.45 (s, 3H), 2.28-2.10 (m, 4H), 2.09-1.94 (m, 2H), 1.92-1.57 (m, 12H), 1.49-1.35 (m, 6H), 1.30-1.09 (m, 3H), 1.03-0.87 (m, 5H), 0.85-0.76 (m, 3H) |
| 456 | D | NA | D | NA | 1068.69 | 1H NMR (400 MHz, DMSO-d6) δ: 9.01-8.89 (m, 1H), 8.45 (s, 1H), 8.29 (br d, J = 7.6 Hz, 1H), 8.24-8.15 (m, 3H), 8.01 (dd, J = 1.2, 8.4 Hz, 1H), 7.52-7.23 (m, 5H), 6.96-6.86 (m, 2H), 6.47 (s, 2H), 6.15-6.04 (m, 1H), 4.88 (br t, J = 7.2 Hz, 1H), 4.54-4.39 (m, 1H), 4.35- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 4.08 (m, 6H), 3.74 (br d, J = 8.8 Hz, 2H), 3.63 (br d, J = 10.2 Hz, 2H), 3.51-3.48 (m, 1H), 3.40-3.30 (m, 1H), 3.29-3.05 (m, 2H), 2.93-2.74 (m, 3H), 2.45 (s, 3H), 2.27-2.11 (m, 4H), 2.06-1.93 (m, 2H), 1.87-1.55 (m, 12H), 1.51-1.40 (m, 4H), 1.35 (d, J = 7.2 Hz, 2H), 1.27-1.09 (m, 3H), 0.96 (br d, J = 6.8 Hz, 5H), 0.83-0.74 (m, 3H) |
| 457 | A | A | D | NA | 1120.73 | 1H NMR (400 MHz, MeOD-d6) δ: 8.99 (s, 1H), 8.41 (d, J = 7.6 Hz, 1H), 7.92 (d, J = 7.6 Hz, 1H), 7.76 (d, J = 6.0 Hz, 1H), 7.51-7.35 (m, 5H), 7.23 (t, J = 7.2 Hz, 1H), 6.89-6.82 (m, 2H), 6.52 (dd, J = 1.6, 6.0 Hz, 1H), 6.14 (s, 2H), 6.04-5.92 (m, 2H), 5.21-5.15 (m, 1H), 5.14-4.86 (m, 2H), 4.49 (br s, 2H), 4.37 (t, J = 7.6 Hz, 1H), 4.29 (br s, 1H), 3.80-3.64 (m, 1H), 3.58 (d, J = 9.6 Hz, 1H), 3.48-3.37 (m, 5H), 3.28-3.24 (m, 2H), 3.15 (br s, 4H), 3.01 (br d, J = 11.6 Hz, 2H), 2.89 (br s, 2H), 2.46 (s, 3H), 2.40 (br s, 4H), 2.26-2.11 (m, 9H), 2.06-1.63 (m, 8H), 1.53 (br s, 1H), 1.38 (d, J = 7.2 Hz, 3H), 1.26-1.08 (m, 2H), 1.01-0.91 (m, 3H), 0.90-0.71 (m, 3H) |
| 458 | A | A | A | A | 1120.74 | 1H NMR (400 MHz, MeOD-d6) δ: 8.99 (s, 1H), 8.41 (d, J = 7.6 Hz, 1H), 7.92 (d, J = 7.6 Hz, 1H), 7.76 (d, J = 6.0 Hz, 1H), 7.51-7.35 (m, 5H), 7.23 (t, J = 7.2 Hz, 1H), 6.89-6.82 (m, 2H), 6.52 (dd, J = 1.6, 6.0 Hz, 1H), 6.14 (s, 2H), 6.04-5.92 (m, 2H), 5.21-5.15 (m, 1H), 5.14-4.86 (m, 2H), 4.49 (br s, 2H), 4.37 (t, J = 7.6 Hz, 1H), 4.29 (br s, 1H), 3.80-3.64 (m, 1H), 3.58 (d, J = 9.6 Hz, 1H), 3.48-3.37 (m, 5H), 3.28-3.24 (m, 2H), 3.15 (br s, 4H), 3.01 (br d, J = 11.6 Hz, 2H), 2.89 (br s, 2H), 2.46 (s, 3H), 2.40 (br s, 4H), 2.26-2.11 (m, 9H), 2.06-1.63 (m, 8H), 1.53 (br s, 1H), 1.38 (d, J = 7.2 Hz, 3H), 1.26-1.08 (m, 2H), 1.01-0.91 (m, 3H), 0.90-0.71 (m, 3H). |

TABLE 2C-continued

| Ex. # | *BRM DC$_{50}$ (nM) | **BRM D$_{max}$ (%)† | *BRG1 DC$_{50}$ (nM) | **BRG1 D$_{max}$ (%)† | Observed Mass (2nd Observed Mass) | HNMR |
|---|---|---|---|---|---|---|
| Target protein degradation via exemplary bifunctional degradation compounds of Table 1C | | | | | | |
| 459 | A | A | D | A | 1148.63 | 1H NMR (400 MHz, DMSO-d6) δ: 13.86 (d, J = 8.0 Hz, 1H), 11.35-11.06 (m, 1H), 9.28-9.06 (m, 1H), 8.60 (d, J = 7.6 Hz, 1H), 7.94 (d, J = 7.2 Hz, 1H), 7.57-7.28 (m, 7H), 7.23-7.12 (m, 1H), 7.01-6.85 (m, 2H), 6.41-6.27 (m, 1H), 6.20-5.99 (m, 1H), 5.25 (s, 2H), 4.94-4.89 (m, 4H), 4.81 (s, 2H), 4.60 (s, 2H), 4.44-4.26 (m, 2H), 3.87-3.58 (m, 5H), 3.52-3.48 (m, 4H), 3.42-3.31 (m, 1H), 3.27-2.99 (m, 4H), 2.52 (d, J = 2.0 Hz, 1H), 2.46 (s, 5H), 2.37-2.31 (m, 1H), 2.24 (d, J = 7.2 Hz, 3H), 2.11-1.63 (m, 7H), 1.50-1.33 (m, 3H), 1.02-0.92 (m, 3H), 0.89-0.75 (m, 3H) |
| 460 | A | A | C | A | | 1H NMR (400 MHz, DMSO-d6) δ: 8.68 (s, 1H), 7.91 (d, J = 6.0 Hz, 1H), 7.55 (dd, J = 1.6, 8.2 Hz, 1H), 7.44-7.40 (m, 2H), 7.39-7.29 (m, 4H), 7.04 (dd, J = 0.8, 8.4 Hz, 1H), 6.92-6.84 (m, 1H), 6.34 (dd, J = 2.0, 6.0 Hz, 1H), 6.02 (d, J = 2.0 Hz, 1H), 5.94 (s, 1H), 5.45-5.24 (m, 2H), 5.08 (t, J = 7.2 Hz, 1H), 4.78 (s, 2H), 4.66 (dd, J = 6.0, 8.2 Hz, 1H), 4.41-4.32 (m, 4H), 4.25-4.20 (m, 2H), 3.94-3.87 (m, 1H), 3.84-3.75 (m, 1H), 3.70 (br d, J = 5.2 Hz, 2H), 3.74-3.58 (m, 87H), 3.57-3.53 (m, 2H), 3.52-3.45 (m, 2H), 3.39 (s, 4H), 3.28-3.22 (m, 2H), 3.19-3.13 (m, 2H), 2.88-2.73 (m, 4H), 2.70-2.61 (m, 2H), 2.54 (s, 4H), 2.48-2.41 (m, 5H), 2.28-2.19 (m, 3H), 2.14-2.06 (m, 3H), 1.87 (br dd, J = 2.0, 4.4 Hz, 1H), 1.50 (d, J = 7.2 Hz, 3H), 1.04 (d, J = 6.8 Hz, 3H), 0.94 (d, J = 6.8 Hz, 3H) |
| 461 | D | NA | D | NA | 1067.67 | 1H-NMR (300 MHz, CD3OD, ppm) δ 8.85 (s, 1H), 7.74 (s, 1H), 7.42 (m, 5H), 7.24 (s, 1H), 7.14 (s, 1H), 6.92 (d, J = 9 Hz, 2H), 6.58 (s, 1H), 6.41 (s, 1H), 6.23 (s, 1H), 6.07 (s, 1H), 4.59 (s, 1H), 4.44 (s, 1H), 4.41 (m, 6H), 3.56 (m, 3H), 3.29 (s, 1H), 3.22 (s, 4H), 3.10 (s, 4H), 2.46 (m, 2H), 2.82 (s, 6H), 2.17 ( m, 7 H), 2.05 (s, 6H), |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 1.95 (m, 3H), 1.50 (s, 2H), 1.31 (s, 1H), 1.07 (s, 3H), 0.94 (m, 4H) |
| 462 | A | A | C | A | 1067.67 | 1H-NMR (300 MHz, CD3OD, ppm) δ 8.87 (s, 1H), 7.74 (d, J = 9 Hz, 1H), 7.57 (m, 5H), 7.32 (d, J = 9 Hz, 1H), 7.14 (d, J = 9 Hz, 1H), 6.92 (s, 2H), 6.89 (s, 1H), 6.38 (m, 1H), 6.19 (s, 1 H), 6.02 (s, 1H), 4.80 (s, 1H), 4.52 (s, 1H), 4.40 (m, 6H), 3.67 (m, 1H), 3.47 (s, 1H), 3.32 (s, 1 H), 3.27 (m, 1H), 3.18 (m, 2H), 2.94 (s, 4H), 2.45 (m, 5H), 2.25 (m, 6H), 2.04 (s, 5H), 1.94 (m, 3H), 1.67 (s, 2H), 1.30 (s, 3H), 1.07 (s, 1H), 1.05 (s, 3H), 0.90 (m, 4H) |
| 463 | D | NA | D | NA | 1069.66 | 1H NMR (300 MHz, Methanol-d4) δ (ppm): 8.89 (d, J = 9.2 Hz ,1H), 8.61 (d, J = 7.1 Hz, 1H), 8.00 (d, J = 6.2 Hz, 1H), 7.72 (d, J = 7.6 Hz, 1H), 7.55-7.34 (m, 4H), 7.28 (t, J = 7.2 Hz, 1H), 6.93 (t, J = 7.9 Hz, 2H), 6.49 (d, J = 6.2 Hz, 1H), 6.11 (s, 1H), 5.31 (d, J = 5.5 Hz, 1H), 4.97 (d, J = 6.8 Hz, 2H), 4.59 (d, J = 7.0 Hz, 3H), 4.43 (s, 2H), 3.80 (d, J = 9.1 Hz, 3H), 3.71 (s, 6H), 3.65 (d, J = 4.2 Hz, 2H), 3.32 (s, 3H), 3.13 (m, 2H), 2.54-2.44 (m, 8H), 2.41 (s, 3H), 2.05 (s, 7H), 1.51 (d, J = 7.0 Hz, 3H), 1.08 (d, J = 6.7 Hz, 3H), 0.90 (dd, J = 19.4, 6.7 Hz, 3H). |
| 464 | A | A | B | A | 1069.66 | 1H NMR (400 MHz, DMSO-d6) δ (ppm): 14.13 (s, 1H), 9.01 (s, 1H), 8.43 (s, 1H), 8.04-7.95 (m, 2H), 7.57-7.25 (m, 6H), 7.15-6.89 (m, 2H), 6.51 (s, 1H), 6.12-6.03 (m, 3H), 5.15-4.73 (m, 5H), 4.40-4.24 (m, 5H), 3.73 (s, 1H), 3.47 (s, 2H), 3.01 (s, 2H), 2.68 (s, 4H), 2.35 (s, 5H), 2.21 (s, 6H), 1.98 (s, 4H), 1.81 (s, 3H), 1.42 (s, 5H), 1.27 (s, 2H), 0.99-0.83 (m, 7H). |
| 465 | A | A | B | A | 1040.67 | 1H NMR (400 MHz, DMSO-d6) δ: 9.03-8.79 (m, 1H), 8.53-8.37 (m, 2H), 8.18 (d, J = 16.8 Hz, 3H), 8.00 (d, J = 7.6 Hz, 1H), 7.50-7.33 (m, 4H), 7.26 (t, J = 7.2 Hz, 1H), 6.97-6.88 (m, 2H), 6.51 (s, 2H), 6.12-5.87 (m, 1H), 4.97-4.85 (m, 1H), 4.41- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 4.25 (m, 3H), 4.19 (s, 3H), 3.74-3.61 (m, 6H), 3.17 (d, J = 8.8 Hz, 1H), 2.99-2.84 (m, 3H), 2.45 (s, 3H), 2.40-2.32 (m, 3H), 2.22 (d, J = 7.2 Hz, 3H), 2.12 (s, 2H), 2.08-1.97 (m, 5H), 1.87-1.74 (m, 3H), 1.72-1.61 (m, 5H), 1.48-1.35 (m, 3H), 0.95 (d, J = 6.4 Hz, 5H), 0.85-0.74 (m, 3H). |
| 466 | D | NA | D | NA | 1040.65 | 1H NMR (400 MHz, DMSO-d6) δ: 9.02-8.89 (m, 1H), 8.48 (s, 1H), 8.32 (d, J = 7.6 Hz, 1H), 8.19 (d, J = 9.6 Hz, 2H), 8.14 (s, 1H), 8.00 (d, J = 7.2 Hz, 1H), 7.51-7.23 (m, 5H), 6.96-6.88 (m, 2H), 6.53 (s, 2H), 6.17-5.99 (m, 1H), 5.16-4.82 (m, 2H), 4.45-4.11 (m, 6H), 3.78-3.45 (m, 6H), 3.25-3.02 (m, 2H), 2.96-2.80 (m, 1H), 2.57 (s, 2H), 2.47-2.42 (m, 5H), 2.31-2.01 (m, 9H), 1.96-1.54 (m, 8H), 1.48-1.31 (m, 3H), 0.96 (d, J = 6.4 Hz, 5H), 0.84-0.73 (m, 3H). |
| 467 | A | A | C | A | 1040.66 | 1H NMR (400 MHz, DMSO-d6) δ: 9.00-8.78 (m, 1H), 8.48 (s, 1H), 8.41 (d, J = 7.6 Hz, 1H), 8.20 (d, J = 4.0 Hz, 2H), 7.99 (d, J = 7.2 Hz, 1H), 7.48-7.24 (m, 5H), 6.96-6.89 (m, 2H), 6.54 (s, 2H), 6.10-5.90 (m, 1H), 5.14-4.86 (m, 2H), 4.42-4.15 (m, 6H), 3.73-3.64 (m, 2H), 3.64-3.55 (m, 2H), 3.46 (s, 2H), 3.21 (s, 2H), 2.96-2.78 (m, 3H), 2.56 (s, 1H), 2.51-2.49 (m, 1H), 2.45 (s, 3H), 2.37-2.11 (m, 8H), 2.11-1.86 (m, 4H), 1.81-1.61 (m, 6H), 1.47-1.33 (m, 3H), 1.08-0.92 (m, 5H), 0.85-0.77 (m, 3H). |
| 468 | D | NA | D | NA | 1040.66 | 1H NMR (400 MHz, DMSO-d6) δ: 9.01-8.88 (m, 1H), 8.47 (s, 1H), 8.32 (d, J = 7.6 Hz, 1H), 8.20 (d, J = 2.4 Hz, 2H), 8.13 (s, 1H), 7.99 (dd, J1 = 1.6, J2 = 8.4 Hz, 1H), 7.53-7.18 (m, 5H), 6.98-6.87 (m, 2H), 6.54 (s, 2H), 6.15-6.03 (m, 1H), 5.13-4.83 (m, 2H), 4.54-4.30 (m, 3H), 4.29-4.14 (m, 3H), 3.75 (d, J = 8.8 Hz, 1H), 3.64-3.52 (m, 2H), 3.48 (dd, J1 = 4.4, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | J2 = 10.4 Hz, 4H), 3.31-3.28 (m, 2H), 2.93-2.81 (m, 2H), 2.52 (d, J = 1.6 Hz, 2H), 2.46-2.44 (m, 3H), 2.36-2.14 (m, 7H), 2.13-1.87 (m, 4H), 1.82-1.57 (m, 6H), 1.48-1.32 (m, 3H), 0.96 (d, J = 6.4 Hz, 5H), 0.84-0.72 (m, 3H). |
| 469 | D | NA | D | NA | 1121.73 | 1H NMR (400 MHz, DMSO-d6) δ: 9.06-8.86 (m, 1H), 8.29-8.16 (m, 1H), 7.92 (br d, J = 7.6 Hz, 1H), 7.77 (br d, J = 4.8 Hz, 1H), 7.67-7.47 (m, 2H), 7.46-7.39 (m, 2H), 7.33 (br d, J = 7.2 Hz, 1H), 7.28-7.19 (m, 1H), 6.93-6.81 (m, 2H), 6.52 (br d, J = 5.2 Hz, 1H), 6.20-6.09 (m, 2H), 5.97 (br s, 2H), 5.24-5.08 (m, 1H), 5.01-4.85 (m, 1H), 4.49 (br s, 2H), 4.43 (br s, 1H), 4.29 (br dd, J = 1.6, 3.6 Hz, 1H), 3.69 (br d, J = 8.4 Hz, 1H), 3.55 (br s, 3H), 3.25 (br s, 4H), 3.02 (br d, J = 12.0 Hz, 2H), 2.97-2.82 (m, 2H), 2.68 (br s, 3H), 2.46 (br s, 6H), 2.34 (br s, 1H), 2.32-2.24 (m, 2H), 2.22-2.11 (m, 5H), 2.10-2.02 (m, 2H), 1.98 (br d, J = 1.2 Hz, 3H), 1.88-1.72 (m, 5H), 1.65 (ddd, J = 2.4, 4.4, 7.2 Hz, 1H), 1.52-1.29 (m, 7H), 0.97 (br d, J = 5.6 Hz, 2H), 0.89-0.71 (m, 4H) |
| 470 | D | NA | D | NA | 1069.66 | 1H NMR (400 MHz, Methanol-d4) δ (ppm): 8.87 (s, 1H), 8.22 (d, J = 2.4 Hz, 1H), 7.71 (dt, J = 7.9, 2.8 Hz, 1H), 7.53-7.33 (m, 5H), 7.32-7.24 (m, 1H), 6.93 (t, J = 8.0 Hz, 2H), 6.54 (t, J = 2.8 Hz, 1H), 6.10 (s, 1H), 5.16-4.91 (m, 3H), 4.64-4.55 (m, 3H), 4.46-4.40 (m, 2H), 3.80 (d, J = 9.2 Hz, 1H), 3.73 (d, J = 10.4 Hz, 2H), 3.69-3.36 (m, 8H), 3.26-3.16 (m, 3H), 2.63-2.50 (m, 4H), 2.47 (brs, 3H), 2.44-2.36 (m, 1H), 2.33-2.14 (m, 5H), 2.13-2.03 (m, 2H), 1.99-1.90 (m, 3H), 1.50 (d, J = 7.0 Hz, 3H), 1.07 (d, J = 6.6 Hz, 3H), 0.94 (dd, J = 12.4, 6.7 Hz, 3H). |
| 471 | A | A | C | A | 1069.65 | 1H NMR (300 MHz, DMSO-d6) δ (ppm): 14.15 (s, 1H), 9.00 (s, 1H), 8.41 (d, J = 7.6 Hz, 1H), 8.29 (d, J = 2.3 Hz, 1H), 7.97-7.88 (m, 1H), |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 7.55-7.32 (m, 5H), 7.24 (t, J = 7.8 Hz, 1H), 6.87 (t, J = 9.1 Hz, 2H), 6.49 (s, 1H), 6.10-6.01 (m, 3H), 5.10 (d, J = 3.8 Hz, 1H), 5.06-4.88 (m, 2H), 4.84 (brs, 2H), 4.44-4.26 (m, 3H), 4.25-4.22 (m, 2H), 3.74-3.61(m, 2H), 3.49-3.43 (m, 1H), 3.07 (d, J = 11.5 Hz, 2H), 2.77 (brs, 3H), 2.67 (brs, 2H), 2.48-2.38 (m, 7H), 2.30-2.11 (m, 6H), 2.08-1.95 (m, 3H), 1.85-1.76 (m, 3H), 1.49-1.36 (m, 6H), 0.97 (d, J = 6.4 Hz, 3H), 0.83 (t, J = 8.6 Hz, 3H). |
| 472 | D | NA | D | NA | 1119.74 | 1H NMR: (400 MHz, DMSO-d6) δ: 9.02-8.96 (m, 1H), 8.21-8.15 (m, 2H), 7.92 (d, J = 8.0 Hz, 1H), 7.76 (d, J = 6.0 Hz, 1H), 7.53-7.46 (m, 2H), 7.45-7.39 (m, 2H), 7.32 (d, J = 8.4 Hz, 1H), 7.26-7.19 (m, 1H), 6.91-6.82 (m, 2H), 6.52 (dd, J = 1.6, 6.0 Hz, 1H), 6.16-6.10 (m, 2H), 5.97 (s, 2H), 5.18 (quin, J = 6.8 Hz, 1H), 5.08-4.94 (m, 1H), 4.89 (quin, J = 7.2 Hz, 1H), 4.53-4.47 (m, 2H), 4.42 (t, J = 7.6 Hz, 1H), 4.32-4.23 (m, 1H), 3.68 (br d, J = 8.8 Hz, 1H), 3.61 (br d, J = 3.2 Hz, 2H), 3.49-3.38 (m, 2H), 3.30-3.21 (m, 3H), 3.02 (br d, J = 11.6 Hz, 2H), 2.86 (br d, J = 10.4 Hz, 2H), 2.79-2.67 (m, 2H), 2.53 (d, J = 2.0 Hz, 2H), 2.48-2.44 (m, 5H), 2.32-2.22 (m, 1H), 2.22-2.09 (m, 6H), 2.08-1.92 (m, 5H), 1.81 (ddd, J = 5.2, 7.2, 12.8 Hz, 1H), 1.68-1.56 (m, 4H), 1.46 (br d, J = 7.2 Hz, 1H), 1.36 (d, J = 7.2 Hz, 3H), 1.09 (br dd, J = 6.0, 12.0 Hz, 6H), 0.96 (d, J = 6.8 Hz, 2H), 0.83 (br d, J = 6.8 Hz, 3H), 0.75 (d, J = 6.8 Hz, 1H). |
| 473 | A | A | A | A | 1119.74 | 1H NMR (400 MHz, DMSO-d6) δ: 8.98 (s, 1H), 8.38 (d, J = 7.6 Hz, 1H), 8.18 (s, 1H), 7.91 (d, J = 7.6 Hz, 1H), 7.76 (d, J = 6.0 Hz, 1H), 7.50-7.41 (m, 3H), 7.39-7.33 (m, 2H), 7.26-7.18 (m, 1H), 6.90-6.80 (m, 2H), 6.51 (dd, J = 1.6, 6.0 Hz, 1H), 6.16-6.07 (m, 2H), 5.96 (s, 2H), 5.17 (quin, J = 6.4 Hz, 1H), 5.06-4.84 (m, |

TABLE 2C-continued

| Ex. # | *BRM DC$_{50}$ (nM) | **BRM D$_{max}$ (%)† | *BRG1 DC$_{50}$ (nM) | **BRG1 D$_{max}$ (%)† | Observed Mass (2nd Observed Mass) | HNMR |
|---|---|---|---|---|---|---|
| | | | | | | 2H), 4.48 (br s, 2H), 4.36 (t, J = 7.6 Hz, 1H), 4.28 (br s, 1H), 3.71 (br dd, J = 4.2, 10.4 Hz, 1H), 3.63-3.53 (m, 4H), 3.46-3.36 (m, 3H), 3.25 (br d, J = 11.2 Hz, 3H), 3.01 (br d, J = 11.2 Hz, 2H), 2.85 (br d, J = 10.4 Hz, 2H), 2.72 (br t, J = 11.6 Hz, 2H), 2.45 (s, 4H), 2.22-2.09 (m, 6H), 2.05-1.91 (m, 5H), 1.79 (ddd, J = 4.8, 8.0, 12.8 Hz, 1H), 1.63 (br t, J = 11.6 Hz, 4H), 1.56-1.41 (m, 2H), 1.39-1.27 (m, 3H), 1.17-1.04 (m, 6H), 0.99-0.90 (m, 3H), 0.85-0.75 (m, 3H). |
| 474 | A | A | A | A | 1121.72 | 1H NMR (400 MHz, DMSO-d6) δ: 8.99 (s, 1H), 8.39 (d, J = 7.6 Hz, 1H), 7.92 (d, J = 7.6 Hz, 1H), 7.76 (d, J = 6.0 Hz, 1H), 7.50 (s, 1H), 7.44 (d, J = 8.0 Hz, 2H), 7.41-7.35 (m, 2H), 7.23 (t, J = 7.6 Hz, 1H), 6.91-6.81 (m, 2H), 6.52 (br d, J = 5.2 Hz, 1H), 6.16-6.08 (m, 2H), 6.02-5.92 (m, 2H), 5.10 (d, J = 3.6 Hz, 1H), 4.99-4.89 (m, 1H), 4.49 (br s, 2H), 4.37 (t, J = 7.6 Hz, 1H), 4.29 (br d, J = 2.0 Hz, 1H), 3.72 (dd, J = 4.4, 10.4 Hz, 1H), 3.57 (br d, J = 10.0 Hz, 2H), 3.52-3.36 (m, 5H), 3.25 (br d, J = 11.2 Hz, 2H), 3.02 (br d, J = 11.6 Hz, 2H), 2.93 (br t, J = 10.0 Hz, 2H), 2.71-2.62 (m, 2H), 2.46 (s, 3H), 2.40-2.32 (m, 3H), 2.16 (br dd, J = 6.8, 18.0 Hz, 6H), 2.09-1.89 (m, 6H), 1.79 (ddd, J = 5.2, 8.0, 12.4 Hz, 5H), 1.68-1.57 (m, 1H), 1.49-1.34 (m, 7H), 1.00-0.91 (m, 3H), 0.86-0.75 (m, 3H) |
| 475 | D | NA | D | NA | 1122.72 | 1H NMR: (400 MHz, DMSO-d6) δ: 9.13-8.90 (m, 1H), 8.64-8.43 (m, 1H), 8.25 (d, J = 7.6 Hz, 1H), 8.20 (s, 1H), 7.92 (d, J = 8.0 Hz, 1H), 7.76 (d, J = 6.0 Hz, 2H), 7.70-7.65 (m, 1H), 7.50 (s, 1H), 7.23 (t, J = 7.6 Hz, 1H), 6.95-6.79 (m, 2H), 6.52 (br d, J = 4.8 Hz, 1H), 6.20-6.07 (m, 2H), 5.96 (s, 2H), 5.23-5.00 (m, 1H), 4.99-4.86 (m, 1H), 4.49 (br s, 2H), 4.41 (t, J = 7.6 Hz, 1H), 4.31-4.21 (m, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 1H), 3.68 (d, J = 8.8 Hz, 1H), 3.59-3.50 (m, 5H), 3.28-3.22 (m, 7H), 3.02 (br d, J = 11.6 Hz, 2H), 2.97-2.81 (m, 2H), 2.67-2.65 (m, 3H), 2.43-2.37 (m, 3H), 2.26 (br dd, J = 7.2, 15.2 Hz, 1H), 2.16 (br dd, J = 6.8, 16.8 Hz, 5H), 2.10-2.01 (m, 3H), 2.00-1.92 (m, 2H), 1.87-1.70 (m, 5H), 1.68-1.58 (m, 1H), 1.53-1.33 (m, 7H), 0.96 (d, J = 6.4 Hz, 2H), 0.85-0.79 (m, 3H), 0.75 (d, J = 6.8 Hz, 1H) |
| 476 | A | A | C | A | 1122.72 | 1HNMR: (400 MHz, DMSO-d6) δ: 9.00 (s, 1H), 8.53 (d, J = 1.6 Hz, 1H), 8.47 (d, J = 7.2 Hz, 1H), 7.92 (d, J = 8.0 Hz, 1H), 7.83-7.74 (m, 2H), 7.73-7.67 (m, 1H), 7.50 (s, 1H), 7.26-7.19 (m, 1H), 6.91-6.81 (m, 2H), 6.55-6.48 (m, 1H), 6.16-6.08 (m, 2H), 6.01-5.92 (m, 2H), 5.24-4.98 (m, 2H), 4.94 (br t, J = 7.2 Hz, 1H), 4.49 (br s, 2H), 4.36 (t, J = 7.6 Hz, 1H), 4.31-4.24 (m, 1H), 3.71 (br dd, J = 4.0, 10.8 Hz, 1H), 3.57 (br d, J = 10.0 Hz, 2H), 3.52-3.38 (m, 4H), 3.25 (br d, J = 11.2 Hz, 2H), 3.02 (br d, J = 12.0 Hz, 2H), 2.94 (br t, J = 9.6 Hz, 2H), 2.70 (br s, 1H), 2.66 (s, 3H), 2.47-2.36 (m, 2H), 2.30-2.10 (m, 7H), 2.08 (s, 1H), 1.79 (br dd, J = 4.8, 8.2 Hz, 5H), 1.70-1.57 (m, 1H), 1.52-1.33 (m, 7H), 1.24 (s, 1H), 0.95 (br d, J = 6.4 Hz, 3H), 0.79 (d, J = 6.8 Hz, 3H) |
| 477 | D | NA | D | NA | 1104.76 | 1H NMR: (400 MHz, DMSO-d6) δ: 8.93-8.24 (m, 1H), 7.91 (d, J = 6.8 Hz, 1H), 7.75 (d, J = 6.0 Hz, 1H), 7.50-7.40 (m, 2H), 7.39-7.32 (m, 3H), 7.27-7.19 (m, 2H), 6.93-6.79 (m, 3H), 6.55-6.45 (m, 1H), 6.17-6.08 (m, 2H), 5.97 (s, 2H), 5.16 (m, 1H), 5.10 (d, J = 4.0 Hz, 1H), 4.97-4.89 (m, 1H), 4.55-4.46 (m, 2H), 4.42 (t, J = 8.0 Hz, 1H), 4.27 (m, 1H), 3.88-3.79 (m, 1H), 3.68 (d, J = 8.8 Hz, 1H), 3.56-3.48 (m, 4H), 3.46-3.41 (m, 4H), 3.24 (d, J = 12.0 Hz, 2H), 3.01 (d, J = 12.0 Hz, 2H), 2.97-2.78 (m, 2H), 2.71- |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 2.61 (m, 3H), 2.38 (s, 2H), 2.35-2.30 (m, 3H), 2.29-2.25 (m, 4H), 2.22-2.08 (m, 6H), 2.07-1.90 (m, 4H), 1.86-1.71 (m, 4H), 1.46 (d, J = 7.2 Hz, 1H), 1.36 (d, J = 7.2 Hz, 3H), 0.95 (d, J = 6.8 Hz, 2H), 0.81 (d, J = 6.8 Hz, 3H), 0.75 (d, J = 6.8 Hz, 1H) |
| 478 | A | A | C | A | 1104.76 | 1H NMR: (400 MHz, DMSO-d6) δ: 8.80-8.40 (m, 1H), 7.91 (d, J = 7.6 Hz, 1H), 7.76 (d, J = 6.0 Hz, 1H), 7.49 (s, 1H), 7.44-7.33 (m, 4H), 7.27-7.19 (m, 2H), 6.81-6.93 (m, 3H), 6.51 (d, J = 4.8 Hz, 1H), 6.16-6.08 (m, 2H), 6.02-5.90 (m, 2H), 5.24-4.89 (m, 3H), 4.49 (s, 2H), 4.40-4.33 (m, 1H), 4.28 (s, 1H), 3.72 (dd, J = 10.8, 4.0 Hz, 1H), 3.56 (d, J = 9.6 Hz, 2H), 3.50-3.39 (m, 4H), 3.25 (d, J = 12.0 Hz, 3H), 3.01 (d, J = 12.0 Hz, 2H), 2.93 (m, 2H), 2.74 (s, 1H), 2.44-2.38 (m, 3H), 2.28-2.26 (s, 3H), 2.33-1.91 (m, 12H), 1.88-1.75 (m, 5H), 1.67 (s, 1H), 1.53-1.23 (m, 7 H), 1.00-0.92 (m, 3H), 0.84-0.76 (m, 3H) |
| 479 | D | NA | D | NA | 1089.63 | 1H NMR (400 MHz, DMSO-d6,ppm) δ 8.99 (m, J = 9.0, 3.1 Hz, 1H), 8.49 (s, 1H), 8.38 (m, J = 7.5, 2.3 Hz, 1H), 8.16 (s, 1H), 8.04 (m, J = 5.4, 2.8 Hz, 1H), 7.91 (d, J = 7.9 Hz, 1H), 7.80-7.62 (m, 3H), 7.50 (s, 1H), 7.26-7.10 (m, 3H), 6.85 (m, J = 13.5, 7.6 Hz, 2H), 6.54 (m, J = 6.2, 2.1 Hz, 1H), 6.18 (d, J = 2.1 Hz, 1H), 6.07 (d, J = 3.1 Hz, 1H), 5.97 (s, 2H), 5.30 (p, J = 6.0 Hz, 1H), 4.92 (m, J = 12.7, 6.9, 5.9 Hz, 2H), 4.50 (s, 2H), 4.41 (t, J = 7.8 Hz, 1H), 4.25 (s, 1H), 4.16-4.08 (m, 2H), 3.74 (d, J = 8.7 Hz, 1H), 3.55 (d, J = 10.1 Hz, 1H), 3.45 (m, J = 9.3, 3.5 Hz, 2H), 3.24 (t, J = 9.8 Hz, 4H), 3.02 (d, J = 11.6 Hz, 2H), 2.65 (d, J = 8.1 Hz, 3H), 2.54-2.21 (d, 8H), 1.74 (m, J = 12.6, 7.9, 4.9 Hz, 2H), 1.48 (d, J = 7.0 Hz, 1H), 1.38 (m, J = 7.2, 3.2 Hz, 2H), 1.23 (s, 1H), 1.10 (d, J = 6.2 Hz, 2H), 1.09-0.96 (m, 3H), 0.83 |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | (s, 3H), 0.81-0.72 (m, 1H). |
| 480 | A | A | D | A | 1089.63 | 1H NMR (400 MHz, DMSO-d6,ppm): δ 8.99 (s, 1H), 8.52 (d, J = 2.3 Hz, 1H), 8.48 (d, J = 7.4 Hz, 1H), 8.05 (d, J = 2.8 Hz, 1H), 7.91 (d, J = 7.9 Hz, 1H), 7.81-7.74 (m, 2H), 7.69 (d, J = 8.2 Hz, 1H), 7.50 (s, 1H), 7.26-7.12 (m, 3H), 6.85 (m, J = 13.4, 7.8 Hz, 2H), 6.57-6.51 (m, 1H), 6.18 (d, J = 2.1 Hz, 1H), 6.08 (s, 1H), 5.97 (s, 2H), 5.31 (p, J = 6.1 Hz, 1H), 4.93 (t, J = 6.7 Hz, 2H), 4.36-4.28 (t, J = 7.9 Hz, 2H), 4.15 (m, J = 21.3, 10.4, 5.4 Hz, 1H), 3.74-3.60 (m, 1H), 3.49-3.40 (m, 2H), 3.25 (d, J = 11.5 Hz, 2H), 3.02 (d, J = 11.6 Hz, 2H), 2.65 (s, 3H), 2.61 (s, 2H), 2.54 (d, J = 5.8 Hz, 3H), 2.29-2.13 (m, 3H), 2.12-2.05(m, 4H), 2.10 (d, J = 20.2 Hz, 1H), 2.00-1.93 (m, 3H), 1.76 (m, J = 13.3, 8.3, 4.7 Hz, 2H), 1.48 (d, J = 7.1 Hz, 3H), 1.41 (d, J = 7.0 Hz, 1H), 1.11 (td, J = 12.1, 10.7, 6.3 Hz, 1H), 1.07-0.96 (m, 1H), 0.95 (d, J = 6.7 Hz, 3H), 0.85-0.76 (m, 3H). |
| 481 | A | A | D | NA | 955.56 | 1H NMR (400 MHz, MeOD-d4) δ: 8.78-8.73 (m, 1H), 8.34 (br s, 1H), 7.75-7.52 (m, 2H), 7.37 (s, 1H), 7.35-7.26 (m, 3H), 7.20 (s, 1H), 7.12 (t, J = 7.6 Hz, 1H), 6.84-6.73 (m, 2H), 6.44 (br d, J = 6.0 Hz, 1H), 6.13-6.08 (m, 1H), 6.04 (s, 1H), 4.97-4.87 (m, 1H), 4.64-4.52 (m, 1H), 4.47-4.25 (m, 4H), 4.05-3.95 (m, 1H), 3.83-3.69 (m, 1H), 3.66-3.38 (m, 3H), 3.28-3.22 (m, 3H), 3.17-3.12 (m, 1H), 3.07-2.89 (m, 3H), 2.77-2.63 (m, 2H), 2.41-2.34 (m, 3H), 2.31 (s, 1H), 2.17-2.13 (m, 1H), 2.12-2.08 (m, 3H), 2.06-2.02 (m, 2H), 1.95-1.77 (m, 3H), 1.52-1.36 (m, 3H), 1.04-0.93 (m, 3H). |
| 482 | D | NA | D | NA | 955.56 | 1H NMR (400 MHz, MeOD-d4) δ: 8.90-8.86 (m, 1H), 8.44 (br s, 1H), 7.81-7.69 (m, 2H), 7.50 (s, 1H), 7.45-7.32 (m, 4H), 7.27-7.21 (m, 1H), 6.93- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 6.87 (m, 2H), 6.57 (dd, J = 1.9, 6.2 Hz, 1H), 6.29 (s, 1H), 6.24-6.15 (m, 1H), 5.04-4.93 (m, 1H), 4.83-4.66 (m, 1H), 4.64-4.49 (m, 4H), 4.48-4.36 (m, 1H), 4.22 (d, J = 8.0 Hz, 1H), 3.82-3.53 (m, 3H), 3.44-3.35 (m, 3H), 3.31-3.26 (m, 2H), 3.21-3.12 (m, 2H), 2.97-2.81 (m, 2H), 2.61-2.51 (m, 1H), 2.50-2.45 (m, 3H), 2.29-2.27 (m, 1H), 2.24 (s, 3H), 2.22-2.14 (m, 3H), 2.11-2.06 (m, 1H), 2.01-1.92 (m, 1H), 1.58-1.44 (m, 3H), 0.98-0.83 (m, 3H) |
| 483 | D | NA | D | NA | 1118.66 | 1H NMR: (400 MHz, DMSO-d6) δ: 9.02-8.96 (m, 1H), 8.40 (br d, J = 8.0 Hz, 1H), 7.97-7.90 (m, 1H), 7.66-7.57 (m, 1H), 7.52-7.47 (m, 1H), 7.46-7.41 (m, 2H), 7.40-7.31 (m, 3H), 7.03-6.93 (m, 2H), 6.84-6.72 (m, 2H), 6.27 (d, J = 7.2 Hz, 1H), 6.22 (s, 1H), 5.26-5.18 (m, 1H), 4.93-4.75 (m, 3H), 4.66-4.48 (m, 3H), 4.47-4.40 (m, 1H), 4.34-4.23 (m, 3H), 3.81 (br d, J = 8.8 Hz, 4H), 3.63-3.56 (m, 6H), 3.45 (br dd, J = 4.4, 9.6 Hz, 2H), 3.23-3.08 (m, 4H), 2.45 (s, 3H), 2.44-2.40 (m, 2H), 2.31-2.20 (m, 3H), 2.12-1.94 (m, 4H), 1.93-1.72 (m, 3H), 1.63-1.50 (m, 1H), 1.36 (d, J = 7.2 Hz, 3H), 0.98 (d, J = 6.8 Hz, 3H), 0.84 (d, J = 6.8 Hz, 3H) |
| 484 | A | A | C | A | 1118.66 | 1H NMR (400 MHz, DMSO-d6) δ: 9.02-8.97 (m, 1H), 8.42 (d, J = 7.6 Hz, 1H), 7.97 (d, J = 7.2 Hz, 1H), 7.56 (d, J = 7.6 Hz, 1H), 7.51 (s, 1H), 7.49-7.45 (m, 1H), 7.44 (s, 1H), 7.42-7.35 (m, 3H), 7.05 (d, J = 8.4 Hz, 2H), 6.98 (t, J = 7.6 Hz, 1H), 6.90-6.86 (m, 1H), 6.29 (s, 1H), 6.24 (s, 1H), 5.27-5.19 (m, 1H), 4.97-4.83 (m, 3H), 4.75-4.56 (m, 3H), 4.42-4.24 (m, 3H), 3.76-3.42 (m, 7H), 3.38-3.12 (m, 4H), 3.07-2.82 (m, 1H), 2.55-2.52 (m, 5H), 2.47-2.39 (m, 5H), 2.30-2.17 (m, 3H), 2.10-1.88 (m, 5H), 1.84-1.60 (m, 3H), 1.49-1.36 (m, 3H), 1.01-0.94 |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | (m, 3H), 0.89-0.78 (m, 3H |
| 485 | D | NA | D | NA | 1068.66 | 1H NMR: (400 MHz, DMSO-d6) δ: 9.03-8.96 (m, 1H), 8.49 (d, J = 1.6 Hz, 1H), 8.35 (d, J = 7.6 Hz, 1H), 7.91 (d, J = 7.2 Hz, 1H), 7.79-7.63 (m, 3H), 7.49 (s, 1H), 7.22 (t, J = 7.6 Hz, 1H), 6.89-6.80 (m, 2H), 6.52 (dd, J = 1.6, 6.0 Hz, 1H), 6.16-6.10 (m, 1H), 6.06 (s, 1H), 5.97 (s, 2H), 5.25-5.01 (m, 2H), 4.97-4.82 (m, 1H), 4.54-4.45 (m, 2H), 4.44-4.35 (m, 1H), 4.32-4.21 (m, 2H), 4.19-4.07 (m, 2H), 3.74 (d, J = 8.8 Hz, 1H), 3.60-3.52 (m, 1H), 3.47 (br dd, J = 4.8, 10.8 Hz, 1H), 3.24 (br d, J = 11.6 Hz, 2H), 3.18-3.09 (m, 1H), 3.01 (br d, J = 11.6 Hz, 2H), 2.67-2.63 (m, 3H), 2.31-2.23 (m, 5H), 2.20-2.14 (m, 2H), 2.08-2.02 (m, 1H), 1.99-1.82 (m, 5H), 1.78-1.66 (m, 3H), 1.64-1.46 (m, 3H), 1.38 (d, J = 7.2 Hz, 2H), 1.34-1.24 (m, 1H), 1.15-1.03 (m, 2H), 0.99-0.88 (m, 4H), 0.86-0.78 (m, 3H), 0.75 (d, J = 6.8 Hz, 1H). |
| 486 | A | A | D | A | 1068.66 | 1H NMR: (400 MHz, DMSO-d6) δ: 9.00 (s, 1H), 8.55-8.46 (m, 2H), 7.92 (d, J = 7.2 Hz, 1H), 7.80-7.74 (m, 2H), 7.73-7.66 (m, 1H), 7.49 (s, 1H), 7.26-7.19 (m, 1H), 6.90-6.80 (m, 2H), 6.52 (dd, J = 1.6, 6.0 Hz, 1H), 6.13 (d, J = 1.6 Hz, 1H), 6.07 (s, 1H), 5.97 (s, 2H), 5.22-5.04 (m, 2H), 4.93 (quin, J = 7.2 Hz, 1H), 4.49 (br s, 2H), 4.35 (t, J = 8.0 Hz, 1H), 4.30-4.22 (m, 2H), 4.19-4.10 (m, 2H), 3.72-3.60 (m, 2H), 3.47-3.41 (m, 2H), 3.24 (br d, J = 11.2 Hz, 2H), 3.19-3.12 (m, 1H), 3.01 (br d, J = 11.2 Hz, 2H), 2.65 (s, 3H), 2.30-2.15 (m, 7H), 2.06-1.87 (m, 5H), 1.79-1.69 (m, 3H), 1.59 (q, J = 6.4 Hz, 2H), 1.50-1.30 (m, 4H), 1.20-1.06 (m, 2H), 1.01-0.89 (m, 5H), 0.85-0.74 (m, 3H) |
| 487 | D | NA | D | NA | 1067.67 | 1H NMR: (400 MHz, DMSO-d6) δ: 9.01-8.96 (m, 1H), 8.36 (s, 1H), 8.29 (d, J = 8.0 Hz, 1H), 7.94-7.88 (m, 1H), 7.76 |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | (d, J = 6.0 Hz, 1H), 7.50-7.47 (m, 1H), 7.44-7.38 (m, 2H), 7.31 (d, J = 8.4 Hz, 2H), 7.25-7.18 (m, 1H), 6.89-6.81 (m, 2H), 6.52 (dd, J = 2.0, 6.0 Hz, 1H), 6.13 (d, J = 2.8 Hz, 1H), 6.06 (s, 1H), 5.97 (s, 2H), 5.25-4.96 (m, 2H), 4.94-4.80 (m, 1H), 4.51-4.45 (m, 2H), 4.41 (t, J = 7.6 Hz, 1H), 4.31-4.22 (m, 2H), 4.19-4.09 (m, 2H), 3.74 (d, J = 8.8 Hz, 1H), 3.58-3.47 (m, 3H), 3.26 (br s, 2H), 3.18-3.13 (m, 1H), 3.01 (br d, J = 11.6 Hz, 2H), 2.47-2.44 (m, 3H), 2.31-2.21 (m, 5H), 2.21-2.14 (m, 2H), 2.09-2.01 (m, 1H), 1.97-1.83 (m, 4H), 1.77 (ddd, J = 4.8, 7.6, 12.8 Hz, 1H), 1.69 (br d, J = 13.2 Hz, 2H), 1.63-1.52 (m, 2H), 1.45 (d, J = 7.2 Hz, 1H), 1.38-1.31 (m, 3H), 1.17-1.03 (m, 2H), 0.98-0.88 (m, 4H), 0.82 (d, J = 6.8 Hz, 3H), 0.75 (d, J = 6.8 Hz, 1H) |
| 488 | A | A | C | A | 1067.67 | 1H NMR (400 MHz, DMSO-d6) δ: 9.01-8.96 (m, 1H), 8.45-8.38 (m, 1H), 7.92 (dd, J = 1.2, 8.0 Hz, 1H), 7.77 (d, J = 6.0 Hz, 1H), 7.50 (s, 1H), 7.44 (d, J = 8.4 Hz, 2H), 7.39-7.33 (m, 2H), 7.26-7.19 (m, 1H), 6.90-6.80 (m, 2H), 6.52 (dd, J = 2.0, 6.0 Hz, 1H), 6.13 (d, J = 2.0 Hz, 1H), 6.07 (s, 1H), 5.97 (s, 2H), 5.23-5.00 (m, 2H), 4.97-4.84 (m, 1H), 4.49 (br s, 2H), 4.36 (t, J = 8.0 Hz, 1H), 4.32-4.24 (m, 2H), 4.15 (br t, J = 6.8 Hz, 2H), 3.69 (dd, J = 4.4, 10.8 Hz, 1H), 3.63 (d, J = 9.6 Hz, 1H), 3.45-3.42 (m, 2H), 3.24 (br d, J = 11.2 Hz, 2H), 3.19-3.14 (m, 1H), 3.01 (br d, J = 11.6 Hz, 2H), 2.45 (s, 3H), 2.31-2.14 (m, 7H), 2.06-1.87 (m, 5H), 1.82-1.68 (m, 3H), 1.59 (q, J = 6.6 Hz, 2H), 1.47-1.30 (m, 4H), 1.19-1.06 (m, 2H), 1.01-0.89 (m, 5H), 0.84-0.76 (m, 3H) |
| 489 | D | NA | D | NA | 1092.66 | 1H NMR: (400 MHz, DMSO-d6) δ 8.99 (s, 1H), 8.59 (d, J = 7.6 Hz, 1H), 8.42 (d, J = 7.6 Hz, 1H), 7.97 (s, 1H), 7.80 (d, J = 6.0 Hz, 1H), 7.74 (dd, J = 1.6, 7.6 Hz, 1H), 7.48-7.42 (m, 2H), 7.40- |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 7.35 (m, 2H), 7.17-7.10 (m, 1H), 6.89-6.77 (m, 3H), 6.58 (dd, J = 2.0, 6.0 Hz, 1H), 6.22 (d, J = 1.6 Hz, 1H), 6.10 (s, 1H), 5.25-5.15 (m, 1H), 4.92 (quin, J = 7.2 Hz, 1H), 4.54 (br s, 2H), 4.38 (t, J = 7.6 Hz, 1H), 4.33-4.25 (m, 2H), 4.21 (br t, J = 5.6 Hz, 2H), 4.05 (br d, J = 1.6 Hz, 2H), 3.75-3.54 (m, 2H), 3.49-3.42 (m, 1H), 3.32-3.15 (m, 5H), 2.80-2.71 (m, 2H), 2.70-2.61 (m, 2H), 2.46 (s, 3H), 2.38-2.18 (m, 6H), 2.17-2.08 (m, 2H), 2.07-1.88 (m, 3H), 1.84-1.71 (m, 5H), 1.50-1.35 (m, 5H), 1.01-0.91 (m, 3H), 0.88-0.75 (m, 3H) |
| 490 | D | NA | D | NA | 1070.65 | 1H NMR (400 MHz, DMSO-d6) δ 14.12 (s, 1H), 9.22-9.01 (m, 1H), 9.00-8.80 (m, 1H), 8.75-8.51 (m, 1H), 8.50-8.25 (m, 1H), 8.05-7.81 (m, 1H), 7.80-7.60 (m, 1H), 7.55-7.39 (m, 1H), 7.30-7.02 (m, 1H), 7.00-6.65 (m, 2H), 6.50-6.23 (m, 1H), 6.20-6.10 (m, 1H), 6.09-6.05 (m, 1H), 6.00-5.87 (m, 2H), 5.35-5.15 (m, 1H), 5.14-5.02 (m, 1H), 5.00-4.90 (m, 1H), 4.63-4.41 (m, 3H), 4.40-4.10 (m, 4H), 3.80-3.70 (m, 1H), 3.60-3.40 (m, 2H), 3.28-3.15 (m, 3H), 3.09-2.90 (m, 2H), 2.82-2.58 (m, 6H), 2.35-2.21 (m, 5H), 2.20-2.01 (m, 5H), 2.00-1.90 (m, 2H), 1.88-1.69 (m, 3H), 1.56-1.45 (m, 1H), 1.44-1.32 (m, 4H), 1.31-1.20 (m, 1H), 1.10-0.90(m, 3H), 0.85-0.70 (m, 3H). |
| 491 | A | A | D | NA | 1070.65 | 1H NMR (400 MHz, DMSO-d6) δ 14.15 (s, 1H), 9.20-9.01 (m, 1H), 9.00-8.80 (m, 1H), 8.65-8.56 (m, 1H), 8.55-8.30 (m, 1H), 8.00-7.85 (m, 1H), 7.84-7.72 (m, 1H), 7.60-7.35 (m, 1H), 7.30-7.10 (m, 1H), 6.98-6.70 (m, 2H), 6.60-6.40 (m, 1H), 6.20-6.01 (m, 2H), 6.00-5.80 (m, 2H), 5.31-5.14 (m, 1H), 5.13-5.06 (m, 1H), 5.05-4.90 (m, 1H), 4.60-4.52 (m, 2H), 4.51-4.30 (m, 1H), 4.29-4.13(m, 4H), 3.80-3.68 (m, 1H), 3.67-3.55 (m, 1H), 3.54-3.40 (m, 1H), 3.23-3.18 (m, 3H), 3.03-2.97 (m, 2H), 2.78-2.71 |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | (m, 1H), 2.70-2.66 (m, 3H), 2.65-2.60 (m, 2H), 2.32-2.21 (m, 5H), 2.20-2.05 (m, 4H), 2.04-1.92 (m, 3H), 1.86-1.70 (m, 3H), 1.55-1.43 (m, 3H), 1.42-1.36 (m, 2H), 1.35-1.20(m, 1H), 1.06-0.89 (m, 3H), 0.88-0.75(m, 3H). |
| 492 | D | NA | D | NA | 1067.68 | 1H NMR (400 MHz, DMSO-d6, ppm): δ 14.09 (s, 1H), 8.98 (d, J = 7.8 Hz, 1H), 8.30 (d, J = 7.8 Hz, 1H), 7.90-7.89 (m, 1H), 7.66 (d, J = 6.4 Hz, 1H), 7.52-7.48 (m, 1H), 7.46-7.42(m, 2H), 7.31-7.20 (m, 1H), 7.27-7.18 (m, 1H), 6.90-6.81 (m, 2H), 6.30 (s, 1H), 6.08 (s, 1H), 5.99 (s, 2H), 5.73-5.71 (m, 1H), 5.10 (s, 1H), 5.05-4.83 (m, 1H), 4.55-4.38 (m, 3H), 4.26-4.11 (m, 5H), 3.74 (d, J = 8.6 Hz, 1H), 3.59-3.37 (m, 2H), 3.29-3.19(m, 2H), 3.07-2.96(m, 2H), 2.82-2.59 (m, 2H), 2.47-2.45(m, 1H), 2.44-2.43 (m, 3H), 2.31-2.20 (m, 3H), 2.21-2.09 (m, 5H), 2.07 (s, 1H), 2.0-1.91 (m, 3H), 1.83-1.69 (m, 3H), 1.49-1.31 (m, 5H), 1.28-1.09 (m, 2H), 1.08-1.02 (m, 1H), 1.01-0.70 (m, 6H) |
| 493 | A | A | C | A | 1067.68 | 1H NMR (400 MHz, DMSO-d6, ppm): δ 14.11 (s, 1H), 8.98 (s, 1H), 8.40 (d, J = 7.7 Hz, 1H), 7.90 (d, J = 7.9 Hz, 1H), 7.66 (d, J = 6.2 Hz, 1H), 7.48-7.43 (m, 3H), 7.36 (d, J = 7.9 Hz, 2H), 7.22-7.18 (m, 1H), 6.86-6.80 (m, 2H), 6.60-6.48 (m, 1H), 6.23-6.15 (m, 1H), 6.09 (s, 1H), 5.97 (s, 2H), 5.71 (s, 1H), 5.09 (d, J = 3.7 Hz, 1H), 4.95-4.85 (m, 1H), 4.50-4.32 (m, 3H), 4.30-4.16 (m, 4H), 4.12-4.07 (m, 1H), 3.74-3.61 (m, 2H), 3.49-3.39 (m, 1H), 3.11-2.95 (m, 2H), 2.82-2.71(m, 2H), 2.70-2.60 (m, 2H), 2.47-2.41 (m, 3H), 2.29-2.19 (m, 3H), 2.18-2.05 (m, 6H), 2.04-1.88(m, 4H), 1.83-1.70(m, 3H), 1.48-1.31 (m, 5H), 1.21-1.07 (m, 2H), 1.0-0.90 (m, 3H), 0.86-0.75(m, 3H). |
| 494 | A | A | D | A | 943.57 | 1H NMR (400 MHz, DMSO-d6) δ: 8.97 (s, 1H), 8.38 (d, J = 7.6 Hz, 1H), 8.20 (s, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 1H), 7.90 (d, J = 6.8 Hz, 1H), 7.78 (d, J = 6.0 Hz, 1H), 7.50-7.47 (m, 1H), 7.45-7.40 (m, 2H), 7.39-7.31 (m, 2H), 7.21 (t, J = 7.6 Hz, 1H), 6.89-6.80 (m, 2H), 6.55-6.50 (m, 1H), 6.20 (s, 1H), 6.14 (d, J = 1.6 Hz, 1H), 5.96 (s, 2H), 5.07 (s, 1H), 4.91 (t, J = 7.2 Hz, 1H), 4.49 (s, 2H), 4.36 (t, J = 7.6 Hz, 1H), 4.29-4.18 (m, 3H), 3.97 (d, J = 9.6 Hz, 1H), 3.70 (dd, J = 4.4 Hz, J = 10.8 Hz, 1H), 3.26 (s, 3H), 3.13-2.94 (m, 3H), 2.53-2.52 (m, 2H), 2.46-2.42 (m, 4H), 2.17 (s, 5H), 2.05-1.71 (m, 7H), 1.43-1.34 (m, 3H), 0.98 (d, J = 6.8 Hz, 3H) |
| 495 | D | NA | D | NA | 943.57 | 1H NMR (400 MHz, DMSO-d6) δ: 9.00-8.96 (m, 1H), 8.28 (d, J = 3.6 Hz, 1H), 8.26 (s, 1H), 7.92-7.87 (m, 1H), 7.79 (d, J = 6.0 Hz, 1H), 7.50-7.29 (m, 5H), 7.21 (t, J = 7.6 Hz, 1H), 6.89-6.80 (m, 2H), 6.53 (dd, J = 2.0 Hz, J = 6.0 Hz, 1H), 6.29-6.24 (m, 1H), 6.16 (d, J = 1.6 Hz, 1H), 5.96 (s, 2H), 5.28-4.94 (m, 1H), 4.92-4.85 (m, 1H), 4.49 (s, 2H), 4.42 (t, J = 7.6 Hz, 1H), 4.29-4.19 (m, 3H), 4.09 (d, J = 7.2 Hz, 1H), 3.54-3.46 (m, 4H), 3.01 (d, J = 11.2 Hz, 3H), 2.52 (s, 1H), 2.45-2.38 (m, 5H), 2.22-2.09 (m, 6H), 2.08-1.73 (m, 6H), 1.44-1.32 (m, 3H), 0.80-0.72 (m, 3H) |
| 496 | A | A | A | A | 1036.67 | 1H NMR (400 MHz, DMSO-d6) δ: 13.95-13.62 (m, 1H), 8.98 (s, 1H), 8.56-8.48 (m, 1H), 8.38 (d, J = 7.6 Hz, 1H), 8.26-8.15 (m, 2H), 8.01 (dd, J = 1.2, 8.4 Hz, 1H), 7.51-7.42 (m, 2H), 7.40-7.33 (m, 2H), 7.30-7.22 (m, 1H), 6.95-6.87 (m, 2H), 6.50 (s, 2H), 6.12-5.95 (m, 1H), 5.46-5.34 (m, 1H), 5.19-4.99 (m, 1H), 4.91 (quin, J = 7.2 Hz, 1H), 4.36 (t, J = 8.0 Hz, 1H), 4.32-4.21 (m, 2H), 3.71 (dd, J = 4.4, 10.4 Hz, 1H), 3.62-3.50 (m, 3H), 3.46-3.38 (m, 1H), 3.25 (dt, J = 4.4, 8.8 Hz, 1H), 3.08-2.96 (m, 1H), 2.76-2.67 (m, 2H), 2.65- |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 2.57 (m, 2H), 2.45 (s, 3H), 2.29-2.15 (m, 5H), 2.08-1.86 (m, 5H), 1.83-1.65 (m, 8H), 1.64-1.52 (m, 1H), 1.48-1.29 (m, 5H), 1.17-1.02 (m, 2H), 0.99-0.90 (m, 3H), 0.84-0.73 (m, 3H) |
| 497 | A | A | A | A | 1036.67 | 1H NMR (400 MHz, DMSO-d6) δ: 8.98 (s, 1H), 8.53 (s, 1H), 8.38 (d, J = 7.6 Hz, 1H), 8.22 (s, 1H), 8.21-8.16 (m, 2H), 8.01 (dd, J = 1.6, 8.4 Hz, 1H), 7.54-7.33 (m, 4H), 7.31-7.20 (m, 1H), 7.02-6.85 (m, 2H), 6.51 (s, 2H), 6.16-5.88 (m, 1H), 5.50-5.30 (m, 1H), 4.91 (quin, J = 7.2 Hz, 1H), 4.39-4.20 (m, 3H), 3.74-3.69 (m, 1H), 3.59 (br d, J = 12.0 Hz, 3H), 3.45-3.38 (m, 3H), 3.26-3.22 (m, 1H), 3.06-2.99 (m, 1H), 2.75-2.70 (m, 1H), 2.65-2.58 (m, 2H), 2.45 (s, 3H), 2.29-2.17 (m, 5H), 2.08 (br d, J = 6.8 Hz, 2H), 2.04-1.88 (m, 3H), 1.81-1.65 (m, 8H), 1.63-1.53 (m, 1H), 1.47-1.31 (m, 5H), 1.22-1.02 (m, 2H), 1.01-0.90 (m, 3H), 0.86-0.71 (m, 3H) |
| 498 | D | NA | D | NA | 1023.65 | 1H NMR: (400 MHz, DMSO-d6) δ: 9.02-8.89 (m, 1H), 8.21 (d, J = 7.6 Hz, 1H), 7.92 (d, J = 8.0 Hz, 1H), 7.77 (d, J = 6.0 Hz, 1H), 7.62-7.46 (m, 2H), 7.45-7.38 (m, 2H), 7.34-7.31 (m, 1H), 7.23 (t, J = 7.6 Hz, 1H), 6.91-6.80 (m, 2H), 6.55-6.49 (m, 1H), 6.20-6.09 (m, 2H), 5.97 (s, 2H), 5.10 (br s, 1H), 5.05-4.95 (m, 1H), 4.89 (t, J = 7.2 Hz, 1H), 4.53-4.47 (m, 2H), 4.43 (t, J = 7.6 Hz, 1H), 4.32-4.23 (m, 1H), 3.70 (d, J = 8.8 Hz, 1H), 3.61-3.40 (m, 2H), 3.29-3.23 (m, 2H), 3.20-3.07 (m, 4H), 3.02 (br d, J = 11.6 Hz, 2H), 2.53 (br s, 1H), 2.48-2.42 (m, 6H), 2.39 (br d, J = 6.4 Hz, 4H), 2.31-2.23 (m, 1H), 2.22-2.07 (m, 5H), 2.06-1.90 (m, 3H), 1.86-1.76 (m, 1H), 1.70-1.62 (m, 1H), 1.47 (d, J = 7.2 Hz, 1H), 1.36 (d, J = 7.2 Hz, 2H), 0.97 (d, J = 6.8 Hz, 2H), 0.83 (d, J = 6.8 Hz, 3H), 0.76 (d, J = 6.8 Hz, 1H) |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| 499 | A | A | A | A | 1023.65 | 1H NMR (400 MHz, DMSO-d6) δ: 8.99 (s, 1H), 8.39 (d, J = 7.6 Hz, 1H), 7.92 (d, J = 7.6 Hz, 1H), 7.77 (d, J = 6.0 Hz, 1H), 7.50 (s, 1H), 7.44 (d, J = 8.0 Hz, 2H), 7.40-7.35 (m, 2H), 7.23 (t, J = 7.6 Hz, 1H), 6.90-6.82 (m, 2H), 6.52 (br d, J = 6.4 Hz, 1H), 6.18-6.08 (m, 2H), 5.97 (s, 2H), 5.26-5.05 (m, 1H), 5.04-4.86 (m, 2H), 4.49 (br s, 2H), 4.41-4.34 (m, 1H), 4.29 (br s, 1H), 3.76-3.66 (m, 1H), 3.58 (d, J = 10.0 Hz, 1H), 3.42 (br d, J = 10.6 Hz, 1H), 3.31-3.21 (m, 3H), 3.15 (br s, 4H), 3.02 (br d, J = 11.2 Hz, 2H), 2.47-2.39 (m, 10H), 2.26-2.09 (m, 6H), 2.05-1.93 (m, 3H), 1.85-1.74 (m, 1H), 1.71-1.60 (m, 1H), 1.48-1.35 (m, 3H), 1.00-0.91 (m, 3H), 0.80 (br d, J = 6.8 Hz, 3H) |
| 500 | D | NA | D | NA | 1087.66 | 1H NMR (400 MHz, CD3OD-d4) δ: 9.07-9.01 (m, 1H), 8.58-8.50 (m, 1H), 7.95-7.82 (m, 1H), 7.79-7.64 (m, 2H), 7.43 (s, 1H), 7.21 (t, J = 7.6 Hz, 1H), 6.91-6.81 (m, 2H), 6.56-6.48 (m, 1H), 6.13 (s, 1H), 6.05-5.86 (m, 1H), 5.14-5.07 (m, 1H), 5.07-4.98 (m, 1H), 4.64-4.48 (m, 4H), 4.42-4.14 (m, 3H), 3.89-3.58 (m, 3H), 3.37 (s, 1H), 3.31 (br s, 1H), 3.15-3.05 (m, 2H), 2.87-2.71 (m, 3H), 2.67-2.60 (m, 1H), 2.59-2.49 (m, 3H), 2.43-2.02 (m, 14H), 1.90-1.73 (m, 2H), 1.64-1.46 (m, 5H), 1.09-1.00 (m, 2H), 0.93-0.87 (m, 3H), 0.84 (d, J = 6.8 Hz, 1H) |
| 501 | A | A | D | NA | 1087.65 | 1H NMR (400 MHz, CD3OD-d4) δ: 9.08-9.01 (m, 1H), 8.51-8.41 (m, 1H), 7.79-7.60 (m, 3H), 7.48-7.42 (m, 1H), 7.26-7.18 (m, 1H), 6.92-6.83 (m, 2H), 6.56-6.50 (m, 1H), 6.13 (s, 1H), 6.03 (d, J = 8.8 Hz, 1H), 5.16-5.01 (m, 2H), 4.60-4.42 (m, 4H), 4.42-4.27 (m, 3H), 3.88-3.59 (m, 3H), 3.37-3.34 (m, 2H), 3.12 (d, J = 11.6 Hz, 2H), 2.89-2.70 (m, 4H), 2.57-2.53 (m, 3H), 2.48-2.10 (m, |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 13H), 2.01-1.81 (m, 3H), 1.67-1.52 (m, 5H), 1.09-1.03 (m, 3H), 0.94-0.88 (m, 3H) |
| 502 | A | A | C | A | 1086.66 | 1H NMR: (400 MHz, DMSO-d6) δ: 10.09-9.63 (m, 1H), 9.07-8.94 (m, 1H), 8.40 (d, J = 7.6 Hz, 1H), 7.97 (d, J = 7.2 Hz, 1H), 7.61-7.51 (m, 2H), 7.50-7.42 (m, 2H), 7.41-7.34 (m, 2H), 7.21 (dt, J = 3.2, 8.8 Hz, 1H), 7.07-6.82 (m, 4H), 6.29 (s, 1H), 6.15 (s, 1H), 5.23 (br s, 2H), 4.97-4.80 (m, 4H), 4.53 (br s, 2H), 4.43-4.24 (m, 3H), 3.79-3.67 (m, 2H), 3.64-3.37 (m, 8H), 3.26-3.00 (m, 4H), 2.46 (s, 5H), 2.31-2.17 (m, 3H), 2.16-1.97 (m, 4H), 1.91 (br s, 2H), 1.84-1.75 (m, 1H), 1.64 (br d, J = 11.2 Hz, 1H), 1.50-1.35 (m, 3H), 1.04-0.94 (m, 3H), 0.87-0.78 (m, 3H) |
| 503 | D | NA | D | NA | 1070.65 | 1H NMR (400 MHz, Methanol-d4) δ (ppm): 9.03 (s, 1H), 8.01 (s, 1H), 7.84 (s, 1H), 7.68 (s, 2H), 7.55 (s, 1H), 7.35 (s, 1H), 6.99 (s, 2H), 6.84 (s, 1H), 6.26 (s, 1H), 6.08 (s, 1H), 5.35-5.14 (m, 2H), 4.63 (s, 3H), 4.45 (s, 2H), 3.85-3.48 (m, 9H), 3.22 (s, 3H), 2.70 (s, 3H), 2.59 (s, 5H), 2.43 (s, 5H), 2.22 (s, 3H), 1.98 (s, 4H), 1.63 (s, 3H), 1.36-1.26 (m, 1H), 1.08 (s, 3H), 1.00-0.85 (m, 4H). |
| 504 | D | NA | D | NA | 1070.64 | 1H NMR (300 MHz, DMSO-d6) δ (ppm): 14.11 (s, 1H), 9.12 (s, 1H), 8.57 (s, 1H), 8.02 (s, 1H), 7.90 (s, 1H), 7.77 (s, 1H), 7.66 (s, 1H), 7.48 (s, 1H), 7.22 (s, 1H), 6.85 (s, 2H), 6.53 (s, 1H), 6.13 (s, 2H), 5.96 (s, 2H), 5.20 (s, 1H), 5.10 (s, 2H), 4.49 (s, 3H), 4.38 (s, 1H), 4.29 (s, 2H), 3.67 (s, 2H), 3.46 (s, 3H), 3.24 (s, 1H), 3.01 (s, 2H), 2.69 (s, 4H), 2.23 (s, 9H), 1.96 (s, 7H), 1.60-1.37 (m, 5H), 1.21 (s, 2H), 0.94 (s, 3H), 0.88-0.76 (m, 4H). |
| 505 | B | A | D | NA | 1125.73 | "1H NMR (400 MHz, MeOD-d4) δ: 8.82 (s, 1H), 8.48-8.21 (m, 2H), 7.77-7.51 (m, 4H), 7.37 (s, 1H), 7.17-7.09 (m, 1H), 6.85-6.73 (m, 2H), 6.45 (br d, J = 5.2 Hz, 1H), 6.06-6.00 (m, 1H), 5.97-5.84 |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | (m, 1H), 5.27-5.17 (m, 1H), 5.03-4.96 (m, 1H), 4.42-4.36 (m, 1H), 4.36-4.32 (m, 1H), 4.31-4.27 (m, 1H), 3.75-3.65 (m, 1H), 3.63-3.56 (m, 1H), 3.54-3.48 (m, 1H), 3.43-3.32 (m, 1H), 3.31-3.23 (m, 5H), 3.01 (br d, J = 11.6 Hz, 2H), 2.58-2.53 (m, 3H), 2.34-2.19 (m, 5H), 2.18-2.02 (m, 6H), 1.96-1.92 (m, 4H), 1.87-1.81 (m, 1H), 1.53-1.47 (m, 2H), 1.46-1.43 (m, 3H), 1.42-1.36 (m, 1H), 1.27-1.25 (m, 2H), 1.15-1.12 (m, 3H), 0.94 (d, J = 6.8 Hz, 3H), 0.83-0.76 (m, 9H)." |
| 506 | A | A | B | A | 1148.64 | 1H NMR: (400 MHz, DMSO-d6) δ: 9.02-8.93 (m, 1H), 8.41 (d, J = 7.6 Hz, 1H), 8.15 (s, 1H), 7.73 (d, J = 6.0 Hz, 1H), 7.62 (d, J = 7.6 Hz, 1H), 7.49-7.31 (m, 8H), 7.15 (t, J = 7.6 Hz, 1H), 6.50 (d, J = 5.2 Hz, 1H), 6.23 (s, 2H), 6.10 (s, 2H), 5.18-5.13 (m, 1H), 4.94-4.87 (m, 2H), 4.45 (s, 2H), 4.39-4.34 (m, 1H), 4.35-4.21 (m, 5H), 3.73-3.61 (m, 2H), 3.55-3.29 (m, 5H), 3.02 (d, J = 10.8 Hz, 2H), 2.88 (s, 4H), 2.45 (s, 3H), 2.30-2.21 (m, 5H), 2.16-1.97 (m, 3H), 1.92 (s, 2H), 1.84-1.72 (m, 3H), 1.52-1.35 (m, 5H), 0.99-0.92 (m, 3H), 0.85-0.75 (m, 3H) |
| 507 | D | NA | D | NA | 1068.66 | "1H NMR: (400 MHz, DMSO-d6) δ: 9.01-8.93 (m, 1H), 8.18 (s, 1H), 8.14 (d, J = 7.2 Hz, 1H), 7.92 (br d, J = 8.0 Hz, 1H), 7.78 (d, J = 6.0 Hz, 1H), 7.52-7.27 (m, 5H), 7.23 (t, J = 7.6 Hz, 1H), 6.90-6.83 (m, 2H), 6.53 (br d, J = 4.8 Hz, 1H), 6.19-6.08 (m, 2H), 5.98 (s, 2H), 5.27-5.17 (m, 1H), 4.91 (br t, J = 7.2 Hz, 1H), 4.50 (br s, 2H), 4.38-4.05 (m, 5H), 3.92-3.72 (m, 2H), 3.44-3.41 (m, 2H), 3.29-3.21 (m, 6H), 3.02 (br d, J = 11.6 Hz, 2H), 2.81-2.55 (m, 4H), 2.46 (s, 3H), 2.37-1.93 (m, 10H), 1.83-1.63 (m, 3H), 1.52-1.28 (m, 5H), 1.00-0.86 (m, 3H), 0.84-0.72 (m, 3H)." |
| 508 | D | NA | D | NA | 1068.66 | "1H NMR: (400 MHz, DMSO-d6) δ: 8.98 (s, 1H), 8.42 (br d, |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | J = 7.2 Hz, 1H), 8.16 (s, 2H), 7.91 (br d, J = 7.6 Hz, 1H), 7.77 (br d, J = 6.0 Hz, 1H), 7.53-7.34 (m, 5H), 7.23 (br t, J = 7.6 Hz, 1H), 6.91-6.82 (m, 2H), 6.53 (br d, J = 5.2 Hz, 1H), 6.13 (br d, J = 7.6 Hz, 2H), 6.02-5.90 (m, 2H), 5.19 (br s, 1H), 5.02-4.83 (m, 1H), 4.49 (br s, 2H), 4.32-4.22 (m, 5H), 3.76-3.73 (m, 2H), 3.52-3.49 (m, 1H), 3.26-3.32 (m, 4H), 3.02 (br d, J = 11.6 Hz, 2H), 2.78-2.68 (m, 4H), 2.48 (s, 3H), 2.38-2.08 (m, 10H), 1.97 (br s, 3H), 1.78-1.56 (m, 3H), 1.45-1.35 (m, 5H), 1.00-0.92 (m, 3H), 0.81 (br d, J = 6.4 Hz, 3H)." |
| 509 | A | A | D | A | 1042.65 | 1H NMR: (400 MHz, DMSO-d6) δ: 9.01 (s, 1H), 8.60-8.41 (m, 2H), 7.92 (d, J = 8.1 Hz, 1H), 7.83-7.76 (m, 2H), 7.74-7.67 (m, 1H), 7.50 (s, 1H), 7.26-7.19 (m, 1H), 6.90-6.80 (m, 2H), 6.54 (dd, J = 1.6, 6.0 Hz, 1H), 6.16 (d, J = 2.0 Hz, 1H), 6.08 (s, 1H), 6.01-5.89 (m, 2H), 5.13-5.00 (m, 1H), 4.94 (t, J = 7.2 Hz, 1H), 4.50 (br s, 2H), 4.36 (t, J = 8.0 Hz, 1H), 4.27 (br t, J = 5.6 Hz, 3H), 4.24-4.16 (m, 2H), 3.79-3.52 (m, 2H), 3.44 (br d, J = 11.6 Hz, 1H), 3.30-3.22 (m, 3H), 3.02 (br d, J = 11.2 Hz, 3H), 2.80 (br d, J = 10.8 Hz, 1H), 2.66 (s, 3H), 2.58 (br d, J = 5.6 Hz, 2H), 2.46-2.35 (m, 3H), 2.30-2.11 (m, 5H), 2.11-1.85 (m, 5H), 1.76 (ddd, J = 4.8, 8.0, 12.8 Hz, 1H), 1.55-1.35 (m, 3H), 0.96 (t, J = 6.0 Hz, 6H), 0.87-0.76 (m, 3H) |
| 510 | A | A | A | A | 1026.64 | 1H NMR: (400 MHz, METHANOL-d4) δ: 8.91-8.81 (m, 1H), 8.46 (br s, 1H), 7.87-7.77 (m, 1H), 7.76-7.64 (m, 1H), 7.52-7.34 (m, 5H), 7.27-7.14 (m, 1H), 6.95-6.81 (m, 2H), 6.62 (dd, J = 2.0, 6.4 Hz, 1H), 6.31-6.23 (m, 1H), 6.01-5.88 (m, 1H), 5.11-4.95 (m, 1H), 4.57-4.35 (m, 6H), 4.32-4.17 (m, 2H), 3.83 (dd, J = 4.0, 10.8 Hz, 1H), 3.66 (d, J = 10.0 Hz, 1H), 3.62-3.46 (m, 3H), 3.41-3.33 (m, 4H), 3.14-3.03 (m, 2H), 3.01- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 2.86 (m, 2H), 2.49-2.43 (m, 3H), 2.40-2.29 (m, 1H), 2.27-2.08 (m, 5H), 2.05-1.91 (m, 3H), 1.80 (br t, J = 5.2 Hz, 3H), 1.63-1.45 (m, 5H), 1.04 (d, J = 6.4 Hz, 3H), 0.92-0.81 (m, 3H) |
| 511 | D | NA | D | NA | 1026.64 | 1H NRM: (400 MHz, METHANOL-d4) δ: 8.92-8.77 (m, 1H), 8.45 (s, 1H), 7.82 (d, J = 6.0 Hz, 1H), 7.73-7.63 (m, 1H), 7.54-7.31 (m, 5H), 7.26-7.16 (m, 1H), 7.02-6.81 (m, 2H), 6.62 (dd, J = 2.0, 6.4 Hz, 1H), 6.26 (d, J = 2.0 Hz, 1H), 6.07-5.91 (m, 1H), 4.97 (q, J = 7.2 Hz, 1H), 4.64-4.47 (m, 5H), 4.45-4.34 (m, 1H), 4.29-4.16 (m, 2H), 3.75 (d, J = 9.2 Hz, 1H), 3.72-3.57 (m, 2H), 3.56-3.46 (m, 2H), 3.34 (br d, J = 12.0 Hz, 4H), 3.07 (br d, J = 11.6 Hz, 2H), 2.93 (br t, J = 11.6 Hz, 2H), 2.49-2.43 (m, 3H), 2.36 (td, J = 6.8, 9.2 Hz, 1H), 2.29-2.07 (m, 5H), 2.03-1.88 (m, 3H), 1.77 (br t, J = 5.6 Hz, 3H), 1.61-1.42 (m, 5H), 1.04 (d, J = 6.8 Hz, 3H), 0.96-0.82 (m, 3H) |
| 512 | A | A | C | A | 1125.75 | 1H NMR: (400 MHz, DMSO-d6) δ: 8.98 (s, 1H), 8.42 (d, J = 8.0 Hz, 1H), 8.16 (s, 2H), 7.91 (dd, J = 1.6, 8.0 Hz, 1H), 7.77-7.72 (m, 2H), 7.49 (m, 1H), 7.44-7.42 (m, 2H), 7.37-7.33 (m, 2H), 7.24-7.20 (m, 1H), 6.88-6.83 (m, 2H), 6.52 (dd, J = 2.0, 6.0 Hz, 1H), 6.13 (d, J = 2.0 Hz, 1H), 5.96 (s, 1H), 5.21-5.16 (m, 1H), 4.93-4.87 (m, 1H), 4.51-4.44 (m, 4H), 4.28-4.25 (m, 2H), 3.62-3.54 (m, 2H), 3.26-3.23 (m, 5H), 3.01 (d, J = 14.0 Hz, 4H), 2.89-2.77 (m, 6H), 2.45 (s, 3H), 2.33-2.31 (m, 2H), 2.18-1.95 (m, 11H), 1.79-1.66 (m, 4H), 1.47-1.37 (m, 6H), 1.15-1.09 (m, 2H), 0.93 (m, 9H)." |
| 513 | D | NA | D | NA | 929.41 | 1H NMR: (400 MHz, DMSO-d6) δ : 8.97 (s, 1H), 8.89-8.28 (m, 1H), 7.94-7.84 (m, 1H), 7.78 (d, J = 6.0 Hz, 1H), 7.51-7.45 (m, 1H), 7.44-7.39 (m, 2H), 7.37-7.30 (m, 2H), 7.21 (t, J = 7.6 Hz, 1H), 6.89- |

TABLE 2C-continued

| Ex. # | *BRM DC$_{50}$ (nM) | **BRM D$_{max}$ (%)† | *BRG1 DC$_{50}$ (nM) | **BRG1 D$_{max}$ (%)† | Observed Mass (2nd Observed Mass) | HNMR |
|---|---|---|---|---|---|---|
| Target protein degradation via exemplary bifunctional degradation compounds of Table 1C | | | | | | |
| | | | | | | 6.80 (m, 2H), 6.54 (dd, J = 1.6, 6.0 Hz, 1H), 6.28-6.22 (m, 1H), 6.19-6.14 (m, 1H), 5.95 (br d, J = 6.4 Hz, 1H), 5.18-4.93 (m, 1H), 4.92-4.84 (m, 1H), 4.53-4.41 (m, 3H), 4.29-4.20 (m, 3H), 4.06 (d, J = 8.4 Hz, 1H), 3.66-3.49 (m, 3H), 3.48-3.39 (m, 1H), 3.29 (s, 5H), 3.25 (br d, J = 11.6 Hz, 2H), 3.17 (dd, J = 6.8, 9.6 Hz, 1H), 3.06-2.98 (m, 2H), 2.45-2.44 (m, 3H), 2.21-2.14 (m, 5H), 2.08-1.90 (m, 3H), 1.45-1.31 (m, 3H), 1.01-0.86 (m, 3H)." |
| 514 | D | NA | D | NA | 929.40 | 1H NMR (400 MHz, DMSO-d6) δ : 8.99-8.95 (m, 1H), 8.42 (d, J = 8.0 Hz, 1H), 7.89 (d, J = 8.0 Hz, 1H), 7.80-7.70 (m, 1H), 7.47 (s, 1H), 7.45-7.40 (m, 2H), 7.39-7.32 (m, 2H), 7.20 (br t, J = 7.2 Hz, 1H), 6.90-6.78 (m, 2H), 6.53 (dd, J = 2.0, 6.0 Hz, 1H), 6.25 (s, 1H), 6.23-6.18 (m, 1H), 5.95 (br d, J = 6.4 Hz, 1H), 5.13 (br s, 1H), 5.00-4.83 (m, 1H), 4.49 (br s, 2H), 4.40-4.25 (m, 4H), 4.02 (d, J = 9.6 Hz, 1H), 3.87-3.80 (m, 1H), 3.79-3.72 (m, 1H), 3.68-3.61 (m, 1H), 3.47-3.36 (m, 3H), 3.29 (s, 2H), 3.23 (br dd, J = 8.0, 9.2 Hz, 2H), 3.01 (br dd, J = 6.8, 11.2 Hz, 2H), 2.44 (s, 3H), 2.20-2.15 (m, 5H), 2.06-1.90 (m, 4H), 1.84-1.74 (m, 1H), 1.44-1.36 (m, 3H), 0.81 (d, J = 6.8 Hz, 3H). |
| 515 | D | NA | D | NA | 1092.49 | 1H NMR: (400 MHz, METHANOL-d4) δ: 10.01-9.78 (m, 1H), 9.04-8.97 (m, 1H), 8.58 (d, J = 5.6 Hz, 1H), 8.40 (d, J = 7.6 Hz, 1H), 8.25 (s, 1H), 8.05-7.95 (m, 2H), 7.49-7.42 (m, 2H), 7.41-7.30 (m, 3H), 7.07 (d, J = 8.0 Hz, 1H), 7.03-6.94 (m, 2H), 6.91 (br d, J = 6.0 Hz, 1H), 6.34 (d, J = 1.2 Hz, 1H), 6.17-6.01 (m, 1H), 5.25 (br s, 1H), 4.97-4.88 (m, 3H), 4.53 (br s, 2H), 4.36 (br t, J = 7.6 Hz, 3H), 4.31 (br s, 2H), 3.77-3.68 (m, 5H), 3.57 (br d, J = 10.4 Hz, 4H), 3.50-3.39 (m, 4H), 3.19-3.02 (m, 2H), 2.46 (s, 5H), 2.30-2.18 (m, 3H), 2.16-2.00 (m, 4H), |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 1.97-1.86 (m, 2H), 1.84-1.76 (m, 1H), 1.73-1.56 (m, 1H), 1.50-1.33 (m, 3H), 1.02-0.93 (m, 3H), 0.88-0.77 (m, 3H) |
| 516 | D | NA | D | NA | 1107.50 | 1H NMR: (400 MHz, CDC13) δ: 8.99-8.98 (m, 1H), 8.39 (d, J = 7.6 Hz, 1H), 8.13 (s, 1H), 7.90-7.88 (m, 1H), 7.81-7.60 (m, 2H), 7.48-7.43 (m, 2H), 7.39-7.35 (m, 2H), 7.19-7.15 (m, 1H), 6.89-6.85 (m, 3H), 6.57-6.51 (m, 2H), 6.18 (d, J = 2.0 Hz, 1H), 6.13 (s, 1H), 5.83 (s, 1H), 5.23-5.20 (m, 1H), 5.10-5.00 (m, 1H), 4.93-4.89 (m, 1H), 4.56 (s, 2H), 4.38-4.26 (m, 5H), 3.72-3.66 (m, 2H), 3.48-3.39 (m, 3H), 3.17-3.02 (m, 3H), 2.45 (s, 3H), 2.38-2.20 (m, 9H), 2.07-2.00 (m, 3H), 1.94-1.75 (m, 4H), 1.64-1.45 (m, 3H), 1.38 (d, J = 6.8 Hz, 3H), 0.99-0.96 (m, 3H), 0.85-0.80 (m, 3H). |
| 517 | A | A | C | A | 1228.42 | 1H NMR: (400 MHz, DMSO-d6)δ: 8.96 (s, 1H), 8.46 (d, J = 6.4 Hz, 1H), 8.15 (s, 1H), 7.74 (d, J = 5.2 Hz, 1H), 7.61 (d, J = 7.5 Hz, 1H), 7.50-7.31 (m, 7H), 7.17 (s, 1H), 6.65-6.47 (m, 2H), 6.18-5.96 (m, 2H), 5.15 (s, 1H), 4.91 (t, J = 7.2 Hz, 1H), 4.77-4.60 (m, 1H), 4.46 (s, 3H), 4.40-4.30 (m, 1H), 4.23 (s, 1H), 3.84-3.62 (m, 2H), 3.45 (s, 2H), 3.35-2.80 (m, 6H), 2.53-2.51 (m, 3H), 2.49 (s, 3H), 2.43 (s, 3H), 2.34-2.19 (m, 6H), 2.12 (s, 1H), 1.68 (s, 1H), 1.97-1.55 (m, 6H), 1.45-1.28 (m, 3H), 0.95 (d, J = 6.0 Hz, 3H), 0.79 (d, J = 6.4 Hz, 3H) |
| 518 | D | NA | D | NA | 1009.47 | 1H NMR: (400 MHz, DMSO-d6) δ: 8.97 (s, 1H), 8.34 (s, 2H), 7.96 (d, J = 7.2 Hz, 1H), 7.88 (d, J = 8.0 Hz, 1H), 7.53 (s, 1H), 7.29-7.49 (m, 4H), 7.23 (m, J = 7.6 Hz, 1H), 6.99 (d, J = 4.8 Hz, 1H), 6.91-6.83 (m, 2H), 6.56 (s, 1H), 6.07 (s, 1H), 5.88-5.77 (m, 1H), 4.92-4.80 (m, 2H), 4.76 (s, 1H), 4.60-4.50 (m, 1H), 4.42 (m, J = 7.6 Hz, 1H), 4.37-4.23 (m, 3H), 3.93-3.81 (m, 4H), 3.68 (d, J = 8.8 Hz, 9H), 3.55-3.19 (m, 3H), 3.07-2.83 |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | (m, 2H), 2.78-2.68 (m, 2H), 2.48-2.42 (m, 3H), 2.31-2.10 (m, 2H), 2.10-1.88 (m, 3H), 1.83-1.72 (m, 1H), 1.48-1.31 (m, 3H), 0.97-0.71 (m, 6H) |
| 519 | D | NA | D | NA | 1009.47 | 1H NMR: (400 MHz, DMSO-d6) δ: 8.97-9.00 (m, 1H), 8.35-8.42 (m, 2H), 7.96 (s, 1H), 7.88 (d, J = 7.6 Hz, 1H), 7.53 (s, 1H), 7.49-7.41 (m, 2H), 7.39-7.33 (m, 2H), 7.24 (t, J = 7.2 Hz, 1H), 6.99 (s, 1H), 6.92-6.82 (m, 2H), 6.56 (s, 1H), 6.08 (s, 1H), 5.85-5.69 (m, 1H), 4.91 (m, J = 7.2 Hz, 1H), 4.85-4.72 (m, 2H), 4.56 (s, 1H), 4.38-4.24 (m, 4H), 4.03 (s, 1H), 3.90 (d, J = 2.4 Hz, 2H), 3.77-3.65 (m, 1H), 3.57 (d, J = 9.6 Hz, 9 H), 3.35 (d, J = 12.4 Hz, 3H), 3.02 (d, J = 11.6 Hz, 1H), 2.90 (s, 1H), 2.75 (s, 2H), 2.45 (s, 3H), 2.28 (d, J = 7.2 Hz, 2H), 2.00 (s, 3H), 1.73-1.83 (m, 1H), 1.34-1.46 (m, 3H), 0.94 (d, J = 6.4 Hz, 3H), 0.75-0.83 (m, 3H) |
| 520 | A | A | B | A | 1028.50 | 1H NMR: (400 MHz, DMSO-d6) δ: 8.98 (s, 1H), 8.42 (d, J = 7.2 Hz, 1H), 8.17 (s, 2H), 7.91 (dd, J = 1.2, 8.0 Hz, 1H), 7.78-7.74 (m, 2H), 7.50 (m, 1H), 7.44-7.42 (m, 2H), 7.38-7.33 (m, 2H), 7.24-7.20 (m, 1H), 6.88-6.82 (m, 2H), 6.52 (dd, J = 2.0, 6.0 Hz, 1H), 6.13 (d, J = 2.0 Hz, 1H), 5.98-5.94 (s, 2H), 5.22-5.17 (m, 1H), 4.93-4.86 (m, 1H), 4.49-4.42 (m, 4H), 4.32-4.28 (m, 2H), 3.62-3.54 (m, 2H), 3.28-3.23 (m, 4H), 3.03-2.99 (m, 4H), 2.91-2.85 (m, 2H), 2.74-2.68 (m, 2H), 2.45 (s, 3H), 2.36-2.15 (m, 7H), 2.07-1.95 (m, 3H), 1.84-1.72 (m, 3H), 1.51-1.43 (m, 2H), 1.38 (d, J = 6.8 Hz, 3H), 0.93 (m, 9H)." |
| 521 | D | | | | | 1H NMR (400 MHz, DMSO-d6.ppm): δ 14.11 (s, 1H), 8.97 (d, J = 10.0 Hz, 1H), 8.42 (d, J = 1.8 Hz, 2H), 8.19 (d, J = 7.8 Hz, 1H), 7.91-7.77 (m, 2H), 7.52-7.18 (m, 6H), 6.85 (m, 2H), 6.55 (m, 1H), 6.20-6.14 (m, 2H), 5.96 (s, 2H), 5.32 (m, |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 1H), 5.10-4.82 (m, 3H), 4.55-4.43 (m, 3H), 4.27 (d, J = 6.1 Hz, 1H), 3.69-3.43 (m, 5H), 3.27-3.17 (m, 5H), 3.02 (d, J = 11.6 Hz, 2H), 2.63-2.60 (m, 7H), 2.45 (d, J = 9.2 Hz, 3H), 2.26-2.17 (m, 3H), 2.09-1.80 (m, 4H), 1.46 (d, J = 7.0 Hz, 1H), 1.35 (d, J = 6.9 Hz, 2H), 1.23 (s, 1H), 0.96 (d, J = 6.6 Hz, 2H), 0.82-0.75 (m, 4H). |
| 522 | A | A | | | | 1H NMR (400 MHz, DMSO-d6.ppm): δ 14.11 (s, 1H), 8.98 (s, 1H), 8.42-8.38 (m, 3H), 7.9-7.78 (m, 2H), 7.50-7.18 (m,6H), 6.92-6.80 (m, 2H), 6.55 (m, 1H), 6.20-6.13 (m, 2H), 5.96 (s, 2H), 5.32 (m, 1H), 5.16-5.05 (m, 2H), 4.92 (m, 1H), 4.50 (d, J = 4.3 Hz, 2H), 4.36-4.29 (m, 2H), 3.72-3.54 (m, 4H), 3.43 (m, 1H), 3.29-3.18 (m, 6H), 3.02 (d, J = 11.6 Hz, 2H), 2.61-2.54 (m, 7H), 2.45 (s, 3H), 2.22-2.18 (m, 3H), 1.97-1.95 (m, 3H), 1.79 (m, 1H), 1.45-1.38 (m, 3H), 1.23 (s, 1H), 0.96 (t, J = 6.8 Hz, 3H), 0.81 (m, 3H). |
| 523 | D | | | | | 1H NMR: (400 MHz, DMSO-d6) δ: 13.85 (s, 1H), 8.95 (d, J = 4.8 Hz, 1H), 8.42-8.38 (m, 1H), 8.11-8.17 (m, 1H), 7.80 (d, J = 8.0 Hz, 1H), 7.50-7.38 (m, 4H), 7.29-7.23 (m, 2H), 7.13-7.09 (m, 1H), 6.93-6.88 (m, 2H), 6.23-6.15 (m, 1H), 5.15-5.08 (m, 1H), 5.02-4.96 (m, 1H), 4.55-4.49 (m, 1H), 4.33-4.26 (m, 1H), 3.83-3.79 (m, 1H), 3.71-3.47 (m, 12H), 2.44-2.39 (m, 3H), 2.29-2.10 (m, 5H), 2.07-1.92 (m, 1H), 0.96-0.32 (m, 6H). |
| 524 | D | | | | | 1H NMR: (400 MHz, DMSO-d6) δ: 13.85 (s, 1H), 8.96 (d, J = 4.8 Hz, 1H), 8.44 (d, J = 8.4 Hz, 1H), 8.09 (d, J = 9.6 Hz, 1H), 7.80 (dd, J = 1.6, 8.0 Hz, 1H), 7.52-7.49 (m, 2H), 7.42-7.39 (m, 2H), 7.29-7.23 (m, 2H), 7.12-7.10 (m, 1H), 6.93-6.88 (m, 2H), 6.20 (s, 1H), 5.11-5.02 (m, 2H), 4.44 (t, J = 7.6 Hz, 1H), 4.35-4.34 (m, 1H), 3.78-3.71 (m, 2H), 3.66-3.54 (m, 10H), 3.43- |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| | | | | | | 3.40 (m, 1H), 2.44 (s, 3H), 2.34-2.33 (m, 1H), 2.26-2.17 (m, 3H), 2.03-1.89 (m, 2H), 0.97-0.88 (m, 3H), 0.73 (d, J = 6.4 Hz, 3H). |
| 525 | D | | | | | 1H NMR: (400 MHz, DMSO-d6) δ: 13.86-13.84 (m, 1H), 9.01-8.96 (m, 1H), 8.32 (d, J = 8.0 Hz, 1H), 8.10-8.08 (m, 1H), 7.81-7.78 (m, 1H), 7.47-7.42 (m, 1H), 7.40-7.38 (m, 2H), 7.34-7.32 (m, 1H), 7.29-7.23 (m, 2H), 7.13-7.08 (m, 1H), 6.93-6.88 (m, 2H), 6.23-6.22 (m, 1H), 5.13-5.07 (m, 1H), 5.00-4.95 (m, 1H), 4.57-4.46 (m, 1H), 4.26-4.21 (m, 1H), 3.85-3.83 (m, 1H), 3.70-3.47 (m, 12H), 2.44-2.43 (m, 3H), 2.27-2.17 (m, 4H), 2.10-2.02 (m, 1H), 1.91-1.75 (m, 1H), 0.97-0.70 (m, 6H). |
| 526 | D | | | | | 1H NMR: (400 MHz, DMSO-d6) δ: 13.87-13.84 (m, 1H), 8.97-8.96 (m, 1H), 8.46 (d, J = 7.6 Hz, 1H), 8.10-8.07 (m, 1H), 7.80 (dd, J = 1.6, 8.0 Hz, 1H), 7.45-7.38 (m, 4H), 7.30-7.23 (m, 2H), 7.12-7.08 (m, 1H), 6.92-6.88 (m, 2H), 6.21-6.14 (m, 1H), 5.09-4.98 (m, 2H), 4.42 (t, J = 7.6 Hz, 1H), 4.27 (s, 1H), 3.75-3.52 (m, 12H), 3.43-3.41 (m, 1H), 2.44-2.43 (m, 3H), 2.28-2.17 (m, 4H), 2.06-2.00 (m, 1H), 1.92-1.75 (m, 1H), 0.96 (d, J = 6.4 Hz, 3H), 0.80-0.75 (m, 3H). |
| 527 | D | | | | | 1H NMR: (400 MHz, DMSO-d6) δ: 9.00-8.97 (m, 1H), 8.35 (d, J = 8.4 Hz, 1H), 8.29-8.13 (m, 2H), 8.08 (s, 1H), 7.59 (td, J = 2.4, 7.6 Hz, 1H), 7.52-7.47 (m, 1H), 7.47-7.39 (m, 4H), 7.36 (t, J = 7.6 Hz, 1H), 7.01 (d, J = 8.0 Hz, 1H), 6.96 (t, J = 7.6 Hz, 1H), 6.25-6.12 (m, 1H), 5.13-5.05 (m, 1H), 5.01-4.94 (m, 1H), 4.56-4.48 (m, 1H), 4.36-4.25 (m, 1H), 3.82 (d, J = 8.8 Hz, 1H), 3.68-3.41 (m, 7H), 2.63 (br t, J = 7.2 Hz, 2H), 2.47-2.40 (m, 3H), 2.22-2.10 (m, 4H), 2.06-1.95 (m, 1H), 1.65-1.51 (m, 4H), 1.47-1.34 (m, 2H), 0.96 (d, J = 6.8 Hz, 2H), 0.79 (d, J = |

TABLE 2C-continued

| Target protein degradation via exemplary bifunctional degradation compounds of Table 1C | | | | | | |
|---|---|---|---|---|---|---|
| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
| | | | | | | 6.8 Hz, 2H), 0.44 (d, J = 6.8 Hz, 1H), 0.34 (d, J = 6.8 Hz, 1H) |
| 528 | D | | | | | "1H NMR (400 MHz, DMSO-d6) δ: 9.02-8.94 (m, 1H), 8.29 (d, J = 8.0 Hz, 1H), 8.25-8.11 (m, 1H), 8.10-8.04 (m, 1H), 7.62-7.55 (m, 1H), 7.50-7.31 (m, 5H), 7.05-6.92 (m, 2H), 6.24-6.21 (m, 1H), 5.14-5.06 (m, 1H), 5.00-4.91 (m, 1H), 4.58-4.45 (m, 1H), 4.31-4.18 (m, 1H), 3.84 (d, J = 8.6 Hz, 1H), 3.66-3.38 (m, 7H), 2.66-2.59 (m, 2H), 2.48-2.42 (m, 3H), 2.23-2.15 (m, 3H), 1.94-1.73 (m, 1H), 1.66-1.51 (m, 4H), 1.46-1.35 (m, 2H), 0.99-0.81 (m, 3H), 0.81-0.68 (m, 3H)" |
| 529 | D | | | | | 1H NMR: (400 MHz, DMSO-d6) δ: 9.03-8.91 (m, 1H), 8.41 (d, J = 8.4 Hz, 1H), 8.34-8.18 (m, 2H), 8.09 (s, 1H), 7.58 (dd, J = 1.2, 7.6 Hz, 1H), 7.53-7.48 (m, 2H), 7.46-7.40 (m, 2H), 7.39-7.33 (m, 1H), 7.02 (d, J = 8.0 Hz, 1H), 6.99-6.93 (m, 1H), 6.21 (s, 1H), 5.04 (q, J = 7.2 Hz, 1H), 4.45 (t, J = 7.6 Hz, 1H), 4.39-4.25 (m, 1H), 3.84-3.70 (m, 2H), 3.65-3.51 (m, 2H), 3.49-3.39 (m, 3H), 2.63 (br t, J = 7.6 Hz, 2H), 2.46 (s, 3H), 2.28-2.17 (m, 4H), 2.06-1.93 (m, 2H), 1.66-1.50 (m, 4H), 1.44-1.36 (m, 2H), 0.97-0.87 (m, 3H), 0.76-0.70 (m, 3H)." |
| 530 | D | | | | | 1H NMR: (400 MHz, DMSO-d6) δ: 9.01-8.94 (m, 1H), 8.42 (d, J = 8.0 Hz, 1H), 8.31 (br d, J = 4.8 Hz, 1H), 8.11-8.04 (m, 1H), 7.58 (dd, J = 1.6, 7.6 Hz, 1H), 7.49-7.31 (m, 5H), 7.02 (d, J = 8.0 Hz, 1H), 6.96 (t, J = 7.6 Hz, 1H), 6.25-6.12 (m, 1H), 5.07-4.96 (m, 2H), 4.42 (t, J = 7.6 Hz, 1H), 4.32-4.23 (m, 1H), 3.78-3.37 (m, 7H), 2.67-2.58 (m, 2H), 2.47-2.44 (m, 3H), 2.29-2.15 (m, 3H), 2.07-1.99 (m, 1H), 1.93-1.75 (m, 1H), 1.67-1.51 (m, 4H), 1.47-1.33 (m, 2H), 1.01-0.94 (m, 3H), 0.83-0.74 (m, 3H)" |

TABLE 2C-continued

Target protein degradation via exemplary bifunctional degradation compounds of Table 1C

| Ex. # | *BRM $DC_{50}$ (nM) | **BRM $D_{max}$ (%)† | *BRG1 $DC_{50}$ (nM) | **BRG1 $D_{max}$ (%)† | Observed Mass (2nd Observed Mass) | HNMR |
|---|---|---|---|---|---|---|
| 532 | D | | | | | 1H NMR (400 MHz, Methanol-d4) δ 8.89 (s, 1H), 7.80-7.71 (m, 2H), 7.44-7.28 (m, 5H), 7.28-7.20 (m, 1H), 6.90-6.74(m, 2H), 6.54 (m, 1H), 6.14-6.06 (s, 2H), 5.13-5.01 (m, 2H), 4.63-4.30 (m, 7H), 3.82-3.63 (m, 3H), 3.44-3.34 (m, 2H), 3.23-3.12 (m, 2H), 2.86-2.79 (m, 4H), 2.64 (m, 2H), 2.49 (s, 3H), 2.46-2.35 (m, 7H), 2.30-2.17 (m, 7H), 2.15-1.89 (m, 3H), 1.63 (m, 2H), 1.30 (m, 1H), 1.08 (m, 3H), 1.00-0.88 (m, 3H). |
| 533 | A | A | | | | 1H NMR (400 MHz, Methanol-d4) δ 8.90 (s, 1H), 7.81-7.73 (m, 2H), 7.49 (m, 5H), 7.25 (m, 1H), 6.91 (m, 2H), 6.55 (m, 1H), 6.15-6.04 (s, 2H), 5.19-5.04 (m, 2H), 4.55-4.45 (m, 4H), 4.38 (m, 3H), 3.87 (m, 1H), 3.67 (m, 2H), 3.37 (m, 2H), 3.13 (m, 2H), 2.92-2.79 (m, 4H), 2.74-2.59 (m, 2H), 2.51-2.48 (m, 3H), 2.47-2.33 (m, 7H), 2.31-2.12 (m, 7H), 1.98-1.90 (m, 3H), 1.64 (m, 2H), 1.30 (m, 2H), 1.08 (m, 3H), 0.92 (m, 4H). |
| 534 | D | | | | | |
| 535 | A | A | | | | |

†when tested at the top concentration of between 0.3 and 10 μM

*DC50 (nM)

A < 2.5

2.5 ≤ B < 10

10 ≤ C < 30

D ≥ 30

NA not calculated/no curve fit

**Dmax (% degraded)

A > 75

50 < B ≤ 75

C ≤ 50

NA not calculated/no curve fit

TABLE 2D

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| 536 | D | NA | 1052.50 | 1H-NMR (300 MHz, CD3OD, ppm) δ 8.86 (s, 1H), 7.79-7.70 (m, 3H), 7.40-7.37 (m, 7H), 7.23 (s, 1H), 6.51 (d, J = 3 Hz, 1H), 6.08 (d, J = 21 Hz, 2H), 5.20-5.01 (m, 2H), 4.98-4.86 (m, 4H), 4.43-4.41 (m, 3H), 3.72-3.67 (m, 2H), 3.33-3.31 (s, 7H), 3.19-3.12 (m, 2H), 2.77-2.62 (m, 4H), 2.56 (s, 3H), 2.40 (s, 4H), 2.19-2.01 (m, 5H), 1.83-1.80 (m, 3H), 1.53-1.51 (m, 5H), 1.05 (d, J = 6.6 Hz, 3H), 0.91 (d, J = 6.6 Hz, 3H) |

TABLE 2D-continued

| Target protein degradation via exemplary bifunctional degradation compounds of Table 1D | | | | |
|---|---|---|---|---|
| Ex No | *$DC_{50}$ (nM) | **$D_{max}$ (%) | MH + 1 | NMR transcript |
| 537 | D | NA | 1052.50 | 1H-NMR (300 MHz, CD3OD, ppm) δ 8.86 (s, 1H), 7.78-7.74 (m, 3H), 7.41-7.40 (m, 7H), 7.21 (s, 1H), 6.50 (d, J = 6 Hz, 1H), 610-5.96 (m, 2H), 5.08-5.00 (m, 2H), 4.67- 4.56 (m, 2H), 4.34-4.30 (m, 3H), 3.79-3.77 (m, 1H), 3.60-3.52 (m, 2H), 3.43-3.41 (m, 7H), 3.06-3.00 (m, 2H), 2.90-2.79 (m, 4H), 2.47 (s, 3H), 2.46 (s, 4H), 2.44-2.24 (m, 6H), 2.09-1.83 (m, 3H), 1.62-1.48 (m, 5H), 1.05 (d, J = 6.3 Hz, 3H), 0.88(d, J = 6.3 Hz, 3H) |
| 538 | D | NA | 792.31 | 1H NMR (400 MHz, MeOD-d4) δ: 8.90-8.85 (m, 1H), 8.33 (s, 1H), 8.16-8.05 (m, 2H), 7.89-7.80 (m, 1H), 7.44-7.31 (m, 4H), 7.30-7.22 (m, 1H), 6.97-6.87 (m, 2H), 6.19-6.11 (m, 1H), 5.02-4.94 (m, 1H), 4.59-4.46 (m, 1H), 4.42 (br t, J = 4.8 Hz, 2H), 4.38-4.29 (m, 1H), 4.09 (d, J = 9.2 Hz, 1H), 3.91-3.66 (m, 2H), 3.66-3.55 (m, 1H), 3.51-3.36 (m, 2H), 3.29-3.12 (m, 1H), 2.47 (s, 3H), 2.45-2.40 (m, 1H), 2.28-2.22 (m, 1H), 2.20 (s, 3H), 1.88 (ddd, J = 4.8, 8.4, 13.2 Hz, 1H), 1.54-1.40 (m, 3H), 1.14-1.00 (m, 3H). |
| 539 | A | A | 1087.48 | 1H NMR (400 MHz, MeOD) δ: 8.96-8.89 (m, 1H), 8.56-8.46 (m, 1H), 7.78-7.68 (m, 2H), 7.51-7.42 (m, 2H), 7.25-7.18 (m, 1H), 6.90-6.83 (m, 2H), 6.52 (dd, J = 2.0, 6.0 Hz, 1H), 6.12 (d, J = 2.0 Hz, 1H), 6.02-5.91 (m, 1H), 5.26-5.07 (m, 2H), 4.75-4.25 (m, 7H), 3.90-3.78 (m, 1H), 3.76-3.57 (m, 2H), 3.54-3.33 (m, 2H), 3.10 (d, J = 11.2 Hz, 2H), 2.89-2.73 (m, 4H), 2.69-2.62 (m, 3H), 2.48-2.06 (m, 13H), 1.96-1.81 (m, 3H), 1.68-1.52 (m, 5H), 1.04 (d, J = 6.4 Hz, 3H), 0.91-0.85 (m, 3H). |
| 540 | D | NA | 1087.48 | 1H NMR (400 MHz, MeOD) δ: 8.97-8.87 (m, 1H), 8.61-8.42 (m, 1H), 7.74 (d, J = 6.0 Hz, 1H), 7.70-7.64 (m, 1H), 7.54-7.39 (m, 2H), 7.23-7.15 (m, 1H), 6.89-6.80 (m, 2H), 6.50 (dd, J = 2.0, 6.0 Hz, 1H), 6.10 (d, J = 2.0 Hz, 1H), 6.05-5.96 (m, 1H), 5.30-5.06 (m, 2H), 4.60-4.26 (m, 7H), 3.78-3.54 (m, 3H), 3.38-3.33 (m, 1H), 3.29 (s, 1H), 3.12-2.98 (m, 2H), 2.86-2.70 (m, 4H), 2.68-2.62 (m, 3H), 2.49-1.99 (m, 13H), 1.96-1.77 (m, 3H), 1.67-1.47 (m, 5H), 1.07-0.82 (m, 6H). |
| 541 | D | NA | 1087.48 | 1H NMR (400 MHz, MeOD) δ: 8.93-8.90 (m, 1H), 8.76-8.65 (m, 1H), 7.77-7.68 (m, 2H), 7.54-7.40 (m, 2H), 7.24-7.18 (m, 1H), 6.90-6.82 (m, 2H), 6.52 (dd, J = 2.0, 6.0 Hz, 1H), 6.12 (s, 1H), 5.92-5.81 (m, 1H), 5.27-5.07 (m, 2H), 4.65-4.55 (m, 1H), 4.53-4.45 (m, 3H), 4.42-4.14 (m, 3H), 3.72-3.51 (m, 3H), 3.34 (s, 2H), 3.10 (d, J = 11.6 Hz, 2H), 2.94-2.70 (m, 3H), 2.69-2.60 (m, 5H), 2.48-2.00 (m, 13H), 1.92-1.72 (m, 2H), 1.66-1.47 (m, 5H), 1.10-0.48 (m, 6H). |
| 542 | D | NA | 1087.48 | 1H NMR (400 MHz, MeOD) δ: 8.91 (s, 1H), 8.80-8.54 (m, 1H), 7.80-7.67 (m, 2H), 7.48-7.41 (m, 2H), 7.21 (t, J = 7.6 Hz, 1H), 6.91-6.83 (m, 2H), 6.52 (dd, J = 2.0, 6.4 Hz, 1H), 6.16-5.42 (m, 2H), 5.24-5.06 (m, 2H), 4.73-4.46 (m, 4H), 4.44-4.27 (m, 3H), 3.86-3.73 (m, 1H), 3.68-3.45 (m, 2H), 3.42-3.33 (m, 2H), 3.18-3.08 (m, 2H), 2.88-2.55 (m, 8H), 2.46-2.07 (m, 13H), 1.92-1.78 (m, 2H), 1.65-1.50 (m, 5H), 1.05-0.77 (m, 6H). |
| 543 | D | NA | 1080.53 | 1H NMR (400 MHz, DDMSO-d6) δ: 8.99-8.97 (m, 1H), 8.29 (d, J = 8.0 Hz, 1H), 8.17 (s, 1H), 7.91 (d, J = 8.0 Hz, 1H), 7.78-7.75 (m, 1H), 7.49-7.47 (m, 1H), 7.43-7.40 (m, 2H), 7.37-7.30 (m, 2H), 7.24-7.20 (m, 1H), 6.92-6.82 (m, 2H), 6.54-6.51 (m, 1H), 6.17-6.11 (m, 1H), 6.07 (s, 1H), 5.97 (s, 2H), 5.20-5.13 (m, 1H), 5.03-4.84 (m, 2H), 4.53-4.39 (m, 3H), 4.26-4.12 (m, 3H), 3.74 (d, J = 8.4 Hz, 1H), 3.56-3.45 (m, 4H), 3.33-3.23 (m, 4H), 3.09-2.99 (m, 3H), 2.91-2.81 (m, 3H), 2.46-2.45 (m, 3H), 2.33-1.93 (m, 10H), 1.80-1.64 (m, 3H), 1.46-1.34 (m, 5H), 1.26-1.03 (m, 2H), 0.97-0.74 (m, 9H). |
| 544 | A | A | 1080.53 | 1H NMR (400 MHz, DMSO-d6) δ: 9.11 (s, 1H), 8.53 (d, J = 7.6 Hz, 1H), 8.29 (s, 1H), 8.03 (d, J = 8.0 Hz, 1H), 7.89-7.86 (m, 1H), 7.62-7.55 (m, 3H), 7.50-7.48 (m, 2H), 7.39-7.33 (m, 1H), 7.05-6.95 (m, 2H), 6.65-6.63 (m, 1H), 6.28-6.20 (m, 2H), 6.10-6.03 (m, 2H), 5.33-5.00 (m, 3H), 4.61 (s, 2H), 4.49 (t, J = 8.0 Hz, 1H), 4.41-4.25 (m, 3H), 3.84-3.74 (m, 3H), 3.58-3.55 (m, 4H), 3.39-3.36 (m, 4H), 3.15-2.97 (m, 5H), 2.66-2.63 (m, 1H), 2.58 (s, 3H), 2.39-2.08 (m, 10H), 1.97-1.78 (m, 3H), 1.58-1.49 (m, 5H), 1.42-1.34 (m, 1H), 1.25-1.18 (m, 1H), 1.10-1.07 (m, 3H), 0.98-0.91 (m, 6H). |
| 545 | B | A | 1080.53 | 1H NMR (400 MHz, DDMSO-d6) δ: 8.99-8.97 (m, 1H), 8.29 (d, J = 8.0 Hz, 1H), 8.17 (s, 1H), 7.91 (d, J = 8.0 Hz, 1H), 7.78-7.75 (m, 1H), 7.49-7.47 (m, 1H), 7.43-7.40 (m, 2H), 7.37-7.30 (m, 2H), 7.24-7.20 (m, 1H), 6.92-6.82 (m, 2H), 6.54-6.51 (m, 1H), 6.17-6.11 (m, 1H), 6.07 (s, 1H), 5.97 (s, 2H), 5.20-5.13 (m, 1H), 5.03-4.84 (m, 2H), 4.53-4.39 (m, 3H), 4.26-4.12 (m, 3H), 3.74 (d, J = 8.4 Hz, 1H), 3.56-3.45 (m, 4H), 3.33-3.23 (m, 4H), |

TABLE 2D-continued

| Target protein degradation via exemplary bifunctional degradation compounds of Table 1D | | | | |
|---|---|---|---|---|
| Ex No | *$DC_{50}$ (nM) | **$D_{max}$ (%) | MH + 1 | NMR transcript |
| | | | | 3.09-2.99 (m, 3H), 2.91-2.81 (m, 3H), 2.46-2.45 (m, 3H), 2.33-1.93 (m, 10H), 1.80-1.64 (m, 3H), 1.46-1.34 (m, 5H), 1.26-1.03 (m, 2H), 0.97-0.74 (m, 9H). |
| 546 | A | A | 1080.53 | 1H NMR (400 MHz, DMSO-d6) δ: 9.11 (s, 1H), 8.53 (d, J = 7.6 Hz, 1H), 8.29 (s, 1H), 8.03 (d, J = 8.0 Hz, 1H), 7.89-7.86 (m, 1H), 7.62-7.55 (m, 3H), 7.50-7.48 (m, 2H), 7.39-7.33 (m, 1H), 7.05-6.95 (m, 2H), 6.65-6.63 (m, 1H), 6.28-6.20 (m, 2H), 6.10-6.03 (m, 2H), 5.33-5.00 (m, 3H), 4.61 (s, 2H), 4.49 (t, J = 8.0 Hz, 1H), 4.41-4.25 (m, 3H), 3.84-3.74 (m, 3H), 3.58-3.55 (m, 4H), 3.39-3.36 (m, 4H), 3.15-2.97 (m, 5H), 2.66-2.63 (m, 1H), 2.58 (s, 3H), 2.39-2.08 (m, 10H), 1.97-1.78 (m, 3H), 1.58-1.49 (m, 5H), 1.42-1.34 (m, 1H), 1.25-1.18 (m, 1H), 1.10-1.07 (m, 3H), 0.98-0.91 (m, 6H). |
| 547 | D | NA | 1080.53 | 1H NMR (400 MHz, MeOD-d4) δ: 8.89-8.83 (m, 1H), 7.78-7.69 (m, 2H), 7.48-7.31 (m, 5H), 7.26-7.19 (m, 1H), 6.92-6.85 (m, 2H), 6.56-6.50 (m, 1H), 6.13-6.12 (m, 1H), 6.01-5.94 (m, 1H), 5.13-5.02 (m, 2H), 4.58-4.39 (m, 6H), 4.25-4.16 (m, 2H), 3.79-3.62 (m, 3H), 3.51-3.36 (m, 1H), 3.15-2.95 (m, 4H), 2.74-2.65 (m, 2H), 2.46 (s, 3H), 2.40-1.90 (m, 14H), 1.76-1.57 (m, 5H), 1.49-1.47 (m, 3H), 1.19-1.12 (m, 3H), 1.09-1.03 (m, 3H), 0.93-0.83 (m, 3H) |
| 548 | A | A | 1080.53 | 1H NMR (400 MHz, MeOD-d4) δ: 8.89-8.84 (m, 1H), 7.78-7.72 (m, 2H), 7.50-7.36 (m, 5H), 7.26-7.20 (m, 1H), 6.93-6.86 (m, 2H), 6.54-6.52 (m, 1H), 6.13-6.12 (m, 1H), 5.99-5.91 (m, 1H), 5.10-5.02 (m, 2H), 4.62-4.35 (m, 5H), 4.28-4.18 (m, 2H), 3.86-3.36 (m, 3H), 3.19-2.87 (m, 5H), 2.74-2.66 (m, 1H), 2.49-2.47 (m, 3H), 2.42-1.85 (m, 15H), 1.79-1.59 (m, 5H), 1.53-1.51 (m, 3H), 1.31-1.21 (m, 1H), 1.16-1.14 (m, 3H), 1.07-1.03 (m, 3H), 0.90-0.88 (m, 3H) |
| 549 | D | NA | 984.44 | 1H NMR (400 MHz, DMSO-d6) δ: 9.01-8.97 (m, 1H), 8.29-8.23 (m, 1H), 7.92 (d, J = 8.0 Hz, 1H), 7.79 (d, J = 6.0 Hz, 1H), 7.51-7.17 (m, 6H), 6.89-6.82 (m, 2H), 6.55 (d, J = 6.0 Hz, 1H), 6.19 (s, 1H), 5.98 (s, 2H), 5.89-5.84 (m, 1H), 5.15-4.78 (m, 2H), 4.51 (br s, 2H), 4.42 (t, J = 7.6 Hz, 1H), 4.34-4.23 (m, 3H), 3.95-3.82 (m, 2H), 3.76-3.39 (m, 11H), 3.26-3.17 (m, 1H), 3.08-2.89 (m, 3H), 2.47-2.43 (m, 3H), 2.27-2.16 (m, 3H), 2.10-1.89 (m, 3H), 1.87-1.70 (m, 1H), 1.45 (d, J = 7.2 Hz, 1H), 1.35 (d, J = 7.2 Hz, 2H), 0.95 (d, J = 6.8 Hz, 2H), 0.88-0.71 (m, 4H) |
| 550 | A | A | 984.44 | 1H NMR (400 MHz, DMSO-d6) δ: 8.99 (s, 1H), 8.41 (d, J = 7.6 Hz, 1H), 7.92 (d, J = 7.6 Hz, 1H), 7.79 (d, J = 6.0 Hz, 1H), 7.52-7.35 (m, 5H), 7.22 (t, J = 7.2 Hz, 1H), 6.89-6.82 (m, 2H), 6.55 (dd, J = 2.0, 6.0 Hz, 1H), 6.20 (d, J = 1.6 Hz, 1H), 5.99 (s, 2H), 5.84 (s, 1H), 5.17-4.85(m, 2H), 4.51 (br s, 2H), 4.39-4.24 (m, 4H), 3.90 (dt, J = 3.6, 7.6 Hz, 2H), 3.75-3.37 (m, 11H), 3.27-3.20 (m, 1H), 3.08-2.88 (m, 3H), 2.48-2.45 (m, 3H), 2.25-2.15 (m, 3H), 2.15-1.94 (m, 3H), 1.78 (ddd, J = 4.8, 8.0, 12.8 Hz, 1H), 1.46-1.33 (m, 3H), 1.00-0.89 (m, 3H), 0.85-0.72 (m, 3H). |
| 551 | A | A | 1102.49 | 1H NMR (400 MHz, DMSO-d6) δ: 14.14 (s, 1H), 9.11-9.16 (m, 1H), 8.34 (d, J = 7.6 Hz, 1H), 7.92 (d, J = 7.2 Hz, 1H), 7.76 (d, J = 6.0 Hz, 1H), 7.50 (s, 1H), 7.38 (dd, J = 10.0, 6.0 Hz, 1H), 7.27-7.18 (m, 2H), 6.91-6.80 (m, 2H), 6.51 (d, J = 6.8 Hz, 1H), 6.16-6.09 (m, 1H), 6.07 (s, 1H), 5.96 (s, 2H), 5.22-5.14 (m, 1H), 5.12 (d, J = 3.6 Hz, 1H), 5.09-4.93 (m, 1H), 4.49 (s, 2H), 4.40 (m, J = 8.0 Hz, 1H), 4.28 (s, 1H), 4.21-4.11 (m, 2H), 3.76 (d, J = 8.8 Hz, 1H), 3.60-3.54 (m, 1H), 3.53-3.44 (m, 1H), 3.25 (d, J = 10.8 Hz, 3H), 3.02 (d, J = 11.6 Hz, 2H), 2.75 (d, J = 11.6 Hz, 2H), 2.38-2.32 (m, 5H), 2.25 (dd, J = 14.4, 7.6 Hz, 1H), 2.21-2.04 (m, 7H), 1.97 (s, 2H), 1.88-1.69 (m, 3H), 1.67-1.54 (m, 4H), 1.50-1.30 (m, 4H), 1.19-1.05 (m, 2H), 0.96 (d, J = 6.8 Hz, 2H), 0.87-0.78 (m, 3H), 0.75 (d, J = 6.4 Hz, 1H) |
| 552 | A | A | 1102.49 | 1H NMR (400 MHz, DMSO-d6) δ: 14.16 (s, 1H), 9.14 (s, 1H), 8.52 (d, J = 7.2 Hz, 1H), 7.92 (d, J = 8.0 Hz, 1H), 7.76 (d, J = 6.0 Hz, 1H), 7.50 (s, 1H), 7.41 (dd, J = 10.0, 6.0 Hz, 1H), 7.30 (dd, J = 10.0, 6.0 Hz, 1H), 7.22 (m, 1H), 6.88-6.82 (m, 2H), 6.51 (d, J = 5.6 Hz, 1H), 6.16-6.10 (m, 1H), 6.08 (s, 1H), 5.98 (s, 2H), 5.23-5.00 (m, 3H), 4.49 (s, 2H), 4.35 (m, J = 8.0 Hz, 1H), 4.29 (s, 1H), 4.21-4.11 (m, 2H), 3.61-3.74 (m, 2H), 3.41-3.48 (m, 1H), 3.24 (d, J = 12.0 Hz, 3H), 3.01 (d, J = 11.2 Hz, 2H), 2.79 (d, J = 10.4 Hz, 2H), 2.36 (s, 5H), 2.18 (d, J = 7.2 Hz, 2H), 2.14-2.07 (m, 4H), 1.97 (d, J = 4.0 Hz, 2H), 1.92-1.75 (m, 3H), 1.67-1.52 (m, 5H), 1.48-1.34 (m, 4H), 1.26-1.09 (m, 3H), 0.95 (d, J = 6.4 Hz, 3H), 0.84-0.77 (m, 3H) |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| 553 | A | A | 1024.53 | 1H NMR (400 MHz, DMSO-d6) δ: 8.91-8.35 (m, 1H), 7.92 (d, J = 7.2 Hz, 1H), 7.79 (d, J = 6.0 Hz, 1H), 7.50 (s, 1H), 7.40 (q, J = 8.8 Hz, 4H), 7.28-7.18 (m, 2H), 6.96-6.79 (m, 3H), 6.58-6.50 (m, 1H), 6.16 (d, J = 1.6 Hz, 1H), 6.08 (s, 1H), 6.01-5.87 (m, 2H), 5.10 (d, J = 3.6 Hz, 1H), 5.04-4.92 (m, 1H), 4.54-4.46 (m, 2H), 4.38 (t, J = 7.6 Hz, 1H), 4.32-4.24 (m, 3H), 4.20 (br d, J = 2.4 Hz, 2H), 3.89-3.68 (m, 1H), 3.67-3.54 (m, 1H), 3.48-3.40 (m, 1H), 3.31-3.20 (m, 4H), 3.07-2.96 (m, 3H), 2.85-2.75 (m, 1H), 2.75-2.64 (m, 2H), 2.64-2.53 (m, 3H), 2.49-2.38 (m, 2H), 2.34 (br d, J = 9.2 Hz, 1H), 2.27-2.23 (m, 1H), 2.23-2.09 (m, 4H), 2.08-1.93 (m, 3H), 1.93-1.83 (m, 1H), 1.78 (ddd, J = 5.2, 8.0, 12.8 Hz, 1H), 1.50-1.35 (m, 3H), 0.96 (dd, J = 2.4, 6.0 Hz, 6H), 0.86-0.76 (m, 3H) |
| 554 | A | A | 1026.48 | 1H NMR (400 MHz, DMSO-d6) δ: 8.99 (s, 1H), 8.42 (d, J = 7.6 Hz, 1H), 7.92 (d, J = 8.0 Hz, 1H), 7.79 (d, J = 6.0 Hz, 1H), 7.50 (s, 1H), 7.44 (d, J = 8.0 Hz, 2H), 7.40-7.34 (m, 2H), 7.23 (t, J = 7.6 Hz, 1H), 6.92-6.81 (m, 2H), 6.56-6.49 (m, 1H), 6.15 (d, J = 2.0 Hz, 1H), 6.09 (s, 1H), 6.01-5.90 (m, 2H), 5.14-4.99 (m, 1H), 4.92 (t, J = 7.2 Hz, 1H), 4.50 (br s, 2H), 4.37 (t, J = 7.6 Hz, 1H), 4.28 (br s, 1H), 4.24-4.19 (m, 4H), 3.76-3.54 (m, 2H), 3.50-3.41 (m, 1H), 3.25 (br d, J = 11.2 Hz, 3H), 3.02 (br d, J = 11.2 Hz, 2H), 2.88 (br d, J = 10.4 Hz, 2H), 2.64 (br t, J = 5.2 Hz, 2H), 2.31-2.08 (m, 4H), 2.07-1.85 (m, 6H), 1.78 (ddd, J = 4.4, 8.0, 12.8 Hz, 1H), 1.69-1.57 (m, 4H), 1.45 (br d, J = 7.2 Hz, 1H), 1.38 (d, J = 7.2 Hz, 3H), 1.30-1.04 (m, 3H), 0.99-0.93 (m, 3H), 0.85-0.78 (m, 3H) |
| 555 | D | NA | 1139.53 | 1H NMR (400 MHz, DMSO-d6) δ 14.15 (s, 1H), 9.00-8.75 (m, 1H), 8.54-8.20 (m, 1H),8.00-7.91 (m, 1H), 7.83-7.70 (m, 1H), 7.55-7.43 (m, 1H), 7.42-7.35 (m, 2H), 7.33-7.26 (m, 1H), 7.25-7.16 (m, 2H), 6.93-6.80 (m, 2H), 6.72-6.60 (m, 1H), 6.58-6.47 (m, 1H), 6.18-6.10 (m, 1H), 6.09-6.05 (m, 1H), 6.00-5.90 (m, 2H), 5.25-5.13 (m, 1H), 5.00-4.68 (m, 1H), 4.60-4.38 (m, 3H), 4.32-4.16 (m, 4H), 3.80-3.65(m, 1H), 3.60-3.45 (m, 2H), 3.05-3.00 (m, 2H), 2.80-2.65 (m, 3H), 2.64-2.60 (m, 2H), 2.48-2.46 (m, 3H), 2.35-2.21 (m, 6H), 2.20-2.15 (m, 2H), 2.14-2.01 (m, 5H), 2.00-1.94 (m, 2H), 1.86-1.63 (m, 6H), 1.60-1.46 (m, 2H), 1.44-1.33(m, 2H), 1.30-1.20 (m, 1H), 1.05-0.90(m, 3H), 0.89-0.80(m, 3H), 0.73-0.71(m, 1H). |
| 556 | A | A | 1139.53 | 1H NMR (400 MHz, DMSO-d6) δ 14.15 (s, 1H), 9.05-8.75 (m, 1H), 8.45-8.30 (m, 1H),8.00-7.88 (m, 1H), 7.80-7.72 (m, 1H), 7.55-7.31 (m, 5H), 7.30-7.12 (m, 2H), 6.92-6.80 (m, 2H), 6.78-6.63 (m, 1H), 6.60-6.57 (m, 1H), 6.20-6.01 (m, 2H), 6.00-5.81(m, 2H), 2.25-5.12 (m, 1H), 5.11-4.95 (m, 1H), 4.83-4.70 (m, 1H), 4.58-4.45 (m, 2H), 4.44-4.34 (m, 1H), 4.32-4.18 (m, 4H), 3.78-3.60 (m, 2H), 3.60-3.40 (m, 2H), 3.25-3.20 (m, 2H), 3.09-2.98 (m, 2H), 2.80-2.70 (m, 2H), 2.69-2.61 (m, 2H), 2.46-2.44 (m, 2H), 2.35-2.23 (m, 5H), 2.20-2.06 (m, 6H), 2.04-1.90 (m, 3H), 1.83-1.65 (m, 5H), 1.62-1.50 (m, 2H), 1.49-1.33 (m, 2H), 1.30-1.20(m, 1H), 1.00-0.90 (m, 3H), 0.88-0.75 (m, 3H). |
| 557 | D | NA | 820.35 | 1H NMR (400 MHz, DMSO-d6) δ: 13.84 (br s, 1H), 8.99-8.94 (m, 1H), 8.48-8.37 (m, 2H), 8.21-8.14 (m, 2H), 7.99 (d, J = 8.0 Hz, 1H), 7.44-7.24 (m, 5H), 6.94-6.88 (m, 2H), 6.47 (s, 2H), 6.27 (s, 1H), 5.06-4.87 (m, 1H), 4.37 (t, J = 7.6 Hz, 1H), 4.30-4.15 (m, 3H), 4.00 (d, J = 9.6 Hz, 1H), 3.70 (br dd, J = 4.2, 10.2 Hz, 1H), 3.53-3.38 (m, 6H), 2.44 (s, 3H), 2.42-2.35 (m, 1H), 2.25-2.15 (m, 3H), 2.06-1.86 (m, 3H), 1.83-1.73 (m, 1H), 1.62-1.46 (m, 2H), 1.44-1.32 (m, 3H), 0.81 (d, J = 6.8 Hz, 3H). |
| 558 | D | NA | 820.35 | 1H NMR (400 MHz, DMSO-d6) δ: 13.83 (br s, 1H), 9.00-8.90 (m, 1H), 8.47-8.30 (m, 2H), 8.23-8.16 (m, 2H), 8.03-7.97 (m, 1H), 7.45-7.24 (m, 5H), 6.95-6.89 (m, 2H), 6.49 (s, 2H), 6.26 (s, 1H), 5.07-4.85 (m, 1H), 4.54-4.38 (m, 1H), 4.30-4.13 (m, 3H), 4.05 (d, J = 8.6 Hz, 1H), 3.72-3.45 (m, 3H), 3.32-3.18 (m, 3H), 3.13-2.93 (m, 1H), 2.48-2.43 (m, 3H), 2.42-2.26 (m, 1H), 2.23-2.13 (m, 3H), 2.09-1.97 (m, 1H), 1.95-1.72 (m, 3H), 1.55-1.45 (m, 2H), 1.44-1.32 (m, 3H), 1.03-0.85 (m, 3H). |
| 559 | D | NA | 806.33 | 1H NMR (400 MHz, DMSO-d6) δ: 13.84 (br s, 1H), 8.98 (s, 1H), 8.50-8.34 (m, 2H), 8.20-8.17 (m, 2H), 7.99 (dd, J = 1.2, 8.0 Hz, 1H), 7.45-7.32 (m, 4H), 7.31-7.22 (m, 1H), 6.95-6.89 (m, 2H), 6.55-6.45 (m, 2H), 6.28 (s, 1H), 4.91 (quin, J = 7.2 Hz, 1H), 4.38 (t, J = 7.6 Hz, 1H), 4.33-4.22 (m, 3H), 4.03 (d, J = 9.6 Hz, 1H), 3.72 (dd, J = 4.4, 10.4 Hz, 1H), 3.56-3.46 (m, 2H), 3.43-3.32 (m, 4H), 2.47-2.44 (m, 3H), 2.43-2.32 (m, 1H), 2.23-2.17 (m, 3H), 2.16-2.07 (m, 2H), 2.06-1.89 (m, 1H), 1.85-1.73 (m, 1H), 1.36 (d, J = 7.2 Hz, 3H), 0.84 (d, J = 6.8 Hz, 3H). |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| 560 | D | NA | 806.33 | 1H NMR (400 MHz, DMSO-d6) δ: 13.83 (br s, 1H), 9.00-8.92 (m, 1H), 8.45-8.30 (m, 2H), 8.22-8.16 (m, 2H), 8.03-7.97 (m, 1H), 7.45-7.24 (m, 5H), 6.95-6.89 (m, 2H), 6.55-6.46 (m, 2H), 6.29-6.26 (m, 1H), 5.23-4.85 (m, 2H), 4.59-4.36 (m, 1H), 4.30-4.18 (m, 3H), 4.08 (d, J = 8.4 Hz, 1H), 3.60-3.42 (m, 3H), 3.30-3.09 (m, 3H), 2.48-2.43 (m, 3H), 2.42-2.31 (m, 1H), 2.22-2.13 (m, 3H), 2.12-1.96 (m, 3H), 1.95-1.69 (m, 1H), 1.44-1.33 (m, 3H), 1.07-1.85(m, 3H). |
| 561 | D | NA | 1117.49 | 1H NMR (400 MHz, CD3OD-d4) δ: 8.98 (s, 1H), 7.77 (d, J = 6.4 Hz, 1H), 7.71 (d, J = 7.2 Hz, 1H), 7.49-7.42 (m, 2H), 7.23 (t, J = 7.2 Hz, 1H), 6.92-6.84 (m, 2H), 6.59 (d, J = 5.2 Hz, 1H), 6.15 (s, 1H), 6.11-6.03 (m, 1H), 5.20-5.10 (m, 1H), 5.09-5.05 (m, 1H), 4.61-4.51 (m, 5H), 4.44 (s, 1H), 4.40-4.32 (m, 1H), 3.99 (s, 3H), 3.79 (d, J = 8.8 Hz, 1H), 3.75-3.69 (m, 1H), 3.68-3.58 (m, 2H), 3.46 (s, 2H), 3.42-3.35 (m, 3H), 3.23-3.07 (m, 4H), 3.04-2.80 (m, 1H), 2.65 (s, 3H), 2.52-2.35 (m, 5H), 2.31-2.22 (m, 3H), 2.19-2.09 (m, 2H), 2.08-1.83 (m, 5H), 1.57-1.43 (m, 3H), 1.06 (d, J = 6.4 Hz, 3H), 0.93 (d, J = 6.4 Hz, 3H). |
| 562 | A | A | 1117.49 | 1H NMR (400 MHz, CD3OD-d4) δ: 9.03-8.93 (m, 1H), 7.79-7.67 (m, 2H), 7.55-7.40 (m, 2H), 7.27-7.15 (m, 1H), 6.93-6.79 (m, 2H), 6.52-6.45 (m, 1H), 6.12 (s, 1H), 6.05-5.87 (m, 1H), 5.18-5.03 (m, 2H), 4.58-4.43 (m, 4H), 4.42-4.25 (m, 3H), 4.07-3.93 (m, 3H), 3.88-3.72 (m, 1H), 3.71-3.49 (m, 2H), 3.47-3.33 (m, 2H), 3.11 (d, J = 11.2 Hz, 2H), 2.89-2.71 (m, 4H), 2.67 (s, 3H), 2.44-1.81 (m, 16H), 1.65-1.42 (m, 5H), 1.10-1.00 (m, 3H), 0.95-0.80 (m, 3H). |
| 563 | D | NA | 1117.49 | 1H NMR(400 MHz, CD3OD-d4) δ: 9.06-8.91 (m, 1H), 7.90-7.60 (m, 3H), 7.44 (s, 1H), 7.27-7.13 (m, 1H), 6.96-6.76 (m, 2H), 6.52 (dd, J = 2.0, 6.0 Hz, 1H), 6.13 (d, J = 2.0 Hz, 1H), 5.92-5.79 (m, 1H), 5.19-5.04 (m, 1H), 5.00-4.90 (m, 1H), 4.69-4.29 (m, 6H), 4.26-3.95 (m, 5H), 3.80-3.46 (m, 3H), 3.21-3.05 (m, 2H), 2.98-2.49 (m, 8H), 2.47-1.69 (m, 16H), 1.61-1.34 (m, 5H), 1.09-0.44 (m, 6H). |
| 564 | D | NA | 1117.49 | 1H NMR (400 MHz, CD3OD-d4)δ: 9.00 (s, 1H), 7.98-7.71 (m, 3H), 7.49 (s, 1H), 7.30-7.17 (m, 1H), 6.99-6.83 (m, 2H), 6.55 (dd, J = 2.0, 6.0 Hz, 1H), 6.20-6.02 (m, 2H), 5.19-5.08 (m, 1H), 5.07-5.02 (m, 1H), 4.69-4.48 (m, 6H), 4.46-4.30 (m, 2H), 4.03 (s, 3H), 3.87-3.82 (m, 1H), 3.69-3.58 (m, 2H), 3.20-3.05 (m, 2H), 2.92-2.65 (m, 8H), 2.56-1.83 (m, 16H), 1.66-1.46 (m, 5H), 0.99-0.78 (m, 6H). |
| 565 | D | NA | 1080.53 | 1H NMR (400 MHz, DDMSO-d6) δ: 8.99-8.97 (m, 1H), 8.29 (d, J = 8.0 Hz, 1H), 8.17 (s, 1H), 7.91 (d, J = 8.0 Hz, 1H), 7.78-7.75 (m, 1H), 7.49-7.47 (m, 1H), 7.43-7.40 (m, 2H), 7.37-7.30 (m, 2H), 7.24-7.20 (m, 1H), 6.92-6.82 (m, 2H), 6.54-6.51 (m, 1H), 6.17-6.11 (m, 1H), 6.07 (s, 1H), 5.97 (s, 2H), 5.20-5.13 (m, 1H), 5.03-4.84 (m, 2H), 4.53-4.39 (m, 3H), 4.26-4.12 (m, 3H), 3.74 (d, J = 8.4 Hz, 1H), 3.56-3.45 (m, 4H), 3.33-3.23 (m, 4H), 3.09-2.99 (m, 3H), 2.91-2.81 (m, 3H), 2.46-2.45 (m, 3H), 2.33-1.93 (m, 10H), 1.80-1.64 (m, 3H), 1.46-1.34 (m, 5H), 1.26-1.03 (m, 2H), 0.97-0.74 (m, 9H). |
| 566 | A | A | 1080.53 | 1H NMR (400 MHz, DMSO-d6) δ: 9.11 (s, 1H), 8.53 (d, J = 7.6 Hz, 1H), 8.29 (s, 1H), 8.03 (d, J = 8.0 Hz, 1H), 7.89-7.86 (m, 1H), 7.62-7.55 (m, 3H), 7.50-7.48 (m, 2H), 7.39-7.33 (m, 1H), 7.05-6.95 (m, 2H), 6.65-6.63 (m, 1H), 6.28-6.20 (m, 2H), 6.10-6.03 (m, 2H), 5.33-5.00 (m, 3H), 4.61 (s, 2H), 4.49 (t, J = 8.0 Hz, 1H), 4.41-4.25 (m, 3H), 3.84-3.74 (m, 3H), 3.58-3.55 (m, 4H), 3.39-3.36 (m, 4H), 3.15-2.97 (m, 5H), 2.66-2.63 (m, 1H), 2.58 (s, 3H), 2.39-2.08 (m, 10H), 1.97-1.78 (m, 3H), 1.58-1.49 (m, 5H), 1.42-1.34 (m, 1H), 1.25-1.18 (m, 1H), 1.10-1.07 (m, 3H), 0.98-0.91 (m, 6H). |
| 567 | B | A | 1040.50 | 1H NMR (400 MHz, DMSO-d6) δ: 8.99-8.78 (m, 1H), 8.41 (d, J = 7.6 Hz, 1H), 8.19 (s, 2H), 8.08 (d, J = 6.0 Hz, 1H), 7.88 (d, J = 8.0 Hz, 1H), 7.49-7.41 (m, 3H), 7.39-7.33 (m, 2H), 7.25-7.18 (m, 1H), 6.89-6.81 (m, 2H), 6.76 (d, J = 2.0 Hz, 1H), 6.69 (dd, J = 2.4 Hz, J = 6.0 Hz, 1H), 6.07-5.88 (m, 3H), 4.94-4.87 (m, 1H), 4.54 (s, 2H), 4.37 (t, J = 8.0 Hz, 1H), 4.28 (s, 1H), 4.11 (t, J = 5.6 Hz, 2H), 3.73-3.68 (m, 4H), 3.65 (s, 4H), 3.29 (d, J = 11.6 Hz, 2H), 3.01 (d, J = 12.0 Hz, 2H), 2.88-2.76 (m, 3H), 2.64-2.52 (m, 2H), 2.45 (s, 3H), 2.33-2.10 (m, 4H), 2.08-1.85 (m, 4H), 1.81-1.75 (m, 1H), 1.57 (d, J = 12.8 Hz, 3H), 1.47-1.31 (m, 4H), 0.99-0.92 (m, 3H), 0.89 (d, J = 6.4 Hz, 3H), 0.84-0.77 (m, 3H) |
| 568 | A | A | 1040.50 | 1H NMR (400 MHz, DMSO-d6) δ: 8.99-8.78 (m, 1H), 8.41 (d, J = 7.6 Hz, 1H), 8.18 (s, 2H), 8.08 (d, J = 6.0 Hz, 1H), 7.88 (d, J = 8.0 Hz, 1H), 7.49-7.33 (m, 5H), 7.26-7.18 (m, 1H), 6.89-6.81 (m, |

TABLE 2D-continued

| Target protein degradation via exemplary bifunctional degradation compounds of Table 1D | | | | |
|---|---|---|---|---|
| Ex No | *$DC_{50}$ (nM) | **$D_{max}$ (%) | MH + 1 | NMR transcript |
| | | | | 2H), 6.76 (d, J = 1.6 Hz, 1H), 6.70 (dd, J = 2.4 Hz, J = 6.0 Hz, 1H), 6.08-5.87 (m, 3H), 4.94-4.85 (m, 1H), 4.55 (s, 2H), 4.36 (t, J = 8.0 Hz, 1H), 4.28 (s, 1H), 4.15 (t, J = 5.6 Hz, 2H), 3.74-3.66 (m, 5H), 3.64 (d, J = 9.6 Hz, 3H), 3.30 (s, 2H), 3.01 (d, J = 11.6 Hz, 3H), 2.88 (d, J = 12.0 Hz, 1H), 2.78 (t, J = 7.2 Hz, 2H), 2.58-2.52 (m, 1H), 2.45 (s, 3H), 2.29-2.16 (m, 5H), 2.08-1.88 (m, 4H), 1.86-1.73 (m, 3H), 1.47-1.35 (m, 3H), 1.28-1.16 (m, 1H), 0.96 (dd, J = 6.4 Hz, J = 12.4 Hz, 6H), 0.85-0.76 (m, 3H) |
| 569 | D | NA | 1153.55 | 1H NMR (400 MHz, DMSO-d6) δ 14.15 (s, 1H), 9.00-8.80 (m, 1H), 8.33-8.21 (m, 1H),7.98-7.88 (m, 1H), 7.87-7.62 (m, 2H), 7.50-7.45 (m, 1H), 7.43-7.35 (m, 2H), 7.34-7.25 (m, 2H), 7.24-7.18 (m, 1H), 6.92-6.78 (m, 2H), 6.56-6.45 (m, 1H), 6.20-6.10 (m, 1H), 6.09-6.03 (m, 1H), 6.00-5.89 (m, 2H), 5.25-5.13 (m, 1H), 5.08-5.02 (m, 1H), 4.98-4.73 (m, 1H), 4.67-4.38 (m, 3H), 4.35-4.15 (m, 4H), 3.80-3.65(m, 1H), 3.60-3.49 (m, 2H), 3.22-3.20 (m, 2H), 3.05-3.00 (m, 2H), 2.75-2.66 (m, 2H), 2.57-2.55 (m, 2H), 2.47-2.45 (m, 3H), 2.38-2.23 (m, 6H), 2.20-2.18 (m, 2H), 2.16-2.02 (m, 5H), 2.00-1.92 (m, 2H), 1.80-1.70 (m, 3H), 1.69-1.57(m, 3H), 1.50-1.32 (m, 3H), 1.30-1.20(m, 1H), 1.00-0.88(m, 3H), 0.87-0.80(m, 3H), 0.72-0.70(m, 1H). |
| 570 | A | A | 1153.55 | 1H NMR (400 MHz, DMSO-d6) δ 14.15 (s, 1H), 9.05-8.90 (m, 1H), 8.48-8.30 (m, 1H),8.00-7.85 (m, 1H), 7.83-7.73 (m, 1H), 7.72-7.62 (m, 1H), 7.52-7.45 (m, 1H), 7.44-7.40 (m, 2H), 7.39-7.30 (m, 2H), 7.29-7.20 (m, 1H), 6.92-6.80 (m, 2H), 6.58-6.45 (m, 1H), 6.20-6.10 (m, 2H), 6.00-5.85 (m, 2H), 5.29-5.13 (m, 1H), 5.11-5.00 (m, 1H), 4.88-4.66 (m, 1H), 4.55-4.45 (m, 2H), 4.44-4.35 (m, 1H), 4.34-4.23(m, 2H), 4.21-4.15 (m, 2H), 3.80-3.60 (m, 2H), 3.59-3.40 (m, 2H), 3.24-3.22 (m, 1H), 3.10-3.00 (m, 2H), 2.82-2.70 (m, 2H), 2.69-2.60 (m, 2H), 2.57-2.55 (m, 2H), 2.47-2.45 (m, 2H), 2.38-2.23 (m, 5H), 2.22-2.06 (m, 7H), 2.05-1.90(m, 3H), 1.82-1.71 (m, 3H) ,1.70-1.50(m, 5H), 1.49-1.32(m, 2H), 1.28-1.22(m, 1H), 1.00-0.90(m, 3H), 0.88-0.78(m, 3H). |
| 571 | D | NA | 1157.54 | 1H NMR (400 MHz, DMSO-d6, ppm):δ 14.08 (s, 1H), 9.01 (d, J = 6.1 Hz, 1H), 8.75 (d, J = 8.9 Hz, 1H), 7.91 (m, 1H), 7.77 (d, J = 5.9 Hz, 1H), 7.56-7.41 (m, 5H), 7.26-7.18 (m, 1H), 6.90-6.80 (m, 2H), 6.52 (m, 1H), 6.40-6.09 (m, 3H), 5.95 (s, 2H), 5.50-4.90 (m, 3H), 4.70-4.49 (m, 3H), 4.33-4.21 (m, 2H), 3.69-3.53 (m, 4H), 3.44 (m, 1H), 3.25 (m, 3H), 3.02 (d, J = 11.6 Hz, 2H), 2.80-2.61 (m, 4H), 2.46 (d, J = 8.8 Hz, 3H), 2.28 (m, 5H), 2.17 (d, J = 7.4 Hz, 2H), 2.05 (d, J = 7.3 Hz, 3H), 1.78 (m, 3H), 1.66 (d, J = 13.8 Hz, 2H), 1.57 (s, 1H), 1.39 (q, J = 10.1, 8.1 Hz, 2H), 1.10 (s, 3H), 0.96 (d, J = 6.6 Hz, 2H), 0.81 (d, J = 6.7, 3.1 Hz, 3H), 0.72 (d, J = 6.7 Hz, 1H). |
| 572 | A | A | 1157.54 | 1H NMR (400 MHz, DMSO-d6, ppm):δ 14.11 (s, 1H), 9.01 (d, J = 2.7 Hz, 1H), 8.91 (d, J = 8.8 Hz, 1H), 7.94-7.87 (m, 1H), 7.77 (d, J = 5.9 Hz, 1H), 7.50 (d, J = 9.5 Hz, 5H), 7.26-7.18 (m, 1H), 6.90-6.80 (m, 2H), 6.52 (m, 1H), 6.16-6.05 (m, 3H), 5.96 (s, 2H), 5.32 (s, 1H), 5.23 (s, 1H), 5.12 (d, J = 3.7 Hz, 1H), 4.49 (d, J = 6.3 Hz, 3H), 4.29 (s, 2H), 3.74 (m, 1H), 3.63-3.58 (m, 3H), 3.43 (d, J = 10.8 Hz, 1H), 3.25 (d, J = 11.3 Hz, 3H), 3.01 (d, J = 11.6 Hz, 2H), 2.74 (s, 3H), 2.47 (s, 2H), 2.30 (s, 4H), 2.20-2.10(m, 4H),, 2.05 (s, 2H), 1.96 (s, 2H), 1.83(m, 3H), 1.76 (m, 2H), 1.47 (s, 2H), 1.23 (s, 3H), 0.96 (dd, J == 10.6, 6.7 Hz, 3H), 0.81 (dd, J = 12.4, 6.6 Hz, 3H). |
| 573 | A | A | 942.47 | 1H NMR (400 MHz, METHANOL-d4) δ: 8.87 (s, 1H), 8.49 (s, 1H), 8.30 (s, 1H), 8.10 (s, 2H), 7.85 (d, J = 8.0 Hz, 1H), 7.52-7.22 (m, 5H), 7.02-6.89 (m, 2H), 6.15-6.00 (m, 1H), 5.08-4.95 (m, 1H), 4.50 (t, J = 8.0 Hz, 1H), 4.46-4.37 (m, 1H), 4.33-4.25 (m, 1H), 3.84 (dd, J = 4.4, 10.8 Hz, 1H), 3.74-3.66 (m, 2H), 3.65-3.50 (m, 2H), 3.48-3.37 (m, 1H), 2.95-2.81 (m, 2H), 2.78-2.51 (m, 4H), 2.49-2.44 (m, 3H), 2.42-2.26 (m, 1H), 2.23-2.13 (m, 1H), 2.11-1.90 (m, 4H), 1.80 (br d, J = 12.8 Hz, 2H), 1.66-1.38 (m, 10H), 1.37-1.23 (m, 2H), 1.04 (d, J = 6.8 Hz, 3H), 0.93-0.81 (m, 3H) |
| 574 | A | A | 942.47 | 1H NMR (400 MHz, METHANOL-d4) δ: 8.87 (s, 1H), 8.49 (s, 1H), 8.30 (s, 1H), 8.10 (s, 2H), 7.85 (d, J = 8.0 Hz, 1H), 7.47-7.21 (m, 5H), 6.99-6.88 (m, 2H), 6.11-6.03 (m, 1H), 5.09-4.97 (m, 1H), 4.50 (t, J = 8.0 Hz, 1H), 4.46-4.37 (m, 1H), 4.35-4.23 (m, 1H), 3.84 (dd, J = 4.2, 10.8 Hz, 1H), 3.75-3.66 (m, 2H), 3.65-3.53 (m, 2H), 3.51-3.38 (m, 1H), 2.95-2.80 (m, 2H), 2.78-2.52 (m, 4H), 2.50-2.45 (m, 3H), 2.42-2.27 (m, 1H), 2.24-2.14 (m, 1H), 2.12-1.91 (m, 4H), 1.80 (br d, J = 11.2 Hz, 2H), 1.64-1.39 (m, 10H), 1.37-1.22 (m, 2H), 1.04 (d, J = 6.8 Hz, 3H), 0.95-0.82 (m, 3H) |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| 575 | C | B | 1006.52 | 1H NMR (400 MHz, DMSO-d6) δ: 14.15 (s, 1H), 8.99-8.20 (m, 1H), 7.91 (d, J = 7.2 Hz, 1H), 7.76 (d, J = 6.0 Hz, 1H), 7.52-7.40 (m, 2H), 7.39-7.31 (m, 3H), 7.27-7.19 (m, 2H), 6.92-6.81 (m, 3H), 6.51 (d, J = 4.8 Hz, 1H), 6.18-6.11 (m, 2H), 5.97 (s, 2H), 5.24-4.87 (m, 3H), 4.56-4.39 (m, 3H), 4.29 (d, J = 3.2 Hz, 1H), 3.70 (d, J = 8.8 Hz, 1H), 3.56 (d, J = 3.2 Hz, 1H), 3.52-3.39 (m, 1H), 3.33-3.06 (m, 7H), 3.02 (d, J = 11.2 Hz, 2H), 2.48-2.33 (m, 7H), 2.30-2.23 (m, 4H), 2.21-2.11 (m, 6H), 2.00-1.93 (m, 2H), 1.86-1.75 (m, 1H), 1.50-1.31 (m, 3H), 0.96 (d, J = 6.8 Hz, 2H), 0.87-0.74(m, 4H) |
| 576 | A | A | 1006.53 | 1H NMR (400 MHz, DMSO- d6) δ: 14.12 (s, 1H), 8.40-8.86 (m, 1H), 7.98-7.86 (m, 1H), 7.76 (d, J = 6.0 Hz, 1H), 7.50 (s, 1H), 7.45-7.35 (m, 4H), 7.27-7.19 (m, 2H), 6.92-6.82 (m, 3H), 6.52 (dd, J = 6.0, 1.6 Hz, 1H), 6.14 (s, 2H), 6.04-5.94 (m, 2H), 5.19 (m, 1H), 4.96 (m, J = 7.2 Hz, 1H), 4.49 (s, 2H), 4.37 (t, J = 8.0 Hz, 1H), 4.29 ( s, 1H), 3.72 (dd, J = 10.0, 4.4 Hz, 1H), 3.58 (d, J = 10.0 Hz, 1H), 3.47-3.39 (m, 1H), 3.25 (d, J = 11.6 Hz, 2 H), 3.15 (s, 4H), 3.02 (d, J = 11.6 Hz, 2H), 2.52 (d, J = 2.0 Hz, 1 H), 2.44 (d, J = 7.6 Hz, 7H), 2.27 (s, 3H), 2.21-2.12 (m, 7H), 2.07-1.92 (m, 3H), 1.79 (m, 1H), 1.49-1.35 (m, 3H), 1.00-0.91 (m, 3H), 0.85-0.74 (m, 3H) |
| 577 | A | A | 1080.53 | 1H NMR (400 MHz, DMSO-d6) δ: 14.15 (br s, 1H), 8.99 (s, 1H), 8.42 (d, J = 7.6 Hz, 1H), 7.92 (d, J = 7.6 Hz, 1H), 7.76 (d, J = 6.0 Hz, 1H), 7.50 (s, 1H), 7.48-7.42 (m, 2H), 7.40-7.35 (m, 2H), 7.25-7.20 (m, 1H), 6.89-6.81 (m, 2H), 6.51 (br d, J = 4.8 Hz, 1H), 6.17-6.06 (m, 2H), 5.97 (s, 2H), 5.22-5.06 (m, 1H), 5.04-4.87 (m, 2H), 4.49 (br s, 2H), 4.38 (t, J = 8.0 Hz, 1H), 4.29 (br s, 1H), 4.16 (br s, 2H), 3.74-3.55 (m, 2H), 3.50-3.43 (m, 1H), 3.25 (br d, J = 11.2 Hz, 2H), 3.02 (br d, J = 11.6 Hz, 2H), 2.73-2.61 (m, 1H), 2.46 (s, 3H), 2.40-1.87 (m, 14H), 1.85-1.52 (m, 7H), 1.48-1.34 (m, 5H), 1.00-0.93 (m, 3H), 0.92-0.87 (m, 3H), 0.85-0.77 (m, 3H) |
| 578 | A | A | 1080.53 | 1H NMR (400 MHz, DMSO-d6) δ: 14.15 (br s, 1H), 9.03-8.91 (m, 1H), 8.28 (d, J = 8.0 Hz, 1H), 7.92 (d, J = 8.0 Hz, 1H), 7.76 (d, J = 6.0 Hz, 1H), 7.51-7.46 (m, 1H), 7.46-7.39 (m, 2H), 7.32 (d, J = 8.4 Hz, 2H), 7.26-7.19 (m, 1H), 6.90-6.82 (m, 2H), 6.51 (br d, J = 6.0 Hz, 1H), 6.15-6.06 (m, 2H), 5.97 (s, 2H), 5.22-5.08 (m, 1H), 5.05-4.85 (m, 2H), 4.56-4.46 (m, 2H), 4.46-4.39 (m, 1H), 4.28 (br s, 1H), 4.21-4.06 (m, 2H), 3.75 (d, J = 8.8 Hz, 1H), 3.60-3.39 (m, 2H), 3.32 (br s, 1H), 3.25 (br d, J = 11.6 Hz, 2H), 3.02 (br d, J = 11.6 Hz, 2H), 2.72-2.55 (m, 1H), 2.47-2.45 (m, 3H), 2.37-1.84 (m, 13H), 1.83-1.49 (m, 7H), 1.49-1.33 (m, 5H), 0.97 (d, J = 6.8 Hz, 2H), 0.93-0.74 (m, 7H) |
| 579 | A | A | 1080.53 | 1H NMR (400 MHz, MeOD-d4) δ: 8.94-8.82 (m, 1H), 7.77-7.69 (m, 2H), 7.48-7.32 (m, 5H), 7.24-7.22 (m, 1H), 6.91-6.84 (m, 2H), 6.54-6.50 (m, 1H), 6.13-6.11 (m, 1H), 6.01-5.94 (m, 1H), 5.13-4.90 (m, 2H), 4.71-4.33 (m, 5H), 4.24-4.14 (m, 2H), 3.80-3.57 (m, 3H), 3.15-2.89 (m, 4H), 2.73-2.53 (m, 2H), 2.49-2.45 (m, 3H), 2.43-2.01 (m, 12H), 1.99-1.88 (m, 1H), 1.80-1.56 (m, 6H), 1.53-1.43 (m, 3H), 1.29-1.08 (m, 4H), 1.05 (d, J = 6.8 Hz, 3H), 1.02-0.93 (m, 1H), 0.93-0.83 (m, 3H) |
| 580 | A | A | 1080.53 | 1H NMR (400 MHz, MeOD-d4) δ: 8.89-8.82 (m, 1H), 7.77-7.70 (m, 2H), 7.47-7.34 (m, 5H), 7.25-7.18 (m, 1H), 6.91-6.84 (m, 2H), 6.54-6.49 (m, 1H), 6.14-6.08 (m, 1H), 5.99-5.91 (m, 1H), 5.10-4.90 (m, 2H), 4.78-4.29 (m, 5H), 4.22-4.20 (m, 2H), 3.86-3.45 (m, 3H), 3.15-2.85 (m, 4H), 2.82-2.49 (m, 2H), 2.48-2.44 (m, 3H), 2.03 (s, 12H), 2.00-1.90 (m, 1H), 1.80-1.56 (m, 6H), 1.56-1.46 (m, 3H), 1.30-1.16 (m, 1H), 1.13-1.10 (m, 3H), 1.08-1.04 (m, 4H), 0.93-0.86 (m, 3H) |
| 581 | A | A | 1080.53 | 1H NMR (400 MHz, DMSO-d6) δ: 9.02-8.88 (m, 1H), 8.27 (d, J = 7.6 Hz, 1H), 7.91 (d, J = 8.0 Hz, 1H), 7.75 (d, J = 6.0 Hz, 1H), 7.49 (s, 1H), 7.47-7.39 (m, 2H), 7.30 (d, J = 8.0 Hz, 2H), 7.21 (t, J = 7.6 Hz, 1H), 6.88-6.79 (m, 2H), 6.50 (br d, J = 6.0 Hz, 1H), 6.17-6.09 (m, 1H), 6.06 (s, 1H), 5.96 (s, 2H), 5.25-4.82 (m, 3H), 4.48 (br d, J = 1.6 Hz, 2H), 4.40 (t, J = 7.6 Hz, 1H), 4.30-4.21 (m, 1H), 4.20-4.08 (m, 2H), 3.74 (d, J = 8.8 Hz, 1H), 3.59-3.34 (m, 3H), 3.24 (br d, J = 10.8 Hz, 2H), 3.01 (br d, J = 11.6 Hz, 2H), 2.92-2.76 (m, 1H), 2.46-2.34 (m, 9H), 2.30-2.21 (m, 1H), 2.19-2.14 (m, 2H), 2.13-2.00 (m, 4H), 1.99-1.89 (m, 2H), 1.83-1.73 (m, 1H), 1.71-1.49 (m, 5H), 1.45 (br d, J = 6.8 Hz, 1H), 1.34 (br d, J = 7.2 Hz, 3H), 1.25-1.04 (m, 1H), 0.95 (d, J = 6.8 Hz, 3H), 0.88-0.72 (m, 6H) |
| 582 | A | A | 1080.53 | 1H NMR (400 MHz, DMSO-d6) δ: 8.99 (s, 1H), 8.41 (d, J = 7.6 Hz, 1H), 7.92 (d, J = 8.0 Hz, 1H), 7.76 (d, J = 6.0 Hz, 1H), 7.50 (s, |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | 1H), 7.44 (d, J = 8.4 Hz, 2H), 7.39-7.34 (m, 2H), 7.22 (t, J = 7.6 Hz, 1H), 6.90-6.82 (m, 2H), 6.51 (br d, J = 6.4 Hz, 1H), 6.12 (br d, J = 7.6 Hz, 1H), 6.07 (s, 1H), 5.99-5.88 (m, 2H), 5.25-4.86 (m, 3H), 4.49 (br s, 2H), 4.37 (t, J = 8.0 Hz, 1H), 4.28 (br d, J = 2.4 Hz, 1H), 4.17 (br t, J = 6.0 Hz, 2H), 3.76-3.53 (m, 2H), 3.49-3.40 (m, 1H), 3.25 (br d, J = 12.0 Hz, 2H), 3.01 (br d, J = 11.2 Hz, 2H), 2.88 (ddd, J = 2.8, 6.4, 11.2 Hz, 1H), 2.46 (s, 9H), 2.18 (br d, J = 7.2 Hz, 4H), 2.13-2.06 (m, 2H), 2.02 (br dd, J = 5.2, 8.0 Hz, 1H), 1.99-1.91 (m, 2H), 1.86-1.74 (m, 1H), 1.72-1.55 (m, 5H), 1.53-1.42 (m, 2H), 1.38 (br d, J = 7.2 Hz, 3H), 1.23-1.11 (m, 1H), 1.03-0.93 (m, 3H), 0.90 (t, J = 6.8 Hz, 3H), 0.84-0.77 (m, 3H) |
| 583 | D | NA | 1094.55 | 1H NMR: EW16236-102-P1A, (400 MHz, MeOD-d4) δ: 8.90-8.81 (m, 1H), 7.77-7.67 (m, 2H), 7.47-7.32 (m, 5H), 7.24-7.18 (m, 1H), 6.91-6.83 (m, 2H), 6.52-6.50 (m, 1H), 6.13-6.11 (m, 1H), 6.02-5.94 (m, 1H), 5.08-4.95 (m, 2H), 4.59-4.55 (m, 1H), 4.52-4.40 (m, 3H), 4.22-4.12 (m, 2H), 3.79-3.56 (m, 3H), 3.14-3.05 (m, 2H), 2.93-2.78 (m, 2H), 2.71-2.56 (m, 1H), 2.50-2.43 (m, 3H), 2.41-1.91 (m, 15H), 1.71-1.54 (m, 4H), 1.47 (d, J = 7.2 Hz, 3H), 1.45-1.36 (m, 2H), 1.13-0.99 (m, 6H), 0.96-0.89 (m, 3H), 0.89-0.73 (m, 4H) |
| 584 | A | A | 1094.55 | 1H NMR (400 MHz, MeOD-d4) δ: 8.90-8.83 (m, 1H), 7.78-7.70 (m, 2H), 7.50-7.34 (m, 5H), 7.25-7.18 (m, 1H), 6.92-6.85 (m, 2H), 6.54-6.49 (m, 1H), 6.13-6.12 (m, 1H), 5.99-5.91 (m, 1H), 5.10-4.99 (m, 2H), 4.54-4.37 (m, 4H), 4.22-4.18 (m, 2H), 3.87-3.45 (m, 3H), 3.15-3.07 (m, 2H), 2.97-2.79 (m, 2H), 2.71-2.59 (m, 1H), 2.49-2.45 (m, 3H), 2.42-1.91 (m, 15H), 1.79-1.60 (m, 4H), 1.60-1.41 (m, 5H), 1.14-1.03 (m, 6H), 0.99-0.74 (m, 7H) |
| 585 | B | A | 1094.55 | 1H NMR (400 MHz, MeOD-d4) δ: 8.89-8.80 (m, 1H), 7.78-7.67 (m, 2H), 7.47-7.31 (m, 5H), 7.25-7.17 (m, 1H), 6.91-6.83 (m, 2H), 6.52-6.50 (m, 1H), 6.12-6.11 (m, 1H), 6.02-5.94 (m, 1H), 5.08-4.94 (m, 2H), 4.58-4.54 (m, 1H), 4.52-4.39 (m, 3H), 4.21-4.12 (m, 2H), 3.79-3.48 (m, 3H), 3.14-3.04 (m, 2H), 2.92-2.76 (m, 2H), 2.69-2.58 (m, 1H), 2.52-2.42 (m, 3H), 2.41-1.84 (m, 15H), 1.72-1.55 (m, 4H), 1.52-1.29 (m, 5H), 1.16-1.00 (m, 6H), 0.97-0.87 (m, 3H), 0.88-0.76 (m, 4H) |
| 586 | A | A | 1094.55 | 1H NMR (400 MHz, MeOD-d4) δ: 8.89-8.84 (m, 1H), 7.78-7.70 (m, 2H), 7.51-7.35 (m, 5H), 7.26-7.18 (m, 1H), 6.92-6.83 (m, 2H), 6.53-6.51 (m, 1H), 6.13-6.12 (m, 1H), 6.00-5.90 (m, 1H), 5.09-4.97 (m, 2H), 4.54-4.37 (m, 4H), 4.23-4.17 (m, 2H), 3.87-3.45 (m, 3H), 3.12-3.09 (m, 2H), 2.97-2.82 (m, 2H), 2.70-2.58 (m, 1H), 2.49-2.45 (m, 3H), 2.43-1.91 (m, 15H), 1.78-1.61 (m, 4H), 1.59-1.41 (m, 5H), 1.14-1.02 (m, 6H), 0.99-0.72 (m, 7H) |
| 587 | D | NA | 1102.50 | 1H NMR (400 MHz, DMSO-d6) δ: 14.34-13.92 (m, 1H), 9.18-9.03 (m, 1H), 8.54-8.40 (m, 1H), 7.92 (d, J = 8.0 Hz, 1H), 7.76 (d, J = 6.0 Hz, 1H), 7.50 (s, 1H), 7.38-7.11 (m, 3H), 6.90-6.80 (m, 2H), 6.51 (br d, J = 6.0 Hz, 1H), 6.15-6.10 (m, 1H), 6.07 (s, 1H), 5.97 (s, 2H), 5.26-5.05 (m, 2H), 5.02-4.90 (m, 1H), 4.49 (br s, 2H), 4.41 (t, J = 8.0 Hz, 1H), 4.31-4.23 (m, 1H), 4.20-4.11 (m, 2H), 3.75 (d, J = 8.8 Hz, 1H), 3.66-3.53 (m, 1H), 3.52-3.44 (m, 1H), 3.25 (br d, J = 11.6 Hz, 2H), 3.02 (br d, J = 11.6 Hz, 2H), 2.82-2.70 (m, 2H), 2.53 (d, J = 2.0 Hz, 2H), 2.38-2.31 (m, 5H), 2.29-2.22 (m, 1H), 2.21-2.15 (m, 2H), 2.14-2.01 (m, 3H), 2.00-1.91 (m, 2H), 1.87-1.70 (m, 3H), 1.67-1.54 (m, 5H), 1.52-1.32 (m, 4H), 1.21-1.06 (m, 2H), 0.96 (d, J = 6.8 Hz, 2H), 0.85-0.78 (m, 3H), 0.76 (d, J = 6.8 Hz, 1H). |
| 588 | A | A | 1102.50 | 1H NMR (400 MHz, DMSO-d6) δ: 9.15 (s, 1H), 8.57 (d, J = 7.6 Hz, 1H), 8.18 (s, 1H), 7.91 (d, J = 8.0 Hz, 1H), 7.75 (d, J = 6.0 Hz, 1H), 7.49 (s, 1H), 7.35-7.27 (m, 1H), 7.25-7.18 (m, 2H), 6.89-6.80 (m, 2H), 6.51 (br d, J = 6.0 Hz, 1H), 6.15-6.09 (m, 1H), 6.06 (s, 1H), 6.00-5.92 (m, 2H), 5.21-5.05 (m, 2H), 4.96 (quin, J = 7.6 Hz, 1H), 4.48 (br s, 2H), 4.36 (t, J = 8.0 Hz, 1H), 4.27 (br s, 1H), 4.17 (br t, J = 6.0 Hz, 2H), 3.73-3.59 (m, 3H), 3.24 (br d, J = 12.4 Hz, 3H), 3.01 (br d, J = 11.6 Hz, 2H), 2.87-2.77 (m, 2H), 2.45-2.39 (m, 3H), 2.35 (s, 3H), 2.08 (br s, 6H), 2.05-1.87 (m, 5H), 1.74 (ddd, J = 4.8, 8.0, 12.8 Hz, 1H), 1.63 (br d, J = 6.4 Hz, 5H), 1.50-1.33 (m, 4H), 1.24-1.11 (m, 2H), 0.99-0.90 (m, 3H), 0.86-0.74 (m, 3H). |
| 589 | D | NA | 1123.55 | 1H NMR (400 MHz, DMSO-d6) δ 14.25 (s, 1H), 9.20-8.83 (m, 2H), 8.75-8.46 (m, 1H),8.38-8.11 (m, 1H), 8.00-7.85 (m, 1H), 7.84-7.60 (m, 1H), 7.57-7.40 (m, 1H), 7.30-7.08 (m, 1H), 7.00-6.70 (m, 2H), 6.60-6.40 (m, 1H), 6.30-6.05 (m, 2H), 6.04-5.83 (m, 2H), 5.32-5.01 (m, 2H), 5.00-4.83 (m, 1H), 4.65-4.40 (m, 3H), 4.39-4.15 (m, 2H), 3.79-3.65 (m, 1H), 3.64-3.40 (m, 4H), 3.30-3.15 (m, 4H),3.10-2.90 (m, 2H), 2.80-2.57 (m, 7H), 2.36-2.25 (m, |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | 4H), 2.21-2.13 (m, 2H), 2.12-1.66 (m, 11H), 1.64-1.48 (m, 3H), 1.46-1.35 (m, 4H), 1.15-1.02 (m, 1H), 1.00-0.90 (m, 3H), 0.88-0.80 (m, 3H), 0.78-0.70 (m, 1H). |
| 590 | A | A | 1123.55 | 1H NMR (400 MHz, DMSO-d6) δ 14.25 (s, 1H), 9.32-9.01 (m, 1H), 9.00-8.75 (m, 1H),8.70-8.58 (m, 1H), 8.57-8.25 (m, 1H), 8.00-7.83 (m, 1H), 7.82-7.65 (m, 1H), 7.60-7.40 (m, 1H), 7.31-7.08 (m, 1H), 7.00-6.75 (m, 2H), 6.65-6.32 (m, 1H), 6.23-6.05 (m, 2H), 6.04-5.91 (m, 2H), 5.32-5.05 (m, 2H), 5.04-4.85 (m, 1H), 4.60-4.45 (m, 2H), 4.44-4.33 (m, 1H), 4.30-4.13 (m, 2H), 3.80-3.50 (m, 4H),3.48-3.37 (m, 1H), 3.10-2.95 (m, 2H), 2.76-2.60 (m, 7H), 2.40-2.22 (m, 5H), 2.21-2.08 (m, 5H), 2.05-1.85 (m, 5H), 1.84-1.32 (m, 12H), 1.25-1.20 (m, 1H), 1.15-1.05 (m, 2H), 1.00-0.90 (m, 3H), 0.85-0.70 (m, 3H). |
| 591 | A | A | 957.48 | |
| 592 | A | A | 983.46 | |
| 593 | A | A | 1109.59 | 1H NMR (400 MHz, DMSO-d6) δ: 13.85 (s, 1H), 9.01-8.90 (m, 1H), 8.45 (s, 1H), 8.24-8.16 (m, 3H), 8.05-7.97 (m, 1H), 7.50-7.40 (m, 2H), 7.34-7.31 (m, 1H), 7.27 (dt, J = 1.6, 7.6 Hz, 1H), 6.97-6.86 (m, 2H), 6.47 (s, 2H), 6.16-6.11 (m, 1H), 5.16-4.82 (m, 2H), 4.55-4.39 (m, 1H), 4.33-4.21 (m, 1H), 4.20-4.08 (m, 1H), 3.68 (d, J = 8.8 Hz, 1H), 3.58-3.38 (m, 5H), 2.99-2.77 (m, 3H), 2.75-2.68 (m, 1H), 2.64-2.55 (m, 2H), 2.46-2.43 (m, 3H), 2.32-2.20 (m, 6H), 2.16-1.89 (m, 5H), 1.87-1.67 (m, 10H), 1.52-1.33 (m, 10H), 1.29-1.04 (m, 5H), 0.96 (d, J = 6.8 Hz, 2H), 0.87-0.72 (m, 4H) |
| 594 | A | A | 1109.59 | 1H NMR (400 MHz, DMSO-d6) δ: 13.85 (s, 1H), 9.02-8.95 (m, 1H), 8.47-8.37 (m, 2H), 8.19 (d, J = 16.8 Hz, 2H), 8.02 (dd, J = 1.5, 8.4 Hz, 1H), 7.48-7.41 (m, 2H), 7.40-7.34 (m, 2H), 7.32-7.23 (m, 1H), 6.96-6.89 (m, 2H), 6.48 (s, 2H), 6.16-5.97 (m, 1H), 5.10 (d, J = 3.4 Hz, 1H), 5.03-4.87 (m, 1H), 4.37 (t, J = 7.8 Hz, 1H), 4.28 (br s, 1H), 4.22-4.11 (m, 1H), 3.77-3.67 (m, 1H), 3.56 (br d, J = 9.8 Hz, 2H), 3.48-3.39 (m, 3H), 2.92 (br t, J = 9.7 Hz, 2H), 2.86-2.77 (m, 1H), 2.70 (br dd, J = 2.6, 10.4 Hz, 1H), 2.65-2.56 (m, 3H), 2.46 (s, 3H), 2.33-2.19 (m, 6H), 2.13-1.94 (m, 4H), 1.83-1.61 (m, 10H), 1.51-1.31 (m, 10H), 1.28-1.02 (m, 5H), 1.01-0.89 (m, 3H), 0.86-0.71 (m, 3H) |
| 595 | A | A | 1109.59 | 1H NMR (400 MHz, DMSO-d6) δ: 13.85 (br s, 1H), 9.03-8.89 (m, 1H), 8.45 (s, 1H), 8.25-8.14 (m, 3H), 8.06-7.98 (m, 1H), 7.52-7.38 (m, 3H), 7.35-7.31 (m, 1H), 7.30-7.24 (m, 1H), 6.96-6.90 (m, 2H), 6.47 (s, 2H), 6.16-6.12 (m, 1H), 5.14-4.82 (m, 2H), 4.56-4.39 (m, 1H), 4.28 (br d, J = 3.2 Hz, 1H), 4.22-4.11 (m, 1H), 3.68 (d, J = 8.8 Hz, 1H), 3.60-3.39 (m, 5H), 2.99-2.77 (m, 3H), 2.70 (br dd, J = 2.8, 10.4 Hz, 1H), 2.64-2.56 (m, 2H), 2.47-2.45 (m, 3H), 2.32-2.20 (m, 6H), 2.15-1.89 (m, 5H), 1.86-1.65 (m, 10H), 1.51-1.29 (m, 10H), 1.28-1.04 (m, 5H), 0.96 (d, J = 6.8 Hz, 2H), 0.86-0.71 (m, 4H) |
| 596 | A | A | 1109.59 | 1H NMR (400 MHz, DMSO-d6) δ: 13.85 (s, 1H), 9.03-8.95 (m, 1H), 8.48-8.35 (m, 2H), 8.19 (d, J = 16.8 Hz, 2H), 8.02 (dd, J = 1.6, 8.4 Hz, 1H), 7.48-7.42 (m, 2H), 7.40-7.34 (m, 2H), 7.30-7.24 (m, 1H), 6.96-6.90 (m, 2H), 6.48 (s, 2H), 6.17-5.92 (m, 1H), 5.10 (d, J = 3.6 Hz, 1H), 5.02-4.87 (m, 1H), 4.37 (t, J = 7.6 Hz, 1H), 4.29 (br d, J = 2.8 Hz, 1H), 4.23-4.13 (m, 1H), 3.71 (br dd, J = 4.4, 10.4 Hz, 1H), 3.56 (br d, J = 9.6 Hz, 2H), 3.51-3.34 (m, 5H), 2.92 (br t, J = 9.6 Hz, 2H), 2.81 (br d, J = 9.2 Hz, 1H), 2.70 (br dd, J = 3.6, 10.0 Hz, 1H), 2.65-2.56 (m, 2H), 2.46 (s, 3H), 2.33-2.16 (m, 6H), 2.13-1.93 (m, 4H), 1.85-1.64 (m, 10H), 1.51-1.31 (m, 10H), 1.25-1.03 (m, 4H), 1.00-0.90 (m, 3H), 0.85-0.76 (m, 3H) |
| 597 | C | A | 1114.61 | 1H NMR (400 MHz, DMSO-d6) δ (ppm): 14.29 (s, 1H), 8.98 (d, J = 6.0 Hz, 1H), 8.25 (d, J = 7.8 Hz, 1H), 7.96-7.89 (m, 1H), 7.55-7.27 (m, 5H), 7.25-7.21 (m, 1H), 6.87 (dd, J = 8.0, 6.5 Hz, 2H), 6.26-6.02 (m, 3H), 5.12-4.84 (m, 2H), 4.53-4.38 (m, 1H), 4.27 (brs, 1H), 4.20-4.12 (m, 2H), 3.79-3.60 (m, 3H), 3.58-3.44 (m, 2H), 3.17-3.12 (m, 2H), 2.98 (t, J = 11.1 Hz, 2H), 2.83-2.62 (m, 5H), 2.46 (d, J = 4.2 Hz, 3H), 2.34-2.27 (m, 4H), 2.26-2.15 (m, 4H), 2.13-1.93 (m, 5H), 1.91-1.74 (m, 6H), 1.74-1.66 (m, 3H), 1.66-1.53 (m, 7H), 1.51-1.43 (m, 2H), 1.35 (d, J = 7.1 Hz, 3H), 1.26-1.00 (m, 5H), 0.96 (d, J = 6.6 Hz, 2H), 0.84-0.81 (m, 3H), 0.75 (d, J = 6.7 Hz, 1H). |
| 598 | A | A | 1114.61 | 1H NMR (400 MHz, DMSO-d6) δ (ppm): 14.29 (s, 1H), 8.98 (d, J = 3.0 Hz, 1H), 8.39 (d, J = 7.7 Hz, 1H), 7.96-7.89 (m, 1H), 7.52 (s, 1H), 7.43 (d, J = 8.4 Hz, 2H), 7.36 (d, J = 8.2 Hz, 2H), 7.27-7.18 (m, 1H), 6.89-6.86 (m, 2H), 6.20 (brs, 2H), 6.06 (s, 1H), 5.11-4.97 (m, 1H), 4.91 (t, J = 7.2 Hz, 1H), 4.37 (t, J = 7.8 Hz, |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | 1H), 4.28 (brs, 1H), 4.17 (t, J = 6.6 Hz, 2H), 3.73-3.60 (m, 4H), 3.47-3.43 (m, 1H), 3.19-3.12 (m, 2H), 2.98 (t, J = 11.2 Hz, 2H), 2.77-2.64 (m, 5H), 2.46 (s, 3H), 2.34-3.28 (m, 4H), 2.26-2.17 (m, 4H), 2.09-1.99 (m, 5H), 1.91-1.78 (m, 5H), 1.78-1.67 (m, 4H), 1.67-1.56 (m, 7H), 1.49-1.32 (m, 5H), 1.26-1.00 (m, 5H), 0.97-0.93 (m, 3H), 0.83-0.79 (m, 3H). |
| 599 | A | A | 1040.54 | 1H NMR (400 MHz, MeOD) δ: 8.90 (s, 1H), 8.38 (s, 1H), 8.30-8.27 (m, 1H), 8.13 (s, 1H), 7.75 (d, J = 8.0 Hz, 1H), 7.50-7.36 (m, 5H), 7.05-7.02 (m, 2H), 6.00 (s, 1H), 5.09-4.93 (m, 1H), 4.54-4.38 (m, 2H), 4.30-4.27 (m, 2H), 3.87-3.84 (m, 1H), 3.78-3.76 (m, 1H), 3.71-3.68 (d, J = 12.0 Hz, 1H), 3.64-3.52 (m, 3H), 3.47-3.44 (m, 1H), 3.24-3.20 (m, 2H), 3.01-2.85 (m, 2H), 2.84-2.58 (m, 5H), 2.50 (s, 3H), 2.37-2.23 (m, 2H), 2.23-2.12 (m, 6H), 2.01-1.95 (m, 2H), 1.85-1.78 (m, 2H), 1.66-1.49 (m, 11H), 1.08 (d, J = 8.0 Hz, 3H), 0.91 (m, J = 8.0 Hz, 3H). |
| 600 | D | NA | 1007.51 | |
| 601 | A | A | 1007.51 | |
| 602 | A | A | 1051.52 | 1H NMR (400 MHz, MeOD-d4) δ: 8.88 (s, 1H), 8.48 (s, 1H), 7.88-7.70 (m, 2H), 7.49-7.23 (m, 5H), 7.29-7.15 (m, 1H), 7.03-6.85 (m, 2H), 6.61-6.54 (m, 1H), 6.24 (s, 1H), 6.13-6.05 (m, 1H), 5.13-4.97 (m, 2H), 4.61-4.37 (m, 4H), 3.89-3.68 (m, 3H), 3.67-3.58 (m, 2H), 3.36-3.34 (m, 2H), 3.27-3.18 (m, 2H), 3.14-2.76 (m, 8H), 2.50-2.45 (m, 3H), 2.41-2.30 (m, 1H), 2.28-2.10 (m, 7H), 2.07-1.92 (m, 4H), 1.88-1.79 (m, 2H), 1.61-1.50 (m, 3H), 1.42-1.27 (m, 2H), 1.05 (d, J = 6.8 Hz, 3H), 0.95-0.85 (m, 3H) |
| 603 | A | A | 1065.53 | |
| 604 | A | A | 1079.55 | |
| 605 | D | NA | 1105.56 | |
| 606 | C | A | 1104.59 | |
| 607 | A | A | 1104.59 | |
| 608 | A | A | 1120.57 | |
| 609 | D | NA | 1086.58 | 1H NMR (400 MHz, Methanol-d4, ppm): δ 8.89 (d, J = 4.8 Hz, 1H), 7.78 (d, J = 7.9 Hz, 1H), 7.54-7.35 (m, 5H), 7.25-7.22 (m, 1H), 6.97-6.89 (m, 2H), 6.13 (s, 1H), 5.05-5.00 (m, 1H), 4.62-4.59 (m, 1H), 4.45 (s, 1H), 4.02-3.94 (m, 1H), 3.79-3.74 (m, 3H), 3.72-3.67 (m, 2H), 3.66-3.62 (m, 1H), 3.47-3.44 (m, 1H), 3.30-3.25 (m, 2H), 3.08-3.00 (m, 2H), 2.87-2.82 (m, 4H), 2.49-2.45 (m, 3H), 2.44-2.36 (m, 9H), 2.34-2.31 (m, 2H), 2.29-1.94 (m, 5H), 1.90 (s, 3H), 1.79-1.74 (m, 5H), 1.65-1.62 (m, 4H), 1.54-1.40 (m, 3H), 1.29-1.25 (m, 3H), 1.07 (d, J = 6.6 Hz, 3H), 1.02-0.79 (m, 4H) |
| 610 | A | A | 1086.58 | 1H NMR (400 MHz, Methanol-d4, ppm): δ 8.88 (s, 1H), 7.77-7.75 (m, 1H), 7.52 (s, 1H), 7.49-7.36 (m, 4H), 7.28-7.22 (m, 1H), 6.92-6.90 (m, 2H), 6.11 (s, 1H), 5.10-5.00 (m, 1H), 4.55-4.52(m, 1H), 4.51-4.49 (m, 1H), 4.08-3.95 (m,1H), 3.85-3.82 (m,1H), 3.81-3.72 (m, 4H), 3.71-3.52 (m, 3H), 3.31-3.22(m, 2H), 3.21-3.05 (m, 4H), 2.95-2.85 (m, 3H), 2.82-2.70 (m, 3H), 2.51-2.48 (m, 3H), 2.47-2.40 (m, 6H), 2.39-2.34 (m, 2H), 2.31-2.02 (m, 5H), 2.00-1.86 (m, 4H), 1.85-1.73 (m, 6H), 1.71-1.62(m, 2H), 1.58 (d, J = 12.4 Hz, 3H), 1.46-1.43(m, 1H), 1.38-1.34 (m, 2H), 1.28 (s, 1H), 1.10-1.06 (m, 3H), 0.91-0.85 (m, 3H) |
| 611 | D | NA | 1218.60 | 1H NMR (400 MHz, DMSO-d6,ppm) δ 14.13 (s, 1H), 8.99 (d, J = 3.6 Hz, 1H), 8.59 (d, J = 8.0 Hz, 1H), 7.91 (d, J = 7.9 Hz, 1H), 7.76 (d, J = 5.9 Hz, 1H), 7.51-7.43 (m, 4H), 7.39 (d, J = 8.0 Hz, 1H), 7.22 (t, J = 7.7 Hz, 1H), 6.85 (m, 2H), 6.55- 6.49 (m, 1H), 6.13 (m, 2H), 6.08-5.96 (m, 3H), 5.22-5.15 (m, 1H), 5.06 (s, 1H), 4.81 (s, 1H), 4.49 (s, 3H), 4.27 (d, J = 15.5 Hz, 2H), 3.74 (s, 1H), 3.57 (d, J = 9.2 Hz, 2H), 3.25 (d, J = 10.9 Hz, 1H), 3.01 (d, J = 11.7 Hz, 2H), 2.93-2.86 (m, 3H), 2.71- 2.63 (m, 4H), 2.45-2.30 (d, J = 5.8 Hz, 3H), 2.30-2.20 (m, 5H), 2.17 (m, 3H), 2.12-2.05 (m, 3H), 1.96 (s, 6H), 1.75 (s, 5H), 1.69 (m, 4H), 1.61 (s, 2H), 1.39 (d, J = 10.5 Hz, 1H), 1.23 (s, 3H), 1.08 (d, J = 11.1 Hz, 2H), 0.96-0.90 (m, 3H), 0.78 (d, J = 6.9 Hz, 3H). |
| 612 | A | A | 1218.61 | 1H NMR (400 MHz, DMSO-d6,) δ 14.13 (s, 1H), 8.99 (d, J = 3.6 Hz, 1H), 8.59 (d, J = 8.0 Hz, 1H), 7.91 (d, J = 7.9 Hz, 1H), 7.76 (d, J = 5.9 Hz, 1H), 7.60-7.39 (m, 5H), 7.22 (t, J = 7.7 Hz, 1H), 6.85 (m, 2H), 6.55-6.49 (m, 1H), 6.13- 6.08 (m, 2H), 6.00-5.96 (m, 3H), 5.22-5.06 (m, 2H), 4.81 (s, 1H), 4.49 (s, 3H), 4.27 (d, J = 15.5 Hz, 2H), 3.74-3.57 (m, 4H), 3.27 (m, 1H),3.25 (m, 1H), 3.01 (d, J = 11.7 Hz, 2H), 2.93- 2.86 (m, 3H), 2.80-2.67 (m, 4H), 2.45 (d, J = 5.8 Hz, 3H), 2.30-2.05 (m, 12H), 1.96 (s, 6H), 1.75-1.61 (m, 9H), 1.39 (d, J = 10.5 Hz, 2H), 1.23 (s, 1H), 1.08 (d, J = 11.1 Hz, 2H), 0.96-0.90 (m, 3H), 0.78 (d, J = 6.9 Hz, 3H). |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| 613 | D | NA | 929.40 | 1H NMR (400 MHz, DMSO-d6) δ 14.15 (s, 1H), 9.05-8.88 (m, 1H), 8.35-8.25 (m, 1H),8.00-7.88 (m, 1H), 7.83-7.73 (m, 1H), 7.54-7.45 (m, 1H), 7.44-7.35 (m, 2H), 7.34-7.25 (m, 1H), 7.24-7.15 (m, 1H), 6.95-6.65 (m, 2H), 6.60-6.48 (m, 1H), 6.25-6.12 (m, 1H), 6.11-6.05(m, 1H), 6.00-5.87 (m, 1H), 5.15-5.03(m, 1H), 4.92-4.80 (m, 1H), 4.58-4.45(m, 2H), 4.44-4.40(m, 1H), 4.35-4.20 (m, 4H),3.78-3.70 (m, 1H), 3.55-3.50 (m, 4H), 3.48-3.45(m, 2H), 3.05-2.95 (m, 2H), 2.45-2.42 (m, 2H), 2.25-2.02 (m, 6H), 2.00-1.90 (m, 2H), 1.82-1.70 (m, 1H), 1.50-1.45 (m, 1H), 1.35-1.30 (m, 2H), 1.26-1.20 (m, 2H), 1.18-1.15 (m, 1H), 1.05-0.90(m, 3H), 0.88-0.86 (m, 1H), 0.85-0.73 (m, 3H). |
| 614 | A | A | 929.40 | 1H NMR (400 MHz, DMSO-d6) δ 14.15 (s, 1H), 9.05-8.90 (m, 1H), 8.50-8.32 (m, 1H),7.99-7.85 (m, 1H), 7.84-7.70 (m, 1H), 7.52-7.32 (m, 4H), 7.25-7.16 (m, 1H), 6.90-6.70 (m, 2H), 6.60-6.47 (m, 1H), 6.23-6.11 (m, 1H), 6.10-6.00 (m, 1H), 5.99-5.83 (m, 2H), 5.18-5.02 (m, 1H), 5.00-4.85 (m, 1H), 4.55-4.45 (m, 2H), 4.40-4.21 (m, 5H), 3.73-3.60 (m, 2H), 3.10-2.99 (m, 3H), 2.25-2.10 (m, 6H), 2.05-1.90 (m, 3H), 1.82-1.70 (m, 1H), 1.42-1.35 (m, 2H), 1.30-1.15 (m, 5H), 1.03-0.90 (m, 3H), 0.88-0.75 (m, 3H). |
| 615 | D | NA | 1072.56 | 1H NMR (400 MHz, Methanol-d4) δ (ppm): 8.90 (s, 1H), 7.70-7.63 (m, 1H), 7.55-7.33 (m, 6H), 7.05-6.97 (m, 2H), 6.17-6.09 (m, 1H), 5.05-4.97 (m, 1H), 4.63-4.55 (m, 1H), 4.50-4.34 (m, 1H), 4.01-3.79 (m, 4H), 3.75 (s, 1H), 3.75-3.61 (m, 2H), 3.57-3.49 (m, 4H), 3.29-3.18 (m, 6H), 3.08-3.01 (m, 4H), 2.94-2.64 (m, 6H), 2.62-2.46 (m, 5H), 2.45-2.36 (m, 1H), 2.35-2.27 (m, 2H), 2.25-2.19 (m, 2H), 2.14-2.01 (m, 2H), 2.01-1.91 (m, 2H), 1.91-1.81 (m, 4H), 1.67-1.54 (m, 2H), 1.54-1.51 (m, 2H), 1.39-1.25 (m, 6H), 1.01-0.82 (m, 6H). |
| 616 | A | A | 1072.56 | 1H NMR (400 MHz, DMSO-d6) δ (ppm): 14.29 (s, 1H), 8.98 (s, 1H), 8.39 (d, 1H), 7.93 (d, 1H), 7.52 (s, 1H), 7.48-7.41 (m, 2H), 7.36 (d, 2H), 7.27-7.17 (m, 1H), 6.92-6.82 (m, 2H), 6.22 (s, 2H), 6.13 (s, 1H), 5.10 (d, 1H), 4.95-4.86 (m, 1H), 4.36 (t, 1H), 4.28 (s, 1H), 3.75-3.62 (m, 3H), 3.56 (d, 2H), 3.50-3.41 (m, 4H), 3.29 (s, 1H), 3.15 (d, 3H), 3.04-2.87 (m, 5H), 2.67 (s, 2H), 2.50-2.80 (m, 2H), 2.40-2.45 (m, 4H), 2.34 (s, 5H), 2.23 (s, 4H), 2.00 (s, 4H), 1.90-1.68 (m, 9H), 1.51-1.40 (m, 3H), 1.41-1.32 (m, 3H), 1.00-0.90 (m, 3H), 0.86-0.75 (m, 3H). |
| 617 | D | NA | 1072.56 | 1HNMR (400 MHz, DMSO-d6) δ 14.30 (s, 1H), 8.98 (m, 1H), 8.20 (m, 1H), 7.96-7.90 (m, 1H), 7.60 (m, 1H), 7.55-7.37 (m, 4H), 7.31 (m, 1H), 6.88 (m, 2H), 6.21-6.12 (s, 3H), 5.20 (d,1H),5.10 (m, 1H), 4.88 (t, J = 7.2 Hz, 1H), 4.42 (t, J = 7.7 Hz, 1H), 4.30-4.24 (m, 1H), 4.11 (s, 1H), 3.67 (m, 3H), 3.60-3.48 (m, 4H), 3.29 (s, 2H), 3.15 (m, 2H), 3.00 (t, J = 11.1 Hz, 5H), 2.68 (s, 4H), 2.45 (m, 3H), 2.26 (s, 4H), 2.14 (m, 7H), 1.96 (s, 7H), 1.76 (m, 5H), 1.66 (m, 1H), 1.49-1.41 (m, 3H), 1.07- 0.82 (m, 6H) |
| 618 | A | A | 1072.56 | 1H NMR (400 MHz, DMSO-d6) δ 14.50 (s, 1H), 8.98 (m, 1H), 8.40 (m, 1H), 7.96-7.90 (m, 1H), 7.60 (m, 1H), 7.55-7.37 (m, 2H), 7.41 (m, 2H), 7.31 (d, J = 7.7 Hz, 1H), 6.98 (s, 2H), 6.20 (d,2H), 6.10 (m, 1H), 5.20-5.08 (m, 1H), 5.00 (m, 1H), 4.88 (t, J = 7.2 Hz, 1H), 4.30-4.24 (m, 1H), 4.11 (s, 1H), 3.67 (m, 3H), 3.60-3.48 (m, 3H), 3.29 (s, 1H), 3.15 (m, 2H), 3.00 (t, J = 11.1 Hz, 2H), 2.88(m, 5H), 2.70(m, 4H), 2.68 (s, 3H), 2.45 (m, 5H), 2.26 (s, 7H), 2.14 (m, 8H), 1.96 (s, 5H), 1.76 (m, 1H), 1.20(m, 2H), 1.01(m, 3H), 1.07-0.82 (m, 3H) |
| 619 | D | NA | 1040.53 | 1H NMR (400 MHz, MeOD) δ: 8.91 (s, 1H), 8.39 (s, 1H), 8.32 (s, 1H), 8.12 (s, 1H), 7.74-7.71 (m, 1H), 7.49-7.38 (m, 5H), 7.06-7.02 (m, 2H), 6.01 (s, 1H), 5.03-4.98 (m, 1H), 4.59 (t, J = 8.0 Hz, 1H), 4.45 (brs, 1H), 4.38-4.25 (m, 3H), 3.79-3.35 (m, 6H), 3.23 (d, J = 4.0 Hz, 2H), 2.97 (t, J = 12.0 Hz, 2H), 2.86-2.58 (m, 5H), 2.50 (s, 3H), 2.41-2.33 (m, 2H), 2.27-2.14 (m, 5H), 2.06-1.96 (m, 3H), 1.81-1.76 (m, 3H), 1.64-1.56 (m, 7H), 1.55-1.50 (m, 5H), 1.08 (d, J = 8.0 Hz, 3H), 0.93 (d, J = 8.0 Hz, 3H). |
| 620 | D | NA | 1105.59 | 1H NMR (400 MHz, DMSO-d6) δ: 14.14 (s, 1H), 8.98-8.20 (m, 1H), 7.91 (d, J = 8.0 Hz, 1H), 7.77 (d, J = 6.0 Hz, 1H), 7.49 (s, 1H), 7.43 (s, 1H), 7.39-7.30 (m, 3H), 7.22 (m, J = 7.6 Hz, 1H), 6.90-6.76 (m, 3H), 6.52 (s, 2H), 6.13 (d, J = 4.2 Hz, 2H), 5.97 (s, 2H), 5.39-5.26 (m, 2H), 5.23-5.05 (m, 2H), 5.02-4.85 (m, 1H), 4.56-4.20 (m, 5H), 3.67 (d, J = 9.2 Hz, 1H), 3.56 (d, J = 17.6 Hz, 3H), 3.49-3.39 (m, 2H), 3.49-3.38 (m, 2H), 3.01 (d, J = 11.2 Hz, 2H), 2.82-2.58 (m, 4H), 2.31 (d, J = 16.8 Hz, 6H), 2.22-2.04 (m, 5H), 1.96 (s, 5H), 1.85-1.55 (m, 6H), 1.48-1.31 (m, 5H), 0.97-0.07 (m, 6H) |
| 621 | A | A | 1105.59 | 1H NMR (400 MHz, DMSO-d6) δ: 14.14 (s, 1H), 8.84-8.36 (m, 1H), 7.91 (d, J = 8.0 Hz, 1H), 7.77 (d, J = 6.0 Hz, 1H), 7.49 (s, 1H), |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | 7.38 (s, 4H), 7.22 (m, 1H), 6.79-6.90 (m, 3H), 6.49-6.57 (m, 2H), 6.12 (d, J = 14.0 Hz, 2H), 5.97 (s, 2H), 5.32 (s, 2H), 5.23-5.08 (m, 2H), 5.03-4.87 (m, 1H), 4.53-4.24 (m, 5H), 3.71 (d, J = 6.0 Hz, 1H), 3.63-3.653 (m, 3H), 3.42 (d, J = 11.2 Hz, 2H), 3.25 (d, J = 11.2 Hz, 2H), 3.01 (d, J = 11.6 Hz, 2H), 2.77-2.60 (m, 4H), 2.36-2.21 (m, 4H), 2.20-2.05 (m, 5H), 1.96 (s, 5H), 1.88-1.54 (m, 6H), 1.47-1.32 (m, 5H), 1.31-1.02 (m, 2H), 0.95 (d, J = 6.4 Hz, 3H), 0.86-0.75 (m, 3H). |
| 622 | A | A | 1104.59 | 1H NMR (400 MHz, DMSO-d6) δ: 14.20 (br s, 1H), 8.47 (d, J = 8.0 Hz, 1H), 7.98 (dd, J = 1.2, 8.0 Hz, 1H), 7.83 (d, J = 6.0 Hz, 1H), 7.59-7.49 (m, 4H), 7.47-7.41 (m, 2H), 7.31-7.25 (m, 1H), 6.96-6.87 (m, 2H), 6.58 (dd, J = 2.0, 6.0 Hz, 1H), 6.45-6.42 (m, 1H), 6.20 (d, J = 1.6 Hz, 1H), 6.16 (s, 1H), 6.03 (s, 2H), 5.29-5.20 (m, 1H), 5.17 (d, J = 3.6 Hz, 1H), 4.99 (quin, J = 7.2 Hz, 1H), 4.55 (br s, 2H), 4.43 (t, J = 7.6 Hz, 1H), 4.38-4.28 (m, 2H), 3.94-3.86 (m, 3H), 3.77 (br dd, J = 4.4, 10.4 Hz, 1H), 3.69-3.58 (m, 3H), 3.47 (br d, J = 9.2 Hz, 2H), 3.34-3.28 (m, 3H), 3.11-3.03 (m, 2H), 2.84-2.72 (m, 4H), 2.39-2.20 (m, 7H), 2.19-2.12 (m, 2H), 2.10-1.95 (m, 5H), 1.91-1.63 (m, 6H), 1.53-1.43 (m, 4H), 1.23-1.10 (m, 2H), 1.03-0.98 (m, 3H), 0.90-0.82 (m, 3H) |
| 623 | D | NA | 1093.52 | 1H NMR (400 MHz, DMSO-d6) δ: 9.06-8.84 (m, 1H), 8.21 (br d, J = 8.4 Hz, 1H), 7.92 (d, J = 8.0 Hz, 1H), 7.76 (d, J = 6.0 Hz, 1H), 7.52-7.29 (m, 5H), 7.22 (s, 1H), 6.89-6.82 (m, 2H), 6.52 (br d, J = 6.4 Hz, 1H), 6.18-6.10 (m, 2H), 5.97 (s, 2H), 5.11 (d, J = 4.0 Hz, 1H), 5.04-4.85 (m, 2H), 4.52-4.46 (m, 2H), 4.42 (t, J = 7.6 Hz, 1H), 4.28 (br d, J = 2.4 Hz, 1H), 3.68 (d, J = 9.2 Hz, 1H), 3.62-3.52 (m, 3H), 3.49-3.39 (m, 1H), 3.31 (br s, 7H), 3.07-2.97 (m, 4H), 2.47-2.43 (m, 5H), 2.32-2.25 (m, 3H), 2.18 (br d, J = 6.4 Hz, 6H), 2.00-1.94 (m, 2H), 1.89-1.75 (m, 3H), 1.71-1.58 (m, 2H), 1.57-1.41 (m, 3H), 1.35 (d, J = 7.2 Hz, 2H), 0.96 (d, J = 6.8 Hz, 2H), 0.82 (br d, J = 6.8 Hz, 4H) |
| 624 | A | A | 1093.52 | 1H NMR (400 MHz, DMSO-d6) δ: 8.99 (s, 1H), 8.40 (d, J = 7.6 Hz, 1H), 7.92 (d, J = 8.0 Hz, 1H), 7.77 (d, J = 6.0 Hz, 1H), 7.53-7.42 (m, 3H), 7.38 (s, 2H), 7.26-7.20 (m, 1H), 6.89-6.82 (m, 2H), 6.55-6.49 (m, 1H), 6.15-6.09 (m, 2H), 5.97 (s, 2H), 5.10 (d, J = 3.6 Hz, 1H), 4.94 (td, J = 7.2, 14.4 Hz, 2H), 4.49 (br s, 2H), 4.37 (t, J = 7.6 Hz, 1H), 4.29 (br s, 1H), 3.71 (dd, J = 4.4, 10.4 Hz, 1H), 3.66-3.53 (m, 3H), 3.42 (br d, J = 11.2 Hz, 1H), 3.31-3.21 (m, 5H), 3.10-2.99 (m, 4H), 2.46 (s, 4H), 2.32 (br s, 3H), 2.26-2.04 (m, 8H), 2.03-1.92 (m, 3H), 1.82 (br s, 3H), 1.65 (br d, J = 10.0 Hz, 2H), 1.59-1.48 (m, 2H), 1.38 (d, J = 7.2 Hz, 3H), 0.95 (d, J = 6.4 Hz, 3H), 0.79 (d, J = 6.8 Hz, 3H) |
| 625 | D | NA | 1037.48 | 1H-NMR (400 MHz, CD3OD, ppm) δ 8.88 (s, 1H), 8.30 (s, 1H), 8.14 (d, J = 5.6 Hz, 1H), 7.91 (d, J = 7.2 Hz, 1H), 7.50-7.43 (m, 6H), 7.38 (d, J = 8.4 Hz, 2H), 7.16 (s, 1H), 6.97 (s, 2H), 6.14 (s, 1H), 5.27 (s, 1H), 5.03-5.01 (m, 1H), 4.87 (s, 1H), 4.45-4.42 (m, 2H), 3.76-3.69 (m, 5H), 3.33-3.31(m, 1H), 2.80-2.77 (m, 4H), 2.77-2.75 (m, 8H), 2.300-2.18 (m, 5H), 2.01-1.99 (m, 1H), 1.88-1.86 (m, 2H), 1.80-1.77 (m, 3H), 1.76-1.73 (m, 5H), 1.26-1.06 (m, 2H), 0.94 (s, 3H), 0.93 (m, 3H) |
| 626 | A | A | 1037.48 | 1H-NMR (400 MHz, CD3OD, ppm) δ 8.88 (s, 1H), 8.30 (s, 1H), 8.14 (d, J = 5.6 Hz, 1H), 7.91 (d, J = 7.2 Hz, 1H), 7.52-7.44 (m, 6H), 7.31-7.28 (m, 2H), 7.02-6.95 (m, 3H), 6.14 (s, 1H), 5.28-5.27 (m, 1H), 5.03-5.01 (m, 1H), 4.87-4.85 (m, 1H), 4.45-4.42 (m, 2H), 3.86-3.79 (m, 1H), 3.70-3.65 (m, 4H), 3.33-3.31(m, 1H), 2.85-2.77 (m, 4H), 2.77-2.75 (m, 8H), 2.30-2.08 (m, 5H), 2.01-1.72 (m, 6H), 1.65-1.53 (m, 5H), 1.27-1.21 (m, 2H), 0.93 (s, 3H), 0.91 (m, 3H) |
| 627 | A | A | 1082.50 | 1H NMR (400 MHz, DMSO-d6) δ: 14.26-14.06 (m, 1H), 8.98 (s, 1H), 8.40 (d, J = 7.6 Hz, 1H), 7.97-7.86 (m, 1H), 7.77 (d, J = 6.0 Hz, 1H), 7.52-7.41 (m, 3H), 7.39-7.31 (m, 2H), 7.22 (t, J = 7.6 Hz, 1H), 6.93-6.79 (m, 2H), 6.59-6.48 (m, 1H), 6.13 (d, J = 2.0 Hz, 1H), 6.09-6.05 (m, 1H), 5.99-5.85 (m, 2H), 5.25-5.14 (m, 1H), 5.11-4.98 (m, 1H), 4.96-4.86 (m, 1H), 4.49 (br s, 2H), 4.37 (t, J = 8.0 Hz, 1H), 4.30-4.23 (m, 2H), 4.18 (br t, J = 5.6 Hz, 2H), 3.74 (br d, J = 2.4 Hz, 1H), 3.64 (d, J = 9.6 Hz, 1H), 3.53 (br d, J = 2.4 Hz, 1H), 3.47-3.41 (m, 1H), 3.25 (br d, J = 12.0 Hz, 2H), 3.09-2.98 (m, 2H), 2.94-2.84 (m, 1H), 2.79-2.70 (m, 1H), 2.67-2.54 (m, 3H), 2.45 (s, 3H), 2.32-2.21 (m, 5H), 2.20-2.14 (m, 2H), 2.05-1.88 (m, 3H), 1.78 (ddd, J = 4.8, 8.0, 12.8 Hz, 1H), 1.68-1.43 (m, 4H), 1.38 (d, J = 7.2 Hz, 3H), 0.96 (t, J = 6.0 Hz, 6H), 0.86-0.76 (m, 3H) |
| 628 | A | A | 1082.50 | 1H NMR (400 MHz, DMSO-d6) δ: 14.12 (s, 1H), 8.98 (s, 1H), 8.39 (d, J = 7.6 Hz, 1H), 7.91 (d, J = 8.0 Hz, 1H), 7.77 (d, J = 6.0 |

TABLE 2D-continued

| Target protein degradation via exemplary bifunctional degradation compounds of Table 1D | | | | |
|---|---|---|---|---|
| Ex No | *$DC_{50}$ (nM) | **$D_{max}$ (%) | MH + 1 | NMR transcript |
| | | | | Hz, 1H), 7.54-7.41 (m, 3H), 7.38-7.33 (m, 2H), 7.27-7.12 (m, 1H), 6.92-6.76 (m, 2H), 6.52 (dd, J = 2.0, 6.0 Hz, 1H), 6.13 (d, J = 1.6 Hz, 1H), 6.07 (s, 1H), 6.00-5.89 (m, 2H), 5.28-5.11 (m, 1H), 5.11-5.01 (m, 1H), 4.91 (br t, J = 7.2 Hz, 1H), 4.49 (br d, J = 1.2 Hz, 2H), 4.37 (t, J = 8.0 Hz, 1H), 4.33-4.22 (m, 2H), 4.18 (br t, J = 6.0 Hz, 2H), 3.70 (dd, J = 4.4, 10.8 Hz, 1H), 3.64 (d, J = 9.6 Hz, 1H), 3.53 (br d, J = 2.8 Hz, 1H), 3.43 (br d, J = 8.8 Hz, 1H), 3.25 (br d, J = 10.4 Hz, 2H), 3.01 (br d, J = 11.6 Hz, 2H), 2.94-2.84 (m, 1H), 2.80-2.68 (m, 1H), 2.64-2.54 (m, 3H), 2.45 (s, 3H), 2.32-2.20 (m, 5H), 2.19-2.12 (m, 2H), 2.06-1.91 (m, 3H), 1.78 (s, 1H), 1.67-1.43 (m, 4H), 1.37 (d, J = 7.2 Hz, 3H), 1.03-0.90 (m, 6H), 0.85-0.77 (m, 3H) |
| 629 | B | A | 1122.55 | 1H NMR (400 MHz, DMSO-d6) δ: 14.15 (s, 1H), 8.75-8.69 (m, 1H), 8.19 (d, J = 8.0 Hz, 1H), 7.92 (dd, J = 1.2, 8.0 Hz, 1H), 7.77 (d, J = 6.0 Hz, 1H), 7.51-7.33 (m, 3H), 7.27-7.20 (m, 2H), 6.90-6.82 (m, 2H), 6.53 (dd, J = 2.0, 6.0 Hz, 1H), 6.17-6.09 (m, 2H), 5.98 (s, 2H), 5.64-5.51 (m, 2H), 5.25-5.15 (m, 1H), 5.12-4.80 (m, 2H), 4.55-4.40 (m, 3H), 4.33-4.23 (m, 2H), 3.73-3.39 (m, 5H), 3.25 (br d, J = 10.8 Hz, 4H), 3.02 (br d, J = 11.6 Hz, 2H), 2.78-2.69 (m, 2H), 2.32-2.22 (m, 5H), 2.22-2.15 (m, 2H), 2.14-2.06 (m, 2H), 2.03-1.90 (m, 5H), 1.86-1.73 (m, 3H), 1.71-1.56 (m, 3H), 1.47-1.31 (m, 5H), 1.16-1.01 (m, 2H), 0.96 (d, J = 6.8 Hz, 2H), 0.86-0.73 (m, 4H) |
| 630 | A | A | 1122.55 | 1H NMR (400 MHz, DMSO-d6) δ: 14.15 (br s, 1H), 8.77-8.67 (m, 1H), 8.37 (d, J = 7.6 Hz, 1H), 7.92 (dd, J = 1.2, 8.0 Hz, 1H), 7.77 (d, J = 6.0 Hz, 1H), 7.54-7.39 (m, 3H), 7.32-7.18 (m, 3H), 6.93-6.82 (m, 2H), 6.53 (dd, J = 2.0, 6.0 Hz, 1H), 6.19-6.06 (m, 2H), 5.98 (s, 2H), 5.62-5.51 (m, 2H), 5.25-5.14 (m, 1H), 5.11 (d, J = 3.6 Hz, 1H), 4.88 (quin, J = 7.2 Hz, 1H), 4.50 (br s, 2H), 4.36 (t, J = 7.6 Hz, 1H), 4.32-4.24 (m, 2H), 3.71 (br dd, J = 4.4, 10.4 Hz, 1H), 3.65-3.52 (m, 3H), 3.41 (br d, J = 9.6 Hz, 1H), 3.25 (br d, J = 10.4 Hz, 2H), 3.02 (br d, J = 11.6 Hz, 2H), 2.77-2.69 (m, 2H), 2.32-2.07 (m, 9H), 2.04-1.91 (m, 5H), 1.84-1.57 (m, 6H), 1.48-1.31 (m, 5H), 1.17-1.03 (m, 2H), 1.00-0.92 (m, 3H), 0.87-0.75 (m, 3H) |
| 631 | A | A | 1104.59 | 1H NMR (400 MHz, DMSO-d6) δ: 14.15 (s, 1H), 8.75-8.69 (m, 1H), 8.19 (d, J = 8.0 Hz, 1H), 7.92 (dd, J = 1.2, 8.0 Hz, 1H), 7.77 (d, J = 6.0 Hz, 1H), 7.51-7.33 (m, 3H), 7.27-7.20 (m, 2H), 6.90-6.82 (m, 2H), 6.53 (dd, J = 2.0, 6.0 Hz, 1H), 6.17-6.09 (m, 2H), 5.98 (s, 2H), 5.64-5.51 (m, 2H), 5.25-5.15 (m, 1H), 5.12-4.80 (m, 2H), 4.55-4.40 (m, 3H), 4.33-4.23 (m, 2H), 3.73-3.39 (m, 5H), 3.25 (br d, J = 10.8 Hz, 4H), 3.02 (br d, J = 11.6 Hz, 2H), 2.78-2.69 (m, 2H), 2.32-2.22 (m, 5H), 2.22-2.15 (m, 2H), 2.14-2.06 (m, 2H), 2.03-1.90 (m, 5H), 1.86-1.73 (m, 3H), 1.71-1.56 (m, 3H), 1.47-1.31 (m, 5H), 1.16-1.01 (m, 2H), 0.96 (d, J = 6.8 Hz, 2H), 0.86-0.73 (m, 4H) |
| 632 | A | A | 981.46 | 1H NMR (400 MHz, METHANOL-d4) δ: 8.91 (s, 1H), 8.47 (s, 1H), 8.34 (d, J = 0.9 Hz, 1H), 8.11 (s, 1H), 7.73 (dd, J = 1.5, 8.1 Hz, 1H), 7.52-7.36 (m, 5H), 7.09-6.97 (m, 2H), 6.04-5.93 (m, 1H), 5.45 (br dd, J = 1.9, 6.9 Hz, 1H), 5.08-4.97 (m, 1H), 4.52 (t, J = 8.2 Hz, 1H), 4.57-4.41 (m, 1H), 4.28 (br t, J = 5.8 Hz, 2H), 3.86 (dd, J = 4.0, 10.9 Hz, 1H), 3.79-3.59 (m, 2H), 3.57-3.45 (m, 2H), 3.26-3.14 (m, 3H), 3.04-2.88 (m, 3H), 2.50 (s, 3H), 2.44-2.31 (m, 3H), 2.30-2.15 (m, 3H), 2.26-1.98 (m, 3H), 1.89-1.74 (m, 6H), 1.65-1.43 (m, 5H), 1.07 (d, J = 6.5 Hz, 3H), 0.97-0.83 (m, 3H). |
| 633 | A | A | 981.45 | 1H NMR (400 MHz, METHANOL-d4) δ: 8.83 (d, J = 6.8 Hz, 1H), 8.37 (s, 1H), 8.25 (d, J = 3.4 Hz, 1H), 8.01 (d, J = 1.3 Hz, 1H), 7.66-7.57 (m, 1H), 7.41-7.21 (m, 5H), 7.00-6.87 (m, 2H), 5.90 (d, J = 6.0 Hz, 1H), 5.34 (br d, J = 7.0 Hz, 1H), 4.99-4.86 (m, 1H), 4.78 (s, 44H), 4.71-4.63 (m, 1H), 4.49 (s, 1H), 4.35 (br s, 1H), 4.24-4.11 (m, 4H), 3.80-3.48 (m, 3H), 3.45-3.33 (m, 2H), 3.16-3.02 (m, 3H), 2.86 (br dd, J = 3.9, 12.5 Hz, 3H), 2.41-2.36 (m, 3H), 2.33-2.08 (m, 5H), 1.98-1.85 (m, 3H), 1.85-1.75 (m, 1H), 1.72-1.60 (m, 5H), 1.56-1.50 (m, 1H), 1.37-1.32 (m, 3H), 0.98 (d, J = 6.6 Hz, 3H), 0.81 (dd, J = 6.7, 9.9 Hz, 3H). |
| 634 | A | A | 1082.50 | 1H NMR (400 MHz, METHANOL-d4) δ: 8.89-8.87 (m, 1H), 7.79-7.73 (m, 2H), 7.49-7.38 (m, 5H), 7.24 (t, J = 7.6 Hz, 1H), 6.93-6.88 (m, 2H), 6.55 (dd, J = 2.0, 6.0 Hz, 1H), 6.14 (d, J = 2.0 Hz, 1H), 6.02 (s, 1H), 5.23-4.96 (m, 2H), 4.85-4.73 (m, 1H), |

TABLE 2D-continued

Target protein degradation via exemplary bifunctional degradation compounds of Table 1D

| Ex No | *DC$_{50}$ (nM) | **D$_{max}$ (%) | MH + 1 | NMR transcript |
|---|---|---|---|---|
| | | | | 4.64-4.25 (m, 7H), 3.85-3.42 (m, 3H), 3.40-3.35 (m, 2H), 3.21-3.00 (m, 4H), 2.83-2.71 (m, 1H), 2.50-2.47 (m, 3H), 2.45-2.13 (m, 12H), 2.07-1.86 (m, 3H), 1.62-1.42 (m, 4H), 1.32-1.21 (m, 1H), 1.19-1.12 (m, 3H), 1.07 (d, J = 6.8 Hz, 3H), 0.95-0.87 (m, 3H). |
| 635 | A | A | 1096.52 | 1H NMR (400 MHz, DMSO-d6) δ: 14.14 (s, 1H), 8.99-8.97 (m, 1H), 8.42-8.26 (m, 1H), 7.91 (d, J = 8.0 Hz, 1H), 7.76 (d, J = 6.0 Hz, 1H), 7.49-7.30 (m, 5H), 7.24-7.20 (m, 1H), 6.87-6.82 (m, 2H), 6.52-6.51 (m, 1H), 6.13 (d, J = 2.0 Hz, 1H), 6.09-6.04 (m, 1H), 5.96 (s, 2H), 5.18-5.09 (m, 2H), 5.03-4.86 (m, 1H), 4.49 (s, 2H), 4.43-4.34 (m, 1H), 4.31-4.26 (m, 2H), 4.11-4.04 (m, 2H), 3.75-3.63 (m, 1H), 3.56- 3.45 (m, 2H), 3.26-3.23 (m, 3H), 3.01 (d, J = 11.6 Hz, 2H), 2.88-2.80 (m, 2H), 2.46-3.45 (m, 3H), 2.27-2.16 (m, 7H), 2.07-1.95 (m, 3H), 1.80-1.75 (m, 3H), 1.46-1.34 (m, 3H), 1.08-0.94 (m, 12H), 0.83-0.74 (m, 4H). |
| 636 | A | A | 1082.50 | 1H NMR (400 MHz, DMSO-d6) δ: 14.13 (s, 1H), 8.98 (s, 1H), 8.84-8.31 (m, 1H), 7.91 (dd, J = 1.2, 8.0 Hz, 1H), 7.77 (d, J = 6.0 Hz, 1H), 7.49 (s, 1H), 7.47-7.41 (m, 2H), 7.39-7.34 (m, 2H), 7.26-7.19 (m, 1H), 6.90-6.81 (m, 2H), 6.52 (dd, J = 2.0, 6.0 Hz, 1H), 6.13 (d, J = 2.0 Hz, 1H), 6.07 (s, 1H), 5.98-5.89 (m, 2H), 5.22-5.14 (m, 1H), 5.08 (d, J = 3.6 Hz, 1H), 4.95-4.86 (m, 1H), 4.49 (br s, 2H), 4.37 (t, J = 7.6 Hz, 1H), 4.32-4.24 (m, 2H), 4.18 (br t, J = 5.6 Hz, 2H), 3.70 (dd, J = 4.4, 10.8 Hz, 1H), 3.64 (d, J = 9.6 Hz, 1H), 3.49-3.39 (m, 1H), 3.27-3.18 (m, 3H), 3.07-2.96 (m, 3H), 2.91 (br d, J = 11.6 Hz, 1H), 2.62-2.55 (m, 1H), 2.45 (s, 3H), 2.31-2.21 (m, 6H), 2.20-2.13 (m, 3H), 2.06-1.90 (m, 3H), 1.86-1.74 (m, 3H), 1.48-1.35 (m, 3H), 1.33-1.23 (m, 1H), 1.10-0.99 (m, 4H), 0.98-0.92 (m, 3H), 0.84-0.76 (m, 3H) |
| 637 | B | A | 1019.40 | 1H NMR (400 MHz, DMSO-d6) δ: 9.01 (d, J = 7.6 Hz, 1H), 8.55-8.50 (m, 1H), 8.40 (d, J = 8.0 Hz, 1H), 8.24 (s, 1H), 8.19 (s, 1H), 7.92-7.84 (m, 2H), 7.78-7.74 (m, 1H), 7.63-7.45 (m, 4H), 7.31 (m, 1H), 7.03-6.90 (m, 3H), 6.19-6.13 (m, 1H), 5.47-5.39 (m, 1H), 5.10-4.90 (m, 1H), 4.59-4.41 (m, 1H), 4.37-4.21 (m, 2H), 3.73-3.54 (m, 9H), 3.12-2.70 (m, 10H), 2.30-2.17 (m, 5H), 2.08-1.81 (m, 6H), 1.75 (d, J = 4.8 Hz, 2H), 1.70 (d, J = 6.8 Hz, 3H), 1.59 (s, 1H), 1.46 (d, J = 7.2 Hz, 1H), 1.41-1.13 (m, 5H), 0.95 (d, J = 6.8 Hz, 2H), 0.85-0.75 (m, 4H) |
| 638 | A | A | 1019.40 | 1H NMR (400 MHz, DMSO-d6) δ: 9.22-8.91 (m, 1H), 8.55-8.51 (m, 1H), 8.47 (d, J = 7.6 Hz, 1H), 8.25 (s, 1H), 8.18 (s, 1H), 7.89-7.82 (m, 2H), 7.76 (d, J = 2.0 Hz, 1H), 7.62-7.49 (m, 4H), 7.32 (t, J = 7.6 Hz, 1H), 7.17-6.92(m, 3H), 6.16 (s, 1H), 5.49-5.39 (m, 1H), 4.98 (m, 1H), 4.75-4.65 (m, 1H), 4.42-4.21 (m, 3H), 3.65 (d, J = 13.2 Hz, 4H), 3.57 (d, J = 9.6 Hz, 2H), 3.54-3.40 (m, 4H), 3.32 (d, J = 8.8 Hz, 2H), 3.12-2.86 (m, 6H), 2.78 (m, J = 12.0 Hz, 3H), 2.32-2.12 (m, 5H), 2.08-1.99 (m, 2H), 1.86 (s, 2H), 1.82-1.75 (m, 2H), 1.70 (d, J = 6.8 Hz, 3H), 1.62 (d, J = 10.8 Hz, 1H), 1.39 (d, J = 7.2 Hz, 3H), 1.30-1.14 (m, 2H), 1.01-0.91 (m, 3H), 0.85-0.76 (m, 3H) |
| 639 | D | NA | 1049.54 | 1H NMR (400 MHz, METHANOL-d4) δ: 8.49-8.28 (m, 2H), 7.77 (d, J = 6.3 Hz, 1H), 7.72 (br d, J = 8.0 Hz, 1H), 7.66 (d, J = 8.1 Hz, 2H), 7.54-7.38 (m, 3H), 7.23 (br t, J = 7.6 Hz, 1H), 6.96-6.84 (m, 2H), 6.57 (br d, J = 4.5 Hz, 1H), 6.17-6.06 (m, 2H), 5.20-5.10 (m, 1H), 5.50-4.92 (m, 1H), 4.55 (br d, J = 7.8 Hz, 3H), 4.47-4.22 (m, 2H), 3.75-3.62 (m, 6H), 3.36 (br d, J = 10.8 Hz, 3H), 3.29 (br s, 1H), 3.22 (br s, 2H), 3.10 (br d, J = 11.5 Hz, 2H), 3.00 (br d, J = 5.1 Hz, 2H), 2.90-2.66 (m, 2H), 2.52-2.41 (m, 4H), 2.35 (br dd, J = 6.6, 9.0 Hz, 1H), 2.29-2.20 (m, 3H), 2.15 (br d, J = 5.1 Hz, 2H), 2.05 (br s, 3H), 1.92 (ddd, J = 4.6, 8.4, 13.1 Hz, 3H), 1.83 (br d, J = 11.3 Hz, 2H), 1.57-1.44 (m, 3H), 1.37 (br d, J = 6.5 Hz, 2H), 1.08-0.94 (m, 3H), 0.93-0.83 (m, 3H). |
| 640 | A | A | 1049.54 | 1H NMR (400 MHz, METHANOL-d4) δ: 8.39 (br s, 1H), 7.77 (d, J = 6.3 Hz, 1H), 7.74 (d, J = 7.3 Hz, 1H), 7.71-7.66 (m, 2H), 7.53-7.41 (m, 3H), 7.27-7.18 (m, 1H), 6.95-6.85 (m, 2H), 6.56 (dd, J = 2.0, 6.3 Hz, 1H), 6.17-6.03 (m, 2H), 5.20-5.11 (m, 1H), 5.02 (q, J = 7.2 Hz, 1H), 4.86 (s, 3H), 4.54-4.50 (m, 3H), 4.40 (br dd, J = 5.8, 12.1 Hz, 3H), 3.83 (dd, J = 4.2, 10.8 Hz, 1H), 3.72 (br d, J = 12.9 Hz, 3H), 3.65-3.57 (m, 2H), 3.54-3.41 (m, 1H), 3.37 (br s, 1H), 3.34 (br d, J = 4.4 Hz, 2H), 3.15-3.08 (m, 3H), 2.97 (br d, J = 7.0 Hz, 2H), 2.90 (br t, J = 11.6 Hz, 2H), 2.51-2.40 (m, 4H), 2.36 (td, J = 6.6, 9.8 Hz, 1H), 2.29-2.22 (m, 2H), 2.21-2.12 (m, 3H), 2.03 (br s, 3H), 1.92 (ddd, J = 4.4, 8.8, 13.2 Hz, 3H), 1.82 (br d, J = 12.6 Hz, 2H), 1.58-1.47 (m, 3H), 1.42-1.30 (m, 2H), 1.08-1.00 (m, 3H), 0.92-0.84 (m, 3H) |

TABLE 2D-continued

| Target protein degradation via exemplary bifunctional degradation compounds of Table 1D | | | | |
|---|---|---|---|---|
| Ex No | *$DC_{50}$ (nM) | **$D_{max}$ (%) | MH + 1 | NMR transcript |
| 641 | D | NA | 1137.40 | 1H NMR (400 MHz, DMSO-d6) δ: 9.04-8.87 (m, 1H), 8.24-8.16 (m, 1H), 7.91 (dd, J = 1.2, 8.0 Hz, 1H), 7.76 (d, J = 6.0 Hz, 1H), 7.55-7.27 (m, 5H), 7.27-7.19 (m, 1H), 6.91-6.77 (m, 2H), 6.52 (dd, J = 2.0, 6.0 Hz, 1H), 6.17-6.09 (m, 2H), 5.97 (s, 2H), 5.27-5.13 (m, 1H), 5.01 (s, 1H), 4.87 (br t, J = 7.2 Hz, 1H), 4.49 (br s, 2H), 4.42 (t, J = 7.6 Hz, 1H), 4.27 (br d, J = 4.8 Hz, 2H), 3.67 (br d, J = 8.8 Hz, 2H), 3.55-3.51 (m, 2H), 3.26 (br s, 6H), 3.13-2.96 (m, 5H), 2.77 (br d, J = 10.4 Hz, 2H), 2.47-2.42 (m, 3H), 2.31-2.10 (m, 11H), 2.06-1.90 (m, 3H), 1.84-1.64 (m, 3H), 1.61-1.38 (m, 6H), 1.35 (d, J = 7.2 Hz, 2H), 0.95 (d, J = 6.8 Hz, 2H), 0.88-0.78 (m, 3H), 0.76 (s, 1H) |
| 642 | A | A | 1109.40 | 1H NMR (400 MHz, METHANOL-d4) δ: 8.87 (s, 1H), 8.52 (br s, 2H), 8.29 (s, 1H), 8.09 (d, J = 2.00 Hz, 2H), 7.85 (d, J = 7.75 Hz, 1H), 7.37-7.46 (m, 4H), 7.27 (t, J = 7.13 Hz, 1H), 6.92-6.97 (m, 2H), 6.04-6.11 (m, 1H), 5.00-5.07 (m, 1H), 4.51 (t, J = 8.13 Hz, 1H), 4.45 (m, 1H), 4.27-4.35 (m, 1H), 4.20-4.26 (m, 1H), 3.85 (dd, J = 10.69, 4.06 Hz, 1H), 3.70 (m, , 2H), 3.54-3.65 (m, 3H), 3.42 (m, 1H), 3.17 (m, 2H), 3.05 (d, J = 7.38 Hz, 2H), 2.88 (m, 4H), 2.77 (m, 3H), 2.62-2.71 (m, 2H), 2.48 (s, 3H), 2.36 (m, 1H), 2.10-2.27 (m, 6H), 1.98 (m, 5H), 1.82 (m, 4H), 1.58-1.62 (m, 4H), 1.41-1.52 (m, 5H), 1.26-1.37 (m, 2H), 1.05 (d, J = 6.50 Hz, 3H), 0.85-0.93 (m, 3H). |
| 643 | A | A | 1135.40 | 1H NMR (400 MHz, DMSO-d6) δ: 9.01-8.95 (m, 1H), 8.23-8.14 (m, 1H), 7.94-7.87 (m, 1H), 7.76 (d, J = 6.0 Hz, 1H), 7.51-7.45 (m, 2H), 7.45-7.37 (m, 2H), 7.34-7.29 (m, 1H), 7.25-7.19 (m, 1H), 6.89-6.81 (m, 2H), 6.52 (dd, J = 2.0, 6.0 Hz, 1H), 6.13 (d, J = 2.0 Hz, 1H), 5.99-5.86 (m, 3H), 5.22-5.15 (m, 1H), 5.13-4.94 (m, 1H), 4.93-4.83 (m, 1H), 4.56-4.46 (m, 2H), 4.42 (dt, J = 3.2, 7.6 Hz, 1H), 4.31-4.22 (m, 2H), 3.67 (d, J = 8.8 Hz, 1H), 3.59-3.50 (m, 2H), 3.23 (br s, 3H), 3.01 (br d, J = 11.6 Hz, 2H), 2.77-2.67 (m, 2H), 2.52 (br s, 2H), 2.46 (br s, 2H), 2.44 (s, 2H), 2.31-2.22 (m, 6H), 2.17 (br d, J = 7.2 Hz, 2H), 2.11-1.87 (m, 7H), 1.85-1.72 (m, 4H), 1.64-1.26 (m, 9H), 1.19-1.08 (m, 3H), 0.96 (d, J = 6.8 Hz, 2H), 0.87-0.80 (m, 3H), 0.76 (d, J = 6.8 Hz, 1H). |
| 644 | A | A | 1135.40 | 1H NMR (400 MHz, DMSO-d6) δ: 14.13 (br s, 1H), 9.02-8.94 (m, 1H), 8.39 (dd, J = 2.8, 7.6 Hz, 1H), 7.95-7.88 (m, 1H), 7.77 (d, J = 6.0 Hz, 1H), 7.49 (s, 1H), 7.47-7.41 (m, 2H), 7.40-7.29 (m, 2H), 7.25-7.19 (m, 1H), 6.90-6.80 (m, 2H), 6.52 (dd, J = 2.0, 6.0 Hz, 1H), 6.13 (d, J = 1.6 Hz, 1H), 5.96 (s, 2H), 5.93-5.87 (m, 1H), 5.24-5.14 (m, 1H), 5.12-5.07 (m, 1H), 4.98-4.85 (m, 1H), 4.49 (br s, 2H), 4.44-4.34 (m, 1H), 4.32-4.22 (m, 2H), 3.76-3.65 (m, 1H), 3.59-3.51 (m, 1H), 3.47-3.39 (m, 1H), 3.29-3.21 (m, 6H), 3.01 (br d, J = 11.6 Hz, 2H), 2.70 (br d, J = 5.2 Hz, 1H), 2.53-2.51 (m, 2H), 2.46-2.44 (m, 3H), 2.31-2.21 (m, 6H), 2.19-2.12 (m, 2H), 2.08-1.88 (m, 6H), 1.85-1.70 (m, 4H), 1.60-1.43 (m, 3H), 1.42-1.31 (m, 5H), 1.17-1.09 (m, 3H), 0.98-0.92 (m, 3H), 0.85-0.75 (m, 3H). |
| 645 | A | A | 1137.40 | 1H NMR (400 MHz, DMSO-d6) δ: 9.11-8.74 (m, 2H), 8.37 (br d, J = 7.6 Hz, 1H), 7.93 (br d, J = 4.8 Hz, 1H), 7.74-7.57 (m, 1H), 7.53-7.41 (m, 3H), 7.38 (br d, J = 8.2 Hz, 3H), 6.98 (br d, J = 17.6 Hz, 2H), 6.81 (br s, 3H), 6.26 (br s, 1H), 6.18 (s, 1H), 5.55-5.27 (m, 1H), 5.26-5.19 (m, 1H), 4.92 (br t, J = 7.2 Hz, 1H), 4.80 (br d, J = 8.0 Hz, 2H), 4.40-4.26 (m, 3H), 3.71 (br d, J = 4.4 Hz, 3H), 3.59-3.57 (m, 3H), 3.17 (br s, 9H), 2.47-2.44 (m, 6H), 2.22 (br dd, J = 6.0, 8.8 Hz, 5H), 2.08-1.92 (m, 6H), 1.81 (br s, 3H), 1.74-1.56 (m, 5H), 1.47 (br d, J = 6.8 Hz, 1H), 1.39 (d, J = 7.2 Hz, 3H), 1.03-0.91 (m, 3H), 0.86-0.73 (m, 3H) |
| 646 | A | A | 1091.40 | 1H NMR (400 MHz, METHANOL-d4) δ: 8.87 (s, 1H), 8.59 (br s, 1H), 7.68-7.82 (m, 2H), 7.35-7.49 (m, 5H), 7.23 (br t, J = 7.13 Hz, 1H), 6.90 (d, J = 7.88 Hz, 2H), 6.55 (d, J = 0.4 Hz, 1H), 6.03-6.18 (m, 2H), 5.10-5.17 (m, 1H), 5.01-5.06 (m, 1H) 4.40-4.49 (m, 4H), 3.83-3.86 (m, 1H), 3.59-3.64 (m, 2H), 3.36 (s, 3H), 3.20-3.28 (m, 6H), 3.07-3.18 (m, 7H), 2.73-2.90 (m, 2H), 2.48 (s, 3H), 2.32-2.42 (m, 4H), 2.10-2.27 (m, 5H), 1.88-2.00 (m, 1H), 1.72-1.81 (m, 2H), 1.58-1.68 (m, 4H), 1.52 (d, J = 6.88 Hz, 3H), 1.05 (d, J = 6.50 Hz, 3H), 0.85-0.93 (m, 3H). |
| 647 | D | NA | 1091.40 | 1H NMR (400 MHz, METHANOL-d4) δ: 8.85-8.89 (m, 1H), 8.56 (br s, 1H), 7.70-7.80 (m, 2H), 7.40-7.48 (m, 3H), 7.33-7.39 (m, 2H), 7.22 (br t, J = 7.63 Hz, 1H), 6.86-6.90 (m, 2H), 6.54 (br d, J = 5.50 Hz, 1H), 6.09-6.17 (m, 2H), 5.10-5.12 (m, 1H), 4.95-5.01 (m, 1H), 4.51-4.52 (m, 2H), 4.41-4.43 (m, 1H), 3.64-3.75 (m, 3H), 3.17-3.25 (m, 6H), 3.09-3.12 (m, 2H), 3.00-3.04 (m, 2H), 2.88-2.97 m, 4H), 2.69-2.81 (m, 1H), 2.47-- |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | 2.51 (m, 4H), 2.32-2.41 (m, 4H), 2.19-2.27 (m, 3H), 2.12-2.17 (m, 2H), 1.93-2.00 (m, 1H), 1.65-1.74 (m, 4H), 1.55-1.64 (m, 5H), 1.49 (br d, J = 7.00 Hz, 3H), 1.06 (d, J = 6.63 Hz, 3H), 0.91 (d, J = 6.63 Hz, 3H). |
| 648 | A | A | 1095.40 | 1H NMR (400 MHz, CHLOROFORM-d) δ = 8.87 (s, 1H), 8.56 (br s, 1H), 8.28 (br s, 1H), 8.08 (br d, J = 4.0 Hz, 2H), 7.85 (br d, J = 7.5 Hz, 1H), 7.35-7.48 (m, 4H), 7.27 (br t, J = 7.5 Hz, 1H), 6.95 (br d, J = 7.9 Hz, 2H), 6.02-6.12 (m, 1H), 4.98-5.07 (m, 1H), 4.51 (br s, 1H), 4.44 (br s, 1H), 4.26 (br s, 1H), 3.84 (br dd, J = 10.6, 3.8 Hz, 1H), 3.69 (br d, J = 11.9 Hz, 2H), 3.57-3.65 (m, 2H), 3.44-3.57 (m, 2H), 3.17 (br d, J = 10.1 Hz, 2H), 3.05 (br s, 3H), 2.86 (br t, J = 11.7 Hz, 2H), 2.53-2.71 (m, 5H), 2.48 (s, 3H), 2.27-2.39 (m, 2H), 2.10-2.23 (m, 3H), 1.87-2.01 (m, 7H), 1.81 (br d, J = 12.9 Hz, 2H), 1.74 (br s, 2H), 1.59 (br d, J = 5.6 Hz, 3H), 1.52 (br d, J = 6.9 Hz, 3H), 1.23-1.46 (m, 6H), 1.04 (br d, J = 6.3 Hz, 3H), 0.85-0.93 ppm (m, 3H) |
| 649 | D | NA | 1161.40 | 1H NMR (400 MHz, CDCl3) δ = 8.71 (s, 1H), 8.46 (s, 1H), 7.92 (d, J = 8.0 Hz, 1H), 7.55 (d, J = 8.0 Hz, 1H), 7.45-7.33 (m, 5H), 7.33-7.28 (m, 2H), 7.05 (d, J = 8.0 Hz, 1H), 6.90 (t, J = 8.0 Hz, 1H), 6.37 (dd, J = 8.0, 4.0 Hz, 1H), 6.04 (d, J = 4.0 Hz, 1H), 5.92 (s, 1H), 5.37-5.29 (m, 1H), 5.09-4.95 (m, 3H), 4.86-4.74 (m, 1H), 4.68-4.59 (m, 1H), 4.41 (s, 2H), 4.37-4.29 (m, 1H), 3.76-3.68 (m, 1H), 3.67-3.55 (m, 3H), 3.32-3.23 (m, 2H), 3.21-2.94 (m, 12H), 2.88-2.79 (m, 1H), 2.55 (s, 4H), 2.50-2.42 (m, 5H), 2.28-2.00 (m, 10H), 1.97-1.86 (m, 2H), 1.70 (s, 2H), 1.64-1.52 (m, 3H), 1.41 (d, J = 8.0 Hz, 3H), 1.06 (d, J = 8.0 Hz, 3H), 0.94 (br d, J = 8.0 Hz, 3H). |
| 650 | D | NA | 1161.40 | 1H NMR (400 MHz, CDCl3) δ = 8.70 (s, 1H), 8.50 (s, 1H), 7.91 (d, J = 8.0 Hz, 1H), 7.51-7.59 (m, 2H), 7.37-7.46 (m, 4H), 7.28-7.32 (m, 2H), 7.02-7.09 (m, 1H), 6.90 (t, J = 8.0 Hz, 1H), 6.37 (dd, J = 8.0, 4.0 Hz, 1H), 6.03 (d, J = 4.0 Hz, 1H), 5.92 (s, 1H), 5.39-5.30 (m, 1H), 5.03-5.14 (m, 1H), 4.89 (s, 2H), 4.64-4.70 (m, 1H), 4.58 4.64 (m, 1H), 4.40 (s, 2H), 4.37-4.30 (m, 1H), 3.83-3.74 (m, 1H), 3.68-3.58 (m, 3H), 3.50 (br d, J = 8.0 Hz, 1H), 3.07-3.32 (m, 11H), 2.92-3.06 (m, 6H), 2.80-2.88 (m, 1H), 2.54-2.59 (m, 3H), 2.08-2.31 (m, 9H), 1.96-2.05 (m, 1H), 1.94-1.83 (m, 2H), 1.76-1.66 (m, 2H), 1.56-1.63 (m, 3H), 1.52 (d, J = 8.0 Hz, 3H), 1.06 (d, J = 8.0 Hz, 3H), 0.94 (d, J = 8.0 Hz, 3H) |
| 651 | D | NA | 1139.40 | 1H NMR (400 MHz, MeOD-d4) δ: 9.03-8.89 (m, 1H), 7.82-7.71 (m, 2H), 7.47 (s, 1H), 7.45-7.33 (m, 1H), 7.30-7.09 (m, 3H), 6.94-6.83 (m, 2H), 6.53 (dd, J = 2.0, 6.0 Hz, 1H), 6.17-6.03 (m, 2H), 5.18-5.07 (m, 1H), 4.98 (d, J = 7.2 Hz, 1H), 4.62-4.55 (m, 1H), 4.51 (br s, 2H), 4.44 (br d, J = 1.6 Hz, 1H), 4.38 (br t, J = 6.0 Hz, 1H), 3.82-3.48 (m, 5H), 3.35 (s, 3H), 3.11 (d, J = 11.6 Hz, 2H), 2.89-2.72 (m, 4H), 2.48-2.34 (m, 8H), 2.34-2.09 (m, 9H), 2.01-1.92 (m, 1H), 1.88 (br dd, J = 4.4, 10.4 Hz, 2H), 1.82-1.66 (m, 3H), 1.59 (br d, J = 7.2 Hz, 2H), 1.49 (d, J = 7.2 Hz, 3H), 1.31-1.13 (m, 2H), 1.05 (d, J = 6.8 Hz, 2.5H), 0.97-0.89 (m, 3H), 0.85 (d, J = 6.8 Hz, 0.5H) |
| 652 | A | A | 1139.40 | 1H NMR (400 MHz, MeOD-d4) δ: 8.98 (s, 1H), 7.81-7.69 (m, 2H), 7.47 (s, 1H), 7.44-7.35 (m, 1H), 7.29-7.13 (m, 3H), 6.93-6.83 (m, 2H), 6.53 (dd, J = 2.0, 6.0 Hz, 1H), 6.15-5.99 (m, 2H), 5.17-5.06 (m, 1H), 5.03 (d, J = 7.2 Hz, 1H), 4.56-4.48 (m, 3H), 4.47-4.33 (m, 2H), 3.84 (dd, J = 4.0, 10.8 Hz, 1H), 3.71-3.43 (m, 4H), 3.40-3.32 (m, 3H), 3.11 (d, J = 11.6 Hz, 2H), 2.90-2.68 (m, 4H), 2.46-2.34 (m, 8H), 2.28-2.06 (m, 9H), 1.96 (ddd, J = 4.4, 8.8, 13.2 Hz, 1H), 1.91-1.68 (m, 5H), 1.65-1.47 (m, 5H), 1.33-1.16 (m, 2H), 1.04 (d, J = 6.8 Hz, 3H), 0.93-0.82 (m, 3H) |
| 653 | A | A | 1137.40 | 1H NMR (400 MHz, DMSO-d6) δ: 14.25-14.04 (m, 1H), 8.99 (s, 1H), 8.38 (br d, J = 8.4 Hz, 1H), 7.92 (d, J = 6.8 Hz, 1H), 7.77 (d, J = 6.0 Hz, 1H), 7.55-7.31 (m, 5H), 7.28-7.17 (m, 1H), 6.99-6.76 (m, 2H), 6.58-6.43 (m, 1H), 6.12 (d, J = 13.2 Hz, 2H), 5.98 (s, 2H), 5.19 (br s, 1H), 5.11 (d, J = 3.6 Hz, 1H), 4.89-4.78 (m, 2H), 4.49 (br s, 2H), 4.41 (s, 1H), 4.28 (br t, J = 5.6 Hz, 2H), 3.81-3.68 (m, 1H), 3.64-3.54 (m, 4H), 3.42 (br d, J = 10.8 Hz, 1H), 3.28-3.20 (m, 3H), 3.01 (br d, J = 11.2 Hz, 2H), 2.79-2.61 (m, 4H), 2.46 (s, 3H), 2.36-2.24 (m, 5H), 2.18 (br d, J = 7.2 Hz, 3H), 2.09 (br s, 2H), 1.96 (br s, 5H), 1.85-1.56 (m, 6H), 1.40 (br d, J = 10.0 Hz, 2H), 1.09 (br dd, J = 1.2, 12.6 Hz, 2H), 0.94 (d, J = 6.8 Hz, 3H), 0.79 (br d, J = 6.8 Hz, 3H) |
| 654 | A | A | 1135.40 | 1H NMR (400 MHz, DMSO-d6) δ: 9.70 (br s, 1H), 9.02-8.81 (m, 1H), 8.34 (d, J = 8.0 Hz, 1H), 7.90-7.78 (m, 2H), 7.53-7.34 (m, 5H), 7.26 (t, J = 7.2 Hz, 1H), 6.94-6.85 (m, 2H), 6.61 (br s, 1H), 6.24-6.01 (m, 4H), 5.29-4.99 (m, 2H), 4.81-4.66 (m, 1H), |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | 4.57 (br s, 2H), 4.44-4.36 (m, 1H), 4.35-4.23 (m, 2H), 3.79-3.37 (m, 9H), 3.13-2.89 (m, 6H), 2.80 (br t, J = 11.6 Hz, 2H), 2.48-2.45 (s, 3H), 2.42-2.32 (m, 4H), 2.26-2.14 (m, 3H), 2.11-1.96 (m, 6H), 1.93-1.71 (m, 7H), 1.32-1.04 (m, 3H), 1.02-0.88 (m, 6H), 0.87-0.76 (m, 3H) |
| 655 | D | NA | 1121.40 | 1H NMR (400 MHz, MeOD-d4) δ: 8.90-8.82 (m, 1H), 7.80-7.69 (m, 2H), 7.50-7.33 (m, 5H), 7.26-7.17 (m, 1H), 6.92-6.84 (m, 2H), 6.54 (d, J = 6.4 Hz, 1H), 6.13 (d, J = 1.2 Hz, 2H), 5.16-5.08 (m, 1H), 4.99 (dd, J = 7.2, 3.6 Hz, 1H), 4.81-4.74 (m, 1H), 4.61-4.55 (m, 2H), 4.51 (s, 2H), 4.43 (s, 1H), 4.36 (d, J = 6.4 Hz, 1H), 3.76-3.60 (m, 4H), 3.58-3.44 (m, 2H), 3.35 (s, 1H), 3.15-2.94 (m, 4H), 2.92-2.84 (m, 1H), 2.63 (d, J = 10.4 Hz, 4H), 2.49-2.34 (m, 9H), 2.28-2.18 (m, 3H), 2.15 (s, 2.01-1.88 (m, 4H), 1.85 (d, J = 12.4 Hz, 1H), 1.71 (s, 3H), 1.61-1.45 (m, 4H), 1.23 (d, J = 10.0 Hz, 1H), 1.07-0.83 (m, 6H) |
| 656 | A | A | 1121.40 | 1H NMR (400 MHz, 400 MHz, MeOD-d4) δ: 8.89-8.83 (m, 1H), 7.79-7.71 (m, 2H), 7.49-7.35 (m, 5H), 7.27-7.19 (m, 1H), 6.93-6.85 (m, 2H), 6.57-6.52 (m, 1H), 6.16-6.10 (m, 2H), 5.15 (d, J = 3.2 Hz, 1H), 5.09-4.98 (m, 1H), 4.79-4.73 (m, 1H), 4.57 (s, 1H), 4.55-4.48 (m, 3H), 4.44 (s, 1H), 4.42-4.36 (m, 1H), 3.84 (dd, J = 10.8, 4.0 Hz, 1H), 3.78-3.67 (m, 1H), 3.66-3.58 (m, 2H), 3.55 (dd, J = 8.4, 4.0 Hz, 2H), 3.36 (s, 1H), 3.11 (d, J = 11.2 Hz, 4H), 3.03-2.61 (m, 6H), 2.52-2.32 (m, 8H), 2.28-2.11 (m, 5H), 2.07-1.93 (m, 4H), 1.92-1.71 (m, 4H), 1.66-1.50 (m, 4H), 1.28 (d, J = 7.6 Hz, 1H), 1.05 (d, J = 6.4 Hz, 3H), 0.94-0.86 (m, 3H). |
| 657 | A | A | 1121.40 | 1H NMR (400 MHz, 400 MHz, MeOD-d4) δ: 8.86 (s, 1H), 7.79-7.69 (m, 2H), 7.48-7.34 (m, 5H), 7.22 (m, J = 7.6 Hz, 1H), 6.92-6.84 (m, 2H), 6.54 (d, J = 6.4 Hz, 1H), 6.15-6.04 (m, 2H), 5.14 (d, J = 3.6 Hz, 1H), 5.07-4.96 (m, 1H), 4.79-4.69 (m, 1H), 4.60-4.34 (m, 6H), 3.87-3.66 (m, 2H), 3.65-3.50 (m, 4H), 3.35 (s, 1H), 3.09 (d, J = 11.2 Hz, 4H), 2.93 (m, J = 11.2 Hz, 1H), 2.79-2.65 (m, 4H) 2.53-2.31 (m, 9H), 2.28-2.09 (m, 5H), 2.07-1.92 (m, 4H), 1.91-1.70 (m, 4H), 1.69-1.56 (m, 1H), 1.51 (d, J = 7.2 Hz, 3H), 1.35-1.23 (m, 1H), 1.05 (d, J = 6.4 Hz, 3H), 0.93-0.86 (m, 3H). |
| 658 | | | 1048.40 | 1H NMR (400 MHz, CHLOROFORM-d) δ = 8.27 (s, 3H), 7.91 (d, J = 8.0 Hz, 1H), 7.55-7.50 (m, 1H), 7.46-7.40 (m, 2H), 7.32-7.28 (m, 1H), 7.25-7.19 (m, 3H), 7.07-7.00 (m, 1H), 6.93-6.85 (m, 1H), 6.36 (dd, J = 6.0, 2.0 Hz, 1H), 6.01 (d, J = 2.0 Hz, 1H), 5.87 (s, 1H), 5.36-5.26 (m, 1H), 5.25-5.15 (m, 2H), 4.99-4.90 (m, 1H), 4.74 (dd, J = 8.4, 4.8 Hz, 1H), 4.65-4.55 (m, 1H), 4.43-4.36 (m, 2H), 4.34-4.26 (m, 1H), 3.69-3.63 (m, 3H), 3.57-3.49 (m, 3H), 3.30-3.20 (m, 3H), 3.19-3.10 (m, 2H), 3.09-2.98 (m, 4H), 2.87-2.76 (m, 4H), 2.58-2.50 (m, 1H), 2.47-2.40 (m, 5H), 2.28-2.07 (m, 5H), 2.05-1.95 (m, 2H), 1.95-1.80 (m, 4H), 1.74-1.62 (m, 1H), 1.43-1.27 (m, 5H), 1.10-1.00 (m, 3H), 0.95-0.87 (m, 3H) |
| 659 | D | NA | 1091.40 | 1H NMR (400 MHz, CHLOROFORM-d) δ: 8.64-8.69 (m, 1H), 7.87 (d, J = 6.00 Hz, 1H), 7.53 (d, J = 7.13 Hz, 1H), 7.28-7.41 (m, 6H), 7.25 (s, 1H), 7.03 (d, J = 8.13 Hz, 1H), 6.88 (t, J = 7.32 Hz, 1H), 6.32 (dd, J = 6.00, 1.75 Hz, 1H), 5.99 (d, J = 1.75 Hz, 1H), 5.86-5.90 (m, 1H), 4.93-5.09 (m, 2H), 4.85 (s, 2H), 4.78 (dd, J = 8.19, 4.19 Hz, 1H), 4.61 (quin, J = 5.44 Hz, 1H), 4.36 (m, 2H), 3.70 (dd, J = 10.51, 5.75 Hz, 1H), 3.52-3.59 (m, 2H), 3.07-3.27 (m, 9H), 2.56-2.65 (m, 3H), 2.52 (s, 3H), 2.39-2.46 (m, 3H), 2.34-2.37 (m, 2H), 2.15-2.23 (m, 4H), 2.07-2.13 (m, 3H), 1.96-2.01 (m, 1H), 1.74-1.81 (m, 2H), 1.48-1.62 (m, 7H), 1.39 (br d, J = 6.88 Hz, 3H), 1.28-1.34 (m, 2H), 1.04 (d, J = 6.50 Hz, 3H), 0.93 (br d, J = 6.63 Hz, 3H). |
| 660 | A | A | 1091.40 | 1H NMR (400 MHz, CHLOROFORM-d) δ = 8.67 (s, 1H), 7.87 (d, J = 6.0 Hz, 1H), 7.51-7.62 (m, 2H), 7.36-7.43 (m, 4H), 7.29 (s, 1H), 7.25 (s, 1H), 7.03 (d, J = 8.1 Hz, 1H), 6.88 (t, J = 7.6 Hz, 1H), 6.32 (dd, J = 6.0, 1.6 Hz, 1H), 5.99 (d, J = 1.6 Hz, 1H), 5.89 (s, 1H), 4.99-5.13 (m, 2H), 4.85 (s, 2H), 4.65 ( t, J = 7.1 Hz, 1H), 4.59 (s, 1H), 4.37 (s, 2H), 3.77 (dd, J = 10.4, 4.8 Hz, 1H), 3.62 (dd, J = 10.4, 3.2 Hz, 1H), 3.48 (d, J = 10.0 Hz, 1H), 3.07-3.26 (m, 9H), 2.61 (d, J = 7.2 Hz, 2H), 2.53 (s, 3H), 2.38-2.49 (m, 4H), 2.34 (s, 2H), 2.20 (d, J = 4.6 Hz, 4H), 2.07-2.13 (m, 3H), 1.96-2.01 (m, 1H), 1.72-1.83 (m, 5H), 1.58 (s, 4H), 1.50 (d, J = 6.9 Hz, 3H), 1.25-1.37 (m, 2H), 1.04 (d, J = 6.4 Hz, 3H), 0.92 (d, J = 6.4 Hz, 3H). |
| 661 | A | A | 1151.40 | 1H NMR (400 MHz, DMSO-d6) δ: 14.14 (br s, 1H), 8.99 (s, 1H), 8.40 (d, J = 8.4 Hz, 1H), 7.92 (d, J = 7.6 Hz, 1H), 7.77 (d, J = 6.0 Hz, 1H), 7.50 (s, 1H), 7.47-7.40 (m, 2H), 7.40-7.29 (m, 2H), 7.22 (s, 1H), 6.91-6.78 (m, 2H), 6.52 (br d, J = 6.0 Hz, 1H), 6.12 |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | (d, J = 13.2 Hz, 2H), 5.97 (s, 2H), 5.26-5.15 (m, 1H), 5.10 (br d, J = 3.2 Hz, 1H), 4.91 (br d, J = 6.0 Hz, 1H), 4.49 (br s, 3H), 4.36 (t, J = 7.6 Hz, 1H), 4.32-4.20 (m, 2H), 3.77-3.66 (m, 1H), 3.65-3.52 (m, 3H), 3.52-3.37 (m, 4H), 3.25 (br d, J = 10.0 Hz, 3H), 3.01 (br d, J = 11.6 Hz, 2H), 2.77-2.59 (m, 4H), 2.46 (s, 3H), 2.31-2.22 (m, 4H), 2.18 (br d, J = 7.2 Hz, 2H), 2.12-2.05 (m, 2H), 2.04-1.91 (m, 5H), 1.89-1.57 (m, 8H), 1.47-1.33 (m, 2H), 1.17-1.01 (m, 2H), 0.95 (br d, J = 6.8 Hz, 3H), 0.85-0.73 (m, 3H) |
| 662 | B | A | | 1H NMR (400 MHz, DMSO-d6) δ: 14.28-14.01 (m, 1H), 9.18-8.87 (m, 1H), 8.34 (d, J = 8.0 Hz, 1H), 7.92 (d, J = 8.0 Hz, 1H), 7.77 (d, J = 6.0 Hz, 1H), 7.52-7.36 (m, 5H), 7.28-7.17 (m, 1H), 6.96-6.79 (m, 2H), 6.61-6.46 (m, 1H), 6.11 (d, J = 20.0 Hz, 2H), 5.97 (s, 2H), 5.23-5.15 (m, 1H), 5.12 (d, J = 4.0 Hz, 1H), 4.99-4.76 (m, 1H), 4.68-4.44 (m, 3H), 4.43-4.33 (m, 1H), 4.32-4.22 (m, 1H), 3.82-3.71 (m, 1H), 3.62-3.53 (m, 2H), 3.45-3.38 (m, 2H), 3.25 (br d, J = 11.6 Hz, 4H), 3.19-3.10 (m, 1H), 3.01 (br d, J = 11.6 Hz, 2H), 2.79-2.58 (m, 3H), 2.47 (s, 3H), 2.33 (s, 2H), 2.29 (br d, J = 2.8 Hz, 3H), 2.18 (br d, J = 7.2 Hz, 3H), 2.13-2.06 (m, 2H), 1.95 (br d, J = 6.8 Hz, 6H), 1.89-1.81 (m, 2H), 1.76 (br s, 2H), 1.69 (br d, J = 14.8 Hz, 2H), 1.62 (br d, J = 2.0 Hz, 1H), 1.40 (q, J = 10.0 Hz, 2H), 1.18-1.01 (m, 2H), 1.01-0.91 (m, 2H), 0.87 (br d, J = 6.4 Hz, 2H), 0.82-0.71 (m, 3H) |
| 663 | B | B | | 1H NMR (400 MHz, DMSO-d6) δ: 14.14 (br s, 1H), 9.00-8.96 (m, 1H), 8.30 (d, J = 8.0 Hz, 1H), 7.92 (d, J = 8.0 Hz, 1H), 7.78 (d, J = 6.0 Hz, 1H), 7.54-7.35 (m, 5H), 7.23 (t, J = 7.6 Hz, 1H), 6.90-6.83 (m, 2H), 6.53 (br d, J = 6.0 Hz, 1H), 6.14 (s, 1H), 6.09 (s, 1H), 5.97 (s, 2H), 5.24-4.89 (m, 2H), 4.78-4.65 (m, 1H), 4.53-4.47 (m, 2H), 4.47-4.40 (m, 1H), 4.39-4.25 (m, 2H), 3.83-3.37 (m, 4H), 3.30-3.13 (m, 7H), 3.02 (br d, J = 11.2 Hz, 2H), 2.78-2.59 (m, 4H), 2.48-2.46 (m, 3H), 2.31-2.23 (m, 4H), 2.22-2.14 (m, 3H), 1.97 (br s, 6H), 1.82-1.60 (m, 7H), 1.24-0.96 (m, 3H), 0.93-0.80 (m, 6H), 0.79-0.69 (m, 3H) |
| 664 | A | A | 1109.40 | 1H NMR(400 MHz, CHLOROFORM-d) δ = 8.87 (s, 1H), 8.47 (s, 2H), 8.30 (br s, 1H), 8.09 (s, 2H), 7.85 (br d, J = 7.0 Hz, 1H), 7.36-7.47 (m, 4H), 7.27 (br t, J = 7.6 Hz, 1H), 6.95 (br d, J = 8.0 Hz, 2H), 6.04-6.12 (m, 1H), 4.95-5.08 (m, 1H), 4.51 (br t, J = 8.1 Hz, 1H), 4.44 (br s, 1H), 4.31 (br s, 1H), 4.01 (br s, 1H), 3.84 (br dd, J = 10.8, 4.1 Hz, 1H), 3.71 (br d, J = 11.9 Hz, 2H), 3.63 (br d, J = 9.8 Hz, 2H), 3.50-3.60 (m, 1H), 3.47 (br d, J = 9.6 Hz, 1H), 3.37 (br s, 1H), 3.25 (br s, 2H), 3.07 (br s, 3H), 2.88 (br s, 5H), 2.76 (br s, 1H), 2.52 (br s, 1H), 2.48 (s, 3H), 2.30-2.31 (m, 1H), 2.28-2.43 (m, 1H), 2.19 (br dd, J = 12.8, 8.1 Hz, 3H), 1.92-2.07 (m, 5H), 1.82 (br d, J = 10.0 Hz, 4H), 1.74 (br s, 2H), 1.56-1.65 (m, 5H), 1.52 (br d, J = 7.0 Hz, 3H), 1.43-1.49 (m, 1H), 1.27-1.41 (m, 3H), 1.01-1.08 (m, 3H), 0.86-0.93 ppm (m, 3H) |
| 665 | A | A | 1095.40 | 1H NMR (400 MHz, METHANOL-d4) 8: 8.89 (s, 1H), 8.52 (s, 1H), 8.31 (br s, 1H), 8.11 (s, 2H), 7.87 (br d, J = 6.88 Hz, 1H), 7.38-7.48 (m, 4H), 7.29 (t, J = 7.63 Hz, 1H), 6.96-6.98 (m, 2H), 6.06-6.14 (m, 1H), 5.00-5.11 (m, 1H), 4.53 (t, J = 8.07 Hz, 1H), 4.42-4.48 (m, 1H), 4.26-4.32 (m, 1H), 3.82-3.95 (m, 2H), 3.71-3.73 (m, 2H), 3.61-3.66 (m, 3H), 3.25-3.27 (m, 2H), 3.15-3.18 (m, 3H), 2.89 (br t, J = 11.51 Hz, 3H), 2.77-2.81 (m, 3H), 2.59-2.65 (m, 2H), 2.50 (s, 3H), 2.32-2.43 (m, 2H), 2.18-2.23 (m, 2H), 1.90-2.06 (m, 8H), 1.82-1.84 (m, 4H), 1.60-1.62 (m, 4H), 1.54 (d, J = 7.00 Hz, 3H), 1.27-1.49 (m, 5H) 1.07 (d, J = 6.50 Hz, 3H), 0.88-0.95 (m, 3H). |
| 666 | A | A | 1157.30 | 1H NMR (400 MHz, DMSO-d6) δ: 14.14 (br s, 1H), 9.20 (s, 1H), 8.44 (d, J = 7.6 Hz, 1H), 7.91 (dd, J = 1.2, 8.0 Hz, 1H), 7.77 (d, J = 6.0 Hz, 1H), 7.49 (s, 1H), 7.27-7.15 (m, 3H), 6.91-6.81 (m, 2H), 6.52 (dd, J = 2.0, 6.0 Hz, 1H), 6.16-6.07 (m, 2H), 5.97 (s, 2H), 5.23-5.15 (m, 1H), 5.12 (d, J = 3.6 Hz, 1H), 4.94 (t, J = 7.2 Hz, 1H), 4.49 (br s, 2H), 4.38-4.25 (m, 3H), 3.77-3.69 (m, 1H), 3.62-3.53 (m, 3H), 3.45-3.38 (m, 2H), 3.25 (br d, J = 10.0 Hz, 3H), 3.01 (br d, J = 11.6 Hz, 2H), 2.76-2.68 (m, 2H), 2.66 (br s, 1H), 2.31-2.24 (m, 6H), 2.20-2.15 (m, 2H), 2.13-2.02 (m, 3H), 1.96 (br d, J = 6.4 Hz, 4H), 1.84-1.58 (m, 6H), 1.48-1.32 (m, 5H), 1.16-1.02 (m, 2H), 1.01-0.96 (m, 2H), 0.93 (br d, J = 6.4 Hz, 3H), 0.84-0.74 (m, 3H). |
| 667 | C | A | 1151.40 | 1H NMR (400 MHz, DMSO-d6) δ: 9.07-8.96 (m, 1H), 8.44 (d, J = 8.4 Hz, 1H), 8.25 (s, 1H), 7.92 (d, J = 7.2 Hz, 1H), 7.78 (d, J = 6.0 Hz, 1H), 7.55-7.47 (m, 3H), 7.47-7.39 (m, 2H), 7.26-7.19 (m, 1H), 6.91-6.82 (m, 2H), 6.53 (dd, J = 1.6, 6.0 Hz, 1H), 6.12 (d, J = 18.4 Hz, 2H), 5.98 (s, 2H), 5.23-5.16 (m, 1H), 5.09-4.99 |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | (m, 1H), 4.54-4.43 (m, 3H), 4.40-4.24 (m, 2H), 3.80-3.75 (m, 1H), 3.57-3.51 (m, 7H), 3.29-3.24 (m, 7H), 3.02 (br d, J = 11.6 Hz, 2H), 2.77-2.68 (m, 2H), 2.47 (s, 3H), 2.31-2.15 (m, 6H), 2.10 (br d, J = 6.8 Hz, 2H), 2.05-1.89 (m, 6H), 1.82-1.52 (m, 5H), 1.40 (q, J = 9.6 Hz, 2H), 1.16-1.03 (m, 2H), 1.02-0.85 (m, 3H), 0.83-0.73 (m, 3H) |
| 668 | A | A | 1151.40 | 1H NMR (400 MHz, DMSO-d6) δ: 9.07-8.96 (m, 1H), 8.44 (d, J = 8.4 Hz, 1H), 8.25 (s, 1H), 7.92 (d, J = 7.0 Hz, 1H), 7.78 (d, J = 6.0 Hz, 1H), 7.55-7.47 (m, 3H), 7.47-7.39 (m, 2H), 7.26-7.19 (m, 1H), 6.91-6.82 (m, 2H), 6.53 (dd, J = 1.6, 6.0 Hz, 1H), 6.12 (d, J = 18.4 Hz, 2H), 5.98 (s, 2H), 5.23-5.16 (m, 1H), 5.09-4.99 (m, 1H), 4.54-4.43 (m, 3H), 4.40-4.24 (m, 2H), 3.80-3.75 (m, 1H), 3.57-3.51 (m, 7H), 3.29-3.24 (m, 7H), 3.02 (br d, J = 11.6 Hz, 2H), 2.77-2.68 (m, 2H), 2.47 (s, 3H), 2.31-2.15 (m, 6H), 2.10 (br d, J = 6.8 Hz, 2H), 2.05-1.89 (m, 6H), 1.82-1.52 (m, 5H), 1.40 (q, J = 9.6 Hz, 2H), 1.16-1.03 (m, 2H), 1.02-0.85 (m, 3H), 0.83-0.73 (m, 3H) |
| 669 | C | B | 1165.40 | 1H NMR (400 MHz, DMSO-d6) δ: 14.15-14.13 (m, 1H), 9.03-8.95 (m, 1H), 8.37 (d, J = 8.4 Hz, 1H), 7.96-7.75 (m, 2H), 7.54-7.37 (m, 5H), 7.27-7.19 (m, 1H), 6.91-6.82 (m, 2H), 6.55-6.51 (m, 1H), 6.18-6.08 (m, 2H), 5.98 (s, 2H), 5.25-5.03 (m, 2H), 4.98-4.86 (m, 1H), 4.52-4.48 (m, 2H), 4.44-4.24 (m, 3H), 3.79-3.75 (m, 1H), 3.66-3.52 (m, 3H), 3.28-3.20 (m, 7H), 3.04-3.00 (m, 2H), 2.80-2.60 (m, 4H), 2.37-2.05 (m, 12H), 2.03-1.90 (m, 7H), 1.83-1.67 (m, 4H), 1.85-1.34 (m, 5H), 1.18-1.02 (m, 2H), 1.00-0.86 (m, 3H), 0.80-0.74 (m, 3H) |
| 670 | A | A | 1165.40 | 1H NMR (400 MHz, DMSO-d6) δ: 14.18-14.11 (m, 1H), 8.99 (s, 1H), 8.42 (d, J = 8.4 Hz, 1H), 7.97-7.88 (m, 1H), 7.78 (d, J = 6.0 Hz, 1H), 7.50 (s, 1H), 7.48-7.44 (m, 2H), 7.40-7.33 (m, 2H), 7.27-7.20 (m, 1H), 6.90-6.82 (m, 2H), 6.54-6.52 (m, 1H), 6.17-6.09 (m, 2H), 6.02-5.93 (m, 2H), 5.26-5.01 (m, 2H), 4.98-4.90 (m, 1H), 4.52-4.48 (m, 2H), 4.41-4.24 (m, 3H), 3.78-3.54 (m, 1H), 3.26-3.21 (m, 6H), 3.03-3.29 (m, 2H), 2.79-2.60 (m, 6H), 2.35-2.27 (m, 6H), 2.22-2.08 (m, 3H), 2.13-2.05 (m, 3H), 2.00-1.91 (m, 6H), 1.82-1.68 (m, 6H), 1.48-1.34 (m, 3H), 1.17-1.02 (m, 3H), 0.98-0.91 (m, 3H), 0.82-0.76 (m, 3H) |
| 671 | A | A | 1146.30 | 1H NMR (400 MHz, DMSO-d6) δ: 9.00 (s, 1H), 8.70 (d, J = 8.0 Hz, 1H), 8.17 (s, 1H), 7.91 (d, J = 8.0 Hz, 1H), 7.77 (d, J = 6.0 Hz, 1H), 7.53-7.45 (m, 5H), 7.24-7.20 (m, 1H), 6.88-6.83 (m, 2H), 6.53-6.51 (m, 1H), 6.12 (d, J = 7.2 Hz, 2H), 5.99-5.97 (m, 2H), 5.20-5.12 (m, 3H), 4.89 (s, 2H), 4.38 (t, J = 8.0 Hz, 1H), 4.30-4.27 (m, 2H), 3.76-3.73 (m, 1H), 3.61-3.55 (m, 4H), 3.02-3.00 (m, 4H), 2.75-2.72 (m, 3H), 2.46 (s, 3H), 2.29-1.96 (m, 18H), 1.84-1.61 (m, 7H), 1.44-1.37 (m, 2H), 1.14-1.06 (m, 2H), 0.97-0.93 (m, 3H), 0.83-0.77 (m, 3H). |
| 672 | A | A | 1160.40 | 1H NMR (400 MHz, DMSO-d6) δ: 14.14 (s, 1H), 9.00 (s, 1H), 8.57 (d, J = 8.8 Hz, 1H), 7.92 (dd, J = 8.0, 1.2 Hz, 1H), 7.77 (d, J = 6.0 Hz, 1H), 7.52-7.45 (m, 3H), 7.44-7.36 (m, 2H), 7.26-7.19 (m, 1H), 6.90-6.81 (m, 2H), 6.53 (dd, J = 6.0, 2.0 Hz, 1H), 6.18-6.09 (m, 2H), 5.98 (s, 2H), 5.24-5.08 (m, 1H), 4.96 (m, 1H), 4.49 (s, 2H), 4.40-4.21 (m, 3H), 3.74 (dd, J = 10.4, 4.0 Hz, 1H), 3.65-3.54 (m, 3H), 3.44 (d, J = 10.8 Hz, 1H), 3.25 (d, J = 10.4 Hz, 3H), 3.01 (d, J = 11.2 Hz, 2H), 2.76-2.60 (m, 6H), 2.46 (s, 3H), 2.37-2.13 (m, 8H), 2.12-2.06 (m, 3H), 1.96 (s, 6H), 1.87-1.75 (m, 3H), 1.70 (d, J = 12.8 Hz, 2H), 1.63 (s, 1H), 1.46-1.34 (m, 2H), 1.16-1.02 (m, 2H), 0.99-0.91 (m, 3H), 0.84-0.76 (m, 3H) |
| 673 | C | B | 1160.40 | 1H NMR (400 MHz, DMSO-d6) δ: 14.14 (s, 1H), 9.03-8.96 (m, 1H), 8.45 (d, J = 8.4 Hz, 1H), 7.91 (d, J = 6.8 Hz, 1H), 7.77 (d, J = 5.6 Hz, 1H), 7.52-7.39 (m, 5H), 7.26-7.18 (m, 1H), 6.91-6.80 (m, 2H), 6.52 (dd, J = 6.0, 1.6 Hz, 1H), 6.11 (d, J = 17.2 Hz, 2H), 5.97 (s, 2H), 5.24-5.08 (m, 1H), 4.96-4.80 (m, 1H), 4.49 (s, 2H), 4.42-4.23 (m, 3H), 3.76 (dd, J = 10.4, 4.8 Hz, 1H), 3.60 (s, 1H), 3.55 (d, J = 9.6 Hz, 1H), 3.40 (d, J = 11.2 Hz, 1H), 3.30-3.18 (m, 4H), 3.01 (d, J = 11.2 Hz, 2H), 2.82-2.62 (m, 3H), 2.46 (s, 3H), 2.33 (s, 1H), 2.32-2.25 (m, 4H), 2.23-2.03 (m, 7H), 1.96 (s, 7H), 1.81-1.52 (m, 6H), 1.46-1.22 (m, 3H), 1.15-1.02 (m, 2H), 0.98-0.84 (m, 3H), 0.80-0.74 (m, 3H). |
| 674 | A | A | 1105.40 | 1H NMR (400 MHz, MeOD-d4) δ: 8.14 (s, 1H), 7.83-7.68 (m, 2H), 7.61 (d, J = 8.4 Hz, 2H), 7.48-7.37 (m, 3H), 7.28-7.16 (m, 1H), 6.97-6.81 (m, 2H), 6.53 (dd, J = 2.0, 6.0 Hz, 1H), 6.13 (d, J = 2.0 Hz, 1H), 6.08 (s, 1H), 5.17-5.08 (m, 1H), 5.02 (q, J = 7.2 Hz, 1H), 4.57-4.48 (m, 3H), 4.46-4.33 (m, 2H), 3.84 (dd, J = 4.0, 10.8 Hz, 1H), 3.70-3.48 (m, 4H), 3.40-3.34 (m, 2H), 3.11 (br d, J = 11.6 Hz, 2H), 2.91-2.68 (m, 4H), 2.44-2.34 (m, 8H), |

TABLE 2D-continued

| Target protein degradation via exemplary bifunctional degradation compounds of Table 1D | | | | |
|---|---|---|---|---|
| Ex No | *$DC_{50}$ (nM) | **$D_{max}$ (%) | MH + 1 | NMR transcript |
| | | | | 2.27-2.06 (m, 9H), 1.99-1.63 (m, 7H), 1.62-1.47 (m, 5H), 1.29-1.15 (m, 2H), 1.05 (d, J = 6.4 Hz, 3H), 0.95-0.81 (m, 3H) |
| 675 | A | A | 1122.40 | 1H NMR (400 MHz, DMSO-d6) δ: 14.15 (s, 1H), 9.01 (s, 1H), 8.54-8.46 (m, 2H), 7.92 (dd, J = 1.2, 8.0 Hz, 1H), 7.80-7.76 (m, 2H), 7.71 (s, 1H), 7.50 (s, 1H), 7.27-7.19 (m, 1H), 6.91-6.81 (m, 2H), 6.53 (dd, J = 2.0, 6.1 Hz, 1H), 5.98 (s, 2H), 5.25-5.15 (m, 1H), 5.12 (d, J = 3.6 Hz, 1H), 4.94 (s, 1H), 4.50 (br s, 2H), 4.39-4.23 (m, 3H), 3.70 (br s, 1H), 3.65-3.52 (m, 3H), 3.44 (s, 1H), 3.28-3.23 (m, 3H), 3.02 (br d, J = 11.2 Hz, 3H), 2.72 (br d, J = 1.6 Hz, 1H), 2.66 (s, 3H), 2.32-2.23 (m, 4H), 2.18 (br d, J = 7.2 Hz, 3H), 2.10 (br d, J = 7.2 Hz, 2H), 2.06-1.89 (m, 6H), 1.81-1.67 (m, 5H), 1.62 (br dd, J = 2.4, 4.8 Hz, 1H), 1.41 (br d, J = 7.2 Hz, 6H), 1.15-1.05 (m, 2H), 1.00-0.89 (m, 3H), 0.85-0.75 (m, 3H). |
| 676 | B | A | 1075.30 | 1H NMR (400 MHz, MeOD-d4) δ: 8.92-8.79 (m, 1H), 7.78 (d, J = 6.0 Hz, 1H), 7.71 (dd, J = 1.2, 8.0 Hz, 1H), 7.50-7.29 (m, 5H), 7.27-7.17 (m, 1H), 6.95-6.82 (m, 2H), 6.53 (dd, J = 2.0, 6.0 Hz, 1H), 6.18 (d, J = 2.0 Hz, 1H), 6.13-6.04 (m, 1H), 5.01-4.93 (m, 2H), 4.61-4.54 (m, 1H), 4.50 (br s, 2H), 4.42 (br s, 1H), 3.76-3.56 (m, 3H), 3.55-3.45 (m, 2H), 3.41 (s, 2H), 3.35 (br s, 2H), 3.18-3.04 (m, 4H), 2.92 (br d, J = 9.6 Hz, 2H), 2.75-2.52 (m, 3H), 2.51-2.44 (m, 3H), 2.41-2.30 (m, 1H), 2.26-2.08 (m, 5H), 2.07-2.01 (m, 2H), 1.98-1.80 (m, 5H), 1.73-1.60 (m, 2H), 1.59-1.42 (m, 3H), 1.08-0.92 (m, 3H), 0.91-0.81 (m, 3H) |
| 677 | A | A | 1075.40 | 1H NMR (400 MHz, MeOD-d4) δ: 8.90-8.80 (m, 1H), 7.84-7.65 (m, 2H), 7.55-7.29 (m, 5H), 7.27-7.17 (m, 1H), 6.97-6.80 (m, 2H), 6.58-6.48 (m, 1H), 6.17 (d, J = 2.0 Hz, 1H), 6.12-5.99 (m, 1H), 5.03 (q, J = 7.2 Hz, 1H), 4.68-4.56 (m, 1H), 4.54-4.45 (m, 3H), 4.44-4.37 (m, 1H), 3.88-3.69 (m, 1H), 3.65-3.57 (m, 2H), 3.55-3.46 (m, 2H), 3.34 (br s, 3H), 3.19-3.05 (m, 4H), 2.87 (br s, 2H), 2.71 (br s, 1H), 2.59-2.45 (m, 4H), 2.41-2.30 (m, 1H), 2.26-2.09 (m, 5H), 2.06-1.75 (m, 8H), 1.74-1.61 (m, 2H), 1.59-1.46 (m, 3H), 1.04 (d, J = 6.4 Hz, 3H), 0.93-0.81 (m, 3H) |
| 678 | A | A | 1048.40 | |
| 679 | A | A | 1157.40 | 1H NMR (400 MHz, DMSO-d6) δ: 14.14 (br s, 1H), 9.15 (s, 1H), 8.56 (d, J = 7.2 Hz, 1H), 7.91 (dd, J = 1.2, 8.0 Hz, 1H), 7.77 (d, J = 6.0 Hz, 1H), 7.49 (s, 1H), 7.37-7.27 (m, 1H), 7.26-7.18 (m, 2H), 6.89-6.81 (m, 2H), 6.52 (dd, J = 2.0, 6.0 Hz, 1H), 6.17-6.05 (m, 2H), 6.01-5.92 (m, 2H), 5.24-5.05 (m, 3H), 4.49 (br s, 2H), 4.40-4.20 (m, 3H), 3.69 (br dd, J = 4.4, 10.8 Hz, 1H), 3.64-3.51 (m, 3H), 3.45-3.39 (m, 1H), 3.25 (br d, J = 10.4 Hz, 3H), 3.01 (br d, J = 11.6 Hz, 2H), 2.77-2.69 (m, 2H), 2.65 (br s, 1H), 2.34-2.24 (m, 5H), 2.22-2.13 (m, 3H), 2.09 (br d, J = 6.4 Hz, 2H), 2.04-1.91 (m, 5H), 1.75 (br d, J = 3.2 Hz, 4H), 1.49-1.37 (m, 5H), 1.32-1.17 (m, 4H), 1.14-1.03 (m, 2H), 0.98-0.91 (m, 4H), 0.84-0.74 (m, 3H). |
| 680 | D | NA | 1157.40 | 1H NMR (400 MHz, DMSO-d6) δ: 9.16-9.10 (m, 1H), 8.28 (s, 1H), 8.25 (s, 1H), 7.91 (d, J = 6.8 Hz, 1H), 7.77 (d, J = 6.0 Hz, 1H), 7.49 (s, 1H), 7.38 (dd, J = 10.0, 6.4 Hz, 1H), 7.28-7.18 (m, 2H), 6.89-6.81 (m, 2H), 6.55-6.49 (m, 1H), 6.13 (d, J = 8.4 Hz, 2H), 5.97 (s, 2H), 5.18 (s, 1H), 5.02 (m, 1H), 4.49 (s, 2H), 4.44-4.18 (m, 3H), 3.68 (d, J = 9.2 Hz, 2H), 3.54 (d, J = 8.0 Hz, 2H), 3.25 (d, J = 11.2 Hz, 6H), 3.01 (d, J = 10.8 Hz, 2H), 2.60-2.74 (m, 4H), 2.34-2.37 (m, 3H), 2.31-2.34 (m, 1H), 2.22-2.31 (m, 5H), 2.17 (br d, J = 7.2 Hz, 2H), 2.02-2.12 (m, 3H), 1.96 (br s, 4H), 1.76 (br d, J = 12.4 Hz, 3H), 1.65 (br s, 3H), 1.46 (d, J = 7.2 Hz, 1H), 1.33-1.42 (m, 4H), 1.06 (br d, J = 11.2 Hz, 2H), 0.95 (d, J = 6.8 Hz, 2H), 0.72-0.85 (m, 4H) |
| 681 | A | A | 1157.30 | 1H NMR (400 MHz, DMSO-d6) δ: 9.13 (s, 1H), 8.48 (d, J = 7.6 Hz, 1H), 8.15 (s, 1H), 7.94-7.89 (m, 1H), 7.77 (d, J = 6.0 Hz, 1H), 7.49 (s, 1H), 7.45-7.37 (m, 1H), 7.30 (dd, J = 10.4, 6.4 Hz, 1H), 7.25-7.19 (m, 1H), 6.90-6.81 (m, 2H), 6.52 (dd, J = 6.0, 1.6 Hz, 1H), 6.16-6.09 (m, 2H), 6.01-5.94 (m, 2H), 5.23-5.15 (m, 1H), 5.09 (dd, J = 14.0, 6.8 Hz, 2H), 4.49 (s, 2H), 4.34 (m, 1H), 4.32-4.23 (m, 2H), 3.77-3.67 (m, 1H), 3.65-3.51 (m, 4H), 3.40 (s, 2H), 3.26 (s, 2H), 3.01 (d, J = 11.2 Hz, 2H), 2.77-2.71 (m, 2H), 2.70-2.66 (m, 2H), 2.36 (s, 3H), 2.34-2.24 (m, 5H), 2.22-2.10 (m, 5H), 2.08-1.99 (m, 3H), 1.96 (d, J = 4.8 Hz, 2H), 1.78 (dd, J = 8.0, 4.8 Hz, 3H), 1.72 (s, 1H), 1.69 (s, 1H), 1.47-1.36 (m, 5H), 1.10 (d, J = 11.2 Hz, 2H), 0.94 (d, J = 6.4 Hz, 3H) 0.82-0.75 (m, 3H). |
| 682 | B | A | 1139.40 | 1H NMR (400 MHz, DMSO-d6) δ: 9.01-8.88 (m, 1H), 8.38 (s, 1H), 8.23 (d, J = 8.0 Hz, 1H), 7.91 (dd, J = 1.6, 8.0 Hz, 1H), 7.77 (d, J = 6.0 Hz, 1H), 7.49 (s, 1H), 7.45-7.36 (m, 2H), 7.31 (d, J = 8.4 Hz, 1H), 7.22 (s, 1H), 6.90-6.80 (m, 2H), 6.52 (dd, J = 2.0, |

TABLE 2D-continued

Target protein degradation via exemplary bifunctional degradation compounds of Table 1D

| Ex No | *DC$_{50}$ (nM) | **D$_{max}$ (%) | MH + 1 | NMR transcript |
|---|---|---|---|---|
| | | | | 6.0 Hz, 1H), 6.20-6.11 (m, 2H), 5.97 (s, 2H), 5.25-5.12 (m, 1H), 5.06-4.77 (m, 1H), 4.49 (br s, 2H), 4.42 (t, J = 7.6 Hz, 1H), 4.27 (br d, J = 6.0 Hz, 2H), 3.69 (d, J = 8.8 Hz, 1H), 3.53 (br d, J = 4.4 Hz, 2H), 3.27-3.14 (m, 6H), 3.01 (br d, J = 12.0 Hz, 4H), 2.74 (br d, J = 3.2 Hz, 2H), 2.47-2.39 (m, 6H), 2.28 (br s, 5H), 2.17 (br d, J = 7.2 Hz, 4H), 2.07-1.90 (m, 3H), 1.89-1.51 (m, 7H), 1.49-1.29 (m, 5H), 0.95 (d, J = 6.8 Hz, 2H), 0.88-0.67 (m, 4H) |
| 683 | A | A | 1139.40 | 1H NMR (400 MHz, DMSO-d6) δ: 8.97 (s, 1H), 8.40 (d, J = 7.6 Hz, 1H), 8.29 (s, 1H), 7.91 (dd, J = 1.6, 8.0 Hz, 1H), 7.76 (d, J = 6.0 Hz, 1H), 7.54-7.30 (m, 5H), 7.23-7.14 (m, 1H), 6.93-6.80 (m, 2H), 6.51 (dd, J = 2.0, 6.0 Hz, 1H), 6.17-6.07 (m, 2H), 5.96 (s, 2H), 5.22-4.97 (m, 2H), 4.90 (t, J = 7.2 Hz, 1H), 4.48 (br s, 2H), 4.35 (t, J = 8.0 Hz, 1H), 4.30-4.19 (m, 2H), 3.70 (br dd, J = 3.6, 10.4 Hz, 1H), 3.56 (br d, J = 9.6 Hz, 2H), 3.26-3.21 (m, 5H), 3.00 (br d, J = 11.2 Hz, 5H), 2.80-2.69 (m, 2H), 2.44 (s, 3H), 2.30-2.24 (m, 4H), 2.21-2.12 (m, 5H), 2.04-1.92 (m, 3H), 1.88-1.56 (m, 8H), 1.46-1.34 (m, 5H), 0.99-0.89 (m, 3H), 0.78 (d, J = 6.8 Hz, 3H) |
| 684 | C | B | 1107.40 | 1H NMR (400 MHz, DMSO-d6) δ: 9.02-8.88 (m, 1H), 8.26-8.15 (m, 2H), 7.91 (dd, J = 1.6, 8.0 Hz, 1H), 7.77 (d, J = 6.0 Hz, 1H), 7.51-7.44 (m, 2H), 7.44-7.38 (m, 2H), 7.31 (d, J = 8.4 Hz, 1H), 7.25-7.18 (m, 1H), 6.90-6.80 (m, 2H), 6.52 (dd, J = 2.0, 6.0 Hz, 1H), 6.13 (s, 2H), 5.97 (s, 2H), 5.23-5.13 (m, 1H), 5.07-4.94 (m, 1H), 4.87 (quin, J = 7.2 Hz, 1H), 4.49 (br s, 2H), 4.41 (t, J = 7.6 Hz, 1H), 4.27 (br d, J = 5.2 Hz, 2H), 3.67 (br d, J = 8.8 Hz, 3H), 3.23 (br s, 2H), 3.01 (br d, J = 11.2 Hz, 3H), 2.79-2.69 (m, 3H), 2.52-2.52 (m, 2H), 2.46 (s, 1H), 2.44 (s, 2H), 2.31-2.22 (m, 5H), 2.21-2.09 (m, 5H), 2.08-1.86 (m, 4H), 1.82-1.64 (m, 5H), 1.48-1.32 (m, 7H), 0.95 (d, J = 6.8 Hz, 2H), 0.81 (d, J = 6.8 Hz, 3H), 0.74 (d, J = 6.8 Hz, 1H). |
| 685 | A | A | 1107.40 | 1H NMR (400 MHz, DMSO-d6) δ: 8.98 (s, 1H), 8.40 (d, J = 8.0 Hz, 1H), 8.21 (s, 1H), 7.92 (dd, J = 1.2, 8.0 Hz, 1H), 7.77 (d, J = 6.0 Hz, 1H), 7.49 (s, 1H), 7.43 (d, J = 8.0 Hz, 2H), 7.39-7.33 (m, 2H), 7.25-7.19 (m, 1H), 6.89-6.81 (m, 2H), 6.52 (dd, J = 2.0, 6.0 Hz, 1H), 6.15-6.10 (m, 2H), 5.97 (s, 2H), 5.24-4.99 (m, 2H), 4.91 (quin, J = 7.2 Hz, 1H), 4.49 (br s, 2H), 4.36 (t, J = 7.6 Hz, 1H), 4.28 (br s, 2H), 3.74-3.61 (m, 4H), 3.55 (br d, J = 9.6 Hz, 1H), 3.01 (br d, J = 11.2 Hz, 3H), 2.77-2.71 (m, 3H), 2.45 (s, 3H), 2.29 (br dd, J = 7.2, 11.6 Hz, 4H), 2.24-2.13 (m, 6H), 2.07-1.92 (m, 4H), 1.84-1.68 (m, 6H), 1.49-1.32 (m, 8H), 0.97-0.92 (m, 3H), 0.84-0.76 (m, 3H). |
| 686 | D | NA | 1140.30 | 1H NMR (400 MHz, METHANOL-d4) δ: 8.91-8.82 (m, 1H), 7.76 (d, J = 6.0 Hz, 1H), 7.69 (ddd, J = 1.6, 4.8, 7.6 Hz, 1H), 7.46-7.33 (m, 5H), 7.25-7.16 (m, 1H), 6.91-6.83 (m, 2H), 6.52 (dd, J = 1.6, 6.0 Hz, 1H), 6.12 (s, 1H), 6.10-5.93 (m, 1H), 5.16-5.07 (m, 1H), 4.67-4.48 (m, 3H), 4.47-4.31 (m, 4H), 3.87-3.73 (m, 1H), 3.72-3.64 (m, 1H), 3.62-3.42 (m, 2H), 3.36-3.32 (m, 2H), 3.30 (br s, 1H), 3.21-3.04 (m, 4H), 3.03-2.95 (m, 2H), 2.86-2.76 (m, 1H), 2.62-2.51 (m, 1H), 2.49-2.45 (m, 3H), 2.43-2.37 (m, 4H), 2.36-2.04 (m, 8H), 2.03-1.57 (m, 9H), 1.09-1.01 (m, 3H), 0.95-0.80 (m, 3H) |
| 687 | D | NA | 1140.30 | 1H NMR (400 MHz, METHANOL-d4) δ: 8.94-8.81 (m, 1H), 7.82-7.69 (m, 2H), 7.59-7.38 (m, 5H), 7.24 (t, J = 7.6 Hz, 1H), 6.96-6.82 (m, 2H), 6.60-6.49 (m, 1H), 6.15 (s, 1H), 6.06-5.86 (m, 1H), 5.22-5.06 (m, 1H), 4.62 (td, J = 8.0, 13.6 Hz, 1H), 4.53 (br s, 3H), 4.44-4.26 (m, 3H), 3.93-3.65 (m, 2H), 3.64-3.42 (m, 2H), 3.37 (s, 3H), 3.32 (s, 1H), 3.18-2.91 (m, 6H), 2.82-2.55 (m, 2H), 2.52-2.46 (m, 3H), 2.45-2.39 (m, 4H), 2.34-2.20 (m, 5H), 2.18-2.05 (m, 3H), 2.00-1.77 (m, 4H), 1.76-1.52 (m, 4H), 1.11-1.00 (m, 2H), 0.93 (dd, J = 6.8, 12.8 Hz, 2H), 0.85 (d, J = 6.8 Hz, 1H), 0.60-0.36 (m, 1H) |
| 688 | D | NA | 1188.50 | |
| 689 | A | A | 1188.40 | |
| 690 | A | A | 1137.40 | |
| 691 | A | A | 1137.40 | |
| 692 | A | A | | 1H NMR (400 MHz, MeOD-d4) δ: 8.81-8.72 (m, 1H), 7.73-7.57 (m, 2H), 7.40-7.22 (m, 5H), 7.12 (t, J = 7.2 Hz, 1H), 6.85-6.71 (m, 2H), 6.43 (dd, J = 2.0, 6.0 Hz, 1H), 6.08-5.90 (m, 2H), 5.04-4.98 (m, 1H), 4.97-4.86 (m, 1H), 4.52-4.37 (m, 5H), 4.36-4.24 (m, 2H), 3.79-3.42 (m, 5H), 3.26-3.23 (m, 1H), 3.03-2.97 (m, 2H), 2.94-2.80 (m, 2H), 2.73-2.58 (m, 2H), 2.39-2.35 (m, 3H), |

TABLE 2D-continued

| Target protein degradation via exemplary bifunctional degradation compounds of Table 1D | | | | |
|---|---|---|---|---|
| Ex No | $^*DC_{50}$ (nM) | $^{**}D_{max}$ (%) | MH + 1 | NMR transcript |
| | | | | 2.34-2.23 (m, 5H), 2.18-2.02 (m, 5H), 1.93-1.74 (m, 3H), 1.74-1.59 (m, 3H), 1.51-1.33 (m, 5H), 1.29-1.16 (m, 4H), 0.98-0.70 (m, 12H) |
| 693 | A | A | | 1H NMR (400 MHz, DMSO-d6) δ: 14.19 (s, 1H), 9.07-8.69 (m, 1H), 8.40 (d, J = 7.6 Hz, 1H), 7.94 (dd, J = 1.6, 8.4 Hz, 1H), 7.81 (d, J = 6.0 Hz, 1H), 7.57 (s, 1H), 7.49-7.42 (m, 2H), 7.40-7.34 (m, 2H), 7.25 (s, 1H), 6.99-6.81 (m, 2H), 6.63 (dd, J = 2.0, 6.0 Hz, 1H), 6.40 (s, 2H), 6.20 (d, J = 2.0 Hz, 1H), 6.11 (s, 1H), 5.25-5.17 (m, 1H), 5.13-4.99 (m, 1H), 4.92 (t, J = 7.2 Hz, 1H), 4.37 (t, J = 7.6 Hz, 1H), 4.33-4.25 (m, 2H), 3.72 (br dd, J = 4.8, 10.4 Hz, 1H), 3.67-3.49 (m, 7H), 3.47-3.39 (m, 1H), 3.30-3.23 (m, 1H), 3.18 (br s, 3H), 2.81-2.60 (m, 4H), 2.53 (d, J = 2.0 Hz, 1H), 2.46 (s, 3H), 2.39-2.15 (m, 5H), 2.11 (br d, J = 6.8 Hz, 2H), 2.06-1.87 (m, 3H), 1.85-1.51 (m, 6H), 1.49-1.34 (m, 5H), 1.18-1.01 (m, 2H), 1.00-0.90 (m, 3H), 0.87-0.75 (m, 3H) |
| 694 | D | NA | | |
| 695 | A | A | | |
| 696 | D | NA | | |
| 697 | D | NA | | 1H NMR (400 MHz, MeOD-d4) δ: 8.40 (s, 1H), 8.17-8.04 (m, 2H), 7.85 (dd, J = 1.6, 8.4 Hz, 1H), 7.75-7.62 (m, 2H), 7.56-7.38 (m, 2H), 7.31-7.19 (m, 1H), 7.00-6.88 (m, 2H), 6.14-5.97 (m, 1H), 5.36 (dd, J = 2.0, 6.8 Hz, 1H), 5.13-4.90 (m, 2H), 4.54 (t, J = 8.0 Hz, 1H), 4.45-4.29 (m, 2H), 3.77-3.54 (m, 5H), 3.10-2.93 (m, 1H), 2.88-2.65 (m, 4H), 2.45-2.11 (m, 8H), 2.09-1.99 (m, 2H), 1.92 (ddd, J = 4.8, 8.4, 13.2 Hz, 1H), 1.84-1.60 (m, 8H), 1.57-1.41 (m, 5H), 1.30-1.12 (m, 2H), 1.04 (d, J = 6.8 Hz, 2.6H), 0.97-0.87 (m, 3H), 0.84 (d, J = 6.8 Hz, 0.4H) |
| 698 | A | A | | 1H NMR (400 MHz, MeOD-d4) δ: 8.42 (s, 1H), 8.19-8.06 (m, 2H), 7.88 (dd, J = 1.6, 8.4 Hz, 1H), 7.76-7.60 (m, 2H), 7.57-7.40 (m, 2H), 7.27 (dt, J = 1.6, 7.6 Hz, 1H), 7.01-6.89 (m, 2H), 6.12-5.88 (m, 1H), 5.38 (dq, J = 2.0, 6.8 Hz, 1H), 5.03 (q, J = 6.8 Hz, 1H), 4.80-4.57 (m, 1H), 4.50 (t, J = 8.0 Hz, 1H), 4.45-4.32 (m, 2H), 3.90-3.72 (m, 1H), 3.70-3.42 (m, 4H), 3.09-2.96 (m, 1H), 2.91-2.78 (m, 2H), 2.76-2.65 (m, 2H), 2.45-2.25 (m, 5H), 2.22-1.98 (m, 5H), 1.97-1.87 (m, 1H), 1.87-1.65 (m, 7H), 1.61-1.45 (m, 5H), 1.31-1.14 (m, 2H), 1.10-0.99 (m, 3H), 0.96-0.82 (m, 3H) |
| 699 | A | A | | 1H NMR (400 MHz, DMSO-d6) δ: 9.21-8.85 (m, 1H), 8.52 (d, J = 8.0 Hz, 1H), 8.27-8.25 (m, 2H), 8.24-8.19 (m, 1H), 8.07-7.98 (d, J = 8.0 Hz, 1H), 7.66-7.61 (s, 1H), 7.59-7.46 (m, 5H), 7.39-7.29 (m, 1H), 7.06-7.03 (m, 1H), 7.02-6.89 (m, 3H), 6.73-6.59 (s, 1H), 6.31-6.21 (s, 1H), 6.17-6.04 (m, 2H), 5.29-5.18 (m, 1H), 5.10-4.96 (m, 1H), 4.74-4.67 (s, 2H), 4.53-4.45 (m, 2H), 4.44-4.38 (m, 1H), 3.89-3.65 (m, 6H), 3.64-3.54 (m, 4H), 3.17-3.01 (m, 4H), 2.94-2.84 (m, 2H), 2.58 (s, 3H), 2.38-2.24 (m, 5H), 2.20-2.08 (m, 4H), 2.04-1.80 (m, 8H), 1.75-1.56 (m, 3H),1.53-1.46 (m, 3H), 1.38-1.16 (m, 3H), 1.10-1.05 (m, 3H), 0.94-0.87 (m, 3H). |
| 700 | D | NA | | |
| 701 | D | NA | | 1H NMR (400 MHz, DMSO-d6) δ: 9.19-8.92 (m, 1H), 8.30-8.20 (m, 1H), 8.14 (s, 1H), 7.91 (d, J = 8.0 Hz, 1H), 7.76 (d, J = 6.0 Hz, 1H), 7.51-7.18 (m, 6H), 6.90-6.79 (m, 2H), 6.52 (d, J = 4.4 Hz, 1H), 6.24-5.92 (m, 4H), 5.23-5.13 (m, 1H), 4.86-4.66 (m, 1H), 4.54-4.36 (m, 4H), 4.35-4.20 (m, 5H), 3.76 (s, 1H), 3.45-3.40 (m, 2H), 3.24 (d, J = 11.2 Hz, 3H), 3.00 (d, J = 11.2 Hz, 2H), 2.91-2.68 (m, 5H), 2.55-2.51 (m, 2H), 2.46-2.37 (m, 3H), 2.36-2.14 (m, 8H), 2.07-1.91 (m, 3H), 1.78 (s, 4H), 1.46 (s, 4H), 1.10-0.62 (m, 5H), 0.41-0.20 (m, 1H) |
| 702 | D | NA | | 1H NMR (400 MHz, DMSO-d6) δ: 9.02-8.89 (m, 1H), 8.42 (t, J = 7.2 Hz, 1H), 8.15 (s, 1H), 7.91 (d, J = 8.0 Hz, 1H), 7.76 (d, J = 6.0 Hz, 1H), 7.52-7.28 (m, 5H), 7.26-7.13 (m, 1H), 6.89-6.79 (m, 2H), 6.56-6.43 (m, 1H), 6.19-5.87 (m, 4H), 5.17 (d, J = 4.0 Hz, 1H), 4.99-4.62 (m, 1H), 4.54-4.33 (m, 5H), 4.36-4.23 (m, 4H), 3.74 (s, 1H), 3.65-3.63 (m, 1H), 3.31-3.15 (m, 4H), 3.01 (d, J = 11.2 Hz, 2H), 2.89-2.61 (m, 5H), 2.58-2.52 (m, 1H), 2.45 (s, 2H), 2.35-2.15 (m, 9H), 2.03-1.89 (m, 3H), 1.77 (s, 4H), 1.62-1.37 (m, 5H), 1.01-0.67 (m, 6H) |
| 703 | B | A | | 1H NMR(400 MHz, DMSO-d6) δ: 14.21-14.06 (m, 1H), 9.02-8.95 (m, 1H), 8.19 (d, J = 8.0 Hz, 1H), 7.91 (d, J = 8.0 Hz, 1H), 7.76 (d, J = 6.0 Hz, 1H), 7.52-7.45 (m, 2H), 7.45-7.37 (m, 2H), 7.31 (dd, J = 3.2, 8.4 Hz, 1H), 7.22 (t, J = 7.6 Hz, 1H), 6.90-6.80 (m, 2H), 6.51 (dd, J = 1.6, 6.0 Hz, 1H), 6.14 (d, J = 4.0 Hz, 2H), 5.96 (s, 2H), 5.19-4.97 (m, 2H), 4.93-4.80 (m, 1H), 4.49 (br s, 2H), 4.41 (t, J = 7.6 Hz, 1H), 4.27 (br dd, J = 4.0, 8.8 Hz, 1H), |

TABLE 2D-continued

Target protein degradation via exemplary bifunctional degradation compounds of Table 1D

| Ex No | *$DC_{50}$ (nM) | **$D_{max}$ (%) | MH + 1 | NMR transcript |
|---|---|---|---|---|
| | | | | 3.68 (d, J = 9.2 Hz, 1H), 3.57-3.51 (m, 1H), 3.30-3.20 (m, 6H), 3.01 (br d, J = 11.6 Hz, 3H), 2.47-2.43 (m, 5H), 2.42-2.35 (m, 3H), 2.21-2.08 (m, 5H), 2.07-1.87 (m, 5H), 1.84-1.74 (m, 1H), 1.45 (d, J = 7.2 Hz, 1H), 1.34 (dd, J = 1.6, 7.2 Hz, 3H), 0.95 (d, J = 6.8 Hz, 2H), 0.88-0.80 (m, 6H), 0.74 (d, J = 6.8 Hz, 1H). |
| 704 | A | A | | 1H NMR(400 MHz, DMSO-d6) δ: 8.99 (s, 1H), 8.41 (d, J = 8.0 Hz, 1H), 7.92 (d, J = 8.8 Hz, 1H), 7.77 (d, J = 6.0 Hz, 1H), 7.51 (s, 1H), 7.47-7.42 (m, 2H), 7.40-7.35 (m, 2H), 7.28-7.18 (m, 1H), 6.92-6.82 (m, 2H), 6.57-6.50 (m, 1H), 6.14 (d, J = 12.4 Hz, 2H), 5.98 (s, 2H), 5.17-5.08 (m, 1H), 4.96-4.88 (m, 1H), 4.49 (br s, 2H), 4.41-4.34 (m, 1H), 4.32-4.25 (m, 1H), 3.76-3.64 (m, 1H), 3.57 (d, J = 9.6 Hz, 1H), 3.26 (br dd, J = 2.4, 10.4 Hz, 4H), 3.20-3.06 (m, 5H), 3.03 (br d, J = 11.6 Hz, 2H), 2.46 (s, 7H), 2.23-2.09 (m, 6H), 2.07-1.92 (m, 5H), 1.83-1.73 (m, 1H), 1.50-1.43 (m, 1H), 1.38 (d, J = 7.2 Hz, 3H), 0.95 (br d, J = 6.0 Hz, 3H), 0.88 (d, J = 6.4 Hz, 3H), 0.84-0.77 (m, 3H). |
| 705 | A | A | | 1H NMR (400 MHz, MeOD-d4) δ: 8.99-8.76 (m, 1H), 7.84-7.69 (m, 2H), 7.57-7.18 (m, 6H), 7.00-6.82 (m, 2H), 6.62-6.46 (m, 1H), 6.22-6.01 (m, 2H), 4.51-4.43 (m, 3H), 3.93-3.55 (m, 6H), 3.15-3.09 (m, 2H), 2.95-2.59 (m, 8H), 2.58-2.37 (m, 7H), 2.32-2.12 (m, 9H), 2.09-1.98 (m, 8H), 1.89-1.68 (m, 4H), 1.61-1.47 (m, 3H), 1.20-1.01 (m, 9H), 0.95-0.84 (m, 3H) |
| 707 | A | A | | 1H NMR (400 MHz, DMSO-d6) δ: 14.30 (br s, 1H), 9.03-8.65 (m, 1H), 8.39 (d, J = 7.6 Hz, 1H), 7.93 (d, J = 7.2 Hz, 1H), 7.53 (s, 1H), 7.44 (d, J = 8.0 Hz, 2H), 7.39-7.33 (m, 2H), 7.27-7.19 (m, 1H), 6.92-6.83 (m, 2H), 6.23 (s, 2H), 6.09 (s, 1H), 5.12-4.98 (m, 1H), 4.91 (t, J = 7.2 Hz, 1H), 4.42-4.22 (m, 3H), 3.78-3.64 (m, 3H), 3.62-3.52 (m, 3H), 3.51-3.36 (m, 3H), 3.30 (br s, 1H), 3.26-3.19 (m, 1H), 3.19-3.09 (m, 2H), 3.06-2.91 (m, 3H), 2.76-2.70 (m, 1H), 2.63 (br dd, J = 3.5, 6.8 Hz, 1H), 2.45 (s, 3H), 2.42-2.34 (m, 2H), 2.28 (br d, J = 11.2 Hz, 1H), 2.25-2.15 (m, 5H), 2.08 (br d, J = 6.8 Hz, 2H), 2.04-1.90 (m, 5H), 1.87-1.53 (m, 9H), 1.38 (br d, J = 7.2 Hz, 5H), 1.22 (d, J = 7.2 Hz, 3H), 1.14-1.03 (m, 2H), 0.99-0.89 (m, 3H), 0.85-0.74 (m, 3H). |
| 708 | A | A | | |
| 713 | B | A | | |
| 714 | D | NA | | |
| 715 | A | A | | |
| 716 | A | A | | |

*DC50 (nM)
A < 2.5
2.5 ≤ B < 10
10 ≤ C < 30
D ≥ 30
NA not calculated/no curve fit
**Dmax (% degraded)
A > 75
50 < B ≤ 75
C ≤ 50
NA not calculated/no curve fit A novel bifunctional molecule, which contains a SMARCA2, BRAHMA or BRM protein recruiting moiety and an E3 Ligase recruiting moiety, through PROTAC technology is described. The bifunctional molecules of the present disclosure actively degrade SMARCA2, leading to robust cellular proliferation suppression and apoptosis induction. PROTAC mediated protein degradation provides a promising strategy in targeting the pathological proteins "undruggable" by traditional approaches.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A compound having the chemical structure:

PTM-L-ULM, or a pharmaceutically acceptable salt thereof, wherein:

(a) the ULM is:

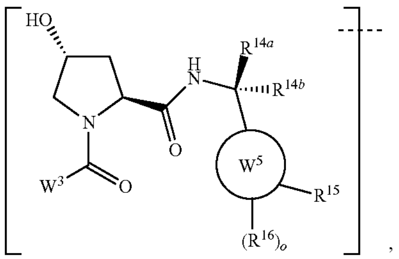

wherein:

$W^3$ is an optionally substituted aryl, optionally substituted heteroaryl, or

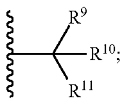

$R^9$ and $R^{10}$ are each independently hydrogen, optionally substituted alkyl, optionally substituted cycloalkyl, optionally substituted hydroxyalkyl, optionally substituted heteroaryl, or haloalkyl, or $R^9$, $R^{10}$, and the carbon atom to which they are attached form an optionally substituted cycloalkyl;

$R^{11}$ is an optionally substituted heterocyclyl, optionally substituted alkoxy, optionally substituted heteroaryl, optionally substituted aryl,

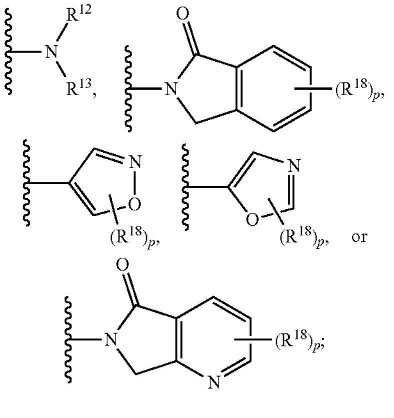

$R^{12}$ is H or optionally substituted alkyl;

$R^{13}$ is H, optionally substituted alkyl, optionally substituted alkylcarbonyl, optionally substituted (cycloalkyl) alkylcarbonyl, optionally substituted aralkylcarbonyl, optionally substituted arylcarbonyl, optionally substituted (heterocyclyl) carbonyl, or optionally substituted arylalkyl;

one of $R^{14a}$ and $R^{14b}$ is H, amino, haloalkyl, optionally substituted alkyl, optionally substituted alkoxy, optionally substituted hydroxyl alkyl, optionally substituted alkylamino, optionally substituted amide, optionally substituted alkyl-amide, optionally substituted alkyl-cyano, optionally substituted alkyl-phosphate, optionally substituted heteroalkyl, optionally substituted alkyl-heterocycloalkyl, optionally substituted alkoxy-heterocycloalkyl, $COR^{26}$, alkyl-$COR^{26}$, $CONR^{27a}R^{27b}$, $NHCOR^{26}$, or $NCH_3COR^{26}$; and the other of $R^{14a}$ and $R^{14b}$ is H; or $R^{14a}$ and $R^{14b}$ together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxy or aziridinyl;

$W^5$ is optionally substituted phenyl, optionally substituted naphthyl, or an optionally substituted 5-10 membered heteroaryl;

$R^{15}$ is H, halogen, CN, C≡CH, OH, $NO_2$, $NR^{27a}R^{27b}$, $OR^{27a}$, $CONR^{27a}R^{27b}$, $N^{R27a}R^{27b}$ $SO_2NR^{27a}R^{27b}$, $NR^{27a}SO_2R^{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl;

each $R^{16}$ is independently halogen, CN, optionally substituted alkyl, optionally substituted alkylamino, optionally substituted haloalkyl, hydroxy, or optionally substituted haloalkoxy;

is 0, 1, 2, 3, or 4;

each $R^{18}$ is independently H, halogen, optionally substituted alkoxy, cyano, optionally substituted alkyl, haloalkyl, or haloalkoxy;

each $R^{26}$ is independently H, OH, optionally substituted alkyl, or $NR^{27a}R^{27b}$;

each $R^{27a}$ and $R^{27b}$ is independently H, optionally substituted alkyl, or optionally substituted cycloalkyl, or $R^{27a}$ and $R^{27b}$ together with the nitrogen atom to which they are attached form a 4-6 membered heterocyclyl;

p is 0, 1, 2, 3, or 4; and the  indicates the site of attachment of the L;

(b) the L is $(A^L)_q$-, wherein:

$(A^L)_q$ is a group which is connected to the ULM and the PTM;

q is an integer from 1 to 100;

each $A^L$ is independently $CR^{L1}R^{L2}$, O, S, SO, $SO_2$, $NR^{L3}$, $SO_2NR^{L3}$, $SONR^{L3}$, $CONR^{L3}$ $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 1-6 $R^{L1}$ and/or $R^{L2}$ groups, $C_{3-11}$heterocyclyl optionally substituted with 1-6 $R^{L1}$ and/or $R^{L2}$ groups, aryl optionally substituted with 1-6 $R^{L1}$ and/or $R^{L2}$ groups, or heteroaryl optionally substituted with 1-6 $R^{L1}$ and/or $R^{L2}$ groups, where $R^{L1}$ or $R^{L2}$, each independently are optionally linked to other groups to form cycloalkyl or heterocyclyl moiety optionally substituted with 1-4 $R^{L5}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)$ $(C_{1-8}alkyl)$, OH, $NH_2$, SH, $SO_2C_{1\text{-}8}$alkyl, $P(O)(OC_{1\text{-}8}$alkyl) ($C_{1\text{-}8}$alkyl), P(O)($OC_{1\text{-}8}$alkyl$)_2$, C≡C—$C_{1\text{-}8}$alkyl, C≡CH, CH═CH($C_{1\text{-}8}$alkyl), C($C_{1\text{-}8}$alkyl)═CH($C_{1\text{-}8}$alkyl), C($C_{1\text{-}8}$alkyl)═C($C_{1\text{-}8}$alkyl$)_2$, $Si(OH)_3$, Si($C_{1\text{-}8}$alkyl$)_3$, Si(OH)($C_{1\text{-}8}$alkyl$)_2$, $COC_{1\text{-}8}$alkyl, $CO_2H$, CN, $CF_3$, $CHF_2$, $CH_2F$, $NO_2$, $SF_5$, $SO_2NHC_{1\text{-}8}$alkyl, $SO_2N$($C_{1\text{-}8}$alkyl$)_2$, $SONHC_{1\text{-}8}$alkyl, SON($C_{1\text{-}8}$alkyl$)_2$, $CONHC_{1\text{-}8}$alkyl, CON($C_{1\text{-}8}$alkyl$)_2$, N($C_{1\text{-}8}$alkyl) CONH($C_{1\text{-}8}$alkyl), N($C_{1\text{-}8}$alkyl)CON($C_{1\text{-}8}$alkyl$)_2$, NHCONH($C_{1\text{-}8}$alkyl), NHCON($C_{1\text{-}8}$alkyl$)_2$, $NHCONH_2$, N($C_{1\text{-}8}$alkyl)$SO_2$NH($C_{1\text{-}8}$alkyl), N($C_{1\text{-}8}$alkyl)$SO_2$N($C_{1\text{-}8}$alkyl$)_2$, NH $SO_2$NH($C_{1\text{-}8}$alkyl), NH $SO_2$N($C_{1\text{-}8}$alkyl$)_2$, or NH $SO_2NH_2$; and (c) the PTM is:

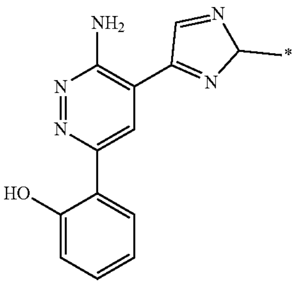

or

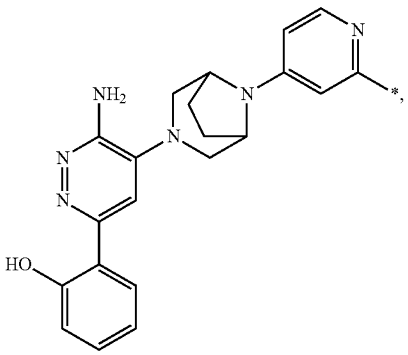

wherein

 is the attachment point to the L.

2. The compound according to claim 1, wherein the PTM is:

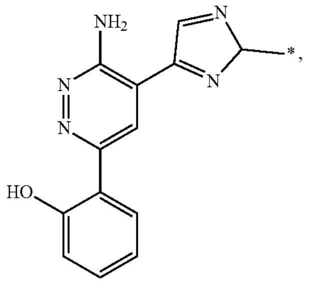

wherein  is the attachment point to the L.

3. The compound according to claim 1, wherein the PTM is:

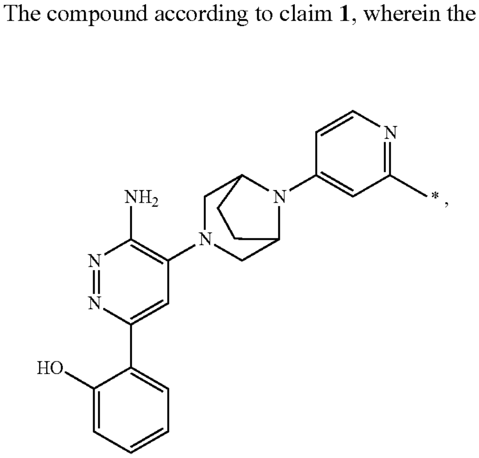

wherein  is the attachment point to the L.

4. The compound according to claim 1, wherein:

$W^3$ is

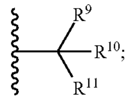

$R^9$ and $R^{10}$ are independently hydrogen, optionally substituted alkyl, optionally substituted hydroxyalkyl, or haloalkyl;

$R^{11}$ is

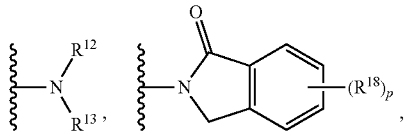

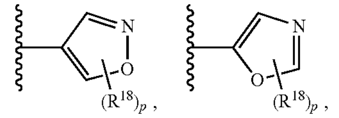

or

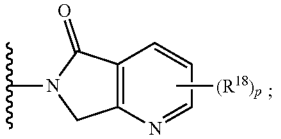

$R^{12}$ is H or optionally substituted alkyl;

$R^{13}$ is H, optionally substituted alkyl, optionally substituted alkylcarbonyl, optionally substituted (cycloalkyl) alkylcarbonyl, optionally substituted aralkylcarbonyl, optionally substituted arylcarbonyl, optionally substituted (heterocyclyl) carbonyl, or optionally substituted arylalkyl;

one of $R^{14a}$ and $R^{14b}$ is H, amino, haloalkyl, optionally substituted alkyl, optionally substituted alkoxy, optionally substituted hydroxyl alkyl, optionally substituted alkylamino, optionally substituted amide, optionally substituted alkyl-amide, optionally substituted alkyl-cyano, optionally substituted alkyl-phosphate, optionally substituted heteroalkyl, optionally substituted alkyl-heterocycloalkyl, optionally substituted alkoxy-heterocycloalkyl, $COR^{26}$, alkyl-$COR^{26}$, $CONR^{27a}R^{27b}$, $NHCOR^{26}$, or $NCH_3COR^{26}$; and the other of $R^{14a}$ and $R^{14b}$ is H;

$W^5$ is optionally substituted phenyl or optionally substituted 5-10 membered heteroaryl; and $R^{15}$ is optionally substituted aryl, optionally substituted heteroaryl, optionally substituted cycloalkyl, or optionally substituted heterocyclyl.

5. The compound according to claim 1, wherein the ULM is:

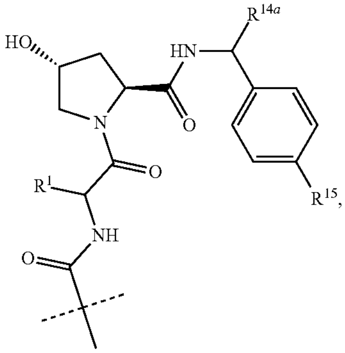

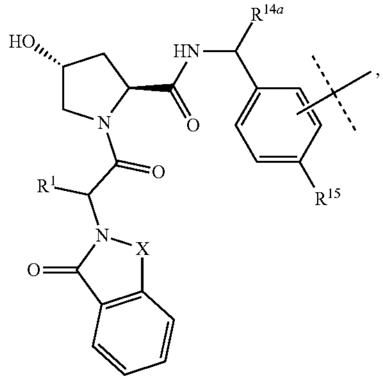

or

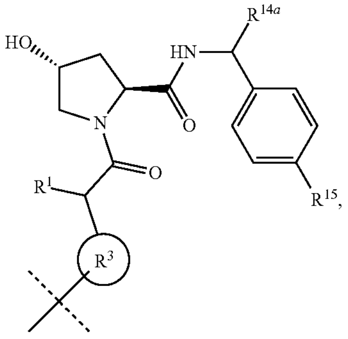

wherein:

$R^1$ is H, optionally substituted alkyl, optionally substituted cycloalkyl, optionally substituted hydroxyalkyl, optionally substituted heteroaryl, or haloalkyl;

$R^{14a}$ is H, haloalkyl, or optionally substituted alkyl;

$R^{15}$ is H, halogen, CN, C≡CH, OH, $NO_2$, optionally substituted heteroaryl, optionally substituted aryl, optionally substituted alkyl, optionally substituted haloalkyl, optionally substituted haloalkoxy, optionally substituted cycloalkyl, or optionally substituted heterocyclyl;

X is $CH_2$;

$R^3$ is an optionally substituted 5 or 6 membered heteroaryl; and the

indicates the site of attachment of the L.

6. The compound of claim 1, wherein the ULM is:

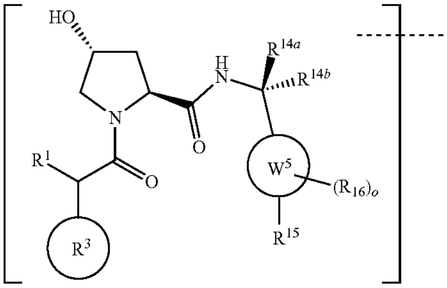

or

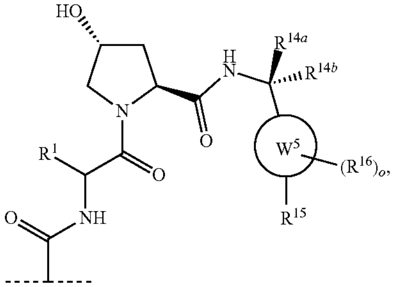

wherein:

$R^1$ is H, optionally substituted alkyl or optionally substituted cycloalkyl;

$R^3$ is an optionally substituted 5-6 membered heteroaryl;

$W^5$ is optionally substituted phenyl, optionally substituted naphthyl, or optionally substituted pyridinyl;

one of $R^{14a}$ and $R^{14b}$ is H, optionally substituted alkyl, haloalkyl, optionally substituted alkoxy, optionally substituted hydroxyl alkyl, optionally substituted alkylamino, optionally substituted amide, optionally substituted alkyl-amide, optionally substituted alkyl-cyano, optionally substituted alkyl-phosphate, optionally substituted heteroalkyl, optionally substituted alkyl-heterocycloalkyl, optionally substituted alkoxy-heterocycloalkyl, $COR^{26}$, alkyl-$COR^{26}$, $CONR^{27a}R^{27b}$, $NHCOR^{26}$, or $NCH_3COR^{26}$; and the other of $R^{14a}$ and $R^{14b}$ is H; or $R^{14a}$ and $R^{14b}$ together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxy or aziridinyl;

$R^{15}$ is CN, C≡CH, fluoroalkyl, or

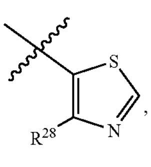

,

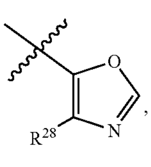

,

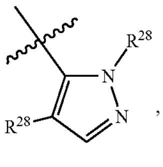

,

-continued

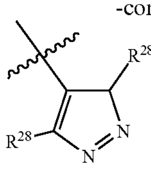
,
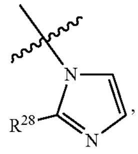
, optionally substituted

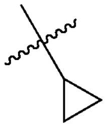
;

each $R^{16}$ is independently selected from halogen, CN, optionally substituted alkyl, optionally substituted haloalkyl, hydroxy, and haloalkoxy;

each $R^{26}$ is independently H, OH, optionally substituted alkyl, or $NR^{27a}R^{27b}$;

each $R^{27a}$ and $R^{27b}$ is independently H, optionally substituted alkyl, optionally substituted 3-5 membered cycloalkyl, or $R^{27a}$ and $R^{27b}$ together with the nitrogen atom to which they are attached form a 4-6 membered heterocyclyl;

$R^{28}$ is H, optionally substituted alkyl, optionally substituted alkoxy, optionally substituted heteroalkyl, optionally substituted alkylamino, optionally substituted hydroxyalkyl, amino, optionally substituted alkynyl, or optionally substituted cycloalkyl;

is 0, 1, or 2; and

 and  indicate the site of attachment of the L.

7. The compound of claim 1, wherein the ULM is:

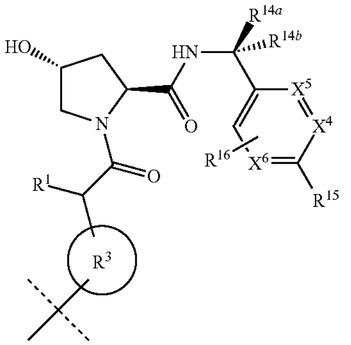
or

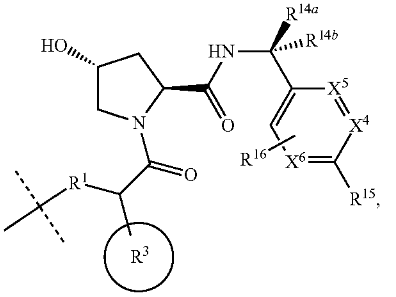
, wherein:

$R^3$ is an optionally substituted 5-6 membered heteroaryl;

is 0, 1, or 2;

each of $X^4$, $X^5$, and $X^6$ is CH or N, wherein no more than 2 are N;

$R^1$ is $C_{1-6}$ alkyl;

one of $R^{14a}$ and $R^{14b}$ is H, alkyl, haloalkyl, optionally substituted alkoxy, optionally substituted hydroxyl alkyl, optionally substituted alkylamino, optionally substituted amide, optionally substituted alkylamide, optionally substituted alkyl-cyano, optionally substituted alkyl-phosphate, optionally substituted heteroalkyl, optionally substituted alkyl-heterocycloalkyl, optionally substituted alkoxy-heterocycloalkyl, $COR^{26}$, $CONR^{27a}R^{27b}$, $NHCOR^{26}$, or $NCH_3COR^{26}$; and the other of $R^{14a}$ and $R^{14b}$ is H; or $R^{14a}$ and $R^{14b}$ together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxy or aziridinyl;

each $R^{27a}$ and $R^{27b}$ is independently H, $C_{1-6}$ alkyl, or 3-5 membered cycloalkyl;

$R^{15}$ is

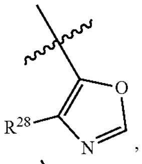
,
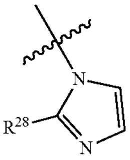
,
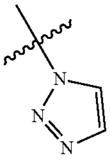
,
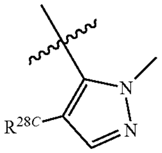
, or CN;

$R^{28}$ is H, methyl, $CH_2N(Me)_2$, $CH_2OH$, $CH_2O(C_{1-4}alkyl)$, $CH_2NHC(O)C_{1-4}alkyl$, $NH_2$,

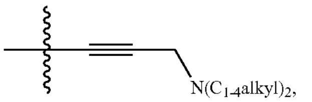
or
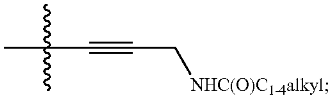
;

$R^{28C}$ is H, methyl, fluoro, or chloro;

$R^{16}$ is $C_{1-4}$alkyl, fluoro, chloro, CN, or $C_{1-4}$haloalkoxy; and the

indicates the site of attachment of the L.

8. The compound of claim 7, wherein one of $R^{14a}$ and $R^{14b}$ is H, $C_{1-4}$ alkyl, $C_{1-4}$ haloalkyl, $C_{1-4}$ hydroxyalkyl, $C_{1-4}$ alkyloxyalkyl, $C_{1-4}$ alkyl-$NR^{27a}R^{27b}$ or $CONR^{27a}R^{27b}$.

9. The compound of claim 7, wherein the ULM is:
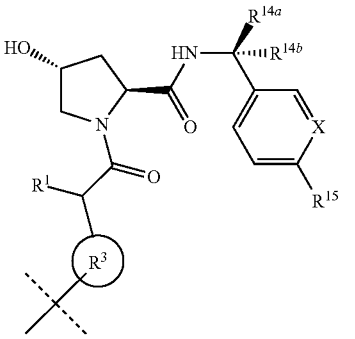
or
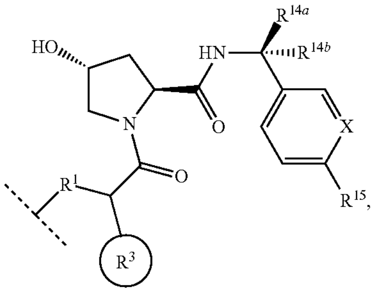
wherein X is CH or N,
and the
indicates the site of attachment of the L.
10. The compound of claim 7, wherein $R^3$ is isoxazolyl, 4-chloroisoxazolyl, 4-fluoroisoxazolyl, or pyrazolyl.
11. The compound of claim 1, wherein the ULM is:
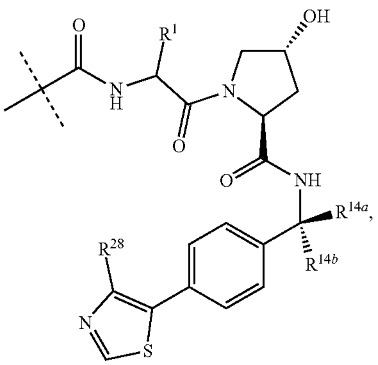
-continued
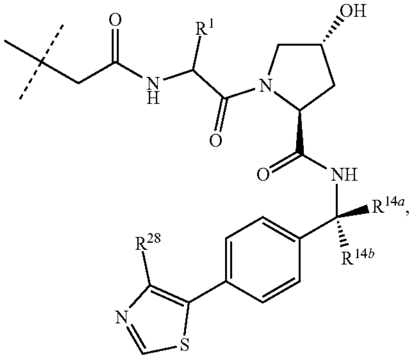
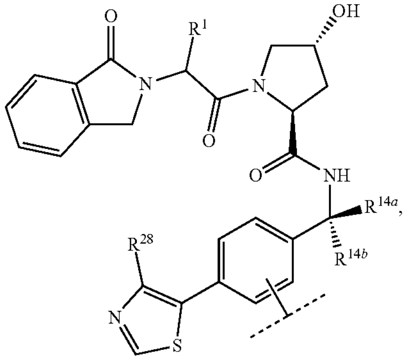
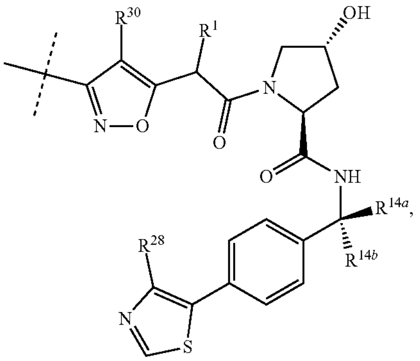
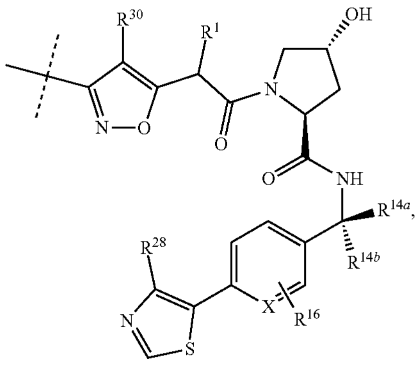
or -continued
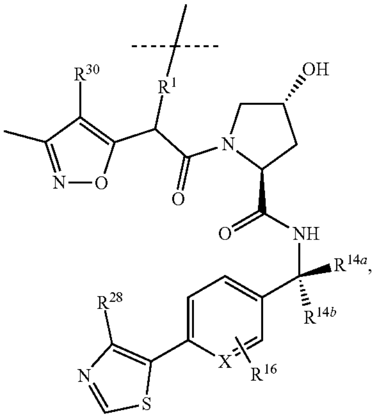
wherein:
X is CH or N;
$R^{28}$ is H, methyl, $CH_2N(Me)_2$, $CH_2OH$, $CH_2O(C_{1-4}alkyl)$, $CH_2NHC(O)C_{1-4}alkyl$, $NH_2$,
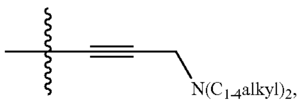
or
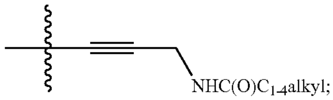
$R^{30}$ is H, F, or Cl; and the
indicates the site of attachment of the L.
12. The compound of claim 11, wherein the ULM is:
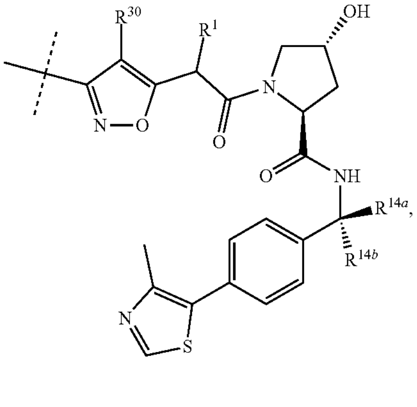
-continued
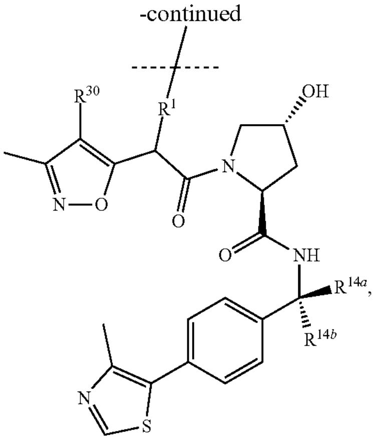
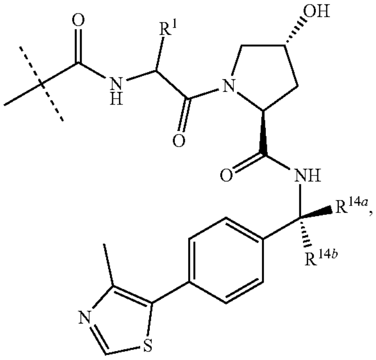
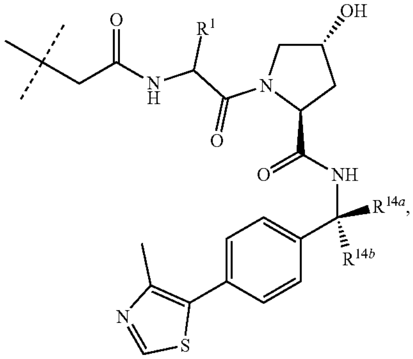
or
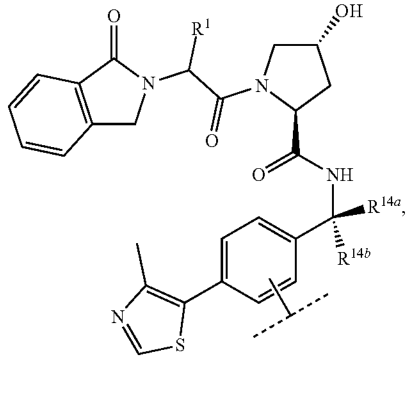
wherein the
indicates the site of attachment of the L.

13. The compound of claim 1, wherein the ULM is:
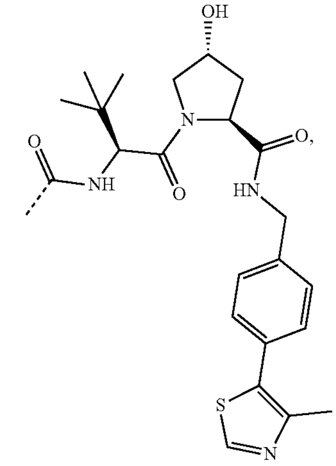
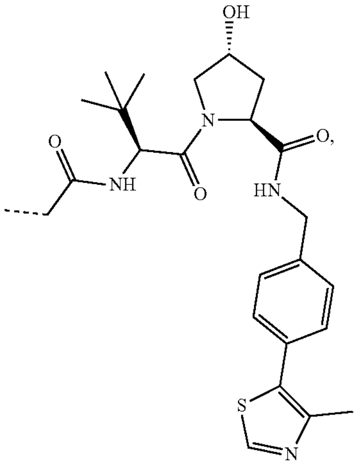
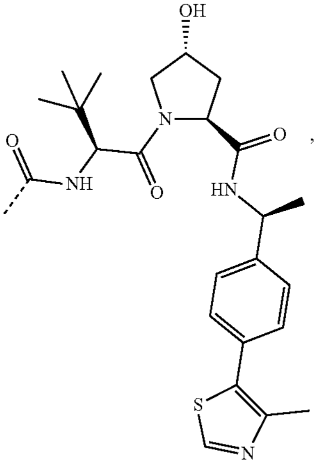
-continued
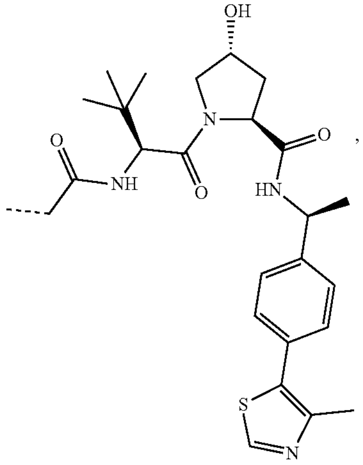
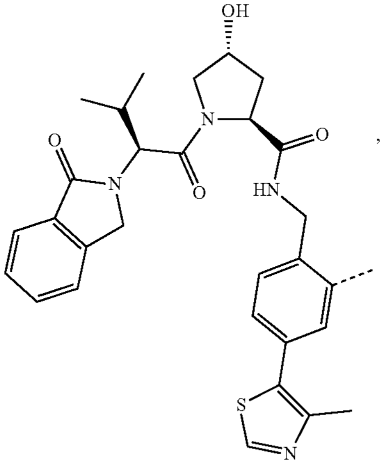
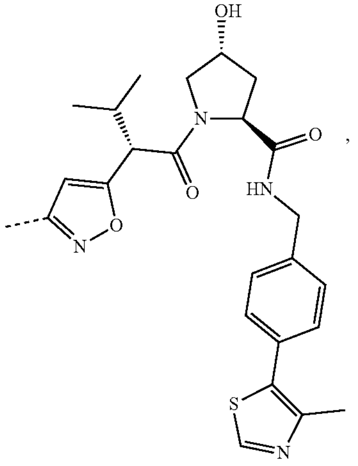

-continued
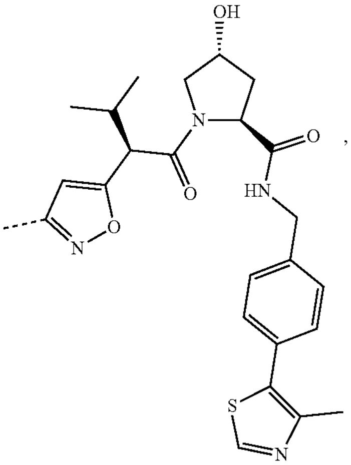
,
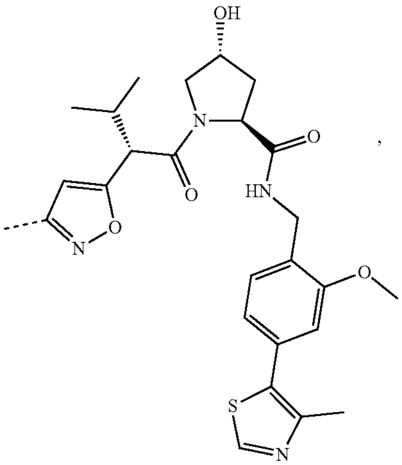
,
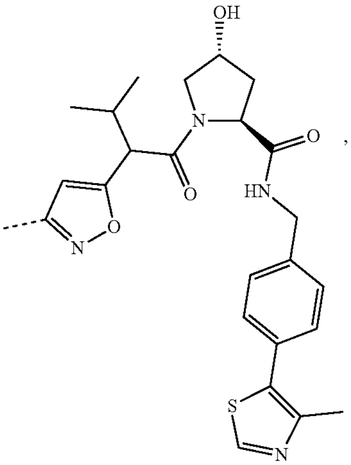
,
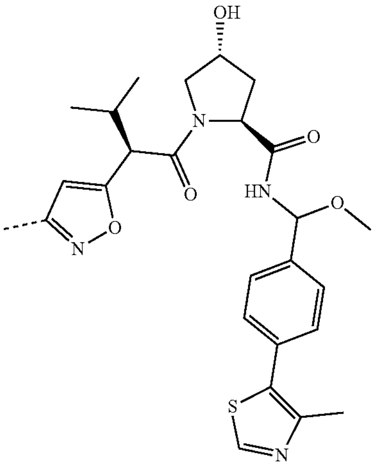
,
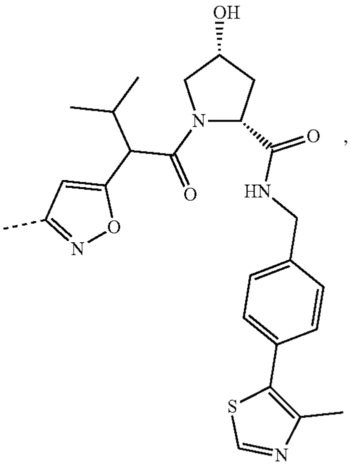
,
-continued
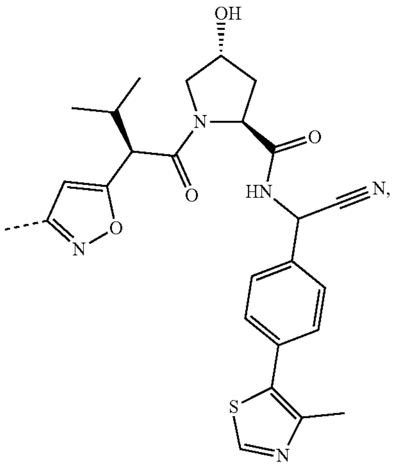
, -continued
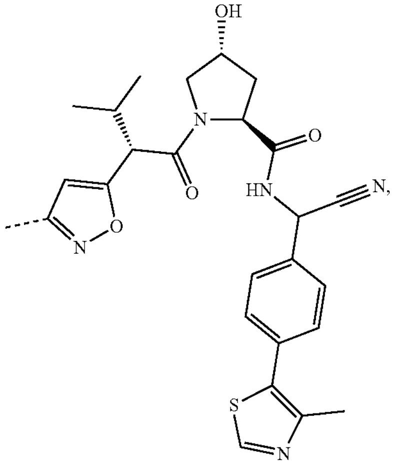
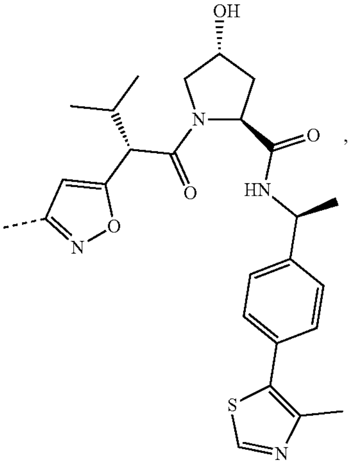
,
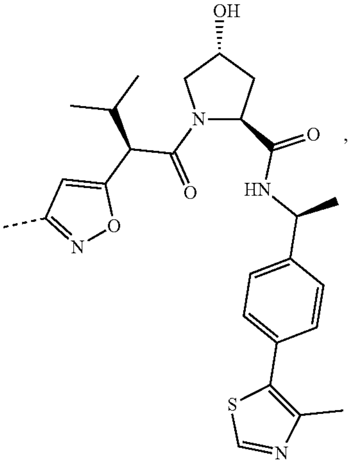
,
-continued
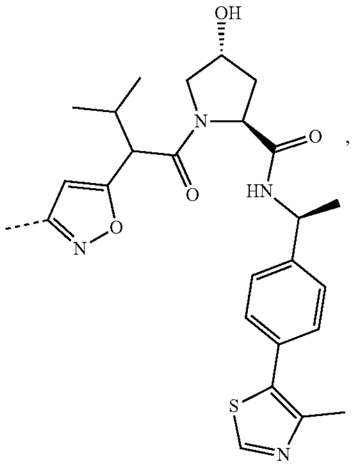
,
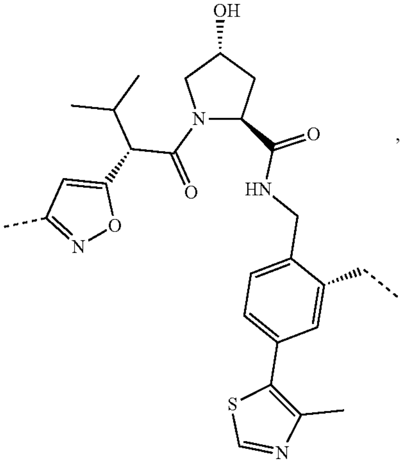
,
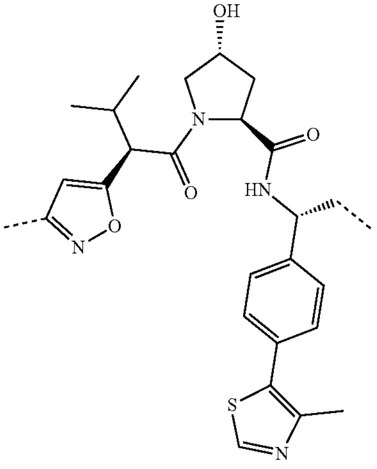
, -continued
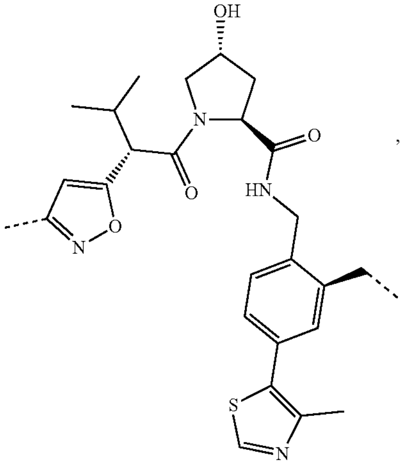
,
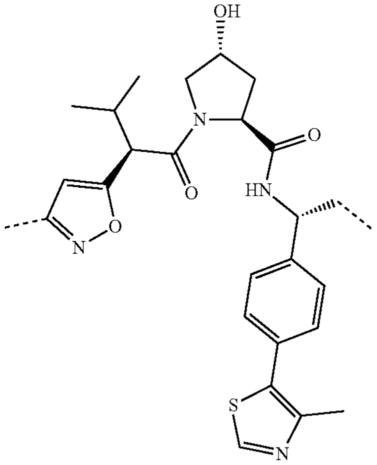
,
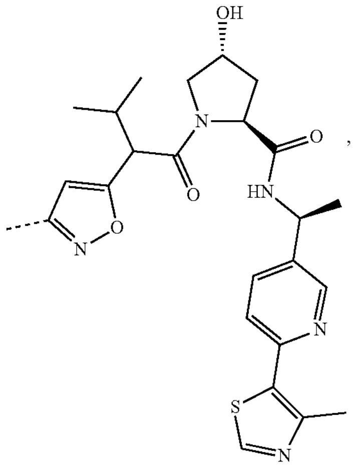
,
-continued
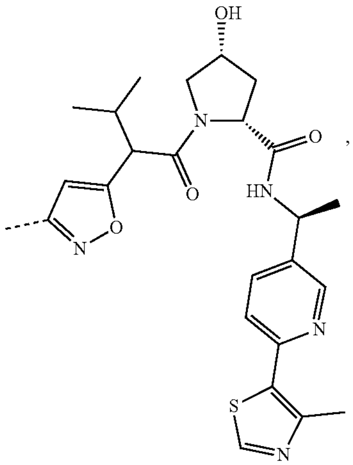
,
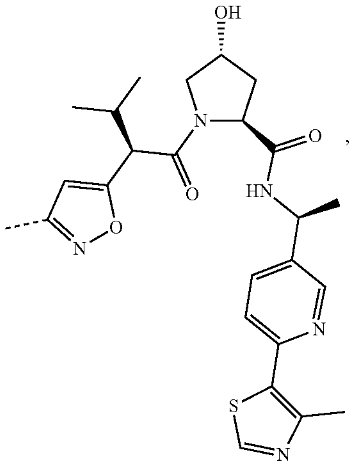
,
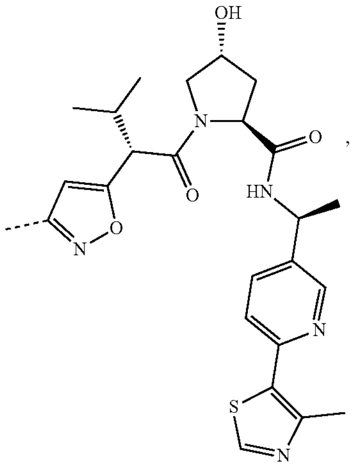
, -continued
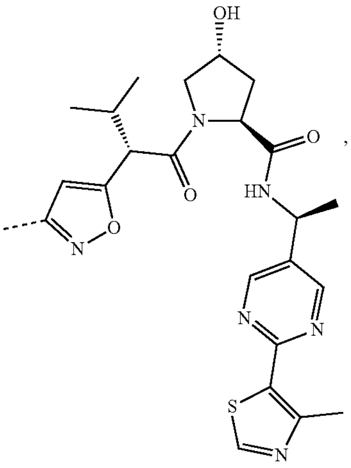
,
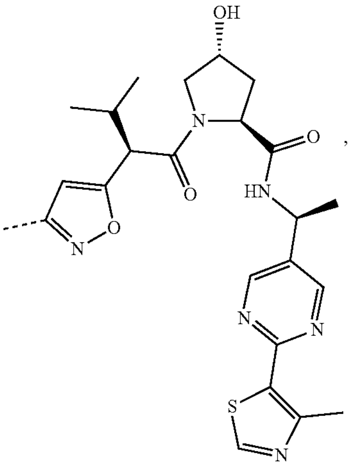
,
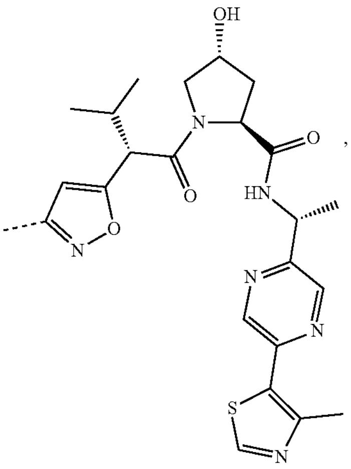
,
-continued
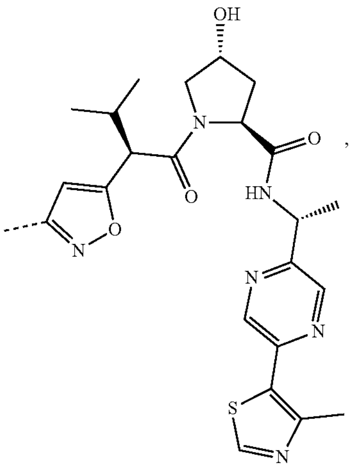
,
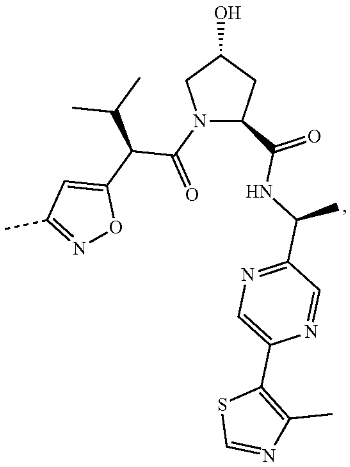
,
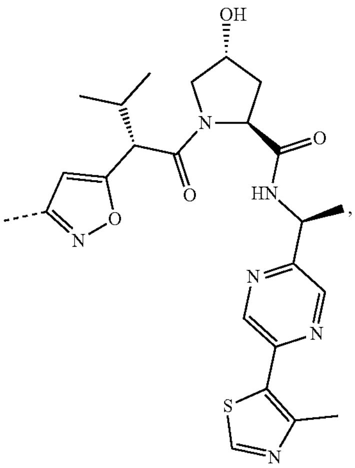
, -continued
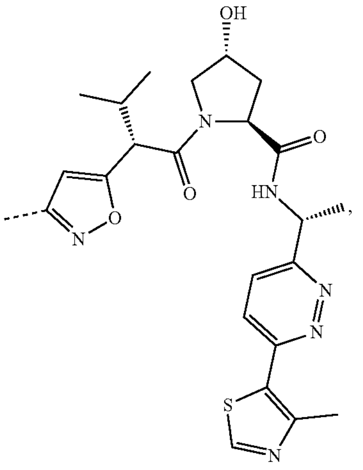
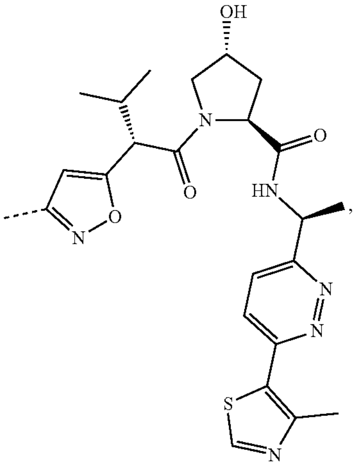
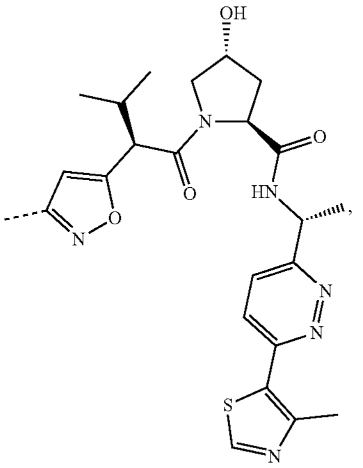
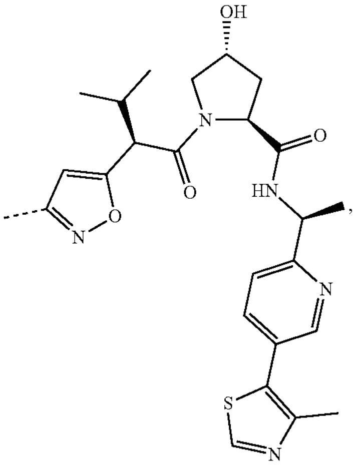
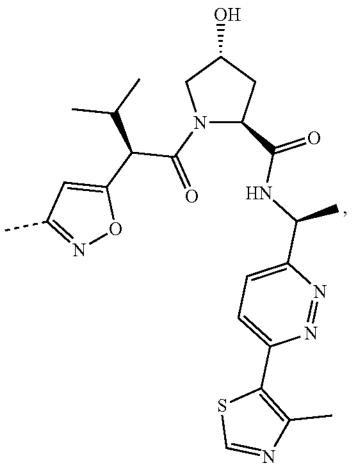
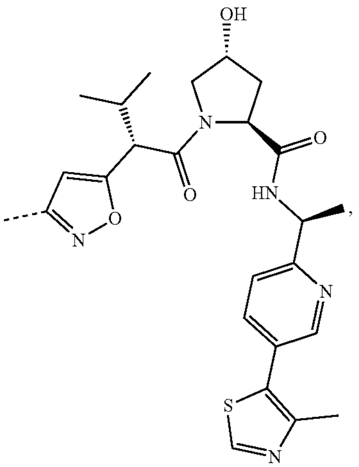
-continued -continued
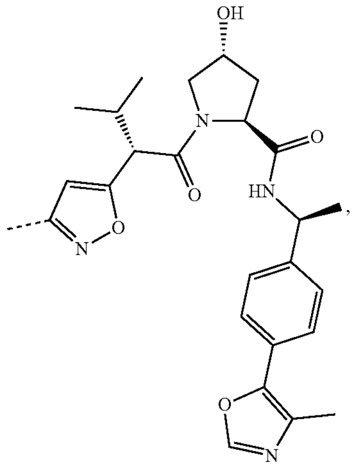
,
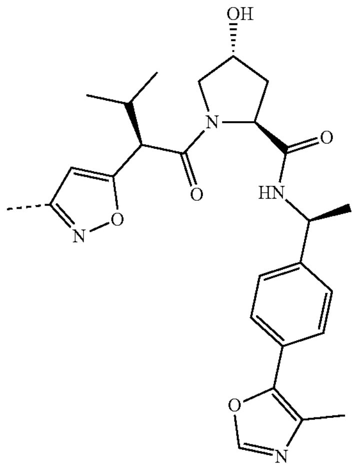
,
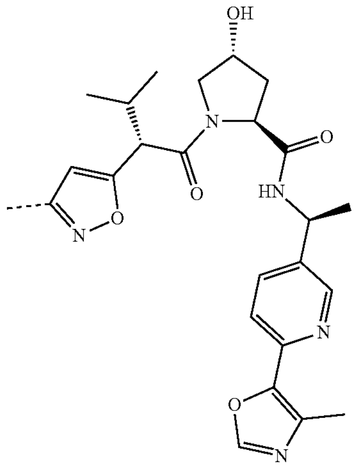
,
-continued
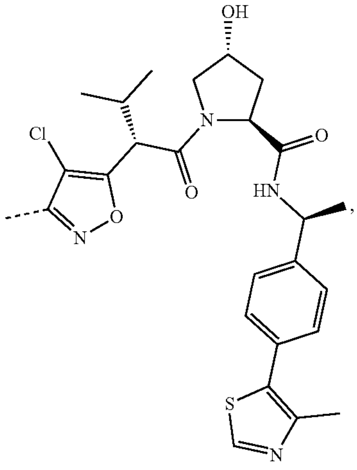
,
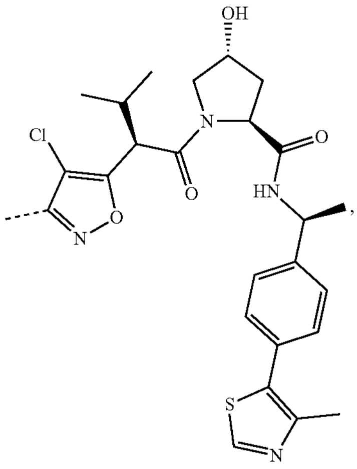
,
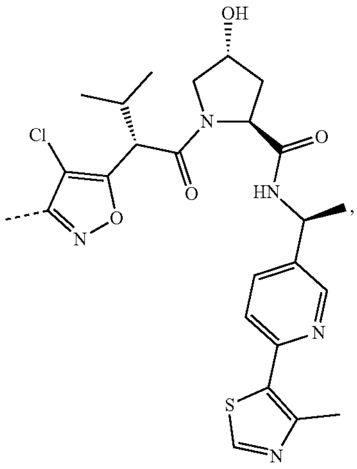
, -continued
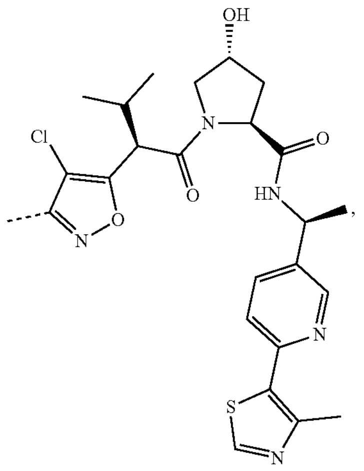
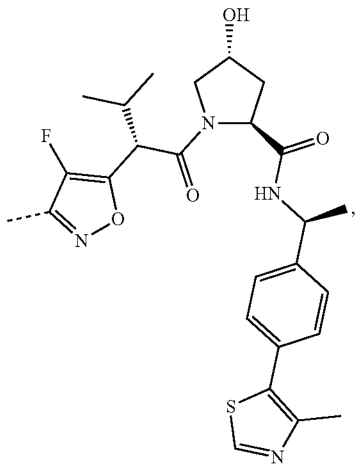
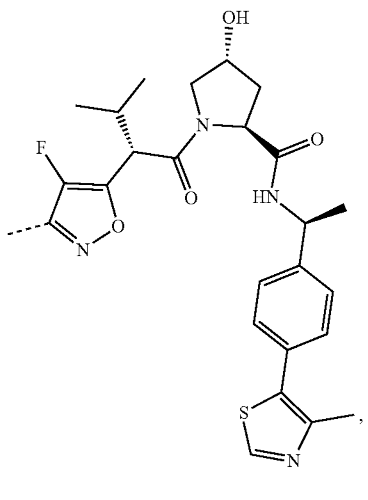
-continued
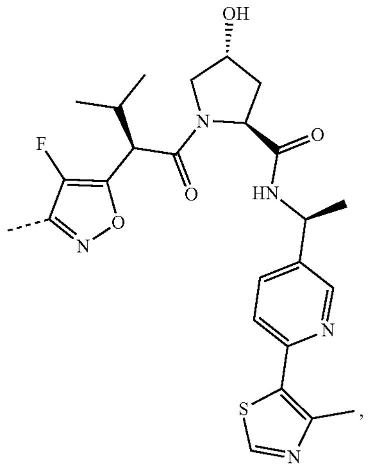
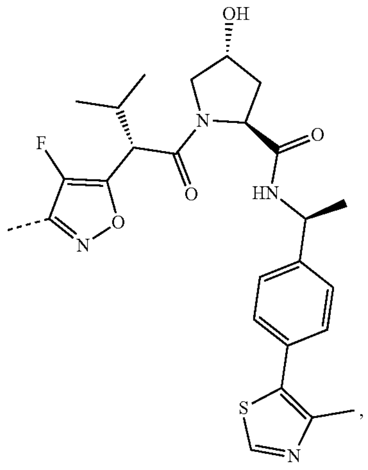
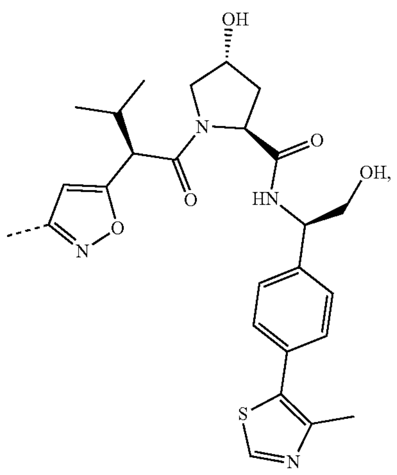

-continued
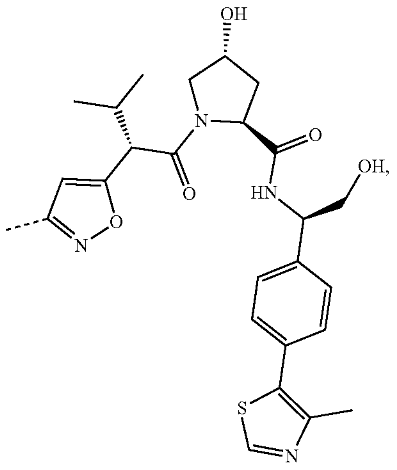
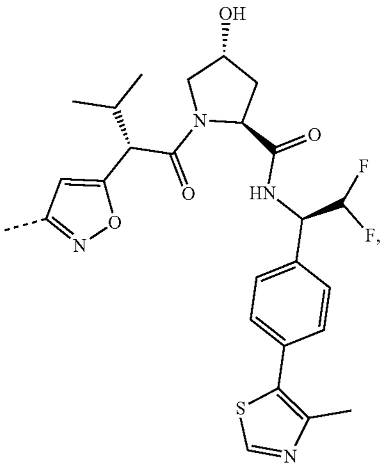
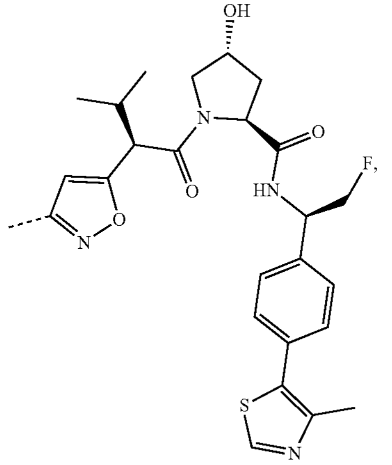
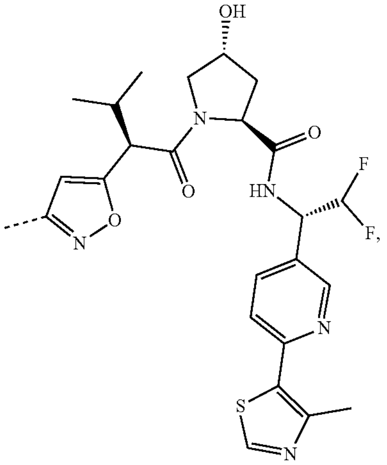
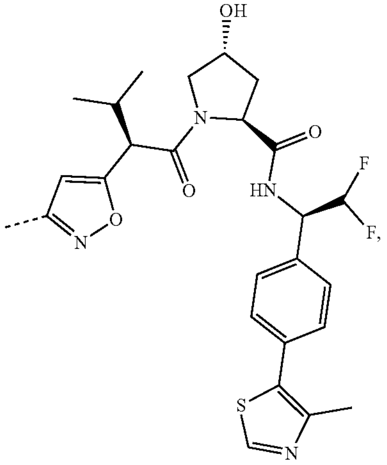
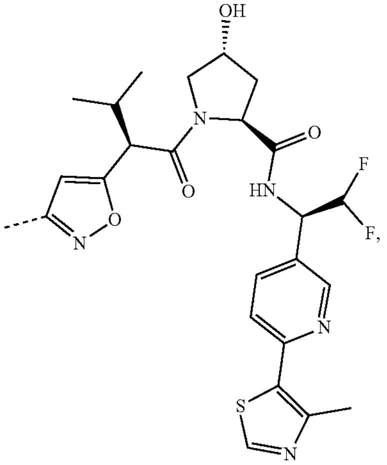
-continued -continued
-continued
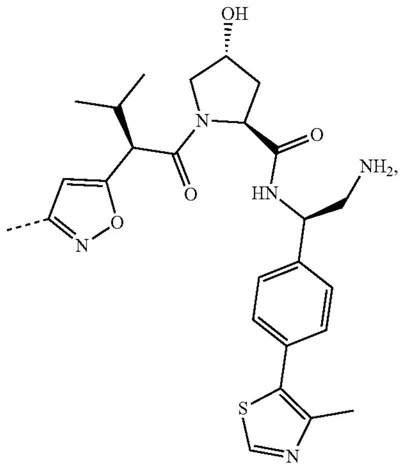
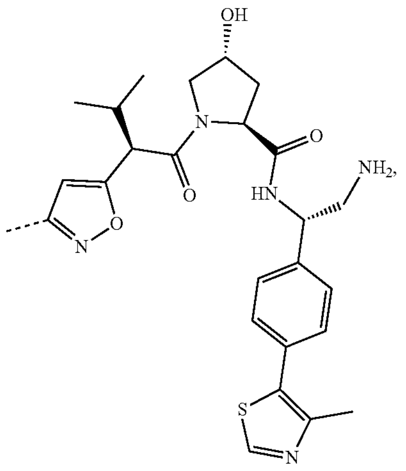
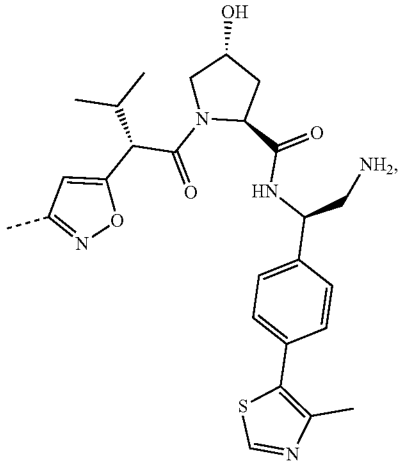
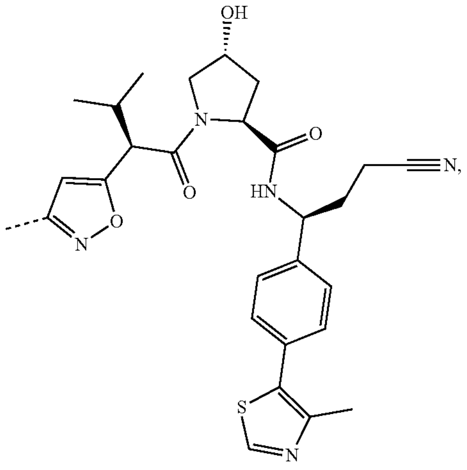
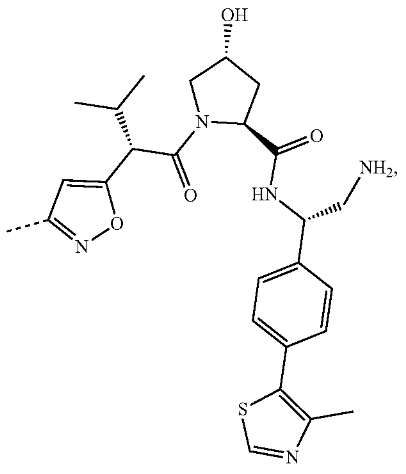
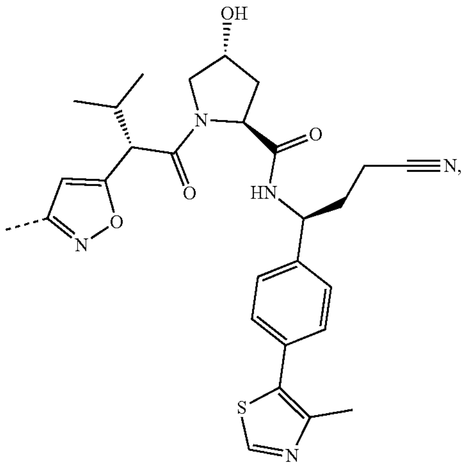

-continued
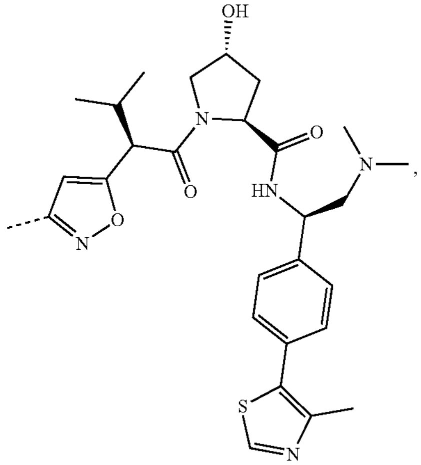
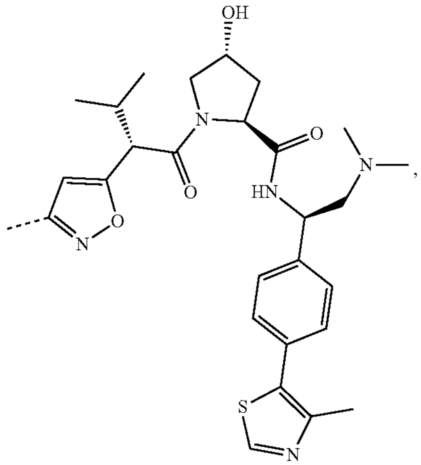
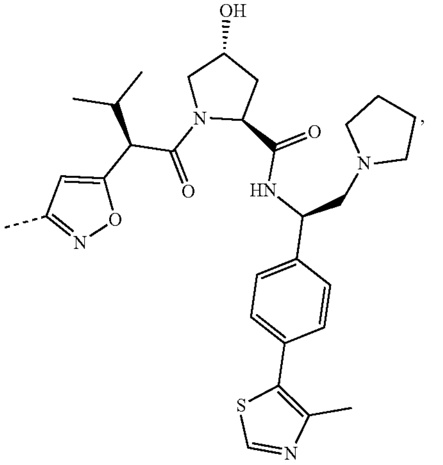
-continued
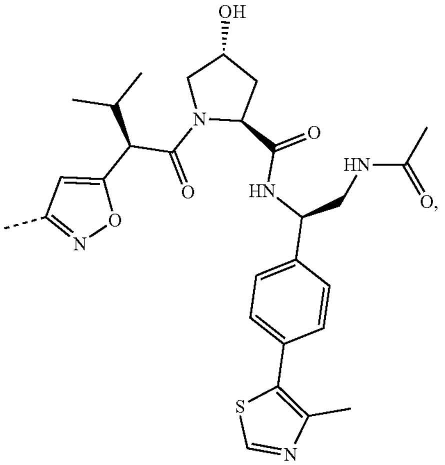
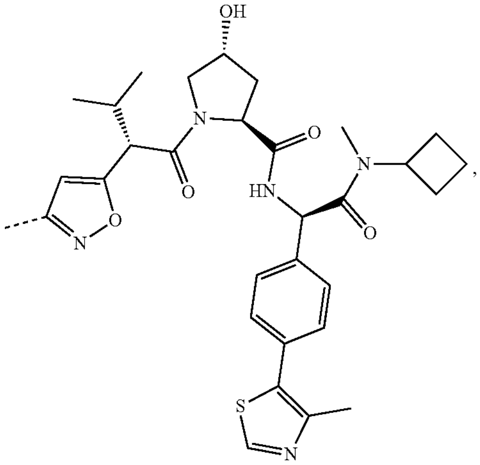
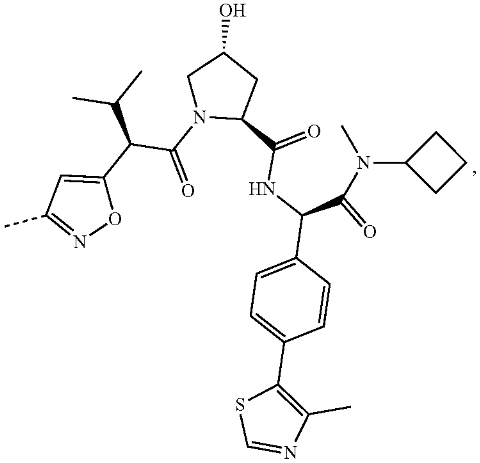

-continued
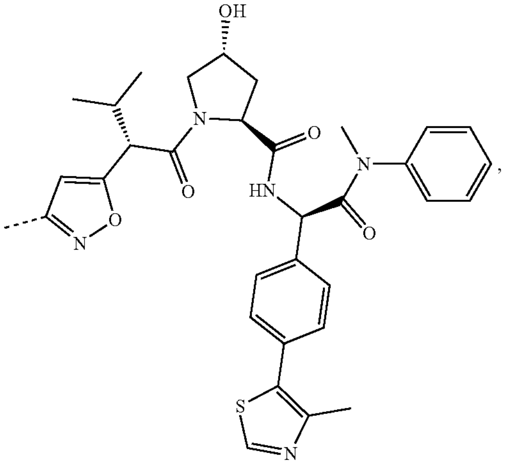
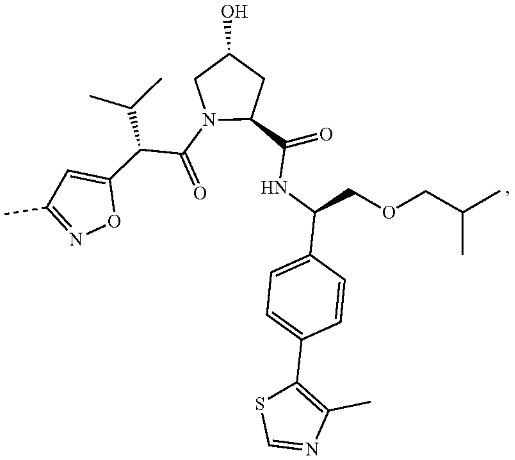
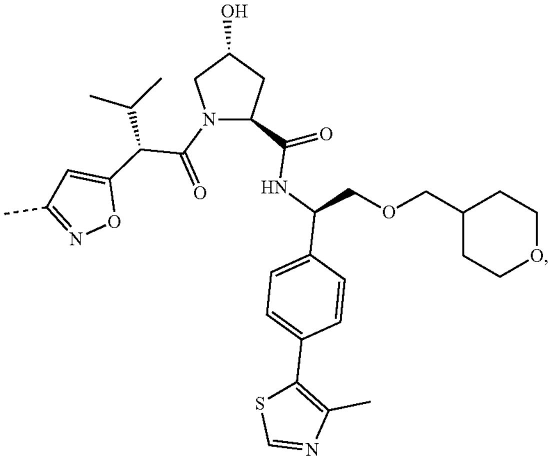
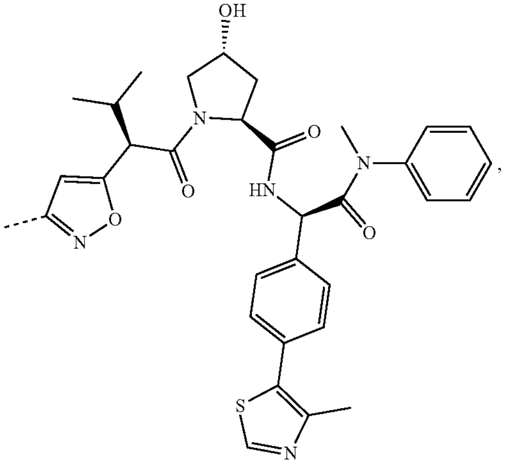
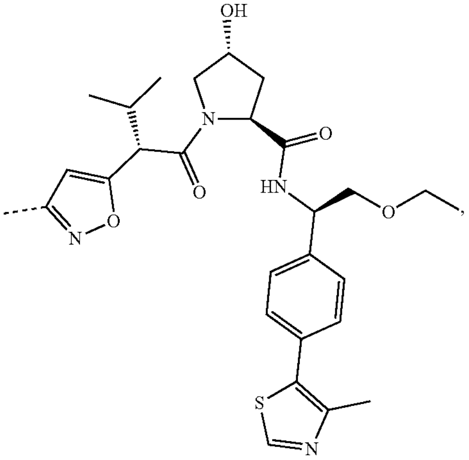
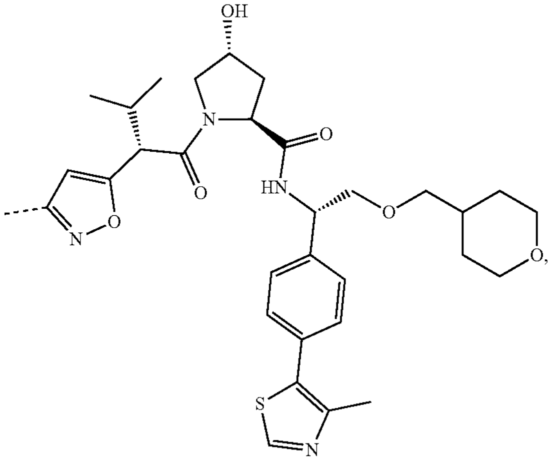

-continued
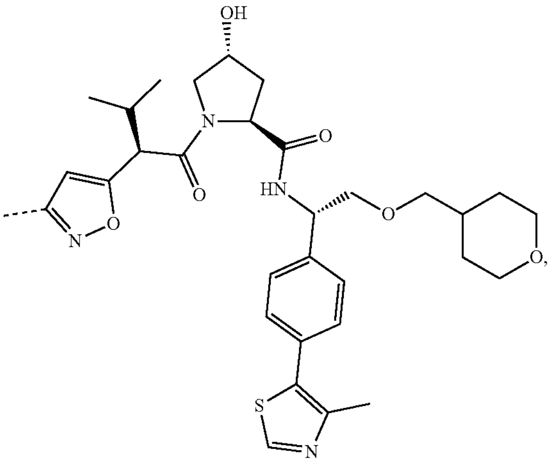
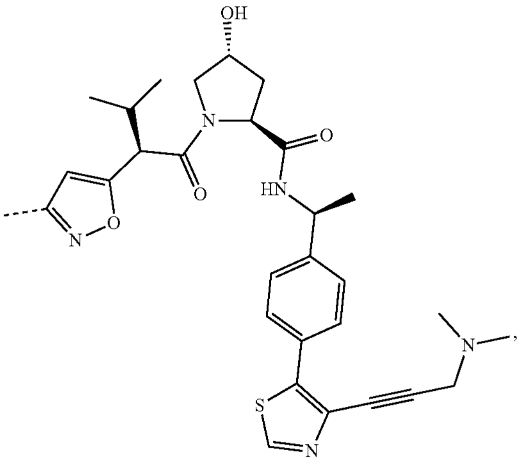
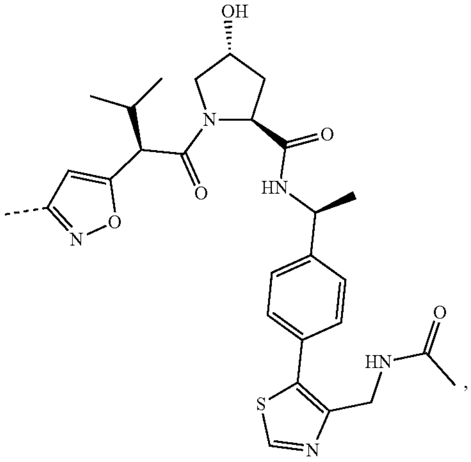
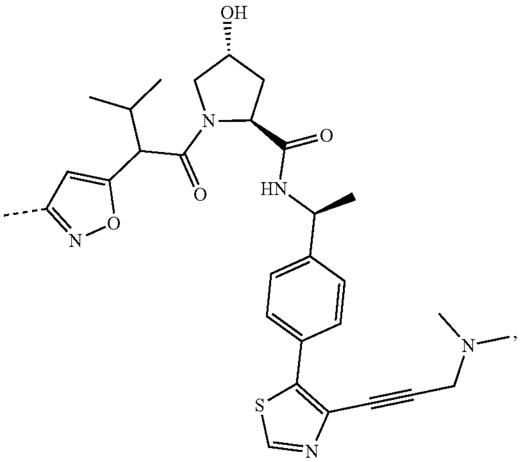
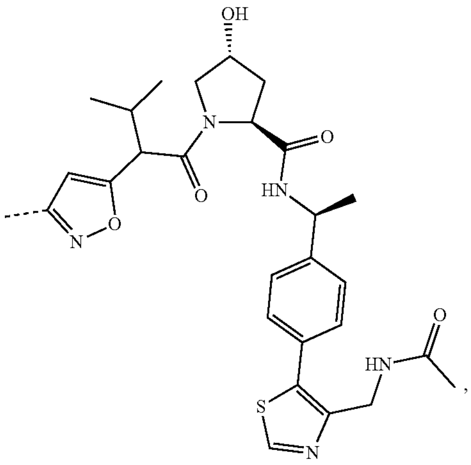
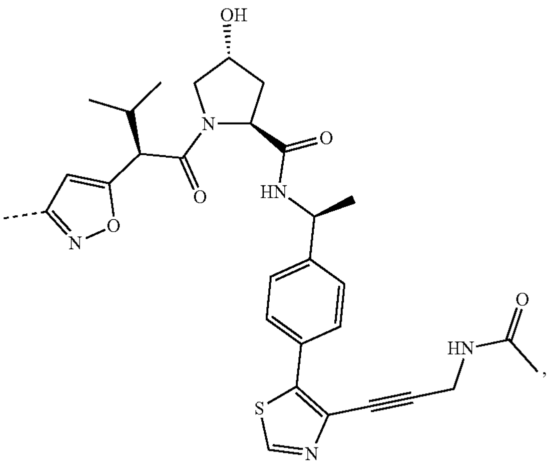

-continued
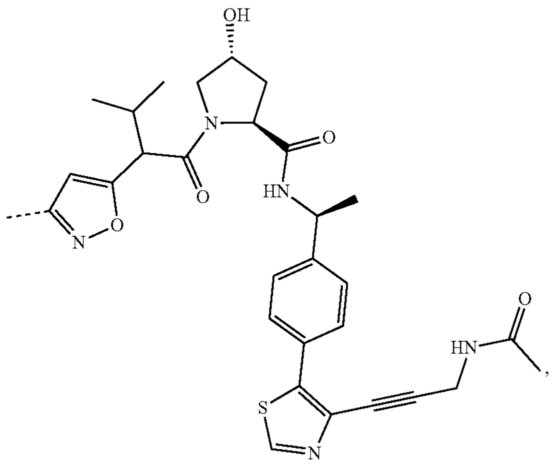
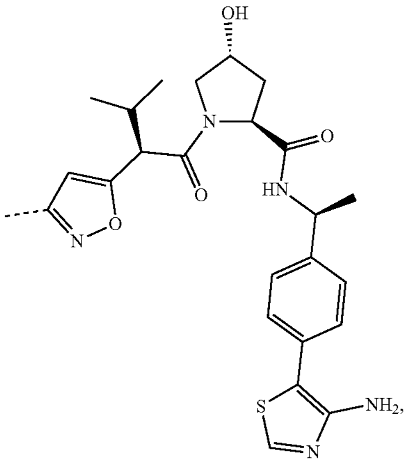
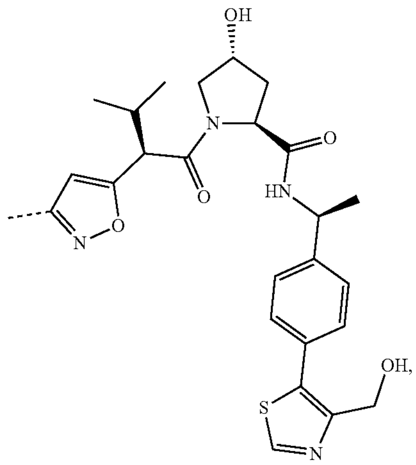
-continued
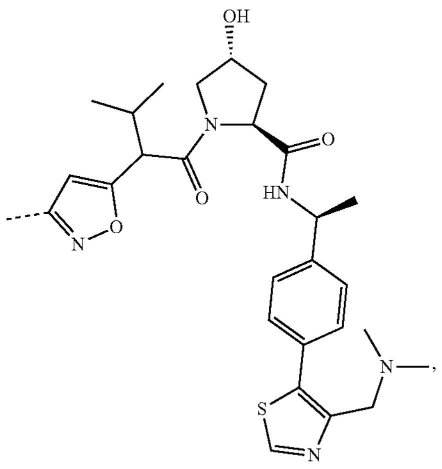
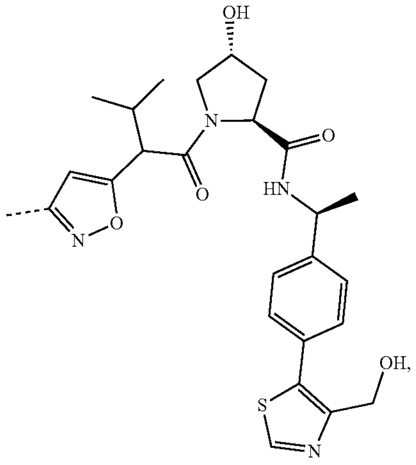
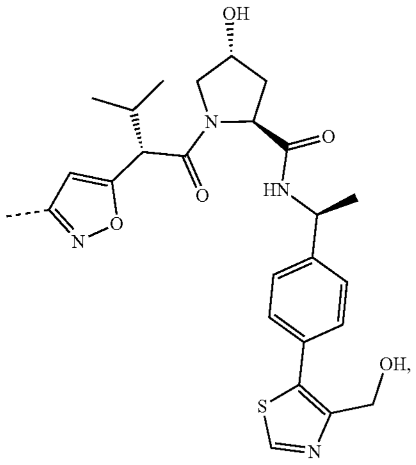

-continued
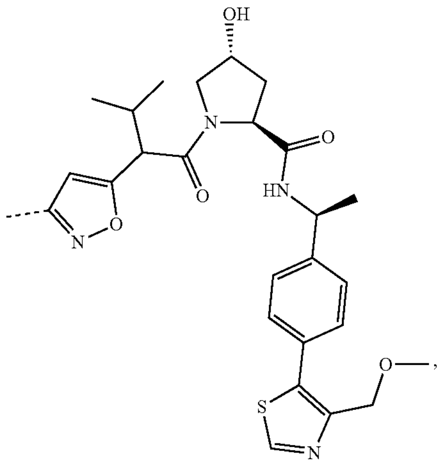
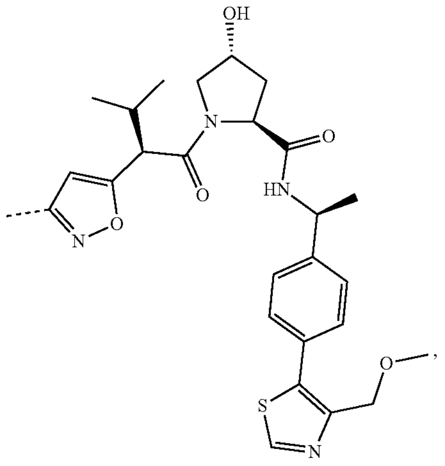
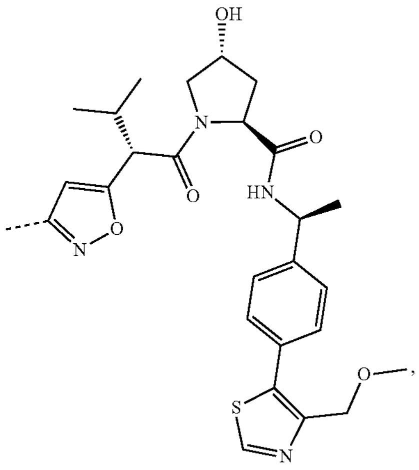
-continued
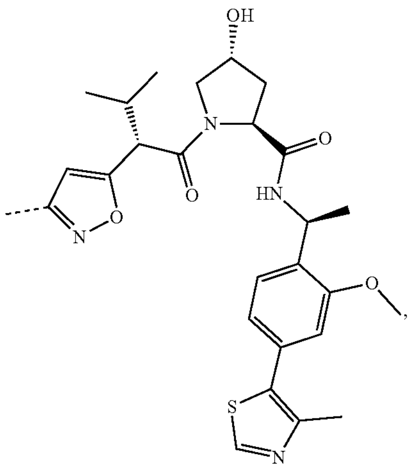
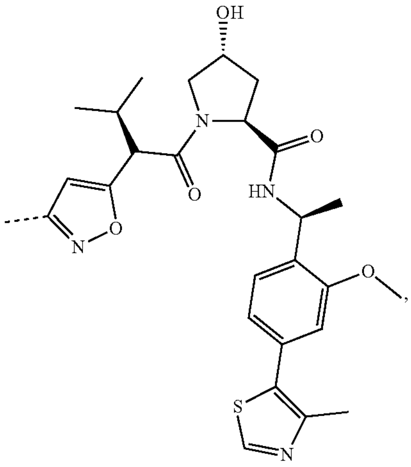
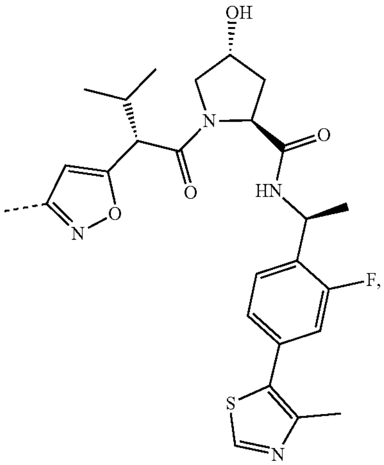

-continued
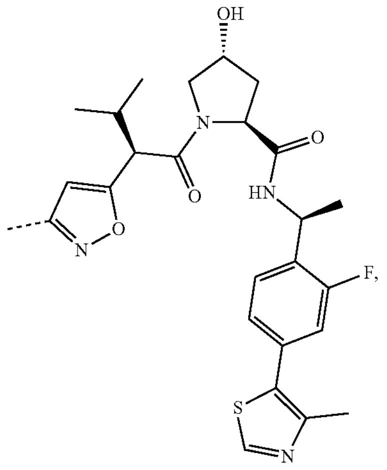
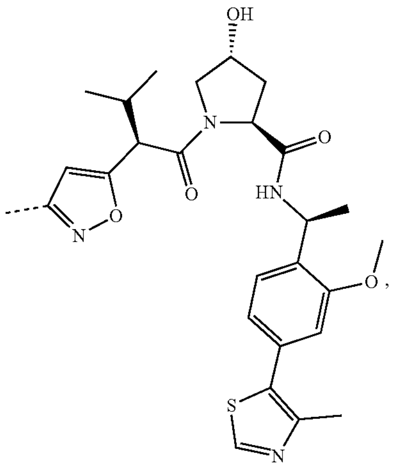
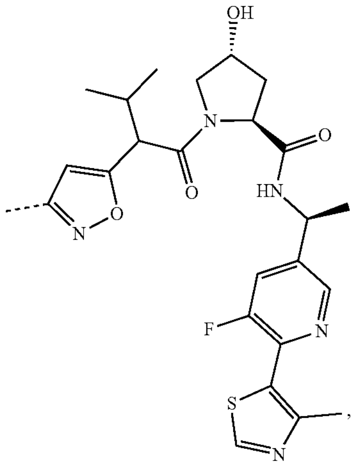
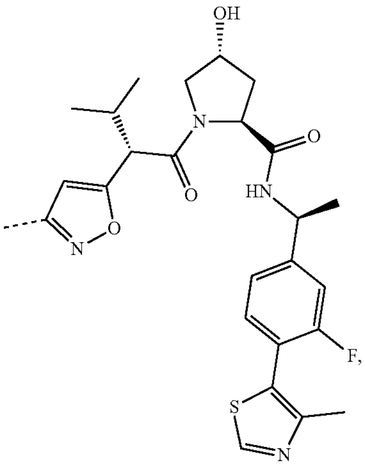
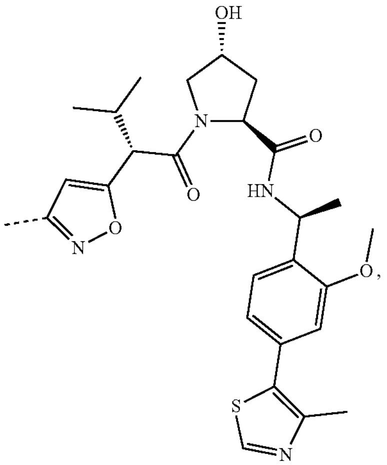
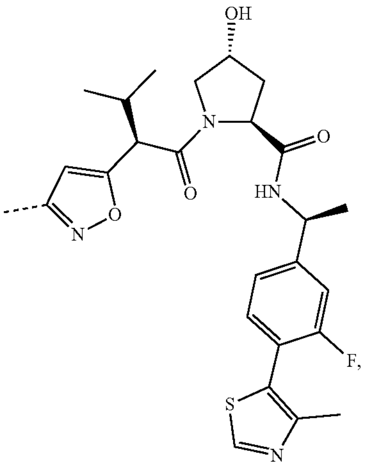

-continued
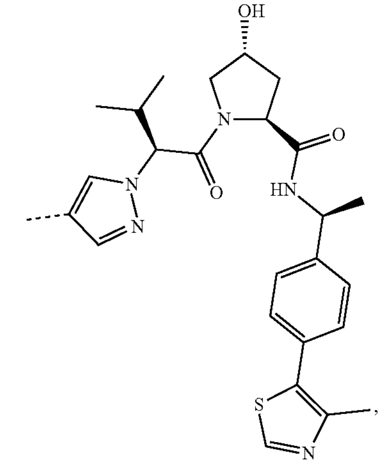
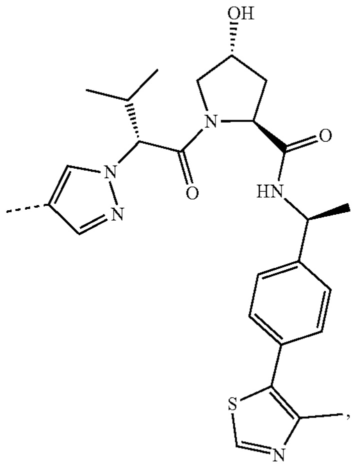
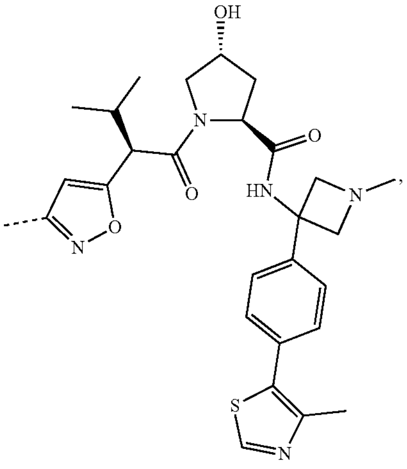
-continued
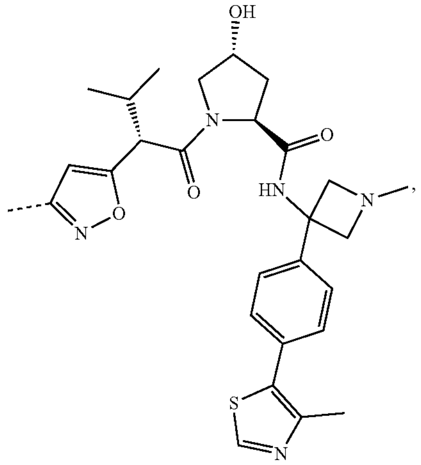
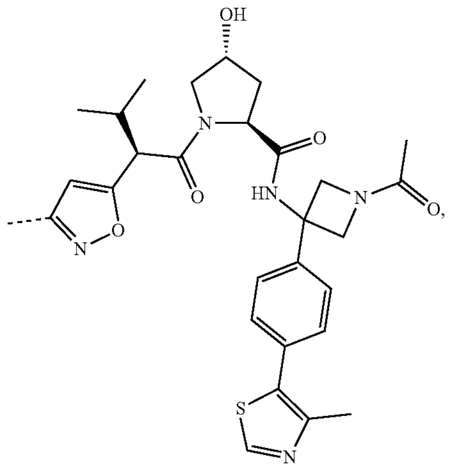
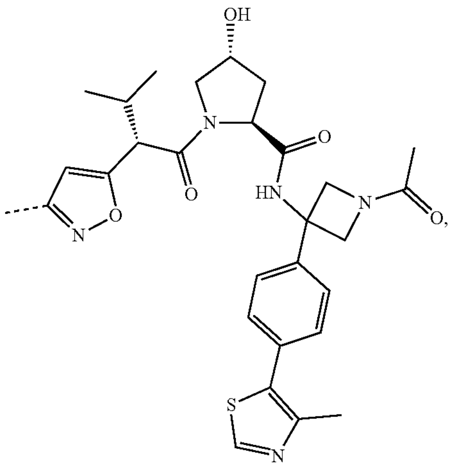

-continued
-continued
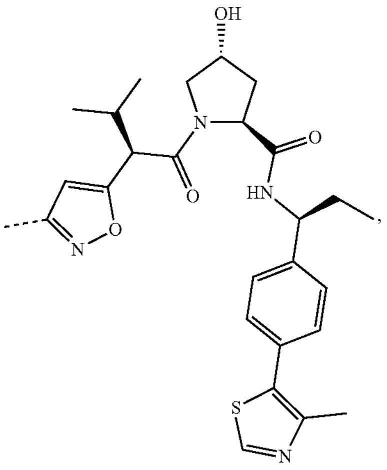
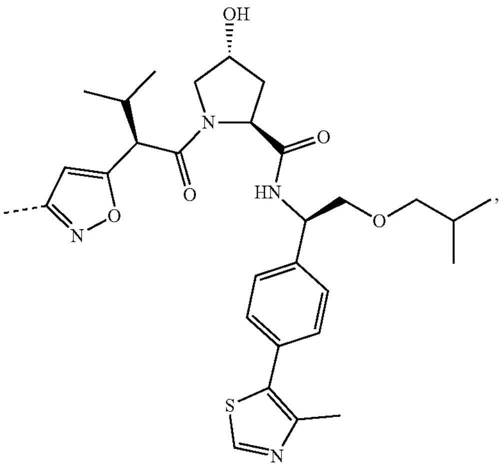
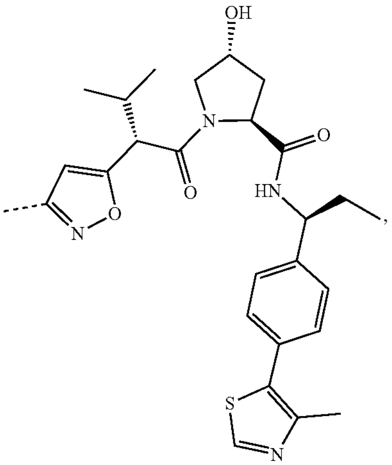
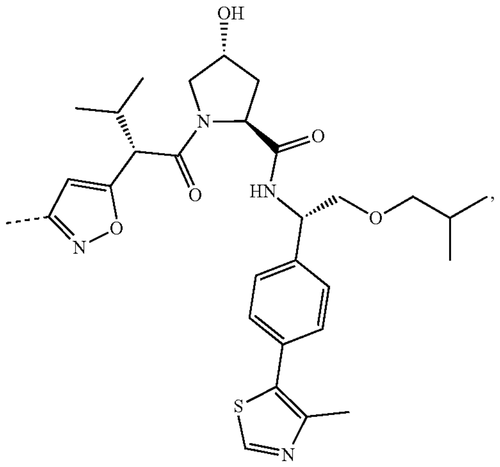
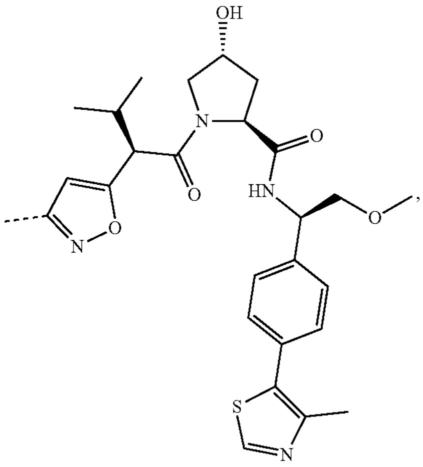
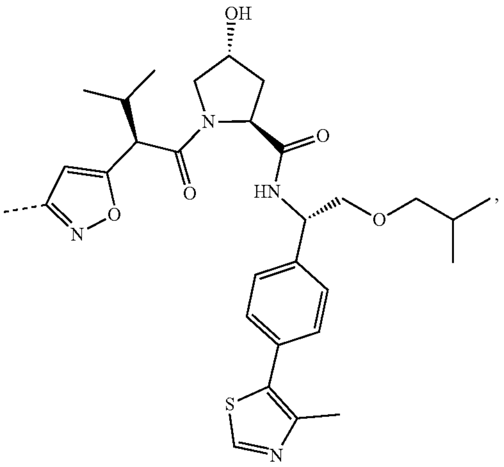

-continued
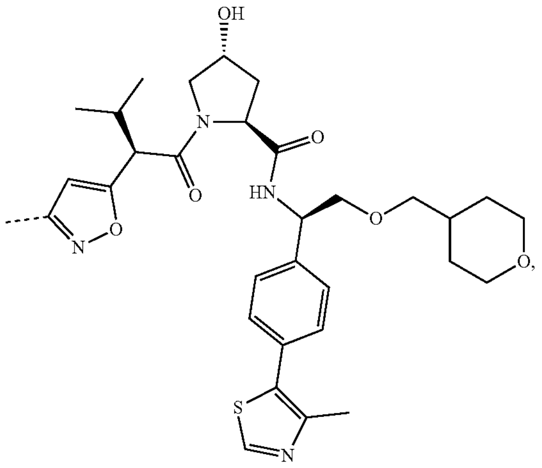
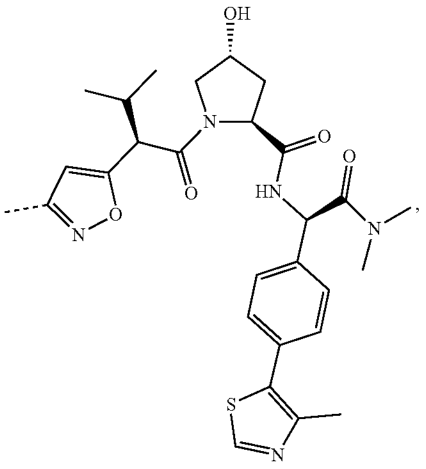
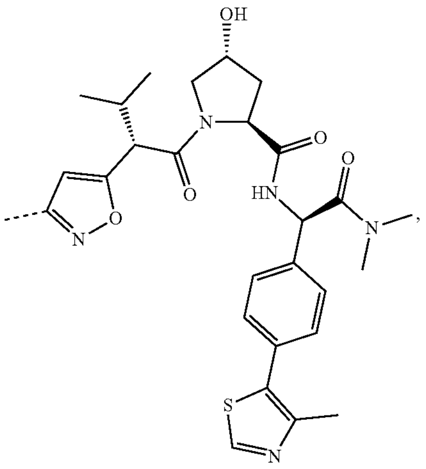
-continued
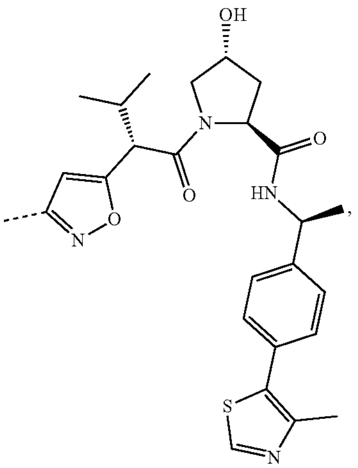
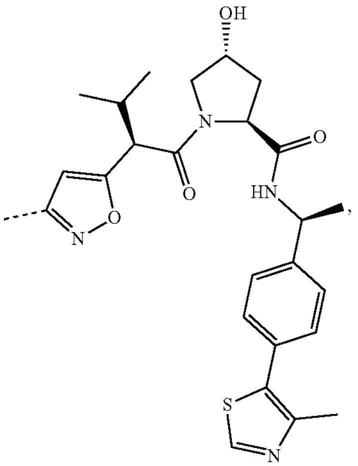
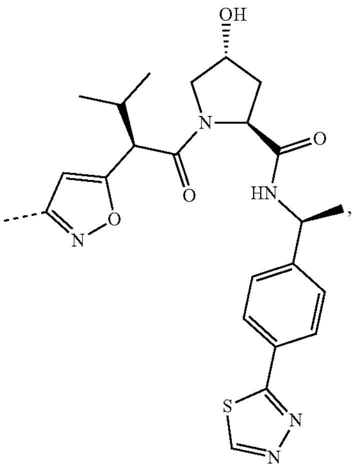

-continued
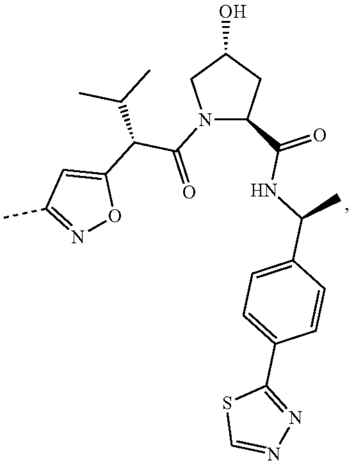
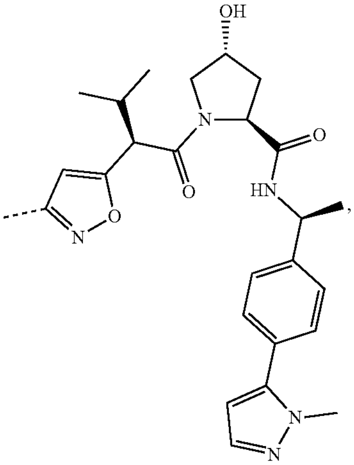
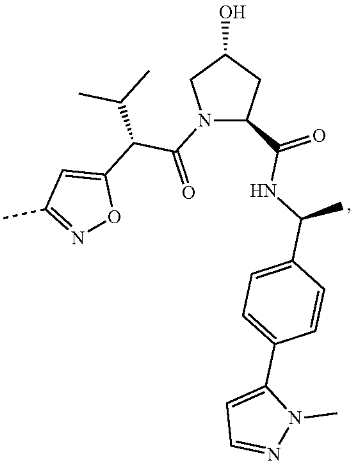
-continued
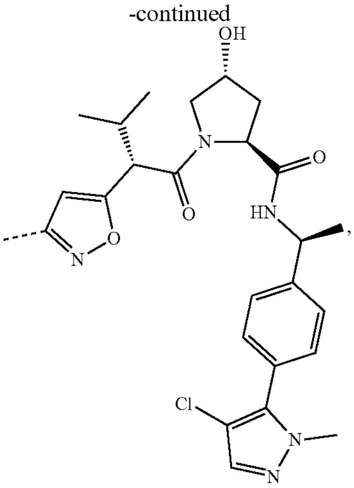
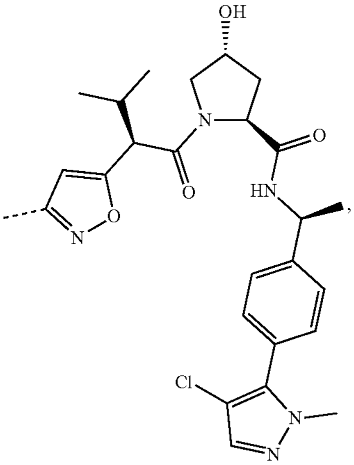
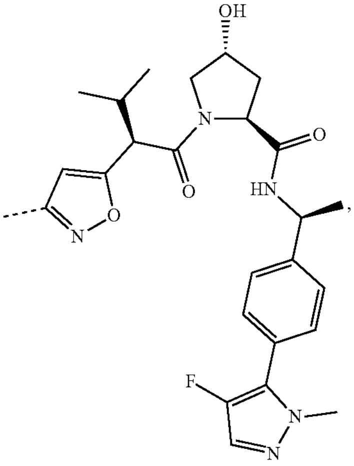

-continued
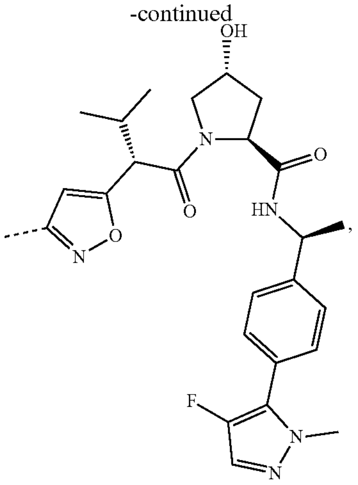
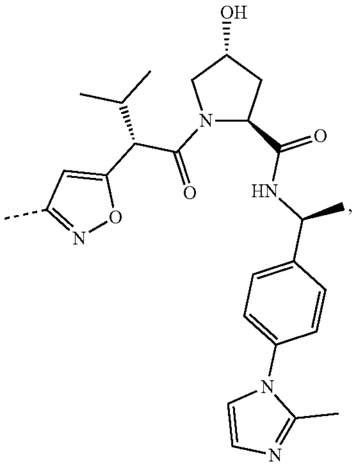
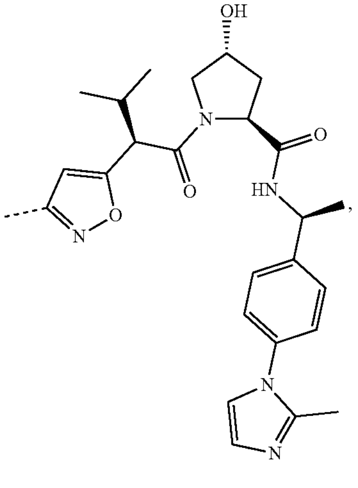
-continued
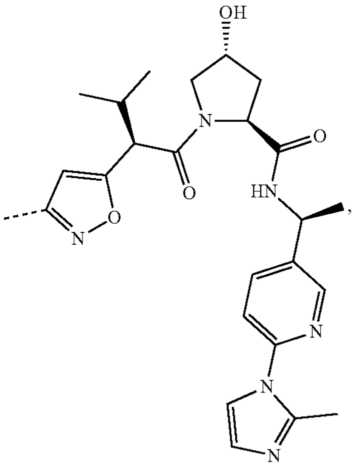
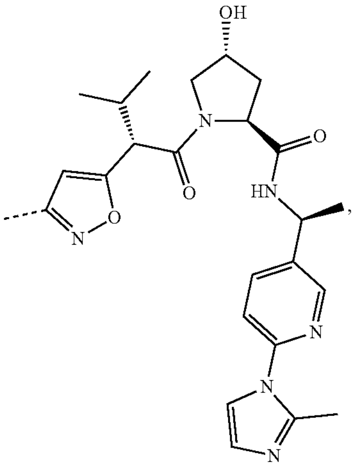
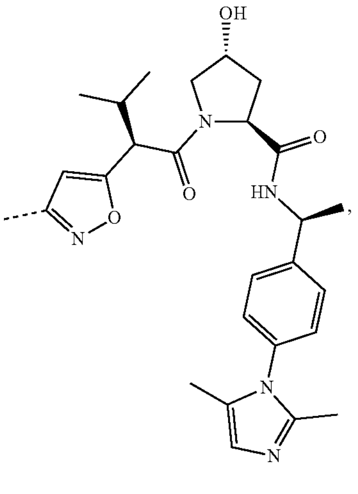

-continued
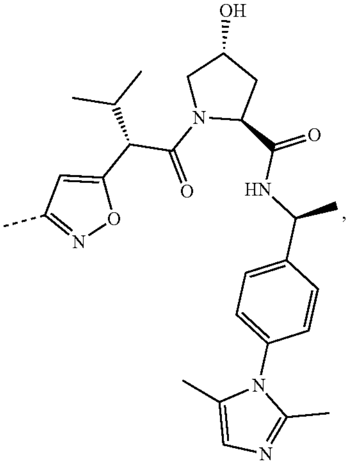
,
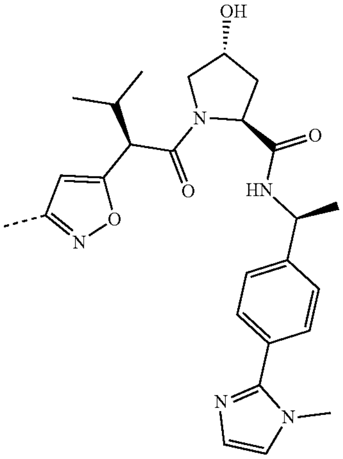
,
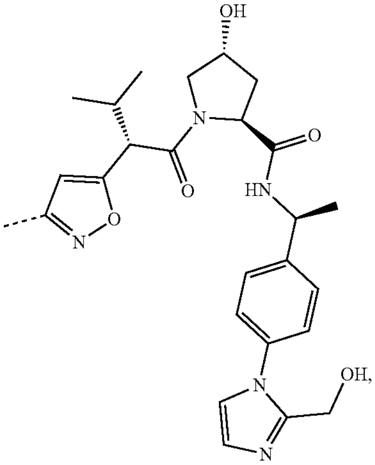
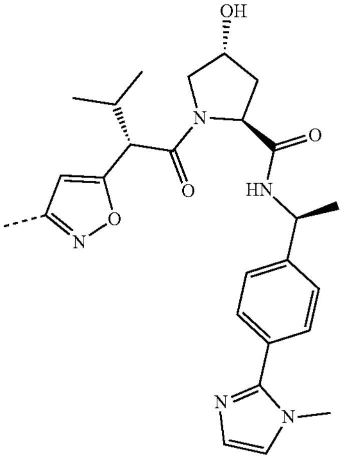
,
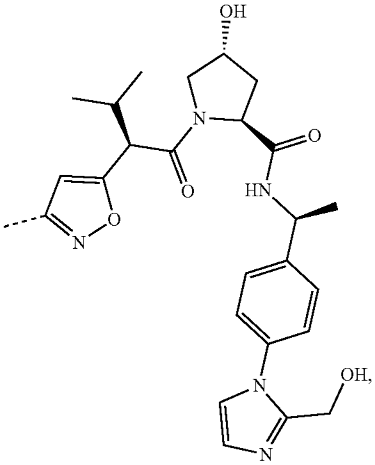
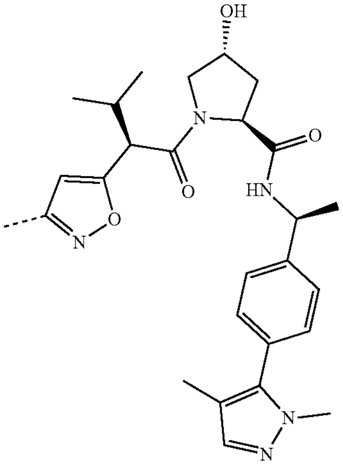
, -continued
-continued
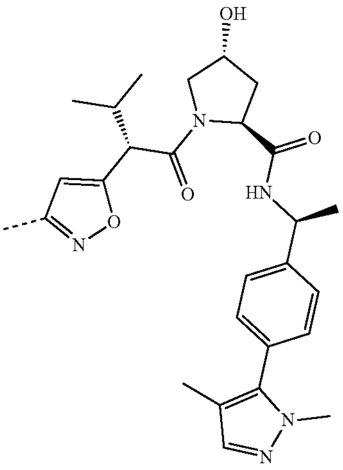
,
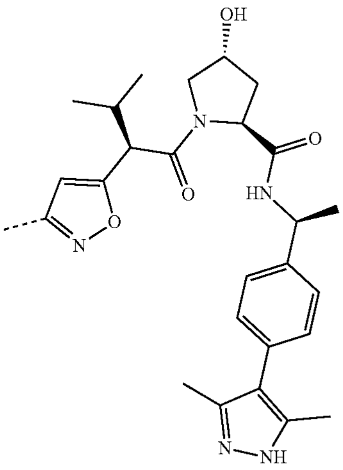
,
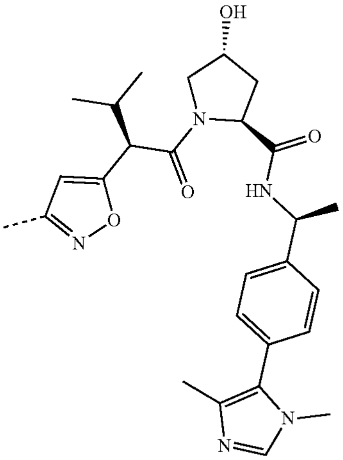
,
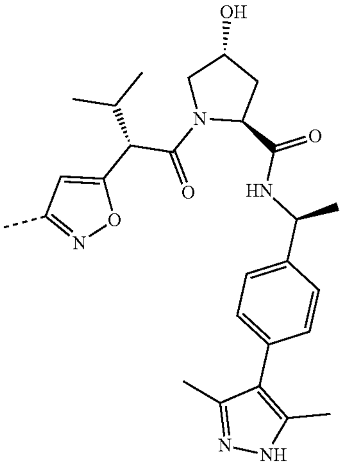
,
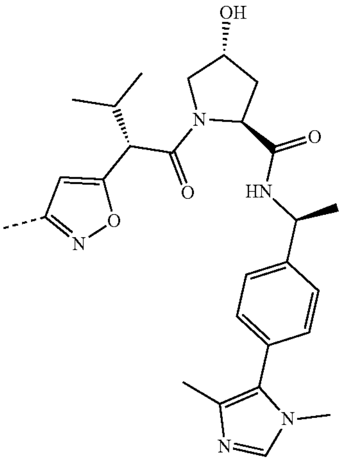
,
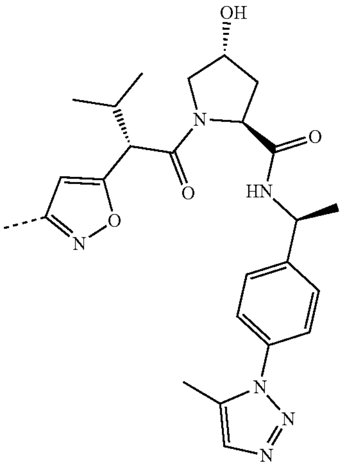
, -continued
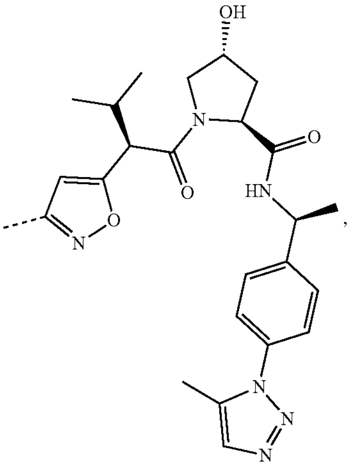
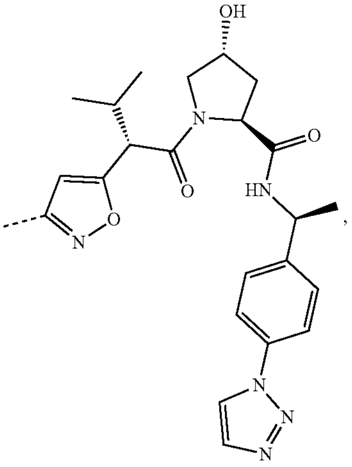
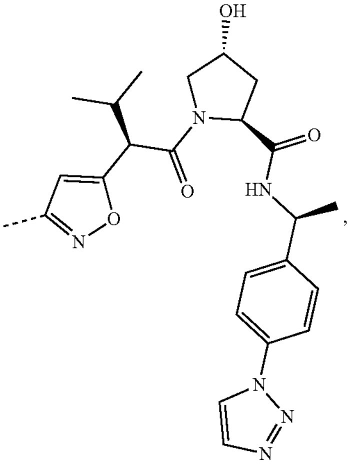
-continued
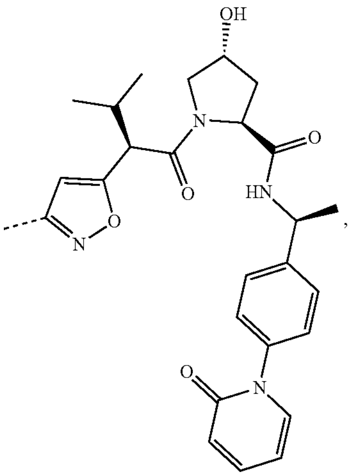
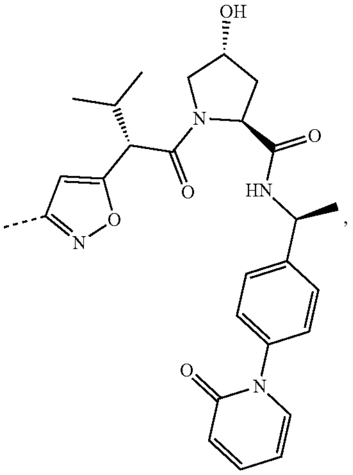
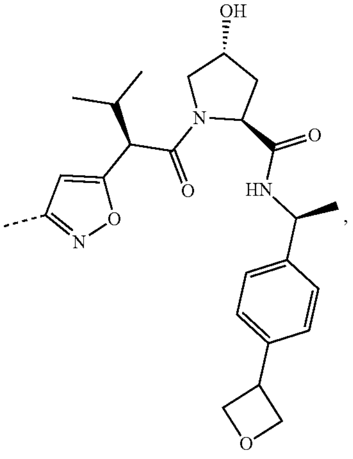

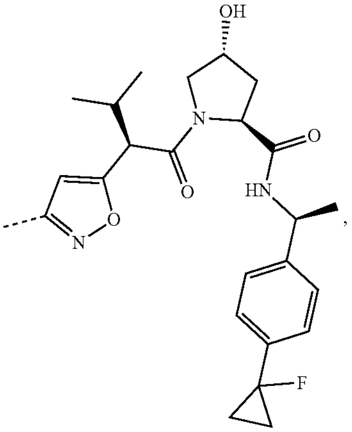
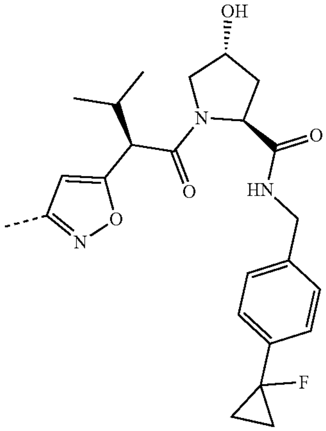
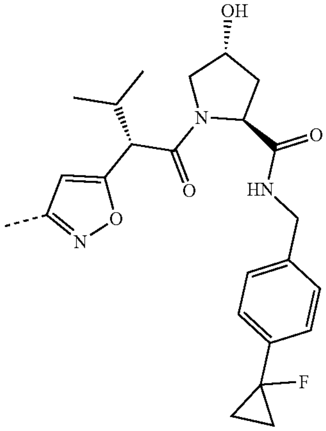
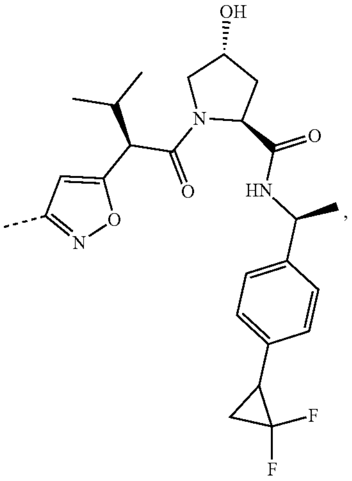
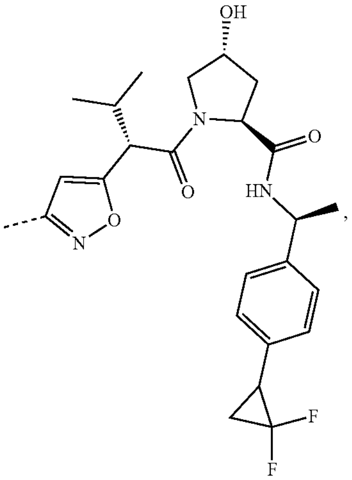
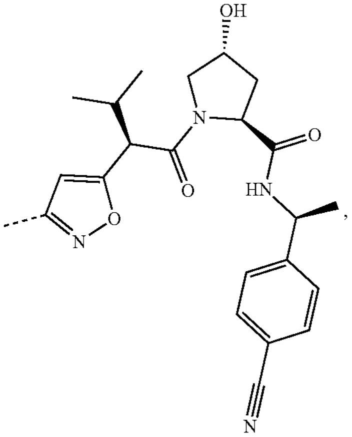

-continued
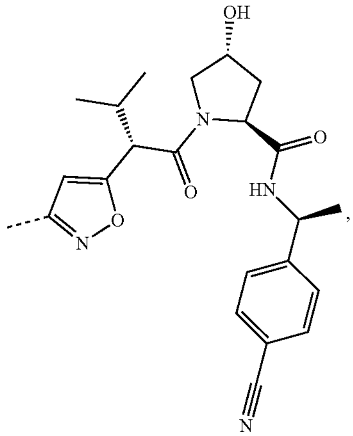
,
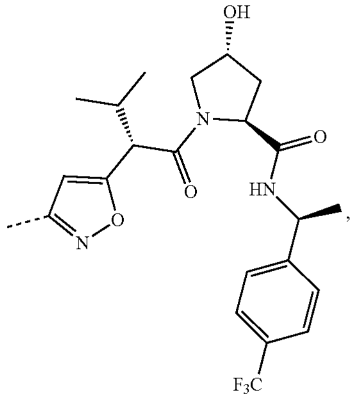
,
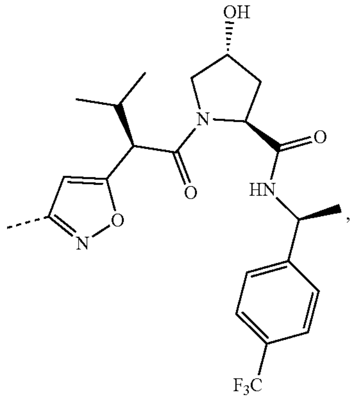
,
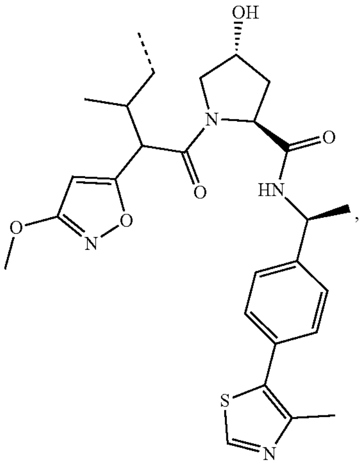
,
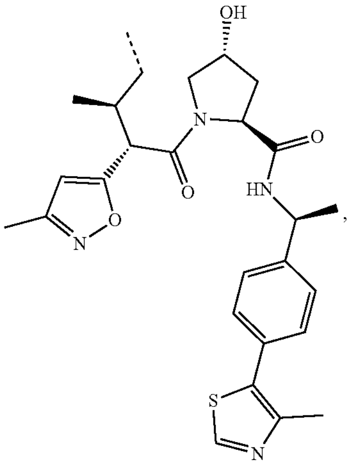
,
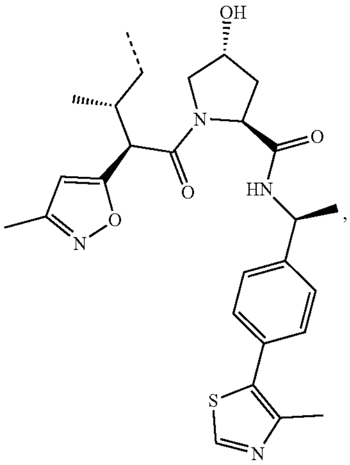
,
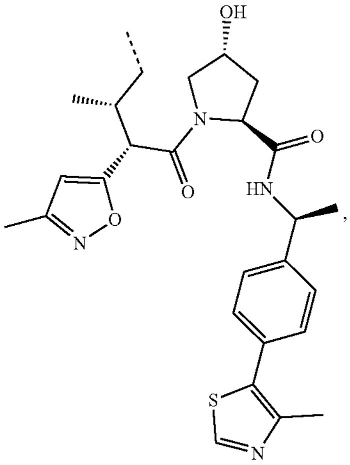
, -continued
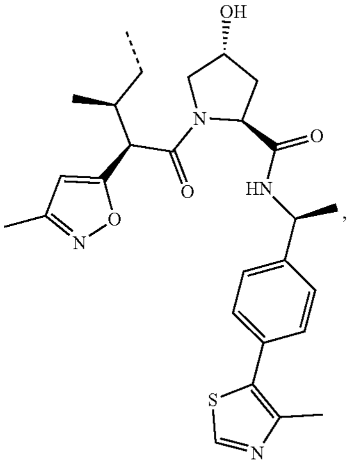
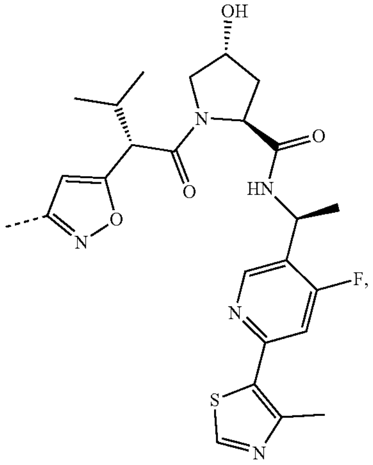
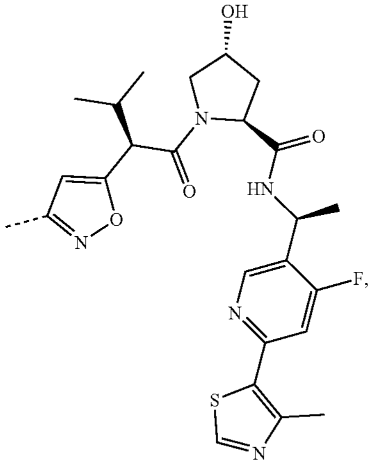
-continued
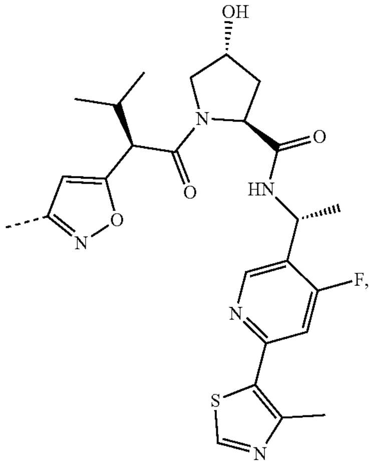
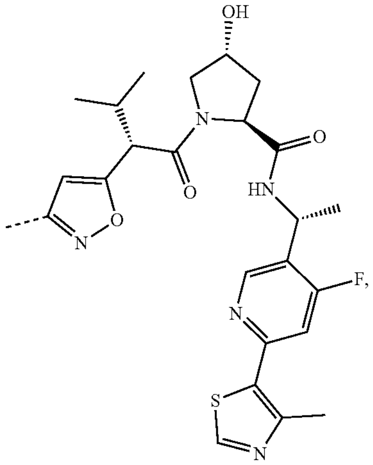
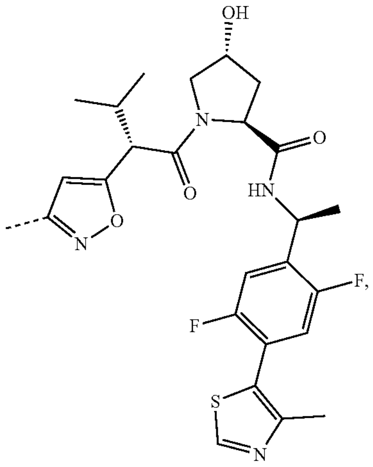

-continued
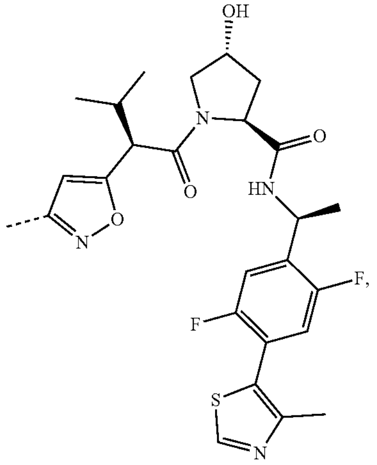
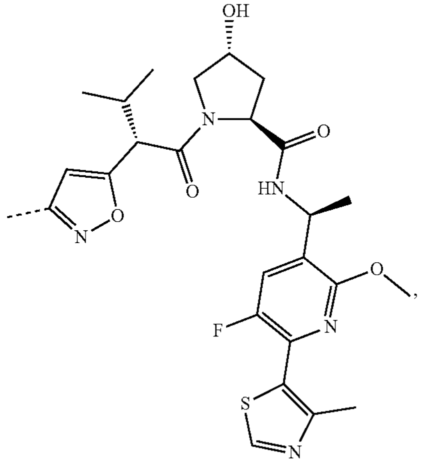
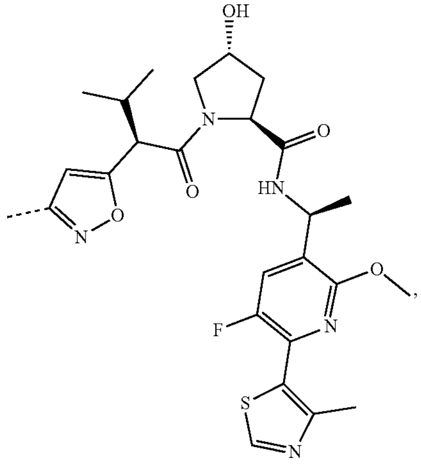
-continued
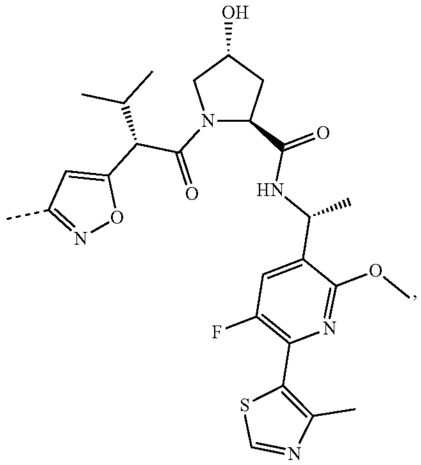
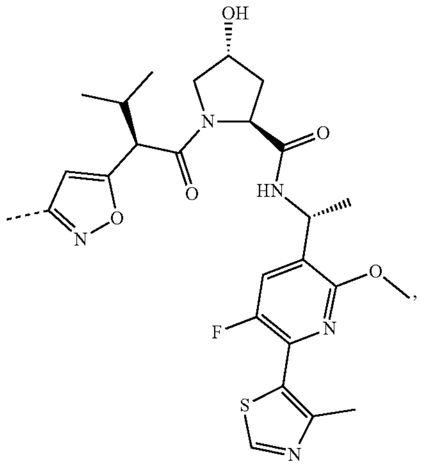
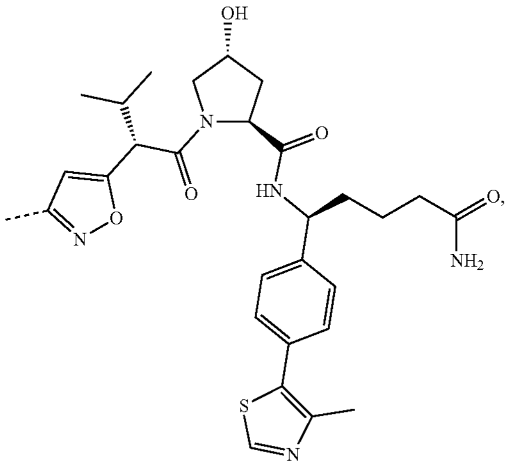

-continued
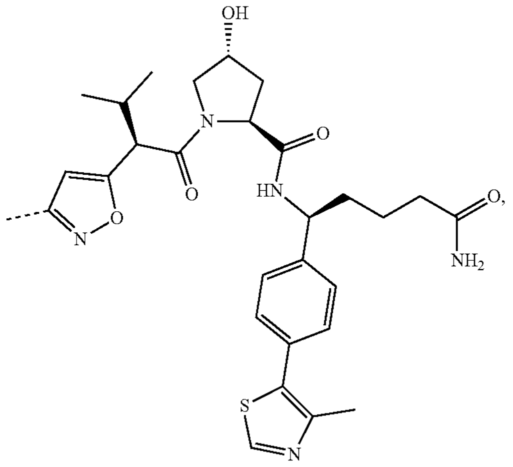
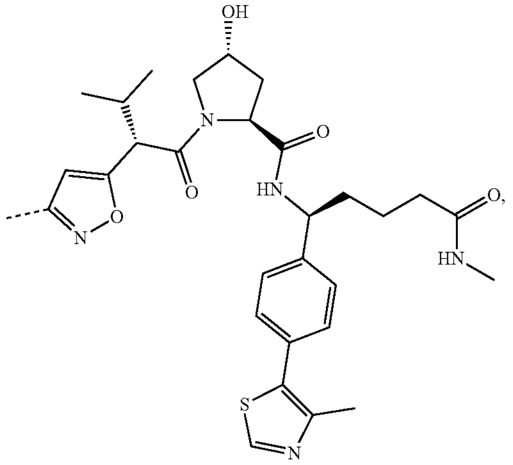
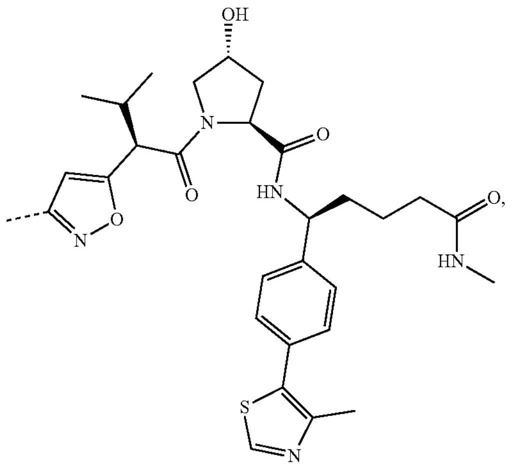
-continued
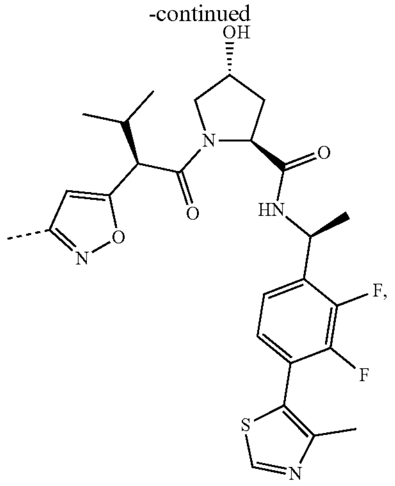
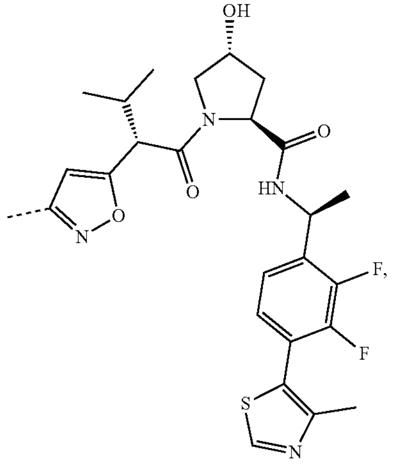
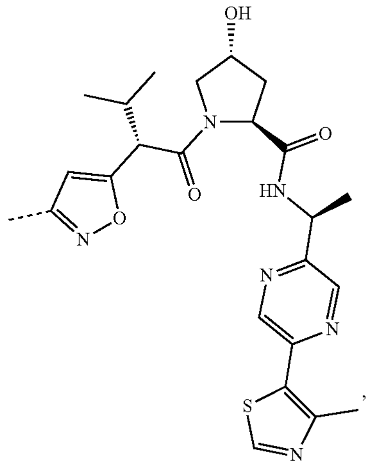

-continued
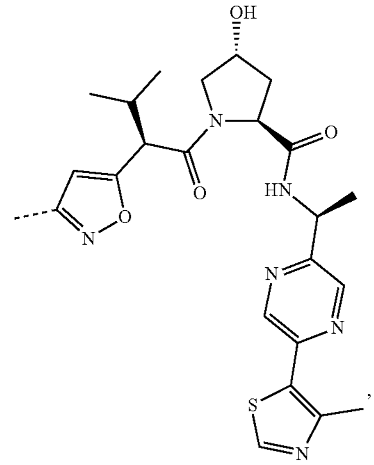
,
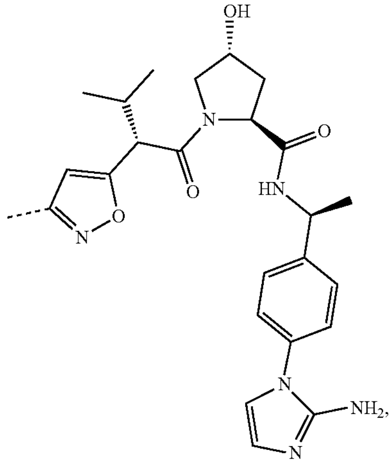
,
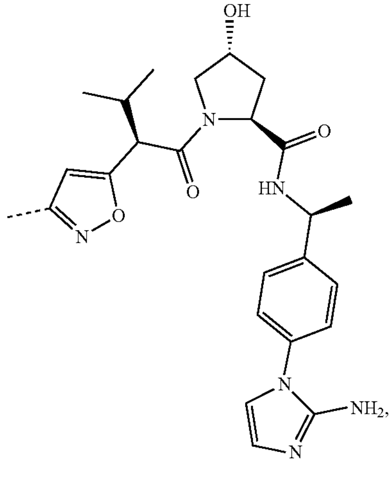
,
-continued
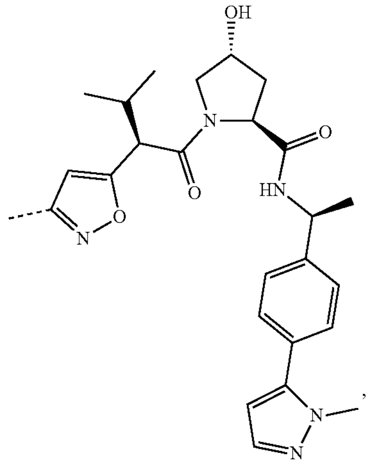
,
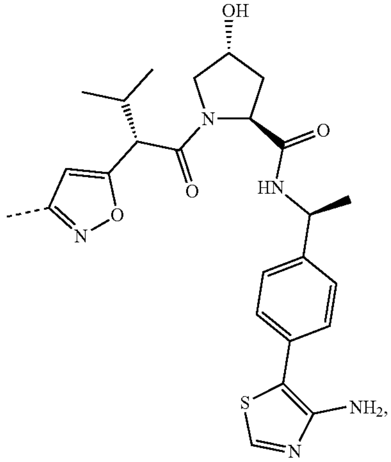
,
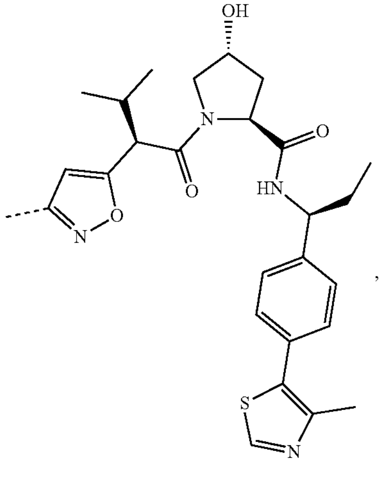
, -continued
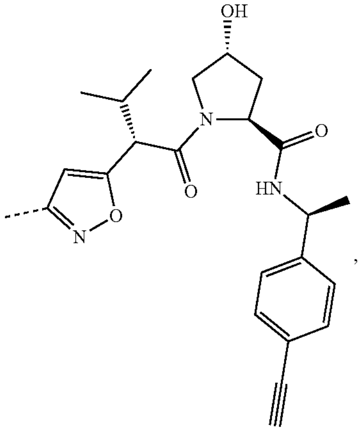
,
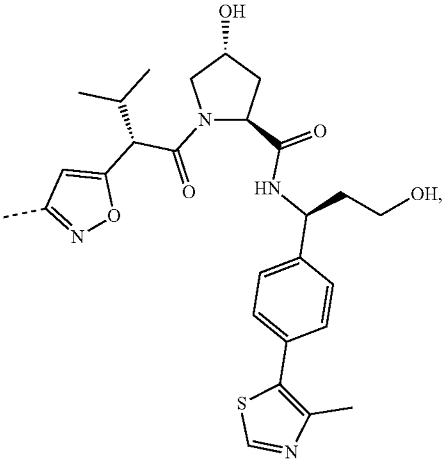
OH,
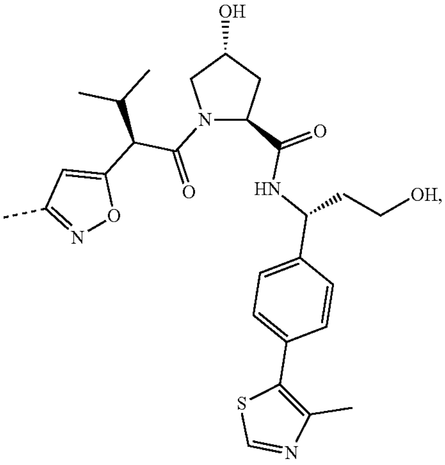
OH,
-continued
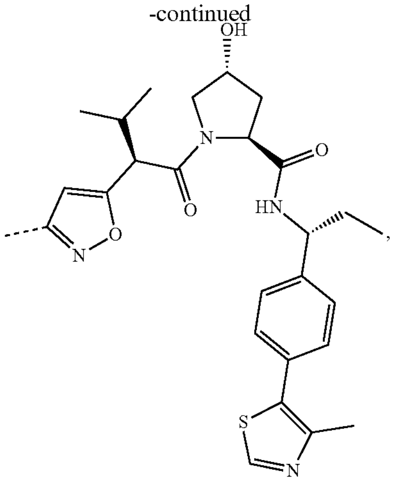
,
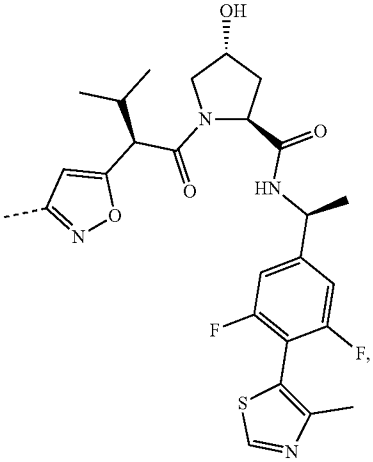
F,
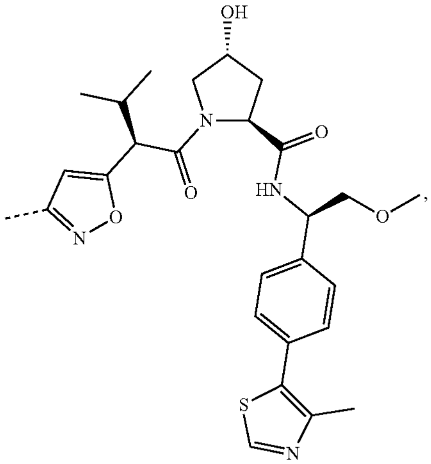
, -continued
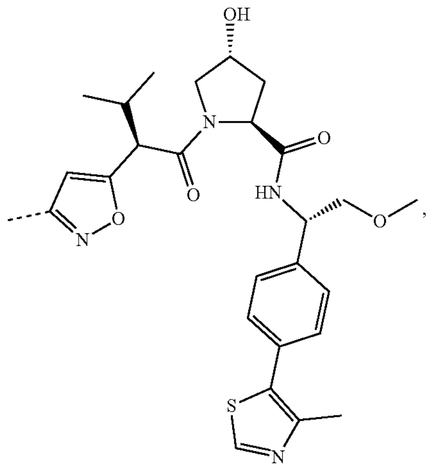
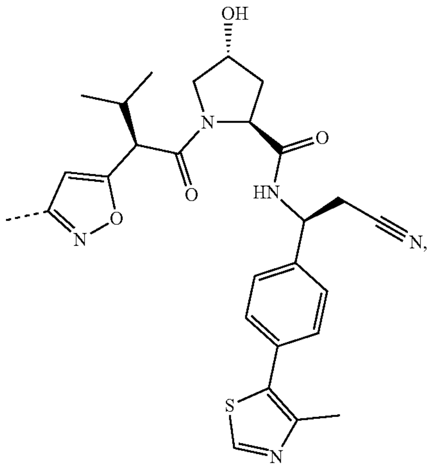
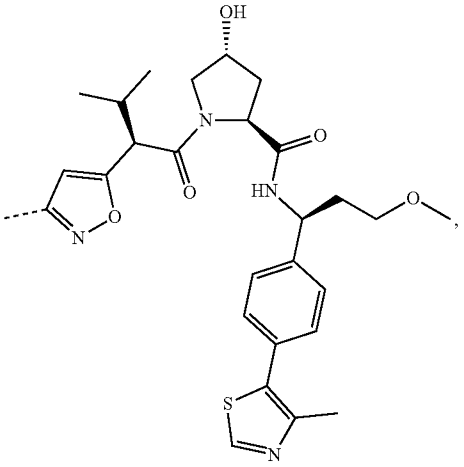
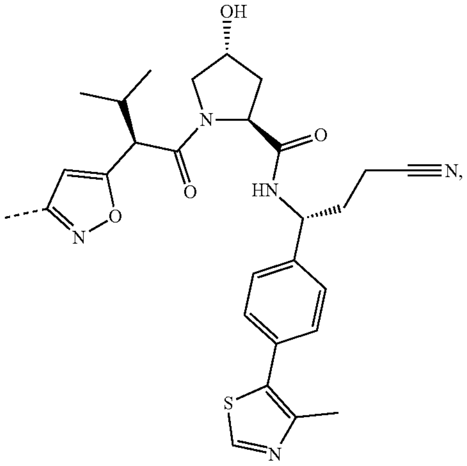
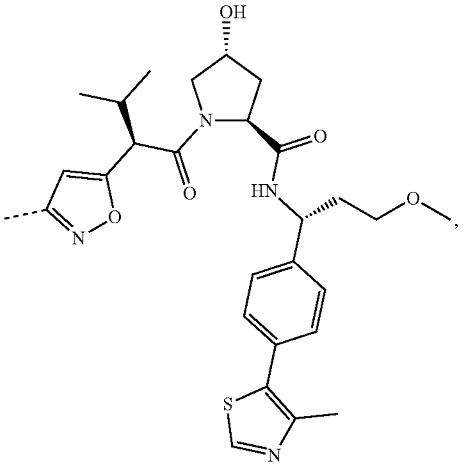
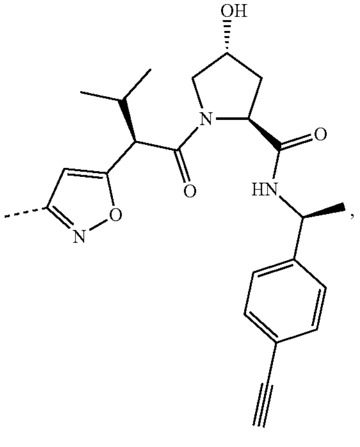

-continued
-continued
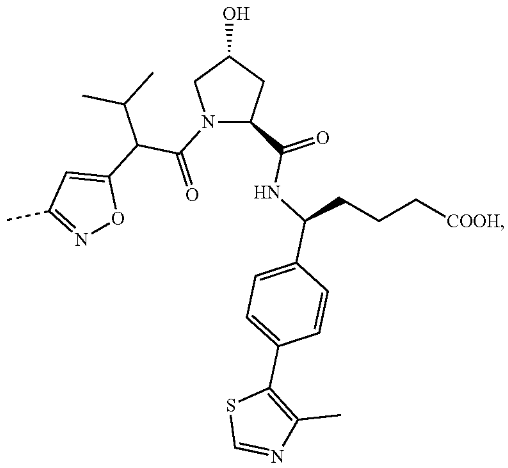
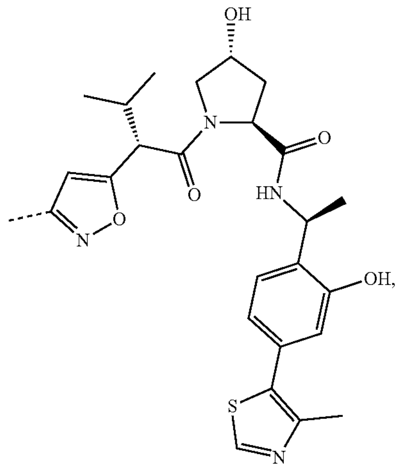
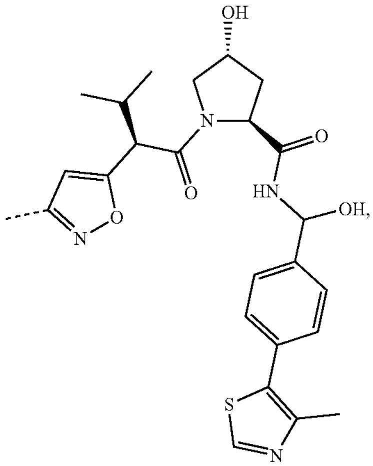
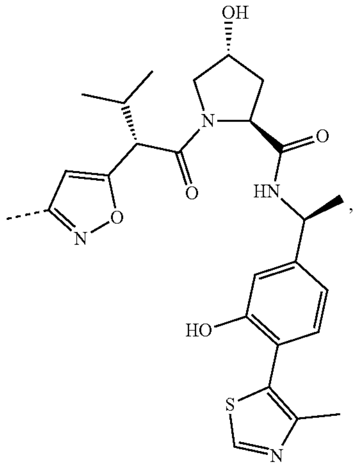
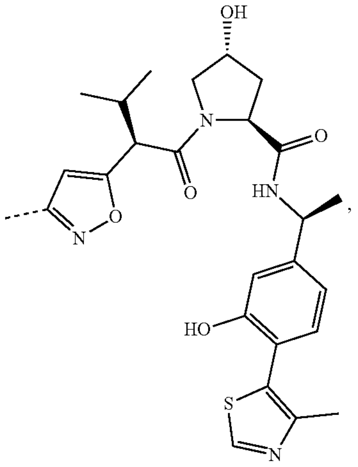
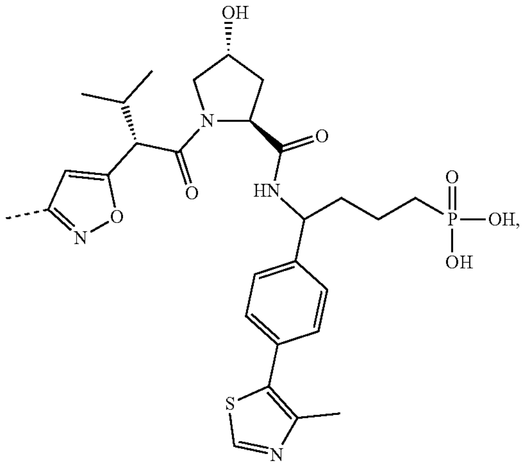

-continued
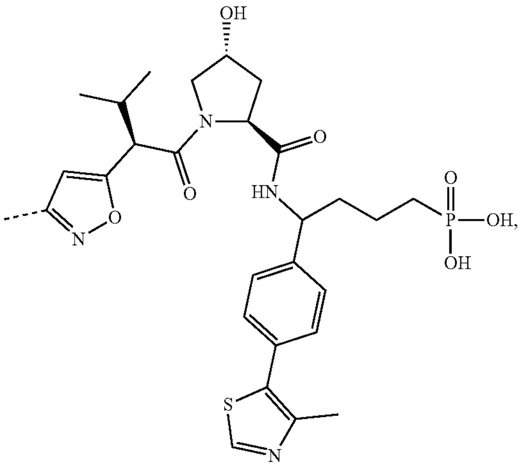
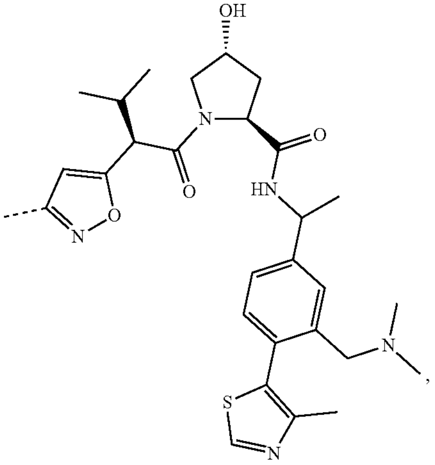
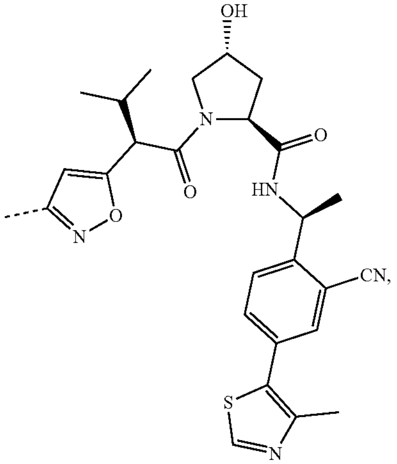
-continued
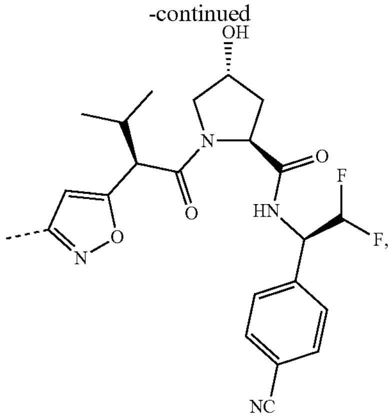
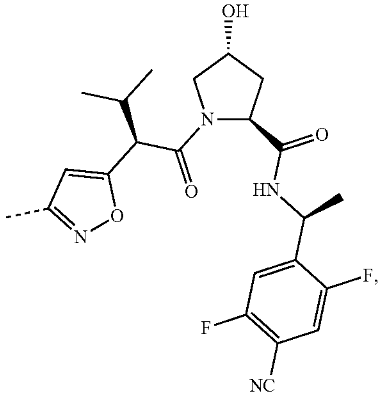
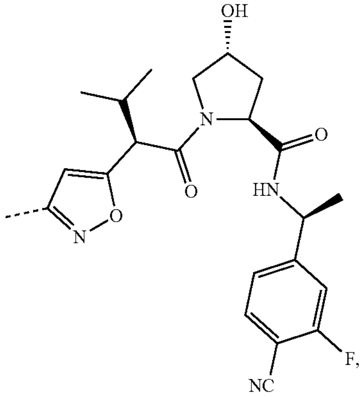
or
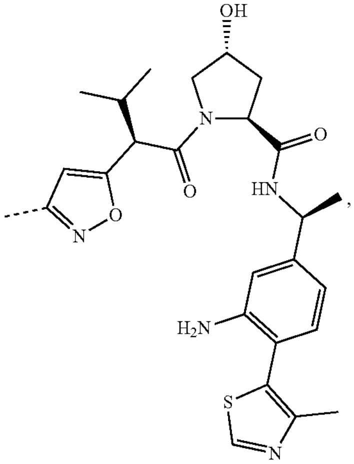
wherein the  indicates the site of attachment of the L.

14. The compound of claim 1, wherein:

each $A^L$ is independently $CR^{L1}R^{L2}$, O, $SONR^{L3}$, $CONR^{L3}$, $NR^{L3}CONR^{L4}$, CO, $CR^{L1}{=}CR^{L2}$, C≡C, $C_{3-11}$cycloalkyl optionally substituted with 1-6 $R^{L1}$ and/or $R^{L2}$ groups, $C_{3-11}$heterocyclyl optionally substituted with 1-6 $R^{L1}$ and/or $R^{L2}$ groups, aryl optionally substituted with 1-6 $R^{L1}$ and/or $R^{L2}$ groups, or heteroaryl optionally substituted with 1-6 $R^{L1}$ and/or $R^{L2}$ groups, where $R^{L1}$ or $R^{L2}$, each independently are optionally linked to other groups to form cycloalkyl or heterocyclyl moiety, optionally substituted with 1-4 $R^{L5}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $NHC_{1-8}$alkyl, $N(C_{1-8}alkyl)_2$, OH, $NH_2$, SH, C≡CH, CN, $CF_3$, $CHF_2$, $CH_2F$, or $NO_2$.

15. The compound according to claim 1, wherein the L is:

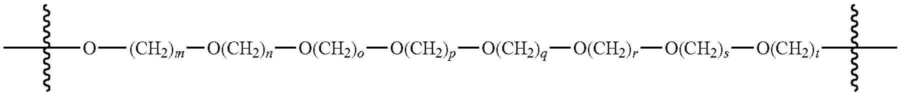,

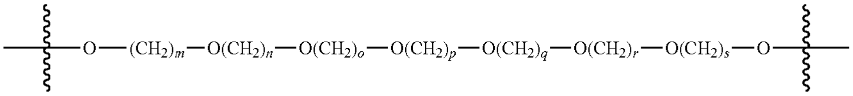,

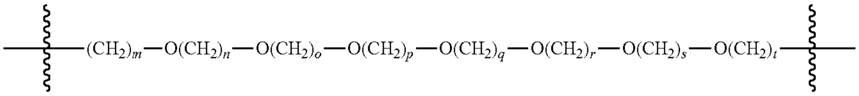,

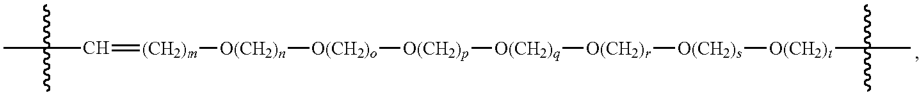,

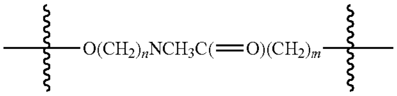, 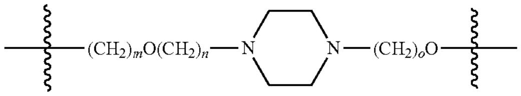,

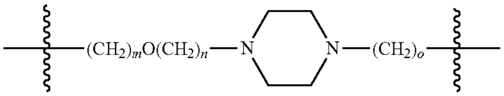, 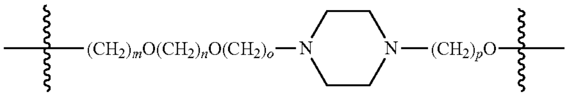,

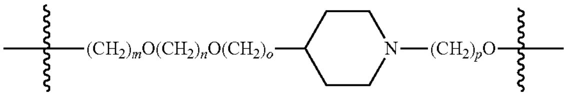, 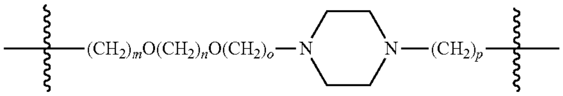,

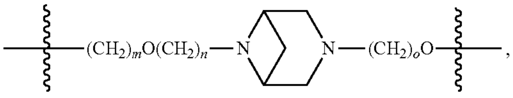, 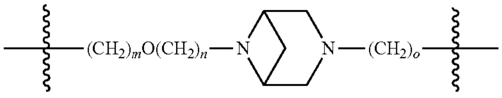,

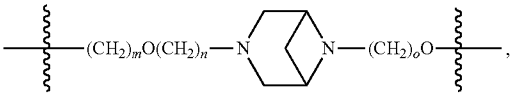, 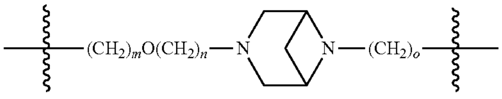,

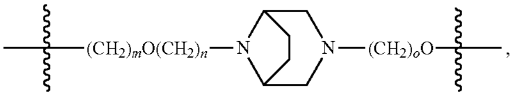, 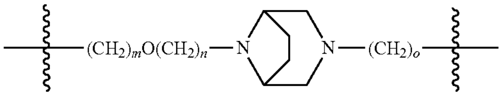,

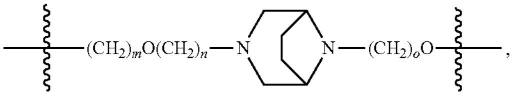, 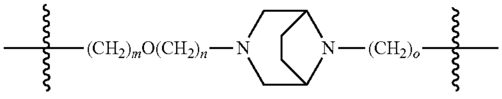,

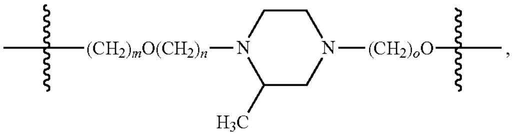, 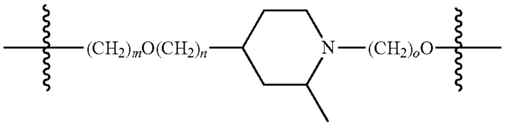,

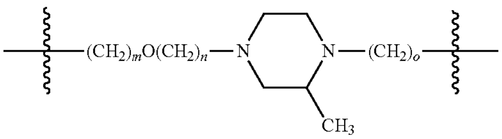, 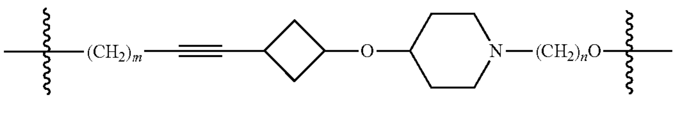,

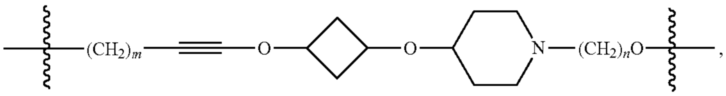,

-continued
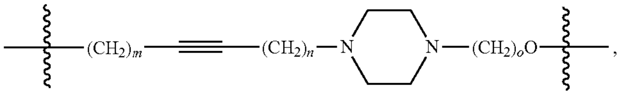,
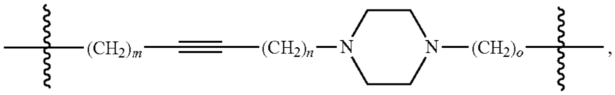,
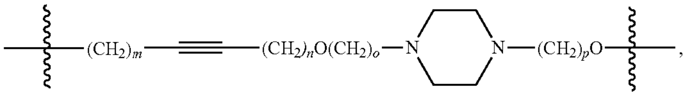,
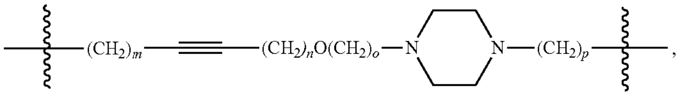, 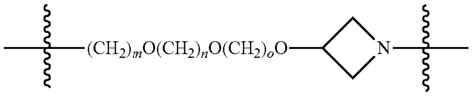,
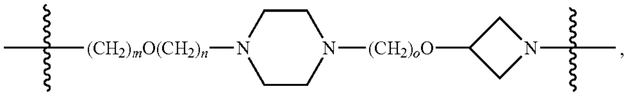,
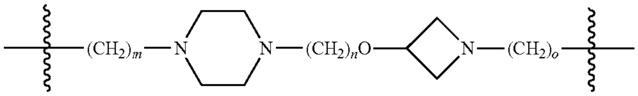,
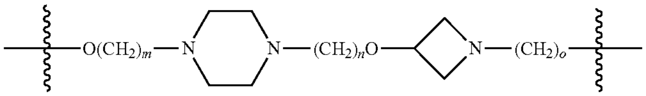,
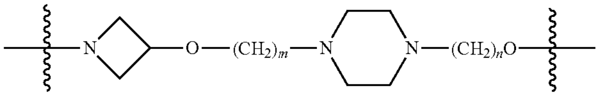,
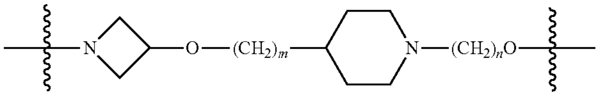,
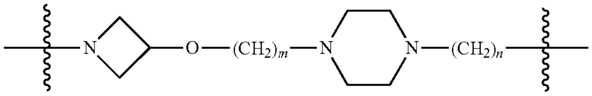,
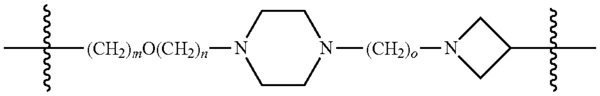, 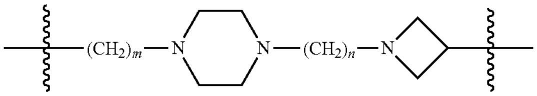,
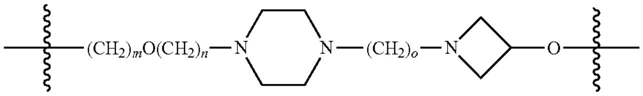,
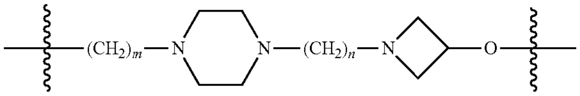,
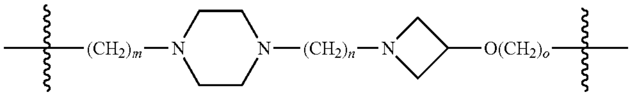,
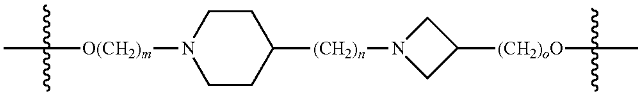,
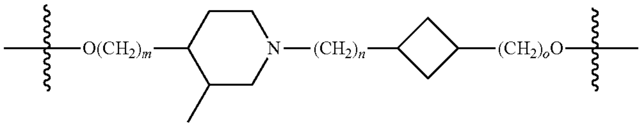,
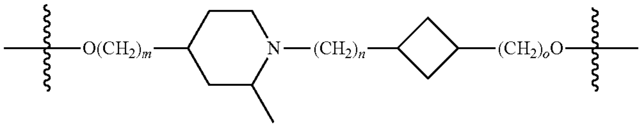, -continued
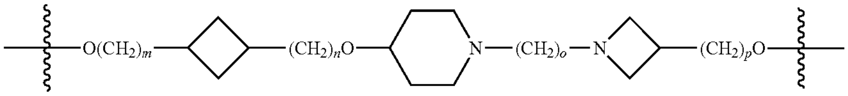,
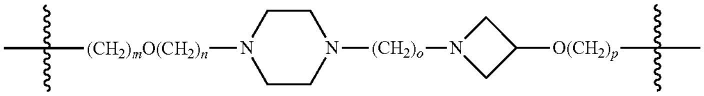,
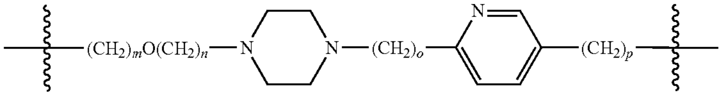,
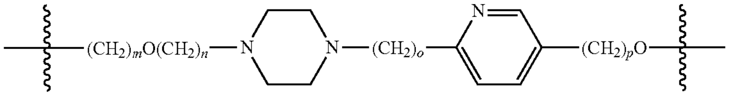,
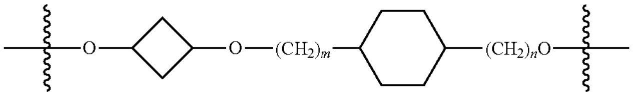,
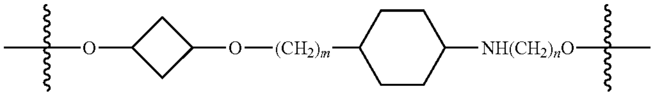,
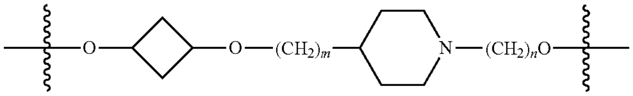,
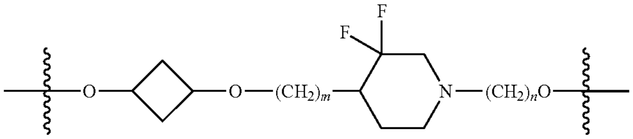,
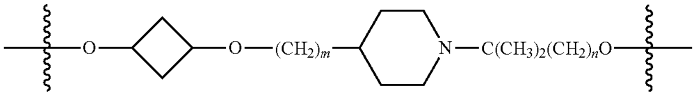,
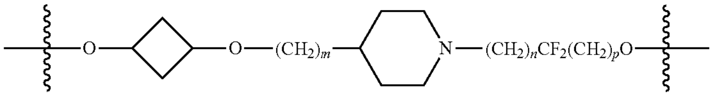,
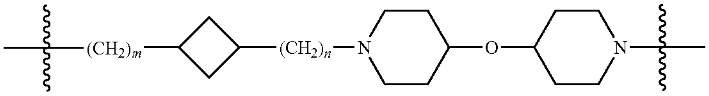,
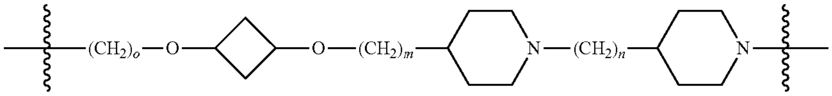,
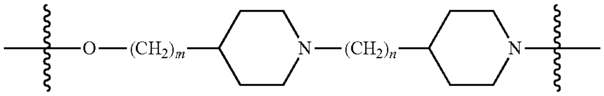,
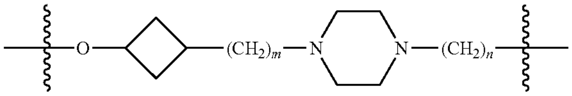,
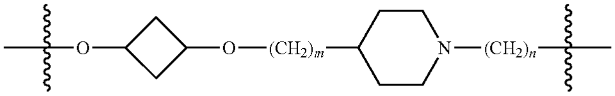,
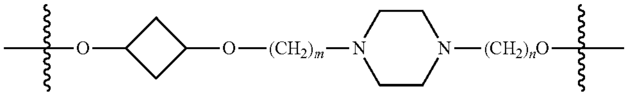,
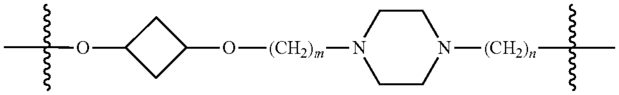, -continued
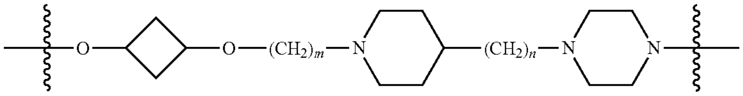,
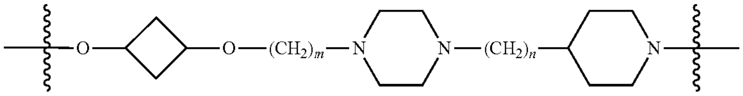,
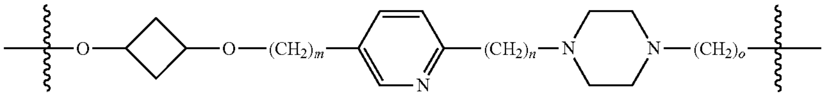,
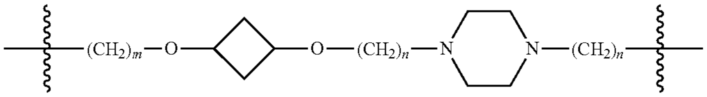,
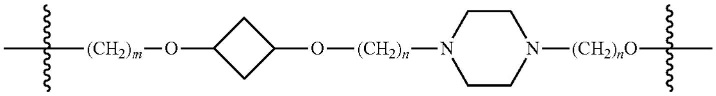,
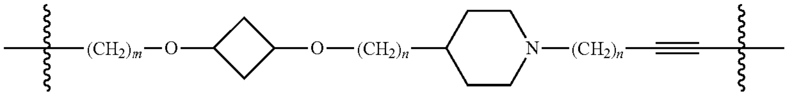,
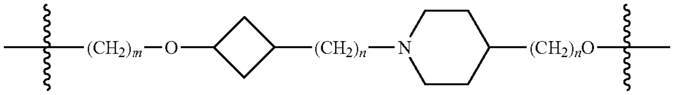,
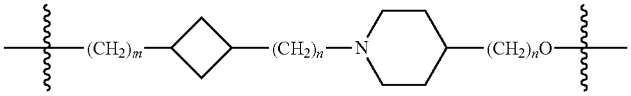,
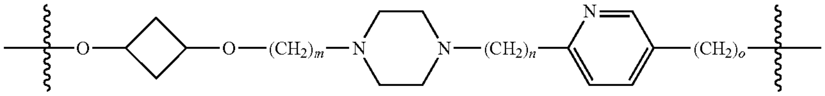,
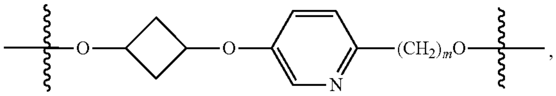, 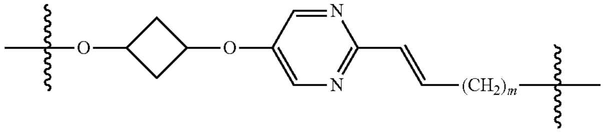,
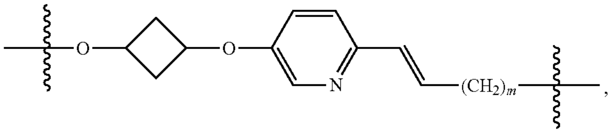,
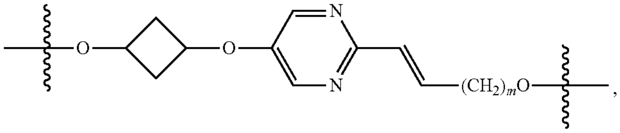,
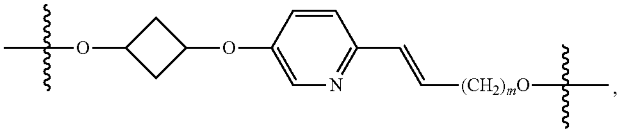,
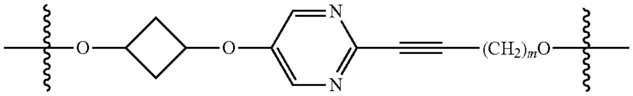,
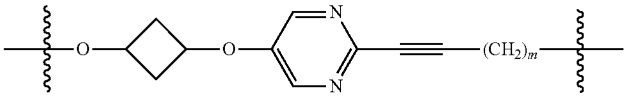,

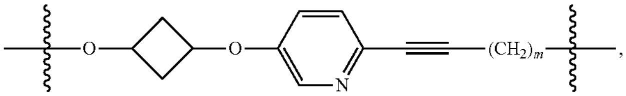,
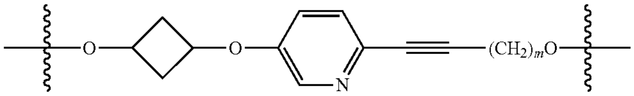,
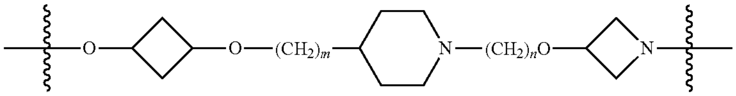,
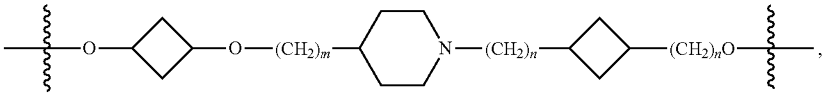,
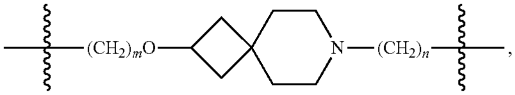, 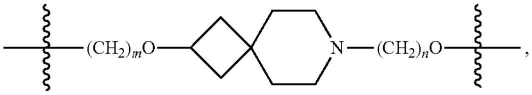,
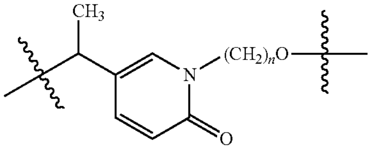, 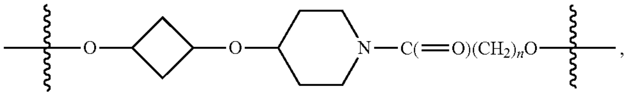,
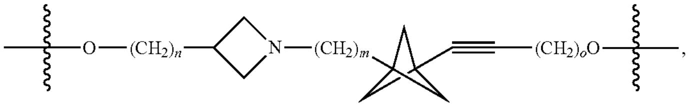,
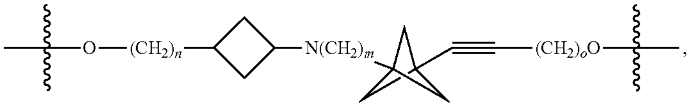,
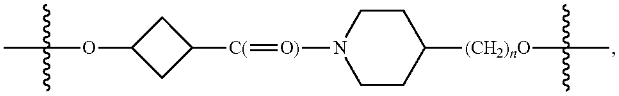,
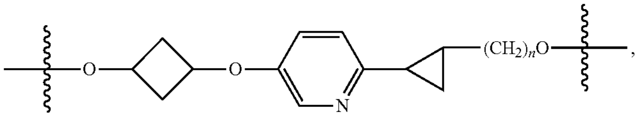,
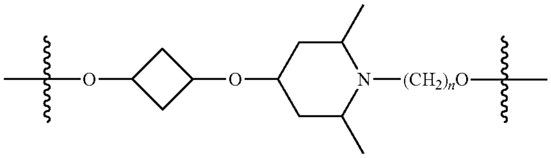,
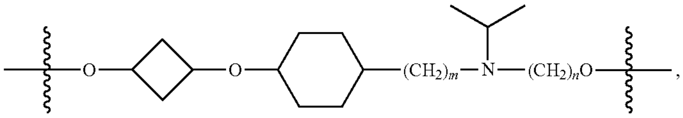,
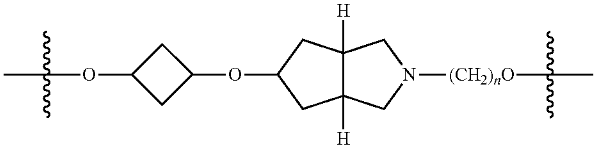,
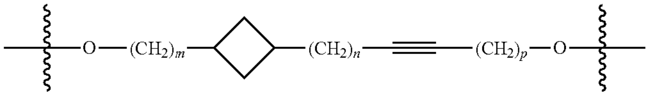,
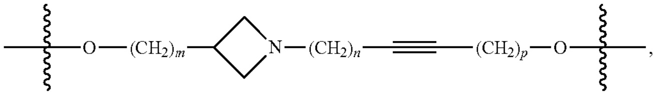, -continued
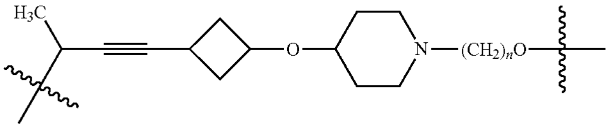,
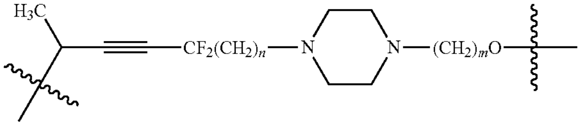,
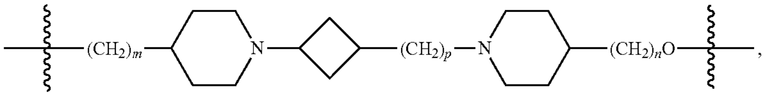,
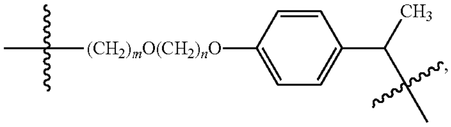,
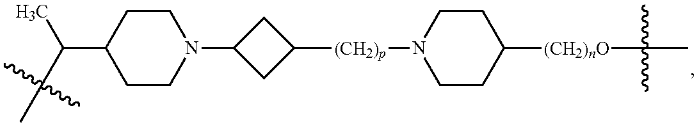, 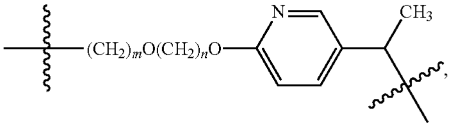,
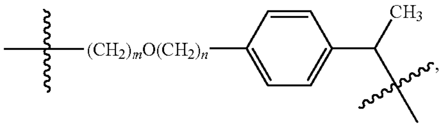, 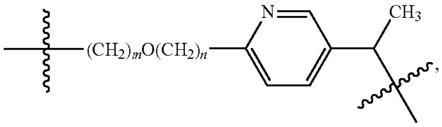,
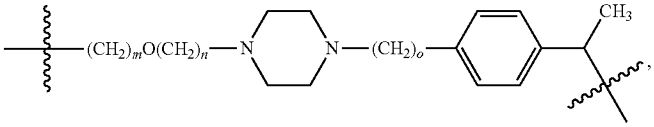,
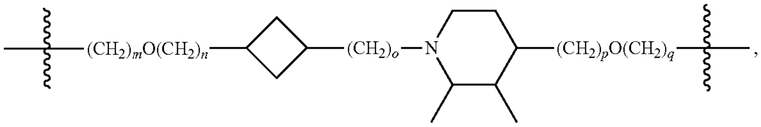,
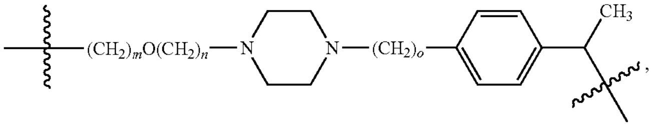,
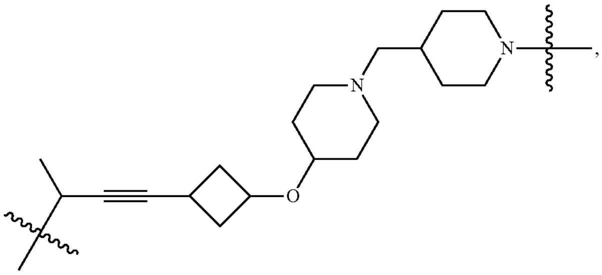,
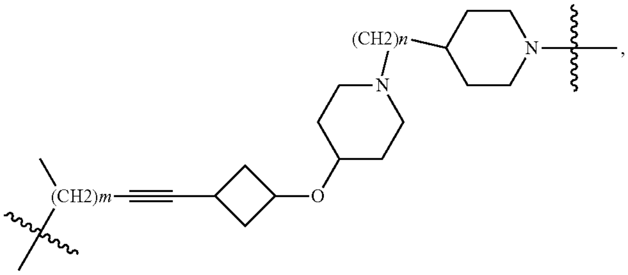, -continued
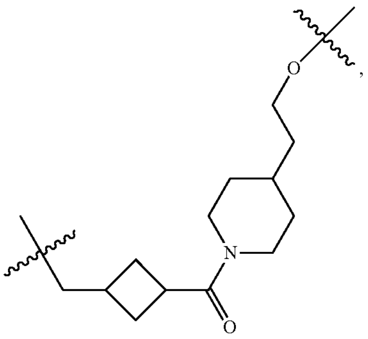
, or
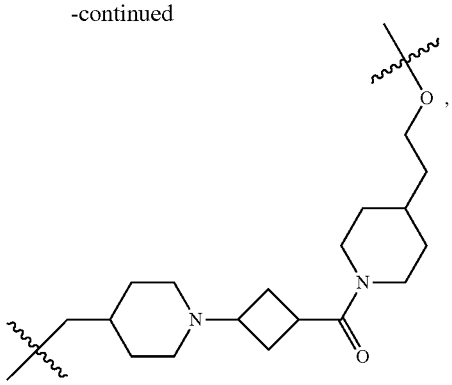
,
wherein m, n, o, p, q, r, s and t of the L are each independently selected from 0, 1, 2, 3, and 4.
16. The compound according to claim 1, wherein the L is:
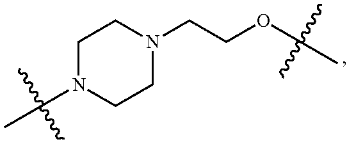
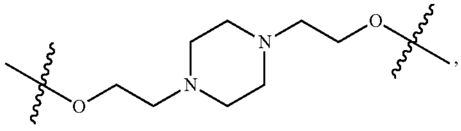
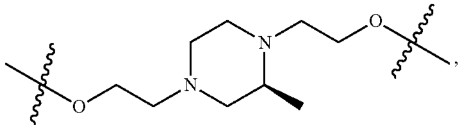
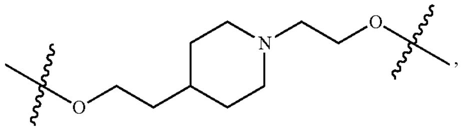
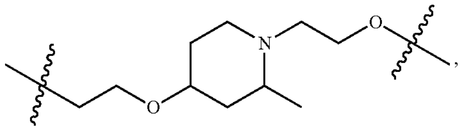
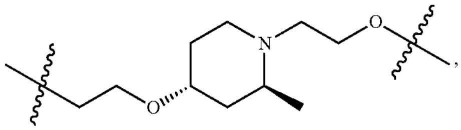
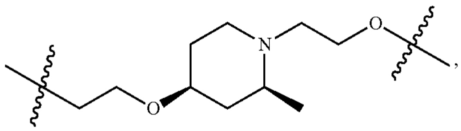
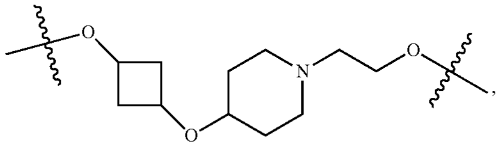
-continued
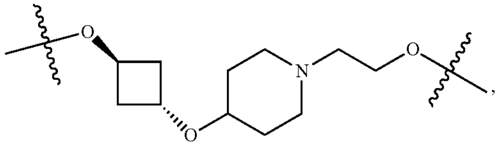
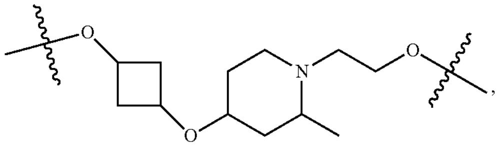
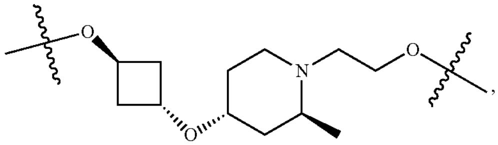
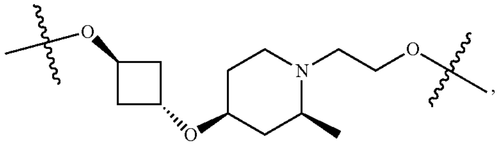
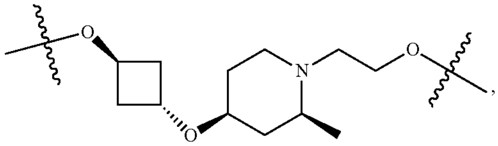
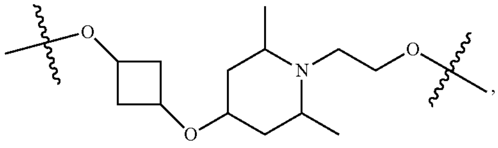
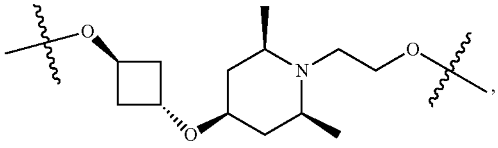
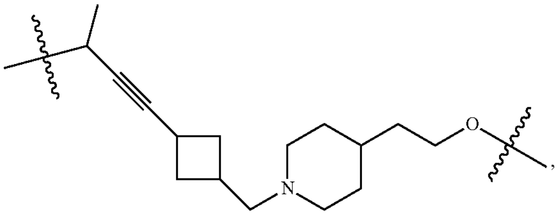

-continued
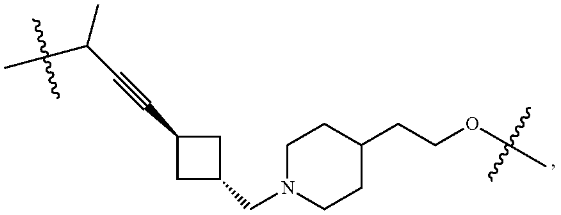
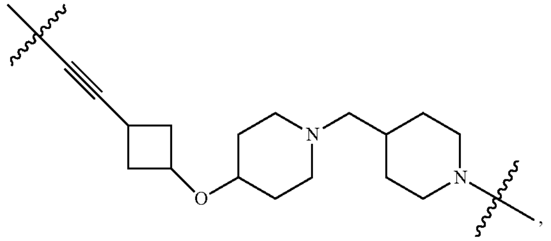
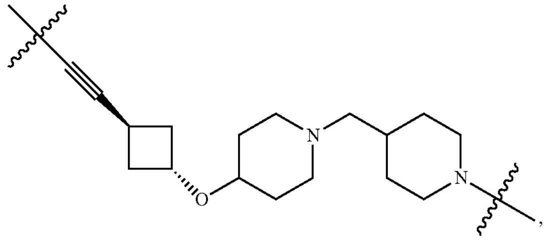
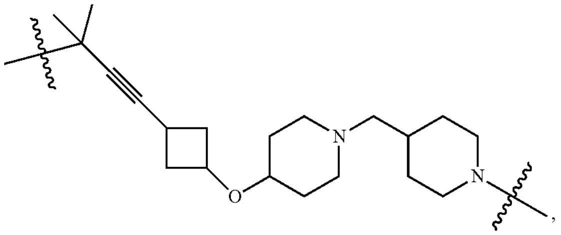
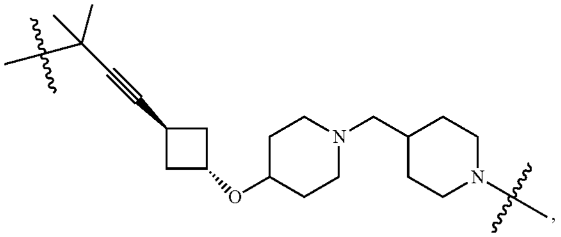
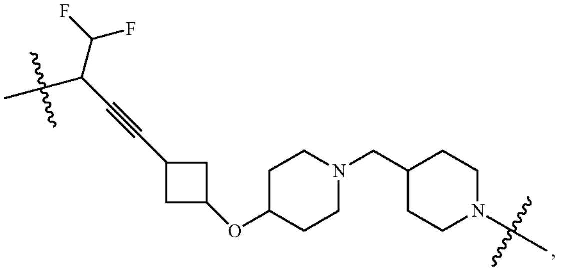
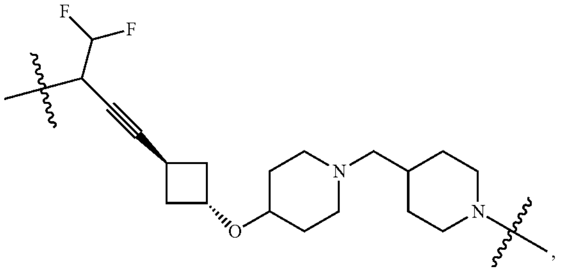
-continued
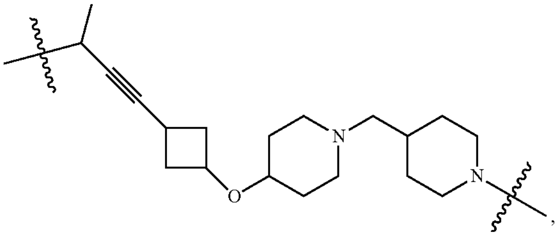
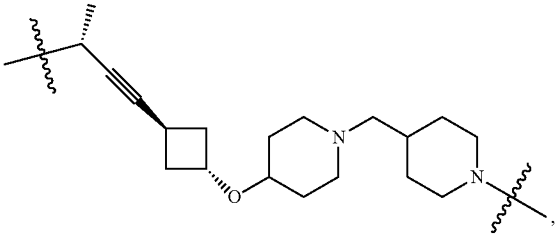
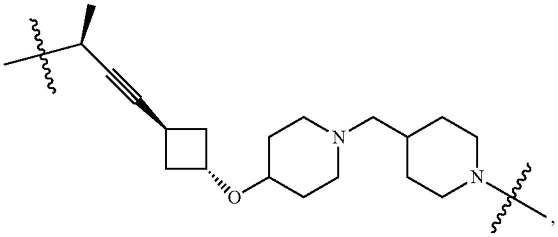
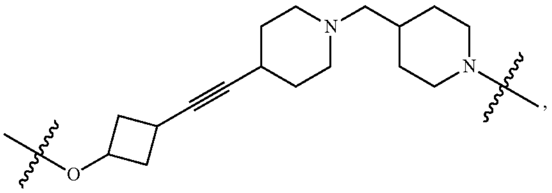
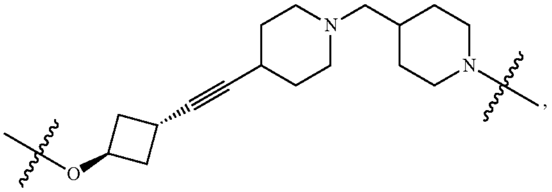
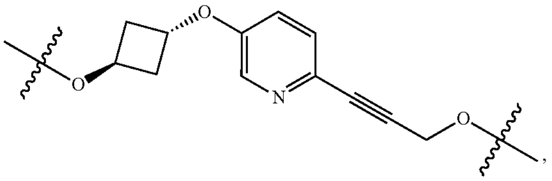
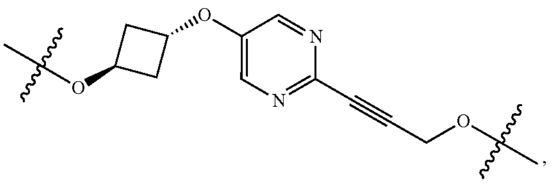
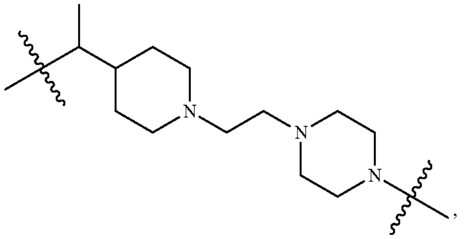

-continued
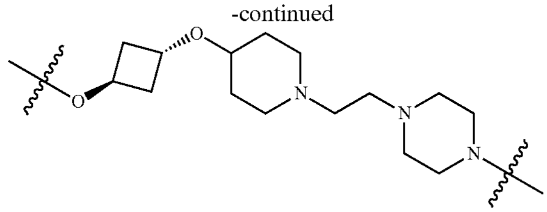
,
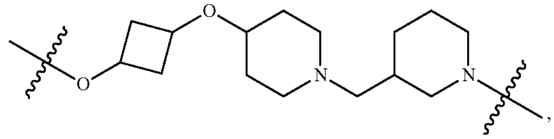
,
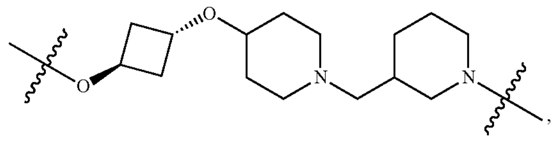
,
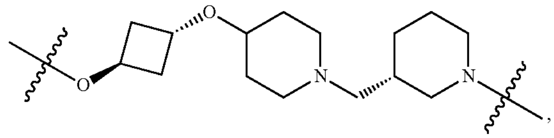
,
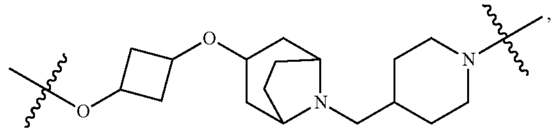
,
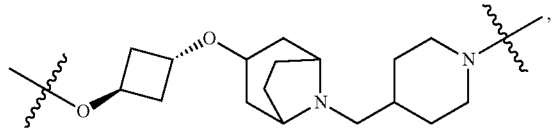
,
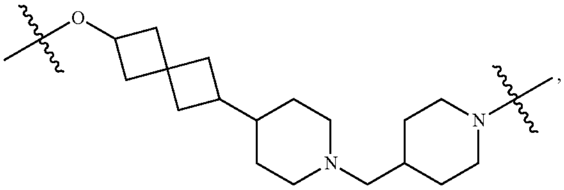
,
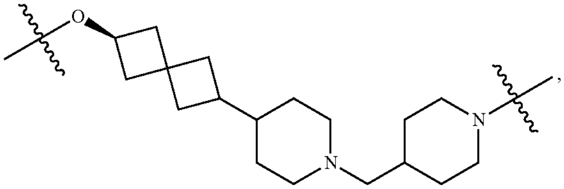
,
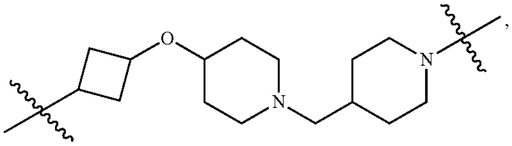
,
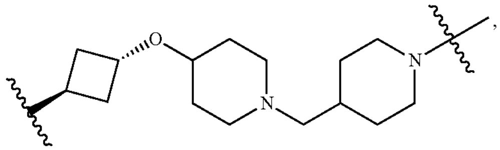
,
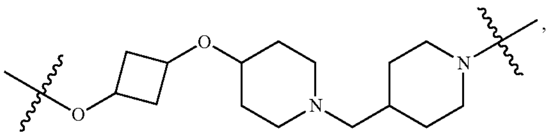
,
-continued
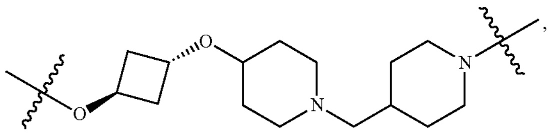
,
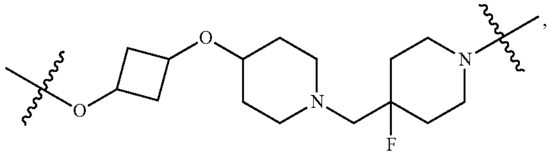
,
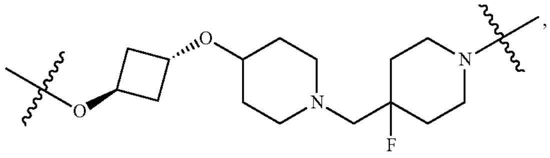
,
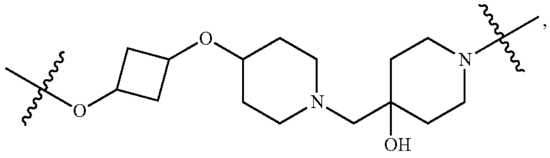
,
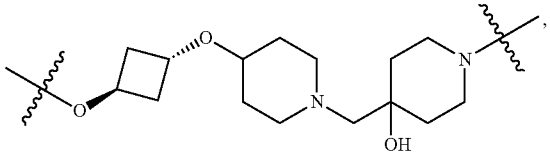
,
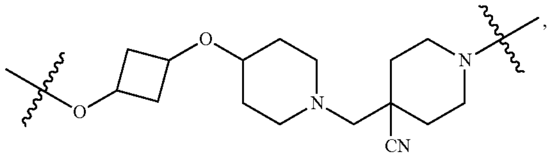
,
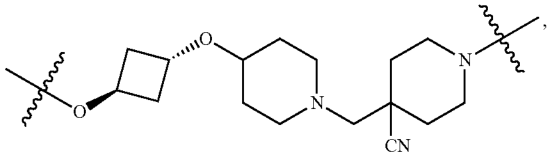
,
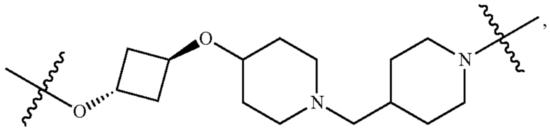
,
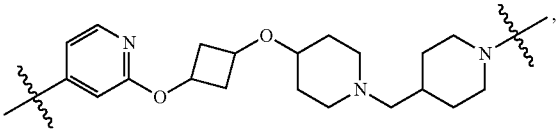
,
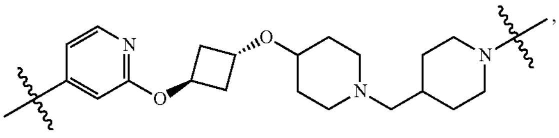
,
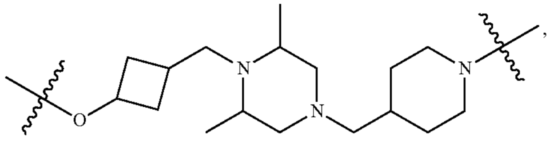
, -continued
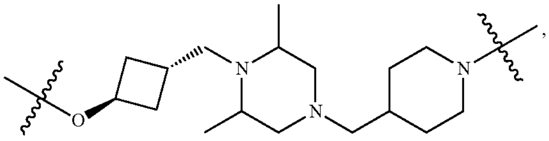,
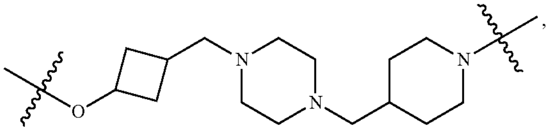,
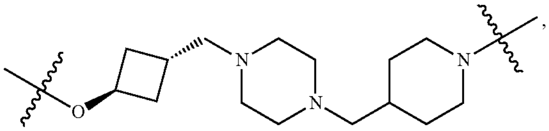,
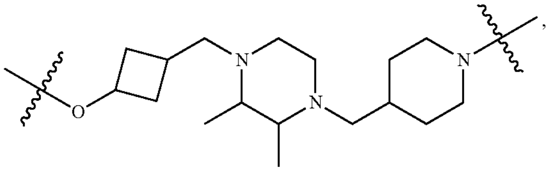,
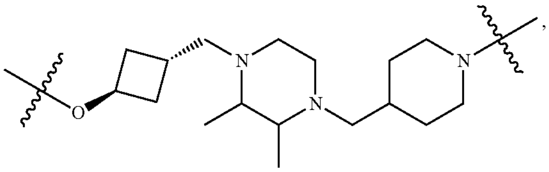,
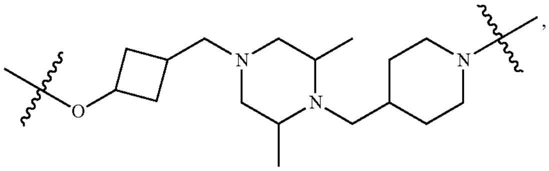,
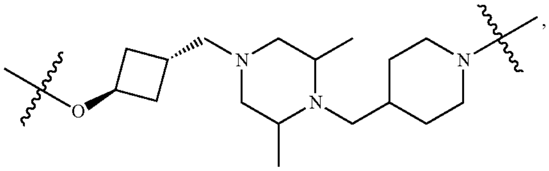,
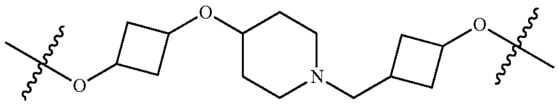,
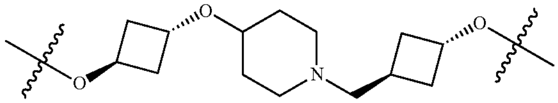,
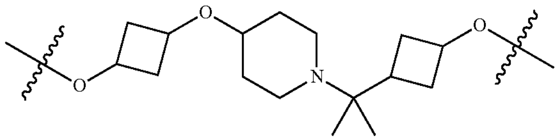,
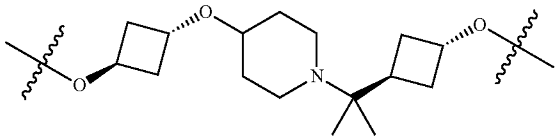,
-continued
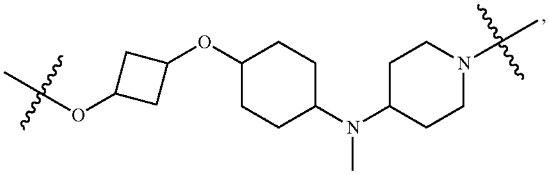,
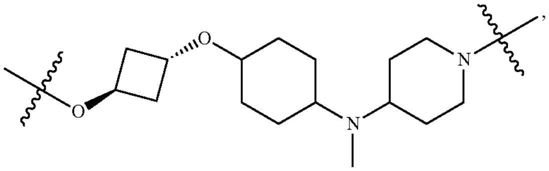,
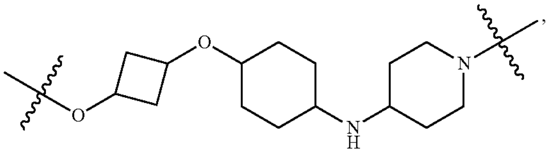,
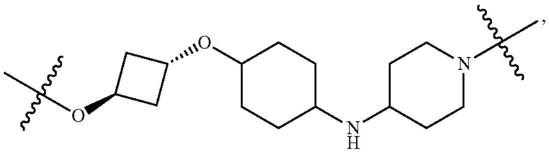,
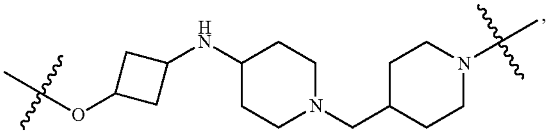,
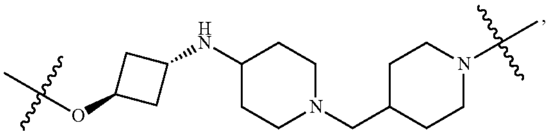,
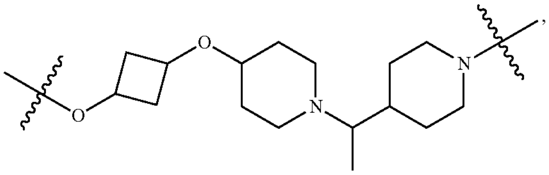,
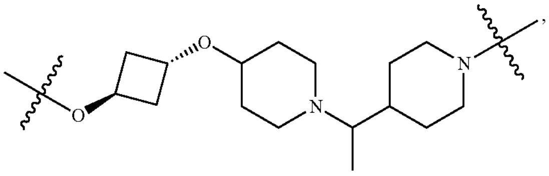,
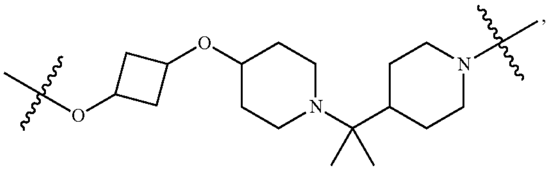,
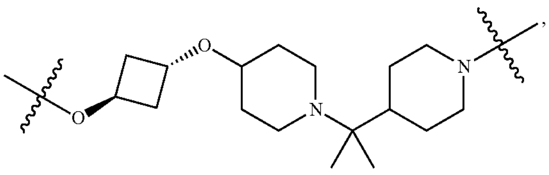, -continued
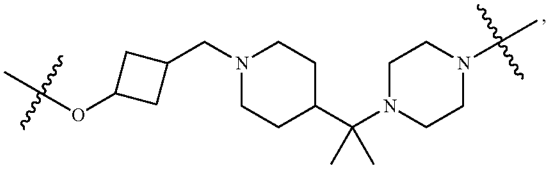
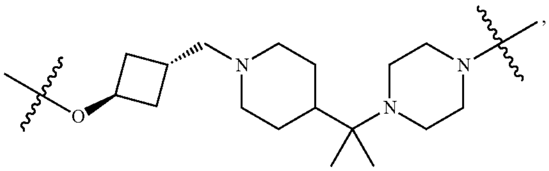
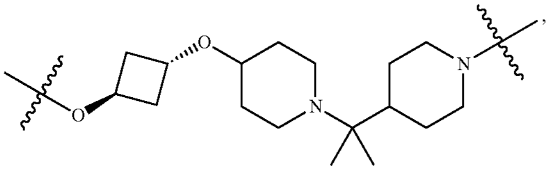
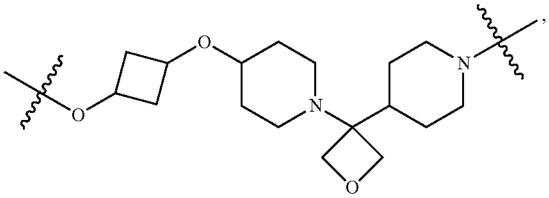
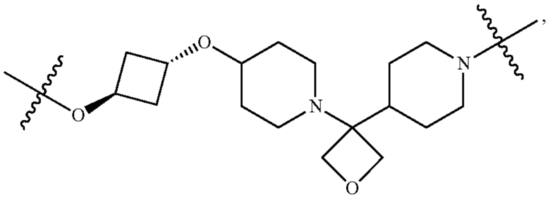
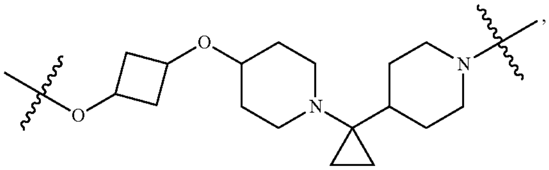
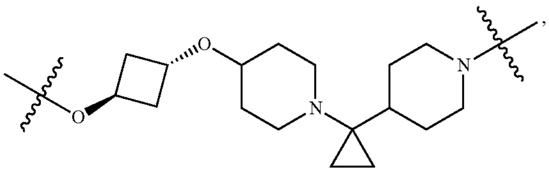
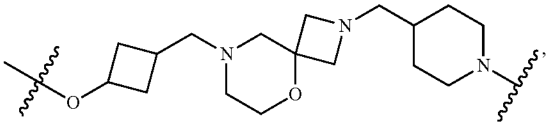
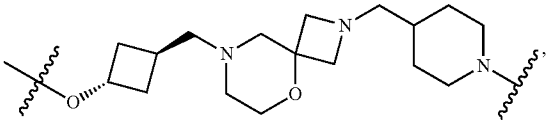
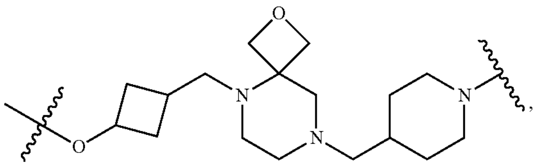
-continued
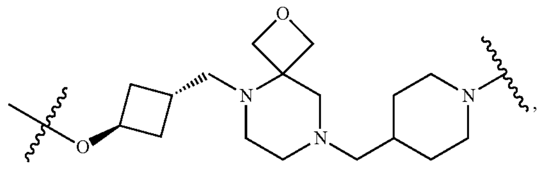
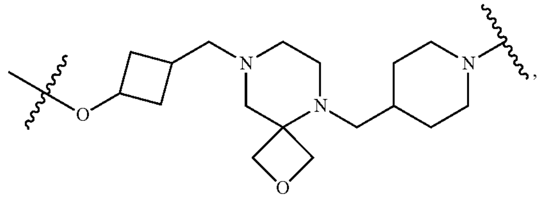
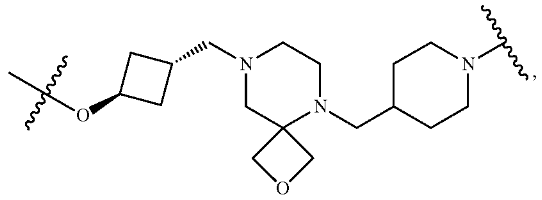
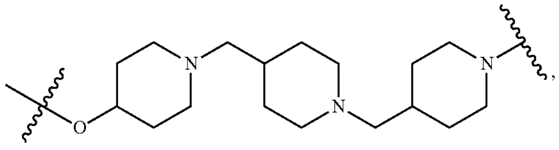
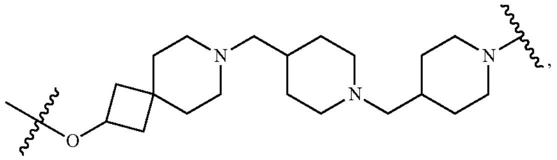
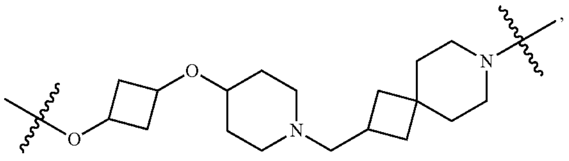
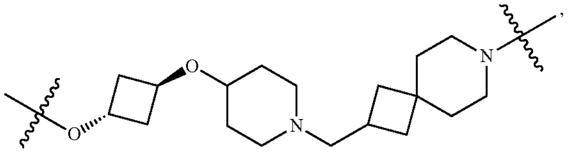
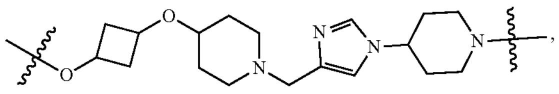
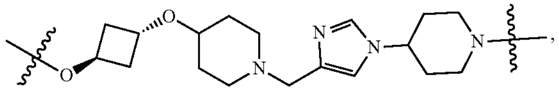
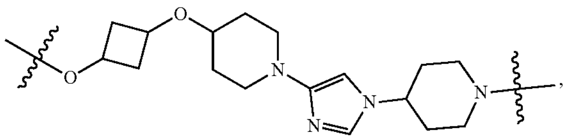
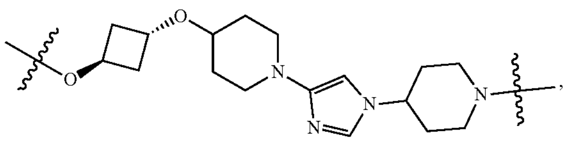

-continued
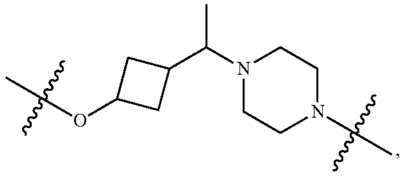
,
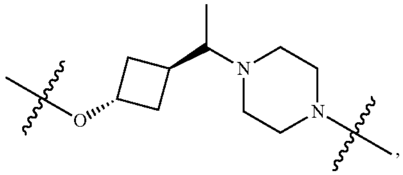
,
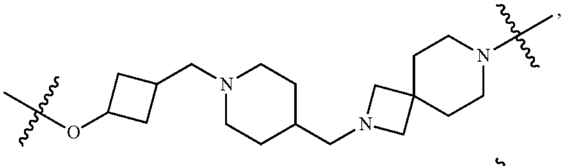
,
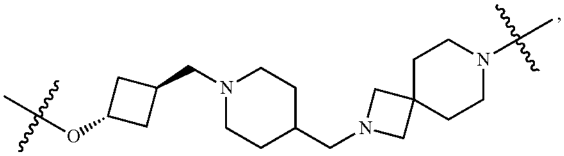
,
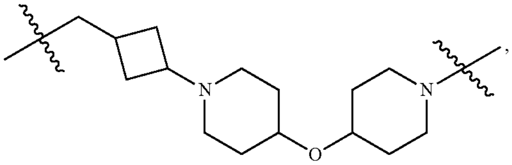
,
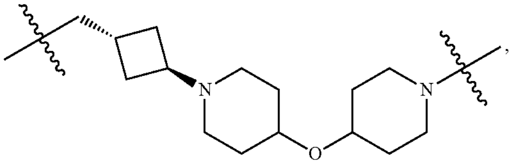
,
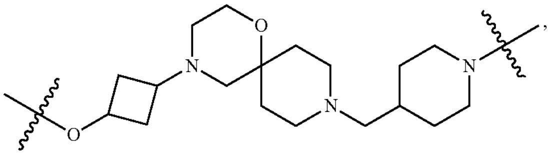
,
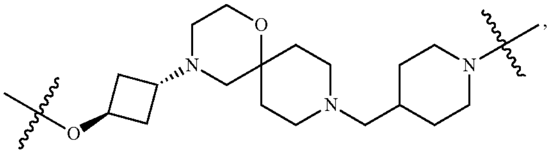
,
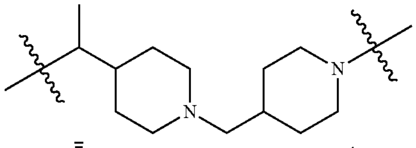
,
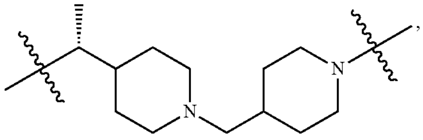
,
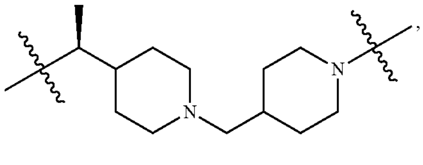
,
-continued
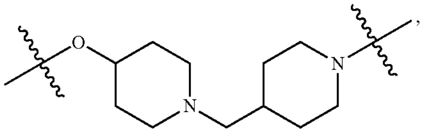
,
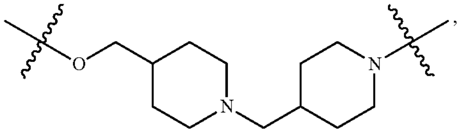
,
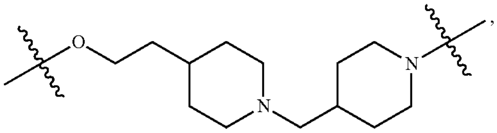
,
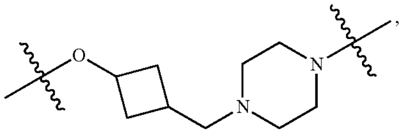
,
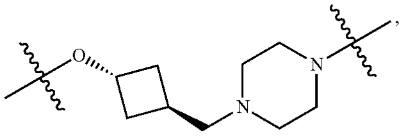
,
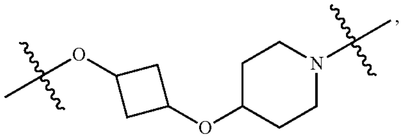
,
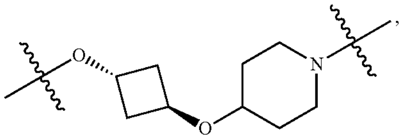
,
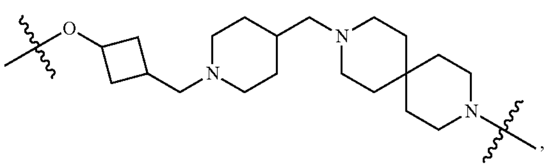
,
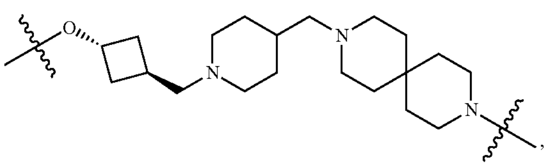
,
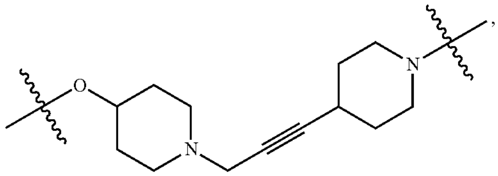
,
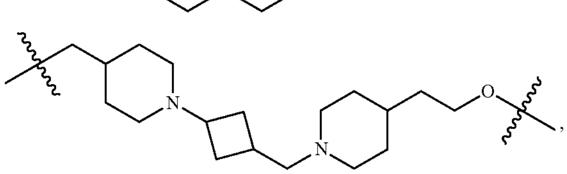
, -continued
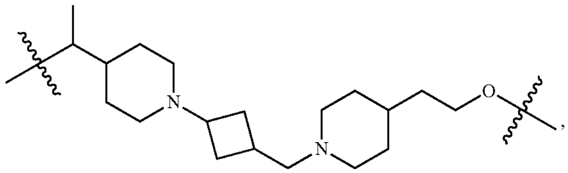
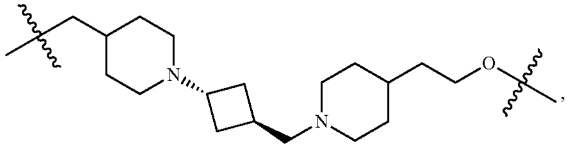
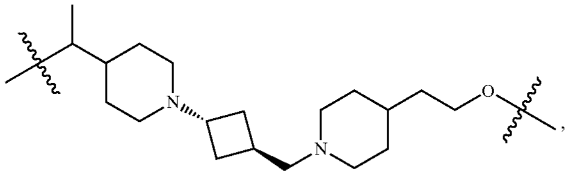
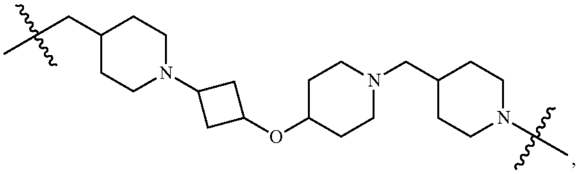
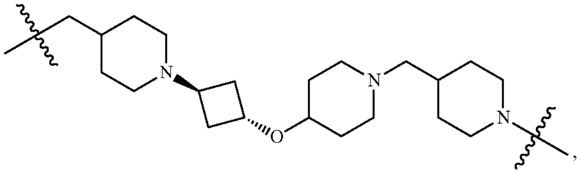
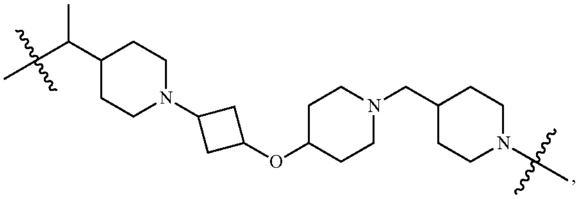
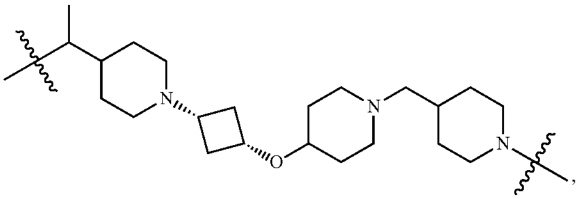
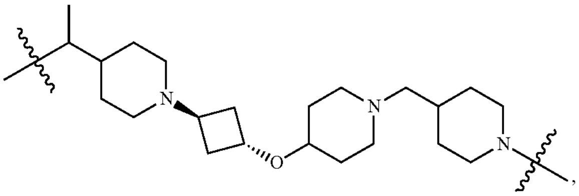
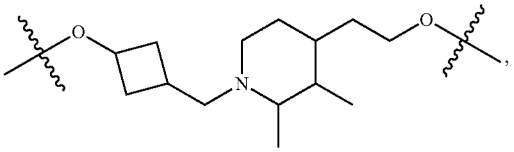
-continued
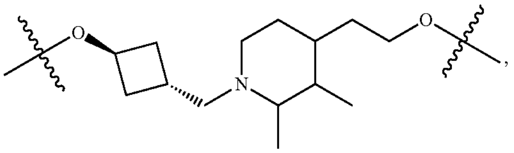
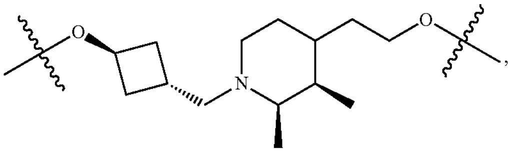
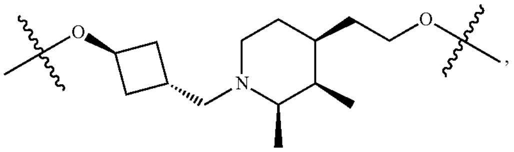
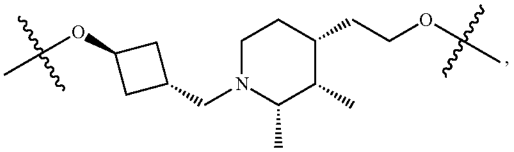
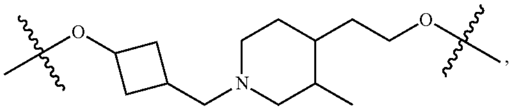
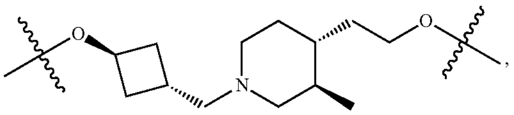
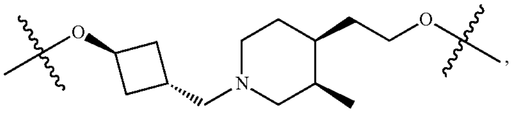
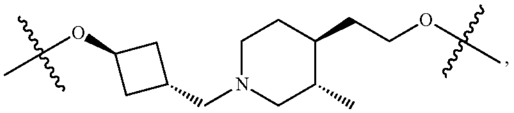
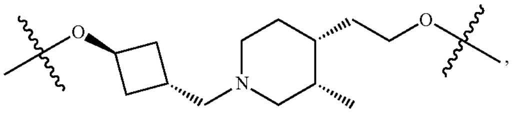
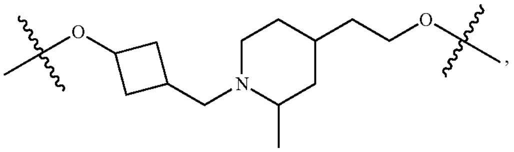
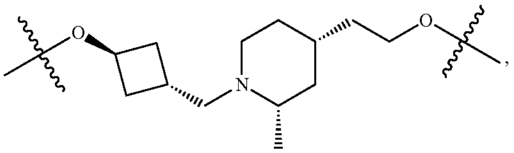
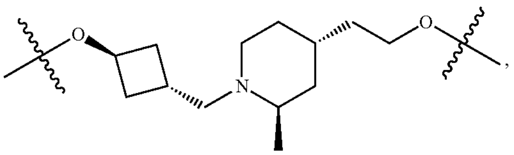

-continued
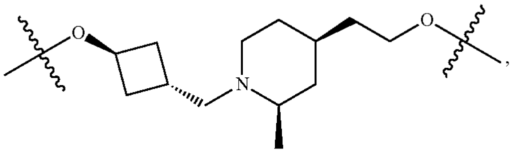
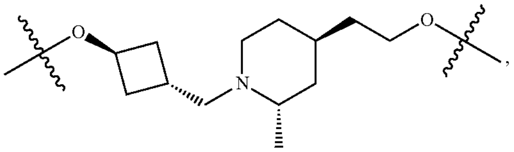
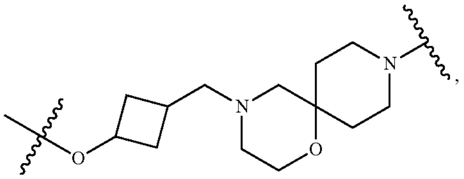
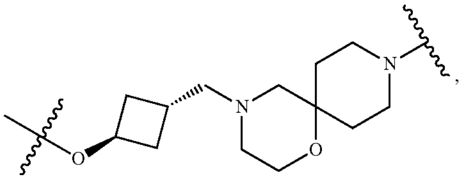
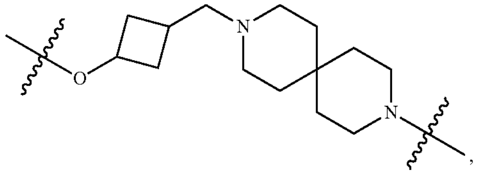
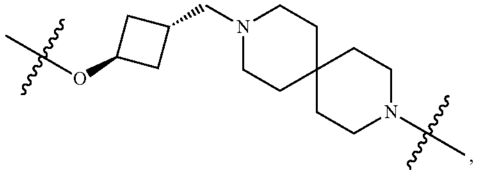
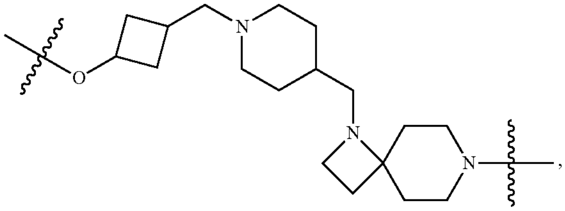
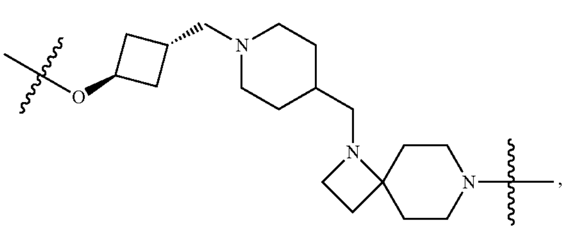
-continued
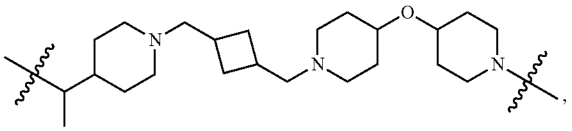
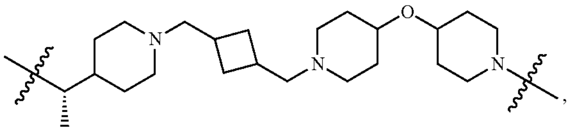
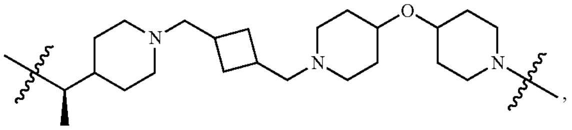
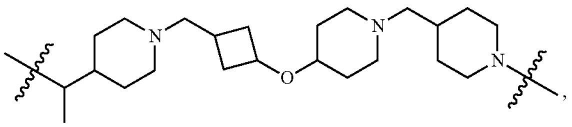
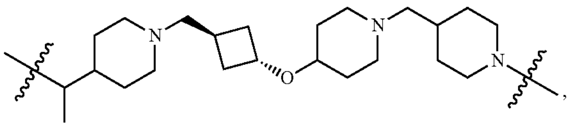
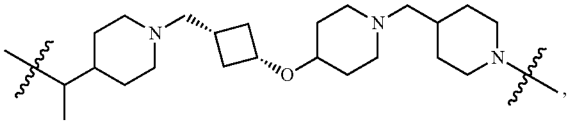
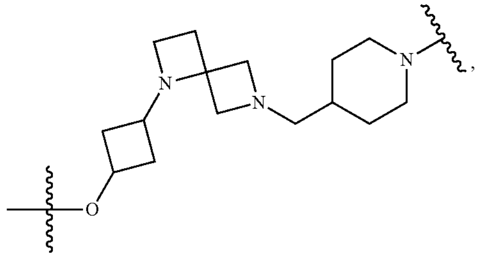
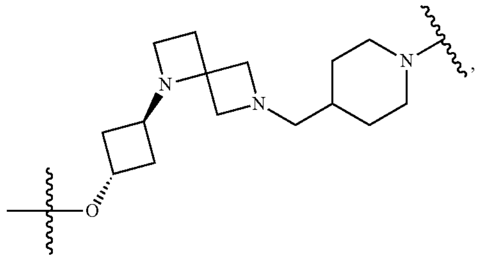

-continued

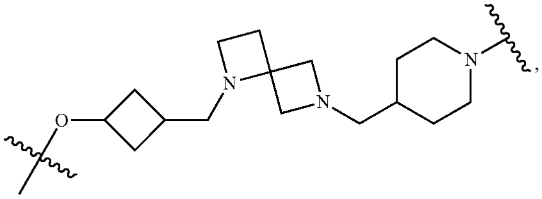
,

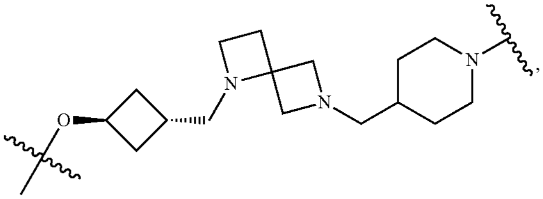
,

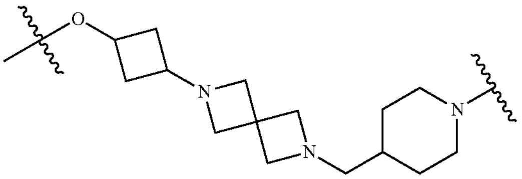
,

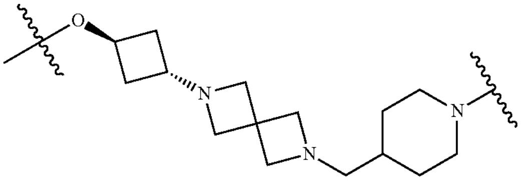
,

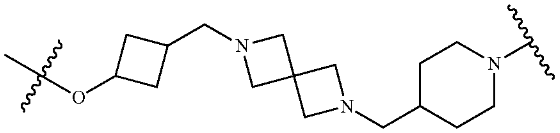
,

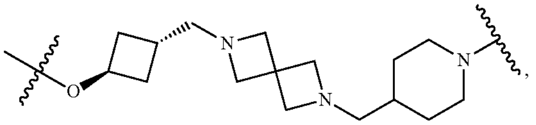
, or

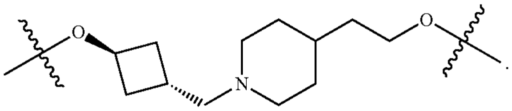
.

17. A pharmaceutical composition comprising the compound of claim 1, and a pharmaceutically acceptable carrier.

18. The pharmaceutical composition of claim 17, wherein the pharmaceutical composition further comprises an additional bioactive agent.

19. The pharmaceutical composition of claim 18, wherein the additional bioactive agent is an anti-cancer agent.

20. A method for treating a disease or disorder or ameliorating at least one symptom of the disease or disorder, comprising administering a therapeutically effective amount of the compound of claim 1, or a pharmaceutically acceptable salt thereof, to a subject, wherein the disease or disorder is associated with SMARCA2 or SMARCA4, and the compound or pharmaceutically acceptable salt thereof is effective in treating or ameliorating at least one symptom of the disease or disorder.

21. The method of claim 20, wherein the disease or disorder is associated with SMARCA2 accumulation and aggregation.

22. The method of claim 20, wherein the disease or disorder is cancer.

23. The method of claim 22, wherein the cancer is a cancer with a SMARCA4 mutation.

24. The method of claim 22, wherein the cancer is a SMARCA4-deficient cancer or a cancer with decreased expression of SMARCA4 relative to normal SMARCA4 expression.

25. The method of claim 22, wherein the cancer is lung cancer or non-small cell lung cancer.

26. A method for treating a disease or disorder or ameliorating at least one symptom of the disease or disorder, comprising administering a pharmaceutical composition comprising the compound of claim 1, or a pharmaceutically acceptable salt thereof, and a pharmaceutically acceptable carrier to a subject, wherein the disease or disorder is associated with SMARCA2 or SMARCA4, and the compound, or pharmaceutically acceptable salt thereof, is effective in treating or ameliorating at least one symptom of the disease or disorder.

27. A compound selected from any one of the following:

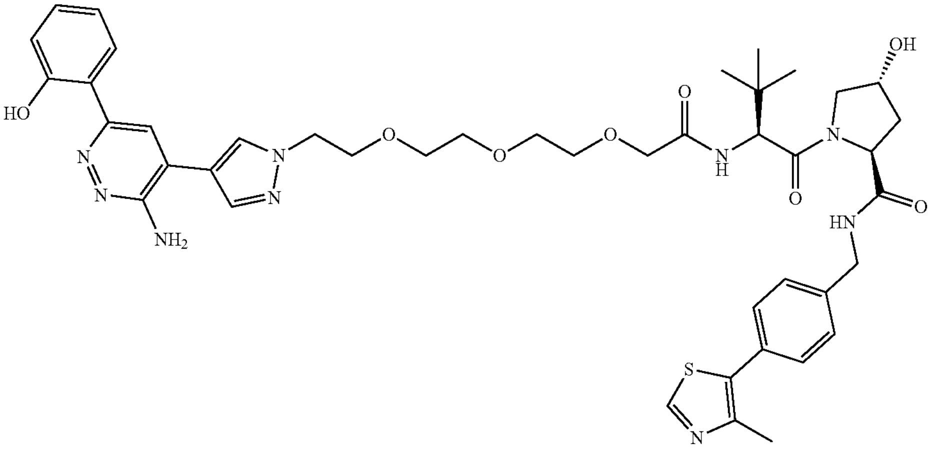

-continued
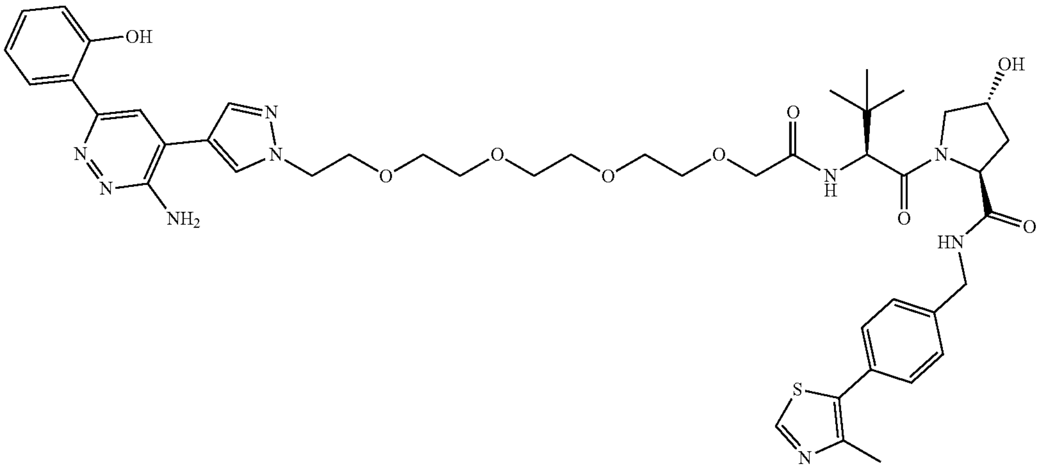
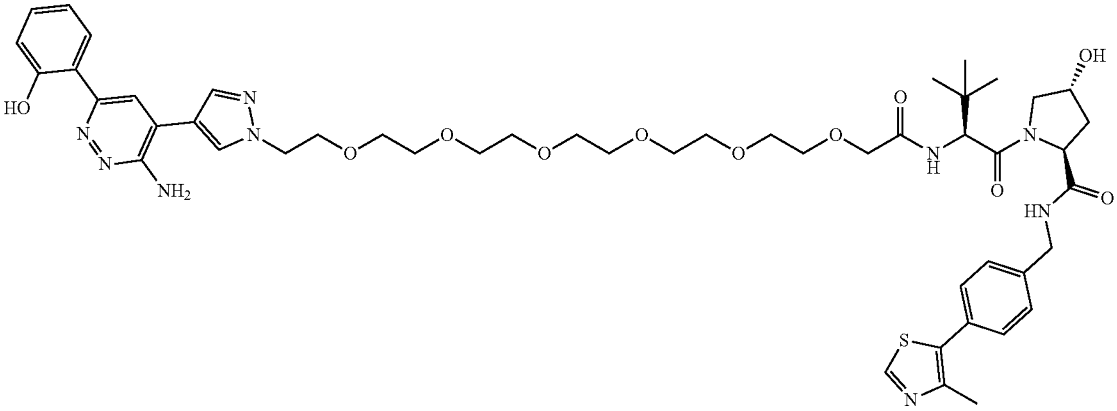
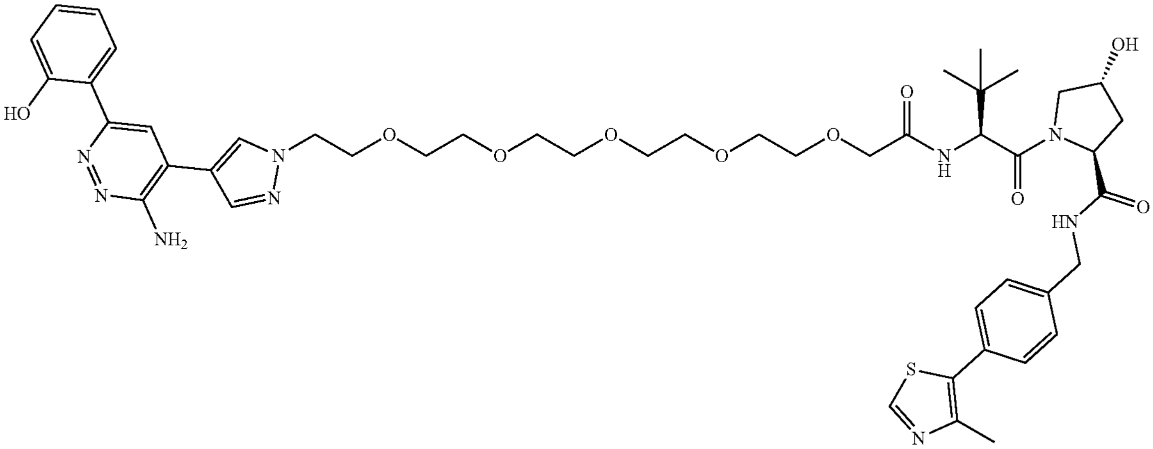
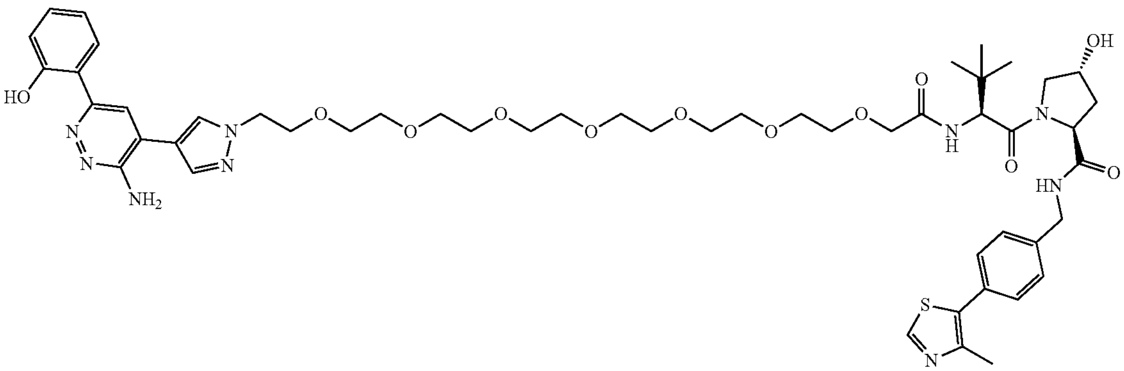

-continued
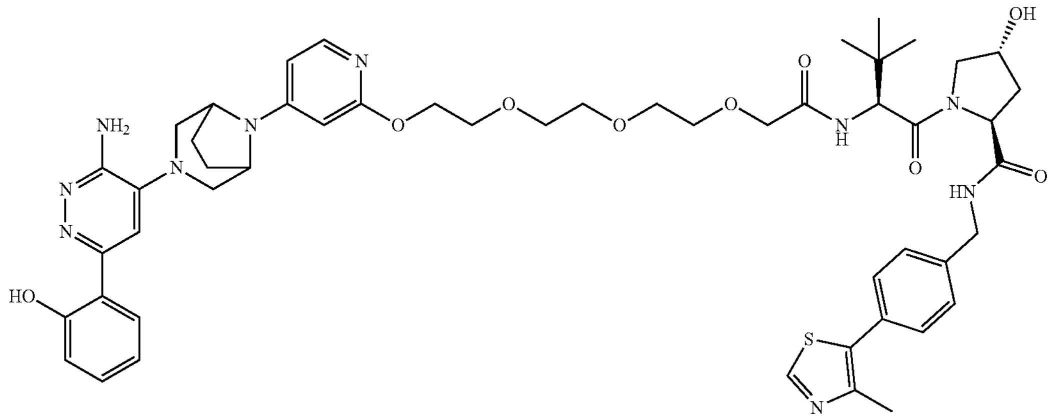
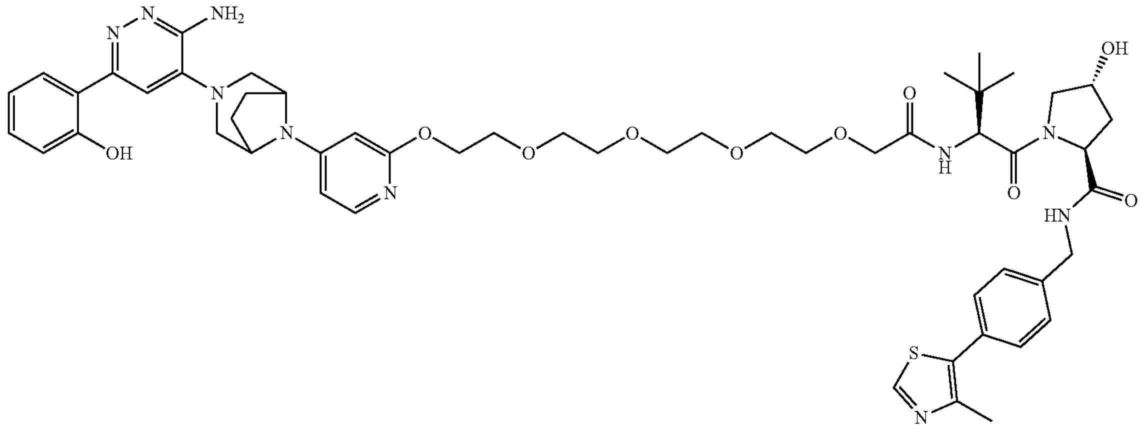
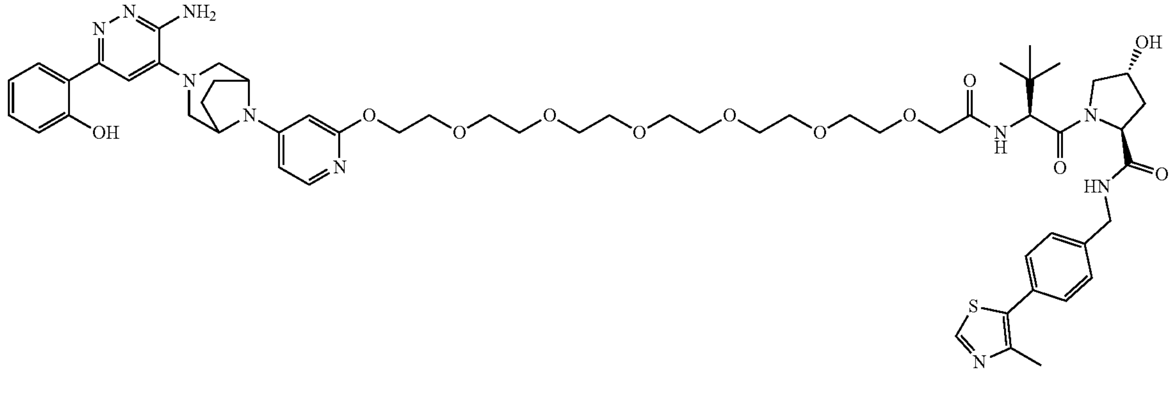
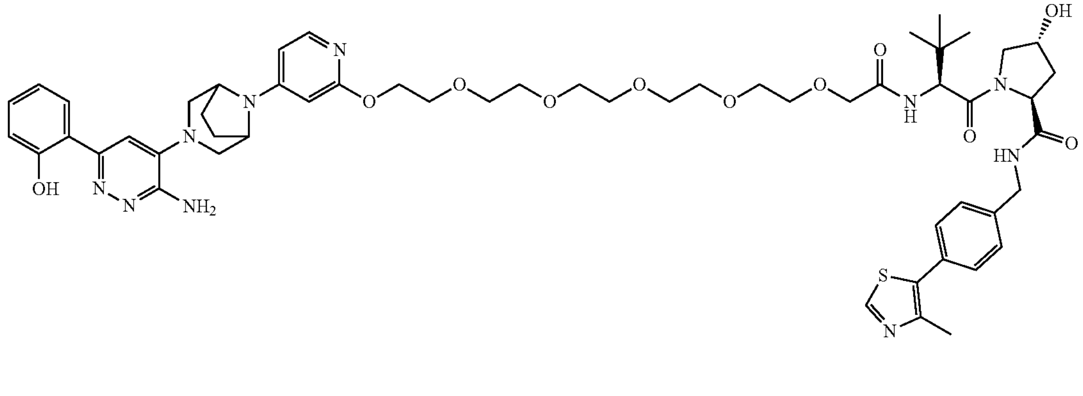

-continued
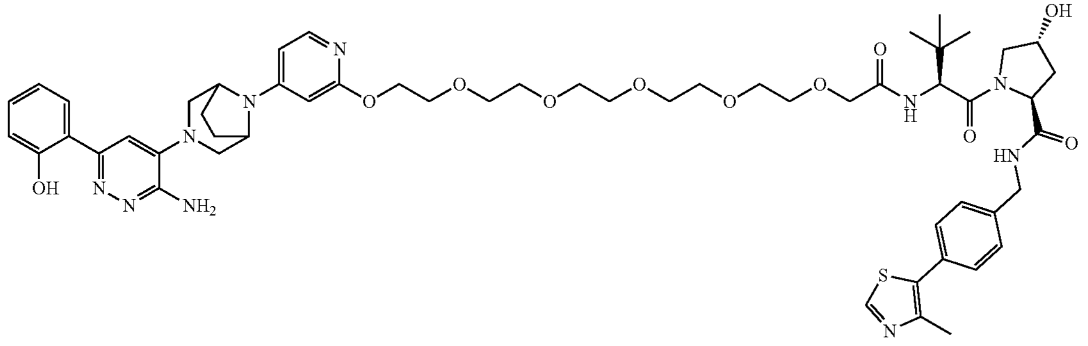
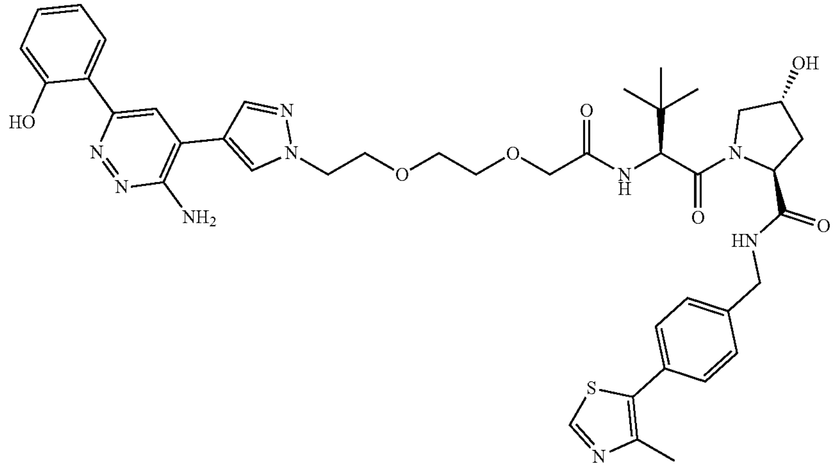
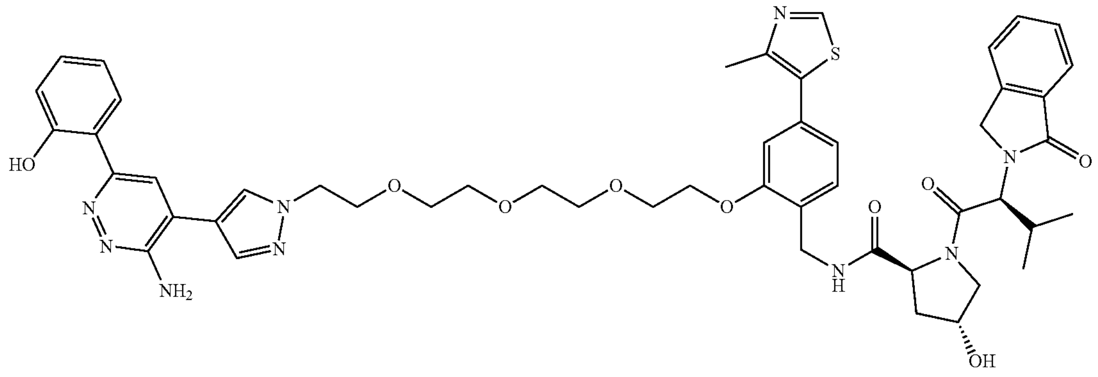
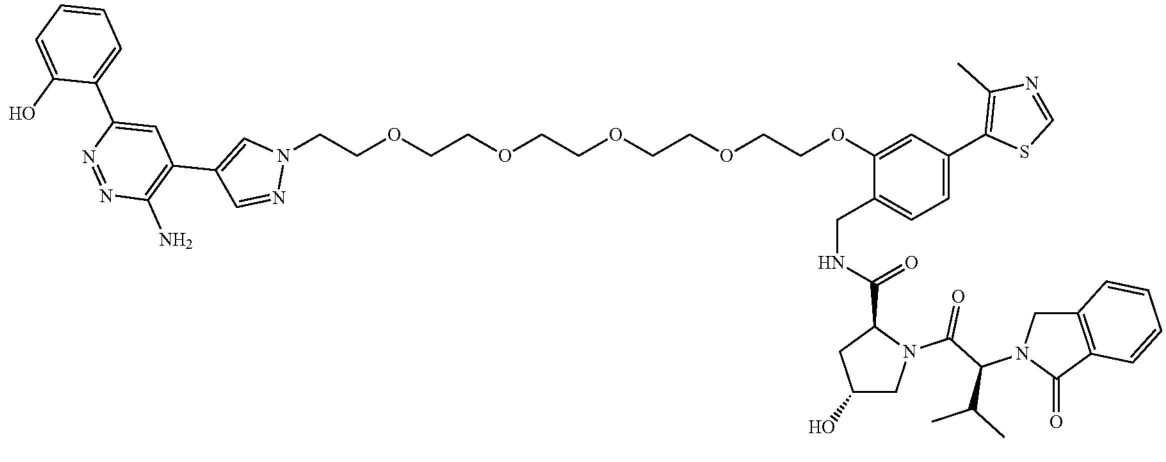

-continued
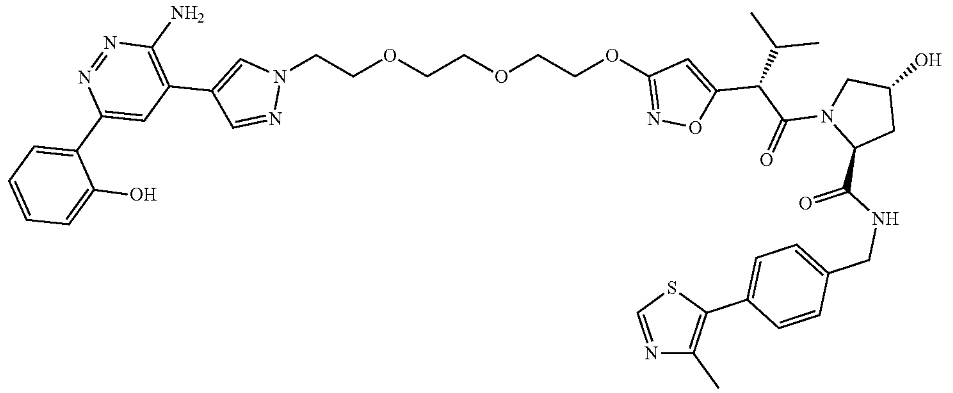
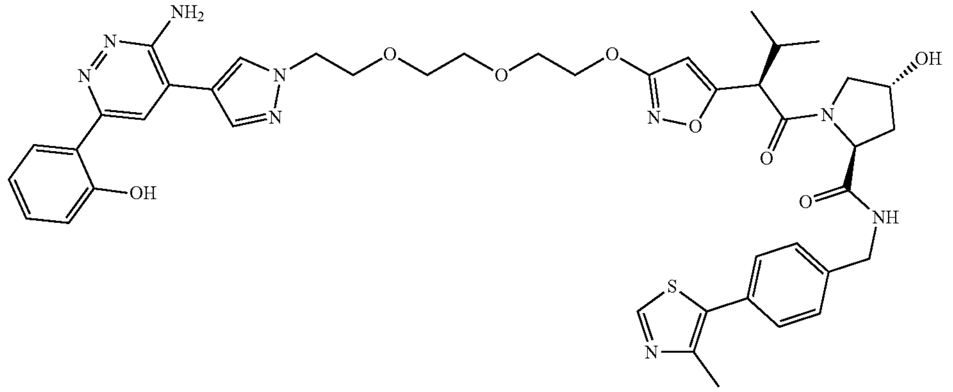
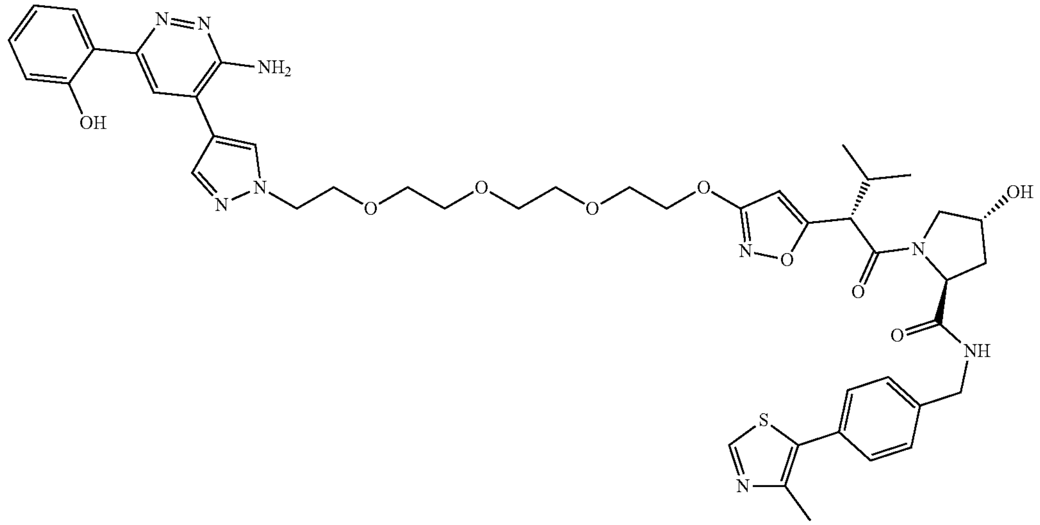

-continued
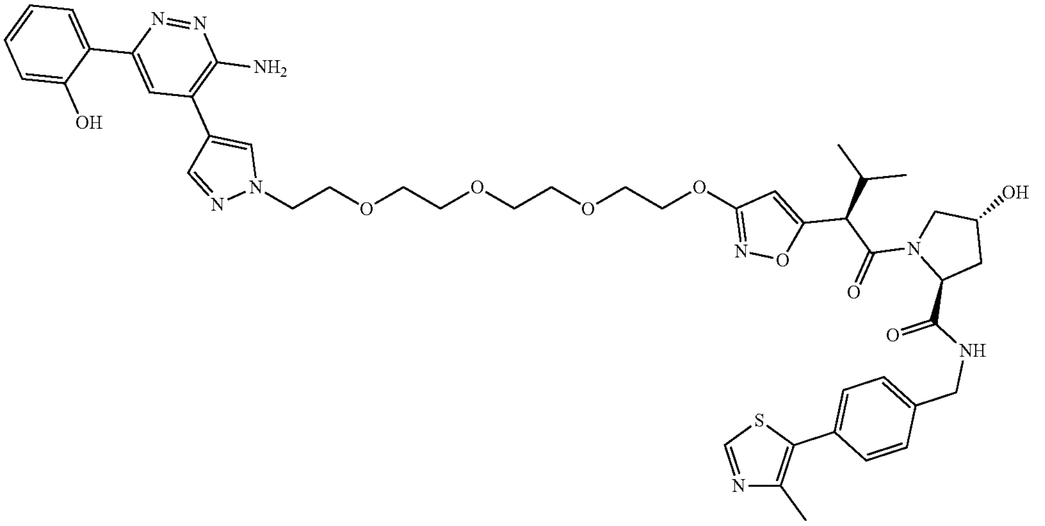
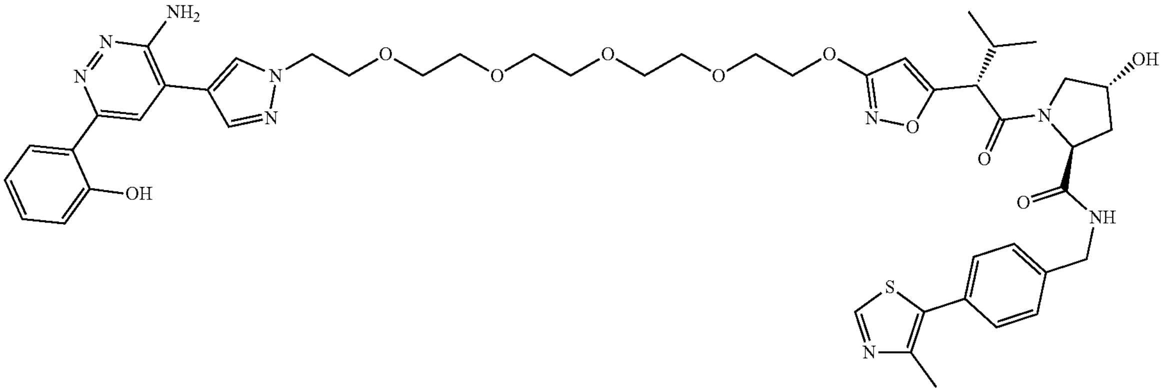
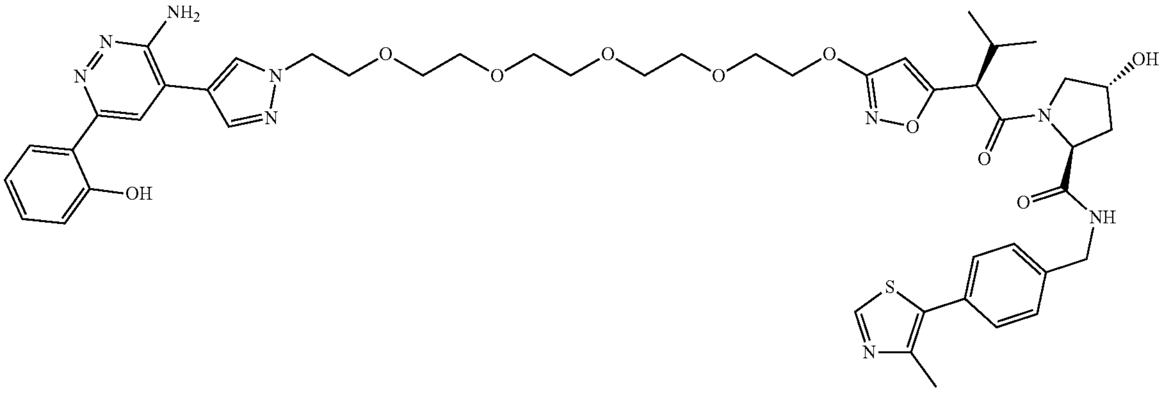
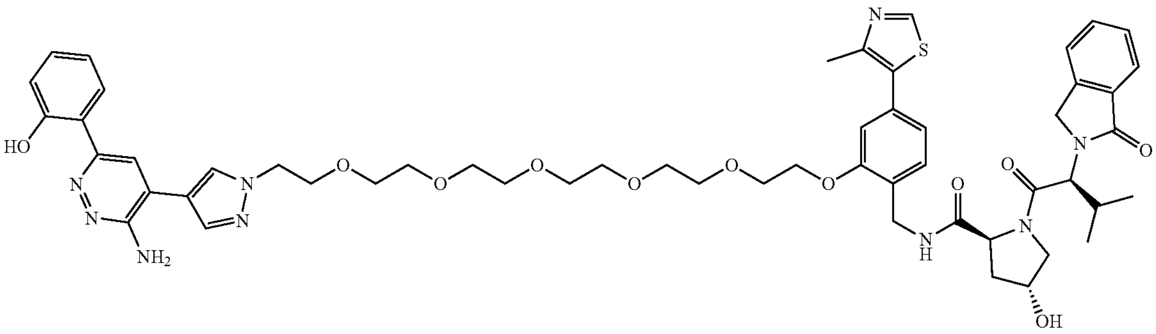

-continued
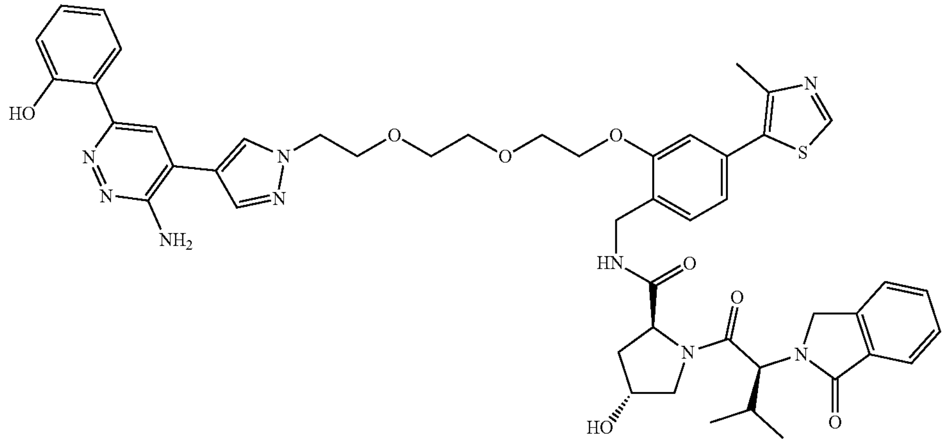
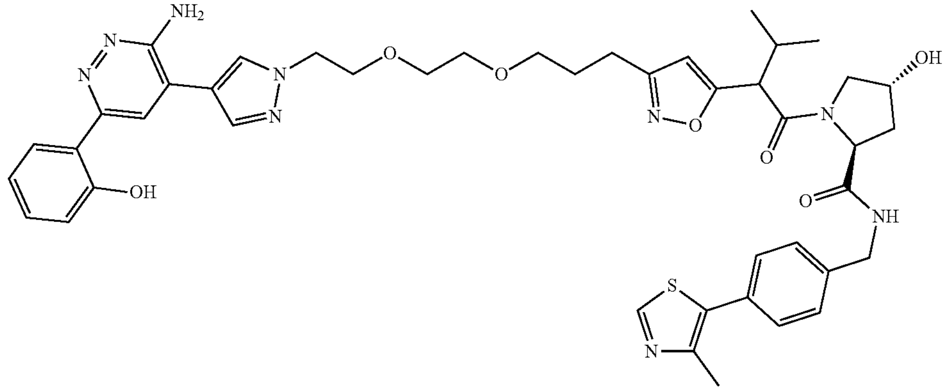
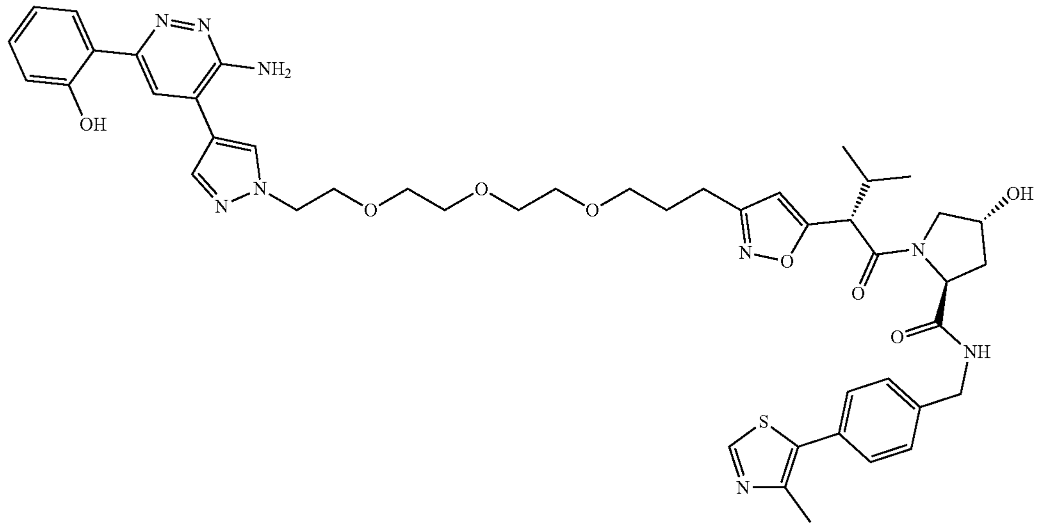

-continued
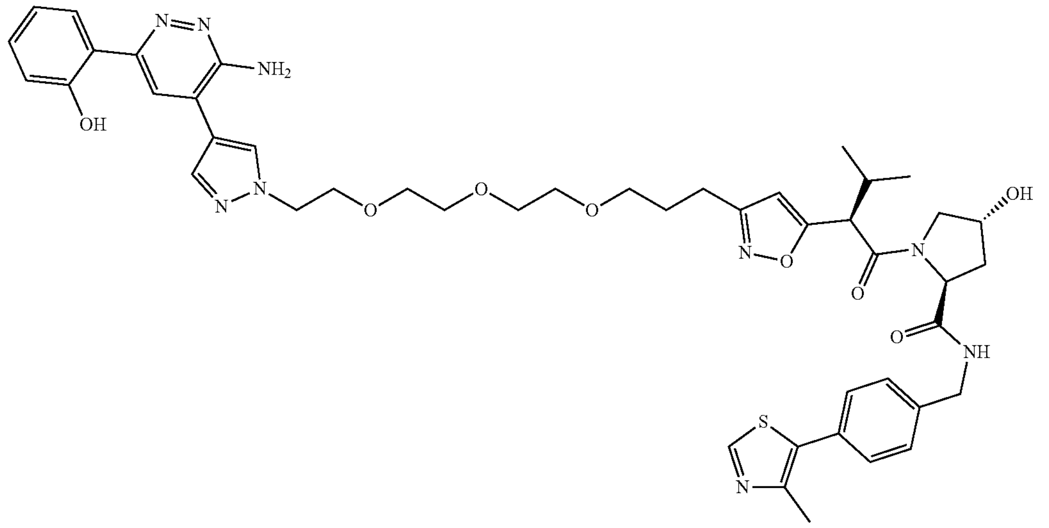
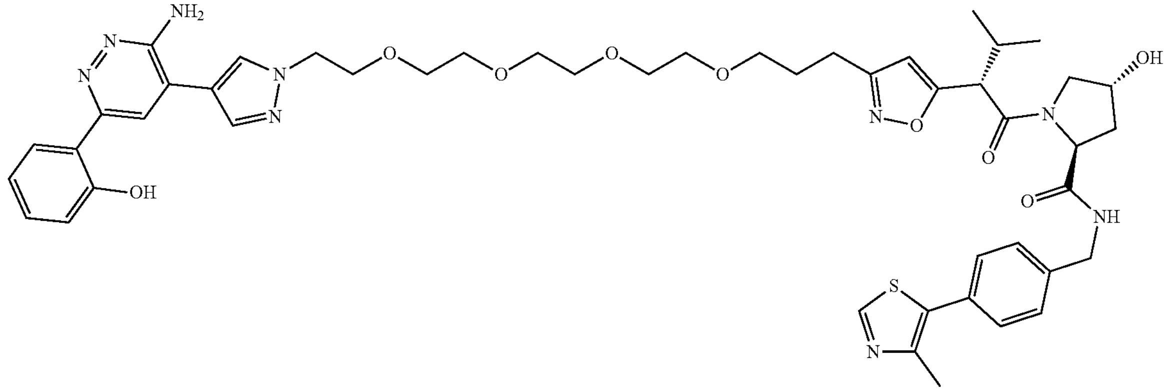
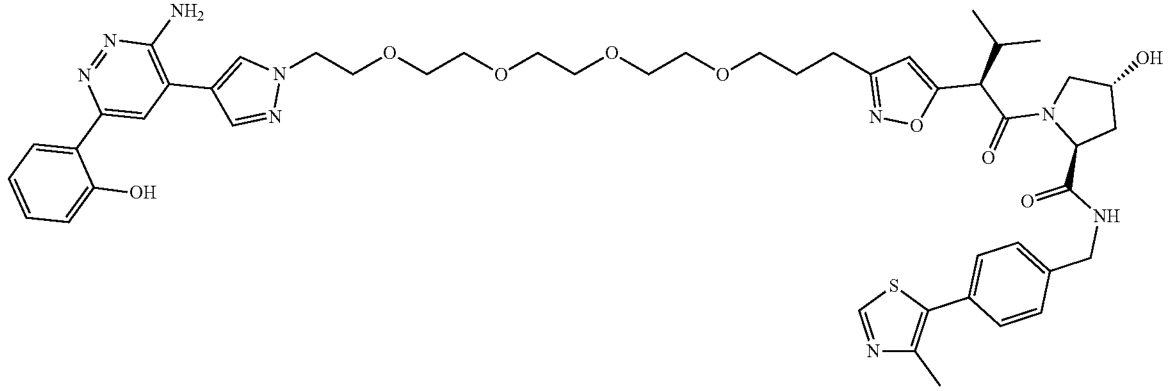
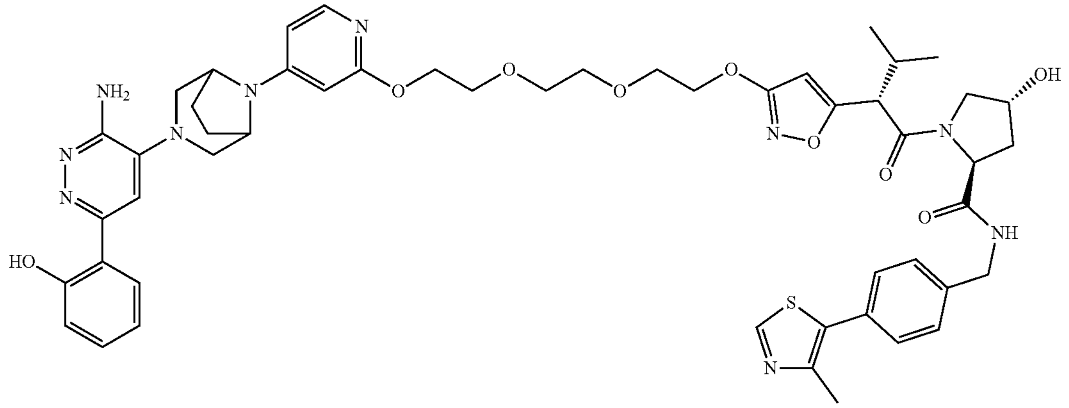

-continued
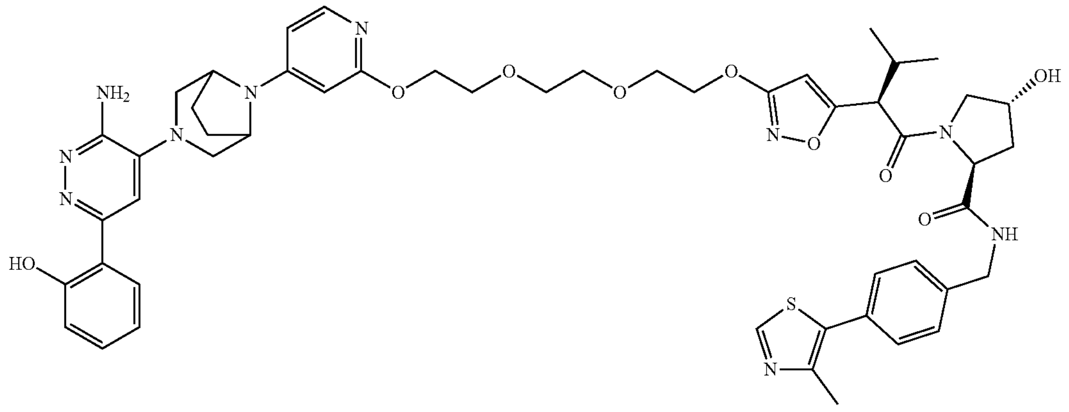
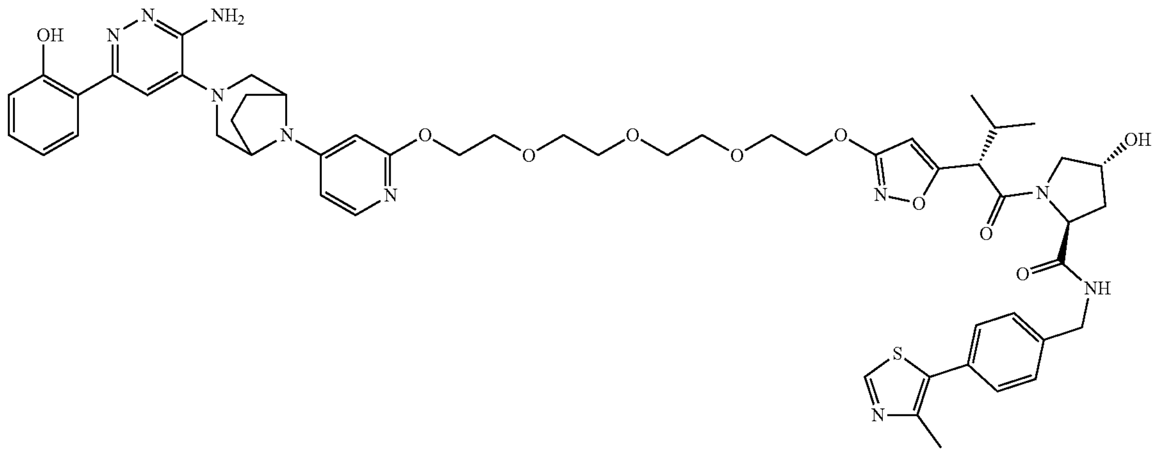
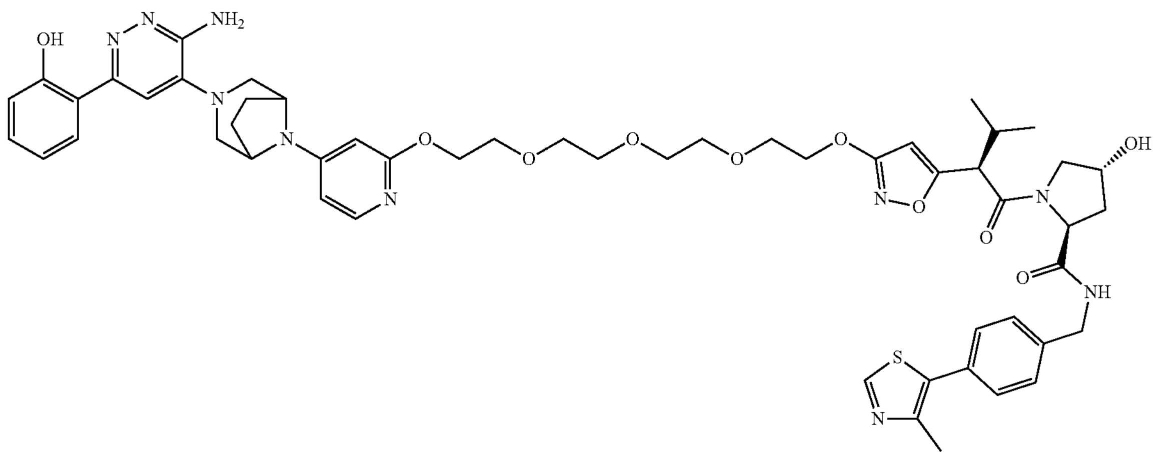

-continued
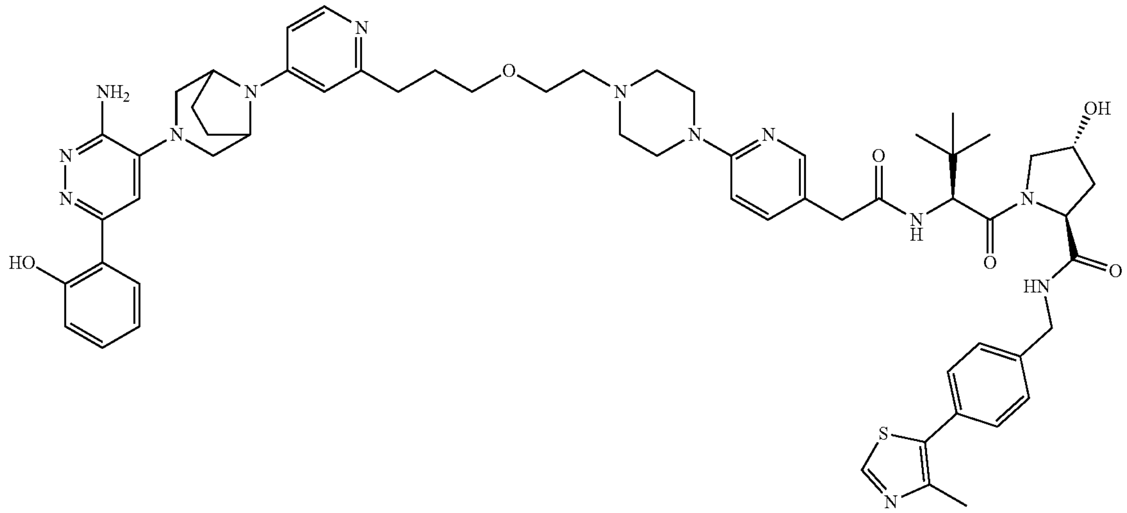
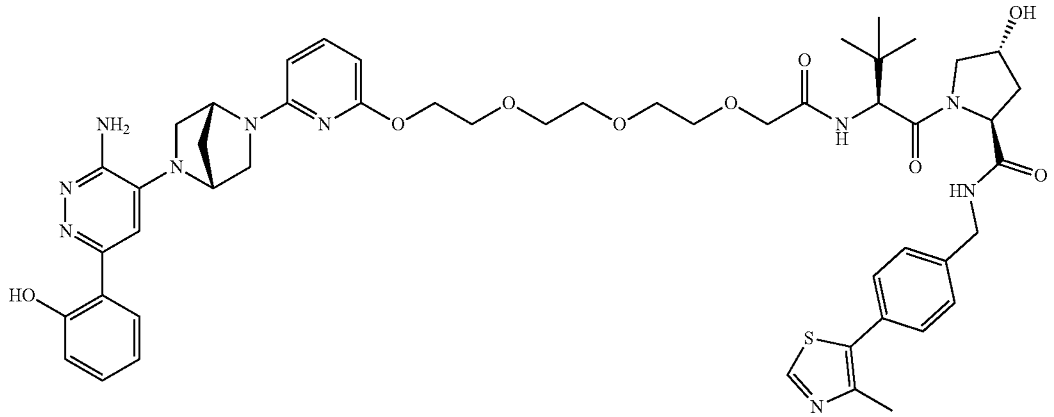
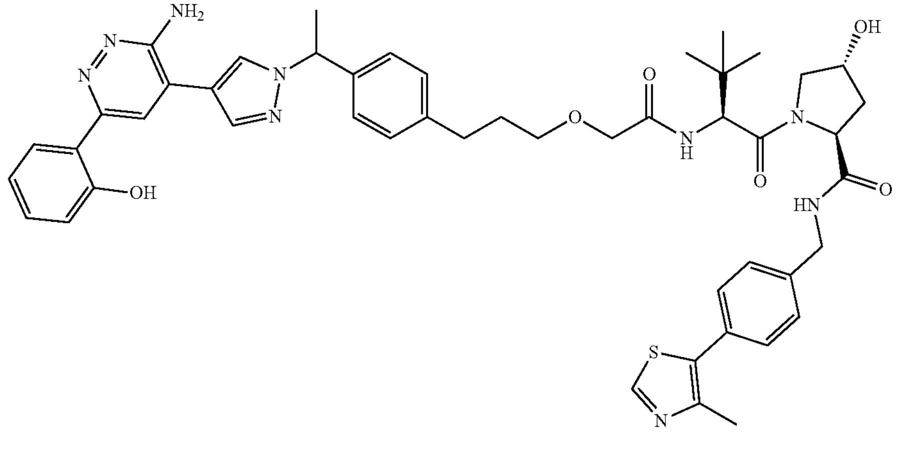

-continued
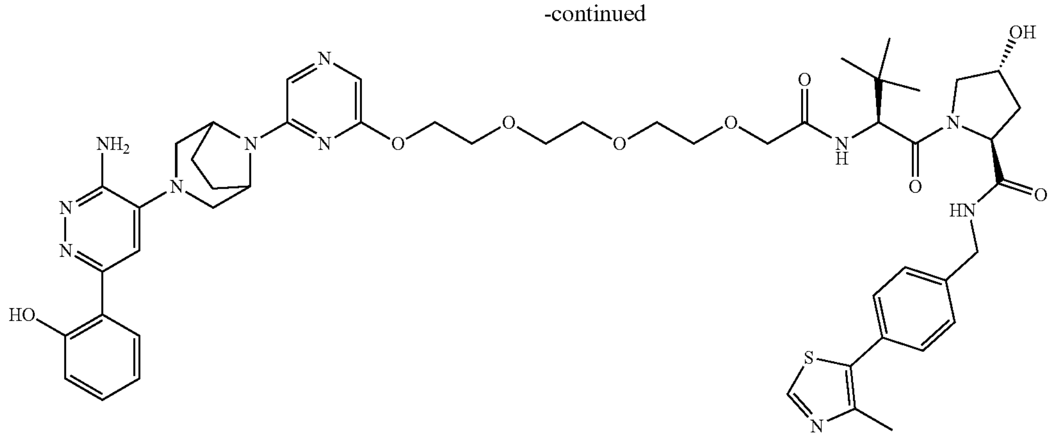
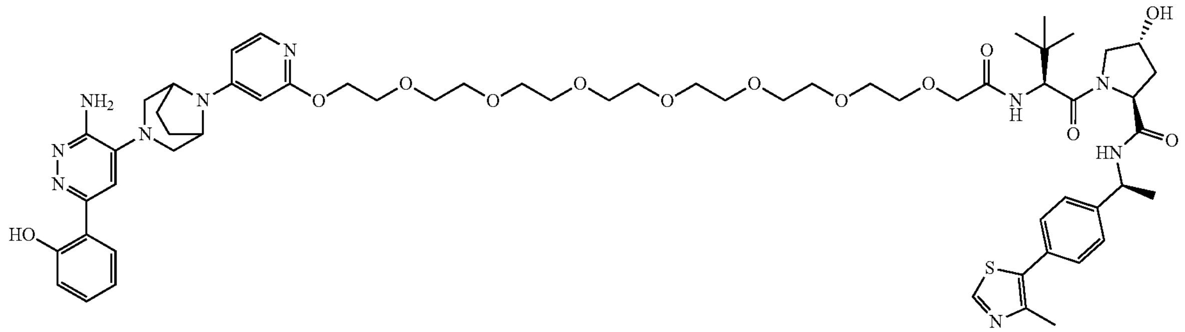
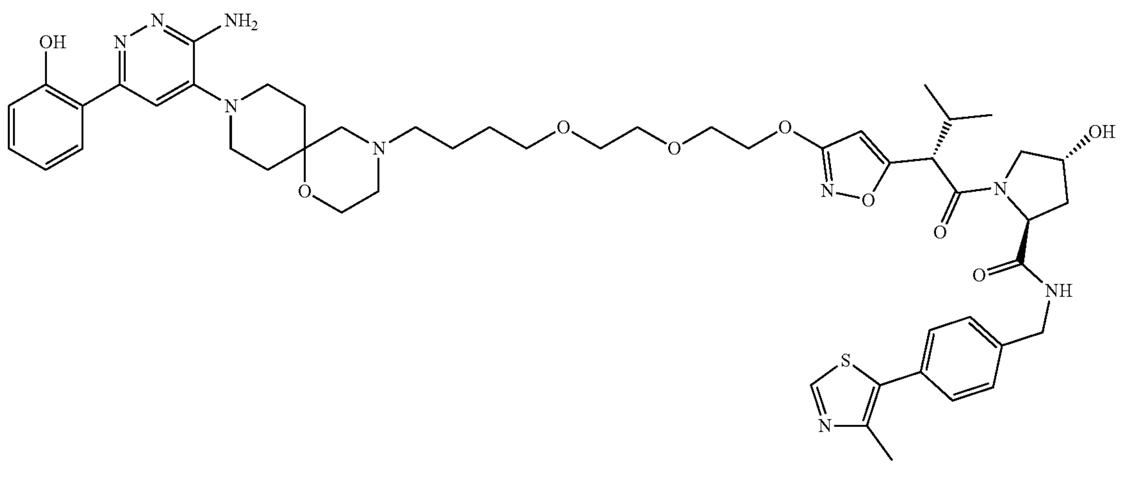

-continued
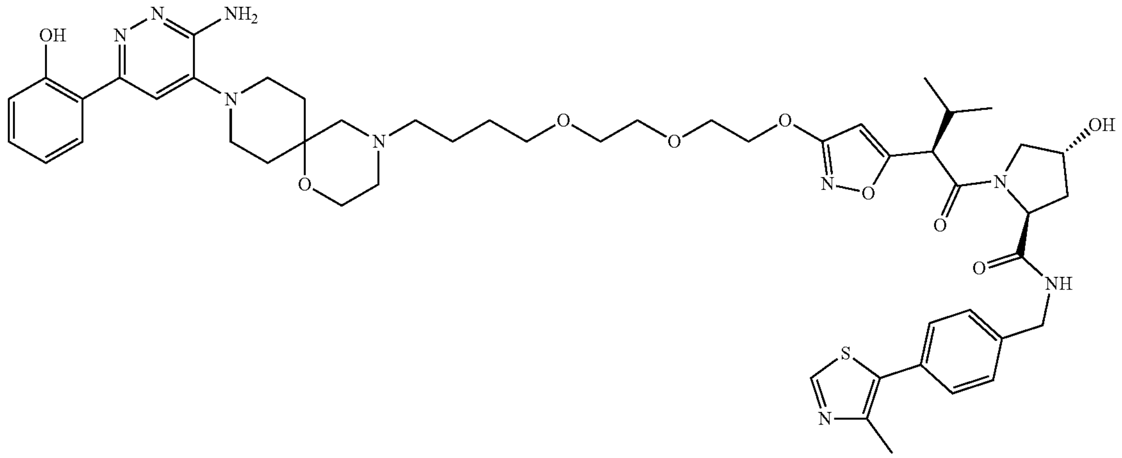
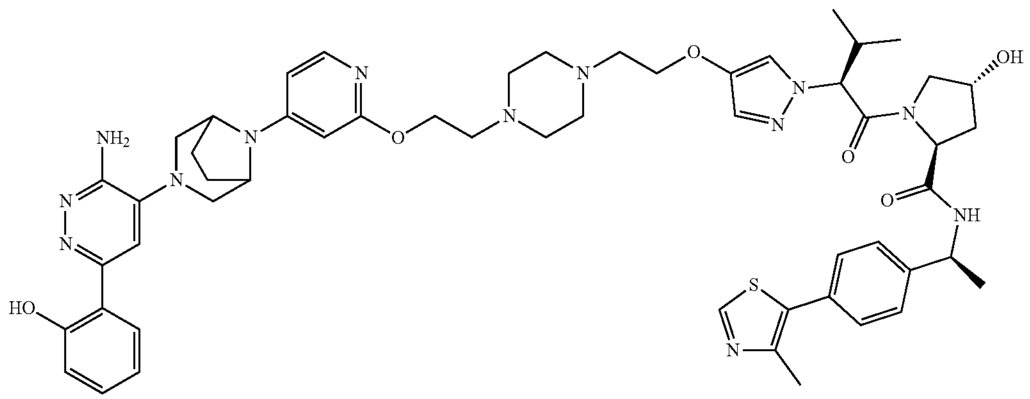
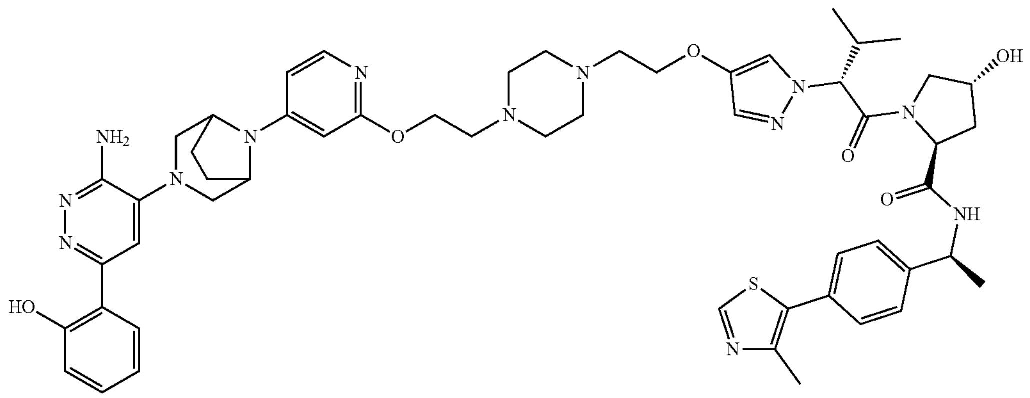

-continued
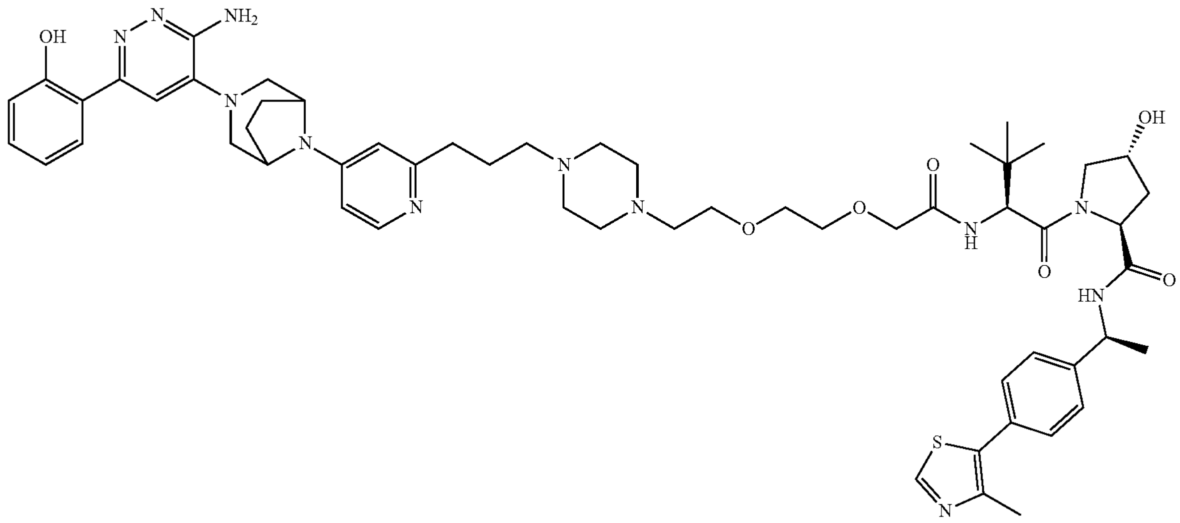
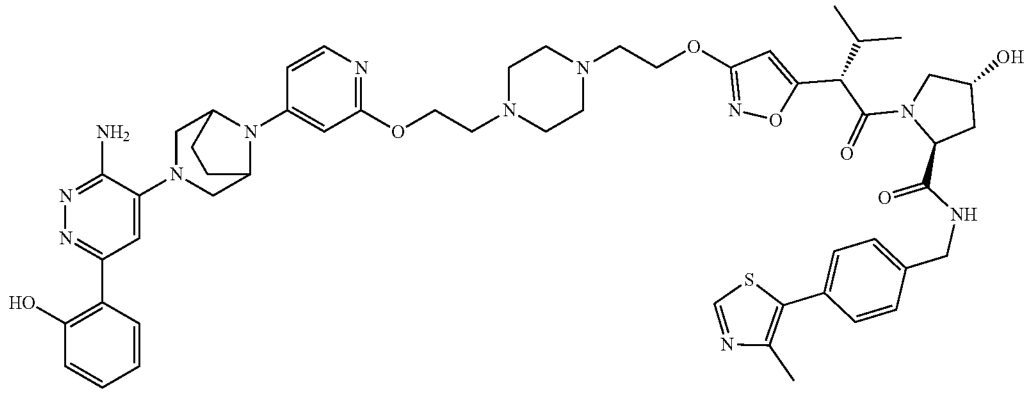
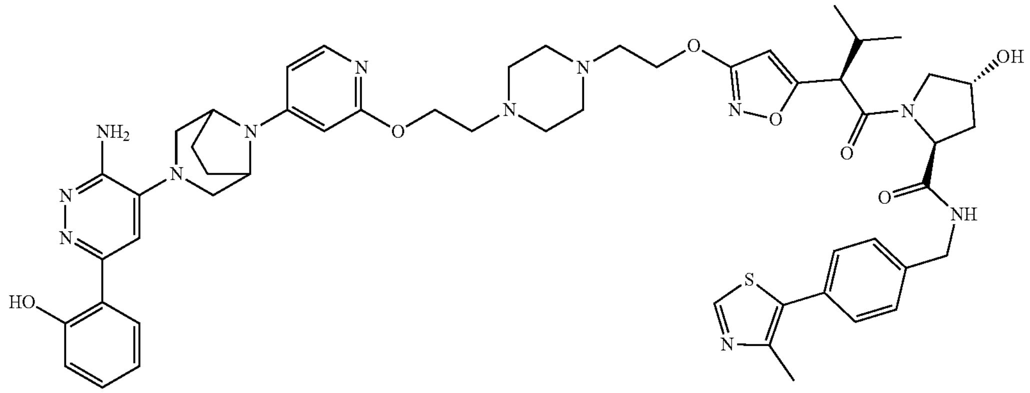
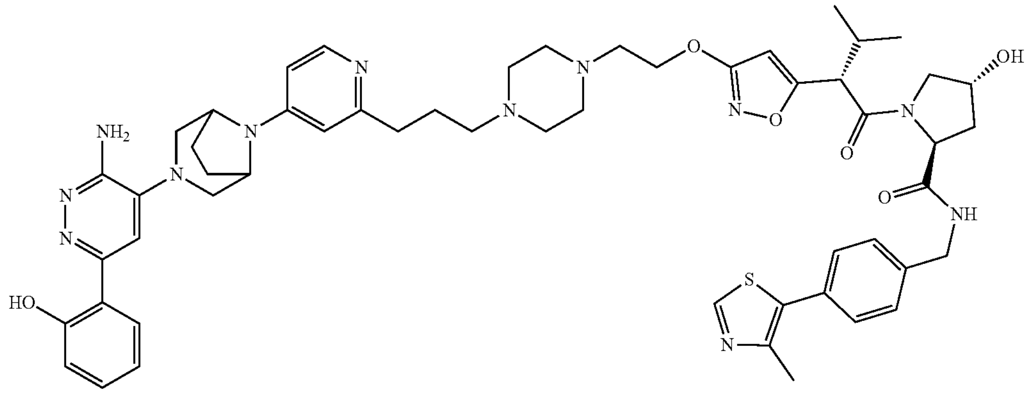

-continued
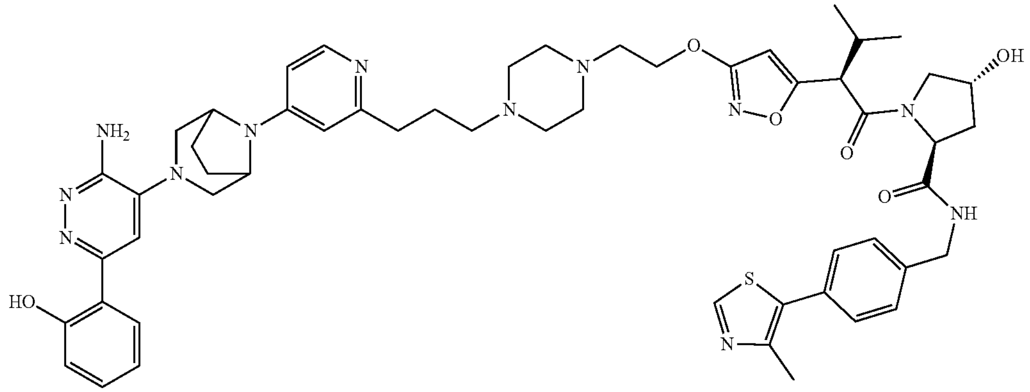
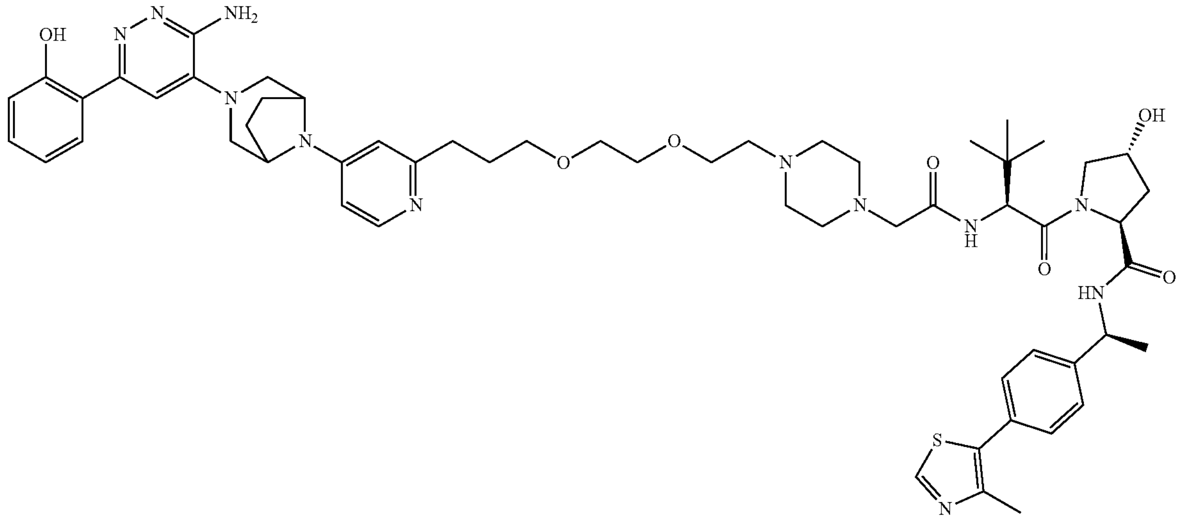
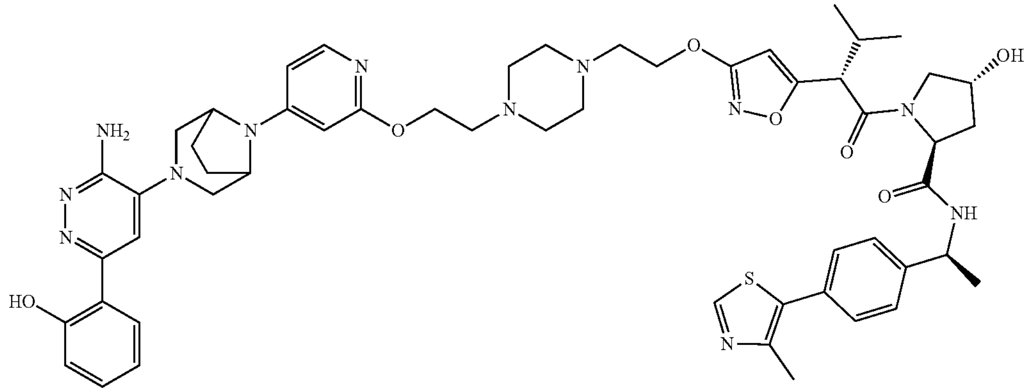
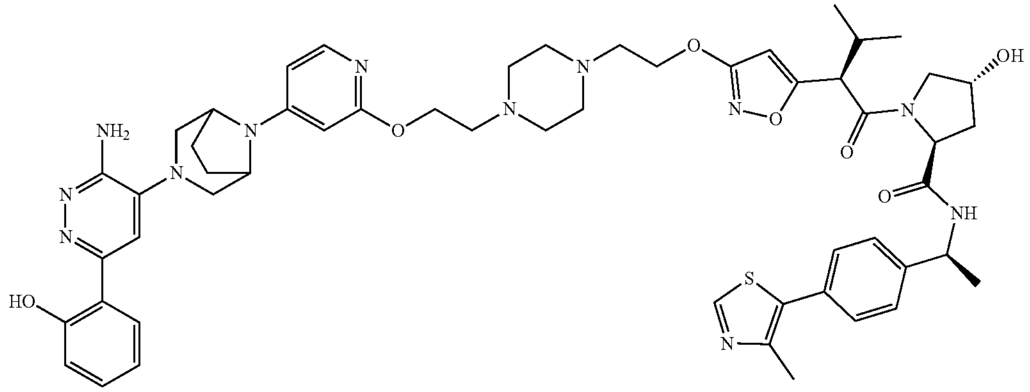

-continued
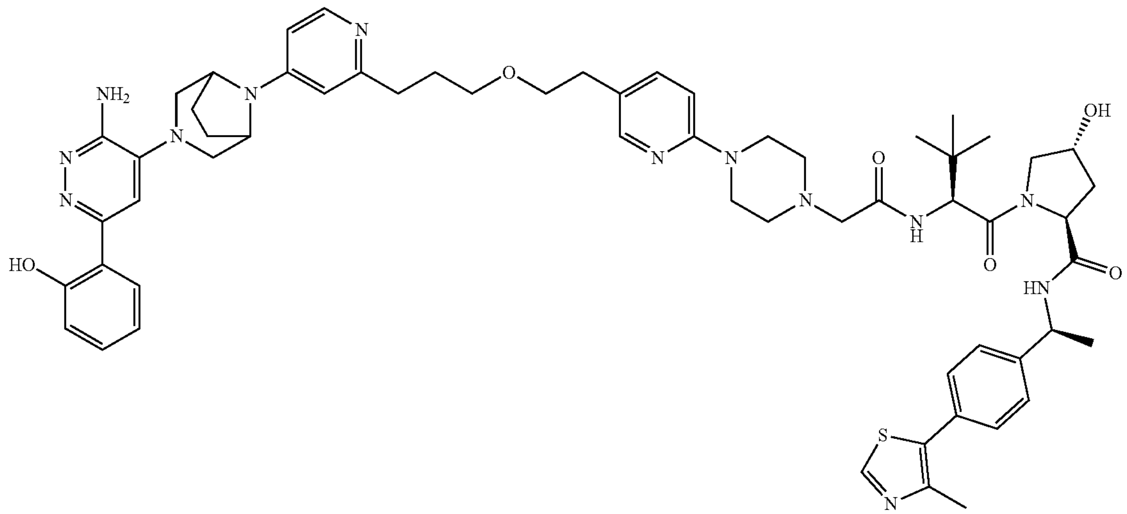
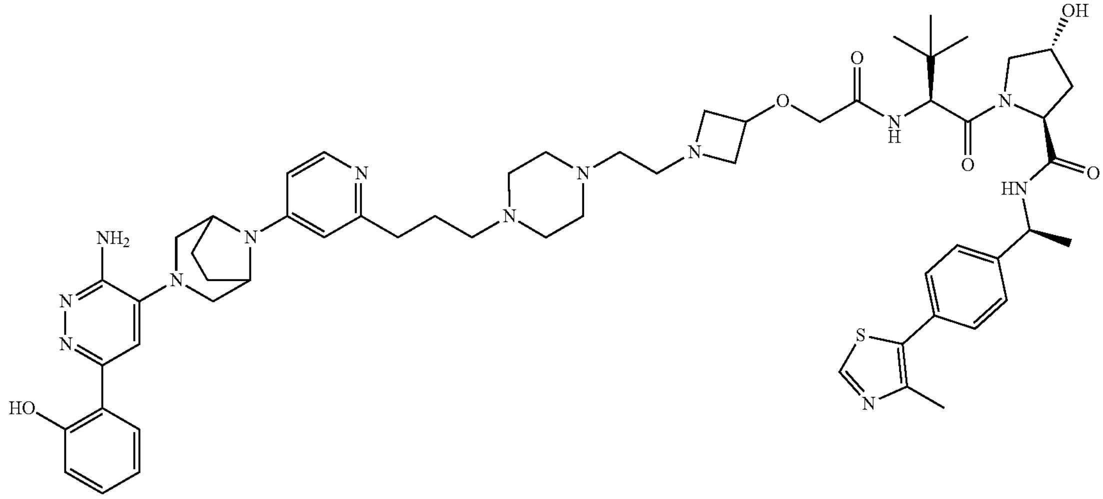
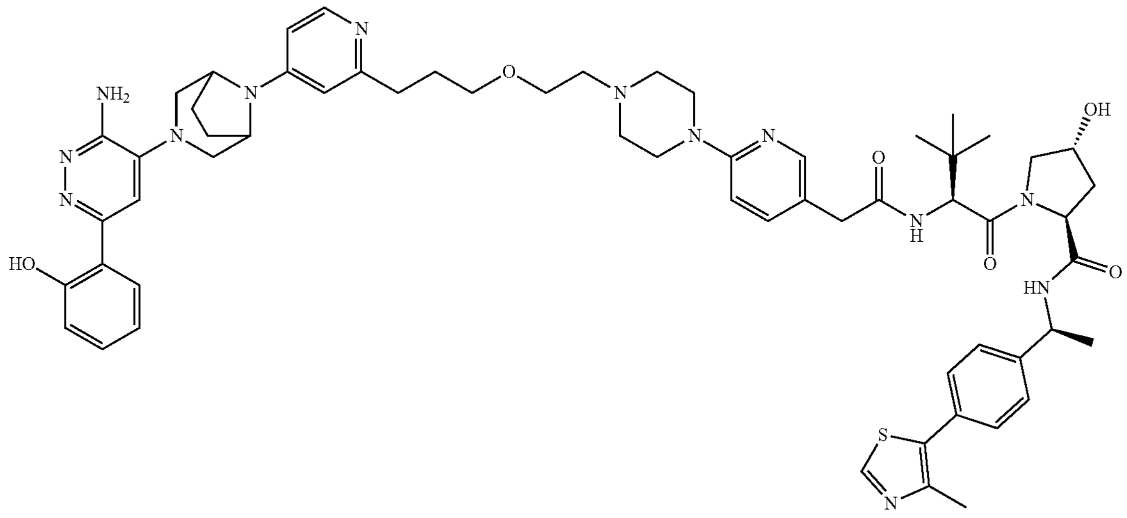

-continued
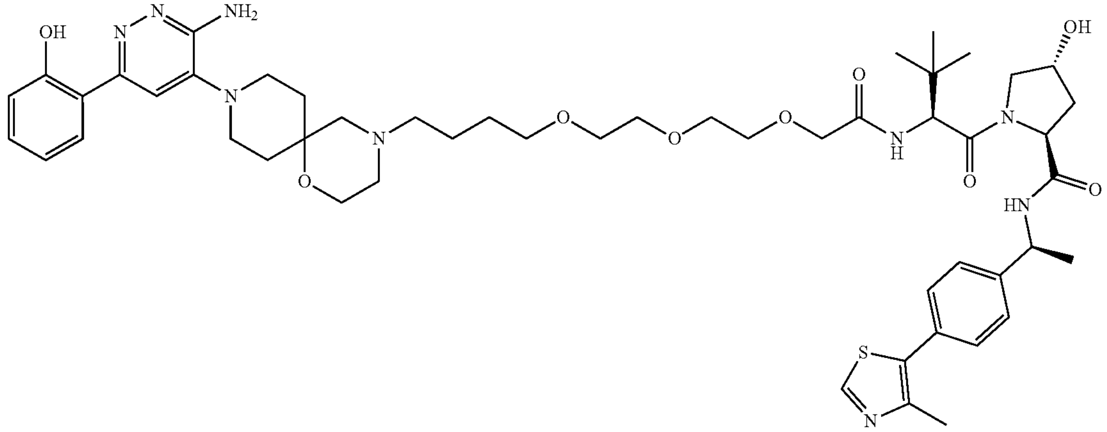
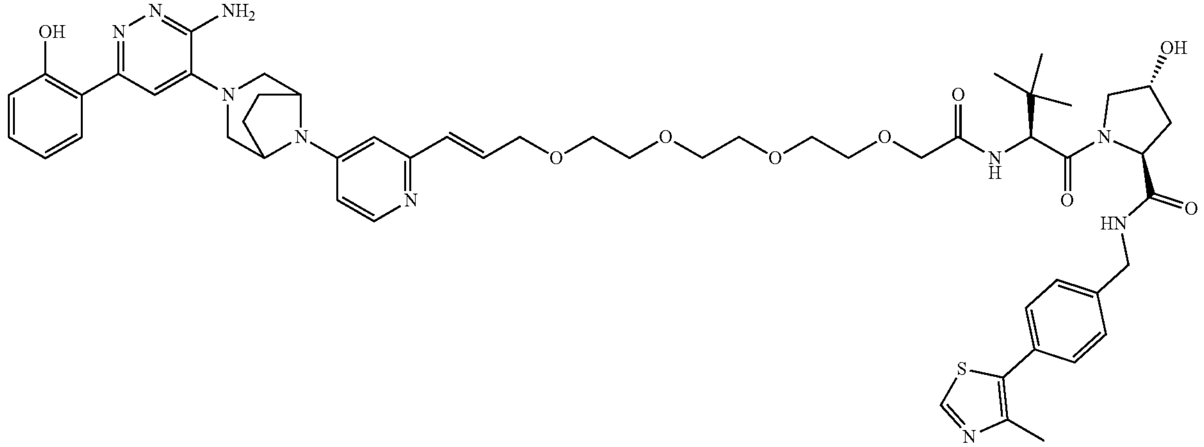
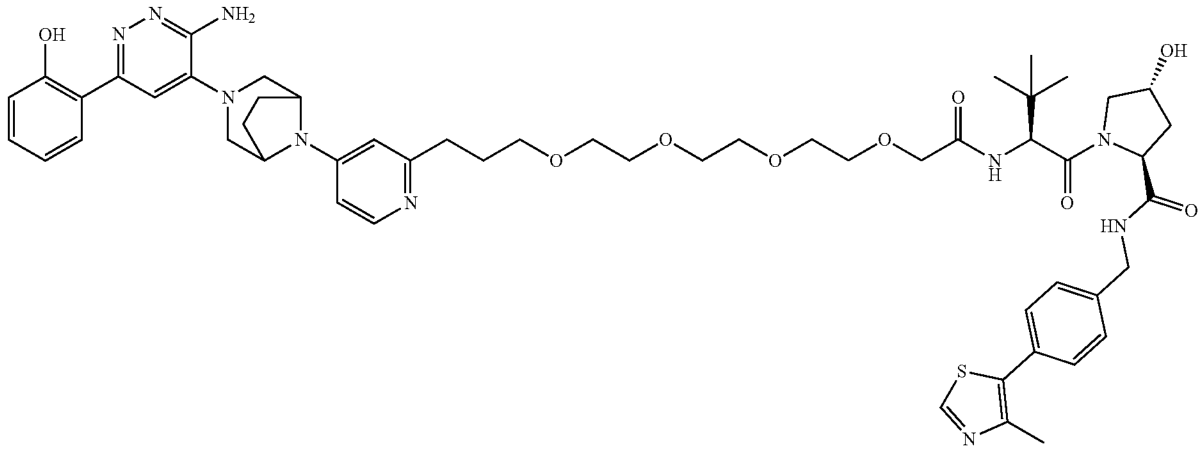
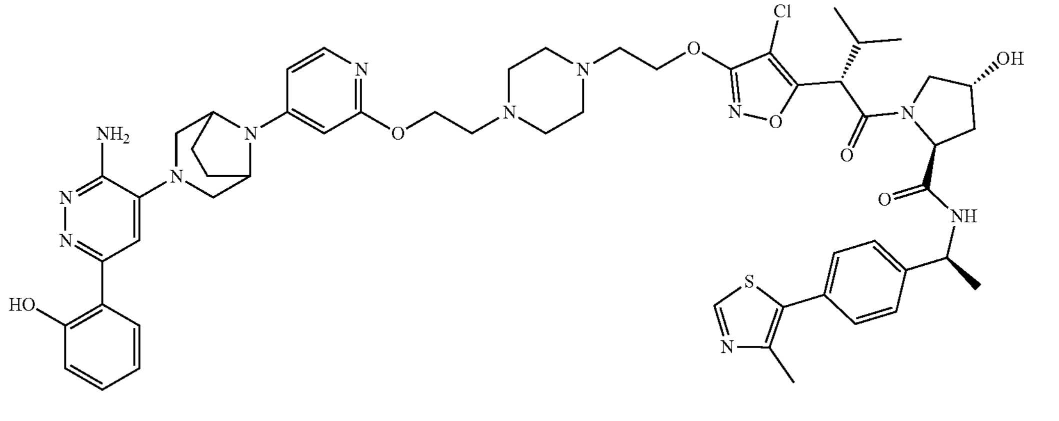

-continued
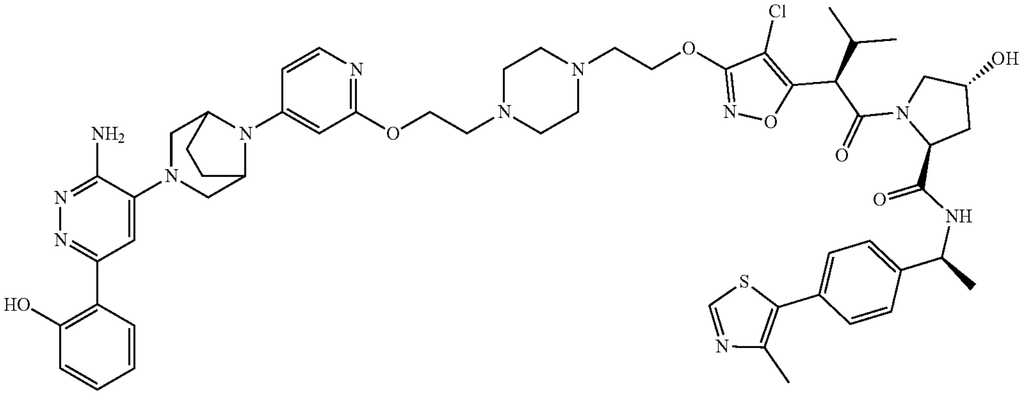
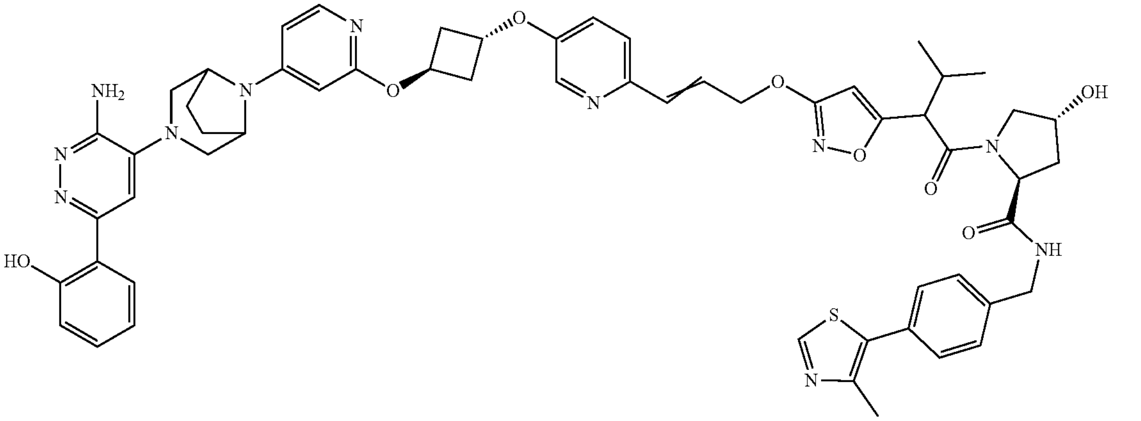
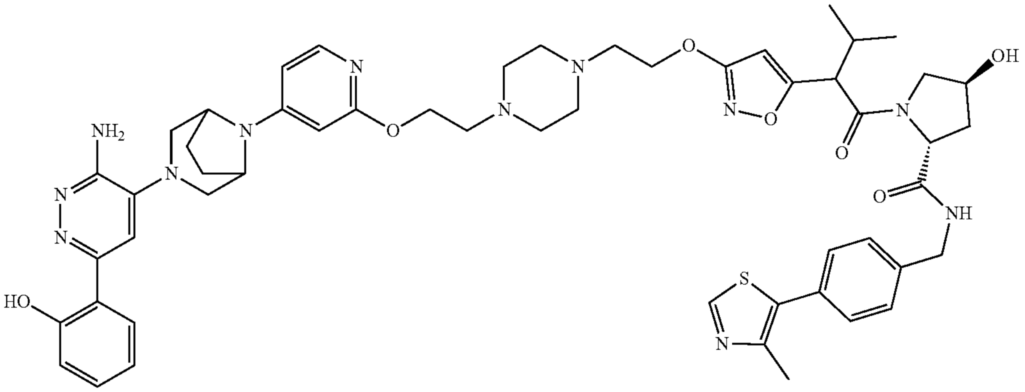
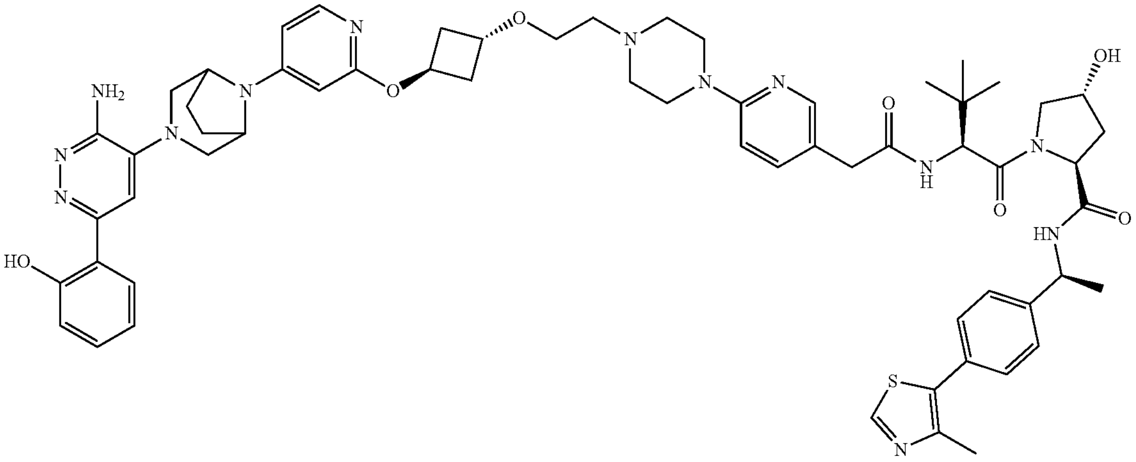

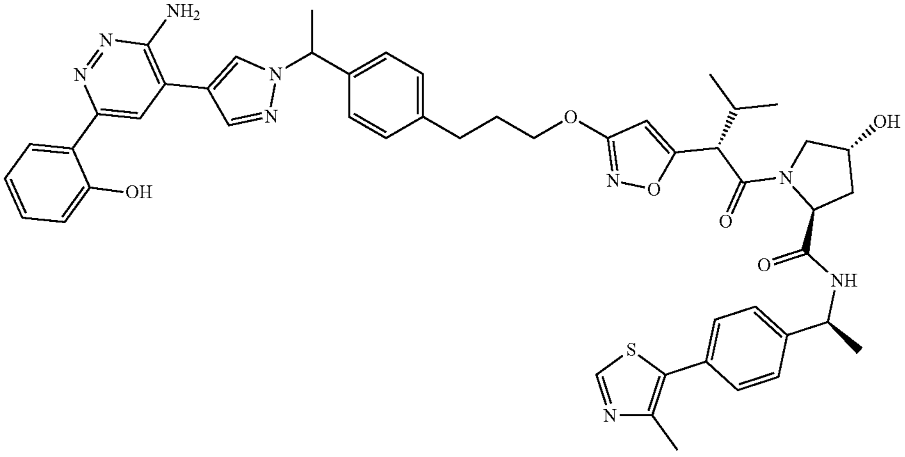
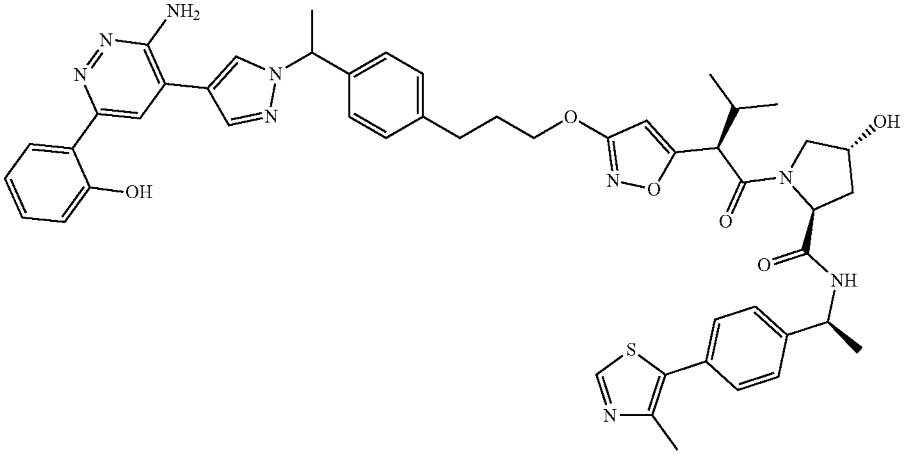
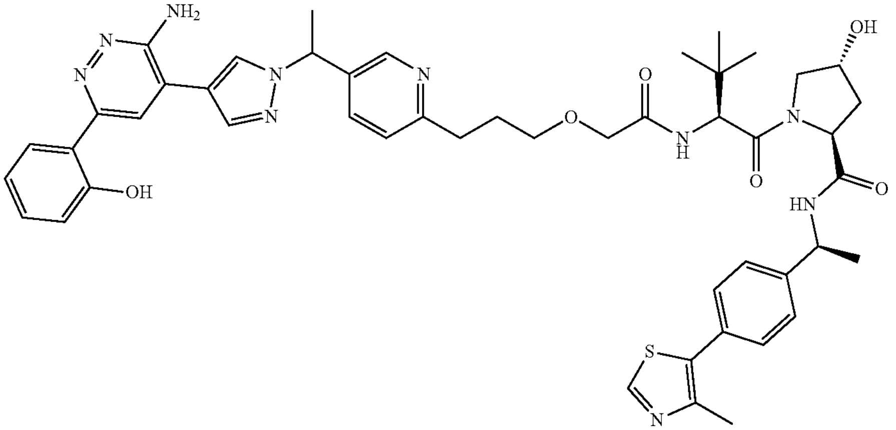

-continued
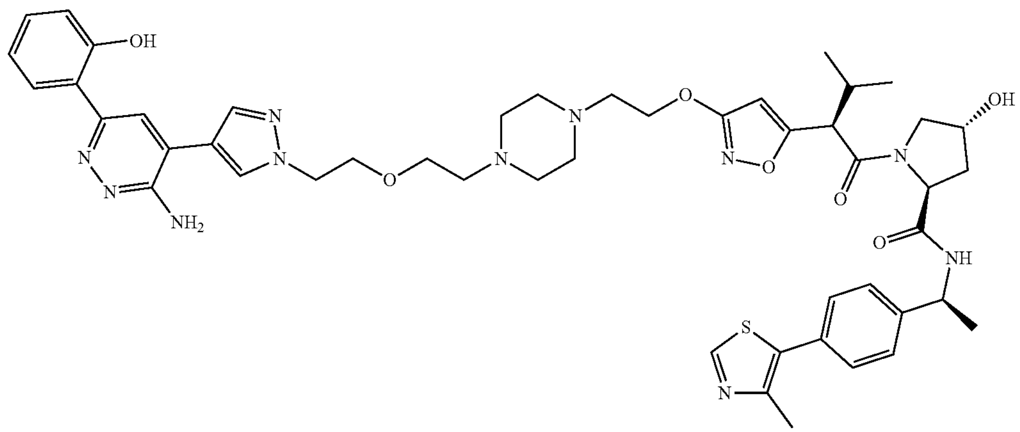
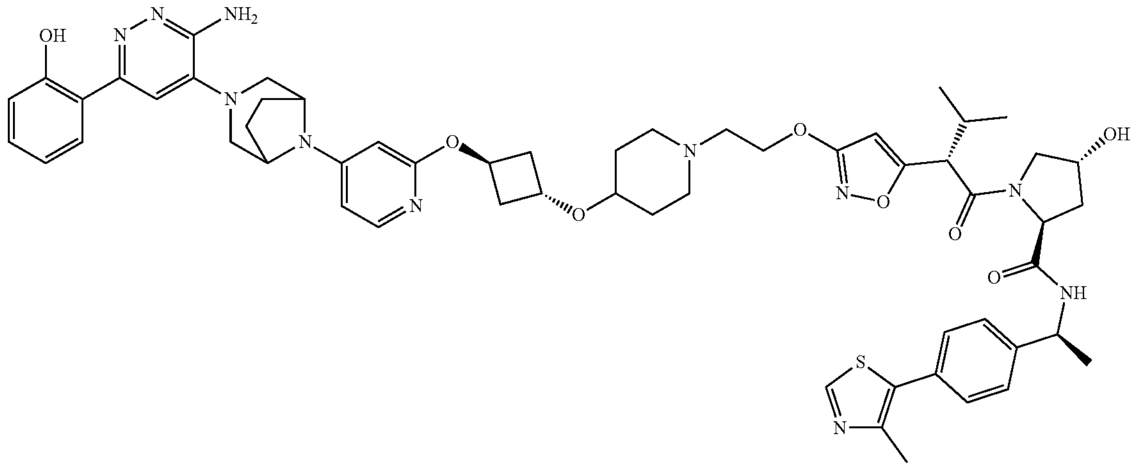
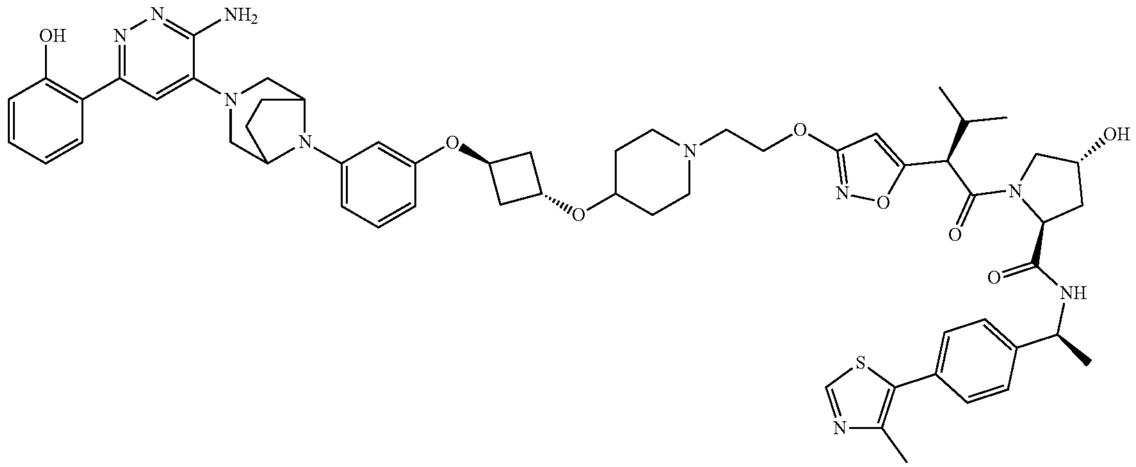

-continued
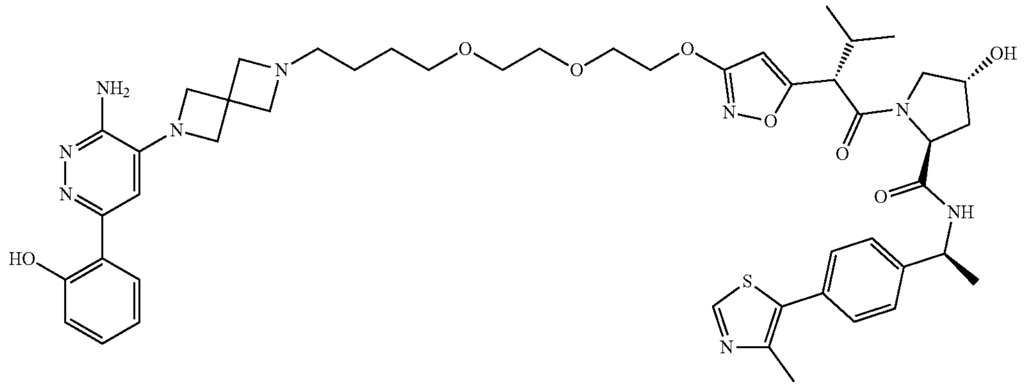
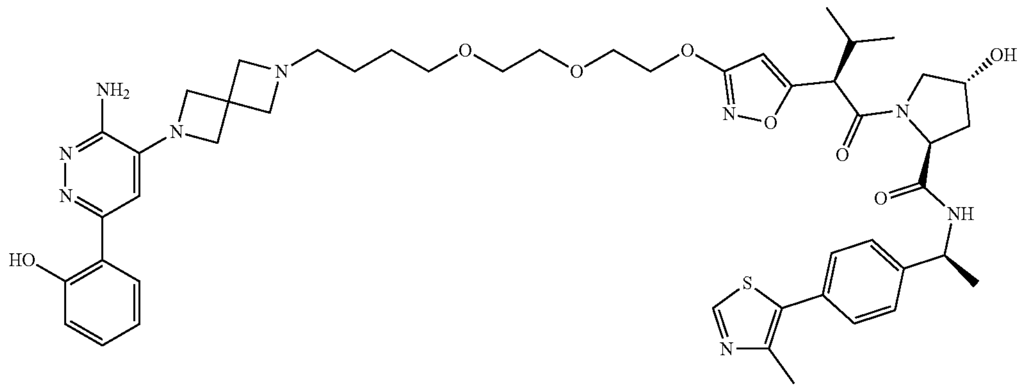
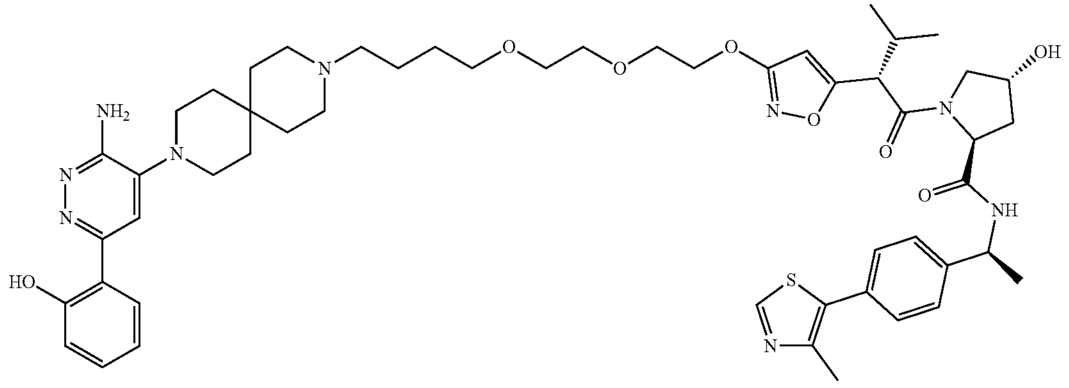
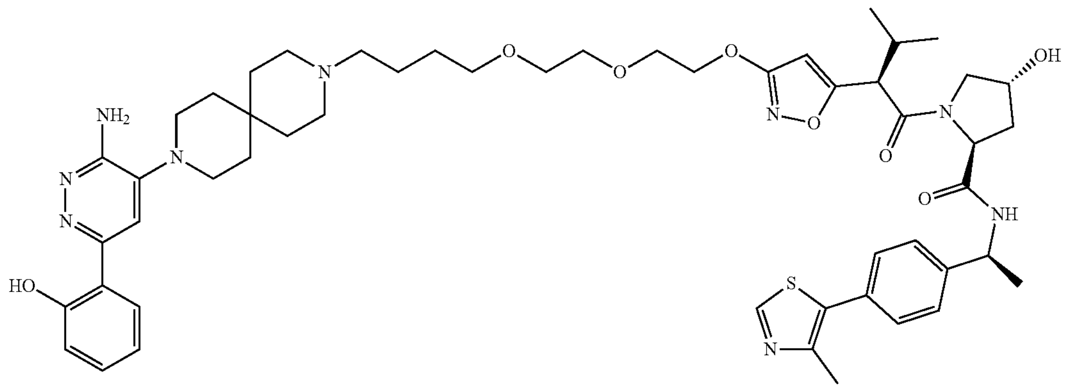

-continued
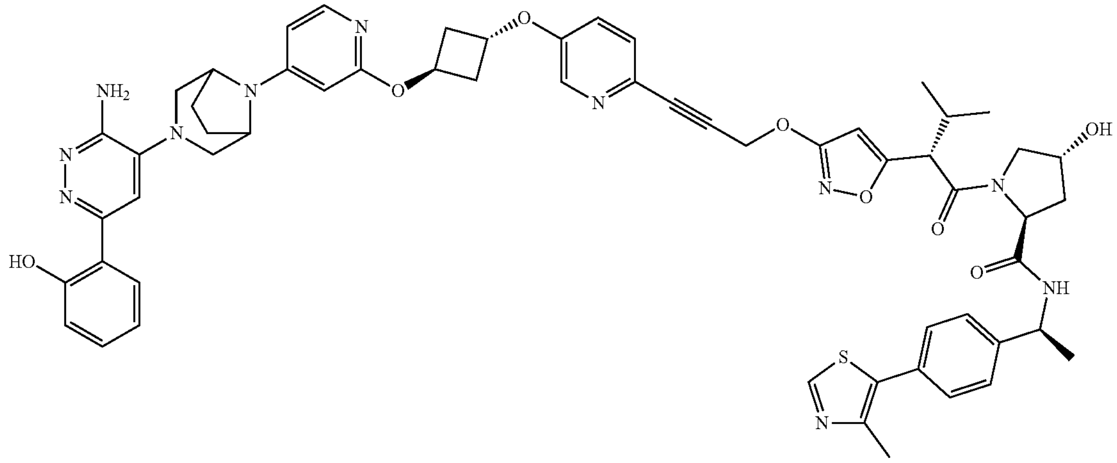
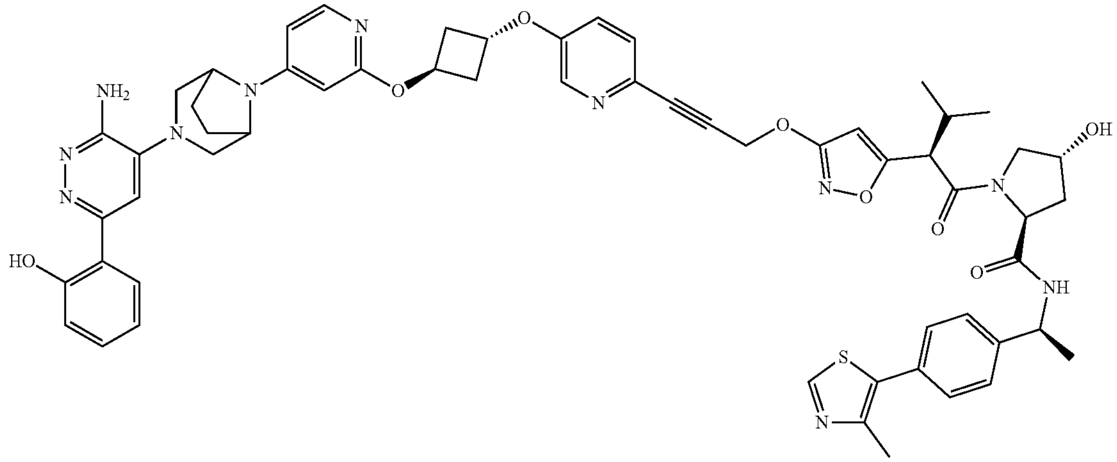
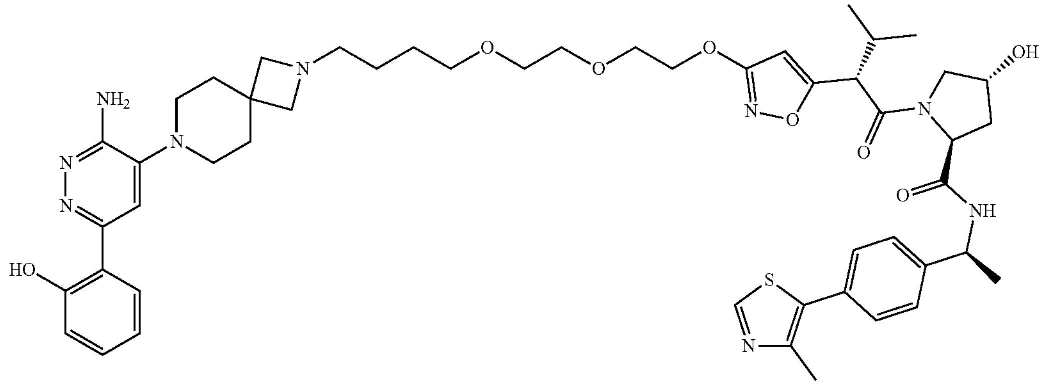
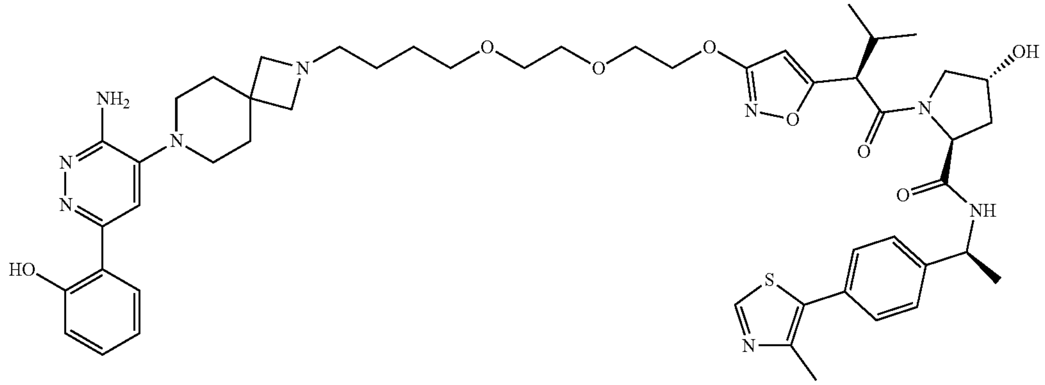

-continued
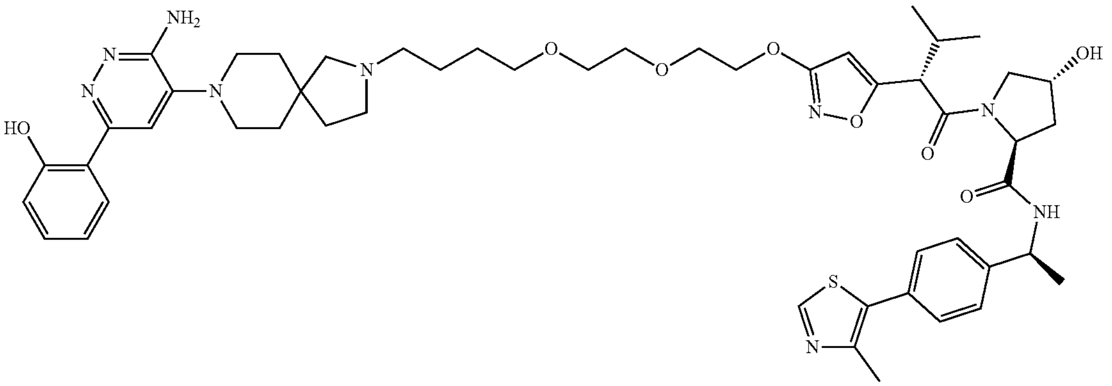
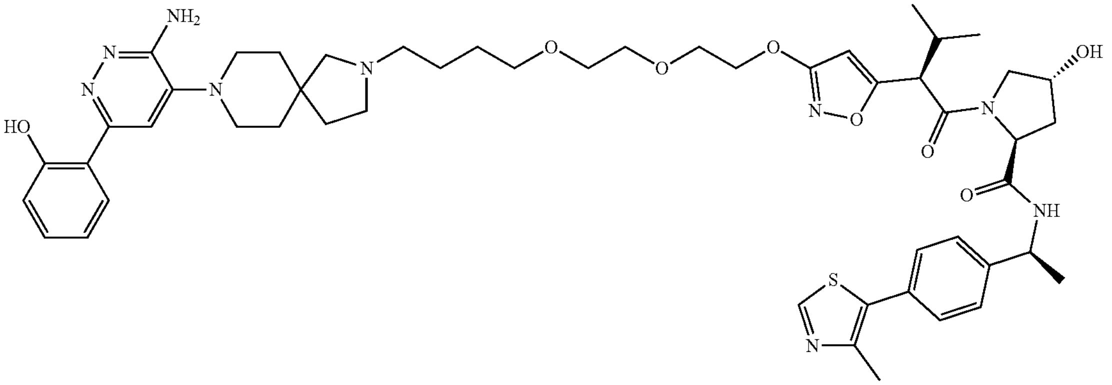
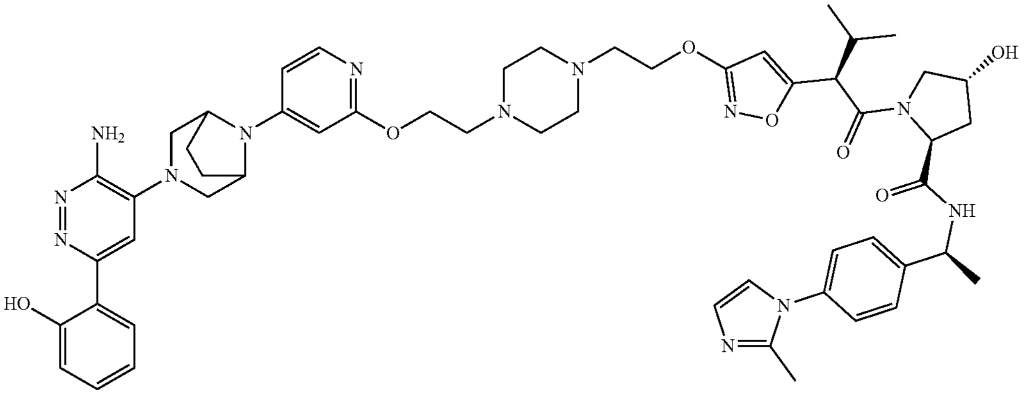
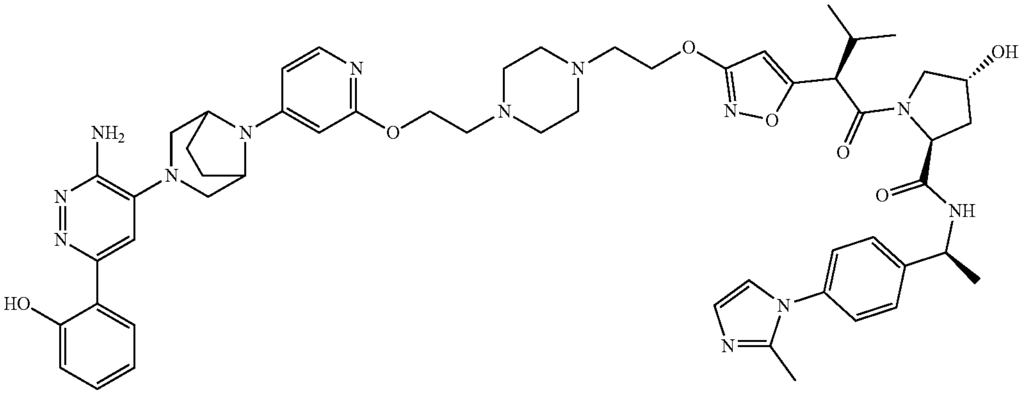

-continued
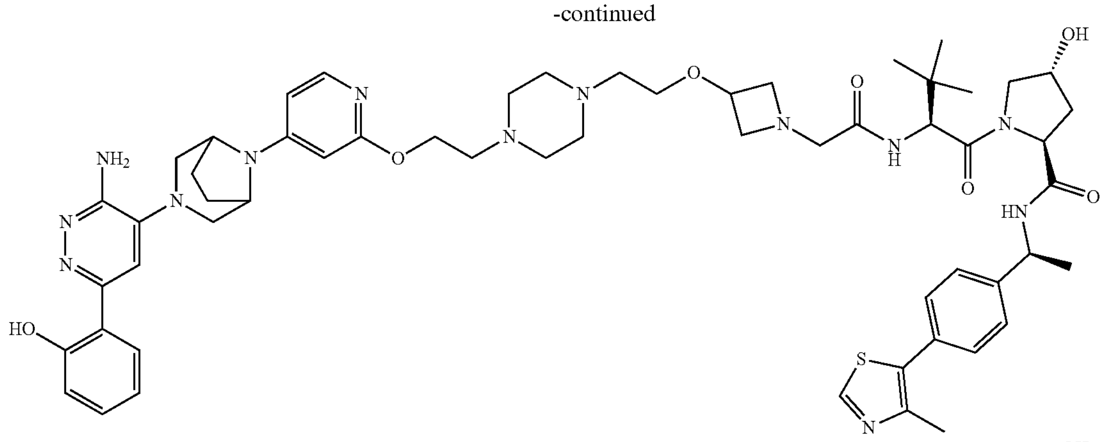
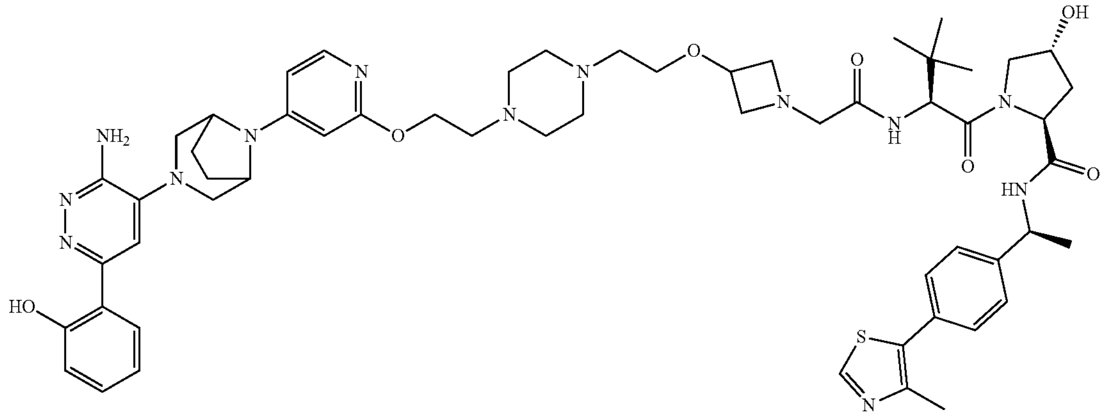
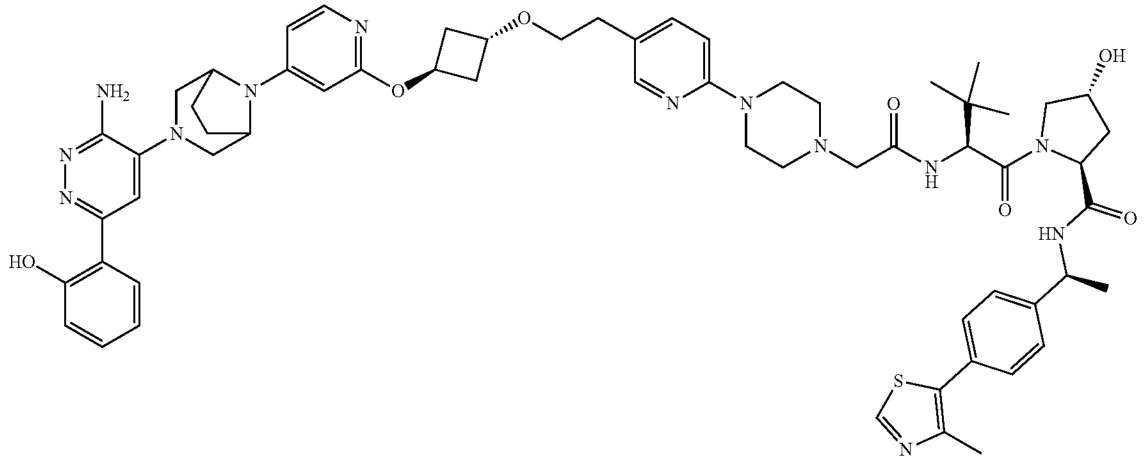
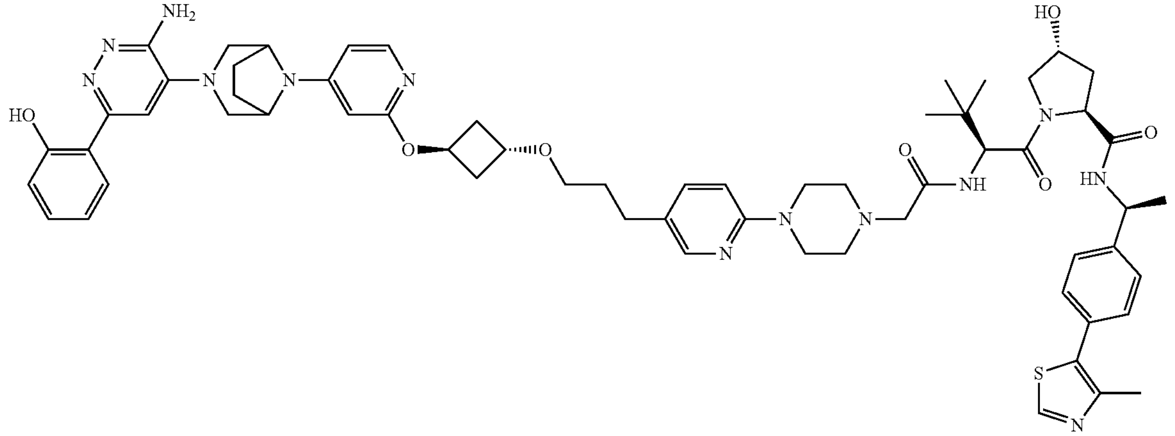

-continued
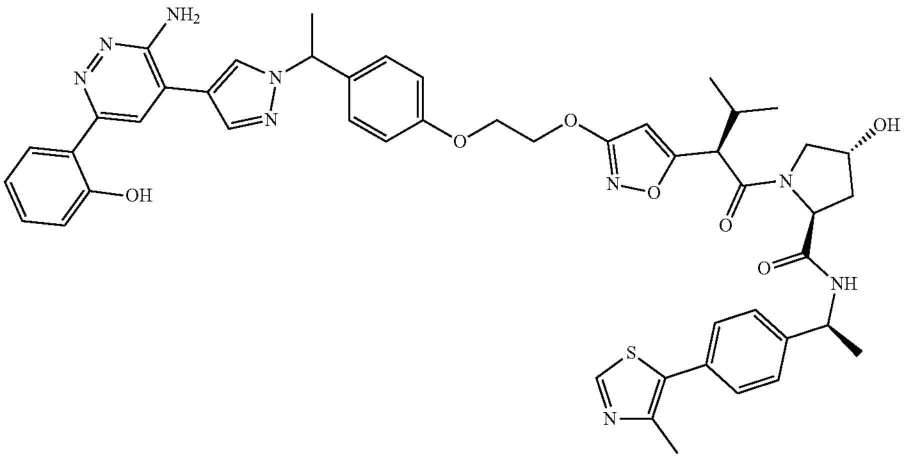
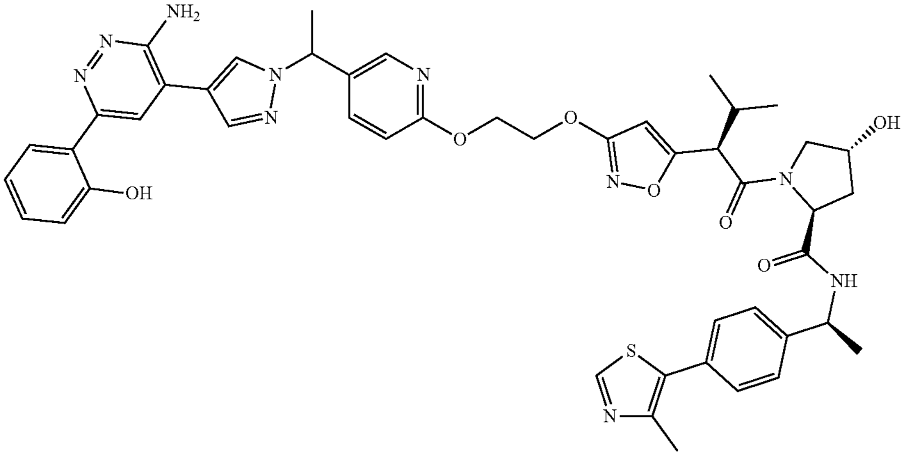
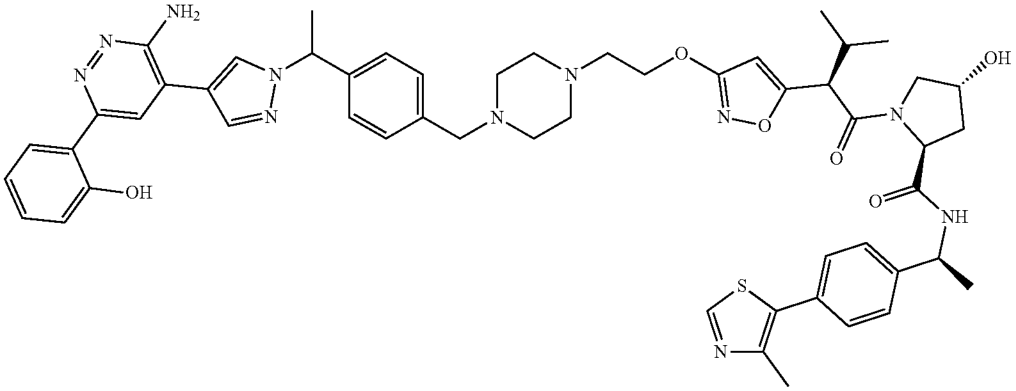
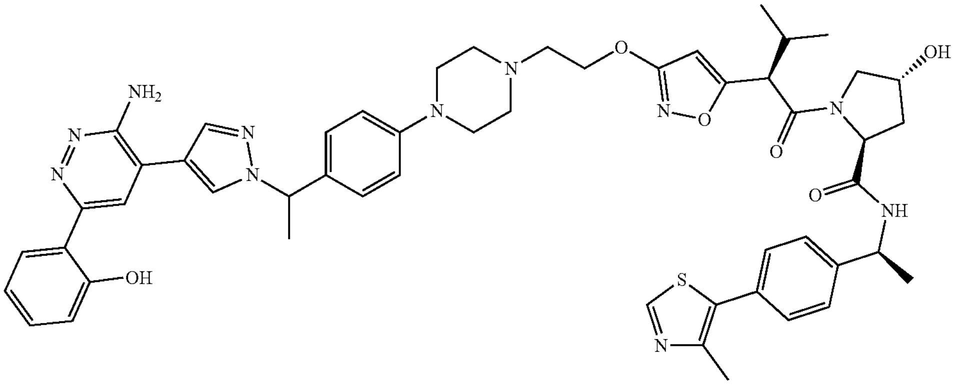

-continued
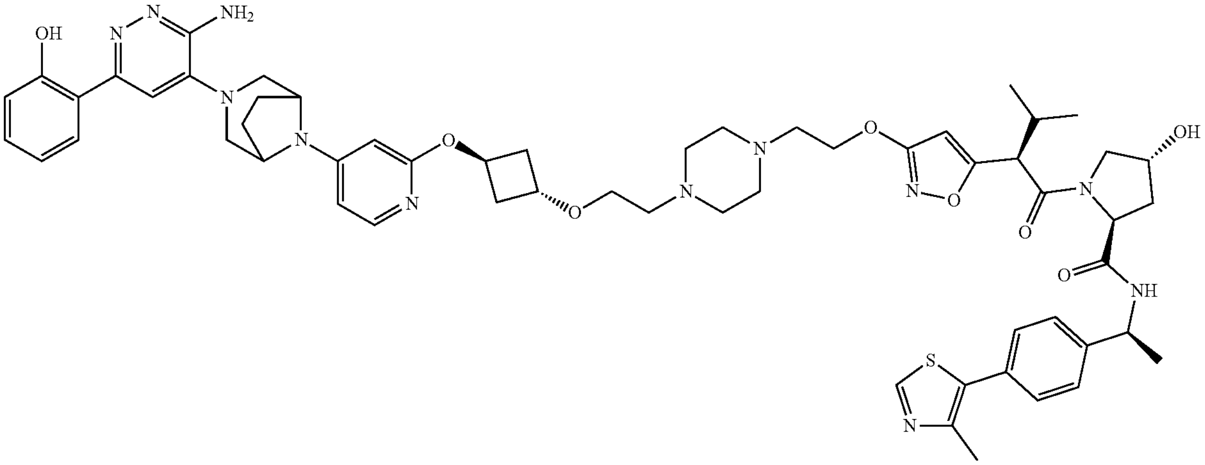
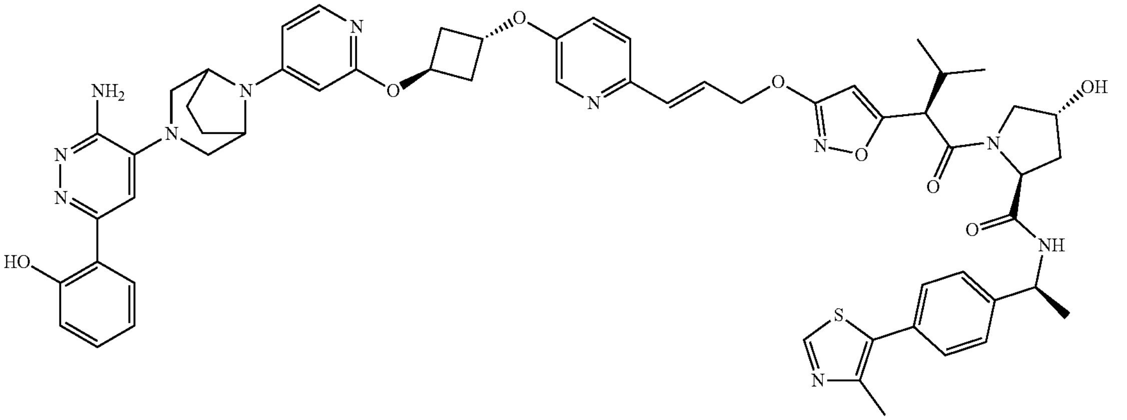
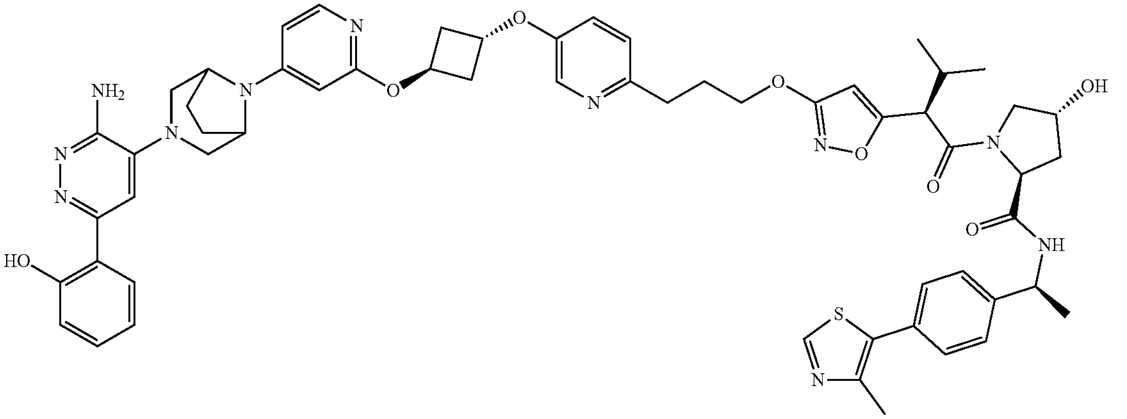
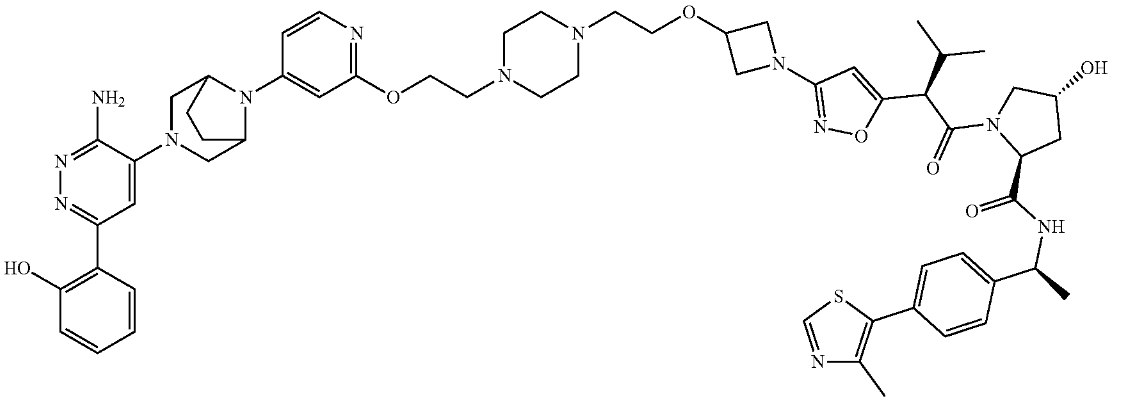

-continued
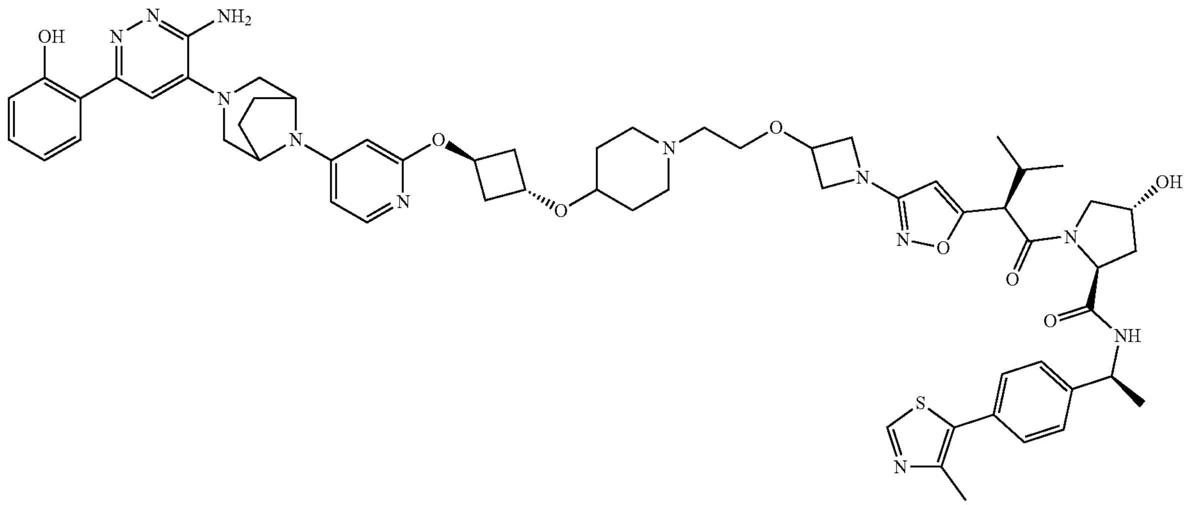
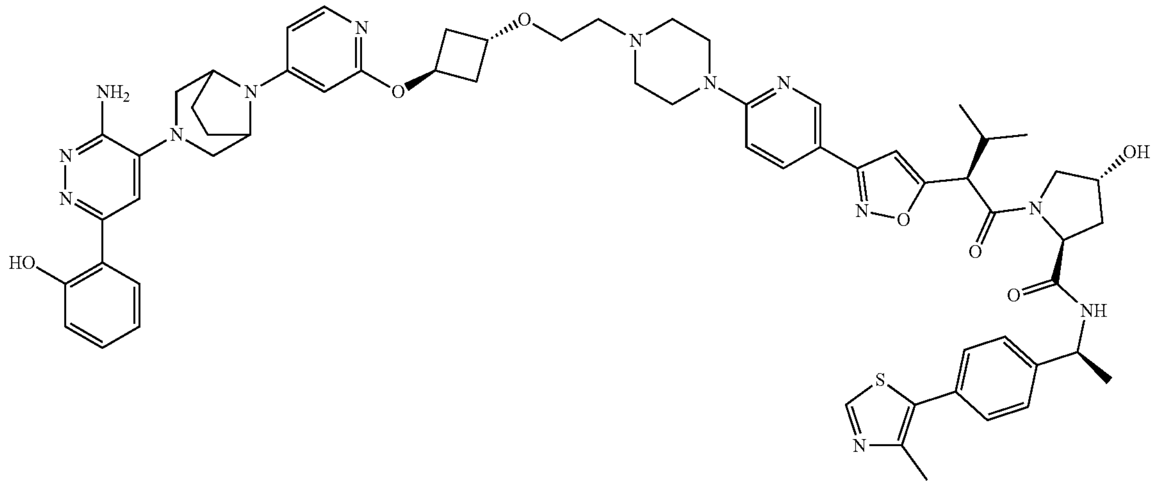
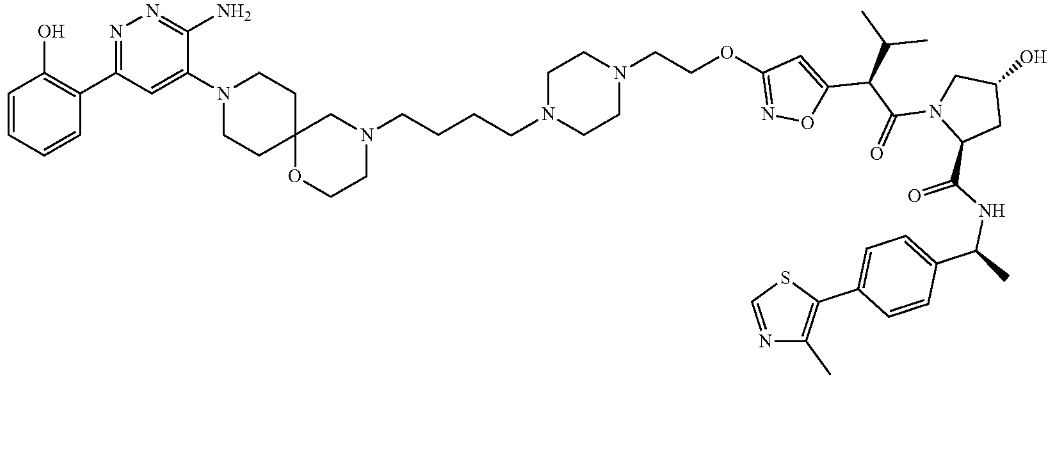

-continued
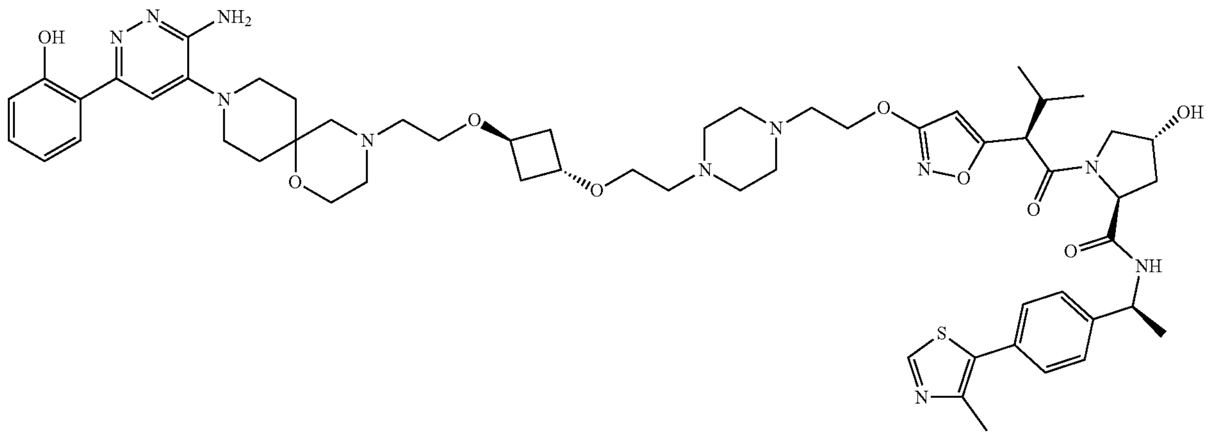
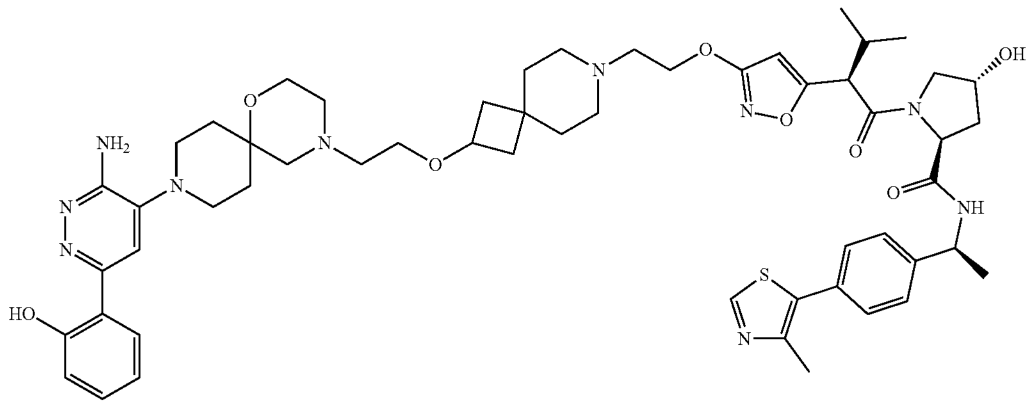
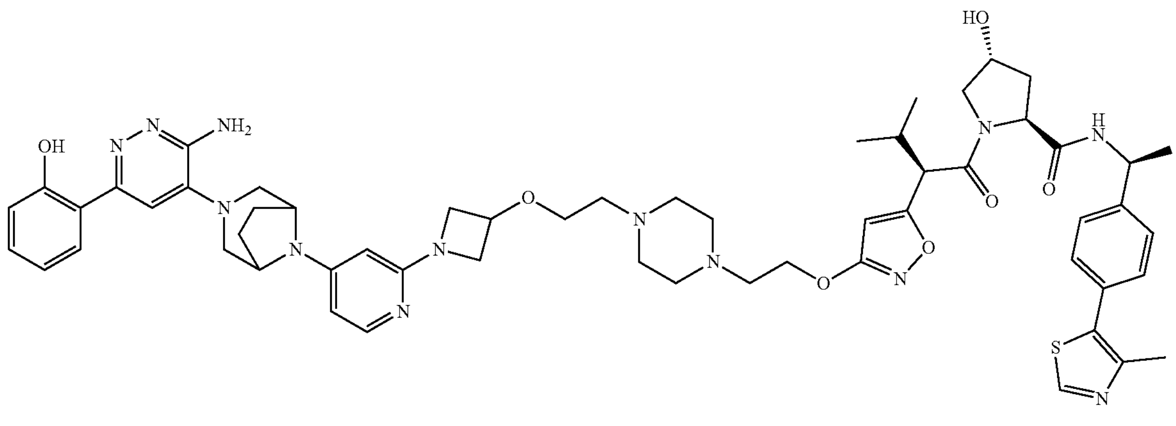

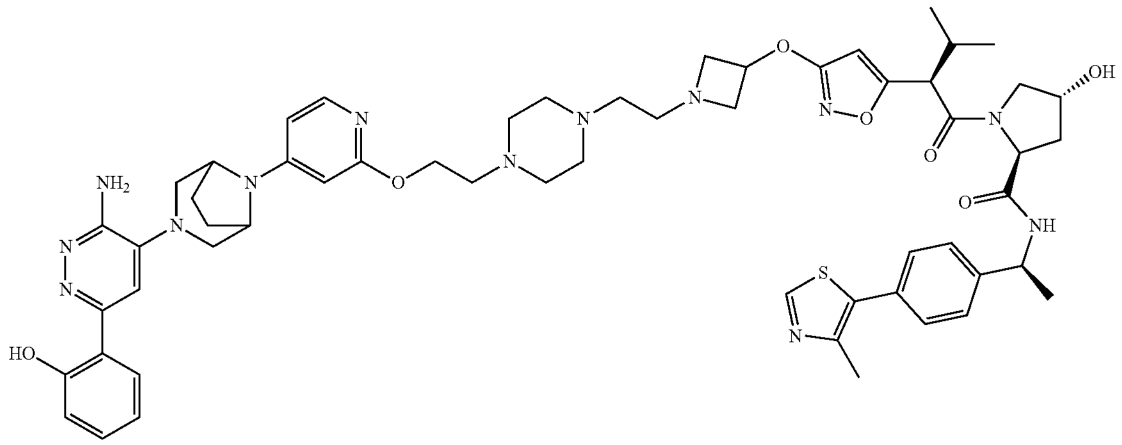
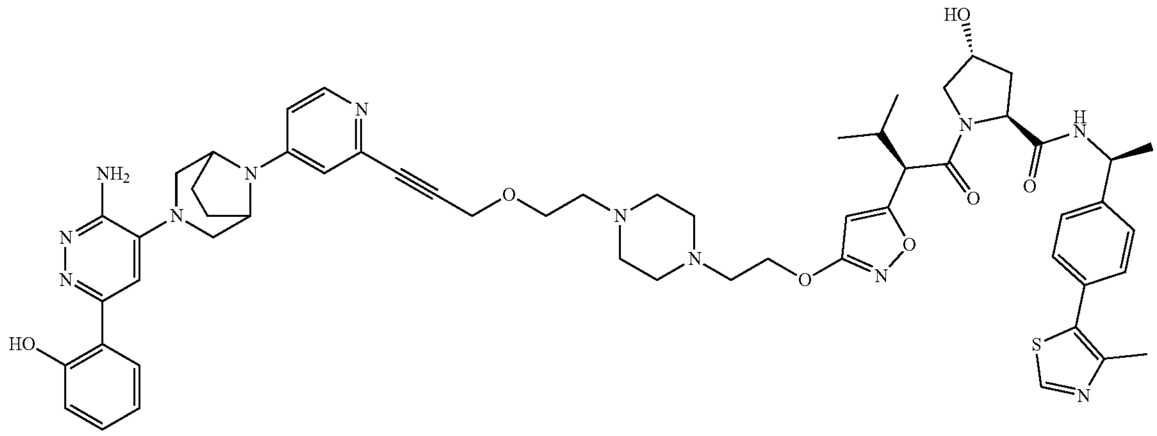
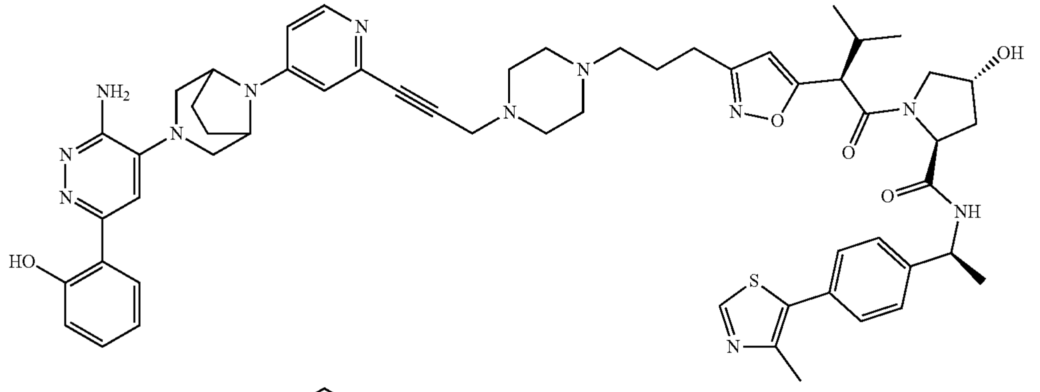
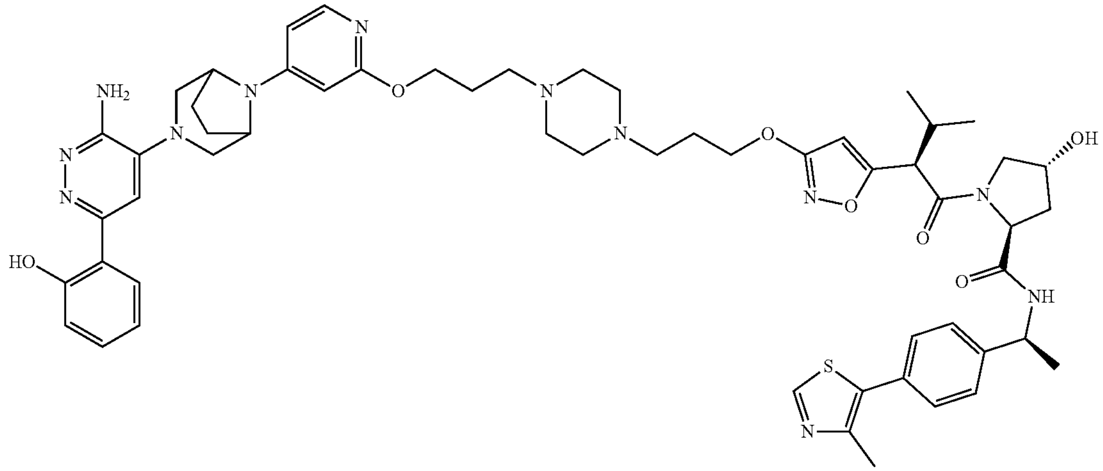

-continued
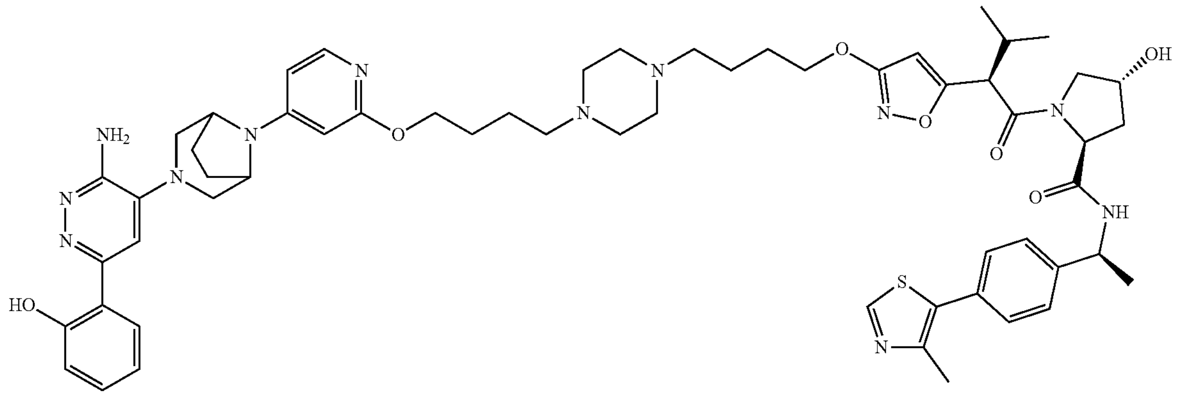
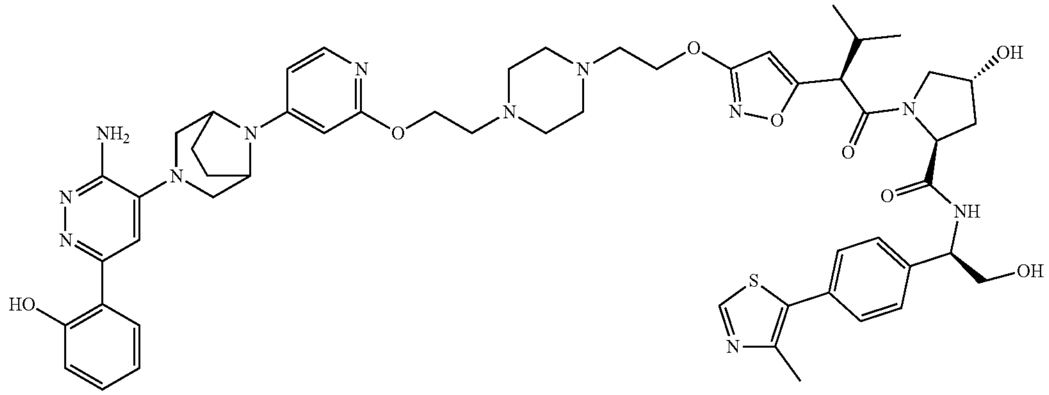
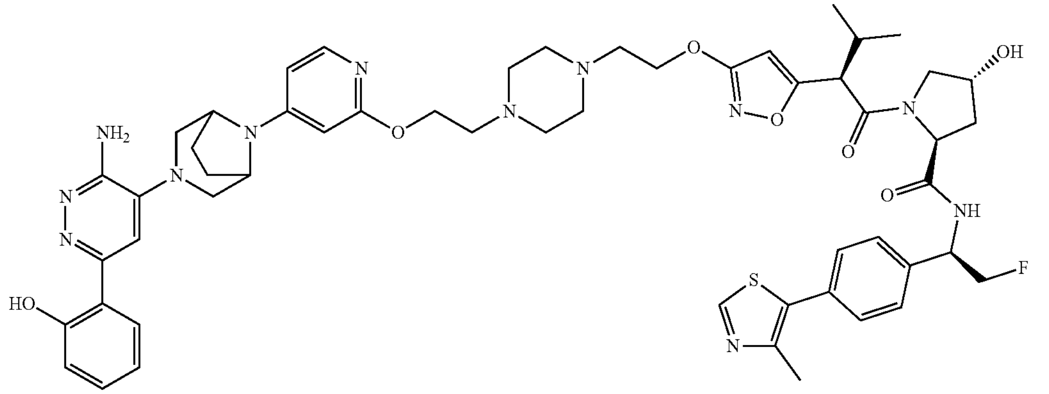
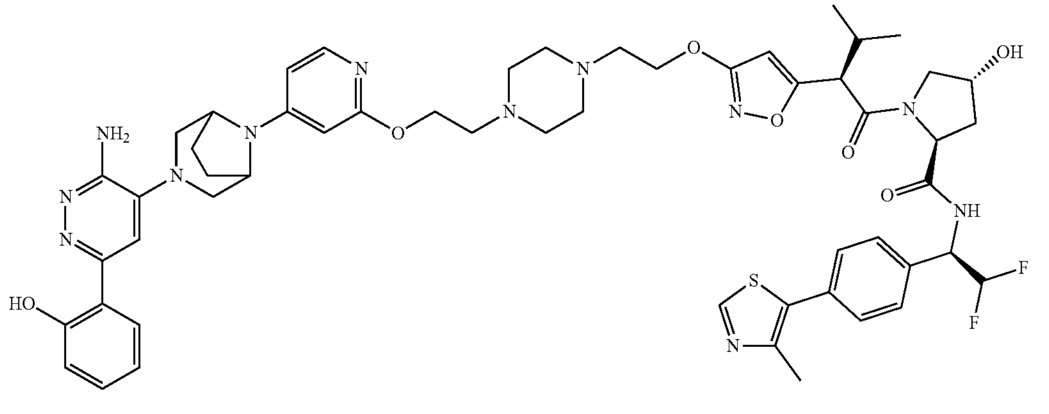

-continued
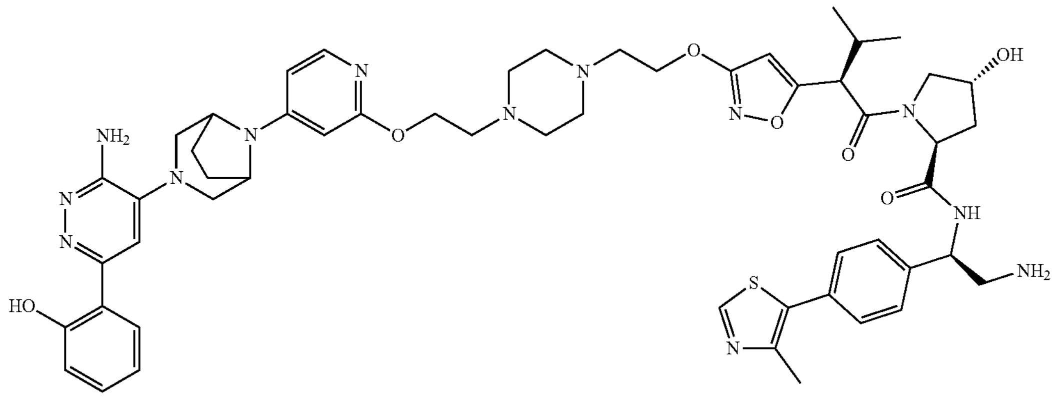
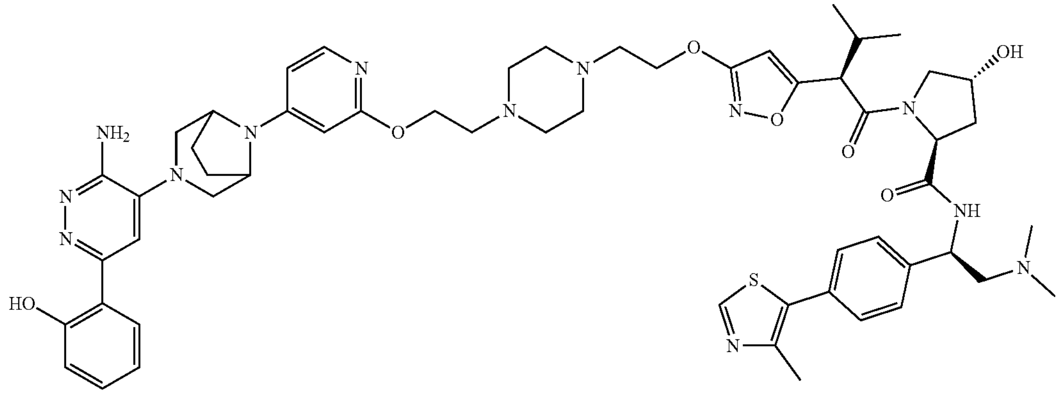
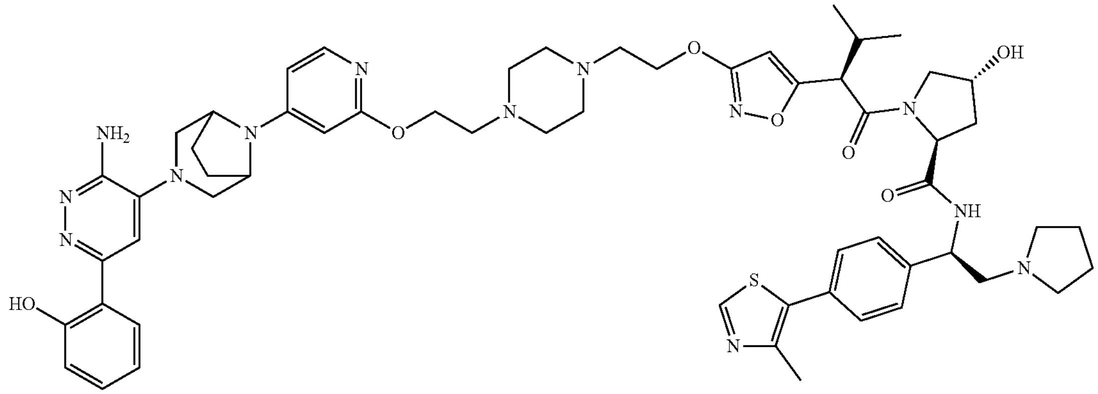
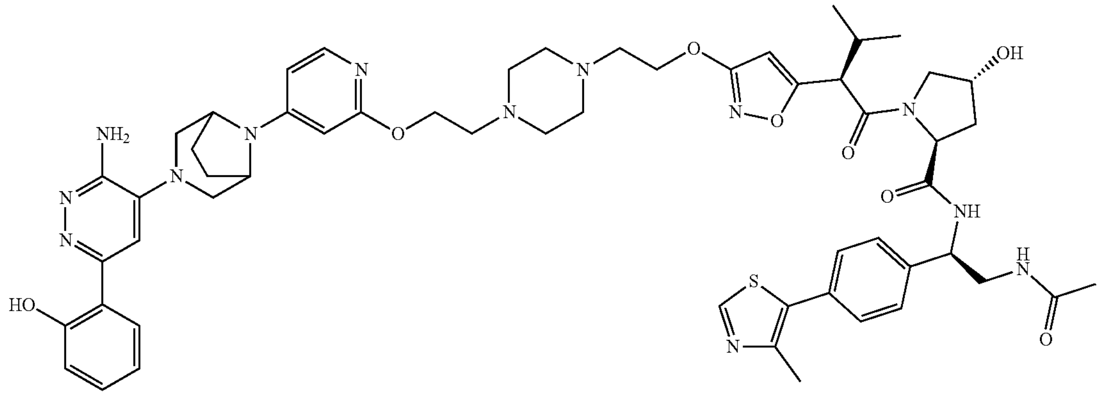

-continued
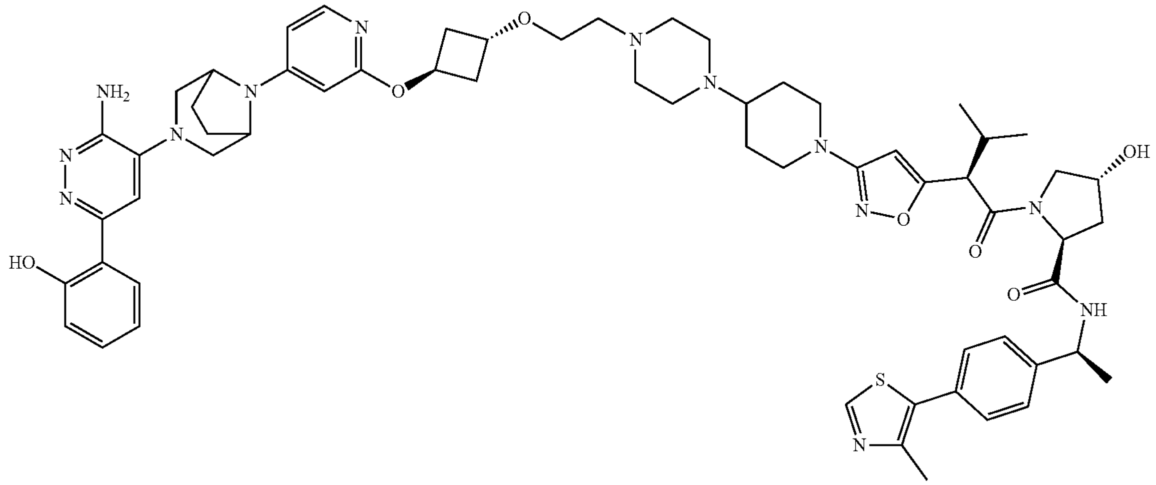
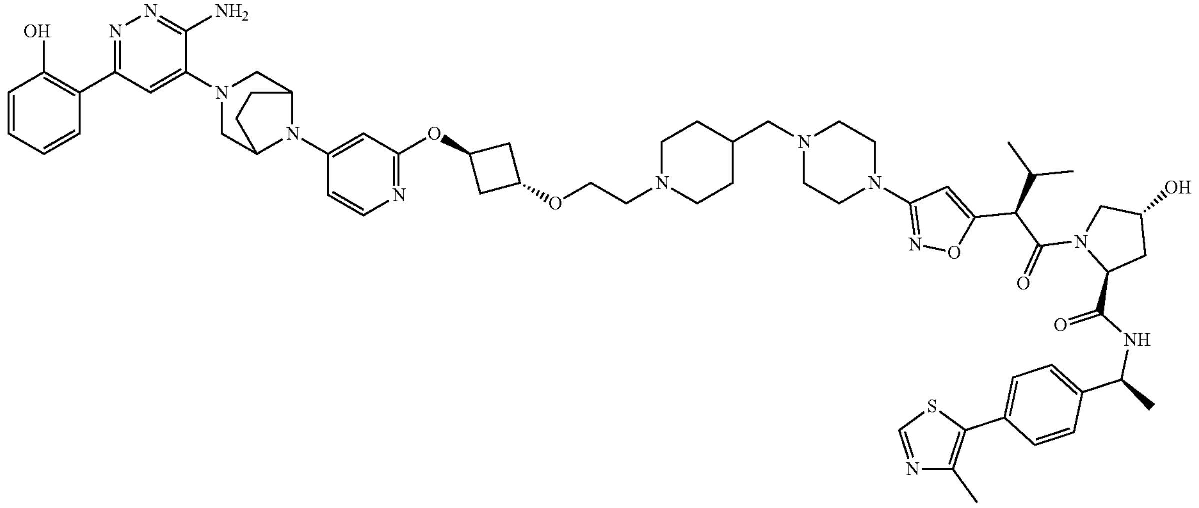
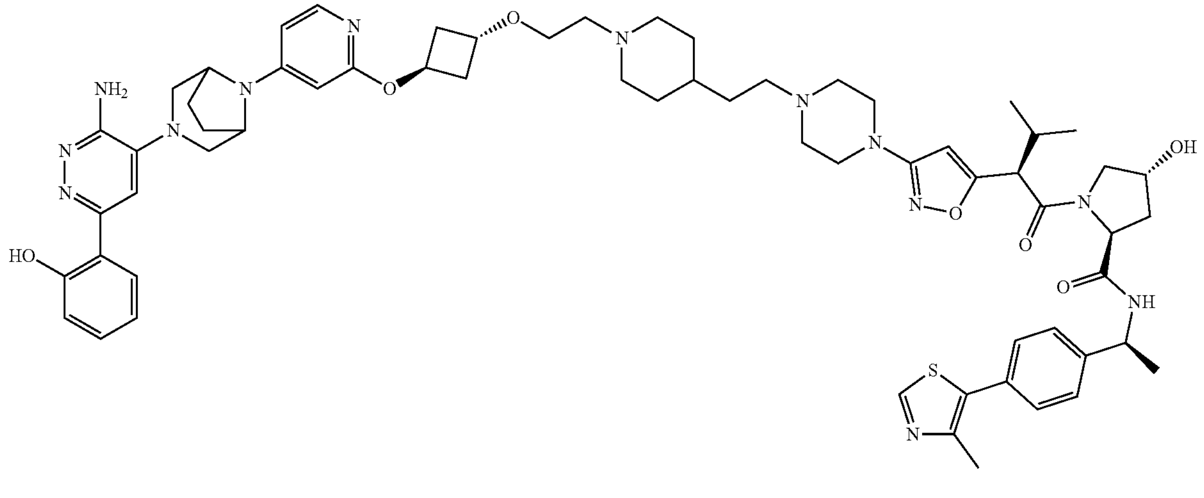

-continued
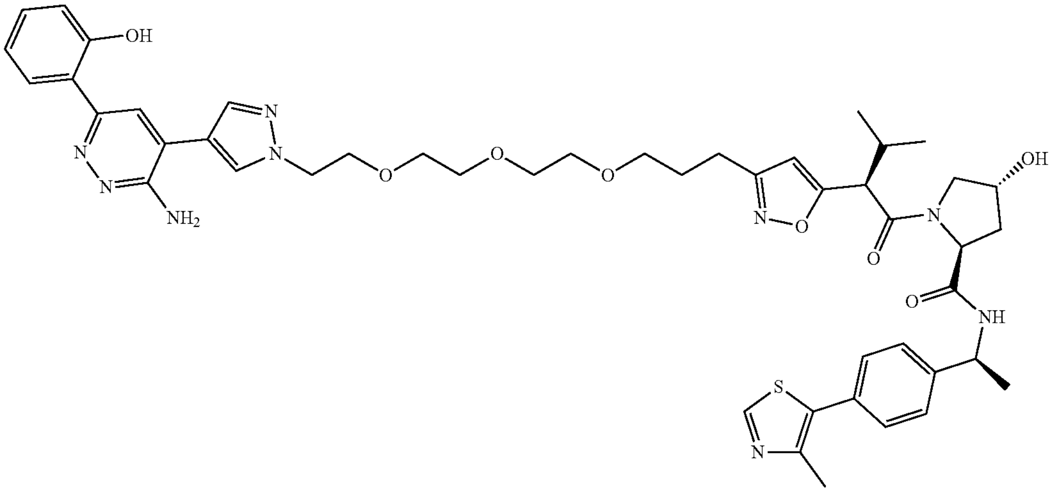
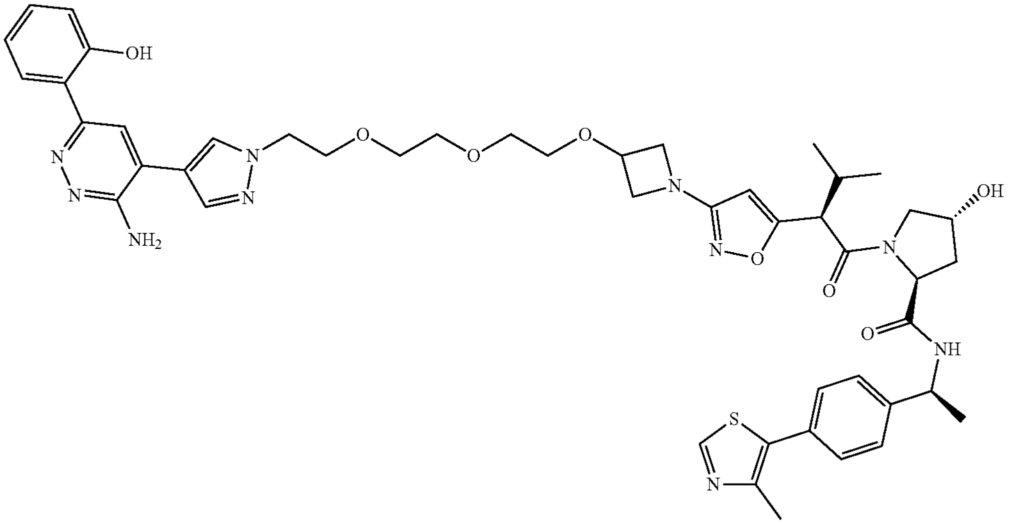
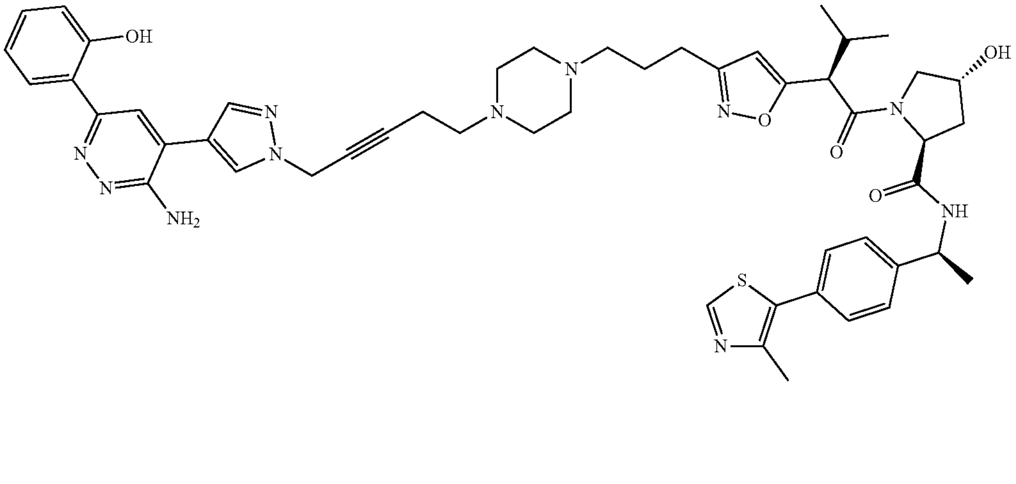

-continued
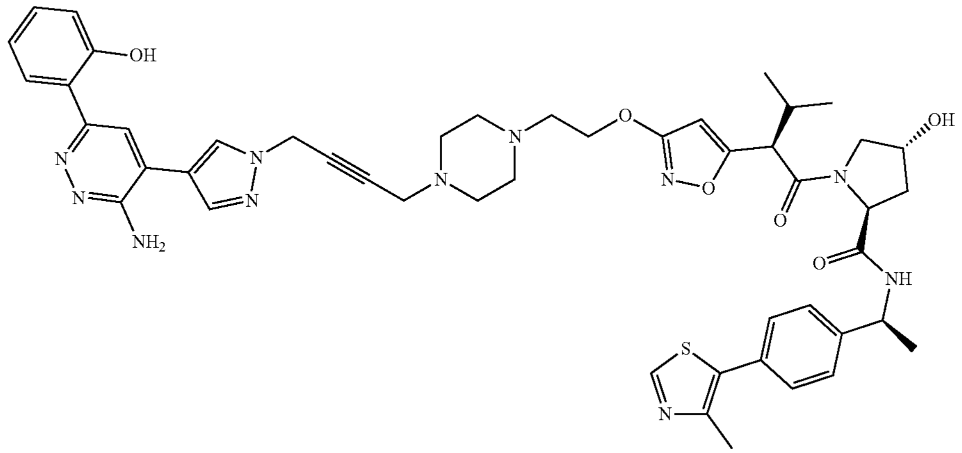
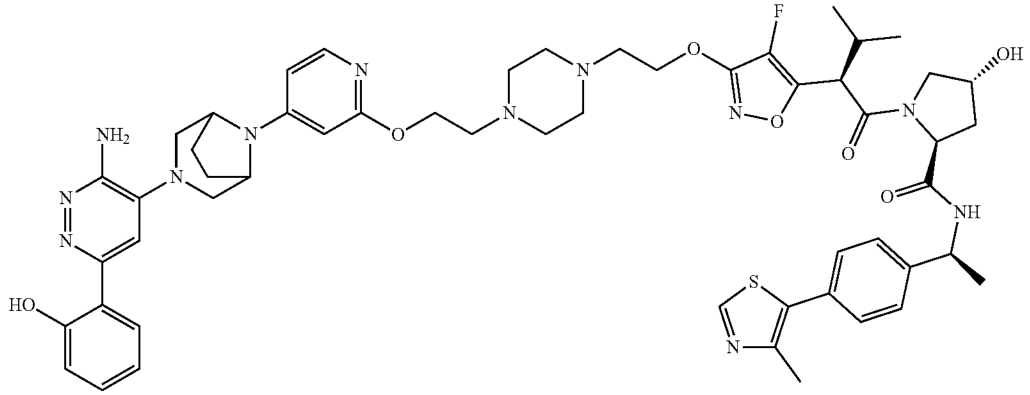
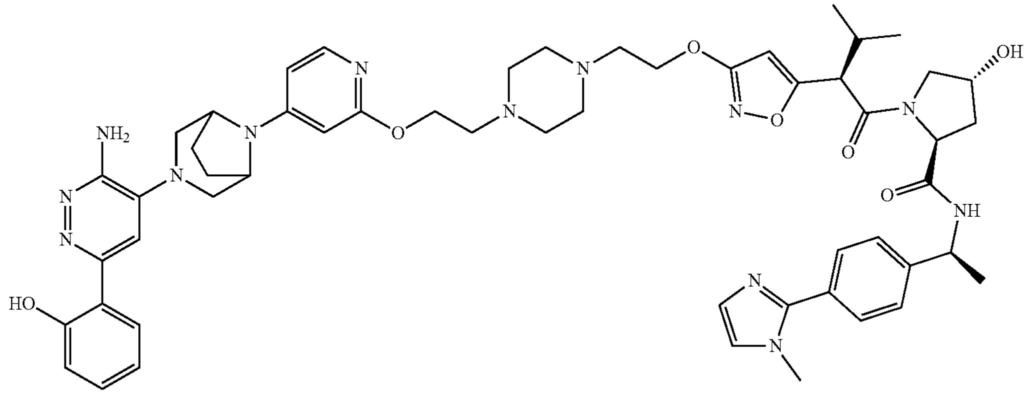
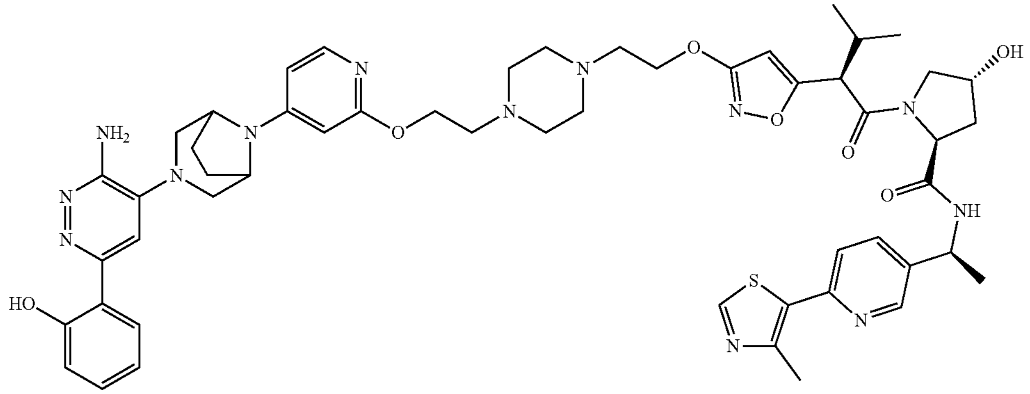

-continued
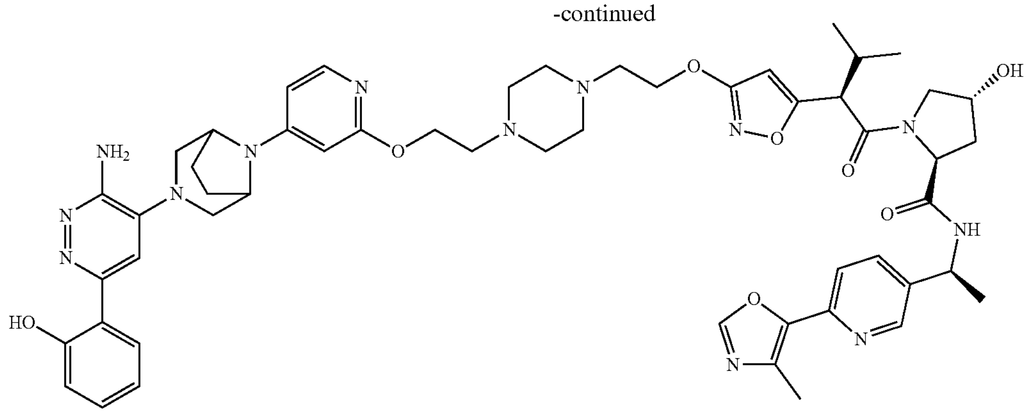
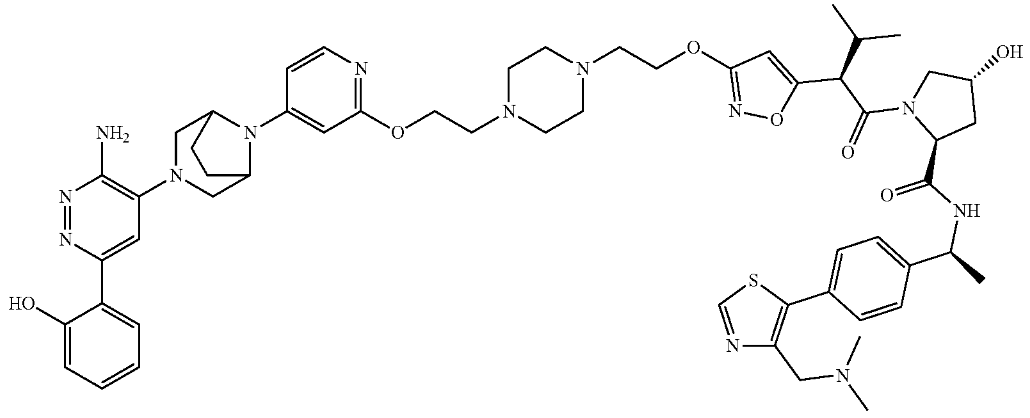 [SMILES: CC(C)[C@@H](C(=O)N1C[C@H](O)C[C@H]1C(=O)N[C@@H](C)c1ccc(-c2scnc2CN(C)C)cc1)c1cc(OCCN2CCN(CCOc3cc(N4C5CCC4CN(c4cc(-c6ccccc6O)nnc4N)C5)ccn3)CC2)no1]
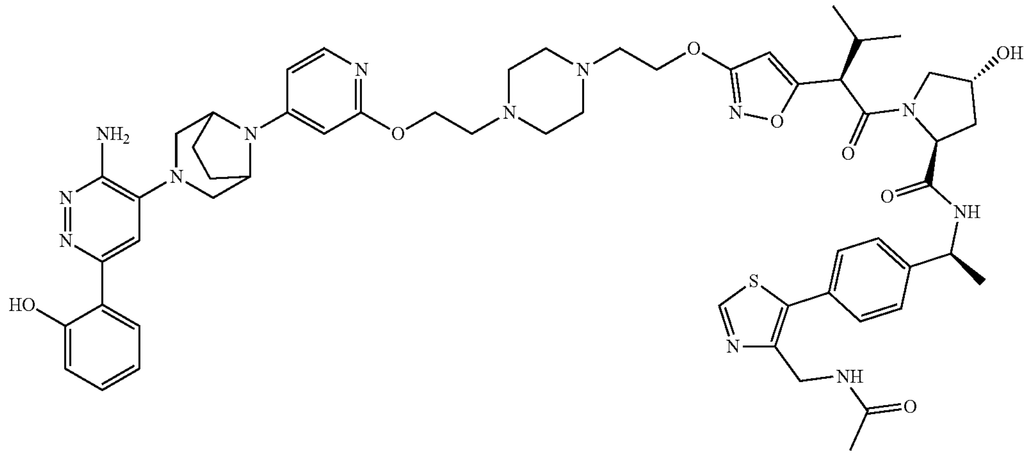

-continued
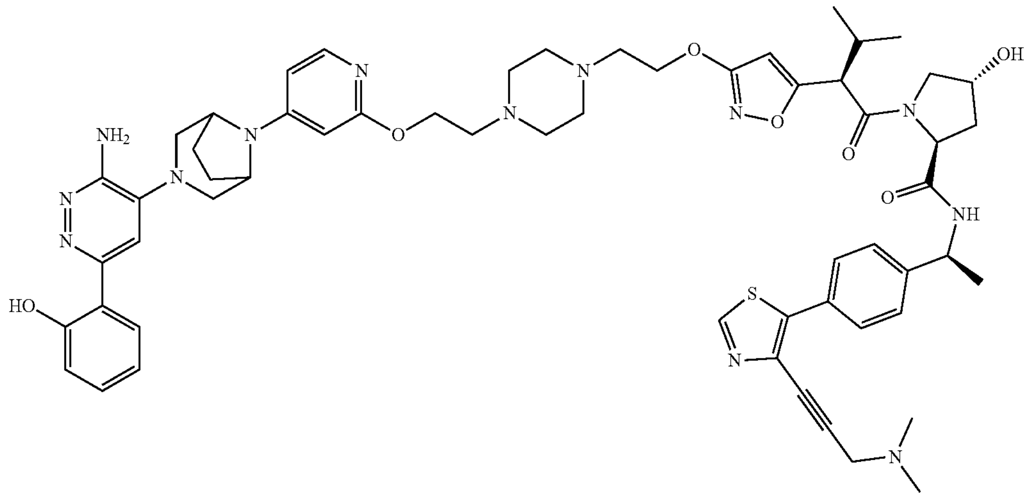
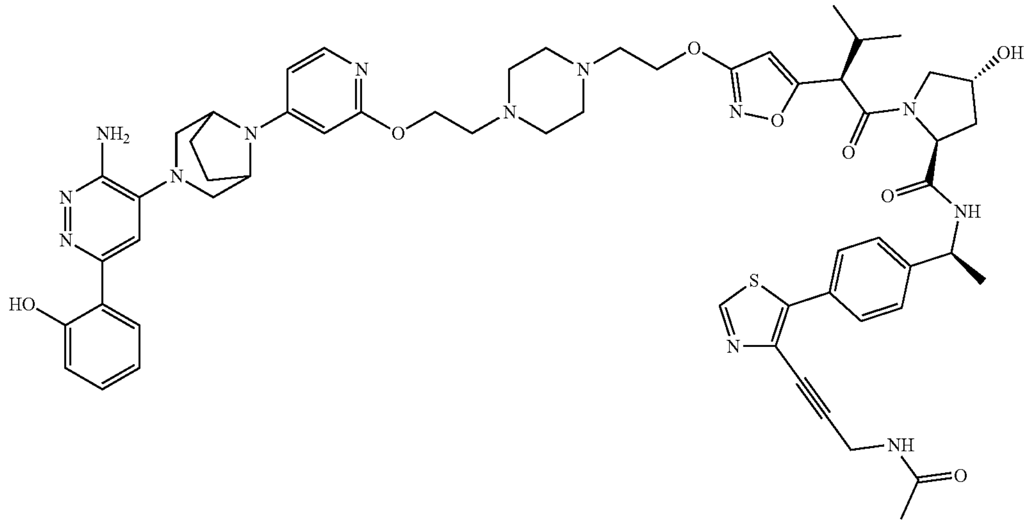
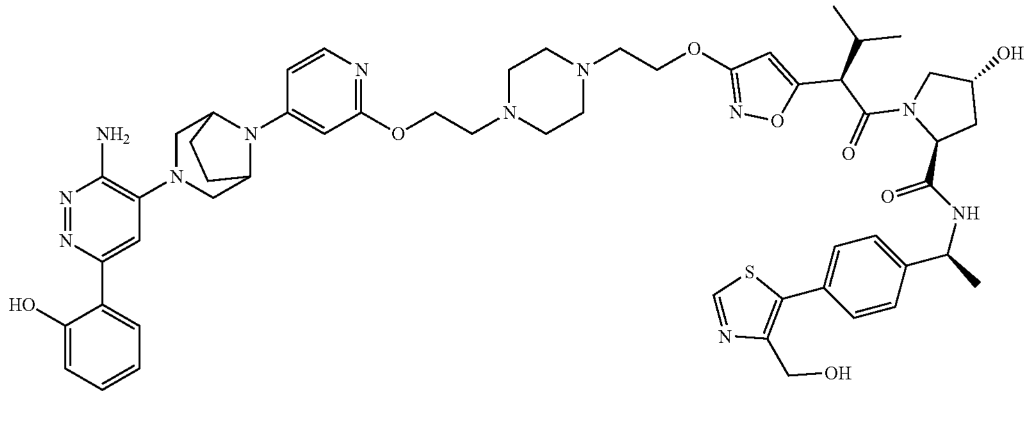

-continued
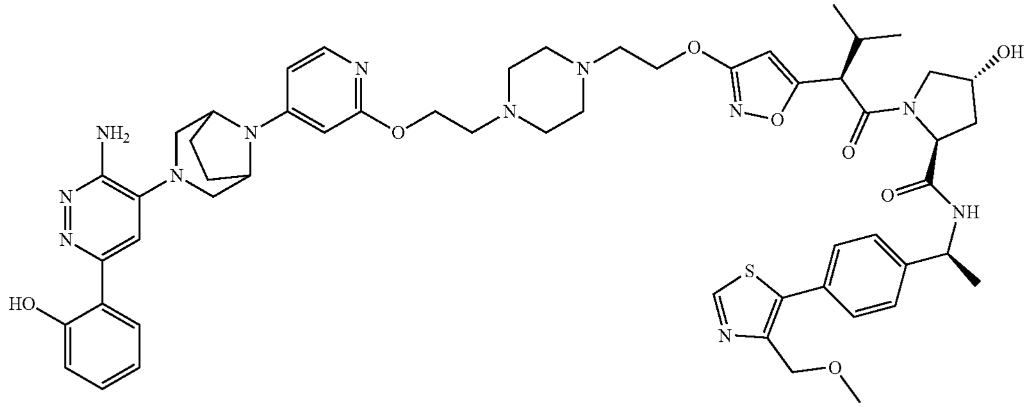
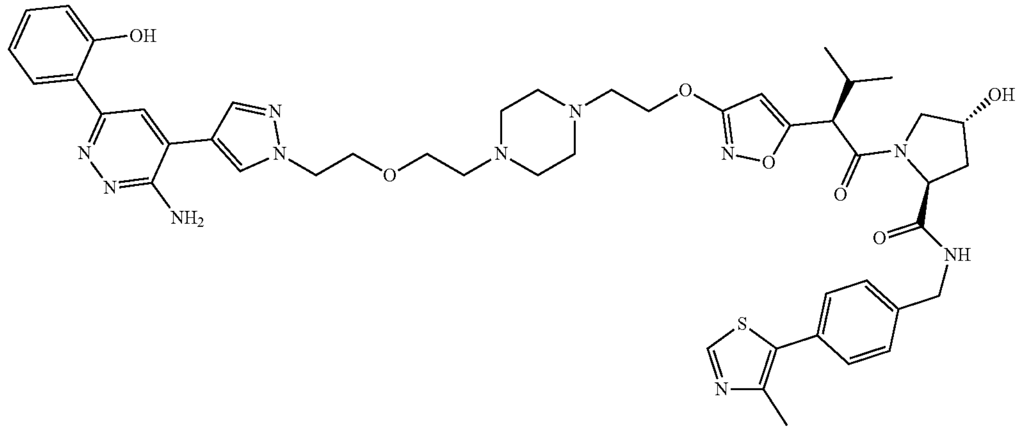
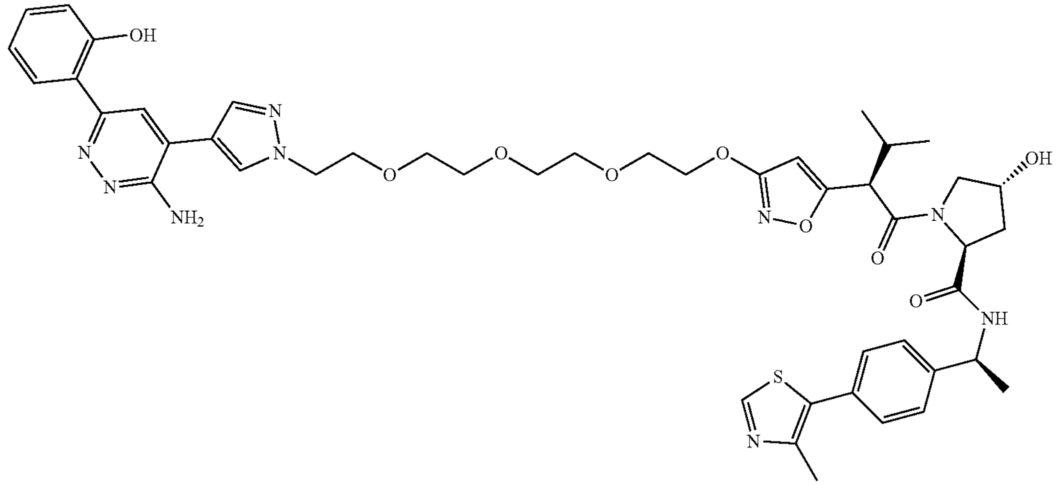
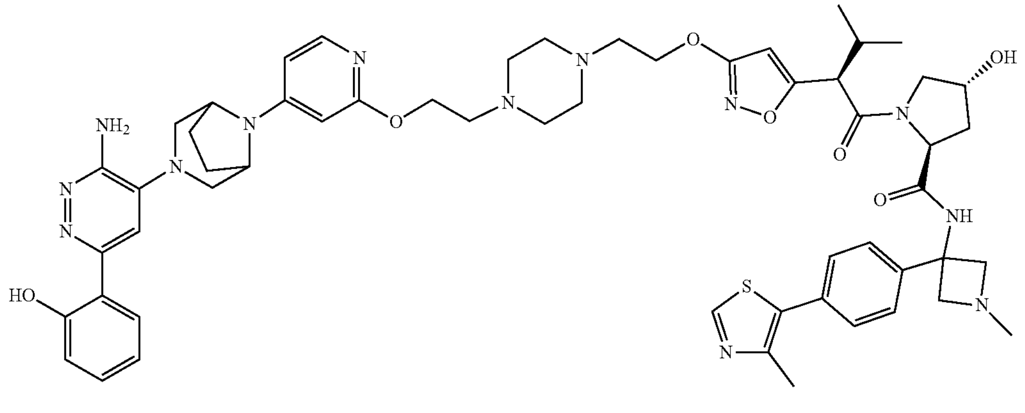

-continued
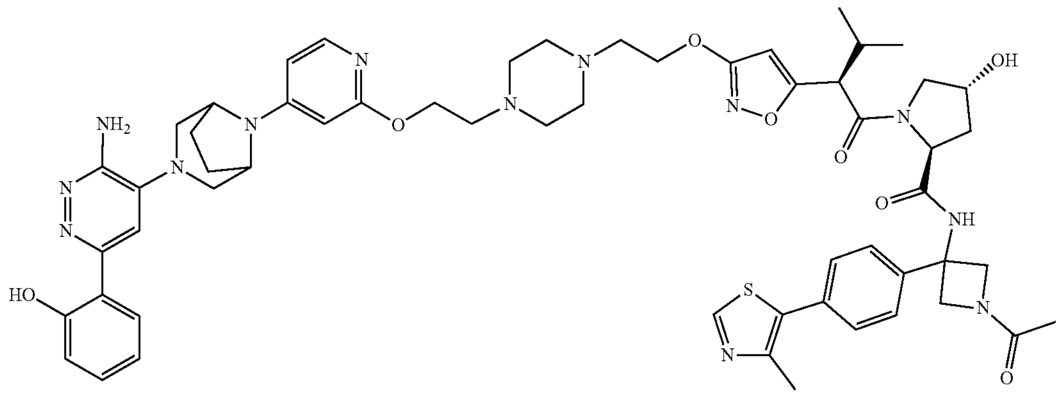
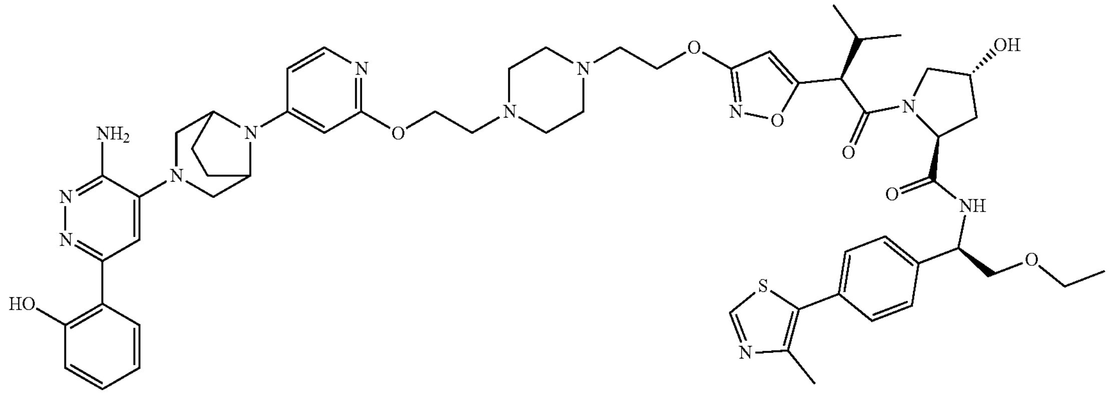
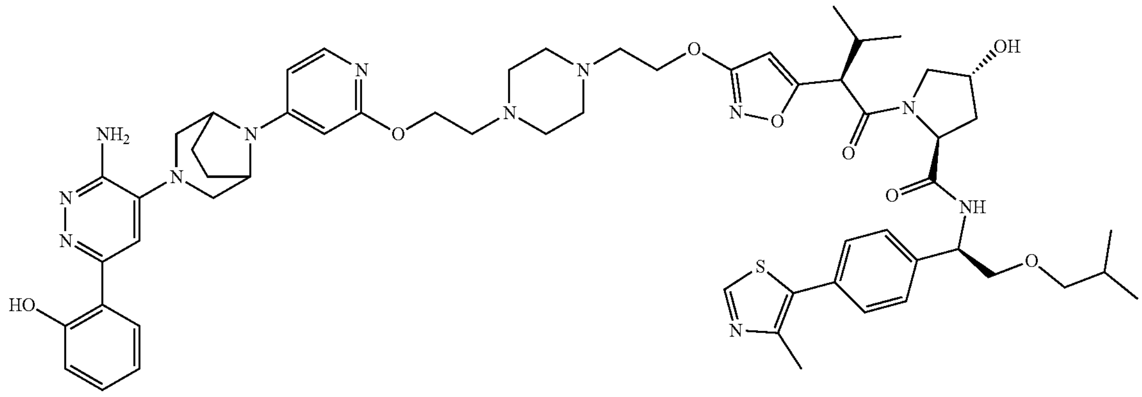
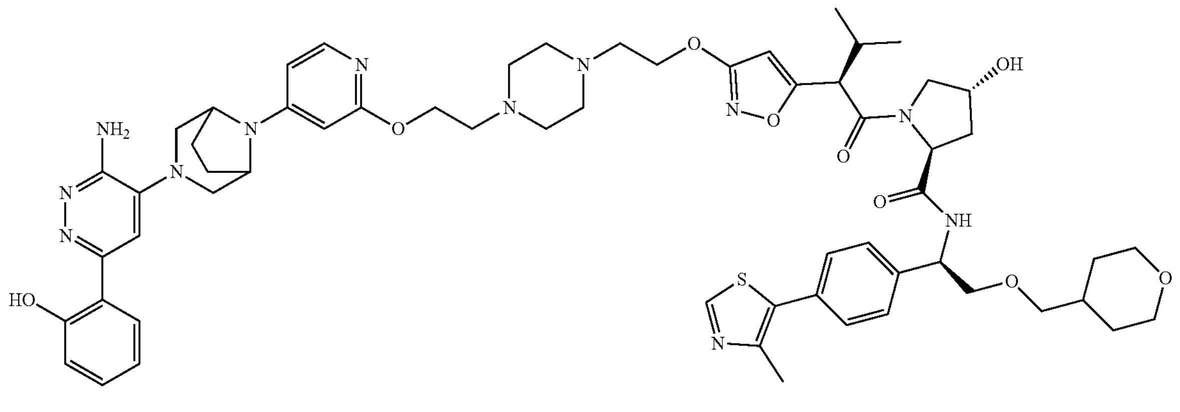

-continued
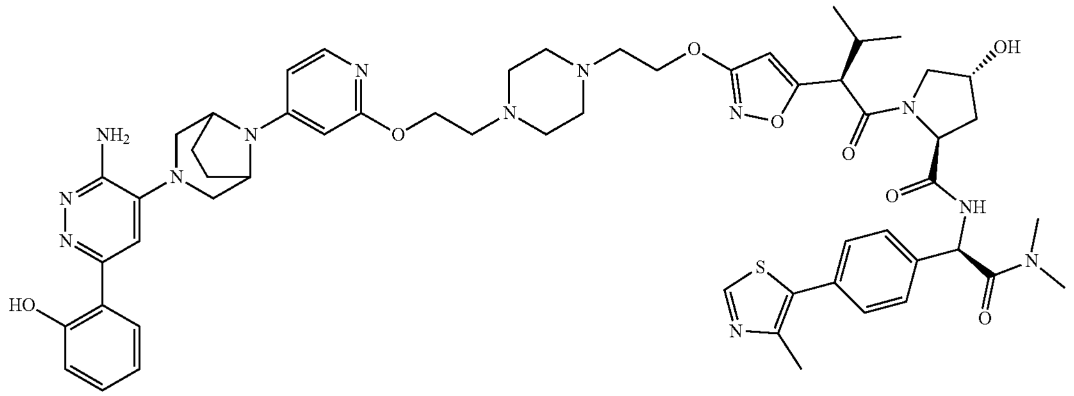
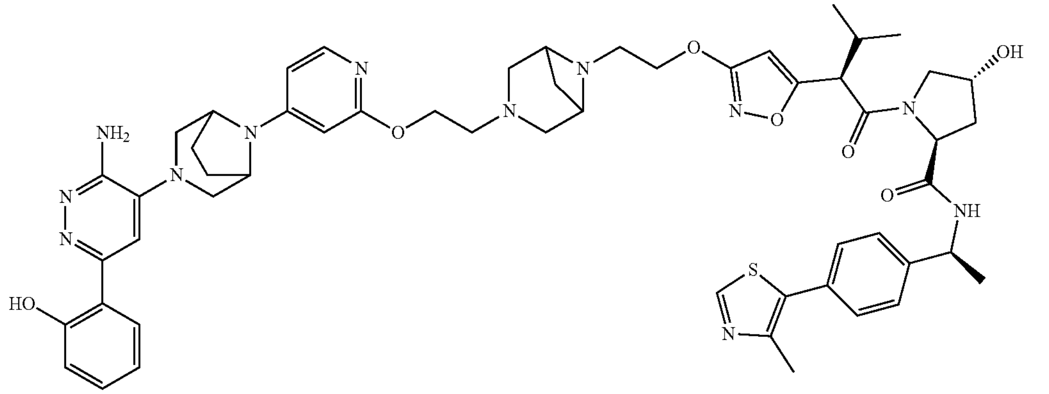
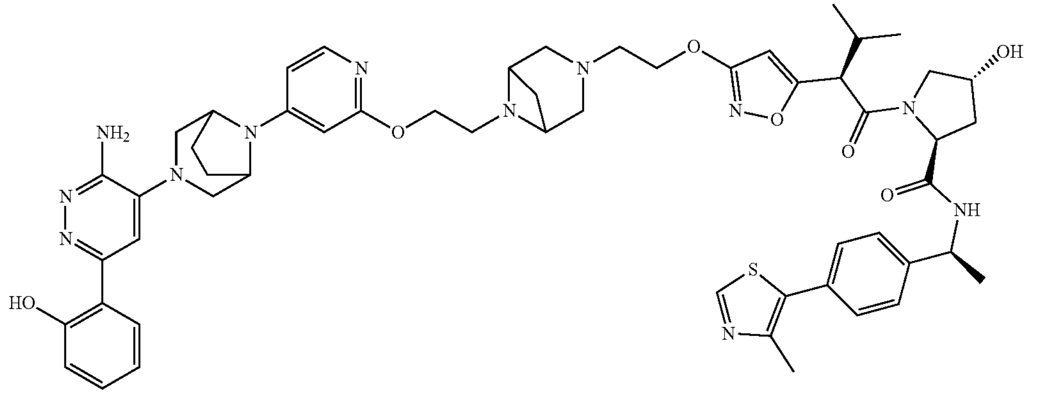
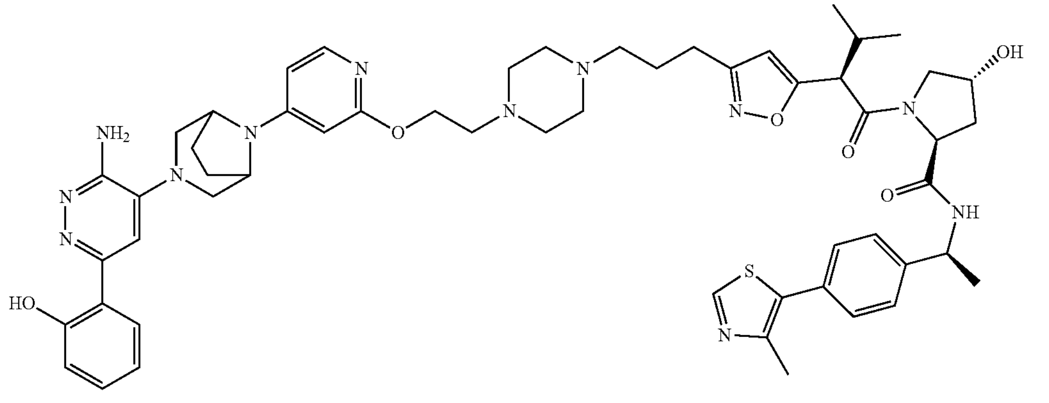

-continued
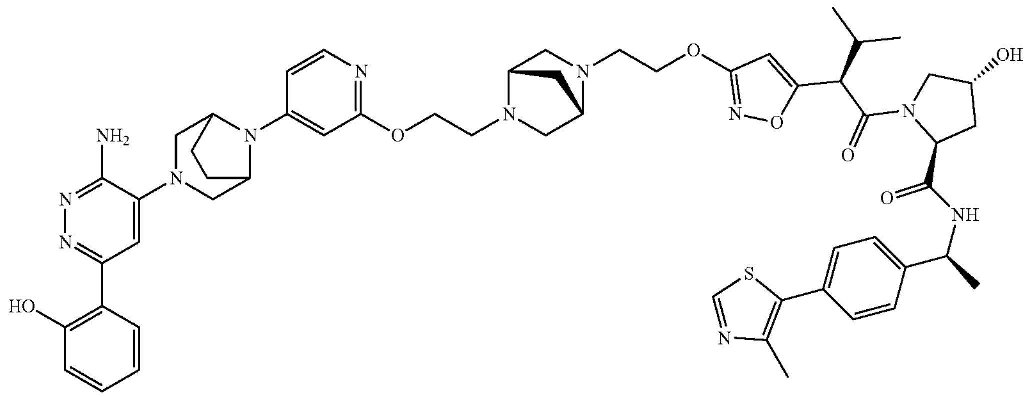
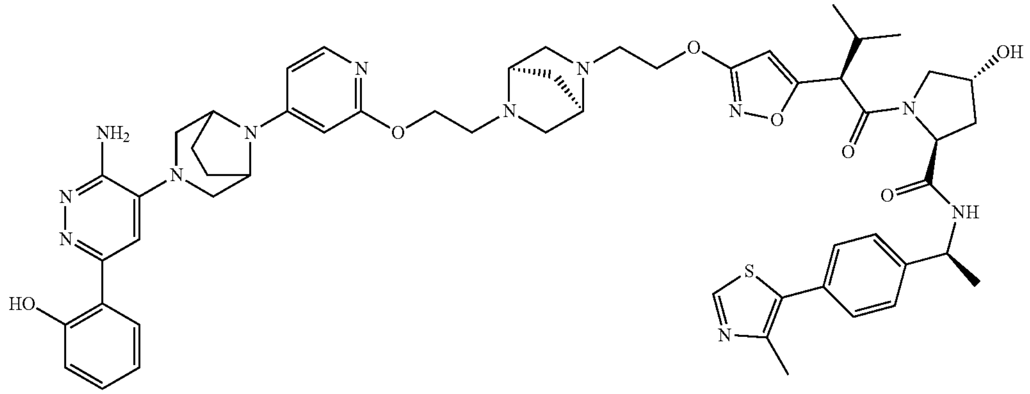
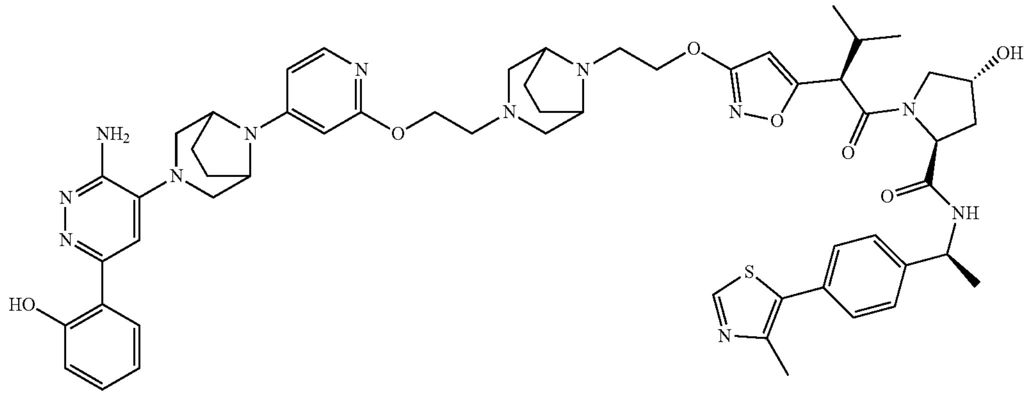
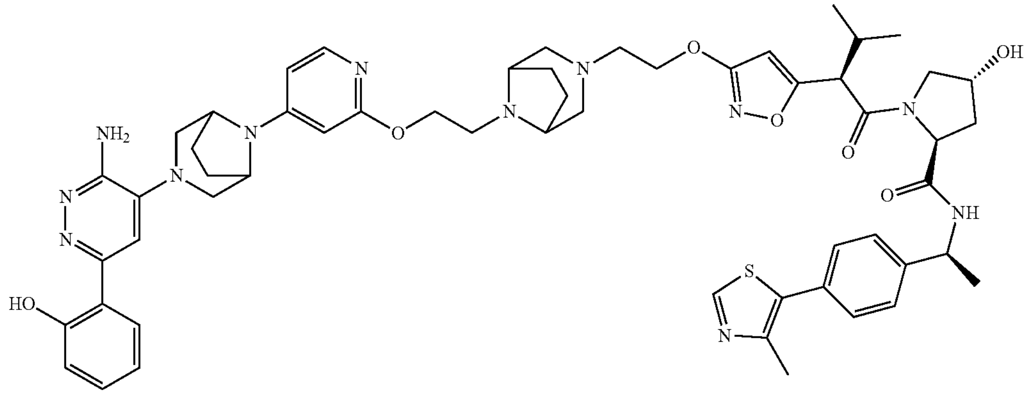

-continued
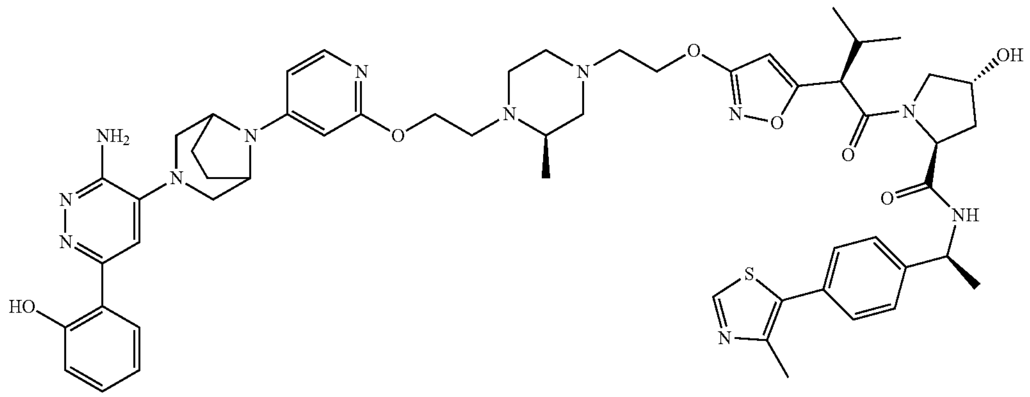
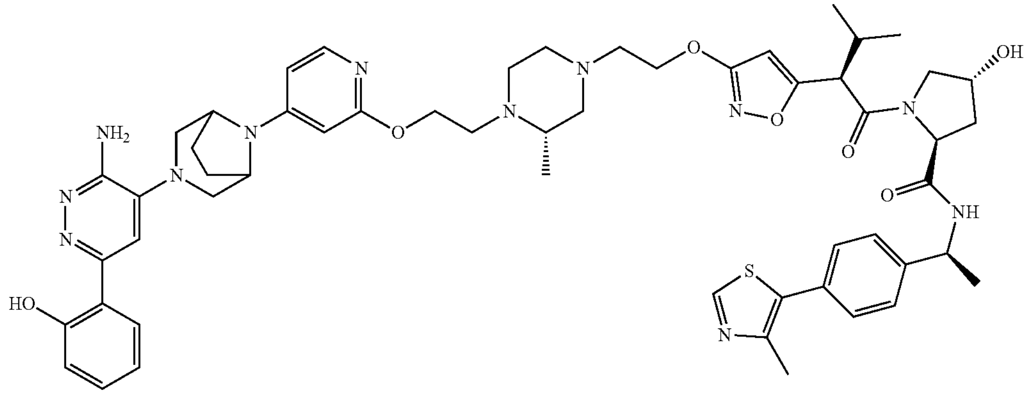
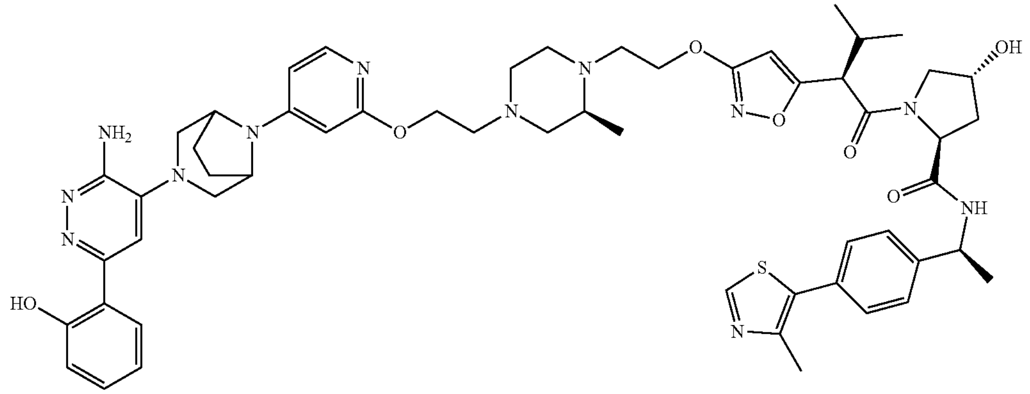
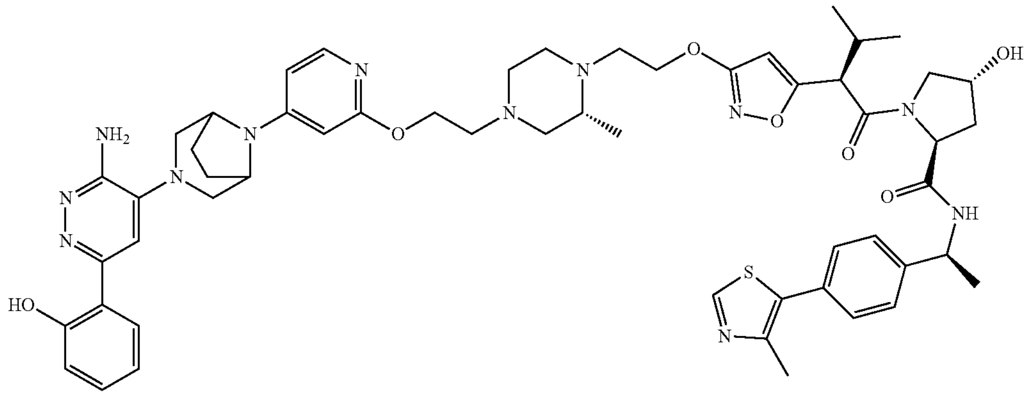

-continued
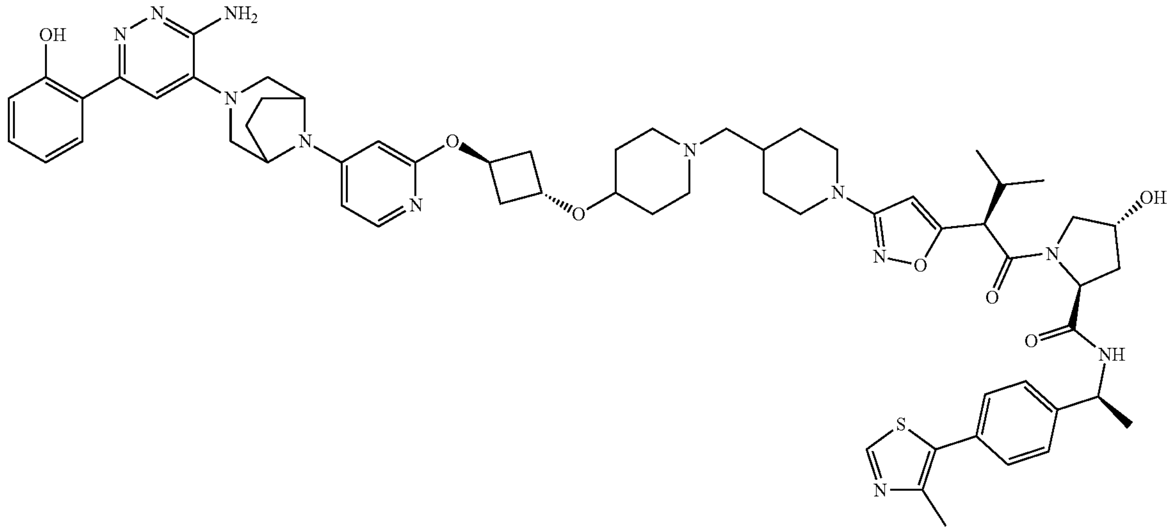
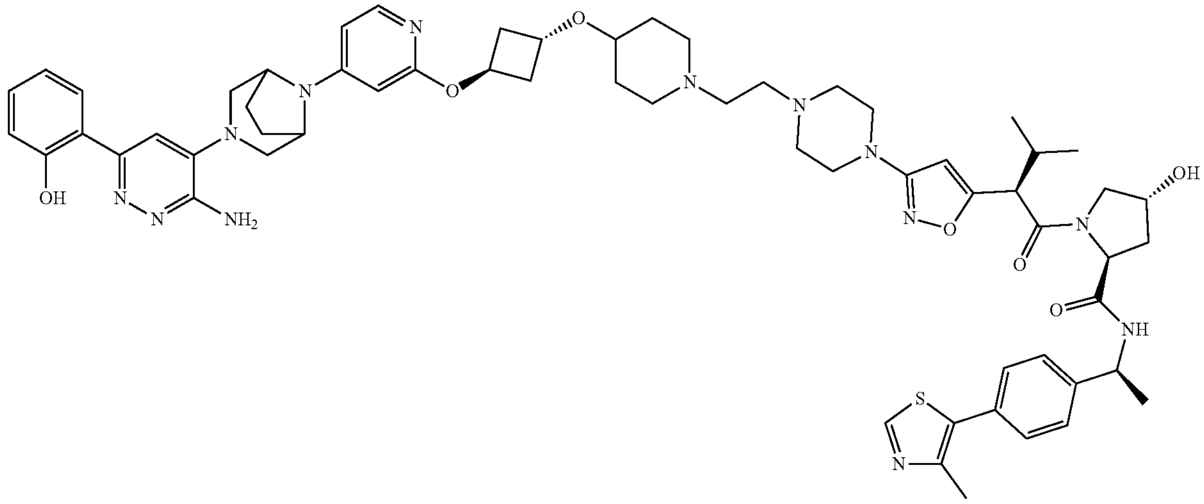
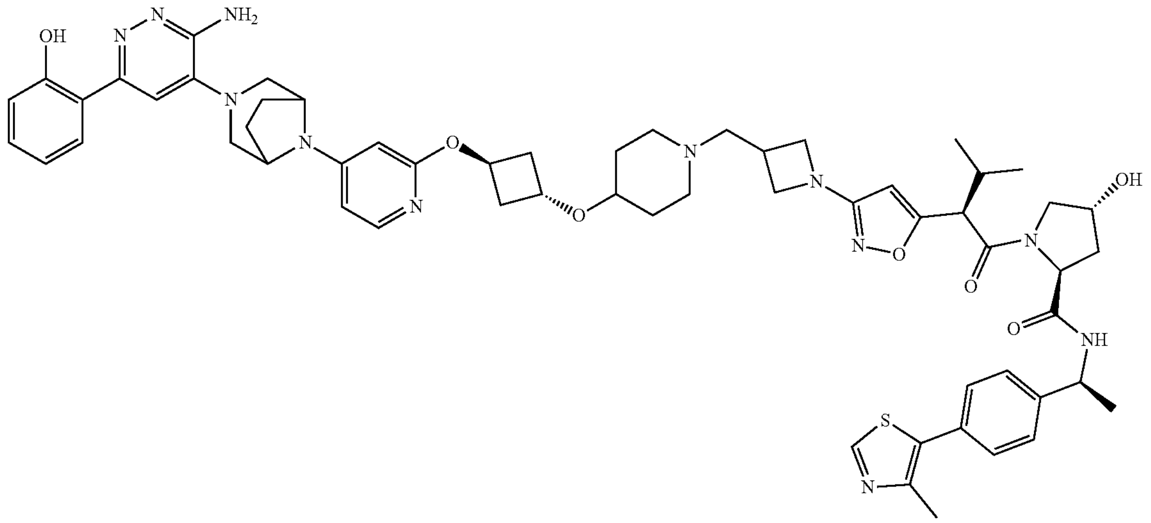

-continued
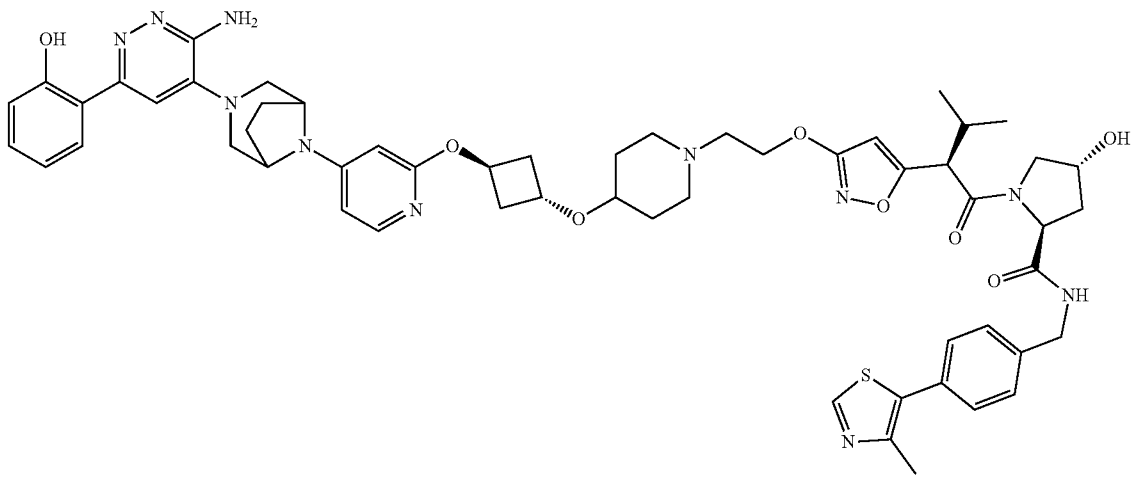
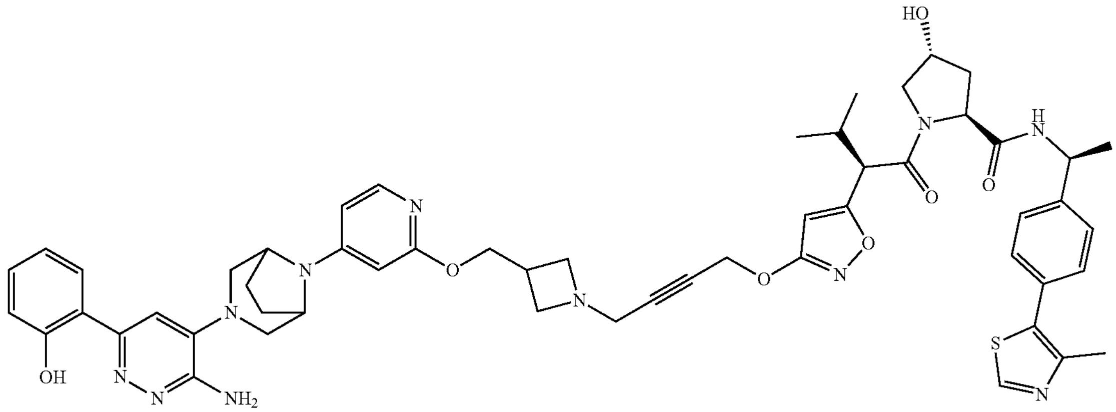
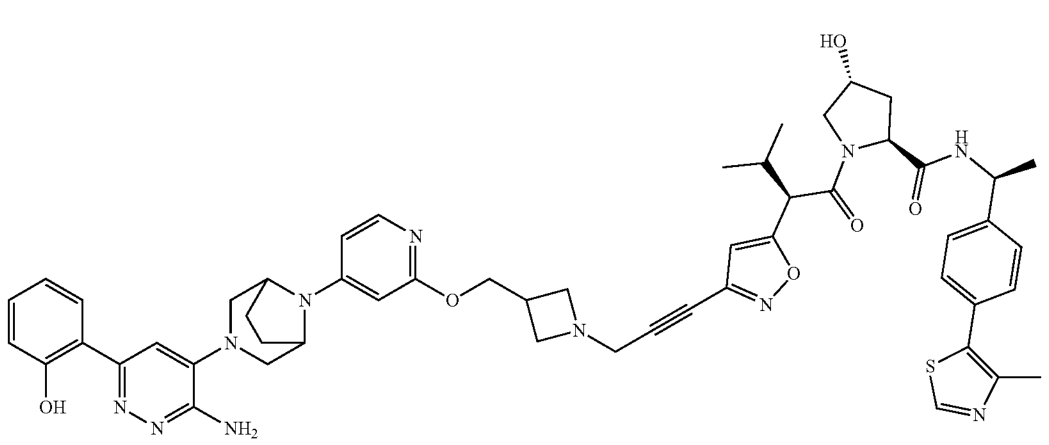

-continued
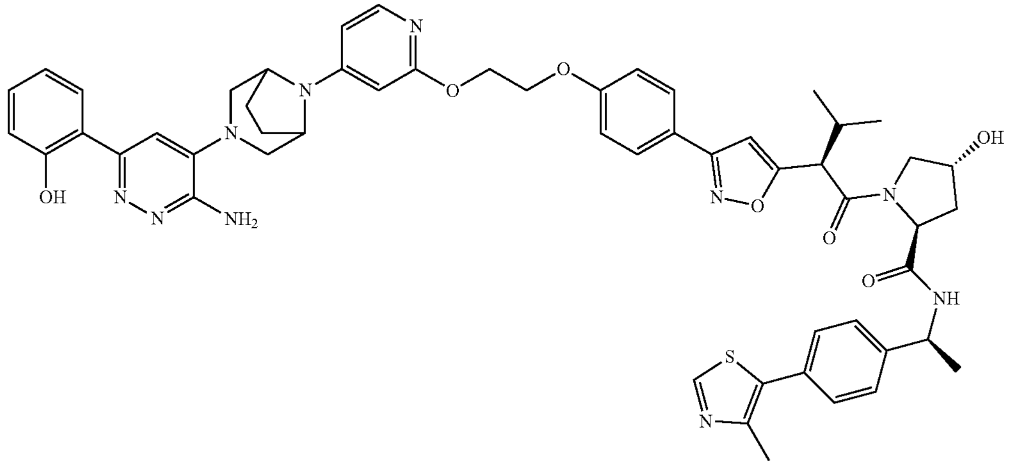
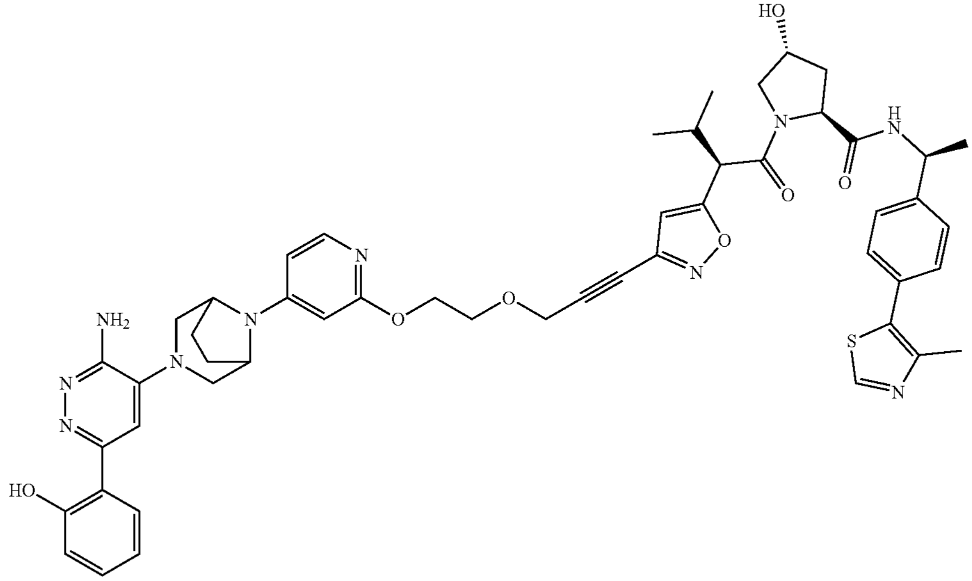
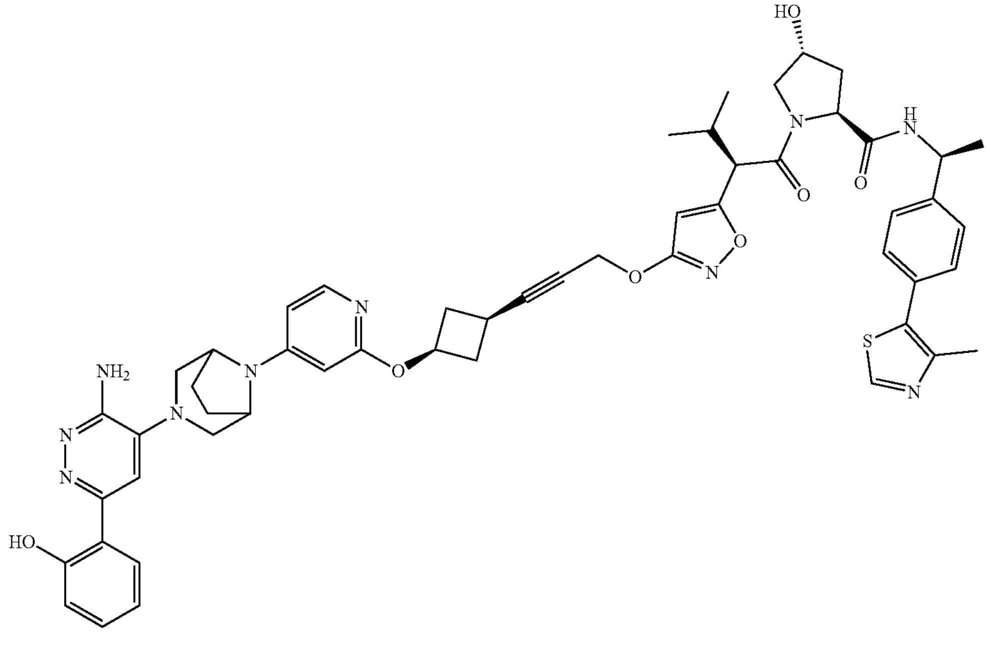

-continued
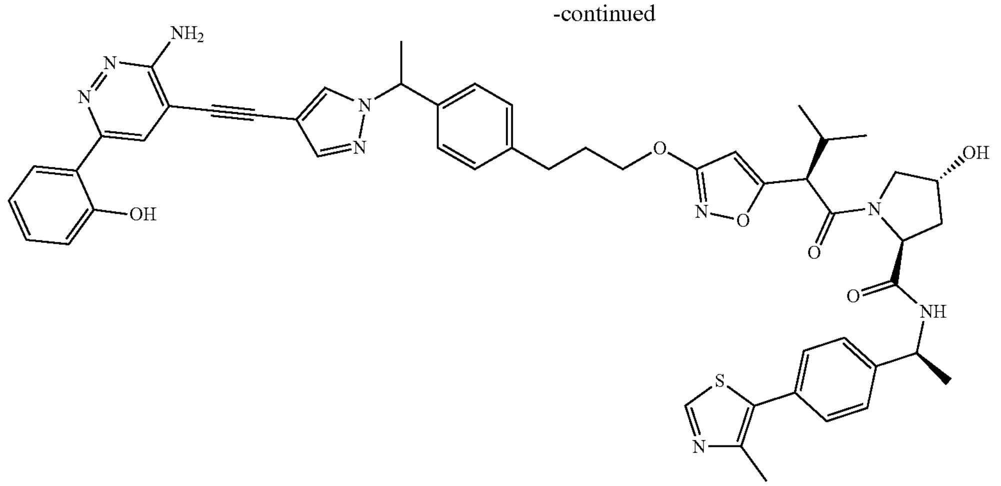
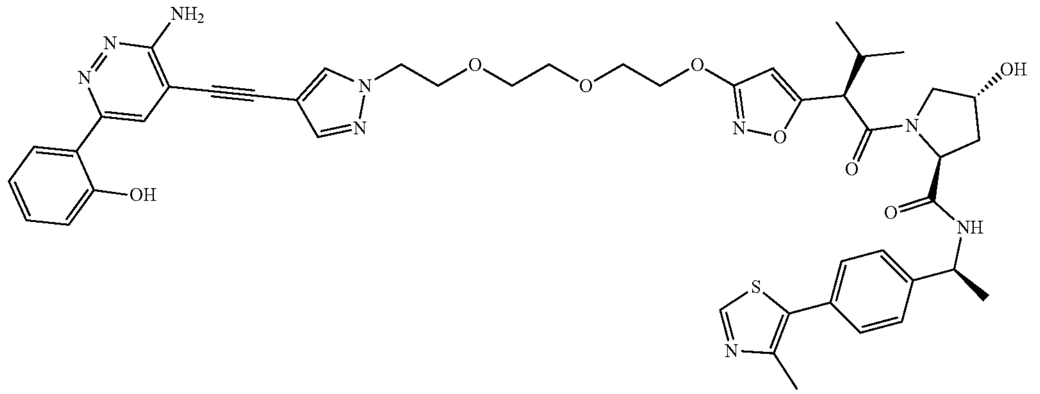
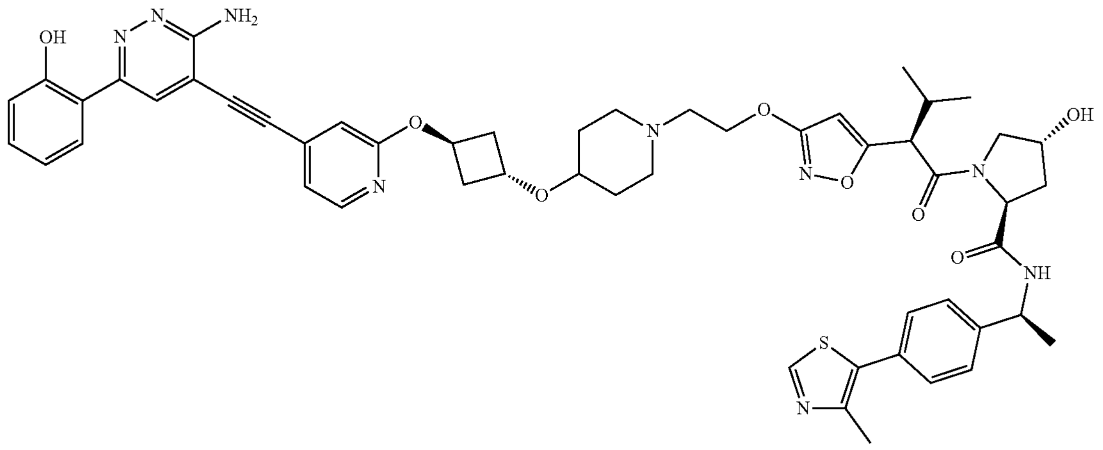

-continued
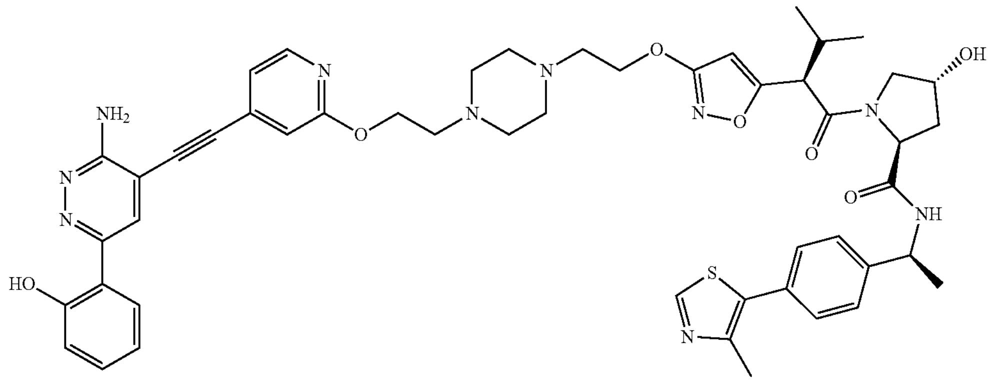
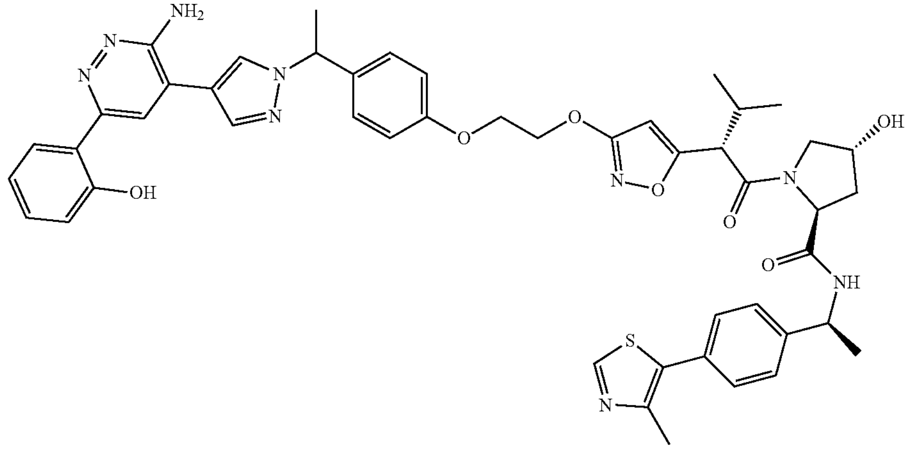
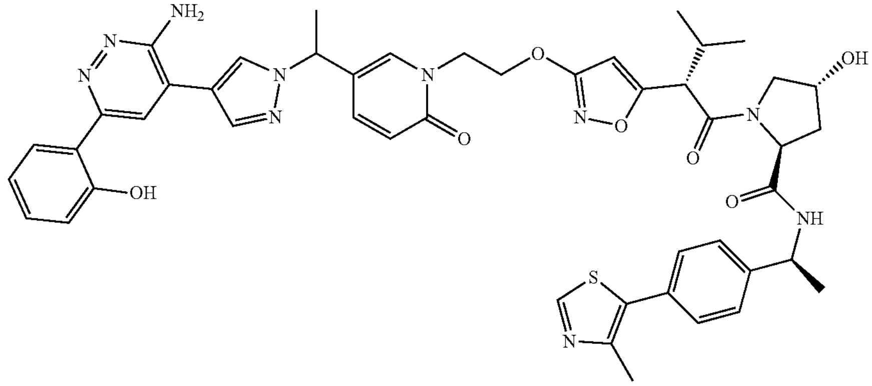
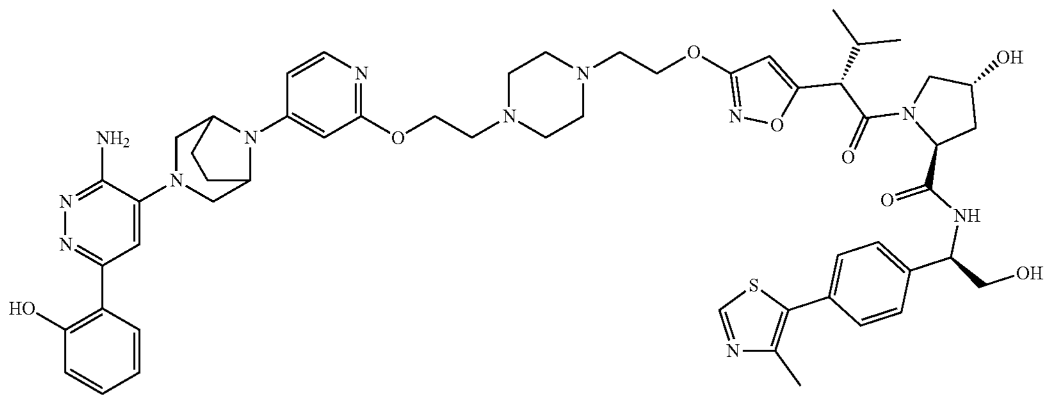

-continued
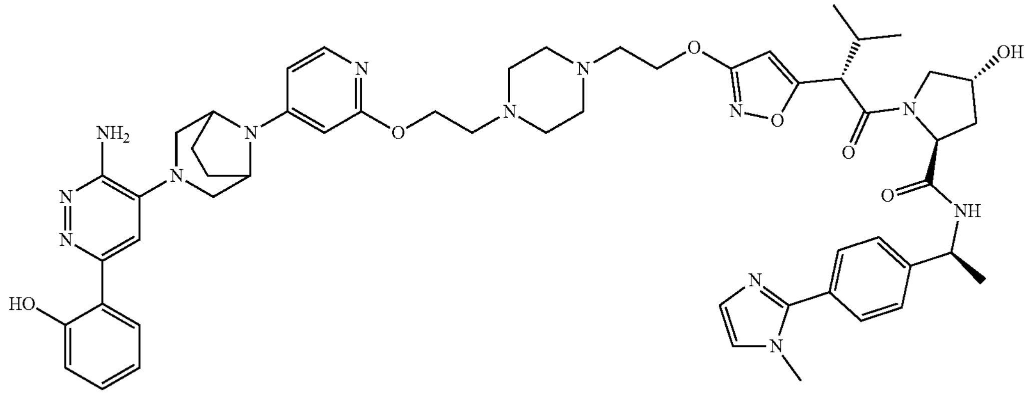
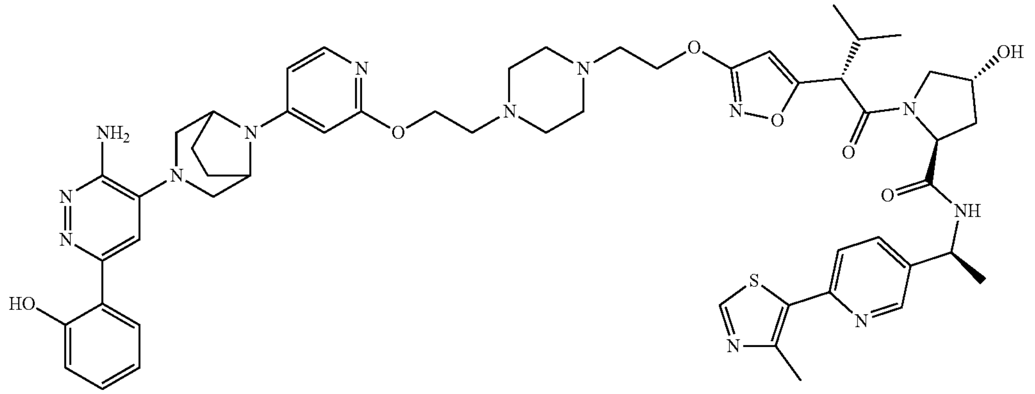
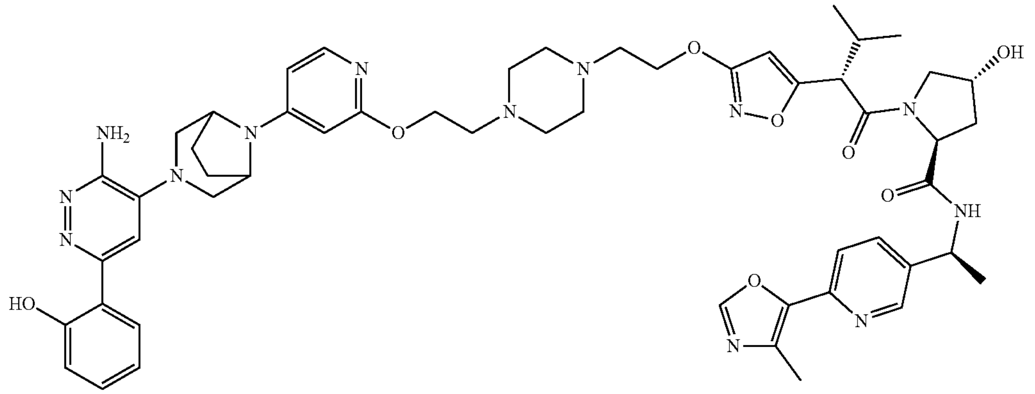
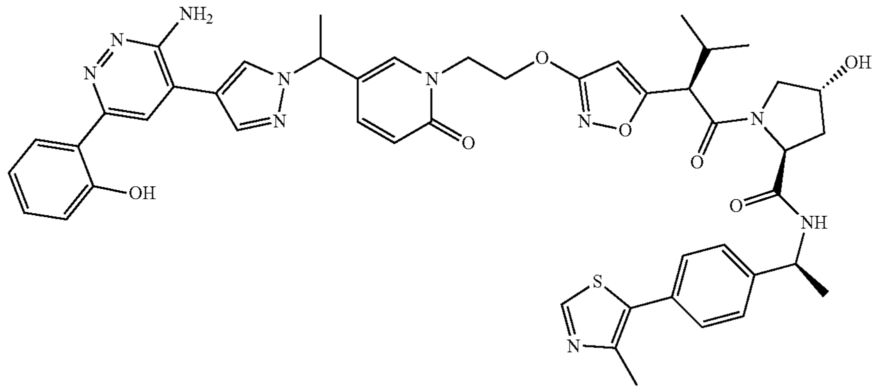

-continued
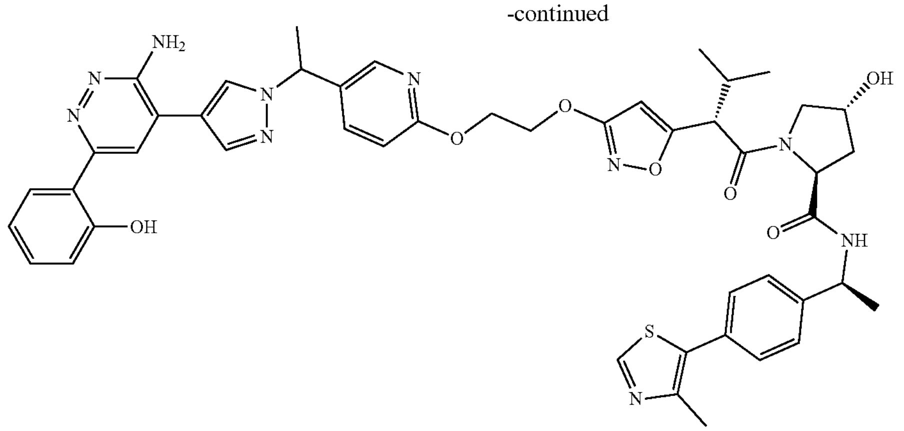
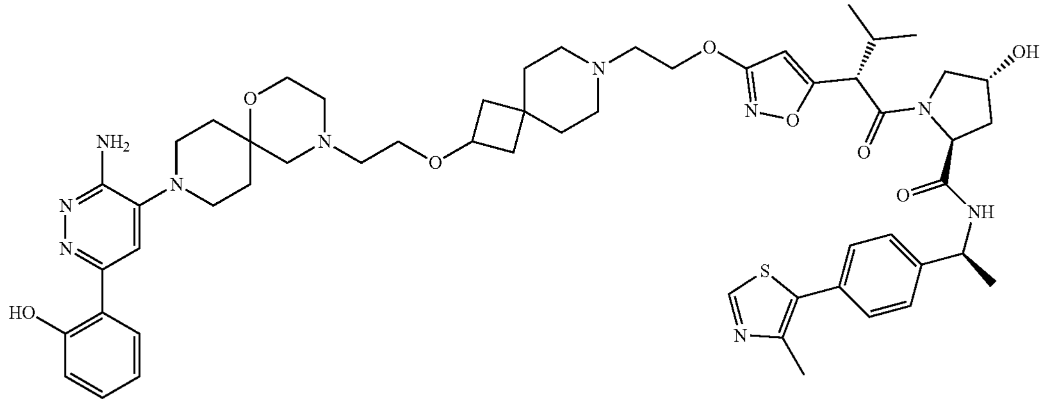
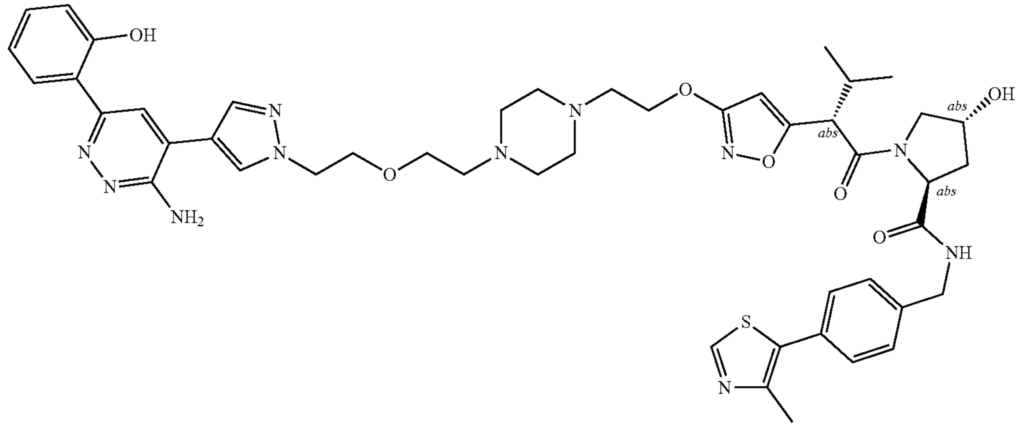
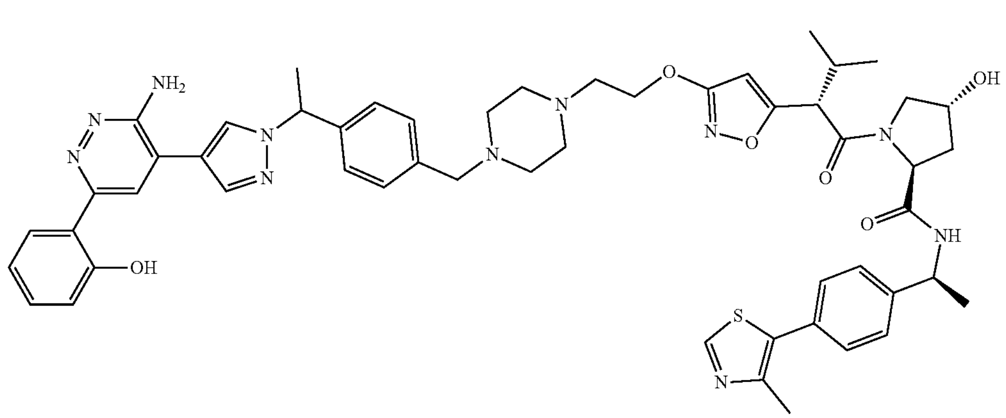

-continued
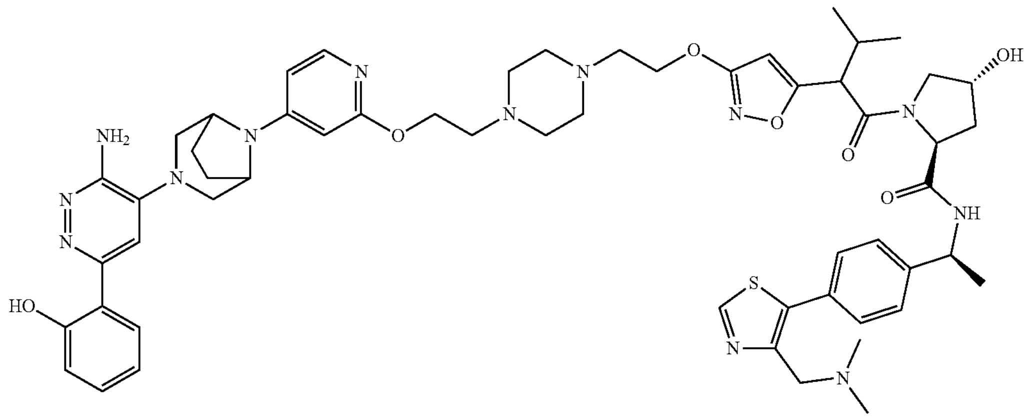
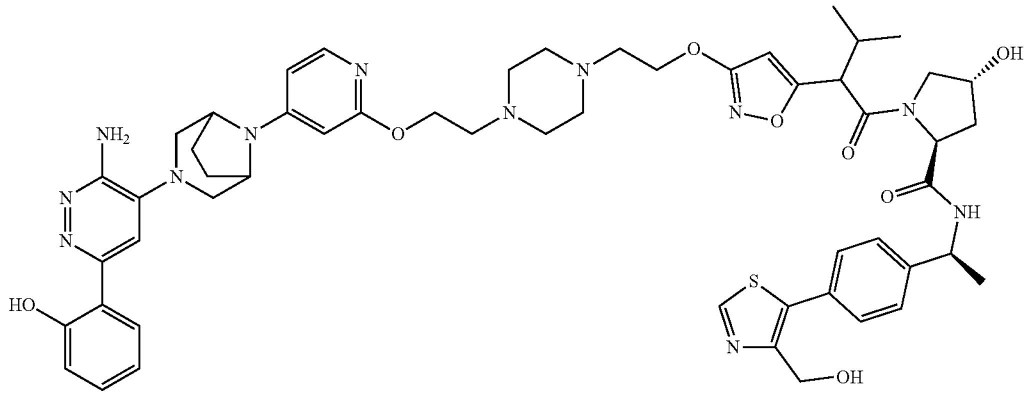
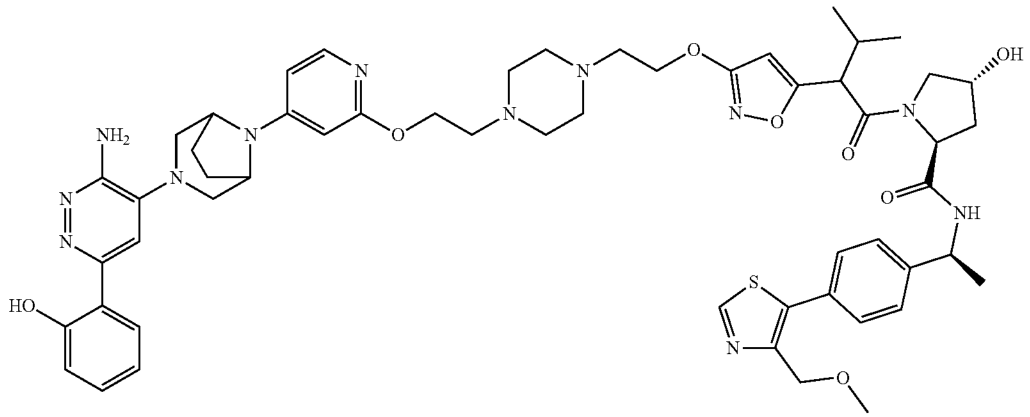
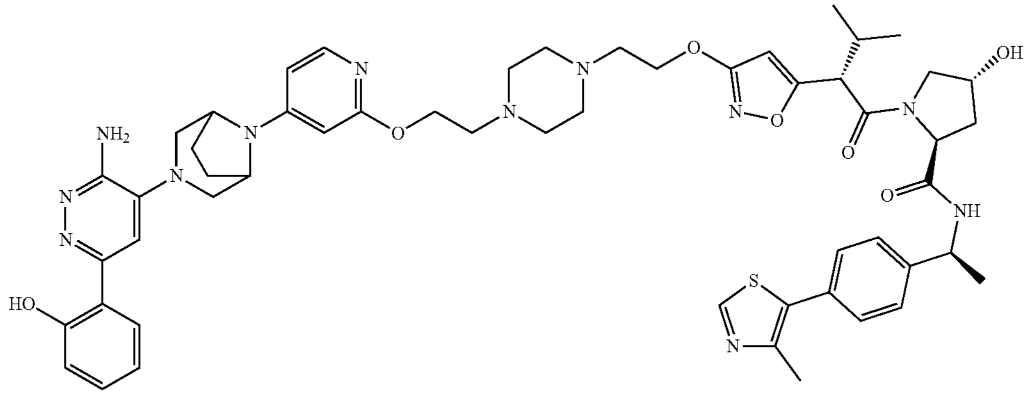

-continued
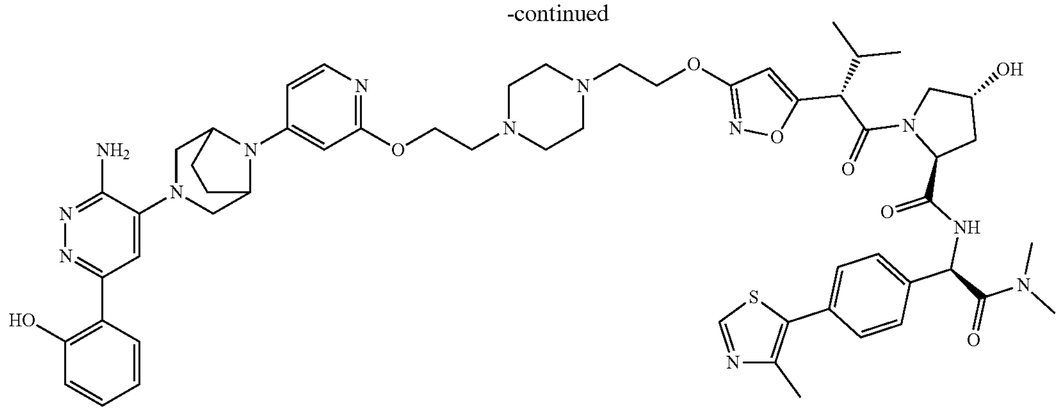
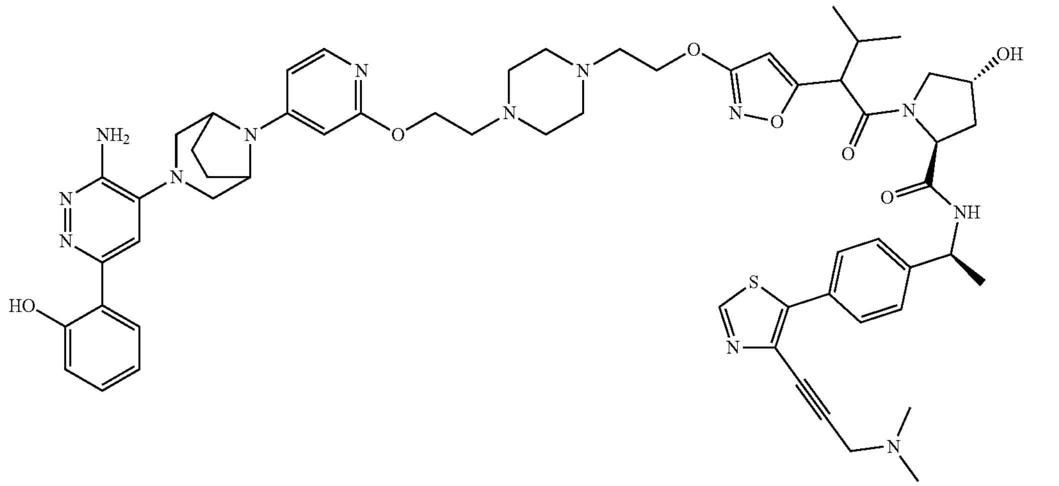
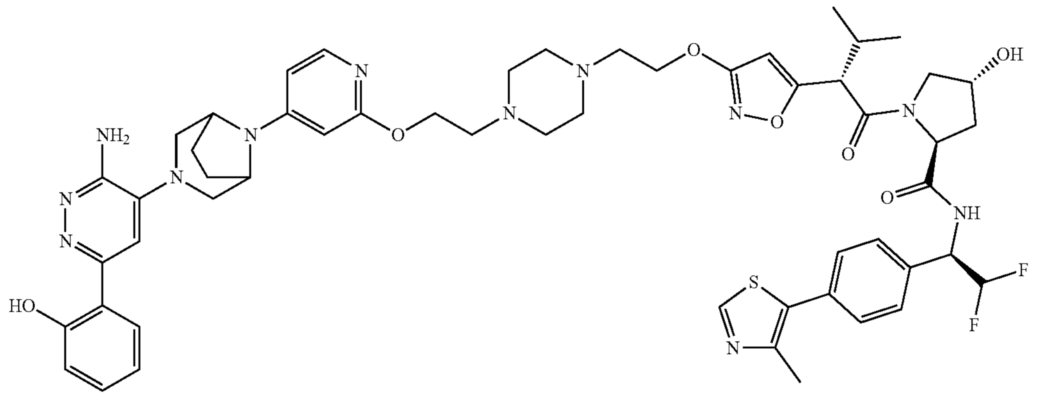
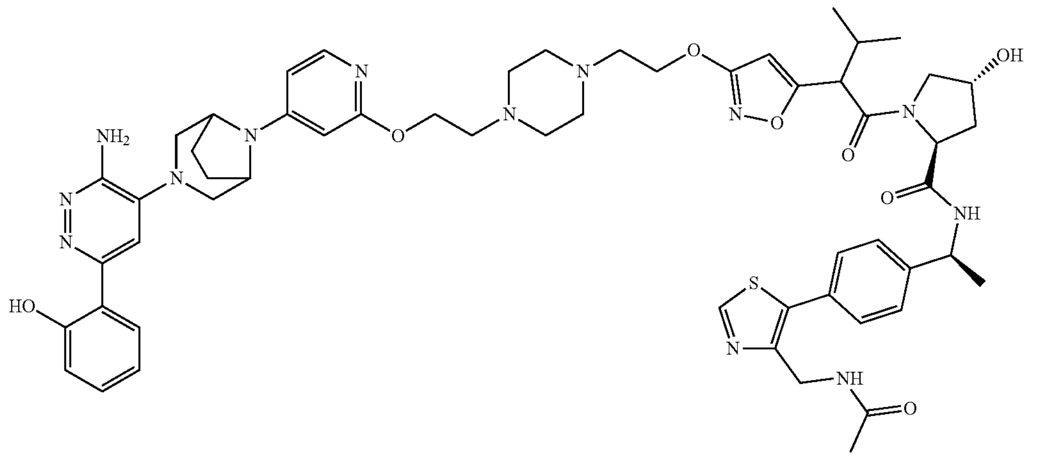

-continued
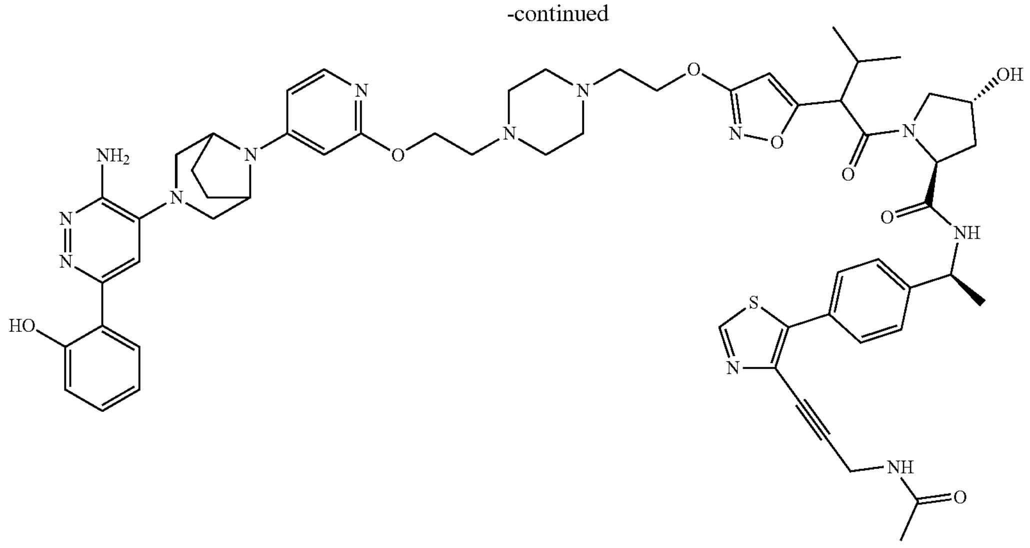
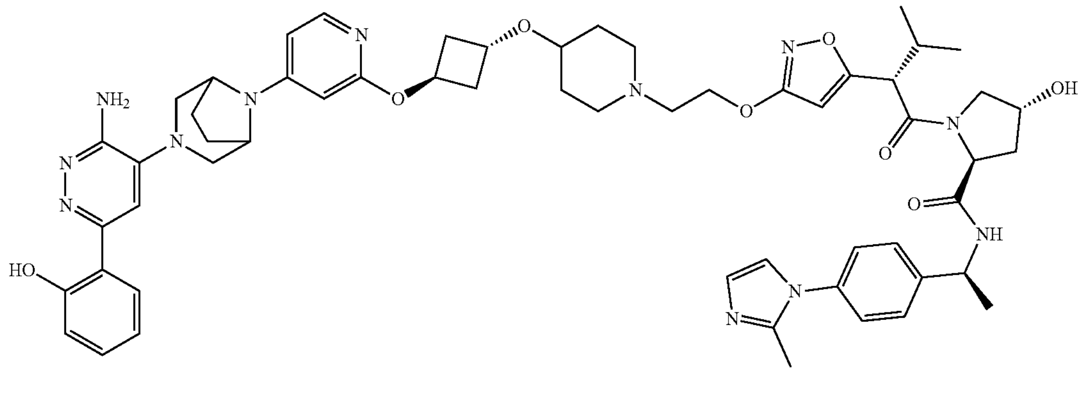
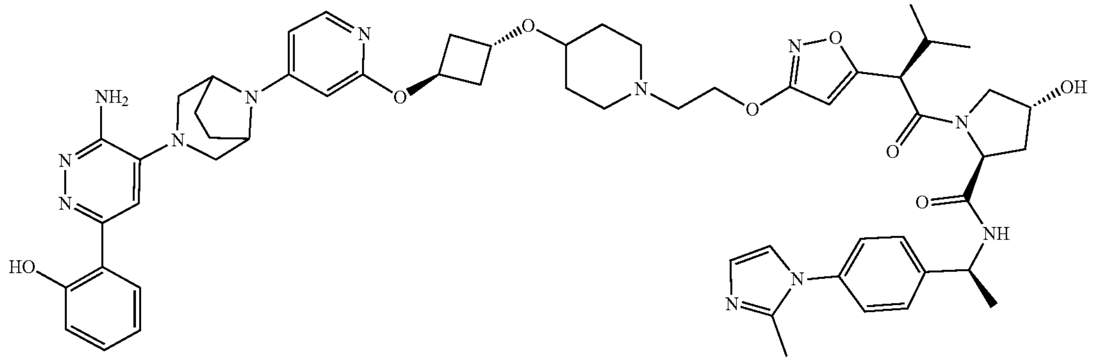

-continued
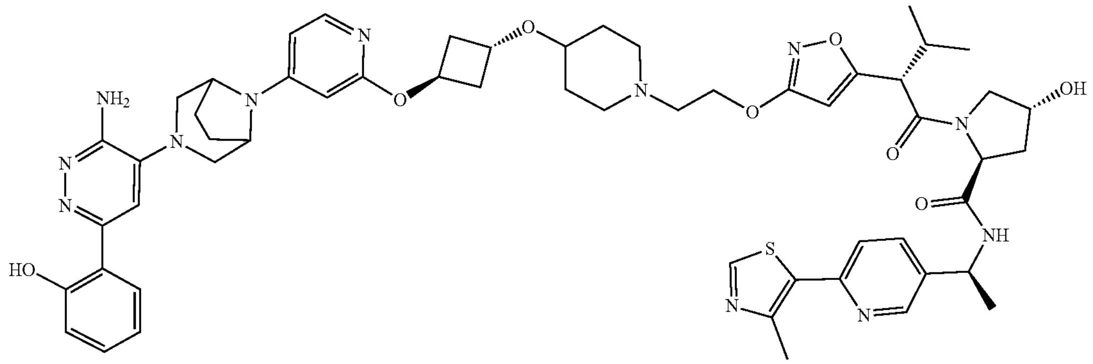
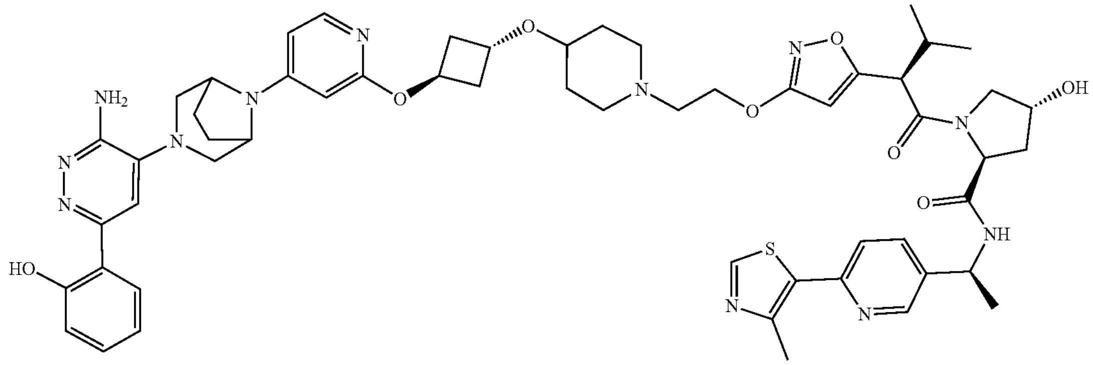
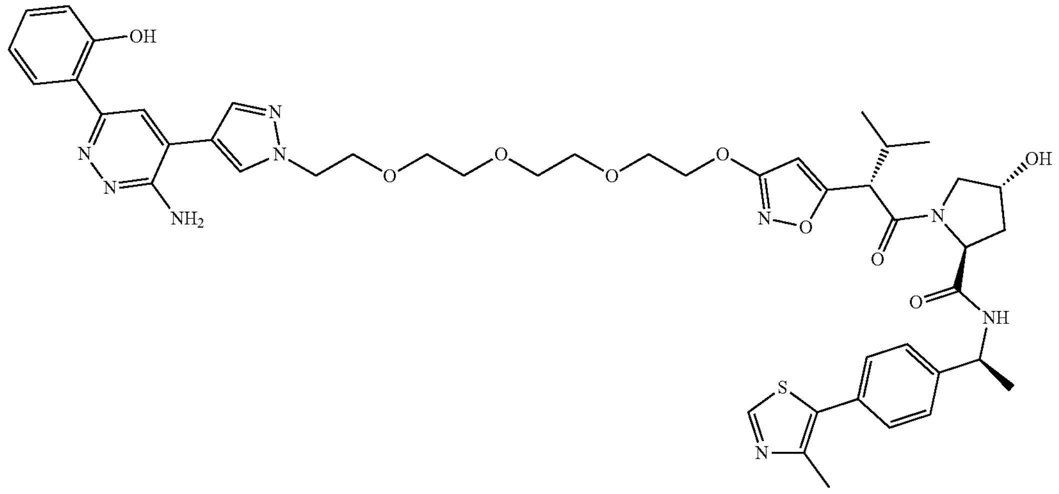
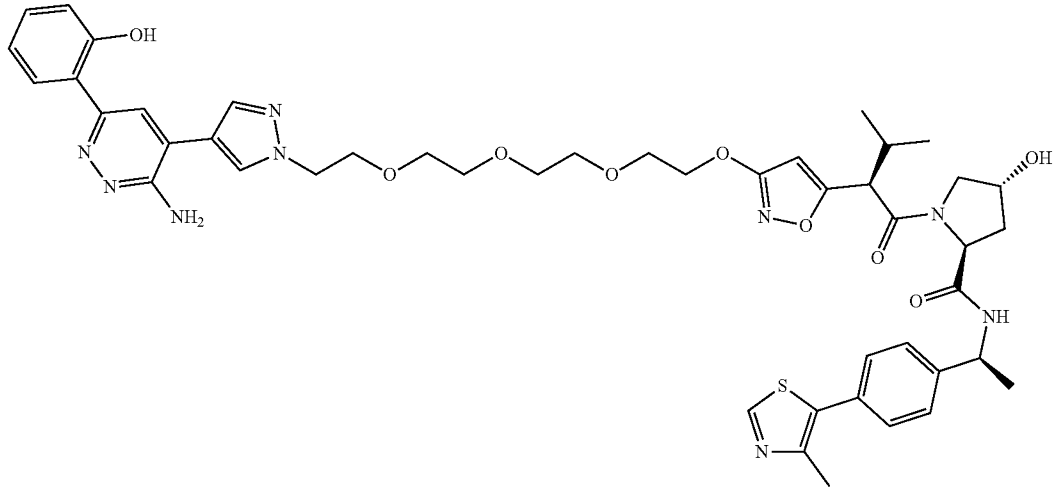

-continued
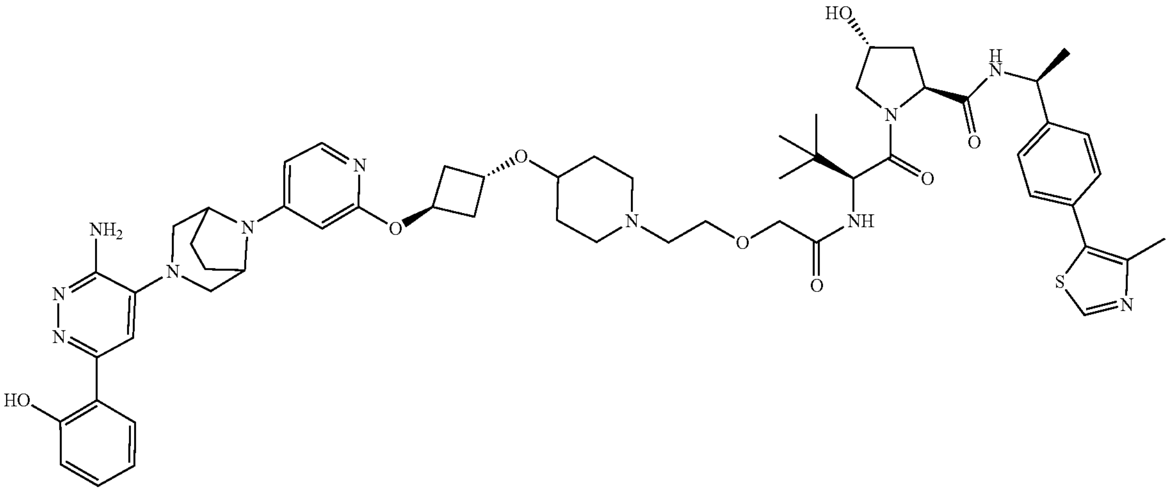
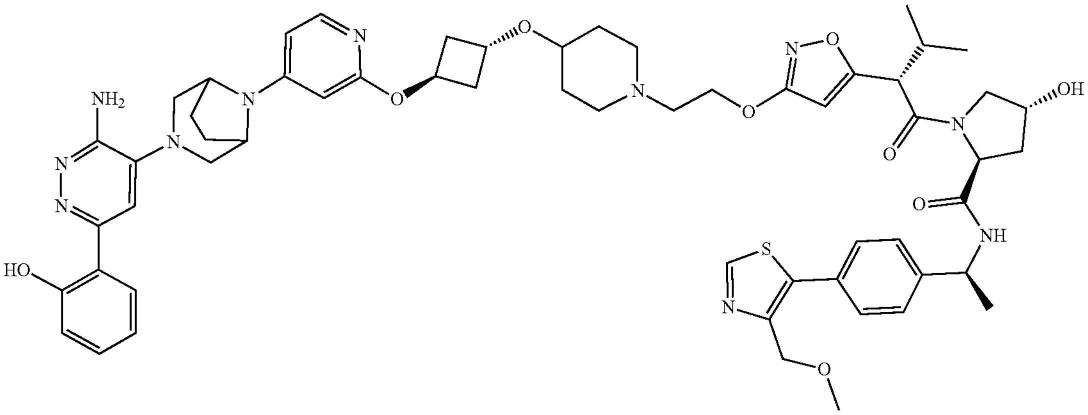
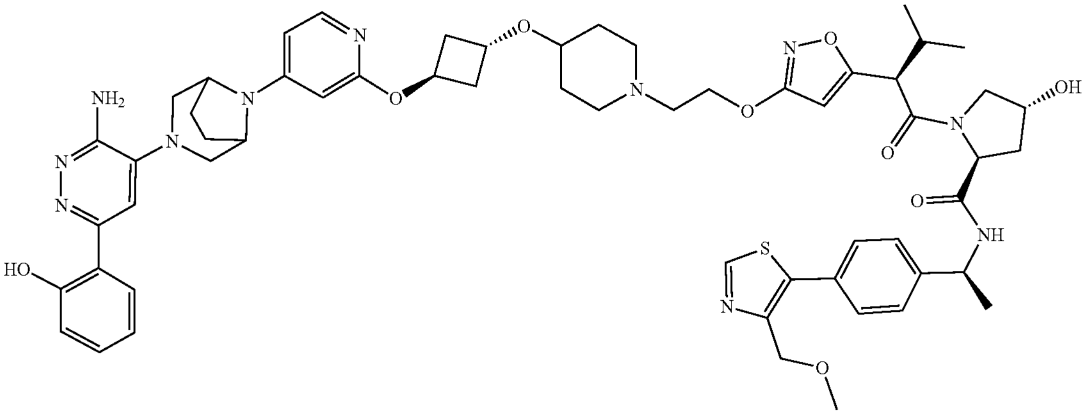
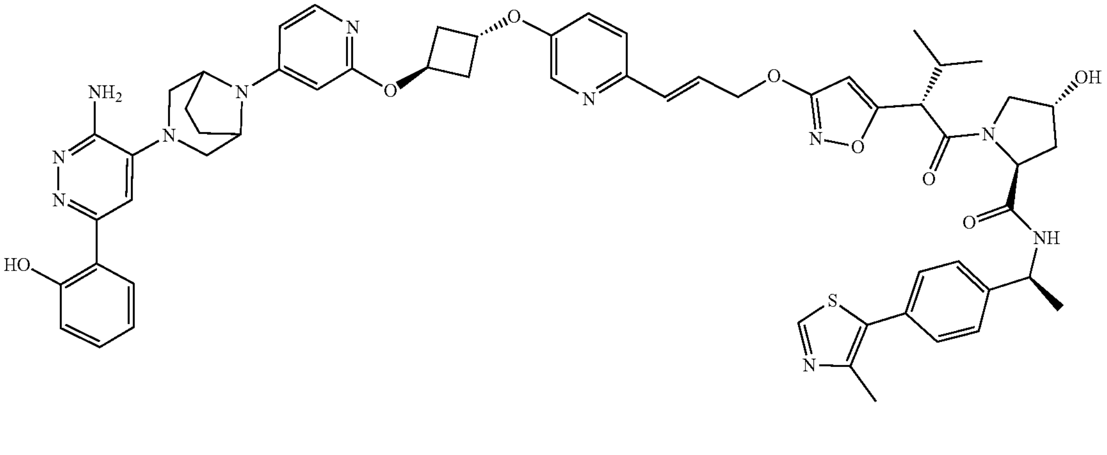

-continued
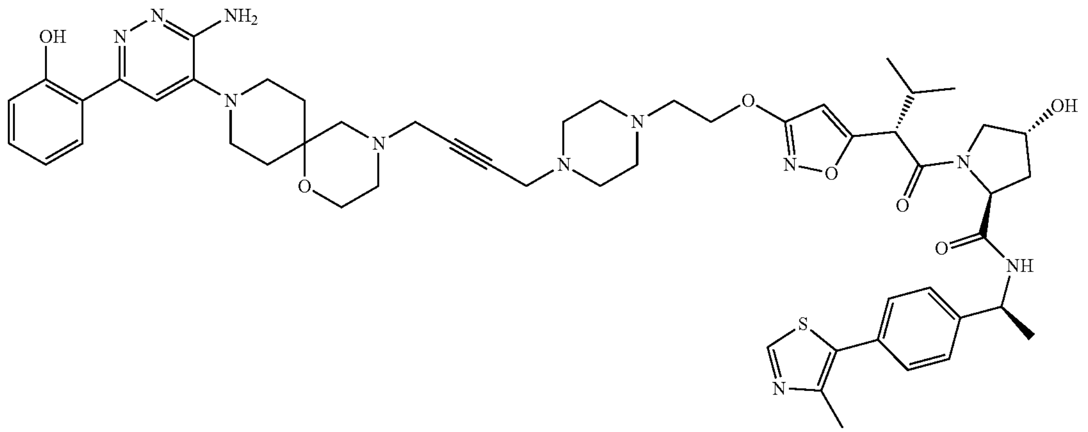
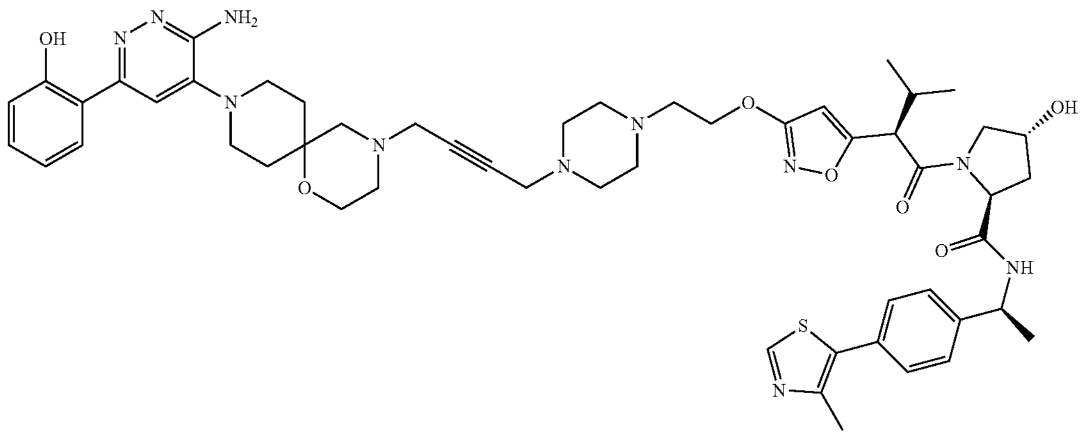
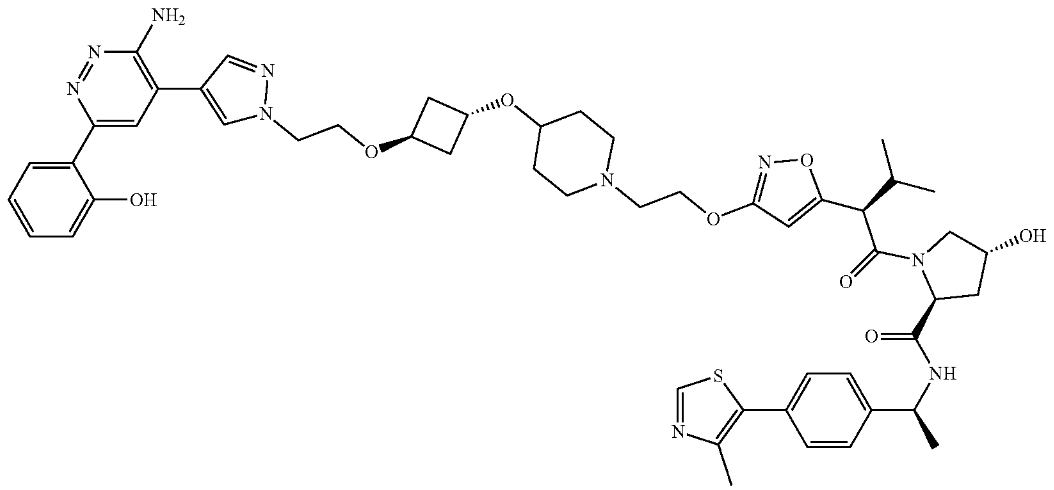
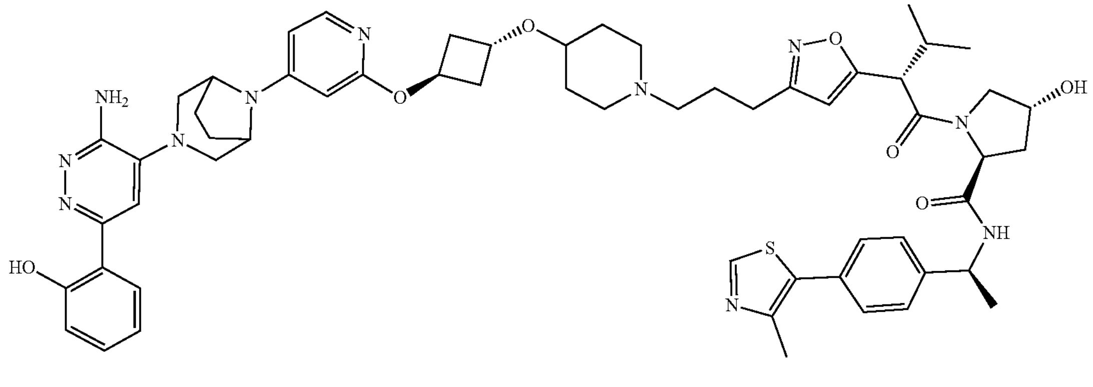

-continued
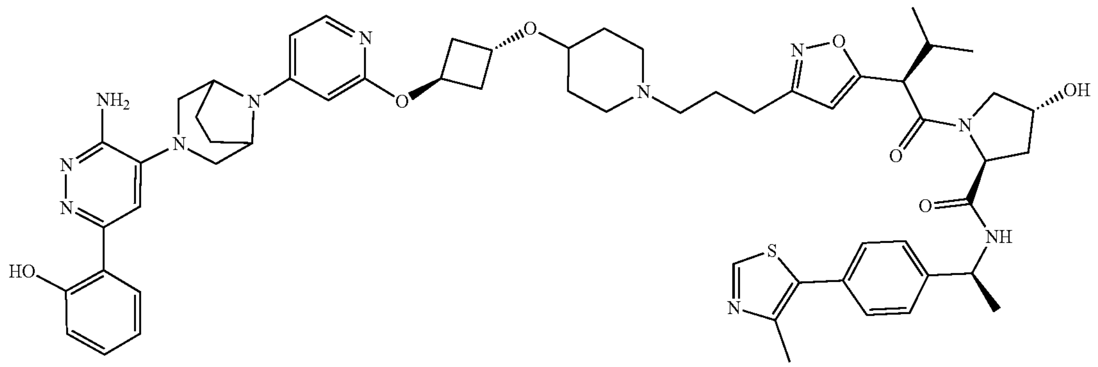
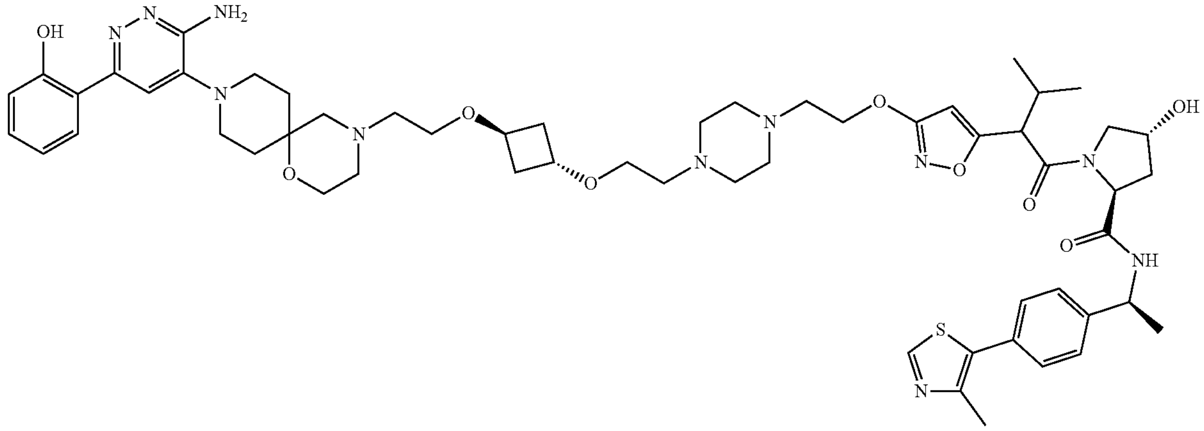
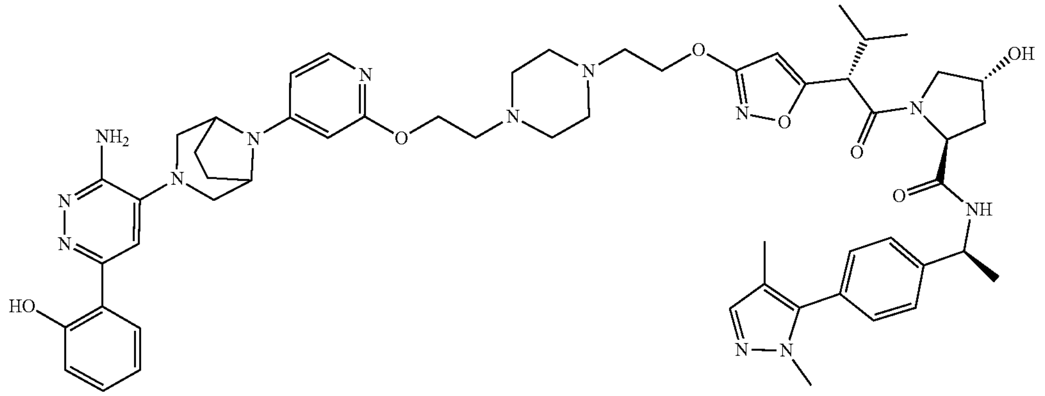
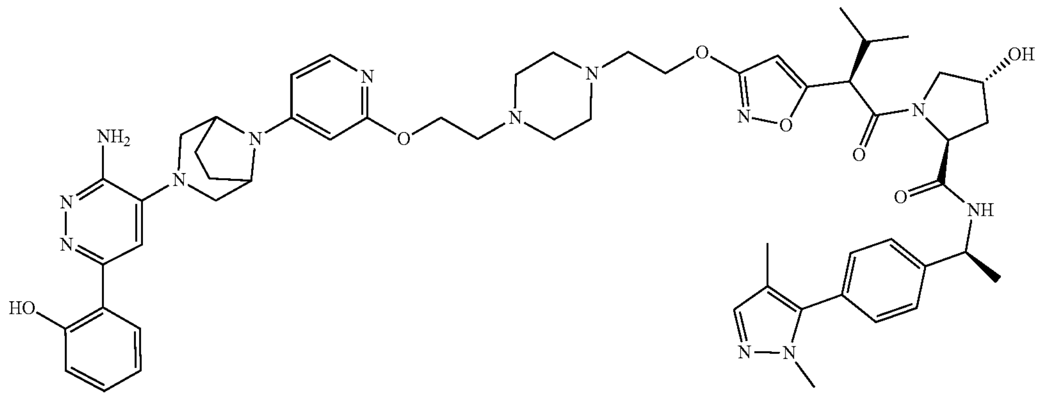

-continued
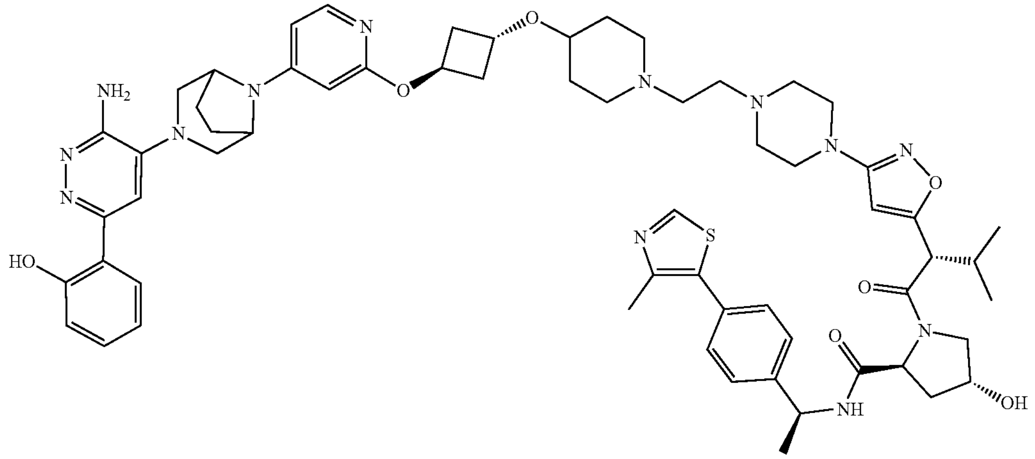
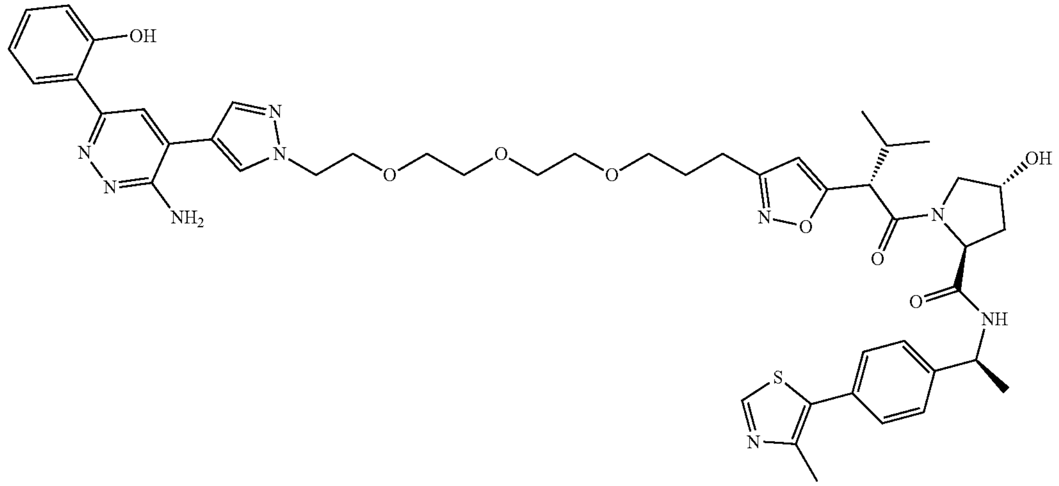
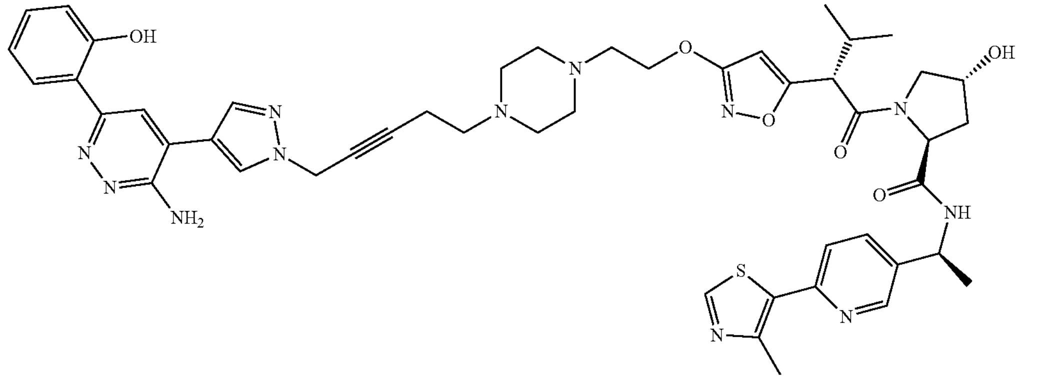
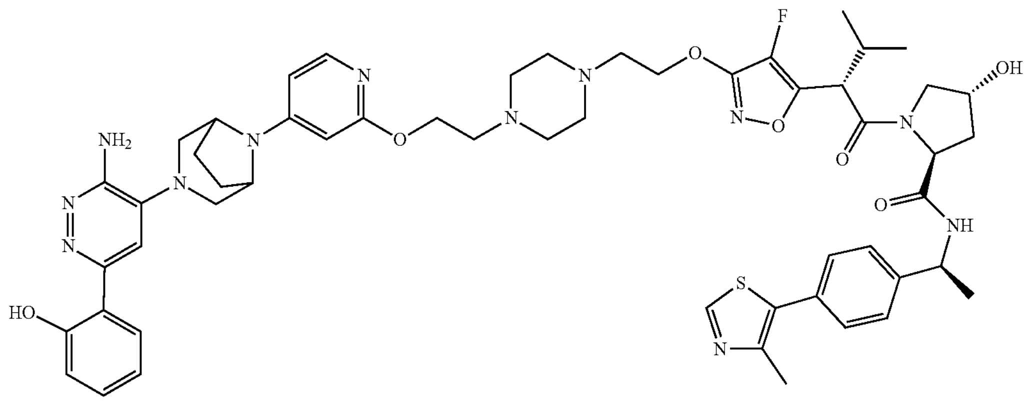

-continued
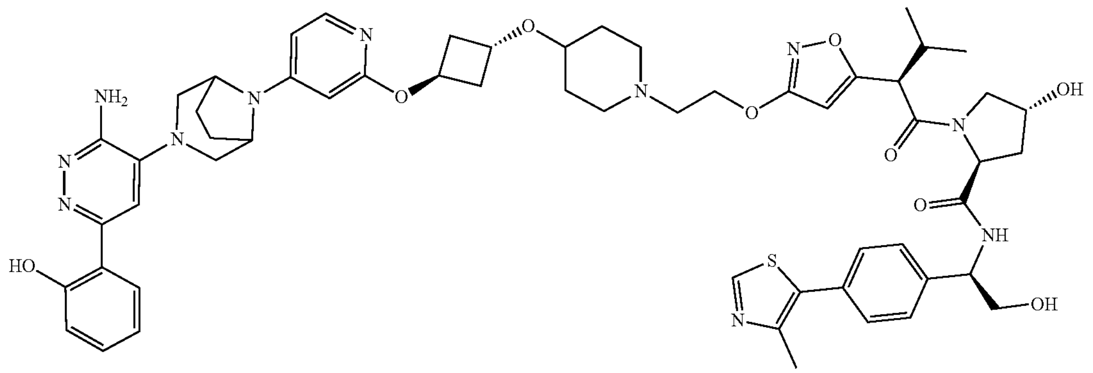
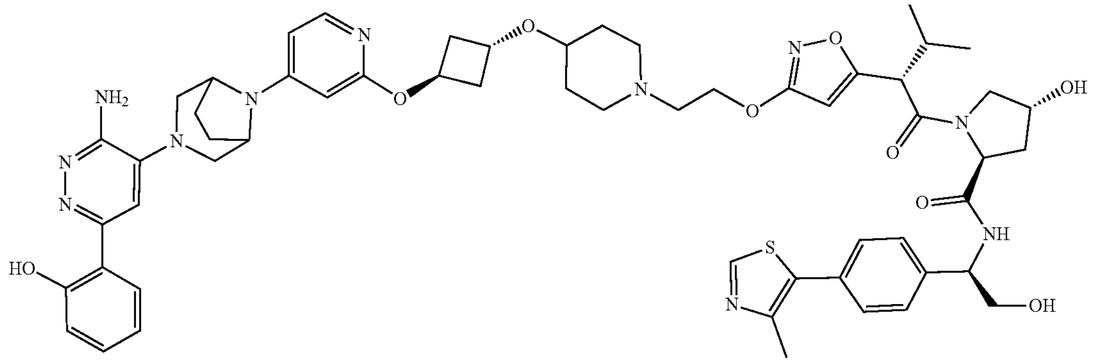
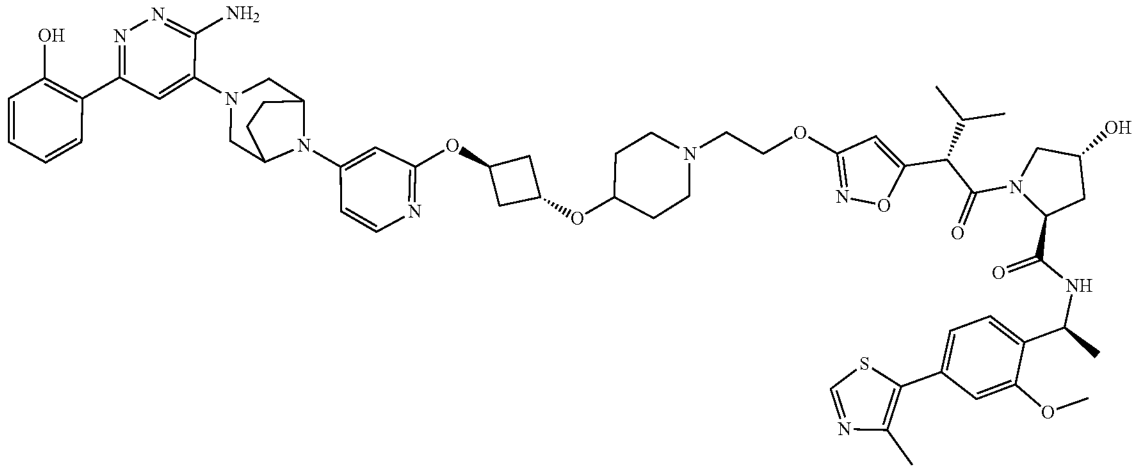
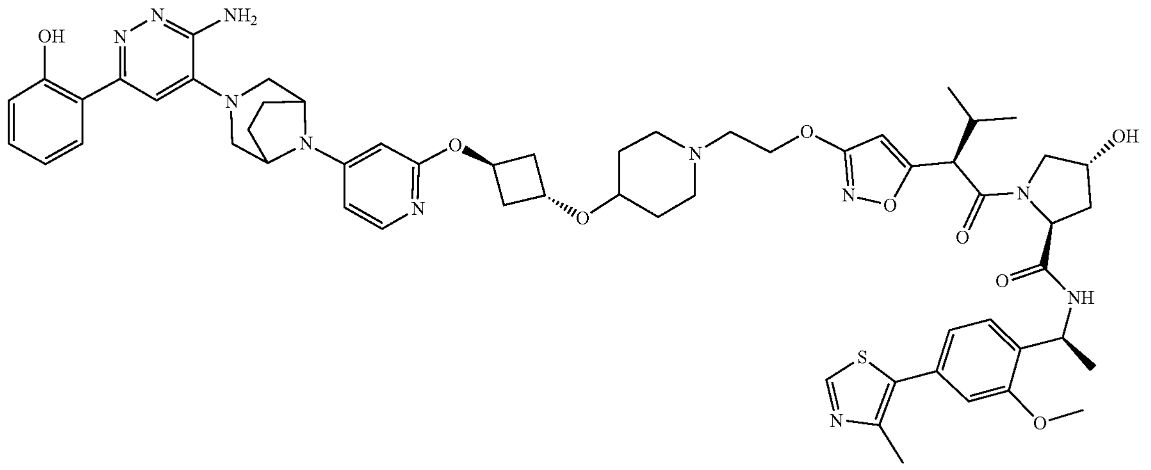

-continued
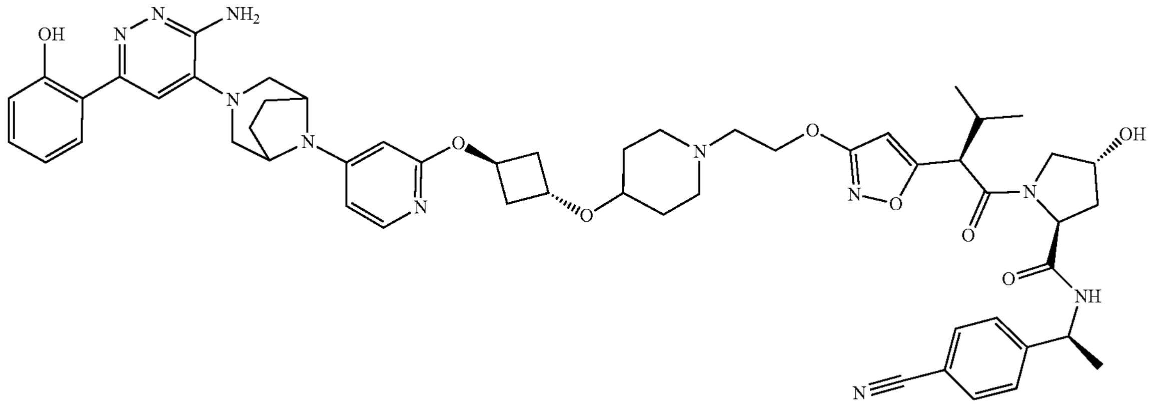
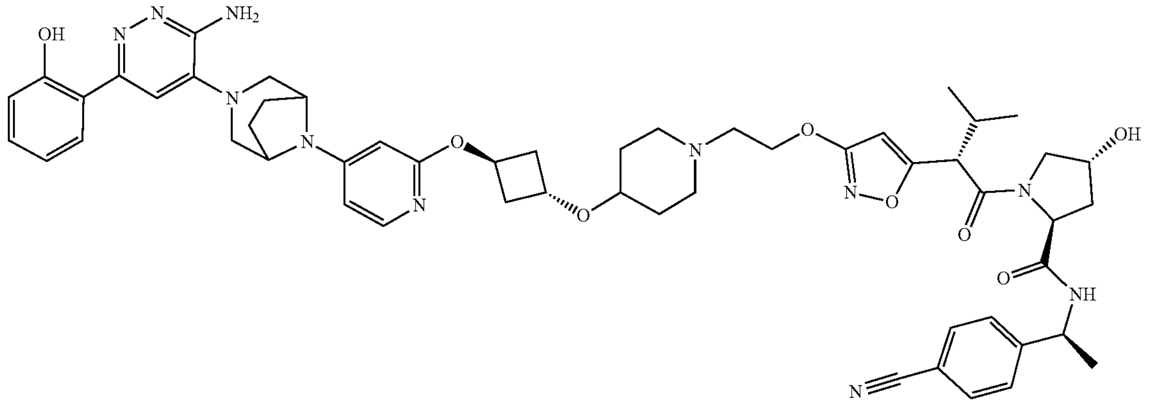
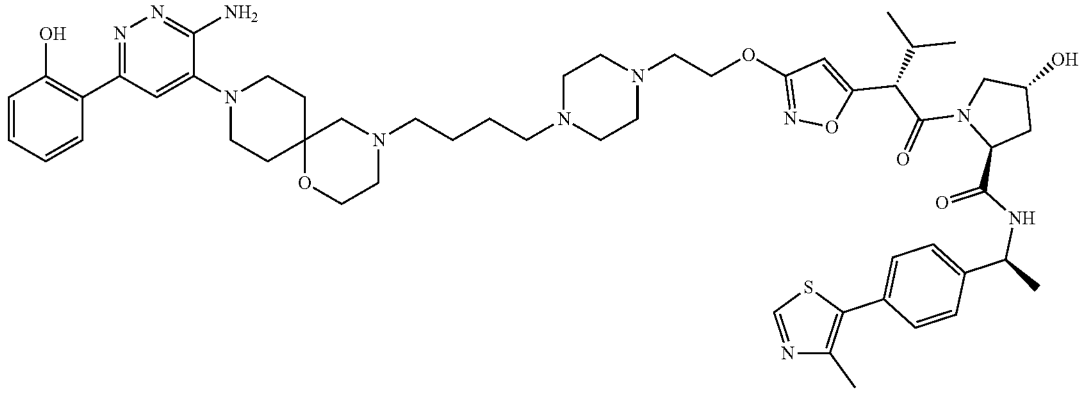
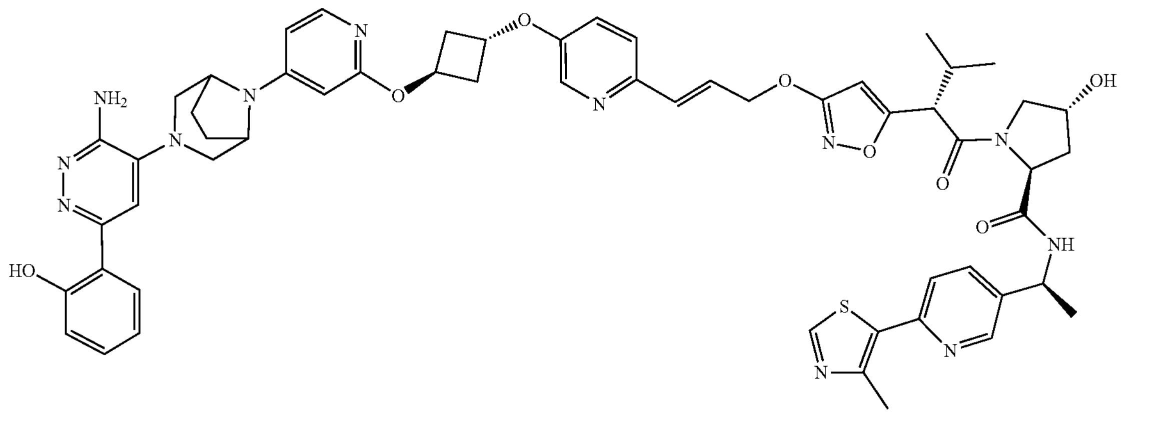

-continued
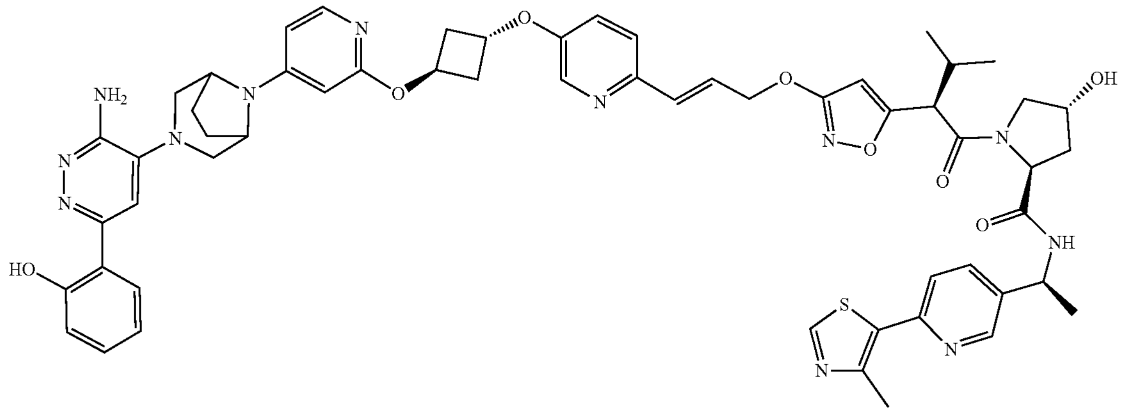
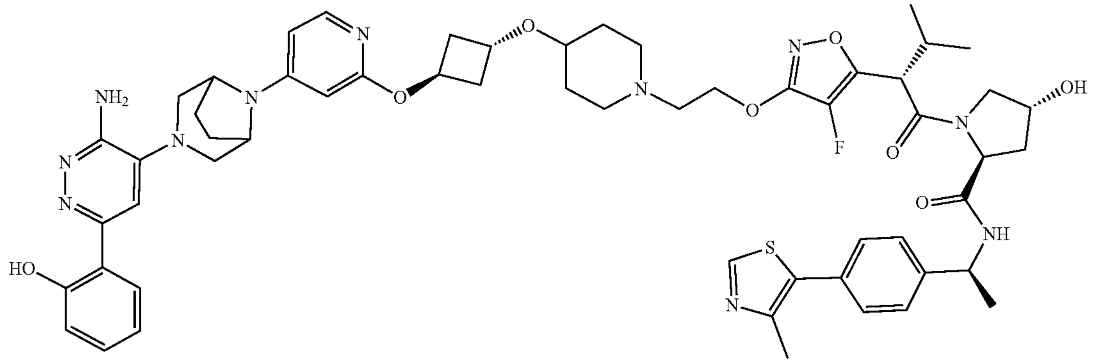
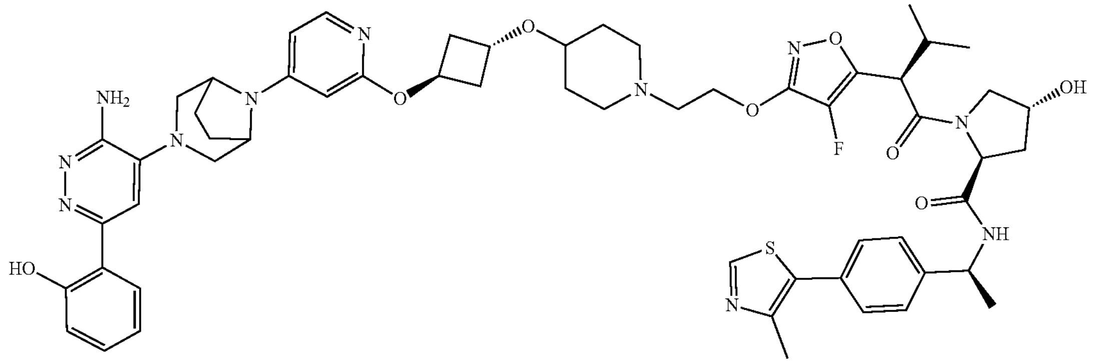
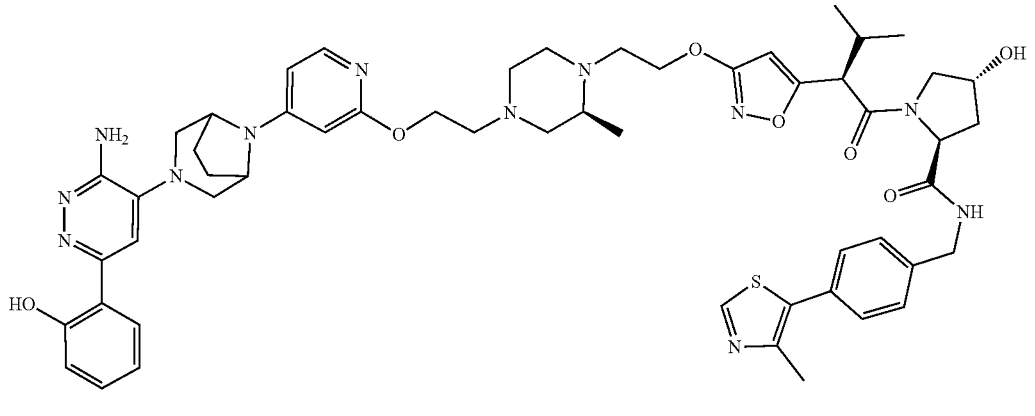

-continued
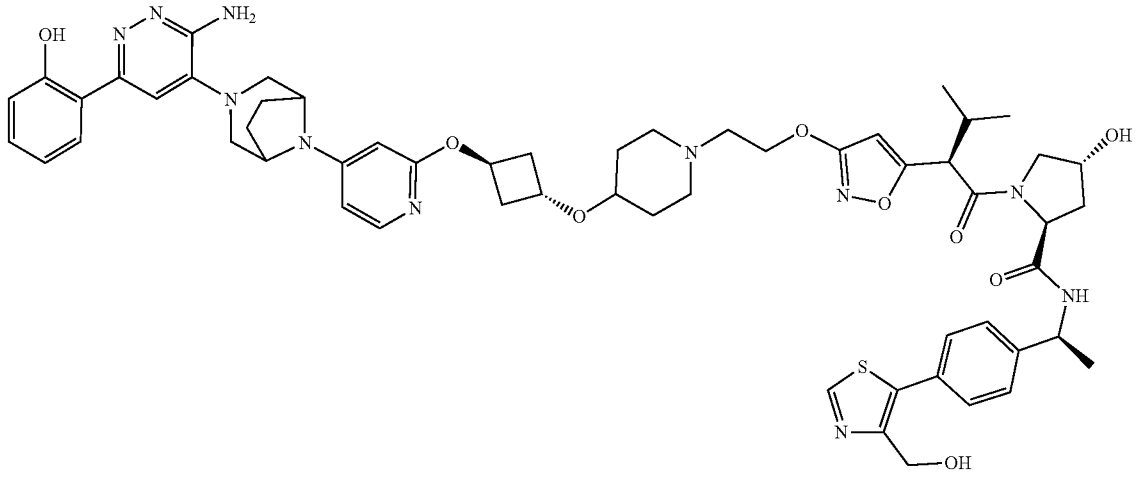
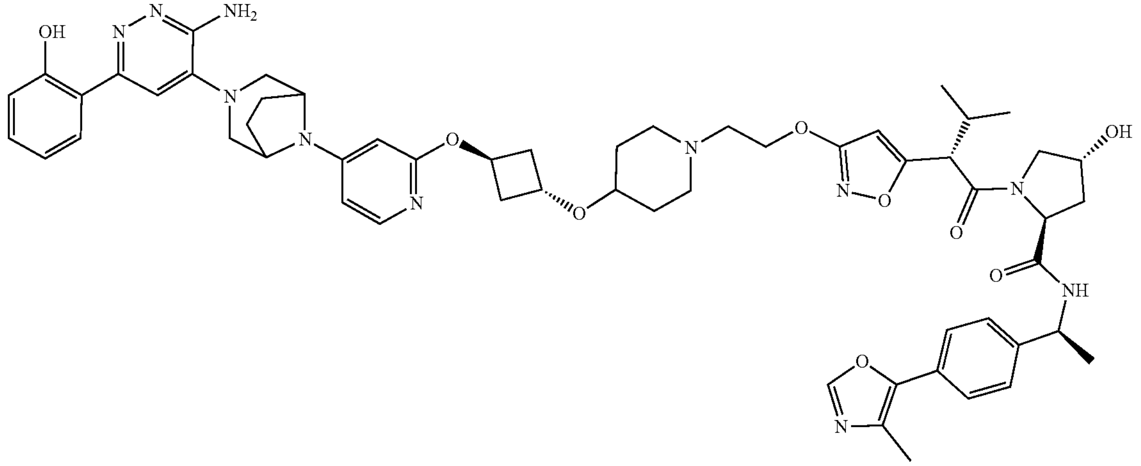
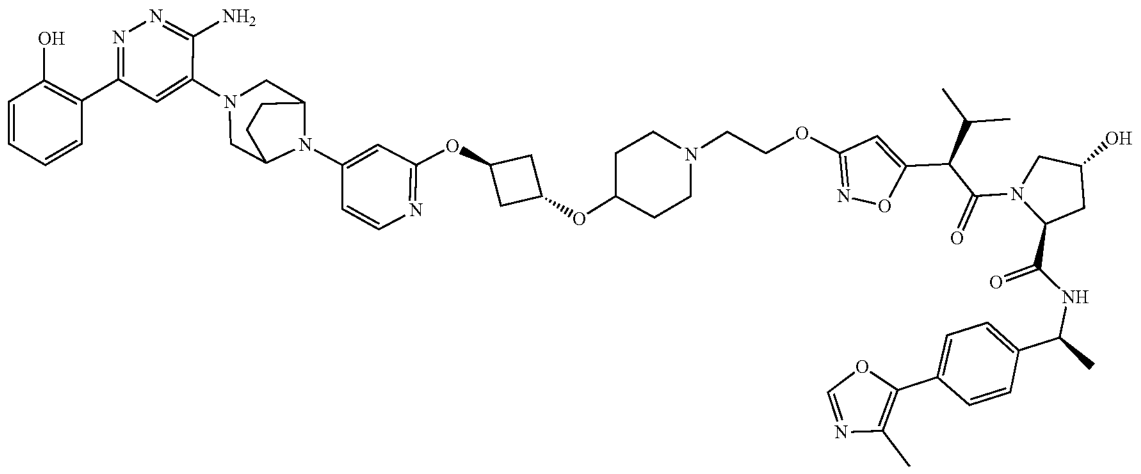

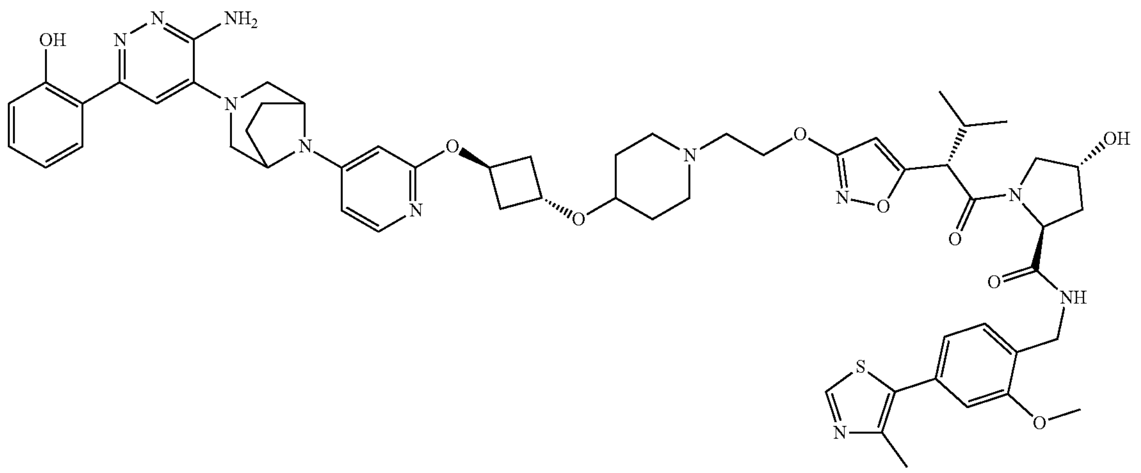 [SMILES: COc1cc(-c2scnc2C)ccc1CNC(=O)[C@@H]1C[C@@H](O)CN1C(=O)[C@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C]
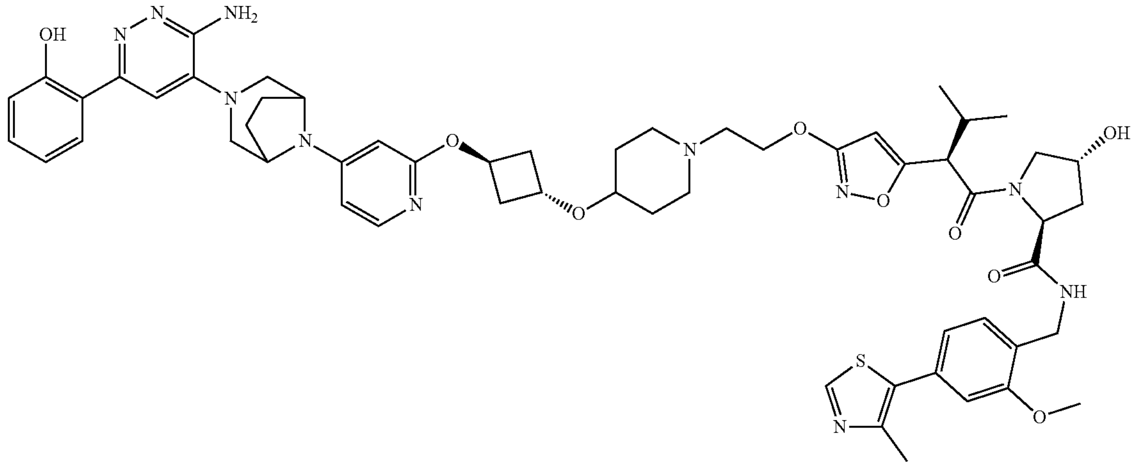 [SMILES: COc1cc(-c2scnc2C)ccc1CNC(=O)[C@@H]1C[C@@H](O)CN1C(=O)[C@@H](c1cc(OCCN2CCC(O[C@H]3C[C@H](Oc4cc(N5C6CCC5CN(c5cc(-c7ccccc7O)nnc5N)C6)ccn4)C3)CC2)no1)C(C)C]
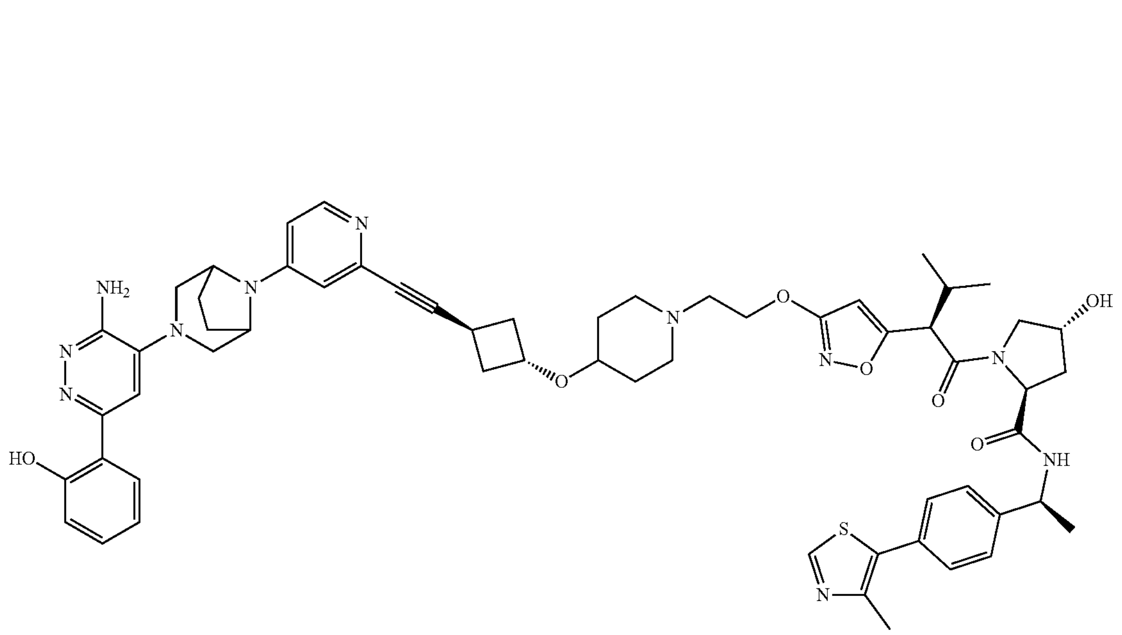 [SMILES: Cc1ncsc1-c1ccc([C@H](C)NC(=O)[C@@H]2C[C@@H](O)CN2C(=O)[C@@H](c2cc(OCCN3CCC(O[C@H]4C[C@H](C#Cc5cc(N6C7CCC6CN(c6cc(-c8ccccc8O)nnc6N)C7)ccn5)C4)CC3)no2)C(C)C)cc1]

-continued
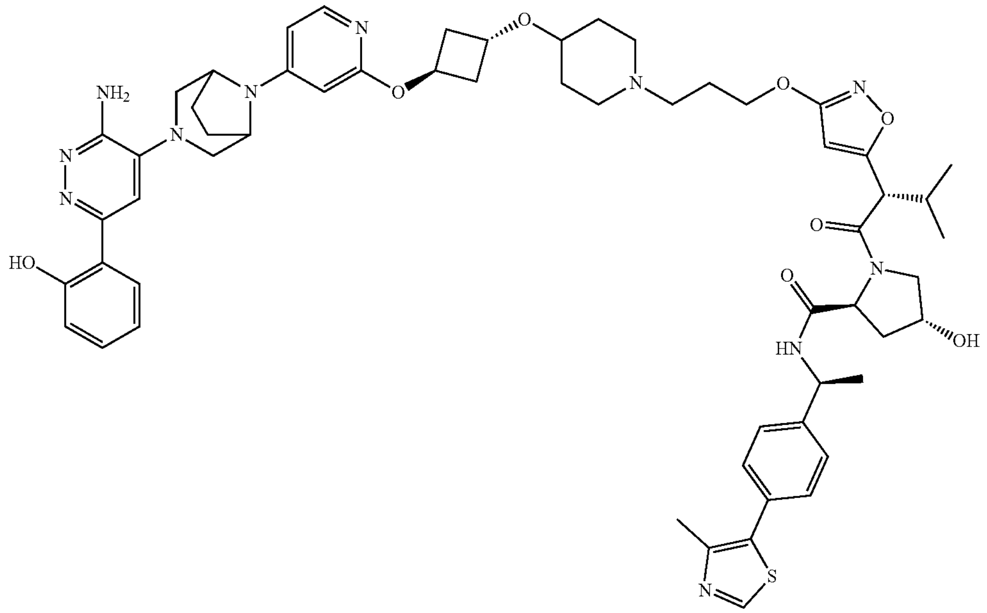
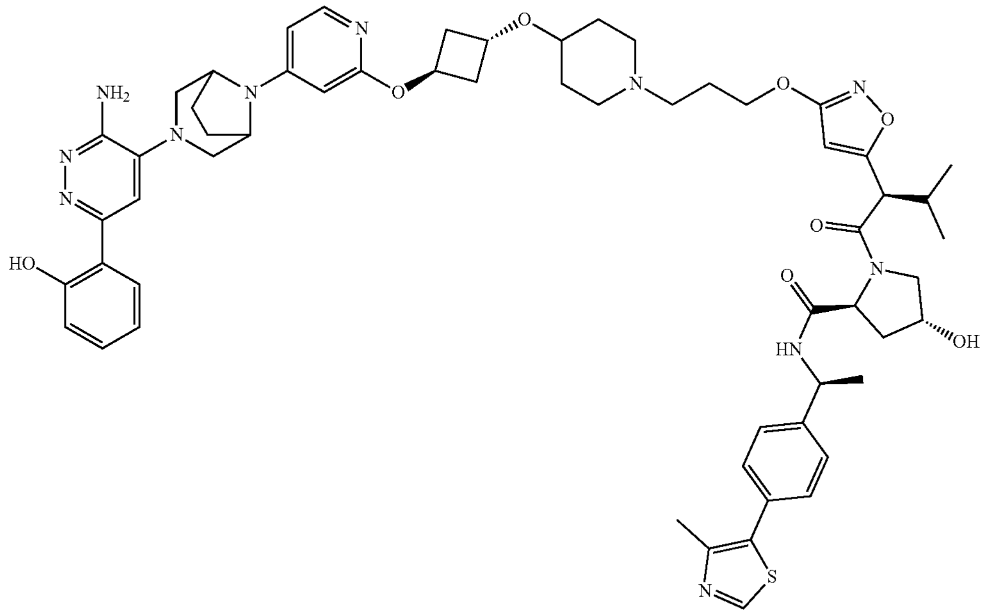
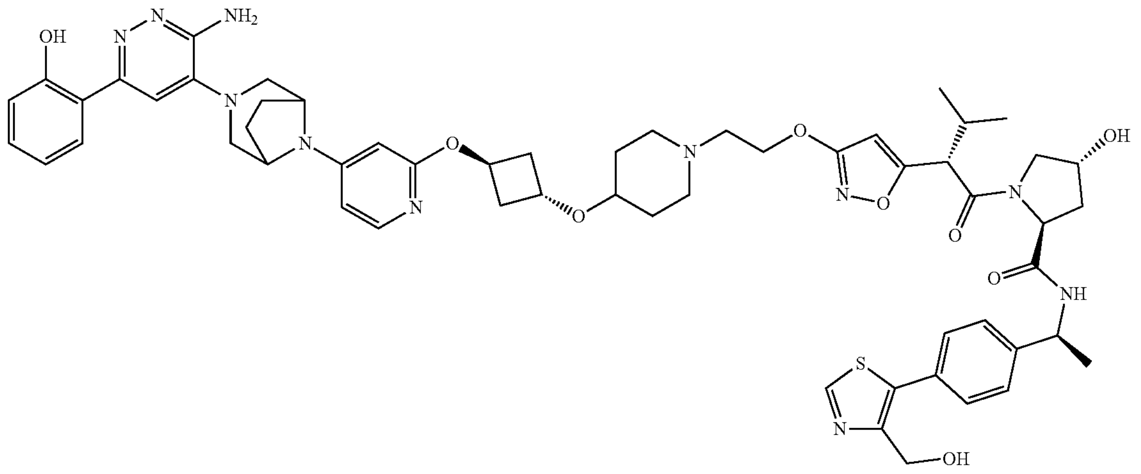 [SMILES: CC(C)[C@H](C(=O)N1C[C@H](O)C[C@H]1C(=O)N[C@@H](C)c1ccc(-c2scnc2CO)cc1)c1cc(OCCN2CCC(O[C@H]3C[C@H](Oc4cc(N5C6CCC5CN(c5cc(-c7ccccc7O)nnc5N)C6)ccn4)C3)CC2)no1]

-continued
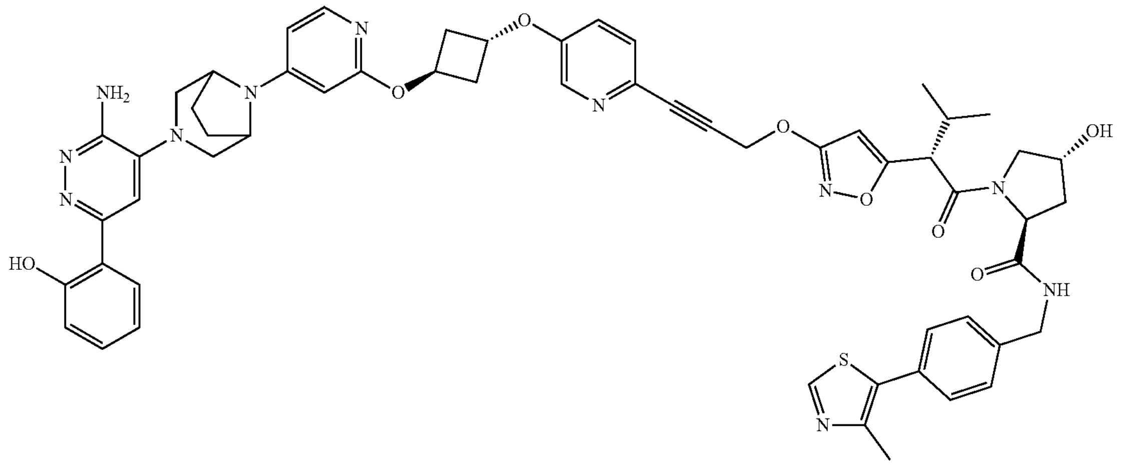
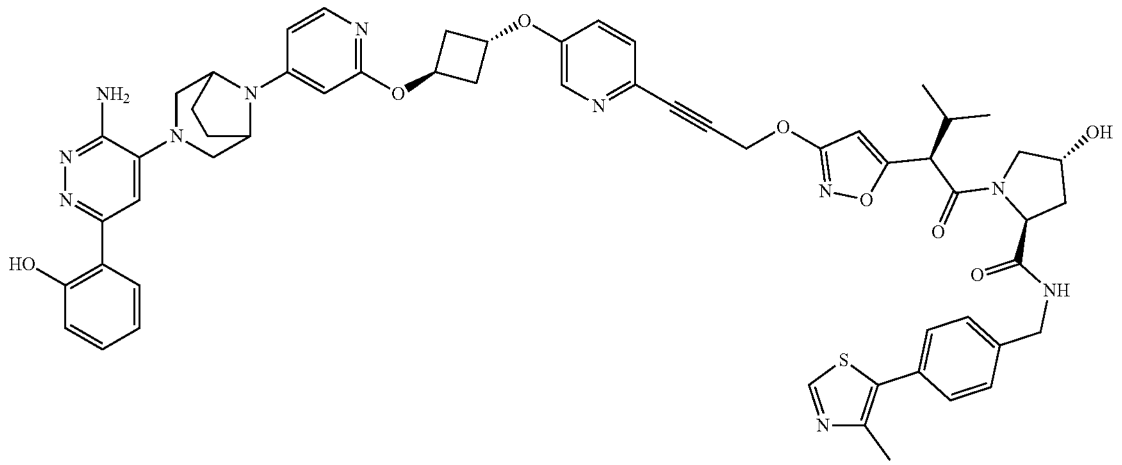
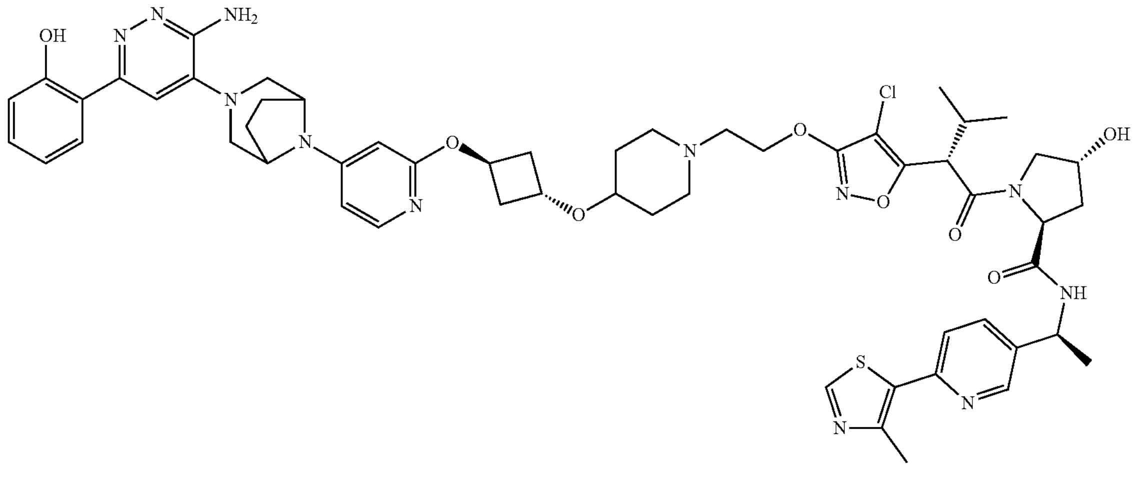

-continued
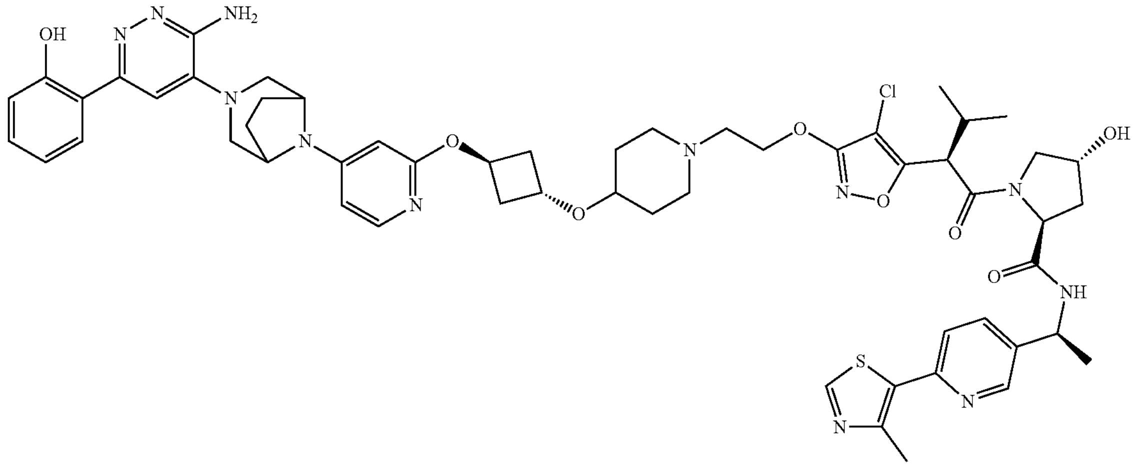
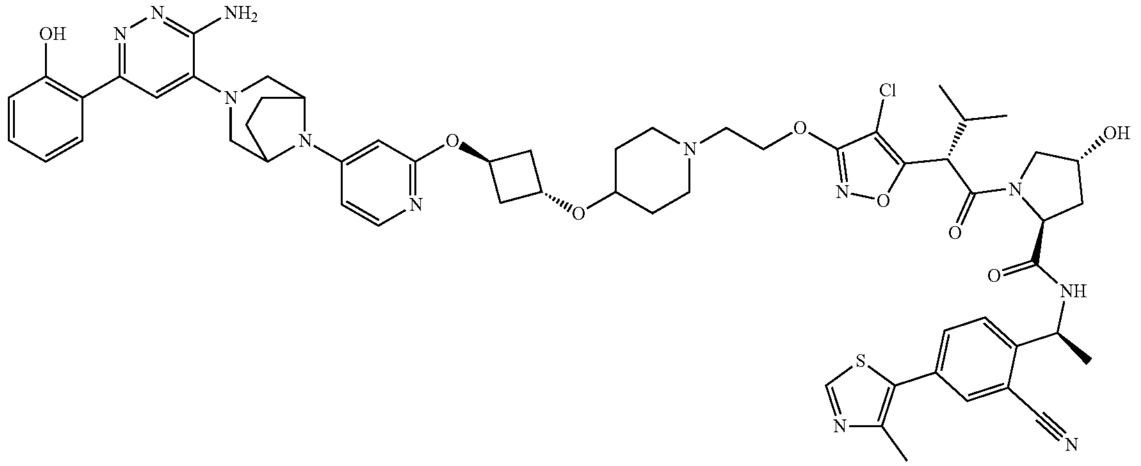
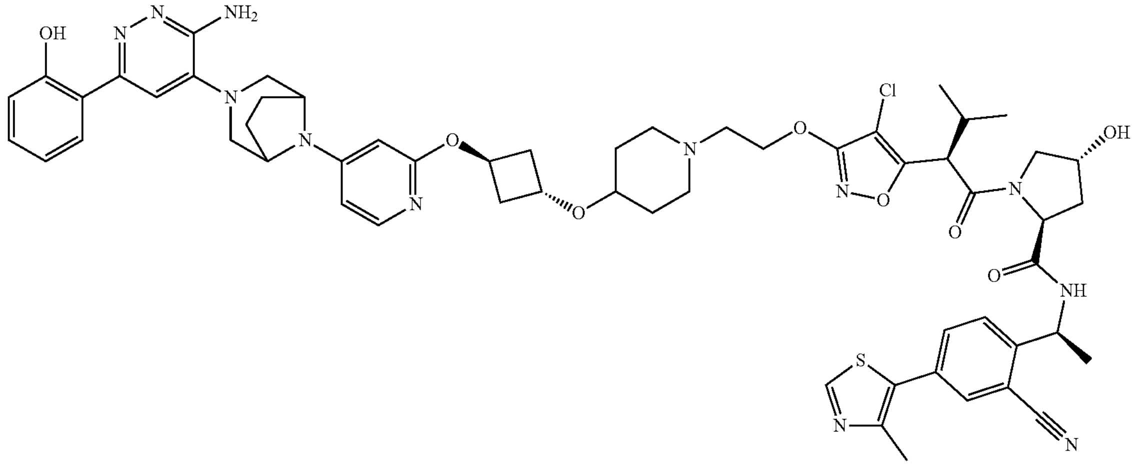

-continued
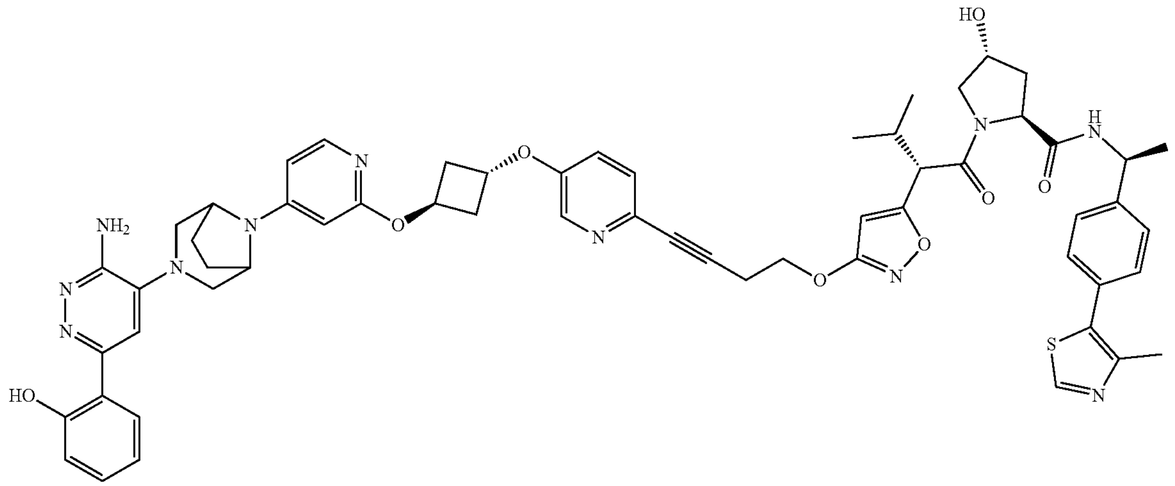
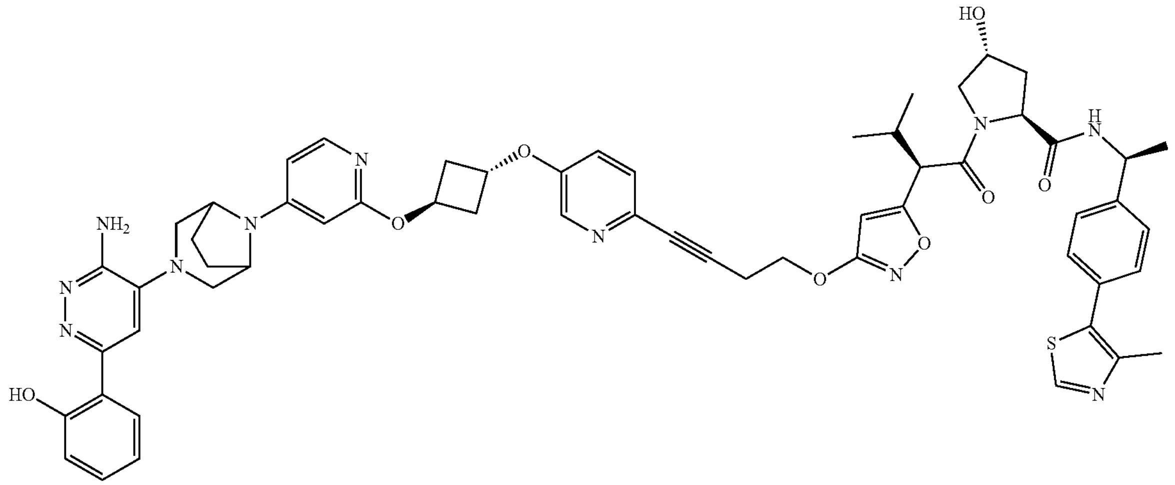
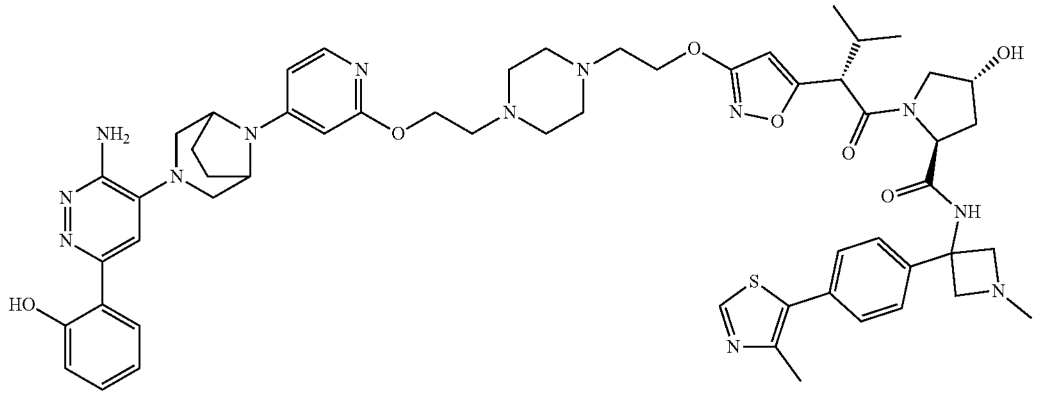

-continued
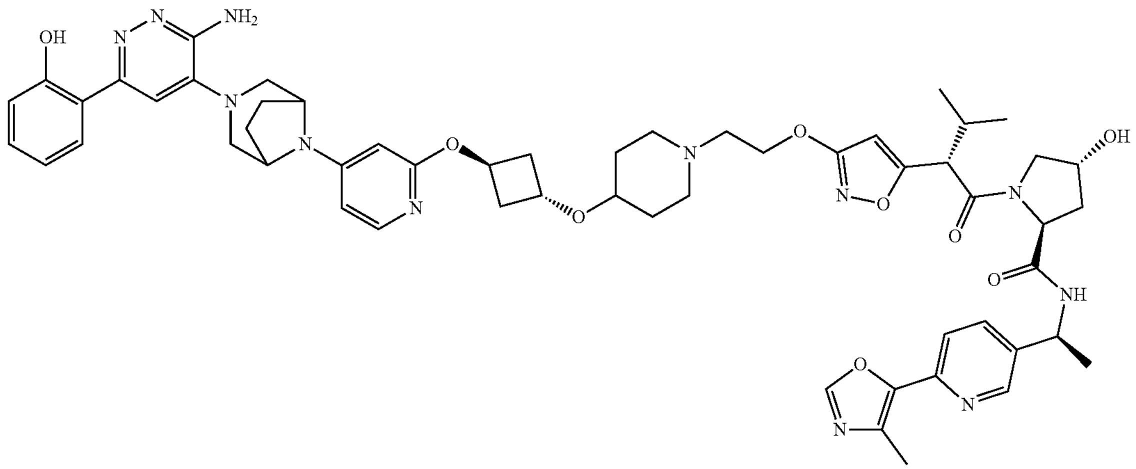
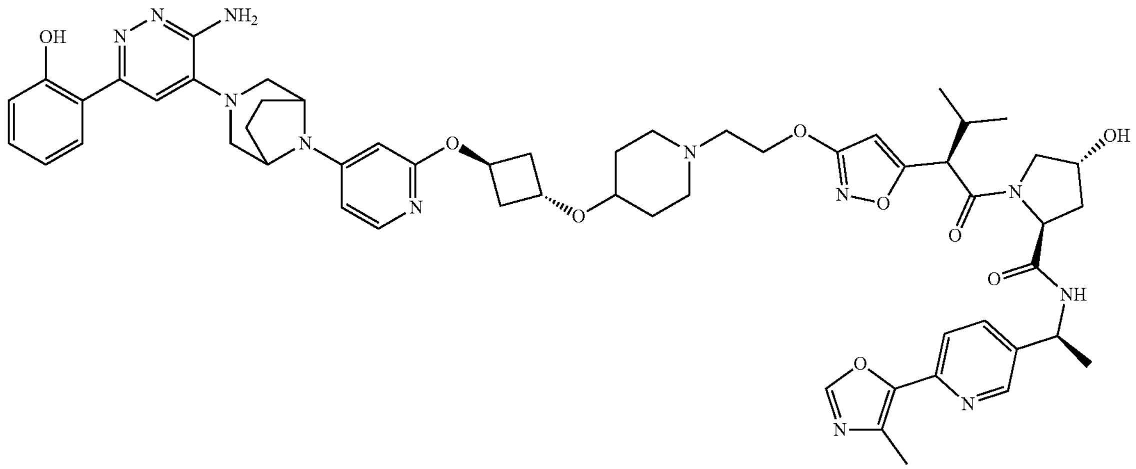
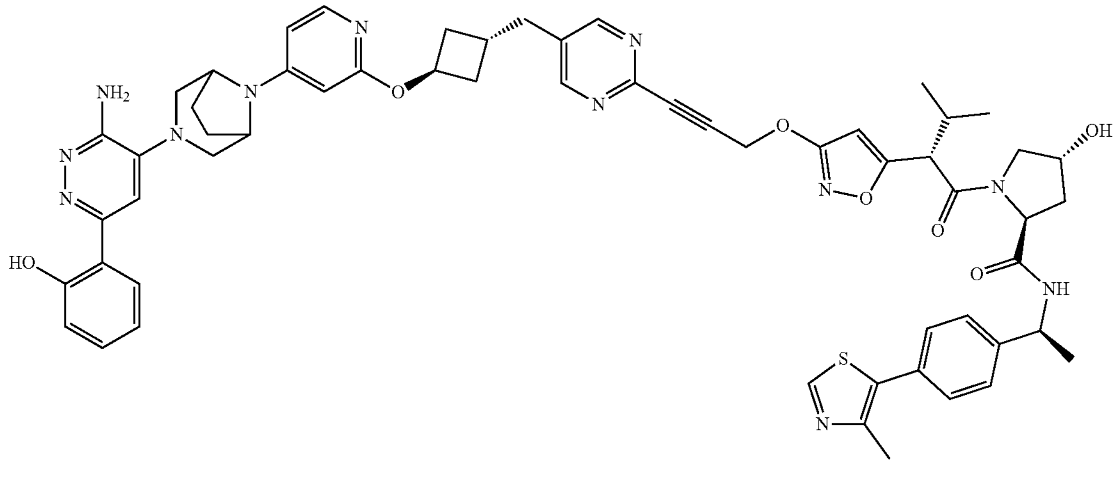

-continued
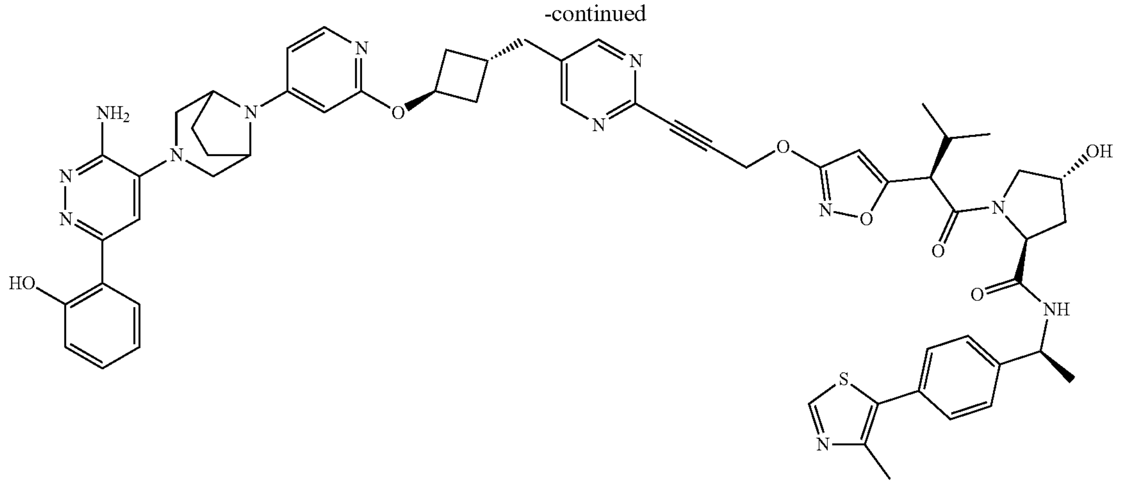
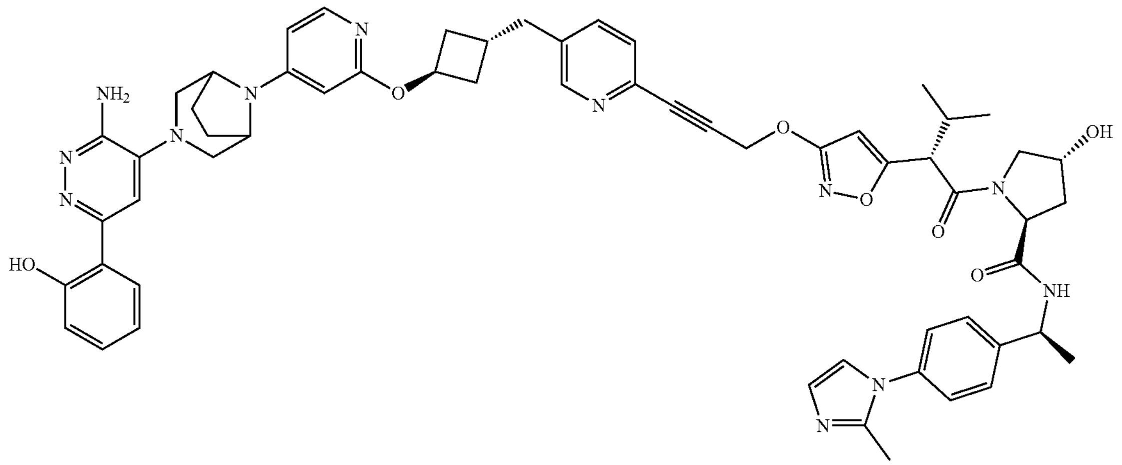
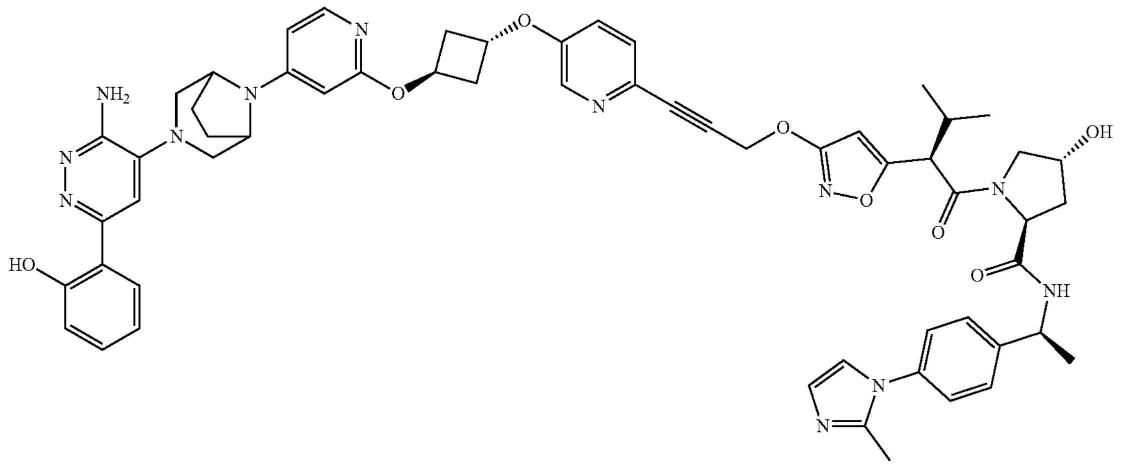

-continued
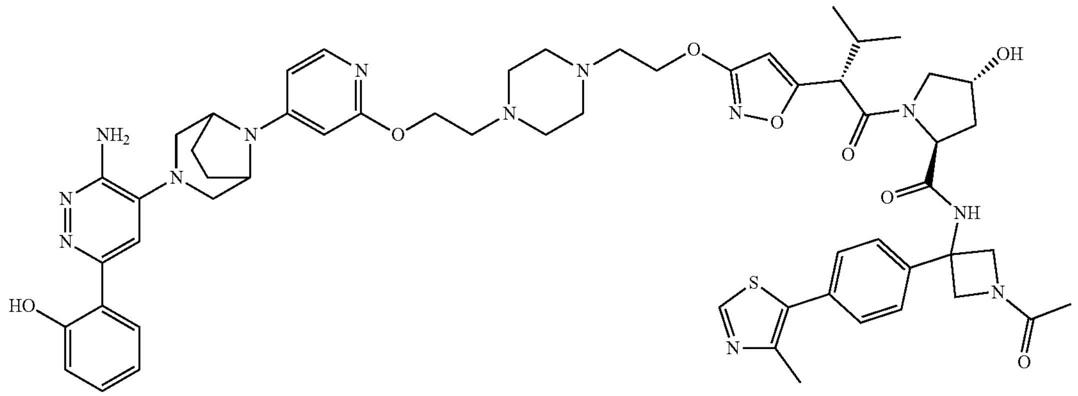
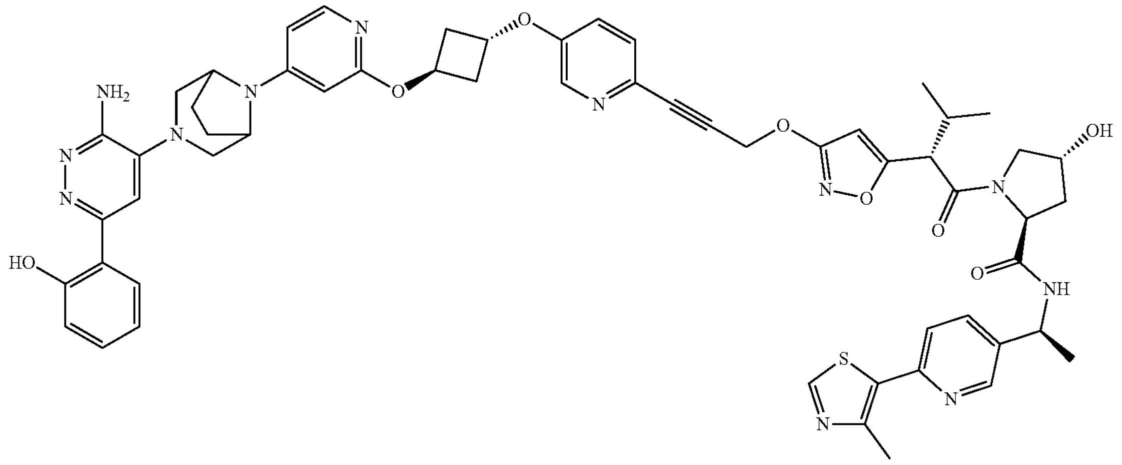
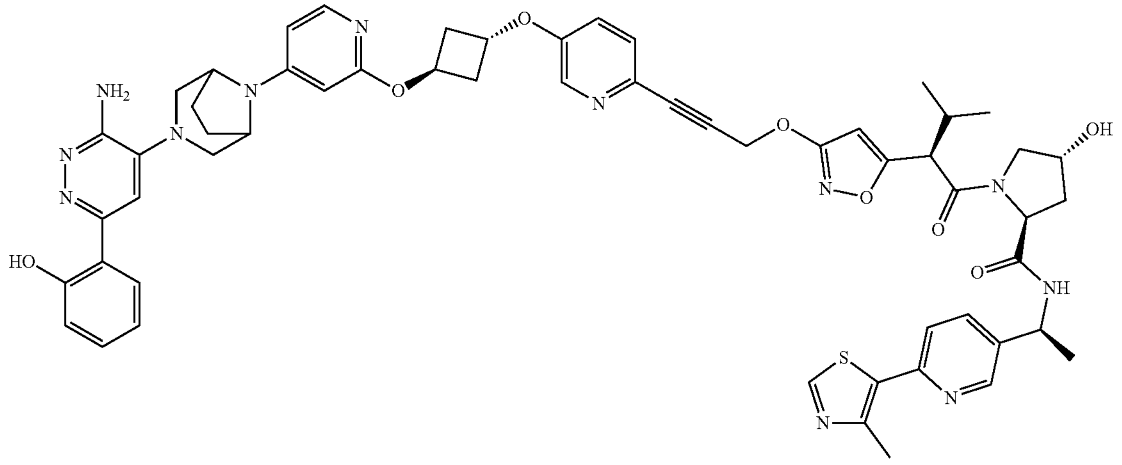
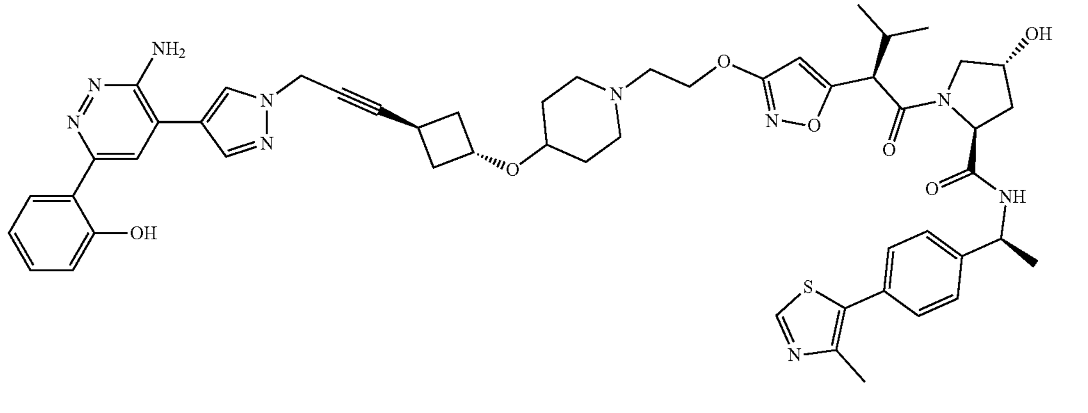

-continued
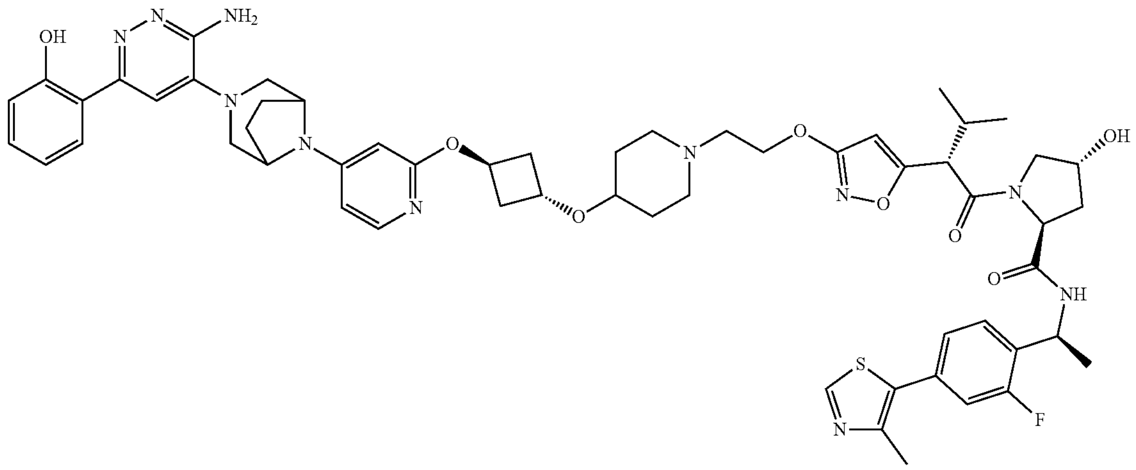
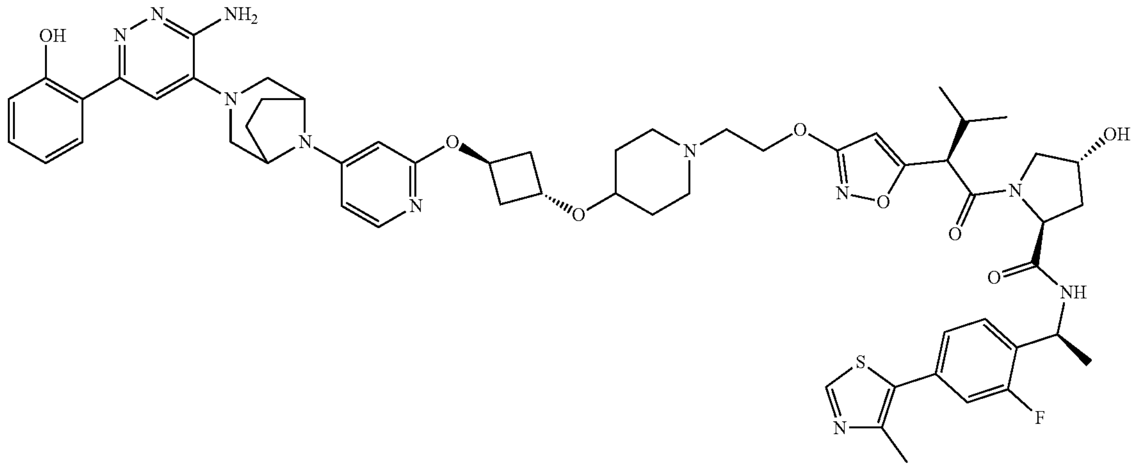
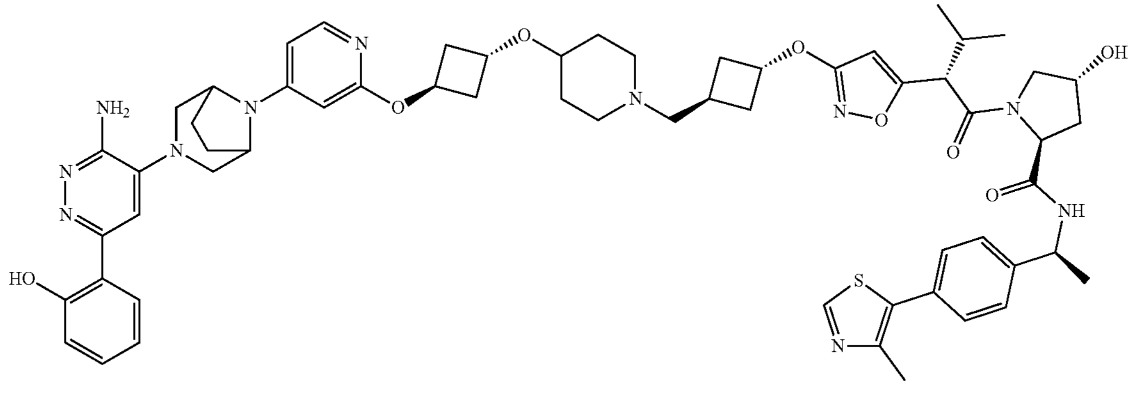
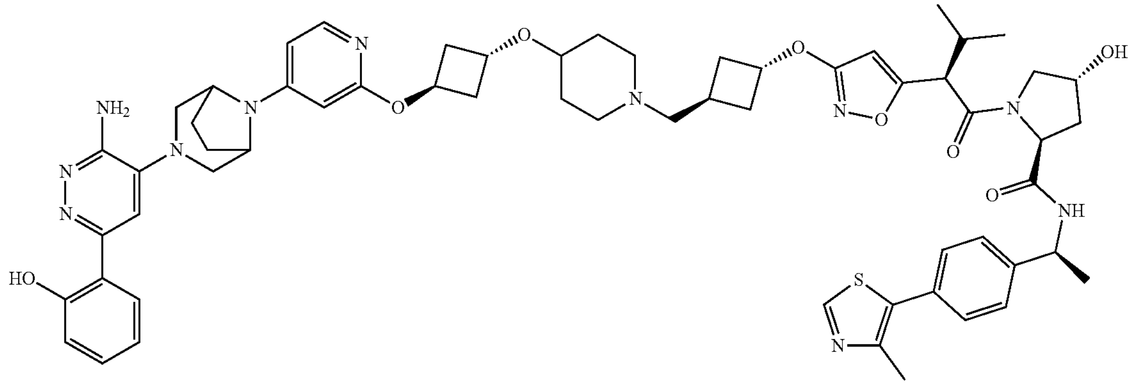

-continued
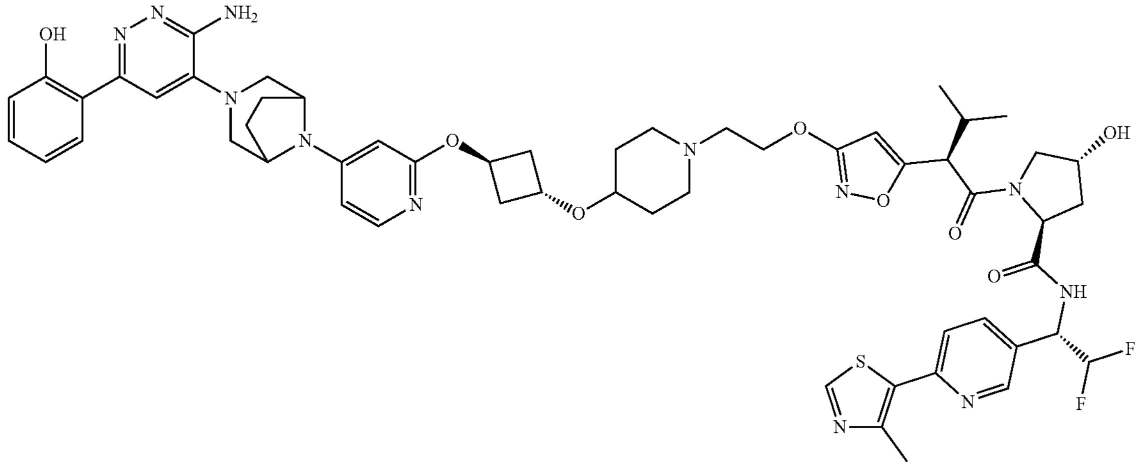
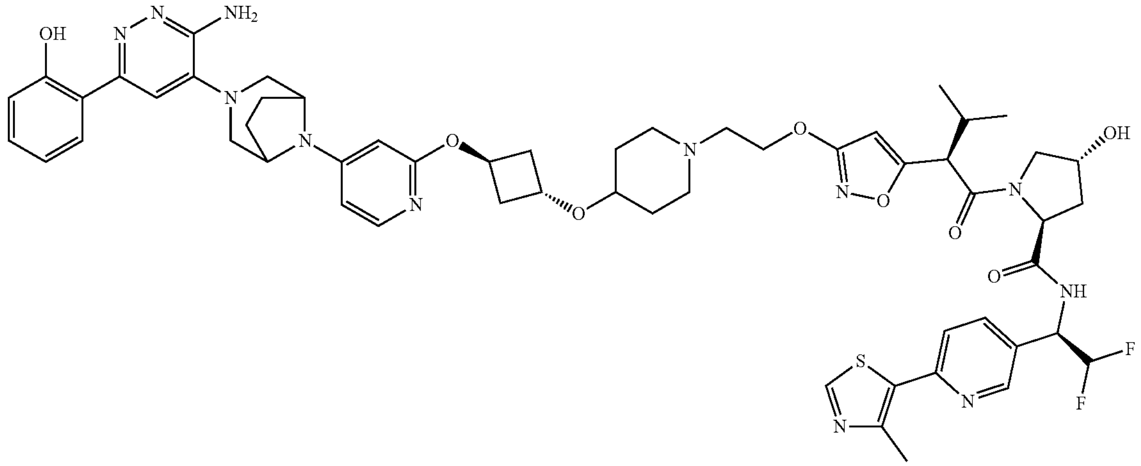
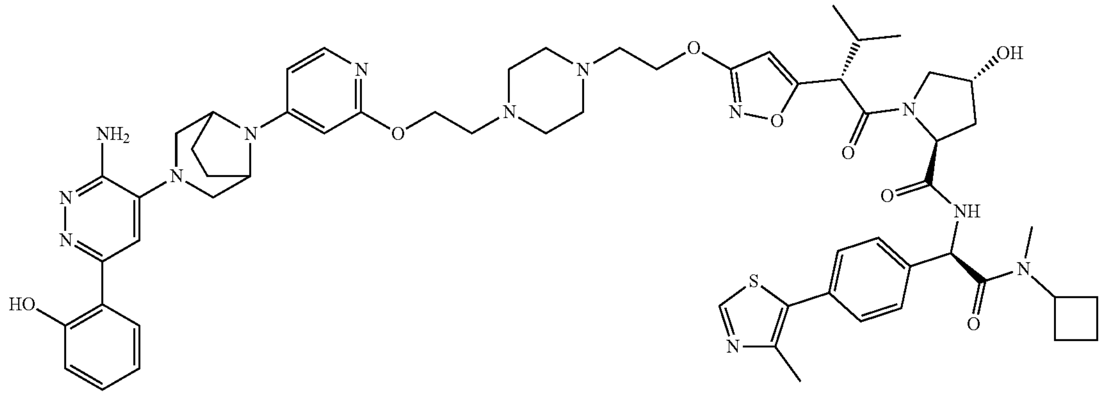
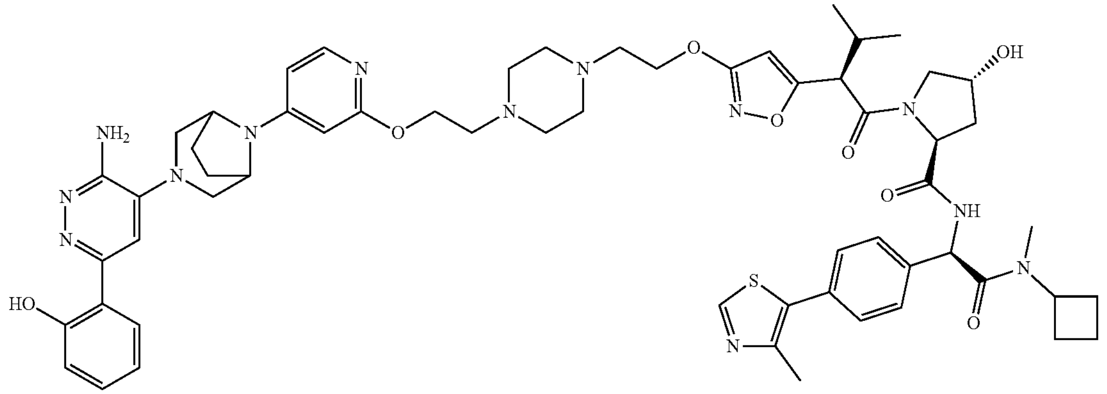

-continued
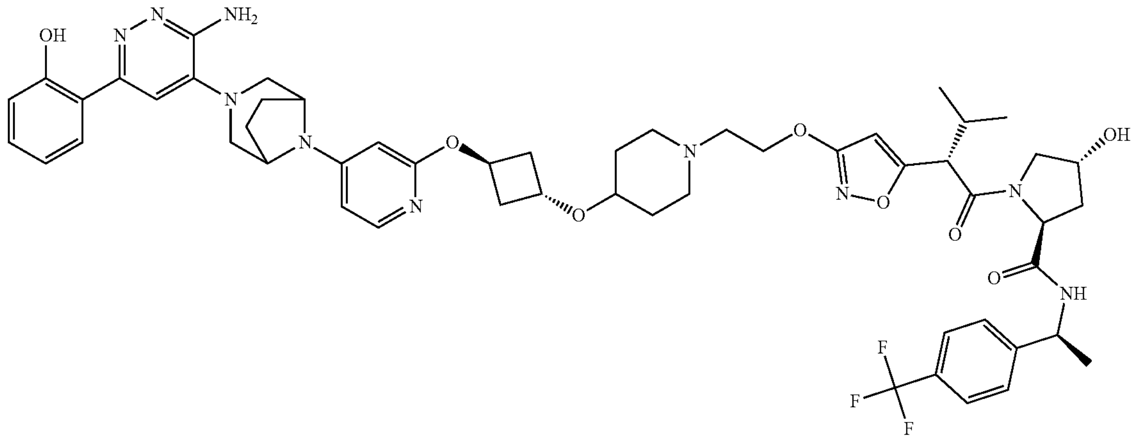
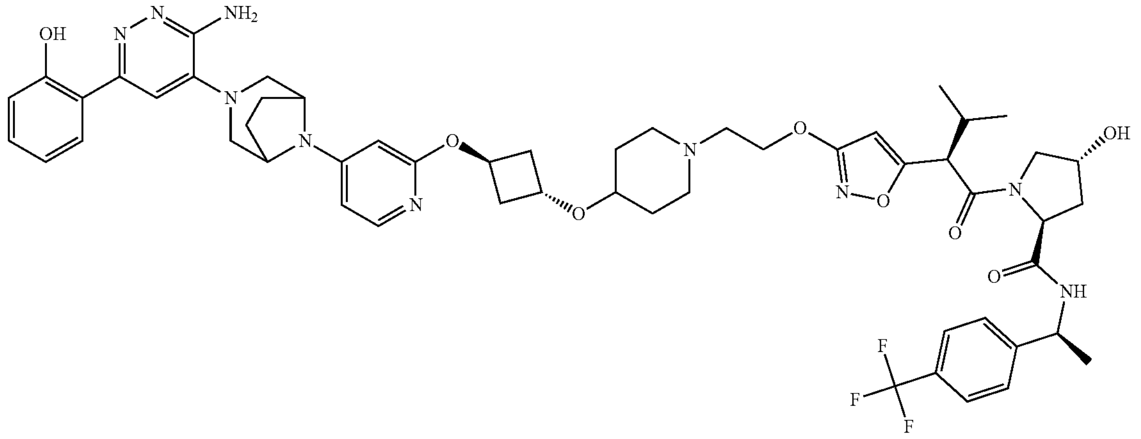
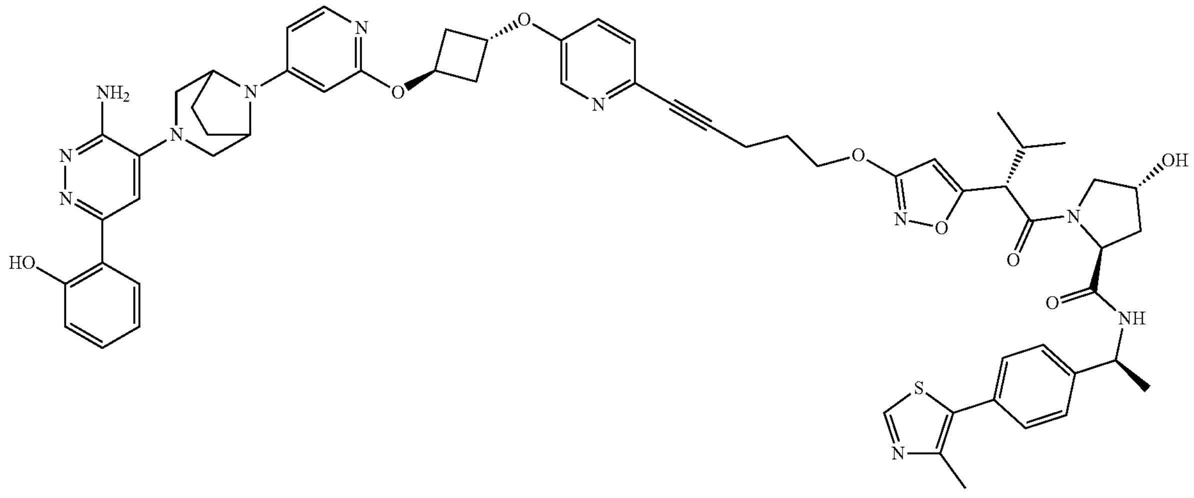

-continued
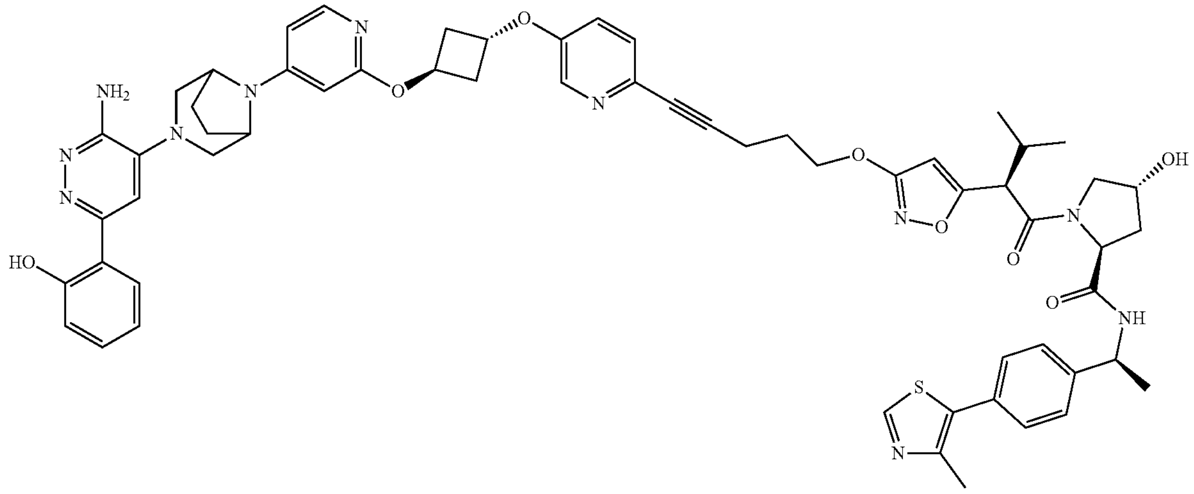
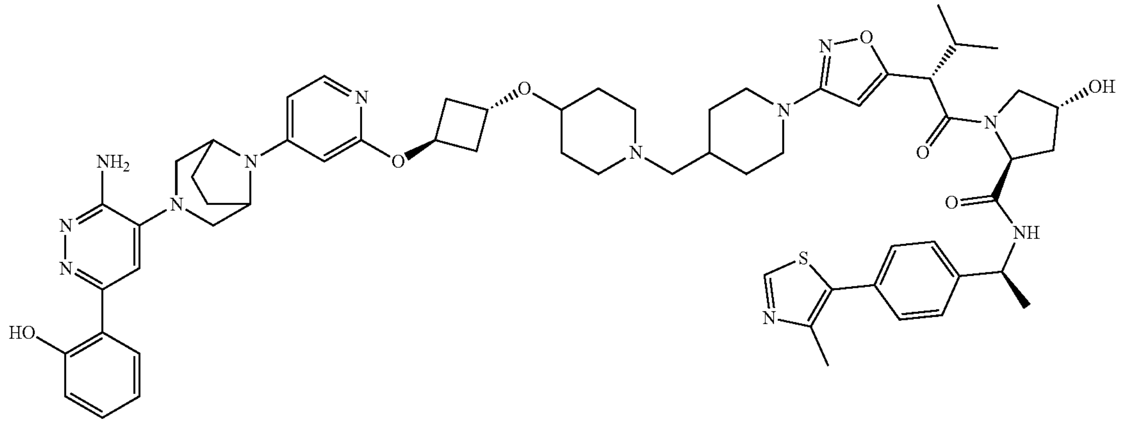
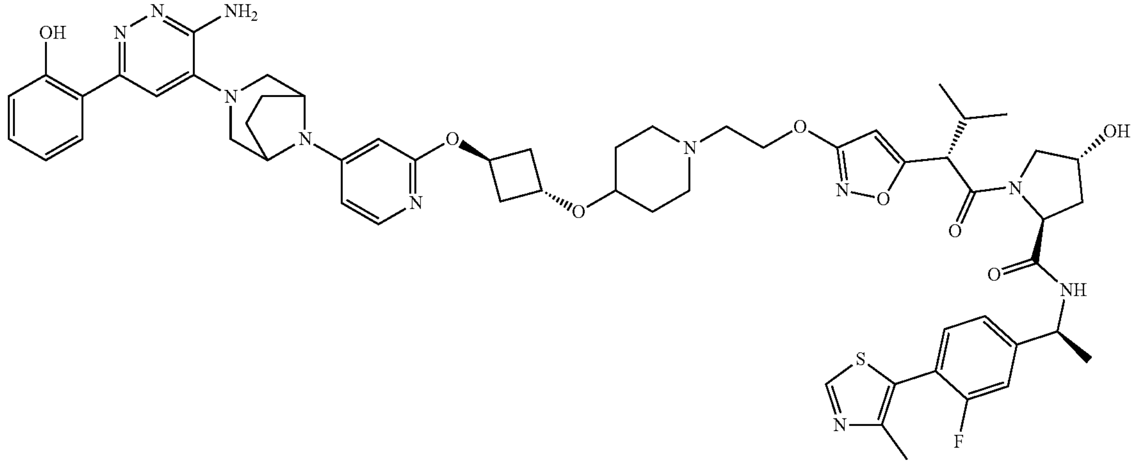

-continued
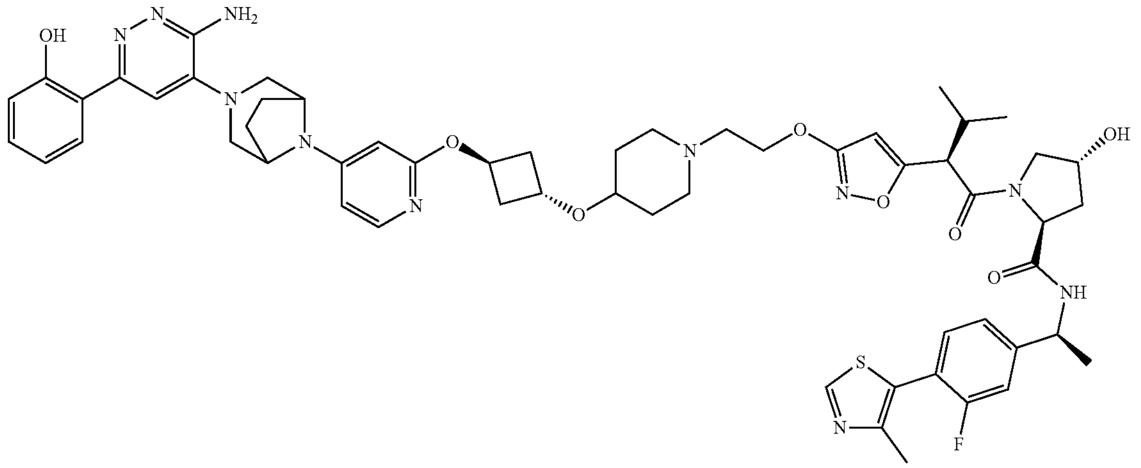
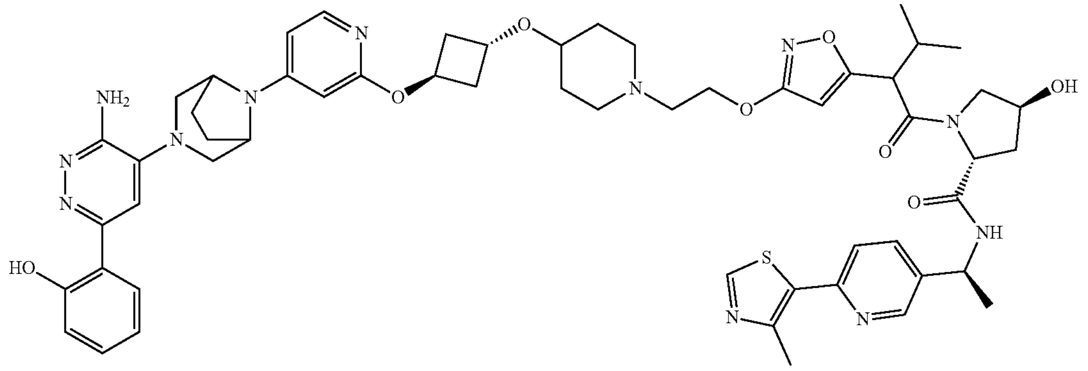
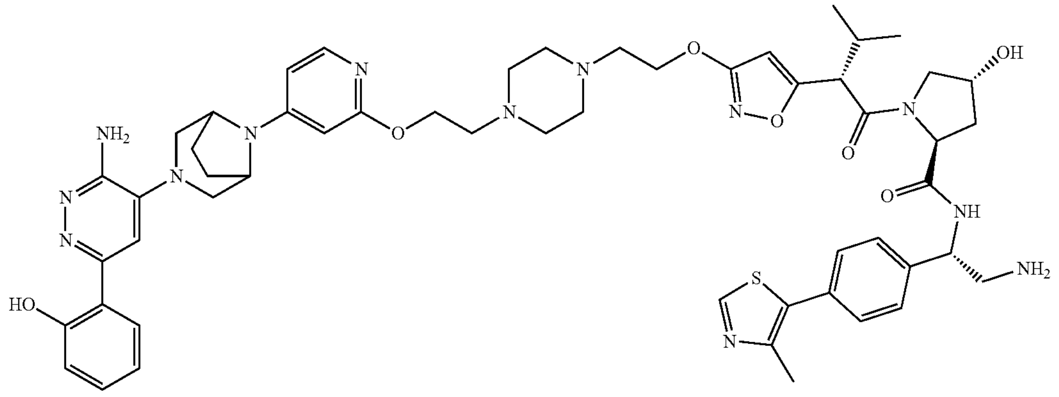
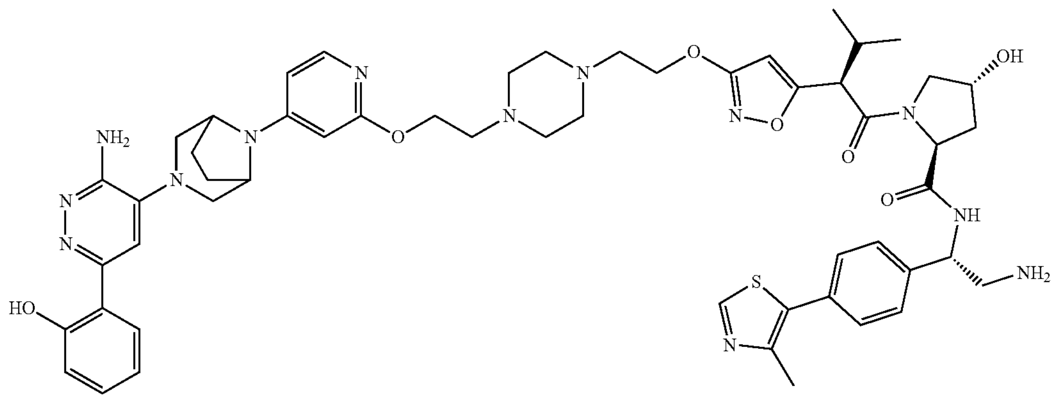

-continued
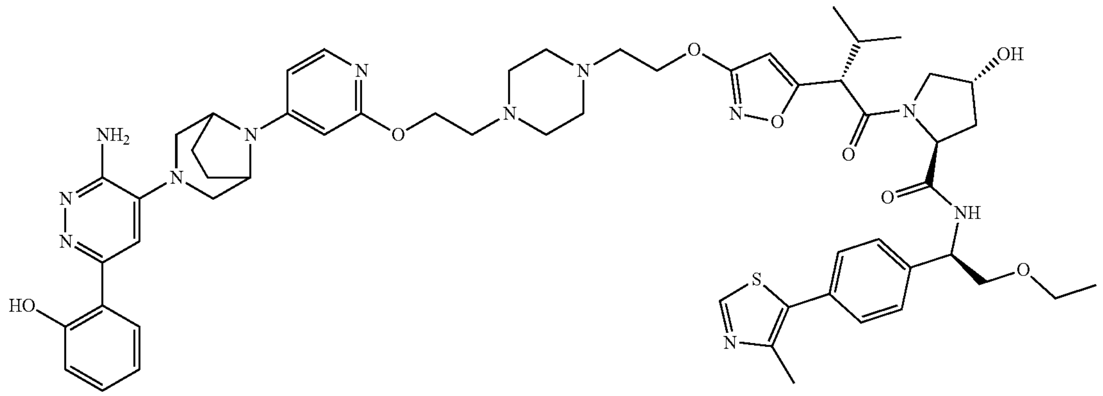
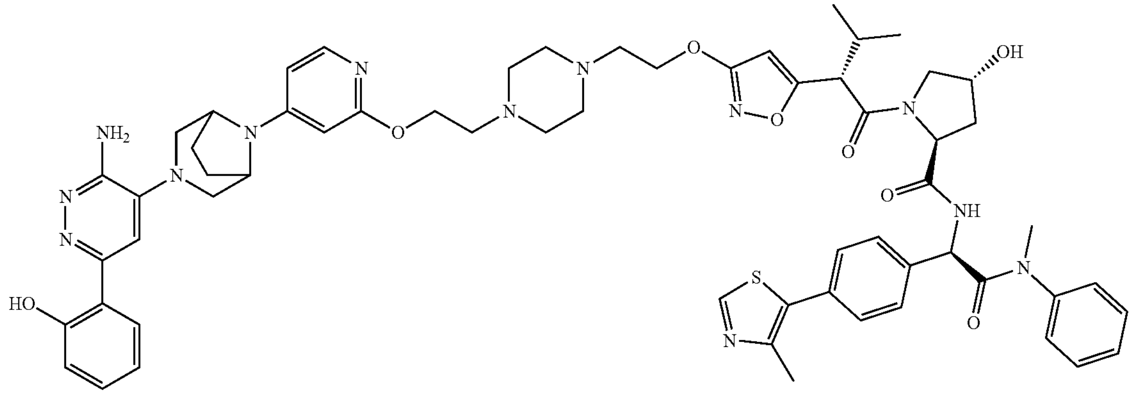
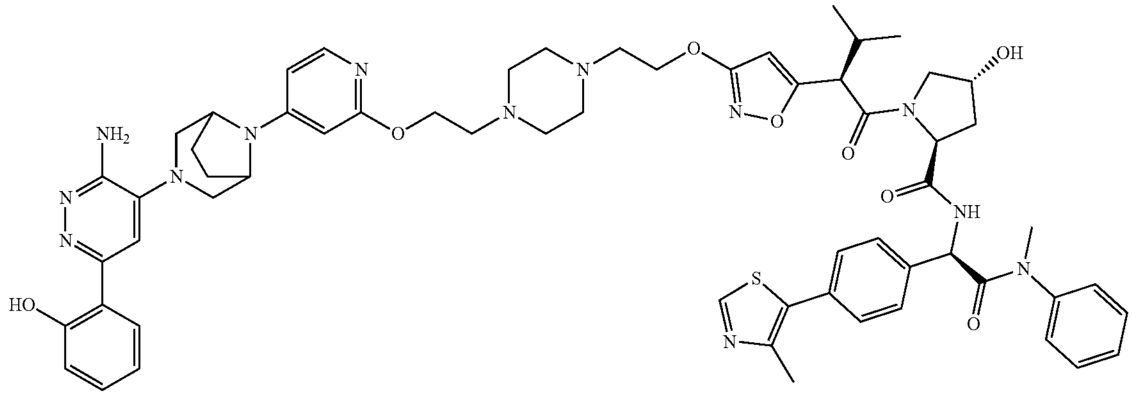
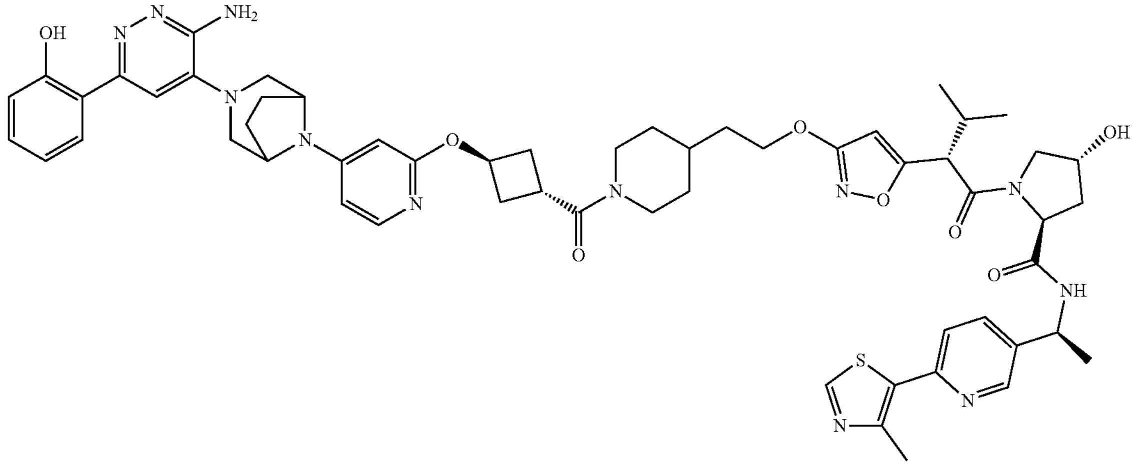

-continued
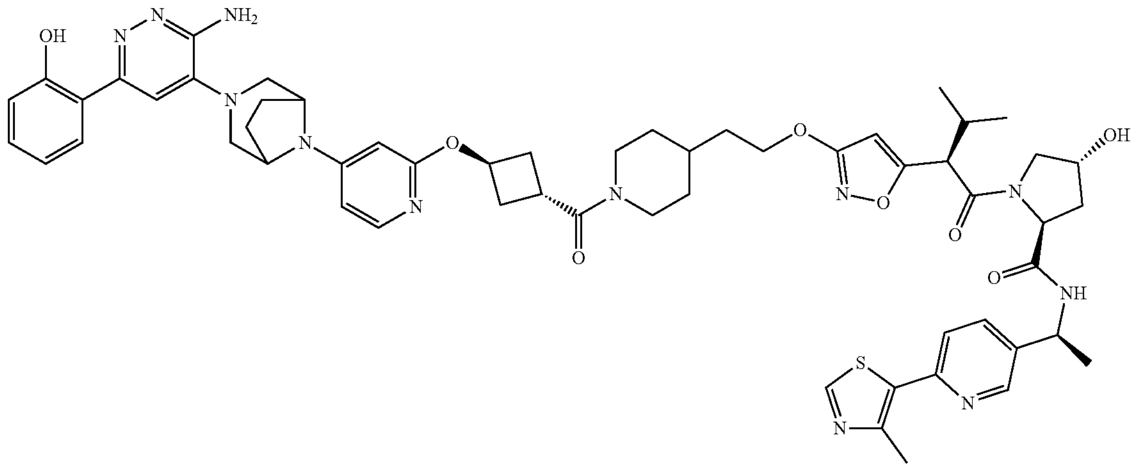
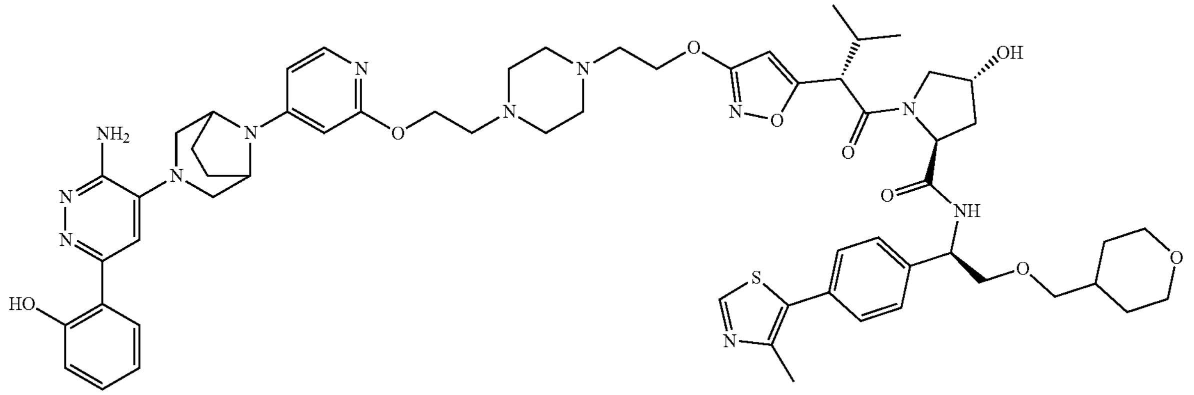
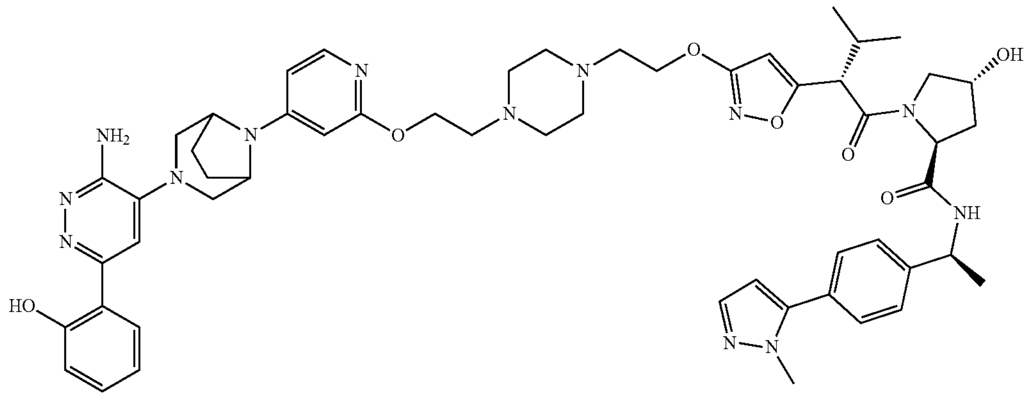
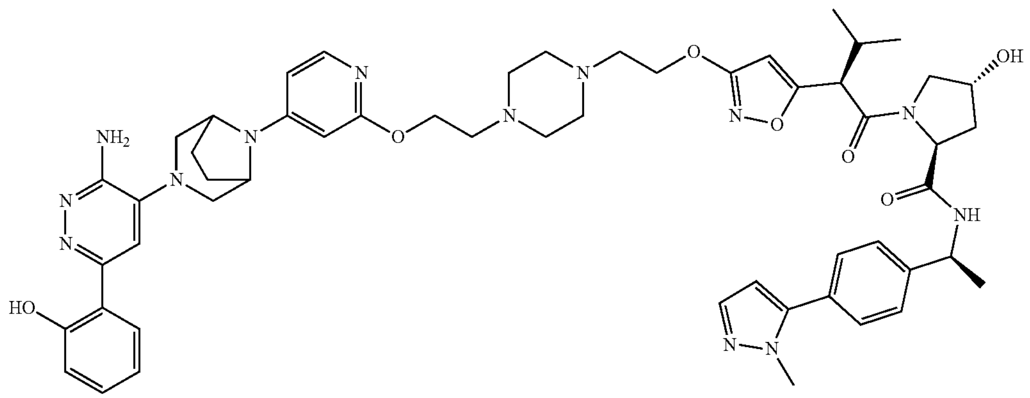

-continued
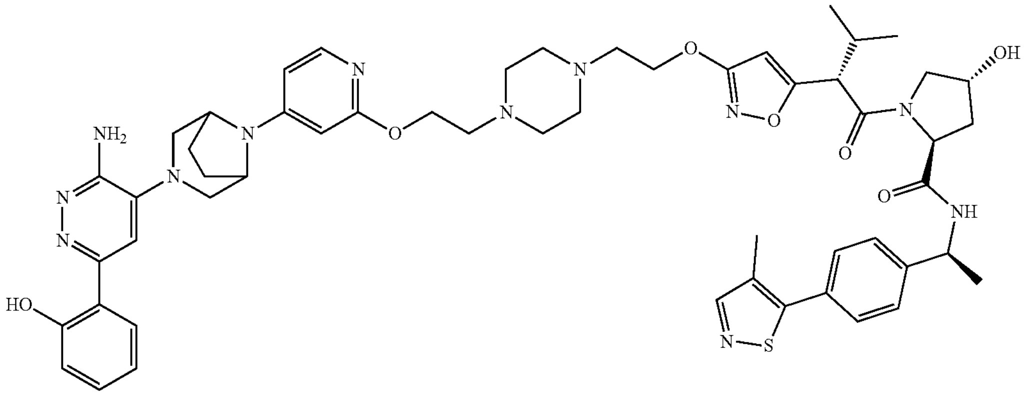
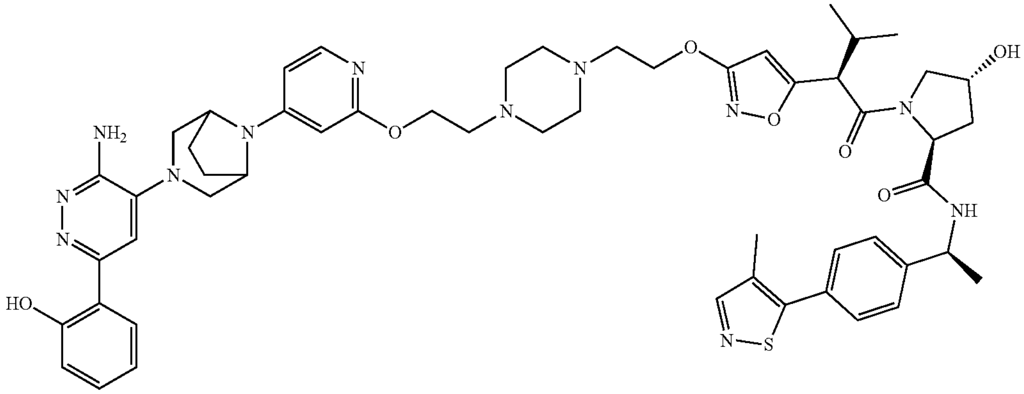
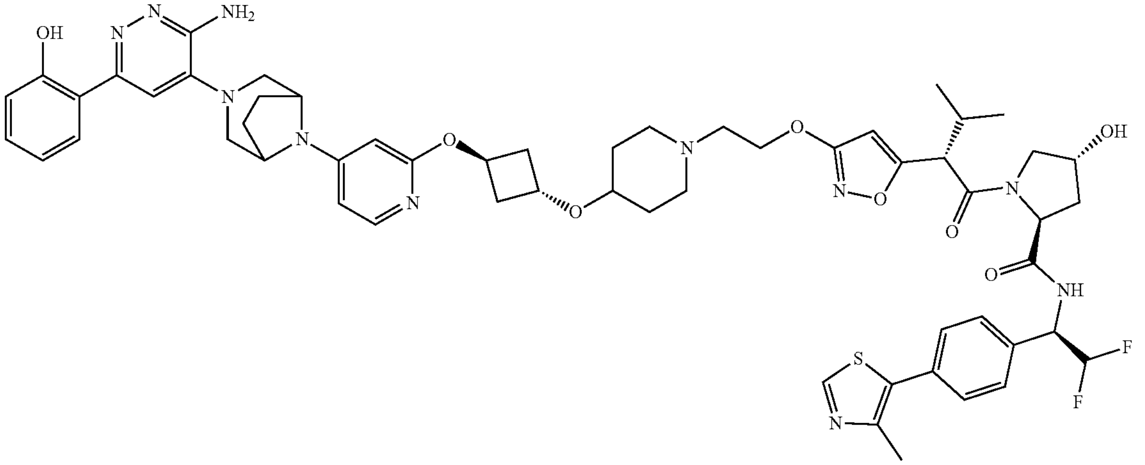
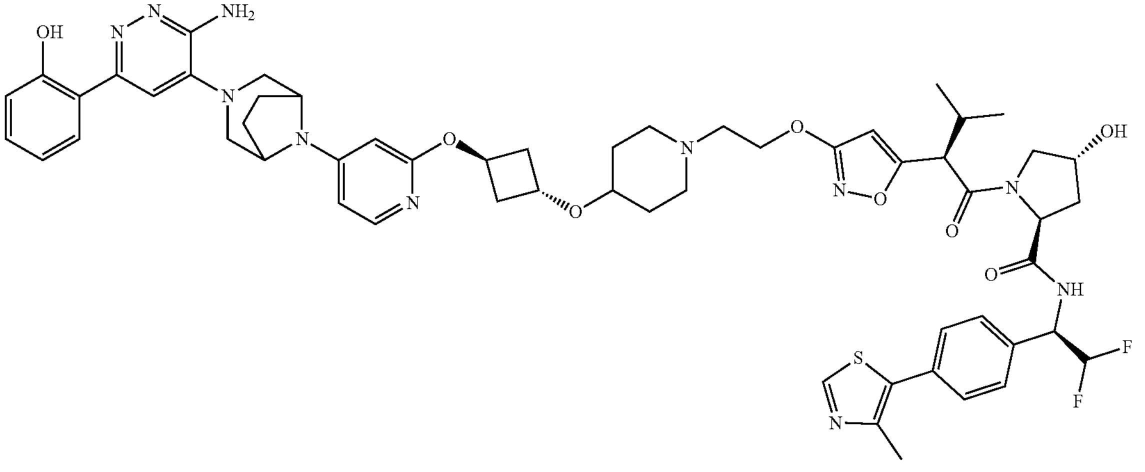

-continued
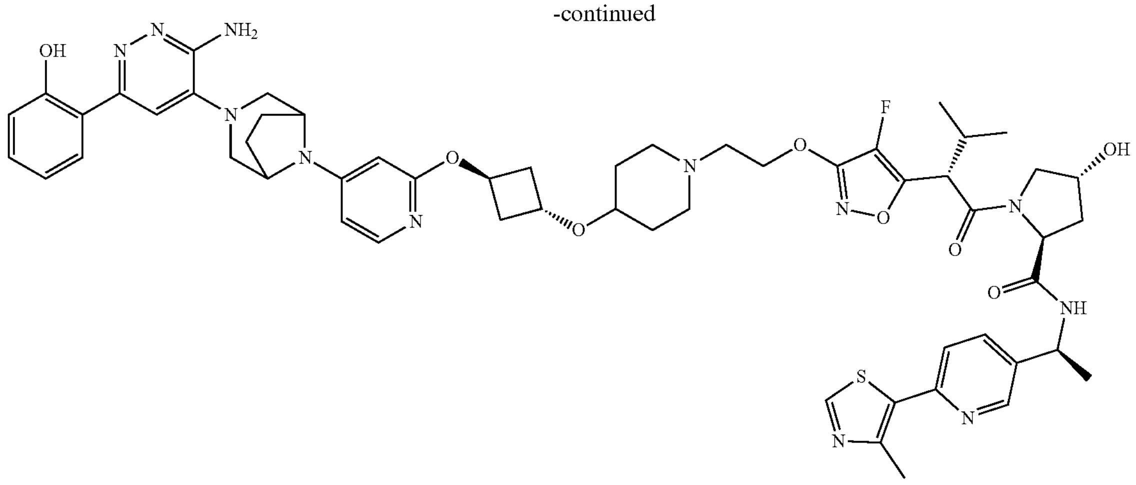
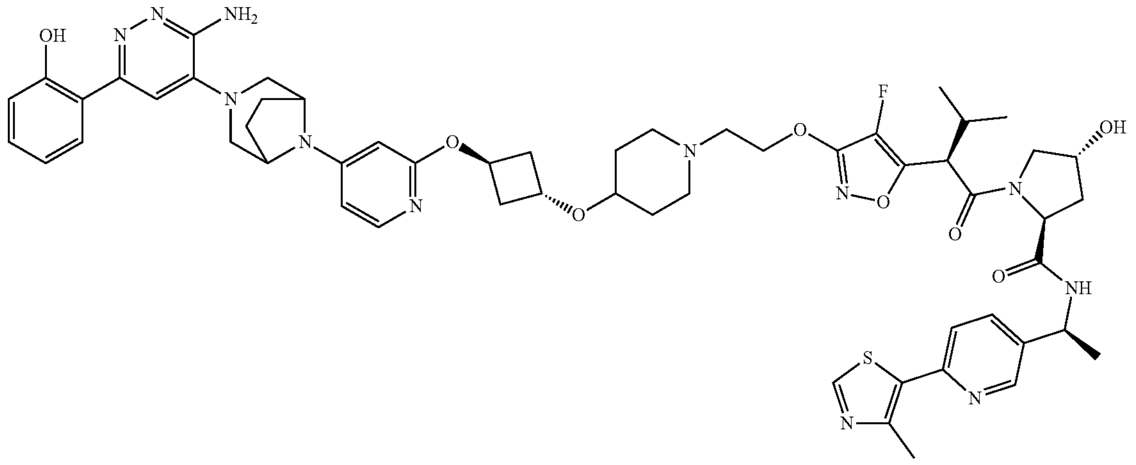
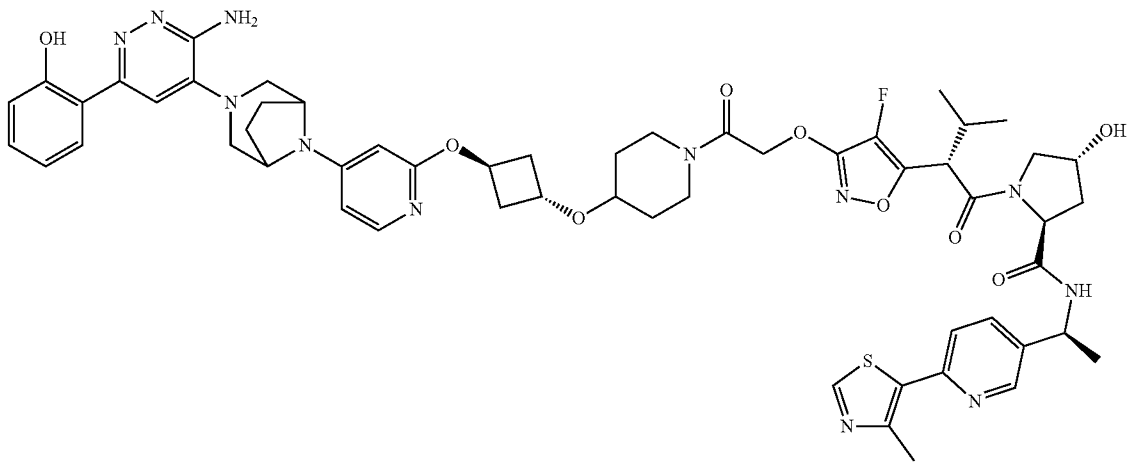

-continued
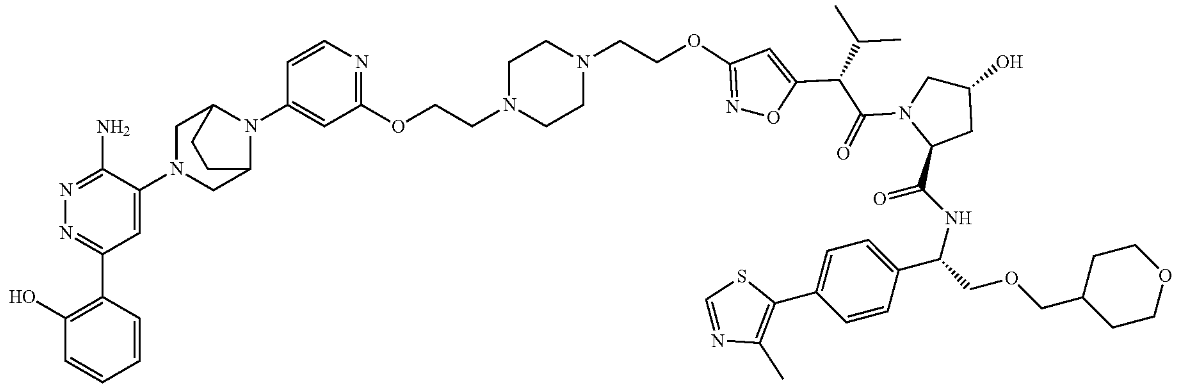
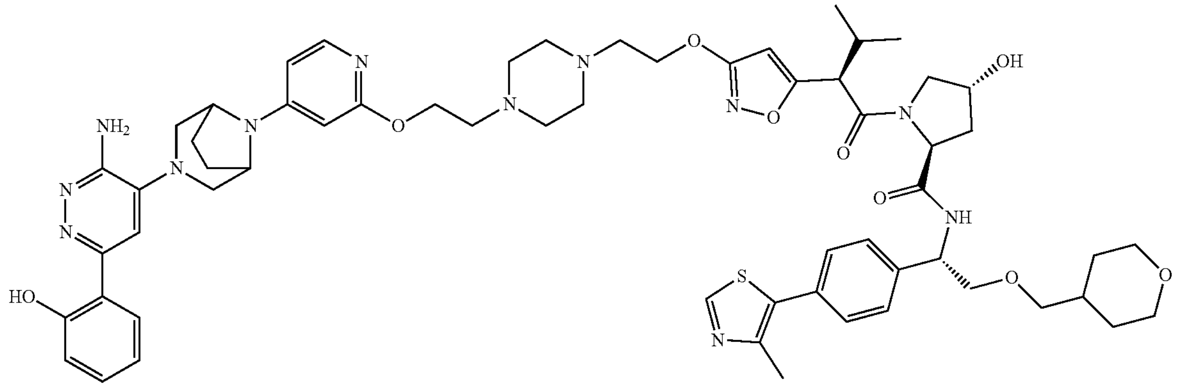
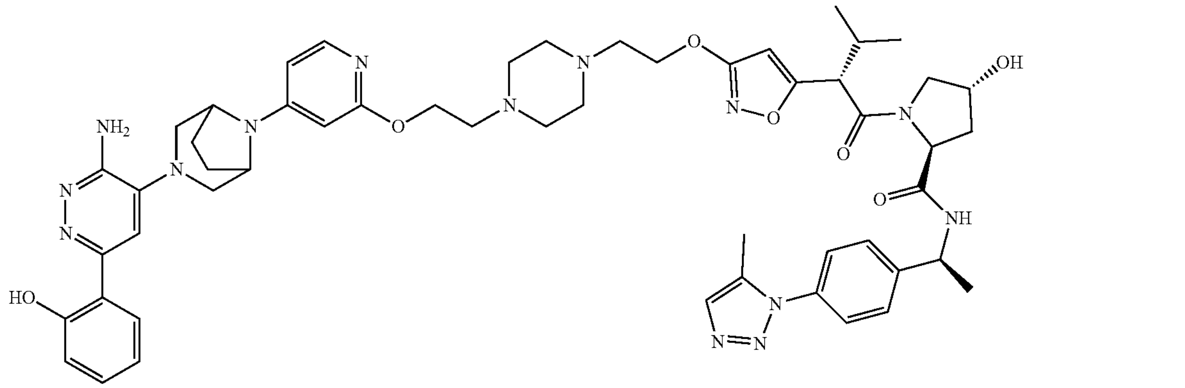
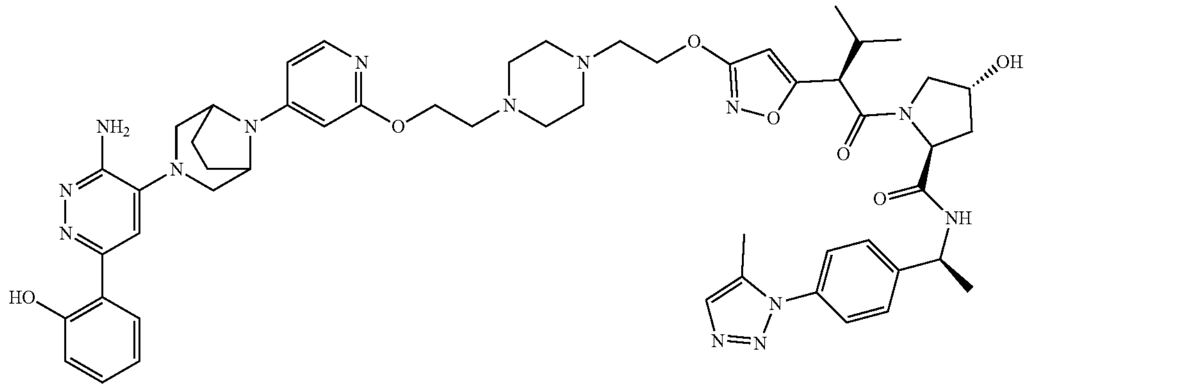

-continued
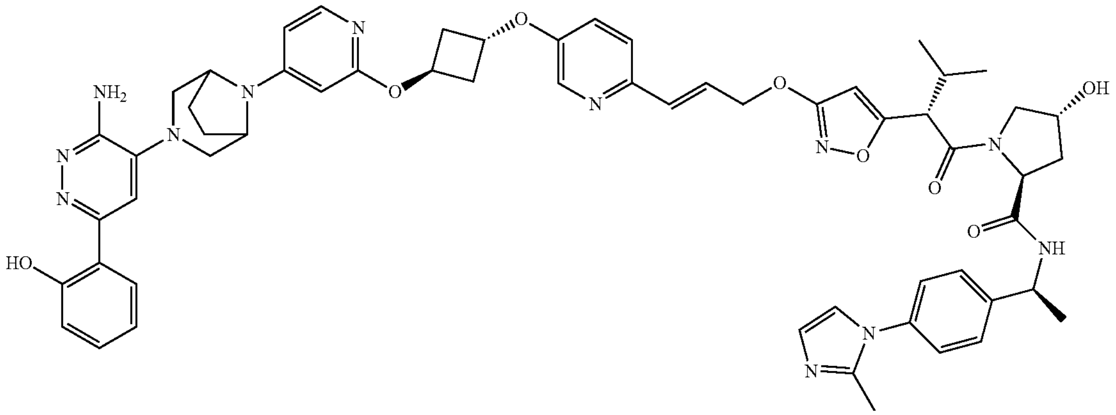
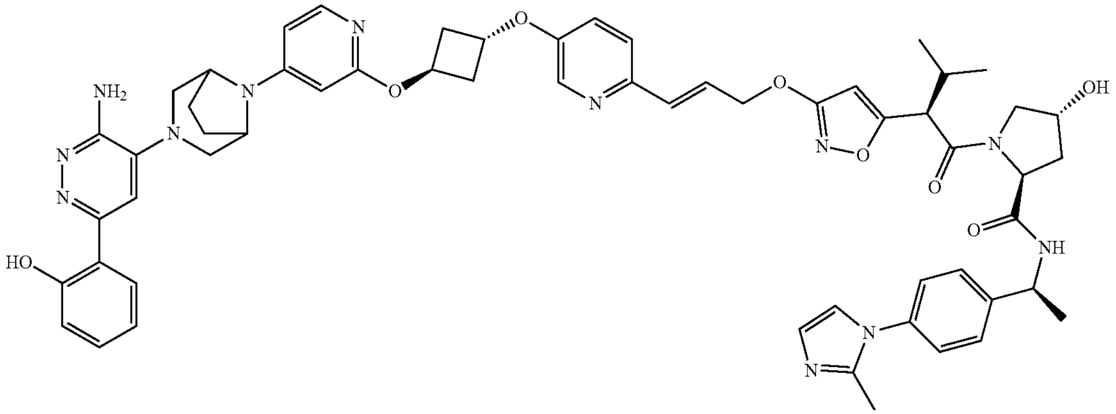
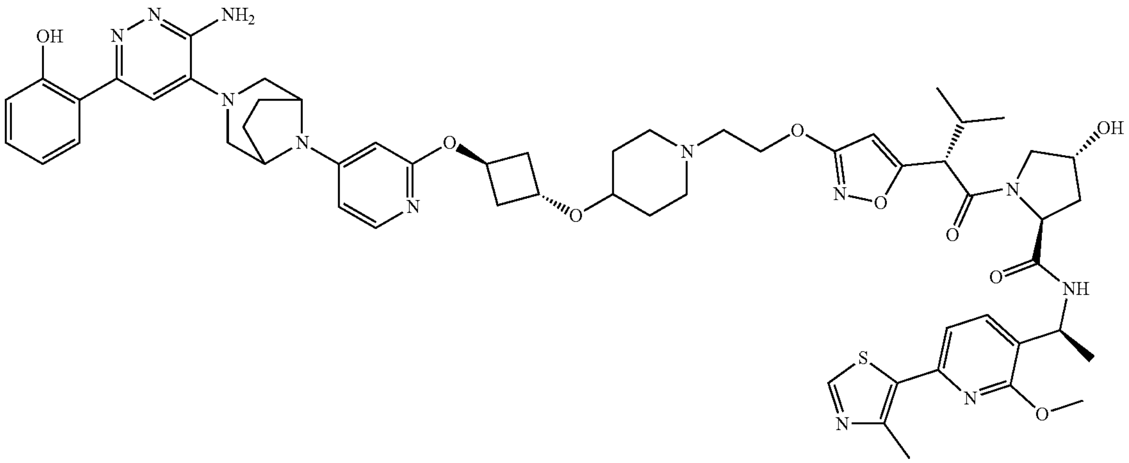

-continued
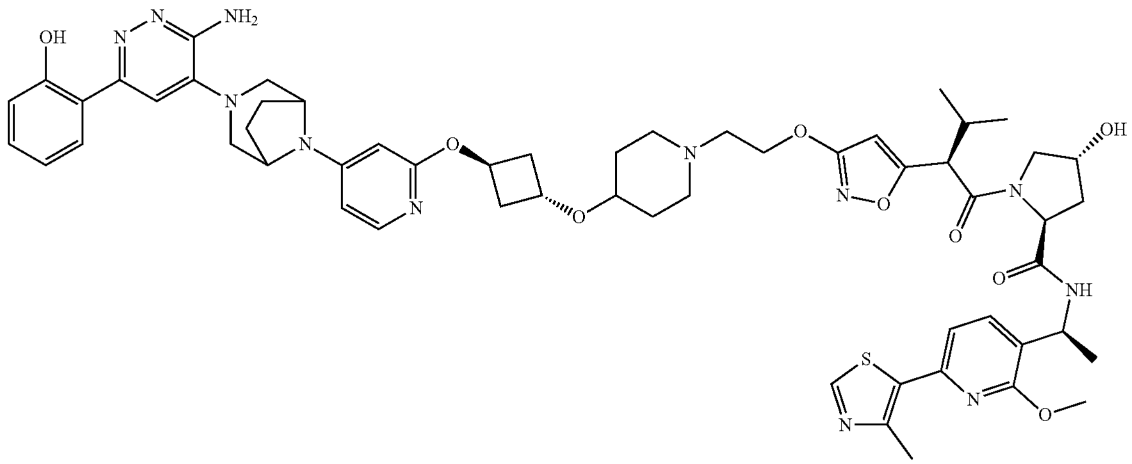
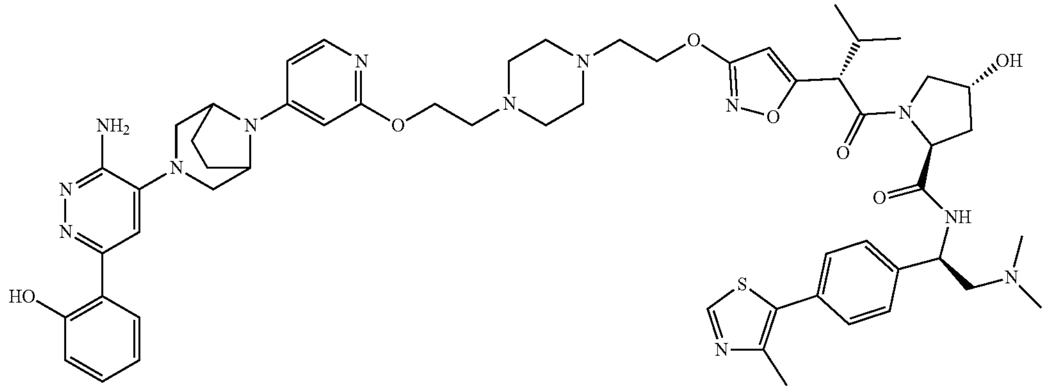
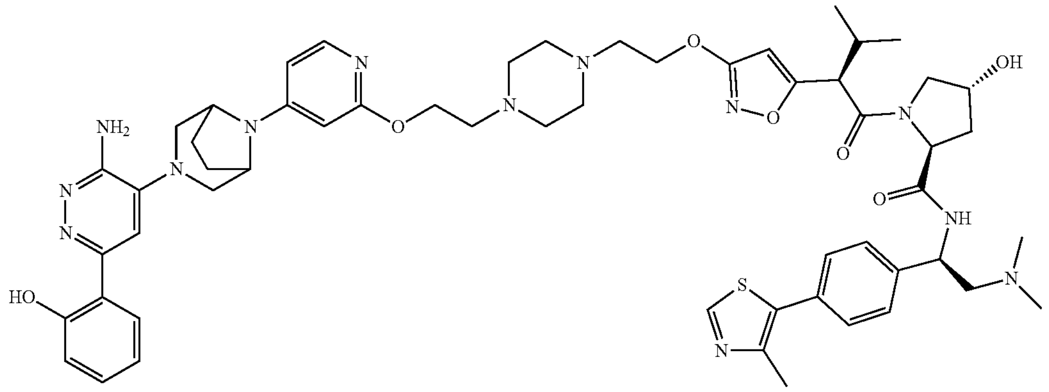
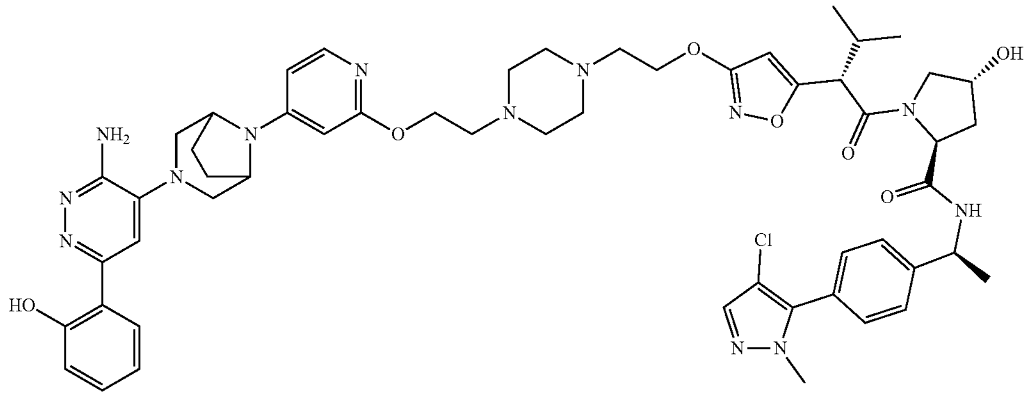

-continued
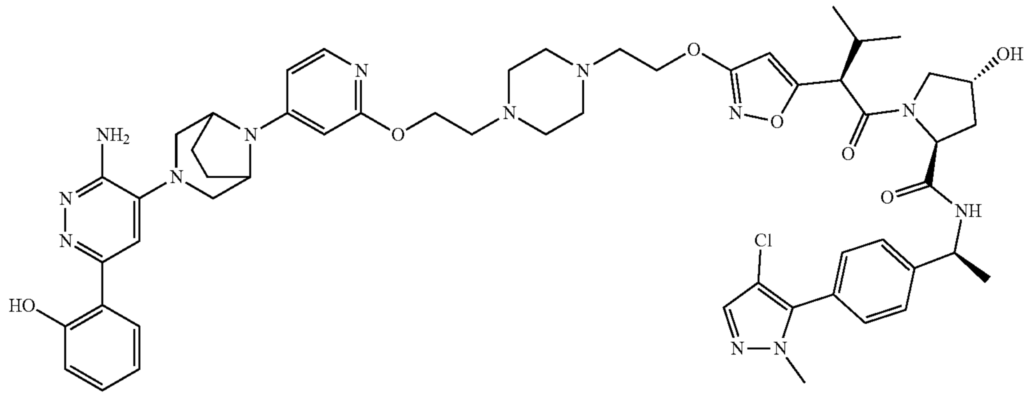
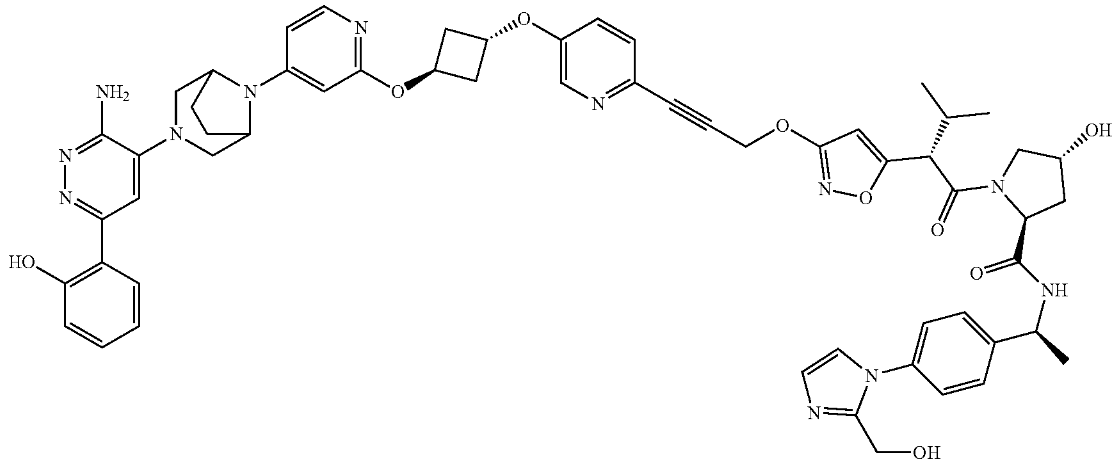
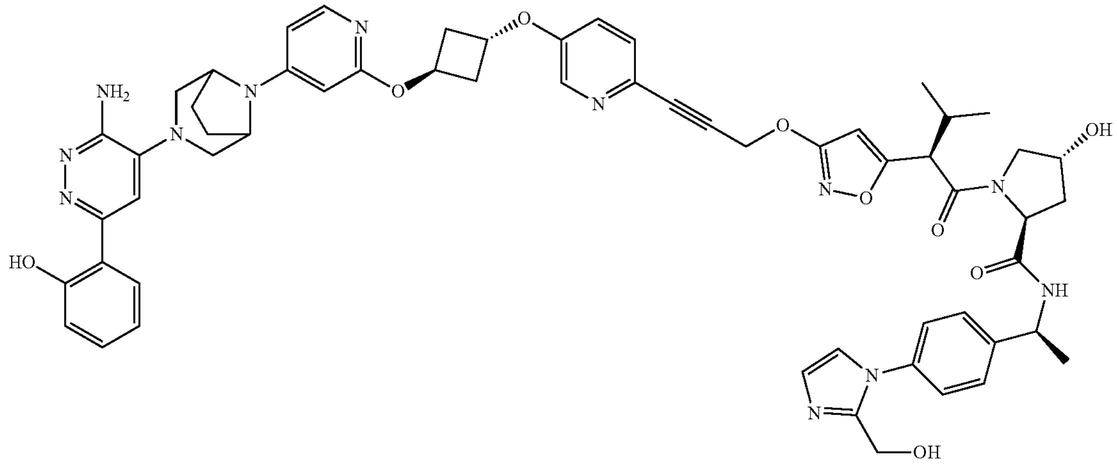

-continued
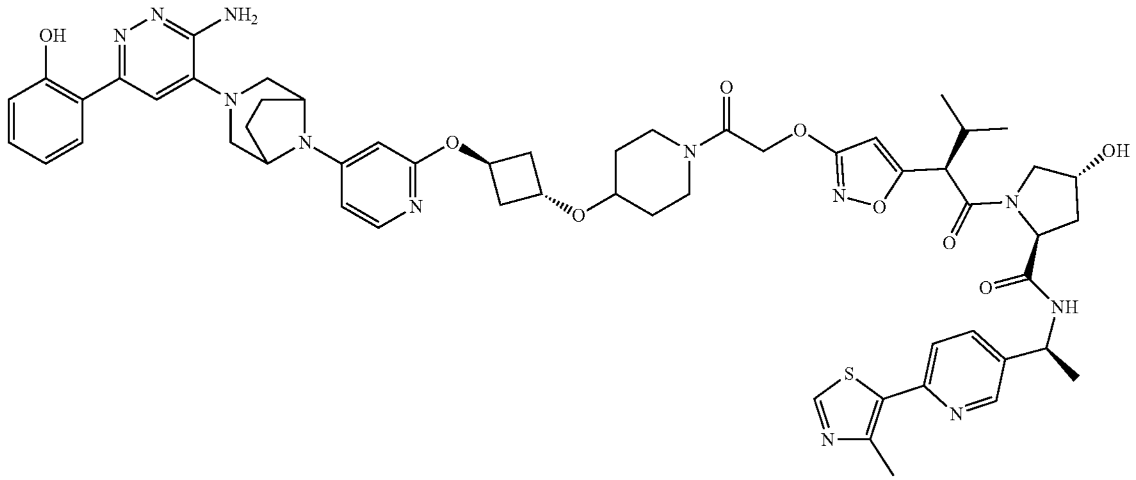
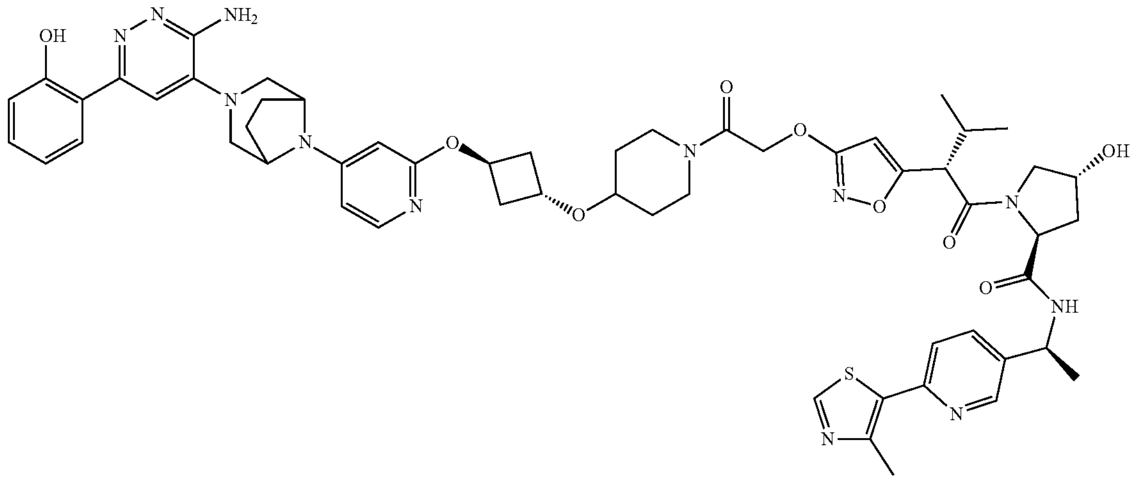
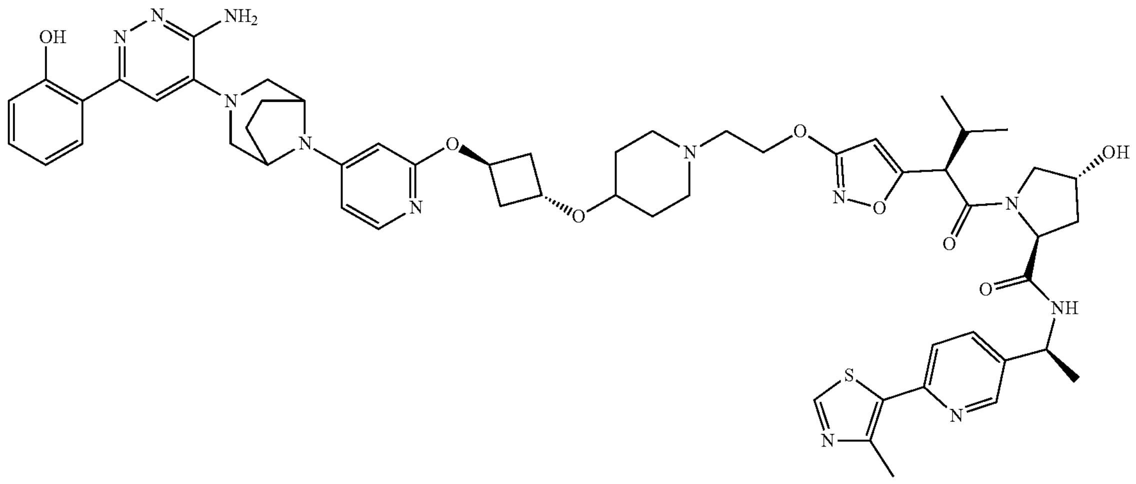

-continued
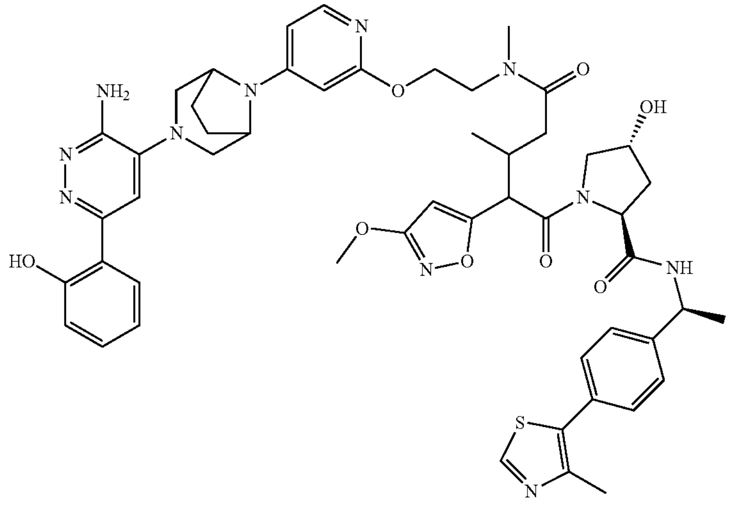
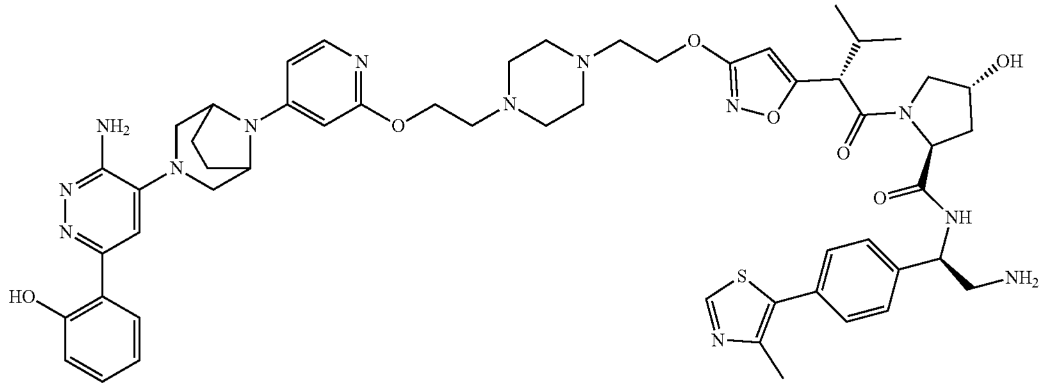
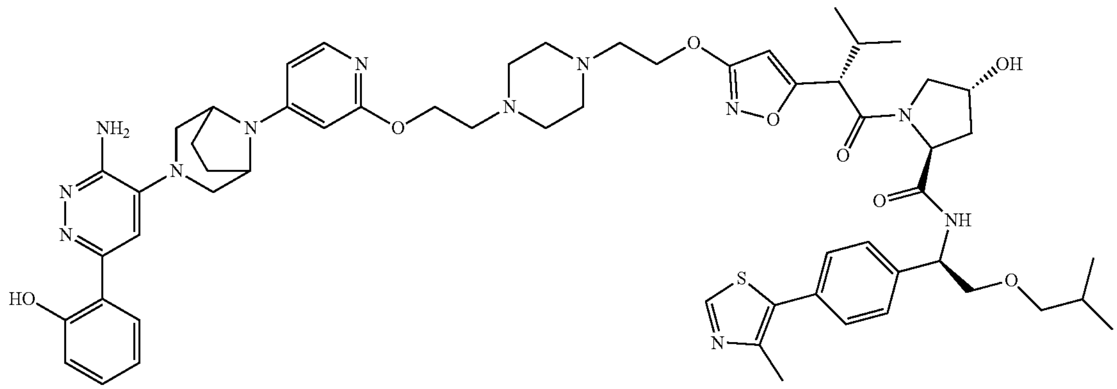
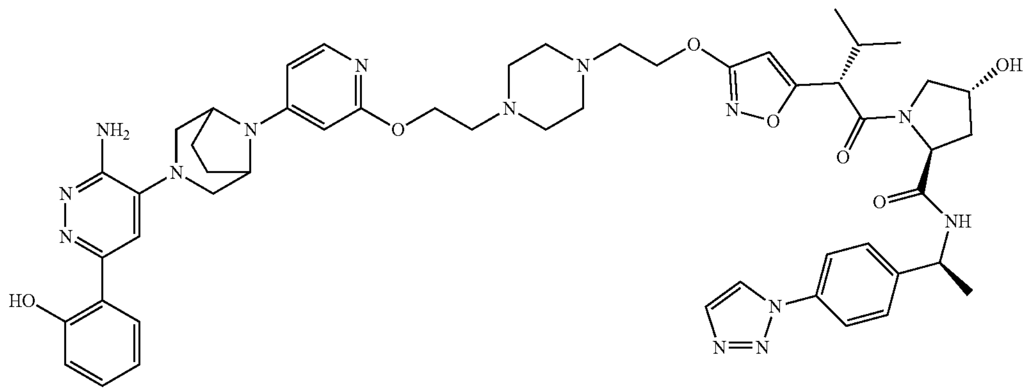

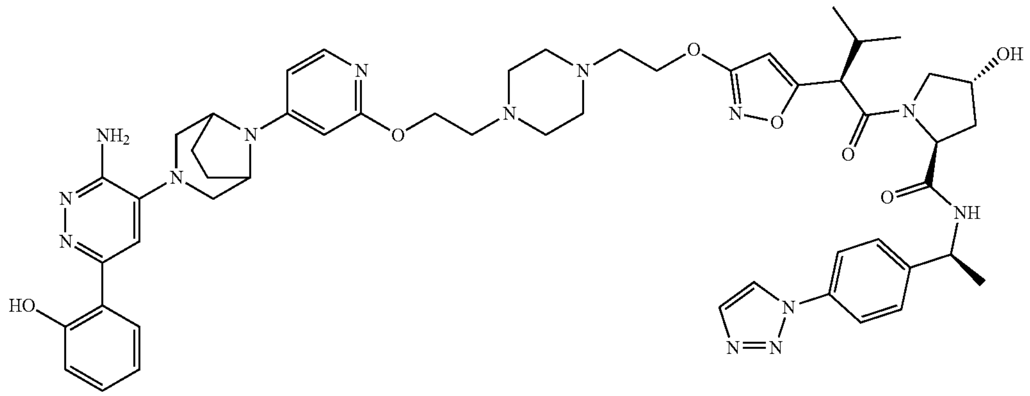
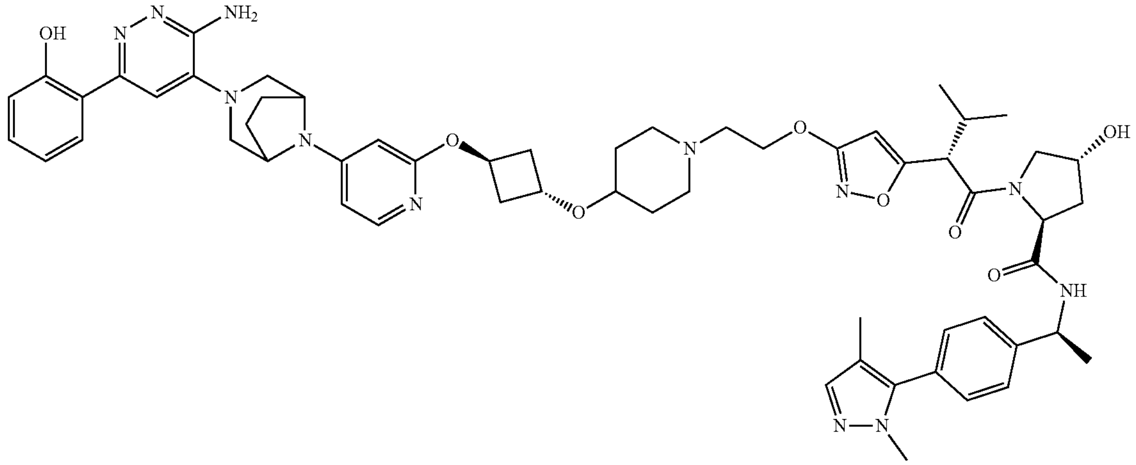
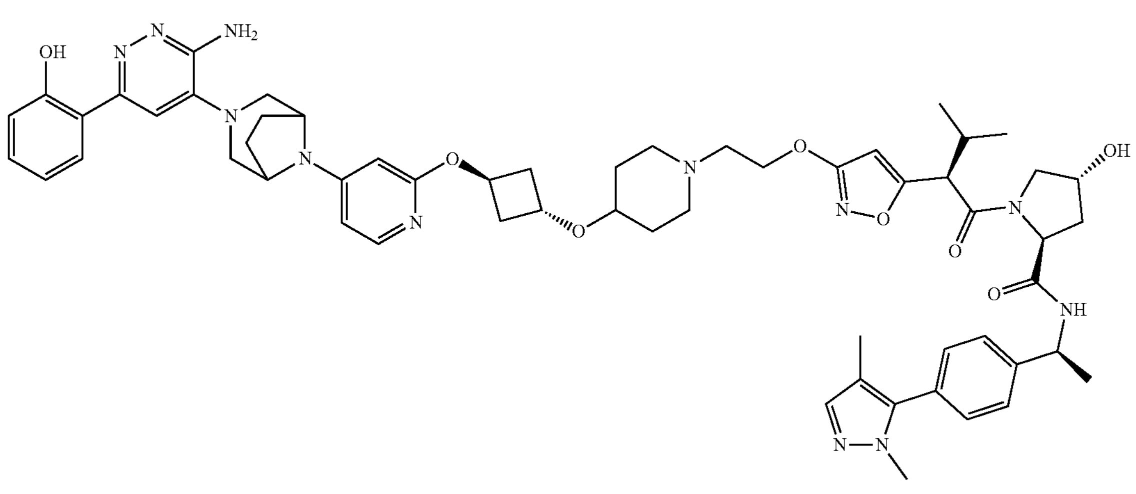

-continued
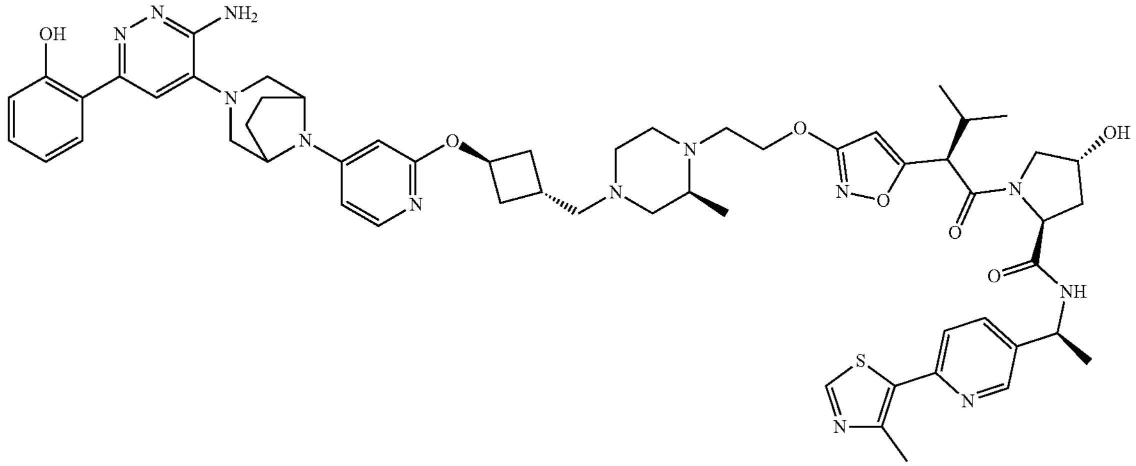
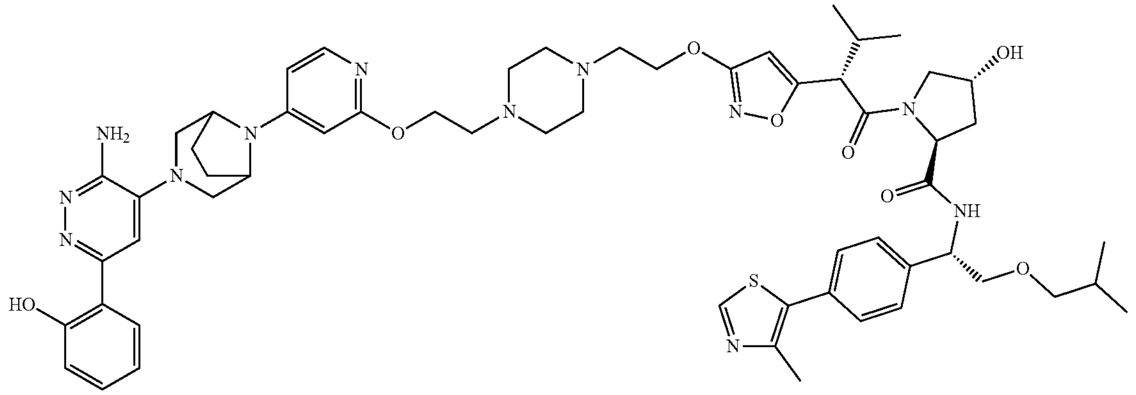
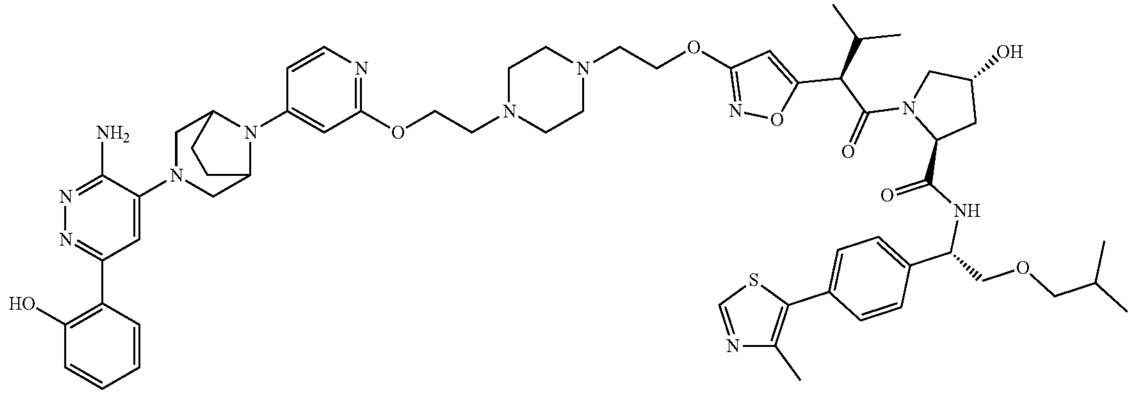
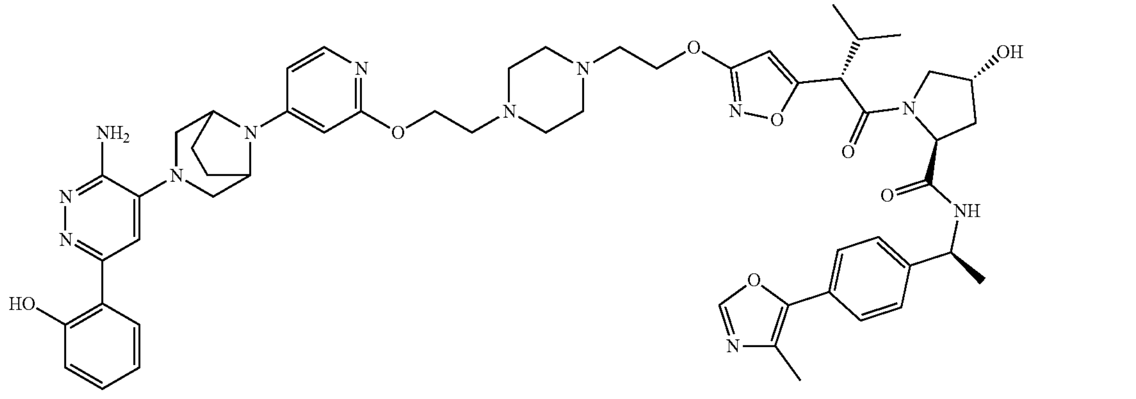

-continued
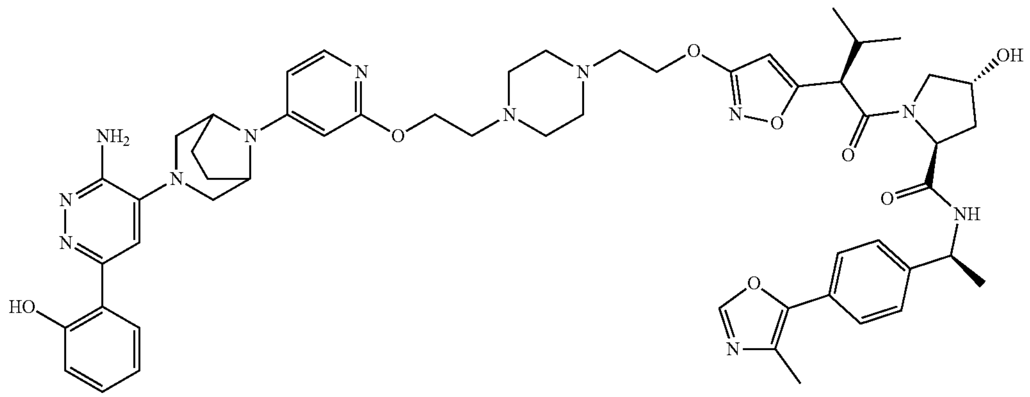
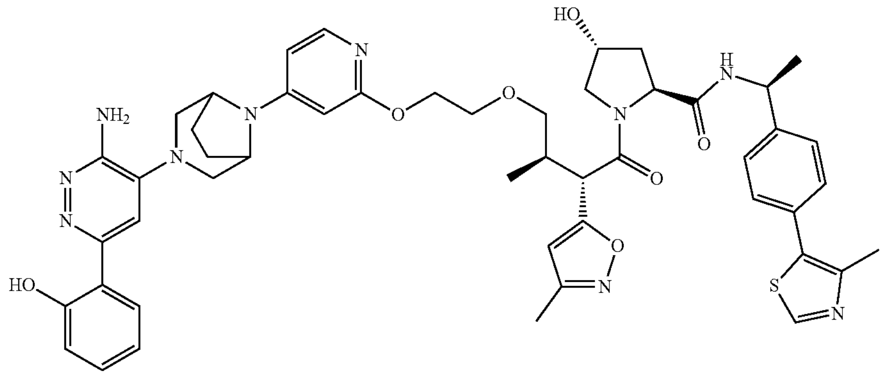
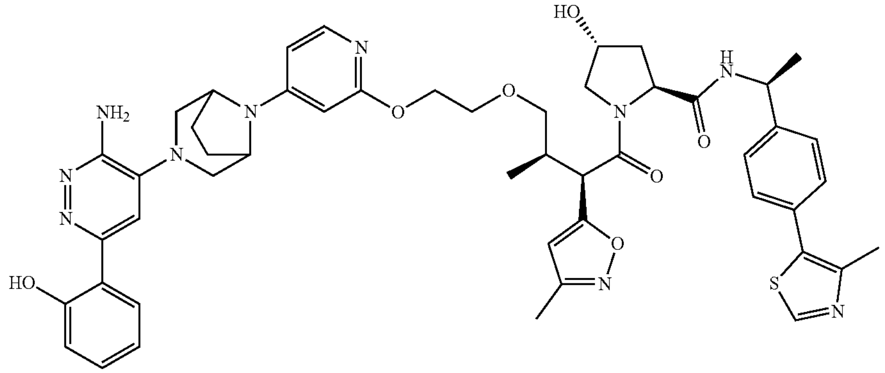
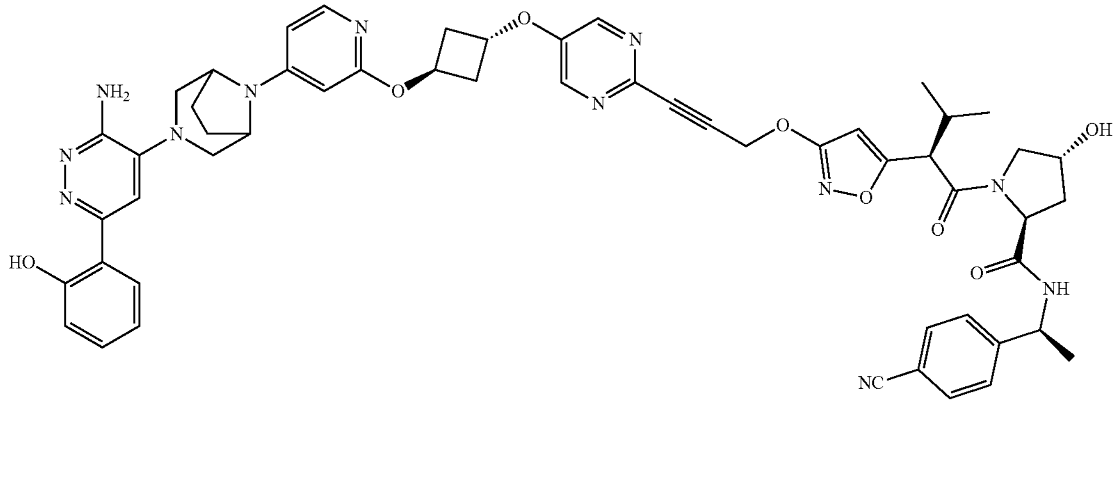

-continued
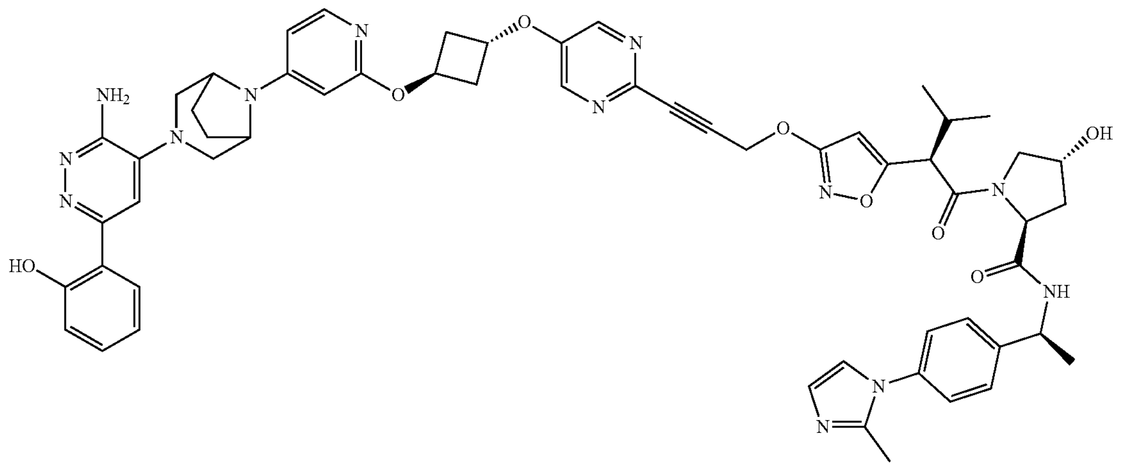
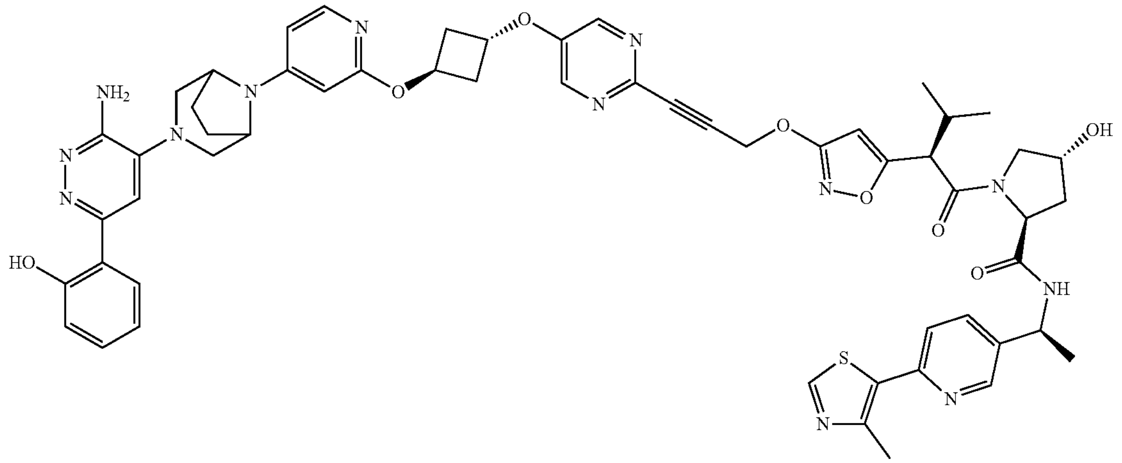
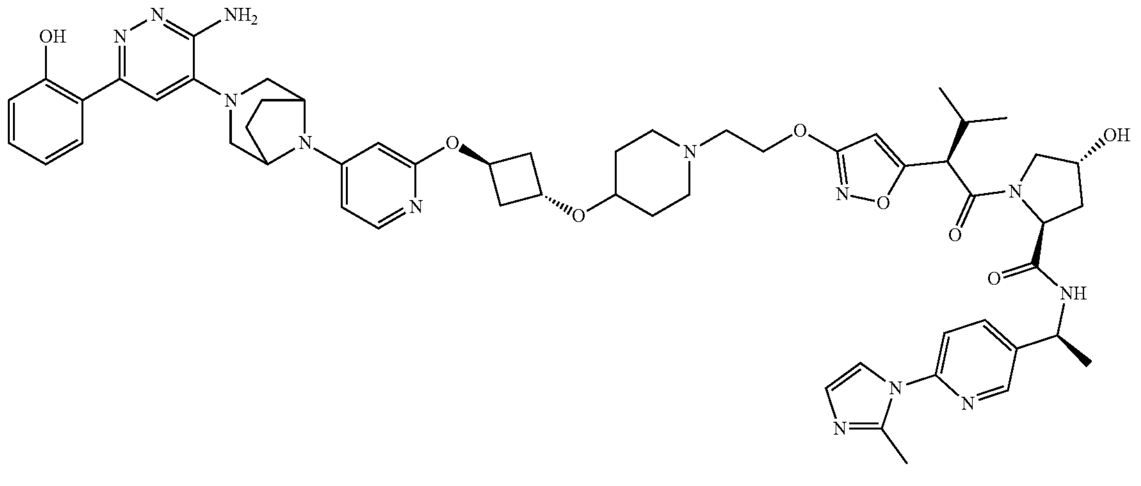

-continued
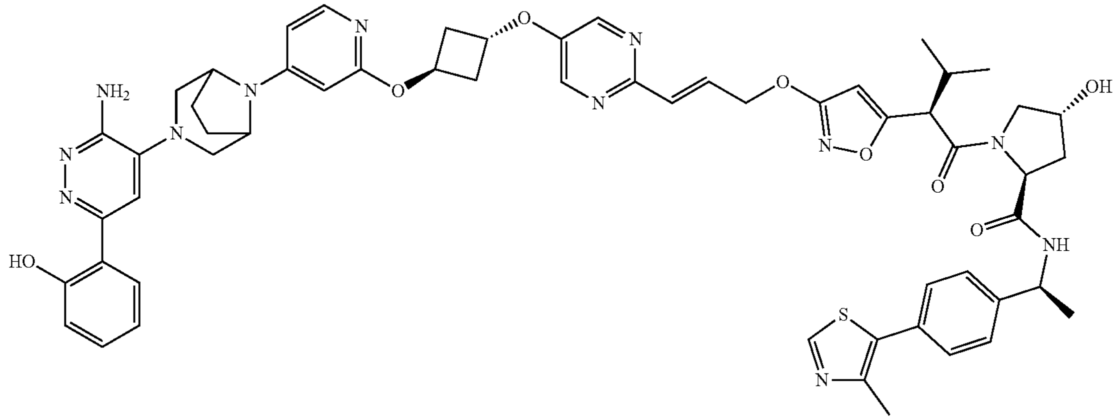
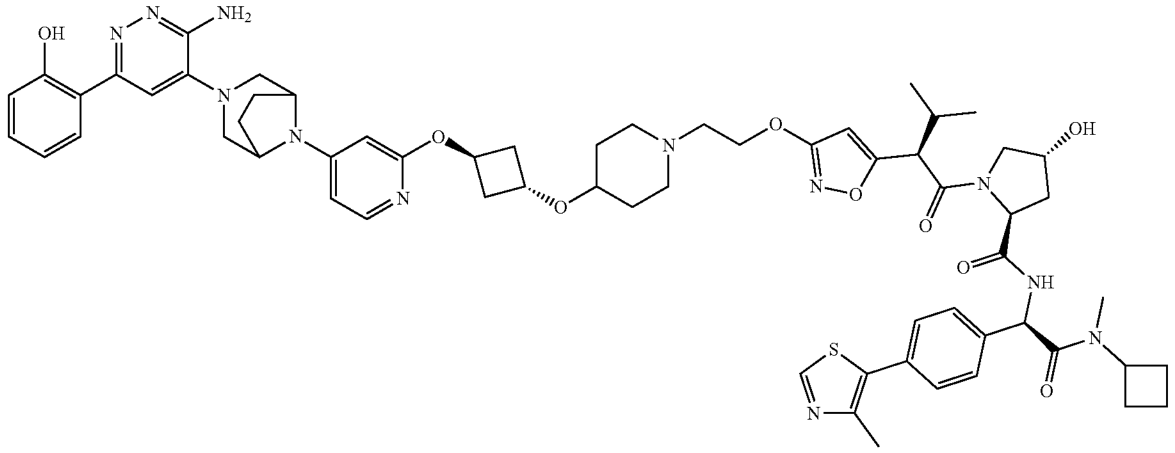
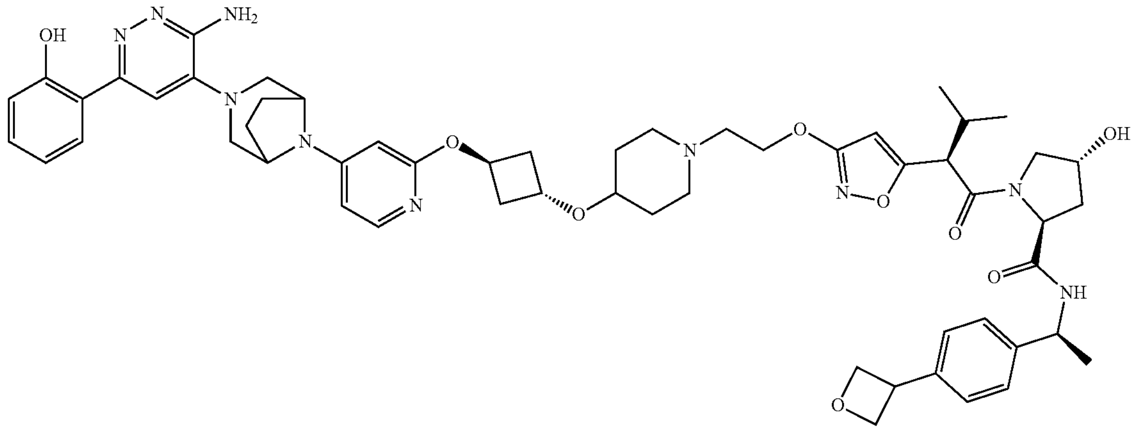
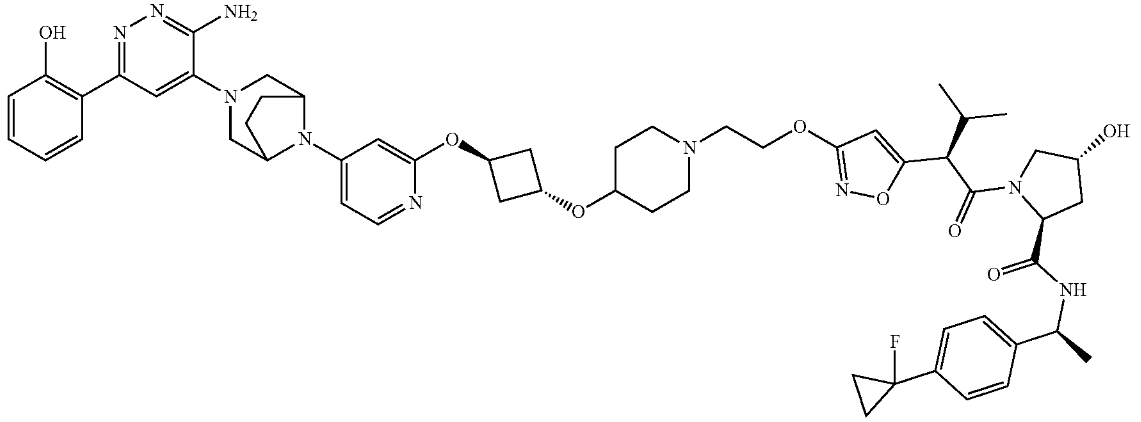

-continued
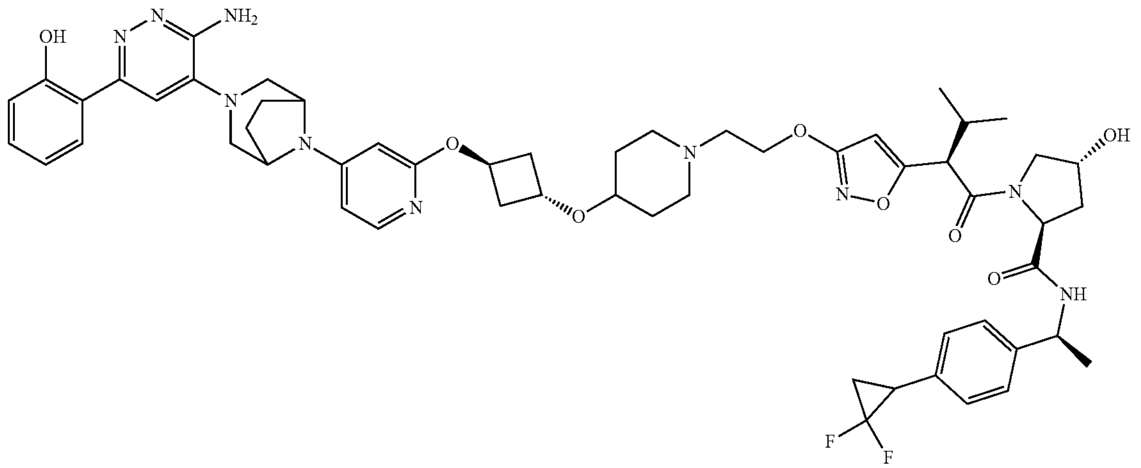
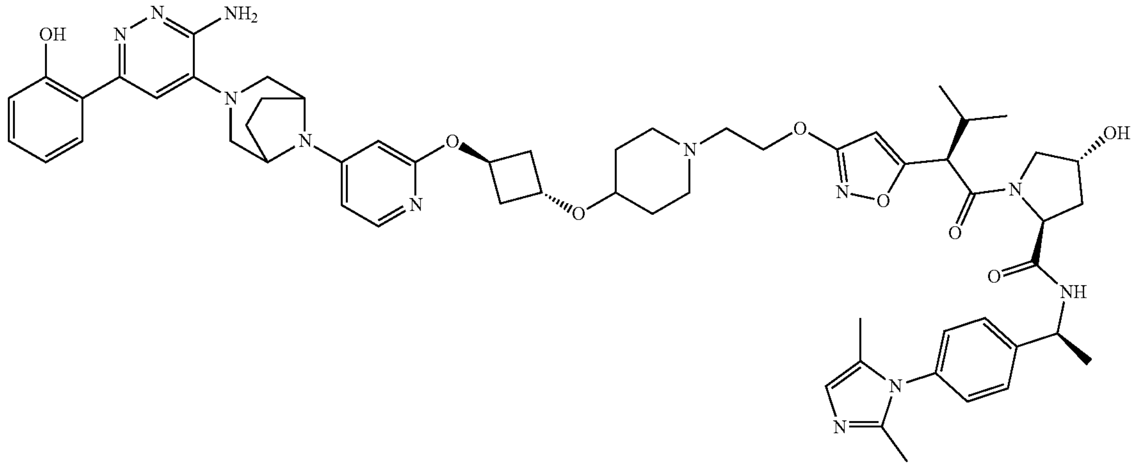
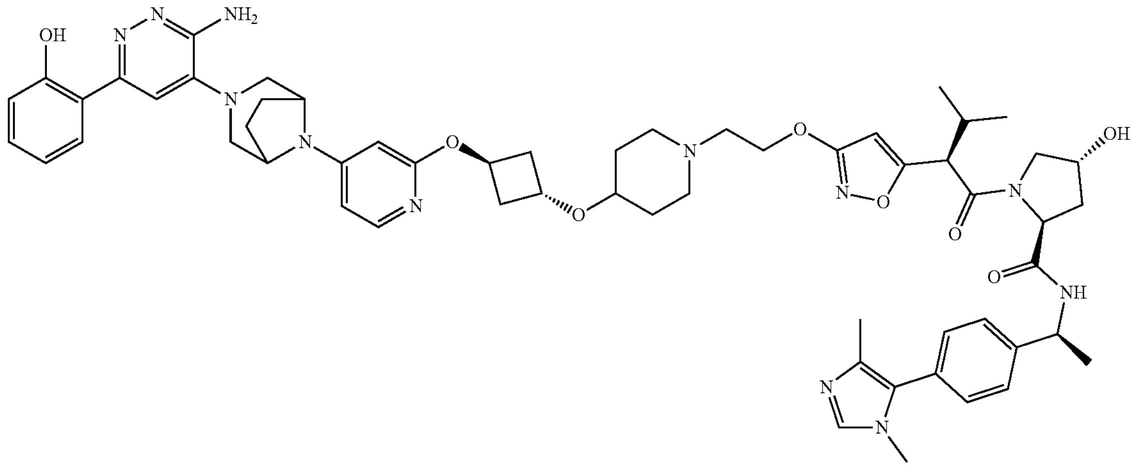

-continued
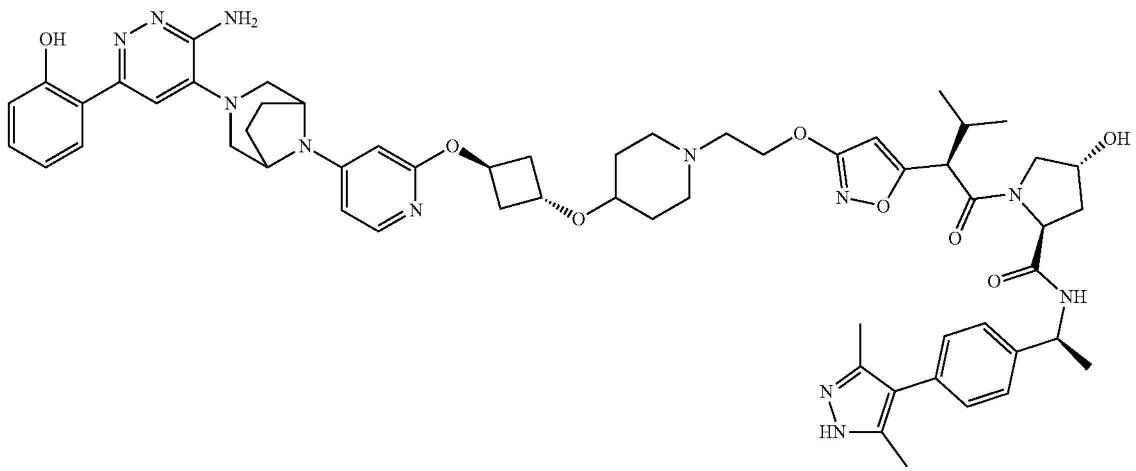
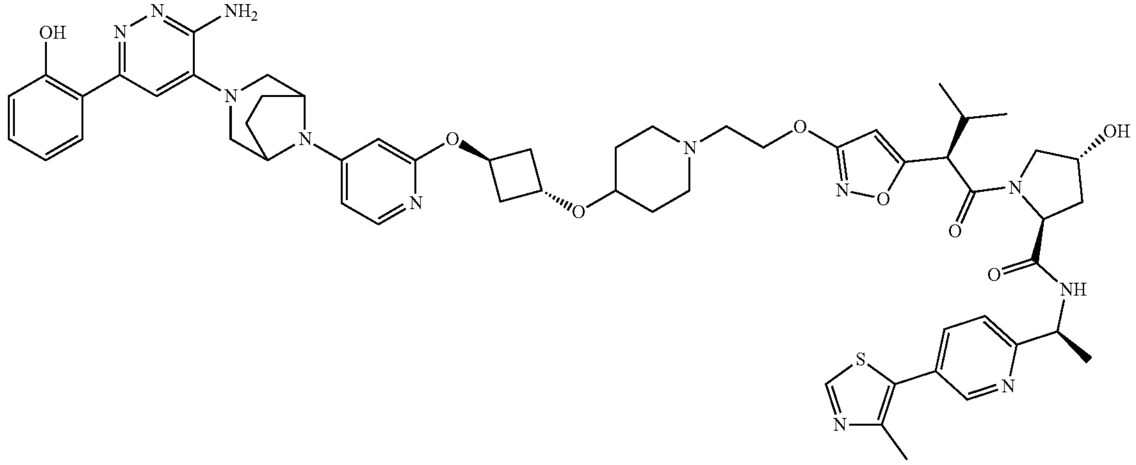
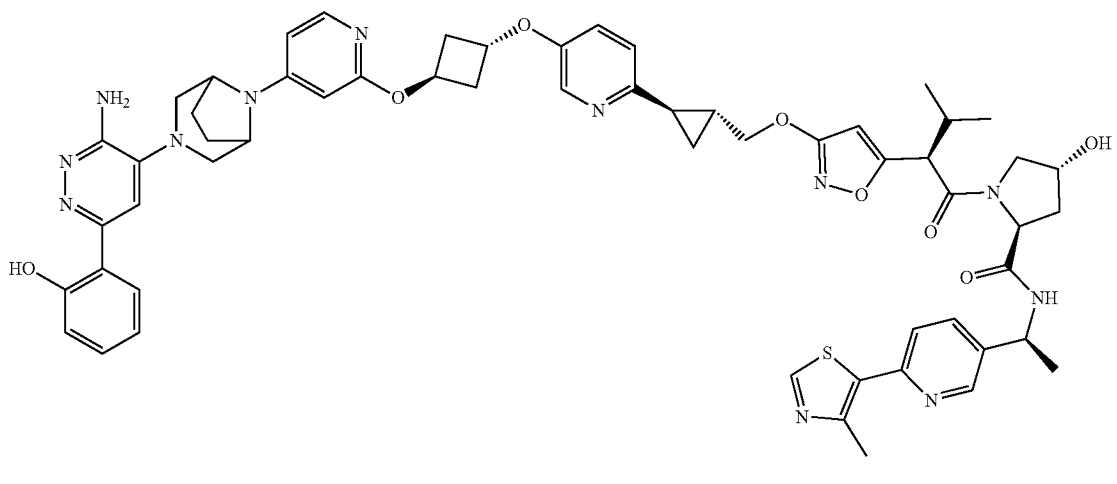

-continued
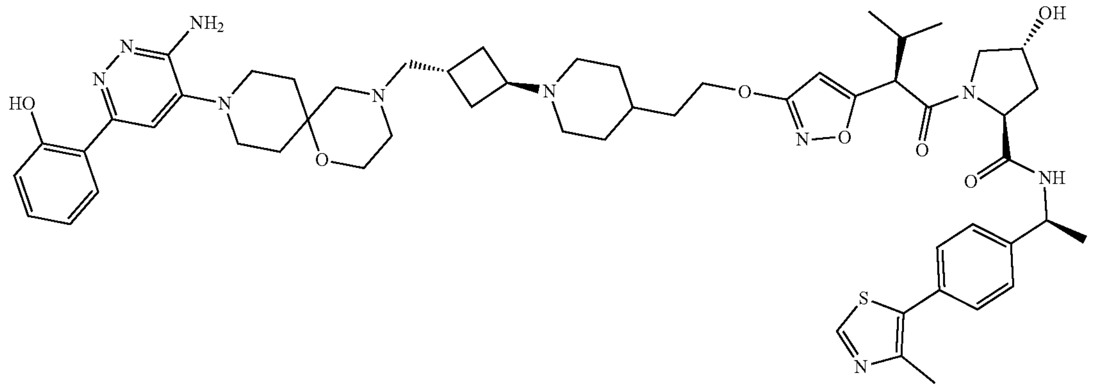
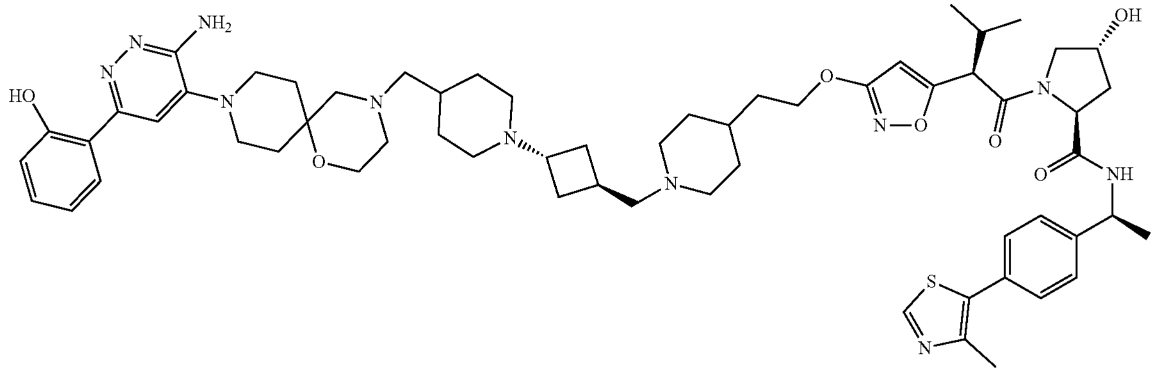
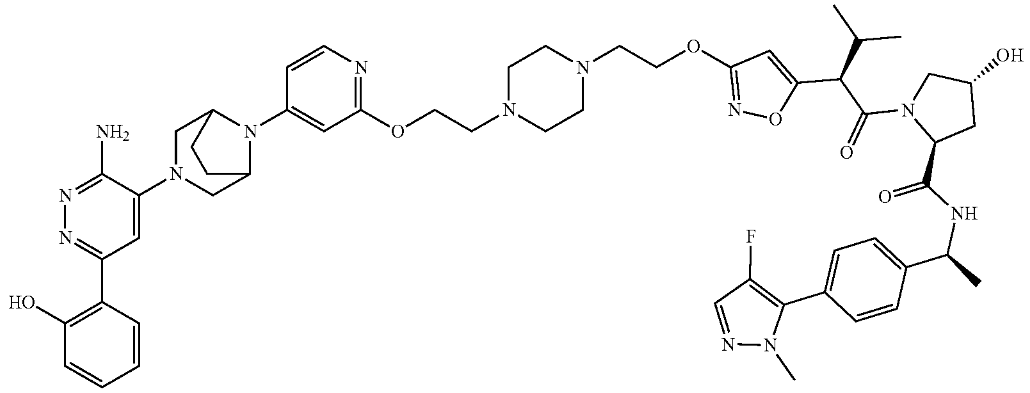
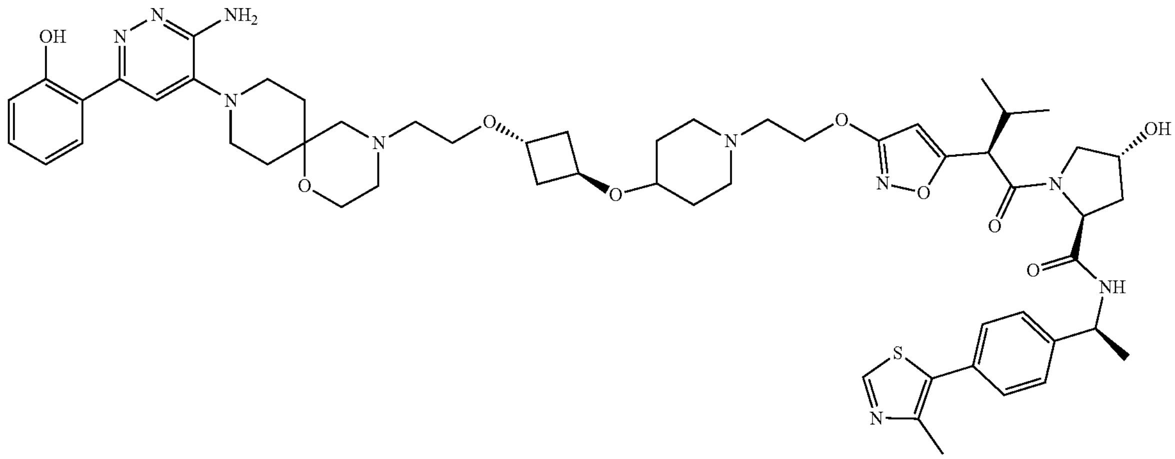

-continued
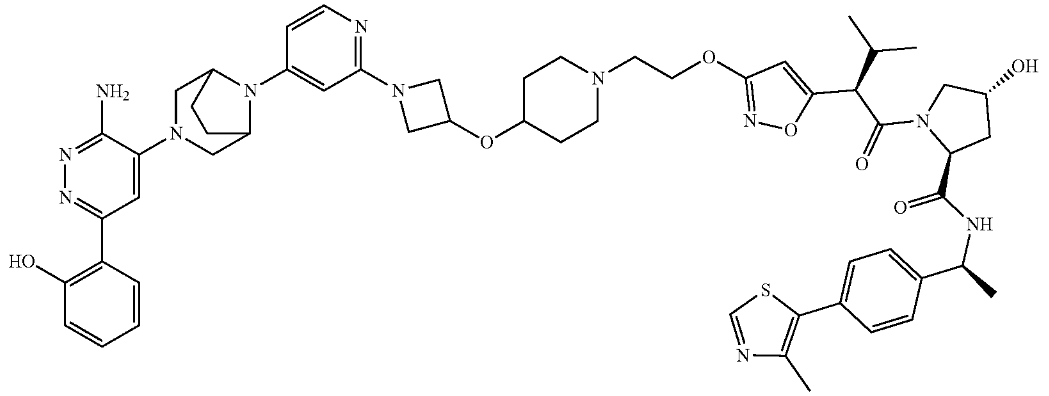
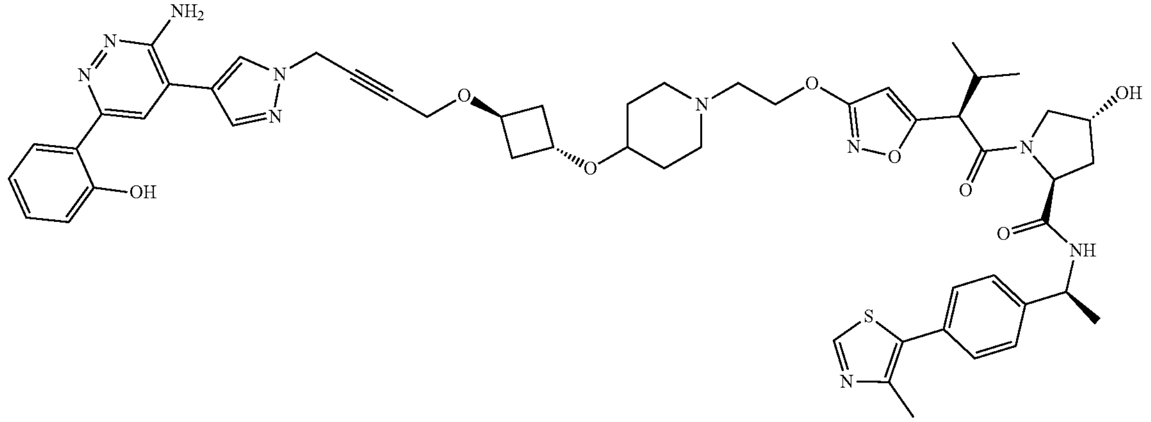
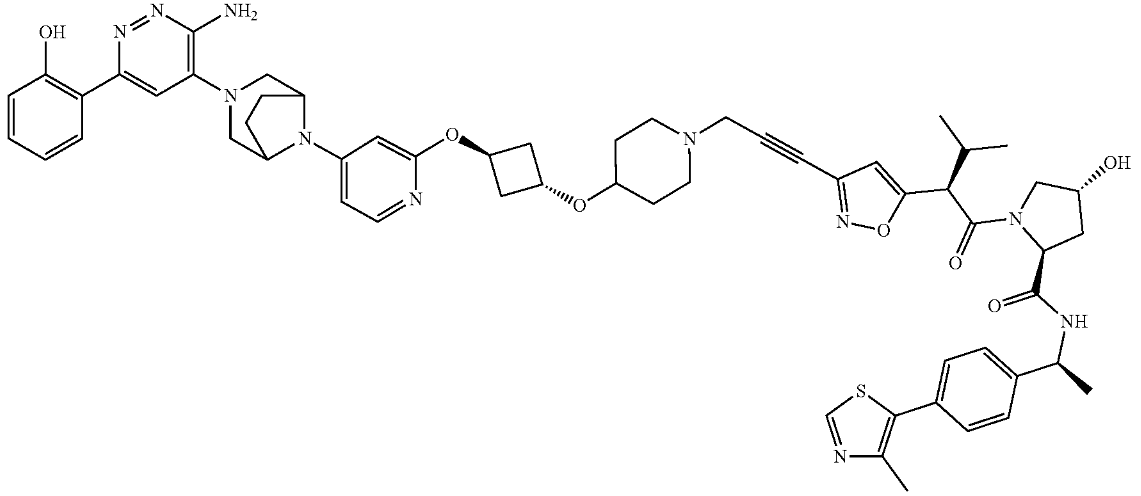
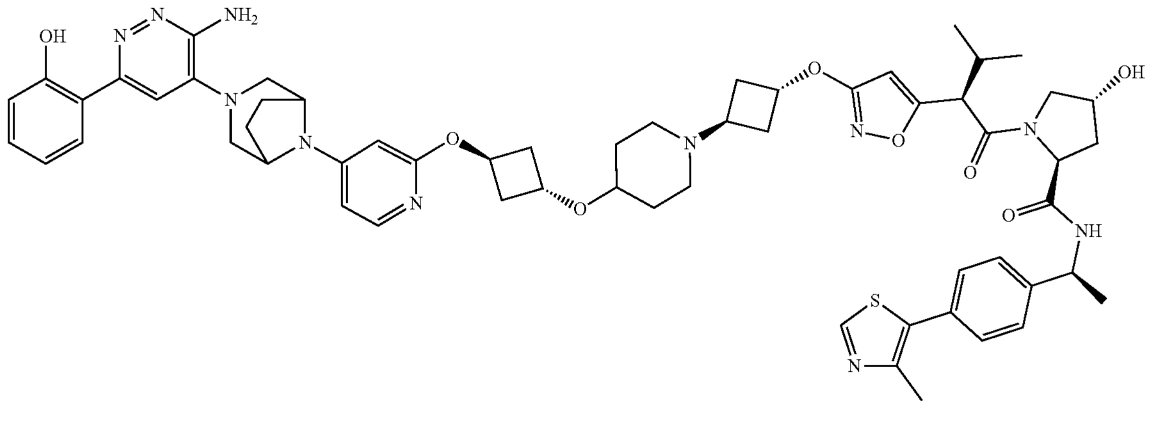

-continued
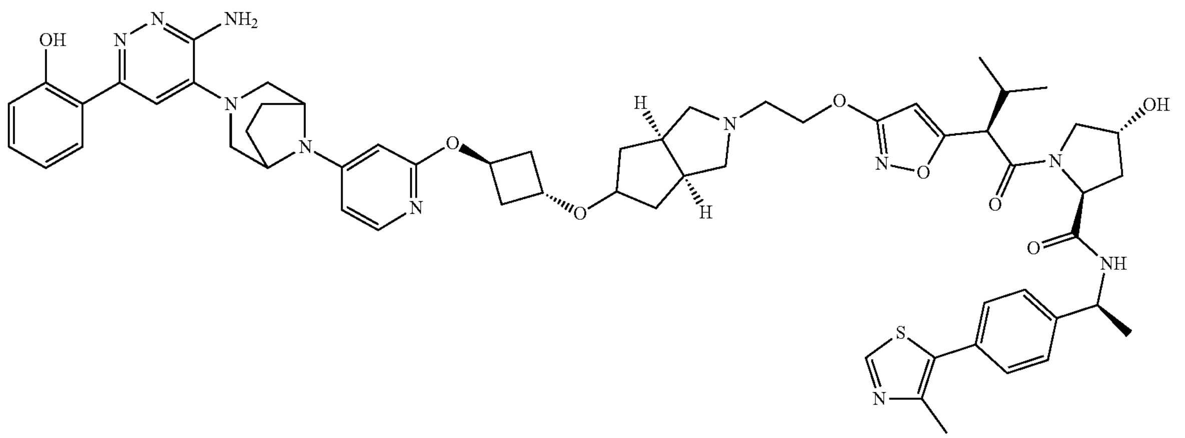
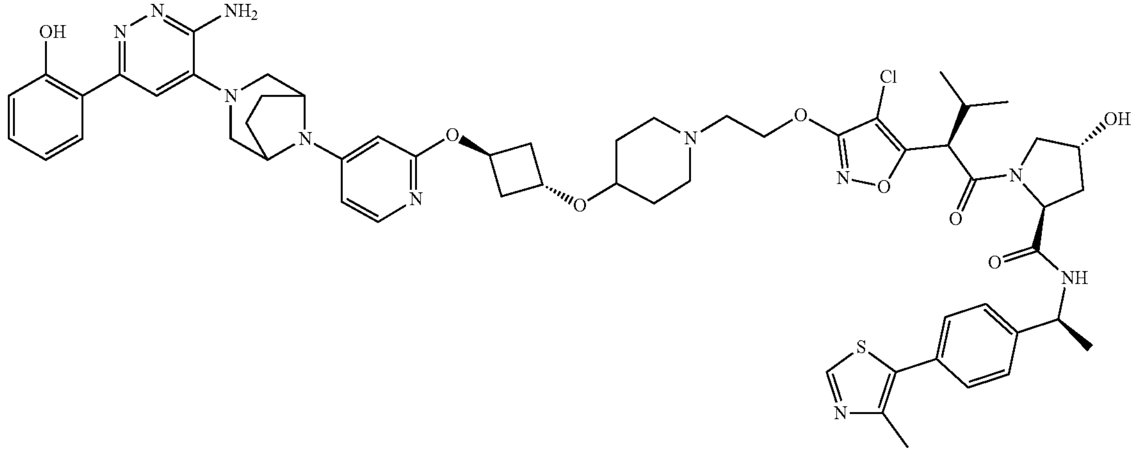
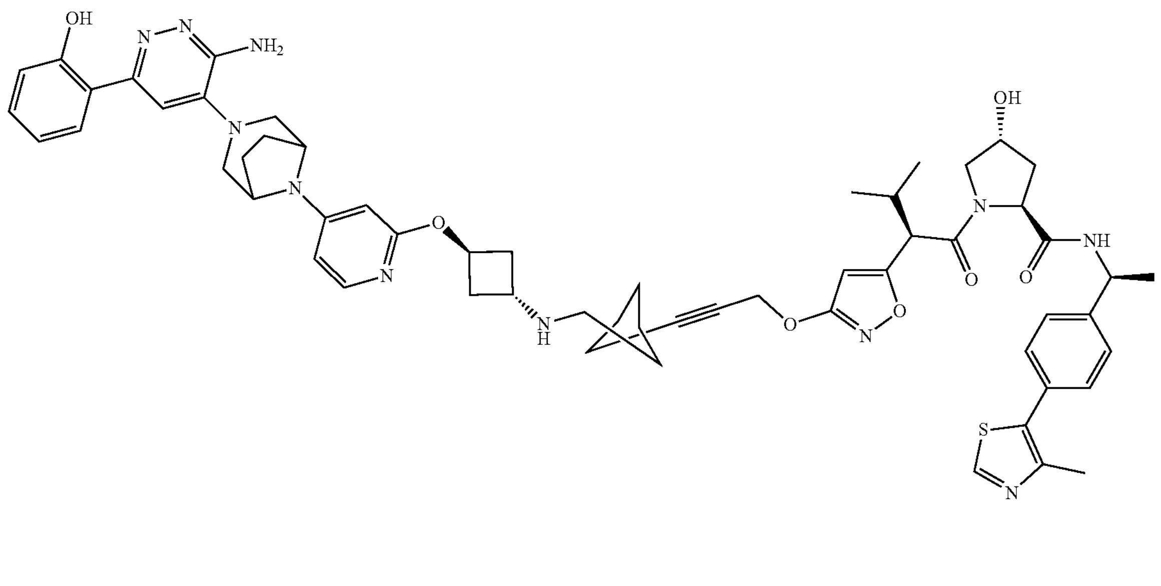 [SMILES: Cc1ncsc1-c1ccc([C@H](C)NC(=O)[C@@H]2C[C@@H](O)CN2C(=O)[C@@H](c2cc(OCC#CCCCCCCN[C@H]3C[C@H](Oc4cc(N5C6CCC5CN(c5cc(-c7ccccc7O)nnc5N)C6)ccn4)C3)no2)C(C)C)cc1]

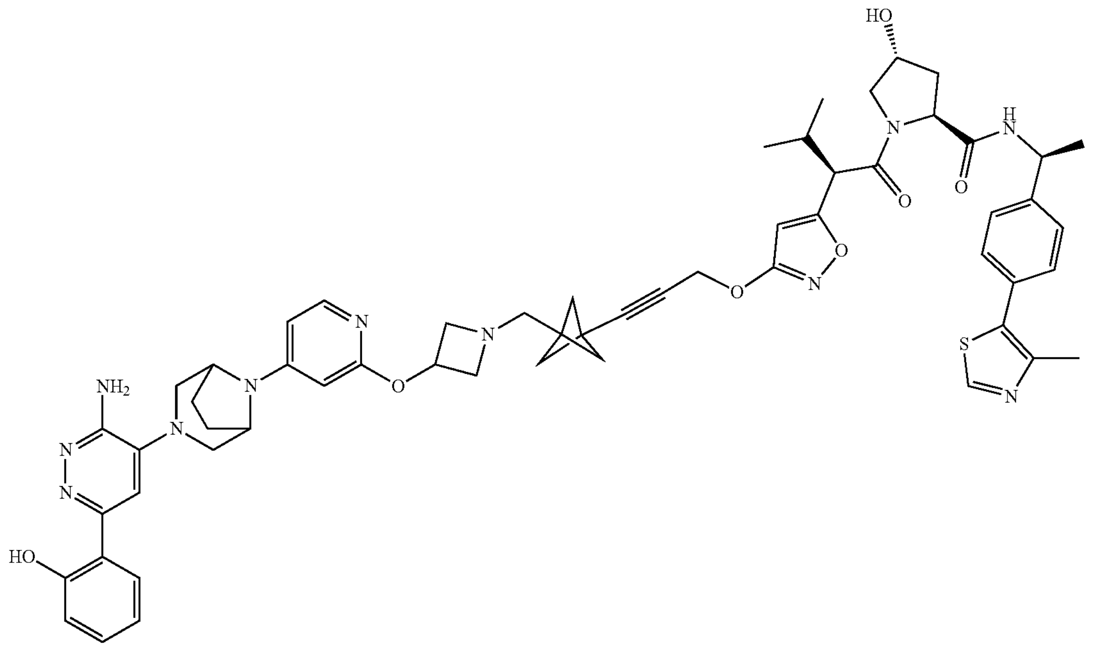
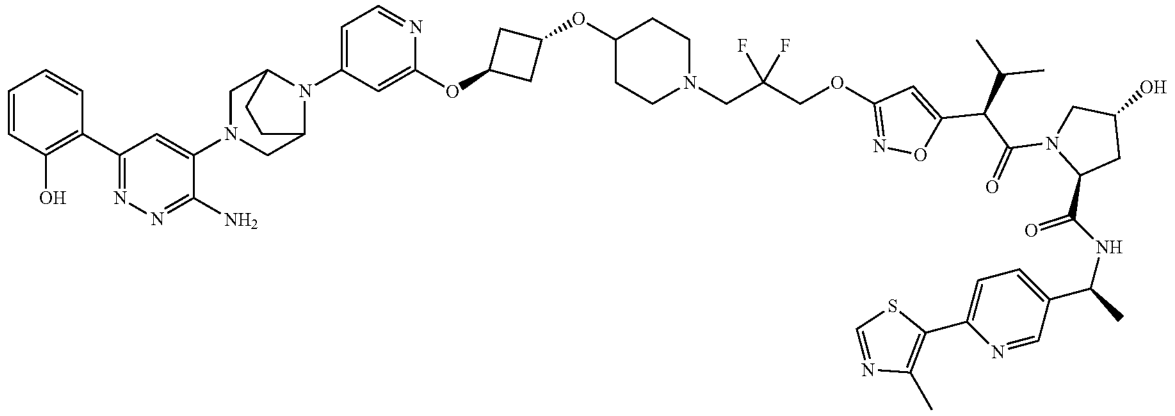
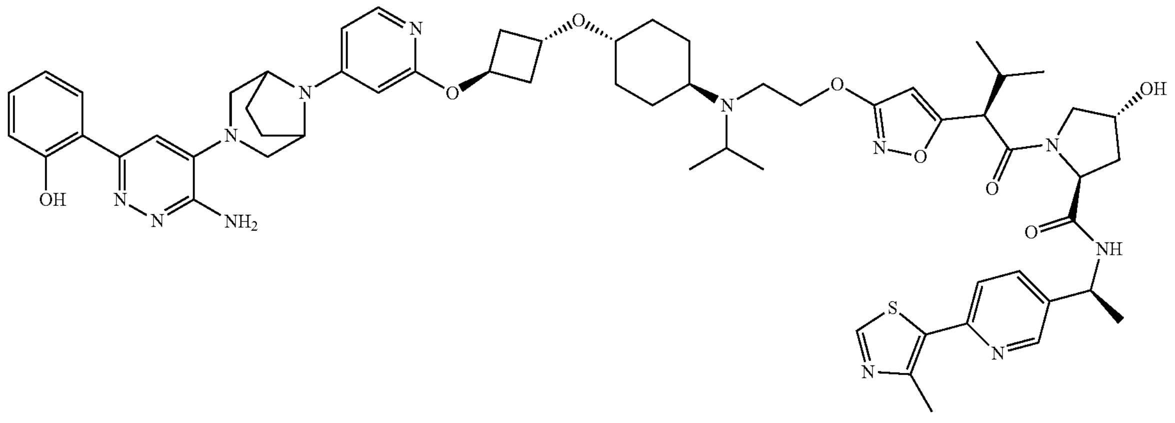

-continued
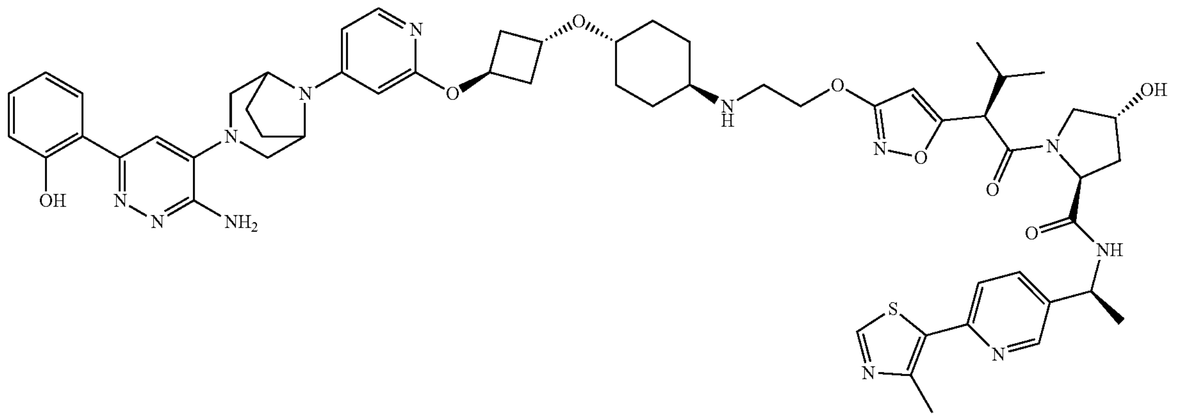
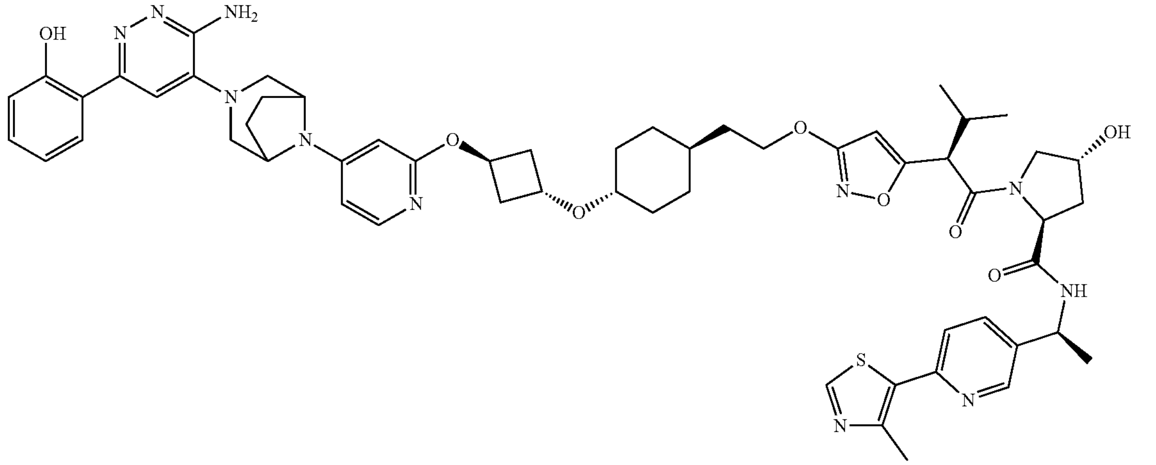
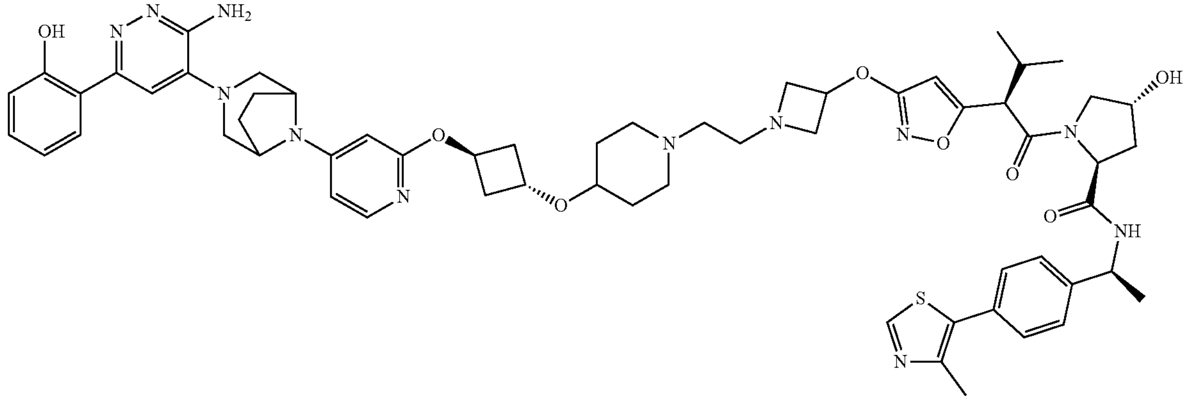

-continued
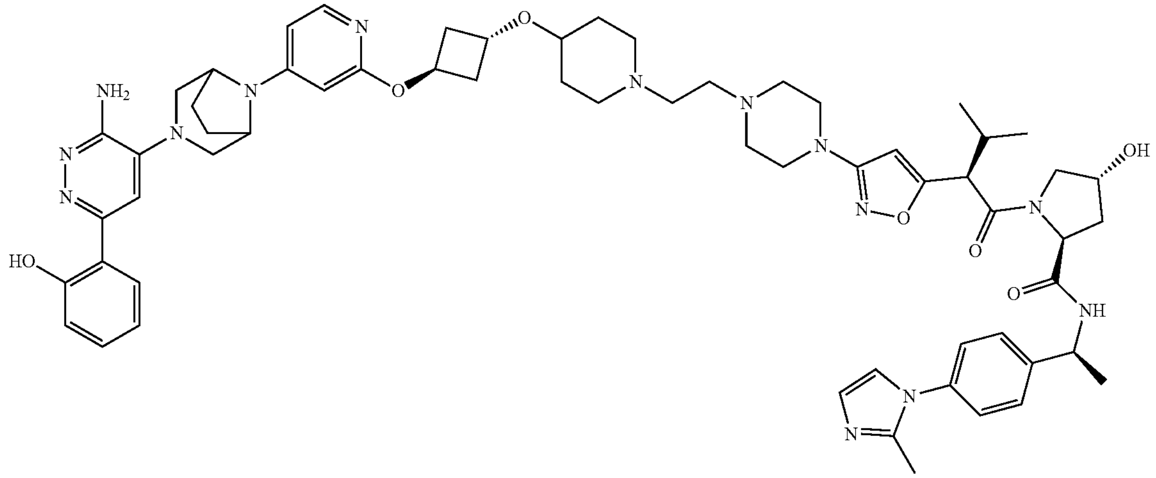
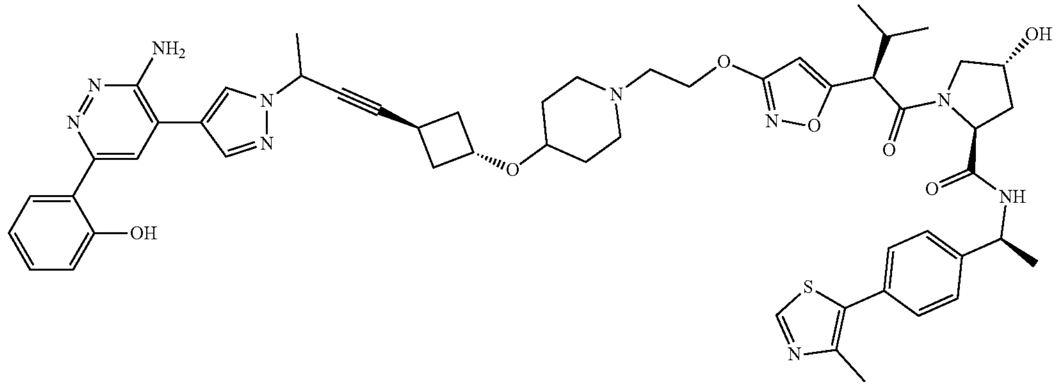
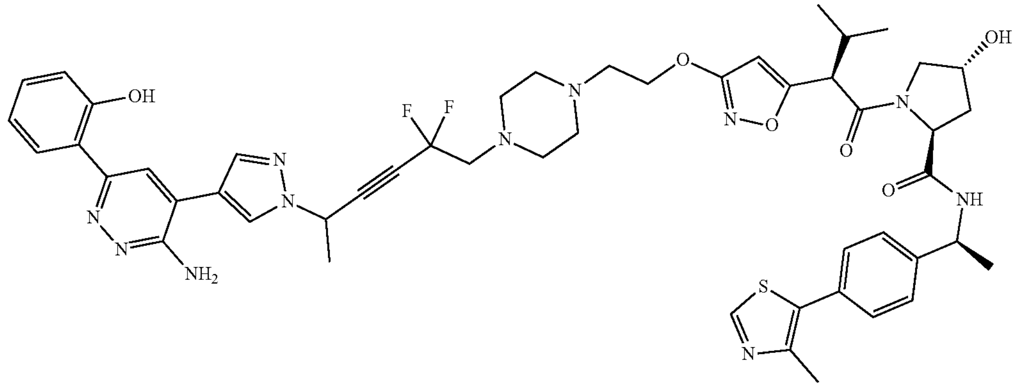
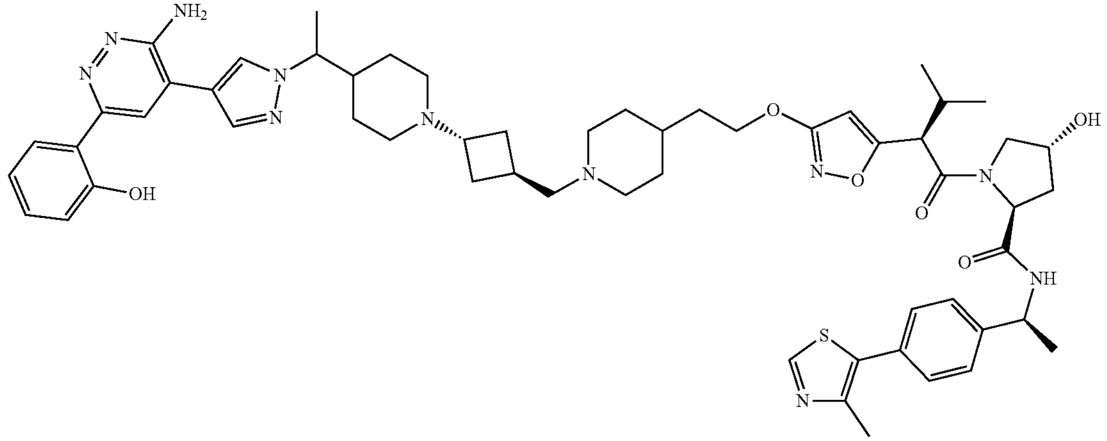

-continued
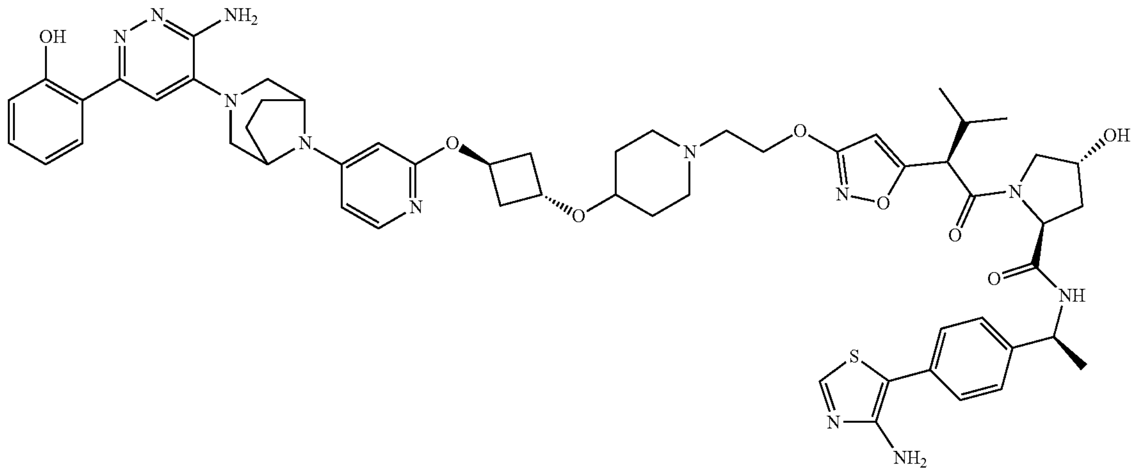
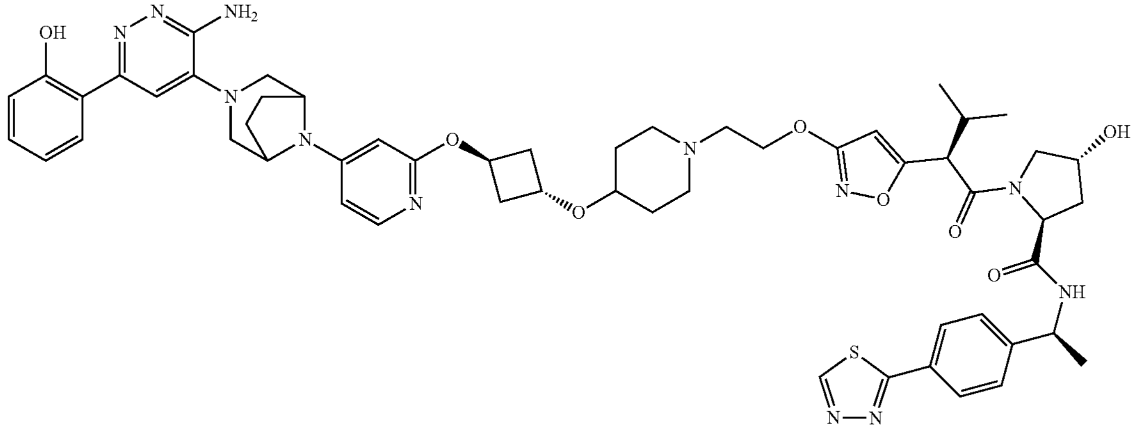
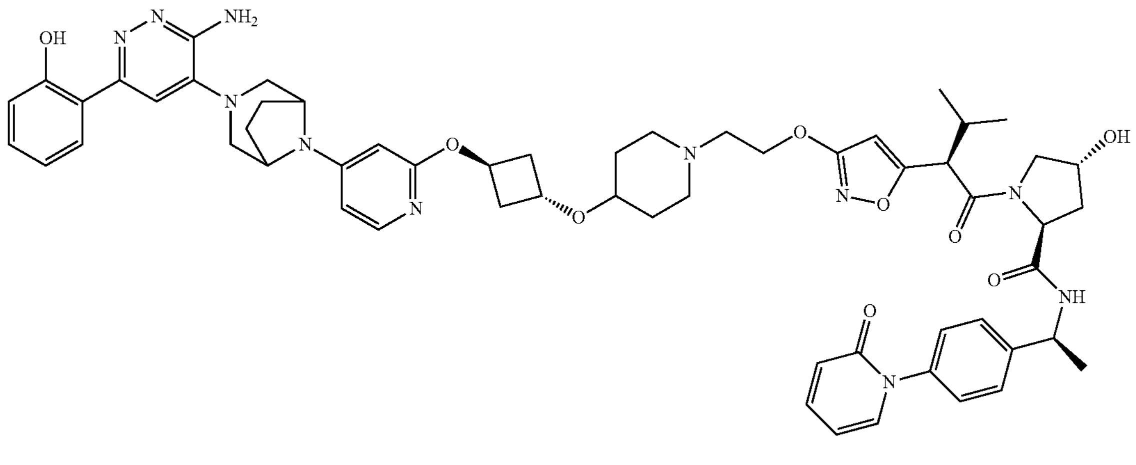

-continued
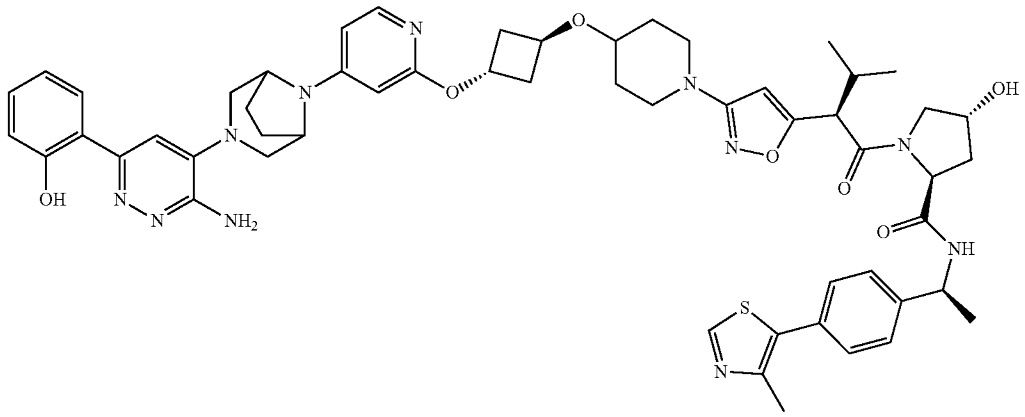
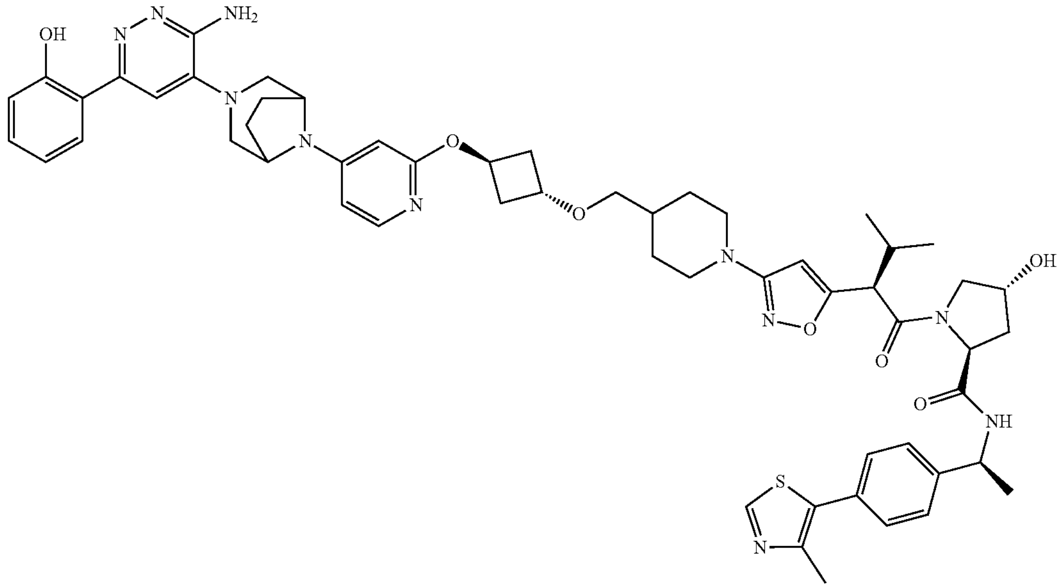
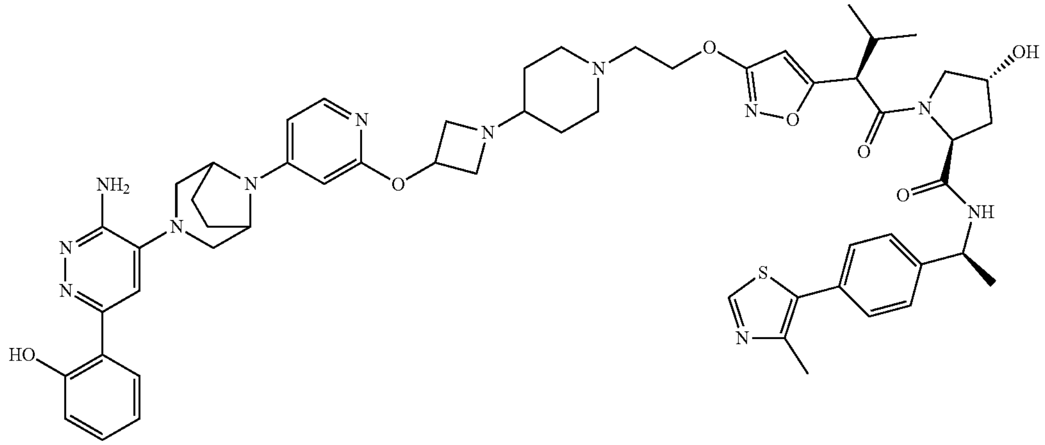

-continued
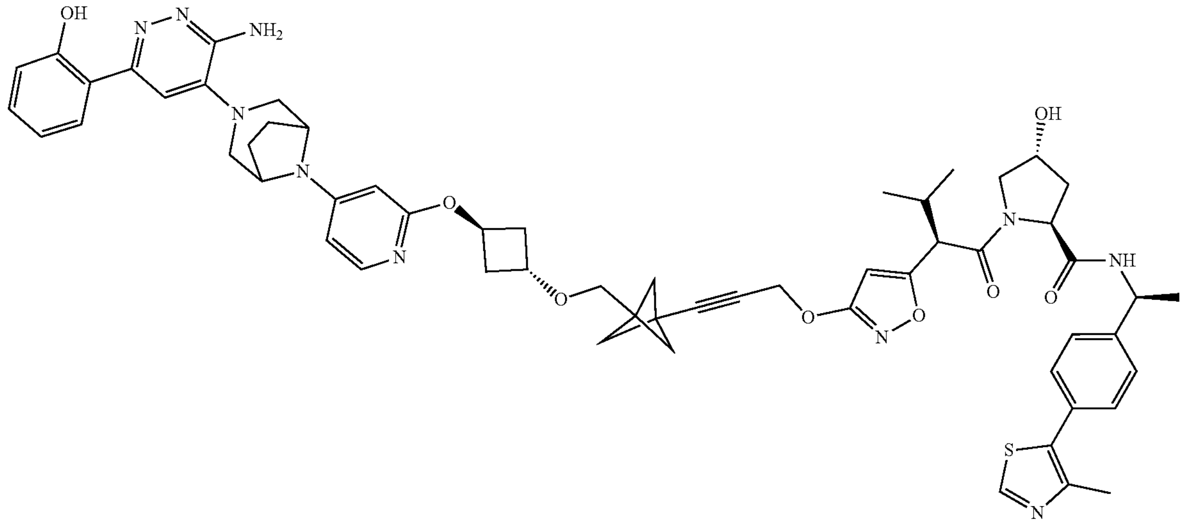
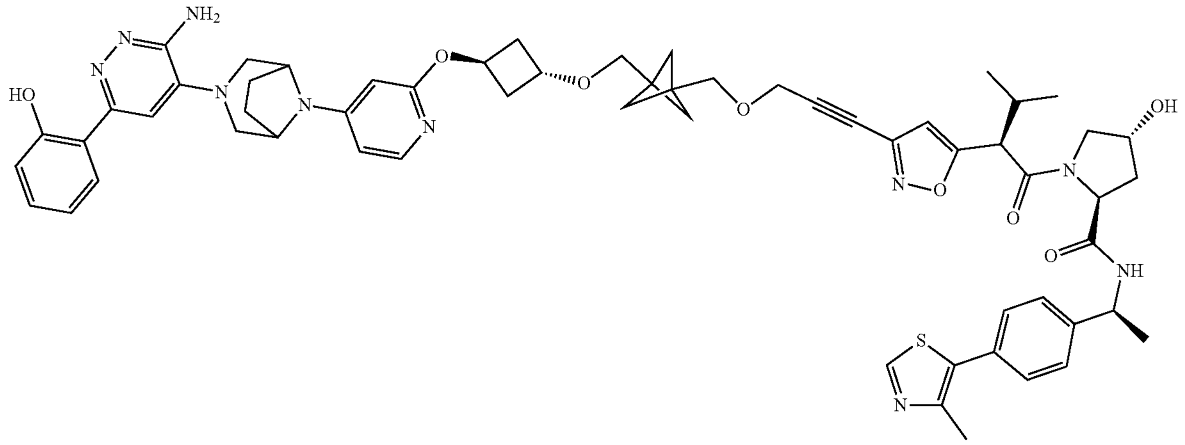
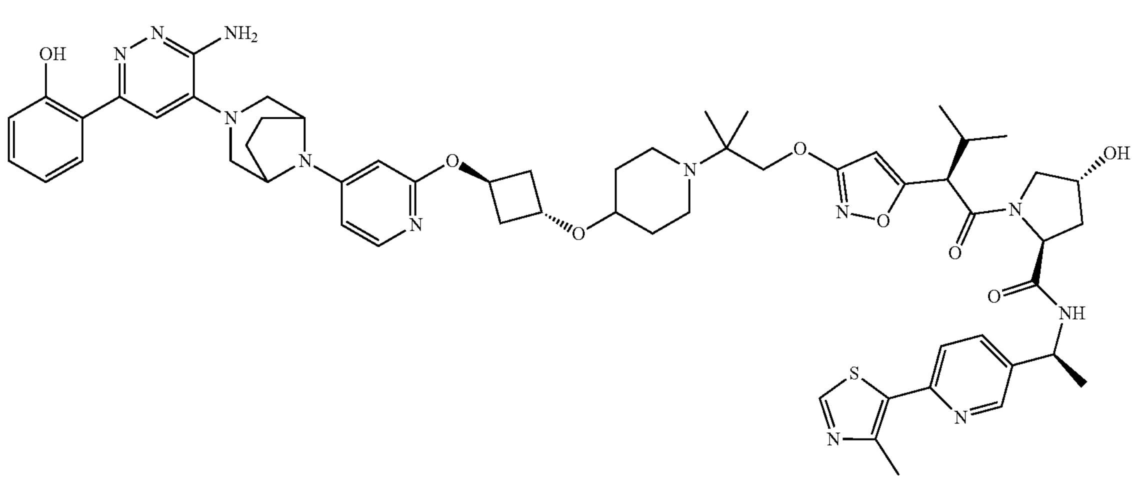

-continued
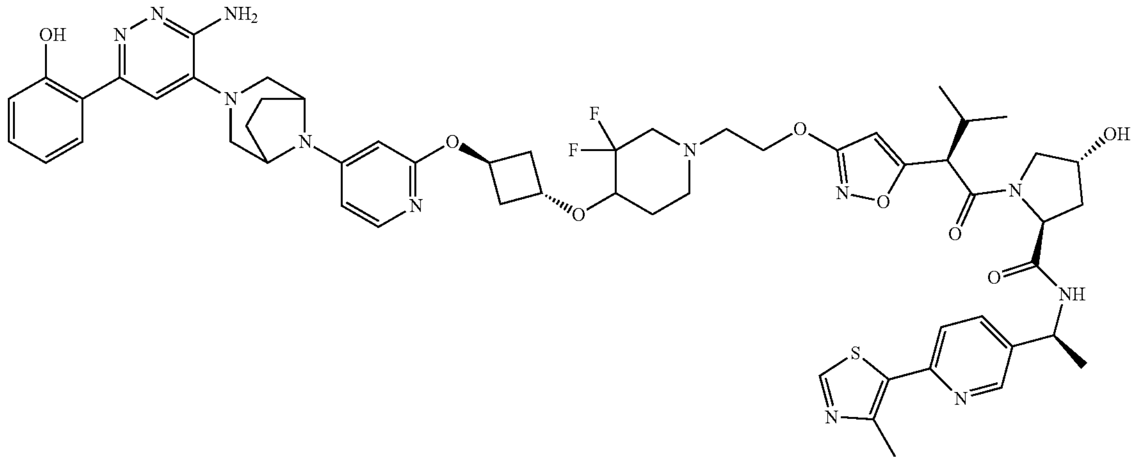
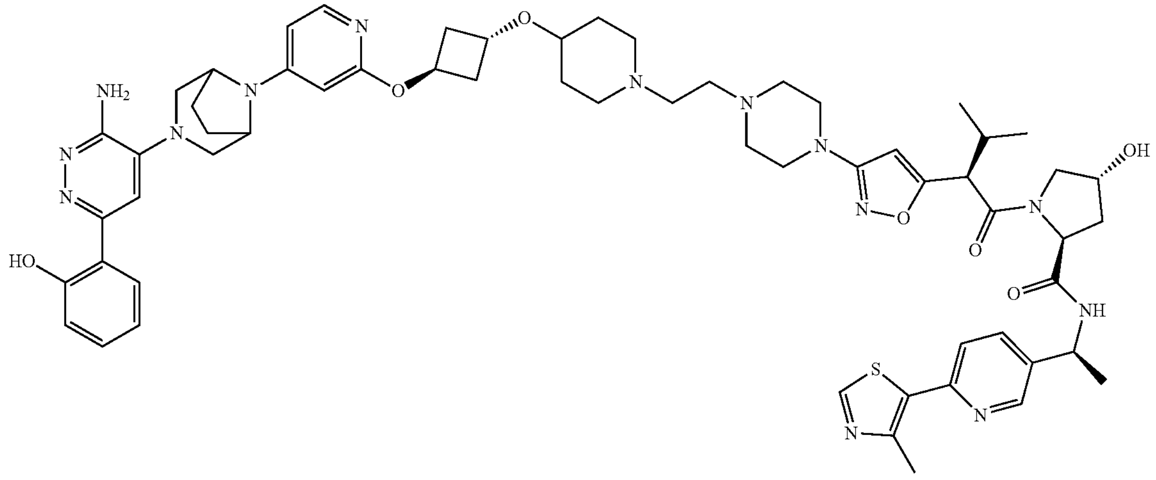
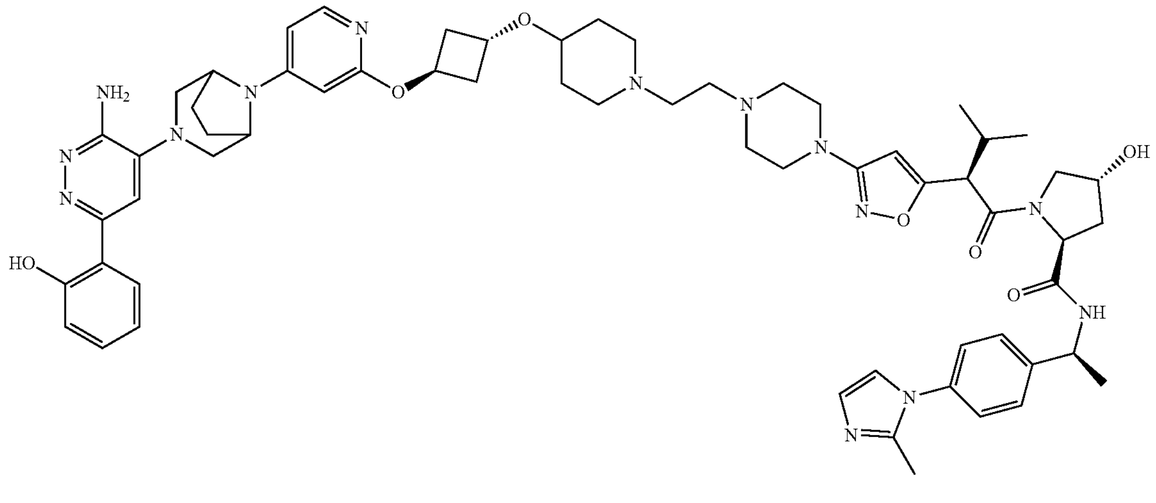

2405
2406
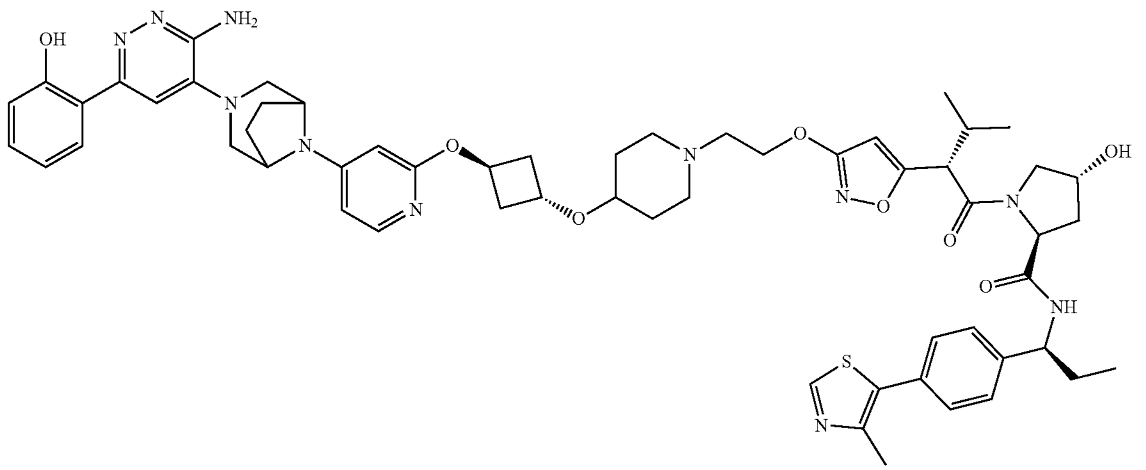
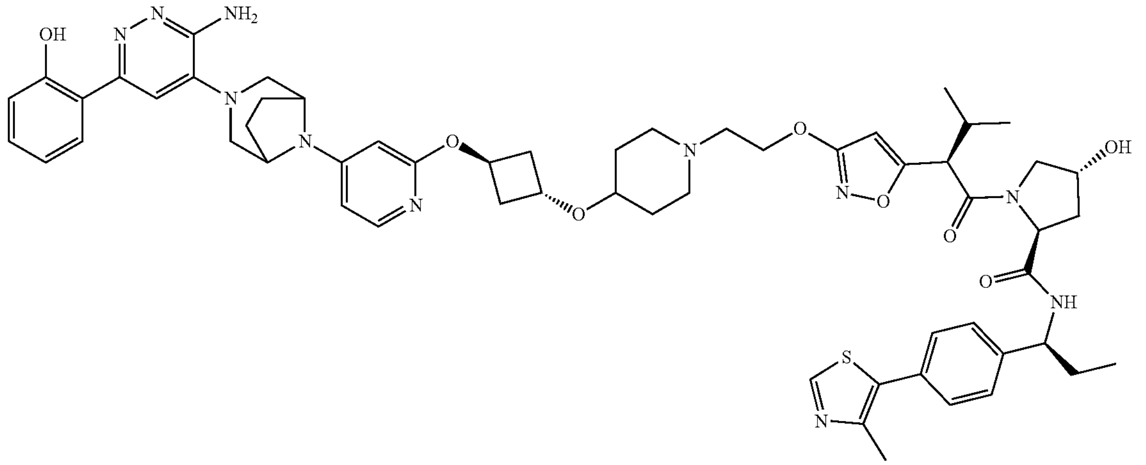
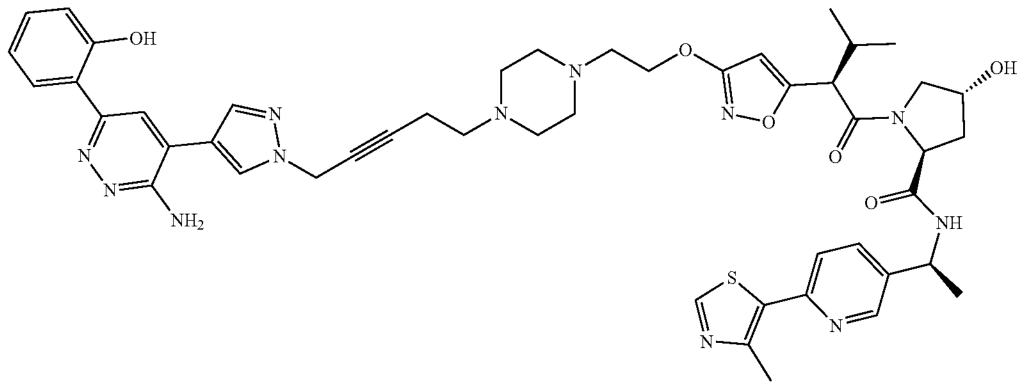

-continued
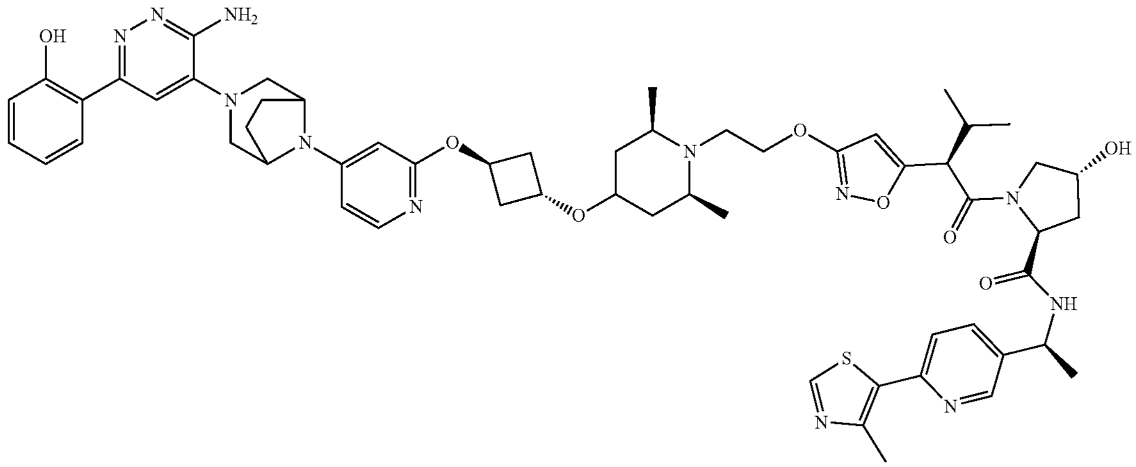
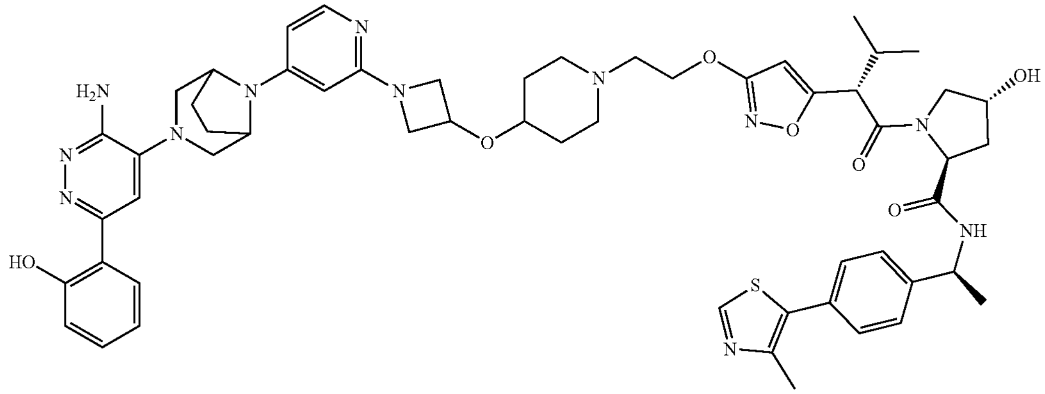
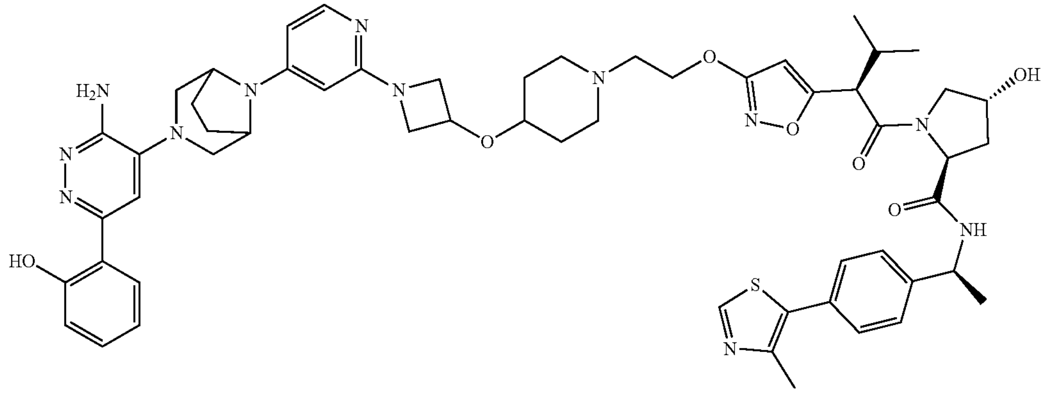
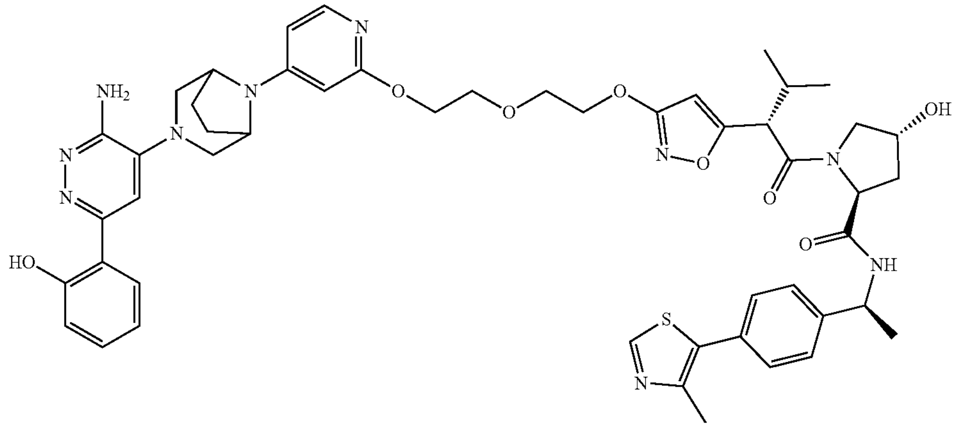

-continued
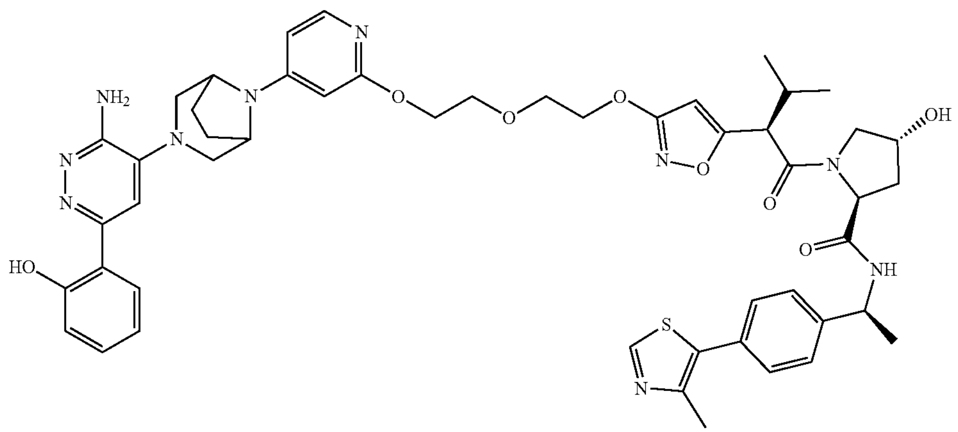
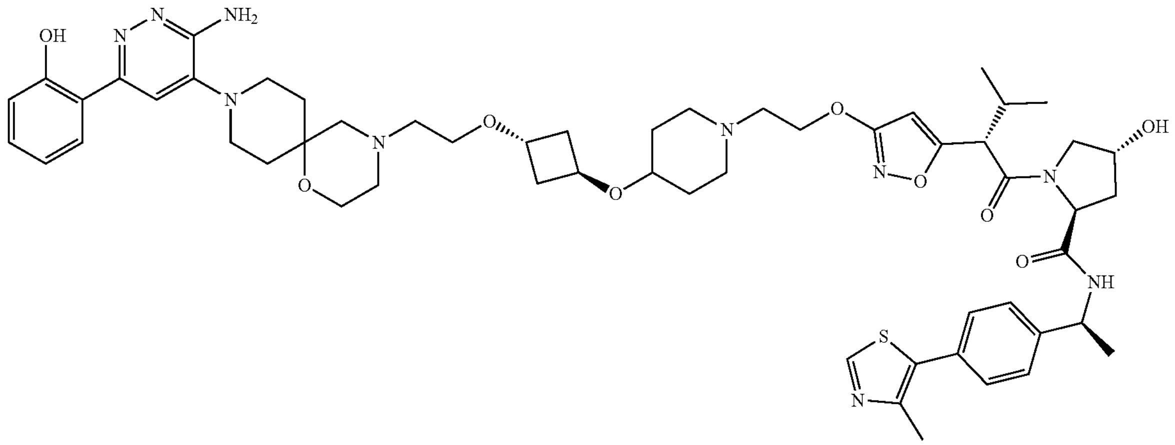
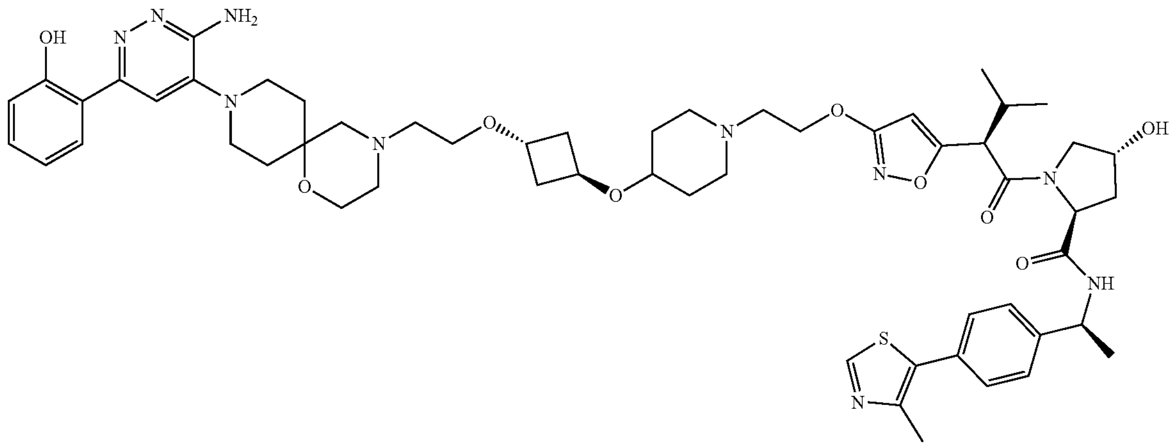

-continued
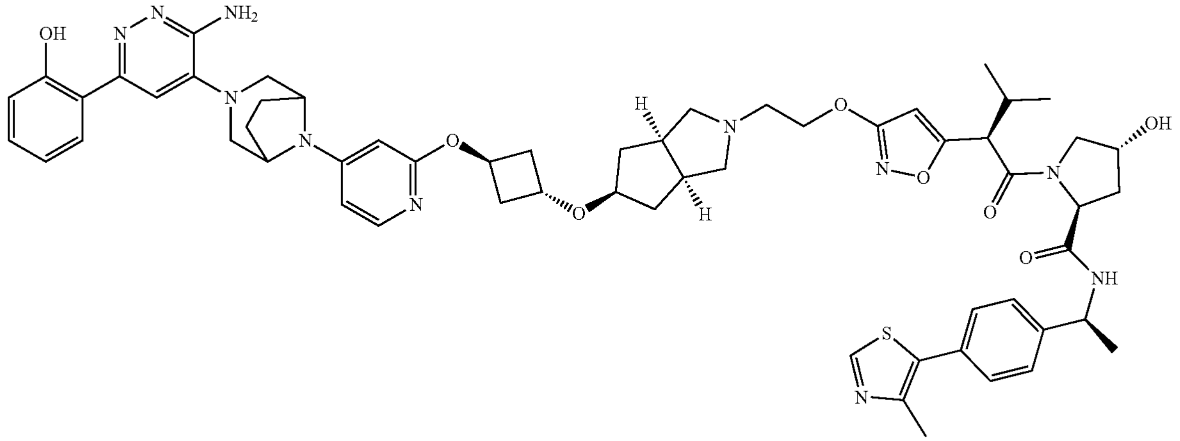
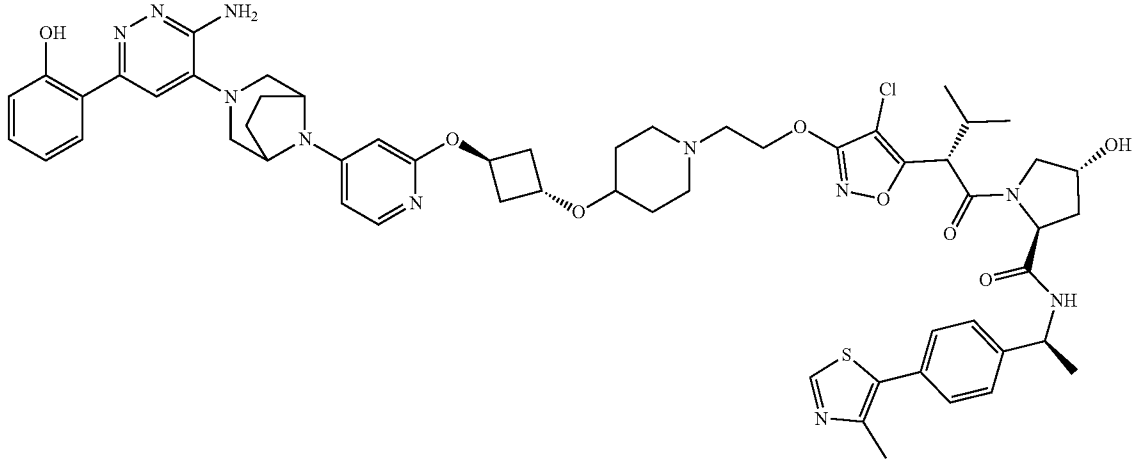
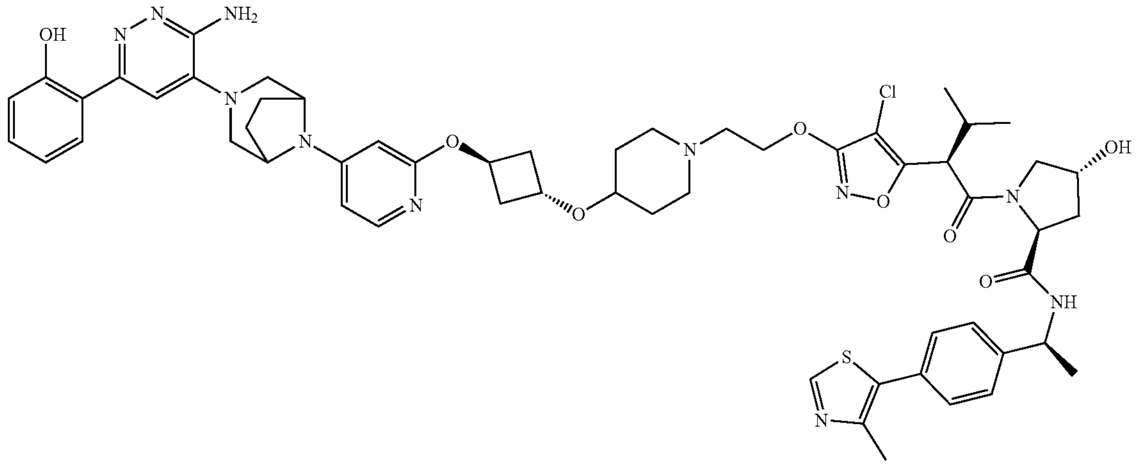

-continued
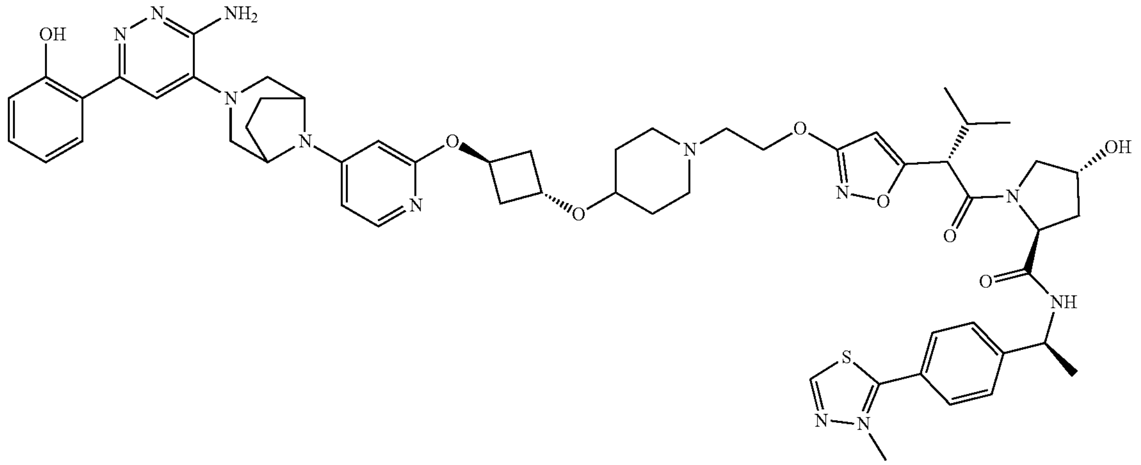
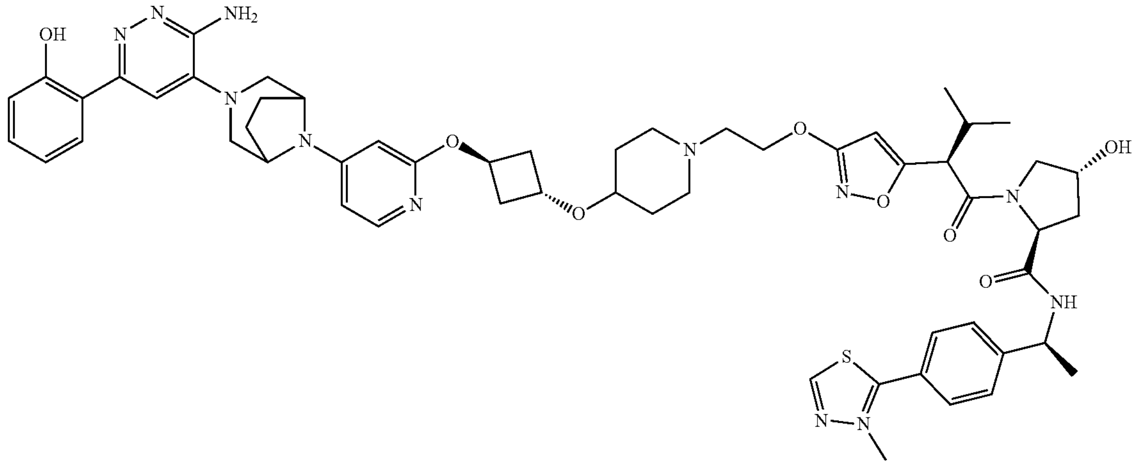
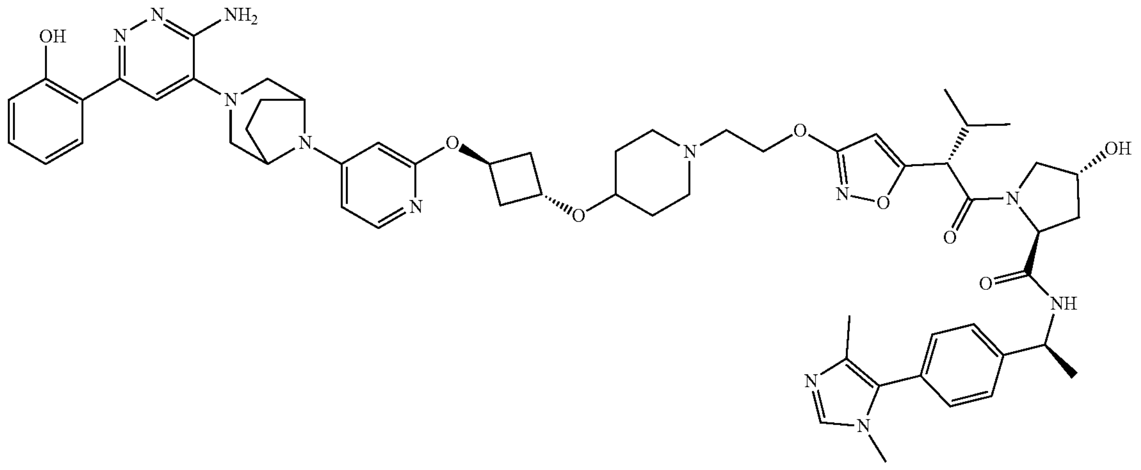

-continued
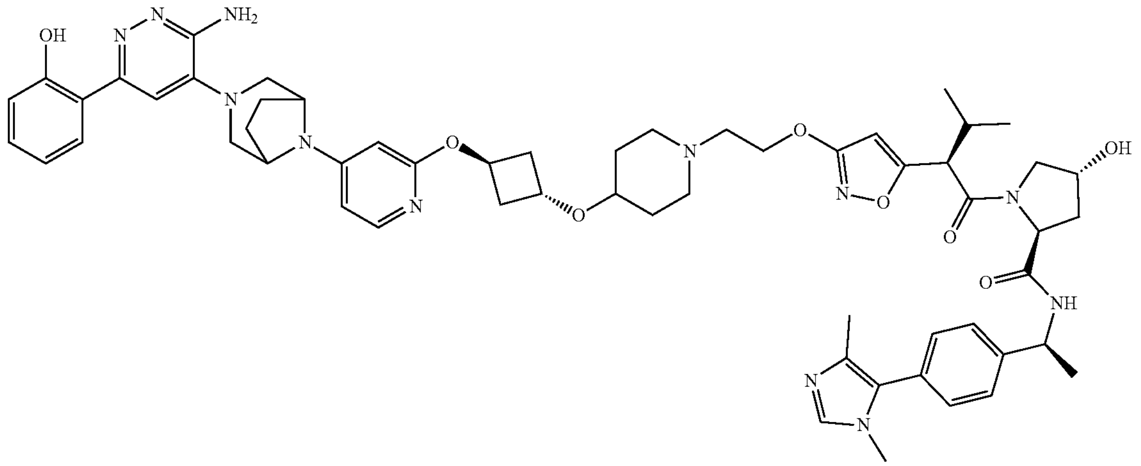
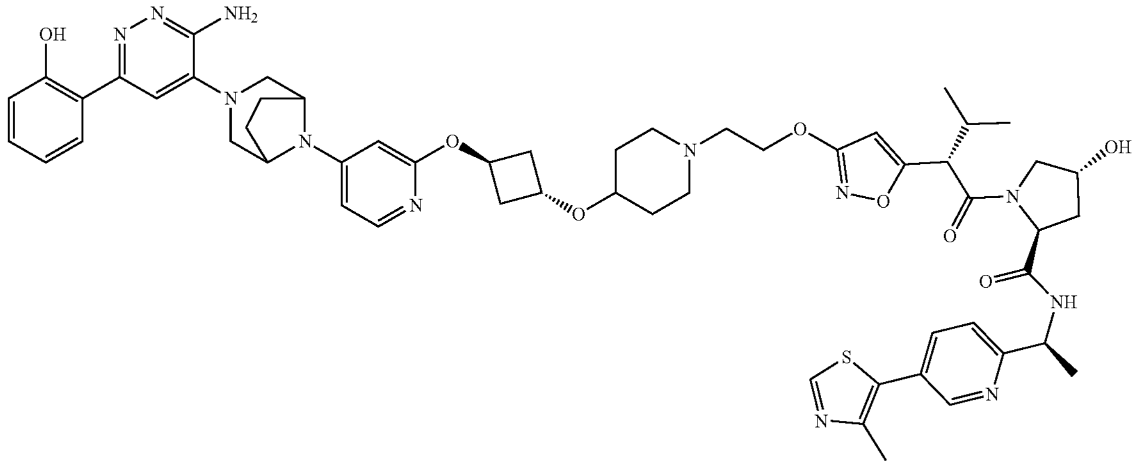
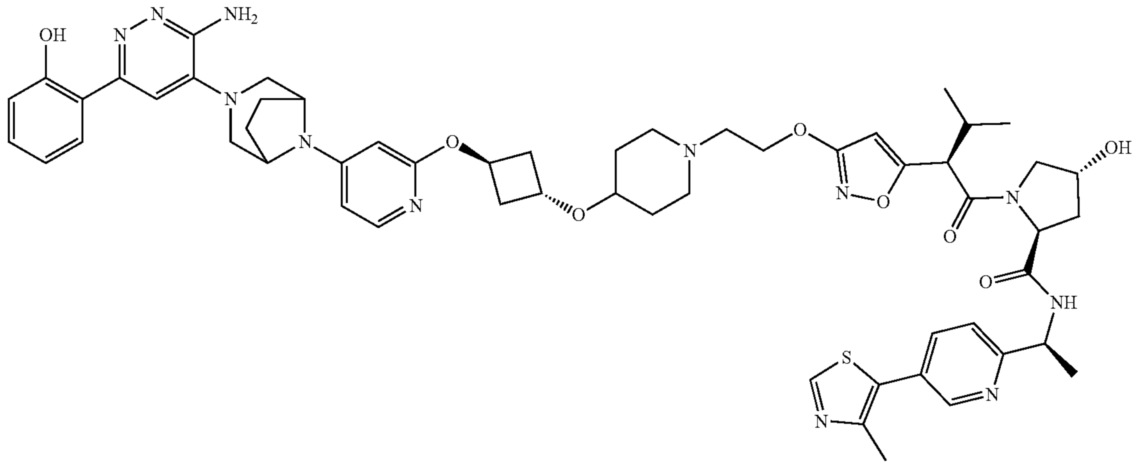

-continued
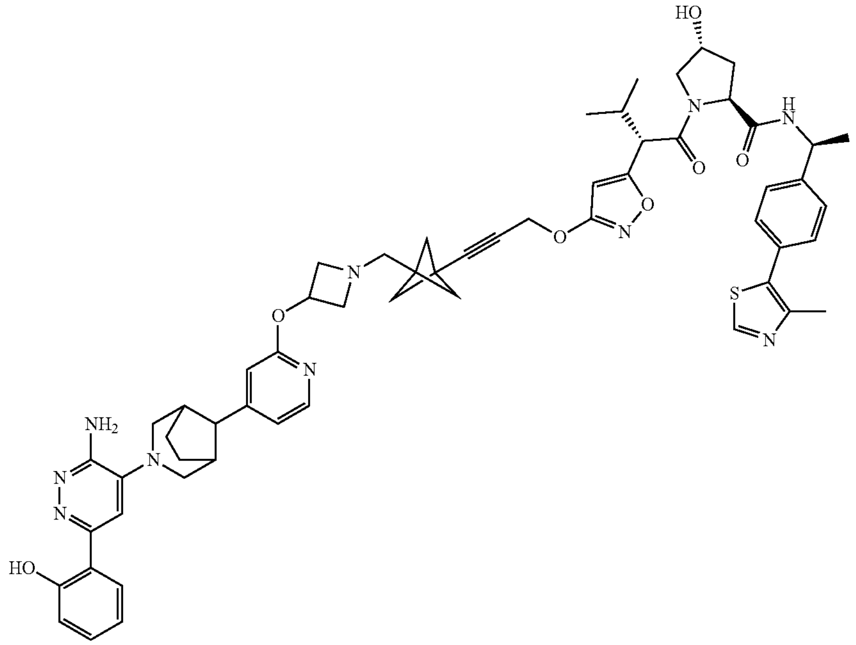
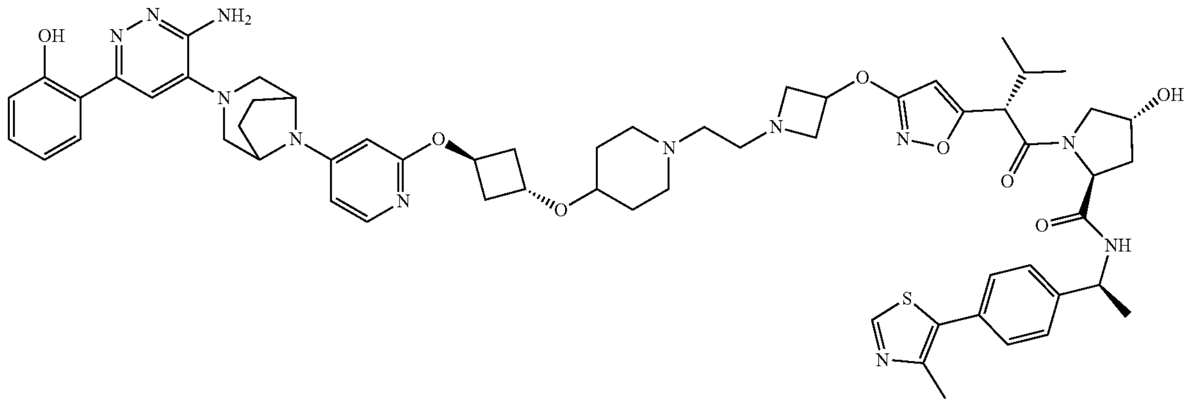
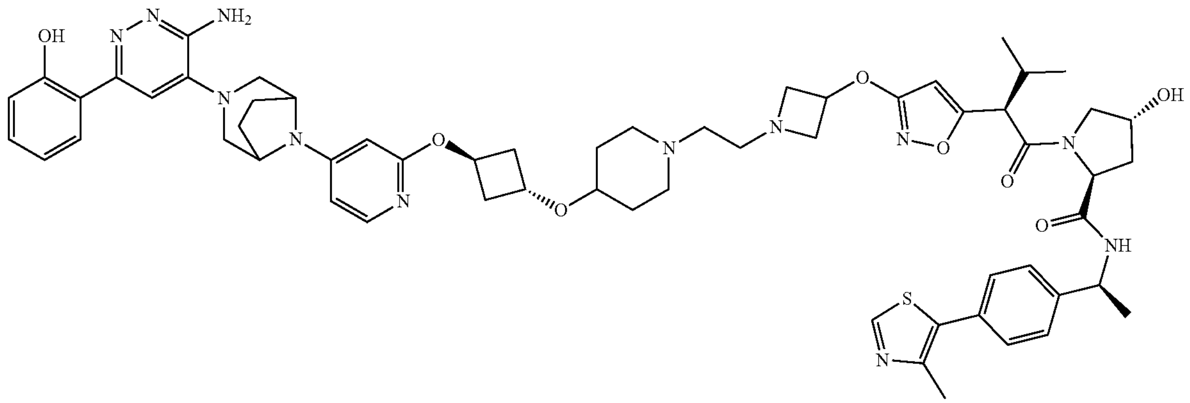

-continued
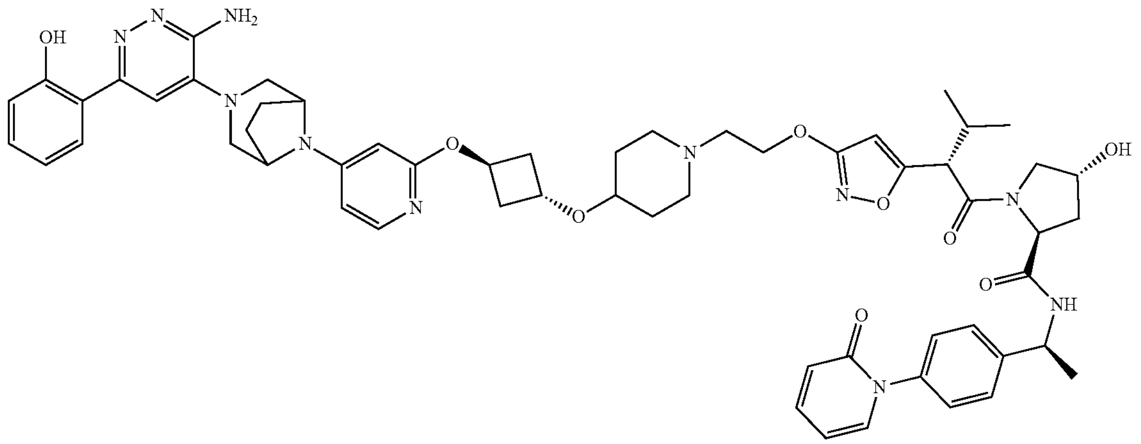
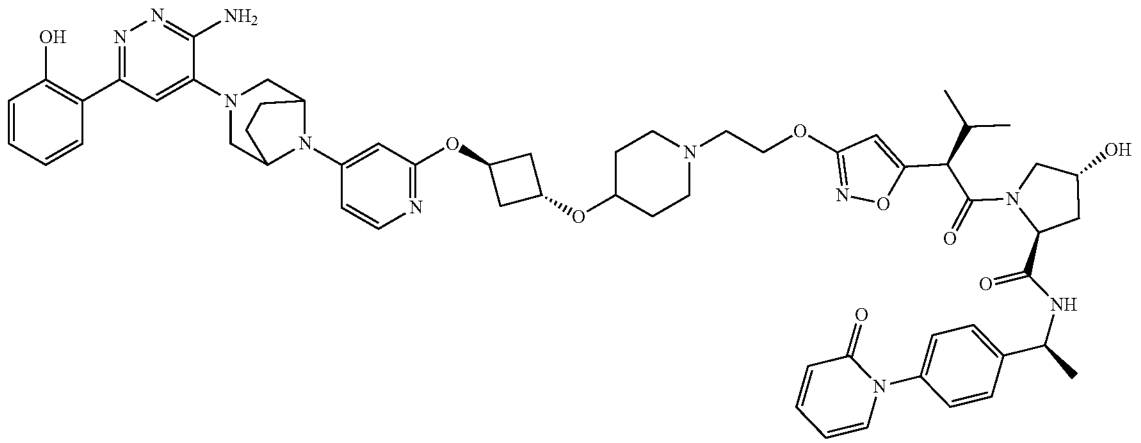
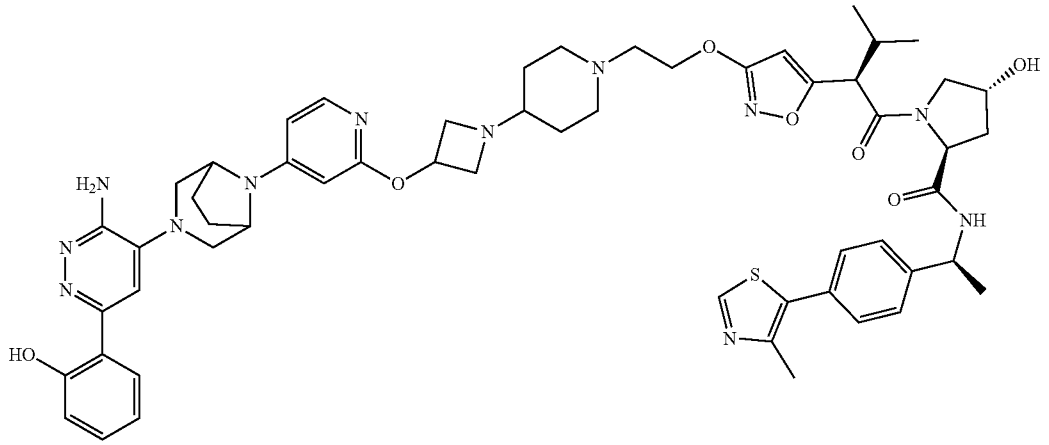

-continued
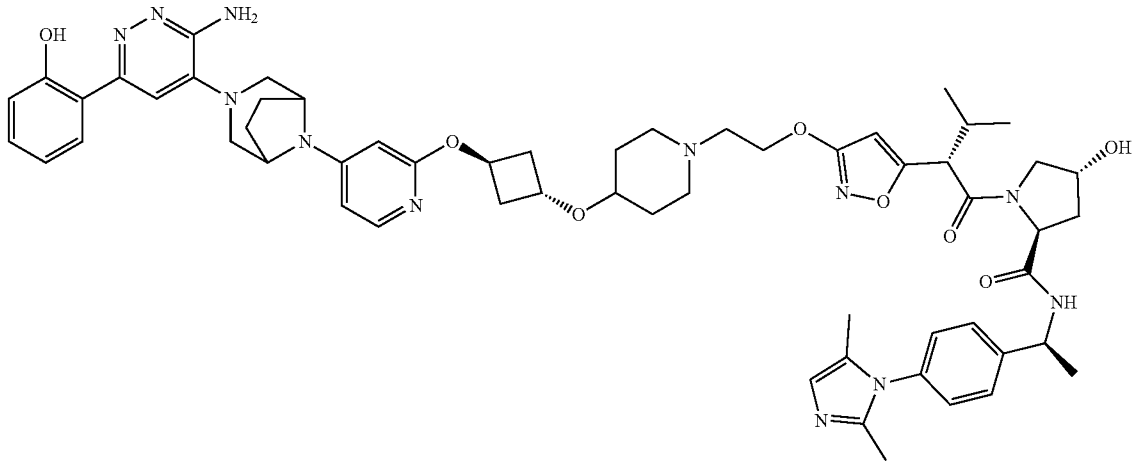
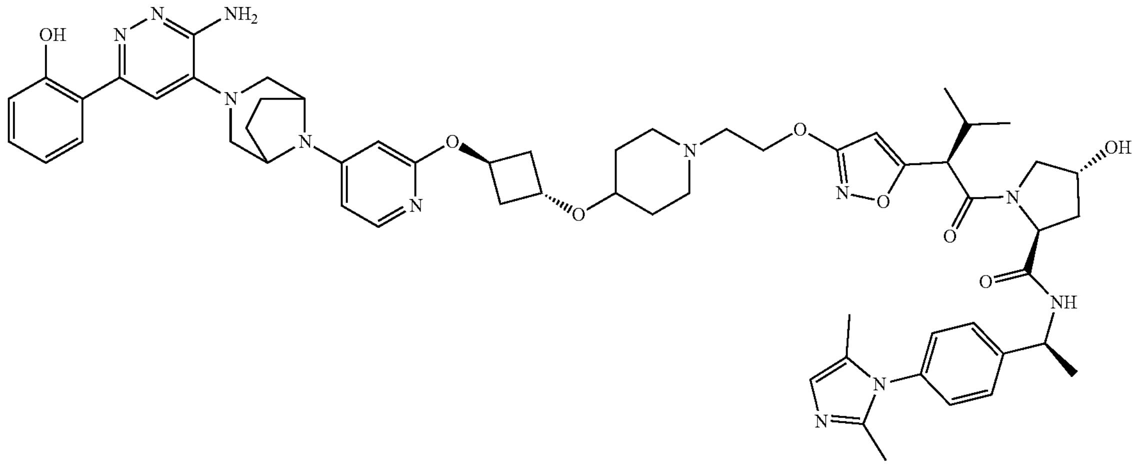
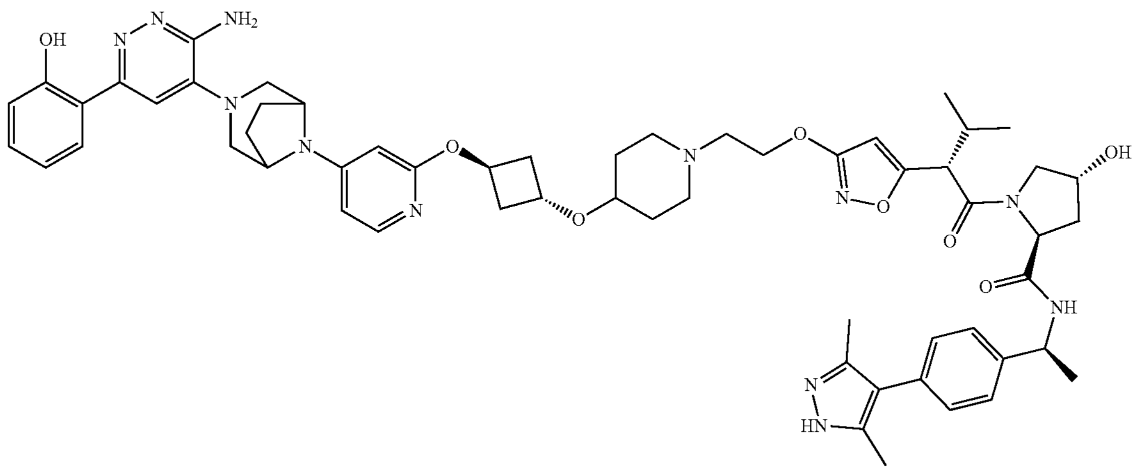 [SMILES: Cc1n[nH]c(C)c1-c1ccc([C@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cc1]

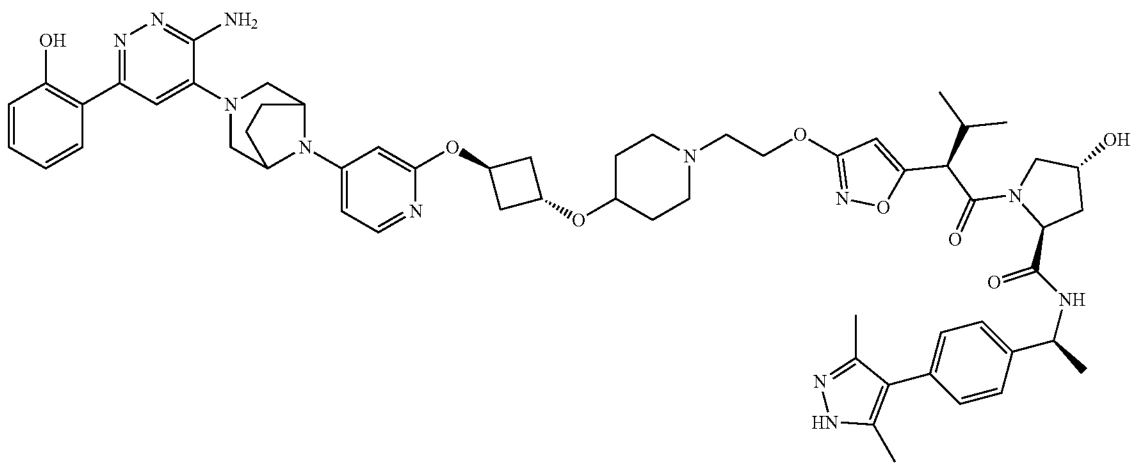
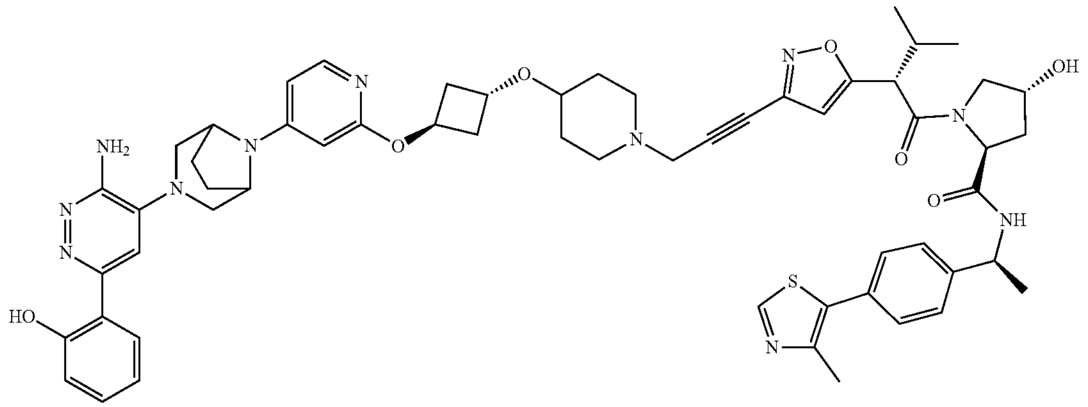
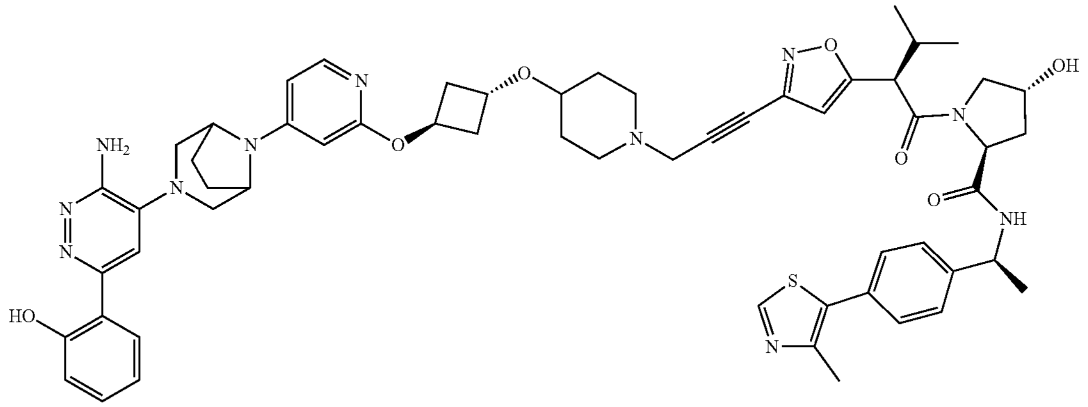

-continued
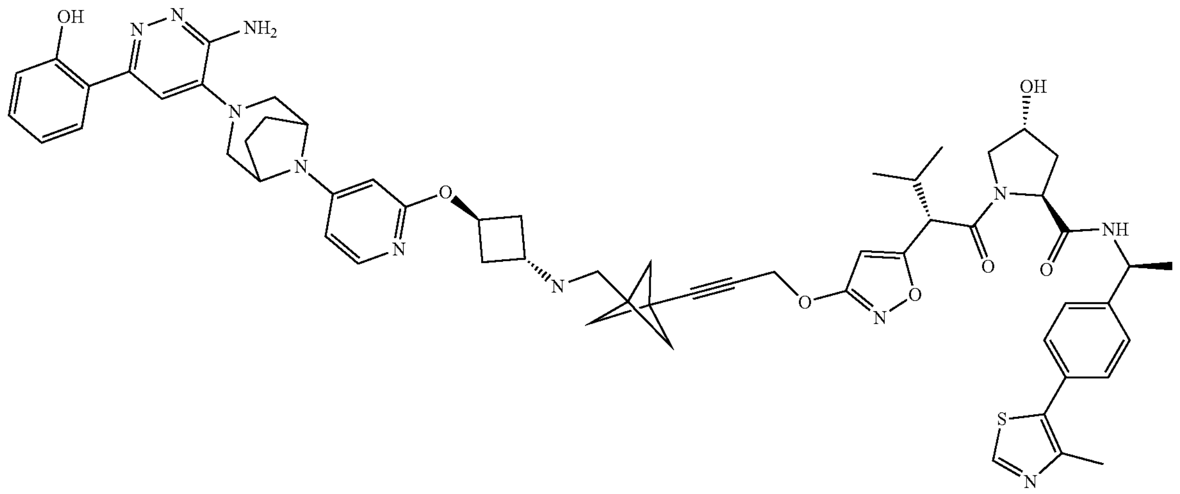
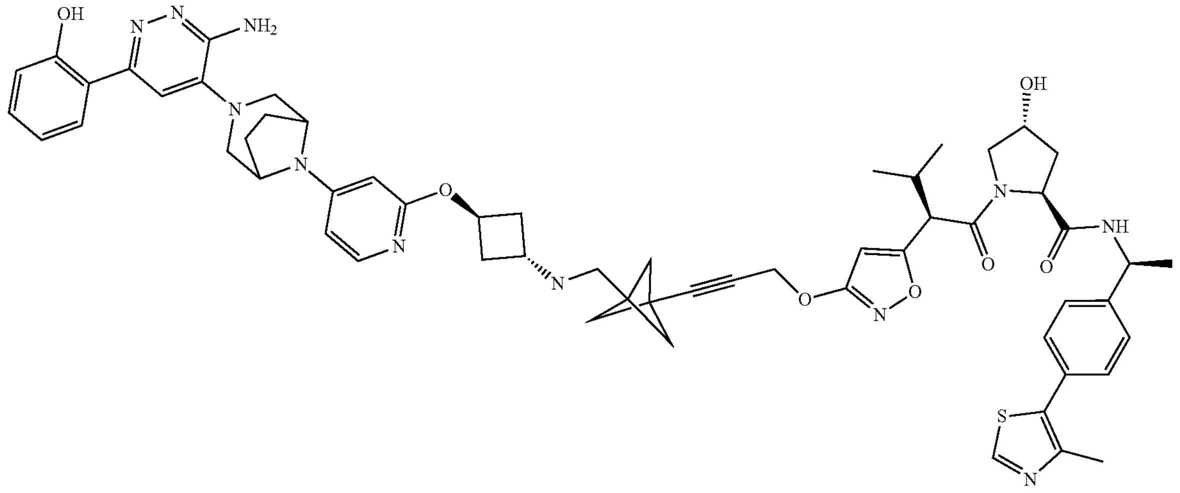
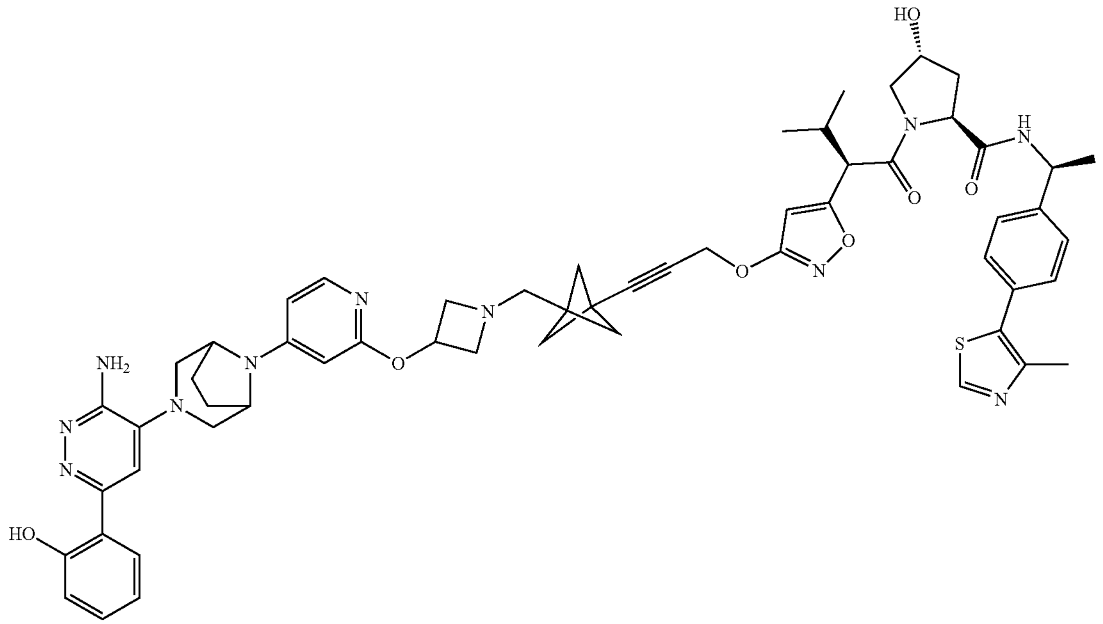

-continued
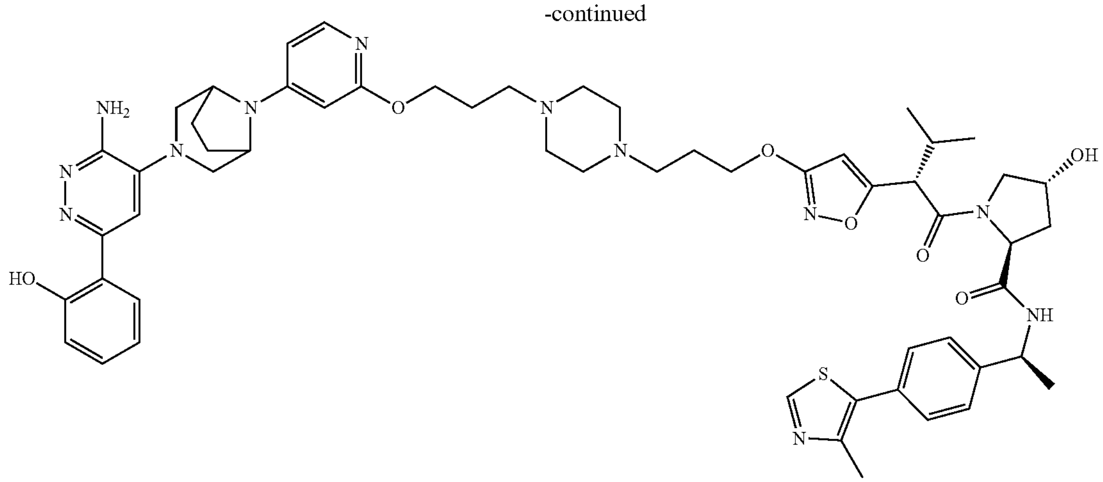
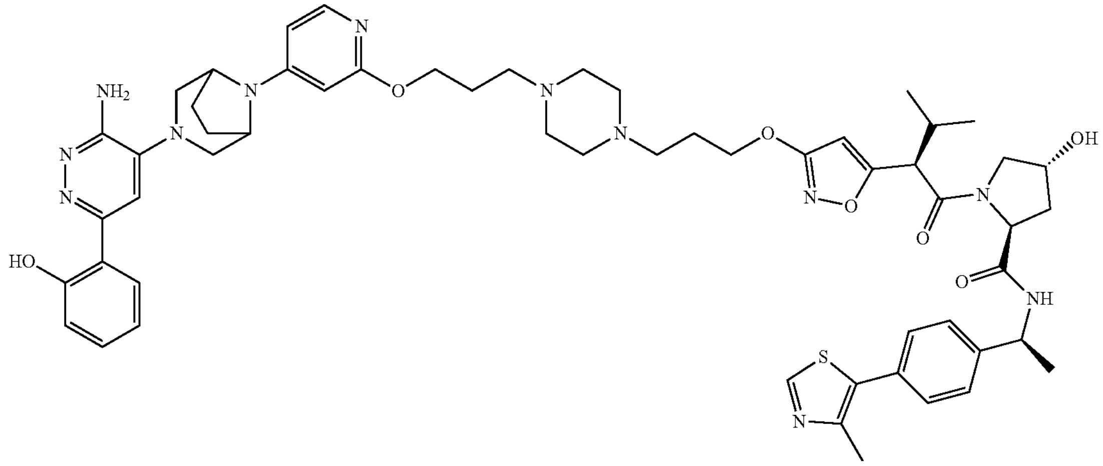
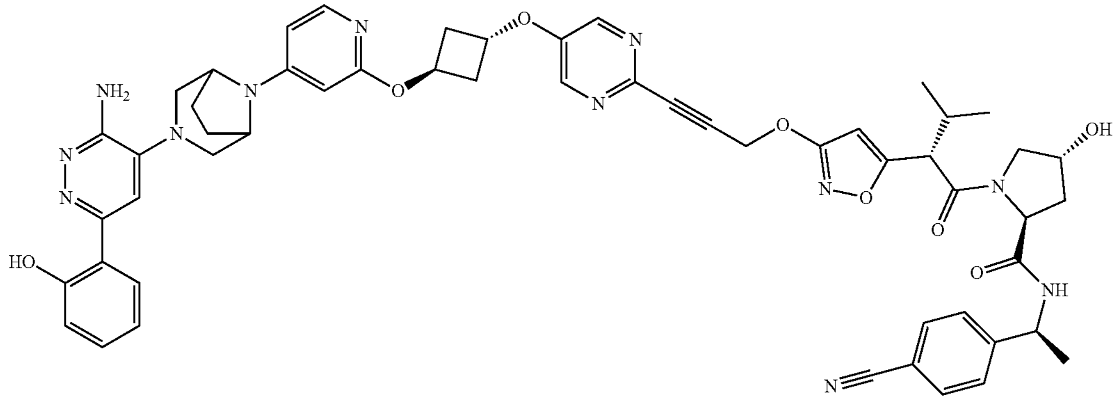
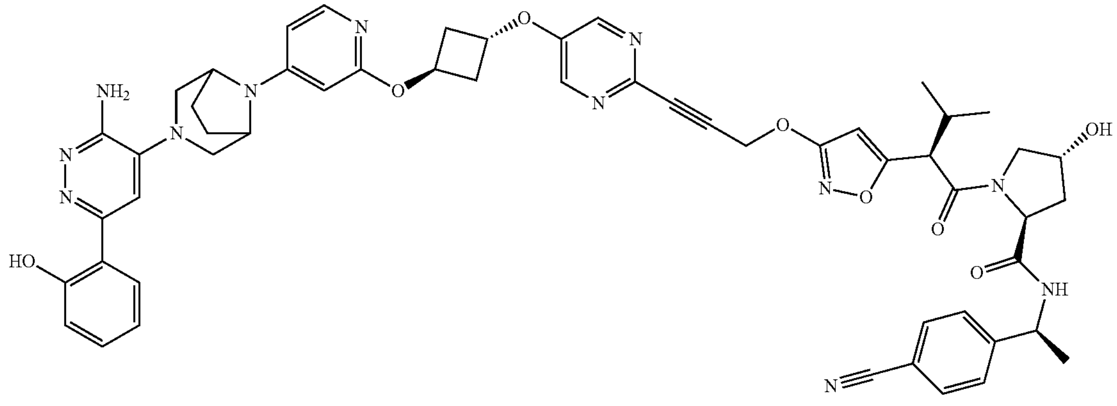

-continued
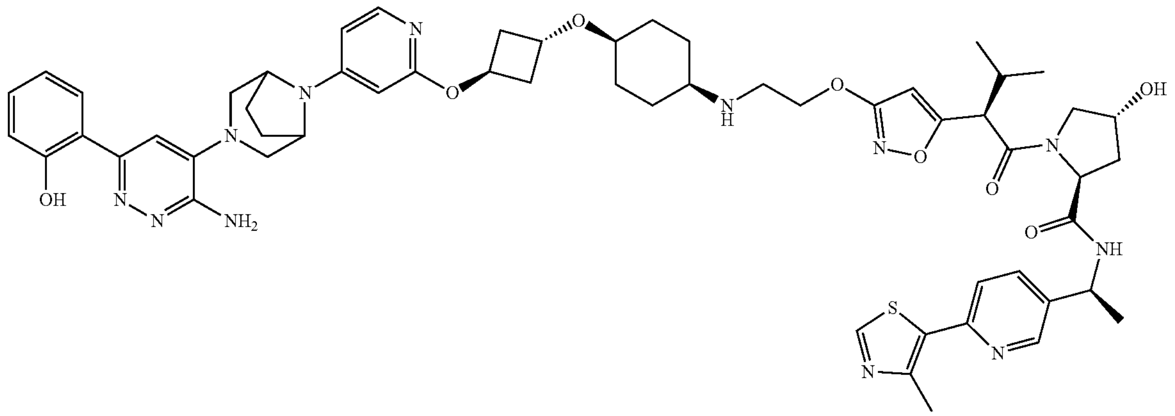
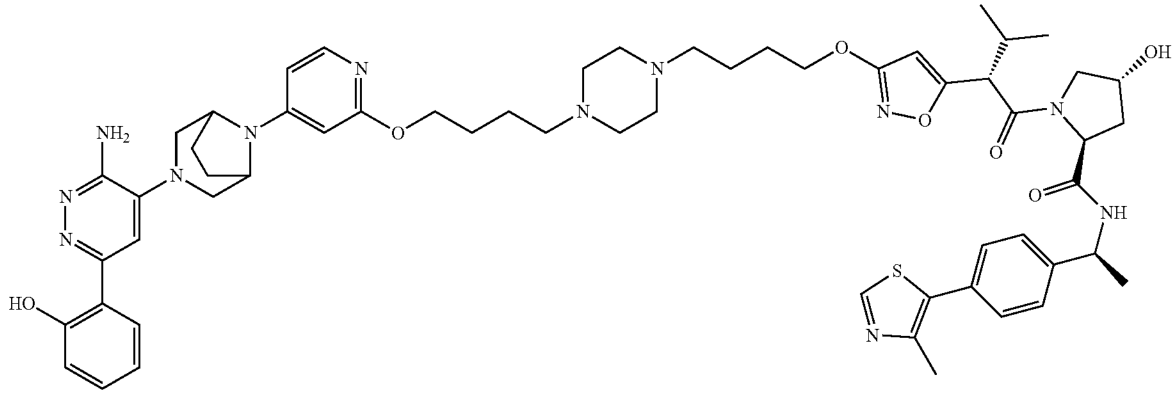
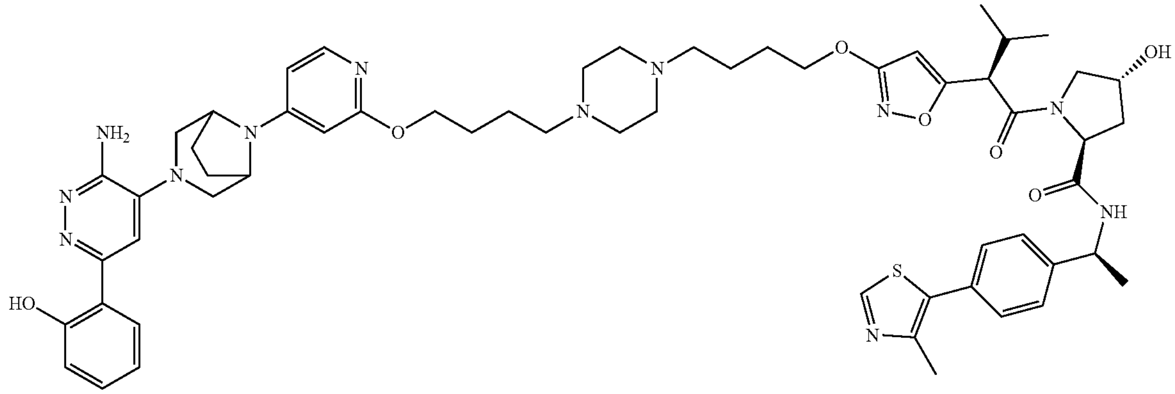
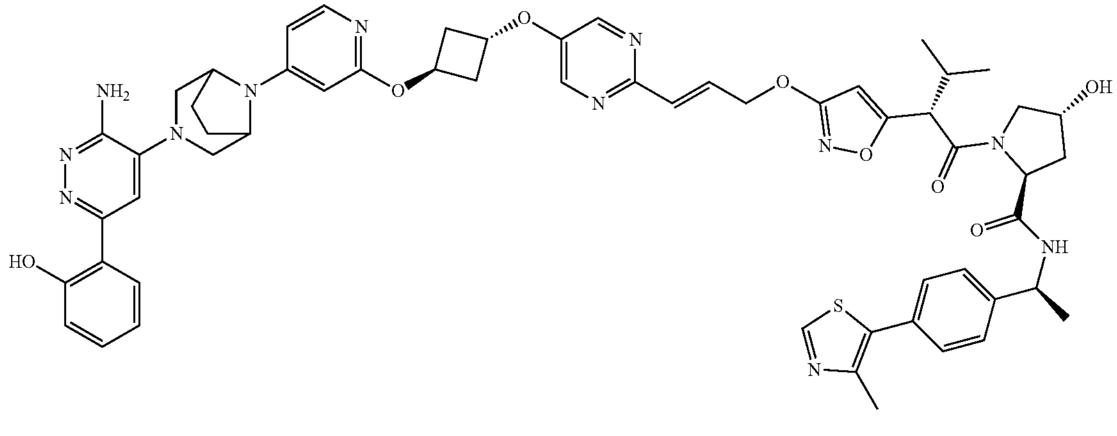

-continued
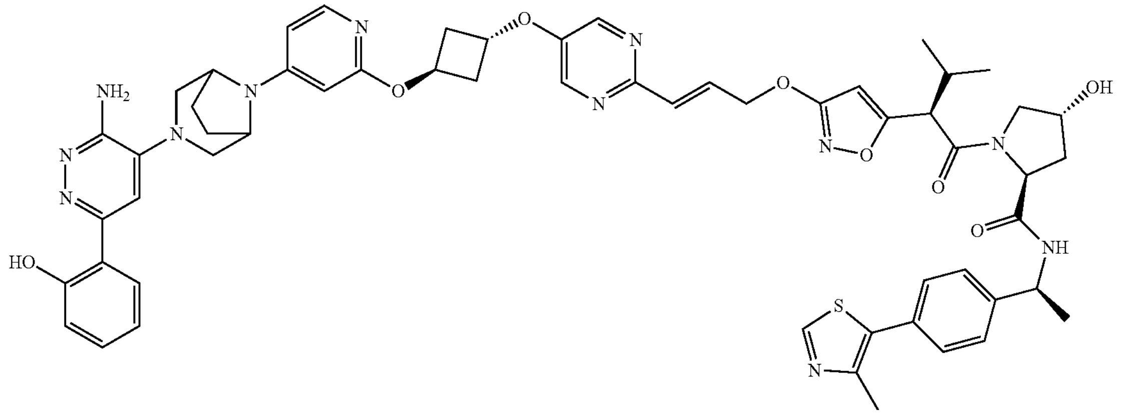
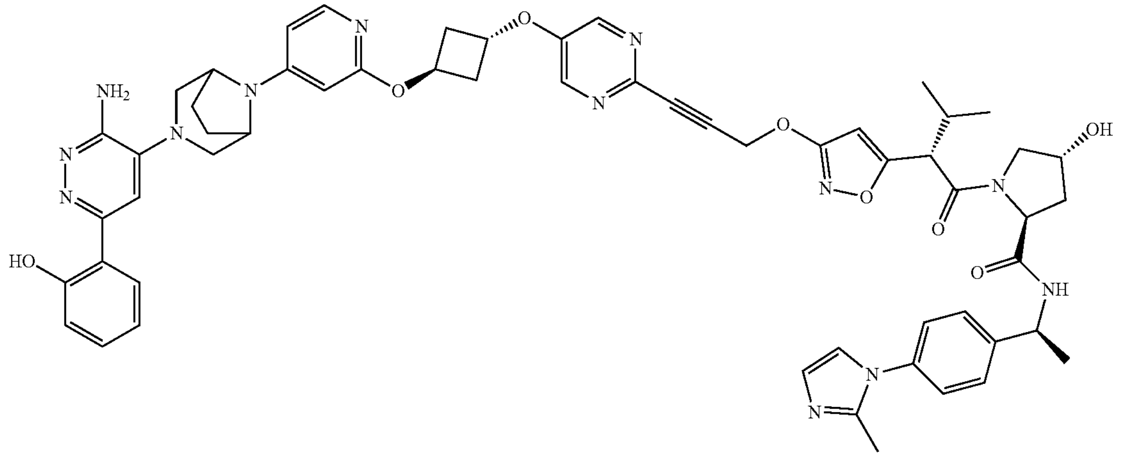
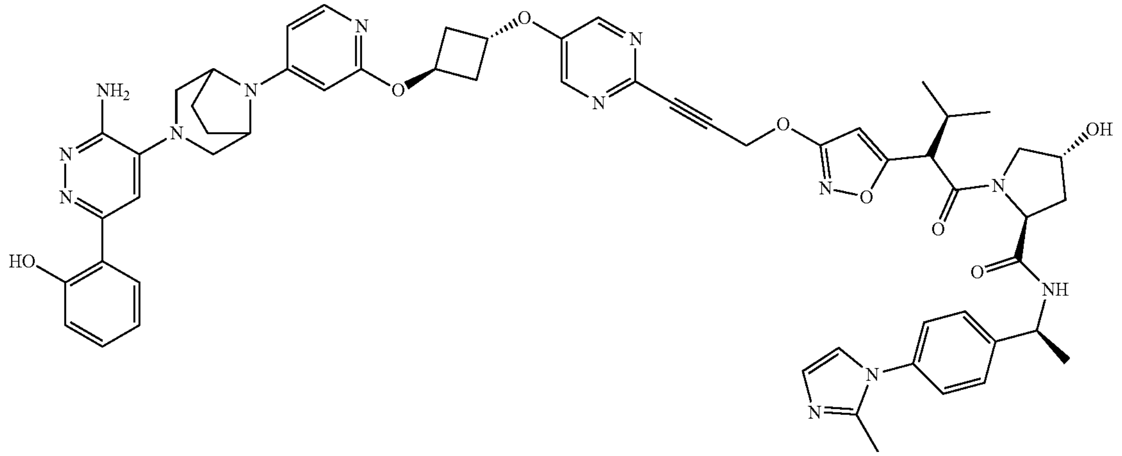

-continued
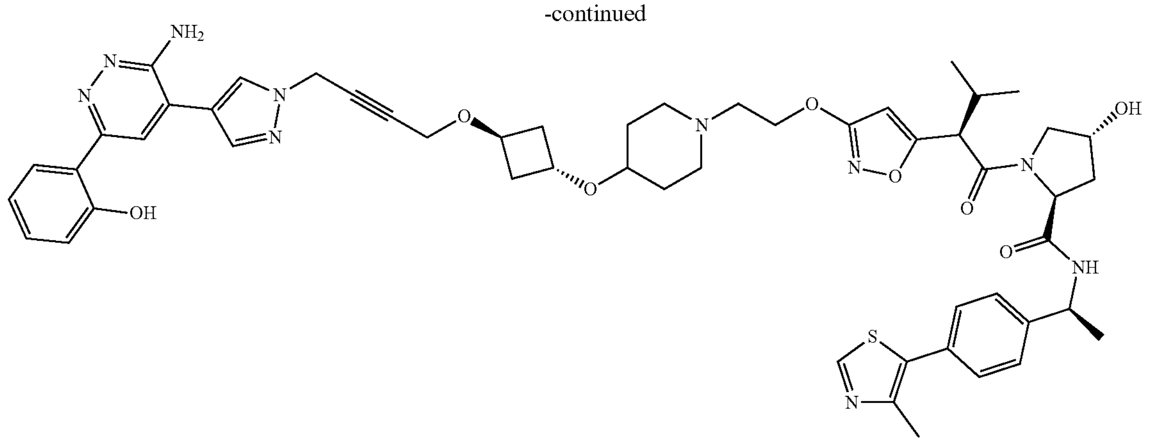
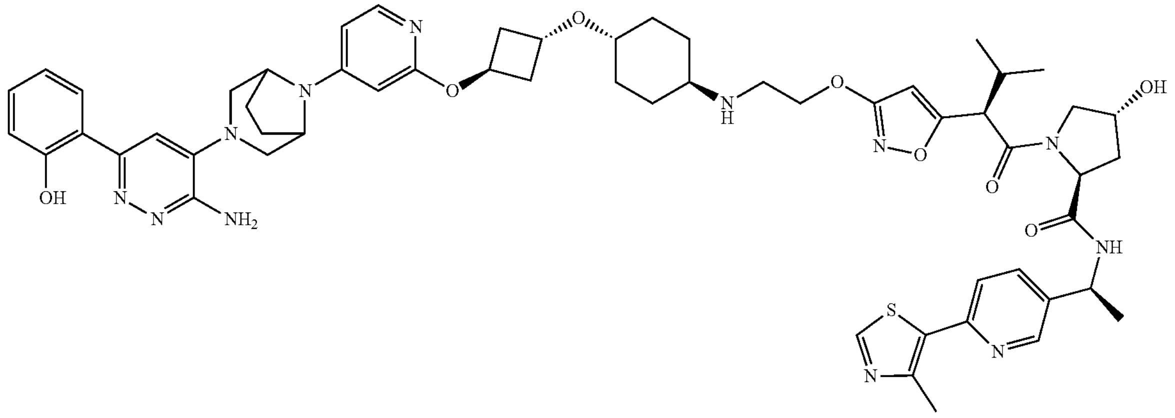
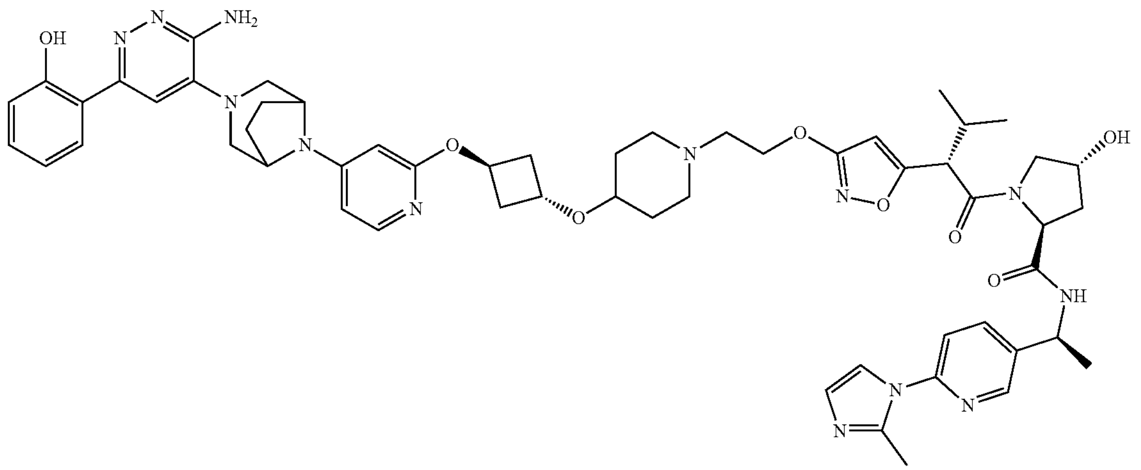

-continued
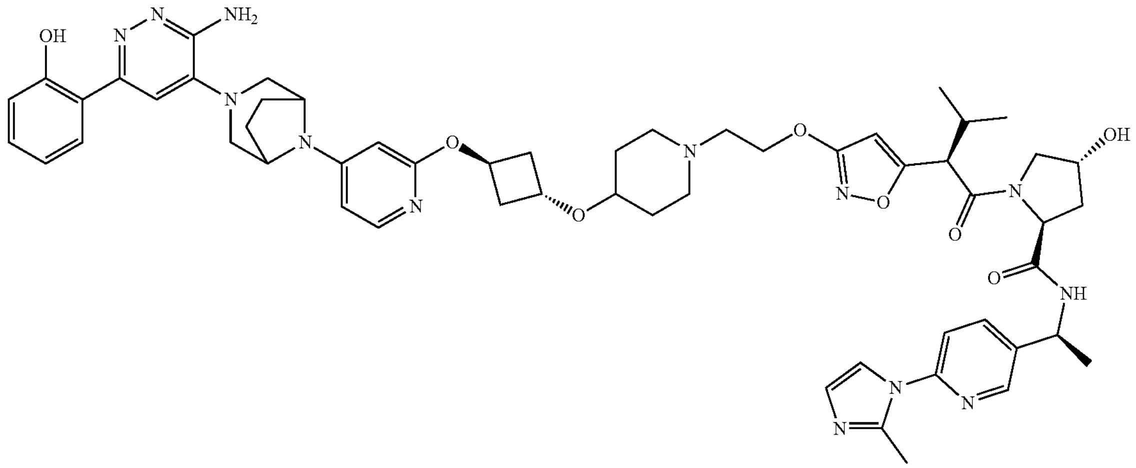
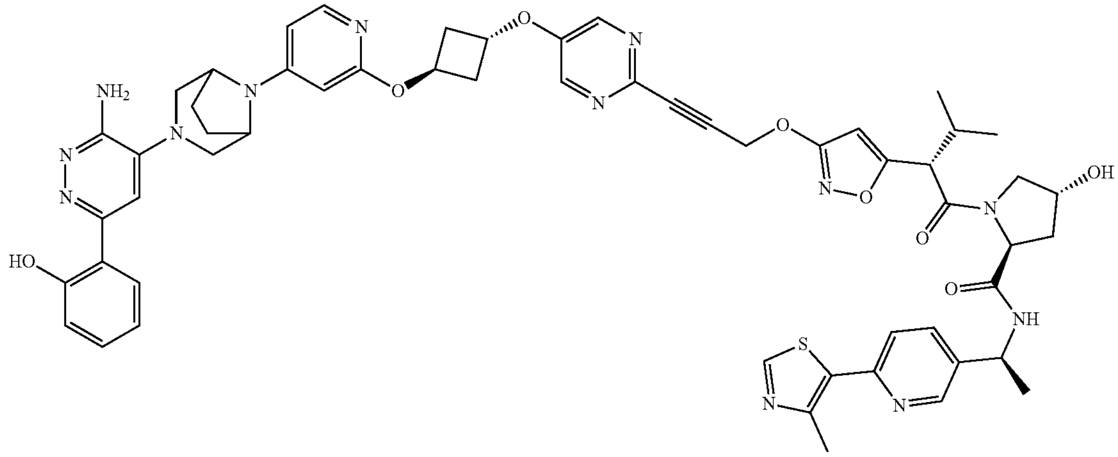
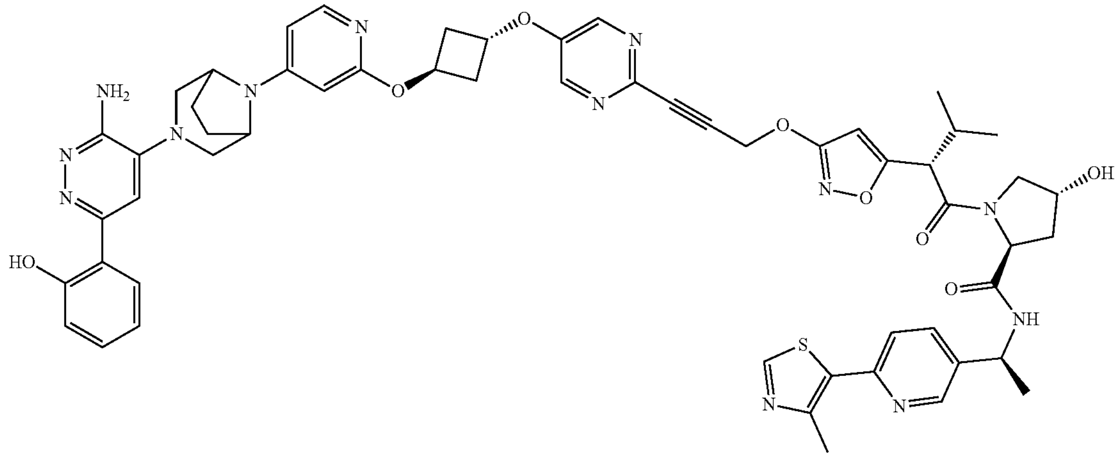

-continued
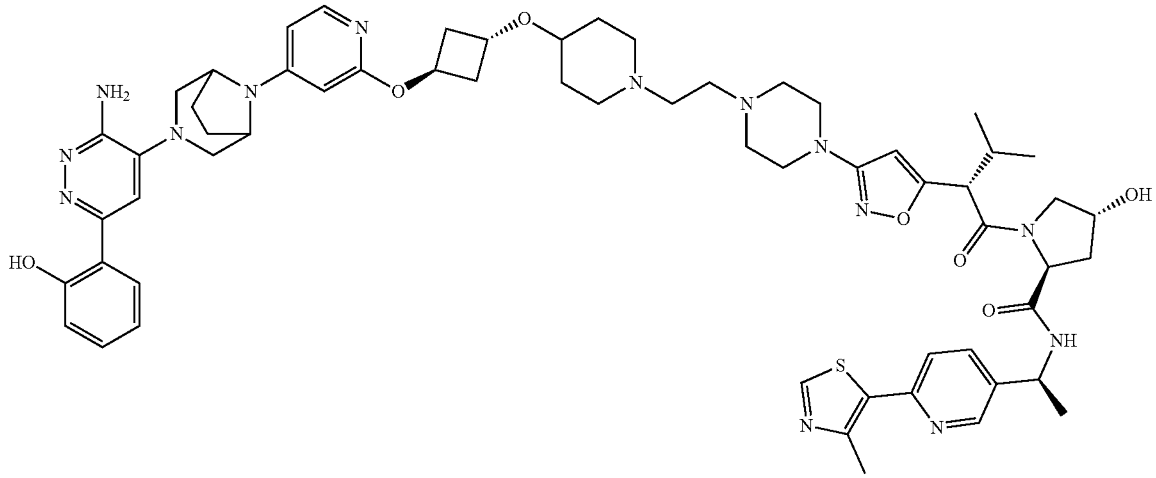
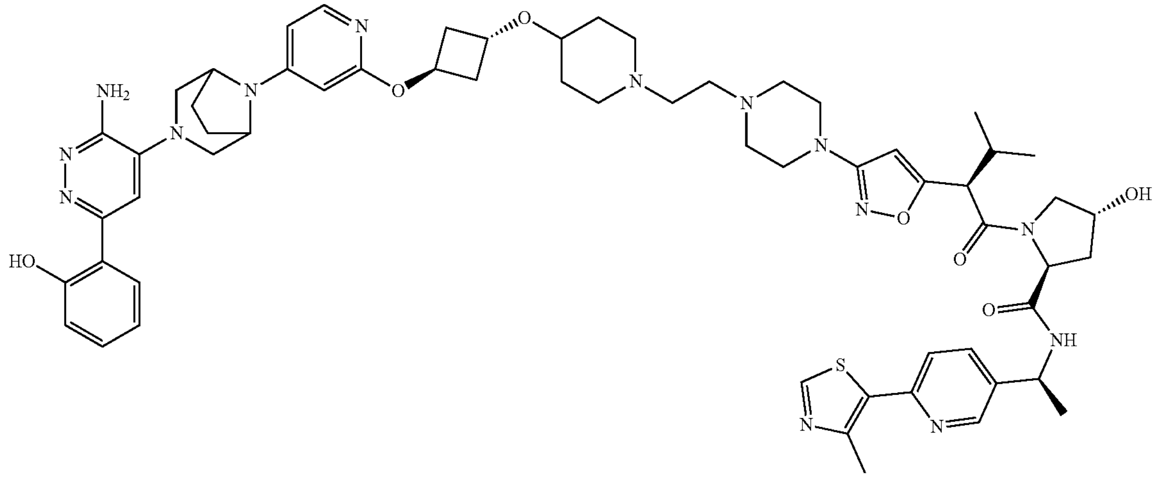
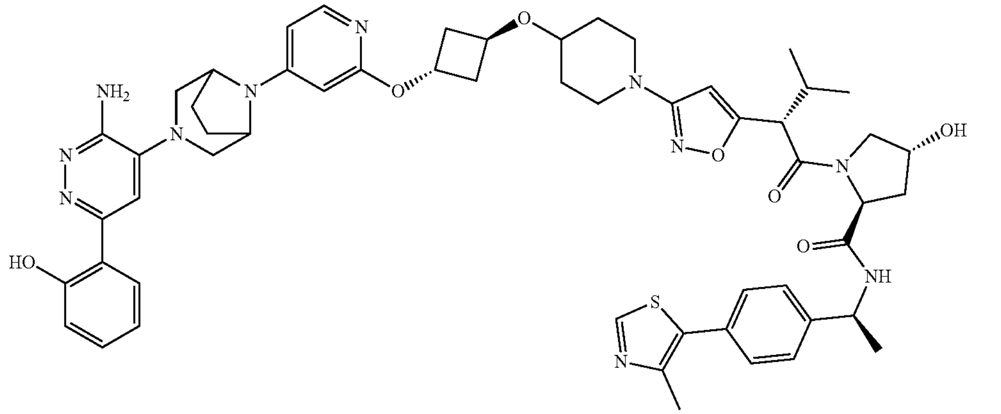

-continued
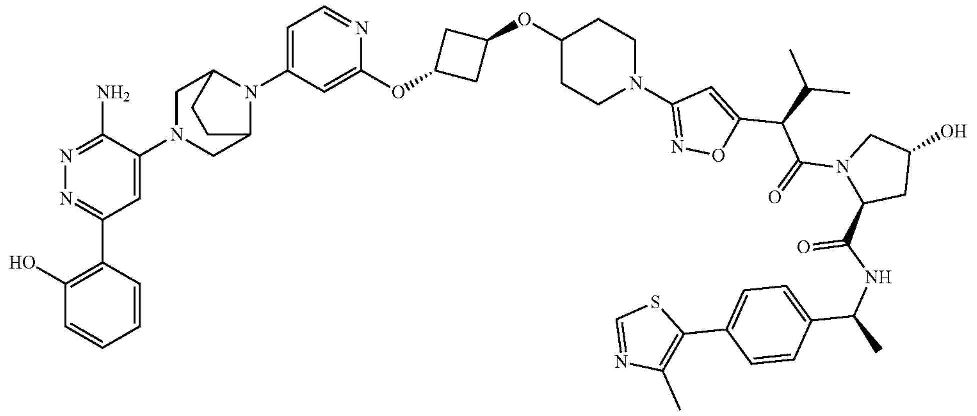
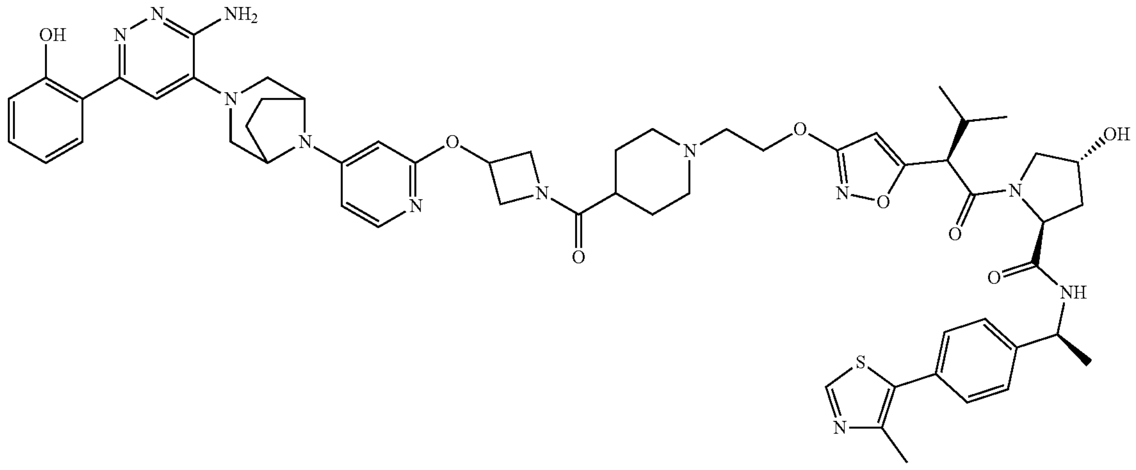
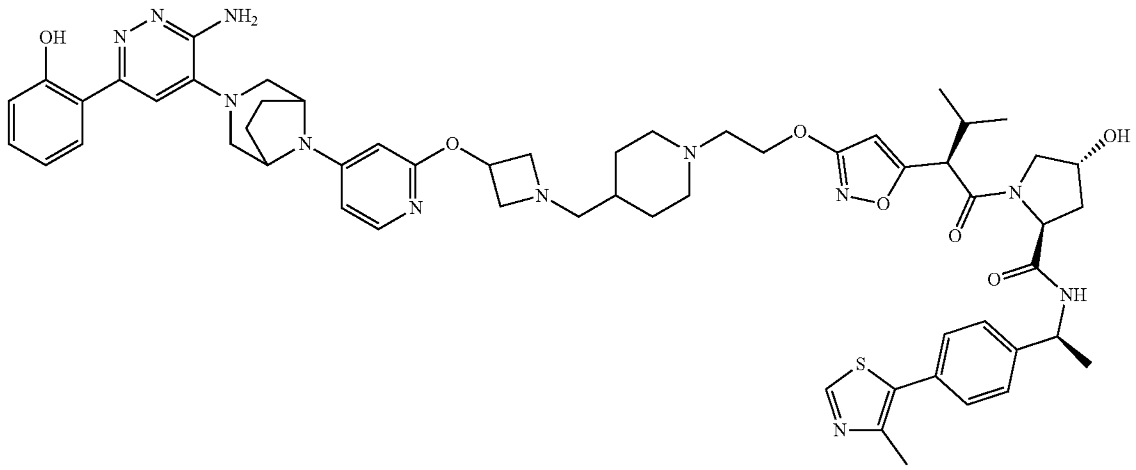

-continued
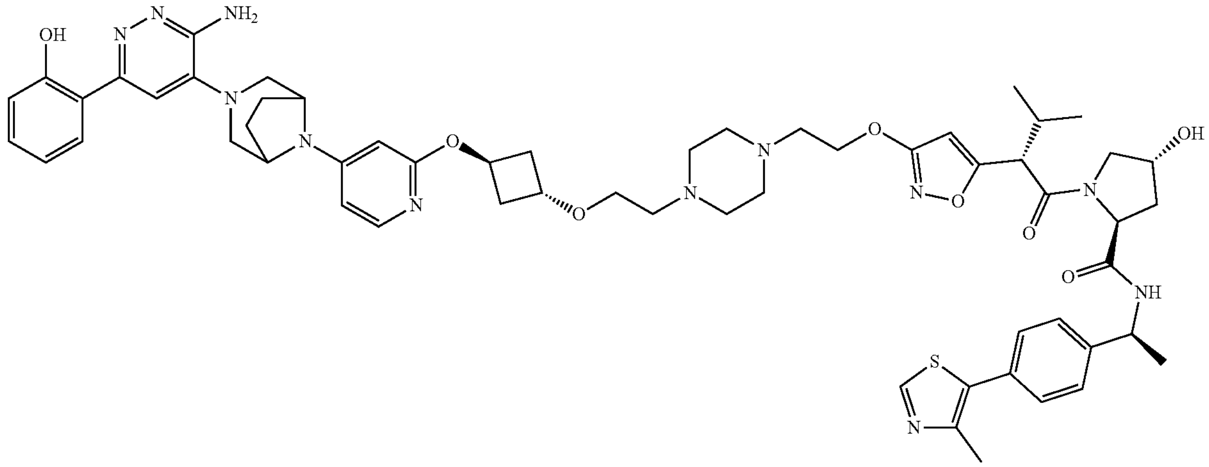
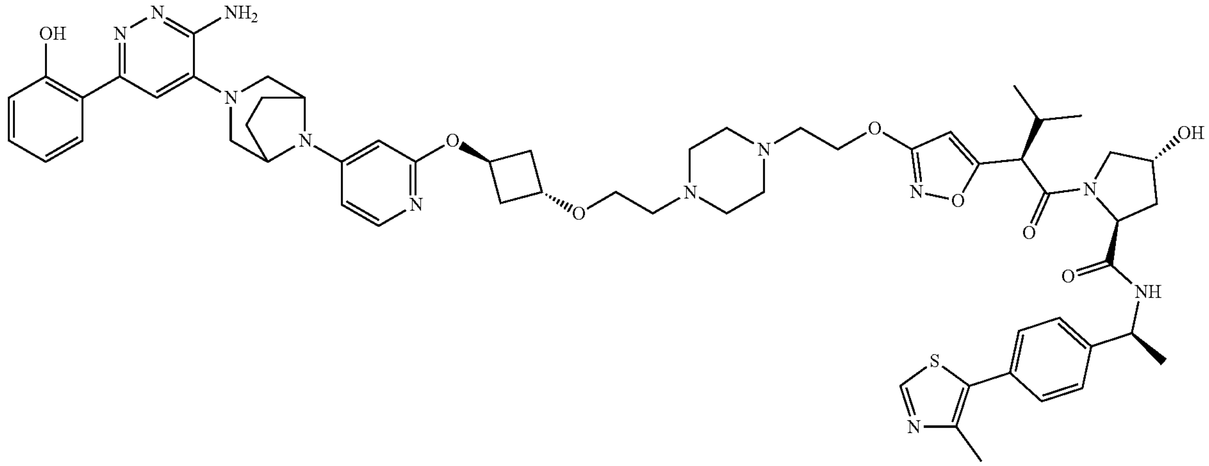
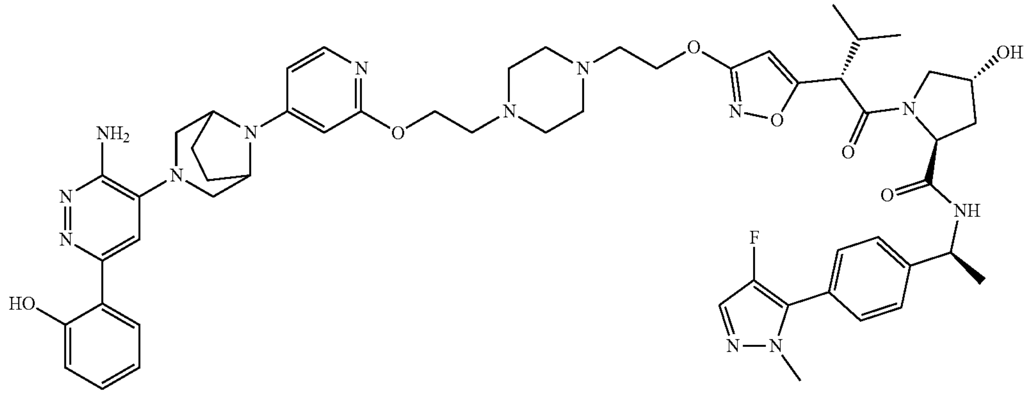
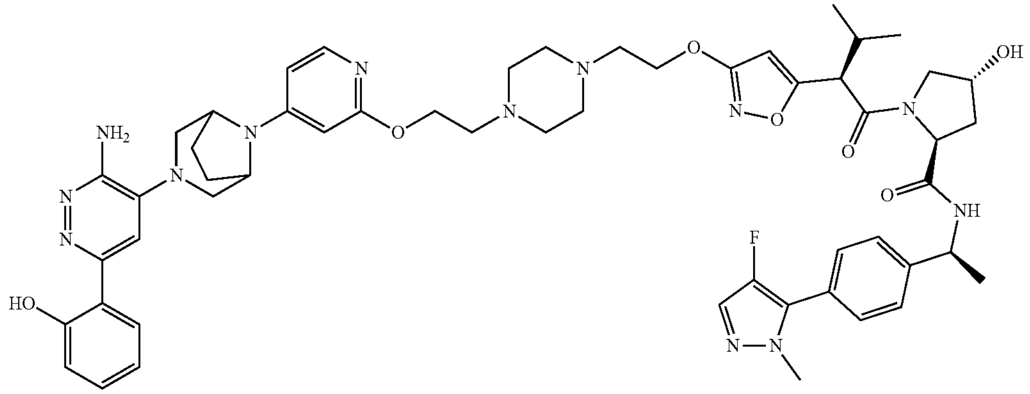

-continued
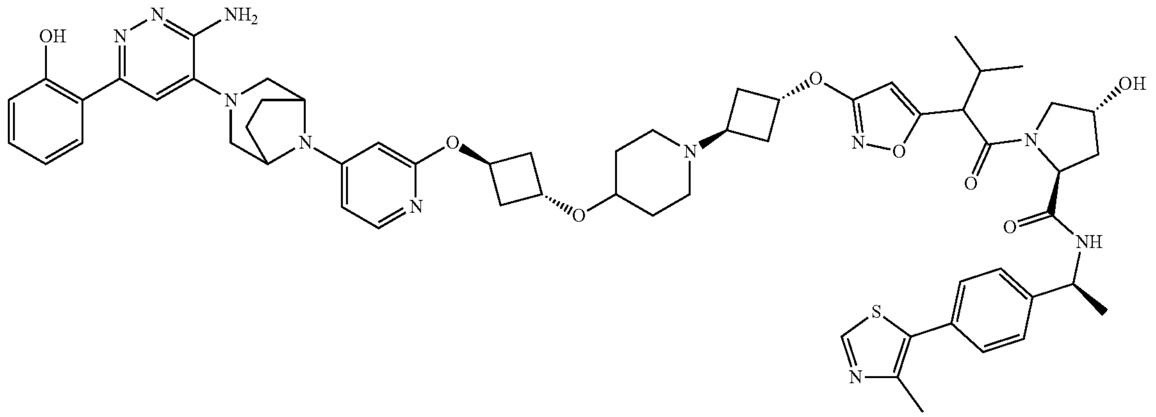
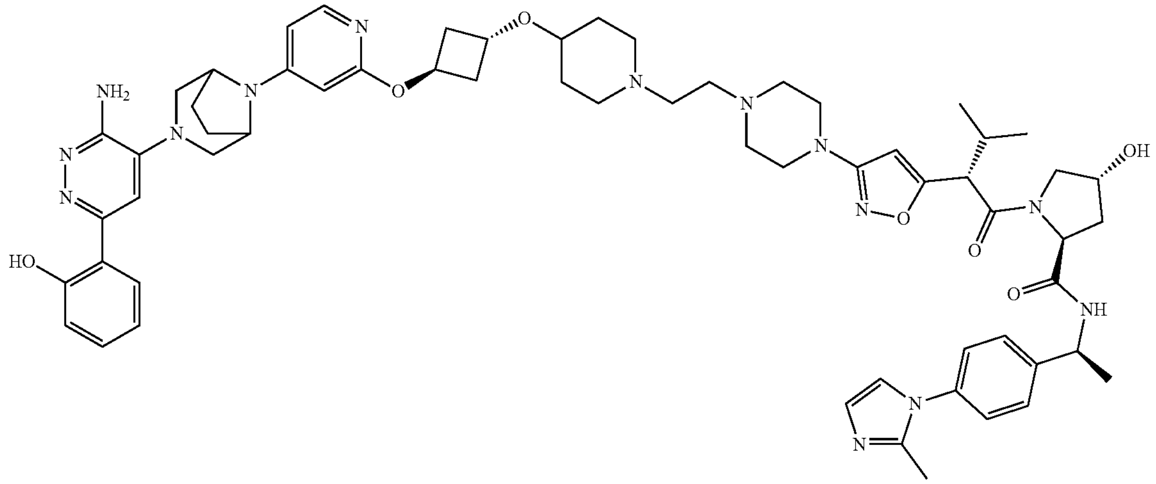
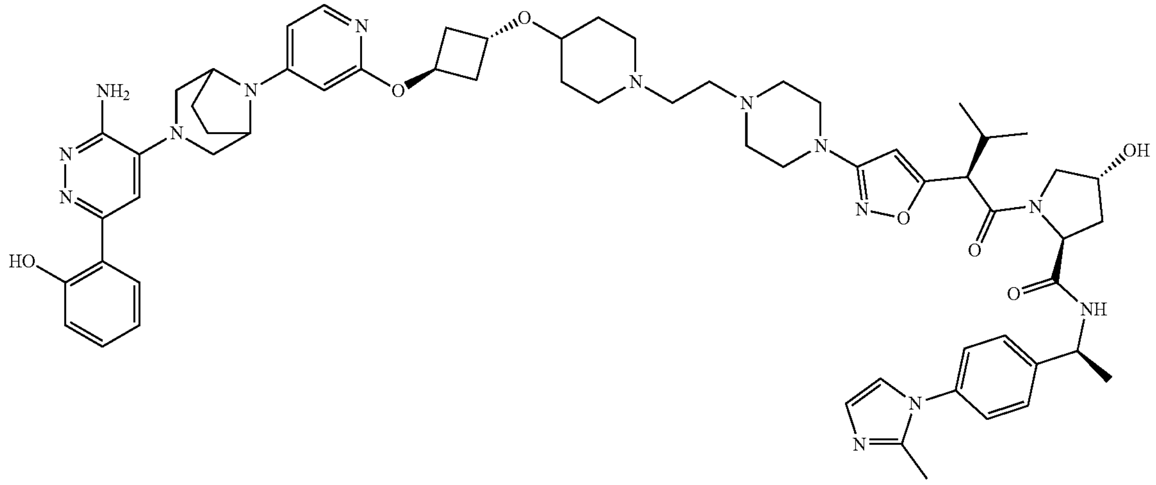

-continued
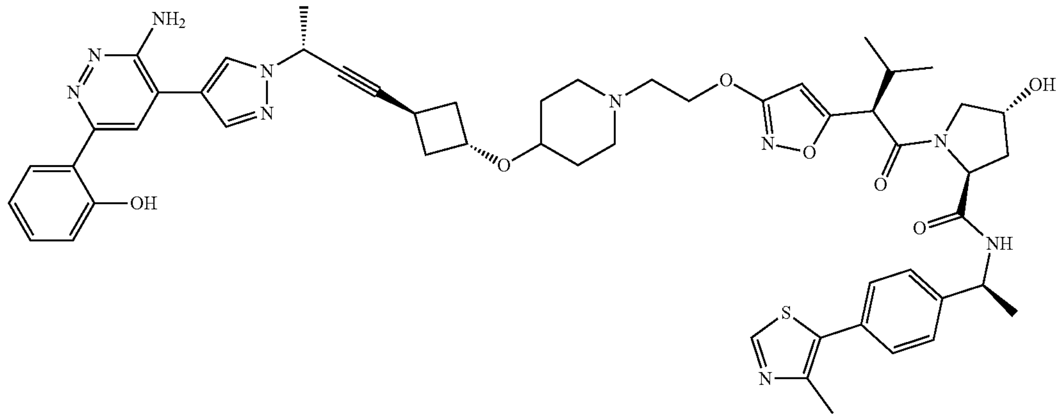
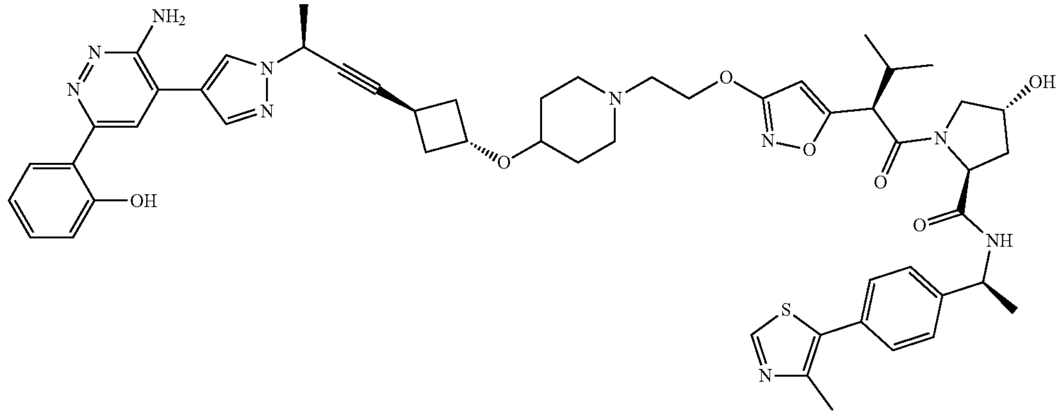
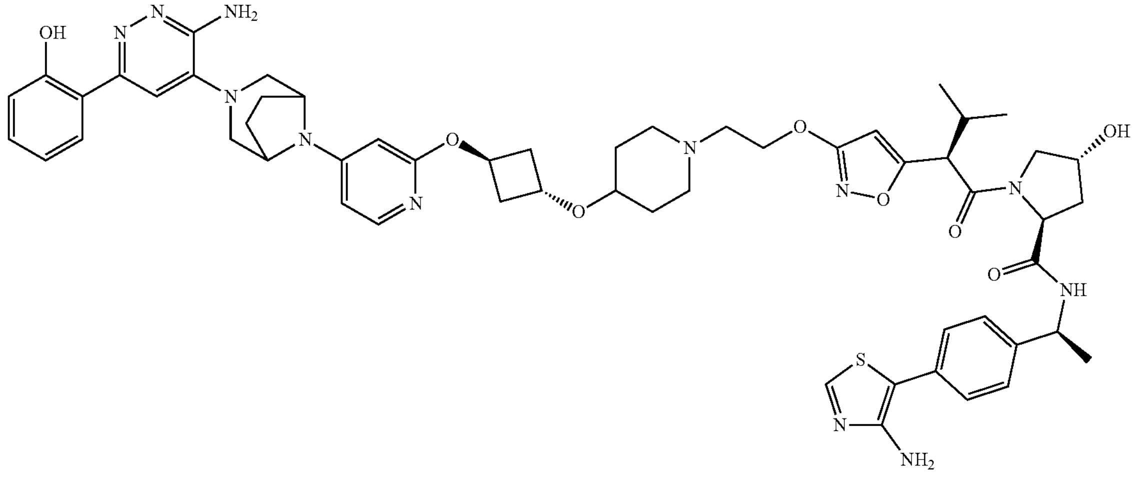

-continued
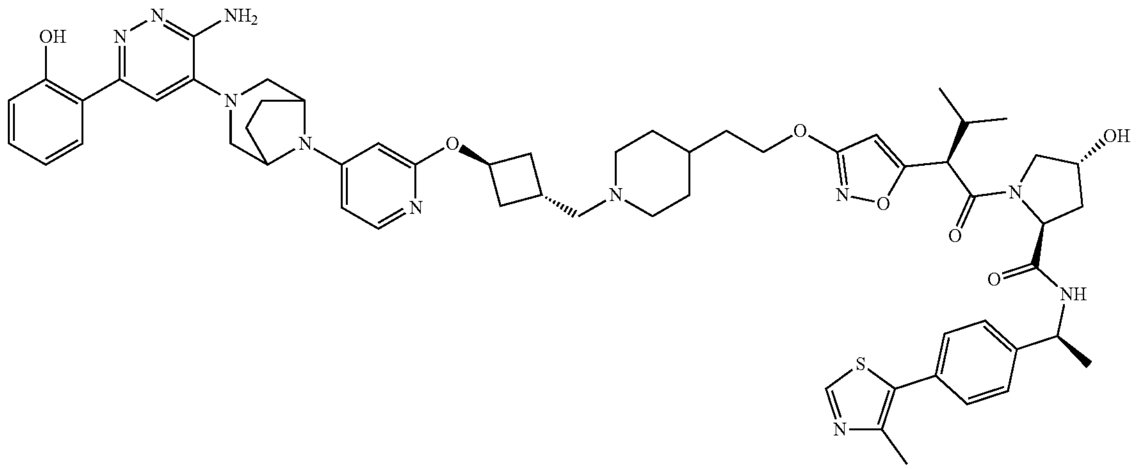
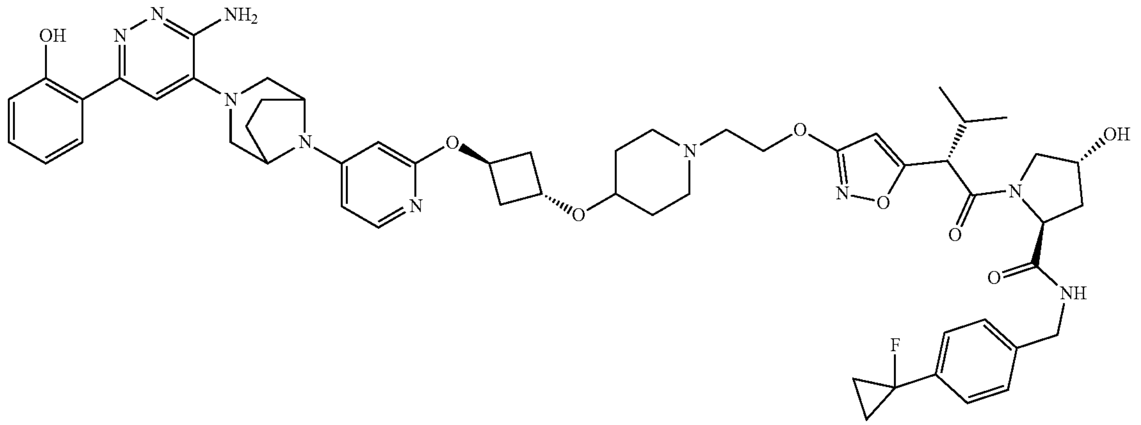
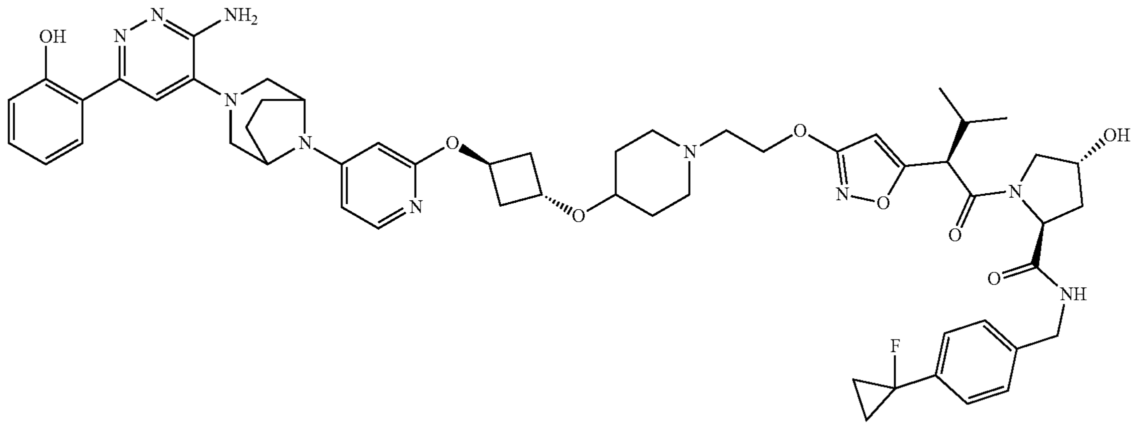

-continued
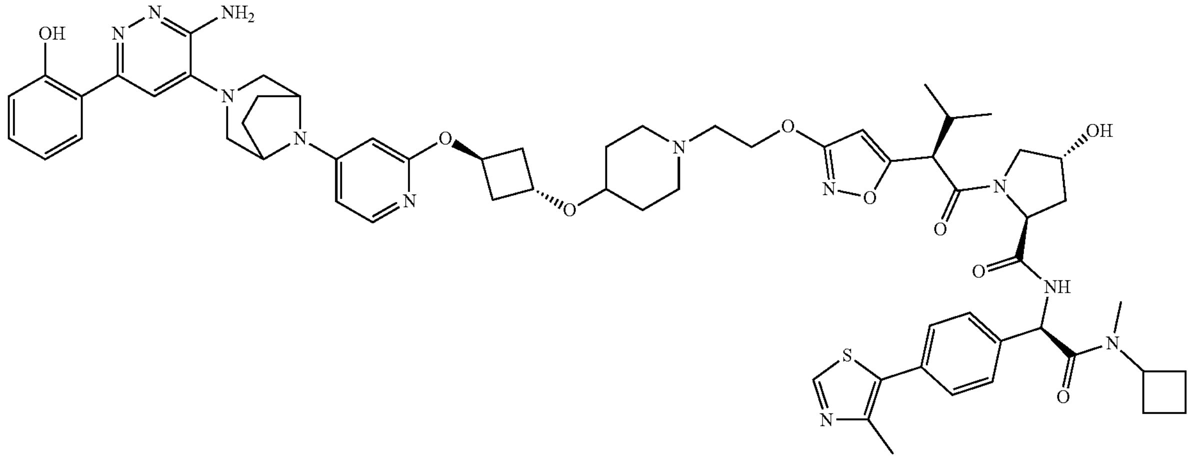
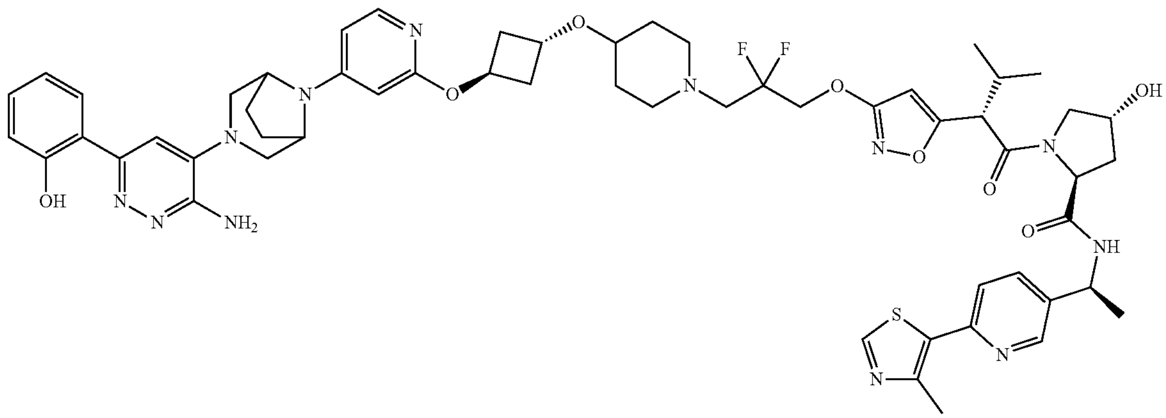
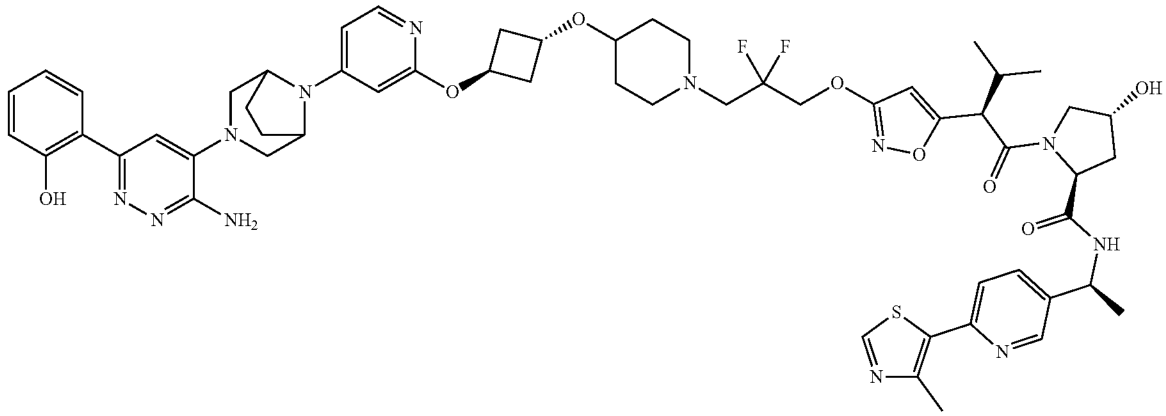

-continued
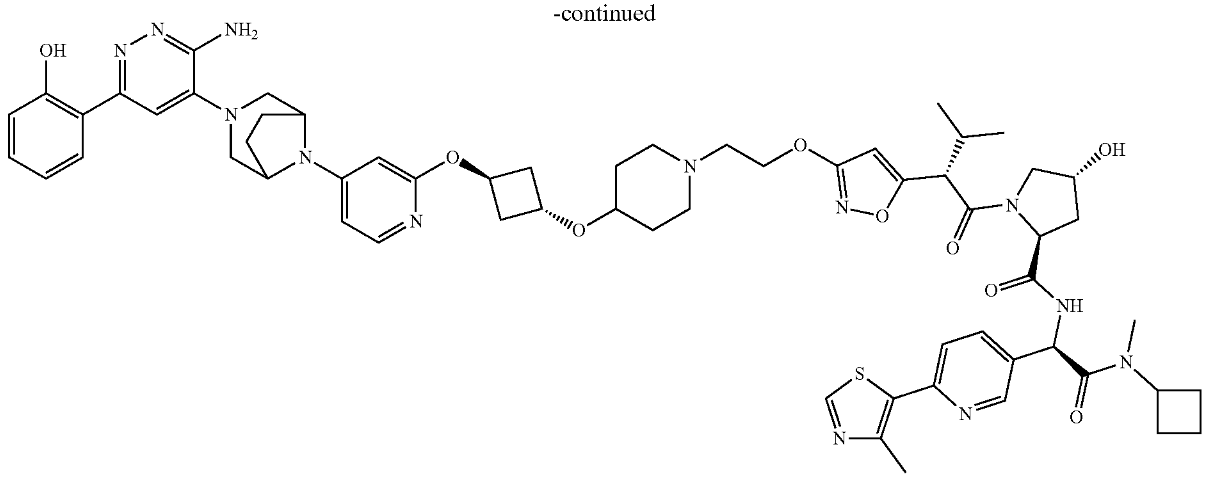
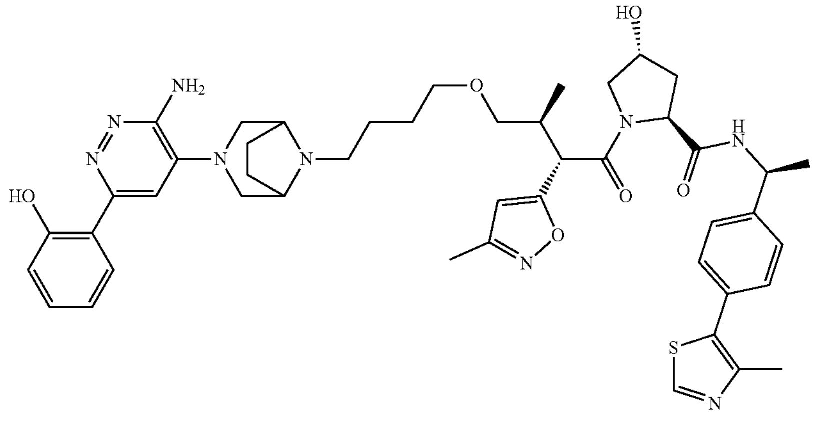
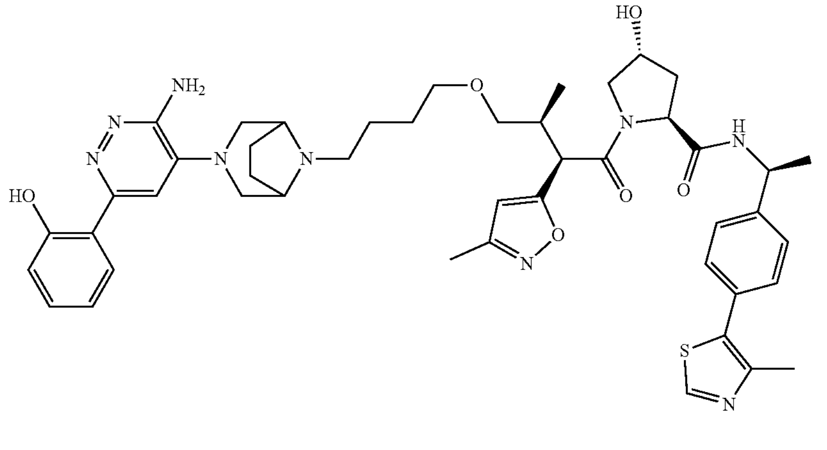

-continued
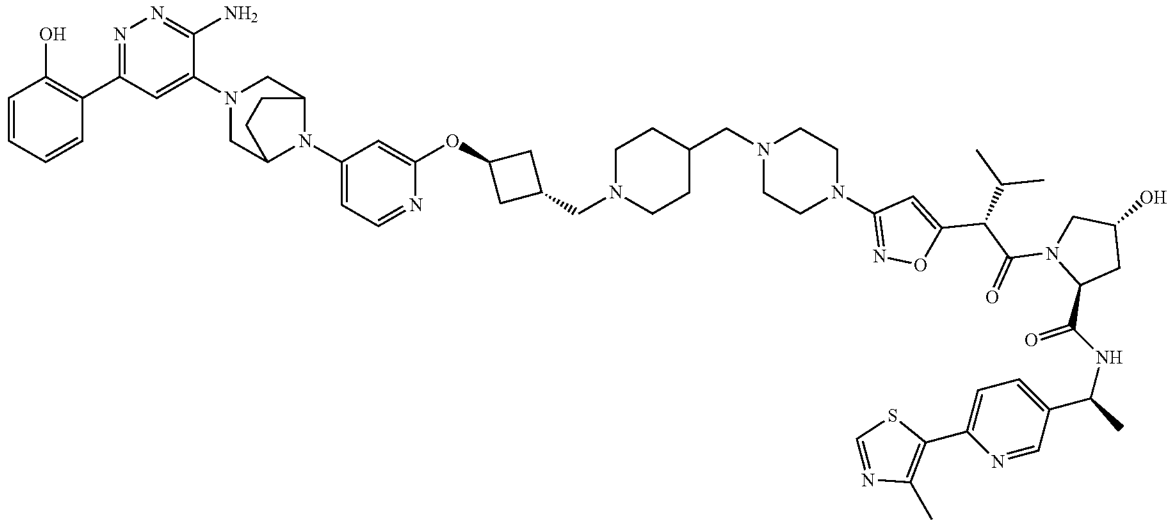
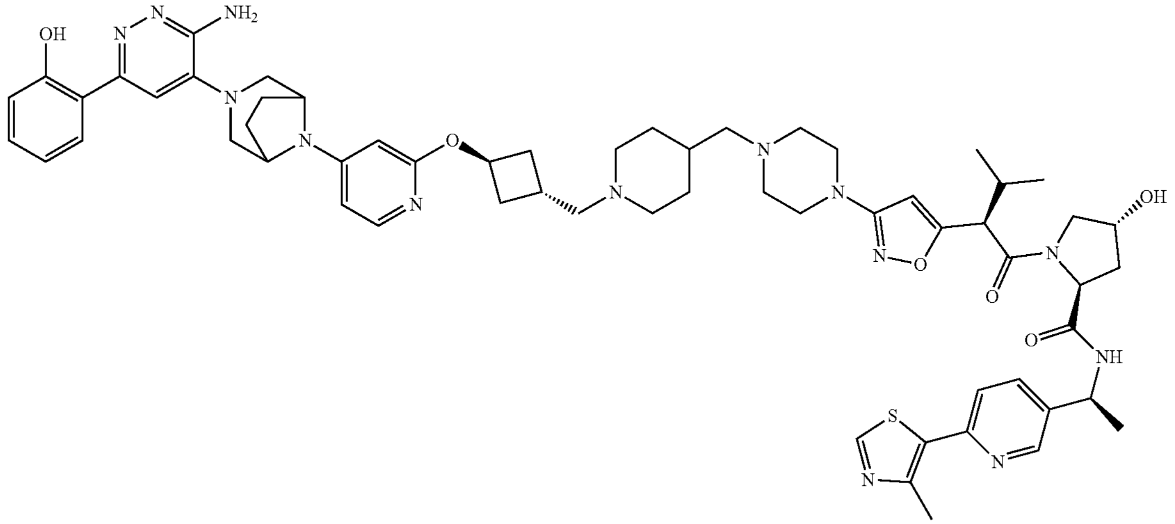
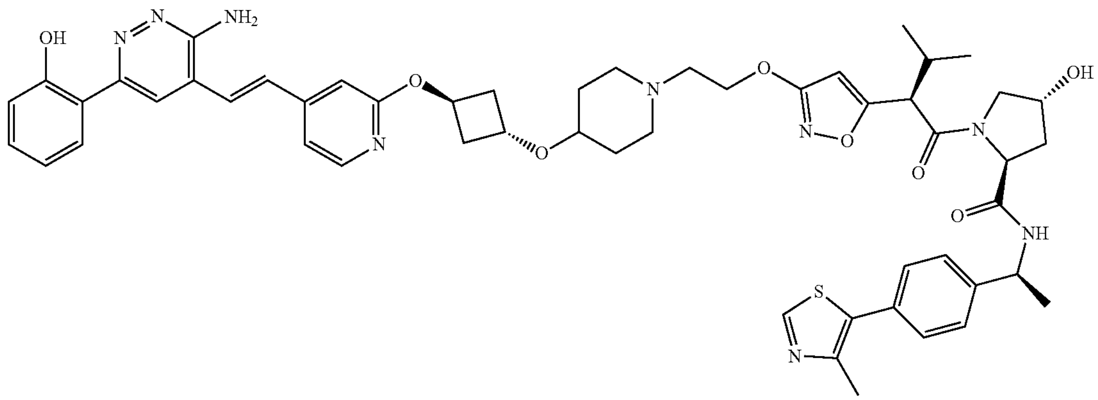

-continued
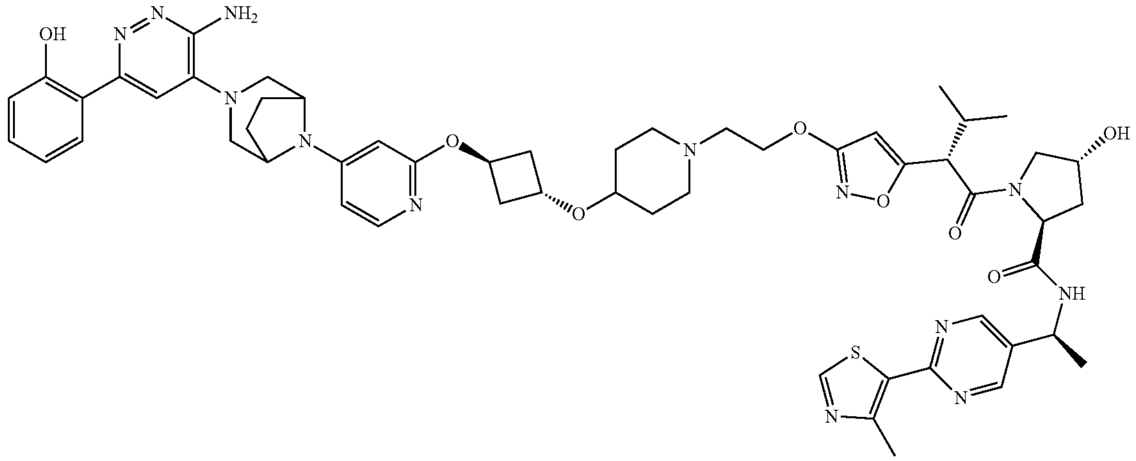
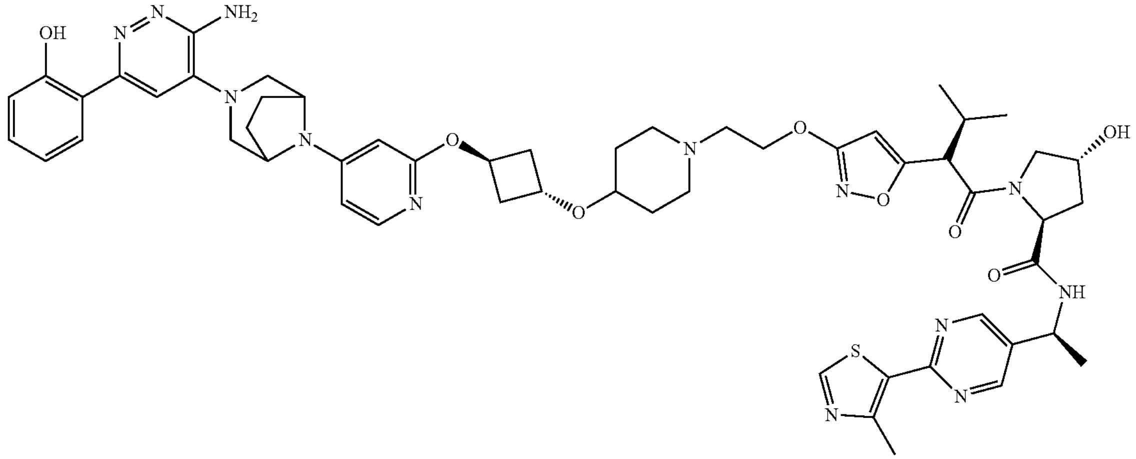
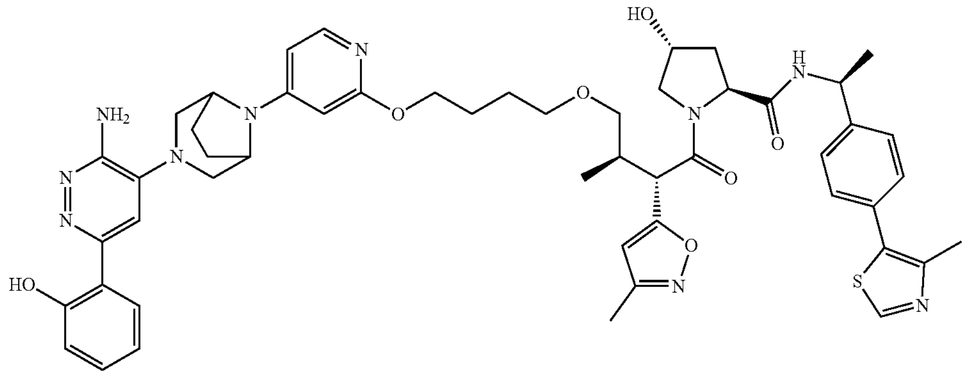
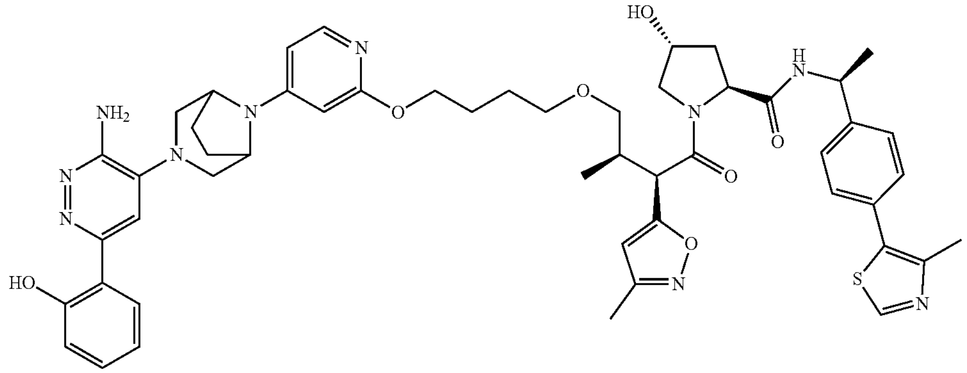

-continued
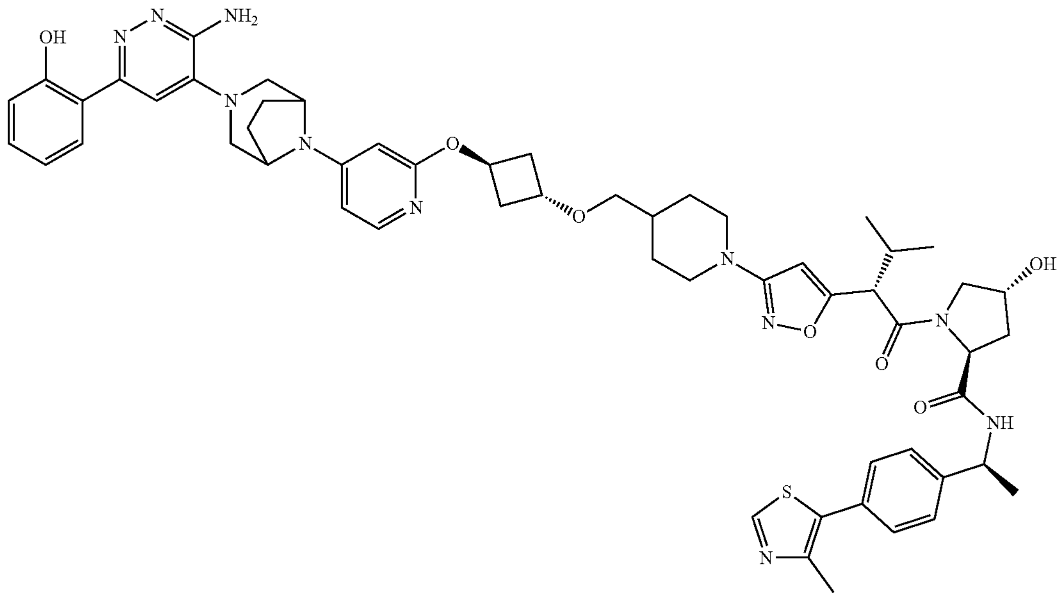
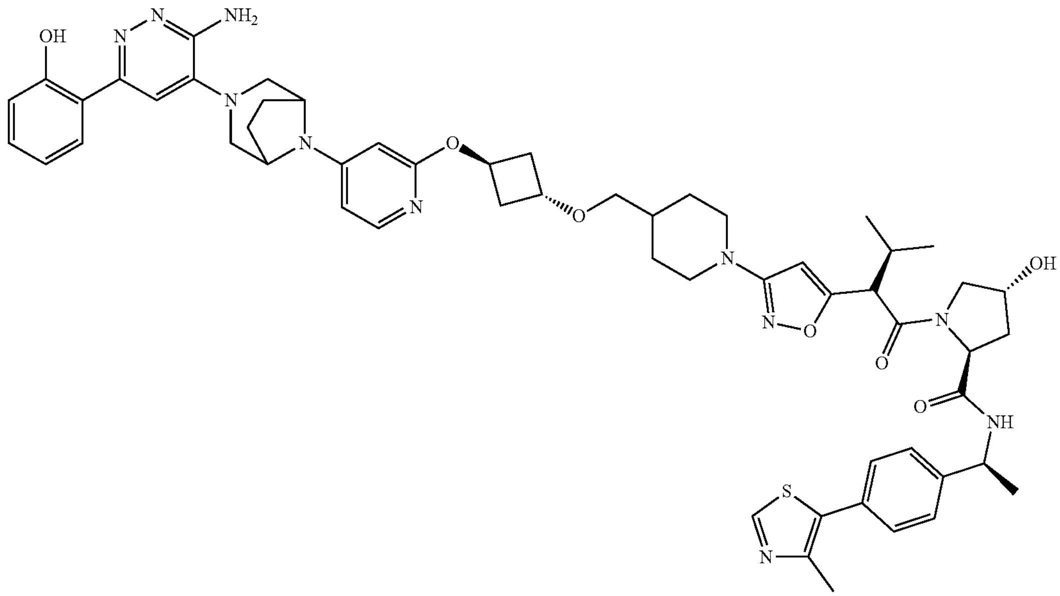
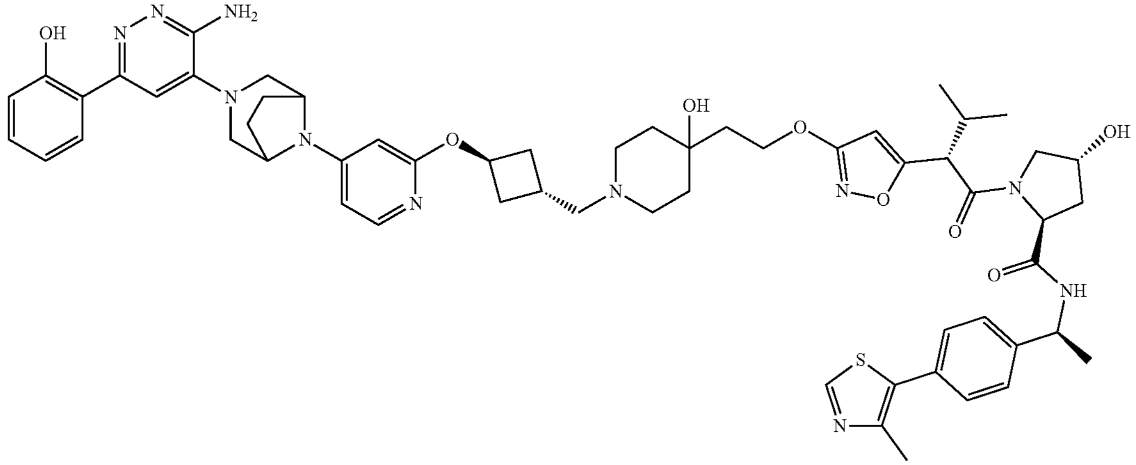

-continued
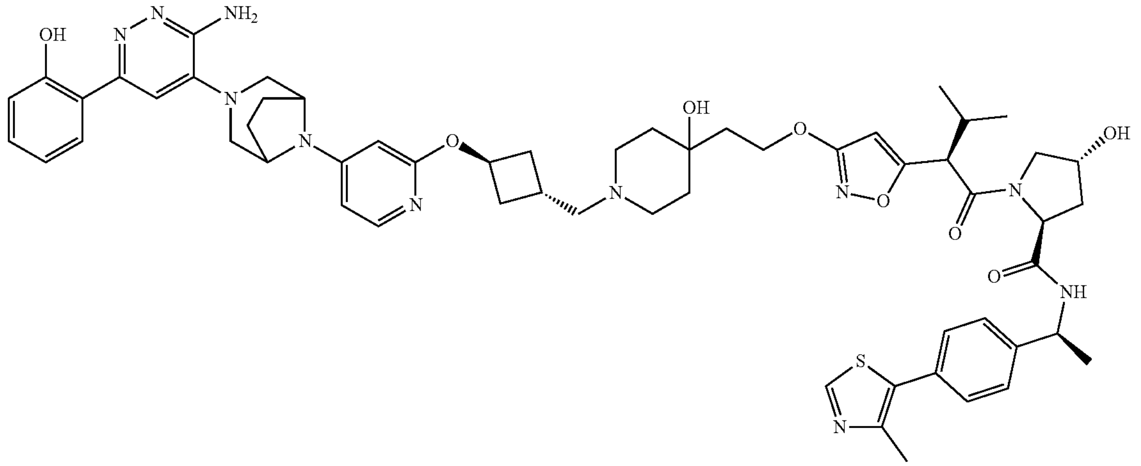
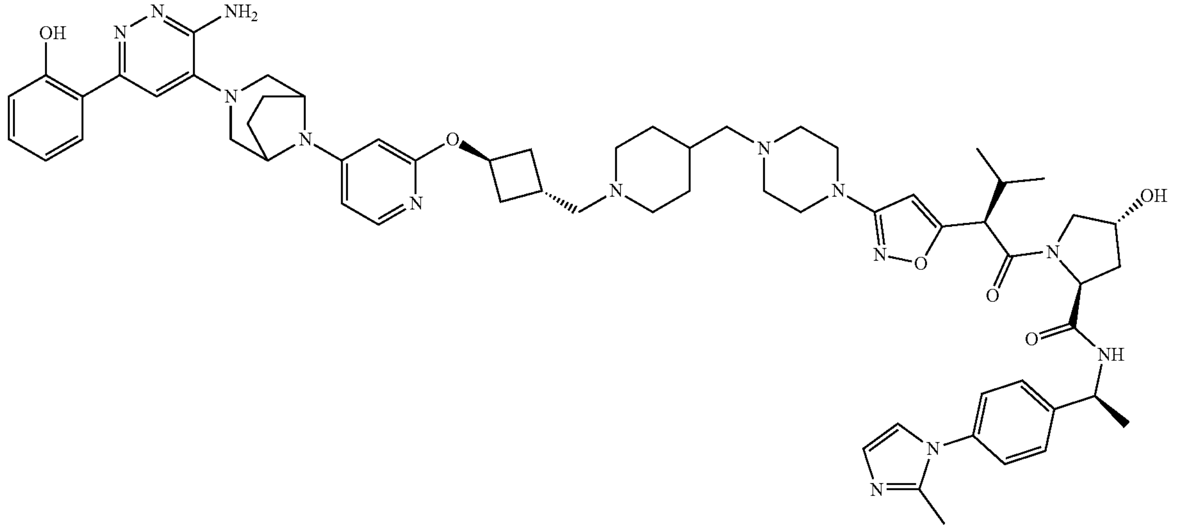
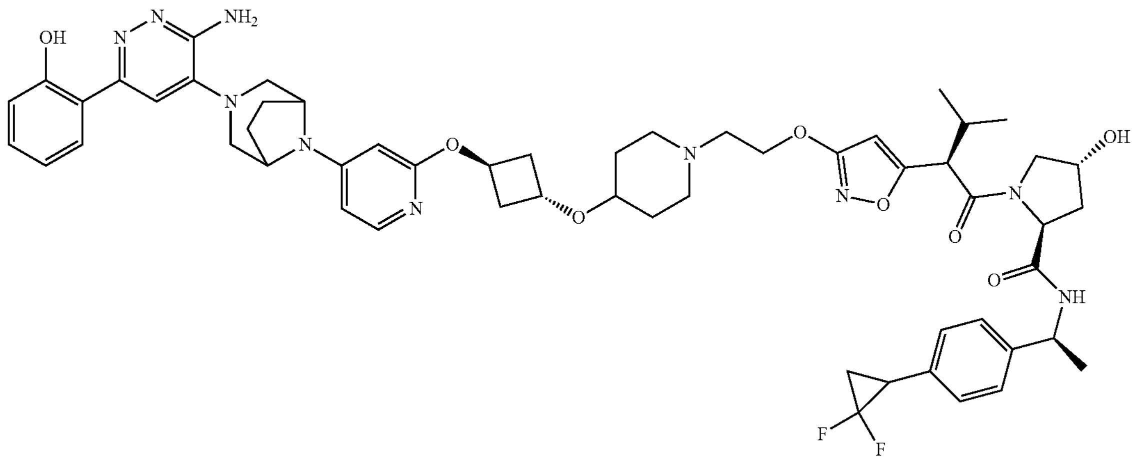

-continued
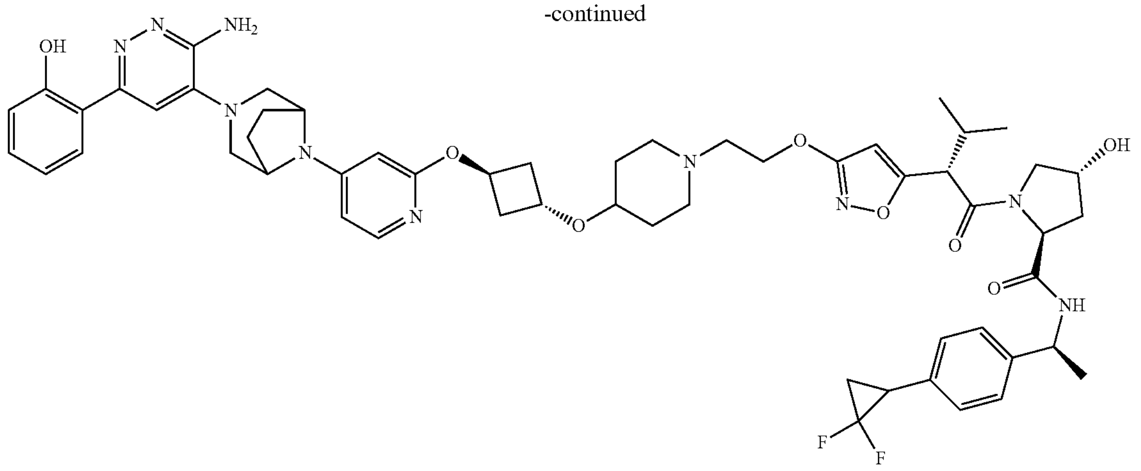
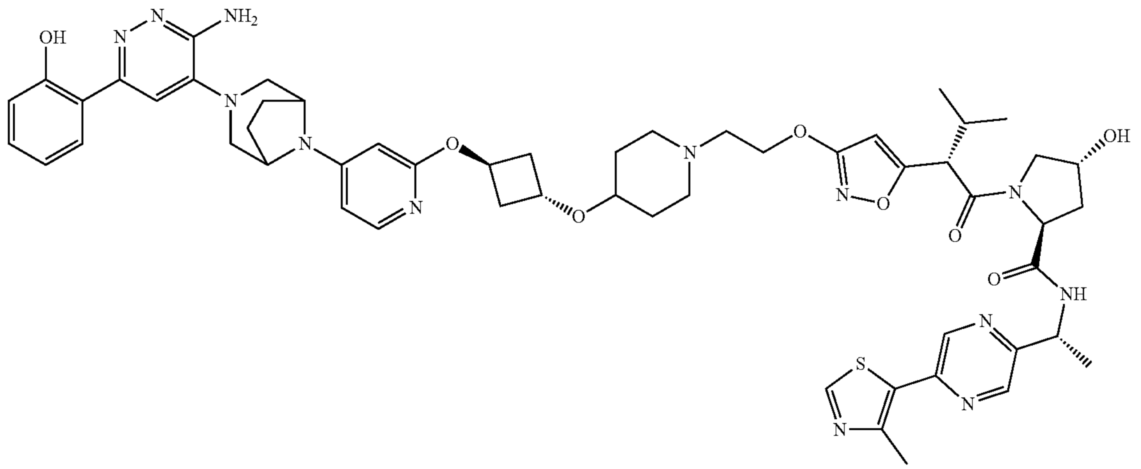 [SMILES: Cc1ncsc1-c1cnc([C@@H](C)NC(=O)[C@@H]2C[C@@H](O)CN2C(=O)[C@H](c2cc(OCCN3CCC(O[C@H]4C[C@H](Oc5cc(N6C7CCC6CN(c6cc(-c8ccccc8O)nnc6N)C7)ccn5)C4)CC3)no2)C(C)C)cn1]
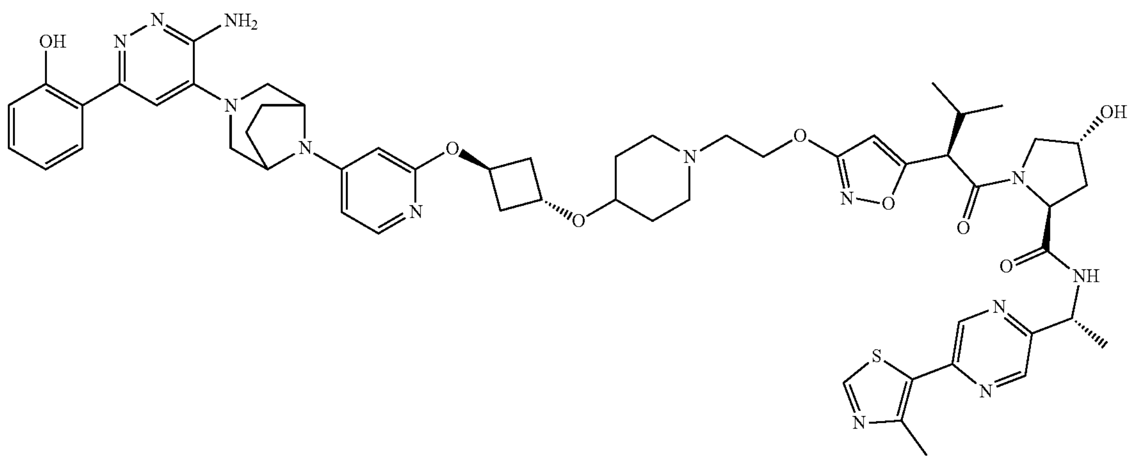

-continued
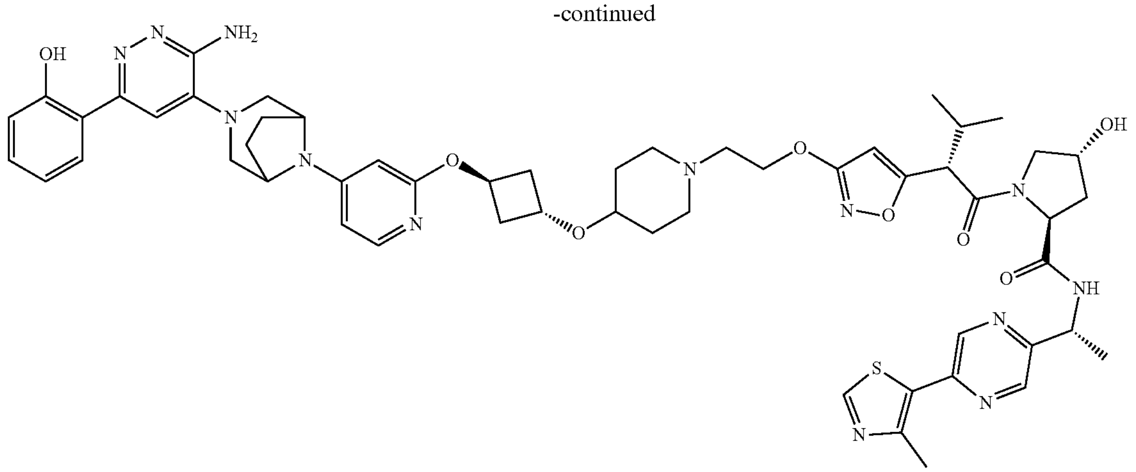
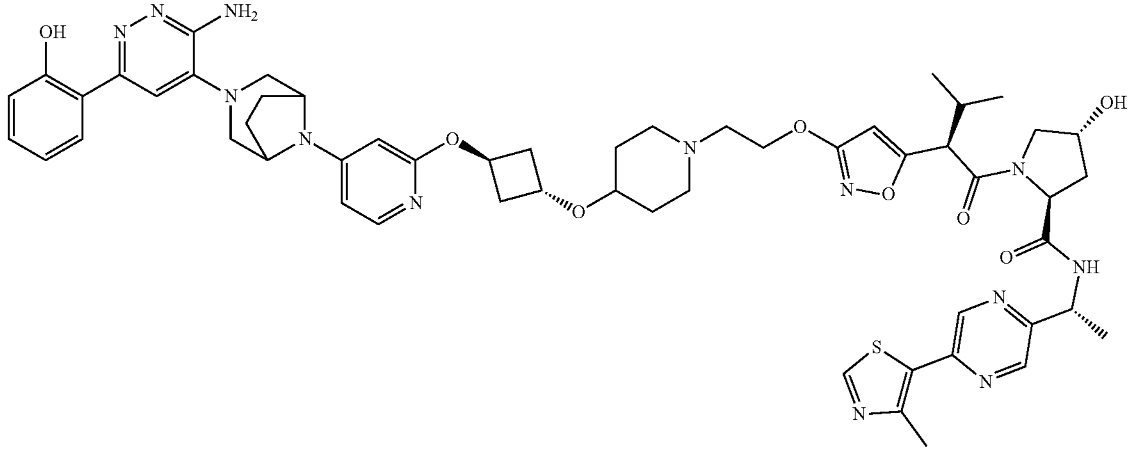
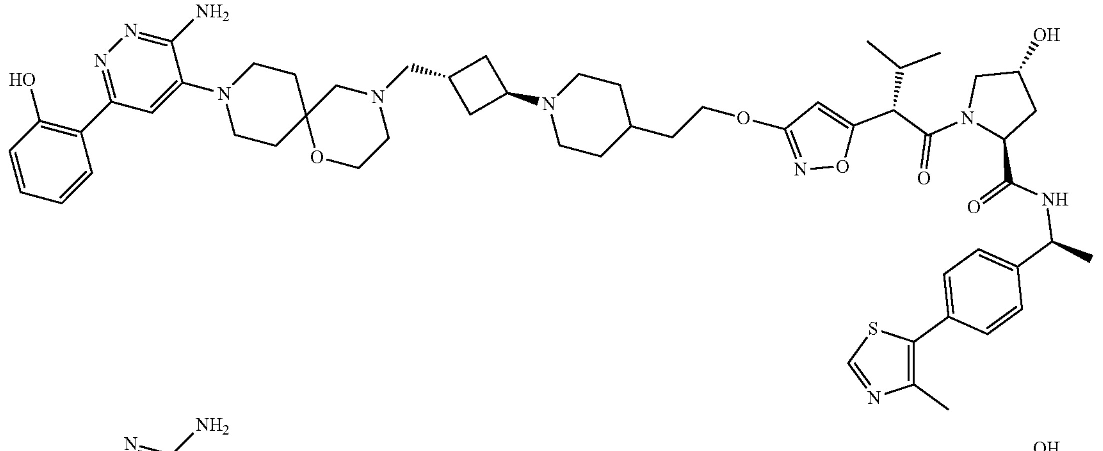
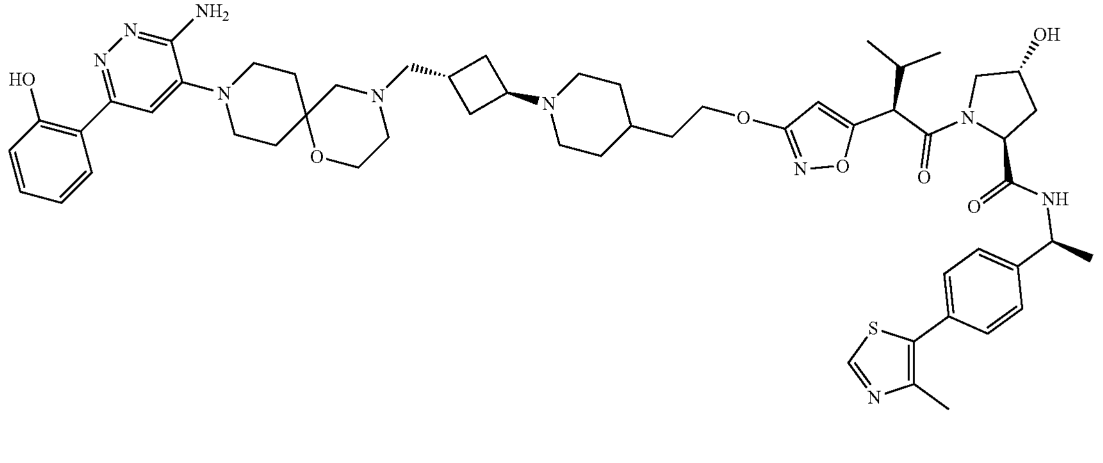

-continued
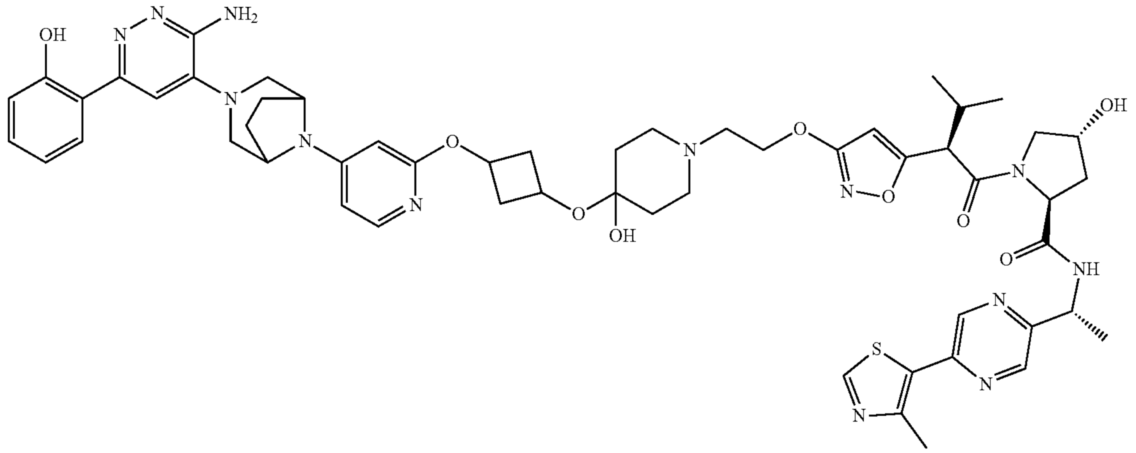
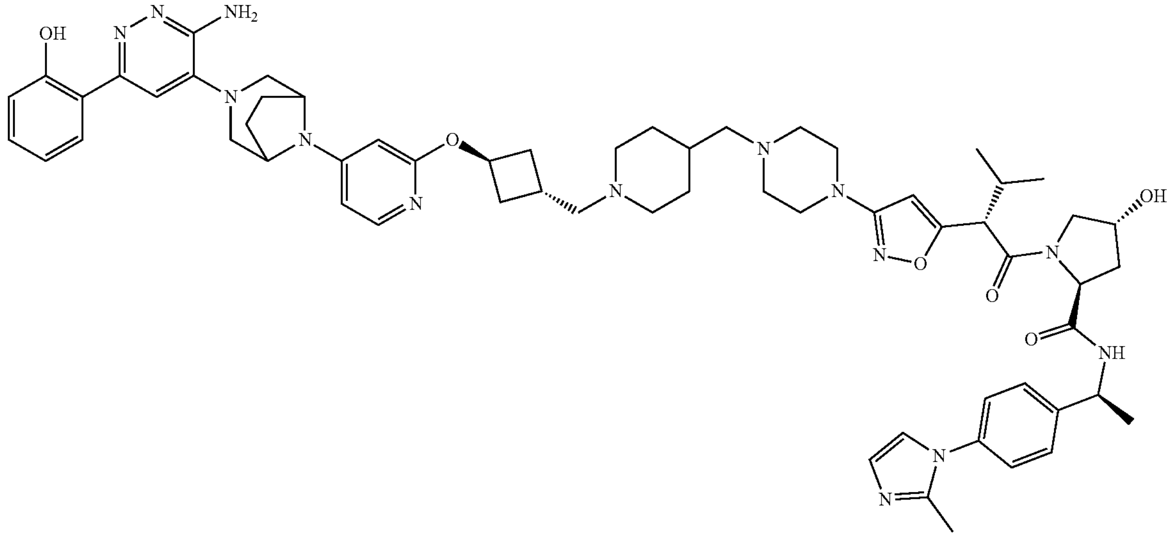
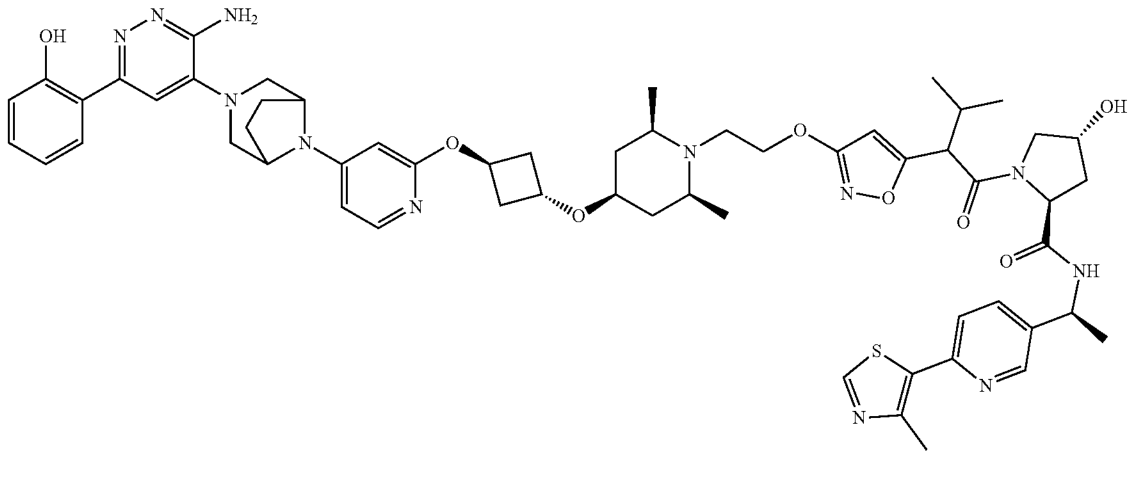

-continued
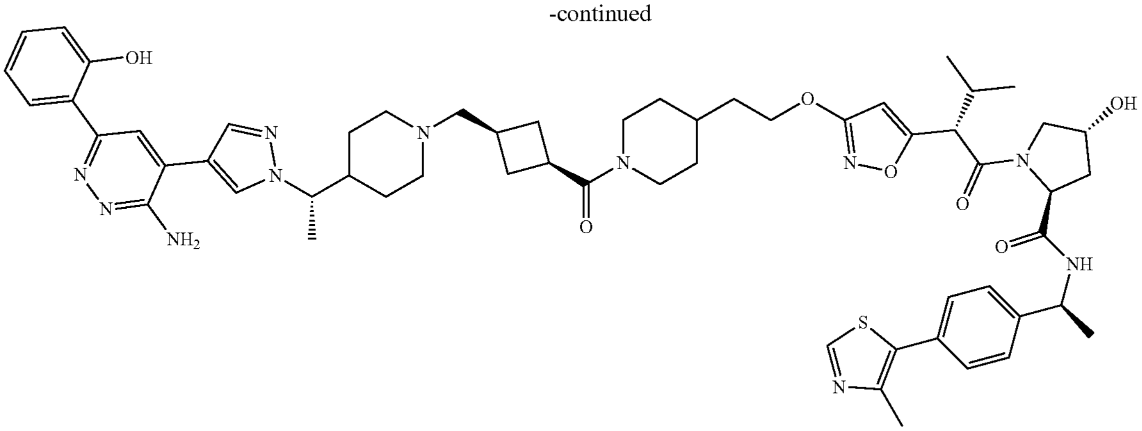
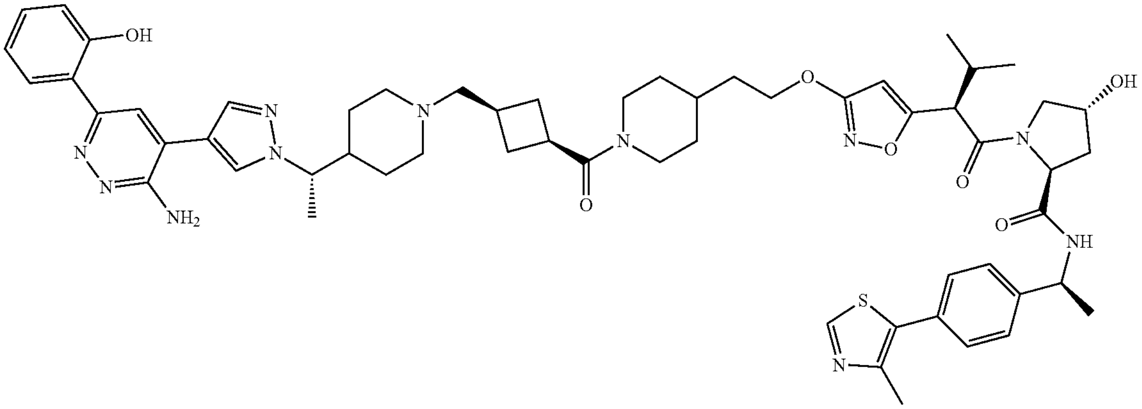
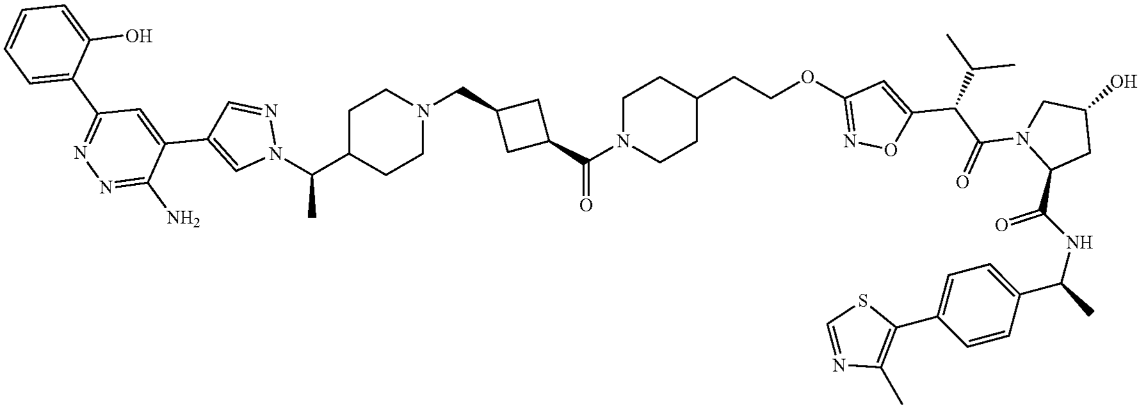
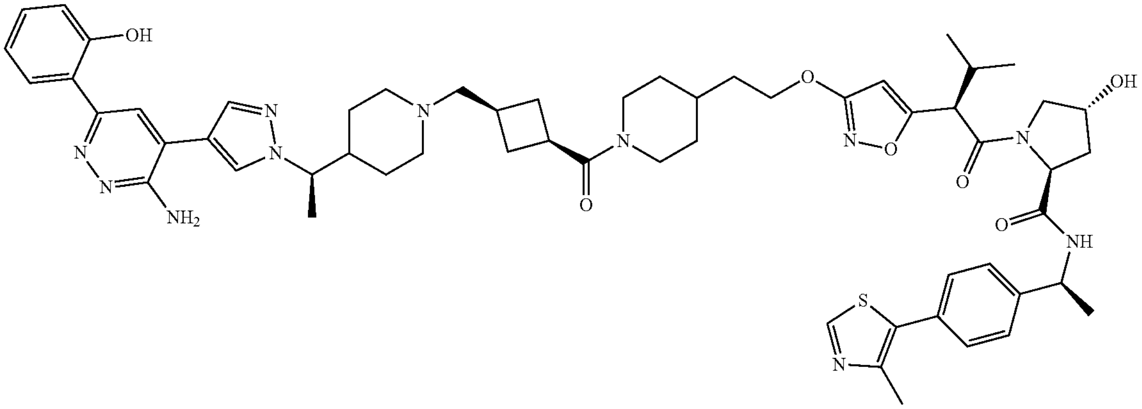

-continued
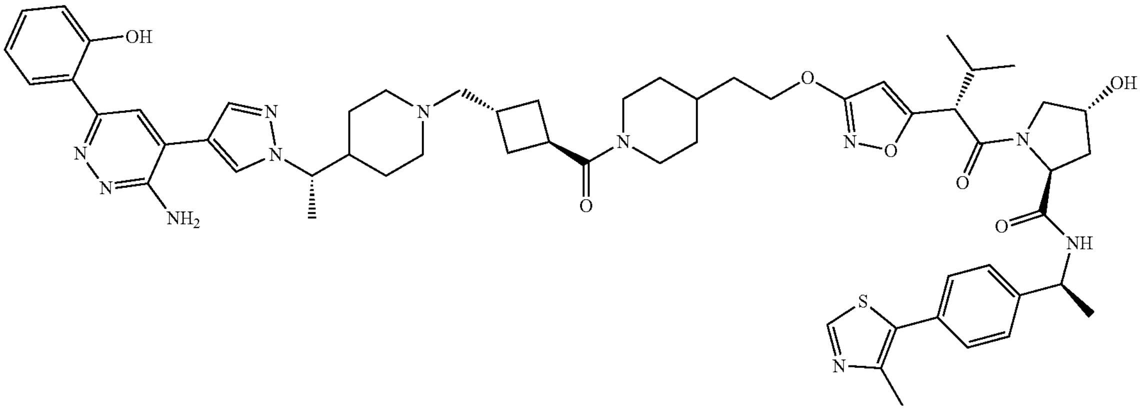
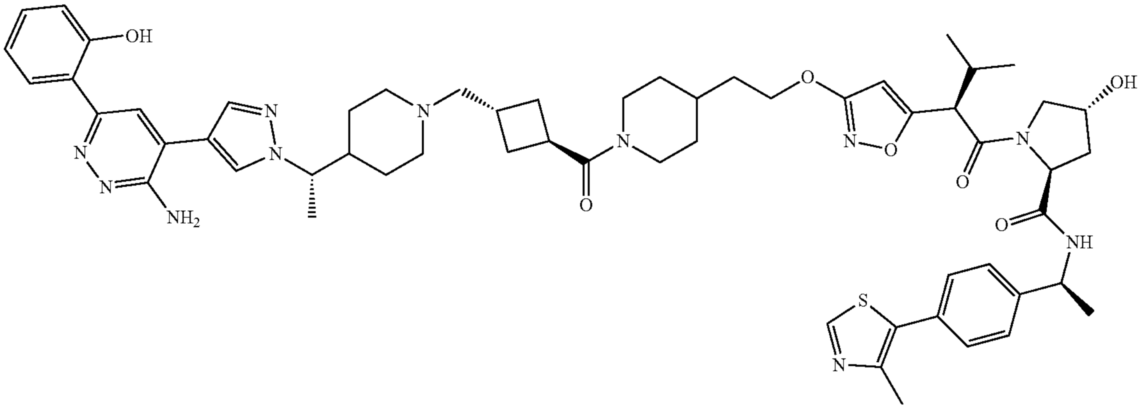
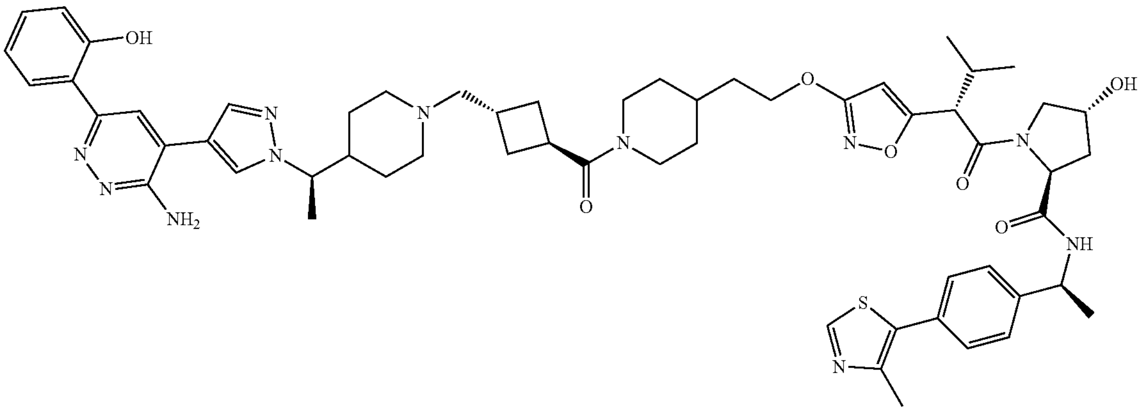
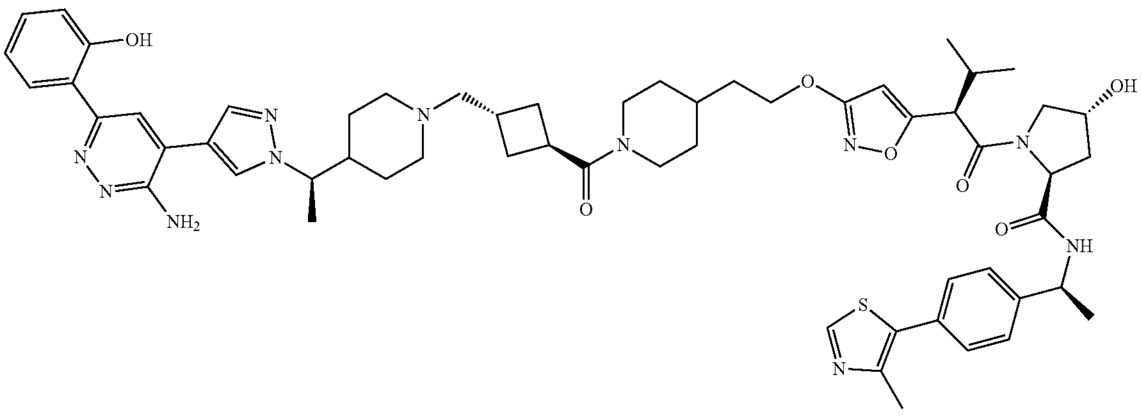

-continued
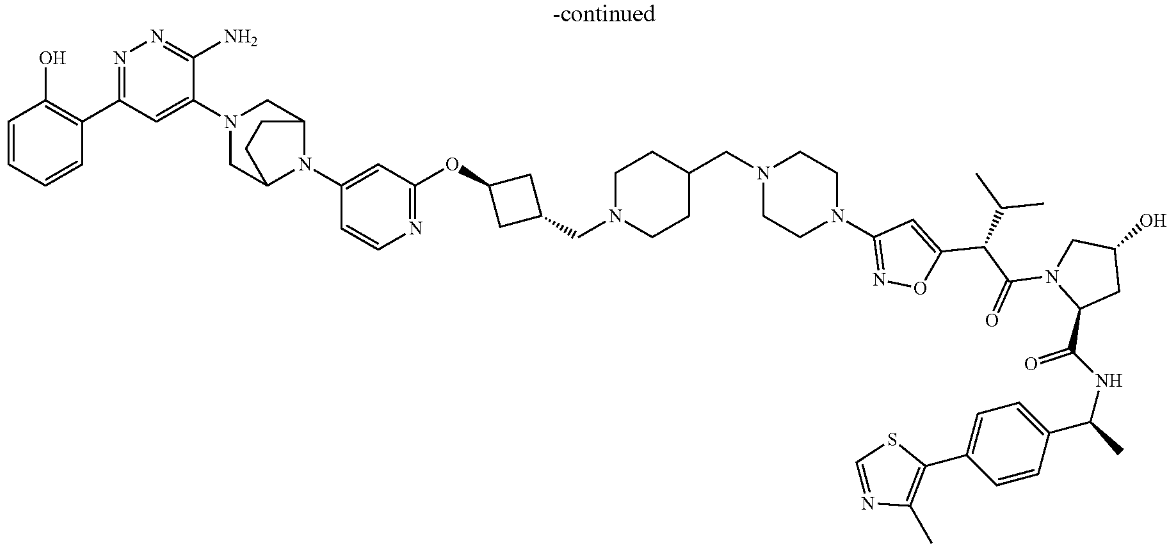
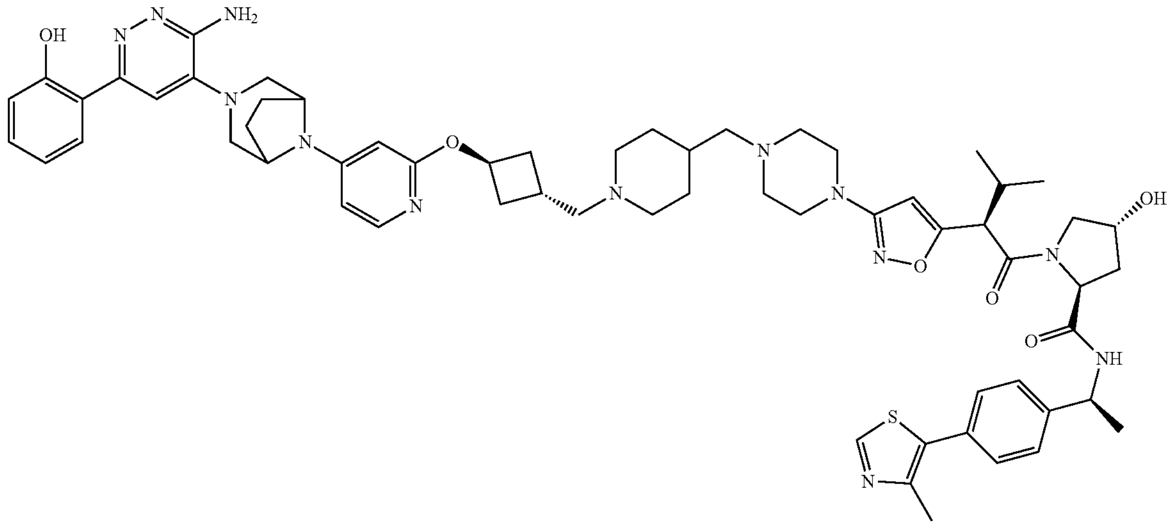
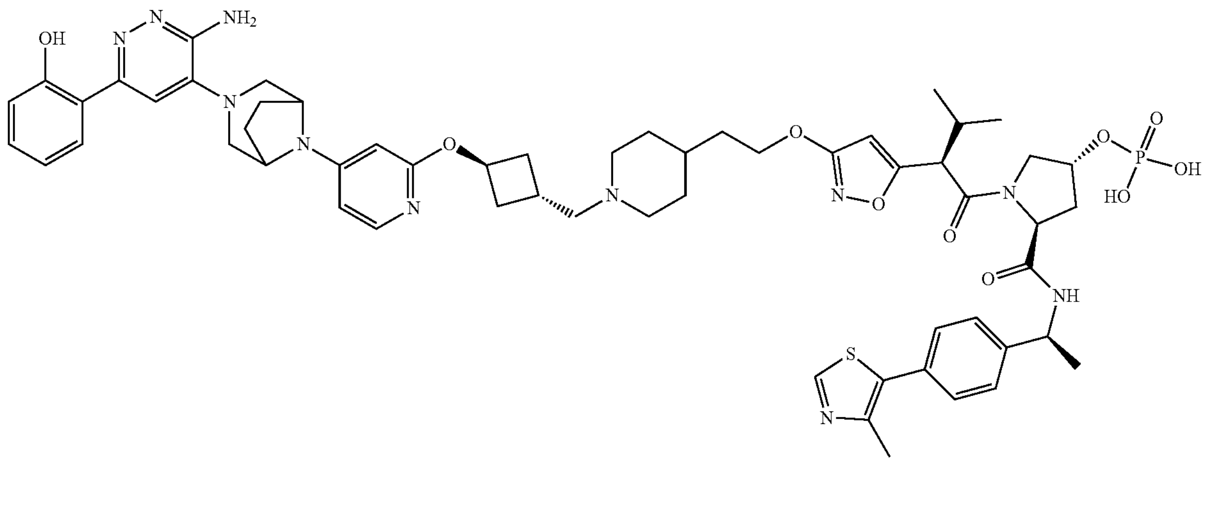

-continued
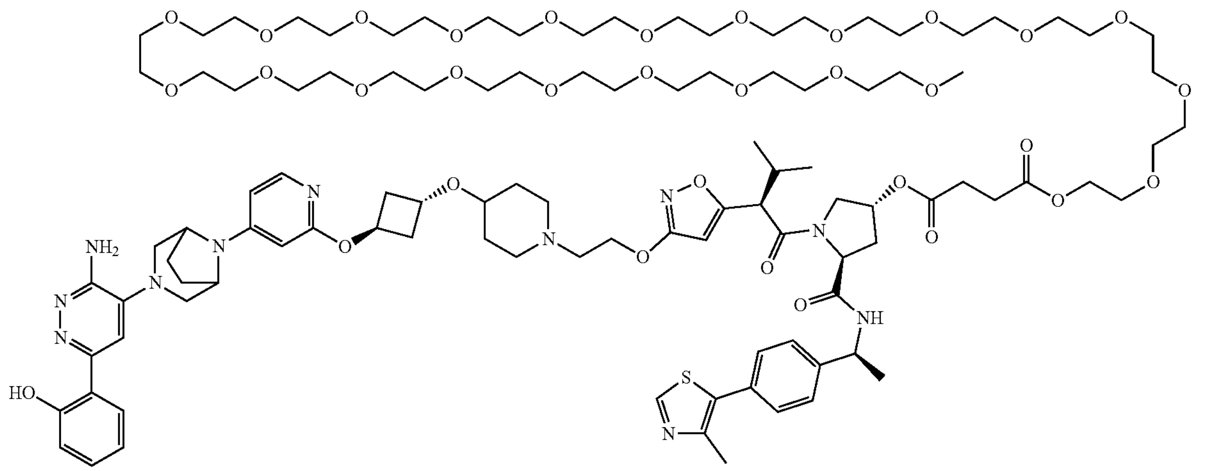
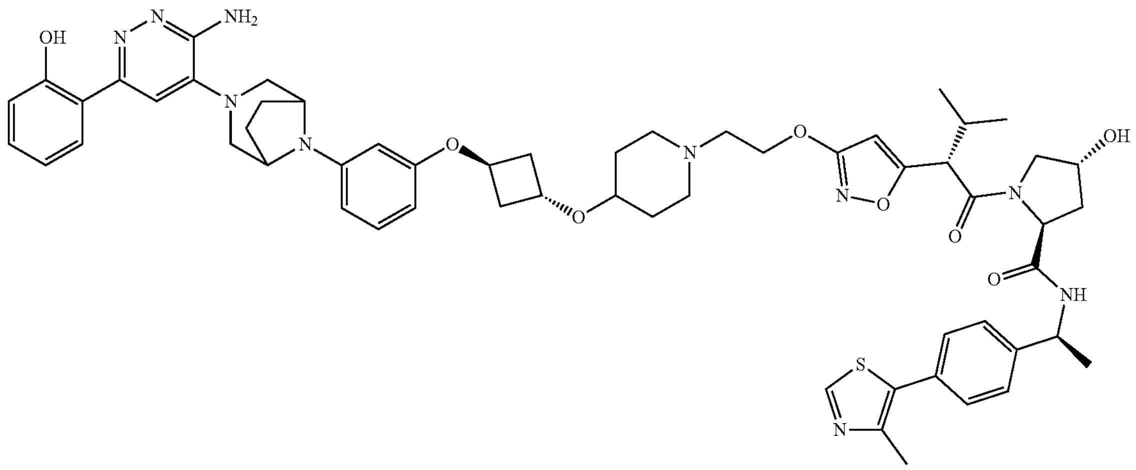
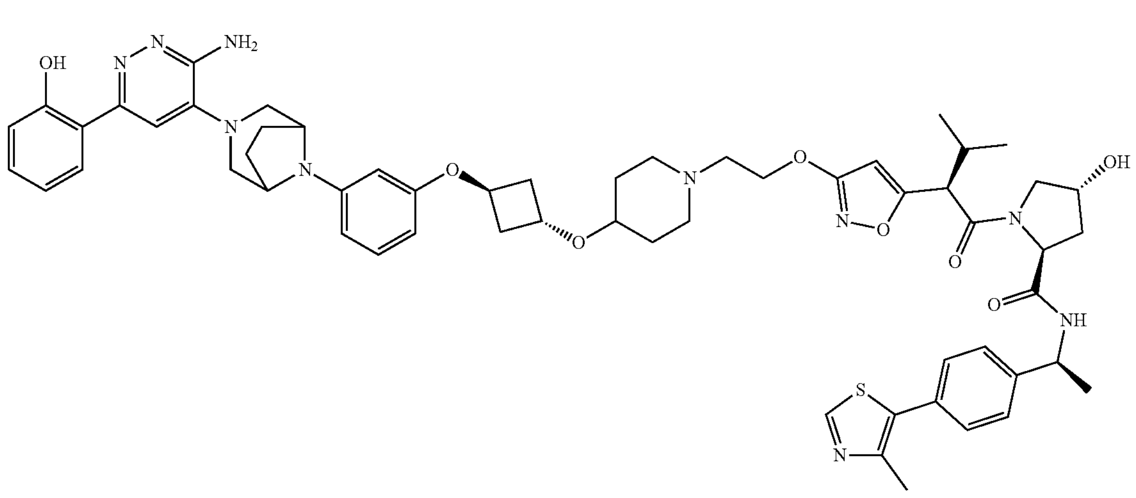

-continued
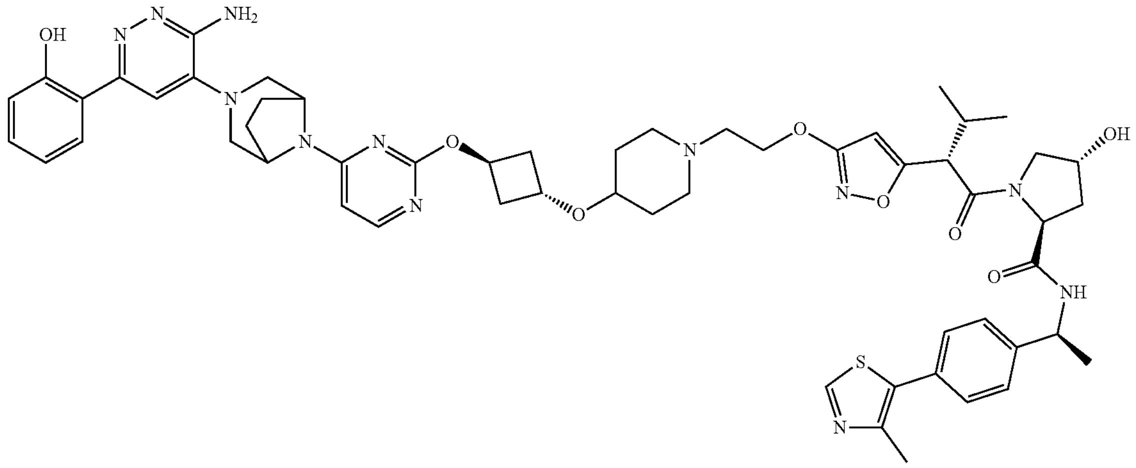
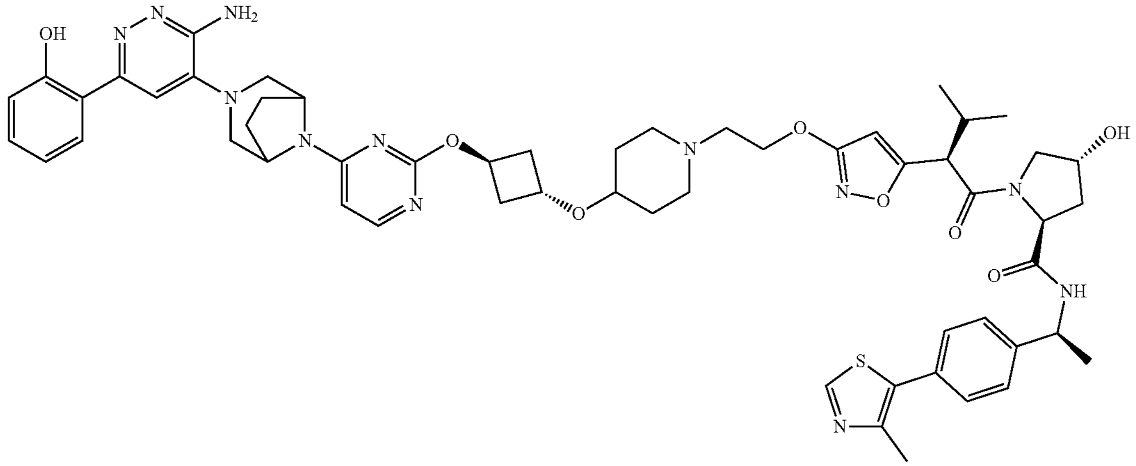
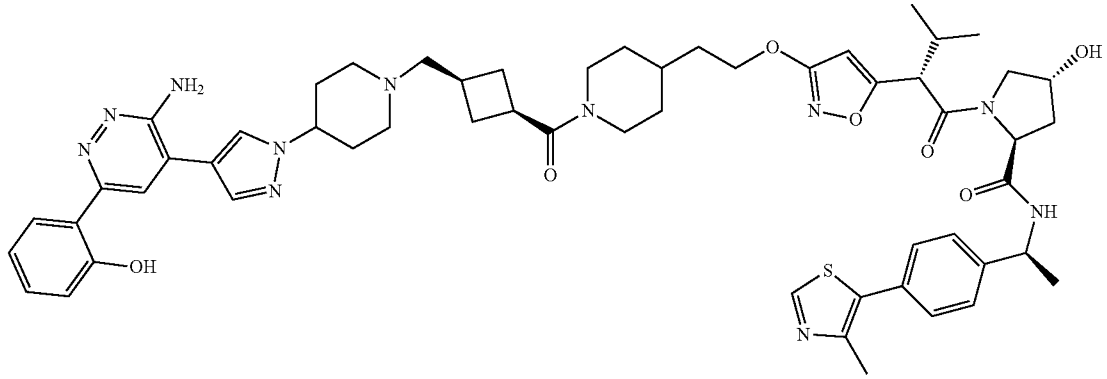
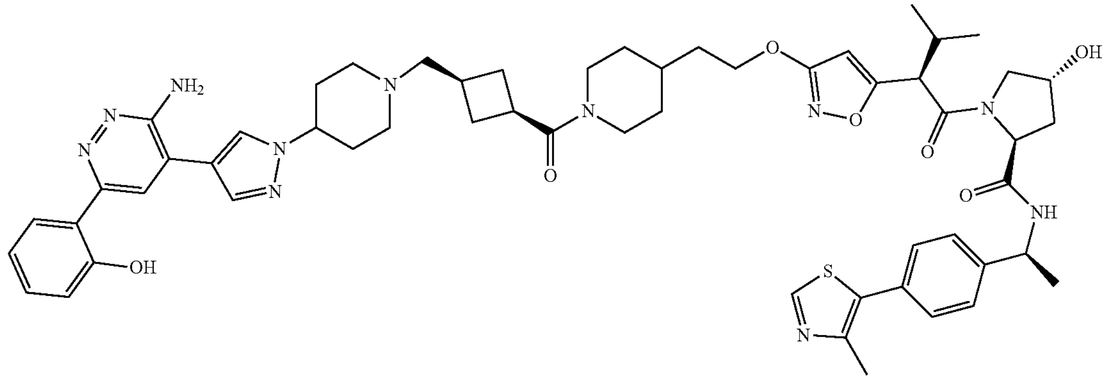

-continued
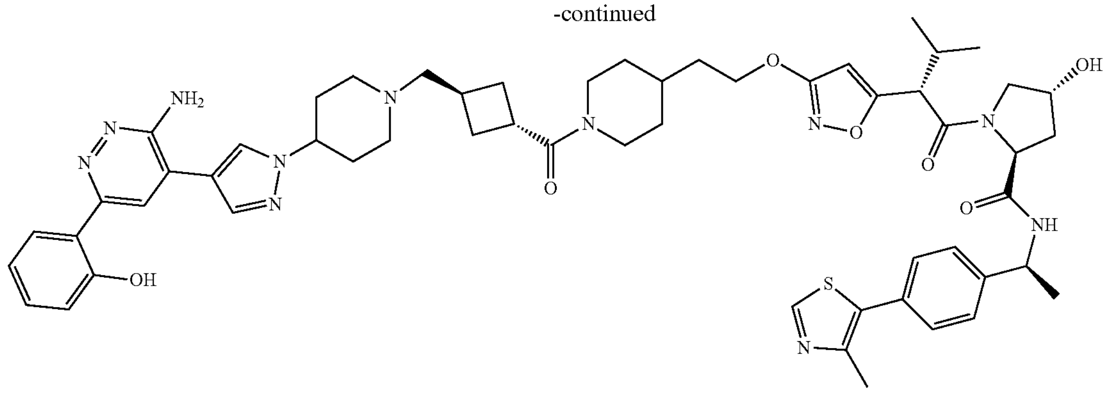
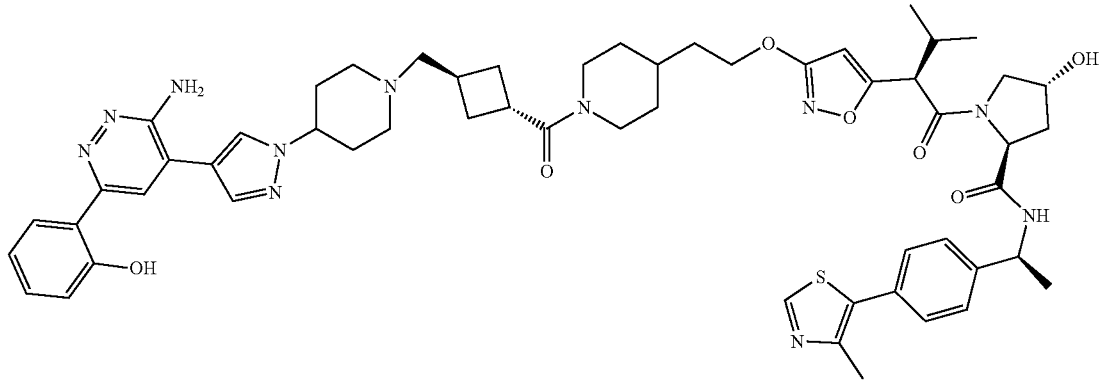
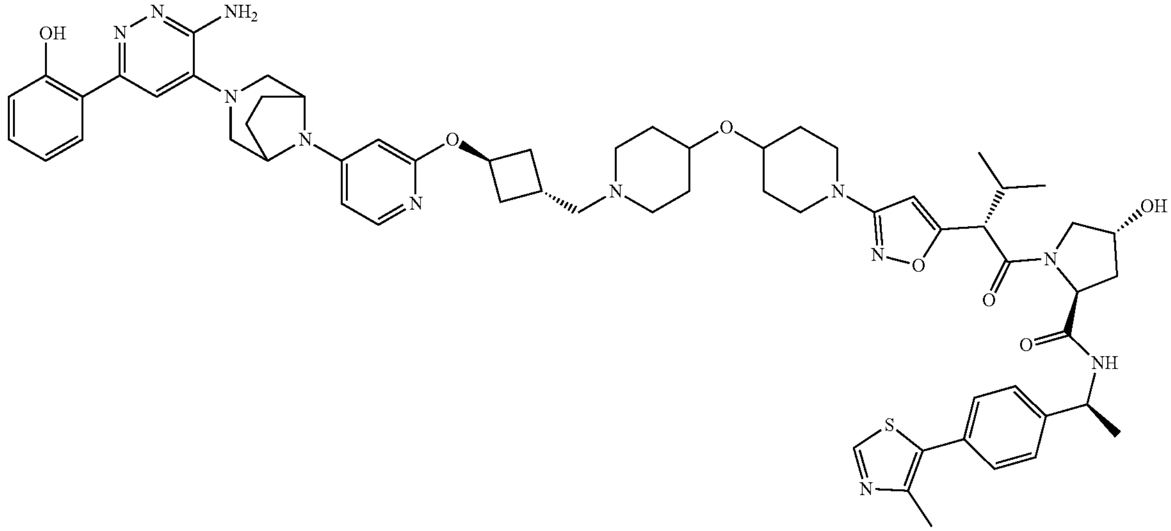

-continued
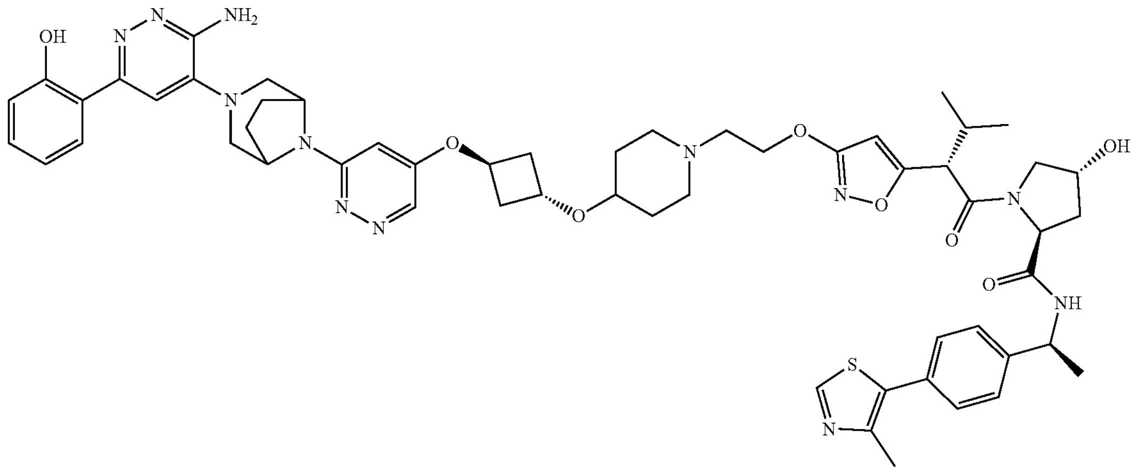
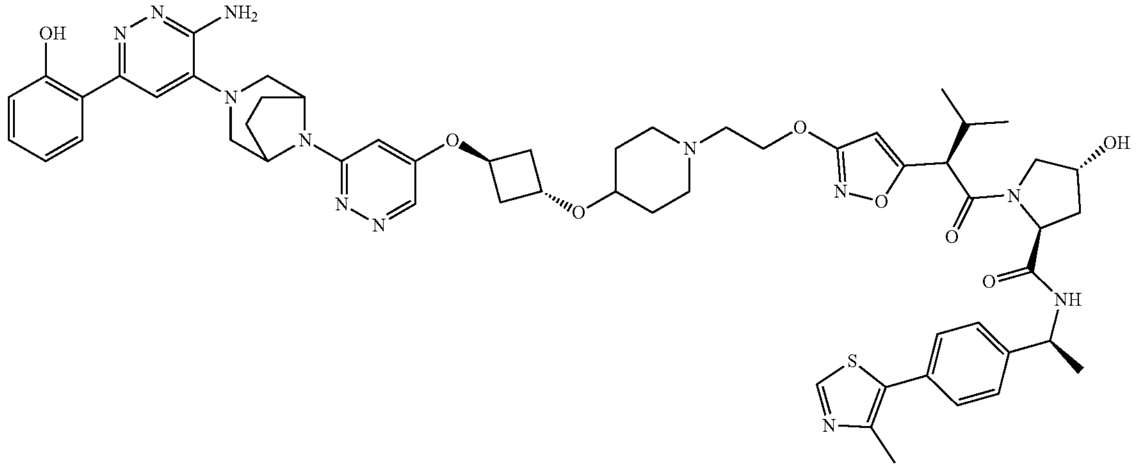
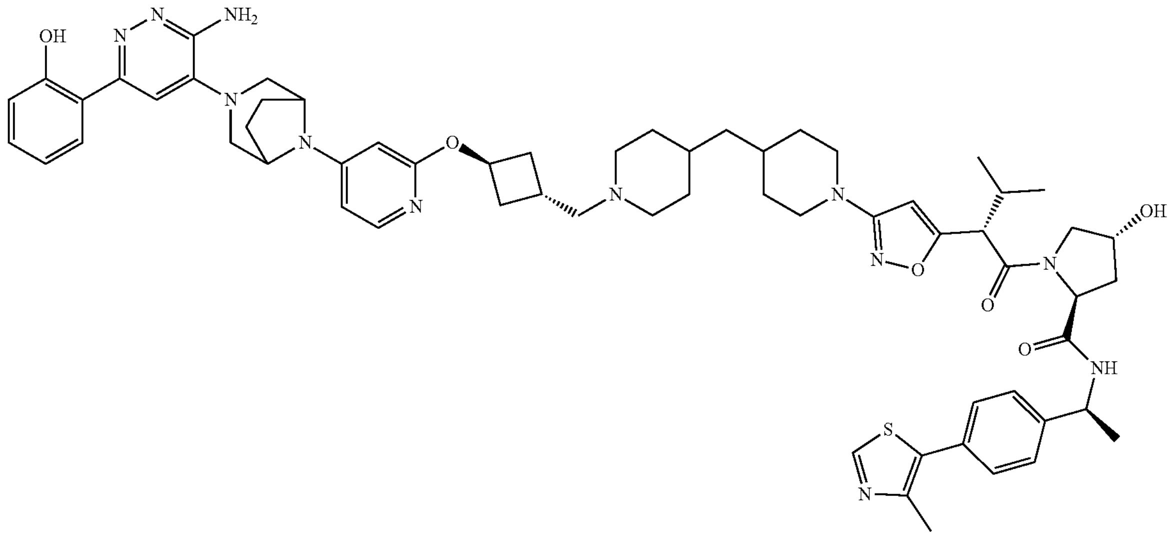

-continued
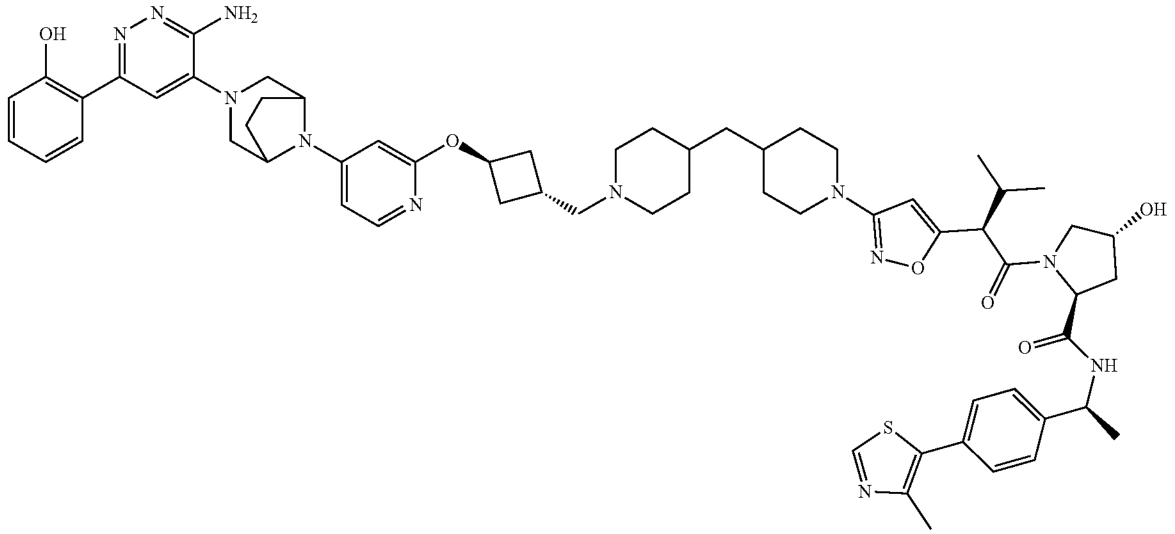
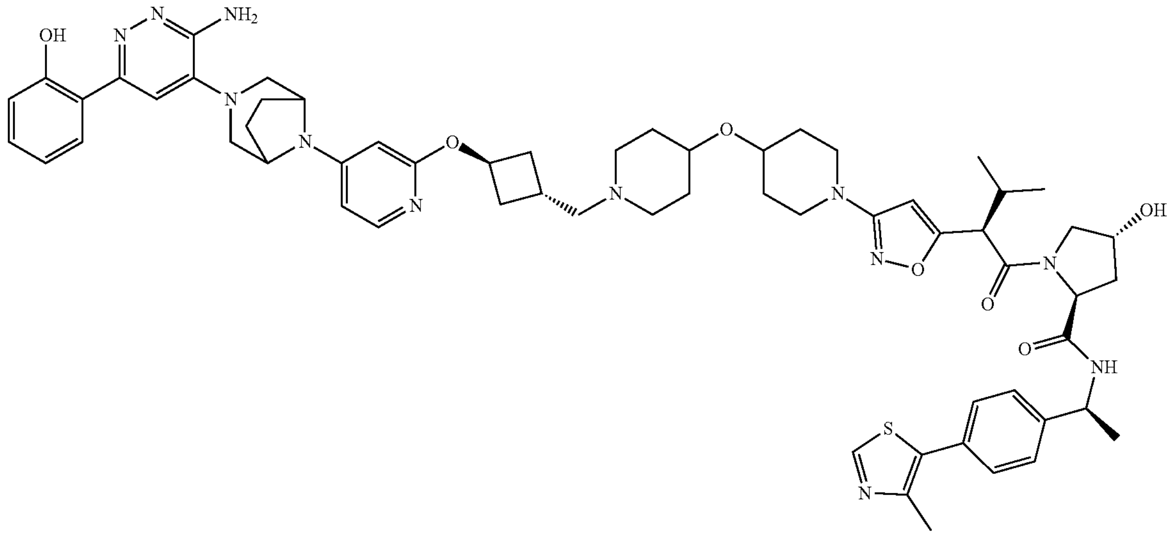
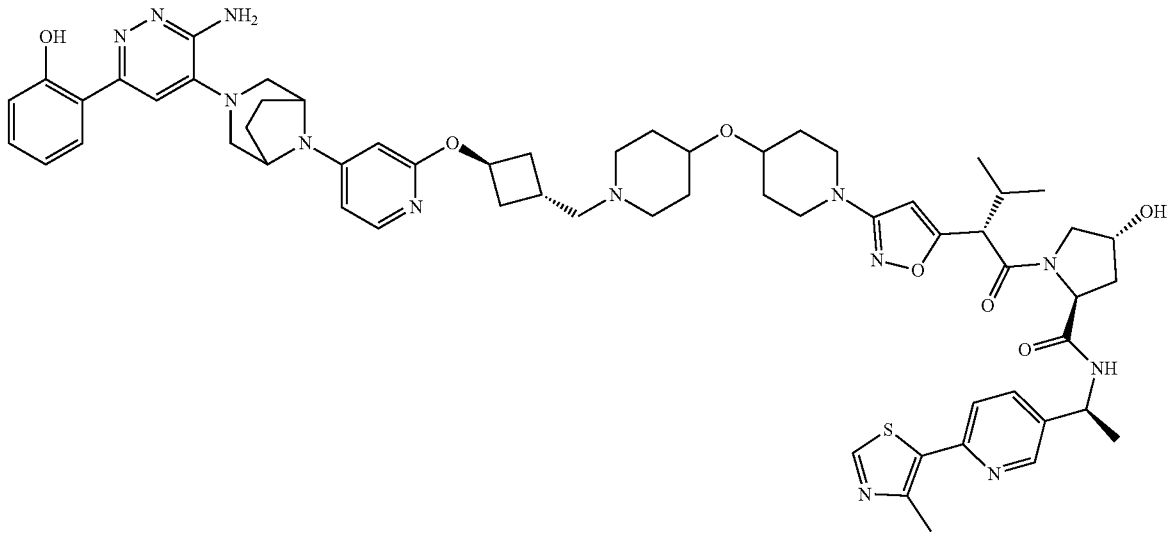

-continued
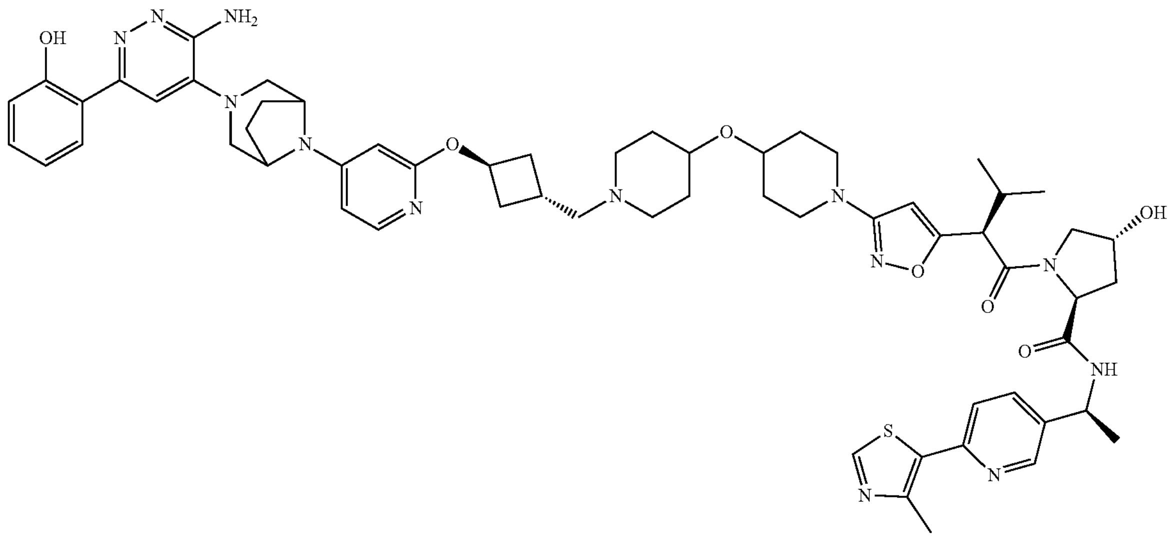
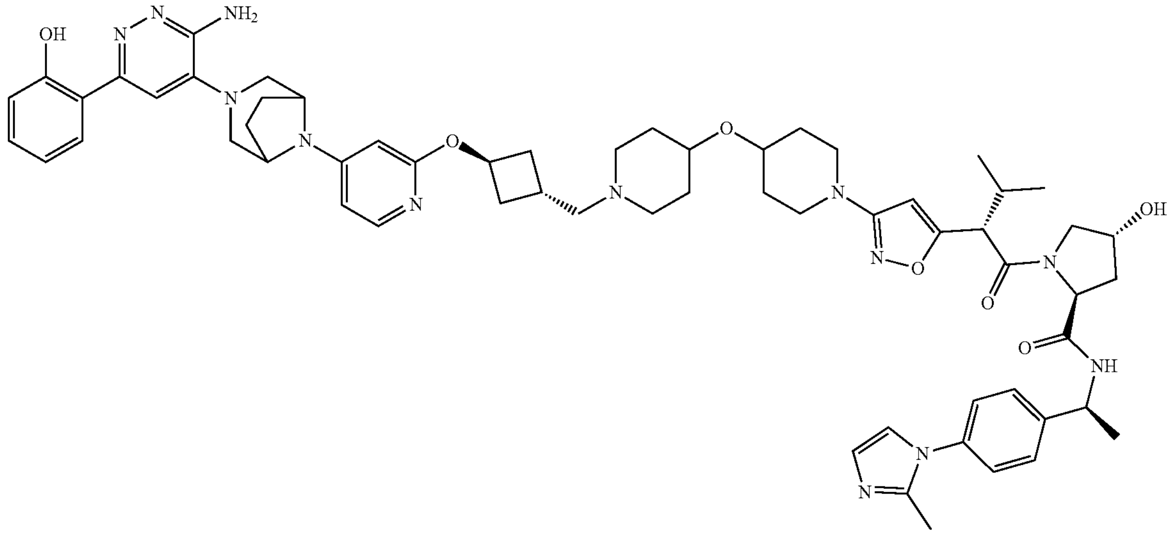
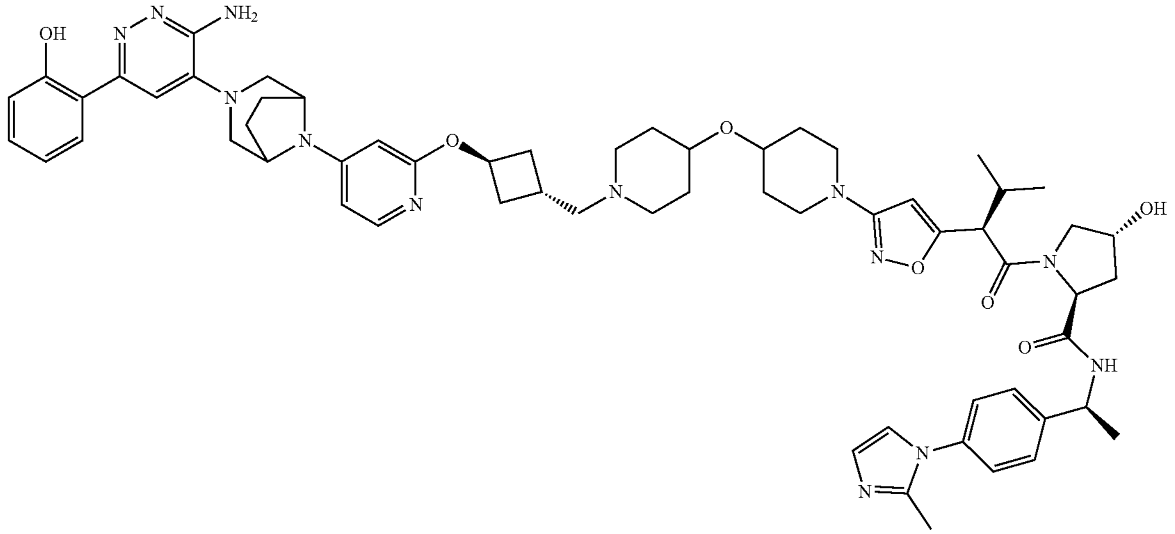

-continued
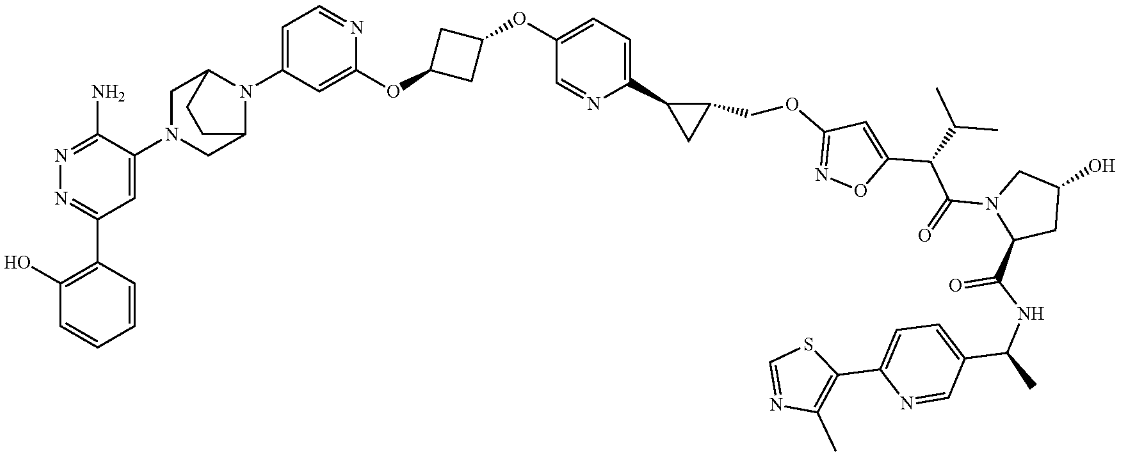
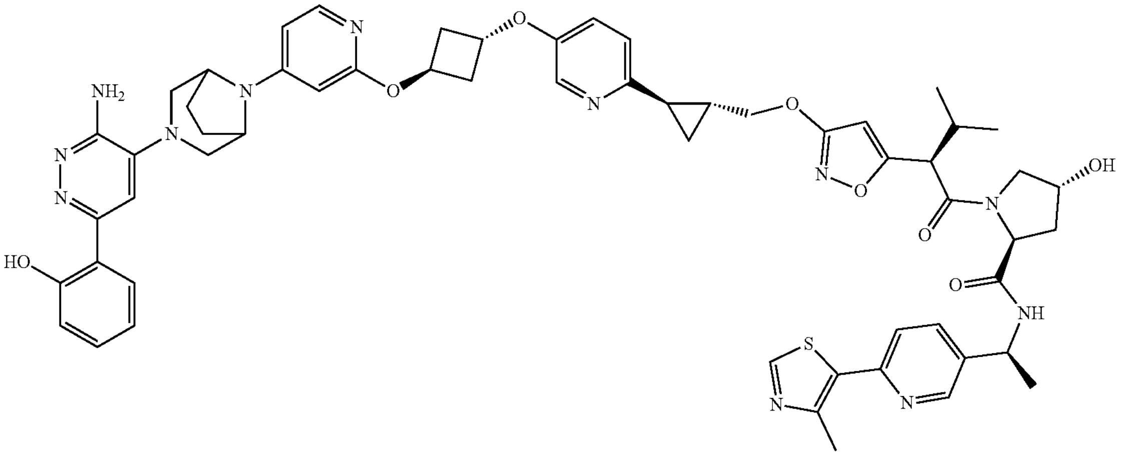
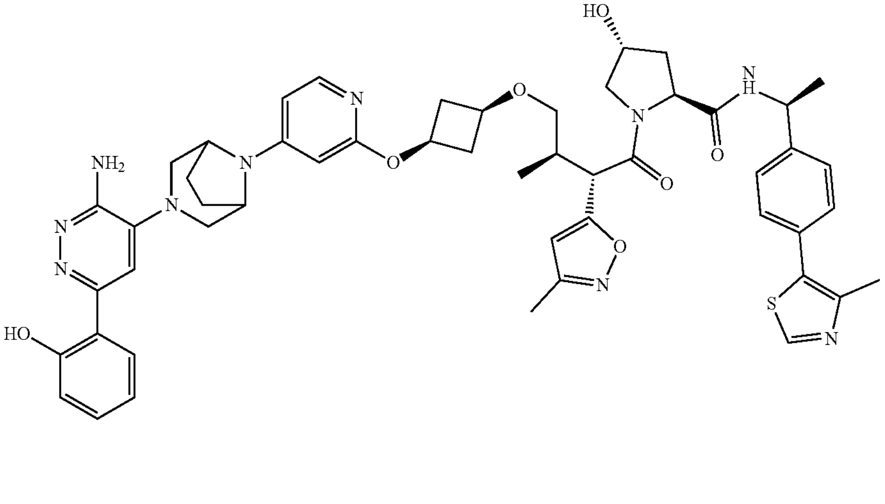

-continued
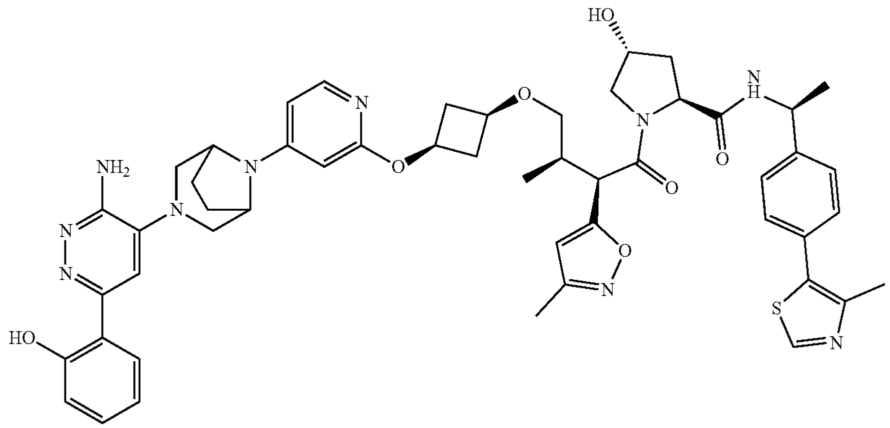
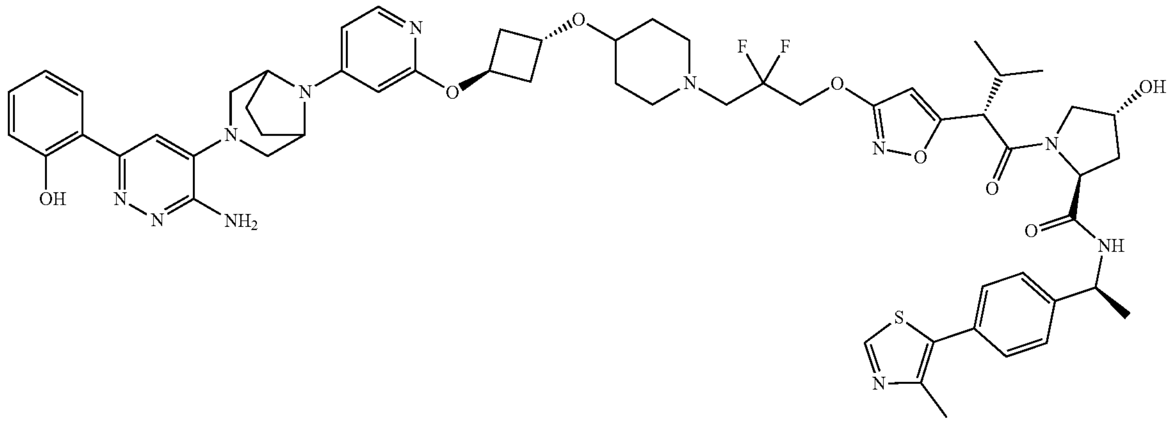
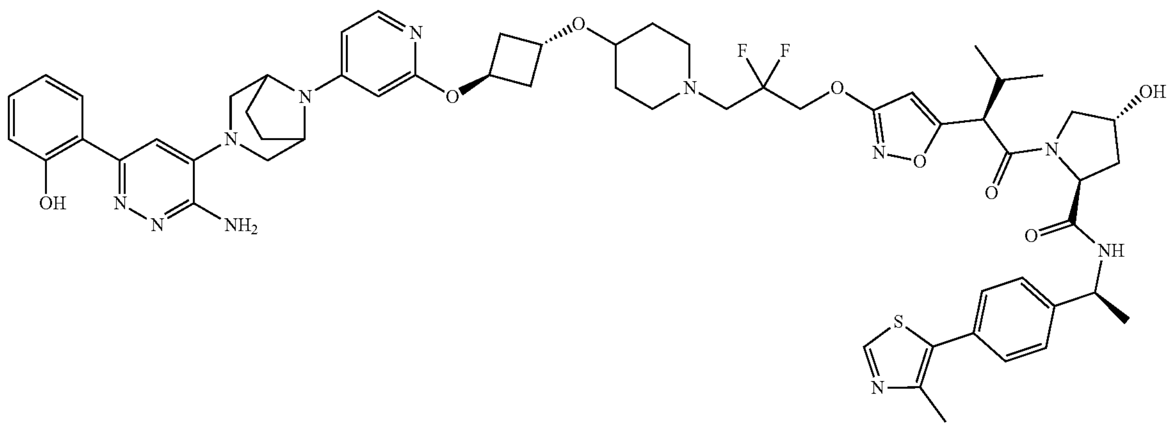

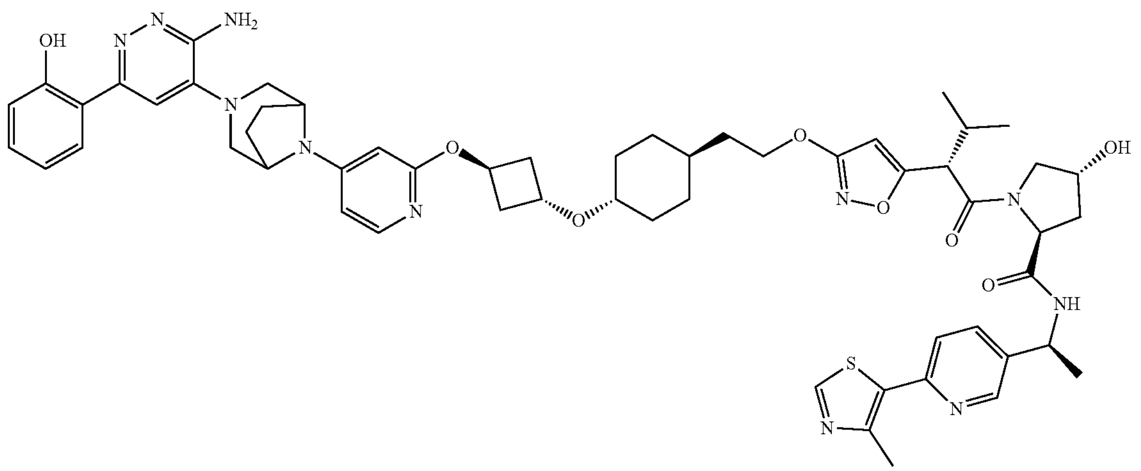
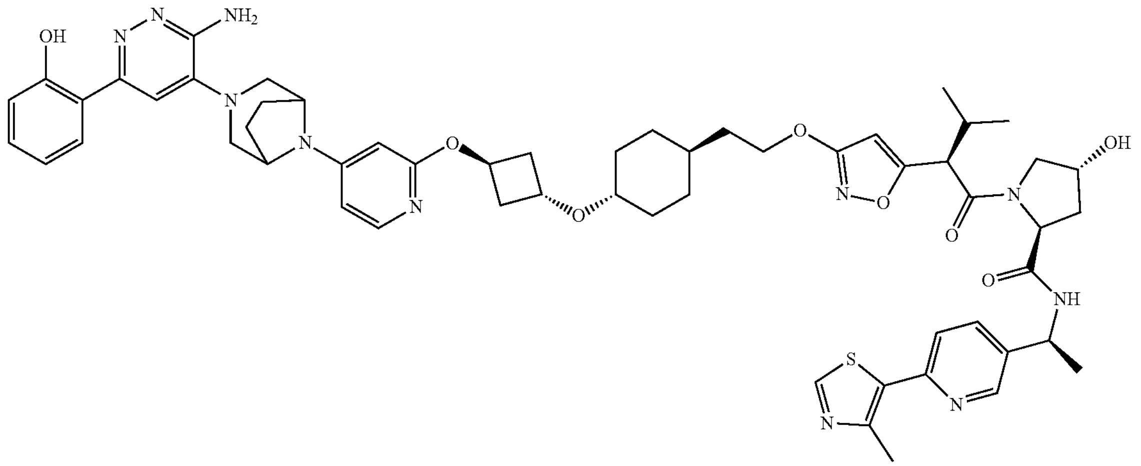
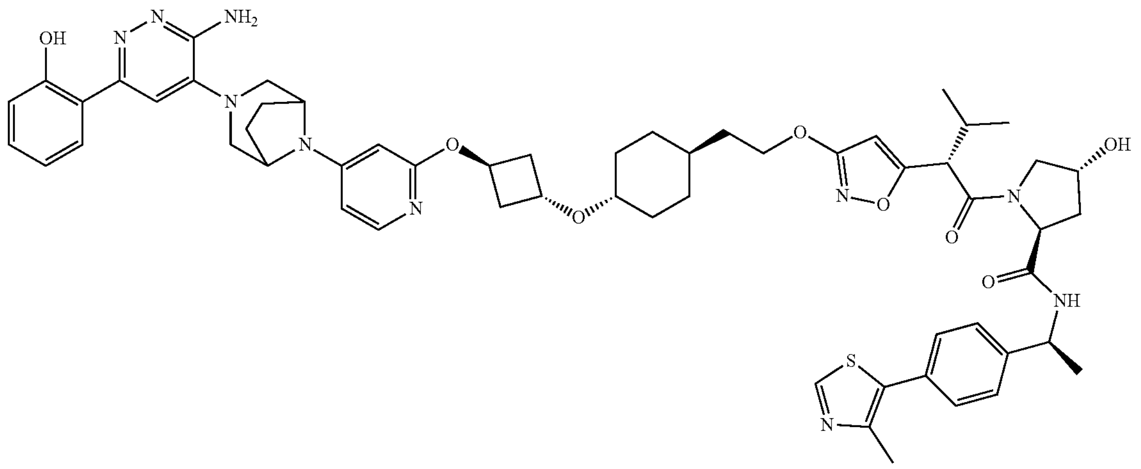

-continued
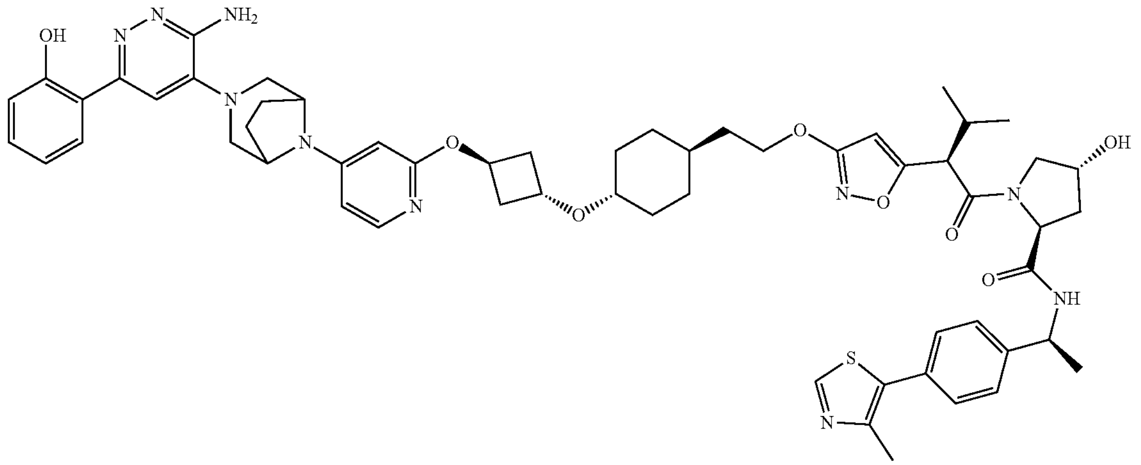
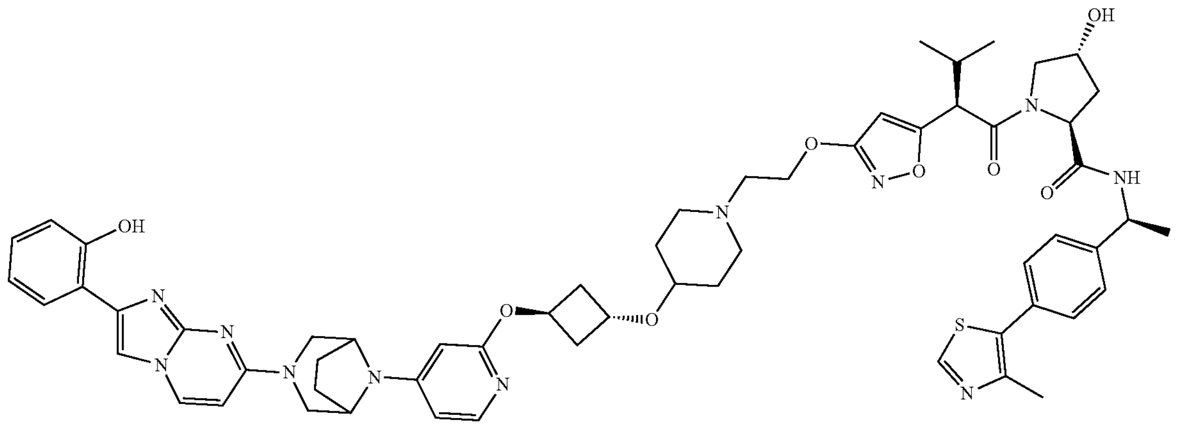
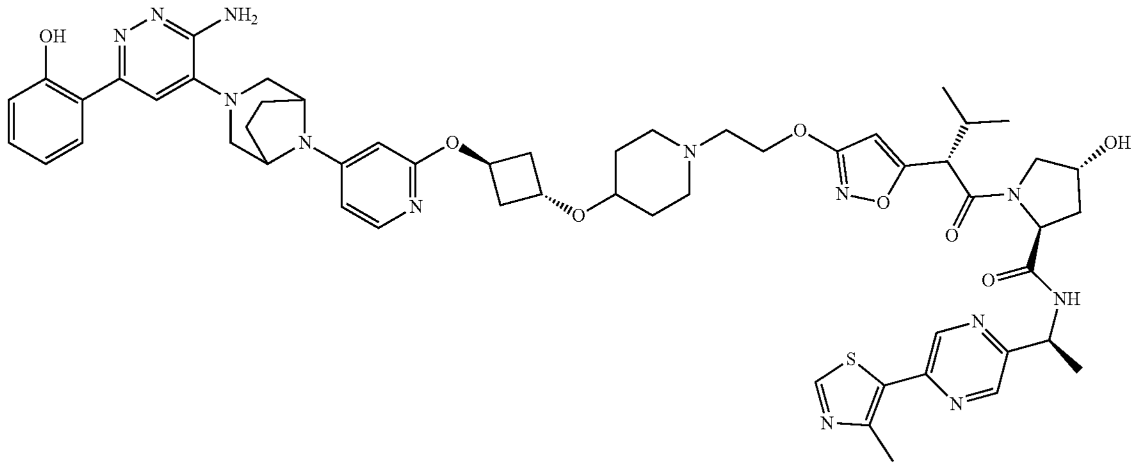

-continued
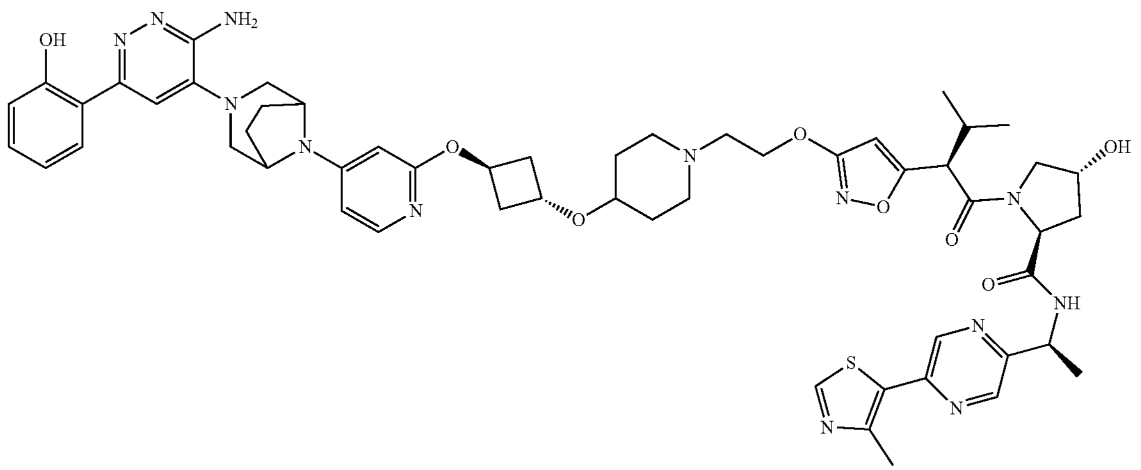
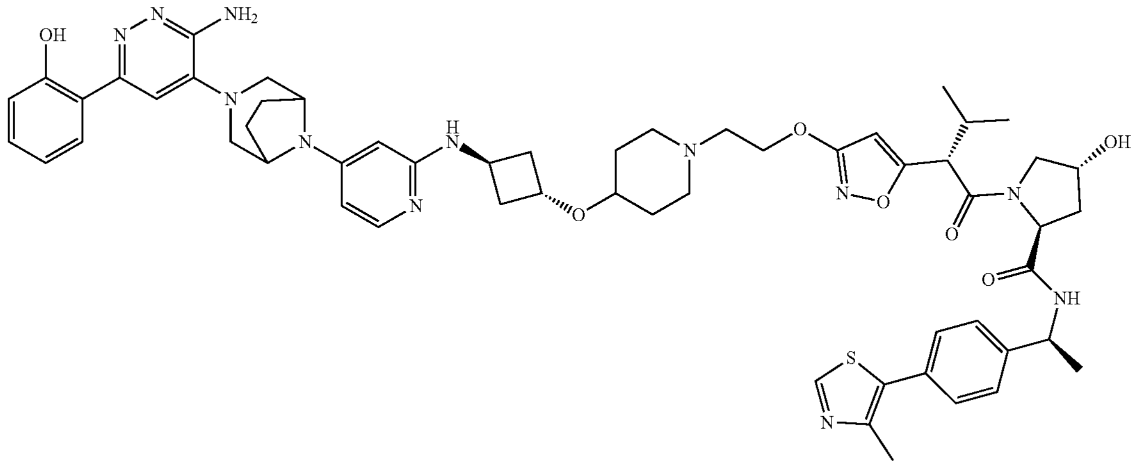
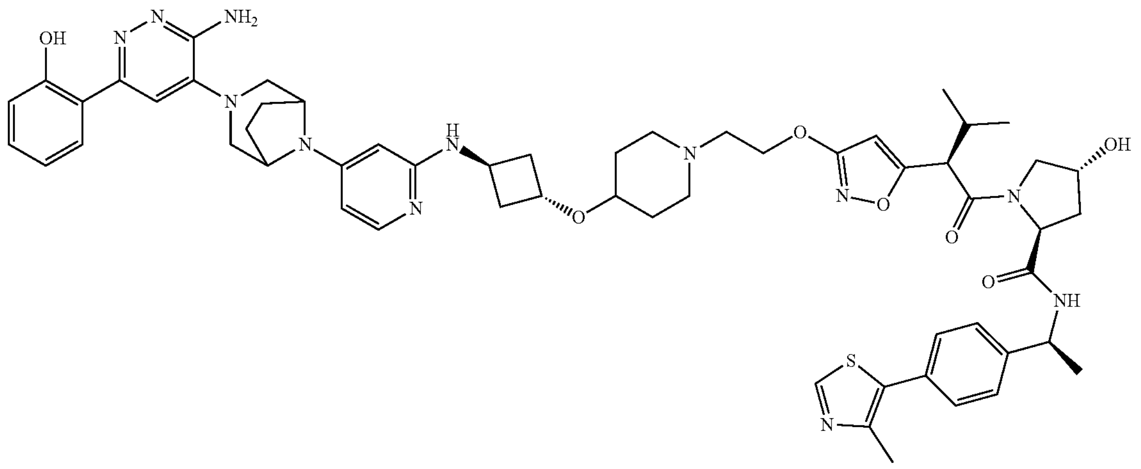

-continued
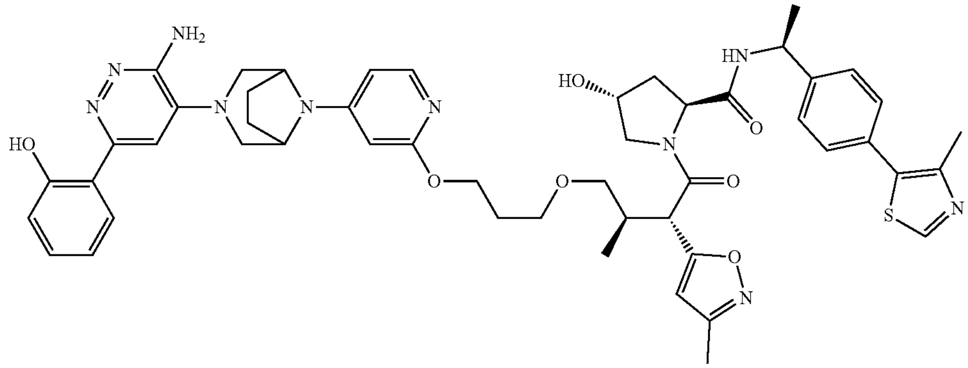
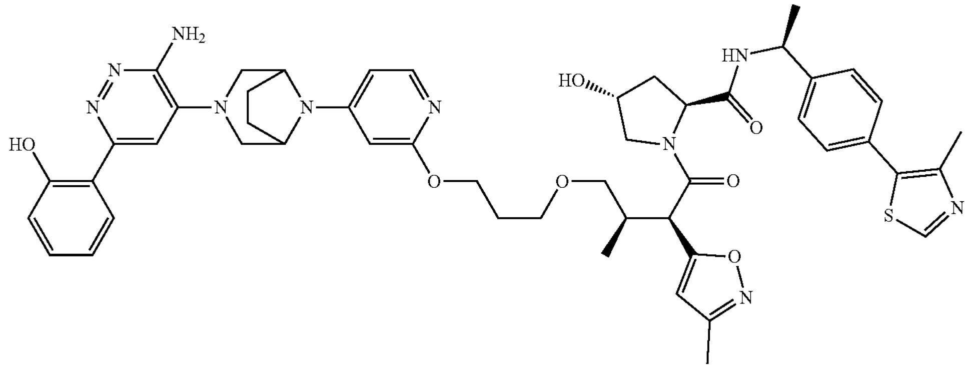
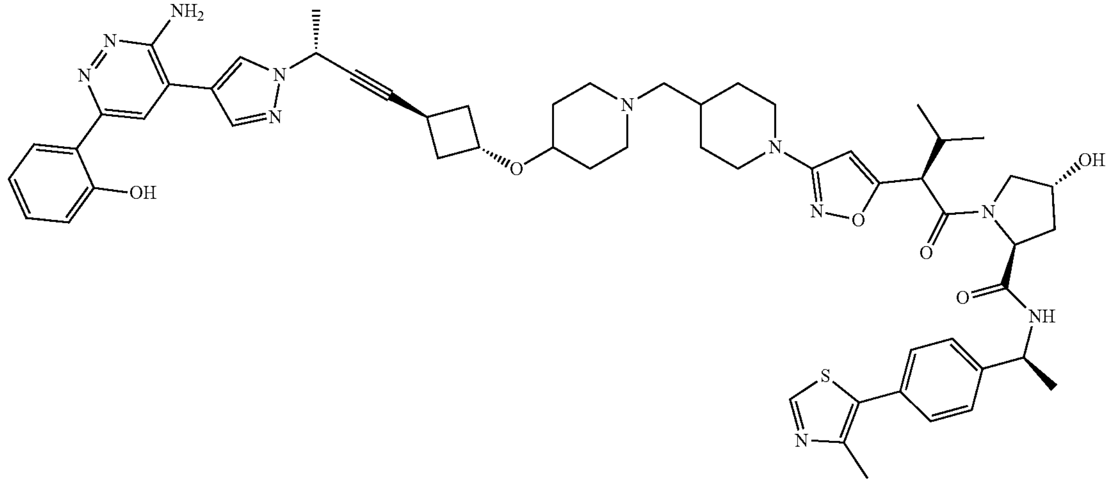
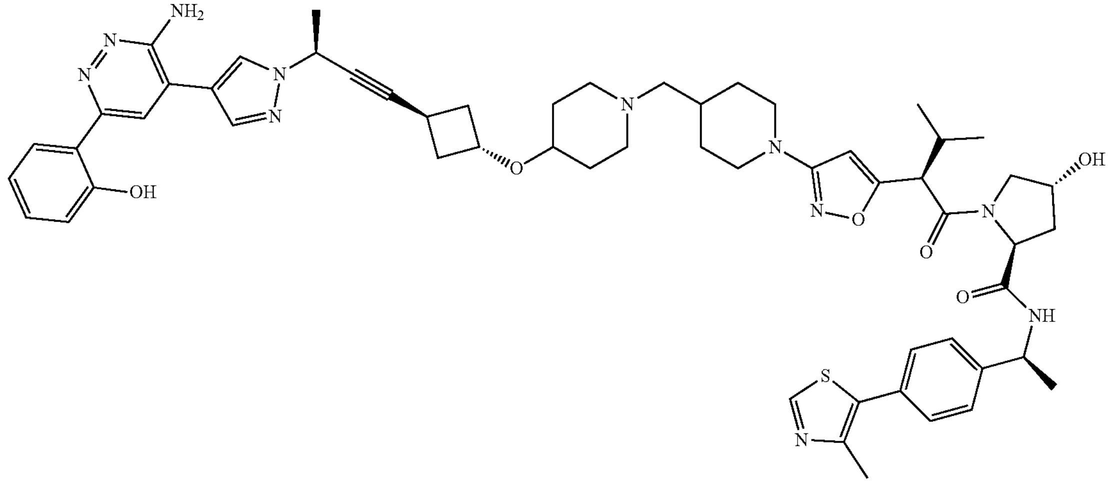

-continued
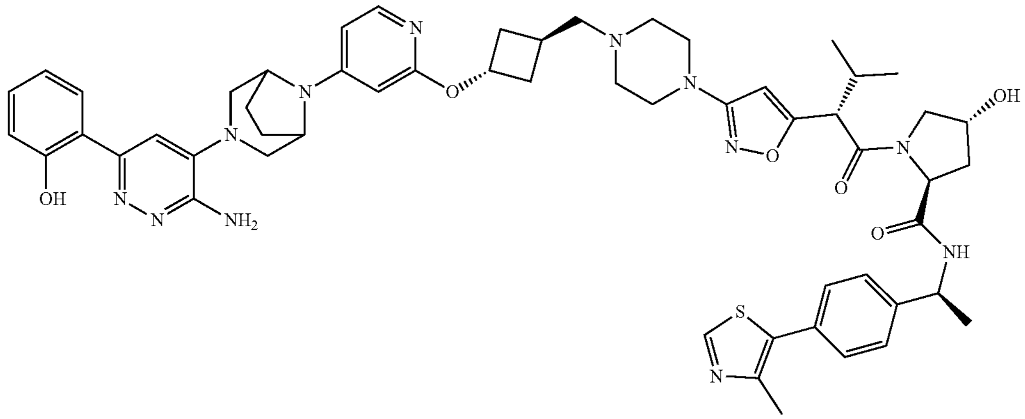
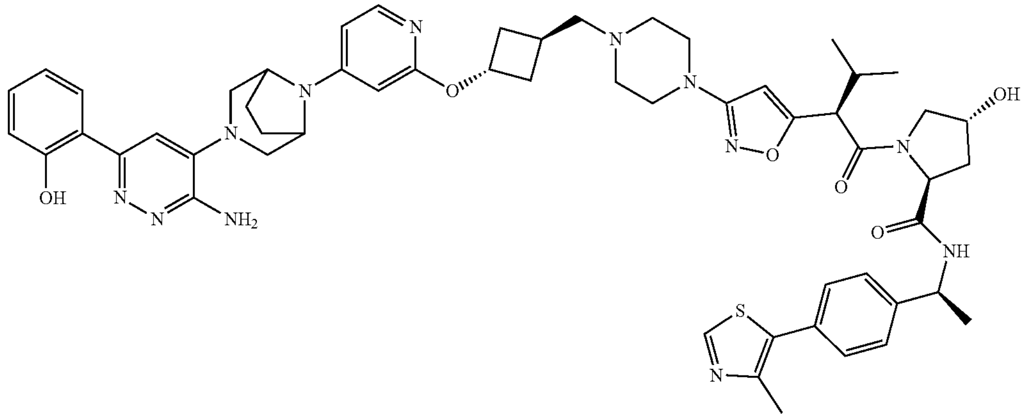
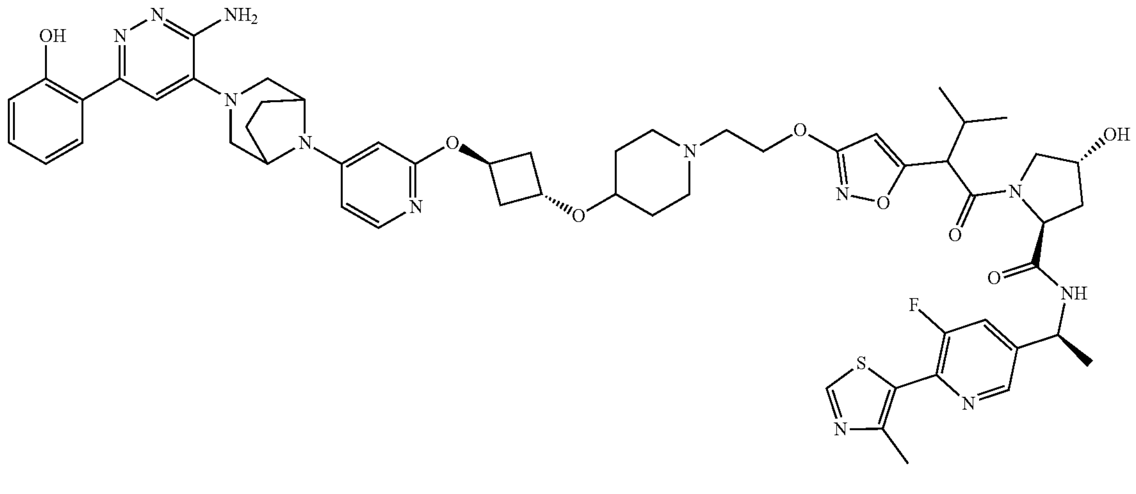

-continued
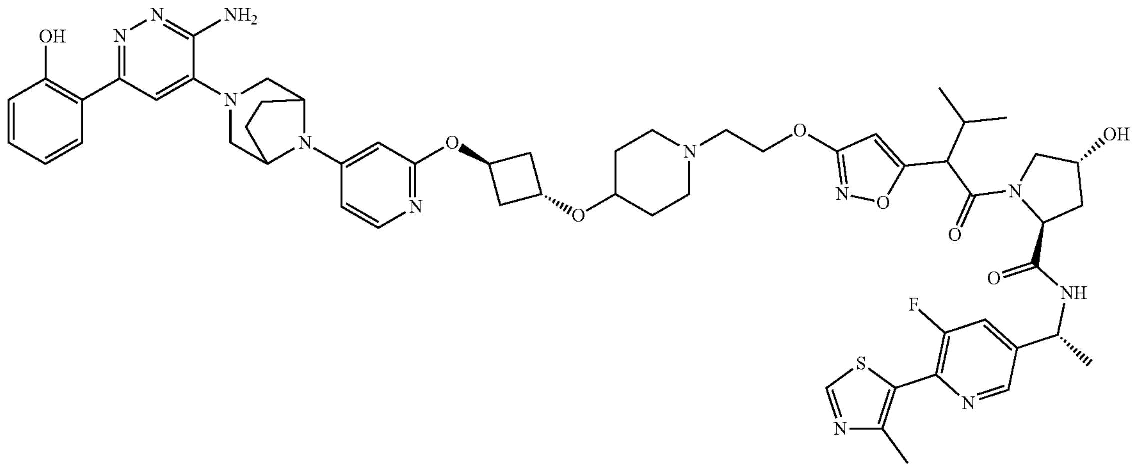
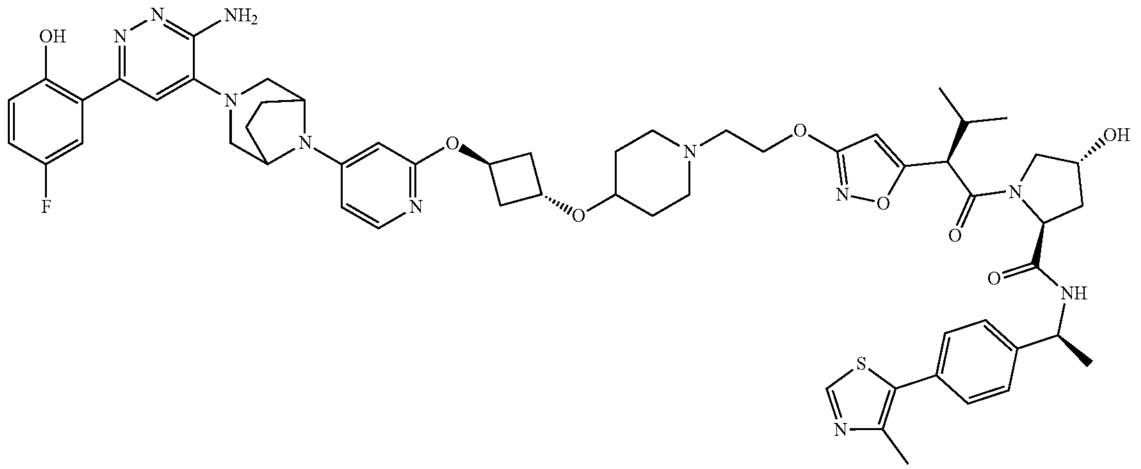
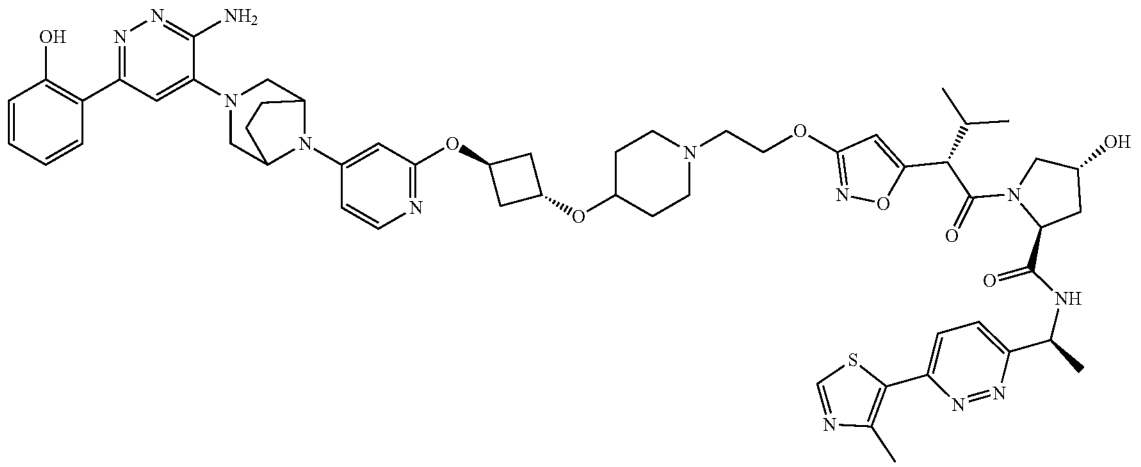

-continued
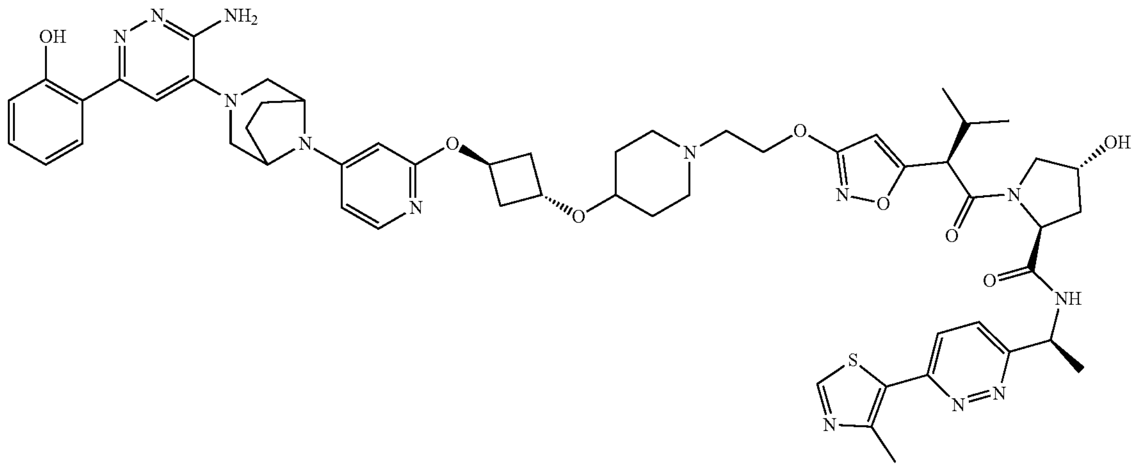
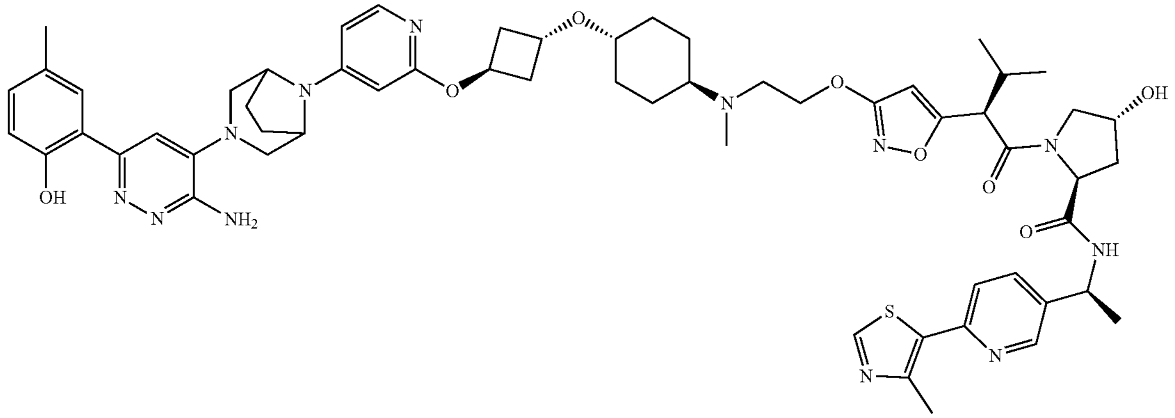
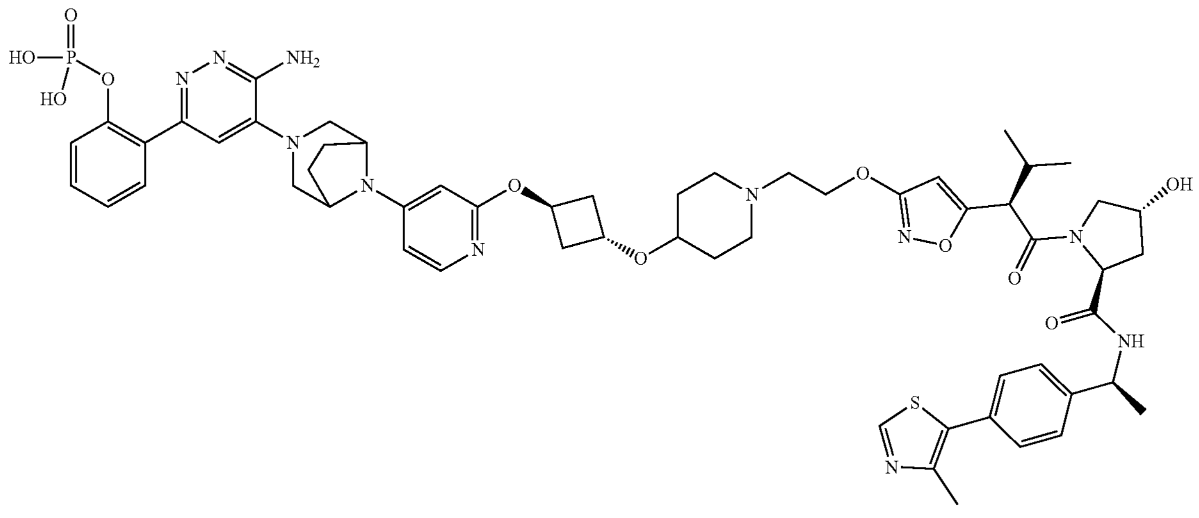

-continued
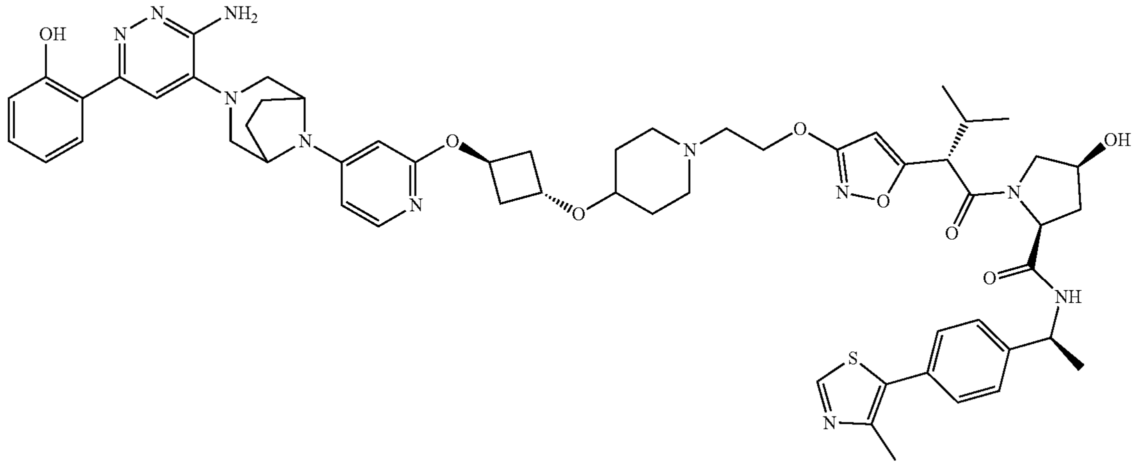
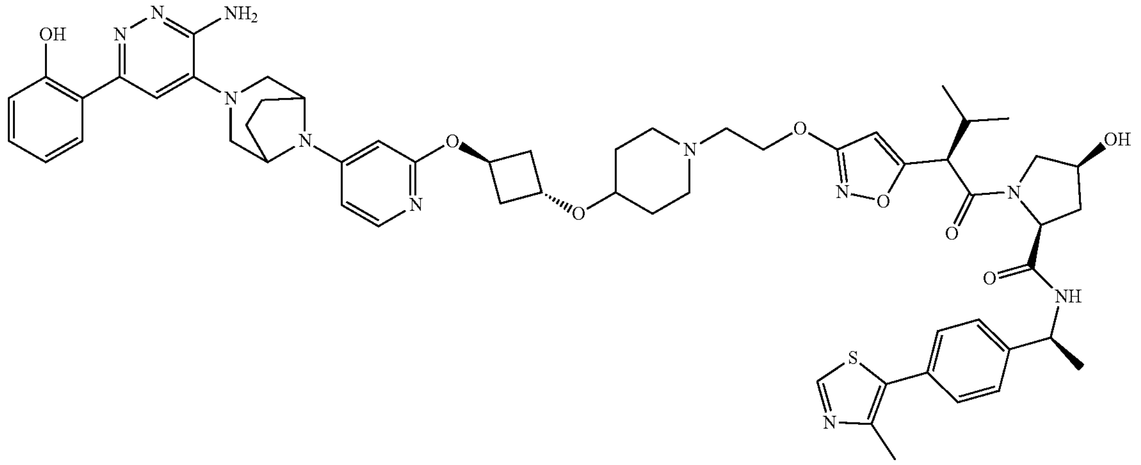
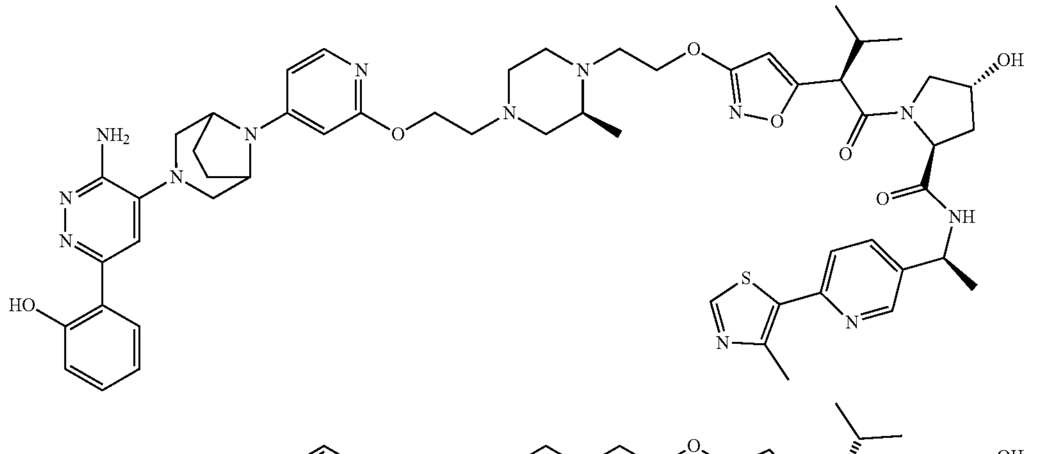
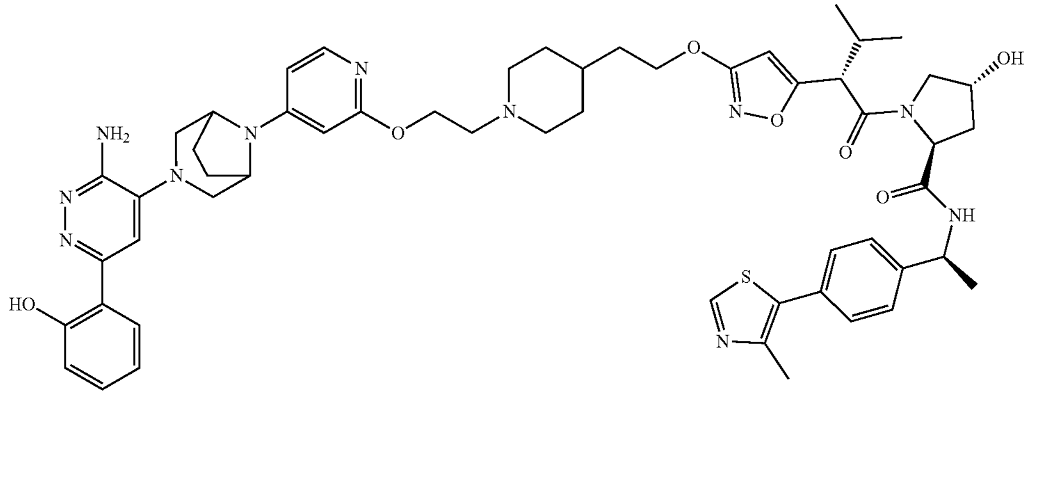

-continued
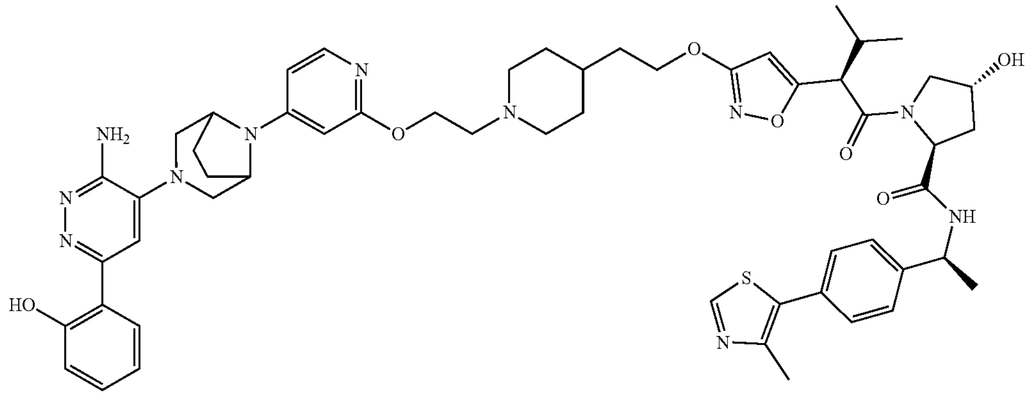
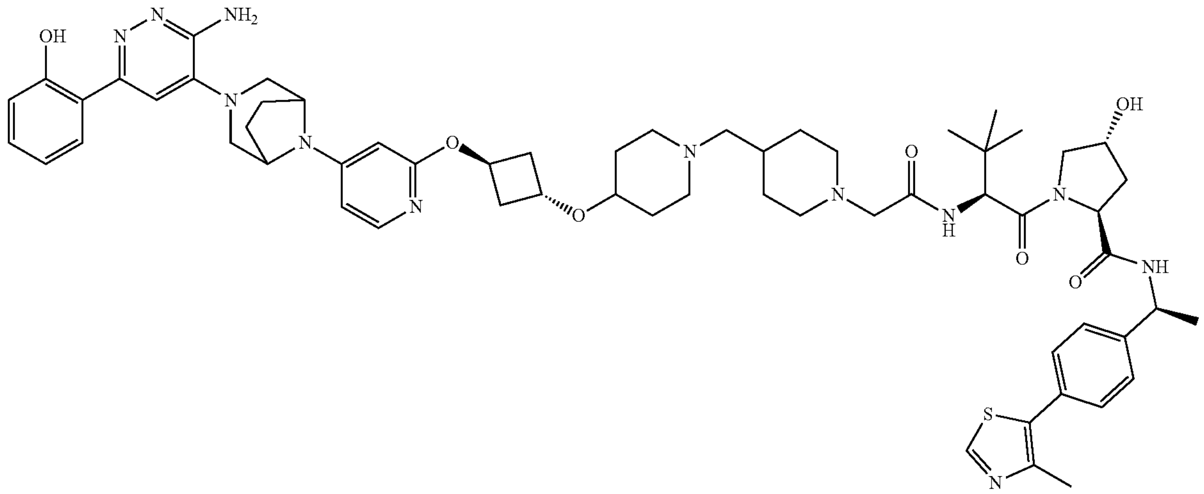
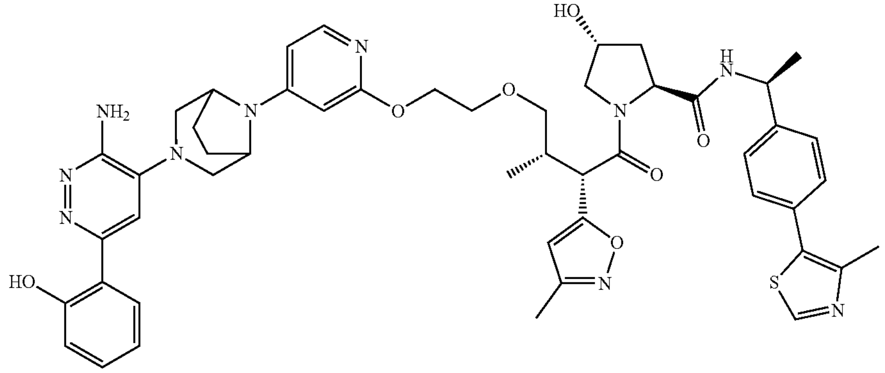

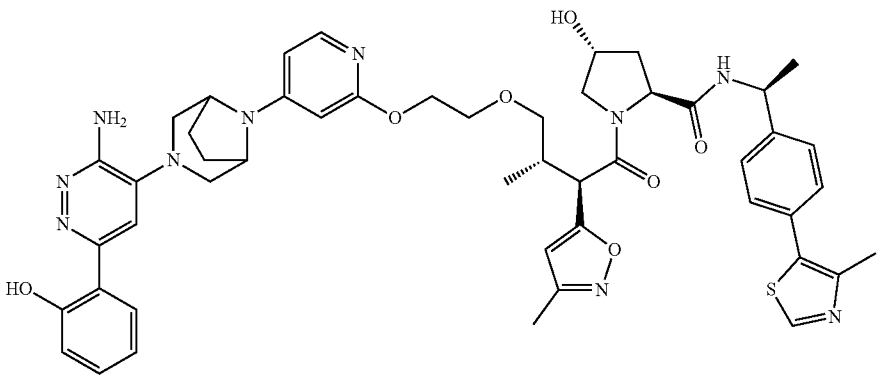
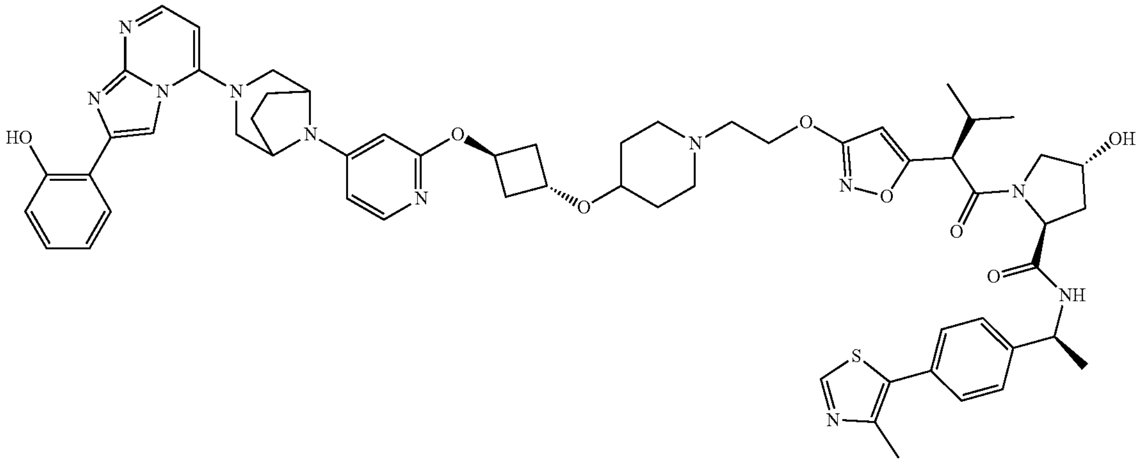
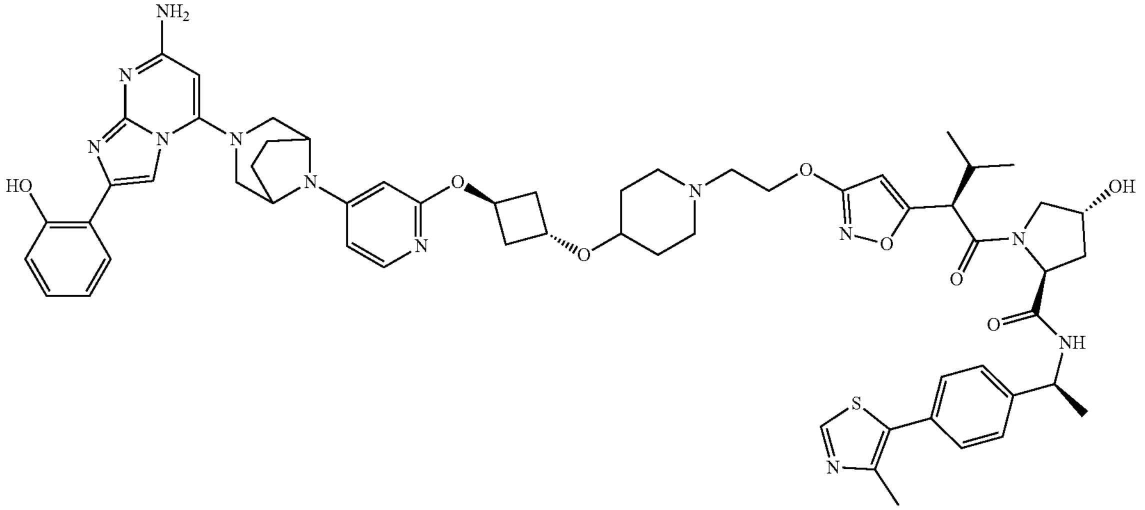

-continued
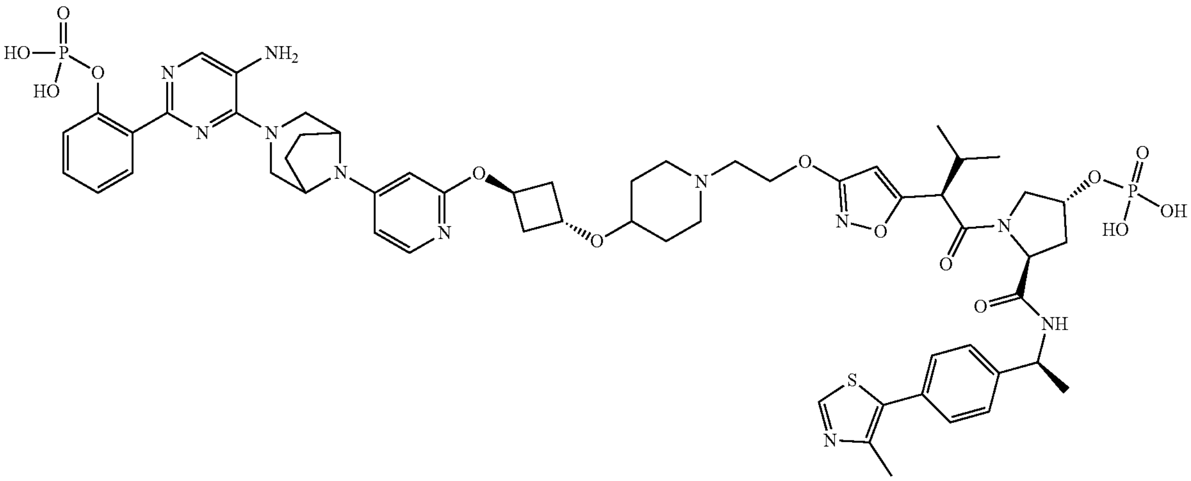
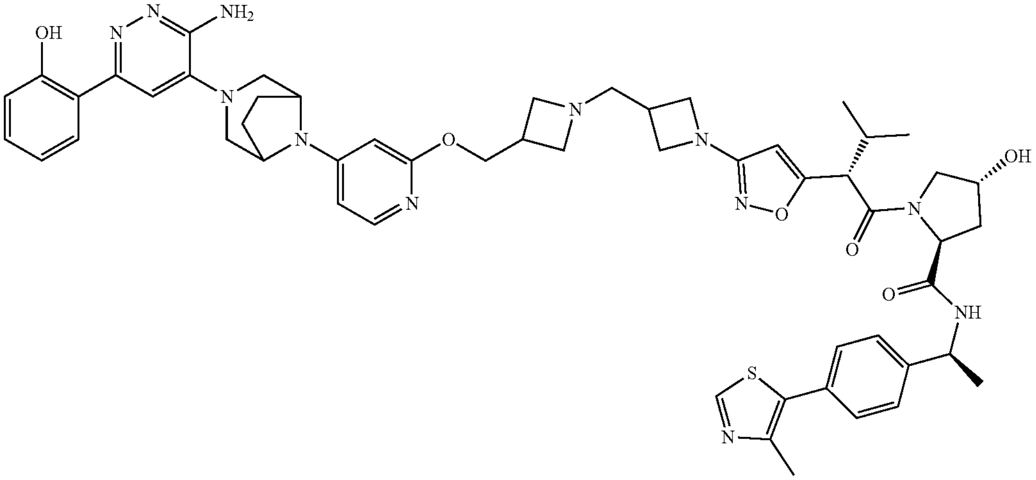
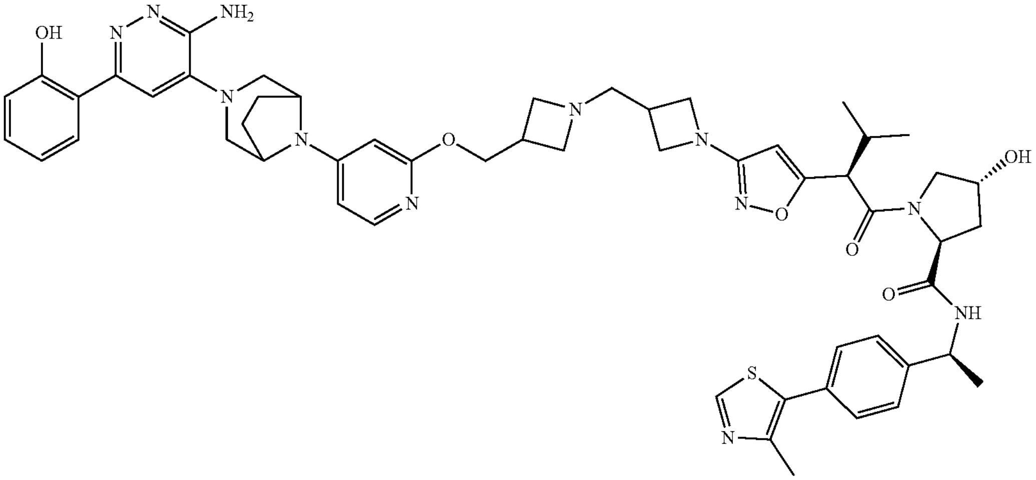

-continued
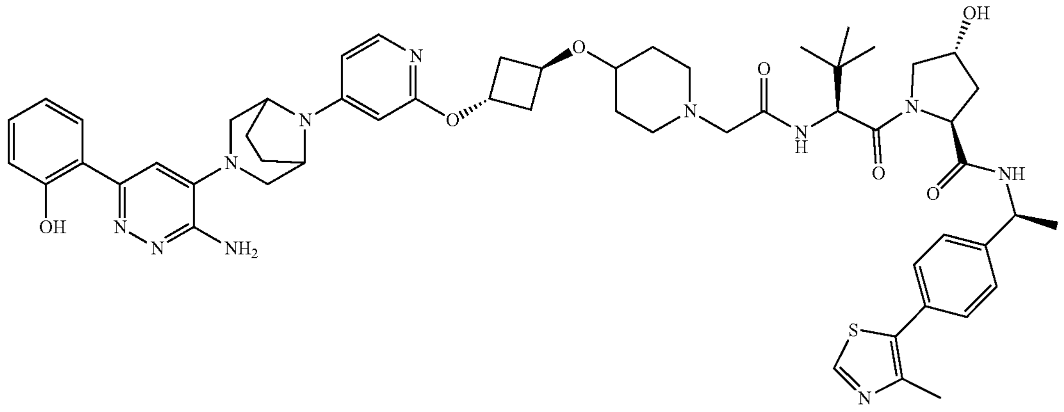
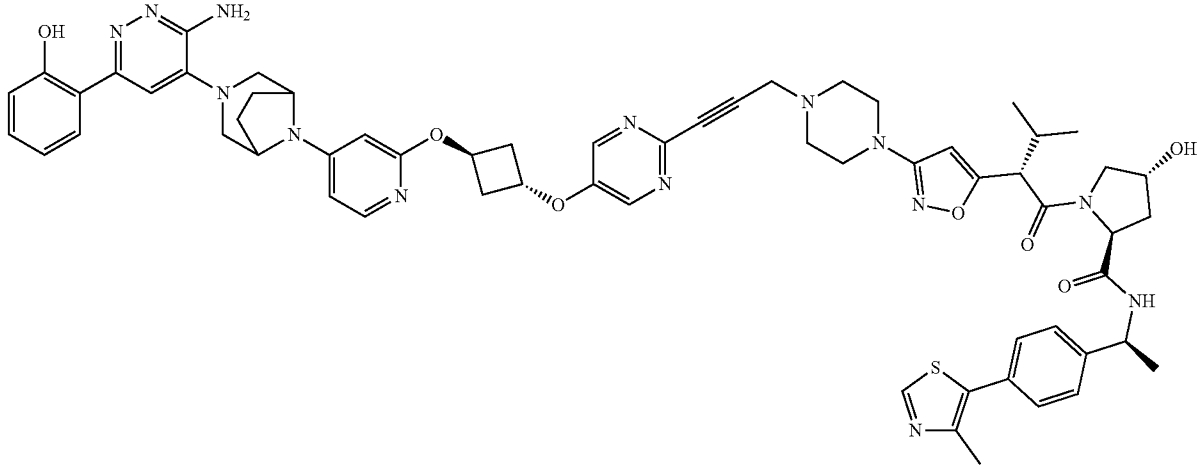
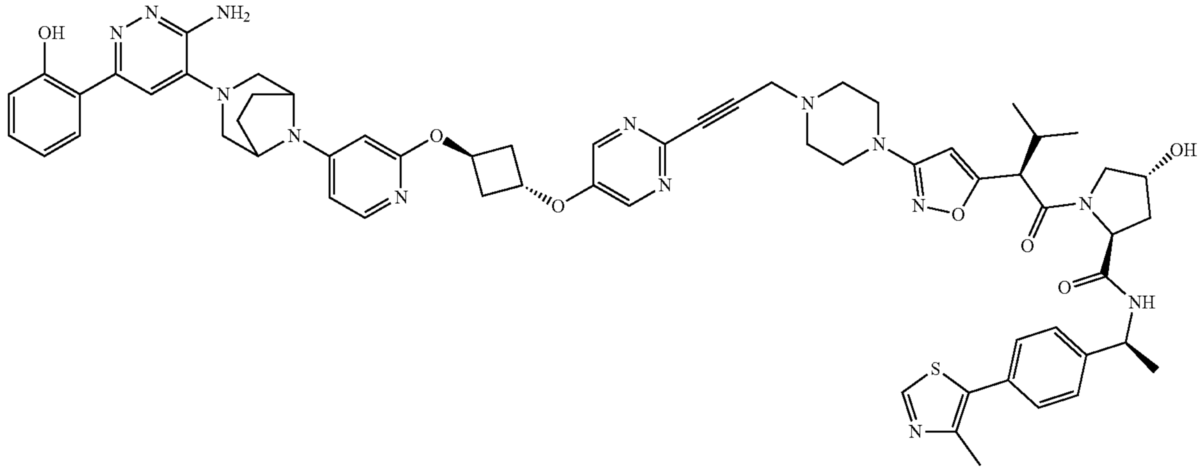

-continued
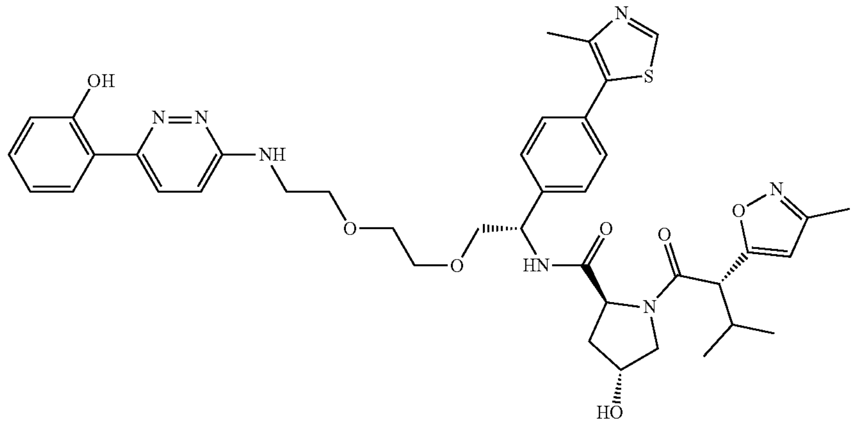
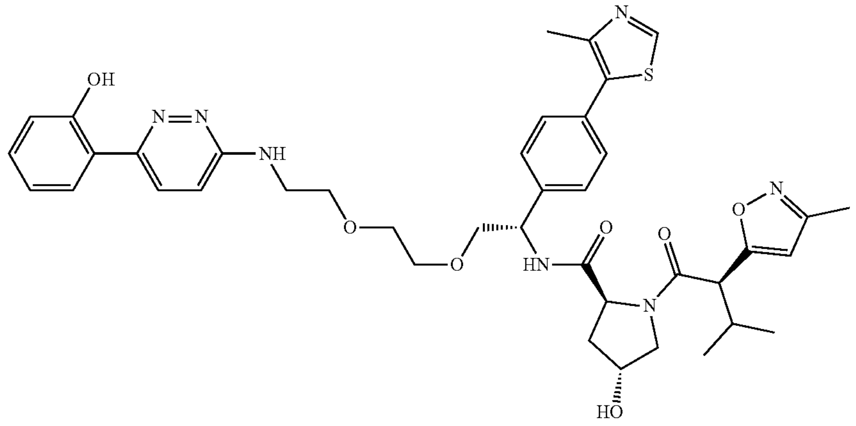
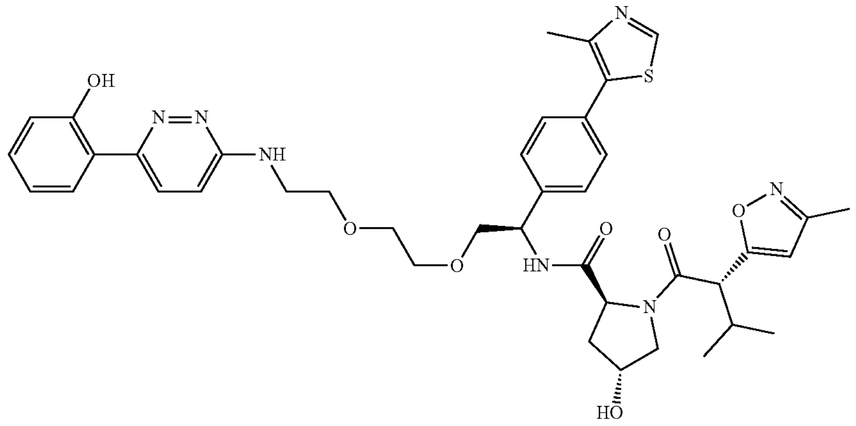
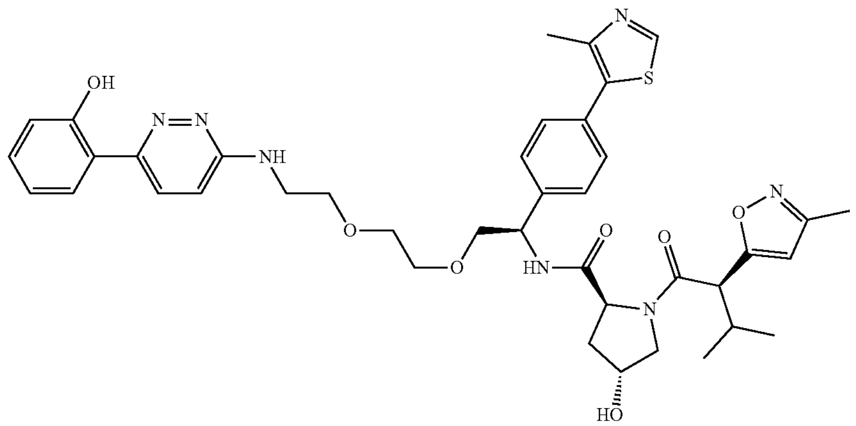

-continued
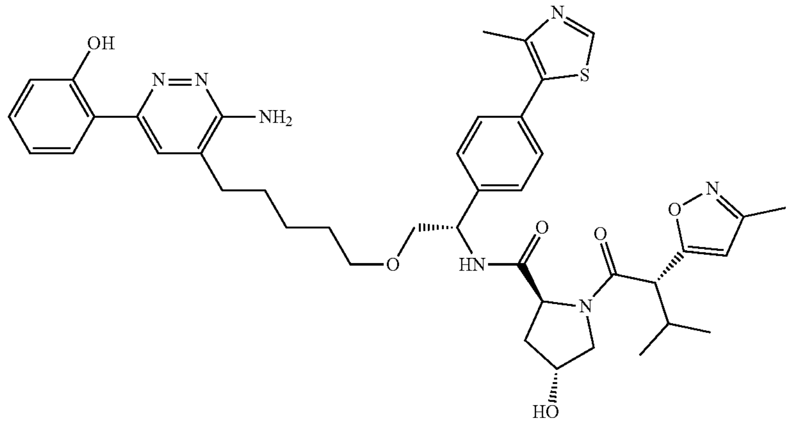
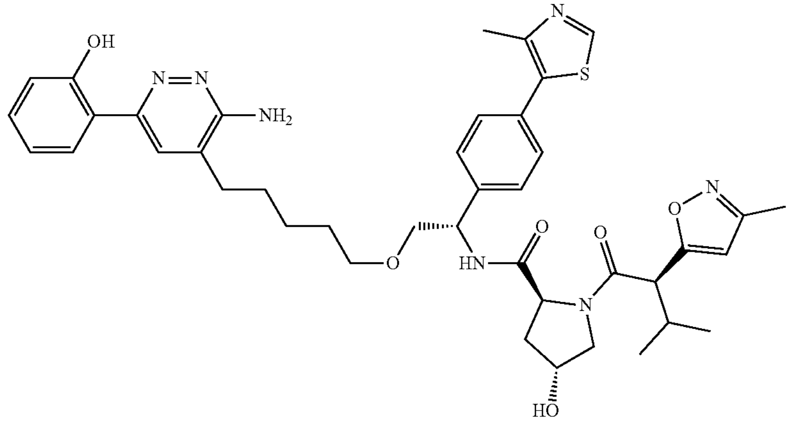
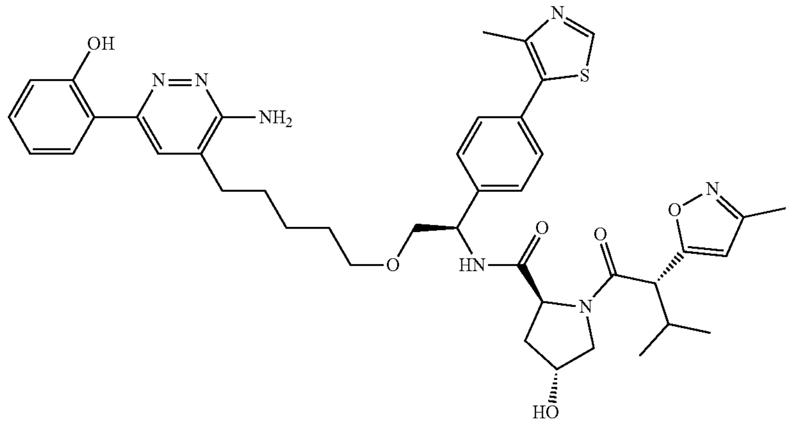
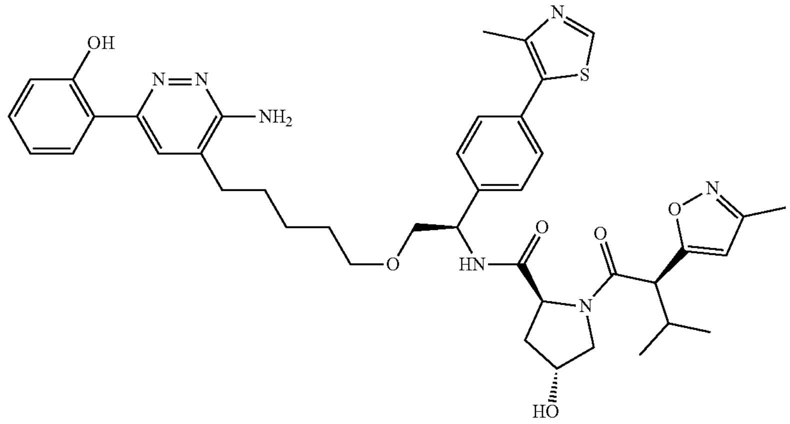

-continued
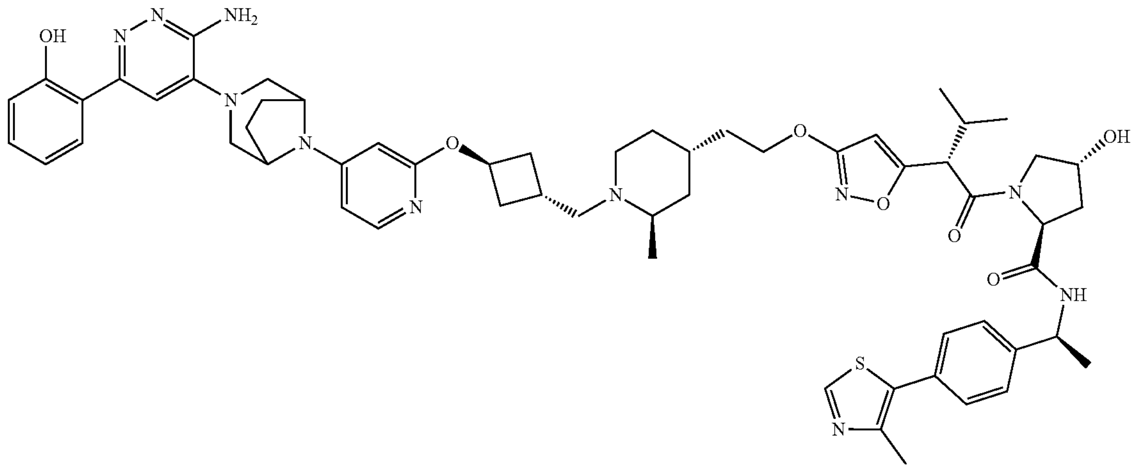
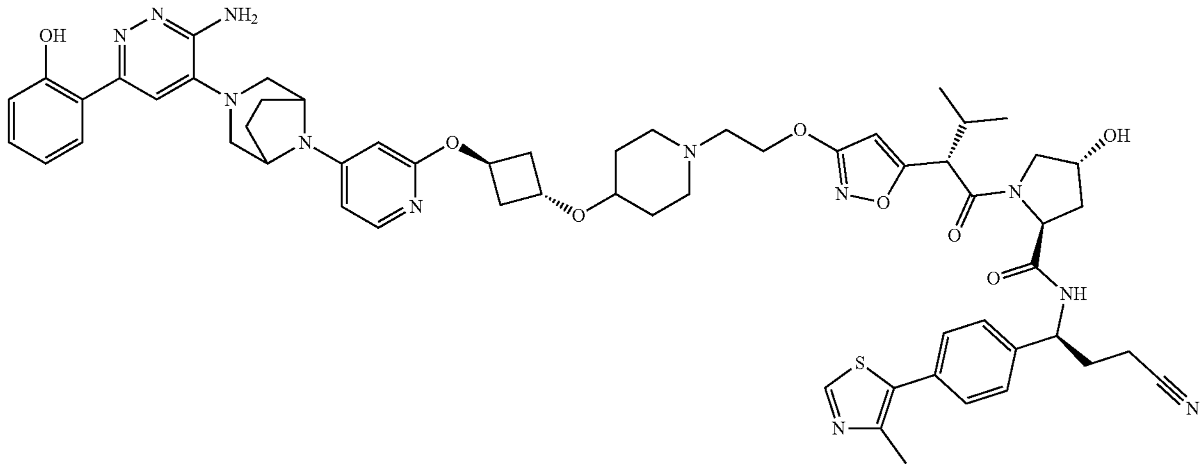
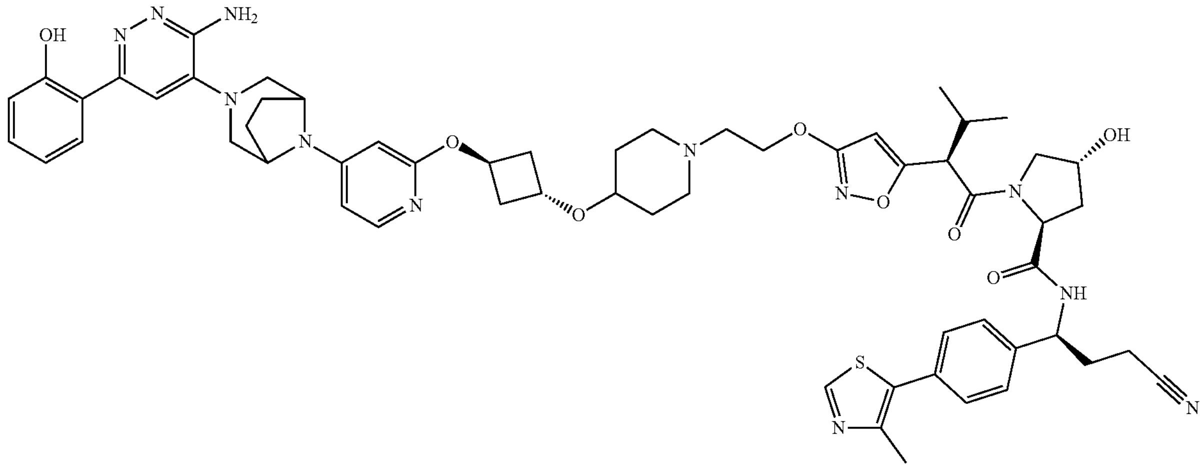

-continued

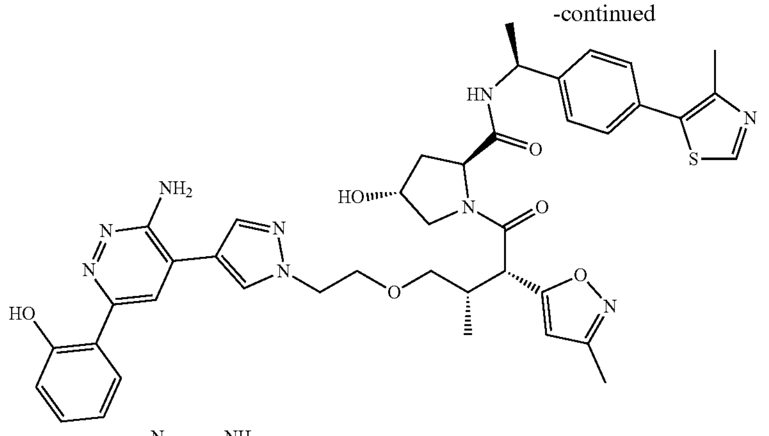

or

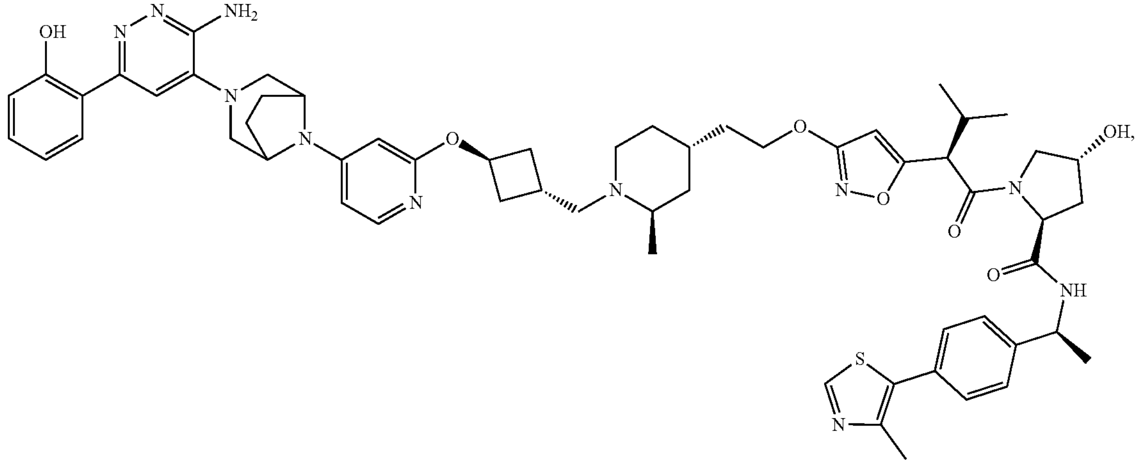 [SMILES: Cc1ncsc1-c1ccc([C@H](C)NC(=O)[C@@H]2C[C@@H](O)CN2C(=O)[C@@H](c2cc(OCC[C@H]3CCN(C[C@H]4C[C@H](Oc5cc(N6C7CCC6CN(c6cc(-c8ccccc8O)nnc6N)C7)ccn5)C4)[C@H](C)C3)no2)C(C)C)cc1]

or a pharmaceutically acceptable salt thereof.

28. The compound of claim 27, wherein the compound has a $D_{max}$ greater than or equal to 80%.

29. A pharmaceutical composition comprising an effective amount of the compound of claim 27, and a pharmaceutically acceptable carrier.

30. A method for treating a disease or disorder or ameliorating at least one symptom of the disease or disorder, comprising administering a therapeutically effective amount of the compound of claim 27, or a pharmaceutically acceptable salt thereof, to a subject, wherein the disease or disorder is associated with SMARCA2 or SMARCA4, and the compound, or pharmaceutically acceptable salt thereof, is effective in treating or ameliorating at least one symptom of the disease or disorder.

* * * * *